US012473285B2

(12) United States Patent
Nicewonger et al.

(10) Patent No.: US 12,473,285 B2
(45) Date of Patent: Nov. 18, 2025

(54) DCN-1 MODULATING COMPOUNDS AND METHODS OF USE THEREOF

(71) Applicant: Cellarity, Inc., Somerville, MA (US)

(72) Inventors: Robert Brian Nicewonger, Tyngsboro, MA (US); Mauricio Cortes, Wellesley, MA (US); Colin Diner, Somerville, MA (US); Ragy Haddad, Cambridge, MA (US); Sriram Krishnamoorthy, Acton, MA (US); Na Li, Winchester, MA (US); Frank Lovering, Acton, MA (US); Kristen Marino, Stoneham, MA (US); Samuel Miller, Cambridge, MA (US); Qing Tang, Boxborough, MA (US); Atli Thorarensen, Stow, MA (US); Ravi Ujjinamatada, Lexington, MA (US); David Zhang, West Roxbury, MA (US)

(73) Assignee: Cellarity, Inc., Somerville, MA (US)

( * ) Notice: Subject to any disclaimer, the term of this patent is extended or adjusted under 35 U.S.C. 154(b) by 0 days.

(21) Appl. No.: 18/935,099

(22) Filed: Nov. 1, 2024

(65) Prior Publication Data

US 2025/0163057 A1 May 22, 2025

Related U.S. Application Data

(60) Provisional application No. 63/682,745, filed on Aug. 13, 2024, provisional application No. 63/661,551, filed on Jun. 18, 2024, provisional application No. 63/655,541, filed on Jun. 3, 2024, provisional application No. 63/618,581, filed on Jan. 8, 2024, provisional application No. 63/547,249, filed on Nov. 3, 2023.

(51) Int. Cl.
*C07D 471/04* (2006.01)

(52) U.S. Cl.
CPC .................................. *C07D 471/04* (2013.01)

(58) Field of Classification Search
CPC .................................................. C07D 471/04
USPC ......................................................... 546/112
See application file for complete search history.

(56) References Cited

U.S. PATENT DOCUMENTS

| | | | | |
|---|---|---|---|---|
| 10,525,048 | B2 * | 1/2020 | Min | C07D 401/06 |
| 2014/0057938 | A1 | 2/2014 | Dounay et al. | |
| 2022/0017908 | A1 | 1/2022 | Rahl et al. | |

FOREIGN PATENT DOCUMENTS

| | | | |
|---|---|---|---|
| EP | 3609876 | B1 | 3/2022 |
| WO | 2017049295 | A1 | 3/2017 |
| WO | 2018183411 | A1 | 10/2018 |
| WO | 2020257790 | A1 | 12/2020 |

OTHER PUBLICATIONS

Kim et al., "Improvement of Oral Bioavailability of Pyrazolo-Pyridone Inhibitors of the Interaction of DCN1/2 and UBE2M," J. Med. Chem. 2021;64:5850-5862.

Kim et al., "Discovery of Novel Pyrazolo-pyridone DCN1 Inhibitors Controlling Cullin Neddylation," J. Med. Chem. 2019;62(18):8429-8442.

Zhou et al., "Selective inhibition of cullin 3 neddylation through covalent targeting DCN1 protects mice from acetaminophen-induced liver toxicity," Nature Communications 2021;12:2621.

Scott et al., "Blocking an N-terminal acetylation-dependent protein interaction inhibits an E3 ligase," Nature Chemical Biology 2017;13:850-857.

Hammill et al. "Discovery of an Orally Bioavailable Inhibitor of Defective in Cullin Neddylation 1 (DCN1)-Mediated Cullin Neddylation," J. Med. Chem. 2018;61:2694-2706.

Hammill et al., "Piperidinyl Ureas Chemically Control Defective in Cullin Neddylation 1 (DCN1)-Mediated Cullin Neddylation," J. Med. Chem. 2018;61:2680-2693.

Shi et al., "An efficient synthesis of new class of pyrazolo[3,4-b]pyridine-6-one derivatives by a novel cascade reaction," Journal of Heterocyclic Chemistry 2007;44(5):1013-1017.

PCT International Search Report for PCT/US2024/054169 dated Feb. 12, 2025.

PCT International Search Report for PCT/US2024054133 dated Feb. 18, 2025.

PCT International Search Report for PCT/US2024/054278 dated Feb. 20, 2025.

PubChem_CID_155415365, create date: Jan. 30, 2021, p. 2 formula.

* cited by examiner

*Primary Examiner* — Niloofar Rahmani

(74) *Attorney, Agent, or Firm* — Dechert LLP; John P. Rearick; Joseph W. Arico

(57) ABSTRACT

The present disclosure provides DCN-1 modulating compounds, pharmaceutically acceptable salts thereof, pharmaceutical compositions, and their use for treating sickle cell disorders, diseases, and conditions. Such compounds are of Formula I:

I

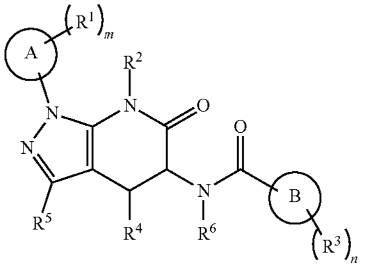

or a pharmaceutically acceptable salt thereof.

30 Claims, 24 Drawing Sheets

DCN-1 MODULATING COMPOUNDS AND METHODS OF USE THEREOF

CROSS-REFERENCE TO RELATED APPLICATIONS

This application claims the benefit of U.S. Provisional Application Nos. 63/547,249, filed Nov. 3, 2023; 63/618,581, filed Jan. 8, 2024; 63/655,541, filed Jun. 3, 2024; 63/661,551, filed Jun. 18, 2024; and 63/682,745, filed Aug. 13, 2024; the entirety of each of which is hereby incorporated by reference.

TECHNICAL FIELD OF THE INVENTION

The present disclosure relates generally to various compounds and compositions useful in the treatment of hemoglobin-related disorders including sickle cell disorders, diseases, and conditions, and thalassemia.

BACKGROUND OF THE INVENTION

Hemoglobinopathies are diseases that affect hemoglobin that include sickle cell disease and thalassemia. Sickle cell disease or disorder is a group of inherited red blood cell disorders that affect hemoglobin and can block blood flow to the body. Specifically, a defective beta hemoglobin chain in sickle cell patients twists and changes the shape of each red blood cell from a doughnut-like shape into a “sickled” or croissant shape that can clog small blood vessels and prevent the delivery of oxygen around the body. Sickle-cell disease is characterized by various acute and chronic complications, which are associated with significant morbidity and mortality in an afflicted subject. Thalassemia is also an inherited red blood cell disorder that is caused by a defect in the beta-globin gene, controlling the production of the beta-globin chains of hemoglobin. Accordingly, a patient suffering from thalassemia can’t make enough normal hemoglobin and thus has relatively fewer red blood cells and lower blood oxygen levels than people who do not suffer from the disease. Thalassemia patients may not make enough of either or both of the alpha or beta proteins in hemoglobin.

The cullin family of ubiquitination E3s are the most well-characterized substrates of neddylation. Upon neddylation, the cullins constellate the cullin-RING E3 UB ligase family (CRLs), which has approximately 300 members. The CRLs regulate diverse biological processes including cell cycle, signal transduction, DNA replication, and viral modulation. CRL dysfunction is implicated in a number of human diseases, including cancer. Drug discovery efforts targeting the CRLs and the associated proteasomal protein degradation machinery have been extensive and continue to grow. The neddylation pathway has been successfully targeted by MLN4924 (Pevonedistat), an inhibitor of NEDD8’s E1 enzyme, that completely blocks NEDD8 ligation to substrates. MLN4924 is currently being tested in oncology clinical trials. An inhibitor of the COP9 signalosome, responsible for de-neddylation of the CRLs, has been reported and also displays anti-tumor activity. Defective in cullin neddylation 1 (DCN-1) is a protein that interacts with cullins and is required for neddylation. DCN-1 is also known as DCUN1D1, DCNL1 or Squamous Cell Carcinoma-related Oncogene (SCCRO). DCN1 is the most well characterized isoform due to its common amplification as part of a large 3q26.3 amplicon in squamous cell carcinomas (SCC) and other tumors. DCN1 amplification in SCC negatively correlates with cause-specific survival, suggesting that targeting DCN1 may be of clinical utility in cancers. Its role in other diseases remains under-explored.

There remains a need to find therapeutic agents, methods, and therapies for the treatment of hemoglobin-related disorders including sickle cell disorders, diseases and conditions and thalassemia. The present invention fulfils this need and provides other related advantages.

BRIEF DESCRIPTION OF FIGURES

In FIG. 2, the data shows expression of fetal hemoglobin (HbF) in CD34+ humanized mouse models.

FIG. 3A shows expression based on normalization to housekeeping genes. FIG. 3B shows the amount of fetal hemoglobin gene expression (HBG1) relative to total hemoglobin (fetal plus adult beta chain hemoglobin genes (HBG1+ HBB)). FIG. 3C shows expression based on normalization to the number of glycophorin A (GlyA), a surface marker found on red blood cells, positive human erythroid precursor cells in the bone marrow.

In FIG. 10A, all treatment groups show increased percentage of HbF expression in GlyA+ cells. In FIG. 10B, most treatment groups show increased HbF protein levels when normalized for % GlyA+ cells.

DETAILED DESCRIPTION OF CERTAIN EMBODIMENTS

Figure 1A:
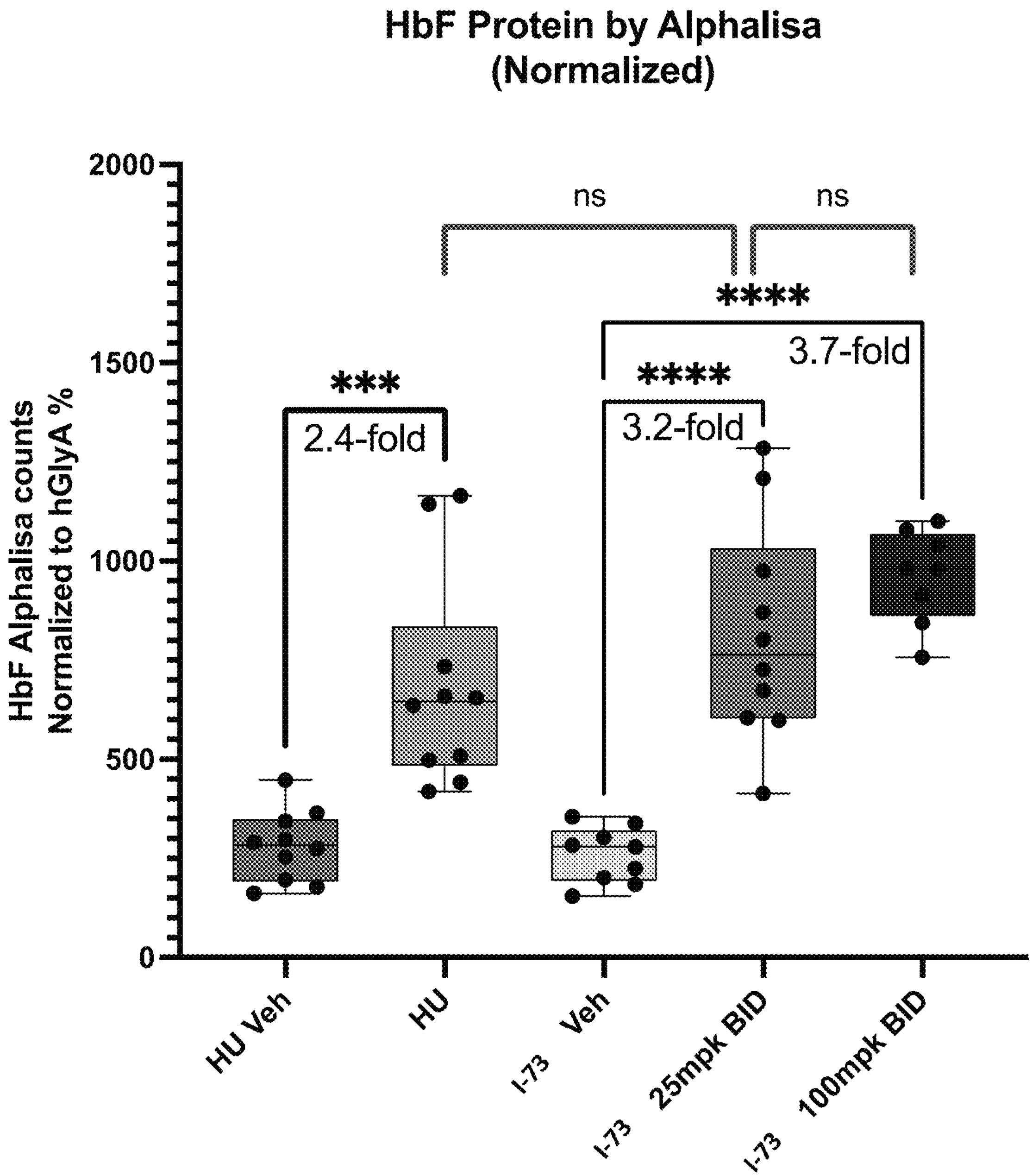
FIGS. 1A, 1B and 1C show induction of fetal hemoglobin in humanized mice by treatment with I-73 vs. hydroxyurea (HU) control. Human hematopoietic stem cell-reconstituted NBSGW mice were treated with the indicated doses of hydroxyurea (HU) or I-73 for three weeks. Fetal hemoglobin protein (HbF) expression was assessed by AlphaLISA™ and the results are shown in FIG. 1A. Fetal hemoglobin gene expression (HBG1) were assessed by Nanostring™ and the results are shown in FIG. 1B. The ratio of fetal (HBG) to adult hemoglobin gene (HBB) expression induced by I-73 was compared to that induced by hydroxyurea and the results are shown in FIG. 1C.

1. General Description of Certain Embodiments of the Invention; Definitions

It has now been found that the compounds and compositions of the disclosure can modulate DCN-1, induce fetal hemoglobin and are useful in treating hemoglobin-related disorders including sickle cell disorders, diseases and conditions and thalassemia.

In one aspect, the present disclosure provides a compound of Formula I:

I

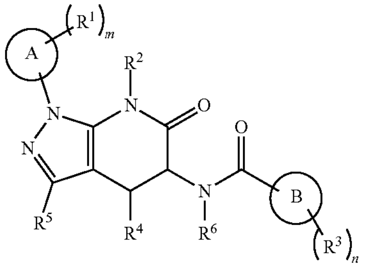

or a pharmaceutically acceptable salt thereof, wherein:

Ring A is phenyl, 3-8 membered saturated or partially unsaturated monocyclic carbocyclic ring, or a 5-6 membered monocyclic heteroaromatic ring having 1-4 heteroatoms independently selected from nitrogen, oxygen, and sulfur;

Ring B is phenyl or a 5-6 membered monocyclic heteroaromatic ring having 1-4 heteroatoms independently selected from nitrogen, oxygen, and sulfur;

each occurrence of $R^1$ is independently optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, or —NRS(O)$_2$R;

$R^2$ is an optionally substituted group selected from $C_{1-6}$ aliphatic or a 3-8 membered saturated or partially unsaturated monocyclic carbocyclic ring;

each occurrence of $R^3$ is independently an optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, or —NRS(O)$_2$R;

$R^4$ is phenyl, a 3-8 membered saturated or partially unsaturated monocyclic carbocyclic ring, or a substituted $C_{1-6}$ aliphatic; wherein $R^4$ is optionally substituted with p instances of $R^7$;

$R^5$ is a substituent comprising a warhead group;

$R^6$ is hydrogen or an optionally substituted $C_{1-6}$ aliphatic group;

each occurrence of $R^7$ is independently optionally substituted $C_{1-6}$ aliphatic, halogen, —CN, —NC, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, —NRS(O)$_2$R, phenyl, or a 5-6 membered heteroaromatic ring having 1-3 heteroatoms selected from nitrogen, sulfur, and oxygen;

each occurrence of R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur;

m is 0, 1, 2, 3, 4, or 5;

n is 0, 1, 2, 3, 4, or 5; and p is 0, 1, 2, 3, 4, or 5.

In one aspect, the present disclosure provides a compound of Formula Ia:

Ia

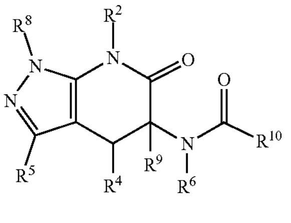

or a pharmaceutically acceptable salt thereof, wherein:

$R^8$ is phenyl, a 3-8 membered saturated or partially unsaturated monocyclic carbocyclic ring, a 4-10 membered saturated or partially unsaturated bicyclic carbocyclic ring, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, an 8-10 membered bicyclic heteroaromatic ring having 1-5 heteroatoms independently selected from nitrogen, oxygen, and sulfur, or a $C_{1-6}$ aliphatic; wherein $R^8$ is optionally substituted with m instances of $R^1$;

$R^{10}$ is phenyl, a 3-8 membered saturated or partially unsaturated monocyclic carbocyclic ring, a 4-10 membered saturated or partially unsaturated bicyclic carbocyclic ring, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, an 8-10 membered bicyclic heteroaromatic ring having 1-5 heteroatoms independently selected from nitrogen, oxygen, and sulfur, or a $C_{1-6}$ aliphatic; wherein $R^{10}$ is optionally substituted with n instances of $R^3$;

each occurrence of $R^1$ is independently optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, or —NRS(O)$_2$R;

$R^2$ is hydrogen, an optionally substituted group selected from $C_{1-6}$ aliphatic or a 3-8 membered saturated or partially unsaturated monocyclic carbocyclic ring;

each occurrence of $R^3$ is independently an optionally substituted $C_{1-6}$ aliphatic, an optionally substituted 3-8 membered saturated or partially unsaturated monocyclic carbocyclic ring, an optionally substituted 4-10 membered saturated or partially unsaturated bicyclic carbocyclic ring, an optionally substituted 3-8 membered saturated or partially unsaturated monocyclic heterocyclic ring having 1-2 heteroatoms independently selected from nitrogen, oxygen, and sulfur, an optionally substituted 5-10 membered bicyclic heterocyclic ring having 1-4 heteroatoms independently selected from nitrogen, oxygen, and sulfur, an optionally substituted 5-6 membered monocyclic heteroaromatic ring having 1-4 heteroatoms independently selected from nitrogen, oxygen, and sulfur, an optionally substituted 8-10 membered bicyclic heteroaromatic ring having 1-5 heteroatoms independently selected from nitrogen, oxygen, and sulfur, optionally substituted phenyl, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, or —NRS(O)$_2$R;

$R^4$ is phenyl, a 3-8 membered saturated or partially unsaturated monocyclic carbocyclic ring, a 4-10 membered bicyclic carbocyclic ring, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur, or a $C_{1-6}$ aliphatic; wherein $R^4$ is optionally substituted with p instances of $R^7$;

$R^5$ is a substituent comprising a warhead group;

$R^6$ is hydrogen or an optionally substituted $C_{1-6}$ aliphatic group;

each occurrence of $R^7$ is independently optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, —NRS(O)$_2$R, optionally substituted phenyl, or an optionally substituted 5-6 membered heteroaromatic ring having 1-3 heteroatoms selected from nitrogen, sulfur, and oxygen;

$R^9$ is hydrogen or an optionally substituted $C_{1-6}$ aliphatic group;

each occurrence of R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur;

m is 0, 1, 2, 3, 4, or 5;

n is 0, 1, 2, 3, 4, or 5; and p is 0, 1, 2, 3, 4, or 5.

As defined generally above, Ring A is selected from phenyl, 3-8 membered saturated or partially unsaturated monocyclic carbocyclic ring and, a 5-6 membered monocyclic heteroaromatic ring having 1-4 heteroatoms independently selected from nitrogen, oxygen, and sulfur.

In some embodiments, Ring A is phenyl. In some embodiments, Ring A is a 3-8 membered saturated monocyclic carbocyclic ring. In some embodiments, Ring A is a 3-8 membered partially unsaturated monocyclic carbocyclic ring. In some embodiments, Ring A is a 5-6 membered monocyclic heteroaromatic ring having 1-4 heteroatoms independently selected from nitrogen, oxygen, and sulfur.

In some embodiments, Ring A is phenyl.

In some embodiments, Ring A is selected from those depicted in Table 1, below.

As defined generally above, Ring B is selected from phenyl, and a 5-6 membered monocyclic heteroaromatic ring having 1-4 heteroatoms independently selected from nitrogen, oxygen, and sulfur.

In some embodiments, Ring B is phenyl. In some embodiments, Ring B is a 5-6 membered monocyclic heteroaromatic ring having 1-4 heteroatoms independently selected from nitrogen, oxygen, and sulfur.

In some embodiments, Ring B is phenyl.

In some embodiments, Ring B is selected from those depicted in Table 1, below.

As defined generally above, each occurrence of $R^1$ is independently optionally substituted $C_{1-6}$ aliphatic, halogen, —CN, —NC, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, or —NRS(O)$_2$R.

In some embodiments, $R^1$ is a $C_{1-6}$ aliphatic group. In some embodiments, $R^1$ is a substituted $C_{1-6}$ aliphatic group.

In some embodiments, $R^1$ is halogen. In some embodiments, $R^1$ is —CN. In some embodiments, $R^1$ is —NC. In some embodiments, $R^1$ is —C(O)R. In some embodiments, $R^1$ is —C(O)OR. In some embodiments, $R^1$ is —OC(O)R. In some embodiments, $R^1$ is —$C(O)N(R)_2$. In some embodiments, $R^1$ is —N(R)C(O)R. In some embodiments, $R^1$ is —$N(R)C(O)N(R)_2$. In some embodiments, $R^1$ is —OC(O)$N(R)_2$. In some embodiments, $R^1$ is —N(R)C(O)OR. In some embodiments, $R^1$ is —OR. In some embodiments, $R^1$ is —$N(R)_2$. In some embodiments, $R^1$ is —$NO_2$. In some embodiments, $R^1$ is —SR. In some embodiments, $R^1$ is —S(O)R. In some embodiments, $R^1$ is —$S(O)_2R$. In some embodiments, $R^1$ is —$S(O)_2N(R)_2$. In some embodiments, $R^1$ is —$NRS(O)_2R$.

In some embodiments, $R^1$ is selected from

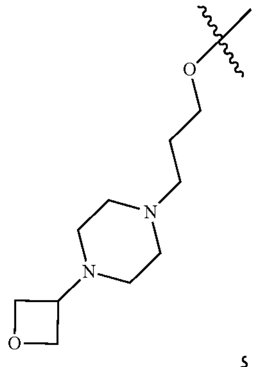
,
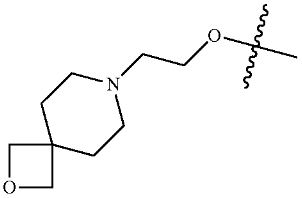
,
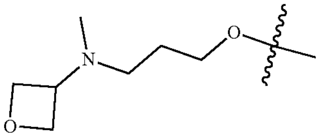
,
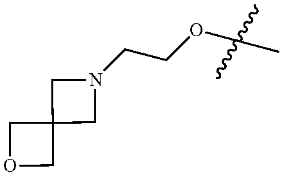
,
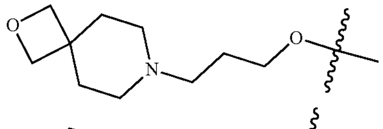
,
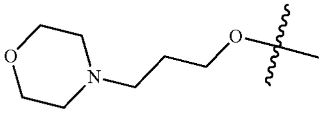
,
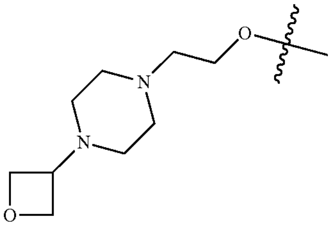
, -continued

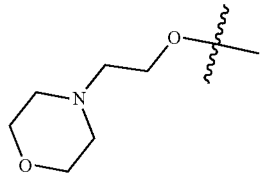
,
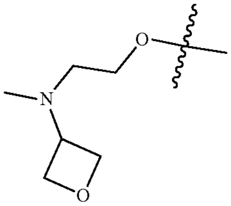
, and
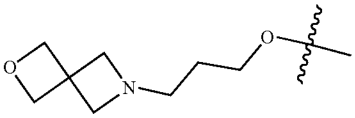
.

In some embodiments, $R^1$ is selected from those depicted in Table 1, below.

As defined generally above, $R^2$ is an optionally substituted group selected from $C_{1-6}$ aliphatic, or a 3-8 membered saturated or partially unsaturated monocyclic carbocyclic ring.

In some embodiments, $R^2$ is a $C_{1-6}$ aliphatic group. In some embodiments, $R^2$ is a substituted $C_{1-6}$ aliphatic group. In some embodiments, $R^2$ is a 3-8 membered saturated monocyclic carbocyclic ring. In some embodiments, $R^2$ is a 3-8 membered partially unsaturated monocyclic carbocyclic ring. In some embodiments, $R^2$ is a substituted 3-8 membered saturated monocyclic carbocyclic ring. In some embodiments, $R^2$ is a substituted 3-8 membered partially unsaturated monocyclic carbocyclic ring.

In some embodiments, $R^2$ is hydrogen.

In some embodiments, $R^2$ is selected from

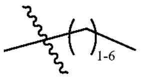
,
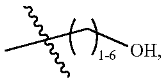
,
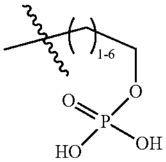
, and
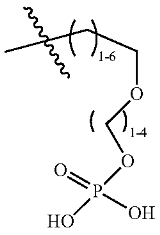
.

In some embodiments, $R^2$ is selected from ethyl,

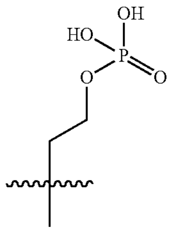

and

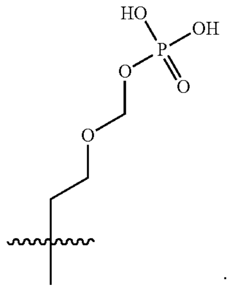

.

In some embodiments, $R^2$ is selected from $C_{1-6}$ alkyl optionally substituted with 1, 2, 3, 4, 5, or 6 halogen or deuterium atoms.

In some embodiments, $R^2$ is selected from methyl, —$CD_3$, —$CF_3$, ethyl, —$CH_2CF_3$, n-propyl, isopropyl, n-butyl, and s-butyl.

In some embodiments, $R^2$ is ethyl.

In some embodiments, $R^2$ is selected from H, methyl, ethyl,

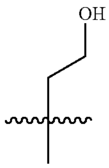

,

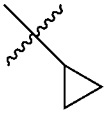

,

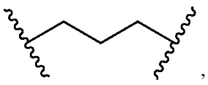

, and

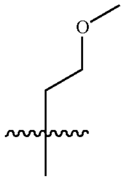

.

In some embodiments, $R^2$ is selected from those depicted in Table 1, below.

As defined generally above, each occurrence of $R^3$ is independently optionally substituted $C_{1-6}$ aliphatic, halogen, —CN, —NC, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, or —NRS(O)$_2$R.

As defined generally above, each occurrence of $R^3$ is independently an optionally substituted $C_{1-6}$ aliphatic, an optionally substituted 3-8 membered saturated or partially unsaturated monocyclic carbocyclic ring, an optionally substituted 4-10 membered saturated or partially unsaturated bicyclic carbocyclic ring, an optionally substituted 3-8 membered saturated or partially unsaturated monocyclic heterocyclic ring having 1-2 heteroatoms independently selected from nitrogen, oxygen, and sulfur, an optionally substituted 5-10 membered bicyclic heterocyclic ring having 1-4 heteroatoms independently selected from nitrogen, oxygen, and sulfur, an optionally substituted 5-6 membered monocyclic heteroaromatic ring having 1-4 heteroatoms independently selected from nitrogen, oxygen, and sulfur, an optionally substituted 8-10 membered bicyclic heteroaromatic ring having 1-5 heteroatoms independently selected from nitrogen, oxygen, and sulfur, optionally substituted phenyl, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, or —NRS(O)$_2$R.

In some embodiments, $R^3$ is a $C_{1-6}$ aliphatic group. In some embodiments, $R^3$ is a substituted $C_{1-6}$ aliphatic group. In some embodiments, $R^3$ is halogen. In some embodiments, $R^3$ is —CN. In some embodiments, $R^3$ is —NC. In some embodiments, $R^3$ is —C(O)R. In some embodiments, $R^3$ is —C(O)OR. In some embodiments, $R^3$ is —OC(O)R. In some embodiments, $R^3$ is —C(O)N(R)$_2$. In some embodiments, $R^3$ is —N(R)C(O)R. In some embodiments, $R^3$ is —N(R)C(O)N(R)$_2$. In some embodiments, $R^3$ is —OC(O)N(R)$_2$. In some embodiments, $R^3$ is —N(R)C(O)OR. In some embodiments, $R^3$ is —OR. In some embodiments, $R^3$ is —N(R)$_2$. In some embodiments, $R^3$ is —$NO_2$. In some embodiments, $R^3$ is —SR. In some embodiments, $R^3$ is —S(O)R. In some embodiments, $R^3$ is —S(O)$_2$R. In some embodiments, $R^3$ is —S(O)$_2$N(R)$_2$. In some embodiments, $R^3$ is —NRS(O)$_2$R.

In some embodiments, $R^3$ is a $C_{1-6}$ aliphatic group. In some embodiments, $R^3$ is a substituted $C_{1-6}$ aliphatic group. In some embodiments, $R^3$ is a 3-8 membered saturated or partially unsaturated monocyclic carbocyclic ring. In some embodiments, $R^3$ is a 4-10 membered saturated or partially unsaturated bicyclic carbocyclic ring. In some embodiments, $R^3$ is a 3-8 membered saturated or partially unsaturated monocyclic heterocyclic ring having 1-2 heteroatoms independently selected from nitrogen, oxygen, and sulfur. In some embodiments, $R^3$ is a 5-10 membered bicyclic heterocyclic ring having 1-4 heteroatoms independently selected from nitrogen, oxygen, and sulfur. In some embodiments, $R^3$ is a 5-6 membered monocyclic heteroaromatic ring having 1-4 heteroatoms independently selected from nitrogen, oxygen, and sulfur. In some embodiments, $R^3$ is an 8-10 membered bicyclic heteroaromatic ring having 1-5 heteroatoms independently selected from nitrogen, oxygen, and sulfur. In some embodiments, $R^3$ is phenyl. In some embodiments, $R^3$ is a substituted 3-8 membered saturated or partially unsaturated monocyclic carbocyclic ring. In some embodiments, $R^3$ is a substituted 4-10 membered saturated or partially unsaturated bicyclic carbocyclic ring. In some embodiments, $R^3$ is a substituted 3-8 membered saturated or partially unsaturated monocyclic heterocyclic ring having 1-2 heteroatoms independently selected from nitrogen, oxygen, and sulfur. In some embodiments, $R^3$ is a substituted 5-10 membered bicyclic heterocyclic ring having 1-4 heteroatoms independently selected from nitrogen, oxygen, and sulfur. In some embodiments, $R^3$ is a substituted 5-6 membered monocyclic heteroaromatic ring having 1-4 heteroatoms independently selected from nitrogen, oxygen, and sulfur. In some embodiments, $R^3$ is a substituted 8-10 membered bicyclic heteroaromatic ring having 1-5 heteroatoms independently selected from nitrogen, oxygen, and sulfur. In some embodiments, $R^3$ is a substituted phenyl. In some embodiments, $R^3$ is halogen. In some embodiments, $R^3$ is —CN. In some embodiments, $R^3$ is —C(O)R. In some embodiments, $R^3$ is —C(O)OR. In some embodiments, $R^3$ is —OC(O)R. In some embodiments, $R^3$ is —C(O)N(R)$_2$. In some embodiments, $R^3$ is —N(R)C(O)R. In some embodiments, $R^3$ is —N(R)C(O)N(R)$_2$. In some embodiments, $R^3$ is —OC(O)N(R)$_2$. In some embodiments, $R^3$ is —N(R)C(O)OR. In some embodiments, $R^3$ is —OR. In some embodiments, $R^3$ is —N(R)$_2$. In some embodiments, $R^3$ is —$NO_2$. In some embodiments, $R^3$ is —SR. In some embodiments, $R^3$ is —S(O)R. In some embodiments, $R^3$ is —S(O)$_2$R. In some embodiments, $R^3$ is —S(O)$_2$N(R)$_2$. In some embodiments, $R^3$ is —NRS(O)$_2$R.

In some embodiments, $R^3$ is a $C_{1-6}$ alkyl group, —$C_{1-6}$ alkylene-OR, —$C_{2-4}$ alkenyl, —$C_{2-4}$ alkynyl, halogen, —OR, —C(O)R, —CN, —C(O)$NR_2$, —NHMe, —$NMe_2$, or —$NH_2$.

In some embodiments, $R^3$ is methyl, ethyl, F, Cl, —CN, —$CF_3$,

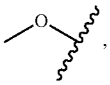, 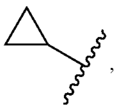, 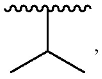, 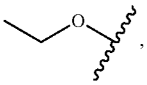,

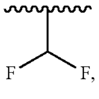 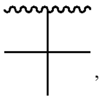, 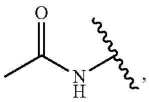, 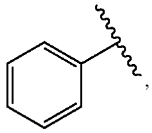,

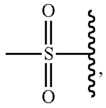, 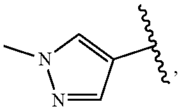, 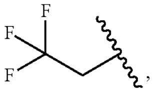,

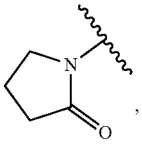, 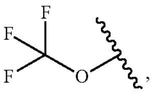, 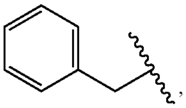,

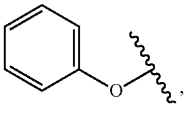, 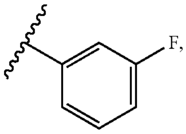 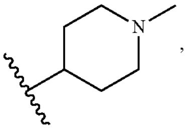,

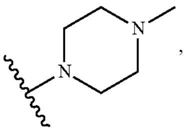, 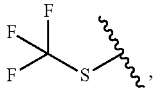, 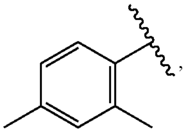,

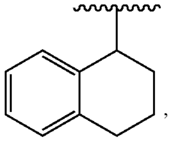, 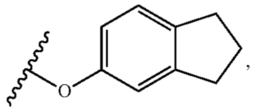,

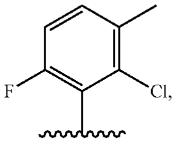 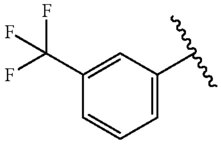,

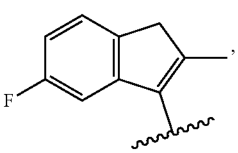, 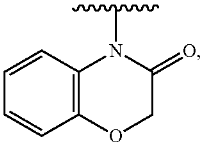

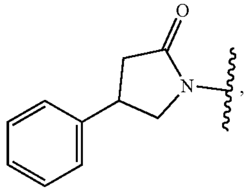, 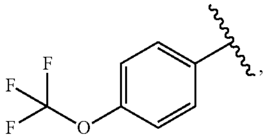,

-continued

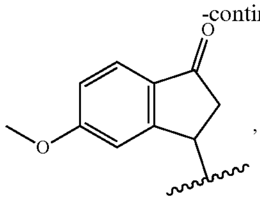, or 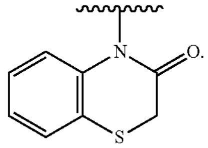

In some embodiments, $R^3$ is —$CF_3$.

In some embodiments, $R^3$ is selected from those depicted in Table 1, below.

As defined generally above, $R^4$ is phenyl, a 3-8 membered saturated or partially unsaturated monocyclic carbocyclic ring, or a substituted $C_{1-6}$ aliphatic; wherein $R^4$ is optionally substituted with p instances of $R^7$.

In some embodiments, $R^4$ is phenyl. In some embodiments, $R^4$ is a 3-8 membered saturated monocyclic carbocyclic ring. In some embodiments, $R^4$ is a 3-8 membered partially unsaturated monocyclic carbocyclic ring. In some embodiments, $R^4$ is a substituted $C_{1-6}$ aliphatic.

As defined generally above, $R^4$ is phenyl, a 3-8 membered saturated or partially unsaturated monocyclic carbocyclic ring, a 4-10 membered bicyclic carbocyclic ring, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur, or a $C_{1-6}$ aliphatic; wherein $R^4$ is optionally substituted with p instances of $R^7$.

In some embodiments, $R^4$ is phenyl. In some embodiments, $R^4$ is a 3-8 membered saturated monocyclic carbocyclic ring. In some embodiments, $R^4$ is a 3-8 membered partially unsaturated monocyclic carbocyclic ring. In some embodiments, $R^4$ is a 4-10 membered bicyclic carbocyclic ring. In some embodiments, $R^4$ is an 8-10 membered bicyclic aromatic carbocyclic ring. In some embodiments, $R^4$ is a 3-8 membered saturated or partially unsaturated monocyclic heterocyclic ring having 1-2 heteroatoms independently selected from nitrogen, oxygen, and sulfur. In some embodiments, $R^4$ is a 5-10 membered bicyclic heterocyclic ring having 1-4 heteroatoms independently selected from nitrogen, oxygen, and sulfur. In some embodiments, $R^4$ is a 5-6 membered monocyclic heteroaromatic ring having 1-4 heteroatoms independently selected from nitrogen, oxygen, and sulfur. In some embodiments, $R^4$ is an 8-10 membered bicyclic heteroaromatic ring having 1-5 heteroatoms independently selected from nitrogen, oxygen, and sulfur. In some embodiments, $R^4$ is a $C_{1-6}$ aliphatic.

In some embodiments, $R^4$ is phenyl. In some embodiments, $R^4$ is a 3-8 membered saturated monocyclic carbocyclic ring. In some embodiments, $R^4$ is a 3-8 membered partially unsaturated monocyclic carbocyclic ring. In some embodiments, $R^4$ is a substituted $C_{1-6}$ aliphatic.

In some embodiments, $R^4$ is selected from phenyl substituted with p instances of $R^7$ and cyclopropyl substituted with p instances of $R^7$.

In some embodiments, $R^4$ is selected from

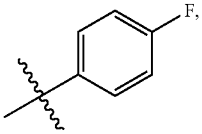 [SMILES: *c1ccc(F)cc1]
, cyclopropyl and phenyl.

In some embodiments, $R^4$ is selected from

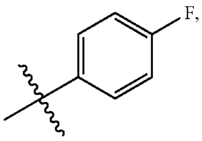 [SMILES: *c1ccc(F)cc1]
, cyclopropyl, cyclopentyl, cyclobutyl, methyl, ethyl,

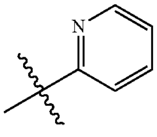
,
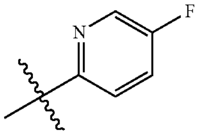
, and
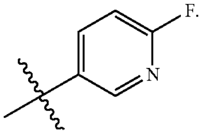
.

In some embodiments, $R^4$ is selected from those depicted in Table 1, below.

As defined generally above, $R^5$ is a substituent comprising a warhead group.

In some embodiments, the warhead group comprises an electrophilic group capable of reacting with a nucleophile under biological conditions to form a covalent bond to the nucleophile. In some embodiments, the warhead group comprises an electrophilic group capable of reacting with the thiol group of a cysteine under biological conditions to form a covalent bond to the cysteine. In some embodiments, the warhead group comprises an epoxide, a Michael acceptor (e.g., substituted or unsubstituted acrylamide, substituted or unsubstituted acrylate, substituted or unsubstituted alpha halo acetamide), an alkyl chloride, alkyl bromide, alkyl iodide, a sulfonyl halide, an alpha-halo ketone, an alpha-halo amide, an aldehyde, an aminonitrile, an N-cyanamide, a nitrile, a vinyl sulfone, a vinyl sulfonamide, or an anhydride. In some embodiments, the warhead groups comprise those described in Table 1c.

In some embodiments, the warhead group is $-L^2-Y$, wherein:

$L^2$ is a covalent bond or a bivalent $C_{1-8}$ saturated or unsaturated, straight or branched, hydrocarbon chain, wherein one, two, or three methylene units of $L^2$ are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —C(O)O—, —S—, —SO—, —$SO_2$—, —O—P(O)(OR)O—, —C(=S)—, —C(=NR)—, —N=N—, or —C(=$N_2$)—;

Y is hydrogen, $C_{1-6}$ aliphatic optionally substituted with oxo, halogen, $NO_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and each $R^e$ is independently selected from -Q-Z, oxo, $NO_2$, halogen, CN, a suitable leaving group, or a $C_{1-6}$ aliphatic optionally substituted with oxo, halogen, $NO_2$, or CN, wherein:

Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—N(R)C(O)—, —C(O)N(R)—, —N(R)$SO_2$—, or —$SO_2$N(R)—; and Z is hydrogen or $C_{1-6}$ aliphatic optionally substituted with oxo, halogen, $NO_2$, or CN.

In certain embodiments, $L^2$ is a covalent bond. In certain embodiments, $L^2$ is a bivalent $C_{1-8}$ saturated or unsaturated, straight or branched, hydrocarbon chain. In certain embodiments, $L^2$ is —$CH_2$—.

In certain embodiments, $L^2$ is a covalent bond, —$CH_2$—, —NH—, —$CH_2$NH—, —NH$CH_2$—, —NHC(O)—, —NHC(O)$CH_2$OC(O)—, —$CH_2$NHC(O)—, —NH$SO_2$—, —NH$SO_2CH_2$—, —NHC(O)$CH_2$OC(O)—, or —$SO_2$NH—.

In some embodiments, $L^2$ is a bivalent $C_{2-8}$ straight or branched, hydrocarbon chain wherein $L^2$ has at least one double bond and one or two additional methylene units of $L^2$ are optionally and independently replaced by —NRC(O)—, —C(O)NR—, —N(R)$SO_2$—, —$SO_2$N(R)—, —S—, —S(O)—, —$SO_2$—, —OC(O)—, —C(O)O—, cyclopropylene, —O—, —N(R)—, —O—P(O)(OR)O—, or —C(O)—.

In certain embodiments, $L^2$ is a bivalent $C_{2-8}$ straight or branched, hydrocarbon chain wherein $L^2$ has at least one double bond and at least one methylene unit of $L^2$ is replaced by —C(O)—, —NRC(O)—, —C(O)NR—, —N(R)$SO_2$—, —$SO_2$N(R)—, —S—, —S(O)—, —$SO_2$—, —OC(O)—, or —C(O)O—, and one or two additional methylene units of $L^2$ are optionally and independently replaced by cyclopropylene, —O—, —N(R), or —C(O)—.

In some embodiments, $L^2$ is a bivalent $C_{2-8}$ straight or branched, hydrocarbon chain wherein $L^2$ has at least one double bond and at least one methylene unit of $L^2$ is replaced by —C(O)—, and one or two additional methylene units of $L^2$ are optionally and independently replaced by cyclopropylene, —O—, —N(R)—, —O—P(O)(OR)O—, or —C(O)—. In some embodiments, $L^2$ is a bivalent $C_{2-8}$ straight or branched, hydrocarbon chain wherein $L^2$ has at least one double bond and at least one methylene unit of $L^2$ is replaced by —C(O)—, and one or two additional methylene units of $L^2$ are optionally and independently replaced by cyclopropylene, —O—, —N(R)—, —O—P(O)(OR)O—, or —C(O)—, wherein at least one double bond is located in an alpha-beta position relative to a —C(O)—.

As described above, in certain embodiments, $L^2$ is a bivalent $C_{2-8}$ straight or branched, hydrocarbon chain wherein $L^2$ has at least one double bond. One of ordinary skill in the art will recognize that such a double bond may exist within the hydrocarbon chain backbone or may be "exo" to the backbone chain and thus forming an alkylidene group. By way of example, such an $L^2$ group having an alkylidene branched chain includes —$CH_2$C(=$CH_2$)$CH_2$. Thus, in some embodiments, $L^2$ is a bivalent $C_{2-8}$ straight or branched, hydrocarbon chain wherein $L^2$ has at least one alkylidenyl double bond. In some embodiments, $L^2$ is a bivalent $C_{2-8}$ straight or branched, hydrocarbon chain wherein $L^2$ has at least one alkylidenyl double bond located in an alpha-beta position relative to a —C(O)—. Exemplary $L^2$ groups include —NHC(O)C(=$CH_2$)$CH_2$—.

In certain embodiments, $L^2$ is a bivalent $C_{2-8}$ straight or branched, hydrocarbon chain wherein $L^2$ has at least one double bond and at least one methylene unit of $L^2$ is replaced by —C(O)—. In certain embodiments, $L^2$ is —C(O)CH=CH($CH_3$), —C(O)CH=CH$CH_2$NH($CH_3$)—, —C(O)CH=CH($CH_3$)—, —C(O)CH=CH—, —$CH_2$C(O)CH=CH—, —$CH_2$C(O)CH=CH($CH_3$)—, —$CH_2CH_2$C(O)CH=CH—, —$CH_2CH_2$C(O)CH=CH$CH_2$—, —$CH_2CH_2$C(O)CH=CH$CH_2$NH($CH_3$)—, —$CH_2CH_2$C(O)CH=CH($CH_3$)—, or —CH($CH_3$)OC(O)CH=CH—.

In certain embodiments, $L^2$ is a bivalent $C_{2-8}$ straight or branched, hydrocarbon chain wherein $L^2$ has at least one double bond and at least one methylene unit of $L^2$ is replaced by —OC(O)—.

In some embodiments, $L^2$ is a bivalent $C_{2-8}$ straight or branched, hydrocarbon chain wherein $L^2$ has at least one double bond and at least one methylene unit of $L^2$ is replaced by —NRC(O)—, —C(O)NR—, —N(R)$SO_2$—, —$SO_2$N(R)—, —S—, —S(O), —$SO_2$—, —OC(O)—, or —C(O)O—, and one or two additional methylene units of $L^2$ are optionally and independently replaced by cyclopropylene, —O—, —N(R)—, or —C(O)—. In some embodiments, $L^2$ is —$CH_2$OC(O)CH=CH$CH_2$—, —$CH_2$—OC(O)CH=CH—, or —CH(CH=$CH_2$)OC(O)CH=CH—.

In certain embodiments, $L^2$ is —NRC(O)CH=CH—, —NRC(O)CH=CH$CH_2$N($CH_3$)—, —NRC(O)CH=CH$CH_2$O—, —$CH_2$NRC(O)CH=CH—, —NR$SO_2$CH=CH—, —NR$SO_2$CH=CH$CH_2$—, —NRC(O)(C=$N_2$)C(O)—, —NRC(O)CH=CH$CH_2$N($CH_3$)—, —NR$SO_2$CH=CH—, —NR$SO_2$CH=CH$CH_2$—, —NRC(O)CH=CH$CH_2$O—, —NRC(O)C(=$CH_2$)$CH_2$—, —$CH_2$NRC(O)—, —$CH_2$NRC(O)CH=CH—, —$CH_2CH_2$NRC(O)—, or —$CH_2$NRC(O)cyclopropylene-, wherein each R is independently hydrogen or optionally substituted $C_{1-6}$ aliphatic.

In certain embodiments, $L^2$ is —NHC(O)CH=CH—, —NHC(O)CH=CH$CH_2$N($CH_3$)—, —NHC(O)CH—CH$CH_2$O—, —$CH_2$NHC(O)CH=CH—, —NH$SO_2$CH=CH—, —NH$SO_2$CH=CH$CH_2$—, —NHC(O)(C=$N_2$)C(O)—, —NHC(O)CH=CH$CH_2$N($CH_3$)—, —NH$SO_2$CH=CH—, —NH$SO_2$CH=CH$CH_2$—, —NHC(O)CH=CH$CH_2$O—, —NHC(O)C(=$CH_2$)$CH_2$—, —$CH_2$NHC(O)—, —$CH_2$NHC(O)CH=CH—, —$CH_2CH_2$NHC(O)—, or —$CH_2$NHC(O)cyclopropylene-.

In some embodiments, $L^2$ is a bivalent $C_{2-8}$ straight or branched, hydrocarbon chain wherein $L^2$ has at least one triple bond. In certain embodiments, $L^2$ is a bivalent $C_{2-8}$ straight or branched, hydrocarbon chain wherein $L^2$ has at least one triple bond and one or two additional methylene units of $L^2$ are optionally and independently replaced by —NRC(O)—, —C(O)NR—, —S—, —S(O)—, —$SO_2$—, —C(=S)—, —C(=NR)—, —O—, —N(R)—, or —C(O)—. In some embodiments, $L^2$ has at least one triple bond and at least one methylene unit of $L^2$ is replaced by —N(R)—, —N(R)C(O)—, —C(O)—, —C(O)O—, or —OC(O)—, or —O—. In some embodiments, $L^2$ has at least one triple bond and at least one methylene unit of $L^2$ is replaced by —N(R)—, —N(R)C(O)—, —C(O)—, —C(O)O—, or —OC(O)—, or —O—, wherein at least one triple bond is located in an alpha-beta position relative to a —C(O)—.

Exemplary $L^2$ groups include —C≡C—, —C≡C$CH_2$N(isopropyl)-, NHC(O)C≡C$CH_2CH_2$—, —$CH_2$—C≡C≡$CH_2$—, —C=C$CH_2$O—, —$CH_2$C(O)C≡C—, —C(O)C≡C—, or —$CH_2$OC(=O)C≡C—.

In certain embodiments, $L^2$ is a bivalent $C_{2-8}$ straight or branched, hydrocarbon chain wherein one methylene unit of $L^2$ is replaced by cyclopropylene and one or two additional methylene units of $L^2$ are independently replaced by —C(O)—, —NRC(O)—, —C(O)NR—, —N(R)$SO_2$—, or —$SO_2$N(R)—. Exemplary $L^2$ groups include —NHC(O)-cyclopropylene-$SO_2$— and —NHC(O)-cyclopropylene-.

In certain embodiments, $L^2$ is a bivalent $C_{2-8}$ straight or branched, hydrocarbon chain wherein one methylene unit of $L^2$ is replaced by —O—P(O)(OR)O—.

As defined generally above, Y is hydrogen, $C_{1-6}$ aliphatic optionally substituted with oxo, halogen, $NO_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 $R^e$ groups, each $R^e$ is independently selected from -Q-Z, oxo, $NO_2$, halogen, CN, a suitable leaving group, or $C_{1-6}$ aliphatic, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and, Z is hydrogen or $C_{1-6}$ aliphatic optionally substituted with oxo, halogen, $NO_2$, or CN.

In certain embodiments, Y is hydrogen. In some embodiments, when L is a covalent bond, Y is other than hydrogen.

In certain embodiments, Y is $C_{1-6}$ aliphatic optionally substituted with oxo, halogen, $NO_2$, or CN. In some embodiments, Y is $C_{2-6}$ alkenyl optionally substituted with oxo, halogen, $NO_2$, or CN. In other embodiments, Y is $C_{2-6}$ alkynyl optionally substituted with oxo, halogen, $NO_2$, or CN. In some embodiments, Y is $C_{2-6}$ alkenyl. In other embodiments, Y is $C_{2-4}$ alkynyl.

In other embodiments, Y is $C_{1-6}$ alkyl substituted with oxo, halogen, $NO_2$, or CN. Such Y groups include —$CH_2$F, —$CH_2$Cl, —$CH_2$CN, and —$CH_2NO_2$.

In certain embodiments, Y is a saturated 3-6 membered monocyclic ring having 0-3 heteroatoms independently selected from nitrogen, oxygen, or sulfur, wherein Y is substituted with 1-4 $R^e$ groups, wherein each Reis as defined above in warhead group -$L^2$-Y.

In some embodiments, Y is a saturated 3-4 membered heterocyclic ring having 1 heteroatom selected from oxygen or nitrogen wherein said ring is substituted with 1-2 $R^e$ groups, wherein each $R^e$ is as defined above in warhead group is -$L^2$-Y. Exemplary such rings are epoxide and oxetane rings, wherein each ring is substituted with 1-2 $R^e$ groups, wherein each Reis as defined above in warhead group is -$L^2$-Y.

In other embodiments, Y is a saturated 5-6 membered heterocyclic ring having 1-2 heteroatom selected from oxygen or nitrogen wherein said ring is substituted with 1-4 $R^e$ groups, wherein each $R^e$ is as defined above in warhead group -$L^2$-Y. Such rings include piperidine and pyrrolidine, wherein each ring is substituted with 1-4 $R^e$ groups, wherein each Reis as defined above in warhead group is -$L^2$-Y. In certain embodiments, Y is

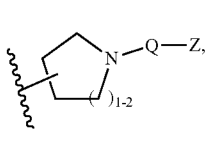

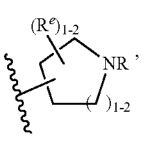

, or

-continued

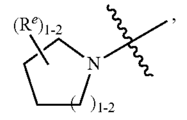

wherein each R, Q, Z, and $R^e$ is as defined above in warhead group $-L^2-Y$.

In some embodiments, Y is a saturated 3-6 membered carbocyclic ring, wherein said ring is substituted with 1-4 $R^e$ groups, wherein each Reis as defined above in warhead group $-L^2-Y$. In certain embodiments, Y is cyclopropyl, cyclobutyl, cyclopentyl, or cyclohexyl, wherein each ring is substituted with 1-4 $R^e$ groups, wherein each $R^e$ is as defined above in warhead group $-L^2-Y$. In certain embodiments, Y is

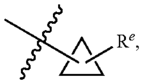

wherein $R^e$ is as defined above in warhead group $-L^2-Y$.

In certain embodiments, Y is cyclopropyl optionally substituted with halogen, CN or $NO_2$.

In certain embodiments, Y is a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above in warhead group $-L^2-Y$.

In some embodiments, Y is a partially unsaturated 3-6 membered carbocyclic ring, wherein said ring is substituted with 1-4 $R^e$ groups, wherein each $R^e$ is as defined above in warhead group $-L^2-Y$. In some embodiments, Y is cyclopropenyl, cyclobutenyl, cyclopentenyl, or cyclohexenyl wherein each ring is substituted with 1-4 $R^e$ groups, wherein each Reis as defined above in warhead group $-L^2-Y$. In certain embodiments, Y is

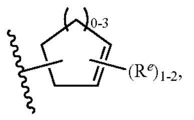

wherein each $R^e$ is as defined above in warhead group $-L^2-Y$.

In certain embodiments, Y is a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above in warhead group $-L^2-Y$. In certain embodiments, Y is selected from:

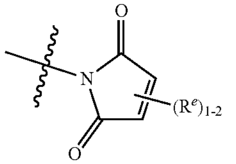

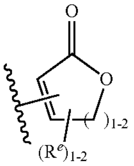

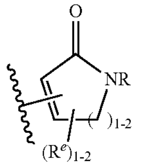

-continued

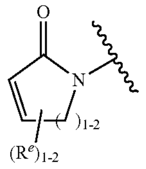

wherein each R is as defined above and described herein and $R^e$ is as defined above in warhead group $-L^2-Y$.

In certain embodiments, Y is a 6-membered aromatic ring having 0-2 nitrogens wherein said ring is substituted with 1-4 $R^e$ groups, wherein each $R^e$ group is as defined above in warhead group $-L^2-Y$. In certain embodiments, Y is phenyl, pyridyl, or pyrimidinyl, wherein each ring is substituted with 1-4 $R^e$ groups, wherein each $R^e$ is as defined above in warhead group $-L^2-Y$.

In some embodiments, Y is selected from:

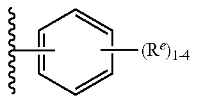

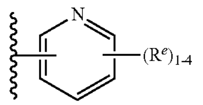

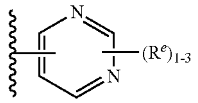

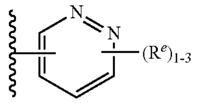

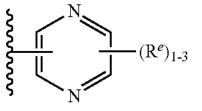

wherein each $R^e$ is as defined above in warhead group $-L^2-Y$.

In other embodiments, Y is a 5-membered heteroaryl ring having 1-3 heteroatoms independently selected from nitrogen, oxygen, or sulfur, wherein said ring is substituted with 1-3 $R^e$ groups, wherein each $R^e$ group is as defined above in warhead group $-L^2-Y$. In some embodiments, Y is a 5 membered partially unsaturated or aryl ring having 1-3 heteroatoms independently selected from nitrogen, oxygen, and sulfur, wherein said ring is substituted with 1-4 $R^e$ groups, wherein each $R^e$ group is as defined above in warhead group $-L^2-Y$. Exemplary such rings are isoxazolyl, oxazolyl, thiazolyl, imidazolyl, pyrazolyl, pyrrolyl, furanyl, thienyl, triazole, thiadiazole, and oxadiazole, wherein each ring is substituted with 1-3 $R^e$ groups, wherein each $R^e$ group is as defined above in warhead group $-L^2-Y$. In certain embodiments, Y is selected from:

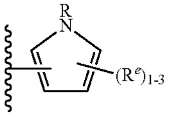

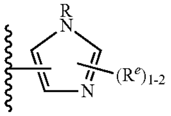

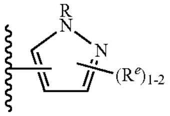

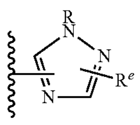

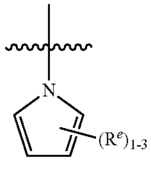

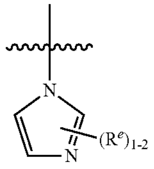

-continued

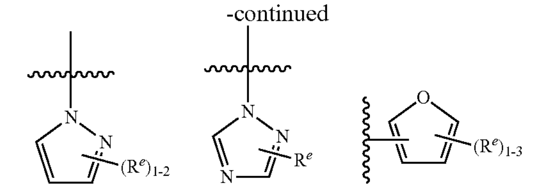

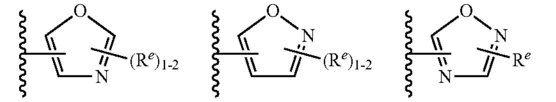

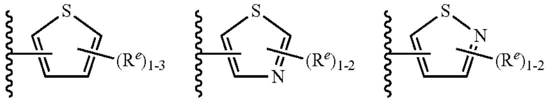

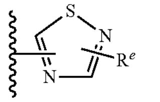

wherein each R is as defined above and described herein and $R^e$ is as defined above in warhead group $-L^2$-Y.

In certain embodiments, Y is an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein Reis as defined above in warhead group $-L^2$-Y. According to another aspect, Y is a 9-10 membered bicyclic, partially unsaturated, or aryl ring having 1-3 heteroatoms independently selected from nitrogen, oxygen, or sulfur, wherein said ring is substituted with 1-4 $R^e$ groups, wherein $R^e$ is as defined above in warhead group $-L^2$-Y. Exemplary such bicyclic rings include 2,3-dihydrobenzo[d]isothiazole, wherein said ring is substituted with 1-4 $R^e$ groups, wherein Reis as defined above in warhead group $-L^2$-Y.

As defined generally above, each $R^e$ group is independently selected from -Q-Z, oxo, $NO_2$, halogen, CN, a suitable leaving group, or $C_{1-6}$ aliphatic optionally substituted with oxo, halogen, $NO_2$, or CN, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R), —N(R)$SO_2$—, or —$SO_2$N(R)—; and Z is hydrogen or $C_{1-6}$ aliphatic optionally substituted with oxo, halogen, $NO_2$, or CN.

In certain embodiments, $R^e$ is $C_{1-6}$ aliphatic optionally substituted with oxo, halogen, $NO_2$, or CN. In other embodiments, $R^e$ is oxo, $NO_2$, halogen, or CN.

In some embodiments, $R^e$ is -Q-Z, wherein Q is a covalent bond and Z is hydrogen (i.e., $R^e$ is hydrogen). In other embodiments, $R^e$ is -Q-Z, wherein Q is a bivalent $C_{1-6}$ saturated or unsaturated, straight or branched, hydrocarbon chain, wherein one or two methylene units of Q are optionally and independently replaced by —NR—, —NRC(O)—, —C(O)NR—, —S—, —O—, —C(O)—, —SO—, or —$SO_2$—. In other embodiments, Q is a bivalent $C_{2-6}$ straight or branched, hydrocarbon chain having at least one double bond, wherein one or two methylene units of Q are optionally and independently replaced by —NR—, —NRC(O)—, —C(O)NR—, —S—, —O—, —C(O)—, —SO—, or —$SO_2$—. In certain embodiments, the Z moiety of the $R^e$ group is hydrogen. In some embodiments, -Q-Z is —NHC(O)CH═$CH_2$ or —C(O)CH═$CH_2$.

In certain embodiments, each $R^e$ is independently selected from oxo, $NO_2$, CN, fluoro, chloro, —NHC(O)CH═$CH_2$, —C(O)CH═$CH_2$, —$CH_2$CH═$CH_2$, —C≡CH, —C(O)O$CH_2$Cl, —C(O)O$CH_2$F, —C(O)O$CH_2$CN, —C(O)$CH_2$Cl, —C(O)$CH_2$F, —C(O)$CH_2$CN, or —$CH_2$C(O)$CH_3$.

In certain embodiments, $R^e$ is a suitable leaving group, i.e., a group that is subject to nucleophilic displacement. A "suitable leaving" is a chemical group that is readily displaced by a desired incoming chemical moiety such as the thiol moiety of a cysteine of interest. In some embodiments, the warhead group modifies a cysteine of DCN-1. In some embodiments, the cysteine of DCN-1 is Cys115. Suitable leaving groups are well known in the art, e.g., see, "Advanced Organic Chemistry," Jerry March, 5th Ed., pp. 351-357, John Wiley and Sons, N.Y. Such leaving groups include, but are not limited to, halogen, alkoxy, sulfonyloxy, optionally substituted alkylsulfonyloxy, optionally substituted alkenylsulfonyloxy, optionally substituted arylsulfonyloxy, acyl, and diazonium moieties. Examples of suitable leaving groups include chloro, iodo, bromo, fluoro, acetoxy, methanesulfonyloxy (mesyloxy), tosyloxy, triflyloxy, nitrophenylsulfonyloxy (nosyloxy), and bromo-phenylsulfonyloxy (brosyloxy).

In certain embodiments, the following embodiments, and combinations of $-L^2$-Y apply:

(a) $L^2$ is a bivalent $C_{2-8}$ straight or branched, hydrocarbon chain wherein $L^2$ has at least one double bond and one or two additional methylene units of $L^2$ are optionally and independently replaced by —NRC(O)—, —C(O)NR—, —N(R)$SO_2$—, —$SO_2$N(R)—, —S—, —S(O)—, —$SO_2$—, —OC(O)—, —C(O)O—, cyclopropylene, —O—, —N(R)—, —O—P(O)(OR)O—, or —C(O)—; and Y is hydrogen or $C_{1-6}$ aliphatic optionally substituted with oxo, halogen, $NO_2$, or CN; wherein $-L^2$-Y comprises an alpha, beta-unsaturated carbonyl moiety; or (b) $L^2$ is a bivalent $C_{2-8}$ straight or branched, hydrocarbon chain wherein $L^2$ has at least one double bond and at least one methylene unit of $L^2$ is replaced by —C(O)—, —NRC(O)—, —C(O)NR—, —N(R)$SO_2$—, —$SO_2$N(R)—, —S—, —S(O)—, —$SO_2$—, —OC(O)—, or —C(O)O—, and one or two additional methylene units of $L^2$ are optionally and independently replaced by cyclopropylene, —O—, —N(R)—, or —C(O); and Y is hydrogen or $C_{1-6}$ aliphatic optionally substituted with oxo, halogen, $NO_2$, or CN; wherein $-L^2$-Y comprises an alpha, beta-unsaturated carbonyl moiety; or (c) $L^2$ is a bivalent $C_{2-8}$ straight or branched, hydrocarbon chain wherein $L^2$ has at least one double bond and at least one methylene unit of $L^2$ is replaced by —C(O)—, and one or two additional methylene units of $L^2$ are optionally and independently replaced by cyclopropylene, —O—, —N(R)—, or —C(O)—; and Y is hydrogen or $C_{1-6}$ aliphatic optionally substituted with oxo, halogen, $NO_2$, or CN; wherein $-L^2$-Y comprises an alpha, beta-unsaturated carbonyl moiety; or (d) $L^2$ is a bivalent $C_{2-8}$ straight or branched, hydrocarbon chain wherein $L^2$ has at least one double bond and at least one methylene unit of $L^2$ is replaced by —C(O); and Y is hydrogen or $C_{1-6}$ aliphatic optionally substituted with oxo, halogen, $NO_2$, or CN; wherein $-L^2$-Y comprises an alpha, beta-unsaturated carbonyl moiety; or (e) $L^2$ is a bivalent $C_{2-8}$ straight or branched, hydrocarbon chain wherein $L^2$ has at least one double bond and at least one methylene unit of $L^2$ is replaced by —OC(O); and Y is hydrogen or $C_{1-6}$ aliphatic optionally substituted with oxo, halogen, $NO_2$, or CN; wherein $-L^2$-Y comprises an alpha, beta-unsaturated carbonyl moiety; or (f) $L^2$ is —NRC(O)CH═CH—, —NRC(O)CH═CHCH$_2$N(CH$_3$)—, —NRC(O)CH═CHCH$_2$O—, CH$_2$NRC(O)CH═CH—, —NRSO$_2$CH═CH—, —NRSO$_2$CH═CHCH$_2$—, —NRC(O)(C═N$_2$)—, —NRC(O)(C═N$_2$)C(O)—, —NRC(O)CH═CHCH$_2$N(CH$_3$)—, —NRSO$_2$CH═CH—, —NRSO$_2$CH═CHCH$_2$—, —NRC(O)CH═CHCH$_2$O—, —NRC(O)C(═CH$_2$)CH$_2$, —CH$_2$NRC(O), —CH$_2$NRC(O)CH═CH—, —CH$_2$CH$_2$NRC(O)—, or —CH$_2$NRC(O)cyclopropylene-; wherein R is H or optionally substituted $C_{1-6}$ aliphatic; and Y is hydrogen or $C_{1-6}$ aliphatic optionally substituted with oxo, halogen, $NO_2$, or CN; wherein $-L^2$-Y comprises an alpha, beta-unsaturated carbonyl moiety; or (g) $L^2$ is —NHC(O)CH═CH—, —NHC(O)CH═CHCH$_2$N(CH$_3$)—, —NHC(O)CH═CHCH$_2$O—, —CH$_2$NHC(O)CH═CH—, —NHSO$_2$CH═CH—, —NHSO$_2$CH═CHCH$_2$—, —NHC(O)(C═N$_2$)—, —NHC(O)(C═N$_2$)C(O)—, —NHC(O)CH═CHCH$_2$N(CH$_3$)—, —NHSO$_2$CH═CH—, —NHSO$_2$CH═CHCH$_2$—, —NHC(O)CH═CHCH$_2$O—, —NHC(O)C(═CH$_2$)CH$_2$—, —CH$_2$NHC(O)—, —CH$_2$NHC(O)CH═CH—, —CH$_2$CH$_2$NHC(O)—, or —CH$_2$NHC(O)cyclopropylene-; and Y is hydrogen or $C_{1-6}$ aliphatic optionally substituted with oxo, halogen, $NO_2$, or CN; wherein $-L^2$-Y comprises an alpha, beta-unsaturated carbonyl moiety; or (h) $L^2$ is a bivalent $C_{2-8}$ straight or branched, hydrocarbon chain wherein $L^2$ has at least one alkylidenyl double bond and at least one methylene unit of $L^2$ is replaced by —C(O)—, —NRC(O)—, —C(O)NR—, —N(R)SO$_2$—, —SO$_2$N(R)—, —S—, —S(O), —SO$_2$—, —OC(O)—, or —C(O)O—, and one or two additional methylene units of $L^2$ are optionally and independently replaced by cyclopropylene, —O—, —N(R)—, or —C(O)—; and Y is hydrogen or $C_{1-6}$ aliphatic optionally substituted with oxo, halogen, $NO_2$, or CN; wherein $-L^2$-Y comprises an alpha, beta-unsaturated carbonyl moiety; or (i) $L^2$ is a bivalent $C_{2-8}$ straight or branched, hydrocarbon chain wherein $L^2$ has at least one triple bond and one or two additional methylene units of $L^2$ are optionally and independently replaced by —NRC(O)—, —C(O)NR—, —N(R)SO$_2$—, —SO$_2$N(R), —S—, —S(O)—, —SO$_2$—, —OC(O)—, or —C(O)O—, and Y is hydrogen or $C_{1-6}$ aliphatic optionally substituted with oxo, halogen, $NO_2$, or CN; wherein $-L^2$-Y comprises an alpha, beta-unsaturated carbonyl moiety; or (j) $L^2$ is —C≡C—, —C≡CCH$_2$N(isopropyl)-, —NHC(O)C≡CCH$_2$CH$_2$—, —CH$_2$—C≡C≡CH$_2$—, —C≡CCH$_2$O—, —CH$_2$C(O)C≡C—, —C(O)C≡C—, or —CH$_2$C(═O)C≡C—; and Y is hydrogen or $C_{1-6}$ aliphatic optionally substituted with oxo, halogen, $NO_2$, or CN; wherein $-L^2$-Y comprises an alpha, beta-unsaturated carbonyl moiety; or (k) $L^2$ is a bivalent $C_{2-8}$ straight or branched, hydrocarbon chain wherein one methylene unit of $L^2$ is replaced by cyclopropylene and one or two additional methylene units of $L^2$ are independently replaced by —NRC(O)—, —C(O)NR—, —N(R)SO$_2$—, —SO$_2$N(R)—, —S—, —S(O)—, —SO$_2$—, —OC(O)—, or —C(O)O—; and Y is hydrogen or $C_{1-6}$ aliphatic optionally substituted with oxo, halogen, $NO_2$, or CN; wherein $-L^2$-Y comprises an alpha, beta-unsaturated carbonyl moiety; or (l) $L^2$ is a covalent bond and Y is selected from:

(i) $C_{1-6}$ alkyl substituted with oxo, halogen, $NO_2$, or CN;

(ii) $C_{2-6}$alkenyl optionally substituted with oxo, halogen, $NO_2$, or CN; or (iii) $C_{2-6}$alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above in warhead group $-L^2$-Y; or (v) a saturated 5-6 membered heterocyclic ring having 1-2 heteroatom selected from oxygen or nitrogen wherein said ring is substituted with 1-4 $R^e$ groups, wherein each $R^e$ is as defined above in warhead group $-L^2$-Y; or (vi)

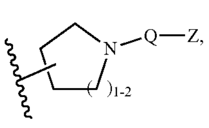

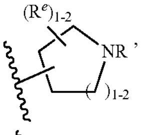

, or

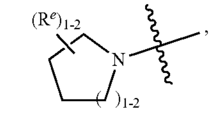

wherein each R, Q, Z, and $R^e$ is as defined above in warhead group $-L^2$-Y; or (vii) a saturated 3-6 membered carbocyclic ring, wherein said ring is substituted with 1-4 $R^e$ groups, wherein each $R^e$ is as defined above in warhead group $-L^2$-Y; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above in warhead group $-L^2$-Y; or (ix) a partially unsaturated 3-6 membered carbocyclic ring, wherein said ring is substituted with 1-4 $R^e$ groups, wherein each Reis as defined above in warhead group $-L^2$-Y; or (x)

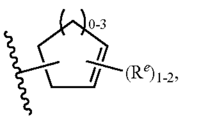

wherein each $R^e$ is as defined above in warhead group $-L^2$-Y; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above in warhead group $-L^2$-Y; or (xii)

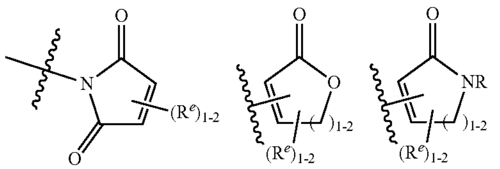 or

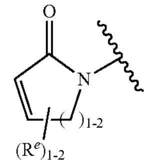

wherein each R is as defined above and described herein and $R^e$ is as defined above in warhead group $-L^2-Y$; or (xiii) a 6-membered aromatic ring having 0-2 nitrogens wherein said ring is substituted with 1-4 $R^e$ groups, wherein each $R^e$ group is as defined above in warhead group $-L^2-Y$; or (xiv)

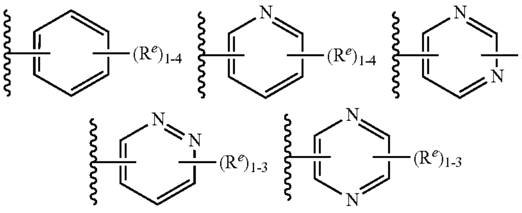

wherein each $R^e$ is as defined above in warhead group $-L^2-Y$; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above in warhead group $-L^2-Y$; or (xvi)

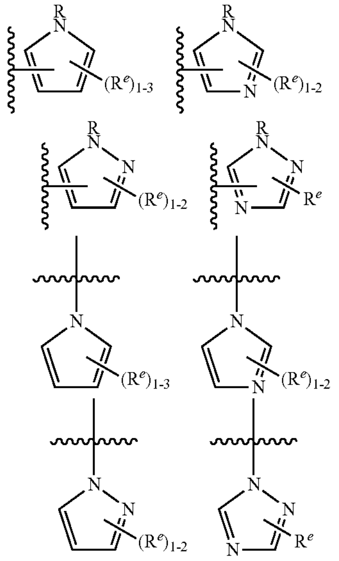

-continued

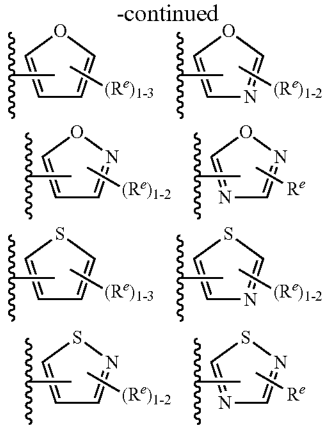

wherein each R is as defined above and described herein and $R^e$ is as defined above in warhead group $-L^2-Y$; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above in warhead group $-L^2-Y$;

(m) $L^2$ is —C(O)— and Y is selected from:

(i) $C_{1-6}$ alkyl substituted with oxo, halogen, $NO_2$, or CN; or (ii) $C_{2-6}$alkenyl optionally substituted with oxo, halogen, $NO_2$, or CN; or (iii) $C_{2-6}$alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above in warhead group $-L^2-Y$; or (v) a saturated 5-6 membered heterocyclic ring having 1-2 heteroatom selected from oxygen or nitrogen wherein said ring is substituted with 1-4 $R^e$ groups, wherein each $R^e$ is as defined above in warhead group $-L^2-Y$; or (vi)

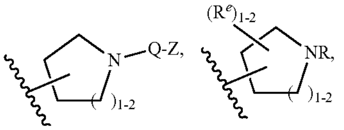 or

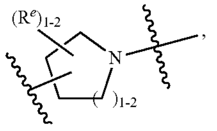

wherein each R, Q, Z, and $R^e$ is as defined above in warhead group $-L^2-Y$; or (vii) a saturated 3-6 membered carbocyclic ring, wherein said ring is substituted with 1-4 $R^e$ groups, wherein each $R^e$ is as defined above in warhead group $-L^2-Y$; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above in warhead group -$L^2$-Y; or (ix) a partially unsaturated 3-6 membered carbocyclic ring, wherein said ring is substituted with 1-4 $R^e$ groups, wherein each $R^e$ is as defined above in warhead group -$L^2$-Y; or (x)

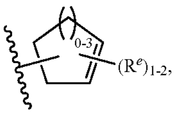

wherein each $R^e$ is as defined above in warhead group -$L^2$-Y; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above in warhead group -$L^2$-Y; or (xii)

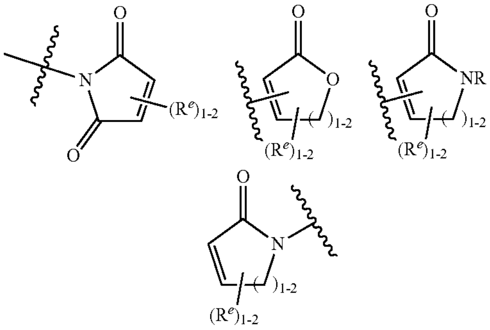

or wherein each R is as defined above and described herein and $R^e$ is as defined above in warhead group -$L^2$-Y; or (xiii) a 6-membered aromatic ring having 0-2 nitrogens wherein said ring is substituted with 1-4 $R^e$ groups, wherein each $R^e$ group is as defined above in warhead group -$L^2$-Y; or (xiv)

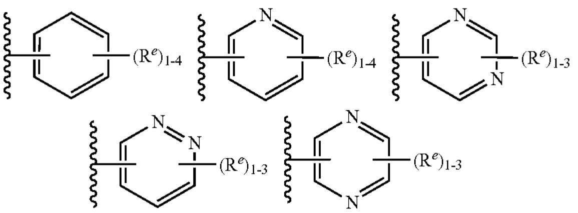

wherein each Reis as defined above in warhead group -$L^2$-Y; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above in warhead group -$L^2$-Y; or (xvi)

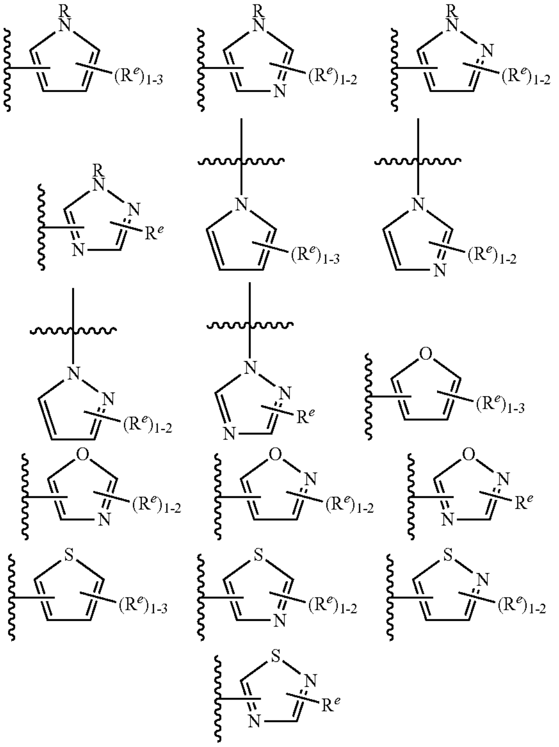

wherein each R is as defined above and described herein and $R^e$ is as defined above in warhead group -$L^2$-Y; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above in warhead group -$L^2$-Y;

(n) $L^2$ is —N(R)C(O)— and Y is selected from:

(i) $C_{1-6}$ alkyl substituted with oxo, halogen, $NO_2$, or CN; or (ii) $C_{2-6}$alkenyl optionally substituted with oxo, halogen, $NO_2$, or CN; or (iii) $C_{2-6}$alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above in warhead group -$L^2$-Y; or (v) a saturated 5-6 membered heterocyclic ring having 1-2 heteroatom selected from oxygen or nitrogen wherein said ring is substituted with 1-4 $R^e$ groups, wherein each $R^e$ is as defined above in warhead group -$L^2$-Y; or (vi)

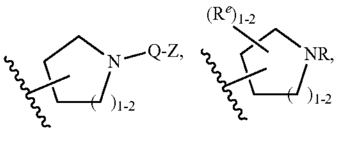

or

-continued

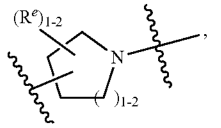

wherein each R, Q, Z, and Reis as defined above in warhead group $-L^2$-Y; or (vii) a saturated 3-6 membered carbocyclic ring, wherein said ring is substituted with 1-4 $R^e$ groups, wherein each $R^e$ is as defined above in warhead group $-L^2$-Y; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above in warhead group $-L^2$-Y; or (ix) a partially unsaturated 3-6 membered carbocyclic ring, wherein said ring is substituted with 1-4 $R^e$ groups, wherein each $R^e$ is as defined above in warhead group $-L^2$-Y; or (x)

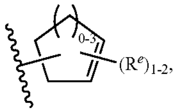

wherein each $R^e$ is as defined above in warhead group $-L^2$-Y; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above in warhead group $-L^2$-Y; or (xii)

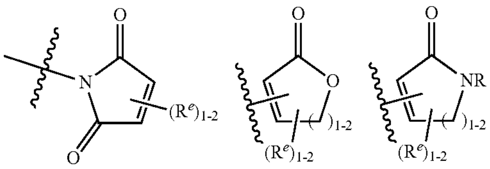

or

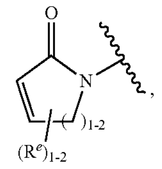

wherein each R and $R^e$ is as defined above in warhead group $-L^2$-Y; or (xiii) a 6-membered aromatic ring having 0-2 nitrogens wherein said ring is substituted with 1-4 $R^e$ groups, wherein each $R^e$ group is as defined above in warhead group $-L^2$-Y; or (xiv)

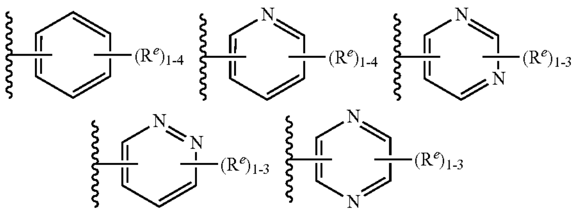

wherein each $R^e$ is as defined above in warhead group $-L^2$-Y; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above in warhead group $-L^2$-Y; or (xvi)

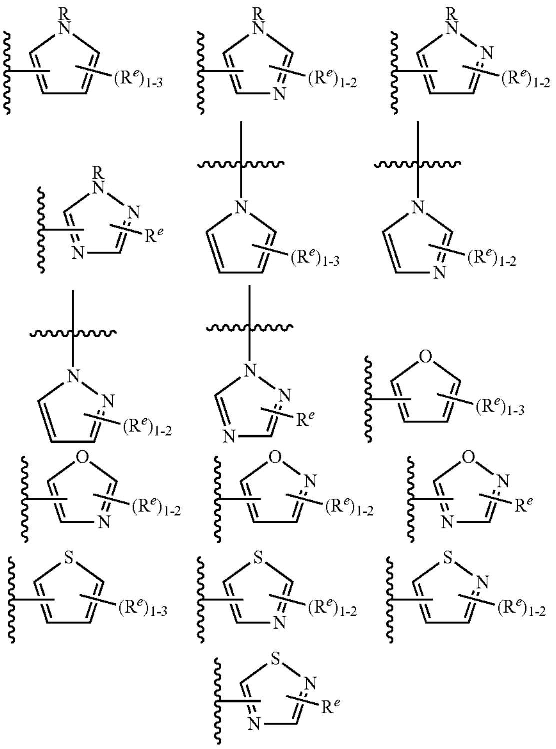

wherein each R is as defined above and described herein and $R^e$ is as defined above in warhead group $-L^2$-Y; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein Reis as defined above in warhead group $-L^2$-Y;

(o) $L^2$ is a bivalent $C_{1-8}$ saturated or unsaturated, straight or branched, hydrocarbon chain; and Y is selected from:

(i) $C_{1-6}$ alkyl substituted with oxo, halogen, $NO_2$, or CN;

(ii) $C_{2-6}$alkenyl optionally substituted with oxo, halogen, $NO_2$, or CN; or (iii) $C_{2-6}$alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above in warhead group $-L^2$-Y; or (v) a saturated 5-6 membered heterocyclic ring having 1-2 heteroatom selected from oxygen or nitrogen wherein said ring is substituted with 1-4 $R^e$ groups, wherein each $R^e$ is as defined above in warhead group $-L^2$-Y; or (vi)

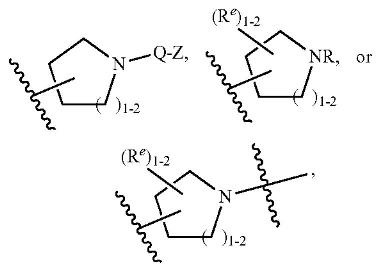

or wherein each R, Q, Z, and Reis as defined above in warhead group $-L^2$-Y; or (vii) a saturated 3-6 membered carbocyclic ring, wherein said ring is substituted with 1-4 $R^e$ groups, wherein each $R^e$ is as defined above in warhead group $-L^2$-Y; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above in warhead group $-L^2$-Y; or (ix) a partially unsaturated 3-6 membered carbocyclic ring, wherein said ring is substituted with 1-4 $R^e$ groups, wherein each $R^e$ is as defined above in warhead group $-L^2$-Y; or (x)

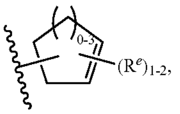

wherein each Reis as defined above in warhead group $-L^2$-Y; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above in warhead group $-L^2$-Y; or (xii)

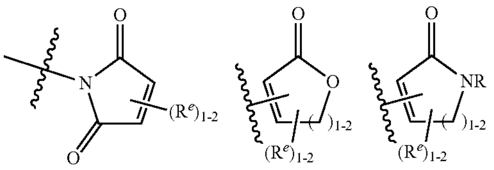

or

-continued

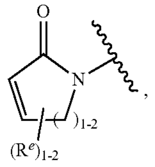

wherein each R is as defined above and described herein and $R^e$ is as defined above in warhead group $-L^2$-Y; or (xiii) a 6-membered aromatic ring having 0-2 nitrogens wherein said ring is substituted with 1-4 $R^e$ groups, wherein each $R^e$ group is as defined above in warhead group $-L^2$-Y; or (xiv)

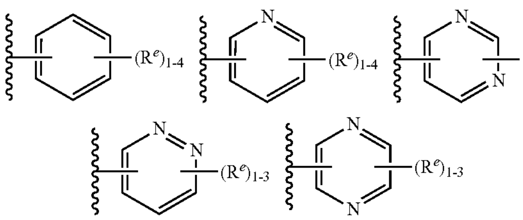

wherein each $R^e$ is as defined above in warhead group $-L^2$-Y; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above in warhead group $-L^2$-Y; or (xvi)

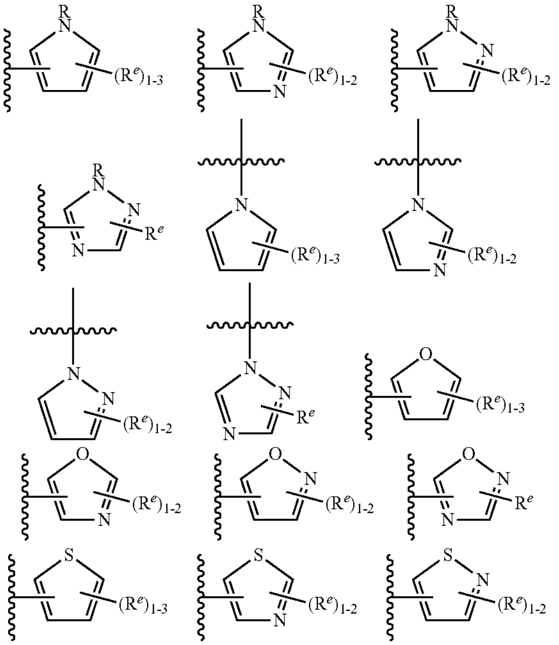

-continued

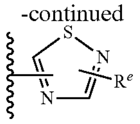

wherein each R is as defined above and described herein and $R^e$ is as defined above in warhead group $-L^2$-Y; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above in warhead group $-L^2$-Y;

(p) $L^2$ is a covalent bond, $-CH_2-$, —NH—, —C(O)—, $-CH_2NH-$, $-NHCH_2-$, —NHC(O)—, $-NHC(O)CH_2OC(O)-$, $-CH_2NHC(O)-$, $-NHSO_2-$, $-NHSO_2CH_2-$, $-NHC(O)CH_2OC(O)-$, or $-SO_2NH-$; and Y is selected from:

(i) $C_{1-6}$ alkyl substituted with oxo, halogen, $NO_2$, or CN; or (ii) $C_{2-6}$alkenyl optionally substituted with oxo, halogen, $NO_2$, or CN; or (iii) $C_{2-6}$alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above in warhead group $-L^2$-Y; or (v) a saturated 5-6 membered heterocyclic ring having 1-2 heteroatom selected from oxygen or nitrogen wherein said ring is substituted with 1-4 $R^e$ groups, wherein each $R^e$ is as defined above in warhead group $-L^2$-Y; or (vi)

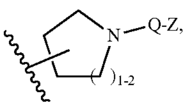

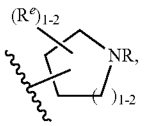

or

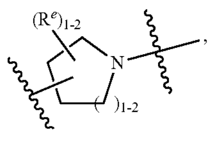

wherein each R, Q, Z, and Reis as defined above in warhead group $-L^2$-Y; or (vii) a saturated 3-6 membered carbocyclic ring, wherein said ring is substituted with 1-4 $R^e$ groups, wherein each $R^e$ is as defined above in warhead group $-L^2$-Y; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above in warhead group $-L^2$-Y; or (ix) a partially unsaturated 3-6 membered carbocyclic ring, wherein said ring is substituted with 1-4 $R^e$ groups, wherein each $R^e$ is as defined above in warhead group $-L^2$-Y; or (x)

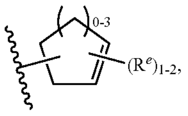

wherein each $R^e$ is as defined above in warhead group $-L^2$-Y; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above in warhead group $-L^2$-Y; or (xii)

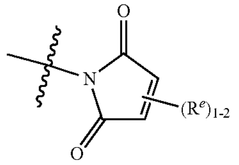

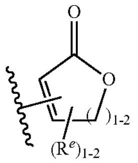

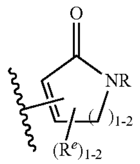

or

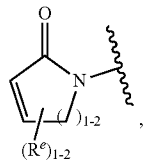

wherein each R and $R^e$ is as defined above in warhead group $-L^2$-Y; or (xiii) a 6-membered aromatic ring having 0-2 nitrogens wherein said ring is substituted with 1-4 $R^e$ groups, wherein each $R^e$ group is as defined above in warhead group $-L^2$-Y; or (xiv)

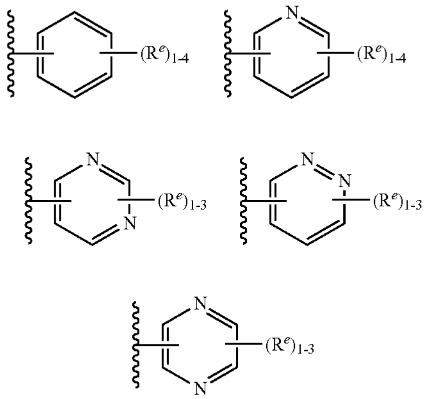

wherein each Reis as defined above in warhead group $-L^2$-Y; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above in warhead group $-L^2$-Y; or (xvi)

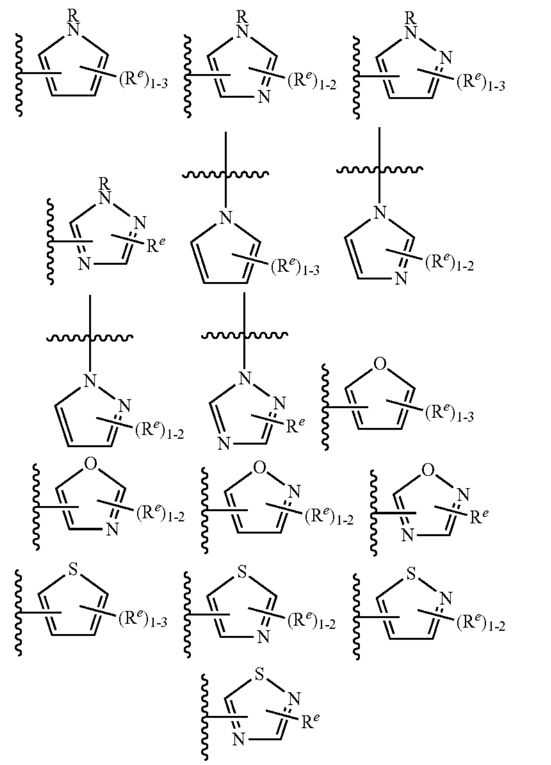

wherein each R is as defined above and described herein and $R^e$ is as defined above in warhead group $-L^2$-Y; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above in warhead group $-L^2$-Y;

(q) $L^2$ is a bivalent $C_{1-8}$ saturated or unsaturated, straight or branched, hydrocarbon chain, wherein one, two, or three methylene units of $L^2$ are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —C(O)O—, —S—, —SO—, —$SO_2$—, —O—P(O)(OR)O—, —C(═S)—, —C(═NR)—, —N═N—, or —C(═$N_2$)—; and Y is hydrogen or $C_{1-6}$ aliphatic optionally substituted with oxo, halogen, $NO_2$, or CN, wherein $-L^2$-Y comprises an alpha, beta-unsaturated carbonyl moiety;

(r) $L^2$ is a bivalent $C_{1-8}$ saturated or unsaturated, straight or branched, hydrocarbon chain, wherein one, two, or three methylene units of $L^2$ are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —C(O)O—, —S—, —SO—, —$SO_2$—, —O—P(O)(OR)O—, —C(═S)—, —C(═NR)—, —N═N—, or —C(═$N_2$)—; and Y is hydrogen or $C_{1-6}$ aliphatic optionally substituted with oxo, halogen, $NO_2$, or CN, wherein $-L^2$-Y comprises an alpha halo carbonyl moiety.

In certain embodiments, a Y group is selected from those set forth in Table 1a, below.

In certain embodiments, $R^5$ is $L^2$-Y. In certain embodiments, the following embodiments, and combinations of $-L^2$-Y apply:

$L^2$ is a covalent bond or a bivalent $C_{2-8}$ straight or branched, hydrocarbon chain wherein one or two methylene units of $L^2$ are optionally and independently replaced by —NRC(O)—, —C(O)NR—, —N(R)$SO_2$—, —$SO_2$N(R)—, —S—, —O—, —NR—, —S(O)—, —$SO_2$—, —C(O)—, —OC(O)—, or —C(O)O—; and additionally one methylene unit of $L^2$ is optionally replaced by an optionally substituted ring selected from a 3-8 membered saturated or partially unsaturated monocyclic carbocyclic ring, a 4-10 membered bicyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur; and Y is hydrogen, halogen, —COOR, —CN, —CON$(R)_2$, —NRCN, $NO_2$, —N$(R)_2$, optionally substituted $C_{1-8}$ aliphatic, or an optionally substituted ring selected from a 3-8 membered saturated or partially unsaturated monocyclic carbocyclic ring, a 4-10 membered bicyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, and an 8-10 membered bicyclic heteroaromatic ring having 1-5 heteroatoms independently selected from nitrogen, oxygen, and sulfur; wherein $-L^2$-Y comprises an alpha, beta-unsaturated carbonyl moiety, amide, cyano group, halogen, carbonyl, alkynyl group, sulfonyl group, or epoxide.

In certain embodiments, $R^5$ is $L^2$-Y. In certain embodiments, the following embodiments, and combinations of $-L^2$-Y apply:

$L^2$ is a covalent bond or a bivalent $C_{2-8}$ straight or branched, hydrocarbon chain wherein one or two methylene units of $L^2$ are optionally and independently replaced by —NRC(O)—, —C(O)NR—, —N(R)$SO_2$—, —$SO_2$N(R)—, —S—, —O—, —NR—, —S(O)—, —$SO_2$—, —C(O)—, —OC(O)—, or —C(O)O—; and additionally one methylene unit of $L^2$ is optionally replaced by an optionally substituted ring selected from a 3-8 membered saturated or partially unsaturated monocyclic carbocyclic ring, or a 3-8 membered saturated or partially unsaturated monocyclic heterocyclic ring having 1-2 heteroatoms independently selected from nitrogen, oxygen, and sulfur; and Y is hydrogen, halogen, —$COOR^f$, —CN, —$CONR^f_2$, —$NR^f$CN, $NO_2$, —$NR^f_2$, $C_{1-8}$ aliphatic optionally substituted with halogen, $NO_2$, or CN, or an optionally substituted ring selected from a 3-8 membered saturated or partially unsaturated monocyclic carbocyclic ring, phenyl, a 3-8 membered saturated or partially unsaturated monocyclic heterocyclic ring having 1-2 heteroatoms independently selected from nitrogen, oxygen, and sulfur, and a 5-10 membered bicyclic heterocyclic ring having 1-4 heteroatoms independently selected from nitrogen, oxygen, and sulfur; wherein $-L^2$-Y comprises an alpha, beta-unsaturated carbonyl moiety, amide, cyano group, halogen, carbonyl, alkynyl group, sulfonyl group, or epoxide; and wherein each occurrence of $R^f$ is independently H, or straight or branched $C_{1-6}$ alkyl, $C_{2-6}$ alkenyl, or $C_{2-6}$ alkynyl group optionally substituted with 1, 2 or 3 halogen atoms.

In certain embodiments, $R^5$ is $L^2$-Y. In certain embodiments, the following embodiments and combinations of $-L^2$-Y apply:

$L^2$ is a covalent bond or a bivalent $C_{2-8}$ straight or branched, hydrocarbon chain wherein one or two methylene units of $L^2$ are optionally and independently replaced by —NRC(O)—, —C(O)NR—, —N(R)$SO_2$—, —$SO_2$N(R)—, —S—, —S(O)—, —$SO_2$—, —C(O)—, —OC(O)—, or —C(O)O—; and additionally one methylene unit of $L^2$ is optionally replaced by a ring selected from

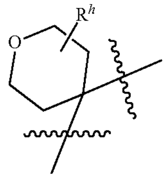, 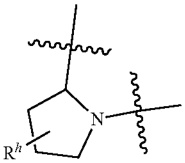,

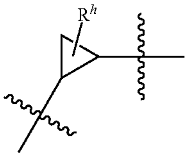, 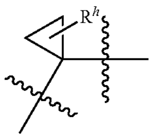,

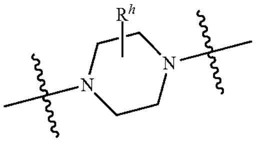, 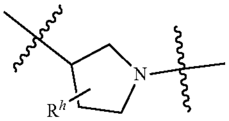,

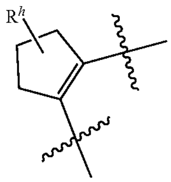, 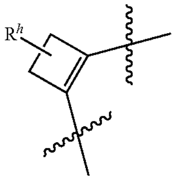,

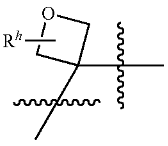, and 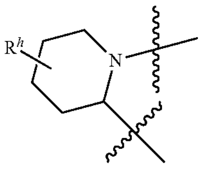;

and Y is hydrogen, halogen, —COOR$^f$, —CN, —CONR$^f_2$, —NR$^f$CN, $NO_2$, —NR$^f_2$, epoxide, $C_{1-8}$ aliphatic optionally substituted with halogen, $NO_2$, or CN, or a ring selected from

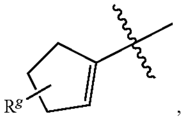, 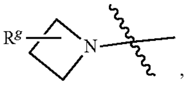,

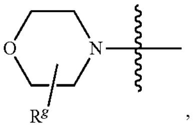, 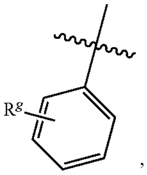, 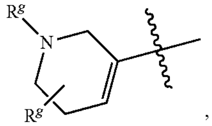,

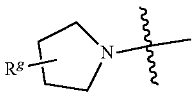, 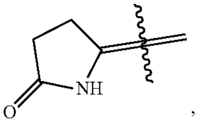,

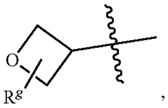, 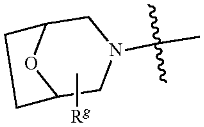,

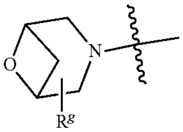, 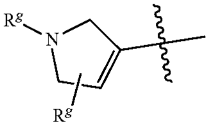,

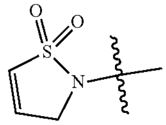, 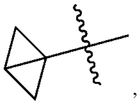, 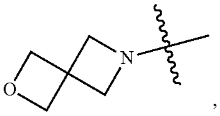,

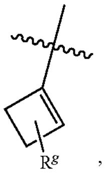, 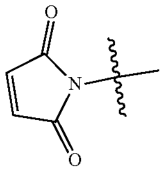, 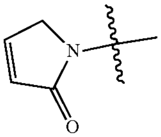,

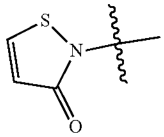, 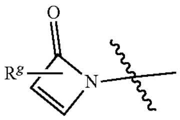, 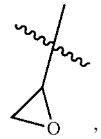,

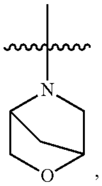, 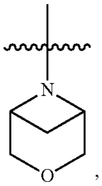, 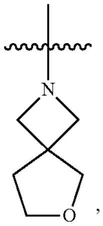, 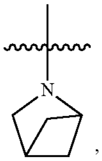, 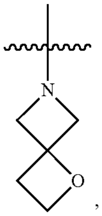,

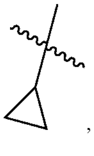, and 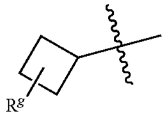;

wherein $-L^2$-Y comprises an alpha, beta-unsaturated carbonyl moiety, amide, cyano group, halogen, carbonyl, $C_{2-6}$ alkynyl group, sulfonyl group, or epoxide; wherein each occurrence of $R^f$ is independently H, or straight or branched $C_{1-6}$ alkyl, $C_{2-6}$ alkenyl, or $C_{2-6}$ alkynyl group optionally substituted with 1, 2 or 3 halogen atoms; and wherein each occurrence of R& and Rh is independently H, halogen, or OH, or straight or branched $C_{1-6}$ alkyl, $C_{2-6}$ alkenyl, or $C_{2-6}$ alkynyl group optionally substituted with 1, 2 or 3 halogen atoms.

In certain embodiments, $R^5$ is $L^2$-Y, wherein the following definitions of -$L^2$-Y apply: $L^2$ is a covalent bond or a bivalent optionally substituted $C_{2-10}$ straight or branched hydrocarbon chain wherein one, two or three methylene units of $L^2$ are optionally and independently replaced by —NRC(O)—, —C(O)NR—, —N(R)$SO_2$—, —$SO_2$N(R)—, —S—, —O—, —NR—, —S(O)—, —$SO_2$—, —C(O)—, —OC(O)—, or —C(O)O—; $C_{2-10}$ straight or branched, hydrocarbon chain is optionally substituted with 1, 2, 3, or 4 independently selected halogen atoms and optionally substituted with one —CN or —OR group; and additionally one methylene unit of $L^2$ is optionally replaced by an optionally substituted ring selected from a 3-8 membered saturated or partially unsaturated monocyclic carbocyclic ring, a 4-10 membered bicyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur; and Y is hydrogen, halogen, —COOR, —CN, —CON$(R)_2$, —CONRCN, —NRCN, $NO_2$, —N$(R)_2$, optionally substituted $C_{1-8}$ aliphatic, or an optionally substituted ring selected from a 3-8 membered saturated or partially unsaturated monocyclic carbocyclic ring, a 4-10 membered bicyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, and an 8-10 membered bicyclic heteroaromatic ring having 1-5 heteroatoms independently selected from nitrogen, oxygen, and sulfur; wherein -$L^2$-Y comprises an alpha, beta-unsaturated carbonyl moiety, amide, cyano group, halogen, carbonyl, alkynyl group, sulfonyl group, or epoxide.

In certain embodiments, $R^5$ is $L^2$-Y. In certain embodiments, the following definitions of -$L^2$-Y apply:

$L^2$ is a covalent bond or a bivalent optionally substituted $C_{2-10}$ straight or branched hydrocarbon chain wherein one, two or three methylene units of $L^2$ are optionally and independently replaced by —NRC(O)—, —C(O)NR—, —N(R)$SO_2$, —$SO_2$N(R), —S—, —O—, —NR—, —S(O)—, —$SO_2$—, —C(O)—, —OC(O)—, or —C(O)O—; $C_{2-10}$ straight or branched hydrocarbon chain is optionally substituted with 1, 2, 3, or 4 independently selected halogen atoms and optionally substituted with one —CN or —OR group; and additionally one methylene unit of $L^2$ is optionally replaced by an optionally substituted ring selected from a 3-8 membered saturated or partially unsaturated monocyclic carbocyclic ring, or a 3-8 membered saturated or partially unsaturated monocyclic heterocyclic ring having 1-2 heteroatoms independently selected from nitrogen, oxygen, and sulfur; and Y is hydrogen, halogen, —COOR$^f$, —CN, —CONR$^f_2$, —CONR$^f$CN, —NR$^f$CN, $NO_2$, —NR$^f_2$, $C_{1-8}$ aliphatic optionally substituted with halogen, $NO_2$, or CN, or an optionally substituted ring selected from a 3-8 membered saturated or partially unsaturated monocyclic carbocyclic ring, phenyl, a 3-8 membered saturated or partially unsaturated monocyclic heterocyclic ring having 1-2 heteroatoms independently selected from nitrogen, oxygen, and sulfur, and a 5-10 membered bicyclic heterocyclic ring having 1-4 heteroatoms independently selected from nitrogen, oxygen, and sulfur; wherein -$L^2$-Y comprises an alpha, beta-unsaturated carbonyl moiety, amide, cyano group, halogen, carbonyl, alkynyl group, sulfonyl group, or epoxide; and wherein each occurrence of $R^f$ is independently H, or straight or branched $C_{1-6}$ alkyl, $C_{2-6}$ alkenyl, or $C_{2-6}$ alkynyl group optionally substituted with 1, 2 or 3 halogen atoms.

In certain embodiments, $R^5$ is $L^2$-Y. In certain embodiments, the following definitions of -$L^2$-Y apply:

$L^2$ is a covalent bond or a bivalent $C_{2-10}$ straight or branched hydrocarbon chain wherein one, two or three methylene units of $L^2$ are optionally and independently replaced by —NRC(O)—, —C(O)NR—, —N(R)$SO_2$—, —$SO_2$N(R)—, —S—, —O—, —NR—, —S(O), —$SO_2$—, —C(O)—, —OC(O)—, or —C(O)O—; $C_{2-10}$ straight or branched hydrocarbon chain is optionally substituted with 1, 2, 3, or 4 independently selected halogen atoms and optionally substituted with one —CN or —OR group; and additionally one methylene unit of $L^2$ is optionally replaced by a ring selected from

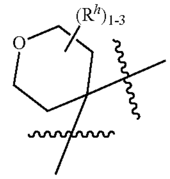
,
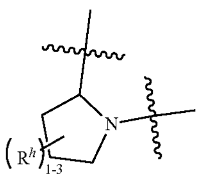
,
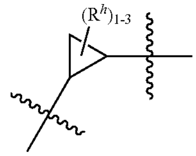
,
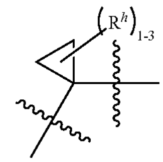
,
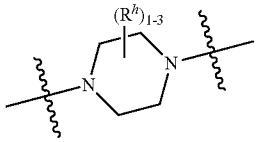
,
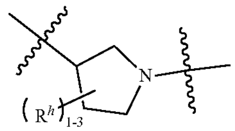
,
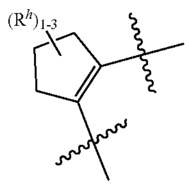
,
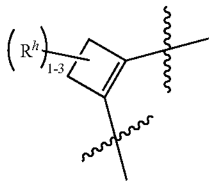
, -continued
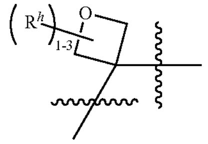,
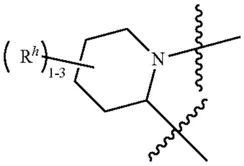,
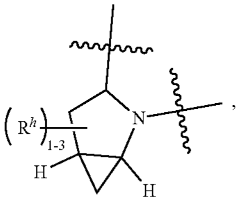,
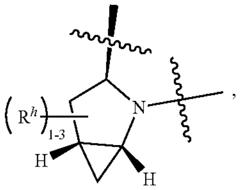,
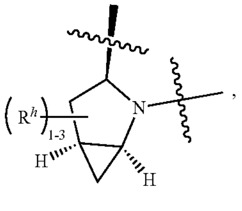,
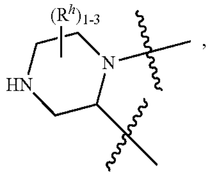,
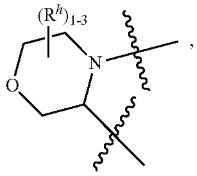,
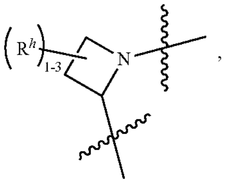,
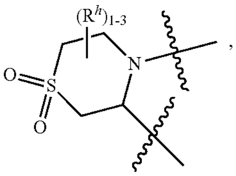,
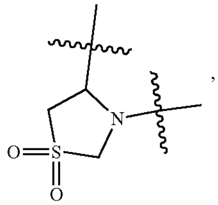,
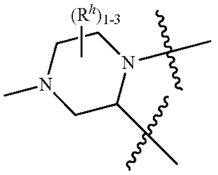,
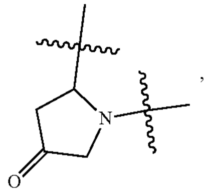,
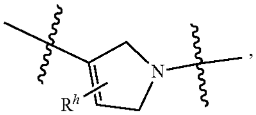, and
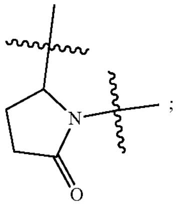;
and Y is hydrogen, halogen, —COOR$^f$, —CN, —CONR$^f_2$, —CONR$^f$CN, —NR$^f$CN, $NO_2$, —NR$^f_2$, epoxide, $C_{1-8}$ aliphatic optionally substituted with halogen, $NO_2$, or CN, or a ring selected from
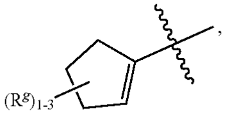,
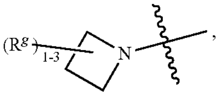,
-continued
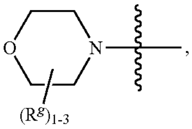,
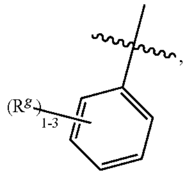,
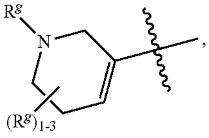,
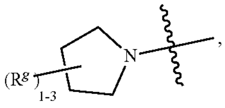,
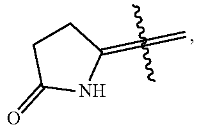,
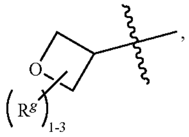,
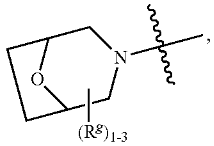,
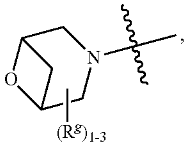,
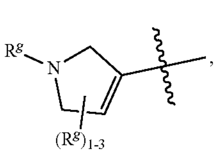,
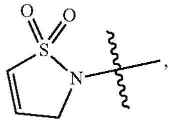,
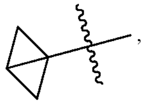,
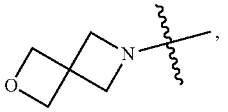,
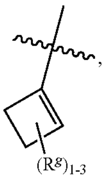,
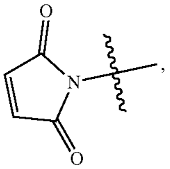,
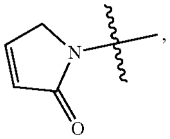,
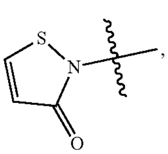,
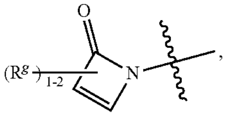,
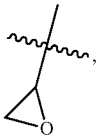,
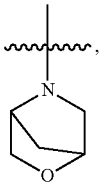,
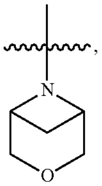,
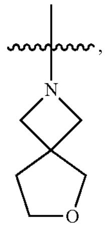,
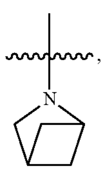,
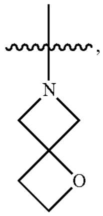,
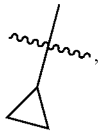, -continued

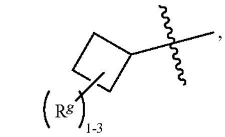, 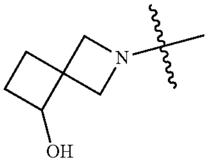,

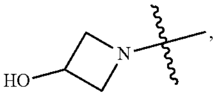, 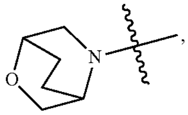,

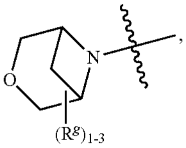, 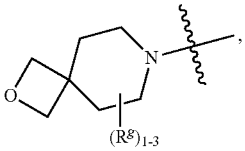,

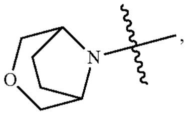, 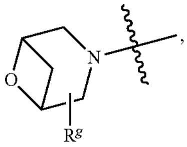,

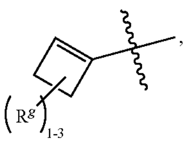, 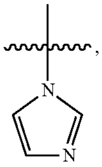, 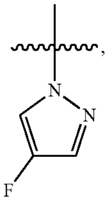, and

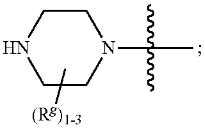;

wherein $-L^2-Y$ comprises an alpha, beta-unsaturated carbonyl moiety, amide, cyano group, halogen, carbonyl, $C_{2-6}$ alkynyl group, sulfonyl group, or epoxide; wherein each occurrence of $R^f$ is independently H, or straight or branched $C_{1-6}$ alkyl, $C_{2-6}$ alkenyl, or $C_{2-6}$ alkynyl group optionally substituted with 1, 2 or 3 halogen atoms; and wherein each occurrence of $R^g$ and $R^h$ is independently H, halogen, or OH, or straight or branched $C_{1-6}$ alkyl, $C_{2-6}$ alkenyl, or $C_{2-6}$ alkynyl group optionally substituted with 1, 2 or 3 halogen atoms.

In certain embodiments, a $L^2$-Y group is selected from those set forth in Table 1c, Table 1d and Table 1e below. In certain embodiments, a warhead group is selected from those set forth in Table 1c, Table 1d and Table 1e below.

In certain embodiments, a warhead group is selected from those set forth in Table 1f below.

TABLE 1a

| Exemplary Y groups | |
|---|---|
| 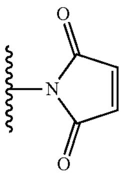 [SMILES: *N1C(=O)C=CC1=O] | a |

TABLE 1a-continued

| Exemplary Y groups | |
|---|---|
| 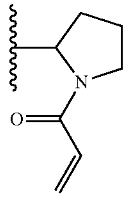 [SMILES: *C1CCCN1C(=O)C=C] | b |
| 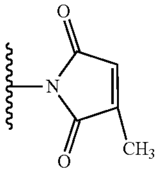 [SMILES: *N1C(=O)C=C(C)C1=O] | c |
| 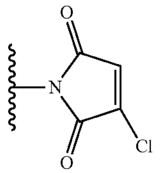 [SMILES: *N1C(=O)C=C(Cl)C1=O] | d |
| 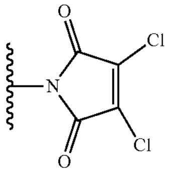 [SMILES: *N1C(=O)C(Cl)=C(Cl)C1=O] | e |
| 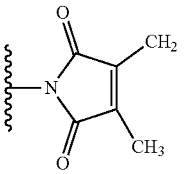 [SMILES: *N1C(=O)C(C)=C(C)C1=O] | f |
| 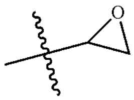 [SMILES: *C1CO1] | g |
| 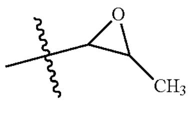 [SMILES: *C1OC1C] | h |
| 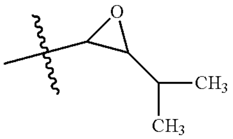 | i |
| 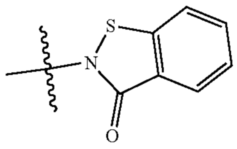 [SMILES: *n1sc2ccccc2c1=O] | j |

TABLE 1a-continued
| Exemplary Y groups | |
|---|---|
| 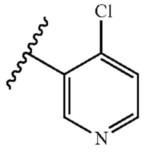 [SMILES: *c1cnccc1Cl] | k |
| 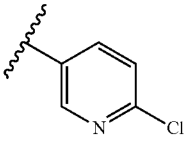 [SMILES: *c1ccc(Cl)nc1] | l |
| 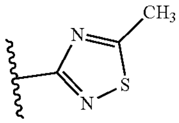 [SMILES: *c1nsc(C)n1] | m |
| 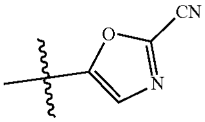 [SMILES: *c1cnc(C#N)o1] | n |
| 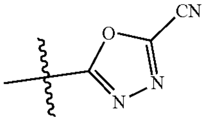 [SMILES: *c1nnc(C#N)o1] | o |
| 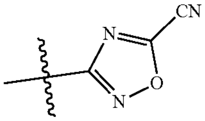 [SMILES: *c1noc(C#N)n1] | p |
| 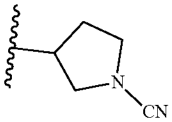 [SMILES: *C1CCN(C#N)C1] | q |
| 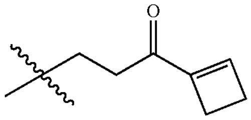 [SMILES: *CCC(=O)C1=CCC1] | r |
| 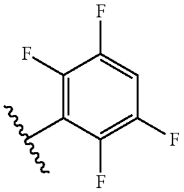 [SMILES: *c1c(F)c(F)cc(F)c1F] | s |
| 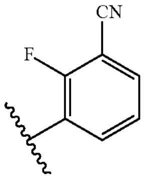 [SMILES: *c1cccc(C#N)c1F] | t |
TABLE 1a-continued
| Exemplary Y groups | |
|---|---|
| 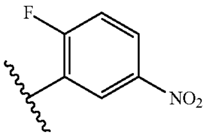 [SMILES: *c1cc([N+](=O)[O-])ccc1F] | u |
| 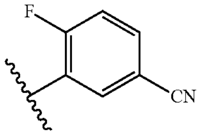 [SMILES: *c1cc(C#N)ccc1F] | v |
| 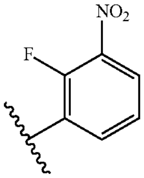 [SMILES: *c1cccc([N+](=O)[O-])c1F] | w |
| 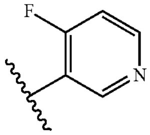 [SMILES: *c1cnccc1F] | x |
| 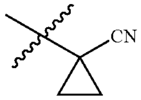 [SMILES: *C1(C#N)CC1] | y |
| 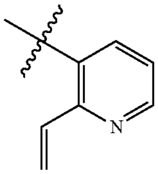 [SMILES: *c1cccnc1C=C] | z |
| 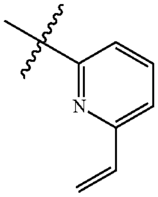 [SMILES: *c1cccc(C=C)n1] | aa |
| 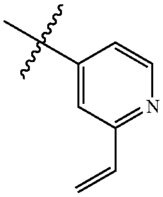 [SMILES: *c1ccnc(C=C)c1] | bb |
| 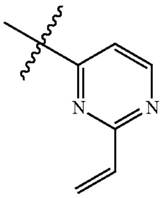 [SMILES: *c1ccnc(C=C)n1] | cc |

TABLE 1a-continued
Exemplary Y groups
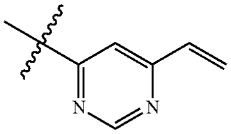 [SMILES: *c1cc(C=C)ncn1]
dd
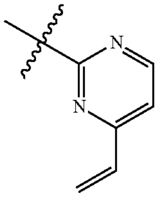 [SMILES: *c1nccc(C=C)n1]
ee
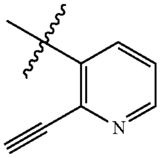 [SMILES: *c1cccnc1C#C]
ff
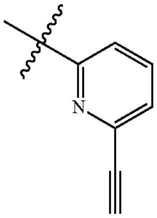 [SMILES: *c1cccc(C#C)n1]
gg
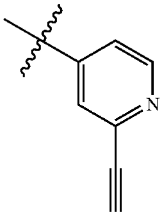
hh
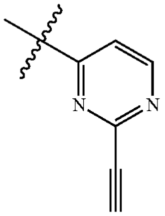
ii
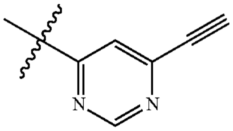 [SMILES: *c1cc(C#C)ncn1]
jj
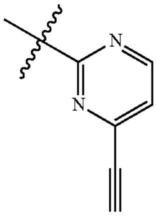 [SMILES: *c1nccc(C#C)n1]
kk
TABLE 1a-continued
Exemplary Y groups
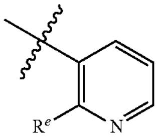
ll
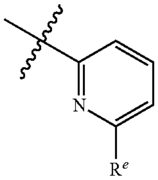
mm
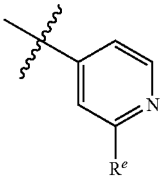
nn
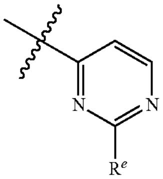
oo
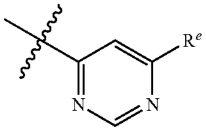
pp
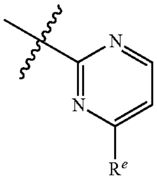
qq
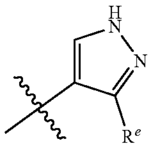
rr
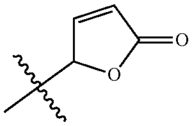 [SMILES: *C1C=CC(=O)O1]
ss
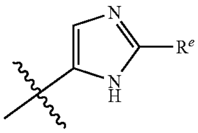
tt TABLE 1a-continued
| Exemplary Y groups | |
|---|---|
| 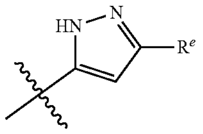 | uu |
| 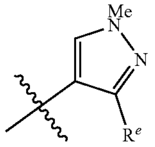 | vv |
| 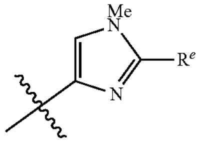 | ww |
| 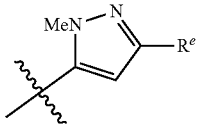 | xx |
| 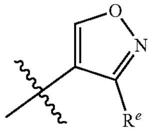 | yy |
| 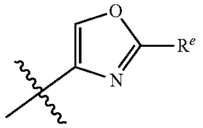 | zz |
| 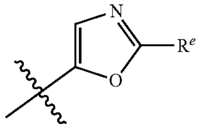 | aaa |
| 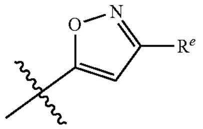 | bbb |
| 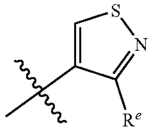 | ccc |
| 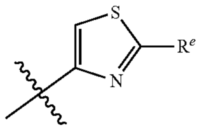 | ddd |
| 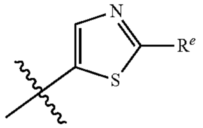 | eee |
| 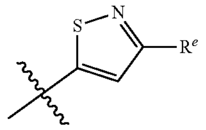 | fff |
| 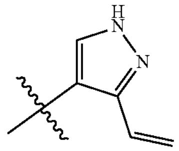 [SMILES: *c1c[nH]nc1C=C] | ggg |
| 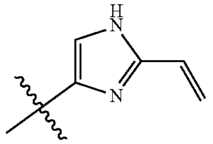 [SMILES: *c1c[nH]c(C=C)n1] | hhh |
| 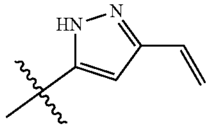 [SMILES: *c1cc(C=C)n[nH]1] | iii |
| 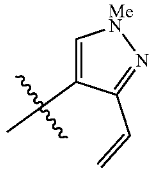 [SMILES: *c1cn(C)nc1C=C] | jjj |
| 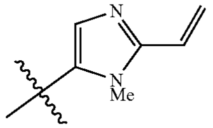 [SMILES: *c1cnc(C=C)n1C] | kkk |
| 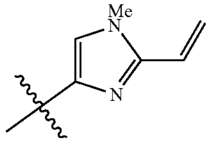 [SMILES: *c1cn(C)c(C=C)n1] | lll |
| 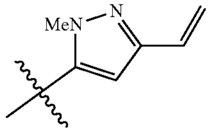 [SMILES: *c1cc(C=C)nn1C] | mmm |
| 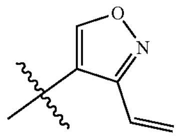 [SMILES: *c1conc1C=C] | nnn |
| 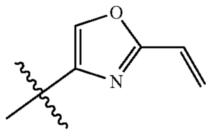 [SMILES: *c1coc(C=C)n1] | ooo |

TABLE 1a-continued
Exemplary Y groups
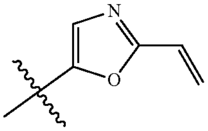 [SMILES: *c1cnc(C=C)o1]
ppp
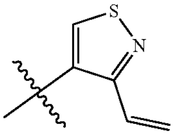 [SMILES: *c1csnc1C=C]
qqq
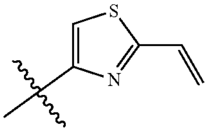 [SMILES: *c1csc(C=C)n1]
rrr
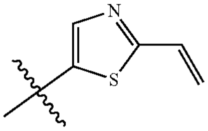 [SMILES: *c1cnc(C=C)s1]
sss
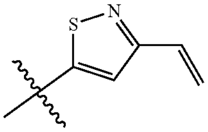 [SMILES: *c1cc(C=C)ns1]
ttt
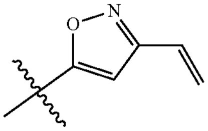 [SMILES: *c1cc(C=C)no1]
uuu
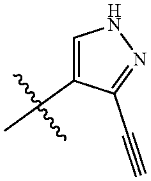 [SMILES: *c1c[nH]nc1C#C]
vvv
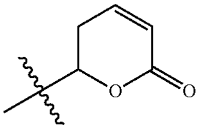 [SMILES: *C1CC=CC(=O)O1]
qqq
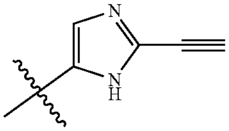 [SMILES: *c1cnc(C#C)[nH]1]
www
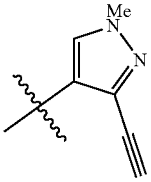 [SMILES: *c1cn(C)nc1C#C]
xxx
TABLE 1a-continued
Exemplary Y groups
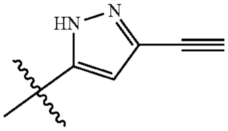 [SMILES: *c1cc(C#C)n[nH]1]
yyy
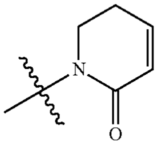 [SMILES: *N1CCC=CC1=O]
zzz
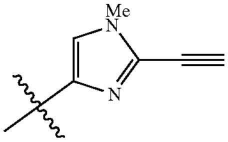 [SMILES: *c1cn(C)c(C#C)n1]
aaaa
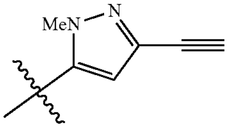 [SMILES: *c1cc(C#C)nn1C]
bbb
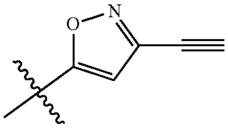 [SMILES: *c1cc(C#C)no1]
cccc
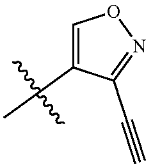 [SMILES: *c1conc1C#C]
dddd
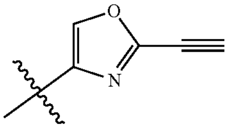 [SMILES: *c1coc(C#C)n1]
eeee
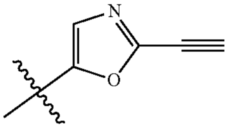 [SMILES: *c1cnc(C#C)o1]
ffff
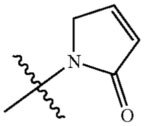 [SMILES: *N1CC=CC1=O]
gggg
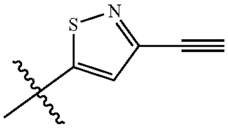 [SMILES: *c1cc(C#C)ns1]
hhhh TABLE 1a-continued
| Exemplary Y groups | |
|---|---|
| 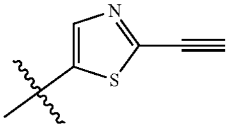 [SMILES: *c1cnc(C#C)s1] | iiii |
| 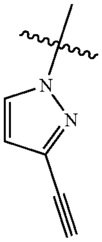 [SMILES: *n1ccc(C#C)n1] | jjjj |
| 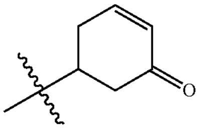 [SMILES: *C1CC=CC(=O)C1] | kkkk |
| 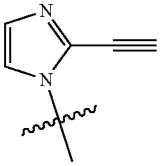 [SMILES: *n1ccnc1C#C] | llll |
| 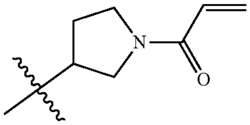 [SMILES: *C1CCN(C(=O)C=C)C1] | mmmm |
| 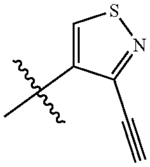 [SMILES: *c1csnc1C#C] | nnnn |
| 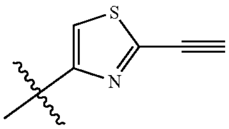 [SMILES: *c1csc(C#C)n1] | oooo |
| 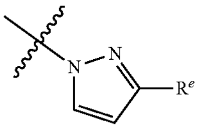 | pppp |
| 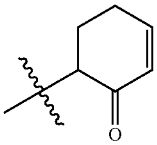 [SMILES: *C1CCC=CC1=O] | qqqq |
TABLE 1a-continued
| Exemplary Y groups | |
|---|---|
| 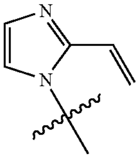 [SMILES: *n1ccnc1C=C] | rrrr |
| 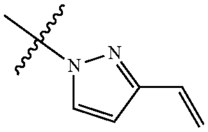 [SMILES: *n1ccc(C=C)n1] | ssss |
| 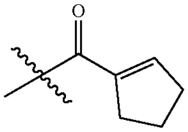 [SMILES: *C(=O)C1=CCCC1] | tttt |
| 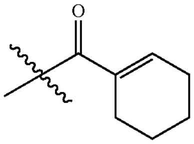 [SMILES: *C(=O)C1=CCCCC1] | uuuu |
| 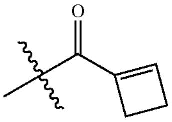 [SMILES: *C(=O)C1=CCC1] | vvvv |
| 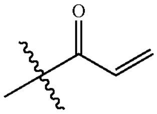 [SMILES: *C(=O)C=C] | wwww |
| 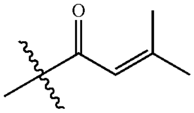 [SMILES: *C(=O)C=C(C)C] | xxxx |
| 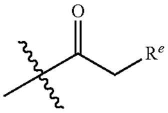 | yyyy |
| 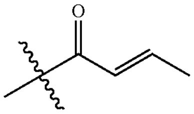 [SMILES: *C(=O)/C=C/C] | zzzz |
| 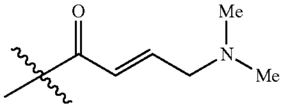 [SMILES: *C(=O)/C=C/CN(C)C] | aaaaa |
| 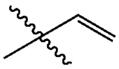 [SMILES: *C=C] | bbbbb |

TABLE 1a-continued

| Exemplary Y groups | |
|---|---|
| 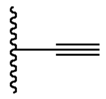 [SMILES: *C#C] | ccccc |

wherein each $R^e$ is independently a suitable leaving group, $NO_2$, CN or oxo.

In certain embodiments, a warhead group is $-C\equiv CH$, $-C\equiv CCH_2NH$(isopropyl), $-NHC(O)C\equiv CCH_2CH_3$, $-CH_2-C\equiv C\equiv CH_3$, $-C\equiv CCH_2OH$, $-CH_2C(O)C\equiv CH$, $-C(O)C\equiv CH$, or $-CH_2C(=O)C=CH$. In some embodiments, a warhead group is selected from $NHC(O)CH=CH_2$, $-NHC(O)CH=CHCH_2N(CH_3)_2$, or $-CH_2NHC(O)CH=CH_2$.

In certain embodiments, a warhead group is selected from those set forth in Table 1b, below, wherein each wavy line indicates the point of attachment to the rest of the molecule. In certain embodiments, $R^5$ is selected from those set forth in Table 1b.

TABLE 1b

| Exemplary Warhead Groups | |
|---|---|
| 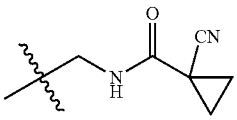 [SMILES: *CNC(=O)C1(C#N)CC1] | a |
| 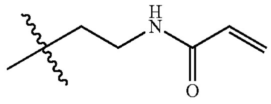 [SMILES: *CCNC(=O)C=C] | b |
| 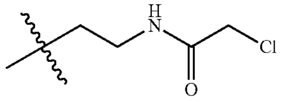 [SMILES: *CCNC(=O)CCl] | c |
| 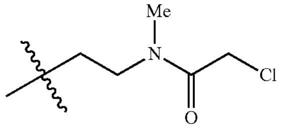 [SMILES: *CCN(C)C(=O)CCl] | d |
| 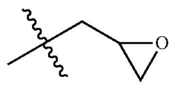 [SMILES: *CC1CO1] | e |
| 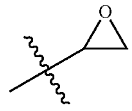 [SMILES: *C1CO1] | f |
| 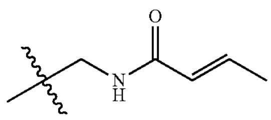 [SMILES: *CNC(=O)/C=C/C] | g |
| 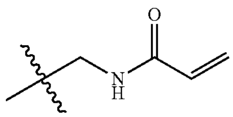 [SMILES: *CNC(=O)C=C] | h |

TABLE 1b-continued

| Exemplary Warhead Groups | |
|---|---|
| 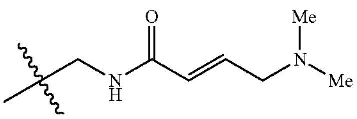 [SMILES: *CNC(=O)/C=C/CN(C)C] | i |
| 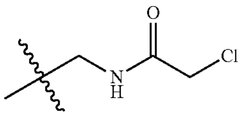 [SMILES: *CNC(=O)CCl] | j |
| 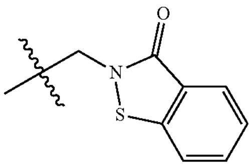 [SMILES: *Cn1sc2ccccc2c1=O] | k |
| 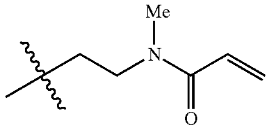 [SMILES: *CCN(C)C(=O)C=C] | l |
| 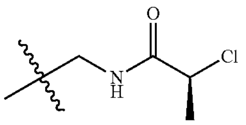 [SMILES: *CNC(=O)[C@H](C)Cl] | m |
| 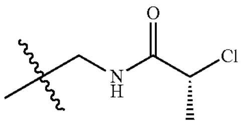 [SMILES: *CNC(=O)[C@@H](C)Cl] | n |
| 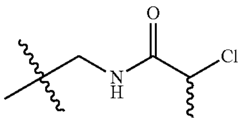 [SMILES: *CNC(=O)C(C)Cl] | o |
| 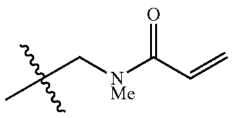 [SMILES: *CN(C)C(=O)C=C] | p |
| 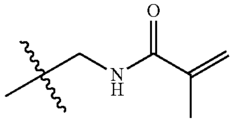 [SMILES: *CNC(=O)C(=C)C] | q |
| 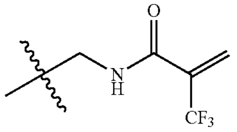 | r |
| 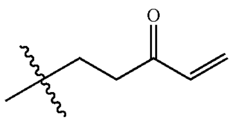 [SMILES: *CCC(=O)C=C] | s |

TABLE 1b-continued
| Exemplary Warhead Groups | |
| --- | --- |
| 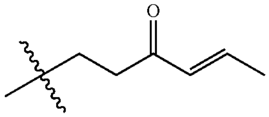 [SMILES: *CCC(=O)/C=C/C] | t |
| 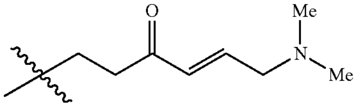 [SMILES: *CCC(=O)/C=C/CN(C)C] | u |
| 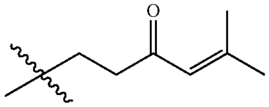 [SMILES: *CCC(=O)C=C(C)C] | v |
| 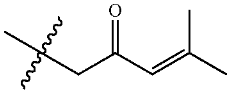 [SMILES: *CC(=O)C=C(C)C] | w |
| 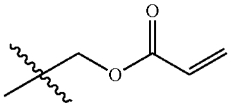 [SMILES: *COC(=O)C=C] | x |
| 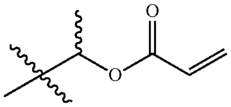 [SMILES: *C(C)OC(=O)C=C] | y |
| 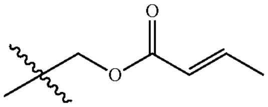 [SMILES: *COC(=O)/C=C/C] | z |
| 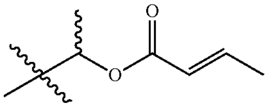 [SMILES: *C(C)OC(=O)/C=C/C] | aa |
| 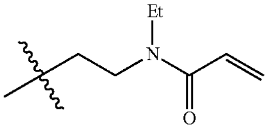 [SMILES: *CCN(CC)C(=O)C=C] | bb |
| 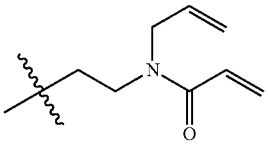 [SMILES: *CCN(CC=C)C(=O)C=C] | cc |
| 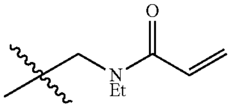 | dd |
| 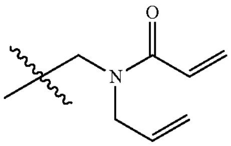 [SMILES: *CN(CC=C)C(=O)C=C] | ee |
TABLE 1b-continued
| Exemplary Warhead Groups | |
| --- | --- |
| 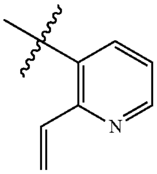 [SMILES: *c1cccnc1C=C] | ff |
| 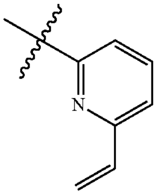 [SMILES: *c1cccc(C=C)n1] | gg |
| 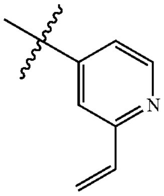 [SMILES: *c1ccnc(C=C)c1] | hh |
| 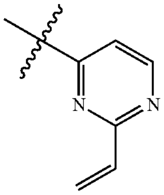 [SMILES: *c1ccnc(C=C)n1] | ii |
| 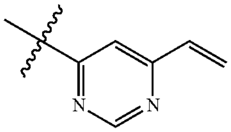 [SMILES: *c1cc(C=C)ncn1] | jj |
| 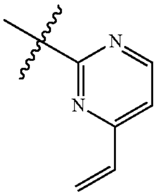 [SMILES: *c1nccc(C=C)n1] | kk |
| 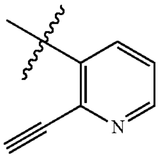 [SMILES: *c1cccnc1C#C] | ll |
| 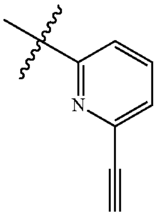 [SMILES: *c1cccc(C#C)n1] | mm |

TABLE 1b-continued
| Exemplary Warhead Groups | |
|---|---|
| 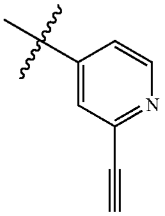 [SMILES: *c1ccnc(C#C)c1] | nn |
| 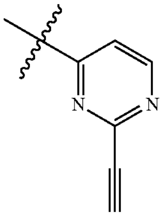 [SMILES: *c1ccnc(C#C)n1] | oo |
| 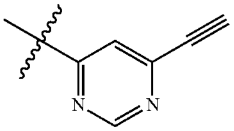 [SMILES: *c1cc(C#C)ncn1] | pp |
| 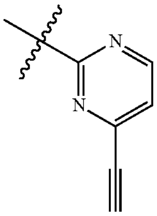 [SMILES: *c1nccc(C#C)n1] | qq |
| 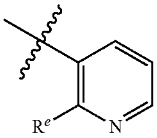 | rr |
| 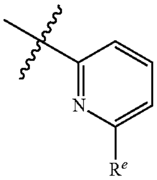 | ss |
| 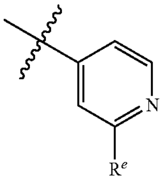 | tt |
| 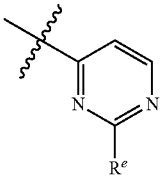 | uu |
TABLE 1b-continued
| Exemplary Warhead Groups | |
|---|---|
| 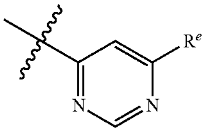 | vv |
| 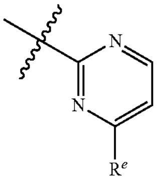 | ww |
| 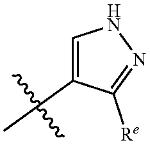 | xx |
| 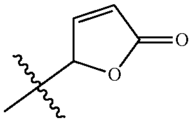 [SMILES: *C1C=CC(=O)O1] | yy |
| 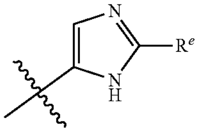 | zz |
| 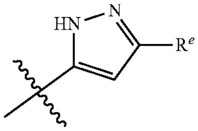 | aaa |
| 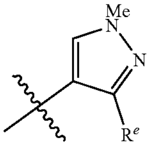 | bbb |
| 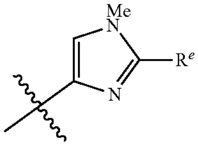 | ccc |
| 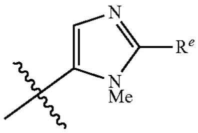 | ddd |
| 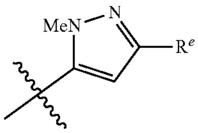 | eee |

TABLE 1b-continued
Exemplary Warhead Groups
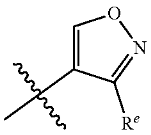
fff
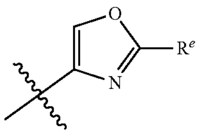
ggg
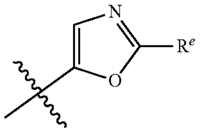
hhh
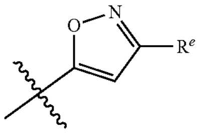
iii
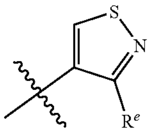
jjj
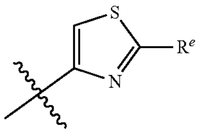
kkk
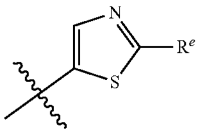
lll
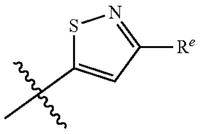
mmm
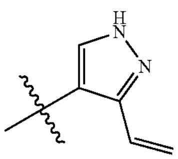 [SMILES: *c1c[nH]nc1C=C]
nnn
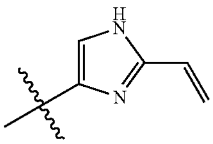 [SMILES: *c1c[nH]c(C=C)n1]
ooo
TABLE 1b-continued
Exemplary Warhead Groups
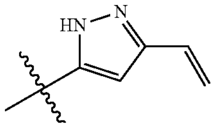 [SMILES: *c1cc(C=C)n[nH]1]
ppp
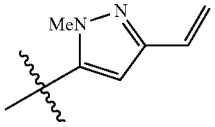 [SMILES: *c1cc(C=C)nn1C]
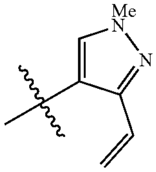 [SMILES: *c1cn(C)nc1C=C]
qqq
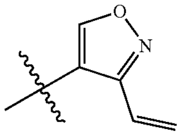 [SMILES: *c1conc1C=C]
rrr
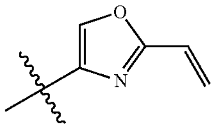 [SMILES: *c1coc(C=C)n1]
sss
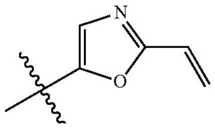 [SMILES: *c1cnc(C=C)o1]
ttt
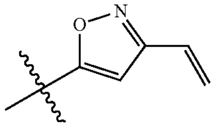 [SMILES: *c1cc(C=C)no1]
uuu
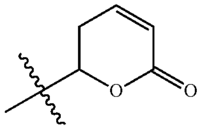
vvv
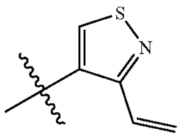 [SMILES: *c1csnc1C=C]
www
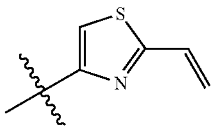 [SMILES: *c1csc(C=C)n1]
xxx TABLE 1b-continued
| Exemplary Warhead Groups | |
|---|---|
| 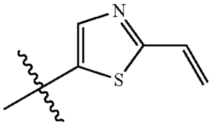 [SMILES: *c1cnc(C=C)s1] | yyy |
| 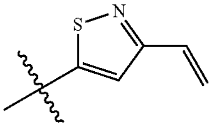 [SMILES: *c1cc(C=C)ns1] | zzz |
| 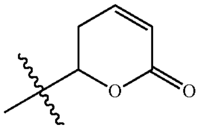 [SMILES: *C1CC=CC(=O)O1] | aaaa |
| 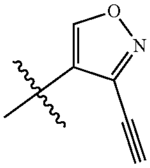 | bbbb |
| 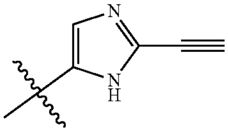 [SMILES: *c1cnc(C#C)[nH]1] | cccc |
| 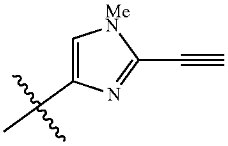 | dddd |
| 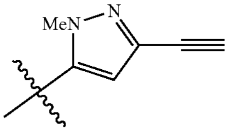 | eeee |
| 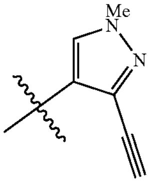 [SMILES: *c1cn(C)nc1C#C] | ffff |
| 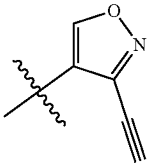 [SMILES: *c1conc1C#C] | gggg |
| 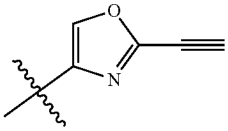 [SMILES: *c1coc(C#C)n1] | hhhh |
TABLE 1b-continued
| Exemplary Warhead Groups | |
|---|---|
| 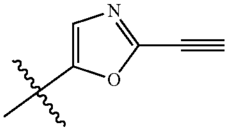 [SMILES: *c1cnc(C#C)o1] | iiii |
| 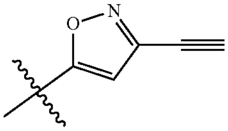 | jjjj |
| 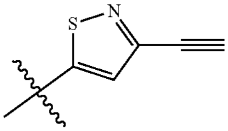 [SMILES: *c1cc(C#C)ns1] | kkkk |
| 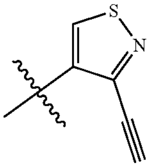 | llll |
| 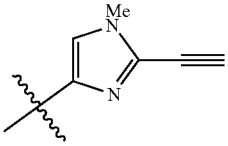 [SMILES: *c1cn(C)c(C#C)n1] | mmmm |
| 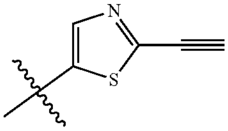 | nnnn |
| 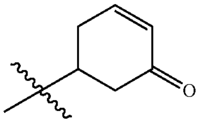 [SMILES: *C1CC=CC(=O)C1] | oooo |
| 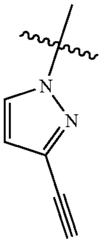 [SMILES: *n1ccc(C#C)n1] | pppp |
| 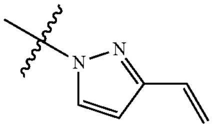 [SMILES: *n1ccc(C=C)n1] | qqqq |

TABLE 1b-continued
Exemplary Warhead Groups
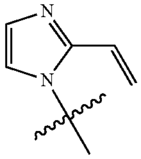 [SMILES: *n1ccnc1C=C]
rrrr
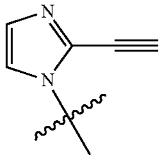 [SMILES: *n1ccnc1C#C]
ssss
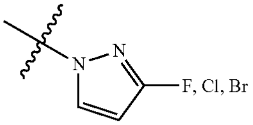
tttt
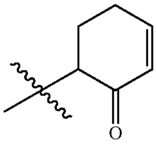 [SMILES: *C1CCC=CC1=O]
uuuu
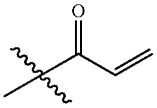 [SMILES: *C(=O)C=C]
vvvv
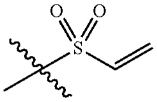 [SMILES: *S(=O)(=O)C=C]
wwww
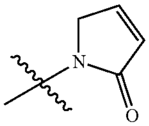 [SMILES: *N1CC=CC1=O]
xxxx
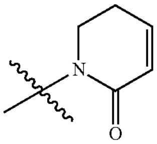 [SMILES: *N1CCC=CC1=O]
yyyy
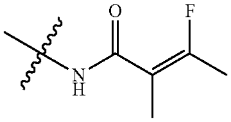 [SMILES: *NC(=O)/C(C)=C(/C)F]
zzzz
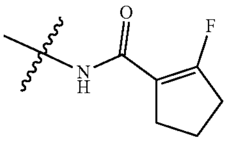 [SMILES: *NC(=O)C1=C(F)CCC1]
aaaaa
TABLE 1b-continued
Exemplary Warhead Groups
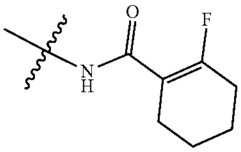 [SMILES: *NC(=O)C1=C(F)CCCC1]
bbbbb
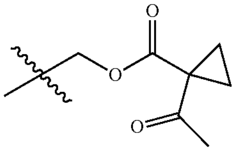 [SMILES: *COC(=O)C1(C(C)=O)CC1]
ccccc
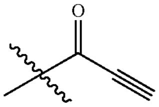 [SMILES: *C(=O)C#C]
ddddd
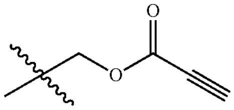 [SMILES: *COC(=O)C#C]
eeeee
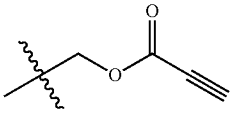 [SMILES: *COC(=O)C#C]
fffff
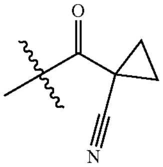 [SMILES: *C(=O)C1(C#N)CC1]
ggggg
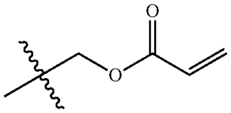 [SMILES: *COC(=O)C=C]
hhhhh
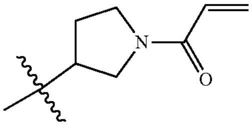 [SMILES: *C1CCN(C(=O)C=C)C1]
iiiii
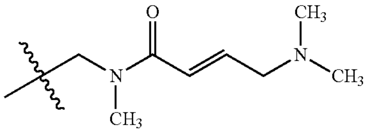
jjjjj
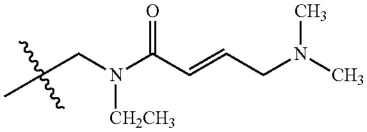 [SMILES: *CN(CC)C(=O)/C=C/CN(C)C]
kkkkk
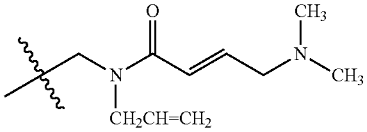
lllll TABLE 1b-continued
| Exemplary Warhead Groups | |
|---|---|
| 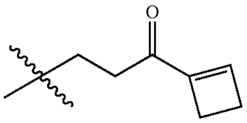 [SMILES: *CCC(=O)C1=CCC1] | mmmmm |
| 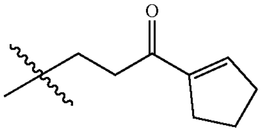 [SMILES: *CCC(=O)C1=CCCC1] | nnnnn |
| 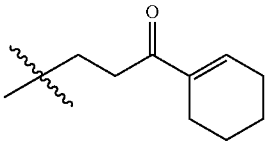 [SMILES: *CCC(=O)C1=CCCCC1] | ooooo |
| 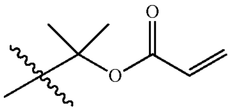 [SMILES: *C(C)(C)OC(=O)C=C] | ppppp |
| 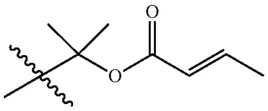 [SMILES: *C(C)(C)OC(=O)/C=C/C] | qqqqq |
| 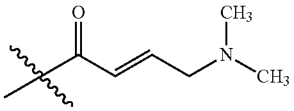 [SMILES: *C(=O)/C=C/CN(C)C] | rrrrr |
| 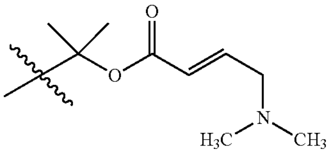 [SMILES: *C(C)(C)OC(=O)/C=C/CN(C)C] | sssss |
| 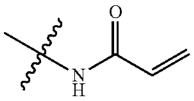 [SMILES: *NC(=O)C=C] | ttttt |
| 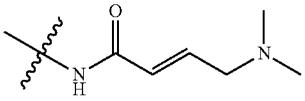 [SMILES: *NC(=O)/C=C/CN(C)C] | uuuuu |
| 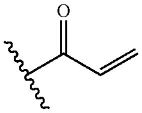 [SMILES: *C(=O)C=C] | vvvvv |
| 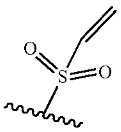 [SMILES: *S(=O)(=O)C=C] | wwwww |
TABLE 1b-continued
| Exemplary Warhead Groups | |
|---|---|
| 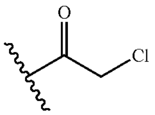 [SMILES: *C(=O)CCl] | xxxxx |
| 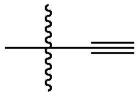 [SMILES: *C#C] | yyyyy |
| 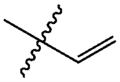 | zzzzz |
| 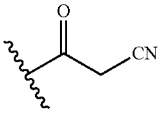 [SMILES: *C(=O)CC#N] | aaaaaa |
| 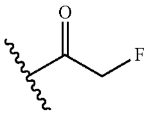 [SMILES: *C(=O)CF] | bbbbbb |
| 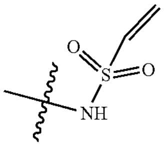 [SMILES: *NS(=O)(=O)C=C] | cccccc |
| 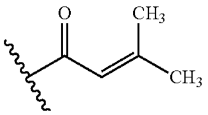 [SMILES: *C(=O)C=C(C)C] | dddddd |
| 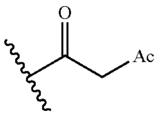 [SMILES: *C(=O)CC(C)=O] | eeeeee |
| 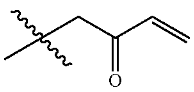 [SMILES: *CC(=O)C=C] | fffff |
| 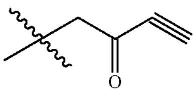 | gggggg |
| 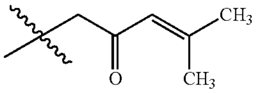 | hhhhhh |
| 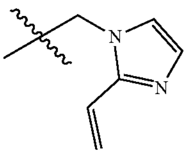 [SMILES: *Cn1ccnc1C=C] | iiiii |

TABLE 1b-continued

| Exemplary Warhead Groups | |
|---|---|
| 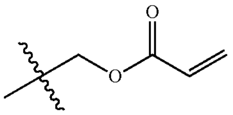 [SMILES: *COC(=O)C=C] | jjjjjj |
| 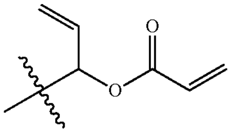 [SMILES: *C(C=C)OC(=O)C=C] | kkkkkk |
| 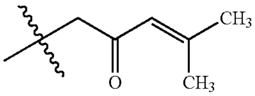 | llllll |
| 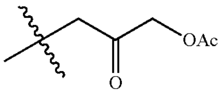 [SMILES: *CC(=O)COC(C)=O] | mmmmmm |
| 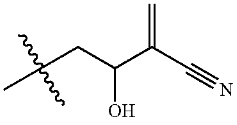 [SMILES: *CC(O)C(=C)C#N] | nnnnnn |
| 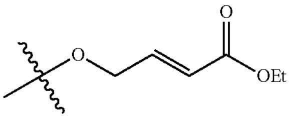 [SMILES: *OC/C=C/C(=O)OCC] | oooooo |
| 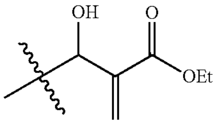 [SMILES: *C(O)C(=C)C(=O)OCC] | pppppp |
| 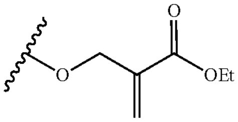 [SMILES: *OCC(=C)C(=O)OCC] | qqqqqq |
| 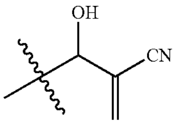 [SMILES: *C(O)C(=C)C#N] | rrrrrr |
| 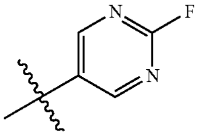 [SMILES: *c1cnc(F)nc1] | ssssss |
| 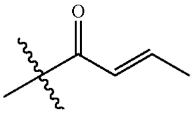 [SMILES: *C(=O)/C=C/C] | tttttt |
| 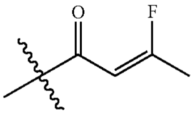 | uuuuuu |

TABLE 1b-continued

| Exemplary Warhead Groups | |
|---|---|
| 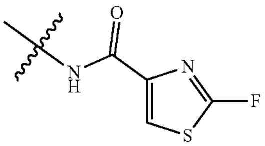 [SMILES: *NC(=O)c1csc(F)n1] | vvvvvv |
| 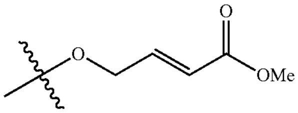 [SMILES: *OC/C=C/C(=O)OC] | wwwwww |
| or | |
| 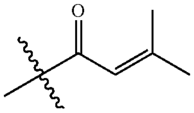 [SMILES: *C(=O)C=C(C)C] | xxxxxx |

wherein each $R^e$ is independently a suitable leaving group, $NO_2$, CN, or oxo.

In some embodiments, Y of a warhead group is an isoxazoline compound or derivative capable of covalently binding to serine. In some embodiments, Y of a warhead group is an isoxazoline compound or derivative described in WO 2010135360, the entire content of which is incorporated herein by reference. As understood by one skilled in the art, an isoxazoline compound or derivative described in WO 2010135360, as Y of a warhead group, can covalently connect to $L^2$ of the warhead group at any reasonable position of the isoxazoline compound or derivative. In some embodiments, Y of a warhead group is:

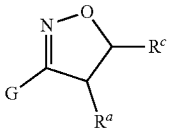

wherein G, $R^a$, and $R^c$ are:

| G | $R^a$ | $R^c$ |
|---|---|---|
| —Br | —H | —H |
| —Cl | —H | —H |
| 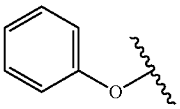 [SMILES: *Oc1ccccc1] | —H | —H |
| 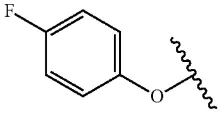 [SMILES: *Oc1ccc(F)cc1] | —H | —H |
| 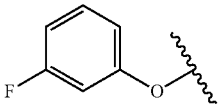 [SMILES: *Oc1cccc(F)c1] | —H | —H |

-continued
| G | $R^a$ | $R^c$ |
|---|---|---|
| 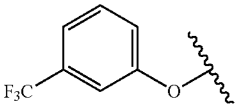 [SMILES: *Oc1cccc(C(F)(F)F)c1] | —H | —H |
| 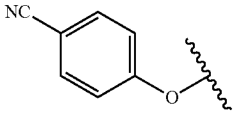 [SMILES: *Oc1ccc(C#N)cc1] | —H | —H |
| 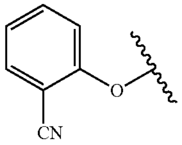 [SMILES: *Oc1ccccc1C#N] | —H | —H |
| 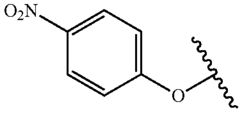 [SMILES: *Oc1ccc([N+](=O)[O-])cc1] | —H | —H |
| 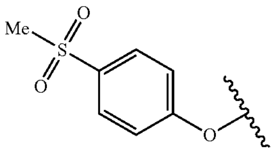 [SMILES: *Oc1ccc(S(C)(=O)=O)cc1] | —H | —H |
| 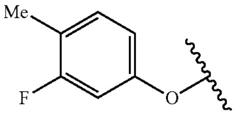 [SMILES: *Oc1ccc(C)c(F)c1] | —H | —H |
| 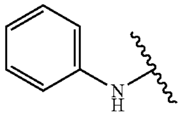 [SMILES: *Nc1ccccc1] | —H | —H |
| 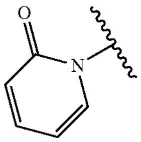 [SMILES: *n1ccccc1=O] | —H | —H |
| 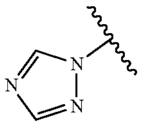 | —H | —H |
| 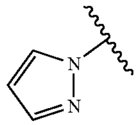 | —H | —H |
| 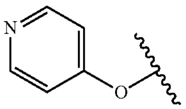 [SMILES: *Oc1ccncc1] | —H | —H |
-continued
| G | $R^a$ | $R^c$ |
|---|---|---|
| 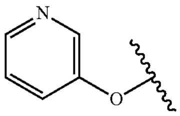 [SMILES: *Oc1cccnc1] | —H | —H |
| 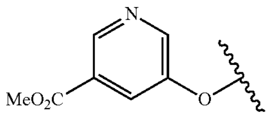 [SMILES: *Oc1cncc(C(=O)OC)c1] | —H | —H |
| 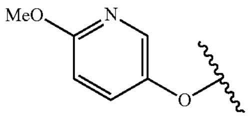 [SMILES: *Oc1ccc(OC)nc1] | —H | —H |
| 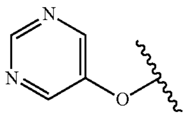 [SMILES: *Oc1cncnc1] | —H | —H |
| 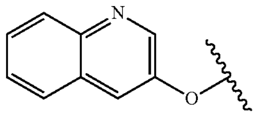 [SMILES: *Oc1cnc2ccccc2c1] | —H | —H |
| 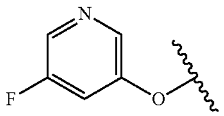 [SMILES: *Oc1cncc(F)c1] | —H | —H |
| 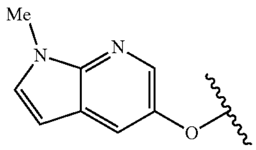 [SMILES: *Oc1cnc2c(ccn2C)c1] | —H | —H |
| —OMe | —H | —H |
| 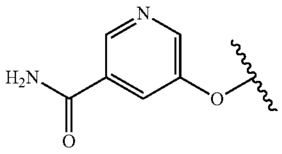 [SMILES: *Oc1cncc(C(N)=O)c1] | —H | —H |
| 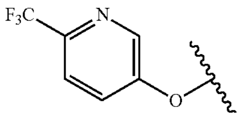 [SMILES: *Oc1ccc(C(F)(F)F)nc1] | —H | —H |
| 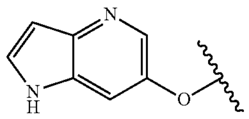 [SMILES: *Oc1cnc2cc[nH]c2c1] | —H | —H |
| 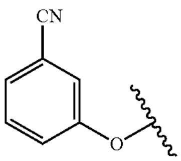 [SMILES: *Oc1cccc(C#N)c1] | —H | —H |

-continued
| G | $R^a$ | $R^c$ |
|---|---|---|
| 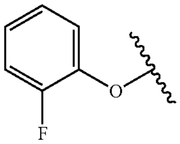 [SMILES: *Oc1ccccc1F] | —H | —H |
| 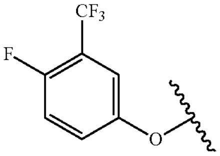 [SMILES: *Oc1ccc(F)c(C(F)(F)F)c1] | —H | —H |
| 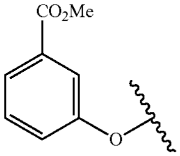 [SMILES: *Oc1cccc(C(=O)OC)c1] | —H | —H |
| 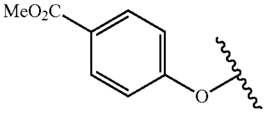 [SMILES: *Oc1ccc(C(=O)OC)cc1] | —H | —H |
| 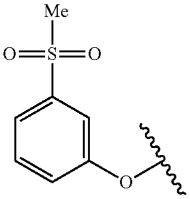 [SMILES: *Oc1cccc(S(C)(=O)=O)c1] | —H | —H |
| 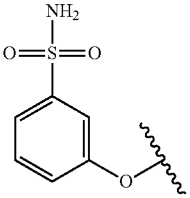 [SMILES: *Oc1cccc(S(N)(=O)=O)c1] | —H | —H |
| 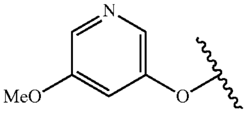 [SMILES: *Oc1cncc(OC)c1] | —H | —H |
| 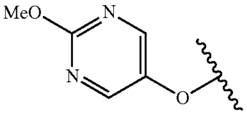 [SMILES: *Oc1cnc(OC)nc1] | —H | —H |
| 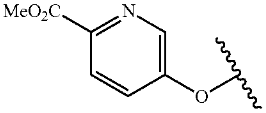 [SMILES: *Oc1ccc(C(=O)OC)nc1] | —H | —H |
| 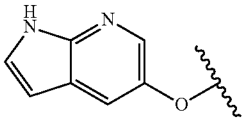 [SMILES: *Oc1cnc2[nH]ccc2c1] | —H | —H |
| 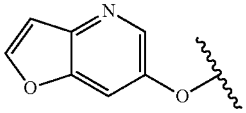 [SMILES: *Oc1cnc2ccoc2c1] | —H | —H |
| 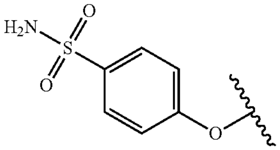 [SMILES: *Oc1ccc(S(N)(=O)=O)cc1] | —H | —H |
| 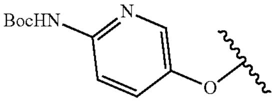 [SMILES: *Oc1ccc(NC(=O)OC(C)(C)C)nc1] | —H | —H |
| 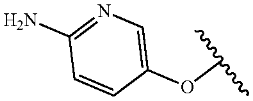 [SMILES: *Oc1ccc(N)nc1] | —H | —H |
| 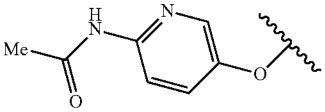 [SMILES: *Oc1ccc(NC(C)=O)nc1] | —H | —H |
| 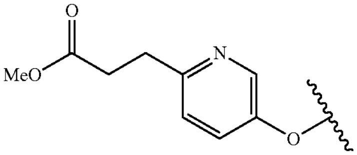 [SMILES: *Oc1ccc(CCC(=O)OC)nc1] | —H | —H |
| 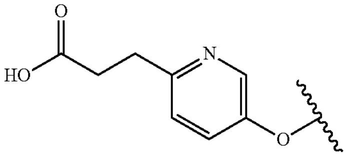 [SMILES: *Oc1ccc(CCC(=O)O)nc1] | —H | —H |
| 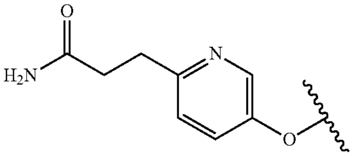 [SMILES: *Oc1ccc(CCC(N)=O)nc1] | —H | —H |
| 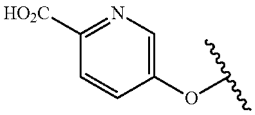 [SMILES: *Oc1ccc(C(=O)O)nc1] | —H | —H |
| 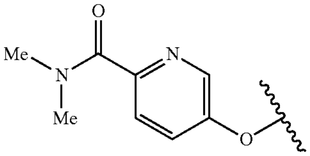 [SMILES: *Oc1ccc(C(=O)N(C)C)nc1] | —H | —H |

-continued

| G | $R^a$ | $R^c$ |
|---|---|---|
| 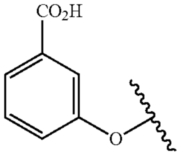 [SMILES: *Oc1cccc(C(=O)O)c1] | —H | —H |
| 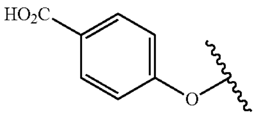 [SMILES: *Oc1ccc(C(=O)O)cc1] | —H | —H |
| 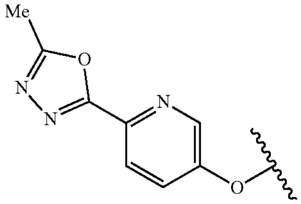 [SMILES: *Oc1ccc(-c2nnc(C)o2)nc1] | —H | —H |
| 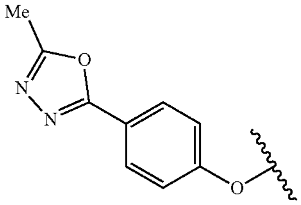 [SMILES: *Oc1ccc(-c2nnc(C)o2)cc1] | —H | —H |
| 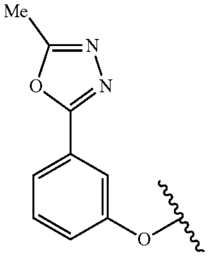 [SMILES: *Oc1cccc(-c2nnc(C)o2)c1] | —H | —H |
| 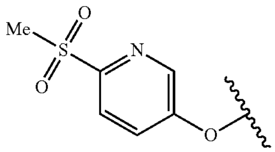 [SMILES: *Oc1ccc(S(C)(=O)=O)nc1] | —H | —H |
| 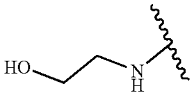 [SMILES: *NCCO] | —H | —H |
| 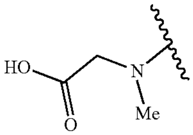 [SMILES: *N(C)CC(=O)O] | —H | —H |
| 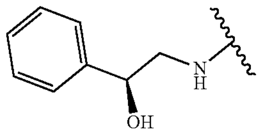 [SMILES: *NC[C@@H](O)c1ccccc1] | —H | —H |

-continued

| G | $R^a$ | $R^c$ |
|---|---|---|
| 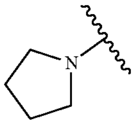 [SMILES: *N1CCCC1] | —H | —H |
| 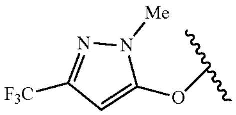 [SMILES: *Oc1cc(C(F)(F)F)nn1C] | —H | —H |
| 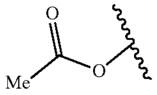 | —H | —H |
| —Br | —$CH_3$ | —H |
| —Br | —$CH_3$ | —H |
| 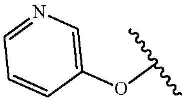 [SMILES: *Oc1cccnc1] | —$CH_3$ | —H |
| —Br | —H | —$CH_3$ |
| 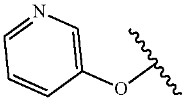 [SMILES: *Oc1cccnc1] | —H | —$CH_3$ |
| —Br | —H | —$CF_3$ |
| 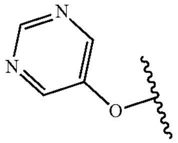 [SMILES: *Oc1cncnc1] | —H | —$CF_3$ |
| —Br | —H | —$CH_2CH_3$ |

In some embodiments, a warhead group is selected from those set forth in Table 1c, below, wherein each wavy line indicates the point of attachment to the rest of the molecule. In some embodiments, $R^5$ is selected from those set forth in Table 1c.

TABLE 1c

| Exemplary Warhead Groups | |
|---|---|
| 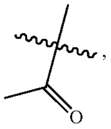 [SMILES: *C(C)=O] | (A1) |
| 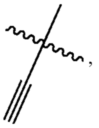 [SMILES: *C#C] | (A2) |

TABLE 1c-continued
| Exemplary Warhead Groups |
|---|
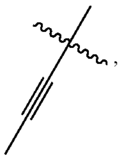 [SMILES: *C#CC]
(A3)
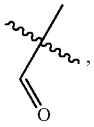
(A4)
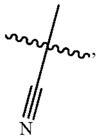 [SMILES: *C#N]
(A5)
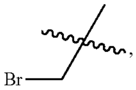
(A6)
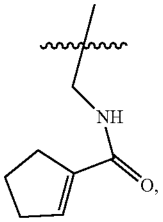 [SMILES: *CNC(=O)C1=CCCC1]
(A7)
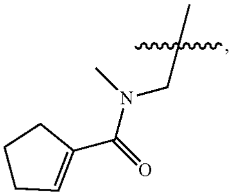 [SMILES: *CN(C)C(=O)C1=CCCC1]
(A8)
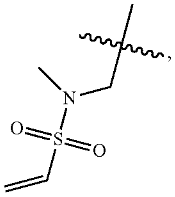 [SMILES: *CN(C)S(=O)(=O)C=C]
(A9)
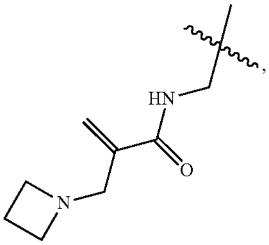 [SMILES: *CNC(=O)C(=C)CN1CCC1]
(A10)
TABLE 1c-continued
| Exemplary Warhead Groups |
|---|
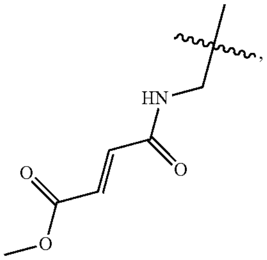 [SMILES: *CNC(=O)/C=C/C(=O)OC]
(A11)
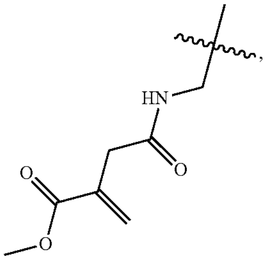 [SMILES: *CNC(=O)CC(=C)C(=O)OC]
(A12)
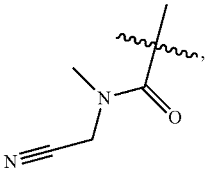 [SMILES: *C(=O)N(C)CC#N]
(A13)
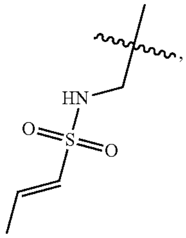 [SMILES: *CNS(=O)(=O)/C=C/C]
(A14)
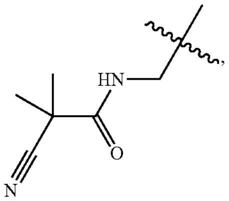 [SMILES: *CNC(=O)C(C)(C)C#N]
(A15)
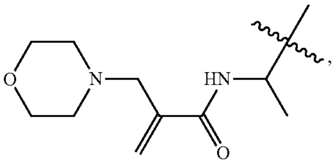 [SMILES: *C(C)NC(=O)C(=C)CN1CCOCC1]
(A16)
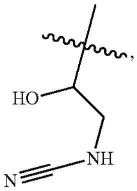
(A17)

TABLE 1c-continued
| Exemplary Warhead Groups |
|---|
| 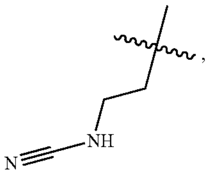 [SMILES: *CCNC#N] (A18) |
| 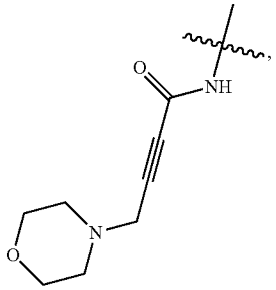 [SMILES: *NC(=O)C#CCN1CCOCC1] (A19) |
| 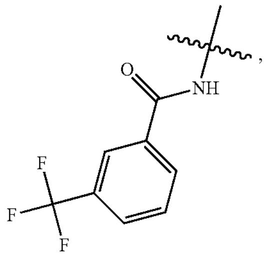 [SMILES: *NC(=O)c1cccc(C(F)(F)F)c1] (A20) |
| 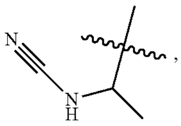 (A21) |
| 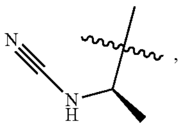 [SMILES: *[C@@H](C)NC#N] (A21a) |
| 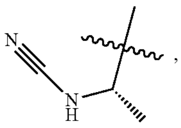 (A21b) |
| 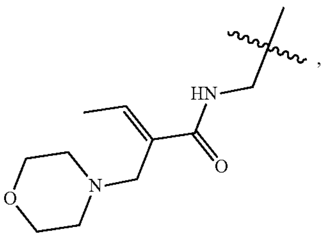 [SMILES: *CNC(=O)/C(=C/C)CN1CCOCC1] (A22) |
TABLE 1c-continued
| Exemplary Warhead Groups |
|---|
| 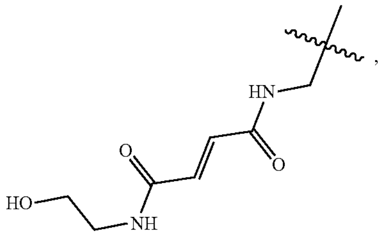 [SMILES: *CNC(=O)/C=C/C(=O)NCCO] (A23) |
| 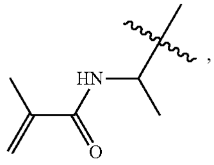 [SMILES: *C(C)NC(=O)C(=C)C] (A24) |
| 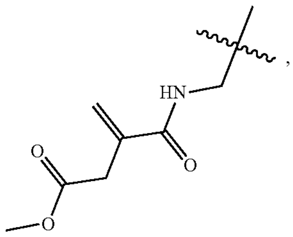 [SMILES: *CNC(=O)C(=C)CC(=O)OC] (A25) |
| 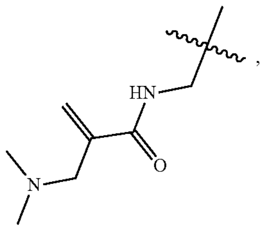 [SMILES: *CNC(=O)C(=C)CN(C)C] (A26) |
| 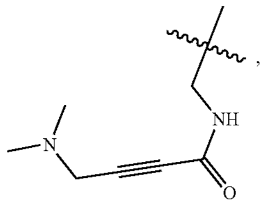 [SMILES: *CNC(=O)C#CCN(C)C] (A27) |
| 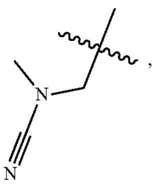 [SMILES: *CN(C)C#N] (A28) |
| 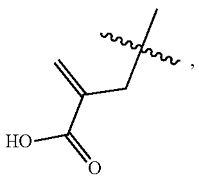 [SMILES: *CC(=C)C(=O)O] (A29) |

TABLE 1c-continued
| Exemplary Warhead Groups |
| --- |
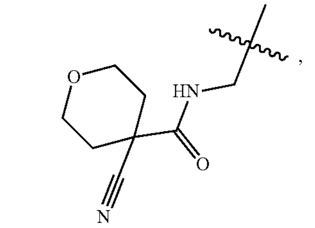 [SMILES: *CNC(=O)C1(C#N)CCOCC1]
(A30)
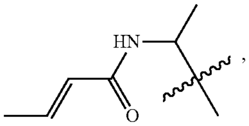 [SMILES: *C(C)NC(=O)/C=C/C]
(A31)
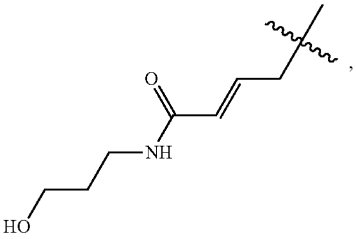 [SMILES: *C/C=C/C(=O)NCCCO]
(A32)
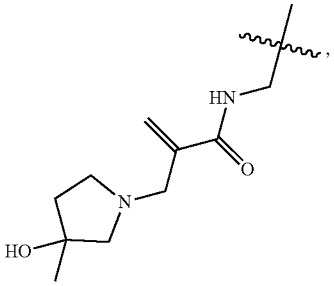 [SMILES: *CNC(=O)C(=C)CN1CCC(C)(O)C1]
(A33)
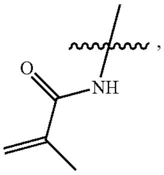 [SMILES: *NC(=O)C(=C)C]
(A34)
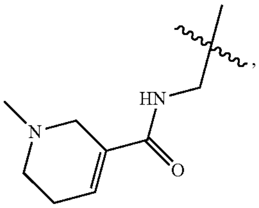 [SMILES: *CNC(=O)C1=CCCN(C)C1]
(A35)
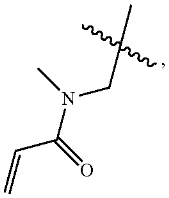 [SMILES: *CN(C)C(=O)C=C]
(A36)
TABLE 1c-continued
| Exemplary Warhead Groups |
| --- |
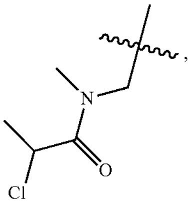 [SMILES: *CN(C)C(=O)C(C)Cl]
(A37)
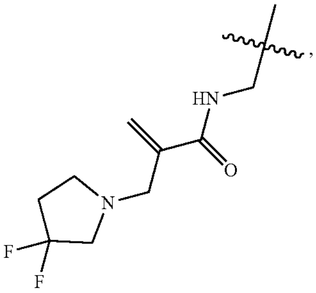 [SMILES: *CNC(=O)C(=C)CN1CCC(F)(F)C1]
(A38)
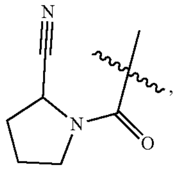 [SMILES: *C(=O)N1CCCC1C#N]
(A39)
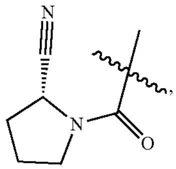 [SMILES: *C(=O)N1CCC[C@@H]1C#N]
(A39a)
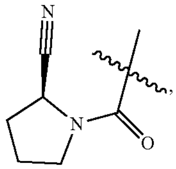 [SMILES: *C(=O)N1CCC[C@H]1C#N]
(A39b)
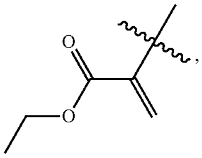 [SMILES: *C(=C)C(=O)OCC]
(A40)
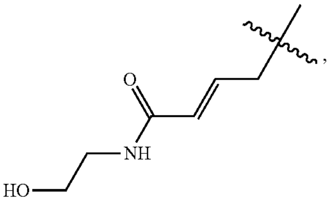 [SMILES: *C/C=C/C(=O)NCCO]
(A41)

TABLE 1c-continued
Exemplary Warhead Groups
(A42)
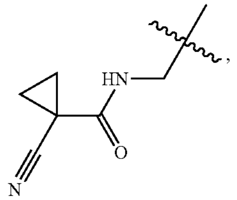 [SMILES: *CNC(=O)C1(C#N)CC1]
(A43)
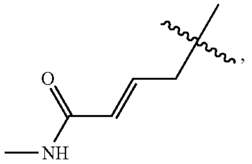 [SMILES: *C/C=C/C(=O)NC]
(A44)
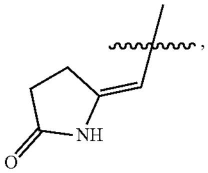 [SMILES: */C=C1\CCC(=O)N1]
(A45)
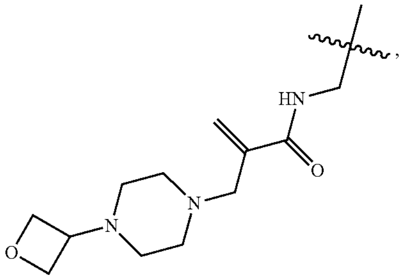 [SMILES: *CNC(=O)C(=C)CN1CCN(C2COC2)CC1]
(A46)
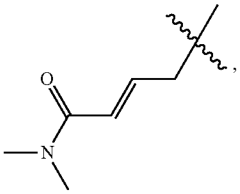 [SMILES: *C/C=C/C(=O)N(C)C]
(A47)
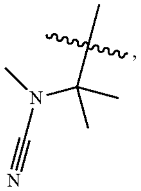 [SMILES: *C(C)(C)N(C)C#N]
(A48)
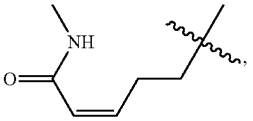 [SMILES: *CC/C=C\C(=O)NC]
(A49)
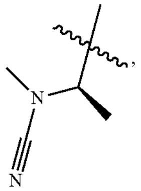 [SMILES: *[C@@H](C)N(C)C#N]
TABLE 1c-continued
Exemplary Warhead Groups
(A50)
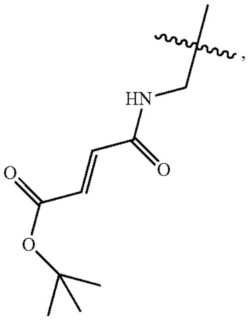 [SMILES: *CNC(=O)/C=C/C(=O)OC(C)(C)C]
(A51)
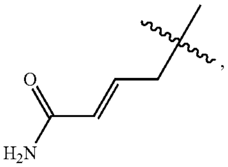 [SMILES: *C/C=C/C(N)=O]
(A52)
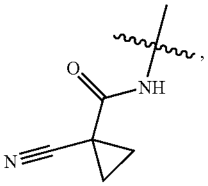 [SMILES: *NC(=O)C1(C#N)CC1]
(A53)
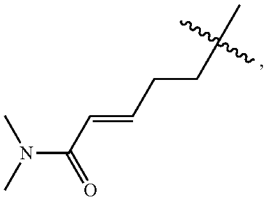 [SMILES: *CC/C=C/C(=O)N(C)C]
(A54)
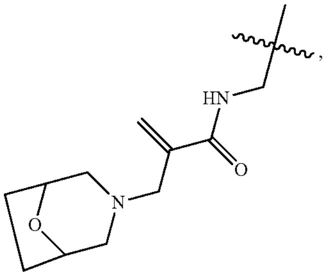 [SMILES: *CNC(=O)C(=C)CN1CC2CCC(C1)O2]
(A55)
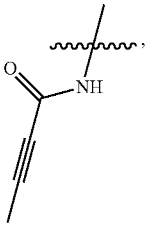 [SMILES: *NC(=O)C#CC]

TABLE 1c-continued
| Exemplary Warhead Groups |
|---|
| 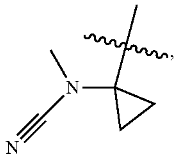 [SMILES: *C1(N(C)C#N)CC1] (A56) |
| 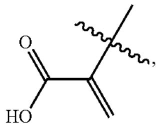 [SMILES: *C(=C)C(=O)O] (A57) |
| 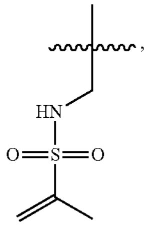 (A58) |
| 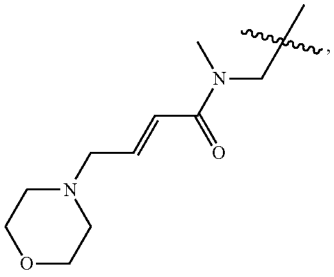 [SMILES: *CN(C)C(=O)/C=C/CN1CCOCC1] (A59) |
| 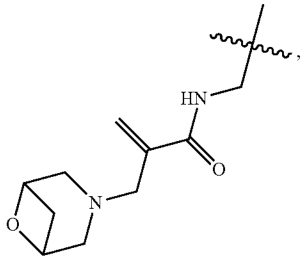 [SMILES: *CNC(=O)C(=C)CN1CC2CC(C1)O2] (A60) |
| 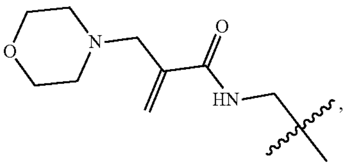 [SMILES: *CNC(=O)C(=C)CN1CCOCC1] (A61) |
| 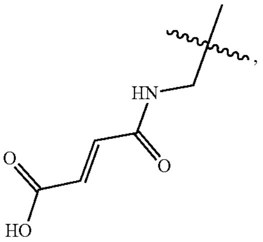 [SMILES: *CNC(=O)/C=C/C(=O)O] (A62) |
TABLE 1c-continued
| Exemplary Warhead Groups |
|---|
| 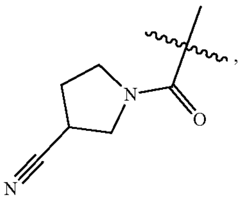 [SMILES: *C(=O)N1CCC(C#N)C1] (A63) |
| 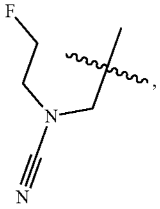 (A64) |
| 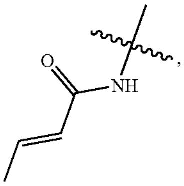 [SMILES: *NC(=O)/C=C/C] (A65) |
| 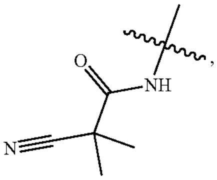 [SMILES: *NC(=O)C(C)(C)C#N] (A66) |
| 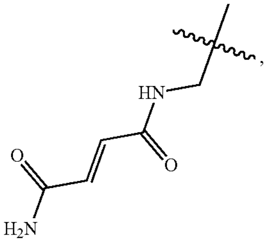 [SMILES: *CNC(=O)/C=C/C(N)=O] (A67) |
| 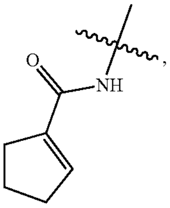 [SMILES: *NC(=O)C1=CCCC1] (A68) |
| 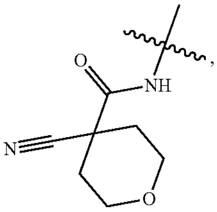 [SMILES: *NC(=O)C1(C#N)CCOCC1] (A69) |

TABLE 1c-continued
| Exemplary Warhead Groups |
| --- |
| 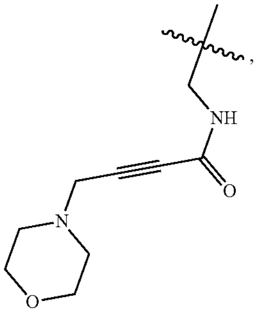 [SMILES: *CNC(=O)C#CCN1CCOCC1], (A70) |
| 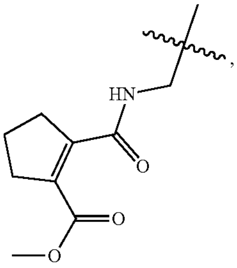 [SMILES: *CNC(=O)C1=C(C(=O)OC)CCC1], (A71) |
| 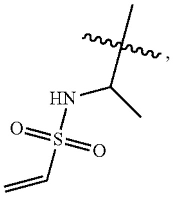 [SMILES: *C(C)NS(=O)(=O)C=C], (A72) |
| 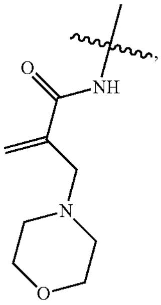 [SMILES: *NC(=O)C(=C)CN1CCOCC1], (A73) |
| 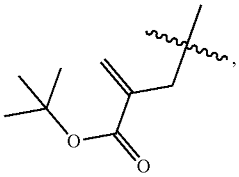 [SMILES: *CC(=C)C(=O)OC(C)(C)C], (A74) |
| 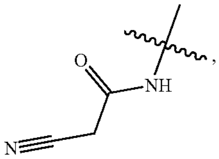 [SMILES: *NC(=O)CC#N], (A75) |
TABLE 1c-continued
| Exemplary Warhead Groups |
| --- |
| 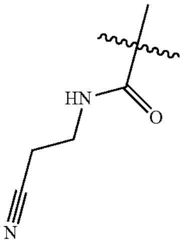 [SMILES: *C(=O)NCCC#N] (A76) |
| 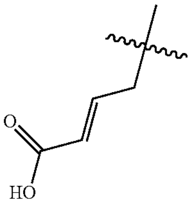 [SMILES: *C/C=C/C(=O)O] (A77) |
| 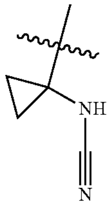 (A78) |
| 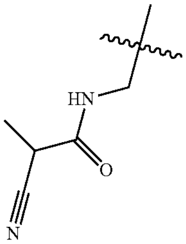 [SMILES: *CNC(=O)C(C)C#N] (A79) |
| 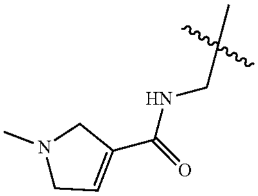 [SMILES: *CNC(=O)C1=CCN(C)C1] (A80) |
| 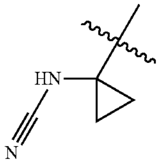 [SMILES: *C1(NC#N)CC1] (A81) |
| 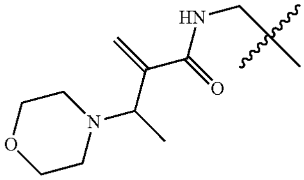 [SMILES: *CNC(=O)C(=C)C(C)N1CCOCC1] (A82) |

TABLE 1c-continued
Exemplary Warhead Groups
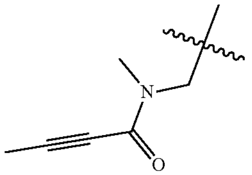 [SMILES: *CN(C)C(=O)C#CC]
(A83)
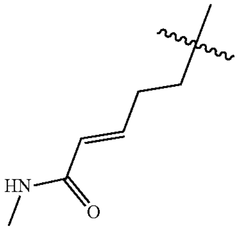 [SMILES: *CC/C=C/C(=O)NC]
(A84)
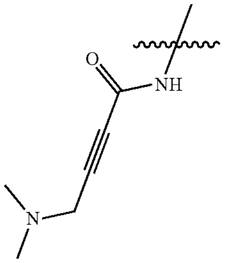 [SMILES: *NC(=O)C#CCN(C)C]
(A85)
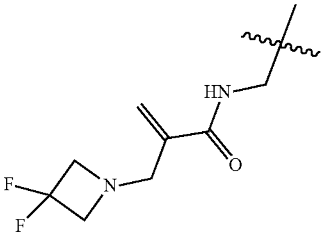 [SMILES: *CNC(=O)C(=C)CN1CC(F)(F)C1]
(A86)
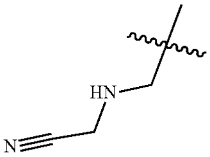 [SMILES: *CNCC#N]
(A87)
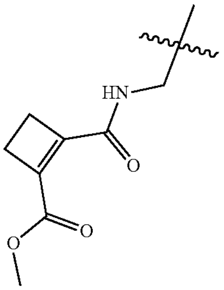 [SMILES: *CNC(=O)C1=C(C(=O)OC)CC1]
(A88)
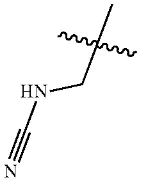 [SMILES: *CNC#N]
(A89)
TABLE 1c-continued
Exemplary Warhead Groups
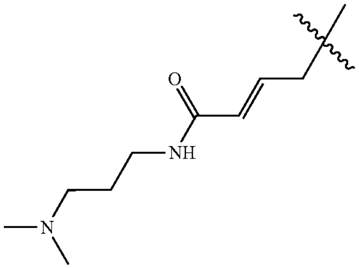 [SMILES: *C/C=C/C(=O)NCCCN(C)C]
(A90)
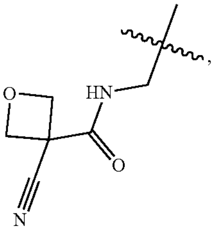 [SMILES: *CNC(=O)C1(C#N)COC1]
(A91)
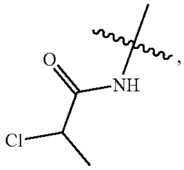 [SMILES: *NC(=O)C(C)Cl]
(A92)
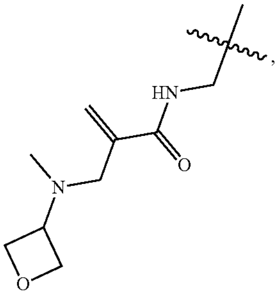 [SMILES: *CNC(=O)C(=C)CN(C)C1COC1]
(A93)
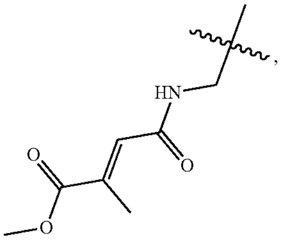 [SMILES: *CNC(=O)/C=C(\C)C(=O)OC]
(A94)
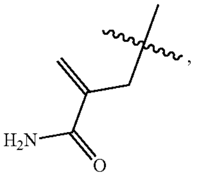
(A95)

TABLE 1c-continued
| Exemplary Warhead Groups | |
|---|---|
| 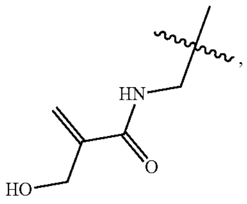 [SMILES: *CNC(=O)C(=C)CO] | (A96) |
| 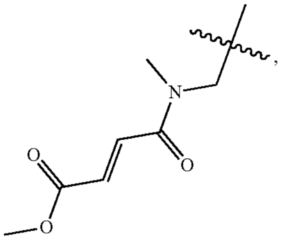 [SMILES: *CN(C)C(=O)/C=C/C(=O)OC] | (A97) |
| 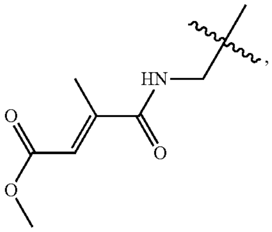 [SMILES: *CNC(=O)/C(C)=C/C(=O)OC] | (A98) |
| 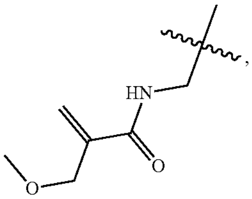 [SMILES: *CNC(=O)C(=C)COC] | (A99) |
| 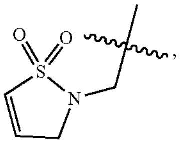 [SMILES: *CN1CC=CS1(=O)=O] | (A100) |
| 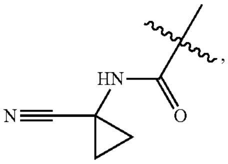 [SMILES: *C(=O)NC1(C#N)CC1] | (A101) |
| 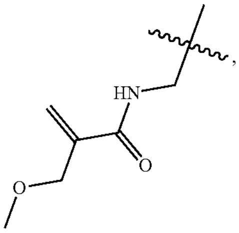 [SMILES: *CNC(=O)C(=C)COC] | (A102) |
TABLE 1c-continued
| Exemplary Warhead Groups | |
|---|---|
| 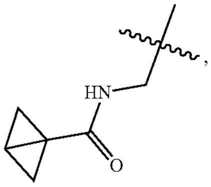 [SMILES: *CNC(=O)C12CC1C2] | (A103) |
| 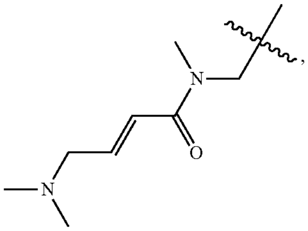 [SMILES: *CN(C)C(=O)/C=C/CN(C)C] | (A104) |
| 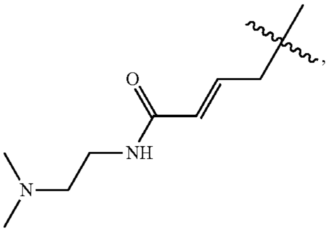 [SMILES: *C/C=C/C(=O)NCCN(C)C] | (A105) |
| 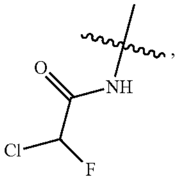 [SMILES: *NC(=O)C(F)Cl] | (A106) |
| 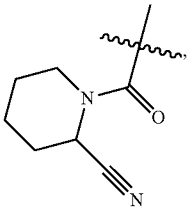 [SMILES: *C(=O)N1CCCCC1C#N] | (A107) |
| 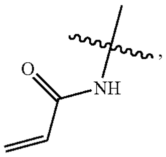 [SMILES: *NC(=O)C=C] | (A108) |
| 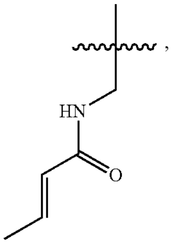 [SMILES: *CNC(=O)/C=C/C] | (A109) |

TABLE 1c-continued
| Exemplary Warhead Groups |
|---|
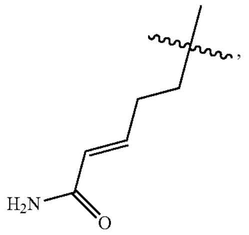 [SMILES: *CC/C=C/C(N)=O]
(A110)
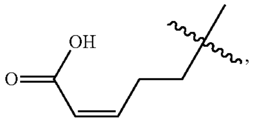 [SMILES: *CC/C=C\C(=O)O]
(A111)
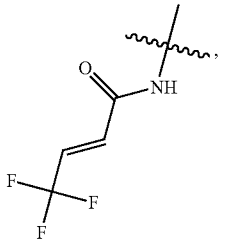 [SMILES: *NC(=O)/C=C/C(F)(F)F]
(A112)
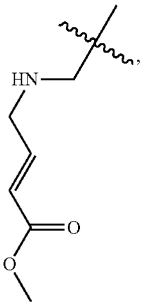 [SMILES: *CNC/C=C/C(=O)OC]
(A113)
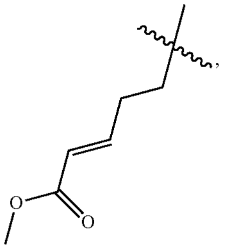 [SMILES: *CC/C=C/C(=O)OC]
(A114)
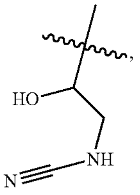 [SMILES: *C(O)CNC#N]
(A115)
TABLE 1c-continued
| Exemplary Warhead Groups |
|---|
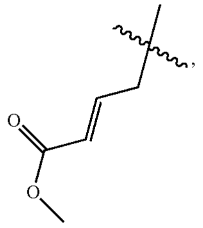 [SMILES: *C/C=C/C(=O)OC]
(A116)
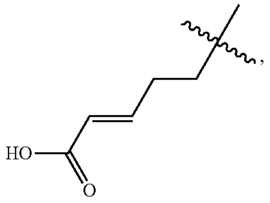 [SMILES: *CC/C=C/C(=O)O]
(A117)
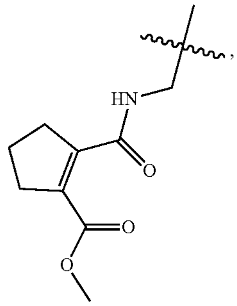 [SMILES: *CNC(=O)C1=C(C(=O)OC)CCC1]
(A118)
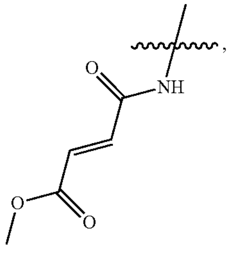 [SMILES: *NC(=O)/C=C/C(=O)OC]
(A119)
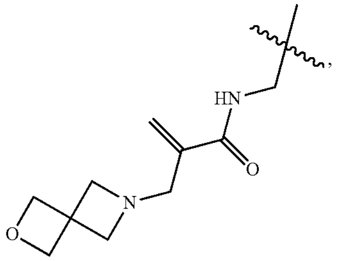 [SMILES: *CNC(=O)C(=C)CN1CC2(COC2)C1]
(A120)
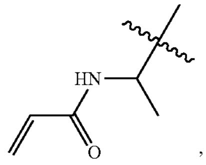 [SMILES: *C(C)NC(=O)C=C]
(A121)
, TABLE 1c-continued
| Exemplary Warhead Groups |
|---|
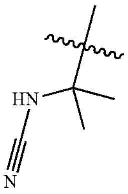
(A122)
,
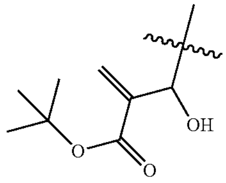
(A123)
,
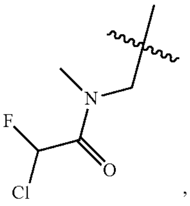
(A124)
,
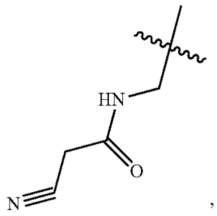 [SMILES: *CNC(=O)CC#N]
(A125)
,
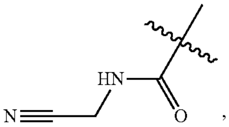 [SMILES: *C(=O)NCC#N]
(A126)
,
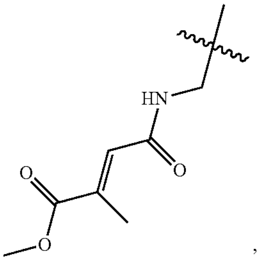 [SMILES: *CNC(=O)/C=C(\C)C(=O)OC]
(A127)
,
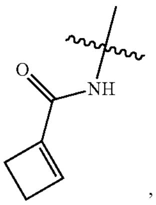 [SMILES: *NC(=O)C1=CCC1]
(A128)
,
TABLE 1c-continued
| Exemplary Warhead Groups |
|---|
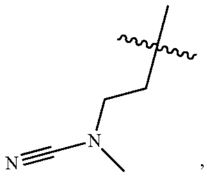 [SMILES: *CCN(C)C#N]
(A129)
,
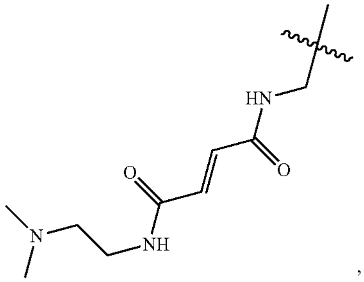 [SMILES: *CNC(=O)/C=C/C(=O)NCCN(C)C]
(A130)
,
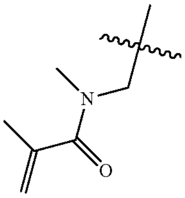
(A131)
,
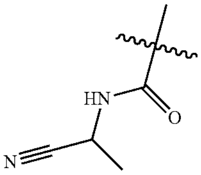
(A132)
,
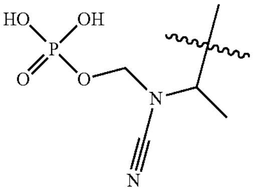
(A133)
,
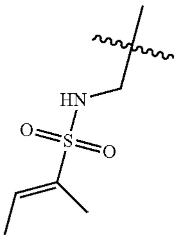
(A134)
,
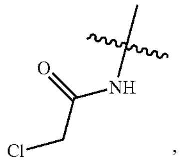 [SMILES: *NC(=O)CCl]
(A135)
, TABLE 1c-continued
Exemplary Warhead Groups
(A136)
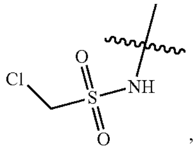 [SMILES: *NS(=O)(=O)CCl]
,
(A137)
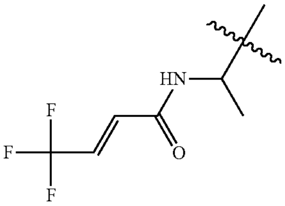
,
(A138)
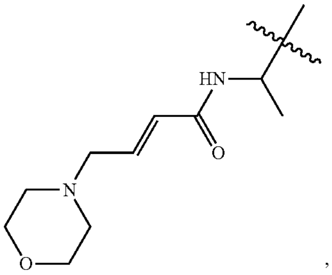 [SMILES: *C(C)NC(=O)/C=C/CN1CCOCC1]
,
(A139)
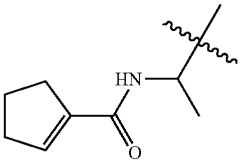
,
(A140)
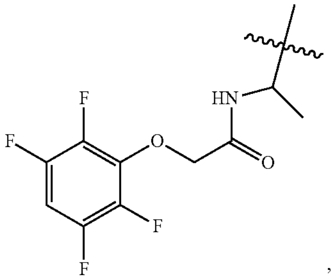 [SMILES: *C(C)NC(=O)COc1c(F)c(F)cc(F)c1F]
,
(A141)
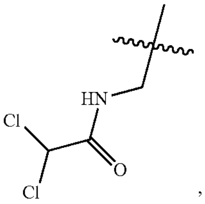 [SMILES: *CNC(=O)C(Cl)Cl]
,
(A142)
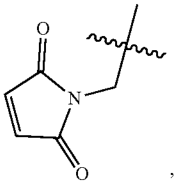 [SMILES: *CN1C(=O)C=CC1=O]
,
TABLE 1c-continued
Exemplary Warhead Groups
(A143)
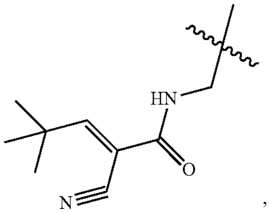 [SMILES: *CNC(=O)/C(C#N)=C/C(C)(C)C]
,
(A144)
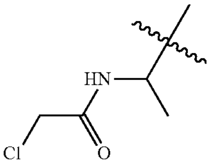
,
(A145)
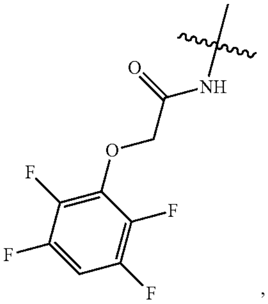 [SMILES: *NC(=O)COc1c(F)c(F)cc(F)c1F]
,
(A146)
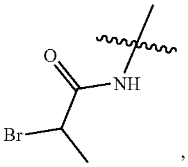 [SMILES: *NC(=O)C(C)Br]
,
(A147)
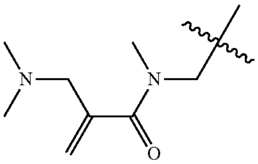
,
(A148)
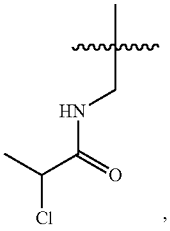 [SMILES: *CNC(=O)C(C)Cl]
,
(A149)
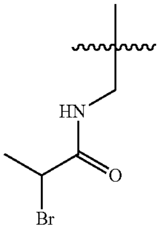
, TABLE 1c-continued
| Exemplary Warhead Groups |
| --- |
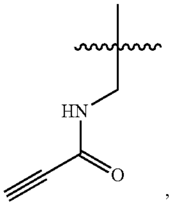 [SMILES: *CNC(=O)C#C]
(A150)
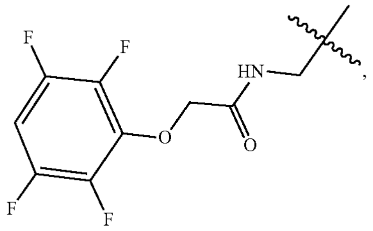 [SMILES: *CNC(=O)COc1c(F)c(F)cc(F)c1F]
(A151)
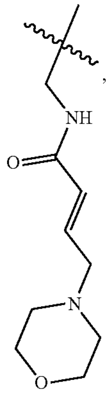 [SMILES: *CNC(=O)/C=C/CN1CCOCC1]
(A152)
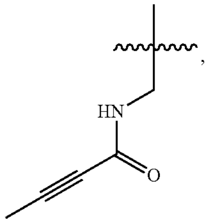 [SMILES: *CNC(=O)C#CC]
(A153)
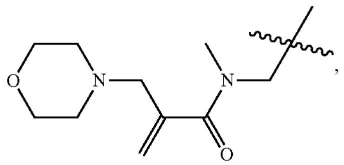 [SMILES: *CN(C)C(=O)C(=C)CN1CCOCC1]
(A154)
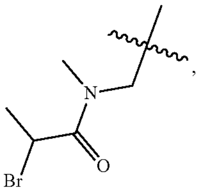 [SMILES: *CN(C)C(=O)C(C)Br]
(A155)
TABLE 1c-continued
| Exemplary Warhead Groups |
| --- |
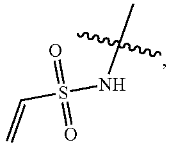 [SMILES: *NS(=O)(=O)C=C]
(A156)
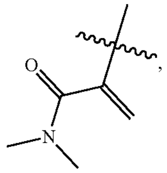 [SMILES: *C(=C)C(=O)N(C)C]
(A157)
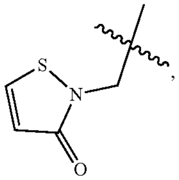 [SMILES: *Cn1sccc1=O]
(A158)
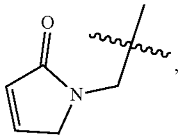 [SMILES: *CN1CC=CC1=O]
(A159)
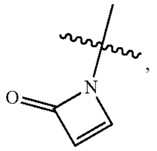 [SMILES: *N1C=CC1=O]
(A160)
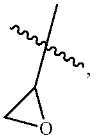 [SMILES: *C1CO1]
(A161)
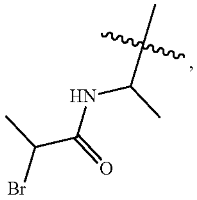 [SMILES: *C(C)NC(=O)C(C)Br]
(A162)
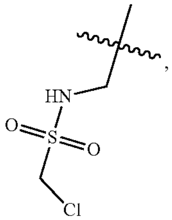 [SMILES: *CNS(=O)(=O)CCl]
(A163)

TABLE 1c-continued
| Exemplary Warhead Groups |
|---|
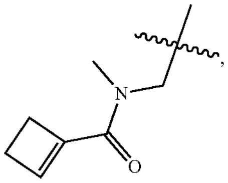 [SMILES: *CN(C)C(=O)C1=CCC1]
(A164)
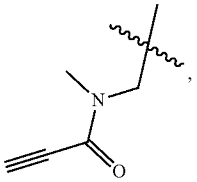 [SMILES: *CN(C)C(=O)C#C]
(A165)
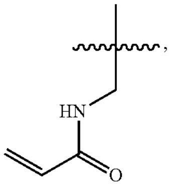 [SMILES: *CNC(=O)C=C]
(A166)
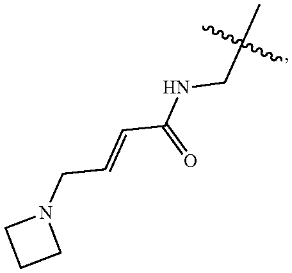 [SMILES: *CNC(=O)/C=C/CN1CCC1]
(A167)
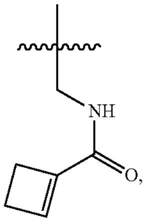 [SMILES: *CNC(=O)C1=CCC1]
(A168)
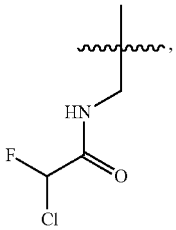
(A169)
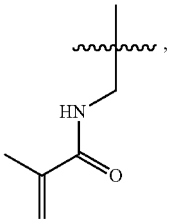 [SMILES: *CNC(=O)C(=C)C]
(A170)
TABLE 1c-continued
| Exemplary Warhead Groups |
|---|
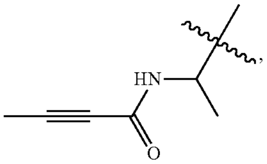 [SMILES: *C(C)NC(=O)C#CC]
(A171)
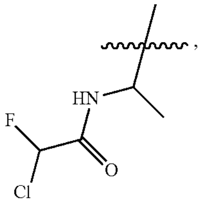 [SMILES: *C(C)NC(=O)C(F)Cl]
(A172)
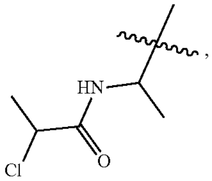 [SMILES: *C(C)NC(=O)C(C)Cl]
(A173)
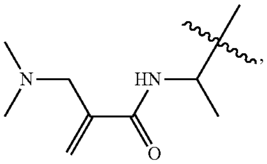 [SMILES: *C(C)NC(=O)C(=C)CN(C)C]
(A174)
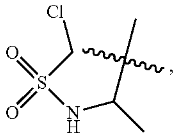 [SMILES: *C(C)NS(=O)(=O)CCl]
(A175)
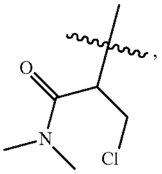 [SMILES: *C(CCl)C(=O)N(C)C]
(A176)
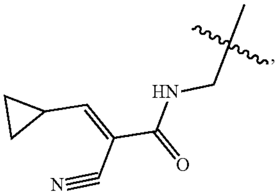 [SMILES: *CNC(=O)/C(C#N)=C/C1CC1]
(A177)
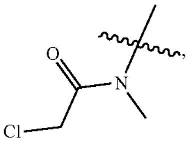 [SMILES: *N(C)C(=O)CCl]
(A178)

TABLE 1c-continued
| Exemplary Warhead Groups |
|---|
| 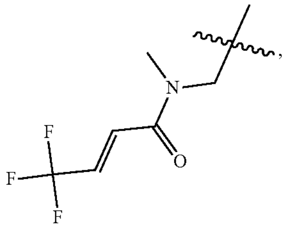 [SMILES: *CN(C)C(=O)/C=C/C(F)(F)F] (A179) |
| 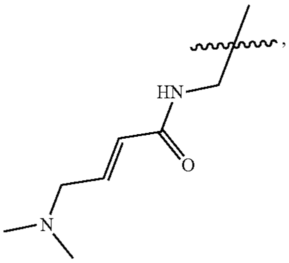 [SMILES: *CNC(=O)/C=C/CN(C)C] (A180) |
| 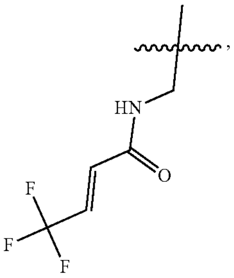 [SMILES: *CNC(=O)/C=C/C(F)(F)F] (A181) |
| 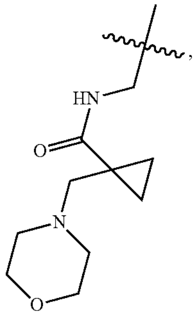 [SMILES: *CNC(=O)C1(CN2CCOCC2)CC1] (A182) |
| 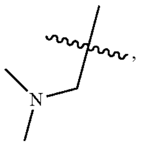 [SMILES: *CN(C)C] (A183) |
| 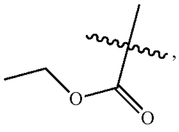 [SMILES: *C(=O)OCC] (A184) |
TABLE 1c-continued
| Exemplary Warhead Groups |
|---|
| 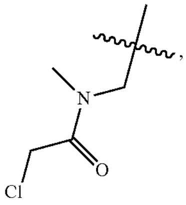 [SMILES: *CN(C)C(=O)CCl] (A185) |
| 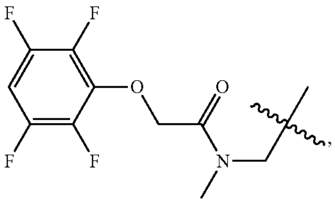 [SMILES: *CN(C)C(=O)COc1c(F)c(F)cc(F)c1F] (A186) |
| 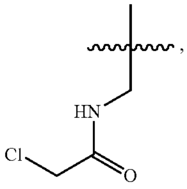 [SMILES: *CNC(=O)CCl] (A187) |
| 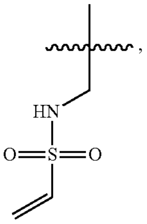 (A188) |
| 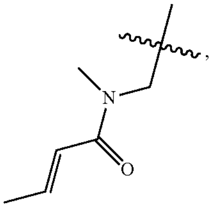 [SMILES: *CN(C)C(=O)/C=C/C] (A189) |
| 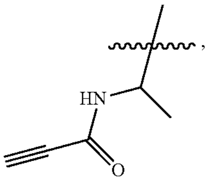 [SMILES: *C(C)NC(=O)C#C] (A190) |
| 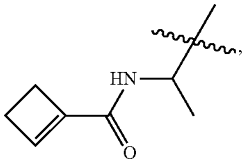 [SMILES: *C(C)NC(=O)C1=CCC1] (A191) |

TABLE 1c-continued

| Exemplary Warhead Groups | |
|---|---|
| 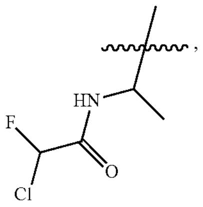 [SMILES: *C(C)NC(=O)C(F)Cl] | (A192) |
| 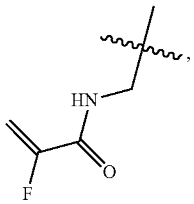 [SMILES: *CNC(=O)C(=C)F] | (A193) |
| 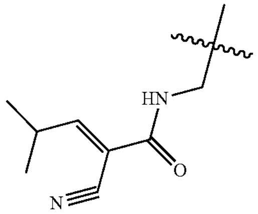 [SMILES: *CNC(=O)/C(C#N)=C/C(C)C] | (A194) |
| and | |
| 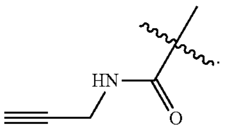 | (A195) |

In some embodiments, $R^5$ is selected from those set forth in Table 1c.

In some embodiments, a warhead group is selected from those set forth in Table 1d, below, wherein each wavy line indicates the point of attachment to the rest of the molecule. In some embodiments, $R^5$ is selected from those set forth in Table 1d.

TABLE 1d

| Exemplary Warhead Groups |
|---|
| 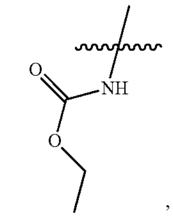 [SMILES: *NC(=O)OCC] , |
| 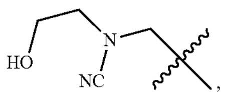 |

TABLE 1d-continued

| Exemplary Warhead Groups |
|---|
| 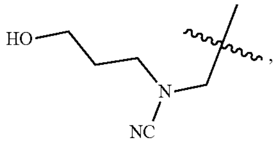 [SMILES: *CN(C#N)CCCO] |
| 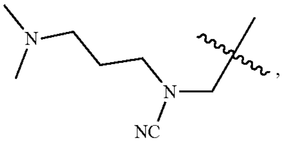 [SMILES: *CN(C#N)CCCN(C)C] |
| 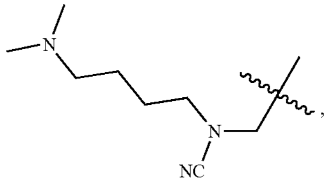 [SMILES: *CN(C#N)CCCCN(C)C] |
| 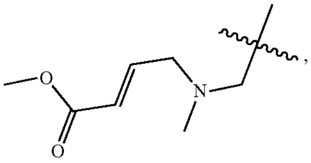 [SMILES: *CN(C)C/C=C/C(=O)OC] |
| 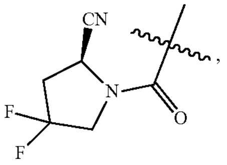 [SMILES: *C(=O)N1CC(F)(F)C[C@H]1C#N] |
| 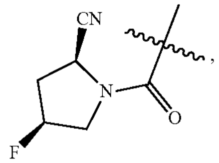 [SMILES: *C(=O)N1C[C@@H](F)C[C@H]1C#N] |
| and |
| 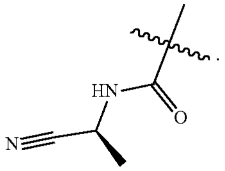 [SMILES: *C(=O)N[C@@H](C)C#N] |

In some embodiments, $R^5$ is selected from those set forth in Table 1d.

In some embodiments, a warhead group is selected from those set forth in Table 1e, below, wherein each wavy line indicates the point of attachment to the rest of the molecule. In some embodiments, $R^5$ is selected from those set forth in Table 1e.

TABLE le
| Exemplary Warhead Groups | |
|---|---|
| 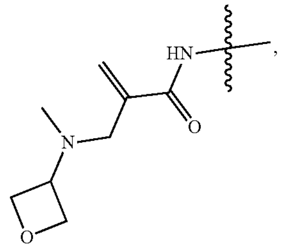 [SMILES: *NC(=O)C(=C)CN(C)C1COC1] | (B1) |
| 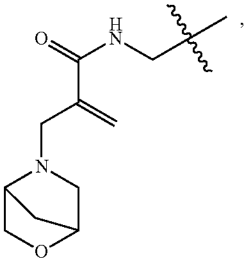 [SMILES: *CNC(=O)C(=C)CN1CC2CC1CO2] | (B2) |
| 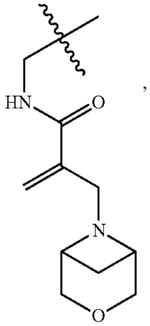 , | (B3) |
| 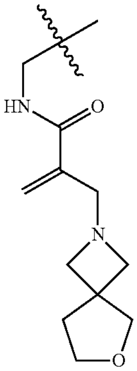 , | (B4) |
| 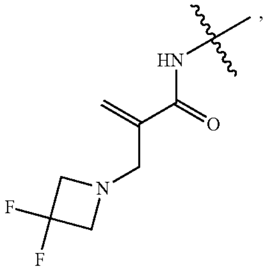 [SMILES: *NC(=O)C(=C)CN1CC(F)(F)C1] | (B5) |
TABLE le-continued
| Exemplary Warhead Groups | |
|---|---|
| 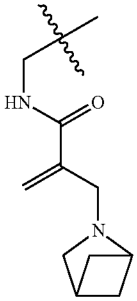 , | (B6) |
| 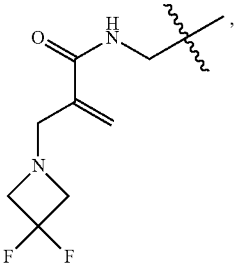 [SMILES: *CNC(=O)C(=C)CN1CC(F)(F)C1] | (B7) |
| 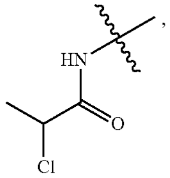 [SMILES: *NC(=O)C(C)Cl] | (B8) |
| 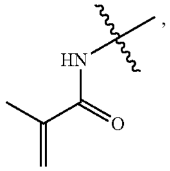 [SMILES: *NC(=O)C(=C)C] | (B9) |
| 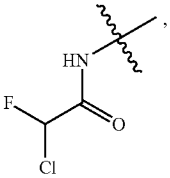 | (B10) |
| 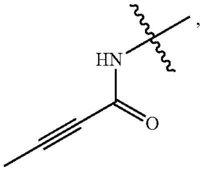 [SMILES: *NC(=O)C#CC] | (B11) |
| 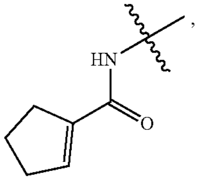 [SMILES: *NC(=O)C1=CCCC1] | (B12) |

TABLE 1e-continued
Exemplary Warhead Groups
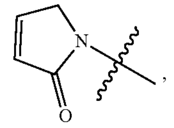 [SMILES: *N1CC=CC1=O]
(B13)
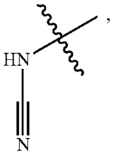
(B14)
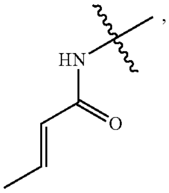 [SMILES: *NC(=O)/C=C/C]
(B15)
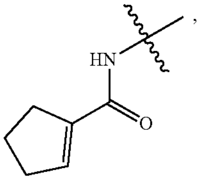 [SMILES: *NC(=O)C1=CCCC1]
(B16)
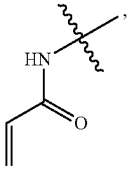 [SMILES: *NC(=O)C=C]
(B17)
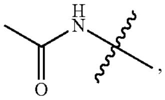 [SMILES: *NC(C)=O]
(B18)
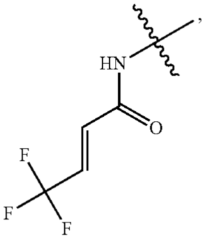 [SMILES: *NC(=O)/C=C/C(F)(F)F]
(B19)
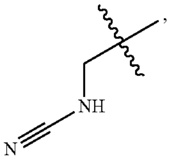 [SMILES: *CNC#N]
(B20)
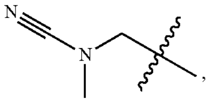
(B21)
TABLE 1e-continued
Exemplary Warhead Groups
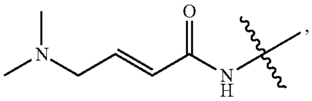 [SMILES: *NC(=O)/C=C/CN(C)C]
(B22)
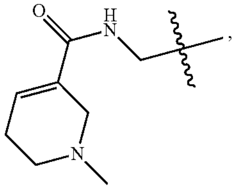 [SMILES: *CNC(=O)C1=CCCN(C)C1]
(B23)
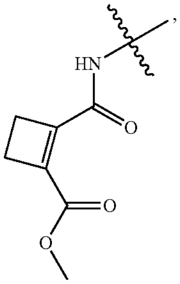 [SMILES: *NC(=O)C1=C(C(=O)OC)CC1]
(B24)
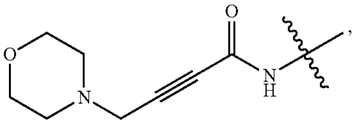 [SMILES: *NC(=O)C#CCN1CCOCC1]
(B25)
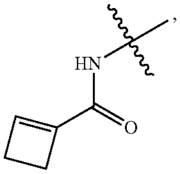 [SMILES: *NC(=O)C1=CCC1]
(B26)
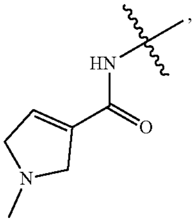 [SMILES: *NC(=O)C1=CCN(C)C1]
(B27)
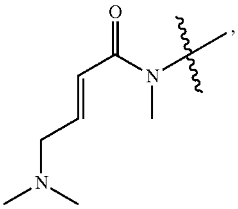 [SMILES: *N(C)C(=O)/C=C/CN(C)C]
(B28)

TABLE 1e-continued
| Exemplary Warhead Groups | |
|---|---|
| 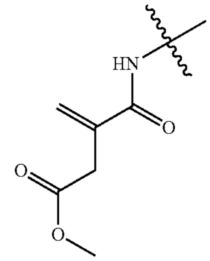 | (B29) |
| 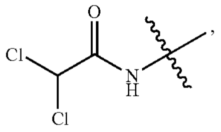 [SMILES: *NC(=O)C(Cl)Cl] | (B30) |
| 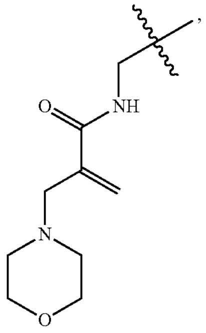 [SMILES: *CNC(=O)C(=C)CN1CCOCC1] | (B31) |
| 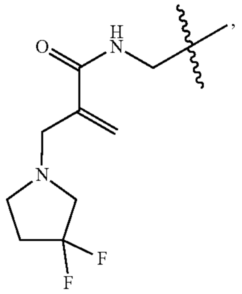 [SMILES: *CNC(=O)C(=C)CN1CCC(F)(F)C1] | (B32) |
| 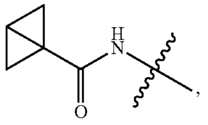 [SMILES: *NC(=O)C12CC1C2] | (B33) |
| 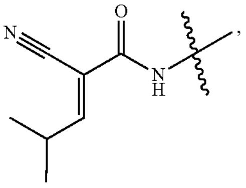 [SMILES: *NC(=O)/C(C#N)=C/C(C)C] | (B34) |
| 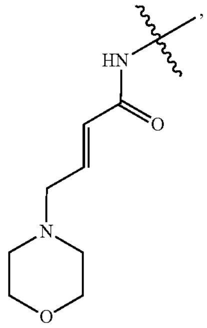 [SMILES: *NC(=O)/C=C/CN1CCOCC1] | (B35) |
| 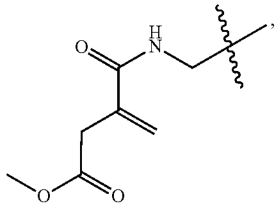 [SMILES: *CNC(=O)C(=C)CC(=O)OC] | (B36) |
| 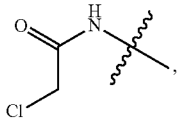 [SMILES: *NC(=O)CCl] | (B37) |
| 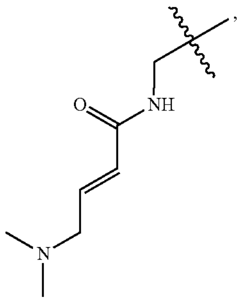 [SMILES: *CNC(=O)/C=C/CN(C)C] | (B38) |
| 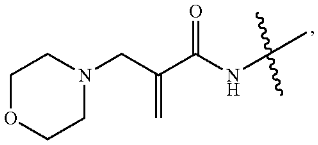 [SMILES: *NC(=O)C(=C)CN1CCOCC1] | (B39) |
| 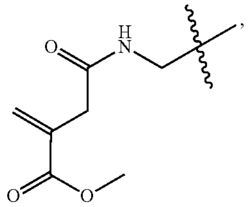 [SMILES: *CNC(=O)CC(=C)C(=O)OC] | (B40) |

TABLE le-continued
| Exemplary Warhead Groups |
| --- |
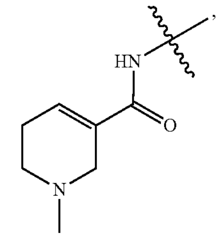 [SMILES: *NC(=O)C1=CCCN(C)C1]
(B41)
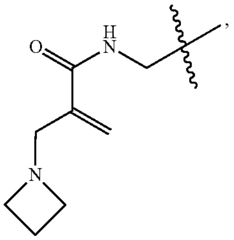 [SMILES: *CNC(=O)C(=C)CN1CCC1]
(B42)
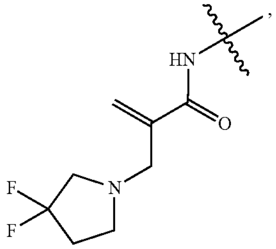 [SMILES: *NC(=O)C(=C)CN1CCC(F)(F)C1]
(B43)
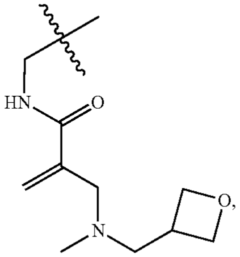 [SMILES: *CNC(=O)C(=C)CN(C)CC1COC1]
(B44)
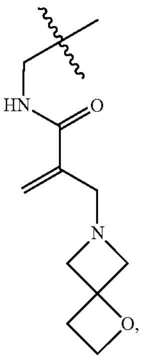 [SMILES: *CNC(=O)C(=C)CN1CC2(CCO2)C1]
(B45)
TABLE le-continued
| Exemplary Warhead Groups |
| --- |
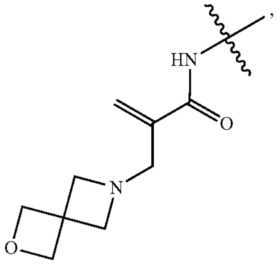 [SMILES: *NC(=O)C(=C)CN1CC2(COC2)C1]
(B46)
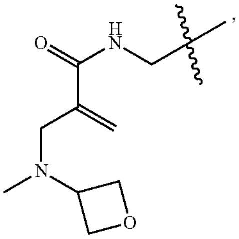 [SMILES: *CNC(=O)C(=C)CN(C)C1COC1]
(B47)
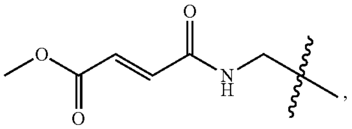 [SMILES: *CNC(=O)/C=C/C(=O)OC]
(B48)
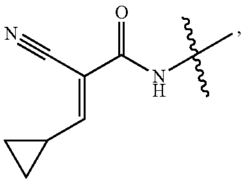 [SMILES: *NC(=O)/C(C#N)=C/C1CC1]
(B49)
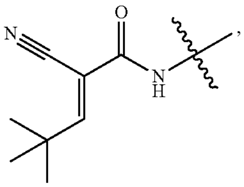 [SMILES: *NC(=O)/C(C#N)=C/C(C)(C)C]
(B50)
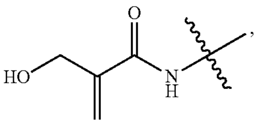 [SMILES: *NC(=O)C(=C)CO]
(B51)
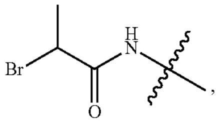
(B52)
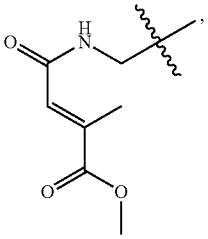 [SMILES: *CNC(=O)/C=C(\C)C(=O)OC]
(B53)

TABLE le-continued
| Exemplary Warhead Groups | |
|---|---|
| 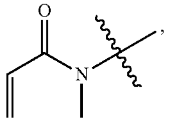 [SMILES: *N(C)C(=O)C=C] | (B54) |
| 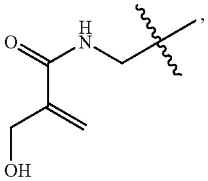 [SMILES: *CNC(=O)C(=C)CO] | (B55) |
| 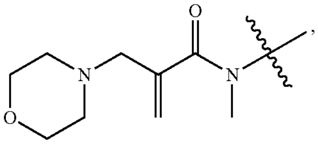 [SMILES: *N(C)C(=O)C(=C)CN1CCOCC1] | (B56) |
| 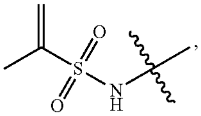 [SMILES: *NS(=O)(=O)C(=C)C] | (B57) |
| 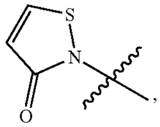 [SMILES: *n1sccc1=O] | (B58) |
| 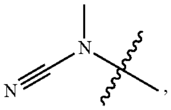 [SMILES: *N(C)C#N] | (B59) |
| 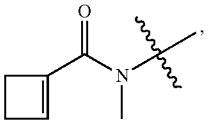 [SMILES: *N(C)C(=O)C1=CCC1] | (B60) |
| 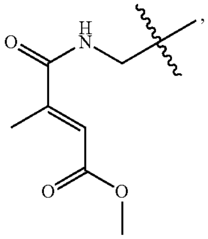 [SMILES: *CNC(=O)/C(C)=C/C(=O)OC] | (B61) |
| 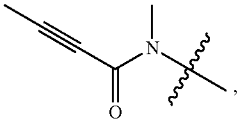 [SMILES: *N(C)C(=O)C#CC] | (B62) |
| 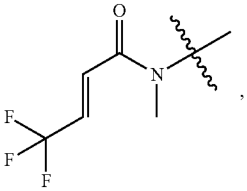 [SMILES: *N(C)C(=O)/C=C/C(F)(F)F] | (B63) |
TABLE le-continued
| Exemplary Warhead Groups | |
|---|---|
| 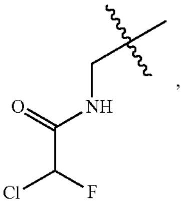 [SMILES: *CNC(=O)C(F)Cl] | (B64) |
| 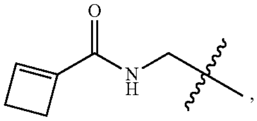 [SMILES: *CNC(=O)C1=CCC1] | (B65) |
| 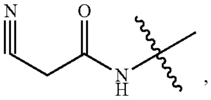 [SMILES: *NC(=O)CC#N] | (B66) |
| 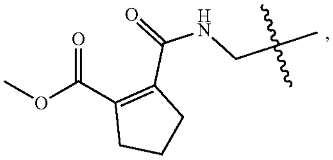 [SMILES: *CNC(=O)C1=C(C(=O)OC)CCC1] | (B67) |
| 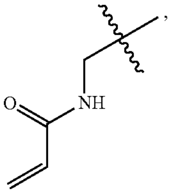 [SMILES: *CNC(=O)C=C] | (B68) |
| 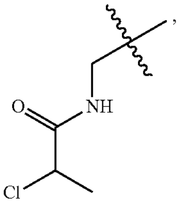 [SMILES: *CNC(=O)C(C)Cl] | (B69) |
| 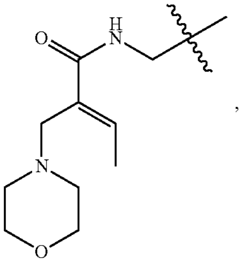 [SMILES: *CNC(=O)/C(=C/C)CN1CCOCC1] | (B70) |

TABLE le-continued
| Exemplary Warhead Groups |
|---|
| 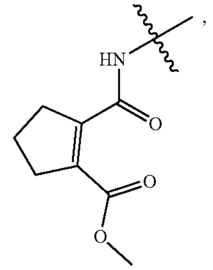 [SMILES: *NC(=O)C1=C(C(=O)OC)CCC1] (B71) |
| 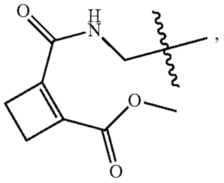 [SMILES: *CNC(=O)C1=C(C(=O)OC)CC1] (B72) |
| 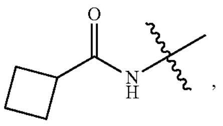 [SMILES: *NC(=O)C1CCC1] (B73) |
| 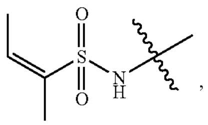 [SMILES: *NS(=O)(=O)/C(C)=C\C] (B74) |
| 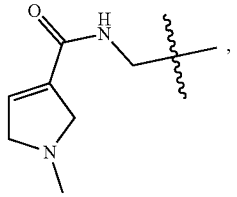 [SMILES: *CNC(=O)C1=CCN(C)C1] (B75) |
| 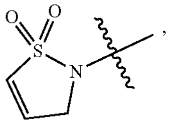 [SMILES: *N1CC=CS1(=O)=O] (B76) |
| 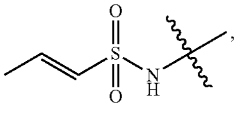 [SMILES: *NS(=O)(=O)/C=C/C] (B77) |
| 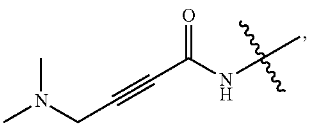 [SMILES: *NC(=O)C#CCN(C)C] (B78) |
TABLE le-continued
| Exemplary Warhead Groups |
|---|
| 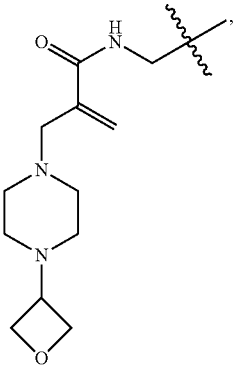 [SMILES: *CNC(=O)C(=C)CN1CCN(C2COC2)CC1] (B79) |
| 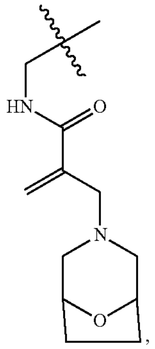 (B80) |
| 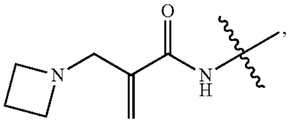 [SMILES: *NC(=O)C(=C)CN1CCC1] (B81) |
| 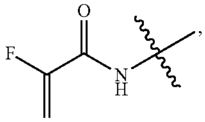 [SMILES: *NC(=O)C(=C)F] (B82) |
| 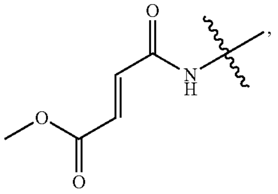 [SMILES: *NC(=O)/C=C/C(=O)OC] (B83) |
| 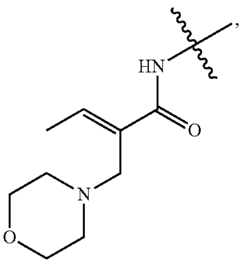 [SMILES: *NC(=O)/C(=C/C)CN1CCOCC1] (B84) |

TABLE le-continued

| Exemplary Warhead Groups | |
|---|---|
| 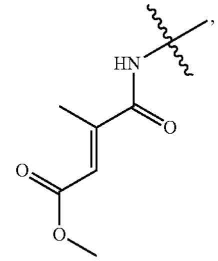 [SMILES: *NC(=O)/C(C)=C/C(=O)OC] | (B85) |
| 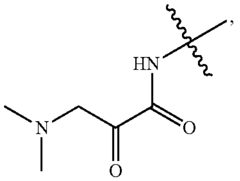 [SMILES: *NC(=O)C(=O)CN(C)C] | (B86) |
| 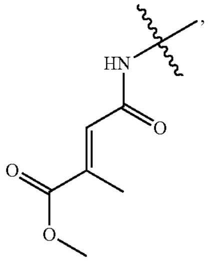 [SMILES: *NC(=O)/C=C(\C)C(=O)OC] | (B87) |
| 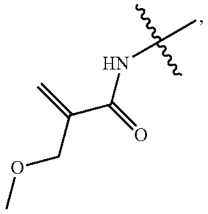 [SMILES: *NC(=O)C(=C)COC] | (B88) |
| 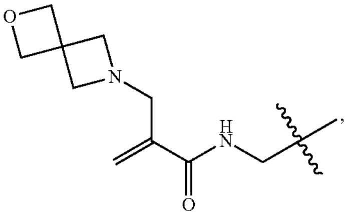 [SMILES: *CNC(=O)C(=C)CN1CC2(COC2)C1] | (B89) |
| 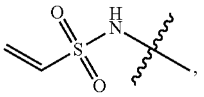 [SMILES: *NS(=O)(=O)C=C] | (B90) |
| 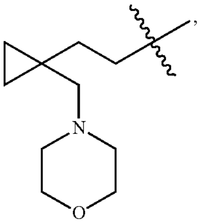 [SMILES: *CCC1(CN2CCOCC2)CC1] | (B91) |
| 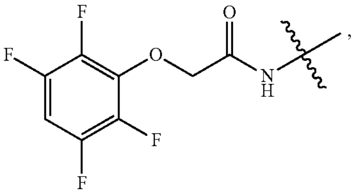 [SMILES: *NC(=O)COc1c(F)c(F)cc(F)c1F] | (B92) |
| 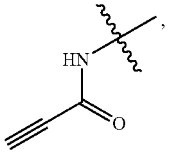 [SMILES: *NC(=O)C#C] | (B93) |
| and | |
| 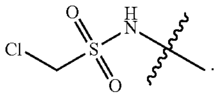 [SMILES: *NS(=O)(=O)CCl] | (B94) |

In some embodiments, $R^5$ is selected from those set forth in Table 1e.

In some embodiments, a warhead group is selected from those set forth in Table 1f, below, wherein each wavy line indicates the point of attachment to the rest of the molecule. In some embodiments, $R^5$ is selected from those set forth in Table 1f.

TABLE 1f

| Exemplary Warhead Groups | |
|---|---|
| 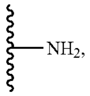 | 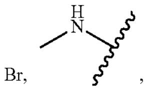 |
| 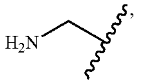 | 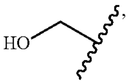 |
| 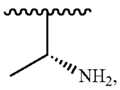 | 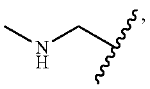 |
| 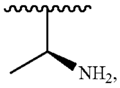 | 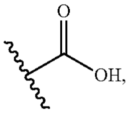 [SMILES: *C(=O)O] |
| 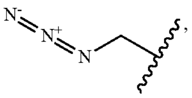 [SMILES: *CN=[N+]=[N-]] | 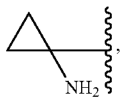 |
| 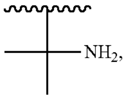 | 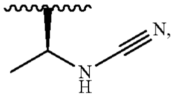 [SMILES: *[C@H](C)NC#N] |

TABLE 1f-continued
Exemplary Warhead Groups
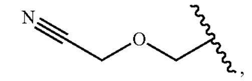 [SMILES: *COCC#N]
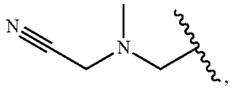
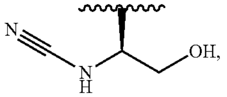 [SMILES: *[C@@H](CO)NC#N]
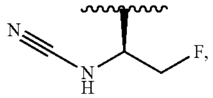 [SMILES: *[C@@H](CF)NC#N]
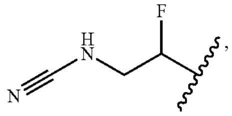
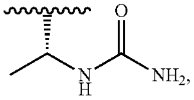 [SMILES: *[C@@H](C)NC(N)=O]
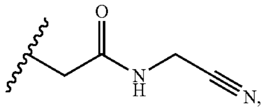 [SMILES: *CC(=O)NCC#N]
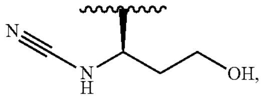 [SMILES: *[C@@H](CCO)NC#N]
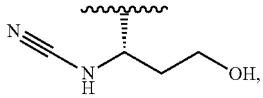 [SMILES: *[C@H](CCO)NC#N]
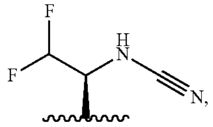 [SMILES: *[C@H](NC#N)C(F)F]
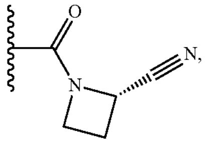 [SMILES: *C(=O)N1CC[C@H]1C#N]
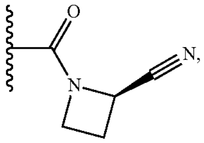 [SMILES: *C(=O)N1CC[C@@H]1C#N]
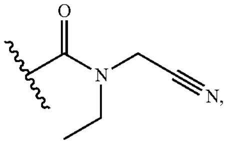 [SMILES: *C(=O)N(CC)CC#N]
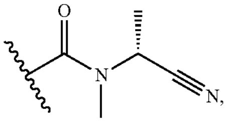 [SMILES: *C(=O)N(C)[C@H](C)C#N]
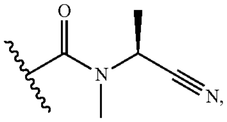 [SMILES: *C(=O)N(C)[C@@H](C)C#N]
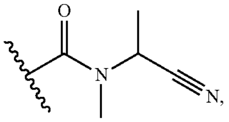 [SMILES: *C(=O)N(C)C(C)C#N]
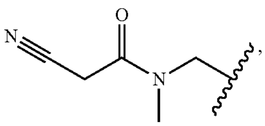 [SMILES: *CN(C)C(=O)CC#N]
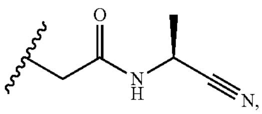 [SMILES: *CC(=O)N[C@@H](C)C#N]
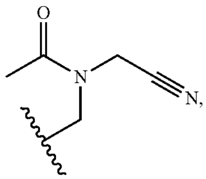 [SMILES: *CN(CC#N)C(C)=O]
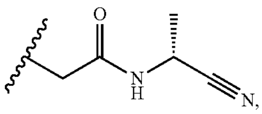 [SMILES: *CC(=O)N[C@H](C)C#N]
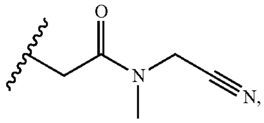 [SMILES: *CC(=O)N(C)CC#N]
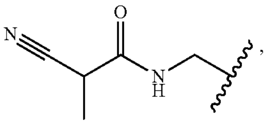 [SMILES: *CNC(=O)C(C)C#N]
TABLE 1f-continued
Exemplary Warhead Groups
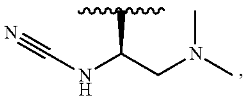 [SMILES: *[C@@H](CN(C)C)NC#N]
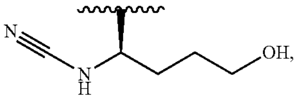 [SMILES: *[C@@H](CCCO)NC#N]
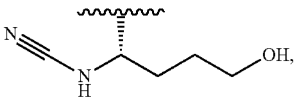 [SMILES: *[C@H](CCCO)NC#N]
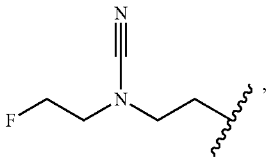 [SMILES: *CCN(C#N)CCF]
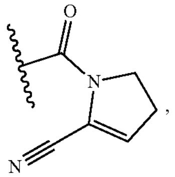 [SMILES: *C(=O)N1CCC=C1C#N]
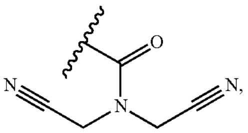 [SMILES: *C(=O)N(CC#N)CC#N]
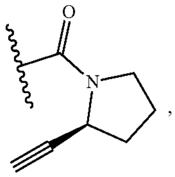 [SMILES: *C(=O)N1CCC[C@H]1C#C]
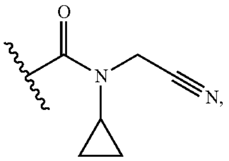 [SMILES: *C(=O)N(CC#N)C1CC1]
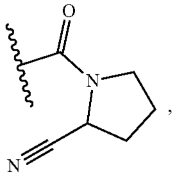 [SMILES: *C(=O)N1CCCC1C#N]
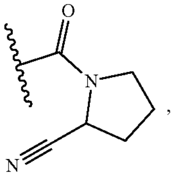 [SMILES: *C(=O)N1CCCC1C#N]
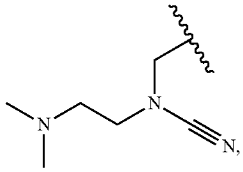 [SMILES: *CN(C#N)CCN(C)C]
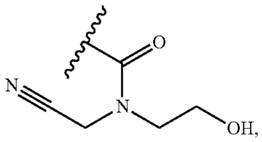 [SMILES: *C(=O)N(CC#N)CCO]
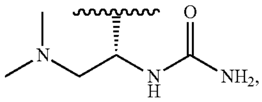 [SMILES: *[C@@H](CN(C)C)NC(N)=O]
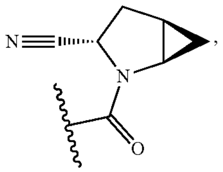 [SMILES: *C(=O)N1[C@H](C#N)C[C@H]2C[C@H]21]

TABLE 1f-continued
| Exemplary Warhead Groups | |
|---|---|
| 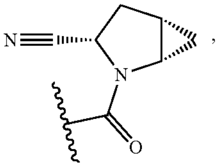 [SMILES: *C(=O)N1[C@H](C#N)C[C@@H]2C[C@@H]21] | 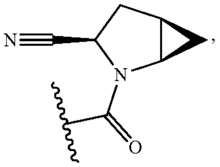 [SMILES: *C(=O)N1[C@@H]2C[C@@H]2C[C@@H]1C#N] |
| 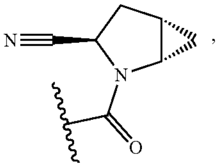 [SMILES: *C(=O)N1[C@@H](C#N)C[C@@H]2C[C@@H]21] | 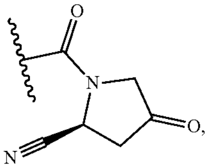 [SMILES: *C(=O)N1CC(=O)C[C@H]1C#N] |
| 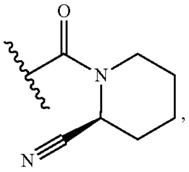 [SMILES: *C(=O)N1CCCC[C@H]1C#N] | 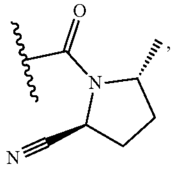 [SMILES: *C(=O)N1[C@H](C)CC[C@H]1C#N] |
| 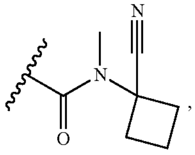 [SMILES: *C(=O)N(C)C1(C#N)CCC1] | 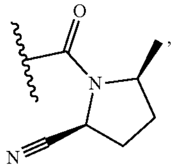 [SMILES: *C(=O)N1[C@H](C#N)CC[C@@H]1C] |
| 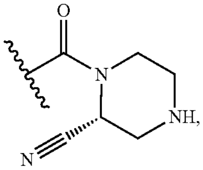 [SMILES: *C(=O)N1CCNC[C@@H]1C#N] | 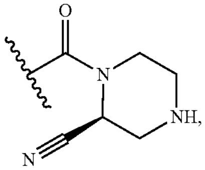 [SMILES: *C(=O)N1CCNC[C@H]1C#N] |
| 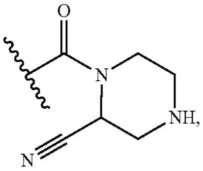 [SMILES: *C(=O)N1CCNCC1C#N] | 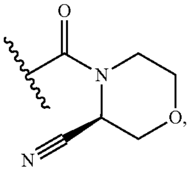 [SMILES: *C(=O)N1CCOC[C@H]1C#N] |
| 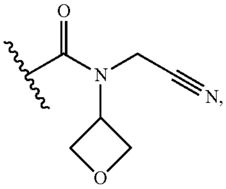 [SMILES: *C(=O)N(CC#N)C1COC1] | 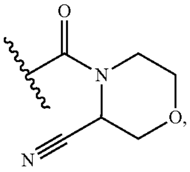 [SMILES: *C(=O)N1CCOCC1C#N] |
| 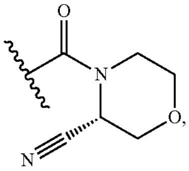 [SMILES: *C(=O)N1CCOC[C@@H]1C#N] | 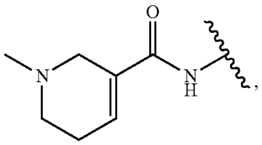 [SMILES: *NC(=O)C1=CCCN(C)C1] |
TABLE 1f-continued
| Exemplary Warhead Groups | |
|---|---|
| 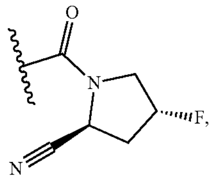 [SMILES: *C(=O)N1C[C@H](F)C[C@H]1C#N] | 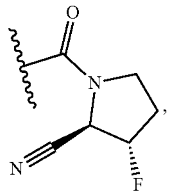 [SMILES: *C(=O)N1CC[C@H](F)[C@H]1C#N] |
| 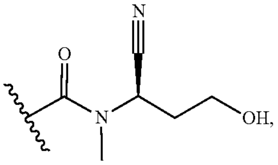 [SMILES: *C(=O)N(C)[C@@H](C#N)CCO] | |
| 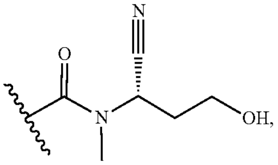 [SMILES: *C(=O)N(C)[C@H](C#N)CCO] | |
| 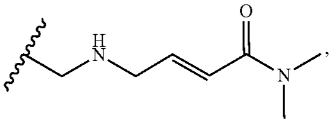 [SMILES: *CNC/C=C/C(=O)N(C)C] | |
| 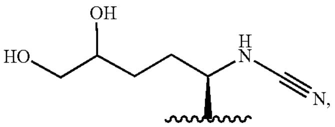 [SMILES: *[C@@H](CCC(O)CO)NC#N] | |
| 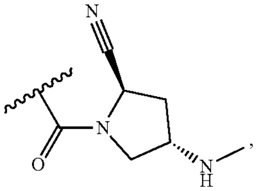 [SMILES: *C(=O)N1C[C@@H](NC)C[C@@H]1C#N] | 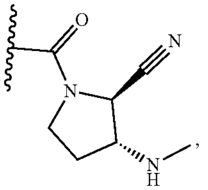 [SMILES: *C(=O)N1CC[C@@H](NC)[C@@H]1C#N] |
| 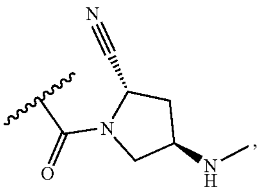 [SMILES: *C(=O)N1C[C@H](NC)C[C@H]1C#N] | 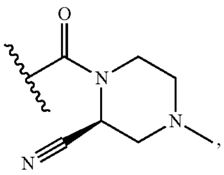 [SMILES: *C(=O)N1CCN(C)C[C@H]1C#N] |
| 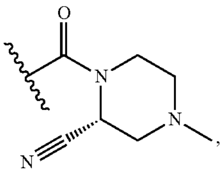 [SMILES: *C(=O)N1CCN(C)C[C@@H]1C#N] | 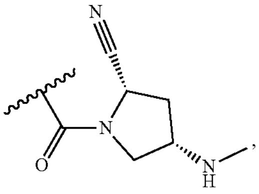 [SMILES: *C(=O)N1C[C@@H](NC)C[C@H]1C#N] |

TABLE 1f-continued
Exemplary Warhead Groups
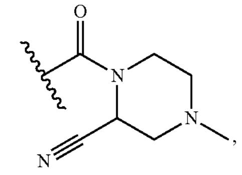 [SMILES: *C(=O)N1CCN(C)CC1C#N]
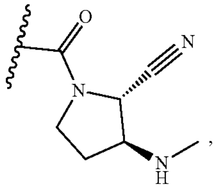 [SMILES: *C(=O)N1CC[C@H](NC)[C@H]1C#N]
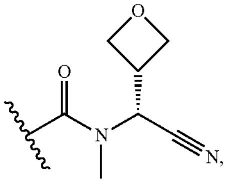 [SMILES: *C(=O)N(C)[C@@H](C#N)C1COC1]
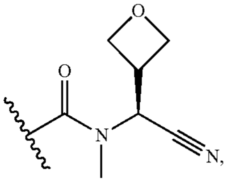 [SMILES: *C(=O)N(C)[C@H](C#N)C1COC1]
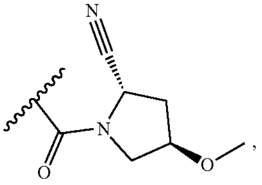 [SMILES: *C(=O)N1C[C@H](OC)C[C@H]1C#N]
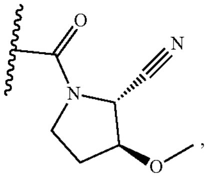 [SMILES: *C(=O)N1CC[C@H](OC)[C@H]1C#N]
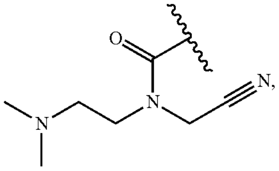 [SMILES: *C(=O)N(CC#N)CCN(C)C]
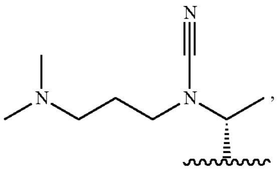 [SMILES: *[C@@H](C)N(C#N)CCCN(C)C]
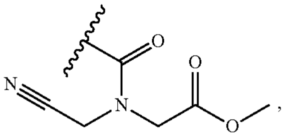 [SMILES: *C(=O)N(CC#N)CC(=O)OC]
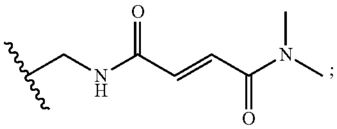 [SMILES: *CNC(=O)/C=C/C(=O)N(C)C]
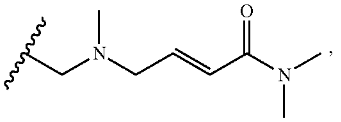 [SMILES: *CN(C)C/C=C/C(=O)N(C)C]
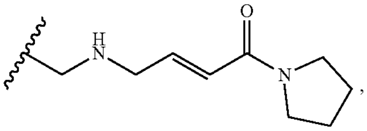 [SMILES: *CNC/C=C/C(=O)N1CCCC1]
TABLE 1f-continued
Exemplary Warhead Groups
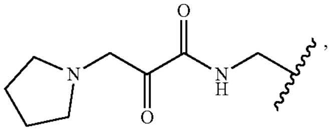 [SMILES: *CNC(=O)C(=O)CN1CCCC1]
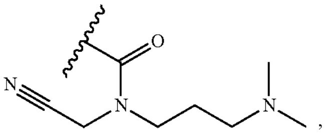 [SMILES: *C(=O)N(CC#N)CCCN(C)C]
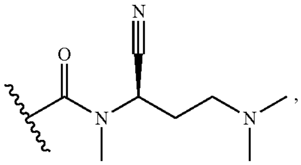 [SMILES: *C(=O)N(C)[C@@H](C#N)CCN(C)C]
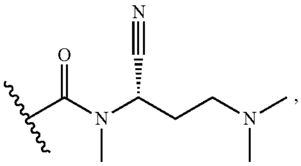 [SMILES: *C(=O)N(C)[C@H](C#N)CCN(C)C]
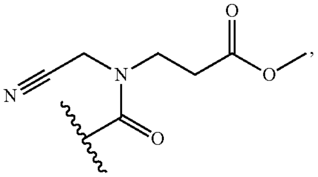 [SMILES: *C(=O)N(CC#N)CCC(=O)OC]
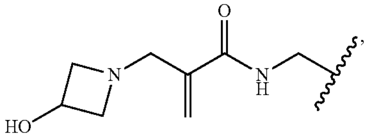 [SMILES: *CNC(=O)C(=C)CN1CC(O)C1]
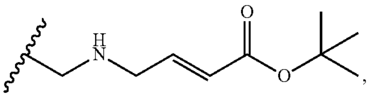 [SMILES: *CNC/C=C/C(=O)OC(C)(C)C]
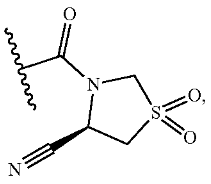 [SMILES: *C(=O)N1CS(=O)(=O)C[C@H]1C#N]
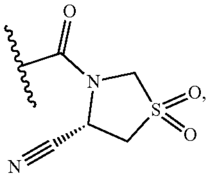 [SMILES: *C(=O)N1CS(=O)(=O)C[C@@H]1C#N]

TABLE 1f-continued
Exemplary Warhead Groups
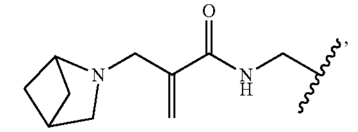 [SMILES: *CNC(=O)C(=C)CN1CC2CC1C2]
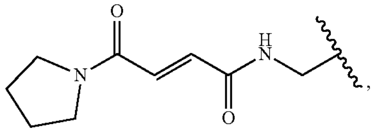 [SMILES: *CNC(=O)/C=C/C(=O)N1CCCC1]
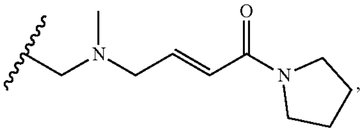 [SMILES: *CN(C)C/C=C/C(=O)N1CCCC1]
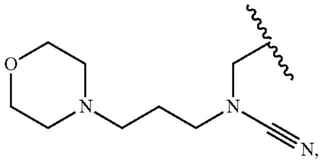 [SMILES: *CN(C#N)CCCN1CCOCC1]
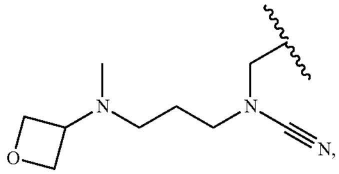 [SMILES: *CN(C#N)CCCN(C)C1COC1]
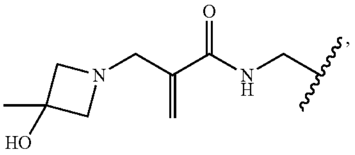 [SMILES: *CNC(=O)C(=C)CN1CC(C)(O)C1]
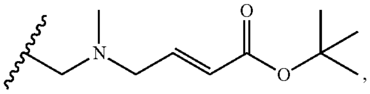 [SMILES: *CN(C)C/C=C/C(=O)OC(C)(C)C]
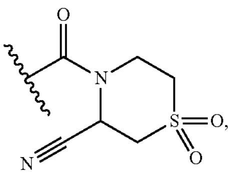 [SMILES: *C(=O)N1CCS(=O)(=O)CC1C#N]
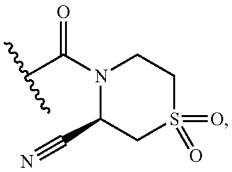 [SMILES: *C(=O)N1CCS(=O)(=O)C[C@H]1C#N]
TABLE 1f-continued
Exemplary Warhead Groups
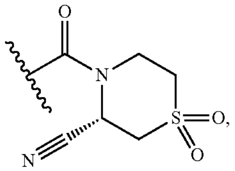 [SMILES: *C(=O)N1CCS(=O)(=O)C[C@@H]1C#N]
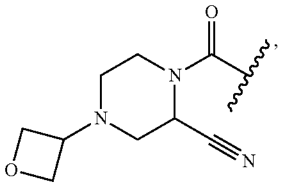 [SMILES: *C(=O)N1CCN(C2COC2)CC1C#N]
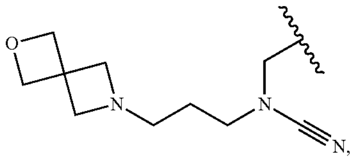 [SMILES: *CN(C#N)CCCN1CC2(COC2)C1]
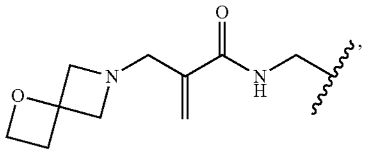 [SMILES: *CNC(=O)C(=C)CN1CC2(CCO2)C1]
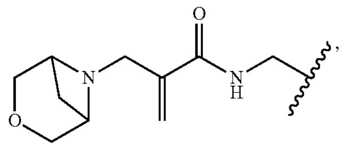 [SMILES: *CNC(=O)C(=C)CN1C2COCC1C2]
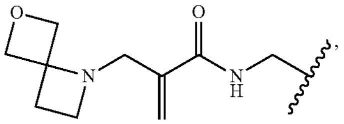 [SMILES: *CNC(=O)C(=C)CN1CCC12COC2]
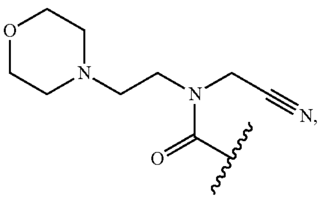 [SMILES: *C(=O)N(CC#N)CCN1CCOCC1]
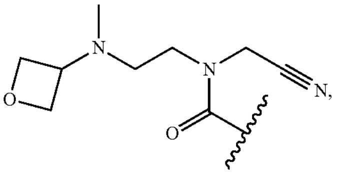 [SMILES: *C(=O)N(CC#N)CCN(C)C1COC1]
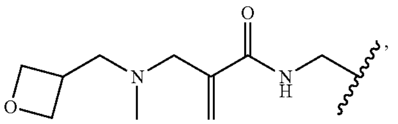 [SMILES: *CNC(=O)C(=C)CN(C)CC1COC1]

TABLE 1f-continued
Exemplary Warhead Groups
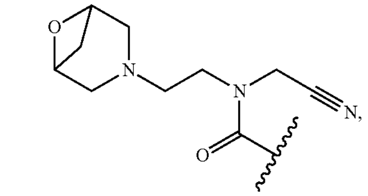 [SMILES: *C(=O)N(CC#N)CCN1CC2CC(C1)O2]
,
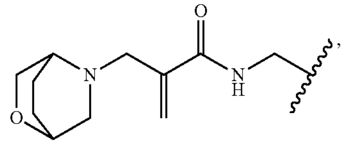 [SMILES: *CNC(=O)C(=C)CN1CC2CCC1CO2]
,
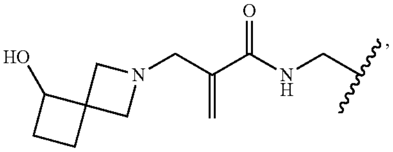 [SMILES: *CNC(=O)C(=C)CN1CC2(CCC2O)C1]
,
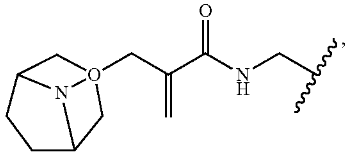
,
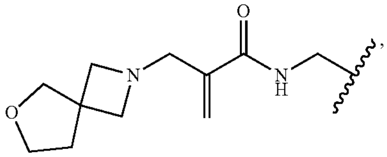 [SMILES: *CNC(=O)C(=C)CN1CC2(CCOC2)C1]
,
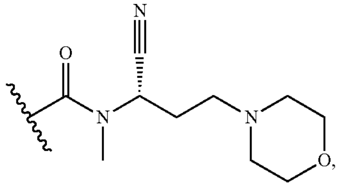 [SMILES: *C(=O)N(C)[C@H](C#N)CCN1CCOCC1]
,
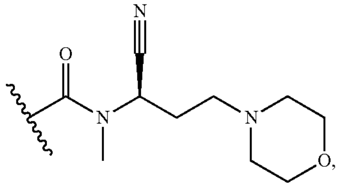 [SMILES: *C(=O)N(C)[C@@H](C#N)CCN1CCOCC1]
,
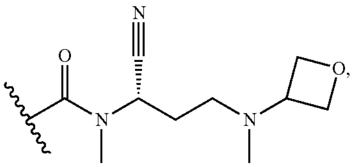 [SMILES: *C(=O)N(C)[C@H](C#N)CCN(C)C1COC1]
,
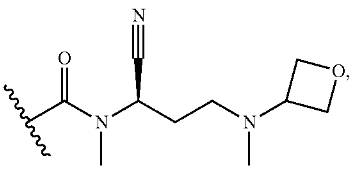 [SMILES: *C(=O)N(C)[C@@H](C#N)CCN(C)C1COC1]
TABLE 1f-continued
Exemplary Warhead Groups
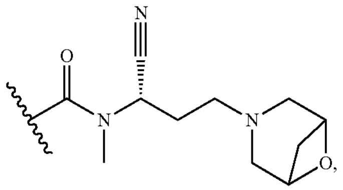 [SMILES: *C(=O)N(C)[C@H](C#N)CCN1CC2CC(C1)O2]
,
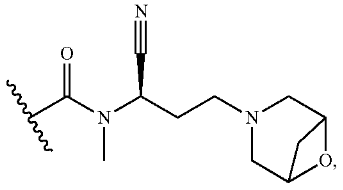 [SMILES: *C(=O)N(C)[C@@H](C#N)CCN1CC2CC(C1)O2]
,
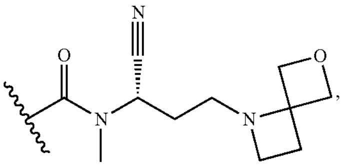 [SMILES: *C(=O)N(C)[C@H](C#N)CCN1CCC12COC2]
,
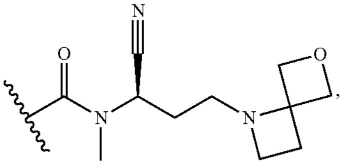 [SMILES: *C(=O)N(C)[C@@H](C#N)CCN1CCC12COC2]
,
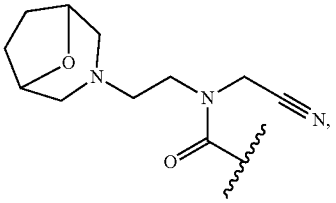 [SMILES: *C(=O)N(CC#N)CCN1CC2CCC(C1)O2]
,
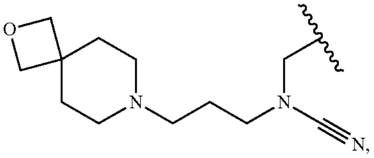 [SMILES: *CN(C#N)CCCN1CCC2(CC1)COC2]
,
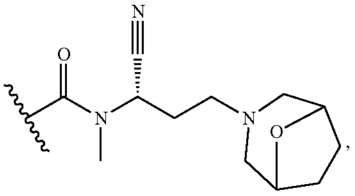 [SMILES: *C(=O)N(C)[C@H](C#N)CCN1CC2CCC(C1)O2]
,
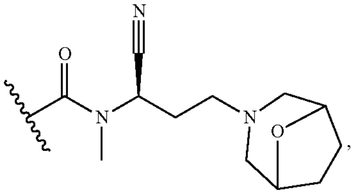 [SMILES: *C(=O)N(C)[C@@H](C#N)CCN1CC2CCC(C1)O2]
, TABLE 1f-continued

| Exemplary Warhead Groups |
| --- |
| 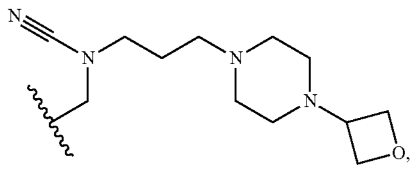 [SMILES: *CN(C#N)CCCN1CCN(C2COC2)CC1] |
| 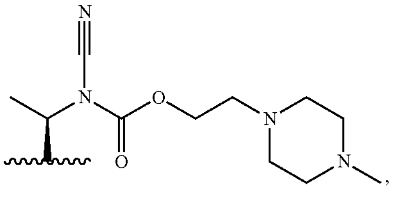 [SMILES: *[C@@H](C)N(C#N)C(=O)OCCN1CCN(C)CC1] |
| 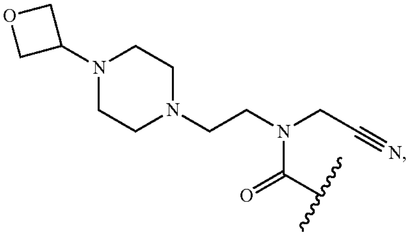 [SMILES: *C(=O)N(CC#N)CCN1CCN(C2COC2)CC1] |
| 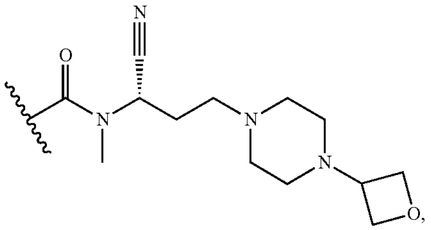 [SMILES: *C(=O)N(C)[C@H](C#N)CCN1CCN(C2COC2)CC1] |
| 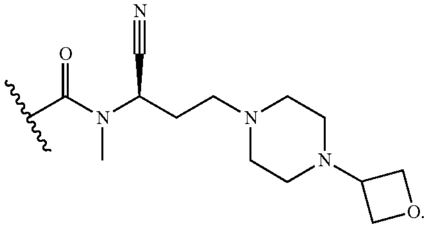 [SMILES: *C(=O)N(C)[C@@H](C#N)CCN1CCN(C2COC2)CC1] |

In some embodiments, $R^5$ is selected from those set forth in Table 1f. In some embodiments the warhead includes a nitrile group. In some embodiments the warhead does not include a vinyl group.

In some embodiments, $R^5$ is selected from those depicted in Table 1, below.

As defined generally above, $R^6$ is hydrogen or an optionally substituted $C_{1-6}$ aliphatic group.

In some embodiments, $R^6$ is hydrogen. In some embodiments, $R^6$ is an optionally substituted $C_{1-6}$ aliphatic group. In some embodiments, $R^6$ is an optionally substituted $C_{1-6}$ aliphatic group.

In some embodiments, $R^6$ is selected from hydrogen,

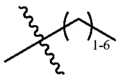
,
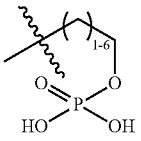
and
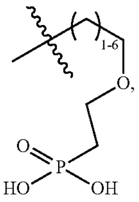

or a pharmaceutically acceptable salt thereof.

In some embodiments, $R^6$ is selected from hydrogen and

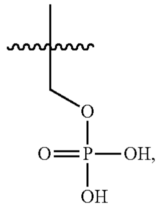 [SMILES: *COP(=O)(O)O]

or a pharmaceutically acceptable salt thereof.

In some embodiments, $R^6$ is selected from those depicted in Table 1, below.

As defined generally above, each occurrence of $R^7$ is independently optionally substituted $C_{1-6}$ aliphatic, halogen, —CN, —NC, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, —NRS(O)$_2$R, phenyl, or a 5-6 membered heteroaromatic ring having 1-3 heteroatoms selected from nitrogen, sulfur, and oxygen.

As defined generally above, each occurrence of $R^7$ is independently optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, —NRS(O)$_2$R, optionally substituted phenyl, or an optionally substituted 5-6 membered heteroaromatic ring having 1-3 heteroatoms selected from nitrogen, sulfur, and oxygen.

In some embodiments, $R^7$ is $C_{1-6}$ aliphatic group. In some embodiments, $R^7$ is substituted $C_{1-6}$ aliphatic group. In some embodiments, $R^7$ is halogen. In some embodiments, $R^7$ is —CN. In some embodiments, $R^7$ is —NC. In some embodiments, $R^7$ is —C(O)R. In some embodiments, $R^7$ is —C(O)OR. In some embodiments, $R^7$ is —OC(O)R. In some embodiments, $R^7$ is —C(O)N(R)$_2$. In some embodiments, $R^7$ is —N(R)C(O)R. In some embodiments, $R^7$ is —N(R)C(O)N(R)$_2$. In some embodiments, $R^7$ is —OC(O)N(R)$_2$. In some embodiments, $R^7$ is —N(R)C(O)OR. In some embodiments, $R^7$ is —OR. In some embodiments, $R^7$ is —N(R)$_2$. In some embodiments, $R^7$ is —$NO_2$. In some embodiments, $R^7$ is —SR. In some embodiments, $R^7$ is —S(O)R. In some embodiments, $R^7$ is —S(O)$_2$R. In some embodiments, $R^7$ is —S(O)$_2$N(R)$_2$. In some embodiments, $R^7$ is —NRS(O)$_2$R. In some embodiments, $R^7$ is phenyl. In some embodiments, $R^7$ is a 5-6 membered heteroaromatic ring having 1-3 heteroatoms selected from nitrogen, sulfur, and oxygen.

In some embodiments, $R^7$ is $C_{1-6}$ aliphatic group. In some embodiments, $R^7$ is substituted $C_{1-6}$ aliphatic group. In some embodiments, $R^7$ is halogen. In some embodiments, $R^7$ is —CN. In some embodiments, $R^7$ is —C(O)R. In some embodiments, $R^7$ is —C(O)OR. In some embodiments, $R^7$ is —OC(O)R. In some embodiments, $R^7$ is —C(O)N(R)$_2$. In some embodiments, $R^7$ is —N(R)C(O)R. In some embodiments, $R^7$ is —N(R)C(O)N(R)$_2$. In some embodiments, $R^7$ is —OC(O)N(R)$_2$. In some embodiments, $R^7$ is —N(R)C(O)OR. In some embodiments, $R^7$ is —OR. In some embodiments, $R^7$ is —N(R)$_2$. In some embodiments, $R^7$ is —$NO_2$. In some embodiments, $R^7$ is —SR. In some embodiments, $R^7$ is —S(O)R. In some embodiments, $R^7$ is —S(O)$_2$R. In some embodiments, $R^7$ is —S(O)$_2$N(R)$_2$. In some embodiments, $R^7$ is —NRS(O)$_2$R. In some embodiments, $R^7$ is phenyl. In some embodiments, $R^7$ is a 5-6 membered heteroaromatic ring having 1-3 heteroatoms selected from nitrogen, sulfur, and oxygen. In some embodiments, $R^7$ is substituted phenyl. In some embodiments, $R^7$ is a substituted 5-6 membered heteroaromatic ring having 1-3 heteroatoms selected from nitrogen, sulfur, and oxygen.

In some embodiments, $R^7$ is halogen. In some embodiments, $R^7$ is selected from F, Cl or Br. In some embodiments, $R^7$ is F.

In some embodiments, $R^7$ is selected from those depicted in Table 1, below.

As defined generally above, $R^8$ is selected from phenyl, 3-8 membered saturated or partially unsaturated monocyclic carbocyclic ring, a 4-10 membered saturated or partially unsaturated bicyclic carbocyclic ring, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, an 8-10 membered bicyclic heteroaromatic ring having 1-5 heteroatoms independently selected from nitrogen, oxygen, and sulfur, and a $C_{1-6}$ aliphatic; wherein $R^8$ is optionally substituted with m instances of $R^1$.

In some embodiments, $R^8$ is phenyl. In some embodiments, $R^8$ is a 3-8 membered saturated monocyclic carbocyclic ring. In some embodiments, $R^8$ is a 3-8 membered partially unsaturated monocyclic carbocyclic ring. In some embodiments, $R^8$ is a 4-10 membered saturated or partially unsaturated bicyclic carbocyclic ring. In some embodiments, $R^8$ is an 8-10 membered bicyclic aromatic carbocyclic ring. In some embodiments, $R^8$ is a 3-8 membered saturated or partially unsaturated monocyclic heterocyclic ring having 1-2 heteroatoms independently selected from nitrogen, oxygen, and sulfur. In some embodiments, $R^8$ is a 5-10 membered bicyclic heterocyclic ring having 1-4 heteroatoms independently selected from nitrogen, oxygen, and sulfur. In some embodiments, $R^8$ is a 5-6 membered monocyclic heteroaromatic ring having 1-4 heteroatoms independently selected from nitrogen, oxygen, and sulfur. In some embodiments, $R^8$ is an 8-10 membered bicyclic heteroaromatic ring having 1-5 heteroatoms independently selected from nitrogen, oxygen, and sulfur. In some embodiments, $R^8$ is a $C_{1-6}$ aliphatic.

In some embodiments, $R^8$ is phenyl.

In some embodiments, $R^8$ is selected from phenyl,

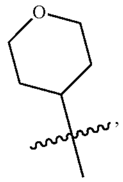,
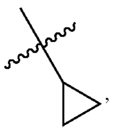,
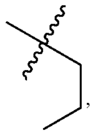,

-continued

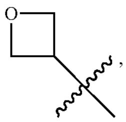,
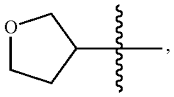, and t-Bu.

In some embodiments, $R^8$ taken together with m instances of $R^1$ is

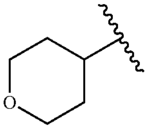,
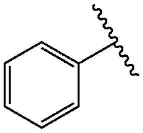,

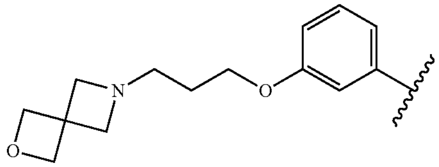,

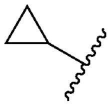,
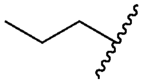,

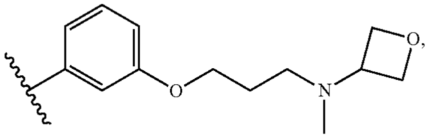

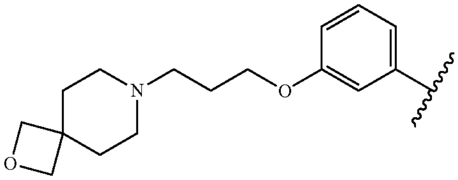,

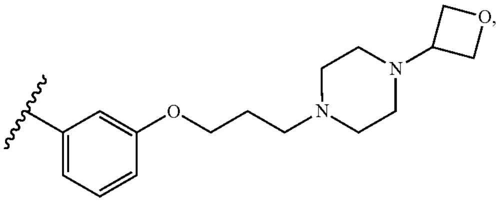

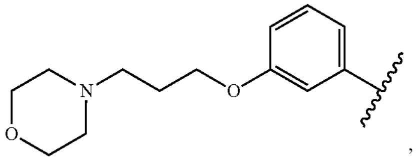,

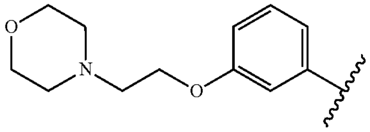,

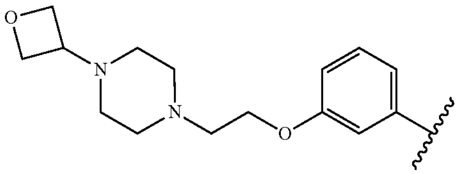,

-continued

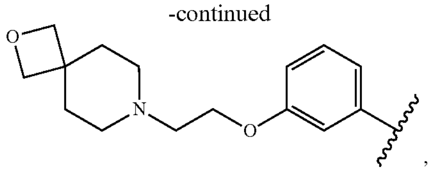,

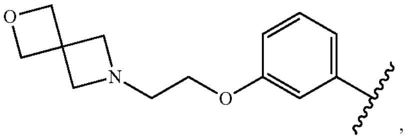,

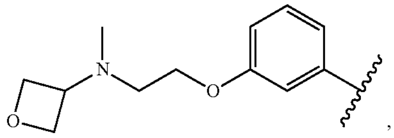, 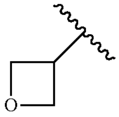,

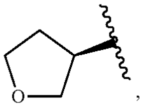, 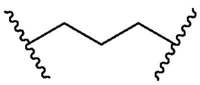, 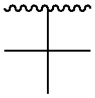, or

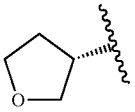.

In some embodiments, $R^8$ is selected from those depicted in Table 1, below.

In some embodiments, $R^9$ is hydrogen. In some embodiments, $R^9$ is an optionally substituted $C_{1-6}$ aliphatic group. In some embodiments, $R^9$ is an optionally substituted $C_{1-6}$ aliphatic group.

In some embodiments, $R^9$ is selected from hydrogen,

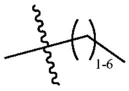, and 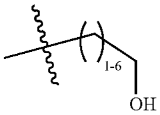

In some embodiments, $R^9$ is selected from hydrogen, methyl, and

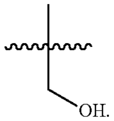 [SMILES: *CO]

In some embodiments, $R^9$ is selected from those depicted in Table 1, below.

As defined generally above, $R^{10}$ is selected from phenyl, a 3-8 membered saturated or partially unsaturated monocyclic carbocyclic ring, a 4-10 membered saturated or partially unsaturated bicyclic carbocyclic ring, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, an 8-10 membered bicyclic heteroaromatic ring having 1-5 heteroatoms independently selected from nitrogen, oxygen, and sulfur, and a $C_{1-6}$ aliphatic; wherein $R^{10}$ is optionally substituted with n instances of $R^3$.

In some embodiments, $R^{10}$ is phenyl. In some embodiments, $R^{10}$ is a 3-8 membered saturated or partially unsaturated monocyclic carbocyclic ring. In some embodiments, $R^{10}$ is a 4-10 membered saturated or partially unsaturated bicyclic carbocyclic ring. In some embodiments, $R^{10}$ is an 8-10 membered bicyclic aromatic carbocyclic ring. In some embodiments, $R^{10}$ is a 3-8 membered saturated or partially unsaturated monocyclic heterocyclic ring having 1-2 heteroatoms independently selected from nitrogen, oxygen, and sulfur. In some embodiments, $R^{10}$ is a 5-10 membered bicyclic heterocyclic ring having 1-4 heteroatoms independently selected from nitrogen, oxygen, and sulfur. In some embodiments, $R^{10}$ is a 5-6 membered monocyclic heteroaromatic ring having 1-4 heteroatoms independently selected from nitrogen, oxygen, and sulfur. In some embodiments, $R^{10}$ is an 8-10 membered bicyclic heteroaromatic ring having 1-5 heteroatoms independently selected from nitrogen, oxygen, and sulfur. In some embodiments, $R^{10}$ is a $C_{1-6}$ aliphatic.

In some embodiments, $R^{10}$ is phenyl.

In some embodiments, $R^{10}$ is

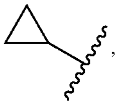, 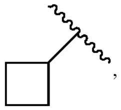, 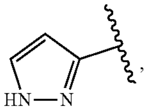, 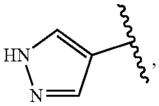,

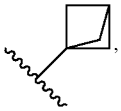, 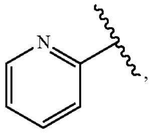, 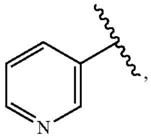,

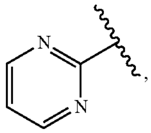, 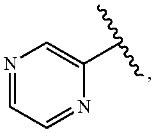, 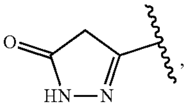,

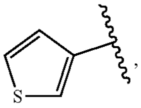, 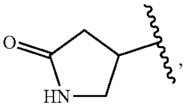, 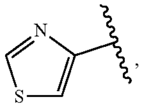,

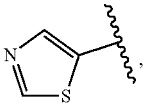, 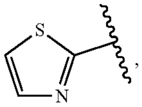, 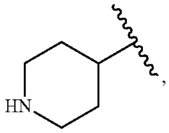,

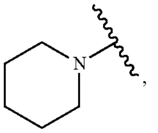, 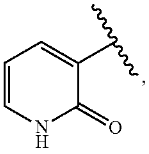, 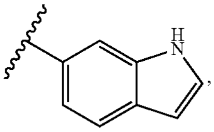,

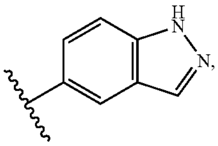, 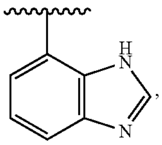,

-continued
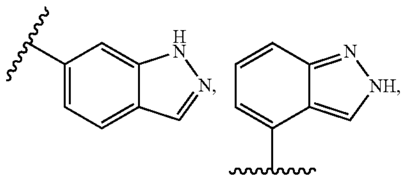
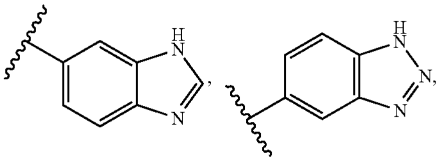
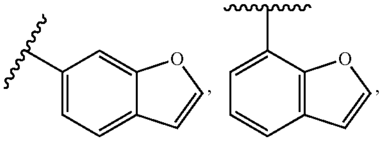
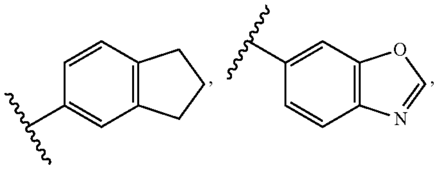
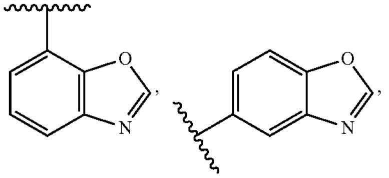
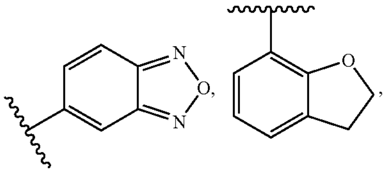
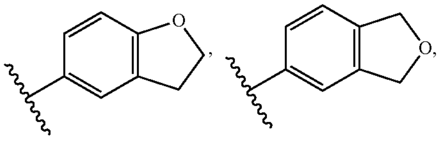
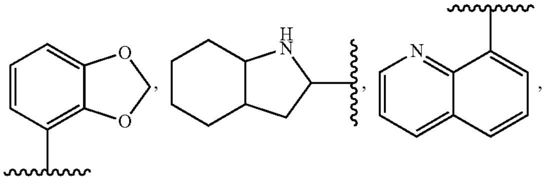
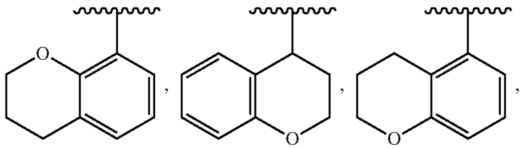
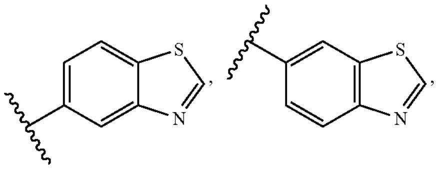
-continued
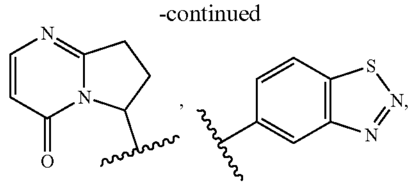
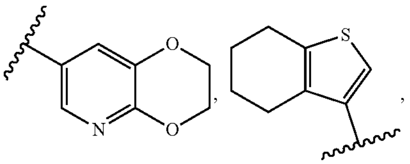
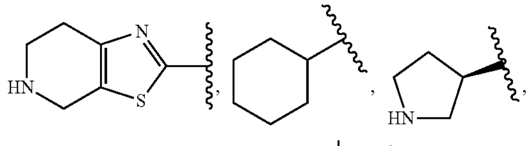
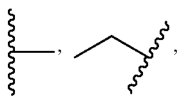
or
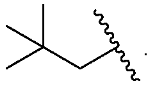
In some embodiments, $R^{10}$ together with n instances of $R^3$ is
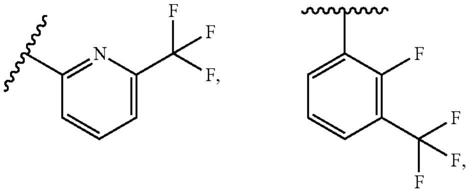
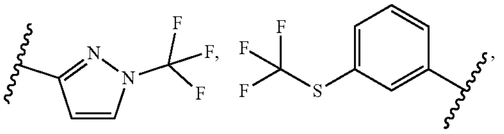
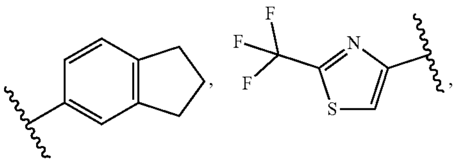
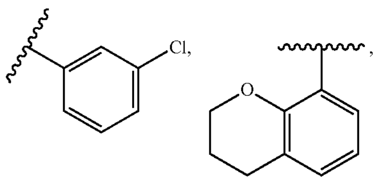
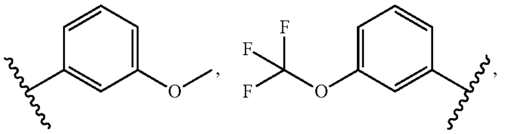
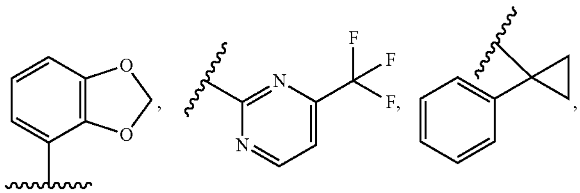

-continued
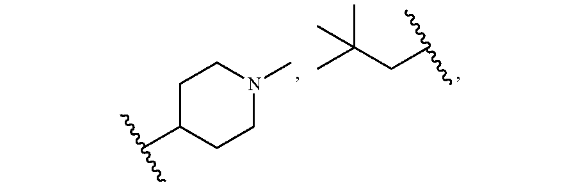
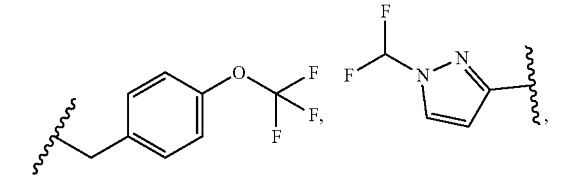
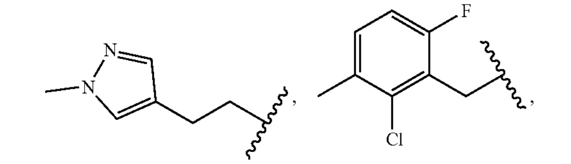
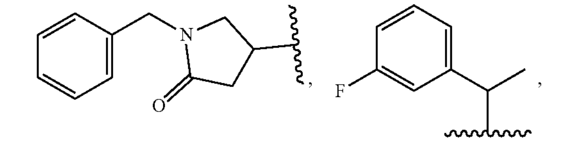
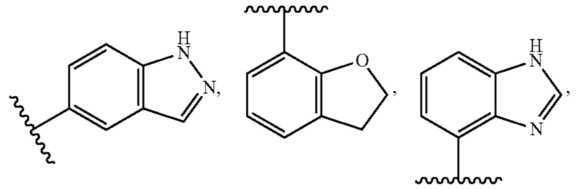
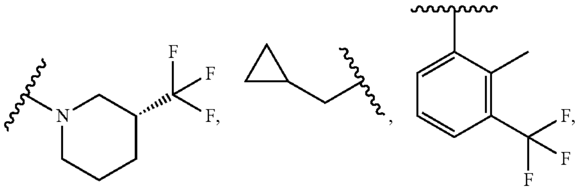
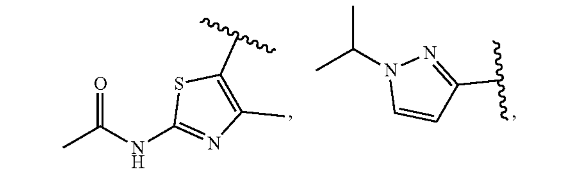
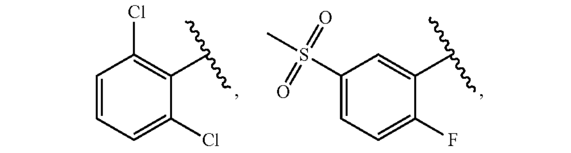
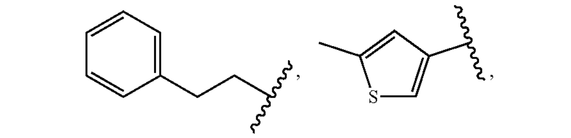
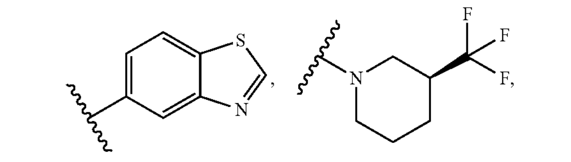
-continued
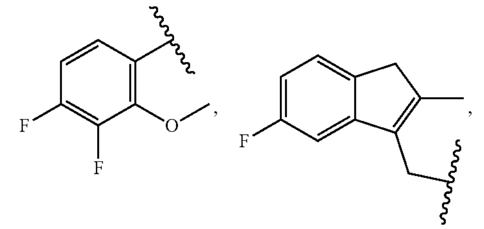
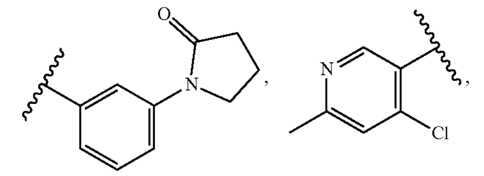
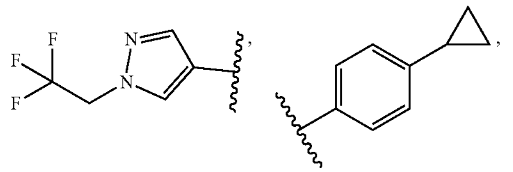
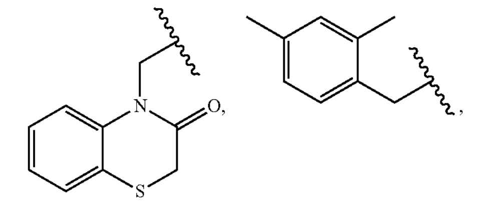
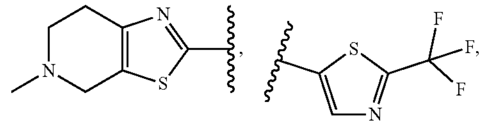
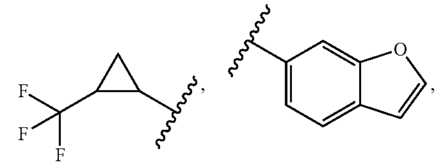
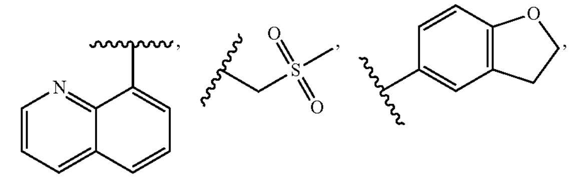
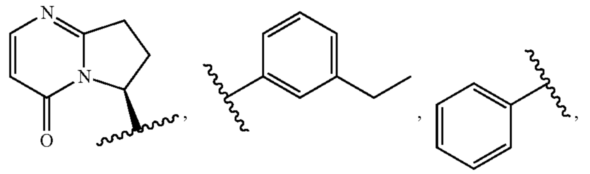
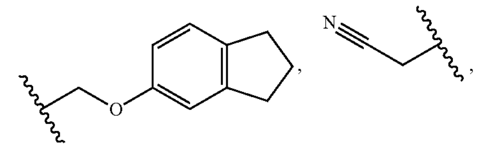

-continued
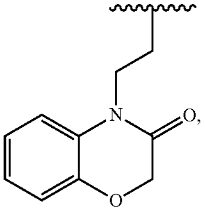, 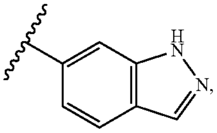,
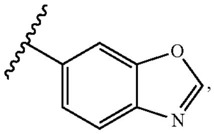, 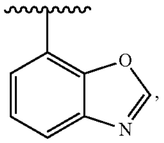,
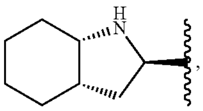, 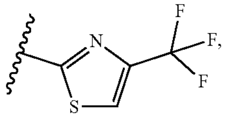,
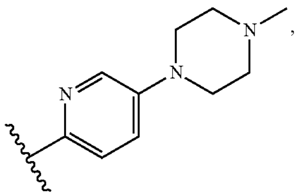, 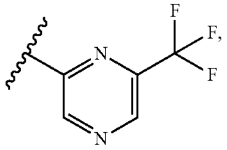
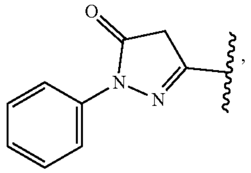, 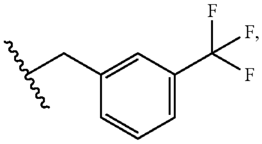
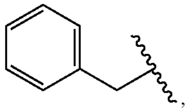, 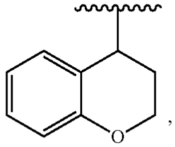,
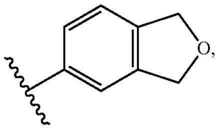, 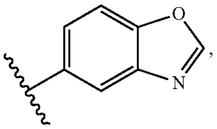,
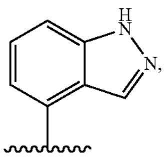, 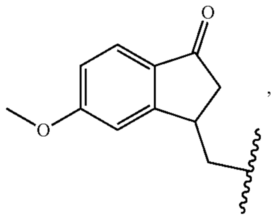,
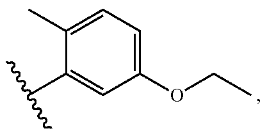, 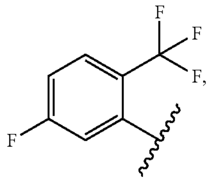,
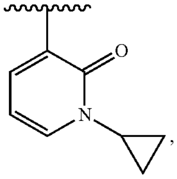, 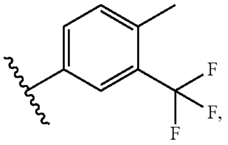,
-continued
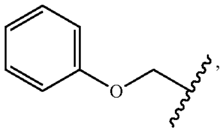, 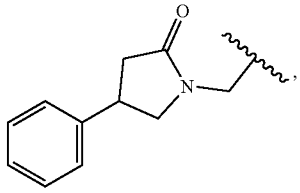,
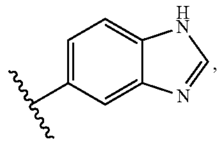, 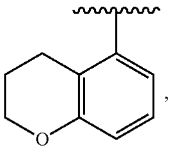,
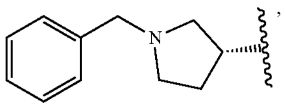, 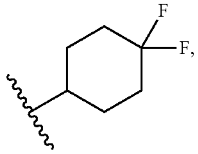,
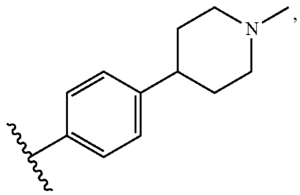, 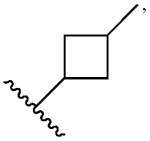,
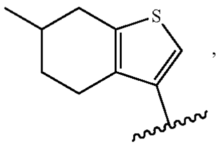, 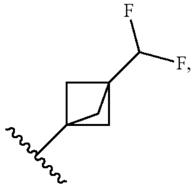,
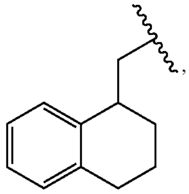, 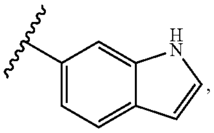,
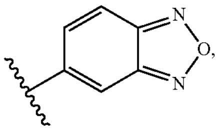, 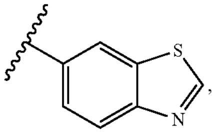,
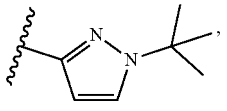, 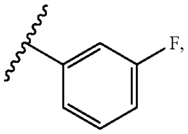,
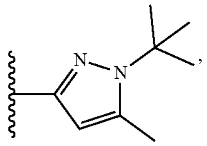, 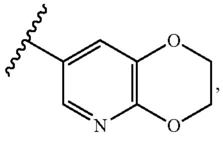, 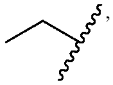, -continued

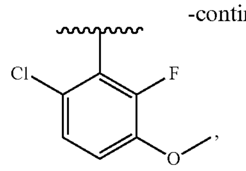,

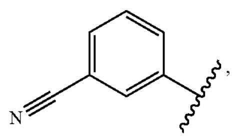,

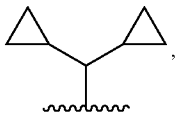,

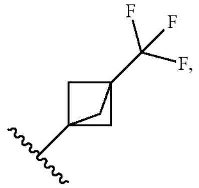,

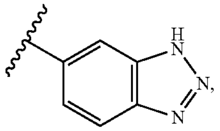,

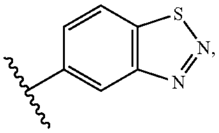 or

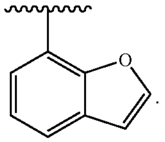.

In some embodiments, $R^{10}$ is selected from those depicted in Table 1, below.

As defined generally above, each occurrence of R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur.

In some embodiments, R is hydrogen. In some embodiments, R is a $C_{1-6}$ aliphatic group. In some embodiments, R is a substituted $C_{1-6}$ aliphatic group. In some embodiments, R is a 3-8 membered saturated monocyclic carbocyclic ring. In some embodiments, R is a 3-8 membered partially unsaturated monocyclic carbocyclic ring. In some embodiments, R is a substituted 3-8 membered saturated monocyclic carbocyclic ring. In some embodiments, R is a substituted 3-8 membered partially unsaturated monocyclic carbocyclic ring. In some embodiments, R is phenyl. In some embodiments, R is a substituted phenyl. In some embodiments, R is an 8-10 membered bicyclic aromatic carbocyclic ring. In some embodiments, R is a substituted 8-10 membered bicyclic aromatic carbocyclic ring. In some embodiments, R is a 4-8 membered saturated monocyclic heterocyclic ring having 1-2 heteroatoms independently selected from nitrogen, oxygen, and sulfur. In some embodiments, R is a 4-8 membered partially unsaturated monocyclic heterocyclic ring having 1-2 heteroatoms independently selected from nitrogen, oxygen, and sulfur. In some embodiments, R is a substituted 4-8 membered saturated monocyclic heterocyclic ring having 1-2 heteroatoms independently selected from nitrogen, oxygen, and sulfur. In some embodiments, R is a substituted 4-8 membered partially unsaturated monocyclic heterocyclic ring having 1-2 heteroatoms independently selected from nitrogen, oxygen, and sulfur. In some embodiments, R is a 5-6 membered monocyclic heteroaromatic ring having 1-4 heteroatoms independently selected from nitrogen, oxygen, and sulfur. In some embodiments, R is a substituted 5-6 membered monocyclic heteroaromatic ring having 1-4 heteroatoms independently selected from nitrogen, oxygen, and sulfur. In some embodiments, R is an 8-10 membered bicyclic heteroaromatic ring having 1-5 heteroatoms independently selected from nitrogen, oxygen, and sulfur. In some embodiments, R is a substituted 8-10 membered bicyclic heteroaromatic ring having 1-5 heteroatoms independently selected from nitrogen, oxygen, and sulfur.

In some embodiments, R is selected from those depicted in Table 1, below.

As defined generally above, m is 0, 1, 2, 3, 4 or 5. In some embodiments, m is 0. In some embodiments, m is 1. In some embodiments, m is 2. In some embodiments, m is 3. In some embodiments, m is 4. In some embodiments, m is 5.

In some embodiments, m is selected from those depicted in Table 1, below.

As defined generally above, n is 0, 1, 2, 3, 4 or 5. In some embodiments, n is 0. In some embodiments, n is 1. In some embodiments, n is 2. In some embodiments, n is 3. In some embodiments, n is 4. In some embodiments, n is 5.

In some embodiments, n is selected from those depicted in Table 1, below.

As defined generally above, p is 0, 1, 2, 3, 4 or 5. In some embodiments, p is 0. In some embodiments, p is 1. In some embodiments, p is 2. In some embodiments, p is 3. In some embodiments, p is 4. In some embodiments, p is 5.

In some embodiments, p is selected from those depicted in Table 1, below.

In one aspect, the present disclosure provides a compound of Formula Ib:

Ib

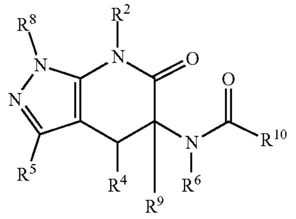

or a pharmaceutically acceptable salt thereof, wherein:

each of $R^1$, $R^2$, $R^3$, $R^4$, $R^6$, $R^7$, $R^8$, $R^9$, $R^{10}$, R, m, n and p are as defined above for Formula Ia, both singly and in combination; and $R^5$ is $L^2$-Y, wherein $L^2$ is a bivalent optionally substituted $C_{2-4}$ straight or branched hydrocarbon chain wherein one methylene unit of $L^2$ is optionally replaced by —NR—, or —C(O); and additionally one methylene unit of $L^2$ is optionally replaced by an optionally substituted ring selected from a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur; and Y is —CN.

In some embodiments of Formula Ib, $R^5$ is $L^2$-Y, wherein:

$L^2$ is a bivalent optionally substituted $C_{2-4}$ straight or branched hydrocarbon chain wherein one methylene unit of $L^2$ is optionally replaced by —NR—, or —C(O); and additionally one methylene unit of $L^2$ is optionally replaced by a ring selected

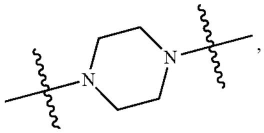
,
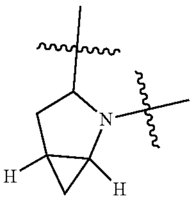
,
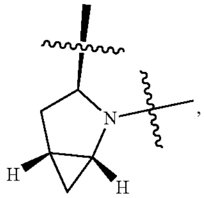
, and
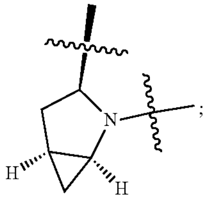
;

and Y is —CN.

In some embodiments of Formula Ib, $R^5$ is

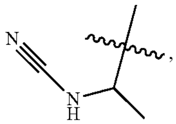
,
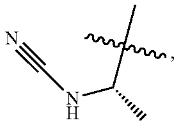
,
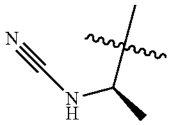
,
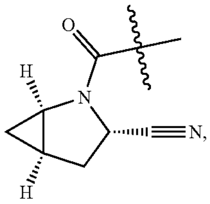
,
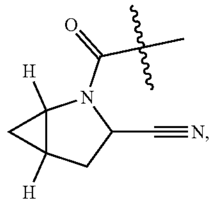
,
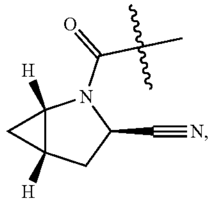
,
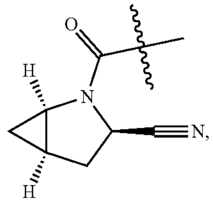
,
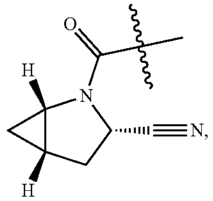
,
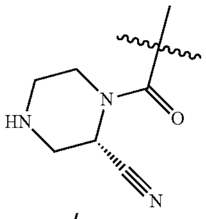
, or
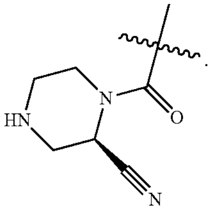
.

In some embodiments, the present disclosure provides a compound of Formula II:

II

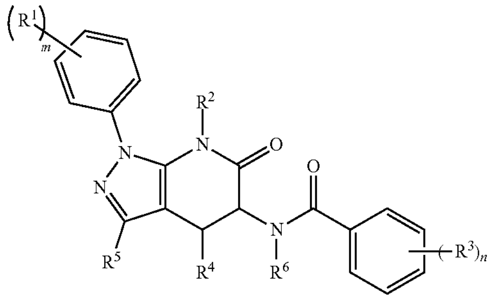

or a pharmaceutically acceptable salt thereof, wherein:

each of $R^1$, $R^2$, $R^3$, $R^4$, $R^5$, $R^6$, m and n are as defined above and described in embodiments herein, both singly and in combination.

In some embodiments, the present disclosure provides compounds of Formula IIia, Formula IIib, Formula IIic or Formula IIid:

IIia

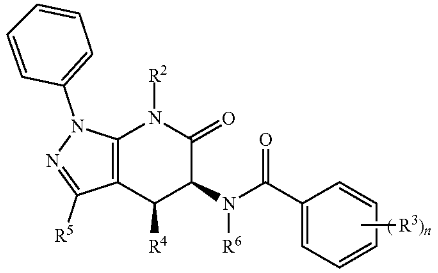

IIib

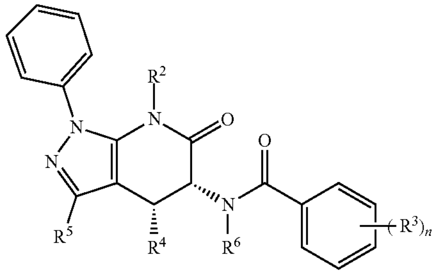

IIic

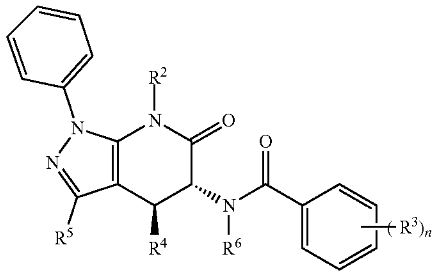

-continued

IIid

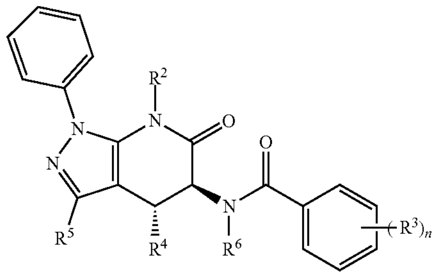

or a pharmaceutically acceptable salt thereof, wherein:

each of $R^2$, $R^3$, $R^4$, $R^5$, $R^6$, and n are as defined above and described in embodiments herein, both singly and in combination.

In some embodiments, the present disclosure provides compounds of Formula IIiia, Formula IIiib, Formula IIiic or Formula IIiid:

IIiia

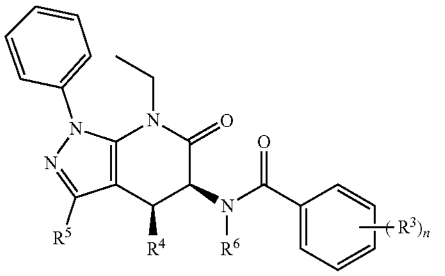

IIiib

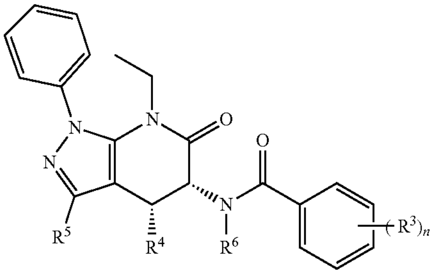

IIiic

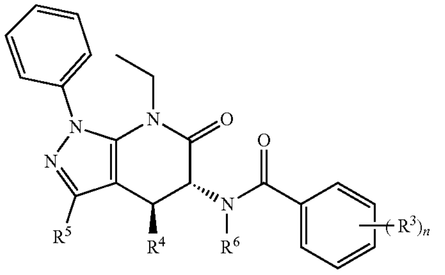

-continued

IIiid

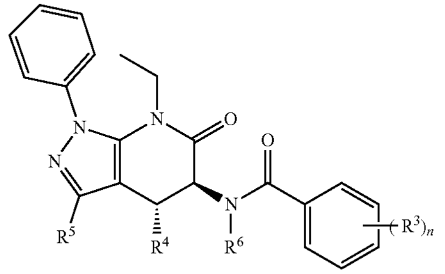

or a pharmaceutically acceptable salt thereof, wherein:

each of $R^3$, $R^4$, $R^5$, $R^6$, and n are as defined above and described in embodiments herein, both singly and in combination.

In some embodiments, the present disclosure provides compounds of Formula IIiia-i, Formula IIiib-i, Formula IIiic-i or Formula IIiid-i:

IIiia-i

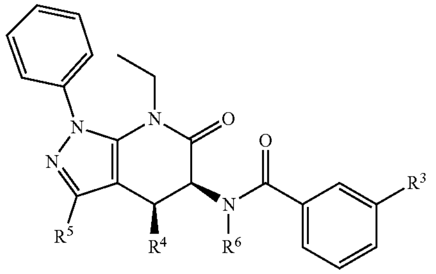

IIiib-i

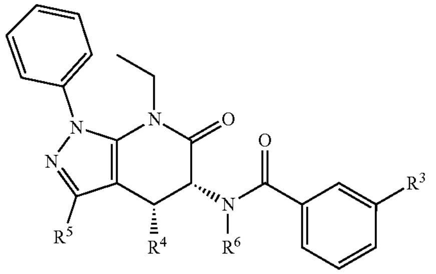

IIiic-i

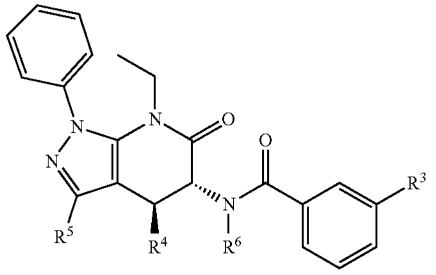

-continued

IIiid-i

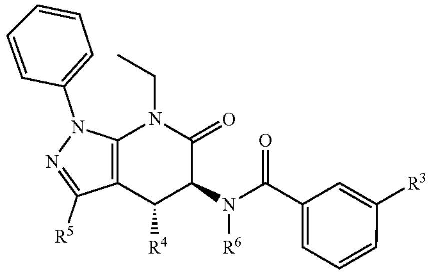

or a pharmaceutically acceptable salt thereof, wherein:

each of $R^3$, $R^4$, $R^5$, and $R^6$ are as defined above and described in embodiments herein, both singly and in combination.

In some embodiments, the present disclosure provides compounds of Formula IIiiia, Formula IIiiib, Formula IIiiic or Formula IIiiid:

IIiiia

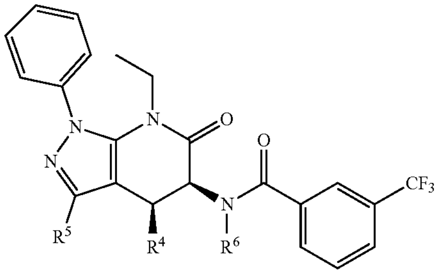

IIiiib

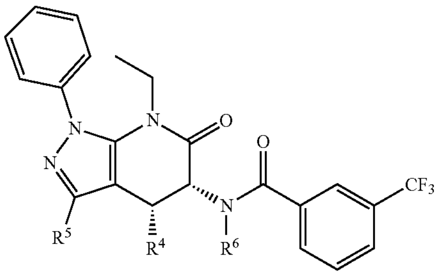

IIiiic

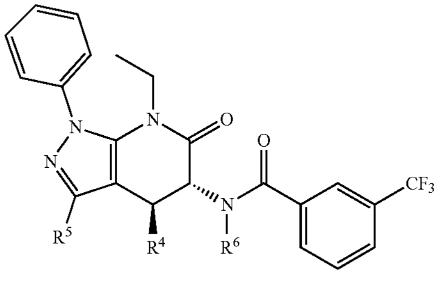

-continued

IIiiid

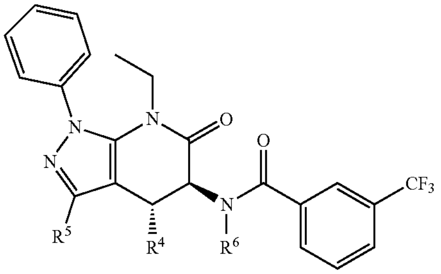

or a pharmaceutically acceptable salt thereof, wherein:

each of $R^4$, $R^5$, and $R^6$ are as defined above and described in embodiments herein, both singly and in combination.

In some embodiments, the present disclosure provides compounds of Formula IIiva, Formula IIivb, Formula IIive or Formula IIivd:

IIiva

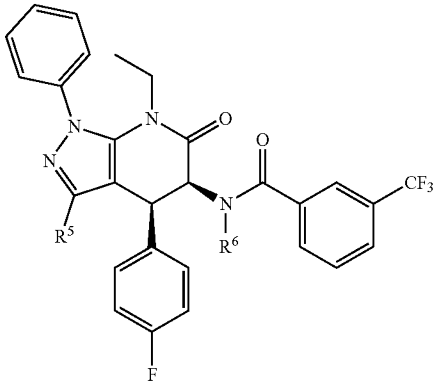

IIivb

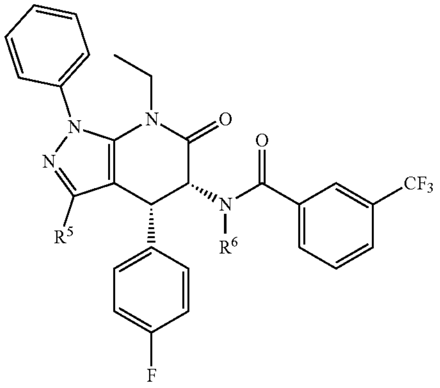

-continued

IIivc

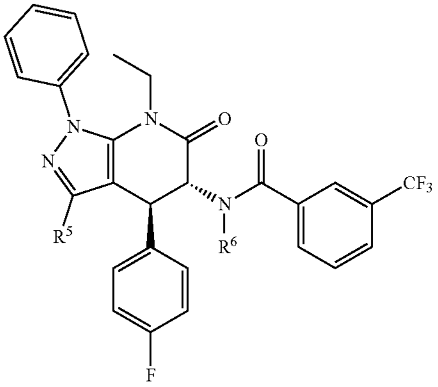

IIivd

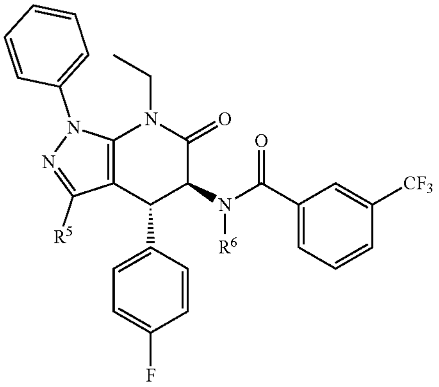

or a pharmaceutically acceptable salt thereof, wherein:

each of $R^5$ and $R^6$ are as defined above and described in embodiments herein, both singly and in combination.

In some embodiments, the present disclosure provides compounds of Formula IIva, Formula IIvb, Formula IIvc or Formula IIvd:

IIva

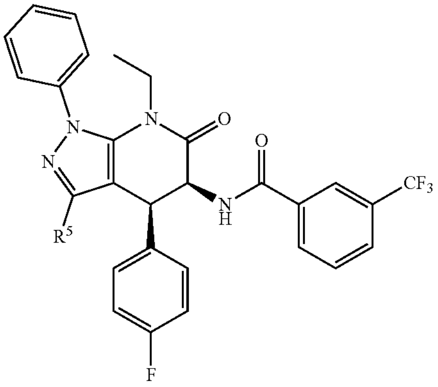

-continued

IIvb

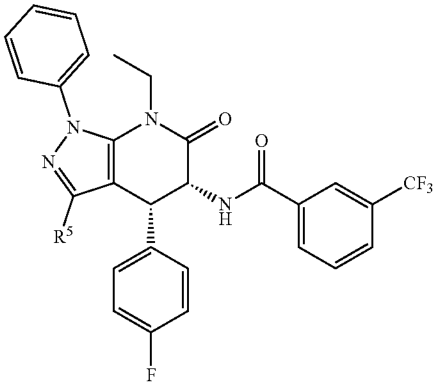

IIvc

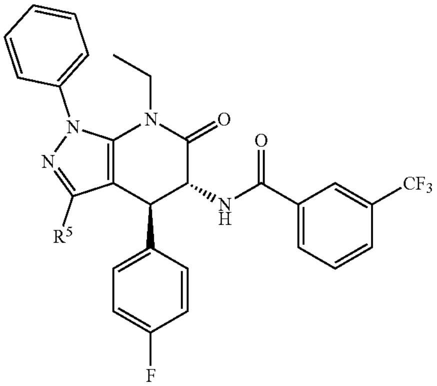

IIvd

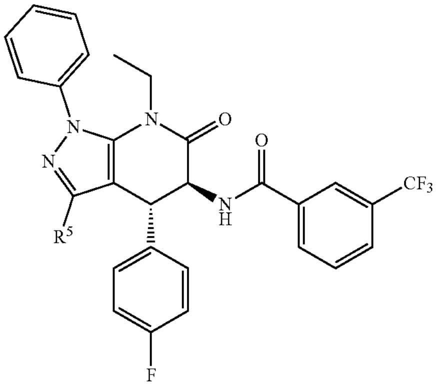

or a pharmaceutically acceptable salt thereof, wherein:

$R^5$ is as defined above and described in embodiments herein, both singly and in combination.

In some embodiments, the present disclosure provides a compound of Formula III:

III

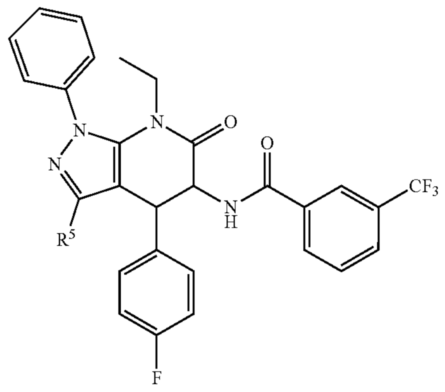

or a pharmaceutically acceptable salt thereof, wherein:

$R^5$ is as defined above and described in embodiments herein, both singly and in combination.

In some embodiments, the present disclosure provides compounds of Formula IIIa, Formula IIIb, Formula IIIc or Formula IIId:

IIIa

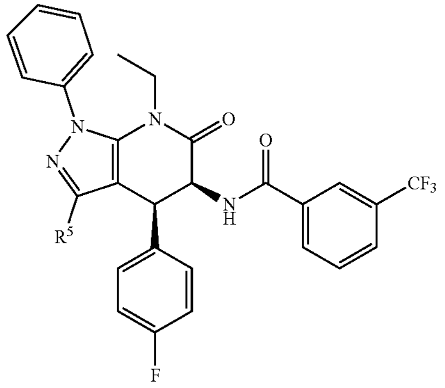

IIIb

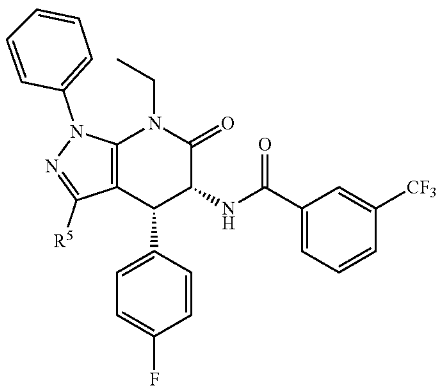

-continued

IIIc

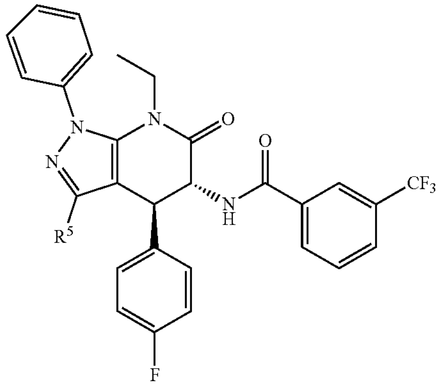

IIId

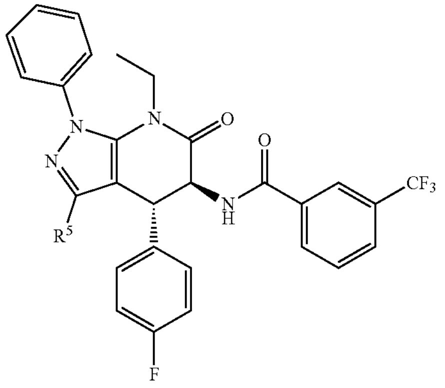

or a pharmaceutically acceptable salt thereof, wherein:

$R^5$ is $L^2$-Y, wherein $L^2$ is a covalent bond, bivalent $C_{2-8}$ straight or branched, hydrocarbon chain wherein one or two methylene units of $L^2$ are optionally independently replaced by —NRC(O)—, —C(O)NR—, —N(R)$SO_2$—, —$SO_2$N(R)—, —S—, —S(O)—, —$SO_2$—, —C(O)—, —OC(O)—, or —C(O)O—; and additionally one methylene unit of $L^2$ is optionally replaced by an optionally substituted 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur; and Y is hydrogen, halogen, —$COOR^f$, —CN, —$CONR^f_2$, —$NR^f$CN, $NO_2$, —$NR^f_2$, epoxide, or a ring selected from an optionally substituted 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, and an 8-10 membered bicyclic heteroaromatic ring having 1-5 heteroatoms independently selected from nitrogen, oxygen, and sulfur, or $C_{1-8}$ aliphatic optionally substituted with halogen, $NO_2$, or CN; wherein $-L^2$-Y comprises an alpha, beta-unsaturated carbonyl moiety, amide, cyano group, halogen, carbonyl, alkynyl group, sulfonyl group, or epoxide; and wherein each occurrence of $R^f$, $R^g$ and $R^h$ is independently H, halogen, OH, or straight or branched $C_{1-6}$ alkyl, $C_{2-6}$ alkenyl, or $C_{2-6}$ alkynyl group optionally substituted with 1, 2 or 3 halogen atoms.

In some embodiments of Formula IIIa, Formula IIIb, Formula IIIc, and Formula IIId, $R^5$ is $L^2$-Y, wherein $L^2$ is a covalent bond, bivalent $C_{2-8}$ straight or branched, hydrocarbon chain wherein one or two methylene units of $L^2$ are optionally independently replaced by —NRC(O)—, —C(O)NR—, —N(R)$SO_2$—, —$SO_2$N(R)—, —S—, —S(O)—, —$SO_2$—, —C(O)—, —OC(O)—, or —C(O)O—; and additionally one methylene unit of $L^2$ is optionally replaced by an optionally substituted 3-8 membered saturated or partially unsaturated monocyclic carbocyclic ring, or a 3-8 membered saturated or partially unsaturated monocyclic heterocyclic ring having 1-2 heteroatoms independently selected from nitrogen, oxygen, and sulfur; and Y is hydrogen, halogen, —COOR$^f$, —CN, —CONR$^f_2$, —NR$^f$CN, $NO_2$, —NR$^f_2$, epoxide, or a ring selected from an optionally substituted 3-8 membered saturated or partially unsaturated monocyclic carbocyclic ring, phenyl, a 3-8 membered saturated or partially unsaturated monocyclic heterocyclic ring having 1-2 heteroatoms independently selected from nitrogen, oxygen, and sulfur, and a 5-10 membered bicyclic heterocyclic ring having 1-4 heteroatoms independently selected from nitrogen, oxygen, and sulfur, or $C_{1-8}$ aliphatic optionally substituted with halogen, $NO_2$, or CN; wherein $-L^2$-Y comprises an alpha, beta-unsaturated carbonyl moiety, amide, cyano group, halogen, carbonyl, alkynyl group, sulfonyl group, or epoxide; and wherein each occurrence of $R^f$, $R^g$ and $R^h$ is independently H, halogen, OH, or straight or branched $C_{1-6}$ alkyl, $C_{2-6}$ alkenyl, or $C_{2-6}$ alkynyl group optionally substituted with 1, 2 or 3 halogen atoms.

In some embodiments of Formula IIIa, Formula IIIb, Formula IIIc, and Formula IIId, $R^5$ is $L^2$-Y, wherein $L^2$ is a covalent bond, bivalent $C_{2-8}$ straight or branched, hydrocarbon chain wherein one or two methylene units of $L^2$ are optionally independently replaced by —NRC(O), —C(O)NR—, —N(R)$SO_2$—, —$SO_2$N(R)—, —S—, —S(O)—, —$SO_2$—, —C(O)—, —OC(O)—, or —C(O)O—; and additionally one methylene unit of $L^2$ is optionally replaced by a ring selected from

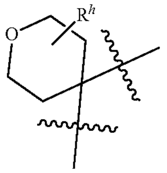,
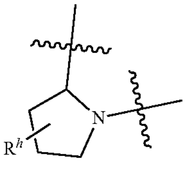,

-continued

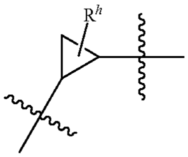,
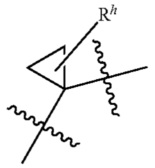,
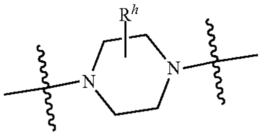,
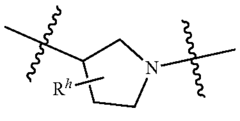,
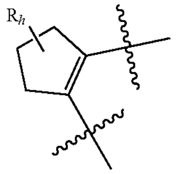,
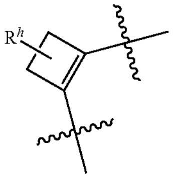,
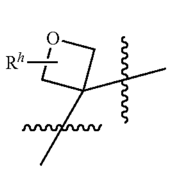, and
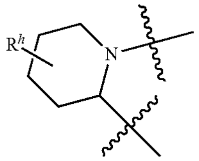;

and Y is hydrogen, halogen, —COOR$^f$, —CN, —CONR$^f_2$, —NR$^f$CN, $NO_2$, —NR$^f_2$, epoxide, or a ring selected from

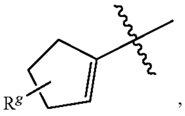,
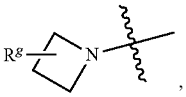,
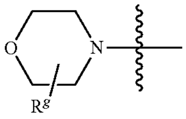,
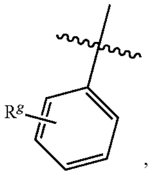,
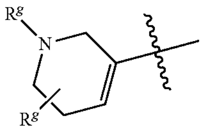,
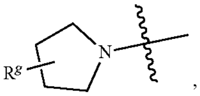,
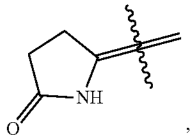,
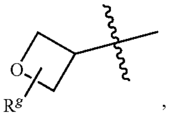,
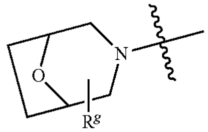,
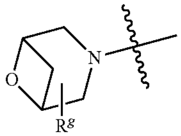,
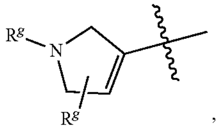,
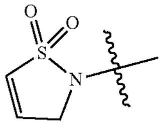,
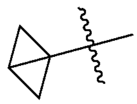,
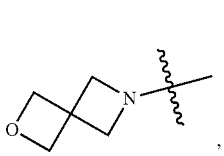,
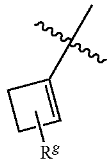,
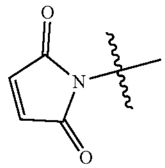, -continued

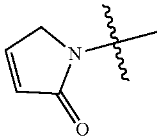, 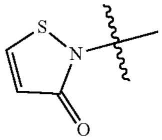, 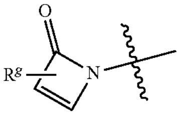,

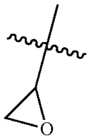, 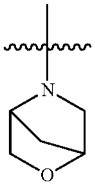, 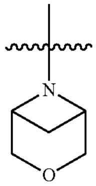, 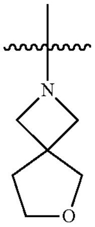, 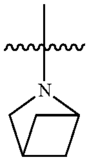,

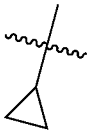, and 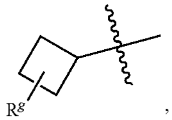, or $C_{1-8}$ aliphatic optionally substituted with halogen, $NO_2$, or CN; wherein $-L^2-Y$ comprises an alpha, beta-unsaturated carbonyl moiety, amide, cyano group, halogen, carbonyl, alkynyl group, sulfonyl group, or epoxide; and wherein each occurrence of $R^f$, $R^g$ and $R^h$ is independently H, halogen, OH, or straight or branched $C_{1-6}$ alkyl, $C_{2-6}$ alkenyl, or $C_{2-6}$ alkynyl group optionally substituted with 1, 2 or 3 halogen atoms.

In some embodiments, the present disclosure provides a compound of Formula IV-a, IV-b or IV-c:

IV-a

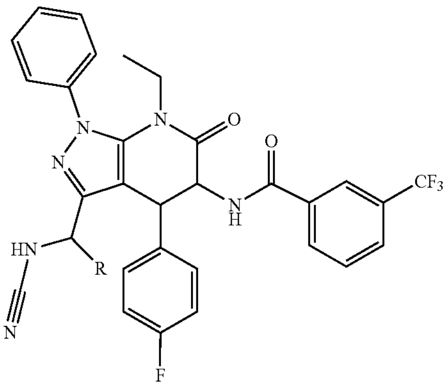

IV-b

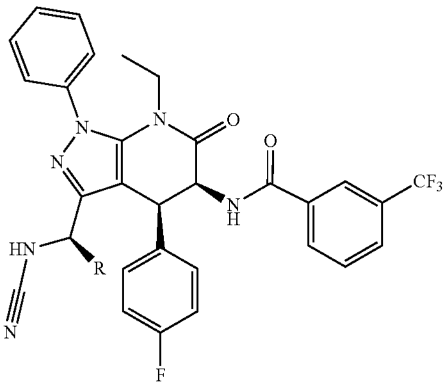

-continued

IV-c

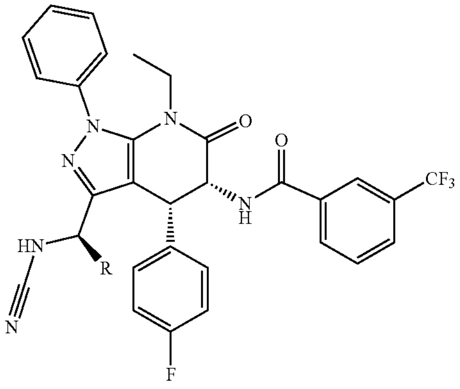

or a pharmaceutically acceptable salt thereof, wherein:

R is as defined above and described in embodiments herein, both singly and in combination.

In some embodiments of Formula IV-a, IV-b, or IV-c, R is selected from methyl,

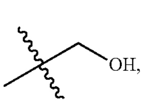 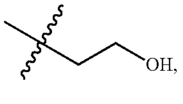 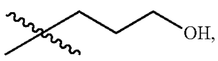

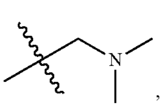, 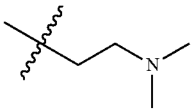 and

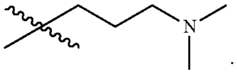.

In some embodiments, the present disclosure provides a compound of Formula V-a, V-b or V-c:

V-a

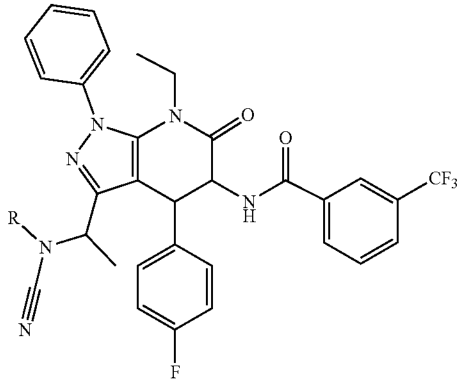

-continued

V-b

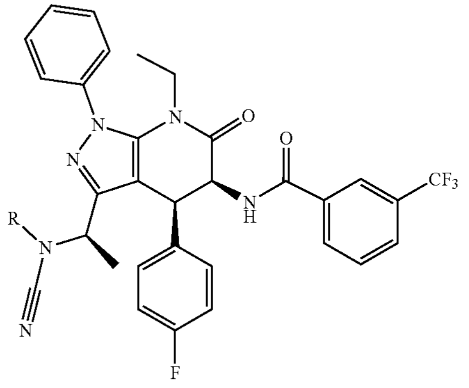

V-c

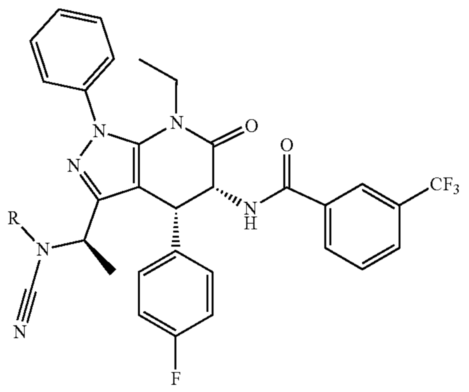

or a pharmaceutically acceptable salt thereof, wherein:

R is as defined above and described in embodiments herein, both singly and in combination.

In some embodiments of Formula V-a, V-b or V-c, R is selected from methyl,

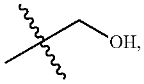, 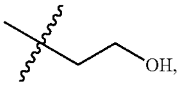, 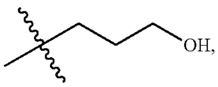,

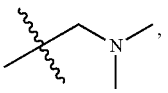, 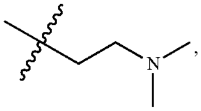,

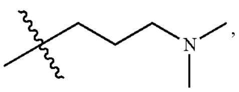, 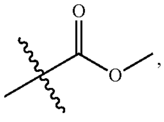,

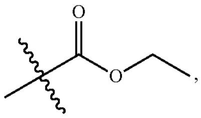, 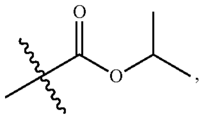,

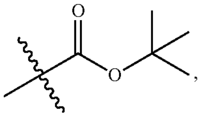, and 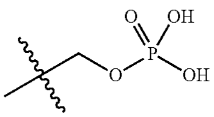

or a pharmaceutically acceptable salt thereof.

In some embodiments, the present disclosure provides a compound of Formula VI-a, VI-b or VI-c:

VI-a

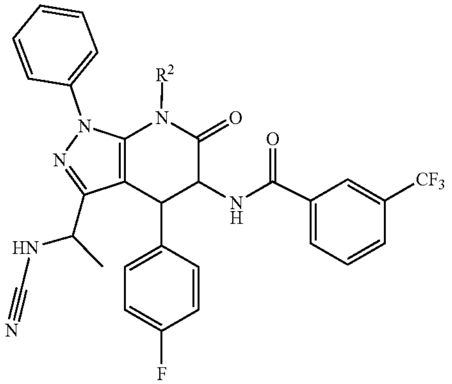

VI-b

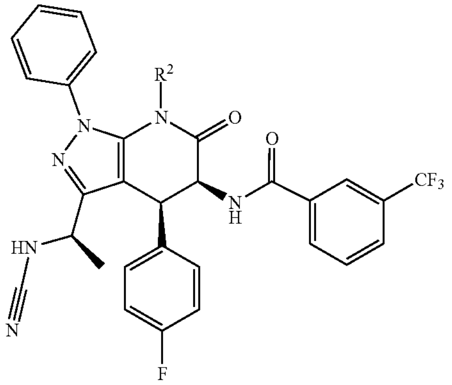

VI-c

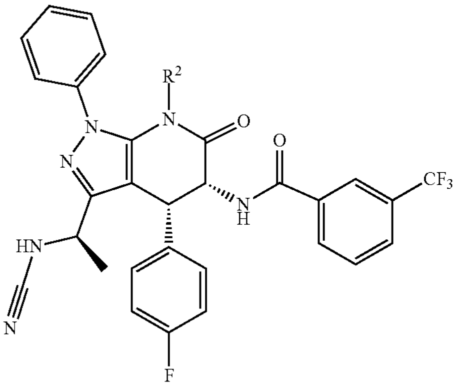

or a pharmaceutically acceptable salt thereof, wherein:

$R^2$ is as defined above and described in embodiments herein, both singly and in combination.

In some embodiments of Formula VI-a, VI-b or VI-c, $R^2$ is selected from ethyl,

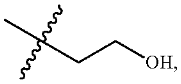, 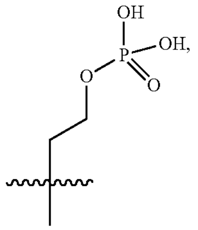 and

-continued

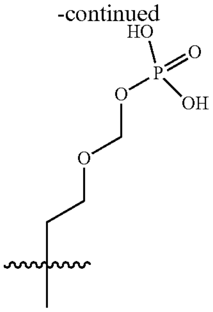

or a pharmaceutically acceptable salt thereof.

In some embodiments, the present disclosure provides compounds of Formula VIIa, Formula VIIb, Formula VIIc or Formula VIId:

VIIa

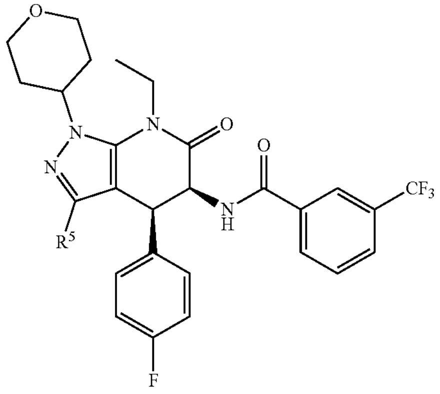

VIIb

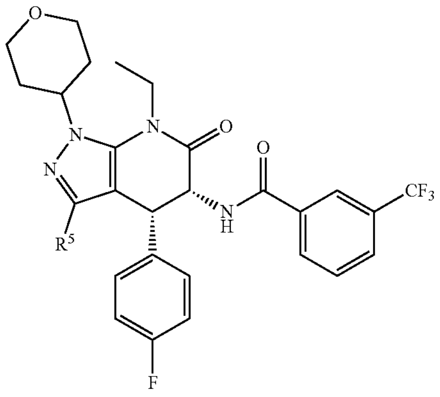

VIIc

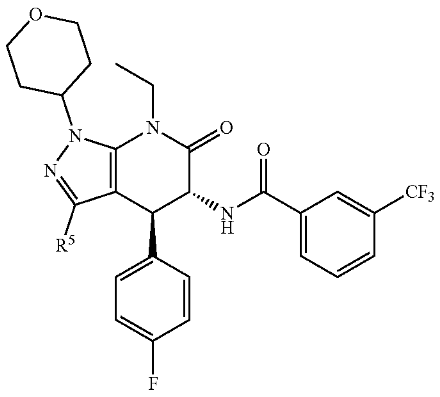

-continued

VIId

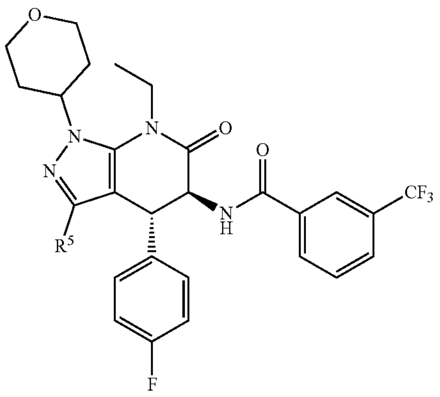

or a pharmaceutically acceptable salt thereof, wherein:

$R^5$ is as defined above and described in embodiments herein, both singly and in combination.

In some embodiments, the present disclosure provides compounds of Formula VIIIa, Formula VIIIb, Formula VIIIc or Formula VIIId:

VIIIa

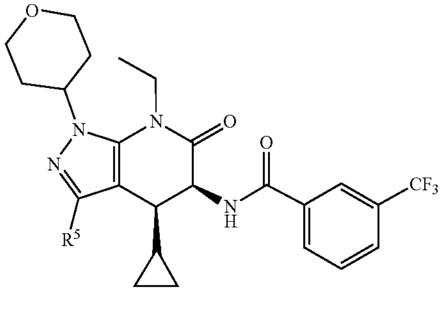

VIIIb

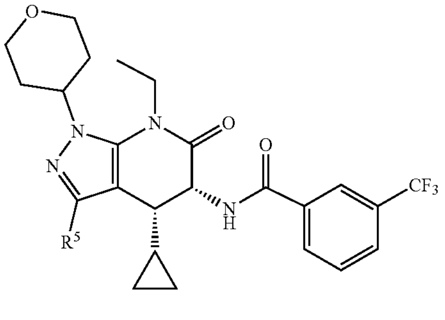

VIIIc

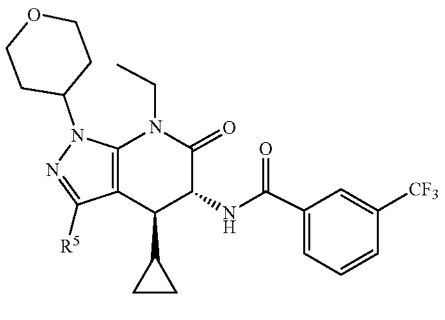

-continued

VIIId

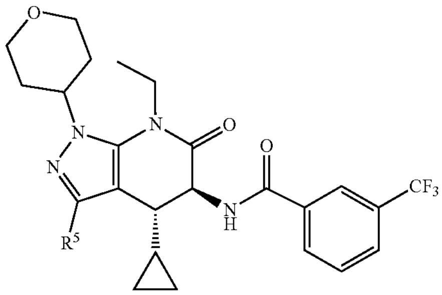

or a pharmaceutically acceptable salt thereof, wherein:

$R^5$ is as defined above and described in embodiments herein, both singly and in combination.

In some embodiments, the present disclosure provides compounds of Formula IXa, Formula IXb, Formula IXc or Formula IXd:

IXa

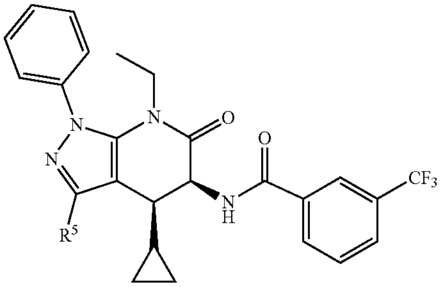

IXb

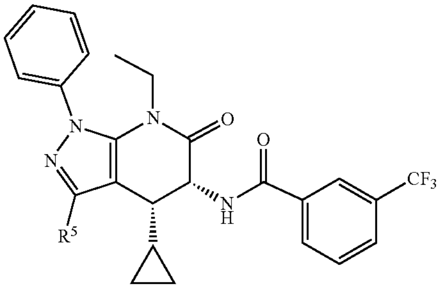

IXc

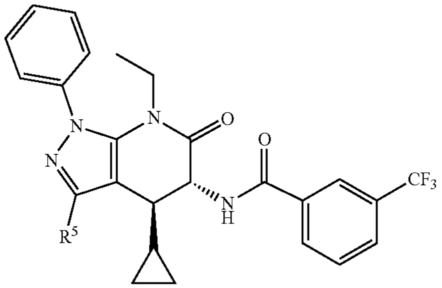

-continued

IXd

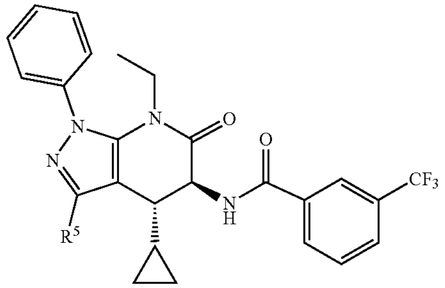

or a pharmaceutically acceptable salt thereof, wherein:

$R^5$ is as defined above and described in embodiments herein, both singly and in combination.

In some embodiments of Formula VIIa, Formula VIIb, Formula VIIc, Formula VIId, Formula VIIIa, Formula VIIIb, Formula VIIIc, Formula VIIId, Formula IXa, Formula IXb, Formula IXc, and Formula IXd, $R^5$ is $L^2$-Y, wherein $L^2$ is a covalent bond or a bivalent optionally substituted $C_{2-10}$ straight or branched hydrocarbon chain wherein one, two or three methylene units of $L^2$ are optionally and independently replaced by —NRC(O)—, —C(O)NR—, —N(R)$SO_2$—, —$SO_2$N(R)—, —S—, —O—, —NR—, —S(O)—, —$SO_2$—, —C(O)—, —OC(O)—, or —C(O)O—; $C_{2-10}$ straight or branched hydrocarbon chain is optionally substituted with 1, 2, 3, or 4 independently selected halogen atoms and optionally substituted with one —CN or —OR group; and additionally one methylene unit of $L^2$ is optionally replaced by an optionally substituted ring selected from a 3-8 membered saturated or partially unsaturated monocyclic carbocyclic ring, a 4-10 membered bicyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur; and Y is hydrogen, halogen, —COOR, —CN, —CON$(R)_2$, —CONRCN, —NRCN, $NO_2$, —N$(R)_2$, optionally substituted $C_{1-8}$ aliphatic, or an optionally substituted ring selected from a 3-8 membered saturated or partially unsaturated monocyclic carbocyclic ring, a 4-10 membered bicyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, and an 8-10 membered bicyclic heteroaromatic ring having 1-5 heteroatoms independently selected from nitrogen, oxygen, and sulfur; wherein -$L^2$-Y comprises an alpha, beta-unsaturated carbonyl moiety, amide, cyano group, halogen, carbonyl, alkynyl group, sulfonyl group, or epoxide.

In some embodiments of Formula VIIa, Formula VIIb, Formula VIIc, Formula VIId, Formula VIIIa, Formula VIIIb, Formula VIIIc, Formula VIIId, Formula IXa, Formula IXb, Formula IXc, and Formula IXd, $R^5$ is $L^2$-Y, wherein $L^2$ is a covalent bond or a bivalent optionally substituted $C_{2-10}$ straight or branched hydrocarbon chain wherein one, two or three methylene units of $L^2$ are optionally and independently replaced by —NRC(O)—, —C(O)NR—, —N(R)$SO_2$—, —$SO_2$N(R)—, —S—, —O—, —NR—, —S(O)—, —$SO_2$—, —C(O)—, —OC(O)—, or —C(O)O—; $C_{2-10}$ straight or branched hydrocarbon chain is optionally substituted with 1, 2, 3, or 4 independently selected halogen atoms and optionally substituted with one —CN or —OR group; and additionally one methylene unit of $L^2$ is optionally replaced by an optionally substituted ring selected from a 3-8 membered saturated or partially unsaturated monocyclic carbocyclic ring, or a 3-8 membered saturated or partially unsaturated monocyclic heterocyclic ring having 1-2 heteroatoms independently selected from nitrogen, oxygen, and sulfur; and Y is hydrogen, halogen, —$COOR^f$, —CN, —$CONR^f_2$, —$CONR^f$CN, —$NR^f$CN, $NO_2$, —$NR^f_2$, $C_{1-8}$ aliphatic optionally substituted with halogen, $NO_2$, or CN, or an optionally substituted ring selected from a 3-8 membered saturated or partially unsaturated monocyclic carbocyclic ring, phenyl, a 3-8 membered saturated or partially unsaturated monocyclic heterocyclic ring having 1-2 heteroatoms independently selected from nitrogen, oxygen, and sulfur, and a 5-10 membered bicyclic heterocyclic ring having 1-4 heteroatoms independently selected from nitrogen, oxygen, and sulfur; wherein -$L^2$-Y comprises an alpha, beta-unsaturated carbonyl moiety, amide, cyano group, halogen, carbonyl, alkynyl group, sulfonyl group, or epoxide; and wherein each occurrence of $R^f$ is independently H, or straight or branched $C_{1-6}$ alkyl, $C_{2-6}$ alkenyl, or $C_{2-6}$ alkynyl group optionally substituted with 1, 2 or 3 halogen atoms.

In some embodiments of Formula VIIa, Formula VIIb, Formula VIIc, Formula VIId, Formula VIIIa, Formula VIIIb, Formula VIIIc, Formula VIIId, Formula IXa, Formula IXb, Formula IXc, and Formula IXd, $R^5$ is $L^2$-Y, wherein $L^2$ is a covalent bond or a bivalent optionally substituted $C_{2-10}$ straight or branched hydrocarbon chain wherein one, two or three methylene units of $L^2$ are optionally and independently replaced by —NRC(O)—, —C(O)NR—, —N(R)$SO_2$—, —$SO_2$N(R)—, —S—, —O—, —NR—, —S(O)—, —$SO_2$—, —C(O)—, —OC(O)—, or —C(O)O—; $C_{2-10}$ straight or branched hydrocarbon chain is optionally substituted with 1, 2, 3, or 4 independently selected halogen atoms and optionally substituted with one —CN or —OR group; and additionally one methylene unit of $L^2$ is optionally replaced by a ring selected from

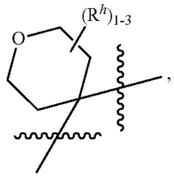,
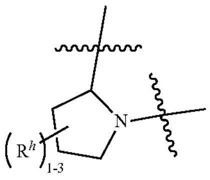,

-continued

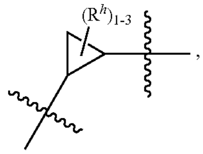,
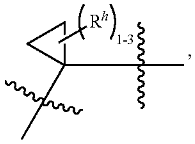,
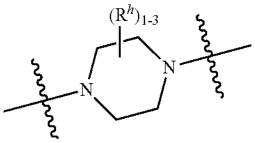,
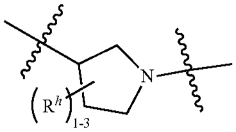,
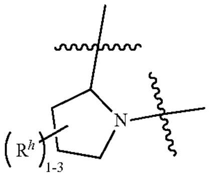,
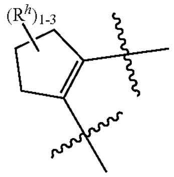,
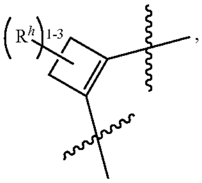,
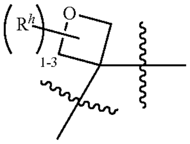,
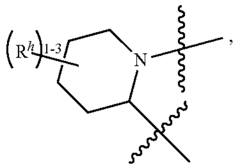,
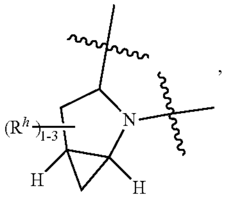,
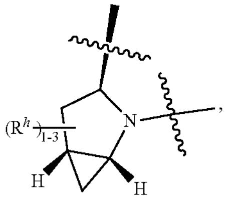,
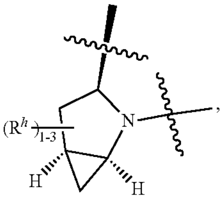,
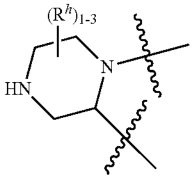,
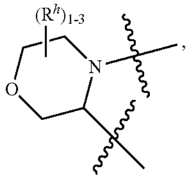,
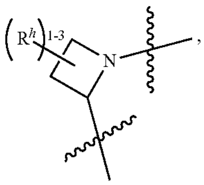,
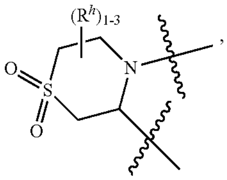,
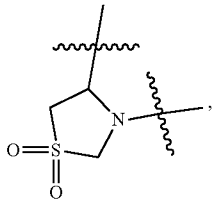,
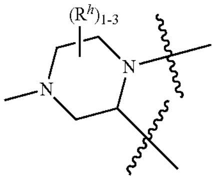, -continued
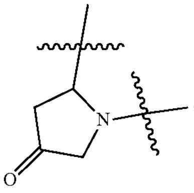,
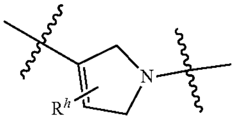, and
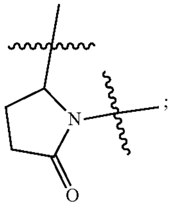;
and Y is hydrogen, halogen, —$COOR^f$, —CN, —$CONR^f_2$, —$CONR^fCN$, —$NR^fCN$, $NO_2$, —$NR^f_2$, epoxide, $C_{1-8}$ aliphatic optionally substituted with halogen, $NO_2$, or CN, or a ring selected from
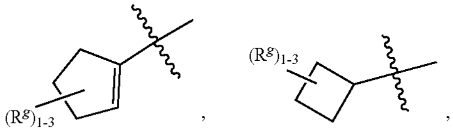,
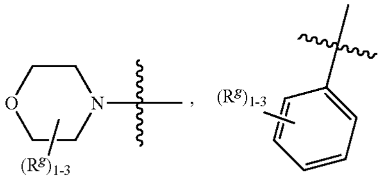,
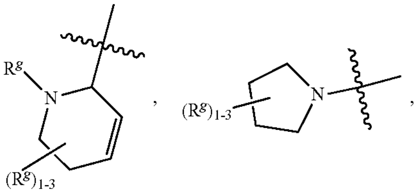,
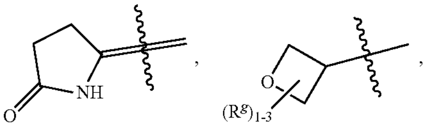,
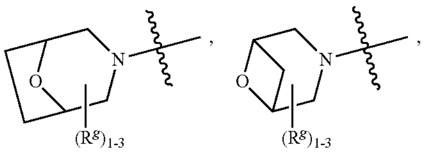,
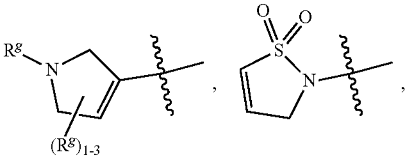,
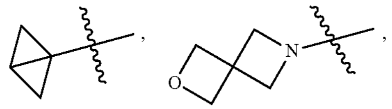,
-continued
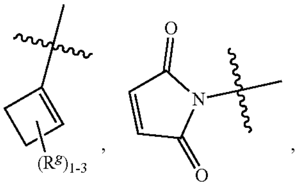,
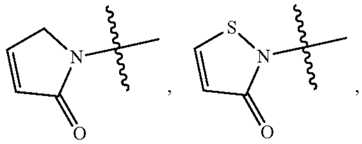,
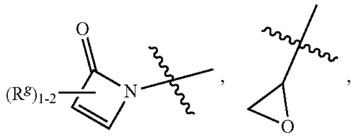,
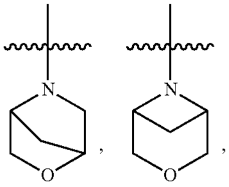,
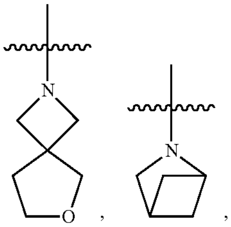,
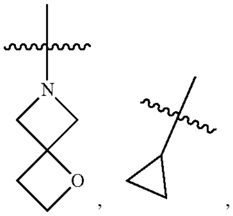,
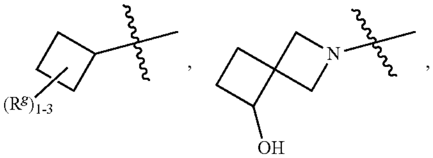,
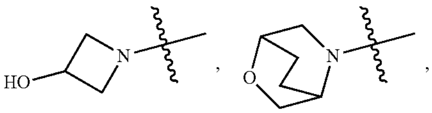,
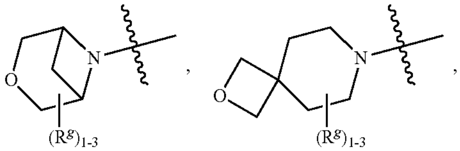,
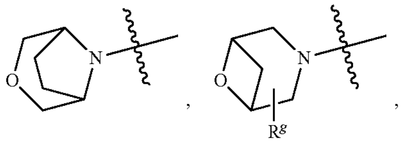, -continued

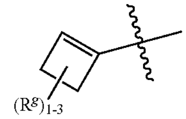

,

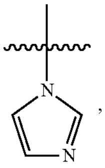

,

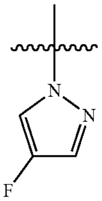

, and

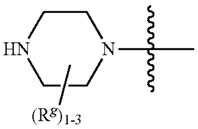

;

wherein $-L^2$-Y comprises an alpha, beta-unsaturated carbonyl moiety, amide, cyano group, halogen, carbonyl, $C_{2-6}$ alkynyl group, sulfonyl group, or epoxide; wherein each occurrence of $R^f$ is independently H, or straight or branched $C_{1-6}$ alkyl, $C_{2-6}$ alkenyl, or $C_{2-6}$ alkynyl group optionally substituted with 1, 2 or 3 halogen atoms; and wherein each occurrence of $R^8$ and $R^h$ is independently H, halogen, or OH, or straight or branched $C_{1-6}$ alkyl, $C_{2-6}$ alkenyl, or $C_{2-6}$ alkynyl group optionally substituted with 1, 2 or 3 halogen atoms.

In some embodiments, the present disclosure provides compounds of Formula Xa, Formula Xb, Formula Xc, Formula Xd, Formula Xe, Formula Xf, Formula Xg or Formula Xh:

Xa

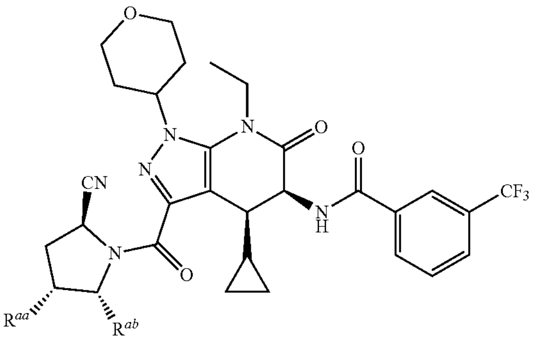

Xb

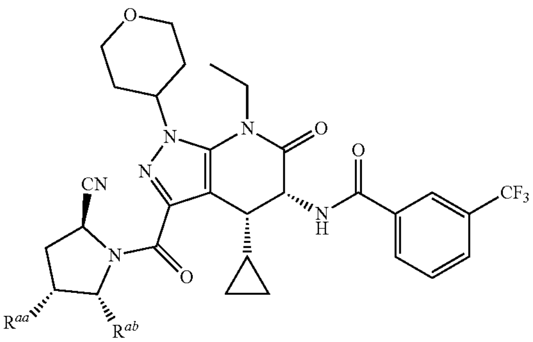

-continued

Xc

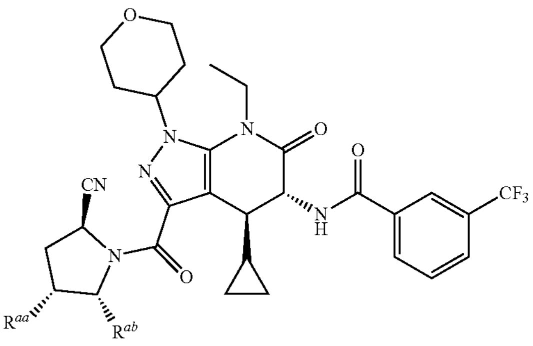

Xd

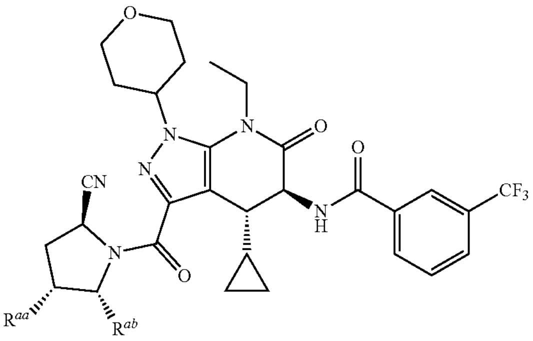

Xe

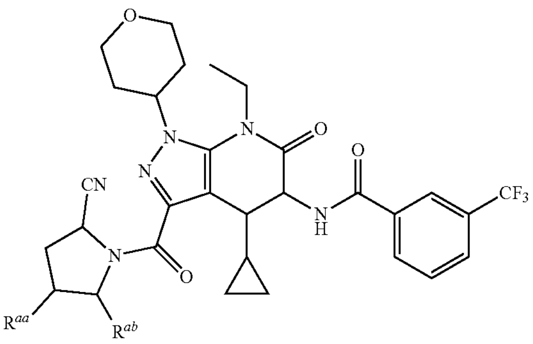

Xf

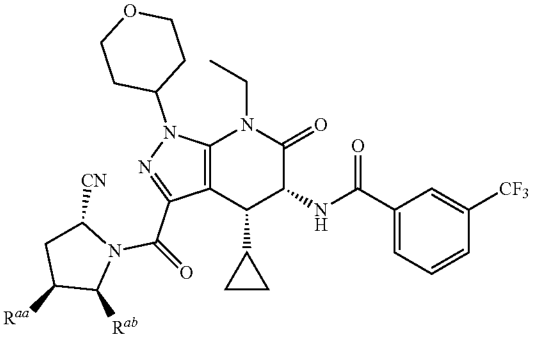

-continued

Xg

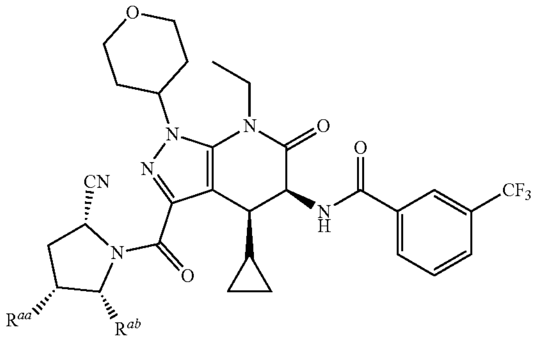

Xh

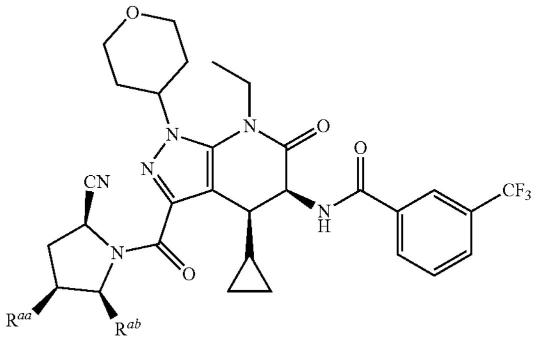

or a pharmaceutically acceptable salt thereof, wherein:

$R^{aa}$ and $R^{ab}$ are independently halogen, methyl, —$NH_2$, and —$NHCH_3$, or $R^{aa}$ and $R^{ab}$ together with the carbon atoms to which they are attached form a 3-6 membered monocyclic carbocyclic ring.

In some embodiments, the present disclosure provides compounds of Formula XIa, Formula XIb, Formula XIc, Formula XId, or Formula XIe:

XIa

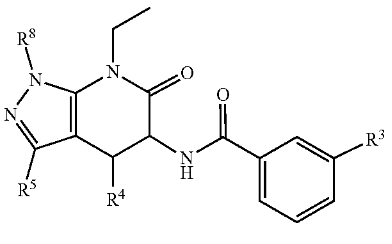

XIb

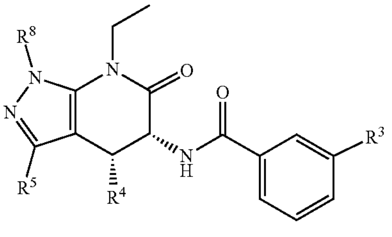

-continued

XIc

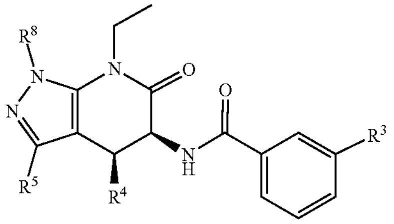

XId

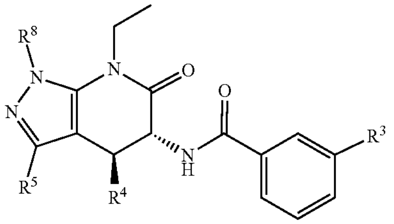

XIe

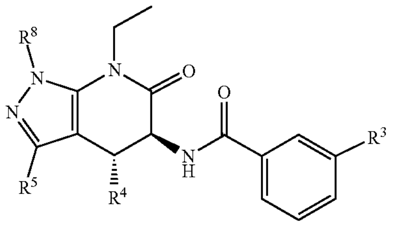

or a pharmaceutically acceptable salt thereof, wherein:

$R^3$ is ethyl or —$CF_3$; $R^4$ is

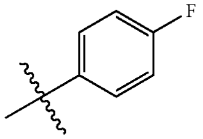 [SMILES: *c1ccc(F)cc1]

or cyclopropyl; $R^8$ is phenyl or

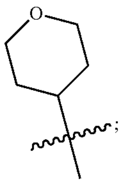 [SMILES: *C1CCOCC1]

and $R^5$ is

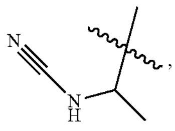,
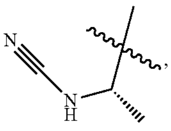,
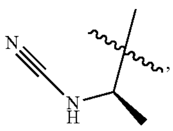,

-continued

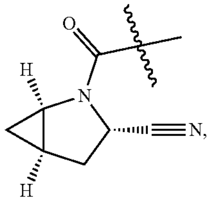,

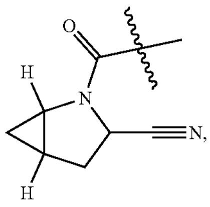,

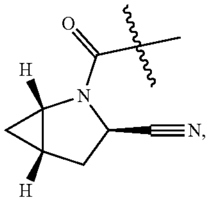,

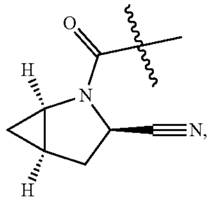,

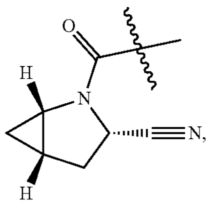,

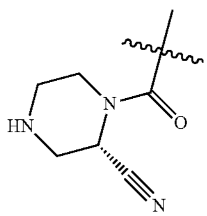, or

-continued

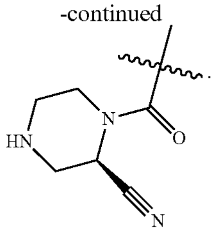.

Exemplary compounds of the disclosure are set forth in Table 1, below.

In some embodiments, compounds of the disclosure do not include compounds described in the PCT publication WO 2020/257790 and U.S. Pat. No. 10,525,048, incorporated herein by reference.

In some embodiments, compounds of the disclosure do not include compounds described in Kim et. al. J. Med. Chem. 2019, 62, 8429-8442 and Kim et. al. J. Med. Chem. 2021, 64, 5850-5862, incorporated herein by reference.

In some embodiments, compounds of the disclosure do not include compounds I-230 and I-202.

In some embodiments, compounds of the disclosure do not include compounds I-230, I-202, I-1, I-29, I-74, I-143 and I-174.

In some embodiments, the compound of the disclosure is compound P-1:

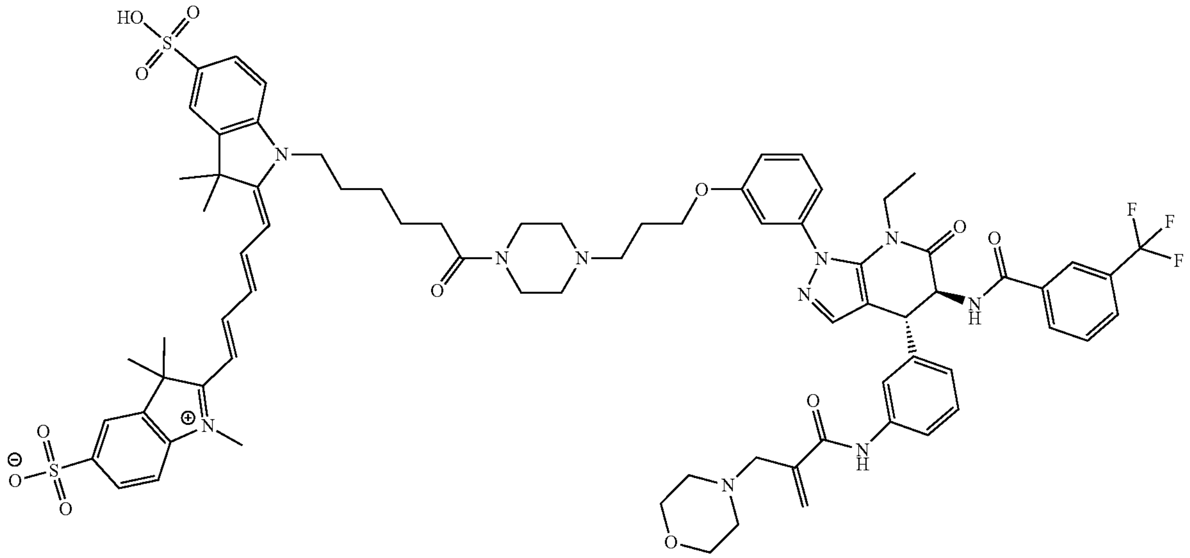 [SMILES: C=C(CN1CCOCC1)C(=O)Nc1cccc([C@@H]2c3cnn(-c4cccc(OCCCN5CCN(C(=O)CCCCCN6/C(=C/C=C/C=C/C7=[N+](C)c8ccc(S(=O)(=O)[O-])cc8C7(C)C)C(C)(C)c7cc(S(=O)(=O)O)ccc76)CC5)c4)c3N(CC)C(=O)[C@H]2NC(=O)c2cccc(C(F)(F)F)c2)c1]

or a pharmaceutically acceptable salt thereof. Compound P-1 or a pharmaceutically acceptable salt thereof may be used in any of the methods of use described herein.

In some embodiments, the present disclosure provides a compound selected from one of the following:
I-3a
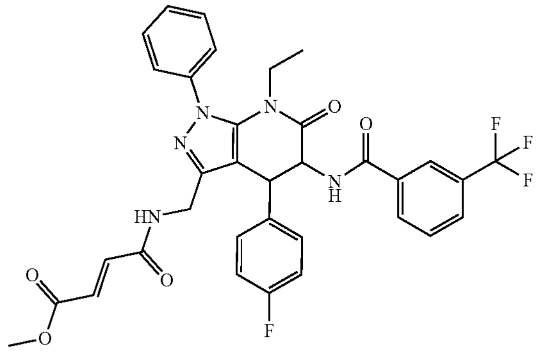
I-5a
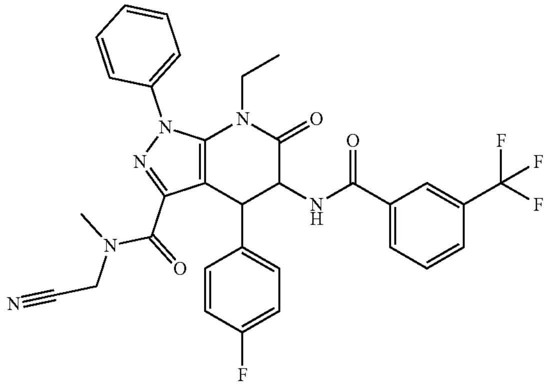
I-256a
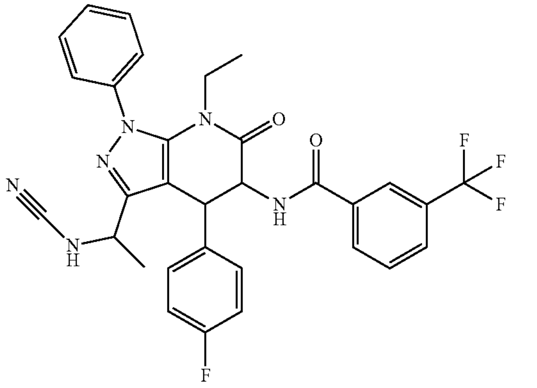
I-34a
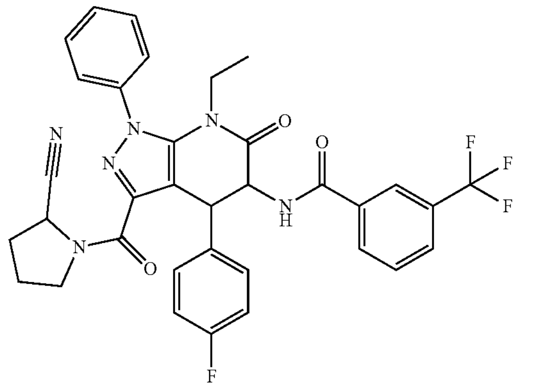
-continued
I-49a
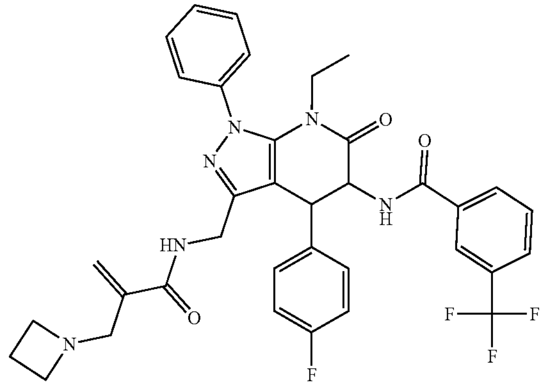
I-92a
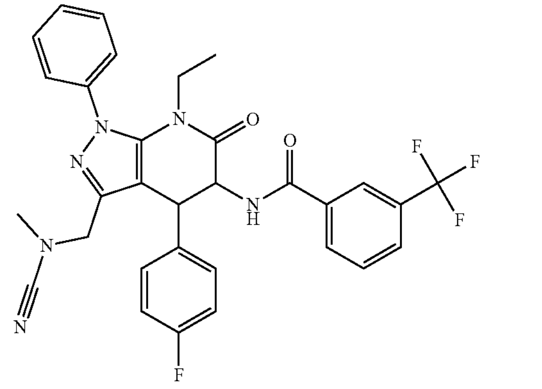
I-112a
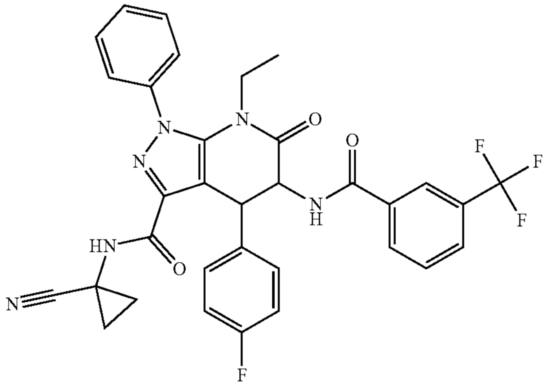
I-140a
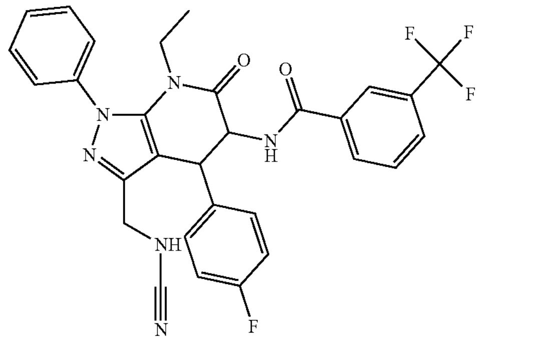

-continued
I-152a
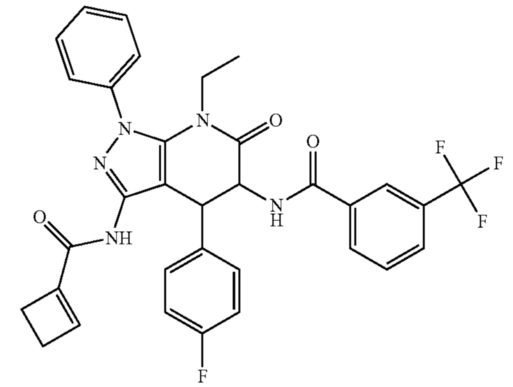
I-256b
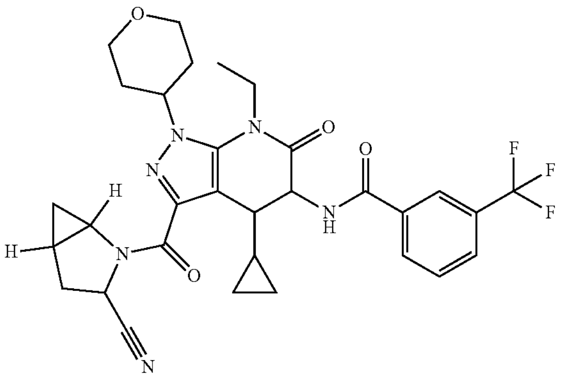
I-363a
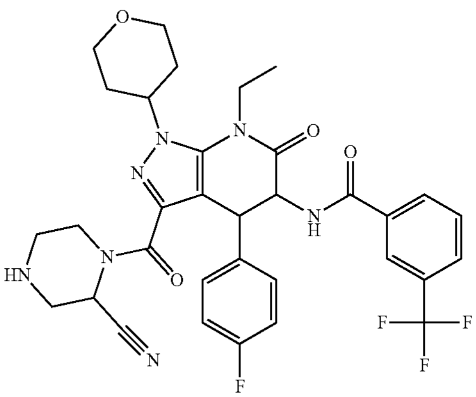
and
I-552a
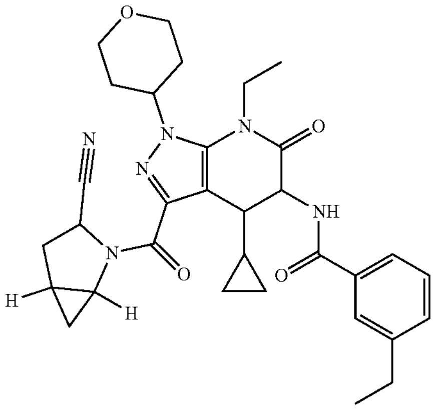
;
or a pharmaceutically acceptable salt thereof.
In some embodiments, the present disclosure provides a compound selected from one of the following:
I-3
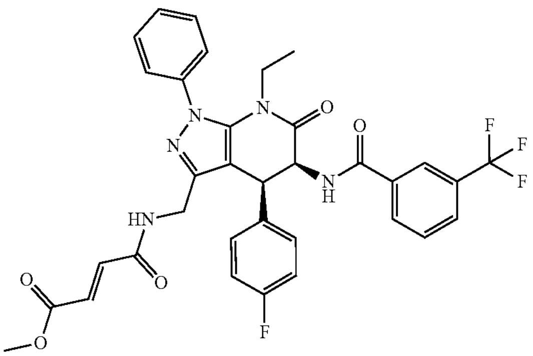
I-5
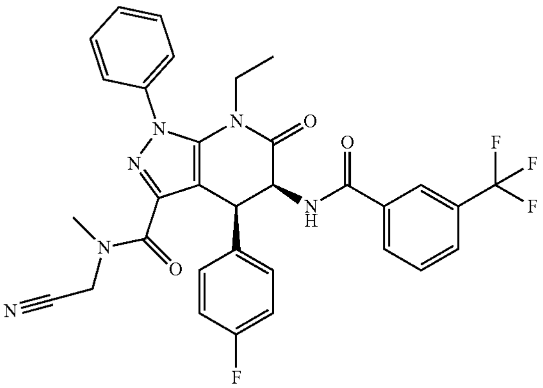
I-13
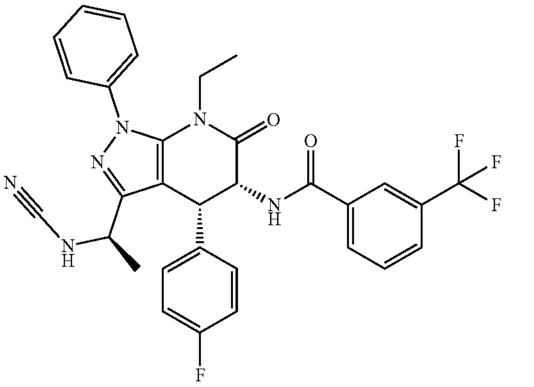

-continued
I-34
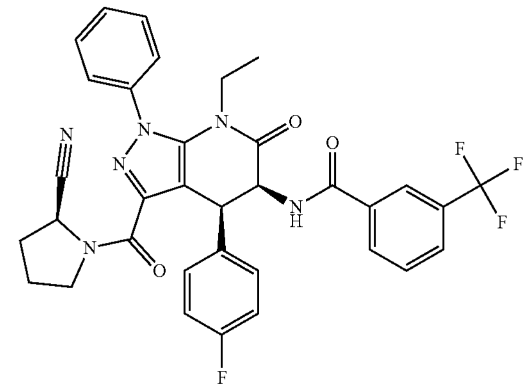
I-49
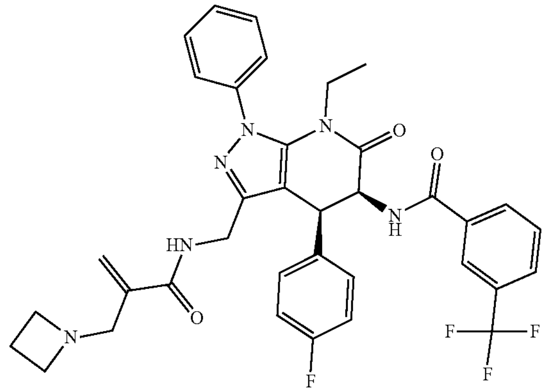
I-73
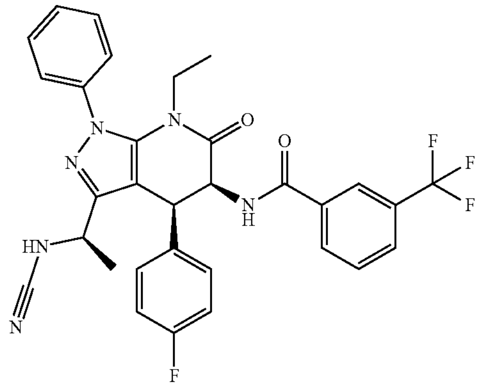
I-92
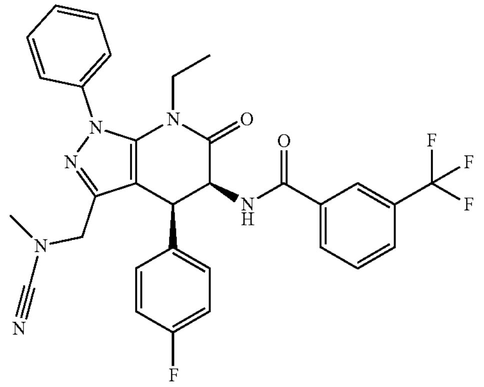
-continued
I-112
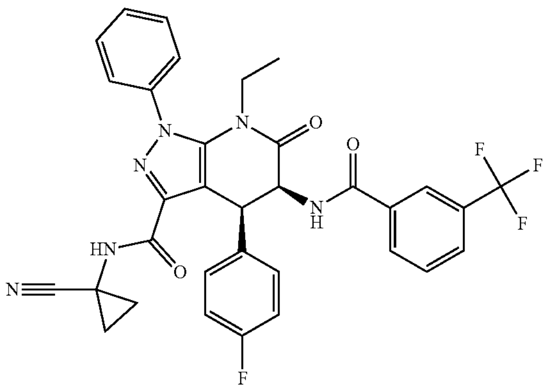
I-139
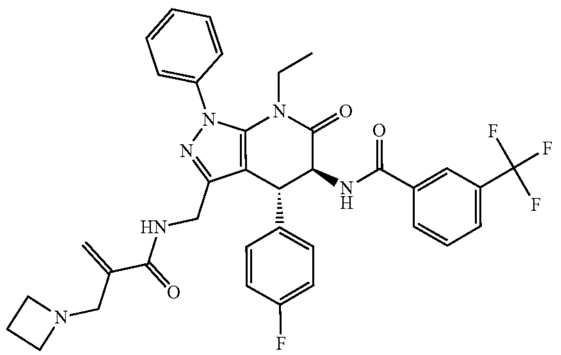
I-140
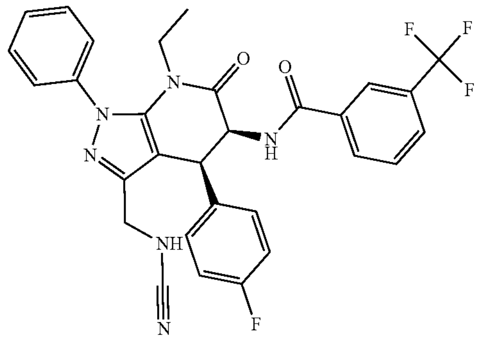
I-152
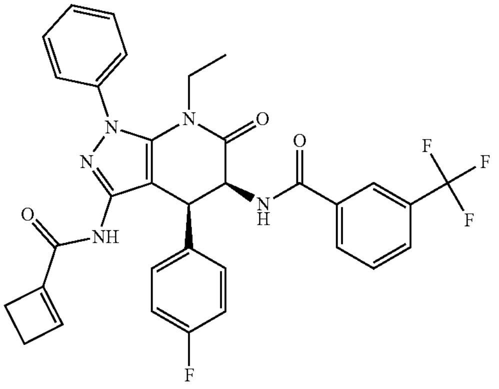

-continued

I-256

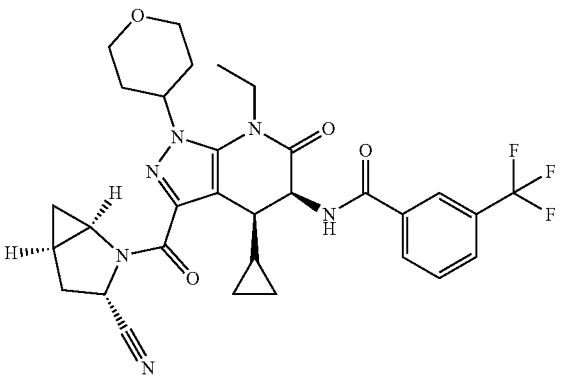

I-703

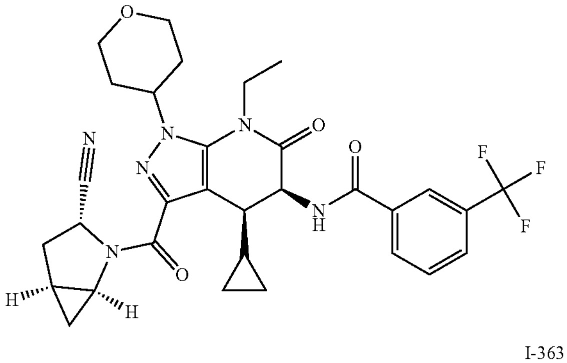

I-363

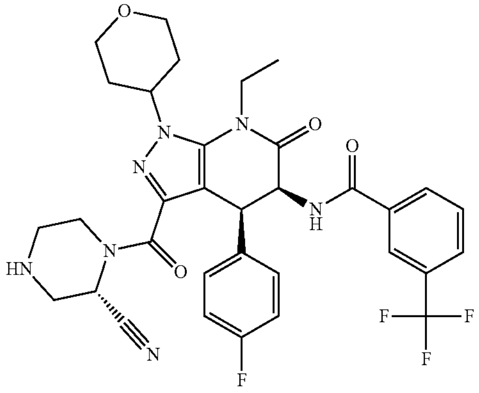

and

I-552

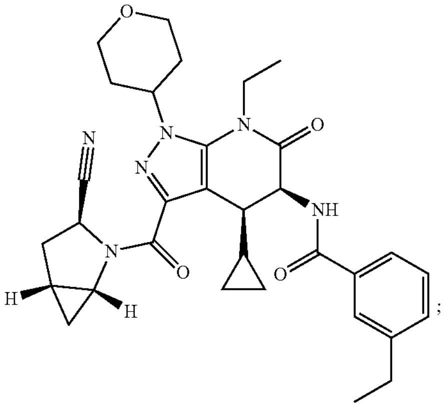

;

or a pharmaceutically acceptable salt thereof.

In some embodiments, the present disclosure provides a pharmaceutical composition comprising a disclosed compound, or a pharmaceutically acceptable salt thereof, and a pharmaceutically acceptable carrier.

In some embodiments, the present disclosure provides a compound shown in Table 1, below, or a pharmaceutically acceptable salt thereof.

Table 1. Exemplary Compounds

I-1

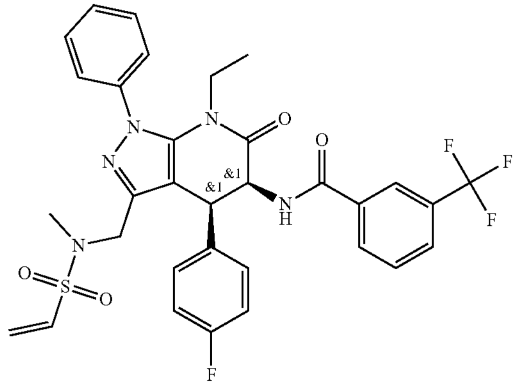

I-2

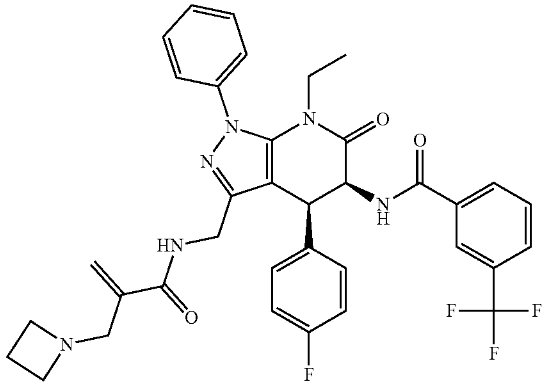

I-3

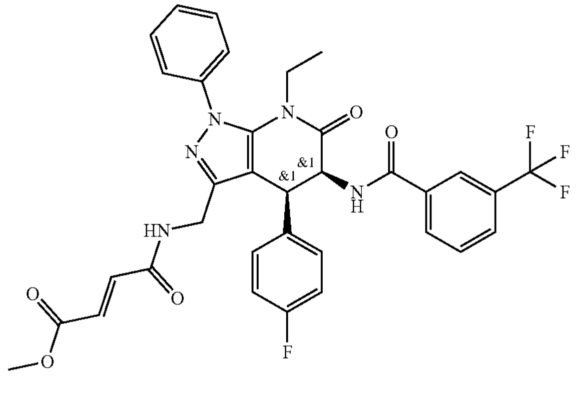

-continued
I-4
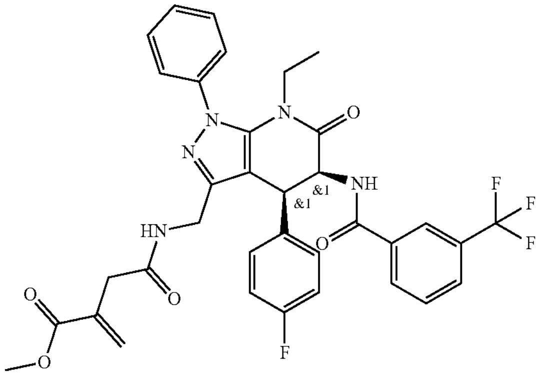
I-5
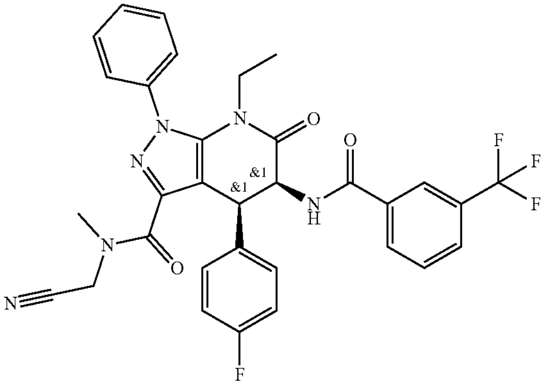
I-6
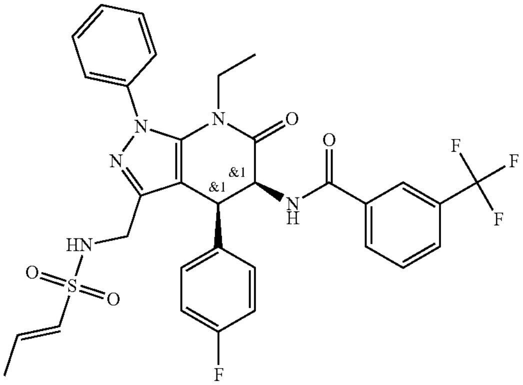
I-7
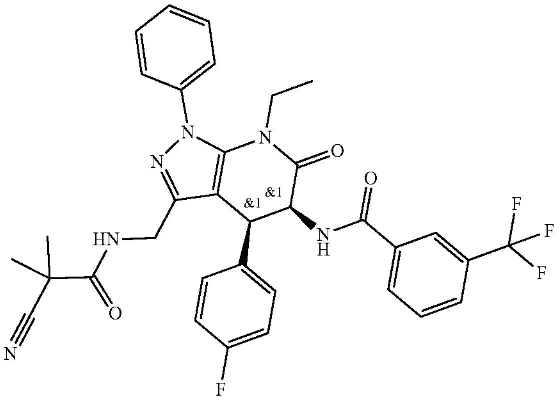
-continued
I-8
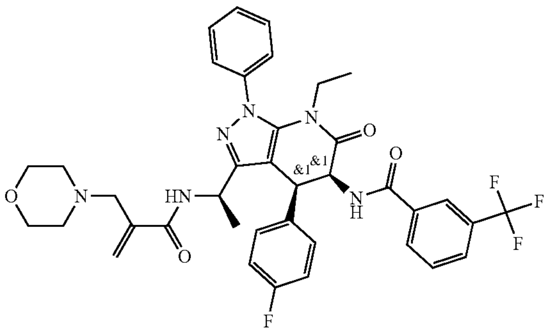
I-9
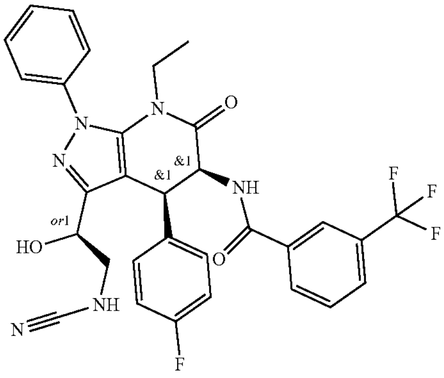
I-10
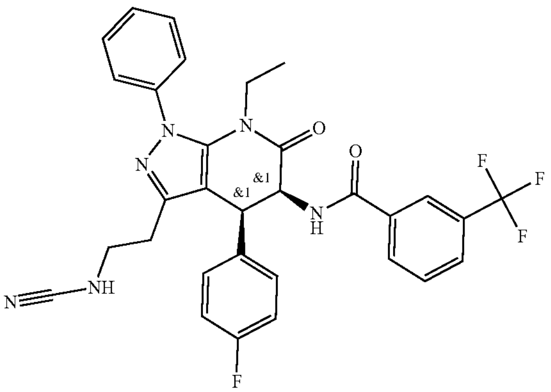
I-11
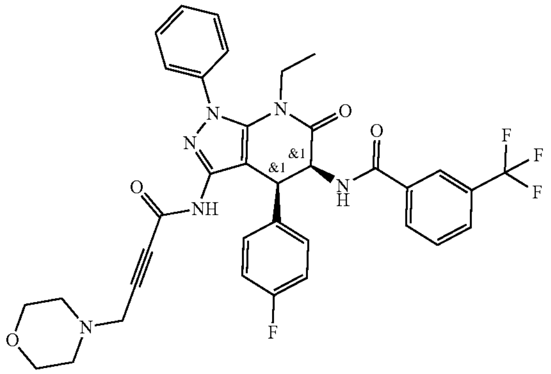

-continued
I-12
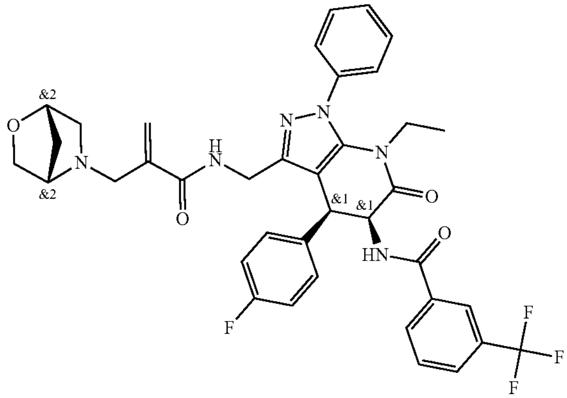
I-13
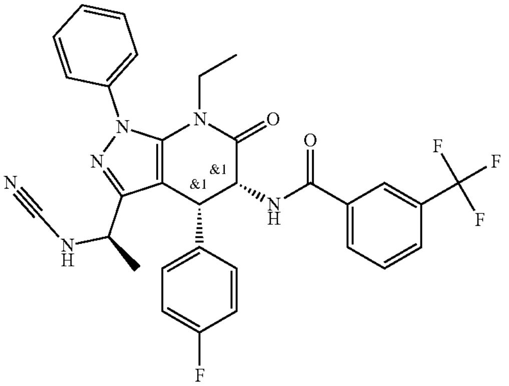
I-14
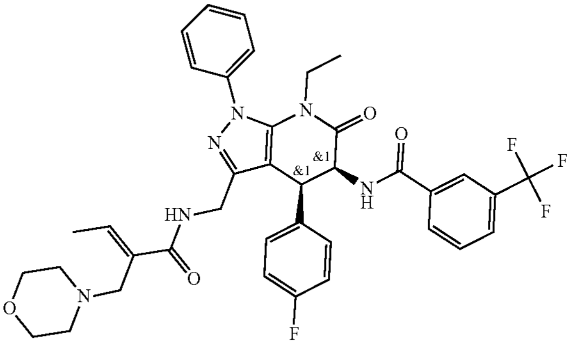
I-15
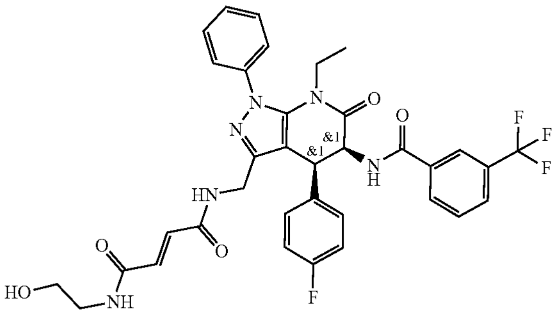
-continued
I-16
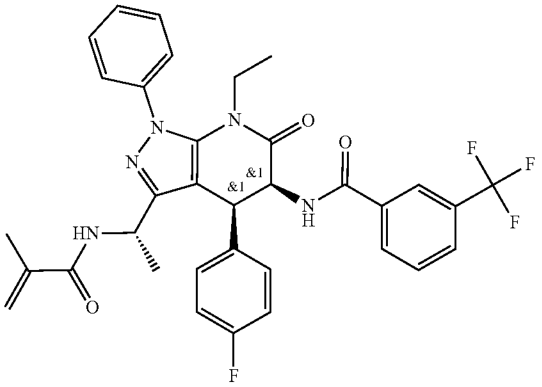
I-17
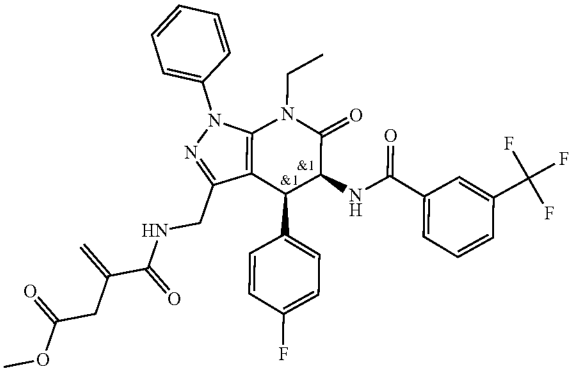
I-18
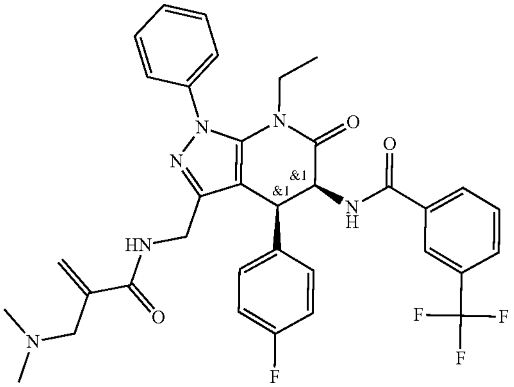
I-19
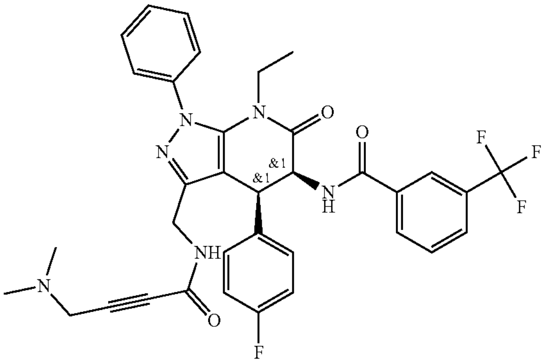

I-20
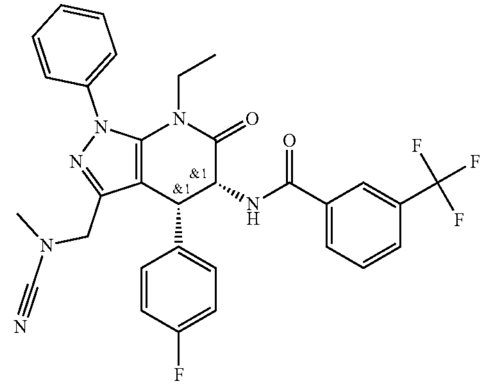
I-21
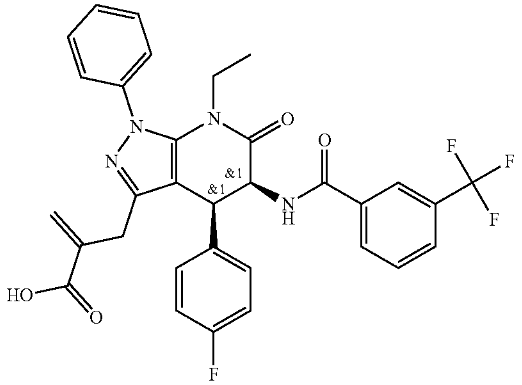
I-22
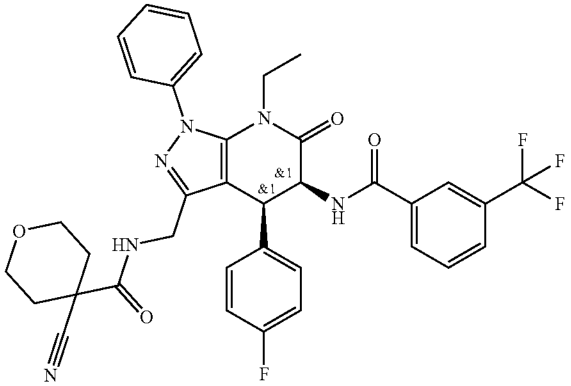
I-23
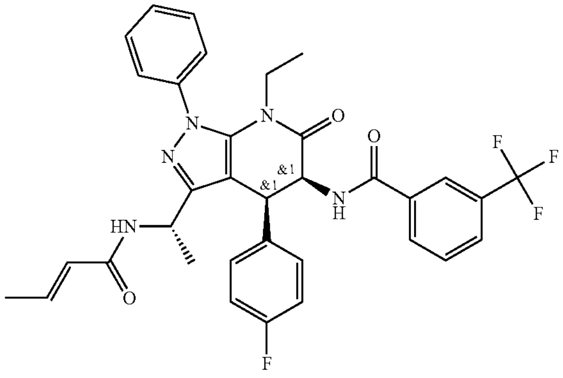
I-24
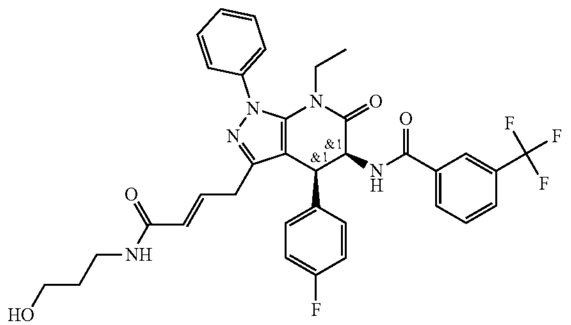
I-25
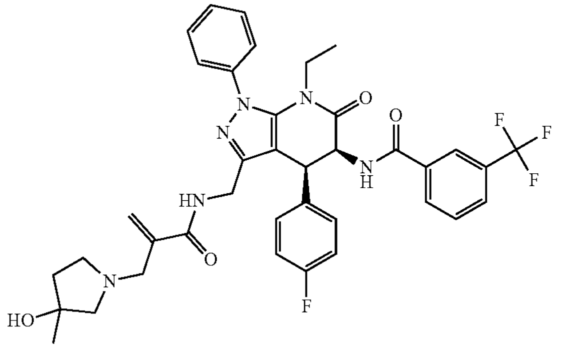
I-26
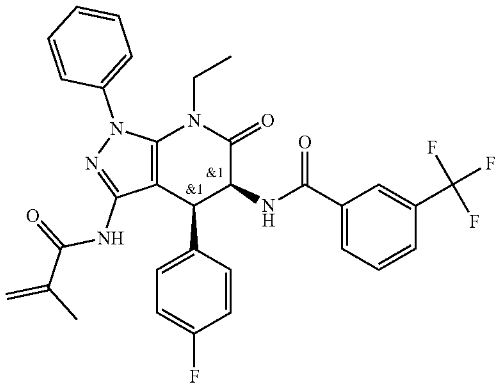
I-27
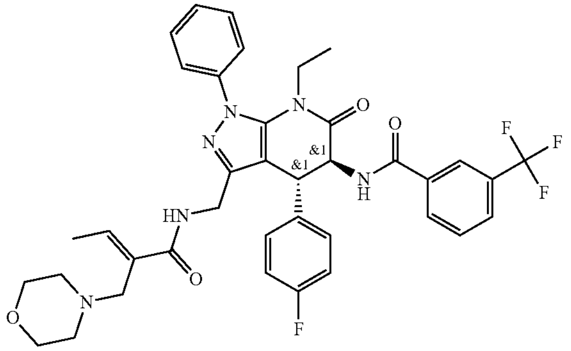

-continued
I-28
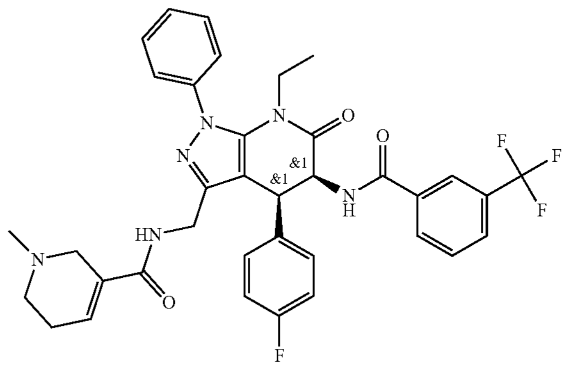
I-29
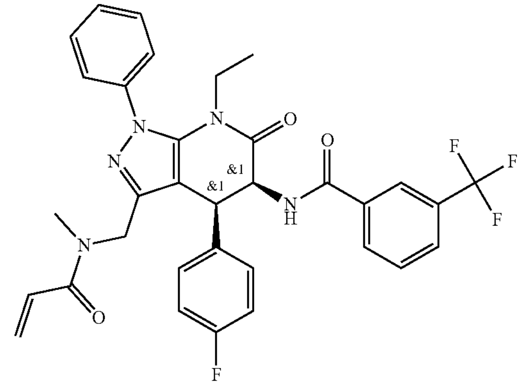
I-30
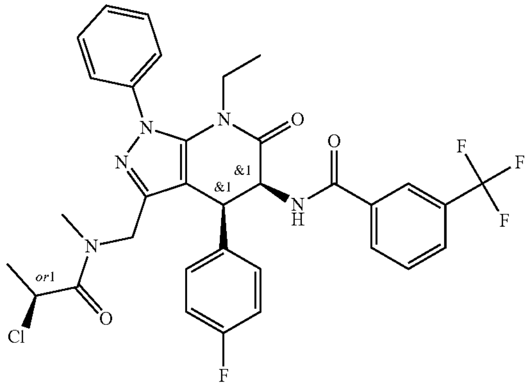
I-31
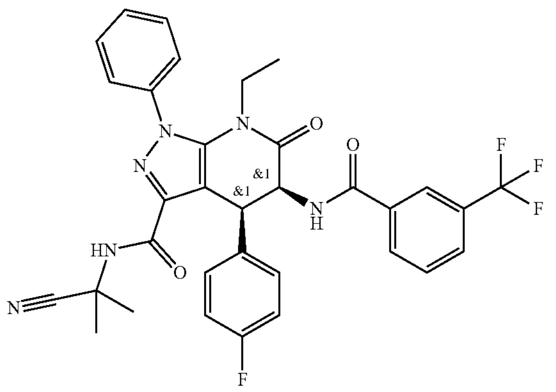
-continued
I-32
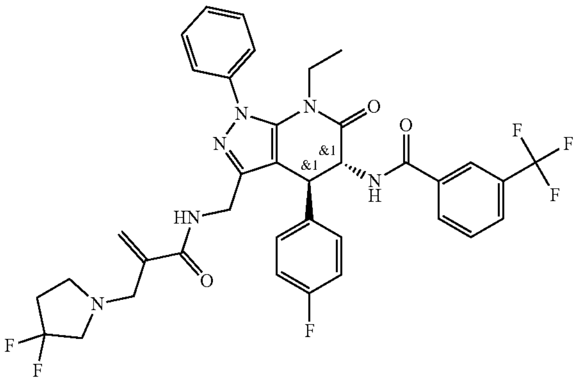
I-33
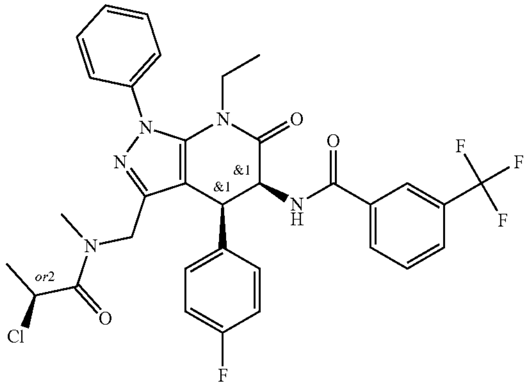
I-34
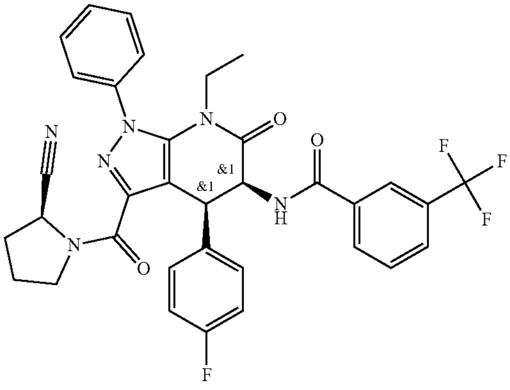
I-35
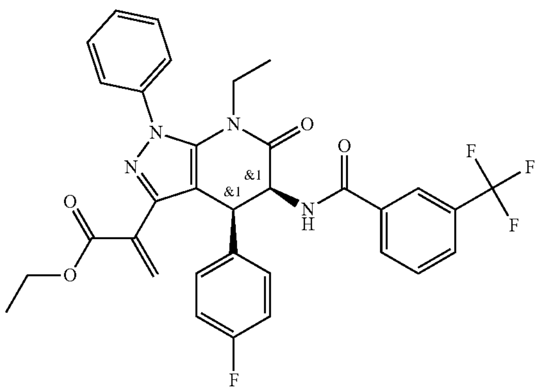

I-36
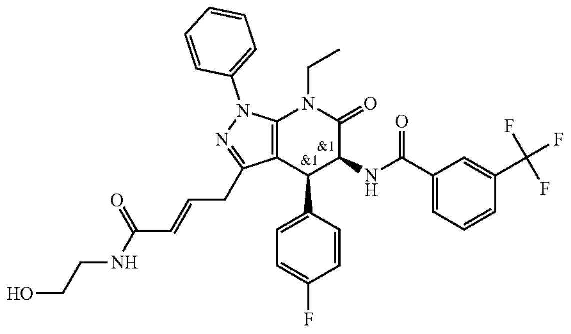
I-37
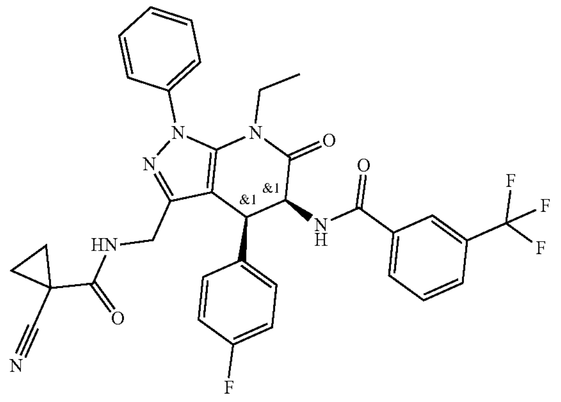
I-38
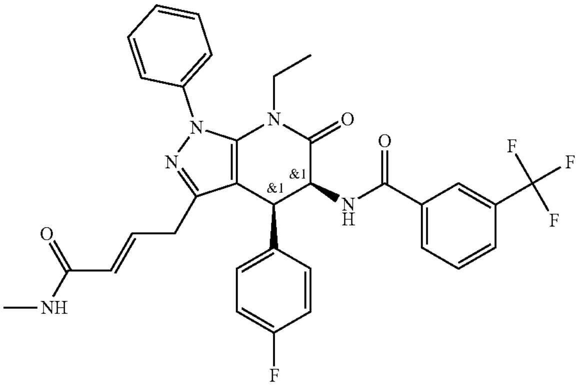
I-39
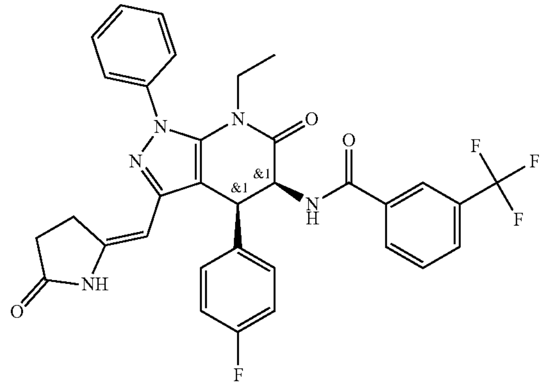
I-40
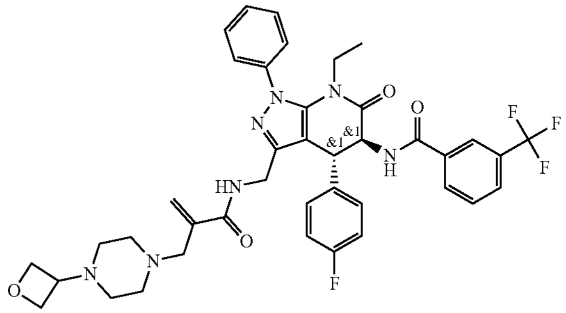
I-41
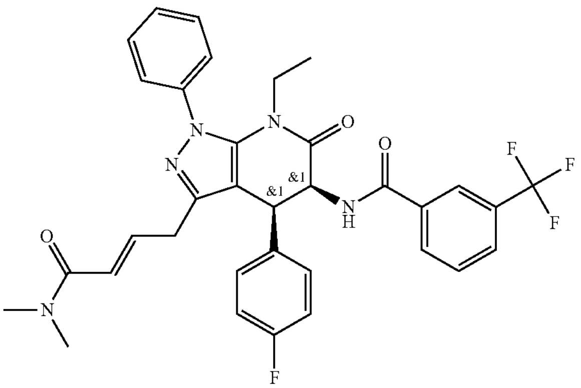
I-42
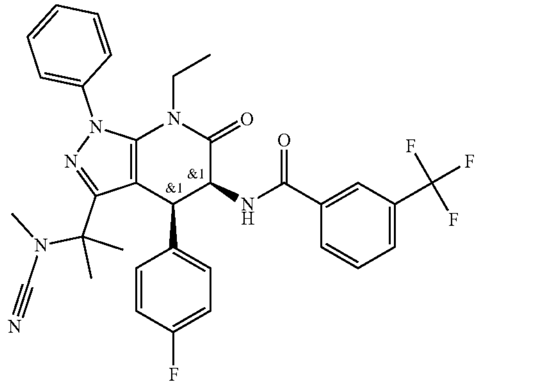

I-43
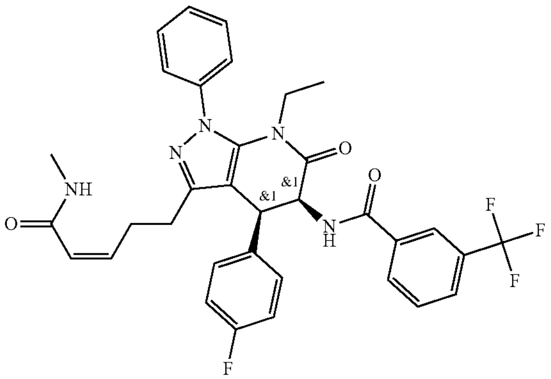
I-44
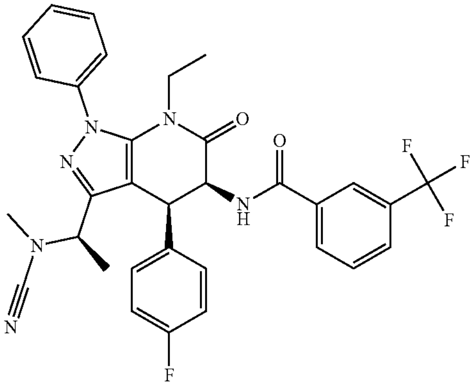
I-45
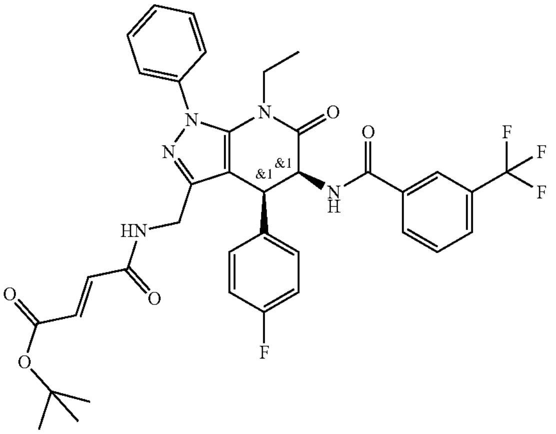
I-46
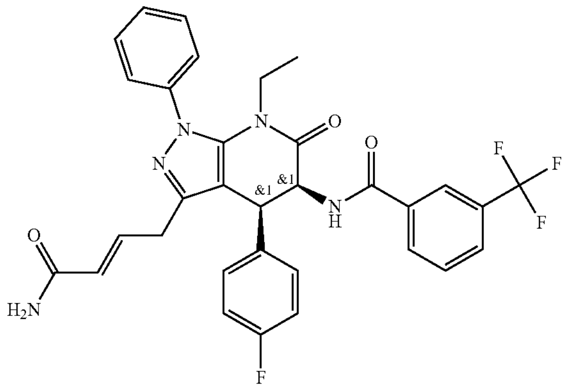
I-47
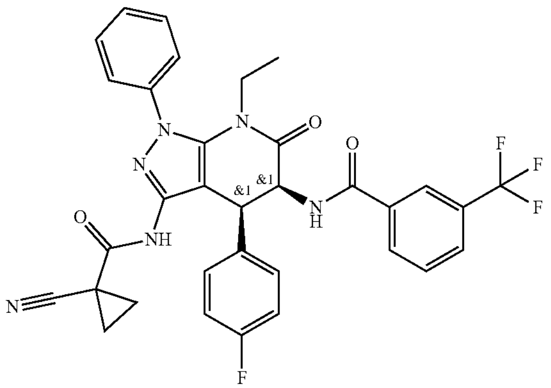
I-48
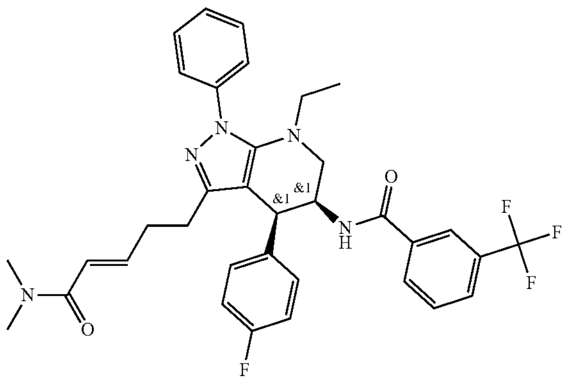
I-49
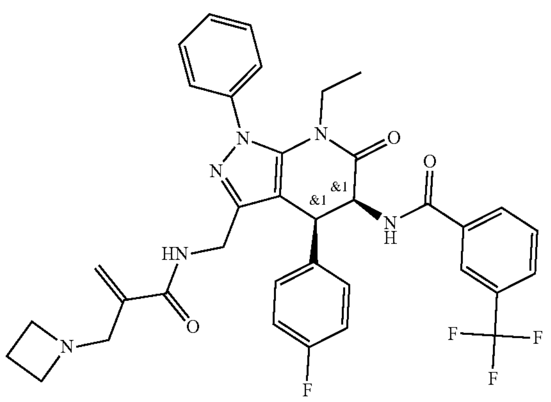

I-50
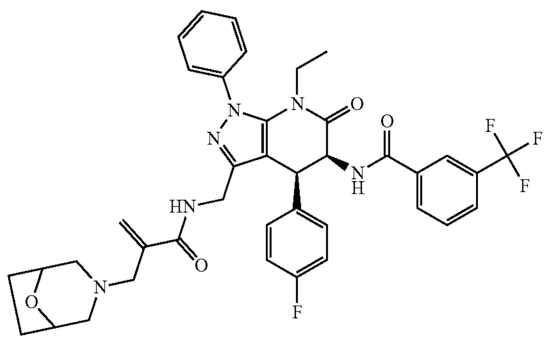
I-51
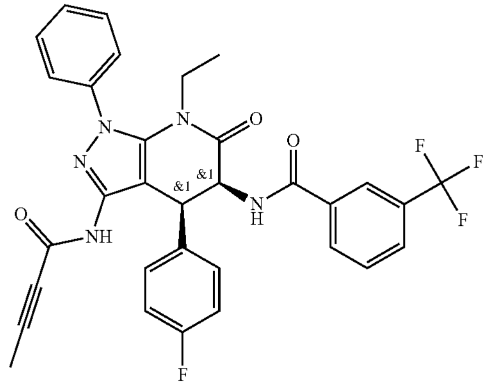
I-52
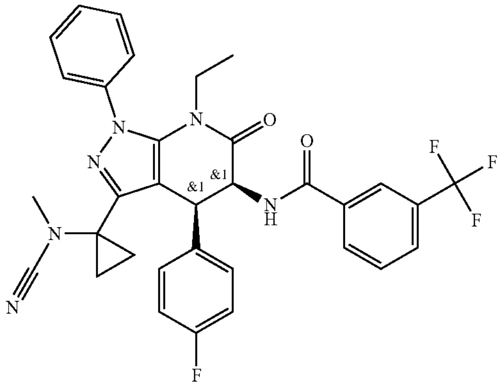
I-53
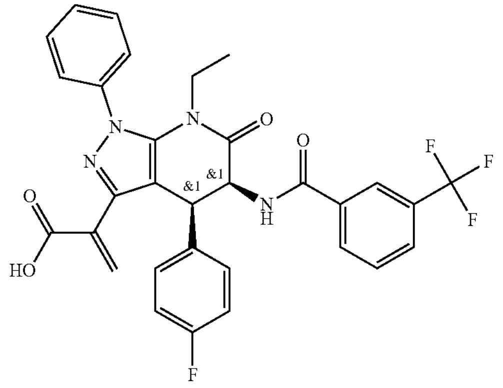
I-54
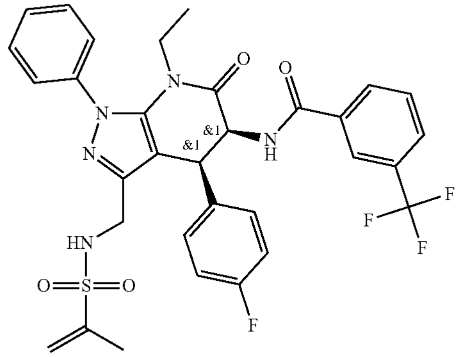
I-55
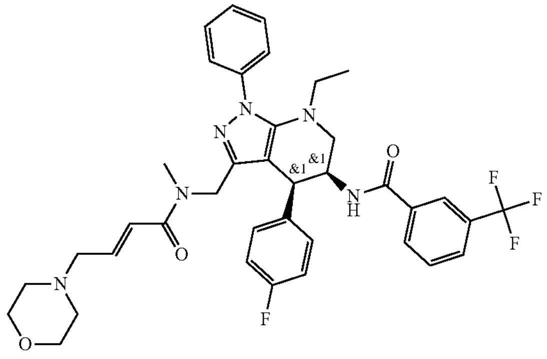
I-56
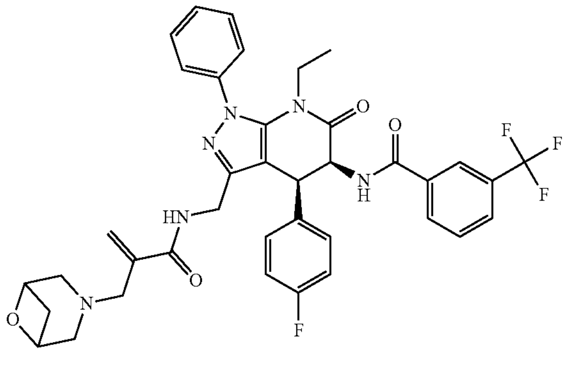
I-57
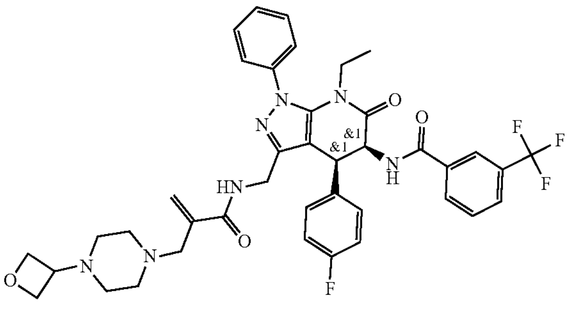

-continued
I-58
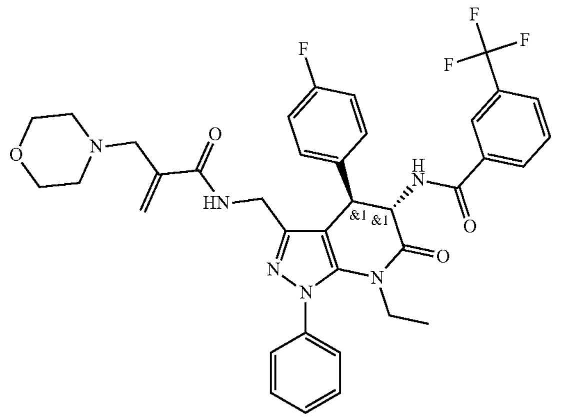
I-59
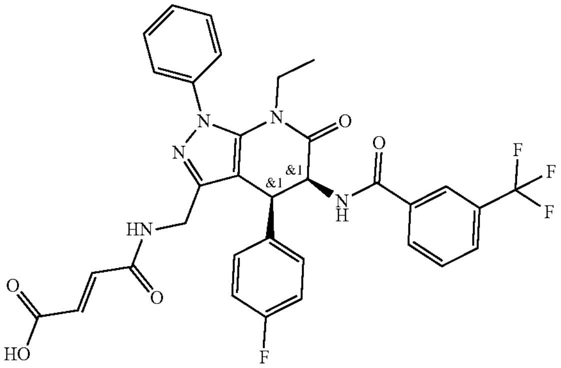
I-60
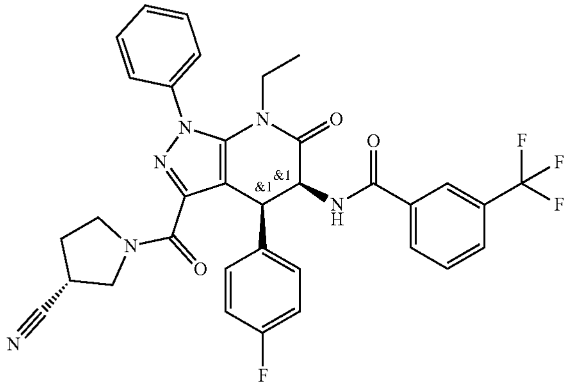
I-61
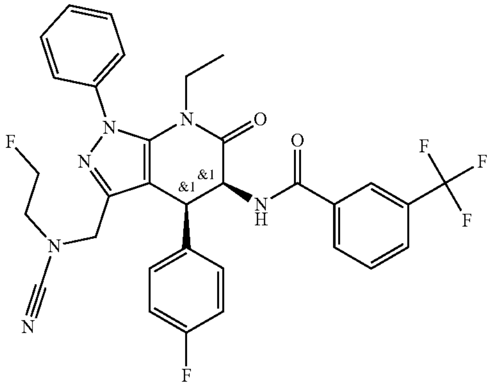
-continued
I-62
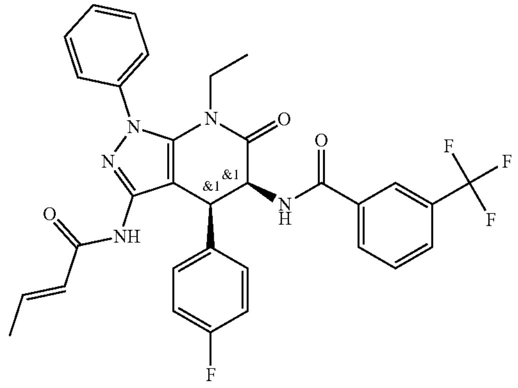
I-63
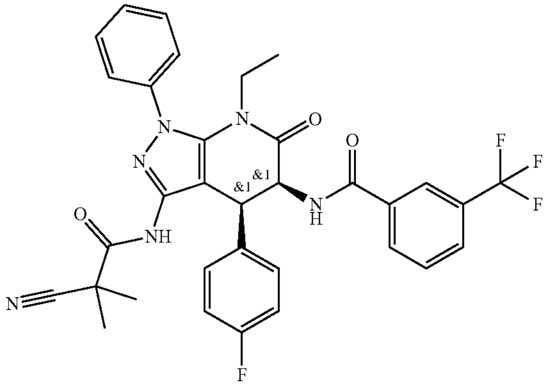
I-64
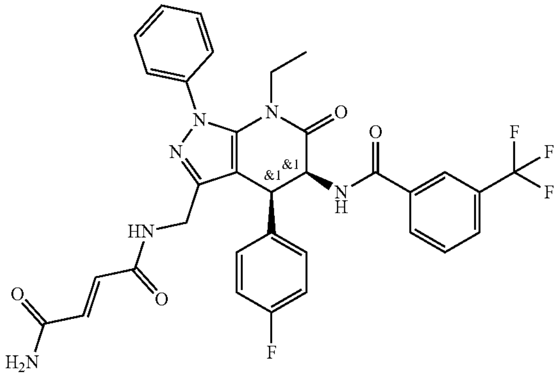
I-65
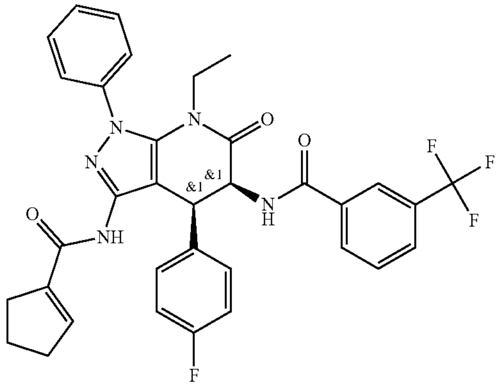

-continued
I-66
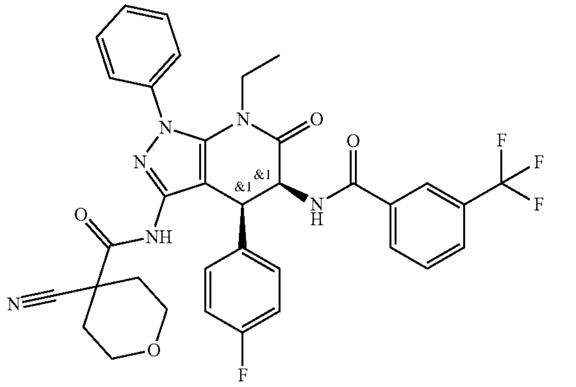
I-67
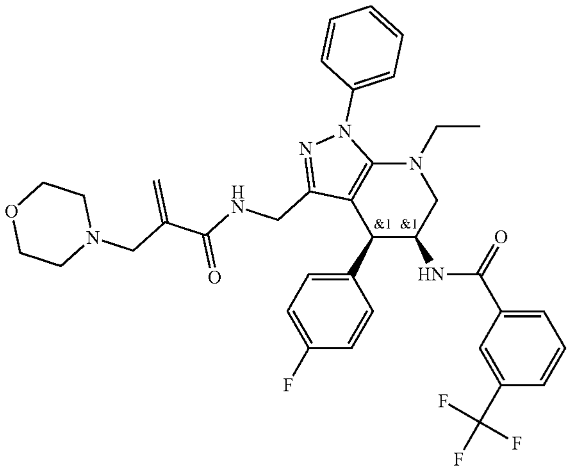
I-68
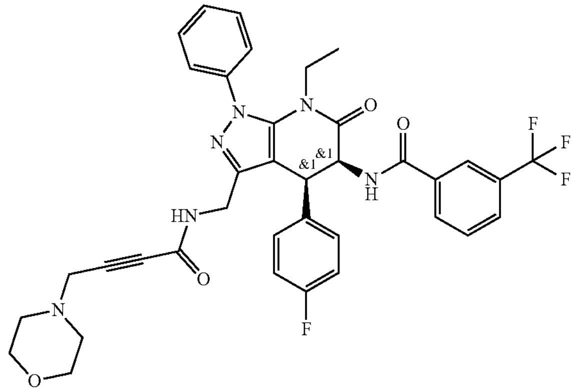
-continued
I-69
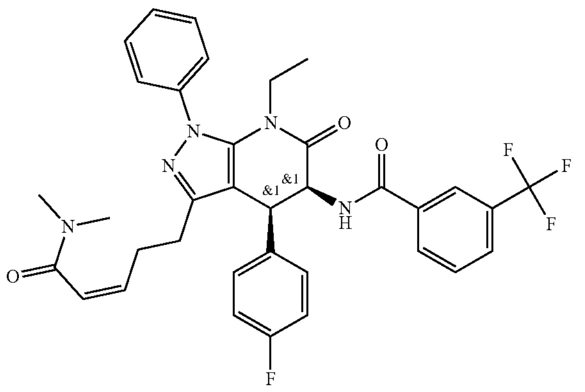
I-70
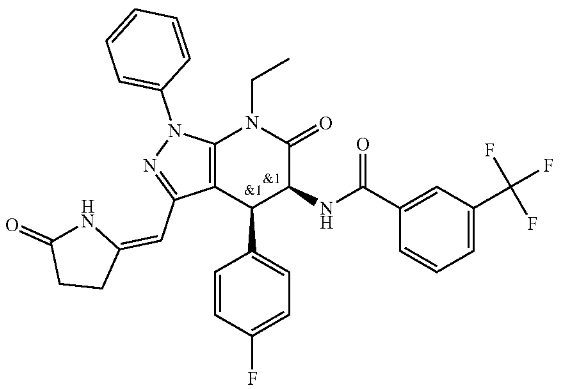
I-71
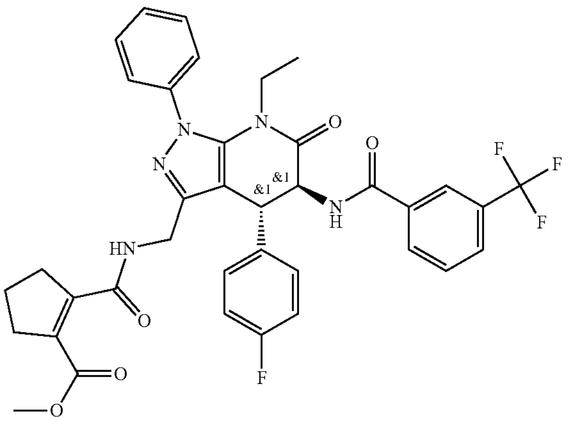
I-72
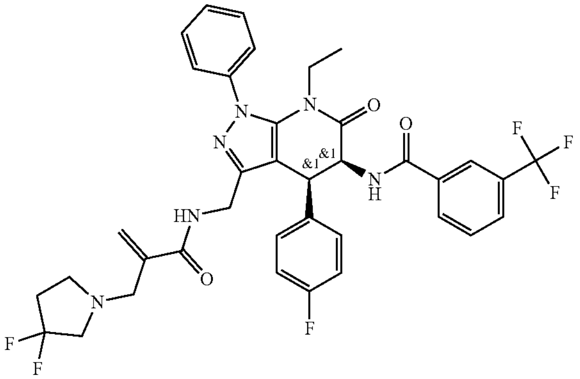

-continued
I-73
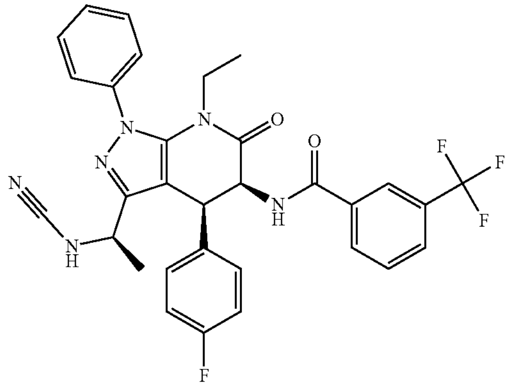
I-74
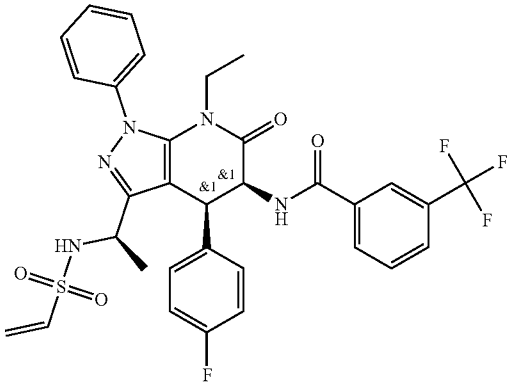
I-75
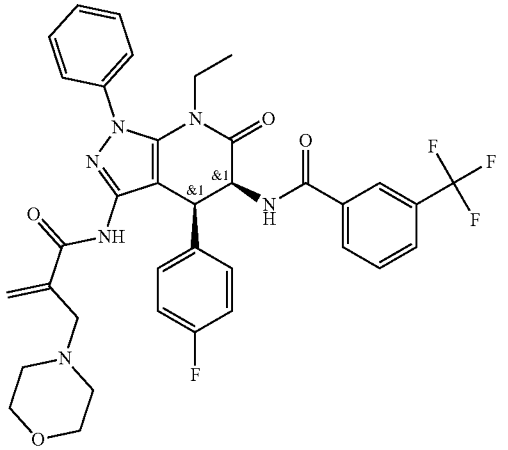
-continued
I-76
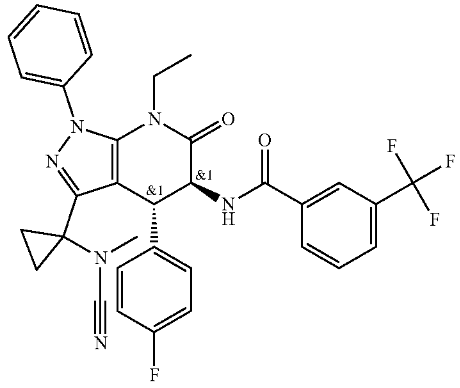
I-77
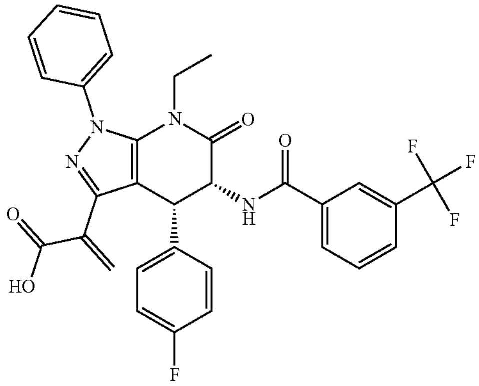
I-78
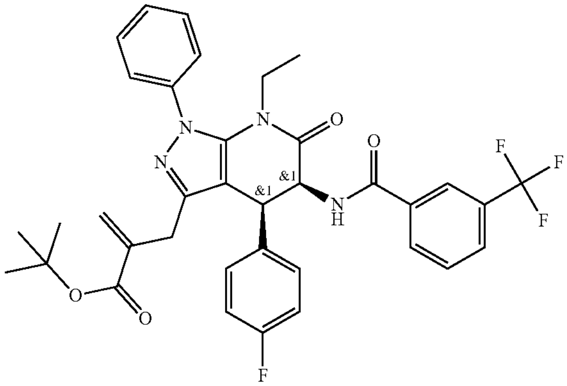
I-79
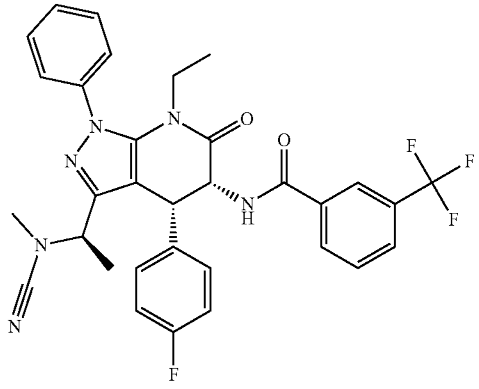

-continued
I-80
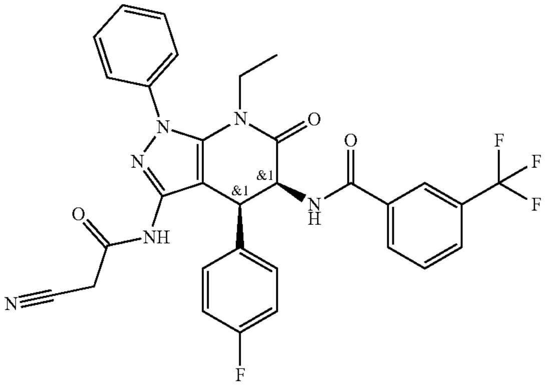
I-81
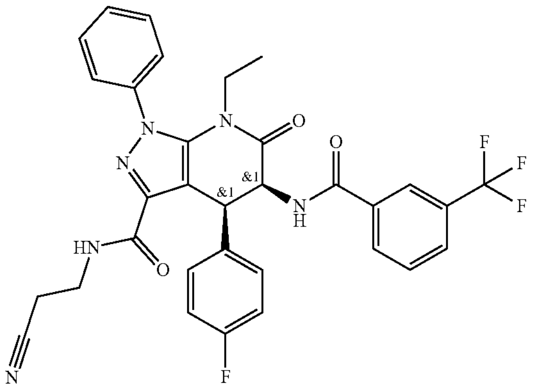
I-82
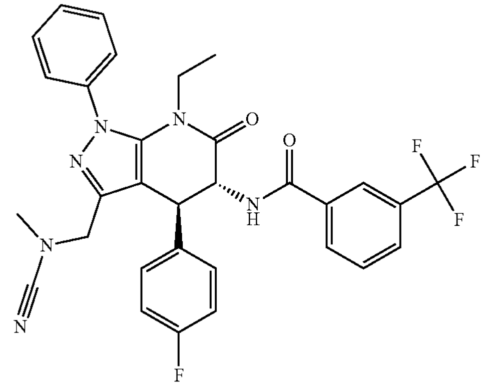
I-83
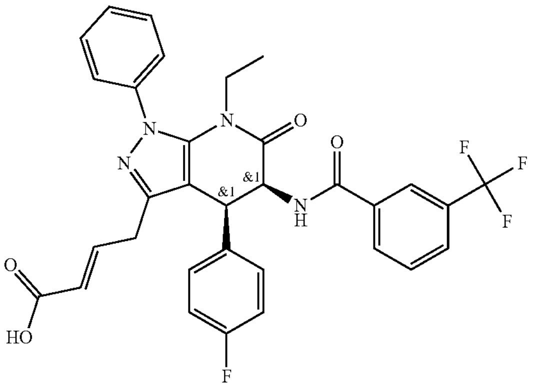
-continued
I-84
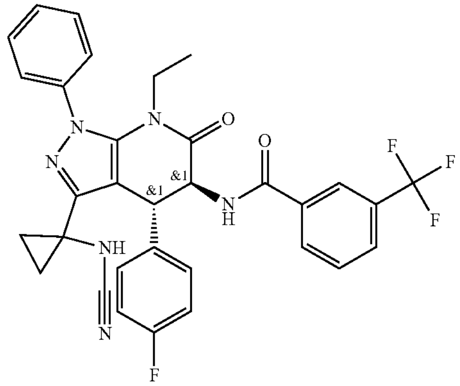
I-85
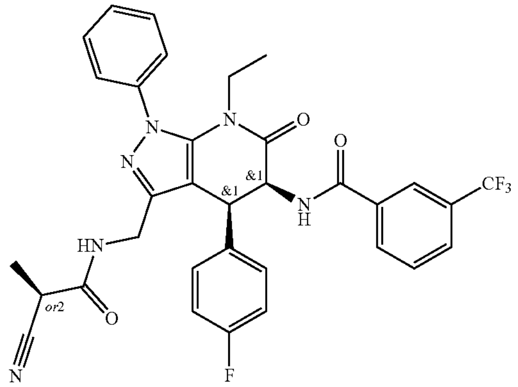
I-86
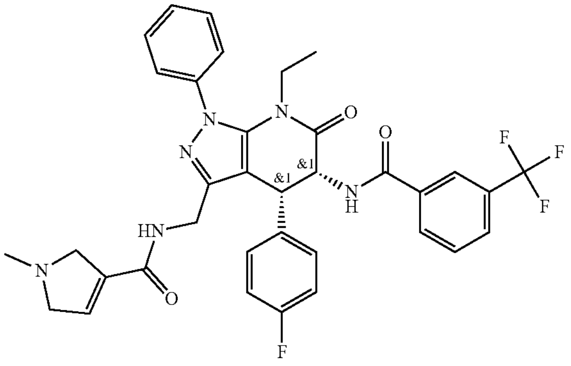
I-87
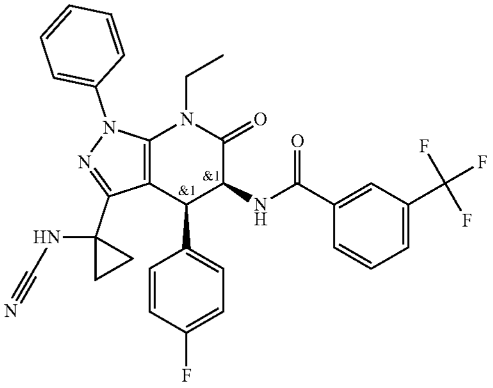

I-88
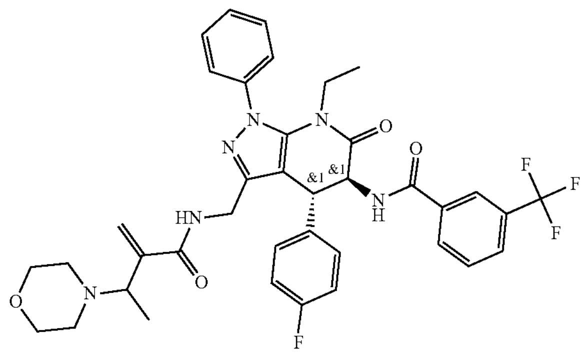
I-89
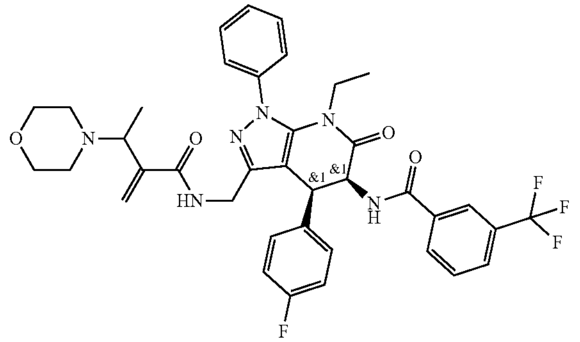
I-90
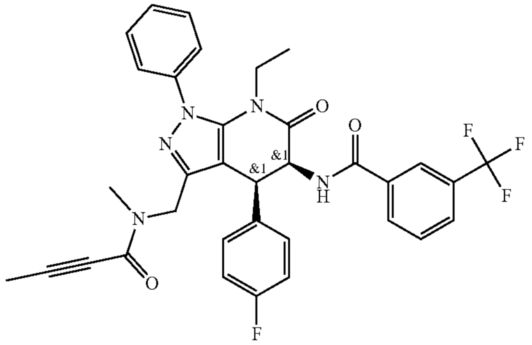
I-91
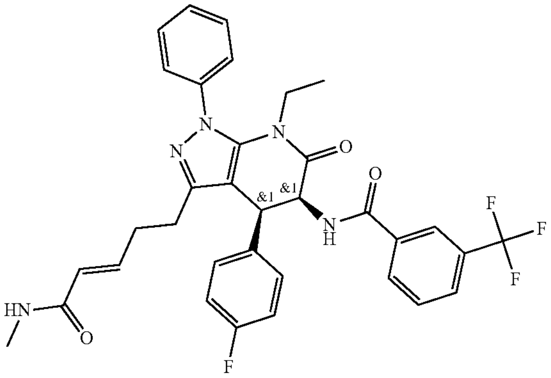
I-92
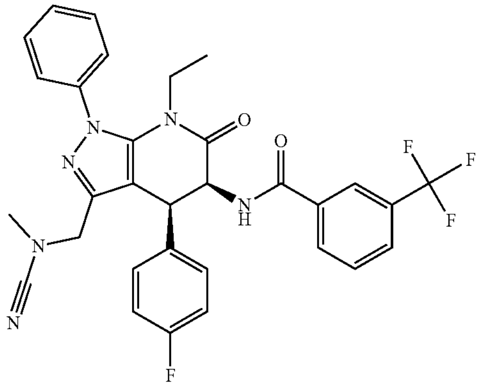
I-93
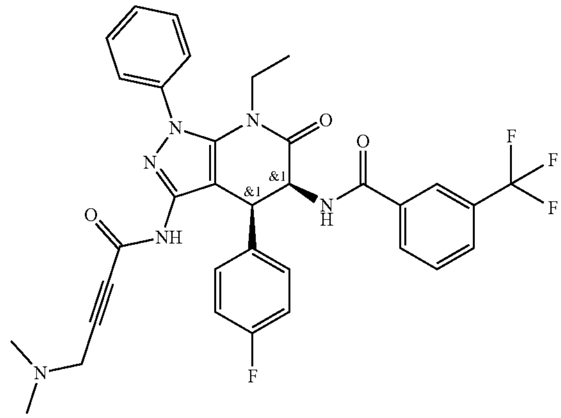
I-94
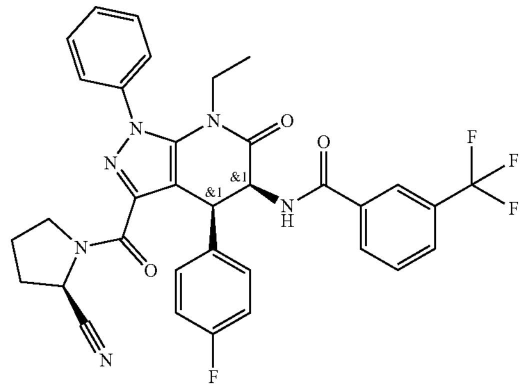
I-95
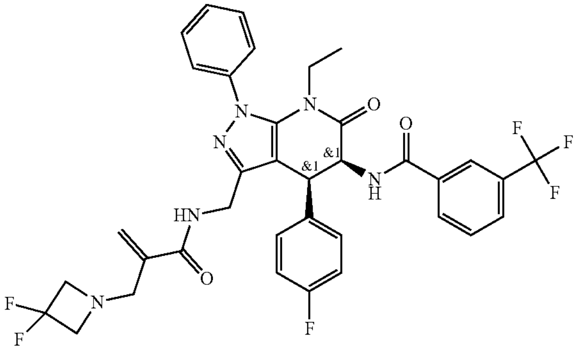

-continued
I-96
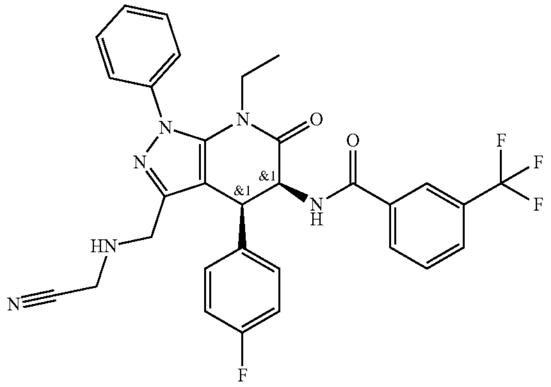
I-97
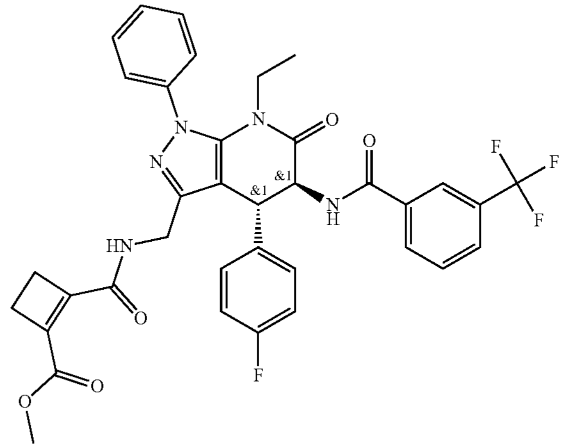
I-98
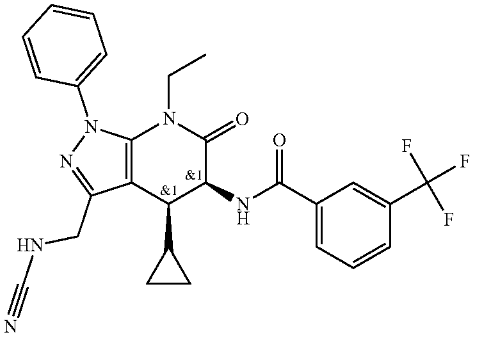
I-99
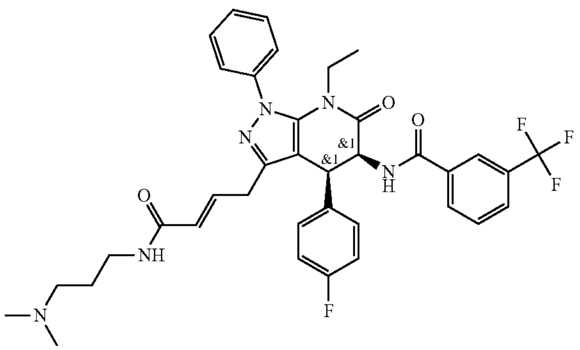
-continued
I-100
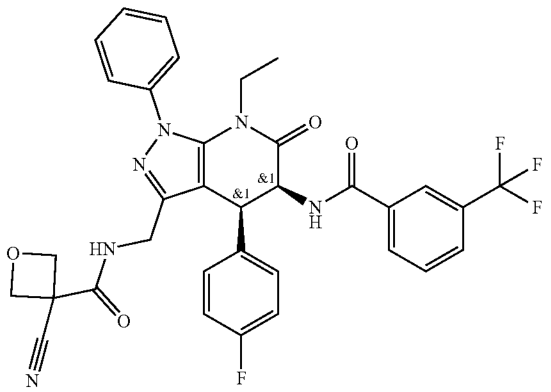
I-101
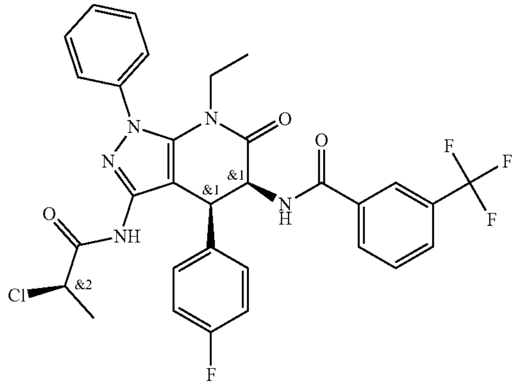
I-102
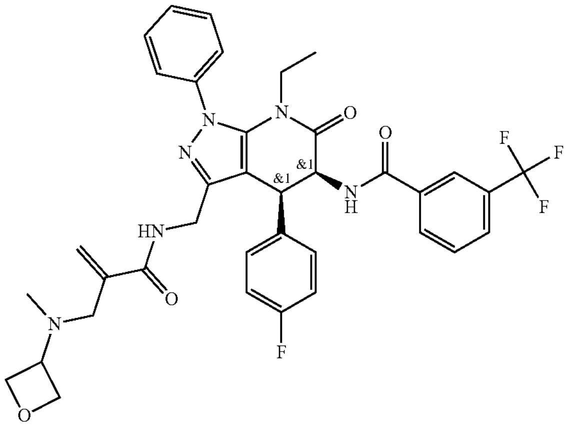
I-103
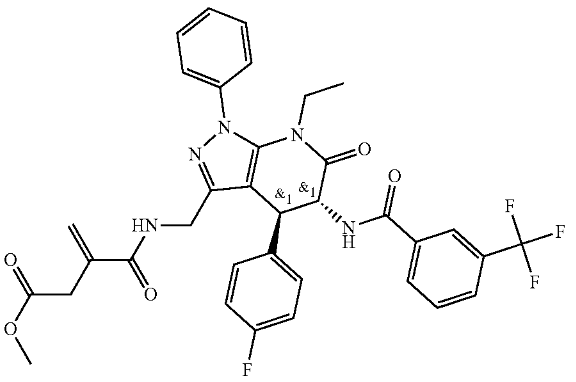

-continued
I-104
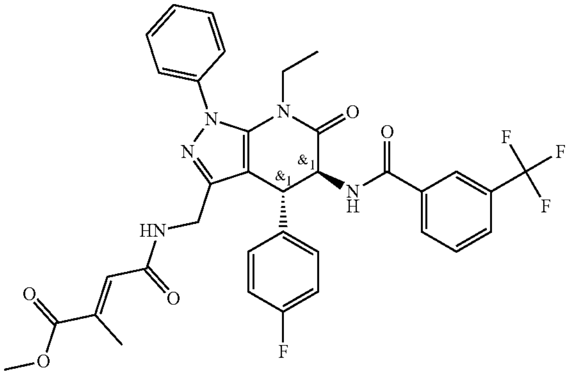
I-105
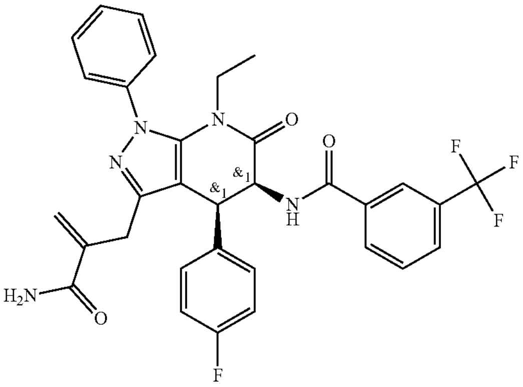
I-106
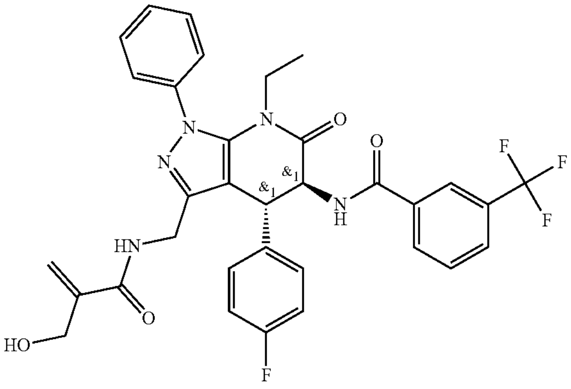
I-107
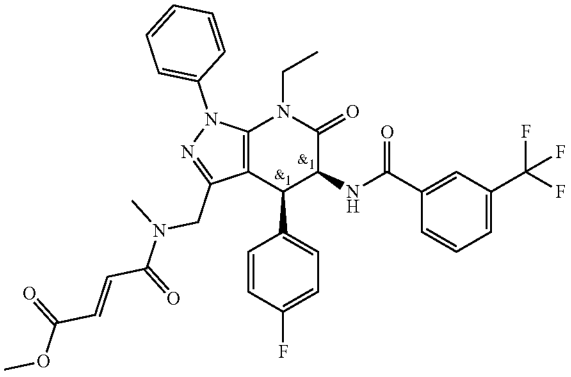
-continued
I-108
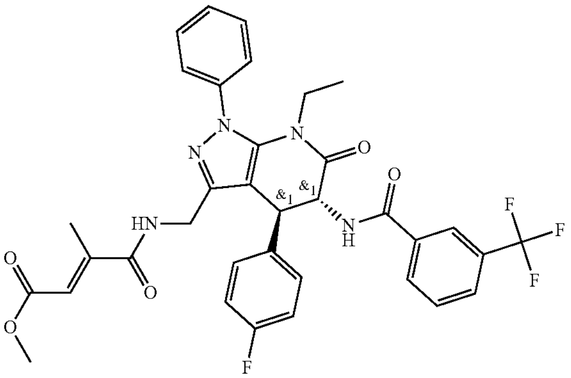
I-109
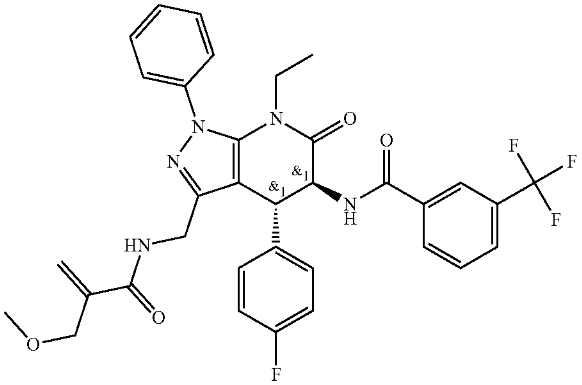
I-110
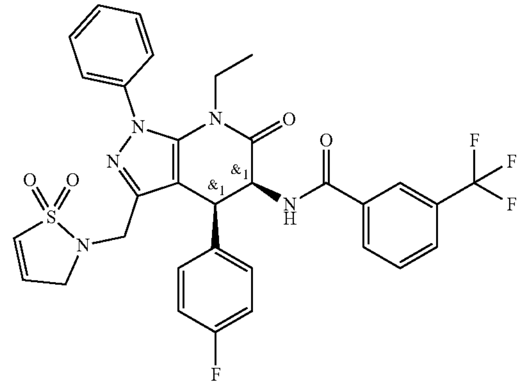
I-111
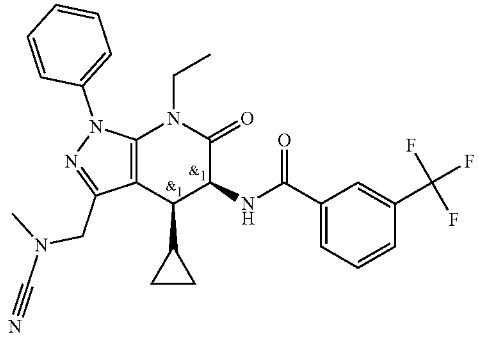

-continued
I-112
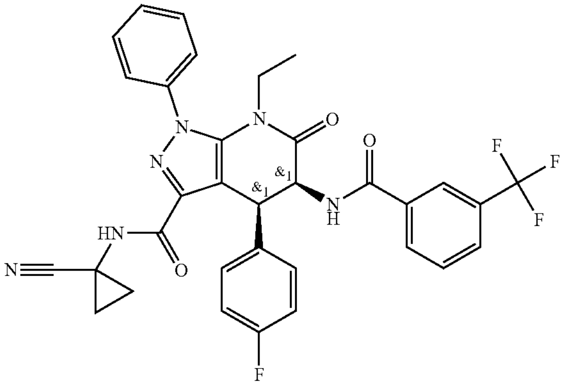
I-113
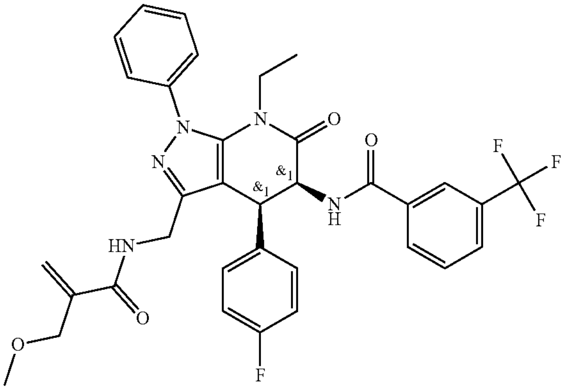
I-114
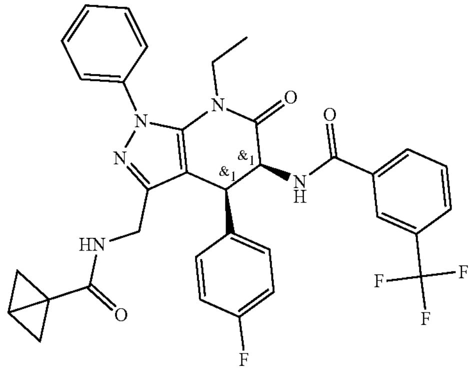
I-115
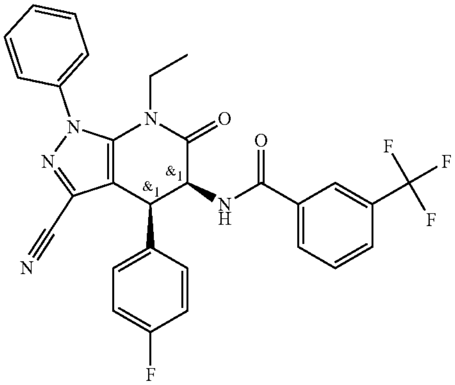
-continued
I-116
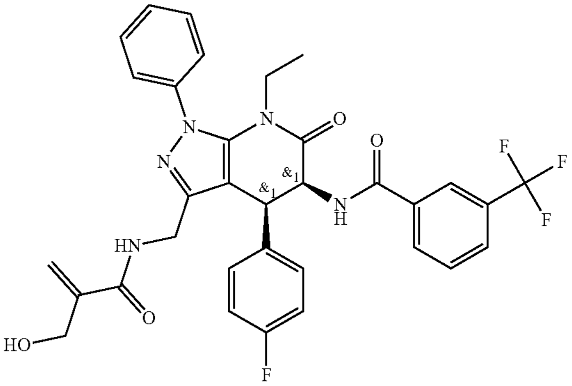
I-117
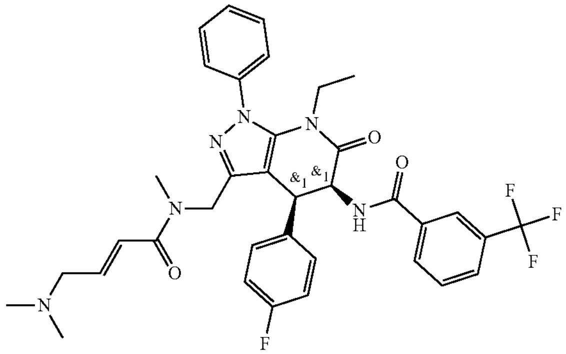
I-118
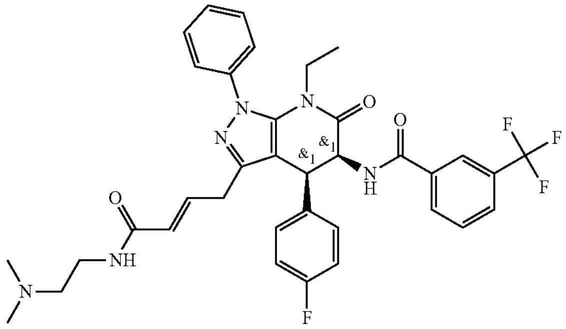

-continued
I-119
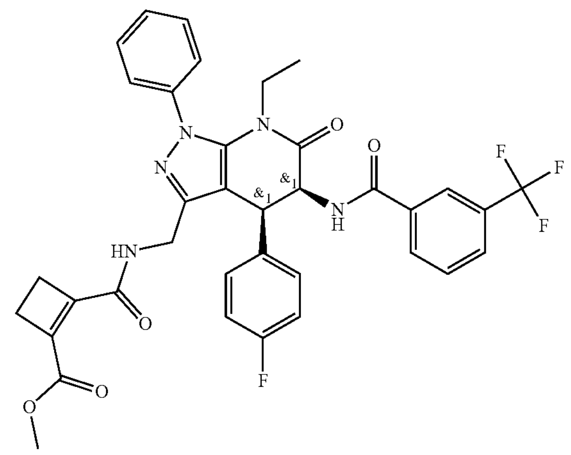
I-120
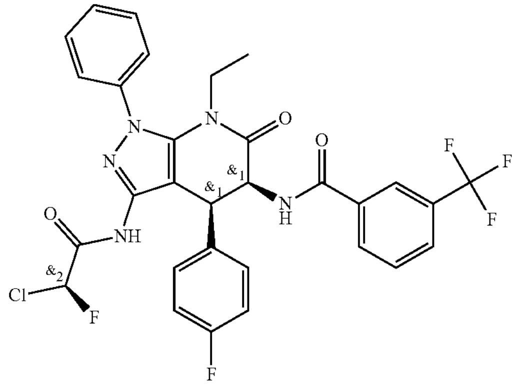
I-121
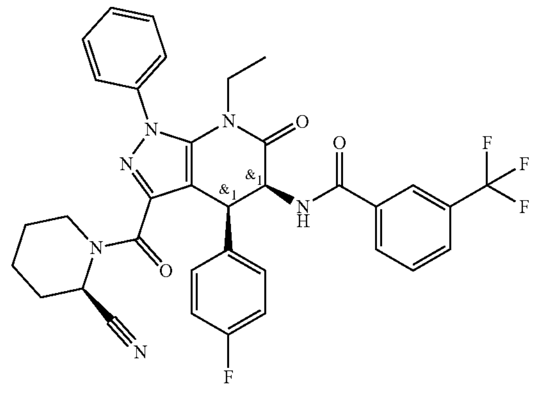
-continued
I-122
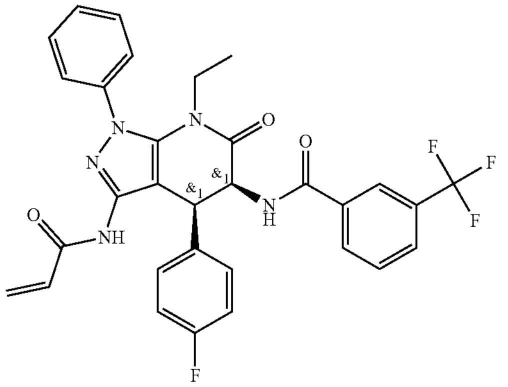
I-123
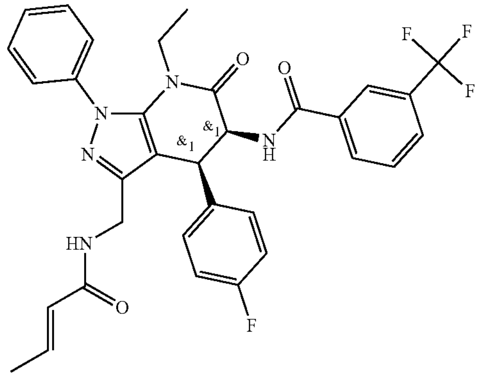
I-124
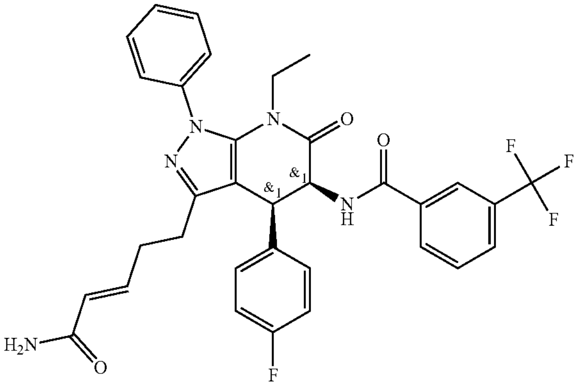
I-125
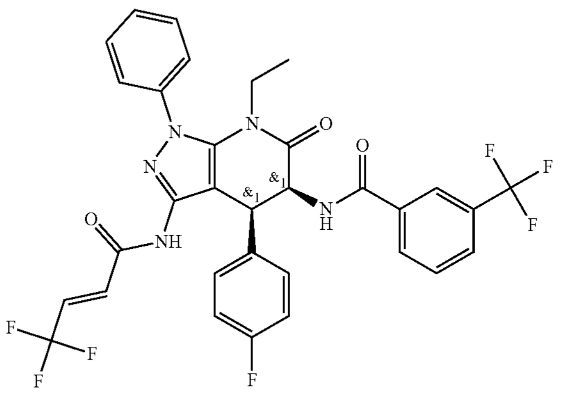

-continued
I-126
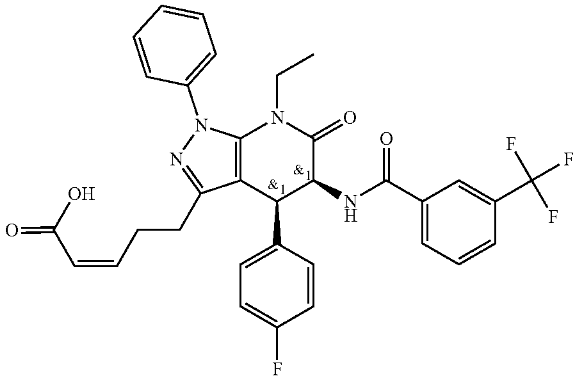
I-127
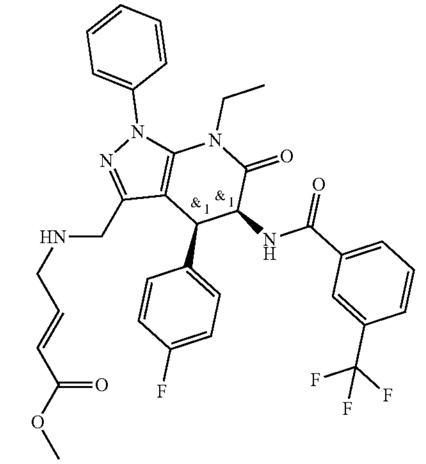
I-128
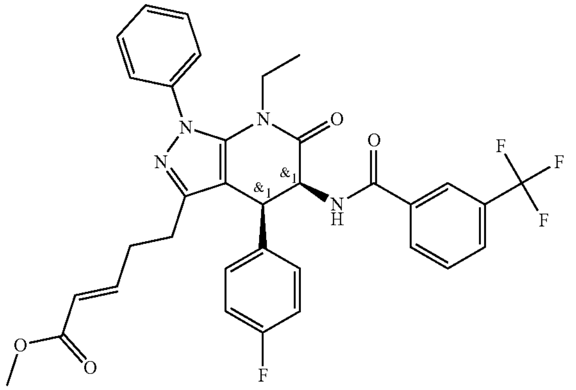
-continued
I-129
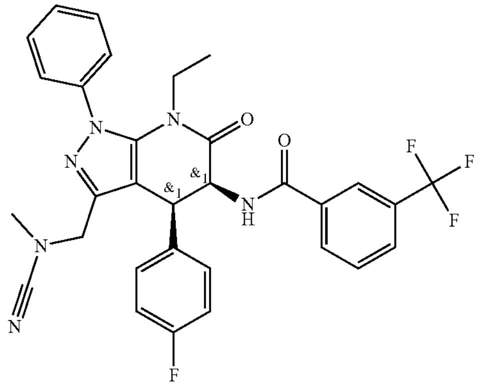
I-130
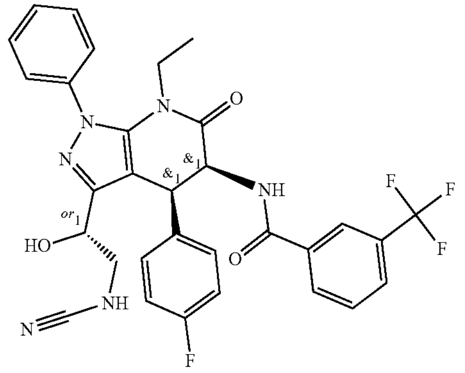
I-131
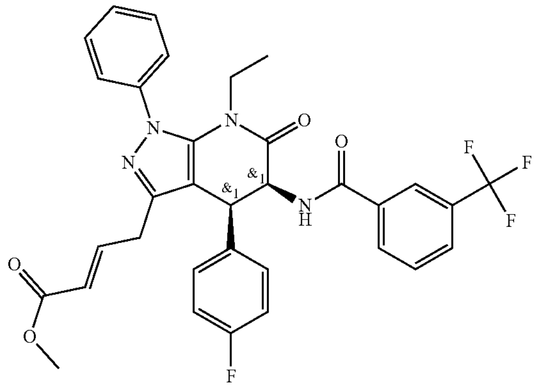
I-132
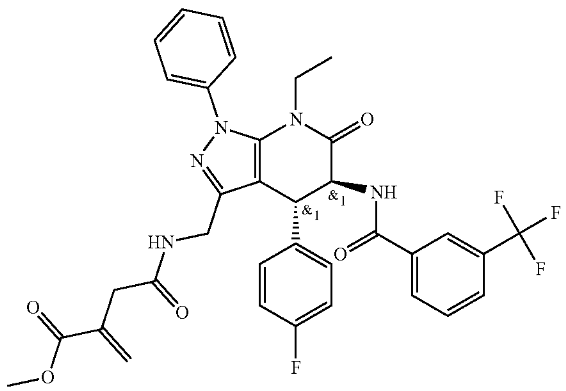

I-133
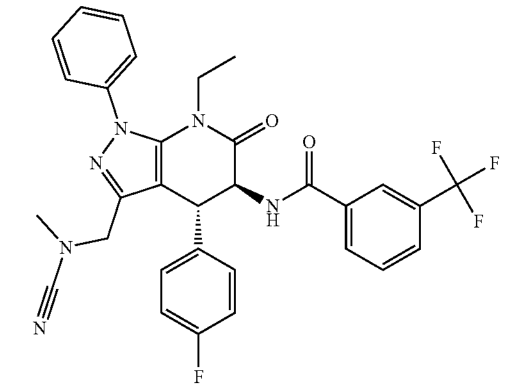
I-134
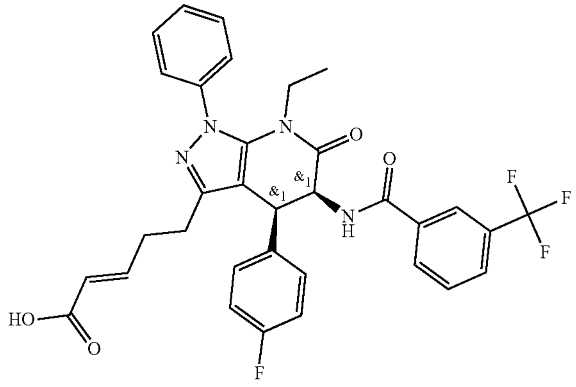
I-135
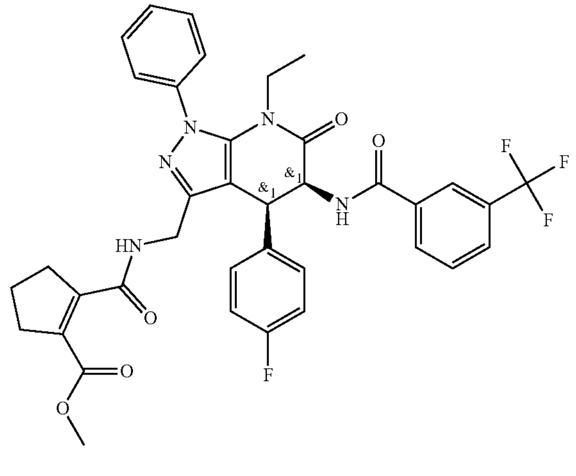
I-136
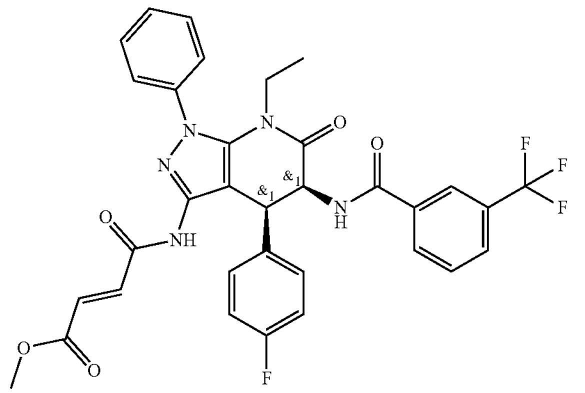
I-137
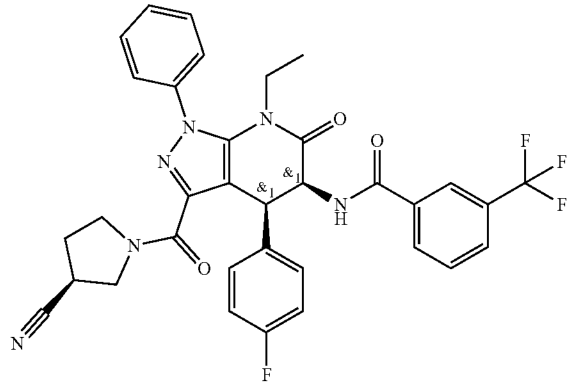
I-138
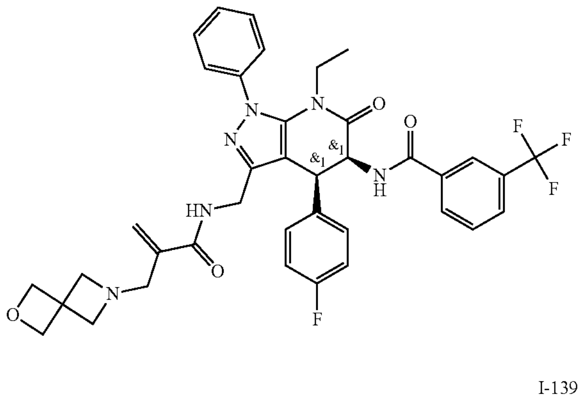
I-139
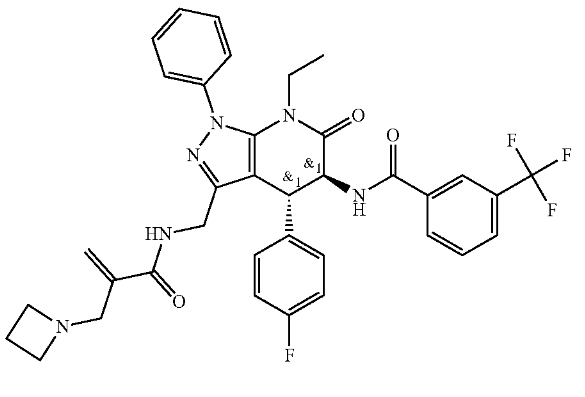

-continued
I-140
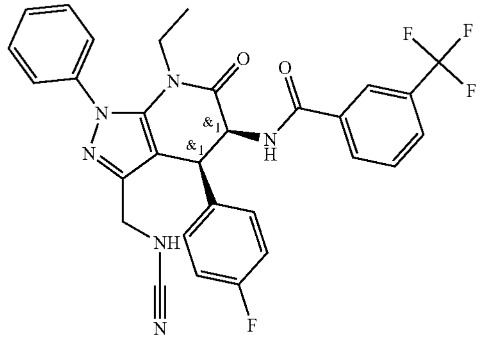
I-141
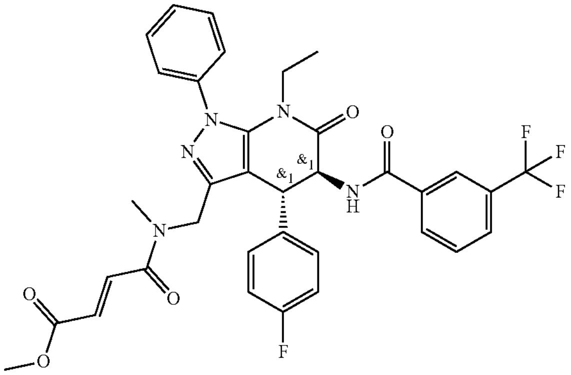
I-142
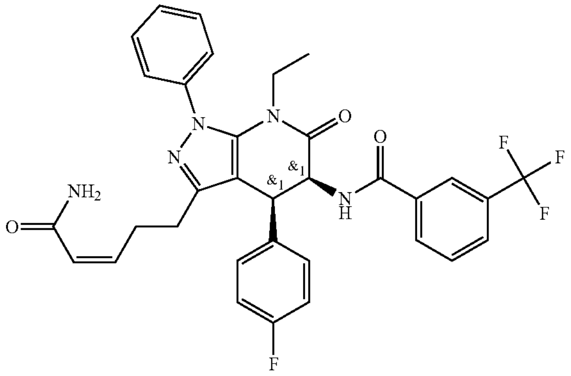
I-143
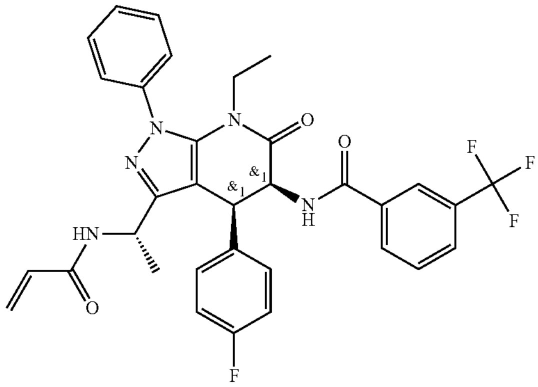
-continued
I-144
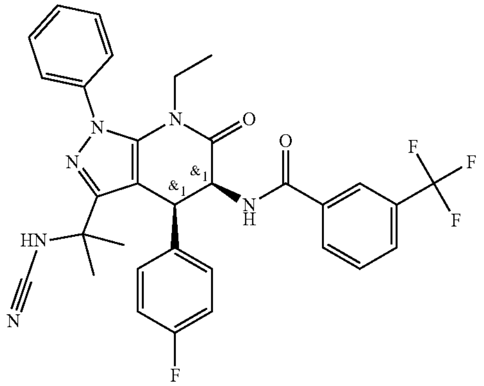
I-145
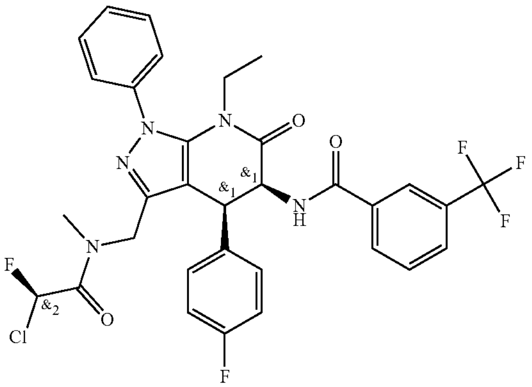
I-146
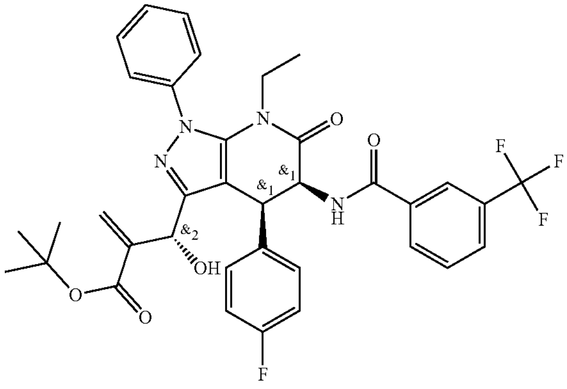
I-147
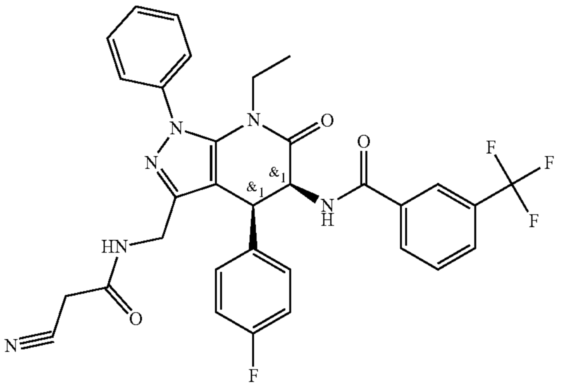

-continued
I-148
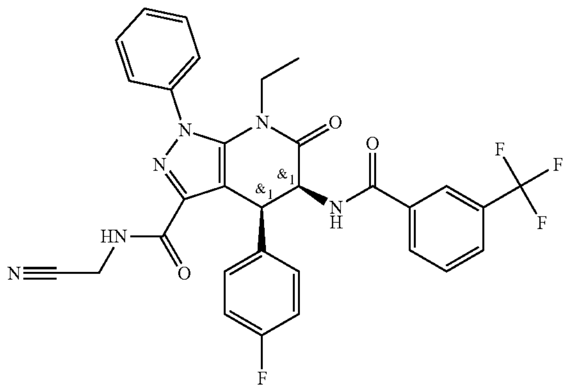
I-149
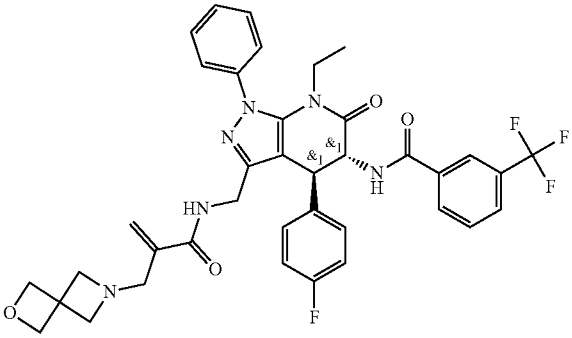
I-150
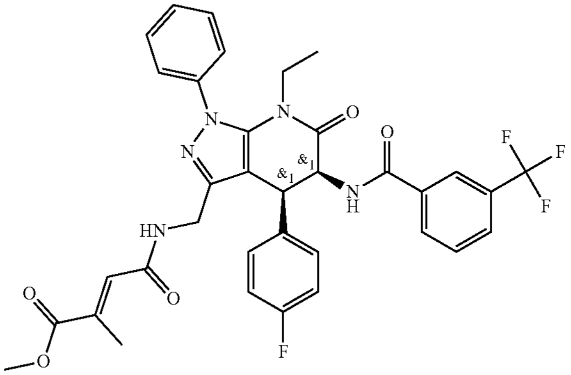
I-151
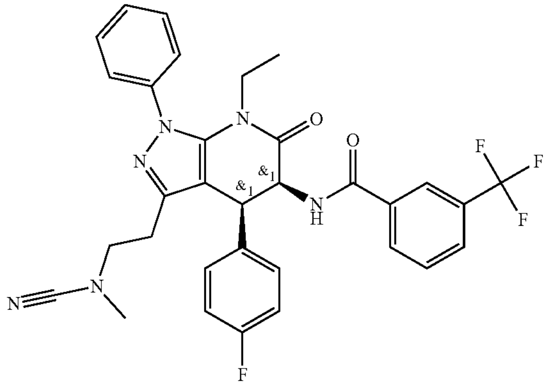
-continued
I-152
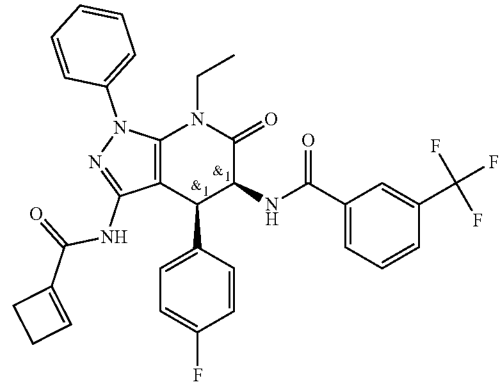
I-153
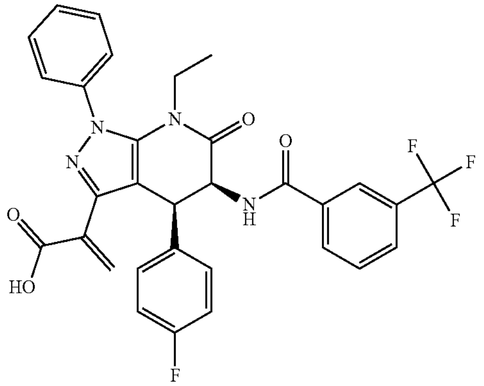
I-154
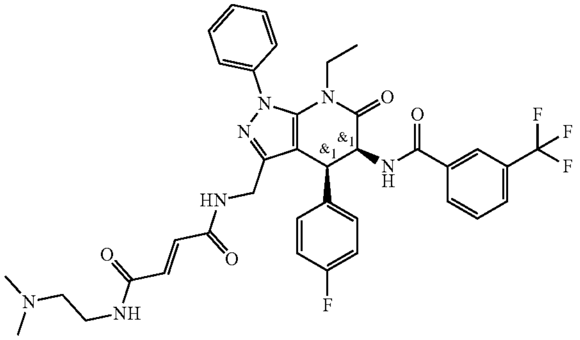
I-155
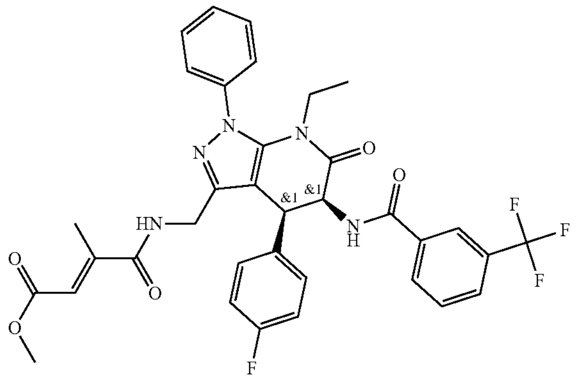

-continued
I-156
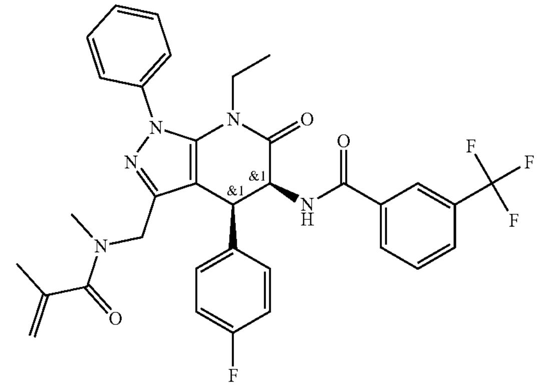
I-157
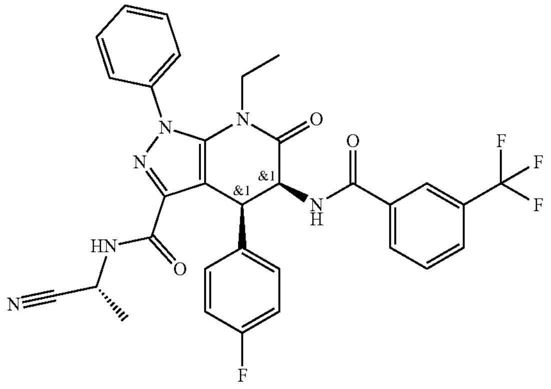
I-158
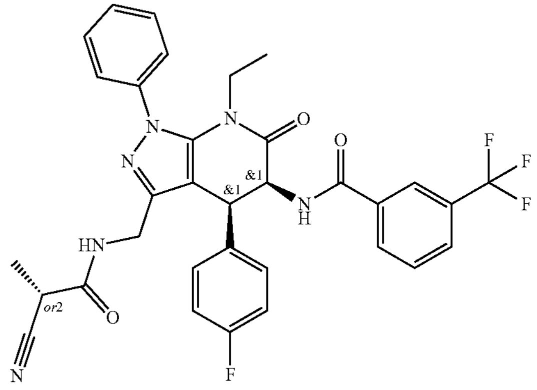
I-159
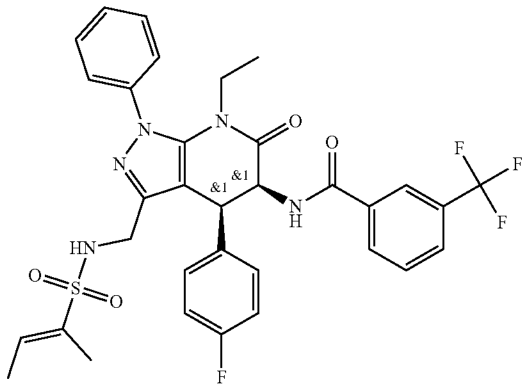
I-160
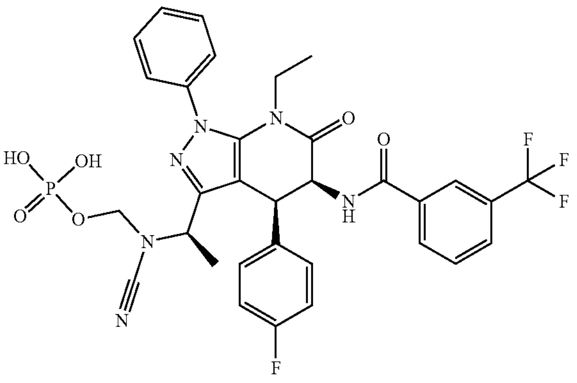
I-161
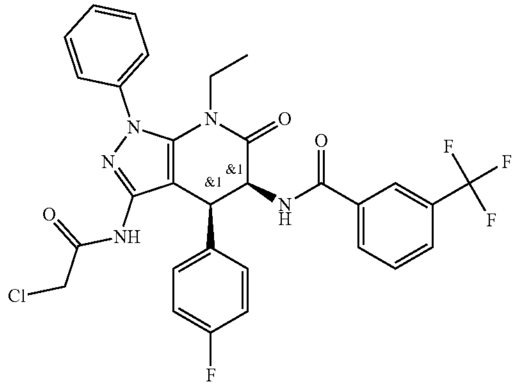

-continued
I-162
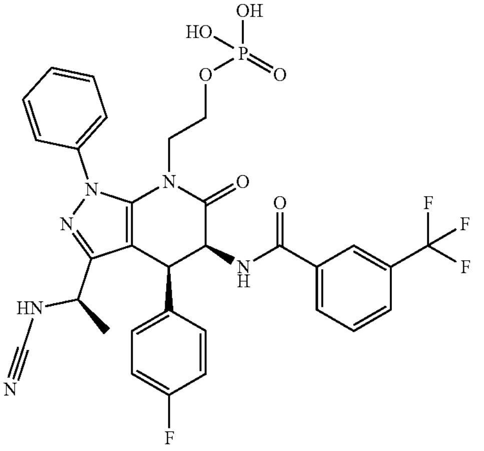
I-163
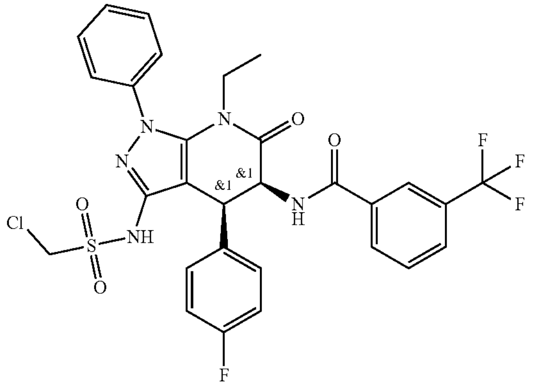
I-164
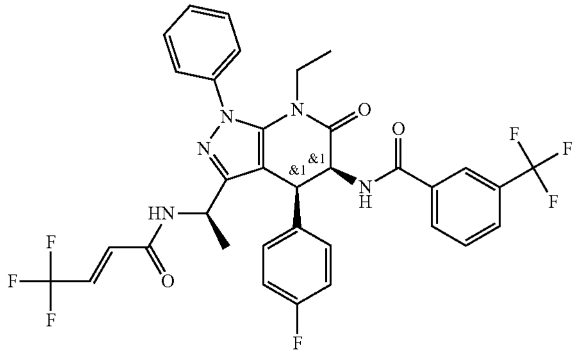
I-165
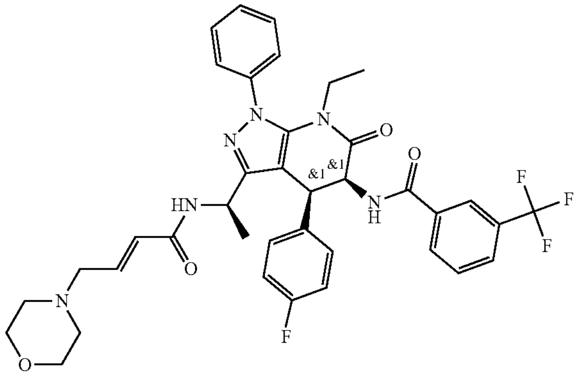
-continued
I-166
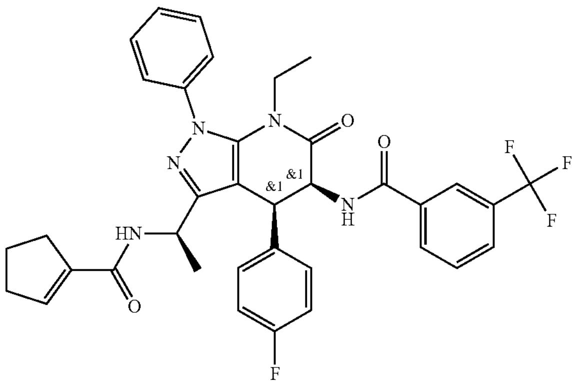
I-167
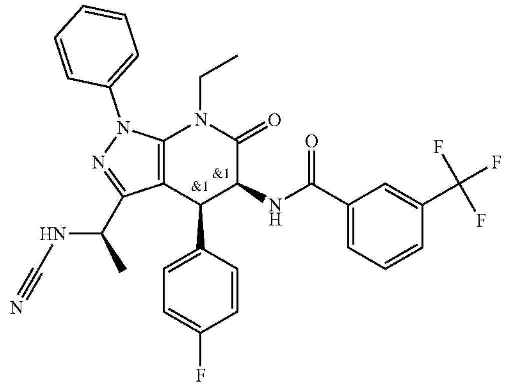
I-168
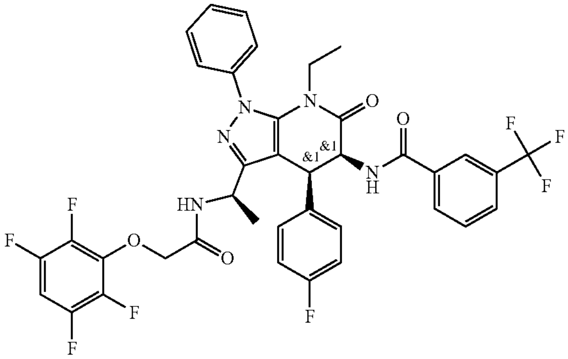
I-169
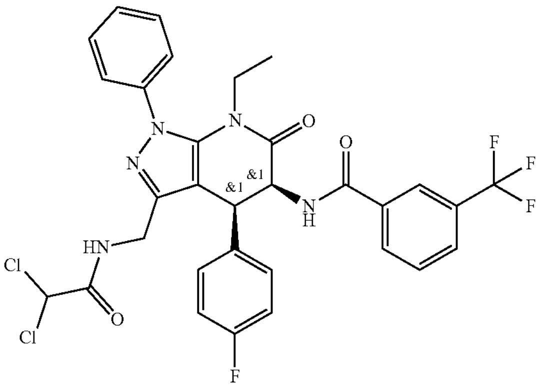

-continued
I-170
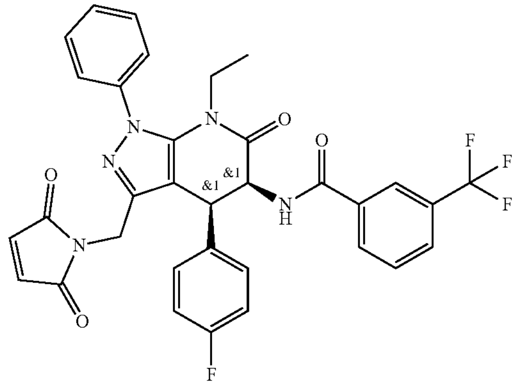
I-171
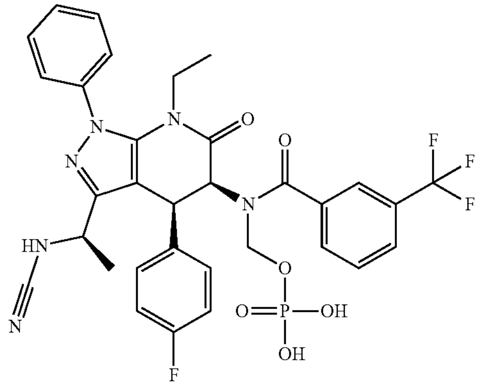
I-172
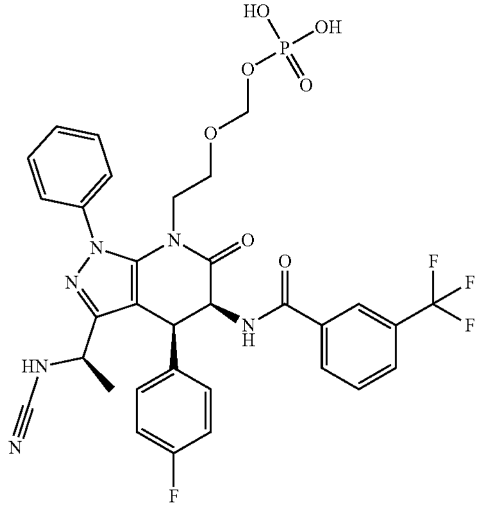
-continued
I-173
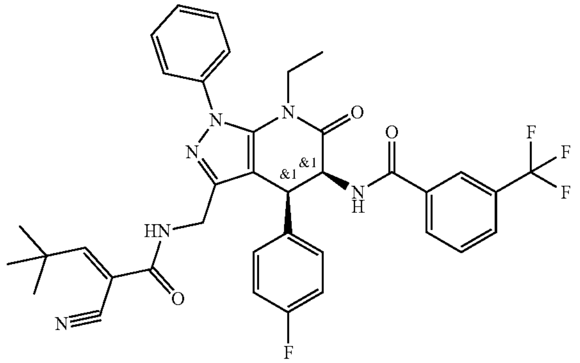
I-174
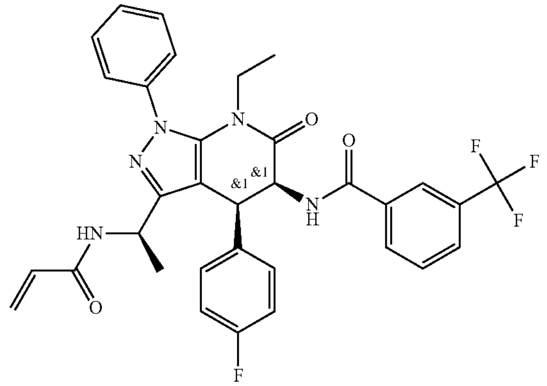
I-175
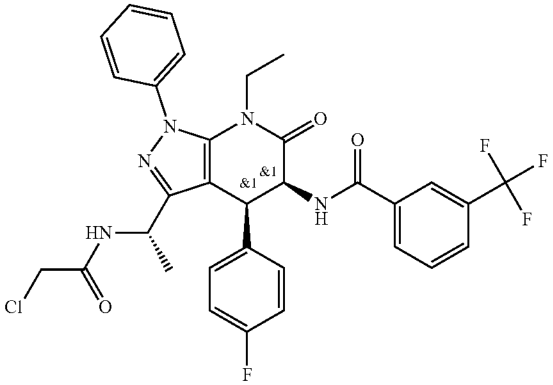
I-176
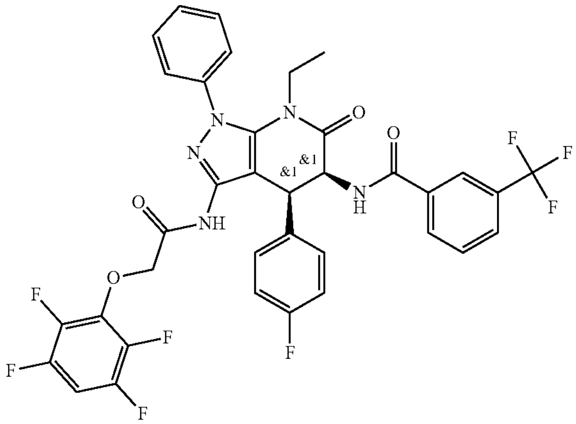

-continued
I-177
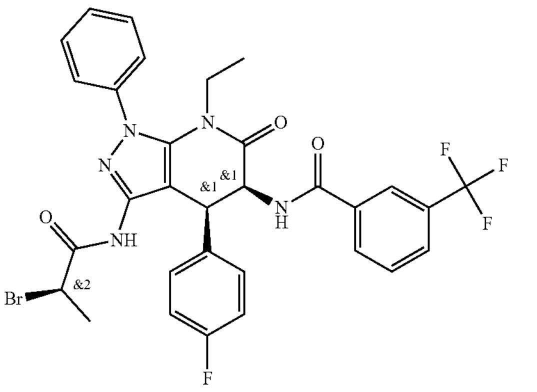
I-178
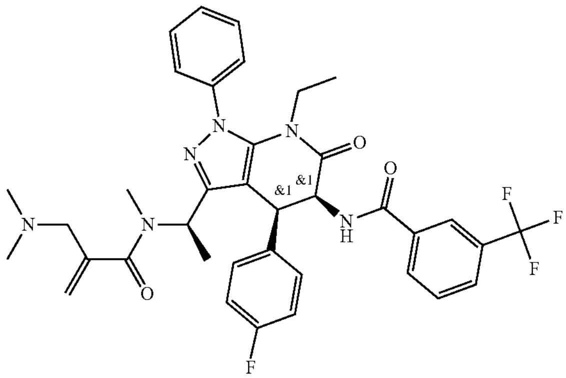
I-179
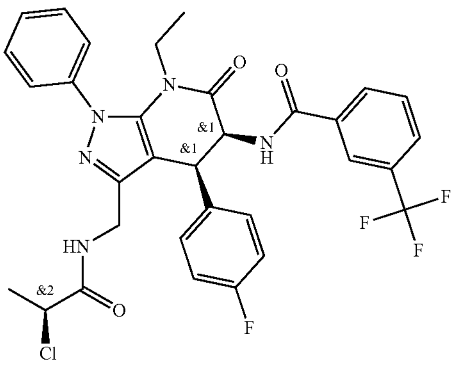
I-180
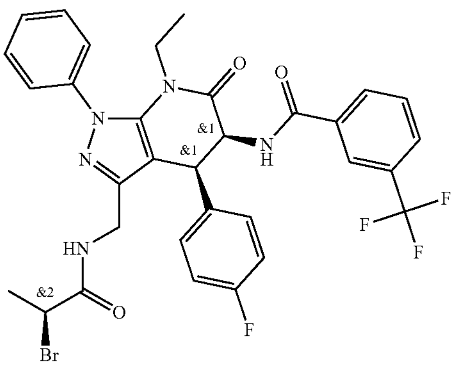
-continued
I-181
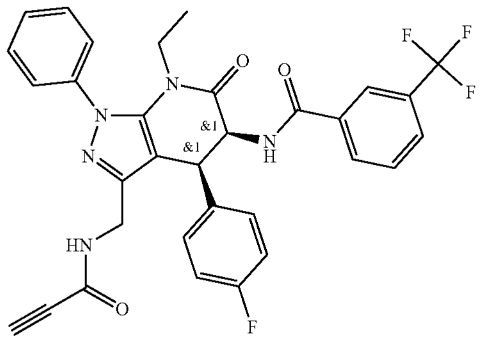
I-182
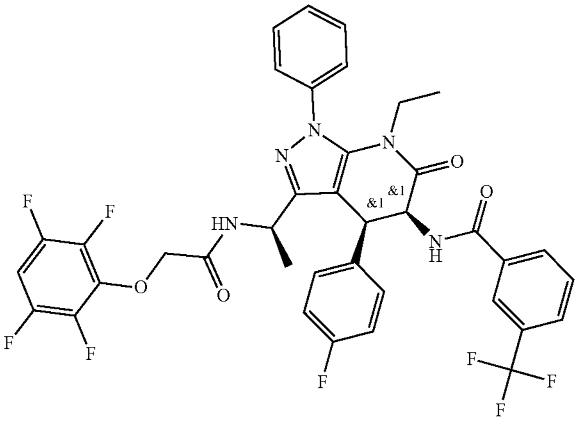
I-183
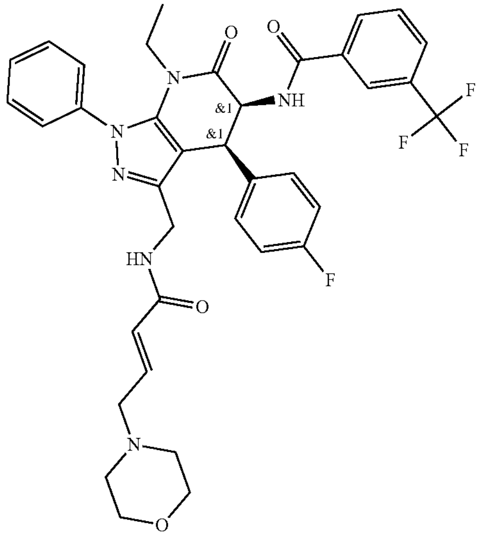

-continued
I-184
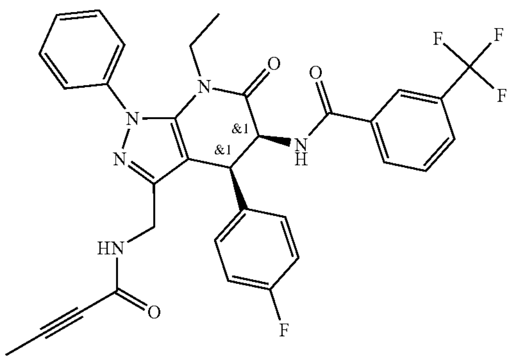
I-185
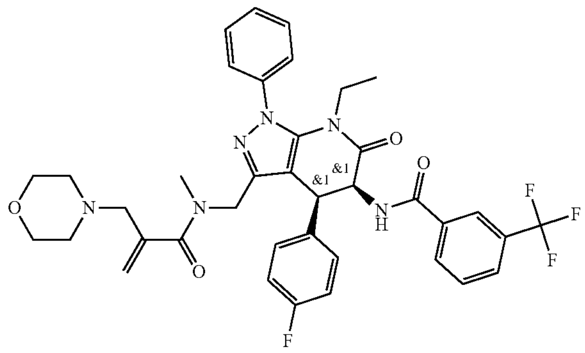
I-186
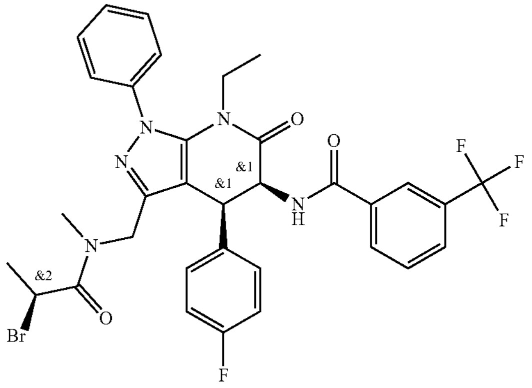
I-187
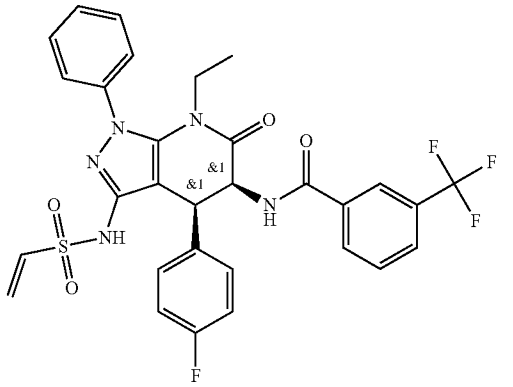
-continued
I-188
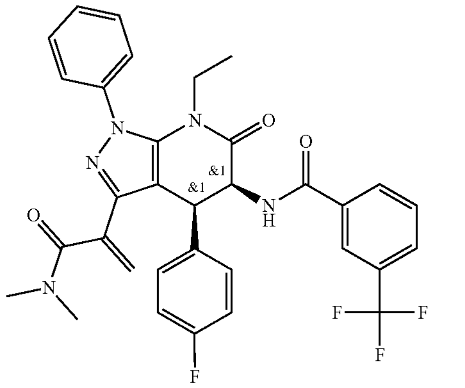
I-189
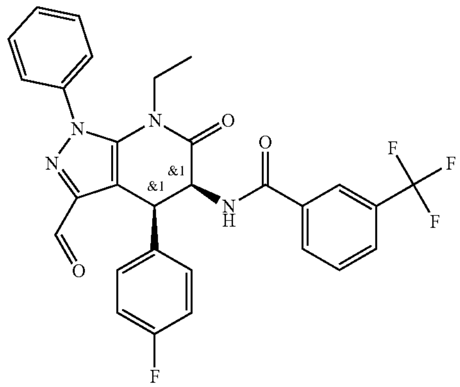
I-190
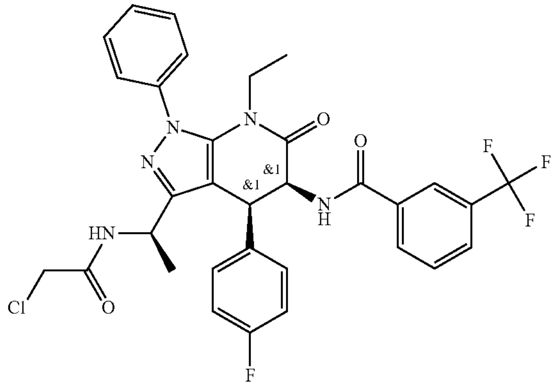
I-191
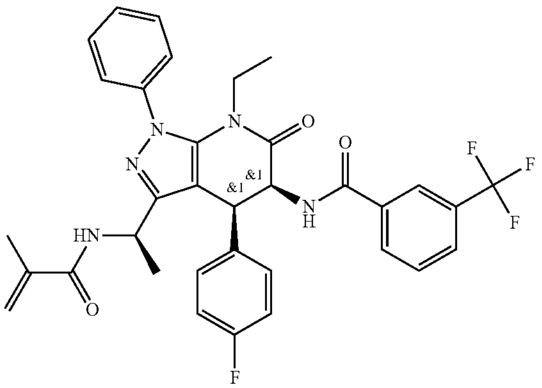

-continued
I-192
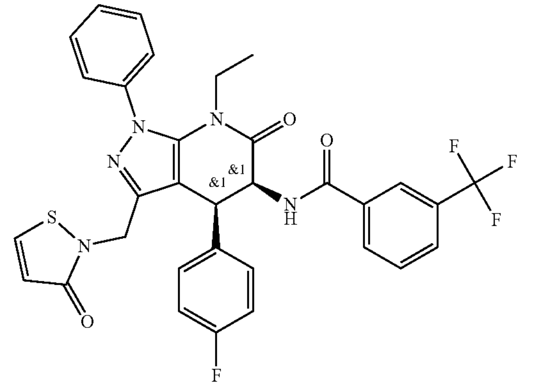
I-193
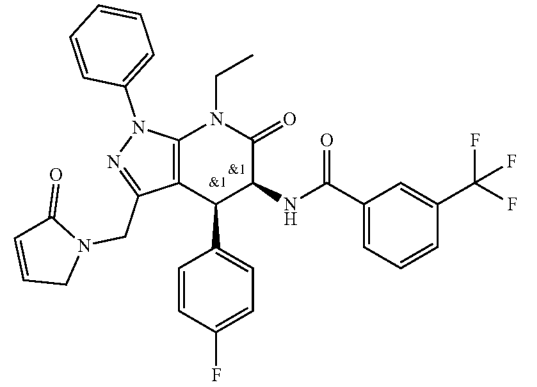
I-194
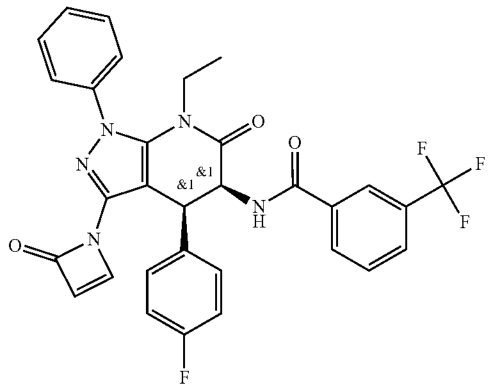
I-195
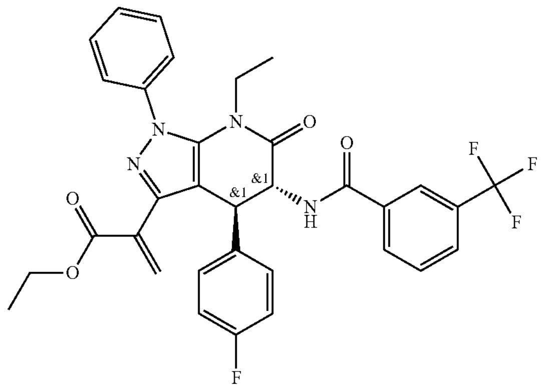
I-196
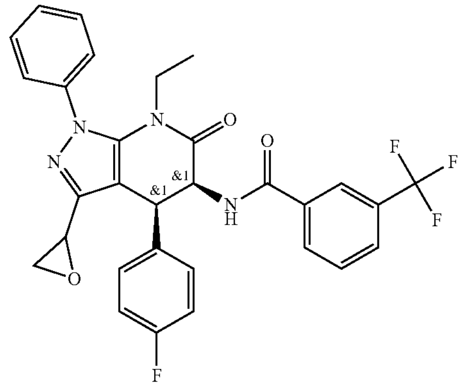
I-197
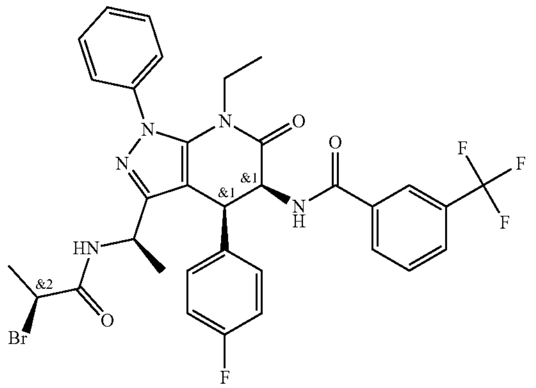
I-198
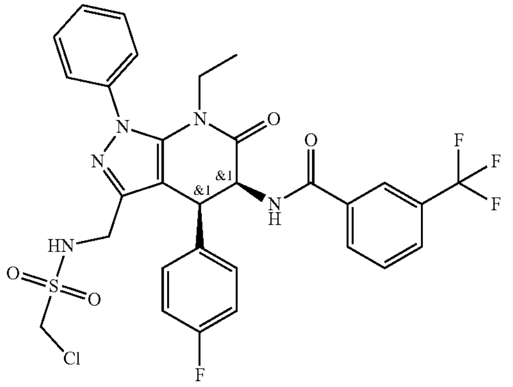

-continued
I-199
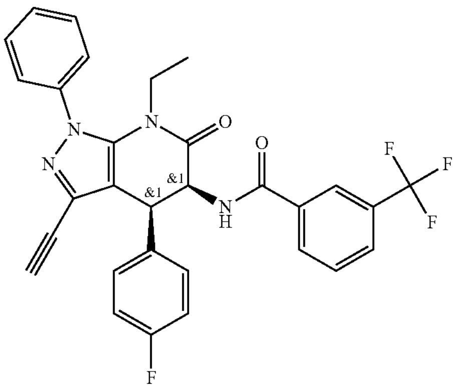
I-200
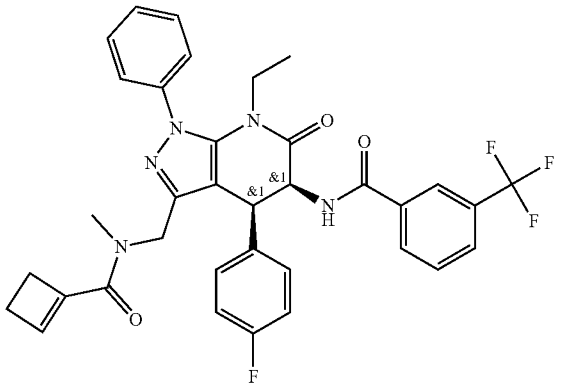
I-201
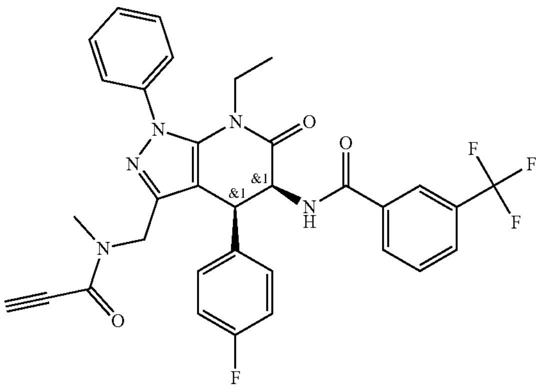
I-202
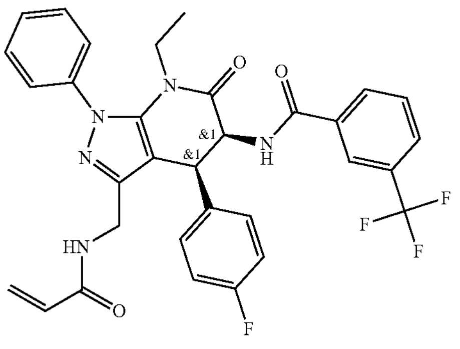
-continued
I-203
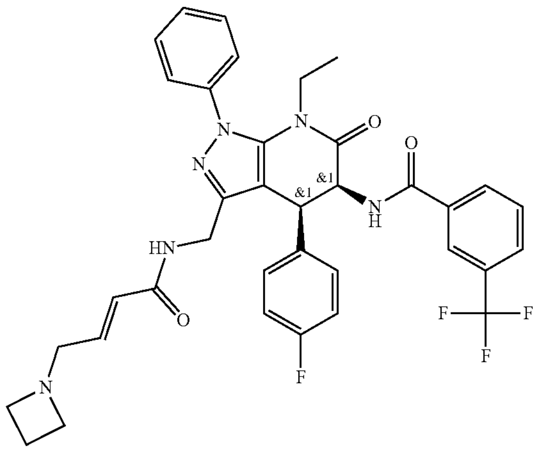
I-204
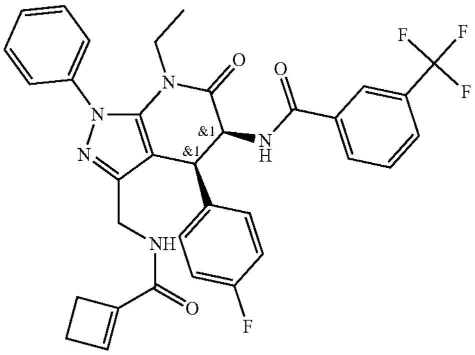
I-205
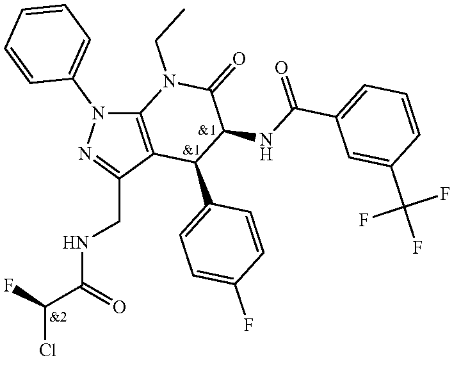
I-206
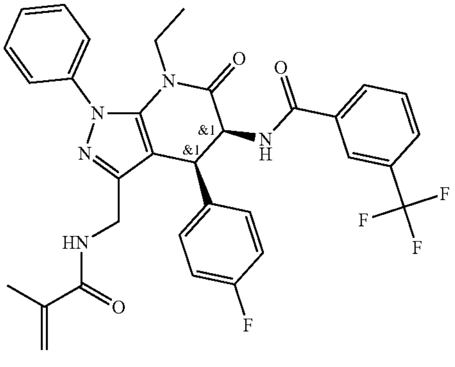

-continued
I-207
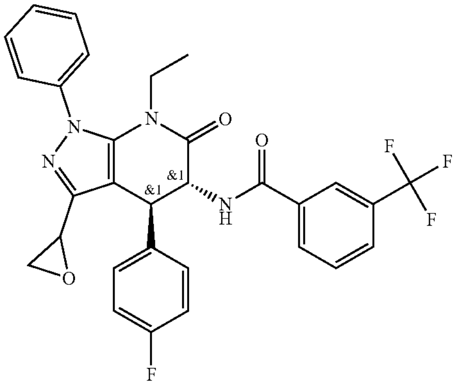
I-208
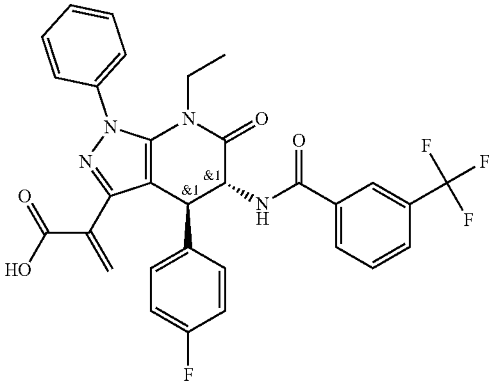
I-209
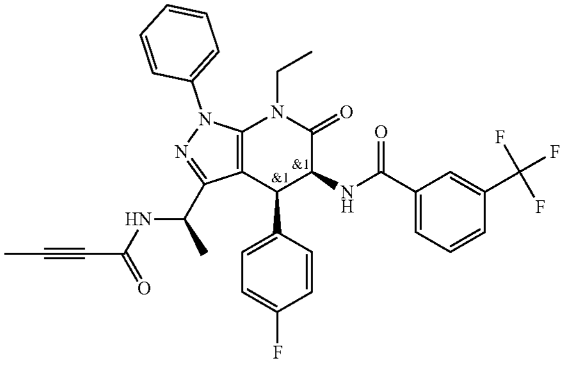
I-210
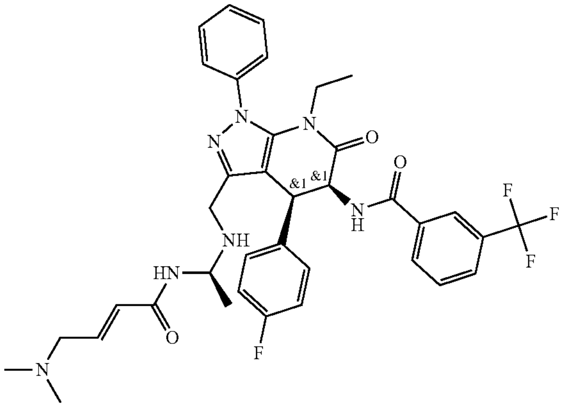
-continued
I-211
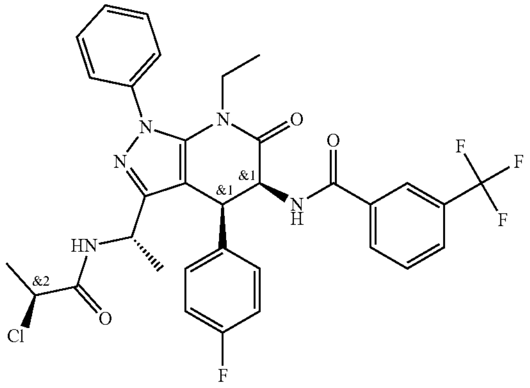
I-212
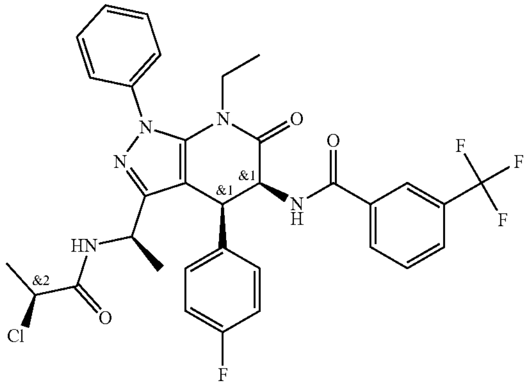
I-213
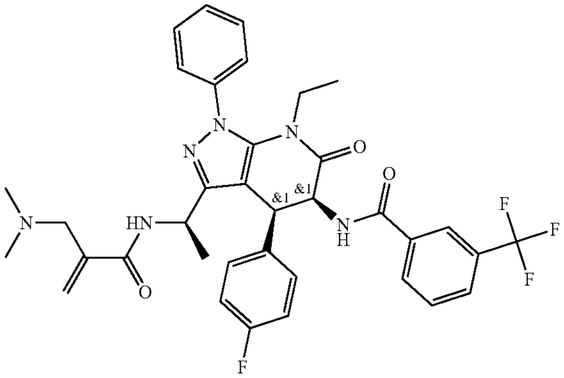
I-214
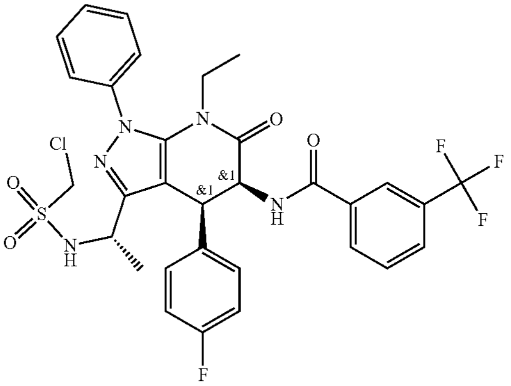

-continued
I-215
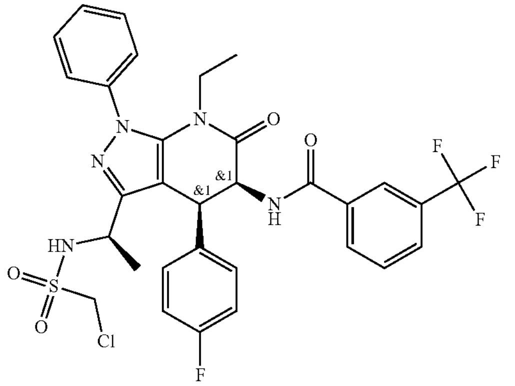
I-216
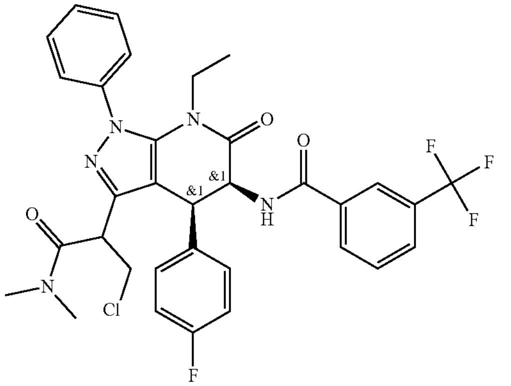
I-217
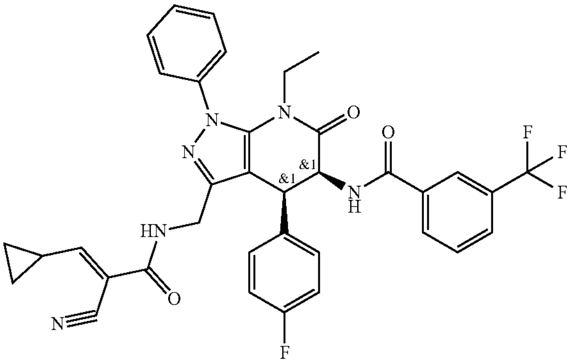
I-218
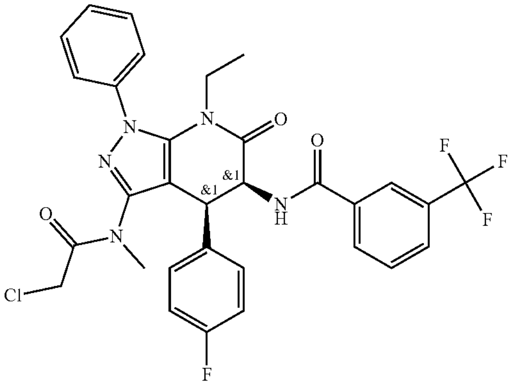
-continued
I-219
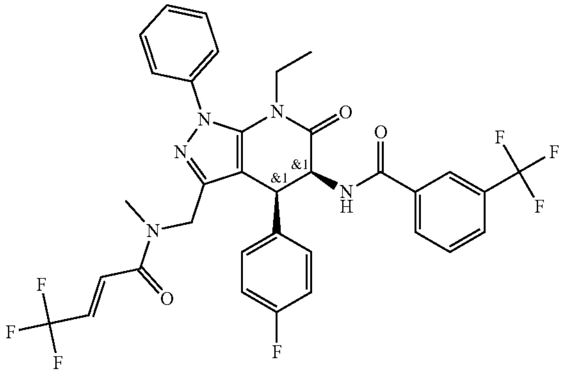
I-220
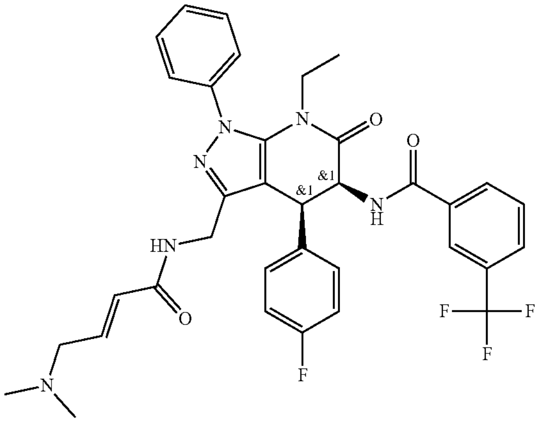
I-221
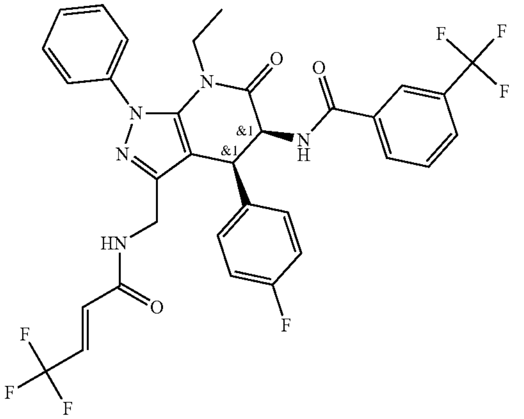

-continued
I-222
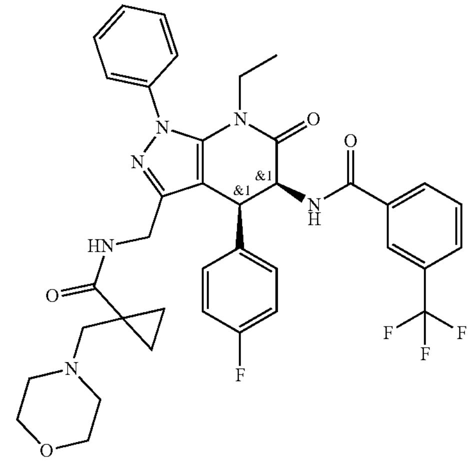
I-225
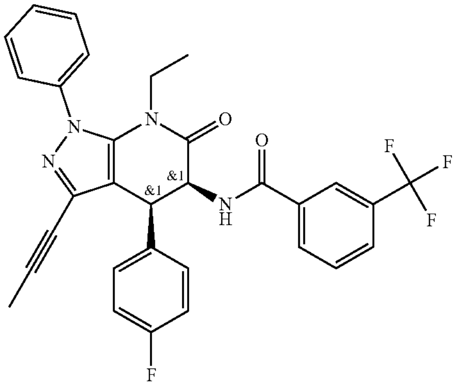
I-227
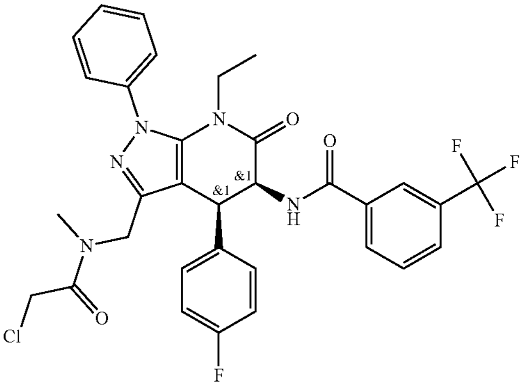
I-228
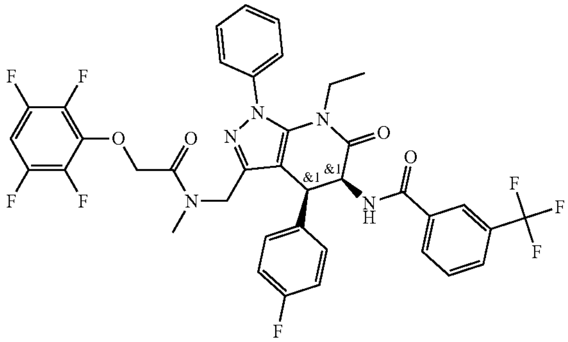
-continued
I-229
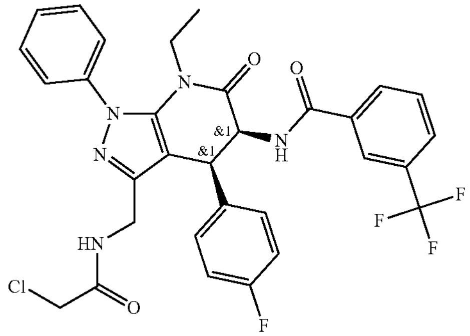
I-230
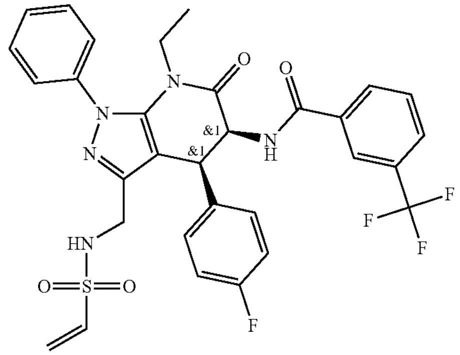
I-231
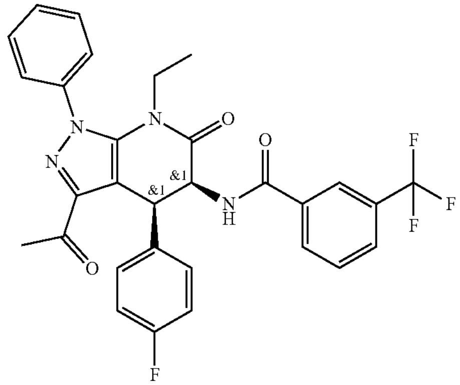
I-232
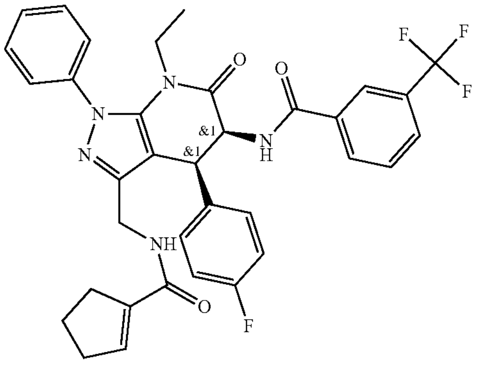

-continued
I-233
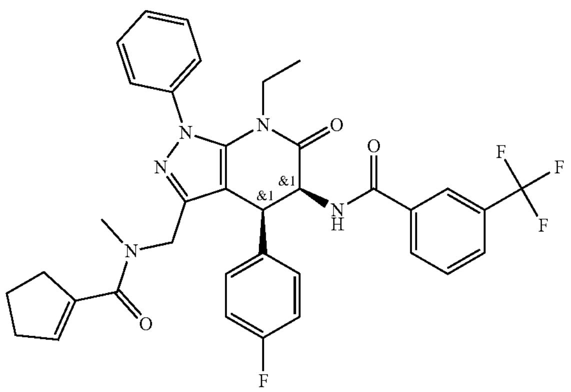
I-234
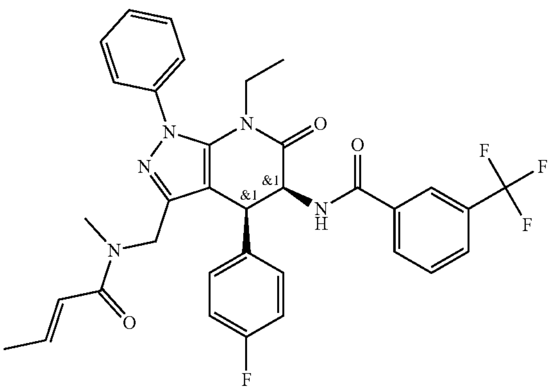
I-235
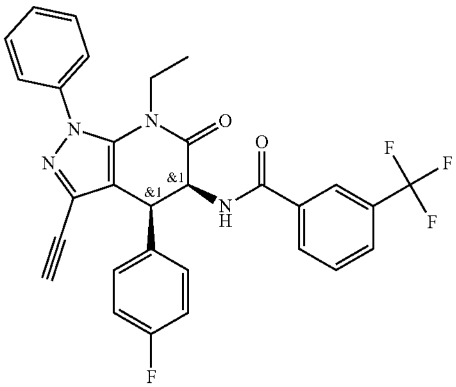
I-236
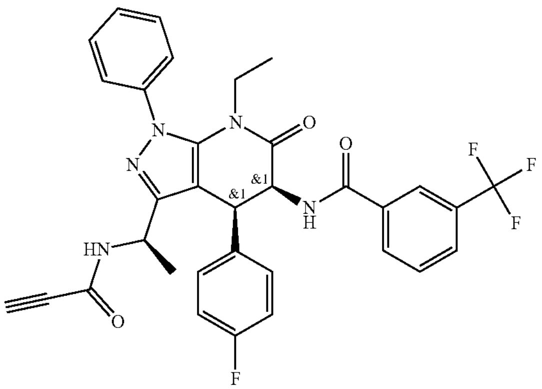
-continued
I-237
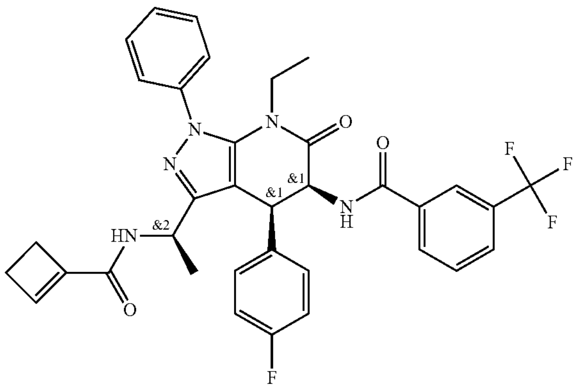
I-238
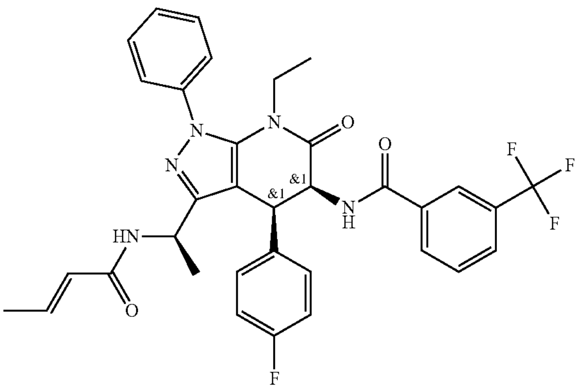
I-239
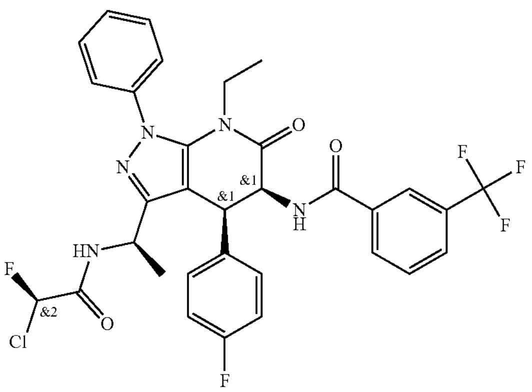

-continued
I-240
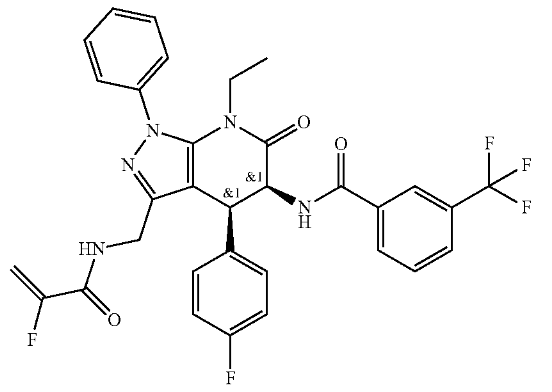
I-241
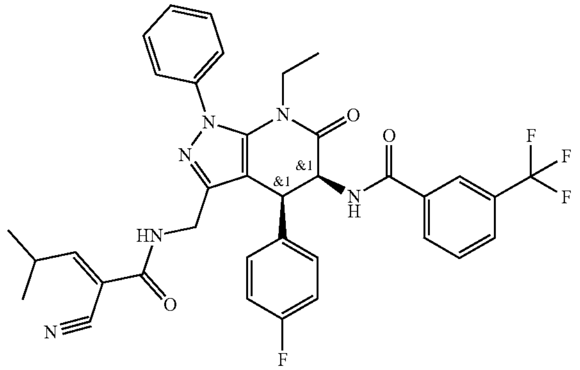
I-242
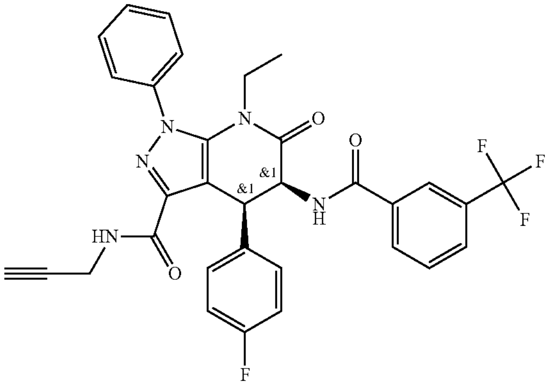
I-244
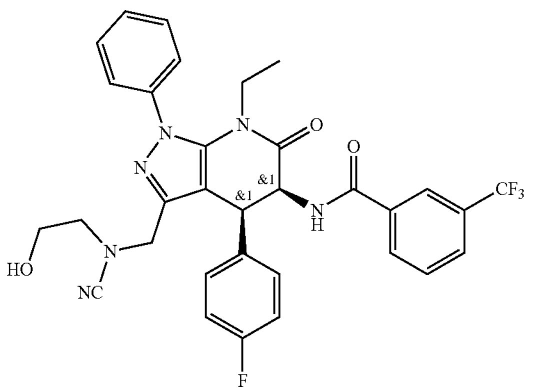
-continued
I-245
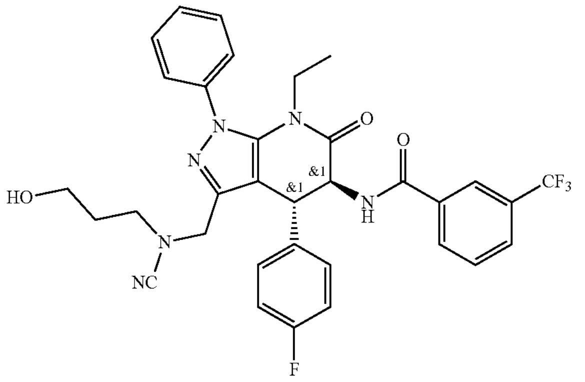
I-246
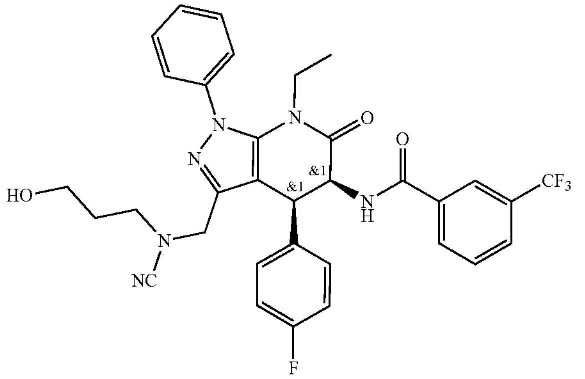
I-247
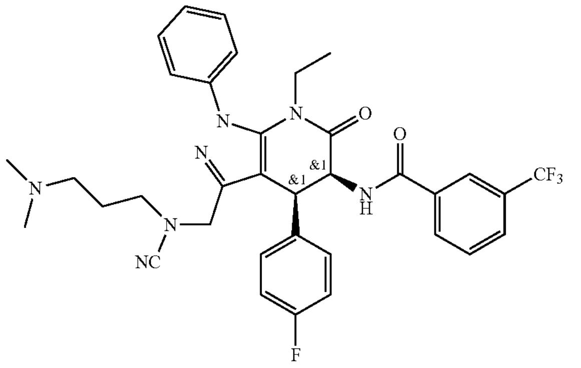
I-248
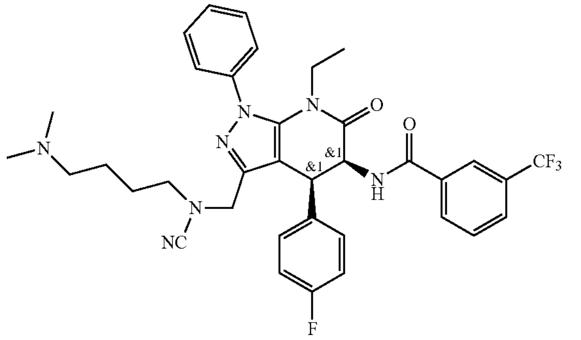

-continued
I-249
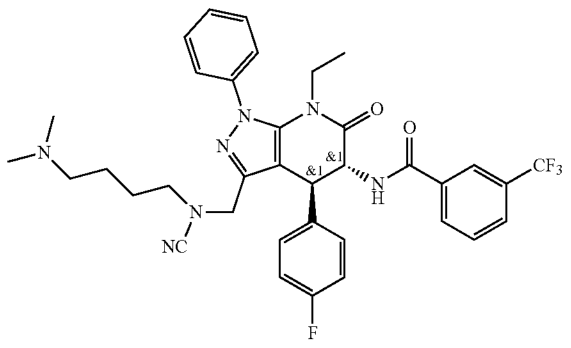
I-250
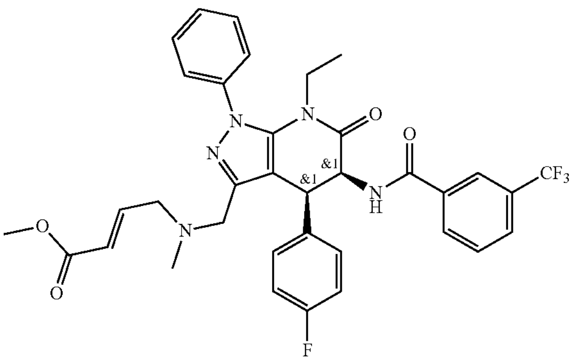
I-251
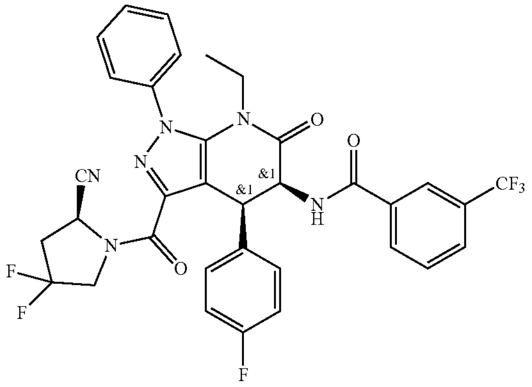
I-252
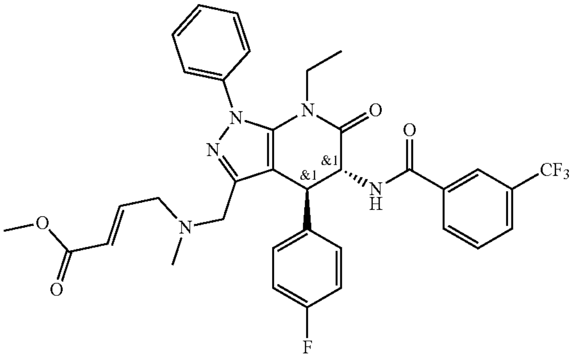
-continued
I-253
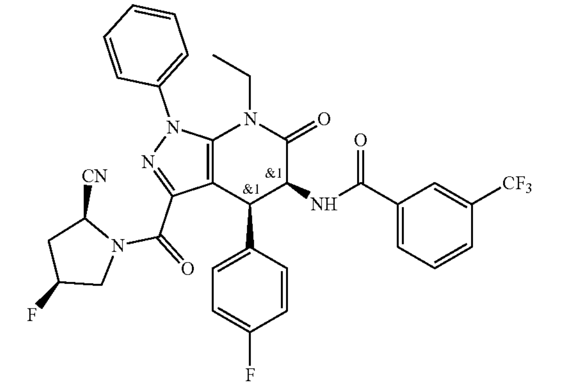
I-254
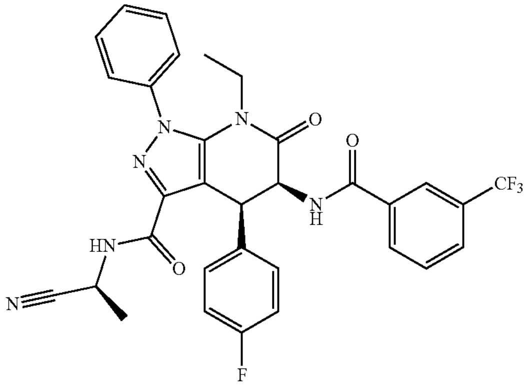
I-255
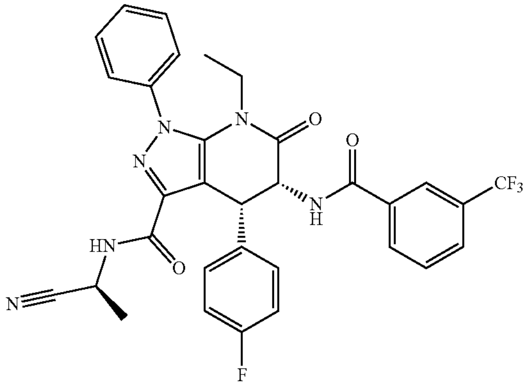
I-256
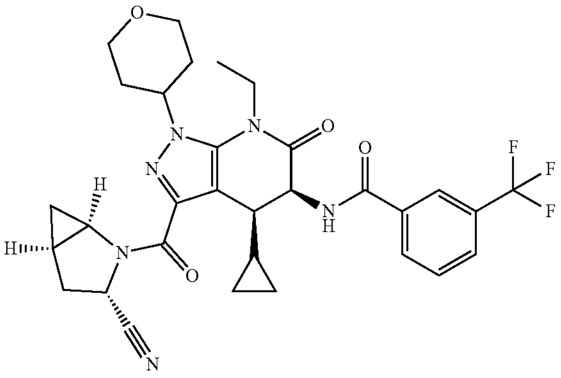

-continued
I-256a
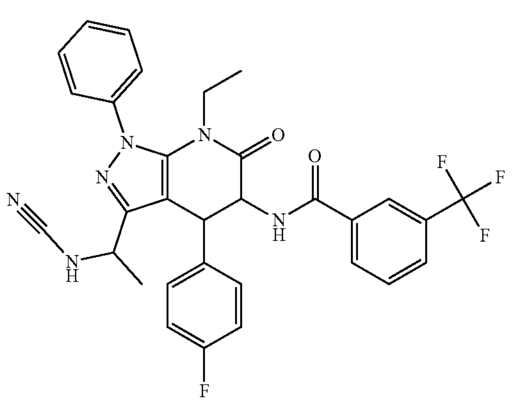
I-256b
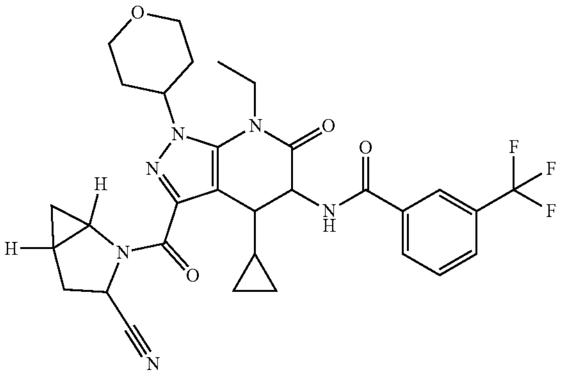
I-270
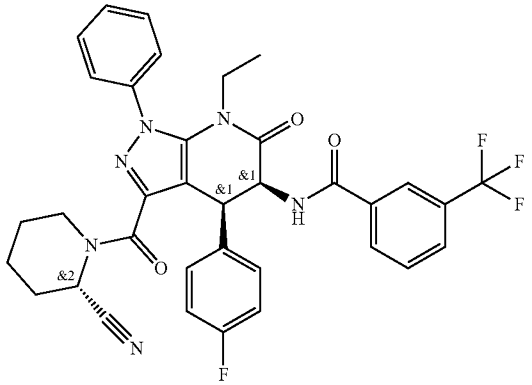
I-271
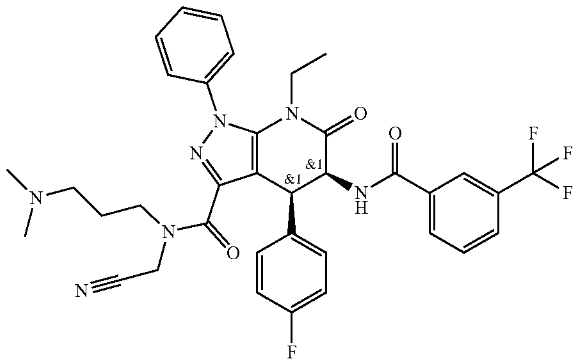
-continued
I-272
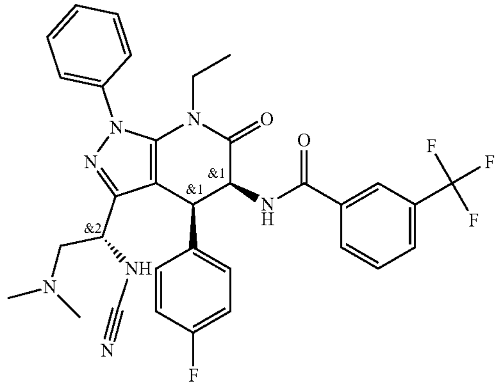
I-273
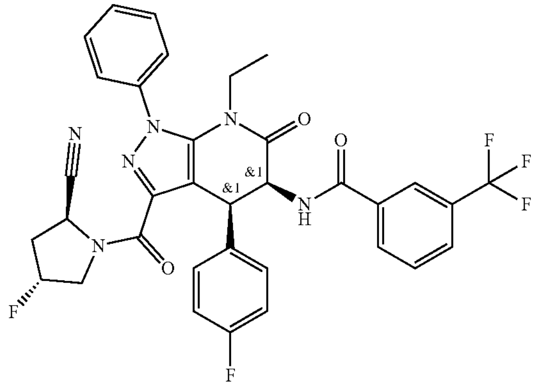
I-274
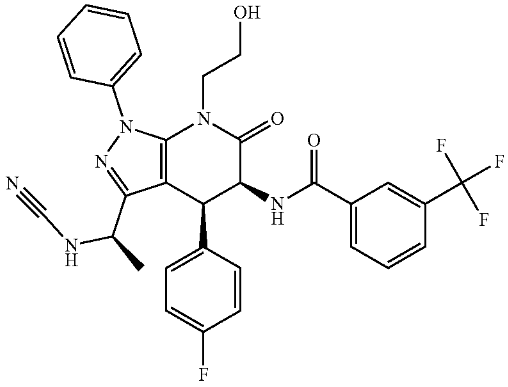
I-275
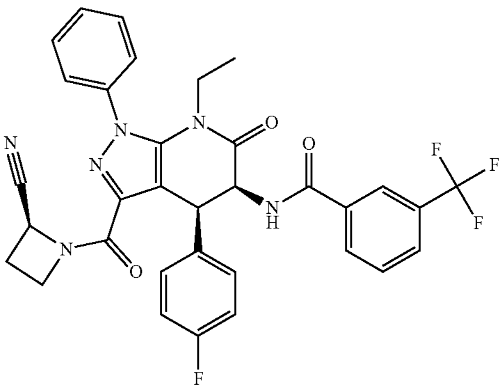

-continued
I-276
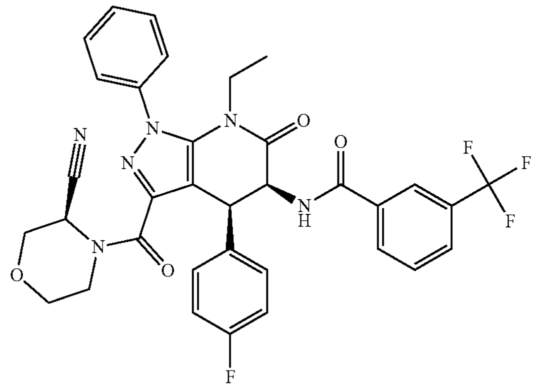
I-277
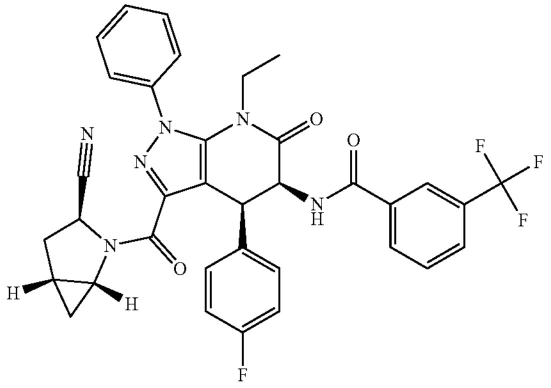
I-278
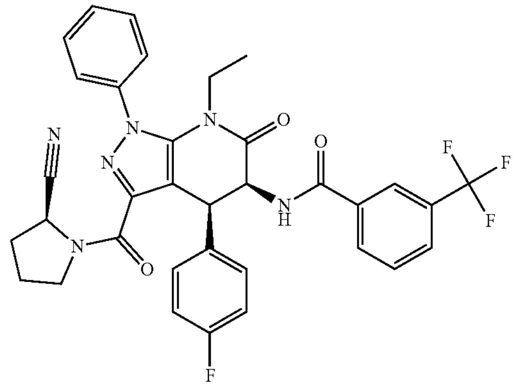
I-279
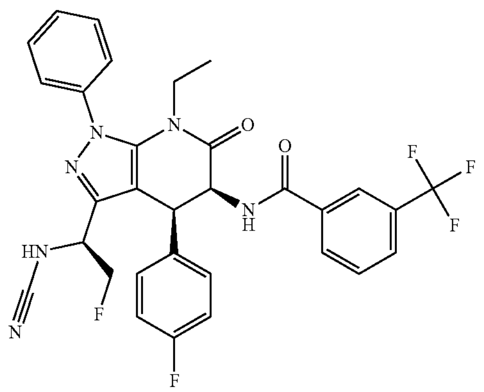
-continued
I-280
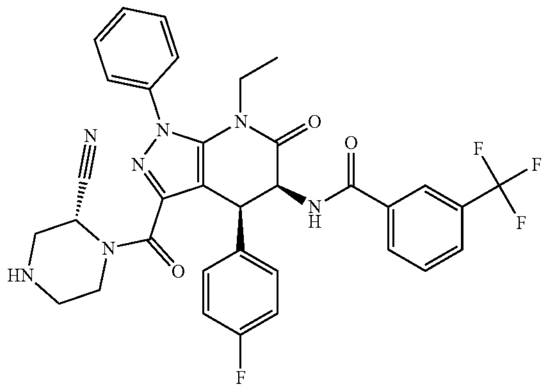
I-281
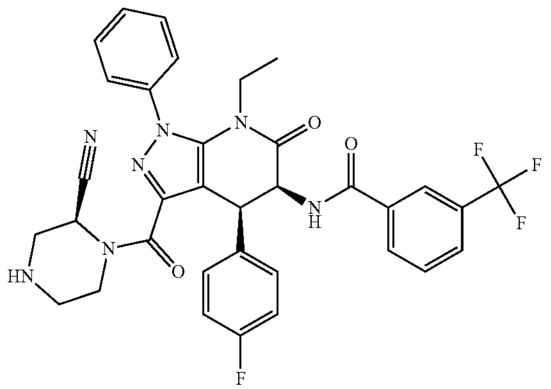
I-282
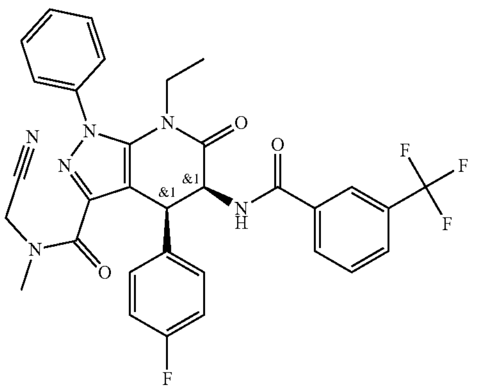
I-283
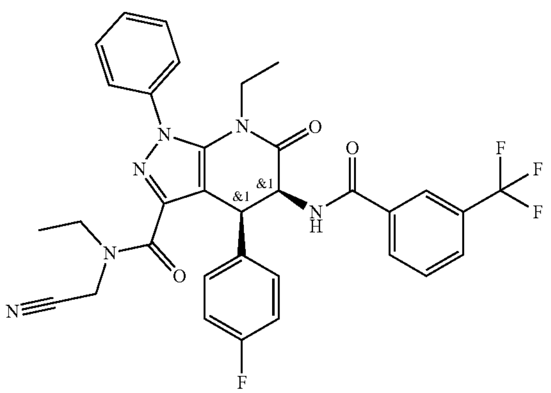

-continued
I-284
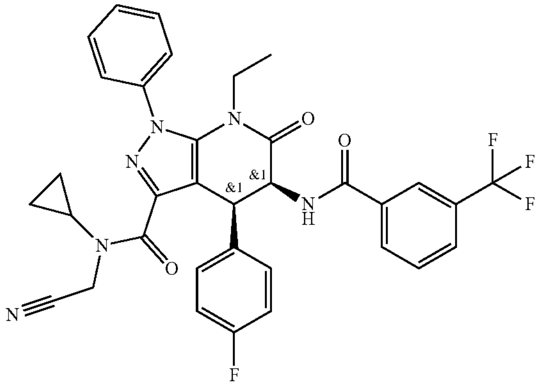
I-285
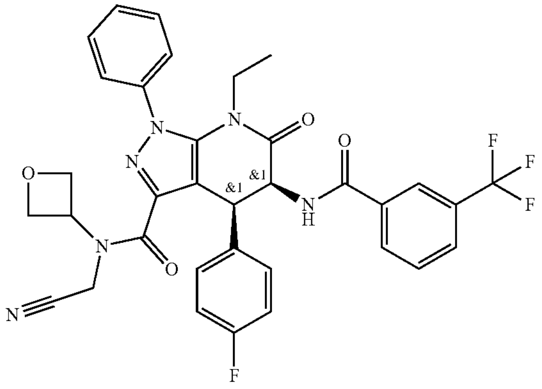
I-286
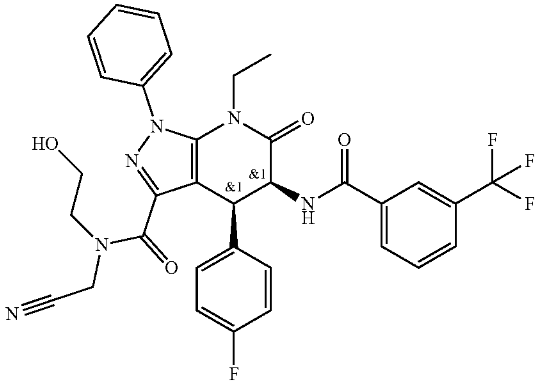
I-287
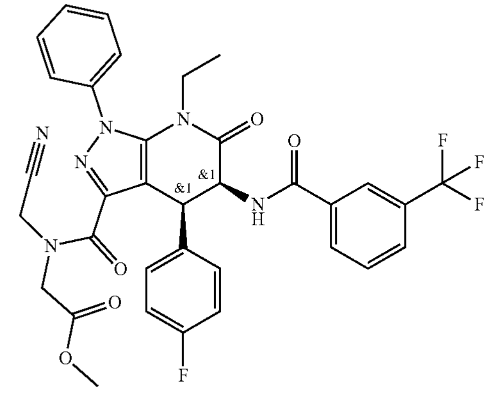
-continued
I-288
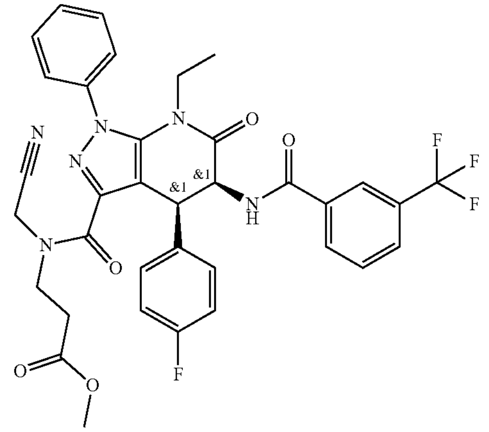
I-289
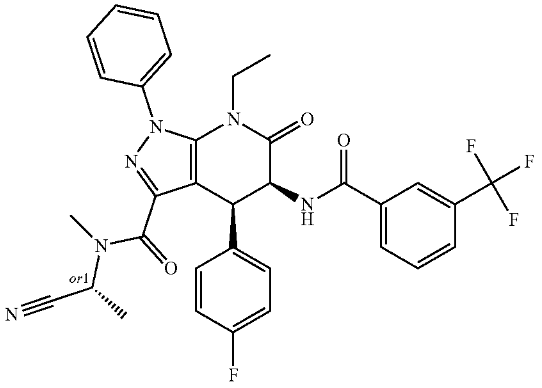
I-290
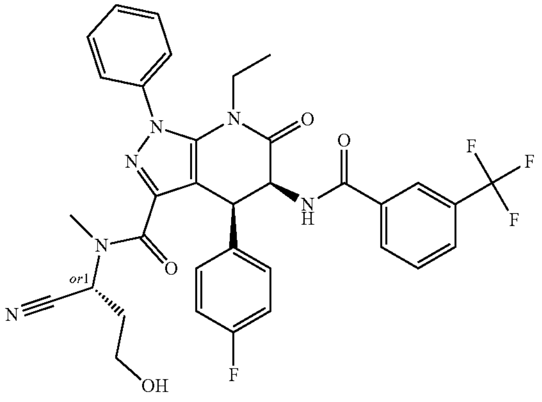

-continued
I-291
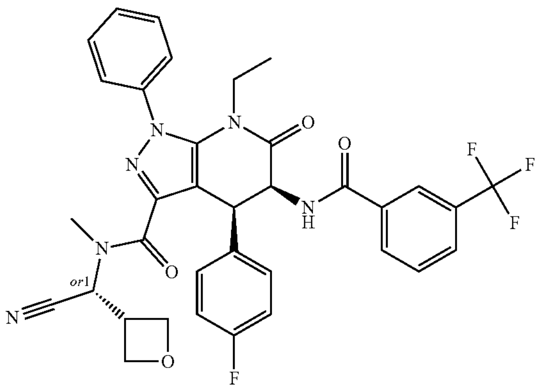
I-292
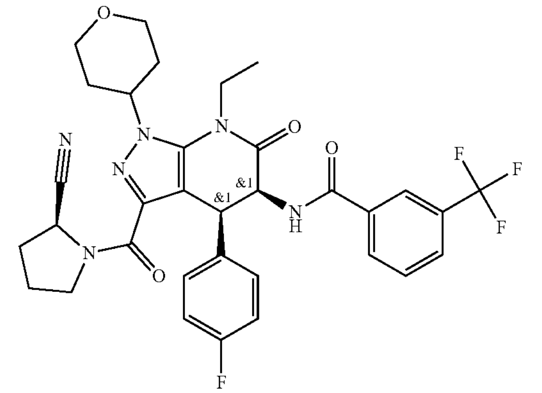
I-293
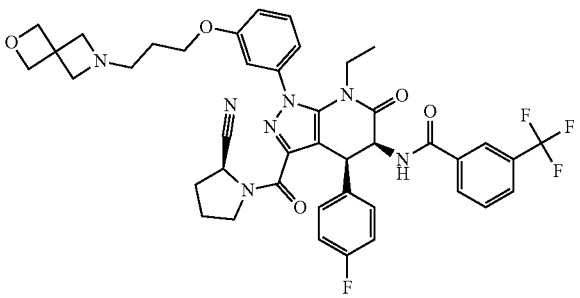
I-294
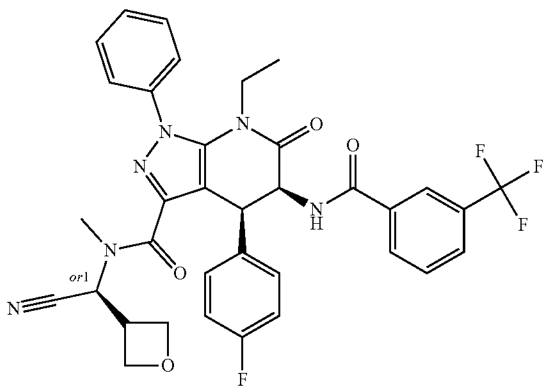
-continued
I-295
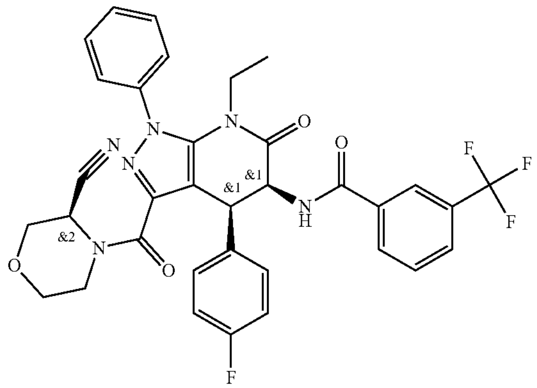
I-296
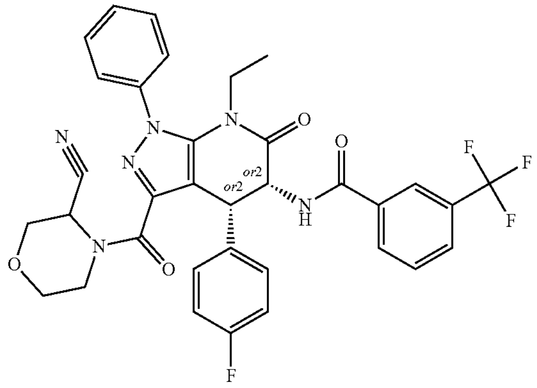
I-297
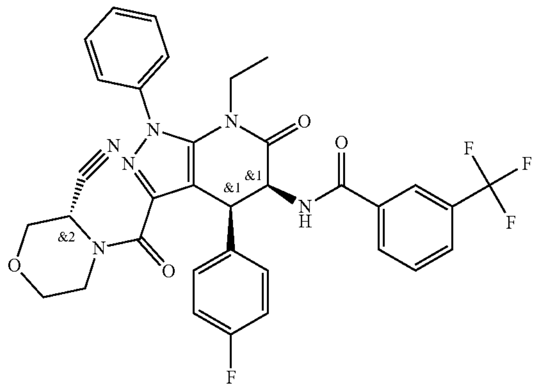
I-298
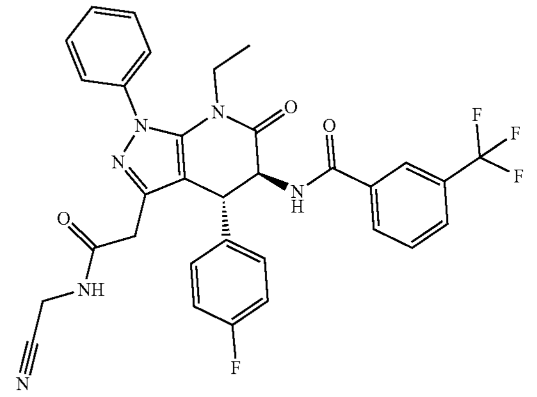

-continued
I-299
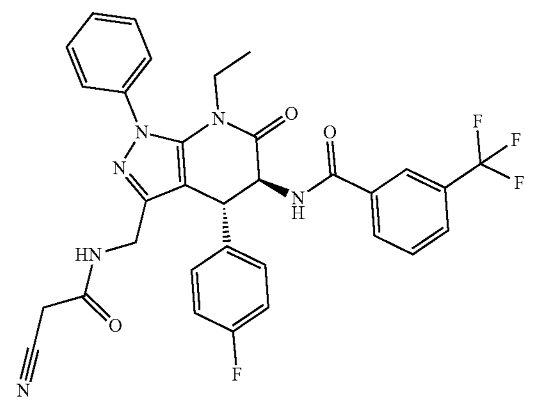
I-300
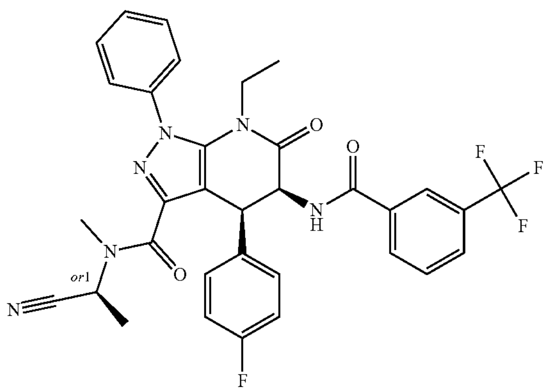
I-301
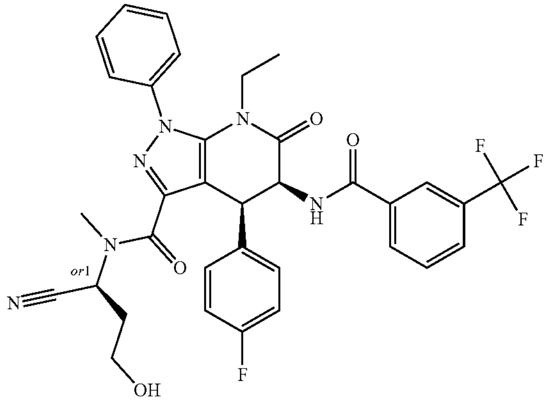
-continued
I-302
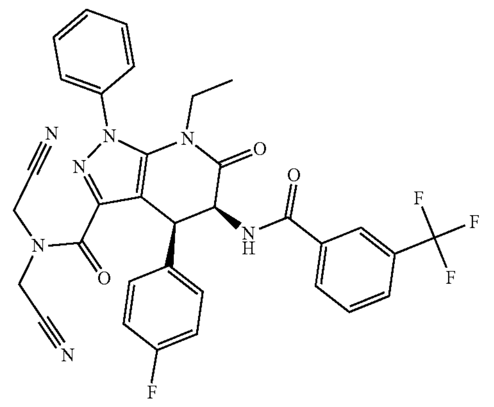
I-303
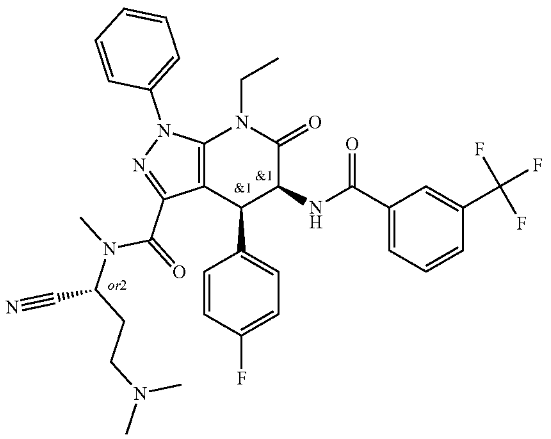
I-304
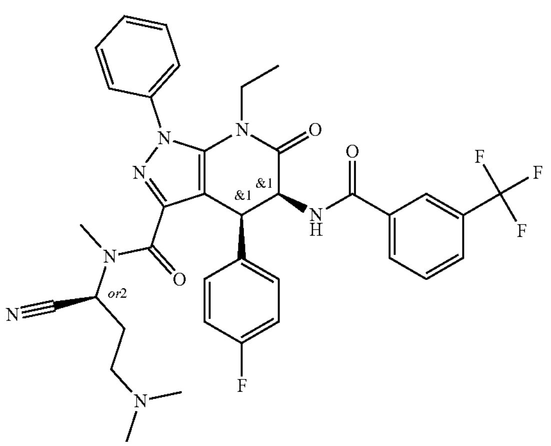

I-305
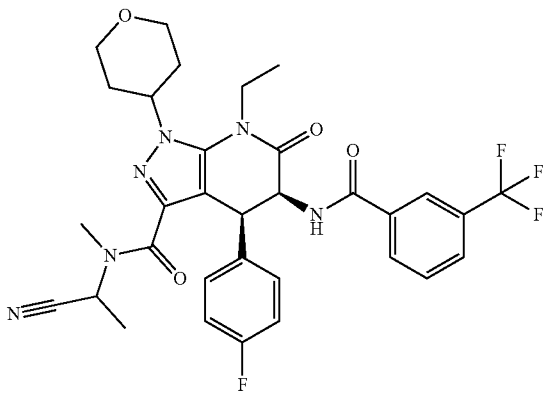
I-306
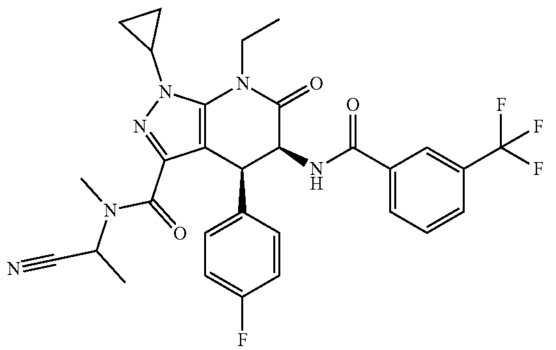
I-307
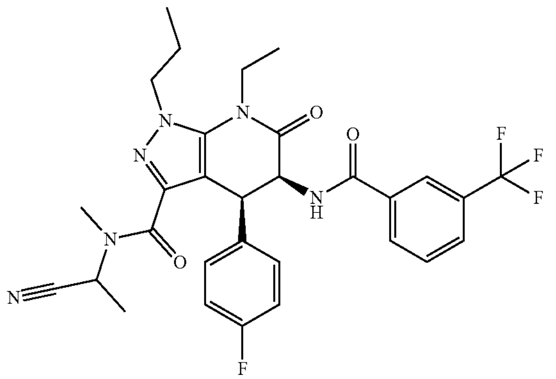
I-308
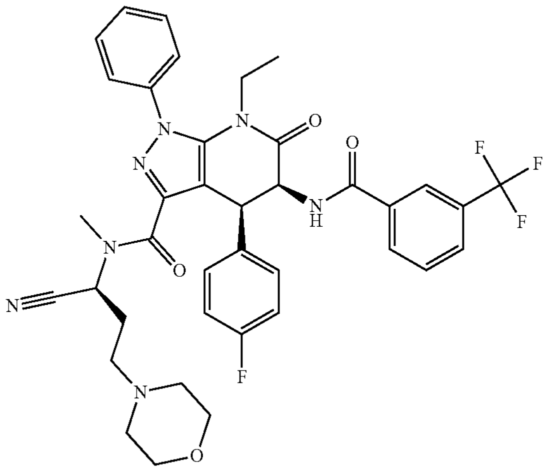
I-309
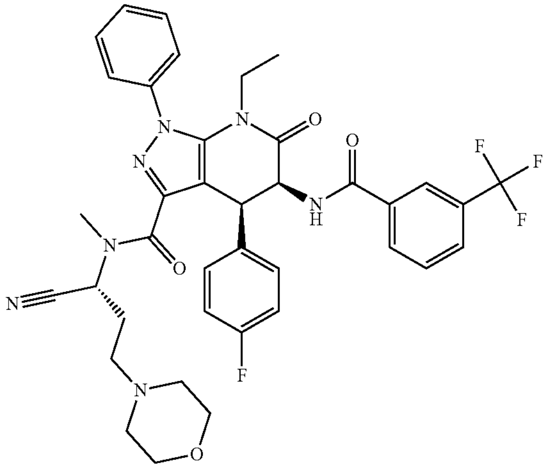
I-310
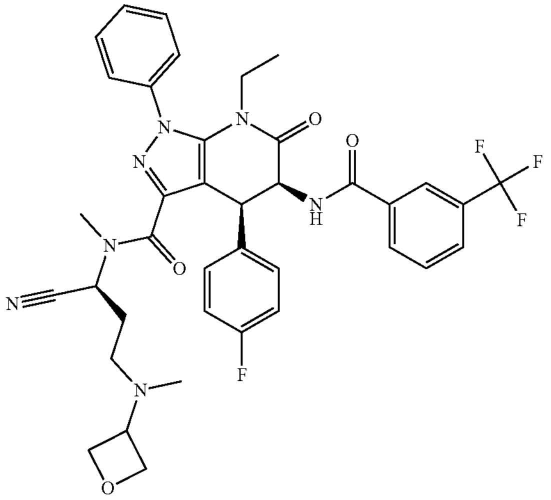

-continued
I-311
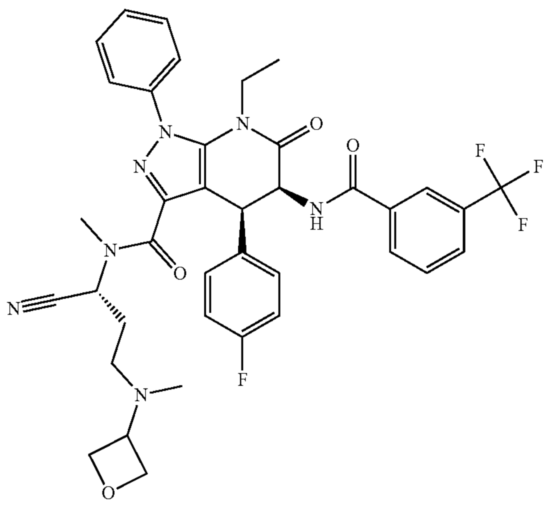
I-312
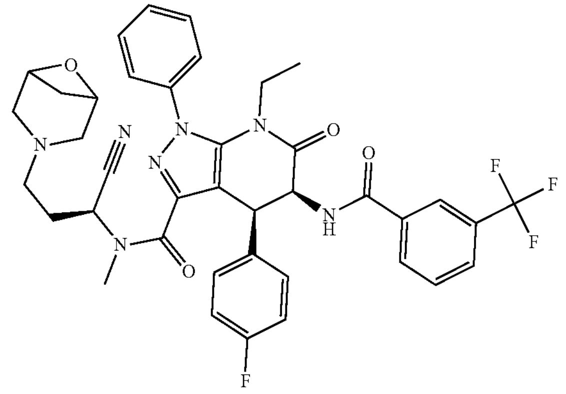
I-313
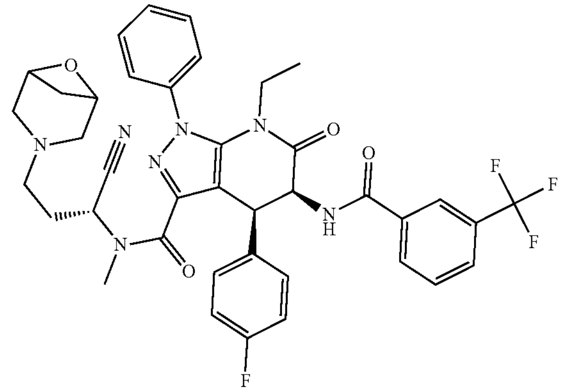
-continued
I-314
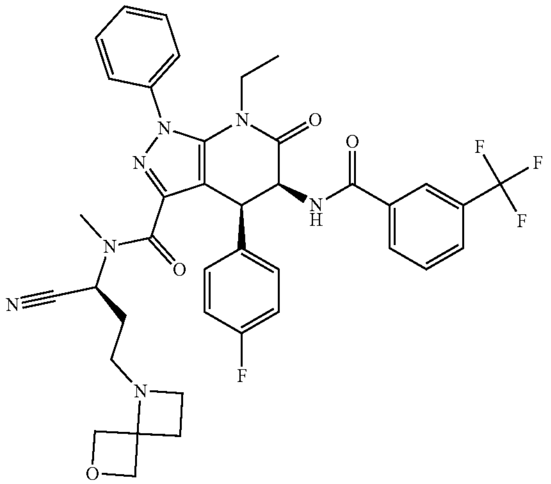
I-315
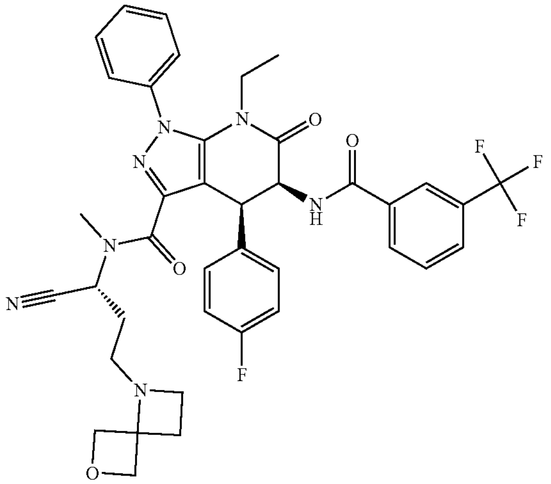
I-316
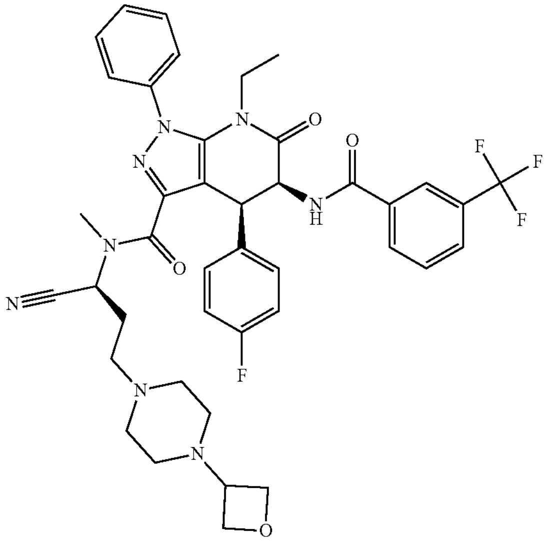

-continued
I-317
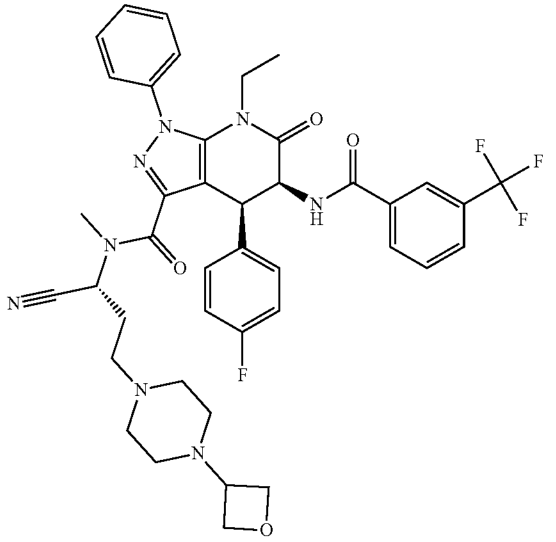
I-318
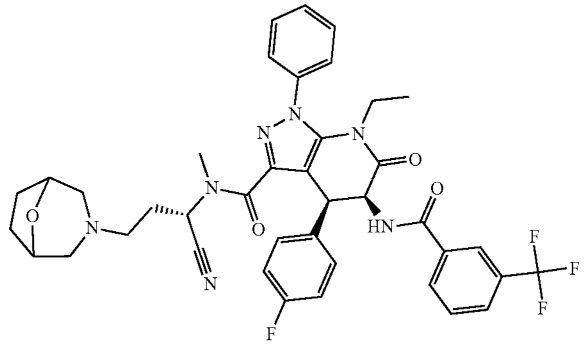
I-319
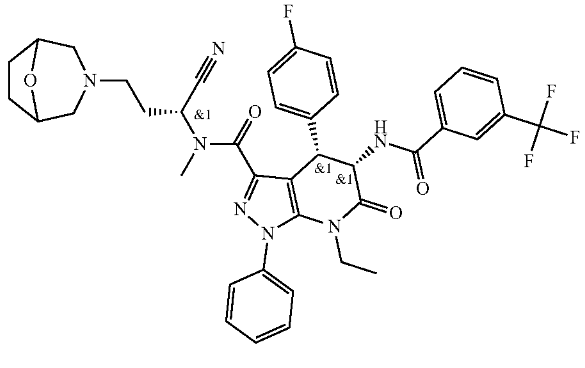
-continued
I-320
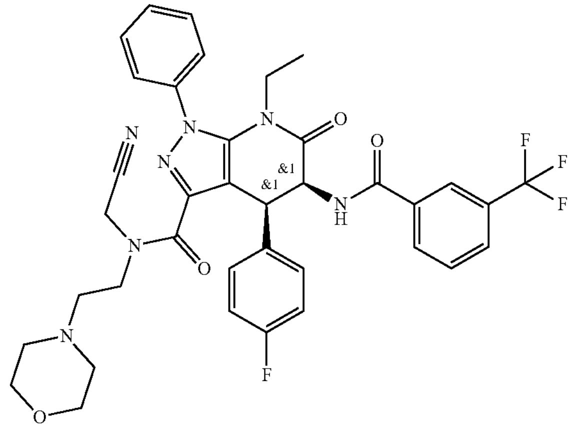
I-321
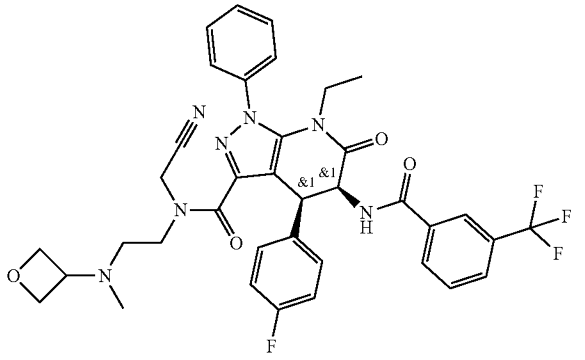
I-322
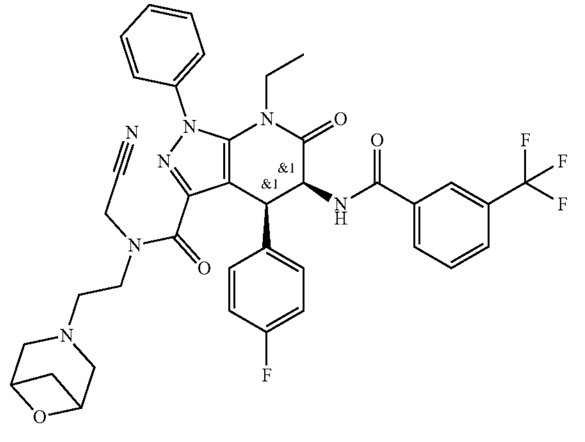

I-323
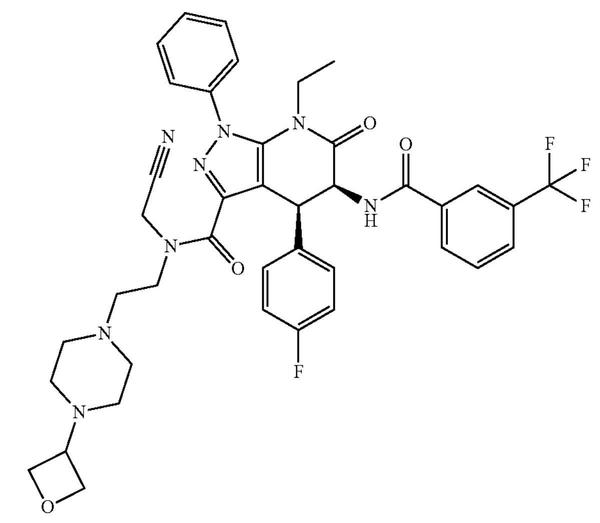
I-324
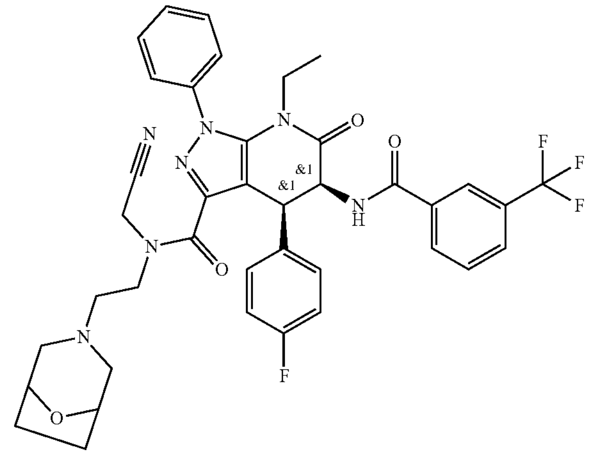
I-325
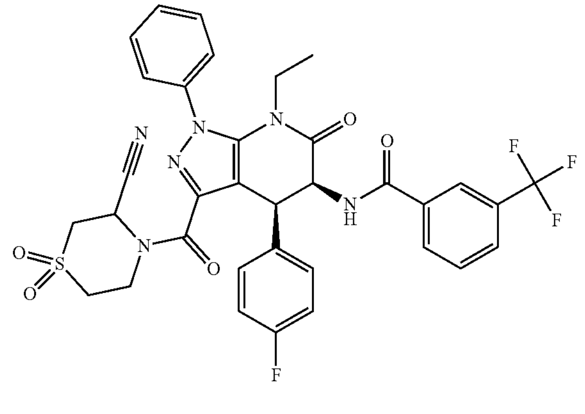
I-326
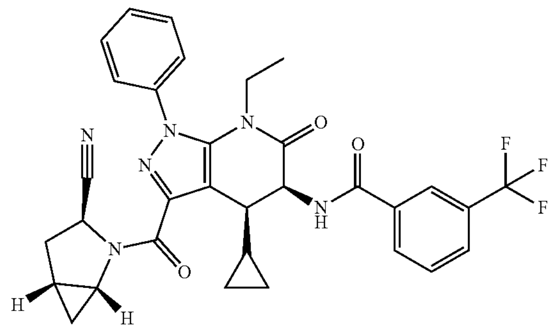
I-327
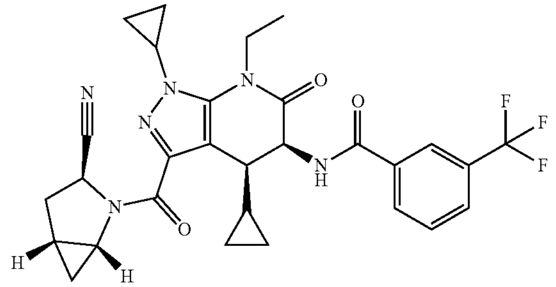
I-328
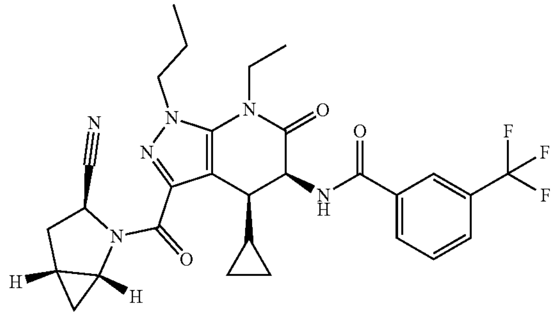

-continued
I-329
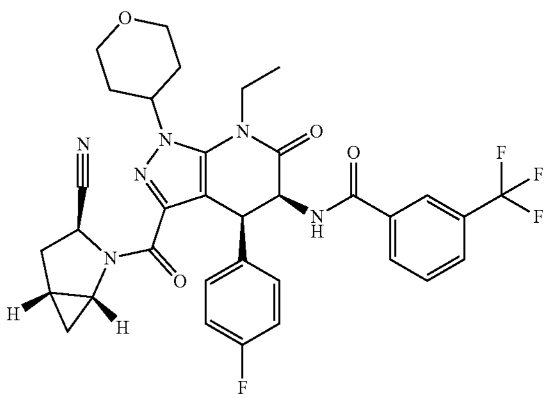
I-330
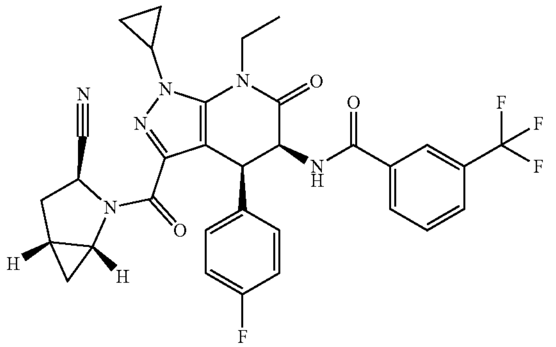
I-333
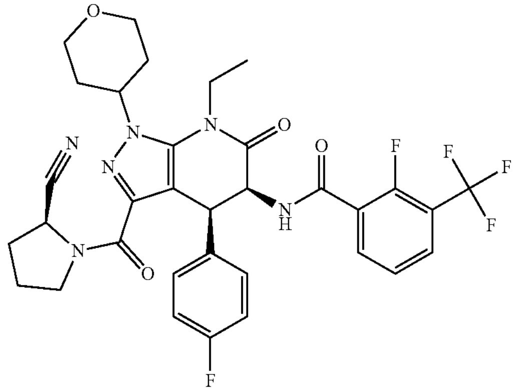
-continued
I-331
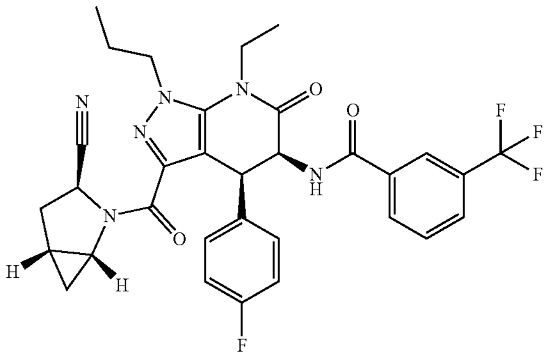
I-332
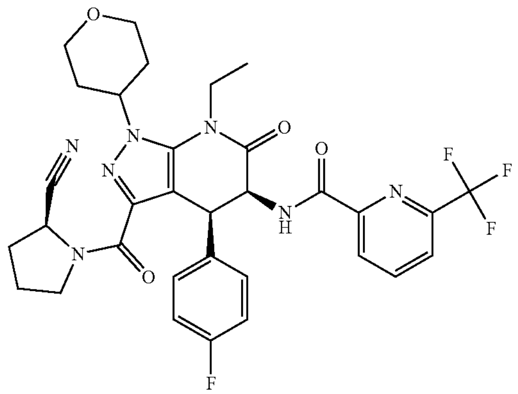
I-334
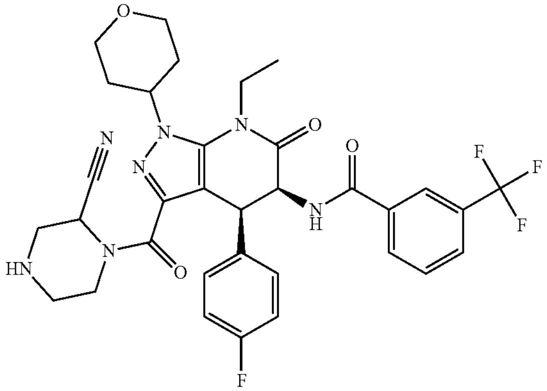

-continued
I-335
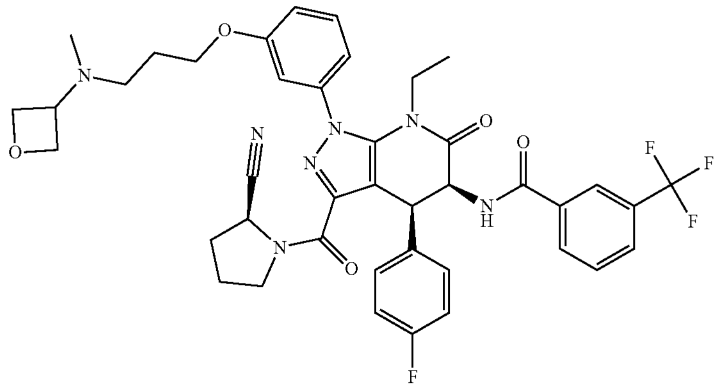
I-336
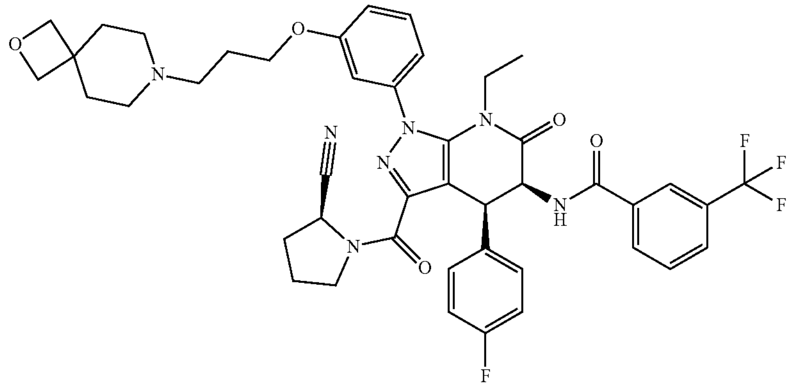
I-337
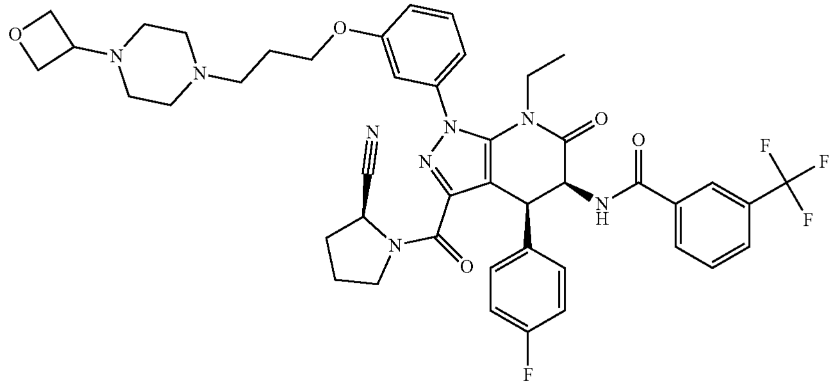
I-338
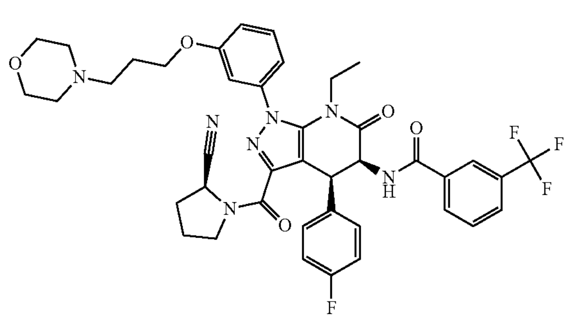
I-339
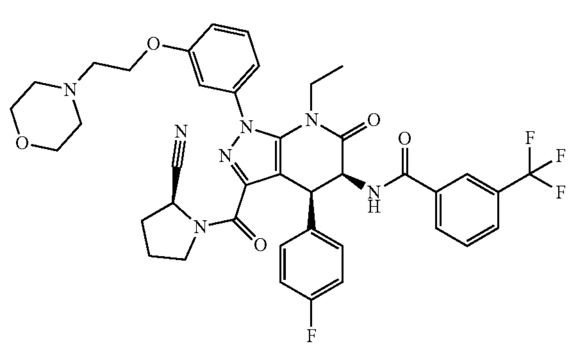

-continued
I-340
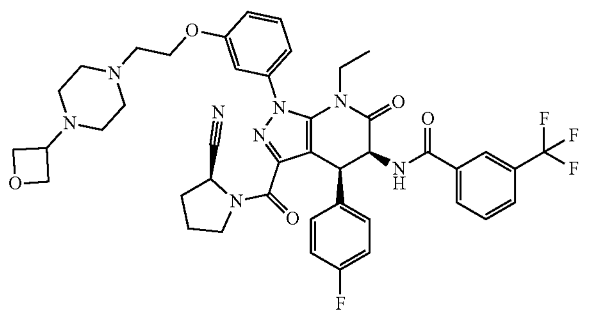
I-341
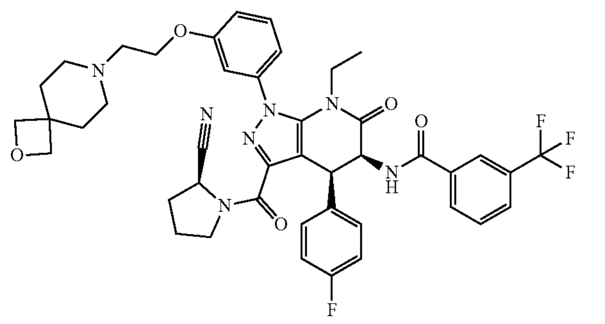
I-342
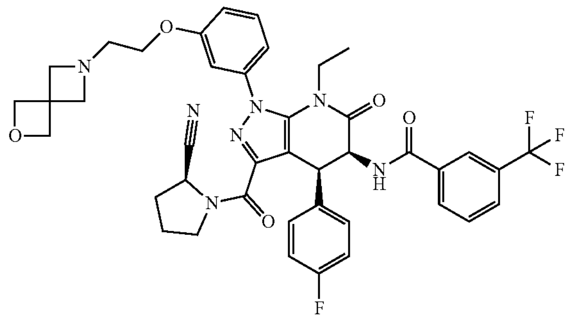
I-343
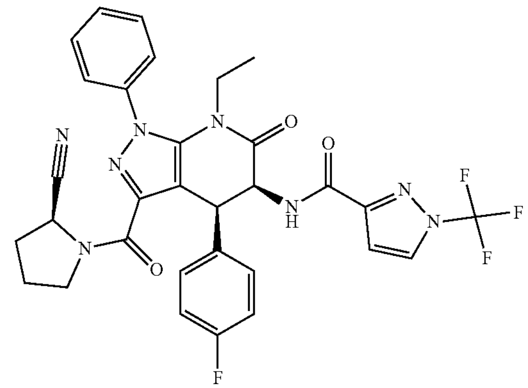
I-344
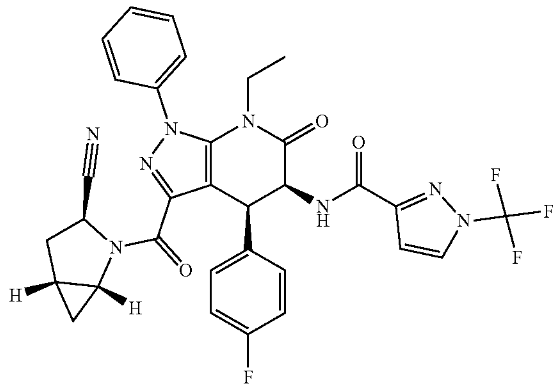
I-345
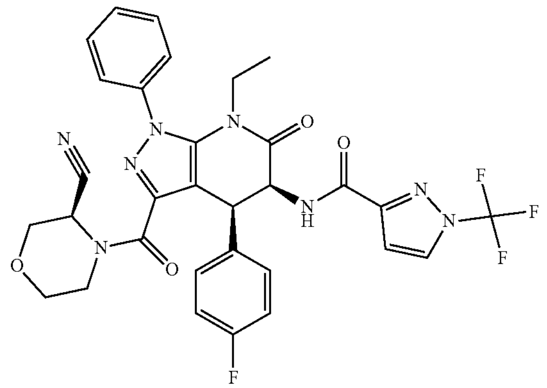
I-346
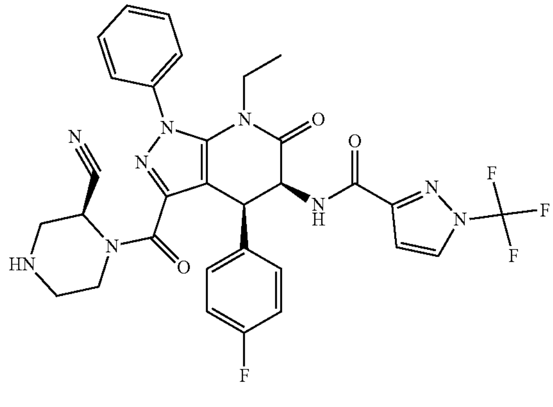
I-347
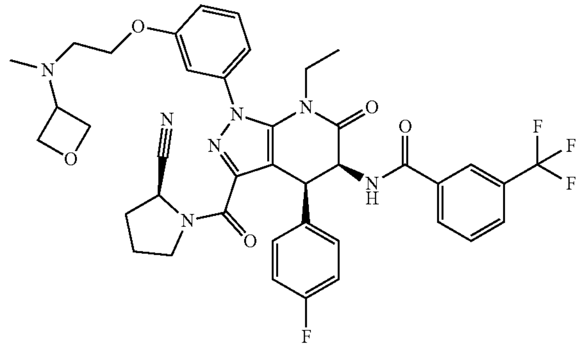

-continued
I-348
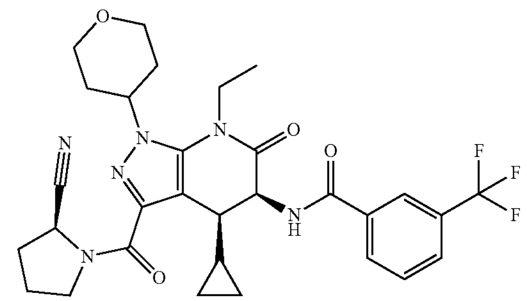
I-349
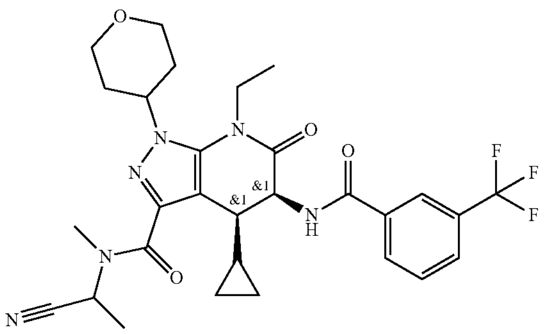
I-350
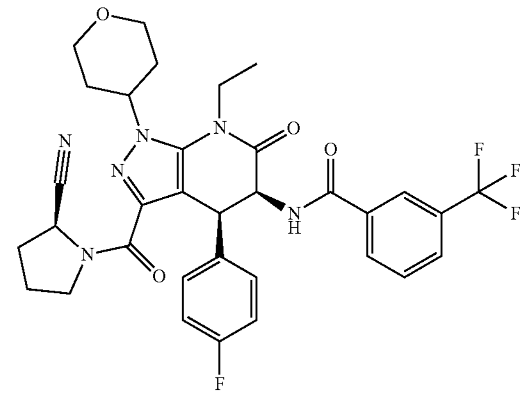
I-351
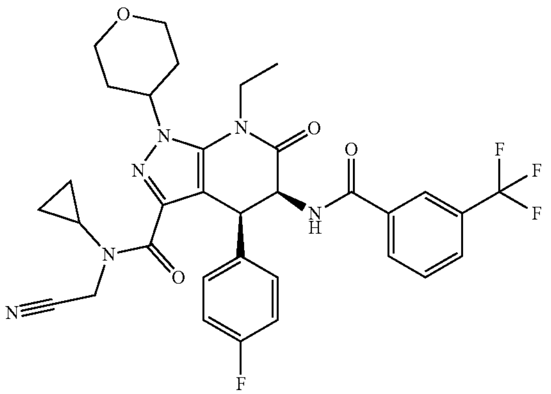
I-352
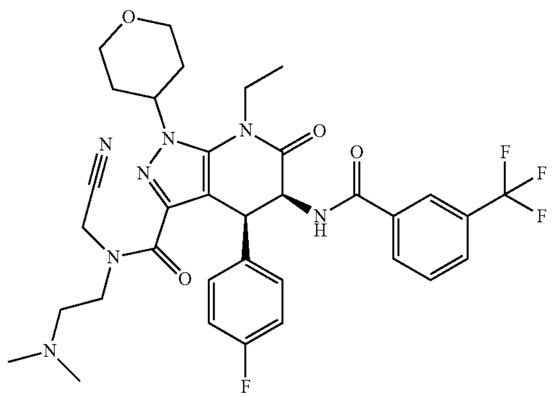
I-353
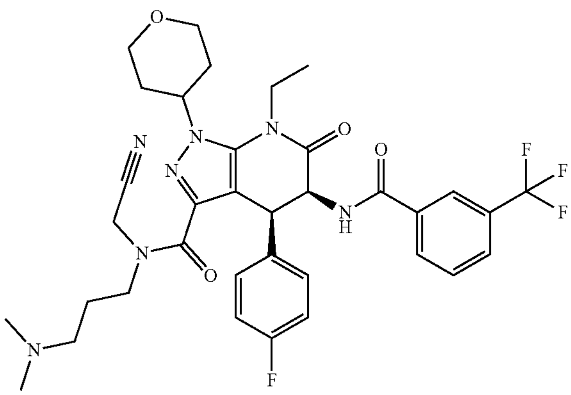
I-354
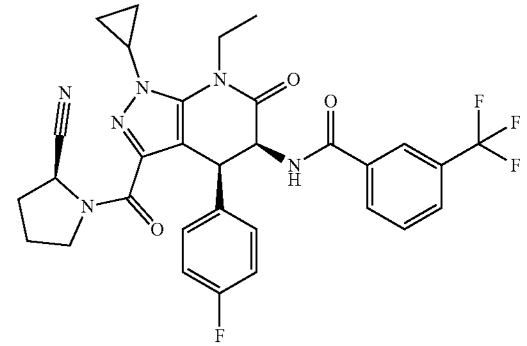
I-355
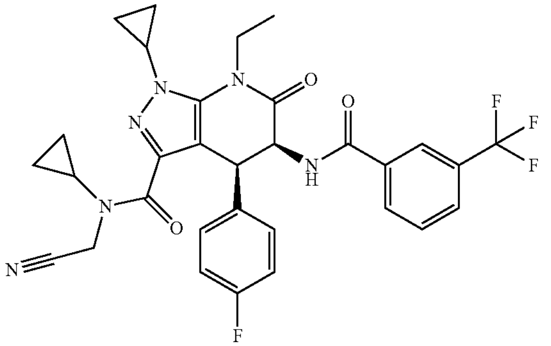

-continued
I-356
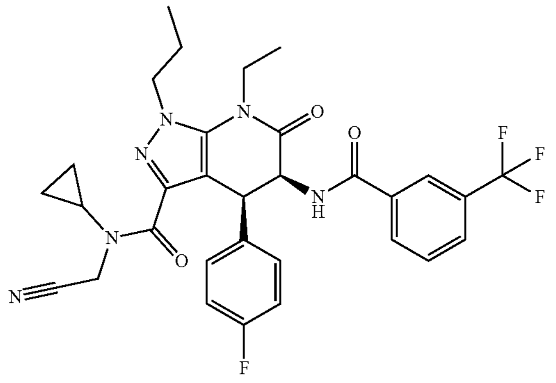
I-357
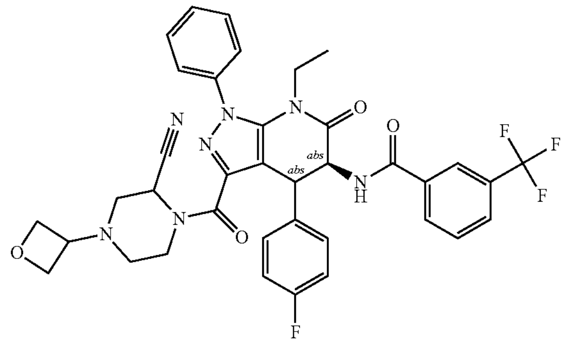
I-358
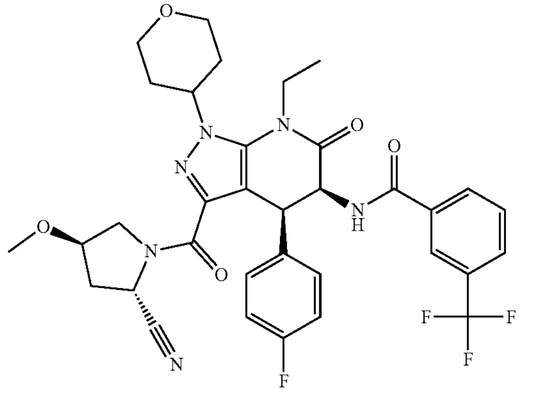
I-359
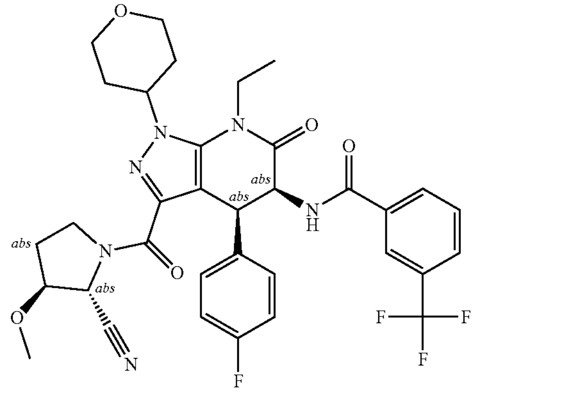
I-360
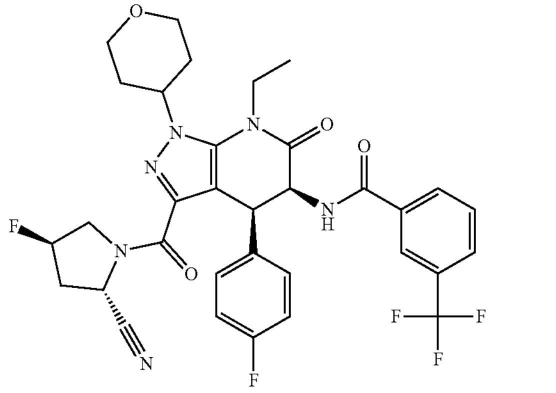
I-361
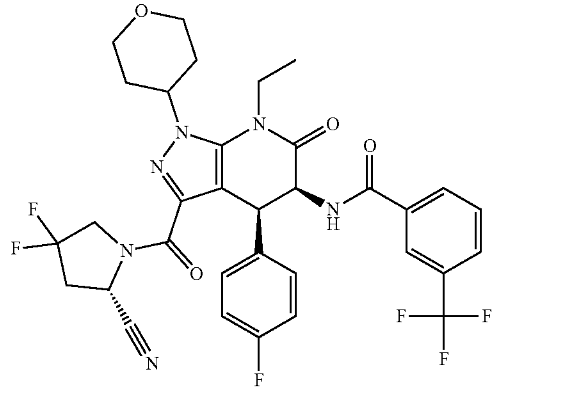
I-362
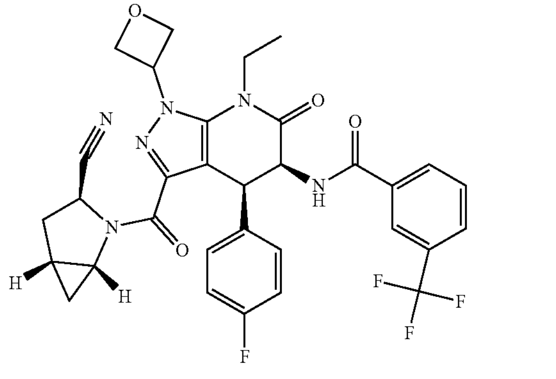
I-363
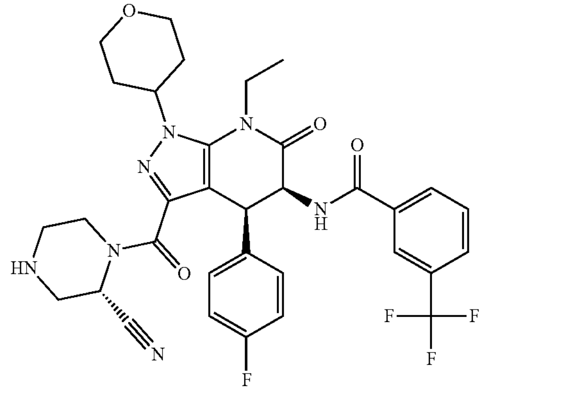

-continued
I-364
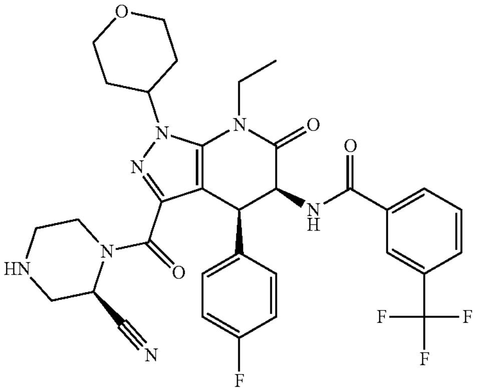
I-365
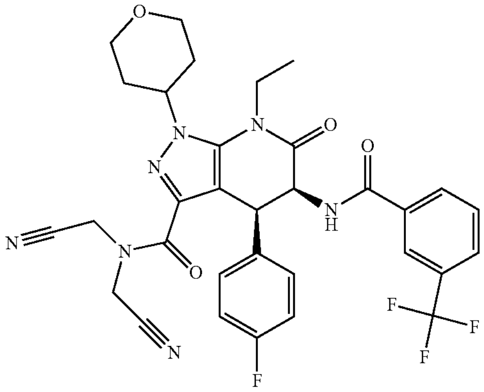
I-366
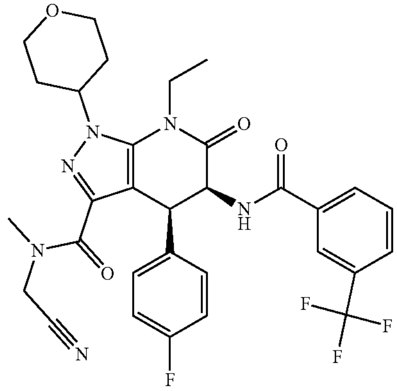
I-367
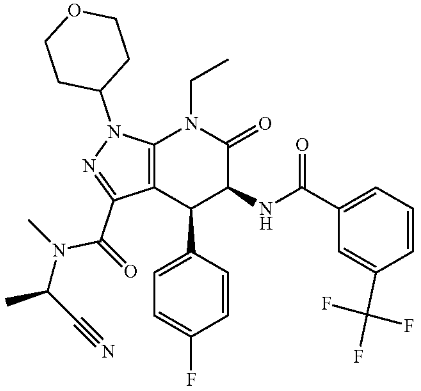
I-368
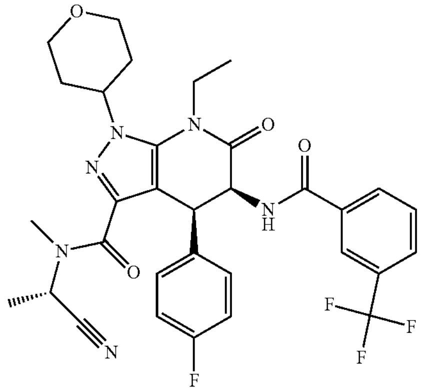
I-369
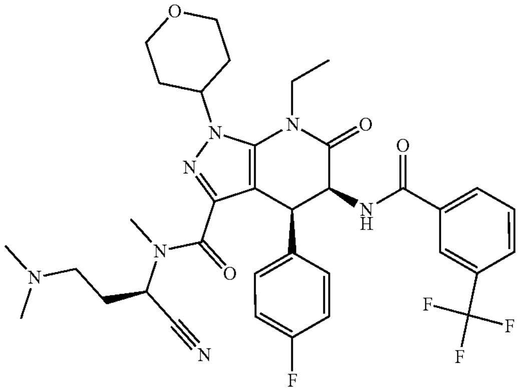
I-370
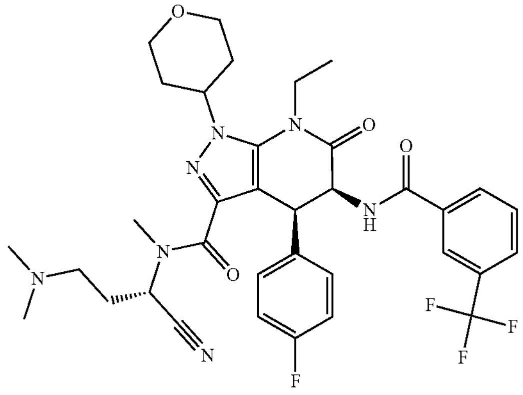
I-371
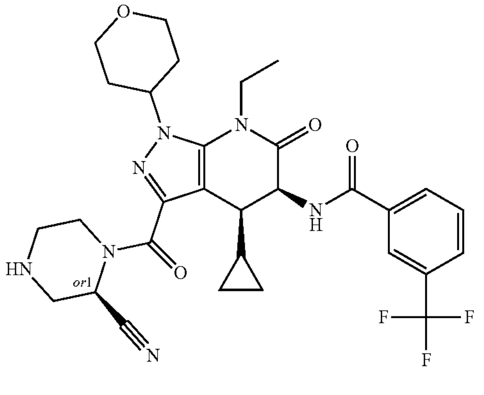

-continued
I-372
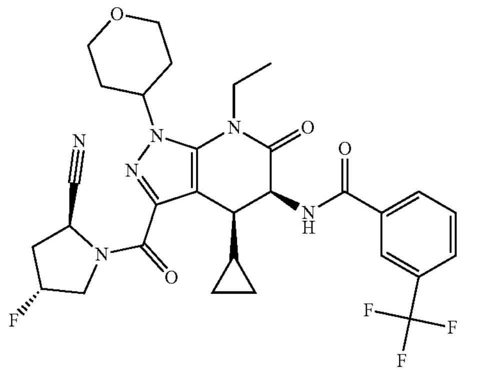
I-373
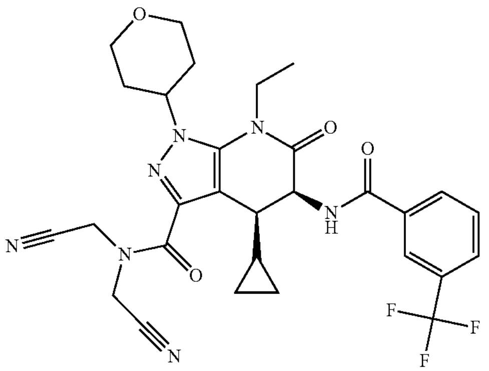
I-374
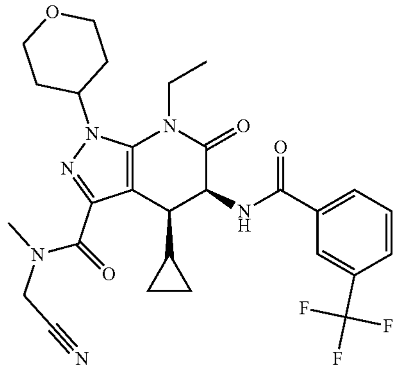
I-375
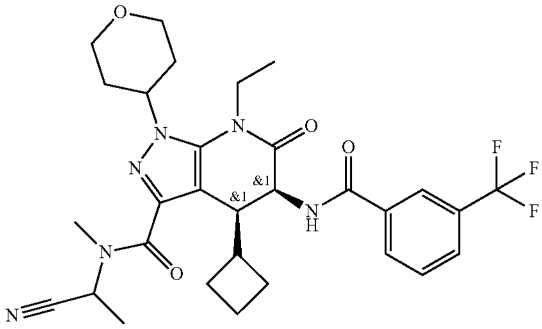
I-376
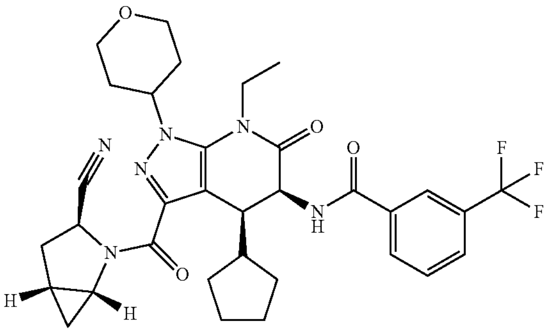
I-377
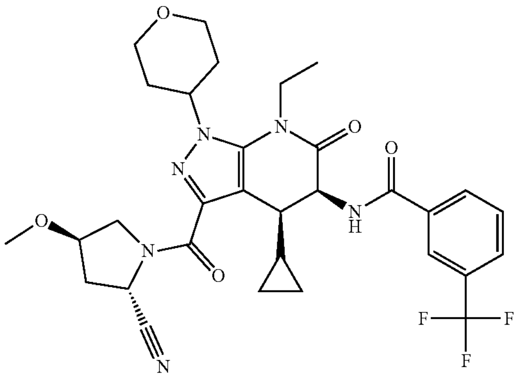
I-378
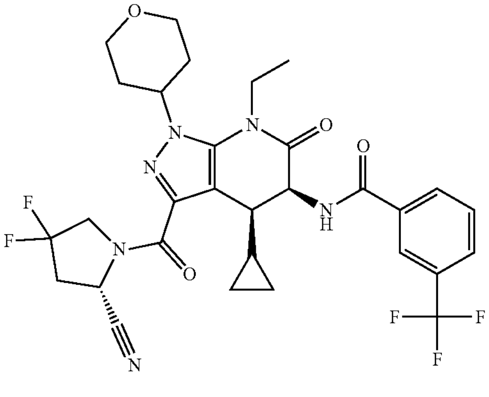

-continued
I-379
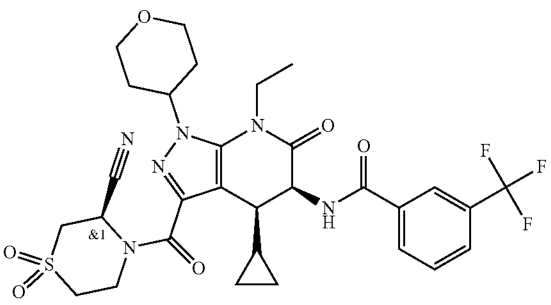
I-380
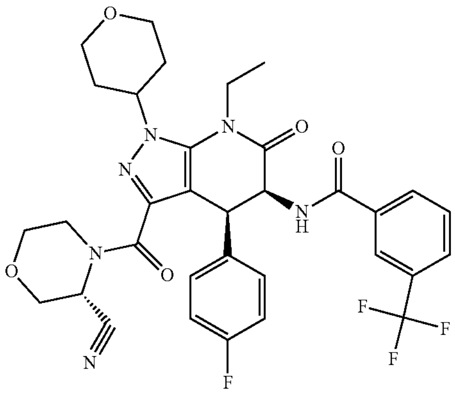
I-381
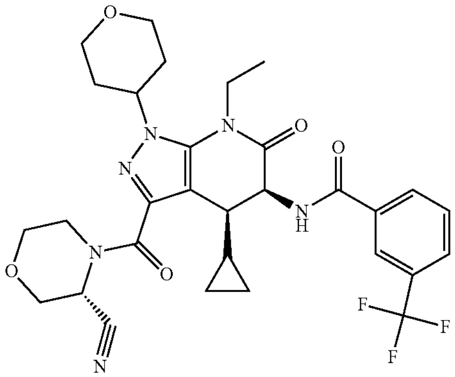
I-382
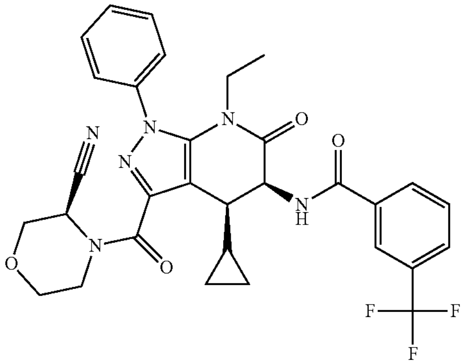
I-383
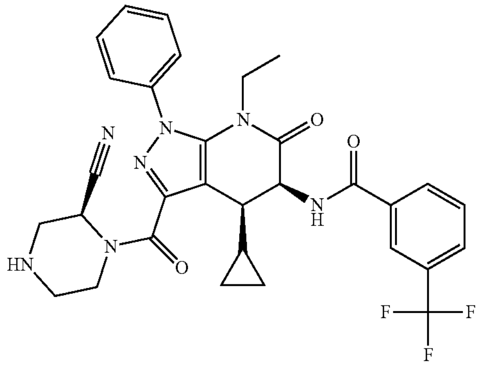
I-384
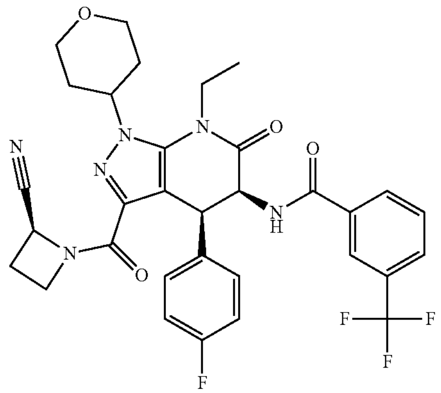
I-385
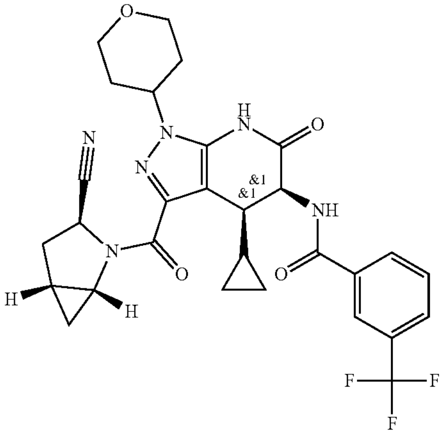
I-386
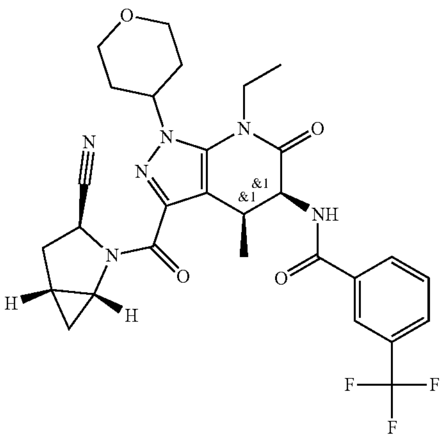

-continued
I-387
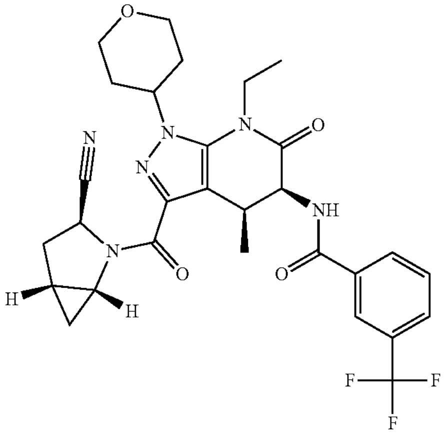
I-388
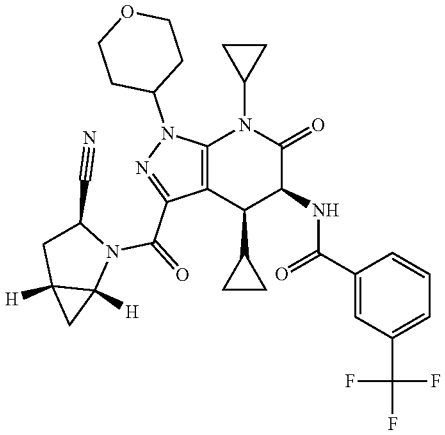
I-389
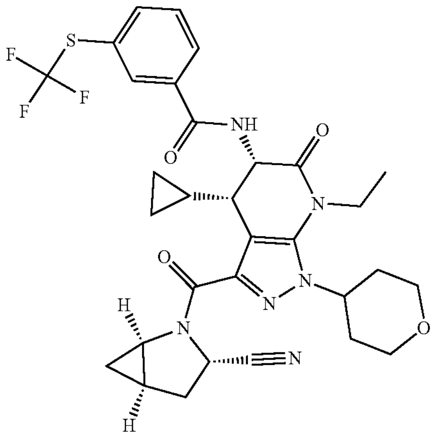
-continued
I-390
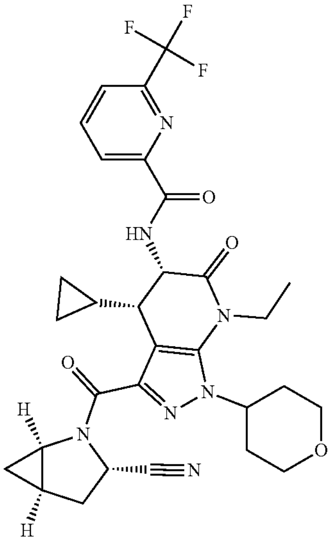
I-391
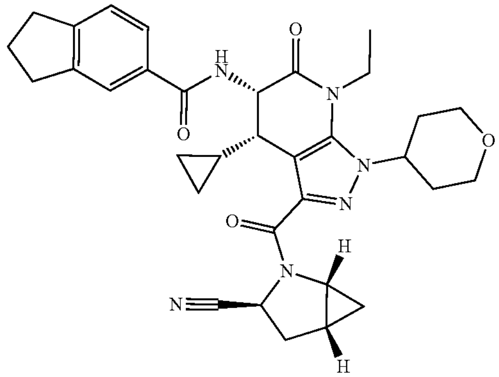
I-392
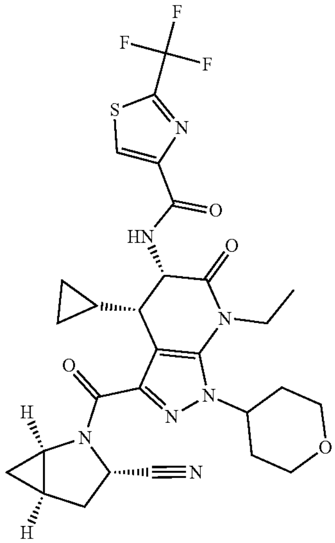

-continued
I-393
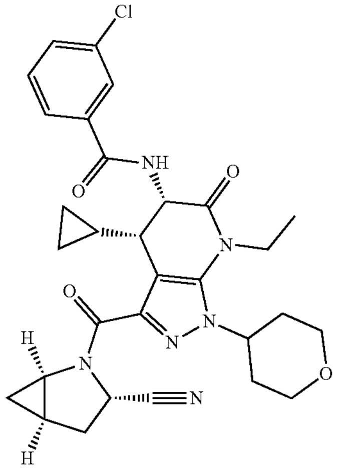
I-394
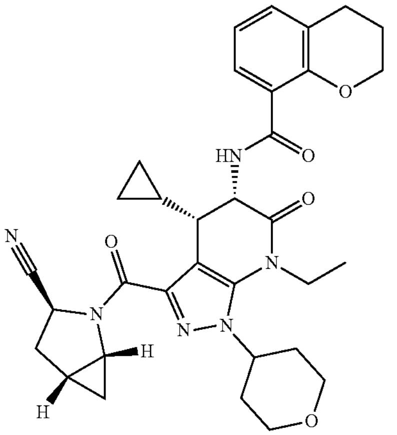
I-395
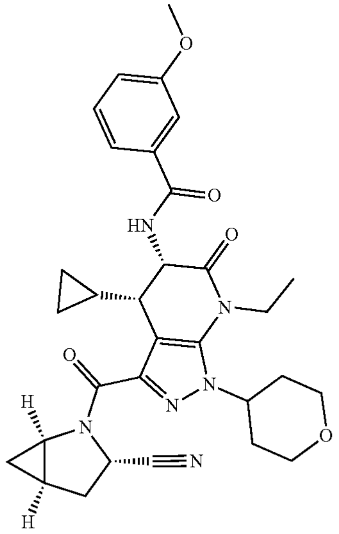
-continued
I-396
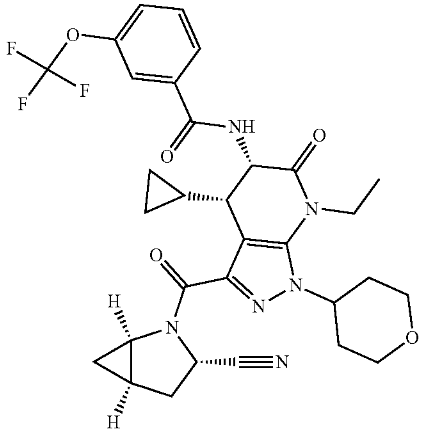
I-397
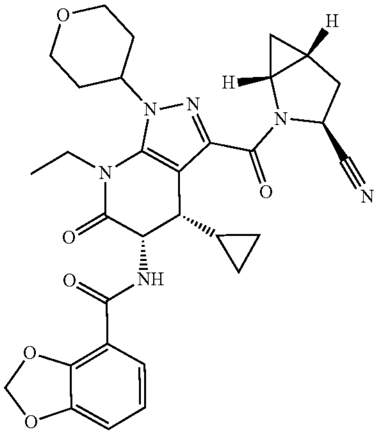
I-398
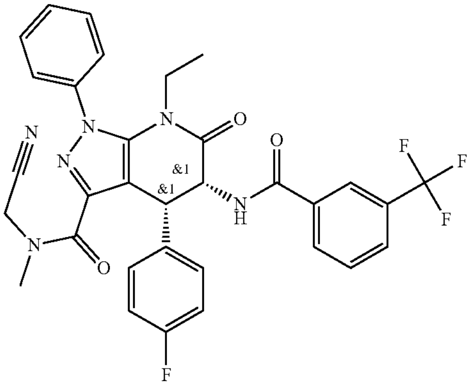

-continued
I-399
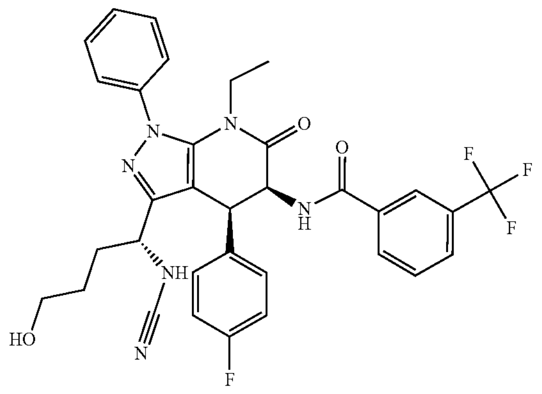
I-400
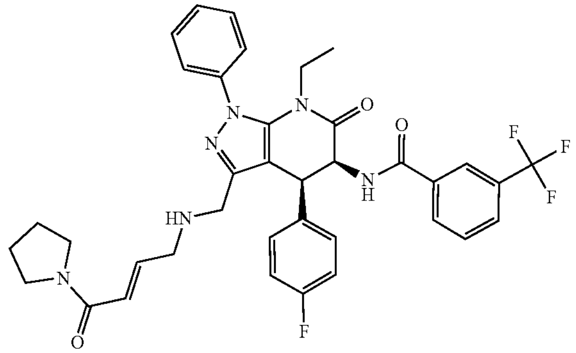
I-401
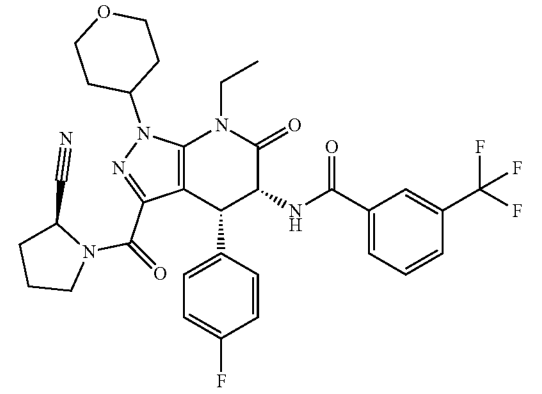
I-402
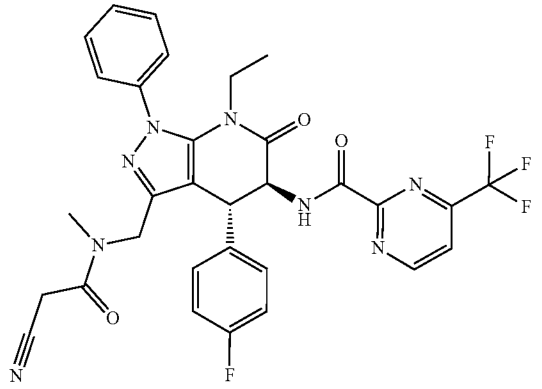
-continued
I-403
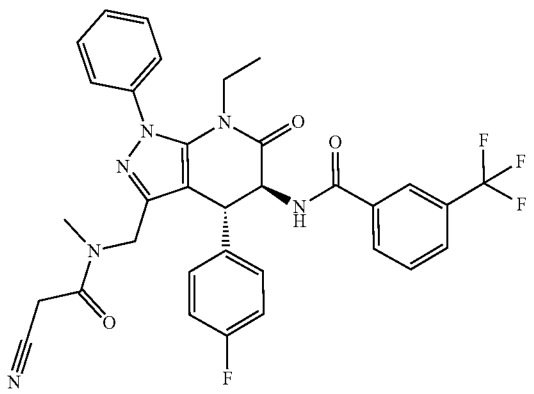
I-405
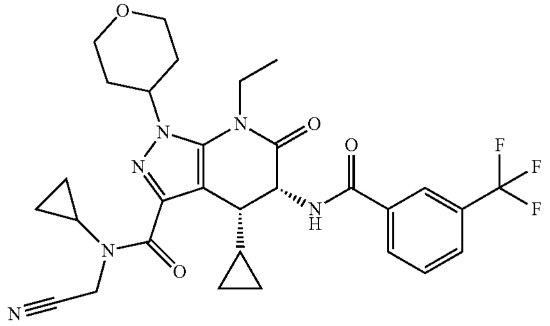
I-406
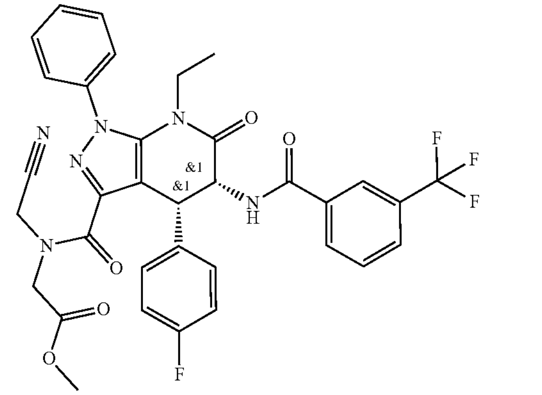
I-407
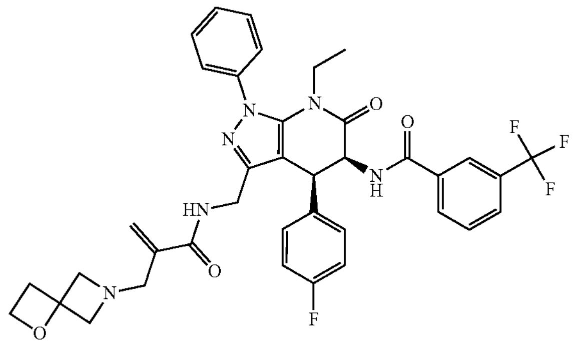

-continued
I-408
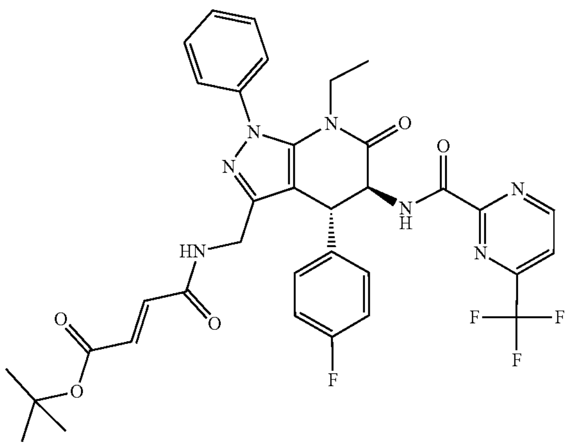
I-409
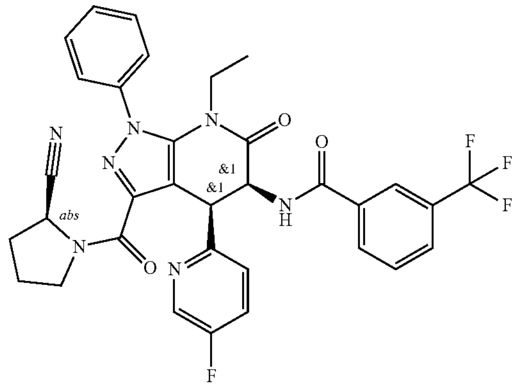
I-410
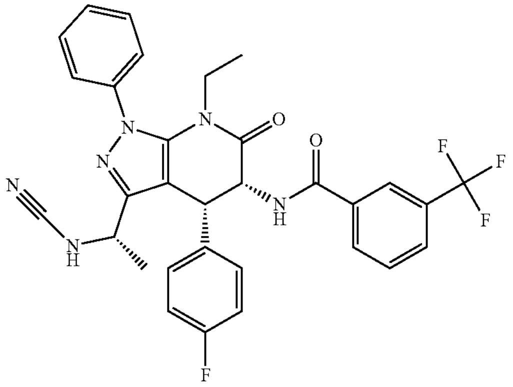
-continued
I-411
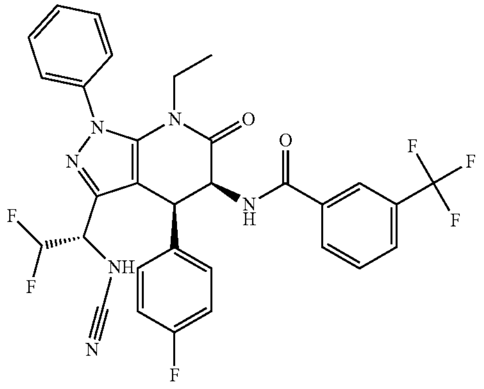
I-412
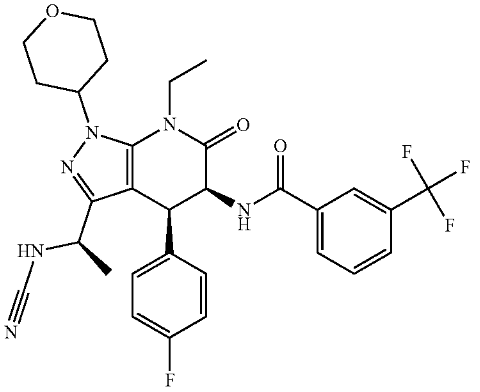
I-413
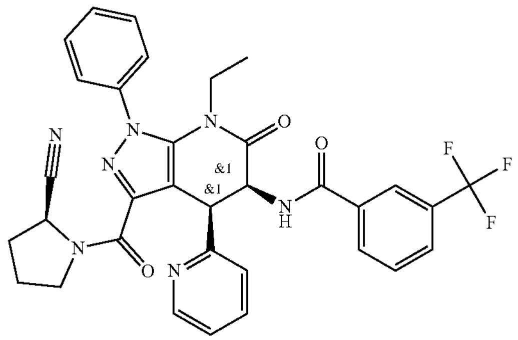
I-414
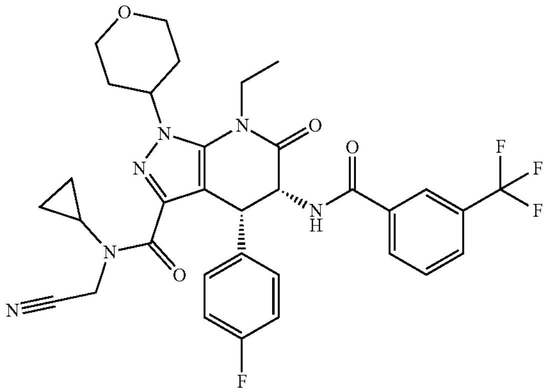

-continued
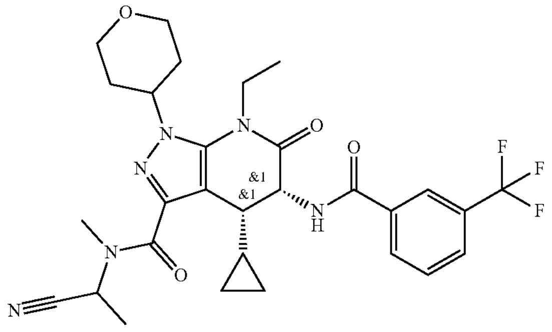
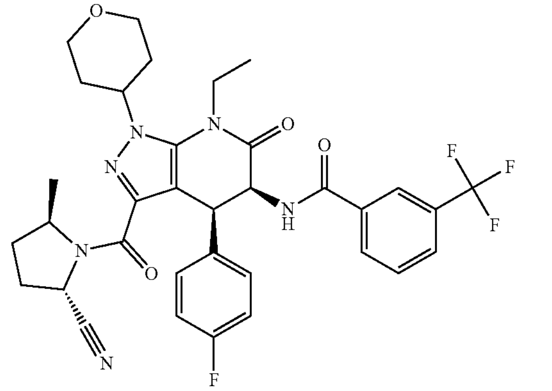
I-417
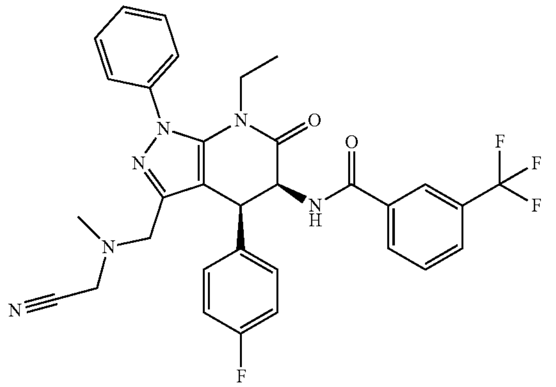
I-418
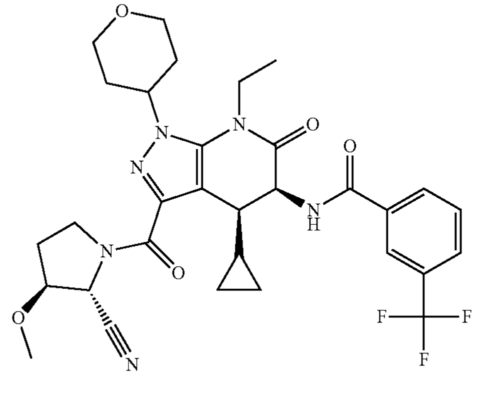
-continued
I-419
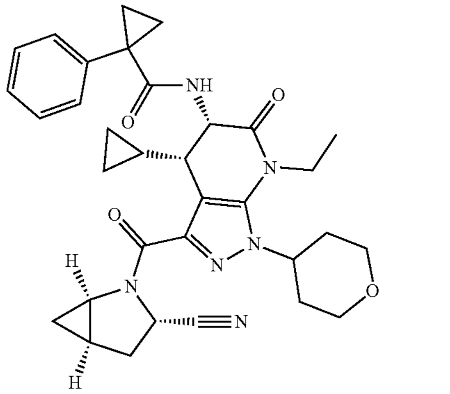
I-420
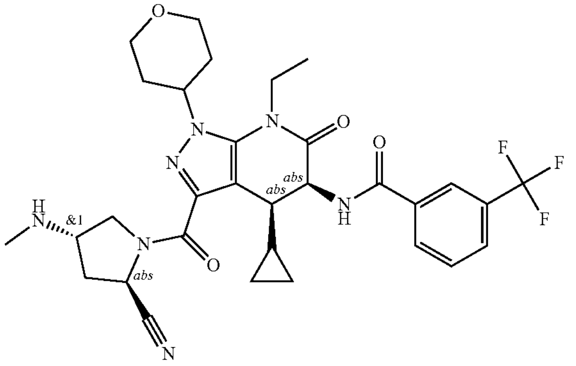
I-421
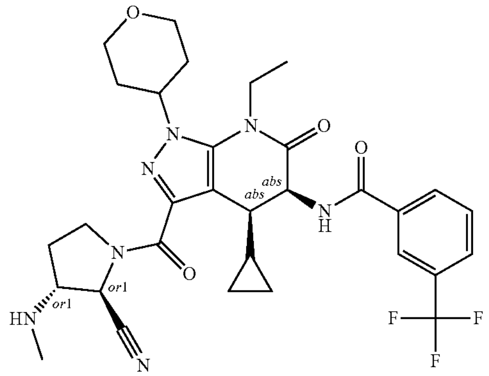
I-422
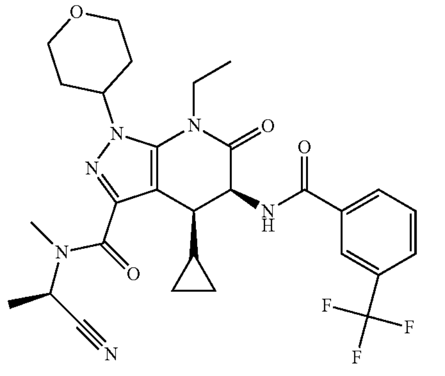

I-423
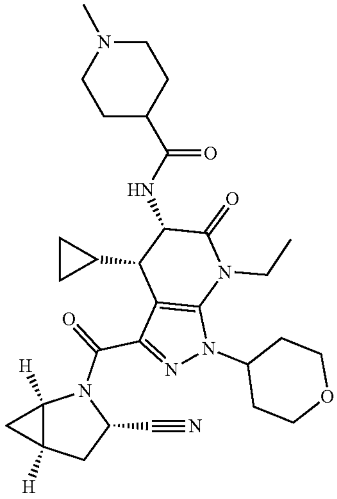
I-424
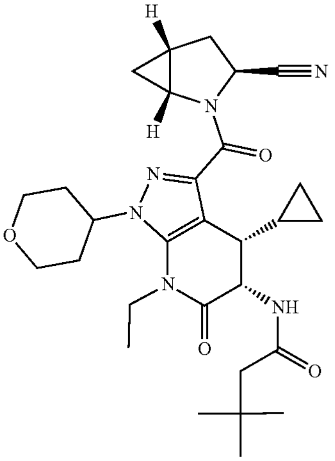
I-425
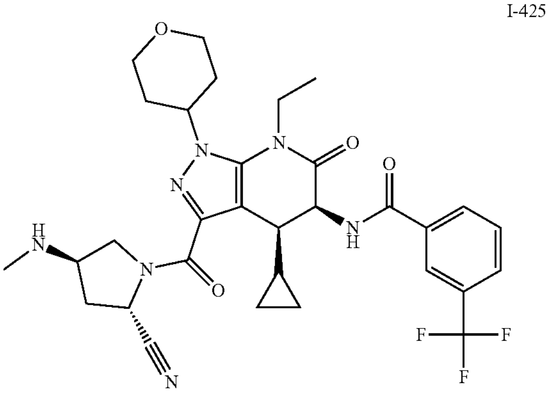
I-426
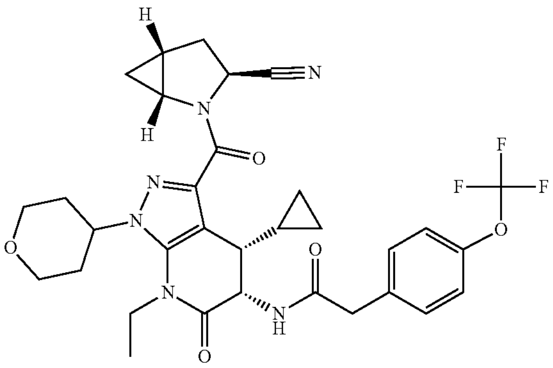
I-427
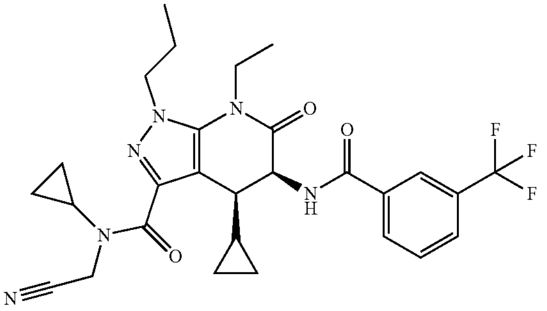
I-428
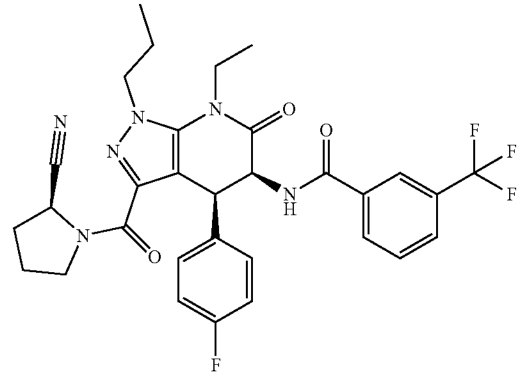
I-429
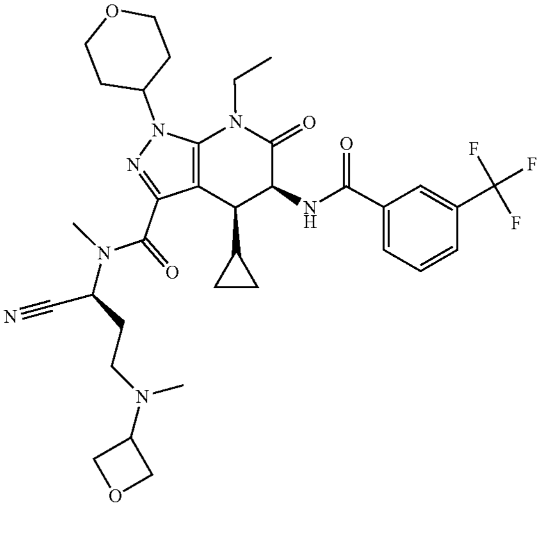

-continued
I-430
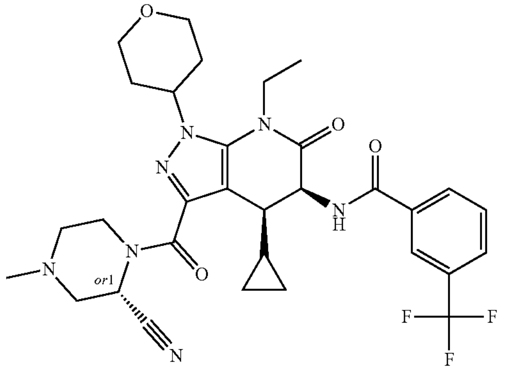
I-431
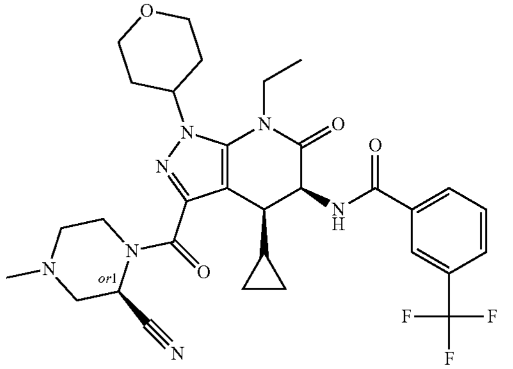
I-432
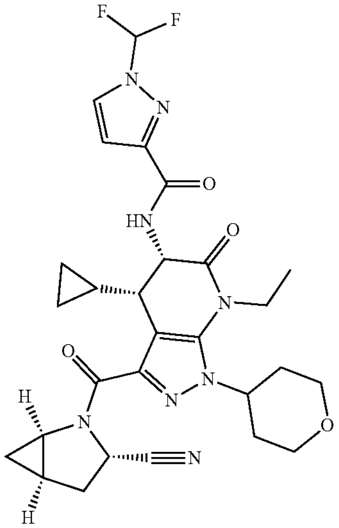
-continued
I-433
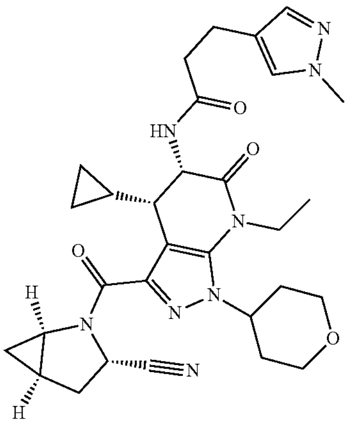
I-434
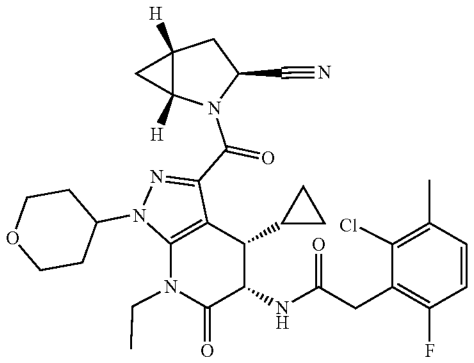
I-435
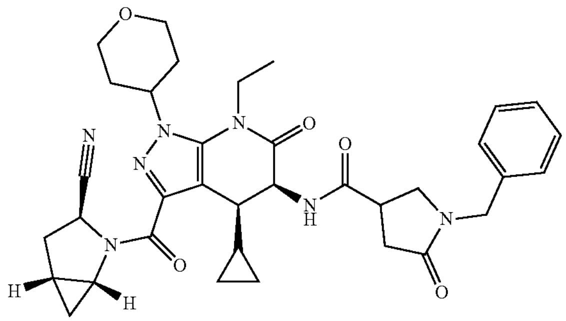
I-436
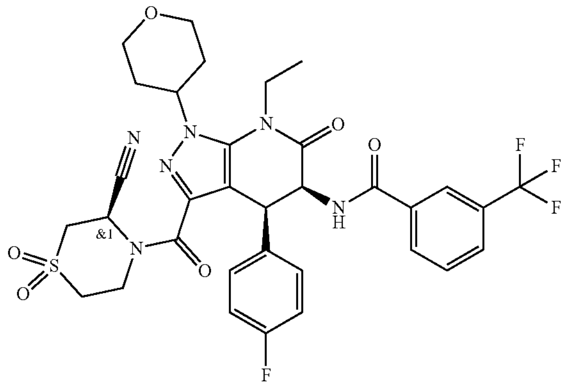

-continued
I-437
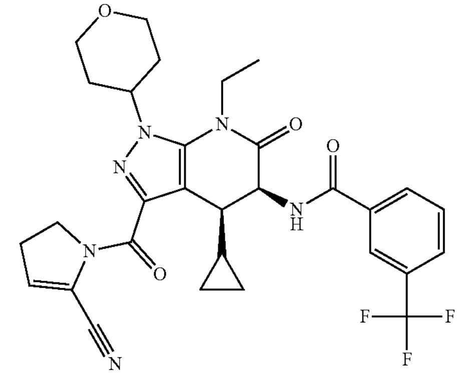
I-438
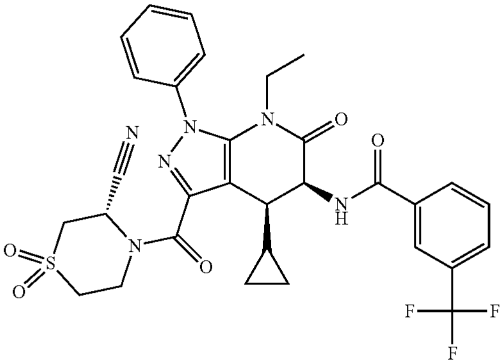
I-439
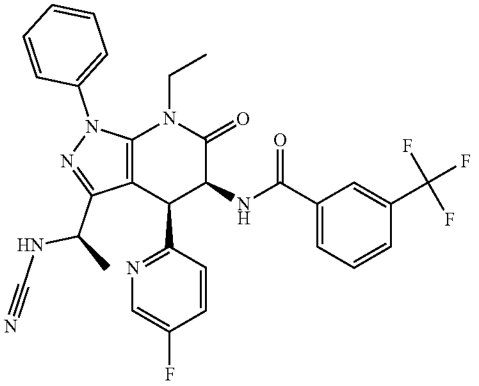
I-440
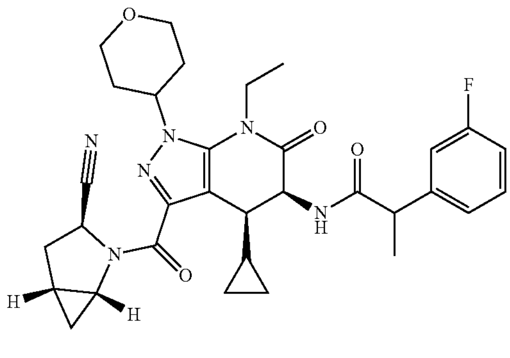
-continued
I-441
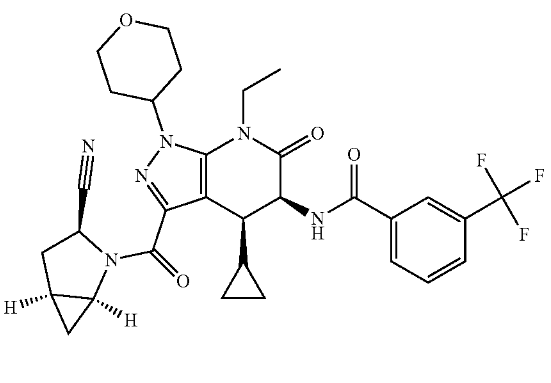
I-442
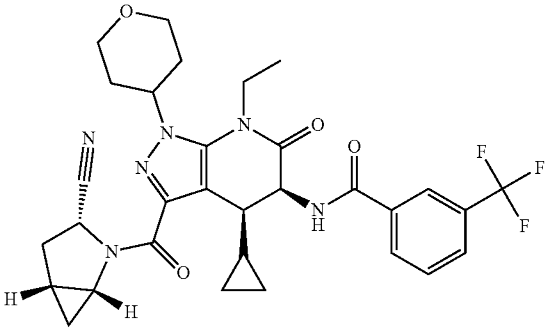
I-444
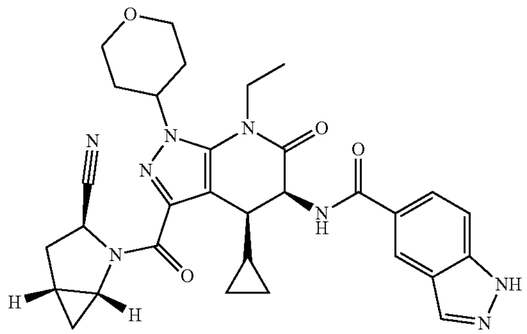
I-445
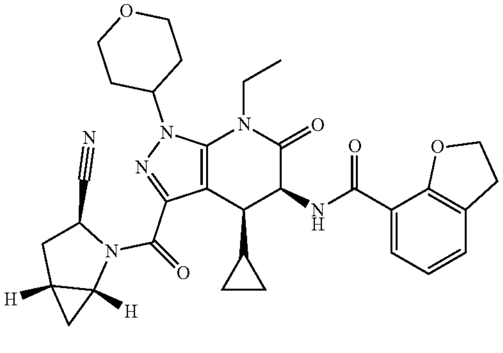

-continued
I-446
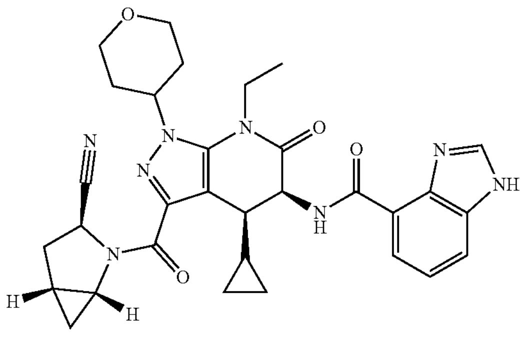
I-447
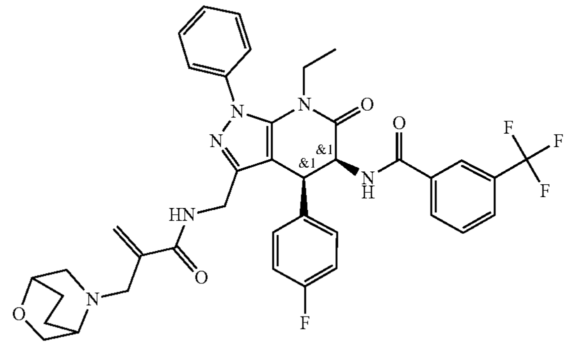
I-448
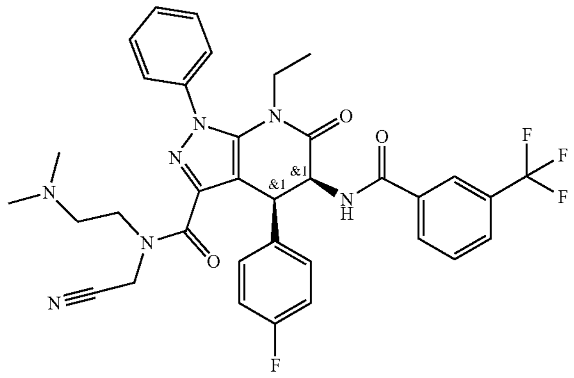
I-450
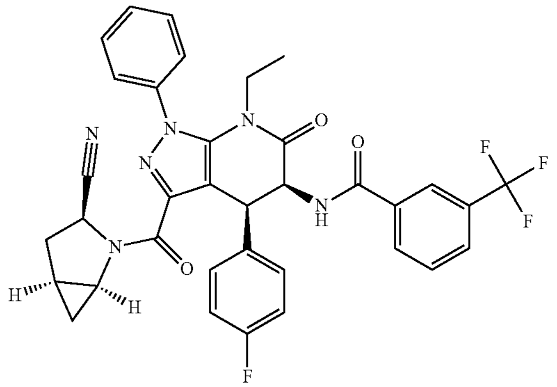
-continued
I-451
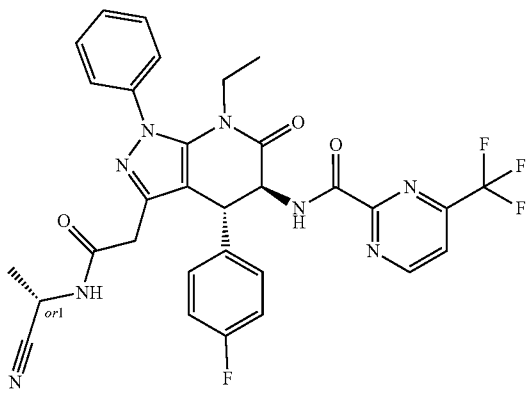
I-452
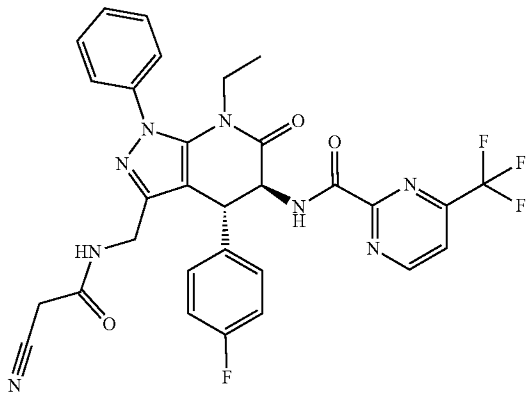
I-453
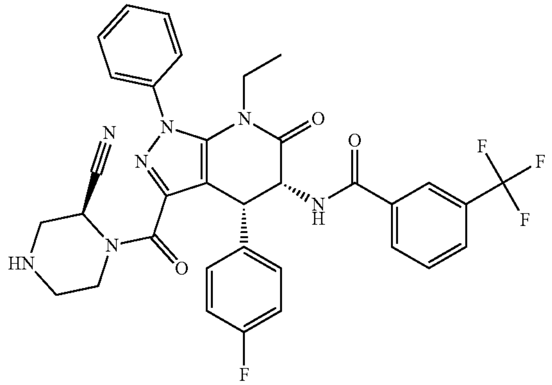
I-454
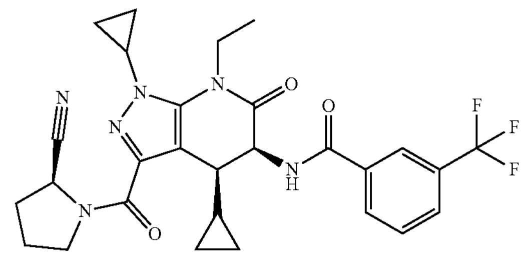

-continued
I-455
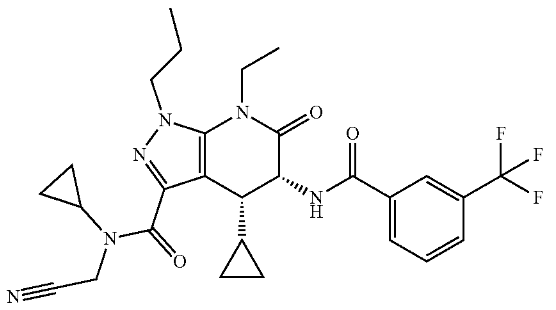
I-456
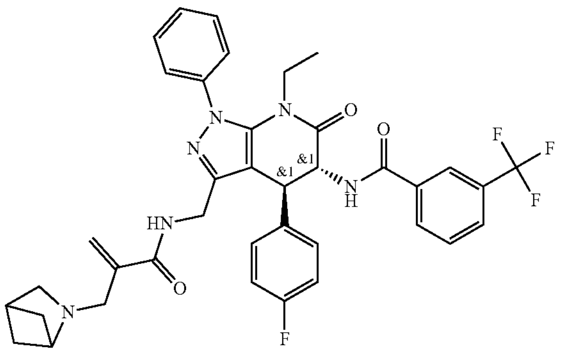
I-457
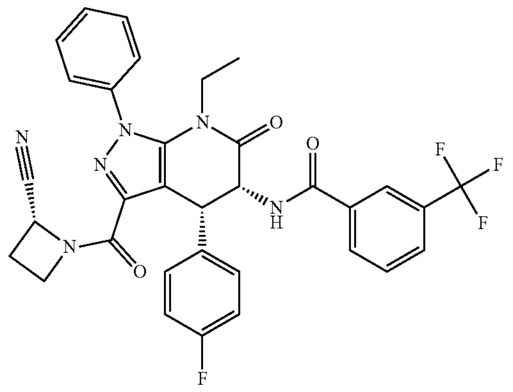
I-458
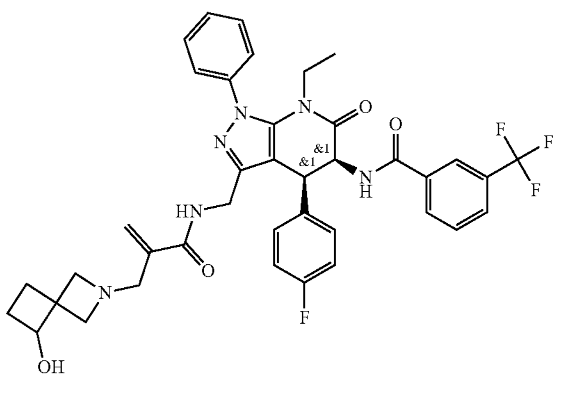
I-459
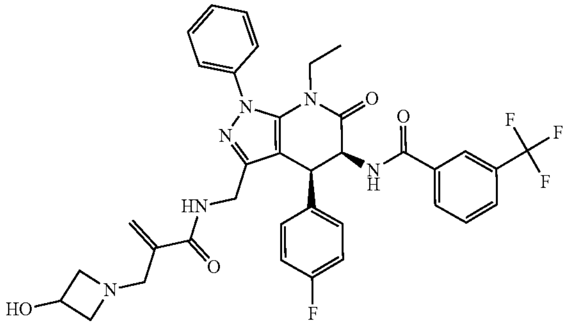
I-460
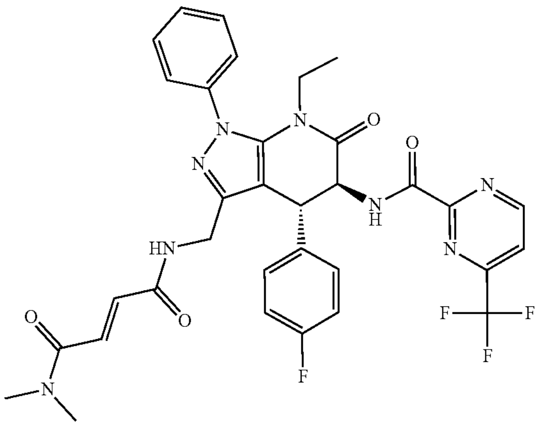
I-461
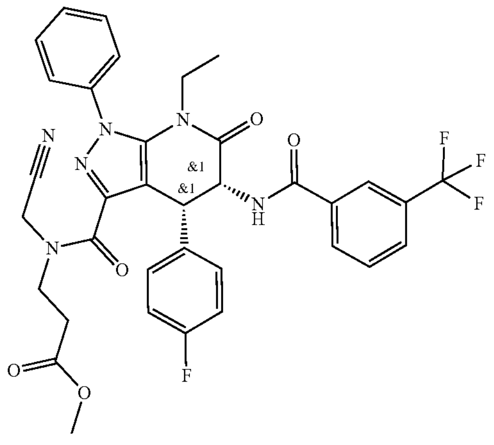
I-462
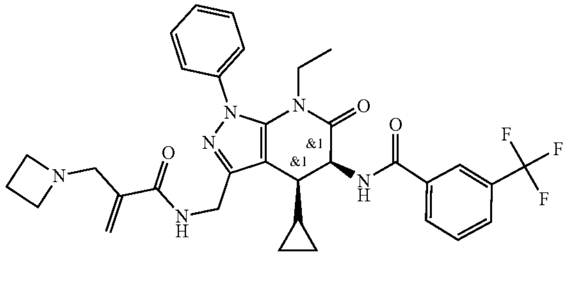

-continued
I-463
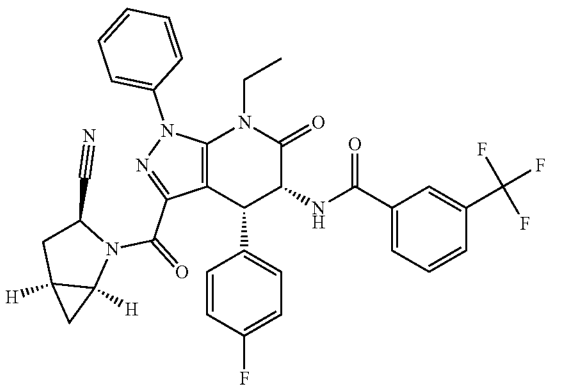
I-464
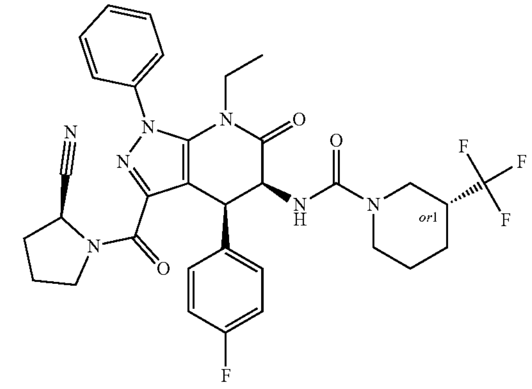
I-465
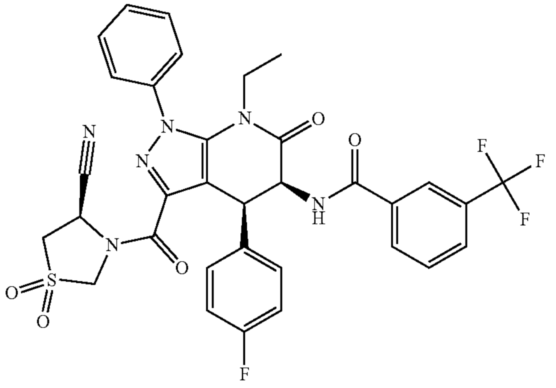
I-466
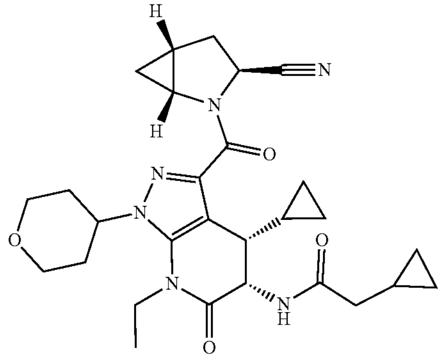
-continued
I-467
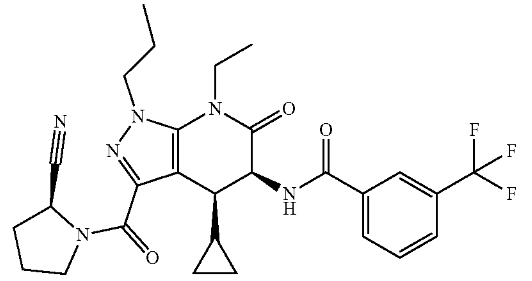
I-468
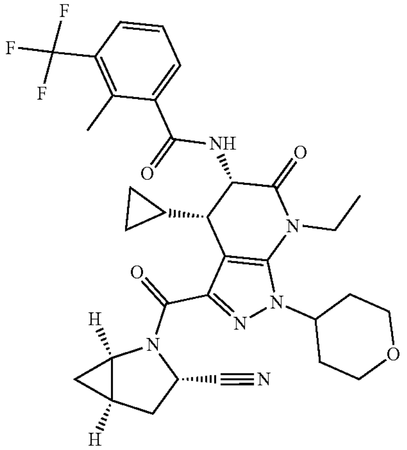
I-469
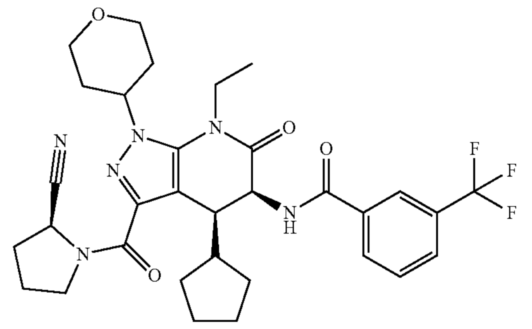
I-470
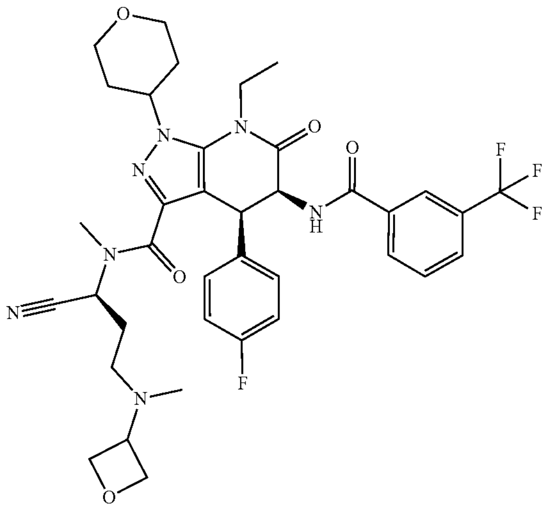

-continued
I-471
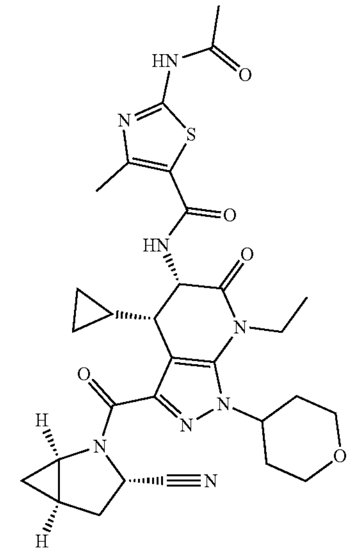
I-472
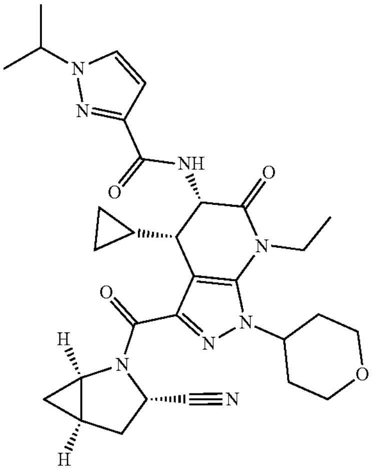
I-473
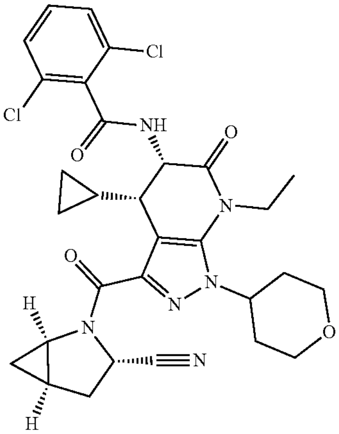
-continued
I-474
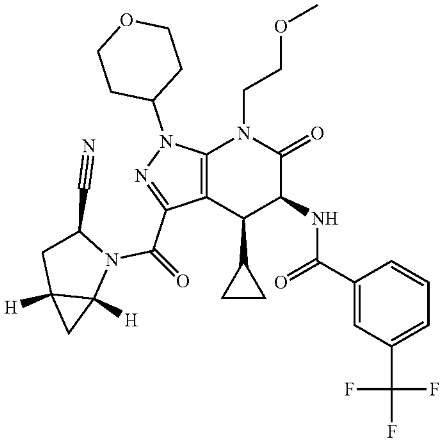
I-475
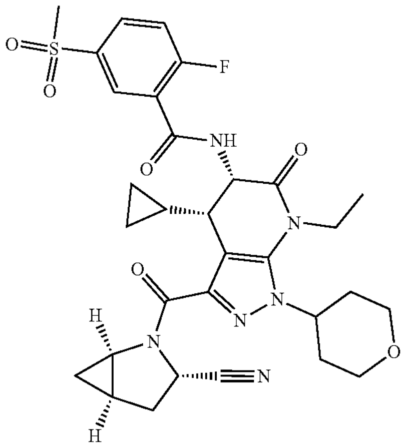
I-476
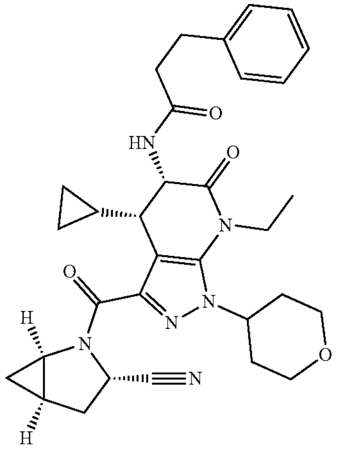

-continued
I-478
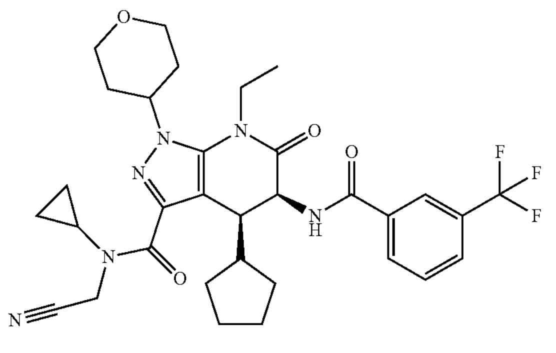
I-479
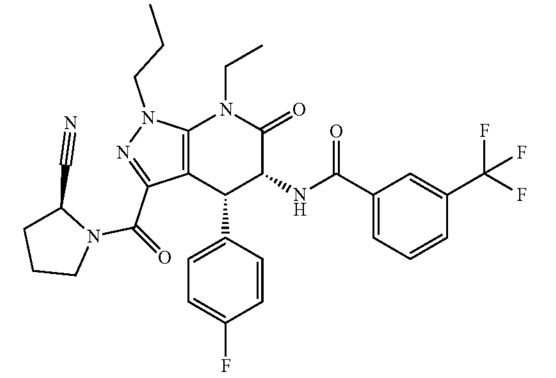
I-480
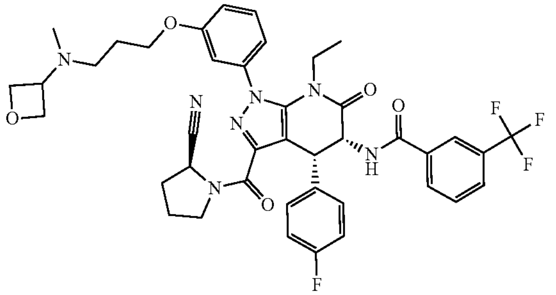
I-481
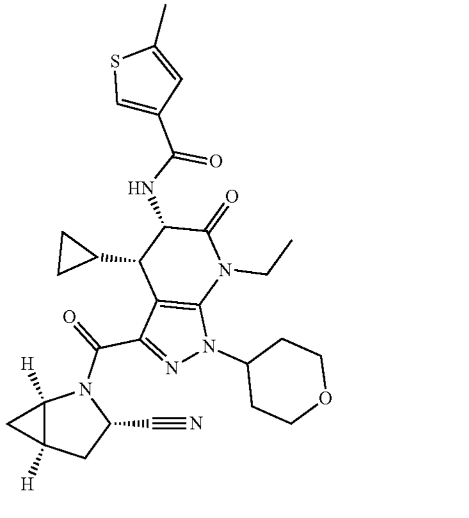
-continued
I-482
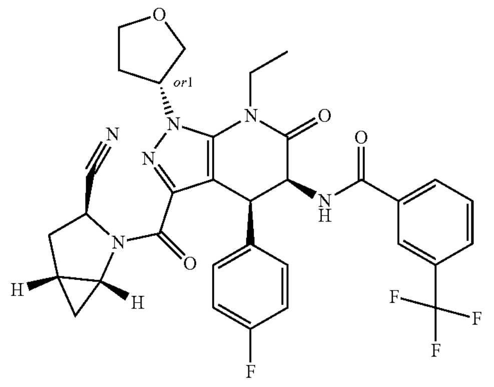
I-483
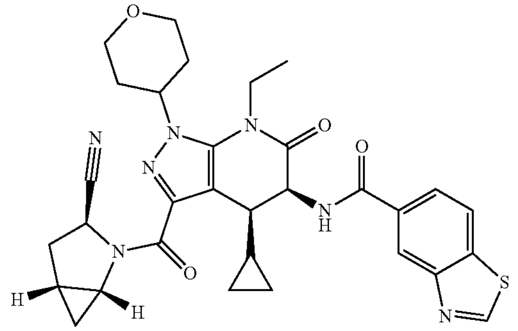
I-486
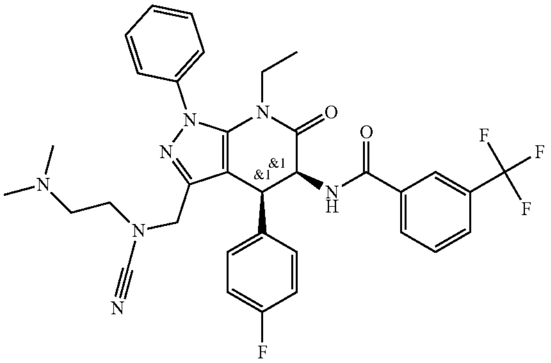
I-487
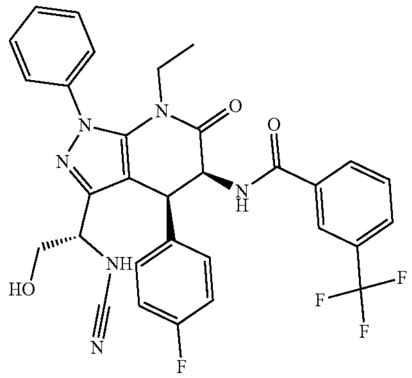

-continued
I-488
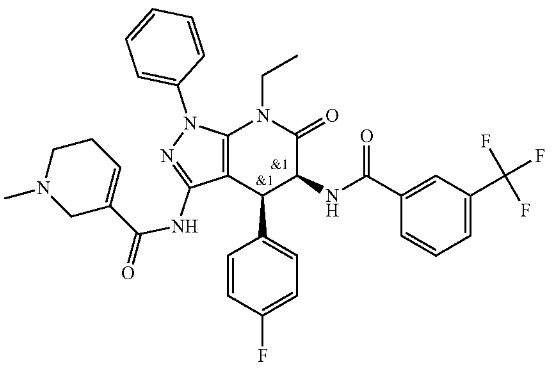
I-489
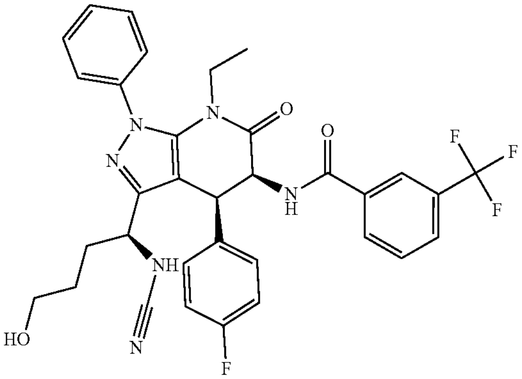
I-490
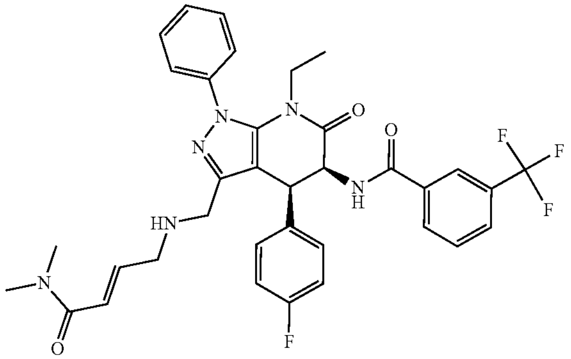
I-491
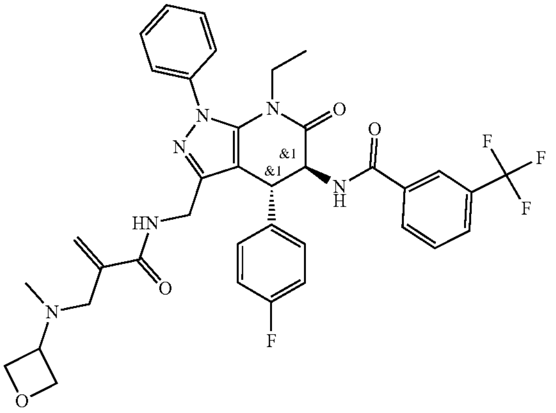
-continued
I-492
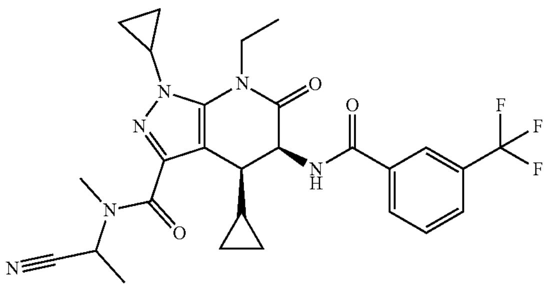
I-494
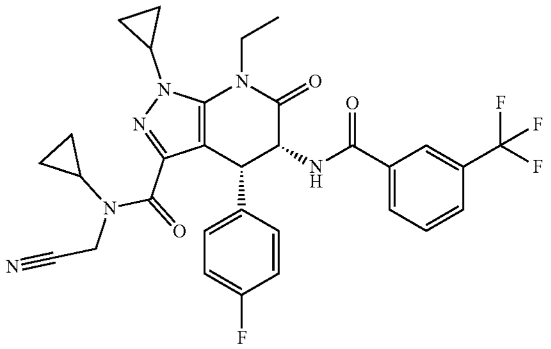
I-495
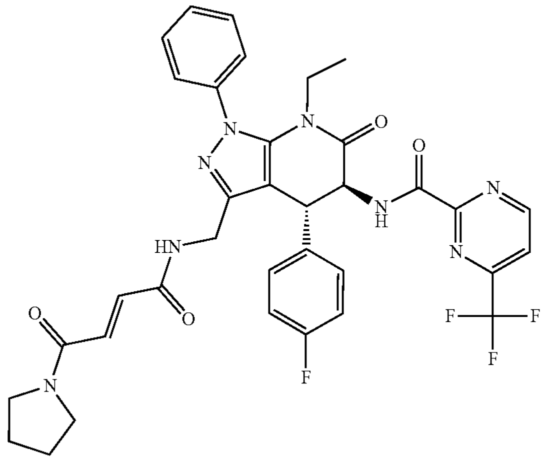
I-496
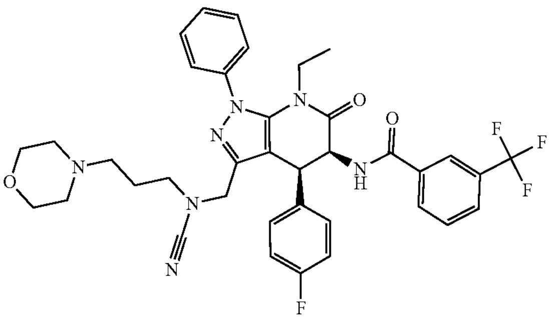

-continued
I-497
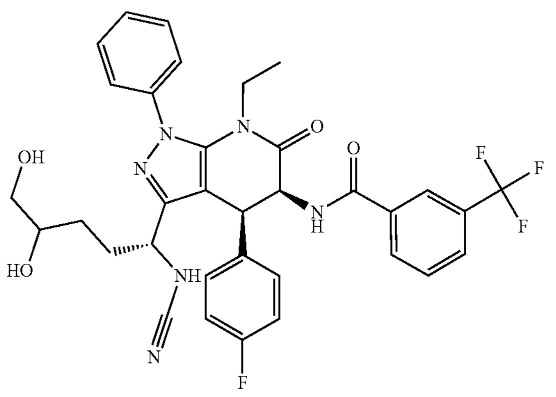
I-498
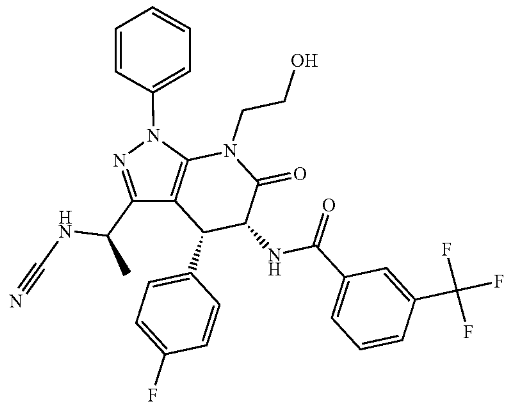
I-499
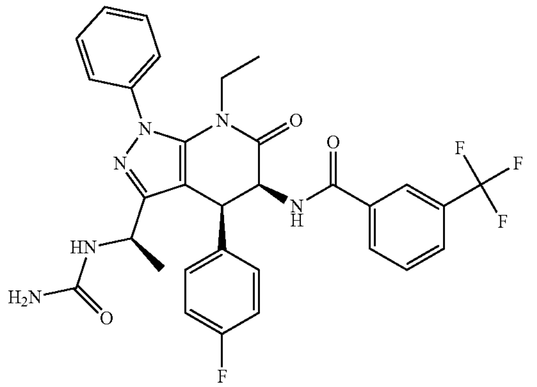
-continued
I-501
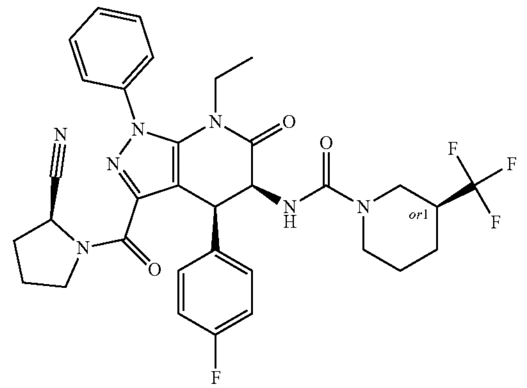
I-502
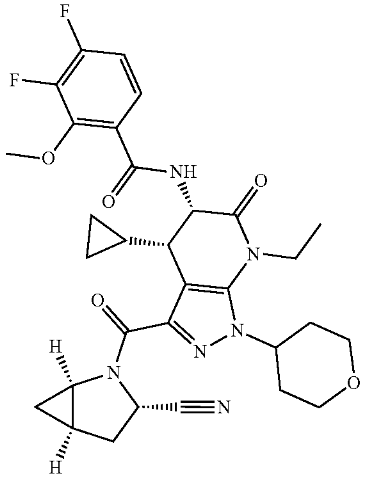
I-503
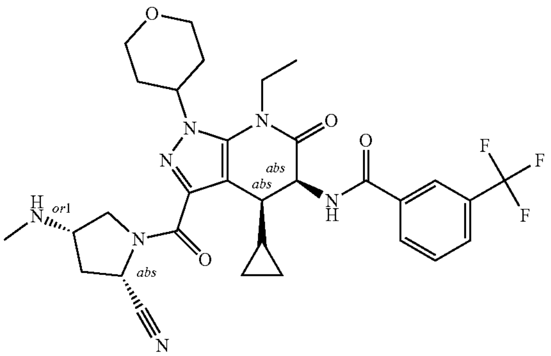
I-504
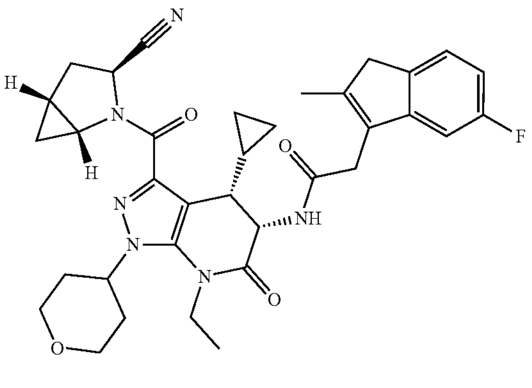

-continued
I-505
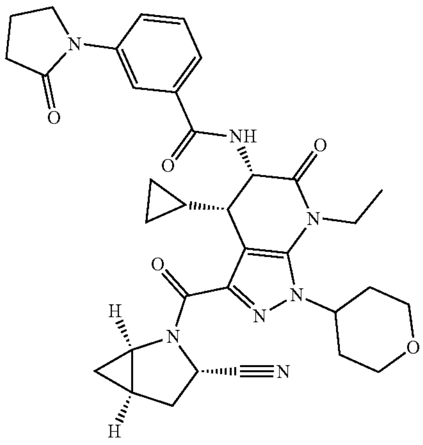
I-506
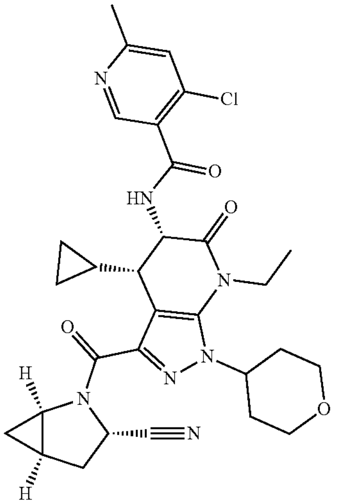
I-507
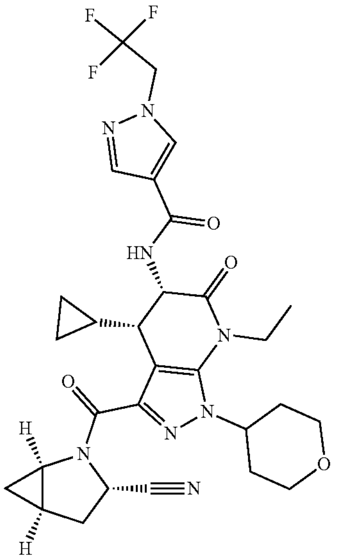
-continued
I-508
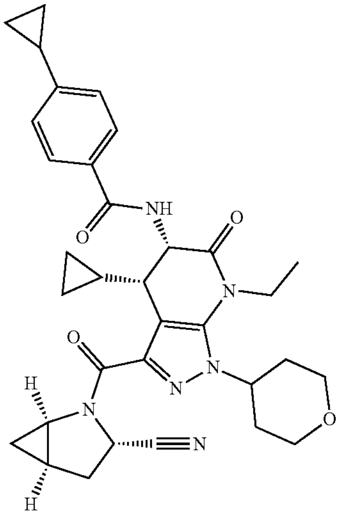
I-509
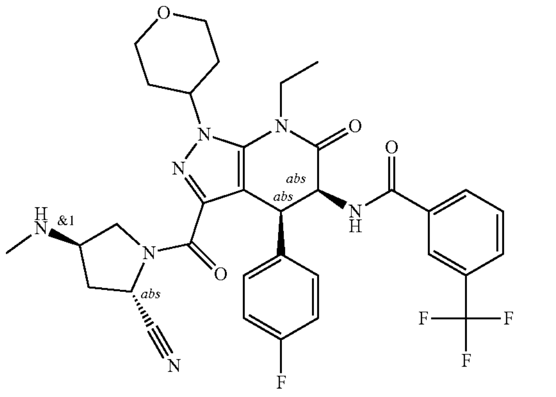
I-510
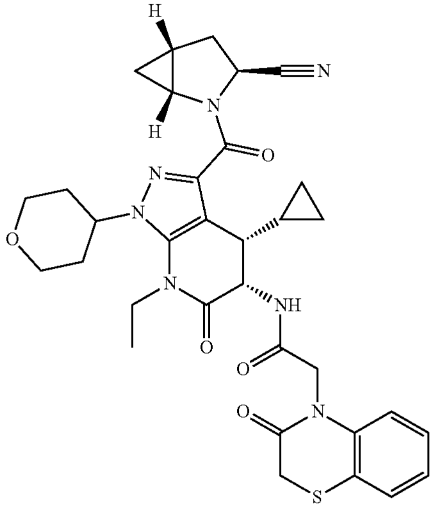

I-511
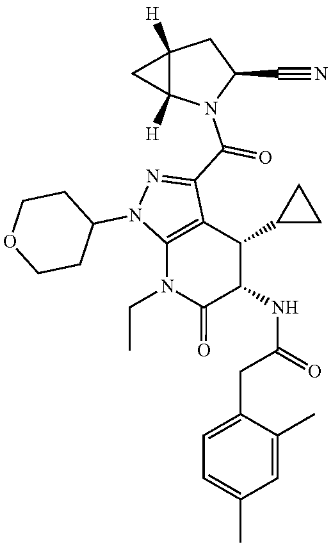
I-512
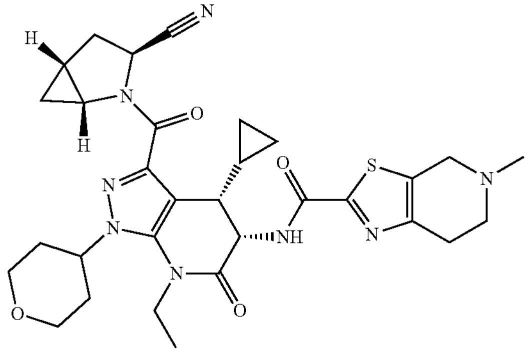
I-513
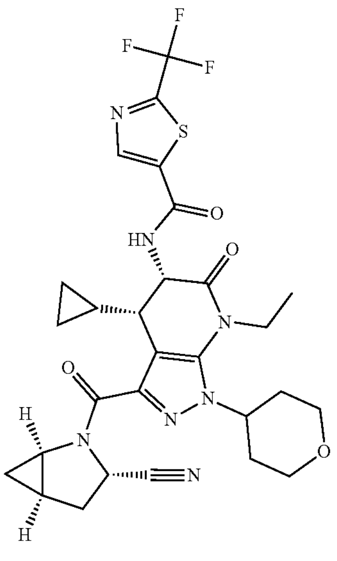
I-514
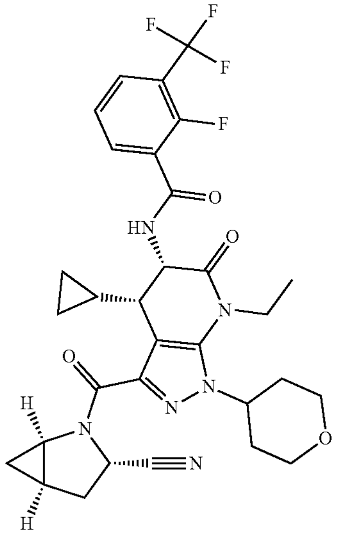
I-515
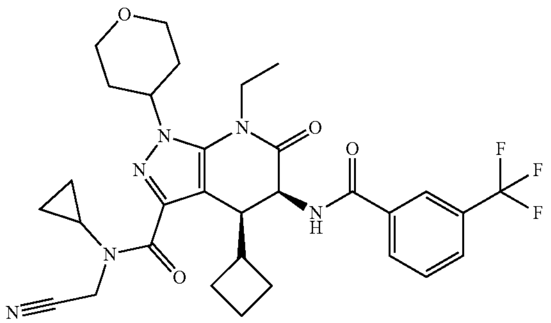
I-516
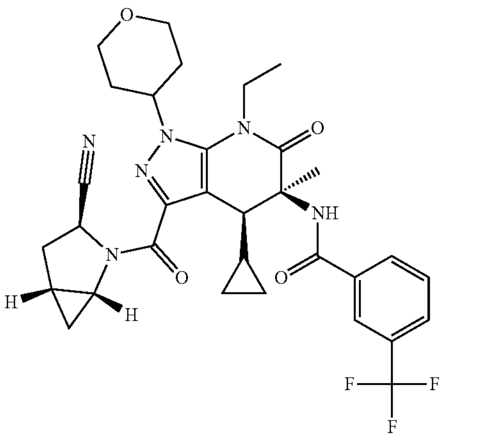
I-517
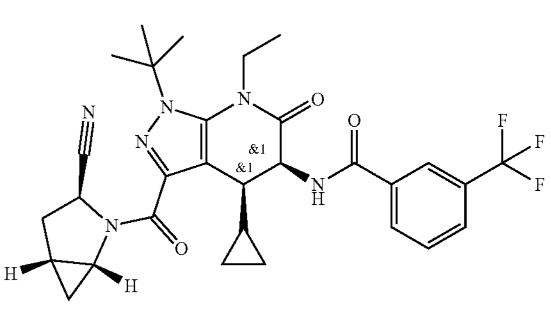

-continued
I-518
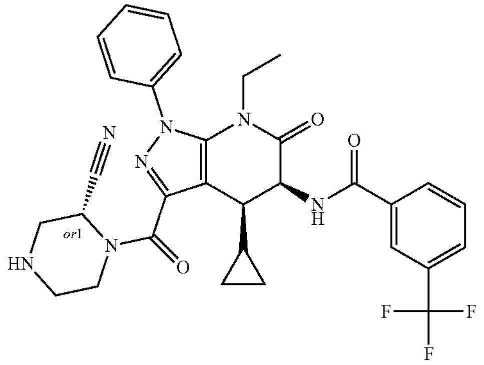
I-519
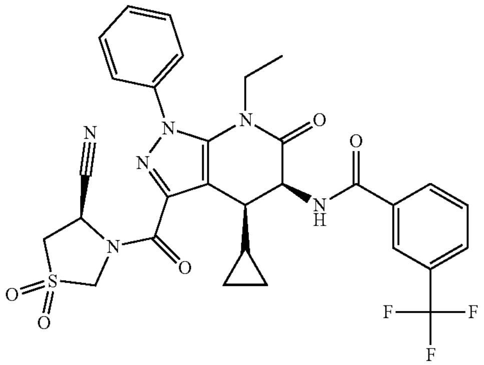
I-521
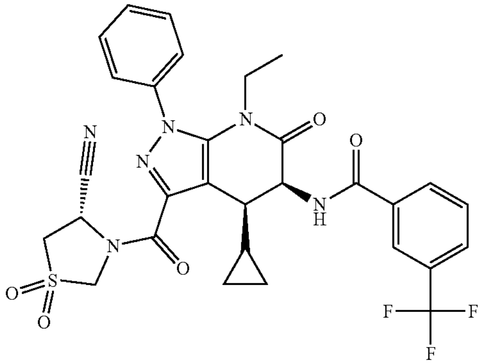
I-522
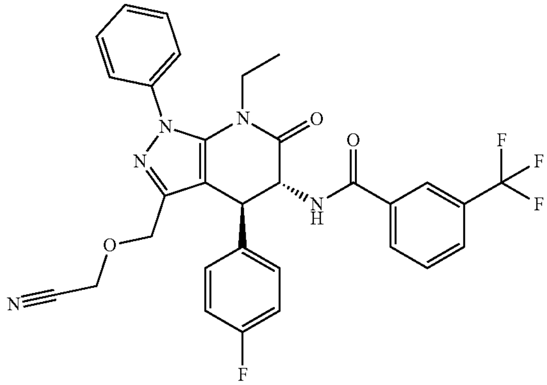
-continued
I-523
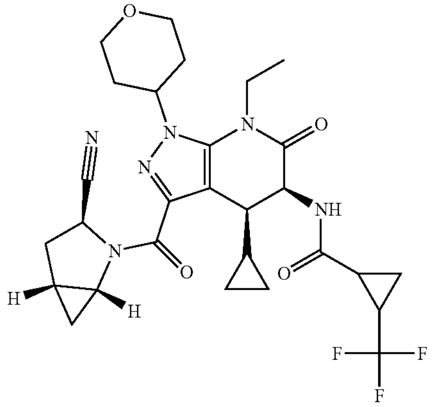
I-524
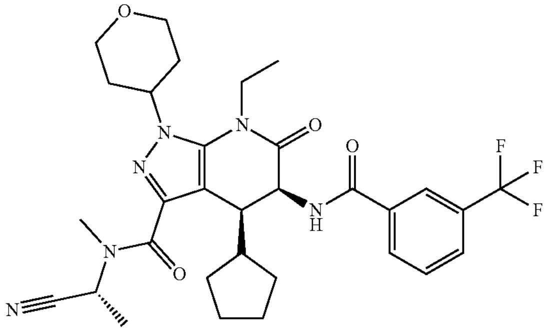
I-525
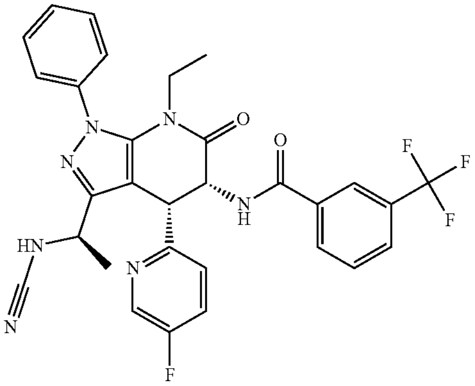
I-526
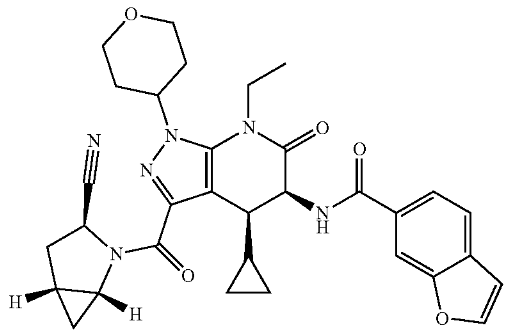

-continued
I-527
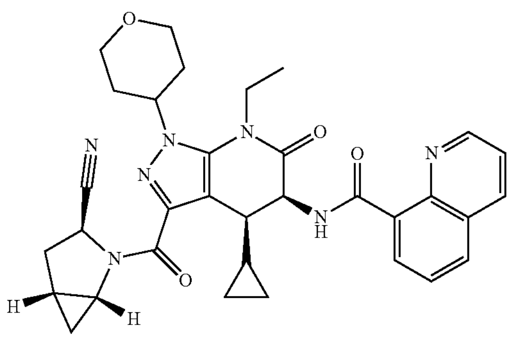
I-528
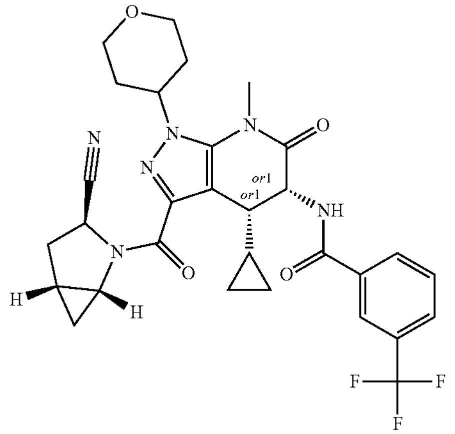
I-530
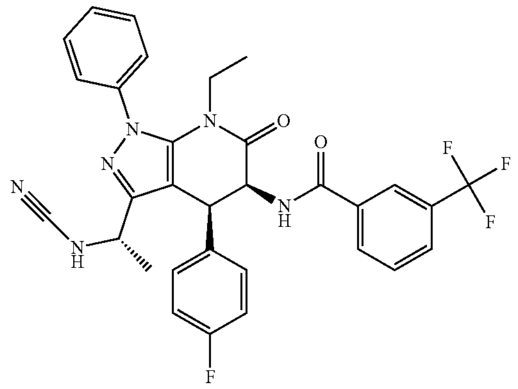
I-531
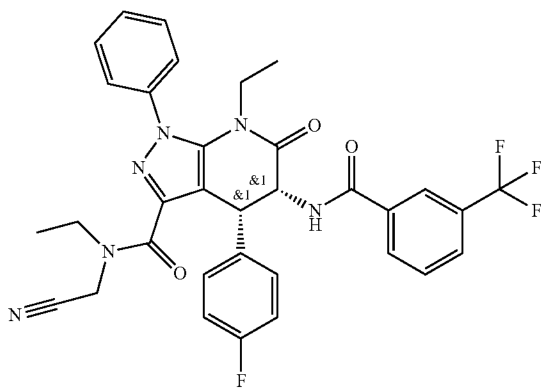
-continued
I-533
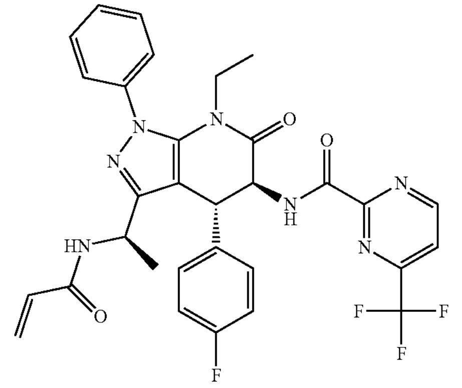
I-534
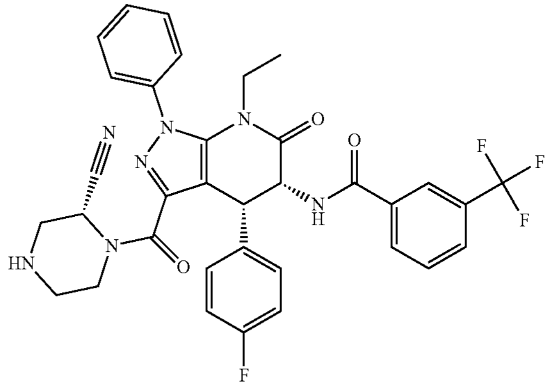
I-535
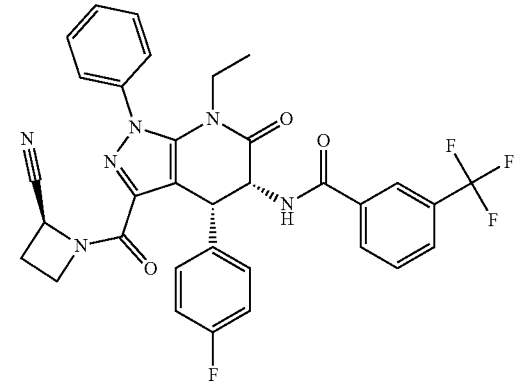
I-536
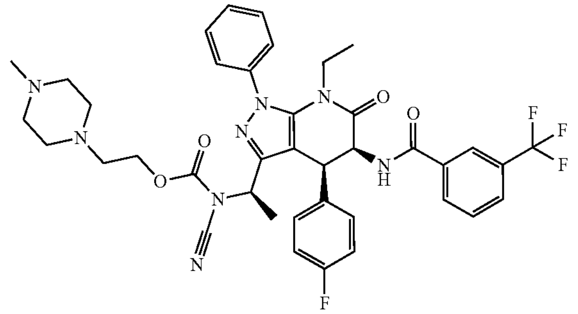

-continued
I-538
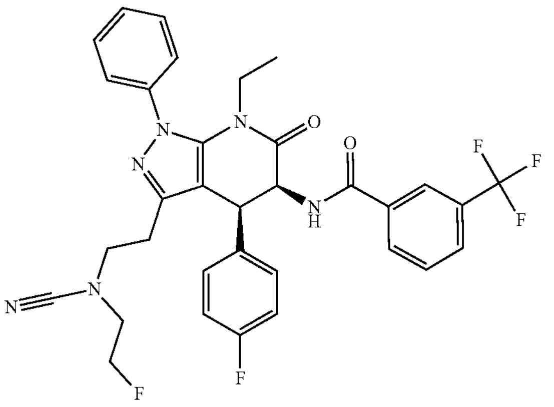
I-539
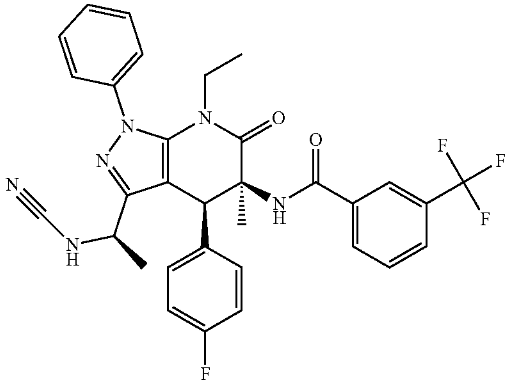
I-540
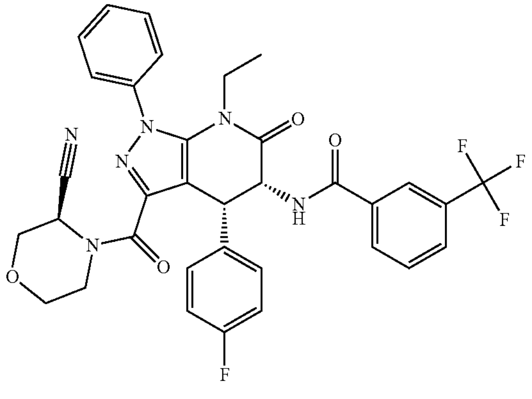
I-541
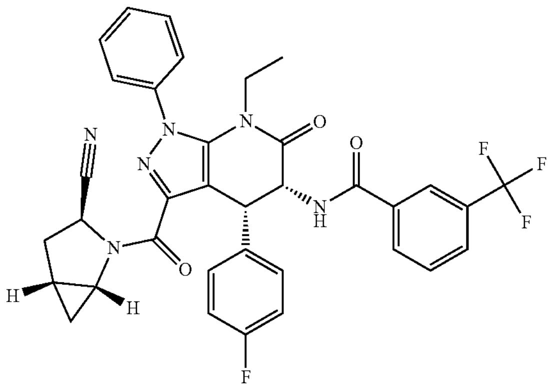
I-542
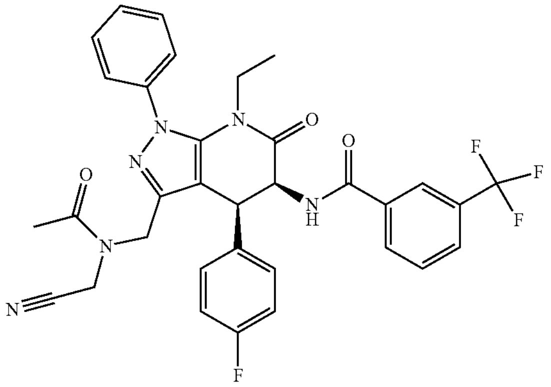
I-543
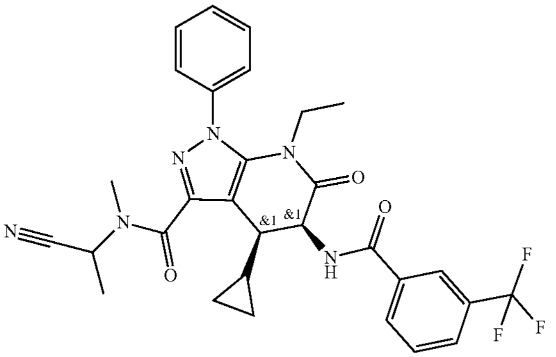
I-544
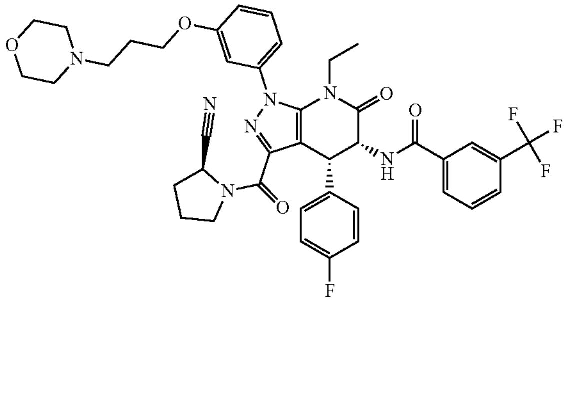

-continued
I-546
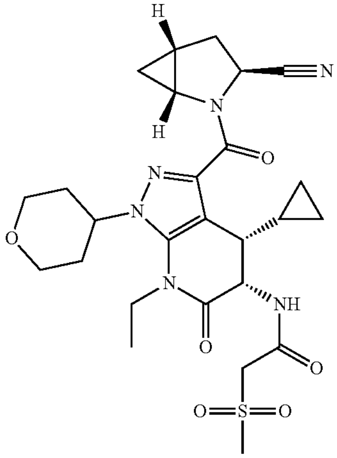
I-547
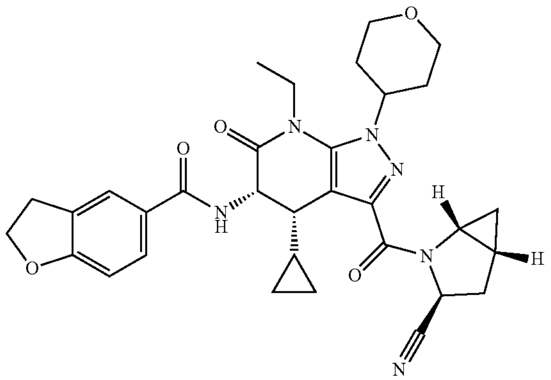
I-548
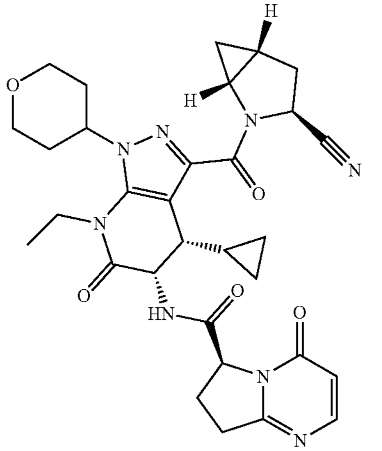
-continued
I-549
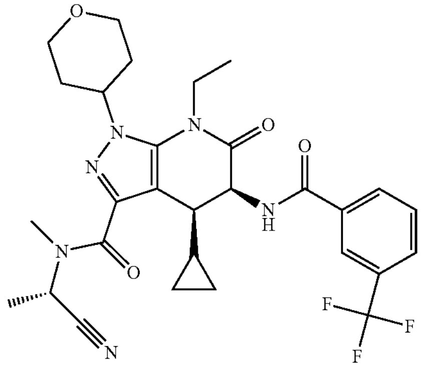
I-550
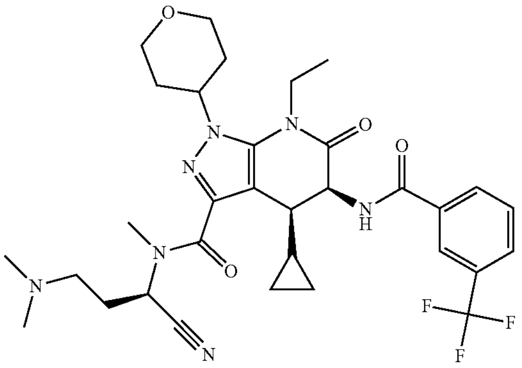
I-551
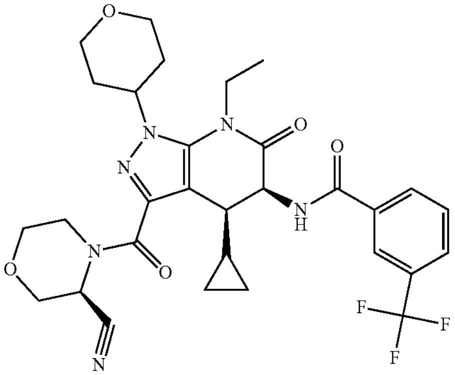
I-552
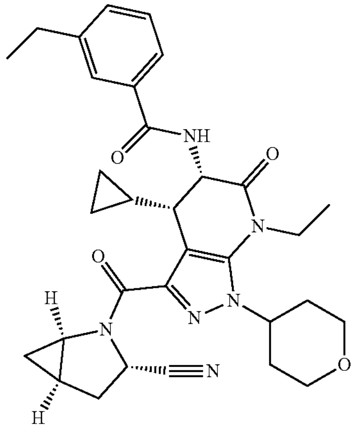

-continued
I-553
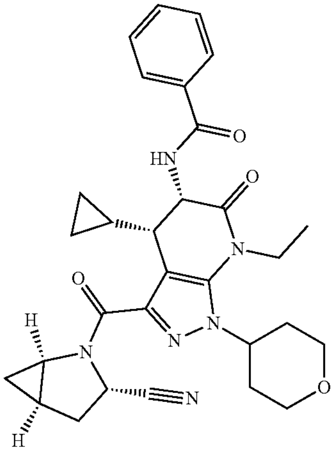
I-554
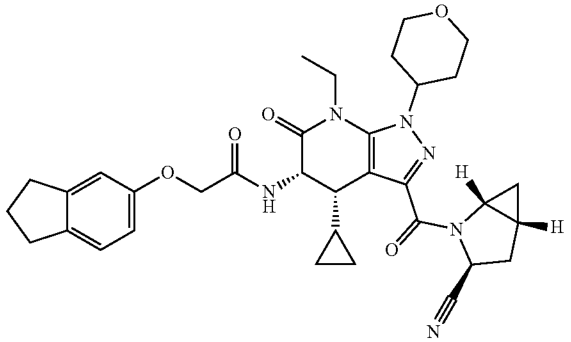
I-555
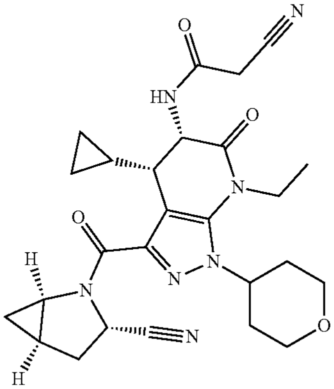
-continued
I-556
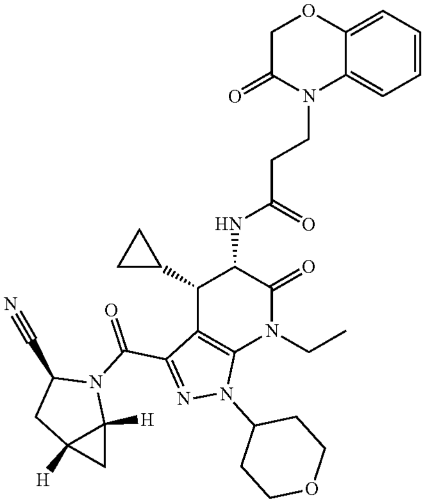
I-557
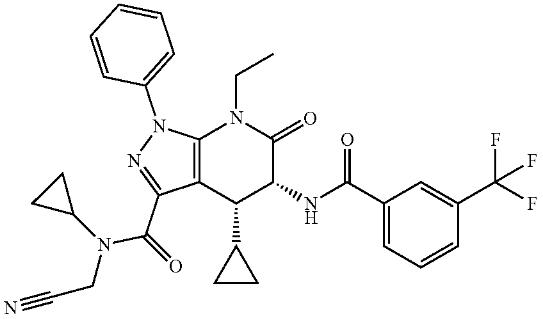
I-558
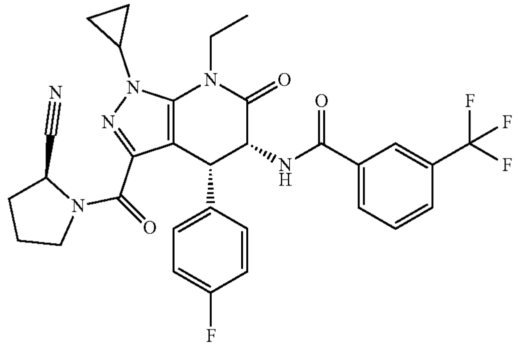
I-559
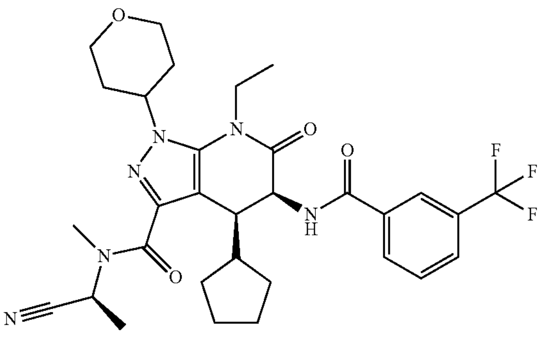

-continued
I-560
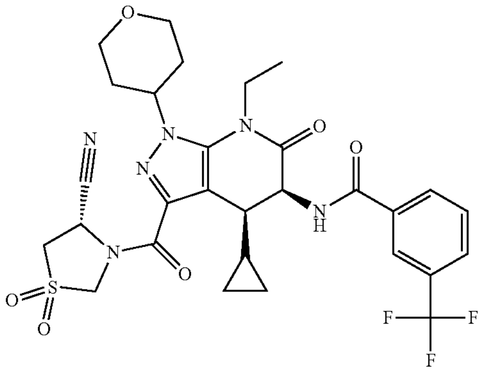
I-561
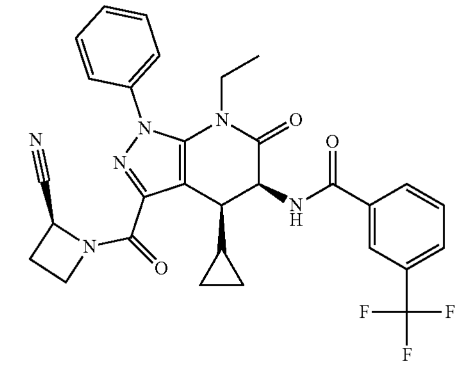
I-562
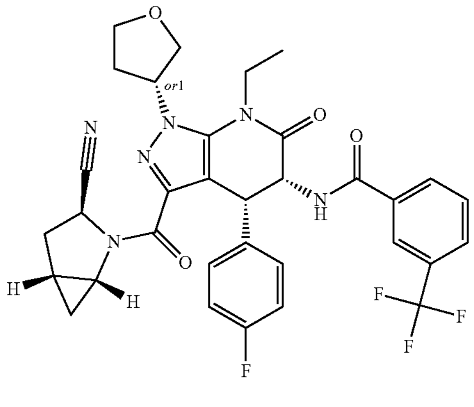
I-563
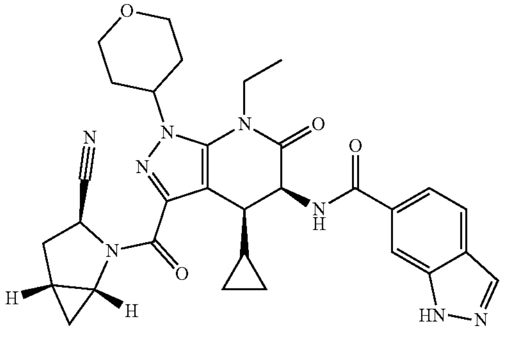
-continued
I-564
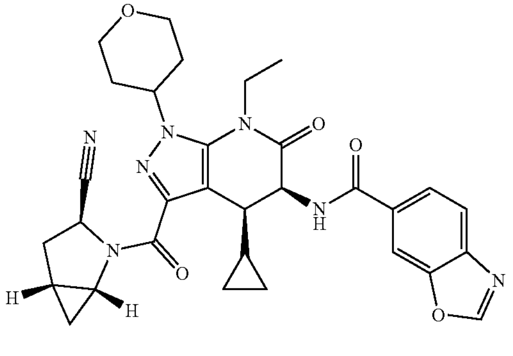
I-565
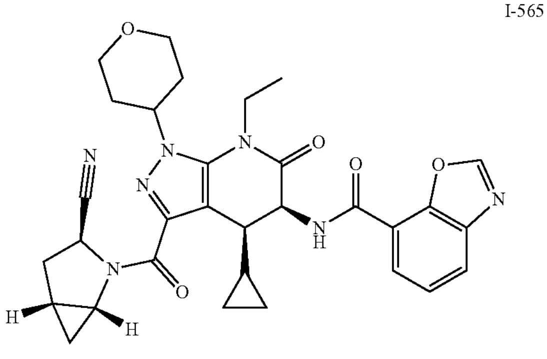
I-566
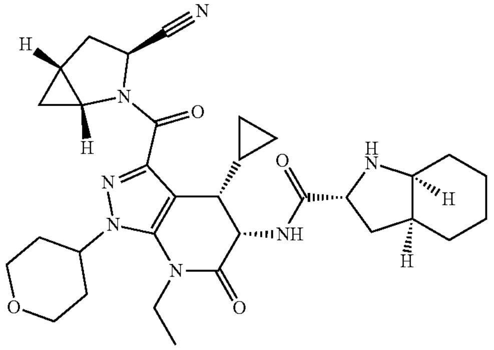
I-567
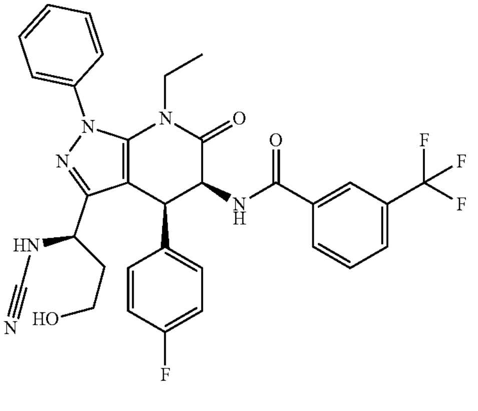

-continued
I-569
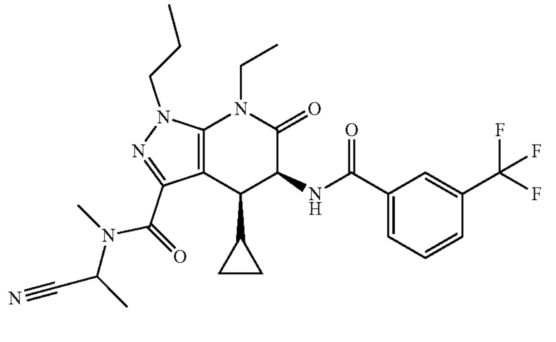
I-570
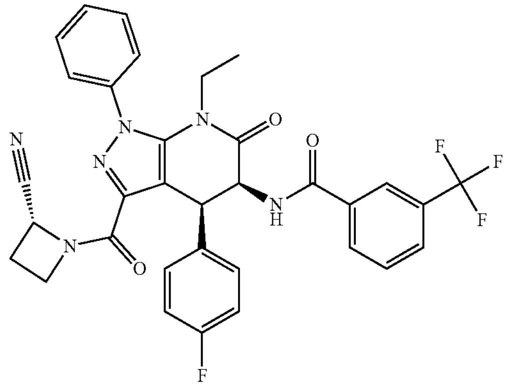
I-571
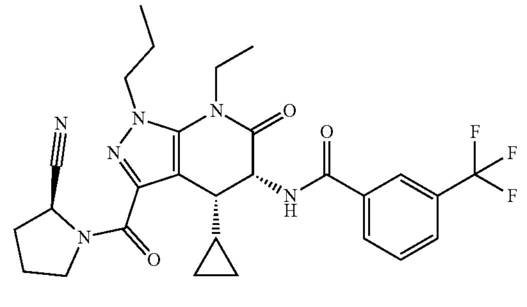
I-572
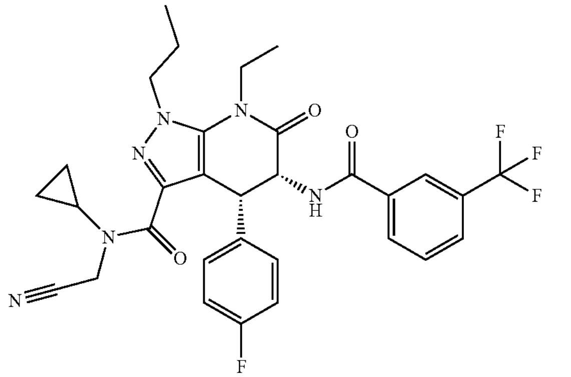
-continued
I-573
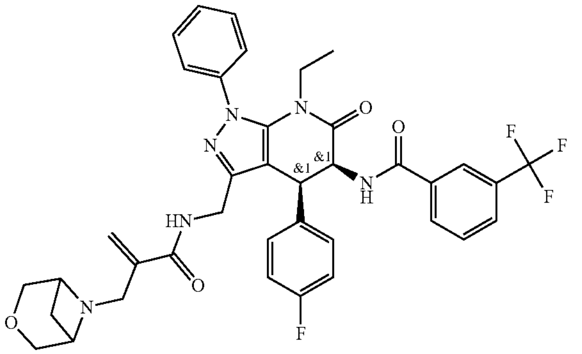
I-574
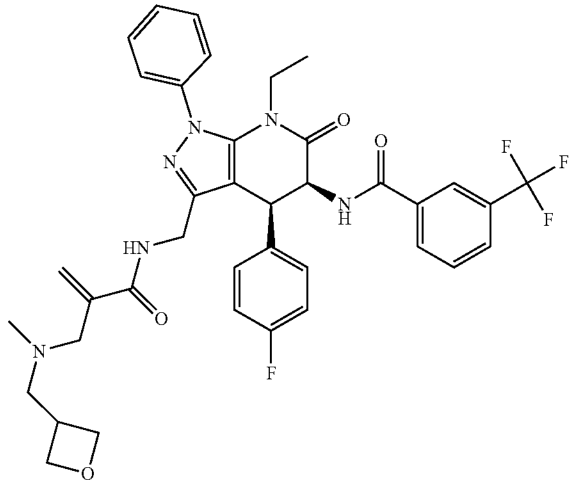
I-576
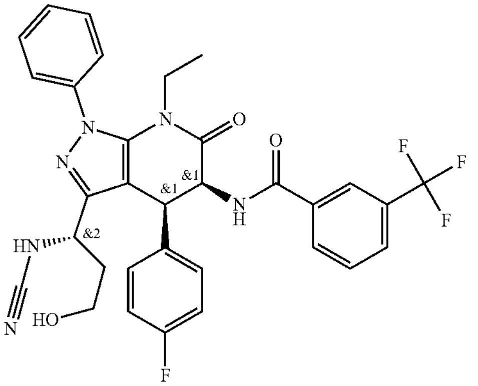
I-577
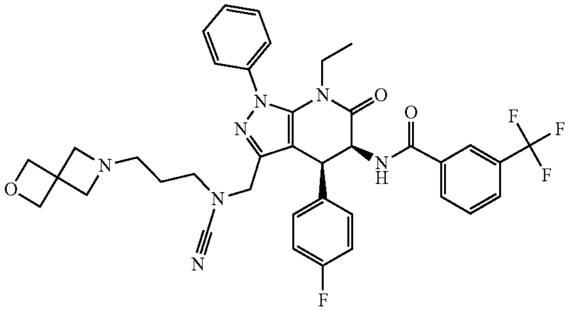

-continued
I-578
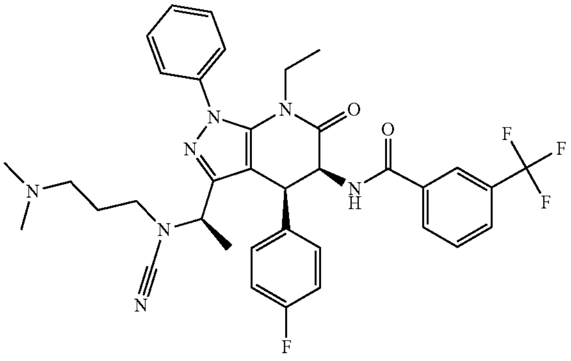
I-583
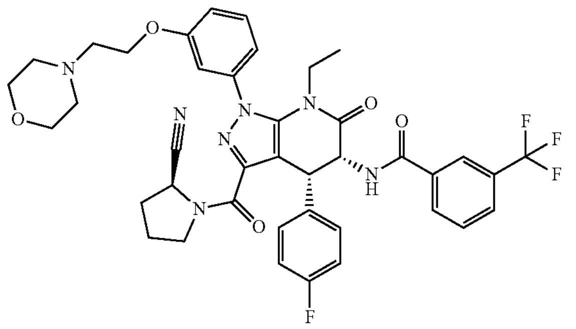
I-579
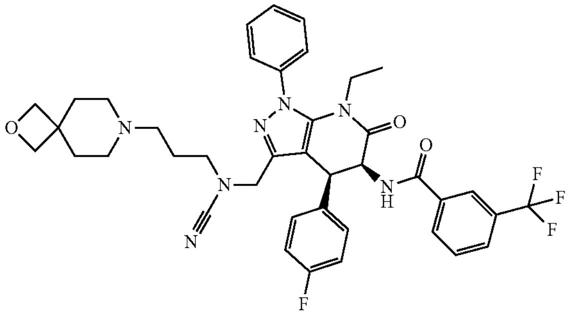
I-584
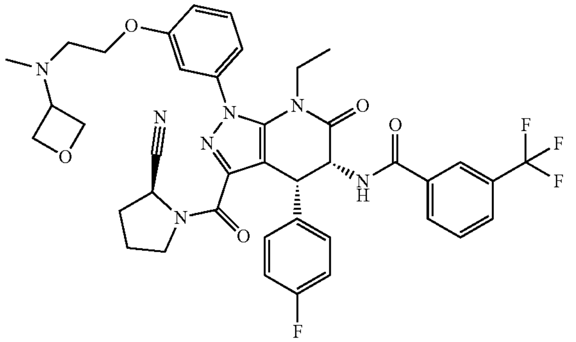
I-581
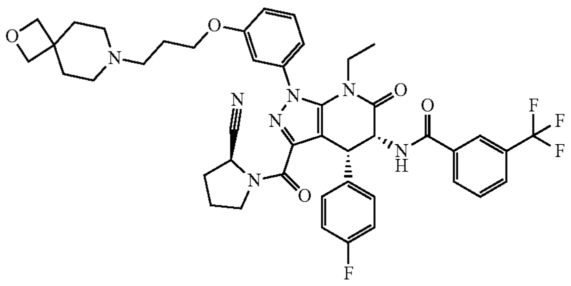
I-585
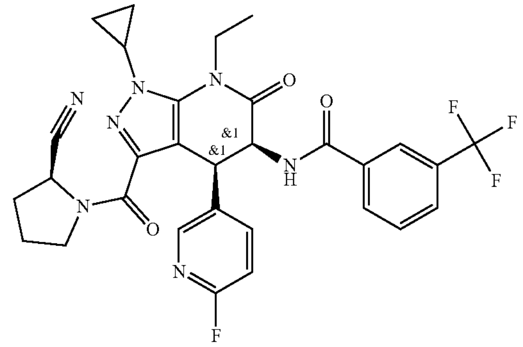
I-582
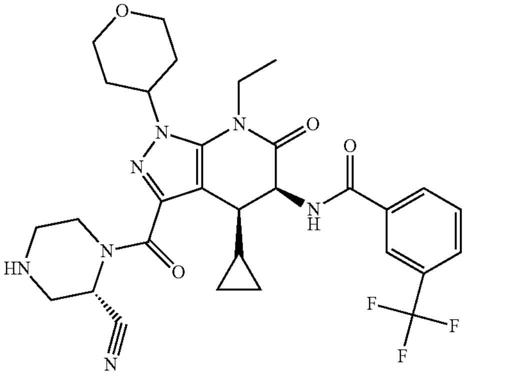
I-586
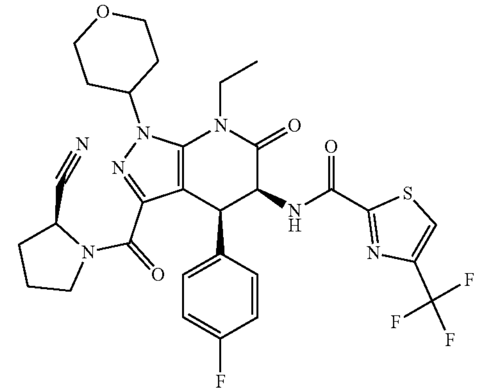

-continued
I-588
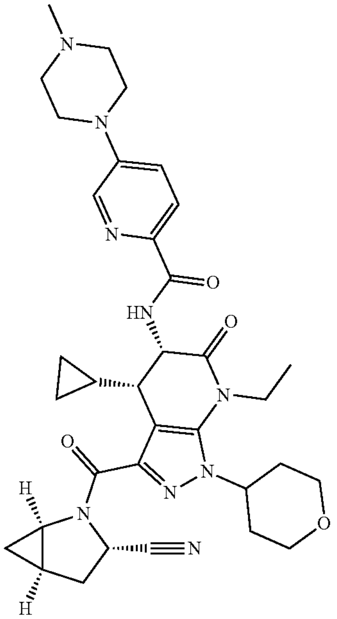
I-589
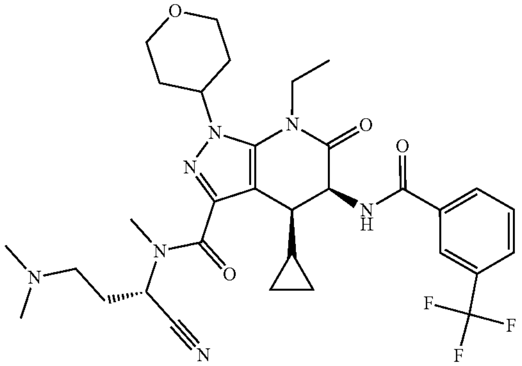
I-590
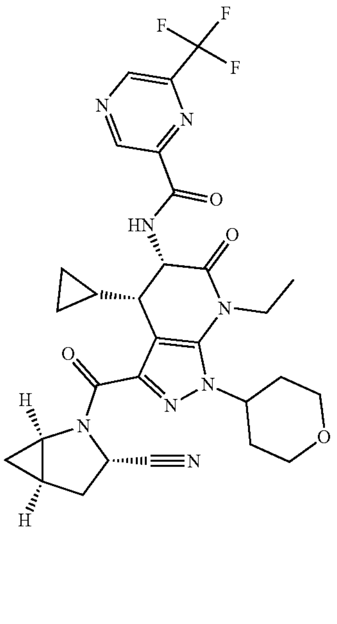
-continued
I-591
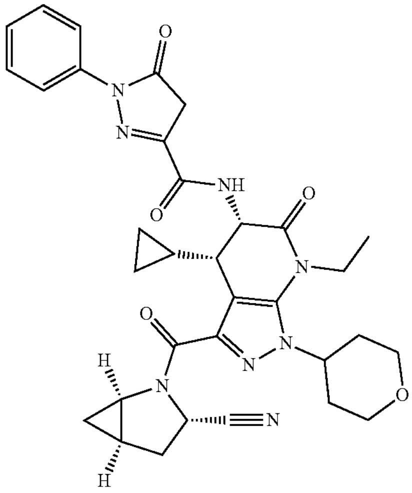
I-592
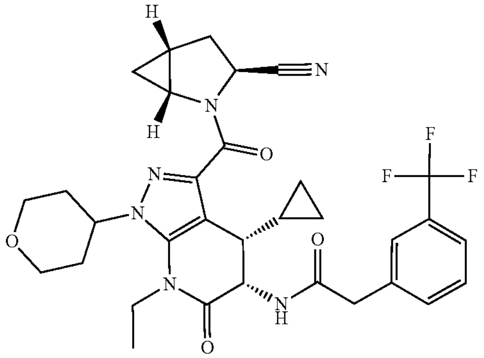
I-593
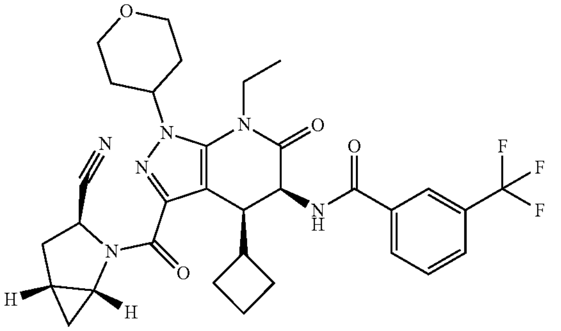
I-594
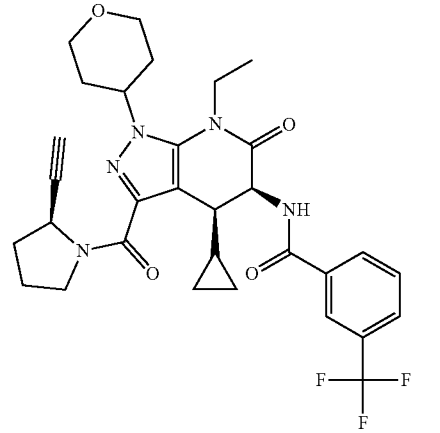

-continued
I-595
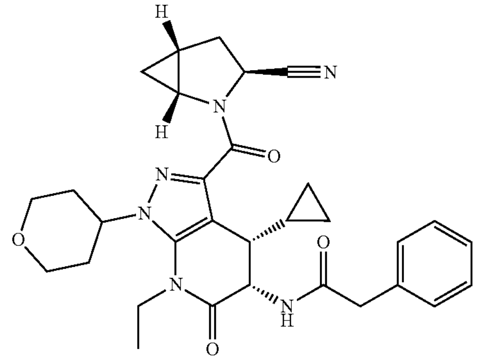
I-596
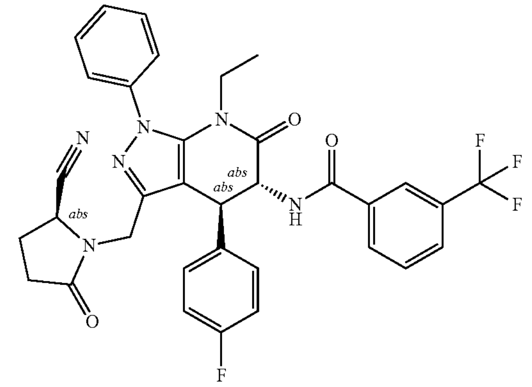
I-597
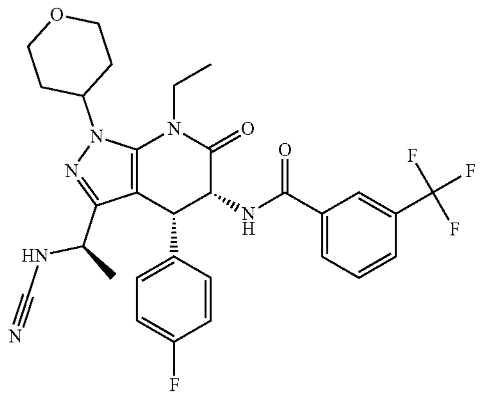
I-598
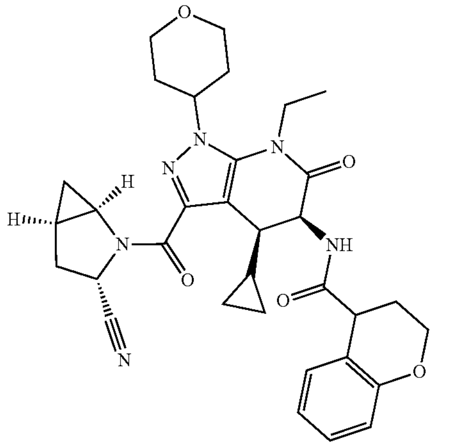
-continued
I-599
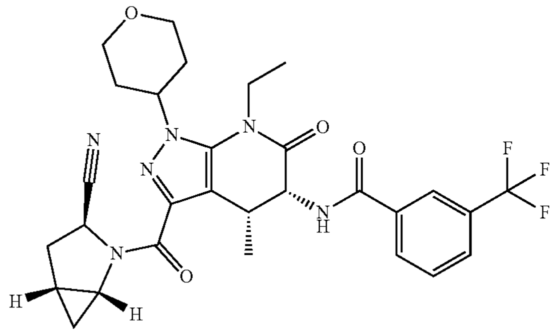
I-600
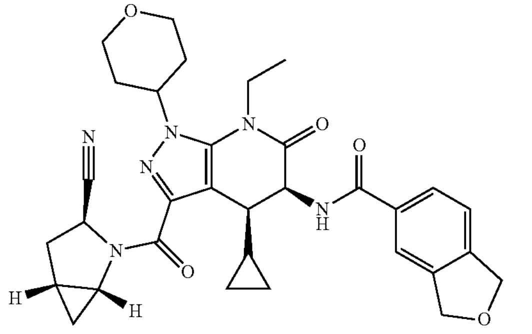
I-601
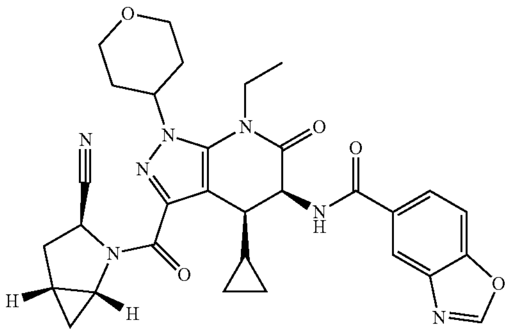
I-602
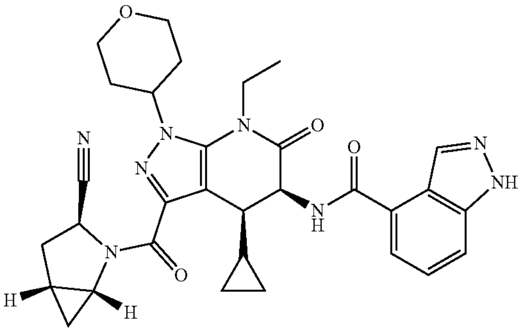

-continued
I-603
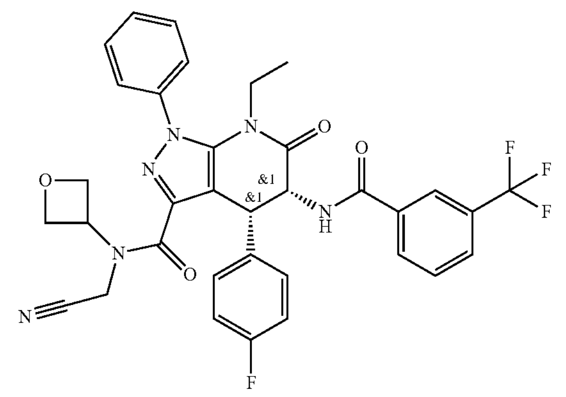
I-604
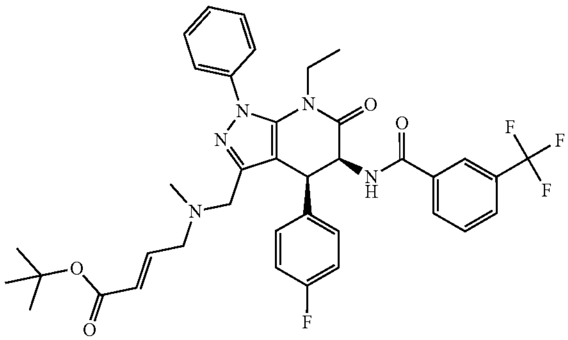
I-605
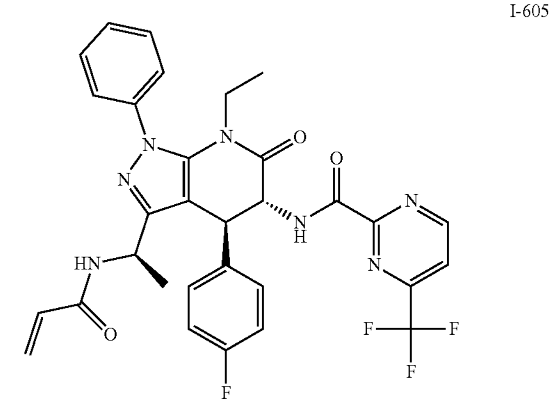
I-606
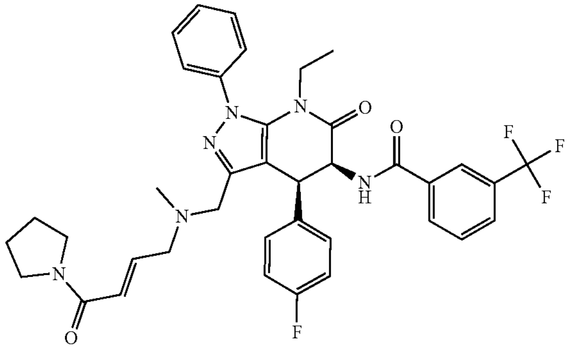
-continued
I-607
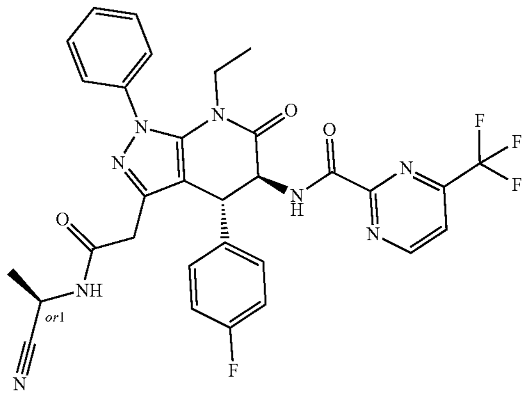
I-608
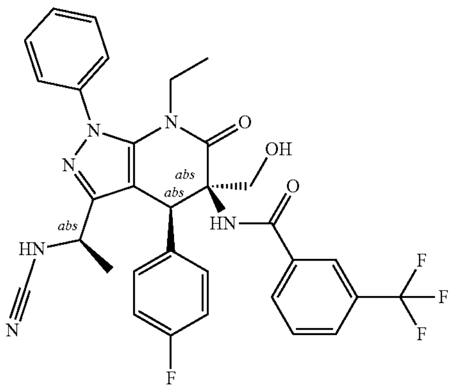
I-609
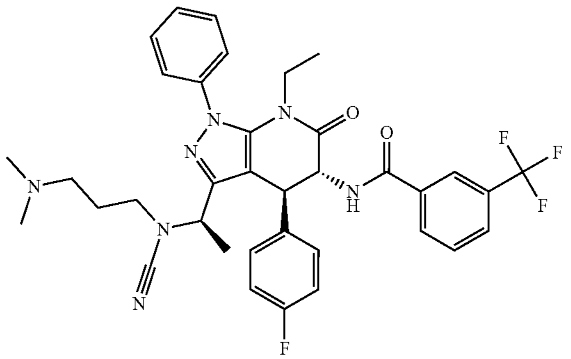
I-611
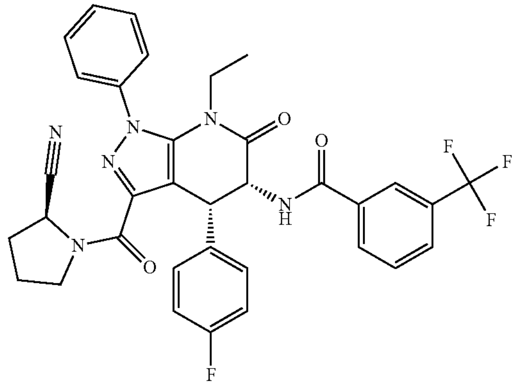

-continued
I-612
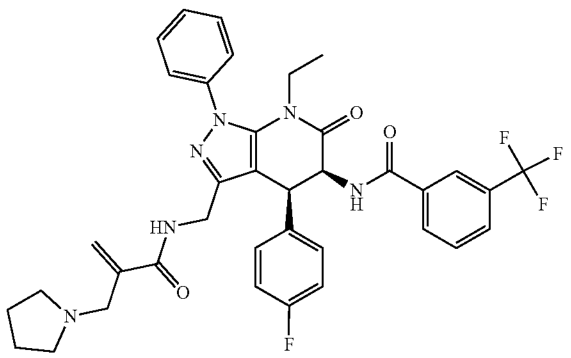
I-613
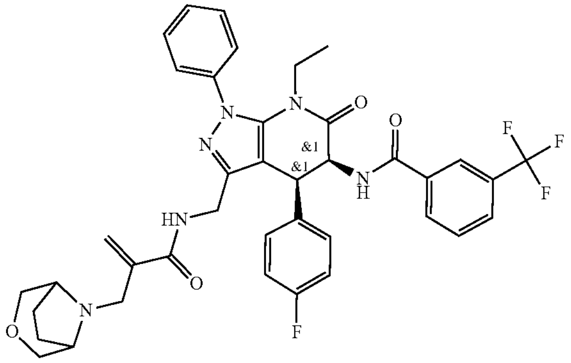
I-614
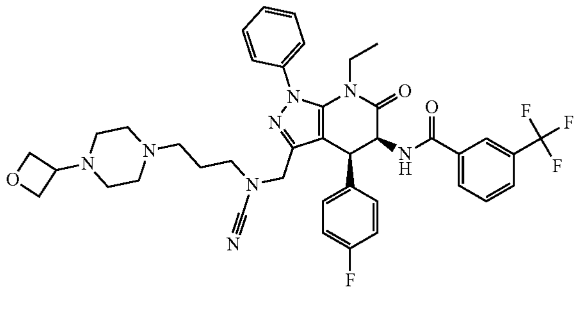
I-615
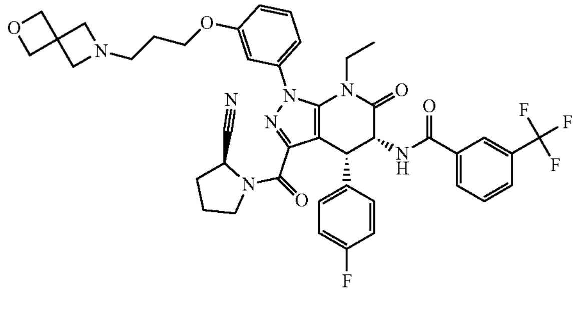
-continued
I-616
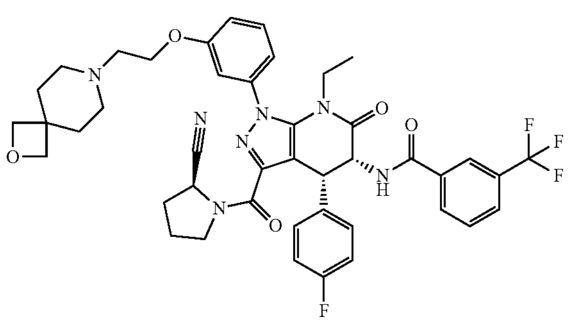
I-617
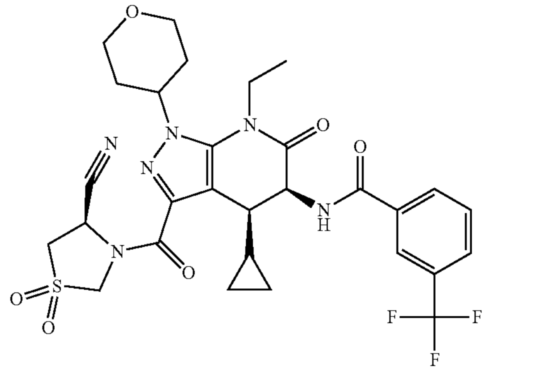
I-618
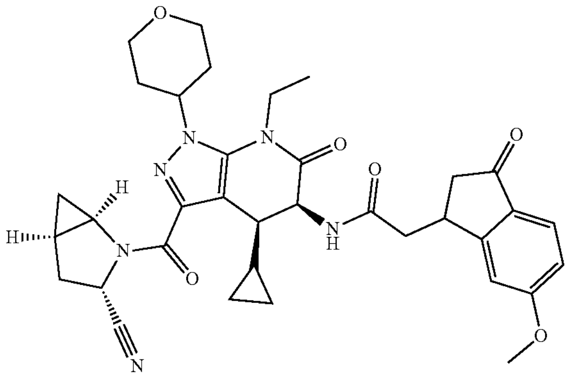
I-619
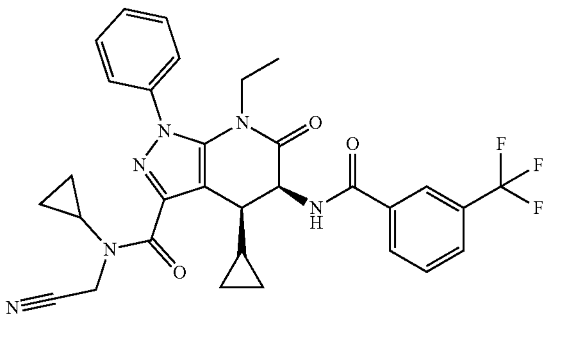

-continued
I-620
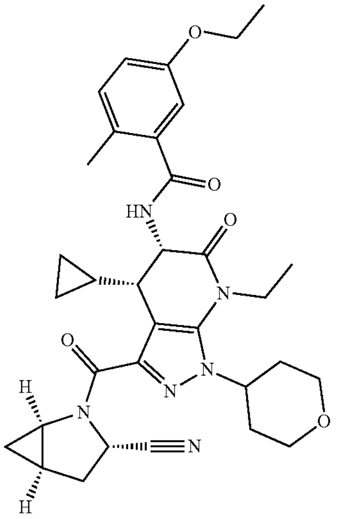
I-621
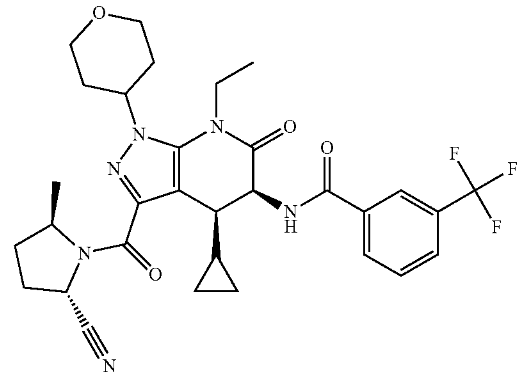
I-622
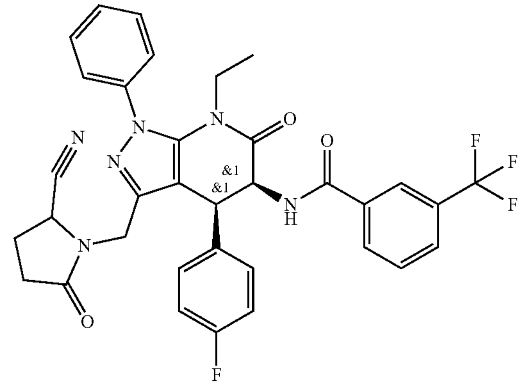
-continued
I-623
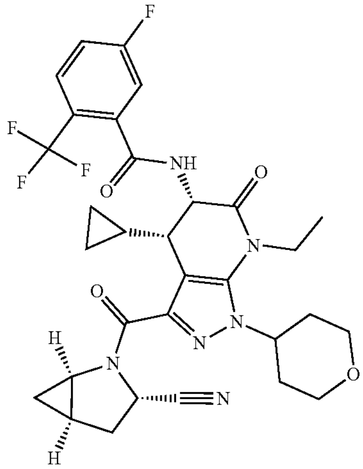
I-624
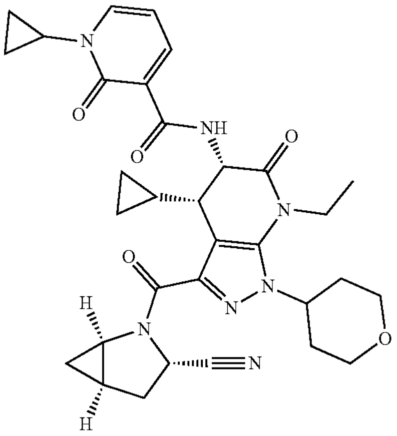
I-625
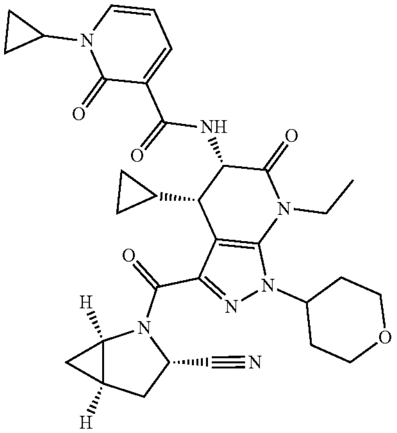

-continued
I-626
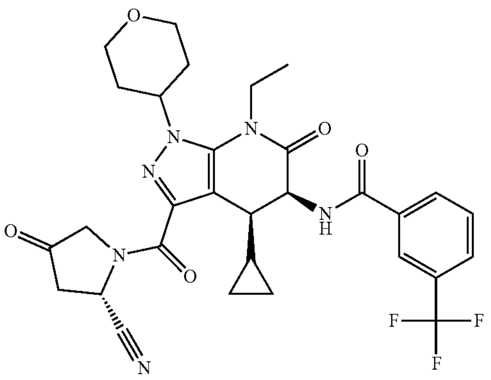
I-627
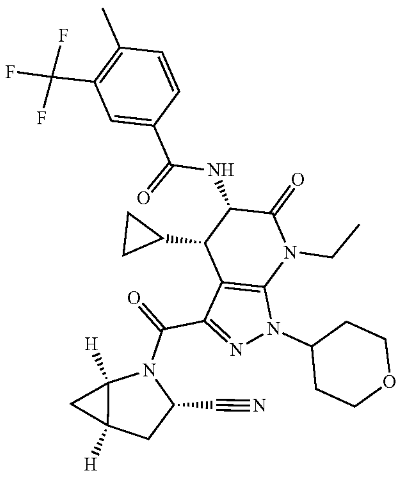
I-628
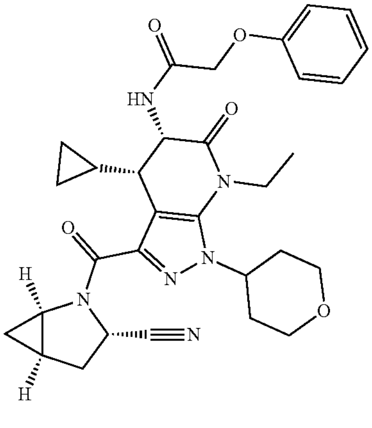
-continued
I-629
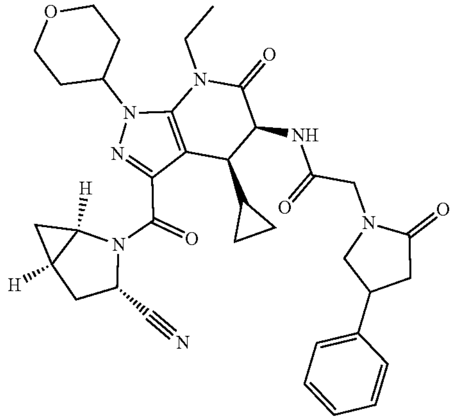
I-630
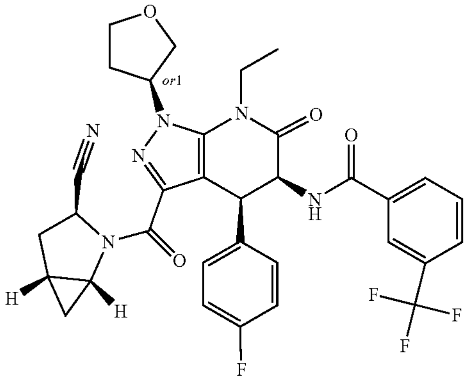
I-631
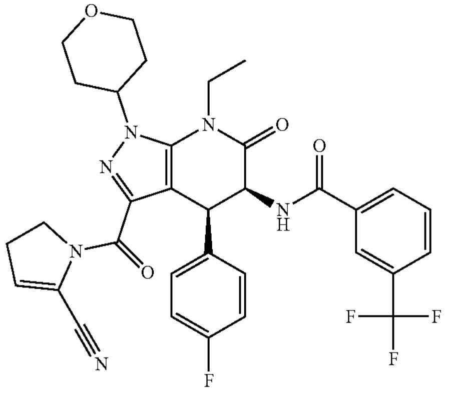
I-632
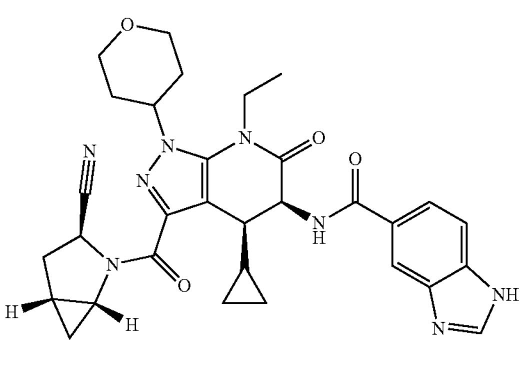

-continued
I-633
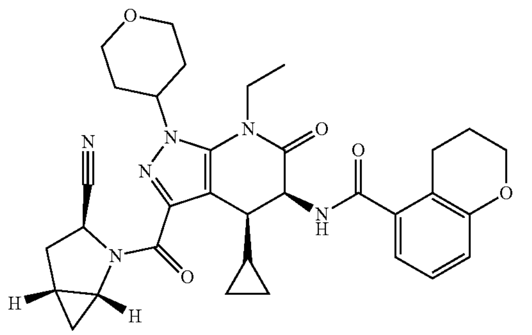
I-634
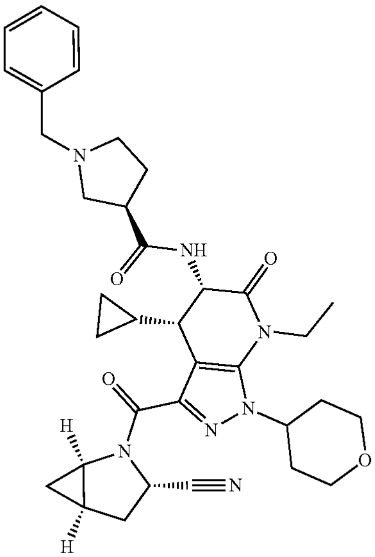
I-635
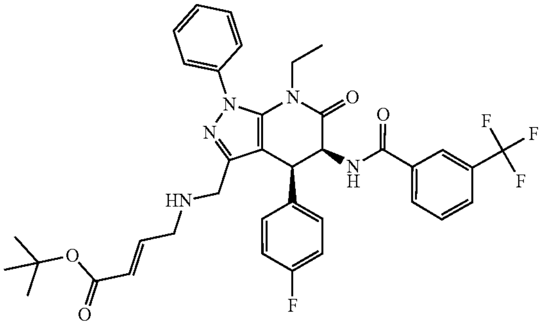
I-636
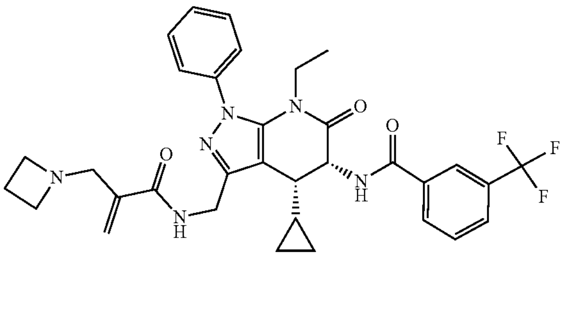
-continued
I-637
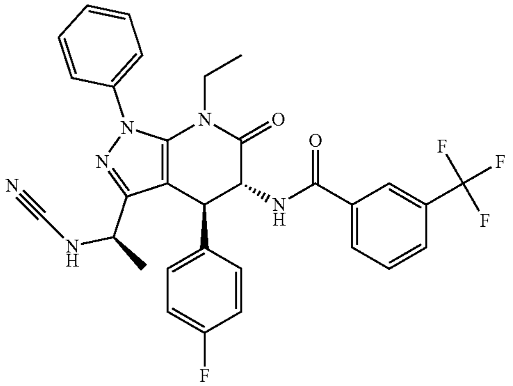
I-638
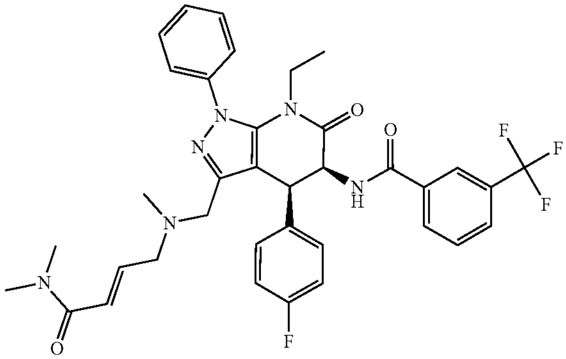
I-639
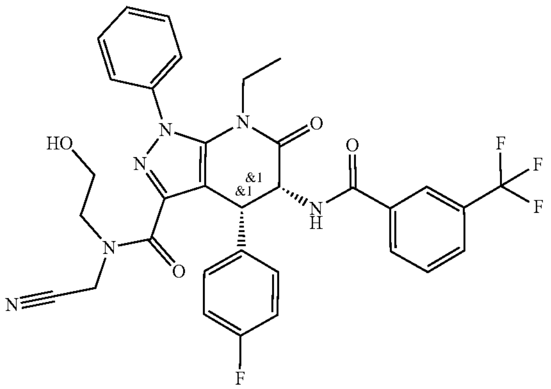
I-640
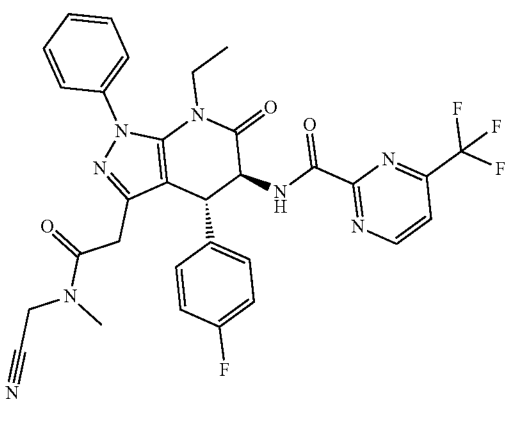

-continued
I-641
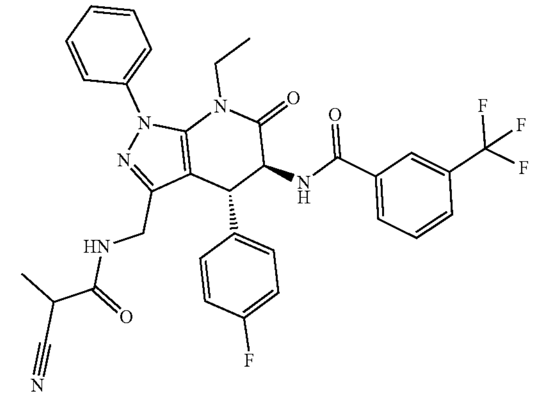
I-642
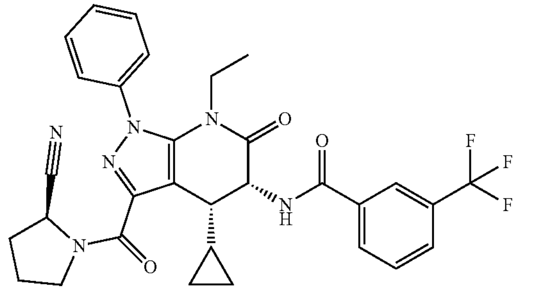
I-643
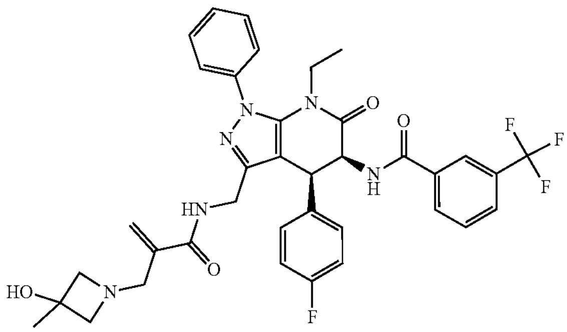
I-644
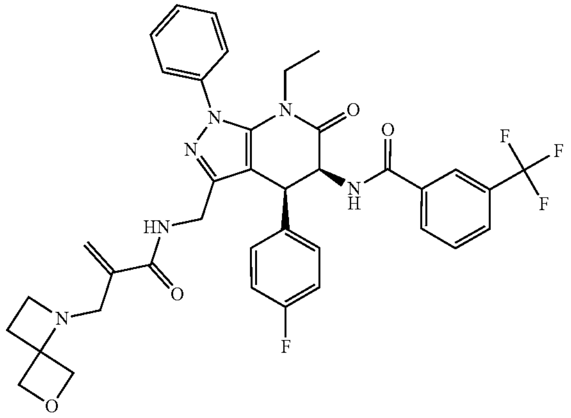
-continued
I-646
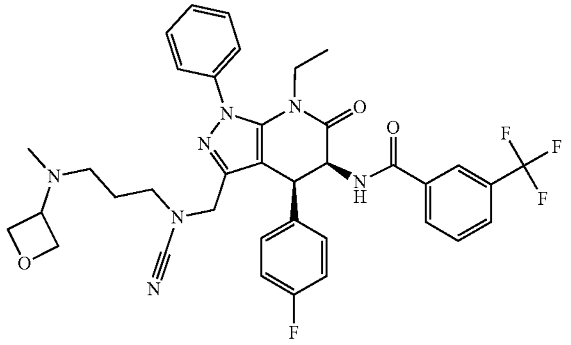
I-647
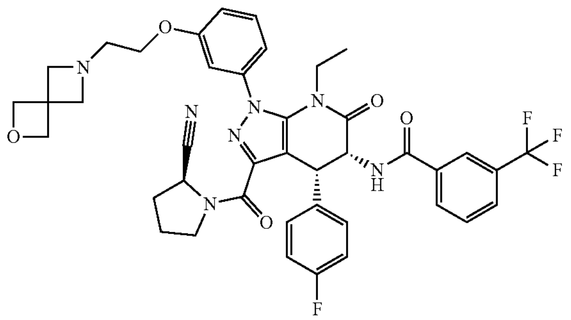
I-648
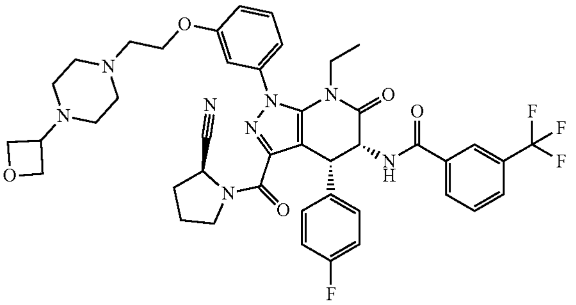
I-649
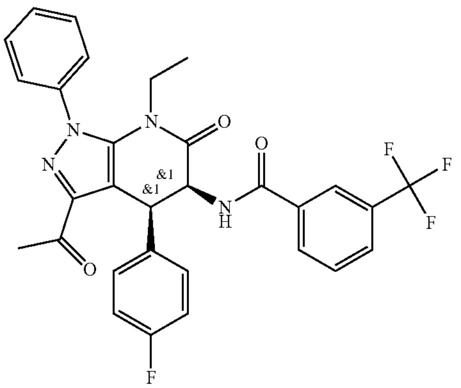

-continued
I-650
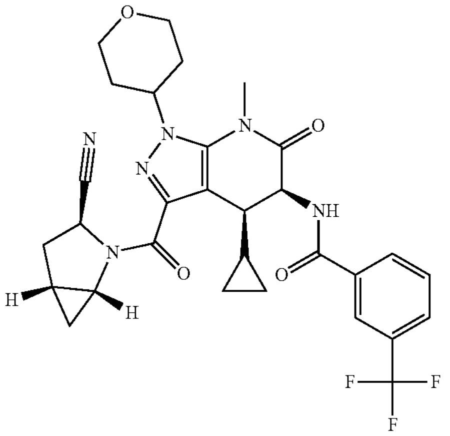
I-652
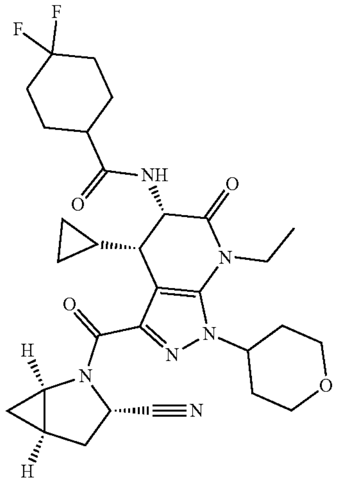
I-653
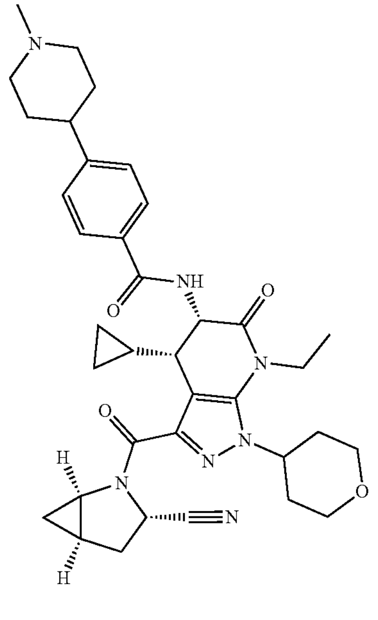
-continued
I-654
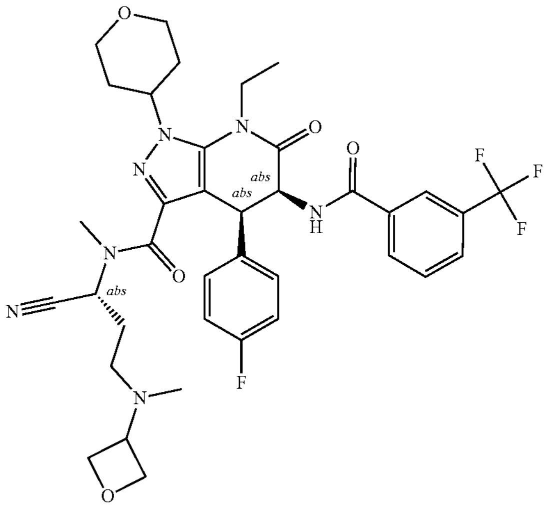
I-655
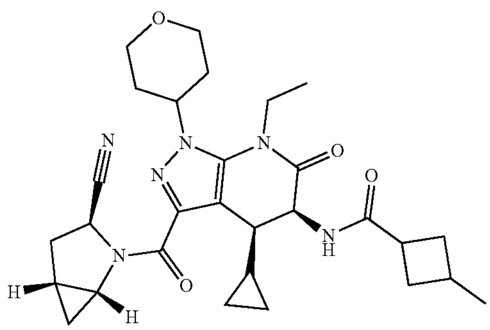
I-656
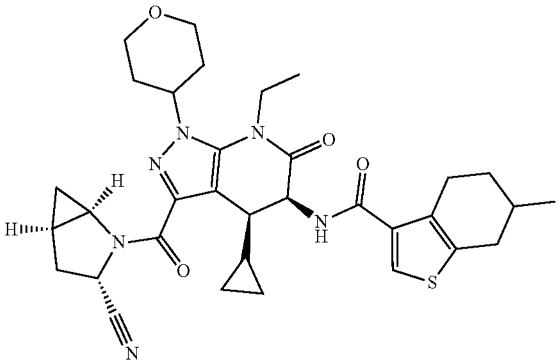
I-658
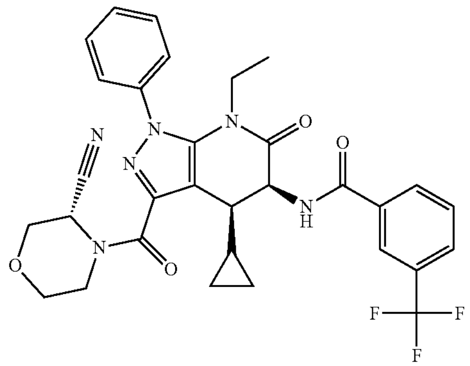

-continued
I-659
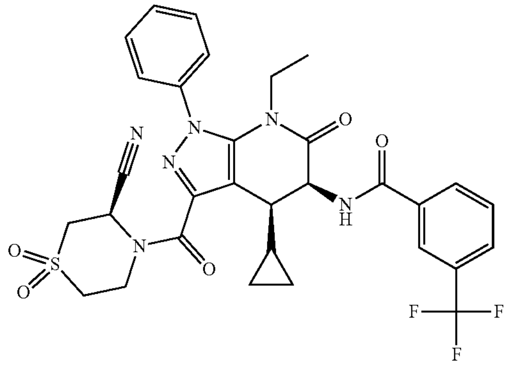
I-660
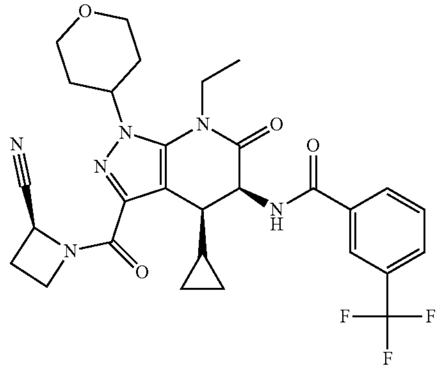
I-661
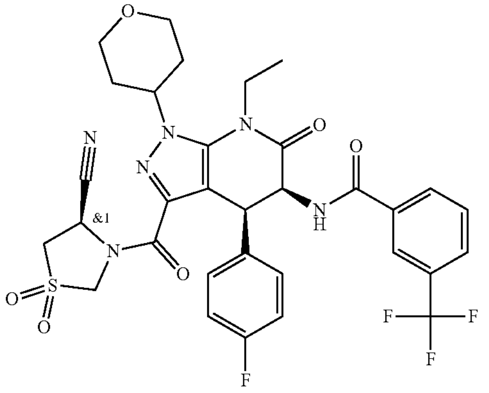
I-662
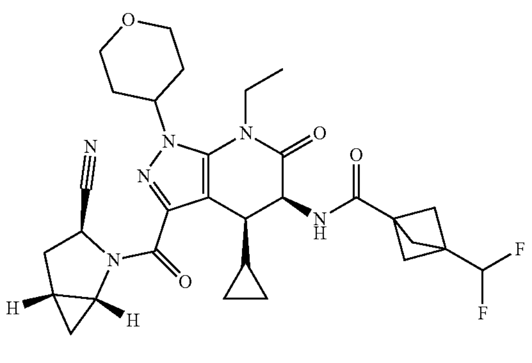
I-663
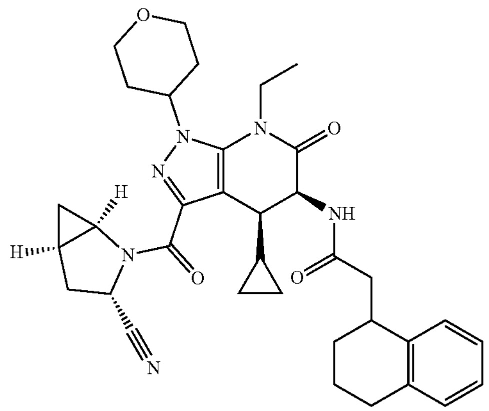
I-664
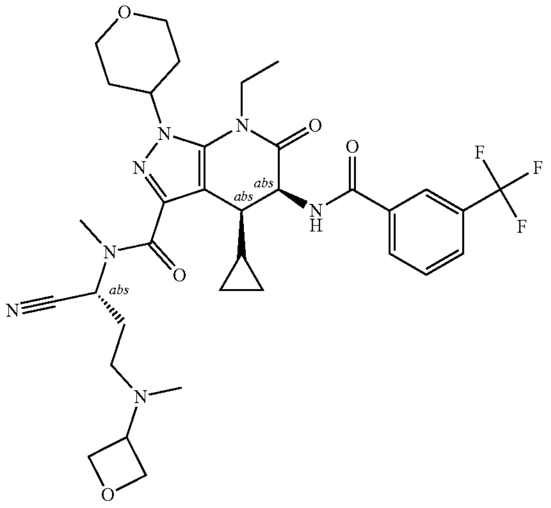
I-666
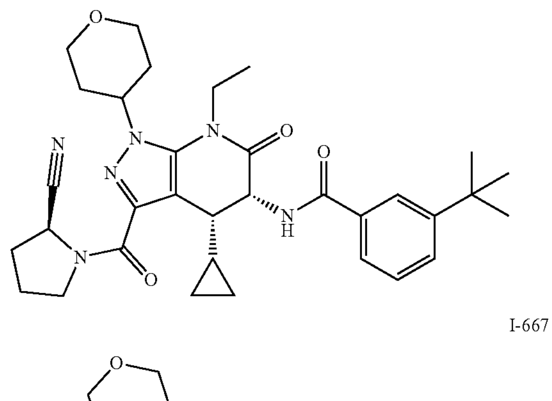
I-667
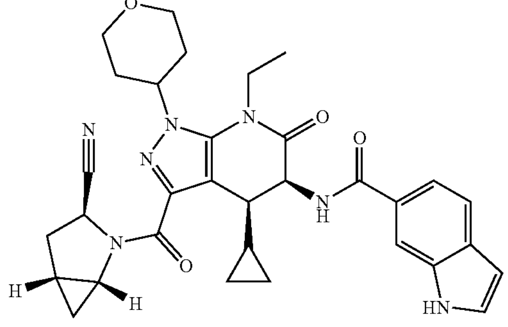

I-668
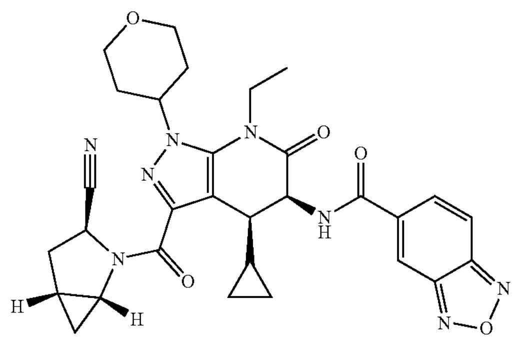
I-669
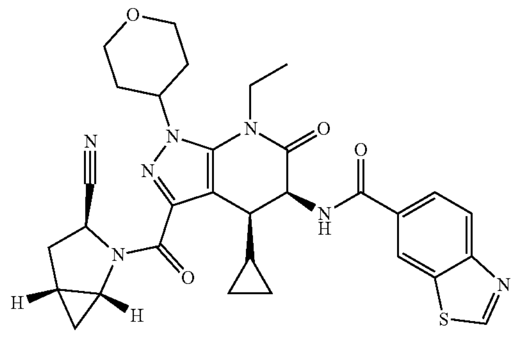
I-673
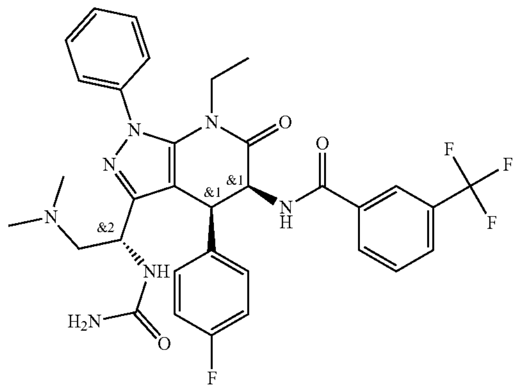
I-674
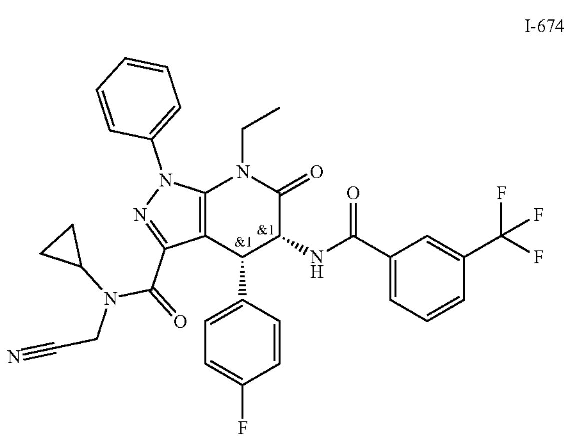
I-676
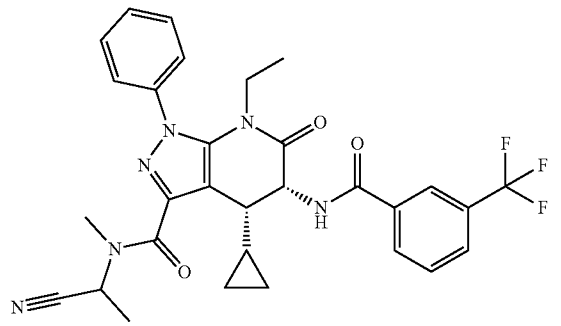
I-677
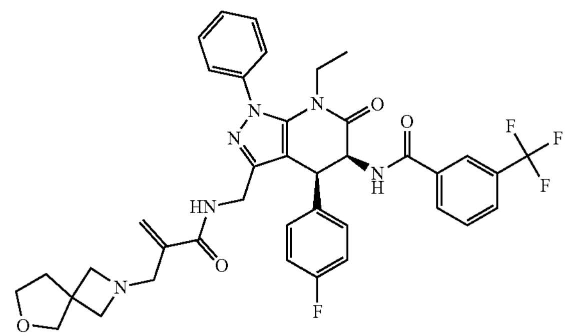
I-679
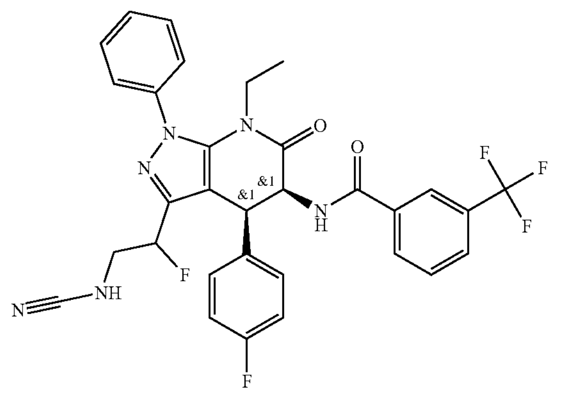
I-680
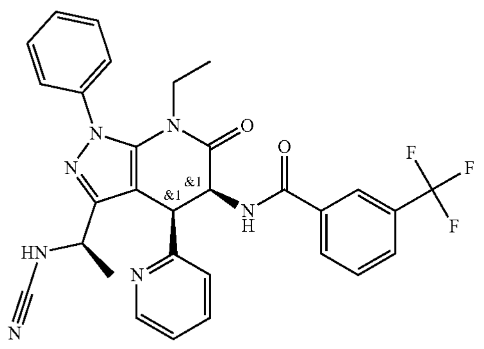

-continued
I-681
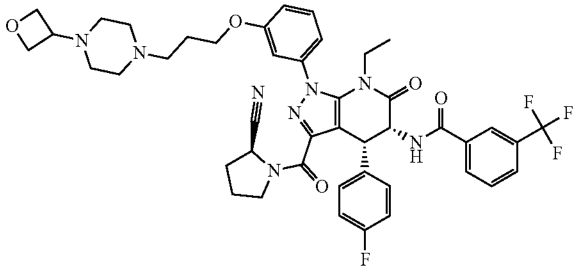
I-682
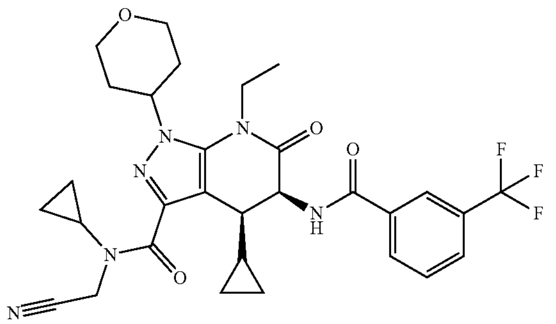
I-683
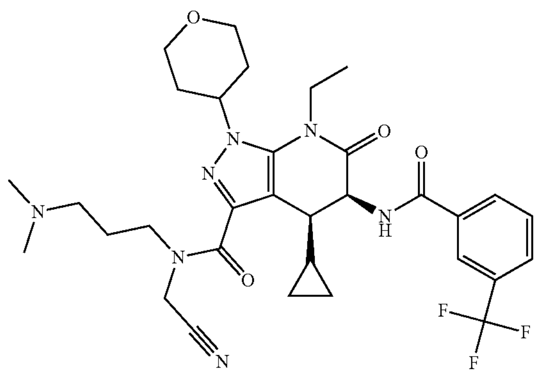
I-684
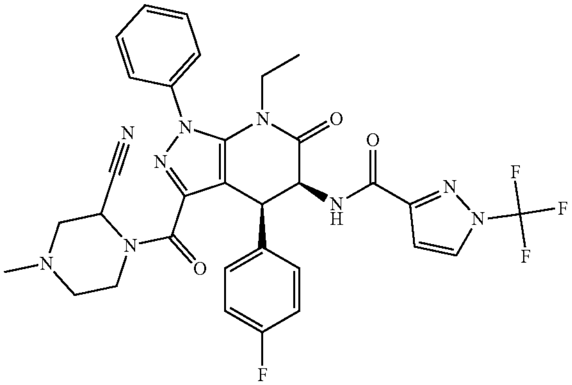
-continued
I-685
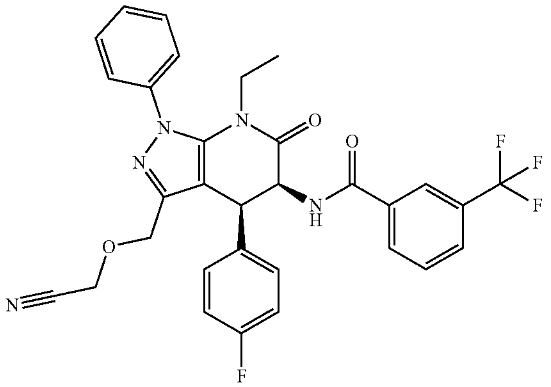
I-686
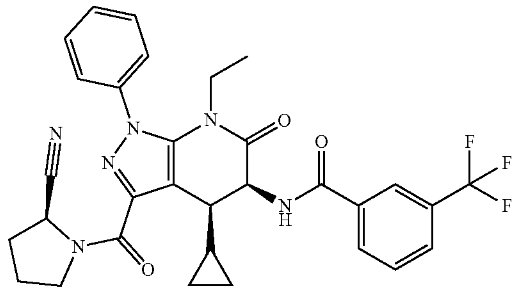
I-687
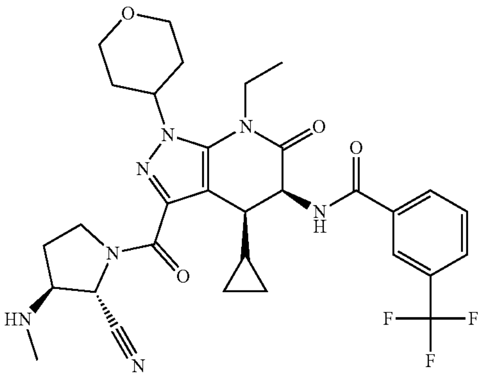
I-688
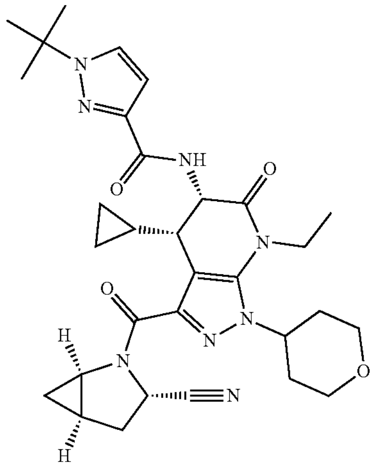

I-689
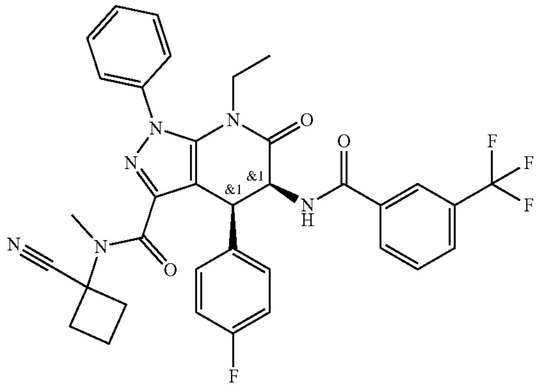
I-690
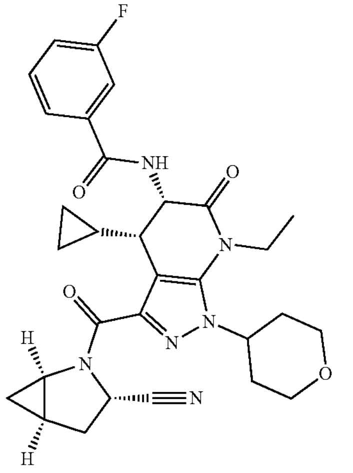
I-691
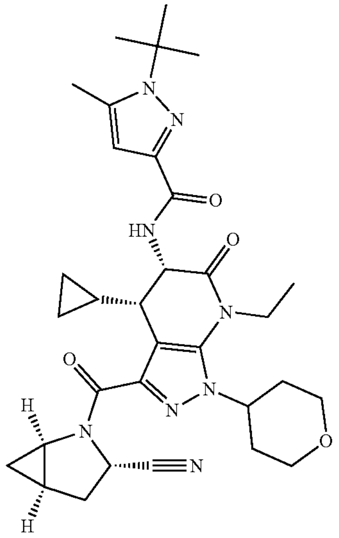
I-692
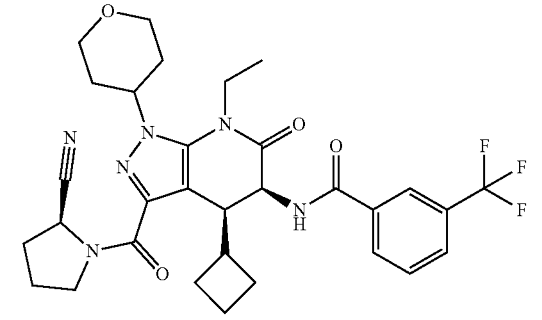
I-693
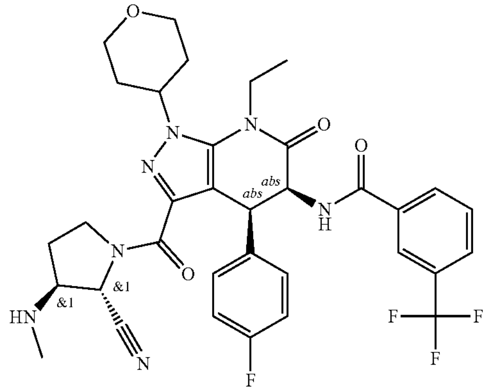
I-694
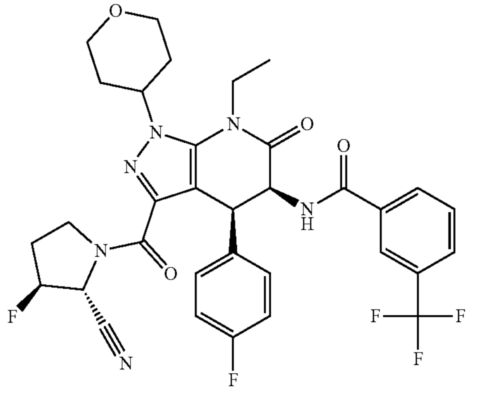
I-695
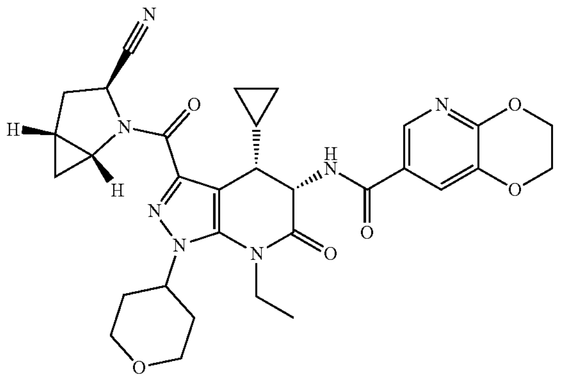

-continued
I-696
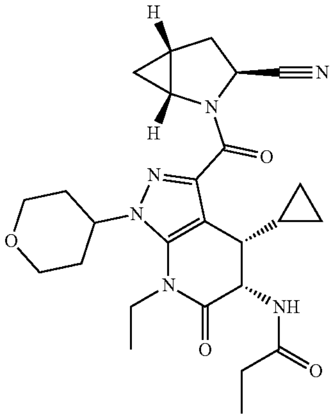
I-697
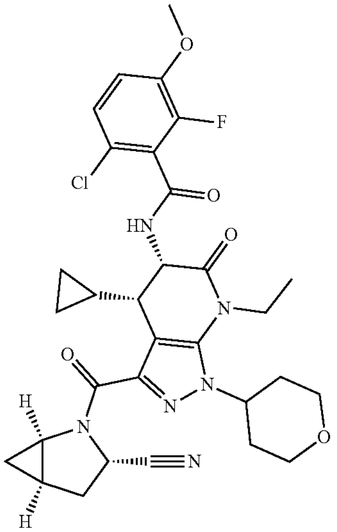
I-698
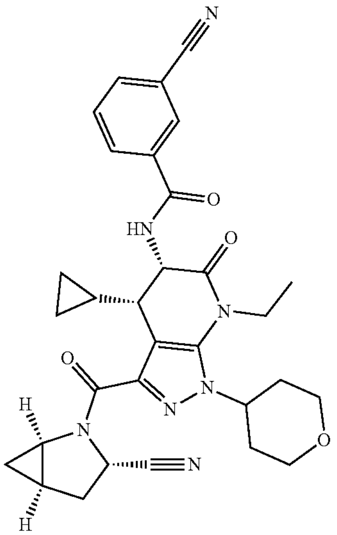
-continued
I-699
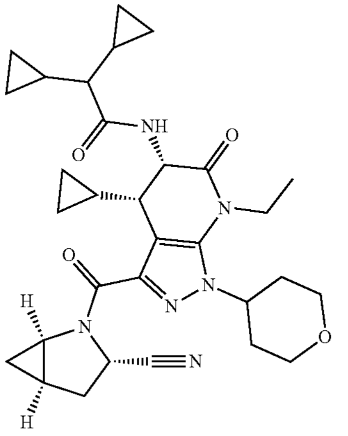
I-700
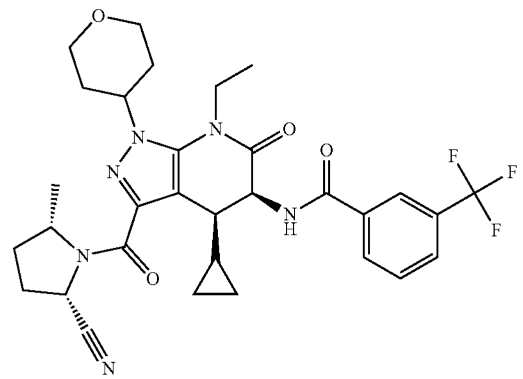
I-701
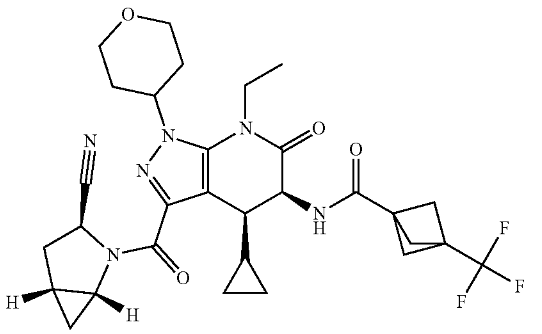
I-702
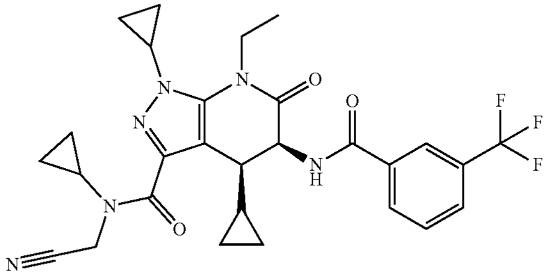

-continued
I-703
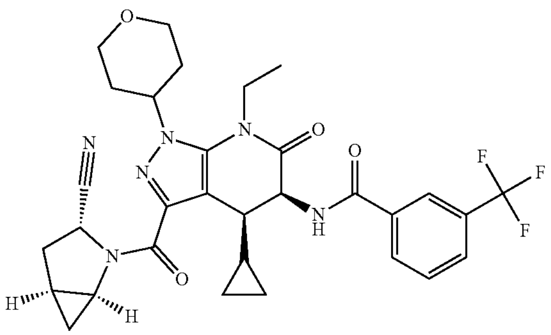
I-704
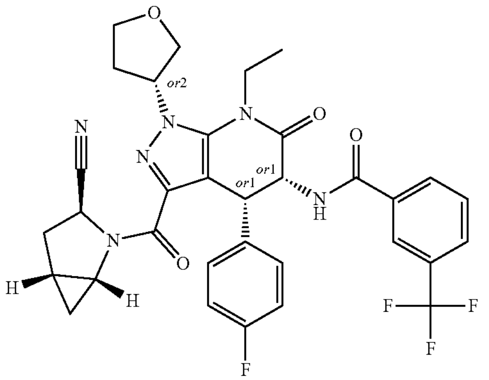
I-705
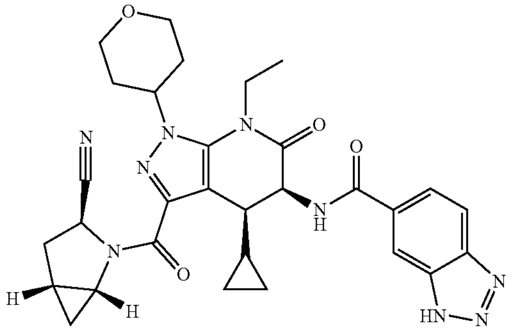
I-706
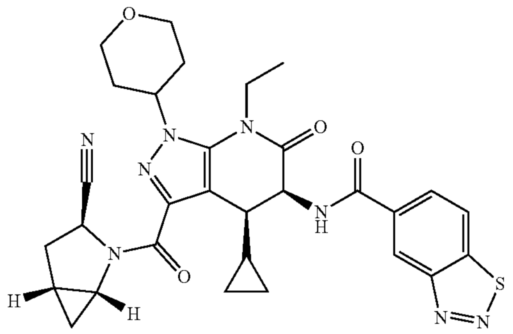
-continued
I-707
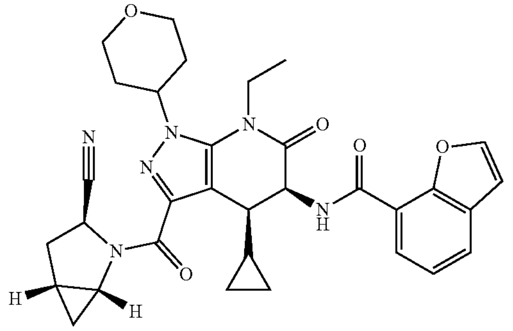
I-3a
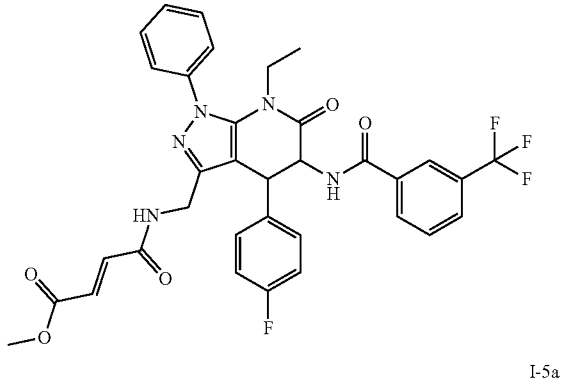
I-5a
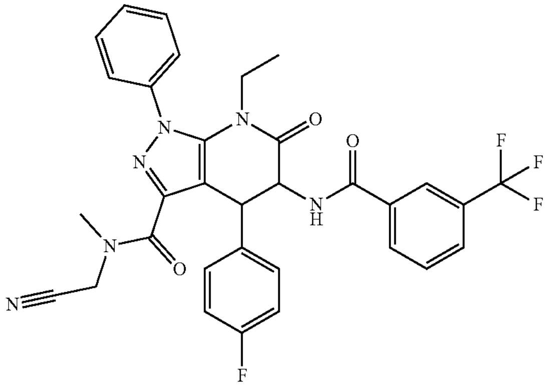
I-34a
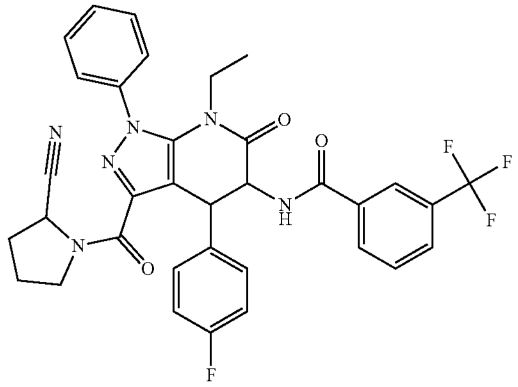

-continued
I-49a
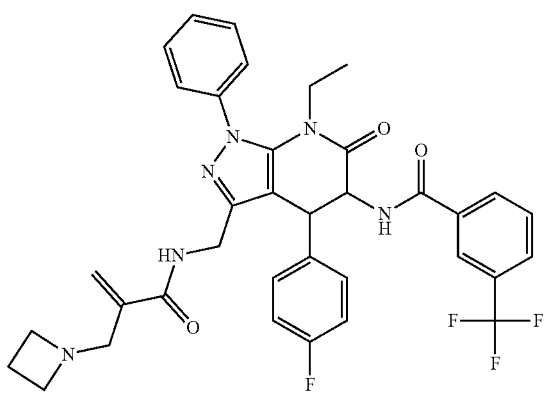
I-92a
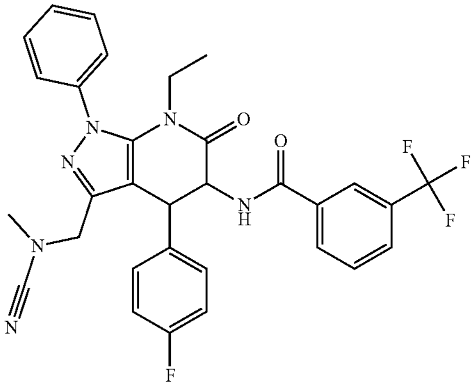
I-112a
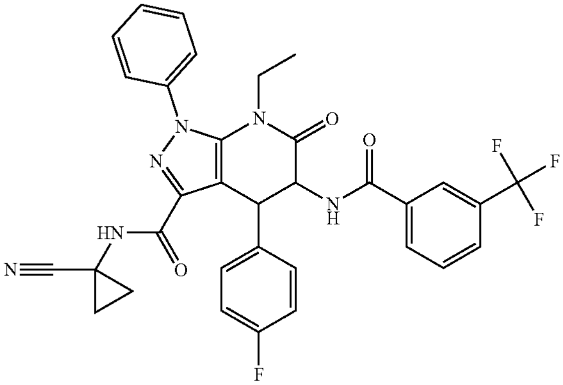
I-140a
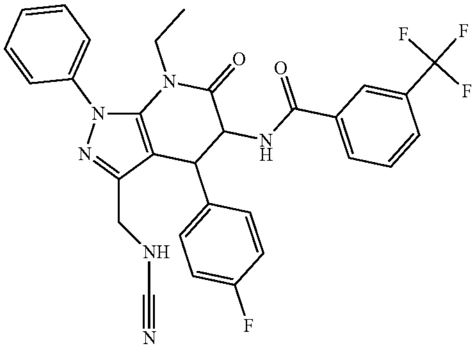
-continued
I-152a
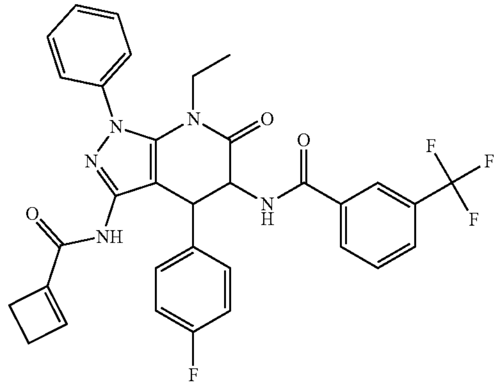
I-363a
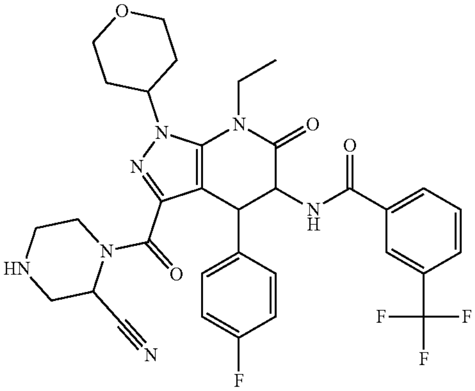
I-552a
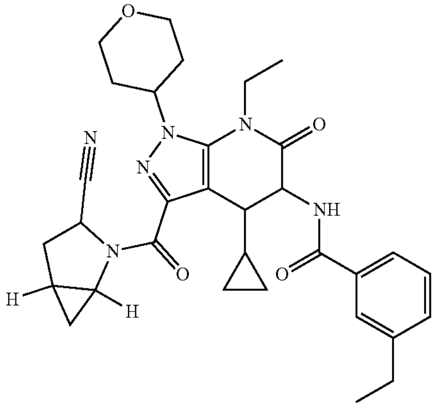
2. Compounds and Related Definitions
As described generally above, the present invention provides a compound of Formula I:
I
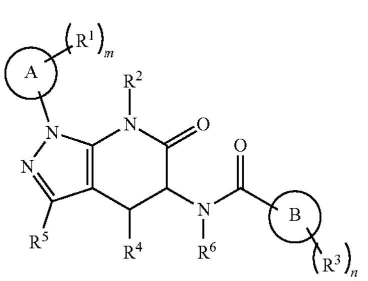
or a pharmaceutically acceptable salt thereof, wherein the variables are as described above.

Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in *Organic Chemistry*, Thomas Sorrell, University Science Books, Sausalito: 1999, and *March's Advanced Organic Chemistry: Reactions, Mechanisms, and Structure*, M. B. Smith and J. March, $7^{th}$ Edition, John Wiley & Sons: 2013; the entire contents of each of which are hereby incorporated by reference.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated, or having one or more units of unsaturation, having one or more atoms in common between the two rings of the ring system. Thus, the term includes any permissible ring fusion, such as ortho-fused or spirocyclic. As used herein, the term "spirocyclic" refers to organic compounds that contain at least two rings with one common atom, generally a quaternary carbon. Generally, the number of carbon atoms linked to the spiro atom in each ring is indicated in ascending order in brackets placed between the spiro prefix and the hydrocarbon name. For example,

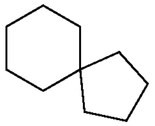

can be represented as spiro[4.5]decane.

As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, and sulfur. As used herein, the term "bridged bicyclic" refers to any bicyclic ring system, i.e. carbocyclic or heterocyclic, saturated, or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, and sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally, or alternatively, any substitutable nitrogen of a bridged bicyclic group is optionally substituted. Exemplary bicyclic rings include:

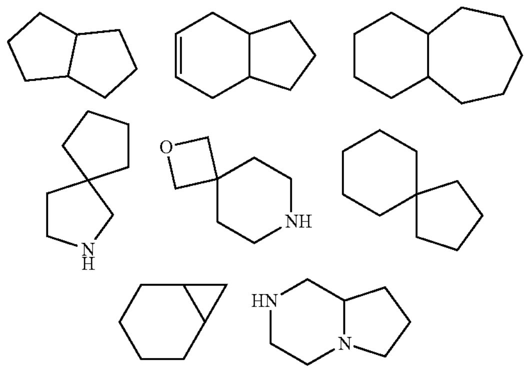

Exemplary bridged bicyclics include:

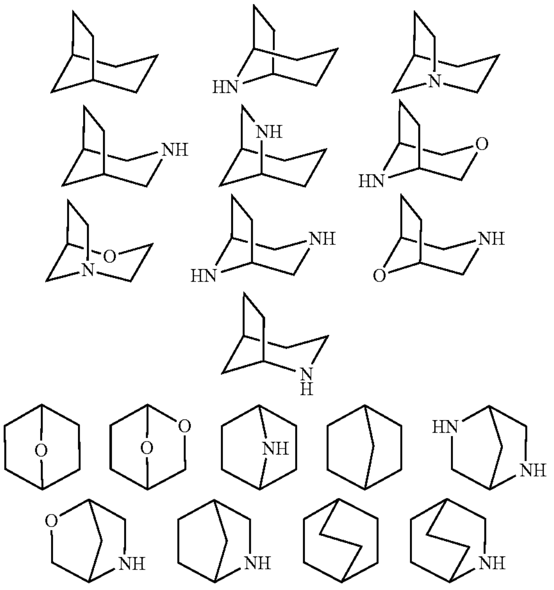

-continued

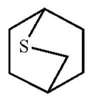 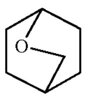 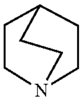 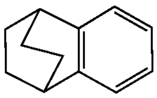
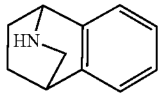 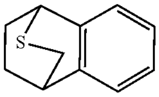 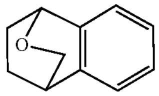

The term “lower alkyl” refers to a $C_{1-4}$ straight or branched alkyl group. Exemplary lower alkyl groups are methyl, ethyl, propyl, isopropyl, butyl, isobutyl, and tert-butyl.

The term “lower haloalkyl” refers to a $C_{1-4}$ straight or branched alkyl group that is substituted with one or more halogen atoms.

The term “heteroatom” means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH(as in pyrrolidinyl) or $NR^+$ (as in N-substituted pyrrolidinyl)).

The term “unsaturated,” as used herein, means that a moiety has one or more units of unsaturation.

As used herein, the term “bivalent $C_{1-8}$ (or $C_{1-6}$) saturated or unsaturated, straight or branched, hydrocarbon chain,” refers to bivalent alkylene, alkenylene, and alkynylene chains that are straight or branched as defined herein.

The term “alkylene” refers to a bivalent alkyl group. An “alkylene chain” is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term “alkenylene” refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term “halogen” means F, Cl, Br, or I.

The term “aryl” used alone or as part of a larger moiety as in “aralkyl,” “aralkoxy,” or “aryloxyalkyl,” refers to monocyclic or bicyclic ring systems having a total of five to fourteen ring members, wherein at least one ring in the system is aromatic and wherein each ring in the system contains 3 to 7 ring members. The term “aryl” may be used interchangeably with the term “aryl ring.” In certain embodiments of the present invention, “aryl” refers to an aromatic ring system which includes, but not limited to, phenyl, biphenyl, naphthyl, anthracyl and the like, which may bear one or more substituents. Also included within the scope of the term “aryl,” as it is used herein, is a group in which an aromatic ring is fused to one or more non-aromatic rings, such as indanyl, phthalimidyl, naphthimidyl, phenanthridinyl, or tetrahydronaphthyl, and the like. The term “phenylene” refers to a multivalent phenyl group having the appropriate number of open valences to account for groups attached to it. For example, “phenylene” is a bivalent phenyl group when it has two groups attached to it (e.g.,

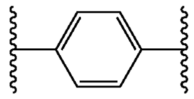 [SMILES: *c1ccc(*)cc1]

); “phenylene” is a trivalent phenyl group when it has three groups attached to it (e.g.,

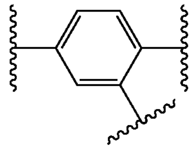 [SMILES: *c1ccc(*)c(*)c1]

). The term “arylene” refers to a bivalent aryl group.

The terms “heteroaryl” and “heteroar-,” used alone or as part of a larger moiety, e.g., “heteroaralkyl,” or “heteroaralkoxy,” refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term “heteroatom” refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms “heteroaryl” and “heteroar-,” as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term “heteroaryl” may be used interchangeably with the terms “heteroaryl ring,” “heteroaryl group,” or “heteroaromatic,” any of which terms include rings that are optionally substituted. The term “heteroaralkyl” refers to an alkyl group substituted with a heteroaryl, wherein the alkyl and heteroaryl portions independently are optionally substituted.

The term “heteroarylene” refers to a multivalent heteroaryl group having the appropriate number of open valences to account for groups attached to it. For example, “heteroarylene” is a bivalent heteroaryl group when it has two groups attached to it; “heteroarylene” is a trivalent heteroaryl group when it has three groups attached to it. The term “pyridinylene” refers to a multivalent pyridine radical having the appropriate number of open valences to account for groups attached to it. For example, “pyridinylene” is a bivalent pyridine radical when it has two groups attached to it (e.g.,

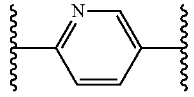 [SMILES: *c1ccc(*)nc1]

); "pyridinylene" is a trivalent pyridine radical when it has three groups attached to it (e.g.,

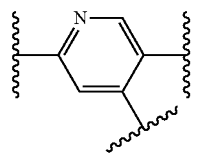 [SMILES: *c1cc(*)c(*)cn1]

).

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH(as in pyrrolidinyl), or $^{+}NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted. The term "oxo-heterocyclyl" refers to a heterocyclyl substituted by an oxo group. The term "heterocyclylene" refers to a multivalent heterocyclyl group having the appropriate number of open valences to account for groups attached to it. For example, "heterocyclylene" is a bivalent heterocyclyl group when it has two groups attached to it; "heterocyclylene" is a trivalent heterocyclyl group when it has three groups attached to it.

As used herein, the term "partially unsaturated" refers to a ring moiety that includes at least one double or triple bond. The term "partially unsaturated" is intended to encompass rings having multiple sites of unsaturation but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent ("optional substituent") at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^{\circ}$; $-(CH_2)_{0-4}OR^{\circ}$; $-O(CH_2)_{0-4}R^{\circ}$, $-O-(CH_2)_{0-4}C(O)OR^{\circ}$; $-(CH_2)_{0-4}CH(OR^{\circ})_2$; $-(CH_2)_{0-4}SR^{\circ}$; $-(CH_2)_{0-4}Ph$, which may be substituted with $R^{\circ}$; $-(CH_2)_{0-4}O(CH_2)_{0-1}Ph$ which may be substituted with $R^{\circ}$; $-CH{=}CHPh$, which may be substituted with $R^{\circ}$; $-(CH_2)_{0-4}O(CH_2)_{0-1}$-pyridyl which may be substituted with $R^{\circ}$; $-NO_2$; $-CN$; $-N_3$; $-(CH_2)_{0-4}N(R^{\circ})_2$; $-(CH_2)_{0-4}N(R^{\circ})C(O)R^{\circ}$; $-N(R^{\circ})C(S)R^{\circ}$; $-(CH_2)_{0-4}N(R^{\circ})C(O)NR^{\circ}_2$; $-N(R^{\circ})C(S)NR^{\circ}_2$; $-(CH_2)_{0-4}N(R^{\circ})C(O)OR^{\circ}$; $-N(R^{\circ})N(R^{\circ})C(O)R^{\circ}$; $-N(R^{\circ})N(R^{\circ})C(O)NR^{\circ}_2$; $-N(R^{\circ})N(R^{\circ})C(O)OR^{\circ}$; $-(CH_2)_{0-4}C(O)R^{\circ}$; $-C(S)R^{\circ}$; $-(CH_2)_{0-4}C(O)OR^{\circ}$; $-(CH_2)_{0-4}C(O)SR^{\circ}$; $-(CH_2)_{0-4}C(O)OSiR^{\circ}_3$; $-(CH_2)_{0-4}OC(O)R^{\circ}$; $-OC(O)(CH_2)_{0-4}SR-$, $SC(S)SR^{\circ}$; $-(CH_2)_{0-4}SC(O)R^{\circ}$; $-(CH_2)_{0-4}C(O)NR^{\circ}_2$; $-C(S)NR^{\circ}_2$; $-C(S)SR^{\circ}$; $-SC(S)SR^{\circ}$, $-(CH_2)_{0-4}OC(O)NR^{\circ}_2$; $-C(O)N(OR^{\circ})R^{\circ}$; $-C(O)C(O)R^{\circ}$; $-C(O)CH_2C(O)R^{\circ}$; $-C(NOR^{\circ})R^{\circ}$; $-(CH_2)_{0-4}SSR^{\circ}$; $-(CH_2)_{0-4}S(O)_2R^{\circ}$; $-(CH_2)_{0-4}S(O)_2OR^{\circ}$; $-(CH_2)_{0-4}OS(O)_2R^{\circ}$; $-S(O)_2NR^{\circ}_2$; $-(CH_2)_{0-4}S(O)R^{\circ}$; $-N(R^{\circ}S(O)_2NR^{\circ}_2$; $-N(R^{\circ}S(O)_2R^{\circ}$; $-N(OR^{\circ})R^{\circ}$; $-C(NH)NR^{\circ}_2$; $-P(O)_2R^{\circ}$; $-P(O)R^{\circ}_2$; $-OP(O)R^{\circ}_2$; $-OP(O)(OR^{\circ}_2$; $SiR^{\circ}_3$; $-(C_{1-4}$ straight or branched alkylene)O—) $N(R^{\circ}_2$; or $-(C_{1-4}$ straight or branched)alkylene)C(O)O—$N(R^{\circ}_2$, wherein each $R^{\circ}$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, and sulfur, which may be substituted as defined below.

Suitable monovalent substituents on $R^{\circ}$ (or the ring formed by taking two independent occurrences of $R^{\circ}$ together with their intervening atoms), are independently halogen, $-(CH_2)_{0-2}R^{\bullet}$, -(halo$R^{\bullet}$, $-(CH_2)_{0-2}OH$, $-(CH_2)_{0-2}OR^{\bullet}$, $-(CH_2)_{0-2}CH(OR^{\bullet})_2$; $-O$(halo$R^{\bullet}$, $-CN$, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\bullet}_3$, $-OSiR^{\bullet}_3$, $-C(O)SR^{\bullet}$, $-(C_{1-4}$ straight or branched alkylene)$C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of $R^{\bullet}$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $—O(C(R^*_2))_{2-3}O—$, or $—S(C(R^*_2))_{2-3}S—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: $—O(CR^*_2)_{2-3}O—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, $—R^●$, -(halo$R^●$, —OH, $—OR^●$, —O(halo$R^●$), —CN, —C(O) OH, $—C(O)OR^●$, $—NH_2$, $—NHR^●$, $—NR^●_2$, or $—NO_2$, wherein each $R^●$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include $—R^†$, $—NR^†_2$, $—C(O)R^†$, $—C(O)OR^†$, $—C(O)C(O)R^†$, $—C(O)CH_2C(O)R^†$, $—S(O)_2R^†$, $—S(O)_2NR^†_2$, $—C(S)NR^†_2$, $—C(NH)NR^†_2$, or $—N(R^†) S(O)_2R^†$; wherein each $R^†$ is independently hydrogen, $C_{1-6}$ aliphatic which may be substituted as defined below, unsubstituted -Oph, or an unsubstituted 5-6-membered saturated, partially unsaturated, or aryl ring having 0-4 heteroatoms independently selected from nitrogen, oxygen, and sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of $R^†$ are independently halogen, $—R^●$, -(halo$R^●$), —OH, $—OR^●$, —O(halo$R^●$), —CN, —C(O)OH, $—C(O)OR^●$, $—NH_2$, $—NHR^●$, $—NR^●_2$, or $—NO_2$, wherein each $R^●$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, and sulfur.

As used herein, the term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66 (1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Salts derived from appropriate bases include alkali metal, alkaline earth metal, ammonium, and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

Compounds containing one or more stereocenters are a mixture of stereoisomers, unless otherwise stated or described (for example, with use of dashed or wedged bonds denoting stereochemistry). Generally, enhanced stereochemical representation introduces three types of identifiers that can be attached to a stereogenic center. A stereochemical group label is composed from an identifier and a group number. Each stereogenic center marked with wedge bonds belongs to one (and only one) stereochemical group. Grouping allows to specify relative relationships among stereogenic centers.

ABS denotes a stereogenic center where the absolute configuration is known. As used herein, "or" denotes a stereogenic center where the relative configuration is known, but the absolute configuration is not known. The structure represents one stereoisomer that is either the structure as drawn (R,S) or the epimer in which the stereogenic centers have the opposite configuration (S,R). One of skill in the art would understand that if a single stereogenic center is present, the designation “or” represents a single isomer for which the absolute configuration is not known. As used herein, “or1”, “or2” denote stereogenic centers where the relative configuration is known, but the absolute configuration is not known when applied to a multi-center stereogroup.

As used herein, “&1” denotes a mixture of two enantiomers, the structure as drawn and the epimer in which the stereogenic centers have the opposite configuration. As used herein, “&1”, “&2” denote a mixture of stereoisomers when applied to a multi-center stereogroup. The designations “and” and “&” are used interchangeably and denote a mixture of stereoisomers. It can be a pair of enantiomers or all the diastereomers.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher’s acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as an atropisomer (e.g., substituted biaryls), all forms of such atropisomers are considered part of this invention.

Chemical names, common names, and chemical structures may be used interchangeably to describe the same structure. If a chemical compound is referred to using both a chemical structure and a chemical name, and an ambiguity exists between the structure and the name, the structure predominates. It should also be noted that any carbon as well as heteroatom with unsatisfied valences in the text, schemes, examples, and tables herein is assumed to have the sufficient number of hydrogen atom(s) to satisfy the valences.

The terms “a” and “an” as used herein mean “one or more” and include the plural unless the context is inappropriate.

The term “alkyl” refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term “cycloalkyl” refers to a monovalent saturated cyclic, bicyclic, or bridged cyclic (e.g., adamantyl) hydrocarbon group of 3-12, 3-8, 4-8, or 4-6 carbons, referred to herein, e.g., as “$C_3$-$C_6$ cycloalkyl,” derived from a cycloalkane. Exemplary cycloalkyl groups include cyclohexyl, cyclopentyl, cyclobutyl, and cyclopropyl. The term “cycloalkylene” refers to a bivalent cycloalkyl group.

The term “haloalkyl” refers to an alkyl group that is substituted with at least one halogen. Exemplary haloalkyl groups include $-CH_2F$, $-CHF_2$, $-CF_3$, $-CH_2CF_3$, $-CF_2CF_3$, and the like. The term “haloalkylene” refers to a bivalent haloalkyl group.

The term “hydroxyalkyl” refers to an alkyl group that is substituted with at least one hydroxyl. Exemplary hydroxyalkyl groups include $-CH_2CH_2OH$, $-C(H)(OH)CH_3$, $-CH_2C(H)(OH)CH_2CH_2OH$, and the like.

The terms “alkenyl” and “alkynyl” are art-recognized and refer to unsaturated aliphatic groups analogous in length and possible substitution to the alkyls described above, but that contain at least one double or triple bond, respectively.

The term “carbocyclylene” refers to a multivalent carbocyclyl group having the appropriate number of open valences to account for groups attached to it. For example, “carbocyclylene” is a bivalent carbocyclyl group when it has two groups attached to it; “carbocyclylene” is a trivalent carbocyclyl group when it has three groups attached to it.

The terms “alkoxyl” or “alkoxy” are art-recognized and refer to an alkyl group, as defined above, having an oxygen radical attached thereto. Representative alkoxyl groups include methoxy, ethoxy, propyloxy, tert-butoxy and the like. The term “haloalkoxyl” refers to an alkoxyl group that is substituted with at least one halogen. Exemplary haloalkoxyl groups include $-OCH_2F$, $-OCHF_2$, $-OCF_3$, $-OCH_2CF_3$, $-OCF_2CF_3$, and the like. The term “hydroxyalkoxyl” refers to an alkoxyl group that is substituted with at least one hydroxyl. Exemplary hydroxyalkoxyl groups include $-OCH_2CH_2OH$, $-OCH_2C(H)(OH)CH_2CH_2OH$, and the like. The term “alkoxylene” refers to a bivalent alkoxyl group.

The term “oxo” is art-recognized and refers to a “=O” substituent. For example, a cyclopentane substituted with an oxo group is cyclopentanone.

The symbol “〰” indicates a point of attachment. The point of attachment can be drawn at the end of the bond in a chemical structure, for example,

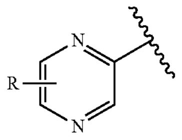

or at the center of the bond in a chemical structure, for example,

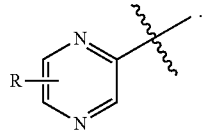

When a chemical structure containing a ring is depicted with a substituent having a bond that crosses a ring bond, the substituent may be attached at any available position on the ring. For example, the chemical structure

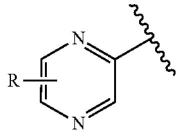

encompasses

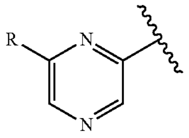

, 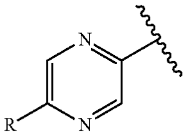

, and

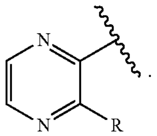

.

In the context of a polycyclic fused ring, when a chemical structure containing a polycyclic fused ring is depicted with one or more substituent(s) having a bond that crosses multiple rings, the one or more substituent(s) may be independently attached to any of the rings crossed by the bond. To illustrate, the chemical structure

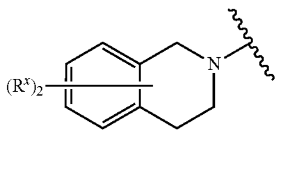

encompasses, for example,

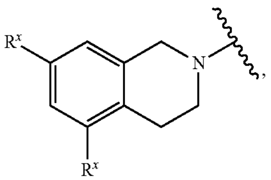

,

-continued

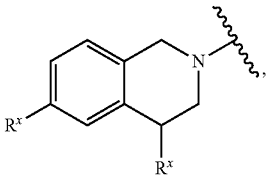

, and

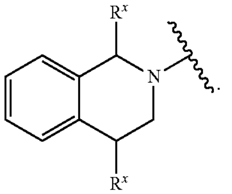

.

When any substituent or variable occurs more than one time in any constituent or the compound of the invention, its definition on each occurrence is independent of its definition at every other occurrence, unless otherwise indicated.

The term “warhead” or “warhead group” as used herein refers to a functional group present on a compound wherein that functional group is capable of reversibly or irreversibly participating in a reaction with a protein. Warheads may, for example, form covalent bonds with the protein. For example, the warhead moiety can be a functional group on an inhibitor that can participate in a bond-forming reaction, wherein a new covalent bond is formed between a portion of the warhead and a donor, for example an amino acid residue of a protein. In some embodiments, the warhead is an electrophile and the “donor” is a nucleophile such as the side chain of a cysteine residue.

One or more compounds of the invention may exist in unsolvated as well as solvated forms with pharmaceutically acceptable solvents such as water, ethanol, and the like, and it is intended that the invention embrace both solvated and unsolvated forms. “Solvate” means a physical association of a compound of this invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. “Solvate” encompasses both solution-phase and isolatable solvates. Non-limiting examples of suitable solvates include ethanolates, methanolates, and the like. “Hydrate” is a solvate wherein the solvent molecule is $H_2O$.

As used herein, the terms “subject” and “patient” are used interchangeably and refer to organisms to be treated by the methods of the present invention. Such organisms preferably include, but are not limited to, mammals (e.g., murines, simians, equines, bovines, porcines, canines, felines, and the like), and, most preferably, includes humans.

The term “$IC_{50}$” is art-recognized and refers to the concentration of a compound that is required to achieve 50% inhibition of the target. The potency of an inhibitor is usually defined by its $IC_{50}$ value. The lower the $IC_{50}$ value the greater the potency of the antagonist and the lower the concentration that is required to inhibit the maximum biological response. In certain embodiments, an inhibitor has an $IC_{50}$ and/or binding constant of less than about 100 μM, less than about 50 μM, less than about 1 μM, less than about 500 nM, less than about 100 nM, less than about 10 nM, or less than about 1 nM.

As used herein, the term “inhibitor” is defined as a compound that binds to and/or inhibits the target with measurable affinity. In some embodiments, inhibition in the presence of the inhibitor is observed in a dose-dependent manner. In some embodiments, the measured signal (e.g., signaling activity or biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or at least about 100% lower than the signal measured with a negative control under comparable conditions.

The terms “measurable affinity” and “measurably inhibit,” as used herein, means a measurable change or inhibition in target activity between a sample comprising a compound of the present invention, or composition thereof an equivalent sample comprising target, in the absence of said compound, or composition thereof.

As used herein, the term “effective amount” refers to the amount of a compound sufficient to effect beneficial or desired results (e.g., a therapeutic, ameliorative, inhibitory, or preventative result). An effective amount can be administered in one or more administrations, applications, or dosages and is not intended to be limited to a particular formulation or administration route.

As used herein, the term “treating” includes any effect, e.g., lessening, reducing, modulating, ameliorating, or eliminating, that results in the improvement of the condition, disease, disorder, and the like, or ameliorating a symptom thereof. In some embodiments, treatment can be administered after one or more symptoms have developed. In other embodiments, treatment can be administered in the absence of symptoms. For example, treatment can be administered to a susceptible individual prior to the onset of symptoms (e.g., in light of a history of symptoms and/or in light of genetic or other susceptibility factors). Treatment can also be continued after symptoms have resolved, for example, to prevent or delay their recurrence.

As used herein, the term “pharmaceutical composition” refers to the combination of an active agent with a carrier, inert or active, making the composition especially suitable for diagnostic or therapeutic use in vivo or ex vivo.

As used herein, the term “pharmaceutically acceptable carrier” refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers, and adjuvants, see e.g., Martin, Remington’s Pharmaceutical Sciences, $15^{th}$ Ed., Mack Publ. Co., Easton, PA [1975].

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions (“inner salts”) may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified.

3. Methods of Use

It has now been found that the compounds and compositions of the disclosure can modulate DCN-1 (also referred to herein as DCN1) and are useful in treating disorders, diseases, and conditions associated with DCN-1. In some embodiments, modulating DCN-1 is inhibiting or reducing the activity of DCN-1. Without being limited to a specific mechanism, as shown herein, inhibiting or reducing the activity of DCN-1 results in reduced neddylation and other downstream effects. It has also been found that the compounds and compositions of the disclosure can modulate DCN-2 (also referred to herein as DCN2) and are useful in treating disorders, diseases, and conditions associated with DCN-2. In some embodiments, modulating DCN-2 is inhibiting or reducing the activity of DCN-2. Without being limited to a specific mechanism, as shown herein, inhibiting or reducing the activity of DCN-2 results in reduced neddylation and other downstream effects.

In one aspect, the present disclosure provides a method of modulating the activity of DCN-1 in vitro or in vivo, comprising contacting DCN-1 with a compound or composition thereof disclosed herein, or a pharmaceutically acceptable salt thereof. In one aspect, the present disclosure provides a method of modulating the activity of DCN-2 in vitro or in vivo, comprising contacting DCN-2 with a compound or composition thereof disclosed herein, or a pharmaceutically acceptable salt thereof.

In some embodiments, the present disclosure provides a method of modulating the activity of DCN-1 and/or DCN-2 in a subject, comprising administering to the subject a compound or composition thereof disclosed herein, or a pharmaceutically acceptable salt thereof.

In one aspect, the disease, disorder, or condition associated with DCN-1 or DCN-2 is a hemoglobinopathy such as sickle cell disorder or disease, or thalassemia disorder or disease.

In some embodiments, the disease, disorder, or condition associated with DCN-1 or DCN-2 is selected from one of those described in He et al. (Int Journal of Biological Macromolecules 227, 2024, 134541). In some embodiments, the disease, disorder, or condition associated with DCN-1 or DCN-2 is cancer (e.g., non-small cell lung cancer or gastric cancer), liver injury (e.g., non-alcoholic fatty liver disease), cardiac remodeling (e.g., atherosclerosis) or neurodegenerative disease (e.g., frontotemporal lobar degeneration). In some embodiments, the disease, disorder, or condition associated with DCN-1 or DCN-2 is characterized by overexpression of DCN-1 and/or DCN-2. In some embodiments, the disease, disorder, or condition associated with DCN-1 and/or DCN-2 overexpression is cancer (e.g., non-small cell lung cancer or gastric cancer).

In one aspect, the disclosure provides compounds and compositions for the treatment of of hemoglobinopathies such as sickle cell disorder or disease or thalassemia disorder or disease. In one aspect, the compounds and compositions described herein induce HbF (fetal hemoglobin; expressed by the gamma globin genes HBG1 and HBG2). It should be appreciated that induction of HbF allows for the treatment of hemoglobinopathies such as sickle cell disorder or disease or thalassemia disorder or disease. Thus, in one aspect, the disclosure provides compounds and compositions for the treatment of sickle cell disease.

In one aspect, the disclosure provides compounds and compositions for the treatment of of hemoglobinopathies such as sickle cell disorder or disease or thalassemia disorder or disease In one aspect, the compounds and compositions described herein induce HbF (fetal hemoglobin; expressed by the gamma globin genes HBG1 and HBG2) and reduce HbA (adult hemoglobin; expressed by the beta globin gene HBB), thus inducing production of fetal hemoglobin and reducing the expression of the hemoglobin beta gene. It should be appreciated that induction of HbF and reduction of HbA allows for the treatment of hemoglobinopathies such as sickle cell disorder or disease or thalassemia disorder or disease. Thus, in one aspect, the disclosure provides compounds and compositions for the treatment of sickle cell disease.

In some embodiments, a compound described herein is an irreversible covalent inhibitor of DCN-1 and/or DCN-2. In some embodiments, an irreversible covalent inhibitor of DCN-1 and/or DCN-2 provided herein can be used to treat diseases associated with DCN-1 and/or DCN-2. In some embodiments, an irreversible covalent inhibitor of DCN-1 and/or DCN-2 provided herein can be used to treat sickle cell disease. In some embodiments, a compound described herein is a reversible covalent inhibitor of DCN-1 and/or DCN-2. In some embodiments, a reversible covalent inhibitor of DCN-1 and/or DCN-2 provided herein can be used to treat diseases associated with DCN-1 and/or DCN-2. In some embodiments, a reversible covalent inhibitor of DCN-1 and/or DCN-2 provided herein can be used to treat sickle cell disease. In some embodiments, a compound described herein is a reversible inhibitor of DCN-1 and/or DCN-2. In some embodiments, a reversible inhibitor of DCN-1 and/or DCN-2 provided herein can be used to treat diseases associated with DCN-1 and/or DCN-2. In some embodiments, a reversible covalent of DCN-1 and/or DCN-2 provided herein can be used to treat sickle cell disease.

In one aspect, the disclosure provides irreversible covalent inhibitors of DCN-1 and/or DCN-2 for the treatment of a disease, disorder, or condition associated with DCN-1 and/or DCN-2. In some embodiments, the disclosure provides irreversible covalent inhibitors of DCN-1 and/or DCN-2 for the treatment of sickle cell disease. In some embodiments, the irreversible covalent inhibitors of DCN-1 and/or DCN-2 irreversibly covalently modify a cysteine of DCN-1 and/or DCN-2. In some embodiments, the irreversible covalent inhibitors of DCN-1 and/or DCN-2 irreversibly covalently modify Cys115 of DCN-1 and/or DCN-2. In some embodiments, the irreversible covalent inhibitor includes a warhead to allow for the covalent modification of DCN-1 and/or DCN-2. In some embodiments the warhead includes a nitrile group. In some embodiments, the warhead does not include a vinyl group.

In one aspect, the disclosure provides reversible covalent inhibitors of DCN-1 and/or DCN-2 for the treatment of a disease, disorder, or condition associated with DCN-1 and/or DCN-2. In some embodiments, the disclosure provides reversible covalent inhibitors of DCN-1 and/or DCN-2 for the treatment of sickle cell disease. In some embodiments, the reversible covalent inhibitors of DCN-1 and/or DCN-2 reversibly covalently modify a cysteine of DCN-1 and/or DCN-2. In some embodiments, the reversible covalent inhibitors of DCN-1 and/or DCN-2 reversibly covalently modify Cys115 of DCN-1 and/or DCN-2. In some embodiments, the reversible covalent inhibitor includes a warhead to allow for the covalent modification of DCN-1 and/or DCN-2. In some embodiments the warhead includes a nitrile group. In some embodiments, the warhead does not include a vinyl group.

In one aspect, the disclosure provides reversible inhibitors of DCN-1 and/or DCN-2 for the treatment of a disease, disorder, or condition associated with DCN-1 or DCN-2. In one aspect, the disclosure provides reversible inhibitors of DCN-1 and/or DCN-2 for the treatment of sickle cell disease.

In some embodiments, the disclosure provides irreversible covalent inhibitors of DCN-1 and/or DCN-2, wherein the compound has a warhead that can irreversible covalently modify a cysteine of DCN-1 and/or DCN-2. In some embodiments, the cysteine is Cys115 of DCN-1 and/or DCN-2. In some embodiments, the disclosure provides reversible covalent inhibitors of DCN-1 and/or DCN-2, wherein the compound has a warhead that can reversible covalently modify a cysteine of DCN-1 and/or DCN-2. In some embodiments, the cysteine is Cys115 of DCN-1 and/or DCN-2.

In one aspect, the disclosure provides a DCN-1 that is covalently modified at Cys115. In some embodiments, the disclosure provides methods and compositions for covalently modifying DCN-1 in a subject. In some embodiments, the disclosure provides methods and compositions for covalently modifying DCN-1 Cys-115 in a subject. In some embodiments, the disclosure provides methods and compositions for covalently modifying DCN-1 Cys-115 in a subject for the treatment of sickle cell disease.

In one aspect, the disclosure provides a DCN-2 that is covalently modified at Cys115. In some embodiments, the disclosure provides methods and compositions for covalently modifying DCN-2 in a subject. In some embodiments, the disclosure provides methods and compositions for covalently modifying DCN-2 Cys-115 in a subject. In some embodiments, the disclosure provides methods and compositions for covalently modifying DCN-2 Cys-115 in a subject for the treatment of sickle cell disease.

In one aspect, the present disclosure provides a method of treating a hemoglobinopathy disorder or disease, comprising administering to a subject in need thereof a compound or composition thereof disclosed herein, or a pharmaceutically acceptable salt thereof. In another aspect, the present disclosure provides a method of inducing or increasing production of fetal hemoglobin. Such methods are useful, for example, in treating hemoglobin-related disorders including sickle cell disorders, diseases and conditions and thalassemia.

In some embodiments, the hemoglobinopathy is a sickle cell disorder or disease.

In some embodiments, the hemoglobinopathy is a thalassemia disorder or disease.

In one aspect, the present disclosure provides a method to increase red blood cell levels and/or hemoglobin levels in a subject in need thereof, treat or prevent an anemia in a subject in need thereof, treat sickle-cell disease in a subject in need thereof, or treat one or more complications of sickle-cell disease in a subject in need thereof, comprising administering to a subject in need thereof a compound disclosed herein, or a pharmaceutically acceptable salt thereof, in combination with hydroxyurea or a pharmaceutically acceptable salt thereof.

In one aspect, the present disclosure provides a method to increase fetal hemoglobin levels in a subject in need thereof, treat or prevent an anemia in a subject in need thereof, treat sickle-cell disease in a subject in need thereof, or treat one or more complications of sickle-cell disease in a subject in need thereof, comprising administering to a subject in need thereof a compound disclosed herein, or a pharmaceutically acceptable salt thereof, in combination with hydroxyurea or a pharmaceutically acceptable salt thereof.

In some embodiments, the present disclosure provides a method for the treatment of a DCN-1 associated disease. In some embodiments, the present disclosure provides a method for the treatment of a DCN-2 associated disease. In some embodiments, the present disclosure provides a method for the treatment of cancers, premalignant conditions (e.g., hyperplasia, metaplasia, and dysplasia), benign tumors, hyperproliferative disorders, and benign dysproliferative disorders. Such methods comprise the step of administering to a subject in need thereof a compound disclosed herein, or a pharmaceutically acceptable salt thereof. In some embodiments, the cancer is characterized by overexpression of DCN-1 and/or DCN-2.

In some embodiments, cancers and related disorders that can be treated or prevented by methods disclosed herein include, but are not limited, to the following: a squamous cell carcinoma, a metastatic squamous cell carcinoma, a non-small cell lung carcinoma, a uterine carcino-sarcoma, an embryonal rhabdomyosarcoma, a glioblastoma, a medulloblastoma, an osteosarcoma, or an adrenocortical tumor. In some embodiments, the cancer and related disorders include a cancer of the lung, cervix, ovary, uterus, esophagus, prostate, or head and neck.

In some embodiments, the cancer of the lung includes a non-small cell lung cancer, including, but not limited to a squamous cell carcinoma, adenocarcinoma, or large cell-undifferentiated carcinoma.

In some embodiments, cancers and related disorders include a hematological malignancy such as a leukemia, a lymphoma, a myeloma, a multiple lymphoma, a B-cell non-Hodgkin's lymphoma, or an acute myeloid leukemia.

In some embodiments, the present disclosure provides a method for the treatment of a cancer, including, but not limited to, leukemia, acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, polycythemia vera, Lymphoma, Hodgkin's disease, non-Hodgkin's disease, multiple myeloma, Waldenstrom's macroglobulinemia, heavy chain disease, solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In some embodiments, the present disclosure provides a method for the treatment of leukemia, including, but not limited to, acute leukemia, acute lymphocytic leukemia; acute myelocytic leukemia, including, but not limited to, myeloblastic, promyelocytic, myelomonocytic, monocytic, erythroleukemia and myelodysplastic syndrome; chronic leukemia, including, but not limited to, chronic myelocytic (granulocytic) leukemia, chronic lymphocytic leukemia, hairy cell leukemia; polycythemia vera; lymphomas, including, but not limited to, Hodgkin's lymphoma, non-Hodgkin's lymphoma; myeloma, including, but not limited, to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumor, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including, but not limited to, pheochromocytom and adrenocortical carcinoma; thyroid cancer, including, but not limited to, papillary or follicular thyroid cancer, medullary thyroid cancer and anaplastic thyroid cancer; pancreatic cancer, including, but not limited to, insulinoma, gastrinoma, glucagonoma, vipoma, somatostatin-secreting tumor, and carcinoid or islet cell tumor; pituitary cancers, including, but not limited to, Cushing's disease, prolactin-secreting tumor, acromegaly, and diabetes insipius; eye cancer, including, but not limited to, ocular melanoma such as iris melanoma, choroidal melanoma, and cilliary body melanoma, and retinoblastoma; vaginal cancer, including, but not limited to, squamous cell carcinoma, adenocarcinoma, and melanoma; vulvar cancer, including, but not limited to, squamous cell carcinoma, melanoma, adenocarcinoma, basal cell carcinoma, sarcoma, and Paget's disease; cervical cancer, including, but not limited to, squamous cell carcinoma, and adenocarcinoma; uterine cancer, including, but not limited to, endometrial carcinoma and uterine sarcoma; ovarian cancers, including, but not limited to, ovarian epithelial carcinoma, borderline tumor, germ cell tumor, and stromal tumor; esophageal cancer, including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancer, including, but not limited to, adenocarcinoma, fungating (polypoid), ulcerating, superficial spreading, diffusely spreading, malignant lymphom, liposarcoma, fibrosarcoma, and carcinosarcoma; colon cancer; rectal cancer; liver cancer, including, but not limited to, hepatocellular carcinoma and hepatoblastoma, gallbladder cancer, including, but not limited to, adenocarcinoma; cholangiocarcinoma, including, but not limited to, pappillary, nodular, and diffuse; lung cancer, including, but not limited to, non-small cell lung cancer, squamous cell carcinoma (epidermoid carcinoma), adenocarcinoma, large-cell carcinoma and small-cell lung cancer; testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor); prostate cancer, including, but not limited to, adenocarcinoma, leiomyosarcoma, and rhabdomyosarcoma; penal cancers; oral cancer, including, but not limited to, squamous cell carcinoma; basal cancers; salivary gland cancer, including, but not limited to, adenocarcinoma, mucoepidermoid carcinoma, and adenoidcystic carcinoma; pharynx cancer, including, but not limited to, squamous cell cancer, and verrucous; skin cancer, including, but not limited to, basal cell carcinoma, squamous cell carcinoma and melanoma, superficial spreading melanoma, nodular melanoma, lentigo malignant melanoma, and acral lentiginous melanoma; kidney cancer, including, but not limited to, renal cell cancer, adenocarcinoma, hypernephroma, fibrosarcoma, and transitional cell cancer (renal pelvis and/or uterer); Wilms' tumor; bladder cancer, including, but not limited to, transitional cell carcinoma, squamous cell cancer, adenocarcinoma, carcinosarcoma. In addition, cancer includes myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In some embodiments, the present disclosure provides a method for the treatment of liver injury. Without being limited to a specific mechanism, targeting neddylation provides a method for the treatment of liver fibrosis and liver injury. (See e.g., Zubiete-Franco et al. Hepatology 65 (2) 2017, 694-709). Thus, in some embodiments, the present disclosure provides a method for the treatment of hepatitis, Non-alcoholic fatty liver disease (NAFLD), alcoholic liver disease, cirrhosis, hemochromatosis, jaundice, autoimmune liver disorders, liver cancer, galactosemia, alpha-1 antitrypsin deficiency, Wilson disease, oxalosis, liver adenoma, Alagille syndrome, primary biliary cholangitis (PBC), and lysosomal acid lipase deficiency (LAL-D).

In some embodiments, the present disclosure provides a method for the treatment of heart disease. Without being limited to a specific mechanism, targeting neddylation, provides a method for the treatment of heart disease (See e.g., Kandala et al., Am. J. Cardiovasc. Dis 4, 2014, 140). Thus, in some embodiments, the present disclosure provides a method for the treatment of arrhythmia. heart failure, coronary artery disease, heart valve disease, congenital heart disease, angina, cardiomyopathy, pericarditis, peripheral artery disease, aortic aneurysm, aortic stenosis, deep vein thrombosis, M1arfan syndrome and rheumatic heart disease.

In some embodiments, the present disclosure provides a method for the treatment of neurodegenerative diseases (See e.g., Villa et al., Eur J. Neurol. 16 (7) 2009, 870. Thus, in some embodiments, the present disclosure provides a method for the treatment of amyotrophic lateral sclerosis, multiple sclerosis, Parkinson's disease, Alzheimer's disease, Huntington's disease, multiple system atrophy, tauopathies and prion diseases.

In some embodiments, the method optionally comprises co-administration of a second therapeutic agent. In some embodiments, the second therapeutic agent is hydroxyurea or a pharmaceutically acceptable salt thereof.

In one aspect, the present disclosure provides a method of treating a hemoglobinopathy disorder or disease, comprising administering to a subject in need thereof a compound disclosed herein, or a pharmaceutically acceptable salt thereof, in combination with a second agent such as hydroxyurea or a pharmaceutically acceptable salt thereof.

In some embodiments, the hemoglobinopathy is a sickle cell disorder or disease.

In some embodiments, the hemoglobinopathy is a thalassemia disorder or disease.

In some embodiments, the compound or pharmaceutically acceptable salt thereof and the hydroxyurea or a pharmaceutically acceptable salt thereof act synergistically.

In some embodiments, the compound or pharmaceutically acceptable salt thereof is selected from one of those shown in Table 1, or a pharmaceutically acceptable salt thereof. In some embodiments, the compound or pharmaceutically acceptable salt thereof is I-73 or a pharmaceutically acceptable salt thereof. In some embodiments, the compound or pharmaceutically acceptable salt thereof is I-13 or a pharmaceutically acceptable salt thereof. In some embodiments, the compound or pharmaceutically acceptable salt thereof is I-256 or a pharmaceutically acceptable salt thereof.

In some embodiments, the compound or pharmaceutically acceptable salt thereof is I-552 or a pharmaceutically acceptable salt thereof. In some embodiments, the compound or pharmaceutically acceptable salt thereof is I-363 or a pharmaceutically acceptable salt thereof.

In one aspect, the present disclosure provides a method of increasing efficacy and/or reducing toxicity of hydroxyurea treatment in a subject undergoing said treatment, comprising administering to the subject a compound disclosed herein, or a pharmaceutically acceptable salt thereof. In some embodiments, the hydroxyurea treatment is for a hemoglobinopathy. In some embodiments, the hydroxyurea treatment is for sickle cell disease. In some embodiments, the hydroxyurea treatment is for a thalassemia disorder.

In some embodiments, the method further comprises the step of decreasing an amount of hydroxyurea being administered to the subject.

In some embodiments, the amount of hydroxyurea being administered is decreased by 10-90%.

In one aspect, the present disclosure provides a method of decreasing the dose of hydroxyurea or a pharmaceutically acceptable salt thereof needed for effective treatment of a hemoglobinopathy disorder or disease, comprising administering to a subject in need thereof a compound disclosed herein, or a pharmaceutically acceptable salt thereof, in combination with hydroxyurea or a pharmaceutically acceptable salt thereof, wherein the dose of hydroxyurea or a pharmaceutically acceptable salt thereof needed for effective treatment of the hemoglobinopathy disorder or disease is less than the dose needed for treatment in the subject using hydroxyurea or a pharmaceutically acceptable salt thereof as a monotherapy.

In some embodiments, the dose of hydroxyurea or a pharmaceutically acceptable salt thereof co-administered with the compound or pharmaceutically acceptable salt thereof is reduced by at least 10%, at least 20%, at least 30%, at least 40%, at least 50%, at least 60%, at least 70%, at least 80%, or at least 90% relative to the dose needed for treatment in the subject using hydroxyurea or a pharmaceutically acceptable salt thereof as a monotherapy.

In some embodiments, the compound or pharmaceutically acceptable salt thereof is selected from one of those shown in Table 1, or a pharmaceutically acceptable salt thereof. In some embodiments, the compound or pharmaceutically acceptable salt thereof is I-73 or a pharmaceutically acceptable salt thereof. In some embodiments, the compound or pharmaceutically acceptable salt thereof is I-13 or a pharmaceutically acceptable salt thereof. In some embodiments, the compound or pharmaceutically acceptable salt thereof is I-256 or a pharmaceutically acceptable salt thereof.

In some embodiments, the compound or pharmaceutically acceptable salt thereof is I-552 or a pharmaceutically acceptable salt thereof. In some embodiments, the compound or pharmaceutically acceptable salt thereof is I-363 or a pharmaceutically acceptable salt thereof.

In some embodiments, the present disclosure provides a method to treat or prevent one or more complications of sickle cell disease including, for example, anemia, anemia crisis, splenomegaly, pain crisis, chest syndrome, acute chest syndrome, blood transfusion requirement, organ damage, pain medicine (management) requirement, splenic sequestration crises, hyperhemolytic crisis, vaso-occlusion, vaso-occlusion crisis, acute myocardial infarction, sickle-cell chronic lung disease, thromboemboli, hepatic failure, hepatomegaly, hepatic sequestration, iron overload and complications of iron overload (e.g., congestive heart failure, cardiac arrhythmia, myocardial infarction, other forms of cardiac disease, diabetes mellitus, dyspnea, hepatic disease and adverse effects of iron chelation therapy), splenic infarction, acute and/or chronic D renal failure, pyelonephritis, aneurysm, ischemic stroke, intraparenchymal hemorrhage, subarachnoid hemorrhage, intraventricular hemorrhage, peripheral retinal ischemia, proliferative sickle retinopathy, vitreous hemorrhage, and/or priapism; comprising administering to a subject in need thereof a disclosed compound or pharmaceutically acceptable salt thereof, optionally in combination with a second therapeutic agent such as hydroxyurea or a pharmaceutically acceptable salt thereof.

In some embodiments, the compound or pharmaceutically acceptable salt thereof acts synergistically in combination with the second therapeutic agent, e.g., hydroxyurea or a pharmaceutically acceptable salt thereof.

4. Combination Therapies

In one aspect, the compounds of the present disclosure are used advantageously in combination with a second therapeutic agent. Such a second therapeutic agent includes, in some embodiments, hydroxyurea or a pharmaceutically acceptable salt thereof.

In some embodiments, the disclosure provides methods for using a compound or combination therapy (for example, a disclosed compound or pharmaceutically acceptable salt thereof in combination with hydroxyurea or a pharmaceutically acceptable salt thereof) to treat or prevent vascular occlusion (vaso-occlusion) in a sickle-cell disease patient in need thereof as well as various complications associated with vaso-occlusion in a sickle-cell disease patient (e.g., vaso-occlusion crisis, pain crisis, etc.). In some embodiments, the disclosure provides methods for using a disclosed compound or combination therapy to treat or prevent anemia in a sickle-cell disease patient in need thereof as well as various complications associated with anemia in a sickle-cell disease patient (e.g., aplastic crisis, hyperhemolytic crisis, etc.). In such methods, a disclosed compound or combination therapy can be used to increase red blood cell levels while reducing the need for red blood cell transfusions and/or iron chelation therapy, and thereby reduce morbidity and mortality associated with iron accumulation in vulnerable tissues/organs. In such methods, a disclosed compound or combination therapy can also be used to reduce the need for other supportive therapies for treating sickle-cell disease [e.g., treatment with hydroxyurea, treatment with an EPO or other EPO agonist, and/or pain management (e.g., treatment with one or more of opioid analgesic agents, non-steroidal anti-inflammatory drugs, and/or corticosteroids)]. In part, a disclosed compound or combination therapy can be used in combination with existing supportive therapies for sickle-cell disease including, for example, transfusion of red blood cells, iron chelation therapy, hydroxyurea therapy, EPO or EPO agonist therapy, and/or pain management therapy. Optionally, a disclosed compound or combination therapy can be used to reduce the amount, duration, etc. of an existing supportive therapy for sickle-cell disease. For example, while transfusion of red blood cells and iron chelation therapy may help treat certain complications of sickle-cell disease, they sometimes result in adverse side effects. Therefore, in certain aspects, a disclosed compound or combination therapy can be used to reduce the amount of a second supportive therapy, e.g., reduce blood cell transfusion burden or reduce the dosage of a chelation therapeutic. In certain aspects, the disclosure provides uses of a disclosed compound or combination therapy (optionally in combination with one or more supportive therapies for sickle-cell disease) for making a medicament for the treatment or prevention of sickle-cell disease, particularly one or more complications of sickle-cell disease as disclosed herein.

5. Compositions

The present disclosure also provides compositions that comprise or deliver a compound as provided herein. In some embodiments, the present disclosure provides compositions comprising a compound provided herein with one or more other components.

In some embodiments, provided compositions comprise and/or deliver a compound described herein. In some embodiments, a provided composition is a pharmaceutical composition that comprises and/or delivers a compound provided herein and further comprises a pharmaceutically acceptable carrier.

Pharmaceutical compositions typically contain an active agent (e.g., a compound described herein) in an amount effective to achieve a desired therapeutic effect while avoiding or minimizing adverse side effects. In some embodiments, provided pharmaceutical compositions comprise a compound described herein and one or more carriers or excipients (e.g., fillers, disintegrants, lubricants, glidants, anti-adherents, and/or anti-statics, etc.) Provided pharmaceutical compositions can be in a variety of forms including oral dosage forms, topical creams, topical patches, iontophoresis forms, suppository, nasal spray and/or inhaler, eye drops, intraocular injection forms, depot forms, as well as injectable and infusible solutions.

Provided pharmaceutical compositions can be prepared with any appropriate available technologies.

In some embodiments, provided compounds are formulated in a unit dosage form for ease of administration and uniformity of dosage. The expression "unit dosage form" as used herein refers to a physically discrete unit of an active agent (e.g., a compound described herein) for administration to a subject. Typically, each such unit contains a predetermined quantity of active agent. In some embodiments, a unit dosage form contains an entire single dose of the agent. In some embodiments, more than one unit dosage form is administered to achieve a total single dose. In some embodiments, administration of multiple unit dosage forms is required, or expected to be required, in order to achieve an intended effect. A unit dosage form may be, for example, a liquid pharmaceutical composition containing a predetermined quantity of one or more active agents, a solid pharmaceutical composition (e.g., a tablet, a capsule, or the like) containing a predetermined amount of one or more active agents, a sustained release formulation containing a predetermined quantity of one or more active agents, or a drug delivery device containing a predetermined amount of one or more active agents, etc.

Provided compositions may be administered in accordance with a dosing regimen (i.e., that includes a single dose or multiple doses separated from one another in time, administered via a particular route of administration) that is (e.g., has been demonstrated to be) effective for treating (e.g., delaying onset of and/or decreasing incidence and/or intensity of) a disease or disorder, for example as described herein.

The present disclosure also provides methods of preparing pharmaceutical compositions provided herein. In some embodiments, provided methods comprise (i) providing a provided compound or a pharmaceutically acceptable salt thereof; and (ii) formulating the compound with suitable excipients to give a pharmaceutical composition.

6. General Methods of Providing the Present Compounds

The compounds of this invention may be prepared or isolated in general by synthetic and/or semi-synthetic methods known to those skilled in the art for analogous compounds and by methods described in detail in the Examples and Figures, herein.

In the schemes and chemical reactions depicted in the detailed description, Examples, and Figures, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, $7^{th}$ Edition, John Wiley & Sons, 2013, *Comprehensive Organic Transformations*, R. C. Larock, $3^{rd}$ Edition, John Wiley & Sons, 2018, and *Protective Groups in Organic Synthesis*, P. G. M. Wuts, $5^{th}$ edition, John Wiley & Sons, 2014, the entirety of each of which is hereby incorporated herein by reference.

As used herein, the phrase "leaving group" (LG) includes, but is not limited to, halogens (e.g., fluoride, chloride, bromide, iodide), sulfonates (e.g., mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protective Groups in Organic Synthesis*, P. G. M. Wuts, $5^{th}$ edition, John Wiley & Sons, 2014, and Philip Kocienski, in *Protecting Groups*, Georg Thieme Verlag Stuttgart, New York, 1994, the entireties of which are incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include 235yridin, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy) methyl, benzyloxymethyl, beta-(trimethylsilyl) ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protective Groups in Organic Synthesis*, P. G. M. Wuts, $5^{th}$ edition, John Wiley & Sons, 2014, and Philip Kocienski, in Protecting Groups, Georg Thieme Verlag Stuttgart, New York, 1994, the entireties of which are incorporated herein by reference. Suitable amino protecting groups include, but are not limited to, aralkylamines, carbamates, cyclic imides, allyl amines, amides, and the like. Examples of such groups include t-butyloxycarbonyl (Boc), ethyloxycarbonyl, methyloxycarbonyl, trichloroethyloxycarbonyl, allyloxycarbonyl (Alloc), benzyloxocarbonyl (Cbz), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

One of skill in the art will appreciate that various functional groups present in compounds of the invention such as aliphatic groups, alcohols, carboxylic acids, esters, amides, aldehydes, halogens, and nitriles can be interconverted by techniques well known in the art including, but not limited to reduction, oxidation, esterification, hydrolysis, partial oxidation, partial reduction, halogenation, dehydration, partial hydration, and hydration. See, for example, *March's Advanced Organic Chemistry: Reactions, Mechanisms, and Structure*, M. B. Smith, and J. March, $7^{th}$ Edition, John Wiley & Sons, 2013, *Comprehensive Organic Transformations*, R. C. Larock, $3^{rd}$ Edition, John Wiley & Sons, 2018, the entirety of each of which is incorporated herein by reference. Such interconversions may require one or more of the aforementioned techniques, and certain methods for synthesizing compounds of the invention are described below.

One of skill in the art will appreciate that various functional groups present in compounds of the invention such as aliphatic groups, alcohols, carboxylic acids, esters, amides, aldehydes, halogens, and nitriles can be interconverted by techniques well known in the art including, but not limited to reduction, oxidation, esterification, hydrolysis, partial oxidation, partial reduction, halogenation, dehydration, partial hydration, and hydration. Such groups and transformations are described in detail in *March's Advanced Organic Chemistry*: Reactions, Mechanisms, and Structure, M. B. Smith and J. March, $7^{th}$ Edition, John Wiley & Sons, 2013, *Comprehensive Organic Transformations*, R. C. Larock, $3^{rd}$ Edition, John Wiley & Sons, 2018, and *Protective Groups in Organic Synthesis*, P. G. M. Wuts, $5^{th}$ edition, John Wiley & Sons, 2014, the entirety of each of which is hereby incorporated herein by reference. Such interconversions may require one or more of the aforementioned techniques, and certain methods for synthesizing compounds of the invention are described below in the Exemplification and Figures.

7. Enumerated Embodiments

The disclosure herein is further presented as a non-limiting list of numbered embodiments.

1. A compound of Formula Ia:

Ia

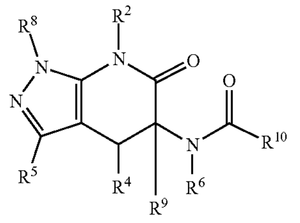

or a pharmaceutically acceptable salt thereof, wherein:

$R^8$ is phenyl, a 3-8 membered saturated or partially unsaturated monocyclic carbocyclic ring, a 4-10 membered saturated or partially unsaturated bicyclic carbocyclic ring, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, an 8-10 membered bicyclic heteroaromatic ring having 1-5 heteroatoms independently selected from nitrogen, oxygen, and sulfur, or a $C_{1-6}$ aliphatic; wherein $R^8$ is optionally substituted with m instances of $R^1$;

$R^{10}$ is phenyl, a 3-8 membered saturated or partially unsaturated monocyclic carbocyclic ring, a 4-10 membered saturated or partially unsaturated bicyclic carbocyclic ring, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, an 8-10 membered bicyclic heteroaromatic ring having 1-5 heteroatoms independently selected from nitrogen, oxygen, and sulfur, or a $C_{1-6}$ aliphatic; wherein $R^{10}$ is optionally substituted with n instances of $R^3$;

each occurrence of $R^1$ is independently optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, or —NRS(O)$_2$R;

$R^2$ is hydrogen, an optionally substituted group selected from $C_{1-6}$ aliphatic or a 3-8 membered saturated or partially unsaturated monocyclic carbocyclic ring;

each occurrence of $R^3$ is independently an optionally substituted $C_{1-6}$ aliphatic, an optionally substituted 3-8 membered saturated or partially unsaturated monocyclic carbocyclic ring, an optionally substituted 4-10 membered saturated or partially unsaturated bicyclic carbocyclic ring, an optionally substituted 3-8 membered saturated or partially unsaturated monocyclic heterocyclic ring having 1-2 heteroatoms independently selected from nitrogen, oxygen, and sulfur, an optionally substituted 5-10 membered bicyclic heterocyclic ring having 1-4 heteroatoms independently selected from nitrogen, oxygen, and sulfur, an optionally substituted 5-6 membered monocyclic heteroaromatic ring having 1-4 heteroatoms independently selected from nitrogen, oxygen, and sulfur, an optionally substituted 8-10 membered bicyclic heteroaromatic ring having 1-5 heteroatoms independently selected from nitrogen, oxygen, and sulfur, optionally substituted phenyl, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, or —NRS(O)$_2$R;

$R^4$ is phenyl, a 3-8 membered saturated or partially unsaturated monocyclic carbocyclic ring, a 4-10 membered bicyclic carbocyclic ring, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur, or a $C_{1-6}$ aliphatic; wherein $R^4$ is optionally substituted with p instances of $R^7$;

$R^5$ is a substituent comprising a warhead group;

$R^6$ is hydrogen or an optionally substituted $C_{1-6}$ aliphatic group;

each occurrence of $R^7$ is independently optionally substituted $C_{1-6}$ aliphatic, halogen, —CN, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —NO$_2$, —SR, —S(O)R, —S(O)$_2$R, —S(O)$_2$N(R)$_2$, —NRS(O)$_2$R, optionally substituted phenyl, or an optionally substituted 5-6 membered heteroaromatic ring having 1-3 heteroatoms selected from nitrogen, sulfur, and oxygen;

$R^9$ is hydrogen or an optionally substituted $C_{1-6}$ aliphatic group;

each occurrence of R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur;

m is 0, 1, 2, 3, 4, or 5;

n is 0, 1, 2, 3, 4, or 5; and p is 0, 1, 2, 3, 4, or 5.

2. A compound of Formula Ib:

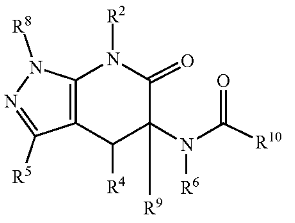

Ib or a pharmaceutically acceptable salt thereof, wherein:

each of $R^1$, $R^2$, $R^3$, $R^4$, $R^6$, $R^7$, $R^8$, $R^9$, $R^{10}$, R, m, n and p are as defined in claim 1, both singly and in combination; and $R^5$ is $L^2$-Y, wherein;

$L^2$ is a bivalent optionally substituted $C_{2-4}$ straight or branched hydrocarbon chain wherein one methylene unit of $L^2$ is optionally replaced by —NR—, or —C(O); and additionally one methylene unit of $L^2$ is optionally replaced by an optionally substituted ring selected from a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur; and Y is —CN.

3. A compound of Formula I:

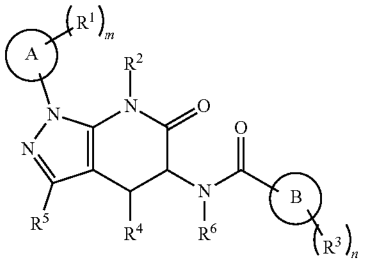

I or a pharmaceutically acceptable salt thereof, wherein:

Ring A is phenyl, 3-8 membered saturated or partially unsaturated monocyclic carbocyclic ring, or a 5-6 membered monocyclic heteroaromatic ring having 1-4 heteroatoms independently selected from nitrogen, oxygen, and sulfur;

Ring B is phenyl or a 5-6 membered monocyclic heteroaromatic ring having 1-4 heteroatoms independently selected from nitrogen, oxygen, and sulfur;

each occurrence of $R^1$ is independently optionally substituted $C_{1-6}$ aliphatic, halogen, —CN, —NC, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, or —NRS(O)$_2$R;

$R^2$ is an optionally substituted group selected from $C_{1-6}$ aliphatic or a 3-8 membered saturated or partially unsaturated monocyclic carbocyclic ring;

each occurrence of $R^3$ is independently an optionally substituted $C_{1-6}$ aliphatic, halogen, —CN, —NC, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, or —NRS(O)$_2$R;

$R^4$ is phenyl, a 3-8 membered saturated or partially unsaturated monocyclic carbocyclic ring, or a substituted $C_{1-6}$ aliphatic; wherein $R^4$ is optionally substituted with p instances of $R^7$;

$R^5$ is a substituent comprising a warhead group;

$R^6$ is hydrogen or an optionally substituted $C_{1-6}$ aliphatic group;

each occurrence of $R^7$ is independently optionally substituted $C_{1-6}$ aliphatic, halogen, —CN, —NC, —C(O)R, —C(O)OR, —OC(O)R, —C(O)N(R)$_2$, —N(R)C(O)R, —N(R)C(O)N(R)$_2$, —OC(O)N(R)$_2$, —N(R)C(O)OR, —OR, —N(R)$_2$, —$NO_2$, —SR, —S(O)R, —S(O)$_2$R, —S(O)$_2$N(R)$_2$, —NRS(O)$_2$R, phenyl, or a 5-6 membered heteroaromatic ring having 1-3 heteroatoms selected from nitrogen, sulfur, and oxygen;

each occurrence of R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur;

m is 0, 1, 2, 3, 4, or 5;

n is 0, 1, 2, 3, 4, or 5; and p is 0, 1, 2, 3, 4, or 5.

4. The compound of enumerated embodiment 1 or 2, wherein $R^5$ is $L^2$-Y, wherein $L^2$ is a covalent bond or a bivalent optionally substituted $C_{2-10}$ straight or branched hydrocarbon chain wherein one, two or three methylene units of $L^2$ are optionally and independently replaced by —NRC(O)—, —C(O)NR—, —N(R)$SO_2$—, —$SO_2$N(R)—, —S—, —O—, —NR—, —S(O)—, —$SO_2$—, —C(O)—, —OC(O)—, or —C(O)O—; $C_{2-10}$ straight or branched, hydrocarbon chain is optionally substituted with 1, 2, 3, or 4 independently selected halogen atoms and optionally substituted with one —CN or —OR group; and additionally one methylene unit of $L^2$ is optionally replaced by an optionally substituted ring selected from a 3-8 membered saturated or partially unsaturated monocyclic carbocyclic ring, a 4-10 membered bicyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur; and Y is hydrogen, halogen, —COOR, —CN, —CON(R)$_2$, —CONRCN, —NRCN, $NO_2$, —N(R)$_2$, optionally substituted $C_{1-8}$ aliphatic, or an optionally substituted ring selected from a 3-8 membered saturated or partially unsaturated monocyclic carbocyclic ring, a 4-10 membered bicyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, and an 8-10 membered bicyclic heteroaromatic ring having 1-5 heteroatoms independently selected from nitrogen, oxygen, and sulfur; wherein -$L^2$-Y comprises an alpha, beta-unsaturated carbonyl moiety, amide, cyano group, halogen, carbonyl, alkynyl group, sulfonyl group, or epoxide.

5. The compound of any one of preceding enumerated embodiments, wherein $R^5$ is $L^2$-Y, wherein $L^2$ is a covalent bond or a bivalent optionally substituted $C_{2-10}$ straight or branched hydrocarbon chain wherein one, two or three methylene units of $L^2$ are optionally and independently replaced by —NRC(O)—, —C(O)NR—, —N(R)$SO_2$—, —$SO_2$N(R)—, —S—, —O—, —NR—, —S(O)—, —$SO_2$—, —C(O)—, —OC(O)—, or —C(O)O—; $C_{2-10}$ straight or branched hydrocarbon chain is optionally substituted with 1, 2, 3, or 4 independently selected halogen atoms and optionally substituted with one —CN or —OR group; and additionally one methylene unit of $L^2$ is optionally replaced by an optionally substituted ring selected from a 3-8 membered saturated or partially unsaturated monocyclic carbocyclic ring, or a 3-8 membered saturated or partially unsaturated monocyclic heterocyclic ring having 1-2 heteroatoms independently selected from nitrogen, oxygen, and sulfur; and Y is hydrogen, halogen, —$COOR^f$, —CN, —$CONR^f_2$, —CONRCN, —$NR^f$CN, $NO_2$, —$NR^f_2$, $C_{1-8}$ aliphatic optionally substituted with halogen, $NO_2$, or CN, or an optionally substituted ring selected from a 3-8 membered saturated or partially unsaturated monocyclic carbocyclic ring, phenyl, a 3-8 membered saturated or partially unsaturated monocyclic heterocyclic ring having 1-2 heteroatoms independently selected from nitrogen, oxygen, and sulfur, and a 5-10 membered bicyclic heterocyclic ring having 1-4 heteroatoms independently selected from nitrogen, oxygen, and sulfur; wherein -$L^2$-Y comprises an alpha, beta-unsaturated carbonyl moiety, amide, cyano group, halogen, carbonyl, alkynyl group, sulfonyl group, or epoxide; and wherein each occurrence of $R^f$ is independently H, or straight or branched $C_{1-6}$ alkyl, $C_{2-6}$ alkenyl, or $C_{2-6}$ alkynyl group optionally substituted with 1, 2 or 3 halogen atoms.

6. The compound of any one of preceding enumerated embodiments, wherein $R^5$ is $L^2$-Y, wherein $L^2$ is a covalent bond or a bivalent $C_{2-10}$ straight or branched hydrocarbon chain wherein one, two or three methylene units of $L^2$ are optionally and independently replaced by —NRC(O)—, —C(O)NR—, —N(R)$SO_2$—, —$SO_2$N(R)—, —S—, —O—, —NR—, —S(O)—, —$SO_2$—, —C(O)—, —OC(O)—, or —C(O)O—; $C_{2-10}$ straight or branched hydrocarbon chain is optionally substituted with 1, 2, 3, or 4 independently selected halogen atoms and optionally substituted with one —CN or —OR group; and additionally one methylene unit of $L^2$ is optionally replaced by a ring selected from

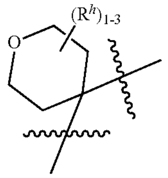
,
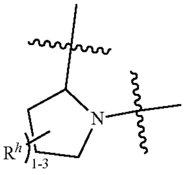
,
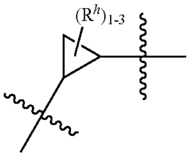
,
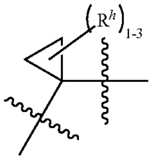
,
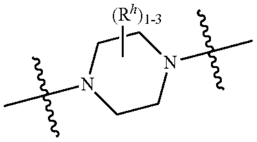
,
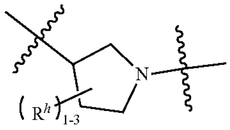
,
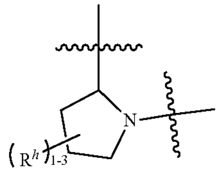
,
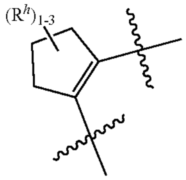
,
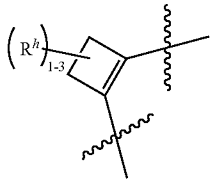
,
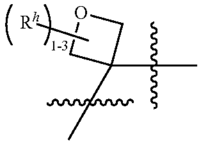
,
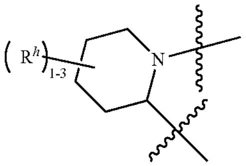
,
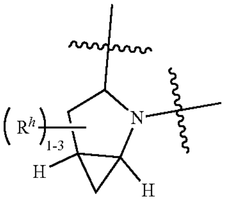
,
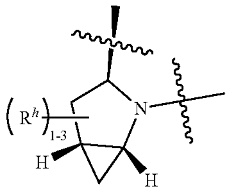
,
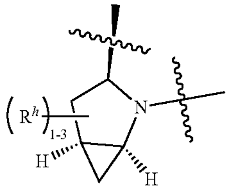
,
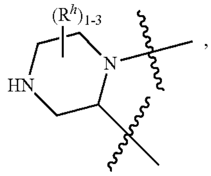
,
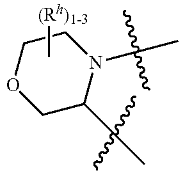
,
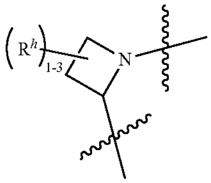
, -continued

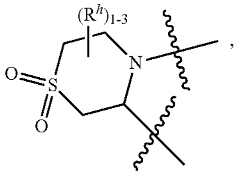,
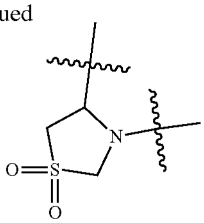,
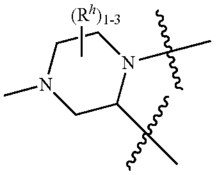,
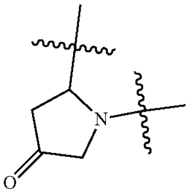,
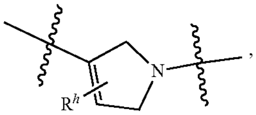, and
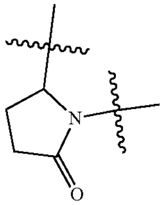;

and Y is hydrogen, halogen, —COOR$^f$, —CN, —CONR$^f_2$, —CONR$^f$CN, —NR$^f$CN, $NO_2$, —NR$^f_2$, epoxide, $C_{1-8}$ aliphatic optionally substituted with halogen, $NO_2$, or CN, or a ring selected from

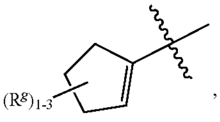,
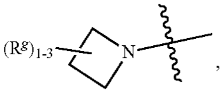,
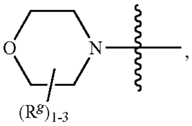,
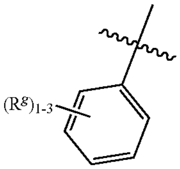,
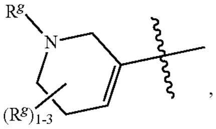,
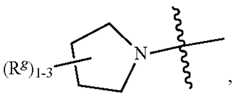,
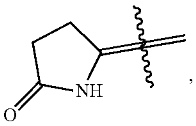,
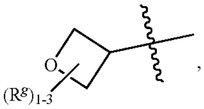,
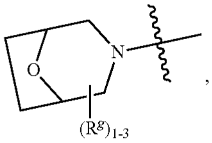,
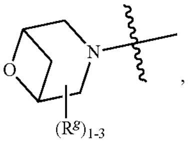,
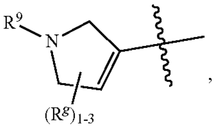,
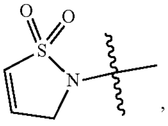,
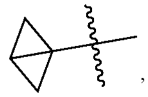, -continued

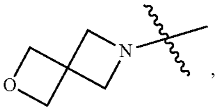,
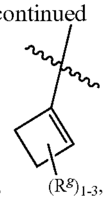,
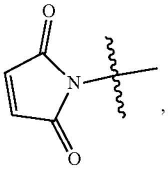,
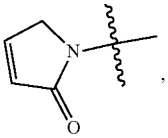,
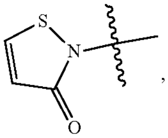,
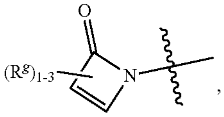,
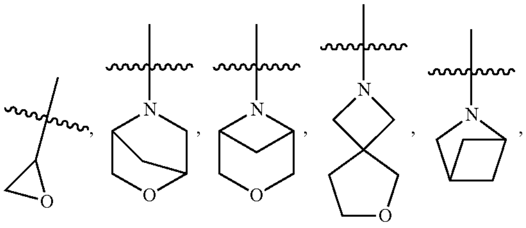,
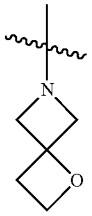,
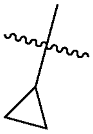,
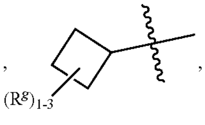,
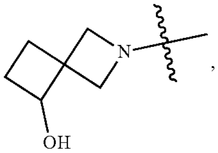,
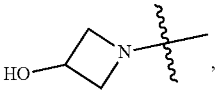,
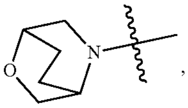,
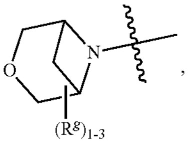,
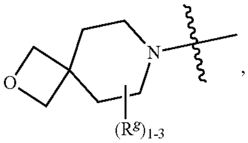,
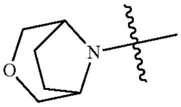,
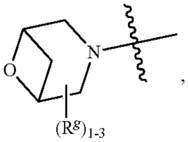,
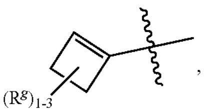,
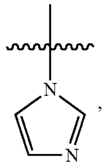,
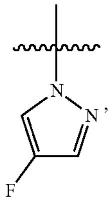, and
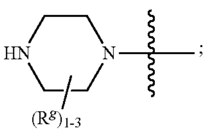;

wherein -L$^2$-Y comprises an alpha, beta-unsaturated carbonyl moiety, amide, cyano group, halogen, carbonyl, $C_{2-6}$ alkynyl group, sulfonyl group, or epoxide; wherein each occurrence of $R^f$ is independently H, or straight or branched $C_{1-6}$ alkyl, $C_{2-6}$ alkenyl, or $C_{2-6}$ alkynyl group optionally substituted with 1, 2 or 3 halogen atoms; and wherein each occurrence of $R^g$ and $R^h$ is independently H, halogen, or OH, or straight or branched $C_{1-6}$ alkyl, $C_{2-6}$ alkenyl, or $C_{2-6}$ alkynyl group optionally substituted with 1, 2 or 3 halogen atoms.

7. The compound of any one of preceding enumerated embodiments, wherein $R^5$ is $L^2$-Y, wherein $L^2$ is a covalent bond or a bivalent $C_{2-8}$ straight or branched, hydrocarbon chain wherein one or two methylene units of $L^2$ are optionally and independently replaced by —NRC(O)—, —C(O)NR—, —N(R)$SO_2$—, —$SO_2$N(R)—, —S—, —O—, —NR—, —S(O)—, —$SO_2$—, —C(O)—, —OC(O)—, or —C(O)O—; and additionally one methylene unit of $L^2$ is optionally replaced by an optionally substituted ring selected from a 3-8 membered saturated or partially unsaturated monocyclic carbocyclic ring, a 4-10 membered bicyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur; and Y is hydrogen, halogen, —COOR, —CN, —CON$(R)_2$, —NRCN, $NO_2$, —N$(R)_2$, optionally substituted $C_{1-8}$ aliphatic, or an optionally substituted ring selected from a 3-8 membered saturated or partially unsaturated monocyclic carbocyclic ring, a 4-10 membered bicyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-10 membered bicyclic heterocyclic ring having 1-4 heteroatoms independently selected from nitrogen, oxygen, and sulfur, a 5-6 membered monocyclic heteroaromatic ring having 1-4 heteroatoms independently selected from nitrogen, oxygen, and sulfur, and an 8-10 membered bicyclic heteroaromatic ring having 1-5 heteroatoms independently selected from nitrogen, oxygen, and sulfur; wherein -$L^2$-Y comprises an alpha, beta-unsaturated carbonyl moiety, amide, cyano group, halogen, carbonyl, alkynyl group, sulfonyl group, or epoxide.

8. The compound of any one of preceding enumerated embodiments, wherein $R^5$ is $L^2$-Y, wherein $L^2$ is a covalent bond or a bivalent $C_{2-8}$ straight or branched, hydrocarbon chain wherein one or two methylene units of $L^2$ are optionally and independently replaced by —NRC(O)—, —C(O)NR—, —N(R)$SO_2$—, —$SO_2$N(R)—, —S—, —O—, —NR—, —S(O)—, —$SO_2$—, —C(O)—, —OC(O)—, or —C(O)O—; and additionally one methylene unit of $L^2$ is optionally replaced by an optionally substituted ring selected from a 3-8 membered saturated or partially unsaturated monocyclic carbocyclic ring, or a 3-8 membered saturated or partially unsaturated monocyclic heterocyclic ring having 1-2 heteroatoms independently selected from nitrogen, oxygen, and sulfur; and Y is hydrogen, halogen, —COOR$^f$, —CN, —CONR$^f_2$, —NR$^f$CN, $NO_2$, —NR$^f_2$, $C_{1-8}$ aliphatic optionally substituted with halogen, $NO_2$, or CN, or an optionally substituted ring selected from a 3-8 membered saturated or partially unsaturated monocyclic carbocyclic ring, phenyl, a 3-8 membered saturated or partially unsaturated monocyclic heterocyclic ring having 1-2 heteroatoms independently selected from nitrogen, oxygen, and sulfur, and a 5-10 membered bicyclic heterocyclic ring having 1-4 heteroatoms independently selected from nitrogen, oxygen, and sulfur; wherein -$L^2$-Y comprises an alpha, beta-unsaturated carbonyl moiety, amide, cyano group, halogen, carbonyl, alkynyl group, sulfonyl group, or epoxide; and wherein each occurrence of $R^f$ is independently H, or straight or branched $C_{1-6}$ alkyl, $C_{2-6}$ alkenyl, or $C_{2-6}$ alkynyl group optionally substituted with 1, 2 or 3 halogen atoms.

9. The compound of any one of any one of preceding enumerated embodiments, wherein $R^5$ is $L^2$-Y, wherein:

$L^2$ is a covalent bond or a bivalent $C_{2-8}$ straight or branched, hydrocarbon chain wherein one or two methylene units of $L^2$ are optionally and independently replaced by —NRC(O)—, —C(O)NR—, —N(R)$SO_2$—, —$SO_2$N(R)—, —S—, —S(O)—, —$SO_2$—, —C(O)—, —OC(O)—, or —C(O)O—; and additionally one methylene unit of $L^2$ is optionally replaced by a ring selected from

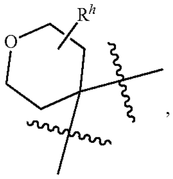,
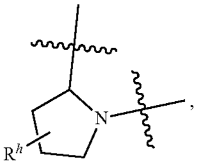,
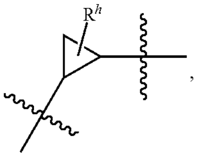,
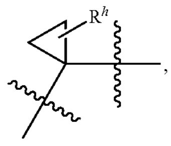,
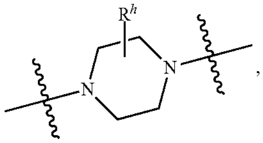,
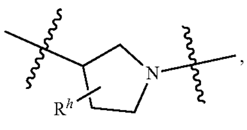,
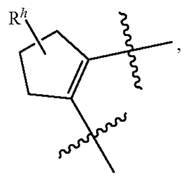,
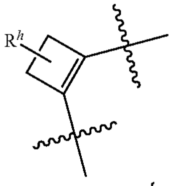,
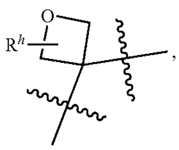, and
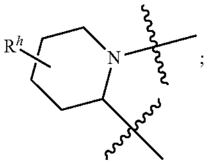;

and Y is hydrogen, halogen, —COOR$^f$, —CN, —CONR$^f_2$, —NR$^f$CN, $NO_2$, —NR$^f_2$, epoxide, $C_{1-8}$ aliphatic optionally substituted with halogen, $NO_2$, or CN, or a ring selected from

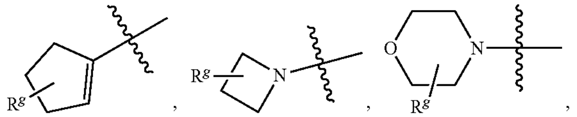
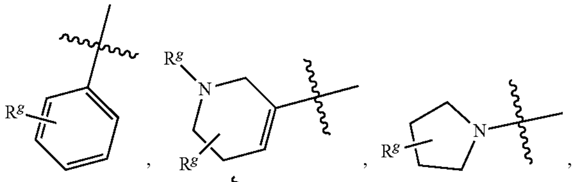
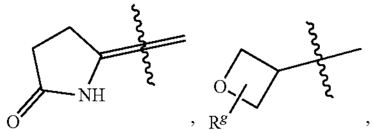
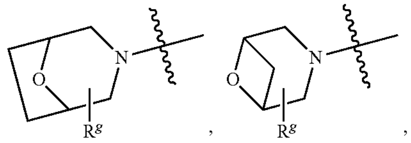
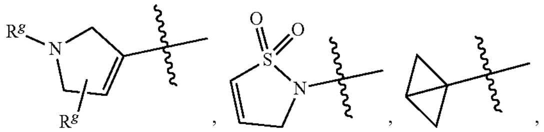
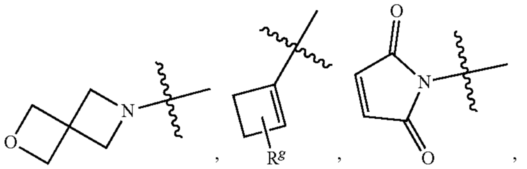
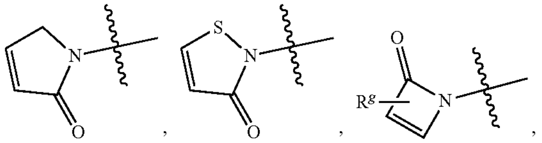
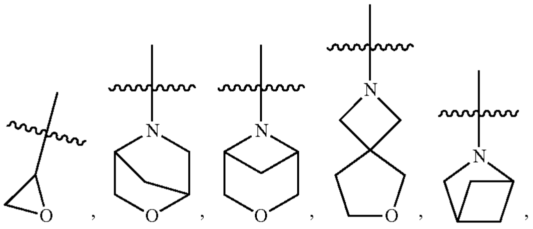
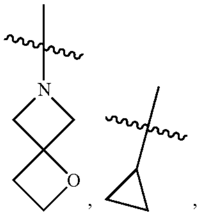

and; wherein $-L^2$-Y comprises an alpha, beta-unsaturated carbonyl moiety, amide, cyano group, halogen, carbonyl, $C_{2-6}$ alkynyl group, sulfonyl group, or epoxide; wherein each occurrence of $R^f$ is independently H, or straight or branched $C_{1-6}$ alkyl, $C_{2-6}$ alkenyl, or $C_{2-6}$ alkynyl group optionally substituted with 1, 2 or 3 halogen atoms; and wherein each occurrence of $R^g$ and $R^h$ is independently H, halogen, OH or straight or branched $C_{1-6}$ alkyl, $C_{2-6}$ alkenyl, or $C_{2-6}$ alkynyl group optionally substituted with 1, 2 or 3 halogen atoms.

10. The compound of any one of any one of preceding enumerated embodiments, wherein $R^5$ is selected from Table 1c, Table 1d or Table 1e.

11. The compound of any one of any one of preceding enumerated embodiments, wherein $R^5$ is selected from Table 1c, Table 1d, Table 1e or Table 1f.

12. The compound of any one of preceding enumerated embodiments, wherein Ring A is phenyl.

13. The compound of any one of preceding enumerated embodiments, wherein Ring B is phenyl.

14. The compound of any one of preceding enumerated embodiments, wherein $R^2$ is selected from ethyl,

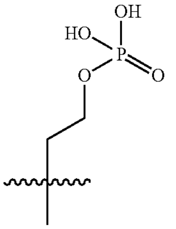
and
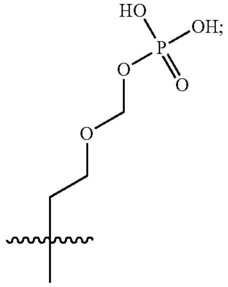

or a pharmaceutically acceptable salt thereof.

15. The compound of any one of preceding enumerated embodiments, wherein $R^2$ is H, methyl, ethyl,

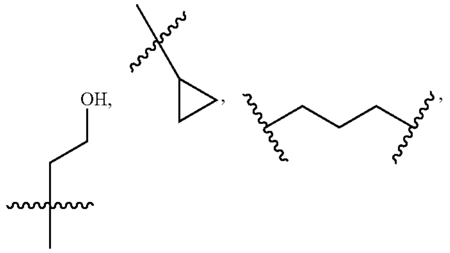
or
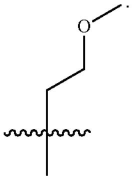

16. The compound of any one of preceding enumerated embodiments, wherein $R^3$ is —$CF_3$.

17. The compound of any one of preceding enumerated embodiments, wherein $R^3$ is methyl, ethyl, F, Cl, —CN, —$CF_3$,

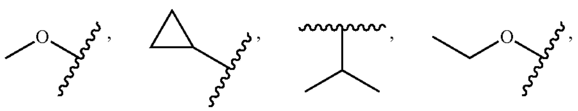
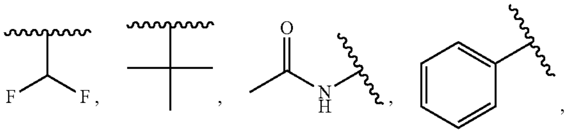

-continued

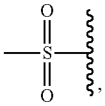,
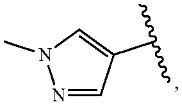,
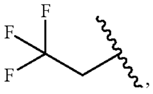,
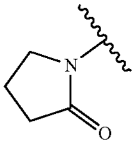,
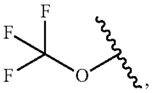,
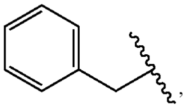,
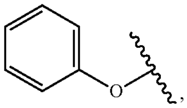,
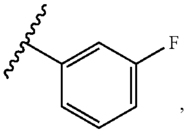,
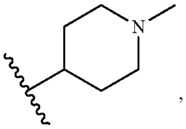,
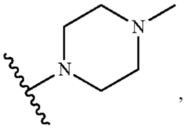,
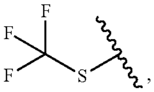,
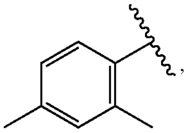,
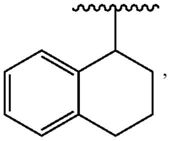,
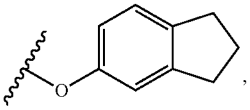,
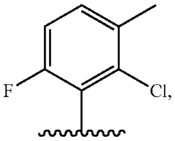,
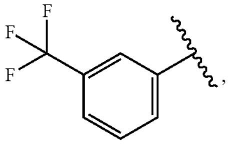,
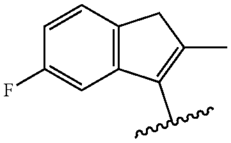,
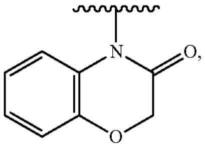,
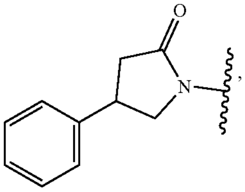,
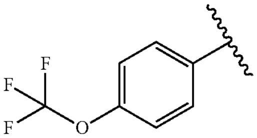,
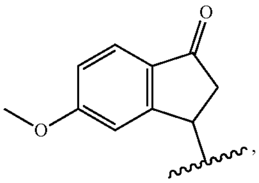, or
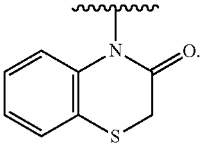.

18. The compound of any one of preceding enumerated embodiments, wherein $R^4$ is selected from

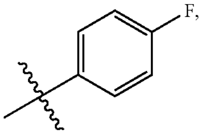 [SMILES: *c1ccc(F)cc1]

cyclopropyl and phenyl.

19. The compound of any one of preceding enumerated embodiments, wherein $R^4$ is from

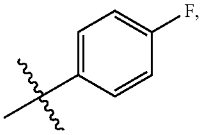 [SMILES: *c1ccc(F)cc1]

cyclopropyl, cyclopentyl, cyclobutyl, methyl, ethyl,

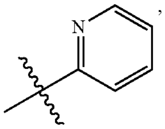,
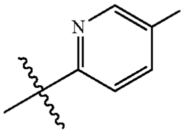, or
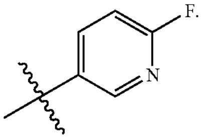.

20. The compound of any one of preceding enumerated embodiments, wherein $R^6$ is selected from hydrogen and

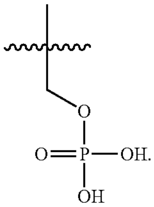 [SMILES: *COP(=O)(O)O].

21. The compound of any one of preceding enumerated embodiments, wherein $R^7$ is F.

22. The compound of any one of preceding enumerated embodiments, wherein $R^7$ is F, Cl or Br.

23. The compound of any one of preceding enumerated embodiments, wherein $R^8$ is phenyl,

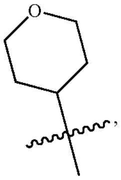,
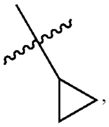,
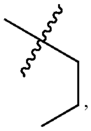,
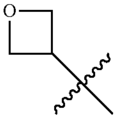,
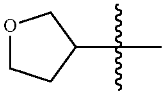, or t-Bu.

24. The compound of any one of preceding enumerated embodiments, wherein $R^9$ is hydrogen, methyl, and
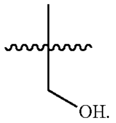 [SMILES: *CO]
25. The compound of any one of preceding enumerated embodiments, wherein $R^{10}$ is
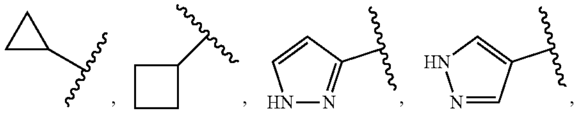
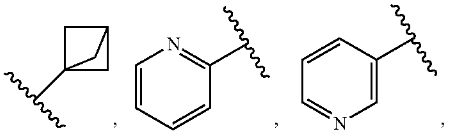
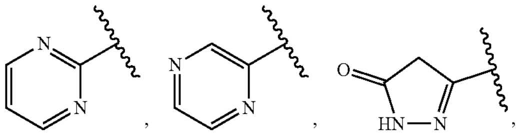
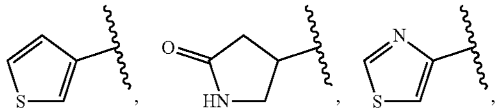
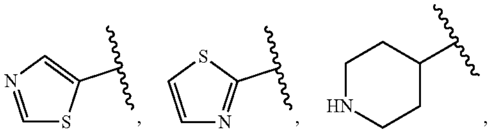
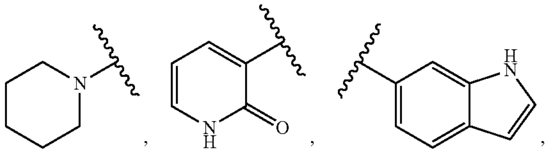
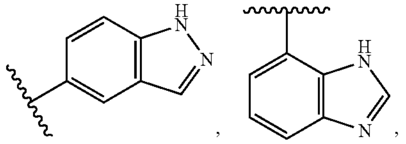
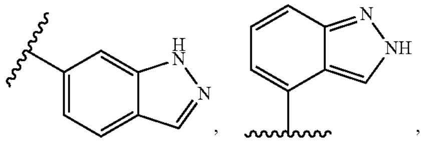
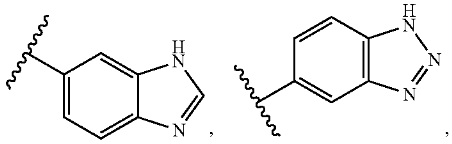
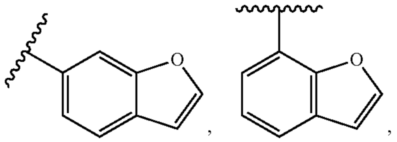
-continued
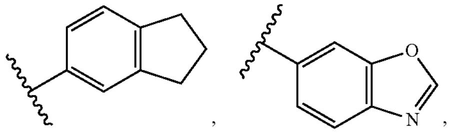
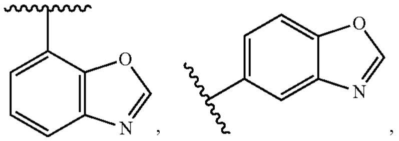
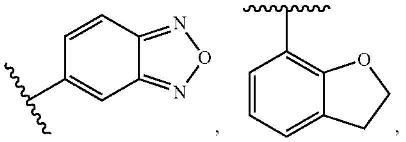
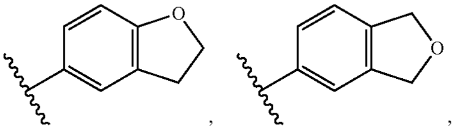
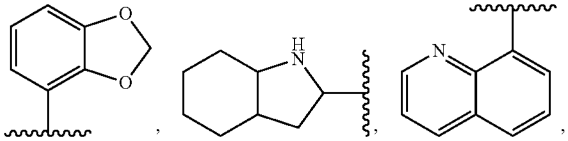
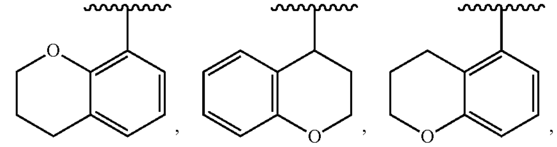
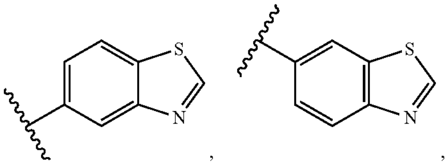
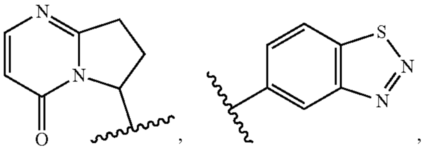
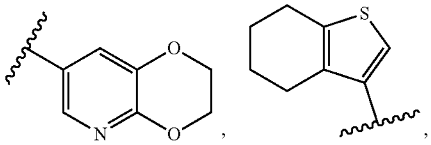
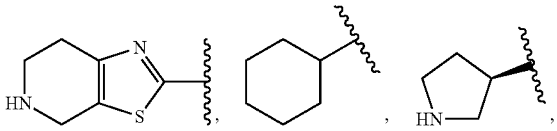
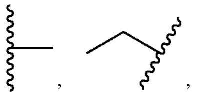
or
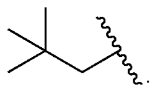

26. The compound of any one of preceding enumerated embodiments, wherein $R^1$ is

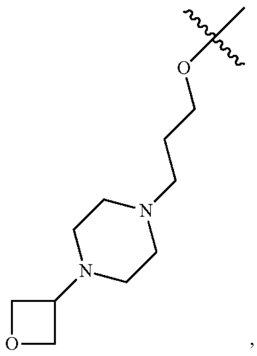
,
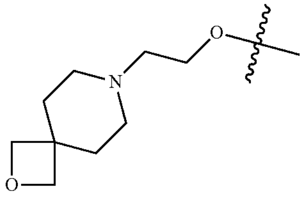
,
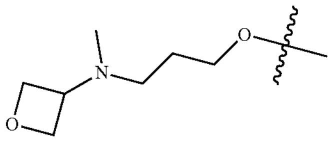
,
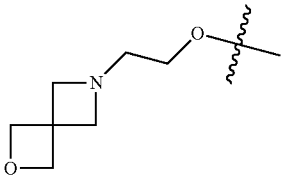
,
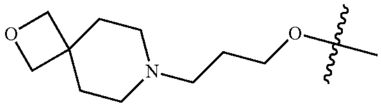
,
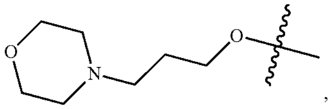
,
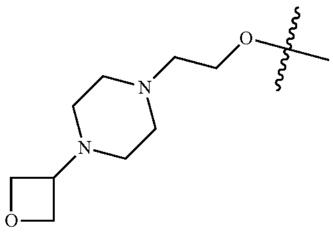
,
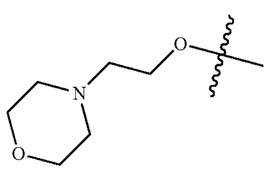
,
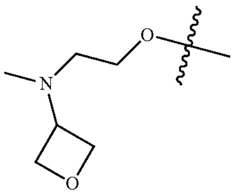
, or
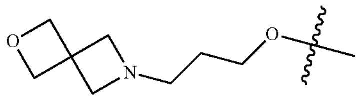
.

27. The compound of any one of preceding enumerated embodiments, wherein the compound is of Formula II:

II

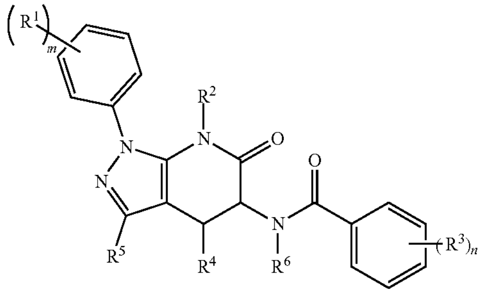

or a pharmaceutically acceptable salt thereof.

28. The compound of any one of preceding enumerated embodiments, wherein the compound is of Formula IIa, Formula IIb, Formula IIc or Formula IId:

IIa

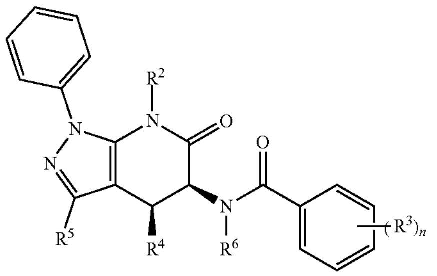

IIb

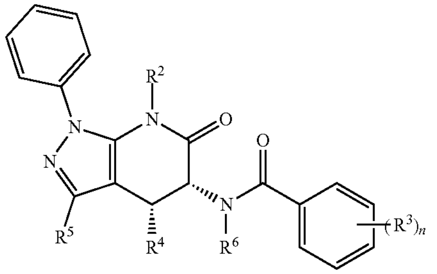

IIc

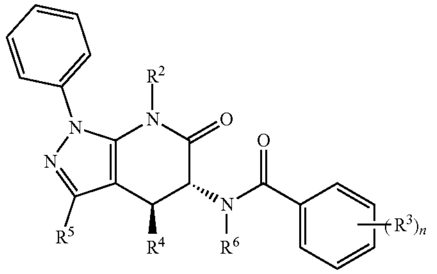

IId

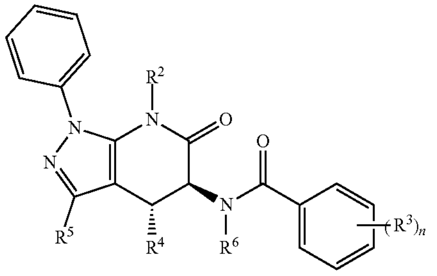

or a pharmaceutically acceptable salt thereof.

29. The compound of any one of preceding enumerated embodiments, wherein the compound is of Formula IIiia, Formula IIiib, Formula IIiic or Formula IIiid:

IIiia

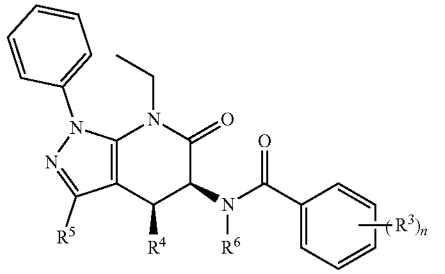

IIiib

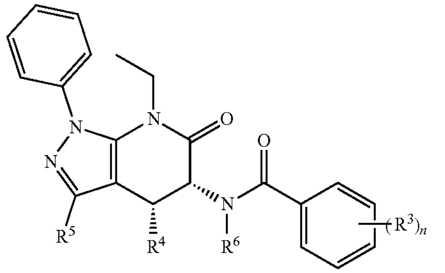

IIiic

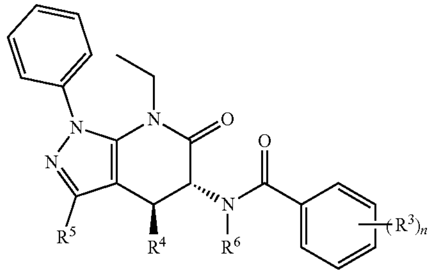

IIiid

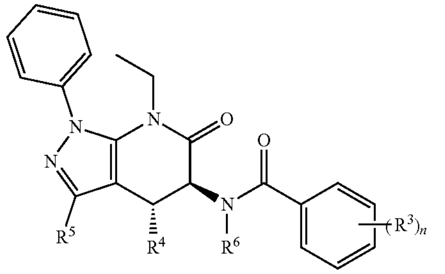

or a pharmaceutically acceptable salt thereof.

30. The compound of any one of preceding enumerated embodiments, wherein the compound is of Formula IIiia-i, Formula IIiib-i, Formula IIiic-i or Formula IIiid-i:

IIiia-i

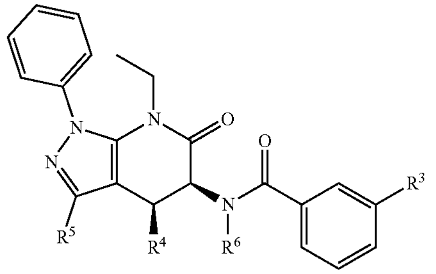

IIiib-i

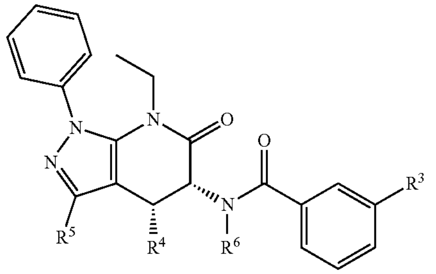

IIiic-i

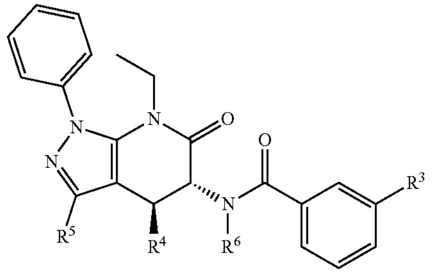

IIiid-i

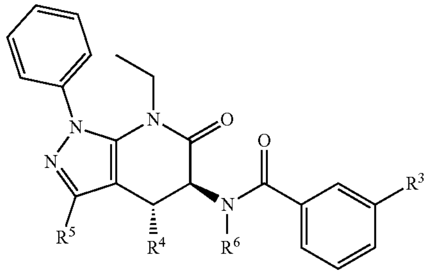

or a pharmaceutically acceptable salt thereof.

31. The compound of any one of preceding enumerated embodiments, wherein the compound is of Formula IIiiia, Formula IIiiib, Formula IIiiic or Formula IIiiid:

IIiiia

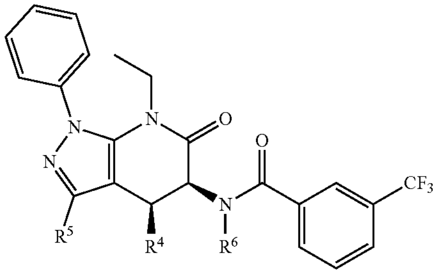

-continued

IIiiib

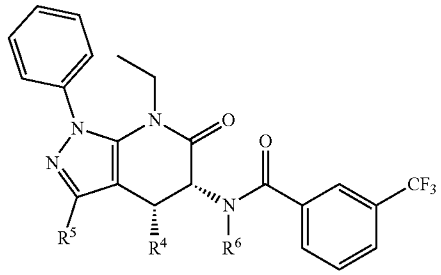

IIiiic

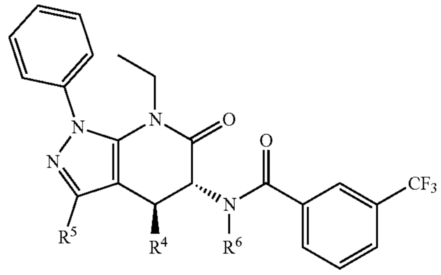

IIiiid

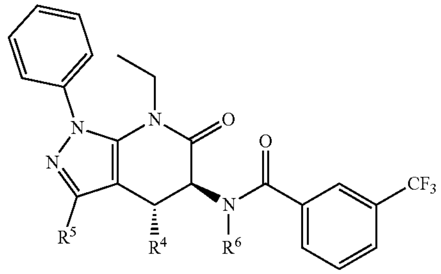

or a pharmaceutically acceptable salt thereof.

32. The compound of any one of preceding enumerated embodiments, wherein the compound is of Formula IIiva, Formula IIivb, Formula IIivc or Formula IIivd:

IIiva

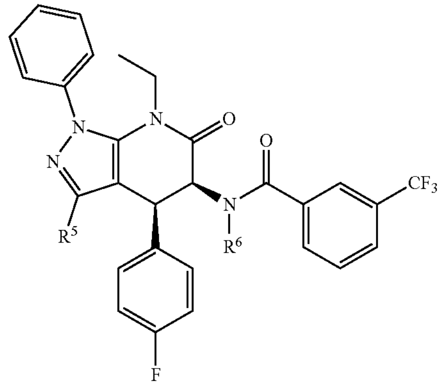

-continued

IIivb

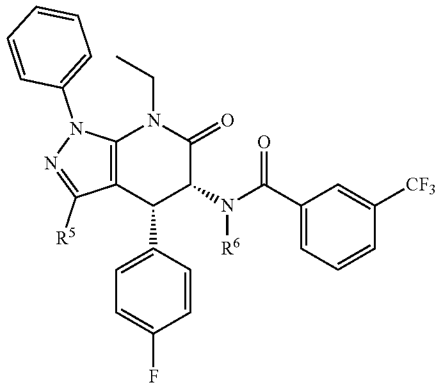

IIivc

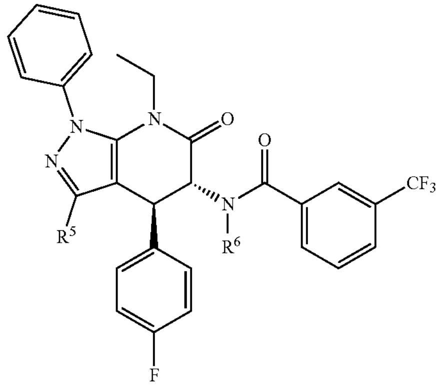

IIivd

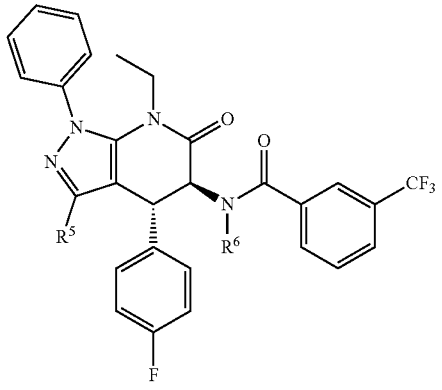

or a pharmaceutically acceptable salt thereof.

33. The compound of any one of preceding enumerated embodiments, wherein the compound is of Formula IIva, Formula IIvb, Formula IIvc or Formula IIvd:

IIva

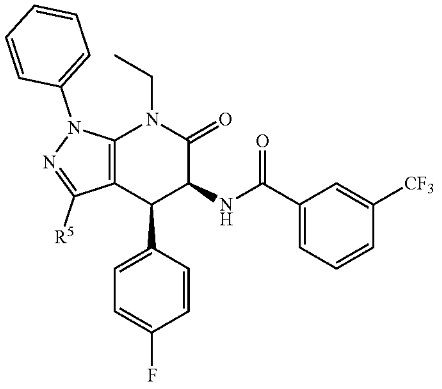

IIvb

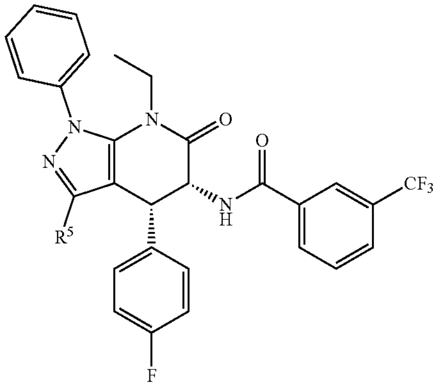

IIvc

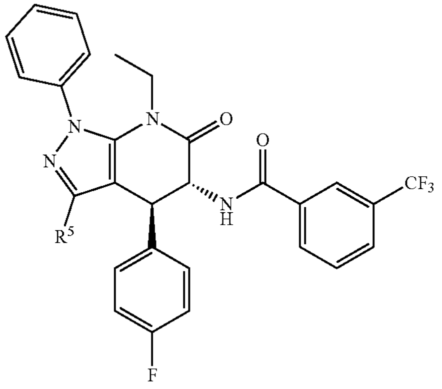

IIvd

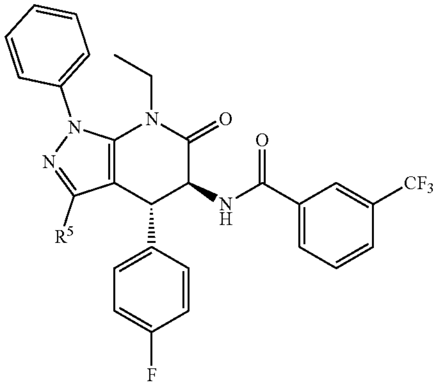

or a pharmaceutically acceptable salt thereof.

34. The compound of any one of preceding enumerated embodiments, wherein the compound is of Formula III:

III

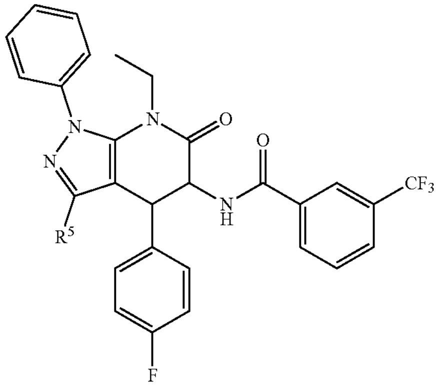

or a pharmaceutically acceptable salt thereof.

35. The compound of any one of preceding enumerated embodiments, wherein the compound is of Formula IIIia, Formula IIIib, Formula IIIic or Formula IIIid:

IIIia

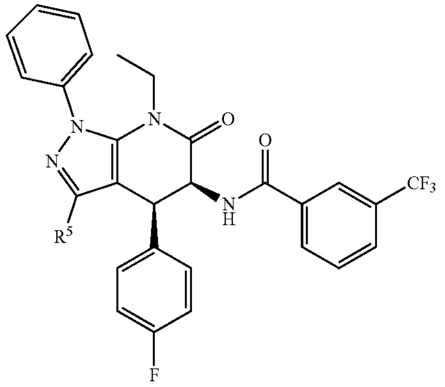

IIIib

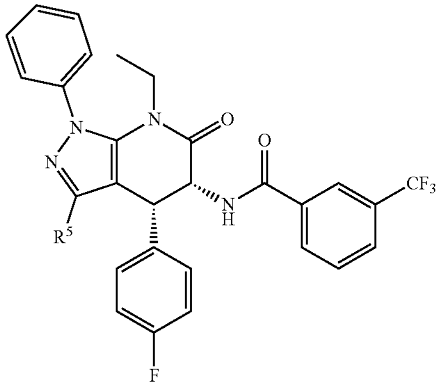

-continued

IIIc

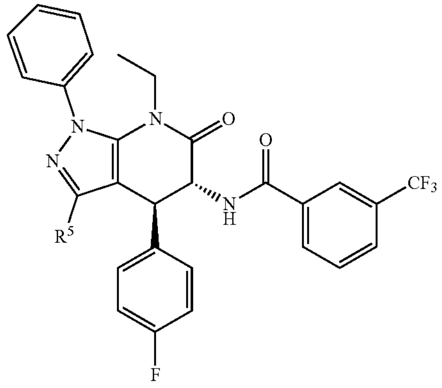

IIId

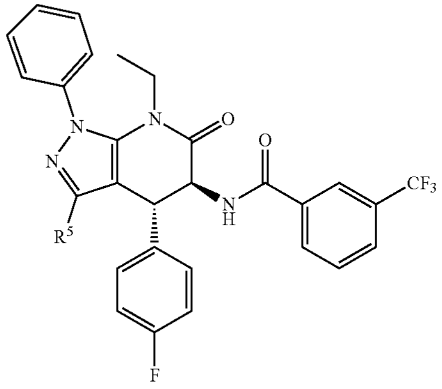

or a pharmaceutically acceptable salt thereof.

36. The compound of any one of preceding enumerated embodiments, wherein the compound is of Formula IV-a, IV-b or IV-c:

IV-a

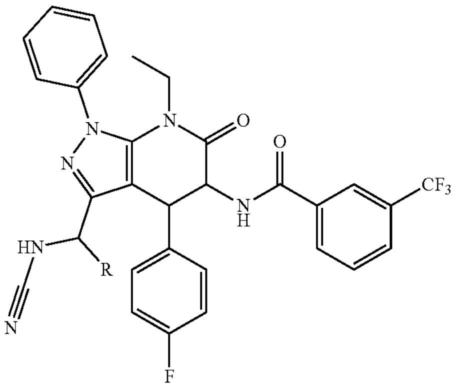

-continued

IV-b

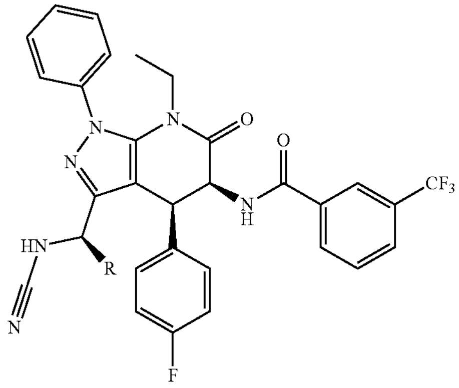

IV-c

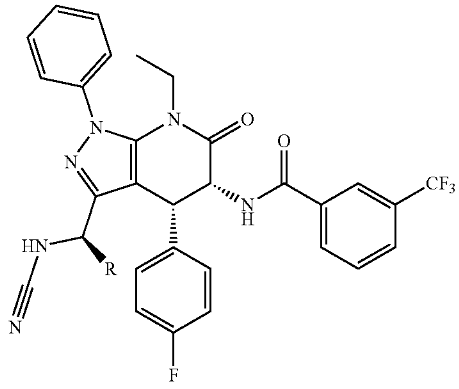

or a pharmaceutically acceptable salt thereof.

37. The compound of enumerated embodiment 35, wherein R is selected from methyl,

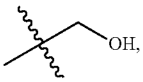 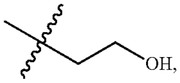 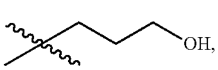

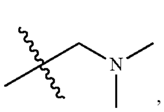 , 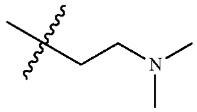 and

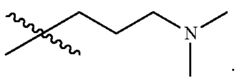 .

38. The compound of any one of preceding enumerated embodiments, wherein the compound is of Formula V-a, V-b or V-c:

V-a
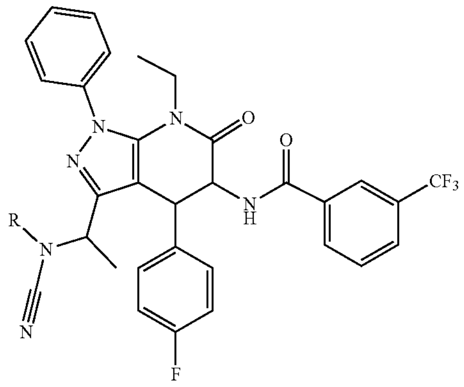
V-b
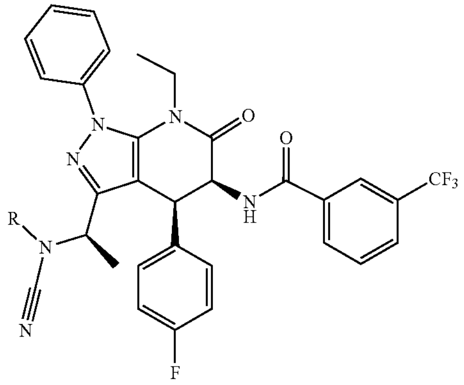
V-c
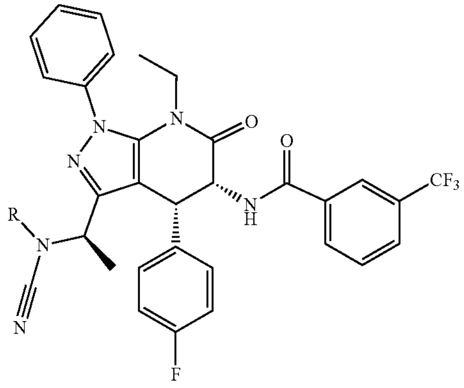
or a pharmaceutically acceptable salt thereof.
39. The compound of enumerated embodiment 37, wherein R is selected from methyl,
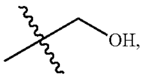,
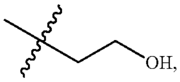,
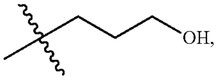,
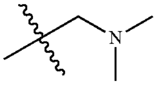,
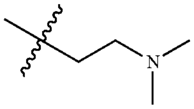,
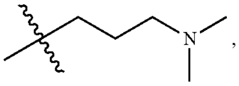,
-continued
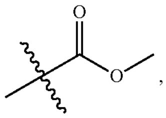,
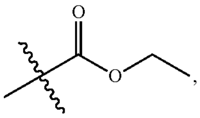,
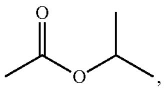,
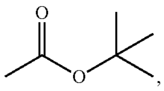, and
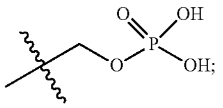;
or a pharmaceutically acceptable salt thereof.
40. The compound of any one of preceding enumerated embodiments, wherein the compound is of Formula VI-a, VI-b or VI-c:
VI-a
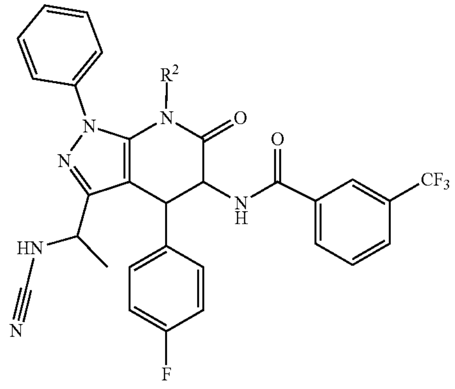
VI-b
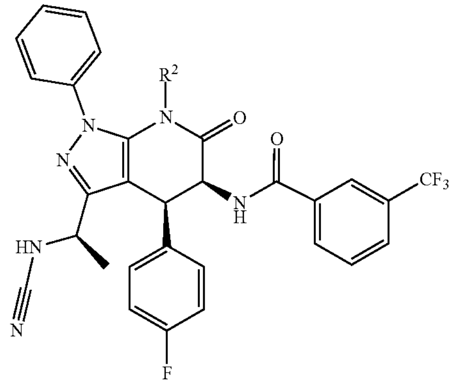

-continued

VI-c

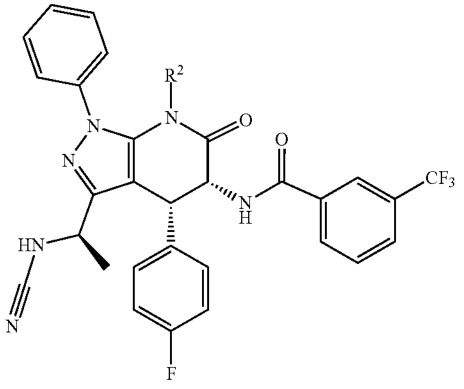

or a pharmaceutically acceptable salt thereof.

41. The compound of enumerated embodiment 39, wherein $R^2$ is selected from ethyl,

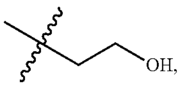

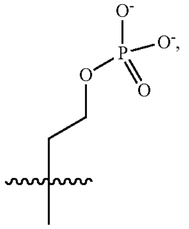

and

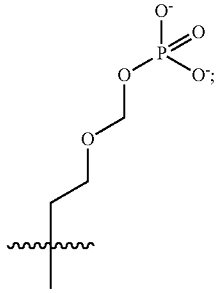

or a pharmaceutically acceptable salt thereof.

42. The compound of any one of preceding enumerated embodiments, wherein the compound is of Formula VIIa, Formula VIIb, Formula VIIc or Formula VIId:

VIIa

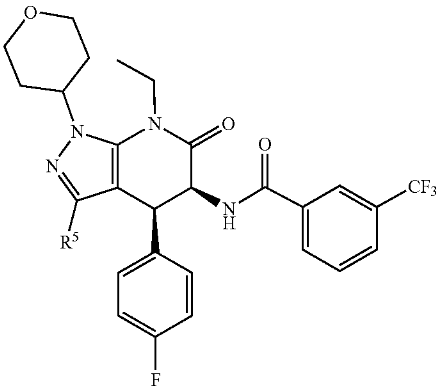

-continued

VIIb

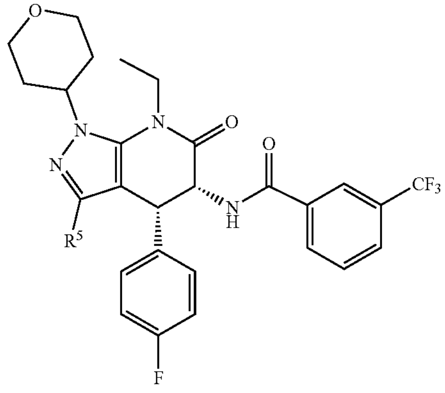

VIIc

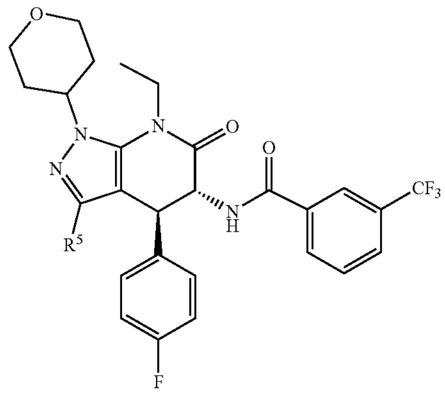

VIId

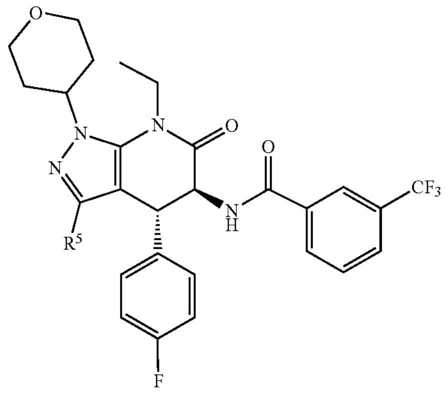

or a pharmaceutically acceptable salt thereof.

43. The compound of any one of preceding enumerated embodiments, wherein the compound is of Formula VIIIa, Formula VIIIb, Formula VIIIc or Formula VIIId:

VIIIa

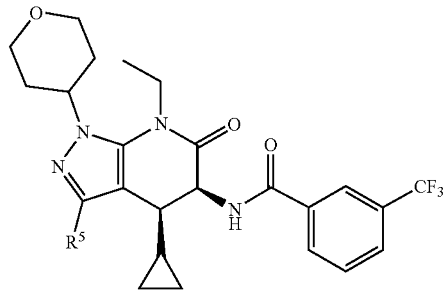

VIIIb

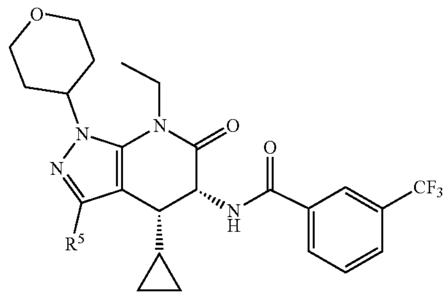

VIIIc

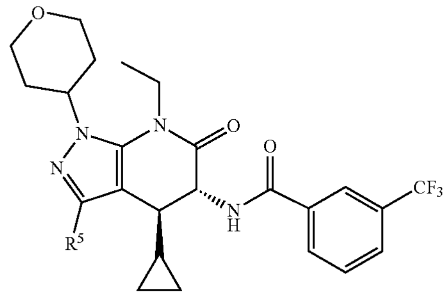

VIIId

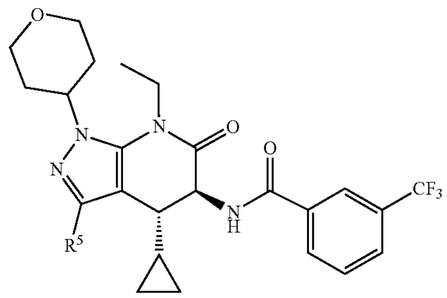

or a pharmaceutically acceptable salt thereof.

44. The compound of any one of preceding enumerated embodiments, wherein the compound is of Formula IXa, Formula IXb, Formula IXc or Formula IXd:

IXa

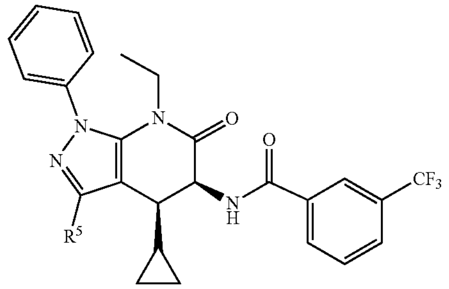

IXb

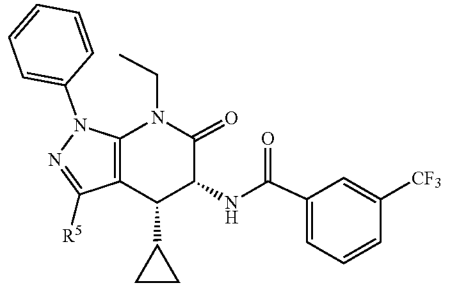

IXc

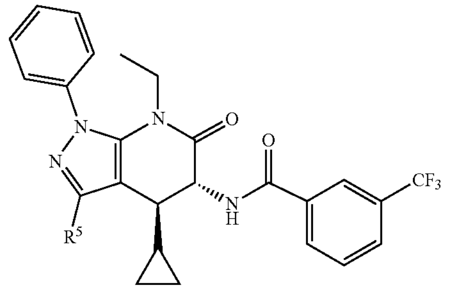

IXd

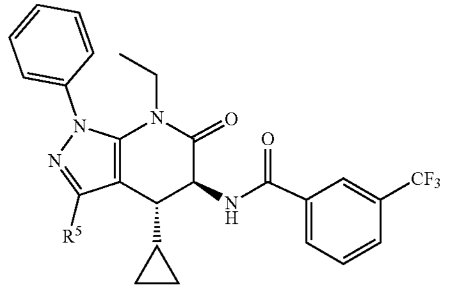

or a pharmaceutically acceptable salt thereof.

45. The compound of any one of preceding enumerated embodiments, wherein the compound is of Formula Xa, Formula Xb, Formula Xc, Formula Xd, Formula Xe, Formula Xf, Formula Xg or Formula Xh:

Xa
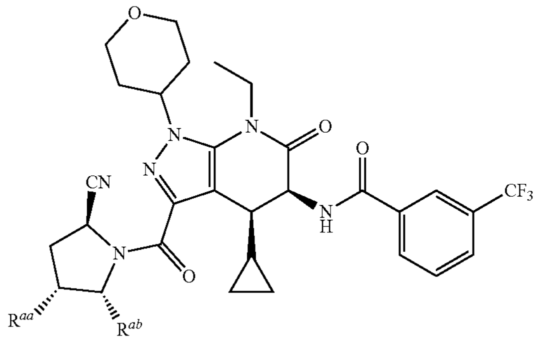
Xb
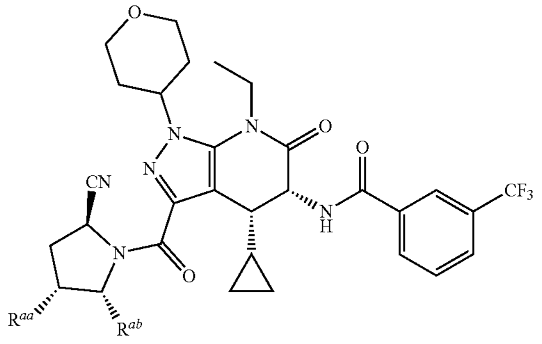
Xc
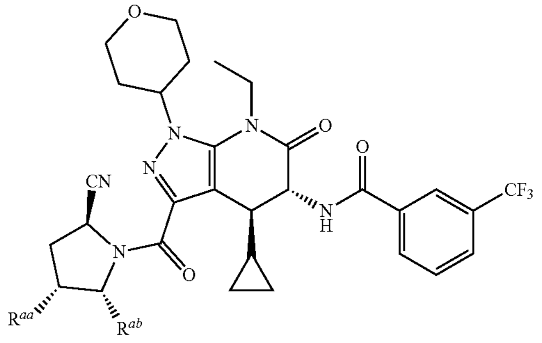
Xd
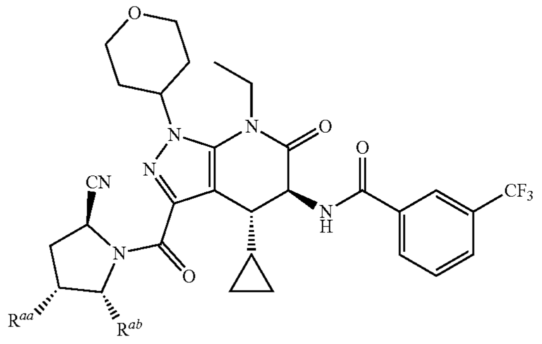
-continued
Xe
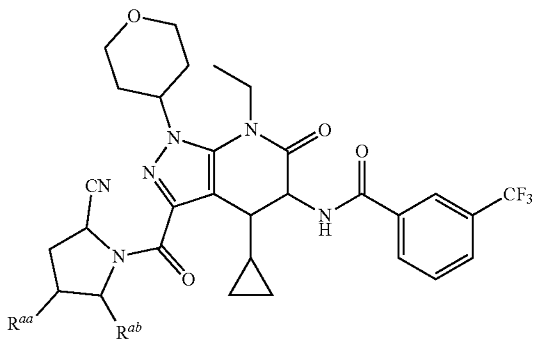
Xf
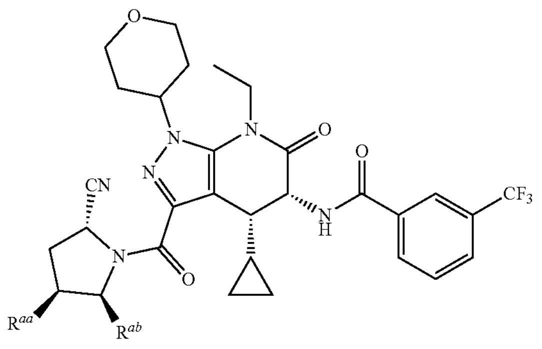
Xg
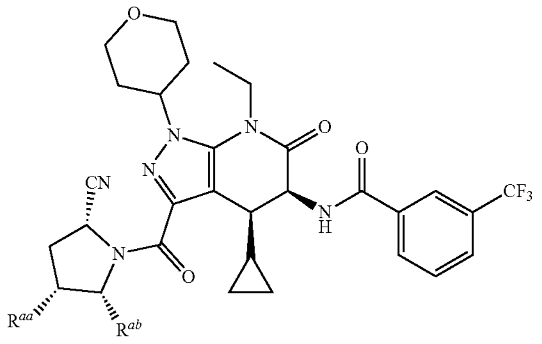
Xh
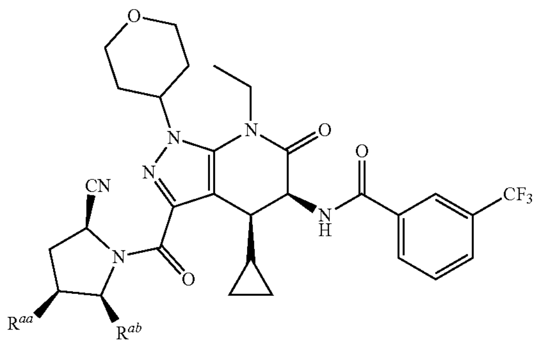
or a pharmaceutically acceptable salt thereof.
46. The compound of any one of preceding enumerated embodiments, wherein the compound is of Formula XIa, Formula XIb, Formula XIc, Formula XId, or Formula XIe:

XIa
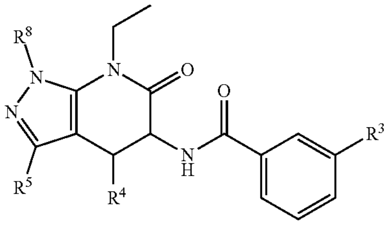
XIb
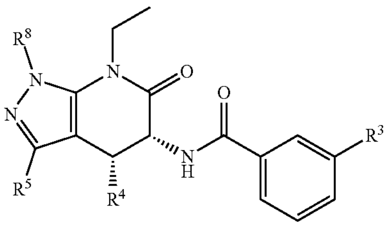
XIc
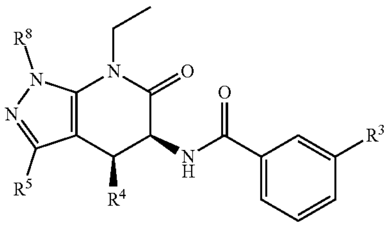
XId
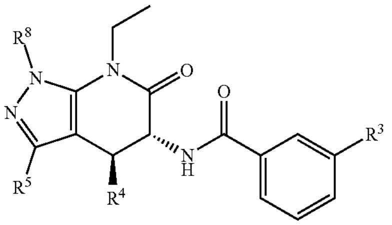
XIe
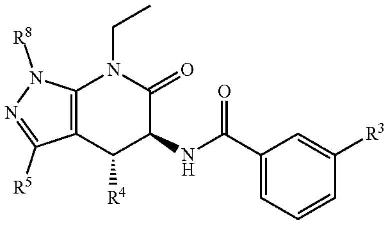
or a pharmaceutically acceptable salt thereof.
47. A compound selected from one of those shown in Table 1, or a pharmaceutically acceptable salt thereof.
48. A compound selected from one of the following:
I-3a
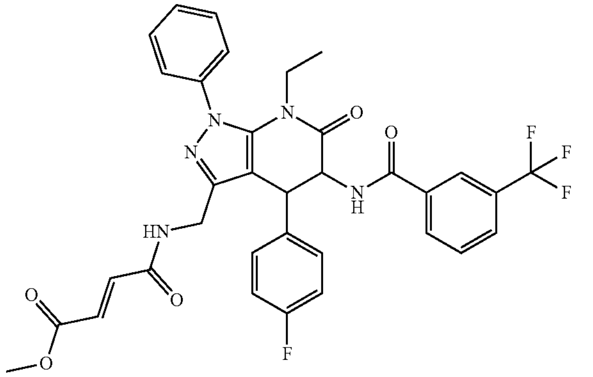
I-5a
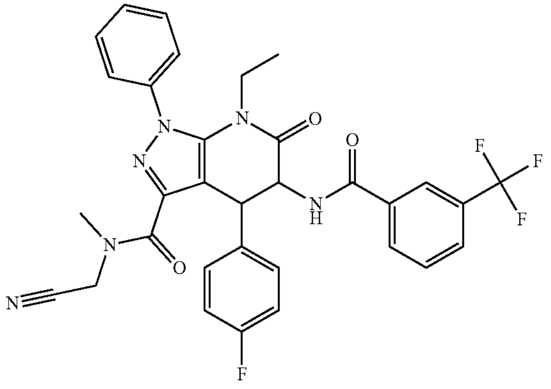
I-256a
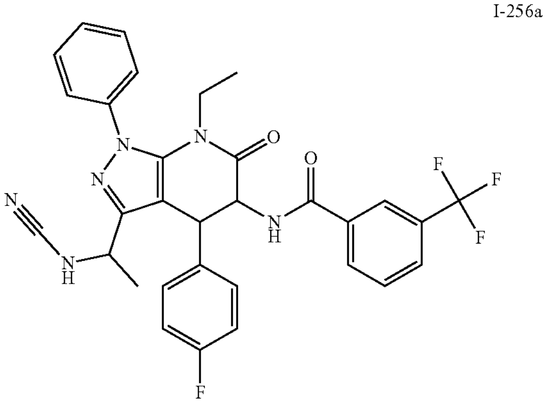
I-34a
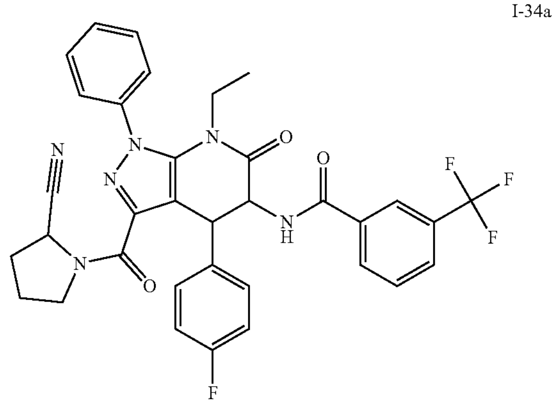

-continued
I-49a
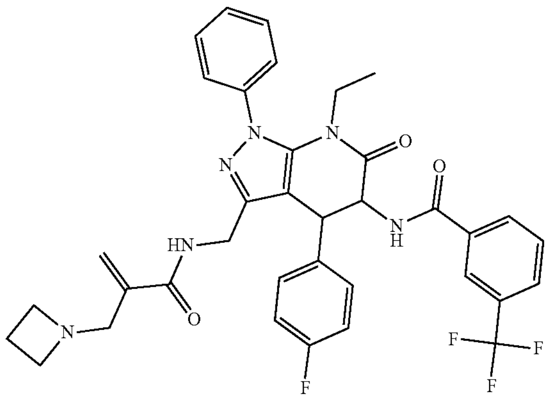
I-92a
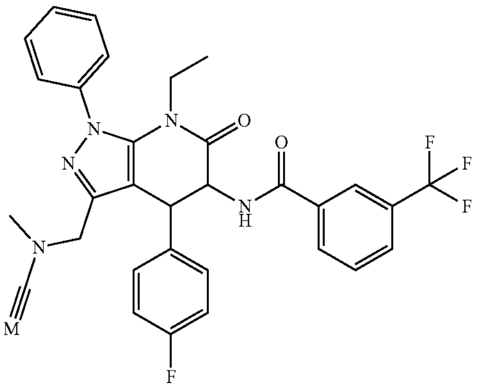
I-112a
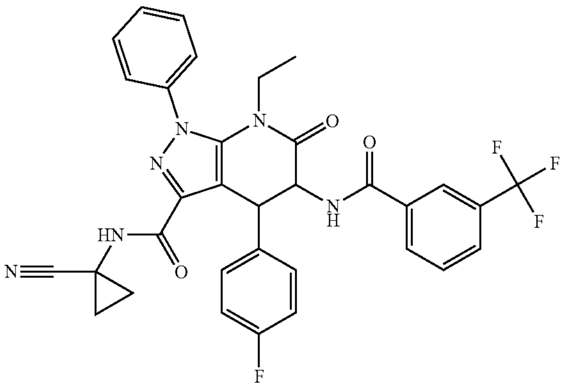
I-140a
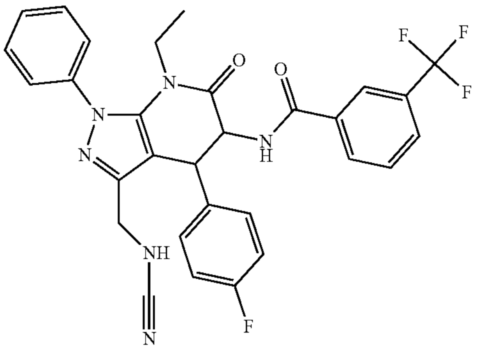
-continued
I-152a
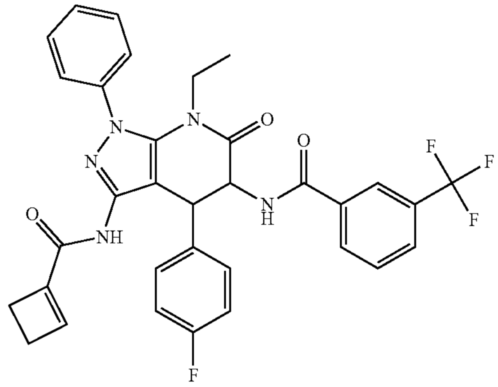
I-256b
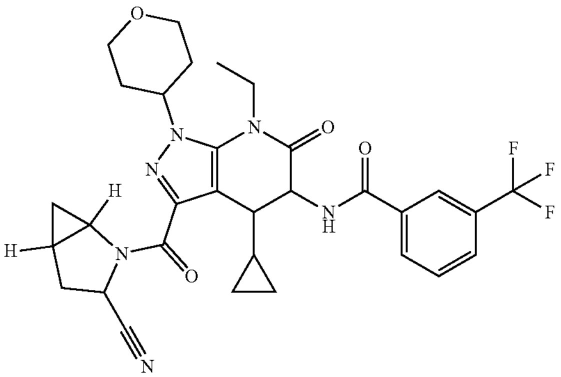
I-363a
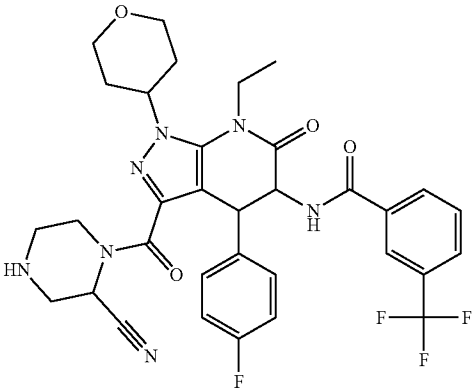
and
I-552a
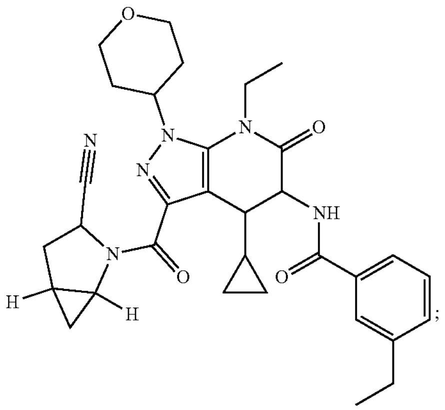
;
or a pharmaceutically acceptable salt thereof.

49. A compound selected from one of the following:
I-3
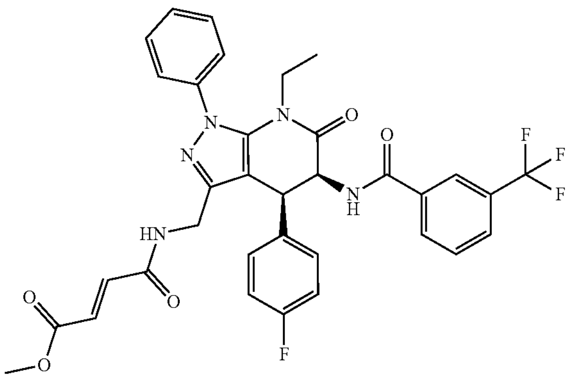
I-5
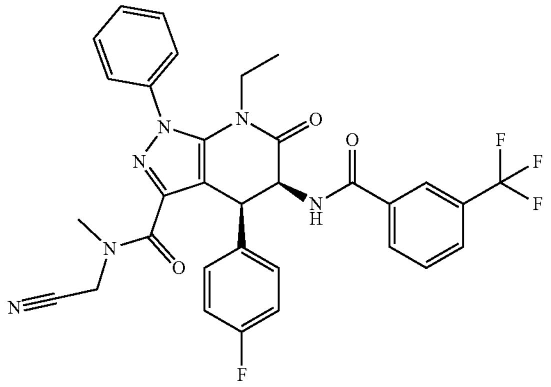
I-13
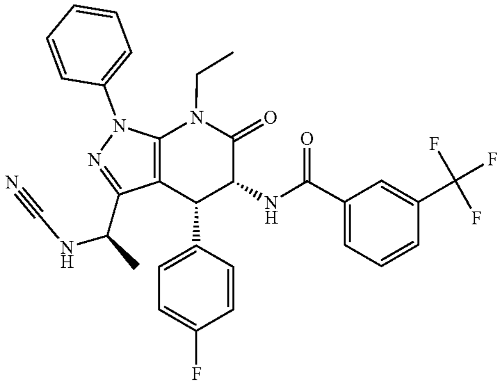
I-34
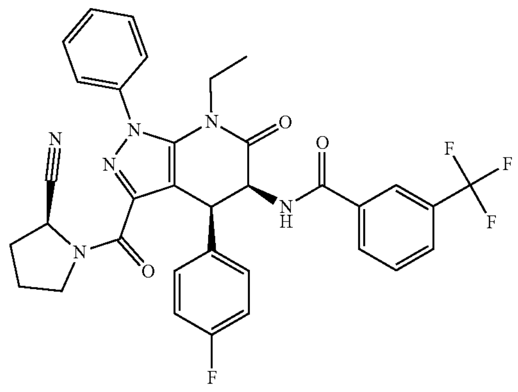
-continued
I-49
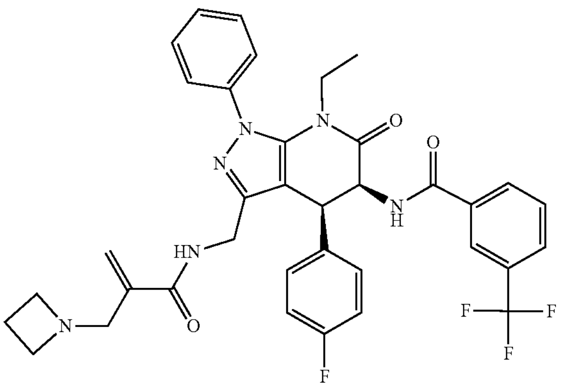
I-73
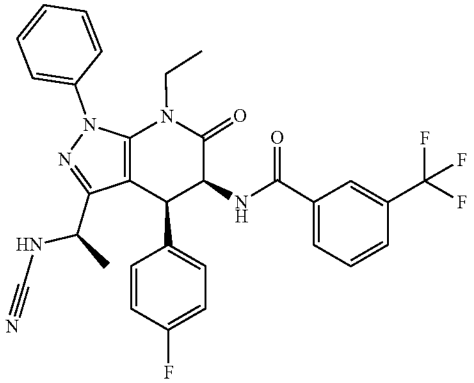
I-92
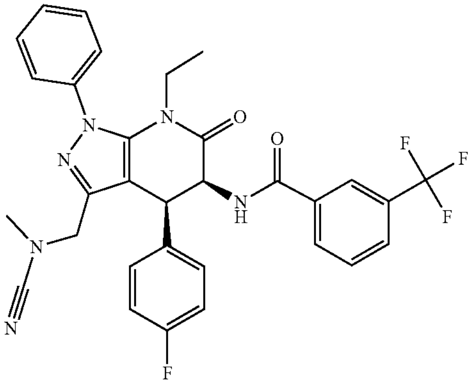
I-112
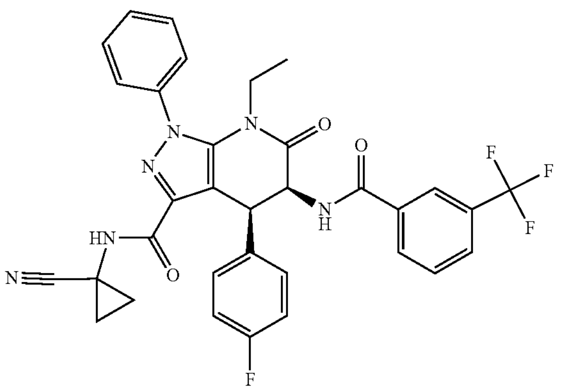

-continued
I-139
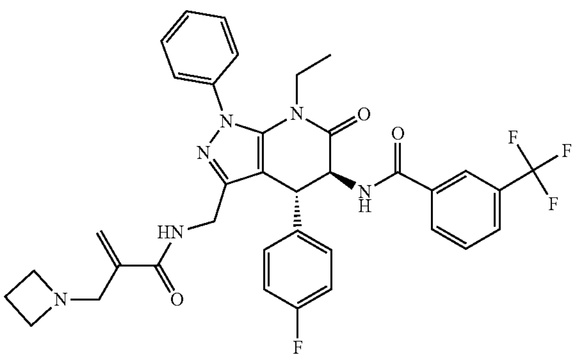
I-140
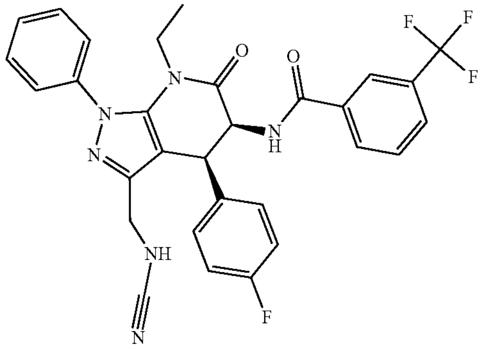
I-152
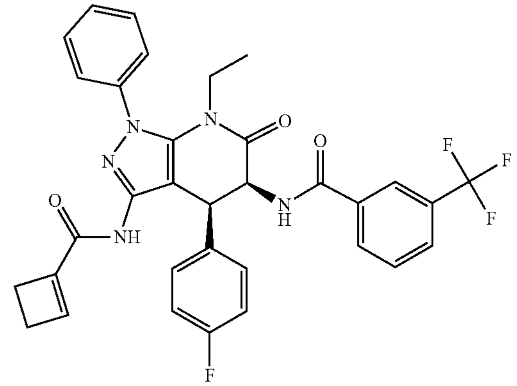
I-256
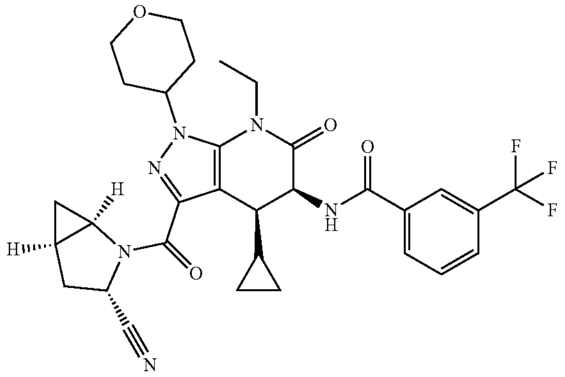
-continued
I-703
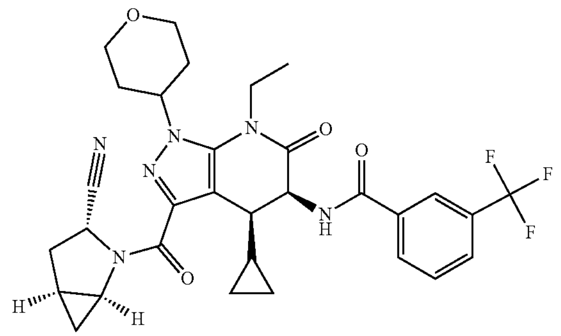
I-363
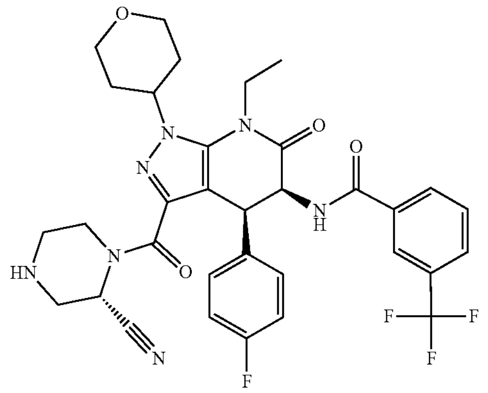
and
I-552
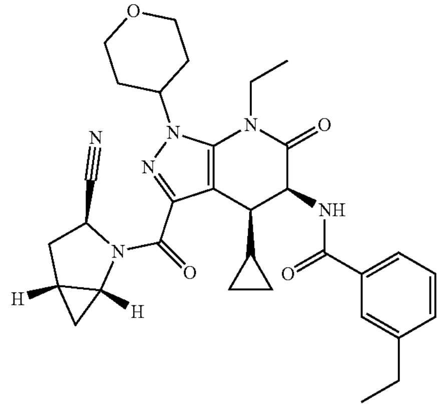
;
or a pharmaceutically acceptable salt thereof.
50. The compound of enumerated embodiment 48, wherein the compound is of the following structure:

I-3a

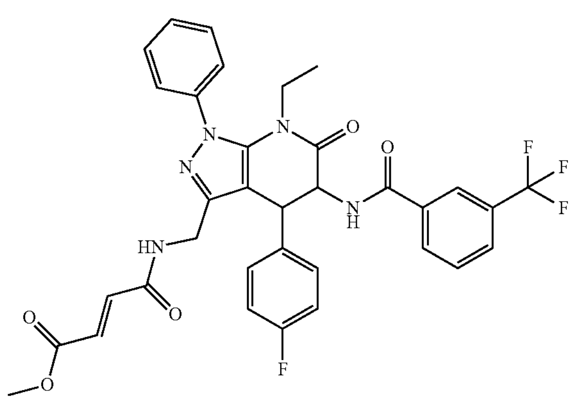

or a pharmaceutically acceptable salt thereof.

51. The compound of enumerated embodiment 48, wherein the compound is of the following structure:

I-5a

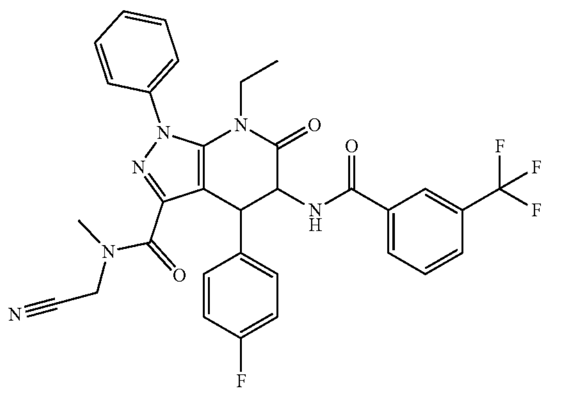

or a pharmaceutically acceptable salt thereof.

52. The compound of enumerated embodiment 48, wherein the compound is of the following structure:

I-256a

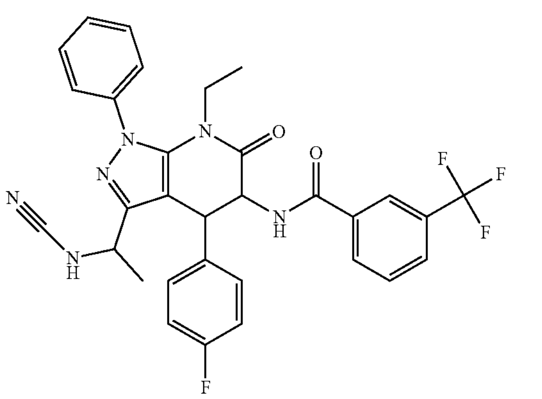

or a pharmaceutically acceptable salt thereof.

53. The compound of enumerated embodiment 48, wherein the compound is of the following structure:

I-34a

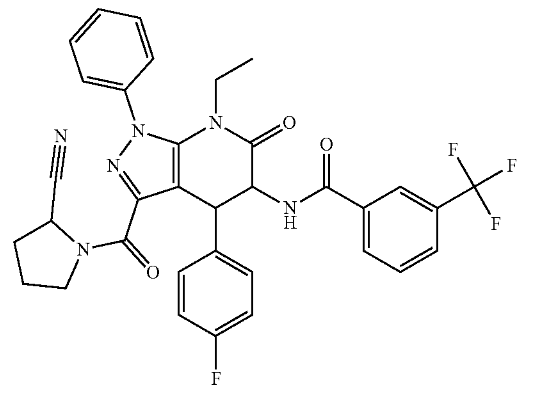

or a pharmaceutically acceptable salt thereof.

54. The compound of enumerated embodiment 48, wherein the compound is of the following structure:

I-49a

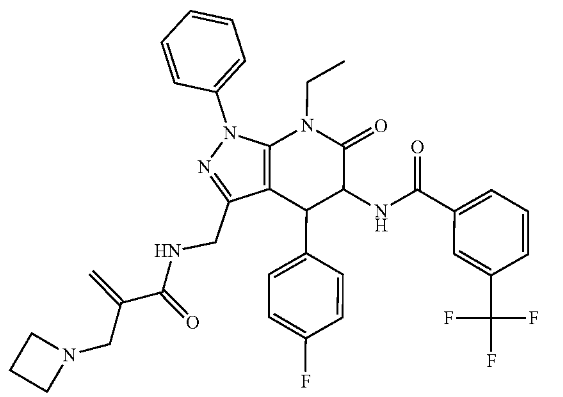

or a pharmaceutically acceptable salt thereof.

55. The compound of enumerated embodiment 48, wherein the compound is of the following structure:

I-92a

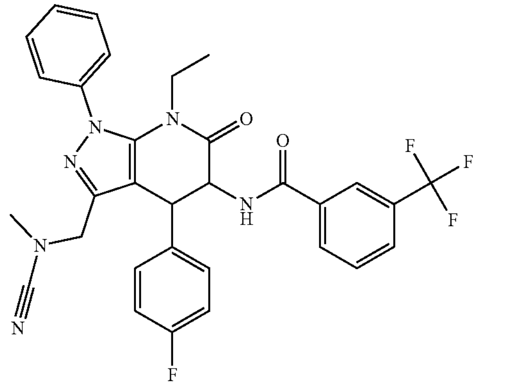

or a pharmaceutically acceptable salt thereof.

56. The compound of enumerated embodiment 48, wherein the compound is of the following structure:

I-112

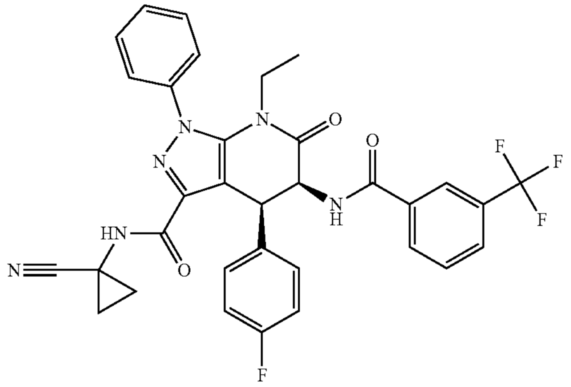

or a pharmaceutically acceptable salt thereof.

57. The compound of enumerated embodiment 48, wherein the compound is of the following structure:

I-140a

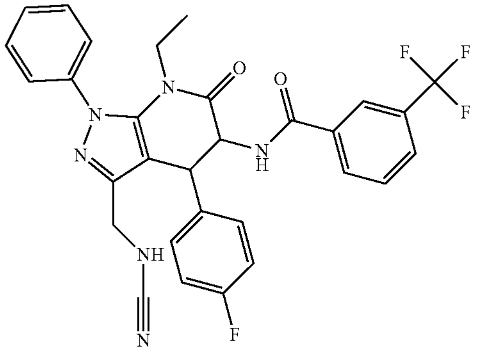

or a pharmaceutically acceptable salt thereof.

58. The compound of enumerated embodiment 48, wherein the compound is of the following structure:

I-152a

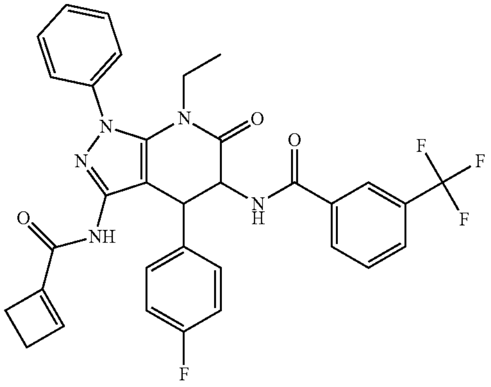

or a pharmaceutically acceptable salt thereof.

59. The compound of enumerated embodiment 48, wherein the compound is of the following structure:

I-256b

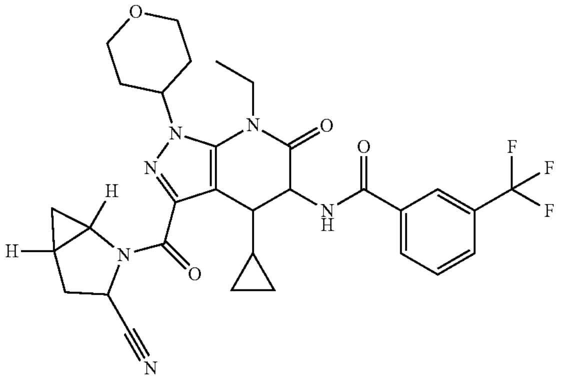

or a pharmaceutically acceptable salt thereof.

60. The compound of enumerated embodiment 48, wherein the compound is of the following structure:

I-363a

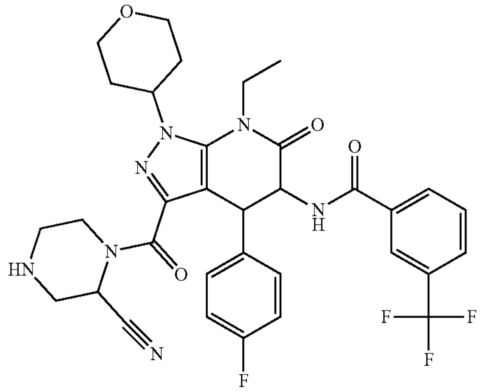

or a pharmaceutically acceptable salt thereof.

61. The compound of enumerated embodiment 48, wherein the compound is of the following structure:

I-552a

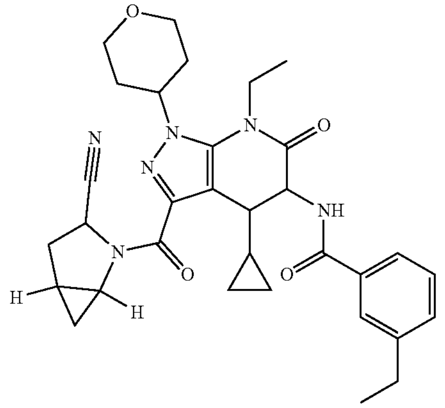

or a pharmaceutically acceptable salt thereof.

62. The compound of enumerated embodiment 49, wherein the compound is of the following structure:

I-3

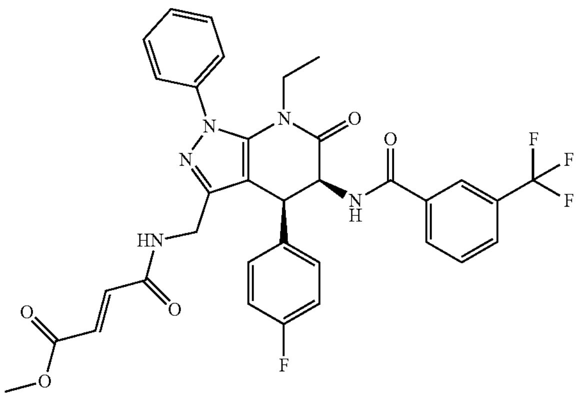

or a pharmaceutically acceptable salt thereof.

63. The compound of enumerated embodiment 49, wherein the compound is of the following structure:

I-5

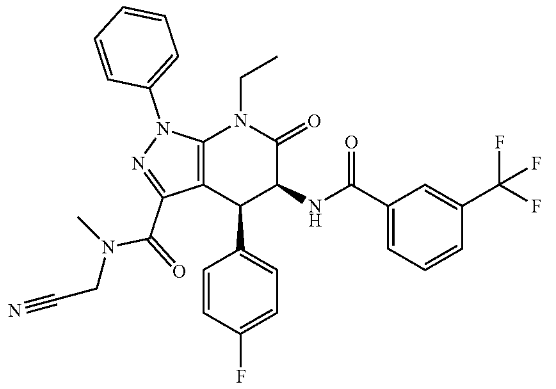

or a pharmaceutically acceptable salt thereof.

64. The compound of enumerated embodiment 49, wherein the compound is of the following structure:

I-13

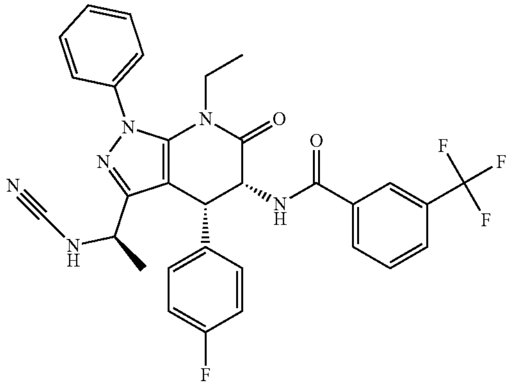

or a pharmaceutically acceptable salt thereof.

65. The compound of enumerated embodiment 49, wherein the compound is of the following structure:

I-34

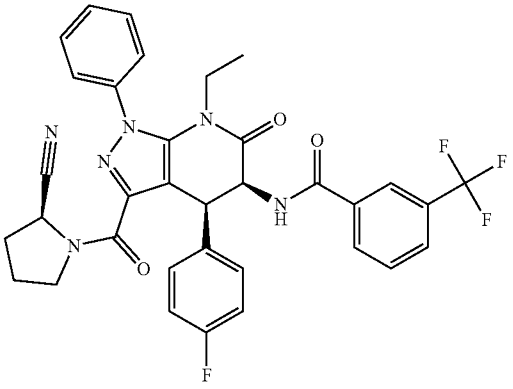

or a pharmaceutically acceptable salt thereof.

66. The compound of enumerated embodiment 49, wherein the compound is of the following structure:

I-49

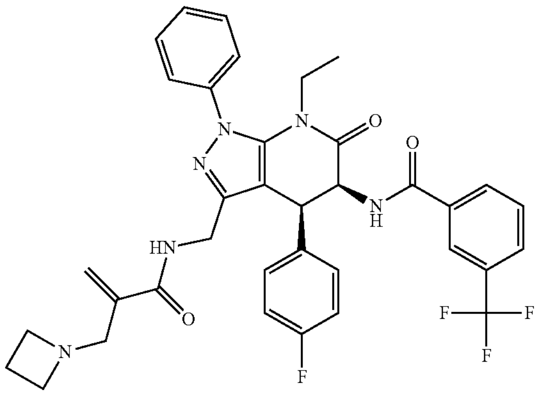

I-139

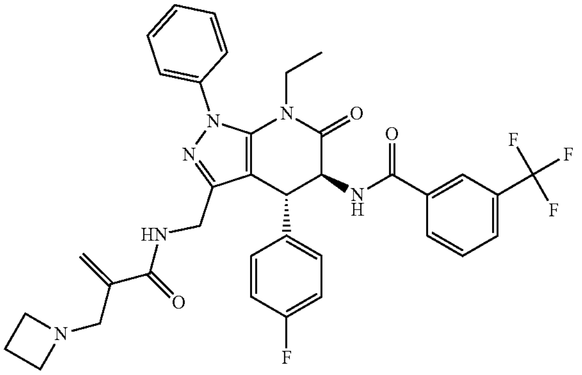

or a pharmaceutically acceptable salt thereof.

67. The compound of enumerated embodiment 49, wherein the compound is of the following structure:

I-73

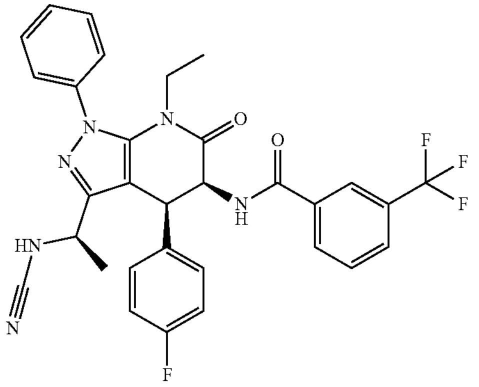

or a pharmaceutically acceptable salt thereof.

68. The compound of enumerated embodiment 49, wherein the compound is of the following structure:

I-92

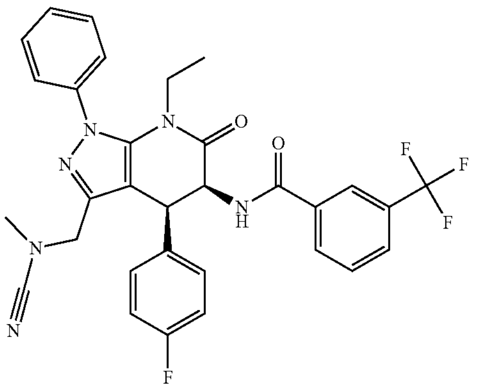

or a pharmaceutically acceptable salt thereof.

69. The compound of enumerated embodiment 49, wherein the compound is of the following structure:

I-112

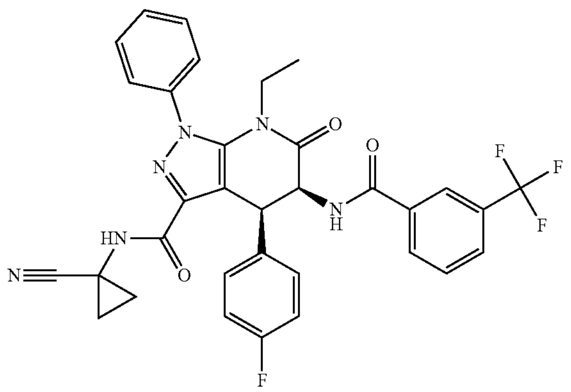

or a pharmaceutically acceptable salt thereof.

70. The compound of enumerated embodiment 49, wherein the compound is of the following structure:

I-140

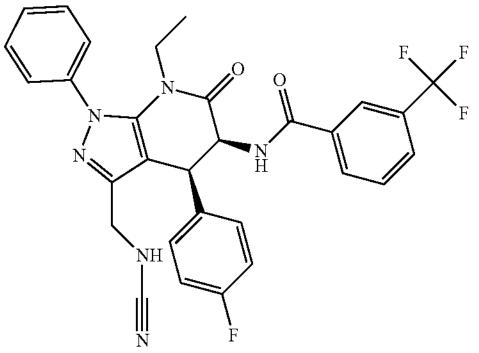

or a pharmaceutically acceptable salt thereof.

71. The compound of enumerated embodiment 49, wherein the compound is of the following structure:

I-152

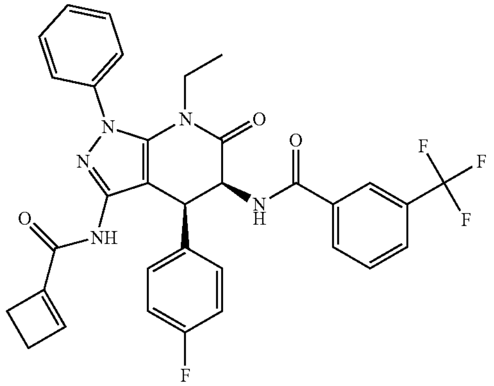

or a pharmaceutically acceptable salt thereof.

72. The compound of enumerated embodiment 49, wherein the compound is of the following structure:

I-256

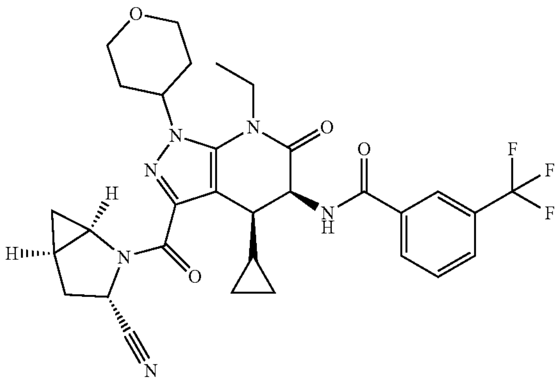

or a pharmaceutically acceptable salt thereof.

73. The compound of enumerated embodiment 49, wherein the compound is of the following structure:

I-703

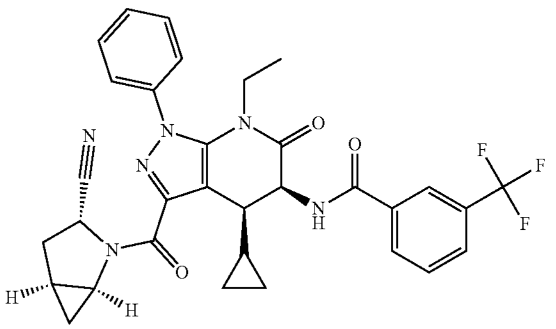

or a pharmaceutically acceptable salt thereof.

74. The compound of enumerated embodiment 49, wherein the compound is of the following structure:

I-363

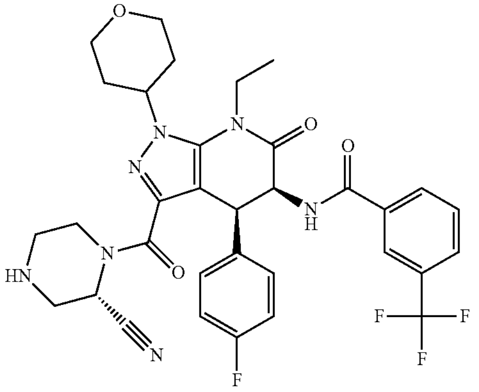

or a pharmaceutically acceptable salt thereof.

75. The compound of enumerated embodiment 49, wherein the compound is of the following structure:

I-552

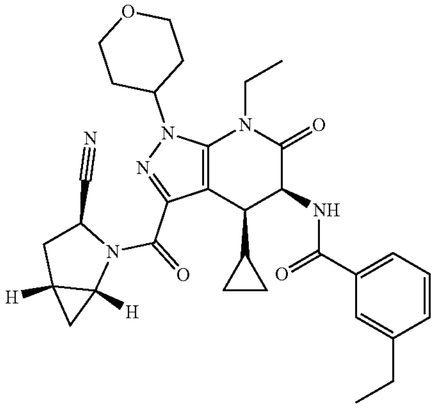

or a pharmaceutically acceptable salt thereof.

76. A pharmaceutical composition comprising the compound of any one of the preceding enumerated embodiments, or a pharmaceutically acceptable salt thereof, and a pharmaceutically acceptable carrier.

77. A pharmaceutical composition comprising the compound of enumerated embodiment 48, or a pharmaceutically acceptable salt thereof, and a pharmaceutically acceptable carrier.

78. A pharmaceutical composition comprising the compound of enumerated embodiment 49, or a pharmaceutically acceptable salt thereof, and a pharmaceutically acceptable carrier.

79. A method of treating a hemoglobinopathy disorder or disease, comprising administering to a subject in need thereof the compound or composition of any one of the preceding enumerated embodiments, or a pharmaceutically acceptable salt thereof.

80. The method of enumerated embodiment 79, wherein the hemoglobinopathy is a sickle cell disorder or disease.

81. The method of enumerated embodiment 79, wherein the hemoglobinopathy is a thalassemia disorder or disease.

82. A method to increase red blood cell levels and/or hemoglobin levels in a subject in need thereof, treat or prevent an anemia in a subject in need thereof, treat sickle-cell disease in a subject in need thereof, or treat one or more complications of sickle-cell disease in a subject in need thereof, comprising administering to a subject in need thereof a compound of any one of the preceding enumerated embodiments, or a pharmaceutically acceptable salt thereof, in combination with hydroxyurea or a pharmaceutically acceptable salt thereof.

83. A method of treating a hemoglobinopathy disorder or disease, comprising administering to a subject in need thereof the compound of any one of preceding enumerated embodiments, or a pharmaceutically acceptable salt thereof, in combination with hydroxyurea or a pharmaceutically acceptable salt thereof.

84. The method of enumerated embodiment 83, wherein the hemoglobinopathy is a sickle cell disorder or disease.

85. The method of enumerated embodiment 83, wherein the hemoglobinopathy is a thalassemia disorder or disease.

86. The method of enumerated embodiment 83, wherein the compound or pharmaceutically acceptable salt thereof and the hydroxyurea or a pharmaceutically acceptable salt thereof act synergistically.

87. A method of increasing efficacy and/or reducing toxicity of hydroxyurea treatment in a subject undergoing said treatment, comprising administering to the subject the compound of any one of the preceding enumerated embodiments, or a pharmaceutically acceptable salt thereof.

88. The method of enumerated embodiment 87, further comprising the step of decreasing an amount of hydroxyurea being administered to the subject.

89. The method of enumerated embodiment 88, wherein the amount of hydroxyurea being administered is decreased by 10-90%.

90. A method of decreasing the dose of hydroxyurea or a pharmaceutically acceptable salt thereof needed for effective treatment of a hemoglobinopathy disorder or disease, comprising administering to a subject in need thereof the compound of any one of the preceding enumerated embodiments, or a pharmaceutically acceptable salt thereof, in combination with hydroxyurea or a pharmaceutically acceptable salt thereof, wherein the dose of hydroxyurea or a pharmaceutically acceptable salt thereof needed for effective treatment of the hemoglobinopathy disorder or disease is less than the dose needed for treatment in the subject using hydroxyurea or a pharmaceutically acceptable salt thereof as a monotherapy.

91. The method of enumerated embodiment 90, wherein the dose of hydroxyurea or a pharmaceutically acceptable salt thereof co-administered with the compound or pharmaceutically acceptable salt thereof is reduced by at least 10%, at least 20%, at least 30%, at least 40%, at least 50%, at least 60%, at least 70%, at least 80%, or at least 90% relative to the dose needed for treatment in the subject using hydroxyurea or a pharmaceutically acceptable salt thereof as a monotherapy

Exemplification

As depicted in the Examples below, exemplary compounds are prepared according to the following general procedures and used in biological assays and other procedures described generally herein. It will be appreciated that, although the general methods depict the synthesis of certain compounds of the present invention, the following general methods, and other methods known to one of ordinary skill in the art, can be applied to all compounds and subclasses and species of each of these compounds, as described herein. Similarly, assays and other analyses can be adapted according to the knowledge of one of ordinary skilled in the art.

Example 1: Synthesis of Compounds I-229, I-123, I-180, I-179, I-206, I-230, I-198, I-184, I-181, I-67, I-221, I-232, I-202, I-182, I-220, I-183, I-240, I-169, I-18, I-205, I-204, I-3 and I-203

NMR:

$^1$H NMR spectrum was recorded on Bruker 400 MHz and Varian 400 MHz instruments internally referenced to a tetramethylsilane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ; Mobile Phase: A: 0.05% Formic acid in water: I (95:5) B: 0.05% Formic acid in CAN; Inj Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/min; Column oven temp. 50° C.; Gradient program: 0% B to 98% B in 2.0 minute, hold till 3.0 min, at 3.2 min B conc is 0% up to 4.0 min.

Method-C: Column: X-Select CSH C18 (50 mm*3.0 mm,2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2,2.0/98, 2.8/98, 3.0/2,3.7/2.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5,1/5,8/100,12/100,14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/2,2/2, 12/90, 16/90; Flow: 1.0 mL/min.; Diluent: I: WATER (80:20).

Method-C: Column: X SELECT CSH C18 (150×4.6 mm, 3.5μ); Mobile Phase A; 0.05% TFA IN WATER: I (95:05); Mobile Phase B: 0.05% TFA IN WATER: I (05:95); Programme: T/B %: 0.01/10, 12/90, 16/90; Flow: 1 mL/min.; Diluent: WATER: I (80:20).

Method-D: Column: X-Bridge CSH C18 (4.6*150) mm 5u Mobile Phase: A-0.1% TFA in water B-Acetonitrile Inj Volume; 5.0 μL, Flow Rate: 1.2. mL/minute Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in HEXANE Mobile Phase B: IPA A/B: 60/40 Flow: 1.0 ml/MIN PDA: OJ-H_015.

Method-F: Column: ACE Excel 2 C18-AR, 100 mm×3.0 mm Mobile Phase A: 0.05% FA in Water; Mobile Phase B: 0.05% FA in Acetonitrile Colum Temperature: 40° C. Flow Rate: 0.6 mL/min Gradient: 0/5, 1/5, 6/90, 8.5/90, 8.8/5, 11/5.

Synthesis of Intermediate Compound 5

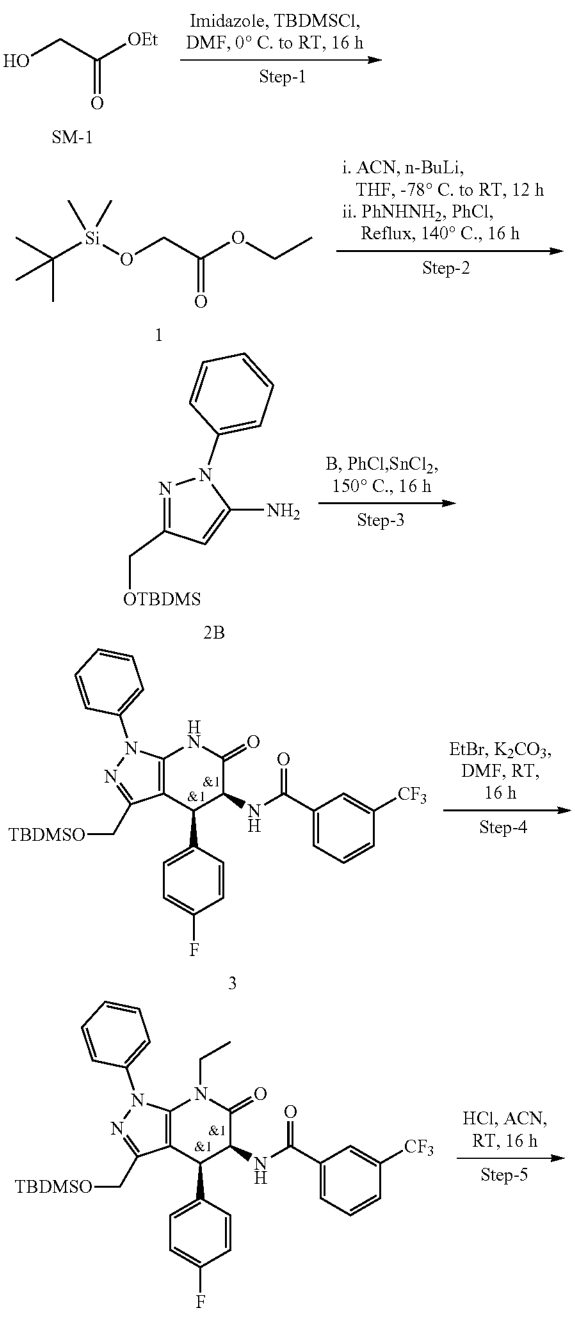

SM-1
1
2B
3
4

-continued

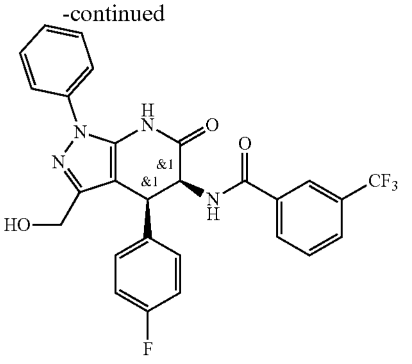

5

Step-1: Synthesis of ethyl 2-((tert-butyldimethylsilyl)oxy)acetate (1)

To stirred solution of compound (SM1) (25 g, 240.1 mmol) in DMF (125 mL) was added imidazole (27.6 g, 312.2 mmol) and TBDMSCl (47.04 g, 312.2 mmol) at 0° C. The reaction mixture was stirred at room temperature for 16 h. After consumption of the starting material (by TLC), the reaction mixture was quenched with water (1.2 lit) and extracted with EtOAc (2×500 mL). The combined organic layer was dried over anhydrous sodium sulfate and concentrated to afford crude compound. The obtained crude compound was purified by using flash column chromatography eluting with 0-20% EtOAC in Heptane. Pure fraction was collected and concentrated under vacuum to afford compound (1) (24 g, 46.1%) as colorless liquid.

$^1$H NMR (400 MHZ, DMSO-d6): δ 4.21 (s, 2H), 4.09 (q, J=6.8 Hz, 2H), 1.18 (t, J=6.8 Hz, 3H), 0.88-0.82 (m, 9H), 0.06-0.07 (m, 6H).

Step-(2i): Synthesis of 3-(((tert-butyldimethylsilyl)oxy)methyl)-1-phenyl-1H-pyrazol-5-amine (2A)

To a stirred solution of acetonitrile (15 mL) in THF (750 mL), n-butyl lithium (2.5 mol/l) in hexanes (115 ml, 290 mmol) was added at −78° C. The reaction mixture was stirred at −78° C. for 30 min. after 30 mins, compound (1) (40 g, 183.18 mmol) dissolved in THF (750 mL) was added to the reaction mixture slowly at same temperature. Slowly allowed the reaction mixture to room temperature and maintained the same for 12 h. Reaction progress was monitored by TLC. After completion of the reaction, the reaction mixture was quenched with water and adjusted pH to 4-5 using 2N aq·HCl solution. The reaction solution was extracted with 2×500 mL ethyl acetate. Combined organic layer was dried over anhydrous sodium sulfate and concentrated under reduced pressure to afford crude compound (2A) (37 g, 94.67%) as a pale-brown oil.

Step-(2ii): Synthesis of 5-[[tert-butyl(dimethyl)silyl]oxymethyl]δδδ-2-phenyl-pyrazol-3-amine (2B)

To a stirred solution of compound (2A) (37 g, 173.42 mmol) in chlorobenzene (110 mL), phenylhydrazine (19 g, 173.94 mmol) was added at room temperature. Raised the reaction mass temperature to 140° C. The reaction mixture stirred at same temperature for 16 h. Reaction progress was monitored by TLC. After completion of starting material, the reaction mixture was quenched with water (100 mL) and extracted with ethyl acetate (2×500 mL). Combined organic layer was dried over anhydrous sodium sulfate, concentrated under reduced pressure to afford crude compound. The obtained crude compound was purified by column chromatography eluting with 15-20% ethyl acetate in pet ether to afford compound (2B) (26.0 g, 35.07%) as a yellow solid.

$^1$H NMR (400 MHZ, DMSO-d6): δ 7.54-7.58 (m, 2H), 7.43-7.48 (m, 2H), 7.29 (dt, J=7.4, 1.2 Hz, 1H), 5.47 (s, 1H), 5.30 (s, 2H), 4.50 (s, 2H), 0.87-0.91 (m, 9H), 0.07 (s, 6H).

LC-MS (Method-B)=304.7 [M+H]$^+$; 70.73% at RT 2.16 min.

Step-3: Synthesis of rac-N-((4R,5R)-3-(((tert-butyldimethylsilyl)oxy)methyl)-4-(4-fluorophenyl)-6-oxo-1-phenyl-4,5,6,7-tetrahydro-1H-pyrazolo[3,4-b]yridine-5-yl)-3-(trifluoromethyl)benzamide (3)

To a stirred solution compound (2B) (26 g, 85.67 mmol) and Int-B (29.19 g, 85.67 mmol) in chlorobenzene (78 ml), tin(II) chloride (1.64 g, 8.56 mmol) was added at room temperature. The reaction mixture was stirred at 140-150° C. for 16 h. Reaction progress was monitored by TLC. After completion of reaction, the reaction mixture was quenched with water (100 mL) and filtered through celite bed and washed with DCM (500 mL). Filtrate was washed with water and extracted with DCM (2×500 mL). Organic layer was dried over anhydrous sodium sulfate and concentrated under reduced pressure. The obtained crude was purified by column chromatography by eluting with 20-30% ethyl acetate in pet ether to afford compound (3) (30 g, 48.6%) as yellow solid.

$^1$H NMR (400 MHZ, DMSO-d6): δ 11.06 (s, 1H), 8.36 (d, J=3.4 Hz, 1H), 8.07 (s, 2H), 7.89 (d, J=7.3 Hz, 1H), 7.58-7.71 (m, 4H), 7.49-7.55 (m, 2H), 7.40 (d, J=6.8 Hz, 1H), 7.03-7.08 (m, 1H), 6.95 (s, 1H), 5.24-5.34 (m, 1H), 4.69 (d, J=6.8 Hz, 1H), 4.56-4.62 (m, 1H), 4.40-4.46 (m, 1H), 0.73 (s, 5H).

LC-MS (Method-A)=639.29 [M+H]$^+$; 88.73% at RT 2.48 min.

Step-4: Synthesis of rac-N-((4R,5R)-3-(((tert-butyldimethylsilyl)oxy)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (4)

To a stirred solution of compound (3) (30 g, 41.33 mmol) in DMF (300 mL), potassium carbonate (7.50 g, 53.73 mmol) and bromoethane (5.45 g, 49.60 mmol) were added at room temperature. The reaction mixture was stirred at room temperature for 16 h. Reaction progress was monitored by TLC. After completion of SM, the reaction mixture was quenched with water and extracted with ethyl acetate. Organic layer was dried over anhydrous sodium sulfate and evaporated under vacuum. The obtained crude was purified by column chromatography by eluting with 15-20% ethyl acetate in heptane to afford compound (4) (15 g, 48.3%) as yellow solid.

$^1$H NMR (400 MHZ, DMSO-d6) ($D_2O$): δ 8.05-8.10 (m, 2H), 7.91 (d, J=7.1 Hz, 1H), 7.68-7.74 (m, 1H), 7.49-7.64 (m, 5H), 7.03-7.10 (m, 2H), 6.90-6.95 (m, 2H), 5.41 (d, J=7.2 Hz, 1H), 4.65-4.69 (m, 1H), 4.62 (d, J=12.5 Hz, 1H), 4.45 (d, J=12.4 Hz, 1H), 2.94-3.08 (m, 2H), 0.79-0.92 (m, 3H), 0.70 (s, 9H), −0.12 (s, 6H).

LC-MS (Method-B)=667.5 [M+H]$^+$; 83.38% at RT 2.52 min.

Step-5: Synthesis of rac-N-((4R,5R)-7-ethyl-4-(4-fluorophenyl)-3-(hydroxymethyl)-6-oxo-1-phenyl-4,5,6,7-tetrahydro-1H-pyrazolo[3,4-b]pyridine-5-yl)-3-(trifluoromethyl)benzamide (5)

To a stirred solution of compound (4) (20 g, 24.90 mmol) in acetonitrile (100 mL), hydrochloric acid (20 mL, 120 mmol) was added. The reaction mixture was stirred at room temperature for 16 h. Reaction progress was monitored by TLC. After completion of reaction, the reaction mixture was quenched with ice water (1000 mL) and extracted with ethyl acetate (2×1500 mL). Organic layer was dried over anhydrous sodium sulfate and concentrated under vacuum to afford crude compound. The crude material was washed with 10% diethyl ether in pentane and dried under vacuum to afford 5 (12.00 g, 83.75%) as a pale-yellow solid.

$^1$H NMR (400 MHZ, DMSO-d6, 25° C.): δ 8.53 (d, J=7.3 Hz, 1H), 8.12-8.17 (m, 2H), 7.92 (d, J=7.8 Hz, 1H), 7.64-7.74 (m, 3H), 7.50-7.61 (m, 3H), 7.10 (t, J=8.9 Hz, 2H), 6.93-7.05 (m, 2H), 5.50 (t, J=7.3 Hz, 1H), 5.11 (t, J=6.0 Hz, 1H), 4.72 (d, J=7.3 Hz, 1H), 4.35-4.41 (m, 1H), 4.24-4.30 (m, 1H), 3.87-3.94 (m, 1H), 2.98-3.08 (m, 1H), 0.91 (t, J=7.1 Hz, 3H).

LC-MS (Method-B)=553.2 [M+H]$^+$; 96.44% at RT 2.26 min.

HPLC (Method-B): 95.87% at RT 9.15 min.

Synthesis of Compound 8

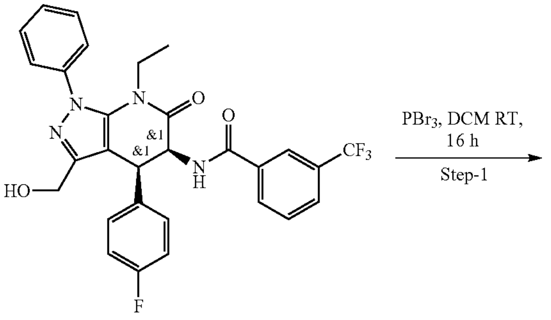

5

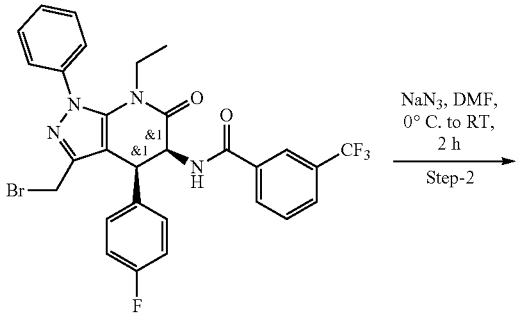

6

-continued

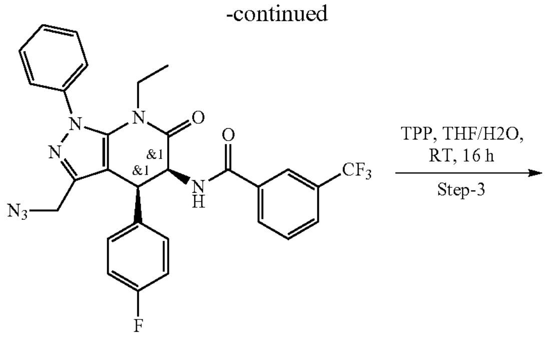

7

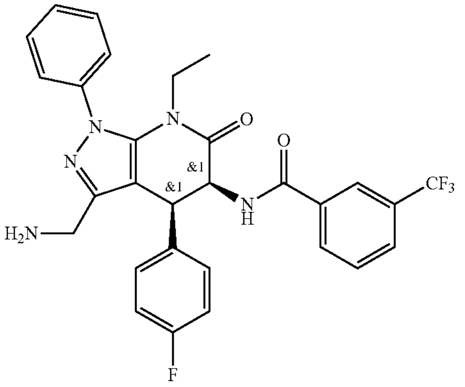

8

Step-1: Synthesis of N-((4S,5S)-3-(bromomethyl)-7-ethyl-4-(4-fluorophenyl)-6-oxo-1-phenyl-4,5,6,7-tetrahydro-1H-pyrazolo[3,4-b]pyridine-5-yl)-3 trifluoromethyl)benzamide (6)

To a stirring solution of compound-5 (1.0 g, 1.8 mmol) in dichloromethane (10.0 mL) and phosphorus tribromide (0.74 g, 2.7 mmol) at 0° C. under inert atmosphere. The reaction mixture was stirred at 25° C. for 3 h. After consumption of the starting material (by TLC), the reaction was diluted into ice cold water (20 mL) and extracted with EtOAc (2×30 mL). The organic layer was dried over anhydrous $Na_2SO_4$, concentrated under reduced pressure. The crude material was purified by medium pressure liquid chromatography by eluting with 30-40% EtOAc/heptane to afford N-((4S,5S)-3-(bromomethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (Compound-6) (500.0 mg, 40%) as a pale yellow solid.

$^1$H NMR (400 MHZ, DMSO-$d_6$) δ=8.55 (d, J=7.2 Hz, 1H), 8.16-8.13 (m, 2H), 7.92 (d, J=7.6 Hz, 1H), 7.72-7.70 (m, 3H), 7.62-7.53 (m, 3H), 7.10 (t, J=8.8 Hz, 2H), 7.01-6.98 (m, 2H), 5.54 (t, J=7.6 Hz, 1H), 4.70-4.63 (m, 2H), 4.38 (d, J=10.8 Hz, 1H), 3.90-3.88 (m, 1H), 3.07-3.02 (m, 1H), 0.93-0.84 (m, 3H).

LC-MS (Method-A)=616.7 [M+H]$^+$; 90.37% at RT 2.54 min.

Step-2: Synthesis of N-((4S,5S)-3-(azidomethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (7)

To a stirring solution of N-((4S,5S)-3-(bromomethyl)-7-ethyl-4-(4-fluorophenyl)-6-oxo-1-phenyl-4,5,6,7-tetrahydro-1H-pyrazolo[3,4-b]pyridine-5-yl)-3 trifluoromethyl)

benzamide 6 (500 mg, 0.81 mmol) in DMF (10.0 mL) and sodium azide (80.0 mg, 1.21 mmol) at 0° C. under inert atmosphere. The reaction mixture was stirred at 25° C. for 3 h. After consumption of the starting material (by TLC), the reaction was diluted with ice cold water (50 mL) and extracted with EtOAc (2×125 mL). The organic layer was dried over anhydrous $Na_2SO_4$, concentrated under reduced pressure. The crude material was purified by medium pressure liquid chromatography by eluting with 10-20% EtOAc/heptane to afford N-((4S,5S)-3-(azidomethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl) benzamide (150 mg, 29.79%) as an Off-white solid.

$^1$H NMR (400 MHZ, DMSO-$d_6$) δ=8.56 (d, J=7.2 Hz, 1H), 8.15-8.12 (m, 2H), 7.92 (d, J=8.0 Hz, 1H), 7.73-7.69 (m, 3H), 7.62-7.53 (m, 3H), 7.10 (t, J=8.8 Hz, 2H), 7.01-6.98 (m, 2H), 5.54 (t, J=7.2 Hz, 1H), 4.65 (d, J=7.2 Hz, 1H), 4.43-4.30 (m, 1H), 3.91-3.86 (m, 1H), 3.08-3.03 (m, 1H), 3.06 (dd, J=7.1, 14.2 Hz, 1H), 0.91 (t, J=7.2 Hz, 3H).

LC-MS (Method-B)=578.2 $[M+H]^+$; 96.65% at RT 2.47 min.

HPLC (Method-B): 96.28% at RT 11.5 min.

Step-3: Synthesis N-((4S,5S)-3-(aminomethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide To a stirred solution of compound (7) (2×2.5 g, 4.33 mmol) in THF/H2O (23+7 mL) and stirred for 5 min. Followed by TPP (3.4 g, 12.99 mmol) was added portion wise at room temperature. The reaction mixture was stirred at room temperature for 16 h. After consumption of starting material (by TLC), the reaction mixture was diluted with water (10 mL) and extracted with EtOAc (2×50 mL). The organic layer was dried over anhydrous $Na_2SO_4$, concentrated under reduced pressure to afford crude. The obtained crude was purified by column chromatography by eluting with 7% of MeOH/DCM to afford compound (8) (4.5 g, 95%) as a yellow solid.

$^1$H NMR (400 MHZ, DMSO-$d_6$) δ=8.54 (d, J=7.2 Hz, 1H), 8.15-8.12 (m, 2H), 7.92 (d, J=8.0 Hz, 1H), 7.73-7.65 (m, 3H), 7.60-7.52 (m, 3H), 7.13-7.08 (m, 2H), 7.02-6.99 (m, 2H), 5.54 (t, J=7.2 Hz, 1H), 4.70 (d, J=7.2 Hz, 1H), 3.94-3.88 (m, 1H), 3.61-3.57 (m, 2H), 3.07-3.02 (m, 1H), 2.67-2.66 (m, 2H), 0.91 (t, J=7.2 Hz, 3H).

LC-MS (Method-B)=551.9 $[M+H]^+$; 95.19% at RT 1.83 min.

HPLC (Method-B): 97.47% at RT 6.27 min.

Scaffold Analogues

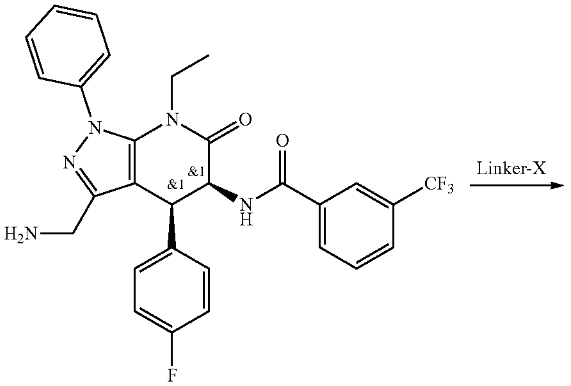

8

-continued

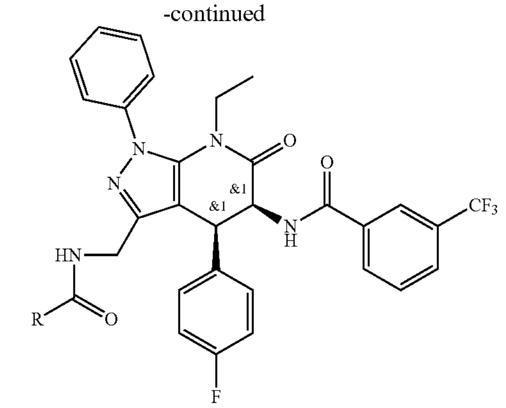

A. $Et_3N$, DCM, RT, 16 h
B. EDC(1.5 eq), HOBT (1.5 eq), DIPEA (3 eq), DMF, RT, 16 h
C. HATU, DIPEA, DMF, RT, 16 h

Method A Procedure:

To a stirred solution of 8 (130 mg, 0.23 mmol) in dichloromethane (5 mL) was added triethylamine (2 equiv.) than Linker X (X=B,C,E,H,I,R,Y) (1.3 equiv.). Then the reaction mixture stirred at room temperature for 16 h. Progress of the reaction was monitored by TLC. Reaction mixture was allowed to room temperature, quenched with water (3 mL), and extracted with ethyl acetate (2×10 mL). Combined organic layers was dried over anhydrous sodium sulfate and concentrated to afford crude compound. The obtained crude compound was purified by silica gel (230-400) column chromatography using ethyl acetate in heptane, eluted in 50% ethyl acetate in heptane to afford pure compound.

Method B Procedure:

To a stirred solution of 8 (200 mg, 0.36 mmol) in DMF (5 mL) was added N,N-Diisopropylethylamine (3 equiv., 1.08 mmol) & EDAC (1.51 equiv., 0.54 mmol) and Linker X (X=D,J,K,L,N,O,P,Q,T,2A,2D) (1.1 equiv.) followed by 1-hydroxybenzotriazole (1.5 equiv., 0.54 mmol) reagent at room temperature. Then the reaction mixture was stirred at room temperature for 16 h. Progress of the reaction was monitored by TLC and LCMS. Reaction mixture was allowed to room temperature, quenched with water (4 mL), and extracted with ethyl acetate (2×20 mL). Combined organic layers was dried over anhydrous sodium sulfate and concentrated to afford crude compound. The obtained crude compound was purified by silica gel (230-400) column chromatography using ethyl acetate in heptane, eluted at 55% ethyl acetate in heptane to afford pure compound.

Method C Procedure:

To a stirred solution of (100 mg, 0.18 mmol) in DMF (5 mL) was added N,N-Diisopropylethylamine (3 equiv., 0.54 mmol) and stirred at room temperature for 10 min. Then Linker X (X=F, G,M,2C) (1.5 equiv.) and HATU (3 equiv., 1.11 mmol) were added. Then the reaction mixture stirred at room temperature for 16 h. Progress of the reaction was monitored by TLC. Reaction mixture was allowed to room temperature, quenched with water (3 mL), and extracted with ethyl acetate (2×10 mL). Combined organic layers was dried over anhydrous sodium sulfate and concentrated to afford crude compound. Obtained crude compound was purified by silica gel (230-400) column chromatography using ethyl acetate in heptane to afford pure compound.

| Sr No. | Compound Number | Linker | Structure (R) | Method | Qty of 4 (mg) | Linker Qty (mg) | Qty (mg) & Nature of compound | Yield (%) |
|---|---|---|---|---|---|---|---|---|
| 1. | I-229 | B | 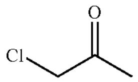 | A | 150 | 33 | 67 (Off-white solid) | 39 |
| 2. | I-123 | C | 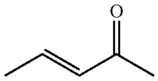 | A | 130 | 27 | 46.6 (Off-white solid) | 31 |
| 3. | I-180 | E | 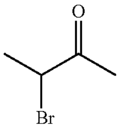 | A | 50 | 23.7 | 35.6 (Off-white solid) | 56 |
| 4. | I-179 | H | 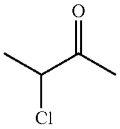 | A | 130 | 32.9 | 66.5 (Pale-yellow solid) | 44 |
| 5. | I-206 | I | 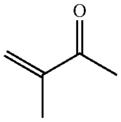 | A | 130 | 27 | 66 (Off-white solid) | 45 |
| 6. | I-230 | R | 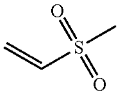 | A | 100 | 25.1 | 15 (White solid) | 12.9 |
| 7. | I-198 | Y | 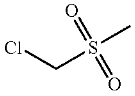 | A | 130 | 45.66 | 55 (White solid) | 34.78 |
| 8. | I-184 | D | 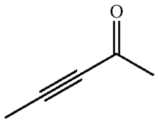 | B | 130 | 19.8 | 90 (Off-white solid) | 62 |
| 9. | I-181 | J | 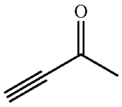 | B | 130 | 21 | 35.5 (White solid) | 25 |
| 10. | I-67 | K | 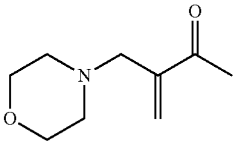 | B | 130 | 44 | 43 (Off-white solid) | 26 |
| 11. | I-221 | L | 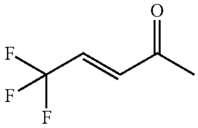 | B | 130 | 36.3 | 45.6 (Off-white solid) | 28.8 |
| 12. | I-232 | N | 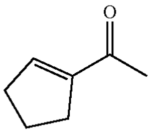 | B | 130 | 29 | 56 (Off-white solid) | 36.8 |

-continued
| Sr No. | Compound Number | Linker | Structure (R) | Method | Qty of 4 (mg) | Linker Qty (mg) | Qty (mg) & Nature of compound | Yield (%) |
|---|---|---|---|---|---|---|---|---|
| 13. | I-202 | O | 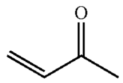 | B | 130 | 67.5 | 67.0 (Off-white solid) | 47 |
| 14. | I-182 | P | 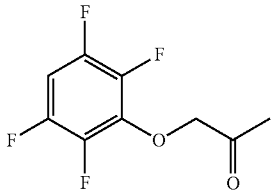 | B | 150 | 45 | 45 (Off-white solid) | 21.8 |
| 15. | I-220 | Q | 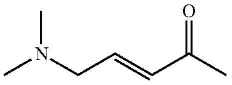 | B | 130 | 33 | 24 (Off-white solid) | 15 |
| 16. | I-183 | T | 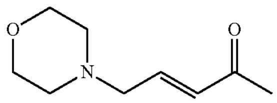 | B | 150 | 60 | 30 (Off-white solid) | 15.7 |
| 17. | I-240 | 2A | 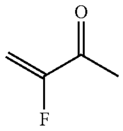 | B | 200 | 35.92 | 90 (Off-white solid) | 37.81 |
| 18. | I-169 | 2D | 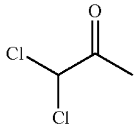 | B | 200 | 51.44 | 85 (Off-white solid) | 33.90 |
| 19. | I-18 | F | 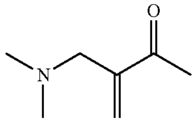 | C | 150 | 75 | 40 (Off-white solid) | 22 |
| 20. | I-205 | G | 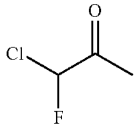 | C | 150 | 45 | 45 (Off-white solid) | 25.7 |
| 21. | I-204 | M | 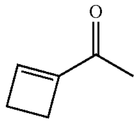 | C | 150 | 29.34 | 45.5 (Off-white solid) | 26 |
| 22. | I-3 | 2C | 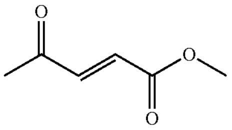 | C | 100 | 35.29 | 57 (Pale-yellow solid) | 46.42 |
| 23. | I-203 | S | 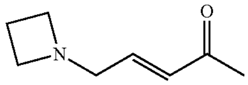 | C | 150 | 70 | 33.7 (Off-white solid) | 18 |

I-229

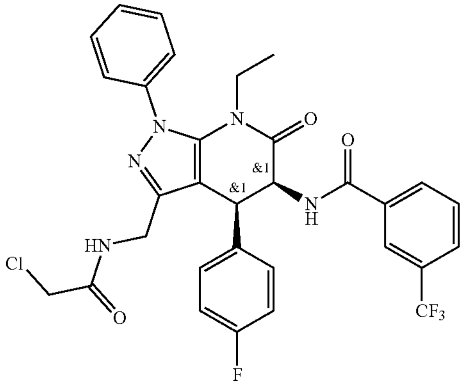

$^1$H NMR (400 MHZ, DMSO-$d_6$) δ=8.53 (d, J=7.6 Hz, 1H), 8.48 (t, J=5.6 Hz, 1H), 8.17-8.13 (m, 2H), 7.92 (d, J=7.6 Hz, 1H), 7.73-7.66 (m, 3H), 7.61-7.51 (m, 3H), 7.10 (t, J=8.8 Hz, 2H), 6.93-6.90 (m, 2H), 5.50 (t, J=7.2 Hz, 1H), 4.55 (d, J=7.2 Hz, 1H), 4.37-4.31 (m, 1H), 4.15-4.10 (m, 1H), 3.93-3.88 (m, 1H), 3.59-3.50 (m, 2H), 3.06-2.99 (m, 1H), 0.90 (t, J=7.2 Hz, 3H).

LC-MS (Method-B)=628.47 $[M+H]^+$; 99.22% at RT 1.45 min.

HPLC (Method-B)=97.34% at RT 9.26 min.

I-123

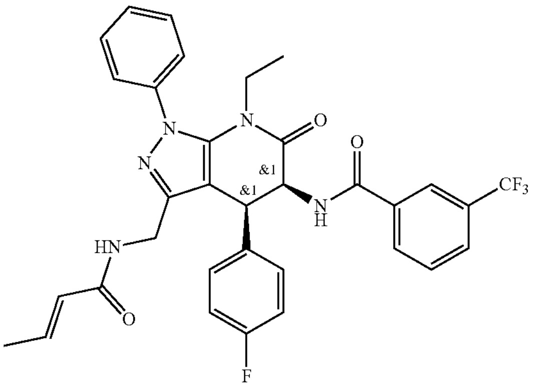

$^1$H NMR (400 MHZ, DMSO-$d_6$) δ=8.53-8.49 (m, 1H), 8.16-8.07 (m, 3H), 7.92 (d, J=7.6 Hz, 1H), 7.73-7.65 (m, 3H), 7.61-7.51 (m, 3H), 7.11-7.01 (m, 2H), 6.93-6.86 (m, 2H), 6.37-6.28 (m, 1H), 5.51-5.42 (m, 2H), 4.54 (d, J=7.2 Hz, 1H), 4.39-4.33 (m, 1H), 4.13-4.08 (m, 1H), 3.94-3.88 (m, 1H), 3.05-2.97 (m, 1H), 1.63-1.61 (m, 3H), 0.90 (t, J=7.2 Hz, 3H).

LC-MS (Method-B)=620.80 $[M+H]^+$; 99.63% at RT 2.06 min.

HPLC (Method-B)=98.49% at RT 8.71 min.

I-180

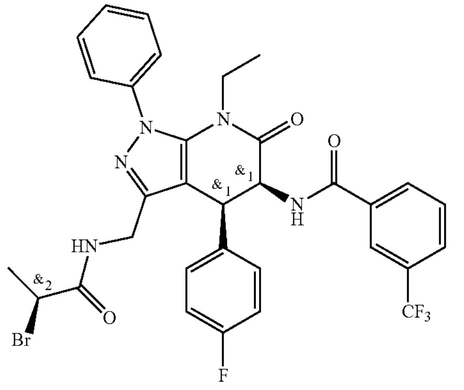

$^1$H NMR (400 MHZ, DMSO-$d_6$) δ=8.60-8.51 (m, 2H), 8.15-8.12 (m, 2H), 7.92 (d, J=8.0 Hz, 1H), 7.73-7.67 (m, 3H), 7.61-7.53 (m, 3H), 7.09 (t, J=8.8 Hz, 2H), 6.96-6.91 (m, 2H), 5.50-5.48 (m, 1H), 4.61-4.54 (m, 1H), 4.32-4.30 (m, 1H), 4.19-4.11 (m, 2H), 3.91-3.89 (m, 1H), 3.04-3.01 (m, 1H), 1.39-1.23 (m, 3H), 0.92-0.84 (m, 3H).

LC-MS (Method-B)=686.0 $[M+H]^+$; 98.45% at RT 2.39 min.

HPLC (Method-B)=99.09% at RT 9.47 min.

I-179

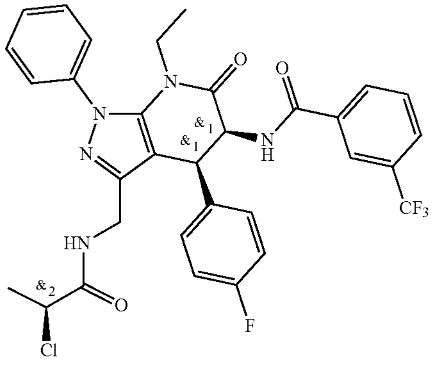

$^1$H NMR (400 MHZ, DMSO-$d_6$) δ=8.61-8.50 (m, 2H), 8.16-8.12 (m, 2H), 7.92 (d, J=7.6 Hz, 1H), 7.73-7.66 (m, 3H), 7.61-7.51 (m, 3H), 7.09 (t, J=8.0 Hz, 2H), 6.96-6.91 (m, 2H), 5.52-5.46 (m, 1H), 4.60-4.54 (m, 1H), 4.36-4.24 (m, 1H), 4.18-4.09 (m, 2H), 3.93-3.86 (m, 1H), 3.06-2.99 (m, 1H), 1.28-1.23 (m, 3H), 0.92-0.84 (m, 3H).

LC-MS (Method-B)=642.63 $[M+H]^+$; 99.90% at RT 1.50 min.

HPLC (Method-B)=99.88% at RT 9.51 min.

I-206

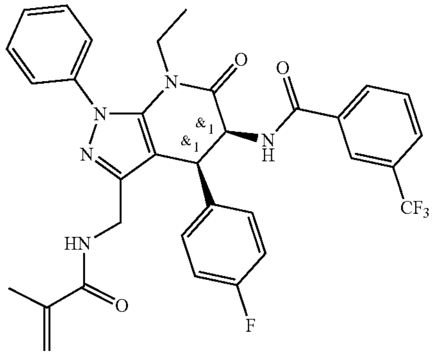

$^1$H NMR (400 MHZ, DMSO-$d_6$) δ=8.47 (d, J=7.6 Hz, 2H), 8.16-8.07 (m, 2H), 7.92 (d, J=8.0 Hz, 1H), 7.73-7.51 (m, 6H), 7.03 (t, J=8.8 Hz, 2H), 6.89-6.85 (m, 2H), 5.48 (t, J=7.2 Hz, 1H), 5.32 (s, 1H), 5.06 (s, 1H), 4.58 (d, J=7.2 Hz, 1H), 4.44-4.38 (m, 1H), 4.16-4.11 (m, 1H), 3.93-3.88 (m, 1H), 3.04-2.99 (m, 1H), 1.53 (s, 3H), 0.90 (t, J=7.2 Hz, 3H).

LC-MS (Method-B)=620.80 $[M+H]^+$; 99.71% at RT 2.08 min.

HPLC (Method-B)=97.82% at RT 9.35 min.

I-230

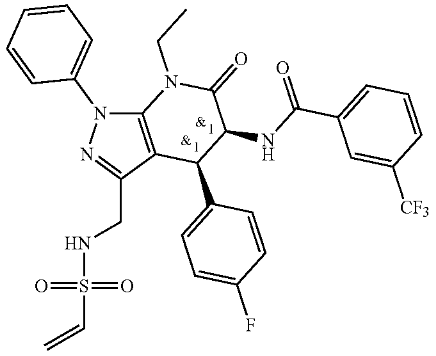

$^1$H NMR (400 MHZ, DMSO-$d_6$) δ=8.53 (d, J=7.6 Hz, 1H), 8.14-8.11 (m, 2H), 7.90 (d, J=7.2 Hz, 1H), 7.69-7.64 (m, 4H), 7.59-7.52 (m, 3H), 7.08 (t, J=8.8 Hz, 2H), 6.99-6.97 (m, 2H), 6.60-6.50 (m, 1H), 5.93-5.89 (m, 2H), 5.48 (s, 1H), 4.67 (d, J=6.8 Hz, 1H), 3.86-3.82 (m, 3H), 3.04-2.99 (m, 1H), 0.88 (t, J=6.8 Hz, 3H).

LC-MS (Method-B)=642.2 $[M+H]^+$; 99.16% at RT 2.33 min.

HPLC (Method-B)=95.88% at RT 9.48 min.

I-198

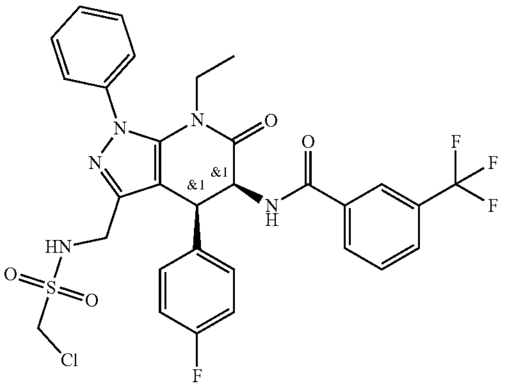

$^1$H NMR (400 MHZ, DMSO-$d_6$) δ=8.54 (d, J=7.6 Hz, 1H), 8.26 (t, J=6.4 Hz, 1H), 8.15-8.12 (m, 2H), 7.92 (d, J=8.0 Hz, 1H), 7.73-7.67 (m, 3H), 7.62-7.52 (m, 3H), 7.10 (t, J=8.8 Hz, 2H), 7.01-6.97 (m, 2H), 5.54 (t, J=7.2 Hz, 1H), 4.84 (d, J=12.0 Hz, 1H), 4.75-4.72 (m, 2H), 4.05-4.01 (m, 2H), 3.93-3.87 (m, 1H), 3.07-3.01 (m, 1H), 0.90 (t, J=7.2 Hz, 3H).

LC-MS (Method-B)=664.0 $[M+H]^+$; 99.04% at RT 2.34 min.

HPLC (Method-B)=99.24% at RT 9.61 min.

I-184

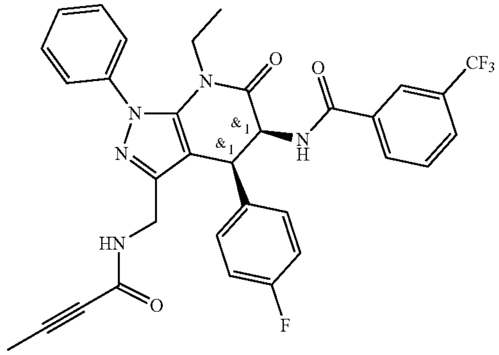

$^1$H NMR (400 MHZ, DMSO-$d_6$) δ=8.67 (t, J=5.6 Hz, 1H), 8.51 (d, J=7.2 Hz, 1H), 8.16-8.13 (m, 2H), 7.93 (d, J=8.0 Hz, 1H), 7.74-7.66 (m, 3H), 7.61-7.52 (m, 3H), 7.10 (t, J=8.8 Hz, 2H), 6.95-6.92 (m, 2H), 5.53-5.49 (m, 1H), 4.58 (d, J=7.2 Hz, 1H), 4.27-4.21 (m, 1H), 4.10-4.05 (m, 1H), 3.94-3.88 (m, 1H), 3.07-2.98 (m, 1H), 1.84 (s, 3H), 0.91 (t, J=6.8 Hz, 3H).

LC-MS (Method-B)=618.2 $[M+H]^+$; 99.14% at RT 2.31 min.

HPLC (Method-B)=99.12% at RT 9.47 min.

I-181

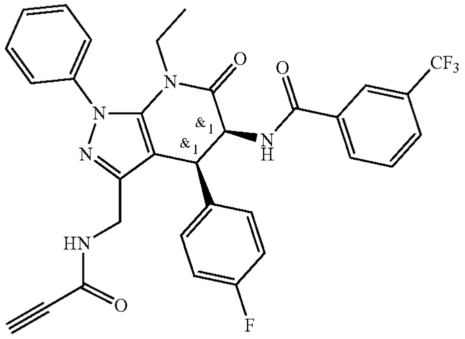

$^1$H NMR (400 MHZ, DMSO-$d_6$) δ=8.99 (t, J=6.0 Hz, 1H), 8.52 (d, J=7.2 Hz, 1H), 8.16-8.13 (m, 2H), 7.93 (d, J=6.8 Hz, 1H), 7.74-7.67 (m, 3H), 7.61-7.52 (m, 3H), 7.08 (t, J=8.8 Hz, 2H), 6.95-6.92 (m, 2H), 5.52 (t, J=7.2 Hz, 1H), 4.58 (d, J=7.2 Hz, 1H), 4.29-4.23 (m, 1H), 4.13-4.08 (m, 1H), 3.97-3.88 (m, 2H), 3.07-2.99 (m, 1H), 0.91 (t, J=7.6 Hz, 3H).

LC-MS (Method-B)=604.2 $[M+H]^+$; 98.41% at RT 2.29 min.

HPLC (Method-B)=97.61% at RT 9.50 min.

I-67

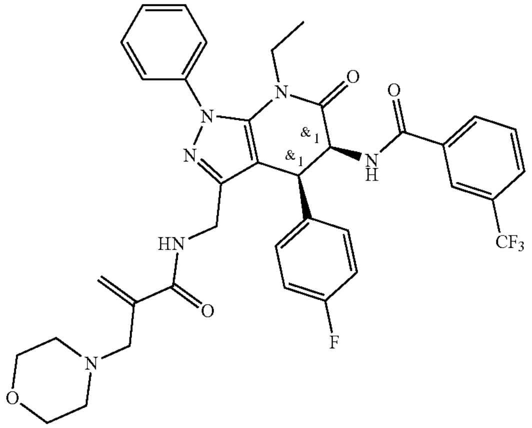

$^1$H NMR (400 MHZ, DMSO-$d_6$) δ=9.13 (s, 1H), 8.52 (d, J=7.6 Hz, 1H), 8.15-8.11 (m, 2H), 7.92 (d, J=8.0 Hz, 1H), 7.73-7.66 (m, 3H), 7.61-7.53 (m, 3H), 7.07 (t, J=8.8 Hz, 2H), 6.95-6.92 (m, 2H), 5.74 (s, 1H), 5.50 (t, J=7.2 Hz, 1H), 5.32 (s, 1H), 4.56 (d, J=7.2 Hz, 1H), 4.31-4.30 (m, 1H), 4.26-4.24 (m, 1H), 3.92-3.90 (m, 1H), 3.40-3.37 (m, 4H), 3.05-3.01 (m, 2H), 2.90-2.87 (m, 1H), 2.25-2.20 (m, 4H), 0.92-0.84 (m, 3H).

LC-MS (Method-B)=705.58 $[M+H]^+$; 99.30% at RT 2.11 min.

HPLC (Method-B)=98.83% at RT 9.54 min.

I-221

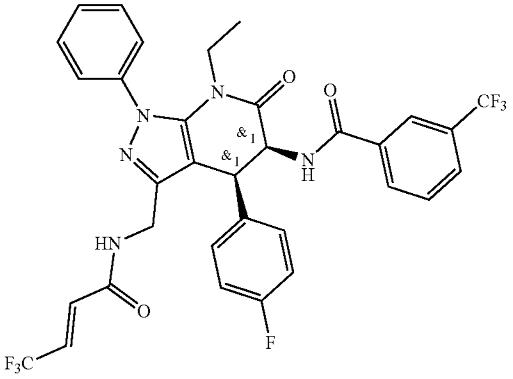

$^1$H NMR (400 MHZ, DMSO-$d_6$) δ=8.79-8.77 (m, 1H), 8.52 (d, J=7.6 Hz, 1H), 8.17-8.13 (m, 2H), 7.92 (d, J=7.6 Hz, 1H), 7.73-7.66 (m, 3H), 7.61-7.52 (m, 3H), 6.99 (t, J=8.8 Hz, 2H), 6.87-6.83 (m, 2H), 6.46-6.41 (m, 1H), 6.18-6.14 (m, 1H), 5.50 (t, J=7.2 Hz, 1H), 4.58-4.50 (m, 2H), 4.16-4.11 (m, 1H), 3.94-3.88 (m, 1H), 3.03-2.98 (m, 1H), 0.89 (t, J=6.8 Hz, 3H).

LC-MS (Method-B)=674.72 $[M+H]^+$; 99.80% at RT 2.12 min.

HPLC (Method-B)=99.18% at RT 9.60 min.

I-232

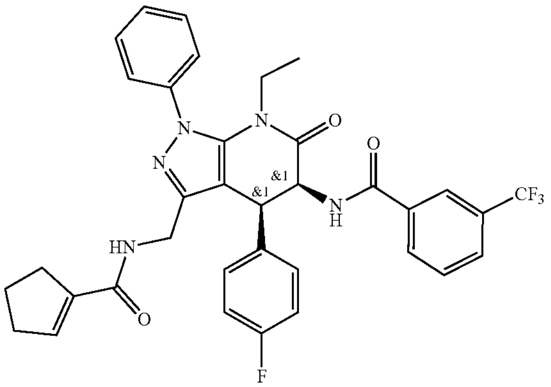

$^1$H NMR (400 MHZ, DMSO-$d_6$) δ=8.47 (d, J=6.8 Hz, 1H), 8.17-8.14 (m, 2H), 7.93-7.88 (m, 2H), 7.73-7.52 (m, 6H), 7.01-6.99 (m, 2H), 6.82 (s, 2H), 6.04 (s, 1H), 5.48 (t, J=7.2 Hz, 1H), 4.55-4.48 (m, 2H), 4.09-4.04 (m, 1H), 3.90 (s, 1H), 3.17-3.16 (m, 1H), 3.01-3.00 (m, 1H), 2.20 (s, 2H), 1.94 (s, 1H), 1.67-1.66 (m, 2H), 0.90 (s, 3H).

LC-MS (Method-B)=646.76 $[M+H]^+$; 99.75% at RT 2.10 min.

HPLC (Method-B)=95.05% at RT 9.53 min.

I-202

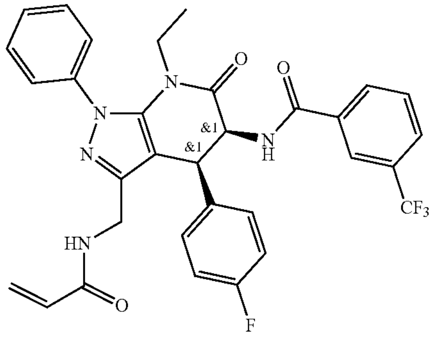

$^1$H NMR (400 MHZ, DMSO-$d_6$) δ=8.50 (d, J=7.2 Hz, 1H), 8.35 (s, 1H), 8.15-8.12 (m, 2H), 7.92 (d, J=7.2 Hz, 1H), 7.73-7.66 (m, 3H), 7.61-7.51 (m, 3H), 7.04 (t, J=8.8 Hz, 2H), 6.91-6.88 (m, 2H), 5.87-5.85 (m, 2H), 5.50 (t, J=7.2 Hz, 1H), 5.39-5.36 (m, 1H), 4.55 (d, J=7.2 Hz, 1H), 4.38-4.33 (m, 1H), 4.18-4.13 (m, 1H), 3.94-3.88 (m, 1H), 3.05-2.99 (m, 1H), 0.90 (t, J=6.8 Hz, 3H).

LC-MS (Method-B)=606.46 $[M+H]^+$; 98.99% at RT 1.43 min.

HPLC (Method-B)=99.00% at RT 9.06 min.

I-182

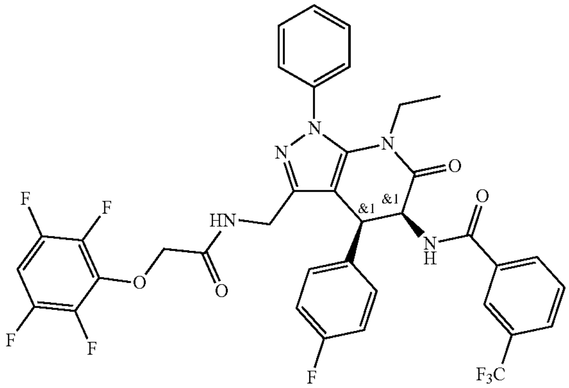

$^1$H NMR (400 MHZ, DMSO-$d_6$) δ=8.51 (d, J=7.2 Hz, 1H), 8.37 (t, J=5.6 Hz, 1H), 8.16-8.12 (m, 2H), 7.92 (d, J=8.0 Hz, 1H), 7.73-7.66 (m, 3H), 7.61-7.51 (m, 4H), 7.04 (t, J=8.8 Hz, 2H), 6.93-6.89 (m, 2H), 5.50 (t, J=7.2 Hz, 1H), 4.56 (d, J=7.2 Hz, 1H), 4.41-4.35 (m, 1H), 4.24-4.14 (m, 3H), 3.92-3.87 (m, 1H), 3.06-2.98 (m, 1H), 0.90 (t, J=6.8 Hz, 3H).

LC-MS (Method-B)=758.2 $[M+H]^+$; 99.73% at RT 2.46 min.

HPLC (Method-D)=99.79% at RT 9.12 min.

I-220

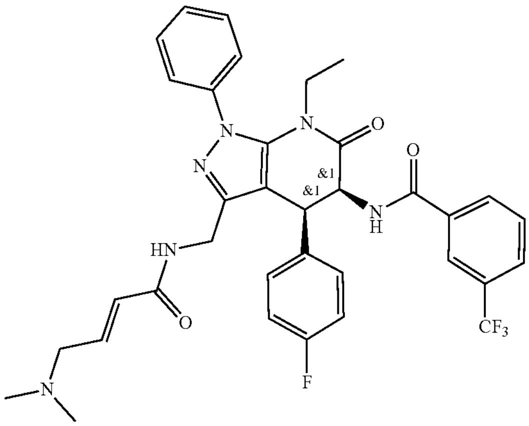

$^1$H NMR (400 MHZ, DMSO-$d_6$) δ=8.50 (d, J=7.2 Hz, 1H), 8.22 (t, J=6.0 Hz, 1H), 8.15-8.12 (m, 2H), 7.92 (d, J=7.6 Hz, 1H), 7.73-7.51 (m, 6H), 7.03 (t, J=8.4 Hz, 2H), 6.90-6.86 (m, 2H), 6.35-6.29 (m, 1H), 5.62-5.58 (m, 1H), 5.49 (t, J=7.2 Hz, 1H), 4.54 (d, J=7.2 Hz, 1H), 4.40-4.35 (m, 1H), 4.15-4.10 (m, 1H), 3.93-3.88 (m, 1H), 3.04-2.98 (m, 1H), 2.86-2.80 (m, 2H), 2.06 (s, 6H), 0.90 (t, J=6.8 Hz, 3H).

LC-MS (Method-B)=663.2 $[M+H]^+$; 98.67% at RT 2.24 min.

HPLC (Method-B)=98.42% at RT 8.66 min.

I-183

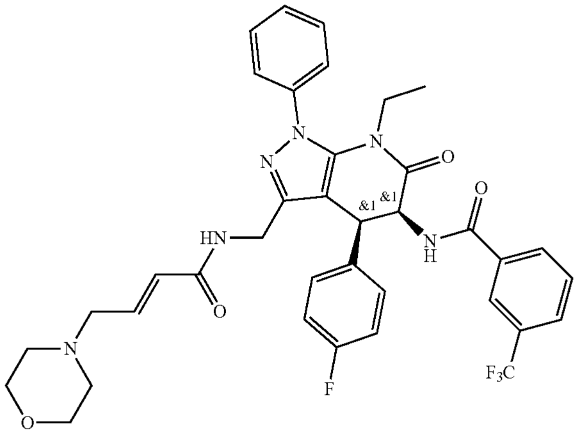

$^1$H NMR (400 MHZ, DMSO-$d_6$) δ=8.45-8.39 (m, 1H), 8.21-8.11 (m, 3H), 7.92 (d, J=7.6 Hz, 1H), 7.73-7.67 (m, 3H), 7.61-7.51 (m, 3H), 7.03 (t, J=8.8 Hz, 2H), 6.89 (s, 2H), 6.34-6.29 (m, 1H), 5.66-5.62 (m, 1H), 5.50-5.46 (m, 1H), 4.55-4.54 (m, 1H), 4.40-4.35 (m, 1H), 4.15-4.11 (m, 1H), 3.93-3.87 (m, 1H), 3.54-3.53 (m, 4H), 3.05-3.01 (m, 1H), 2.89 (s, 2H), 2.27 (s, 4H), 0.90 (t, J=7.2 Hz, 3H).

LC-MS (Method-D)=705.52 $[M+H]^+$; 95.18% at RT 1.96 min.

HPLC (Method-B)=98.37% at RT 8.77 min.

I-240

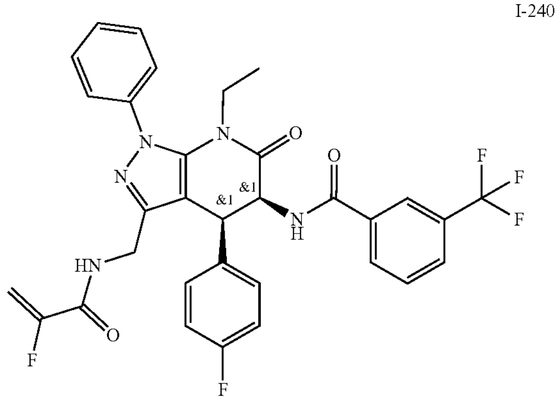 [SMILES: C=C(F)C(=O)NCc1nn(-c2ccccc2)c2c1[C@H](c1ccc(F)cc1)[C@H](NC(=O)c1cccc(C(F)(F)F)c1)C(=O)N2CC]

$^1H$ NMR (400 MHZ, DMSO-$d_6$) δ=8.68 (t, J=6.4 Hz, 1H), 8.48 (d, J=7.2 Hz, 1H), 8.16-8.13 (m, 2H), 7.92 (d, J=7.6 Hz, 1H), 7.73-7.66 (m, 3H), 7.61-7.51 (m, 3H), 7.03 (t, J=8.8 Hz, 2H), 6.89-6.86 (m, 2H), 5.50 (t, J=7.2 Hz, 1H), 5.29-5.16 (m, 1H), 5.00-4.95 (m, 1H), 4.59 (d, J=7.2 Hz, 1H), 4.44-4.39 (m, 1H), 4.18-4.13 (m, 1H), 3.93-3.87 (m, 1H), 3.04-2.99 (m, 1H), 0.90 (t, J=7.2 Hz, 3H).

LC-MS (Method-B)=624.48 $[M+H]^+$; 96.53% at RT 2.11 min.

HPLC (Method-B)=94.46% at RT 8.83 min.

I-169

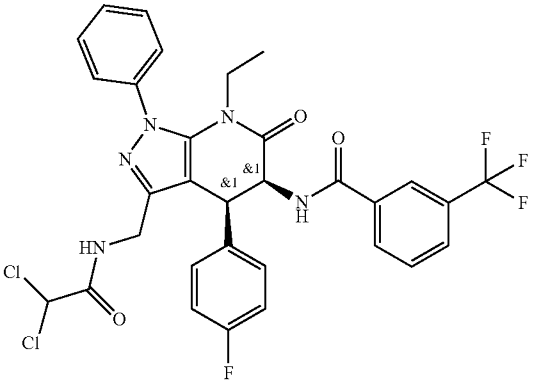

$^1H$ NMR (400 MHZ, DMSO-$d_6$) δ=8.91 (t, J=5.6 Hz, 1H), 8.51 (d, J=7.6 Hz, 1H), 8.15-8.12 (m, 2H), 7.92 (d, J=7.6 Hz, 1H), 7.73-7.67 (m, 3H), 7.61-7.52 (m, 3H), 7.09 (t, J=8.8 Hz, 2H), 6.96-6.93 (m, 2H), 6.14 (s, 1H), 5.51 (t, J=7.2 Hz, 1H), 4.57 (d, J=7.2 Hz, 1H), 4.30-4.19 (m, 2H), 3.92-3.87 (m, 1H), 3.06-3.01 (m, 1H), 0.90 (t, J=6.8 Hz, 3H).

LC-MS (Method-E)=659.8 $[M+H]^+$; 98.90% at RT 2.40 min.

HPLC (Method-B)=98.54% at RT 9.31 min.

I-18

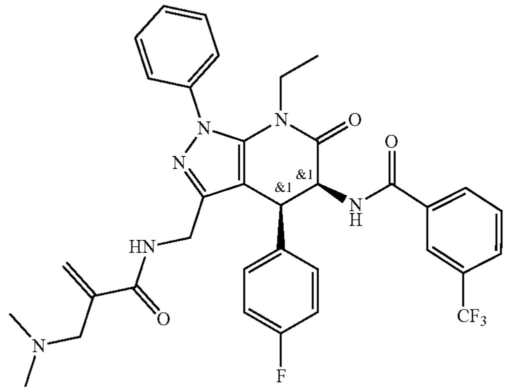

$^1H$ NMR (400 MHZ, DMSO-$d_6$) δ=8.92 (s, 1H), 8.49 (d, J=7.5 Hz, 1H), 8.17-8.12 (m, 2H), 7.92 (d, J=7.6 Hz, 1H), 7.71-7.67 (m, 3H), 7.59-7.52 (m, 3H), 7.05 (t, J=8.8 Hz, 2H), 6.93-6.91 (m, 2H), 5.66-5.50 (m, 2H), 5.26 (s, 1H), 4.56 (d, J=7.2 Hz, 1H), 4.43-4.36 (m, 1H), 4.19-4.14 (m, 1H), 3.90-3.88 (m, 1H), 3.05-3.03 (m, 2H), 2.88-2.85 (m, 1H), 2.00 (s, 6H), 0.91 (t, J=7.2 Hz, 3H).

LC-MS (Method-B)=663.2 $[M+H]^+$; 98.51% at RT 2.50 min.

HPLC (Method-A)=96.85% at RT 6.79 min.

I-205

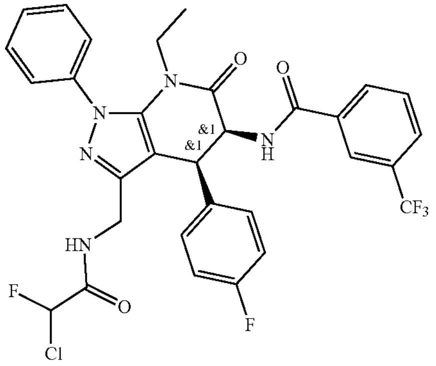

$^1H$ NMR (400 MHZ, DMSO-$d_6$) δ=9.02-8.97 (m, 1H), 8.54-8.51 (m, 1H), 8.15-8.12 (m, 2H), 7.92 (d, J=7.6 Hz, 1H), 7.73-7.67 (m, 3H), 7.61-7.52 (m, 3H), 7.09 (t, J=8.8 Hz, 2H), 6.95-6.91 (m, 2H), 6.35-6.22 (m, 1H), 5.51 (t, J=7.2 Hz, 1H), 5.58 (t, J=7.2 Hz, 1H), 4.38-4.14 (m, 2H), 3.94-3.87 (m, 1H), 3.05-3.00 (m, 1H), 0.90 (t, J=6.4 Hz, 3H).

LC-MS (Method-B)=646.52 $[M+H]^+$; 99.54% at RT 1.48 min.

HPLC (Method-B)=99.14% at RT 9.41 min.

I-204

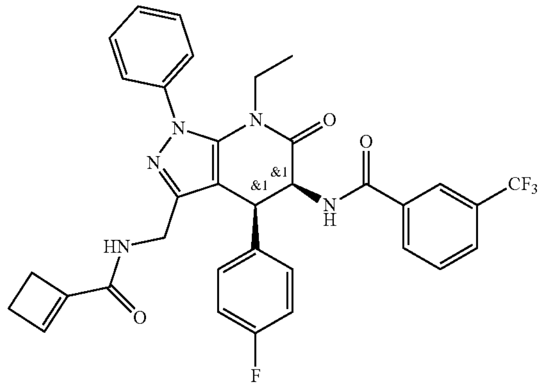

$^1$H NMR (400 MHZ, DMSO-$d_6$) δ=8.48 (d, J=7.2 Hz, 1H), 8.17-8.13 (m, 2H), 8.07-8.04 (m, 1H), 7.92 (d, J=8.0 Hz, 1H), 7.73-7.65 (m, 3H), 7.61-7.51 (m, 3H), 7.03 (t, J=8.8 Hz, 2H), 6.86-6.83 (m, 2H), 6.17 (s, 1H), 5.49 (t, J=7.6 Hz, 1H), 4.53-4.45 (m, 2H), 4.05-4.00 (m, 1H), 3.96-3.87 (m, 1H), 3.05-2.96 (m, 1H), 2.30-2.25 (m, 1H), 2.11 (s, 3H), 0.90 (t, J=7.2 Hz, 3H).

LC-MS (Method-B)=632.60 $[M+H]^+$; 99.27% at RT 1.46 min.

HPLC (Method-B)=97.79% at RT 9.20 min.

I-3

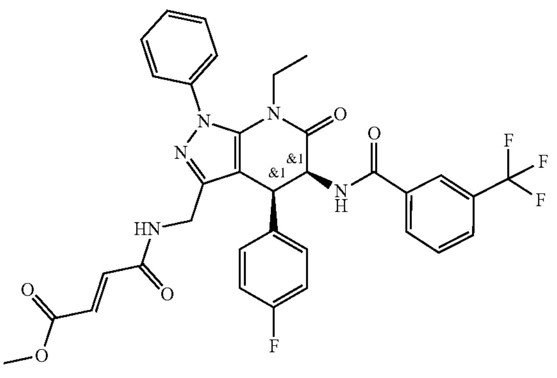

$^1$H NMR (400 MHZ, DMSO-$d_6$) δ=8.79-8.76 (m, 1H), 8.49 (d, J=7.6 Hz, 1H), 8.17-8.13 (m, 2H), 7.92 (d, J=7.6 Hz, 1H), 7.73-7.66 (m, 3H), 7.61-7.51 (m, 3H), 7.00-6.95 (m, 2H), 6.87-6.83 (m, 2H), 6.47-6.43 (m, 1H), 6.27-6.23 (m, 1H), 5.49 (t, J=7.2 Hz, 1H), 4.54-4.44 (m, 2H), 4.19-4.14 (m, 1H), 3.93-3.86 (m, 1H), 3.67 (s, 3H), 3.04-2.98 (m, 1H), 0.89 (t, J=6.8 Hz, 3H).

LC-MS (Method-D)=664.2 $[M+H]^+$; 98.96% at RT 2.28 min.

HPLC (Method-B)=97.69% at RT 9.06 min.

I-203

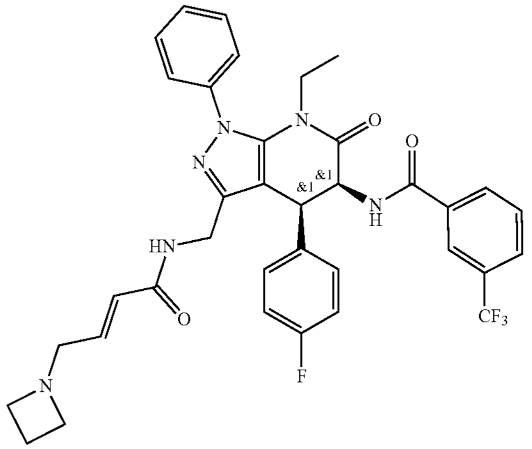

$^1$H NMR (400 MHZ, DMSO-$d_6$) δ=8.49 (d, J=7.6 Hz, 1H), 8.20-8.12 (m, 2H), 7.92 (d, J=7.2 Hz, 1H), 7.73-7.66 (m, 3H), 7.60-7.53 (m, 3H), 7.13-7.01 (m, 2H), 6.97-6.86 (m, 2H), 6.26-6.22 (m, 1H), 5.63-5.59 (m, 1H), 5.51-5.47 (m, 1H), 4.54-4.53 (m, 1H), 4.34-4.32 (m, 1H), 4.20-4.12 (m, 1H), 3.91-3.89 (m, 1H), 3.04-3.00 (m, 6H), 2.71-2.66 (m, 4H), 0.92-0.85 (m, 3H).

LC-MS (Method-D)=675.43 $[M+H]^+$; 97.92% at RT 2.20 min.

HPLC (Method-B)=98.56% at RT 8.98 min.

Example 2: Synthesis of Compound I-73

NMR:

$^1$H NMR spectrum was recorded on Bruker 400 MHz and Varian 400 MHz instruments internally referenced to a tetramethylsilane (TMS) signal. Chemical shifts (δ) and coupling constants (J) were expressed in parts per million and hertz, respectively.

LC-MS:

Method-A: LC-MS_X-Select (Formic acid); Column: X-Select CSH C18 (3.0*50) mm 2.5μ.

Mobile Phase: A: 0.05% Formic acid in water: I (95:5) B: 0.05% Formic acid in CAN.

Inj Volume: 2.0 μL, Column oven temperature: 50 C; Flow Rate: 1.2 mL/min.

Gradient program: 0% B to 98% B in 2.0 minute, hold till 3.0 min, at 3.2 min B conc is 0% up to 4.0 min.

Method-B: Column: X-Bridge BEH C18, (50 mm*3.0 mm,2.5μ) Mobile Phase

A: 2.5 mM Ammonium Bicarbonate in Water+5% I Mobile Phase B: 100% I Flow rate: 1.0 mL/min. Column temperature: 40° C. Gradient Program (B %): 0.0/2, 0.3/2, 2.0/98, 2.8/98, 3.0/2,3.7/2.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5,1/5,8/100,12/100,14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/2,2/2, 12/90, 16/90; Flow: 1.0 mL/min.; Diluent: I: WATER (80:20).

Method-C: Column Name: CHIRALPAK-IK (250×4.6 mm, 5 μm) MobilePhase A: n-HEXANE MobilePhase B: ETOH: MEOH (50/50) Column ID: M-ARDCAL\OLD-028 Flow rate: 1.0 ml/min.

Method-D: Column Name: CHIRALPAK-IC (250×4.6 mm, 5 μm) Column ID: M-ARD-CAL/OLD-005 Mobile-Phase A: 0.1% DEA n-Hexane MobilePhase B: DCM: IPA (50:50) Flow rate: 1.0 ml/min.

Method-E: COLUMN: CHIRALPAK-IG (250×4.6 mm, 5 μm) M.P-A: n-HEXANE M.P-B: ETOH:MEOH (1:1) A/B: 70/30 Flow: 1.0 ml/min.

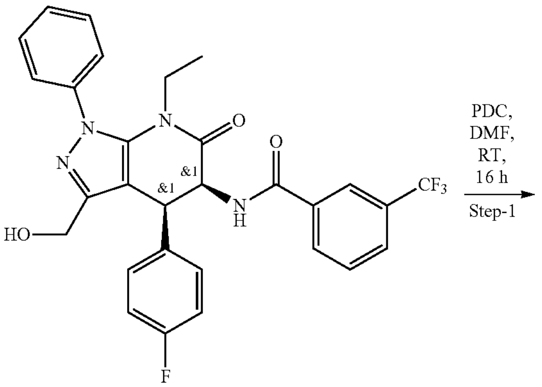

5

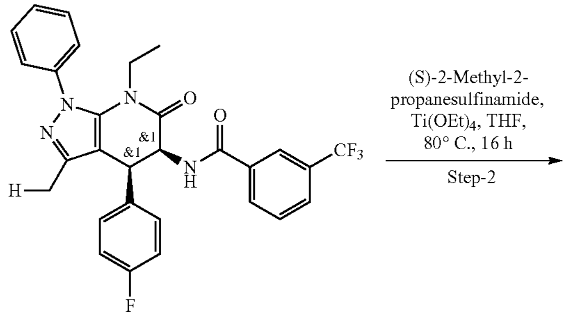

6

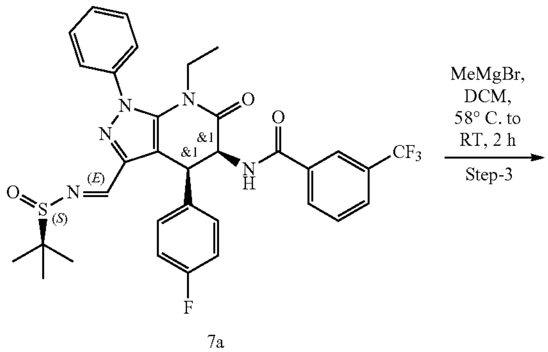

7a

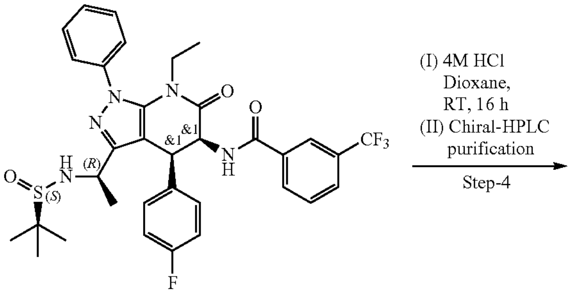

7b

-continued

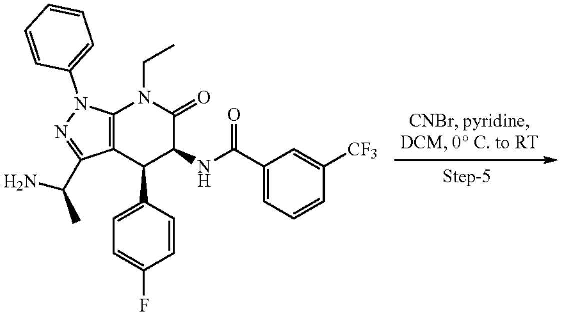

A

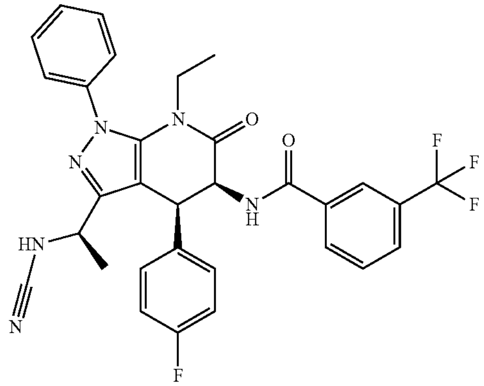

I-73

Step-1: Synthesis of rac-N-((4R,5R)-7-ethyl-4-(4-fluorophenyl)-3-formyl-6-oxo-1-phenyl-4,5,6,7-tetrahydro-1H-pyrazolo[3,4-b]pyridin-5-yl)-3-(trifluoromethyl)benzamide (6)

To a stirred solution of compound-5 (3.0 g, 5.43 mmol) in DMF (30.0 mL) at 0° C., pyridinium dichromate (2.50 g, 6.51 mmol) was added slowly. The reaction mixture was stirred at 25° C. for 16 h. After consumption of the starting material (by TLC), the reaction mixture was quenched with ice cold water (50 mL) and extracted with ethyl acetate (3×40 mL). The organic layer was dried over anhydrous $Na_2SO_4$ and concentrated under reduced pressure. The crude material was purified by medium pressure liquid chromatography by eluting 15-30% EtOAc/heptane to afford compound (6) (2.20 g, 67%) as an off-white solid.

$^1$H NMR (400 MHZ, CHLOROFORM-d, 27° C.): δ 9.88 (s, 1H), 8.61 (d, J=7.2 Hz, 1H), 8.16-8.13 (m, 2H), 7.92-7.90 (m, 1H), 7.83-7.82 (m, 2H), 7.72-7.64 (m, 4H), 7.10 (t, J=8.4 Hz, 2H), 7.01 (t, J=5.2 Hz, 2H), 5.57 (t, J=7.2 Hz, 1H), 4.90 (d, J=7.2 Hz, 1H), 3.91-3.85 (m, 1H), 3.05-3.00 (m, 1H), 0.89 (t, J=6.8 Hz, 3H).

LC-MS (Method-B)=551.1 $[M+H]^+$; 91.53% at RT 2.45 min.

HPLC (Method-B)=97.30% at RT 9.32 min.

Chiral HPLC (Method-C)=Peak-1:14.17% at RT 4.28 min.

Peak-2:85.83% at RT 6.47 min.

Step-2: Synthesis of N-((4RS,5RS)-3-((E)-(((S)-tert-butylsulfinyl)imino)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (7a)

To a stirred solution of compound (6) (2.2 g, 4.0 mmol) in THF (22 mL) was added (s)-2-methylpropane-2-sulfinamide (0.97 g, 8.0 mmol) followed by titanium (IV) ethoxide (1.9 g, 8.0 mmol) at 0° C. The reaction mixture was stirred at 80° C. for 16 h. Progress of the reaction was monitored by TLC. After consumption of the reaction, the reaction mixture was poured into ice cold $NH_4Cl$ solution (150 mL) and extracted with EtOAc (2×150 mL). The organic layer was dried over anhydrous $Na_2SO_4$, concentrated under reduced pressure. The crude material was washed with diethyl ether, filtered, and dried to afford compound (7a) (2.70 g, 96.00%) as an off-white solid.

$^1$H NMR (400 MHZ, DMSO-$d_6$) δ=8.52 (d, J=6.4 Hz, 1H), 8.39 (s, 1H), 8.12-8.10 (m, 2H), 7.92 (d, J=7.6 Hz, 1H), 7.83-7.81 (m, 2H), 7.72-7.62 (m, 4H), 7.10 (t, J=8.8 Hz, 2H), 6.96-6.93 (m, 2H), 5.57 (t, J=6.8 Hz, 1H), 4.99 (d, J=7.2 Hz, 1H), 3.90-3.88 (m, 1H), 3.04-3.02 (m, 1H), 1.17 (s, 9H), 0.94-0.84 (m, 3H).

LC-MS (Method-B)=654.1 [M+H]$^+$; 97.29% at RT 2.51 min.

HPLC (Method-B)=87.97% at RT 9.60 min.

Chiral HPLC (Method-C)=98.99% at RT 7.60 min.

Step-3: Synthesis of N-((4RS,5RS)-3-((R)-1-(((S)-tert-butylsulfinyl)amino)ethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (7b)

To a stirred solution of compound (7a) (2.70 g, 4.13 mmol) in DCM (54 mL) was added $CH_3MgBr$ (3.0 M in diethyl ether) (4.3 g, 12.4 mmol) at −58° C. Reaction was stirred at same temperature for 1 h and then allowed to room temperature, reaction was stirred for 2 h. After consumption of the starting material (by TLC), the reaction was poured into ice cold $NH_4Cl$ solution (25 mL) and extracted with DCM (2×125 mL). The organic layer was dried over anhydrous $Na_2SO_4$, concentrated under reduced pressure. The obtained crude material was washed with diethyl ether to afford (7b) (2.4 g, 69%) as an off-white solid. Obtained crude material was used for the next step without any further purification.

$^1$H NMR (400 MHZ, DMSO-d6) δ=8.50-8.42 (m, 1H), 8.15-8.11 (m, 1H), 7.97-7.91 (m, 1H), 7.73-7.52 (m, 6H), 7.18-7.09 (m, 2H), 6.98-6.95 (m, 2H), 5.46 (t, J=7.2 Hz, 1H), 5.17-5.15 (m, 1H), 4.75 (d, J=6.8 Hz, 1H), 4.23-4.19 (m, 2H), 3.90-3.85 (m, 1H), 3.09-3.04 (m, 1H), 1.47 (d, J=6.8 Hz, 2H), 1.32-1.14 (m, 2H), 1.07-0.81 (m, 11H).

LC-MS (Method-A)=670.39 [M+H]$^+$; 81.08% at RT 2.48, 2.51 min.

HPLC (Method-B)=58.15% at RT 9.14 min.

Chiral HPLC (Method-C)=Peak-1:87.82% at RT 5.85 min.

Peak-2:10.23% at RT 8.93 min.

Step-4: Synthesis of N-((4S,5S)-3-((R)-1-aminoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (Compound A)

To a stirring solution of compound (7b) (2.4 g, 3.3 mmol) in dichloromethane (25 mL) was added (4M Dioxane in HCl, 3.3 mL) at room temperature under inert atmosphere. The reaction mixture was stirred at 25° C. for 16 h. Progress of the reaction was monitored by TLC. After consumption of the starting material (by TLC), reaction mixture was concentrated under reduced pressure to get crude compound. The Obtained crude compound was purified by Chiral HPLC. Peak-4 from Chiral HPLC was evaporated under reduced pressure to afford compound A (0.7 g, 40%) as an off-white solid.

$^1$H NMR (400 MHZ, DMSO-d6) δ=8.53 (d, J=7.2 Hz, 1H), 8.16-8.13 (m, 2H), 7.92 (d, J=8.0 Hz, 1H), 7.73-7.53 (m, 6H), 7.11 (t, J=8.8 Hz, 2H), 7.01-6.99 (m, 2H), 5.50 (t, J=7.2 Hz, 1H), 4.71 (d, J=6.8 Hz, 1H), 4.04 (d, J=6.0 Hz, 1H), 3.91-3.86 (m, 2H), 3.08-3.03 (m, 2H), 1.13-1.04 (m, 3H), 0.92 (t, J=6.0 Hz, 3H).

LC-MS (Method-B)=566.3 [M+H]$^+$; 83.40% at RT 2.42 min.

HPLC (Method-B)=97.11% at RT 8.75 min.

Crude Chiral HPLC (Method-D):

Peak-1:8.20% at RT 5.45 min. Peak-2:0.6% at RT 7.47 min.

Peak-3:27.89% at RT 9.06 min. Peak-4=63.22% at RT 11.46 min (desired).

Step-5: Synthesis of N-((4S,5S)-3-((R)-1-cyanamidoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-73)

To a stirring solution of compound (compound A) (Peak-4 from step-4) (350 mg, 0.618 mmol) in dichloromethane (18 mL) were added pyridine (0.14 g, 1.85 mmol) and cyanogen bromide 5M in I (0.24 g, 0.61 mmol) at 0° C. under inert atmosphere. The reaction mixture was stirred at room temperature for 16 h. Progress of the reaction was monitored by LCMS and TLC. After consumption of the starting material (monitored by TLC), the reaction mixture was quenched with ice cold solution of saturated $NaHCO_3$ (10 mL), extracted with DCM (2×10 mL). The combined organic layer was dried over anhydrous $Na_2SO_4$ and concentrated under reduced pressure to get crude compound and was purified by medium pressure liquid chromatography eluting with 0-45% EA in Heptane, product containing fractions were collected to afford I-73 (90.00 mg, 23.8%) as a light brown solid.

$^1$H NMR (400 MHZ, DMSO-d6) δ 8.53 (d, J=7.2 Hz, 1H), 8.16-8.13 (m, 2H), 7.92 (d, J=8.0 Hz, 1H), 7.73-7.68 (m, 3H), 7.62-7.52 (m, 3H), 7.26 (d, J=5.2 Hz, 1H), 7.11 (t, J=4.8 Hz, 2H), 7.01-6.97 (m, 2H), 5.54 (t, J=7.6 Hz, 1H), 4.67 (d, J=6.8 Hz, 1H), 4.33-4.27 (m, 1H), 3.91-3.85 (m, 1H), 3.09-3.02 (m, 1H), 1.23-1.20 (m, 3H), 0.91 (t, J=7.2 Hz, 3H).

LC-MS (Method-B)=591.24 [M+H]$^+$; 98.75% at RT 2.17 min.

HPLC (Method-B)=97.09% at RT 8.91 min.

Chiral HPLC (Method-E)=99.30% at RT 5.74 min.

Example 3: TR-FRET Assay

The TR-FRET assay was designed following the Scott et al. protocol (Scott et al., Nat Chem Biol. 2017 August; 13 (8): 850-857. Doi: 10.1038/nchembio.2386). The recombinant form of the DCN1 (DCUND1) protein PONY domain was produced using an *E. coli* expression system at Viva Biotech (China). The DCN1 protein was biotinylated (EZ sulfo-NHS-LC-biotin; Thermofisher) for labeling with streptavidin terbium (Tb) cryptate in the reaction. The probe was changed to a non-covalent DCN1 inhibitor labeled with carboxyfluorescein (FAM; Zhou et al., *Nat Commun.* 2017; 8:1150. Doi: 10.1038/s41467-017-01243-7). Buffer conditions were modified to enhance protein stability by exchanging Tween20 for TritonX and increasing NaCl to 200 mM. The compounds were screened against 5 nM DCN1 and 20 nM FAM-probe or 0.31 nM DCN1 and 900 nM total probe (100 nM FAM-labeled plus 800 nM unlabeled). The TR-FRET ratio between Tb-DCN1 and the FAM-labeled probe was measured in a 384-well opti-plate (Perkin Elmer) using a plate reader (BMG) at 1, 5, and 24 hrs after treatment with compound (final DMSO concentration of 0.1%). The ratio was normalized to the high (DCN1 and FAM-probe) and low (DCN1 and no probe) controls for a readout of % activity (=100*(x−low)/(high−low).

Example 4: Intact Protein MS Analysis with the RapidFire-TOF System

DCN1 protein, His-TEV-DCN1, were expressed in *E. Coli*. The His-tagged protein was first purified with an Ni-NTA column. The His-tag was cleaved using His-tag TEV protease and the His-tags were removed using a second Ni-NTA column. Protein purity was verified with SDS-PAGE and intact MS. DCN1 was dissolved in a buffer containing 25 mM Tris-HCl, 200 mM NaCl, and 1 mM DTT at 400 nM. 11 concentrations of compounds were added to the DCN1 solution and incubated at room temperature for 3 hours, unless otherwise specified. The reaction plates were quenched by adding 0.2% formic acid. Quenched assay plates were analyzed with an Agilent RapidFire 360 system connected to an Agilent 6545 Q-TOF mass spectrometer equipped with an AJS source. 10 μL of sample volume was loaded onto a custom packed cartridge (4 μL, PLRP-S 30 μm/1000 Å pore; Optimize Technologies) with loading buffer (dd$H_2O$ with 0.09% (vol/vol) formic acid and 0.01% (vol/vol) trifluoroacetic acid; 1.25 ml/min) for 6 seconds before being eluted directly into the mass spectrometer in elution buffer (80% acetonitrile with 0.09% (vol/vol) formic acid and 0.01% (vol/vol) trifluoroacetic acid; 0.5 ml/min) for 7 seconds. The cartridge was re-equilibrated with loading buffer for 1 second before collection of the next sample. The Q-TOF was operated in TOF-only positive ionization mode set to the following parameters: Gas Temp=350 C, Drying Gas=7 l/min, Nebulizer=50 psi, Sheath Gas Temp=400 C, Sheath Gas Flow=12 l/min, Vcap=4000 V, Nozzle Voltage=1000 V, Fragmentor=125 V, Skimmer=65 V and Oct 1 RF Vpp=750V. Raw MS data files were deconvoluted and analyzed using the Agilent MassHunter Bioconfirm software package to identify both parent protein and expected compound adduct mass signatures.

Example 5: Synthesis of Compound I-13

NMR:

$^1$H NMR spectrum was recorded on Bruker 400 MHz and Varian 400 MHz instruments internally referenced to a tetramethylsilane (TMS) signal. Chemical shifts (8) and coupling constants (J) were expressed in parts per million and hertz, respectively.

LC-MS:

Method-A: LCMS_X-Select (Formic acid); Column: X-Select CSH C18 (3.0*50) mm 2.5μ. Mobile Phase: A: 0.05% Formic acid in water: I (95:5) B: 0.05% Formic acid in CAN Inj Volume: 2.0 μL, Column oven temperature: 50° C.; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

Method-C: Column: X-Select CSH C18, (50 mm*3.0 mm, 2.5μ) Mobile Phase A: 0.05% TFA in Water Mobile Phase B: 0.05% TFA in Acetonitrile Flow rate: 1.0 mL/min. Column temperature: 40° C. Gradient Program (B %): 0.0/2, 0.3/2,2.0/98, 2.8/98, 3.0/2,3.7/2.

Method-D: Column: X-Select CSH C18 (3.0*50 mm, 2.5 μm), Mobile Phase A: 2.5 Mm Ammonium Bicarbonate in $H_2O$+5% I Mobile Phase B: 100% I, Gradient % B: 0/2, 0.3/2,2.0/98,2.8/98,3.0/2,3.7/2.

Method-E: Column: X-Bridge BEH C18, (50 mm*3.0 mm, 2.5μ) Mobile Phase A: 2.5 mM Ammonium Bicarbonate in Water+5% I Mobile Phase B: 100% I Flow rate: 1.0 mL/min. Column temperature: 40° C. Gradient Program (B %): 0.0/2, 0.3/2, 2.0/98, 2.8/98, 3.0/2,3.7/2.

HPLC:

Method-A: Column: X Select CSH C18 (150×4.6) mm, 3.5μ; Mobile phase A: 0.1% FA in Water: I (95:05); Mobile phase B: Acetonitrile; Gradient Programme: T/B %: 0.01/5, 1/5,8/100,12/100,14/5, 18/5; Flow rate: 1.2 ml/min.

Method-B: Column: X-Bridge CSH C18 (150×4.6 mm, 3.5 μm); Mobile Phase-A: 5 mM $NH_4HCO_3$; Mobile Phase-B: I; Programme: T/B %: 0.01/2,2/2,12/90,16/90; Flow rate: 1.0 mL/min.; Diluent: I: WATER (80:20).

Method-C: Column: X SELECT CSH C18 (150×4.6 mm, 3.5μ); Mobile Phase A: 0.05% TFA in water: I (95:05); Mobile Phase B: 0.05% TFA in water: CAN (05:95); Programme: T/B %: . 0.01/10,12/90,16/90; Flow rate: 1 mL/min.; Diluent: WATER: I (80:20).

Method-D: Column: X-Bridge CSH C18 (4.6*150) mm 5u Mobile Phase: A-0.1% TFA in water B-Acetonitrile Inj Volume; 5.0 μL, Flow Rate: 1.2 mL/minute Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in Hexane Mobile Phase B: IPA A/B: 60/40 Flow: 1.0 ml/MIN PDA: OJ-H_015.

Method-F: Column: ACE Excel 2 C18-AR, 100 mm×3.0 mm Mobile Phase A: 0.05% TFA in Water Mobile Phase B: 0.05% TFA in Acetonitrile Colum Temperature: 40° C. Flow Rate: 0.6 mL/min Gradient: 0/5, 1/5, 6/90, 8.5/90, 8.8/5, 11/5.

Method-G: Column: CHIRAL PAK-IC (250×4.6 mm, 5 μm) Mobile Phase A: 0.1% DEA in Hexane Mobile Phase B: EtOH/MeOH (50/50) A: B: 80/20 Flow 1.0 ml/min.

Method-H: Column: X-Bridge C18 (4.6*150) mm 5u Mobile Phase: A-5 mM Ammonium Acetate B-Acetonitrile Flow Rate: 1.0. mL/minute Gradient program: Time (min)/B Conc.: 0.01/5, 1.0/5, 8.0/100, 12.0/100, 14.0/5, 18.0/5.

Method-I: Column: CHIRALCEL-OJ-H (250×4.6 mm, 5 μm) mobile Phase A: n-Hexane; Mobile Phase B: EtOH: MeOH (1:1) A/B: 50/50 Flow: 1.0 ml/min.

Method-J: Column: CHIRALCEL-OX-H Mobile Phase A: n-Hexane Mobile Phase B: IPA Flow: 1.0 ml/min.

Method-K: Column Name: CHIRALPAK-IG (250×4.6 mm, 5 μm), Mobile Phase A: 0.1% DEA n-Hexane, Mobile Phase B: DCM: MeOH (50:50), Flow rate: 1.0 ml/min.

Method-L: Column IC-5 (30×250*4.6 mm,5μ) Mobile phase A N-Hexane Mobile phase B IPA: DCM (1:1) Eluent A: B: −70-30 Total Flow rate (mL/min) 42.

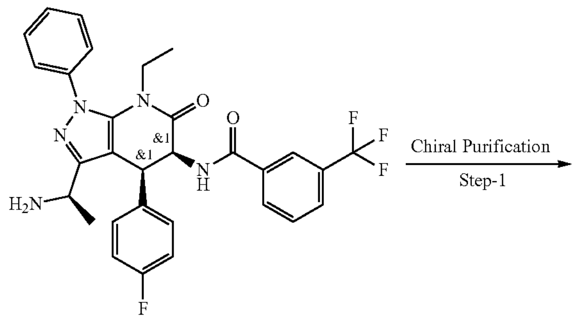

5-1

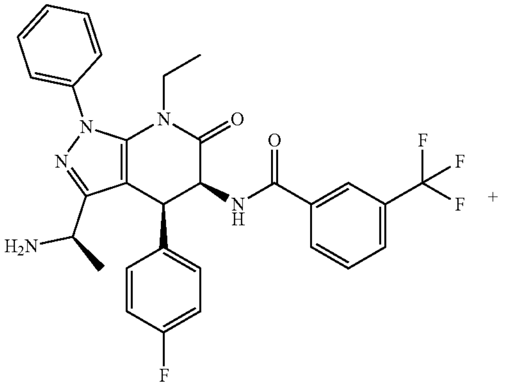

5-2

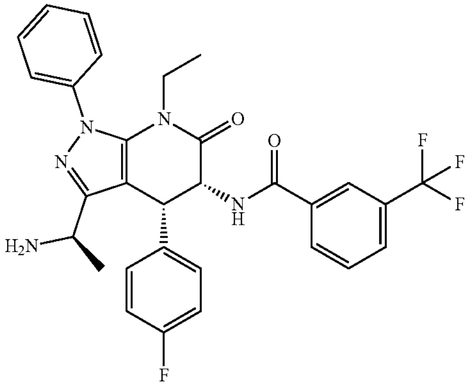

5-3

Step-1: Synthesis of N-((4R*,5R*)-3-((R)-1-aminoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (Compound 5-2) & N-((4R*,5R*)-3-((R)-1-aminoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (Compound 5-3)

The compound 5-1 (500 mg, 0.88 mmol) was purified by Chiral-HPLC (Method-K) purification and two fractions were collected. Both fractions were collected and concentrated to afford Fraction-1 5-2 (150 mg, 28.87%) and Fraction-2 mixture (300 mg). Fraction-2 was further purified by Chiral-HPLC (Method-L) purification and product containing fractions were collected and concentrated to afford pure compound 5-3 (150 mg, 49.50%).

$^1$H NMR (400 MHZ, DMSO-$d_6$) δ=8.50 (d, J=7.2 Hz, 1H), 8.16 (t, J=6.4 Hz, 2H), 7.93 (d, J=7.6 Hz, 1H), 7.73-7.65 (m, 3H), 7.59 (t, J=6.8 Hz, 2H), 7.53-7.49 (m, 1H), 7.12 (t, J=8.8 Hz, 2H), 7.01-6.97 (m, 2H), 5.51 (t, J=7.2 Hz, 1H), 4.72 (d, J=7.2 Hz, 1H), 3.92-3.86 (m, 2H), 3.10-3.01 (m, 1H), 1.23 (s, 2H), 1.10 (d, J=6.8 Hz, 3H), 0.91 (t, J=6.8 Hz, 3H).

LC-MS (Method-B)=566.2 [M+H]$^+$; 99.00% at RT 2.51 min.

HPLC (Method-B)=96.95% at RT 8.64 min.

Chiral HPLC (Method-K)=98.62% at RT 12.44 min.

Compound 5-3:

$^1$H NMR (400 MHZ, DMSO-$d_6$) δ=8.52 (d, J=7.2 Hz, 1H), 8.16 (t, J=6.4 Hz, 2H), 7.93 (d, J=7.6 Hz, 1H), 7.73-7.65 (m, 3H), 7.59 (t, J=7.2 Hz, 2H), 7.53-7.49 (m, 1H), 7.12 (t, J=8.8 Hz, 2H), 7.00-6.97 (m, 2H), 5.51 (t, J=7.2 Hz, 1H), 4.72 (d, J=7.2 Hz, 1H), 3.91-3.85 (m, 2H), 3.07 (m, 2H), 1.74 (s, 1H), 1.10 (d, J=6.4 Hz, 3H), 0.93 (t, J=6.8 Hz, 3H).

LC-MS (Method-C)=566.2 [M+H]$^+$; 99.76% at RT 2.37 min.

HPLC (Method-B)=99.48% at RT 8.72 min.

Chiral HPLC (Method-L)=100% at RT 7.95 min.

Synthesis of I-13

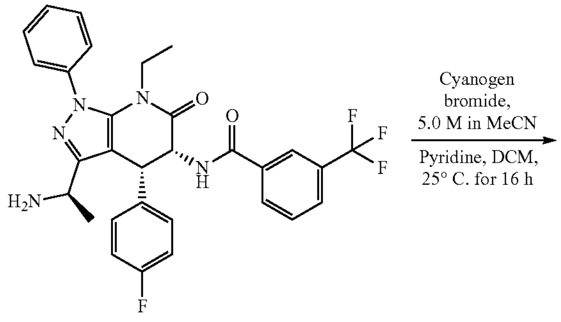

5-3

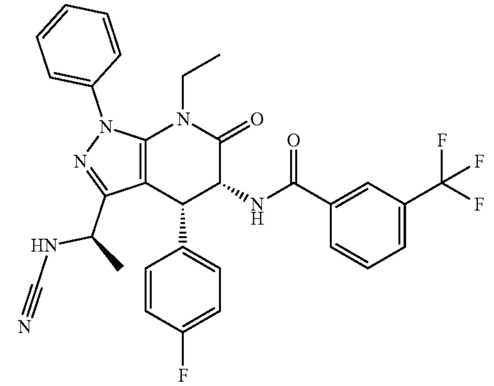

I-13

Step-1: Synthesis of N-((4R,5R)-3-((R)-1-cyanamidoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide I-13)

To a stirring solution of Compound 5-3 (120 mg, 0.212 mmol) in dichloromethane (6 mL) was added pyridine (0.05 g, 0.63 mmol) and cyanogen bromide 5M in I (0.08 g, 0.21 mmol) at 25° C. under inert atmosphere. Then the reaction mixture was stirred at 25° C. for 16 h. The reaction progress was monitored by TLC and LCMS. After consumption of starting material, the reaction mixture was quenched with ice cold water (10 mL) and extracted with DCM (2×10 mL). The combined organic layer was dried over anhydrous sodium sulphate and concentrated under reduced pressure to afford the crude compound. The obtained crude was purified by Prep-HPLC and followed by lyophilization to afford the pure I-13 (32 mg, 25.19%) as a pale-brown solid.

$^1$H NMR (400 MHZ, DMSO-d6) δ=8.54 (d, J=7.6 Hz, 1H), 8.16 (t, J=4.8 Hz, 2H), 7.93 (d, J=8.0 Hz, 1H), 7.73-7.68 (m, 3H), 7.62-7.52 (m, 3H), 7.26 (d, J=5.2 Hz, 1H), 7.13 (t, J=8.8 Hz, 2H), 7.00-6.97 (m, 2H), 5.55 (t, J=7.2 Hz, 1H), 4.68 (d, J=7.2 Hz, 1H), 4.33-4.27 (m, 1H), 3.91 (m, 1H), 3.09 (m, 1H), 1.22 (d, J=6.8 Hz, 3H), 0.93 (t, J=6.8 Hz, 3H).

LC-MS (Method-B)=591.2 $[M+H]^+$; 99.01% at RT 2.37 min.

HPLC (Method-B)=97.84% at RT 8.97 min.

Chiral HPLC (Method-G)=99.47% at RT 6.13 min.

Example 6: Induction of Fetal Hemoglobin in a Humanized Mouse Model

A humanized mouse model was developed in which the clinical standard of care treatment, hydroxyurea (HU), was demonstrated to induce both fetal hemoglobin mRNA (HBG1) and protein (HbF). An exemplified compound, I-73, was shown to achieve in vivo serum exposure levels in wild-type mice predicted to be sufficient for fetal hemoglobin induction. Upon treatment with I-73, an induction of both HBG1 mRNA and HbF protein was observed in human erythroid progenitor cells in the humanized mouse model. The ratio of fetal HBG1 hemoglobin mRNA to adult hemoglobin mRNA (HBB) induced by I-73 is significantly greater than HU standard of care.

Results: To evaluate induction of target cell activity in the bone marrow, a humanized mouse model was developed. This model entails the reconstitution of human hematopoietic progenitor cells within the bone marrow of immunodeficient nonirradiated NOD.Cg-Kit$^{W-41J}$ Tyr+Prkdc$^{scid}$ Il2rg$^{tm1\,Wjl}$/ThomJ (NBSGW) strain recipient mice. These mice are competent to engraft and differentiate human erythroid progenitor cells that express human adult hemoglobin mRNA and protein subunits within bone marrow. Notably, this model does not permit the final differentiation of erythroid precursor cells into enucleated circulating erythrocytes and, hence, precludes the evaluation of human hemoglobin in circulating blood. Hydroxyurea, a small molecule used as the standard of care in the treatment of Sickle Cell Disease, significantly induces fetal hemoglobin mRNA and protein within the human progenitor cell compartment providing confidence in translational relevance of the model.

Figure 1B:
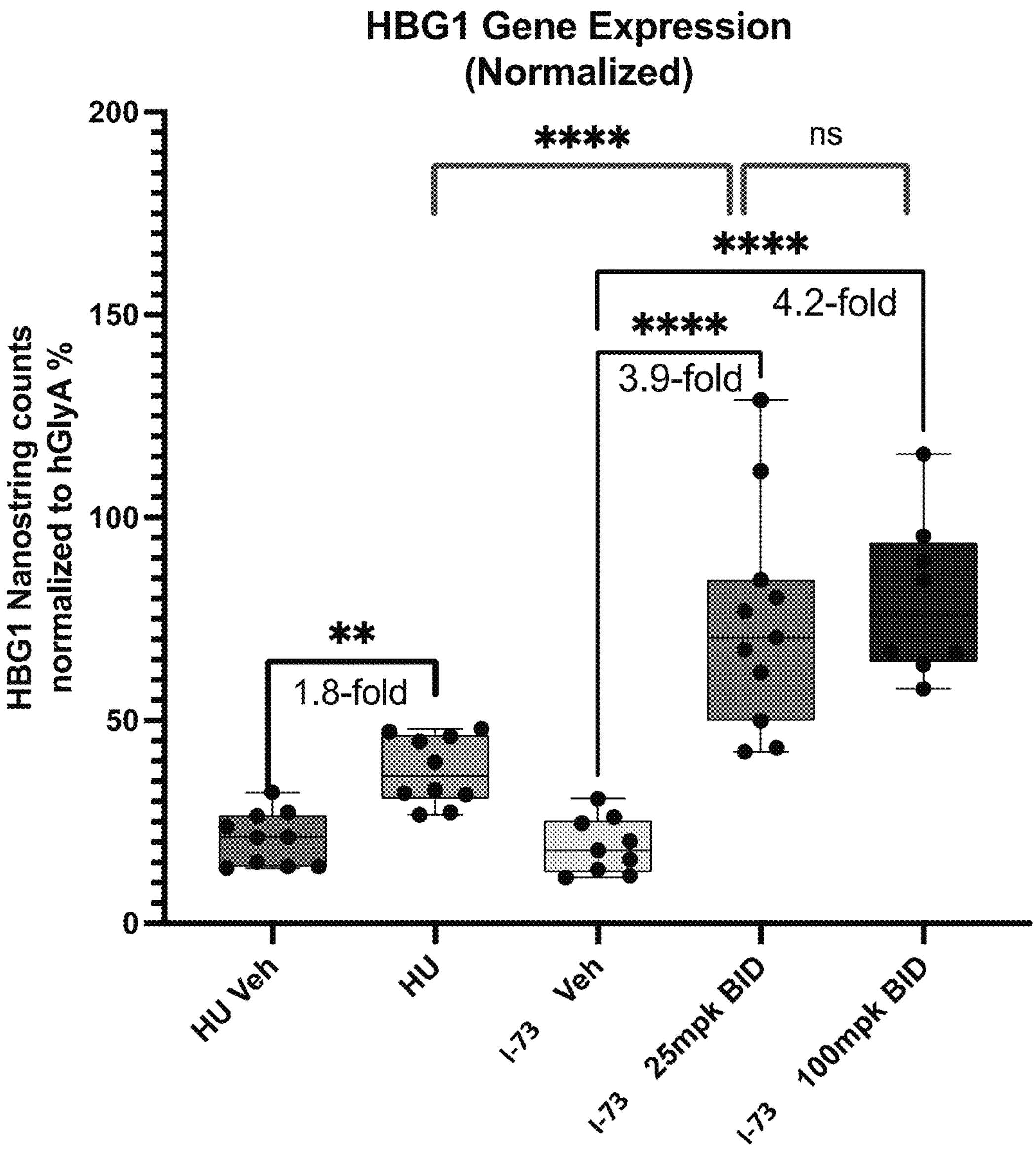
Figure 1C:
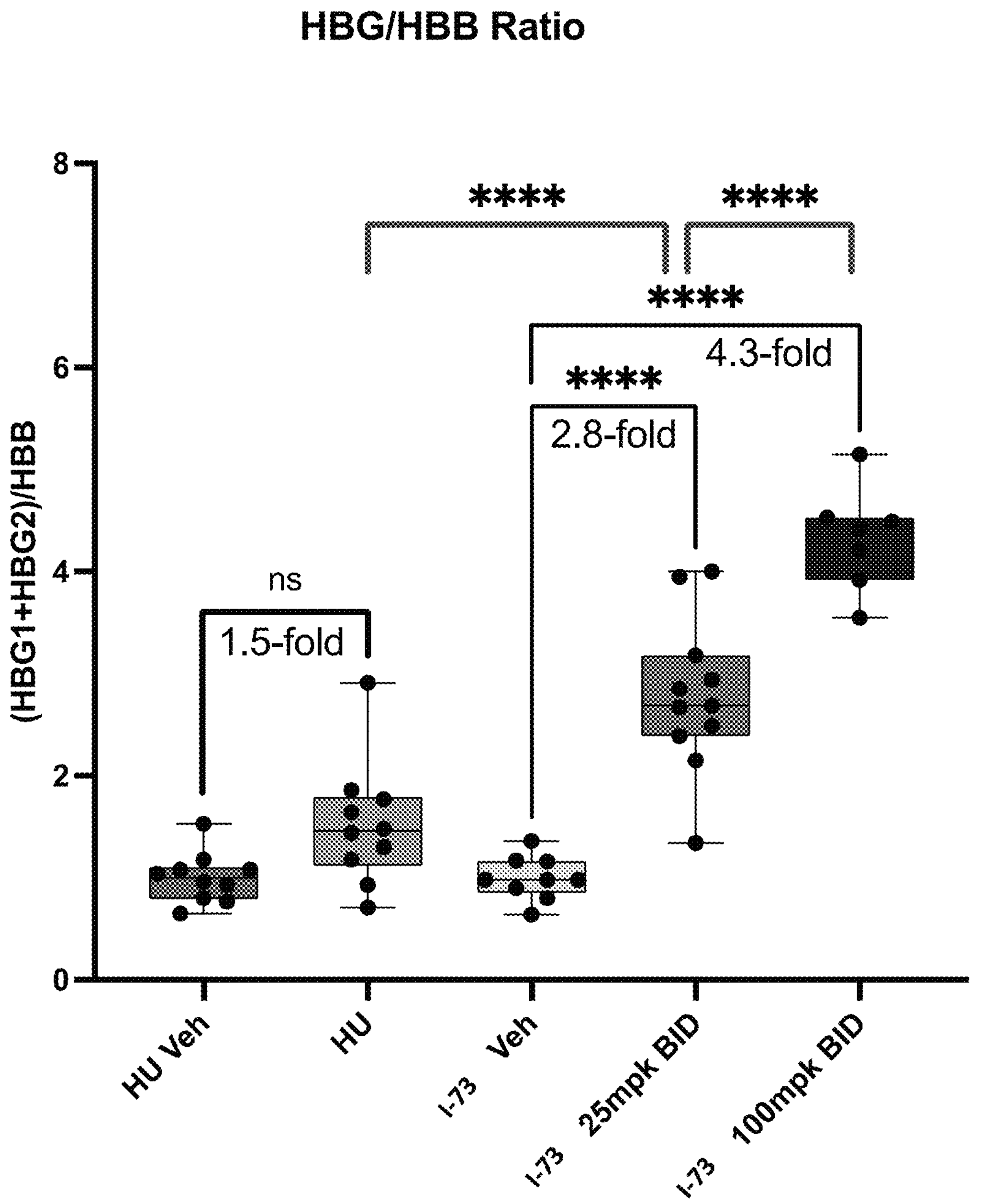
Figure 2:
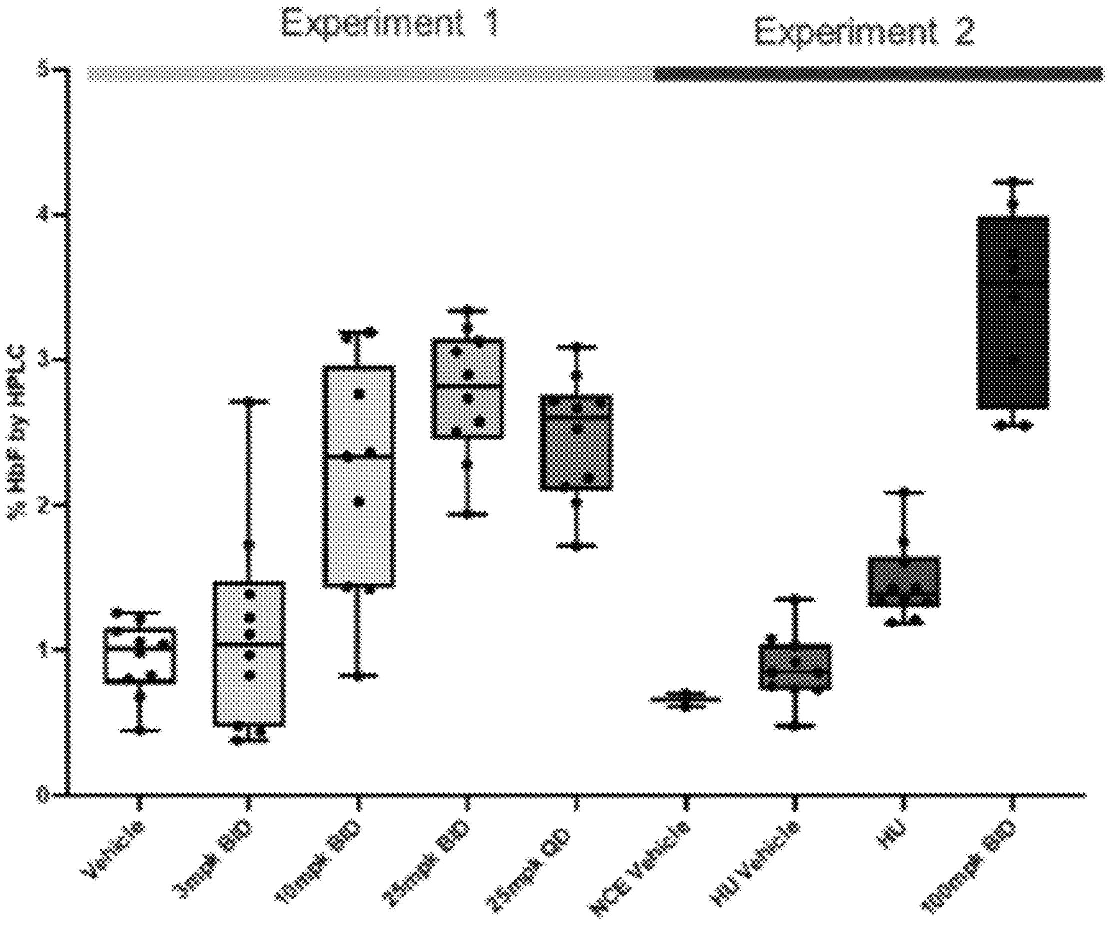
FIG. 2 depicts a graph showing fetal hemoglobin protein (HbF) expression for various dosages of I-73 (Experiment 1), and I-73 compared to vehicle and hydroxyurea (Experiment 2).
Figure 3A:
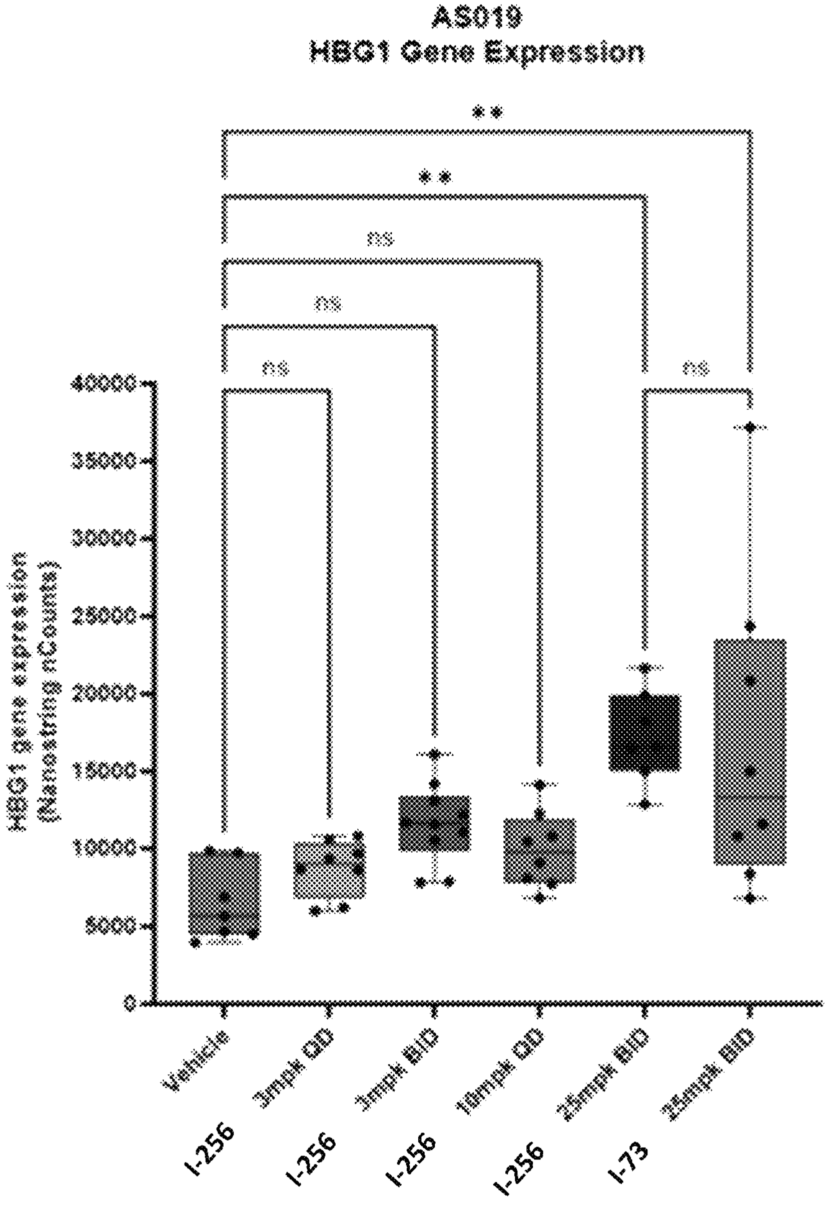
FIGS. 3A, 3B and 3C show Nanostring data on induction of the HbF gene, HBG1 by I-256 and I-73.
Figure 3B:
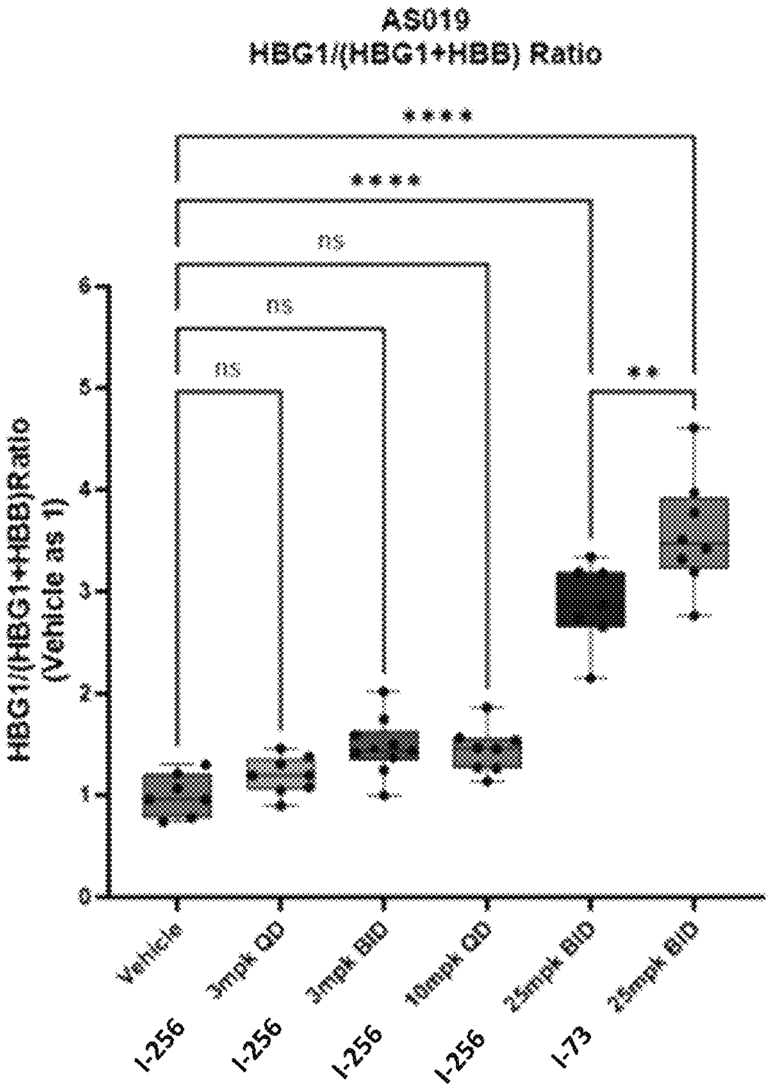
Figure 3C:
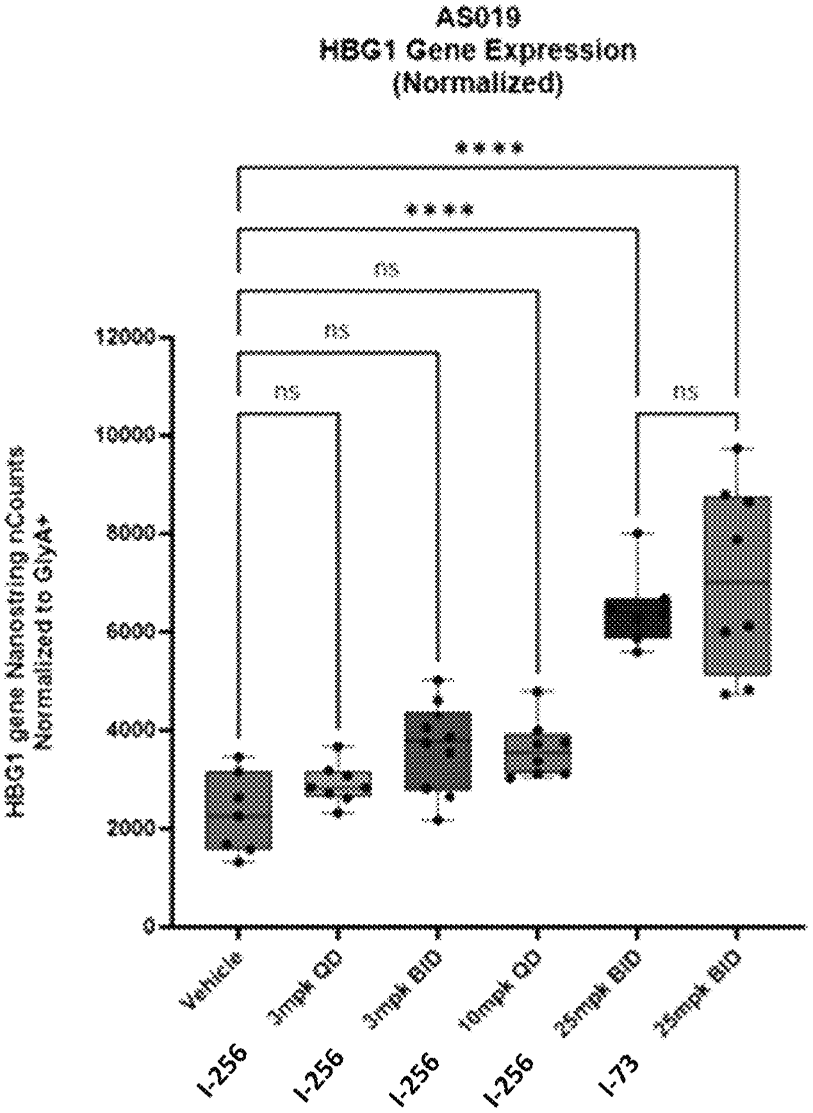
Figure 4A:
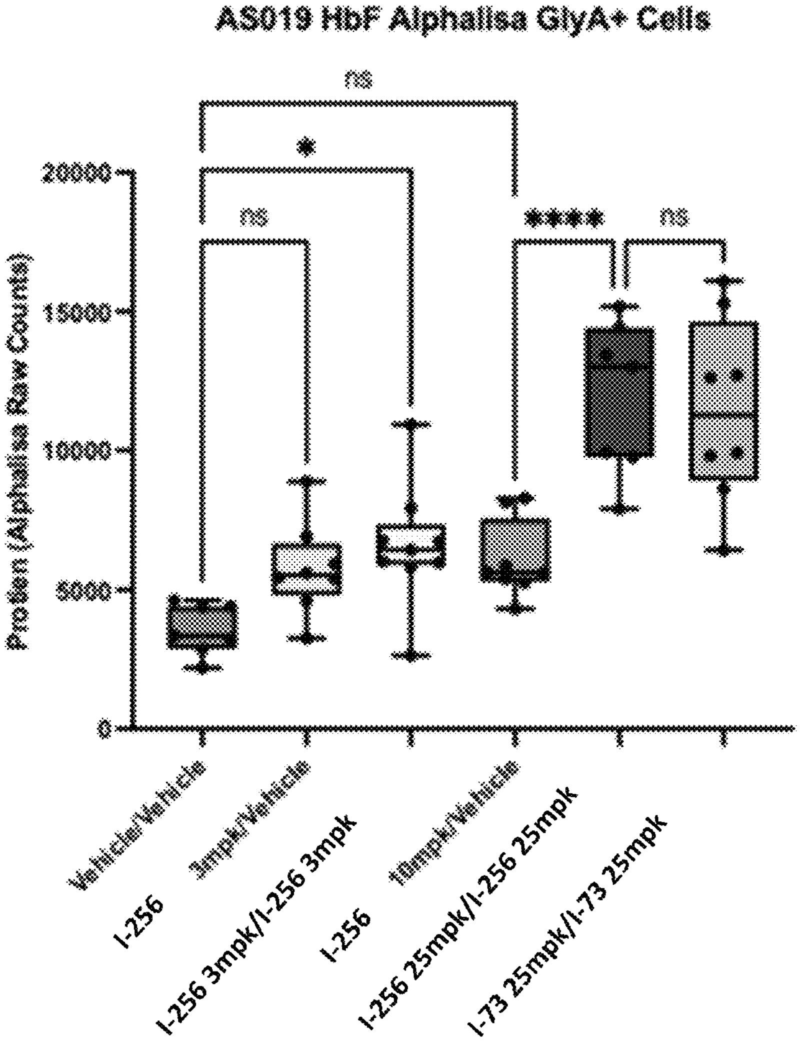
FIG. 4A shows HbF protein detected from FACS sorted GlyA+ human erythroid precursor cells exposed to I-73 and I-256.
Figure 4B:
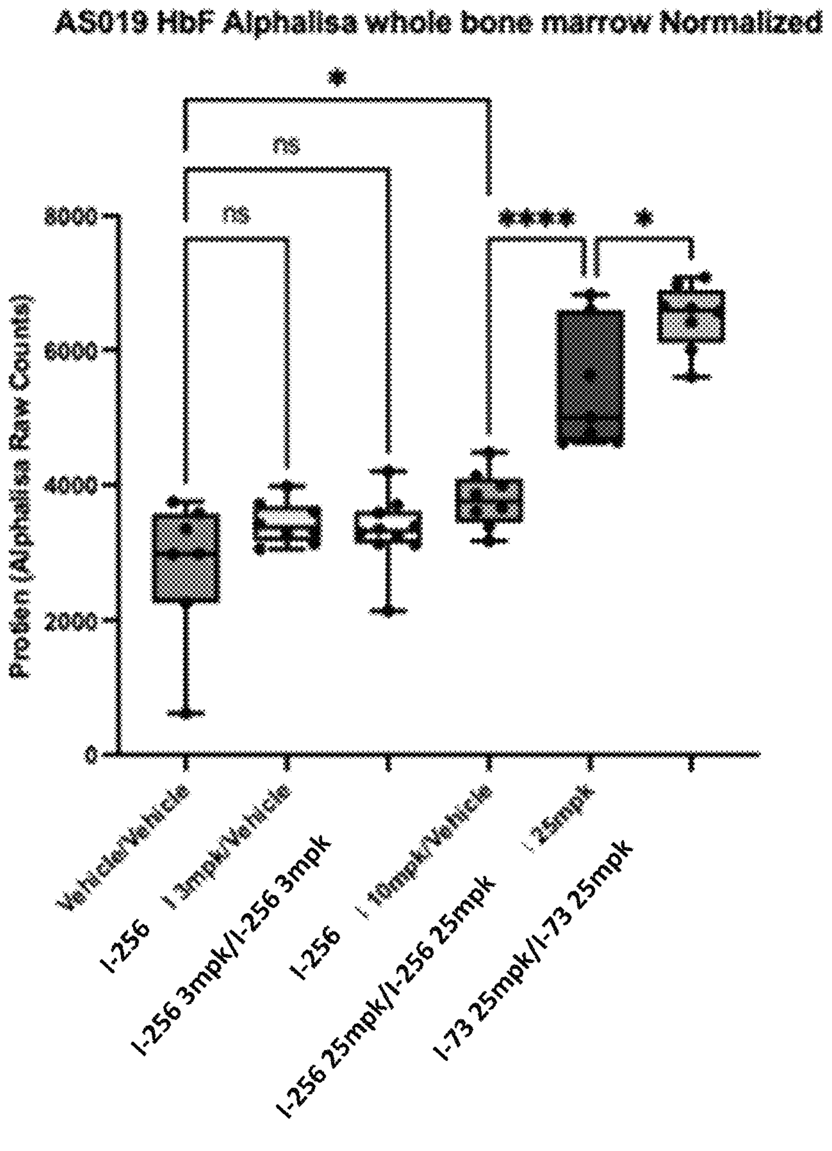
FIG. 4B shows HbF protein detected from unsorted bone marrow cells but then normalized to the percentage of GlyA+ cells in the bone marrow.
Figure 5:
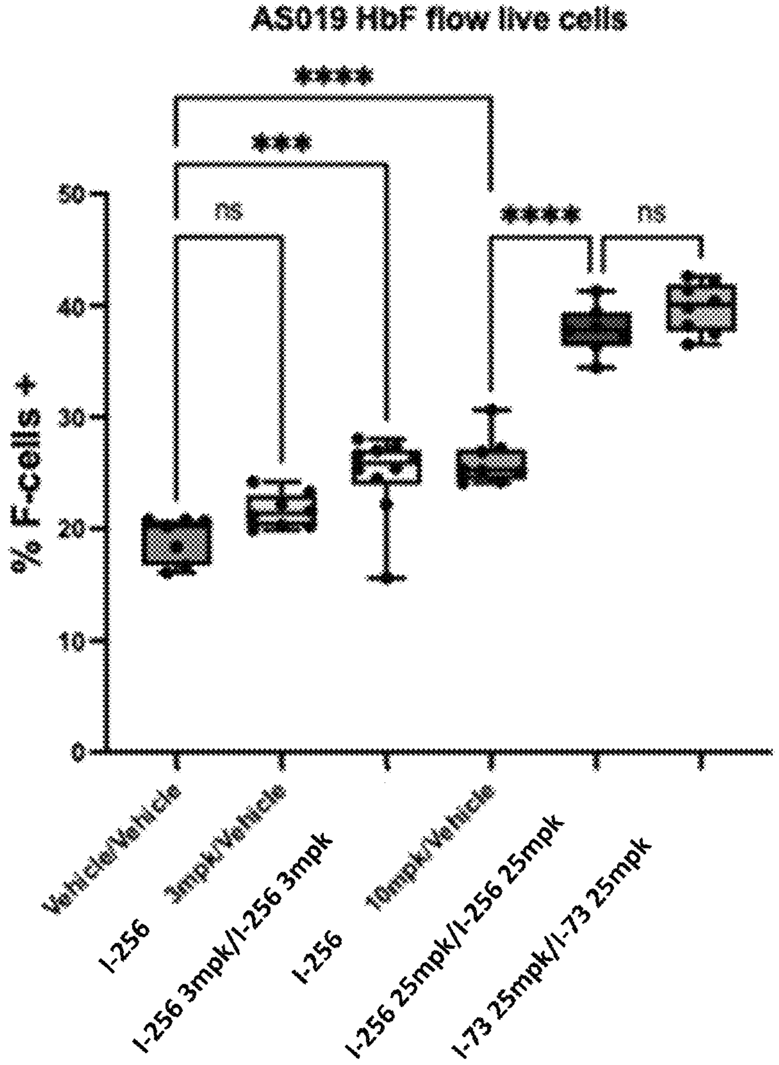
FIG. 5 is FACS results showing the percentage of GlyA+ cells which also have detectable HbF protein levels in them (called F-cells).

In preliminary pharmacokinetic studies, dosing of I-73 at 25 and 100 mg/kg was found to achieve serum concentrations equivalent to or greater than that required to inhibit DCN-1. Based on these exposure results, humanized mice were treated with either the clinical standard of care compound, hydroxyurea (50 mg/kg; bid), or I-73, at 25 and 100 mg/kg (bid), by oral gavage over a three-week period. At the end of the treatment period, bone marrow was harvested for flow cytometry, as well as for assessment of HbF protein and fetal hemoglobin (HBG1) mRNA levels. Levels of both HbF protein and HBG1 mRNA were normalized to the percentage of human erythroid progenitor cells in the bone marrow of each mouse as determined by immunofluorescence staining for human Glycophorin A cell membrane expression. When compared to vehicle-treated mice, I-73 at both the 25 and 100 mg/kg (bid) dosing regimens significantly increases HbF protein levels in bone marrow as detected by AlphaLISA™ (FIG. 1A). Notably, no significant difference in HbF protein levels was observed between mice treated with the 25 and the 100 mg/kg doses, suggesting that 25 mg/kg may represent a maximally effective dose. Similarly, detection of HBG1 mRNA by Nanostring™ demonstrated enhanced transcript levels following treatment with both doses of I-73 (FIG. 1B). In addition, relative levels of fetal hemoglobin to those of potentially sickling-prone adult hemoglobin (HBB) was assessed. At both doses, I-73 induced significantly greater ratios of HBG1 to HBB mRNA than did hydroxyurea (FIG. 1C).

Results from this study support the hypothesis of DCN-1 as a potentially important modulator of fetal hemoglobin and demonstrate that one such covalent DCN-1 inhibitor, I-73, shows promising activity in a relevant in vivo model.

Materials and Methods: NBSGW Humanized Mouse Model for HbF Induction

Animals

Female, 6-week-old NOD.Cg-Kit$^{W-41J}$ Tyr+Prkdc$^{scid}$ Il2rg$^{tm1\,Wjl}$/ThomJ (NBSGW) mice (Jackson Laboratory strain #02662) were used for these studies. The mice were acclimatized to laboratory conditions for 5 days prior to inoculation.

Cell Preparation and Inoculation

GCSF-mobilized human CD34+ cells were removed from liquid nitrogen storage, thawed in a 37° C. water bath and transferred quickly into a 50 mL conical tube. Cryovial was rinsed once with thaw buffer, 0.1% BSA in phosphate buffered saline (PBS), and buffer was transferred and combined with the original contents in the 50 mL conical tube. Next, doubling volumes of thaw buffer was added to the conical and gently swirled for ~30 seconds to one minute until the volume in the conical was 32 mL. Cells and buffer were centrifuged at 300 G for 8 minutes, and the supernatants were aspirated. Cells were counted by resuspending in 1 mL of thawing buffer per million of cells to a target concentration range of 0.5 to 2M/ml and counting with AOPI (1:1) on a luna cell counter to confirm the concentration of cells/mL. The cell concentration was adjusted to 3×10^6 cells/ml. For each mouse, 300 thousand cells in 0.1 ml were injected into the tail vein with a 25-gauge needle.

Engraftment Checkpoint

On day 56 after human cell adoptive transfer, whole blood was collected from each mouse by submandibular bleed and a 100 μL sample of EDTA whole blood was transferred to a 2 ml tube containing 1.8 mL ACK Lysing Buffer at room temperature (RT), and then inverted to mix. Samples were incubated at RT for 15 min in the dark to lyse. After lysis, samples are centrifuged at 500×g for 5 minutes at RT to enable supernatant decanting. Remaining cells were washed with 1 mL of PBS-0.5% BSA and centrifuged at 500×g for 5 minutes at 4° C. Supernatant was decanted and cells were stained with leukocyte markers (human and mouse CD45 antibodies; BD347464, BD557659) to confirm human cell engraftment. Mice having less than one percent, or greater than ten percent, human CD45 positive cells were excluded from the subsequent study. Remaining mice were then randomized into treatment groups based on percentage of human cell engraftment. Each treatment group included 10-11 mice.

Compound Administration

Compound I-73 was dissolved in a 5% Cremophor RH40, 20% hydroxylpropyl-β-cyclodextrin solution. Hydroxyurea was solubilized in PBS. Formulations were prepared fresh daily. Commencing on day 84 post human cell engraftment, mice were treated by oral gavage with either I-73, hydroxyurea or their respective vehicles, for a period of three weeks using either once daily (QD) or twice daily (BID) dosing regimens. Mice were monitored daily for body weight and condition. Mice which lost greater than 20% body weight prior to study completion were removed from the study and humanely euthanized.

Bone Marrow Collection and Analysis

After 21 days of dosing, all mice were euthanized and prepared for bone marrow collection. Both femurs were collected from each mouse by first disinfecting the skin with 70% ethanol and then, using a pair of scissors and forceps, removing the limb and dissecting the muscles both above and below the femur and tibia, taking care not to damage the bone. Femurs were placed in PBS-0.5% BSA-2 mM EDTA-containing tubes on ice during collections. Each femur was flushed to extract marrow with 1 mL of 0.5% BSA-PBS 2 mM EDTA using a 27 gauge needle a total of three times. Extracted cells were counted and aliquoted to prepare for analysis. For detection of fetal (HbF) and adult (HbB) hemoglobin protein, bone marrow cells expressing human glycophorin A (GlyA) were isolated by flow cytometry and frozen. Frozen cells were submitted to the HPLC core facility at the University of Alabama at Birmingham for analysis. For assessment of fetal hemoglobin mRNA (HBG1) expression by Nanostring™, whole RBC-lysed bone marrow cells were used. Resulting mRNA expression levels were normalized based on the percentage of GlyA positive cells in the bone marrow of each mouse.

Example 7: Synthesis of Compounds I-140, I-110, I-217, I-241, I-173, I-170 and I-193

NMR:

$^1$H NMR spectrum was recorded on Bruker 400 MHz and Varian 400 MHz instruments internally referenced to a tetramethylsilane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ; Mobile Phase: A: 0.05% Formic acid in water: I (95:5) B: 0.05% Formic acid in CAN; Inj Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/min; Column oven temp. 50° C.; Gradient program: 0% B to 98% B in 2.0 minute, hold till 3.0 min, at 3.2 min B conc is 0% up to 4.0 min.

Method-C: Column: X-Select CSH C18 (50 mm*3.0 mm,2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2,2.0/98, 2.8/98, 3.0/2,3.7/2.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5, 1/5,8/100, 12/100,14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/2,2/2, 12/90, 16/90; Flow: 1.0 mL/min.; Diluent: I: WATER (80:20).

Method-C: Column: X SELECT CSH C18 (150×4.6 mm, 3.5μ); Mobile Phase A; 0.05% TFA IN WATER: I (95:05); Mobile Phase B: 0.05% TFA IN WATER: I (05:95); Programme: T/B %: 0.01/10, 12/90, 16/90; Flow: 1 mL/min.; Diluent: WATER: I (80:20).

Method-D: Column: X-Bridge CSH C18 (4.6*150) mm 5u Mobile Phase: A-0.1% TFA in water B-Acetonitrile Inj Volume; 5.0 μL, Flow Rate: 1.2. mL/minute Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in HEXANE Mobile Phase B: IPA A/B: 60/40 Flow: 1.0 ml/MIN PDA: OJ-H_015.

Method-F: Column: ACE Excel 2 C18-AR, 100 mm×3.0 mm Mobile Phase A: 0.05% FA in Water; Mobile Phase B: 0.05% FA in Acetonitrile Colum Temperature: 40° C. Flow Rate: 0.6 mL/min Gradient: 0/5, 1/5, 6/90, 8.5/90, 8.8/5, 11/5.

Synthesis of I-140

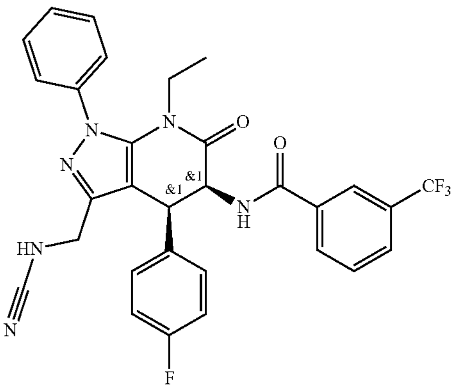

To a stirred solution of 8 as described in example 1 (200 mg, 0.36 mmol) in DMF (5 mL) was added 1,2-benziodoxole-1 (3 h)-carbonitrile, 3-oxo-(135.5 mg, 0.47 mmol). Then the reaction mixture was stirred at room temperature for 6 h. Progress of the reaction was monitored by TLC. Reaction mixture was allowed to room temperature, quenched with water (4 mL), and extracted with ethyl acetate (2×20 mL). Combined organic layers were dried over anhydrous sodium sulfate and concentrated to afford crude compound. Obtained crude compound was purified by silica gel (230-400) column chromatography using ethyl acetate in heptane, eluted in 25% ethyl acetate in heptane to obtained pure compound I-140 (55 mg, 26.04%) as a white solid.

$^1$H NMR (400 MHZ, DMSO-$d_6$) δ=8.54 (d, J=7.6 Hz, 1H), 8.15-8.12 (m, 2H), 7.92 (d, J=8.0 Hz, 1H), 7.73-7.68 (m, 3H), 7.62-7.52 (m, 3H), 7.18-7.08 (m, 3H), 7.01-6.97 (m, 2H), 6.54 (t, J=7.2 Hz, 1H), 4.66 (d, J=7.6 Hz, 1H), 4.03-3.97 (m, 2H), 3.94-3.85 (m, 1H), 3.08-3.03 (m, 1H), 0.91 (t, J=7.2 Hz, 3H). LC-MS (Method-A)=577.1 $[M+H]^+$; 94.43% at RT 3.53 min. HPLC (Method-B)=92.65% at RT 8.63 min.

Synthesis of I-110

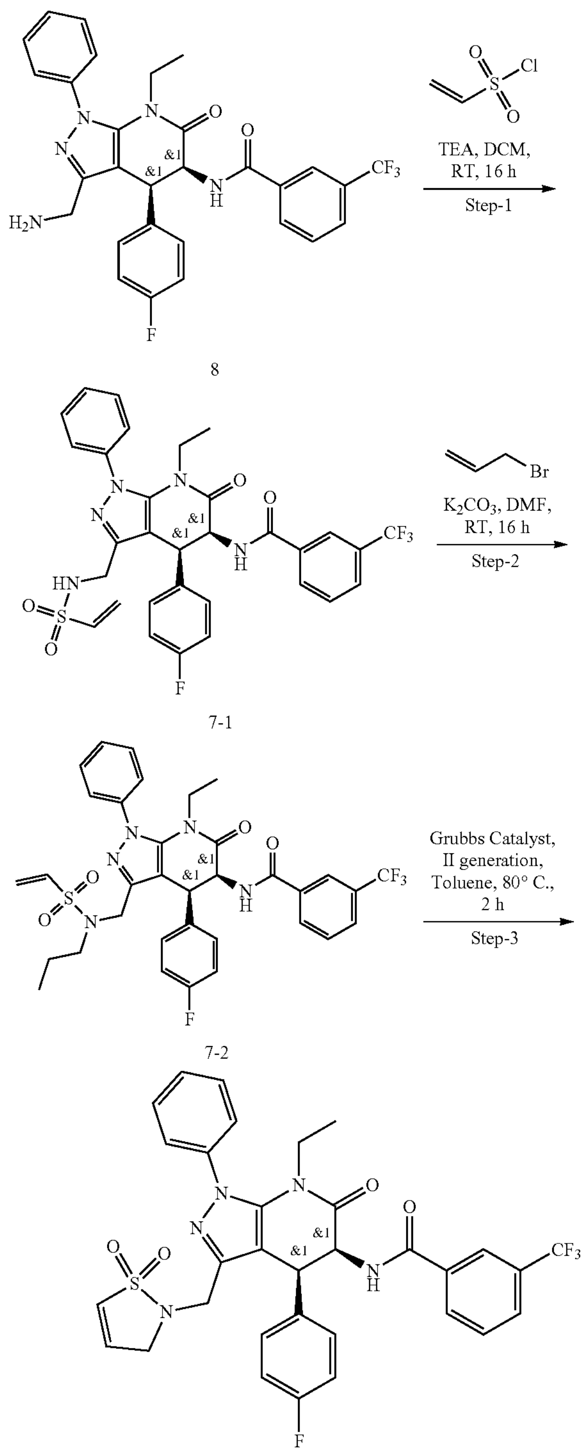

8

7-1

7-2

I-110

Step-1: Synthesis of rac-N-((4R,5R)-7-ethyl-4-(4-fluorophenyl)-6-oxo-1-phenyl-3-(vinylsulfonamidomethyl)-4,5,6,7-tetrahydro-1H-pyrazolo[3,4-b]pyridine-5-yl)-3-(trifluoromethyl)benzamide To a stirred solution of 8 (500 mg, 0.90 mmol) in dichloromethane (10 mL) was added triethyl amine (275.2 mg, 2.72 mmol) and ethenesulfonyl chloride (126.2 mg, 0.99 mmol) reagent added at room temperature, stirred the reaction at room temperature for 16 h. Progress of the reaction was monitored by TLC. Reaction mixture was allowed to room temperature, quenched with water (5 mL), and extracted with DCM (2×20 mL), combined organic layers was dried over anhydrous sodium sulfate and concentrated to afford crude compound. Obtained crude compound was purified by silica gel (230-400) column chromatography using ethyl acetate in heptane, eluted at 25% ethyl acetate in heptane to afford pure Compound-2 (400 mg, 68.77%) as an off-white solid.

$^1$H NMR (400 MHZ, DMSO-$d_6$) δ=8.49 (d, J=7.6 Hz, 1H), 8.16-8.13 (m, 2H), 7.93-7.91 (m, 1H), 7.75-7.54 (m, 8H), 7.10 (t, J=8.8 Hz, 2H), 7.01-6.97 (m, 2H), 6.61-6.54 (m, 1H), 5.95-5.91 (m, 2H), 5.50 (t, J=6.8 Hz, 1H), 4.69 (d, J=7.2 Hz, 1H), 3.93-3.83 (m, 3H), 3.06-3.01 (m, 1H), 0.92-0.84 (m, 3H). LC-MS (Method-B)=642.48 [M+H]$^+$; 85.48% at RT 2.11 min.

Step-2: Synthesis of rac-N-((4R,5R)-3-((N-allylvinylsulfonamido)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide To a stirred solution of Compound-7-1 (400 mg, 0.62 mmol) in DMF (5 mL) was added Potassium carbonate (129 mg, 0.93 mmol) and 3-bromoprop-1-ene (113.1 mg, 0.93 mmol) at room temperature. Then the reaction mixture was stirred at room temperature for 16 h. Progress of the reaction mixture was monitored by TLC. Reaction mixture was then quenched with water (5 mL), and extracted with ethyl acetate (2×20 mL). Combined organic layers was dried over anhydrous sodium sulfate and concentrated to afford crude compound. Obtained crude compound was purified by silica gel (230-400) column chromatography using ethyl acetate in heptane, eluted at 35% to 45% of ethyl acetate in heptane to afford pure Compound-3 (300 mg, 65.65%) as a pale-yellow solid.

$^1$H NMR (400 MHZ, DMSO-$d_6$) δ=8.50 (d, J=6.8 Hz, 1H), 8.15-8.12 (m, 2H), 7.92-7.91 (m, 1H), 7.30-7.67 (m, 3H), 7.62-7.55 (m, 3H), 7.12-7.08 (m, 2H), 6.99-6.95 (m, 2H), 6.73-6.67 (m, 1H), 6.08-5.99 (m, 2H), 5.67-5.60 (m, 1H), 5.50-5.46 (m, 1H), 5.12-5.04 (m, 2H), 4.64 (d, J=7.2 Hz, 1H), 4.14 (s, 2H), 3.91-3.85 (m, 1H), 3.58-3.52 (m, 2H), 3.08-3.02 (m, 1H), 0.93-0.84 (m, 3H). LC-MS (Method-D)=682.1 [M+H]$^+$; 93.96% at RT 2.65 min.

Step-3: Synthesis of I-110

To a stirred solution of Compound-7-2 (350 mg, 0.47 mmol) in toluene (5 mL) was purged with nitrogen for 5 min. Then another round bottom flask (1,3-Bis(2,4,6-trimethylphenyl)-2-imidazolidinylidene)dichloro(phenylmethylene) (tricyclohexylphosphine) ruthenium (Grubbs Catalyst, II generation) (83.58 mg, 0.09 mmol) was added in toluene (3.00 mL) and purged with nitrogen for 5 min. at room temperature. Then the reaction mixture was added the catalyst solution drop wise to the substrate solution. Reaction mixture was heated at 80° C. under $N_2$ reaction for 2 h. Progress of the reaction was monitored by TLC. Reaction mixture was allowed to room temperature, quenched with water (5 mL), and extracted with ethyl acetate (2×20 mL). Combined organic layers was dried over anhydrous sodium sulfate and concentrated to afford crude compound. Obtained crude compound was purified by silica gel (230-400) column chromatography using ethyl acetate in heptane, eluted at 40% ethyl acetate in heptane to afford pure compound I-110 (100 mg, 32.04%) as a pale-yellow solid.

$^1$H NMR (400 MHZ, DMSO-$d_6$) δ=8.49 (d, J=7.6 Hz, 1H), 8.12-8.10 (m, 2H), 7.91 (d, J=7.6 Hz, 1H), 7.71-7.69 (m, 3H), 7.61-7.54 (m, 3H), 7.09-7.05 (m, 3H), 6.98-6.94 (m, 2H), 6.91-6.88 (m, 1H), 5.53 (t, J=7.2 Hz, 1H), 4.65 (d, J=7.2 Hz, 1H), 4.23-4.19 (m, 1H), 4.04-4.00 (m, 1H), 3.91-3.77 (m, 2H), 3.50-3.45 (m, 1H), 3.09-3.04 (m, 1H), 0.92 (t, J=7.2 Hz, 3H). LC-MS (Method-A)=652.30 [M−H]$^-$; 96.09% at RT 2.37 min. HPLC (Method-A)=96.05% at RT 6.33 min.

Synthesis of I-217

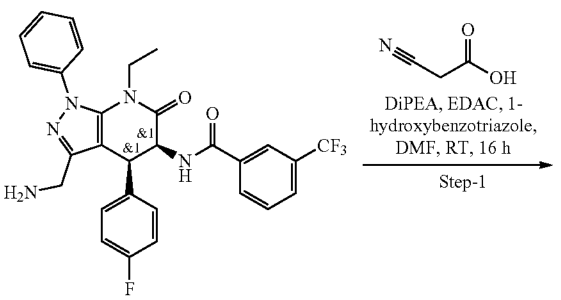

8

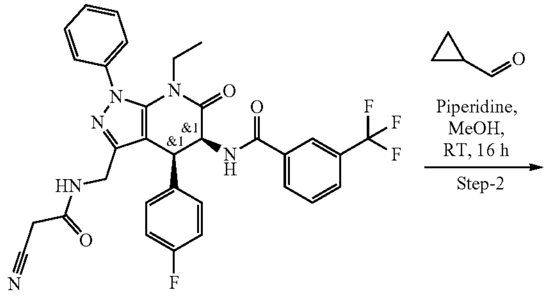

7-3

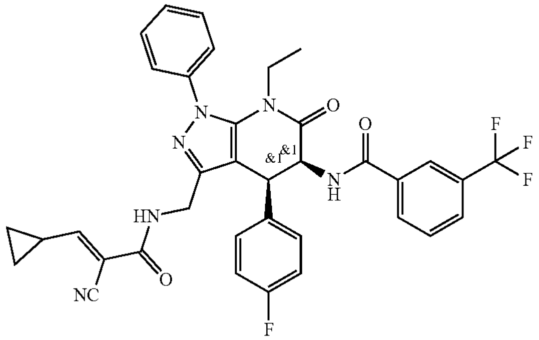

I-217

Step-1: Synthesis of rac-N-((4R,5R)-3-((2-cyanoacetamido)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide To a stirred solution of 8 (1 g, 1.81 mmol) in DMF (10 mL) were added N,N-Diisopropylethylamine (0.71 g, 5.44 mmol) and EDAC (0.53 g, 2.72 mmol) then 2-cyanoacetic acid (0.18 g, 2.17 mmol) and 1-hydroxybenzotriazole (0.37 g, 2.72 mmol) added reagent at room temperature. Then the reaction mixture was stirred at room temperature for 16 h. Progress of the reaction mixture was monitored by TLC. Reaction mixture was allowed to room temperature, quenched with water (100 mL), and extracted with ethyl acetate (2×50 mL). Combined organic layers were dried over anhydrous sodium sulfate and concentrated to afford crude compound. Obtained crude compound was purified by silica gel (230-400) column chromatography using ethyl acetate in heptane, eluted at 20% ethyl acetate in heptane to afford pure compound (700 mg, 61.78%) as a pale-yellow solid.

$^1$H NMR (400 MHZ, DMSO-$d_6$) δ=8.56-8.53 (m, 2H), 8.17-8.14 (m, 2H), 7.93 (d, J=7.6 Hz, 1H), 7.74-7.67 (m, 3H), 7.62-7.52 (m, 3H), 7.11 (t, J=8.8 Hz, 2H), 6.95-6.92 (m, 2H), 4.55 (d, J=7.2 Hz, 1H), 4.34-4.29 (m, 1H), 4.14-4.09 (m, 1H), 3.95-3.87 (m, 1H), 3.21-3.16 (m, 1H), 3.06-3.01 (m, 2H), 0.91 (t, J=6.8 Hz, 3H). LC-MS (Method-B)=619.1 [M+H]$^+$; 99.87% at RT 2.25 min. HPLC (Method-B)=99.78% at RT 8.92 min.

Step-1: Synthesis of I-217

To a stirred solution of Compound-7-3 (250 mg, 0.40 mmol) in methanol (10 mL) was added piperidine (35.11 mg, 0.40 mmol) and cyclopropane carbaldehyde (50.99 mg, 0.72 mmol) at room temperature. Then the reaction mixture was stirred at room temperature for 16 h. Progress of the reaction was monitored by TLC. Reaction mixture was allowed to room temperature, quenched with water (5 mL), and extracted with ethyl acetate (2×20 mL). Combined organic layers were dried over anhydrous sodium sulfate and concentrated to afford crude compound. Obtained crude compound was purified by silica gel (230-400) column chromatography using ethyl acetate in heptane, eluted at 40% to 50% ethyl acetate in heptane to afford pure compound of I-217 (65 mg, 23.74%) as an off white solid.

$^1$H NMR (400 MHZ, DMSO-$d_6$) δ=8.49 (d, J=7.2 Hz, 1H), 8.33-8.30 (m, 1H), 8.18-8.14 (m, 2H), 7.93 (d, J=8.0 Hz, 1H), 7.74-7.65 (m, 3H), 7.61-7.51 (m, 3H), 7.01 (t, J=8.8 Hz, 2H), 6.84-6.81 (m, 2H), 6.47 (d, J=11.2 Hz, 1H), 5.48 (t, J=7.2 Hz, 1H), 4.57-4.47 (m, 2H), 4.12-4.07 (m, 1H), 3.92-3.87 (m, 1H), 3.05-2.96 (m, 1H), 1.71-1.62 (m, 1H), 1.16-1.14 (m, 2H), 0.89 (t, J=6.8 Hz, 3H) 0.83-0.73 (m, 2H). LC-MS (Method-B)=671.0 [M+H]$^+$; 99.46% at RT 2.39 min. HPLC (Method-B)=99.76% at RT 9.19 min.

Step-1: Synthesis of I-241

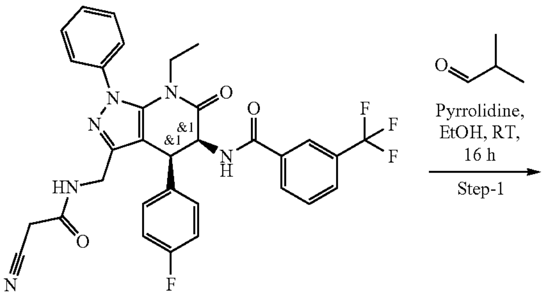

Compound-7-3

-continued

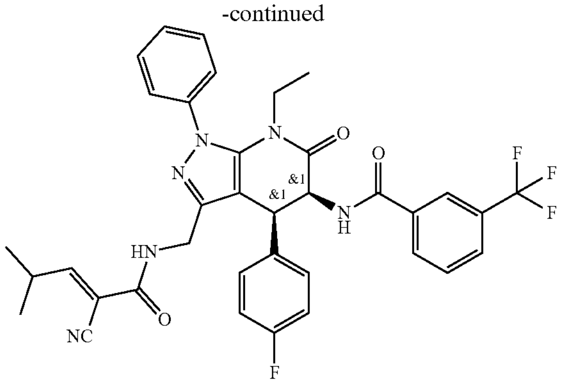

I-241

-continued

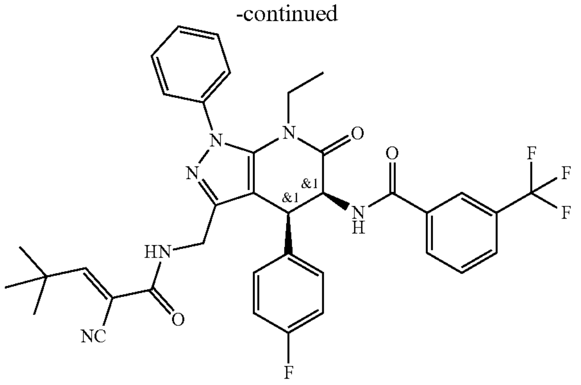

I-173

To a stirred solution of Compound-7-3 (200 mg, 0.32 mmol) in ethanol (5 mL) was added pyrrolidine (4.62 mg, 0.06 mmol) and 2-methylpropanal (25.65 mg, 0.35 mmol) at room temperature. Then the reaction mixture was stirred at room temperature for 6 h. Progress of the reaction mixture was monitored by TLC. Reaction mixture was concentration under vacuum, quenched with water (4 mL) and extracted with ethyl acetate (2×10 mL). Combined organic layers was dried over anhydrous sodium sulfate and concentrated to afford crude compound. Obtained crude compound was purified by silica gel (230-400) column chromatography using ethyl acetate in heptane, eluted at 45% ethyl acetate in heptane to afford pure compound of I-241 (42.46 mg, 52.80%) as an off-white solid.

$^1$H NMR (400 MHZ, DMSO-$d_6$) δ=8.57-8.54 (m, 1H), 8.49 (d, J=7.2 Hz, 1H), 8.18-8.14 (m, 2H), 7.92 (d, J=8.0 Hz, 1H), 7.73-7.66 (m, 3H), 7.61-7.52 (m, 3H), 7.02 (t, J=8.8 Hz, 2H), 6.88-6.83 (m, 3H), 5.49 (t, J=7.2 Hz, 1H), 4.58-4.48 (m, 2H), 4.14-4.09 (m, 1H), 3.93-3.87 (m, 1H), 3.04-2.99 (m, 1H), 2.59-2.54 (m, 1H), 0.99-0.95 (m, 6H), 0.90 (t, J=6.8 Hz, 3H). LC-MS (Method-B)=673.3 $[M+H]^+$; 98.50% at RT 2.59 min. HPLC (Method-B)=95.15% at RT 9.33 min.

To a stirred solution of Compound-7-3 (200 mg, 0.32 mmol) in ethanol (5 mL) was added pyrrolidine (4.62 mg, 0.06 mmol) and 2,2-dimethylpropanal (27.85 mg, 0.32 mmol) at room temperature. Then the reaction mixture was stirred at room temperature for 16 h. Progress of the reaction was monitored by TLC. Reaction mixture was allowed to room temperature, quenched with water (5 mL), and extracted with ethyl acetate (2×20 mL). Combined organic layers was dried over anhydrous sodium sulfate and concentrated to afford crude compound. Obtained crude compound was purified by silica gel (230-400) column chromatography using ethyl acetate in heptane, eluted at 40% ethyl acetate in heptane to get pure compound of I-173 (40 mg, 17.66%) as an off white solid.

$^1$H NMR (400 MHZ, DMSO-$d_6$) δ=8.49 (d, J=7.2 Hz, 2H), 8.18-8.14 (m, 2H), 7.92 (d, J=8.0 Hz, 1H), 7.73-7.66 (m, 3H), 7.61-7.51 (m, 3H), 7.05-7.00 (m, 3H), 6.86-6.83 (m, 2H), 5.49 (t, J=7.2 Hz, 1H), 4.58-4.49 (m, 2H), 4.15-4.10 (m, 1H), 3.92-3.87 (m, 1H), 3.06-2.99 (m, 1H), 1.11 (s, 9H), 0.90 (t, J=6.8 Hz, 3H). LC-MS (Method-B)=686.9 $[M+H]^+$; 93.19% at RT 3.27 min. HPLC (Method-B)=88.25% at RT 9.68 min.

Step-1: Synthesis of I-173

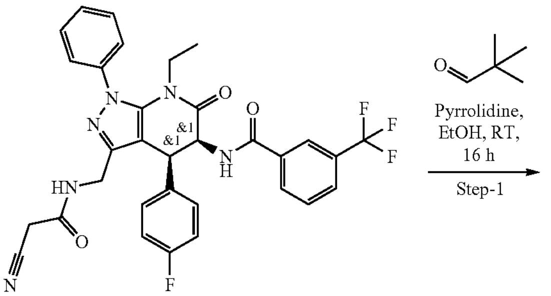

Compound 7-3

Synthesis of I-170

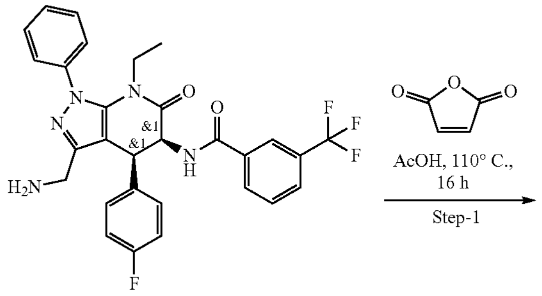

8

-continued

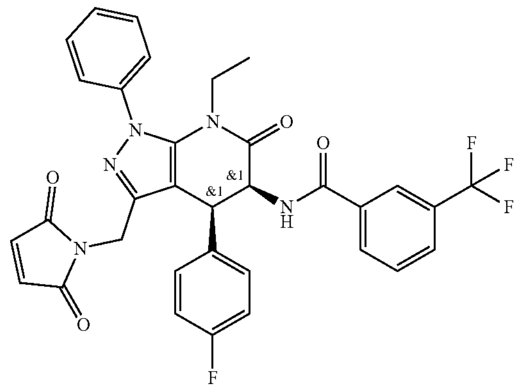

I-170

To a stirring solution of furan-2,5-dione (30.00 mg, 0.30 mmol) in acetic acid (5.00 mL) was added 8 (202.5 mg, 0.36 mmol) at 25° C. under inert atmosphere. The reaction mixture was stirred at 110° C. for 16 h. Progress of the reaction was monitored by TLC. Allow the reaction mixture to room temperature and quenched with ice cold water (10 mL), solids were filtered and dried to get crude compound. Obtained crude product was purified by Prep-HPLC, product containing fractions was collected and lyophilized to afford pure compound I-170 (20 mg, 9.74%) as a white solid.

$^1$H NMR (400 MHZ, DMSO-$d_6$) δ=8.52 (d, J=7.2 Hz, 1H), 8.18-8.14 (m, 2H), 7.92 (d, J=8.0 Hz, 1H), 7.73-7.66 (m, 3H), 7.61-7.51 (m, 3H), 7.04 (t, J=8.8 Hz, 2H), 6.76-6.73 (m, 2H), 6.60 (s, 2H), 5.50 (t, J=7.2 Hz, 1H), 4.67-4.63 (m, 1H), 4.40-4.36 (m, 2H), 3.87 -3.82 (m, 1H), 3.06-2.97 (m, 1H), 0.87 (t, J=7.2 Hz, 3H). LC-MS (Method-E)=631.9 $[M+H]^+$; 95.26% at RT 2.38 min. HPLC (Method-B)= 94.15% at RT 9.49 min.

Synthesis of I-193

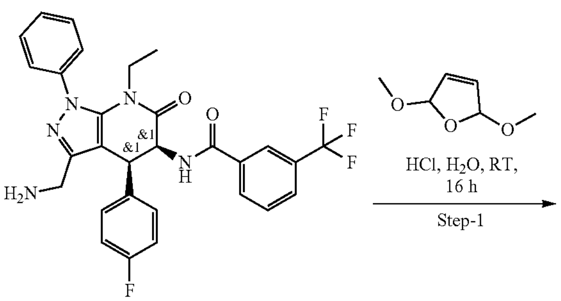

8

-continued

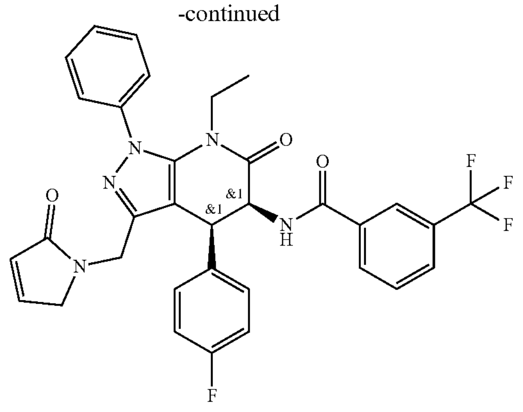

I-193

To a stirred solution of 8 (0.4 g, 0.7 mmol) in hydrochloric acid (0.04 g, 1 mmol), water (0.02 g, 1 mmol) was added 2,5-dimethoxy-2,5-dihydrofuran (0.09 g, 0.7 mmol) at 25° C. Then the reaction mixture was allowed to stir at room temperature for 16 h. Reaction mass was monitored by TLC. Reaction mixture was diluted with water (5 mL) and extract compound into DCM (2×15 mL), dried over sodium sulphate and concentrated under reduced pressure to afford crude compound. Obtained crude was purified by column chromatography 0f 230-400 mesh silica gel. Reaction mixture was eluted at 50-60% of acetone in toluene to afford I-193 (18.60 mg, 4.00%) as a brown solid.

$^1$H NMR (400 MHZ, DMSO-$d_6$) δ=8.48 (d, J=7.2 Hz, 1H), 8.15-8.12 (m, 2H), 7.91 (d, J=7.6 Hz, 1H), 7.72-7.68 (m, 3H), 7.61-7.52 (m, 3H), 7.02 (t, J=8.8 Hz, 2H), 6.88-6.81 (m, 3H), 5.71 (d, J=6.0 Hz, 1H), 5.49 (t, J=7.2 Hz, 1H), 4.73-4.70 (m, 1H), 4.42 (d, J=7.2 Hz, 1H), 4.24-4.20 (m, 1H), 3.89-3.81 (m, 2H), 3.52-3.47 (m, 1H), 3.06-3.00 (m, 1H), 0.90 (t, J=6.8 Hz, 3H). LC-MS (Method-B)=618.2 $[M+H]^+$; 99.49% at RT 2.31 min. HPLC (Method-B)= 97.26% at RT 8.51 min.

Example 8: Synthesis of Compounds I-45, I-64, I-127 and I-59

NMR:

$^1$H NMR spectrum was recorded on Bruker 400 MHz and Varian 400 MHz instruments internally referenced to a tetramethylsilane (TMS) signal. Chemical shifts (δ) and coupling constants (J) were expressed in parts per million and hertz, respectively.

LC-MS:

2.5μ. Mobile Phase: A: 0.05% Formic acid in water: I (95:5) B: 0.05% Formic acid in CAN Inj Volume: 2.0 μL, Column oven temperature: 50° C.; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

Method-C: Column: X-Select CSH C18, (50 mm*3.0 mm, 2.5μ) Mobile Phase A: 0.05% TFA in Water Mobile Phase B: 0.05% TFA in Acetonitrile Flow rate: 1.0 mL/min. Column temperature: 40° C. Gradient Program (B %): 0.0/2, 0.3/2,2.0/98, 2.8/98, 3.0/2,3.7/2.

Method-D: Column: X-Select CSH C18 (3.0*50 mm, 2.5 µm), Mobile Phase A: 2.5 Mm Ammonium Bicarbonate in $H_2O$+5% I Mobile Phase B: 100% I, Gradient % B: 0/2, 0.3/2,2.0/98,2.8/98,3.0/2,3.7/2.

Method-E: Column: X-Bridge BEH C18, (50 mm*3.0 mm, 2.5µ) Mobile Phase A: 2.5 mM Ammonium Bicarbonate in Water+5% I Mobile Phase B: 100% I Flow rate: 1.0 mL/min. Column temperature: 40° C. Gradient Program (B %): 0.0/2, 0.3/2, 2.0/98, 2.8/98, 3.0/2,3.7/2.

HPLC:

Method-A: Column: X Select CSH C18 (150×4.6) mm, 3.5µ; Mobile phase A: 0.1% FA in Water: I (95:05); Mobile phase B: Acetonitrile; Gradient Programme: T/B %: 0.01/5,1/5,8/100,12/100,14/5, 18/5; Flow rate: 1.2 ml/min.

Method-B: Column: X-Bridge CSH C18 (150×4.6 mm, 3.5 µm); Mobile Phase-A: 5 mM $NH_4HCO_3$; Mobile Phase-B: I; Programme: T/B %: 0.01/2,2/2,12/90,16/90; Flow rate: 1.0 mL/min.; Diluent: I: WATER (80:20).

Method-C: Column: X SELECT CSH C18 (150×4.6 mm, 3.5µ); Mobile Phase A: 0.05% TFA in water: I (95:05); Mobile Phase B: 0.05% TFA in water: CAN (05:95); Programme: T/B %: 0.01/10,12/90,16/90; Flow rate: 1 mL/min.; Diluent: WATER: I (80:20).

Method-D: Column: X-Bridge CSH C18 (4.6*150) mm 5u Mobile Phase: A-0.1% TFA in water B-Acetonitrile Inj Volume; 5.0 µL, Flow Rate: 1.2 mL/minute Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5µ) Mobile Phase A: 0.1% DEA in Hexane Mobile Phase B: IPA A/B: 60/40 Flow: 1.0 ml/MIN PDA: OJ-H_015.

Method-F: Column: ACE Excel 2 C18-AR, 100 mm×3.0 mm Mobile Phase A: 0.05% TFA in Water Mobile Phase B: 0.05% TFA in Acetonitrile Colum Temperature: 40° C. Flow Rate: 0.6 mL/min Gradient: 0/5, 1/5, 6/90, 8.5/90, 8.8/5, 11/5.

Method-G: Column: CHIRAL PAK-IC (250×4.6 mm, 5 µm) Mobile Phase A: 0.1% DEA in Hexane Mobile Phase B: EtOH/MeOH (50/50) A: B: 80/20 Flow 1.0 ml/min.

Method-H: Column: X-Bridge C18 (4.6*150) mm 5u Mobile Phase: A-5 mM Ammonium Acetate B-Acetonitrile Flow Rate: 1.0. mL/minute Gradient program: Time (min)/B Conc.: 0.01/5, 1.0/5, 8.0/100, 12.0/100, 14.0/5, 18.0/5.

Method-I: Column: CHIRALCEL-OJ-H (250×4.6 mm, 5 µm) mobile Phase A: n-Hxane; Mobile Phase B: EtOH: MeOH (1:1) A/B: 50/50 Flow: 1.0 ml/min.

Method-J: Column: CHIRALCEL-OX-H Mobile Phase A: n-Hexane Mobile Phase B: IPA Flow: 1.0 ml/min.

Method-K: Column Name: CHIRALPAK-IG (250×4.6 mm, 5 µm), Mobile Phase A: 0.1% DEA n-Hexane, Mobile Phase B: DCM: MeOH (50:50), Flow rate: 1.0 ml/min.

Method-L: Column IC-5 (30×250*4.6 mm,5µ) Mobile phase A N-Hexane Mobile phase B IPA: DCM (1:1) Eluent A: B: −70-30 Total Flow rate (mL/min) 42.

Synthesis of I-59, I-64, and I-45

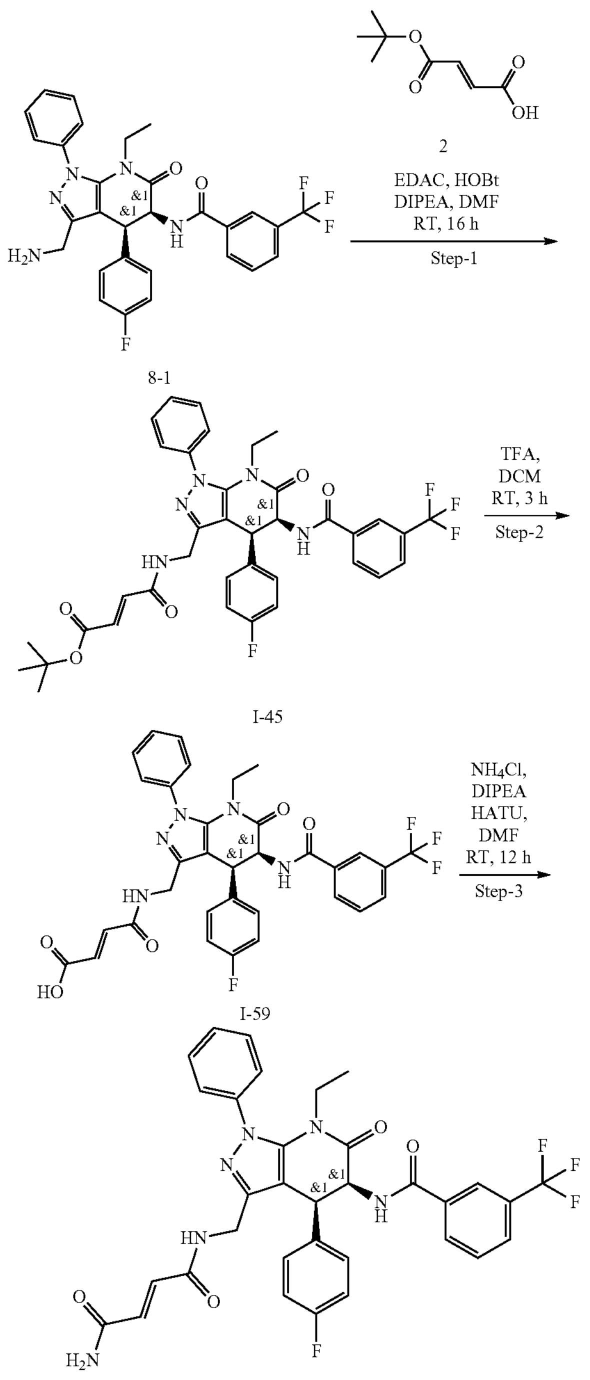

I-64

Step-1: Synthesis of tert-butyl I-4-((((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)methyl)amino)-4-oxobut-2-enoate (I-45)

To a stirred solution of 8-1 (1.0 g, 1.48 mmol) in DMF (5 mL) was added I-4-tert-butoxy-4-oxo-but-2-enoic acid (2) (300 mg, 1.71 mmol), N,N-diisopropylethylamine (0.78 mL, 4.46 mmol), 1-(3-dimethylaminopropyl)-3-ethylcarbodiimide (350 mg, 2.23 mmol), 1-hydroxybenzotriazole (300 mg, 2.23 mmol) at room temperature. The resulting reaction mixture was stirred at room temperature for 16 h. The progress of the reaction was monitored by TLC and LCMS. The reaction mixture was quenched with ice cold water (20 mL) to obtain the solid, which was filtered and triturated with diethyl ether and n-heptane to afford compound (1 g, 89.9%) from that (300 mg) was purified by using combi flash with 60% ethyl acetate in heptane to afford the title compound I-45 (111 mg, 38.5%) as an Off-White solid.

$^1$H NMR (400 MHZ, DMSO-$d_6$) δ=8.73-8.70 (m, 1H), 8.49 (d, J=7.6 Hz, 1H), 8.17-8.13 (m, 2H), 7.92 (d, J=7.6 Hz, 1H), 7.73-7.66 (m, 3H), 7.61-7.53 (m, 3H), 6.97 (t, J=8.8 Hz, 2H), 6.86-6.82 (m, 2H), 6.33 (d, J=15.6 Hz, 1H), 6.12 (d, J=15.6 Hz, 1H), 5.49 (t, J=7.2 Hz, 1H), 4.53-4.46 (m, 2H), 4.14-4.11 (m, 1H), 3.94-3.87 (m, 1H), 3.03-2.98 (m, 1H), 1.42 (s, 9H), 0.89 (t, J=7.2 Hz, 3H). LC-MS (Method-C)=706.2 $[M+H]^+$; 98.03% at RT 6.33 min HPLC (Method-A): 98.48% at RT 6.24 min. Chiral HPLC (Method-A): Peak-1=50% at RT 5.96 min. Peak-2=49.93% at RT 8.39 min.

Step-2: Synthesis of rac-I-4-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)methyl)amino)-4-oxobut-2-enoic acid (I-59)

To a stirred solution of compound (1-45) (3 g, 4.01 mmol) in dichloromethane (15 mL) was added TFA (5 mL) at room temperature. The resulting reaction mixture was stirred at room temperature for 3 h. Progress of the reaction was monitored by TLC. After consumption the reaction mixture was diluted with DCM (300 mL) and washed with water (3×50 mL)). The organic layer was dried over sodium sulphate and concentrated under reduced pressure to afford crude solid was triturated with heptane to afford I-59 (2.30 g, 88.3%) as a brown colored solid.

Step-3: Synthesis of rac-N1-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)methyl)fumaramide (I-64)

To a stirred solution of I-59 (250 mg, 0.38 mmol) in DMF (5 mL), were added ammonium chloride (0.03 g, 0.57 mmol), N,N-Diisopropylethylamine (0.10 g, 0.76 mmol) and HATU (0.22 g, 0.57 mmol) at room temperature. Then the reaction mixture was stirred at room temperature for 12 h. Reaction progress was monitored by TLC and LCMS. After completion of reaction, the reaction mixture was quenched with water (25 mL) and extracted with ethyl acetate (2×50 mL). Organic layer was concentrated under vacuum to afford crude. Obtained crude was submitted for prep-HPLC purification. Pure fractions were lyophilized to afford I-64 (65 mg, 25.78%) as an off-white solid.

$^1$H NMR (400 MHZ, DMSO-$d_6$) δ=8.65 (t, J=5.2 Hz, 1H), 8.48 (d, J=7.6 Hz, 1H), 8.15-8.12 (m, 2H), 7.92 (d, J=8.0 Hz, 1H), 7.73-7.51 (m, 7H), 7.21 (s, 1H), 7.02-6.97 (m, 2H), 6.89-6.86 (m, 2H), 6.62-6.59 (m, 1H), 6.40-6.37 (m, 1H), 5.50 (t, J=7.2 Hz, 1H), 4.56 (d, J=7.2 Hz, 1H), 4.46-4.41 (m, 1H), 4.16-4.11 (m, 1H), 3.93-3.83 (m, 1H), 3.07-2.98 (m, 1H), 0.90 (t, J=7.2 Hz, 3H). LC-MS (Method-B)=649.1 $[M+H]^+$; 99.93% at RT 1.77 min. HPLC (Method-B)=99.40% at RT 8.33 min. Chiral HPLC (Method-D)= Peak-1=48.83% at RT 6.90 min. and Peak-2-48.11% at RT 7.61 min.

Synthesis of I-127:

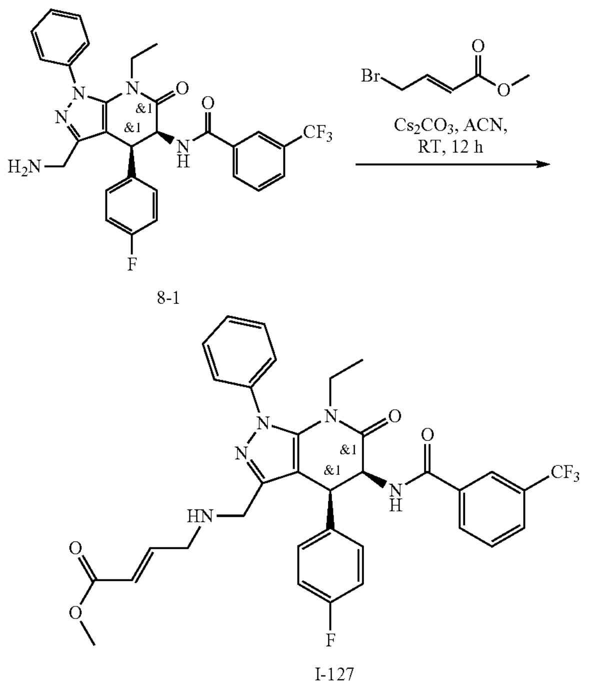

Synthesis of rac-methyl I-4-((((4R,5R)-7-ethyl-4-(4-fluorophenyl)-6-oxo-1-phenyl-5-(3-(trifluoromethyl) benzamido)-4,5,6,7-tetrahydro-1H-pyrazolo[3,4-b] pyridine-3-yl)methyl)amino) but-2-enoate: (I-127)

To a stirred solution of 8-1 (250 mg, 0.45 mmol) in I (5 mL), were added cesium carbonate (0.15 g, 0.45 mmol) and methyl (~{E})-4-bromobut-2-enoate (0.06 g, 0.36 mmol) at room temperature. Then the reaction mixture was stirred at room temperature for 12 h. Progress of the reaction was monitored by TLC. After completion of the reaction, the reaction mixture was quenched with ice water (50 mL) and extracted with ethyl acetate (2×50 mL). The organic layer was dried over anhydrous sodium sulfate and concentrated under vacuum to afford crude compound. Obtained crude was purified through flash column chromatography using 80-90% of ethyl acetate in heptane. Pure fractions were concentrated under vacuum to afford I-127 (40 mg, 12.90%) as white solid.

$^1$H NMR (400 MHZ, DMSO-$d_6$) δ=8.49 (d, J=7.6 Hz, 1H), 8.15-8.12 (m, 2H), 7.92 (d, J=8.0 Hz, 1H), 7.71 (t, J=8.0 Hz, 1H), 7.66-7.64 (m, 2H), 7.58 (t, J=7.2 Hz, 2H), 7.53-7.52 (m, 1H), 7.06 (t, J=8.8 Hz, 2H), 6.99-6.95 (m, 2H), 6.67-6.63 (m, 1H), 5.71 (d, J=16.0 Hz, 1H), 5.49 (t, J=7.2 Hz, 1H), 4.70 (d, J=7.2 Hz, 1H), 3.92-3.86 (m, 1H), 3.67-3.64 (m, 1H), 3.60 (s, 3H), 3.53-3.50 (m, 1H), 3.21-3.12 (m, 2H), 3.09-3.02 (m, 1H), 2.09 (s, 1H), 0.91 (t, J=6.8 Hz, 3H). LC-MS (Method-B)=650.0 $[M+H]^+$; 95.89% at RT 2.37 min. HPLC (Method-B)=93.53% at RT 6.59 min. Chiral-HPLC (Method-C)=Peak-1=50.17% at RT 8.50 min. Peak-2=49.83% at RT 15.93 min.

Example 9: Synthesis of Compounds I-145, I-30, I-33, I-186, I-228, I-90, I-201, I-234, I-219, I-29, I-200, I-233, I-55, I-117, I-178, I-1, I-227, I-156, I-129, and I-185

NMR:

$^1$H NMR spectrum was recorded on Bruker 400 MHz and Varian 400 MHz instruments internally referenced to a tetramethylsilane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: I (95:5) B: 0.05% Formic acid in I Inj Volume: 2.0 μL, Column oven temperature: 50° C.; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

Method-C: Column: X-Select CSH C18, (50 mm*3.0 mm,2.5μ) Mobile Phase A: 0.05% TFA in Water Mobile Phase B: 0.05% TFA in Acetonitrile Flow rate: 1.0 mL/min. Column temperature: 40° C. Gradient Program (B %): 0.0/2, 0.3/2,2.0/98, 2.8/98, 3.0/2,3.7/2.

Method-D: Column: X-Select CSH C18 (3.0*50 mm, 2.5 μm), Mobile Phase A: 2.5 Mm Ammonium Bicarbonate in $H_2O$+5% I Mobile Phase B: 100% I, Gradient % B: 0/2, 0.3/2,2.0/98,2.8/98,3.0/2,3.7/2.

Method-E: Column: X-Bridge BEH C18, (50 mm*3.0 mm,2.5μ) Mobile Phase A: 2.5 mM Ammonium Bicarbonate in Water+5% I Mobile Phase B: 100% ACN Flow rate: 1.0 mL/min. Column temperature: 40° C. Gradient Program (B %): 0.0/2, 0.3/2, 2.0/98, 2.8/98, 3.0/2,3.7/2.

HPLC:

Method-A: Column: X Select CSH C18 (150×4.6) mm,3.5μ; Mobile phase A: 0.1% FA in Water: CAN (95:05); Mobile phase B: Acetonitrile; Gradient Programme: T/B %: 0.01/5,1/5,8/100,12/100,14/5, 18/5; Flow rate: 1.2 ml/min.

Method-B: Column: X-Bridge CSH C18 (150×4.6 mm, 3.5 μm); Mobile Phase-A: 5 mM $NH_4HCO_3$; Mobile Phase-B: I; Programme: T/B %: 0.01/2,2/2,12/90,16/90; Flow rate: 1.0 mL/min.; Diluent: I: WATER (80:20).

Method-C: Column: X SELECT CSH C18 (150×4.6 mm, 3.5μ); Mobile Phase A; 0.05% TFA IN WATER: I (95:05); Mobile Phase B: 0.05% TFA IN WATER: I (05:95); Programme: T/B %: 0.01/10, 12/90, 16/90; Flow rate: 1 mL/min.; Diluent: WATER: I (80:20).

Method-D: Column: X-Bridge CSH C18 (4.6*150) mm 5u Mobile Phase: A-0.1% TFA in water B-Acetonitrile Inj Volume; 5.0 μL, Flow Rate: 1.2 mL/minute Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in HEXANE Mobile Phase B: IPA A/B: 60/40 Flow: 1.0 ml/MIN PDA: OJ-H_015.

Method-F: Column: ACE Excel 2 C18-AR, 100 mm×3.0 mm Mobile Phase A: 0.05% TFA in Water Mobile Phase B: 0.05% TFA in Acetonitrile Colum Temperature: 40° C. Flow Rate: 0.6 mL/min Gradient: 0/5, 1/5, 6/90, 8.5/90, 8.8/5, 11/5.

Method-G: Column: CHIRAL PAK-IC (250×4.6 mm, 5 μm) Mobile Phase A: 0.1% DEA in Hexane Mobile Phase B: ETOH/MEOH (50/50) A: B: 80/20 Flow 1.0 ml/min.

Method-H: Column: X-Bridge C18 (4.6*150) mm 5u Mobile Phase: A-5 mM Ammonium Acetate B-Acetonitrile Flow Rate: 1.0. mL/minute Gradient program: Time (min)/B Conc.: 0.01/5, 1.0/5, 8.0/100, 12.0/100, 14.0/5, 18.0/5.

Synthesis of Compound 9-3

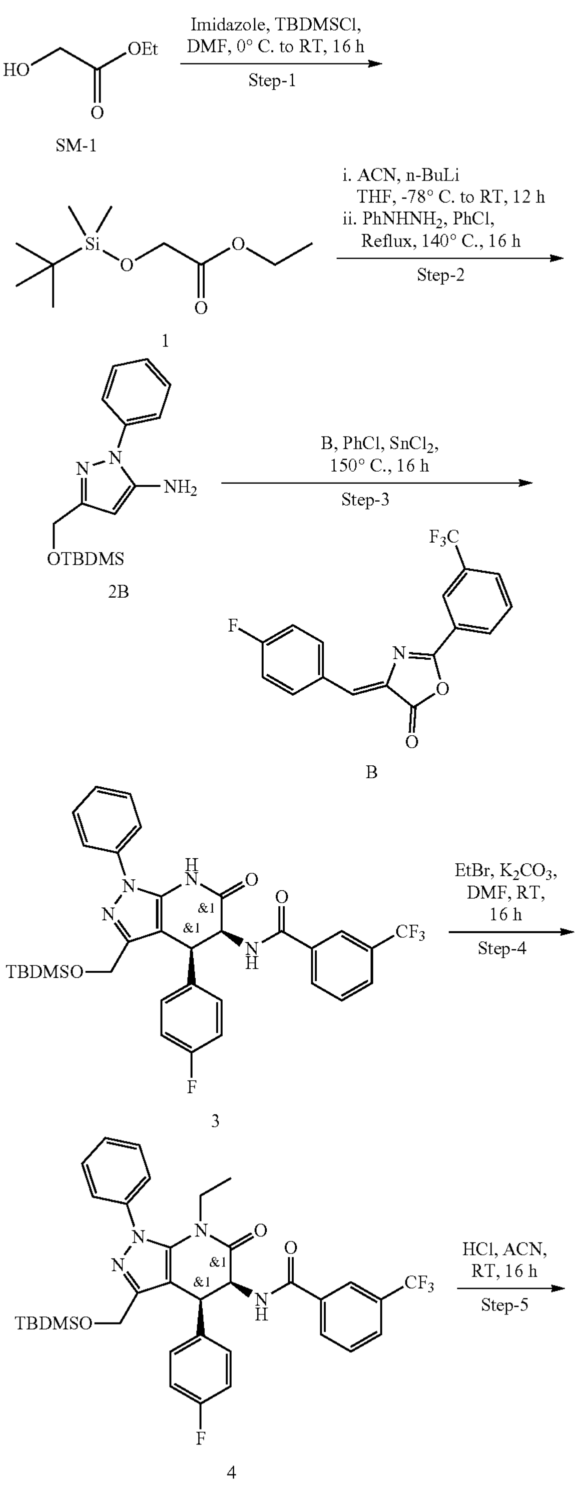

-continued

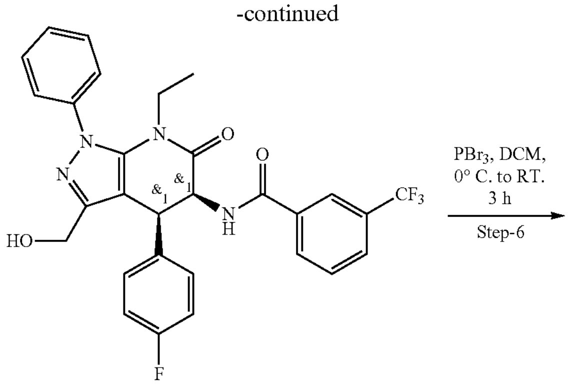

9-1

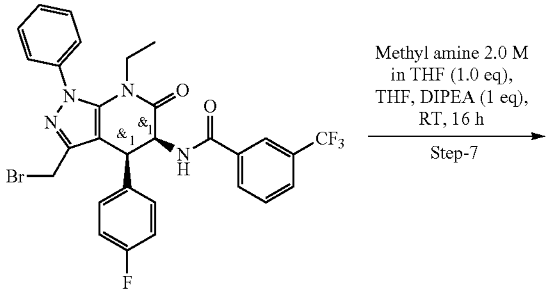

9-2

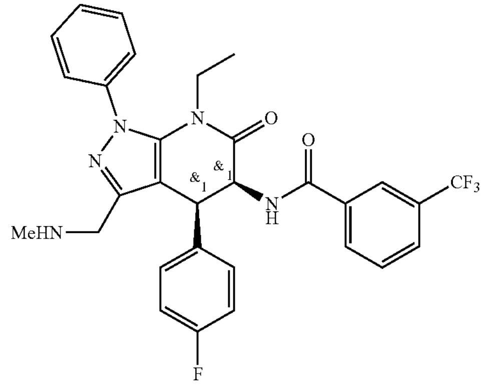

9-3

Step-1: Synthesis of ethyl 2-((tert-butyldimethylsilyl)oxy)acetate (1)

To stirred solution of compound (SM1) (25 g, 240.1 mmol) in DMF (125 mL) was added imidazole (27.6 g, 312.2 mmol) and TBDMSCl (47.04 g, 312.2 mmol) at 0° C. The reaction mixture was stirred at room temperature for 16 h. After consumption of the starting material (by TLC), the reaction mixture was quenched with water (1.2 lit) and extracted with EtOAc (2×500 mL). The combined organic layer was dried over anhydrous sodium sulfate and concentrated to afford crude compound. The obtained crude compound was purified by using flash column chromatography eluting with 0-20% EtOAC in Heptane. Pure fraction was collected and concentrated under vacuum to afford compound (1) (24 g, 46.1%) as colorless liquid.

$^1$H NMR (400 MHZ, DMSO-$d_6$): δ 4.21 (s, 2H), 4.09 (q, J=6.8 Hz, 2H), 1.18 (t, J=6.8 Hz, 3H), 0.88-0.82 (m, 9H), 0.06-0.07 (m, 6H).

Step-(2i): Synthesis of 3-(((tert-butyldimethylsilyl)oxy)methyl)-1-phenyl-1H-pyrazol-5-amine (2A)

To a stirred solution of acetonitrile (15 mL) in THF (750 mL), n-butyl lithium (2.5 mol/l) in hexanes (115 ml, 290 mmol) was added at −78° C. The reaction mixture was stirred at −78° C. for 30 min. after 30 mins, compound (1) (40 g, 183.18 mmol) dissolved in THF (750 mL) was added to the reaction mixture slowly at same temperature. Slowly the reaction mixture was allowed to warm to room temperature and maintained the same for 12 h. Reaction progress was monitored by TLC. After completion of the reaction, the reaction mixture was quenched with water (200 mL) and adjusted pH to 4-5 using 2N aq·HCl solution. The reaction solution was extracted with 2×500 mL ethyl acetate. Combined organic layer was dried over anhydrous sodium sulfate and concentrated under reduced pressure to afford crude compound (2A) (37 g, 94.67%) as a pale-brown oil.

Step-(2ii): Synthesis of 5-[[tert-butyl(dimethyl)silyl]oxymethyl]δδδ-2-phenyl-pyrazol-3-amine (2B)

To a stirred solution of compound (2A) (37 g, 173.42 mmol) in chlorobenzene (110 mL), phenylhydrazine (19 g, 173.94 mmol) was added at room temperature. The reaction mass temperature was raised to 140° C. The reaction mixture was stirred at same temperature for 16 h. Reaction progress was monitored by TLC. After completion of starting material, the reaction mixture was quenched with water (100 mL) and extracted with ethyl acetate (2×500 mL). Combined organic layer was dried over anhydrous sodium sulfate, concentrated under reduced pressure to afford crude compound. The obtained crude compound was purified by column chromatography eluting with 15-20% ethyl acetate in pet ether to afford compound (2B) (26.0 g, 35.07%) as a yellow solid.

$^1$H NMR (400 MHZ, DMSO-d6): δ 7.54-7.58 (m, 2H), 7.43-7.48 (m, 2H), 7.29 (dt, J=7.4, 1.2 Hz, 1H), 5.47 (s, 1H), 5.30 (s, 2H), 4.50 (s, 2H), 0.87-0.91 (m, 9H), 0.07 (s, 6H). LC-MS (Method-B)=304.7 [M+H]$^+$; 70.73% at RT 2.16 min.

Step-3: Synthesis of rac-N-((4R,5R)-3-(((tert-butyldimethylsilyl)oxy)methyl)-4-(4-fluorophenyl)-6-oxo-1-phenyl-4,5,6,7-tetrahydro-1H-pyrazolo[3,4-b]pyridine-5-yl)-3-(trifluoromethyl)benzamide (3)

To a stirred solution compound (2B) (26 g, 85.67 mmol) and Int-B (29.19 g, 85.67 mmol) in chlorobenzene (78 ml), tin(II) chloride (1.64 g, 8.56 mmol) was added at room temperature. The reaction mixture was stirred at 140-150° C. for 16 h. Reaction progress was monitored by TLC. After completion of reaction, the reaction mixture was quenched with water (1000 mL) and filtered through celite bed and washed with DCM (500 mL). Filtrate was washed with water and extracted with DCM (2×500 mL). Organic layer was dried over anhydrous sodium sulfate and concentrated under reduced pressure. The obtained crude was purified by column chromatography by eluting with 20-30% ethyl acetate in pet ether to afford compound (3) (30 g, 48.6%) as yellow solid.

$^1$H NMR (400 MHZ, DMSO-d6): δ 11.06 (s, 1H), 8.36 (d, J=3.4 Hz, 1H), 8.07 (s, 2H), 7.89 (d, J=7.3 Hz, 1H), 7.58-7.71 (m, 4H), 7.49-7.55 (m, 2H), 7.40 (d, J=6.8 Hz, 1H), 7.03-7.08 (m, 1H), 6.95 (s, 1H), 5.24-5.34 (m, 1H), 4.69 (d, J=6.8 Hz, 1H), 4.56-4.62 (m, 1H), 4.40-4.46 (m, 1H), 0.73 (s, 5H). LC-MS (Method-A)=639.29 $[M+H]^+$; 88.73% at RT 2.48 min.

Step-4: Synthesis of rac-N-((4R,5R)-3-(((tert-butyldimethylsilyl)oxy)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (4)

To a stirred solution of compound (3) (30 g, 41.33 mmol) in DMF (300 mL), potassium carbonate (7.50 g, 53.73 mmol) and bromoethane (5.45 g, 49.60 mmol) were added at room temperature. The reaction mixture was stirred at room temperature for 16 h. Reaction progress was monitored by TLC. After completion of SM, the reaction mixture was quenched with water (3 L) and extracted with ethyl acetate (2×1000 mL). Organic layer was dried over anhydrous sodium sulfate and evaporated under vacuum. The obtained crude was purified by column chromatography by eluting with 15-20% ethyl acetate in heptane to afford compound (4) (15 g, 48.3%) as yellow solid.

$^1$H NMR (400 MHZ, DMSO-d6) ($D_2O$): δ 8.05-8.10 (m, 2H), 7.91 (d, J=7.1 Hz, 1H), 7.68-7.74 (m, 1H), 7.49-7.64 (m, 5H), 7.03-7.10 (m, 2H), 6.90-6.95 (m, 2H), 5.41 (d, J=7.2 Hz, 1H), 4.65-4.69 (m, 1H), 4.62 (d, J=12.5 Hz, 1H), 4.45 (d, J=12.4 Hz, 1H), 2.94-3.08 (m, 2H), 0.79-0.92 (m, 3H), 0.70 (s, 9H), −0.12 (s, 6H). LC-MS (Method-B)=667.5 $[M+H]^+$; 83.38% at RT 2.52 min.

Step-5: Synthesis of rac-N-((4R,5R)-7-ethyl-4-(4-fluorophenyl)-3-(hydroxymethyl)-6-oxo-1-phenyl-4,5,6,7-tetrahydro-1H-pyrazolo[3,4-b]pyridine-5-yl)-3-(trifluoromethyl)benzamide (9-1)

To a stirred solution of compound (4) (20 g, 24.90 mmol) in acetonitrile (100 mL), hydrochloric acid (20 mL, 120 mmol) was added. The reaction mixture was stirred at room temperature for 16 h. Reaction progress was monitored by TLC. After completion of reaction, the reaction mixture was quenched with ice water (1000 mL) and extracted with ethyl acetate (2×1000 mL). Organic layer was dried over anhydrous sodium sulfate and concentrated under vacuum to afford crude compound. The crude material was washed with 10% diethyl ether in pentane and dried under vacuum to afford 9-1 (12.00 g, 83.75%) as a pale-yellow solid.

$^1$H NMR (400 MHZ, DMSO-d6, 25° C.): δ 8.53 (d, J=7.3 Hz, 1H), 8.12-8.17 (m, 2H), 7.92 (d, J=7.8 Hz, 1H), 7.64-7.74 (m, 3H), 7.50-7.61 (m, 3H), 7.10 (t, J=8.9 Hz, 2H), 6.93-7.05 (m, 2H), 5.50 (t, J=7.3 Hz, 1H), 5.11 (t, J=6.0 Hz, 1H), 4.72 (d, J=7.3 Hz, 1H), 4.35-4.41 (m, 1H), 4.24-4.30 (m, 1H), 3.87-3.94 (m, 1H), 2.98-3.08 (m, 1H), 0.91 (t, J=7.1 Hz, 3H). LC-MS (Method-B)=553.2 $[M+H]^+$; 96.44% at RT 2.26 min. HPLC (Method-B): 95.87% at RT 9.15 min.

Step-6: Synthesis of rac-N-((4R,5R)-3-(bromomethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (9-2)

To a stirred solution of compound (5) (2.0 g, 3.62 mmol) in DCM (10 mL) was added $PBr_3$ (0.58 mL, 5.4 mmol) at 0° C. The reaction mixture was stirred at room temperature for 3 h. Progress of the reaction was monitored by TLC. After consumption of reaction, the reaction mixture was diluted with water (100 mL) and extracted with DCM (2×100 mL). Organic layer was dried over sodium sulfate, concentrated under vacuum to afford crude. Obtained crude was purified by medium pressure liquid chromatography was eluted with 30-40% ethyl acetate/pentane to afford compound (9-2) (1.55 g, 54%) as an off-white solid.

$^1$H NMR (400 MHZ, DMSO-d6): δ 8.56 (d, J=7.3 Hz, 1H), 8.10-8.20 (m, 2H), 7.92 (d, J=7.3 Hz, 1H), 7.72 (d, J=7.3 Hz, 3H), 7.54-7.63 (m, 3H), 7.07-7.14 (m, 2H), 6.97-7.03 (m, 2H), 5.55 (t, J=7.1 Hz, 1H), 4.39 (d, J=11.2 Hz, 1H), 3.88 (dd, J=14.2, 7.3 Hz, 1H), 3.05 (dd, J=14.4, 7.1 Hz, 1H), 1.24 (s, 3H), 0.85-0.94 (m, 3H). LC-MS (Method-B)=614.7 $[M+H]^+$; 95.53% at RT 2.80 min.

Step-7: Synthesis of rac-N-((4R,5R)-7-ethyl-4-(4-fluorophenyl)-3-((methylamino)methyl)-6-oxo-1-phenyl-4,5,6,7-tetrahydro-1H-pyrazolo[3,4-b]pyridine-5-yl)-3-(trifluoromethyl)benzamide (9-3)

To a stirred solution of compound (9-2) (1.5 g, 2.4 mmol) was added DIPEA (0.41 mL, 2.4 mmol) followed by addition of methyl amine (2.0 M) in THF at room temperature. The reaction mixture was stirred at room temperature for 16 h. Progress of the reaction was monitored by TLC. After consumption of reaction, the reaction mixture was concentrated under vacuum to afford crude. Obtained crude was purified by medium pressure liquid chromatography eluting with 5-10% MeOH/DCM to afford compound (9-3) (750 mg, 57.4%) as an off-white solid.

$^1$H NMR (400 MHZ, DMSO-d6): δ 8.63 (d, J=7.5 Hz, 1H), 8.09-8.21 (m, 2H), 7.93 (d, J=7.9 Hz, 1H), 7.68-7.75 (m, 3H), 7.54-7.68 (m, 3H), 7.14 (t, J=8.8 Hz, 2H), 7.01 (dd, J=8.6, 5.6 Hz, 2H), 5.75 (s, 1H), 5.54 (dt, J=7.3, 3.8 Hz, 1H), 4.71 (d, J=7.3 Hz, 1H), 4.08 (d, J=14.5 Hz, 1H), 3.82-3.97 (m, 2H), 3.06 (dd, J=14.3, 7.0 Hz, 1H), 2.49-2.50 (m, 3H), 0.92 (t, J=7.1 Hz, 3H). LC-MS (Method-B)=564.4 $[M-H]^-$; 90.98% at RT 2.20 min. HPLC (Method-C): Peak-1=49.86% at RT 8.97 min. HPLC (Method-C): Peak-2=50.14% at RT 10.47 min.

Synthesis of Intermediate B

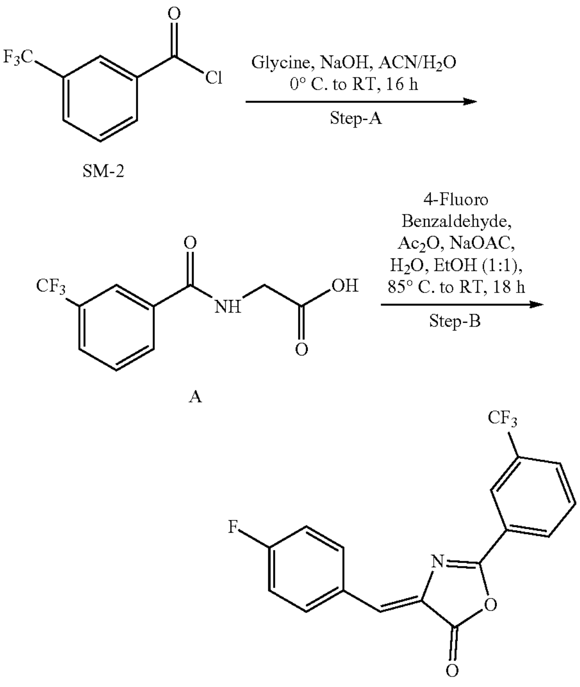

SM-2

A

B

Step-A: Synthesis of (3-(trifluoromethyl)benzoyl)glycine (A)

A stirred solution of glycine (359.89 g, 4794.78 mmol) in I (6 L) was added to NaOH (479.35 g, 11986.95 mmol in 1.2 L of water) solution at 0° C. and stirred for 15 min. 3-(trifluoromethyl)benzoyl chloride (SM-2) (1000 g, 4794.78 mmol) in I (2 L) was added dropwise at 0° C. The reaction mixture was stirred at room temperature for 16 h. After consumption of the starting material (by TLC), the reaction mixture was diluted with water (3 L) and acidified with HCl, and pH was adjusted to 1-3 and extracted with EtOAc (2×10 L). The combined organic layer was washed with brine solution (5 L), dried over anhydrous $Na_2SO_4$, filtered, and concentrated under reduced pressure to afford crude compound. Crude compound was triturated with n-Heptane to get pure Compound-B (1000 g, 84.38%) as a yellow solid.

$^1$H NMR (400 MHZ, DMSO-$d_6$): δ 9.13-9.05 (m, 1H), 8.27-8.13 (m, 2H), 7.93 (d, J=7.5 Hz, 1H), 7.74 (t, J=7.7 Hz, 1H), 3.94 (d, J=5.8 Hz, 2H). LC-MS (Method-A)=248.12 $[M+H]^+$; 98.23% at RT 1.14 min.

Step-B: Synthesis of (Z)-4-(4-fluorobenzylidene)-2-(3-(trifluoromethyl)phenyl)oxazol-5 (4H)-one (B)

To a stirred solution of (A) (1000 g, 4045.8 mmol) in acetic anhydride (1250 g, 12137 mmol) was added 4-Fluoro Benzaldehyde (502.12 g, 4045.8 mmol) and allowed to stir for 10 to 15 min, followed by addition of NaOAc (335 g, 4045.8 mmol). The reaction mixture was heated at 80° C.-85° C. for 4 h. Reaction was monitored by TLC. After completion of reaction, the reaction mass was cooled to room temperature, Ethanol (500 mL) and Water (500 mL) were added, the mass was stirred for 8-10 hr. The reaction mixture was filtered, washed with heptane (100 mL), and dried for 1 h. Obtained compound was azeotroped with toluene (2×500 mL) and filtered with heptane (3 L) to afford compound (B) (800 g, 60%) as a pale-yellow solid. LC-MS (Method-A)=336.1 $[M+H]^+$; 80.55% at RT 1.56 min $^1$H NMR (400 MHZ, DMSO-$d_6$): δ 8.46-8.38 (m, 2H), 8.33 (s, 1H), 8.11 (d, J=7.6 Hz, 1H), 7.90 (t, J=7.8 Hz, 1H), 7.50-7.33 (m, 4H).

Synthesis of Analogs:

General Scheme

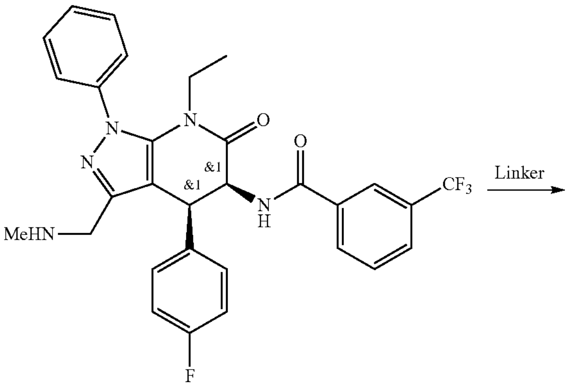

9-3

-continued

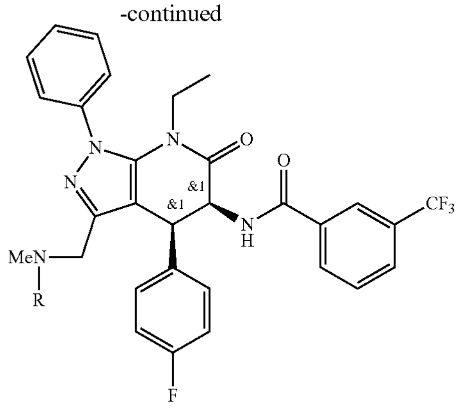

Method A: HBTU, DIPEA, DCM, RT, 16 h
Method B: $Et_3N$, DCM, RT, 16 h
Method C: HBTU, HOBT, DIPEA, DCM, 0° C. to RT, 16 h
Method D: TEA, DCM, RT, 16 h General Method (A):

To a stirring solution of 9-3 (1.0 eq) in DCM (mL) were added linker (1.3 eq), HBTU (1.5 eq) followed by DIPEA (3.2 eq) at room temperature for 16 h. The reaction was monitored by TLC. After completion of the reaction, the reaction mixture was diluted with water (10 mL) and extracted using DCM (2×20 mL). The combined organic layer was dried over sodium sulphate and concentrated under reduced pressure, purified by medium pressure liquid chromatography by eluting with 30-40% EtOAc in heptane.

General Method (B):

To a stirring solution of 9-3 (1.0 eq) in DCM (mL) were added linker (1.3 eq) followed by TEA (2.00 eq) at room temperature and stirred for 16 h. The reaction was monitored by TLC; after completion of reaction, the reaction mixture was quenched with water (10 mL) and extracted using ethyl acetate (2×20 mL). The combined organic layer was dried over sodium sulphate and concentrated under reduced pressure, purified by medium pressure liquid chromatography by eluting with 40% EtOAc in heptane.

General Method I:

To a stirring solution of 9-3 (0.01 g, 0.02 mmol) in DCM (2 mL) were added linker (1.0 eq), HBTU (1.0 eq) and HOBT (1.0 eq) followed by DIPEA (2.5 eq) at 0° C. The reaction mixture was allowed to room temperature and stirred for 16 h. The reaction was monitored by TLC; after completion of reaction, the reaction mixture was quenched with water (10 mL) and extracted using DCM (2×20 mL). The combined organic layer was dried over sodium sulphate and concentrated under reduced pressure. The crude product was purified by prep. HPLC to afford corresponding compound.

General Method (D):

To a stirred solution of 9-3 (1.0 eq) in dichloromethane (10 mL) was added triethylamine (1.1 eq) and Linker (1.2 eq) stirred the reaction at room temperature for 16 h. Progress of the reaction was monitored by TLC. The reaction mixture quenched with water (10 mL) and extracted with DCM (2×20 mL), combined organic layers was dried over anhydrous sodium sulfate and concentrated to afford crude compound above crude compound was purified by silica gel (230-400) column chromatography using ethyl acetate in heptane product eluted in 40% ethyl acetate in heptane, product containing fractions was collected and concentrated to afford pure compound.

-continued

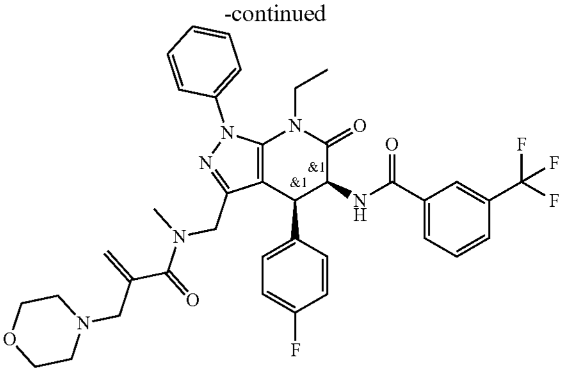

I-185

Synthesis of I-185

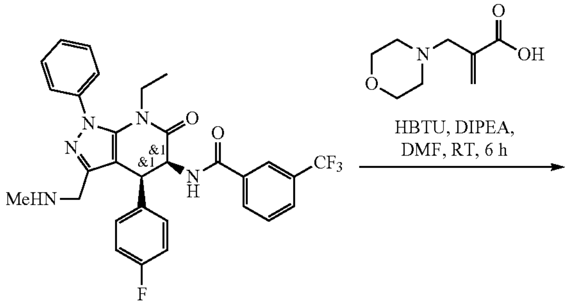

9-3

To a stirred solution of 9-3 (120.0 mg, 0.21 mmol) in DMF was added N,N-diisopropylethylamine (0.12 mL, 0.69 mmol) then added 2-(morpholinomethyl) acrylic acid (47.29 mg, 0.27 mmol) followed by HBTU (120.95 mg, 0.32 mmol) and the reaction was stirred at room temperature for 6 h. Progress of the reaction was monitored by TLC and LC-MS. After completion of reaction, the reaction mixture was quenched with water (10 mL) and extracted with ethyl acetate (2×20 mL), combined organic layer was dried over anhydrous sodium sulfate and concentrated to afford crude compound. Obtained crude compound was purified by silica gel (230-400) column chromatography using ethyl acetate in heptane. Product was eluted in 60% ethyl acetate in heptane, product containing fractions was collected and concentrated to afford pure compound as a white solid I-185 (25 mg, 16.23%). The analogs were synthesized as described in the table below.

| Cpd. Number | Structure (R) | 9-3 Qty (mg) | Linker Qty (mg) | Method | Qty (mg) & nature of compound | Yield (%) |
|---|---|---|---|---|---|---|
| I-233 | 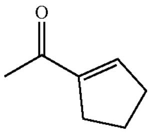 | 120 | 30.95 | A | 35 (White solid) | 25 |
| I-200 | 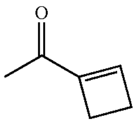 | 120 | 22 | A | 45 (White solid) | 31 |
| I-201 | 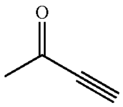 | 120 | 22.3 | A | 20 (White solid) | 18 |
| I-228 | 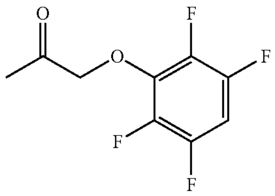 | 120 | 60 | A | 89.8 (White solid) | 75 |

-continued
| Cpd. Number | Structure (R) | 9-3 Qty (mg) | Linker Qty (mg) | Method | Qty (mg) & nature of compound | Yield (%) |
|---|---|---|---|---|---|---|
| I-90 | 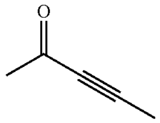 | 120 | 20 | A | 65 (White solid) | 49 |
| I-55 | 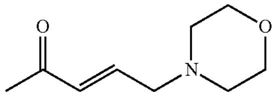 | 120 | 120 | A | 22 (White solid) | 14 |
| I-117 | 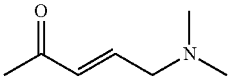 | 130 | 38.5 | A | 45 (White solid) | 27.6 |
| I-145 | 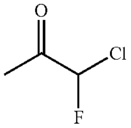 | 130 | 113 | A | 50 (Off white solid) | 33 |
| I-1 | 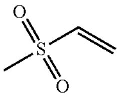 | 150 | 40 | B | 39 (White solid) | 22 |
| I-234 | 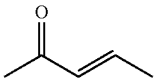 | 130 | 26 | B | 27 (White solid) | 18 |
| I-186 | 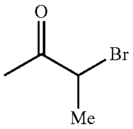 | 50 | 20 | B | 20 (Off white solid) | 32 |
| I-29 | 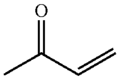 | 130 | 23 | B | 25 (off white solid) | 18 |
| I-30 | 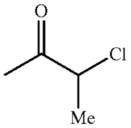 | 120 | 29 | B | 20 (Off white solid | 16 |
| I-33 | 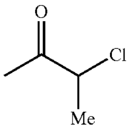 | 120 | 29 | B | 26 (Off white solid) | 21 |
| I-178 | 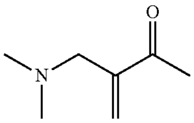 | 100 | 20 | C | 7.87 (Off white solid) | 5 |
| I-219 | 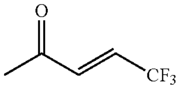 | 150 | 40 | C | 36 (White solid) | 34 |
| I-129 |  | 500 | 121.7 | D | 350.0 (White solid | 66.3 |

-continued

| Cpd. Number | Structure (R) | 9-3 Qty (mg) | Linker Qty (mg) | Method | Qty (mg) & nature of compound | Yield (%) |
|---|---|---|---|---|---|---|
| I-156 | 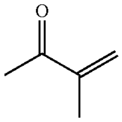 | 120 | 24.4 | D | 55 (White solid | 40 |
| I-227 | 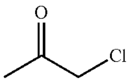 | 100 | 21.8 | D | 42 (White solid | 37 |

I-233

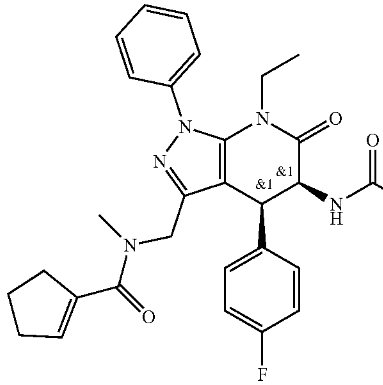

$^1$H NMR (400 MHZ, DMSO-$d_6$) δ=8.52 (d, J=6.8 Hz, 1H), 8.17-8.13 (m, 2H), 7.92 (d, J=7.6 Hz, 1H), 7.73-7.69 (m, 3H), 7.61-7.52 (m, 3H), 7.08-7.06 (m, 2H), 6.88 (s, 2H), 5.48 (t, J=14.4 Hz, 2H), 4.89-4.87 (m, 1H), 4.48-4.46 (m, 1H), 4.14 (s, 1H), 3.91-3.82 (m, 2H), 3.07-3.02 (m, 2H), 2.70-2.66 (m, 2H), 2.29 (s, 3H), 1.74-1.70 (m, 2H), 0.92-0.82 (m, 3H). LCMS (Method-D)=660.2 [M+H]$^+$; 97.67% at RT 2.46 min. HPLC (Method-B): 98.50% at RT 10.04 min.

I-200

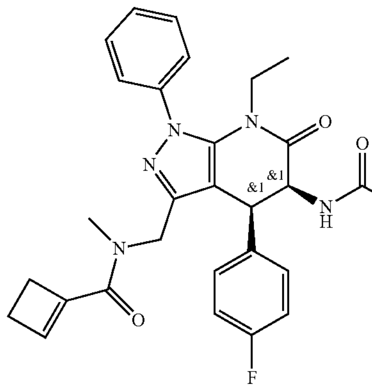

$^1$H NMR (400 MHZ, DMSO-$d_6$) δ=8.48 (d, J=7.2 Hz, 1H), 8.18-8.14 (m, 2H), 7.92 (d, J=8.0 Hz, 1H), 7.73-7.69 (m, 3H), 7.61-7.52 (m, 3H), 7.09-7.03 (m, 2H), 6.83-6.79 (m, 2H), 6.08 (s, 1H), 5.49 (t, J=7.6 Hz, 1H), 5.10 (d, J=14.8 Hz, 1H), 4.39 (d, J=7.6 Hz, 1H), 3.92-3.84 (m, 2H), 3.31-3.01 (m, 1H), 2.67-2.60 (m, 3H), 2.39-2.27 (m, 2H), 1.28-1.23 (m, 1H), 0.92-0.91 (m, 4H). LCMS (Method-D)=646.2 [M+H]$^+$; 95.89% at RT 2.400 min. HPLC (Method-B): 95.66% at RT 9.77 min.

I-201

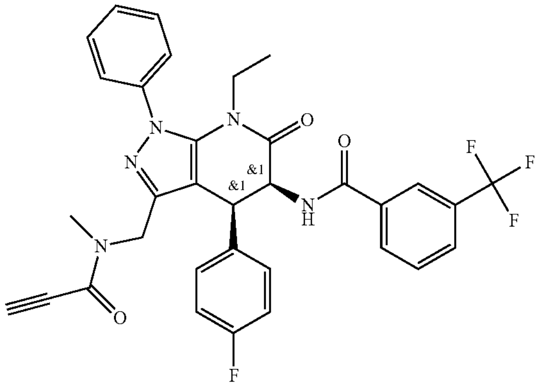

$^1$H NMR (400 MHZ, DMSO-$d_6$) δ=8.55-8.52 (m, 1H), 8.17-8.13 (m, 2H), 7.92 (d, J=7.6 Hz, 1H), 7.73-7.69 (m, 3H), 7.62-7.53 (m, 3H), 7.08 (t, J=8.8 Hz, 2H), 6.92-6.85 (m, 2H), 5.54-5.48 (m, 1H), 4.87-4.77 (m, 1H), 4.60-4.07 (m, 3H), 3.89-3.84 (m, 1H), 2.76 (s, 2H), 2.56 (s, 2H), 0.92-0.89 (m, 3H). LCMS (Method-D)=618.3 [M+H]$^+$; 99.18% at RT 2.12 min. HPLC (Method-B): 99.83% at RT 9.095 min.

I-228

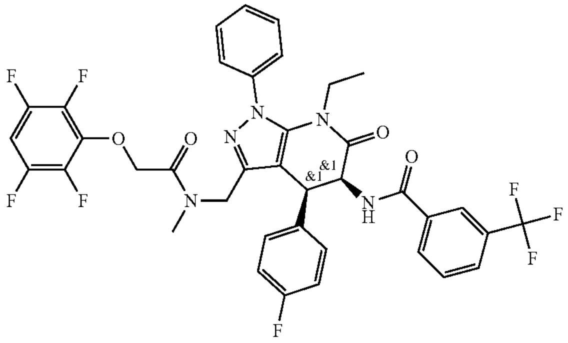

$^1$H NMR (400 MHZ, DMSO-$d_6$) δ=8.59-8.53 (m, 1H), 8.17-8.12 (m, 2H), 7.92 (d, J=7.8 Hz, 1H), 7.73-7.67 (m, 3H), 7.61-7.44 (m, 4H), 7.07-7.02 (m, 2H), 6.98-6.84 (m, 2H), 5.56-5.47 (m, 1H), 5.16-5.15 (m, 1H), 4.83 (dd, J=9.7, 14.9 Hz, 2H), 4.41-4.36 (m, 1H), 4.10 (dd, J=3.2, 14.8 Hz, 1H), 3.89-3.84 (m, 1H), 3.08-3.01 (m, 1H), 2.57 (s, 3H), 0.92-0.85 (m, 3H). LCMS (Method-D)=772.2 [M+H]$^+$; 96.28% at RT 2.52 min. HPLC (Method-B): 95.60% at RT 10.167 min.

I-90

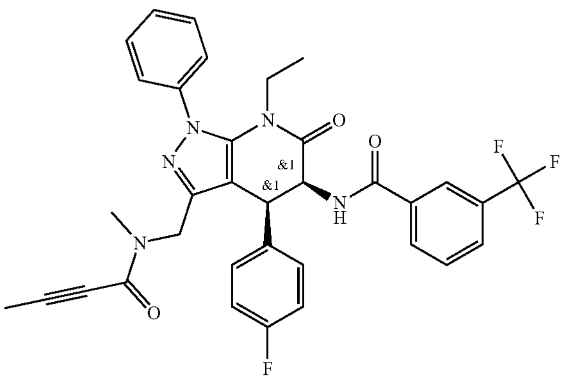

$^1$H NMR (400 MHZ, DMSO-$d_6$) δ=8.57-8.51 (m, Hz, 1H), 8.17-8.13 (m, 2H), 7.92 (d, J=7.6 Hz, 1H), 7.73-7.68 (m, 3H), 7.62-7.52 (m, 3H), 7.12-7.06 (m, 2H), 6.89-6.85 (m, 2H), 5.52-5.48 (m, 1H), 4.87 (dd, J=11.4, 15.3 Hz, 1H), 4.66-4.48 (m, 1H), 4.40-4.02 (m, H), 3.90-3.84 (m, 1H), 3.07-3.01 (m, 1H), 2.70 (s, 2H), 2.51 (s, 3H), 1.98 (s, 1H), 1.88 (s, 2H), 0.91 (t, J=6.8 Hz, 3H). LCMS (Method-D)=632.2 [M+H]$^+$; 95.75% at RT 2.37 min. HPLC (Method-B): 98.11% at RT 9.49 min.

I-55

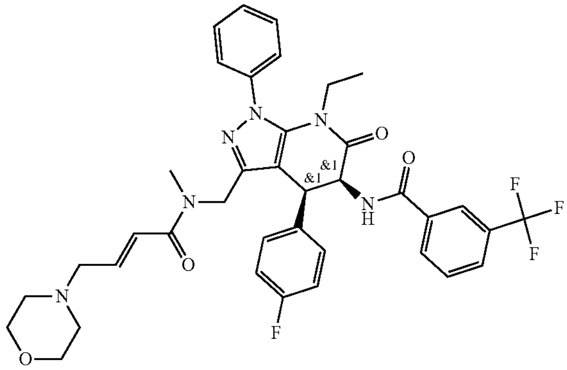

$^1$H NMR (400 MHZ, DMSO-$d_6$) δ=8.49-8.47 (m, Hz, 1H), (s, 1H), 8.17-8.13 (m, 1H), 7.92 (d, J=7.6 Hz, 1H), 7.73-7.68 (m, 3H), 7.61-7.53 (m, 3H), 7.09-7.00 (m, 2H), 6.90-6.81 (m, 2H), 5.53-5.44 (m, 1H), 5.06 (s, 1H), 4.50-4.01 (m, 3H), 3.55-3.51 (m, 4H), 2.99-2.92 (m, 3H), 2.67-2.62 (m, 5H), 2.33-2.27 (m, 4H), 0.92-0.88 (m, 3H). LCMS (Method-E)=719.1 [M+H]$^+$; 99.36% at RT 2.29 min. HPLC (Method-B): 98.84% at RT 9.640 min.

I-117

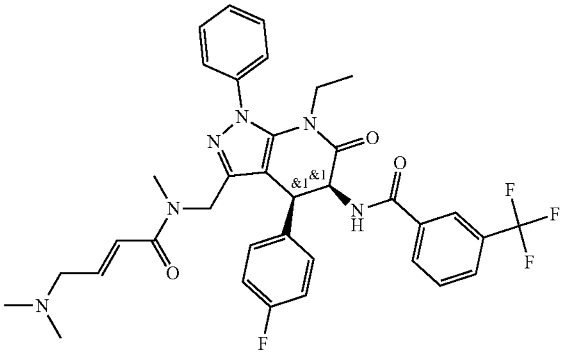

$^1$H NMR (400 MHZ, DMSO-$d_6$) δ 8.50-8.48 (m, 1H), 8.17-8.13 (m, 2H), 7.92 (d, J=7.6 Hz, 1H), 7.73-7.68 (m, 3H), 7.61-7.53 (m, 3H), 7.11-7.01 (m, 2H), 6.84-6.81 (m, 2H), 6.45-6.04 (m, 1H), 6.05 (s, 1H), 5.48 (t, J=6.8 Hz, 1H),), 5.00 (d, J=14.8 Hz, 1H), 4.54-4.42 (m, 2H), 4.04.-3.84 (m, 4H), 3.07-3.01 (m, 2H), 2.64 (s, 3H), 2.22 (s, 4H), 0.90 (t, J=6.8 Hz, 3H). LCMS (Method-D)=677.3 [M+H]$^+$; 98.79% at RT 2.16 min. HPLC (Method-B): 98.42% at RT 9.18 min.

I-145

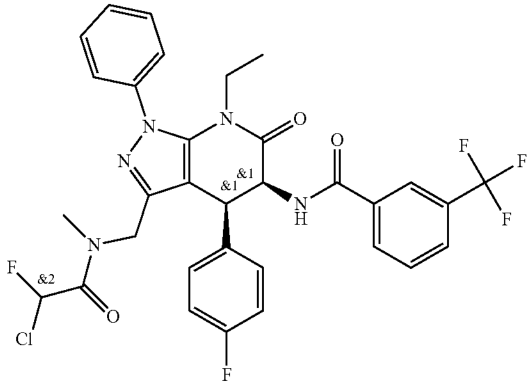

$^1$H NMR (400 MHZ, DMSO-$d_6$) δ 8.53-8.51 (m, 1H), 8.15-8.12 (m, 2H), 7.92 (d, J=7.6 Hz, 1H), 7.72-7.69 (m, 3H), 7.61-7.52 (m, 3H), 7.10-7.03 (m, 2H), 6.94-6.84 (m, 2H), 5.55-5.47 (m, 1H), 4.76 (d, J=14.8 Hz, 1H), 4.55-4.50 (m, 1H), 4.42-4.34 (m, 1H), 4.22-4.18 (m, 1H), 3.89-3.84 (m, 1H), 3.09-3.00 (m, 2H), 2.84 (s, 1H), 2.68 (s, 1H), 0.90 (t, J=6.8 Hz, 3H). LCMS (Method-D)=661.2 [M+H]$^+$; 98.85% at RT 2.42 min. HPLC (Method-B): 93.42% at 9.30 min.

I-1

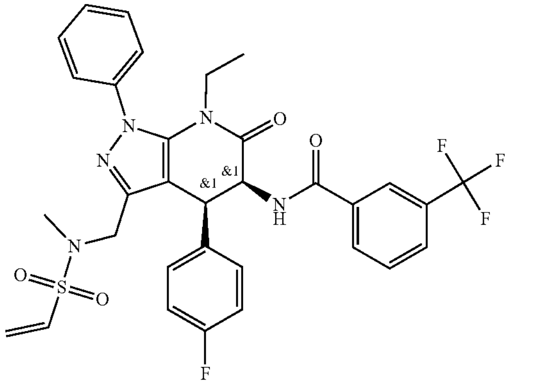

$^1$H NMR (400 MHZ, DMSO-$d_6$) δ=8.53 (d, J=7.6 Hz, 1H), 8.15-8.12 (m, 2H), 7.92 (d, J=7.6 Hz, 1H), 7.72-7.68 (m, 3H), 7.62-7.53 (m, 3H), 7.11-7.07 (m, 2H), 6.98-6.95 (m, 2H), 6.76-6.99 (m, 1H), 6.10-6.04 (m, 2H), 5.53 (t, J=7.6 Hz, 1H), 4.64 (d, J=7.2 Hz, 1H), 4.12-4.04 (m, 2H), 3.91-3.84 (m, 1H), 3.08-3.03 (m, 1H), 2.43 (s, 3H), 0.91 (t, J=6.8 Hz, 3H). LCMS (Method-D)=656.2 [M+H]$^+$; 97.73% at RT 2.43 min. HPLC (Method-B): 98.37% at RT 9.82 min.

I-234

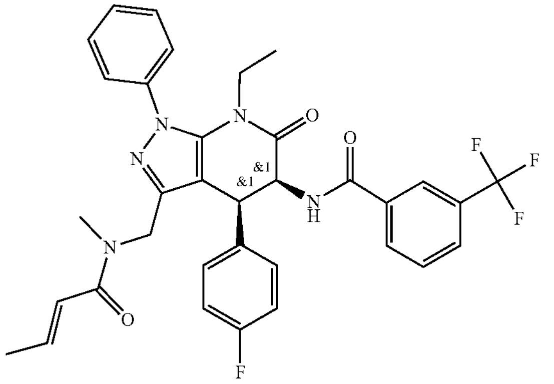

$^1$H NMR (400 MHZ, DMSO-$d_6$) δ=8.48 (d, J=6.8 Hz, 1H), 8.17-8.13 (m, 2H), 7.92 (d, J=7.6 Hz, 1H), 7.73-7.68 (m, 3H), 7.61-7.51 (m, 3H), 7.08-7.01 (m, 2H), 6.89-6.80 (m, 2H), 6.54-6.32 (m, 1H), 5.81 (d, J=14.8 Hz, 1H), 5.48 (t, J=7.6 Hz, 1H), 5.03 (d, J=14.8 Hz, 1H), 4.53-4.41 (m, 2H), 3.98-3.82 (m, 1H), 3.06-3.01 (m, 1H), 2.62 (s, 3H), 1.69 (d, J=6.4 Hz, 3H).0.90 (t, J=7.2 Hz, 3H). LCMS (Method-C)=634.4 [M+H]$^+$; 95.23% at RT 2.26 min. HPLC (Method-A): 95.37% at RT 9.19 min.

I-186

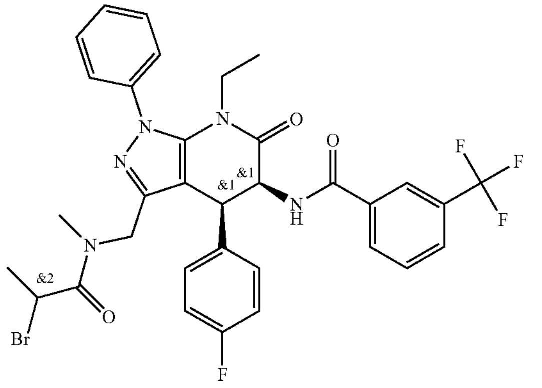

$^1$H NMR (400 MHZ, DMSO-$d_6$) 8.53 (d, J=6.8 Hz, 1H), 8.18-8.10 (m, 2H), 7.92 (d, J=7.6 Hz, 1H), 7.73-7.68 (m, 3H), 7.61-7.54 (m, 3H), 7.13-7.07 (m, 2H), 6.98-6.86 (m, 2H), 5.55-5.43 (m, 1H), 4.94-4.88 (m, 1H), 4.83-4.81 (m, 1H), 4.69-4.64 (m, 1H), 4.56-4.49 (m, 1H), 3.89-3.84 (m, 1H), 3.07-3.00 (m, 1H), 2.93 (d, J=13.6 Hz, 1H). 2.73 (d, J=8.0 Hz, 1H), 1.63-1.51 (m, 1H), 1.45-1.36 (m, 1H), 3.89-3.84 (m, 1H), 1.22 (d, J=6.4 Hz, 1H), 0.92-085 (m, 3H). LCMS (Method-D)=656.0 [M+H]$^+$; 98.69% at RT 2.46 min. HPLC (Method-B): 96.8% at RT 9.87 min.

I-30

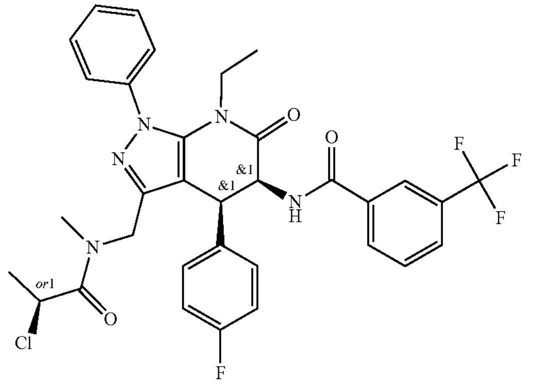

$^1$H NMR (400 MHZ, DMSO-$d_6$) δ=8.56-8.49 (m, 1H), 8.21-8.11 (m, 2H), 7.92 (d, J=7.6 Hz, 1H), 7.70 (q, J=7.7 Hz, 4H), 7.64-7.52 (m, 4H), 7.16-7.05 (m, 3H), 6.88 (dd, J=5.5, 8.5 Hz, 2H), 5.55-5.46 (m, 1H), 4.92 (d, J=14.8 Hz, 1H), 4.41 (d, J=7.0 Hz, 1H), 4.05 (d, J=14.6 Hz, 1H), 3.93-3.81 (m, 1H), 3.10-2.98 (m, 1H), 2.77-2.70 (m, 3H), 1.24 (d, J=6.5 Hz, 3H), 0.95-0.86 (m, 3H). LCMS (Method-D)=656.2 [M+H]$^+$; 98.22% at RT 2.44 min. HPLC (Method-B): 98.95% at RT 10.01 min.

I-33

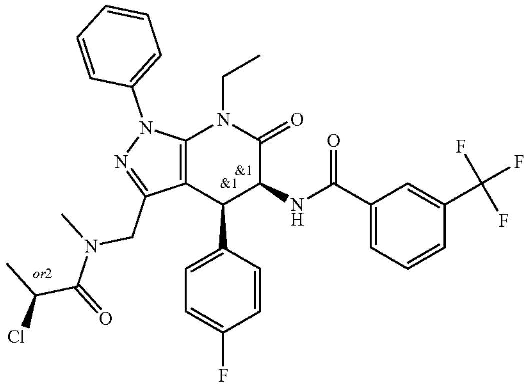

$^1$H NMR (400 MHZ, DMSO-$d_6$) δ=8.59-8.48 (m, 1H), 8.14 (t, J=11.6 Hz, 3H), 7.92 (d, J=8.1 Hz, 1H), 7.77-7.66 (m, 4H), 7.64-7.50 (m, 4H), 7.14-7.04 (m, 3H), 7.00-6.90 (m, 3H), 5.48-5.43 (m, 1H), 4.86-4.79 (m, 1H), 4.68-4.63 (m, 1H), 4.58-4.48 (m, 2H), 4.33-4.26 (m, 1H), 3.81 (s, 1H), 3.11-3.00 (m, 1H), 2.92 (s, 2H), 2.65 (s, 2H), 1.45 (d, J=6.4 Hz, 2H), 1.41-1.35 (m, 1H), 0.90 (t, J=7.0 Hz, 3H). LCMS (Method-D)=656.3 $[M+H]^+$; 98.23% at RT 2.22 min. HPLC (Method-B): 98.89% at RT 9.77 min.

I-219

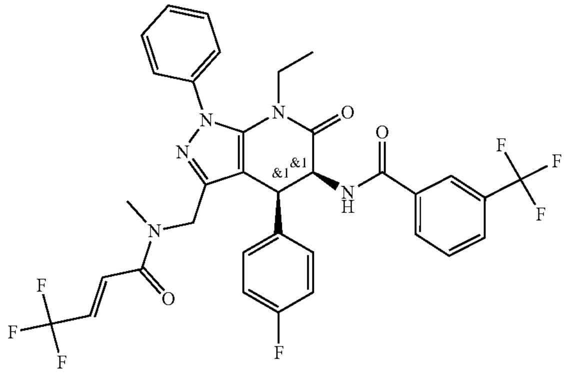

$^1$H NMR (400 MHZ, DMSO-$d_6$) δ=8.58-8.53 (m, 1H), 8.19-8.14 (m, 2H), 7.92 (d, J=7.6 Hz, 1H), 7.73-7.66 (m, 3H), 7.62-7.52 (m, 3H), 7.09-6.98 (m, 2H), 6.89-6.81 (m, 2H), 6.52-6.45 (m, 1H), 5.54-5.48 (m, 1H), 5.13 (d, J=14.8 Hz, 1H), 4.51 (d, J=7.2 Hz, 1H), 4.41 (d, J=7.2 Hz, 1H), 3.99-3.83 (m, 2H), 3.05-3.00 (m, 1H), 2.68 (s, 3H), 0.91-088 (m, 3H). LCMS (Method-D)=688.2 $[M+H]^+$; 99.78% at RT 2.47 min. HPLC (Method-B): 98.64% at RT 9.97 min.

I-29

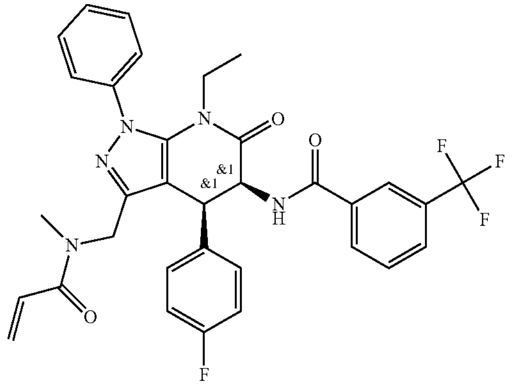

$^1$H NMR (400 MHZ, DMSO-$d_6$) δ=8.53-8.47 (m, 1H), 8.16-8.12 (m, 2H), 7.92 (d, J=7.6 Hz, 1H), 7.72-7.69 (m, 3H), 7.61-7.52 (m, 3H), 7.08-7.01 (m, 2H), 6.93-6.67 (m, 2H), 6.23-6.16 (m, 1H), 5.94-5.84 (m, 1H), 5.50-5.47 (m, 2H), 4.98 (d, J=14.4 Hz, 1H), 4.56-4.51 (m, 1H), 4.45-4.03 (m, 2H), 3.89-3.84 (m, 1H), 3.07-3.02 (m, 1H), 2.67-2.64 (m, 3H), 0.92-085 (m, 3H). LCMS (Method-D)=620.2 $[M+H]^+$; 96.89% at RT 2.33 min. HPLC (Method-A): 95.71% at RT 9.08 min.

I-185

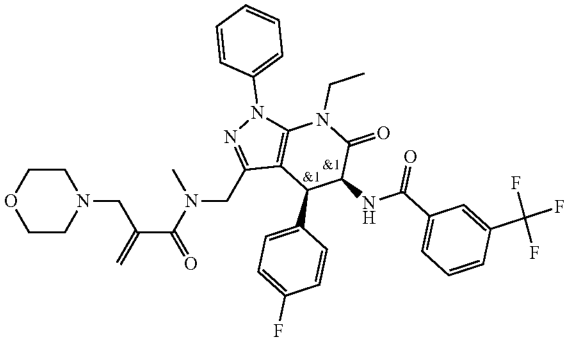

$^1$H NMR (400 MHZ, DMSO-$d_6$) δ=8.53 (d, J=6.4 Hz, 1H), 8.17-8.13 (m, 2H), 7.92 (d, J=7.6 Hz, 1H), 7.73-7.68 (m, 3H), 7.61-7.52 (m, 3H), 7.09 (s, 2H), 6.93 (s, 2H), 5.49 (d, J=6.0 Hz, 1H), 5.21-5.16 (m, 1H), 4.65-4.60 (m, 2H), 4.51-4.49 (m, 2H), 4.39-4.31 (m, 2H), 3.90-3.85 (m, 1H), 3.48 (s, 4H), 3.07-2.98 (m, 2H), 2.79-2.75 (m, 2H), 2.32-2.24 (m, 4H), 0.90 (t, J=6.8 Hz, 3H). LCMS (Method-D)=719.2 $[M+H]^+$; 99.39% at RT 2.37 min. HPLC (Method-B): 99.67% at RT 9.48 min.

I-129

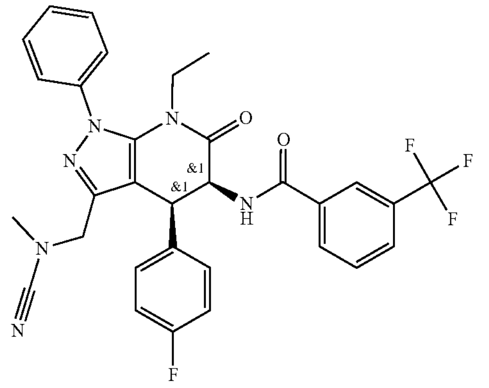

$^1$H NMR (400 MHZ, DMSO-$d_6$) δ=8.56 (d, J=7.2 Hz, 1H), 8.15-8.12 (m, 2H), 7.92 (d, J=7.6 Hz, 1H), 7.73-7.69 (m, 3H), 7.62-7.53 (m, 3H), 7.13-7.09 (m, 2H), 7.02-6.98 (m, 2H), 5.54 (t, J=7.2 Hz, 1H), 4.63 (d, J=7.2 Hz, 1H), 4.22-4.18 (m, 1H), 4.11-4.07 (m, 1H), 3.90-3.83 (m, 1H), 3.10-3.05 (m, 1H), 2.51-2.49 (m, 3H), 0.92 (t, J=6.8 Hz, 3H). LCMS: (Method-D)=591.2 $[M+H]^+$; 99.26% at RT 2.35 min. HPLC (Method-B): 99.11% at RT 8.88 min.

I-156

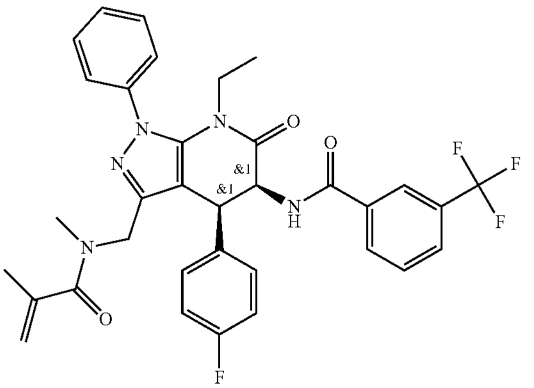

$^1$H NMR (400 MHZ, DMSO-$d_6$) δ=8.52 (d, J=6.8 Hz, 1H), 8.17-8.13 (m, 2H), 7.92 (d, J=7.6 Hz, 1H), 7.73-7.68 (m, 3H), 7.61-7.52 (m, 3H), 7.11-7.07 (m, 2H), 6.92 (br s, 2H), 5.48 (t, J=6.8 Hz, 1H), 5.03 (s, 1H), 4.71-4.24 (m, 4H), 3.91-3.84 (m, 1H), 3.07-3.02 (m, 1H), 2.74 (s, 3H), 1.62 (s, 3H), 0.90 (t, J=6.8 Hz, 3H). LCMS: (Method-D)=634.2 $[M+H]^+$; 98.85% at RT 2.40 min. HPLC (Method-B): 97.45% at RT 9.64 min.

I-227

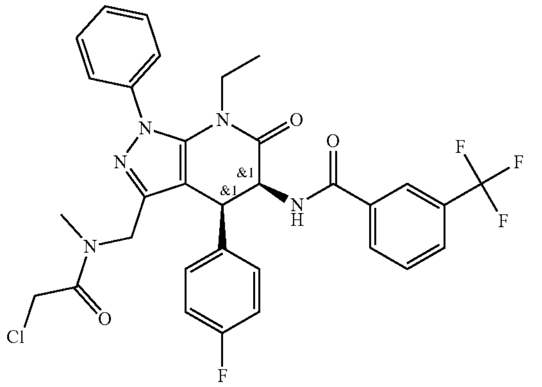

$^1$H NMR (400 MHZ, DMSO-$d_6$) δ=8.52 (d, J=7.6 Hz, 1H), 8.17-8.13 (m, 2H), 7.92 (d, J=8.0 Hz, 1H), 7.73-7.69 (m, 3H), 7.61-7.52 (m, 3H), 7.12-7.08 (m, 2H), 6.88-6.84 (m, 2H), 5.50 (t, J=7.2 Hz, 1H), 4.89 (d, J=14.8 Hz, 1H), 4.47-4.33 (m, 2H), 4.05-3.97 (m, 1H), 3.89-3.84 (m, 1H), 3.45 (s, 1H), 3.07-3.02 (m, 1H), 2.61 (s, 3H), 0.91 (t, J=6.8 Hz, 3H). LCMS: (Method-D)=591.2 $[M+H]^+$; 99.26% at RT 2.35 min. HPLC (Method-B): 99.11% at RT 8.88 min.

I-178

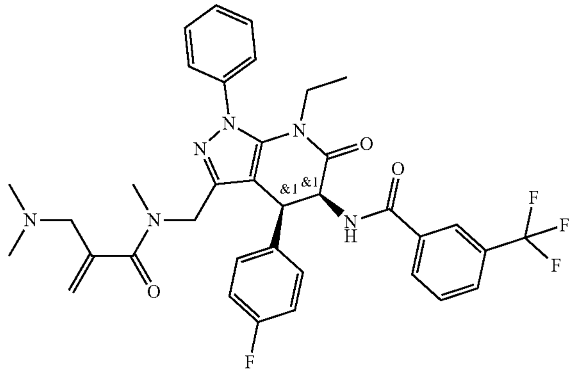

$^1$H NMR (400 MHZ, DMSO-$d_6$) δ=8.52 (d, J=6.0 Hz, 1H), 8.17-8.13 (m, 2H), 7.92 (d, J=8.0 Hz, 1H), 7.73-7.61 (m, 3H), 7.59-7.52 (m, 3H), 7.11-7.07 (m, 2H), 6.98-6.93 (m, 2H), 5.61-5.41 (m, 1H), 5.18 (s, 1H), 4.62-3.88 (m, 4H), 3.86-3.33 (m, 1H), 3.10-2.90 (m, 3H), 2.80 (s, 2H), 2.60-2.58 (m, 1H), 2.07 (s, 6H), 0.90 (t, J=6.8 Hz, 3H). LCMS: (Method-D)=677.2 $[M+H]^+$; 91.80% at RT 2.52 min. HPLC (Method-B): 97.36% at RT 9.52 min.

Example 10: Synthesis of Compounds I-122, I-62, I-26, I-125, I-152, I-65, I-243, I-243, I-187, I-163, I-75, I-161, I-120, I-101, I-177, I-176 and I-51

NMR:

$^1$H NMR spectrum was recorded on Bruker 400 MHz and Varian 400 MHz instruments internally referenced to a tetramethylsilane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A:

0.05% Formic acid in water: I (95:5) B: 0.05% Formic acid in I Inj Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge BEH C18, (50 mm*3.0 mm,2.5μ) Mobile Phase A: 2.5 mM Ammonium Bicarbonate in Water+5% I Mobile Phase B: 100% I Flow rate: 1.0 mL/min. Column temperature: 40° C. Gradient Program (B %): 0.0/2, 0.3/2, 2.0/98, 2.8/98, 3.0/2,3.7/2.

Method-C: Column: X-Select CSH C18 (50 mm*3.0 mm,2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2,2.0/98, 2.8/98, 3.0/2,3.7/2.

HPLC:

Method-A: Column: X Select CSH C18 (150×4.6) mm, 3.5μ; Mobile phase A: 0.1% FA in Water: I (95:05); Mobile phase B: Acetonitrile; Gradient Programme: T/B %: 0.01/5, 1/5,8/100,12/100,14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/2,2/2, 12/90, 16/90; Flow: 1.0 mL/min.; Diluent: I: water (80:20).

Method-C: Column: X SELECT CSH C18 (150×4.6 mm, 3.5μ); Mobile Phase A; 0.05% TFA in water: I (95:05); Mobile Phase B: 0.05% TFA in water: I (05:95); Programme: T/B %: . 0.01/10,12/90,16/90; Flow: 1 mL/min.; Diluent: water: I (80:20).

Method-D: Column: X-Bridge CSH C18 (4.6*150) mm 5μ Mobile Phase: A-0.1% TFA in water B-Acetonitrile Inj Volume; 5.0 μL, Flow Rate: 1.2. mL/minute Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in hexane, Mobile Phase B: IPA A/B: 60/40 Flow: 1.0 ml/MIN PDA: OJ-H_015.

Method-F: Column: ACE Excel 2 C18-AR, 100 mm×3.0 mm Mobile Phase A: 0.05% FA in Water; Mobile Phase B: 0.05% FA in Acetonitrile Colum Temperature: 40° C. Flow Rate: 0.6 mL/min Gradient: 0/5, 1/5, 6/90, 8.5/90, 8.8/5, 11/5.

Method-G: Column: X-Select CSH C18 (4.6*150) mm 5μ Mobile Phase: A-0.1% TFA in water B-Acetonitrile Inj Volume; 5.0 μL, Flow Rate: 1.2. mL/minute Gradient program: Time (min)/B Conc.: 0.01/5, 1.0/5, 8.0/100, 12.0/100, 14.0/5, 18.0/5.

Synthesis of 10-2

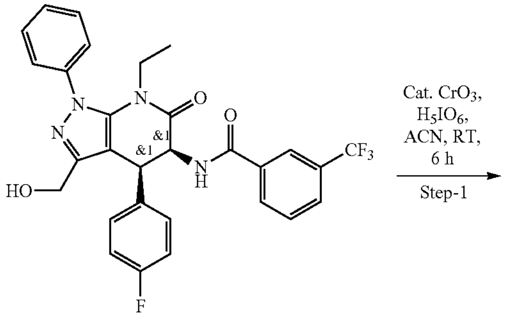

10-1

-continued

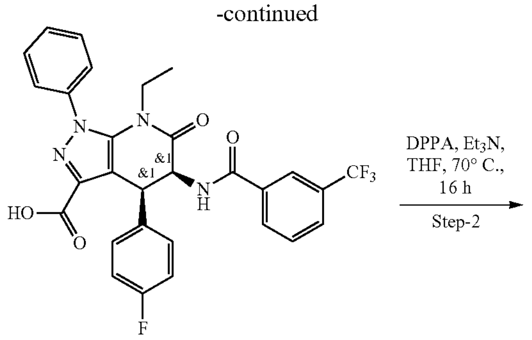

1

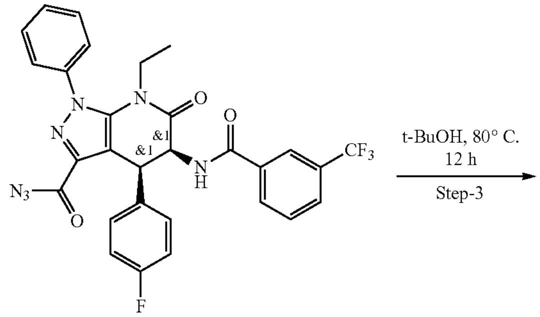

2

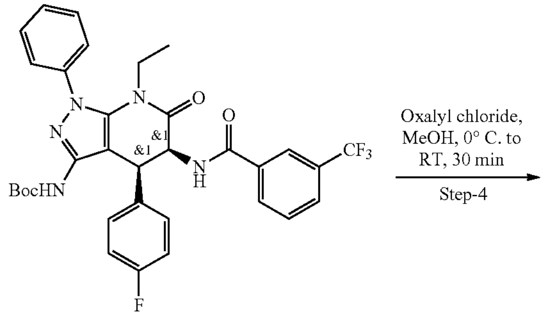

3

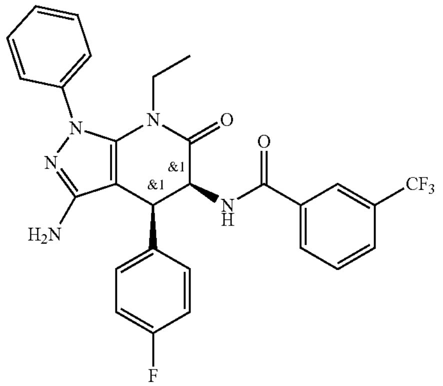

10-2

Step-1: Synthesis of 7-ethyl-4-(4-fluorophenyl)-6-oxo-1-phenyl-5-[[3-(trifluoromethyl)benzoyl]amino]-4,5-dihydropyrazolo[3,4-b]pyridine-3-carboxylic acid (1)

To a stirred solution of 10-1 (5 g, 8.68 mmol) in I (50 mL), periodic acid (4.04 g, 17.38 mmol) and Chromium (III) oxide (0.39 g, 2.606 mmol) was added at 0° C. The reaction mixture was stirred at room temperature for 12 h. Reaction progress was monitored by TLC. After completion of reaction, the reaction mixture was diluted with 10% methanol in DCM and filtered by celite bed. Filtrate was concentrated under vacuum and washed with diethyl ether. The compound was dried under vacuum to afford compound (1) (3.5 g, 69%) as off-white solid.

$^1$H NMR (400 MHZ, DMSO-$d_6$)=13.0 (s, 1H), 8.58 (d, J=7.3 Hz, 1H), 8.19-8.12 (m, 2H), 7.92 (d, J=7.8 Hz, 1H), 7.78 (d, J=6.8 Hz, 2H), 7.71 (t, J=7.8 Hz, 1H), 7.66-7.60 (m, 3H), 7.12-7.06 (m, 2H), 7.00-6.96 (m, 2H), 5.55 (t, J=7.3 Hz, 1H), 4.92 (d, J=7.3 Hz, 1H), 3.88 (dd, J=14.2, 7.3 Hz, 1H), 3.01 (dd, J=14.2, 6.8 Hz, 1H), 0.90 (t, J=6.8 Hz, 3H). LC-MS (Method-A)=567.31 [M+H]$^+$; 96.91% at RT 2.12 min.

Step-2: Synthesis of (4~{S},5~{S})-7-ethyl-4-(4-fluorophenyl)-6-oxo-1-phenyl-5-[[3-(trifluoromethyl)benzoyl]amino]-4,5-dihydropyrazolo[3,4-b]pyridine-3-carbonyl azide (2)

To a stirred solution of compound (1) (3.5 g, 6.0 mmol) in tetrahydrofuran (30 mL) was added diphenylphosphoryl azide (DPPA) (4.2 g, 15 mmol) and triethylamine (1.8 g, 18 mmol) at 0° C. The reaction was refluxed and stirred at 70° C. for 16 h. The reaction progress was monitored by TLC and LCMS. The reaction mixture was extracted by ethyl acetate (2×100 mL) and dried over anhydrous sodium sulphate and concentrated to afford crude compound, which was purified by combi flash to afford compound (2) (2.8 g, 76%) as pale-yellow solid.

$^1$H NMR (400 MHZ, DMSO-$d_6$)=8.61 (d, J=4.4 Hz, 1H), 8.15 (s, 2H), 7.91 (d, J=5.4 Hz, 1H), 7.78-7.63 (m, 6H), 7.09-6.99 (m, 4H), 5.57 (s, 1H), 4.91 (s, 1H), 3.81 (s, 1H), 3.01 (s, 1H), 0.88 (s, 3H). LC-MS (Method-A)=592.2 [M+H]$^+$; 95.68% at RT 2.29 min.

Step-3: Synthesis of tert-butyl ((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)carbamate (3)

To the stirred solution of Compound (2) (2.8 g, 4.5 mmol) in tertiary butanol (25 mL) was stirred at 80° C. for 12 h. Reaction progress was monitored by TLC. After completion of reaction, the reaction mixture was concentrated under vacuum, washed with pentane to afford compound (3) (2.7 g, 75%) as pale-yellow solid.

$^1$H NMR (400 MHZ, CHLOROFORM-d)=9.54 (s, 1H), 9.17 (s, 1H), 8.43 (d, J=7.6 Hz, 1H), 8.15-8.09 (s, 1H), 7.91 (d, J=7.6 Hz, 1H), 7.78-7.51 (m, 6H), 7.10-7.06 (m, 2H), 6.94-6.91 (m, 2H), 5.49-5.45 (m, 1H), 4.75 (d, J=7.2 Hz, 1H), 3.90-3.86 (m, 1H), 3.07 -3.04 (m, 1H), 1.32 (s, 9H), 0.91 (t, J=6.8 Hz, 3H). LC-MS (Method-A)=638.5 [M+H]$^+$; 82.54% at RT 2.30 min.

Step-4: Synthesis of N-((4S,5S)-3-amino-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (10-2)

To a stirred solution of compound (3) (5 g, 6.43 mmol) in methanol (100 mL), oxalyl chloride (4.16 g, 32.15 mmol) was added at 0° C. The reaction was stirred at room temperature for 30 min. Reaction progress was monitored by TLC. After completion of reaction, the reaction mixture was concentrated under vacuum to afford crude compound. Obtained crude was washed with 50% diethyl ether in pentane and filtered under vacuum to afford 10-2 (3 g, 72.91%) as pale green solid.

$^1$H NMR (400 MHZ, DMSO-$d_6$): 8.47 (d, J=7.2 Hz, 1H), 8.15-8.12 (m, 2H), 7.92 (d, J=7.6 Hz, 1H), 7.73-7.69 (m, 1H), 7.61-7.48 (m, 5H), 7.41-7.38 (m, 4H), 5.69-5.66 (m, 1H), 5.52-5.49 (m, 2H), 4.84 (d, J=6.8 Hz, 1H), 3.92-3.86 (m, 1H), 3.08-3.03 (m, 1H), 0.91 (t, J=7.2 Hz, 3H). LC-MS (Method-B)=538.4 [M+H]$^+$; 99.43% at RT 2.30 min. HPLC (Method-B)=99.65% at RT 9.22 min.

Synthesis of Analogs

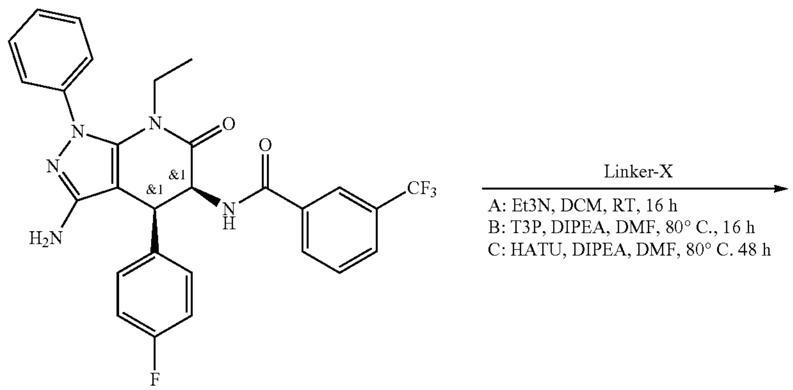

10-2

-continued

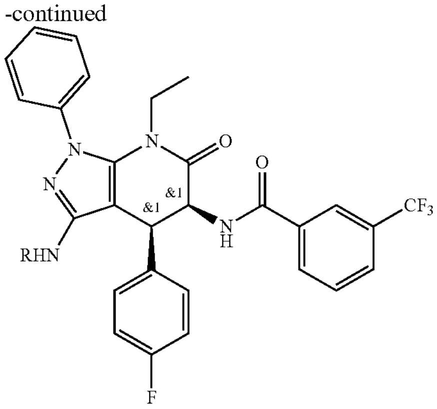

Method A Procedure:

To a stirred solution of 10-2 (200.0 mg, 0.37 mmol) in dichloromethane (0.5 mL) was added triethylamine (3 equiv., 1.116 mmol) and stirred at room temperature for 10 min. Then the Linker X (X=O,C,I,B,Y) (1 equiv., 0.37 mmol) was added. The reaction mixture was stirred at room temperature for 16 h. The progress of reaction mixture was monitored by TLC. Reaction mixture was allowed to room temperature, added 10 mL of water and extracted with EtOAc (2×15 mL). The combined organic layer was separated, dried over $Na_2SO_4$ and evaporated under reduced pressure to afford crude compound. Obtained crude compound was purified by combi-flash by using 60-120 mesh silica gel, 40% EtOAc in heptane as an eluent and evaporated under reduced pressure to afford compound.

Method B Procedure:

To a stirred solution of 10-2 (150.0 mg, 0.27 mmol) in N,N-dimethylformamide (1 mL) were added Linker X (X=L,B) (1.5 equiv., 0.41 mmol) and N,N-diisopropylethylamine (3 equiv., 0.83 mmol) followed by 2,4,6-tripropyl-1,3,5,2,4,6-trioxatriphosphorinane-2,4,6-trioxide (1.67 mol/l) in ethyl acetate (3 equiv., 0.83 mmol). The reaction mixture was heated at 85° C. for 1 h in microwave. The reaction mixture was monitored by TLC. Reaction mixture was allowed to Room temperature, added (10 mL) of water and extracted with EtOAc (2×15 mL). The combined organic layer was separated, dried over $Na_2SO_4$ and evaporated under reduced pressure to afford crude compound. The obtained crude compound was purified by combi-flash by using 60-120 mesh silica gel, 35% EtOAc in heptane as an eluent and afford product evaporated under reduced pressure to afford compound.

Method C Procedure:

To a stirred solution of 10-2 (200.0 mg, 0.37 mmol) in DMF (4 mL) was added N,N-diisopropylethylamine (3 equiv., 1.11 mmol) and stirred at room temperature for 10 min. Then the Linker X (X=N,P) (2 equiv., 0.74 mmol) and HATU (3 equiv., 1.11 mmol) were added. The reaction mixture was heated at 80° C. for 48 h. The progress of reaction mixture was monitored by TLC. After consumption of starting material reaction mixture was allowed to room temperature, added 10 ml of water and extracted with EtOAc (2×20 mL). The combined organic layer was separated, dried over $Na_2SO_4$ and evaporated under reduced pressure to afford crude compound. The obtained crude compound was purified by reverse phase preparative HPLC method to afford compound. The analogs were synthesized according to the conditions shown in the table below.

| Sr No. | Cpd. Number | Linker | Structure (R) | Method | 10-2 (mg) | Linker Qty (mg) | Qty (mg) & Nature of compound | Yield (%) |
|---|---|---|---|---|---|---|---|---|
| 1. | I-122 | O | 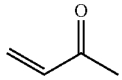 | A | 200 | 31.75 | 25 (Off-white solid) | 13.5 |
| 2. | I-62 | C | 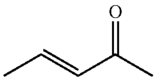 | A | 200 | 46.68 | 26.24 (Off-white solid) | 11.4 |
| 3. | I-26 | I | 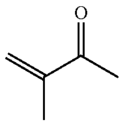 | A | 200 | 38.9 | 75 (Off-white solid) | 33.28 |
| 4. | I-161 | B | 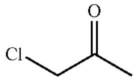 | A | 80 | 20 | 25 (Off-white solid) | 27.3 |

-continued

| Sr No. | Cpd. Number | Linker | Structure (R) | Method | 10-2 (mg) | Linker Qty (mg) | Qty (mg) & Nature of compound | Yield (%) |
|---|---|---|---|---|---|---|---|---|
| 5. | I-163 | Y | 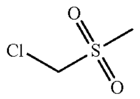 | A | 300 | 83.16 | 22.26 (Off-white solid) | 6.14 |
| 6. | I-125 | L | 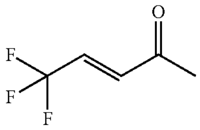 | B | 150 | 58.63 | 35 (Off-white solid) | 19.01 |
| 7. | I-120 | G | 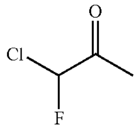 | B | 200 | 26.65 | 40 (Pale pink solid) | 32.43 |
| 8. | I-65 | N | 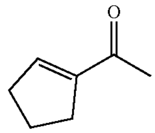 | C | 200 | 83.42 | 55 (Off-white solid) | 23.4 |
| 9. | I-176 | P | 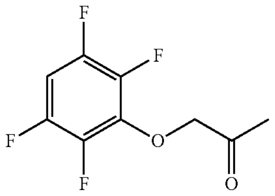 | C | 200 | 166.8 | 43.70 (Off-white solid) | 15.8 |

I-122

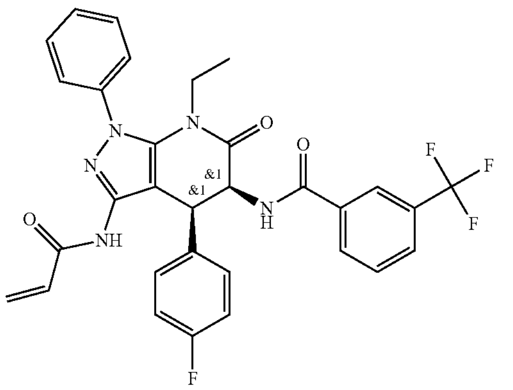

$^1$H NMR (400 MHZ, DMSO-$d_6$): 10.3 (s, 1H), 8.46 (d, J=7.6 Hz, 1H), 8.15-8.12 (m, 2H), 7.91 (d, J=7.6 Hz, 1H), 7.73-7.68 (m, 3H), 7.61-7.51 (m, 3H), 7.06 (t, J=8.8 Hz, 2H), 6.94-6.90 (m, 2H), 6.40-6.33 (m, 1H), 6.19-6.14 (m, 1H), 5.69-5.66 (m, 1H), 5.53 (t, J=7.2 Hz, 1H), 4.98 (d, J=6.8 Hz, 1H), 3.91-3.83 (m, 1H), 3.08-3.03 (m, 1H), 0.91 (t, J=7.2 Hz, 3H). LC-MS (Method-B)=592.2 [M+H]$^+$; 99.98% at RT 2.49 min. HPLC (Method-B)=99.88% at RT 9.58 min.

I-62

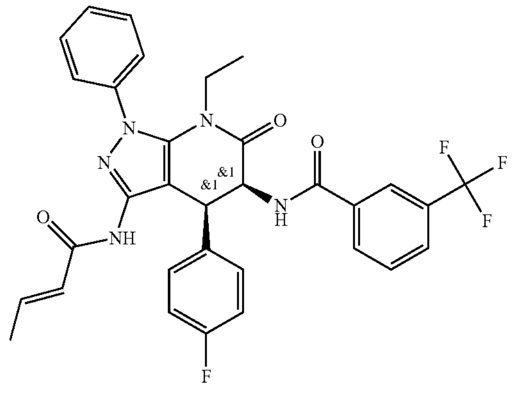

$^1$H NMR (400 MHZ, DMSO-$d_6$): 10.1 (s, 1H), 8.46 (d, J=7.6 Hz, 1H), 8.16-8.11 (m, 2H), 7.91 (d, J=7.6 Hz, 1H), 7.72-7.66 (m, 3H), 7.60-7.50 (m, 3H), 7.06 (t, J=8.8 Hz, 2H), 6.93-6.90 (m, 2H), 5.81-5.80 (m, 1H), 5.52-5.49 (m, 1H), 5.07-5.02 (m, 2H), 4.84 (d, J=6.8 Hz, 1H), 3.90-3.85 (m, 1H), 3.08-2.98 (m, 3H), 0.91 (t, J=6.8 Hz, 3H). LC-MS (Method-A)=606.0 [M+H]$^+$; 97.88% at RT 2.39 min. HPLC (Method-A)=97.63% at RT 9.09 min.

I-26

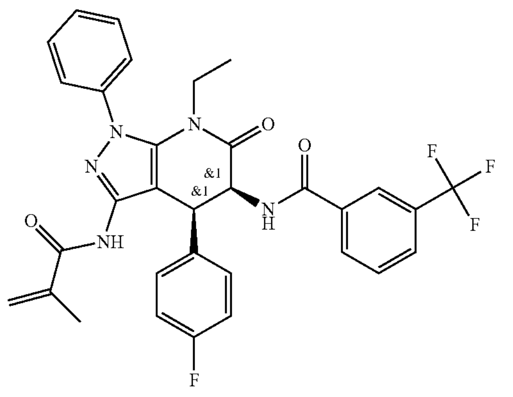

$^1$H NMR (400 MHZ, DMSO-$d_6$): 10.0 (s, 1H), 8.46 (d, J=7.6 Hz, 1H), 8.12-8.10 (m, 2H), 7.91 (d, J=7.6 Hz, 1H), 7.72-7.67 (m, 3H), 7.61-7.51 (m, 3H), 7.06 (t, J=8.8 Hz, 2H), 6.94-6.90 (m, 2H), 5.72 (s, 1H), 5.52 (t, J=7.2 Hz, 1H), 5.43 (s, 1H), 4.77 (d, J=7.2 Hz, 1H), 3.92-3.87 (m, 1H), 3.10-3.06 (m, 1H), 1.82 (m, 3H), 0.91 (t, J=7.2 Hz, 3H). LC-MS (Method-A)=606.33 $[M+H]^+$; 99.88% at RT 2.18 min. HPLC (Method-A)=99.00% at RT 8.40 min.

I-161

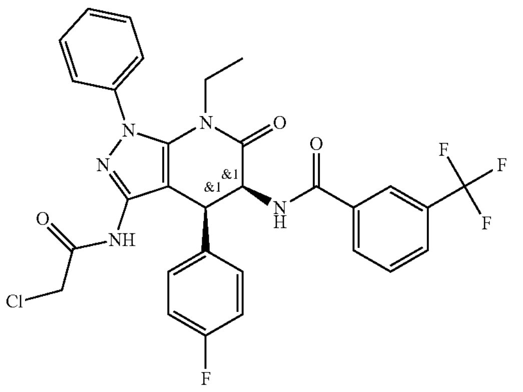

$^1$H NMR (400 MHZ, DMSO-$d_6$): 10.4 (s, 1H), 8.47 (d, J=7.2 Hz, 1H), 8.15-8.12 (m, 2H), 7.91 (d, J=8.0 Hz, 1H), 7.73-7.68 (m, 3H), 7.61-7.50 (m, 3H), 7.07 (t, J=8.8 Hz, 2H), 6.95-6.91 (m, 2H), 5.51 (t, J=7.2 Hz, 1H), 4.83 (d, J=6.8 Hz, 1H), 4.16 (s, 2H), 3.92-3.83 (m, 1H), 3.09-3.00 (m, 1H), 0.93-0.84 (m, 3H). LC-MS (Method-B)=613.92 $[M+H]^+$; 91.97% at RT 2.13 min. HPLC (Method-B)=90.68% at RT 9.32 min.

I-163

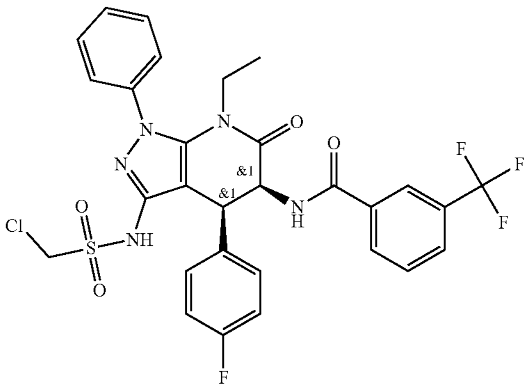

$^1$H NMR (400 MHZ, DMSO-$d_6$): 10.7 (s, 1H), 8.51 (d, J=6.8 Hz, 1H), 8.17-8.13 (m, 2H), 7.92 (d, J=7.6 Hz, 1H), 7.73-7.70 (m, 3H), 7.61-7.52 (m, 3H), 7.10 (t, J=9.2 Hz, 2H), 6.98-6.94 (m, 2H), 5.50 (t, J=7.2 Hz, 1H), 5.09-5.02 (m, 2H), 4.69 (d, J=7.2 Hz, 1H), 3.88-3.83 (m, 1H), 3.07-3.01 (m, 1H), 0.91 (t, J=6.8 Hz, 3H). LC-MS (Method-B)=650.0 $[M+H]^+$; 99.09% at RT 1.99 min. HPLC (Method-B)=99.53% at RT 8.22 min.

I-125

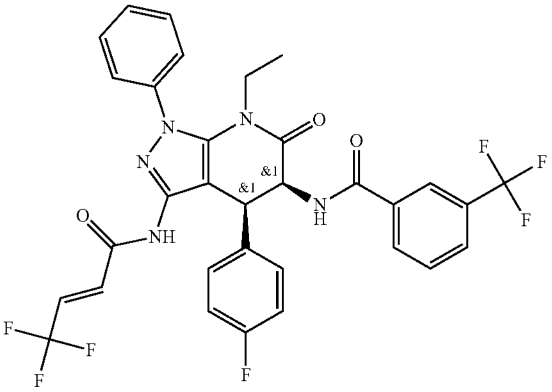

$^1$H NMR (400 MHZ, DMSO-$d_6$): 10.8 (s, 1H), 8.50 (d, J=7.2 Hz, 1H), 8.16-8.13 (m, 2H), 7.92 (d, J=8.8 Hz, 1H), 7.73-7.69 (m, 3H), 7.62-7.52 (m, 3H), 7.07 (t, J=8.8 Hz, 2H), 6.95-6.89 (m, 4H), 5.54 (t, J=6.8 Hz, 1H), 4.96 (d, J=7.2 Hz, 1H), 3.90-3.85 (m, 1H), 3.08-3.02 (m, 1H), 0.91 (t, J=6.8 Hz, 3H). LC-MS (Method-B)=659.9 $[M+H]^+$; 99.39% at RT 2.48 min. HPLC (Method-B)=98.43% at RT 10.05 min.

I-120

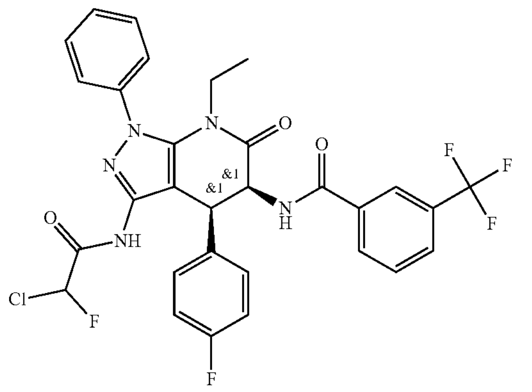

$^1$H NMR (400 MHZ, DMSO-$d_6$): 10.9 (s, 1H), 8.50-8.48 (m, 1H), 8.14-8.11 (m, 2H), 7.91 (d, J=7.6 Hz, 1H), 7.72-7.68 (m, 3H), 7.62-7.53 (m, 3H), 7.09-7.05 (m, 2H), 6.95-6.92 (m, 2H), 6.84-6.70 (m, 1H), 5.55-5.51 (m, 1H), 4.79-4.76 (m, 1H), 3.91-3.85 (m, 1H), 3.10-3.01 (m, 1H), 0.92 (t, J=6.8 Hz, 3H). LC-MS (Method-B)=632.2 [M+H]$^+$; 99.32% at RT 2.41 min. HPLC (Method-B)=97.95% at RT 9.39 min.

I-65

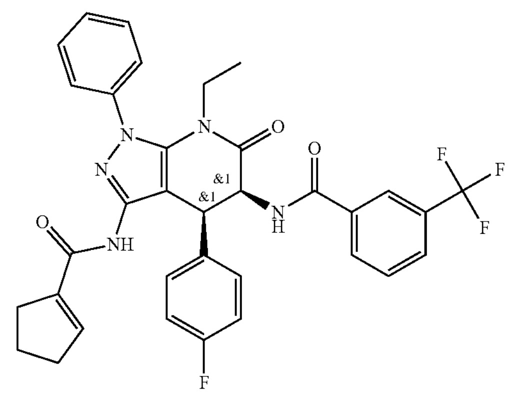

$^1$H NMR (400 MHZ, DMSO-d6, 25° C.): 9.92 (s, 1H), 8.46 (d, J=7.2 Hz, 1H), 8.14-8.11 (m, 2H), 7.91 (d, J=8.0 Hz, 1H), 7.72-7.68 (m, 3H), 7.61-7.51 (m, 3H), 7.06 (t, J=8.8 Hz, 2H), 6.93-6.89 (m, 2H), 6.66 (s, 1H), 5.52 (t, J=7.2 Hz, 1H), 4.82 (d, J=7.2 Hz, 1H), 3.92-3.87 (m, 1H), 3.08-3.01 (m, 1H), 2.44-2.42 (m, 4H), 1.86-1.78 (m, 2H), 0.92 (t, J=7.2 Hz, 3H). LC-MS (Method-B)=632.22 [M+H]$^+$; 98.98% at RT 2.17 min. HPLC (Method-B)=97.01% at RT 9.66 min.

I-176

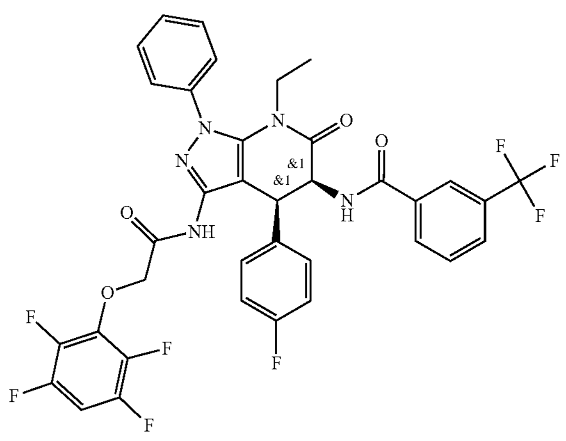

$^1$H NMR (400 MHZ, DMSO-$d_6$): 10.4 (s, 1H), 8.47-8.43 (m, 1H), 8.21-8.13 (m, 2H), 7.93 (d, J=7.6 Hz, 1H), 7.74-7.70 (m, 3H), 7.63-7.48 (m, 4H), 7.07-7.03 (m, 2H), 6.99-6.89 (m, 2H), 5.56-5.51 (m, 1H), 4.93-4.91 (m, 2H), 4.80 (d, J=7.2 Hz, 1H), 3.90-3.86 (m, 1H), 3.09-3.04 (m, 1H), 0.93 (t, J=6.8 Hz, 3H). LC-MS (Method-B)=744.0 [M+H]$^+$; 99.17% at RT 2.52 min. HPLC (Method-B)=99.73% at RT 10.04 min.

Synthesis of I-152

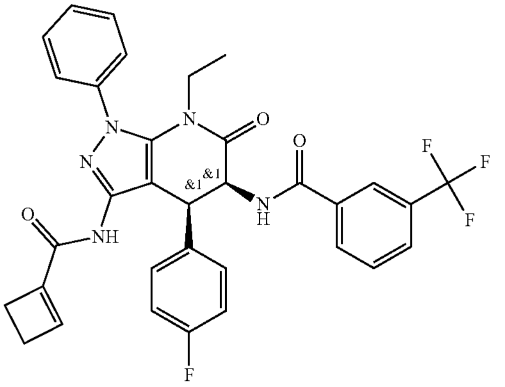

To a stirred solution of 10-2 (200.00 mg, 0.37 mmol) in I (4 mL) was added N,N-diisopropylethylamine (144.3 mg, 1.11 mmol) and stirred at room temperature for 10 min. Then to the reaction mixture cyclobutene-1-carboxylic acid (36.50 mg, 0.37 mmol) and TCFH (213 mg, 0.74 mmol) were added. The reaction mixture was stirred at 80° C. for 16 h. The progress of reaction mixture was monitored by TLC. Reaction mixture was allowed to room temperature, 20 mL of water was added, and extracted with EtOAc (2×25 mL). The combined organic layer was separated, dried over $Na_2SO_4$ and evaporated under reduced pressure to afford crude 240 mg as a brown gum. The obtained crude compound was purified by combi-flash by using 100-200 mesh silica gel, 42% EtOAc in heptane as an eluent and evaporated under reduced pressure to afford I-152 (40.00 mg, 17.41%) as an off-white solid.

$^1$H NMR (400 MHZ, DMSO-$d_6$): 8.06 (s, 1H), 7.89 (d, J=8.0 Hz, 1H), 7.79 (d, J=7.6 Hz, 1H), 7.60-7.48 (m, 6H), 7.04-7.00 (m, 2H), 6.96-6.92 (m, 2H), 6.82 (d, J=6.4 Hz,

1H), 6.70 (s, 1H), 6.66 (s, 1H), 5.31 (t, J=6.4 Hz, 1H), 5.16 (d, J=6.8 Hz, 1H), 4.00-3.91 (m, 1H), 3.24-3.15 (m, 1H), 2.70-2.68 (m, 2H), 2.46-2.44 (m, 2H), 1.03 (t, J=7.2 Hz, 3H). LC-MS (Method-B)=618.2 $[M+H]^+$; 98.17% at RT 2.32 min. HPLC (Method-B): 90.28% at RT 9.55 min.

Synthesis of I-243

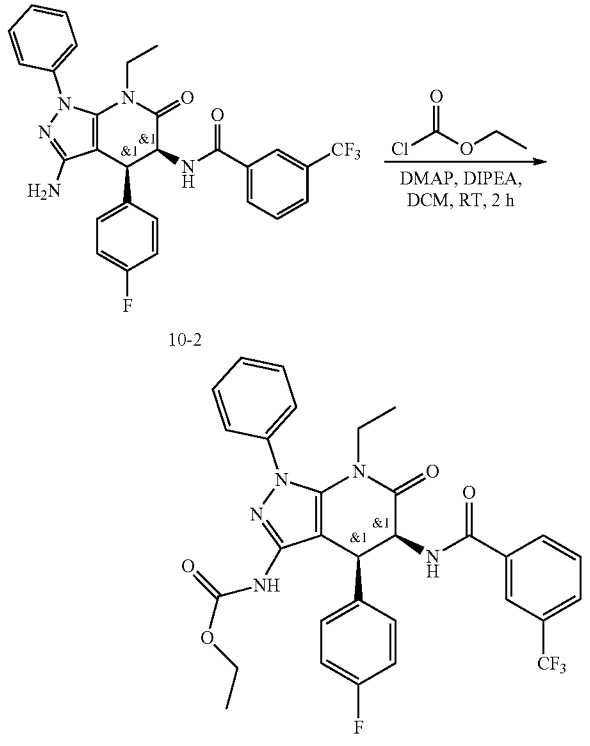

10-2

I-243

To a stirred solution of 10-2 (200 mg, 0.19 mmol) in dichloromethane (20 mL), N,N-diisopropylethylamine (77.9 mg, 0.59 mmol), ethyl chloroformate (26.4 mg, 0.23 mmol) and 4-dimethylaminopyridine (4.86 mg, 0.03 mmol) was added at 0° C. Then the reaction mixture was stirred at room temperature for 2 h. Reaction progress was monitored by TLC. After completion of reaction, reaction mass quenched with water (20 mL) and extracted with ethyl acetate (2×20 mL). The combined organic layer was separated, dried over $Na_2SO_4$ and evaporated under reduced pressure to afford crude. Obtained crude was purified by preparative HPLC to afford I-243 (25 mg, 20.8%) as an off-white solid.

$^1$H NMR (400 MHZ, DMSO-$d_6$): 9.53 (s, 1H), 8.47 (d, J=7.2 Hz, 1H), 8.15-8.11 (m, 2H), 7.92 (d, J=7.6 Hz, 1H), 7.73-7.66 (m, 3H), 7.60-7.50 (m, 3H), 7.08 (t, J=9.2 Hz, 2H), 6.96-6.92 (m, 2H), 5.50 (t, J=6.4 Hz, 1H), 4.73 (d, J=7.2 Hz, 1H), 3.97-3.82 (m, 3H), 3.07-3.02 (m, 1H), 1.06 (t, J=7.2 Hz, 3H), 0.91 ((t, J=7.2 Hz, 3H). LC-MS (Method-B)=610.2 $[M+H]^+$; 99.87% at RT 2.37 min. HPLC (Method-B): 99.89% at RT 9.57 min.

Synthesis of I-187

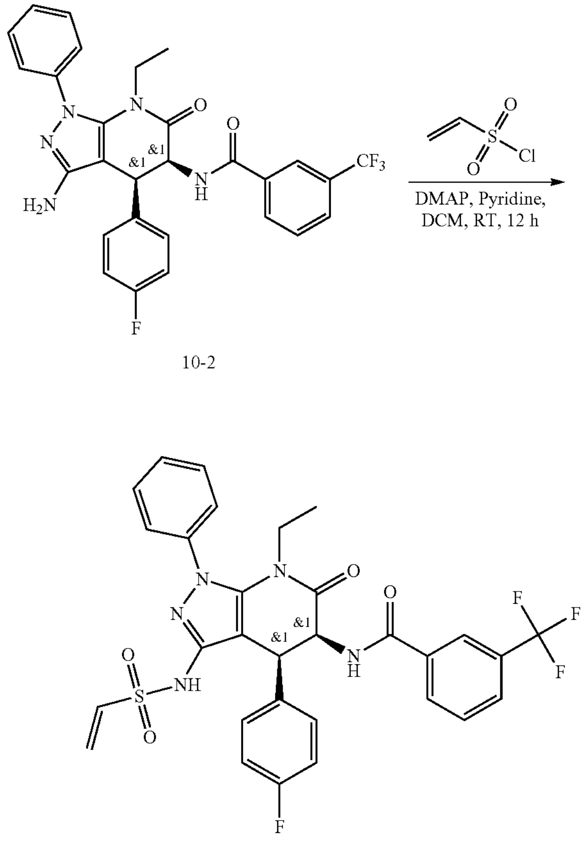

10-2

I-187

To a stirred solution of 10-2 (200 mg, 0.27 mmol) in dichloromethane (10 mL), were added pyridine (33.3 mg, 0.41 mmol), ethenesulfonyl chloride (45.05 mg, 0.34 mmol) at room temperature. The reaction mixture was added 4-dimethylaminopyridine (3.44 mg, 0.02 mmol). Then the reaction mixture stirred at room temperature for 12 h. Reaction progress was monitored by TLC and LCMS. After completion of reaction, quenched the reaction mixture with water and extracted with ethyl acetate. The combined organic layer was separated, dried over $Na_2SO_4$ and evaporated under reduced pressure to afford crude as brown gum. Obtained compound was submitted for prep-HPLC for purification to afford I-187 (12 mg, 6.78%) as off-white solid.

$^1$H NMR (400 MHZ, DMSO-$d_6$): 10.1 (s, 1H), 8.47 (d, J=7.2 Hz, 1H), 8.16-8.13 (m, 2H), 7.92 (d, J=7.6 Hz, 1H), 7.73-7.65 (m, 3H), 7.60-7.50 (m, 3H), 7.09 (t, J=8.8 Hz, 2H), 6.97-6.93 (m, 2H), 6.85-6.78 (m, 1H), 5.99-5.88 (m, 2H), 5.45 (d, J=6.8 Hz, 1H), 4.67 (d, J=5.6 Hz, 1H), 3.88-3.82 (m, 1H), 3.06-3.01 (m, 1H), 0.90 (t, J=7.2 Hz, 3H). LC-MS (Method-B)=628.1 $[M+H]^+$; 99.06% at RT 2.20 min. HPLC (Method-B): 99.81% at RT 8.92 min.

Synthesis of I-51

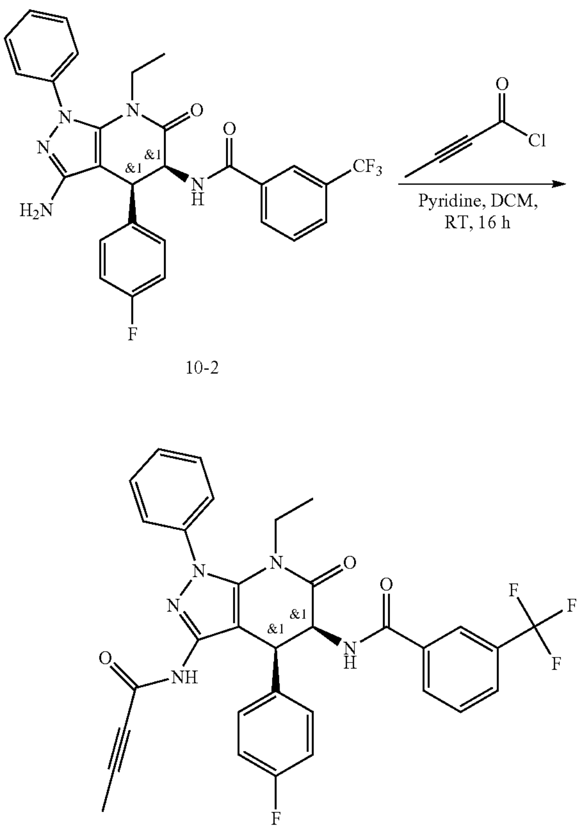

10-2

I-51

To a stirred solution of 10-2 (300.00 mg, 0.27 mmol) in dichloromethane (5 mL) were added pyridine (66.4 mg, 0.83 mmol) and but-2-ynoyl chloride (28.61 mg, 0.27 mmol). The reaction mixture was stirred at room temperature for 16 h. The progress of reaction mixture was monitored by TLC. Reaction mixture was allowed to room temperature, added 25 mL of water, and extracted with EtOAc (2×50 mL). The combined organic layer was separated, dried over $Na_2SO_4$, and evaporated under reduced pressure to afford crude compound 320 mg as a brown gum. The obtained crude compound was purified by combi-flash by using 60-120 mesh silica gel, 50% EtOAc in heptane as an eluent and evaporated under reduced pressure to afford I-51 (20.00 mg, 11.87%) as an off-white solid.

$^1$H NMR (400 MHZ, DMSO-d6): 10.7 (s, 1H), 8.47 (d, J=7.2 Hz, 1H), 8.15-8.11 (m, 2H), 7.91 (d, J=8.0 Hz, 1H), 7.73-7.63 (m, 3H), 7.61-7.51 (m, 3H), 7.07 (t, J=8.8 Hz, 2H), 6.91 (t, J=5.2 Hz, 2H), 5.49 (t, J=7.2 Hz, 1H), 4.74 (d, J=6.4 Hz, 1H), 3.91-3.82 (m, 1H), 3.06-2.99 (m, 1H), 1.96 (s, 3H), 0.90 (t, J=7.2 Hz, 3H). LC-MS (Method-B)=604.2 $[M+H]^+$; 99.91% at RT 2.31 min. HPLC (Method-B): 98.01% at RT 9.28 min.

Synthesis of I-75

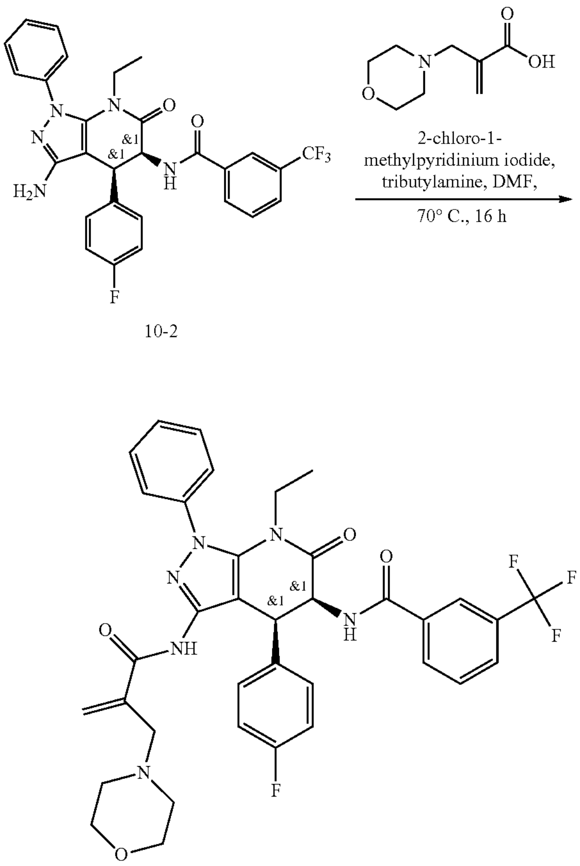

10-2

I-75

To a stirred solution of 10-2 (250 mg, 0.46 mmol) was added 2-(morpholinomethyl) prop-2-enoic acid (79.62 mg, 0.46 mmol) in DMF (2.5 mL). Then the reaction mixture was added tributylamine (264 mg, 1.39 mmol) and 2-chloro-1-methylpyridinium iodide (147.0 mg, 0.55 mmol). Heat the reaction mass at 70° C. for 16 h. Reaction mixture was quenched by ice cold water and extracted by ethyl acetate. The combined organic layer was separated, dried over $Na_2SO_4$, and evaporated under reduced pressure to afford crude. The obtained crude compound was purified by prep HPLC to afford I-75 (20.8 mg, 6.47%) as an off-white solid.

$^1$H NMR (400 MHZ, DMSO-d6): 10.9 (s, 1H), 8.49 (d, J=7.2 Hz, 1H), 8.16-8.13 (m, 2H), 7.92 (d, J=8.0 Hz, 1H), 7.73-7.70 (m, 3H), 7.62-7.54 (m, 3H), 7.07 (t, J=8.8 Hz, 2H), 6.97-6.93 (m, 2H), 5.96 (s, 1H), 5.54-5.51 (m, 2H), 4.91 (d, J=7.2 Hz, 1H), 3.92-3.86 (m, 1H), 3.46-3.38 (m, 4H), 3.26-3.17 (m, 2H), 3.08-3.01 (m, 1H), 2.30-2.33 (m, 4H), 0.92 (t, J=6.8 Hz, 3H). LC-MS (Method-B)=691.2 $[M+H]^+$; 99.45% at RT 2.53 min. HPLC (Method-B): 98.98% at RT 9.63 min.

Synthesis of I-177

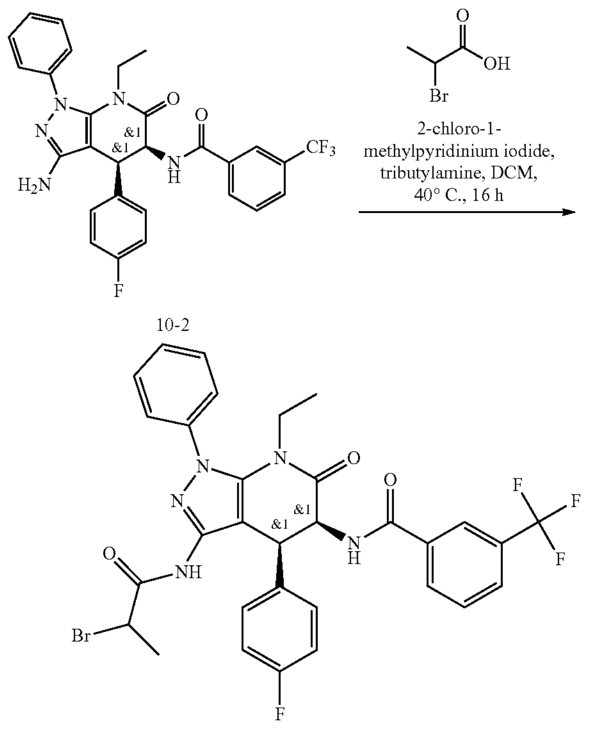

10-2

I-177

To a stirred solution of 10-2 (200.0 mg, 0.37 mmol) in dichloromethane (1 mL) was added tributylamine (211 mg, 1.11 mmol) and stirred at room temperature for 10 min. Then to the reaction mixture was added 2-bromopropanoic acid (56.92 mg, 0.37 mmol) and 2-chloro-1-methylpyridinium iodide (127.4 mg, 0.48 mmol). The reaction mixture was stirred at 40° C. for 16 h. The progress of reaction mixture was monitored by TLC. Reaction mixture was allowed to room temperature, added 10 mL of water, and extracted with DCM (2×15 mL). The combined organic layer was separated, dried over $Na_2SO_4$, and evaporated under reduced pressure to afford crude 210 mg as a brown gum. The obtained crude compound was purified by combi-flash by using 60-120 mesh silica gel, 42% EtOAc in heptane as an eluent and evaporated under reduced pressure to afford I-177 (35.00 mg, 13.99%) as an off white solid.

$^1$H NMR (400 MHZ, DMSO-d6): 10.4-10.3 (m, 1H), 8.49-8.45 (m, 1H), 8.13-8.11 (m, 2H), 7.91 (d, J=7.6 Hz, 1H), 7.72-7.68 (m, 3H), 7.61-7.51 (m, 3H), 7.06 (t, J=8.4 Hz, 2H), 6.97-6.93 (m, 2H), 5.52 (t, J=7.2 Hz, 1H), 4.88-4.83 (m, 1H), 4.65-4.58 (m, 1H), 3.91-3.84 (m, 1H), 3.07-3.03 (m, 1H), 1.78-1.42 (m, 3H), 0.93-0.84 (m, 3H). LC-MS (Method-B)=672.5 $[M+H]^+$; 98.42% at RT 2.32 min. HPLC (Method-B): 98.36% at RT 9.55, 11.88 min.

Synthesis of I-101

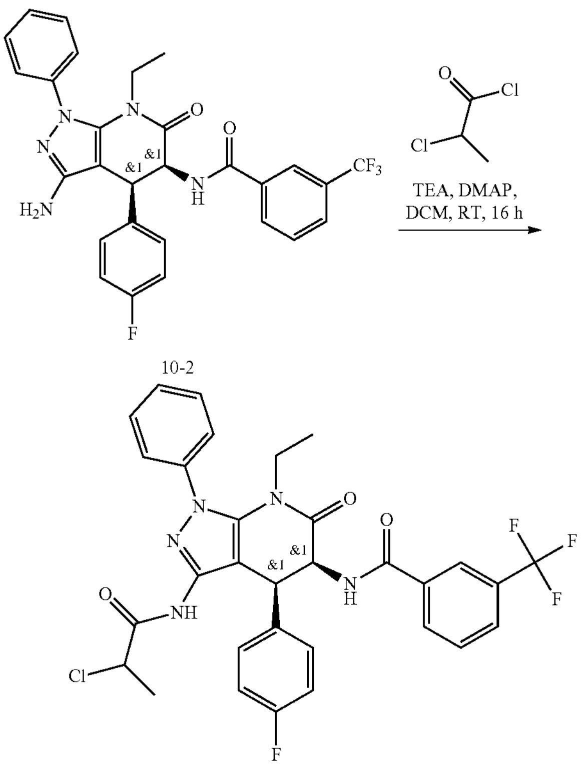

10-2

I-101

To a stirred solution of 10-2 (120.00 mg, 0.22 mmol) in dichloromethane (4 mL) was added triethylamine (67.8 mg, 0.67 mmol) and DMAP (2.7 mg, 0.02 mmol) followed by (R)-2-chloropropanoyl chloride (31.2 mg, 0.24 mmol) in DCM (drop wise) at 0° C. Then the reaction mixture was stirred at room temperature for 16 h. The progress of reaction mixture was monitored by TLC and LCMS. Reaction mixture was quenched with water (20 mL and extracted with DCM (2×20 mL)). The combined organic layer was separated, dried over $Na_2SO_4$, and evaporated under reduced pressure to afford crude compound. The obtained crude compound was purified by reverse phase-prep HPLC and lyophilised to afford I-101 (20.00 mg, 14.3%) as a white solid.

$^1$H NMR (400 MHZ, DMSO-d6): 10.4 (s, 1H), 8.48 (d, J=7.6 Hz, 1H), 8.13-8.11 (m, 2H), 7.91 (d, J=7.2 Hz, 1H), 7.72-7.68 (m, 3H), 7.61-7.53 (m, 3H), 7.07 (t, J=8.8 Hz, 2H), 6.94-6.91 (m, 2H), 5.55-5.51 (m, 1H), 4.83-4.81 (m, 1H), 4.59 (d, J=6.4 Hz, 1H), 3.88-3.86 (m, 1H), 3.09-3.04 (m, 1H), 1.51-1.35 (m, 3H), 0.91 (t, J=6.8 Hz, 3H). LC-MS (Method-B)=628.2 $[M+H]^+$; 99.31% at RT 2.39 min. HPLC (Method-B): 95.98% at RT 9.69 min.

Example 11: Synthesis of Compounds I-167, I-190, I-239, I-212, I-197, I-168, I-209, I-236, I-238, I-191, I-164, I-174, I-237, I-166, I-74, I-215, I-165, I-210, I-213 and I-8

NMR:

$^1$H NMR spectrum was recorded on Bruker 400 MHz and Varian 400 MHz instruments internally referenced to a tetramethylsilane (TMS) signal. Chemical shifts (δ) and coupling constants (J) were expressed in parts per million and hertz, respectively.

LC-MS:

Method-A: LC-MS_X-Select (Formic acid); Column: X-Select CSH C18 (3.0*50) mm 2.5μ. Mobile Phase: A: 0.05% Formic acid in water: I (95:5) B: 0.05% Formic acid in I Inj Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/min; Column oven temp. 50° C. Gradient program: 0% B to 98% B in 2.0 minute, hold till 3.0 min, at 3.2 min B conc is 0% up to 4.0 min.

Method-C: Column: X-Select CSH C18 (50 mm*3.0 mm,2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2,2.0/98, 2.8/98, 3.0/2,3.7/2.

Method-D: Column: X-Select CSH C18 (3.0*50 mm,2.5 μm), Mobile Phase A: 2.5 Mm Ammonium Bicarbonate in $H_2O$+5% I Mobile Phase B: 100% I, Gradient % B: 0/2, 0.3/2,2.0/98,2.8/98,3.0/2,3.7/2.

Method-E: Column: X-Bridge BEH $C_{18}$, (50 mm*3.0 mm,2.5μ) Mobile Phase A: 2.5 mM Ammonium Bicarbonate in Water+5% I Mobile Phase B: 100% I Flow rate: 1.0 mL/min. Column temperature: 40° C. Gradient Program (B %): 0.0/2, 0.3/2, 2.0/98, 2.8/98, 3.0/2,3.7/2.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5, 1/5,8/100,12/100,14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/2,2/2, 12/90, 16/90; Flow: 1.0 mL/min.; Diluent: I:Water (80:20).

Method-C: Column: X SELECT CSH C18 (150×4.6 mm, 3.5μ); Mobile Phase A; 0.05% TFA in water: I (95:05); Mobile Phase B: 0.05% TFA in water: I (05:95); Programme: T/B %: . 0.01/10,12/90,16/90; Flow: 1 mL/min.; Diluent: water: I (80:20).

Method-D: Column: X-Bridge CSH C18 (4.6*150) mm 5μ Mobile Phase: A-0.1% TFA in water B-Acetonitrile Inj Volume; 5.0 μL, Flow Rate: 1.2. mL/minute Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in Hexane Mobile Phase B: IPA A/B: 60/40 Flow: 1.0 ml/MIN PDA: OJ-H_015.

Method-F: Column: ACE Excel 2 C18-AR, 100 mm×3.0 mm Mobile Phase A: 0.05% TFA in Water; Mobile Phase B: 0.05% TFA in Acetonitrile Colum Temperature: 40° C. Flow Rate: 0.6 mL/min Gradient: 0/5, 1/5, 6/90, 8.5/90, 8.8/5, 11/5.

Method-G: Column: CHIRAL PAK-IC (250×4.6 mm, 5 μm) Mobile Phase A: 0.1% DEA in Hexane Mobile Phase B: EtOH/MeOH (50/50) A: B: 80/20 Flow: 1.0 mL/min.

Method-H: Column: ACE Excel 2 C18-AR, 100 mm×3.0 mm Mobile Phase A: 0.05% FA in Water; Mobile Phase B: 0.05% FA in Acetonitrile Colum Temperature: 40° C. Flow Rate: 0.6 mL/min Gradient: 0/5, 1/5, 6/90, 8.5/90, 8.8/5, 11/5.

Method-I: Column: X-Select CSH C18 (4.6*150) mm 5μ Mobile Phase: A-0.1% TFA in water B-Acetonitrile Inj Volume; 5.0 μL, Flow Rate: 1.2. mL/minute Gradient program: Time (min)/B Conc.: 0.01/5, 1.0/5, 8.0/100, 12.0/100, 14.0/5, 18.0/5.

Synthesis of intermediate 11-1

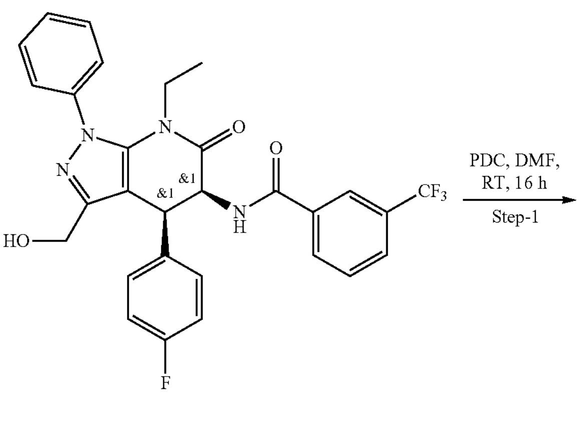

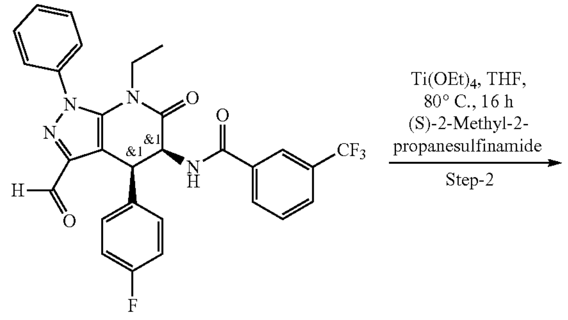

1

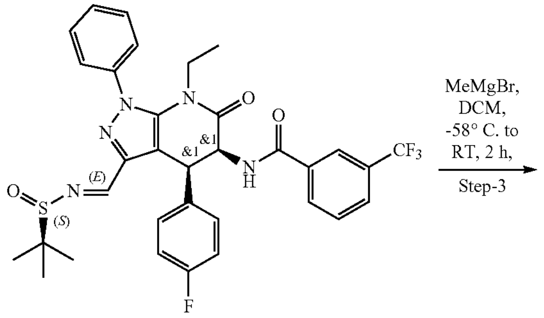

2

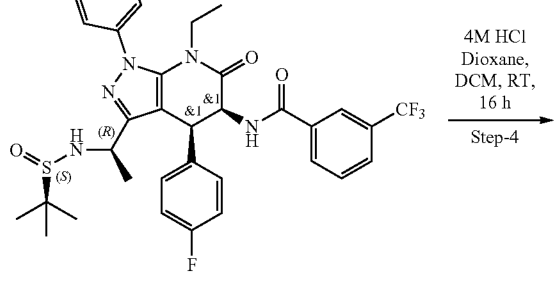

3

-continued

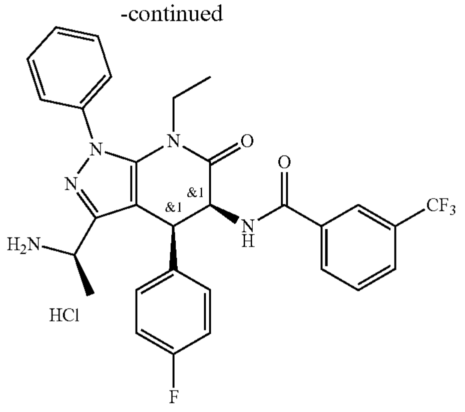

11-1

Step-1: Synthesis of N-((4S,5S)-7-ethyl-4-(4-fluorophenyl)-3-formyl-6-oxo-1-phenyl-4,5,6,7-tetrahydro-1H-pyrazolo[3,4-b]pyridine-5-yl)-3-(trifluoromethyl)benzamide (1)

To a stirred solution of N-((4S,5S)-7-ethyl-4-(4-fluorophenyl)-3-(hydroxymethyl)-6-oxo-1-phenyl-4,5,6,7-tetrahydro-1H-pyrazolo[3,4-b]pyridine-5-yl)-3-(trifluoromethyl)benzamide (2.0 g, 3.5 mmol) in DMF (20.0 mL), was added pyridinium dichromate (1.6 g, 4.2 mmol). The reaction mixture was stirred at 25° C. for 16 h. After consumption of the starting material (by TLC), the reaction mixture was quenched with ice cold water (50 mL) and extracted with diethyl ether (3×40 mL). The organic layer was dried over anhydrous $Na_2SO_4$ and concentrated under reduced pressure. The crude material was purified by medium pressure liquid chromatography by eluting 7-15% EtOAc/heptane to afford compound (1) (1.5 g, 77%) as an off-white semi solid.

$^1$H NMR (400 MHZ, CHLOROFORM-d): δ 9.94 (s, 1H), 8.01 (s, 1H), 7.86 (d, J=7.8 Hz, 1H), 7.79 (d, J=7.8 Hz, 1H), 7.55-7.64 (m, 6H), 7.00-7.05 (m, 2H), 6.92-6.99 (m, 2H), 6.85 (d, J=6.1 Hz, 1H), 5.29-5.34 (m, 1H), 5.23 (d, J=7.6, 1H), 4.00 (dd, J=14.3, 7.2 Hz, 1H), 3.21 (dd, J=14.2, 7.0 Hz, 1H), 1.01 (t, J=7.2 Hz, 3H). LC-MS (Method-B)=551.4 $[M+H]^+$; 98.61% at RT 2.05 min.

Step-2: Synthesis of N-((4S,5S)-3-(I—(((S)-tert-butylsulfinyl)imino)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (2)

To a stirred solution of compound (1) (6.0 g, 11 mmol) in THF (60 mL) was added(s)-2-methylpropane-2-sulfinamide (2.6 g, 21 mmol) and titanium (IV) ethoxide (5.2 g, 22 mmol) at 0° C. The reaction mixture was stirred at 80° C. for 16 h. Progress of the reaction was monitored by TLC. After consumption of the reaction, the reaction mixture was poured into ice cold $NH_4Cl$ solution (150 mL) and extracted with EtOAc (2×150 mL). The organic layer was dried over anhydrous $Na_2SO_4$, concentrated under reduced pressure. The crude material was washed with diethyl ether filtered and dried to afford compound (2) (6.5 g, 85%) as an off-white solid.

$^1$H NMR (400 MHZ, DMSO-d6) δ 8.67-8.51 (m, 1H), 8.39 (d, J=4.0 Hz, 1H), 8.23-8.18 (m, 1H), 8.11 (d, J=8.8 Hz, 1H), 7.92 (t, J=6.8 Hz, 1H), 7.83 (t, J=7.6 Hz, 2H), 7.74-7.61 (m, 3H), 7.09 (q, J=8.8 Hz, 2H), 6.95 (t, J=5.2 Hz, 2H), 5.66-5.55 (m, 1H), 5.28 (s, 1H), 4.98 (dd, J=7.2, 11.2 Hz, 1H), 3.92-3.87 (m, 1H), 3.04-2.99 (m 1H), 1.24-1.17 (m, 3H), 1.11-0.74 (s, 9H). LC-MS (Method-D)=654.2 $[M+H]^+$; 93.00% at RT 2.50 min.

Step-3: Synthesis of N-((4S,5S)-3-((R)-1-aminoethyl)-7-ethyl-4-(4-fluorophenyl)-6-oxo-1-phenyl-4,5,6,7-tetrahydro-1H-pyrazolo[3,4-b]pyridine-5-yl)-3(trifluoromethyl)benzamide (3)

To a stirred solution of compound (2) (6.5 g, 9.9 mmol) in DCM (130 mL), $CH_3MgBr$ (3.0 M) in diethyl ether (34 g, 99 mmol) was added slowly at −58° C. Reaction mixture was allowed to stir at room temperature for 2 h. After consumption of the starting material (by TLC), the reaction was poured into ice cold $NH_4Cl$ solution (125 mL) and extracted with DCM (2×250 mL). The organic layer was dried over anhydrous $Na_2SO_4$ and concentrated under reduced pressure. The obtained crude material was washed with diethyl ether to afford compound (3) (5.85 g, 86%) as an off-white solid.

$^1$H NMR (400 MHZ, DMSO-d6) δ 8.51-8.42 (m, 1H), 8.17-8.11 (m, 2H), 7.92 (d, J=7.6 Hz, 1H), 7.74-7.50 (m, 6H), 7.13-7.08 (m, 2H), 7.03-6.93 (m, 2H), 5.47 (dd, J=7.4, 14.8 Hz, 1H), 5.52-5.41 (m, 1H), 5.28-4.14 (m, 1H), 5.01-4.87 (m, 1H), 4.76-4.70 (m, 1H), 4.64 (d, J=7.2 Hz, 1H), 4.37-4.16 (m, 1H), 3.92-3.85 (m, 1H), 3.09-3.02 (m, 1H), 1.26-1.24 (m, 3H), 1.18-0.87 (m, 9H). LC-MS (Method-E)= 669.9 $[M+H]^+$; 91.73% at RT 2.49, 2.44 min.

Step-4: Synthesis of N-((4S,5S)-3-((R)-1-aminoethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide hydrochloride (11-1)

To a stirred solution of compound (3) (5.4 g, 8.1 mmol) in dichloromethane (54 mL) was added 4M HCl in Dioxane (20 mL) at room temperature under inert atmosphere. The reaction mixture was stirred at 25° C. for 16 h. After consumption of the starting material (by TLC), the reaction mixture was concentrated under reduced pressure. Obtained residue was triturated with diethyl ether to afford 11-1 (4.20 g, 89%) as an off-white solid.

$^1$H NMR (400 MHZ, DMSO-$d_6$) δ=8.59 (d, J=7.2 Hz, 1H), 8.44 (s, 2H), 8.22-8.13 (m, 1H), 8.03 (d, J=8.8 Hz, 1H), 7.92 (d, J=7.6 Hz, 1H), 7.72-7.70 (m, 3H), 7.64-7.58 (m, 3H), 7.16-7.12 (m, 2H), 7.04-6.99 (m, 2H), 5.58-5.52 (m, 1H), 4.76-4.68 (m, 1H), 4.57-4.54 (m, 1H), 3.93-3.86 (m, 1H), 3.11-3.04 (m, 1H), 1.08-1.04 (m, 3H), 0.95-0.81 (m, 3H). LC-MS (Method-B)=566.2 $[M+H]^+$; 96.24% at RT 2.41, 2.28 min. HPLC (Method-B): 92.33% at RT 8.57, 9.21 min. Chiral-HPLC (Method-G): Peak-1:54.93% at RT 4.95 min; Peak-2:26.48% at RT 6.97 min.

Synthesis of Analogues

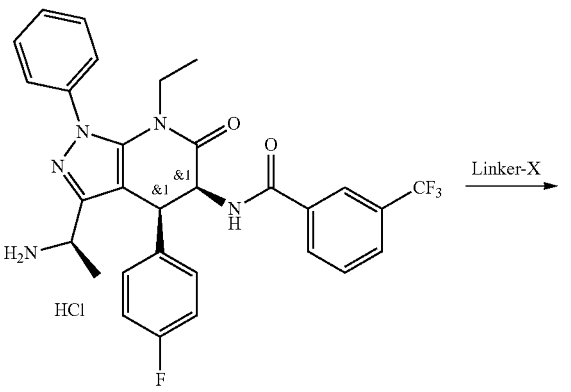

11-1

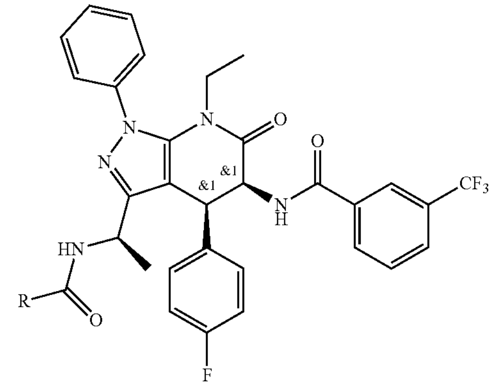

Method A: $Et_3N$, DCM, RT, 16 h
Method B: EDC, HOBT, DIPEA, DMF, RT, 12 h
Method C: HATU, DIPEA, DMF, RT, 12 h
Method D: CNBr, Py, DCM, RT, 16 h
Method E: $T_3P$, DIPEA, DMF, RT, 14 h Method-A Procedure:

To a stirring solution of 11-1 (150 mg, 0.2652 mmol) in dichloromethane (4 mL) were added triethylamine (0.11 g, 1.06 mmol) and Linker-X (X=B, O, H, C, Y, R) (xx mg) at room temperature under inert atmosphere. The reaction mixture was stirred at room temperature for 16 h. Progress of the reaction was monitored by LC-MS and TLC. After consumption of the starting material (monitored by TLC), the reaction mixture was quenched with ice cold water (20 mL), extracted with DCM (2×20 mL). The combined organic layer was dried over anhydrous $Na_2SO_4$ and concentrated under reduced pressure. The crude material was purified by silica gel column, product eluted in 40 to 50% EA in heptane, product containing fractions were collected and concentrated to afford compound.

Method-B Procedure:

To a stirred solution of 11-1 (170 mg, 0.2885 mmol) in DMF (2 mL) was added Linker X (X=E, D, P, L, T, F), HOBT (59.68 mg, 0.43 mmol), DIPEA (114.2 mg, 0.86 mmol) and 3-(ethyliminomethyleneamino)-{N}, {N}-dimethyl-propan-1-amine (EDC) (59.42 mg, 0.37 mmol) at room temperature. The resulting reaction mixture was stirred at room temperature for 12 h. Progress of the reaction was monitored by TLC and LC-MS, after consumption of starting material, reaction mixture was quenched with ice cold water (10 mL) and filter to afford solid was purified by combi flash to afford compound.

Method-C Procedure:

To a stirring solution of Linker-X (X=K, Q) in DMF (4.5 mL) were added DIPEA (0.13 g, 1.061 mmol) and HATU (0.21 g, 0.53 mmol) followed by 11-1 (200 mg, 0.35 mmol) at room temperature under inert atmosphere. The reaction mixture was stirred at 25° C. for 16 h. Progress of the reaction was monitored by TLC. After consumption of the starting material (monitored by TLC), the reaction mixture was quenched with ice cold water (20 mL), extracted with DCM (2×20 mL). The combined organic layer was dried over anhydrous $Na_2SO_4$ and concentrated under reduced pressure. The crude material was purified by flash column chromatography using 40 to 50% ethyl acetate in heptane, product containing fractions were collected and concentrated to afford pure compound. The above obtained compound was further triturated with n-pentane and dried to afford compound.

Method-D Procedure:

To a stirring solution of 11-1 (0.3 g, 0.5 mmol) in dichloromethane (6 mL) were added pyridine (0.1 g, 2 mmol) and cyanogen bromide 5M in I (0.2 g, 0.5 mmol) at 25° C. under inert atmosphere. The reaction mixture was stirred at room temperature for 16 h. Progress of the reaction was monitored by LC-MS and TLC. After consumption of the starting material (monitored by TLC), the reaction mixture was quenched with ice cold water (20 mL), extracted with DCM (2×20 mL). The combined organic layer was dried over anhydrous $Na_2SO_4$ and concentrated under reduced pressure. The crude material was purified by silica gel column, product eluted in 40 to 50% ethyl acetate in heptane, product containing fractions were collected and concentrated to afford pure product as an off-white solid. I-167 (15 mg, 5%) as a white solid.

Method-E Procedure:

To a stirring solution of Linker X (X=J & M) in DMF (4 mL) were added N,N-diisopropylethylamine (0.17 g, 1.3 mmol) and 1-propanephosphonic anhydride in DMF (0.44 g, 0.66 mmol) followed by 11-1 (0.25 g, 0.44 mmol) at 0° C. under inert atmosphere. The reaction mixture was stirred at room temperature for 16 h. Progress of the reaction was monitored by TLC. After consumption of the starting material (monitored by TLC), the reaction mixture was quenched with ice cold water (20 mL), extracted with DCM (2×20 mL). The combined organic layer was dried over anhydrous $Na_2SO_4$ and concentrated under reduced pressure to afford crude compound. The crude material was purified by silica gel column using ethyl acetate in heptane, product eluted in 40 to 50% ethyl acetate in heptane, product containing fractions were collected and concentrated to afford compound. The following table shows the conditions to obtain the final compounds.

| Cpd. Number | Linker | Structure | Method | 11-1 Qty (mg) | Linker Qty (mg) | Qty (mg) & nature of compound | Yield (%) |
|---|---|---|---|---|---|---|---|
| I-190 | B | 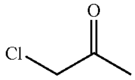 | A | 150 | 38.94 | 22 (Off-white solid) | 12.28 |

-continued
| Cpd. Number | Linker | Structure | Method | 11-1 Qty (mg) | Linker Qty (mg) | Qty (mg) & nature of compound | Yield (%) |
|---|---|---|---|---|---|---|---|
| I-174 | O | 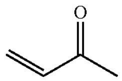 | A | 125 | 24 | 20 (Off-white solid) | 14.60 |
| I-212 | H | 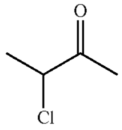 | A | 125 | 33.67 | 52 (Off-white solid) | 35.36 |
| I-238 | C | 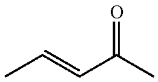 | A | 125 | 27.72 | 17.10 (Off-white solid) | 12.20 |
| I-215 | Y | 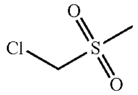 | A | 200 | 80 | 42 (Off-white solid) | 20 |
| I-74 | R | 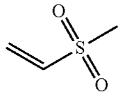 | A | 200 | 40 | 35 (Off-white solid) | 20 |
| I-197 | E | 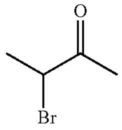 | B | 170 | 90.08 | 10.86 (White solid) | 5.35 |
| I-209 | D | 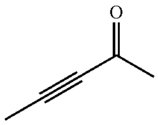 | B | 200 | 29.73 | 45 (Off-white solid) | 19.75 |
| I-168 | P | 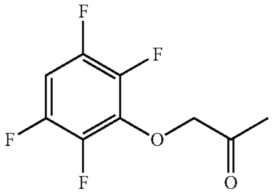 | B | 200 | 112.9 | 14 (Pale-yellow solid) | 5.40 |
| I-164 | L | 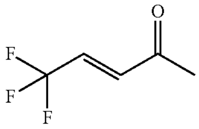 | B | 250 | 92.86 | 92 (Off-white solid) | 30.27 |
| I-165 | T | 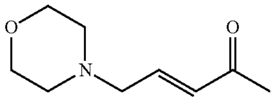 | B | 170 | 102.9 | 68 (Off-white solid) | 31.48 |
| I-213 | F | 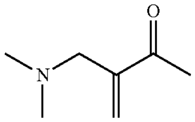 | B | 170 | 74.54 | 10.11 (Off-white solid) | 4.87 |

-continued

| Cpd. Number | Linker | Structure | Method | 11-1 Qty (mg) | Linker Qty (mg) | Qty (mg) & nature of compound | Yield (%) |
|---|---|---|---|---|---|---|---|
| I-166 | N | 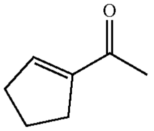 | B | 170 | 82.54 | 10.86 (White solid) | 5.51 |
| I-8 | K | 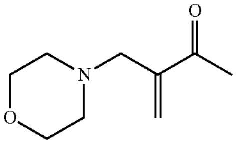 | C | 200 | 70 | 73 (White solid) | 30 |
| I-210 | Q | 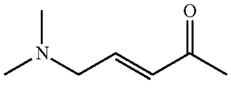 | C | 200 | 55.92 | 13 (Off-white solid) | 5.18 |
| I-239 | G | 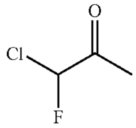 | C | 200 | 55.45 | 65 (Off-white solid) | 29.06 |
| I-167 | A | 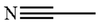 | D | 300 | 200 | 15 (White solid) | 5 |
| I-236 | J | 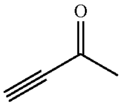 | E | 250 | 46 | 37.20 (Off-white solid) | 13 |
| I-237 | M | 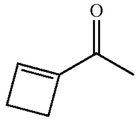 | E | 200 | 40 | 27.01 (White solid) | 10 |

I-190

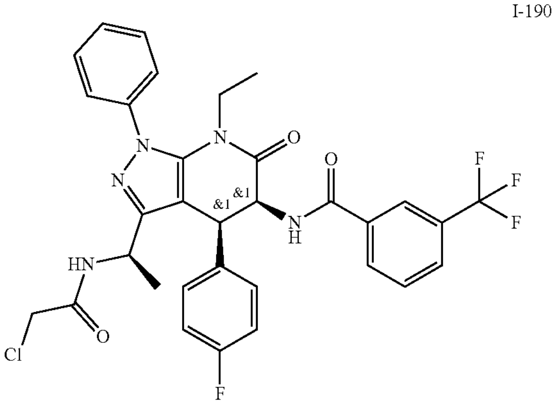 [SMILES: CCN1C(=O)[C@@H](NC(=O)c2cccc(C(F)(F)F)c2)[C@@H](c2ccc(F)cc2)c2c([C@@H](C)NC(=O)CCl)nn(-c3ccccc3)c21]

$^1$H NMR (400 MHZ, DMSO-$d_6$) δ 8.58-8.56 (m, 1H), 8.17-8.14 (m, 2H), 7.92 (d, J=7.6 Hz, 1H), 7.73-7.66 (m, 3H), 7.62-7.51 (m, 4H), 7.12-7.07 (m, 2H), 6.97-6.87 (m, 2H), 5.52-5.47 (m, 1H), 4.86 (t, J=7.2 Hz, 1H), 4.64 (d, J=7.2 Hz, 1H), 3.90-3.81 (m, 2H), 3.60-3.44 (m, 1H), 3.21-3.02 (m, 1H), 1.23 (d, J=6.8 Hz, 3H), 0.92 (d, J=7.2 Hz, 3H). LC-MS (Method-E)=642.0 [M+H]$^+$; 90.41% at RT 5.97 min. HPLC (Method-B): 88.52% at RT 17.23 min.

I-174

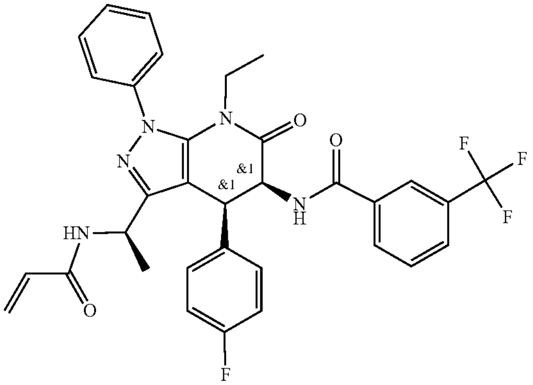

$^1$H NMR (400 MHZ, DMSO-$d_6$) δ 8.53-8.41 (m, 2H), 8.16-8.09 (m, 2H), 7.92 (d, J=8.0 Hz, 1H), 7.73-7.66 (m, 3H), 7.62-7.52 (m, 3H), 7.09-6.83 (m, 4H), 6.04-6.00 (m, 1H), 5.95-5.90 (m, 1H), 5.52-5.47 (m, 1H), 5.42-5.39 (m, 1H), 4.94 (t, J=8 Hz, 1H), 4.63 (d, J=7.2 Hz, 1H), 3.90-3.85 (m, 1H), 3.07-3.02 (m, 1H), 1.33-1.23 (m, 3H), 0.90 (t, J=6.8 Hz, 3H). LC-MS (Method-E)=620.0 [M+H]$^+$; 99.74% at RT 2.35 min. HPLC (Method-B): 99.05% at RT 16.63 min. HPLC-(Method-C): 39:51:8 at RT 7.13, 7.91, 13.0

I-212

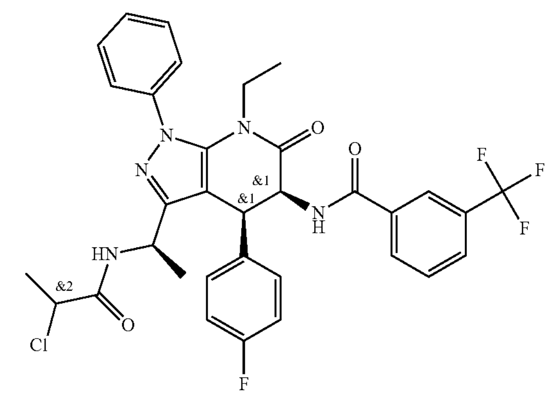

$^1H$ NMR (400 MHZ, DMSO-$d_6$) δ 8.66-8.60 (m, 1H), 8.55-8.49 (m, 1H), 8.19-8.11 (m, 2H), 7.92 (d, J=6.8 Hz, 1H), 7.73-7.67 (m, 3H), 7.60-7.53 (m, 3H), 7.12-7.06 (m, 2H), 6.99-6.90 (m, 2H), 5.55-5.45 (m, 1H), 4.89-4.84 (m, 1H), 4.63-4.59 (m, 1H), 4.48-4.25 (m, 1H), 3.92-3.85 (m, 1H), 3.08-3.02 (m, 1H), 1.47-1.25 (m, 6H), 0.93-0.84 (m, 3H). LC-MS (Method-E)=656.0 $[M+H]^+$; 91.07% at RT 6.09 min. HPLC (Method-B): 86.13% at RT 18.03 min.

I-215

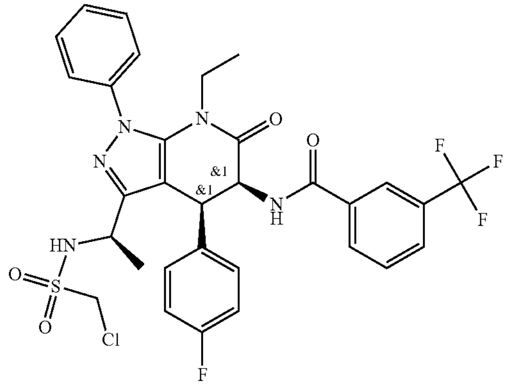

$^1H$ NMR (400 MHZ, DMSO-$d_6$) δ 8.50 (d, J=7.6 Hz, 1H), 8.20-8.12 (m, 3H), 7.91 (d, J=8.0 Hz, 1H), 7.70-7.68 (m, 3H), 7.61-7.54 (m, 3H), 7.12-7.08 (m, 2H), 6.99-6.96 (m, 2H), 5.54 (t, J=7.2 Hz, 1H), 4.82-4.69 (m, 3H), 4.56-4.40 (m, 1H), 3.90-3.84 (m, 1H), 3.06-3.04 (m, 1H), 1.24 (d, J=7.2 Hz, 3H), 0.91 (t, J=7.2 Hz, 3H). LC-MS (Method-D)=678.2 $[M+H]^+$; 98.10% at RT 2.37 min. HPLC (Method-B): 97.32% at RT 11.21 min.

I-238

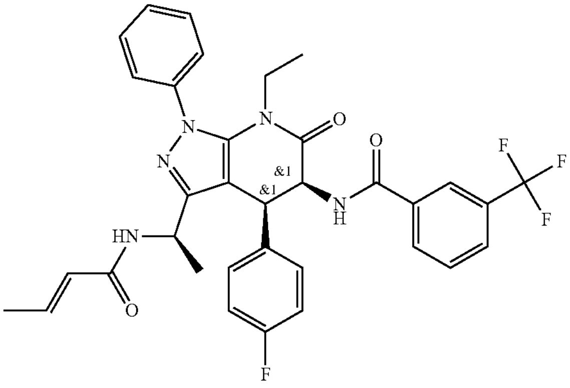

$^1H$ NMR (400 MHZ, DMSO-$d_6$) δ 8.55-8.44 (m, 1H), 8.21-8.13 (m, 3H), 7.92 (d, J=8.0 Hz, 1H), 7.73-7.65 (m, 3H), 7.61-7.50 (m, 3H), 7.11-6.81 (m, 4H), 6.57-6.54 (m, 1H), 5.75-5.61 (m, 1H), 5.56-5.45 (m, 1H), 4.99-4.82 (m, 1H), 4.63 (d, J=7.2 Hz, 1H), 3.94-3.85 (m, 1H), 3.07-3.01 (m, 1H), 1.66-1.56 (m, 2H), 1.33-1.22 (m, 4H), 0.90 (t, J=6.8 Hz, 3H). LC-MS (Method-E)=634.0 $[M+H]^+$; 99.61% at RT 5.94, 5.96 min. HPLC (Method-B): 98.85% at RT 16.86, 17.09 min.

I-74

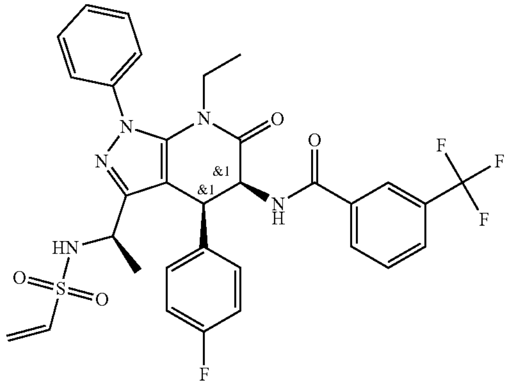

$^1H$ NMR (400 MHZ, DMSO-$d_6$) δ 8.59-8.50 (m, 1H), 8.21-8.13 (m, 2H), 7.91 (d, J=7.2 Hz, 1H), 7.79-7.52 (m, 6H), 7.13-7.08 (m, 2H), 7.02-6.95 (m, 2H), 6.57-6.54 (m, 1H), 6.02-5.87 (m, 2H), 5.50-5.45 (m, 1H), 4.80-4.65 (m, 1H), 4.31-4.22 (m, 1H), 3.90-3.84 (m, 1H), 3.06-3.04 (m, 1H), 1.25 (d, J=3.6 Hz, 3H), 1.02 (d, J=7.2 Hz, 1H), 0.90 (t, J=7.1 Hz, 3H). LC-MS (Method-D)=656.2 $[M+H]^+$; 96.10% at RT 2.38 min. HPLC (Method-B): 93.12% at RT 9.14, 9.23 min.

I-197

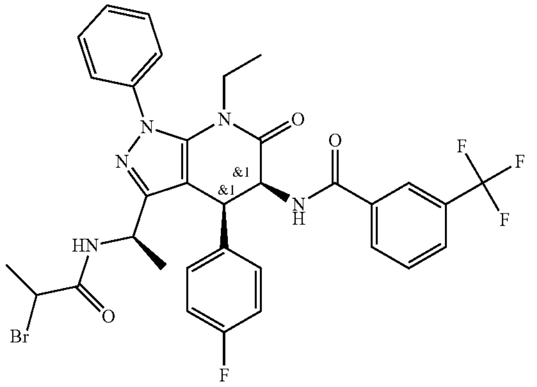

$^1$H NMR (400 MHZ, DMSO-$d_6$) δ 8.67 (t, J=7.6 Hz, 1H), 8.54-8.48 (m, 1H), 8.19-8.09 (m, 2H), 7.92 (d, J=7.2 Hz, 1H), 7.73-7.66 (m, 3H), 7.62-7.51 (m, 3H), 7.13-7.05 (m, 2H), 7.01-6.90 (m, 2H), 5.56-5.44 (m, 1H), 4.84 (t, J=8.0 Hz, 1H), 4.65-4.58 (m, 1H), 4.49-4.19 (m, 1H), 3.95-3.84 (m, 1H), 3.08-3.03 (m, 1H), 1.62-1.16 (m, 6H), 0.91 (t, J=6.8 Hz, 3H). LC-MS (Method-D)=700.2 [M+H]$^+$; 99.58% at RT 2.41 min. HPLC (Method-B): 99.53% at RT 9.48 min.

I-209

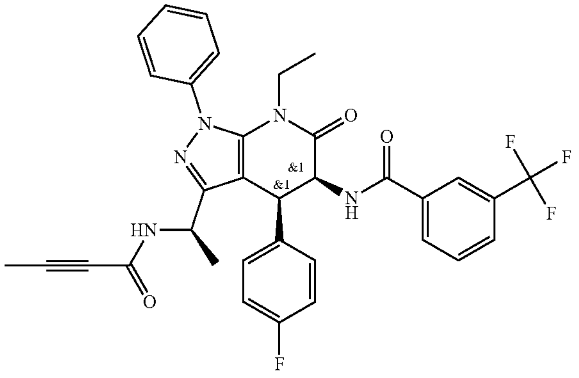

$^1$H NMR (400 MHZ, DMSO-$d_6$) δ 8.73 (d, J=8.0 Hz, 1H), 8.56-8.37 (m, 1H), 8.16-8.13 (m, 2H), 8.01-7.89 (m, 1H), 7.73-7.50 (m, 6H), 7.15-7.05 (m, 2H), 6.96-6.89 (m, 2H), 5.52-5.49 (m, 1H), 5.11-4.84 (m, 1H), 4.64-4.38 (m, 1H), 3.92-3.84 (m, 1H), 3.07-3.02 (m, 1H), 1.89-1.79 (m, 3H), 1.24-1.12 (m, 3H), 0.92 (d, J=6.8 Hz, 3H). LC-MS (Method-D)=632.2 [M+H]$^+$; 98.78% at RT 2.39, 2.30 min. HPLC (Method-B): 90.92% at RT 9.64, 9.93 min.

I-168

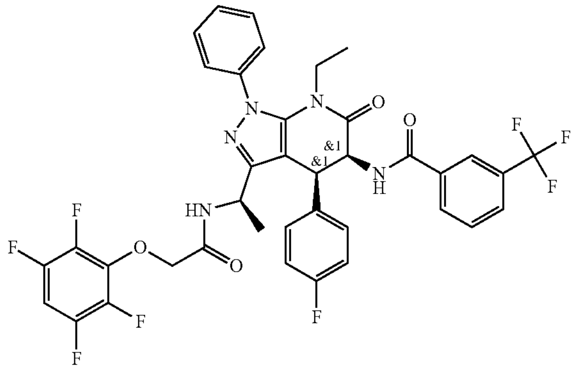

$^1$H NMR (400 MHZ, DMSO-$d_6$) δ 8.55-8.44 (m, 2H), 8.17-8.13 (m, 2H), 7.92 (d, J=7.2 Hz, 1H), 7.73-7.67 (m, 3H), 7.60-7.50 (m, 4H), 7.09-7.04 (m, 2H), 6.96-6.92 (m, 2H), 5.51-5.49 (m, 1H), 4.93-4.89 (m, 1H), 4.69-4.51 (m, 2H), 4.27-4.23 (m, 1H), 3.91-3.84 (m, 1H), 3.07-3.00 (m, 1H), 1.26-1.24 (m, 3H), 0.90 (d, J=7.2 Hz, 3H). LC-MS (Method-A)=772.4 [M+H]$^+$; 98.86% at RT 2.55, 2.48 min. HPLC (Method-B): 93.61% at RT 10.19, 9.81 min.

I-164

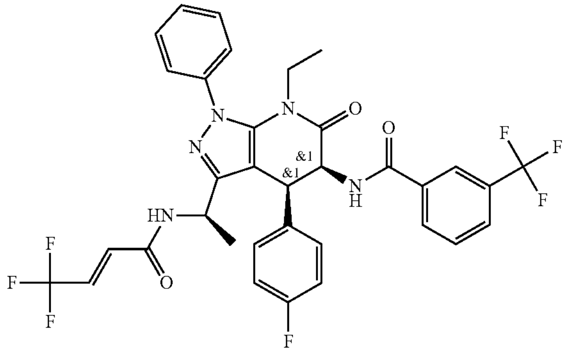

$^1$H NMR (400 MHZ, DMSO-$d_6$) δ 8.86 (d, J=7.6 Hz, 1H), 8.55 (d, J=7.4 Hz, 1H), 8.19-8.11 (m, 2H), 7.93 (d, J=7.8 Hz, 1H), 7.74-7.66 (m, 3H), 7.62-7.51 (m, 3H), 7.10-6.95 (m, 2H), 6.91-6.87 (m, 2H), 6.49-6.40 (m, 1H), 6.39-6.35 (m, 1H), 5.49 (t, J=7.2 Hz, 1H), 4.92 (t, J=7.6 Hz, 1H), 4.66 (d, J=7.2 Hz, 1H), 3.90-3.84 (m, 1H), 3.06-3.01 (m, 1H), 1.41-1.31 (m, 3H), 0.90 (t, J=6.8 Hz, 3H). LC-MS (Method-A)=687.8 [M+H]$^+$; 97.74% at RT 2.46, 2.40, min. HPLC (Method-B): 84.21% at RT 9.68 min.

I-165

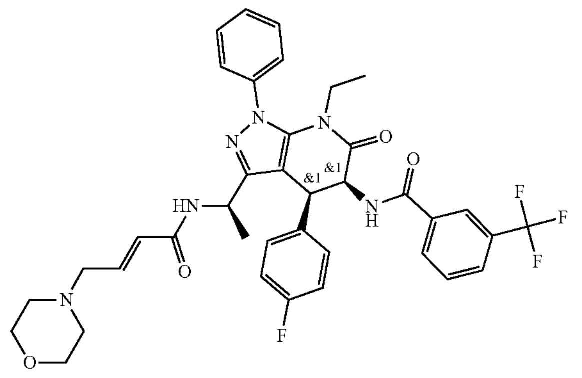

$^1$H NMR (400 MHZ, DMSO-$d_6$) δ 8.50 (d, J=7.6 Hz, 1H), 8.33-8.28 (m, 2H), 8.16-8.12 (m, 2H) 7.92 (d, J=7.6 Hz, 1H), 7.73-7.66 (m, 3H), 7.61-7.50 (m, 3H), 7.10-6.99 (m, 2H), 6.97-6.84 (m, 2H), 6.40-6.33 (m, 1H), 5.84-5.80 (d, J=15.6 Hz, 1H), 5.46-5.45 (t, J=7.2 Hz, 1H), 4.92 (t, J=6.8 Hz, 1H), 4.63 (d, J=7.2 Hz, 1H), 3.92-3.88 (m, 1H), 3.54-3.52 (m, 4H), 3.07-3.01 (m, 1H), 2.93-2.91 (m, 1H), 2.28-2.23 (m, 4H), 1.33-1.24 (m, 3H), 0.90 (t, J=7.1 Hz, 3H). LC-MS (Method-A)=719.66 $[M+H]^+$; 93.21% at RT 1.64 min. HPLC (Method-I): 80.90% at RT 7.10 min.

I-166

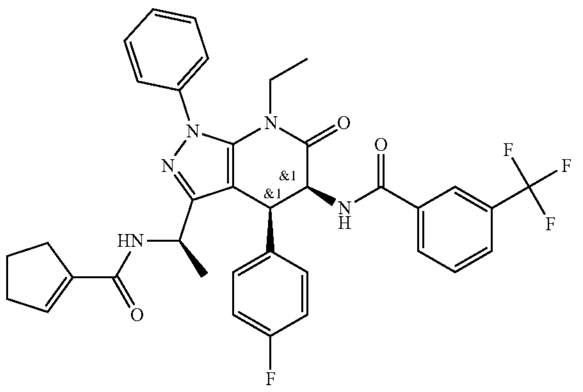

$^1$H NMR (400 MHZ, DMSO-$d_6$): δ 8.52 (d, J=7.2 Hz, 1H), 8.18-8.13 (m, 2H), 7.91 (d, J=7.6 Hz, 1H), 7.88-7.86 (m, 1H), 7.74-7.65 (m, 3H), 7.62-7.50 (m, 3H), 7.06-6.97 (m, 2H), 6.90-6.77 (m, 2H), 6.26 (t, J=2.0 Hz, 1H), 5.51-5.45 (m, 1H), 4.97-4.89 (m, 1H), 4.71 (d, J=7.2 Hz, 1H), 3.95-3.83 (m, 1H), 3.08-2.96 (m, 1H), 2.33-2.08 (m, 4H), 1.76-1.57 (m, 2H), 1.39-1.32 (m, 3H), 0.93-0.88 (m, 3H). LC-MS (Method-D)=660.2 $[M+H]^+$; 97.51% at RT 2.39 min. HPLC (Method-A): 97.09% at RT 9.81 min.

I-213

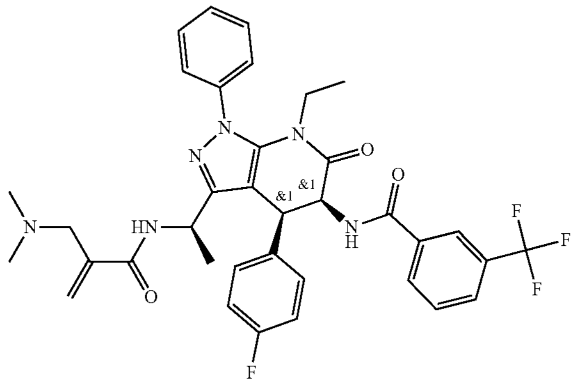

$^1$H NMR (400 MHZ, DMSO-$d_6$) δ 9.41 (d, J=7.6 Hz, 1H), 8.52 (d, J=7.6 Hz, 1H), 8.32 (s, 2H), 8.15-8.12 (m, 2H), 7.92 (d, J=7.6 Hz222, 1H), 7.73-7.52 (m, 5H), 7.12-7.08 (m, 2H), 7.00-6.96 (m, 1H), 5.81 (d, J=1.6 Hz, 1H), 5.53-5.49 (m, 1H), 5.34 (s, 1H), 4.94 (t, J=6.8 Hz, 1H), 4.61 (d, J=7.2 Hz, 1H), 3.92-3.86 (m, 1H), 3.10-3.00 (m, 3H), 2.07 (s, 6H), 1.13 (d, J=6.8 Hz, 3H) 0.92 (t, J=6.8 Hz, 3H). LC-MS (Method-D)=677.2 $[M+H]^+$; 98.12% at RT 2.56 min. HPLC (Method-A): 92.82% at RT 6.69, 6.62 min.

I-8

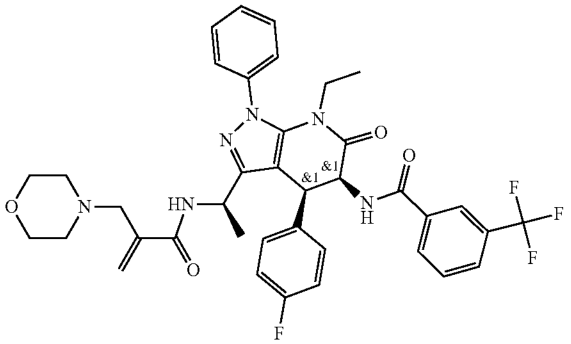

$^1$H NMR (400 MHZ, DMSO-$d_6$): δ 9.60 (d, J=7.6 Hz, 1H), 8.56-8.50 (m, 1H), 8.15-8.12 (m, 2H), 7.92 (d, J=7.6 Hz, 1H), 7.73-7.65 (m, 3H), 7.60-7.53 (m, 3H), 7.13-7.01 (m, 4H), 5.90 (d, J=1.2 Hz, 1H), 5.45 (t, J=7.2 Hz, 1H), 5.38 (d, J=1.2 Hz, 1H), 4.95 (t, J=7.2 Hz, 1H), 4.60-4.53 (m, 1H), 3.92-3.85 (m, 1H), 3.37-3.31 (m, 2H), 3.16-2.98 (m, 2H), 2.67 (m, 3H), 2.32-2.17 (m, 3H), 1.09 (d, J=6.8 Hz, 3H), 0.92 (d, J=6.8 Hz, 3H). LC-MS (Method-E)=716.7 $[M-H]^+$; 94.87% at RT 2.47, 2.42 min. HPLC (Method-B): 85.17% at RT 10.59, 10.48 min.

I-210

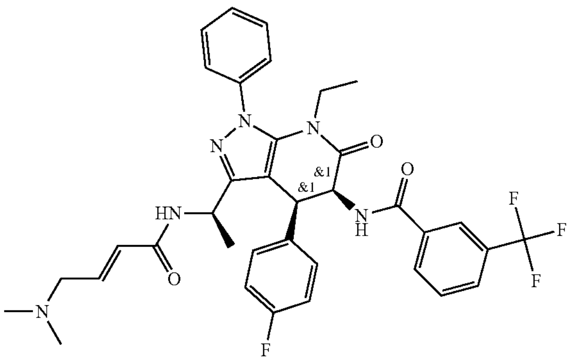

$^1$H NMR (400 MHZ, DMSO-$d_6$): δ 8.50-8.27 (m, 2H), 8.16-8.13 (m, 2H), 7.92 (d, J=7.6 Hz, 1H). 7.73-7.50 (m, 6H), 7.09-6.82 (m, 4H), 6.41-6.23 (m, 1H), 5.82-5.78 (m, 1H), 5.50-5.39 (m, 1H), 5.16-4.91 (m, 1H), 4.64-4.44 (m, 1H), 3.91-3.85 (m, 1H), 3.05-3.02 (m, 1H), 2.85 (d, J=5.6 Hz, 2H), 2.06 (d, J=12.8 Hz, 6H), 1.33-1.23 (m, 3H), 0.90 (t, J=7.2 Hz, 3H). LC-MS (Method-A)=677.98 $[M+H]^+$; 97.57% at RT 1.61 min. HPLC (Method-I): 95.28% at RT 6.85 min.

I-167

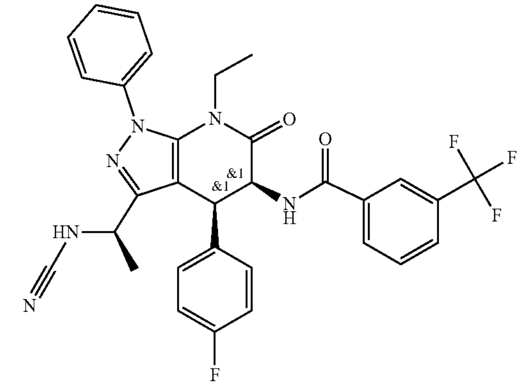

$^1$H NMR (400 MHZ, DMSO-$d_6$): δ 8.54 (d, J=7.6 Hz, 1H), 8.16-8.13 (m, 2H), 7.92 (d, J=8.4 Hz, 1H), 7.73-7.68 (m, 3H), 7.62-7.52 (m, 4H), 7.13-7.09 (m, 2H), 7.00-6.97 (m, 2H), 5.56-5.51 (m, 1H), 4.71-4.66 (m, 1H), 4.32-4.28 (m, 1H), 3.91-3.84 (m, 1H), 3.09-3.04 (m, 1H), 1.23-1.16 (m, 3H), 0.91 (t, J=6.8 Hz, 3H).

LC-MS (Method-E)=591.0 $[M+H]^+$; 98.90% at RT 2.36 min.

HPLC (Method-B): 98.65% at RT 9.48 min.

I-239

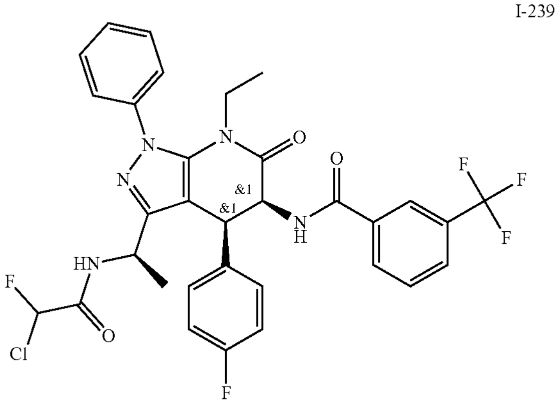 [SMILES: CCN1C(=O)[C@@H](NC(=O)c2cccc(C(F)(F)F)c2)[C@@H](c2ccc(F)cc2)c2c([C@@H](C)NC(=O)C(F)Cl)nn(-c3ccccc3)c21]

$^1$H NMR (400 MHZ, DMSO-$d_6$): δ 9.09 (d, J=8.0 Hz, 1H), 8.55-8.48 (m, 1H), 8.15-8.13 (m, 2H), 7.92 (d, J=7.2 Hz, 1H), 7.73-7.67 (m, 3H), 7.61-7.52 (m, 3H), 7.13-7.04 (m, 2H), 6.98-6.88 (m, 2H), 6.53-6.30 (m, 1H), 5.54-5.48 (m, 1H), 4.94-4.86 (m, 1H), 4.65-4.59 (m, 1H), 3.91-3.83 (m, 1H), 3.07-3.02 (m, 1H), 1.28-1.22 (m, 3H), 0.91 (t, J=6.8 Hz, 3H). LC-MS (Method-D)=659.9 $[M+H]^+$; 100% at RT 2.46, 2.35 min. HPLC (Method-B): 96.40% at RT 9.72, 9.78, 9.25, 9.31 min.

I-236

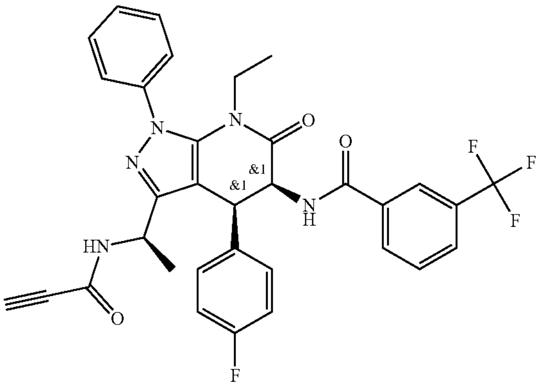

$^1$H NMR (400 MHZ, DMSO-$d_6$): δ 9.07 (d, J=8.0 Hz, 1H), 8.50-8.44 (m, 1H), 8.14 (d, J=12.4 Hz, 2H), 7.92 (d, J=7.6 Hz, 1H), 7.73-7.67 (m, 3H), 7.60-6.53 (m, 3H), 7.10-7.04 (m, 2H), 6.97-6.89 (m, 2H), 5.53-5.49 (m, 1H), 5.08-4.85 (m, 1H), 4.64-4.52 (m, 1H), 4.00 (s, 1H) 3.90-3.85 (m, 1H), 3.07-3.02 (m, 1H), 1.27-1.08 (m, 3H), 0.91 (t, J=6.8 Hz, 3H). LC-MS (Method-E)=618.0 $[M+H]^+$; 99.78% at RT 2.40, 2.29 min. HPLC (Method-B): 97.60% at RT 9.37, 8.93 min.

I-237

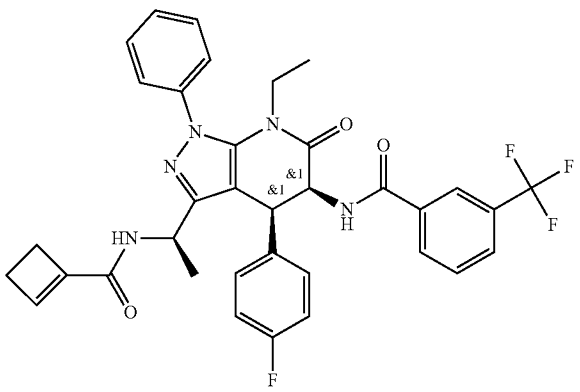

$^1$H NMR (400 MHZ, DMSO-$d_6$): δ 8.51 (d, J=7.6 Hz, 1H), 8.18-8.08 (m, 3H), 7.92 (d, J=7.6 Hz, 1H), 7.78-7.66 (m, 3H), 7.66-6.50 (m, 3H), 7.07-6.99 (m, 2H), 6.91-6.88 (m, 2H), 6.35 (s, 1H), 5.51-5.46 (m, 1H), 4.89 (t, J=7.6 Hz, 1H), 4.70 (d, J=7.2 Hz, 1H), 3.91-3.85 (m, 1H), 3.06-3.01 (m, 1H) 2.42-2.32 (m, 2H), 2.19 (s, 2H), 1.39-1.34 (m, 3H), 0.94-0.84 (m, 3H). LC-MS (Method-D)=646.2 $[M+H]^+$; 96.20% at RT 2.33, 2.24 min. HPLC (Method-B): 92.13% at RT 9.50, 9.08 min.

Synthesis of I-191

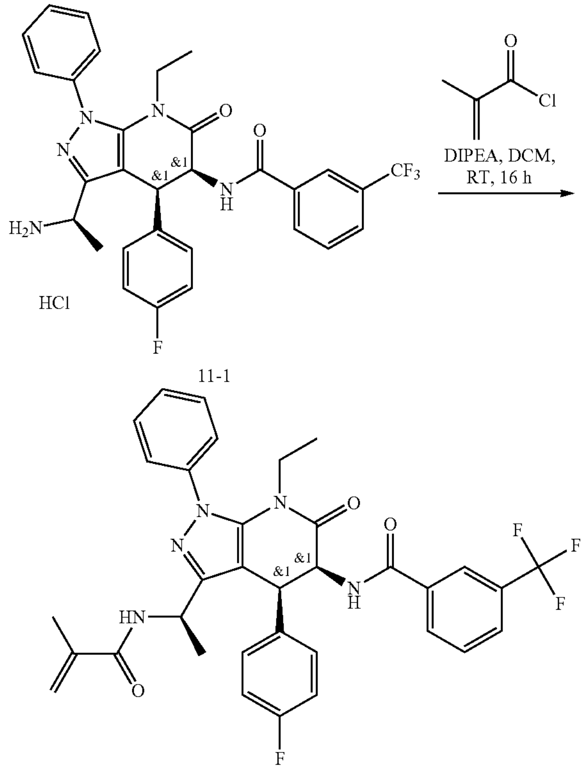

11-1

I-191

To a stirred solution of 11-1 (250 mg, 0.44 mmol) in dichloromethane (5 mL) was added N,N-Diisopropylethylamine (230 mg, 1.77 mmol) and 2-methylprop-2-enoyl chloride (60.07 mg, 0.57 mmol). The reaction mixture was stirred at room temperature for 16 h. The reaction mixture monitored by TLC and LC-MS. The reaction mixture was quenched with water (20 mL) extracted with EtOAc (2×25 mL) and dried over anhydrous $Na_2SO_4$ and concentrated under reduced pressure to afford crude compound. Obtained crude was purified by combi flash to afford I-191 (118.23 mg, 40.95%) as a white solid.

$^1$H NMR (400 MHZ, DMSO-$d_6$) δ 8.51 (d, J=7.6 Hz, 1H), 8.17-8.06 (m, 3H), 7.92 (d, J=7.8 Hz, 1H), 7.73-7.52 (m, 6H), 7.09-6.90 (m, 4H), 5.50-5.46 (m, 1H), 5.19 (t, J=1.4 Hz, 1H), 4.97-4.93 (m, 1H), 4.68 (d, J=6.8 Hz, 1H), 3.91-3.86 (m, 1H), 3.07-3.02 (m, 1H), 1.69 (s, 3H), 1.38-1.26 (m, 3H), 1.10-1.05 (m, 1H), 0.91 (t, J=6.8 Hz, 3H). LC-MS (Method-A)=634.4 $[M+H]^+$; 96.61% at RT 2.60, 2.58 min. HPLC (Method-A): 95.10% at RT 9.41, 9.50 min.

Example 12: Synthesis of Compounds I-81 and I-19

NMR:

$^1$H NMR spectrum was recorded on Bruker 400 MHz and Varian 400 MHZ instruments internally referenced to a tetramethylsilane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: I (95:5) B: 0.05% Formic acid in I Inj Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge BEH $C_{18}$, (50 mm*3.0 mm,2.5μ) Mobile Phase A: 2.5 mM Ammonium Bicarbonate in Water+5% I Mobile Phase B: 100% I Flow rate: 1.0 mL/min. Column temperature: 40° C. Gradient Program (B %): 0.0/2, 0.3/2, 2.0/98, 2.8/98, 3.0/2,3.7/2.

Method-C: Column: X-Select CSH C18 (50 mm*3.0 mm,2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2,2.0/98, 2.8/98, 3.0/2,3.7/2.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5, 1/5,8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/2,2/2, 12/90, 16/90; Flow: 1.0 mL/min.; Diluent: I:Water (80:20).

Method-C: Column: X SELECT CSH C18 (150×4.6 mm, 3.5μ); Mobile Phase A; 0.05% TFA IN Water: I (95:05); Mobile Phase B: 0.05% TFA in water: I(05:95); Programme: T/B %: . 0.01/10,12/90,16/90; Flow: 1 mL/min.; Diluent: water: I (80:20).

Method-D: Column: X-Bridge CSH C18 (4.6*150) mm 5μ Mobile Phase: A-0.1% TFA in water B-Acetonitrile Inj Volume; 5.0 μL, Flow Rate: 1.2. mL/minute Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in Hexane, Mobile Phase B: IPA A/B: 60/40 Flow: 1.0 ml/MIN PDA: OJ-H_015.

Method-F: Column Name: CHIRALPAK-IK (250×4.6 mm, 5 μm) Mobilephase-A: n-Hexane, Mobilephase-B: ETOH/MEOH (50/50) Flow rate: 1.0 mL/min %A/B: 50/50.

Method-G: Column: X-Select CHS C18 (4.6*150) mm 5μ Mobile Phase: A-5 mM Ammonium acetate B-Acetonitrile Inj Volume; 5.0 μL, Flow Rate: 1.0 mL/minute.

Synthesis of I-81

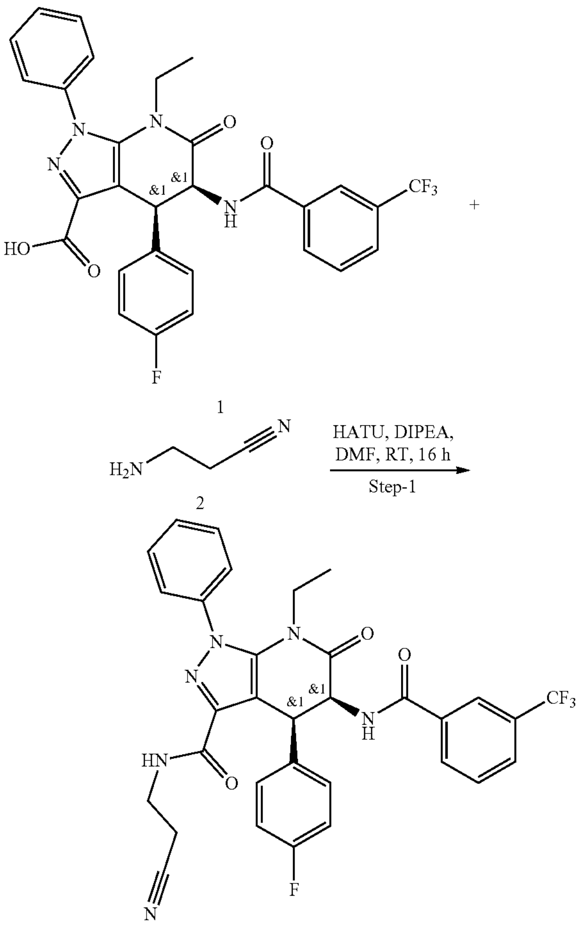

1

2

I-81

Step-1: Synthesis of rac-(4R,5R)—N-(2-cyano-ethyl)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxamide (I-81)

To a stirred solution of rac-(4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxylic acid, 1 (0.150 g, 0.26 mmol) in DMF (2 mL) were added N,N-Diisopropylethylamine (0.173 g, 1.32 mmol), HATU (0.153 g, 0.39 mmol) followed by 3-aminopropanenitrile, 2 (0.018 g, 0.26 mmol) at room temperature under inert atmosphere. The reaction mixture was stirred at same temperature for 16 h. Reaction progress was monitored by TLC and LCMS. After completion of the reaction, the reaction mixture was quenched with ice cold water (20 mL), extracted with EtOAc (2×20 mL), and concentrated under reduced pressure to get the crude, which then was purified by flash column chromatography using EtOAc/Heptane as eluent to get I-81 (50 mg, 30%) as an off white solid.

$^1$HNMR (400 MHZ, DMSO-$d_6$) δ=8.62-8.55 (m, 2H), 8.16-8.13 (m, 2H), 7.93-7.91 (m, 1H), 7.82-7.80 (m, 2H), 7.71 (t, J=7.6 Hz, 1H), 7.66-7.61 (m, 3H), 7.11-7.06 (m, 2H), 7.03-7.00 (m, 2H), 5.53 (t, J=7.2 Hz, 1H), 5.00 (d, J=7.2 Hz, 1H), 3.91-3.86 (m, 1H), 3.46-3.34 (m, 2H), 3.03-2.98 (m, 1H), 2.71 (t, J=6.4 Hz, 2H), 0.89 (t, J=6.8 Hz, 3H). LC-MS (Method-C)=619.1 [M+H]$^+$; 98.148% at RT 6.088 min. HPLC (Method-B)=98.502% at RT 9.197 min.

Synthesis of I-19

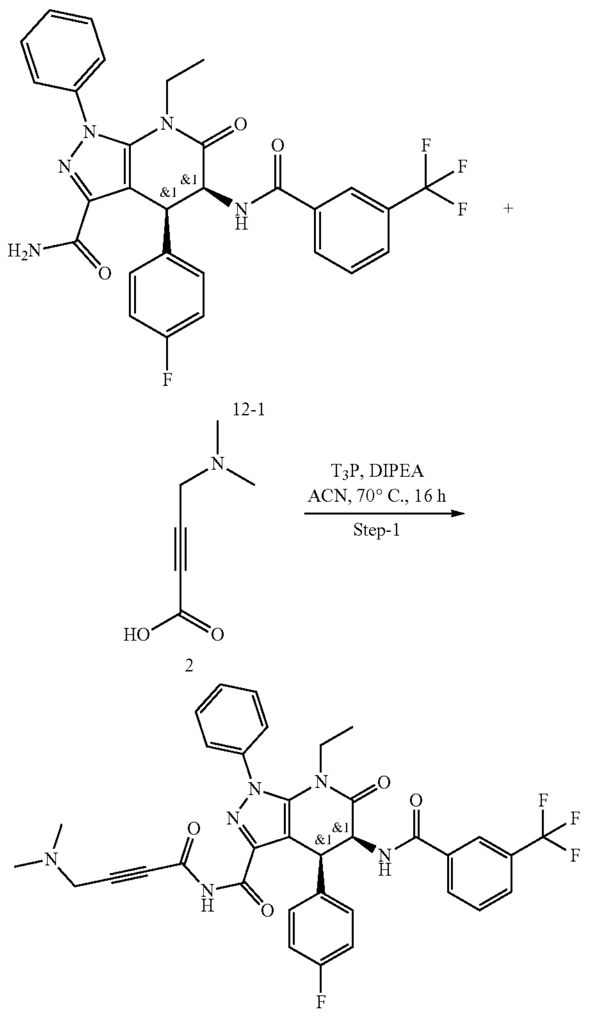

12-1

2

I-19

Step-1: Synthesis of rac-N-((4R,5R)-3-((4-(dimethylamino) but-2-ynamido)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl) benzamide (I-19)

To a stirred solution of 12-1 (0.2 g, 0.36 mmol) in I (5.0 mL) were added N,N-Diisopropylethylamine (0.317 mL, 1.81 mmol), 4-(dimethylamino) but-2-ynoic acid, 2 (0.046 g, 0.36 mmol) and T3P (0.69 g, 1.0 mmol, 50% in ethyl acetate) reagent at room temperature. Reaction was stirred for 16 h at 70° C. Progress of the reaction was monitored by TLC and LCMS. Reaction mixture was allowed to cool to room temperature, quenched with water (20 mL) and extracted with EtOAc (2×20 mL). Combined organic layers were dried over anhydrous sodium sulphate and concentrated to get the crude compound. The obtained crude compound was purified by prep-HPLC, and pure fractions were evaporated to get I-19 (0.025 g, 10%) as white solid.

$^1$HNMR (400 MHZ, DMSO-$d_6$) δ=8.81 (t, J=5.6 Hz, 1H), 8.49 (d, J=7.6 Hz, 1H), 8.16-8.13 (m, 2H), 7.93-7.91 (m, 1H), 7.73-7.66 (m, 3H), 7.61-7.53 (m, 3H), 7.08 (t, J=8.8 Hz, 2H), 6.95-6.91 (m, 2H), 5.51 (t, J=7.2 Hz, 1H), 4.58 (d, J=7.2 Hz, 1H), 4.31-4.26 (m, 1H), 4.13-4.07 (m, 1H), 3.91-3.88 (m, 1H), 3.26 (s, 2H), 3.05-3.00 (m, 2H), 2.12 (s, 6H), 0.91 (t, J=6.8 Hz, 3H). LC-MS (Method-B)=661.1 $[M+H]^+$; 99.728% at RT 2.434 min. HPLC (Method-B)= 99.497% at RT 8.574 min. HPLC-Chiral (Method-F)= 49.762% at RT 4.933 min, 49.532% at RT 6.583 min.

Example 13: Synthesis of Compounds I-31, I-93 and I-11

NMR:

$^1$H NMR spectrum was recorded on Bruker 400 MHz and Varian 400 MHZ instruments internally referenced to a tetramethyl silane (TMS) signal. Chemical shifts (δ) and coupling constants (J) were expressed in parts per million and hertz, respectively.

LCMS:

2.5μ; Mobile Phase: A: 0.05% Formic acid in water: I (95:5); B: 0.05% Formic acid in CAN; Inj Volume: 2.0 μL, Column oven temperature: 50° C.; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

Method-C: Column: X-Select CSH C18, (50 mm*3.0 mm,2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2,2.0/98, 2.8/98, 3.0/2,3.7/2.

Method-D: Column: X-Select CSH C18 (3.0*50 mm, 2.5 μm), Mobile Phase A: 2.5 Mm Ammonium Bicarbonate in $H_2O$+5% CAN; Mobile Phase B: 100% I, Gradient % B: 0/2,0.3/2,2.0/98,2.8/98,3.0/2,3.7/2, Flow rate: 1.0 mL/min.

Method-E: Column: X-Bridge BEH C18, (50 mm*3.0 mm,2.5μ) Mobile Phase A: 2.5 mM Ammonium Bicarbonate in Water+5% CAN; Mobile Phase B: 100% ACN Flow rate: 1.0 mL/min. Column temperature: 40° C. Gradient Program (B %): 0.0/2, 0.3/2, 2.0/98, 2.8/98, 3.0/2,3.7/2.

HPLC:

Method-A: Column: X Select CSH C18 (150×4.6) mm,3.5μ; Mobile phase A: 0.1% FA in Water: CAN (95:05); Mobile phase B: Acetonitrile; Gradient Programme: T/B %: 0.01/5, 1/5,8/100,12/100,14/5, 18/5; Flow rate: 1.2 ml/min.

Method-B: Column: X-Bridge CSH C18 (150×4.6 mm, 3.5 μm); Mobile Phase-A: 5 mM $NH_4HCO_3$; Mobile Phase-B: I; Programme: T/B %: 0.01/2,2/2, 12/90, 16/90; Flow rate: 1.0 mL/min.; Diluent: I:Water (80:20).

Method-C: Column: X SELECT CSH C18 (150×4.6 mm, 3.5μ); Mobile Phase A; 0.05% TFA in water: I (95:05); Mobile Phase B: 0.05% TFA in water: I (05:95); Programme: T/B %: . 0.01/10,12/90,16/90; Flow rate: 1 mL/min.; Diluent: Water: I (80:20).

Method-D: Column: X-Bridge CSH C18 (4.6*150) mm 5μ Mobile Phase: A-0.1% TFA in water; B-Acetonitrile Inj Volume; 5.0 μL, Flow Rate: 1.2 mL/minute; Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in Hexane; Mobile Phase B: IPA A/B: 60/40 Flow: 1.0 ml/MIN PDA: OJ-H_015.

Method-F: Column: ACE Excel 2 C18-AR, 100 mm×3.0 mm Mobile Phase A: 0.05% TFA in Water; Mobile Phase B: 0.05% TFA in Acetonitrile; Colum Temperature: 40° C. Flow Rate: 0.6 mL/min Gradient: 0/5, 1/5, 6/90, 8.5/90, 8.8/5, 11/5.

Method-G: Column: CHIRAL PAK-IC (250×4.6 mm, 5 μm) Mobile Phase A: 0.1% DEA in Hexane; Mobile Phase B: EtOH/MeOH (50/50) A: B: 80/20 Flow 1.0 ml/min.

Method-H: Column: X-Bridge C18 (4.6*150) mm 5μ Mobile Phase: A-5 mM Ammonium Acetate; B-Acetonitrile Flow Rate: 1.0. mL/minute Gradient program: Time (min)/B Conc.: 0.01/5, 1.0/5, 8.0/100, 12.0/100, 14.0/5, 18.0/5.

Method-I: Column: CHIRALPAK-AD-H (250×4.6 mm, 5 μm), Mobile Phase A: 0.1% FA in n-Hexane, Mobile Phase B: ETOH Flow Rate: 1.0. mL/minute.

Method-J: Column: CHIRALCEL-OX-H Mobile Phase A: n-Hexane; Mobile Phase B: IPA, Flow: 1.0 ml/Min.

Method-K: Column: CHIRALPAK-IG (250×4.6 mm, 5 μm), Mobile Phase A: 0.1% DEA n-Hexane, Mobile Phase B: DCM: MEOH (50:50), Flow rate: 1.0 ml/min.

Method-L: Column: CHIRALPAK-IC (250×4.6 mm, 5 μm) Mobile phase-A: MeOH (100%), Flow rate: 1.0 ml/min.

Method-M: Column: CORTECS UPLC C18 (3.0*30 mm, 1.6 μm), Mobile Phase A: 0.05% Formic acid in water, Mobile Phase B: 0.05% Formic acid in I, Gradient: Time/% B: 0/3,0.1/3,1.4/97,2/97, 2.05/3,2.5/3. Flow Rate: 0.85 ml/min.

Synthesis of I-31

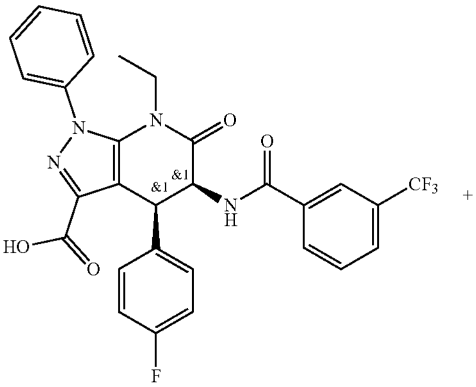

Int-1

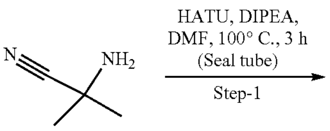

-continued

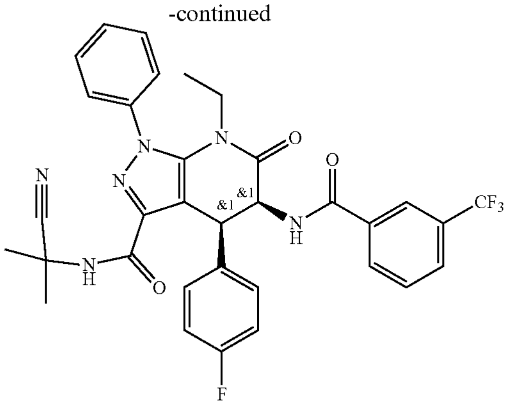

I-31

Step 1: Synthesis of rac-(4R,5R)—N-(2-cyanopropan-2-yl)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxamide (I-31)

To a stirred solution of Int-1 rac-(4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxylic acid (200 mg, 0.3530 mmol) in DMF (5.0 mL), were added N,N-Diisopropylethylamine (0.185 mL, 1.059 mmol), 2-amino-2-methyl-propanenitrile (29.70 mg, 0.3530 mmol) followed by HATU (207.6 mg, 0.5296 mmol) at RT. The vial was sealed and then the reaction mixture was irradiated under microwave at 100° C. for 3 h. Reaction progress was monitored by TLC and LCMS. After completion of SM by TLC, reaction mixture was quenched with water (25 mL) and extracted with EtOAc (2×25 mL). Combined organic layers were dried over sodium sulphate, filtered and concentrated under reduced pressure to obtain crude compound (350 mg). Crude obtained was purified by Prep-HPLC and lyophilised to afford (4~{S},5~{S})-~{N}-(1-cyano-1-methyl-ethyl)-7-ethyl-4-(4-fluorophenyl)-6-oxo-1-phenyl-5-[[3-(trifluoromethyl)benzoyl]amino]-4,5-dihydropyrazo lo[3,4-b]pyridine-3-carboxamide (75 mg, 33.48% Yield) as off-white solid. Prep. HPLC Method: Preparative Column: X-BRIDGE C18 (250*30 mm), 5μ, Mobile Phase A: 10 Mm ABC in $H_20$, Mobile Phase B: 100% I, Gradient (Time/% B): 0/10, 3/10, 12/40, 45/77, 50/99.

$^1$H NMR (400 MHZ, DMSO-$d_6$) δ=8.58 (d, J=7.2 Hz, 1H), 8.52 (s, 1H), 8.18 (t, J=7.2 Hz, 2H), 7.93 (d, J=7.6 Hz, 1H), 7.81 (dd, J=8.0 Hz, 2H), 7.73 (t, J=8.0 Hz, 1H), 7.66-7.61 (m, 3H), 7.11 (t, J=8.8 Hz, 2H), 7.04 (q, J=8.8 Hz, 2H), 5.55 (t, J=7.2 Hz, 1H), 4.96 (d, J=7.2 Hz, 1H), 3.91 (q, J=14.4 Hz, 1H), 3.02 (q, J=14.2 Hz, 1H), 1.64 (d, J=15.2 Hz, 6H), 0.88 (t, J=7.2 Hz, 3H). LCMS (Method-D): 631.0 (M−H)+, 99.716% at RT: 2.322 min. HPLC (Method-B): 99.906% at RT: 9.664 min. C-HPLC (Method-G): 49.48% at RT: 5.526 min, 50.52% at RT: 9.934 min.

Synthesis of I-93

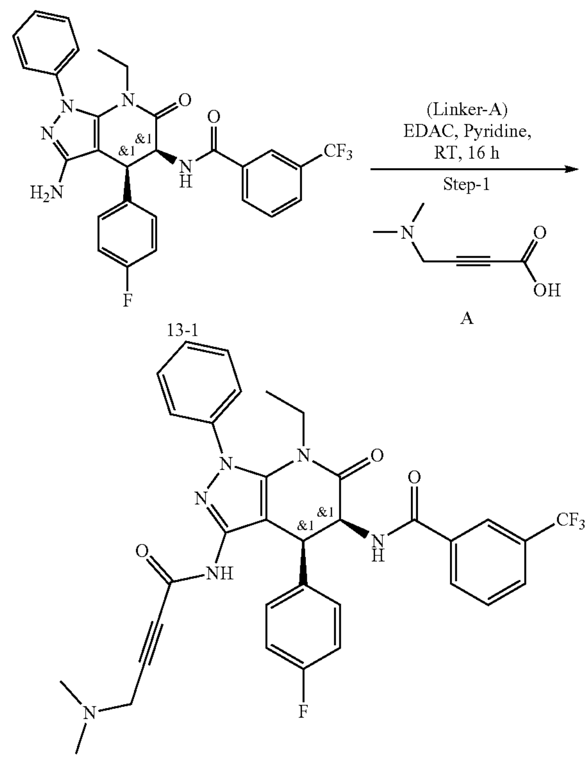

13-1

A

I-93

Step 1: Synthesis of rac-N-((4R,5R)-3-(4-(dimethylamino) but-2-ynamido)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (I-93)

To a stirred solution of 4-(dimethylamino) but-2-ynoic acid (A) (89 mg, 0.70 mmol) in Pyridine (0.5 mL), were added 13-1 (250 mg, 0.47 mmol) and EDAC (180 mg, 0.93 mmol) and the reaction mixture was stirred at RT for 16 h. Reaction progress was monitored by TLC). After completion of SM by TLC, reaction mixture was diluted with water (20 mL) and extracted with EtOAc (2×30 mL). Combined organic layers were dried over sodium sulphate, filtered and concentrated under reduced pressure to obtain crude compound. Crude obtained was purified by Prep-HPLC to afford rac-N-((4R,5R)-3-(4-(dimethylamino) but-2-ynamido)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (1-93) (45 mg, 15% Yield) as an off white solid.

$^1$H NMR (400 MHZ, DMSO-$d_6$) δ=10.9 (s, 1H), 8.47 (br s, 1H), 8.15 (t, J=4.8 Hz, 2H), 7.92 (d, J=8.0 Hz, 1H), 7.73-7.68 (m, 3H), 7.61-7.52 (m, 3H), 7.09 (t, J=8.4 Hz, 2H), 6.92 (s, 2H), 5.52 (t, J=7.2 Hz, 1H), 4.77 (d, J=6.4 Hz, 1H), 3.90 (q, J=14.4 Hz, 1H), 3.37 (s, 2H), 3.08 (q, J=14.4 Hz, 1H), 2.18 (s, 6H), 0.92 (t, J=6.8 Hz, 3H). LCMS (Method-D): 647.1 $(M+H)^+$, 99.53% at RT: 1.95 min. HPLC (Method-B): 99.361% at RT: 8.954 min. C-HPLC (Method-G): 50.116% at RT: 5.715 min, 49.884% at RT: 13.330 min.

Synthesis of (I-11)

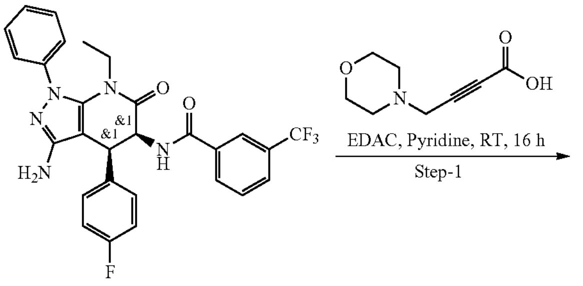

13-1

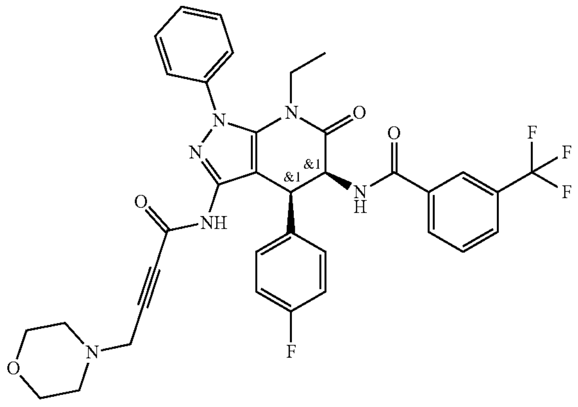

I-11

Step 1: Synthesis of rac-N-((4R,5R)-7-ethyl-4-(4-fluorophenyl)-3-(4-morpholinobut-2-ynamido)-6-oxo-1-phenyl-4,5,6,7-tetrahydro-1H-pyrazolo[3,4-b] pyridine-5-yl)-3-(trifluoromethyl)benzamide (I-11)

To a stirred solution of 4-morpholinobut-2-ynoic acid (120 mg, 0.70 mmol) in Pyridine (4 mL), were added 13-1 (250 mg, 0.47 mmol) and EDAC (180 mg, 0.93 mmol) and the reaction mixture was stirred at RT for 16 h. Reaction progress was monitored by TLC. After completion of SM by TLC, reaction mixture was diluted with water (20 mL) and extracted with EtOAc (2×30 mL). Combined organic layers were dried over sodium sulphate, filtered, and concentrated under reduced pressure to obtain crude compound. Crude obtained was purified by Prep-HPLC to afford rac-N-((4R,5R)-7-ethyl-4-(4-fluorophenyl)-3-(4-morpholinobut-2-ynamido)-6-oxo-1-phenyl-4,5,6,7-tetrahydro-1H-pyrazolo[3,4-b]pyridine-5-yl)-3-(trifluoromethyl)benzamide (I-11) (60.39 mg, 18.87% yield) as off white solid.

Prep. HPLC Method: Preparative Column: X-Select C18 (250*30 MM), 5μ, Mobile Phase A: 10 Mm ABC in $H_20$, Mobile Phase B: 100% I, Gradient (Time/% B): 0/10, 3/10, 10/45, 15/60, 20/65, 25/70, 30/75, 35/80, 60/98.

$^1$H NMR (400 MHZ, DMSO-$d_6$) δ=10.9 (s, 1H), 8.47 (d, J=6.0 Hz, 1H), 8.15 (t, J=5.2 Hz, 2H), 7.92 (d, J=7.6 Hz, 1H), 7.73-7.68 (m, 3H), 7.61-7.52 (m, 3H), 7.12 (t, J=7.6 Hz, 2H), 6.92 (s, 2H), 5.53 (t, J=7.2 Hz, 1H), 4.78 (d, J=6.4 Hz, 1H), 3.91-3.82 (m, 1H), 3.56 (s, 4H), 3.44 (s, 2H), 3.08 (q, J=14.0 Hz, 1H), 2.46 (s, 4H), 0.93 (t, J=6.8 Hz, 3H). LCMS (Method-D): 689.1 $(M+H)^+$, 99.85% at RT: 1.94 min. HPLC (Method-B): 99.752% at RT: 8.972 min.

Chiral-HPLC (Method-G): 49.370% at RT: 6.672 min, 50.63% at RT: 18.211 min.

Example 14: Synthesis of Compounds I-154, I-15 and I-5

NMR:

$^1$H NMR spectrum was recorded on Bruker 400 MHz and Varian 400 MHz instruments internally referenced to a tetramethyl silane (TMS) signal. Chemical shifts (δ) and coupling constants (J) were expressed in parts per million and hertz, respectively.

LCMS:

Method-A: LCMS, X-Select (Formic acid); Column: X-Select CSH C18 (3.0*50) mm 2.5μ; Mobile Phase: A: 0.05% Formic acid in water: I (95:5); B: 0.05% Formic acid in CAN, Inj Volume: 2.0 μL, Column oven temperature: 50° C.; Flow Rate: 1.2 mL/min; Gradient Program (B %): 0.0/2, 0.3/2, 2.0/98, 2.8/98, 3.0/2,3.7/2.

Method-B: Column: X-Bridge BEH C18, (50 mm*3.0 mm,2.5μ) Mobile Phase A: 2.5 mM Ammonium Bicarbonate in Water+5% CAN; Mobile Phase B: 100% I Flow rate: 1.0 mL/min. Column temperature: 40° C. Gradient Program (B %): 0.0/2, 0.3/2, 2.0/98, 2.8/98, 3.0/2, 3.7/2.

Method-D: Column: X-Select CSH C18, (50 mm*3.0 mm,2.5μ) Mobile Phase A: 2.5 mM Ammonium Bicarbonate in Water+5% CAN; Mobile Phase B: 100% I Flow rate: 1.0 mL/min. Column temperature: 40° C. Gradient Program (B %): 0.0/2, 0.3/2, 2.0/98, 2.8/98, 3.0/2, 3.7/2.

Method-E: Column: CORTECS UPLC C18 (3×30 mm, 1.6 μm) Mobile Phase: A: 0.05% FA in Water; B: 0.05% FA in I, Flow rate: 0.85 mL/min (Gradient), Column Oven Temp: 45° C., Gradient Program (B %): 0/3, 0.1/3, 1.4/97, 2/97, 2.05/3, 2.5/3.

Method-F: Column: Poroshell 120 EC-C18 (3×100 mm,2.7 μm) Mobile Phase: A: 0.05% TFA in Water; B: 0.05% TFA in I, Flow rate: 0.80 mL/min (Gradient), Column Oven Temp: 40° C., Gradient Program (B %): 0.01/2, 0.2/2, 3/98, 5/98, 5.2/2, 7/2.

Method-H: Column: BAKERBOND Q2100 C18 (2.1×50 mm, 1.8 μm) Mobile Phase: A: 0.05% FA in Water, Mobile Phase B: 0.05% FA in Acetonitrile, Colum Temperature: 40° C., Flow Rate: 0.6 mL/min, Gradient: 0.0/2, 0.3/2, 2.0/98, 2.8/98, 3.0/2, 3.7/2, Diluent: I:Water.

Method-I: Column: Poroshell 120 EC-C18 (3×100 mm,2.7 μm) Mobile Phase: A: 0.05% TFA in Water; B: 0.05% TFA in I, Flow rate: 0.70 mL/min (Gradient), Column Oven Temp: 40° C., Gradient Program (B %): 0.01/10, 0.2/10, 6/90, 8/90, 8.1/10, 10/10.

HPLC:

Method-A: Column: X Select CSH C18 (150×4.6) mm, 3.5μ; Mobile phase A: 0.1% FA in Water: I (95:05); Mobile phase B: Acetonitrile; Gradient Programme: T/B %: 0.01/5, 1/5, 8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/5, 1.0/5, 8.0/100, 12.0/100, 14.0/5, 18.0/5; Flow: 1.0 mL/min.

Method-C: Column: X SELECT CSH C18 (150×4.6 mm, 3.5μ); Mobile Phase A; 0.05% TFA in water: I (95:05); Mobile Phase B: 0.05% TFA in water: I (05:95); Programme: T/B %: 0.01/10, 12/90, 16/90; Flow: 1 mL/min.; Diluent: WATER: I (80:20).

Method-D: Column: X-Bridge CSH C18 (4.6*150) mm 5μ Mobile Phase: A-0.1% TFA in water B-Acetonitrile Inj Volume; 5.0 μL, Flow Rate: 1.2. mL/minute Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in Hexane Mobile Phase B: IPA A/B: 60/40 Flow: 1.0 ml/Min PDA: OJ-H_015.

Method-F: Column Name: CHIRALPAK-IK (250×4.6 mm, 5 μm) Mobile phase-A: n-Hexane; Mobile phase-B: EtOH/MeOH (1:1) Flow rate: 1.0 mL/min % A/B: 50/50.

Method-H: Column: X-Bridge CSH C18 (150×4.6 mm, 3.5 μm); Mobile Phase-A: 5 mM $NH_4HCO_3$ in water; Mobile Phase-B: I; Programme/B %: Time (min)/B Conc.: 0.01/5, 1.0/5, 8.0/100, 12.0/100, 14.10/5, 18.0/5; Flow: 1.0 mL/min.; Diluent: I:Water (80:20).

Method-I: Column Name: CHIRALPAK-IC (250×4.6 mm, 5 μm) Mobile phase-A: 0.1% TFA in n-Hexane, Mobile phase-B: DCM: IPA (50:50), Flow rate: 1.0 mL/min % A/B: 60/40.

Method-L: Column Name: CHIRALPAK-IA (150*4.6 mm, 3 μm)) Mobile phase-A: n-hexane, Mobile phase-B: EtOH: MeOH (1:1), Flow rate: 1.0 mL/min, % A/B: 70:30.

Method-N: Column: BAKERBOND 1.7μ or 1.8μ C18 100 mm×2.1 mm Mobile Phase A: 0.05% FA in Water, Mobile Phase B: 0.05% FA in Acetonitrile, Colum Temperature: 40° C., Flow Rate: 0.5 mL/min, Gradient: 0/5, 3/5, 6/95, 8.5/95, 8.8/5, 11/5, Diluent: I:Water.

Method-T: Column Name: CHIRALPAK-IC (250*4.6 mm, 5 μm) Mobile phase-A: n-HEXANE, Mobile phase-B: IPA: MeOH (50:50), Flow rate: 1.0 mL/min % A/B: 50/50.

Method-X: Column Name: CHIRALPAK-IK (250×4.6 mm, 5 μm) Mobile phase-A: n-Hexane Mobile phase-B: EtOH/MeOH (1:1) Flow rate: 1.0 mL/min % A/B: 50/50.

Method-Y: Column Name: CHIRALPAK-IK (250×4.6 mm, 5 μm) Mobile phase-A: n-Hexane; Mobile phase-B: IPA/MeOH (1:1) Flow rate: 1.0 mL/min %.

Method-Z: Column Name: CHIRALPAK-IA (150*4.6 mm, 3 μm)) Mobile phase-A: n-hexane, Mobile phase-B: IPA, Flow rate: 1.0 mL/min, % A/B: 70:30.

Method-Z-1: Column Name: CHIRALPAK-IE (250×4.6 mm, 5 μm) Mobile phase-A: n-Hexane/DEA/TFA (100/0.1/0.1%); Mobile phase-B: EtOH/MeOH (1:1) Flow rate: 1.0 mL/min % A/B: 60/40.

Synthesis of I-154

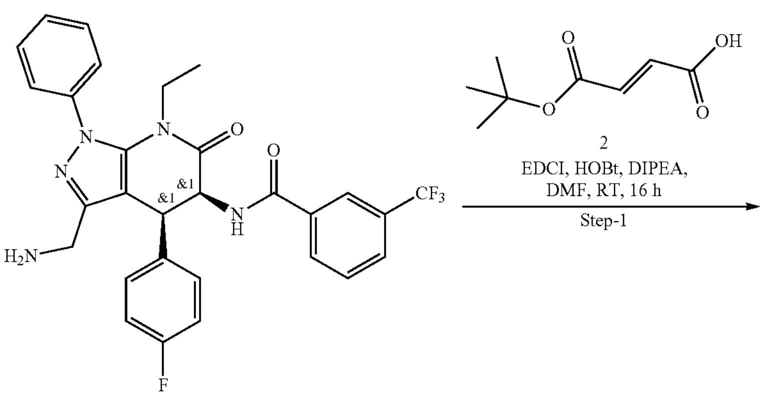

1

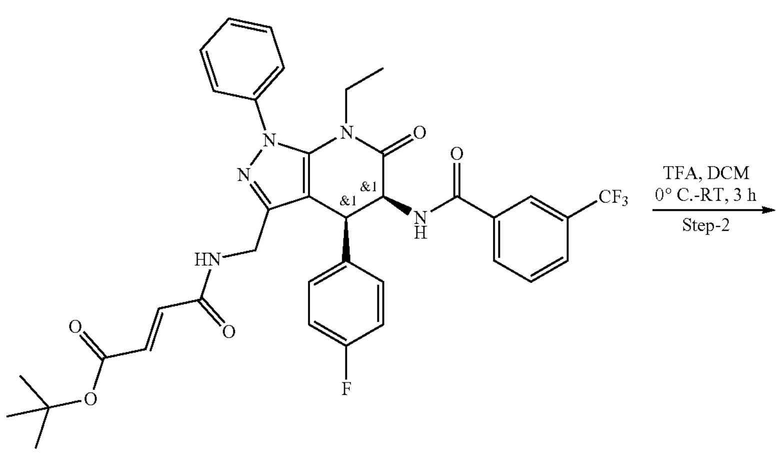

3

-continued

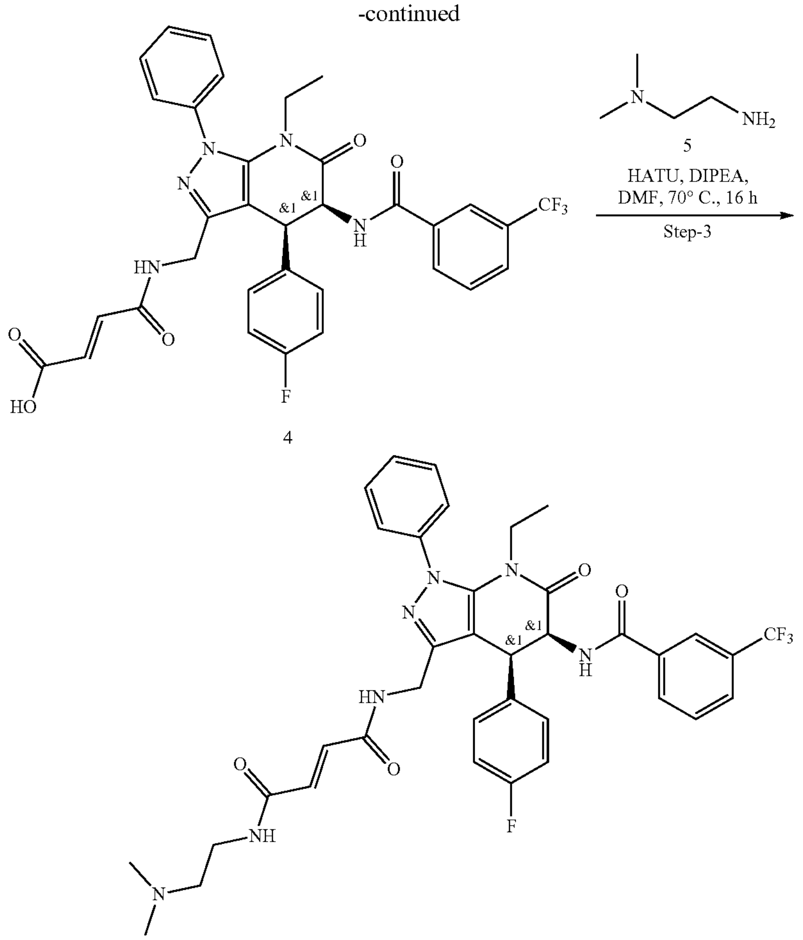

4

I-154

Step-1: Synthesis of rac-tert-butyl I-4-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)methyl)amino)-4-oxobut-2-enoate (3)

To a stirred solution of rac-N-((4R,5R)-3-(aminomethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (1.0 g, 1.487 mmol) in DMF (5 mL) was added I-4-tert-butoxy-4-oxo-but-2-enoic acid (300 mg, 1.710 mmol), N,N-Diisopropylethylamine (0.8 mL, 4.461 mmol), 1-(3-dimethylaminopropyl)-3-ethyl carbodiimide (353 mg, 2.230 mmol), 1-Hydroxybenzotriazole (307.5 mg, 2.230 mmol) at room temperature. The resulting reaction mixture was stirred at room temperature for 16 h. The progress of the reaction was monitored by TLC and LCMS. The reaction mixture was quenched with ice cold water (20 mL) to obtain a solid which was filtered and triturated with Diethyl ether and heptane to afford compound (3) (1.0 g, 89.9%) as a brown coloured solid.

LC-MS (Method-E)=706.4 $[M+H]^+$; 94.37% at RT 1.69 min.

Step-2: Synthesis of rac-I-4-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)methyl)amino)-4-oxobut-2-enoic acid (4)

To a stirred solution of rac-tert-butyl I-4-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)methyl)amino)-4-oxobut-2-enoate (3.0 g, 4.01 mmol) in DCM (15 mL) was added TFA (5 mL) at room temperature. The resulting reaction mixture was stirred at room temperature for 3 h. The progress of the reaction was monitored by TLC. After consumption of the starting material, the reaction mixture was diluted with DCM (250 mL) and washed with water (3×100 mL). The combined organic layer was dried over $Na_2SO_4$ and concentrated under reduced pressure to get crude solid. The obtained solid was triturated with n-heptane to afford the compound (4) (2.30 g, 88.3%) as a brown coloured solid.

$^1$H NMR (400 MHZ, DMSO-d6) δ=12.70 (br s, 1H), 8.74 (t, J=5.6 Hz, 1H), 8.52-8.47 (m, 1H), 8.18-8.12 (m, 2H), 7.92 (d, J=7.9 Hz, 1H), 7.74-7.65 (m, 3H), 7.63-7.53 (m, 3H), 6.99 (t, J=8.7 Hz, 2H), 6.90-6.84 (m, 2H), 6.43 (d, J=15.8 Hz, 1H), 6.26-6.20 (m, 1H), 5.50 (t, J=7.3 Hz, 1H), 4.54 (d, J=7.0 Hz, 1H), 4.47 (dd, J=6.6, 15.3 Hz, 1H), 4.15 (dd, J=5.0, 15.3 Hz, 1H), 3.97-3.85 (m, 1H), 3.02 (dd, J=6.6, 14.1 Hz, 1H), 0.90 (t, J=7.0 Hz, 3H). LC-MS (Method-H)=650.44 $[M+H]^+$; 93.16% at RT 2.16 min.

Step-3: Synthesis of rac-N1-(2-(dimethylamino) ethyl)-N4-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl) methyl)fumaramide (I-154)

To a stirred solution of rac-I-4-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)methyl)amino)-4-oxobut-2-enoic acid (4) (250 mg, 0.384 mmol) in DMF (2 mL) was added N',N'-dimethylethane-1,2-diamine (43.27 mg, 0.481 mmol), N,N-Diisopropylethylamine (0.2 mL, 1.155 mmol), HATU (226.3 mg, 0.577 mmol) at room temperature. The resulting reaction mixture was stirred at room temperature for 16 h. The progress of the reaction was monitored by TLC and LCMS. After consumption of the starting material, the reaction mixture was quenched with ice cold water (20 mL) and extracted with ethyl acetate (3x30 mL), washed with brine and dried over $Na_2SO_4$ to get crude compound. The crude purified by Prep HPLC to afford the title compound I-154 (53 mg, 19.14%) as an Off-white solid.

$^1H$ NMR (400 MHZ, DMSO-$d_6$) δ=9.33 (s, 1H), 8.59 (d, J=7.2 Hz, 1H), 8.19-8.13 (m, 2H), 7.93 (d, J=7.8 Hz, 1H), 7.80 (dd, J=1.9, 7.6 Hz, 2H), 7.72 (t, J=7.8 Hz, 1H), 7.65-7.61 (m, 3H), 7.13-7.07 (m, 2H), 7.05-7.00 (m, 2H), 5.52 (t, J=7.2 Hz, 1H), 4.95 (d, J=7.2 Hz, 1H), 3.93-3.83 (m, 1H), 3.02-2.94 (m, 1H), 1.47-1.41 (m, 2H), 1.29-1.23 (m, 1H), 1.22-1.16 (m, 1H), 0.89 (t, J=7.0 Hz, 3H). LC-MS (Method-I)=720.2 $[M+H]^+$; 98.60% at RT 4.86 min. HPLC (Method-N)=99.49% at RT 4.34 min. Chiral HPLC (Method-Z-1)=Peak-1=49.44% at RT 18.88 min. Peak-2=50.55% at RT 22.66 min.

Step-1: Synthesis of rac-N1-(((4R,5R)-7-ethyl-4-(4-fluorophenyl)-6-oxo-1-phenyl-5-(3-(trifluoromethyl) benzamido)-4,5,6,7-tetrahydro-1H-pyrazolo[3,4-b] pyridine-3-yl)methyl)-N4-(2-hydroxyethyl) fumaramide (I-15)

To a stirred solution of rac-I-4-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)methyl)amino)-4-oxobut-2-enoic acid (1) (200 mg, 0.286 mmol) in DCM (5 mL) were added Triethylamine (0.12 mL, 0.859 mmol) and ethyl chloroformate (0.033 mL, 0.343 mmol) followed by 2-aminoethanol (0.022 mL, 0.343 mmol) at 0° C. The resulting reaction mixture was stirred at room temperature for 16 h. The progress of the reaction was monitored by TLC and LCMS. The reaction mixture was diluted with DCM (100 mL), quenched with water (20 mL) and organic layer washed with brine (20 mL). The combined organic layer was dried $Na_2SO_4$ and concentrated under reduced pressure to get crude. The crude was purified by Prep HPLC followed by lyophilization to afford the title compound I-15 (94 mg, 46.92%) as an off-white solid.

$^1H$ NMR (400 MHZ, DMSO-$d_6$) δ=8.64 (dd, J=5.6, 6.4 Hz, 1H), 8.48 (d, J=7.4 Hz, 1H), 8.30 (t, J=5.8 Hz, 1H), 8.16-8.12 (m, 2H), 7.92 (d, J=7.8 Hz, 1H), 7.73-7.66 (m, 3H), 7.61-7.53 (m, 3H), 7.02-6.97 (m, 2H), 6.90-6.85 (m, 2H), 6.64 (d, J=15.1 Hz, 1H), 6.41 (d, J=15.1 Hz, 1H), 5.50 (t, J=7.3 Hz, 1H), 4.68 (t, J=5.4 Hz, 1H), 4.57-4.54 (m, 1H), 4.46-4.40 (m, 1H), 4.17-4.11 (m, 1H), 3.95-3.86 (m, 1H), 3.44-3.39 (m, 2H), 3.22-3.15 (m, 2H), 3.03 (d, J=7.0, 14.1 Hz, 1H), 0.90 (t, J=7.1 Hz, 3H). LC-MS (Method-I)=693.2 $[M+H]^+$; 99.44% at RT 5.24 min. HPLC (Method-N)=98.60% at RT 5.06 min. Chiral HPLC (Method-X)=Peak-1=49.65% at RT 6.14 min. Peak-2=50.34% at RT 6.60 min.

Synthesis of I-15

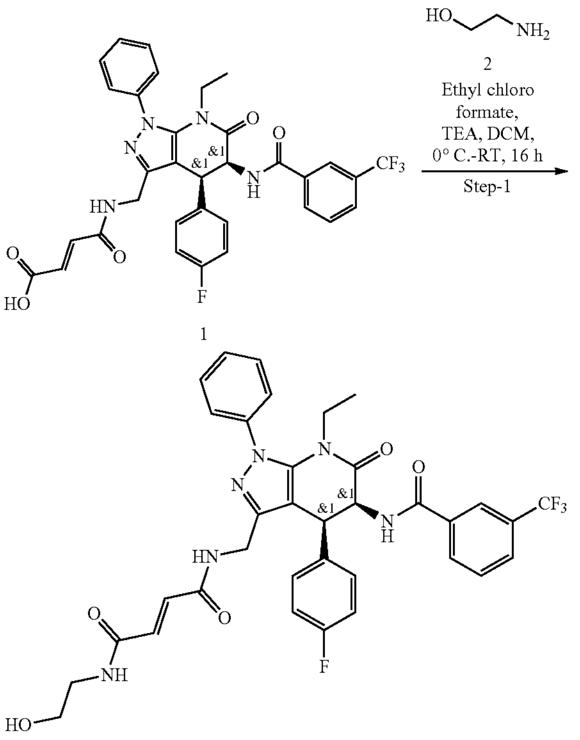

1

I-15

Synthesis of I-5

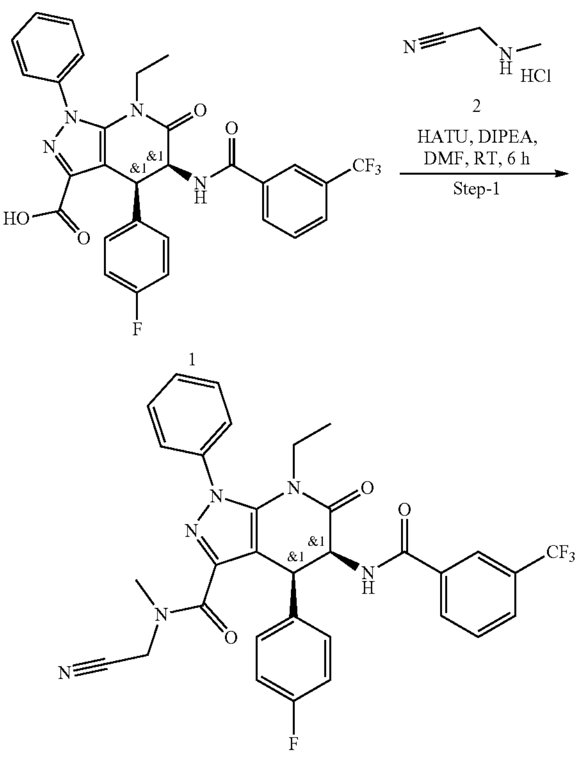

1

I-5

Step-1: Synthesis of rac-(4R,5R)—N-(cyanomethyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamide (I-5)

To a stirred solution of rac-(4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxylic acid (200 mg, 0.335 mmol) (Mixture of RR & SS isomer) in DMF (10 mL) was added HATU (263 mg, 0.670 mmol), methylamino acetonitrile hydrochloride (72.93 mg, 0.670 mmol) and N,N-Diisopropylethylamine (0.23 mL, 1.342 mmol) at 0° C. The reaction mixture stirred at room temperature for 6 h. The reaction mixture was monitored by TLC. After completion of reaction, the reaction mixture was diluted with water (50 mL) and extracted with EtOAc (3×30 mL), the combined organic layers were dried over sodium sulphate and concentrated under reduced pressure to get crude reaction mixture as yellow gummy compound. The crude was purified by FCC using 30-40% EtOAc: Heptane to afford the title compound I-5 (120 mg, 56.10%) (Mixture of RR & SS isomer) as a white solid.

$^1$H NMR (400 MHZ, DMSO-$d_6$) δ=8.55 (d, J=7.1 Hz, 1H), 8.19-8.12 (m, 2H), 7.92 (d, J=7.8 Hz, 1H), 7.81 (br s, 2H), 7.74-7.57 (m, 4H), 7.11-7.04 (m, 2H), 7.01-6.94 (m, 2H), 5.54 (t, J=7.2 Hz, 1H), 5.16-4.85 (m, 2H), 4.54-4.43 (m, 1H), 3.95-3.84 (m, 1H), 3.44-3.36 (m, 2H), 3.04 (dd, J=7.1, 14.4 Hz, 1H), 2.98 (br s, 1H), 0.91 (t, J=6.9 Hz, 3H). LC-MS (Method-I)=629.2 $[M-H]^+$; 97.57% at RT 6.17 min. HPLC (Method-N)=98.70% at RT 6.08 min. Chiral HPLC (Method-Y)=Peak-1=49.97% at RT 6.97 min. Peak-2=50.02% at RT 7.95 min.

NMR:

$^1$H NMR spectrum was recorded on Bruker 400 MHz and Varian 400 MHZ instruments internally referenced to a tetramethyl silane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ; Mobile Phase: A: 0.05% Formic acid in water: I (95:5); B: 0.05% Formic acid in I; Inj Volume: 2.0 μL, Column oven temperature: 50° C.; Flow Rate: 1.2. mL/minute Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C.; Gradient program: 0% B to 98% B in 2.0 minute, hold till 3.0 min, at 3.2 min B conc is 0% up to 4.0 min.

Method-C: Column: X-Select CSH C18, (50 mm*3.0 mm,2.5μ) Mobile Phase A: 0.05% TFA in Water; Mobile Phase B: 0.05% TFA in Acetonitrile; Flow rate: 1.0 mL/min. Column temperature: 40° C. Gradient Program (B %): 0.0/2, 0.3/2,2.0/98, 2.8/98, 3.0/2,3.7/2.

HPLC:

Method-A: Column: X Select CSH C18 (150×4.6) mm,3.5μ; Mobile phase A: 0.1% FA in water: I (95:05); Mobile phase B: Acetonitrile; Gradient Programme: T/B %: 0.01/5, 1/5,8/100,12/100, 14/5, 18/5; Flow rate: 1.2 ml/min.

Method-B: Column: X-SELECT CSH C18 (150×4.6 mm, 3.5 μm); Mobile Phase-A: 5 mM $NH_4HCO_3$; Mobile Phase-B: I; Programme: T/B %: 0.01/2,2/2, 12/90,16/90; Flow: 1.0 mL/min.; Diluent: I: WATER (80:20).

Method-C: Column: X SELECT CSH C18 (150×4.6 mm, 3.5μ); Mobile Phase A; 0.05% TFA in water: I (95:05); Mobile Phase B: 0.05% TFA in water: I (05:95); Programme: T/B %: . 0.01/10,12/90, 16/90; Flow: 1 mL/min.; Diluent: WATER: I (80:20).

Method-D: Column: X-Select CSH C18 (4.6*150) mm 5μ Mobile Phase: A-0.1% TFA in water; B-Acetonitrile Inj Volume; 5.0 μL, Flow Rate: 1.2. mL/minute Gradient program: Time (min)/B Conc.: 0.01/5, 1.0/5, 8.0/100, 12.0/100, 14.0/5, 18.0/5.

Method-E: Column name: CHIRAL PAK-IA (250*4.6,5 μm) mobile phase A: n-hexane; mobile phase B: DCM: MeOH (50:50 program-AB 90:10 flow rate: 1.0 ml/min.

Method-F: COLUMN: CHIRAL PAK-IG (250*4.6 mm, 5 μm) Mobile phase A: 0.1% DEA in n-Hexane; Mobile phase B: DCM: MeOH (50:50) A: B; 80:20 Flow: 1.0 ml/min.

Synthesis of Compound 14-1

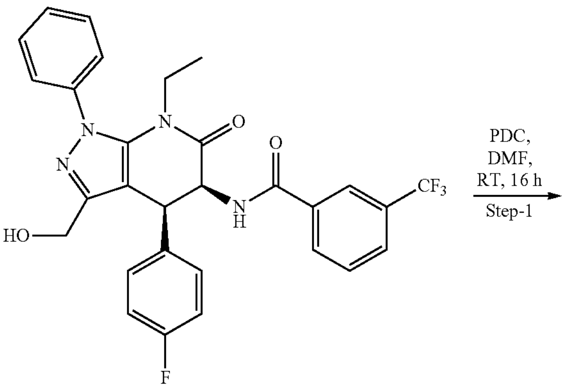

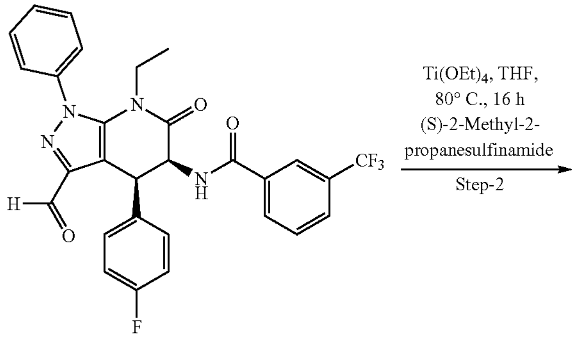

1

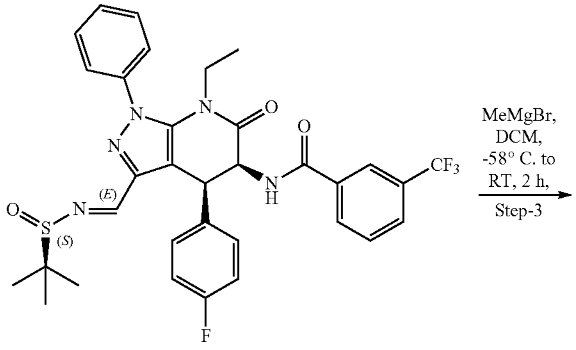

2

-continued

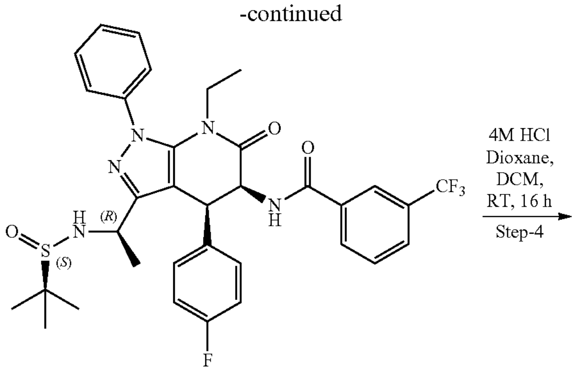

3

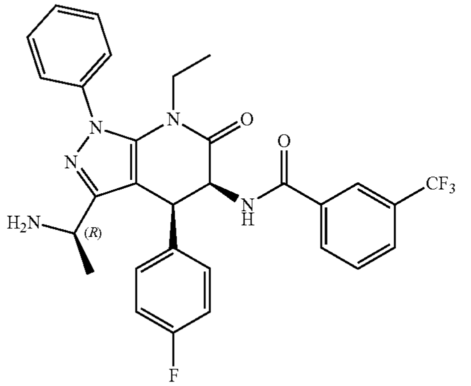

14-1

Step-1: Synthesis of N-((4S,5S)-7-ethyl-4-(4-fluorophenyl)-3-formyl-6-oxo-1-phenyl-4,5,6,7-tetrahydro-1H-pyrazolo[3,4-b]pyridine-5-yl)-3-(trifluoromethyl)benzamide (1)

To a stirred solution of N-((4S,5S)-7-ethyl-4-(4-fluorophenyl)-3-(hydroxymethyl)-6-oxo-1-phenyl-4,5,6,7-tetrahydro-1H-pyrazolo[3,4-b]pyridine-5-yl)-3-(trifluoromethyl)benzamide (2.0 g, 3.5 mmol) in DMF (20.0 mL), pyridinium dichromate (1.6 g, 4.2 mmol) was added. The reaction mixture was stirred at 25° C. for 16 h. After consumption of the starting material (by TLC), the reaction mixture was quenched with ice cold water (50 mL) and extracted with diethyl ether (3×40 mL). The organic layer was dried over anhydrous $Na_2SO_4$ and concentrated under reduced pressure. The crude material was purified by medium pressure liquid chromatography by eluting 7-15% EtOAc/heptane to afford compound (1) (1.5 g, 77%) as an off-white semi solid. LC-MS (Method-B)=551.4 $[M+H]^+$; 98.61% at RT 2.05 min.

Step-2: Synthesis of N-((4S,5S)-3-(I—(((S)-tert-butylsulfinyl)imino)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (2)

To a stirred solution of compound (1) (6.0 g, 11 mmol) in THF (60 mL) was added(s)-2-methylpropane-2-sulfinamide (2.6 g, 21 mmol) and titanium (IV) ethoxide (5.2 g, 22 mmol) at 0° C. The reaction mixture was stirred at 80° C. for 16 h. Progress of the reaction was monitored by TLC. After consumption of the reaction, the reaction mixture was poured into ice cold $NH_4Cl$ solution (150 mL) and extracted with EtOAc (2×150 mL). The organic layer was dried over anhydrous $Na_2SO_4$, concentrated under reduced pressure. The crude material was washed with diethyl ether filtered and dried to afford compound (2) (6.5 g, 85%) as an off-white solid. LC-MS (Method-B)=654.2 $[M+H]^+$; 93.00% at RT 2.50 min.

Step-3: Synthesis of N-((4S,5S)-3-((R)-1-aminoethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (3)

To a stirred solution of compound (2) (6.5 g, 9.9 mmol) in DCM (130 mL), $CH_3MgBr$ (3.0 M) in diethyl ether (34 g, 99 mmol) was added slowly at −58° C. Reaction mixture was allowed to stir at room temperature for 2 h. After consumption of the starting material (by TLC), the reaction was poured into ice cold $NH_4Cl$ solution (25 mL) and extracted with DCM (2×25 mL). The organic layer was dried over anhydrous $Na_2SO_4$ and concentrated under reduced pressure. The obtained crude material was washed with diethyl ether to afford compound (3). LC-MS (Method-B)=669.9 $[M+H]^+$; 49.86% at RT 2.49 min.

Step-4: Synthesis of N-((4S,5S)-3-((R)-1-aminoethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide hydrochloride (14-1)

To a stirred solution of compound (3) (5.4 g, 8.1 mmol) in dichloromethane (54 mL) was added 4M HCl in Dioxane (20 mL) at room temperature under inert atmosphere. The reaction mixture was stirred at 25° C. for 16 h. After consumption of the starting material (by TLC), the reaction mixture was concentrated under reduced pressure. Obtained residue was triturated with diethyl ether to afford 14-1 (4.20 g, 89%) as an off-white solid. LC-MS (Method-B)=566.2 $[M+H]^+$; 84.87% at RT 2.41 min.

Synthesis of 14-2

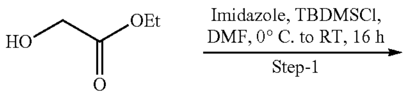

SM-1

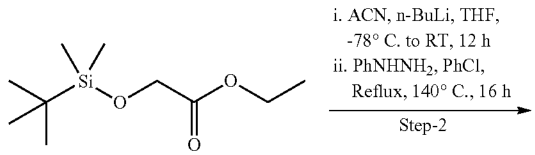

1

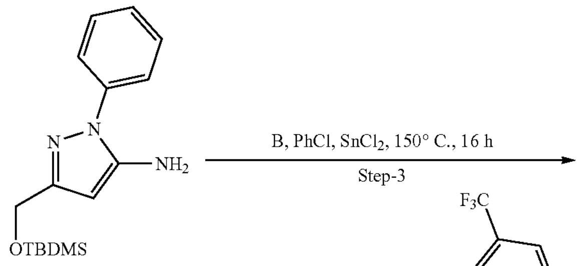

2B

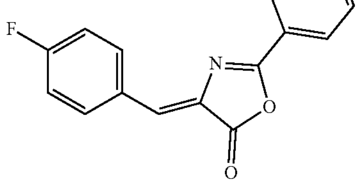

B

-continued

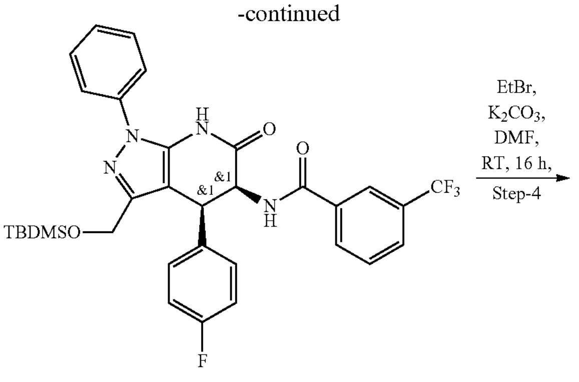

3

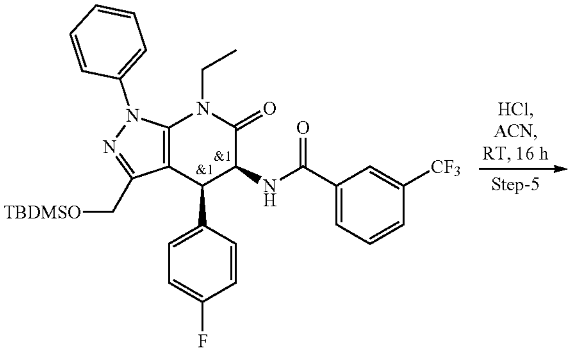

4

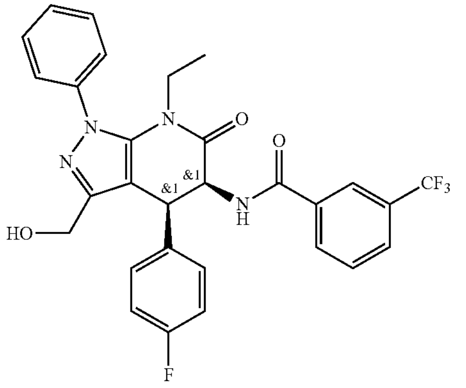

14-2

Step-1: Synthesis of ethyl 2-((tert-butyldimethylsilyl)oxy)acetate (1)

To stirred solution of compound (SM-1) (25 g, 240.1 mmol) in DMF (125 mL) was added imidazole (27.6 g, 312.2 mmol) and TBDMSCl (47.04 g, 312.2 mmol) at 0° C. The reaction mixture was stirred at room temperature for 16 h. After consumption of the starting material (by TLC), the reaction mixture was quenched with water (1000 mL) and extracted with EtOAc (2×1000 mL). The organic layer was dried over anhydrous sodium sulfate and concentrated to afford crude compound. The obtained crude compound was purified by using column chromatography. Pure fraction was collected and concentrated under vacuum to afford compound (1) (24 g, 46.1%) as colorless liquid.

Step-(2A): Synthesis of 3-(((tert-butyldimethylsilyl) oxy)methyl)-1-phenyl-1H-pyrazol-5-amine (2A)

To a stirred solution of acetonitrile (15 mL) in tetrahydrofuran (750 mL), butyl lithium (2.5 mol/l) in hexanes (115 ml, 290 mmol) were added at −78° C. The reaction mixture was stirred at −78° C. for 16 min. Compound (1) (40 g, 183.18 mmol) dissolved in tetrahydrofuran (750 mL) was added to the reaction mixture slowly at the same temperature. The reaction mixture was allowed to reach the room temperature and maintained at the same temperature for 12 h. Reaction progress was monitored by TLC. After completion of the reaction, the reaction mixture was quenched with water (2000 mL) and the pH was adjusted to 4-5 using 2N aq. HCl solution. The reaction mixture was diluted with ethyl acetate (2×2000 mL), then separated the organic and aqueous layers. Organic layer was dried over anhydrous sodium sulfate and concentrated under reduced pressure to afford crude compound (2A) (37 g, 94.67%) as a pale-yellow.

Step-(2B): Synthesis of 5-[[tert-butyl(dimethyl)silyl]oxymethyl]-2-phenyl-pyrazol-3-amine (2B)

To a stirred solution of compound (2A) (37 g, 173.42 mmol) in chlorobenzene (110 mL), phenylhydrazine (19 g, 173.94 mmol) was added at room temperature. The reaction mass temperature was raised to 140° C. The reaction mixture was stirred at same temperature for 16 h. Reaction progress was monitored by TLC. After completion of starting material, the reaction mixture was quenched with water (1 L) and extracted with ethyl acetate (2×2 L). Organic layer was dried over anhydrous sodium sulfate, concentrated under reduced pressure to afford crude compound. The obtained crude compound was purified by column chromatography, eluted with 15-20% ethyl acetate in pet ether to afford compound (2B) (26.0 g, 35.07%) as a yellow solid.

Step-3: Synthesis of rac-N-((4R,5R)-3-(((tert-butyldimethylsilyl)oxy)methyl)-4-(4-fluorophenyl)-6-oxo-1-phenyl-4,5,6,7-tetrahydro-1H-pyrazolo[3,4-b]pyridine-5-yl)-3-(trifluoromethyl)benzamide (3)

To a stirred solution compound (2B) (26 g, 85.67 mmol) and Int-B (29.19 g, 85.67 mmol) in chlorobenzene (78 ml), tin(II) chloride (1.64 g, 8.56 mmol) was added at room temperature. The reaction mixture was stirred at 140-150° C. for 16 h. Reaction progress was monitored by TLC. After completion of reaction, the reaction mixture was quenched with water and filtered through celite bed and washed with DCM. Filtrate was washed with water (2 L) and extracted with DCM (2×2 L) Organic layer was dried over anhydrous sodium sulfate and concentrated under reduced pressure. The obtained crude was purified by column chromatography by eluting with 20-30% ethyl acetate in pet ether to afford compound (3) (30 g, 48.6%) as yellow solid. LC-MS (Method-A)=639.29 $[M+H]^+$; 88.73% at RT 2.48 min.

Step-4: Synthesis of rac-N-((4R,5R)-3-(((tert-butyldimethylsilyl)oxy)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl) benzamide (4)

To a stirred solution of compound (3) (30 g, 41.33 mmol) in DMF (300 mL), potassium carbonate (7.50 g, 53.73 mmol) and bromoethane (5.45 g, 49.60 mmol) were added at room temperature. The reaction mixture was stirred at room temperature for 16 h. Reaction progress was monitored by TLC. After completion of reaction, the reaction mixture was quenched with water (2 L) and extracted with ethyl acetate (2×2 L). Organic layer was dried over anhydrous sodium sulfate and evaporated under vacuum. The obtained crude was purified by column chromatography by eluting with 15-20% ethyl acetate in heptane to afford compound (4) (33 g, 99.38%) as yellow solid. LC-MS (Method-B)=667.5 $[M+H]^+$; 83.38% at RT 2.52 min.

Step-5: Synthesis of rac-N-((4R,5R)-7-ethyl-4-(4-fluorophenyl)-3-(hydroxymethyl)-6-oxo-1-phenyl-4,5,6,7-tetrahydro-1H-pyrazolo[3,4-b]pyridine-5-yl)-3-(trifluoromethyl)benzamide (14-2)

To a stirred solution of compound (4) (20 g, 24.90 mmol) in acetonitrile (100 mL), hydrochloric acid (20 mL, 120 mmol) was added. The reaction mixture was stirred at room temperature for 16 h. Reaction progress was monitored by TLC. After completion of reaction, the reaction mixture was quenched with ice water (1.5 L) and extracted with ethyl acetate (2×1.5 L). Organic layer was dried over anhydrous sodium sulfate and concentrated under vacuum to afford crude compound. The crude material was washed with 10% diethyl ether in pentane and dried under vacuum to afford 14-2 (12.00 g, 83.75%) as a pale-yellow solid. LC-MS (Method-B)=553.2 [M+H]$^+$; 96.44% at RT 2.26 min. HPLC (Method-B): 95.87% at RT 9.15 min.

Synthesis of 14-3

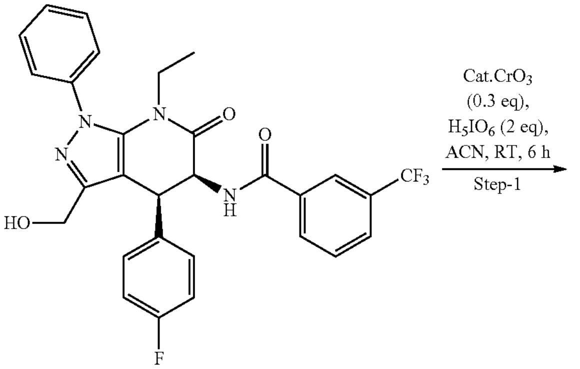

14-2

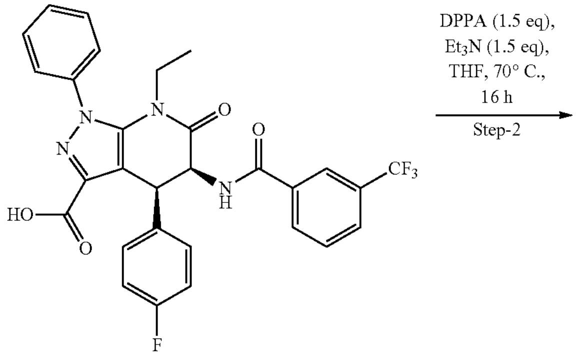

1

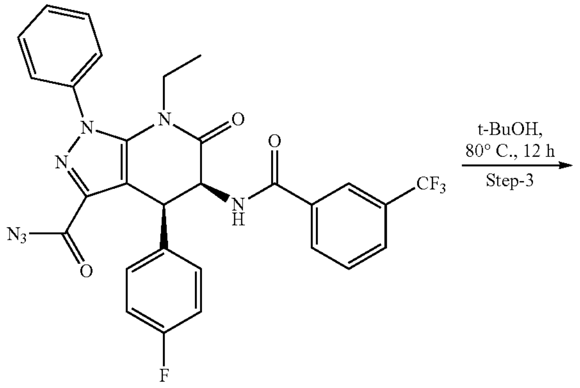

2

-continued

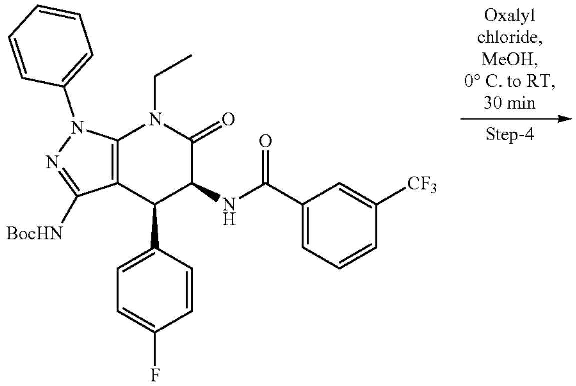

3

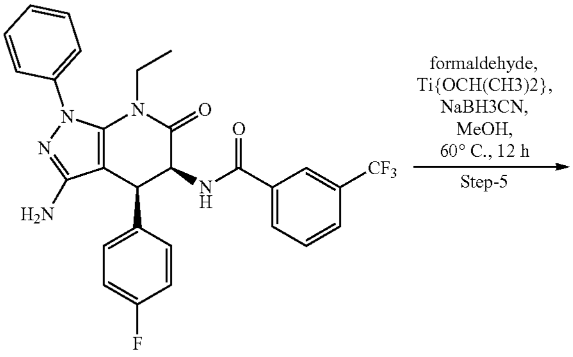

14-3a

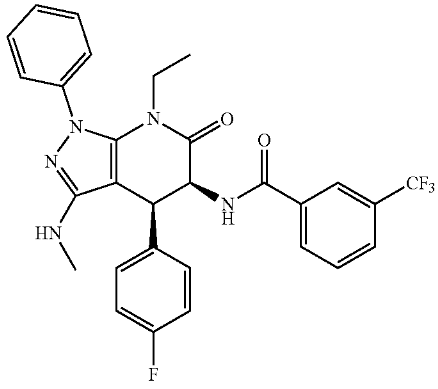

14-3

Step-1: Synthesis of 7-ethyl-4-(4-fluorophenyl)-6-oxo-1-phenyl-5-[[3-(trifluoromethyl)benzoyl]amino]-4,5-dihydropyrazolo[3,4-b]pyridine-3-carboxylic acid (1)

To a stirred solution of 14-2 (5 g, 8.68 mmol) in I (50 mL), periodic acid (4.04 g, 17.38 mmol) and Chromium(III) oxide (0.39 g, 2.606 mmol) was added at 0° C. The reaction mixture was stirred at room temperature for 12 h. Reaction progress was monitored by TLC. After completion of reaction, the reaction mixture was diluted with 10% methanol in DCM and filtered by celite bed. Filtrate was concentrated under vacuum and washed with diethyl ether. The compound was dried under vacuum to afford compound (1) (3.5 g, 69%) as off-white solid. LC-MS (Method-A)=567.31 [M+H]$^+$; 96.91% at RT 2.24 min.

Step-2: Synthesis of (4~{S},5~{S})-7-ethyl-4-(4-fluorophenyl)-6-oxo-1-phenyl-5-[[3-(trifluoromethyl)benzoyl]amino]-4,5-dihydropyrazolo[3,4-b]pyridine-3-carbonyl azide (2)

To a stirred solution of compound (1) (3.5 g, 6.0 mmol) in tetrahydrofuran (30 mL) was added diphenylphosphoryl azide (DPPA) (4.2 g, 15 mmol) and triethylamine (1.8 g, 18 mmol) at 0° C. The reaction was refluxed and stirred at 70° C. for 16 h. The reaction progress was monitored by TLC and LCMS. The reaction mixture was quenched with water (250 mL) extracted by ethyl acetate (2×250 mL) and dried over anhydrous sodium sulphate and concentrated to afford crude compound, which was purified by combi flash to afford compound (2) (2.8 g, 76%) as pale-yellow solid. LC-MS (Method-A)=592.2 $[M+H]^+$; 95.68% at RT 2.29 min.

Step-3: Synthesis of tert-butyl ((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)carbamate (3)

To the stirred solution of Compound (2) (2.8 g, 4.5 mmol) in tertiary butanol (25 mL) was stirred at 80° C. for 12 h. Reaction progress was monitored by TLC. After completion of reaction, the reaction mixture was concentrated under vacuum, washed with pentane to afford compound (3) (2.7 g, 75%) as pale-yellow solid. LC-MS (Method-A)=638.5 $[M+H]^+$; 82.54% at RT 2.30 min.

Step-4: Synthesis of N-((4S,5S)-3-amino-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (14-3a)

To a stirred solution of compound (3) (5 g, 6.43 mmol) in methanol (100 mL), oxalyl chloride (4.16 g, 32.15 mmol) was added at 0° C. The reaction was stirred at room temperature for 30 min. Reaction progress was monitored by TLC. After completion of reaction, the reaction mixture was concentrated under vacuum to afford crude compound. Obtained crude was washed with 50% diethyl ether in pentane and filtered under vacuum to afford 14-3a (3 g, 72.91%) as pale green solid.

Step-5: Synthesis of N-((4S,5S)-7-ethyl-4-(4-fluorophenyl)-3-(methylamino)-6-oxo-1-phenyl-4,5,6,7-tetrahydro-1H-pyrazolo[3,4-b]pyridine-5-yl)-3-(trifluoromethyl)benzamide (14-3)

To a stirred solution of 14-3a (250 mg, 0.39 mmol) in methanol (12 mL), formaldehyde (0.012 g, 0.39 mmol) and titanium (iv) isopropoxide (0.11 g, 0.39 mmol) was added. Then sodium cyanoborohydride (0.02 g, 0.39 mmol) was added to reaction mixture at room temperature. The reaction mixture was stirred at 60° C. for 12 hrs. Reaction progress was monitored by TLC. After completion of reaction, the reaction mixture was filtered through celite pad. Filtrate was concentrated under vacuum and purified by Prep HPLC to afford 14-3 (30 mg, 13.92%) as off-white solid. LC-MS (Method-A)=552.2 $[M+H]^+$; 99.743% at RT 2.55 min.

Prep HPLC method: Preparative Column X-SELECT (250*30 mm), 5 μm Mobile Phase A 10 m M ABC in Water; Mobile Phase B CAN; Flow rate 25 mL; Instrument ID PREP-17 Gradient (Time/% B) 0.01/10,3/10,10/,45,15/60, 20/65,25/70,30/75, 35/80,40/98. HPLC (Method-B): 99.12% at RT 9.66 min.

Synthesis of 14-4

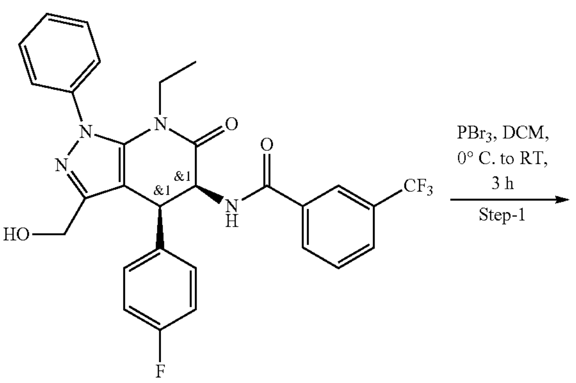

5

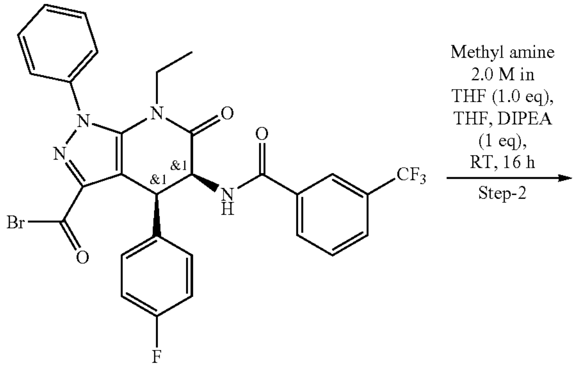

14-4a

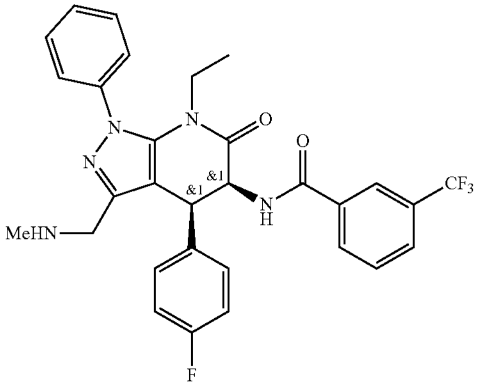

14-4

Step-1: Synthesis of rac-N-((4R,5R)-3-(bromomethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (14-4a)

To a stirred solution of compound (5) (2.0 g, 3.62 mmol) in DCM (10 mL) was added $PBr_3$ (0.58 mL, 5.4 mmol) at 0° C. The reaction mixture was stirred at room temperature for 3 h. Progress of the reaction was monitored by TLC. After consumption of reaction, the reaction mixture was diluted with water (200 mL) and extracted with DCM (2×250 mL). Organic layer was dried over sodium sulfate, concentrated under vacuum to afford crude. Obtained crude was purified by medium pressure liquid chromatography was eluted with 30-40% ethyl acetate/pentane to afford compound (14-4a) (1.55 g, 54%) as an off-white solid. LC-MS (Method-B)= 614.7 $[M+H]^+$; 95.53% at RT 2.80 min.

Step-2: Synthesis of rac-N-((4R,5R)-7-ethyl-4-(4-fluorophenyl)-3-((methylamino)methyl)-6-oxo-1-phenyl-4,5,6,7-tetrahydro-1H-pyrazolo[3,4-b]pyridine-5-yl)-3-(trifluoromethyl)benzamide (14-4)

To a stirred solution of compound (14-4a) (1.5 g, 2.4 mmol) was added DIPEA (0.41 mL, 2.4 mmol) followed by addition of methyl amine (2.0 M) in THF at room temperature. The reaction mixture was stirred at room temperature for 16 h. Progress of the reaction was monitored by TLC. After consumption of reaction, the reaction mixture was concentrated under vacuum to afford crude. Obtained crude was purified by medium pressure liquid chromatography and the desired compound was eluted with 5-10% MeOH/DCM to afford compound (14-4) (750 mg, 57.4%) as an off-white solid. LC-MS (Method-B)=564.4 $[M-H]^-$; 90.98% at RT 2.20 min. HPLC (Method-C): Peak-1=49.86% at RT 8.97 min. HPLC (Method-C): Peak-2=50.14% at RT 10.47 min.

Synthesis of 14-5

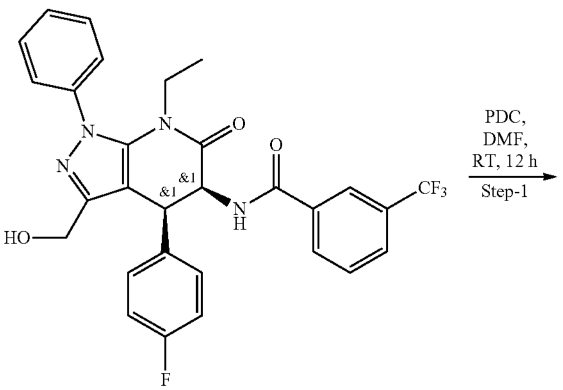

5

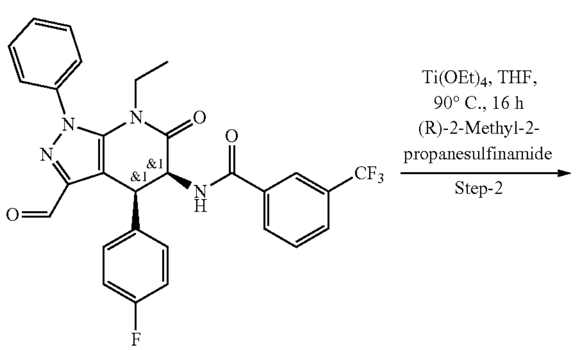

6

-continued

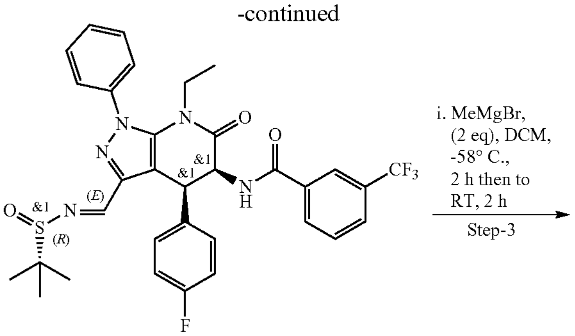

7

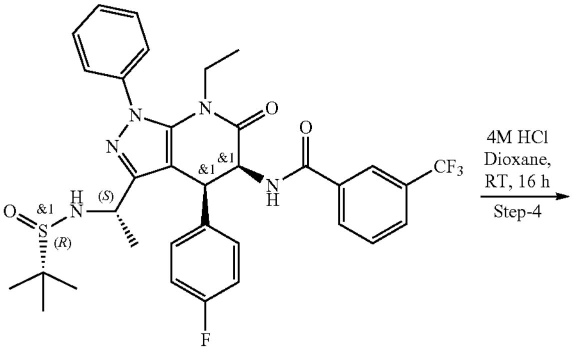

8

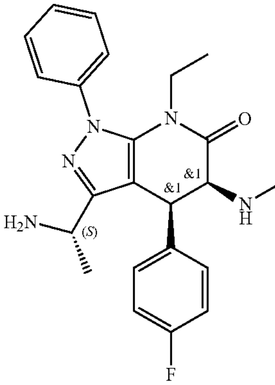

14-5

Step-1: Synthesis of rac-N-((4R,5R)-7-ethyl-4-(4-fluorophenyl)-3-formyl-6-oxo-1-phenyl-4,5,6,7-tetrahydro-1H-pyrazolo[3,4-b]pyridine-5-yl)-3-(trifluoromethyl)benzamide (6)

To a stirred solution of compound (5) (6 g, 9.991 mmol) in DMF (30 ml), pyridinium dichromate (6.25 g, 16.3 mmol) was added at room temperature. Then the reaction mixture was stirred at room temperature for 12 h. Reaction progress was monitored by TLC. After completion of reaction, the reaction mixture was quenched with water (250 mL) and extracted with ethyl acetate (2×300 mL). The reaction mixture was filtered through celite bed. Organic layer was dried over anhydrous sodium sulfate and concentrated to afford crude material. Obtained crude material was purified by flash column chromatography. Combined pure fractions were concentrated under vacuum and washed with ether to afford compound (6) (4 g, 72.0%) as a pale brown solid. LC-MS (Method-B)=551.31 $[M+H]^+$; 99.25% at RT 2.23 min.

Step-2: Synthesis of N-((4RS,5RS)-3-((E)-(((R)-tert-butylsulfinyl)imino)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl) benzamide (7)

To a stirred solution of compound (6) (7 g, 12.72 mmol) in tetrahydrofuran (70 mL) was added titanium (IV) ethoxide (6.82 g, 25.43 mmol) followed by $(R)_2$-methylpropane-2-sulfinamide (3.08 g, 25.43 mmol) at room temperature. The reaction mixture was heated to 90° C. for 16 h. Progress of the reaction was monitored by TLC. After consumption of the reaction, the reaction mixture was allowed to cool to room temperature, quenched with water (250 mL), and extracted with ethyl acetate (2×300 mL). Combined organic layers were dried over anhydrous sodium sulfate and concentrated under reduced pressure to afford crude compound (7) (6.40 g, 76.99%) and it was directly used for next step without any further purification.

Step-3: Synthesis of N-[(4S,5S)-3-[1-(tert-butylsulfinylamino)ethyl]-7-ethyl-4-(4-fluorophenyl)-6-oxo-1-phenyl-4,5-dihydropyrazolo[3,4-b]pyridine-5-yl]-3-(trifluoromethyl)benzamide (8)

To a stirred solution of compound (7) (7 g, 10.71 mmol) in dichloromethane (9.09 g, 107.1 mmol) was added methyl magnesium bromide solution (3.0 mol/l) in diethyl ether (37 g, 107.1 mmol) at −58° C. Then the reaction mixture was allowed to room temperature. The reaction was stirred at room temperature for 2 h. After consumption of the starting material (by TLC), the reaction was poured into ice cold $NH_4Cl$ solution (125 mL) and extracted with DCM (2×300 mL). The organic layer was dried over anhydrous $Na_2SO_4$, concentrated under reduced pressure. The crude material was washed with diethyl ether to afford compound-8 (7 g, 47.83%) as an off-white solid. LC-MS (Method-B)=670.0 $[M+H]^+$; 83.92% at RT 2.36 min. HPLC (Method-B): 81.80% at RT 10.01 min.

Step-4: Synthesis of N-((4RS,5RS)-3-((S)-1-aminoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (14-5)

To a stirred solution of compound (8) (7.0 g, 10 mmol) in dichloromethane (8.9 g, 100 mmol) was added hydrochloric acid (2 mol/l) in diethyl ether (52 mL, 100 mmol) at 0° C. Then the reaction mixture was allowed to reach room temperature. Reaction mixture was stirred at room temperature for 16 h. The organic layer was concentrated under reduced pressure. The crude material was washed with heptane to afford 14-5 (6 g, 93%) as an off-white solid. LC-MS (Method-A)=566.9 $[M+H]^+$; 76.39% at RT 2.04 min. HPLC (Method-F)=38.67% at RT 8.74 min.

Synthesis of 14-6

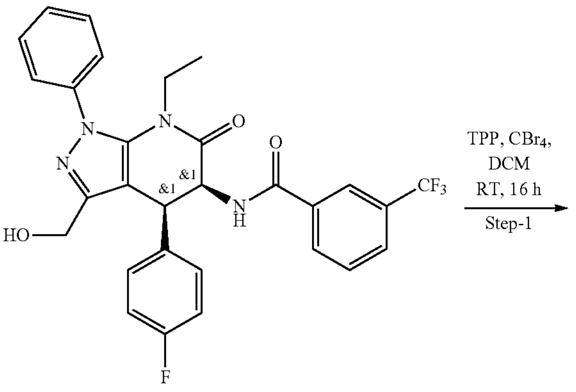

5

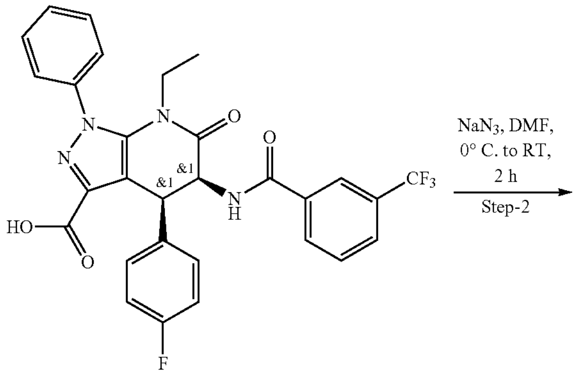

6

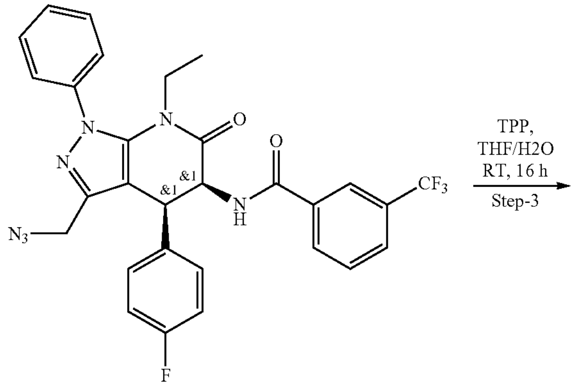

7

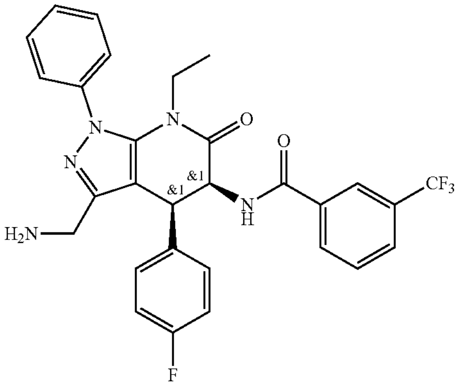

14-6

Step-1: Synthesis of rac-N-((4R,5R)-3-(bromomethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (6)

To a stirred solution of compound (5) (8.5 g, 15.42 mmol) in DCM (20 mL) was added TPP (6.8 g, 26.22 mmol) followed by $CBr_4$ (8.7 g, 26.22 mmol) at room temperature. The reaction mixture was stirred at room temperature for 16 h. After consumption of starting material (by TLC), the reaction mixture was diluted with water (500 mL) and extracted with DCM (2×300 mL). The organic layer was dried over anhydrous $Na_2SO_4$, concentrated under reduced pressure. The obtained crude material was purified by medium pressure liquid column chromatography by eluting with 20% EtOAc in heptane to afford compound (6) (6.0 g, 63.8%) as an off-white solid. LC-MS (Method-A)=615.39 $[M+H]^+$; 91.95% at RT 1.76 min. HPLC (Method-E): Peak-1=51.54% at RT 8.76 min. HPLC (Method-E): Peak-2=48.46% at RT 11.91 min.

Step-2: Synthesis of rac-N-((4R,5R)-3-(azidomethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (7)

To a stirred solution of compound (6) (6.0 g, 9.75 mmol) in DMF (10 mL), was added $NaN_3$ (0.95 g, 14.6 mmol) at 0° C. Then the reaction mixture was stirred at room temperature for 2 h. After consumption of starting material (by TLC), the reaction mixture was diluted with water (200 mL) and extracted EtOAc (2×250 mL). The organic layer was dried over anhydrous $Na_2SO_4$, concentrated under reduced pressure to afford crude. The obtained crude was purified by medium pressure liquid column chromatography by eluting with 25-30% of EtOAc in heptane to afford compound (7) (5.2 g, 92%) as an Off-white solid. LC-MS (Method-A)=578.52 $[M+H]^+$; 99.47% at RT 1.74 min. HPLC (Method-B): 99.74% at RT 9.70 min.

Step-3: Synthesis rac-N-((4R,5R)-3-(aminomethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (14-6)

To a stirred solution of compound (7) (2×2.5 g, 4.33 mmol) in THF/$H_2O$ (23+7 mL) and stirred for 5 min. TPP (3.4 g, 12.99 mmol) was the added portion wise at room temperature. The reaction mixture was stirred at room temperature for 16 h. After consumption of starting material (by TLC), the reaction mixture was diluted with water (250 mL) and extracted with EtOAc (2×250 mL). The organic layer was dried over anhydrous $Na_2SO_4$, concentrated under reduced pressure to afford crude. The obtained crude was purified by column chromatography by eluting with 7% of MeOH/DCM to afford compound (14-6) (4.5 g, 95%) as a yellow solid. LC-MS (Method-A)=550.4 $[M-H]^-$; 96.01% at RT 1.65 min.

Example 15: Synthesis of Compounds I-153, I-77 and I-140, I-7, I-37, I-22, I-34, I-60, I-85, I-158, I-100, I-94, I-137, I-96, I-223, I-121, and I-157

NMR:

$^1H$ NMR spectrum was recorded on Bruker 400 MHz and Varian 400 MHZ instruments internally referenced to a tetramethyl silane (TMS) signal. Chemical shifts (δ) and coupling constants (J) were expressed in parts per million and hertz, respectively.

LCMS:

Method-A: LCMS, X-Select (Formic acid); Column: X-Select CSH C18 (3.0*50) mm 2.5μ. Mobile Phase: A: 0.05% Formic acid in water: I (95:5); B: 0.05% Formic acid in CAN; Inj Volume: 2.0 μL, Column oven temperature: 50° C.; Flow Rate: 1.2 mL/min. Gradient Program (B %): 0.0/2, 0.3/2, 2.0/98, 2.8/98, 3.0/2,3.7/2.

Method-B: Column: X-Bridge BEH C18, (50 mm*3.0 mm,2.5μ) Mobile Phase A: 2.5 mM Ammonium Bicarbonate in Water+5% CAN; Mobile Phase B: 100% CAN; Flow rate: 1.0 mL/min. Column temperature: 40° C. Gradient Program (B %): 0.0/2, 0.3/2, 2.0/98, 2.8/98, 3.0/2, 3.7/2.

Method-C: Column: X-Select CSH C18 (50 mm*3.0 mm,2.5μ) Mobile Phase A: 0.05% TFA in Water; Mobile Phase B: 0.05% TFA in Acetonitrile; Flow rate: 1.0 mL/min. Column temperature: 40° C. Gradient Program (B %): 0.0/2, 0.3/2, 2.0/98, 2.8/98, 3.0/2, 3.7/2.

Method-D: Column: X-Select CSH C18, (50 mm*3.0 mm,2.5μ) Mobile Phase A: 2.5 mM Ammonium Bicarbonate in Water+5% CAN; Mobile Phase B: 100% I Flow rate: 1.0 mL/min. Column temperature: 40° C. Gradient Program (B %): 0.0/2, 0.3/2, 2.0/98, 2.8/98, 3.0/2, 3.7/2.

Method-E: Column: CORTECS UPLC C18 (3×30 mm, 1.6 μm) Mobile Phase: A: 0.05% FA in Water; B: 0.05% FA in I, Flow rate: 0.85 mL/min (Gradient), Column Oven Temp: 45° C., Gradient Program (B %): 0/3, 0.1/3, 1.4/97, 2/97, 2.05/3, 2.5/3.

Method-F: Column: Poroshell 120 EC-C18 (3×100 mm,2.7 μm) Mobile Phase: A: 0.05% TFA in Water; B: 0.05% TFA in I, Flow rate: 0.80 mL/min (Gradient), Column Oven Temp: 40° C., Gradient Program (B %): 0.01/2, 0.2/2, 3/98, 5/98, 5.2/2, 7/2.

Method-G: Column: X-Select BEH C18, (50 mm*3.0 mm,2.5μ) Mobile Phase A: 2.5 mM Ammonium Bicarbonate in Water+5% CAN; Mobile Phase B: 100% I Flow rate: 1.0 mL/min. Column temperature: 40° C. Gradient Program (B %): 0.0/2, 0.3/2, 2.0/98, 2.8/98, 3.0/2, 3.7/2.

Method-H: Column: BAKERBOND Q2100 C18 (2.1×50 mm,1.8 μm) Mobile Phase: A: 0.05% FA in Water, Mobile Phase B: 0.05% FA in Acetonitrile, Column Temperature: 40° C., Flow Rate: 0.6 mL/min, Gradient: 0.0/2, 0.3/2, 2.0/98, 2.8/98, 3.0/2, 3.7/2, Diluent: I:Water.

Method-I: Column: Poroshell 120 EC-C18 (3×100 mm,2.7 μm) Mobile Phase: A: 0.05% TFA in Water B: 0.05% TFA in I, Flow rate: 0.70 mL/min (Gradient), Column Oven Temp: 40° C., Gradient Program (B %): 0.01/10, 0.2/10, 6/90, 8/90, 8.1/10, 10/10.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5, 1/5, 8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/5, 1.0/5, 8.0/100, 12.0/100, 14.0/5, 18.0/5; Flow: 1.0 mL/min.

Method-C: Column: X SELECT CSH C18 (150×4.6 mm, 3.5μ); Mobile Phase A; 0.05% TFA in water: I (95:05); Mobile Phase B: 0.05% TFA in water: I (05:95); Programme: T/B %: 0.01/10, 12/90, 16/90; Flow: 1 mL/min.; Diluent: water: I (80:20).

Method-D: Column: X-Bridge CSH C18 (4.6*150) mm 5μ Mobile Phase: A-0.1% TFA in water; B-Acetonitrile Inj Volume; 5.0 μL, Flow Rate: 1.2. mL/minute Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in Hexane; Mobile Phase B: IPA A/B: 60/40 Flow: 1.0 ml/MIN PDA: OJ-H_015.

Method-F: Column Name: CHIRALPAK-IK (250×4.6 mm, 5 μm) Mobile phase-A: n-Hexane; Mobile phase-B: EtOH/MeOH (1:1) Flow rate: 1.0 mL/min % A/B: 50/50.

Method-G: Column: X-Select CHS C18 (4.6*150) mm 5μ Mobile Phase: A-5 mM Ammonium acetate; B-Acetonitrile; Inj Volume; 5.0 μL, Flow Rate: 1.0 mL/minute.

Method-H: Column: X-Bridge CSH C18 (150×4.6 mm, 3.5 μm); Mobile Phase-A: 5 mM $NH_4HCO_3$ in water; Mobile Phase-B: I; Programme/B %: Time (min)/B Conc.: 0.01/5, 1.0/5, 8.0/100, 12.0/100, 14.10/5, 18.0/5; Flow: 1.0 mL/min.; Diluent: I:Water (80:20).

Method-I: Column Name: CHIRALPAK-IC (250×4.6 mm, 5 μm) Mobile phase-A: 0.1% TFA in n-Hexane, Mobile phase-B: DCM: IPA (50:50), Flow rate: 1.0 mL/min % A/B: 60/40.

Method-J: Column Name: CHIRALPAK-IA (150*4.6 mm, 3 μm)) Mobile phase-A: n-hexane, Mobile phase-B: EtOH: MeOH (1:1), Flow rate: 1.0 mL/min % A/B: 90:10.

Method-K: Column: CHIRALCEL-OX-H (250×4.6 mm, 5μ) Mobile Phase A: n-Hexane, Mobile Phase B: IPA, A/B: 50/50 Flow: 1.0 mL/min.

Method-L: Column Name: CHIRALPAK-IA (150*4.6 mm, 3 μm)) Mobile phase-A: n-hexane, Mobile phase-B: EtOH: MeOH (1:1), Flow rate: 1.0 mL/min, % A/B: 70:30.

Method-M: Column: ACE Excel 2 $C_{18}$-AR (100 mm×3.0 mm, 2.5 μm) Mobile Phase A: 0.05% FA in Water, Mobile Phase B: 0.05% FA in Acetonitrile, Column Temperature: 40° C. Flow Rate: 0.6 mL/min. Gradient: 0/5, 1/5, 6/90, 8.5/90, 8.8/5, 11/5. Diluent: I:Water.

Method-N: Column: BAKERBOND 1.7μ or 1.8μ C18 100 mm×2.1 mm Mobile Phase A: 0.05% FA in Water, Mobile Phase B: 0.05% FA in Acetonitrile, Column Temperature: 40° C., Flow Rate: 0.5 mL/min, Gradient: 0/5, 3/5, 6/95, 8.5/95, 8.8/5, 11/5, Diluent: I:Water.

Method-O: Column Name: CHIRALPAK-IG (250×4.6 mm, 5 μm) Mobile phase-A: n-Hexane Mobile phase-B: EtOH/MeOH (50/50) Flow rate: 1.0 mL/min % A/B: 50/50.

Method-P: Column Name: CHIRALPAK-IG (250×4.6 mm, 5 μm) Mobile phase-A: 0.1% DEA in n-Hexane; Mobile phase-B: ETOH/MEOH (50/50) Flow rate: 1.0 mL/min % A/B: 70/30.

Method-Q: Column: BAKERBOND 1.7μ C18 100 mm×2.1 mm Mobile Phase A: 0.05% TFA in Water, Mobile Phase B: 0.05% TFA in Acetonitrile, Colum Temperature: 40° C., Flow Rate: 0.5 mL/min, Gradient: 0/5, 3/5, 6/95, 8.5/95, 8.8/5, 11/5, Diluent: I:Water.

Method-R: Column Name: CHIRALPAK-IC (250×4.6 mm, 5 μm) Mobile phase-A: n-Hexane, Mobile phase-B: IPA: MeOH (1:1), Flow rate: 1.0 mL/min % A/B: 50/50.

Method-S: Column: CHIRALCEL-OJ-H (250×4.6 mm, 5μ) Mobile Phase A: n-Hexane Mobile Phase B: EtOH/MeOH (1:1) A/B: 50/50 Flow: 1.0 mL/min.

Method-T: Column Name: CHIRALPAK-IC (250×4.6 mm, 5 μm) Mobile phase-A: n-Hexane, Mobile phase-B: IPA: MeOH (50:50), Flow rate: 1.0 mL/min % A/B: 50/50.

Method-U: Column Name: CHIRALPAK-IC (250×4.6 mm, 5 μm) Mobile phase-A: n-Hexane, Mobile phase-B: EtOH: MeOH (50:50), Flow rate: 0.7 mL/min % A/B: 50/50.

Method-V: Column Name: CHIRALPAK-IK (250×4.6 mm, 5 μm) Mobile phase-A: n-Hexane Mobile phase-B: EtOH/MeOH (1:1) Flow rate: 1.0 mL/min % A/B: 70/30.

Synthesis of I-153 & I-77

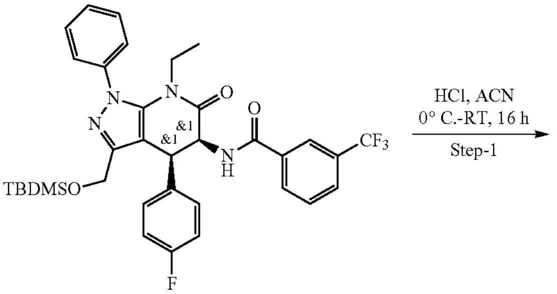

SM-1

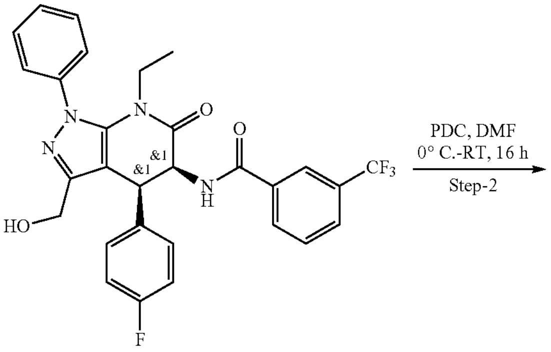

1

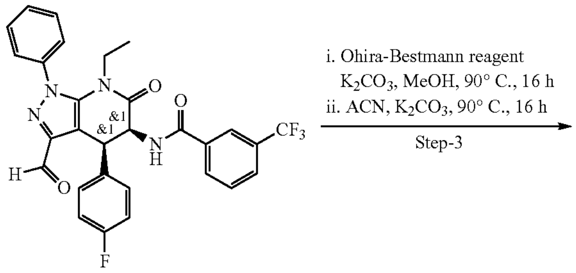

2

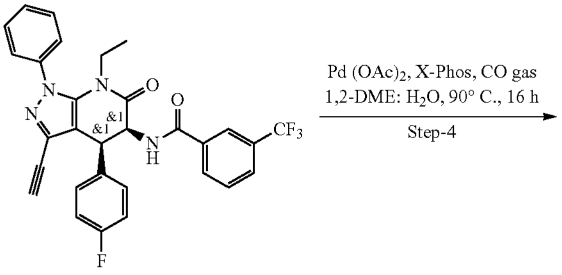

3

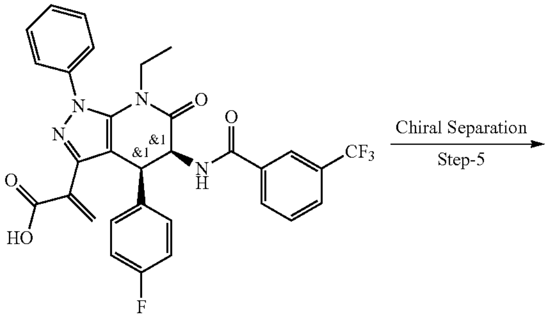

4

-continued

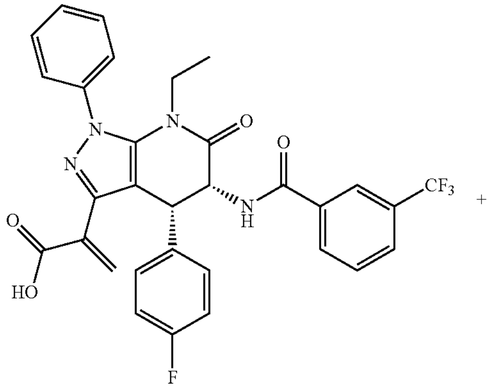

I-77

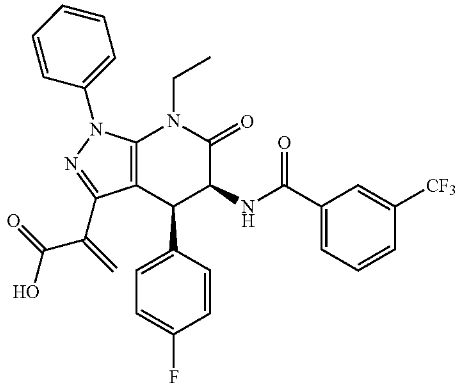

I-153

Step-1: Synthesis of rac-N-((4R,5R)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-3-(trifluoromethyl)benzamide (1)

To the mixture of N-[(4S,5S)-3-[[tert-butyl(dimethyl) silyl]oxy methyl]-7-ethyl-4-(4-fluoro phenyl)-6-oxo-1-phenyl-4,5-dihydro pyrazolo[3,4-b]pyridine-5-yl]-3-(trifluoro methyl)benzamide (SM-1) (9.0 g, 13.50 mmol) (Mixture of RR & SS isomer) in I (100 mL) was added hydrochloric acid (11.25 mL, 67.49 mmol) at 0° C. and stirred at room temperature for 16 h. The reaction was monitored by TLC (50% EA: Heptane, Rf=0.4). After completion of reaction, the mixture was diluted with aqueous sodium bicarbonate solution (100 mL) and extracted with EtOAc (3×250 mL), the combined organic layer was dried over sodium sulphate and concentrated under reduced pressure to get crude reaction mixture as yellow gummy compound. The crude compound was purified by flash chromatography using 30-40% EtOAc: Heptane solvent to get desired product compound (1) (5.0 g, 66.38%) (Mixture of RR & SS isomer) as yellow solid.

$^1$H NMR (400 MHZ, $CDCl_3$) δ=8.02 (s, 1H), 7.86 (d, J=7.6 Hz, 1H), 7.78 (d, J=7.6 Hz, 1H), 7.56-7.43 (m, 6H), 7.01-6.90 (m, 5H), 5.24 (t, J=6.5 Hz, 1H), 4.91 (d, J=7.1 Hz, 1H), 4.61 (d, J=5.9 Hz, 2H), 3.97 (d, J=7.2, 14.2 Hz, 1H), 3.19 (d, J=6.9, 14.0 Hz, 1H), 1.86 (t, J=5.9 Hz, 1H), 1.00 (t, J=7.0 Hz, 3H). LC-MS (Method-E)=553.29 $[M+H]^+$=99.57% at RT 1.55 min.

Step-2: Synthesis of rac-N-((4R,5R)-7-ethyl-4-(4-fluorophenyl)-3-formyl-6-oxo-1-phenyl-4,5,6,7-tetrahydro-1H-pyrazolo[3,4-b]pyridin-5-yl)-3-(trifluoromethyl)benzamide (2)

To a solution of N-[(4S,5S)-7-ethyl-4-(4-fluorophenyl)-3-(hydroxymethyl)-6-oxo-1-phenyl-4,5-dihydropyrazolo[3,4-b]pyridine-5-yl]-3-(trifluoromethyl)benzamide (1) (5.0 g, 9.0 mmol) in DMF (50 mL) at 0° C., pyridinium dichromate (1.20 equiv., 11 mmol) was added slowly. The reaction mixture was stirred at 25° C. for 16 h. After consumption of the starting material (by TLC), the reaction mixture was quenched with ice cold water (100 mL) and extracted with diethyl ether (3×100 mL). The organic layer was dried over anhydrous $Na_2SO_4$ and concentrated under reduced pressure. The crude material was purified by medium pressure liquid chromatography by eluting 15-30% EtOAc in heptane to afford compound (2) (4.0 g, 79%) as an off-white solid.

$^1$H NMR (400 MHZ, DMSO-$d_6$) δ=9.88 (s, 1H), 8.64 (d, J=7.0 Hz, 1H), 8.19-8.10 (m, 2H), 7.92 (d, J=7.7 Hz, 1H), 7.83 (d, J=6.6 Hz, 2H), 7.75-7.60 (m, 4H), 7.14-7.06 (m, 2H), 7.05-6.97 (m, 2H), 5.58 (t, J=7.1 Hz, 1H), 4.90 (d, J=7.2 Hz, 1H), 3.89 (dd, J=7.2, 14.5 Hz, 1H), 3.02 (dd, J=6.9, 14.1 Hz, 1H), 0.90 (t, J=6.9 Hz, 3H). LC-MS (Method-D)=551.2 $[M+H]^+$=97.79% at RT 2.46 min.

Step-3: Synthesis of rac-N-((4R,5R)-7-ethyl-3-ethynyl-4-(4-fluorophenyl)-6-oxo-1-phenyl-4,5,6,7-tetrahydro-1H-pyrazolo[3,4-b]pyridin-5-yl)-3-(trifluoromethyl)benzamide (3)

To a stirred solution of N-[(4S,5S)-7-ethyl-4-(4-fluorophenyl)-3-formyl-6-oxo-1-phenyl-4,5-dihydro pyrazolo[3,4-b]pyridine-5-yl]-3-(trifluoromethyl)benzamide (3) (1.75 g, 3.18 mmol) in methanol (35 mL) were added potassium carbonate (880 mg, 6.36 mmol) followed by dimethyl (1-diazo-2-oxo propyl)phosphonate (Ohira Bestmann reagent) (935 mg, 4.77 mmol) at 25° C. The reaction mixture stirred at 90° C. for 16 h. The progress of the reaction was monitored by TLC. After completion, the reaction mixture was allowed to room temperature and then filtered, washed with ethyl acetate, the filtrate was concentrated under reduced pressure to get 2.31 g of crude material which was a mixture of cis & trans isomers, where trans isomer was major.

Epimerization procedure: To the above crude compound was added I (50 mL, 99.9 mass %) followed by Potassium carbonate (2.0 equiv., 8.45 mmol, 99.9 mass %), and the reaction was stirred at 90° C. for 16 h. Progress of the reaction was monitored by TLC. Reaction mixture was allowed to RT, solids were filtered and filtered cake was washed with ethyl acetate, filtrate was concentrated to get crude material, which was purified by silica gel (230-400 mesh) column chromatography using 15% ethyl acetate in heptane to afford title compound (1.30 g, 2.34 mmol, 98.39 mass %, 55.4% yield) as a white solid. LC-MS (Method-B)=547.5 $[M+H]^+$; 98% at RT 2.49.

Step-4: Synthesis of rac-2-((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) acrylic acid (4)

To a stirred solution of N-[(4S,5S)-7-ethyl-3-ethynyl-4-(4-fluorophenyl)-6-oxo-1-phenyl-4,5-dihydropyrazolo[3,4-b]pyridine-5-yl]-3-(trifluoromethyl)benzamide (3) 1.2 g, (2.4 mmol, 200 mg×6 batches) in 1,2-Dimethoxyethane (24 mL) & water (48 mL) & Al(Otf)$_3$ (240 mg, 0.42 mmol,) and [1-(2-diphenylphosphanyl-1-naphthyl)-2-naphthyl]-diphenyl-phosphane (12.0 mg, 0.024 mmol), followed by Palladium(II) acetate (24.0 mg, 0.12 mmol) was added under the atmosphere of CO gas pressure of 150 psi at 90° C. in a steel bomb for 16 h. The progress of the reaction was monitored by TLC. The reaction mixture was allowed to RT, quenched with water (50 mL), and extracted with EA (2×50 mL), combined organic layers were dried over anhydrous sodium sulfate and concentrated to get crude compound. The above crude compound was purified by silica gel (230-400) column chromatography eluting with a gradient of 5-10% MeOH/DCM followed by prep-HPLC and lyophilization to get pure compound (4) (175 mg, 13.5%) as a white solid.

$^1$H NMR (400 MHZ, DMSO-d$_6$) δ=8.46 (d, J=7.3 Hz, 1H), 8.18-8.12 (m, 2H), 7.92 (d, J=7.8 Hz, 1H), 7.74-7.66 (m, 3H), 7.62-7.51 (m, 3H), 7.11-7.05 (m, 2H), 6.99-6.94 (m, 2H), 5.86 (s, 1H), 5.51 (t, J=7.3 Hz, 1H), 5.42 (s, 1H), 4.67 (d, J=7.1 Hz, 1H), 3.95-3.85 (m, 1H), 3.06 (dd, J=7.1, 14.2 Hz, 1H), 0.92 (t, J=7.1 Hz, 3H). LC-MS (Method-D) =593.2 [M+H]$^+$; 99.42% at RT 1.83 min. HPLC (Method-H)=98.87% at RT 7.02 min.

Step-5: Synthesis of 2-((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) acrylic acid (Peak-1) I-77 & 2-((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) acrylic acid (Peak-2) I-153

The racemic compound 2-[(4S,5S)-7-ethyl-4-(4-fluorophenyl)-6-oxo-1-phenyl-5-[[3-(trifluoro methyl)benzoyl]amino]-4,5-dihydropyrazolo[3,4-b]pyridine-3-yl]prop-2-enoic acid (4) (150 mg, 0.253 mmol) compound was purified using chiral HPLC. The collected fractions were evaporated under reduced pressure to get the pure (Peak-1) I-77 (20 mg, 12.2%) and (Peak-2) I-153 (23 mg, 14.6%) as an Off-White solid.

(Peak-1) I-77:

$^1$H NMR (400 MHZ, DMSO-d$_6$) δ=12.83 (bs, 1H), 8.51 (d, J=7.3 Hz, 1H), 8.19-8.12 (m, 2H), 7.92 (d, J=7.9 Hz, 1H), 7.76-7.69 (m, 3H), 7.65-7.54 (m, 3H), 7.13-7.08 (m, 2H), 6.96 (dd, J=5.5, 8.5 Hz, 2H), 6.08 (d, J=1.0 Hz, 1H), 5.60 (s, 1H), 5.52 (t, J=7.2 Hz, 1H), 4.57 (d, J=7.0 Hz, 1H), 3.96-3.84 (m, 1H), 3.06 (dd, J=6.9, 14.2 Hz, 1H), 0.93 (t, J=7.1 Hz, 3H). LC-MS (Method-D)=593.2 [M+H]$^+$; 91.73% at RT 1.71 min. HPLC (Method-H)=91.62% at RT 6.86 min. Chiral HPLC (Method-I)=Peak-1=36.499% at RT 4.927 min.

(Peak-2) I-153:

$^1$H NMR (400 MHZ, DMSO-d$_6$) δ=12.83 (bs, 1H), 8.51 (d, J=7.3 Hz, 1H), 8.19-8.12 (m, 2H), 7.92 (d, J=7.9 Hz, 1H), 7.76-7.69 (m, 3H), 7.65-7.54 (m, 3H), 7.13-7.08 (m, 2H), 6.96 (dd, J=5.5, 8.5 Hz, 2H), 6.08 (d, J=1.0 Hz, 1H), 5.60 (s, 1H), 5.52 (t, J=7.2 Hz, 1H), 4.57 (d, J=7.0 Hz, 1H), 3.96-3.84 (m, 1H), 3.06 (dd, J=6.9, 14.2 Hz, 1H), 0.93 (t, J=7.1 Hz, 3H). LC-MS (Method-D)=593.2 [M+H]$^+$; 95.48% at RT 1.71 min. HPLC (Method-H)=95.30% at RT 6.84 min. Chiral HPLC (Method-I)=Peak-2=100% at RT 7.80 min.

Synthesis of I-140

Step-1: Synthesis of N-[(4S, 5S)-3-[(cyanoamino) methyl]-7-ethyl-4-(4-fluoro phenyl)-6-oxo-1-phenyl-4,5-dihydro pyrazolo[3,4-b]pyridine-5-yl]-3-(trifluoro methyl)benzamide (I-140)

To a stirred solution of N-[(4S, 5S)-3-(aminomethyl)-7-ethyl-4-(4-fluorophenyl)-6-oxo-1-phenyl-4,5-dihydro pyrazolo[3,4-b]pyridine-5-yl]-3-(trifluoro methyl)benzamide (200 mg, 0.362 mmol) in DMF (5 mL) was added 3-oxo-1,2-benziodoxole-1 (3H)-carbonitrile (135.5 mg, 0.471 mmol) at room temperature. The reaction mixture stirred at room temperature for 6 h. The progress of the reaction was monitored by TLC. The reaction mixture was quenched with water (20 mL) and extracted with EA (3×30 mL), combined organic layers were dried over anhydrous sodium sulfate and concentrated to get crude compound. The crude compound was purified by silica gel (230-400 mesh) column chromatography and eluted with 25% EA in Heptane to obtain the title compound I-140 (55 mg, 26.04%) as a white solid.

$^1$H NMR (400 MHz, DMSO-d$_6$) δ=8.54 (d, J=7.5 Hz, 1H), 8.17-8.12 (m, 2H), 7.92 (d, J=7.9 Hz, 1H), 7.74-7.67 (m, 3H), 7.64-7.54 (m, 3H), 7.17 (t, J=5.6 Hz, 1H), 7.13-7.08 (m, 2H), 7.02-6.97 (m, 2H), 5.54 (t, J=7.4 Hz, 1H), 4.67 (d, J=7.4 Hz, 1H), 3.99 (t, J=5.3 Hz, 2H), 3.95-3.87 (m, 1H), 3.08-3.03 (m, 1H), 0.91 (t, J=7.1 Hz, 3H). LC-MS (Method-F)=577.1 [M+H]$^+$=94.43% at RT 3.53 min. HPLC (Method-H)=92.65% at RT 8.63 min.

Synthesis of I-7, I-100 and I-22

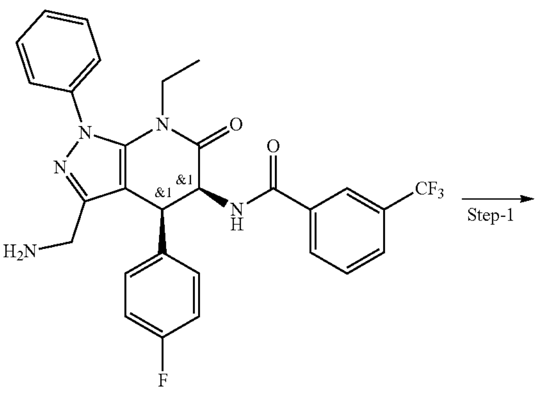

SM-1

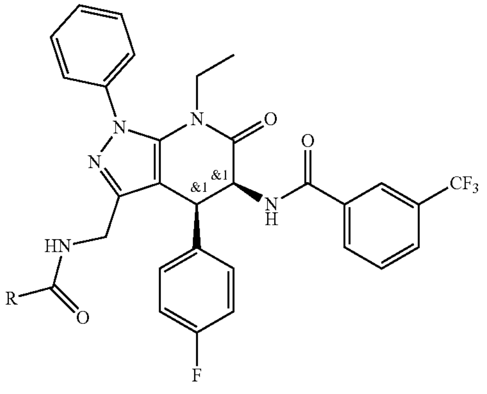

I-7, I-37, I-100 and I-22 a. EDCl, HOBt, DIPEA, DMF, RT, 16 h

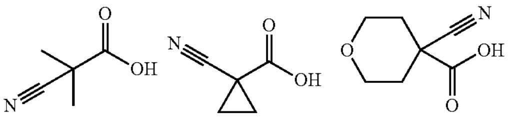

A B C

-continued

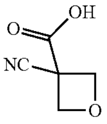

D

Step-1: Synthesis of rac-N-((4R,5R)-3-((2-cyano-2-methylpropanamido)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (I-7)

To a stirred solution of SM-1 (150 mg, 0.272 mmol) in DMF (3 mL) was added N,N-Diisopropylethylamine (A) (0.14 mL, 0.816 mmol), EDAC (79.81 mg, 0.408 mmol), 2-cyano-2-methyl-propanoic acid (39.9 mg, 0.353 mmol) and 1-Hydroxybenzotriazole (56.2 mg, 0.408 mmol) at room temperature. The reaction mixture stirred at room temperature for 16 h. The progress of the reaction was monitored by TLC. The reaction mixture was quenched with water (25 mL) and extracted with EtOAc (2×25 mL), combined organic layers were dried over anhydrous sodium sulfate and concentrated to get crude compound. The crude compound was purified by silica gel (230-400 mesh silica) column chromatography and the compound eluted with 40% EtOAc in Heptane to obtain the title compound of I-7 (65 mg, 36.1%) as a white solid.

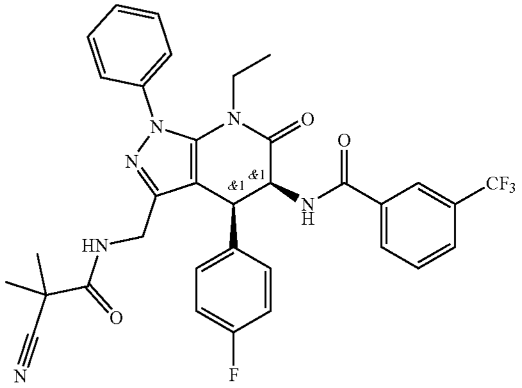 [SMILES: CCN1C(=O)[C@@H](NC(=O)c2cccc(C(F)(F)F)c2)[C@@H](c2ccc(F)cc2)c2c(CNC(=O)C(C)(C)C#N)nn(-c3ccccc3)c21]

$^1$H NMR (400 MHZ, DMSO-d$_6$) δ=8.51-8.42 (m, 2H), 8.18-8.13 (m, 2H), 7.93 (d, J=7.8 Hz, 1H), 7.74-7.70 (m, 3H), 7.69-7.66 (m, 3H), 7.11-7.06 (m, 2H), 6.94-6.90 (m, 2H), 5.47 (t, J=7.1 Hz, 1H), 4.58 (d, J=7.1 Hz, 1H), 4.36 (dd, J=6.4, 15.1 Hz, 1H), 4.18-4.11 (m, 1H), 3.91-3.86 (m, 1H), 3.08-3.01 (m, 1H), 1.23 (s, 3H), 1.15 (s, 3H), 0.91 (t, J=7.1 Hz, 3H). LC-MS (Method-D)=647.2 [M+H]$^+$; 98.42% at RT 2.34 min. HPLC (Method-C)=97.70% at RT 8.92 min. Chiral HPLC (Method-J)=Peak-1=50.70% at RT 10.45 min. Peak-2=49.30% at RT 13.02 min.

Synthesis of rac-N-((4R,5R)-3-((1-cyanocyclopropane-1-carboxamido)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (I-37)

To a stirred solution of SM-1 (150 mg, 0.272 mmol) in DMF (3 mL) was added N,N-Diisopropylethylamine (0.14 mL, 0.816 mmol), EDAC (79.81 mg, 0.408 mmol), 1-cyanocyclopropane-1-carboxylic acid (B) (35.3 mg, 0.353 mmol) and 1-Hydroxybenzotriazole (56.2 mg, 0.408 mmol) at room temperature. Th reaction mixture stirred at room temperature for 16 h. The progress of the reaction was monitored by TLC. The reaction mixture was quenched with water (25 mL) and extracted with EtOAc (2×25 mL), combined organic layers were dried over anhydrous sodium sulfate and concentrated to get crude compound. The crude compound was purified by silica gel (230-400 mesh silica) column chromatography and the compound eluted with 50% EtOAc in Heptane to obtain the title compound of I-37 (68 mg, 37.62%) as a white solid.

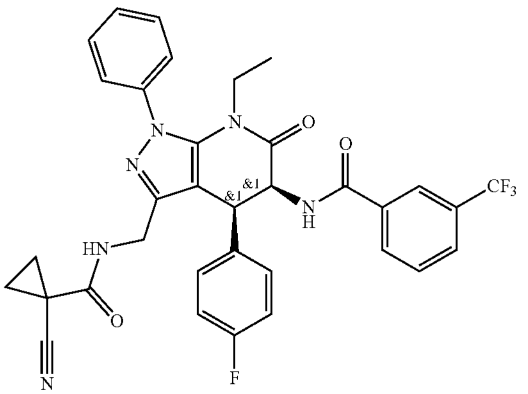 [SMILES: CCN1C(=O)[C@@H](NC(=O)c2cccc(C(F)(F)F)c2)[C@@H](c2ccc(F)cc2)c2c(CNC(=O)C3(C#N)CC3)nn(-c3ccccc3)c21]

$^1$H NMR (400 MHZ, DMSO-d$_6$) δ=8.49 (d, J=7.3 Hz, 1H), 8.36 (t, J=5.9 Hz, 1H), 8.20-8.14 (m, 2H), 7.93 (d, J=7.8 Hz, 1H), 7.74-7.66 (m, 3H), 7.61-7.57 (m, 3H), 7.10 (t, J=8.9 Hz, 2H), 6.91 (dd, J=5.5, 8.6 Hz, 2H), 5.49 (t, J=7.3 Hz, 1H), 4.62 (d, J=7.1 Hz, 1H), 4.39 (dd, J=6.8, 15.2 Hz, 1H), 4.12 (dd, J=4.9, 15.2 Hz, 1H), 3.94-3.85 (m, 1H), 3.08-2.98 (m, 1H), 1.32-1.23 (m, 2H), 1.22-1.16 (m, 1H), 1.05-1.00 (m, 1H), 0.91 (t, J=7.1 Hz, 3H). LC-MS (Method-D)=645.2 [M+H]$^+$; 98.12% at RT 2.32 min. HPLC (Method-B)=97.82% at RT 8.80 min. Chiral HPLC (Method-K)= Peak-1=50.30% at RT 6.43 min. Peak-2=49.69% at RT 7.78 min.

Synthesis of rac-3-cyano-N-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)methyl) oxetane-3-carboxamide (I-100)

To a stirred solution of SM-1 (150 mg, 0.272 mmol) in DMF (5 mL) was added N,N-Diisopropylethylamine (0.14 mL, 0.816 mmol) and 3-cyano oxetane-3-carboxylic acid (D) (44.94 mg, 0.353 mmol) followed by 1-hydroxybenzotriazole (56.25 mg, 0.408 mmol) at room temperature. The reaction mixture stirred at room temperature for 16 h. The progress of the reaction was monitored by TLC. The reaction mixture was quenched with water (25 mL) and extracted with EtOAc (3×25 mL), combined organic layers were dried over anhydrous sodium sulfate and concentrated to get crude compound. The crude compound was purified by silica gel (230-400 mesh) column chromatography and eluted with 50% EA in Heptane to afford the title compound I-100 (63 mg, 34.71%) as a white solid.

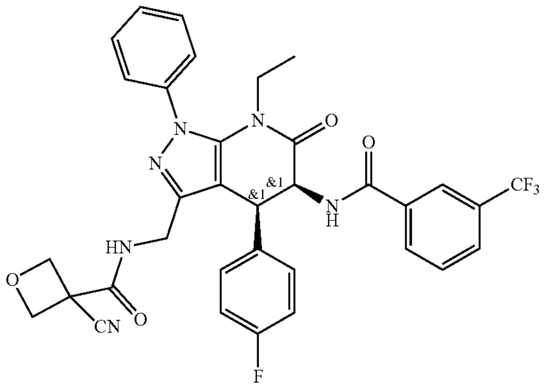 [SMILES: CCN1C(=O)[C@@H](NC(=O)c2cccc(C(F)(F)F)c2)[C@@H](c2ccc(F)cc2)c2c(CNC(=O)C3(C#N)COC3)nn(-c3ccccc3)c21]

$^1H$ NMR (400 MHZ, DMSO-$d_6$) δ=8.90 (t, J=5.8 Hz, 1H), 8.53 (d, J=7.3 Hz, 1H), 8.18-8.12 (m, 2H), 7.92 (d, J=7.8 Hz, 1H), 7.75-7.66 (m, 3H), 7.63-7.52 (m, 3H), 7.12-7.07 (m, 2H), 6.93 (dd, J=5.5, 8.6 Hz, 2H), 5.50 (t, J=7.3 Hz, 1H), 4.63-4.58 (m, 3H), 4.50-4.39 (m, 3H), 4.18 (dd, J=4.9, 15.2 Hz, 1H), 3.95-3.85 (m, 1H), 3.06-3.01 (m, 1H), 0.91 (t, J=7.1 Hz, 3H). LC-MS (Method-D)=661.1 $[M+H]^+$; 98.43% at RT 2.28 min. HPLC (Method-B)=98.52% at RT 8.65 min. Chiral HPLC (Method-S)=Peak-1=50.14% at RT 4.74 min. Peak-2=49.85% at RT 5.45 min.

Synthesis of rac-4-cyano-N-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)methyl)tetrahydro-2H-pyran-4-carboxamide (I-22)

To a stirred solution SM-1 (150 mg, 0.272 mmol) in DMF (3 mL) was added N,N-Diisopropylethylamine (0.14 mL, 0.816 mmol), EDAC (79.81 mg, 0.408 mmol), 4-cyanotetrahydropyran-4-carboxylic acid I (54.86 mg, 0.353 mmol) and 1-Hydroxybenzotriazole (56.2 mg, 0.408 mmol) at room temperature. Th reaction mixture stirred at room temperature for 16 h. The progress of the reaction was monitored by TLC. The reaction mixture was quenched with water (25 mL) and extracted with EtOAc (2×25 mL), combined organic layers were dried over anhydrous sodium sulfate and concentrated to get crude compound. The crude compound was purified by silica gel (230-400 mesh) column chromatography and the compound eluted with 60% EA in Heptane to obtain the title compound of I-22 (95 mg, 50.21%) as a white solid.

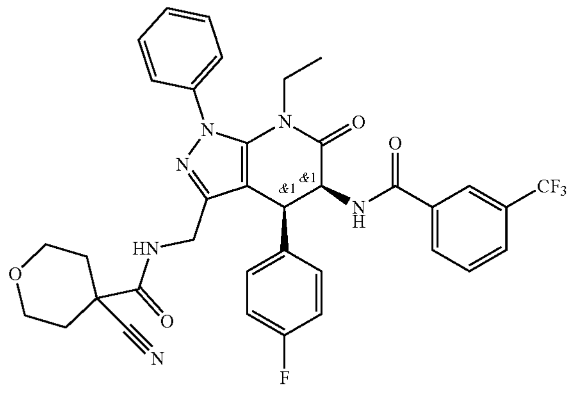 [SMILES: CCN1C(=O)[C@@H](NC(=O)c2cccc(C(F)(F)F)c2)[C@@H](c2ccc(F)cc2)c2c(CNC(=O)C3(C#N)CCOCC3)nn(-c3ccccc3)c21]

$^1H$ NMR (400 MHZ, DMSO-$d_6$) δ=8.63 (t, J=5.8 Hz, 1H), 8.53 (d, J=7.3 Hz, 1H), 8.19-8.13 (m, 2H), 7.93 (d, J=7.8 Hz, 1H), 7.76-7.66 (m, 3H), 7.60 (t, J=7.4 Hz, 2H), 7.56-7.51 (m, 1H), 7.12-7.07 (m, 2H), 6.93 (dd, J=5.5, 8.6 Hz, 2H), 5.48 (t, J=7.2 Hz, 1H), 4.60 (d, J=7.0 Hz, 1H), 4.36 (dd, J=6.4, 15.1 Hz, 1H), 4.19 (dd, J=5.2, 15.1 Hz, 1H), 3.89 (d, J=7.0, 14.3 Hz, 1H), 3.78-3.72 (m, 2H), 3.41-3.35 (m, 2H), 3.03 (dd, J=7.1, 14.3 Hz, 1H), 1.66 (dd, J=1.8, 13.8 Hz, 1H), 1.62-1.55 (m, 2H), 1.51-1.43 (m, 1H), 0.91 (t, J=7.1 Hz, 3H).

LC-MS (Method-D)=689.0 $[M+H]^+$; 97.70% at RT 2.29 min. HPLC (Method-B)=98.84% at RT 8.77 min. Chiral HPLC (Method-L)=Peak-1=50.49% at RT 5.69 min. Peak-2=48.93% at RT 6.62 min.

Synthesis of I-85 & I-158

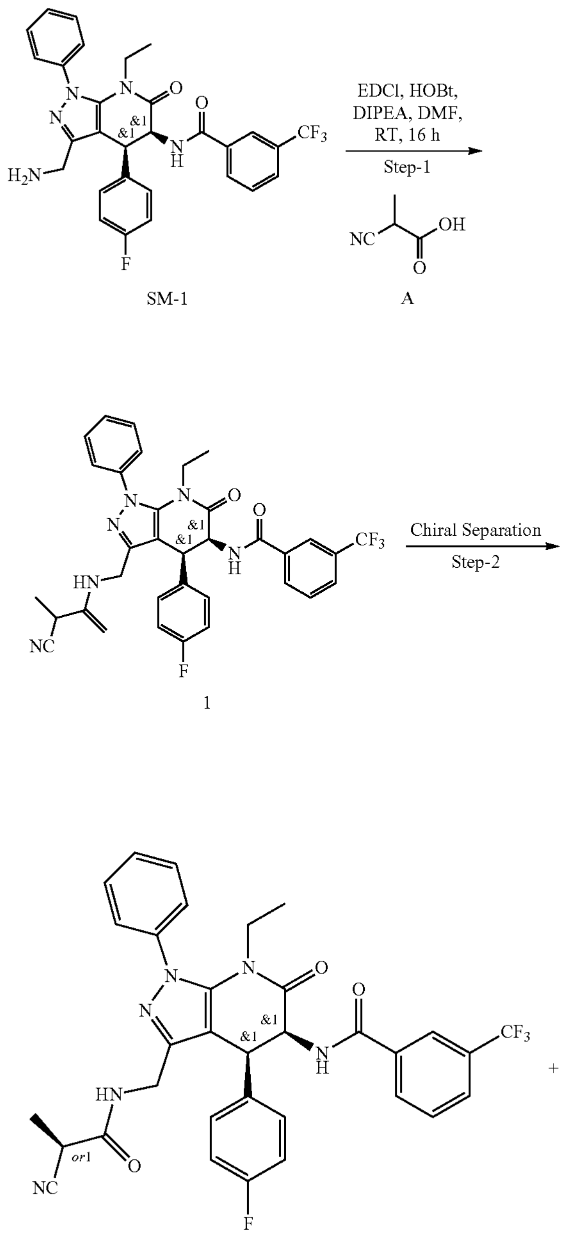

SM-1

A

1

I-85

-continued

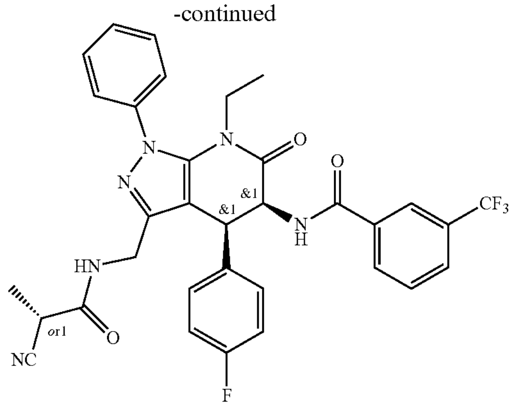

I-158

Step-1: rac-N-((4R,5R)-3-((2-cyanopropanamido)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (1)

To a stirred solution (SM-1) (250 mg, 0.453 mmol) in DMF (5 mL) was added N,N-Diisopropylethylamine (0.23 mL, 1.360 mmol), EDAC (133 mg, 0.68 mmol), 2-cyano-propanoic acid (58.39 mg, 0.589 mmol) and 1-Hydroxybenzotriazole (93.7 mg, 0.68 mmol) at room temperature. The reaction mixture stirred at room temperature for 16 h. The progress of the reaction was monitored by TLC. The reaction mixture was quenched with water and extracted with EtOAc. Combined organic layers were dried over anhydrous sodium sulfate and concentrated to get crude compound. The crude compound was purified by silica gel (230-400 mesh) column chromatography and the compound eluted with 50% EA in Heptane to obtain the compound (1) (210 mg, 72.50%) as a white solid.

$^1$H NMR (400 MHZ, DMSO-$d_6$) δ=8.69-8.59 (m, 1H), 8.54 (dd, J=6.2, 7.1 Hz, 1H), 8.20-8.12 (m, 2H), 7.93 (d, J=7.9 Hz, 1H), 7.77-7.66 (m, 3H), 7.63-7.52 (m, 3H), 7.12-7.07 (m, 2H), 6.94 (dd, J=5.5, 8.5 Hz, 2H), 5.53-5.47 (m, 1H), 4.56 (t, J=6.8 Hz, 1H), 4.37-4.10 (m, 2H), 3.90 (dd, J=7.3, 14.4 Hz, 1H), 3.30-3.21 (m, 1H), 3.08-2.98 (m, 1H), 1.32-1.23 (m, 1H), 1.23-1.06 (m, 2H), 0.91 (t, J=7.1 Hz, 3H). LC-MS (Method-D)=689.0 [M+H]$^+$; 97.68% at RT 2.26 min. HPLC (Method-B)=97.64% at RT 8.66 min. Chiral HPLC (Method-Q)=Peak-1=51.56% at RT 40.20 min. Peak-2=48.23% at RT 40.40 min.

Step-2: Synthesis of N-((4RS,5RS)-3-(((S*)-2-cyanopropanamido)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (Peak-1) I-85 & N-((4RS,5RS)-3-(((R*)-2-cyanopropanamido)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (Peak-2) I-158

The racemic compound Cis (N-[(4S, 5S)-3-[(2-cyano propanoyl amino)methyl]-7-ethyl-4-(4-fluoro phenyl)-6-oxo-1-phenyl-4,5-dihydro pyrazolo[3,4-b]pyridine-5-yl]-3-(trifluoro methyl)benzamide (180 mg, 0.284 mmol) compound (1) was purified by Chiral HPLC to afford (Peak-1) I-85 (45 mg, 25%) as a white solid & (Peak-2) I-158 (98 mg, 54.44%) as a white solid.

(Peak-1) I-85:

$^1$H NMR (400 MHZ, DMSO-$d_6$) δ=8.70-8.57 (m, 1H), 8.54 (t, J=6.6 Hz, 1H), 8.18-8.12 (m, 2H), 7.93 (d, J=7.9 Hz, 1H), 7.74-7.66 (m, 3H), 7.62-7.52 (m, 3H), 7.13-7.06 (m, 2H), 6.94 (dd, J=5.5, 8.5 Hz, 2H), 5.50 (q, J=7.1 Hz, 1H), 4.56 (t, J=6.8 Hz, 1H), 4.37-4.10 (m, 2H), 3.95-3.84 (m, 1H), 3.29-3.22 (m, 1H), 3.09-2.97 (m, 1H), 1.21-1.06 (m, 3H), 0.91 (t, J=7.1 Hz, 3H). LC-MS (Method-D)=633.0 [M+H]$^+$; 99.67% at RT 2.39 min. HPLC (Method-B)=99.35% at RT 8.64 min. Chiral HPLC (Method-R)=Peak-1=50.29% at RT 6.08 min. Peak-2=49.21% at RT 7.25 min.

(Peak-2) I-158:

$^1$H NMR (400 MHZ, DMSO-$d_6$) δ=8.70-8.59 (m, 1H), 8.54 (dd, J=6.1, 7.2 Hz, 1H), 8.18-8.12 (m, 2H), 7.93 (d, J=7.9 Hz, 1H), 7.74-7.66 (m, 3H), 7.61-7.52 (m, 3H), 7.12-7.07 (m, 2H), 6.94 (dd, J=5.5, 8.5 Hz, 2H), 5.51 (q, J=7.1 Hz, 1H), 4.56 (t, J=6.8 Hz, 1H), 4.37-4.09 (m, 2H), 3.90 (d, J=7.1, 14.4 Hz, 1H), 3.28-3.21 (m, 1H), 3.08-2.97 (m, 1H), 1.21-1.06 (m, 3H), 0.91 (t, J=7.0 Hz, 3H). LC-MS (Method-D)=633.0 [M+H]$^+$; 95.76% at RT 2.39 min. HPLC (Method-B)=94.28% at RT 8.63 min. Chiral HPLC (Method-R)=Peak-1=47.01% at RT 7.19 min. Peak-2=47.06% at RT 7.91 min.

Synthesis of analogues: I-157, I-94, I-137, I-121. I-60 and I-34

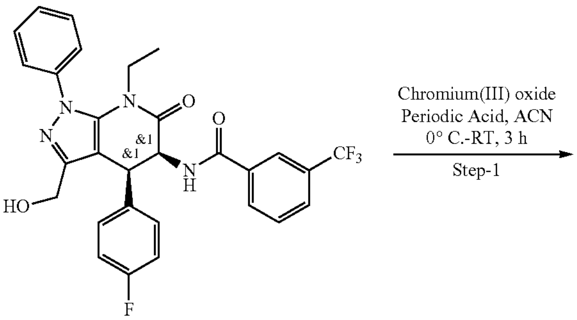

15-1

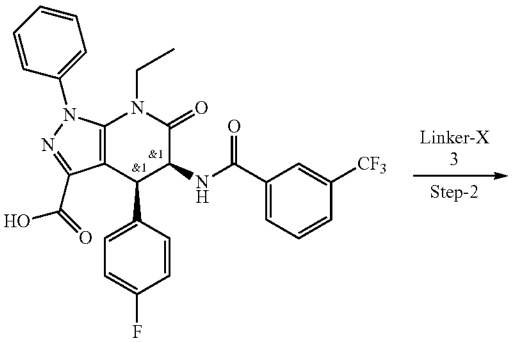

1

-continued

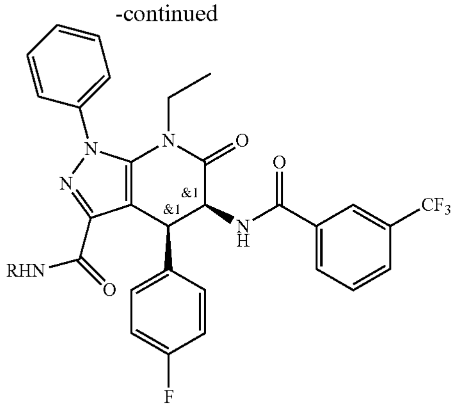

a. HATU, DIPEA, DMF, RT, 16 h

Step-1: Synthesis of rac-(4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxylic acid (1)

To a stirred solution of 15-1 (5.0 g, 9.050 mmol) in I (50 mL) were added periodic Acid (4.210 g, 18.10 mmol) and Chromium (III) oxide (413 mg, 2.715 mmol) at 0° C. The reaction mixture stirred at room temperature for 12 h. The reaction progress was monitored by TLC. After completion of reaction, the reaction mass was diluted with 10% methanol in DCM and filtered through Celite bed and washed with 10% methanol in DCM. The filtrate was concentrated under vacuum and the obtained solid was washed with diethyl ether, filtered and the compound was dried under vacuum to afford the compound (1) (3.5 g, 66%) as an off-White solid. $^{1}$H NMR (400 MHZ, $CDCl_3$) δ=13.00 (br s, 1H), 8.58 (d, J=7.3 Hz, 1H), 8.19-8.13 (m, 2H), 7.92 (d, J=7.8 Hz, 1H), 7.78 (d, J=6.8 Hz, 2H), 7.73-7.70 (m, 1H), 7.63 (d, J=7.8 Hz, 2H), 7.12-7.07 (m, 2H), 6.99 (d, J=5.4 Hz, 2H), 5.55 (t, J=7.3 Hz, 1H), 4.92 (d, J=7.3 Hz, 1H), 3.93-3.83 (m, 2H), 3.04-2.98 (m, 1H), 0.90 (t, J=6.8 Hz, 3H). LC-MS (Method-A)=567.31 $[M+H]^+$=96.91% at RT 2.12 min.

Step-2: Amide Coupling: Method-A

To a compound of rac-(4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxylic acid (1) (1.0 equvi., 0.263 mmol) in DMF (3 mL) were added N,N-Diisopropylethylamine (5.0 equvi.) and HATU (1.5 equiv.,) followed by linker-X (1.5 equvi.,) at 0° C. The reaction mixture was stirred at room temperature for 16 h. The progress of the reaction was monitored by TLC. The reaction mixture was quenched with water (25 mL) and extracted with EtOAc (2×25 mL), combined organic layers were dried over anhydrous sodium sulfate and concentrated to get crude compound. The crude compound was purified by silica gel (230-400 mesh silica) column chromatography and the compound was eluted with 60% EtOAc in heptane to obtain the title compound as a white solid. The conditions to obtain the final compounds are shown below.

| Sr No. | Cpd. Number | Linker | Structure (R) | Method | Acid (mg) | Linker Qty (mg) | Qty (mg) & Nature of compound | Yield (%) |
|---|---|---|---|---|---|---|---|---|
| 1. | I-34 | A | 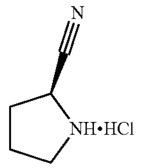 | A | 200 | 70.00 | 25 (Off-white solid) | 10 |
| 2. | I-60 | B | 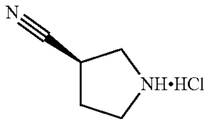 | A | 200 | 73.91 | 30 (Pale-yellow solid) | 13.18 |
| 3. | I-94 | C | 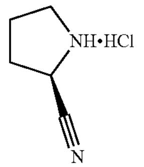 | A | 200 | 72.40 | 30 (Off-White solid) | 13.18 |
| 4. | I-137 | D | 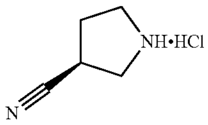 | A | 200 | 73.91 | 40 (White solid) | 16.76 |

-continued

| Sr No. | Cpd. Number | Linker | Structure (R) | Method | Acid (mg) | Linker Qty (mg) | Qty (mg) & Nature of compound | Yield (%) |
|---|---|---|---|---|---|---|---|---|
| 5. | I-121 | E | 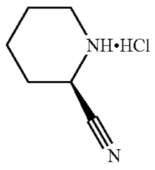 | A | 150 | 29.17 | 58 (White solid) | 16.6 |
| 6. | I-157 | F | 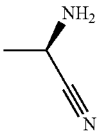 | A | 150 | 18.56 | 30 (White solid) | 18.32 |

I-34

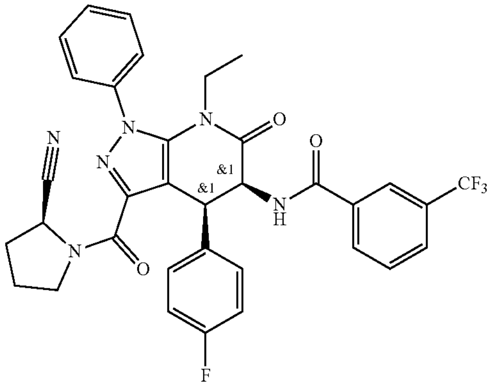

$^1$H NMR (400 MHZ, DMSO-$d_6$) δ=8.61-8.53 (m, 1H), 8.19-8.12 (m, 2H), 7.92 (d, J=7.9 Hz, 1H), 7.83-7.77 (m, 2H), 7.72 (t, J=7.8 Hz, 1H), 7.67-7.60 (m, 3H), 7.11-7.06 (m, 2H), 7.03-6.96 (m, 2H), 5.64-5.45 (m, 1H), 5.00-4.83 (m, 2H), 4.09-3.84 (m, 3H), 3.10-2.99 (m, 1H), 2.20-2.09 (m, 2H), 2.04-1.95 (m, 2H), 0.90 (t, J=6.8 Hz, 3H). LC-MS (Method-H)=645.37 $[M+H]^+$; 99.80% at RT 2.45 min. HPLC (Method-M)=99.53% at RT 6.64 min. Chiral HPLC (Method-L) Peak-1=51.15% at RT 8.23 min. Peak-2=48.85% at RT 11.74 min.

I-60

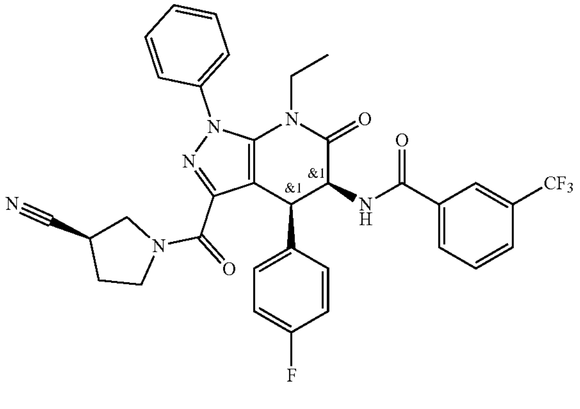

$^1$H NMR (400 MHZ, DMSO-$d_6$) δ=8.57-8.52 (m, 1H), 8.18-8.11 (m, 2H), 7.92 (d, J=7.9 Hz, 1H), 7.83-7.76 (m, 2H), 7.71 (t, J=7.8 Hz, 1H), 7.68-7.56 (m, 3H), 7.11-7.03 (m, 2H), 7.01-6.93 (m, 2H), 5.55-5.47 (m, 1H), 5.04-4.98 (m, 1H), 4.25-3.86 (m, 3H), 3.79-3.40 (m, 2H), 3.07-3.00 (m, 1H), 2.29-2.03 (m, 3H), 0.90 (t, J=7.1 Hz, 3H). LC-MS (Method-H)=645.41 $[M+H]^+$; 96.31% at RT 2.39 min. HPLC (Method-H)=95.14% at RT 9.01 min. Chiral HPLC (Method-F)=Peak-1=50.37% at RT 12.26 min. Peak-2=49.57% at RT 15.21 min.

I-94

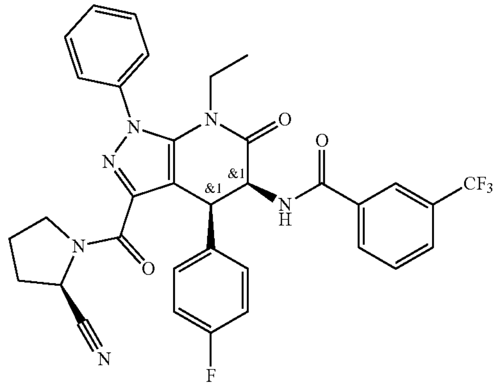

$^1$H NMR (400 MHZ, DMSO-$d_6$) δ=8.59-8.52 (m, 1H), 8.19-8.12 (m, 2H), 7.92 (d, J=7.6 Hz, 1H), 7.88-7.77 (m, 2H), 7.71 (t, J=7.8 Hz, 1H), 7.68-7.58 (m, 4H), 7.11-7.04 (m, 2H), 7.03-6.95 (m, 2H), 5.64-5.44 (m, 2H), 5.09-4.84 (m, 2H), 3.97-3.83 (m, 2H), 3.61-3.42 (m, 1H), 3.11-3.00 (m, 1H), 2.26-2.09 (m, 2H), 2.02-1.96 (m, 1H), 0.92-0.88 (t, J=7.1 Hz, 3H). LC-MS (Method-D)=645.0 $[M+H]^+$; 98.75% at RT 2.43 min. HPLC (Method-B)=98.32% at RT 9.32 min. Chiral HPLC (Method-T)=Peak-1=50.21% at RT 6.27 min. Peak-2-49.78% at RT 7.01 min.

I-137

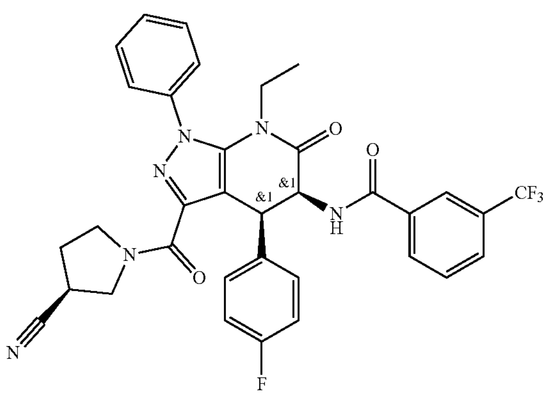

$^1$H NMR (400 MHz, DMSO-$d_6$) δ=8.59-8.49 (m, 1H), 8.18-8.10 (m, 2H), 7.92 (d, J=7.5 Hz, 1H), 7.83-7.76 (m, 2H), 7.71 (t, J=7.8 Hz, 1H), 7.65-7.58 (m, 3H), 7.09-7.04 (m, 2H), 7.02-6.95 (m, 2H), 5.55-5.47 (m, 1H), 5.04-4.97 (m, 1H), 4.26-3.89 (m, 3H), 3.74-3.42 (m, 3H), 3.09-3.01 (m, 1H), 2.22-2.07 (m, 2H), 0.91 (t, J=7.1 Hz, 3H). LC-MS (Method-I)=645.2 $[M+H]^+$; 97.69% at RT 6.14 min. HPLC (Method-N)=95.31% at RT 6.22 min. Chiral HPLC (Method-U)=Peak-1=49.85% at RT 5.81 min. Peak-2=50.15% at RT 6.65 min.

I-121

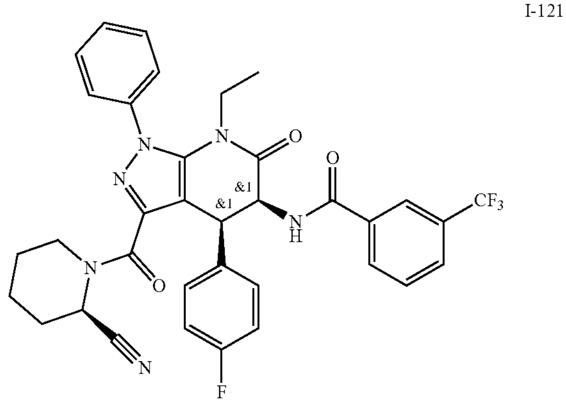 [SMILES: CCN1C(=O)[C@@H](NC(=O)c2cccc(C(F)(F)F)c2)[C@@H](c2ccc(F)cc2)c2c(C(=O)N3CCCC[C@@H]3C#N)nn(-c3ccccc3)c21]

$^1$H NMR (400 MHZ, DMSO-$d_6$) δ=8.59-8.52 (m, 1H), 8.19-8.12 (m, 2H), 7.92 (d, J=7.6 Hz, 1H), 7.88-7.77 (m, 2H), 7.71 (t, J=7.8 Hz, 1H), 7.68-7.58 (m, 3H), 7.11-7.04 (m, 2H), 7.03-6.95 (m, 2H), 6.26-5.64 (m, 2H), 4.85-4.43 (m, 2H), 3.97-3.83 (m, 1H), 3.61-2.66 (m, 2H), 1.90-1.70 (m, 1H), 1.71-1.55 (m, 5H), 0.90 (t, J=7.1 Hz, 3H). LC-MS (Method-D)=659.0 $[M+H]^+$; 98.87% at RT 2.42 min. HPLC (Method-B)=98.18% at RT 9.74 min.

I-157

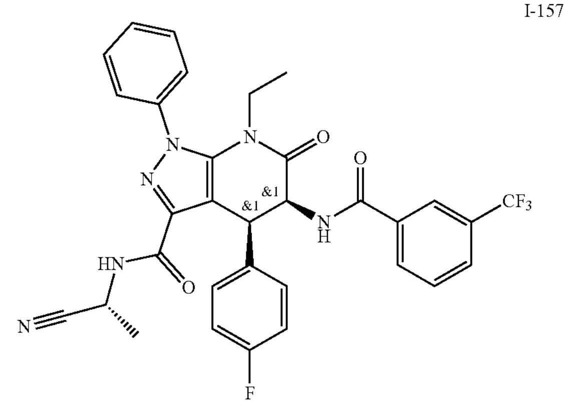 [SMILES: CCN1C(=O)[C@@H](NC(=O)c2cccc(C(F)(F)F)c2)[C@@H](c2ccc(F)cc2)c2c(C(=O)N[C@H](C)C#N)nn(-c3ccccc3)c21]

$^1$H NMR (400 MHZ, DMSO-$d_6$) δ=9.13 (t, J=7.9 Hz, 1H), 8.57 (dd, J=1.6, 7.1 Hz, 1H), 8.16-8.13 (m, 2H), 7.92 (d, J=7.8 Hz, 1H), 7.83-7.73 (m, 2H), 7.71 (t, J=7.8 Hz, 1H), 7.65-7.61 (m, 3H), 7.11-7.08 (m, 2H), 7.12-6.98 (m, 2H), 5.57-5.49 (m, 1H), 5.01-4.86 (m, 2H), 3.91-3.85 (m, 1H), 3.06-2.95 (m, 1H), 1.46 (dd, J=3.3, 7.1 Hz, 3H), 0.90 (t, J=6.9 Hz, 3H). LC-MS (Method-D)=617.0 $[M-H]^+$; 99.81% at RT 2.42 min. HPLC (Method-B)=99.84% at RT 9.29 min.

Synthesis of I-96

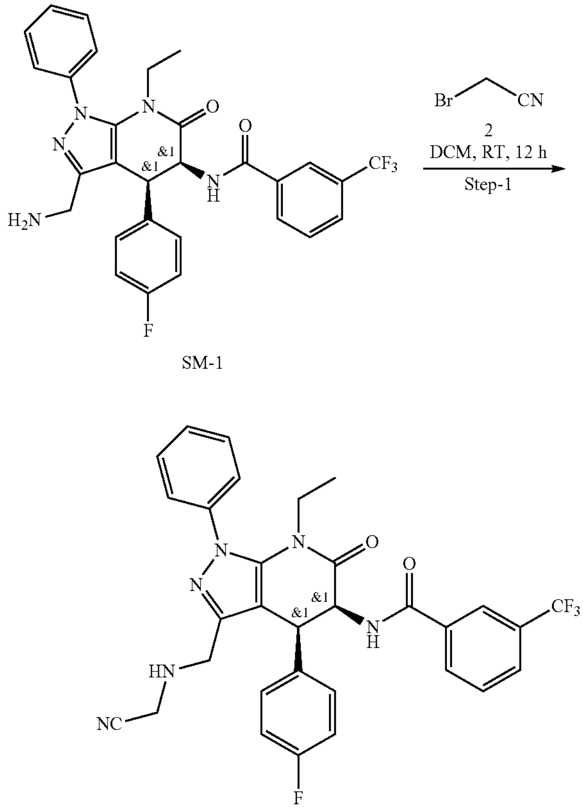

SM-1

I-96

Step-1: rac-N-((4R,5R)-3-(((cyanomethyl)amino)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (I-96)

To a stirred solution of SM-1 (250 mg, 0.453 mmol) in DCM (5.0 mL) was added 2-bromoacetonitrile (54.3 mg, 0.453 mmol) at room temperature. The reaction mixture stirred at room temperature for 12 h. The progress of the reaction was monitored by TLC & LCMS. The reaction mixture was concentrated under vacuum, quenched with water (25 mL), and extracted with DCM (2×25 mL)). The combined organic layers were dried over anhydrous sodium sulfate and concentrated under reduced pressure to obtain the crude compound. The crude compound was purified by silica gel (230-400 mesh) column chromatography and eluted the compound at 45% EtOAc/Heptane to afford the title compound I-96 (35 mg, 12.73%) as a white solid.

$^1$H NMR (400 MHZ, DMSO-$d_6$) δ=8.52 (d, J=7.1 Hz, 1H), 8.17-8.11 (m, 2H), 7.92 (d, J=7.7 Hz, 1H), 7.74-7.64 (m, 3H), 7.59-7.54 (m, 3H), 7.12-7.07 (m, 2H), 7.02-6.96 (m, 2H), 5.50 (t, J=7.3 Hz, 1H), 4.66 (d, J=7.2 Hz, 1H), 3.94-3.85 (m, 1H), 3.69-3.56 (m, 2H), 3.46 (dd, J=2.8, 7.3 Hz, 2H), 3.09-3.00 (m, 1H), 2.80-2.74 (m, 1H), 0.91 (t, J=7.0 Hz, 3H). LC-MS (Method-D)=591.0 $[M+H]^+$; 99.43% at RT 2.25 min. HPLC (Method-B)=98.42% at RT 9.18 min. Chiral HPLC (Method-L)=Peak-1=50.11% at RT 5.01 min. Peak-2=49.89% at RT 6.19 min.

Synthesis of I-223

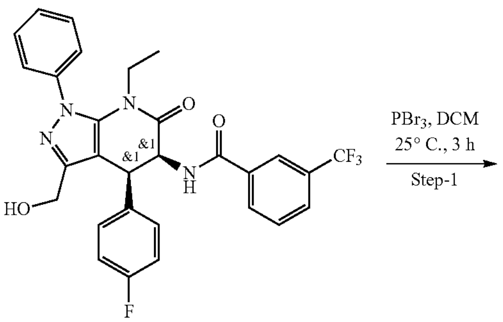

15-1

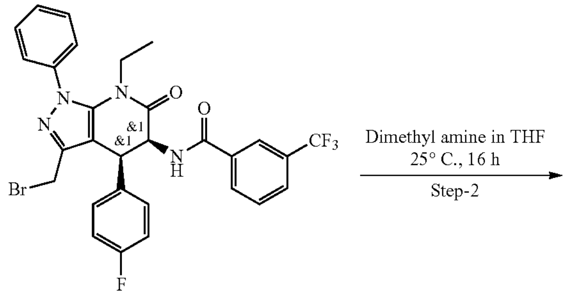

1

-continued

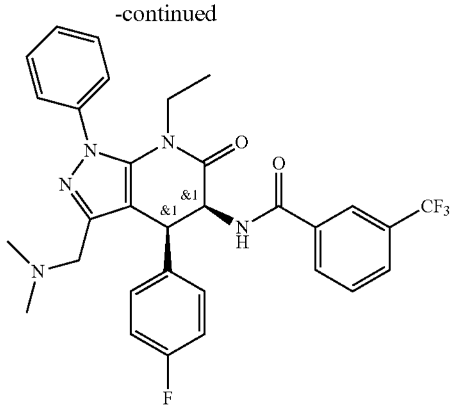

I-223

Step-1: Synthesis of rac-N-((4R,5R)-3-(bromomethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (1)

To a stirring solution of N-[(4S, 5S)-7-ethyl-4-(4-fluoro phenyl)-3-(hydroxy methyl)-6-oxo-1-phenyl-4,5-dihydro-pyrazolo[3,4-b]pyridine-5-yl]-3-(trifluoromethyl)benzamide (1) (300 mg, 0.543 mmol) in DCM (10 mL) was added phosphorus tribromide (0.077 mL, 0.814 mmol) at 0° C. under inert atmosphere. The reaction mixture was stirred at 25° C. for 3 h. After consumption of the starting material (by TLC), the reaction was poured into ice cold water (20 mL) and extracted with EtOAc (2×30 mL). The organic layer was dried over anhydrous $Na_2SO_4$, concentrated under reduced pressure. The crude material was purified by medium pressure liquid chromatography by eluting with 30-40% EtOAc/heptane to obtain compound (2) (250 mg, 59.10%).

$^1$H NMR (400 MHZ, $CDCl_3$) δ=8.06 (br s, 1H), 7.92-7.79 (m, 2H), 7.64-7.47 (m, 6H), 6.97 (br s, 5H), 5.26 (s, 1H), 4.96 (d, J=4.9 Hz, 1H), 4.46-4.25 (m, 2H), 3.97 (d, J=4.9 Hz, 1H), 3.22 (d, J=5.9 Hz, 1H), 1.06-0.97 (t, J=7.0 Hz, 3H). LC-MS (Method-G)=617.31 $[M+2]^+$=79.39% at RT 2.33 min.

Step-2: Synthesis of rac-N-((4R,5R)-3-((dimethylamino)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (I-223)

To a compound N-[(4S, 5S)-3-(bromomethyl)-7-ethyl-4-(4-fluorophenyl)-6-oxo-1-phenyl-4,5-dihydro pyrazolo[3,4-b]pyridine-5-yl]-3-(trifluoromethyl)benzamide (180 mg, 0.263 mmol) was added dimethylamine in THF (0.17 mL, 2.632 mmol) under inert atmosphere at room temperature. The reaction mixture was stirred at 25° C. for 16 h. After consumption of the starting material (by TLC), the reaction was concentrated under vacuum. Then the reaction mixture was quenched with water (10 mL) and extracted with DCM (3×20 mL). The combined organic layers were dried over anhydrous sodium sulfate and concentrated to get crude compound. The crude compound was purified by Prep-HPLC followed by lyophilization to afford the fraction-2 I-223 (20 mg, 9.83%) as white solid.

$^1$H NMR (400 MHZ, DMSO-$d_6$) δ=8.49 (d, J=7.1 Hz, 1H), 8.18-8.10 (m, 2H), 7.92 (d, J=7.5 Hz, 1H), 7.67 (d,

J=7.3 Hz, 3H), 7.61-7.53 (m, 3H), 7.13-7.05 (m, 2H), 7.00-6.96 (m, 2H), 5.48 (t, J=7.3 Hz, 1H), 4.66 (d, J=7.2 Hz, 1H), 3.93-3.85 (m, 1H), 3.25 (d, J=5.9 Hz, 2H), 3.11-3.03 (m, 1H), 2.02 (s, 6H), 0.92 (t, J=7.0 Hz, 3H). LC-MS (Method-D)=580.1 $[M+H]^+$; 99.935% at RT 2.40 min. HPLC (Method-B)=91.762% at RT 9.71 min. Chiral HPLC (Method-P)=Peak-1=49.38% at RT 6.36 min. Peak-2=50.61% at RT 7.51 min.

Example 16: Synthesis of Compounds I-244, I-245, I-246, I-247, I-248 and I-249

NMR:

$^1$H NMR spectrum was recorded on Bruker 400 MHz and Varian 400 MHZ instruments internally referenced to a tetramethylsilane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: I (95:5); B: 0.05% Formic acid in I Inj Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge BEH C18, (50 mm*3.0 mm,2.5μ) Mobile Phase A: 2.5 mM Ammonium Bicarbonate in Water+5% CAN; Mobile Phase B: 100% CAN; Flow rate: 1.0 mL/min. Column temperature: 40° C. Gradient Program (B %): 0.0/2, 0.3/2, 2.0/98, 2.8/98, 3.0/2,3.7/2.

Method-C: Column: X-Select CSH C18 (50 mm*3.0 mm,2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2,2.0/98, 2.8/98, 3.0/2,3.7/2.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5, 1/5,8/100,12/100,14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/2,2/2,12/90,16/90; Flow: 1.0 mL/min.; Diluent: I: WATER (80:20).

Method-C: Column: X SELECT CSH C18 (150×4.6 mm, 3.5μ); Mobile Phase A; 0.05% TFA in water: I (95:05); Mobile Phase B: 0.05% TFA IN WATER: I (05:95); Programme: T/B %: . 0.01/10, 12/90, 16/90; Flow: 1 mL/min.; Diluent: WATER: I (80:20).

Method-D: Column: X-Bridge CSH C18 (4.6*150) mm 5μ Mobile Phase: A-0.1% TFA in water; B-Acetonitrile; Inj Volume; 5.0 μL, Flow Rate: 1.2. mL/minute Gradient program: Time (min)/B Conc.: 0.01/5, 1.0/5, 8.0/100, 12.0/100, 14.0/5, 18.0/5.

Chiral HPLC:

Method-A: Column: CHIRALCEL-OX-H (250×4.6 mm, 5 μm) Mobile Phase A: n-Hexane; Mobile Phase B: EtOH: MeOH (1:1) A/B: 50/50 Flow: 1.0 ml/Min.

Method-B: Column: CHIRALPAK IG (250×4.6 mm, 5 μm) MobilePhase A: 0.1% DEA in n-Hexane; MobilePhase B: IPA A: B-60:40 Flow rate: 1.0 ml/min.

Method-C: Column: CHIRAL PAK IA (250×4.6 mm, 5 μm) MobilePhase A n-Hexane MobilePhase; B: IPA; A: B: 70:30 Flow rate: 1.0 ml/min.

Method-D: Column: CHIRALPAK-IK (250×4.6 mm, 5 μm) Mobile Phase-A: n-Hexane; Mobile Phase-B: IPA: MeOH (50:50) B: 50:50 Flow: 1.0 ML/Min.

Method-E: Column: CHIRALPAK-IK (150×4.6 mm, 3 μm) Mobile Phase A: 0.1% IP Amine in n-Hexane Mobile Phase B: ETOH/MEOH (50/50) A/B: 70/30 Flow: 1.0 ml/Min.

Synthesis of I-244

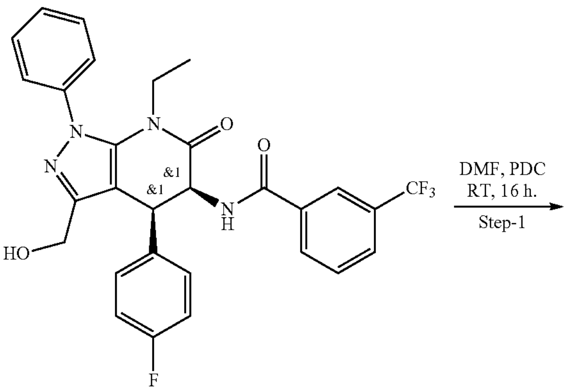

16-1

-continued
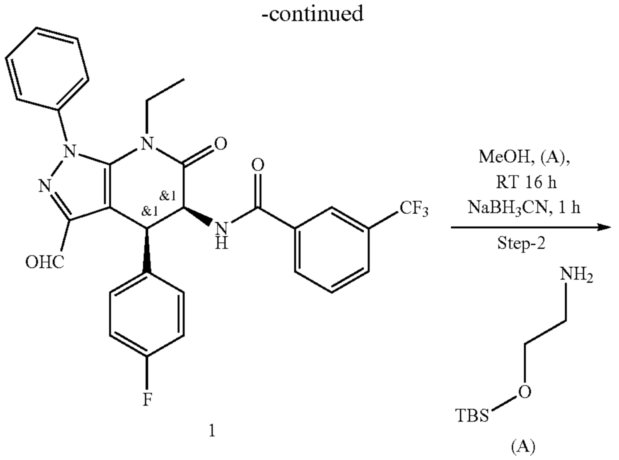
1
(A)
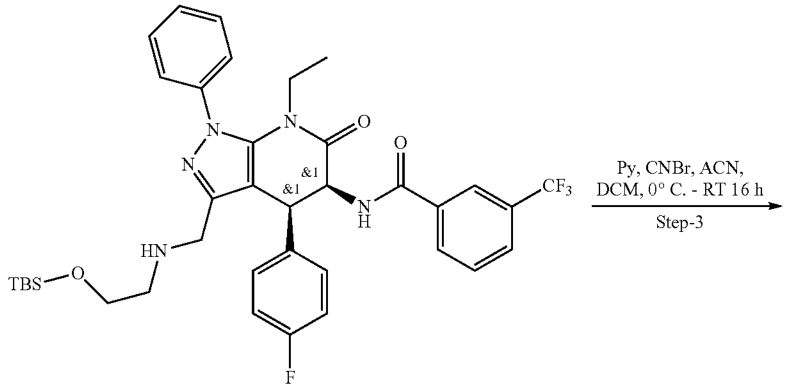
2
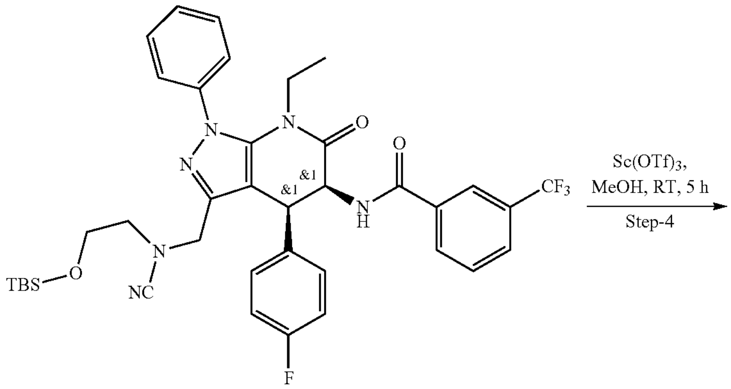
3
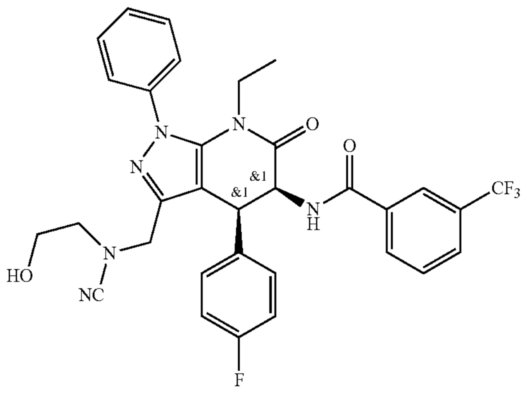
I-244

Step-1: Synthesis of ~{N}-[(4~{S},5~{S})-7-ethyl-4-(4-fluorophenyl)-3-formyl-6-oxo-1-phenyl-4,5-dihydropyrazolo[3,4-b]pyridine-5-yl]-3-(trifluoromethyl)benzamide (1)

To a stirred solution of ~{N}-[(4~{S},5~{S})-7-ethyl-4-(4-fluorophenyl)-3-(hydroxymethyl)-6-oxo-1-phenyl-4,5-dihydropyrazolo[3,4-b]pyridine-5-yl]-3-(trifluoromethyl) benzamide (2 g, 3.620 mmol) in DMF (20 mL) were added pyridinium dichromate (1.66 g, 4.34 mmol) and the reaction mixture was stirred at room temperature for 16 h. The progress of reaction was monitored by TLC. After completion of reaction, the reaction mixture was quenched with ice cold water (200 mL), extracted with EtOAc (2×250 mL). The combined organic layer was dried over anhydrous $Na_2SO_4$ and concentrated under reduced pressure to afford crude product. The crude product was purified by Combi Flash column chromatography (silica gel as stationary phase and 0-50% EtOAc in Heptane as mobile phase) to afford compound (1) (1.6 g, 79%) as a white solid.

$^1$H NMR (400 MHZ, DMSO-$d_6$): 9.86 (s, 1H), 8.63 (d, J=7.2 Hz, 1H), 8.14-8.11 (m, 2H), 7.93-7.89 (m, 1H), 7.82-7.80 (m, 2H), 7.71-7.63 (m, 4H), 7.10-7.06 (m, 2H), 7.01-6.97 (m, 2H), 5.57-5.54 (m, 1H), 4.87 (d, J=7.6 Hz, 1H), 3.89-3.84 (m, 1H), 3.02-2.97 (m, 1H), 0.89-0.83 (m, 3H). LC-MS (Method-A)=549.2 $[M-H]^-$; 99.85% at RT 2.55 min.

Step-2: Synthesis of ~{N}-[(4~{S},5~{S})-3-[[2-[~{tert}-butyl(dimethyl)silyl]oxyethylamino] methyl]-7-ethyl-4-(4-fluorophenyl)-6-oxo-1-phenyl-4,5-dihydropyrazolo[3,4-b]pyridine-5-yl]-3-(trifluoromethyl)benzamide (2)

To a stirred solution of compound (1) (500 mg, 0.84 mmol) in Methanol (5 mL) was added 2-[~{tert}-butyl (dimethyl)silyl]oxyethanamine (0.22 g, 1.26 mmol) at room temperature. Reaction mixture was stirred at room temperature for 16 h. Reaction progress was monitored by TLC. After 16 h, sodium cyanoborohydride (0.16 g, 2.53 mmol) was added and stirred for 1 h. Reaction progress was monitored by TLC and LCMS. After completion, reaction mixture was concentrated under reduced pressure to afford crude compound. Crude compound was purified by silica gel chromatography eluted with 0-50% EA in Heptane, concentrated under reduced pressure to afford compound (2) (280 mg, 29.42%) as a yellow solid.

$^1$H NMR (400 MHZ, DMSO-$d_6$) δ: 8.51 (d, J=7.2 Hz, 1H), 8.15-8.12 (m, 2H), 7.92 (d, J=8.0 Hz, 1H), 7.71 (t, J=8.0 Hz, 1H), 7.66-7.64 (m, 2H), 7.57 (t, J=7.2 Hz, 2H), 7.53-7.49 (m, 1H), 7.08 (t, J=8.8 Hz, 2H), 6.99-6.95 (m, 2H), 5.75 (s, 1H), 5.50-5.46 (m, 1H), 4.69 (d, J=7.2 Hz, 1H), 3.92-3.87 (m, 1H), 3.66 (d, J=14 Hz, 1H), 3.55 (d, J=14 Hz, 1H), 3.42-3.34 (m, 2H), 3.08-3.02 (m, 1H), 2.50-2.38 (m, 2H), 0.91 (t, J=6.8 Hz, 3H), 0.80 (s, 9H), −0.03 (s, 6H). LC-MS (Method-A)=710.41 $[M+H]^+$; 97.81% at RT 1.45 min.

Step-3: Synthesis of ~{N}-[~{rac}-(4~{S},5~{S})-3-[[2-[~{tert}-butyl(dimethyl)silyl]oxyethyl-cyano-amino]methyl]-7-ethyl-4-(4-fluorophenyl)-6-oxo-1-phenyl-4,5-dihydropyrazolo[3,4-b]pyridine-5-yl]-3-(trifluoromethyl)benzamide (3)

To a stirred solution of compound (2) (250.00 mg, 0.35 mmol) in dichloromethane (2.5 mL) was added pyridine (0.16 g, 2.11 mmol) & cyanogen bromide (5.0 mol/L) in qacetonitrile (0.11 mL, 0.56 mmol) at 0° C. to room temperature. Reaction mixture was stirred at room temperature for 16 h. The progress of reaction was monitored by TLC and LCMS. The progress of reaction was monitored by TLC and LCMS. Reaction mixture was allowed to room temperature, Then the reaction mixture quenched with water (25 mL), and extracted with DCM (2×25 mL), combined organic layers were dried over anhydrous sodium sulphate and concentrated to afford crude compound. Obtained crude compound was purified by silica gel (230-400 mesh) column chromatography using eluted with 40% EtOAc in heptane, product containing fractions were collected and concentrated to afford compound (3) (135 mg, 52.16%) as a yellow syrup.

$^1$H NMR (400 MHZ, DMSO-$d_6$) δ: 8.54 (d, J=7.2 Hz, 1H), 8.15-8.12 (m, 2H), 7.92 (d, J=8.0 Hz, 1H), 7.69-7.68 (m, 3H), 7.60-7.57 (m, 3H), 7.10 (t, J=8.0 Hz, 2H), 6.99-6.95 (m, 2H), 5.54 (s, 1H), 4.63 (d, J=6.8 Hz, 1H), 4.30-4.26 (m, 1H), 4.18-4.14 (m, 1H), 3.92-3.85 (m, 1H), 3.51 (s, 2H), 3.04-3.08 (m, 1H), 2.79-2.74 (m, 2H), 1.24 (s, 3H), 0.92-0.82 (m, 9H), −0.05 (s, 6H). LC-MS (Method-B)=735.1 $[M+H]^+$; 96.00% at RT 2.52 min.

Step-4: Synthesis of ~{N}-[~{rac}-(4~{S},5~{S})-3-[[cyano(2-hydroxyethyl)amino]methyl]-7-ethyl-4-(4-fluorophenyl)-6-oxo-1-phenyl-4,5-dihydropyrazolo[3,4-b]pyridine-5-yl]-3-(trifluoromethyl) benzamide (4): I-244

To a stirred solution of compound (3) (100 mg, 0.13 mmol) in methanol (2 mL) was added Scandium (III) trifluoromethanesulfonate (0.07 g, 0.14 mmol) at room temperature. Reaction mixture was stirred at room temperature for 5 h. The progress of reaction was monitored by TLC and LCMS. Reaction mixture was concentrated under vacuum, quenched with ice cold water (20 mL), and extracted with EtOAc (2×20 mL). Combined organic layers were dried over anhydrous sodium sulphate and concentrated to afford crude compound. Obtained crude compound was purified by silica gel (230-400 mesh) column chromatography using ethyl acetate in heptane. Product was eluted in 50% EtOAc in heptane. Product containing fractions were collected and concentrated to afford semi pure compound which was repurified by prep-HPLC to afford I-244 (30 mg, 35.53%) as a white solid.

$^1$H NMR (400 MHZ, DMSO-$d_6$) δ: 9.23-9.04 (m, 1H), 8.64 (d, J=7.3 Hz, 1H), 8.19-8.16 (m, 1H), 8.15 (s, 1H), 7.94 (d, J=7.8 Hz, 1H), 7.76-7.68 (m, 3H), 7.65-7.52 (m, 3H), 7.12 (t, J=8.8 Hz, 2H), 6.97-6.89 (m, 2H), 5.56 (t, J=7.3 Hz, 1H), 4.88-4.80 (m, 1H), 4.60 (d, J=7.4 Hz, 1H), 4.53-4.43 (m, 1H), 4.41-4.34 (m, 1H), 3.91-3.86 (m, 1H), 3.82-3.76 (m, 1H), 3.67-3.59 (m, 1H), 3.37-3.33 (m, 1H), 3.11-3.03 (m, 1H), 0.93 (t, J=6.9 Hz, 3H). LC-MS (Method-C)=621.2 $[M+H]^+$; 98.93% at RT 5.47 min. HPLC (Method-B)=99.36% at RT 8.97 min. Chiral-HPLC (Method-A): Peak-1=49.42% at RT 3.74 min, Peak-2=49.57% at RT 4.52 min.

Synthesis of I-248 & I-249
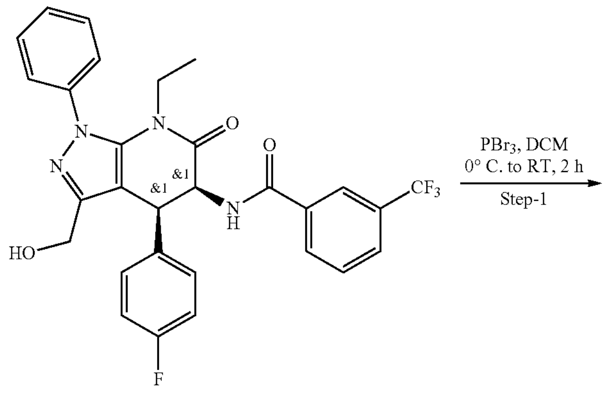
(SM)
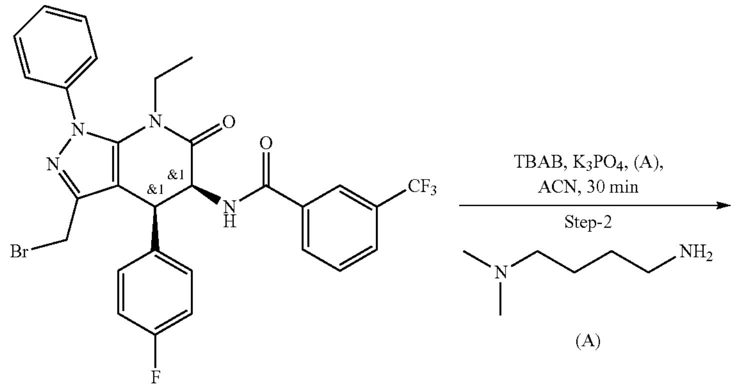
(A)
(1)
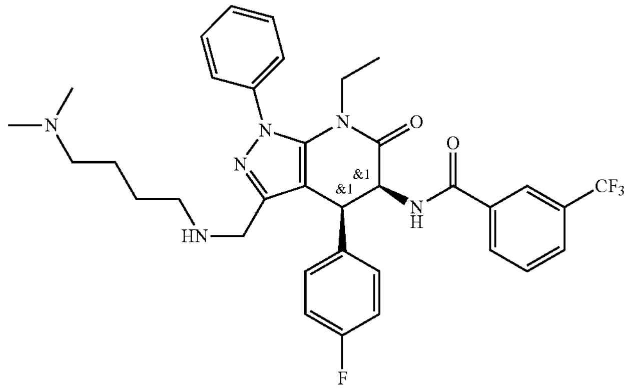
(2a)

-continued

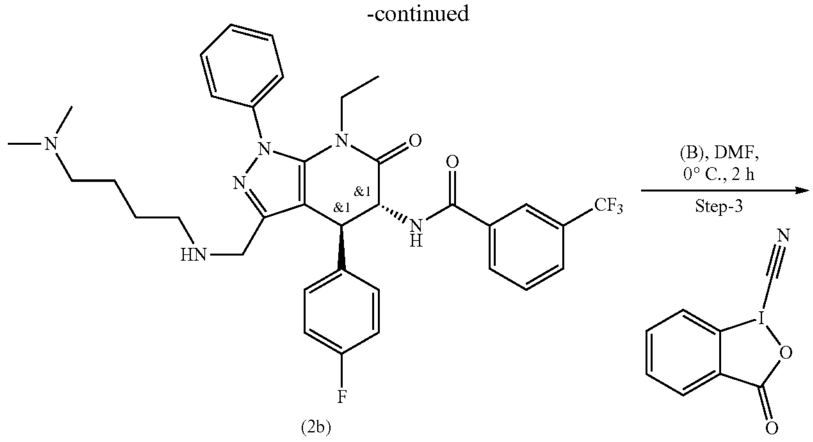

(2b)

(B)

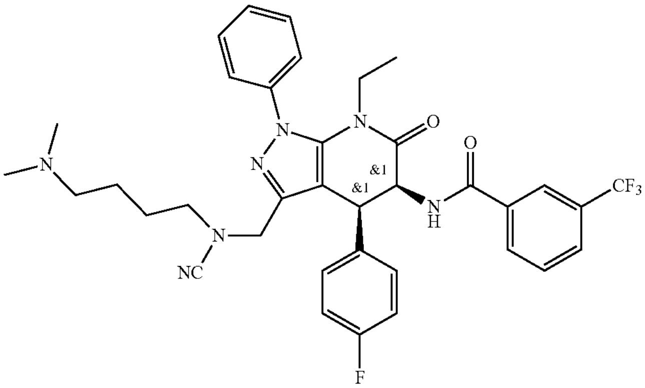

I-248

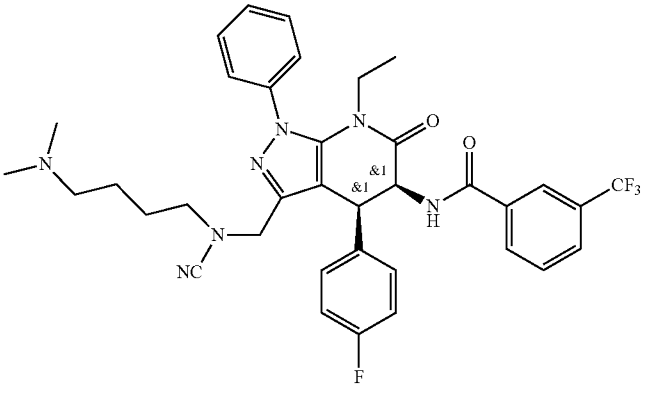

I-249

Step 1: Synthesis of ~{N}-[~{rac}-(4~{S},5~{S})-3-(bromomethyl)-7-ethyl-4-(4-fluoro phenyl)-6-oxo-1-phenyl-4,5-dihydropyrazolo[3,4-b]pyridine-5-yl]-3-(trifluoromethyl)benzamide (1)

To a stirred solution of ~{N}-[(4~{S},5~{S})-7-ethyl-4-(4-fluorophenyl)-3-(hydroxymethyl)-6-oxo-1-phenyl-4,5-dihydropyrazolo[3,4-b]pyridine-5-yl]-3-(trifluoromethyl) benzamide (1.0 g, 1.44 mmol) in dichloromethane (10 mL) was added Phosphorous tribromide (593 mg, 2.17 mmol) at 0° C. and the reaction mixture was stirred at same temperature for 2 h. Reaction progress was monitored by TLC (40-50% EtOAc/Heptane). After completion of starting material by TLC, reaction mixture was directly concentrated under reduced pressure, quenched with water (50 mL), and extracted with EtOAc (2×100 mL). The combined organic layers were dried over anhydrous $Na_2SO_4$, filtered, and concentrated under reduced pressure to obtain crude compound. Obtained crude was purified by silica gel medium pressure liquid column chromatography, eluted at 40-50% EtOAc/Heptane to afford compound (1) (650 mg, 72.22%) as an off-white solid.

$^1$H NMR (400 MHZ, DMSO-$d_6$) δ=8.57 (d, J=6.4 Hz, 1H), 8.16 (d, J=12.4 Hz, 2H), 7.93 (d, J=7.2 Hz, 1H), 7.72 (d, J=6.8 Hz, 3H), 7.62-7.55 (m, 3H), 7.13 (t, J=8.8 Hz, 2H), 7.01 (d, J=5.6 Hz, 2H), 5.56 (t, J=7.2 Hz, 1H), 4.76-4.63 (m, 2H), 4.39 (d, J=11.2 Hz, 1H), 3.88-3.92 (m, 1H), 3.05-3.09 (m, 1H), 0.93 (t, J=6.8 Hz, 3H). LC-MS (Method-A): 617.07 $(M+2H)^+$, 99.16% at RT 1.71 min.

Step 2: Synthesis of ~{N}-[~{rac}-(4~{S},5~{S})-3-[[4-(dimethylamino)butylamino]methyl]-7-ethyl-4-(4-fluorophenyl)-6-oxo-1-phenyl-4,5-dihydropyrazolo[3,4-b]pyridine-5-yl]-3-(trifluoromethyl)benzamide (2)

To a stirred solution of compound (1) (1 g, 1.62 mmol) in I (10 mL) were added tetrabutylammonium bromide (1.04 g, 3.16 mmol), potassium phosphate tribasic (700 mg, 3.20 mmol) and ~{N}',~{N}'-dimethylbutane-1,4-diamine (0.8 mL) and the reaction mass and was stirred for 30 min. Reaction progress was monitored by TLC and LCMS. After completion of starting material by TLC, reaction mass was diluted with water (50 mL) and extracted with EtOAc (2×100 mL). The combined organic layers were dried over anhydrous $Na_2SO_4$, filtered, and concentrated under reduced pressure to obtain crude compound. Obtained crude was purified by silica gel medium pressure liquid column chromatography, eluted at 15-20% MeOH/DCM to afford mixture of 2a and 2b (270 mg, 25.54%) as an off white solid. LC-MS (Method-C)=651.2 $(M+H)^+$, 46.05% at RT 4.62 min. HPLC (Method-D)=54.46% at RT 6.20 min.

Step 3: Synthesis of ~{N}-[(4~{S},5~{S})-3-[[cyano-[4-(dimethylamino)butyl]amino]methyl]-7-ethyl-4-(4-fluorophenyl)-6-oxo-1-phenyl-4,5-dihydropyrazolo[3,4-b]pyridine-5-yl]-3-(trifluoromethyl)benzamide & ~{N}-[(4~{S},5~{R})-3-[[cyano-[4-(dimethylamino)butyl]amino]methyl]-7-ethyl-4-(4-fluorophenyl)-6-oxo-1-phenyl-4,5-dihydropyrazolo[3,4-b]pyridine-5-yl]-3-(trifluoromethyl)benzamide (3): I-248 & I-249

To a stirred solution of compound (2a and 2b mixture) (180.00 mg, 0.27 mmol) in DMF (4 mL), was added 1,2-benziodooxole-1 (3H)-carbonitrile,3-oxo-(103.4 mg, 0.35 mmol) at 0° C. and the reaction mixture was stirred at room temperature for 2 h. Reaction progress was monitored by TLC and LCMS. After completion of starting material by TLC, reaction mass was diluted with water (25 mL) and extracted with EtOAc (2×25 mL). The combined organic layers were dried over anhydrous $Na_2SO_4$, filtered, and concentrated under reduced pressure to obtain crude compound. Obtained crude was purified by silica gel medium pressure liquid column chromatography followed by Prep.HPLC to afford I-248 (25 mg, 13.38%) and I-249 (15 mg, 8.02%) as an off-white solid.

I-248, Cis (peak-2):

$^1H$ NMR (400 MHZ, DMSO-$d_6$) δ: 8.57 (d, J=7.2 Hz, 1H), 8.16 (t, J=5.6 Hz, 2H), 7.93 (d, J=8.0 Hz, 1H), 7.73-7.68 (m, 3H), 7.62-7.55 (m, 3H), 7.13 (t, J=8.8 Hz, 2H), 7.01 (q, J=8.4 Hz, 2H), 5.55 (t, J=7.6 Hz, 1H), 4.64 (d, J=7.2 Hz, 1H), 4.26 (d, J=15.2 Hz, 1H), 4.13 (d, J=14.8 Hz, 1H), 3.90 (q, J=14.4 Hz, 1H), 3.09-3.12 (m, 1H), 2.71-2.62 (m, 2H), 2.04 (s, 8H), 1.29-1.18 (m, 4H), 0.94 (t, J=7.2 Hz, 3H). LC-MS (Method-C): 676.3 $(M+H)^+$, 97.46% at RT 5.32 min. HPLC (Method-B): 98.96% at RT 9.39 min. Chiral-HPLC (Method-E): Peak-1=50.00% at RT 7.76 min, Peak-2=49.99% at RT 10.97 min.

I-249, Trans (peak-1):

$^1H$ NMR (400 MHZ, DMSO-$d_6$) δ=9.01 (d, J=9.2 Hz, 1H), 8.02 (d, J=8.0 Hz, 2H), 7.91 (d, J=7.6 Hz, 1H), 7.72-7.67 (m, 3H), 7.62-7.52 (m, 3H), 7.45-7.50 (m, 2H), 7.20 (t, J=8.8 Hz, 2H), 5.28-5.32 (m, 1H), 4.48 (d, J=12.4 Hz, 1H), 3.75-3.79 (m, 1H), 3.66 (d, J=14.0 Hz, 1H), 3.21 (d, J=14.0 Hz, 1H), 3.10-3.20 (m, 1H), 2.70 (t, J=6.8 Hz, 2H), 2.11 (t, J=6.8 Hz, 2H), 2.06 (s, 6H), 1.37-1.23 (m, 4H), 0.82 (t, J=6.8 Hz, 3H). LC-MS (Method-C)=676.3 $(M+H)^+$, 92.01% at RT 4.91 min. HPLC (Method-B)=98.63% at RT 8.72 min. Chiral-HPLC (Method-E)=Peak-1=49.97% at RT 5.55 min, Peak-2=50.02% at RT 6.43 min.

Synthesis of I-247

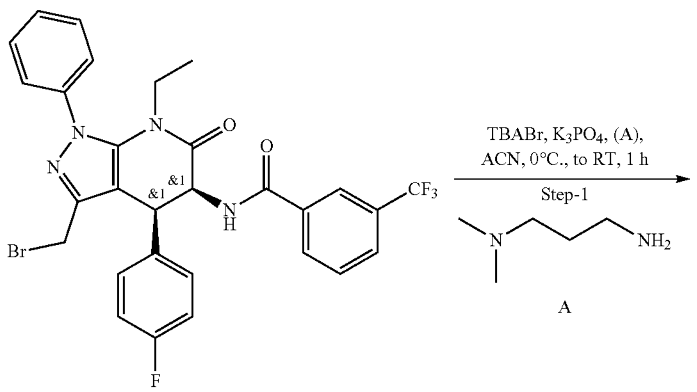

SM-1

-continued

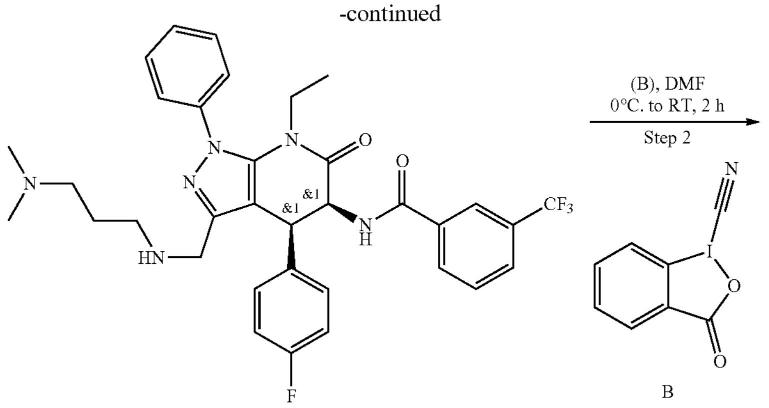

(1) B

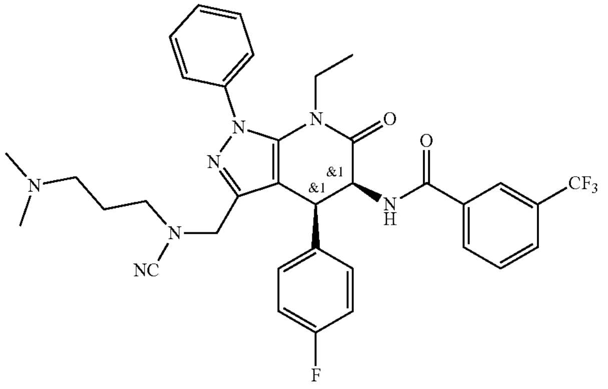

I-247

Step 1: Synthesis of ~{N}-[~{rac}-(4~{S},5~{S})-3-[[3-(dimethylamino)propylamino]methyl]-7-ethyl-4-(4-fluorophenyl)-6-oxo-1-phenyl-4,5-dihydropyrazolo[3,4-b]pyridine-5-yl]-3-(trifluoromethyl) benzamide To a stirred solution of SM-1 (1.2 g, 1.9 mmol) in I (12 mL) were added tetrabutylammonium bromide (1.30 g, 3.95 mmol), potassium phosphate tribasic (860.00 mg, 3.93 mmol) and N,N-Dimethyl-1,3-propanediamine (0.35 mL, 2.8 mmol) and the reaction mixture and was stirred at room temperature for 1 h. Reaction progress was monitored by TLC. After completion of starting material by TLC, reaction mixture was diluted with water (100 mL) and extracted with EtOAc (2×50 mL). The combined organic layers were dried over anhydrous $Na_2SO_4$, filtered, and concentrated under reduced pressure to obtain crude compound. Obtained crude was purified by silica gel medium pressure liquid column chromatography, eluted at 15-17% MeOH/DCM to afford compound (1) (350 mg, 28%) as off-white solid. LC-MS (Method-C): 637.3 $(M+H)^+$, 73.41% at RT 4.53 min. HPLC (Method-D): 78.45% at RT 6.22 min.

Step 2: Synthesis of ~{N}-[(4~{S},5~{S})-3-[[cyano-[3-(dimethylamino)propyl]amino]methyl]-7-ethyl-4-(4-fluorophenyl)-6-oxo-1-phenyl-4,5-dihydropyrazolo[3,4-b]pyridine-5-yl]-3-(trifluoromethyl) benzamide (2): I-247

To a stirred solution of compound (1) (200 mg, 0.31 mmol) in DMF (4 mL), was added 1,2-benziodoxole-1 (3H)-carbonitrile,3-oxo-(117 mg, 0.40 mmol) at 0° C. and the reaction mixture was stirred at room temperature for 2 h. Reaction progress was monitored by TLC. After completion of the starting material by TLC, reaction mixture was diluted with water (25 mL) and reaction mixture and extracted with EtOAc (2×25 mL). The combined organic layers were dried over anhydrous $Na_2SO_4$, filtered, and concentrated under reduced pressure to obtain crude compound. Obtained crude was purified by Prep. HPLC to afford I-247 (40 mg, 19.24%) as off white solid.

$^1H$ NMR (400 MHZ, DMSO-$d_6$) δ: 8.55 (d, J=7.6 Hz, 1H), 8.16 (d, J=13.2 Hz, 2H), 7.93 (d, J=8.0 Hz, 1H), 7.73-7.68 (m, 3H), 7.62-7.53 (m, 3H), 7.13 (t, J=8.8 Hz, 2H), 6.99-7.03 (m, 2H), 5.55 (t, J=7.6 Hz, 1H), 4.65 (d, J=7.2 Hz, 1H), 4.25 (d, J=15.2 Hz, 1H), 4.13 (d, J=15.2 Hz, 1H), 3.88-3.92 (m, 1H), 3.08-3.12 (m, 1H), 2.77-2.65 (m, 2H), 2.02 (s, 8H), 1.45-1.33 (m, 2H), 0.93 (t, J=6.8 Hz, 3H). LCMS (Method-B)=662.2 $(M+H)^+$, 98.17% at RT 2.17 min. HPLC (Method-B)=98.58% at RT 9.37 min. C-HPLC (Method-A)=Peak-1=50.53% at RT 7.60 min, Peak-2=49.46% at RT 9.04 min.

Synthesis of I-245 and I-246
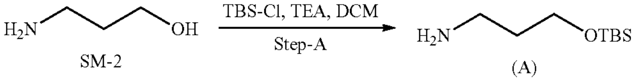
SM-2
(A)
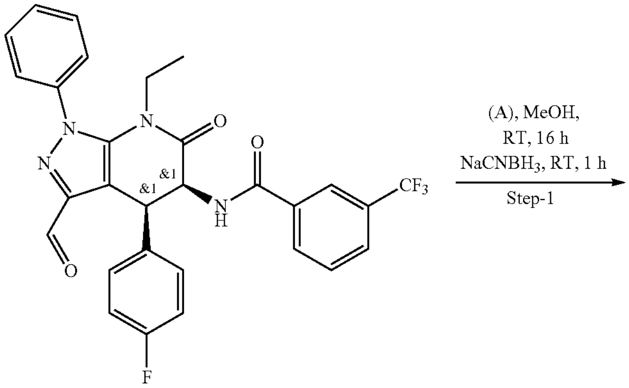
SM-1
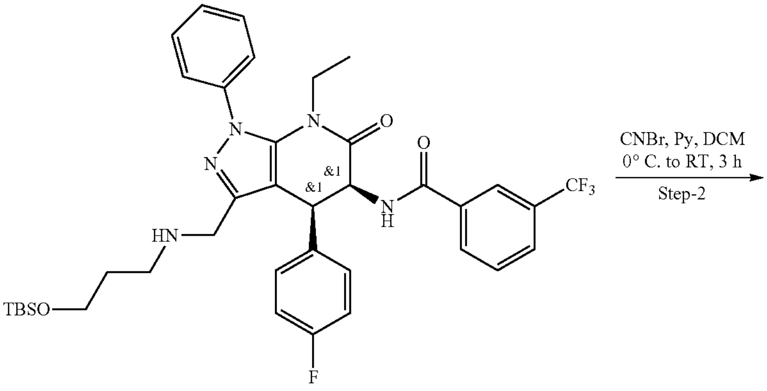
(1)
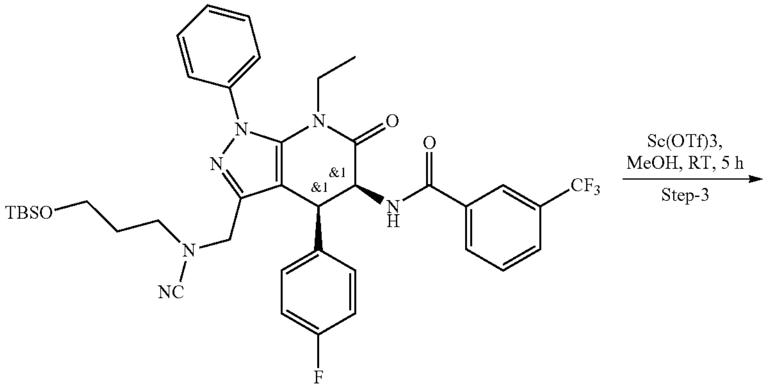
2

-continued

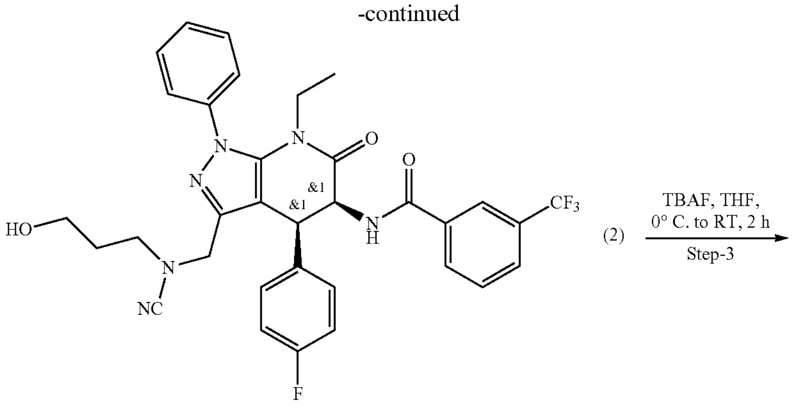

I-246

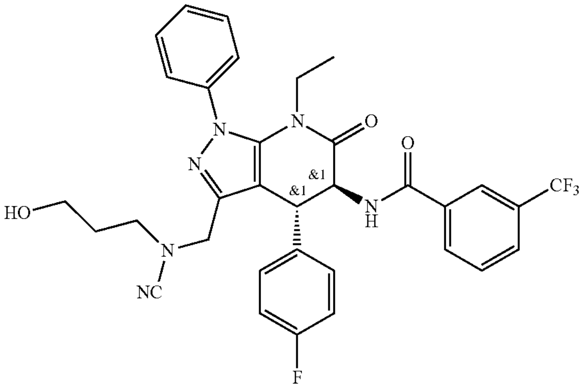

I-245

Step-1: Synthesis of ~{N}-[(4~{S},5~{S})-3-[[3-[~{tert}-butyl(dimethyl)silyl]oxypropylamino]methyl]-7-ethyl-4-(4-fluorophenyl)-6-oxo-1-phenyl-4,5-dihydropyrazolo[3,4-b]pyridine-5-yl]-3-(trifluoromethyl)benzamide (1)

To a stirred solution of ~{N}-[(4~{S},5~{S})-7-ethyl-4-(4-fluorophenyl)-3-formyl-6-oxo-1-phenyl-4,5-dihydropyrazolo[3,4-b]pyridine-5-yl]-3-(trifluoromethyl)benzamide (350 mg, 0.63 mmol) in methanol (3.5 mL) was added 3-[~{tert}-butyl(dimethyl)silyl]oxypropan-1-amine (180 mg, 0.95 mmol) at room temperature. Reaction mixture was stirred at room temperature for 16 h. Reaction progress was monitored by TLC. After 16 h, sodium cyanoborohydride (126 mg, 1.90 mmol) was added and stirred for 1 h. Reaction progress was monitored by TLC. After completion, the reaction mixture was concentrated under reduced pressure to afford crude compound. Crude compound was purified by silica gel chromatography (Column 12 g, Mesh: 230-400 Gradient: 0-50% EA in Heptane) Collected all pure fractions were concentrated under reduced pressure to afford compound (1) (150 mg, 32.27%) as a yellow solid. LC-MS (Method-C)=724.4 $[M+H]^+$; 52.37% at RT 1.62 min.

Step-2: Synthesis of ~{N}-[~{rac}-(4~{S},5~{S})-3-[[3-[~{tert}-butyl(dimethyl)silyl]oxypropyl-cyano-amino]methyl]-7-ethyl-4-(4-fluorophenyl)-6-oxo-1-phenyl-4,5-dihydropyrazolo[3,4-b]pyridine-5-yl]-3-(trifluoromethyl)benzamide (2)

To a stirred solution of compound (1) (150 mg, 0.20 mmol) in dichloromethane (1.5 mL) was added cyanogen bromide (0.04 mL, 0.24 mmol) and pyridine (0.04 g, 0.62 mmol) at 0° C. Reaction mixture was stirred at room temperature for 3 h. Reaction progress was monitored by TLC. After completion, reaction mixture was diluted with ice cold water (20 mL) and extracted with ethyl acetate (2×20 mL). The combined organic layer was dried over sodium sulfate, filtered, and concentrated under reduced pressure to afford crude compound (2) (50 mg, 12.89%) as a brown gummy solid.

$^1H$ NMR (400 MHZ, DMSO-$d_6$) δ: 8.57-8.50 (m, 1H), 8.20-8.10 (m, 2H), 7.96-7.88 (m, 1H), 7.68-7.56 (m, 6H), 7.15-6.92 (m, 4H), 5.58-5.49 (m, 1H), 4.63 (s, 1H), 4.22 (s, 1H), 4.17-4.06 (m, 1H), 3.95-3.82 (m, 1H), 3.46 (s, 2H), 3.16-3.02 (m, 1H), 2.85-2.64 (m, 2H), 1.57-1.35 (m, 1H), 1.28-1.20 (m, 1H), 0.91 (s, 3H), 0.81 (s, 9H), −0.01 (s, 6H). LC-MS (Method-A)=749.0 $[M+H]^+$; 78.83% at RT 2.49 min.

Step-3: Synthesis of N-[rac-(4S,5S)-3-[[cyano(3-hydroxypropyl)amino]methyl]-7-ethyl-4-(4-fluorophenyl)-6-oxo-1-phenyl-4,5-dihydropyrazolo[3,4-b]pyridine-5-yl]-3-(trifluorome thyl)benzamide (3): I-246

To a stirred solution of compound (2) (0.15 g, 0.20 mmol) in Methanol (1 mL) was added Scandium (III) trifluoromethanesulfonate (0.015 g, 0.030 mmol) at room temperature. Then the reaction mass was stirred at room temperature for 5 h. Reaction progress was monitored by TLC. After completion of starting material by TLC, reaction mixture was directly concentrated under reduced pressure, diluted with water (20 mL), and extracted with EtOAc (2×30 mL). The combined organic layers were dried over anhydrous $Na_2SO_4$, filtered, and concentrated under reduced pressure to obtain crude compound. Obtained crude was purified by Prep. HPLC to afford I-246 (0.053 g, 42%) as an off-white solid.

$^1$H NMR (400 MHZ, DMSO-$d_6$) δ: 8.55 (d, J=7.6 Hz, 1H), 8.16 (t, J=5.2 Hz, 2H), 7.93 (d, J=8.0 Hz, 1H), 7.73-7.68 (m, 3H), 7.62-7.53 (m, 3H), 7.13 (t, J=8.8 Hz, 2H), 7.01-6.98 (m, 2H), 5.55 (t, J=7.6 Hz, 1H), 4.65 (d, J=7.2 Hz, 1H), 4.45 (t, J=5.2 Hz, 1H), 4.24 (d, J=15.2 Hz, 1H), 4.13 (d, J=15.2 Hz, 1H), 3.90-3.83 (m, 1H), 3.28-3.26 (m, 2H), 3.10 (q, J=14.2 Hz, 1H), 2.85-2.71 (m, 2H), 1.50-1.39 (m, 2H), 0.93 (t, J=7.2 Hz, 3H). LCMS (Method-B): 635.0 $(M+H)^+$, 99.61% at RT 2.17 min. HPLC (Method-B): 99.59% at RT 8.84 min. C-HPLC (Method-A): 50.20% at RT 6.95 min, 49.80% at RT 8.66 min.

Step-3: Synthesis of ~{N}-[~{rac}-(4~{S},5~{S})-3-[[cyano(3-hydroxypropyl)amino]methyl]-7-ethyl-4-(4-fluorophenyl)-6-oxo-1-phenyl-4,5-dihydropyrazolo[3,4-b]pyridine-5-yl]-3-(trifluoromethyl) benzamide (3) (I-245)

To a stirred solution of compound (2) (40 mg, 0.04 mmol) in tetrahydrofuran (0.4 mL) was added tetrabutylammonium fluoride (1 mol/L) in THF (4 μL, 0.004 mmol) at 0° C. The reaction mixture was stirred at room temperature for 2 h. Reaction progress was monitored by TLC and consumption of starting material was observed. After completion, reaction mixture was diluted with water (5 mL) and extracted with ethyl acetate (2×10 mL). Combined organic layer was dried over sodium sulfate, filtered, and concentrated under reduced pressure to afford crude compound (40 mg) as a Light brown gummy solid. Crude compound was purified by Prep-HPLC. All pure fractions were lyophilized to afford I-245 (8 mg, 4.42%) as an off-white solid.

$^1$H NMR (400 MHZ, DMSO-$d_6$) δ: 8.99 (d, J=6.4 Hz, 1H), 8.02-8.00 (m, 2H), 7.90 (d, J=7.6 Hz, 1H), 7.72-7.67 (m, 3H), 7.62-7.52 (m, 3H), 7.48-7.44 (m, 2H), 7.18 (t, J=8.8 Hz, 2H), 5.31-5.25 (m, 1H), 4.50-4.46 (m, 2H), 3.78-3.73 (m, 1H), 3.64 (d, J=14 Hz, 1H), 3.36-3.33 (m, 2H), 3.19-3.09 (m, 2H), 2.75 (t, J=7.2 Hz, 2H), 1.51 (t, J=7.2 Hz, 2H), 0.80 (t, J=6.8 Hz, 3H). LC-MS (Method-B)=635.0 $[M+H]^+$; 99.67% at RT 2.10 min. HPLC (Method-B)=99.71% at RT 8.31 min. Chiral-HPLC (Method-C): Peak-1=50.00% at RT 5.42 min, Peak-2=49.99% at RT 7.16 min.

Synthesis of Int-A:

To a stirred solution of 3-aminopropan-1-ol (2 g, 26.63 mmol) in dichloromethane (20 mL) were added imidazole (3.7 g, 54 mmol) and tert-Butyldimethylchlorosilane (6.2 g, 40 mmol) at 0° C. Reaction mixture was stirred at room temperature for 3 h. Reaction progress was monitored by TLC. After completion, the reaction mixture was diluted with water (20 mL) and extracted with methanol in DCM (10%) (2×30 mL). The combined organic layer was dried over sodium sulfate, filtered, and concentrated under reduced pressure to afford crude compound. The crude compound was purified by silica gel chromatography (column: 40 g, Mesh: 230-400, Gradient: 0-10% methanol in DCM) Collected all pure fractions concentrated under reduced pressure to afford Int-A (3.5 g, 69%) as a white gummy solid.

$^1$H NMR (400 MHZ, DMSO-$d_6$) δ=6.11 (s, 2H), 3.74 (t, J=5.6 Hz, 2H), 3.07 (t, J=7.2 Hz, 2H), 1.93-1.87 (m, 2H), 0.93-0.83 (m, 9H), 0.83-−0.11 (m, 6H). LC-MS (Method-A)=189.87 $[M+H]^+$; 99.97% at RT 0.20 min.

Example 17: Synthesis of Compounds I-250, I-251, I-252, I-253, I-254 and I-255

NMR:

$^1$H NMR spectrum was recorded on Bruker 400 MHz and Varian 400 MHz instruments internally referenced to a tetramethylsilane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: I (95:5); B: 0.05% Formic acid in I Inj Volume: 2.0 μL, Column oven temperature: 50° C.; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge BEH C18, (50 mm*3.0 mm,2.5μ) Mobile Phase A: 2.5 mM Ammonium Bicarbonate in Water+5% CAN; Mobile Phase B: 100% I Flow rate: 1.0 mL/min. Column temperature: 40° C. Gradient Program (B %): 0.0/2, 0.3/2, 2.0/98, 2.8/98, 3.0/2,3.7/2.

Method-C: Column: X-Select CSH C18 (50 mm*3.0 mm,2.5μ) Mobile Phase A: 0.05% TFA in Water; Mobile Phase B: 0.05% TFA in Acetonitrile; Flow rate: 1.0 mL/min. Column temperature: 40° C. Gradient Program (B %): 0.0/2, 0.3/2,2.0/98, 2.8/98, 3.0/2,3.7/2.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5, 1/5,8/100,12/100,14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/2,2/2,12/90,16/90; Flow: 1.0 mL/min.; Diluent: I:Water (80:20).

Method-C: Column: X SELECT CSH C18 (150×4.6 mm, 3.5μ); Mobile Phase A; 0.05% TFA in water: I (95:05); Mobile Phase B: 0.05% TFA in water: I (05:95); Programme: T/B %: . 0.01/10,12/90,16/90; Flow: 1 mL/min.; Diluent: WATER: I (80:20).

Method-D: Column: X-Bridge CSH C18 (4.6*150) mm 5μ Mobile Phase: A-0.1% TFA in water B-Acetonitrile Inj Volume; 5.0 μL, Flow Rate: 1.2. mL/minute Gradient program: Time (min)/B Conc.: 0.01/5, 1.0/5, 8.0/100, 12.0/100, 14.0/5, 18.0/5.

Chiral HPLC:

Method-A: Column: CHIRALCEL-OX-H (250×4.6 mm, 5 μm) Mobile Phase A: n-Hexane; Mobile Phase B: EtOH: MeOH (1:1) A/B: 50/50 Flow: 1.0 ml/Min.

Method-B: Column: CHIRALPAK IG (250×4.6 mm, 5 μm) MobilePhase A: 0.1% DEA in n-Hexane; MobilePhase B: IPA; A: B-60:40 Flow rate: 1.0 ml/min.

Method-C: Column: CHIRAL PAK IA (250×4.6 mm, 5 μm) MobilePhase A n-Hexane; Mobile Phase B: IPA; A: B-70:30 Flow rate: 1.0 ml/min.

Method-D: Column: CHIRALPAK-IK (250×4.6 mm, 5 μm) Mobile Phase-A: n-Hexane; Mobile Phase-B: IPA: MeOH (50:50) B: 50:50 Flow: 1.0 mL/min.

Synthesis of N-((4RS,5RS)-3-1-2-cyano-4,4-difluoropyrrolidine-1-carbonyl)-7-ethyl-4-(4-fluorophenyl)-6-oxo-1-phenyl-4,5,6,7-tetrahyde-1H-pyrazolo[3,4-b]pyridine-5-yl)-3-(trifluoromethyl) benzamide (I-251)

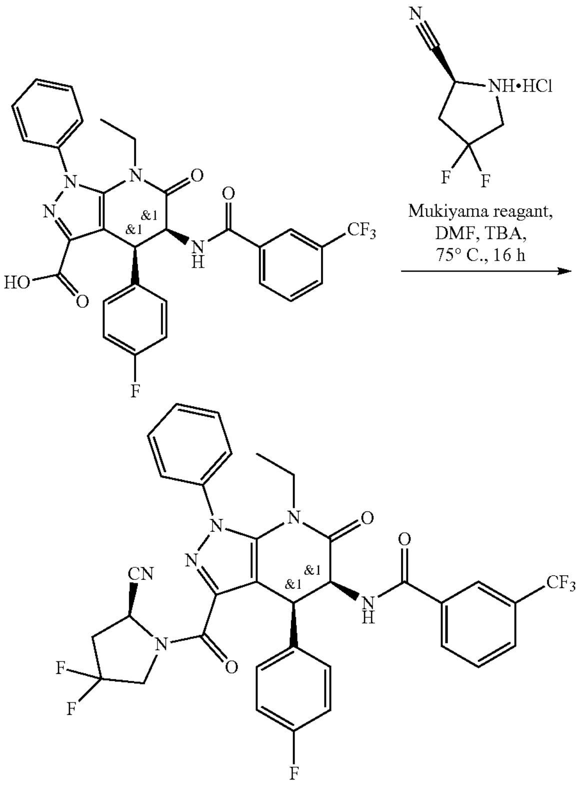

I-251

To a stirred solution of rac-(4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxylic acid (200 mg, 0.35 mmol) in DMF (5 mL) was added tributylamine (0.2 g, 1.05 mmol) followed by (S)-4,4-difluoropyrrolidine-2-carbonitrile hydrochloride (0.07 g, 0.45 mmol) and 2-chloro-1-methylpyridinium iodide (0.13 g, 0.52 mmol) at room temperature. Then the reaction mixture was stirred at 75° C. for 16 h. Progress of the reaction was monitored by TLC and LCMS. Reaction mixture was allowed cool to room temperature then quenched with ice water (25 mL) and extracted with EtOAc (2×25 mL). Combined organic layers were dried over anhydrous sodium sulfate and concentrated to afford crude compound. The crude compound was purified by silica gel (230-400) column chromatography using ethyl acetate in heptane. Product was eluted with 60% EtOAc in heptane. Product containing fractions were collected and concentrated to afford pure compound as a white solid. The compound was purified by pre-HPLC I-251 (30 mg, 12.36%) as an off-white solid.

$^1$H NMR (400 MHZ, DMSO-$d_6$) δ=8.61-8.53 (m, 1H), 8.17-8.13 (m, 2H), 7.92 (d, J=8.0 Hz, 1H), 7.87-7.81 (m, 2H), 7.73-7.60 (m, 4H), 7.10-7.06 (m, 2H), 7.02-6.97 (m, 2H), 5.49-5.47 (m, 1H), 5.26-5.18 (m, 1H), 5.06-4.95 (m, 1H), 4.56-4.32 (m, 2H), 3.92-3.88 (m, 1H), 3.07-2.99 (m, 1H), 2.88-2.78 (m, 2H), 0.90 (t, J=7.2 Hz, 3H). LC-MS (Method-B)=679.0 $[M-H]^-$; 99.82% at RT 2.41 min. HPLC (Method-B): 99.79% at RT 9.74 min. Chiral HPLC (Method-A): Peak-1=49.57% at RT 5.34 min. Peak-2=50.42% at RT 5.66 min.

Synthesis of N-((4RS,5RS)-3-((2R,4R)-2-cyano-4-fluoropyrrolidine-1-carbonyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl) benzamide (I-253)

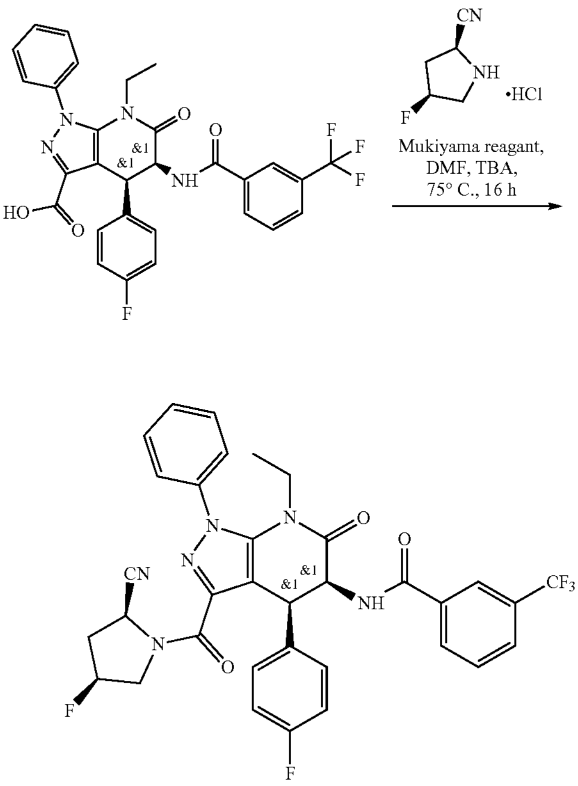

I-253

To a stirred solution of rac-(4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxylic acid (200 mg, 0.35 mmol) in DMF (5 mL) was added tributylamine (0.20 g, 1.05 mmol) followed by (2S,4S)-4-fluoropyrrolidine-2-carbonitrile.hydrochloride (0.07 g, 0.45 mmol) and 2-chloro-1-methylpyridinium iodide (0.13 g, 0.52 mmol) at room temperature. Then the reaction mixture was stirred at 75° C. for 16 h. Progress of the reaction was monitored by TLC Reaction mixture was allowed to cool to room temperature, then quenched with ice water (50 mL) and extracted with EtOAc (2×25 mL). Combined organic layers were dried over anhydrous sodium sulfate and concentrated to afford crude compound. Obtained crude compound was purified by silica gel (230-400) column chromatography using ethyl acetate in heptane. Product was eluted with 60% EtOAc in heptane. Product containing fractions were collected and concentrated to afford pure compound as a white solid. The compound was purified by pre-HPLC I-253 (25 mg, 10.58%) as an off-white solid.

$^1$H NMR (400 MHZ, DMSO-$d_6$) δ=8.60-8.52 (m, 1H), 8.17-8.13 (m, 2H), 7.92 (d, J=8.0 Hz, 1H), 7.86-7.78 (m, 2H), 7.73-7.59 (m, 4H), 7.10-6.95 (m, 4H), 5.92-4.98 (m, 4H), 4.49-3.71 (m, 3H), 3.30-3.01 (m, 1H), 2.44 (s, 2H), 0.92-0.87 (m, 3H). LC-MS (Method-B)=661.0 $[M-H]^-$; 99.88% at RT 2.34 min. HPLC (Method-B): 99.84% at RT 9.49 min. Chiral HPLC (Method-A): Peak-1=48.03% at RT 6.62 min. Peak-2=51.96% at RT 6.69 min.

Synthesis of rac-methy I-4-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)(methyl)amino)but-2-enoate (I-250) & rac-methyl I-4((((4R,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)(methyl)amino)but-2-enoate (I-252)

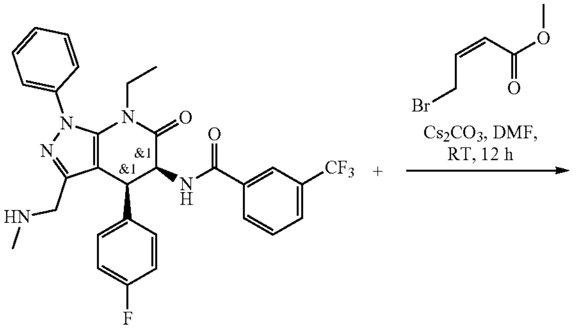

17-1

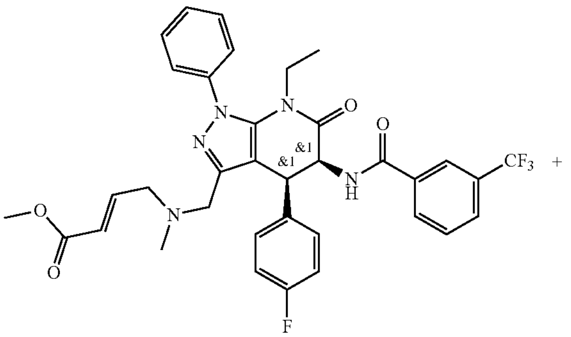

I-250

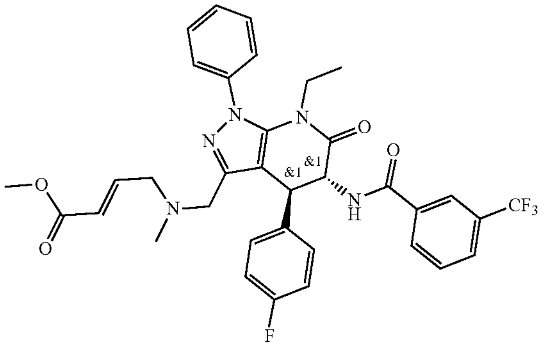

I-252

Step-1: Synthesis of rac-methyl I-4-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)methyl)(methyl)amino) but-2-enoate (I-250) & rac-methyl I-4-((((4R,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)methyl)(methyl)amino) but-2-enoate (I-252)

To a stirred solution of 17-1 (200 mg, 0.35 mmol) in DMF (5.00 mL) was added Cesium carbonate (0.23 g, 0.70 mmol) and methyl (~{Z})-4-bromobut-2-enoate (0.08 g, 0.45 mmol) reagent at room temperature. Then the reaction mixture was stirred at room temperature for 12 h. Progress of the reaction was monitored by TLC & LCMS. Reaction mixture was allowed to room temperature, quenched with ice water (50 mL), and extracted with EtOAc (2×50 mL), combined organic layers were dried over anhydrous sodium sulphate and concentrated to afford crude compound. Obtained crude compound was purified by silica gel (230-400) column chromatography using ethyl acetate in heptane. Product was eluted with 60% EtOAc in heptane, product containing fractions were collected and concentrated to afford pure compound, which was purified by pre-HPLC to afford I-250 (25 mg, 10.65%) and I-252 (15 mg, 6.39%) as an off-white solid.

I-250

$^1$H NMR (400 MHZ, DMSO-$d_6$) δ=8.49 (d, J=7.2 Hz, 1H), 8.16-8.13 (m, 2H), 7.92 (d, J=8.0 Hz, 1H), 7.73-7.65 (m, 3H), 7.60-7.52 (m, 3H), 7.06 (t, J=8.8 Hz, 2H), 6.97-6.94 (m, 2H), 6.47-6.43 (m, 1H), 5.77-5.73 (m, 1H), 5.48 (t, J=7.2 Hz, 1H), 4.66 (t, J=7.2 Hz, 1H), 3.88-3.87 (m, 1H), 3.60 (s, 3H), 3.49 (d, J=13.6 Hz, 1H), 3.31-3.28 (m, 1H), 3.05-2.99 (m, 3H), 2.00 (s, 3H), 0.91 (t, J=6.8 Hz, 3H). LC-MS (Method-B)=664.1 $[M+H]^+$; 99.60% at RT 2.52 min. HPLC (Method-B): 99.52% at RT 9.97 min. Chiral HPLC (Method-A): Peak-1=49.79% at RT 6.79 min. Peak-2=50.21% at RT 8.20 min.

I-252

$^1$H NMR (400 MHZ, DMSO-$d_6$) δ=9.00 (s, 1H), 8.01-8.00 (m, 2H), 7.90 (d, J=8.0 Hz, 1H), 7.70 (t, J=8.4 Hz, 1H), 7.67-7.65 (m, 2H), 7.58 (t, J=7.2 Hz, 2H), 7.53-7.49 (m, 1H), 7.41-7.37 (m, 2H), 7.14 (t, J=8.8 Hz, 2H), 6.63-6.56 (m, 1H), 5.85 (d, J=16.0 Hz, 1H), 5.18-5.13 (m, 1H), 4.40 (d, J=10.8 Hz, 1H), 3.65-3.60 (m, 4H), 3.27-3.20 (m, 1H), 2.93-2.90 (m, 2H), 2.79-2.66 (m, 2H), 1.82 (s, 3H), 0.79 (t, J=6.8 Hz, 3H). LC-MS (Method-B)=664.1 $[M+H]^+$; 99.82% at RT 2.42 min. HPLC (Method-B): 99.89% at RT 9.49 min. Chiral HPLC (Method-A): Peak-1=49.15% at RT 6.04 min. Peak-2=52.85% at RT 8.99 min.

Synthesis of (4S,5S)-N-((S)-1-cyanoethyl)-7-ethyl-4-(4-fluorophenyl)-6-oxo-1-phenyl-5-(3-trifluoromethyl)benzamido)-4,5,6,7-tetrahydro-1H-pyrazolo[3,4-b]pyridine-3-carboxamide (I-254) & (4R,5R)-N-((S)-1-cyanoethyl)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxamide (I-255)

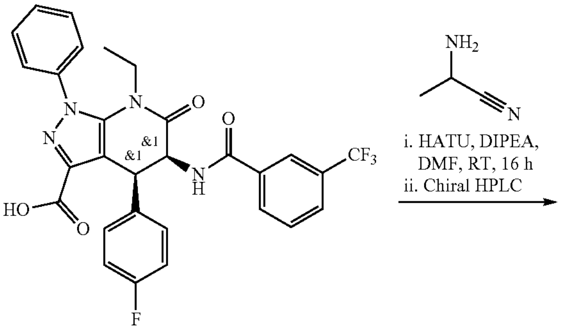

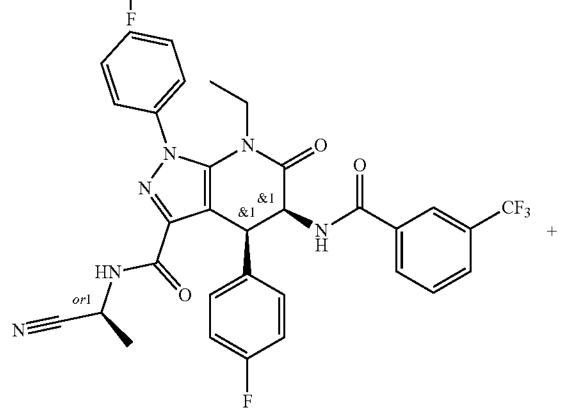

I-254

-continued

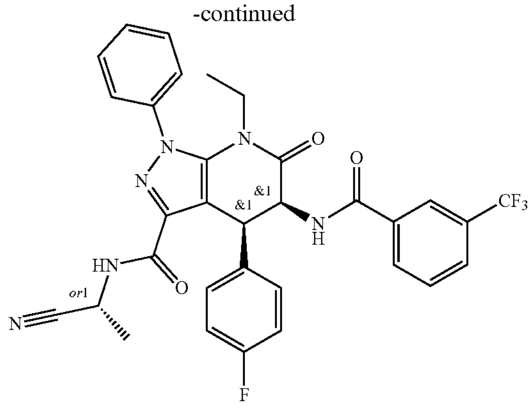

I-255

To a stirred solution of rel-(4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxylic acid (300 mg, 0.52 mmol) in DMF (2 mL) was added N,N-Diisopropylethylamine (0.34 g, 2.64 mmol), HATU (0.31 g, 0.79 mmol) followed by 2-aminopropanenitrile (0.03 g, 0.52 mmol) at room temperature under inert atmosphere. The reaction mixture was stirred at room temperature for 16 h. Reaction progress was monitored by TLC and LCMS. After completion of the reaction, the reaction mixture was diluted with cold water (50 mL) and compound was extracted with EtOAc (2×50 mL). The combined organic layers were dried over $Na_2SO_4$ and concentrated under reduced pressure to afford the crude which was further purified by chiral purification to afford I-255 (20 mg, 6.105%) and I-254 (24 mg, 7.32%) as a pale yellow solid.

I-255

$^1$H NMR (400 MHZ, $CDCl_3$-$d_6$) δ=8.01 (s, 1H), 7.85 (d, J=7.6 Hz, 1H), 7.78 (t, J=7.6 Hz, 1H), 7.64-7.59 (m, 3H), 7.57-7.53 (m, 3H), 7.09-7.02 (m, 3H), 6.98-6.94 (m, 2H), 6.80 (d, J=6.4 Hz, 1H), 5.31 (t, J=7.2 Hz, 1H), 5.24 (d, J=7.2 Hz, 1H), 5.09-5.05 (m, 1H), 4.01-3.96 (m, 1H), 3.19-3.14 (m, 1H), 1.59 (d, J=7.2 Hz, 2H), 1.00 (t, J=6.8 Hz, 3H). LC-MS (Method-B)=617.01 $[M-H]^-$; 98.72% at RT 2.25 min. HPLC (Method-B): 99.86% at RT 9.47 min. HPLC-C (Method-A): 100% at RT 11.96 min.

I-254

$^1$H NMR (400 MHZ, DMSO-$d_6$) δ=9.11 (d, J=8.0 Hz, 1H), 8.56 (d, J=6.8 Hz, 1H), 8.16-8.13 (m, 2H), 7.92 (d, J=8.0 Hz, 1H), 7.83-7.80 (m, 2H), 7.71 (t, J=8.0 Hz, 1H), 7.67-7.61 (m, 3H), 7.08 (t, J=8.8 Hz, 2H), 7.02-6.99 (m, 2H), 5.55 (t, J=7.2 Hz, 1H), 4.99 (d, J=7.2 Hz, 1H), 4.92-4.88 (m, 1H), 3.91-3.85 (m, 1H), 3.03-2.98 (m, 1H), 1.45 (d, J=7.2 Hz, 3H), 0.89 (t, J=7.2 Hz, 3H). LC-MS (Method-C)=619.1 $[M+H]^+$; 95.65% at RT 6.26 min.

HPLC (Method-B): 95.11% at RT 6.13 min. HPLC-C (Method-A): 98.69% at RT 21.87 min.

Example 18: Synthesis of Compounds I-115, I-224, I-189, I-226, I-196, I-207, I-192, I-199, I-235, I-225, I-188, I-35, I-195, I-53, I-208, I-216 and I-194

NMR:

$^1$H NMR spectrum was recorded on Bruker 400 MHz and Varian 400 MHz instruments internally referenced to a tetramethylsilane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: I (95:5) B: 0.05% Formic acid in ACN; Inj Volume: 2.0 μL, Column oven temperature: 50° C.; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge BEH C18, (50 mm*3.0 mm,2.5μ) Mobile Phase A: 2.5 mM Ammonium Bicarbonate in Water+5% I Mobile Phase B: 100% I Flow rate: 1.0 mL/min. Column temperature: 40° C. Gradient Program (B %): 0.0/2, 0.3/2, 2.0/98, 2.8/98, 3.0/2,3.7/2.

Method-C: Column: X-Select CSH C18 (50 mm*3.0 mm,2.5μ) Mobile Phase A: 0.05% TFA in Water; Mobile Phase B: 0.05% TFA in Acetonitrile; Flow rate: 1.0 mL/min. Column temperature: 40° C. Gradient Program (B %): 0.0/2, 0.3/2,2.0/98, 2.8/98, 3.0/2,3.7/2.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5, 1/5,8/100,12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/2,2/2,12/90,16/90; Flow: 1.0 mL/min.; Diluent: I:Water (80:20).

Method-C: Column: X SELECT CSH C18 (150×4.6 mm, 3.5μ); Mobile Phase A; 0.05% TFA in water: I (95:05); Mobile Phase B: 0.05% TFA IN WATER: I (05:95); Programme: T/B %: . 0.01/10, 12/90, 16/90; Flow: 1 mL/min.; Diluent: WATER: I (80:20).

Method-D: Column: X-Bridge CSH C18 (4.6*150) mm 5μ Mobile Phase: A-0.1% TFA in water B-Acetonitrile Inj Volume; 5.0 μL, Flow Rate: 1.2. mL/minute; Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in Hexane Mobile Phase B: IPA A/B: 60/40 Flow: 1.0 ml/MIN PDA: OJ-H_015.

Synthesis of Compound 18-1

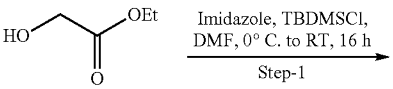

SM-1

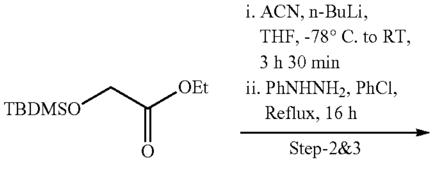

1

-continued

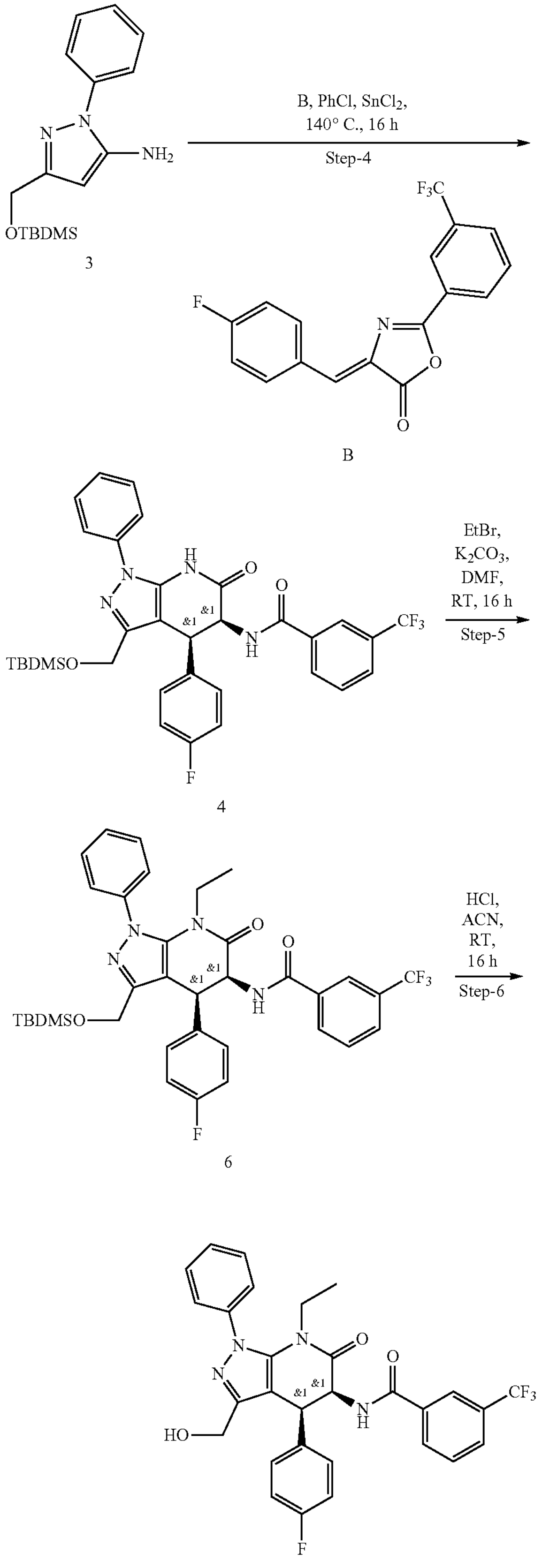

3

B

4

6

18-1

Step-(1): Synthesis of ethyl 2-[~{tert}-butyl(dimethyl)silyl]oxyacetate

To stirred solution of compound (SM1) (500 g, 4803 mmol) in DMF (2500 mL) was added imidazole (950.82 g, 6243 mmol) and TBDMSCl (950.82 g, 6243 mmol) at 0° C. The reaction mixture was stirred at room temperature for 16 h. After consumption of the starting material (by TLC), the reaction mixture was quenched with water (15 L) and extracted with EtOAc (2×10 L). Combined organic layer was washed with water (2×5 lit), brine (1×5 lit), and dried over anhydrous sodium sulfate, concentrated to afford compound (1) (1 kg, 95%) as colorless liquid.

$^1$H NMR (400 MHZ, DMSO-$d_6$) δ=4.22 (s, 2H), 4.13-4.08 (m, 2H), 1.19 (t, J=7.2 Hz, 3H), 0.90-0.84 (m, 9H), 0.05-0.02 (m, 6H).

Step-(2): Synthesis of 4-((tert-butyldimethylsilyl)oxy)-3-oxobutanenitrile (2)

To a stirred solution of acetonitrile (179 mL, 3434 mmol) in tetrahydrofuran (2500 mL), butyl lithium (2.5 mol/l) in hexanes (1437 ml, 3434 mmol) were added at −78° C. The reaction mixture was stirred at −78° C. for 30 min. Compound (1) (500 g, 2289 mmol) dissolved in tetrahydrofuran (2500 mL) was added to the reaction mixture slowly at same temperature. After 30 mins, the reaction mixture was allowed to stir at room temperature and the temperature was maintained for 3 h. Reaction progress was monitored by TLC. After completion of the reaction, the reaction mixture was quenched with ice cold water (200 mL) and pH adjusted to 4-5 using 2N aq. HCl solution. The reaction mixture was extracted with ethyl acetate (2×5 lit). Combined organic layer was dried over anhydrous sodium sulfate and concentrated under reduced pressure to afford crude compound (2) (450 g, 92%) as brown oil. The reaction crude was taken for next step without purification based on TLC only.

Step-(3): Synthesis of 3-(((tert-butyldimethylsilyl)oxy)methyl)-1-phenyl-1H-pyrazol-5-amine (3)

To a stirred solution of compound (2) (50 g, 233 mmol) in chlorobenzene (250 mL), phenylhydrazine (32.9 g, 304 mmol) was added at room temperature. The reaction mass temperature was raised to 140° C. The reaction mixture was stirred at same temperature for 16 h. Reaction progress was monitored by TLC. After completion of starting material, the reaction mixture was quenched with water (200 mL), and extracted with ethyl acetate (2×500 mL). Combined organic layer was dried over anhydrous sodium sulfate, concentrated under reduced pressure to afford crude compound. The obtained crude compound was purified by column chromatography eluting with 15-20% ethyl acetate in pet ether to afford compound (3) (34.0 g, 48%) as a pale brown solid.

$^1$H NMR (400 MHZ, DMSO-d6) δ=7.56 (d, J=7.2 Hz, 2H), 7.45 (t, J=7.6 Hz, 2H), 7.30-7.28 (m, 1H), 5.46 (s, 1H), 5.29 (s, 2H), 4.49 (s, 2H), 0.88 (s, 9H), 0.07 (s, 6H).

LC-MS (Method-B)=304.0 $[M+H]^+$; 98.55% at RT 2.40 min.

Step-4: Synthesis of rac-N-((4R,5R)-3-(((tert-butyldimethylsilyl)oxy)methyl)-4-(4-fluorophenyl)-6-oxo-1-phenyl-4,5,6,7-tetrahydro-1H-pyrazolo[3,4-b]pyridine-5-yl)-3-(trifluoromethyl)benzamide (4)

To a stirred solution compound (3) (60 g, 198 mmol) and Int-B (67.62 g,198 mmol) in chlorobenzene (180 ml), tin(II)

chloride (4.92 g, 25.7 mmol) was added at room temperature. The reaction mixture was stirred at 140° C. for 16 h. Reaction progress was monitored by TLC. After completion of reaction, the reaction mixture was quenched with water (100 ml) and filtered through celite bed, and the bed was washed with DCM (200 mL). Layers were separated and further extracted with DCM (1×100 mL). Organic layer was dried over anhydrous sodium sulfate and concentrated under reduced pressure. The obtained crude was purified by column chromatography by eluting with 20-30% ethyl acetate in pet ether to afford compound (4) (40 g, 32%) as pale brown solid.

$^1$H NMR (400 MHZ, DMSO-$d_6$) δ=11.0 (s, 1H), 8.48 (d, J=7.2 Hz, 1H), 8.15-8.13 (m, 2H), 7.97 (d, J=8.0 Hz, 1H), 7.78-7.69 (m, 3H), 7.62-7.58 (m, 2H), 7.49-7.46 (m, 1H), 7.14 (t, J=8.8 Hz, 2H), 7.04-7.01 (m, 2H), 5.38 (t, J=6.8 Hz, 1H), 4.76 (d, J=7.2 Hz, 1H), 4.67 (d, J=12.4 Hz, 1H), 4.51 (d, J=12.4 Hz, 1H), 0.74 (s, 9H), 0.01 (s, 6H). LC-MS (Method-B)=639.0 $[M+H]^+$; 96.89% at RT 2.78 min.

Step-5: Synthesis of rac-N-((4R,5R)-3-(((tert-butyldimethylsilyl)oxy)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl) benzamide (5)

To a stirred solution of compound (4) (60 g, 82.66 mmol) in DMF (600 mL), potassium carbonate (15.0 g, 107.45 mmol) and bromoethane (10.9 g, 99.2 mmol) were added at room temperature. The reaction mixture was stirred at room temperature for 16 h. Reaction progress was monitored by TLC. After completion of reaction, the reaction mixture was quenched with water and extracted with ethyl acetate. Organic layer was dried over anhydrous sodium sulfate and evaporated under vacuum. The obtained crude was purified by column chromatography by eluting with 15-20% ethyl acetate in heptane to afford compound (5) (40 g, 65%) as yellow solid.

$^1$H NMR (400 MHZ, $CDCl_3$) δ=8.06 (s, 1H), 7.89 (d, J=8.0 Hz, 1H), 7.79 (d, J=8.0 Hz, 1H), 7.60-7.48 (m, 6H), 6.98-6.90 (m, 5H), 5.26-5.23 (m, 1H), 4.94 (d, J=7.2 Hz, 1H), 4.72 (d, J=12.4 Hz, 1H), 4.61 (d, J=12.4 Hz, 1H), 3.99-3.94 (m, 1H), 3.22-3.17 (m, 1H), 1.03-0.88 (m, 3H), 0.74 (s, 9H), 0.06 (s, 6H). LC-MS (Method-A)=667.53 $[M+H]^+$; 98% at RT 2.65 min.

Step-6: Synthesis of rac-N-((4R,5R)-7-ethyl-4-(4-fluorophenyl)-3-(hydroxymethyl)-6-oxo-1-phenyl-4,5,6,7-tetrahydro-1H-pyrazolo[3,4-b]pyridine-5-yl)-3-(trifluoromethyl)benzamide (18-1)

To a stirred solution of compound (5) (80 g, 120 mmol) in acetonitrile (800 mL), hydrochloric acid (80 mL, 6M) was added. The reaction mixture was stirred at room temperature for 16 h. Reaction progress was monitored by TLC. After completion of reaction, the reaction mixture was quenched with ice water and extracted with ethyl acetate. Organic layer was dried over anhydrous sodium sulfate and concentrated under vacuum to afford crude compound. The crude material was washed with 10% diethyl ether in pentane and dried under vacuum to afford 18-1 (56 g, 85%) as a pale-yellow solid. The pure compound was submitted to Chiral SFC purification to separate isomers, Peak-2 (23.02 g) and Peak-1 (23.94 g).

$^1$H NMR (400 MHZ, DMSO-$d_6$) δ=8.52 (d, J=7.2 Hz, 1H), 8.15-8.12 (m, 2H), 7.92 (d, J=7.6 Hz, 1H), 7.73-7.65 (m, 3H), 7.60-7.52 (m, 3H), 7.09 (t, J=8.8 Hz, 2H), 7.00-6.96 (m, 2H), 5.52 (t, J=7.2 Hz, 1H), 5.11 (t, J=5.6 Hz, 1H), 4.72 (d, J=7.2 Hz, 1H), 4.40-4.35 (m, 1H), 4.29-4.24 (m, 1H), 3.94-3.88 (m, 1H), 3.05-3.00 (m, 1H), 0.90 (t, J=7.2 Hz, 3H). LC-MS (Method-A)=553.1 $[M+H]^+$; 96.60% at RT 5.72 min. HPLC (Method-A)=96.71% at RT 5.80 min.

Synthesis of Int. B

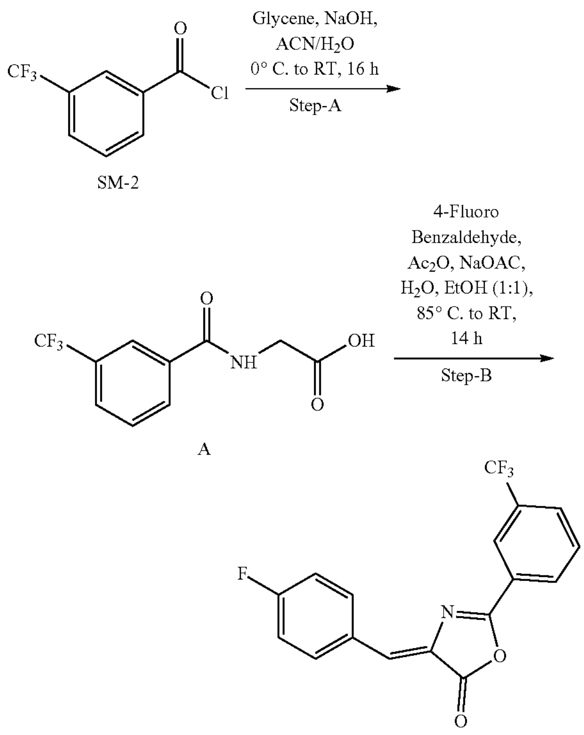

SM-2

A

B

Step-A: Synthesis of (3-(trifluoromethyl)benzoyl)glycine (A)

A stirred solution of glycine (359.89 g, 4794.78 mmol) in I (6 L) was added to a NaOH (479.35 g, 11986.95 mmol in 1.2 L of water) solution at 0° C. and stirred for 5 min. 3-(trifluoromethyl)benzoyl chloride (SM-2) (1000 g, 4794.78 mmol) in I (2 L) was then added dropwise at 0° C. The reaction mixture was stirred at room temperature for 16 h. After consumption of the starting material (by TLC), the reaction mixture was diluted with water and acidified with HCl, and pH adjusted to 1-3 and extracted with EtOAc (2×10 L). The combined organic layer was washed with brine solution (5 L), dried over anhydrous $Na_2SO_4$, filtered, and concentrated under reduced pressure to afford crude compound. Crude compound was triturated with n-Heptane to get pure Compound-B (1000 g, 84.38%) as a yellow solid.

$^1$H NMR (400 MHZ, DMSO-$d_6$) δ=9.13-9.05 (m, 1H), 8.27-8.13 (m, 2H), 7.93 (d, J=7.5 Hz, 1H), 7.74 (t, J=7.7 Hz, 1H), 3.94 (d, J=5.8 Hz, 2H). LC-MS (Method-A)=248.12 $[M+H]^+$; 98.23% at RT 1.14 min.

Step-B: Synthesis of (Z)-4-(4-fluorobenzylidene)-2-(3-(trifluoromethyl)phenyl)oxazol-5 (4H)-one (B)

To a stirred solution of (A) (1000 g, 4045.8 mmol) in acetic anhydride (1250 g, 12137 mmol) was added 4-fluorobenzaldehyde (502.12 g, 4045.8 mmol) and the reaction mixture was allowed to stir for 10 to 15 min. To this mixture, NaOAc (335 g, 4045.8 mmol) was added at room temperature. The reaction mixture was heated at 85° C. for 14 h. Reaction was monitored by TLC. After completion of reaction, the reaction mass was cooled to room temperature, ethanol (500 mL) and water (500 mL) was added, and the mass was stirred for 3-4 hr. The reaction mixture was filtered, washed with heptane (100 mL), and dried for 1 h. Obtained compound was azeotroped with toluene (1 L) and filtered with heptane (3 L) to afford compound (B) (800 g, 60%) as a pale yellow solid.

$^1$H NMR (400 MHZ, DMSO-d6) δ=8.46-8.38 (m, 2H), 8.33 (s, 1H), 8.11 (d, J=7.6 Hz, 1H), 7.90 (t, J=7.8 Hz, 1H), 7.50-7.33 (m, 4H). LC-MS (Method-A)=336.1 $[M+H]^+$; 80.55% at RT 1.56 min.

Synthesis of I-224

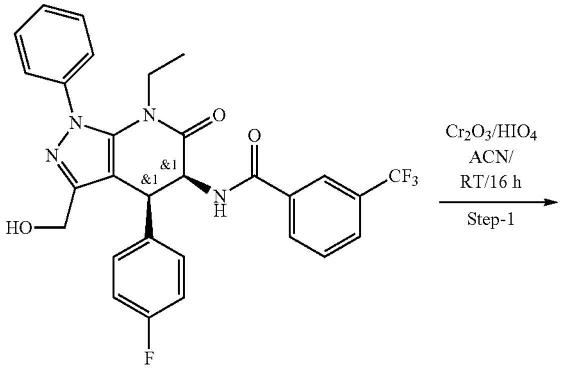

18-1

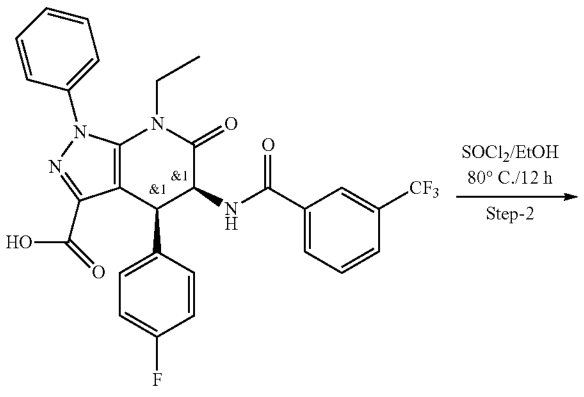

1

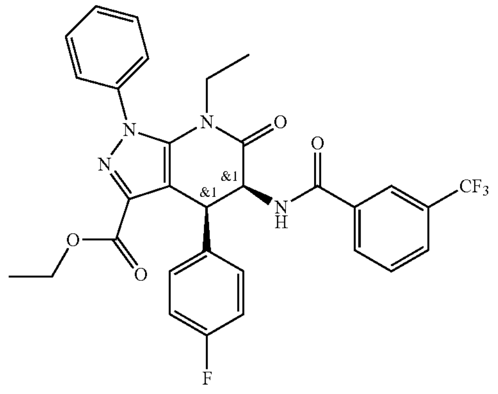

I-244

Step-1: Synthesis of rac-(4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxylic acid (1)

To a stirred solution of 18-1 (3 g, 5.32 mmol) in I (30 mL), periodic acid (2.5 g, 11 mmol) and Chromium (III) oxide (0.25 g, 1.6 mmol) were added at 0° C. The reaction mass was stirred for 16 h at room temperature. Reaction progress was monitored by TLC. After completion of reaction, the reaction mixture was diluted with 10% methanol in DCM, filtered through celite bed and washed with 10% methanol in DCM. Filtrate was concentrated under vacuum and washed with diethyl ether and filtered under vacuum. The compound was dried under vacuum to afford compound (1) (2.2 g, 38%) as an off-white solid.

$^1$H NMR (400 MHZ, DMSO-$d_6$) δ=9.90 (s, 1H), 8.64 (d, J=7.2 Hz, 1H), 8.16-8.13 (m, 2H), 7.92 (d, J=6.4 Hz, 1H), 7.84-7.81 (m, 2H), 7.73-7.64 (m, 4H), 7.10 (t, J=8.8 Hz, 2H), 7.02-6.99 (m, 2H), 5.57 (t, J=7.2 Hz, 1H), 4.89 (d, J=7.2 Hz, 1H), 3.91-3.86 (m, 1H), 3.17-3.15 (m, 1H), 0.90 (t, J=7.2 Hz, 3H). LC-MS (Method-A)=567.3 [M+H]+; 51.58% at RT 2.43 min.

Step-2: Synthesis of rac-ethyl (4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxylate (I-224)

To a stirred solution of compound (1) (200 mg, 0.183 mmol) in ethanol (20 mL), was added thionyl chloride (43.8 mg, 0.36 mmol) slowly at 0° C. The reaction mixture was stirred at 80° C. for 12 h. Reaction progress was monitored by TLC. After completion of reaction, reaction mixture was concentrated under vacuum to afford crude product. Obtained crude was purified by flash column chromatography (100-200 mesh) with 30-40% ethyl acetate in pet ether. Pure fractions were concentrated under vacuum and washed with pentane to afford (I-224) (60 mg, 54.3%) as an off-white solid.

$^1$H NMR (400 MHZ, DMSO-$d_6$) δ=8.59 (d, J=7.2 Hz, 1H), 8.16-8.13 (m, 2H), 7.92 (d, J=7.6 Hz, 1H), 7.80-7.78 (m, 2H), 7.73-7.63 (m, 4H), 7.12-7.08 (m, 2H), 7.00-6.97 (m, 2H), 5.57 (t, J=7.2 Hz, 1H), 4.88 (d, J=7.2 Hz, 1H), 4.23-4.14 (m, 2H), 3.90-3.85 (m, 1H), 3.05-2.98 (m, 1H), 1.13 (t, J=6.8 Hz, 3H), 0.90 (t, J=6.8 Hz, 3H). LC-MS (Method-B)=596.2 $[M+H]^+$; 98.52% at RT 2.43 min. HPLC (Method-B)=99.85% at RT 9.83 min.

Synthesis of I-189 & I-115

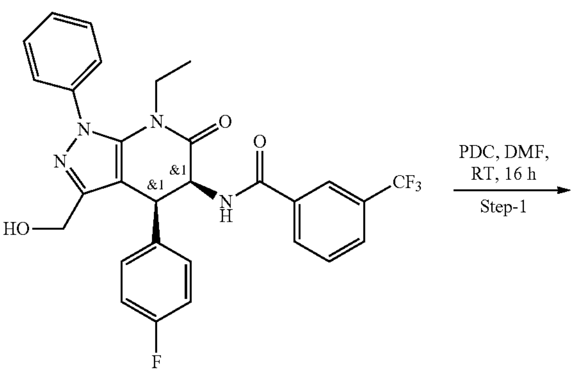

18-1

-continued

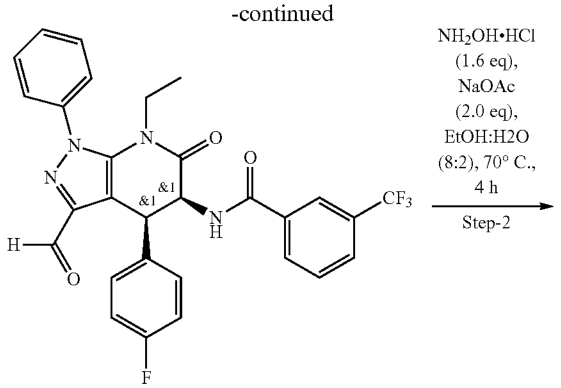

I-189

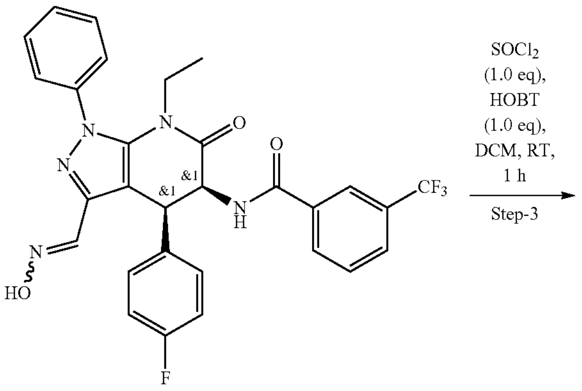

2

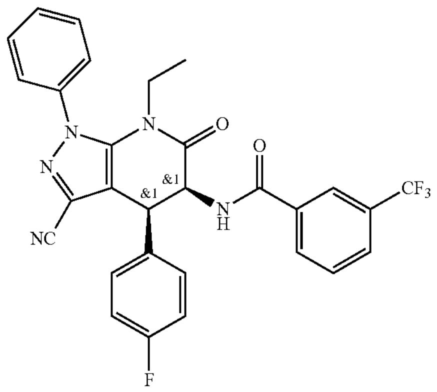

I-115

Step-1: Synthesis of rac-N-((4R,5R)-7-ethyl-4-(4-fluorophenyl)-3-formyl-6-oxo-1-phenyl-4,5,6,7-tetrahydro-1H-pyrazolo[3,4-b]pyridine-5-yl)-3-(trifluoromethyl)benzamide (I-189)

To a stirred solution of 18-1 (500 mg, 0.90 mmol) in DMF (5 mL) was added Pyridinium dichloromate (408 mg, 1.08 mmol) at 0° C. Then the reaction mixture was stirred at room temperature for 16 h. Reaction progress was monitored by TLC. After completion of reaction, the reaction mixture was quenched with water (50 mL) and extracted with EtOAc (2×50 mL). The combined organic layer was dried under sodium sulphate and concentrated under reduced pressure to afford crude compound. The obtained crude compound was purified by medium pressure liquid chromatography to afford I-189 (0.42 g, 84.33%) as a pale-yellow solid.

$^1$H NMR (400 MHZ, DMSO-$d_6$) δ=9.88 (s, 1H), 8.63 (d, J=7.6 Hz, 1H), 8.16-8.13 (m, 2H), 7.92 (d, J=8.0 Hz, 1H), 7.84-7.82 (m, 2H), 7.73-7.61 (m, 4H), 7.12-7.08 (m, 2H), 7.03-6.99 (m, 2H), 5.57 (t, J=7.2 Hz, 1H), 4.90 (d, J=7.2 Hz, 1H), 3.93-3.84 (m, 1H), 3.05-2.99 (m, 1H), 0.89 (t, J=6.8 Hz, 3H). LC-MS (Method-B)=551.2 $[M+H]^+$; 7.36% at RT 2.43 min. HPLC (Method-B)=98.62% at RT 9.80 min.

Step-2: Synthesis of (2)

To a stirred solution of compound (I-189) (250 mg, 0.45 mmol) was added NaOAc (74.5 mg, 0.90 mmol) and dissolved in EtOH (3 mL) and $H_2O$ (1 mL). Then to the reaction mixture was added $NH_2OH·HCl$ (50 mg, 0.71 mmol) and the reaction mixture was stirred at 70° C. for 4 h. Reaction progress was monitored by TLC. After completion of reaction, reaction mixture was concentrated under vacuum to afford crude compound. Obtained crude was dissolved in $H_2O$ (25 mL) and extracted with EtOAc (2×25 mL). The combined organic layer was dried under sodium sulphate and concentrated under reduced pressure to afford crude compound (2) (220 mg, 85.9%) as an off-white solid.

$^1$H NMR (400 MHZ, CHLOROFORM-d) δ=8.10 (s, 1H), 8.04 (s, 1H), 7.87 (d, J=7.6 Hz, 1H), 7.79 (d, J=7.6 Hz, 1H), 7.59-7.53 (m, 5H), 7.29 (s, 1H), 6.99-6.90 (m, 5H), 5.29-5.26 (m, 1H), 5.15 (d, J=7.2 Hz, 1H), 4.01-3.96 (m, 1H), 3.23-3.17 (m, 1H), 1.28-1.24 (m, 1H), 1.01 (t, J=7.2 Hz, 3H). LC-MS (Method-B)=566.2 $[M+H]^+$; 96.09% at RT 2.28 min.

Step-3: Synthesis of rac-N-((4R,5R)-3-cyano-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (I-115)

To a stirred solution of compound (II) (200 mg, 0.35 mmol) dissolved in DCM (3 mL) was added HOBt (47.7 mg, 0.35 mmol) cooled to 0° C. Then $SOCl_2$ (41.7 mg, 0.35 mmol) was added and the reaction mixture was stirred at room temperature for 1 h. Reaction progress was monitored by TLC. After completion of reaction, the reaction mixture was dissolved in $H_2O$ (25 mL) and extracted with EtOAc (2×25 mL). The combined organic layer was dried under sodium sulphate and concentrated under reduced pressure to afford crude compound. Obtained crude compound was purified by medium pressure liquid chromatography using 100-200 silica gel. Product was eluted in 30% EtOAc in heptane to afford I-115 (150 mg, 77.7%) as an off-white solid.

$^1$H NMR (400 MHZ, DMSO-$d_6$) δ=8.72 (d, J=7.6 Hz, 1H), 8.16-8.13 (m, 2H), 7.92 (d, J=8.0 Hz, 1H), 7.83-7.79 (m, 2H), 7.73-7.63 (m, 4H), 7.17-7.12 (m, 2H), 7.08-7.04 (m, 2H), 5.66 (t, J=7.2 Hz, 1H), 4.67 (d, J=7.2 Hz, 1H), 3.84-3.79 (m, 1H), 3.05-2.99 (m, 1H), 0.88 (t, J=7.2 Hz, 3H). LC-MS (Method-B)=548.2 $[M+H]^+$; 98.36% at RT 2.48 min. HPLC (Method-B)=98.41% at RT 9.74 min Synthesis of I-226 & I-192

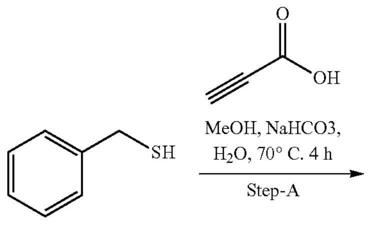

SM

-continued

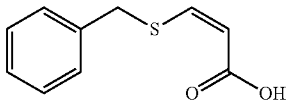

A

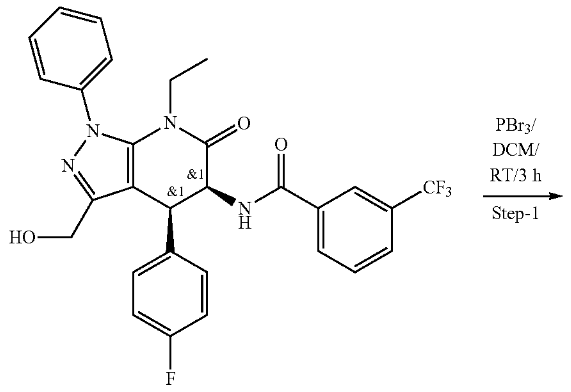

18-1

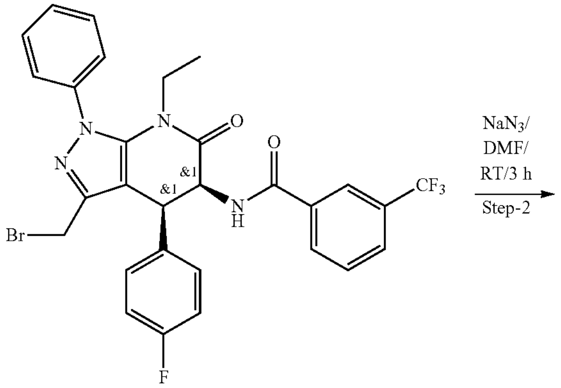

I-226

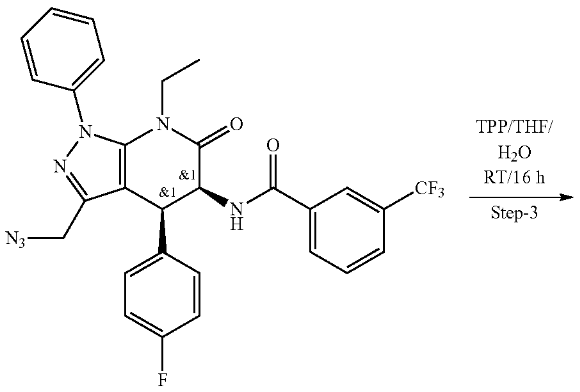

18-2

-continued

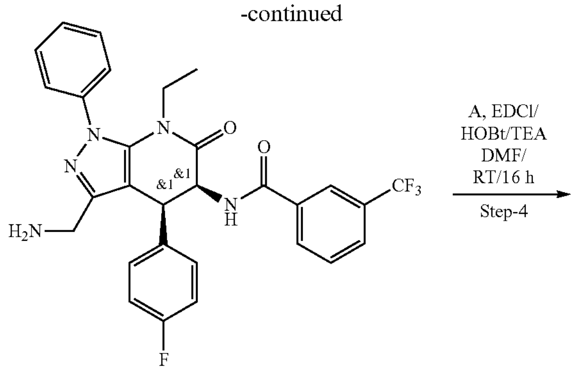

3

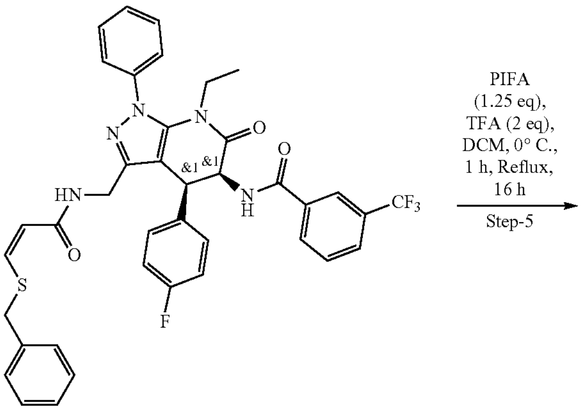

4

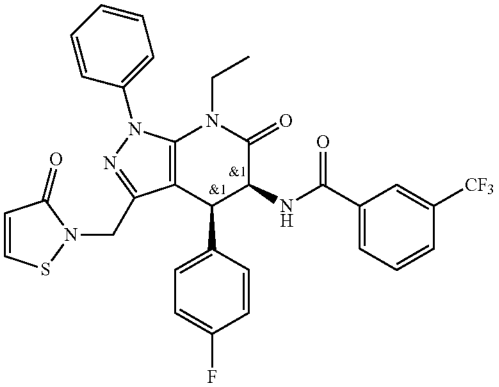

I-192

Step-1: Synthesis of rac-N-((4R,5R)-3-(bromomethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide I-226 (1)

To a stirred solution of 18-1 (6.0 g, 0.010 mmol) in DCM (60 mL) was added $PBr_3$ (4.4 g, 0.016 mmol) at 0° C. Then the reaction mixture was stirred at room temperature for 3 h. Reaction progress was monitored by TLC. After completion of reaction, the reaction mixture was diluted with $H_2O$ (100 mL) and extracted with EtOAc (2×300 mL). The combined organic layer was dried under sodium sulphate and concentrated under reduced pressure to afford crude compound. The obtained crude compound was purified by medium pressure liquid chromatography eluted with 30-40% ethyl acetate in heptane pure fraction was collected and concentrated to afford I-226 (5.4 g, 81%) as a pale-yellow solid.

$^1$H NMR (400 MHZ, DMSO-$d_6$) δ=8.56 (d, J=7.6 Hz, 1H), 8.16-8.13 (m, 2H), 7.92 (d, J=7.6 Hz, 1H), 7.74-7.69 (m, 3H), 7.62-7.55 (m, 3H), 7.31-7.08 (m, 2H), 7.01-6.98 (m, 2H), 5.54 (t, J=7.2 Hz, 1H), 4.70-4.63 (m, 2H), 4.38 (d, J=11.2 Hz, 1H), 3.92-3.85 (m, 1H), 3.07-3.00 (m, 1H), 0.91 (t, J=6.8 Hz, 3H). LC-MS (Method-B)=615.29 [M+H]$^+$; 97.38% at RT 2.29 min. HPLC (Method-B)=99.57% at RT 10.2 min. Chiral HPLC (Method-E)=Peak-1=50.23% at RT 5.68 min. Peak-2=49.77% at RT 7.83 min.

Step-2: Synthesis of rac-N-((4R,5R)-3-(azidomethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide 18-2

To a stirred solution of compound (I) (500 mg, 0.81 mmol) in DMF (10.0 mL) was added sodium azide (0.08 g, 1.21 mmol) at 0° C. under inert atmosphere. The reaction mixture was stirred at room temperature for 3 h. After consumption of the starting material (by TLC), the reaction was diluted into ice cold water (50 mL) and extracted with EtOAc (2×125 mL). The organic layer was dried over anhydrous $Na_2SO_4$, and concentrated under reduced pressure. The crude material was purified by medium pressure liquid chromatography by eluting with 10-20% EtOAc/heptane to afford 18-2 (150 mg, 29.79%) as an off-white solid.

$^1$H NMR (400 MHZ, DMSO-$d_6$) δ=8.56 (d, J=7.2 Hz, 1H), 8.15-8.12 (m, 2H), 7.92 (d, J=8.0 Hz, 1H), 7.73-7.69 (m, 3H), 7.62-7.53 (m, 3H), 7.13-7.08 (m, 2H), 7.01-6.98 (m, 2H), 5.54 (t, J=7.2 Hz, 1H), 4.65 (d, J=7.2 Hz, 1H), 4.45-4.30 (m, 2H), 3.91-3.86 (m, 1H), 3.08-3.03 (m, 1H), 0.91 (t, J=7.2 Hz, 3H). LC-MS (Method-B)=578.2 [M+H]$^+$; 96.65% at RT 2.47 min. HPLC (Method-B)=93.18% at RT 11.5 min. Chiral HPLC (Method-E)=Peak-1=50.42% at RT 7.66 min. Peak-2=43.93% at RT 9.17 min.

Step-3: Synthesis of rac-N-((4R,5R)-3-(aminomethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (3)

To a stirred solution of 18-2 (5.00 g, 0.008 mmol) in THF/$H_2O$ (3:1) (23+7 mL) was added TPP(6.81 g, 0.025 mmol) portion wise at room temperature. Then the reaction mixture was stirred at room temperature for 16 h. After consumption of the starting material (by TLC), the reaction was diluted into water (200 mL) and extracted with EtOAc (2×300 mL). The organic layer was dried over anhydrous $Na_2SO_4$, and concentrated under reduced pressure. The crude compound was purified by medium pressure liquid chromatography by eluting with 7% MeOH/DCM to afford crude compound (4.5 g, 95%) as yellow solid.

$^1$H NMR (400 MHZ, DMSO-$d_6$) δ=8.52 (d, J=7.2 Hz, 1H), 8.15-8.12 (m, 2H), 7.92 (d, J=6.4 Hz, 1H), 7.73-7.65 (m, 3H), 7.60-7.56 (m, 2H), 7.54-7.52 (m, 1H), 7.13-7.08 (m, 2H), 7.02-6.99 (m, 2H), 5.51-5.55 (m, 1H), 4.70 (d, J=7.2 Hz, 1H), 3.94-3.88 (m, 1H), 3.61-3.57 (m, 2H), 3.07-3.02 (m, 1H), 2.66-2.67 (m, 2H), 0.93-0.88 (m, 3H). LC-MS (Method-A)=551.9 [M+H]$^+$; 95.19% at RT 1.83 min. HPLC (Method-A)=97.47% at RT 6.27 min.

Step-4: Synthesis of rac-N-((4R,5R)-3-(((Z)-3-(benzylthio)acrylamido)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (4)

To a stirred solution of (~{E})-3-benzylsulfanylprop-2-enoic acid (0.2 g, 0.9 mmol) in DMF (5 mL) was added compound (3) (0.5 g, 0.9 mmol) and triethylamine (0.3 g, 3 mmol) and the reaction mixture was stirred for 5 min. Then 1-hydroxybenzotriazole (0.2 g, 1 mmol), and EDAC (0.3 g, 1 mmol) was added at 0° C., and the reaction mixture was stirred at room temperature for 16 h. Reaction mass was monitored by TLC. After completion of the reaction diluted with water (50 mL) and filter the solid precipitated to afford pure compound (4) (0.45 g, 70%) as an off-white solid.

$^1$H NMR (400 MHZ, DMSO-$d_6$) δ=8.40 (d, J=7.6 Hz, 1H), 8.13-8.05 (m, 2H), 7.93 (d, J=7.6 Hz, 1H), 7.73-7.52 (m, 6H), 7.34-7.22 (m, 6H), 6.83-6.78 (m, 4H), 5.48 (t, J=8.4 Hz, 1H), 4.50-4.31 (m, 1H), 4.06-4.05 (m, 2H), 3.90-3.87 (m, 1H), 3.03-3.01 (m, 1H), 2.89-2.73 (m, 4H), 0.89 (t, J=6.8 Hz, 3H). LC-MS (Method-B)=728.0 [M+H]$^+$; 82.14% at RT 2.57 min.

Step-5: Synthesis of rac-N-((4R,5R)-7-ethyl-4-(4-fluorophenyl)-6-oxo-3-((3-oxoisothiazol-2 (3H)-yl)methyl)-1-phenyl-4,5,6,7-tetrahydro-1H-pyrazolo[3,4-b]pyridine-5-yl)-3-(trifluoromethyl)benzamide (I-192)

To a stirred solution of [phenyl-(2,2,2-trifluoroacetyl)oxy-$\lambda^3$-iodanyl] 2,2,2-trifluoroacetate (0.12 g, 0.27 mmol), in dichloromethane (2 mL) was added TFA (0.071 g, 0.62 mmol), followed by compound (4) (0.15 g, 0.21 mmol) dissolved in DCM (2 mL) by drop wise addition at 0° C. Then the reaction mixture was stirred at the same temperature for 1 h and refluxed for 16 h. Reaction mass was monitored by TLC. After completion of reaction, the reaction mixture was quenched with water (10 mL) and extracted with DCM (2×20 mL). The combined organic layer was dried with sodium sulphate, and concentrated under reduced pressure to afford crude compound. The crude compound was purified by column chromatography of 100-200 mesh silica where the pure compound was eluted at 50-60% of EtOAc in hexane to afford I-192 as an off-white solid.

$^1$H NMR (400 MHZ, DMSO-$d_6$) δ=8.48 (d, J=7.2 Hz, 1H), 8.17-8.11 (m, 3H), 7.91 (d, J=8.0 Hz, 1H), 7.72-7.68 (m, 3H), 7.62-7.53 (m, 3H), 7.02-6.98 (m, 2H), 6.84-6.80 (m, 2H), 5.83 (d, J=6.0 Hz, 1H), 5.49 (t, J=7.2 Hz, 1H), 4.99 (d, J=15.2 Hz, 1H), 4.59-4.50 (m, 2H), 3.90-3.84 (m, 1H), 3.06-3.01 (m, 1H), 0.89 (t, J=7.2 Hz, 3H). LC-MS (Method-B)=635.9 [M+H]$^+$; 99.23% at RT 2.27 min. HPLC (Method-B)=99.70% at RT 8.99 min.

Synthesis of Int-A:

To a stirred solution of prop-2-ynoic acid (2 g, 28.55 mmol) in methanol (26 mL), and water (34 mL), sodium carbonate (3.36 g, 31.41 mmol) and phenylmethanethiol (SM) (3.54 g, 28.55 mmol) were added at 25° C. After addition, the temperature was raised to 70° C. and allowed to stir for 4 h. Reaction mass was monitored by TLC. After completion of reaction, the pH was adjusted with 2N HCl and filtered to afford compound-A (4.5 g, 81%) as off-white solid.

$^1$H NMR (400 MHZ, DMSO-$d_6$) δ=12.09 (s, 1H), 7.40-7.24 (m, 6H), 5.81-5.76 (m, 1H), 4.16-4.09 (m, 2H).

Synthesis of I-196 & I-207

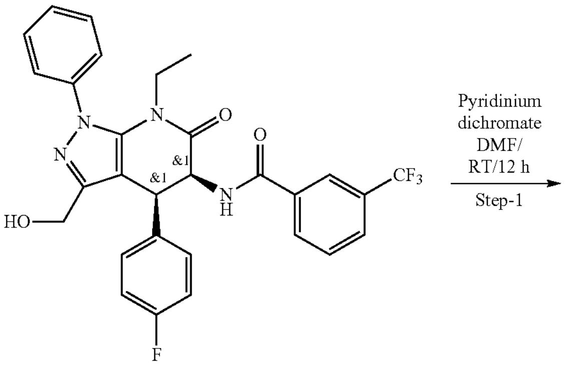

18-1

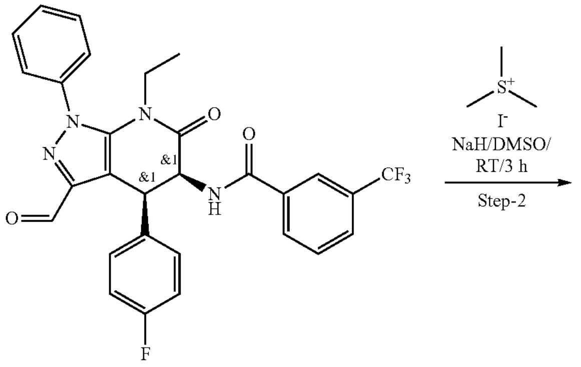

1

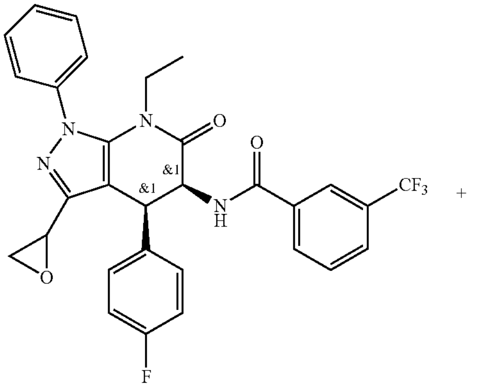

I-196

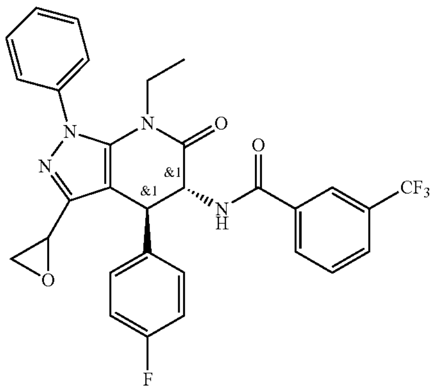

I-207

Step-1: Synthesis of rac-N-((4R,5R)-7-ethyl-4-(4-fluorophenyl)-3-formyl-6-oxo-1-phenyl-4,5,6,7-tetrahydro-1H-pyrazolo[3,4-b]pyridine-5-yl)-3-(trifluoromethyl)benzamide (1)

To a stirred solution of 18-1 (6 g, 10.4 mmol) in DMF (60 mL), pyridinium dichromate (6.25 g, 16.3 mmol) was added at room temperature. Then the reaction mixture was stirred at room temperature for 12 h. Reaction progress was monitored by TLC. After completion of reaction, the reaction mixture was quenched with water (200 mL) and filtered through celite bed and extracted with ethyl acetate (2×300 mL). The organic layer was dried over anhydrous sodium sulfate and concentrated to afford crude compound. Obtained crude material was purified through flash column chromatography (100-200 mesh) with 50-60% ethyl acetate in pet ether. Combined pure fractions was concentrated under vacuum and washed with ether to afford compound (1) (3.5 g, 58%) as a pale brown solid.

$^1$H NMR (400 MHZ, DMSO-$d_6$) δ=9.90 (s, 1H), 8.64 (d, J=7.2 Hz, 1H), 8.16-8.13 (m, 2H), 7.92 (d, J=6.4 Hz, 1H), 7.84-7.81 (m, 2H), 7.73-7.64 (m, 4H), 7.10 (t, J=8.8 Hz, 2H), 7.02-6.99 (m, 2H), 5.57 (t, J=7.2 Hz, 1H), 4.89 (d, J=7.2 Hz, 1H), 3.91-3.86 (m, 1H), 3.17-3.15 (m, 1H), 0.90 (t, J=7.2 Hz, 3H). LC-MS (Method-A)=551.5 $[M+H]^+$; 95.59% at RT 2.47 min.

Step-2: Synthesis of N-((4RS,5RS)-7-ethyl-4-(4-fluorophenyl)-3-((S*)-oxiran-2-yl)-6-oxo-1-phenyl-4,5,6,7-tetrahydro-1H-pyrazolo[3,4-b]pyridine-5-yl)-3-(trifluoromethyl)benzamide (I-196) & N-((4RS, 5SR)-7-ethyl-4-(4-fluorophenyl)-3-((S*)-oxiran-2-yl)-6-oxo-1-phenyl-4,5,6,7-tetrahydro-1H-pyrazolo [3,4-b]pyridine-5-yl)-3-(trifluoromethyl)benzamide (I-207)

To a stirred solution of trimethylsulfoniumiodide (258.00 mg, 1.26 mmol) in DMSO (8 mL) was added sodium hydride (45 mg, 1.85 mmol) at 0° C. Then the reaction mixture was stirred at room temperature for 1 h. Compound (1) (500 mg, 0.90 mmol) was then added at 0° C. Then the reaction mixture was stirred at room temperature for 2 h. Reaction progress was monitored by TLC. After completion of reaction, the reaction mass was diluted with water (25 mL) and extracted with ethyl acetate (2×25 mL). The organic layer was dried over anhydrous sodium sulfate and concentrated to afford I-196 (16.65 mg, 32%) as an off-white solid and I-207 (90.50 mg, 17%) as an off-white solid.

I-196:

$^1$H NMR (400 MHZ, DMSO-$d_6$) δ=8.52 (d, J=7.2 Hz, 1H), 8.16-8.13 (m, 2H), 7.92 (d, J=7.6 Hz, 1H), 7.72-7.69 (m, 2H), 7.62-7.53 (m, 4H), 7.14-7.10 (m, 2H), 6.98-6.95 (m, 2H), 5.51 (t, J=7.2 Hz, 1H), 4.60 (d, J=7.2 Hz, 1H), 3.92-3.85 (m, 2H), 3.02-2.91 (m, 2H), 2.43-2.41 (m, 1H), 0.90 (t, J=6.8 Hz, 3H). LC-MS (Method-B)=565.2 $[M+H]^+$; 97.34% at RT 2.44 min. HPLC (Method-B)=95.13% at RT 9.78 min. Chiral HPLC (Method-E)=Peak-1=37.59% at RT 4.85 min. Peak-2=62.41% at RT 8.12 min.

I-207:

$^1$H NMR (400 MHZ, DMSO-$d_6$) δ=9.08-9.03 (m, 1H), 8.02-8.01 (m, 2H), 7.91 (d, J=7.6 Hz, 1H), 7.73-7.64 (m, 3H), 7.61-7.51 (m, 3H), 7.49-7.43 (m, 2H), 7.20-7.15 (m, 2H), 5.33-5.19 (m, 1H), 4.48 (d, J=11.2 Hz, 1H), 3.75-3.64 (m, 1H), 3.18-3.07 (m, 1H), 2.98-2.66 (m, 3H), 0.80 (t, J=7.2 Hz, 3H). LC-MS (Method-B)=565.2 $[M+H]^+$; 99.72% at RT 2.26 min. HPLC (Method-B)=99.38% at RT 9.19 min. Chiral HPLC (Method-E)=Peak-1=57.07% at RT 5.59 min. Peak-2=26.39% at RT 7.17 min. Peak-3=16.55% at RT 14.3 min.

Synthesis of I-199 & I-235: Step-1: Synthesis rac-N-((4R,5R)-7-ethyl-4-(4-fluorophenyl)-3-formyl-6-oxo-1-phenyl-4,5,6,7-tetrohydro-1H-pyrazolo[3,4-b]pyridine-5-yl)-3-(trifluoromethyl) benzamide (I)

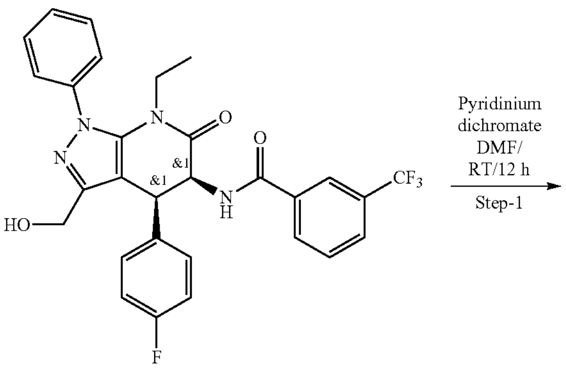

18-1

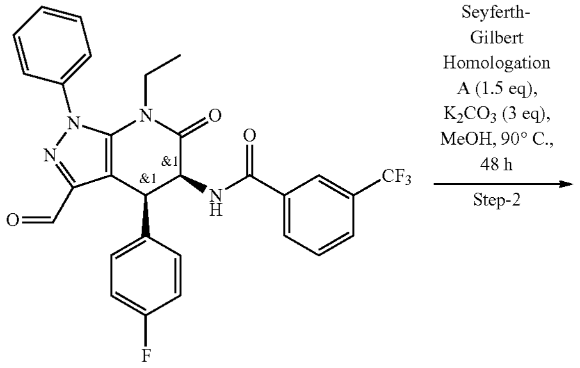

1

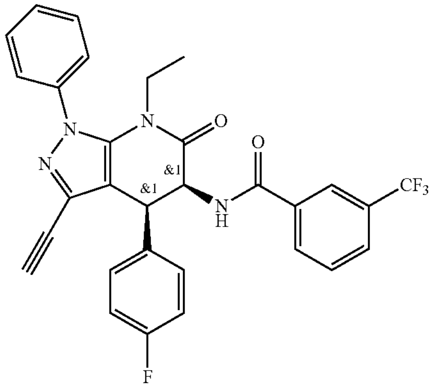

+

I-199

-continued

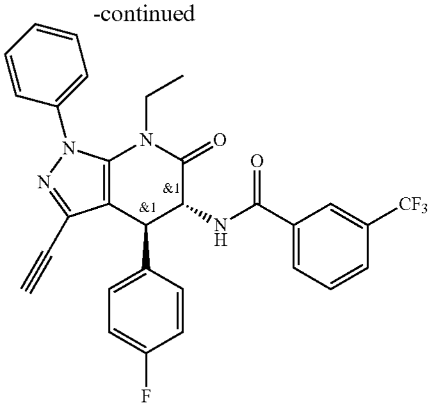

I-235

To a stirred solution of 18-1 (6 g, 10.4 mmol) in DMF (60 mL), pyridinium dichromate (6.25 g, 16.3 mmol) was added at room temperature. Then the reaction mixture was stirred at room temperature for 12 h. Reaction progress was monitored by TLC. After completion of reaction, the reaction mixture was quenched with water (600 mL) and filtered through celite bed and extracted with ethyl acetate (2×300 mL). The organic layer was dried over anhydrous sodium sulfate and concentrated to afford crude compound. Obtained crude material was purified through flash column chromatography (100-200 mesh) with 50-60% ethyl acetate in pet ether. Combined pure fractions was concentrated under vacuum and washed with ether to afford compound (I) (3.5 g, 58%) as a pale brown solid.

$^1H$ NMR (400 MHZ, DMSO-$d_6$) δ=9.90 (s, 1H), 8.64 (d, J=7.2 Hz, 1H), 8.16-8.13 (m, 2H), 7.92 (d, J=6.4 Hz, 1H), 7.84-7.81 (m, 2H), 7.73-7.64 (m, 4H), 7.10 (t, J=8.8 Hz, 2H), 7.02-6.99 (m, 2H), 5.57 (t, J=7.2 Hz, 1H), 4.89 (d, J=7.2 Hz, 1H), 3.91-3.86 (m, 1H), 3.17-3.15 (m, 1H), 0.90 (t, J=7.2 Hz, 3H). LC-MS (Method-A)=551.5 $[M+H]^+$; 95.59% at RT 2.47 min.

Step-2: Synthesis of N-((4S,5S)-7-ethyl-3-ethynyl-4-(4-fluorophenyl)-6-oxo-1-phenyl-4,5,6,7-tetrahydro-1H-pyrazolo[3,4-b]pyridine-5-yl)-3-(trifluoromethyl)benzamide (I-199) and N-((4S,5R)-7-ethyl-3-ethynyl-4-(4-fluorophenyl)-6-oxo-1-phenyl-4,5,6,7-tetrahydro-1H-pyrazolo[3,4-b]pyridine-5-yl)-3-(trifluoromethyl)benzamide (I-235)

To a stirred solution of compound (I) (2 g, 3.41 mmol) in methanol (50 mL) was added potassium carbonate (0.94 g, 6.83 mmol) and dimethyl (1-diazo-2-oxopropyl)phosphonate (1.00 g, 5.12 mmol) and the reaction mixture was stirred at 90° C. temperature for 48 h. Progress of the reaction mixture was monitored by TLC. Reaction mixture was allowed to stir at room temperature, quenched with water (100 mL), and extracted with ethyl acetate (2×150 mL). The combined organic layers were dried over anhydrous sodium sulfate and concentrated to afford crude compound. The obtained crude compound was purified by silica gel (230-400) column chromatography using ethyl acetate in heptane. Product was eluted in 20% EtOAc in heptane. Product containing fractions were collected and concentrated to afford pure compound (I-199) (500 mg, 25.72%) and (I-235) (800.0 mg, 40.72%) as a white solid.

(I-199):

$^1$H NMR (400 MHZ, DMSO-$d_6$) δ=8.62 (d, J=7.2 Hz, 1H), 8.16-8.13 (m, 2H), 7.92 (d, J=8.0 Hz, 1H), 7.75-7.69 (m, 3H), 7.64-7.57 (m, 3H), 7.14-7.09 (m, 2H), 7.02-6.98 (m, 2H), 5.55 (t, J=7.2 Hz, 1H), 4.54 (d, J=7.2 Hz, 1H), 4.35 (s, 1H), 3.91-3.82 (m, 1H), 3.02-2.97 (m, 1H), 0.89 (t, J=7.2 Hz, 3H). LC-MS (Method-B)=547.2 $[M+H]^+$; 98.33% at RT 2.48 min. HPLC (Method-B)=96.10% at RT 9.88 min. Chiral HPLC (Method-E)=Peak-1=47.37% at RT 9.68 min. Peak-2=52.63% at RT 12.8 min.

(I-235):

$^1$H NMR (400 MHZ, DMSO-$d_6$) δ=9.90 (d, J=8.8 Hz, 1H), 8.01-8.00 (m, 2H), 7.90 (d, J=7.6 Hz, 1H), 7.72-7.69 (m, 3H), 7.62-7.56 (m, 3H), 7.42-7.39 (m, 2H), 7.14-7.10 (m, 2H), 5.31-5.26 (m, 1H), 4.41 (d, J=12.4 Hz, 1H), 3.76-3.71 (m, 2H), 3.17-3.10 (m, 1H), 0.80 (t, J=6.8 Hz, 3H). LC-MS (Method-B)=547.24 $[M+H]^+$; 98.15% at RT 2.23 min. HPLC (Method-B)=98.23% at RT 9.47 min. Chiral HPLC (Method-E)=Peak-1=50.03% at RT 6.31 min. Peak-2=49.96% at RT 20.0 min.

Synthesis of rac-ethyl 2-((4R,5R)-7-ethyl-4-(4-fluorophenyl)-6-oxo-1-phenyl-5-(3-(trifluoromethyl)benzamido)-4,5,6,7-tetrohydro-1H-pyrazolo[3,4-b]pyridine-3-yl)acrylate (I-35)

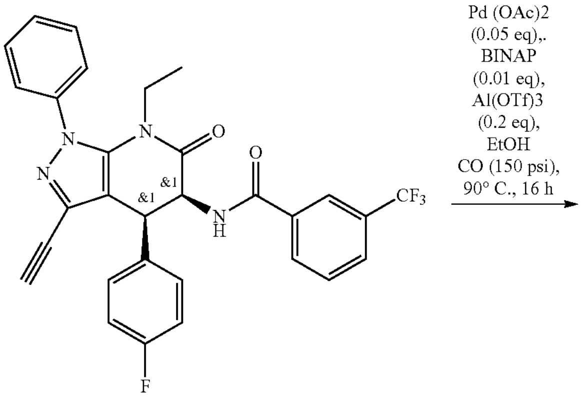

I-199

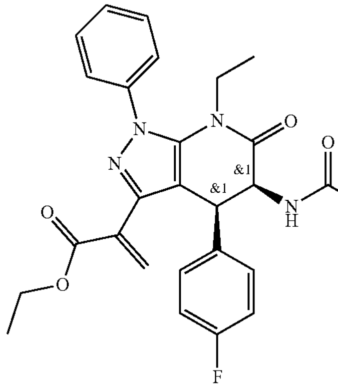

I-35

To a stirred solution of I-199 (130 mg, 0.23 mmol) in ethanol (5 mL) was added palladium (II) acetate (0.0026 g, 0.011 mmol) and (r)-(+)-2,2'-bis(diphenylphosphino)-1,1'-binaphthyl (0.0014 g, 0.0023 mmol),aluminum triflate (21.80 mg,0.046 mmol), under CO gas and the reaction mixture was stirred at 90° C. for 16 h. Progress of the reaction mixture was monitored by TLC. Reaction mixture was allowed to stir at room temperature, quenched with water (20 mL), and extracted with ethyl acetate (2×20 mL). The combined organic layer was dried over anhydrous sodium sulfate and concentrated to afford crude compound. Obtained crude compound was purified by silica gel (230-400) column chromatography using ethyl acetate in heptane and eluted in 5-10% MeOH/DCM. Compound containing fractions were collected and concentrated to afford I-35 (51.05 mg, 33%) as a white solid.

$^1$H NMR (400 MHZ, DMSO-$d_6$) δ=8.54 (d, J=7.2 Hz, 1H), 8.16-8.12 (m, 2H), 7.92 (d, J=7.6 Hz, 1H), 7.76-7.69 (m, 3H), 7.63-7.54 (m, 3H), 7.13-7.09 (m, 2H), 6.97-6.94 (m, 2H), 6.09 (s, 1H), 5.70 (s, 1H), 5.52 (t, J=7.2 Hz, 1H), 4.51 (d, J=7.2 Hz, 1H), 4.16-4.08 (m, 1H), 3.96-3.85 (m, 2H), 3.10-3.02 (m, 1H), 1.12 (t, J=6.8 Hz, 3H), 0.92 (t, J=7.2 Hz, 3H). LC-MS (Method-B)=621.2 $[M+H]^+$; 98.35% at RT 2.54 min. HPLC (Method-B)=95.90% at RT 10.1 min. Chiral HPLC (Method-E)=Peak-1=49.09% at RT 7.64 min. Peak-2=48.98% at RT 9.21 min.

Synthesis of rac-2-((4R,5R)-7-ethyl-4-(4-fluorophenyl)-6-oxo-1-phenyl-5-(3-(trifluoromethyl)benzamido)-4,5,6,7-tetrohydro-1H-pyrazolo[3,4-b]pyridine-3-yl)acrylic acid (I-53)

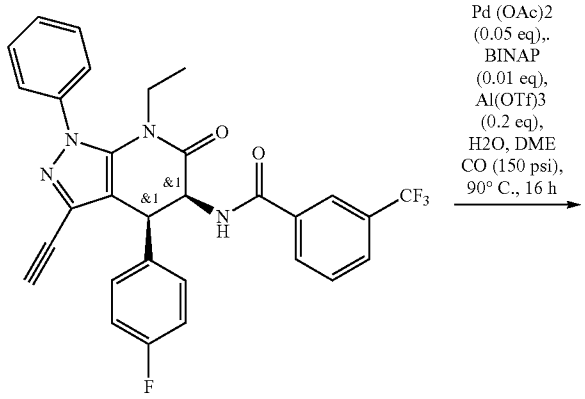

I-199

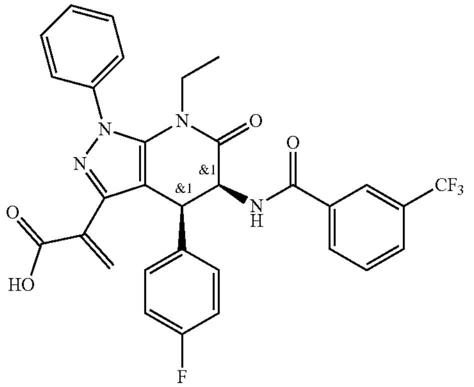

I-53

To a stirred solution of I-199 (300 mg, 0.54 mmol) in 1,2-dimethoxyethane (4 mL) & water (8 mL) was added [1-(2-diphenylphosphanyl-1-naphthyl)-2-naphthyl]-diphenyl-phosphane (0.0034 g, 0.0054 mmol) and Palladium(II) acetate (0.0064 g, 0.027 mmol), aluminum triflate (21.80 mg,0.046 mmol) under CO gas and the reaction mixture was stirred at 90° C. for 16 h. Progress of the reaction was monitored by TLC. Reaction mixture was allowed to stir at room temperature, quenched with water (25 mL) and extracted with EtOAc (2×50 mL). Combined organic layers were dried over anhydrous sodium sulfate and concentrated to afford crude compound. Obtained crude compound was purified by silica gel (230-400) column chromatography using MeOH/DCM, Product was eluted in 5-10% MeOH/DCM, product containing fractions were collected and concentrated to afford pure compound as a white solid. Obtained pure compound was purified by prep-HPLC, product containing fractions were collected and lyophilized to afford I-53 (175.0 mg, 44.9%) as an off-white solid.

$^1$H NMR (400 MHZ, DMSO-$d_6$) δ=8.45 (d, J=7.2 Hz, 1H), 8.15-8.12 (m, 2H), 7.91 (d, J=8.0 Hz, 1H), 7.72-7.68 (m, 3H), 7.55-7.52 (m, 3H), 7.10-7.06 (m, 2H), 6.97-6.93 (m, 2H), 5.86 (s, 1H), 5.50 (t, J=7.2 Hz, 1H), 5.41 (s, 1H), 4.67 (d, J=6.8 Hz, 1H), 3.92-3.86 (m, 1H), 3.05-3.00 (m, 1H), 0.92 (t, J=7.2 Hz, 3H).—(OH-Proton not observed in 1H NMR). LC-MS (Method-B)=593.2 $[M+H]^+$; 99.48% at RT 1.83 min. HPLC (Method-B)=98.87% at RT 7.02 min. Chiral HPLC (Method-E)=Peak-1=51.45% at RT 7.25 min. Peak-2=48.54% at RT 9.64 min.

Synthesis of ethyl rac-ethyl 2-((4R,5S)-7-ethyl-4-(4-fluorophenyl)-6-oxo-1-phenyl-5-(3-(trifluoromethyl)benzamido)-4,5,6,7-tetrohydro-1H-pyrazolo[3,4-b]pyridine-3-yl)acrylate (I-195)

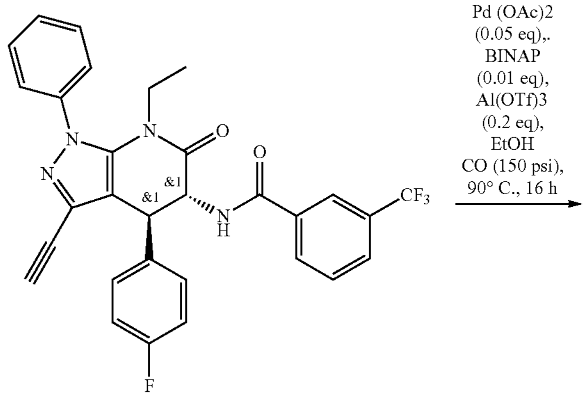

I-235

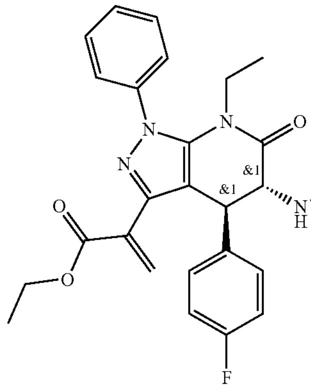

I-195

To a stirred solution of I-235 (200 mg, 0.366 mmol) in palladium (II) acetate (0.0041 g, 0.018 mmol) was added ethanol (10 mL) and (R)-(+)-2,2'-bis(diphenylphosphino)-1,1'-binaphthyl (0.0023 g, 0.0036 mmol), aluminum triflate (21.80 mg,0.046 mmol) under CO gas and stirred at 90° C. for 16 h. Progress of the reaction mixture was monitored by TLC. Reaction mixture was allowed to room temperature, quenched with water (20 mL, and extracted with DCM (2×20 mL). The combined organic layer was dried over anhydrous sodium sulfate and concentrated to afford crude compound. Obtained crude compound was purified by silica gel (230-400) column chromatography using Ethyl acetate in heptane. Compound was eluted in 5% MeOH/DCM, product containing fractions were collected and concentrated to afford (I-195) (80 mg, 35.22%) as an off-white solid.

$^1$H NMR (400 MHz, DMSO-$d_6$) δ=8.95 (d, J=8.8 Hz, 1H), 8.01-7.99 (m, 2H), 7.90 (d, J=8.0 Hz, 1H), 7.74-7.68 (m, 3H), 7.62-7.52 (m, 3H), 7.24-7.21 (m, 2H), 7.03-6.99 (m, 2H), 5.92-5.89 (m, 2H), 5.13-5.08 (m, 1H), 4.36 (d, J=12.8 Hz, 1H), 3.91-3.75 (m, 3H), 3.17-3.07 (m, 1H), 1.16-1.07 (m, 3H), 0.87-0.80 (m, 3H). LC-MS (Method-B)=621.2 $[M+H]^+$; 92.38% at RT 2.33 min. HPLC (Method-B)=84.56% at RT 9.41 min. Chiral HPLC (Method-E)=Peak-1=48.08% at RT 3.89 min. Peak-2=51.91% at RT 5.10 min.

Synthesis of rac-2-((4R,5S)-7-ethyl-4-(4-fluorophenyl)-6-oxo-1-phenyl-5-(3-(trifluoromethyl)benzamido)-4,5,6,7-tetrohydro-1H-pyrazolo[3,4-b]pyridine-3-yl)acrylic acid (I-208)

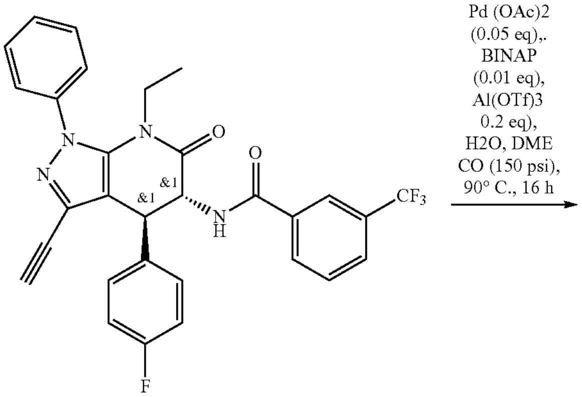

I-235

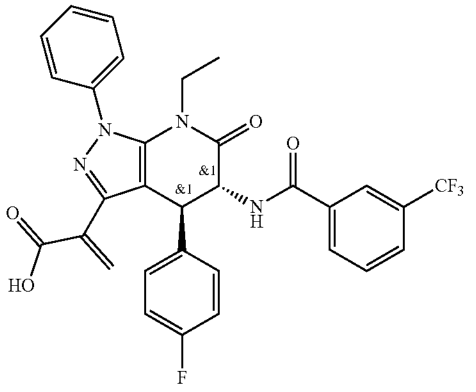

I-208

To a stirred solution of I-235 (300 mg, 0.54 mmol) in in 1,2-Dimethoxyethane (5 mL) & water (5 mL) was added palladium (II) acetate (0.0061 g, 0.027 mmol) and (R)-(+)-2,2'-bis(diphenylphosphino)-1,1'-binaphthyl (0.0035 g, 0.0054 mmol), aluminum triflate (21.80 mg,0.046 mmol) under CO gas and stirred at 90° C. for 16 h. Progress of the reaction was monitored by TLC. Reaction mixture was allowed to stir at room temperature, quenched with water (30 mL) and extracted with EtOAc (2×30 mL). Combined organic layer was dried over anhydrous sodium sulfate and concentrated to afford crude compound. Obtained crude compound was purified by silica gel (230-400) column chromatography using MeOH/DCM. Product was eluted in 5-10% MeOH/DCM. Product containing fractions were collected and concentrated to afford pure compound I-208 (80.0 mg, 24.60%) as a white solid.

$^{1}H$ NMR (400 MHZ, DMSO-$d_6$) δ=12.3 (s, 1H), 8.96 (d, J=8.8 Hz, 1H), 8.02-7.99 (m, 2H), 7.90 (d, J=8.0 Hz, 1H), 7.72-7.51 (m, 6H), 7.25-7.21 (m, 2H), 7.02-6.99 (m, 2H), 5.89-5.79 (m, 2H), 5.13-5.08 (m, 1H), 4.40 (d, J=12.4 Hz, 1H), 3.76-3.71 (m, 1H), 3.17-3.10 (m, 1H), 0.83 (t, J=6.8 Hz, 3H). LC-MS (Method-B)=593.2 $[M+H]^+$; 98.94% at RT 1.93 min. HPLC (Method-B)=97.96% at RT 6.23 min.

-continued

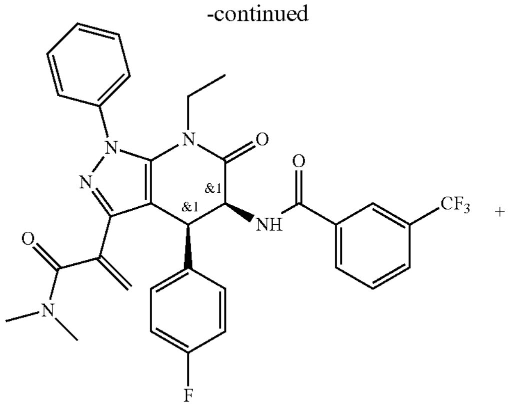

I-188

Synthesis of I-216

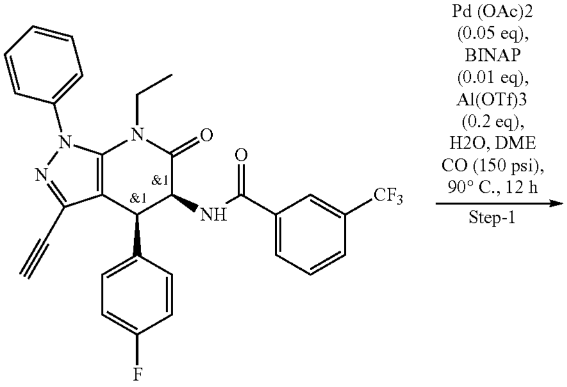

I-199

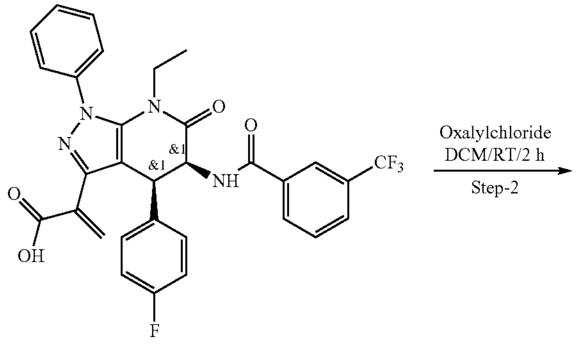

I-53

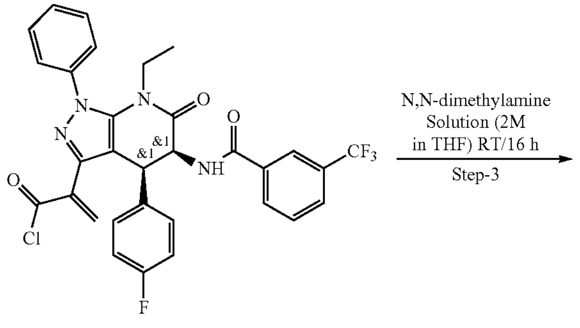

2

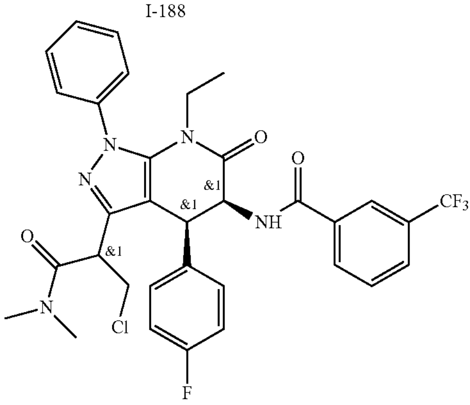

I-216

Step-1: Synthesis of rac-2-((4R,5R)-7-ethyl-4-(4-fluorophenyl)-6-oxo-1-phenyl-5-(3-(trifluoromethyl) benzamido)-4,5,6,7-tetrahydro-1H-pyrazolo[3,4-b] pyridine-3-yl) acrylic acid (1)

To a stirred solution of I-199 (180 mg, 0.32 mmol) in dichloromethane (2 mL) and 1,2-Dimethoxyethane (2 mL) was added Palladium(II) acetate (0.0038 g, 0.016 mmol) and (R)-(+)-2,2'-bis(diphenylphosphino)-1,1'-binaphthyl (0.021 g, 0.032 mmol) at room temperature. Reaction mixture was stirred at 90° C. for 12 h. After consumption of the starting material (by TLC), reaction mixture was allowed to stir at room temperature, quenched with water (20 mL) and extracted with DCM (2×20 mL). The combined organic layer was dried over anhydrous sodium sulfate and concentrated to afford crude compound. Obtained crude compound was purified by silica gel (230-400) column chromatography using ethyl acetate in heptane. Product was eluted in 10% MeOH/DCM. Product containing fractions were collected and concentrated to afford pure compound (I) (100 mg, 51.00%) as a pale-yellow solid.

$^{1}H$ NMR (400 MHZ, DMSO-$d_6$) δ=8.45 (d, J=7.2 Hz, 1H), 8.15-8.12 (m, 2H), 7.91 (d, J=8.0 Hz, 1H), 7.72-7.68 (m, 3H), 7.55-7.52 (m, 3H), 7.10-7.06 (m, 2H), 6.97-6.93 (m, 2H), 5.86 (s, 1H), 5.50 (t, J=7.2 Hz, 1H), 5.41 (s, 1H), 4.67 (d, J=6.8 Hz, 1H), 3.92-3.86 (m, 1H), 3.05-3.00 (m, 1H), 0.92 (t, J=7.2 Hz, 3H).—(OH-proton not observed in 1H NMR). LC-MS (Method-B)=593.2 $[M+H]^+$; 99.48% at RT 1.83 min. HPLC (Method-B)=98.87% at RT 7.02 min. Chiral HPLC (Method-E)=Peak-1=51.45% at RT 7.25 min. Peak-2=48.54% at RT 9.64 min.

Step-2: Synthesis of rac-2-((4R,5R)-7-ethyl-4-(4-fluorophenyl)-6-oxo-1-phenyl-5-(3-(trifluoromethyl) benzamido)-4,5,6,7-tetrahydro-1H-pyrazolo[3,4-b] pyridine-3-yl) acryloyl chloride (2)

To a stirred solution of compound (I) (50.0 mg, 0.084 mmol) in dichloromethane (5 mL) was added oxalyl chloride (0.021 g, 0.16 mmol) at 0° C. The reaction temperature was raised to room temperature and stirred at room temperature for 2 h. After consumption of the starting material (by TLC) the reaction mixture was concentrated under reduced pressure. The crude material was washed with DEE to afford compound (II) (50.0 mg, 97.0%) as an off-white solid. Reaction was confirmed by TLC with EtOH non-polar spot was formed.

Step-3: rac-N-((4R,5R)-3-(3-(dimethylamino)-3-oxoprop-1-en-2-yl)-7-ethyl-4-(4-fluorophenyl)-6-oxo-1-phenyl-4,5,6,7-tetrahydro-1H-pyrazolo[3,4-b] pyridine-5-yl)-3-(trifluoromethyl)benzamide (I-188) and rac-N-((4R,5R)-3-(3-chloro-1-(dimethylamino)-1-oxopropan-2-yl)-7-ethyl-4-(4-fluorophenyl)-6-oxo-1-phenyl-4,5,6,7-tetrahydro-1H-pyrazolo[3,4-b] pyridine-5-yl)-3-(trifluoromethyl)benzamide (I-216)

To a stirred solution of compound (II) (50 mg, 0.081 mmol) in dichloromethane (5 mL) was added dimethylamine (2 mol/L) in THF (0.08 mL, 0.16 mmol). Then the reaction mixture was stirred at room temperature for 16 h. Progress of the reaction mixture was monitored by TLC and LCMS. The reaction mixture was quenched with water (10 mL) and extracted with 10% MeOH\DCM (2×15 mL). The combined organic layer was dried over anhydrous sodium sulfate and concentrated to afford crude compound. Obtained crude was purified with column chromatography. The compound was eluted at (sp-1) 15 to 20% and (sp-2) was eluted at 30-35% EtOAc\heptane to afford (I-188) (15 mg, 30%) as white solid and (I-216) (20 mg, 37%) as an off-white solid.

I-188:

$^1$H NMR (400 MHZ, DMSO-$d_6$) δ=8.52 (d, J=6.8 Hz, 1H), 8.19-8.14 (m, 2H), 7.92 (d, J=8.0 Hz, 1H), 7.74-7.69 (m, 3H), 7.63-7.55 (m, 3H), 7.15-7.11 (m, 2H), 6.99-6.95 (m, 2H), 5.55-5.47 (m, 1H), 5.24 (s, 2H), 4.53 (d, J=7.2 Hz, 1H), 3.90-3.84 (m, 1H), 3.05-3.00 (m, 1H), 2.50-2.49 (s, 6H), 0.91 (t, J=7.2 Hz, 3H). LC-MS (Method-B)=619.9 $[M+H]^+$; 99.35% at RT 2.38 min. HPLC (Method-B)=97.77% at RT 9.49 min. Chiral HPLC (Method-E)=Peak-1=50.12% at RT 6.11 min. Peak-2=49.88% at RT 8.21 min.

I-216

$^1$H NMR (400 MHZ, DMSO-$d_6$) δ=8.50-8.47 (m, 1H), 8.20-8.13 (m, 2H), 7.92 (d, J=8.4 Hz, 1H), 7.74-7.68 (m, 3H), 7.62-7.54 (m, 3H), 7.14-7.08 (m, 2H), 6.95-6.84 (m, 2H), 5.49-5.43 (m, 2H), 4.67-4.50 (m, 1H), 4.35-4.33 (m, 1H), 4.07-3.42 (m, 3H), 3.06-3.05 (m, 1H), 2.86-2.71 (m, 4H), 2.22 (s, 1H), 0.82-0.97 (m, 3H). LC-MS (Method-B)=656.2 $[M+H]^+$; 97.50% at RT 2.40 min. HPLC (Method-B)=96.47% at RT 9.73, 9.82 min.

Synthesis of I-194

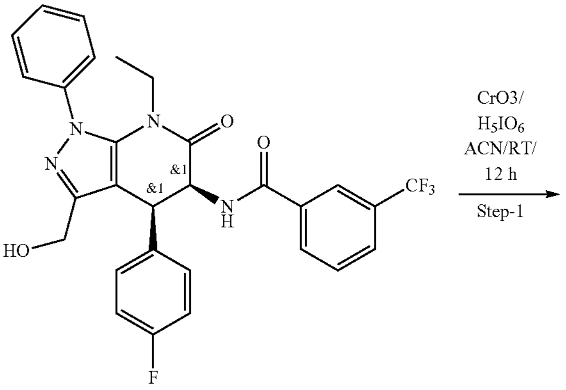

18-1

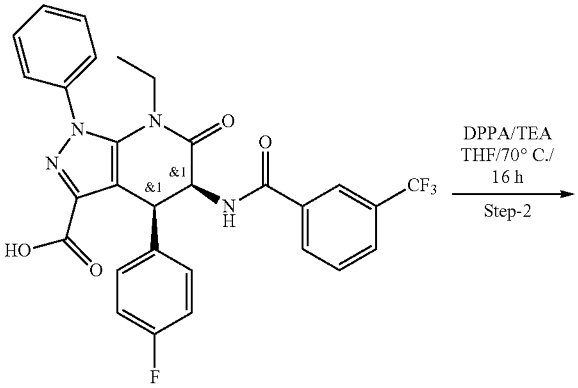

1

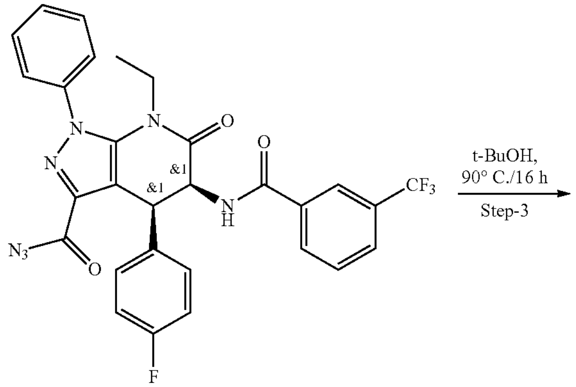

2

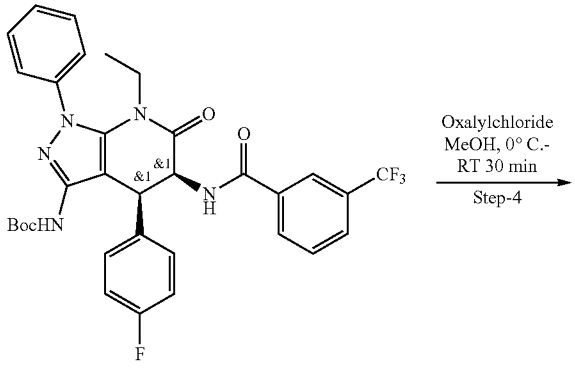

3

-continued

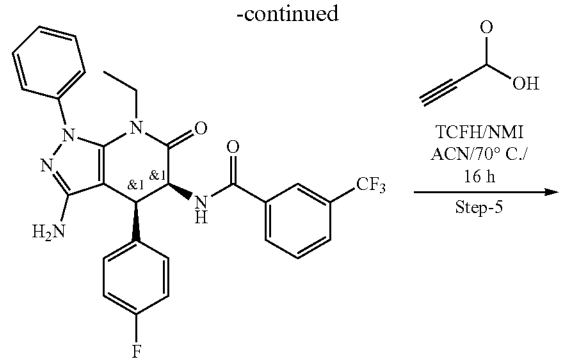

18-3

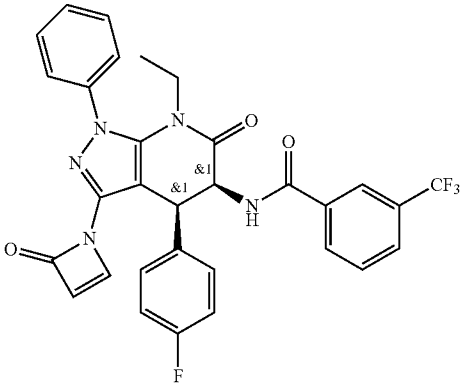

I-194

Step-1: Synthesis of rac-(4R,5R)-7-ethyl-4-(4-fluorophenyl)-6-oxo-1-phenyl-5-(3-(trifluoromethyl) benzamido)-4,5,6,7-tetrahydro-1H-pyrazolo[3,4-b] pyridine-3-carboxylic acid (1)

To a stirred solution of 18-1 (3 g, 5.321 mmol) in I (30 mL), periodic acid (2.5 g, 11 mmol) and Chromium (III) oxide (0.25 g, 1.6 mmol) were added at 0° C. The reaction mass was stirred for 12 h at room temperature. Reaction progress was monitored by TLC. After completion of reaction, the reaction mixture was diluted with 10% methanol in DCM and filtered through celite bed and washed with 10% methanol in DCM. Filtrate was concentrated under vacuum and washed with diethyl ether and filtered under vacuum. The compound was dried under vacuum to afford compound (I) (2.2 g, 38%) as an off-white solid.

$^1$H NMR (400 MHZ, DMSO-$d_6$) δ=9.90 (s, 1H), 8.64 (d, J=7.2 Hz, 1H), 8.16-8.13 (m, 2H), 7.92 (d, J=6.4 Hz, 1H), 7.84-7.81 (m, 2H), 7.73-7.64 (m, 4H), 7.10 (t, J=8.8 Hz, 2H), 7.02-6.99 (m, 2H), 5.57 (t, J=7.2 Hz, 1H), 4.89 (d, J=7.2 Hz, 1H), 3.91-3.86 (m, 1H), 3.17-3.15 (m, 1H), 0.90 (t, J=7.2 Hz, 3H). LC-MS (Method-A)=567.3 $[M+H]^+$; 51.58% at RT 2.43 min.

Step-2: Synthesis of rac-(4R,5R)-7-ethyl-4-(4-fluorophenyl)-6-oxo-1-phenyl-5-(3-(trifluoromethyl) benzamido)-4,5,6,7-tetrahydro-1H-pyrazolo[3,4-b] pyridine-3-carbonyl azide (2)

To a stirred solution of compound (1) (3.5 g, 6.0 mmol) in tetrahydrofuran (50 mL) was added diphenylphosphoryl azide (DPPA) (4.2 g, 15 mmol) and triethylamine (TEA) (1.8 g, 18 mmol) at 0° C. The reaction mixture was refluxed and stirred at 70° C. for 16 h. The reaction mixture was monitored by TLC and LCMS. The reaction mixture was quenched with water (200 mL) extracted by ethyl acetate (2×300 mL) and dried over anhydrous sodium sulphate and concentrated to afford crude compound, which was purified by combi flash using 100-200 mesh silica with 70-100% ethyl acetate in pet ether. Pure fractions were concentrated under vacuum to afford compound (2) (2.8 g, 76%) as a pale-yellow solid.

$^1$H NMR (400 MHZ, DMSO-$d_6$) δ=8.64 (d, J=7.2 Hz, 1H), 8.14 (s, 2H), 7.92 (d, J=6.4 Hz, 1H), 7.78 (s, 2H), 7.68 (s, 1H), 7.63 (m, 3H), 7.09 (m, 2H), 6.99 (m, 2H), 5.58 (m, 1H), 4.89 (m, 1H), 3.91 (m, 1H), 3.15 (m, 1H), 0.88 (s, 3H). LC-MS (Method-A)=592.3 $[M+H]^+$; 95.62% at RT 2.29 min.

Step-3: Synthesis of rac-tert-butyl ((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)carbamate (3)

To a stirred solution of compound (2) (2.8 g, 4.5 mmol) in t-BuOH (30 mL) was refluxed and stirred for 16 h at 90° C. The reaction mixture was monitored by TLC and LCMS. The reaction mixture was concentrated under vacuum to afford crude compound, which was purified by washing with pentane to afford compound (3) (2.5 g, 76%) as off-white solid.

$^1$H NMR (400 MHZ, DMSO-$d_6$) δ=9.17 (s, 1H), 8.43 (d, J=7.6 Hz, 1H), 8.15-8.09 (m, 1H), 7.91 (d, J=7.6 Hz, 1H), 7.72-7.64 (m, 5H), 7.61-7.51 (m, 4H), 7.10-7.06 (m, 1H), 6.94-6.91 (m, 1H), 5.47 (t, J=6.8 Hz, 1H), 4.75 (d, J=7.2 Hz, 1H), 3.90-3.86 (m, 1H), 3.09-3.04 (m, 1H), 1.34 (s, 9H), 0.93-0.84 (m, 3H). LC-MS (Method-A)=637.5 $[M+H]^+$; 88.18% at RT 2.51 min.

Step-4: Synthesis of rac-N-((4R,5R)-3-amino-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (4)

To a stirred solution of compound (3) (1 g, 1.50 mmol) in methanol (20 mL), oxalyl chloride (0.97 g, 7.52 mmol) was added at 0° C. Then the reaction mass was stirred at room temperature for 30 min. Reaction progress was monitored by TLC, and the reaction mixture was continued to stir at room temperature for 12 h. The reaction was monitored by TLC. After completion of reaction, the reaction mass was concentrated under vacuum to afford crude compound. The obtained crude compound was triturated with 10% diethyl ether in pentane to afford compound (4) (700 mg, 71.79%) as pale-yellow solid.

$^1$H NMR (400 MHZ, DMSO-$d_6$) δ=8.50 (d, J=6.8 Hz, 1H), 8.15-8.12 (m, 2H), 7.92 (d, J=8.0 Hz, 1H), 7.73-7.69 (m, 1H), 7.71 (t, J=8.0 Hz, 1H), 7.58-7.56 (m, 2H), 7.54-7.50 (m, 2H), 7.44-7.40 (m, 1H), 7.12-7.08 (m, 2H), 7.02-6.98 (m, 2H), 5.46 (t, J=7.2 Hz, 1H), 4.58 (d, J=7.2 Hz, 1H), 3.91-3.85 (m, 1H), 3.08-3.03 (m, 1H), 1.34-1.30 (m, 1H), 0.92 (t, J=7.2 Hz, 3H). LC-MS (Method-A)=538.81 $[M+H]^+$; 83.30% at RT 2.10 min.

Step-5: Synthesis of N-((4S,5S)-7-ethyl-4-(4-fluorophenyl)-6-oxo-3-(2-oxoazet-1 (2H)-yl)-1-phenyl-4,5,6,7-tetrahydro-1H-pyrazolo[3,4-b]pyridine-5-yl)-3-(trifluoromethyl)benzamide (I-194)

To the stirred solution of compound (4) (200 mg, 0.30 mmol) in I (5 mL, 93.8 mmol) were added prop-2-ynoic acid (0.04 g, 0.61 mmol), chloro-N,N,N',N'-tetramethylformamidinium hexafluorophosphate (TCFH) (0.13 g, 0.46 mmol) and 1-methylimidazole (NMI) (0.07 g, 0.92 mmol) at room temperature. Then the reaction mixture was stirred at 70° C. for 16 h. Reaction progress was monitored by TLC. The pure spot fraction was concentrated the extracted to get crude product. Obtained crude was purified by flash column chromatography using 40-50% ethyl acetate in pet ether. Pure fractions were concentrated and dried under vacuum to afford compound (A & B) I-194 (30 mg, 15.49%) as off white solid.

$^1$H NMR (400 MHZ, $CDCl_3$) δ=7.99 (s, 1H), 7.88-7.89 (m, 3H), 7.60-7.51 (m, 6H), 7.07-6.97 (m, 4H), 6.79 (d, J=6.0 Hz, 1H), 6.02 (d, J=6.4 Hz, 1H), 5.38-5.34 (m, 1H), 5.10 (d, J=7.2 Hz, 1H), 3.86-3.80 (m, 1H), 3.64-3.58 (m, 1H), 0.83 (t, J=7.2 Hz, 3H). LC-MS (Method-B)=590.2 [M+H]$^+$; 96.09% at RT 2.27 min. HPLC (Method-B)=90.18% at RT 9.06 min. Chiral HPLC (Method-E)=Peak-1=50.13% at RT 21.9 min. Peak-2=49.86% at RT 23.5 min Synthesis of I-225

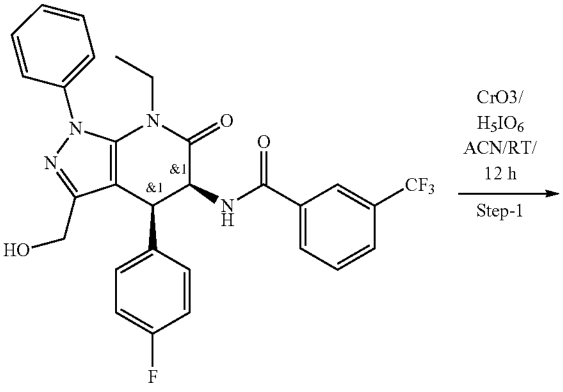

18-1

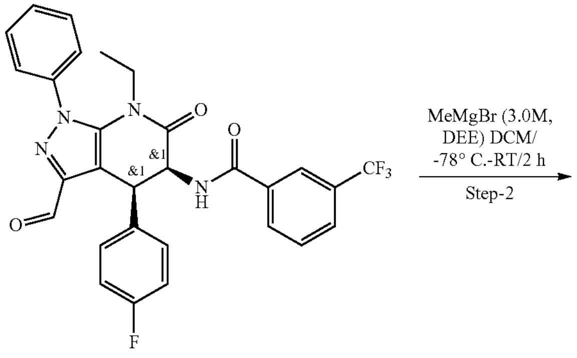

1

-continued

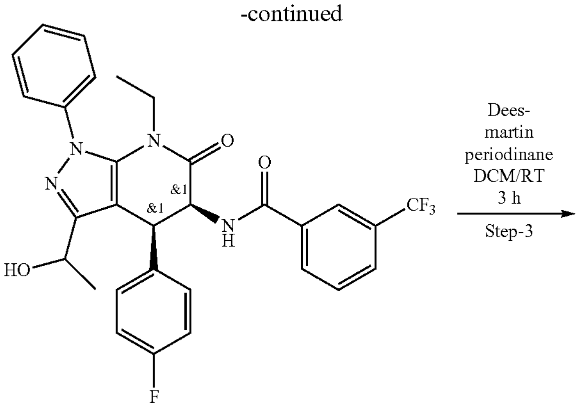

2

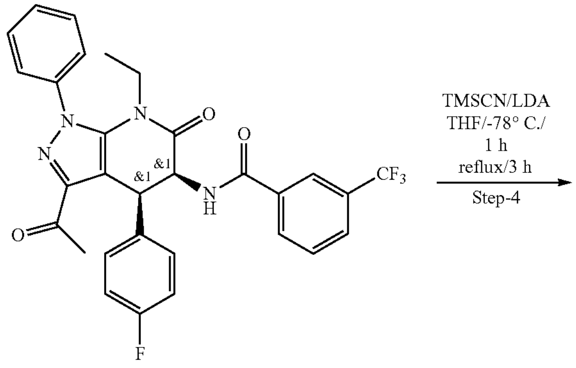

3

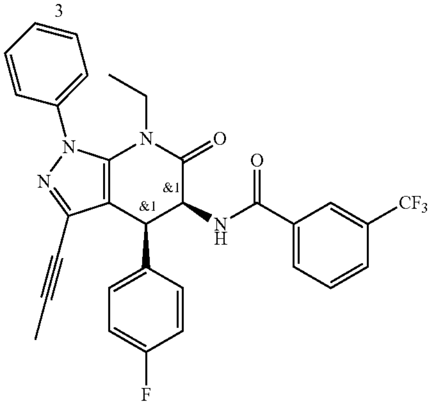

I-225

Step-1: Synthesis of rac-N-((4R,5R)-7-ethyl-4-(4-fluorophenyl)-3-formyl-6-oxo-1-phenyl-4,5,6,7-tetrahydro-1H-pyrazolo[3,4-b]pyridine-5-yl)-3-(trifluoromethyl)benzamide (1)

To a stirred solution of 18-1 (6 g, 10.43 mmol) in DMF (60 mL), pyridinium dichromate (6.25 g, 16.3 mmol) was added at room temperature. Then the reaction mixture was stirred at room temperature for 12 h. Reaction progress was monitored by TLC. After completion of reaction, the reaction mixture was quenched with water (300 mL) and filtered through celite bed. The reaction mass was extracted with ethyl acetate (2×500 mL). The organic layer was dried over anhydrous sodium sulfate and concentrated to afford crude compound. Obtained crude material was purified through flash column chromatography (100-200 mesh) with 50-60% ethyl acetate in pet ether. Combined pure fractions was concentrated under vacuum and washed with ether to afford compound (1) (3.5 g, 58%) as a pale brown solid.

$^1$H NMR (400 MHZ, DMSO-$d_6$) δ=9.90 (s, 1H), 8.64 (d, J=7.2 Hz, 1H), 8.16-8.13 (m, 2H), 7.92 (d, J=6.4 Hz, 1H), 7.84-7.81 (m, 2H), 7.73-7.64 (m, 4H), 7.10 (t, J=8.8 Hz, 2H), 7.02-6.99 (m, 2H), 5.57 (t, J=7.2 Hz, 1H), 4.89 (d, J=7.2 Hz, 1H), 3.91-3.86 (m, 1H), 3.17-3.15 (m, 1H), 0.90 (t, J=7.2 Hz, 3H). LC-MS (Method-A)=551.5 $[M+H]^+$; 95.59% at RT 2.47 min.

Step-2: Synthesis of rac-N-((4R,5R)-7-ethyl-4-(4-fluorophenyl)-3-(1-hydroxyethyl)-6-oxo-1-phenyl-4,5,6,7-tetrahydro-1H-pyrazolo[3,4-b]pyridine-5-yl)-3-(trifluoromethyl)benzamide (2)

To a stirred solution of compound (I) (0.8 g, 1 mmol) in dichloromethane (10.00 mL, 156 mmol) was added methyl magnesium bromide solution (3.0 mol/L) in diethyl ether at −78° C. Then the reaction mixture was stirred at room temperature for 2 h. Progress of the reaction was monitored by TLC. Reaction mixture was allowed to stir at room temperature, quenched with water (100 mL), and extracted with DCM (2×100 mL). The combined organic layers were dried over anhydrous sodium sulfate and concentrated to afford crude compound. Obtain crude compound was purified by silica gel (230-400) column chromatography using ethyl acetate in heptane. Product was eluted in 30% EtOAc in heptane. Product containing fractions were collected and concentrated to afford compound (2) (0.6 g, 70%) as a white solid.

$^1$H NMR (400 MHZ, DMSO-$d_6$) δ=8.52-8.48 (m, 1H), 8.16-8.13 (m, 2H), 7.92 (d, J=8.0 Hz, 1H), 7.73-7.65 (m, 3H), 7.60-7.50 (m, 3H), 7.12-7.07 (m, 2H), 6.99-6.95 (m, 2H), 5.75 (s, 1H), 5.51-5.47 (m, 1H), 5.11 (d, J=5.2 Hz, 1H), 4.82-4.77 (m, 1H), 3.93-3.86 (m, 1H), 3.17-3.02 (m, 1H), 1.31 (d, J=6.4 Hz, 2H), 1.02-0.99 (m, 1H), 0.94-0.89 (m, 3H). LC-MS (Method-B)=567.2 $[M+H]^+$; 80.15% at RT 2.30 min.

Step-3: Synthesis of rac-N-((4R,5R)-3-acetyl-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (3)

To a stirring solution of compound (II) (800 mg, 1.41 mmol) in dichloromethane (10.0 mL) was added Dess-martin periodinane (0.92 g, 2.11 mmol) at 0° C. under inert atmosphere. The reaction mixture was stirred at room temperature for 3 h. After consumption of the starting material (by TLC), the reaction was diluted into ice cold water (50 mL) and extracted with EtOAc (2×125 mL). The organic layer was dried over anhydrous $Na_2SO_4$, and concentrated under reduced pressure. The crude compound was purified by medium pressure liquid chromatography by eluting with 10-20% EtOAc/heptane to afford compound (3) (260 mg, 29.36%) as a color-less oil.

$^1$H NMR (400 MHZ, DMSO-$d_6$) δ=8.58 (d, J=6.8 Hz, 1H), 8.15-8.12 (m, 2H), 7.91 (d, J=8.0 Hz, 1H), 7.82-7.80 (m, 2H), 7.72-7.64 (m, 4H), 7.11-7.06 (m, 2H), 7.01-6.97 (m, 2H), 5.52 (t, J=7.2 Hz, 1H), 4.93 (d, J=7.2 Hz, 1H), 3.91-3.86 (m, 1H), 3.03-2.98 (m, 1H), 2.50-2.44 (m, 3H), 0.91-0.84 (m, 3H). LC-MS (Method-B)=564.7 $[M+H]^+$; 91.13% at RT 2.50 min.

Step-4: Synthesis of rac-N-((4R,5R)-7-ethyl-4-(4-fluorophenyl)-6-oxo-1-phenyl-3-(prop-1-yn-1-yl)-4,5,6,7-tetrahydro-1H-pyrazolo[3,4-b]pyridine-5-yl)-3-(trifluoromethyl)benzamide (I-225)

To a stirred solution of diisopropylamine (0.05 g, 0.53 mmol) butyl lithium (1.5 mol/L) in cyclohexane (0.35 mL, 0.5314 mmol, 1.5 mol/L) in Tetrahydrofuran (10.0 mL) was added under argon atmosphere at −78° C. Reaction mixture was stirred for 20 min and trimethylsilyl cyanide (0.053 g, 0.53 mmol) was added to the reaction mixture drop wise at −78° C. Reaction mixture was stirred at −78° C. for 30 min. Then the solution of compound (III) (250 mg, 0.44 mmol) in tetrahydrofuran (2.0 mL) at −78° C. was added and stirred for 1 h and reflux for 3 h. Progress of the reaction was monitored by TLC and LCMS. Reaction mixture was allowed to RT, quenched with water (50 mL), and extracted with ethyl acetate (2×50 mL). The combined organic layers were dried over anhydrous sodium sulfate and concentrated to afford crude compound. Crude compound was purified by silica gel (230-400) column chromatography using ethyl acetate in heptane. Product was eluted in 20-40% EtOAc in heptane. Product containing fractions were collected and concentrated to afford I-225 (19.0 mg, 7.42%) as an off-white solid.

$^1$H NMR (400 MHZ, DMSO-$d_6$) δ=8.60 (d, J=7.2 Hz, 1H), 8.16-8.13 (m, 2H), 7.92 (d, J=8.0 Hz, 1H), 7.73-7.69 (m, 3H), 7.62-7.55 (m, 3H), 7.13-7.09 (m, 2H), 7.01-6.98 (m, 2H), 5.51 (d, J=7.2 Hz, 1H), 4.52 (d, J=7.2 Hz, 1H), 3.89-3.83 (m, 1H), 3.03-2.98 (m, 1H), 1.99 (s, 3H), 0.88 (t, J=7.2 Hz, 3H). LC-MS (Method-B)=561.2 $[M+H]^+$; 96.90% at RT 2.45 min. HPLC (Method-B)=87.52% at RT 10.04 min.

Example 19: Synthesis of Compounds I-80, I-136, I-63, I-47, I-66, and I-114

NMR:

$^1$H NMR spectrum was recorded on Bruker 400 MHz and Varian 400 MHz instruments internally referenced to a tetramethyl silane (TMS) signal. Chemical shifts (d) and coupling constants (J) were expressed in parts per million and hertz, respectively.

LCMS:

Method-A: LCMS, X-Select (Formic acid); Column: X-Select CSH C18 (3.0*50) mm 2.5μ; Mobile Phase: A: 0.05% Formic acid in water: I (95:5) B: 0.05% Formic acid in CAN; Inj Volume: 2.0 μL, Column oven temperature: 50° C.; Flow Rate: 1.2 mL/min. Gradient Program (B %): 0.0/2, 0.3/2, 2.0/98, 2.8/98, 3.0/2,3.7/2.

Method-B: Column: X-Bridge BEH C18, (50 mm*3.0 mm,2.5μ) Mobile Phase A: 2.5 mM Ammonium Bicarbonate in Water+5% CAN; Mobile Phase B: 100% I Flow rate: 1.0 mL/min. Column temperature: 40° C.; Gradient Program (B %): 0.0/2, 0.3/2, 2.0/98, 2.8/98, 3.0/2, 3.7/2.

Method-C: Column: X-Select CSH C18 (50 mm*3.0 mm,2.5μ) Mobile Phase A: 0.05% TFA in Water; Mobile Phase B: 0.05% TFA in Acetonitrile; Flow rate: 1.0 mL/min. Column temperature: 40° C. Gradient Program (B %): 0.0/2, 0.3/2, 2.0/98, 2.8/98, 3.0/2, 3.7/2.

HPLC:

Method-A: Column: X Select CSH C18 (150×4.6) mm, 3.5μ; Mobile phase A: 0.1% FA in Water: I (95:05); Mobile phase B: Acetonitrile; Gradient Programme: T/B %: 0.01/5, 1/5, 8/100, 12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/5, 1.0/5, 8.0/100, 12.0/100, 14.0/5, 18.0/5; Flow: 1.0 mL/min.

Method-C: Column: X SELECT CSH C18 (150×4.6 mm, 3.5μ); Mobile Phase A; 0.05% TFA in water: I (95:05); Mobile Phase B: 0.05% TFA in water: I (05:95); Programme: T/B %: 0.01/10, 12/90, 16/90; Flow: 1 mL/min.; Diluent: water: I (80:20).

Method-E: Column: CHIRALCEL-OJ-H (250×4.6 mm, 5μ) Mobile Phase A: 0.1% DEA in Hexane; Mobile Phase B: IPA A/B: 60/40 Flow: 1.0 ml/MIN PDA: OJ-H_015.

Chiral—HPLC:

Method-A: Column Name: CHIRALPAK-IA (150*4.6 mm, 3 μm)) Mobile phase-A: n-hexane, Mobile phase-B: EtOH: MeOH (1:1), Flow rate: 1.0 mL/min % A/B: 90:10.

Method-B: Column: CHIRALCEL-OX-H (250×4.6 mm, 5μ) Mobile Phase A: n-Hexane, Mobile Phase B: IPA, A/B: 50/50 Flow: 1.0 mL/min.

Method-C: Column Name: CHIRALPAK-IC (250×4.6 mm, 5 μm) Mobile phase-A: 0.1% TFA in n-Hexane, Mobile phase-B: DCM: IPA (50:50), Flow rate: 1.0 mL/min % A/B: 60/40.

Synthesis of 19-2

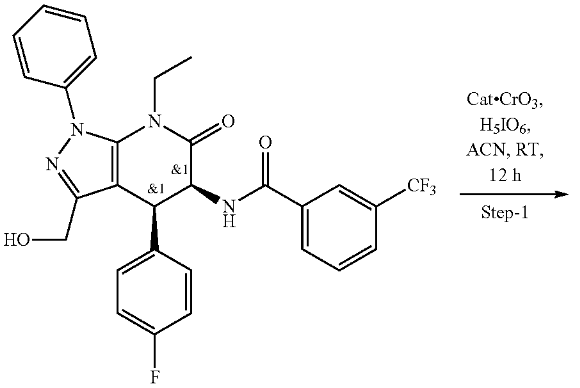

19-1

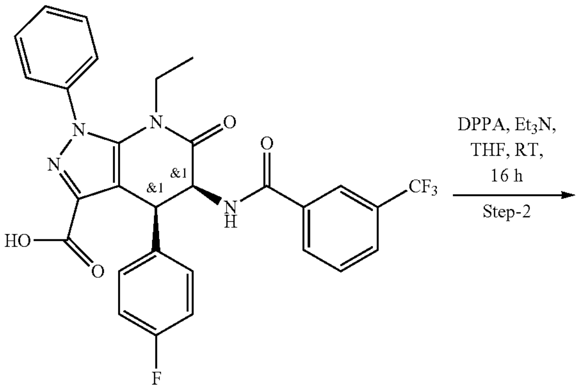

1

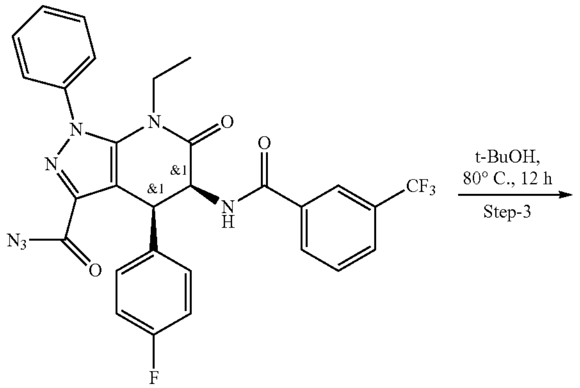

2

-continued

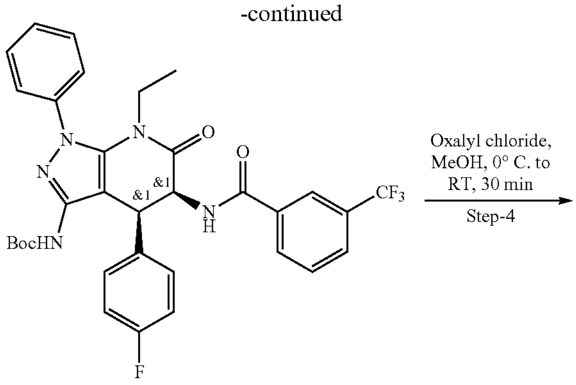

3

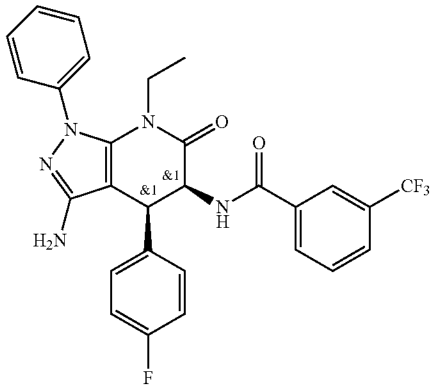

19-2

Step-1: Synthesis of 7-ethyl-4-(4-fluorophenyl)-6-oxo-1-phenyl-5-[[3-(trifluoromethyl)benzoyl]amino]-4,5-dihydropyrazolo[3,4-b]pyridine-3-carboxylic acid (1)

To a stirred solution of compound 19-1 (5 g, 8.68 mmol) in I (50 mL), periodic acid (4.04 g, 17.38 mmol) and Chromium (III) oxide (0.39 g, 2.606 mmol) was added at 0° C. The reaction mixture was stirred at room temperature for 12 h. Reaction progress was monitored by TLC. After completion of reaction, the reaction mixture was diluted with 10% methanol in DCM and filtered by celite bed. Filtrate was concentrated under vacuum and washed with diethyl ether. The compound was dried under vacuum to afford compound (1) (3.5 g, 69%) as off-white solid.

$^1H$ NMR (400 MHZ, DMSO-$d_6$)=13.0 (s, 1H), 8.58 (d, J=7.3 Hz, 1H), 8.19-8.12 (m, 2H), 7.92 (d, J=7.8 Hz, 1H), 7.78 (d, J=6.8 Hz, 2H), 7.71 (t, J=7.8 Hz, 1H), 7.66-7.60 (m, 3H), 7.12-7.06 (m, 2H), 7.00-6.96 (m, 2H), 5.55 (t, J=7.3 Hz, 1H), 4.92 (d, J=7.3 Hz, 1H), 3.88 (dd, J=14.2, 7.3 Hz, 1H), 3.01 (dd, J=14.2, 6.8 Hz, 1H), 0.90 (t, J=6.8 Hz, 3H). LC-MS (Method-A)=567.31 $[M+H]^+$; 96.91% at RT 2.12 min.

Step-2: Synthesis of rac-(4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carbonyl azide (2)

To a stirred solution of compound (1) (3.5 g, 6.0 mmol) in tetrahydrofuran (30 mL) was added diphenylphosphoryl azide (DPPA) (4.2 g, 15 mmol) and triethylamine (1.8 g, 18 mmol) at 0° C. The reaction was stirred at RT for 16 h. The reaction progress was monitored by TLC and LCMS. The reaction mixture was quenched with water (250 mL) extracted by ethyl acetate (2×300 mL) and dried over anhydrous sodium sulphate and concentrated to afford crude compound, which was purified by combi flash to afford compound (2) (2.8 g, 76%) as pale-yellow solid.

$^1$H NMR (400 MHZ, DMSO-$d_6$)=8.61 (d, J=4.4 Hz, 1H), 8.15 (s, 2H), 7.91 (d, J=5.4 Hz, 1H), 7.78-7.63 (m, 6H), 7.09-6.99 (m, 4H), 5.57 (s, 1H), 4.91 (s, 1H), 3.81 (s, 1H), 3.01 (s, 1H), 0.88 (s, 3H). LC-MS (Method-A)=592.2 $[M+H]^+$; 95.68% at RT 2.29 min.

Step-3: Synthesis of tert-butyl ((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-yl)carbamate (3)

Compound (2) (2.8 g, 4.5 mmol) in tertiary butanol (25 mL) was stirred at 80° C. for 12 h. Reaction progress was monitored by TLC. After completion of reaction, the reaction mixture was concentrated under vacuum, washed with pentane to afford compound (3) (2.7 g, 75%) as pale-yellow solid.

$^1$H NMR (400 MHZ, CHLOROFORM-d)=9.54 (s, 1H), 9.17 (s, 1H), 8.43 (d, J=7.6 Hz, 1H), 8.15-8.09 (s, 1H), 7.91 (d, J=7.6 Hz, 1H), 7.78-7.51 (m, 6H), 7.10-7.06 (m, 2H), 6.94-6.91 (m, 2H), 5.49-5.45 (m, 1H), 4.75 (d, J=7.2 Hz, 1H), 3.90-3.86 (m, 1H), 3.07-3.04 (m, 1H), 1.32 (s, 9H), 0.91 (t, J=6.8 Hz, 3H). LC-MS (Method-A)=638.5 $[M+H]^+$; 82.54% at RT 2.30 min

Step-4: Synthesis of N-((4S,5S)-3-amino-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (19-2)

To a stirred solution of compound (3) (5 g, 6.43 mmol) in methanol (100 mL), oxalyl chloride (4.16 g, 32.15 mmol) was added at 0° C. The reaction was stirred at room temperature for 30 min. Reaction progress was monitored by TLC. After completion of reaction, the reaction mixture was concentrated under vacuum to afford crude compound. Obtained crude was washed with 50% diethyl ether in pentane and filtered under vacuum to afford 19-2 (3 g, 72.91%) as pale green solid.

$^1$H NMR (400 MHZ, DMSO-$d_6$): 8.47 (d, J=7.2 Hz, 1H), 8.15-8.12 (m, 2H), 7.92 (d, J=7.6 Hz, 1H), 7.73-7.69 (m, 1H), 7.61-7.48 (m, 5H), 7.41-7.38 (m, 4H), 5.69-5.66 (m, 1H), 5.52-5.49 (m, 2H), 4.84 (d, J=6.8 Hz, 1H), 3.92-3.86 (m, 1H), 3.08-3.03 (m, 1H), 0.91 (t, J=7.2 Hz, 3H). LC-MS (Method-B)=538.4 $[M+H]^+$; 99.43% at RT 2.30 min.

HPLC (Method-B)=99.65% at RT 9.22 min.

Synthesis of Corresponding Analogues

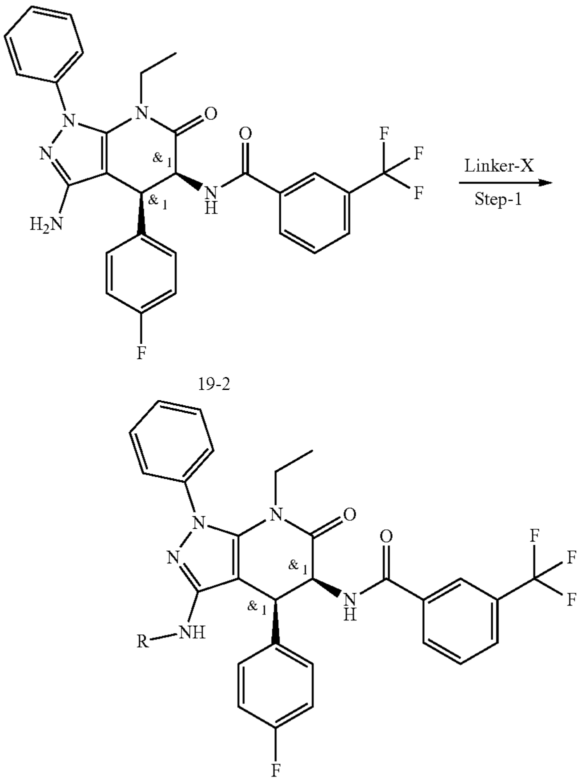

A. Mukaiyama reagent/Bu3N/DMF/RT/16 h
B. 2-cyanoacetic acid, EDAC/1-hyrdoxybenzotriazole/DIPEA/DMF/RT/16 h
C 4-cyanotetrahydropyran-4-carboxylic acid, 1-propanephosphonic anydride, N, N-Diisopropylethylamine, RT, 16 h Method A Procedure:

To a stirred solution of Linker (X) (180 mg, 1.4 mmol) in DMF (10 mL) was added compound 19-2 (250 mg, 0.47 mmol), tributylamine (0.57 mL, 2.3 mmol), 2-chloro-1-methylpyridinium iodide (180 mg, 0.70 mmol). Then the reaction mixture was stirred at room temperature for 16 h. After consumption of the starting material (by TLC), the reaction mixture was diluted with water (20 mL) and extracted by using EtOAc (2×25 mL). The organic layer was dried over anhydrous $Na_2SO_4$, filtered, and concentrated under reduced pressure. The obtained crude material was purified by silica gel column chromatography and the compound was eluted with 35-40% EtOAc: PE to afford desired compound.

Method-B Procedure (1-80):

To a stirred solution of 2-cyanoacetic acid (120 mg, 1.4 mmol) in DMF (3.6 mL, 47 mmol) was added 19-2 (250 mg, 0.47 mmol), EDAC (180 mg, 0.93 mmol), 1-hydroxybenzotriazole (130 mg, 0.93 mmol), and DIPEA (303 mg, 2.35 mmol) at room temperature. The reaction mixture was stirred at room temperature for 16 h. After consumption of the starting material (by TLC), the reaction mixture was diluted with water (25 mL) and extracted with EtOAc (2×25 mL). The organic layer was dried over anhydrous $Na_2SO_4$, filtered, and concentrated under reduced pressure. The obtained crude material was purified by mixing with previous batch using silica gel column chromatography followed by purification by SFC. The compound was eluted at 35-40% EtOAc: PE to afford the title compound 1-80 (21 mg, 7.5%) as an off-white colour solid.

Method-C Procedure (I-66):

To a stirred solution of 4-cyanotetrahydropyran-4-carboxylic acid (140 mg, 0.93 mmol) in I (3.7 mL, 70 mmol) was added 19-2 (250 mg, 0.47 mmol), 1-propanephosphonic anhydride (450 mg, 1.4 mmol) and N,N-Diisopropylethylamine (0.32 mL, 1.9 mmol) at room temperature. The reaction mixture was stirred at room temperature for 16 h. After consumption of the starting material (by TLC), the reaction mixture was diluted with water (20 mL) and extracted with EtOAc (2×20 mL). The organic layer was dried over anhydrous $Na_2SO_4$, filtered, and concentrated under reduced pressure. The obtained crude material was purified by silica gel column chromatography and compound was eluted with 35-40% EtOAc: PE to afford the title compound I-66 (37 mg, 12%) as an off-white colour solid.

LC-MS (Method-A)=633.2 $[M+H]^+$; 98.67% at RT 2.50 min. HPLC (Method-A)=99.12% at RT 6.39 min. Chiral HPLC (Method-A)=Peak-1=49.94% at RT 3.63 min. Peak-2=50.06% at RT 4.03 min.

I-47

$^1$H NMR (400 MHZ, DMSO-$d_6$) δ=10.31 (s, 1H), 8.50 (d, J=7.4 Hz, 1H), 8.13-8.07 (m, 1H), 7.91 (d, J=7.5 Hz, 1H), 7.73-7.66 (m, 3H), 7.63-7.48 (m, 3H), 7.10-7.04 (m, 2H), 6.97-6.91 (m, 2H), 5.54 (t, J=7.4 Hz, 1H), 4.70 (d, J=7.4 Hz, 1H), 3.89 (m, 1H), 3.16-3.02 (m, 1H), 1.58-1.52 (m, 3H), 1.45-1.43 (m, 1H), 1.23 (s, 1H), 0.92 (t, J=7.1 Hz, 3H). LC-MS (Method-B)=631.1 $[M+H]^+$; 97.67% at RT 2.30 min. HPLC (Method-A)=96.53% at RT 8.90 min. Chiral HPLC (Method-A)=Peak-1=50.13% at RT 4.18 min. Peak-2=49.87% at RT 5.13 min.

| Sr. No | Cpd. Number | Structure | Method | 19-2 (mg) | Linker Qty (mg) | Qty (mg) & nature of compound | Yield (%) |
|---|---|---|---|---|---|---|---|
| 1. | I-136 | 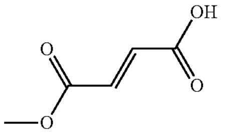 | A | 250 | 180 | 93 (off-white) | 31 |
| 2. | I-63 | 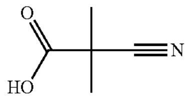 | A | 250 | 110 | 83.37 (off-white) | 28.74 |
| 3. | I-47 | 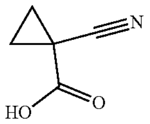 | A | 250 | 100 | 55.92 (off-white) | 19.28 |
| 4. | I-80 | 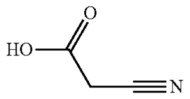 | B | 250 | 120 | 21 (off-white) | 75 |
| 5. | I-66 | 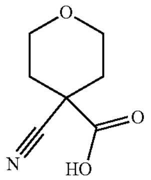 [SMILES: N#CC1(C(=O)O)CCOCC1] | C | 250 | 140 | 37 (off-white) | 12 |

I-136

$^1$H NMR (400 MHZ, DMSO-$d_6$) δ=10.77 (s, 1H), 8.50 (d, J=7.2 Hz, 1H), 8.18-8.09 (m, 2H), 7.92 (d, J=7.6 Hz, 1H), 7.76-7.67 (m, 3H), 7.64-7.49 (m, 3H), 7.15 (d, J=15.4 Hz, 1H), 7.10-7.03 (m, 2H), 6.96-6.90 (m, 2H), 6.64 (d, J=15.5 Hz, 1H), 5.54 (t, J=7.2 Hz, 1H), 4.96 (d, J=7.1 Hz, 1H), 3.94-3.83 (m, 1H), 3.71 (s, 3H), 3.11-3.01 (m, 1H), 0.94 (t, J=7.1 Hz, 3H). LC-MS (Method-C)=650.2 $[M+H]^+$; 98.06% at RT 3.66 min. HPLC (Method-A)=98.17% at RT 6.41 min. Chiral HPLC (Method-B)=Peak-1=50.10% at RT 6.11 min. Peak-2=48.89% at RT 9.33 min.

I-63

$^1$H NMR (400 MHZ, DMSO-$d_6$) δ=10.31 (s, 1H), 8.50 (d, J=7.4 Hz, 1H), 8.13-8.08 (m, 2H), 7.91 (d, J=7.5 Hz, 1H), 7.74-7.67 (m, 3H), 7.64-7.57 (m, 2H), 7.57-7.52 (m, 1H), 7.11-7.04 (m, 2H), 6.97-6.91 (m, 2H), 5.54 (t, J=7.4 Hz, 1H), 4.70 (d, J=7.4 Hz, 1H), 3.89 (d, J=7.4, Hz, 1H), 3.14-3.04 (m, 1H), 1.49 (d, J=13.6 Hz, 6H), 0.92 (t, J=7.1 Hz, 3H).

I-80

$^1$H NMR (400 MHZ, DMSO-$d_6$) δ=10.51 (br s, 1H), 8.52-8.45 (m, 1H), 8.19-8.11 (m, 2H), 7.92 (d, J=7.9 Hz, 1H), 7.75-7.68 (m, 3H), 7.63-7.50 (m, 3H), 7.08 (t, J=8.9 Hz, 2H), 6.98-6.90 (m, 2H), 5.51 (t, J=7.2 Hz, 1H), 4.82 (d, J=7.5 Hz, 1H), 3.95-3.75 (m, 3H), 3.11-2.98 (m, 1H), 0.91 (t, J=7.1 Hz, 3H). LC-MS (Method-C)=605.2 $[M+H]^+$; 98.32% at RT 3.52 min. HPLC (Method-A)=99.41% at RT 6.15 min. Chiral HPLC (Method-A)=Peak-1=50.17% at RT 5.03 min. Peak-2=49.83% at RT 7.67 min.

I-66

$^1$H NMR (400 MHZ, DMSO-$d_6$) δ=10.53 (s, 1H), 8.52 (d, J=7.4 Hz, 1H), 8.13-8.08 (m, 2H), 7.91 (d, J=7.9 Hz, 1H), 7.74-7.66 (m, 3H), 7.63-7.58 (m, 3H), 7.12-7.03 (m, 2H), 6.98-6.90 (m, 2H), 5.55 (t, J=7.4 Hz, 1H), 4.69 (d, J=7.3 Hz, 1H), 3.94-3.64 (m, 3H), 3.55-3.39 (m, 2H), 3.15-3.02 (m, 1H), 2.04-1.85 (m, 4H), 0.92 (t, J=7.1 Hz, 3H). LC-MS (Method-B)=675.0 $[M+H]^+$; 98.73% at RT 2.29 min. HPLC (Method-B)=98.14% at RT 8.81 min. Chiral HPLC (Method-A)=Peak-1=49.60% at RT 5.38 min. Peak-2=50.39% at RT 9.06 min.

Synthesis of I-114

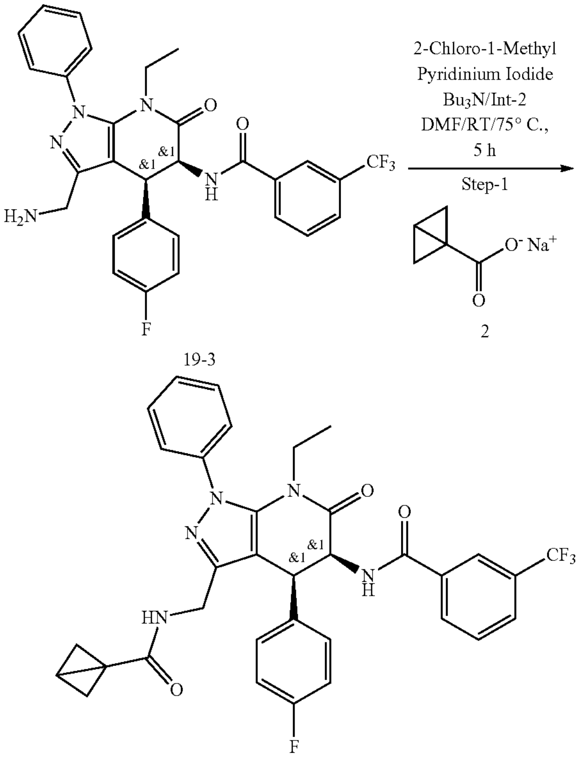

19-3

2

I-114

N-[[(4S, 5S)-7-ethyl-4-(4-fluoro phenyl)-6-oxo-1-phenyl-5-[[3-(trifluoro methyl)benzoyl]amino]-4,5-dihydropyrazolo[3,4-b]pyridine-3-yl]methyl]bicyclo [1.1.0]butane-1-carboxamide (I-114)

To a stirred solution of 19-3 (300 mg, 0.544 mmol) in DMF (2 mL) was added tributylamine (309 mg, 1.632 mmol), 2-chloro-1-methylpyridinium iodide (214.9 mg, 0.816 mmol), and sodium bicyclo[1.1.0]butane-1-carboxylate (2) (97.98 mg, 0.816 mmol) at room temperature. The reaction mixture was stirred at 70 to 75° C. for 5 h. The reaction progress was monitored by TLC. The reaction mixture was allowed to cool to room temperature, quenched with water (25 mL) and extracted by using EtOAc (2×25 mL). The combined organic layer was dried over anhydrous $Na_2SO_4$, filtered, and concentrated under reduced pressure. The obtained crude material was purified by silica gel (230-400 mesh) column chromatography using ethyl acetate in heptane and the compound was eluted with 40% EtOAc in heptane to afford the title compound I-114 (20 mg, 5.75%) as a white solid.

$^1H$ NMR (400 MHZ, DMSO-$d_6$) δ=8.50 (d, J=7.3 Hz, 1H), 8.20-8.12 (m, 2H), 7.98-7.91 (m, 2H), 7.72 (t, J=7.8 Hz, 1H), 7.68-7.64 (m, 2H), 7.62-7.51 (m, 3H), 7.11-7.05 (m, 2H), 6.94-6.88 (m, 2H), 5.47 (t, J=7.2 Hz, 1H), 4.56 (d, J=7.1 Hz, 1H), 4.38-4.30 (m, 1H), 4.13 (dd, J=5.4, 15.1 Hz, 1H), 3.96-3.85 (m, 1H), 3.07-2.96 (m, 1H), 1.94 (t, J=3.5 Hz, 2H), 1.51 (t, J=2.6 Hz, 1H), 0.90 (t, J=7.1 Hz, 3H), 0.67 (d, J=2.3 Hz, 1H), 0.63 (d, J=1.1 Hz, 1H). LC-MS (Method-B)=675.0 $[M+H]^+$; 98.73% at RT 2.29 min. HPLC (Method-B)=98.14% at RT 8.81 min. Chiral HPLC (Method-A)=Peak-1=49.60% at RT 5.38 min. Peak-2=50.39% at RT 9.06 min.

Example 20: Synthesis of Compounds I-175, I-211, I-23, I-16, I-143, and I-214

NMR:

$^1H$ NMR spectrum was recorded on Bruker 400 MHz and Varian 400 MHz instruments internally referenced to a tetramethyl silane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: I (95:5) B: 0.05% Formic acid in I Inj Volume: 2.0 μL, Column oven temperature: 50° C.; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

Method-C: Column: X-Select CSH C18, (50 mm*3.0 mm,2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2,2.0/98, 2.8/98, 3.0/2,3.7/2.

Method-D: Column: X-Select CSH C18 (3.0*50 mm, 2.5 μm), Mobile Phase A: 2.5 Mm Ammonium Bicarbonate in $H_2O$+5% CAN; Mobile Phase B: 100% I, Gradient % B: 0/2,0.3/2,2.0/98,2.8/98,3.0/2,3.7/2.

Method-E: Column: X-Bridge BEH $C_{18}$, (50 mm*3.0 mm,2.5μ) Mobile Phase A: 2.5 mM Ammonium Bicarbonate in Water+5% I Mobile Phase B: 100% ACN Flow rate: 1.0 mL/min. Column temperature: 40° C. Gradient Program (B %): 0.0/2, 0.3/2, 2.0/98, 2.8/98, 3.0/2,3.7/2.

HPLC:

Method-A: Column: X Select CSH C18 (150×4.6) mm,3.5μ; Mobile phase A: 0.1% FA in Water: CAN (95:05); Mobile phase B: Acetonitrile; Gradient Programme: T/B %: 0.01/5, 1/5,8/100,12/100,14/5, 18/5; Flow rate: 1.2 ml/min.

Method-B: Column: X-Bridge CSH C18 (150×4.6 mm, 3.5 μm); Mobile Phase-A: 5 mM $NH_4HCO_3$; Mobile Phase-B: I; Programme: T/B %: 0.01/2,2/2,12/90,16/90; Flow rate: 1.0 mL/min.; Diluent: I: WATER (80:20).

Method-C: Column: X SELECT CSH C18 (150×4.6 mm, 3.5p); Mobile Phase A; 0.05% TFA I water: I (95:05); Mobile Phase B: 0.05% TFA in water: I (05:95); Programme: T/B %: . 0.01/10,12/90,16/90; Flow rate: 1 mL/min.; Diluent: water: I (80:20).

Method-D: Column: X-Bridge CSH C18 (4.6*150) mm 5μ Mobile Phase: A-0.1% TFA in water B-Acetonitrile Inj Volume; 5.0 μL, Flow Rate: 1.2 mL/minute Gradient program: Time (min)/B Conc.: 0.01/5, 1.0/5, 8.0/100, 12.0/100, 14.0/5, 18.0/5.

Method-E: Column: CHIRAL PAK-IC (250×4.6 mm, 5 μm) Mobile Phase A: 0.1% DEA in Hexane; Mobile Phase B: EtOH/MeOH (50/50) A: B: 80/20 Flow 1.0 ml/min.

Method-F: Column: ACE Excel 2 C18-AR, 100 mm×3.0 mm Mobile Phase A: 0.05% TFA in Water; Mobile Phase B:

0.05% TFA in Acetonitrile Colum Temperature: 40° C. Flow Rate: 0.6 mL/min Gradient: 0/5, 1/5, 6/90, 8.5/90, 8.8/5, 11/5.

Method-G: COLUMN: CHIRAL PAK-IK (250×4.6 mm,5im) Mobile Phase A: n-Hexane; Mobile Phase B: IPA A: B: 50:50 Flow: 1.0 mL/min.

Method-H: Column: X-Bridge C18 (4.6*150) mm 5μ Mobile Phase: A—5 mM Ammonium Acetate B—Acetonitrile Flow Rate: 1.0. mL/minute Gradient program: Time (min)/B Conc.: 0.01/5, 1.0/5, 8.0/100, 12.0/100, 14.0/5, 18.0/5.

Synthesis of 20-1

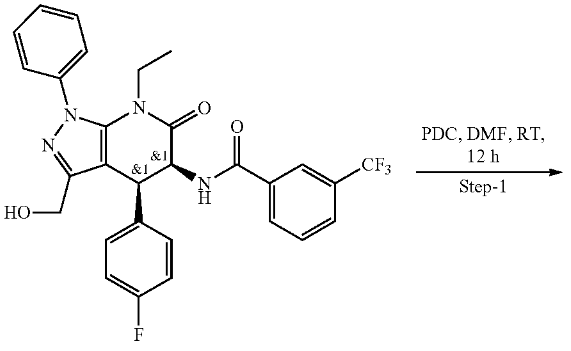

5

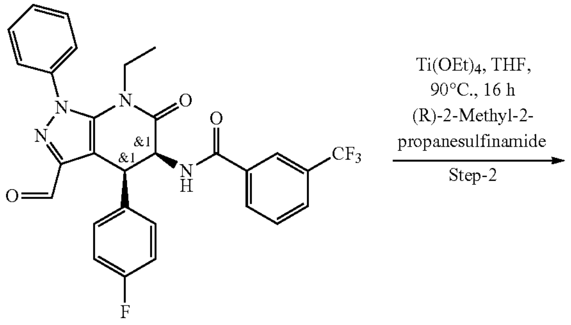

6

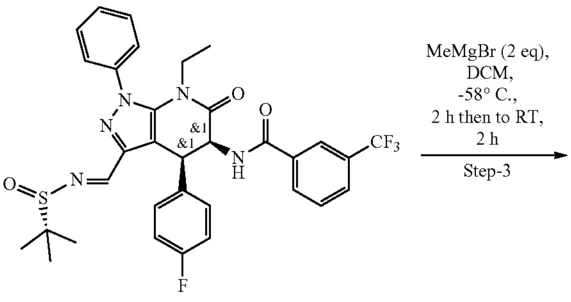

7

-continued

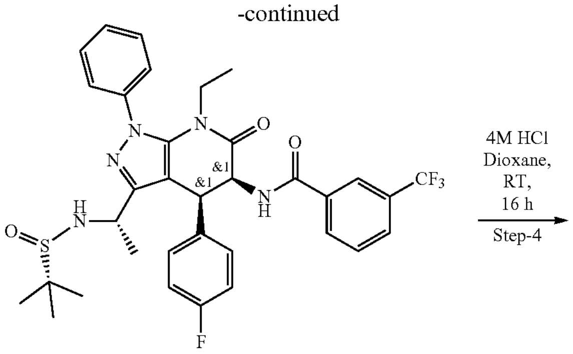

8

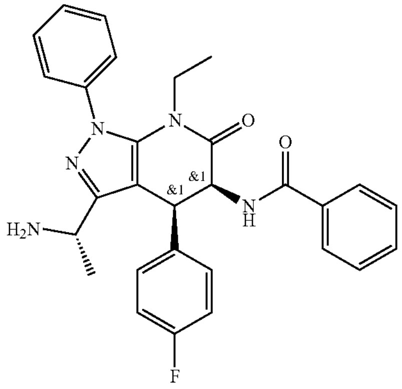

20-1

Step-1: Synthesis of rac-N-((4R,5R)-7-ethyl-4-(4-fluorophenyl)-3-formyl-6-oxo-1-phenyl-4,5,6,7-tetrahydro-1H-pyrazolo[3,4-b]pyridine-5-yl)-3-(trifluoromethyl)benzamide (6)

To a stirred solution of compound (5) (6 g, 9.991 mmol) in DMF (30 mL), pyridinium dichromate (6.25 g, 16.3 mmol) was added at room temperature. Then the reaction mixture was stirred at room temperature for 12 h. Reaction progress was monitored by TLC. After completion of reaction, the reaction mixture was quenched with water (200 mL) and extracted with ethyl acetate (2×500 mL). The reaction mixture was filtered through celite bed. Organic layer was dried over anhydrous sodium sulphate and concentrated to afford crude material. Obtained crude material was purified by flash column chromatography. Combined pure fractions were concentrated under vacuum and washed with ether to afford compound (6) (4 g, 72.0%) as a pale brown solid.

$^1$H NMR (400 MHZ, DMSO-$d_6$) δ=9.86 (s, 1H), 8.59 (d, J=6.4 Hz, 2H), 8.14-8.11 (m, 2H), 7.89-7.80 (m, 3H), 7.69-7.63 (m, 3H), 7.08-7.00 (m, 4H), 5.55 (s, 1H), 4.88 (d, J=7.6 Hz, 1H), 3.89-3.84 (m, 1H), 3.05-2.98 (m, 1H), 0.88 (s, 3H). LC-MS (Method-B)=551.31 $[M+H]^+$; 99.25% at RT 2.23 min.

Step-2: Synthesis of N-((4S,5S)-3-(I—(((R)-tert-butylsulfinyl)imino)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (7)

To a stirred solution of compound (6) (7 g, 12.72 mmol) in tetrahydrofuran (70 mL) was added titanium (iv) ethoxide (6.82 g, 25.43 mmol) followed by (R)$_2$-methylpropane-2-sulfinamide (3.08 g, 25.43 mmol) at room temperature. The reaction mixture was heated to 90° C. for 16 h. Progress of the reaction was monitored by TLC. After consumption of the reaction, the reaction mixture was allowed to room temperature, quenched with water (500 mL), and extracted with ethyl acetate (2×500 mL). Combined organic layers were dried over anhydrous sodium sulphate and concentrated under reduced pressure to afford crude compound (7) (6.40 g, 76.99%) and it was directly used for next step without any further purification.

$^1$H NMR (400 MHZ, DMSO-d$_6$): =8.68-8.51 (m, 1H), 8.39 (d, J=3.6 Hz, 1H), 8.24-8.18 (m, 1H), 8.12-8.10 (m, 1H), 7.92 (t, J=6.8 Hz, 1H), 7.86-7.81 (m, 2H), 7.74-7.60 (m, 4H), 7.12-7.06 (m, 2H), 6.96-6.93 (m, 2H), 5.56-5.55 (m, 1H), 4.98 (dd, J=11.4, 7.4 Hz, 1H), 3.93-3.87 (m, 1H), 3.06-2.97 (m, 1H), 1.19-1.51 (m, 3H), 1.08 (s, 9H).

Step-3: Synthesis of N-[(4S,5S)-3-[1-(tert-butylsulfinylamino)ethyl]-7-ethyl-4-(4-fluorophenyl)-6-oxo-1-phenyl-4,5-dihydropyrazolo[3,4-b]pyridine-5-yl]-3-(trifluoromethyl)benzamide (8)

To a stirred solution of compound (7) (7 g, 10.71 mmol) in dichloromethane (9.09 g, 107.1 mmol) was added methyl magnesium bromide solution (3.0 mol/l) in diethyl ether (37 g, 107.1 mmol) at −58° C. Then the reaction mixture was allowed to room temperature. The reaction was stirred at room temperature for 2 h. After consumption of the starting material (by TLC), the reaction was poured into ice cold $NH_4Cl$ solution (150 mL) and extracted with DCM (2×500 mL). The organic layer was dried over anhydrous $Na_2SO_4$, concentrated under reduced pressure. The crude material was washed with diethyl ether to afford compound-8 (7 g, 47.83%) as an off-white solid. LC-MS (Method-A)=670.8 [M+H]$^+$; 57.65% at RT 2.16, 2.22, 2.25, 2.29 min.

Step 4: Synthesis of N-((4S,5S)-3-((S)-1-aminoethyl)-7-ethyl-4-(4-fluorophenyl)-6-oxo-1-phenyl-4,5,6,7,-tetrahydro-1H-pyrazolo[3,4-b]pyridine-5-yl)-3-(trifluoromethyl)benzamide (20-1)

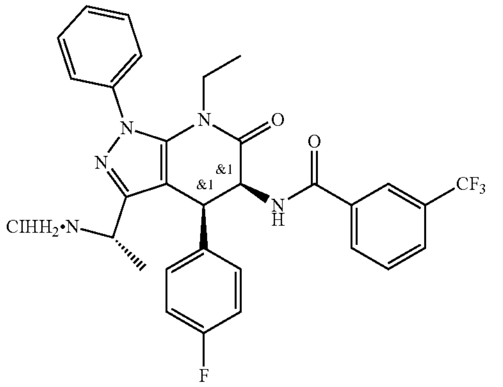

20-1

To a stirred solution of compound (8) (7.0 g, 10 mmol) in dichloromethane (8.9 g, 100 mmol) was added hydrochloric acid (2 mol/l) in diethyl ether (52 mL, 100 mmol) at 0° C. Then the reaction mixture was allowed to room temperature. Reaction mixture was stirred at room temperature for 16 h. The organic layer was concentrated under reduced pressure. The crude material was washed with heptane to afford 20-1 (6 g, 93%) as an off-white solid.

$^1$H NMR (400 MHZ, DMSO-d$_6$) δ=8.67-8.60 (m, 1H), 8.36 (s, 1H), 8.20-8.11 (m, 1H), 7.93 (d, J=7.8 Hz, 1H), 7.77-7.67 (m, 3H), 7.66-7.56 (m, 3H), 7.15 (t, J=8.2 Hz, 2H), 7.06-6.96 (m, 2H), 5.61-5.52 (m, 1H), 4.76-4.66 (m, 1H), 4.58 (q, J=6.5 Hz, 1H), 3.97-3.83 (m, 1H), 3.13-3.02 (m, 1H), 1.39 (d, J=6.8 Hz, 1H), 1.14-1.07 (m, 2H), 1.04 (d, J=6.8 Hz, 2H), 0.98-0.88 (m, 3H). LC-MS (Method-A)=566.9 [M+H]$^+$; 76.39% at RT 2.04 min. HPLC (Method-A)=90.24% at RT 6.36 min. HPLC-(Method C): 15.8:38:9:37 at RT 7.8, 8.99, 10.1, 16.4 min.

Synthesis of Analogues

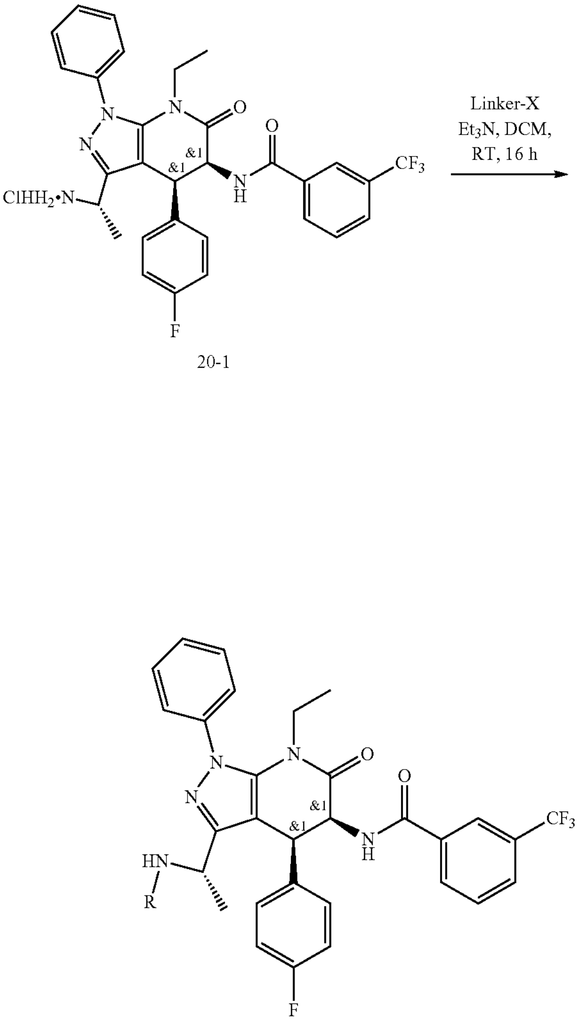

20-1

Method-B Procedure:

To a stirring solution of 20-1 (1.0 eq) in DCM (mL) were added linker (1.3 eq) followed by TEA (2.00 eq) at room temperature and stirred for 6 h. The reaction was monitored by TLC; after completion of reaction, the reaction mixture was quenched with water (20 mL) and extracted using ethyl acetate (2×25 mL). The combined organic layer was dried over sodium sulphate and concentrated under reduced pressure. The crude obtained was purified by medium pressure liquid chromatography by eluting with 40% EtOAc in heptane. The reaction conditions and yields of the resulting products are shown below.

| Sr. No | Cpd. Number | Linker Structure | Method | 20-1 Qty (mg) | Linker Qty (mg) | Qty (mg) & of nature compound | Yield (%) |
|---|---|---|---|---|---|---|---|
| 1. | I-175 | 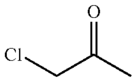 | B | 130 | 33 | 25 (White solid) | 16 |
| 2. | I-211 | 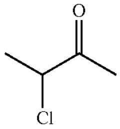 | B | 130 | 38 | 46 (Whitesolid) | 30 |
| 3. | I-23 | 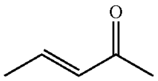 | B | 130 | 30 | 120 (White solid) | 86 |
| 4. | I-16 | 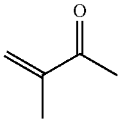 | B | 130 | 31 | 44 (White solid) | 30 |
| 5. | I-143 | 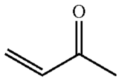 | B | 200 | 48.01 | 52 (White solid) | 22.70 |
| 6. | I-214 | 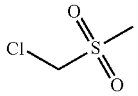 | B | 130 | 35 | 35 (White solid) | 21 |

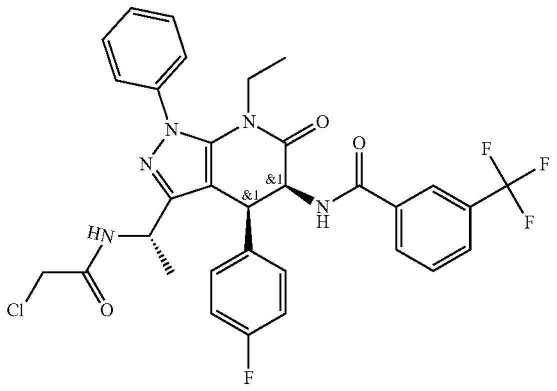 [SMILES: CCN1C(=O)[C@@H](NC(=O)c2cccc(C(F)(F)F)c2)[C@@H](c2ccc(F)cc2)c2c([C@H](C)NC(=O)CCl)nn(-c3ccccc3)c21]

I-175:

$^1$H NMR (400 MHZ, DMSO-$d_6$) δ=8.58-8.53 (m, 2H), 8.17-8.13 (m, 2H), 7.92 (d, J=7.6 Hz, 1H), 7.73-7.66 (m, 3H), 7.62-7.53 (m, 3H), 7.13-7.07 (m, 2H), 6.97-6.89 (m, 2H), 5.52-5.47 (m, 1H), 4.88-4.84 (m, 1H), 4.64 (d, J=7.2 Hz 1H), 3.92-3.81 (m, 1H), 3.60-3.44 (m, 1H), 3.07-3.00 (m, 1H), 1.35-1.33 (m, 1H), 1.23 (d, J=6.8 Hz, 3H), 0.90 (t, J=7.2 Hz, 3H). LCMS (Method-B)=644.2 [M+H]$^+$; 98.28% at RT 2.35 min. HPLC (Method-B): 96.39% at RT 9.43 min. Chiral HPLC (Method-E): Peak-1=42.11% at RT 4.80 min; Peak-2=43.76% at RT 5.86 min.

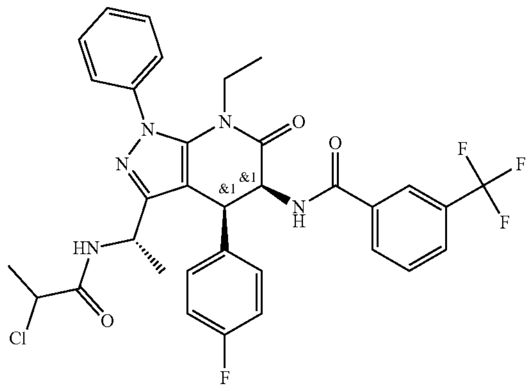 [SMILES: CCN1C(=O)[C@@H](NC(=O)c2cccc(C(F)(F)F)c2)[C@@H](c2ccc(F)cc2)c2c([C@H](C)NC(=O)C(C)Cl)nn(-c3ccccc3)c21]

I-211:

$^1$H NMR (400 MHZ, DMSO-$d_6$) δ=8.66-8.60 (m, 1H), 8.55-8.51 (m, 1H), 8.18-8.11 (m, 2H), 7.92 (d, J=7.6 Hz, 1H), 7.73-7.66 (m, 3H), 7.61-7.51 (m, 3H), 7.12-7.06 (m, 2H), 6.99-6.90 (m, 2H), 5.55-5.45 (m, 1H), 4.89-4.82 (m, 1H), 4.63-4.59 (m, 1H), 4.48-4.18 (m, 1H), 3.92-3.85 (m, 1H), 3.08-3.02 (m, 1H), 1.47-1.08 (m, 6H), 0.91 (t, J=6.8 Hz, 3H). LCMS (Method-B)=656.2 [M+H]$^+$; 99.34% at RT 2.41 min. HPLC (Method-B): 99.46% at RT 9.71 min. Chiral HPLC (Method-E): Peak-1=20.89% at RT 4.36 min; Peak-2=37.94% at RT 5.75 min.

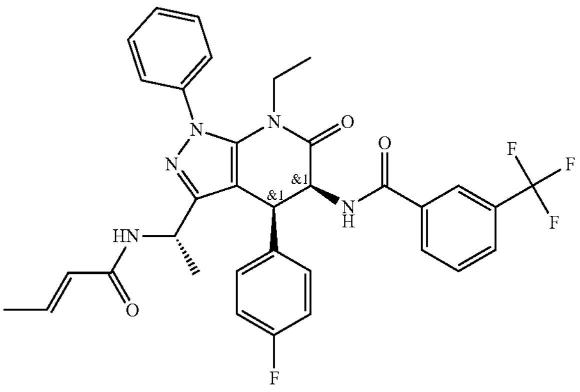 [SMILES: C/C=C/C(=O)N[C@@H](C)c1nn(-c2ccccc2)c2c1[C@H](c1ccc(F)cc1)[C@H](NC(=O)c1cccc(C(F)(F)F)c1)C(=O)N2CC]

I-23:

$^1H$ NMR (400 MHZ, DMSO-$d_6$) δ=8.53-8.45 (m, 1H), 8.17-8.07 (m, 3H), 7.92 (d, J=7.6 Hz, 1H), 7.73-7.65 (m, 3H), 7.61-7.50 (m, 3H), 7.10-6.82 (m, 4H), 6.40-6.35 (m, 1H), 5.65-5.61 (m, 1H), 5.51-5.46 (m, 1H), 4.92-4.88 (m, 1H), 4.63 (d, J=7.2 Hz, 1H), 3.92-3.85 (m, 1H), 3.07-3.01 (m, 1H), 1.68-1.56 (m, 3H), 1.33-1.11 (m, 3H), 0.92-0.79 (m, 3H). LCMS (Method-B)=634.2 $[M+H]^+$; 100% at RT 2.33, 2.24 min. HPLC (Method-B): 98.75% at RT 9.26, 8.87 min. Chiral HPLC (Method-G): Peak-1=46.92% at RT 5.04 min; Peak-2=53.07% at RT 7.14 min.

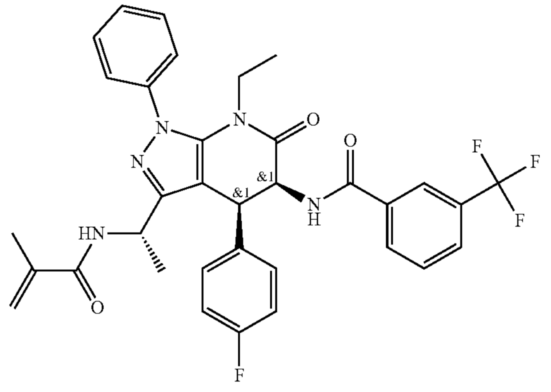 [SMILES: C=C(C)C(=O)N[C@@H](C)c1nn(-c2ccccc2)c2c1[C@H](c1ccc(F)cc1)[C@H](NC(=O)c1cccc(C(F)(F)F)c1)C(=O)N2CC]

I-16:

$^1H$ NMR (400 MHZ, DMSO-$d_6$) δ=8.53-8.42 (m, 1H), 8.16-8.07 (m, 3H), 7.92 (d, J=8.0 Hz, 1H), 7.79-7.66 (m, 3H), 7.62-7.50 (m, 3H), 7.09-6.99 (m, 2H), 6.93-6.82 (m, 2H), 5.50 (d, J=1.6 Hz, 1H), 5.45 (m, 1H), 5.19 (d, J=1.6 Hz, 1H), 4.96-4.93 (m, 1H), 4.68 (d, J=7.2 Hz, 1H), 3.92-3.86 (m, 1H), 3.07-3.01 (m, 1H), 1.69 (m, 3H), 1.42-1.23 (m, 3H), 0.91 (t, J=6.8 Hz, 3H). LCMS (Method-B)=634.2 $[M+H]^+$; 97.59% at RT 2.38 min. HPLC (Method-B): 96.14% at RT 9.70, 9.62 min. Chiral HPLC (Method-E): Peak-1=42.47% at RT 4.77 min; Peak-2=44.17% at RT 6.02 min.

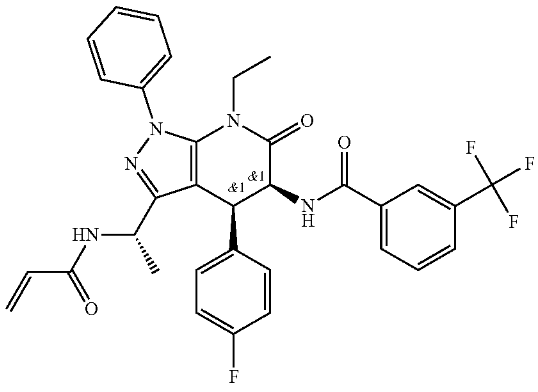 [SMILES: C=CC(=O)N[C@@H](C)c1nn(-c2ccccc2)c2c1[C@H](c1ccc(F)cc1)[C@H](NC(=O)c1cccc(C(F)(F)F)c1)C(=O)N2CC]

I-143:

$^1H$ NMR (400 MHZ, DMSO-$d_6$) δ=8.52 (d, J=7.6 Hz, 1H), 8.43 (d, J=8.4 Hz, 1H), 8.16-8.13 (m, 2H), 7.92 (d, J=8.0 Hz, 1H), 7.73-7.66 (m, 3H), 7.60-7.52 (m, 3H), 7.09-6.91 (m, 4H), 6.04-5.90 (m, 2H), 5.52-5.39 (m, 2H), 4.96-4.92 (m, 1H), 4.63 (d, J=7.2 Hz, 1H), 3.91-3.87 (m, 1H), 3.05-3.03 (m, 1H), 1.34-1.22 (m, 3H), 0.92-0.84 (m, 3H). LCMS (Method-D)=620.2 $[M+H]^+$; 98.32% at RT 2.30, 2.20 min. HPLC (Method-B): 95.45% at RT 9.96, 9.46 min. Chiral HPLC (Method-G): Peak-1=31.11% at RT 5.19 min; Peak-2=38.98% at RT 5.77 min.

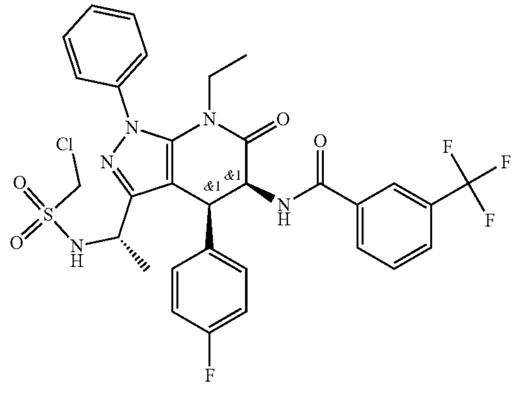 [SMILES: CCN1C(=O)[C@@H](NC(=O)c2cccc(C(F)(F)F)c2)[C@@H](c2ccc(F)cc2)c2c([C@H](C)NS(=O)(=O)CCl)nn(-c3ccccc3)c21]

I-214:

$^1H$ NMR (400 MHz, DMSO-$d_6$) δ=8.50 (d, J=7.2 Hz, 1H), 8.20-8.13 (m, 3H), 7.92 (d, J=7.6 Hz, 1H), 7.73-7.66 (m, 3H), 7.62-7.54 (m, 3H), 7.12-7.08 (m, 2H), 6.99-6.96 (m, 2H), 5.55-5.52 (m, 1H), 4.82-4.70 (m, 3H), 4.52-4.48 (m, 1H), 3.90-3.85 (m, 1H), 3.09-3.03 (m, 1H), 1.24 (d, J=6.8 Hz, 3H), 0.91 (t, J=6.8 Hz, 3H). LCMS (Method-B) =678.2 $[M+H]^+$; 97.17% at RT 2.38 min. HPLC (Method-B): 95.73% at RT 9.80 min. Chiral HPLC (Method-E): Peak-1=48.15% at RT 4.88 min; Peak-2=24.54% at RT 5.50 min.

Example 21: Synthesis of Compounds I-107 and I-141

NMR:

$^1H$ spectrum was recorded on Bruker 400 MHz and Varian 400 MHz instruments internally referenced to a tetramethylsilane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: I (95:5); B: 0.05% Formic acid in I Inj Volume: 2.0 μL, Column oven temperature: 50° C.; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5,1/5,8/100,12/100,14/5, 18/5; Flow rate: 1.2 ml/min.

Method-B: Column: X-Bridge CSH C18 (150×4.6 mm, 3.5 μm); Mobile Phase-A: 5 mM $NH_4HCO_3$; Mobile Phase-B: I; Programme: T/B %: 0.01/2,2/2,12/90,16/90; Flow rate: 1.0 mL/min.; Diluent: I:Water (80:20).

Method-C: Column: X SELECT CSH C18 (150×4.6 mm, 3.5μ); Mobile Phase A; 0.05% TFA in water: I (95:05); Mobile Phase B: 0.05% TFA in water: I (05:95); Programme: T/B %: 0.01/10,12/90, 16/90; Flow rate: 1 mL/min.; Diluent: water: I (80:20).

Chiral HPLC:

Method-A: Mobile Phase A: n-Hexane, Mobile Phase B: ETOH: MeOH (50/50).

Method-B: Column: chiralpakik (250*4.6 mm, 5 μm), Mobile Phase A: n-Hexane, Mobile Phase B: IPA: MeOH (1:1) A/B: 75:25 Flow: 1.0 ml/MI.

Synthesis of 21-3

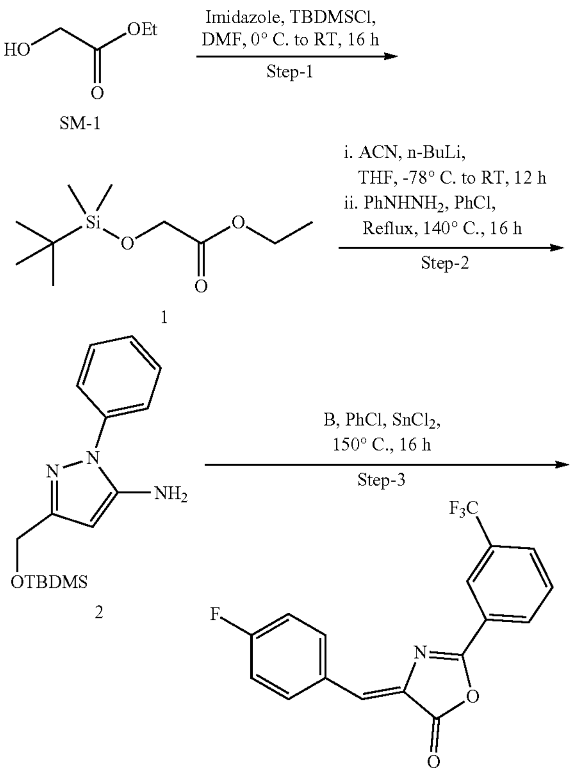

SM-1

1

2

B

-continued

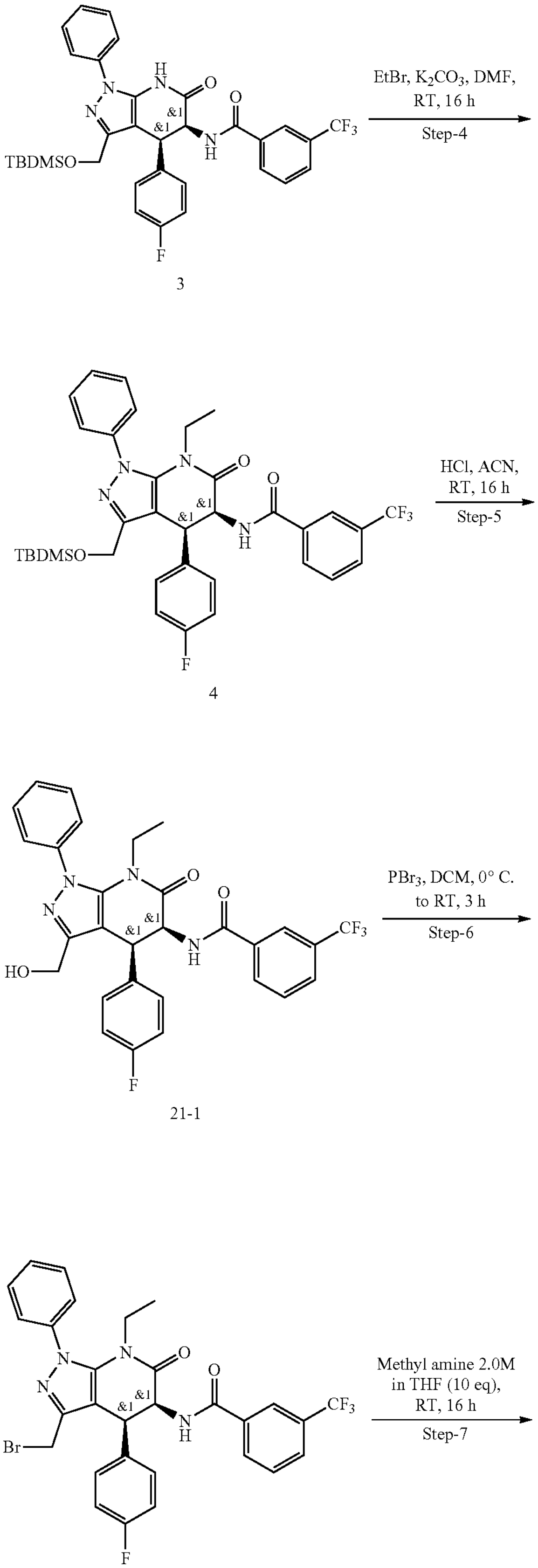

3

4

21-1

21-2

-continued

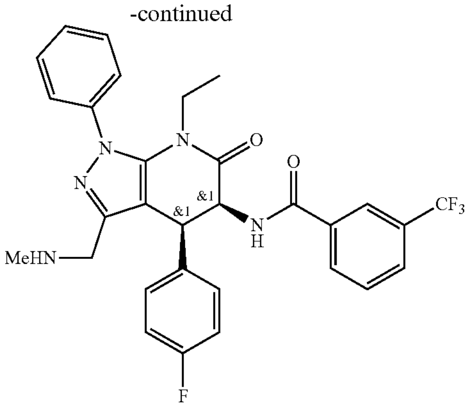

21-3

Step-1: Synthesis of ethyl 2-((tert-butyldimethylsilyl)oxy)acetate (1)

To stirred solution of compound (SM-1) (25 g, 240.1 mmol) in DMF (125 mL) was added imidazole (27.6 g, 312.2 mmol) and TBDMSCl (47.04 g, 312.2 mmol) at 0° C. The reaction mixture was stirred at room temperature for 16 h. After consumption of the starting material (by TLC), the reaction mixture was quenched with water (1.2 L) and extracted with EtOAc (2×500 mL). The combined organic layer was dried over anhydrous sodium sulfate and concentrated to afford crude compound. The obtained crude compound was purified by flash column chromatography eluting with 0-20% EtOAc in heptane. Pure fraction was collected and concentrated under vacuum to afford compound (1) (24 g, 46.1%) as colorless liquid.

$^1$H NMR (400 MHZ, DMSO-$d_6$): δ 4.21 (s, 2H), 4.09 (q, J=6.8 Hz, 2H), 1.18 (t, J=6.8 Hz, 3H), 0.88-0.82 (m, 9H), 0.07-0.06 (m, 6H).

Step-(2i): Synthesis of 3-(((tert-butyldimethylsilyl)oxy)methyl)-1-phenyl-1H-pyrazol-5-amine (2A)

To a stirred solution of acetonitrile (15 mL) in THF (750 mL), n-butyl lithium (2.5 mol/l) in hexanes (115 ml, 290 mmol) was added at −78° C. The reaction mixture was stirred at −78° C. for 30 min. After 30 mins, compound (1) (40 g, 183.18 mmol) dissolved in THF (750 mL) was added to the reaction mixture slowly at same temperature. The reaction mixture was warmed to room temperature and maintained the same for 12 h. Reaction progress was monitored by TLC. After completion of the reaction, the reaction mixture was quenched with water and pH was adjusted to 4-5 using 2N aq·HCl solution. The reaction solution was extracted with 2×500 mL ethyl acetate. The combined organic layer was dried over anhydrous sodium sulfate and concentrated under reduced pressure to afford crude compound (2A) (37 g, 94.67%) as a pale-brown oil.

Step-(2ii): Synthesis of 5-[[tert-butyl(dimethyl)silyl]oxymethyl]δδδ-2-phenyl-pyrazol-3-amine (2B)

To a stirred solution of compound (2A) (37 g, 173.42 mmol) in chlorobenzene (110 mL), phenylhydrazine (19 g, 173.94 mmol) was added at room temperature. The reaction mass temperature was raised to 140° C. The reaction mixture was stirred at same temperature for 16 h. Reaction progress was monitored by TLC. After completion of starting material, the reaction mixture was quenched with water (100 mL) and extracted with ethyl acetate (2×500 mL). Combined organic layer was dried over anhydrous sodium sulfate, concentrated under reduced pressure to afford crude compound. The obtained crude compound was purified by column chromatography eluting with 15-20% ethyl acetate in pet ether to afford compound (2B) (26.0 g, 35.07%) as a yellow solid.

$^1$H NMR (400 MHZ, DMSO-$d_6$): δ 7.58-7.54 (m, 2H), 7.48-7.43 (m, 2H), 7.29 (d, J=7.4, 1.2 Hz, 1H), 5.47 (s, 1H), 5.30 (s, 2H), 4.50 (s, 2H), 0.91-0.87 (m, 9H), 0.07 (s, 6H). LC-MS (Method-B)=304.7 [M+H]$^+$; 70.73% at RT 2.16 min.

Step-3: Synthesis of rac-N-((4R,5R)-3-(((tert-butyldimethylsilyl)oxy)methyl)-4-(4-fluorophenyl)-6-oxo-1-phenyl-4,5,6,7-tetrahydro-1H-pyrazolo[3,4-b]pyridine-5-yl)-3-(trifluoromethyl)benzamide (3)

To a stirred solution of compound (2) (26 g, 85.67 mmol) and Int-B (29.19 g, 85.67 mmol) in chlorobenzene (78 ml), tin(II) chloride (1.64 g, 8.56 mmol) was added at room temperature. The reaction mixture was stirred at 150° C. for 16 h. Reaction progress was monitored by TLC. After completion of reaction, the reaction mixture was quenched with water (100 mL) and filtered through celite bed and washed with DCM (500 mL). Filtrate was washed with water and extracted with DCM (2×500 mL). Organic layer was dried over anhydrous sodium sulfate and concentrated under reduced pressure. The obtained crude was purified by column chromatography by eluting with 20-30% ethyl acetate in pet ether to afford compound (3) (30 g, 48.6%) as yellow solid.

$^1$H NMR (400 MHZ, DMSO-$d_6$): δ 11.06 (s, 1H), 8.36 (d, J=3.4 Hz, 1H), 8.07 (s, 2H), 7.89 (d, J=7.3 Hz, 1H), 7.71-7.58 (m, 4H), 7.55-7.49 (m, 2H), 7.40 (d, J=6.8 Hz, 1H), 7.08-7.03 (m, 1H), 6.95 (s, 1H), 5.34-5.24 (m, 1H), 4.69 (d, J=6.8 Hz, 1H), 4.62-4.56 (m, 1H), 4.46-4.40 (m, 1H), 0.73 (s, 5H). LC-MS (Method-A)=639.29 [M+H]$^+$; 88.73% at RT 2.48 min.

Step-4: Synthesis of rac-N-((4R,5R)-3-(((tert-butyldimethylsilyl)oxy)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (4)

To a stirred solution of compound (3) (30 g, 41.33 mmol) in DMF (300 mL), potassium carbonate (7.50 g, 53.73 mmol) and bromoethane (5.45 g, 49.60 mmol) were added at room temperature. The reaction mixture was stirred at room temperature for 16 h. Reaction progress was monitored by TLC. After completion of SM, the reaction mixture was quenched with water and extracted with ethyl acetate. Organic layer was dried over anhydrous sodium sulfate and evaporated under vacuum. The obtained crude was purified by column chromatography by eluting with 15-20% ethyl acetate in heptane to afford compound (4) (15 g, 48.3%) as yellow solid.

$^1$H NMR (400 MHZ, DMSO-d6) ($D_2O$): δ=8.10-8.05 (m, 2H), 7.91 (d, J=7.1 Hz, 1H), 7.78-7.64 (m, 1H), 7.64-7.49 (m, 5H), 7.10-7.03 (m, 2H), 6.95-6.90 (m, 2H), 5.41 (d, J=7.2 Hz, 1H), 4.65-4.69 (m, 1H), 4.62 (d, J=12.4 Hz, 1H), 4.45 (d, J=12.4 Hz, 1H), 3.08-2.94 (m, 2H), 0.92-0.79 (m, 3H), 0.70 (s, 9H), 0.12 (s, 6H). LC-MS (Method-B)=667.5 [M+H]$^+$; 83.38% at RT 2.52 min

Step-5: Synthesis of rac-N-((4R,5R)-7-ethyl-4-(4-fluorophenyl)-3-(hydroxymethyl)-6-oxo-1-phenyl-4,5,6,7-tetrahydro-1H-pyrazolo[3,4-b]pyridine-5-yl)-3-(trifluoromethyl)benzamide (21-1)

To a stirred solution of compound (4) (20 g, 24.90 mmol) in acetonitrile (100 mL), hydrochloric acid (20 mL, 120 mmol) was added. The reaction mixture was stirred at room temperature for 16 h. Reaction progress was monitored by TLC. After completion of reaction, the reaction mixture was quenched with ice water and extracted with ethyl acetate. Organic layer was dried over anhydrous sodium sulfate and concentrated under vacuum to afford crude compound. The crude material was washed with 10% diethyl ether in pentane and dried under vacuum to afford 21-1 (12.00 g, 83.75%) as a pale-yellow solid.

$^1$H NMR (400 MHZ, DMSO-d6, 25° C.): δ=8.53 (d, J=7.3 Hz, 1H), 8.17-8.12 (m, 2H), 7.92 (d, J=7.8 Hz, 1H), 7.74-7.64 (m, 3H), 7.61-7.50 (m, 3H), 7.10 (t, J=8.9 Hz, 2H), 7.05-6.93 (m, 2H), 5.50 (t, J=7.3 Hz, 1H), 5.11 (t, J=6.0 Hz, 1H), 4.72 (d, J=7.3 Hz, 1H), 4.41-4.35 (m, 1H), 4.30-4.24 (m, 1H), 3.94-3.87 (m, 1H), 3.08-2.98 (m, 1H), 0.91 (t, J=7.1 Hz, 3H). LC-MS (Method-B)=553.2 [M+H]$^+$; 96.44% at RT 2.26 min. HPLC (Method-B): 95.87% at RT 9.15 min.

Step-6: Synthesis of rac-N-((4R,5R)-3-(bromomethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (21-2)

To a stirred solution of compound (5) (2.0 g, 3.62 mmol) in DCM (10 mL) was added $PBr_3$ (0.58 mL, 5.4 mmol) at 0° C. The reaction mixture was stirred at room temperature for 3 h. Progress of the reaction was monitored by TLC. After consumption of reaction, the reaction mixture was diluted with water and extracted with DCM. Organic layer was dried over sodium sulfate, concentrated under vacuum to afford crude. Obtained crude was purified by medium pressure liquid chromatography was eluted with 30-40% ethyl acetate/pentane to afford compound (21-2) (1.55 g, 54%) as an off-white solid.

$^1$H NMR (400 MHZ, DMSO-d6): δ 8.56 (d, J=7.3 Hz, 1H), 8.20-8.10 (m, 2H), 7.92 (d, J=7.3 Hz, 1H), 7.72 (d, J=7.3 Hz, 3H), 7.63-7.54 (m, 3H), 7.14-7.07 (m, 2H), 7.03-6.97 (m, 2H), 5.55 (t, J=7.1 Hz, 1H), 4.39 (d, J=11.2 Hz, 1H), 3.88 (dd, J=14.2, 7.3 Hz, 1H), 3.05 (dd, J=14.4, 7.1 Hz, 1H), 1.24 (s, 3H), 0.85-0.94 (m, 3H). LC-MS (Method-B)=614.7 [M+H]$^+$; 95.53% at RT 2.80 min.

Step-7: Synthesis of rac-N-((4R,5R)-7-ethyl-4-(4-fluorophenyl)-3-((methylamino)methyl)-6-oxo-1-phenyl-4,5,6,7-tetrahydro-1H-pyrazolo[3,4-b]pyridine-5-yl)-3-(trifluoromethyl)benzamide (21-3)

To a stirred solution of compound (21-2) (1.5 g, 2.4 mmol) was added by addition of methyl amine (2.0 M. in THF, 10 eq) at room temperature. The reaction mixture was stirred at room temperature for 16 h. Progress of the reaction was monitored by TLC. After consumption of reaction, the reaction mixture was concentrated under vacuum to afford crude. Obtained crude was purified by medium pressure liquid chromatography eluting with 5-10% MeOH/DCM to afford compound (21-3) (750 mg, 57.4%) as an off-white solid.

$^1$H NMR (400 MHZ, DMSO-$d_6$): δ 8.50 (d, J=7.5 Hz, 1H), 8.15-8.11 (m, 2H), 7.91 (d, J=7.9 Hz, 1H), 7.73-7.63 (m, 3H), 7.60-7.50 (m, 3H), 7.14 (t, J=8.8 Hz, 2H), 7.01 (dd, J=8.6, 5.6 Hz, 2H), 5.75 (s, 1H), 5.49 (dt, J=7.3, 3.8 Hz, 1H), 4.69 (d, J=7.3 Hz, 1H), 3.93-3.87 (m, 1H), 3.56-3.46 (m, 2H), 3.08-3.03 (m, 1H), 2.13 (s, 3H), 0.92 (t, J=7.1 Hz, 3H), LC-MS (Method-B)=564.4 [M−H]$^-$; 96.50% at RT 2.509 min. HPLC (Method-C): 95.35% at RT 9.34 min.

Synthesis of Int. B

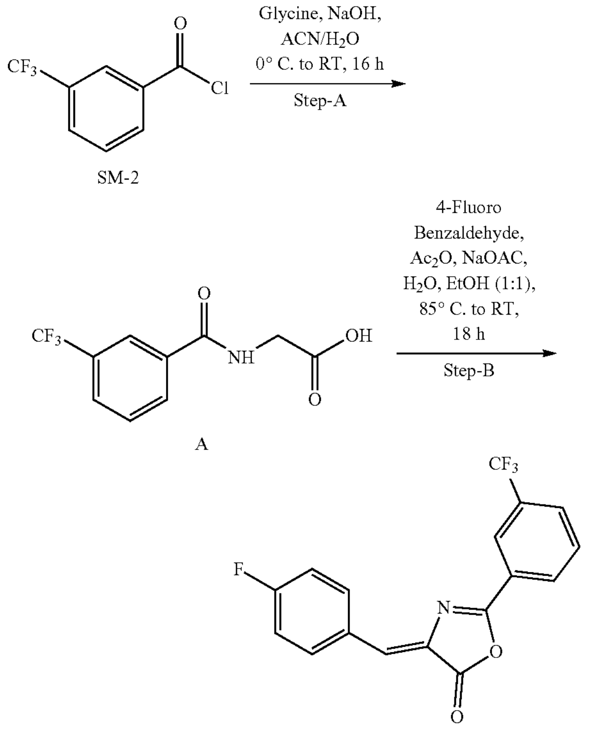

SM-2

A

B

Step-A: Synthesis of (3-(trifluoromethyl)benzoyl)glycine (A)

A stirred solution of glycine (359.89 g, 4794.78 mmol) in I (6 L) was added to a NaOH (479.35 g, 11986.95 mmol in 1.2 L of water) solution at 0° C. and stirred for 15 min. 3-(trifluoromethyl)benzoyl chloride (SM-2) (1000 g, 4794.78 mmol) in I (2 L) was added dropwise at 0° C. The reaction mixture was stirred at room temperature for 16 h. After consumption of the starting material (by TLC), the reaction mixture was diluted with water and acidified with HCl, and pH adjusted 1-3 and extracted with EtOAc (2×10 L). The combined organic layer was washed with brine solution (5 L), dried over anhydrous $Na_2SO_4$, filtered, and concentrated under reduced pressure to afford crude compound. Crude compound was triturated with n-Heptane to get pure Compound-B (1000 g, 84.38%) as a yellow solid.

$^1$H NMR (400 MHZ, DMSO-$d_6$): δ 9.13-9.05 (m, 1H), 8.27-8.13 (m, 2H), 7.93 (d, J=7.5 Hz, 1H), 7.74 (t, J=7.7 Hz, 1H), 3.94 (d, J=5.8 Hz, 2H). LC-MS (Method-A)=248.12 [M+H]$^+$; 98.23% at RT 1.14 min.

Step-B: Synthesis of (Z)-4-(4-fluorobenzylidene)-2-(3-(trifluoromethyl)phenyl)oxazol-5 (4H)-one (B)

To a stirred solution of (A) (1000 g, 4045.8 mmol) in acetic anhydride (1250 g, 12137 mmol) was added 4-Fluoro Benzaldehyde (502.12 g, 4045.8 mmol) and the reaction mixture was allowed to stir for 10 to 15 min, followed by addition of NaOAc (335 g, 4045.8 mmol). The reaction mixture was heated at 80° C.-85° C. for 4 h. Reaction was monitored by TLC. After completion of reaction, the reaction mass was cooled to room temperature, ethanol (500 mL) and water (500 mL) were added, and the mass was stirred for 8-10 hr. The reaction mixture was filtered, washed with heptane (100 mL), and dried for 1 h. Obtained compound was azeotroped with toluene (2×500 mL) and filtered with heptane (3 L) to afford compound (B) (800 g, 60%) as a pale-yellow solid. LC-MS (Method-A)=336.1 $[M+H]^+$; 80.55% at RT 1.56 min.

$^1$H NMR (400 MHZ, DMSO-$d_6$): δ 8.46-8.38 (m, 2H), 8.33 (s, 1H), 8.11 (d, J=7.6 Hz, 1H), 7.90 (t, J=7.8 Hz, 1H), 7.50-7.33 (m, 4H).

Synthesis of methyl (~{E})-4-[[(4~{R},5~{S})-7-ethyl-4-(4-fluorophenyl)-6-oxo-1-phenyl-5-[[3-(trifluoromethyl)benzoyl]amino]-4,5-dihydrapyrazolo[3,4-b]pyridine-3-yl]methyl-methyl-amino]-4-oxo-but-2-enoate (I-107) and methyl (~{E})-4-[[(4~{S},5~{S})-7-ethyl-4-(4-fluorophenyl)-6-oxo-1-phenyl-5-[[3-(trifluoromethyl)benzoyl]amino]-4,5-dihydrapyrazolo[3,4-b]pyridine-3-yl]methyl-methyl-amino]-4-oxo-but-2-enoate (I-141)

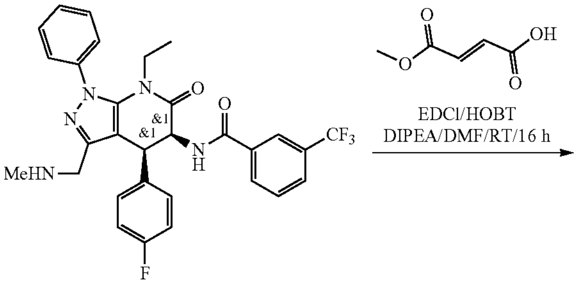

21-3

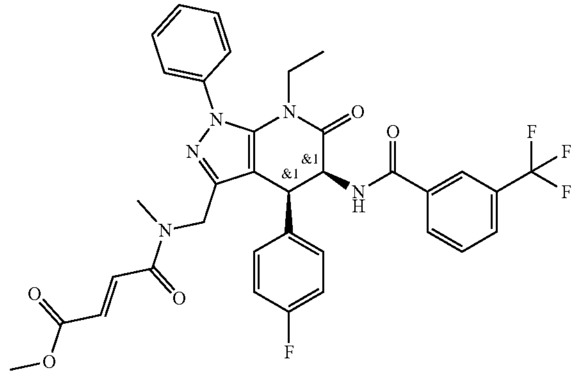

I-107

-continued

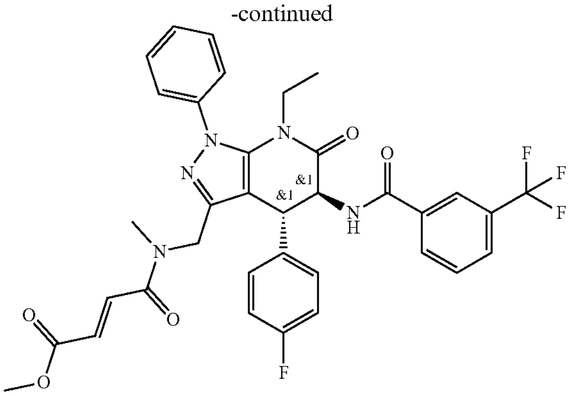

I-141

To a stirred solution of 21-3 (200.0 mg, 0.35 mmol) in DMF (5 mL) was added N,N-diisopropylethylamine (0.18 mL, 106 mmol) and EDCI (103.0 mg 0.53 mmol), followed by ({E})-4-methoxy-4-oxo-but-2-enoic acid (69.0 mg, 0.53 mmol) and the reaction mixture was stirred to 5 min. HOBT (73.0 mg, 0.53 mmol) was added and the reaction mixture was stirred at room temperature for 16 h. Progress of the reaction was monitored by TLC and LC-MS. After completion of reaction, the reaction mixture was quenched with water (25 mL) and extracted with ethyl acetate (2×50 mL). Combined organic layer was dried over anhydrous sodium sulfate and concentrated to afford crude compound. Obtained crude compound was purified by silica gel (230-400) column chromatography using ethyl acetate in heptane. Product was eluted in 60% ethyl acetate in heptane. Product containing fractions were collected and concentrated to afford pure compound as a white solid. Obtained pure compound was purified by prep-HPLC. Product containing fractions were collected and lyophilized to afford I-107 (18.0 mg 7.51%) and I-141 (36.0 mg, 3.91%) as off white solid.

I-107

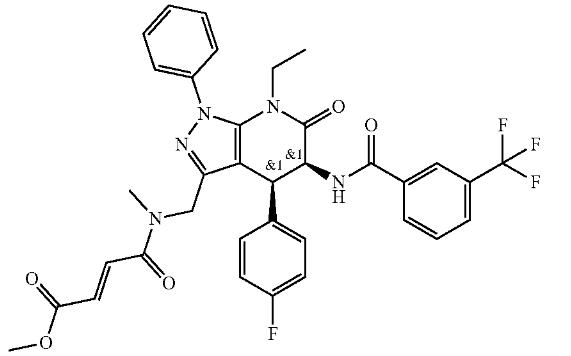

$^1$H NMR (400 MHZ, DMSO-$d_6$) δ=8.56-8.51 (m, 1H), 8.18-8.14 (m, 2H), 7.92 (d, J=7.6 Hz, 1H), 7.73-7.68 (m, 3H), 7.61-7.41 (m, 3H), 7.08-6.98 (m, 2H), 6.90-6.80 (m, 2H), 6.72-6.39 (m, 1H), 6.30-5.07 (m, 2H), 4.63-3.98 (m, 3H), 3.90-3.83 (m, 1H), 3.69-3.67 (m, 3H), 3.07-2.99 (m, 1H), 2.70-2.69 (m, 3H), 0.91-0.88 (m, 3H). LC-MS (Method-B)=678.0 $[M+H]^+$; 99.96% at RT 2.34 min. HPLC (Method-B)=99.80% at RT 8.89 min. Chiral HPLC (Method-A)=Peak-1=50.46% at RT 6.64 min. Peak-2=49.54% at RT 8.30 min.

I-141

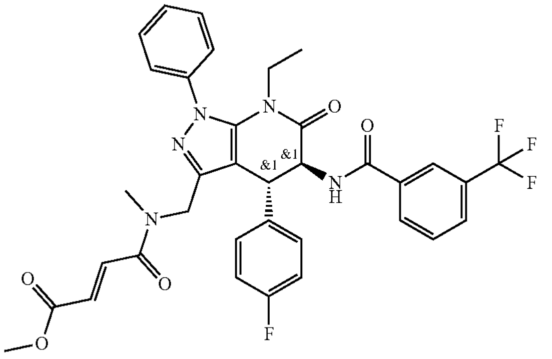

$^1$H NMR (400 MHZ, DMSO-$d_6$) δ=9.15-9.02 (m, 1H), 8.01-8.00 (m, 2H), 7.91 (d, J=7.2 Hz, 1H), 7.73-7.63 (m, 3H), 7.61-7.44 (m, 3H), 7.43-7.41 (m, 2H), 7.33-7.30 (m, 1H), 7.18-7.16 (m, 3H), 6.39-6.31 (m, 1H), 5.23-5.06 (m, 1H), 4.37 (d, J=10.0 Hz, 1H), 4.11-3.91 (m, 2H), 3.80-3.67 (m, 3H), 3.44-3.88 (m, 1H), 2.88-2.67 (m, 3H), 0.81-0.77 (m, 3H). LC-MS (Method-B)=778.0 $[M+H]^+$; 99.70% at RT 2.22 min. HPLC (Method-A)=96.19% at RT 6.09 min. Chiral HPLC (Method-A)=Peak-1=50.1% at RT 4.88 min. Peak-2=49.9% at RT 5.57 min.

Example 22: Synthesis of Compounds I-147

NMR:

[1]H spectrum was recorded on Bruker 400 MHz and Varian 400 MHz instruments internally referenced to a tetramethylsilane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: I (95:5) B: 0.05% Formic acid in CAN. InJ Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge BEH C18, (50 mm*3.0 mm,2.5μ) Mobile Phase A: 2.5 mM Ammonium Bicarbonate in Water+5% CAN; Mobile Phase B: 100% I Flow rate: 1.0 mL/min. Column temperature: 40° C. Gradient Program (B %): 0.0/2, 0.3/2, 2.0/98, 2.8/98, 3.0/2,3.7/2.

Method-C: Column: X-Select CSH C18 (50 mm*3.0 mm,2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2,2.0/98, 2.8/98, 3.0/2,3.7/2.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5, 1/5,8/100,12/100, 14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/2,2/2, 12/90, 16/90; Flow: 1.0 mL/min.; Diluent: I:Water (80:20).

Method-C: Column: X SELECT CSH C18 (150×4.6 mm, 3.5μ); Mobile Phase A; 0.05% TFA in water: I (95:05); Mobile Phase B: 0.05% TFA in water: I (05:95); Programme: T/B %: . 0.01/10,12/90,16/90; Flow: 1 mL/min.; Diluent: water: I (80:20).

Method-D: Column: X-Bridge C18 (4.6*150) mm 5μ Mobile Phase: A—5 mM Amm Acetate in H20 B—Acetonitrile InJ Volume; 5.0 μL, Flow Rate: 1.0 mL/minute.

Chiral-HPLC:

Method-A: Column: CHIRALCEL-OX-H (250×4.6 mm, 5 μm) Mobile Phase A: n-Hexane; Mobile Phase B: EtOH: MeOH (1:1) A/B: 50/50 Flow: 1.0 ml/MIN.

Method-B: Column: CHIRALPAK IG (250×4.6 mm, 5 μm) Mobile Phase A: 0.1% DEA in n-Hexane; MobilePhase B: IPA A B: 60:40 Flow rate: 1.0 ml/min.

Method-C: Column Name: CHIRALPAK-IC (250×4.6 mm, 5 μm) Mobile phase-A: n-Hexane; Mobile phase-B: DCM: IPA (50:50) Flow rate: 1.0 ml/min % A/B: 50:50.

Method-D: Column: CHIRALPAK IC (250×4.6 mm, 5 μm) Mobile Phase A: 0.1% TFA n-Hexane; Mobile Phase B: IPA A: B: 80/20 FLOW: 1.0 ml/min.

Method-E: Column Name: CHIRALPAK-IG (250*4.6 mm, 5 μm) Mobilephase-A: 0.1% DEA in Hexane; Mobilephase-B: EtOH: MeOH (50:50) Flow rate: 1.0 ml/min % A/B: 50:50.

General Scheme

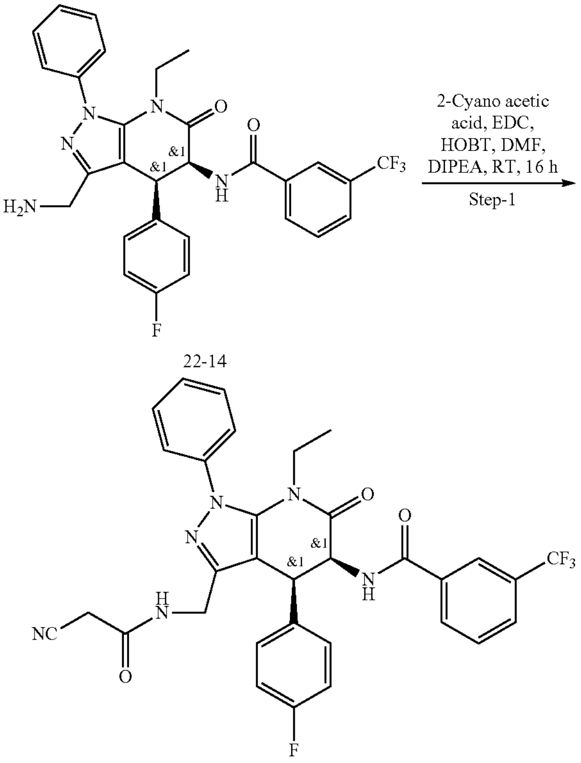

22-14

I-147

Synthesis of rac-N-((4R,5R)-3-((2-cyanoacetamido)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (I-147)

To a stirred solution of 22-14 (1.00 g, 1.81 mmol) in DMF (10 mL) was added DIPEA (0.71 g, 5.44 mmol), EDCI (0.53 g, 2.72 mmol), compound B (0.18 g, 2.17 mmol) and 1-hydroxybenzotriazole (0.37 g, 2.72 mmol) were added at room temperature. The resulting solution was stirred for 16 h at RT. The progress of the reaction was monitored by TLC.

Reaction mixture was quenched with water and extracted with EtOAc. Combined organic layers were dried over anhydrous sodium sulphate and concentrated to get crude compound. The above crude compound was purified by silica gel column chromatography using 20% EtOAc/Heptane and was concentrated under reduced pressure to afford I-147 (0.70 g, 61.78%) as light-yellow solid.

$^1$H NMR (400 MHZ, DMSO-$d_6$) δ=8.57-8.51 (m, 2H), 8.21-8.11 (m, 2H), 7.93 (d, J=7.8 Hz, 1H), 7.75-7.52 (m, 6H), 7.16-7.04 (m, 2H), 6.99-6.89 (m, 2H), 5.51 (t, J=7.4 Hz, 1H), 4.55 (d, J=7.3 Hz, 1H), 4.31 (dd, J=6.6, 15.4 Hz, 1H), 4.12 (dd, J=5.0, 15.3 Hz, 1H), 3.97-3.84 (m, 1H), 3.22-3.14 (m, 1H), 3.08-2.98 (m, 2H), 0.91 (t, J=7.0 Hz, 3H). LCMS (Method-B)=619.10 $[M+H]^+$; 99.87% at RT 2.25 min. HPLC (Method-B)=99.78% at RT 8.92 min. Chiral HPLC (Method-E)=Peak-1=49.51% at RT 4.93 min Peak-2=50.49% RT at 6.76 min.

Example 23: Synthesis of Compound I-79

NMR:

$^1$H spectrum was recorded on Bruker 400 MHz and Varian 400 MHz instruments internally referenced to a tetramethylsilane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: I (95:5); B: 0.05% Formic acid in I. Inj Volume: 2.0 μL, Column oven temperature: 50 C; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge BEH C18, (50 mm*3.0 mm,2.5μ) Mobile Phase A: 2.5 mM Ammonium Bicarbonate in Water+5% CAN; Mobile Phase B: 100% CAN; Flow rate: 1.0 mL/min. Column temperature: 40° C. Gradient Program (B %): 0.0/2, 0.3/2, 2.0/98, 2.8/98, 3.0/2,3.7/2.

Method-C: Column: X-Select CSH C18 (50 mm*3.0 mm,2.5μ) Mobile Phase A: 0.05% TFA in Water; Mobile Phase B: 0.05% TFA in Acetonitrile; Flow rate: 1.0 mL/min. Column temperature: 40° C. Gradient Program (B %): 0.0/2, 0.3/2,2.0/98, 2.8/98, 3.0/2,3.7/2.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5,1/5,8/100,12/100,14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/2,2/2,12/90,16/90; Flow: 1.0 mL/min.; Diluent: I:Water (80:20).

Method-C: Column: X SELECT CSH C18 (150×4.6 mm, 3.5μ); Mobile Phase A; 0.05% TFA in water: I (95:05); Mobile Phase B: 0.05% TFA in water: I (05:95); Programme: T/B %: . 0.01/10,12/90,16/90; Flow: 1 mL/min.; Diluent: water: I (80:20).

Method-D: Column: X-Bridge CSH C18 (4.6*150) mm 5μ Mobile Phase: A-0.1% TFA in water; B-Acetonitrile Inj Volume; 5.0 μL, Flow Rate: 1.2. mL/minute Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in Hexane; Mobile Phase B: IPA A/B: 60/40 Flow: 1.0 ml/MIN PDA: OJ-H_015.

Method-F: Column Name: CHIRALPAK-IK (250×4.6 mm, 5 μm) Mobilephase-A: n-Hexane; Mobilephase-B: ETOH/MEOH (50/50) Flow rate: 1.0 mL/min % A/B: 50/50.

Method-G: Column: X-Select CHS C18 (4.6*150) mm 5μ Mobile Phase: A-5 mM Ammonium acetate; B-Acetonitrile Inj Volume; 5.0 μL, Flow Rate: 1.0 mL/minute.

Synthesis of 23-1 and 23-2

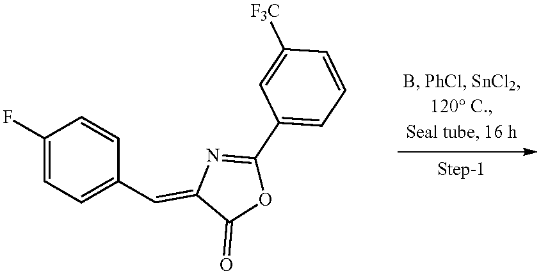

SM-1

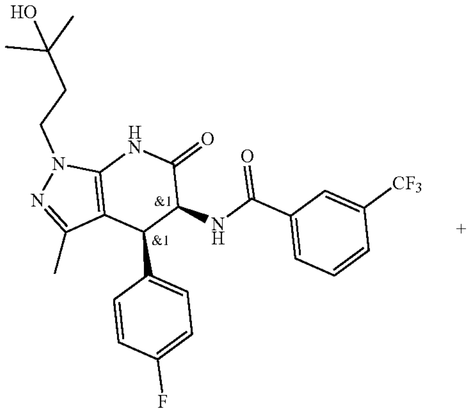

1

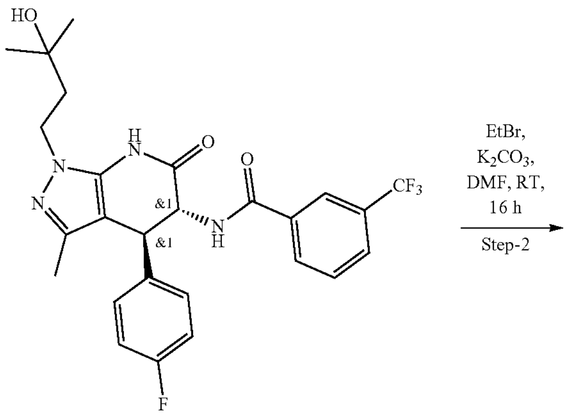

1A

-continued

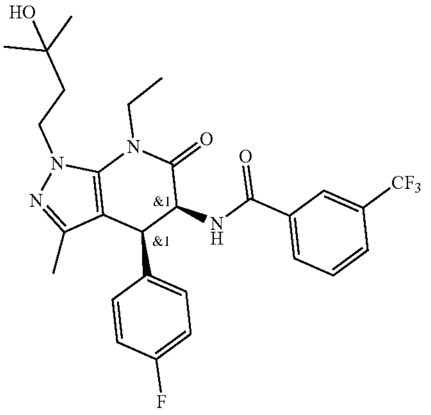

23-2

+

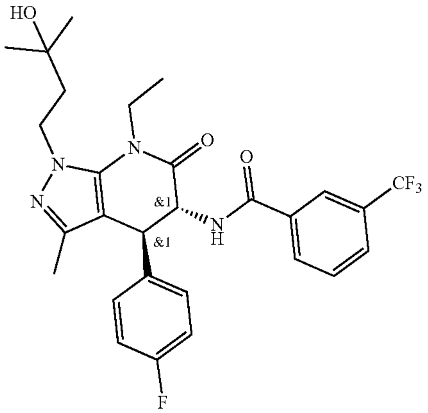

23-1

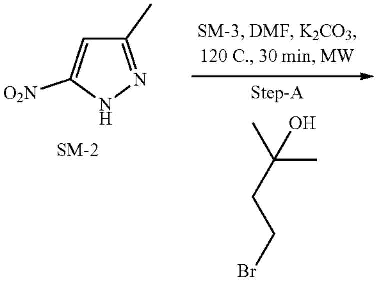

SM-2

SM-3

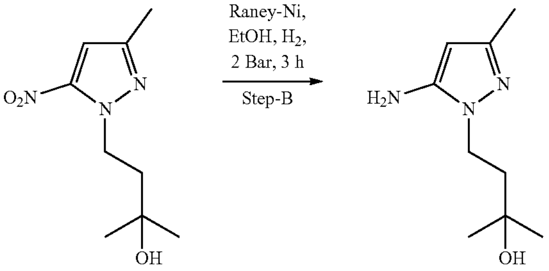

A

B

-continued

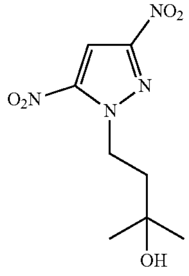

A'

Step-A: Synthesis of 2-methyl-4-(3-methyl-5-nitro-pyrazol-1-yl)butan-2-ol (A)

To a stirred solution of SM-2 (1.0 g, 7.9 mmol) and $K_2CO_3$ (2.4 g, 17 mmol) in DMF (15 mL) was added SM-3 (1.6 g, 9.4 mmol), then stirred at 120° C. for 30 min. After completion of the reaction, the reaction mixture was poured into water (100 mL) and extracted with EtOAc (2×250 mL). The organic layer was washed with water (2×100 mL) and dried over anhydrous sodium sulphate. The organic layer was concentrated under reduced pressure to obtain the crude product. Then, the crude material was purified by FCC chromatography. Eluting with 20% EtO Ac/heptane afforded A (0.3 g, 18% Yield) and eluting with 50% EtOAc/heptane to afforded A' (0.85 g, 51%)—as yellow syrup.

Data for A:

$^1$HNMR (400 MHZ, DMSO-d$_6$) δ=7.03 (s, 1H), 4.52 (t, J=7.6 Hz, 2H), 4.45 (s, 1H), 2.21 (s, 3H), 1.84 (t, J=8.4 Hz, 2H), 1.14 (s, 6H). LC-MS (Method-B)=214.1 [M+H]$^+$; 97.03% at RT 1.817 min.

Data for A':

$^1$HNMR (400 MHZ, DMSO-d$_6$) δ=6.82 (s, 1H), 4.51 (s, 1H), 4.20 (t, J=7.6 Hz, 2H), 2.35 (s, 3H), 1.85 (t, J=8.0 Hz, 2H), 1.14 (s, 6H). LC-MS (Method-B)=214.1 [M+H]$^+$; 88.01% at RT 1.717 min.

Step-B: Synthesis of 4-(5-amino-3-methyl-pyrazol-1-yl)-2-methyl-butan-2-ol (B)

To a stirred solution of A (0.3 g, 1.40 mmol) in ethanol (5.0 mL) was added Raney-Ni (60 mg) and stirred for 3 h at room temperature under $H_2$ at 50 psi. After completion of the reaction, the catalyst was filtered through celite bed and washed with 5% MeOH/DCM and evaporated to afford B (0.25 g, 96%) as yellow syrup.

$^1$HNMR (400 MHZ, DMSO-d$_6$) δ=5.06-5.05 (m, 1H), 4.93 (s, 2H), 4.40-4.39 (m, 1H), 3.81-3.77 (m, 2H), 1.95-1.94 (m, 3H), 1.73-1.70 (m, 2H), 1.10-1.09 (m, 6H). LC-MS (Method-B)=184.2 [M+H]$^+$; 95.72% at RT 1.233 min.

Step-1: Synthesis of N-[rac-(4S,5R)-4-(4-fluorophenyl)-1-(3-hydroxy-3-methyl-butyl)-3-methyl-6-oxo-5,7-dihydro-4H-pyrazolo[3,4-b]pyridine-5-yl]-3-(trifluoromethyl)benzamide (1A)

To a stirred solution of SM (0.45 g, 1.34 mmol) and B (0.246 g, 1.34 mmol) in chlorobenzene (10 mL) was added $SnCl_2$ (0.056 g, 0.26 mmol) and the reaction mixture was stirred for 16 h at 120° C. After the completion, the reaction mixture was poured into water (50 mL) and extracted with EtOAc (2×100 mL) The organic layer was washed with water (twice) and dried over anhydrous $Na_2SO_4$. The organic layer was concentrated under reduced pressure to obtain crude. The crude material was purified by FCC chromatography. Eluting with 50% EtOAc/heptane afforded 1 (0.120 g, 17%) and eluting with 80% EtOAc/heptane afforded 1A (0.225 g) as off white solid.

Data for 1A:

$^1$HNMR (400 MHZ, DMSO-$d_6$) δ=10.99 (s, 1H), 8.92 (d, J=8.8 Hz, 1H), 8.02-7.99 (m, 2H), 7.89 (d, J=7.2 Hz, 1H), 7.69 (t, J=7.6 Hz, 1H), 7.34-7.30 (m, 2H), 7.11 (t, J=8.8 Hz, 2H), 4.85-4.80 (m, 1H), 4.38 (s, 1H), 4.32-4.29 (m, 1H), 4.12-3.92 (m, 3H), 3.16 (d, J=5.6 Hz, 1H), 1.81 (t, J=7.6 Hz, 2H), 1.36 (s, 3H), 1.12 (s, 6H). LC-MS (Method-B)=519.2 $[M+H]^+$; 74.42% at RT 2.067 min.

Data for 1:

$^1$HNMR (400 MHZ, DMSO-$d_6$) δ=11.18 (s, 1H), 8.45 (d, J=6.8 Hz, 1H), 8.01-8.00 (m, 2H), 7.88 (d, J=7.6 Hz, 1H), 7.67 (t, J=8.4 Hz, 1H), 7.06 (t, J=8.8 Hz, 2H), 6.95-6.92 (m, 2H), 5.15 (t, J=7.2 Hz, 1H), 4.44-4.38 (m, 2H), 4.14-3.97 (m, 2H), 1.89-1.82 (m, 5H), 1.13 (s, 6H). LC-MS (Method-B)=519.1 $[M+H]^+$; 99.67% at RT 2.067 min.

Step-2: Synthesis of N-[rac-(4S,5S)-7-ethyl-4-(4-fluorophenyl)-1-(3-hydroxy-3-methyl-butyl)-3-methyl-6-oxo-4,5-dihydropyrazolo[3,4-b]pyridine-5-yl]-3-(trifluoromethyl)benzamide (23-2)

To the solution of 1 (0.1 g, 0.192 mmol) in DMF (3.0 mL) were added $K_2CO_3$ (0.034 g, 0.25 mmol) and bromoethane (0.027 g, 0.25 mmol) at 0° C., and stirred for 6 h at room temperature. After completion of the reaction, the reaction mixture was poured into water and extracted with EtOAc (2×50 mL). The organic layer was washed with water (twice) and dried over anhydrous $Na_2SO_4$. The organic layer was concentrated under reduced pressure to obtain the crude product. The crude material was purified by FCC chromatography by eluting with 40% EtOAc/heptane to afford 23-2 (0.050 g, 47%) as an off white solid.

$^1$HNMR (400 MHZ, DMSO-$d_6$) δ=8.45 (d, J=87.2 Hz, 1H), 8.12-8.09 (m, 2H), 7.91 (d, J=8.0 Hz, 1H), 7.70 (t, J=7.6 Hz, 1H), 7.10-7.04 (m, 2H), 6.96-6.93 (m, 2H), 5.17 (t, J=7.2 Hz, 1H), 4.51 (s, 1H), 4.38 (d, J=7.6 Hz, 1H), 4.26-4.12 (m, 3H), 3.88-3.83 (m, 1H), 1.95-1.85 (m, 5H), 1.29 (t, J=6.8 Hz, 3H), 1.17 (s, 3H), 1.15 (s, 3H). LC-MS (Method-B)=547.3 $[M+H]^+$; 96.630% at RT 2.303 min. HPLC (Method-B)=95.041% at RT 8.505 min. HPLC-Chiral (Method-F)=46.26% at RT 12.324 min, 49.91% at RT 15.631 min.

Step-2: Synthesis of N-[rac-(4S,5R)-7-ethyl-4-(4-fluorophenyl)-1-(3-hydroxy-3-methyl-butyl)-3-methyl-6-oxo-4,5-dihydropyrazolo[3,4-b]pyridine-5-yl]-3-(trifluoromethyl)benzamide (23-1)

To a stirred solution of 1A (0.23 g, 0.44 mmol) in DMF (6.0 mL) were added $K_2CO_3$ (0.079 g, 0.57 mmol) and bromoethane (0.063 g, 0.57 mmol) at 0° C. and the reaction mixture was stirred for 16 h at room temperature. After completion, the reaction mixture was poured into water and extracted with EtOAc (2×50 mL). The organic layer was washed with water (twice) and dried over anhydrous $Na_2SO_4$. The organic layer was concentrated under reduced vacuum to crude. The crude material was purified by preparative purification to afford 23-1 (0.125 g, 51.6%) as off white solid.

$^1$HNMR (400 MHZ, DMSO-$d_6$) δ=8.93 (d, J=8.8 Hz, 1H), 7.98-7.97 (m, 2H), 7.89 (d, J=8.0 Hz, 1H), 7.69 (t, J=7.6 Hz, 1H), 7.34-7.30 (m, 2H), 7.14 (t, J=8.8 Hz, 2H), 5.01-4.96 (m, 1H), 4.50 (s, 1H), 4.29-4.15 (m, 3H), 4.13-4.02 (m, 1H), 3.87-3.78 (m, 1H), 1.96-1.79 (m, 2H), 1.34 (s, 3H), 1.21 (t, J=6.8 Hz, 3H), 1.16 (s, 3H), 1.15 (s, 3H). LC-MS (Method-B)=547.1 $[M+H]^+$; 99.84% at RT 2.171 min. HPLC (Method-A)=98.07% at RT 5.788 min.

NMR:

$^1$H NMR spectrum was recorded on Bruker 400 MHz and Varian 400 MHz instruments internally referenced to a tetramethyl silane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ; Mobile Phase: A: 0.05% Formic acid in water: I (95:5); B: 0.05% Formic acid in I Inj Volume: 2.0 μL, Column oven temperature: 50° C.; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

Method-C: Column: X-Select CSH C18, (50 mm*3.0 mm, 2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2,2.0/98, 2.8/98, 3.0/2,3.7/2.

Method-D: Column: X-Select CSH C18 (3.0*50 mm, 2.5 μm), Mobile Phase A: 2.5 Mm Ammonium Bicarbonate in $H_2O$+5% CAN; Mobile Phase B: 100% I, Gradient % B: 0/2,0.3/2,2.0/98,2.8/98,3.0/2,3.7/2, Flow rate: 1.0 mL/min.

Method-E: Column: X-Bridge BEH $C_{18}$, (50 mm*3.0 mm, 2.5μ) Mobile Phase A: 2.5 mM Ammonium Bicarbonate in Water+5% CAN; Mobile Phase B: 100% ACN Flow rate: 1.0 mL/min. Column temperature: 40° C. Gradient Program (B %): 0.0/2, 0.3/2, 2.0/98, 2.8/98, 3.0/2,3.7/2.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5,1/5,8/100,12/100,14/5, 18/5; Flow rate: 1.2 ml/min.

Method-B: Column: X-Bridge CSH C18 (150×4.6 mm, 3.5 μm); Mobile Phase-A: 5 mM $NH_4HCO_3$; Mobile Phase-B: I; Programme: T/B %: 0.01/2, 2/2, 12/90,1 6/90; Flow rate: 1.0 mL/min.; Diluent: I: WATER (80:20).

Method-C: Column: X SELECT CSH C18 (150×4.6 mm, 3.5μ); Mobile Phase A; 0.05% TFA in water: I (95:05); Mobile Phase B: 0.05% TFA in water: I (05:95); Programme: T/B %: . 0.01/10,12/90,16/90; Flow rate: 1 mL/min.; Diluent: WATER: I (80:20).

Method-D: Column: X-Bridge CSH C18 (4.6*150) mm 5μ Mobile Phase: A-0.1% TFA in water; B-Acetonitrile Inj Volume; 5.0 μL, Flow Rate: 1.2 mL/minute Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: n-Hexane; Mobile Phase B: IPA A/B: 50/50 Flow: 1.0 ml/MIN PDA: OJ-H_015.

Method-F: Column: ACE Excel 2 C18-AR, 100 mm×3.0 mm Mobile Phase A: 0.05% TFA in Water; Mobile Phase B: 0.05% TFA in Acetonitrile; Column Temperature: 40° C.; Flow Rate: 0.6 mL/min Gradient: 0/5, 1/5, 6/90, 8.5/90, 8.8/5, 11/5.

Method-G: Column: CHIRAL PAK-IC (250×4.6 mm, 5 μm) Mobile Phase A: 0.1% DEA in Hexane; Mobile Phase B: EtOH/MeOH (50/50) A: B: 80/20 Flow 1.0 ml/min.

Method-H: Column: X-Bridge C18 (4.6*150) mm 5μ Mobile Phase: A-5 mM Ammonium Acetate; B-Acetonitrile; Flow Rate: 1.0. mL/minute Gradient program: Time (min)/B Conc.: 0.01/5, 1.0/5, 8.0/100, 12.0/100, 14.0/5, 18.0/5.

Method-I: Column: CHIRALPAK-AD-H (250×4.6 mm, 5 μm), Mobile Phase A: 0.1% FA in n-Hexane, Mobile Phase B: EtOH Flow Rate: 1.0. mL/minute.

Method-J: Column: CHIRALPAK-IK (250*4.6 mm, 5 μm), Mobile Phase A: n-Hexane Mobile Phase B: IPA: MeOH, Flow: 1.0 ml/MIN.

Method-K: Column: CHIRALPAK-IG (250×4.6 mm, 5 μm), Mobile Phase A: 0.1% DEA n-Hexane, Mobile Phase B: DCM: MEOH (50:50), Flow rate: 1.0 ml/min.

Method-L: Column: CHIRALPAK-IC (250×4.6 mm, 5 μm) Mobile phase-A: MeOH (100%), Flow rate: 1.0 ml/min.

Method-M: Column: CORTECS UPLC C18 (3.0*30 mm, 1.6 μm), Mobile Phase A: 0.05% Formic acid in water, Mobile Phase B: 0.05% Formic acid in I, Gradient: Time/% B: 0/3,0.1/3,1.4/97,2/97, 2.05/3,2.5/3. Flow Rate: 0.85 ml/min.

Synthesis of I-79

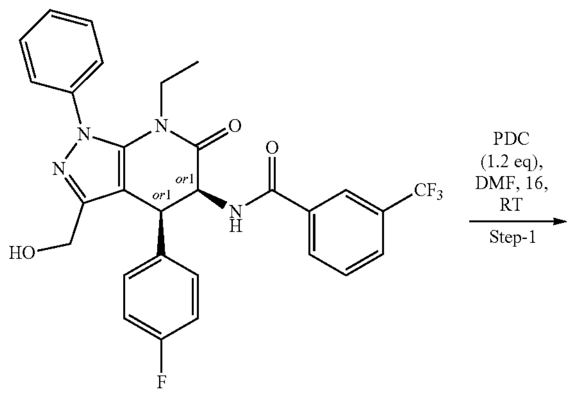

23-2

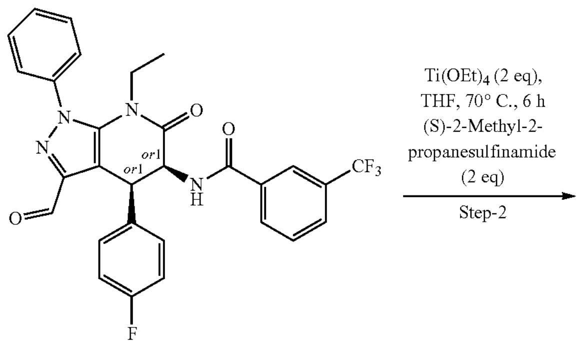

1

-continued

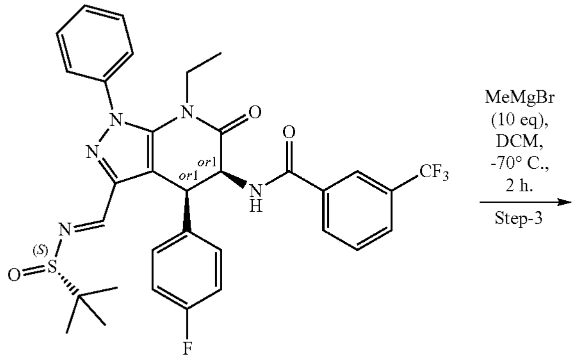

2

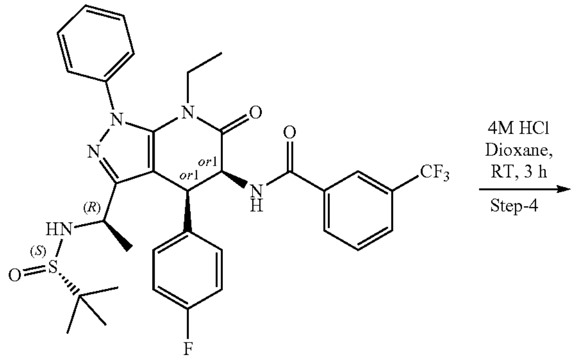

3

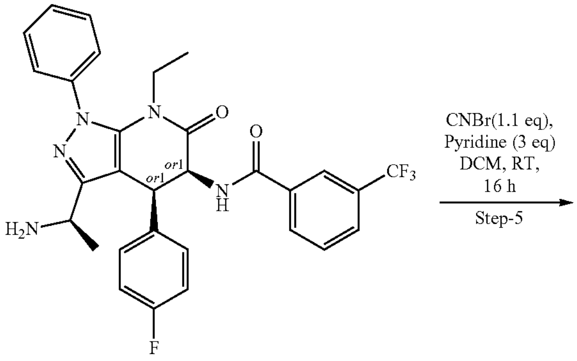

4

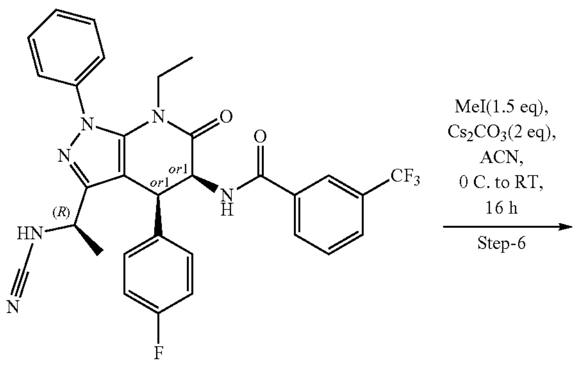

5

-continued

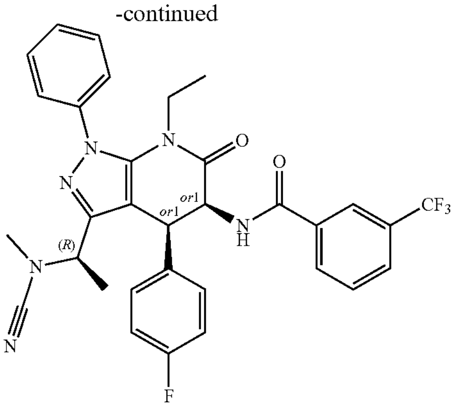

I-79

Step 1: Synthesis of rel-N-((4R,5R)-7-ethyl-4-(4-fluorophenyl)-3-formyl-6-oxo-1-phenyl-4,5,6,7-tetrahydro-1H-pyrazolo[3,4-b]pyridine-5-yl)-3-(trifluoromethyl)benzamide To a stirred solution of rel-N-((4R,5R)-7-ethyl-4-(4-fluorophenyl)-3-(hydroxymethyl)-6-oxo-1-phenyl-4,5,6,7-tetrahydro-1H-pyrazolo[3,4-b]pyridine-5-yl)-3-(trifluoromethyl)benzamide (2.5 g, 4.5 mmol) in DMF (25.00 mL) was added slowly Pyridinium dichromate (2.050 g, 5.340 mmol) at 0° C. and the reaction mixture was stirred at RT for 16 h. Reaction progress was monitored by TLC (50% EtOAc/Heptane). After completion of SM by TLC, reaction mixture was quenched with ice cold water (250 mL) and extracted with EtOAc (2×500 mL). The combined organic layers were dried over anhydrous sodium sulfate, filtered, and concentrated under reduced pressure to obtain crude compound. The crude product was purified by silica gel flash column chromatography, eluted at 7-15% EtOAc/Heptane to afford rel-N-((4R,5R)-7-ethyl-4-(4-fluorophenyl)-3-formyl-6-oxo-1-phenyl-4,5,6,7-tetrahydro-1H-pyrazolo[3,4-b]pyridine-5-yl)-3-(trifluoromethyl)benzamide (1.85 g, 74% yield) as off-white semi solid. $^1$H NMR (400 MHZ, $CDCl_3$) δ=9.92 (s, 1H), 7.99 (s, 1H), 7.84 (d, J=7.2 Hz, 1H), 7.77 (d, J=7.6 Hz, 1H), 7.57 (s, 4H), 7.10-7.00 (m, 2H), 6.95 (t, J=8.4 Hz, 2H), 6.83 (d, J=5.2 Hz, 1H), 5.31 (t, J=6.4 Hz, 1H), 5.22 (d, J=7.2 Hz, 1H), 4.01-3.96 (m, 1H), 3.21-3.16 (m, 1H), 1.24 (s, 1H), 1.01 (t, J=6.8 Hz, 3H), 0.90-0.75 (m, 1H). LCMS (Method-D): 551.1 $(M+H)^+$, 98.87% at RT: 2.45 min. C-HPLC (Method-E): 23.77% at RT: 4.185 min, 74.84% at RT: 5.894 min.

Step 2: Synthesis of N-((4R*,5R*)-3-(I—(((S)-tert-butylsulfinyl)imino)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide To a stirred solution of rel-N-((4R,5R)-7-ethyl-4-(4-fluorophenyl)-3-formyl-6-oxo-1-phenyl-4,5,6,7-tetrahydro-1H-pyrazolo[3,4-b]pyridine-5-yl)-3-(trifluoromethyl)benzamide (2.0 g, 3.6 mmol) in THF (30.00 mL) was added(S)-2-methylpropane-2-sulfinamide (900.00 mg, 7.4257 mmol) followed by Titanium (IV) ethoxide (1.6 mL, 7.2 mmol) at 0° C. and the reaction mixture was stirred at 80° C. for 16 h. Reaction progress was monitored by TLC (50% EtOAc/Heptane). After completion of SM by TLC, reaction mixture was quenched with ice cold $NH_4Cl$ solution (250 mL) and extracted with EtOAc (2×250 mL). The combined organic layers were dried over anhydrous sodium sulfate, filtered and concentrated under reduced pressure to afford N-((4R*,5R*)-3-(I—(((S)-tert-butylsulfinyl)imino)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (2.1 g, 82% Yield) as off white solid. LCMS (Method-D): 654.1 $(M+H)^+$, 88.46% at RT: 2.53 min. C-HPLC (Method-K): 98.04% at RT: 16.058 min.

Step 3: Synthesis of N-((4R*,5R*)-3-((R)-1-(((S)-tert-butylsulfinyl)amino)ethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide To a stirred solution of N-((4R*,5R*)-3-(I—(((S)-tert-butylsulfinyl)imino)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (1.0 g, 1.5 mmol) in DCM (15.00 mL) was added $CH_3MgBr$ 3.0 M in DEE (5.0 mL, 15 mmol) drop wise at −70° C. and reaction mixture was stirred at same temperature for 2 h. Reaction progress was monitored by TLC (70% EtOAc/Heptane). After completion of SM by TLC, reaction mass was quenched with cold $NH_4Cl$ solution (50 mL) and extracted with DCM (2×100 mL). The combined organic layers were dried over anhydrous $Na_2SO_4$, filtered and concentrated under reduced pressure to afford N-((4R*,5R*)-3-(I-1-(((S)-tert-butylsulfinyl)amino)ethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (800.00 mg, 78% Yield) as off white solid. LCMS (Method-D): 670.2 $(M+H)^+$, 59.22% at RT: 2.49 min. C-HPLC (Method-K): 77.10% at RT: 6.314 min, 19.20% at RT: 12.319 min.

Step 4: Synthesis of N-((4R*,5R*)-3-((R)-1-aminoethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide To a stirred solution of N-((4R*,5R*)-3-(1-1-(((S)-tert-butylsulfinyl)amino)ethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (2.5 g, 3.7 mmol) in dichloromethane (25 mL) was added HCl 4.0 M in Dioxane (2.5 mL, 10 mmol) drop wise at 0° C. and the reaction mixture was stirred at RT for 16 h. Reaction progress was monitored by TLC (50% EtOAc/Heptane, $R_f$=0.1). After completion of SM by TLC, reaction mass was directly concentrated under reduced pressure to obtain crude as off white solid. The crude product was purified by reverse phase prep. HPLC using Column: X-Bridge (250*20 mm), 5μ (AMC-Y-008), Mobile Phase A: 10 Mm ABC IN Water, Mobile Phase B: 100% I, Flow rate: 25 mL, Gradient (Time/% B): 0/10, 3/10, 20/35, 30/40, 60/98. Prep. HPLC provided 100 mg (Peak-1) of minor diastereomer and 1.4 g of major diastereomer (Peak-2).1.4 g of major diastereomer, which was further subjected for chiral HPLC purification to get 150 mg Peak-1 and 450 mg peak-2 N-((4R*,5R*)-3-((R)-1-aminoethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (450 mg, 21% yield) as off white solid. Peak-2 should be expected desired R-isomer as per RRT which was matched with previous batch through co-injection.

$^1$H NMR (400 MHZ, DMSO-$d_6$) δ=8.48 (d, J=7.2 Hz, 1H), 8.16 (t, J=6.4 Hz, 2H), 7.93 (d, J=7.6 Hz, 1H), 7.73-7.65 (m, 3H), 7.59-7.49 (m, 3H), 7.12 (t, J=8.8 Hz, 2H), 7.01 (t, J=5.6 Hz, 2H), 5.51 (t, J=7.2 Hz, 1H), 4.73 (d, J=7.2 Hz, 1H), 3.91-3.86 (m, 2H), 3.09 (q, J=14.2 Hz, 1H), 1.82 (s, 2H), 1.11 (d, J=6.8 Hz, 3H), 0.93 (t, J=7.2 Hz, 3H). LCMS (Method-B): 566.19 $(M+H)^+$, 98.01% at RT: 2.30 min. C-HPLC (Method-K): 99.54% at RT: 12.397 min.

Step 5: Synthesis of N-((4R*,5R*)-3-((R)-1-cyanamidoethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide To a stirred solution of N-((4R*,5R*)-3-((R)-1-aminoethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (150 mg, 0.2652 mmol) in dichloromethane (2 mL) was added pyridine (0.06 mL) followed by cyanogen bromide (0.075 mL) at RT and the reaction mixture was stirred for 16 h at RT. Reaction progress was monitored by TLC (10% MeOH/DCM, $R_f$=0.7). After completion of SM by TLC, reaction mass was quenched with ice cold water (25 mL) and extracted with DCM (2×25 mL). The combined organic layers were dried over anhydrous sodium sulfate, filtered and concentrated under reduced pressure to obtain crude compound. The crude product was purified by silica gel flash column chromatography, eluted at 45-55% EtOAc/heptane to afford N-((4R*,5R*)-3-(I-1-cyanamidoethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (60 mg, 38.31% yield) as an off white solid.

$^1$H NMR (400 MHZ, DMSO-$d_6$) δ=8.54 (d, J=7.2 Hz, 1H), 8.16 (d, J=12.8 Hz, 2H), 7.93 (d, J=7.2 Hz, 1H), 7.73 (t, J=9.6 Hz, 3H), 7.62-7.54 (m, 3H), 7.26 (d, J=4.4 Hz, 1H), 7.13 (t, J=8.4 Hz, 2H), 7.00 (t, J=5.6 Hz, 2H), 5.55 (t, J=6.8 Hz, 1H), 4.68 (d, J=6.8 Hz, 1H), 4.32 (t, J=6.0 Hz, 1H), 3.92-3.85 (m, 1H), 3.09 (q, J=14.4 Hz, 1H), 1.22 (d, J=6.4 Hz, 3H), 0.93 (t, J=6.4 Hz, 3H). LCMS (Method-D): 591.4 $(M+H)^+$, 97.89% at RT: 2.32 min. C-HPLC (Method-K): 99.42% at RT: 7.910 min.

Step 6: Synthesis of N-((4R*,5R*)-7-ethyl-4-(4-fluorophenyl)-3-((R)-1-(N-methylcyanamido)ethyl)-6-oxo-1-phenyl-4,5,6,7-tetrahydro-1H-pyrazolo[3,4-b]pyridine-5-yl)-3-(trifluoromethyl)benzamide To a stirred solution of N-((4R*,5R*)-3-(I-1-cyanamidoethyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl)benzamide (60 mg, 0.1016 mmol) in I (0.5 mL) was added Cesium carbonate (68 mg, 0.208 mmol) and iodomethane (0.02 mL) at 0° C. and the reaction mixture was stirred at RT for 16 h. Reaction progress was monitored by TLC (50% EtOAc/Heptane, $R_f$=0.5). After completion of SM by TLC, reaction mass was concentrated under reduced pressure, diluted with water (20 mL), and extracted with EtOAc (2×20 mL). The combined organic layers were dried over anhydrous sodium sulfate, filtered and concentrated under reduced pressure to obtain crude compound 90 mg from 2 batches. Crude obtained was purified by reverse phase prep. HPLC using Preparative Column: YMC C18 (20*250) mm, 5μ, Mobile phase-A: 0.1% FA in water, Mobile phase-B: 100% I, Flow rate: 15 ml/min, Gradient (Time/% B): 0/25,3/25,10/40,30/90 to afford N-((4R*,5R*)-7-ethyl-4-(4-fluorophenyl)-3-(I-1-(N-methylcyanamido)ethyl)-6-oxo-1-phenyl-4,5,6,7-tetrahydro-1H-pyrazolo[3,4-b]pyridine-5-yl)-3-(trifluoromethyl)benzamide (55.00 mg, 89.54% yield) as an off-white solid.

$^1$H NMR (400 MHZ, DMSO-$d_6$) δ=8.55 (d, J=7.2 Hz, 1H), 8.16 (t, J=5.6 Hz, 2H), 7.93 (d, J=7.6 Hz, 1H), 7.73 (t, J=7.2 Hz, 3H), 7.62-7.53 (m, 3H), 7.14 (t, J=8.8 Hz, 2H), 7.01 (q, J=8.4 Hz, 2H), 5.56 (t, J=7.2 Hz, 1H), 4.64 (d, J=7.2 Hz, 1H), 4.27 (q, J=13.8 Hz, 1H), 3.90 (q, J=14.2 Hz, 1H), 3.11 (q, J=14.4 Hz, 1H), 2.60 (s, 3H), 1.34 (d, J=7.2 Hz, 3H), 0.93 (t, J=6.8 Hz, 3H). LCMS (Method-C): 605.19 $(M+H)^+$, 99.70% at RT: 1.61 min. HPLC (Method-B): 99.34% at RT: 9.662 min. C-HPLC (Method-K): 99.95% at RT: 7.999 min.

Example 24: Synthesis of Compounds I-82 and I-133

NMR:

$^1$H spectrum was recorded on Bruker 400 MHz and Varian 400 MHz instruments internally referenced to a tetramethyl silane (TMS) signal. Chemical shifts (δ) and coupling constants (J) were expressed in parts per million and hertz, respectively.

LC-MS:

Method-A: LCMS_X-Select (Formic acid); Column: X-Select CSH C18 (3.0*50) mm 2.5μ. Mobile Phase: A: 0.05% Formic acid in water: I (95:5); B: 0.05% Formic acid in CAN. Inj Volume: 2.0 μL, Column oven temperature: 50 C; Flow Rate: 1.2. mL/minute Gradient program: 0% B to 98% B in 2.0 minute, hold till 3.0 min, at 3.2 min B conc is 0% up to 4.0 min.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C. Gradient program: 0% B to 98% B in 2.0 minute, hold till 3.0 min, at 3.2 min B conc is 0% up to 4.0 min.

HPLC:

Method-A: Column: X Select CSH C18 (150×4.6) mm,3.5μ; Mobile phase A: 0.1% FA in water: I (95:05); Mobile phase B: Acetonitrile; Gradient Programme: T/B %: 0.01/5, 1/5,8/100,12/100,14/5, 18/5; Flow rate: 1.2 ml/min.

Method-B: Column: X-SELECT CSH C18 (150×4.6 mm, 3.5 μm); Mobile Phase-A: 5 mM $NH_4HCO_3$; Mobile Phase-B: I; Programme: T/B %: 0.01/2,2/2,12/90,16/90; Flow: 1.0 mL/min.; Diluent: I:Water (80:20).

Chiral SFC Method:

Peak-1: Column:—CHIRALPAK IG (250×4.6) mm, 5 m, M.P-: n-Hexane/DCM/MeOH (80/10/10), Flow: 1.0 mL/min UV: 220 nm.

Peak-2: CHIRALPAK IG (250×4.6) mm,5 m, M.P-: n-Hexane/DCM/MeOH (80/10/10), Flow: 1.0 mL/min UV: 220 nm.

Synthesis of 24-1, 24-2, and 24-3
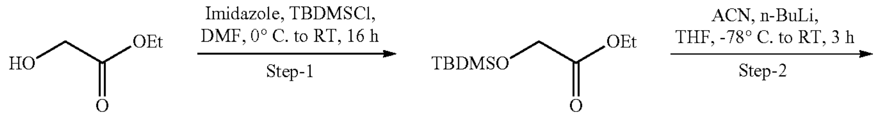
SM-1
1
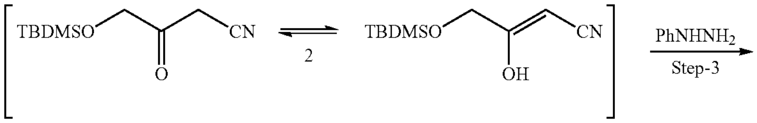
2
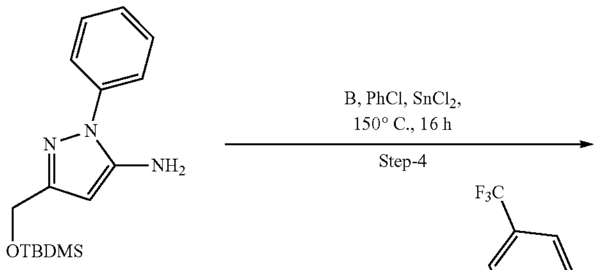
3
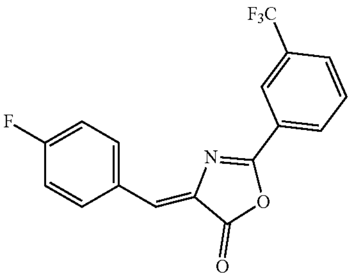
B
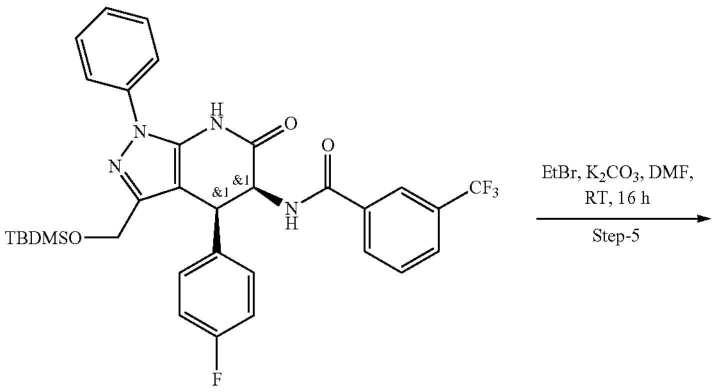
4
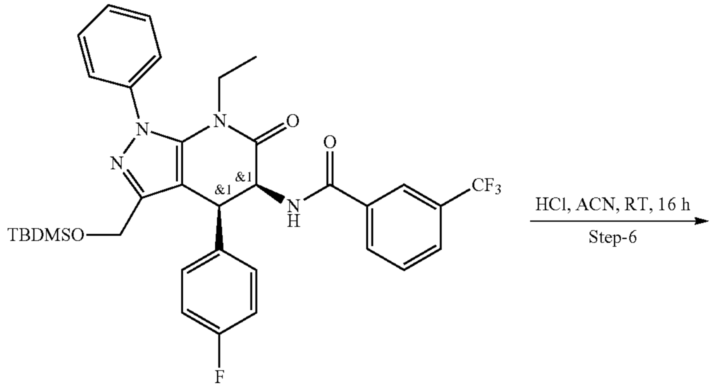
5

-continued

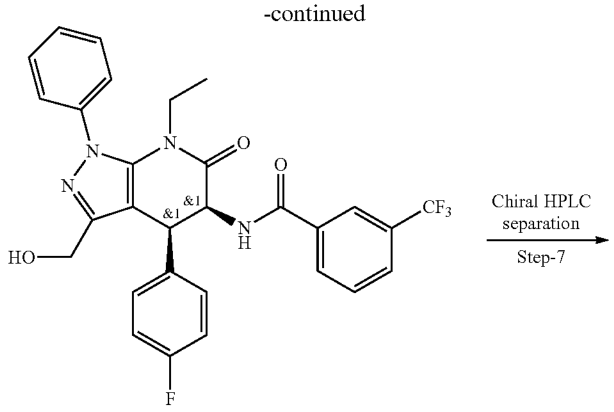

24-1

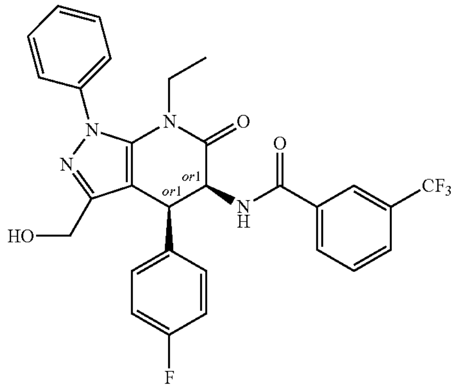

24-2

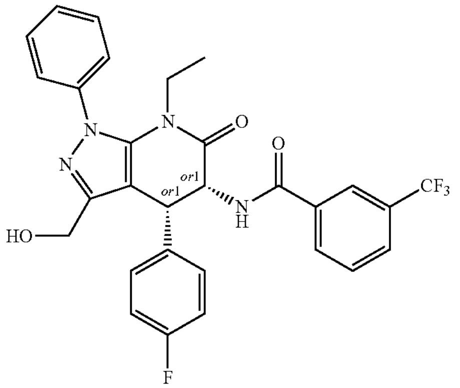

24-3

Step-(1): Synthesis of ethyl 2-[~{tert}-butyl(dimethyl)silyl]oxyacetate

To stirred solution of compound (SM1) (500 g, 4803 mmol) in DMF (2500 mL) was added imidazole (950.82 g, 6243 mmol) and TBDMSCl (950.82 g, 6243 mmol) at 0° C. The reaction mixture was stirred at room temperature for 16 h. After consumption of the starting material (by TLC), the reaction mixture was quenched with water (15 L) and extracted with EtOAc (2×10 L). Combined organic layer was washed with water (2×5 lit), brine (1×5 lit), and dried over anhydrous sodium sulfate, concentrated to afford compound (1) (1 kg, 95%) as colorless liquid.

$^1$H NMR (400 MHZ, DMSO-$d_6$) δ=4.22 (s, 2H), 4.13-4.08 (m, 2H), 1.19 (t, J=7.2 Hz, 3H), 0.90-0.84 (m, 9H), 0.05-0.02 (m, 6H).

Step-(2): Synthesis of 4-((tert-butyldimethylsilyl)oxy)-3-oxobutanenitrile (2)

To a stirred solution of acetonitrile (179 mL, 3434 mmol) in tetrahydrofuran (2500 mL), butyl lithium (2.5 mol/l) in hexanes (1437 ml, 3434 mmol) were added at −78° C. The reaction mixture was stirred at −78° C. for 30 min. Compound (1) (500 g, 2289 mmol) dissolved in tetrahydrofuran (2500 mL) was added to the reaction mixture slowly at the same temperature. After 30 mins, the reaction mixture was allowed to stir at room temperature and maintained the same for 3 h. Reaction progress was monitored by TLC. After completion of the reaction, the reaction mixture was quenched with ice cold water (200 mL) and adjusted pH to 4-5 using 2N aq·HCl solution. The reaction mixture was extracted with ethyl acetate (2×5 lit). Combined organic layer was dried over anhydrous sodium sulfate and concentrated under reduced pressure to afford crude compound (2) (450 g, 92%) as brown oil. The crude was taken for next step without purification.

Step-(3): Synthesis of 3-(((tert-butyldimethylsilyl)oxy)methyl)-1-phenyl-1H-pyrazol-5-amine (3)

To a stirred solution of compound (2) (50 g, 233 mmol) in chlorobenzene (250 mL), phenylhydrazine (32.9 g, 304 mmol) was added at room temperature. The reaction mass temperature as raised to 140° C. The reaction mixture was stirred at same temperature for 16 h. Reaction progress was monitored by TLC. After completion of starting material, the reaction mixture was quenched with water (200 mL) and extracted with ethyl acetate (2×500 mL). Combined organic layer was dried over anhydrous sodium sulfate, concentrated under reduced pressure to afford crude compound. The obtained crude compound was purified by column chromatography eluting with 15-20% ethyl acetate in pet ether to afford compound (3) (34.0 g, 48%) as a pale brown solid.

$^1$H NMR (400 MHZ, DMSO-$d_6$) δ=7.56 (d, J=7.2 Hz, 2H), 7.45 (t, J=7.6 Hz, 2H), 7.30-7.28 (m, 1H), 5.46 (s, 1H), 5.29 (s, 2H), 4.49 (s, 2H), 0.88 (s, 9H), 0.07 (s, 6H). LC-MS (Method-B)=304.0 [M+H]$^+$; 98.55% at RT 2.40 min.

Step-4: Synthesis of rac-N-((4R,5R)-3-(((tert-butyldimethylsilyl)oxy)methyl)-4-(4-fluorophenyl)-6-oxo-1-phenyl-4,5,6,7-tetrahydro-1H-pyrazolo[3,4-b]pyridine-5-yl)-3-(trifluoromethyl)benzamide (4)

To a stirred solution of compound (3) (60 g, 198 mmol) and Int-B (67.62 g,198 mmol) in chlorobenzene (180 ml), tin(II) chloride (4.92 g, 25.7 mmol) was added at room temperature. The reaction mixture was stirred at 140-150° C. for 16 h. Reaction progress was monitored by TLC. After completion of reaction, the reaction mixture was quenched with water (100 ml) and filtered through celite bed, and the bed was washed with DCM (200 mL). Layers were separated and further extracted with DCM (1×100 mL). Organic layer was dried over anhydrous sodium sulfate and concentrated under reduced pressure. The obtained crude was purified by column chromatography by eluting with 20-30% ethyl acetate in pet ether to afford compound (4) (40 g, 32%) as pale brown solid.

$^1$H NMR (400 MHZ, DMSO-d$_6$) δ=11.0 (s, 1H), 8.48 (d, J=7.2 Hz, 1H), 8.15-8.13 (m, 2H), 7.97 (d, J=8.0 Hz, 1H), 7.78-7.69 (m, 3H), 7.62-7.58 (m, 2H), 7.49-7.46 (m, 1H), 7.14 (t, J=8.8 Hz, 2H), 7.04-7.01 (m, 2H), 5.38 (t, J=6.8 Hz, 1H), 4.76 (d, J=7.2 Hz, 1H), 4.67 (d, J=12.4 Hz, 1H), 4.51 (d, J=12.4 Hz, 1H), 0.74 (s, 9H), 0.01 (s, 6H). LC-MS (Method-B)=639.0 [M+H]$^+$; 96.89% at RT 2.78 min.

Step-5: Synthesis of rac-N-((4R,5R)-3-(((tert-butyldimethylsilyl)oxy)methyl)-7-ethyl-4-(4-fluorophenyl)-6-oxo-1-phenyl-4,5,6,7-tetrahydro-1H-pyrazolo[3,4-b]pyridine-5-yl)-3-(trifluoromethyl) benzamide (5)

To a stirred solution of compound (4) (60 g, 82.66 mmol) in DMF (600 mL), potassium carbonate (15.0 g, 107.45 mmol) and bromoethane (10.9 g, 99.2 mmol) were added at room temperature. The reaction mixture was stirred at room temperature for 16 h. Reaction progress was monitored by TLC. After completion of reaction, the reaction mixture was quenched with water and extracted with ethyl acetate. Organic layer was dried over anhydrous sodium sulfate and evaporated under vacuum. The obtained crude was purified by column chromatography by eluting with 15-20% ethyl acetate in heptane to afford compound (5) (40 g, 65%) as yellow solid.

$^1$H NMR (400 MHZ, CDCL3) δ=8.06 (s, 1H), 7.89 (d, J=8.0 Hz, 1H), 7.79 (d, J=8.0 Hz, 1H), 7.60-7.48 (m, 6H), 6.98-6.90 (m, 5H), 5.26-5.23 (m, 1H), 4.94 (d, J=7.2 Hz, 1H), 4.72 (d, J=12.4 Hz, 1H), 4.61 (d, J=12.4 Hz, 1H), 3.99-3.94 (m, 1H), 3.22-3.17 (m, 1H), 1.03-0.88 (m, 3H), 0.74 (s, 9H), 0.06 (s, 6H). LC-MS (Method-A)=667.53 [M+H]$^+$; 98% at RT 2.65 min.

Step-6: Synthesis of rac-N-((4R,5R)-7-ethyl-4-(4-fluorophenyl)-3-(hydroxymethyl)-6-oxo-1-phenyl-4,5,6,7-tetrahydro-1H-pyrazolo[3,4-b]pyridine-5-yl)-3-(trifluoromethyl)benzamide (24-1)

To a stirred solution of compound (5) (80 g, 120 mmol) in acetonitrile (800 mL), hydrochloric acid (80 mL, 6M) was added. The reaction mixture was stirred at room temperature for 16 h. Reaction progress was monitored by TLC. After completion of reaction, the reaction mixture was quenched with ice water and extracted with ethyl acetate. Organic layer was dried over anhydrous sodium sulfate and concentrated under vacuum to afford crude compound. The crude material was washed with 10% diethyl ether in pentane and dried under vacuum to afford 24-1 (56 g, 85%) as a pale-yellow solid. The pure compound was submitted to Chiral SFC purification to separate isomers, 24-2-Peak-2 (23.02 g) and 24-3-Peak-1 (23.94 g).

Peak-1: rel-N-((4R,5R)-7-ethyl-4-(4-fluorophenyl)-3-(hydroxymethyl)-6-oxo-1-phenyl-4,5,6,7-tetrahydro-1H-pyrazolo[3,4-b]pyridine-5-yl)-3-(trifluoromethyl)benzamide. (24-3).

$^1$H NMR (400 MHZ, DMSO-d$_6$) δ=8.52 (d, J=7.2 Hz, 1H), 8.15-8.12 (m, 2H), 7.92 (d, J=7.6 Hz, 1H), 7.73-7.65 (m, 3H), 7.60-7.52 (m, 3H), 7.09 (t, J=8.8 Hz, 2H), 7.00-6.96 (m, 2H), 5.52 (t, J=7.2 Hz, 1H), 5.11 (t, J=5.6 Hz, 1H), 4.72 (d, J=7.2 Hz, 1H), 4.40-4.35 (m, 1H), 4.29-4.24 (m, 1H), 3.94-3.88 (m, 1H), 3.05-3.00 (m, 1H), 0.90 (t, J=7.2 Hz, 3H). LC-MS (Method-A)=553.1 [M+H]$^+$; 96.60% at RT 5.72 min. HPLC (Method-A)=96.71% at RT 5.80 min. HPLC (Chiral)=98.20% at RT 5.07 min.

SOR: $[\alpha]_D^{25}$ 198.08 (c 0.05% in DCM)

Peak-2: rel-N-((4R,5R)-7-ethyl-4-(4-fluorophenyl)-3-(hydroxymethyl)-6-oxo-1-phenyl-4,5,6,7-tetrahydro-1H-pyrazolo[3,4-b]pyridine-5-yl)-3-(trifluoromethyl)benzamide. (24-2).

$^1$H NMR (400 MHZ, DMSO-d$_6$) δ=8.52 (d, J=7.2 Hz, 1H), 8.15-8.12 (m, 2H), 7.92 (d, J=7.6 Hz, 1H), 7.73-7.65 (m, 3H), 7.60-7.50 (m, 3H), 7.09 (t, J=8.8 Hz, 2H), 7.00-6.97 (m, 2H), 5.50 (t, J=7.2 Hz, 1H), 5.11 (s, 1H), 4.72 (d, J=7.2 Hz, 1H), 4.39-4.36 (m, 1H), 4.28-4.25 (m, 1H), 3.94-3.88 (m, 1H), 3.05-3.00 (m, 1H), 0.90 (t, J=6.8 Hz, 3H). LC-MS (Method-A)=553.1 [M−H]$^+$; 96.80% at RT 5.72 min. HPLC (Method-A)=97.11% at RT 5.80 min. HPLC (Chiral)=98.84% at RT 6.56 min.

SOR:

$[\alpha]_D^{25}$--211.440 (c 0.05% in DCM)

Synthesis of Int. B

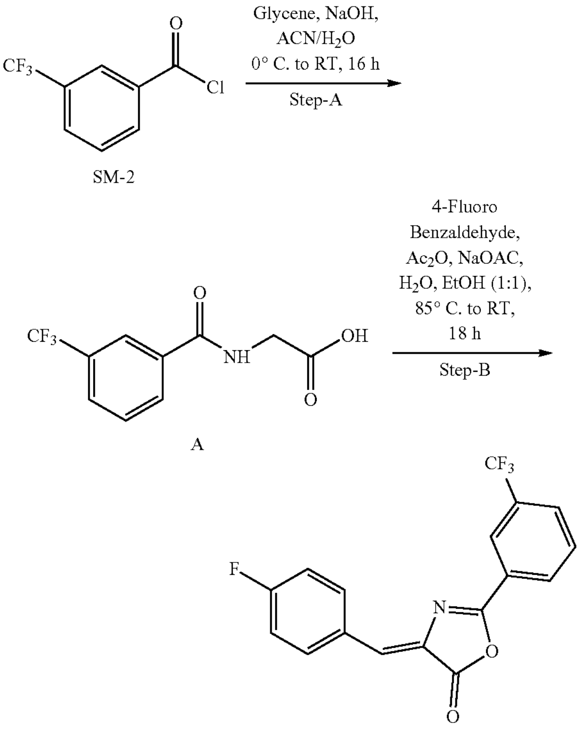

SM-2

A

B

Step-A: Synthesis of (3-(trifluoromethyl)benzoyl)glycine (A)

A stirred solution of glycine (359.89 g, 4794.78 mmol) in I (6 L) was added to a NaOH (479.35 g, 11986.95 mmol in 1.2 L of water) solution at 0° C. and stirred for 5 min followed by 3-(trifluoromethyl)benzoyl chloride (SM-2)

(1000 g, 4794.78 mmol) in I (2 L) which was added dropwise at 0° C. The reaction mixture was stirred at room temperature for 16 h. After consumption of the starting material (by TLC), the reaction mixture was diluted with water and acidified with HCl, and pH was adjusted to 1-3 and extracted with EtOAc (2x10 L). The combined organic layer was washed with brine solution (5 L), dried over anhydrous $Na_2SO_4$, filtered, and concentrated under reduced pressure to afford crude compound. Crude compound was triturated with n-heptane to get pure Compound-B (1000 g, 84.38%) as a yellow solid.

$^1$H NMR (400 MHZ, DMSO-$d_6$) δ=9.13-9.05 (m, 1H), 8.27-8.13 (m, 2H), 7.93 (d, J=7.5 Hz, 1H), 7.74 (t, J=7.7 Hz, 1H), 3.94 (d, J=5.8 Hz, 2H). LC-MS (Method-A)=248.12 $[M+H]^+$; 98.23% at RT 1.14 min.

Step-B: Synthesis of (Z)-4-(4-fluorobenzylidene)-2-(3-(trifluoromethyl)phenyl)oxazol-5(4H)-one (B)

To a stirred solution of (A) (1000 g, 4045.8 mmol) in acetic anhydride (1250 g, 12137 mmol) was added 4-Fluoro Benzaldehyde (502.12 g, 4045.8 mmol) and allowed to stir for 10 to 15 min. To this mixture, NaOAc (335 g, 4045.8 mmol) was added at room temperature. The reaction mixture was heated at 80° C.-85° C. for 14 h. Reaction was monitored by TLC. After completion of reaction, the reaction mass was cooled to room temperature, added ethanol (500 mL) and water (500 mL), and the mass was stirred for 3-4 hr. The reaction mixture was filtered, washed with heptane (100 mL), and dried for 1 h. Obtained compound was azeotroped with toluene (1 L) and filtered with heptane (3 L) to afford compound (B) (800 g, 60%) as a pale yellow solid.

$^1$H NMR (400 MHZ, DMSO-$d_6$) δ=8.46-8.38 (m, 2H), 8.33 (s, 1H), 8.11 (d, J=7.6 Hz, 1H), 7.90 (t, J=7.8 Hz, 1H), 7.50-7.33 (m, 4H). LC-MS (Method-A)=336.1 $[M+H]^+$; 80.55% at RT 1.56 min.

NMR:

$^1$H NMR spectrum was recorded on Bruker 400 MHz and Varian 400 MHz instruments internally referenced to a tetramethyl silane (TMS) signal. Chemical shifts (δ) and coupling constants (J) were expressed in parts per million and hertz, respectively.

LCMS:

Method-A: Column: CORTECS UPLC C18 (3x30 mm Instrument ID:-AMC-LCMS-17 Mobile Phase A: 0.05% FA in water; B: 0.05% FA in CAN Flow: 0.85 ml/min T/B %: 0/3,0.1/3,1.4/97,2.0/97,2.05/3,2.5/3.

Method-B: Column: BAKERBOND Q2100 C18 (2.1x50 mm Instrument ID:-AMC-LCMS-16 Mobile Phase A: 0.05% FA in Water Column Temperature: 45.0° C.; Mobile phase B: 0.05% FA in CAN; Flow: 0.6 ml/min; Gradient B %: 0.0/2_0.3/2_2.0/98_2.8/98_3.0/2_3.7/2.

Method-C: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C.; Gradient program: 0% B to 98% B in 2.0 minute, hold till 3.0 min, at 3.2 min B conc is 0% up to 4.0 min.

Method-D: Column: X-Bridge BEH C18, (50 mm*3.0 mm,2.5μ) Mobile Phase A: 2.5 mM Ammonium Bicarbonate in Water+5% CAN; Mobile Phase B: 100% CAN; Flow rate: 1.0 mL/min. Column temperature: 40° C. Gradient Program (B %): 0.0/2, 0.3/2, 2.0/98, 2.8/98, 3.0/2,3.7/2.

HPLC:

Method-A: Column: X Select CSH C18 (150x4.6) mm,3.5μ; Mobile phase A: 0.1% FA in water: I (95:05); Mobile phase B: Acetonitrile; Gradient Programme: T/B %: 0.01/5, 1/5,8/100,12/100, 14/5, 18/5; Flow rate: 1.2 ml/min.

Method-B: Column: X-SELECT CSH C18 (150x4.6 mm, 3.5 μm); Mobile Phase-A: 5 mM $NH_4HCO_3$; Mobile Phase-B: I; Programme: T/B %: 0.01/2,2/2, 12/90, 16/90; Flow: 1.0 mL/min.; Diluent: I:Water (80:20).

Method-C: Column: X SELECT CSH C18 (150x4.6 mm, 3.5μ); Mobile Phase A; 0.05% TFA in water: I (95:05); Mobile Phase B: 0.05% TFA in water: I (05:95); Programme: T/B %: . 0.01/10,12/90, 16/90; Flow: 1 mL/min.; Diluent: water: I (80:20).

Chiral HPLC:

Method-A: Column: CHIRALCEL-OJ-H (250x4.6 mm, 5μ) Mobile Phase A: 0.1% DEA in Hexane; Mobile Phase B: IPA A/B: 60/40 Flow: 1.0 ml/MIN PDA: OJ-H_015

Method-B: Column: CHIRALPAK IG (250x4.6 mm, 5 μm) Mobile Phase A: n-Hexane; Mobile Phase B: DCM: IPA (1:1) A B: 60:40 Flow rate: 1.0 ML/MIN Method-C: Column: CHIRALPAK-IA (250x4.6 mm, 5 μm) A B: 70/30 MobilePhase A: n-Hexane MobilePhase B: EtOH: MeOH (1:1) Flow rate: 1.00 ml/min Synthesis of I-82 and I-133

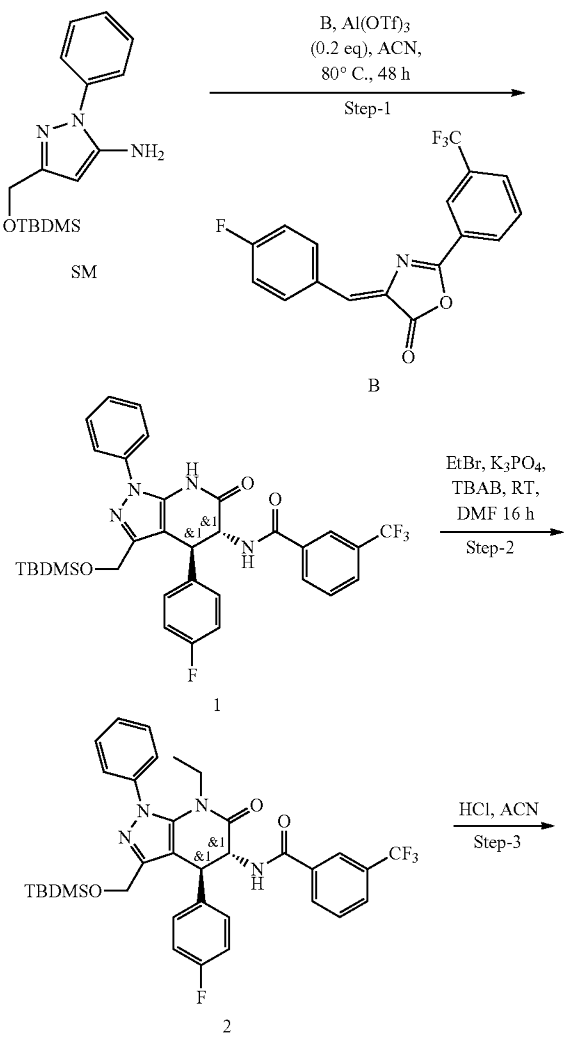

SM B 1 2

-continued

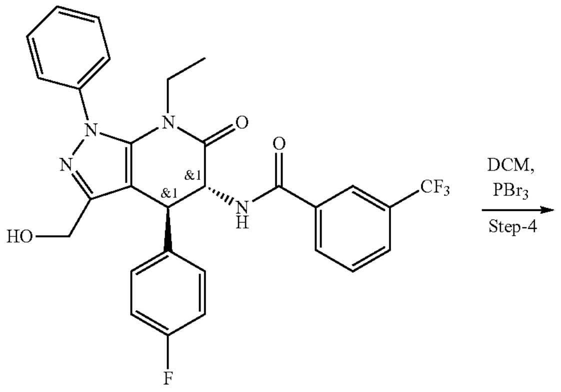

3

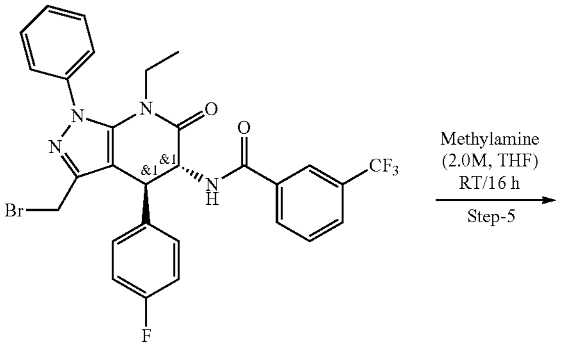

4

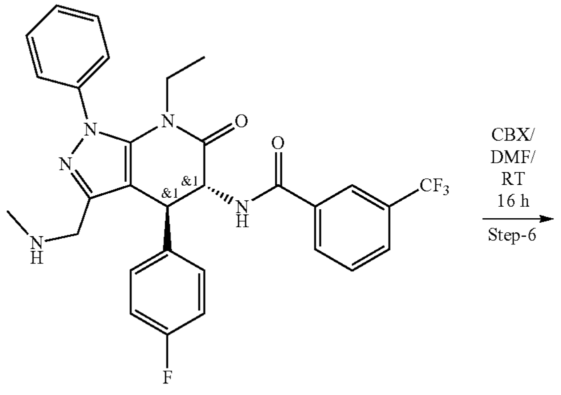

5

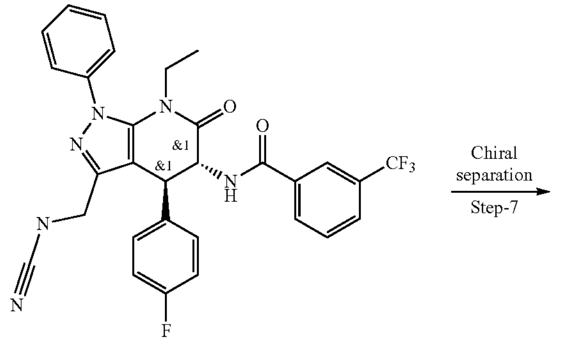

6

-continued

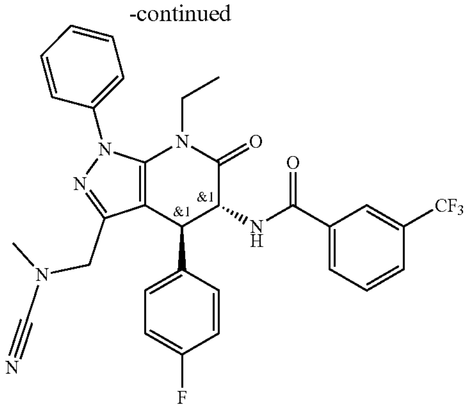

I-82

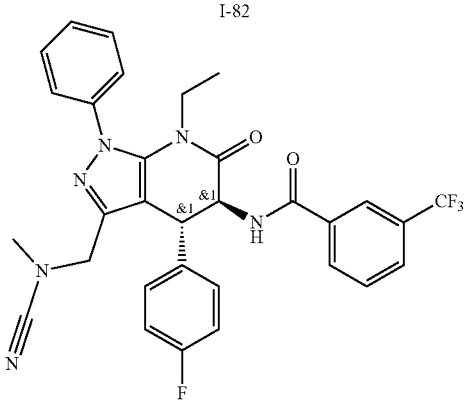

I-133

Step-1: Synthesis of ~{N}-[(4~{S},5~{R})-3-[[~{tert}-butyl(dimethyl)silyl]oxymethyl]-4-(4-fluorophenyl)-6-oxo-1-phenyl-5,7-dihydro-4~{H}-pyrazolo[3,4-b]pyridine-5-yl]-3-(trifluoromethyl) benzamide compound (1)

To a stirred solution compound (SM) (10.0 g, 29.83 mmol) and Int-B (11.85 g, 38.78 mmol) in acetonitrile (100 ml), was added aluminum trifluoromethanesulfonate (2.85 g, 5.96 mmol) at room temperature. The reaction mixture was stirred at 90° C. for 16 h. Reaction progress was monitored by TLC. After completion of reaction, the reaction mixture was quenched with water and extracted with ethyl acetate. The organic layer was dried over anhydrous sodium sulfate and evaporated under vacuum. The obtained crude was purified by column chromatography 230-400 mesh silica gel by eluting with 50% ethyl acetate in heptane to afford compound (1) (5.0 g, 26%) as a brown solid.

$^1$H NMR (400 MHZ, DMSO-$d_6$) δ=10.9 (s, 1H), 8.99 (d, J=8.4 Hz, 1H), 8.04 (s, 2H), 7.89 (d, J=7.3 Hz, 1H), 7.89 (d, J=7.3 Hz, 1H), 7.61-7.51 (m, 4H), 7.40-7.36 (m, 3H), 7.13 (d, J=8.8 Hz, 2H), 5.50 (t, J=7.3 Hz, 1H), 4.43 (d, J=10.8 Hz, 1H), 4.15 (d, J=12.4 Hz, 1H), 3.84 (d, J=11.6 Hz, 1H), 0.75 (s, 9H), 0.15 (s, 6H). LC-MS (Method-A)=639.4 [M+H]$^+$; 98.12% at RT 1.91 min.

Step-2: Synthesis of ~{N}-[(4~{S},5~{R})-3-[[~{tert}-butyl(dimethyl)silyl]oxymethyl]-7-ethyl-4-(4-fluorophenyl)-6-oxo-1-phenyl-4,5-dihydropyrazolo[3,4-b]pyridine-5-yl]-3-(trifluoromethyl) benzamide compound (2)

To a stirred solution of compound (1) (5 g, 7.8 mmol) in I (40 mL), was added potassium phosphate tribasic (3.4 g, 16 mmol) and tetrabutylammonium bromide (5.2 g, 16 mmol) and bromoethane (1.7 g, 16 mmol) at 0° C. The reaction mixture was stirred at room temperature for 16 h. Reaction progress was monitored by TLC. After completion of reaction, the reaction mixture was quenched with water and extracted with ethyl acetate. Organic layer was dried over anhydrous sodium sulfate and evaporated under vacuum. The obtained crude was purified by column chromatography 100-200 mesh silica gel by eluting with 15-20% ethyl acetate in heptane to afford compound (2) (2.30 g, 44%) as pale yellow solid.

$^1$H NMR (400 MHZ, DMSO-d6): δ=9.03 (d, J=8.8 Hz, 1H), 8.02 (s, 2H), 7.91 (d, J=7.1 Hz, 1H), 7.73-7.67 (m, 3H), 7.65-7.50 (m, 4H), 7.40-7.37 (m, 2H), 7.16-7.12 (m, 2H), 5.16 (t, J=10.4 Hz, 1H), 5.40 (d, J=10.8 Hz, 1H), 3.84 (d, J=12.4 Hz, 1H), 3.69-3.65 (m, 1H), 3.22-3.17 (m, 1H), 0.74 (s, 12H), 0.15 (s, 6H). LC-MS (Method-A)=667.35 $[M+H]^+$; 93.26% at RT 1.97 min.

Step-3: Synthesis of ~{N}-[(4~{S},5~{R})-7-ethyl-4-(4-fluorophenyl)-3-(hydroxymethyl)-6-oxo-1-phenyl-4,5-dihydropyrazolo[3,4-b]pyridine-5-yl]-3-(trifluoromethyl)benzamide compound (3)

To a stirred solution of compound (2) (2.3 g, 3.4 mmol) in acetonitrile (20 mL), was added hydrochloric acid (12 mL, 3.4 mmol) at 25° C. The reaction mixture was stirred at room temperature for 16 h. Reaction progress was monitored by TLC. After completion of reaction, the reaction mixture was concentrated under vacuum to afford crude compound. The crude material was washed with pentane and dried under vacuum to afford (2.3 g, 83.75%) as a pale-yellow solid.

$^1$H NMR (400 MHZ, DMSO-d6): δ=9.04 (d, J=8.8 Hz, 1H), 8.02 (s, 2H), 7.90 (d, J=8.0 Hz, 1H), 7.72-7.64 (m, 4H), 7.60-7.49 (m, 4H), 7.42-7.39 (m, 2H), 7.15-7.11 (m, 2H), 5.24-5.18 (m, 1H), 4.42 (d, J=12.0 Hz, 1H), 3.86 (d, J=12.0 Hz, 1H), 3.74-3.69 (m, 1H), 3.53 (d, J=12.4 Hz, 1H), 3.17-3.11 (m, 1H), 0.81 (t, J=6.8 Hz, 3H).

LC-MS (Method-B)=553.8 $[M+H]^+$; 84.91% at RT 2.28 min.

Step-4: Synthesis of ~{N}-[(4~{S},5~{R})-3-(bromomethyl)-7-ethyl-4-(4-fluorophenyl)-6-oxo-1-phenyl-4,5-dihydropyrazolo[3,4-b]pyridine-5-yl]-3-(trifluoromethyl)benzamide compound (4)

To a stirred solution of compound (3) (1.0 g, 1.810 mmol) in DCM (10 mL) was added phosphorus tribromide (0.74 g, 2.715 mmol) at 0° C. The reaction mixture was stirred at room temperature for 2 h. After consumption of starting material (by TLC), the reaction mixture was quenched with aq. $NaHCO_3$ and extracted with DCM. The organic layer was dried over anhydrous $Na_2SO_4$ and concentrated under reduced pressure. The obtained crude material was purified by column chromatography 100-200 mesh silica gel by eluting with 30-40% ethyl acetate in heptane to afford compound (4) (0.38 g, 34%) as an off-white solid.

$^1$H NMR (400 MHz, DMSO-$d_6$) δ=8.99 (d, J=8.8 Hz, 1H), 8.01 (s, 2H), 7.90 (d, J=7.2 Hz, 1H), 7.72-7.67 (m, 3H), 7.61-7.47 (m, 5H), 7.21-7.17 (m, 2H), 5.33-5.28 (m, 1H), 4.42 (d, J=12.4 Hz, 1H), 4.09 (d, J=10.8 Hz, 1H), 3.72-3.67 (m, 1H), 3.47 (d, J=10.8 Hz, 1H), 3.30-3.11 (m, 1H), 0.81 (t, J=6.8 Hz, 3H). LC-MS (Method-A)=617.25 $[M+H]^+$; 95.27% at RT 1.70 min.

Step-5: Synthesis of ~{N}-[(4~{S},5~{R})-7-ethyl-4-(4-fluorophenyl)-3-(methylaminomethyl)-6-oxo-1-phenyl-4,5-dihydropyrazolo[3,4-b]pyridine-5-yl]-3-(trifluoromethyl)benzamide compound (5)

A solution of compound (4) (0.91 g, 1.5 mmol) in methylamine (2.0 mol/L) was stirred in THF (7.4 mL, 15 mmol) at 0° C. The reaction mixture was stirred at room temperature for 16 h. Reaction progress was monitored by TLC. After completion of reaction the reaction mixture was diluted with water and extracted with EtOAc which was concentrated under reduced pressure to afford crude. The obtained crude material was washed with diethyl ether to afford compound (5) (700 mg, 80%) as off white solid.

$^1$H NMR (400 MHZ, DMSO-$d_6$) δ=9.90 (d, J=8.8 Hz, 1H), 8.01 (s, 2H), 7.90 (d, J=7.6 Hz, 1H), 7.72-7.43 (m, 8H), 7.18-7.14 (m, 2H), 5.75 (s, 1H), 5.24 (d, J=11.6 Hz, 1H), 4.42 (d, J=12.0 Hz, 1H), 3.76-3.73 (m, 1H), 3.31-3.10 (m, 1H), 2.98 (d, J=13.2 Hz, 1H), 2.66-2.50 (m, 1H), 1.98 (s, 3H), 0.80 (t, J=6.8 Hz, 3H). LC-MS (Method-A)=566.4 $[M+H]^+$; 95.36% at RT 1.28 min.

Step-6&7: Synthesis of N-((4S,5R)-7-ethyl-4-(4-fluorophenyl)-3-((N-methylcyanamido)methyl)-6-oxo-1-phenyl-4,5,6,7-tetrahydro-1H-pyrazolo[3,4-b]pyridin-5-yl)-3-(trifluoromethyl)benzamide I-82 and N-((4R,5S)-7-ethyl-4-(4-fluorophenyl)-3-((N-methylcyanamido)methyl)-6-oxo-1-phenyl-4,5,6,7-tetrahydro-1H-pyrazolo[3,4-b]pyridin-5-yl)-3-(trifluoromethyl)benzamide I-133

To a stirred solution of compound (5) (300.0 mg, 0.5 mmol) in DMF (3 mL) was added 1,2-benziodoxole-1 (3 h)-carbonitrile, 3-oxo-(200 mg 0.6 mmol) at 25° C. and stirred the reaction at room temperature for 16 h. Progress of the reaction was monitored by TLC and LC-MS. After completion of reaction, the reaction mixture was quenched with ice cold water and extracted with ethyl acetate. The combined organic layer was dried over anhydrous $Na_2SO_4$ and concentrated to afford crude compound. Obtained crude compound was purified by silica gel (100-200) column chromatography using ethyl acetate in heptane. Product was eluted in 50-60% ethyl acetate in heptane, as off white solid. The obtained solid was dissolved in 1 mL of DCM and washed with pentane and submitted to chiral separation. After evaporation, fractions were lyophilized to afford I-82 (70.41 mg 73.0%) and I-133 (53.68 mg 56.0%) as a white solid compound.

I-82

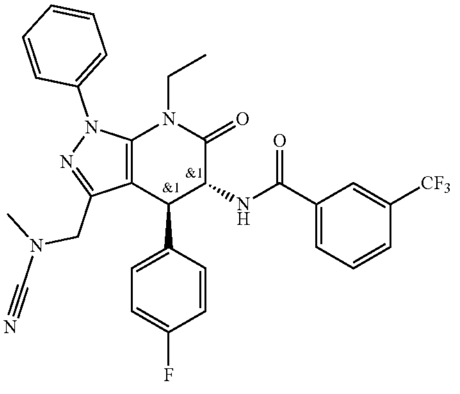

$^1H$ NMR (400 MHZ, $CDCl_3$) δ=7.89 (s, 1H), 7.80 (d, J=8.0 Hz, 1H), 7.73 (d, J=8.0 Hz, 1H), 7.55-7.44 (m, 8H), 7.12-7.07 (m, 2H), 6.57 (d, J=8.8 Hz, 1H), 5.45 (dd, J=12.8 Hz, J=8.8 Hz, 1H), 4.29 (d, J=12.8 Hz, 1H), 3.87-3.82 (m, 1H), 3.62 (d, J=13.6 Hz, 1H), 3.26-3.21 (m, 1H), 3.17-3.14 (m, 1H), 2.60 (m, 3H), 0.92 (t, J=6.8 Hz, 3H). LC-MS (Method-B)=591.24 $[M+H]^+$; 98.05% at RT 2.05 min. HPLC (Method-B)=98.58% at RT 8.43 min. Chiral HPLC (Method-B)=Peak-1=100% at RT 6.81 min.

I-133

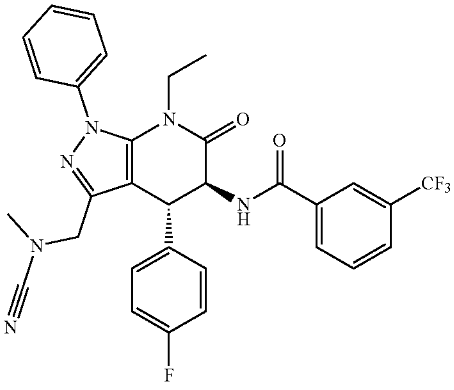

$^1H$ NMR (400 MHZ, $CDCl_3$) δ=7.89 (s, 1H), 7.80 (d, J=8.0 Hz, 1H), 7.73 (d, J=8.0 Hz, 1H), 7.55-7.44 (m, 8H), 7.12-7.07 (m, 2H), 6.57 (d, J=8.8 Hz, 1H), 5.45 (dd, J=12.8 Hz, J=8.8 Hz, 1H), 4.29 (d, J=12.8 Hz, 1H), 3.87-3.82 (m, 1H), 3.62 (d, J=13.6 Hz, 1H), 3.26-3.21 (m, 1H), 3.17-3.14 (m, 1H), 2.60 (m, 3H), 0.92 (t, J=6.8 Hz, 3H). LC-MS (Method-B)=591.24 $[M+H]^+$; 99.46% at RT 2.04 min. HPLC (Method-B)=99.42% at RT 8.42 min. Chiral HPLC (Method-B)=Peak-1=98.04% at RT 8.13 min.

Example 25: Synthesis of Compounds I-222 and I-68

NMR:

$^1H$ NMR spectrum was recorded on Bruker 400 MHz and Varian 400 MHZ instruments internally referenced to a tetramethylsilane (TMS) signal. Chemical shifts (δ) and coupling constants (J) were expressed in parts per million and hertz, respectively.

LCMS:

Method-A: LCMS_X-Select (Formic acid); Column: X-Select CSH C18 (3.0*50) mm 2.5μ. Mobile Phase: A: 0.05% Formic acid in water: I (95:5); B: 0.05% Formic acid in I. Inj Volume: 2.0 μL, Column oven temperature: 50° C.; Flow Rate: 1.2 mL/min. Gradient program: 0% B to 98% B in 2.0 minute, hold till 3.0 min, at 3.2 min B conc is 0% up to 4.0 min.

Method-B: Column: X-Bridge BEH $C_{18}$, (50 mm*3.0 mm,2.5μ) Mobile Phase A: 2.5 mM Ammonium Bicarbonate in Water+5% CAN; Mobile Phase B: 100% I Flow rate: 1.0 mL/min. Column temperature: 40° C. Gradient Program (B %): 0.0/2, 0.3/2, 2.0/98, 2.8/98, 3.0/2,3.7/2.

Method-C: Column: X-Select CSH C18 (50 mm*3.0 mm,2.5μ) Mobile Phase A: 0.05% TFA in Water; Mobile Phase B: 0.05% TFA in Acetonitrile Flow rate: 1.0 mL/min. Column temperature: 40° C. Gradient Program (B %): 0.0/2, 0.3/2,2.0/98, 2.8/98, 3.0/2,3.7/2.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5, 1/5,8/100, 12/100,14/5, 18/5; Flow rate: 1.2 mL/min.

Method-B: Column: X-Bridge CSH C18 (150×4.6 mm, 3.5 μm); Mobile Phase-A: 5 mM $NH_4HCO_3$ in water; Mobile Phase-B: I; Programme/B %: 0.01/2,2/2,12/90, 16/90; Flow: 1.0 mL/min.; Diluent: I:Water (80:20).

Method-C: Column: X SELECT CSH C18 (150×4.6 mm, 3.5μ); Mobile Phase A; 0.05% TFA in water: I (95:05); Mobile Phase B: 0.05% TFA in water: I (05:95); Programme: T/B %: . 0.01/10,12/90,16/90; Flow: 1 mL/min.; Diluent: WATER: I (80:20).

Method-D: Column: X-Bridge CSH C18 (4.6*150) mm 5μ Mobile Phase: A-0.1% TFA in water; B-Acetonitrile Inj Volume; 5.0 μL, Flow Rate: 1.2. mL/minute; Gradient program: Time (min)/B Conc.: 0.01/5, 1.0/5, 8.0/100, 12.0/100, 14.0/5, 18.0/5.

Method-E: Column: CHIRALCEL-OJ-H (250×4.6 mm, 5μ) Mobile Phase A: 0.1% DEA in Hexane; Mobile Phase B: IPA A/B: 60/40; Flow: 1.0 ml/MIN PDA: OJ-H_015

Method-F: Column Name: CHIRALPAK-IK (250×4.6 mm, 5 μm) Mobilephase-A: n-Hexane; Mobile phase-B: EtOH/MeOH (50/50); Flow rate: 1.0 mL/min; % A/B: 50/50.

Method-G: Column: X-Select CHS C18 (4.6*150) mm 5μ Mobile Phase: A-5 mM Ammonium acetate; B-Acetonitrile; Inj Volume; 5.0 μL, Flow Rate: 1.0 mL/minute.

Synthesis of 25-2

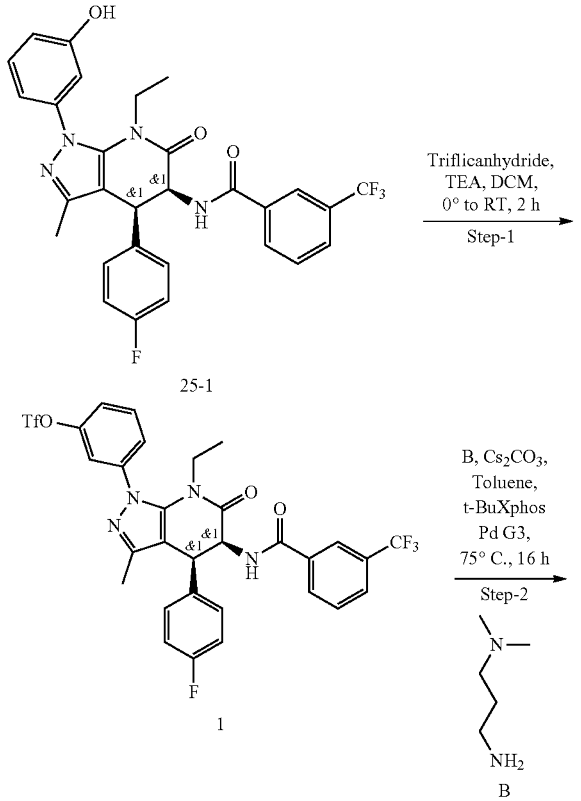

-continued

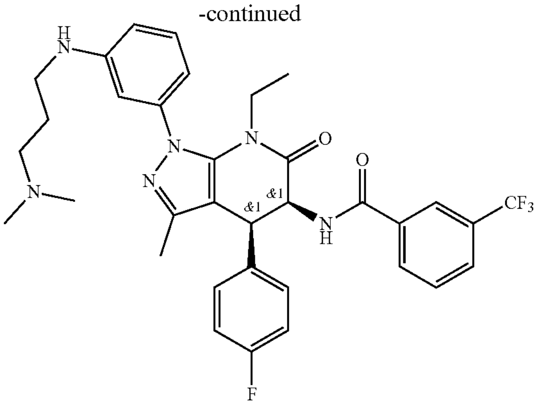

25-2

Step 1: Synthesis of [3-[rac-(4S,5S)-7-ethyl-4-(4-fluorophenyl)-3-methyl-6-oxo-5-[[3-(trifluoromethyl)benzoyl]amino]-4,5-dihydropyrazolo[3,4-b]pyridine-1-yl]phenyl]trifluoromethanesulfonate (1)

To a stirred solution of 25-1 (0.1 g, 0.181 mmol) in DCM (2 mL) were added triethylamine (0.036 g, 0.362 mmol) and trifluoromethanesulfonic anhydride (0.0619 g, 0.217 mmol) at 0° C. under inert atmosphere. The reaction mixture was stirred at 25° C. for 2 h. Progress of the reaction was monitored by TLC. After consumption of the starting material (monitored by TLC), the reaction mixture was quenched with ice cold water (5 mL) and extracted with DCM (2×5 mL). The combined organic layer was dried over anhydrous $Na_2SO_4$ and concentrated under reduced pressure to afford crude compound. The crude compound was purified by flash column chromatography and compound was eluted in 20% EtOAc in heptane to afford 1 (0.1 g, 80%) as off white solid.

$^1$HNMR (400 MHZ, DMSO-$d_6$) δ=8.59 (d, J=6.8 Hz, 1H), 8.16 (d, J=11.6 Hz, 2H), 7.97-7.65 (m, 6H), 7.13 (t, J=8.4 Hz, 2H), 7.02 (d, J=5.2 Hz, 2H), 5.56 (t, J=6.8 Hz, 1H), 4.51 (d, J=6.8 Hz, 1H), 3.99-3.96 (m, 1H), 3.03-2.98 (m, 1H), 2.05 (s, 3H), 0.94 (t, J=6.4 Hz, 3H). LC-MS (Method-B)=685.0 $[M+H]^+$; 56.75% at RT 2.63 min.

Step 2: Synthesis of N-[rac-(4S,5S)-1-[3-[3-(dimethylamino)propylamino]phenyl]-7-ethyl-4-(4-fluorophenyl)-3-methyl-6-oxo-4,5-dihydropyrazolo[3,4-b]pyridine-5-yl]-3-(trifluoromethyl)benzamide (25-2)

To a stirred solution of 1 (0.2 g, 0.292 mmol) in 1,4-dioxane (1.46 mL) were added cesium carbonate (0.115 g, 0.350 mmol) and ~{N}',~{N}'-dimethylpropane-1,3-diamine (0.0358 g, 0.350 mmol) under argon atmosphere. To this solution was added tBuXPhos-Pd-G3 (0.0118 g, 0.0146 mmol) under nitrogen atmosphere at 25° C. The reaction mixture was stirred at 75° C. for 16 h. Progress of the reaction was monitored by LCMS and TLC. After consumption of the starting material (monitored by TLC), the reaction mixture was quenched with ice cold water (10 mL) and extracted with DCM (2×10 mL). The combined organic layer was dried over anhydrous $Na_2SO_4$ and concentrated under reduced pressure to afford the crude compound. The crude material was purified by prep-HPLC, product containing fractions were collected and evaporated to afford pure 25-2 (0.030 g, 15%) as an off-white solid.

$^1$HNMR (400 MHZ, DMSO-$d_6$) δ=9.24 (s, 1H), 8.55 (d, J=7.2 Hz, 1H), 8.14-8.11 (m, 2H), 7.92 (d, J=7.6 Hz, 1H), 7.71 (t, J=7.6 Hz, 1H), 7.24 (t, J=8.4 Hz, 1H), 7.15-7.09 (m, 2H), 7.03-6.97 (m, 2H), 6.77-6.76 (m, 2H), 6.70-6.68 (m, 1H), 6.06 (s, 1H), 5.47 (t, J=7.2 Hz, 1H), 4.50 (d, J=7.2 Hz, 1H), 3.94-3.89 (m, 1H), 3.33 (s, 6H), 3.16-3.14 (m, 4H), 2.78 (bs, 4H), 2.02 (s, 3H), 1.91-1.97 (m, 1H), 0.96 (t, J=7.2 Hz, 3H). LC-MS (Method-C)=637.3 $[M+H]^+$; 95.556% at RT 5.221 min. HPLC (Method-A)=95.40% at RT 4.581 min. HPLC (Method-E)=56.45% at RT 3.739 min, 41.96% at RT 5.256 min.

Synthesis of I-222

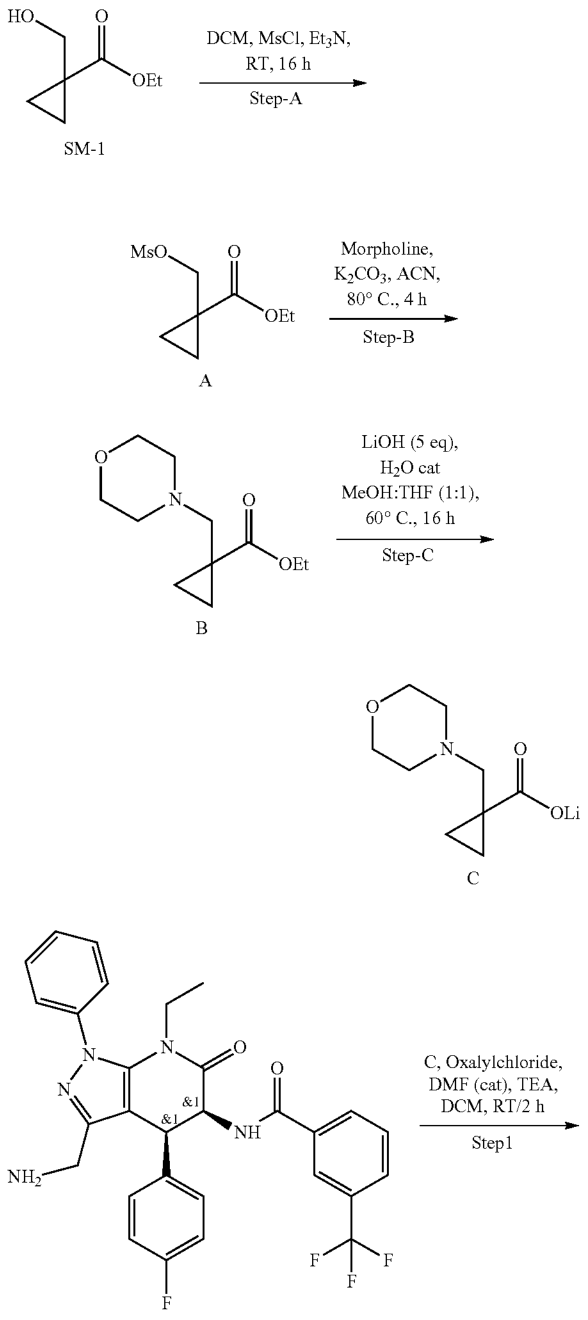

25-3

-continued

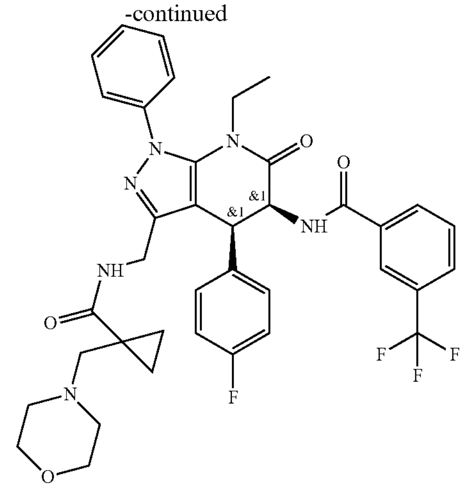

I-222

Step-A: Synthesis of ethyl 1-(((methylsulfonyl)oxy) methyl)cyclopropane-1-carboxylate (A)

To stirred solution of SM-1 (2 g, 13.873 mmol) and MsCl (1.62 g, 13.873 mmol) in dichloromethane (80 mL) was added triethylamine (1.55 g, 15.260 mmol) at 0° C. and the reaction mixture was allowed to stir at RT for 16 h. Progress of the reaction was monitored by TLC. After completion of the reaction, reaction mixture was diluted with ice cold water (1×10 mL), washed saturated $Na_2CO_3$ (25 mL) and saturated with brine (25 mL). The organic layer was dried over $Na_2SO_4$ and evaporated to afford A (3 g, 13.498 mmol, 97.298% Yield) as a pale-yellow oil which was used for next step without purification.

$^1$HNMR (400 MHZ, $CDCl_3$): δ=4.31 (s, 2H), 4.17-4.11 (q, 4H), 3.05 (s, 3H), 1.42-1.396 (q, 2H), 1.25-1.24 (t, 4H), 1.04-1.01 (q, 2H).

Step-B: Synthesis of ethyl 1-(morpholinomethyl)cyclopropane-1-carboxylate (B)

To stirring solution of A (3 g, 13.498 mmol) and potassium carbonate (2.07 g, 14.847 mmol) in acetonitrile (30 mL) was added morpholine (1.30 g, 14.847 mmol) at RT and the reaction mixture was allowed stir at 80° C. for 4 h. The progress of the reaction was monitored by TLC. After completion of the reaction, reaction mass was concentrated under reduced pressure and diluted with water and extracted with EtOAc, which was dried over $Na_2SO_4$ and concentrated to give crude B (2 g, 9.3778 mmol, 69.47% yield) as colorless oily liquid which was used for next step without purification.

$^1$HNMR (400 MHZ, DMSO-$d_6$): δ=4.06-4.01 (q, 2H), 3.53-3.51 (t, 4H), 2.54 (s, 2H), 2.37 (s, 4H), 1.17-1.15 (t, 4H), 1.074 (t, 2H), 0.82 (t, 2H).

Step-C: Synthesis of lithium 1-(morpholinomethyl)cyclopropane-1-carboxylate I

To a stirred solution ethyl $(B)_{500}$ mg, 2.3444 mmol) in the mixture of solvents THF (5 mL) and methanol (5 mL) (1:1) was added water (0.2 mL) followed by LiOH (0.28 g, 11.722 mmol) at rt and the reaction mixture was allowed to stir at 60° C. for 16 h. The progress of the reaction was monitored by TLC. After completion of the reaction (monitored by TLC), reaction mixture was dried over rotovap and co-distilled with toluene to get free salt of lithium 1-(morpholinomethyl)cyclopropane-1-carboxylate (400 mg, 2.15 mmol, 92.12% yield) as a pale yellow colored powder.

$^1$H NMR (400 MHZ, DMSO-$d_6$): δ=3.58 (s, 4H), 2.36 (s, 6H), 0.87 (s, 2H), 0.34 (s, 2H).

Step-1: Synthesis of N-[(4S,5S)-7-ethyl-4-(4-fluorophenyl)-3-[[[1-(morpholinomethyl)cyclopropanecarbonyl]amino]methyl]-6-oxo-1-phenyl-4,5-dihydropyrazolo[3,4-b]pyridine-5-yl]-3-(trifluoromethyl) benzamide (I-222)

To a stirred solution of I 1-(morpholinomethyl)cyclopropanecarboxylic acid (0.0839 g, 0.453 mmol) in DCM (3 mL) was added DMF (0.0033 g, 0.0453 mmol) followed by oxalyl chloride (0.0871 g, 0.680 mmol) at 0° C. under inert atmosphere. The reaction mixture was stirred at 0° C. for 1 h. After completion of reaction, the reaction mixture was concentrated carefully under reduced pressure and inert atmosphere, then the reaction mixture was diluted with DCM. (25-3) (0.25 g, 0.4533 mmol) and triethylamine (0.231 g, 2.267 mmol) drop wise at 0° C. were added to the solution under inert atmosphere. The reaction progress was monitored by TLC and LCMS. After completion of the reaction, the reaction mixture was quenched with cold water, then diluted and extracted with EtOAc. The obtained crude was submitted for prep purification to obtain I-222 (0.016 mg, 4.9%) as a white solid. (Preparative Column X-BRIDGE C18 (250*30 mm) 5μ, AMC-Y-PREP-008, Mobile Phase A 10 MM ABC in water, Mobile Phase B 100% ACN, Flow rate 25 ml, Gradient (Time/% B) 0/5,3/5, 10/40,40/75,40.1/99,44/99,44.1/5,49/5).

$^1$HNMR (400 MHZ, DMSO-$d_6$) δ=9.63-9.61 (m, 1H), 8.54 (d, J=6.0 Hz, 1H), 8.15-8.12 (m, 2H), 7.92 (d, J=6.8 Hz, 1H), 7.73-7.66 (m, 3H), 7.62-7.53 (m, 3H), 7.13-7.09 (m, 2H), 6.96-6.93 (m, 2H), 5.48 (t, J=5.6 Hz, 1H), 4.53 (d, J=5.6 Hz, 1H), 4.31-4.18 (m, 2H), 3.94-3.90 (m, 1H), 3.39 (bs, 4H), 3.05-3.01 (m, 1H), 2.40-2.10 (m, 6H), 0.94-0.90 (m, 4H), 0.84-0.80 (m, 1H), 0.46-0.42 (m, 1H), 0.37-0.33 (m, 1H). LC-MS (Method-C)=719.0 $[M+H]^+$; 99.603% at RT 2.487 min. HPLC (Method-B)=98.036% at RT 9.349 min.

Synthesis of 25-4 and 25-5

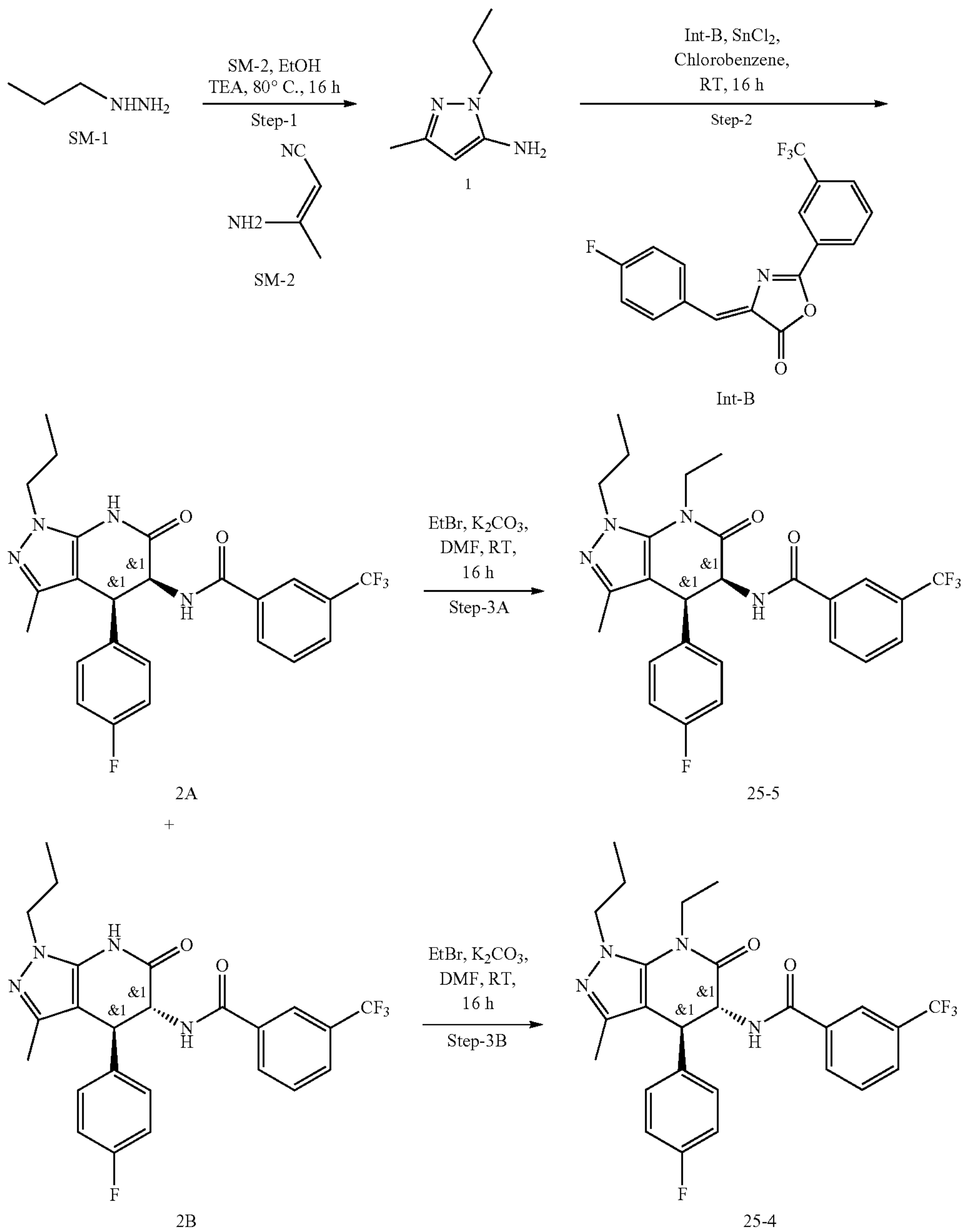

Step-1: Synthesis of 5-methyl-2-propyl-pyrazol-3-amine (B)

To a stirred solution of SM-1 (0.5 g, 4.52 mmol) in ethanol (5 mL) were added triethylamine (3.18 mL, 22.60 mmol) and (SM-2) I-3-aminobut-2-enenitrile (0.371 g, 4.52 mmol) at room temperature and the reaction mixture was stirred at 80° C. for 16 h. The reaction progress was monitored by TLC (30% ethyl acetate in heptane). After completion, the reaction mixture was concentrated under vacuum to get the crude compound, the crude compound was washed with heptane. The heptane layer was concentrated to afford 1 (0.0120 g, 8%) as a pale-yellow liquid.

$^1$HNMR (400 MHZ, DMSO-$d_6$) δ=5.03 (s, 1H), 4.95 (s, 2H), 3.67 (t, J=7.2 Hz, 2H), 1.94 (s, 3H), 1.62 (q, J=14.4 Hz, 2H), 0.81 (t, J=7.6 Hz, 3H). LC-MS (Method-B)=139.94 $[M+H]^+$; 46.43% at RT 1.12 min.

Step-2: Synthesis of N-[rac-(4S,5R or S)-4-(4-fluorophenyl)-3-methyl-6-oxo-1-propyl-5,7-dihydro-4H-pyrazolo[3,4-b]pyridine-5-yl]-3-(trifluoromethyl) benzamide (2A/2B)

To the solution of B (3.5 g, 25 mmol) in chlorobenzene (25 mL) were added 1 (7.6 g, 23 mmol) and $SnCl_2$ (0.48 g, 2.5 mmol) at 25° C. under inert atmosphere and stirred for 16 h. Progress of the reaction was monitored by LCMS. After consumption of the starting material (monitored by TLC), the reaction mixture was quenched with ice cold water (10 mL), and extracted with EtOAc (2×30 mL). The combined organic layer was dried over anhydrous sodium sulphate and concentrated under reduced pressure to afford the crude compound. The crude material was purified by silica-gel column chromatography. The product was eluted in 10 to 40% EtOAc in heptane, and product containing fractions were concentrated to get 2A (0.3 g, 2.5%) and 2B (0.5 g, 3.8%) as pale-yellow solid.

Data for 2B:

$^1$HNMR (400 MHZ, DMSO-$d_6$) δ=11.97 (s, 1H), 8.90 (d, J=8.0 Hz, 1H), 8.00 (bs, 2H), 7.90-7.86 (m, 1H), 7.60-7.67 (m, 1H), 7.31 (bs, 2H), 7.10-7.05 (m, 2H), 7.81 (t, J=9.6 Hz, 1H), 4.30 (d, J=12.0 Hz, 1H), 3.89-3.87 (m, 3H), 1.68-1.66 (m, 2H), 1.34 (s, 3H), 0.83 (bs, 3H). LC-MS (Method-A)=475.68 $[M+H]^+$; 95.78% at RT 2.126 min.

Data for 2A:

$^1$HNMR (400 MHZ, DMSO-$d_6$) δ=11.19 (s, 1H), 8.47 (d, J=6.8 Hz, 1H), 8.05 (bs, 2H), 7.90 (d, J=6.8 Hz, 1H), 7.70 (t, J=8.0 Hz, 1H), 7.09 (d, J=8.8 Hz, 1H), 7.70 (t, J=6.4 Hz, 1H), 7.09 (t, J=8.8 Hz, 2H), 6.96 (t, J=5.6 Hz, 2H), 5.196 (t, J=8.0 Hz, 1H), 4.45 (d, J=6.8 Hz, 1H), 4.08-4.04 (m, 2H), 1.9 (s,3H), 1.75-1.69 (m, 2H), 0.88 (t, J=8.0 Hz, 3H). LC-MS (Method-A)=475.68 $[M+H]^+$; 94.14% at RT 2.11.7126 min.

Step-3B: Synthesis of N-[rac-(4S,5R)-7-ethyl-4-(4-fluorophenyl)-3-methyl-6-oxo-1-propyl-4,5-dihydro-pyrazolo[3,4-b]pyridine-5-yl]-3-(trifluoromethyl) benzamide (25-4)

To a stirred solution of 2B (0.3 g, 0.63 mmol) in DMF (3 mL) were added potassium carbonate (0.174 g, 1.26 mmol) and bromoethane (0.094 mL, 1.26 mmol) at 0° C. under inert atmosphere. The reaction mixture was stirred at 25° C. for 16 h. Progress of the reaction was monitored by LCMS and TLC. After consumption of the starting material (monitored by TLC), the reaction mixture was quenched with ice cold water (10 mL), and extracted with EtOAc (2×10 mL). The combined organic layer was dried over anhydrous sodium sulphate and concentrated under reduced pressure to afford crude compound. The crude material was purified by silica gel column chromatography. The product was eluted in 20 to 30% EtOAc in heptane, product containing fractions were collected and concentrated to afford pure 25-4 (0.1 g, 30%) as a white solid.

$^1$HNMR (400 MHZ, DMSO-$d_6$) δ=8.93 (d, J=9.2 Hz, 1H), 7.98-7.96 (m, 2H), 7.89 (d, J=8.0 Hz, 1H), 7.69 (t, J=7.6 Hz, 1H), 7.34-7.30 (m, 2H), 7.14 (t, J=9.2 Hz, 2H), 5.01-4.95 (m, 1H), 4.29 (d, J=12.4 Hz, 1H), 4.11-4.01 (m, 3H), 3.80-3.74 (m, 1H), 1.81-1.78 (m, 2H), 1.34 (s, 3H), 1.17 (t, J=7.2 Hz, 3H), 0.89 (t, J=7.6 Hz, 3H). LC-MS (Method-A)=501.30 $[M+H]^+$; 96.96% at RT 2.26 min. HPLC (Method-A)=97.90% at RT 5.760 min. HPLC-Chiral (Method-F)=49.999% at RT 5.032 min, 58.499% at RT 6.834 min.

Step-3A: Synthesis of N-[rac-(4S,5S)-7-ethyl-4-(4-fluorophenyl)-3-methyl-6-oxo-1-propyl-4,5-dihydro-pyrazolo[3,4-b]pyridine-5-yl]-3-(trifluoromethyl) benzamide (25-5)

To a stirred solution of 2A (0.4 g, 0.843 mmol) in DMF (4 mL) were added potassium carbonate (0.233 g, 1.68 mmol) and bromoethane (0.126 mL, 1.68 mmol) at 0° C. under inert atmosphere. The reaction mixture was stirred at 25° C. for 16 h. Progress of the reaction was monitored by LCMS and TLC. After consumption of the starting material (monitored by TLC), the reaction mixture was quenched with ice cold water (10 mL) and extracted with EtOAc (2×10 mL). The combined organic layer was dried over anhydrous sodium sulphate and concentrated under reduced pressure to afford the crude compound. The crude material was purified by prep purification to afford pure 25-5 (0.115 g, 26%) as a pale-yellow solid.

$^1$HNMR (400 MHZ, DMSO-$d_6$) δ=8.47 (d, J=7.2 Hz, 1H), 8.12-8.09 (m, 2H), 7.92-7.90 (m, 1H), 7.70 (t, J=7.6 Hz, 1H), 7.10-7.06 (m, 2H), 6.96-6.93 (m, 2H), 5.17 (t, J=7.2 Hz, 1H), 4.39 (d, J=7.2 Hz, 1H), 4.20-4.06 (m, 3H), 3.82-3.77 (m, 1H), 1.96 (s, 3H), 1.83-1.76 (m, 2H), 1.26 (t, J=6.8 Hz, 3H), 0.90 (t, J=7.6 Hz, 3H). LC-MS (Method-A)=503.74 $[M+H]^+$; 99.63% at RT 2.404 min. HPLC (Method-A)=99.78% at RT 6.159 min. HPLC-Chiral (Method-F)=51.748% at RT 3.522 min, 48.252% at RT 4.331 min.

Synthesis of 25-6 and 25-7:

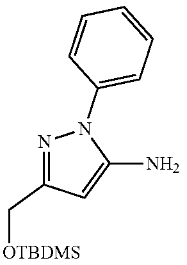

SM-1

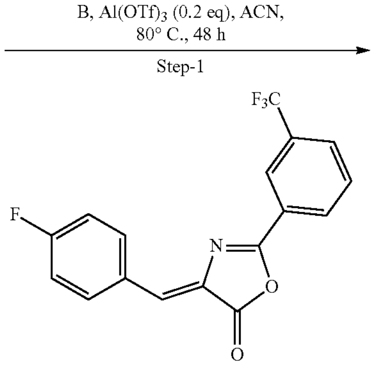

B

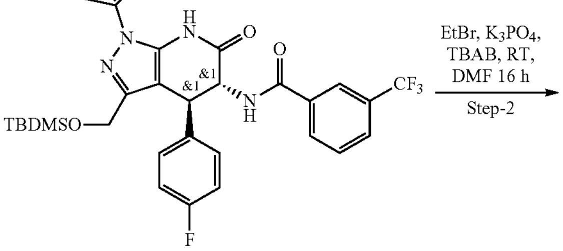

1

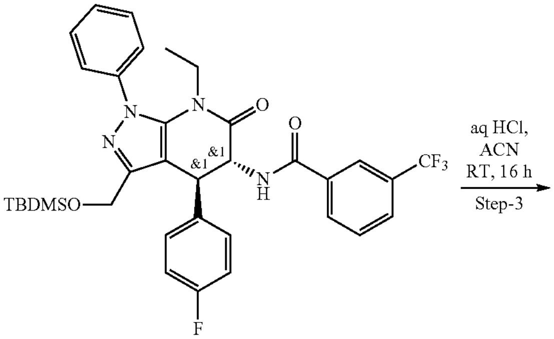

2

-continued

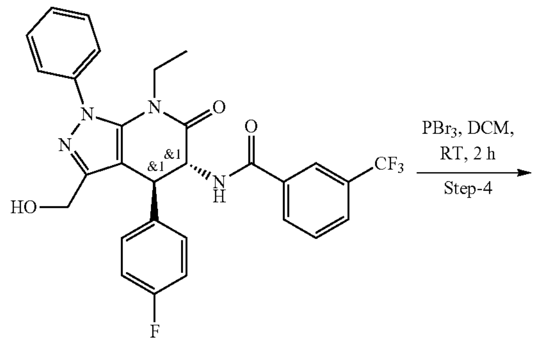

3

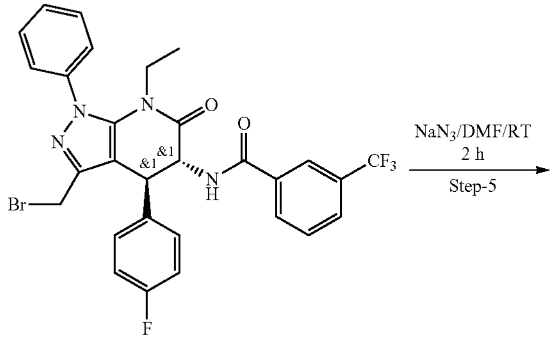

4

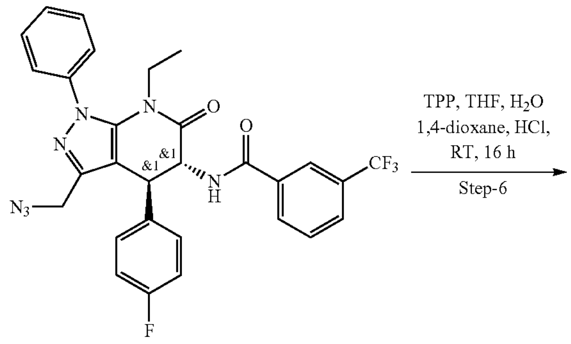

5

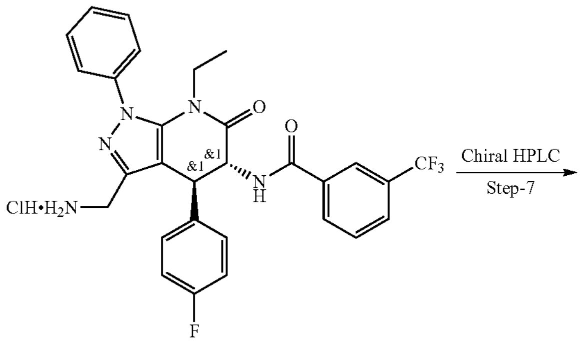

6

-continued

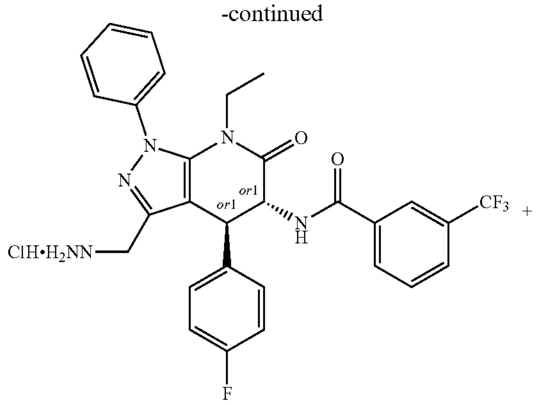

25-6

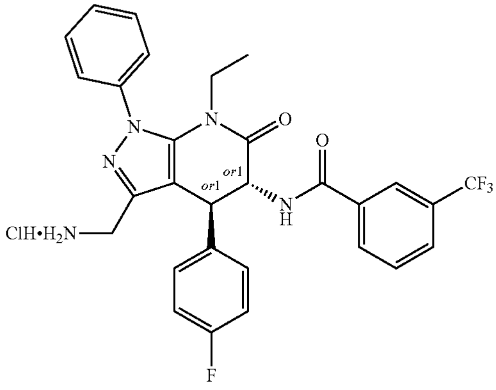

25-7

Step-1: Synthesis of N-[rac-(4S,5R)-3-[[tert-butyl (dimethyl)silyl]oxymethyl]-4-(4-fluorophenyl)-6-oxo-1-phenyl-5,7-dihydro-4H-pyrazolo[3,4-b]pyridine-5-yl]-3-(trifluoromethyl)benzamide (1)

To a stirred solution of B 10.00 g, 29.83 mmol) in I (100 mL) were added SM-1 (11.77 g, 38.78 mmol) and $Al(Otf)_3$ (2.85 g, 5.96 mmol). The resulting solution was stirred for 48 h at 80° C. Progress of the reaction was monitored by TLC. Reaction mixture was allowed to cool to room temperature, quenched with water and extracted with EtOAc. The combined organic layers were dried over anhydrous sodium sulphate and concentrated to get the crude compound. The obtained crude compound was purified by silica gel (230-400) column chromatography using ethyl acetate in heptane. Product was eluted in 50% EtOAc in heptane. The product containing fractions were collected and concentrated to get 1 (5.0 g, 26%) as a brown solid.

$^1$HNMR (400 MHz, DMSO-$d_6$) δ=10.92 (s, 1H), 9.00 (d, J=8.4 Hz, 1H), 8.05 (bs, 2H), 7.95-7.90 (m, 1H), 7.75-7.72 (m, 1H), 7.61-7.52 (m, 4H), 7.41-7.36 (m, 3H), 7.13 (t, J=8.8 Hz, 2H), 5.00-4.95 (m, 1H), 4.44 (d, J=10.8 Hz, 1H), 4.15 (d, J=12.4 Hz, 1H), 3.84 (d, J=11.6 Hz, 1H), 0.75 (s, 9H), 0.15 (s, 3H), 0.16 (s, 3H). LC-MS (Method-A)=639.4 $[M+H]^+$; 98.12% at RT 1.91 min.

Step-2: Synthesis of N-[rac-(4S,5R)-3-[[tert-butyl (dimethyl)silyl]oxymethyl]-7-ethyl-4-(4-fluorophenyl)-6-oxo-1-phenyl-4,5-dihydropyrazolo[3,4-b] pyridine-5-yl]-3-(trifluoromethyl)benzamide (3)

To a stirred solution of 1 (5.0 g, 7.8 mmol) in I (40.00 mL) were added $K_3PO_4$ (3.4 g, 16 mmol), tetrabutylammonium bromide (5.2 g, 16 mmol) and bromoethane (1.2 mL, 16 mmol) at 0° C. and the reaction mixture was allowed to stir at RT for 16 h. Reaction progress was monitored by TLC. After completion of reaction, the reaction mixture was diluted with water and extracted with EtOAc. The combined organic layer was dried over sodium sulphate and concentrated under reduced pressure to afford crude compound. The crude was purified by column chromatography of 100-200 mesh silica gel and eluted at 15-20% of EtOAc in heptane to get 2 (2.3 g, 44%) as pale-yellow solid.

$^1$HNMR (400 MHZ, DMSO-$d_6$) δ=9.03 (d, J=8.8 Hz, 1H), 8.03 (bs, 2H), 7.91 (d, J=7.6 Hz, 1H), 7.73-7.66 (m, 3H), 7.61-7.50 (m, 3H), 7.39 (t, J=8.0 Hz, 2H), 7.15 (t, J=8.8 Hz, 2H), 5.17 (t, J=10.4 Hz, 1H), 4.41 (d, J=10.8 Hz, 1H), 4.16 (d, J=11.6 Hz, 1H), 3.84 (d, J=12.4 Hz, 1H), 3.69-3.66 (m, 1H), 3.22-3.17 (m, 1H), 0.82-0.74 (m, 12H), 0.15 (s, 3H), 0.16 (s, 3H). LC-MS (Method-A)=667.35 $[M+H]^+$; 93.26% at RT 1.952 min.

Step-3: N-[rac-(4S,5R)-7-ethyl-4-(4-fluorophenyl)-3-(hydroxymethyl)-6-oxo-1-phenyl-4,5-dihydropyrazolo[3,4-b]pyridine-5-yl]-3-(trifluoromethyl)benzamide (4)

To a stirred solution of 2 (2.3 g, 3.4 mmol) in I (20 mL) was added HCl (12 mL) at 25° C. and the reaction mixture was stirred for 16 h. Reaction progress was monitored by TLC. After completion of the reaction, solvent was evaporated and washed with pentane to afford 4 (1.0 g, 53%) as pale-yellow solid compound.

$^1$HNMR (400 MHZ, DMSO-$d_6$) δ=9.04 (d, J=8.8 Hz, 1H), 8.02 (bs, 2H), 7.90 (d, J=8.0 Hz, 1H), 7.73-7.64 (m, 3H), 7.60-7.49 (m, 3H), 7.43-7.39 (m, 2H), 7.14 (t, J=8.8 Hz, 2H), 5.24-5.19 (m, 1H), 4.43 (d, J=12.0 Hz, 1H), 3.87 (d, J=12.0 Hz, 1H), 3.75-3.69 (m, 1H), 3.54 (d, J=12.4 Hz, 1H), 3.17-3.12 (m, 1H), 0.81 (t, J=6.8 Hz, 3H). LC-MS (Method-A)=553.8 $[M+H]^+$; 84.91% at RT 2.28 min.

Step-4: N-[rac-(4S,5R)-3-(bromomethyl)-7-ethyl-4-(4-fluorophenyl)-6-oxo-1-phenyl-4,5-dihydropyrazolo[3,4-b]pyridine-5-yl]-3-(trifluoromethyl)benzamide (5)

To a stirred solution of 3 (1 g, 1.810 mmol) in DCM (10.0 mL) was added $PBr_3$ (0.258 mL, 2.71 mmol) at 0° C. After the addition, the reaction mixture was stirred for 2 h at room temperature. Reaction progress was monitored by TLC. After completion of the reaction, the reaction mixture was quenched with aq. $NaHCO_3$ and extracted into DCM layer. The organic layer was dried over sodium sulphate and concentrated under reduced pressure to obtain the crude. The crude compound was purified by column chromatography of 100-200 mesh silica gel and eluted at 30-40% EtOAc in heptane to get 4 (0.38 g, 34%) as an off white solid.

$^1$HNMR (400 MHZ, DMSO-$d_6$) δ=9.00 (d, J=8.8 Hz, 1H), 8.01 (bs, 2H), 7.91 (d, J=7.2 Hz, 1H), 7.73-7.68 (m, 3H), 7.61-7.48 (m, 6H), 7.19 (t, J=8.0 Hz, 2H), 5.34-5.28 (m, 1H), 4.42 (d, J=12.4 Hz, 1H), 4.09 (d, J=10.8 Hz, 1H), 3.72-3.67 (m, 1H), 3.47 (d, J=10.8 Hz, 1H), 3.17-3.12 (m, 1H), 0.81 (t, J=6.8 Hz, 3H). LC-MS (Method-A)=615.17/617.25 $[M+H]^+$; 95.27% at RT 1.692 min.

Step-5: N-[rac-(4S,5R)-3-(azidomethyl)-7-ethyl-4-(4-fluorophenyl)-6-oxo-1-phenyl-4,5-dihydropyrazolo[3,4-b]pyridine-5-yl]-3-(trifluoromethyl)benzamide (6)

To a stirred solution of 4 (0.38 g, 0.62 mmol) in DMF (4 mL) was added $NaN_3$ (0.061 g, 0.93 mmol) at 25° C. After the addition, the reaction mixture was allowed to stir for 2 h at room temperature. Reaction progress was monitored by TLC. After completion of reaction, water was added to reaction mixture and stirred for 30 min. to afford solid. The solid was filtered to obtain 5 (0.29 g, 81%) as off white solid.

$^1$HNMR (400 MHZ, DMSO-$d_6$) δ=8.96 (d, J=8.8 Hz, 1H), 7.98-7.86 (m, 3H), 7.69-7.64 (m, 2H), 7.59-7.49 (m, 2H), 7.44-7.40 (m, 1H), 7.16 (t, J=8.8 Hz, 1H), 5.30-5.25 (m, 1H), 4.41 (d, J=12.4 Hz, 1H), 3.80-3.70 (m, 2H), 3.44-3.40 (m, 1H), 3.10-3.03 (m, 1H), 2.86 (s, 2H), 2.70 (s, 2H), 0.78 (t, J=6.8 Hz, 3H). LC-MS (Method-A)=578.30 $[M+H]^+$; 96.13% at RT 1.692 min.

Step-6: N—[rel-(4S,5R)-3-(aminomethyl)-7-ethyl-4-(4-fluorophenyl)-6-oxo-1-phenyl-4,5-dihydropyrazolo[3,4-b]pyridine-5-yl]-3-(trifluoromethyl)benzamide (25-6 and 25-7)

To stirred solution of 5 (0.29 g, 0.50 mmol) in THF (3 mL), and water (1 mL) was added triphenyl phosphate (0.50 g, 1.5 mmol) at 25° C. and stirred for 16 h at the same temperature. Reaction progress was monitored by TLC. After completion of the reaction, the reaction mixture was diluted with water (25 mL) and the compound was extracted into EtOAc (2×25 mL) and the organic layer was dried over sodium sulphate, concentrated under reduced pressure to obtain the crude compound. The crude was purified by column chromatography of 230-400 mesh silica and eluted at 5% MeOH in DCM as pale-yellow solid was obtained). To this was added 4.0 M HCl in dioxane at 0° C. and stirred at room temperature for 90 min. After completion of reaction, DCM was evaporated and washed with diethyl ether to obtain racemic compound. The racemic compound (0.019 g, 6.8%) was further submitted to Chiral and Achiral prep purification to get 25-6 (peak 1) and 25-7 (peak 2).

Chiral prep purification: No. of Injections 15 inj (10 mg/inj), Column Chiral PAK IK (30×250*mm,5μ), Mobile phase A: 0.05% IP Amine n-Hexane, Mobile phase B: EtOH-MeOH (1:1), Eluent A: 70-30, Total Flow rate (mL/min): 46, Diluent: MP, Detection: 254 nm.

Data for 25-6 (Peak 1):

$^1$HNMR (400 MHZ, DMSO-$d_6$) δ=8.32 (s, 1H), 8.01-7.99 (m, 2H), 7.91-7.89 (m, 1H), 7.72-7.68 (m, 1H), 7.66-7.64 (m, 2H), 7.60-7.56 (m, 2H), 7.53-7.52 (m, 1H), 7.47-7.44 (m, 2H), 7.18 (t, J=8.8 Hz, 2H), 5.30-5.25 (m, 1H), 4.43 (d, J=12.0 Hz, 1H), 3.80-3.75 (m, 1H), 3.17-3.06 (m, 1H), 3.00-2.88 (m, 2H), 0.82 (t, J=7.2 Hz, 3H). LC-MS (Method-A)=552.62 $[M+H]^+$; 99.62% at RT 1.831 min. HPLC (Method-A)=99.67% at RT 4.896 min.

Data for 25-7 (Peak 2):

$^1$HNMR (400 MHZ, DMSO-$d_6$) δ=9.00 (d, J=8.8 Hz, 1H), 8.29 (s, 1H), 8.01-7.99 (m, 2H), 7.91-7.89 (m, 1H), 7.70 (t, J=8.0 Hz, 1H), 7.66-7.64 (m, 2H), 7.60-7.59 (m, 2H), 7.54-7.44 (m, 3H), 7.18 (t, J=8.8 Hz, 2H), 5.30-5.25 (m, 1H), 4.44 (d, J=12.4 Hz, 1H), 3.81-3.75 (m, 1H), 3.17-3.07 (m, 1H), 2.96-2.93 (m, 2H), 0.82 (t, J=6.8 Hz, 3H). LC-MS (Method-A)=550.30 $[M-H]^+$; 99.26% at RT 1.857 min. HPLC (Method-A)=99.73% at RT 4.229 min.

Synthesis of I-68:

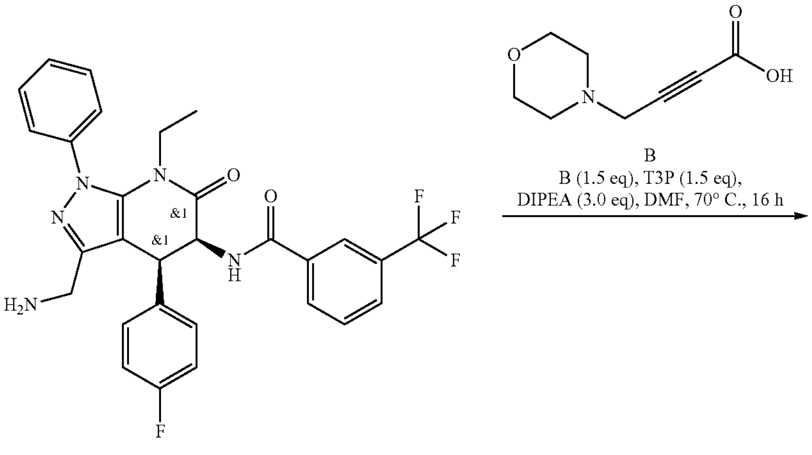

25-3

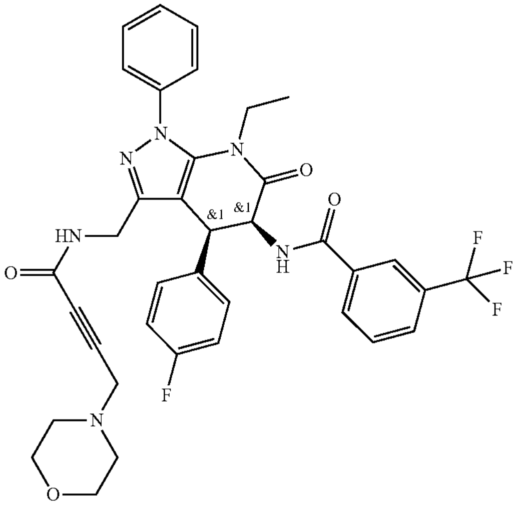

I-68

Step-1: Synthesis of ~{N}-[~{rac}-(4~{S},5~{S})-7-ethyl-4-(4-fluorophenyl)-3-[(4-morpholinobut-2-ynoylamino)methyl]-6-oxo-1-phenyl-4,5-dihydropyrazolo[3,4-b]pyridine-5-yl]-3-(trifluoromethyl) benzamide (I-68)

To a stirred solution of B (0.096 g, 0.54 mmol) in DMF (2 mL) were added N,N-Diisopropylethylamine (0.190 mL, 1.08 mmol), T3P(0.32 mL, 0.54 mmol, 50% in ethyl acetate) and ~{N}-[~{rac}-(4~{S},5~{S})-3-(aminomethyl)-7-ethyl-4-(4-fluorophenyl)-6-oxo-1-phenyl-4,5-dihydropyrazolo[3,4-b]pyridine-5-yl]-3-(trifluoromethyl)benzamide (0.2 g, 0.36 mmol) reagent at room temperature. Reaction was stirred for 16 h at 70° C. Progress of the reaction was monitored by TLC. Reaction mixture was allowed to room temperature, quenched with water (25 mL), and extracted with EtOAc (2x25 mL). Combined organic layers were dried over anhydrous sodium sulphate and concentrated under reduced pressure to get the crude compound. The above crude compound was purified by prep-HPLC, product containing fractions were collected and lyophilized to get pure I-68 (0.060 g, 23%) as a light brown solid.

$^1$HNMR (400 MHZ, DMSO-$d_6$) δ=8.85 (t, J=6.0 Hz, 1H), 8.49 (d, J=7.2 Hz, 1H), 8.16-8.12 (m, 2H), 7.92 (d, J=7.6 Hz, 1H), 7.73-7.66 (m, 3H), 7.61-7.52 (m, 3H), 7.11-7.06 (m, 2H), 6.95-6.91 (m, 2H), 5.51 (t, J=7.2 Hz, 1H), 4.57 (d, J=7.2 Hz, 1H), 4.32-4.27 (m, 1H), 4.12-4.07 (m, 1H), 3.93-3.88 (m, 1H), 3.55 (t, J=4.8 Hz, 3H), 3.05-3.00 (m, 1H), 2.39 (t, J=4.8 Hz, 3H), 0.91 (t, J=7.2 Hz, 1H). LC-MS (Method-B)=703.1 [M−H]$^+$; 96.319% at RT 2.145 min. HPLC (Method-B)=97.70% at RT 8.634 min.

NMR $^1$H NMR spectrum was recorded on Bruker 400 MHZ, Agilent-NMR-vnmrs400 and Varian-NMR-vnmrs400 instruments internally referenced to a tetramethylsilane (TMS) signal. Chemical shifts (δ) and coupling constants (J) were expressed in parts per million and hertz, respectively.

LCMS

Method-A: LCMS_X-Select (Formic acid); Column: X-Select CSH C18 (3.0*50) mm 2.5μ. Mobile Phase: A: 0.05% Formic acid in water: I (95:5) B: 0.05% Formic acid in CAN. Inj Volume: 2.0 μL, Column oven temperature: 50 C; Flow Rate: 1.2. mL/minute; Gradient program: 0% B to 98% B in 2.0 minute, hold till 3.0 min, at 3.2 min B conc is 0% up to 4.0 min.

Synthesis of 25-8:

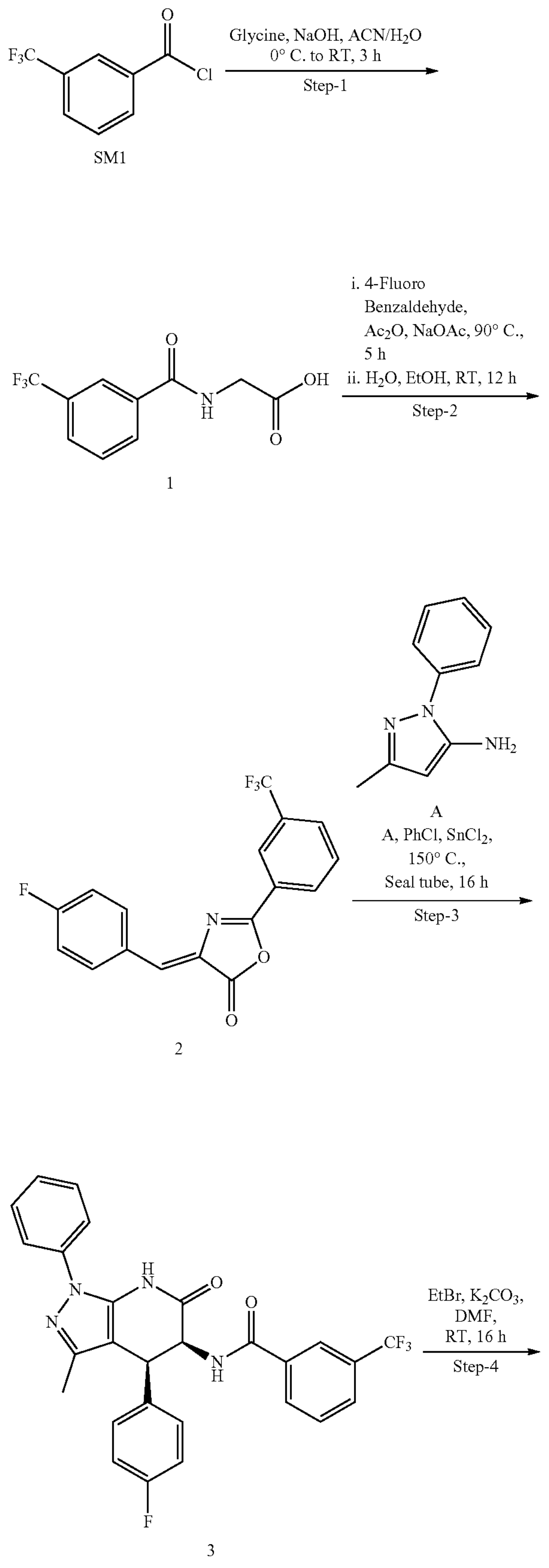

-continued

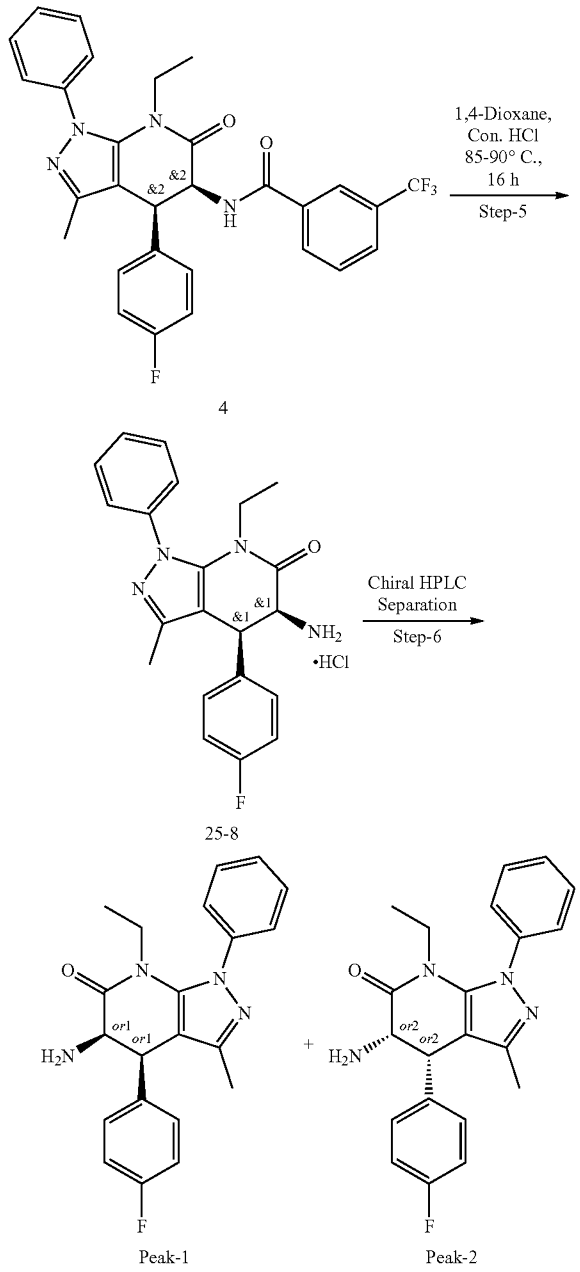

Step-1: Synthesis of (3-(trifluoromethyl)benzoyl)glycine (1)

To a solution of glycine (18.20 g, 242.71 mmol) in I (100 mL) was added NaOH (24.27 g, 606.79 mmol) in $H_2O$ (50 mL) at 0° C. After stirring for 5 min, 3-(trifluoromethyl) benzoyl chloride (SM1) (50 g, 242.71 mmol) in I (100 mL) was added dropwise. The reaction mixture was stirred at room temperature for 3 h. After consumption of the starting material (by TLC), the reaction mixture was diluted with water and extracted with EtOAc (2×500 mL). The organic layer was dried over anhydrous $Na_2SO_4$, filtered and concentrated under reduced pressure. The obtained crude was washed with heptane and dried under vacuum to afford compound (1) (72 g, 60%) as an off white solid. LC-MS (Method-A)=248.27 $[M+H]^+$; 92.46% at RT 0.996 & 1.065 min.

Step-2: Synthesis of (Z)-4-(4-fluorobenzylidene)-2-(3-(trifluoromethyl)phenyl)oxazol-5 (4H)-one (2)

To a mixture of compound (1) (8.0 g, 32.36 mmol) and 4-fluoro benzaldehyde (4.0 g, 32.36 mmol) in acetic anhydride (9.9 g, 97.09 mmol) was added to NaOAc (2.6 g, 32.36 mmol). The reaction mixture was heated at 90° C. for 5 h to obtain yellow solid. After consumption of the starting material (by TLC), EtOH & $H_2O$ (1:1) (30 mL) were added to the reaction mixture and stirred at room temperature for 12 h. The reaction mixture was filtered, washed with heptane, and dried under vacuum followed by co-distilled with toluene to afford compound (2) (6.5 g, 60%) as pale-yellow solid.

Step-3: Synthesis of (N-((4S,5S)-4-(4-fluorophenyl)-3-methyl-6-oxo-1-phenyl-4,5,6,7-tetrahydro-1H-pyrazolo[3,4-b]pyridine-5-yl)-3-(trifluoromethyl)benzamide (3)

To a mixture of compound (2) (10.0 g, 29.82 mmol) and 3-methyl-1-phenyl-1H-pyrazol-5-amine (A) (5.67 g, 32.81 mmol) in chlorobenzene (12.0 mL) was added $SnCl_2$ (0.563 g, 2.98 mmol) in a sealed tube. The reaction mixture was heated at 150° C. for 16 h. After consumption of starting material (by TLC), the reaction mixture was diluted with water (500 mL) and extracted with EtOAc (2×1000 mL). The organic layer was dried over anhydrous $Na_2SO_4$ filtered and concentrated under reduced pressure. The crude compound was purified by medium pressure liquid column chromatography by eluting with 30-35% EtOAc in heptane to afford compound (3) (7.0 g, 46.6%) as pale yellow solid. $^1$H NMR (400 MHZ, DMSO-$d_6$) δ=11.07-11.02 (m, 1H), 8.48-8.43 (m, 1H), 8.09-8.05 (m, 2H), 7.92-7.88 (m, 1H), 7.73-7.67 (m, 1H), 7.63-7.59 (m, 2H), 7.54-7.49 (m, 2H), 7.41-7.35 (m, 1H), 7.13-7.07 (m, 2H), 7.05-7.00 (m, 2H), 5.37-5.31 (m, 1H), 4.58-4.53 (m, 1H), 2.05-2.01 (m, 3H).

Step-4: synthesis of N-((4S,5S)-7-ethyl-4-(4-fluorophenyl)-3-methyl-6-oxo-1-phenyl-4,5,6,7-tetrahydro-1H-pyrazolo[3,4-b]pyridine-5-yl)-3-(trifluoromethyl)benzamide (4)

To a stirred solution of compound (3) (7.0 g, 13.76 mmol) in DMF (15 mL) was added $K_2CO_3$ (1.89 g, 16.51 mmol) at room temperature. After stirring for 10 min, ethyl bromide (1.65 g, 15.14 mmol) in DMF (5 mL) was added. The reaction mixture was stirred for 16 h. After consumption of starting material (by TLC), the reaction mixture was diluted with water (500 mL) and extracted with EtOAc (2×500 mL). The organic layer was dried over anhydrous $Na_2SO_4$, filtered and concentrated under reduced pressure. The crude material was purified by medium pressure liquid column chromatography by eluting with 25-30% EtOAc in heptane to afford compound (4) (3.5 g, 47.9%) as an off white solid.

Step-5: Synthesis of (4S,5S)-5-amino-7-ethyl-4-(4-fluorophenyl)-3-methyl-1-phenyl-1,4,5,7-tetrahydro-6H-pyrazolo[3,4-b]pyridine-6-one hydrochloride (25-8)

To a stirred solution of compound (4) (3.0 g, 5.59 mmol) in 1,4-dioxane (10 mL) was added conc. HCl (3.0 mL) solution. The reaction mixture was heated at 85° C.-90° C. for 16 h. After consumption of starting material (by TLC), the reaction mixture was concentrated under reduced pressure. The crude material was purified by medium pressure liquid column chromatography by eluting with 10-12% MeOH in DCM to obtain pale yellow solid compound. The product was further triturated with heptane and dried to afford 25-8 (1.5 g, 66.96%) as an off white solid.

Step-6: Synthesis of rel-(4R,5S)-5-amino-7-ethyl-4-(4-fluorophenyl)-3-methyl-1-phenyl-1,4,5,7-tetrahydro-6H-pyrazolo[3,4-b]pyridine-6-one (25-8) & rel-(4R,5S)-5-amino-7-ethyl-4-(4-fluorophenyl)-3-methyl-1-phenyl-1,4,5,7-tetrahydro-6H-pyrazolo[3,4-b]pyridine-6-one (25-8)

Compound 25-8 was subjected to chiral preparative HPLC purification to obtain as Peak-1 (550 mg) and Peak-2 (550 mg) as an off white solid.

Chiral HPLC method: Description: COLUMN: CHIRAL PAK-IG (250×4.6 mm, 5 μm); Mobile Phase A: 0.1% DEA in n-Hexane; Mobile Phase B: IPA A: B: 75:25; Flow: 1.0 mL/min.

NMR:

$^1$H NMR spectrum was recorded on Bruker 400 MHz and Varian 400 MHz instruments internally referenced to a tetramethylsilane (TMS) signal. Chemical shifts (δ) and coupling constants (J) were expressed in parts per million and hertz, respectively.

LC-MS:

Method-A: Column: Bakerbond Q2100 C18 1.8 um; 2.1×50 mm Mobile Phase A: 0.05% FA in Water; Mobile Phase B: 0.05% FA in CAN; Flow Rate: 0.6 ml; Oven Temperature: 40° C.; Gradient Program (Time/B %): 0_5, 0.2_5,2.3_98,3.3_98,3.5_5,4.

Method-B: Column: X-Bridge C18 (3.0*50) mm 2.5μ; Mobile Phase: A: 2.5 mM Ammonium Bicarbonate in water; B: Acetonitrile; Flow Rate: 1.2 mL/minute; Column oven temp. 50° C.; Gradient program: 0% B to 98% B in 2.0 minute, hold till 3.0 min, at 3.2 min B conc is 0% up to 4.0 min.

Method-C: Column: X-Select CSH C18, (50 mm*3.0 mm,2.5μ) Mobile Phase A: 0.05% TFA in Water; Mobile Phase B: 0.05% TFA in Acetonitrile; Flow rate: 1.0 mL/min. Column temperature: 40° C.; Gradient Program (B %): 0.0/2, 0.3/2,2.0/98, 2.8/98, 3.0/2,3.7/2.

HPLC:

Method-A: Column: X Select CSH C18 (150×4.6) mm,3.5μ; Mobile phase A: 0.1% FA in Water: I (95:05); Mobile phase B: Acetonitrile; Gradient Programme: T/B %: 0.01/5, 1/5,8/100,12/100, 14/5, 18/5; Flow rate: 1.2 ml/min.

Method-B: Column: X-Bridge CSH C18 (150×4.6 mm, 3.5 μm); Mobile Phase-A: 5 mM $NH_4HCO_3$; Mobile Phase-B: I; Programme: T/B %: 0.01/2,2/2,12/90, 16/90; Flow rate: 1.0 mL/min.; Diluent: I:Water (80:20).

Method-C: Column: X-Select CSH C18 (4.6*150) mm 5μ Mobile Phase: A-0.1% TFA in water; B-Acetonitrile; Inj Volume; 5.0 μL, Flow Rate: 1.2. mL/minute; Gradient program: Time (min)/B Conc.: 0.01/5, 1.0/5, 8.0/100, 12.0/100, 14.0/5, 18.0/5.

Chiral HPLC:

Method-A: Column: CHIRALCEL-OJ-H (250×4.6 mm, 5μ) Mobile Phase A: 0.1% DEA in Hexane; Mobile Phase B: IPA A/B: 60/40; Flow: 1.0 ml/Min; PDA: OJ-H_015

Method-B: Column: CHIRALPAK IG (250×4.6 mm, 5 μm) Mobile Phase A: n-Hexane; Mobile Phase B: DCM: IPA (1:1) A B: 60:40 Flow rate: 1.0 mL/min.

Method-C: Column: CHIRALPAK-IA (250×4.6 mm, 5 μm) A B: 70/30 Mobile Phase A: n-Hexane; Mobile Phase B: EtOH: MeOH (1:1) Flow rate: 1.00 ml/min.

Synthesis of 25-1:

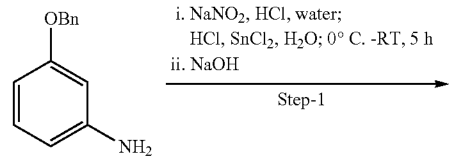

SM-1

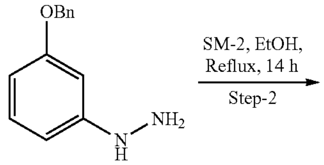

1

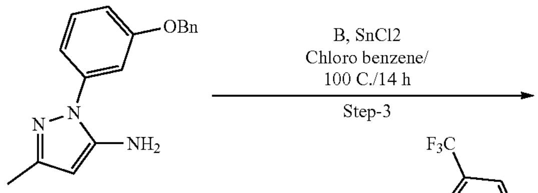

2

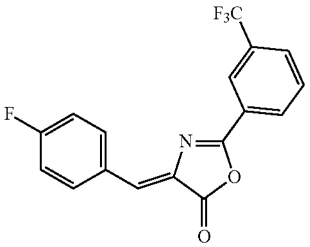

B

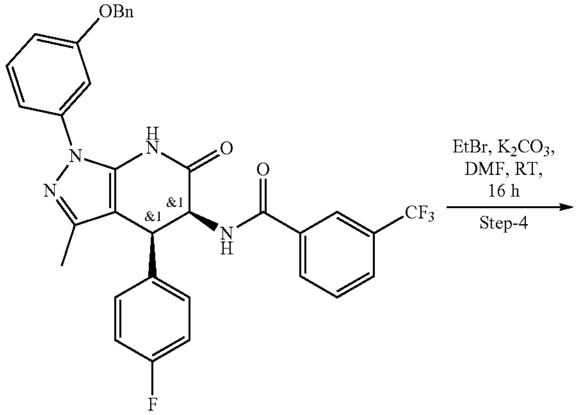

3

-continued

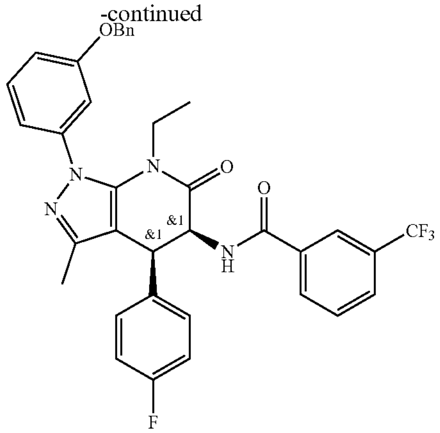

4

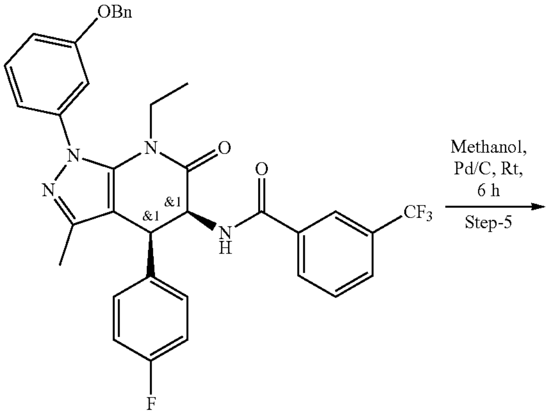

4

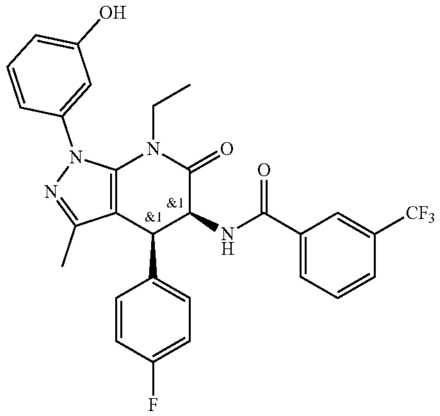

25-1

Step-1: Synthesis of 3-benzyloxy-~{N}-methyl-aniline compound (1)

A solution of 3-benzyloxyaniline (SM-1) (30.0 g, 151 mmol) in hydrochloric acid (333 mL) was stirred for 20-30 min at room temperature. The reaction mixture was cooled to −5° C. to 0° C., then sodium nitrite (18.9 g, 271 mmol) dissolved in chilled water (200 mL) was added. The reaction mixture was stirred for 60-75 min. In another round bottom flask tin(II) chloride (144 g, 753 mmol) was dissolved in hydrochloric acid (111 mL) and stirred for 30-40 min at room temperature. The reaction mixture was cooled to −5° C. to 0° C. and above diazonium salt solution was slowly added to this mixture. After addition, the reaction mixture was stirred at −5° C. to 0° C. for 30-40 min, then the reaction mixture was allowed to stir at room temperature for 90-180 min. Reaction progress was monitored by TLC. After completion of reaction, the reaction mixture was filtered through Buchner funnel and washed with (15 mL) water and dried under vacuum completely. It was co-distilled with toluene (3×30 mL), dried on rotavap completely to afford pure compound (1) (15.0 g, 46.7%) as a light brown solid. Compound was directly used for next step.

$^1$H NMR (400 MHZ, $CDCl_3$) δ=7.40-7.35 (m, 2H), 7.26-7.18 (m, 4H), 6.94-6.87 (m, 2H), 6.63-6.41 (m, 3H), 4.73 (s, 2H), 4.59 (s, 1H), 4.14-4.09 (m, 1H). LC-MS (Method-A)=215.19 $[M+H]^+$; 84.64% at RT 1.05 min.

Step-2: Synthesis of 2-(3-benzyloxyphenyl)-5-methyl-pyrazol-3-amine (2)

A solution of compound (1) (5.0 g, 23 mmol) and (SM-2) (~{Z})-3-aminobut-2-enenitrile (2.3 g, 28 mmol) in ethanol (50 mL) were stirred at 80-90° C. for 12-14 h. Reaction progress was monitored by TLC. After completion of reaction, the reaction mixture was concentrated under reduced pressure, diluted with water (2×500 mL) & extracted with EtOAc (2× 500 mL) separated. Organic layer was concentrated under reduced pressure. Crude compound was purified by combi-flash chromatography, eluted at 20% of EtOAc in heptane to afford compound (2) (3.50 g, 54%) as a light brown solid.

$^1$H NMR (400 MHZ, $CDCl_3$) δ=7.44-7.12 (m, 7H), 6.94-6.92 (m, 2H), 5.44 (s, 1H), 5.10 (s, 2H), 3.74 (s, 2H), 2.29 (s, 3H). LC-MS (Method-A)=280.6 $[M+H]^+$; 69.96% at RT 1.93 min.

Step-3: Synthesis of ~{N}-[~{rac}-(4~{S},5~{S})-1-(3-benzyloxyphenyl)-4-(4-fluorophenyl)-3-methyl-6-oxo-5,7-dihydro-4~{H}-pyrazolo[3,4-b]pyridine-5-yl]-3-(trifluoromethyl)benzamide (3)

To a stirred solution of compound (2) (3.5 g, 8.8 mmol) and Int-B (2.4 g, 7.0 mmol) in chlorobenzene (80 mL) was added tin(II) chloride (0.50 g, 2.6 mmol) and the reaction mixture was stirred at 100° C. for 12-14 h. Reaction progress was monitored by TLC. After completion of reaction, the reaction mixture was concentrated under reduced pressure and diluted with water (2×250 mL) & extracted with EtOAc (2×350 mL) and separated. Organic layer was dried with over anhydrous $Na_2SO_4$ and concentrated under reduced pressure. Obtained crude compound was purified by combi-flash chromatography eluted at 50% of EtOAc in heptane to afford compound (3) (4.0 g, 74%) as a light brown solid.

$^1$H NMR (400 MHZ, DMSO-$d_6$) δ=11.0 (m, 1H), 8.46 (d, J=7.2 Hz, 1H), 8.07 (s, 2H), 7.90 (d, J=7.6 Hz, 1H), 7.69 (t, J=8.0 Hz, 1H), 7.50-7.40 (m, 6H), 7.27-7.19 (m, 2H), 7.11-7.02 (m, 5H), 5.36-5.30 (m, 1H), 4.54 (d, J=7.2 Hz, 1H), 4.05-4.00 (m, 2H), 1.17 (t, J=7.2 Hz, 3H). LC-MS (Method-A)=615.33 $[M+H]^+$; 80.64% at RT 2.55 min.

Step-4: Synthesis of ~{N}-[~{rac}-(4~{S},5~{S})-1-(3-benzyloxyphenyl)-7-ethyl-4-(4-fluorophenyl)-3-methyl-6-oxo-4,5-dihydropyrazolo[3,4-b]pyridine-5-yl]-3-(trifluoromethyl)benzamide (4)

A solution of compound (3) (4.0 g, 3.5 mmol), in DMF (40 mL) was cooled to 0° C. then potassium carbonate (1.5 g, 11 mmol) was added followed by bromo ethane (1.1 g, 11 mmol). The reaction mixture was allowed to stir at room temperature for 16 h. Reaction progress was monitored by TLC. After completion of reaction, the reaction mixture was diluted with water (200 mL) & extracted with EtOAc (2×350 mL) and separated. Organic layer was concentrated under reduced pressure to afford crude compound (3.2 g). Obtained Crude compound was purified by combi-flash eluted at 20% EtOAc in heptane to afford compound (4) (2.5 g, 100%) as a pale-yellow solid.

$^1$H NMR (400 MHZ, DMSO-$d_6$) δ=8.53 (d, J=7.2 Hz, 1H), 8.15-8.12 (s, 2H), 7.91 (d, J=8.0 Hz, 1H), 7.71 (t, J=8.0 Hz, 1H), 7.48-7.44 (m, 3H), 7.41-7.33 (m, 4H), 7.22 (d, J=8.0 Hz, 1H), 7.15-7.08 (m, 3H), 7.00-6.97 (m, 2H), 5.50 (d, J=7.2 Hz, 1H), 5.18 (s, 2H), 4.50 (d, J=7.6 Hz, 1H), 3.88-3.82 (m, 1H), 3.04-2.99 (m, 1H), 2.03 (s, 3H), 0.90 (t, J=7.2 Hz, 3H). LC-MS (Method-A)=643.2 $[M+H]^+$; 91.77% at RT 2.64 min.

Step-5: Synthesis of ~{N}-[~{rac}-(4~{S},5~{S})-7-ethyl-4-(4-fluorophenyl)-1-(3-hydroxyphenyl)-3-methyl-6-oxo-4,5-dihydropyrazolo[3,4-b]pyridine-5-yl]-3-(trifluoromethyl)benzamide 25-1

To a stirred solution of compound (4) (2.0 g, 2.9 mmol) in methanol (10 mL) was added Pd/C (20.0 mg) and stirred for 6 h at room temperature. Reaction progress was monitored by TLC. After completion of reaction, the reaction mixture was filtered through celite-bed, washed with MeOH (15 ml), and concentrated under reduced pressure to afford crude compound (1.5 g). Obtained crude was purified by column chromatography, combi-flash by using 100-200 mesh silica gel compound and was eluted with 60% ethyl acetate in heptane and concentrated under vacuum to afford pure compound 25-1 (1.3 g, 79%) as an off-white solid.

$^1$H NMR (400 MHZ, DMSO-$d_6$) δ=10.0 (s, 1H), 8.51 (d, J=6.8 Hz, 1H), 8.13 (d, J=11.2 Hz, 2H), 7.91 (d, J=7.6 Hz, 1H), 7.70 (t, J=7.6 Hz, 1H), 7.33 (t, J=8.0 Hz, 1H), 7.10 (t, J=8.8 Hz, 2H), 7.03-6.97 (m, 4H), 6.88 (d, J=8.0 Hz, 1H), 5.47 (t, J=7.2 Hz, 1H), 4.50 (d, J=7.2 Hz, 1H), 3.93-3.88 (m, 1H), 3.17-3.11 (m, 1H), 2.02 (s, 3H), 0.94 (t, J=7.2 Hz, 3H). LC-MS (Method-B)=553.3 $[M+H]^+$; 96.01% at RT 2.30 min. HPLC (Method-C)=97.36% at RT 6.19 min. Chiral HPLC (Method-C)=Peak-1=50.04% at RT 4.33 min, Peak-2=49.96% at RT 5.13 min.

To Synthesis of 25-9:

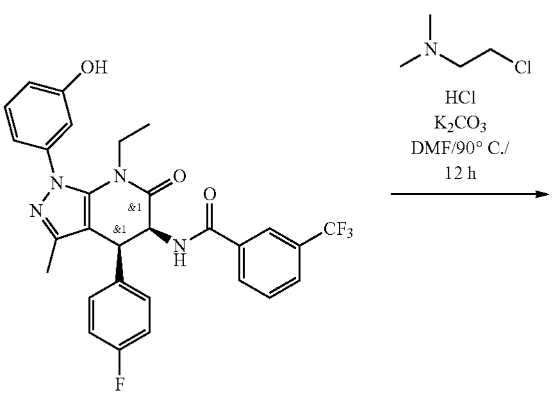

25-1

-continued

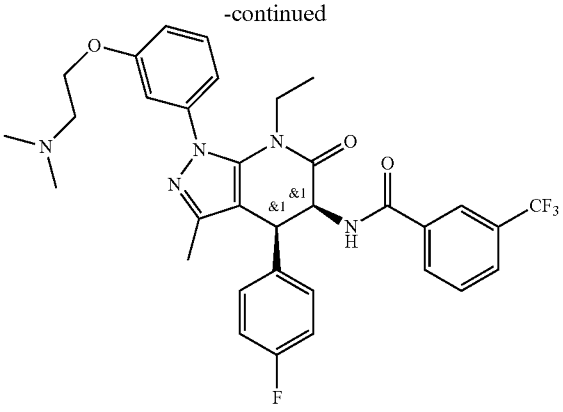

25-9

Synthesis of ~{N}-[~{rac}-(4~{S},5~{S})-1-[3-[2-(dimethylamino)ethoxy]phenyl]-7-ethyl-4-(4-fluoro-phenyl)-3-methyl-6-oxo-4,5-dihydropyrazolo[3,4-b]pyridine-5-yl]-3-(trifluoromethyl)benzamide To a stirred solution of 25-1 (0.4 g, 0.7 mmol) in DMF (10 mL) was added potassium carbonate (0.3 g, 2 mmol) and 2-chloroethyl(dimethyl) ammonium chloride (0.2 g, 1 mmol) and stirred at 90° C. for 12 h. Reaction progress was monitored by TLC. After completion of reaction, the reaction mixture was diluted with water (50 mL) & extracted with EtOAc (2×50 mL) and separated. Organic layer was concentrated under reduced pressure to afford crude compound (410 mg). Obtained crude was purified by preparative purification to afforded 25-9 (0.04 g, 9%) as an off-white solid.

$^1$H NMR (400 MHZ, DMSO-$d_6$) δ=8.54 (d, J=7.2 Hz, 1H), 8.15-8.12 (m, 2H), 7.92 (d, J=8.0 Hz, 1H), 7.71 (t, J=7.6 Hz, 1H), 7.43 (t, J=8.4 Hz, 1H), 7.25-7.19 (m, 2H), 7.10-6.99 (m, 5H), 5.51 (t, J=6.8 Hz, 1H), 4.50 (d, J=7.2 Hz, 1H), 4.11-4.10 (m, 2H), 3.93-3.88 (m, 1H), 3.17-3.08 (m, 1H), 2.63 (t, J=6.8 Hz, 2H), 2.21 (s, 6H), 2.03 (s, 3H), 0.94 (t, J=6.8 Hz, 3H). LC-MS (Method-C)=624.2 $[M+H]^+$; 96.90% at RT 3.19 min. HPLC (Method-B)=95.06% at RT 9.23 min. Chiral HPLC (Method-C)=Peak-1=51.04% at RT 6.95 min, Peak-2=48.96% at RT 9.46 min.

Synthesis of 25-10 & 25-11:

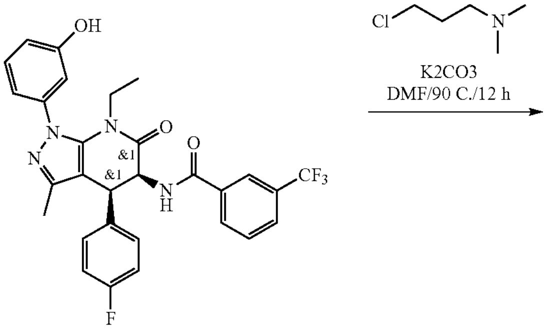

25-1

-continued

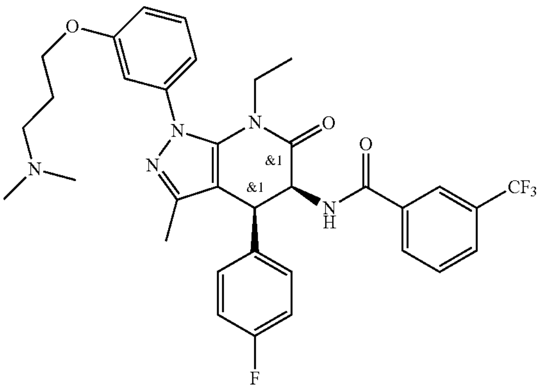

25-10

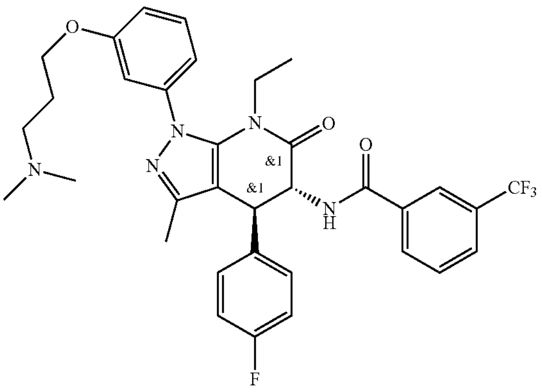

25-11

Synthesis of N-[rac-(4R,5S)-1-[3-[3-(dimethylamino)propoxy]phenyl]-7-ethyl-4-(4-fluorophenyl)-3-methyl-6-oxo-4,5-dihydropyrazolo[3,4-b]pyridine-5-yl]-3-(trifluoromethyl)benzamide and N-[rac-(4S,5S)-1-[3-[3-(dimethylamino)propoxy]phenyl]-7-ethyl-4-(4-fluorophenyl)-3-methyl-6-oxo-4,5-dihydropyrazolo[3,4-b]pyridine-5-yl]-3-(trifluoromethyl)benzamide To a stirred solution of 25-1 (0.4 g, 0.7 mmol) and 3-chloro-N,N-dimethylpropan-1-amine hydrochloride (0.2 g, 1 mmol) in DMF (10 mL) was added $K_2CO_3$ (3.0 g, 2 mmol) and stirred at 90° C. for 12 h. Reaction progress was monitored by TLC. After completion of reaction, the reaction mixture was diluted with water (250 mL) & extracted with EtOAc (2×50 mL) and separated. Organic layer was concentrated under reduced pressure to afford crude compound (410 mg). Obtained crude compound was purified by Prep-HPLC. The two fractions were collected and concentrated to afford 25-11 (0.07 g, 20%) and 25-10 (0.07 g, 20%) as an off-white solid.

25-11

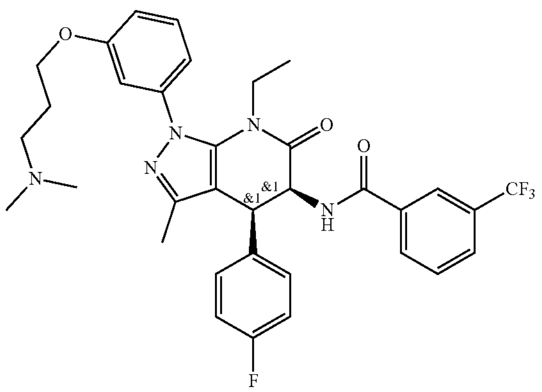

$^1$H NMR (400 MHz, DMSO-$d_6$) δ=8.97 (d, J=8.8 Hz, 1H), 8.01-8.00 (m, 2H), 7.90 (d, J=8.0 Hz, 1H), 7.70 (t, J=7.6 Hz, 1H), 7.46-7.40 (m, 3H), 7.19-7.15 (m, 4H), 7.05-7.03 (m, 1H), 5.28 (dd, J=12.4 Hz, J=8.8 Hz, 1H), 4.35 (d, J=12.4 Hz, 1H), 4.06 (t, J=6.4 Hz, 2H), 3.81-3.76 (m, 1H), 3.13-3.11 (m, 1H), 2.35 (t, J=7.2 Hz, 2H), 2.13 (s, 6H), 1.87-1.84 (m, 2H), 1.44 (s, 3H), 0.84 (t, J=6.8 Hz, 3H). LC-MS (Method-C)=638.5 $[M+H]^+$; 95.38% at RT 4.83 min. HPLC (Method-B)=96.03% at RT 8.82 min. Chiral HPLC (Method-C)=Peak-1=51.35% at RT 4.84 min, Peak-2=48.65% at RT 8.90 min.

25-10

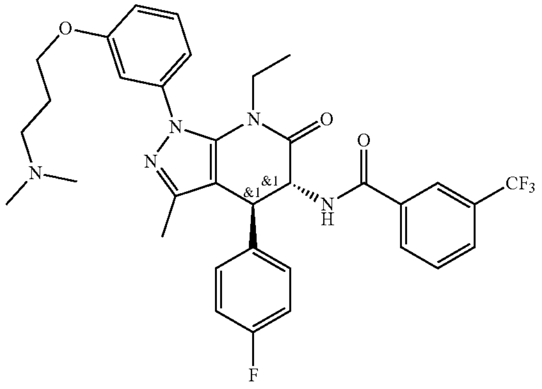

$^1$H NMR (400 MHZ, DMSO-$d_6$) δ=8.54 (d, J=7.2 Hz, 1H), 8.15-8.12 (m, 2H), 7.92 (d, J=8.0 Hz, 1H), 7.71 (t, J=7.6 Hz, 1H), 7.43 (t, J=8.4 Hz, 1H), 7.24-7.19 (m, 2H), 7.13-7.00 (m, 5H), 5.51 (t, J=6.8 Hz, 1H), 4.50 (d, J=7.2 Hz, 1H), 4.09-4.04 (m, 2H), 3.93-3.88 (m, 1H), 3.17-3.08 (m, 1H), 2.36 (t, J=6.8 Hz, 2H), 2.14 (s, 6H), 2.03 (s, 3H), 1.89-1.82 (m, 2H), 0.94 (t, J=7.2 Hz, 3H). LC-MS (Method-A)=636.43 $[M-H]^-$; 96.06% at RT 1.97 min. HPLC (Method-B)=95.72% at RT 9.62 min. Chiral HPLC (Method-C)=Peak-1=50.27% at RT 4.27 min, Peak-2=49.73% at RT 4.93 min.

Synthesis of 25-12:

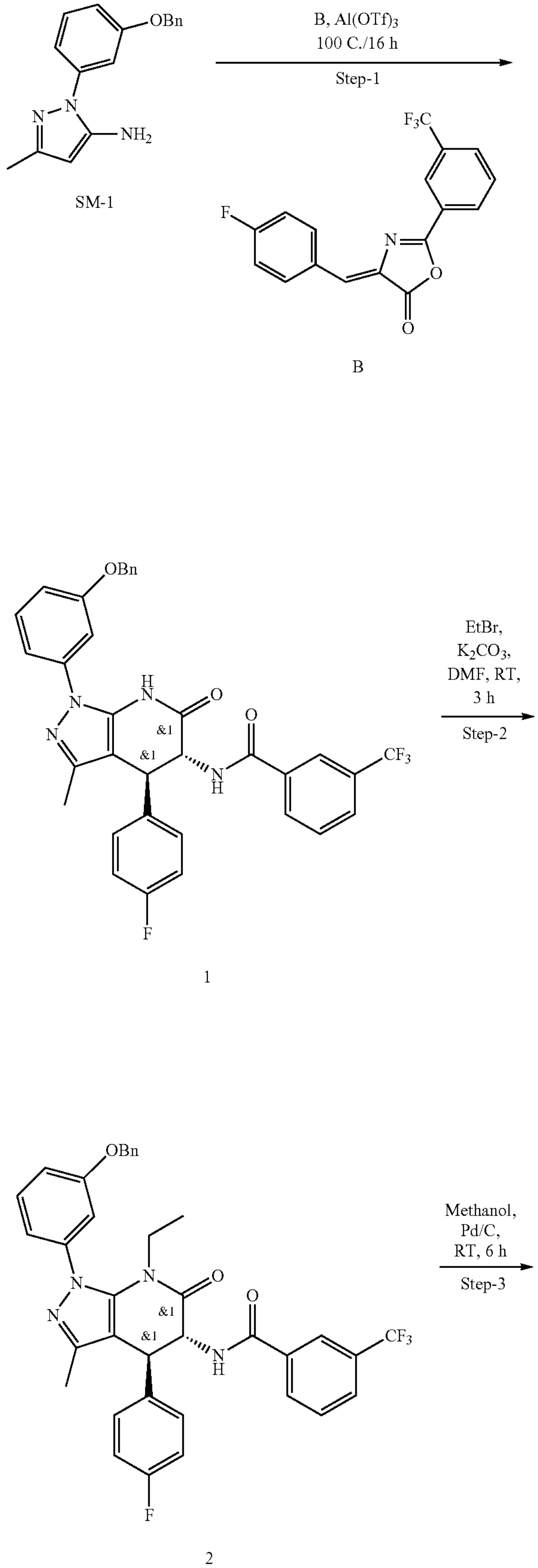

-continued

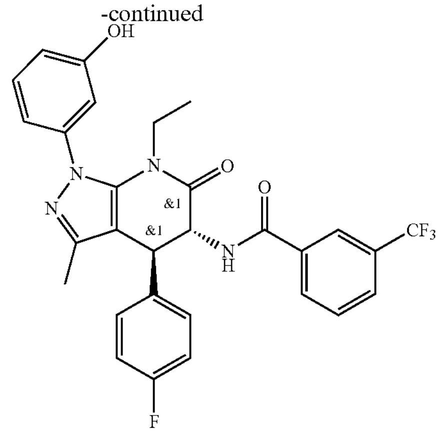

25-12

Step-1: Synthesis of N-[rac-(4S,5R)-1-(3-benzyloxyphenyl)-4-(4-fluorophenyl)-3-methyl-6-oxo-5,7-dihydro-4H-pyrazolo[3,4-b]pyridine-5-yl]-3-(trifluoromethyl)benzamide. Compound (1)

To a stirred solution of SM-1 (1.0 g, 3.5 mmol) in I (20 mL) was added Int-B (1.5 g, 3.5 mmol), followed by the addition of Aluminum trifluoromethanesulfonate (0.51 g, 1.1 mmol), and stirred the reaction mixture at 100° C. for 16 h. Reaction progress was monitored by TLC. After completion of reaction, the reaction mixture was concentrated under reduced pressure and diluted with water (150 mL) & extracted with EtOAc (2×200 mL) and separated. Organic layer was dried with over anhydrous $Na_2SO_4$ and concentrated under reduced pressure to afford a crude compound. Obtained crude compound was purified by column chromatography, combi-flash by using 100-200 mesh silica gel. The compound was eluted with 60% ethyl acetate in heptane and concentrated under vacuum to afford pure compound (1) (0.8 g, 31%), as a yellow solid.

$^1H$ NMR (400 MHZ, DMSO-$d_6$) δ=10.8 (m, 1H), 8.95 (d, J=8.8 Hz, 1H), 8.03-8.02 (m, 2H), 7.90 (d, J=8.0 Hz, 1H), 7.70 (t, J=7.6 Hz, 1H), 7.49-7.32 (m, 8H), 7.21-7.14 (m, 4H), 7.01 (d, J=6.4 Hz, 1H), 5.18 (s, 2H), 5.06-5.01 (m, 1H), 4.40 (d, J=12.4 Hz, 1H), 0.85 (t, J=6.4 Hz, 3H). LC-MS (Method-B)=615.2 $[M+H]^+$; 72.60% at RT 2.16 min.

Step-2: Synthesis of N-[rac-(4S,5R)-1-(3-benzyloxyphenyl)-7-ethyl-4-(4-fluorophenyl)-3-methyl-6-oxo-4,5-dihydropyrazolo[3,4-b]pyridine-5-yl]-3-(trifluoromethyl)benzamide compound (2)

A solution of compound (1) (0.8 g, 0.9 mmol) in DMF (15 mL) was cooled to 0-5° C., then potassium carbonate (0.4 g, 3 mmol) was added and stirred for 10 min. Then slowly bromoethane (0.5 g, 5 mmol) was added and the reaction mixture was stirred at room temperature for 3 h. Reaction progress was monitored by TLC. After completion of reaction, the reaction mixture was concentrated under reduced pressure and diluted with water (60 ml) & extracted with EtOAc (2×60 mL) and separated. It was concentrated under reduced pressure to afford a crude compound (0.9 g). Obtained crude compound was purified by column chromatography, combi-flash by using 100-200 mesh silica gel. The compound was eluted with 25% ethyl acetate in heptane and concentrated under vacuum pump to afford pure compound (2) (0.5 g, 70%), as a brown solid.

$^1H$ NMR (400 MHZ, DMSO-$d_6$) δ=8.96 (d, J=8.8 Hz, 1H), 8.00-7.87 (m, 3H), 7.91 (d, J=8.0 Hz, 1H), 7.68 (t, J=7.6 Hz, 1H), 7.46-7.26 (m, 9H), 7.18-7.11 (m, 4H), 5.28-5.18 (m, 3H), 4.34 (d, J=12.0 Hz, 1H), 3.74-3.69 (m, 1H), 3.05-2.99 (m, 1H), 1.43 (s, 3H), 0.84-0.76 (m, 3H). LC-MS (Method-B)=643.1 $[M+H]^+$; 89.40% at RT 2.53 min.

Step-3: Synthesis of N-[rac-(4S,5R)-7-ethyl-4-(4-fluorophenyl)-1-(3-hydroxyphenyl)-3-methyl-6-oxo-4,5-dihydropyrazolo[3,4-b]pyridine-5-yl]-3-(trifluoromethyl)benzamide 25-12

To a stirred solution of compound (2) (0.5 g, 0.7 mmol) in methanol (10 mL) was added Pd/C (100 mg) and the reaction mixture was stirred at room temperature for 6 h. Reaction progress was monitored by TLC. After completion of reaction, the reaction mixture was filtered through celite-bed, washed with MeOH (15 mL), and concentrated under reduced pressure to afford a crude compound (0.4 g). The crude compound was purified by column chromatography, combi-flash by using 100-200 mesh silica gel. The compound was eluted 60% ethyl acetate in heptane and concentrated under vacuum to afford pure compound 25-12 (0.23 g, 60%), as an off-white solid.

$^1H$ NMR (400 MHZ, DMSO-$d_6$) δ=9.91 (s, 1H), 8.97 (d, J=8.8 Hz, 1H), 8.01-7.99 (m, 2H), 7.89 (d, J=8.0 Hz, 1H), 7.69 (t, J=7.6 Hz, 1H), 7.44-7.40 (m, 2H), 7.32 (t, J=8 . . . 0 Hz, 1H), 7.16 (t, J=8.8 Hz, 2H), 7.01-6.97 (m, 2H), 6.99-6.97 (m 2H), 6.87-6.85 (m 1H), 5.26-5.27 (m, 1H), 4.35 (d, J=12.8 Hz, 1H), 3.84-3.78 (m, 1H), 3.31-3.12 (m, 1H), 1.44 (s, 3H), 0.85 (t, J=6.8 Hz, 3H). LC-MS (Method-A)=553.1 $[M+H]^+$; 97.80% at RT 2.25 min. HPLC (Method-C)=97.77% at RT 5.65 min. Chiral HPLC (Method-C)= Peak-1=49.74% at RT 3.76 min, Peak-2=50.26% at RT 4.16 min.

Example 26: Synthesis of Compound I-256

NMR:

$^1H$ NMR spectrum was recorded on Bruker 400 MHz and 300 MHz instruments internally referenced to a tetramethylsilane (TMS) signal. Chemical shifts (δ) and coupling constants (J) were expressed in parts per million and hertz, respectively.

LCMS:

Method-M (LCMS-13): Column: YMC-Triart C18, 50*3.0 mm, 3 μm, Mobile Phase: A: Water/0.05% ammonia water; B: Acetonitrile, Flow Rate: 1.2 mL/min. Oven Temperature: 40 C, Gradient program (B %): 0.01/50, 2.00/95, 2.80/95, 2.81/30.

The synthesis is described in the schemes below.

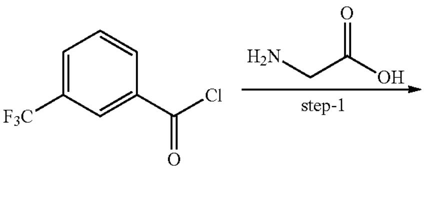

-continued
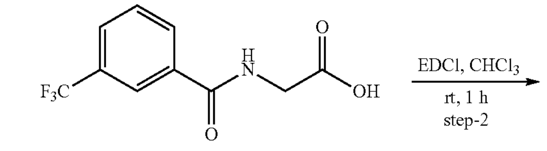
1
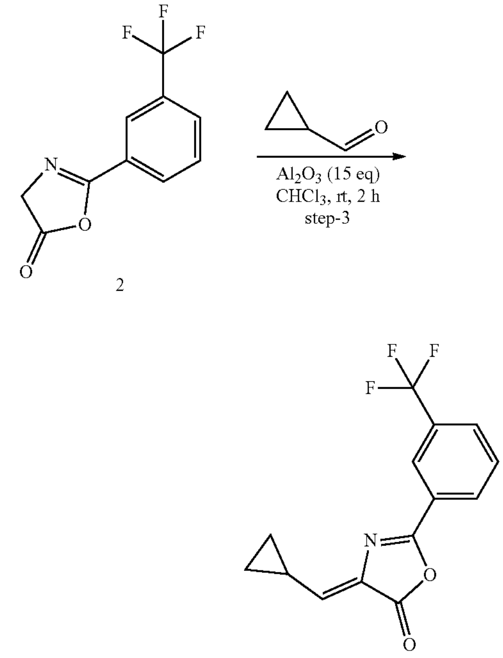
2
INT-B
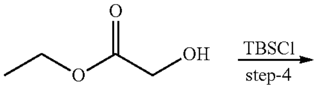
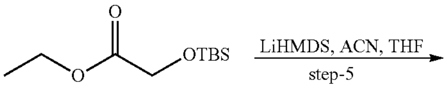
3
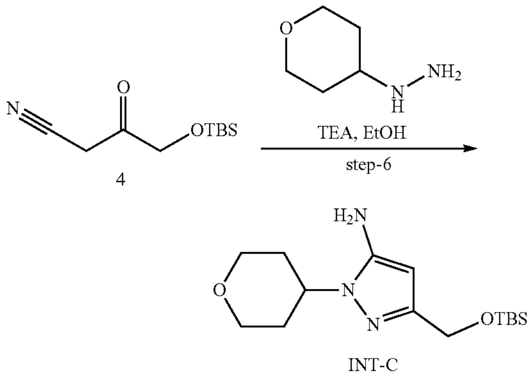
4
INT-C
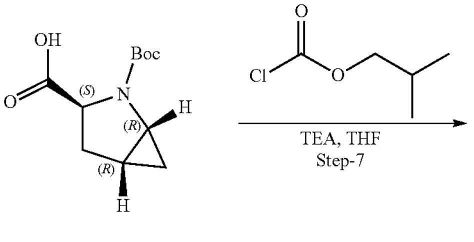
-continued
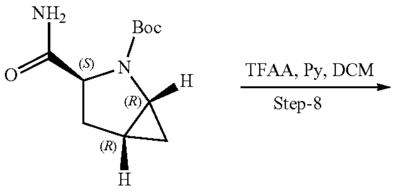
5
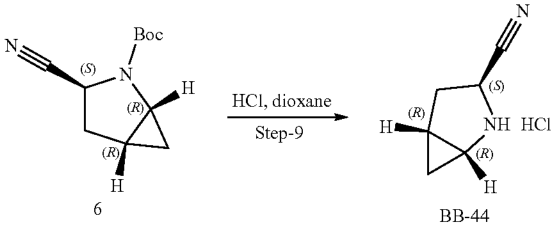
6
BB-44
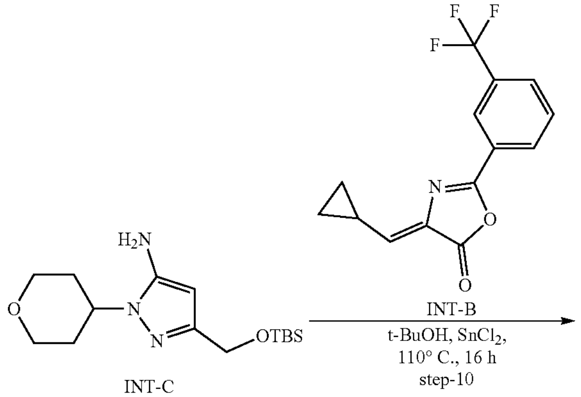
INT-C
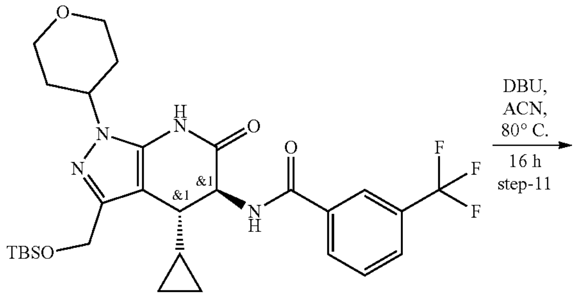
7
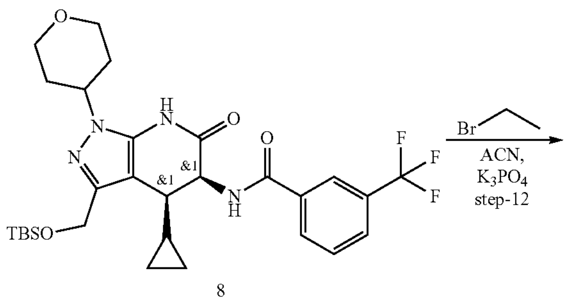
8

-continued

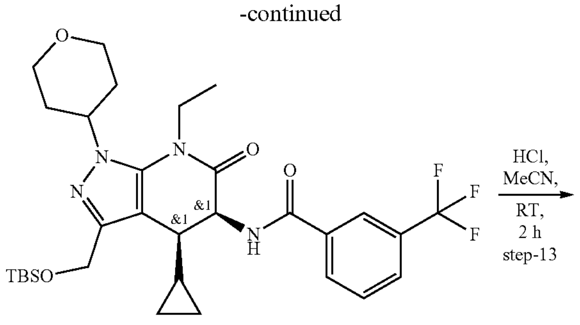

9

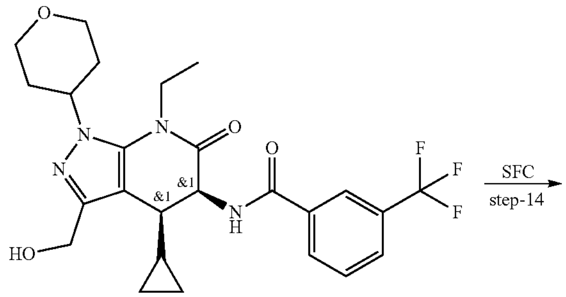

10

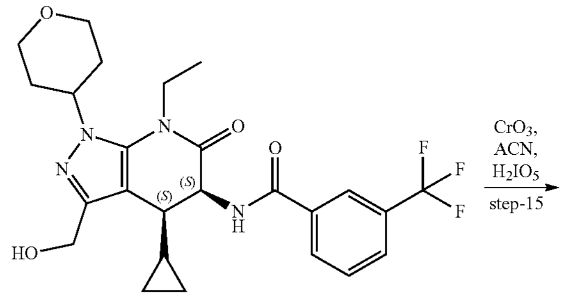

11

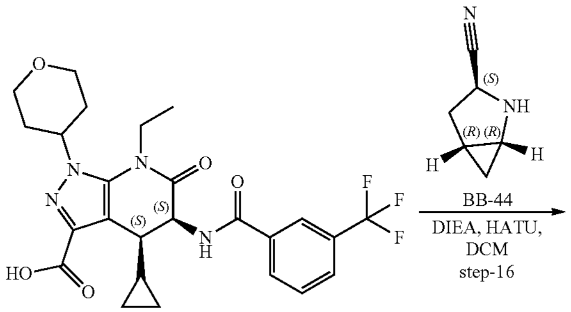

12

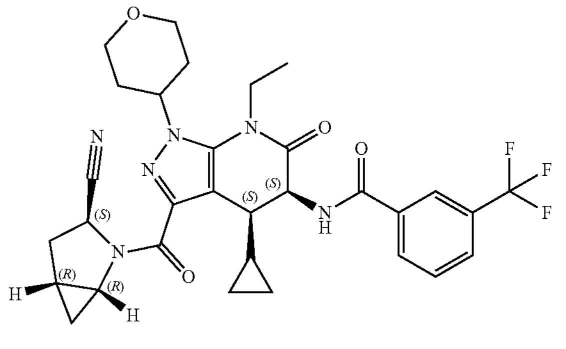

I-256

(1)

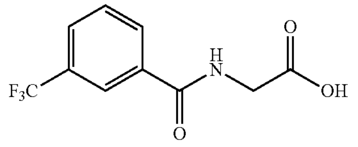

3-(trifluoromethyl)benzoyl)glycine

Into a 20 L 4-necked round-bottom flask were added glycine (378 g, 5.03 mol, 1.05 equiv), ACN (6000 mL), $H_2O$ (4000 mL) and NaOH (479 g, 12.0 mol, 2.50 equiv) at room temperature. To the above mixture was added 3-(trifluoromethyl)benzoyl chloride (1000 g, 4.79 mol, 1.00 equiv) dropwise over 1 h at −5° C. The resulting mixture was stirred for additional 5 h at room temperature. The mixture was acidified to pH 6 with conc. HCl. The resulting mixture was extracted with EtOAc (2×2 L). The combined organic layers were washed with brine (2×2 L), dried over anhydrous $Na_2SO_4$. After filtration, the filtrate was concentrated under reduced pressure. The residue was purified by trituration with PE (2 L). This resulted in {[3-(trifluoromethyl)phenyl]formamido}acetic acid (990 g, 83%) as a white solid.

(2)

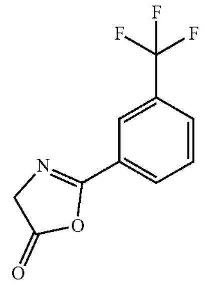

2-(3-(trifluoromethyl)phenyl)oxazol-5(4H)-one

A solution of {[3-(trifluoromethyl)phenyl]formamido}acetic acid (350 g, 1.42 mol, 1.00 equiv) and (3-[[(ethylimino)methylidene]amino]propyl)dimethylamine hydrochloride (299 g, 1.56 mol, 1.10 equiv) in trichloromethane (3.5 L) was stirred at room temperature for 1 h. The reaction was quenched with Water (3 L) at room temperature. The resulting mixture was extracted with EtOAc (3×1 L). The combined organic layers were washed with brine (3×1 L), dried over anhydrous $Na_2SO_4$. Desired product could be detected by LCMS. The crude product was used in the next step directly without further purification.

(INT-B)

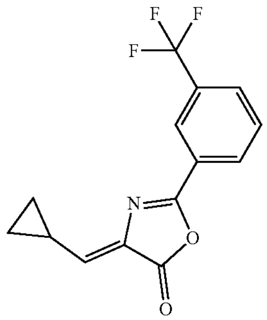

2-(3-(trifluoromethyl)phenyl)oxazol-5(4H)-one

A solution of 2-[3-(trifluoromethyl)phenyl]-4H-1,3-oxazol-5-one (300 g, 1.31 mol, 1.00 equiv) and $Al_2O_3$ (2002 g, 19.6 mol, 15.0 equiv), cyclopropanecarbaldehyde (82.6 g, 1.18 mol, 0.900 equiv) in trichloromethane (3 L) was stirred at room temperature for 1 h. The resulting mixture was filtered, the filter cake was washed with DCM (6×500 mL). The filtrate was concentrated under reduced pressure. The residue was purified by trituration with PE (100 mL). This resulted in (4Z)-4-(cyclopropylmethylidene)-2-[3-(trifluoromethyl)phenyl]-1,3-oxazol-5-one (93 g) as a white solid. LCMS Calculated for $C_{14}H_{11}F_3NO_2$: 281.07; Observed: 282.1 $[M+H]^+$.

(3)

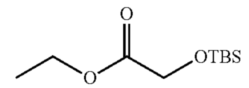

ethyl 2-((tert-butyldimethylsilyl)oxy)acetate

To a stirred solution of ethyl 2-hydroxyacetate (200 g, 1.92 mol, 1.00 equiv) and imidazole (196 g, 2.88 mol, 1.50 equiv) in DMF (2 L) were added TBSCl (347 g, 2.31 mol, 1.20 equiv) dropwise at room temperature under nitrogen atmosphere. The reaction mixture was stirred for 2.0 hours at room temperature. The mixture was diluted with water (5 L). The mixture was extracted with EtOAc (2×5 L). The combined organic phase was washed with brine (5 L), dried over anhydrous sodium sulfate, filtered and concentrated in vacuum. The residue was purified by silica gel chromatography, eluted with PE: EtOAc=10:90 to afford ethyl 2-[(tert-butyldimethylsilyl)oxy]acetate (320 g, 76%) as a light yellow oil.

(4)

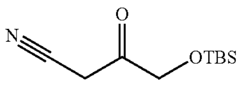

4-((tert-butyldimethylsilyl)oxy)-3-oxobutanenitrile

A solution of MeCN (11.3 g, 275 mmol, 1.20 equiv) in THF (500 mL) was treated with LiHMDS (59.6 mL, 298 mmol, 1.30 equiv) for 0.5 h at −78° C. under nitrogen atmosphere followed by the addition of ethyl 2-[(tert-butyldimethylsilyl)oxy]acetate (50.0 g, 229 mmol, 1.00 equiv) dropwise at −78° C. The resulting mixture was stirred for 1 h at room temperature under nitrogen atmosphere. The reaction was quenched with sat. $NH_4Cl$ (aq.) at room temperature. The resulting mixture was extracted with EtOAc (2×500 mL). The combined organic layers were washed with brine (2×500 mL), dried over anhydrous $Na_2SO_4$. After filtration, the filtrate was concentrated under reduced pressure. This resulted in 4-[(tert-butyldimethylsilyl)oxy]-3-oxobutanenitrile (48 g, 98%) as a yellow solid. The crude product was used in the next step directly without further purification.

3-(((tert-butyldimethylsilyl)oxy)methyl)-1-(tetrahydro-2H-pyran-4-yl)-1H-pyrazol-5-amine (INT-C)

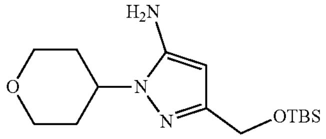

To a mixture of 4-[(tert-butyldimethylsilyl)oxy]-3-oxobutanenitrile (50.0 g, 234 mmol, 1.00 equiv) and oxan-4-ylhydrazine (29.9 g, 257 mmol, 1.10 equiv) in EtOH (500 ml) was added TEA (47.4 g, 469 mmol, 2.00 equiv) dropwise at room temperature. The resulting mixture was stirred for 3 h at room temperature under air atmosphere. The resulting mixture was concentrated under vacuum. The residue was purified by silica gel column chromatography, eluted with PE/EtOAc (5:1) to afford 3-(((tert-butyldimethylsilyl)oxy)methyl)-1-(tetrahydro-2H-pyran-4-yl)-1H-pyrazol-5-amine (21 g, 28%) as a yellow oil. LCMS Calculated for $C_{15}H_{29}N_3O_2Si$: 311.20; Observed: 312.2 $[M+H]^+$.

tert-butyl (1R,3S,5R)-3-carbamoyl-2-azabicyclo[3.1.0]hexane-2-carboxylate (5)

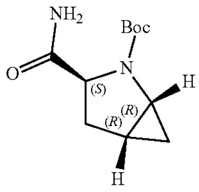

A solution of (1R,3S,5R)-2-(tert-butoxycarbonyl)-2-azabicyclo[3.1.0]hexane-3-carboxylic acid (1.00 g, 4.37 mmol, 1.00 equiv) in THF (10 mL) was treated with $Et_3N$ (884 mg, 8.74 mmol, 2.00 equiv) at 0° C. for 50 min followed by the addition of 2-methylpropyl carbonochloridate (890 mg, 6.56 mmol, 1.50 equiv) in portions at 0° C. for 2 h. The resulting mixture was stirred at room temperature for 2 h. Add the mixture dropwise to the ammonia solution. The resulting mixture was extracted with EtOAc (3×20 mL). The combined organic layers were washed with brine (1×50 mL), dried over anhydrous $Na_2SO_4$. After filtration, the filtrate was concentrated under reduced pressure. The residue was purified by silica gel column chromatography, eluted with PE/EtOAc (5:1) to afford tert-butyl (1R,3S,5R)-3-carbamoyl-2-azabicyclo[3.1.0]hexane-2-carboxylate (850 mg, 85% yield) as a yellow oil.

tert-butyl (1R,3S,5R)-3-cyano-2-azabicyclo[3.1.0]hexane-2-carboxylate (6)

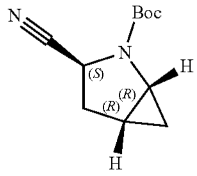

Into a 50 mL 3-necked round-bottom flask were added tert-butyl (1R,3S,5R)-3-carbamoyl-2-azabicyclo[3.1.0]hexane-2-carboxylate (850 mg, 3.76 mmol, 1.00 equiv), DCM (10 mL) and Py (1.20 g, 15.0 mmol, 4.00 equiv) at room temperature. To the above mixture was added 2,2,2-trifluoroacetyl 2,2,2-trifluoroacetate (1.58 g, 7.52 mmol, 2.00 equiv) dropwise at 0° C. The resulting mixture was stirred at 0° C. for additional 3 h. The resulting mixture was diluted with water (50 mL). The resulting mixture was extracted with $CH_2Cl_2$ (2×20 mL). The combined organic layers were washed with brine (2×40 mL), dried over anhydrous $Na_2SO_4$. After filtration, the filtrate was concentrated under reduced pressure. The residue was purified by silica gel column chromatography, eluted with PE/EtOAc (1:1) to afford tert-butyl (1R,3S,5R)-3-cyano-2-azabicyclo [3.1.0]hexane-2-carboxylate (500 mg) as a white solid.

(1R,3S,5R)-2-azabicyclo[3.1.0]hexane-3-carbonitrile (BB-44)

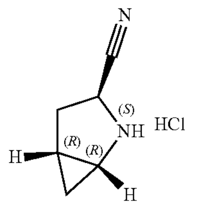

BB-44

To the solution of tert-butyl (1R,3S,5R)-3-cyano-2-azabicyclo[3.1.0]hexane-2-carboxylate (500 mg, 2.38 mmol, 1.00 equiv) in DCM (5 mL) was added HCl/dioxane (4 M, 2.4 mL, 9.54 mmol, 4.00 eq). The resulting mixture was stirred at room temperature for 4 h under nitrogen atmosphere. The resulting mixture was concentrated under reduced pressure. The residue (200 mg) was used to next step without further purification.

rac-N-((4R,5S)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamides (7)

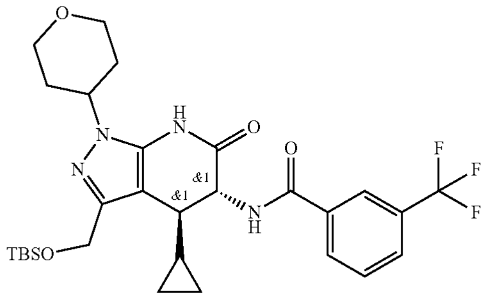

A solution of 3-(((tert-butyldimethylsilyl)oxy)methyl)-1-(tetrahydro-2H-pyran-4-yl)-1H-pyrazol-5-amine (197 g, 632 mmol, 1.00 equiv), $SnCl_2$ (12.0 g, 63.2 mmol, 0.10 equiv) and (Z)-4-(cyclopropylmethylene)-2-(3-(trifluoromethyl)phenyl)oxazol-5 (4H)-one (160 g, 569 mmol, 0.90 equiv) in t-BuOH (2000 mL) was stirred at 110° C. for 16 h. The mixture was allowed to cool down to room temperature. The resulting mixture was concentrated under reduced pressure. The residue was purified by silica gel column chromatography, eluted with PE/EtOAc (2:1) to afford rac-N-((4R,5S)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (400 g) as a yellow oil. LCMS Calculated for $C_{29}H_{39}F_3N_4O_4Si$: 592.27; Observed: 593.4 $[M+H]^+$.

rac-N-((4R,5R)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (8)

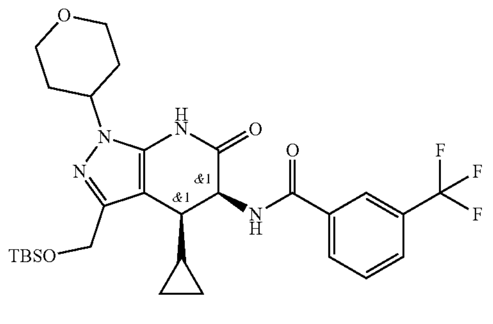

A solution of rac-N-((4R,5S)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (400 g, 674 mmol, 1.00 equiv) and DBU (390 g, 2.56 mol, 3.80 equiv) in ACN (1000 mL) was stirred at 80° C. for 16 h. The mixture was allowed to cool down to room temperature. The resulting mixture was concentrated under reduced pressure. The resulting mixture was diluted with $H_2O$ (2000 mL). The resulting mixture was extracted with EtOAc (3×1000 mL). The combined organic layers were washed with brine (1×500 mL), dried over anhydrous $Na_2SO_4$. After filtration, the filtrate was concentrated under reduced pressure. The residue was purified by silica gel column chromatography, eluted with PE/EA (2:1) to afford rac-N-((4R,5R)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (330 g, 82.5% yield) as a yellow oil. LCMS Calculated for $C_{29}H_{39}F_3N_4O_4Si$: 592.27; Observed: 593.4 $[M+H]^+$.

rac-N-((4R,5R)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (9)

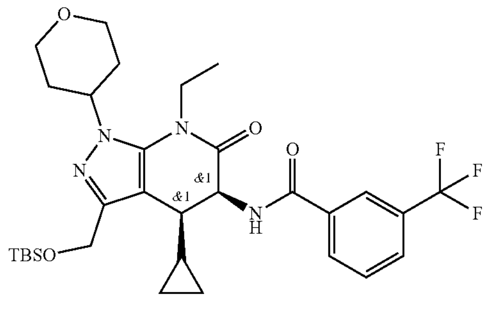

A solution of rac-N-((4R,5R)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (330 g, 557 mmol, 1.00 equiv), bromoethane (72.8 g, 668 mmol, 1.20 equiv) and $K_3PO_4$ (236 g, 1.11 mol, 1.50 equiv) in ACN (3000 mL) was stirred at 50° C. for 16 h. The mixture was allowed to cool down to room temperature. The mixture was allowed to cool down to room temperature. The resulting mixture was concentrated under reduced pressure. The residue was purified by silica gel column chromatography, eluted with PE/EtOAc (1:1) to afford rac-N-((4R,5R)-3-(((tert-butyldimethylsilyl)oxy)methyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (225 g, 65.1% yield) as a yellow solid. LCMS Calculated for $C_{31}H_{43}F_3N_4O_4Si$: 620.30; Observed: 621.3 [M+H]$^+$.

rac-N-((4R,5R)-4-cyclopropyl-7-ethyl-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (10)

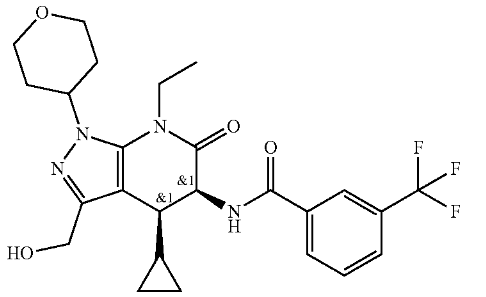

To a stirred mixture of rac-N-((4R,5R)-3-(((tert-butyldimethylsilyl)oxy)methyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (225 g, 362 mmol, 1.00 equiv) in MeCN (1000 mL) was added HCl (1000 mL, 2 mol/L in $H_2O$) in portions at room temperature. The mixture was stirred for 2 h at room temperature. The resulting mixture was concentrated under reduced pressure. The mixture was basified to pH 7 with saturated $NaHCO_3$ (aq.). The resulting mixture was extracted with EtOAc (3×1000 mL). The combined organic layers were washed with $H_2O$ (3×500 mL), dried over anhydrous $Na_2SO_4$. After filtration, the filtrate was concentrated under reduced pressure. The residue was purified by silica gel column chromatography, eluted with PE/EA (1:1) to afford rac-N-((4R,5R)-4-cyclopropyl-7-ethyl-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (125 g, 68.1% yield) as a yellow solid. LCMS Calculated for $C_{25}H_{29}F_3N_4O_4$: 506.21; Observed: 507.2 [M+H]$^+$.

N-((4S,5S)-4-cyclopropyl-7-ethyl-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (11)

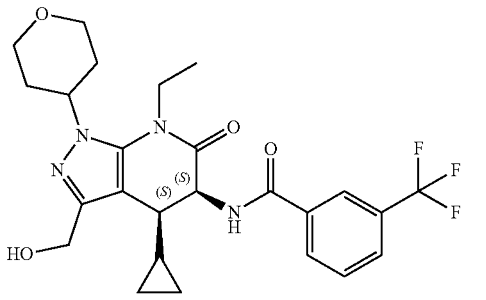

The crude product (125 g) was purified by Prep-chiral SFC with the following conditions (Column: XA-CHIRALPAK IG, 5*30 cm, 10 μm; Mobile Phase A: $CO_2$, Mobile Phase B: MEOH (0.1% 2M $NH_3$-MEOH); Flow rate: 150 mL/min; Gradient: isocratic 50% B; Column Temperature (C): 35; Back Pressure (bar): 100; Wave Length: 220 nm; RT1(min): 4; RT2(min): 6; Sample Solvent: MEOH; Injection Volume: 8 mL) to afford N-[(4S,5S)-4-cyclopropyl-7-ethyl-3-(hydroxymethyl)-1-(oxan-4-yl)-6-oxo-4H,5H-pyrazolo[3,4-b]pyridin-5-yl]-3-(trifluoromethyl)benzamide (60 g) as a white solid. LCMS Calculated for $C_{25}H_{29}F_3N_4O_4$: 506.21; Observed: 507.2 [M+H]$^+$. Optical Rotation: +27.996 (c=0.1 g/100 mL in MeOH, T=25° C.).

(4S,5S)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (12)

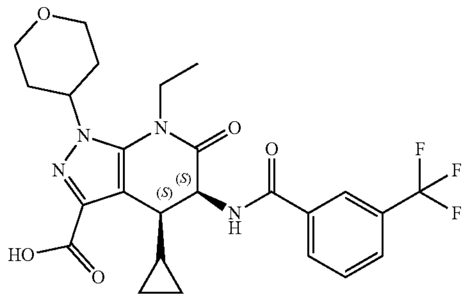

A solution of N-((4S,5S)-4-cyclopropyl-7-ethyl-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (30.0 g, 59.2 mmol, 1 equiv), periodic acid (40.5 g, 177 mmol, 3.00 equiv) and $CrO_3$ (2.96 g, 29.6 mmol, 0.300 equiv) in MeCN (300 mL) was stirred at room temperature for 16 h. The reaction was quenched with $N_2S_2O_3$ (900 ml) at room temperature. The resulting mixture was extracted with EtOAc (3×1000 mL). The combined organic layers were washed with brine (3×500 mL), dried over anhydrous $Na_2SO_4$. After filtration, the filtrate was concentrated under reduced pressure. The residue was purified by silica gel column chromatography, eluted with $CH_2Cl_2$/MeOH (10:1) to afford (4S,5S)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (26.0 g, 84% yield) as a yellow solid. LCMS Calculated for $C_{25}H_{27}F_3N_4O_5$: 520.19; Observed: 521.2 [M+H]$^+$. Optical rotation: +8.9 (c=0.1 g/100 mL in MeOH, T=25° C.)

N-((4S,5S)-3-((1R,3S,5R)-3-cyano-2-azabicyclo[3.1.0]hexane-2-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-256)

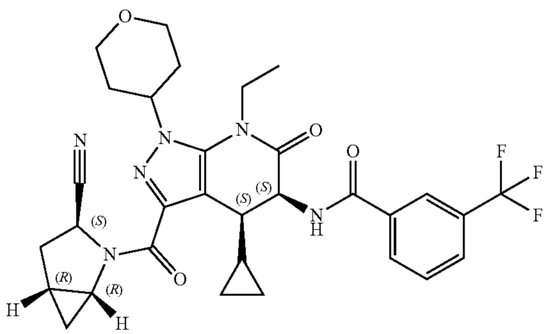

A solution of (4S,5S)-4-cyclopropyl-7-ethyl-1-(oxan-4-yl)-6-oxo-5-[3-(trifluoromethyl)benzamido]-4H,5H-pyrazolo[3,4-b]pyridine-3-carboxylic acid (100 mg, 0.192 mmol, 1.00 equiv), HATU (110 mg, 0.288 mmol, 1.50 equiv) and DIEA (497 mg, 0.384 mmol, 2.00 equiv) in DMF (1 mL) was stirred at room temperature for 30 min. To the above mixture was added (1R,3S,5R)-2-azabicyclo[3.1.0]hexane-3-carbonitrile (24.9 mg, 2.30 mmol, 1.2 equiv) in portions at room temperature. The resulting mixture was stirred at room temperature for additional 2 h. The resulting mixture was purified by reversed-phase flash chromatography with the following conditions: column, C18 silica gel; mobile phase, MeCN in water (0.1% FA), 10% to 60% gradient in 15 min; detector, UV 254 nm. This resulted in N-((4S,5S)-3-((1R,3S,5R)-3-cyano-2-azabicyclo[3.1.0]hexane-2-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (17.2 mg, 14% yield, 99.2% purity) as a white solid.

For all cell pasagings, cells were centrifuged at 300 g for 8 minutes at room temperature and cell number were normalized by MANTIS and Integra VIAFLO 384. All the compounds are diluted in DMSO and added to complete media by Formulatrix FAST and mixed starting from day −2. Cells were counted by Luna cell counter with AOPI Staining Solution (Nexcelom Bioscience, CS2-0106-25 mL) on day −2. Cells were counted by BD FACSCelesta Flow Cytometer with CountBright™ Plus Absolute Counting Beads (Thermal Fisher Scientific, C36995) and SYTOX AADvanced™ Ready Flow™ Reagent (Invitrogen, R37173) for other passages. Cells were cultured at 37° C. and 5% $CO_2$. DMSO concentration was kept at 0.1% to minimize any effects to the cells by the vehicle. Due to the insolubility of positive control, it was freshly made every 6 weeks with stock concentration at 3 mM while stock concentration for other compounds are 10 mM. Compound plates were kept at room temptureture to protect from light to avoid multiple freeze and thaw cycle.

| | |
|---|---|
| 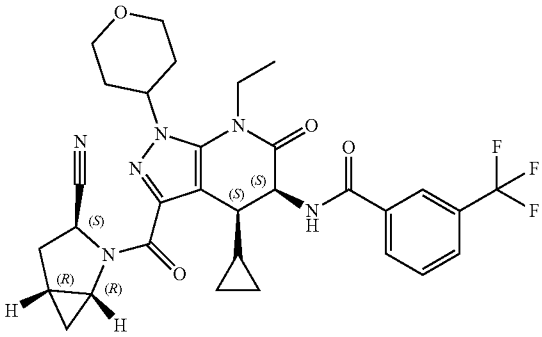<br>I-256 | $^1$H NMR (400 MHz, DMSO-$d_6$) δ 9.01 (d, J = 8.0 Hz, 1H), 8.31 (s, 1H), 8.25 (d, J = 7.9 Hz, 1H), 7.96 (d, J = 7.8 Hz, 1H), 7.76 (t, J = 7.8 Hz, 1H), 5.61-4.90 (m, 1H), 4.51 (m, 1H), 4.34 (d, J = 6.4 Hz, 1H), 4.18-4.01 (m, 2H), 3.98-3.81 (m, 2H), 3.58-3.45 (m, 2H), 3.42 (t, J = 6.4 Hz, 1H), 2.59 (s, 1H), 2.49-2.34 (m, 2H), 2.31-2.23 (m, 1H), 2.15-2.04 (m, 1H), 2.03-1.81 (m, 3H), 1.28 (t, J = 6.9 Hz, 3H), 0.93 (m, 1H), 0.84 (s, 1H), 0.62 (s, 1H), 0.51-0.46 (m, 1H), 0.24-0.10 (m, 3H). LCMS Calculated for $C_{31}H_{33}F_3N_6O_4$: 610.25; Observed (Method-M): 609.3 [M − H]$^-$, 99.2% at RT 1.507 min. |

Example 27: HBG1 Nanostring Assay

A Nanostring Assay was performed to evaluate the ability of the compounds to induce expression of the fetal hemoglobin gene HBG1 in cells. The data are shown as EC50, with stronger inducers having a lower EC50 value and higher YMax. CD34 culture and sample preparation Mobilized peripheral blood (mPB) derived CD34+ hematopoietic stem and progenitor cells (HSPCs) were thawed and plated at 500,000 cells/ml on day of cell thaw (day−4) in StemSpan (StemCell Tech, 09600) complete media supplemented with 1% StemSpan CC100 (StemCell Tech, 02690), and 0.2% human recombinant thrombopoietin (StemCell Tech, 02822). Forty eight hours later (day −2), the cells were passaged at a density of 200,000 cells/ml (100 ul/well in 96 well culture plate) in complete expantion media. The cells were plated at 200,000 cells/ml on day 0 and day 3, 400,000 cells/ml on day 5 in phase 1 erythroid differentiation containing StemSpan with 2.5 U/mL of EPO (R&D systems, 287-TC-500), 0.5 mg/mL of Holo-Transferrin (Sigma, T0665-500 MG), 1× Glutamine (Gluta-Max) (Gibco, 35050-061), 5 L/mL Lipid Mixture (Sigma, L0288-100 ML), 50 ng/mL SCF (R&D Systems, 255-SV-050), 10 ng/ml IL-3 (R&D Systems, 203-IL010) and 10 ng/mL Insulin (Sigma, 19278-5 ML) all 200 ul per well in 96 well culture plate. Cells were then passaged at 500,000 cells/ml and 200 μl per well on day 7 in phase 2 Erythroid differentiation (Phase 1 erythroid differentiation removing IL-3) until collection day (Day10). The culture conditions were used for both control DMSO as well as experimental treatments.

On the collection day (Day 10), 100K cells were collected and stored at −80° C. For direct hybridization for Nanostring, 100K cell pellet was lyzed in 25 μL of RLT (QIAGEN, 79216) with 1× β-Mercaptoethanol (Gibco, 21985-023) and shaked at 300-500 RPM for 5 minutes at room temperature. Cell lysate was stored in −80° C. after lysis.

Hybridization and Imaging

All hybridizations were done in a total volume of 15 μL (3 μL of RNA lysate added to master mix of 12 μL probe A/B, capture probe/reporter probes, proteinase K and attenuation oligos suspended in hybridization buffer). Samples were hybridized at 67° C. for 22 hr. Following hybridization, the tripartide complexes were purified, immobilized by nCounter Prep Station and imaged by Digital Analyzer (nCounter MAX/FLEX Analysis System), to generate digital counts of barcodes corresponding to each target in the multiplexed reaction. Labeled barcodes obtained from unamplified extracts were counted at 555 images or field of view (FOV). The barcode counts for each sample were recorded in Reporter Code Count (RCC) files that are imported into nSolver analysis software (provided with CodeSet by NS) for quality control evaluation.

Quality Control (QC) Metrics and Data Analysis

The quality control (QC) metric included limit of detection QC by checking for wells with less than 100 total counts for positive controls.

Hybridization signals were normalized against the ERCC positive controls and CodeSet Content (housekeeping gene). Briefly, this involved first calculating a sample-specific scaling factor by calculating arithmetic mean of geomeans of all ERCC positive controls with counts more than zero in all samples. Then this arithmetic mean was divided by the geometric mean of each lane to generate a lane-specific normalization factor. All negative controls and target-specific signal values were then normalized by multiplying counts values with their sample-specific scaling factor. The acceptable range for scaling factors is 0.3-3.0. For housekeeping gene(s) normalization, first calculating the arithmetic mean of geometric means of selected housekeeping genes for each lane for all samples. Then this arithmetic mean was divided by the geometric mean of each lane to generate a lane-specific normalization factor followed by multiplying the counts for every gene by its lane-specific normalization factor. The acceptable range for housekeeping genes normalization scaling factors is 0.1-10.

HBG1 dose-response curves, % Emax and EC50 values were generated by Dotmatic with setting control DMSO as 0% and biology control as 100%. When reporting EC50, Top will be fixed as 100% for compounds with observed Emax>=50%. For compounds with observed Emax<50% is reporting either inactive or max observed Emax.

Compounds with an EC50 less than or equal to 100.0 nM are designated as "+++". Compounds with an EC50 greater than 100.0 nM and less than or equal to 1000.0 nM are designated as "++". Compounds with an EC50 greater than 1000.0 nM are designated as "+". The results are shown in Table 1-I below.

Additional results are shown in Table 1-Ia below. The Nanostring Ymax observed data is relative to a control compound, presented in % which is shown in Table 1-I and Table 1-Ia below.

The Nanostring Ymax observed data is relative to a control compound (C1 shown in Example 41), presented in % which is shown in Table 1-I below. Compounds with a Nanostring Ymax greater than or equal to 0.0 and less than or equal to 50.0 are designated as "+". Compounds with a Nanostring Ymax greater than 50.0 and less than or equal to 100.0 are designated as "++". Compounds with a Nanostring Ymax greater than 100.0 are designated as "+++". ND means not determined.

TABLE 1-I

| HBG1 Nanostring Assay | | |
|---|---|---|
| Compound I-No. | Nanostring EC50 (nM) | Nanostring Ymax obs (%) |
| 1 | + | ++ |
| 2 | ND | ++ |
| 3 | +++ | +++ |
| 4 | ++ | ++ |
| 7 | + | + |
| 8 | + | ++ |
| 10 | ++ | ++ |
| 13 | + | + |
| 18 | ++ | + |
| 19 | +++ | +++ |
| 20 | + | + |
| 26 | ++ | ++ |
| 27 | ++ | ++ |
| 29 | + | + |
| 32 | ++ | ++ |
| 34 | ND | ++ |
| 35 | ++ | + |
| 37 | + | + |
| 38 | + | + |
| 40 | ND | ++ |
| 49 | ND | ++ |
| 51 | ++ | +++ |
| 53 | + | +++ |
| 58 | + | + |
| 60 | + | ++ |

TABLE 1-I-continued

| HBG1 Nanostring Assay | | |
|---|---|---|
| Compound I-No. | Nanostring EC50 (nM) | Nanostring Ymax obs (%) |
| 62 | + | + |
| 65 | + | ++ |
| 66 | + | + |
| 72 | ++ | ++ |
| 73 | +++ | ++ |
| 74 | ++ | ++ |
| 75 | ND | +++ |
| 77 | + | + |
| 87 | ++ | ++ |
| 88 | + | + |
| 89 | ND | ++ |
| 92 | ++ | ++ |
| 97 | ++ | ++ |
| 101 | + | ++ |
| 102 | ND | ++ |
| 103 | ++ | + |
| 104 | + | ++ |
| 106 | + | ++ |
| 107 | +++ | +++ |
| 108 | + | ++ |
| 110 | + | + |
| 112 | ++ | +++ |
| 116 | + | + |
| 117 | + | + |
| 119 | ++ | ++ |
| 122 | + | ++ |
| 125 | ++ | +++ |
| 127 | ++ | ++ |
| 129 | + | + |
| 132 | + | + |
| 136 | + | + |
| 139 | ND | ++ |
| 140 | ++ | ++ |
| 141 | + | ++ |
| 143 | + | + |
| 147 | + | + |
| 148 | ND | + |
| 151 | + | ++ |
| 152 | ++ | +++ |
| 153 | ++ | ++ |
| 161 | ++ | ++ |
| 167 | ++ | ++ |
| 173 | ++ | ++ |
| 177 | + | ++ |
| 178 | ++ | ++ |
| 179 | + | + |
| 180 | + | + |
| 181 | +++ | + |
| 184 | ND | ++ |
| 185 | ND | ++ |
| 190 | + | ++ |
| 192 | ++ | + |
| 197 | + | ++ |
| 201 | +++ | + |
| 202 | ND | + |
| 203 | ++ | + |
| 204 | + | + |
| 206 | + | + |
| 227 | ++ | ++ |
| 230 | + | ++ |
| 236 | +++ | + |
| 241 | ND | + |
| 246 | + | ++ |
| 247 | +++ | ++ |
| 248 | ND | ++ |
| 250 | + | ++ |
| 251 | ++ | + |
| 253 | + | ++ |
| 254 | + | ++ |
| 256 | +++ | +++ |

TABLE 1-Ia

| HBG1 Nanostring Assay | | |
|---|---|---|
| Compound No. | Nanostring EC50 (nM) | Nanostring Ymax obs (%) |
| I-266 | + | + |
| I-256 | +++ | +++ |
| I-270 | ++ | ++ |
| I-273 | ND | +++ |
| I-274 | ND | + |
| I-277 | +++ | +++ |
| I-278 | +++ | +++ |
| I-292 | +++ | +++ |
| I-334 | +++ | +++ |
| I-350 | +++ | +++ |
| I-358 | +++ | +++ |
| I-359 | +++ | +++ |
| I-360 | +++ | +++ |
| I-361 | +++ | +++ |
| I-362 | +++ | ++ |
| I-363 | +++ | +++ |
| I-364 | +++ | ++ |
| I-369 | +++ | +++ |
| I-370 | +++ | +++ |
| I-371 | ++ | ++ |
| I-372 | ++ | ++ |
| I-374 | +++ | +++ |
| I-377 | +++ | +++ |
| I-378 | +++ | ++ |
| I-379 | +++ | +++ |
| I-383 | +++ | ++ |
| I-386 | +++ | +++ |
| I-387 | +++ | +++ |
| I-399 | ++ | ++ |
| I-407 | ND | + |
| I-411 | ++ | ++ |
| I-418 | +++ | +++ |
| I-422 | ++ | +++ |
| I-447 | +++ | +++ |
| I-456 | ND | ++ |
| I-458 | ND | ++ |
| I-459 | +++ | ++ |
| I-491 | +++ | ++ |
| I-552 | +++ | +++ |
| I-573 | ND | ++ |
| I-574 | +++ | ++ |
| I-576 | + | + |
| I-582 | ++ | +++ |
| I-612 | ND | ++ |
| I-613 | ND | +++ |
| I-617 | ND | + |
| I-637 | ND | + |
| I-643 | +++ | ++ |
| I-644 | + | ++ |
| I-661 | +++ | ++ |
| I-677 | ND | +++ |
| I-692 | +++ | +++ |

Example 28: AlphaLISA Assay

An AlphaLISA assay was performed to evaluate the ability of the compounds to suppress neddylation, which is downstream from DCN-1 and DCN-2. A stronger inhibition of DCN-1 and DCN-2 is expected to result in a suppression of neddylation as shown by a lower AlphaLISA signal. The AlphaLISA assay for detecting Cullin-3 (CUL3) neddylation was performed according to manufacturer instructions (Revvity, Hopkinton, MA). Briefly, TF1 cells (ATCC) were plated in Iscove's Modified Dulbecco's Medium (IMDM) without supplements in 384-well plates. These cells were treated with 11 concentrations for 3 hours before lysing them with AlphaLISA lysis buffer, 5X (Revvity). To detect the level of CUL3 neddylation, biotinylated anti-NEDD8 antibody, was added followed by AlphaLISA Acceptor beads conjugated with anti-CUL3 antibody. After overnight incubation, Streptavidin-coated Alpha Donor beads were added and incubated for 1 hour. The AlphaLISA signal was then read on a VICTOR Nivo Multimode Microplate Reader (Revvity, Hopkinton, MA). The positive control was 1 μM DI-1548, which is reported to reduce CUL3 neddylation, also referred to as C-1 in Example 41 (Zhou et al. Nature Comm. 2021). The neddylation signal was normalized such that the percent inhibition is 0% for vehicle control and 100% for positive control. The dose-response curves were fitted with the Hill equation to obtain IC50 values (Graphpad Prism).

Compounds with an $IC_{50}$ less than or equal to 100.0 nM are designated as "+++". Compounds with an $IC_{50}$ greater than 100.0 nM and less than or equal to 1000.0 nM are designated as "++". Compounds with an $IC_{50}$ greater than 1000.0 nM are designated as "+". The results are shown in Table 1-II below.

Additional results are shown in Table 1-IIa below.

TABLE 1-II

| AlphaLISA Assay | |
|---|---|
| Compound I-No. | Neddylation IC50 (nM) |
| 1 | +++ |
| 2 | +++ |
| 3 | +++ |
| 4 | +++ |
| 5 | +++ |
| 7 | ++ |
| 8 | ++ |
| 12 | +++ |
| 13 | ++ |
| 18 | +++ |
| 19 | +++ |
| 20 | + |
| 25 | +++ |
| 26 | ++ |
| 27 | +++ |
| 29 | + |
| 32 | +++ |
| 34 | +++ |
| 35 | ++ |
| 37 | ++ |
| 40 | +++ |
| 49 | +++ |
| 50 | +++ |
| 51 | ++ |
| 53 | ++ |
| 56 | +++ |
| 57 | +++ |
| 58 | +++ |
| 62 | ++ |
| 65 | +++ |
| 67 | ++ |
| 73 | +++ |
| 74 | +++ |
| 75 | +++ |
| 76 | + |
| 77 | + |
| 80 | +++ |
| 84 | + |
| 88 | +++ |
| 89 | +++ |
| 92 | ++ |
| 97 | +++ |
| 101 | ++ |
| 102 | +++ |
| 103 | + |
| 104 | ++ |
| 106 | ++ |
| 107 | +++ |
| 108 | +++ |
| 110 | ++ |
| 112 | ++ |
| 117 | + |
| 122 | ++ |

TABLE 1-II-continued

| AlphaLISA Assay | |
|---|---|
| Compound I-No. | Neddylation IC50 (nM) |
| 125 | +++ |
| 127 | +++ |
| 129 | ++ |
| 132 | ++ |
| 136 | +++ |
| 138 | +++ |
| 139 | +++ |
| 140 | +++ |
| 143 | + |
| 147 | ++ |
| 148 | ++ |
| 149 | +++ |
| 150 | + |
| 152 | ++ |
| 153 | +++ |
| 161 | +++ |
| 167 | +++ |
| 173 | +++ |
| 177 | ++ |
| 178 | +++ |
| 179 | ++ |
| 180 | ++ |
| 181 | +++ |
| 184 | ++ |
| 185 | ++ |
| 190 | + |
| 192 | ++ |
| 197 | + |
| 201 | ++ |
| 202 | ++ |
| 203 | ++ |
| 204 | ++ |
| 206 | ++ |
| 227 | +++ |
| 230 | +++ |
| 236 | +++ |
| 241 | +++ |
| 244 | ++ |
| 246 | ++ |
| 247 | +++ |
| 248 | +++ |
| 249 | ++ |
| 250 | +++ |
| 251 | +++ |
| 253 | +++ |
| 254 | +++ |
| 255 | + |
| 256 | +++ |

TABLE 1-IIa

| AlphaLISA Assay | |
|---|---|
| Compound No. | Neddylation IC50 (nM) |
| I-266 | ++ |
| I-256 | +++ |
| I-270 | +++ |
| I-271 | +++ |
| I-272 | +++ |
| I-273 | +++ |
| I-274 | +++ |
| I-275 | +++ |
| I-276 | +++ |
| I-277 | +++ |
| I-278 | +++ |
| I-279 | +++ |
| I-280 | +++ |
| I-281 | +++ |
| I-282 | +++ |
| I-283 | +++ |
| I-284 | +++ |
| I-285 | +++ |

TABLE 1-IIa-continued

| AlphaLISA Assay | |
|---|---|
| Compound No. | Neddylation IC50 (nM) |
| I-286 | +++ |
| I-287 | +++ |
| I-288 | +++ |
| I-289 | +++ |
| I-290 | +++ |
| I-291 | +++ |
| I-292 | +++ |
| I-293 | +++ |
| I-294 | +++ |
| I-295 | +++ |
| I-296 | +++ |
| I-297 | +++ |
| I-298 | ++ |
| I-299 | ++ |
| I-300 | +++ |
| I-301 | +++ |
| I-302 | +++ |
| I-303 | +++ |
| I-304 | +++ |
| I-305 | +++ |
| I-306 | +++ |
| I-307 | +++ |
| I-308 | +++ |
| I-309 | +++ |
| I-310 | +++ |
| I-311 | +++ |
| I-312 | +++ |
| I-313 | +++ |
| I-314 | +++ |
| I-315 | +++ |
| I-316 | +++ |
| I-317 | +++ |
| I-318 | +++ |
| I-319 | +++ |
| I-320 | +++ |
| I-321 | +++ |
| I-322 | +++ |
| I-323 | +++ |
| I-324 | +++ |
| I-325 | +++ |
| I-326 | +++ |
| I-327 | +++ |
| I-328 | +++ |
| I-329 | +++ |
| I-330 | +++ |
| I-331 | +++ |
| I-332 | +++ |
| I-333 | +++ |
| I-334 | +++ |
| I-335 | +++ |
| I-336 | +++ |
| I-337 | +++ |
| I-338 | +++ |
| I-339 | +++ |
| I-340 | +++ |
| I-341 | +++ |
| I-342 | +++ |
| I-343 | +++ |
| I-344 | +++ |
| I-345 | +++ |
| I-346 | +++ |
| I-347 | +++ |
| I-348 | +++ |
| I-349 | +++ |
| I-350 | +++ |
| I-351 | +++ |
| I-352 | +++ |
| I-353 | +++ |
| I-354 | +++ |
| I-355 | +++ |
| I-356 | +++ |
| I-357 | +++ |
| I-358 | +++ |
| I-359 | +++ |
| I-360 | +++ |
| I-361 | +++ |

TABLE 1-IIa-continued

| AlphaLISA Assay | |
|---|---|
| Compound No. | Neddylation IC50 (nM) |
| I-362 | +++ |
| I-363 | +++ |
| I-364 | +++ |
| I-365 | +++ |
| I-366 | +++ |
| I-367 | +++ |
| I-368 | +++ |
| I-369 | +++ |
| I-370 | +++ |
| I-371 | +++ |
| I-372 | +++ |
| I-373 | +++ |
| I-374 | +++ |
| I-375 | +++ |
| I-376 | +++ |
| I-377 | +++ |
| I-378 | +++ |
| I-379 | +++ |
| I-380 | +++ |
| I-381 | +++ |
| I-382 | +++ |
| I-383 | +++ |
| I-384 | +++ |
| I-385 | +++ |
| I-386 | +++ |
| I-387 | +++ |
| I-388 | +++ |
| I-389 | +++ |
| I-390 | +++ |
| I-391 | +++ |
| I-392 | +++ |
| I-393 | +++ |
| I-394 | +++ |
| I-395 | +++ |
| I-396 | +++ |
| I-397 | +++ |
| I-398 | + |
| I-399 | +++ |
| I-400 | ++ |
| I-401 | + |
| I-402 | ++ |
| I-403 | ++ |
| I-405 | + |
| I-406 | ++ |
| I-407 | +++ |
| I-408 | ++ |
| I-409 | ++ |
| I-410 | ++ |
| I-411 | +++ |
| I-412 | ++ |
| I-413 | +++ |
| I-414 | + |
| I-415 | + |
| I-416 | ++ |
| I-417 | ++ |
| I-418 | +++ |
| I-420 | + |
| I-421 | ++ |
| I-422 | +++ |
| I-425 | +++ |
| I-427 | ++ |
| I-428 | +++ |
| I-429 | +++ |
| I-430 | +++ |
| I-431 | ++ |
| I-432 | ++ |
| I-436 | +++ |
| I-437 | + |
| I-438 | +++ |
| I-439 | +++ |
| I-441 | + |
| I-442 | + |
| I-444 | ++ |
| I-445 | +++ |
| I-446 | + |
| I-447 | +++ |

TABLE 1-IIa-continued

| AlphaLISA Assay | |
|---|---|
| Compound No. | Neddylation IC50 (nM) |
| I-448 | + |
| I-450 | ++ |
| I-451 | + |
| I-452 | + |
| I-453 | + |
| I-454 | +++ |
| I-455 | + |
| I-456 | +++ |
| I-457 | + |
| I-458 | +++ |
| I-459 | +++ |
| I-460 | + |
| I-461 | + |
| I-462 | +++ |
| I-463 | + |
| I-464 | + |
| I-465 | +++ |
| I-467 | ++ |
| I-469 | +++ |
| I-470 | +++ |
| I-474 | ++ |
| I-476 | + |
| I-478 | ++ |
| I-479 | + |
| I-480 | + |
| I-481 | +++ |
| I-482 | +++ |
| I-483 | + |
| I-486 | +++ |
| I-487 | ++ |
| I-488 | +++ |
| I-489 | +++ |
| I-490 | ++ |
| I-491 | +++ |
| I-492 | +++ |
| I-494 | + |
| I-495 | + |
| I-496 | +++ |
| I-497 | +++ |
| I-498 | + |
| I-499 | ++ |
| I-501 | + |
| I-503 | + |
| I-506 | + |
| I-509 | +++ |
| I-514 | +++ |
| I-515 | ++ |
| I-516 | +++ |
| I-517 | ++ |
| I-518 | +++ |
| I-519 | +++ |
| I-521 | +++ |
| I-522 | + |
| I-524 | +++ |
| I-525 | + |
| I-526 | +++ |
| I-527 | ++ |
| I-528 | + |
| I-530 | +++ |
| I-531 | ++ |
| I-533 | ++ |
| I-534 | + |
| I-535 | + |
| I-536 | ++ |
| I-538 | ++ |
| I-539 | +++ |
| I-540 | + |
| I-541 | + |
| I-542 | ++ |
| I-543 | ++ |
| I-544 | + |
| I-548 | + |
| I-549 | +++ |
| I-550 | +++ |
| I-551 | ++ |
| I-552 | +++ |

TABLE 1-IIa-continued

| AlphaLISA Assay | |
|---|---|
| Compound No. | Neddylation IC50 (nM) |
| I-557 | + |
| I-558 | + |
| I-559 | +++ |
| I-560 | +++ |
| I-561 | +++ |
| I-562 | + |
| I-563 | + |
| I-564 | + |
| I-565 | +++ |
| I-566 | + |
| I-567 | + |
| I-569 | +++ |
| I-570 | ++ |
| I-571 | + |
| I-572 | + |
| I-573 | +++ |
| I-574 | +++ |
| I-576 | +++ |
| I-577 | + |
| I-578 | ++ |
| I-579 | +++ |
| I-581 | + |
| I-582 | +++ |
| I-583 | + |
| I-584 | + |
| I-585 | ++ |
| I-586 | +++ |
| I-589 | +++ |
| I-593 | +++ |
| I-594 | + |
| I-595 | + |
| I-596 | + |
| I-597 | + |
| I-599 | ++ |
| I-600 | +++ |
| I-601 | ++ |
| I-602 | + |
| I-603 | ++ |
| I-604 | + |
| I-605 | + |
| I-606 | + |
| I-607 | + |
| I-608 | + |
| I-609 | + |
| I-611 | + |
| I-612 | +++ |
| I-613 | +++ |
| I-614 | +++ |
| I-615 | + |
| I-616 | + |
| I-617 | +++ |
| I-619 | ++ |
| I-621 | + |
| I-622 | + |
| I-624 | +++ |
| I-625 | + |
| I-626 | +++ |
| I-628 | ++ |
| I-629 | + |
| I-630 | +++ |
| I-631 | ++ |
| I-632 | + |
| I-633 | ++ |
| I-634 | + |
| I-635 | ++ |
| I-636 | + |
| I-637 | + |
| I-638 | + |
| I-639 | + |
| I-640 | ++ |
| I-641 | ++ |
| I-642 | + |
| I-643 | +++ |
| I-644 | +++ |
| I-646 | +++ |
| I-647 | + |

TABLE 1-IIa-continued

| AlphaLISA Assay | |
|---|---|
| Compound No. | Neddylation IC50 (nM) |
| I-648 | + |
| I-649 | + |
| I-650 | +++ |
| I-654 | +++ |
| I-656 | +++ |
| I-658 | + |
| I-659 | +++ |
| I-660 | +++ |
| I-661 | +++ |
| I-662 | + |
| I-664 | ++ |
| I-666 | + |
| I-667 | +++ |
| I-668 | ++ |
| I-669 | ++ |
| I-673 | + |
| I-674 | + |
| I-676 | + |
| I-677 | + |
| I-679 | +++ |
| I-680 | +++ |
| I-681 | + |
| I-682 | +++ |
| I-683 | +++ |
| I-684 | +++ |
| I-685 | ++ |
| I-686 | ++ |
| I-687 | +++ |
| I-689 | ++ |
| I-692 | +++ |
| I-693 | +++ |
| I-694 | +++ |
| I-697 | + |
| I-699 | + |
| I-700 | ++ |
| I-702 | ++ |
| I-703 | + |
| I-704 | ++ |
| I-705 | + |
| I-706 | +++ |
| I-707 | +++ |

Example 29: HbF HPLC Cell Culture and Analysis

A Cell Culture Assay was performed to evaluate the ability of compounds to induce fetal hemoglobin in a cell culture. The amount fetal hemoglobin protein induced was measured by HPLC.

Cell culture began on Day −4 (thaw day). Thaw buffer was prepared by sterile filtering 6 mL of Human Serum Albumin and 144 mL of PBS to make sterile 1% I/PBS. Cells were removed from liquid nitrogen storage and mostly thawed in a 37° C. water bath. Once the ice in the cryovials was melted, cells were transferred quickly into a 50 ml conical tube. Cryovial was rinsed once with thaw buffer and buffer was transferred over to the conical tube as well. Next, doubling volumes of thaw buffer was added to the conical and gently swirled for ~30 seconds to one minute (for example: 2 mL was added and swirled, then 4 mL, then 8 mL, and so on) until the volume in the conical is 32 mL. Cells and buffer were centrifuged at 300 G for 8 minutes, and the supernatant was aspirated. Another 32 mL of thaw buffer was added slowly, swirling the tube. The tube was again centrifuged at 300 G for 8 minutes and the supernatant was aspirated. Cells were counted by resuspending in 1 mL of expansion media and counting with AOPI to determine the concentration of cells/mL.

On day 2, Passage & Treatment Day, each cell culture well was counted. Next fresh CD34 Expansion Media was made which contained StemSpan SFEM, CC100 and TPO all from StemCell technologies. Appropriate volume of cells was collected, centrifuged at 300 g and resuspended in fresh media. Cells were plated in treatment format at a density of 200,000 cells/ml, 25,000 cells/well. Finally, they were treated with test compounds as well as positive and negative controls.

On Days 0, 3 & 5 the same process was carried out. First, each cell culture well was counted. Next Phase 1 Erythroid Differentiation Media was freshly made, which contained StemSpan SFEM, 2.5 U/ml EPO, 0.5 mg/ml Holo-TF, 1× Glutamax, 5 μl/ml chemically defined lipid mixture, 10 ng/ml insulin, 50 ng/ml SCF, 10 ng/ml IL-3. Appropriate volume of cells was collected, centrifuged at 300 g and resuspended in fresh media. Cells should now be in fresh wells at a density of 100,000 cells/ml. 60,000 cells, 60,000 cells and 100,000 cells for days 0, 3, 5 respectively. Finally, fresh compound was added to each well at each timepoint (Days 0, 3 & 5).

On Day 7 media and cell culture density changes. Each cell culture well was counted. Next, Phase 2 Erythroid Differentiation Media was freshly made, which contains StemSpan SFEM, 2.5 U/ml EPO, 0.5 mg/ml Holo-TF, 1× Glutamax, 5 μl/ml chemically defined lipid mixture, 10 ng/ml insulin, 50 ng/ml SCF. Appropriate volume of cells was collected, centrifuged at 300 g and resuspended in fresh media. Cells were plated in fresh wells at a density of 500,000 cells/ml, 300,000 cells/well. Finally, fresh compound was added to each well at Day 7 timepoint.

On Day 10 media formulation is once again changed. Each cell culture well was counted. Fresh Phase 3 Erythroid Differentiation Media was made which contains StemSpan SFEM, 2.5 U/ml EPO, 0.5 mg/ml Holo-TF, 1× Glutamax, 5 μl/ml chemically defined lipid mixture, 10 ng/ml insulin. Appropriate volume of cells was collected, centrifuged at 300 g and resuspended in fresh media. Cells were plated in fresh wells at a density of 500,000 cells/ml, 500,000 cells/well. Finally, fresh compound was added to each well at Day 10 timepoint.

On Day 12 the cell density is once again changed. Each cell culture well was counted. Fresh Phase 3 Erythroid Differentiation Media was made. Appropriate volume of cells was collected, centrifuged at 300 g and resuspended in fresh media. Cells were plated in fresh wells at a density of 1,000,000 cells/ml, 1,000,000 cells/well. Finally fresh compound was added to each well.

Day 14 ($18^{th}$ day of experiment) refers to the terminal day of culture. Each cell culture well was counted. Next between 150K and 650K cells were placed in a uniquely labeled 1.5 ml standard tube. Cells were centrifuged in media at 300 g for 8 minutes, then as much of the media as possible was removed without disturbing the pellet. The pellet was washed with 500 μl dPBS and once again spun at 300 g for 8 minutes. As much of the supernatant as possible was removed without disturbing the pellet and immediately frozen at −80° C. Cell pellets are now ready for HPLC lysis and analysis.

All centrifugations were run at 300× G for 8 minutes at room temperature. Cells were cultured in a standard incubator at 37° C. and 5% C). Cell culture plates were either a 96-well treated plate for Day −2 or 24-well cell culture treated plates for day 0 through 14. Culture wells were counted using a 1:1 mix of cells and AOPI. Counting was done on Nexcelom Cellaca.

Methods for assaying % HBF and % F+ cells are well known in the art. Non-limiting examples include high performance liquid chromatography (HPLC), flow cytometry, or ion-exchange chromatography. The HbF % is usually measured by HPLC. The flow cytometry assay, the standard clinical method, may be used for assaying % F+ cells by immunofluorescent techniques. In addition to flow cytometry, ion-exchange chromatography may be used to measure the fraction HbF relative to all other hemoglobin (HbF/HbA+HbF).

Compounds with an EC50 less than or equal to 50.0 nM are designated as "+++". Compounds with an EC50 greater than 50.0 nM and less than or equal to 200.0 nM are designated as "++". Compounds with an EC50 greater than 200.0 nM are designated as "+". The results are shown in Table 1-III below.

Additional results are shown in Table 1-IIIa below.

The Hemoglobin HPLC Ymax observed data is relative to a control compound, presented in % which is shown in Table 1-III below. Compounds with a Hemoglobin HPLC Ymax greater than or equal to 0.0 and less than or equal to 65.0 are designated as "+". Compounds with a Hemoglobin HPLC Ymax greater than 65.0 and less than or equal to 100.0 are designated as "++". Compounds with a Hemoglobin HPLC Ymax greater than 100.0 are designated as "+++".

Additional results are shown in Table 1-IIIa below.

TABLE 1-III

HbF HPLC Cell Culture Assay

| Compound I-No. | Hemoglobin HPLC EC50 (nM) | Hemoglobin HPLC Ymax obs (%) |
|---|---|---|
| 3 | ++ | ++ |
| 5 | ++ | ++ |
| 34 | + | ++ |
| 49 | +++ | ++ |
| 73 | + | ++ |
| 92 | + | + |
| 112 | + | +++ |
| 139 | +++ | ++ |
| 140 | + | + |
| 152 | + | ++ |
| 256 | ++ | ++ |

TABLE 1-IIIa

HbF HPLC Cell Culture Assay

| Compound No. | Hemoglobin HPLC EC50 (nM) | Hemoglobin HPLC Ymax obs (%) |
|---|---|---|
| I-256 | ++ | ++ |
| I-277 | +++ | ++ |
| I-278 | + | + |
| I-281 | +++ | ++ |
| I-285 | +++ | ++ |
| I-294 | ++ | ++ |
| I-304 | +++ | ++ |
| I-334 | ++ | ++ |
| I-350 | +++ | ++ |
| I-372 | ++ | ++ |
| I-377 | ++ | ++ |
| I-418 | +++ | +++ |
| I-422 | ++ | ++ |
| I-661 | + | ++ |
| I-692 | + | ++ |

Example 30: TR-FRET Assay

A TR-FRET assay was performed to evaluate the ability of the compounds to bind the DCN-1 protein.

The TR-FRET assay was designed following the Scott et al. protocol (Scott et al., Nat Chem Biol. 2017 August; 13

(8): 850-857. Doi: 10.1038/nchembio.2386). The recombinant form of the DCN1 (DCUND1) protein PONY domain was produced using an *E. coli* expression system at Viva Biotech (China). The DCN1 protein was biotinylated (EZ sulfo-NHS-LC-biotin; Thermofisher) for labeling with streptavidin terbium (Tb) cryptate in the reaction. The probe was changed to a non-covalent DCN1 inhibitor labeled with carboxyfluorescein (FAM; Zhou et al., *Nat Commun.* 2017; 8:1150. Doi: 10.1038/s41467-017-01243-7). Buffer conditions were modified to enhance protein stability by exchanging Tween20 for TritonX and increasing NaCl to 200 mM. The compounds were screened against 5 nM DCN1 and 20 nM FAM-probe or 0.31 nM DCN1 and 900 nM total probe (100 nM FAM-labeled plus 800 nM unlabeled). The TR-FRET ratio between Tb-DCN1 and the FAM-labeled probe was measured in a 384-well opti-plate (Perkin Elmer) using a plate reader (BMG) at 1, 5, and 24 hrs after treatment with compound (final DMSO concentration of 0.1%). The ratio was normalized to the high (DCN1 and FAM-probe) and low (DCN1 and no probe) controls for a readout of % activity (=100*(x−low)/(high−low). The % activity across concentrations is used to determine the IC50.

Compounds with an $IC_{50}$ less than or equal to 200.0 nM are designated as "++++". Compounds with an $IC_{50}$ greater than 200.0 nM and less than or equal to 1000.0 nM are designated as "+++". Compounds with an $IC_{50}$ greater than 1000.0 nM and less than or equal to 3000.0 nM are designated as "++". Compounds with an $IC_{50}$ greater than 3000.0 nM are designated as "+". The results are shown in Table 2 below.

Additional results are shown in Table 2a below.

TABLE 2

| | TR-FRET Assay | |
|---|---|---|
| Compound No. | TR FRET IC50 1 hr (nM) | TR FRET IC50 24 hr (nM) |
| I-1 | ++++ | ++++ |
| I-2 | ++++ | ++++ |
| I-3 | ++++ | ++++ |
| I-4 | ++++ | ++++ |
| I-5 | ++++ | ++++ |
| I-6 | +++ | ++++ |
| I-7 | ++ | ++ |
| I-8 | ++++ | ++++ |
| I-9 | +++ | ++ |
| I-10 | +++ | ++++ |
| I-11 | +++ | ++++ |
| I-12 | ++++ | ++++ |
| I-13 | ++ | ++ |
| I-14 | ++++ | ++++ |
| I-15 | ++ | ++ |
| I-16 | +++ | ++ |
| I-17 | ++ | ++ |
| I-18 | ++++ | ++++ |
| I-19 | ++++ | ++++ |
| I-20 | ++ | ++ |
| I-21 | ++ | ++ |
| I-22 | ++ | ++ |
| I-23 | ++ | ++ |
| I-24 | ++ | ++ |
| I-25 | ++++ | ++++ |
| I-26 | ++++ | ++++ |
| I-27 | ++++ | ++++ |
| I-28 | +++ | ++++ |
| I-29 | ++ | ++ |
| I-30 | + | ++ |
| I-31 | ++ | ++ |
| I-32 | ++++ | ++++ |
| I-33 | ++ | ++ |
| I-34 | ++++ | ++++ |
| I-35 | + | ++++ |

TABLE 2-continued

| | TR-FRET Assay | |
|---|---|---|
| Compound No. | TR FRET IC50 1 hr (nM) | TR FRET IC50 24 hr (nM) |
| I-36 | ++ | ++ |
| I-37 | ++ | ++ |
| I-38 | ++ | ++ |
| I-39 | ++ | ++ |
| I-40 | ++++ | ++++ |
| I-41 | ++ | ++ |
| I-42 | ++ | ++ |
| I-43 | +++ | ++ |
| I-44 | +++ | ++++ |
| I-45 | ++ | ++++ |
| I-46 | ++ | ++ |
| I-47 | ++++ | ++++ |
| I-48 | ++++ | ++++ |
| I-49 | ++++ | ++++ |
| I-50 | ++++ | ++++ |
| I-51 | +++ | +++ |
| I-52 | ++ | ++ |
| I-53 | ++ | +++ |
| I-54 | +++ | +++ |
| I-55 | ++ | ++ |
| I-56 | ++++ | ++++ |
| I-57 | ++++ | ++++ |
| I-58 | ++++ | ++++ |
| I-59 | ++ | ++ |
| I-60 | ++++ | +++ |
| I-61 | +++ | +++ |
| I-62 | ++++ | +++ |
| I-63 | ++++ | +++ |
| I-64 | ++ | +++ |
| I-65 | ++++ | +++ |
| I-66 | ++++ | +++ |
| I-67 | ++++ | ++++ |
| I-68 | +++ | +++ |
| I-69 | +++ | +++ |
| I-70 | ++ | ++ |
| I-71 | +++ | +++ |
| I-72 | +++ | +++ |
| I-73 | ++++ | ++++ |
| I-74 | ++++ | ++++ |
| I-75 | ++++ | ++++ |
| I-76 | ++ | ++ |
| I-77 | ++ | ++ |
| I-78 | ++ | ++ |
| I-79 | ++ | ++ |
| I-80 | ++ | ++ |
| I-81 | ++ | ++ |
| I-82 | ++ | ++ |
| I-83 | ++ | ++ |
| I-84 | ++ | ++ |
| I-85 | ++ | ++ |
| I-86 | +++ | +++ |
| I-87 | +++ | ++++ |
| I-88 | ++++ | ++++ |
| I-89 | ++++ | ++++ |
| I-90 | + | + |
| I-91 | +++ | +++ |
| I-92 | +++ | ++++ |
| I-93 | ++++ | ++++ |
| I-94 | +++ | +++ |
| I-95 | +++ | +++ |
| I-96 | +++ | +++ |
| I-97 | ++++ | +++ |
| I-98 | +++ | ++++ |
| I-99 | +++ | +++ |
| I-100 | +++ | +++ |
| I-101 | +++ | +++ |
| I-102 | ++++ | ++++ |
| I-103 | +++ | +++ |
| I-104 | +++ | +++ |
| I-105 | +++ | +++ |
| I-106 | +++ | +++ |
| I-107 | ++++ | ++++ |
| I-108 | +++ | +++ |
| I-109 | +++ | +++ |
| I-110 | +++ | +++ |

TABLE 2-continued

| TR-FRET Assay | | |
|---|---|---|
| Compound No. | TR FRET IC50 1 hr (nM) | TR FRET IC50 24 hr (nM) |
| I-111 | ++ | +++ |
| I-112 | ++ | +++ |
| I-113 | +++ | +++ |
| I-114 | +++ | +++ |
| I-115 | + | + |
| I-116 | +++ | +++ |
| I-117 | +++ | +++ |
| I-118 | +++ | +++ |
| I-119 | +++ | +++ |
| I-120 | +++ | +++ |
| I-121 | ++++ | ++++ |
| I-122 | ++++ | ++++ |
| I-123 | +++ | +++ |
| I-124 | +++ | +++ |
| I-125 | + | +++ |
| I-126 | +++ | +++ |
| I-127 | ++++ | ++++ |
| I-128 | ++ | +++ |
| I-129 | +++ | ++++ |
| I-130 | +++ | +++ |
| I-131 | ++ | +++ |
| I-132 | +++ | ++++ |
| I-133 | +++ | +++ |
| I-134 | +++ | +++ |
| I-135 | +++ | +++ |
| I-136 | +++ | ++++ |
| I-137 | +++ | +++ |
| I-138 | ++++ | ++++ |
| I-139 | ++++ | ++++ |
| I-140 | ++++ | ++++ |
| I-141 | +++ | ++++ |
| I-142 | +++ | +++ |
| I-143 | +++ | +++ |
| I-144 | ++ | +++ |
| I-145 | +++ | +++ |
| I-146 | ++ | +++ |
| I-147 | ++ | +++ |
| I-148 | ++ | +++ |
| I-149 | ++++ | ++++ |
| I-150 | ++ | +++ |
| I-151 | +++ | ++++ |
| I-152 | ++++ | ++++ |
| I-153 | +++ | ++++ |
| I-154 | +++ | ++++ |
| I-155 | ++ | +++ |
| I-156 | +++ | +++ |
| I-157 | ++ | +++ |
| I-158 | +++ | +++ |
| I-159 | ++ | +++ |
| I-249 | +++ | +++ |
| I-253 | ++ | ++++ |
| I-251 | ++++ | ++++ |
| I-247 | ++++ | ++++ |
| I-246 | +++ | +++ |
| I-244 | ++ | +++ |
| I-256 | ++++ | ++++ |
| I-254 | +++ | ++++ |
| I-255 | ++ | ++ |
| I-248 | +++ | ++++ |
| I-250 | +++ | ++++ |

TABLE 2a

| TR-FRET Assay | | |
|---|---|---|
| Compound No. | TR FRET IC50 1 hr (nM) | TR FRET IC50 24 hr (nM) |
| I-266 | +++ | +++ |
| I-256 | ++++ | ++++ |
| I-270 | ++++ | ++++ |
| I-271 | ++++ | ++++ |

TABLE 2a-continued

| TR-FRET Assay | | |
|---|---|---|
| Compound No. | TR FRET IC50 1 hr (nM) | TR FRET IC50 24 hr (nM) |
| I-272 | ++++ | ++++ |
| I-273 | ++++ | ++++ |
| I-274 | ++++ | ++++ |
| I-275 | ++++ | ++++ |
| I-276 | +++ | ++++ |
| I-277 | ++++ | ++++ |
| I-278 | +++ | ++++ |
| I-279 | ++++ | ++++ |
| I-280 | ++++ | ++++ |
| I-281 | ++++ | ++++ |
| I-282 | ++++ | ++++ |
| I-283 | ++++ | ++++ |
| I-284 | ++++ | ++++ |
| I-285 | ++++ | ++++ |
| I-286 | ++++ | ++++ |
| I-287 | ++++ | ++++ |
| I-288 | ++++ | ++++ |
| I-289 | ++++ | ++++ |
| I-290 | ++++ | ++++ |
| I-291 | ++++ | ++++ |
| I-292 | ++++ | ++++ |
| I-293 | ++++ | ++++ |
| I-294 | ++++ | ++++ |
| I-295 | ++ | ++++ |
| I-296 | ++ | ++++ |
| I-297 | ++ | ++++ |
| I-298 | +++ | +++ |
| I-299 | ++++ | +++ |
| I-300 | ++++ | ++++ |
| I-301 | ++++ | ++++ |
| I-302 | ++++ | ++++ |
| I-303 | ++++ | ++++ |
| I-304 | ++++ | ++++ |
| I-305 | ++++ | ++++ |
| I-306 | ++++ | ++++ |
| I-307 | ++++ | ++++ |
| I-308 | ++++ | ++++ |
| I-309 | ++++ | ++++ |
| I-310 | ++++ | ++++ |
| I-311 | ++++ | ++++ |
| I-312 | ++++ | ++++ |
| I-313 | ++++ | ++++ |
| I-314 | ++++ | ++++ |
| I-315 | ++++ | ++++ |
| I-316 | ++++ | ++++ |
| I-317 | ++++ | ++++ |
| I-318 | ++ | ++++ |
| I-319 | ++ | ++++ |
| I-320 | ++++ | ++++ |
| I-321 | ++++ | ++++ |
| I-322 | ++++ | ++++ |
| I-323 | ++++ | ++++ |
| I-324 | +++ | ++++ |
| I-325 | ++++ | ++++ |
| I-326 | ++++ | ++++ |
| I-327 | ++++ | ++++ |
| I-328 | ++++ | ++++ |
| I-329 | ++++ | ++++ |
| I-330 | ++++ | ++++ |
| I-331 | ++++ | ++++ |
| I-332 | +++ | ++++ |
| I-333 | +++ | ++++ |
| I-334 | ++++ | ++++ |
| I-335 | ++ | ++++ |
| I-336 | ++++ | ++++ |
| I-337 | ++++ | ++++ |
| I-338 | ++ | ++++ |
| I-339 | ++ | ++++ |
| I-340 | ++++ | ++++ |
| I-341 | ++++ | ++++ |
| I-342 | ++++ | ++++ |
| I-343 | ++ | ++++ |
| I-344 | +++ | ++++ |
| I-345 | +++ | ++++ |
| I-346 | +++ | ++++ |

TABLE 2a-continued

| TR-FRET Assay | | |
|---|---|---|
| Compound No. | TR FRET IC50 1 hr (nM) | TR FRET IC50 24 hr (nM) |
| I-347 | +++ | ++++ |
| I-348 | +++ | ++++ |
| I-349 | ++++ | ++++ |
| I-350 | ++++ | ++++ |
| I-351 | ++++ | ++++ |
| I-352 | ++++ | ++++ |
| I-353 | ++++ | ++++ |
| I-354 | ++++ | ++++ |
| I-355 | ++++ | ++++ |
| I-356 | +++ | ++++ |
| I-357 | ++++ | ++++ |
| I-358 | ++++ | ++++ |
| I-359 | ++++ | ++++ |
| I-360 | ++++ | ++++ |
| I-361 | ++++ | ++++ |
| I-362 | ++++ | ++++ |
| I-363 | ++++ | ++++ |
| I-364 | ++++ | ++++ |
| I-365 | ++++ | ++++ |
| I-366 | ++++ | ++++ |
| I-367 | ++++ | ++++ |
| I-368 | ++++ | ++++ |
| I-369 | ++++ | ++++ |
| I-370 | ++++ | ++++ |
| I-371 | +++ | ++++ |
| I-372 | ++++ | ++++ |
| I-373 | ++++ | ++++ |
| I-374 | +++ | ++++ |
| I-375 | ++++ | ++++ |
| I-376 | ++++ | ++++ |
| I-377 | ++++ | ++++ |
| I-378 | ++++ | ++++ |
| I-379 | ++++ | ++++ |
| I-380 | ++++ | ++++ |
| I-381 | ++++ | ++++ |
| I-382 | +++ | ++++ |
| I-383 | ++++ | ++++ |
| I-384 | ++++ | ++++ |
| I-385 | ++ | ++++ |
| I-386 | ++++ | ++++ |
| I-387 | ++++ | ++++ |
| I-388 | ++++ | ++++ |
| I-389 | ++++ | ++++ |
| I-390 | ++++ | ++++ |
| I-391 | ++++ | ++++ |
| I-392 | ++++ | ++++ |
| I-393 | ++++ | ++++ |
| I-394 | ++++ | ++++ |
| I-395 | ++++ | ++++ |
| I-396 | ++++ | ++++ |
| I-397 | ++++ | ++++ |
| I-398 | ++ | ++ |
| I-399 | ++++ | ++++ |
| I-400 | ++++ | ++++ |
| I-401 | ++ | ++ |
| I-402 | ++ | ++ |
| I-403 | +++ | +++ |
| I-405 | ++ | ++ |
| I-406 | +++ | ++++ |
| I-407 | ++++ | ++++ |
| I-408 | ++++ | ++++ |
| I-409 | ++ | ++++ |
| I-410 | ++ | +++ |
| I-411 | ++++ | ++++ |
| I-412 | ++++ | ++++ |
| I-413 | ++ | ++++ |
| I-414 | ++ | ++ |
| I-415 | ++ | ++ |
| I-416 | ++ | +++ |
| I-417 | ++ | +++ |
| I-418 | ++++ | ++++ |
| I-419 | ++ | ++ |
| I-420 | ++ | ++ |
| I-421 | ++ | ++++ |
| I-422 | ++++ | ++++ |

TABLE 2a-continued

| TR-FRET Assay | | |
|---|---|---|
| Compound No. | TR FRET IC50 1 hr (nM) | TR FRET IC50 24 hr (nM) |
| I-423 | ++ | ++ |
| I-424 | ++ | ++ |
| I-425 | ++++ | ++++ |
| I-426 | ++ | ++ |
| I-427 | ++ | +++ |
| I-428 | +++ | ++++ |
| I-429 | ++++ | ++++ |
| I-430 | +++ | ++++ |
| I-431 | +++ | +++ |
| I-432 | +++ | ++++ |
| I-433 | ++ | ++ |
| I-434 | ++ | ++ |
| I-435 | ++ | ++ |
| I-436 | ++++ | ++++ |
| I-437 | ++ | ++++ |
| I-438 | ++++ | ++++ |
| I-439 | ++++ | ++++ |
| I-440 | ++ | ++ |
| I-441 | ++ | +++ |
| I-442 | ++ | +++ |
| I-444 | ++ | +++ |
| I-445 | ++++ | ++++ |
| I-446 | ++ | ++ |
| I-447 | ++++ | ++++ |
| I-448 | ++++ | ++++ |
| I-450 | ++ | ++ |
| I-451 | ++ | ++ |
| I-452 | ++ | ++ |
| I-453 | ++ | +++ |
| I-454 | ++ | +++ |
| I-455 | ++ | ++ |
| I-456 | ++++ | ++++ |
| I-457 | ++ | ++ |
| I-458 | ++++ | ++++ |
| I-459 | ++++ | ++++ |
| I-460 | +++ | +++ |
| I-461 | ++ | ++ |
| I-462 | ++++ | ++++ |
| I-463 | ++ | ++ |
| I-464 | ++ | ++ |
| I-465 | ++++ | ++++ |
| I-466 | ++ | ++ |
| I-467 | ++ | ++++ |
| I-468 | ++++ | ++++ |
| I-469 | ++ | ++++ |
| I-470 | ++++ | ++++ |
| I-471 | ++ | ++ |
| I-472 | +++ | ++++ |
| I-473 | ++ | ++ |
| I-474 | ++ | +++ |
| I-475 | ++ | ++ |
| I-476 | ++ | ++ |
| I-478 | ++ | ++++ |
| I-479 | ++ | ++ |
| I-480 | ++ | ++ |
| I-481 | ++++ | ++++ |
| I-482 | ++++ | ++++ |
| I-483 | ++ | +++ |
| I-486 | +++ | ++++ |
| I-487 | +++ | ++++ |
| I-488 | +++ | ++++ |
| I-489 | +++ | ++++ |
| I-490 | ++++ | ++++ |
| I-491 | +++ | ++++ |
| I-492 | +++ | +++ |
| I-494 | ++ | ++ |
| I-495 | +++ | +++ |
| I-496 | ++++ | ++++ |
| I-497 | ++++ | ++++ |
| I-498 | ++ | ++ |
| I-499 | ++ | ++ |
| I-501 | ++ | +++ |
| I-502 | ++ | +++ |
| I-503 | ++ | +++ |
| I-504 | ++ | ++ |

TABLE 2a-continued

| TR-FRET Assay | | |
|---|---|---|
| Compound No. | TR FRET IC50 1 hr (nM) | TR FRET IC50 24 hr (nM) |
| I-505 | ++ | ++ |
| I-506 | ++ | ++ |
| I-507 | ++ | ++ |
| I-508 | ++ | ++++ |
| I-509 | ++++ | ++++ |
| I-510 | ++ | ++ |
| I-511 | ++ | ++ |
| I-512 | ++ | ++ |
| I-513 | ++ | ++ |
| I-514 | ++++ | ++++ |
| I-515 | +++ | ++++ |
| I-516 | ++++ | ++++ |
| I-517 | ++ | +++ |
| I-518 | +++ | ++++ |
| I-519 | ++++ | ++++ |
| I-521 | ++ | ++++ |
| I-522 | ++ | ++ |
| I-523 | ++ | ++ |
| I-524 | +++ | ++++ |
| I-525 | ++ | ++ |
| I-526 | ++++ | ++++ |
| I-527 | +++ | ++++ |
| I-528 | ++ | ++ |
| I-530 | +++ | ++++ |
| I-531 | ++ | ++++ |
| I-533 | +++ | +++ |
| I-534 | ++ | ++ |
| I-535 | ++ | ++ |
| I-536 | ++++ | ++++ |
| I-538 | +++ | ++++ |
| I-539 | ++++ | ++++ |
| I-540 | ++ | ++ |
| I-541 | ++ | ++ |
| I-542 | ++ | +++ |
| I-543 | ++++ | ++++ |
| I-544 | ++ | ++ |
| I-546 | ++ | ++ |
| I-547 | +++ | ++++ |
| I-548 | ++ | ++ |
| I-549 | +++ | ++++ |
| I-550 | ++++ | ++++ |
| I-551 | +++ | +++ |
| I-552 | ++++ | ++++ |
| I-553 | +++ | ++++ |
| I-554 | ++ | ++ |
| I-555 | ++ | ++ |
| I-556 | ++ | ++ |
| I-557 | ++ | ++ |
| I-558 | ++ | ++ |
| I-559 | +++ | ++++ |
| I-560 | ++++ | ++++ |
| I-561 | ++ | ++++ |
| I-562 | ++ | ++ |
| I-563 | ++ | ++ |
| I-564 | ++ | ++ |
| I-565 | +++ | ++++ |
| I-566 | ++ | ++ |
| I-567 | ++ | ++ |
| I-569 | +++ | ++++ |
| I-570 | ++ | +++ |
| I-571 | ++ | ++ |
| I-572 | ++ | ++ |
| I-573 | ++++ | ++++ |
| I-574 | ++++ | ++++ |
| I-576 | +++ | ++++ |
| I-577 | +++ | +++ |
| I-578 | ++ | ++ |
| I-579 | ++++ | ++++ |
| I-581 | ++ | +++ |
| I-582 | ++++ | ++++ |
| I-583 | ++ | ++ |
| I-584 | ++ | ++ |
| I-585 | ++ | ++++ |
| I-586 | ++ | +++ |
| I-588 | ++ | ++ |

TABLE 2a-continued

| TR-FRET Assay | | |
|---|---|---|
| Compound No. | TR FRET IC50 1 hr (nM) | TR FRET IC50 24 hr (nM) |
| I-589 | ++++ | ++++ |
| I-590 | ++ | ++ |
| I-591 | ++ | ++ |
| I-592 | ++ | ++ |
| I-593 | ++++ | ++++ |
| I-594 | ++ | ++ |
| I-595 | ++ | ++ |
| I-596 | ++ | ++ |
| I-597 | ++ | ++ |
| I-598 | ++ | ++ |
| I-599 | ++ | ++ |
| I-600 | +++ | ++++ |
| I-601 | ++ | +++ |
| I-602 | ++ | ++ |
| I-603 | ++ | ++++ |
| I-604 | ++ | ++ |
| I-605 | ++ | ++ |
| I-606 | +++ | +++ |
| I-607 | +++ | ++ |
| I-608 | ++ | ++++ |
| I-609 | ++++ | ++++ |
| I-611 | ++ | ++ |
| I-612 | ++++ | ++++ |
| I-613 | ++++ | ++++ |
| I-614 | +++ | ++++ |
| I-615 | ++ | +++ |
| I-616 | ++ | ++ |
| I-617 | ++++ | ++++ |
| I-618 | ++ | ++ |
| I-619 | ++ | ++++ |
| I-620 | ++++ | ++++ |
| I-621 | ++ | ++ |
| I-622 | ++ | ++ |
| I-623 | ++ | ++ |
| I-624 | +++ | +++ |
| I-625 | ++ | ++ |
| I-626 | ++++ | ++++ |
| I-627 | ++++ | ++++ |
| I-628 | ++ | ++ |
| I-629 | ++ | ++ |
| I-630 | ++++ | ++++ |
| I-631 | +++ | ++++ |
| I-632 | ++ | ++ |
| I-633 | ++ | +++ |
| I-634 | ++ | ++ |
| I-635 | ++ | ++++ |
| I-636 | ++ | ++ |
| I-637 | ++ | +++ |
| I-638 | ++++ | ++++ |
| I-639 | ++ | ++ |
| I-640 | ++ | ++ |
| I-641 | +++ | +++ |
| I-642 | ++ | ++ |
| I-643 | ++++ | ++++ |
| I-644 | ++++ | ++++ |
| I-646 | ++++ | ++++ |
| I-647 | ++ | ++ |
| I-648 | ++ | ++ |
| I-649 | ++ | ++ |
| I-650 | ++++ | ++++ |
| I-652 | ++ | ++ |
| I-653 | ++ | ++ |
| I-654 | ++++ | ++++ |
| I-655 | ++ | ++ |
| I-656 | ++++ | ++++ |
| I-658 | ++ | +++ |
| I-659 | ++++ | ++++ |
| I-660 | ++++ | ++++ |
| I-661 | ++++ | ++++ |
| I-662 | ++ | ++ |
| I-663 | ++ | ++ |
| I-664 | +++ | +++ |
| I-666 | ++ | ++ |
| I-667 | +++ | ++++ |
| I-668 | ++ | ++ |

TABLE 2a-continued

| TR-FRET Assay | | |
|---|---|---|
| Compound No. | TR FRET IC50 1 hr (nM) | TR FRET IC50 24 hr (nM) |
| I-669 | ++ | +++ |
| I-673 | +++ | +++ |
| I-674 | ++ | ++ |
| I-676 | ++ | ++ |
| I-677 | ++++ | ++++ |
| I-679 | +++ | ++++ |
| I-680 | +++ | ++++ |
| I-681 | ++ | ++ |
| I-682 | +++ | ++++ |
| I-683 | +++ | ++++ |
| I-684 | ++++ | ++++ |
| I-685 | ++++ | ++++ |
| I-686 | ++ | ++++ |
| I-687 | ++++ | ++++ |
| I-688 | +++ | ++++ |
| I-689 | ++ | ++++ |
| I-690 | +++ | ++++ |
| I-691 | ++ | ++++ |
| I-692 | +++ | ++++ |
| I-693 | ++++ | ++++ |
| I-694 | ++++ | ++++ |
| I-695 | ++ | ++ |
| I-696 | ++ | ++ |
| I-697 | ++ | ++ |
| I-698 | +++ | +++ |
| I-699 | ++ | ++ |
| I-700 | ++ | +++ |
| I-701 | ++ | ++ |
| I-702 | ++ | +++ |
| I-703 | ++ | ++ |
| I-704 | ++ | ++++ |
| I-705 | ++ | ++ |
| I-706 | ++ | +++ |
| I-707 | ++++ | ++++ |

Example 31: Intact Protein MS Analysis with the RapidFire-TOF System

An MS assay was performed to evaluate the ability of the compounds to covalently modify DCN-1.

DCN1 protein, His-TEV-DCN1, were expressed in *E. Coli*. The His-tagged protein was first purified with an Ni-NTA column. The His-tag was cleaved using His-tag TEV protease and the His-tags were removed using a second Ni-NTA column. Protein purity was verified with SDS-PAGE and intact MS. DCN1 was dissolved in a buffer containing 25 mM Tris-HCl, 200 mM NaCl, and 1 mM DTT at 400 nM. 11 concentrations of compounds were added to the DCN1 solution and incubated at room temperature for 3 hours, unless otherwise specified. The reaction plates were quenched by adding 0.2% formic acid. Quenched assay plates were analyzed with an Agilent RapidFire 360 system connected to an Agilent 6545 Q-TOF mass spectrometer equipped with an AJS source. 10 μL of sample volume was loaded onto a custom packed cartridge (4 μL, PLRP-S 30 μm/1000 Å pore; Optimize Technologies) with loading buffer ($ddH_2O$ with 0.09% (vol/vol) formic acid and 0.01% (vol/vol) trifluoroacetic acid; 1.25 ml/min) for 6 seconds before being eluted directly into the mass spectrometer in elution buffer (80% acetonitrile with 0.09% (vol/vol) formic acid and 0.01% (vol/vol) trifluoroacetic acid; 0.5 ml/min) for 7 seconds. The cartridge was re-equilibrated with loading buffer for 1 second before collection of the next sample. The Q-TOF was operated in TOF-only positive ionization mode set to the following parameters: Gas Temp=350 C, Drying Gas=7 l/min, Nebulizer=50 psi, Sheath Gas Temp=400 C, Sheath Gas Flow=12 l/min, Vcap=4000 V, Nozzle Voltage=1000 V, Fragmentor=125 V, Skimmer=65 V and Oct 1 RF Vpp=750V. Raw MS data files were deconvoluted and analyzed using the Agilent MassHunter Bioconfirm software package to identify both parent protein and expected compound adduct mass signatures.

The MS data is presented in % adduct formation which is shown in Table 3 below. Compounds with an MS Emax % adduct formation greater than or equal to 0.0 and less than or equal to 30.0 are designated as "+". Compounds with an MS Emax % adduct formation greater than 30.0 and less than or equal to 80.0 are designated as "++". Compounds with an MS Emax % adduct formation greater than 80.0 and less than or equal to 100.0 are designated as "+++".

Additional MS data is presented in % adduct formation which is shown in Table 3a below.

TABLE 3

| Intact Protein MS Analysis | |
|---|---|
| Compound No. | % Adduct Formation |
| I-1 | +++ |
| I-3 | +++ |
| I-4 | +++ |
| I-5 | +++ |
| I-7 | + |
| I-8 | + |
| I-10 | ++ |
| I-12 | +++ |
| I-13 | ++ |
| I-16 | + |
| I-18 | +++ |
| I-19 | +++ |
| I-20 | ++ |
| I-23 | + |
| I-26 | + |
| I-27 | + |
| I-29 | + |
| I-30 | + |
| I-32 | + |
| I-33 | + |
| I-34 | +++ |
| I-35 | + |
| I-37 | + |
| I-38 | + |
| I-51 | + |
| I-53 | ++ |
| I-55 | + |
| I-57 | ++ |
| I-58 | + |
| I-60 | + |
| I-62 | + |
| I-65 | + |
| I-66 | + |
| I-67 | + |
| I-72 | + |
| I-73 | +++ |
| I-74 | +++ |
| I-75 | +++ |
| I-77 | + |
| I-80 | + |
| I-83 | + |
| I-87 | +++ |
| I-88 | + |
| I-90 | + |
| I-92 | +++ |
| I-97 | + |
| I-101 | + |
| I-103 | + |
| I-104 | + |
| I-106 | + |
| I-107 | +++ |
| I-108 | + |
| I-110 | + |
| I-112 | +++ |
| I-115 | + |

TABLE 3-continued

| Intact Protein MS Analysis | |
|---|---|
| Compound No. | % Adduct Formation |
| I-116 | + |
| I-117 | + |
| I-119 | + |
| I-120 | + |
| I-121 | ++ |
| I-122 | ++ |
| I-123 | + |
| I-125 | ++ |
| I-129 | +++ |
| I-131 | + |
| I-132 | ++ |
| I-136 | +++ |
| I-138 | +++ |
| I-140 | +++ |
| I-141 | + |
| I-143 | + |
| I-145 | + |
| I-147 | + |
| I-148 | +++ |
| I-149 | +++ |
| I-151 | +++ |
| I-152 | + |
| I-153 | ++ |
| I-156 | + |
| I-161 | + |
| I-163 | + |
| I-164 | + |
| I-165 | + |
| I-166 | + |
| I-167 | +++ |
| I-168 | + |
| I-169 | + |
| I-170 | + |
| I-173 | +++ |
| I-174 | + |
| I-175 | + |
| I-176 | + |
| I-177 | + |
| I-178 | +++ |
| I-179 | + |
| I-180 | + |
| I-181 | + |
| I-182 | + |
| I-183 | + |
| I-184 | + |
| I-185 | + |
| I-186 | + |
| I-187 | +++ |
| I-188 | + |
| I-189 | + |
| I-190 | + |
| I-191 | + |
| I-192 | ++ |
| I-193 | + |
| I-194 | + |
| I-195 | + |
| I-196 | + |
| I-197 | + |
| I-198 | + |
| I-199 | + |
| I-200 | + |
| I-201 | +++ |
| I-202 | + |
| I-203 | + |
| I-204 | + |
| I-205 | + |
| I-206 | + |
| I-207 | + |
| I-208 | + |
| I-209 | + |
| I-210 | + |
| I-211 | + |
| I-212 | + |
| I-213 | +++ |
| I-214 | + |
| I-215 | + |

TABLE 3-continued

| Intact Protein MS Analysis | |
|---|---|
| Compound No. | % Adduct Formation |
| I-216 | + |
| I-217 | + |
| I-218 | + |
| I-219 | + |
| I-220 | + |
| I-221 | + |
| I-225 | + |
| I-227 | ++ |
| I-228 | + |
| I-229 | + |
| I-230 | +++ |
| I-232 | + |
| I-233 | + |
| I-234 | + |
| I-235 | + |
| I-236 | +++ |
| I-237 | + |
| I-238 | + |
| I-239 | + |
| I-240 | + |
| I-241 | +++ |
| I-242 | + |
| I-251 | +++ |
| I-256 | +++ |

TABLE 3a

| Intact Protein MS Analysis | |
|---|---|
| Compound No. | % Adduct Formation |
| I-256 | +++ |
| I-270 | +++ |
| I-271 | +++ |
| I-272 | +++ |
| I-273 | +++ |
| I-274 | +++ |
| I-275 | ++ |
| I-276 | +++ |
| I-277 | +++ |
| I-278 | +++ |
| I-279 | +++ |
| I-280 | +++ |
| I-281 | +++ |
| I-282 | +++ |
| I-283 | +++ |
| I-284 | +++ |
| I-285 | +++ |
| I-286 | + |
| I-287 | +++ |
| I-288 | +++ |
| I-289 | +++ |
| I-290 | + |
| I-291 | +++ |
| I-292 | +++ |
| I-293 | +++ |
| I-294 | +++ |
| I-295 | +++ |
| I-296 | ++ |
| I-297 | +++ |
| I-298 | + |
| I-299 | + |
| I-300 | +++ |
| I-301 | ++ |
| I-302 | +++ |
| I-303 | ++ |
| I-304 | +++ |
| I-305 | +++ |
| I-306 | ++ |
| I-307 | +++ |
| I-308 | +++ |
| I-309 | + |
| I-310 | +++ |

TABLE 3a-continued

| Intact Protein MS Analysis | |
|---|---|
| Compound No. | % Adduct Formation |
| I-311 | + |
| I-312 | +++ |
| I-313 | ++ |
| I-314 | +++ |
| I-315 | +++ |
| I-316 | +++ |
| I-317 | +++ |
| I-318 | +++ |
| I-319 | ++ |
| I-320 | +++ |
| I-321 | +++ |
| I-322 | +++ |
| I-323 | +++ |
| I-324 | +++ |
| I-325 | +++ |
| I-326 | +++ |
| I-327 | +++ |
| I-328 | +++ |
| I-329 | +++ |
| I-330 | +++ |
| I-331 | +++ |
| I-332 | +++ |
| I-333 | +++ |
| I-334 | +++ |
| I-335 | +++ |
| I-336 | +++ |
| I-337 | +++ |
| I-338 | +++ |
| I-339 | +++ |
| I-340 | +++ |
| I-341 | +++ |
| I-342 | +++ |
| I-343 | ++ |
| I-344 | ++ |
| I-345 | +++ |
| I-346 | +++ |
| I-347 | +++ |
| I-348 | ++ |
| I-349 | +++ |
| I-350 | ++ |
| I-351 | +++ |
| I-352 | +++ |
| I-353 | +++ |
| I-354 | ++ |
| I-355 | +++ |
| I-356 | +++ |
| I-357 | ++ |
| I-358 | +++ |
| I-359 | +++ |
| I-360 | +++ |
| I-361 | +++ |
| I-362 | +++ |
| I-363 | +++ |
| I-364 | +++ |
| I-365 | +++ |
| I-366 | +++ |
| I-367 | +++ |
| I-368 | +++ |
| I-369 | +++ |
| I-370 | +++ |
| I-371 | +++ |
| I-372 | +++ |
| I-373 | ++ |
| I-374 | +++ |
| I-375 | +++ |
| I-376 | +++ |
| I-377 | +++ |
| I-378 | +++ |
| I-379 | +++ |
| I-380 | +++ |
| I-381 | +++ |
| I-382 | +++ |
| I-383 | +++ |
| I-384 | + |
| I-385 | +++ |
| I-386 | +++ |

TABLE 3a-continued

| Intact Protein MS Analysis | |
|---|---|
| Compound No. | % Adduct Formation |
| I-387 | +++ |
| I-388 | ++ |
| I-389 | +++ |
| I-390 | +++ |
| I-391 | +++ |
| I-392 | +++ |
| I-393 | +++ |
| I-394 | +++ |
| I-395 | +++ |
| I-396 | +++ |
| I-397 | +++ |

Example 32: Materials and Methods: NBSGW Humanized Mouse Model for HbF Induction Animals Female, 6-week-old NOD.Cg-KitW-41J Tyr+ Prkdcscid Il2rgtm1Wjl/ThomJ (NBSGW) mice (Jackson Laboratory strain #02662) were used for these studies. The mice were acclimatized to laboratory conditions for 5 days prior to inoculation.

Cell Preparation and Inoculation

GCSF-mobilized human CD34+ cells were removed from liquid nitrogen storage, thawed in a 37C water bath and transferred quickly into a 50 mL conical tube. Cryovial was rinsed once with thaw buffer, 0.1% BSA in phosphate buffered saline (PBS), and buffer was transferred combined with the original contents in the 50 ml conical tube. Next, doubling volumes of thaw buffer was added to the conical and gently swirled for ~30 seconds to one minute until the volume in the conical was 32 mL. Cells and buffer were centrifuged at 300 G for 8 minutes, and the supernatants were aspirated. Cells were counted by resuspending in 1 mL of thawing buffer per million of cells to a target concentration range of 0.5 to 2M/ml) and counting with AOPI (1:1) on a luna cell counter to confirm the concentration of cells/mL. The cell concentration was adjusted to 3×10^6 cells/ml. For each mouse, 300 thousand cells in 0.1 ml were injected into the tail vein with a 25-gauge needle.

Engraftment Checkpoint

On day 56 after human cell adoptive transfer, whole blood was collected from each mouse by submandibular bleed and a 100 μL sample of EDTA whole blood was transferred to a 2 ml tube containing 1.8 mL ACK Lysing Buffer at room temperature (RT), and then inverted to mix. Samples were incubated at RT for 15 min in the dark to lyse. After lysis, samples were centrifuged at 500×g for 5 minutes at RT to enable supernatant decanting. Remaining cells were washed with 1 mL of PBS-0.5% BSA and centrifuged at 500×g for 5 minutes at 4C. Supernatant was decanted and cells were stained with leukocyte markers (human and mouse CD45 antibodies; BD347464, BD557659) to confirm human cell engraftment. Mice having less than one percent, or greater than ten percent, human CD45 positive cells were excluded from the subsequent study. The remaining mice were then randomized into treatment groups based on percentage of human cell engraftment. Each treatment group included 10-11 mice.

Compound Administration

Compound I-73, I-256, I-552 or I-363 was dissolved in a 5% Cremophor RH40, 20% hydroxylpropyl-b-cyclodextrin solution. Hydroxyurea was solubilized in PBS. Formulations were prepared fresh daily. Commencing on day 84 post human cell engraftment, mice were treated by oral gavage with either I-73, I-256, I-552 or I-363 hydroxyurea or their respective vehicles, for a period of three weeks using either once daily (QD) or twice daily (BID) dosing regimens. Mice were monitored daily for body weight and condition. Mice which lost greater than 20% body weight prior to study completion were removed from the study and humanely euthanized.

Bone Marrow Collection and Analysis

After 21 days of dosing, all mice were euthanized and prepared for bone marrow collection. Femurs were collected from each mouse by first disinfecting the skin with 70% ethanol and then, using a pair of scissors and forceps, removing the limb and dissecting the muscles both above and below the femur and tibia, taking care not to damage the bone. Femurs were placed in PBS-0.5% BSA-2 mM EDTA-containing tubes on ice during collections. Each femur was flushed to extract marrow with 1 mL of 0.5% BSA-PBS 2 mM EDTA using a 27 gauge needle a total of three times. Extracted cells were counted and aliquoted to prepare for analysis. Whole bone marrow cells were used to analyze the levels of HbF protein and gene levels (HBG1 and HBB). HbF protein levels were analyzed by flow cytometry (% F-cells) or by AlphaLisa. HbF gene (HBG1) expression was analyzed by Nanostring. (The details for the Nanostring and AlphaLisa assays are provided in the preceding examples). An antibody against Glycophorin A (GlyA), a marker for human red blood cells, was used to purify GlyA positive cells by magnetic sorting. Cell lysate from GlyA positive cells was used for HPLC analysis and percentage of fetal HbF and adult HbB was calculated.

The data can be found in FIG. 1A-1C, FIG. 2, FIG. 3A-3C, FIG. 4A-4B, FIG. 5, FIG. 10A-10B, FIG. 11A-11C, FIG. 12A-12B and FIG. 13A-13C.

Example 33: Induction of Fetal Hemoglobin by Hydroxyurea and I-73 in Human CD34+Cell Reconstituted Immunodeficient Mice and Analysis of Hypothesized Synergistic Effect Between Hydroxyurea and I-73

In Vivo Pharmacology Report

Study Overview

The clinical standard of care in the treatment of sickle cell disease (SCD), hydroxyurea (HU), ameliorates symptoms by increasing the levels of non-sickling fetal hemoglobin within the erythroid cells of patients. However, HU is often associated with adverse reactions due to its cytotoxic nature. Hence, it remains of high interest to identify alternative treatments for SCD employing less toxic mechanisms of action.

The current study was undertaken to determine the effect of I-73, when treated in combination with HU, on levels of HBG1 and HbF induction in the humanized mice. Following a three-week treatment period, it was observed that both fetal hemoglobin mRNA and protein were greater in mice treated with the I-73/HU combination than those treated with either of these compounds alone.

Experimental Design

Humanized Mouse Model

The model employed for assessment of induction of fetal hemoglobin by I-73 and hydroxyurea involved the use of human stem cell-reconstituted immunodeficient mice. Specifically, three hundred thousand human CD34-positive cells from G-CSF-mobilized human peripheral blood monocytes (PBMCs) were injected into the tail veins of NOD.Cg-KitW-41J Tyr+Prkdcscid Il2rgtm1Wjl/ThomJ (NBSGW) mice (JAX Strain No. 026622) on day 0. Twelve weeks later, mice were checked for human cell engraftment by sampling PBMCs from blood taken from the tail vein and staining for expression of murine or human CD45 by flow cytometry. After removing from the study those mice having greater than 10% human cells or less than 1% human cells in their peripheral blood, the remaining mice were randomized into treatment groups based on the human cell percentage. Thirteen weeks post engraftment, treatment was initiated with either hydroxyurea, I-73, or a combination of both compounds. Hydroxyurea was formulated in PBS (pH 7.4) and I-73 was formulated in 5% Cremophor RH 40/20% hydroxypropyl-β-cyclodextrin (Crem-CD) daily. Mice received either PBS or hydroxyurea each morning and I-73 or Crem-CD each afternoon by oral gavage. After twenty days of daily treatment, the mice were euthanized and their bone marrow (femurs, tibia and critae) were individually collected for subsequent analysis.

HBG1 mRNA Induction

Bone marrow cell pellets (total 500K cells) were lysed in 20 μL of RLT (QIAGEN, 79216) with 1× β-mercaptoethanol (Gibco, 21985-023) and $H_2O$ followed by hybridizations. Hybridizations were done in a total volume of 15 μL [3 μL of RNA lysate added to master mix of 12 μL probe A/B (purchased from IDT), capture probe/reporter probes (NanoString™, XT TagSet-24, 121000602), proteinase K (Fisher Scientific, EO0491) and $H_2O$ suspended in hybridization buffer]. Samples were hybridized at 65° C. for 22 hr. Following hybridization, the tripartide complexes were purified, immobilized by nCounter Prep Station and imaged by Digital Analyzer (nCounter MAX/FLEX Analysis System), to generate digital counts of barcodes corresponding to each target in the multiplexed reaction. Labeled barcodes obtained from unamplified extracts were counted at 555 images or field of view (FOV). The barcode counts for each sample were recorded in Reporter Code Count (RCC) files that are imported into nSolver analysis software (provided with CodeSet by NS) for quality control evaluation.

Fetal Hemoglobin Induction

To assess levels of fetal hemoglobin by AlphaLISA, cells (200 k bone marrow cells/well) were lysed by resuspending pellets in 200 μL of lysis buffer plus protease inhibitor cocktail (100×), mixed well and incubating at room temperature for 30 minutes on the plate shaker @ 300 RPMs. Samples were then diluted 1:10 in a new 96-well round bottom plate by taking 10 μL of lysate and adding 90 μL of AlphaLISA immunoassay buffer. To create the "reaction plate", 20 μL of Acceptor Beads (50 ug/mL final concentration) was added to each well using a multi-channel pipet. 10 μL of diluted cell lysate was added to the wells and mixed well. 20 μL of AlphaLISA immunoassay buffer was added to each well. Biotinylated antibody (final concentration) was then added to each well. The reaction plate on then placed on a plate shaker at 300 rpm for one hour to incubate at room temperature. After the first incubation was complete, 50 μL of Donor Beads (80 mg/mL final concentration) was added to each well and mixed well, keeping the plate in the dark. The covered plate was placed on a shaker at 350 rpm for 30 minutes to incubate at room temperature. After incubation, all 100 μL in each to an AlphaPlate in the dark. Plates were read on a VictorNIVO using the "Alpha 96 Well" setting. Alpha reading was programmed as the default setting with emission at 700 ms and 575/110n.

For determination of HbF levels by high performance liquid chromatography (HPLC), approximately 1 million GlyA-positive sorted cells were placed in 1.5 mL Eppendorf tubes, washed once with PBS and supernatant was aspirated. Samples were shipped to Augusta University on dry ice to be analyzed using standard HPLC methods.

Stratification/Randomization

Following the human cell engraftment check at week 12, mice were randomized into groups based on percentage of human CD45+ cells within the PBMC compartment.

In-Life Endpoints

Individual mouse body weights, general body condition and behavior were assessed daily. Mice losing greater than 20% of their body weight since initiation of treatment were removed from the study and humanely euthanized.

Organ/Tissue/Blood Collection

Blood was collected from individual mice by submandibular bleeding on day 21 of dosing. The next day, bone marrow was collected from femurs, tibia and critae from both hind legs of euthanized mice (6 bones per animal) and filtered through a 40 μM cell strainer.

Formulation 30 mg I-73 were added to 6 mL 10% Cremphor RH40, vortexed and sonicated for 30 min. An equal volume of 40% HP-β-CD, vortex was added, and the tube was vortexed and sonicated for an additional 10 min. Fresh suspensions were prepared daily.

Statistical Analysis

Nanostring data were analyzed using GraphPad Prism software, Version 10.0.0. Normality was tested via a Shapiro-Wilk normality test, and visual inspection of Log transformed data and residuals. If samples are normally distributed, statistical significance was determined using ordinary one-way ANOVA and Tukey's ad hoc testing versus DMSO was performed. Data without a normal distribution were Log transformed and then analyzed using an ordinary One-way ANOVA and Tukey's ad hoc testing versus DMSO. Statistical significance was determined for AlphaLISA and HPLC data by non-parametric t-test (Kolmogrov-Smirnov).

Results

Induction of HBG1 mRNA

Figure 6:
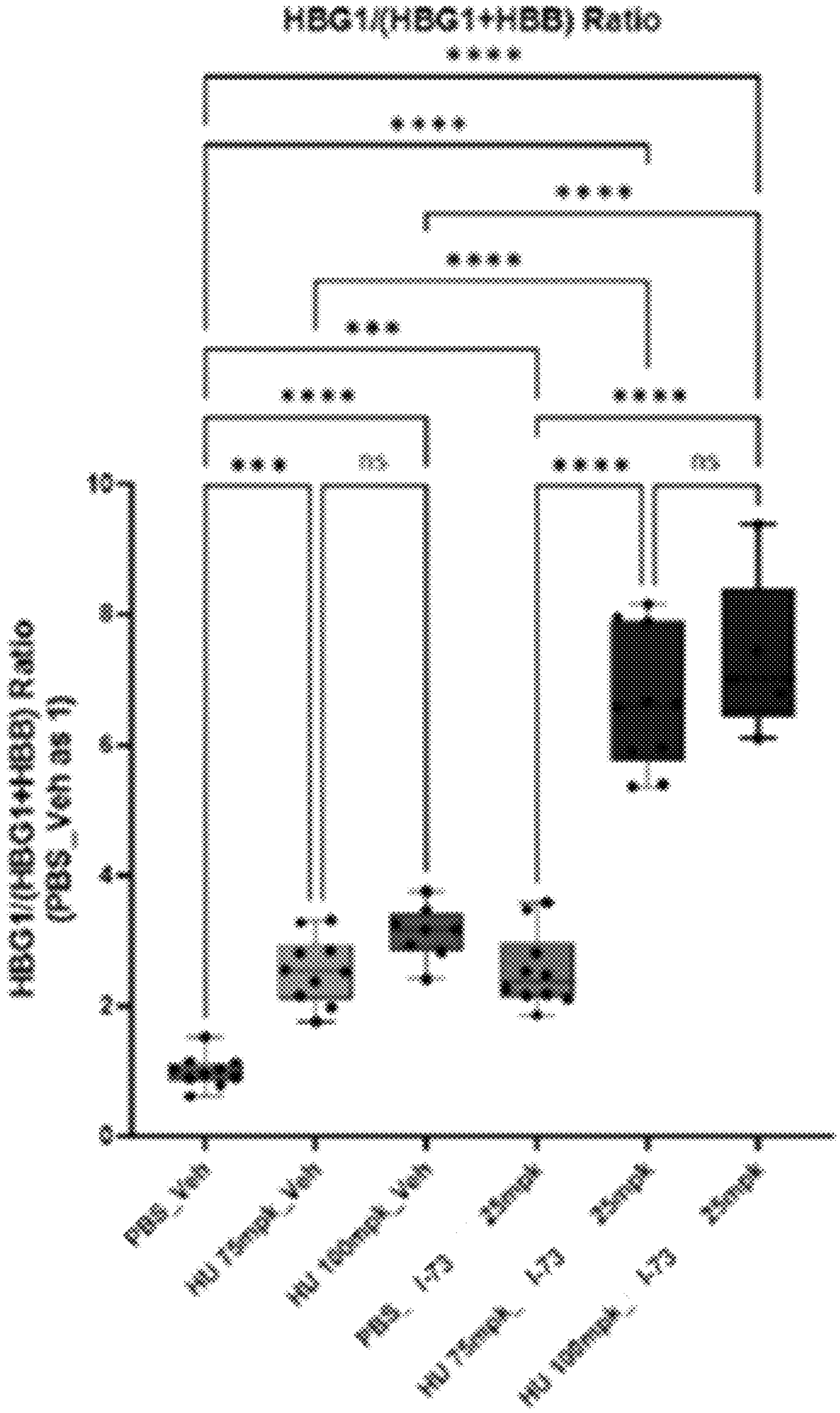
FIG. 6 shows ratio of fetal to adult beta-hemoglobin mRNA in bone marrow cells of humanized mice treated with hydroxyurea (HU) and/or I-73. The treatment combination of HU and I-73 induced a greater ratio of fetal HBG1 to total beta hemoglobin mRNA (fetal HBG1 plus adult-type HBB) than in mice treated with either compound alone. Statistical differences were determined using ordinary one-way ANOVA and Tukey’s ad hoc testing versus DMSO. ns: non statistically significant, *$p<0.001$ and **$p<0.0001$.

The ratio of fetal hemoglobin mRNA to total beta hemoglobin mRNA (HBG1/(HBG1 plus HBB) was greatly enhanced in mice treated with a combination of HU and I-73. As shown in FIG. 6, ratio of fetal to adult beta-hemoglobin mRNA in bone marrow cells of humanized mice treated with hydroxyurea and/or I-73. Treatment combination of HU and I-73 induced a greater ratio of fetal HBG1 to total beta hemoglobin mRNA (fetal HBG1 plus adult-type HBB) than in mice treated with either compound alone. Statistical differences were determined using ordinary one-way ANOVA and Tukey's ad hoc testing versus DMSO. ns: non statistically significant, *$p<0.001$ and **$p<0.0001$.

Induction of Fetal Hemopoietic Protein as Determined by HPLC

Figure 7:
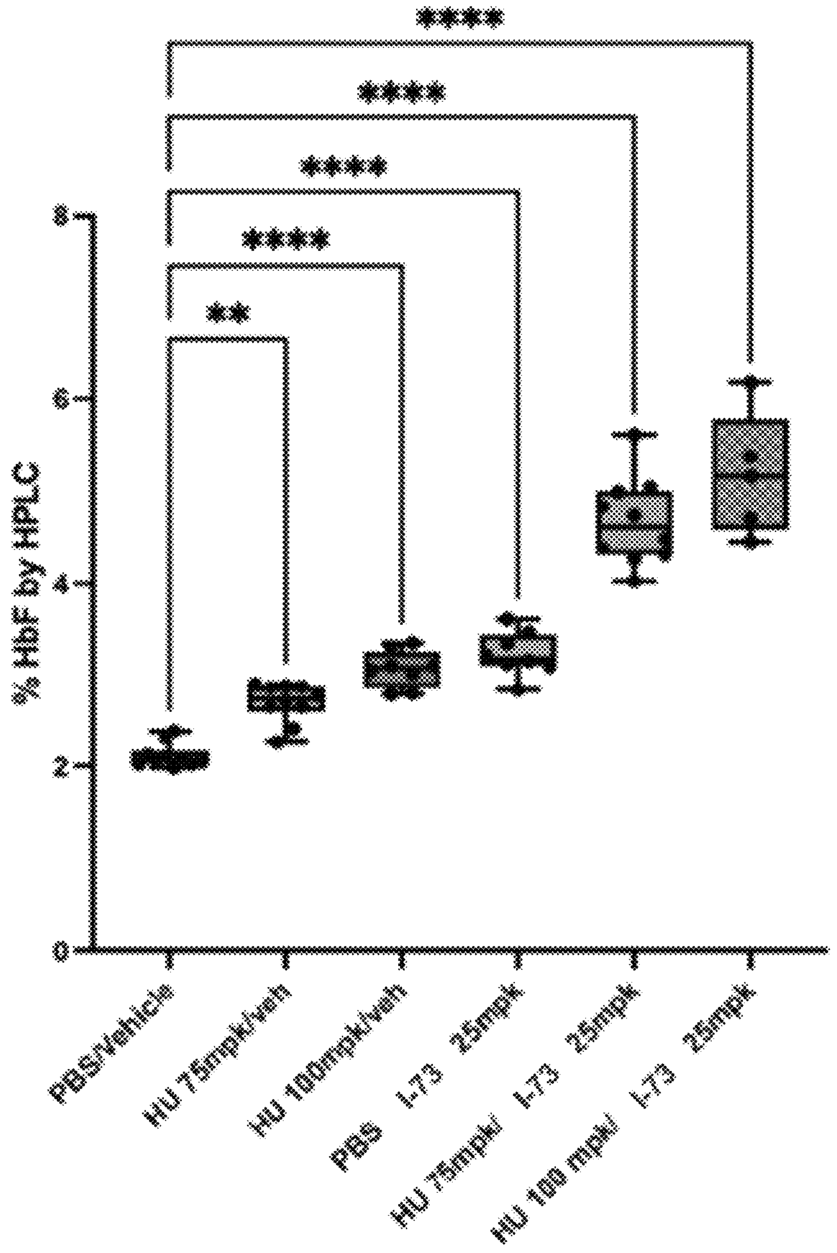
FIG. 7 shows expression of fetal hemoglobin (HbF) levels in glycophorin A-expressing cells in treated humanized mice by HPLC. Bone marrow cells expressing GlyA were isolated by flow cytometry and analyzed for expression of fetal (HbF) and adult (HbB) hemoglobin. Results are expressed as the ratio of fetal hemoglobin in relationship to the total beta hemoglobin (HbF plus HbB) expression level. Statistical significance was determined by non-parametric t-test (Kolmogrov-Smirnov).
Figure 8:
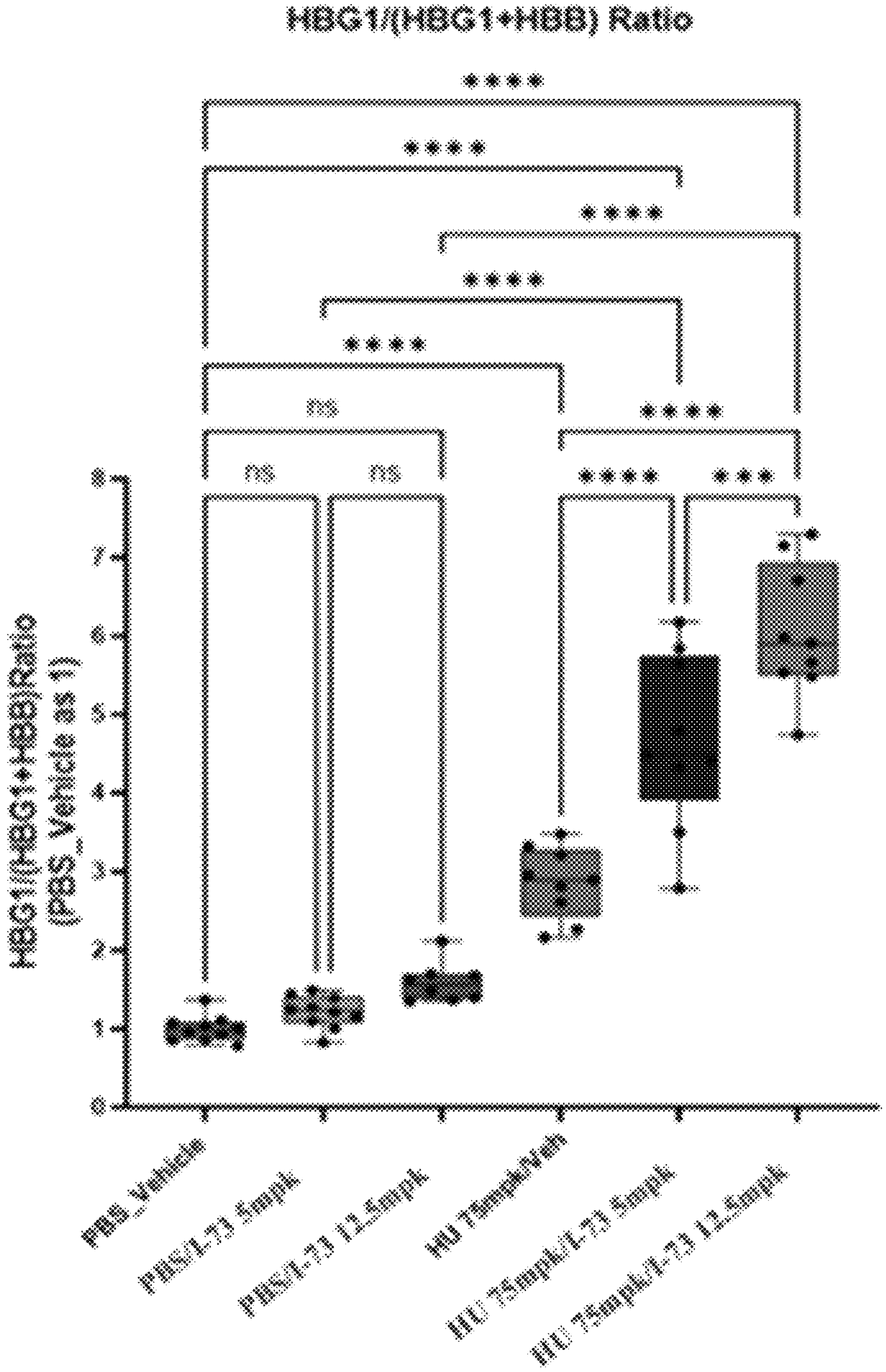
FIG. 8 shows ratio of fetal to adult beta-hemoglobin mRNA in bone marrow cells of humanized mice treated with hydroxyurea and/or I-73. Treatment combination of HU and I-73 induced a greater ratio of fetal HBG1 to total beta hemoglobin mRNA (fetal HBG1 plus adult-type HBB) than in mice treated with either compound alone. The dose levels are lower that the dose levels shown in FIG. 6.
Figure 9:
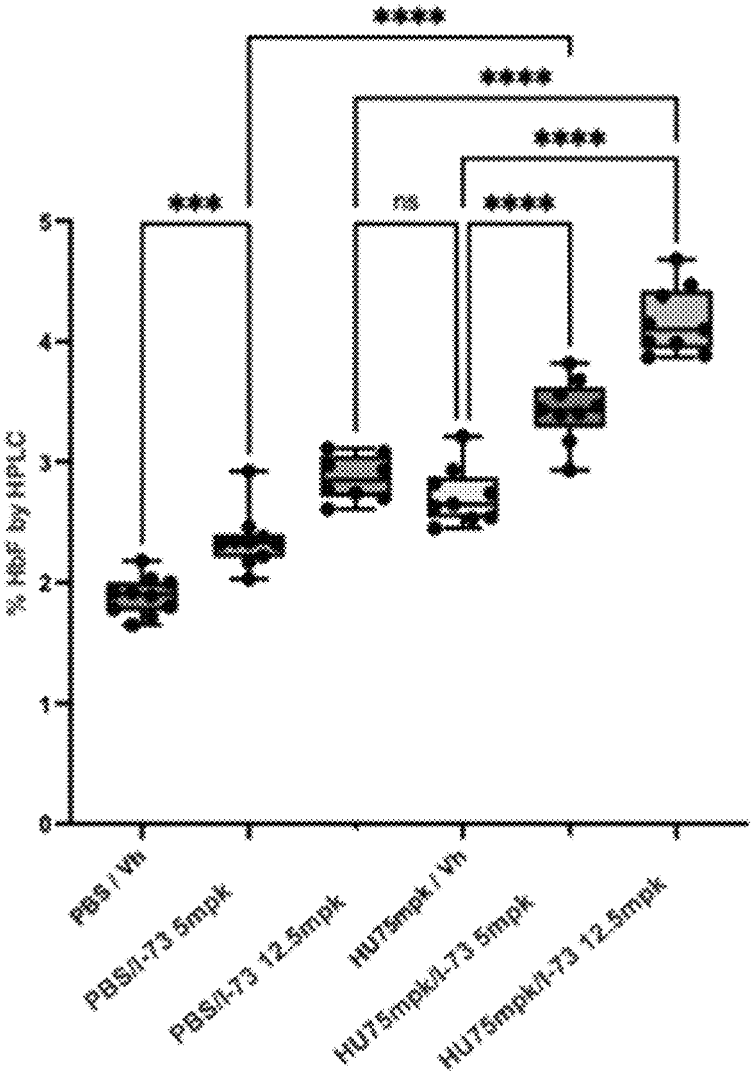
FIG. 9 shows the HbF protein level by HPLC in cells exposed to I-73, HU or a combination thereof.
Figure 10A:
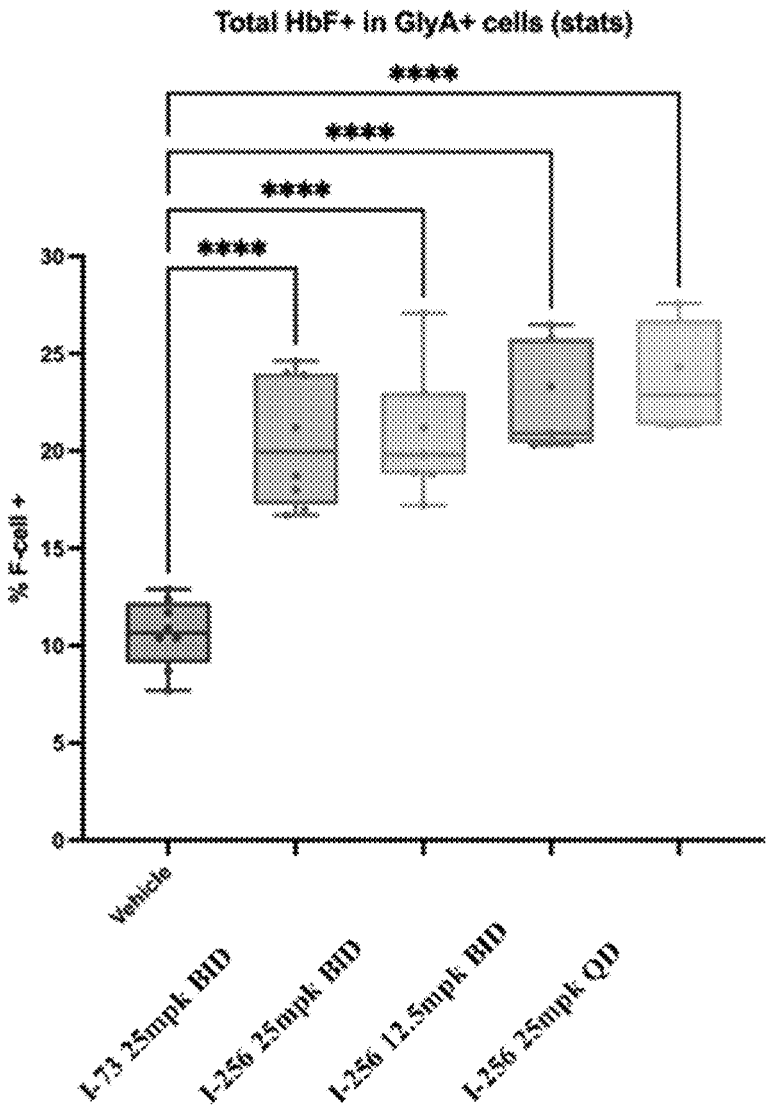
FIGS. 10A and 10B show F-cell and HbF AlphaLISA analysis for cells exposed to compounds I-73 and I-256.
Figure 10B:
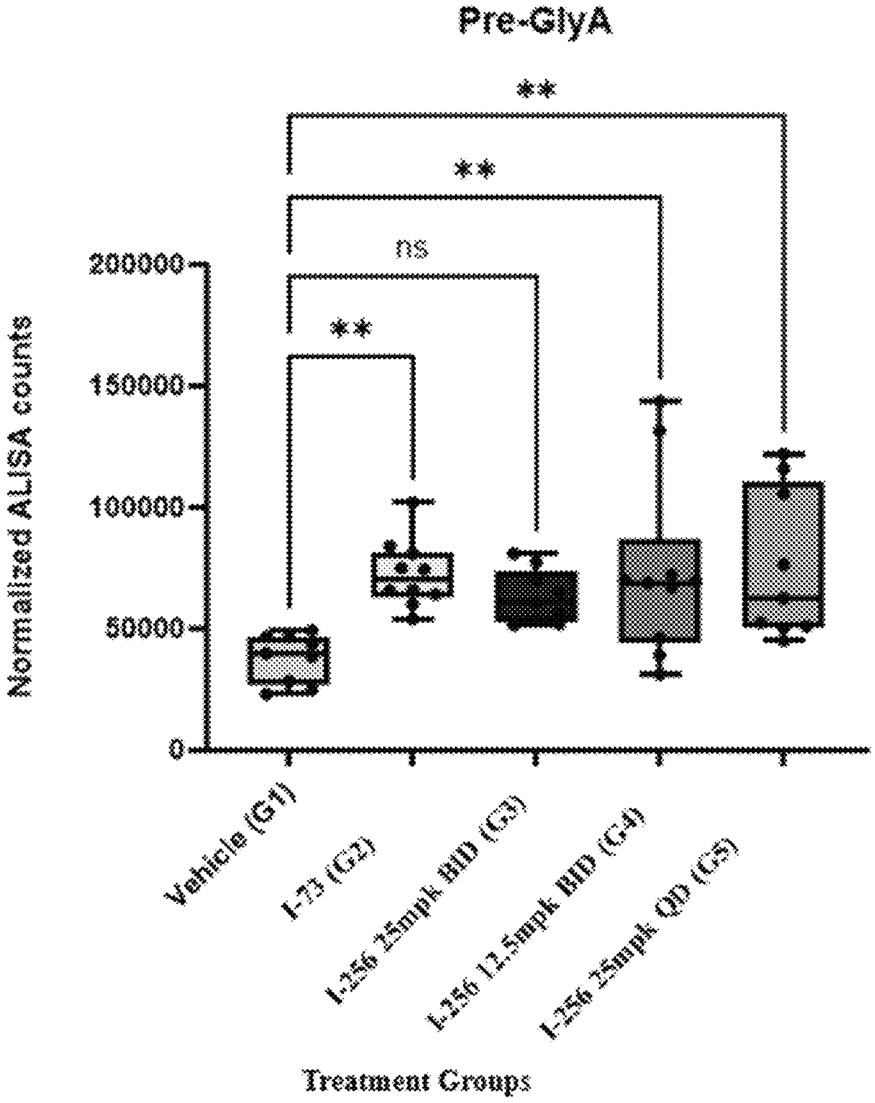
Figure 11A:
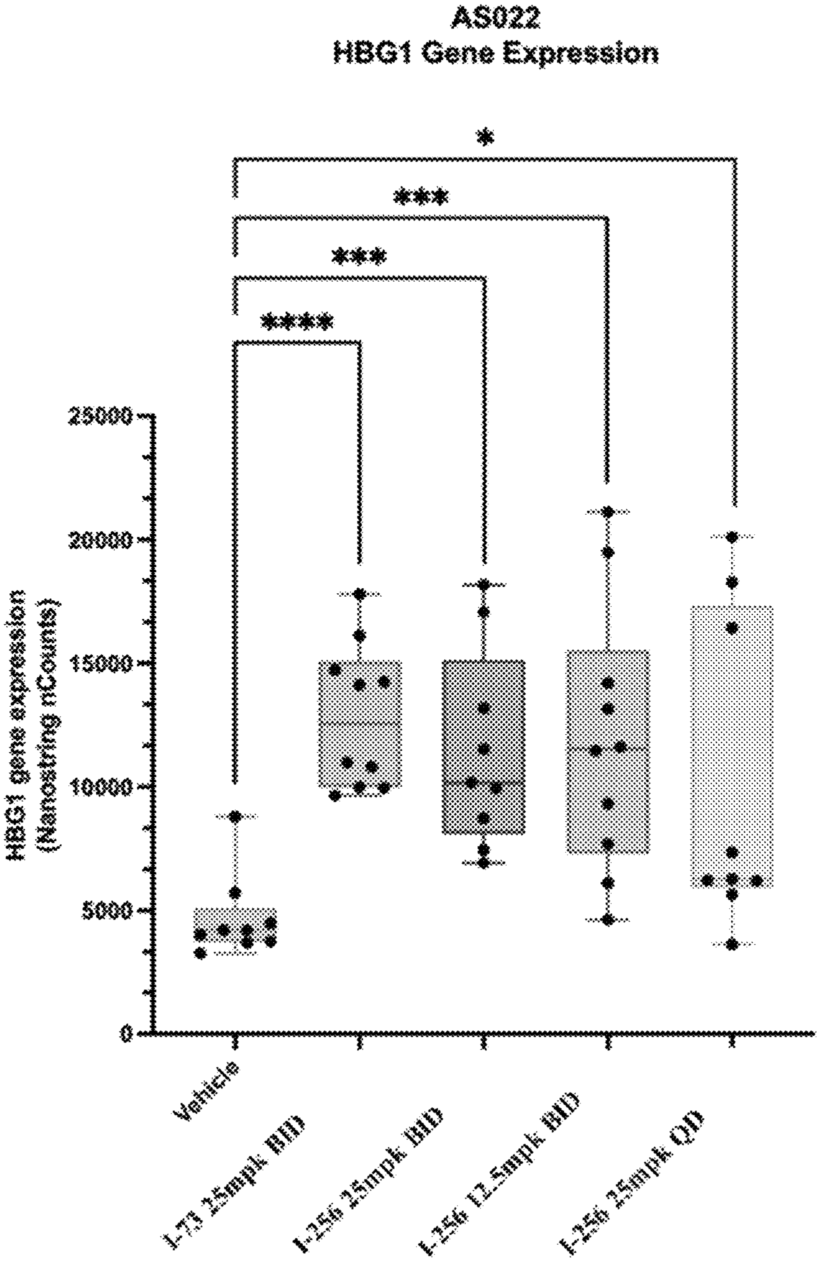
FIGS. 11A, 11B and 11C show increased HBG1 expression compared to vehicle by compounds I-73 and I-256 at various doses and treatment regimes. Data shown both as HBG1 alone or as HBG1 to total beta hemoglobin mRNA (fetal HBG1 plus adult-type HBB).
Figure 11B:
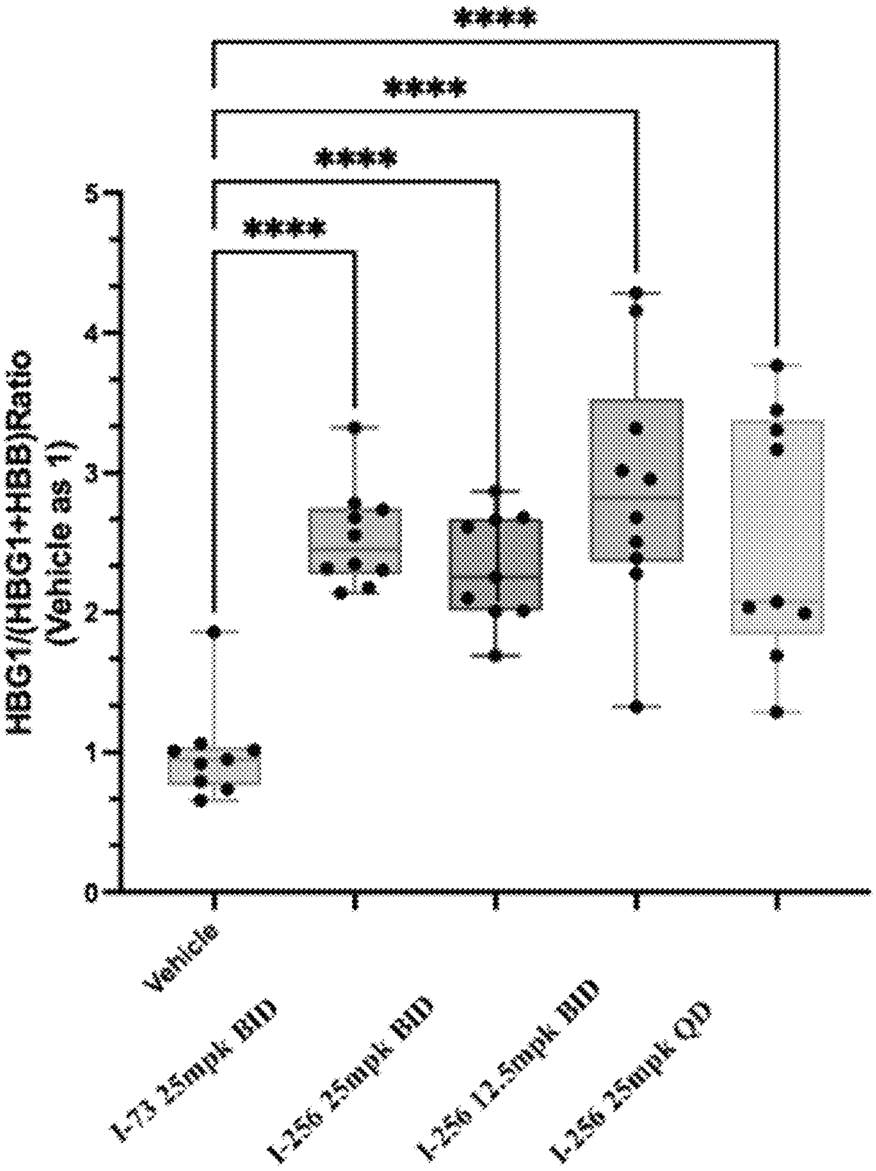
Figure 11C:
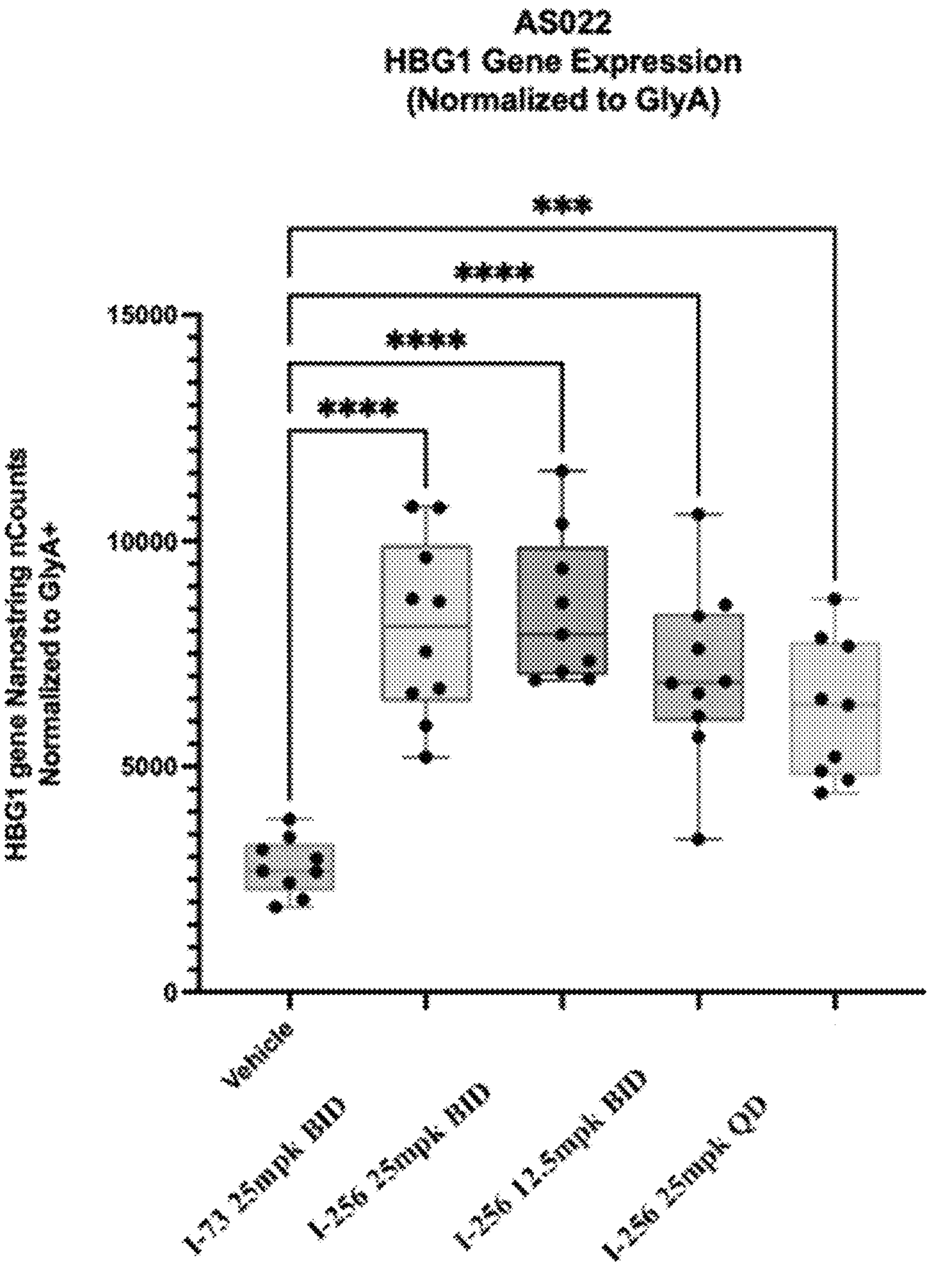
Figure 12A:
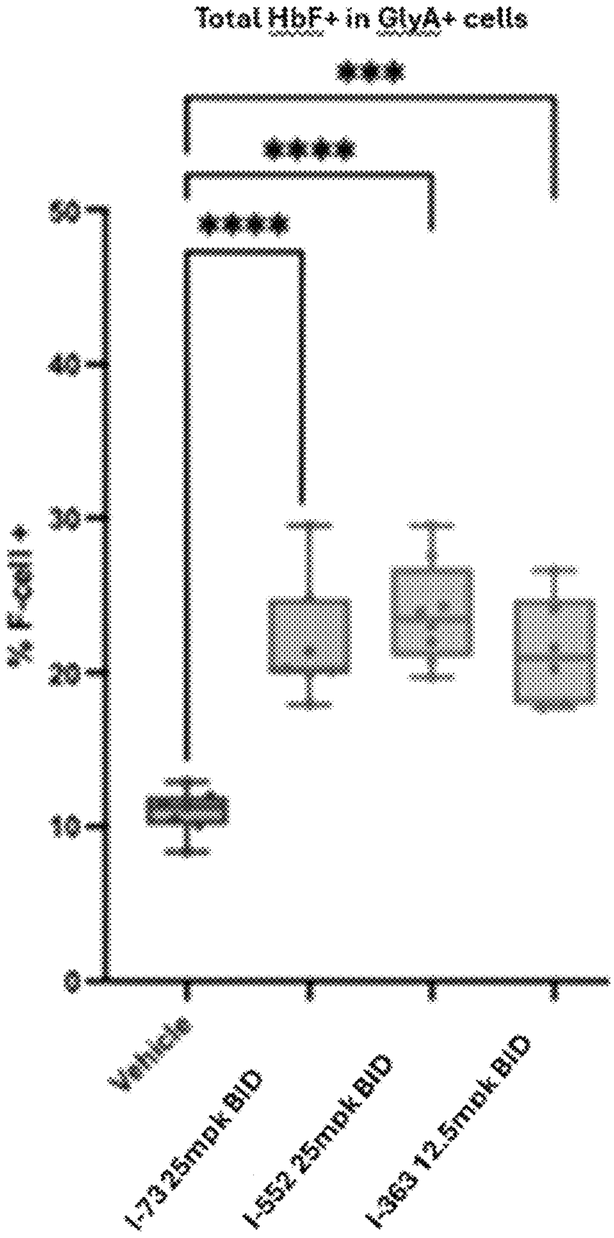
FIGS. 12A, 12B, 13A, 13B and 13C show additional compounds I-552 and I-363 that were evaluated for their ability to induce fetal hemoglobin protein (FIG. 12) as shown by percentage F-cells (flow-cytometry) and HPLC. HBG1 expression, is shown both as HBG1 alone or as HBG1 to total beta hemoglobin mRNA (fetal HBG1 plus adult-type HBB), both measured by NanoString.
Figure 12B:
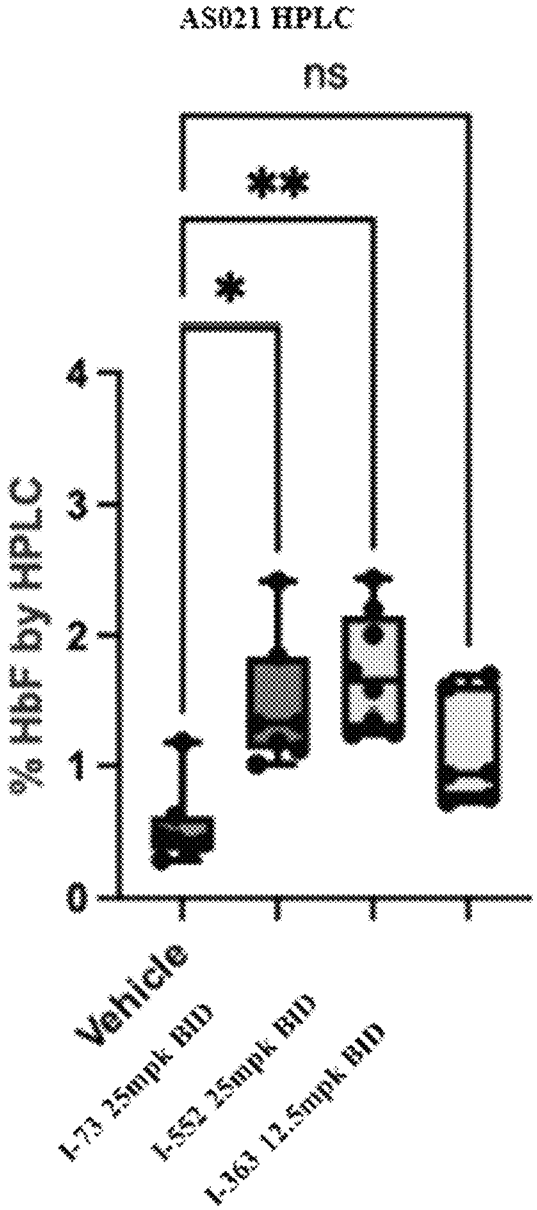
Figure 13A:
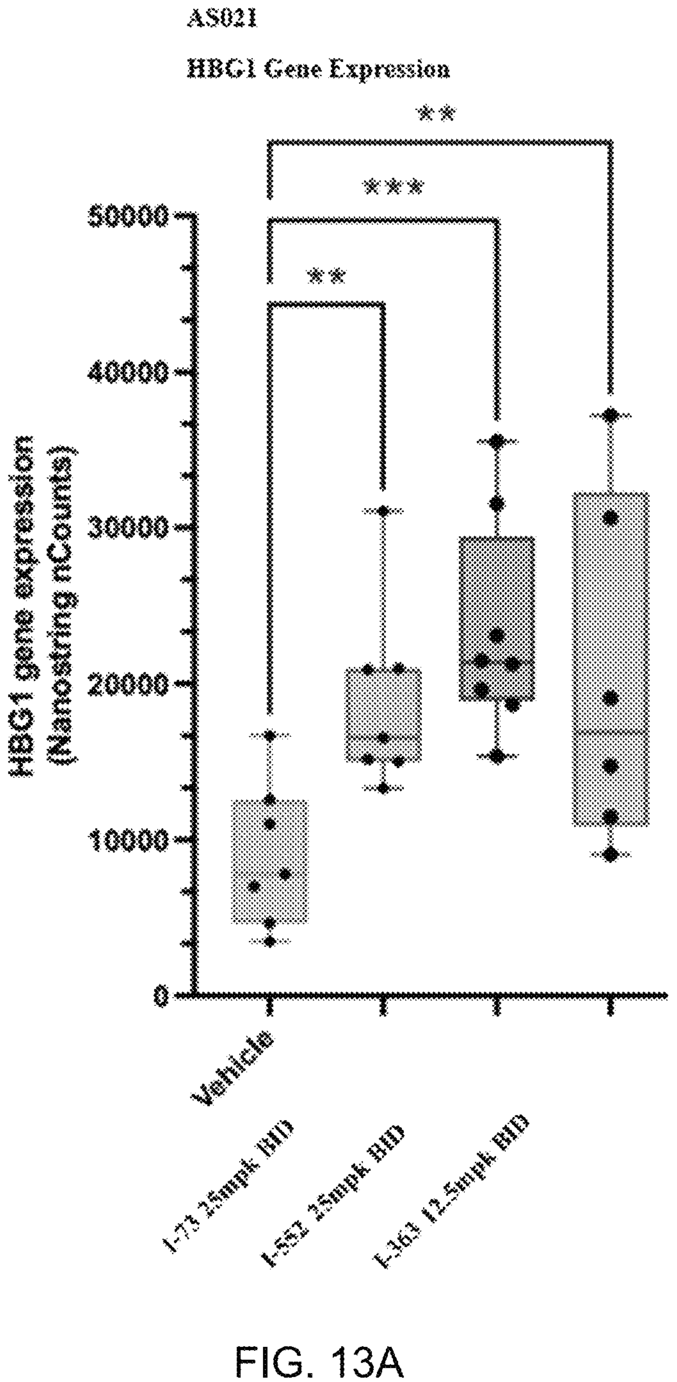
Figure 13B:
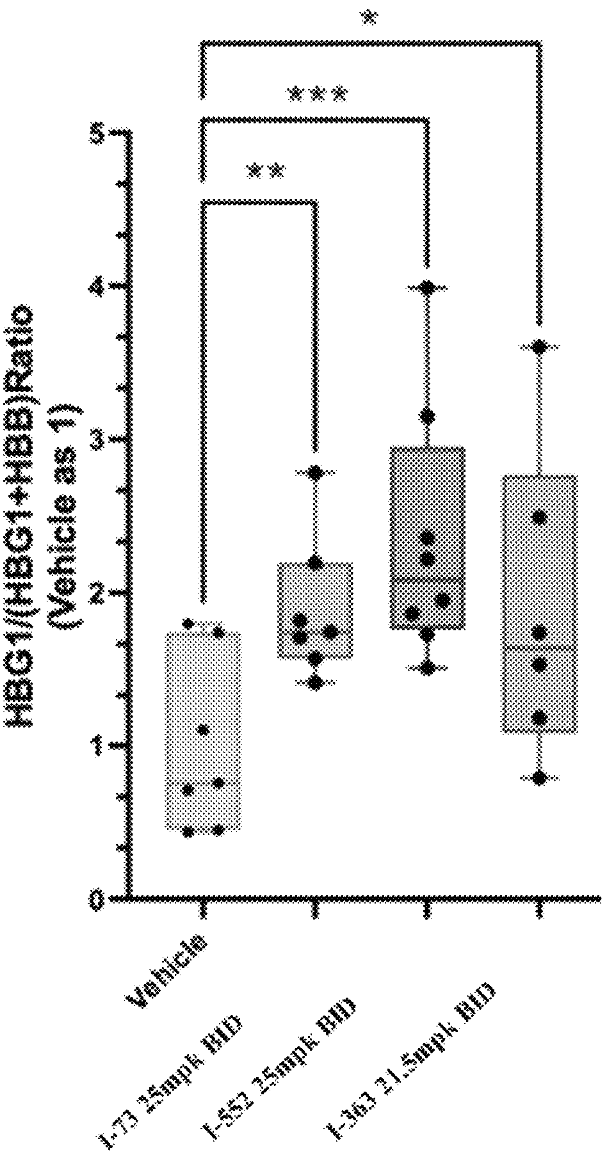
Figure 13C:
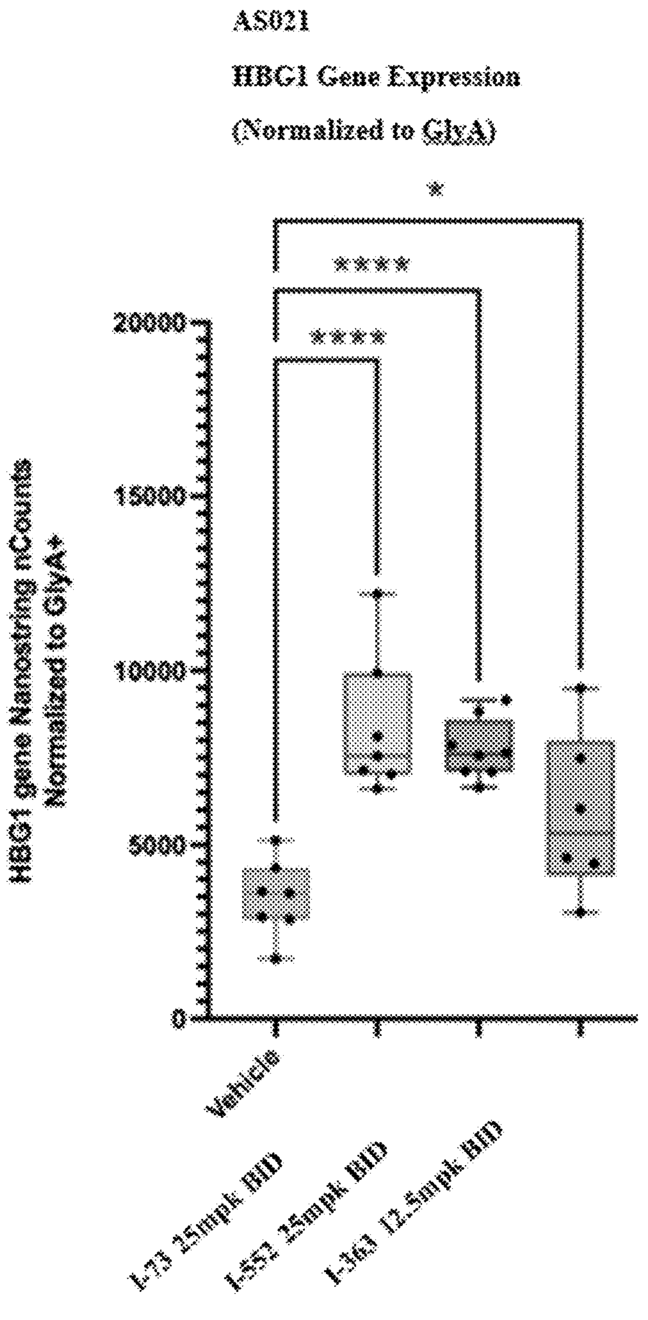

To assess levels of fetal hemoglobin using a method orthogonal to AlphaLISA, GlyA-positive bone marrow cells were isolated by flow cytometry and analyzed for hemoglobin type by HPLC. Results shown in FIG. 7 demonstrate that treatment of humanized mice with hydroxyurea or I-73 resulted in a significant increase in the percentage of HbF protein as compared with levels in the vehicle treatment group. Notably, those mice treated with a combination of HU and I-73 demonstrated much higher percentage of HbF than those mice treated with either compound alone.

Conclusion

Treatment of humanized mice with hydroxyurea or I-73 did not alter the percentage of bone marrow cells expressing human CD45. In contrast, treatment with HU, either alone or in combination with I-73, led to a dose-dependent increase in the percentage of bone marrow cells expressing the erythroid cell marker, glycophorin A, suggesting an expansion of this population.

Within the erythroid progenitor cell compartment, both compounds induced significant levels of fetal hemoglobin in human stem cell-engrafted mice when compared with levels in vehicle-treated mice. The current study extends these findings by demonstrating that treatment with a combination of HU and I-73 greatly enhances HBG1 and HbF induction as compared with those levels in mice treated with either compound alone, as determined by orthogonal methods. Whereas, on a per erythroid progenitor cell basis, I-73 treatment alone induced increased levels of HbF as determined by AlphaLISA, HU treatment mediated an apparent expansion of the erythroid progenitor cell population but with less HbF induction on a per GlyA-positive cell basis. Hence, treatment with a combination of I-73 and HU, leading to greatly enhanced HbF levels in the total bone marrow population, may result from both of these mechanisms acting in concert.

The data from this study demonstrate the capability of I-73, alone or when combined with HU, to induce high levels of fetal hemoglobin expression and support the potential of this compound to treat patients with Sickle cell disease.

Analysis of Synergistic Effect

INTRODUCTION

This study was a pharmacological study to investigate the effect of compound I-73 on the selective induction of fetal hemoglobin mRNA (HBG1) and fetal hemoglobin protein (HbF) in stem cell-engrafted mice when administered alone or in combination with Hydroxyurea (HU). Mice were randomized to receive either Vehicle, HU 75 mg/kg, or HU 100 mg/kg in the morning, and either Vehicle or I-73 25 mg/kg in the afternoon.

Objective

The objective of this analysis was to assess the presence of a synergistic effect between I-73 and HU administered in combination on levels of HBG1 and HbF induction. The outcomes of interest were: HbF %, HBG1 normalized to GlyA+, HBG1/(HBG1+HBB), HBG1, AlphaLISA counts, and AlphaLISA counts normalized to GlyA+.

Methods

Each outcome of interest was analyzed using a two-factor analysis of variance (ANOVA) with interaction terms. The two factors in the model were level of HU (Vehicle, HU 75 mg/kg, or HU 100 mg/kg) and level of I-73 (Vehicle or I-73 25 mg/kg). Interaction terms between HU and I-73 were included to model the hypothesized synergistic effect. Residual plots and diagnostics were used to assess the validity of the statistical assumptions, namely homoscedasticity (constant variance) and normality of the residuals. When there was clear evidence of heteroscedasticity (non-constant variance) with the residual variance increasing as the predicted value of the outcome increased, a weighted least squares (WLS) ANOVA was utilized in lieu of an ordinary least squares (OLS) ANOVA. When the residuals displayed a significant deviation from normality, the outcome of interest was transformed using an appropriate (e.g., square root) transformation. For each outcome, a synergistic effect between I-73 and a given level of HU was declared statistically significant if the interaction term had a positive estimate and the p-value was <0.05.

Results

HbF %

HbF % was analyzed using WLS ANOVA to account for heteroscedasticity in the residuals. The interaction terms for HbF % were significant (p<0.0001 and p=0.0033), indicating statistically significant synergistic effects. The estimates and 95% confidence intervals (CIs) for the synergistic effects between I-73 and HU 75 mg/kg and between I-73 and HU 100 mg/kg were 0.86 (0.48, 1.24) and 1.00 (0.35, 1.65), respectively. For example, treating a mouse with I-73 25 mg/kg alone will on average increase HbF % over vehicle by 1.11. Treating a mouse with HU 75 mg/kg alone will on average increase HbF % over vehicle by 0.59. When a mouse is treated with HU 75 mg/kg in combination with I-73 25 mg/kg, HbF % will on average increase over vehicle by 2.56 (1.11+0.59+0.86). Treating mice with HU 75 mg/kg in combination with I-73 25 mg/kg induces a synergistic effect increasing HbF % by an additional 0.86.

HBG1/GlyA+

HBG1 normalized to GlyA+ (HBG1/GlyA+) was analyzed using OLS ANOVA without any data transformation. The interaction terms for HBG1/GlyA+ were significant (p=0.0125 and p-0.0084), indicating statistically significant synergistic effects. The estimates and 95% CIs for the synergistic effects between I-73 and HU 75 mg/kg and between I-73 and HU 100 mg/kg were 619 (140, 1098) and 751 (202, 1300), respectively.

HBG1/(HBG1+HBB)

The ratio HBG1/(HBG1+HBB) was analyzed using WLS ANOVA to account for heteroscedasticity in the residuals. The interaction terms for HBG1/(HBG1+HBB) were significant (p<0.0001 and p<0.0001), indicating statistically significant synergistic effects. The estimates and 95% CIs for the synergistic effects between I-73 and HU 75 mg/kg and between I-73 and HU 100 mg/kg were 0.054 (0.036, 0.072) and 0.057 (0.031, 0.082), respectively.

HBG1

HBG1 values were first analyzed with OLS ANOVA; however, the residuals displayed a significant deviation from normality. To address non-normality of the residuals, the HBG1 values were transformed using a square root transformation, and the residual diagnostics were examined. The residuals from the transformed data satisfied the assumption of normality, but still displayed heteroscedasticity. To account for heteroscedasticity, the square root transformed values were analyzed using WLS ANOVA. The interaction terms for square root of HBG1 were significant (p<0.0001 and p=0.0034), indicating statistically significant synergistic effects. The estimates and confidence intervals were back transformed and presented on the original scale. The estimates and 95% CIs for the synergistic effects between I-73 and HU 75 mg/kg and between I-73 and HU 100 mg/kg were 2113 (609, 4525) and 3268 (395, 8925), respectively.

AlphaLISA Counts

AlphaLISA counts were analyzed using WLS ANOVA to account for heteroscedasticity in the residuals. The interaction terms were significant (p<0.0001 and p<0.0001), indicating statistically significant synergistic effects. The estimates and 95% CIs for the synergistic effects between I-73 and HU 75 mg/kg and between I-73 and HU 100 mg/kg were 35087 (22257, 47916) and 60983 (41675, 80290), respectively.

AlphaLISA Counts/GlyA+

AlphaLISA counts normalized to GlyA+ were analyzed with OLS ANOVA and without any data transformation. The interaction terms were not statistically significant at the alpha=0.05 level. However, the estimated interaction terms were positive, and the p-values were relatively small (p=0.1425 and p=0.0594), suggesting that there may be a synergistic effect. The estimates and 95% CIs for the synergistic effects between I-73 and HU 75 mg/kg and between I-73 and HU 100 mg/kg were 873 (−304, 2050) and 1295 (−54, 2644), respectively.

Conclusion

These results when taken together demonstrate strong evidence for the presence of synergistic effects between I-73 and HU 75 mg/kg and between I-73 and HU 100 mg/kg. The point estimates for these effects were consistently positive across all endpoints, and were statistically significant for five of the six total measures (HbF %, HBG1 normalized to GlyA+, HBG1/(HBG1+HBB), HBG1, and AlphaLISA counts).

Example 34: Synthesis of Compound I-363

NMR:

$^{1}$H NMR spectrum was recorded on Bruker 400 MHz and 300 MHz instruments internally referenced to a tetramethylsilane (TMS) signal. Chemical shifts (δ) and coupling constants (J) were expressed in parts per million and hertz, respectively.

LCMS

Method-N(LCMS-13): Column: L-column3 C18, 50*3.0 mm, 3 μm, Mobile Phase: A: Water/0.05% ammonia water; B: Acetonitrile, Flow Rate: 1.2 mL/min. Oven Temperature: 40 C, Gradient program (B %): 0.01/5, 2.00/95, 2.80/95, 2.81/5.

HPLC

Method-A: Column: Cortecs C18+, 100*4.6 mm, 2.7 μm. Mobile Phase: A: 0.1% MSA; B: Acetonitrile, Flow Rate: 1.5 mL/min. Oven Temperature: 40 C, Gradient program (B %): 6.00/50, 10.00/95, 12.00/95.

Chiral HPLC

Method-F: Column: CHIRALPAK IC-3, 50*4.6 mm, 3 μm IC30CC-SC002; Mobile Phase A: n-Hexane/DCM=3/1, Mobile Phase B: EtOH (0.1% EDA), Conc. of Pump B: 10.0%; Flow rate: 1.0 ml/min; Oven Temperature: 25 C.

Synthesis of N-((4S,5s)-3-((S)-2-cyanopiperazine-1-carbonyl)-7-ethyl-4-(4-fluorophenyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-363)

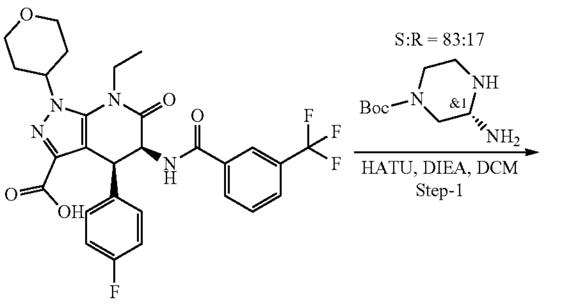

I-657

-continued

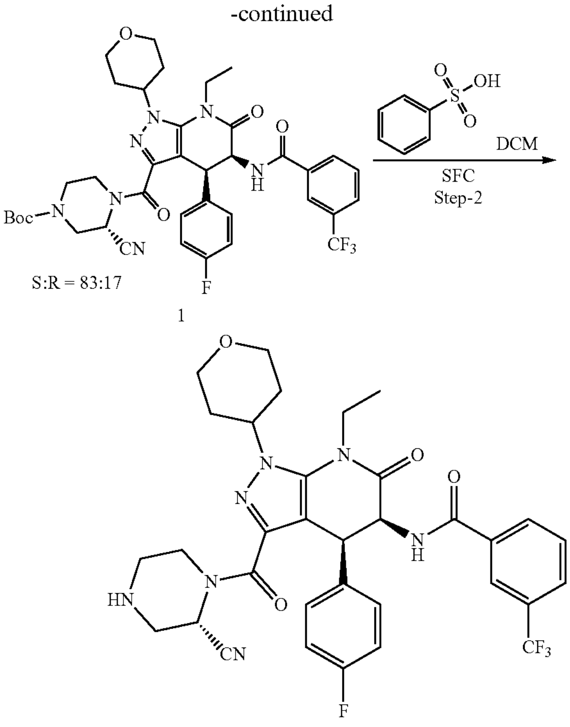

S:R = 83:17

1

I-363 tert-butyl (S)-3-cyano-4-((4S,5S)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carbonyl)piperazine-1-carboxylate (1)

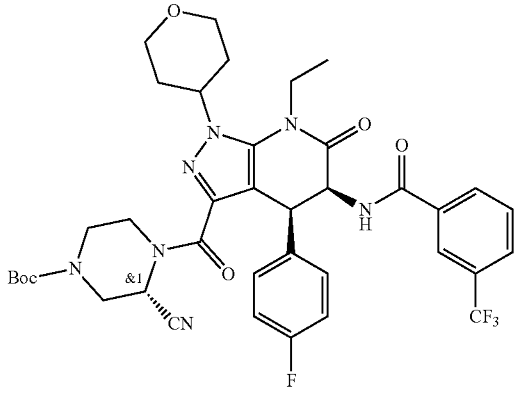

S:R = 83:17

A solution of (4S,5S)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (15.0 g, 26.1 mmol, 1.00 equiv) in DCM (150 mL) was treated with HATU (12.9 g, 33.9 mmol, 1.30 equiv) and DIEA (10.1 g, 78.3 mmol, 3.00 equiv) at room temperature for 10 min under nitrogen atmosphere followed by the addition of tert-butyl (3S)-3-cyanopiperazine-1-carboxylate (S:R=83:17) (6.62 g, 31.3 mmol, 1.20 equiv) in portions at room temperature. The resulting mixture was stirred at room temperature for 1 h under nitrogen atmosphere. The reaction was quenched with water at room temperature. The resulting mixture was extracted with EtOAc (2×150 mL). The combined organic layers were washed with brine (1×150 mL), dried over anhydrous $Na_2SO_4$. After filtration, the filtrate was concentrated under reduced pressure The residue was purified by silica gel column chromatography, eluted with petroleum ether/ethyl acetate (1:1) to afford a mixture (14.3 g, 71.34% yield, 90% LCMS purity) of tert-butyl (S)-3-cyano-4-((4S,5S)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carbonyl)piperazine-1-carboxylate (83:17) and tert-butyl (R)-3-cyano-4-((4S,5S)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carbonyl)piperazine-1-carboxylate (83:17) as a yellow solid.

LCMS Calculated for $C_{38}H_{41}F_4N_7O_6$: 767.31; Observed: 767.4 $[M+H]^+$

N-((4S,5S)-3-((S)-2-cyanopiperazine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-363)

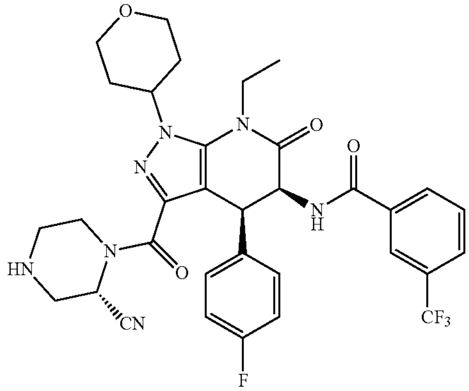 [SMILES: CCN1C(=O)[C@@H](NC(=O)c2cccc(C(F)(F)F)c2)[C@@H](c2ccc(F)cc2)c2c(C(=O)N3CCNC[C@H]3C#N)nn(C3CCOCC3)c21]

A solution of the above mixture (14.3 g, 18.6 mmol, 1.00 equiv) and benzenesulfonic acid (3.54 g, 22.4 mmol, 1.20 equiv) in DCM (40.0 mL) was stirred at 40° C. overnight under nitrogen atmosphere. The mixture was allowed to cool down to room temperature.

The reaction was quenched with sat. $NaHCO_3$(aq.) at room temperature. The resulting mixture was extracted with DCM (2×150 mL). The combined organic layers were washed with brine (1×150 mL), dried over anhydrous $Na_2SO_4$. After filtration, the filtrate was concentrated under reduced pressure. The crude product was purified by Prep-CHIRAL-SFC with the following conditions (Column: (R, R)-WHELK-O1-Kromasil, 3*25 cm, 5 μm; Mobile Phase A: $CO_2$, Mobile Phase B: MEOH: DCM=2: 1 (0.1% 2M $NH_3$-MeOH); Flow rate: 80 mL/min; Gradient: isocratic 45% B; Column Temperature (C): 35; Back Pressure (bar): 100; Wave Length: 220 nm; RT1(min): 4.5; RT2(min): 5.6; Sample Solvent: MeOH; Injection Volume: 1.5 mL) to afford the desired product (9 g, 98.3% purity) as a white solid. The crude product (9 g, 98.3% purity) was purified by DAC with the following conditions (Column: Xselect-CSH-C18 Column, 50*250 mm, 5 μm; Mobile Phase A: Water (5% $NH_4HCO_3$), Mobile Phase B: ACN; Flow rate: 90 mL/min; Gradient: isocratic 5%-50% 12 min; Wave Length: 254 nm/220 nm; RT1(min): 11.5) to afford N-((4S,5S)-3-((S)-2-cyanopiperazine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl) benzamide (1.9 g, 15.2% yield, 99.5% purity) as a white solid.

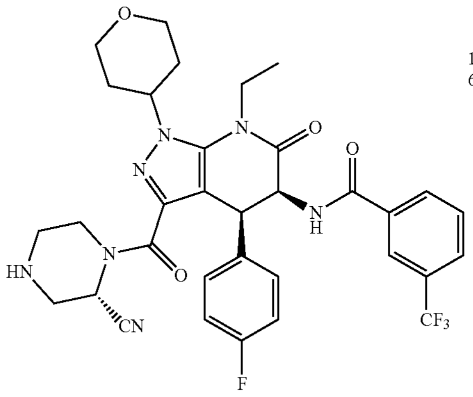

I-366

$^1H$ NMR (300 MHz, DMSO-$d_6$) δ 8.53 (d, J = 7.1 Hz, 1H), 8.19-8.08 (m, 2H), 7.92 (d, J = 7.8 Hz, 1H), 7.71 (t, J = 7.8 Hz, 1H), 7.07 (t, J = 8.8 Hz, 2H), 6.94 (dd, J = 8.7, 5.5 Hz, 2H), 6.27 (s, 0.5H), 5.45 (s, 0.5H), 5.27-5.21 (m, 1H), 4.73 (d, J = 6.9 Hz, 1H), 4.66-4.51 (m, 1H), 4.36-3.85 (m, 4H), 3.67-3.44 (m, 2H), 3.29-3.06 (m, 2H), 3.02-2.71 (m, 3H), 2.69-2.58 (m, 1H), 2.43-2.23 (m, 2H), 2.17 (d, J = 12.4 Hz, 1H), 2.03 (s, 2H), 1.33 (t, J = 7.0 Hz, 3H). LCMS Calculated for $C_{33}H_{33}F_4N_7O_4$: 667.25; Observed (Method-N): 666.3 [M − H]$^-$, 99.5% at RT 1.82 min;
HPLC (Method-A): 99.52% at RT 5.30 min
Chiral-HPLC (Method-F): 99.46% at RT 2.43 min

Example 35: Synthesis of Compound I-552

NMR:

$^1H$ NMR spectrum was recorded on Bruker 400 MHz and 300 MHz instruments internally referenced to a tetramethylsilane (TMS) signal. Chemical shifts (δ) and coupling constants (J) were expressed in parts per million and hertz, respectively.

LCMS:

Method-X (LCMS-25): Column: L-column3 C18 3.0*30 mm 3 μm, Mobile Phase: A: 5 mM $NH_4HCO_3$ in water; B: Acetonitrile, Flow Rate: 1.2 mL/min. Oven Temperature: 40 C, Gradient program (B %): 0.00/10.0, 0.30/40, 1.80/70, 2.20/95, 2.90/95, 2.91/10

Chiral-SFC:

Method-M: Column: Amylose-C Neo 100×4.6 mm 3.0 μm; Co-Solvent: EtOH (20 mM $NH_3$); Gradient (B): 2.50/50, 3.70/50, 3.71/10. Flow rate: 3.0 ml/min; Column Temperature: 40 C.

Synthesis of N-((4S,5S)-3-((1R,3S,5R)-3-cyano-2-azabicyclo[3.1.0]hexane-2-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-ethylbenzamide (I-552)

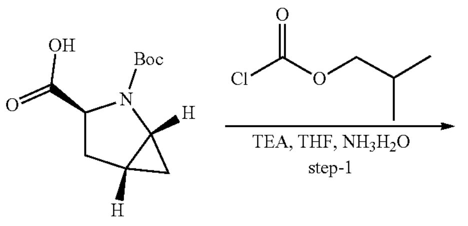

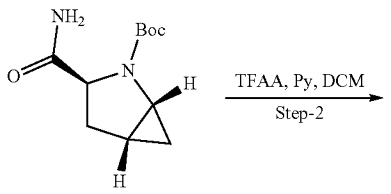

14

-continued

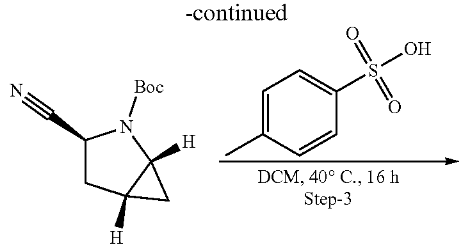

15

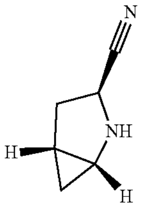

16

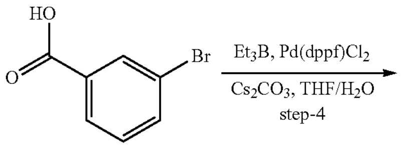

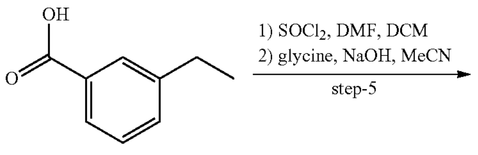

1

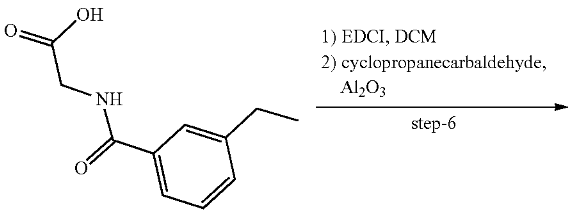

3

-continued

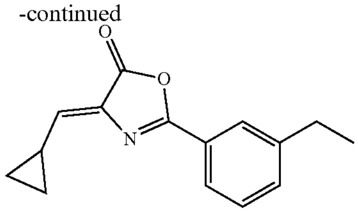

5

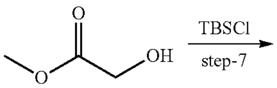

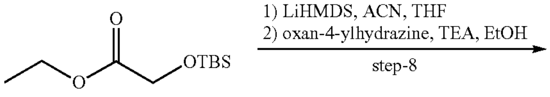

6

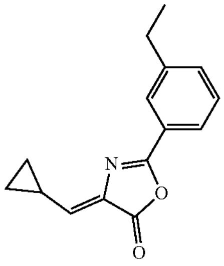

5

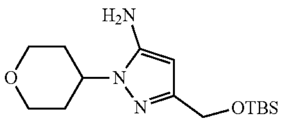

8

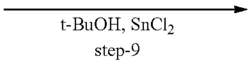

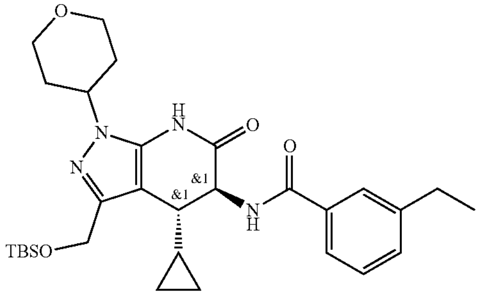

9 step-10

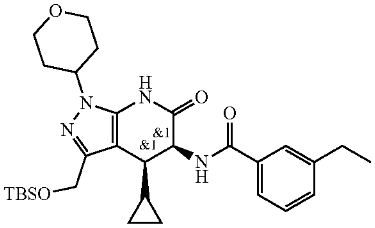

10

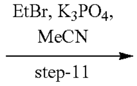

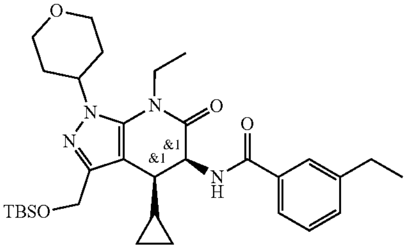

11

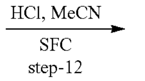

-continued

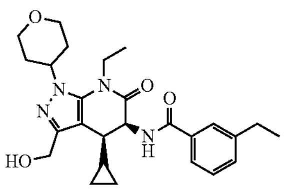

12A

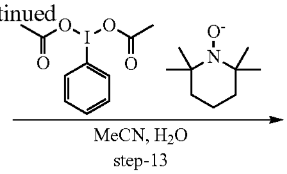

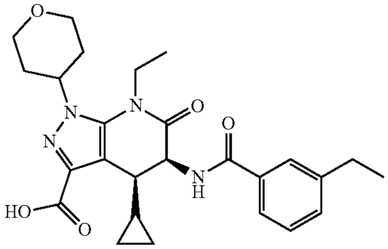

13

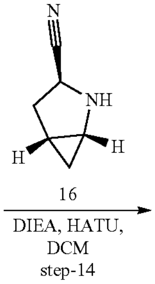

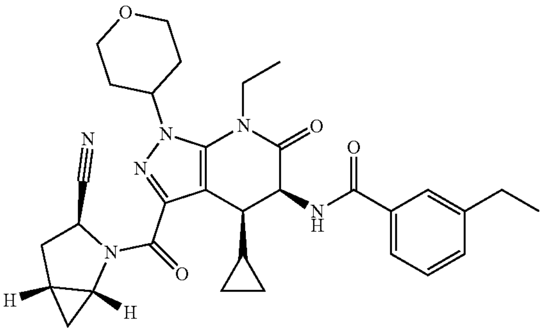

I-552

Experimental Details tert-butyl (1R,3S,5R)-3-carbamoyl-2-azabicyclo [3.1.0]hexane-2-carboxylate (14)

tert-butyl (1R,3S,5R)-3-carbamoyl-2-azabicyclo[3.1.0]hexane-2-carboxylate (14)

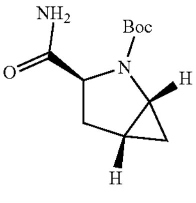

A solution of (1R,3S,5R)-2-(tert-butoxycarbonyl)-2-azabicyclo[3.1.0]hexane-3-carboxylic acid (249 g, 1.09 mol, 1.00 equiv) in THF (1500 mL) was treated with $Et_3N$ (220 g, 2.18 mol, 2.00 equiv) at 0° C. for 50 min followed by the addition of 2-methylpropyl carbonochloridate (222 g, 1.63 mol, 1.50 equiv) in portions at 0° C. for 2 h. The resulting mixture was stirred at room temperature for 2 h. Add the mixture dropwise to the ammonia solution. The resulting mixture was stirred for 10 min at room temperature under air atmosphere. The resulting mixture was extracted with EtOAc (3×2.0 L). The combined organic layers were washed with brine (3×3 L), dried over anhydrous $Na_2SO_4$. After filtration, the filtrate was concentrated under reduced pressure. The residue was purified by silica gel column chromatography, eluted with petroleum ether/ethyl acetate (5:1) to afford tert-butyl (1R,3S,5R)-3-carbamoyl-2-azabicyclo[3.1.0]hexane-2-carboxylate (224 g, 90.3% yield, 96% purity) as a yellow oil.

LCMS Calculated for $C_{11}H_{18}N_2O_3$: 226.13; Observed: 227.1 $[M+H]^+$ tert-butyl (1R,3S,5R)-3-cyano-2-azabicyclo[3.1.0]hexane-2-carboxylate (15)

tert-butyl (1R,3S,5R)-3-cyano-2-azabicyclo[3.1.0]hexane-2-carboxylate (15)

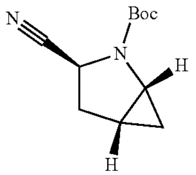

Into a 1000 mL 3-necked round-bottom flask were added tert-butyl (1R,3S,5R)-3-carbamoyl-2-azabicyclo[3.1.0]hexane-2-carboxylate (45.0 g, 198 mmol, 1.00 equiv), DCM (500 mL) and Pyridine (62.9 g, 795 mmol, 4.00 equiv) at room temperature. To the above mixture was added 2,2,2-trifluoroacetyl 2,2,2-trifluoroacetate (83.5 g, 397 mmol, 2.00 equiv) dropwise over 30 min at 0° C. The resulting mixture was stirred at 0° C. for additional 3 h. The resulting mixture was diluted with water (500 mL). The resulting mixture was extracted with $CH_2Cl_2$ (2×200 mL). The combined organic layers were washed with brine (2×200 mL), dried over anhydrous $Na_2SO_4$. After filtration, the filtrate was concentrated under reduced pressure. The residue was purified by silica gel column chromatography, eluted with petroleum ether/ethyl acetate (1:1) to afford tert-butyl (1R,3S,5R)-3-cyano-2-azabicyclo[3.1.0]hexane-2-carboxylate (40 g, 96.5% yield, 90% purity) as a white solid.

LCMS Calculated for $C_{11}H_{16}N_2O_2$: 208.12; Observed: 209.1 $[M+H]^+$

Step-11. (1R,3S,5R)-2-azabicyclo[3.1.0]hexane-3-carbonitrile (16)

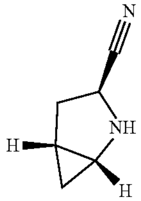

Into a 1000 mL round-bottom flask were added 4-methylbenzenesulfonic acid (39.7 g, 230 mmol, 1.20 equiv) and tert-butyl (1R,3S,5R)-3-cyano-2-azabicyclo[3.1.0]hexane-2-carboxylate (40.0 g, 208 mmol, 1.00 equiv) at room temperature. The resulting mixture was stirred at 40° C. for 16 h under nitrogen atmosphere. The mixture was allowed to cool down to room temperature. The resulting mixture was diluted with water (500 mL). The resulting mixture was extracted with $CH_2Cl_2$ (2×200 mL). The combined organic layers were washed with brine (2×200 mL), dried over anhydrous $Na_2SO_4$. After filtration, the filtrate was concentrated under reduced pressure. The residue was purified by silica gel column chromatography, eluted with petroleum ether/ethyl acetate (0:1) to afford (1R,3S,5R)-2-azabicyclo[3.1.0]hexane-3-carbonitrile (15 g, 72.1% yield, 95% purity) as a light yellow solid.

LCMS Calculated for $C_6H_8N_2$: 108.07; Observed: 109.0 $[M+H]^+$ 3-ethylbenzoic acid (1)

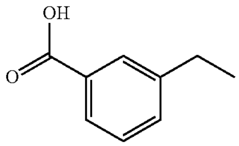

To a stirred solution of m-bromobenzoic acid (400 g, 1.99 mol, 1.00 equiv) and triethylborane (214 g, 2.19 mol, 1.10 equiv) in THF (3.40 L) and $H_2O$ (340 mL) were added $Cs_2CO_3$ (1297 g, 3.98 mol, 2.00 equiv) and $Pd(dppf)Cl_2$ (146 g, 199 mmol, 0.100 equiv) dropwise at room temperature under nitrogen atmosphere. The resulting mixture was stirred at 90° C. overnight under nitrogen atmosphere. The mixture was allowed to cool down to room temperature. The resulting mixture was extracted with EtOAc (2×2 L). The combined organic layers were washed with brine (2×2 L), dried over anhydrous $Na_2SO_4$. After filtration, the filtrate was concentrated under reduced pressure. The residue was purified by silica gel column chromatography, eluted with Petroleum ether/ethyl acetate (1:1) to afford 3-ethylbenzoic acid (253 g, 84.3% yield, 85% purity) as a white solid.

LCMS Calculated for: $C_9H_{10}O_2$, 150.07; Observed: 149.1 $[M-H]^-$ (3-ethylbenzoyl)glycine (3)

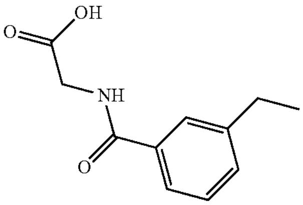

To a stirred solution of 3-ethylbenzoic acid (253 g, 1.68 mol, 1.00 equiv) and thionyl chloride (241 g, 2.02 mol, 1.20 equiv) in DCM (1.70 L) was added DMF (1.70 mL) dropwise at room temperature under nitrogen atmosphere. The resulting mixture was stirred at room temperature for 1 h under nitrogen atmosphere. The resulting mixture was concentrated under reduced pressure. The crude product was added to the stirred solution of glycine (127 g, 1.69 mol, 1.05 equiv) and NaOH (161 g, 4.02 mol, 2.50 equiv) in MeCN (1.80 L) dropwise at 0° C. under nitrogen atmosphere. The resulting mixture was stirred at room temperature for 3 h under nitrogen atmosphere. The mixture was acidified to pH 3 with HCl (aq.). The resulting mixture was concentrated under reduced pressure. The precipitated solids were collected by filtration and washed with petroleum ether (2×1 L). This resulted in (3-ethylbenzoyl)glycine (295 g, 42% yield, 90% purity) as a white solid.

LCMS Calculated for: $C_{11}H_{13}NO_3$, 207.09; Observed: 208.1 $[M+H]^+$ 2-(3-ethylphenyl)oxazol-5 (4H)-one (5)

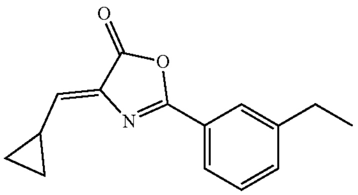 [SMILES: CCc1cccc(C2=N/C(=C\C3CC3)C(=O)O2)c1]

A solution of (3-ethylbenzoyl)glycine (295 g, 1.42 mmol, 1.00 equiv) and 1-Ethyl-3-(3-dimethylaminopropyl) carbodiimide hydrochloride (271 g, 1424 mmol, 1.00 equiv) in DCM (1.80 L) was stirred at room temperature for 2 h under nitrogen atmosphere. The resulting mixture was washed with water (2×3 L) and brine (1×3 L), dried over anhydrous sodium sulfate, filtered. To the above filtrate was added cyclopropanecarbaldehyde (109 g, 1.56 mol, 1.10 equiv) and $Al_2O_3$ (1452 g, 14.2 mol, 10.0 equiv). The resulting mixture was stirred at room temperature for 2 h under nitrogen atmosphere. The resulting mixture was filtered, the filter cake was washed with DCM (2×2 L). The filtrate was concentrated under reduced pressure. The residue was purified by silica gel column chromatography, eluted with Petroleum ether/EtOAc (1:1) to afford (4Z)-4-(cyclopropylmethylidene)-2-(3-ethylphenyl)-1,3-oxazol-5-one (100 g, 28.0% yield, 80% purity) as a white solid.

LCMS Calculated for $C_{15}H_{15}NO_2$: 241.11; Observed: 242.1 $[M+H]^+$ ethyl 2-((tert-butyldimethylsilyl)oxy)acetate (6)

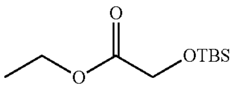

To a stirred solution of ethyl 2-hydroxyacetate (200 g, 1.92 mol, 1.00 equiv) and Imidazole (196 g, 2.88 mol, 1.50 equiv) in DMF (2 L) were added TBSCl (347 g, 2.31 mol, 1.20 equiv) dropwise at room temperature under nitrogen atmosphere. The reaction mixture was stirred for 2.0 h at room temperature. The mixture was diluted with water (5 L). The mixture was extracted with EtOAc (2×5 L). The combined organic phase was washed with brine (5 L), dried over anhydrous sodium sulfate, filtered and concentrated in vacuum. The residue was purified by silica gel chromatography, eluted with Petroleum ether/EtOAc (10:1) to afford ethyl 2-[(tert-butyldimethylsilyl)oxy]acetate (320 g, 76%) as a light yellow oil.

3-(((tert-butyldimethylsilyl)oxy)methyl)-1-(tetrahydro-2H-pyran-4-yl)-1H-pyrazol-5-amine (8)

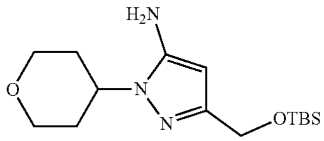 [SMILES: CC(C)(C)[Si](C)(C)OCc1cc(N)n(C2CCOCC2)n1]

A solution of MeCN (11.3 g, 275 mmol, 1.20 equiv) in THF (500 mL) was treated with LiHMDS (59.6 mL, 298 mmol, 1.30 equiv) for 0.5 h at −78° C. under nitrogen atmosphere followed by the addition of ethyl 2-[(tert-butyldimethylsilyl)oxy]acetate (50.0 g, 229 mmol, 1.00 equiv) dropwise at −78° C. The resulting mixture was stirred for 1 h at room temperature under nitrogen atmosphere. The reaction was quenched with sat. $NH_4Cl$ (aq.) at room temperature. The resulting mixture was extracted with EtOAc (2×500 mL). The combined organic layers were washed with brine (2×500 mL), dried over anhydrous $Na_2SO_4$. After filtration, the filtrate was concentrated under reduced pressure. This resulted in 4-((tert-butyldimethylsilyl)oxy)-3-oxobutanenitrile (48 g, crude) as a yellow solid. The crude product was added the solution of oxan-4-ylhydrazine (29.9 g, 257 mmol, 1.10 equiv) and TEA (47.4 g, 469 mmol, 2.00 equiv) in EtOH (500 ml) at room temperature. The resulting mixture was stirred for 3 h at 80° C. under nitrogen atmosphere. The resulting mixture was concentrated under vacuum. The residue was purified by silica gel column chromatography, eluted with Petroleum ether/EtOAc (5:1) to afford 3-(((tert-butyldimethylsilyl)oxy)methyl)-1-(tetrahydro-2H-pyran-4-yl)-1H-pyrazol-5-amine (21 g, 28% yield) as a yellow oil.

LCMS Calculated for $C_{15}H_{29}N_3O_2Si$: 311.20; Observed: 312.2 $[M+H]^+$ rac-N-((4R,5S)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-ethylbenzamide (9)

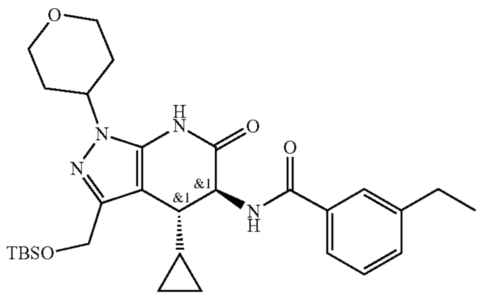 [SMILES: CCc1cccc(C(=O)N[C@@H]2C(=O)Nc3c(c(CO[Si](C)(C)C(C)(C)C)nn3C3CCOCC3)[C@H]2C2CC2)c1]

To a stirred solution of 3-(((tert-butyldimethylsilyl)oxy)methyl)-1-(tetrahydro-2H-pyran-4-yl)-1H-pyrazol-5-amine (100 g, 321 mmol, 1.00 equiv) and (4Z)-4-(cyclopropylmethylidene)-2-(3-ethylphenyl)-1,3-oxazol-5-one (77.5 g, 321 mmol, 1.00 equiv) in t-BuOH (2.00 L) was added $SnCl_2$ (6.09 g, 32.1 mmol, 0.10 equiv) in portions at room temperature under nitrogen atmosphere. The resulting mixture was stirred at 110° C. overnight under nitrogen atmosphere. The mixture was allowed to cool down to room temperature.

The resulting mixture was concentrated under reduced pressure. The residue was purified by silica gel column chromatography, eluted with Petroleum ether/EtOAc (1:1) to afford rac-N-((4R,5S)-3-(((tert-butyldimeth ylsilyl)oxy) methyl)-4-cyclopropyl-6-oxo-1-(tetrahydro-2H-pyran-4-yl)-4,5,6,7-tetrahydro-1H-pyrazolo[3,4-b]pyridin-5-yl)-3-ethylbenzamide (80.0 g, 45% yield, 85% purity) as a yellow solid.

LCMS Calculated for $C_{30}H_{44}N_4O_4Si$: 552.31; Observed: 553.3 $[M+H]^+$ rac-N-((4R,5R)-3-(((tert-butyldimethylsilyl)oxy) methyl)-4-cyclopropyl-6-oxo-1-(tetrahydro-2H-pyran-4-yl)-4,5,6,7-tetrahydro-1H-pyrazolo[3,4-b] pyridin-5-yl)-3-ethylbenzamide (10)

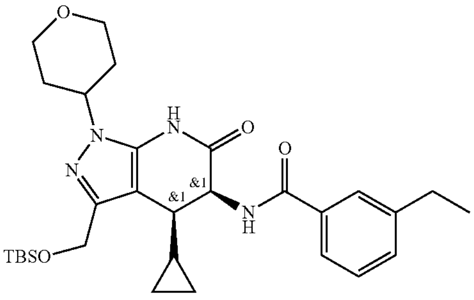 [SMILES: CCc1cccc(C(=O)N[C@@H]2C(=O)Nc3c(c(CO[Si](C)(C)C(C)(C)C)nn3C3CCOCC3)[C@@H]2C2CC2)c1]

A solution of rac-N-((4R,5S)-3-(((tert-butyldimethylsilyl) oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-ethylbenzamide (80 g, 145 mmol, 1.00 equiv) and DBU (83.7 g, 550 mmol, 3.80 equiv) in MeCN (1.00 L) was stirred at 80° C. overnight under nitrogen atmosphere. The mixture was allowed to cool down to room temperature. The reaction was quenched with water at room temperature. The mixture was acidified to pH 5 with citric acid aqueous solution. The resulting mixture was extracted with EtOAc (2×1 L). The combined organic layers were washed with brine (2×500 mL), dried over anhydrous $Na_2SO_4$. After filtration, the filtrate was concentrated under reduced pressure. The residue was purified by silica gel column chromatography, eluted with Petroleum ether/EtOAc (1:1) to afford rac-N-((4R,5R)-3-(((tert-butyldimethylsilyl)oxy) methyl)-4-cyclopropyl-6-oxo-1-(tetrahydro-2H-pyran-4-yl)-4,5,6,7-tetrahydro-1H-pyrazolo[3,4-b]pyridin-5-yl)-3-ethylbenzamide (60 g, 75.0% yield, 86% purity) as a white solid.

LCMS Calculated for: $C_{30}H_{44}N_4O_4Si$, 552.31; Observed: 553.3 $[M+H]^+$ rac-N-((4R,5R)-3-(((tert-butyldimethylsilyl)oxy) methyl)-4-cyclopropyl-7-ethyl-6-oxo-1-(tetr ahydro-2H-pyran-4-yl)-4,5,6,7-tetrahydro-1H-pyrazolo[3,4-b]pyridin-5-yl)-3-ethylbenzami de (11)

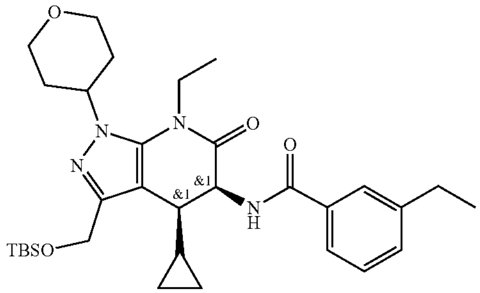 [SMILES: CCc1cccc(C(=O)N[C@@H]2C(=O)N(CC)c3c(c(CO[Si](C)(C)C(C)(C)C)nn3C3CCOCC3)[C@@H]2C2CC2)c1]

To a stirred solution of rac-N-((4R,5R)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-ethylbenzamide (60.0 g, 111 mmol, 1.00 equiv) and $K_3PO_4$ (47.3 g, 222 mmol, 2.00 equiv) in MeCN (800 mL) was added bromoethane (14.6 g, 133 mmol, 1.20 equiv) dropwise at room temperature under nitrogen atmosphere. The resulting mixture was stirred at 70° C. overnight under nitrogen atmosphere. The mixture was allowed to cool down to room temperature. The reaction was quenched with water at room temperature. The resulting mixture was extracted with EtOAc (2×600 mL). The combined organic layers were washed with brine (2×600 mL), dried over anhydrous $Na_2SO_4$. After filtration, the filtrate was concentrated under reduced pressure. The residue was purified by silica gel column chromatography, eluted with Petroleum ether/ethyl acetate (3:1) to afford rac-N-((4R,5R)-3-(((tert-butyldimethylsilyl)oxy)methyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-ethylbenzamide (45.0 g, 69.5% yield, 90% purity) as a white solid.

LCMS Calculated for $C_{32}H_{48}N_4O_4Si$: 580.34; Observed: 581.3 $[M+H]^+$

N-((4S,5S)-4-cyclopropyl-7-ethyl-3-(hydroxymethyl)-6-oxo-1-(tetrahydro-2H-pyran-4-yl)-4,5,6,7-tetrahydro-1H-pyrazolo[3,4-b]pyridin-5-yl)-3-ethylbenzamide (12A)

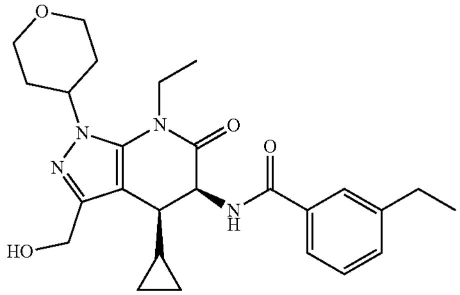 [SMILES: CCc1cccc(C(=O)N[C@@H]2C(=O)N(CC)c3c(c(CO)nn3C3CCOCC3)[C@@H]2C2CC2)c1]

A solution of rac-N-((4R,5R)-3-(((tert-butyldimethylsilyl)oxy)methyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-ethylbenzamide (45.0 g, 77.5 mmol, 1.00 equiv) and HCl (250 mL, 2.0 M) in MeCN (250 mL) was stirred at room temperature for 1 h under nitrogen atmosphere. The reaction was quenched with water at room temperature. The resulting mixture was extracted with EtOAc (2×300 mL). The combined organic layers were washed with brine (2×300 mL), dried over anhydrous $Na_2SO_4$. After filtration, the filtrate was concentrated under reduced pressure. This resulted in rac-N-((4R,5R)-4-cyclopropyl-7-ethyl-3-(hydroxymethyl)-6-oxo-1-(tetrahydro-2H-pyran-4-yl)-4,5,6,7-tetrahydro-1H-pyrazolo[3,4-b]pyridin-5-yl)-3-ethylbenzamide (32 g, 90% purity). The racemate product (32.0 g) was purified by Prep-Chair-SFC with the following conditions (Column: CHIRALPAK IA, 3*25 cm, 5 μm; Mobile Phase A: $CO_2$, Mobile Phase B: MEOH (0.1% 2M $NH_3$-MEOH); Flow rate: 80 mL/min; Gradient: isocratic 30% B; Column Temperature (C): 35; Back Pressure (bar): 100; Wave Length: 220 nm; RT1(min): 4; RT2(min): 6.4; Sample Solvent: MEOH; Injection Volume: 3 mL) to afford N-((4S,5S)-4-cyclopropyl-7-ethyl-3-(hydroxymethyl)-6-oxo-1-(tetrahydro-2H-pyran-4-yl)-4,5,6,7-tetrahydro-1H-pyrazolo[3,4-b]pyridin-5-yl)-3-ethylbenzamide (12 g, 37.5% yield, 99% purity) as a white solid.

LCMS Calculated for $C_{26}H_{34}N_4O_4$: 466.26; Observed: 467.3 $[M+H]^+$

Chiral-SFC (Method-M): 100% at RT 1.302 min

Optical rotation: [a]=+20.97 (C=0.1 g/100 ml in MeOH, T=25° C.)

(4S,5S)-4-cyclopropyl-7-ethyl-5-(3-ethylbenzamido)-1-(oxan-4-yl)-6-oxo-4H,5H-pyrazolo[3,4-b]pyridine-3-carboxylic acid (13)

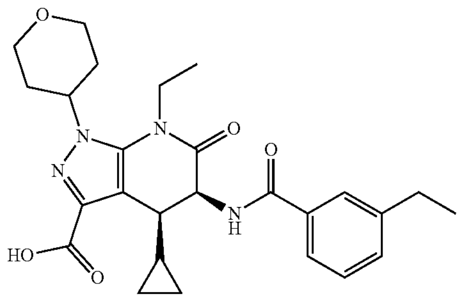 [SMILES: CCc1cccc(C(=O)N[C@@H]2C(=O)N(CC)c3c(c(C(=O)O)nn3C3CCOCC3)[C@@H]2C2CC2)c1]

To a stirred solution of N-((4S,5S)-4-cyclopropyl-7-ethyl-3-(hydroxymethyl)-6-oxo-1-(tetrahydro-2H-pyran-4-yl)-4,5,6,7-tetrahydro-1H-pyrazolo[3,4-b]pyridin-5-yl)-3-ethylbenzamide (12.0 g, 25.7 mmol, 1.00 equiv) and $H_2O$ (46.3 g, 2.57 mol, 100 equiv) in MeCN (120 mL) were added (acetyloxy)(phenyl)-l^[3]-iodanyl acetate (24.8 g, 77.1 mmol, 3.00 equiv) and 2,2,6,6-tetramethylpiperidin-1-olate (2.01 g, 12.8 mmol, 0.50 equiv) in portions at room temperature under nitrogen atmosphere. The resulting mixture was stirred at room temperature for 2 h under nitrogen atmosphere. The reaction was quenched with water at room temperature. The resulting mixture was extracted with EtOAc (2×100 mL). The combined organic layers were washed with brine (2×100 mL), dried over anhydrous $Na_2SO_4$. After filtration, the filtrate was concentrated under reduced pressure. The residue was purified by silica gel column chromatography, eluted with $CH_2Cl_2$/MeOH (10:1) to afford (4S,5S)-4-cyclopropyl-7-ethyl-5-(3-ethylbenzamido)-1-(oxan-4-yl)-6-oxo-4H,5H-pyrazolo[3,4-b]pyridine-3-carboxyl ic acid (12 g, 97.1% yield, 95% purity) as a white solid.

LCMS Calculated for $C_{26}H_{32}N_4O_5$: 480.24; Observed: 481.3 $[M+H]^+$

N-((4S,5S)-3-((1R,3S,5R)-3-cyano-2-azabicyclo[3.1.0]hexane-2-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-ethylbenzamide (I-552)

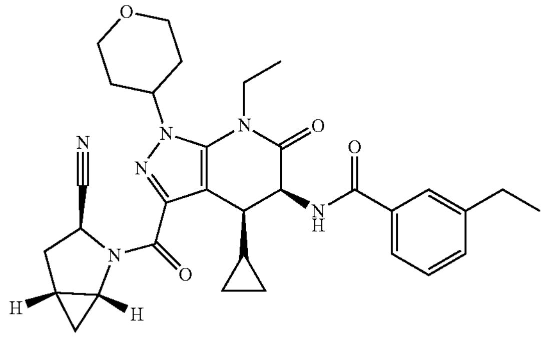 [SMILES: CCc1cccc(C(=O)N[C@@H]2C(=O)N(CC)c3c(c(C(=O)N4[C@H](C#N)C[C@H]5C[C@H]54)nn3C3CCOCC3)[C@@H]2C2CC2)c1]

A solution of (4S,5S)-4-cyclopropyl-7-ethyl-5-(3-ethylbenzamido)-1-(oxan-4-yl)-6-oxo-4H,5H-pyrazolo[3,4-b]pyridine-3-carboxylic acid (6.00 g, 12.5 mmol, 1.00 equiv) in DCM (60.0 mL) was treated with DIEA (2.10 g, 16.2 mmol, 1.30 equiv) and HATU (5.70 g, 15.0 mmol, 1.20 equiv) at room temperature for 10 min under nitrogen atmosphere followed by the addition of (1R,3S,5R)-2-azabicyclo[3.1.0]hexane-3-carbonitrile (1.49 g, 13.7 mmol, 1.10 equiv) at room temperature. The resulting mixture was stirred at room temperature for 1 h under nitrogen atmosphere. The resulting mixture was concentrated under reduced pressure. The residue was purified by Prep-HPLC with the following conditions (Column: CHIRALPAK IA, 3*25 cm, 5 μm; Mobile Phase A: $CO_2$, Mobile Phase B: MEOH (0.1% 2M $NH_3$-MEOH); Flow rate: 80 mL/min; Gradient (B %): isocratic 30% B; Column Temperature (C): 35; Back Pressure (bar): 100; Wave Length: 220 nm; RT1 (min): 4; RT2(min): 6.4; Sample Solvent: MEOH; Injection Volume: 3 mL) to afford N-((4S,5S)-3-((1R,3S,5R)-3-cyano-2-azabicyclo[3.1.0]hexane-2-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-ethylbenzamide (5.2 g, 72.9% yield, 99.9% purity) as a white solid.

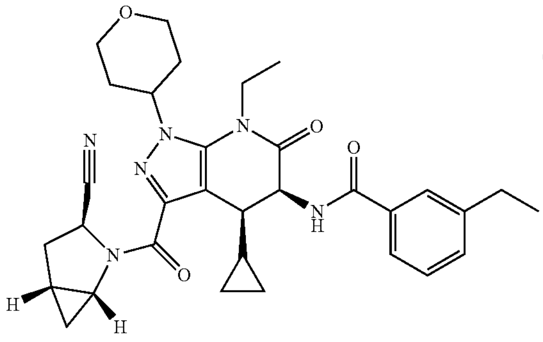 [SMILES: CCc1cccc(C(=O)N[C@@H]2C(=O)N(CC)c3c(c(C(=O)N4[C@H](C#N)C[C@H]5C[C@H]54)nn3C3CCOCC3)[C@@H]2C2CC2)c1]

I-552

$^1$H NMR (400 MHz, DMSO-$d_6$) δ 8.43-8.33 (m, 1H), 7.79 (s, 1H), 7.77-7.70 (m, 1H), 7.47-7.36 (m, 2H), 5.01 (dd, J = 7.6, 6.0 Hz, 1H), 4.96-4.80 (m, 1H), 4.58-4.45 (m, 1H), 4.37-4.27 (m, 1H), 4.17-3.98 (m, 2H), 3.98-3.79 (m, 2H), 3.62-3.45 (m, 2H), 3.45-3.35 (m, 1H), 2.69 (q, J = 7.6 Hz, 2H), 2.49-2.33 (m, 2H), 2.33-2.20 (m, 1H), 2.15-2.02 (m, 1H), 2.02-1.79 (m, 3H), 1.31-1.19 (m, 6H), 1.12-0.88 (m, 1H), 0.86-0.74 (m, 1H), 0.67-0.56 (m, 1H), 0.54-0.43 (m, 1H), 0.33-0.01 (m, 3H). LCMS Calculated for $C_{32}H_{38}N_6O_4$: 570.30; Observed (Method-X): 569.3 $[M - H]^-$, 99.9% at RT 1.405 min.

Example 36: Synthesis of Compounds

NMR:

$^1$H NMR spectrum was recorded on Bruker 400 MHz and 300 MHz instruments internally referenced to a tetramethylsilane (TMS) signal. Chemical shifts (δ) and coupling constants (J) were expressed in parts per million and hertz, respectively.

LCMS

Method-A (LCMS-25): Column: L-column3 C18 3.0*30 mm 3 μm, Mobile Phase: A: 5 mM $NH_4HCO_3$ in water; B: Acetonitrile, Flow Rate: 1.2 mL/min. Oven Temperature: 40 C, Gradient program (B %): 0.00/10.0, 1.4/95, 1.9/95, 1.91/10

Method-B (LCMS-10/24): Column: HALO C18, 30*3.0 mm, 2 μm, Mobile Phase: A: Water/0.05% TFA; B: Acetonitrile, Flow Rate: 1.5 mL/min. Oven Temperature: 40 C, Gradient program (B %): 0.01/5, 1.5/95, 1.9/95, 1.91/5

Method-C(LCMS-10): Column: CORTECS C18+,30*3.0 mm,2.7 μm, Mobile Phase: A: Water/0.05% TFA; B: Acetonitrile, Flow Rate: 1.5 mL/min. Oven Temperature: 40 C, Gradient program (B %): 0.01/5, 1.5/95, 1.9/95, 1.91/5

Method-D (LCMS-13): Column: HPH-C18, 50*3.0 mm, 2.7 μm, Mobile Phase: A: Water/0.05% ammonia water; B: Acetonitrile, Flow Rate: 1.2 mL/min. Oven Temperature: 40 C, Gradient program (B %): 0.50/55, 3.50/70, 4.00/95, 4.80/95, 4.81/5.

Method-E (LCMS-29): Column: SB-Aq 4.6*50 mm 1.8 μm, Mobile Phase: A: Water/0.02% FA; B: Acetonitrile0.02% FA, Flow Rate: 1.5 mL/min. Oven Temperature: 40 C, Gradient program (B %): 0.00/5.0, 2.00/95.0, 2.90/95.0, 2.91/5.0.

Method-F (LCMS-10): Column: CORTECS C18+,30*3.0 mm,2.7 μm, Mobile Phase: A: Water/0.05% TFA; B: Acetonitrile, Flow Rate: 1.5 mL/min. Oven Temperature: 40 C, Gradient program (B %): 0.30/30, 1.80/60, 2.20/95, 2.80/95, 2.81/5.

Method-G (LCMS-24): Column: SB-Aq 4.6*50 mm 1.8 μm, Mobile Phase: A: Water/0.05% TFA; B: Acetonitrile, Flow Rate: 1.5 mL/min. Oven Temperature: 40 C, Gradient program (B %): 0.00/5, 0.30/40, 1.80/80, 2.20/95, 2.80/95, 2.81/5.

Method-H (LCMS-10): Column: SB-Aq 4.6*50 mm 1.8 μm, Mobile Phase: A: Water/0.05% TFA; B: Acetonitrile, Flow Rate: 1.5 mL/min. Oven Temperature: 40 C, Gradient program (B %): 0.00/5, 0.40/40, 3.20/70, 4.10/95, 4.80/95, 4.81/5.

Method-I (LCMS-13): Column: HPH-C18, 50*3.0 mm, 2.7 μm, Mobile Phase: A: Water/0.05% ammonia water; B: Acetonitrile, Flow Rate: 1.2 mL/min. Oven Temperature: 40 C, Gradient program (B %): 0.01/5, 0.50/50, 2.10/80, 2.60/95, 3.30/95, 3.31/5.

Method-J (LCMS-13): Column: HPH-C18, 50*3.0 mm, 2.7 μm, Mobile Phase: A: Water/0.05% ammonia water; B: Acetonitrile, Flow Rate: 1.2 mL/min. Oven Temperature: 40 C, Gradient program (B %): 0.01/5, 2.00/95, 2.80/95, 2.81/5.

Method-K (LCMS-29): Column: CORTECS C18+, 30*3.0 mm,2.7 μm, Mobile Phase: A: Water/0.02% FA; B: Acetonitrile0.02% FA, Flow Rate: 1.5 mL/min. Oven Temperature: 40 C, Gradient program (B %): 0.00/5.0, 1.50/95.0, 1.90/95.0, 1.91/5.0.

Method-L (LCMS-13): Column: Atlantis Premiser BEH C18 AX, 50*4.6 mm,2.5 μm, Mobile Phase: A: Water/0.05% ammonia water; B: Acetonitrile, Flow Rate: 1.2 mL/min. Oven Temperature: 40 C, Gradient program (B %): 0.01/50, 2.00/95, 2.80/95, 2.81/50.

Method-M (LCMS-13): Column: YMC-Triart C18, 50*3.0 mm,3 μm, Mobile Phase: A: Water/0.05% ammonia water; B: Acetonitrile, Flow Rate: 1.2 mL/min. Oven Temperature: 40 C, Gradient program (B %): 0.01/50, 2.00/95, 2.80/95, 2.81/30.

Method-N(LCMS-13): Column: L-column3 C18, 50*3.0 mm, 3 μm, Mobile Phase: A: Water/0.05% ammonia water; B: Acetonitrile, Flow Rate: 1.2 mL/min. Oven Temperature: 40 C, Gradient program (B %): 0.01/5, 2.00/95, 2.80/95, 2.81/5.

Method-O (LCMS-13): Column: HPH-C18, 100*4.6 mm, 2.7 μm, Mobile Phase: A: Water/0.05% ammonia water; B: Acetonitrile, Flow Rate: 1.2 mL/min. Oven Temperature: 40 C, Gradient program (B %): 0.01/40, 5.50/70, 6.5/95, 7.50/95, 7.51/40, Method-P(LCMS-13): Column: L-column3 C18, 50*3.0 mm, 3 μm, Mobile Phase: A: Water/0.05% ammonia water; B: Acetonitrile, Flow Rate: 1.2 mL/min. Oven Temperature: 40 C, Gradient program (B %): 0.01/5, 0.50/50, 2.10/80, 2.60/95, 3.30/95, 3.31/5.

Method-Q (LCMS-13): Column: HPH-C18, 50*3.0 mm, 2.7 μm, Mobile Phase: A: Water/0.05% ammonia water; B: Acetonitrile, Flow Rate: 1.2 mL/min. Oven Temperature: 40 C, Gradient program (B %): 0.01/5, 0.50/50, 2.10/80, 2.60/95, 3.30/95, Method-R (LCMS-29): Column: HALO 90A, PCS C18 30*3 mm 2.7 μm, Mobile Phase: A: Water/0.02% FA; B: Acetonitrile0.02% FA, Flow Rate: 1.5 mL/min. Oven Temperature: 40 C, Gradient program (B %): 0.00/5.0, 1.50/95.0, 1.90/95.0, 1.91/5.0.

Method-S (LCMS-13): Column: YMC-Triart C18, 50*3.0 mm,3 μm, Mobile Phase: A: Water/0.05% ammonia water;

B: Acetonitrile, Flow Rate: 1.2 mL/min. Oven Temperature: 40 C, Gradient program (B %): 0.01/30, 3.50/95, 4.80/95, 4.81/30.

Method-T (LCMS-10): Column: SB-Aq, 50*4.6 mm, 1.8 μm, Mobile Phase: A: Water/0.05% TFA; B: Acetonitrile, Flow Rate: 1.5 mL/min. Oven Temperature: 40 C, Gradient program (B %): 0.30/30, 1.80/60, 2.20/95, 2.80/95, 2.81/5.

Method-U (LCMS-13): Column: Atlantis Premiser BEH C18 AX, 50*4.6 mm,2.5 μm, Mobile Phase: A: Water/0.05% ammonia water; B: Acetonitrile, Flow Rate: 1.2 mL/min. Oven Temperature: 40 C, Gradient program (B %): 0.01/50, 3.50/80, 4.00/95, 4.80/95, 4.81/50.

Method-V (LCMS-13): Column: HPH-C18, 50*3.0 mm, 2.7 μm, Mobile Phase: A: Water/0.05% ammonia water; B: Acetonitrile, Flow Rate: 1.2 mL/min. Oven Temperature: 40 C, Gradient program (B %): 0.01/5, 2.00/95, 2.80/95, 2.81/5.

Method-W (LCMS-13): Column: YMC-Triart C18, 50*3.0 mm,3 μm, Mobile Phase: A: Water/0.05% ammonia water; B: Acetonitrile, Flow Rate: 1.2 mL/min. Oven Temperature: 40 C, Gradient program (B %): 0.01/5, 2.00/95, 2.80/95, 2.81/5.

Method-X (LCMS-25): Column: L-column3 C18 3.0*30 mm 3 μm, Mobile Phase: A: 5 mM $NH_4HCO_3$ in water; B: Acetonitrile, Flow Rate: 1.2 mL/min. Oven Temperature: 40 C, Gradient program (B %): 0.00/10.0, 0.30/40, 1.80/70, 2.20/95, 2.90/95, 2.91/10

Method-Y (LCMS-10/24): Column: HALO C18, 30*3.0 mm, 2 μm, Mobile Phase: A: Water/0.05% TFA; B: Acetonitrile, Flow Rate: 1.5 mL/min. Oven Temperature: 40 C, Gradient program (B %): 0.01/5, 2.00/40, 2.50/95, 2.80/95, 2.81/5

Method-Z (LCMS-13): Column: HPH-C18, 50*3.0 mm, 2.7 μm, Mobile Phase: A: Water/0.05% ammonia water; B: Acetonitrile, Flow Rate: 1.2 mL/min. Oven Temperature: 40 C, Gradient program (B %): 0.01/5, 0.50/30, 2.10/60, 2.50/95, 2.80/95, 2.81/5.

Method-AA (LCMS-10): Column: CORTECS C18+, 30*3.0 mm,2.7 μm, Mobile Phase: A: Water/0.05% TFA; B: Acetonitrile, Flow Rate: 1.5 mL/min. Oven Temperature: 40 C, Gradient program (B %): 0.00/5, 1.80/45, 2.20/95, 2.80/95, 2.81/5.

Method-AB (LCMS-29): Column: CORTECS C18+, 30*3.0 mm,2.7 μm, Mobile Phase: A: Water/0.02% FA; B: Acetonitrile0.02% FA, Flow Rate: 1.5 mL/min. Oven Temperature: 40 C, Gradient program (B %): 0.00/5.0, 1.80/40, 2.30/95.0, 2.80/95.0, 2.81/5.0.

Method-AC (LCMS-13): Column: HPH-C18, 50*3.0 mm, 2.7 μm, Mobile Phase: A: Water/0.05% ammonia water; B: Acetonitrile, Flow Rate: 1.2 mL/min. Oven Temperature: 40 C, Gradient program (B %): 0.01/5, 0.50/40, 2.10/70, 2.50/95, 2.80/95, 2.81/5.

Method-AD (LCMS-10): Column: CORTECS C18+, 30*3.0 mm,2.7 μm, Mobile Phase: A: Water/0.05% TFA; B: Acetonitrile, Flow Rate: 1.5 mL/min. Oven Temperature: 40 C, Gradient program (B %): 0.30/20, 1.80/50, 2.20/95, 2.80/95, 2.81/5.

Method-AE (LCMS-10): Column: Cortecs T3, 50*3.0 mm, 2.7 μm, Mobile Phase: A: Water/0.05% TFA; B: Acetonitrile, Flow Rate: 1.5 mL/min. Oven Temperature: 40 C, Gradient program (B %): 0.01/5, 2.20/95, 2.80/95, 2.81/5.

Method-AF (LCMS-29): Column: SB-Aq 4.6*50 mm 1.8 μm, Mobile Phase: A: Water/0.02% FA; B: Acetonitrile0.02% FA, Flow Rate: 1.5 mL/min. Oven Temperature: 40 C, Gradient program (B %): 0.00/5.0, 3.00/50, 4.00/95.0, 4.80/95.0, 4.81/5.0.

Method-AG (LCMS-13): Column: HPH-C18, 50*3.0 mm, 2.7 μm, Mobile Phase: A: Water/0.05% ammonia water; B: MeOH, Flow Rate: 1.0 mL/min. Oven Temperature: 40 C, Gradient program (B %): 0.00/40, 4.00/95, 5.80/95, 5.81/40.

Method-AH (LCMS-13): Column: HPH-C18, 50*3.0 mm, 2.7 μm, Mobile Phase: A: Water/0.05% ammonia water; B: Acetonitrile, Flow Rate: 1.2 mL/min. Oven Temperature: 40 C, Gradient program (B %): 0.01/5, 0.80/40, 3.60/70, 4.00/95, 4.80/95, 4.81/5.

Method-AI (LCMS-10): Column: SB-Aq 4.6*50 mm 1.8 μm, Mobile Phase: A: Water/0.05% TFA; B: Acetonitrile/0.05% TFA, Flow Rate: 1.5 mL/min. Oven Temperature: 40 C, Gradient program (B %): 0.00/5, 0.30/30, 1.80/60, 2.20/95, 2.80/95, 2.81/5.

Method-AJ (LCMS-10): Column: CORTECS C18+, 30*3.0 mm,2.7 μm, Mobile Phase: A: Water/0.05% TFA; B: Acetonitrile, Flow Rate: 1.5 mL/min. Oven Temperature: 40 C, Gradient program (B %): 0.01/5, 1.60/40, 2.20/95, 2.80/95, 2.81/5

Method-AK (LCMS-29): Column: SB-Aq 4.6*50 mm 1.8 μm, Mobile Phase: A: Water/0.02% FA; B: Acetonitrile0.02% FA, Flow Rate: 1.5 mL/min. Oven Temperature: 40 C, Gradient program (B %): 0.00/5.0, 0.40/20, 3.00/50, 4.00/95.0, 4.80/95.0, 4.81/5.0.

Method-AL (LCMS-25): Column: L-column3 C18 3.0*30 mm 3 μm, Mobile Phase: A: 5 mM $NH_4HCO_3$ in water; B: Acetonitrile, Flow Rate: 1.2 mL/min. Oven Temperature: 40 C, Gradient program (B %): 0.00/10.0, 1.80/50, 2.30/95, 2.90/95, 2.91/10

Method-AM (LCMS-10): Column: ZORBAX SB-Aq, 50*4.6 mm, 1.8 μm, Mobile Phase: A: Water/0.05% TFA; B: Acetonitrile, Flow Rate: 1.5 mL/min. Oven Temperature: 40 C, Gradient program (B %): 0.01/5, 2.00/95, 2.80/95, 2.81/5.

Method-AN (LCMS-13): Column: Atlantis Premier BEH C18 AX, 4.6*50 mm, 2.5 μm, Mobile Phase: A: Water/0.05% ammonia water; B: Acetonitrile, Flow Rate: 1.2 mL/min. Oven Temperature: 40 C, Gradient program (B %): 0.01/5, 0.50/40, 2.10/70, 2.50/95, 2.80/95, 2.81/5.

Method-AO (LCMS-24): Column: HALO C18, 30*3.0 mm, 2 μm, Mobile Phase: A: Water/0.05% TFA; B: Acetonitrile, Flow Rate: 1.5 mL/min. Oven Temperature: 40 C, Gradient program (B %): 0.01/5, 0.30/40, 1.80/70, 2.20/95, 2.80/95, 2.81/5.

Method-AP (LCMS-13): Column: YMC-Triart C18, 50*3.0 mm,3 μm, Mobile Phase: A: Water/0.05% ammonia water; B: Acetonitrile, Flow Rate: 1.2 mL/min. Oven Temperature: 40 C, Gradient program (B %): 0.01/5, 0.50/65, 2.10/90, 2.60/95, 3.30/95, 3.31/5.

Method-AQ (LCMS-13): Column: YMC-Triart C18, 50*3.0 mm,3 μm, Mobile Phase: A: Water/0.05% ammonia water; B: Acetonitrile, Flow Rate: 1.2 mL/min. Oven Temperature: 40 C, Gradient program (B %): 0.01/5, 0.80/45, 3.60/75, 4.00/90, 4.80/95, 4.81/5.

Method-AR (LCMS-29): Column: Kinetex XB-C18, 30*3.0 mm, 1.7 μm; Mobile Phase: A: Water/0.1% FA; B: Acetonitrile0.07% FA, Flow Rate: 1.5 mL/min. Oven Temperature: 40 C, Gradient program (B %): 0.00/5.0, 1.50/95.0, 1.90/95.0, 1.91/5.0.

Method-AS (LCMS-10): Column: SB-Aq, 30*3.0 mm, 1.8 μm, Mobile Phase: A: Water/0.05% TFA; B: Acetonitrile, Flow Rate: 1.5 mL/min. Oven Temperature: 40 C, Gradient program (B %): 0.01/5, 1.5/95, 1.9/95, 1.91/5

Method-AT (LCMS-13): Column: L-column3 C18, 50*3.0 mm, 3 μm, Mobile Phase: A: Water/0.05% ammonia water; B: Acetonitrile, Flow Rate: 1.2 mL/min. Oven Temperature: 40 C, Gradient program (B %): 0.01/5, 0.80/50, 3.60/80, 4.00/95, 4.80/95, 4.81/5.

Chiral HPLC:

Method-A: CHIRALPAK IF-3, 50*4.6 mm, 3 μm IF30CB-CP002; Mobile Phase: A: n-Hexane/DCM=5/1 B: IPA (0.1% DEA); Conc. of Pump B: 30.0%; Flow rate: 1.0 ml/min; Column Temperature: 25 C.

Method-B: CHIRALPAK IH-3, 100*4.6 mm, 3 μm IH30CC-BT002; Mobile Phase: A: n-Hexane/THF=4/1 B: MeOH; Conc. of Pump B: 2.0%; Flow rate: 1.0 ml/min; Column Temperature: 25 C.

Method-C: CHIRALPAK IH-3, 50*4.6 mm, 3 μm IH30CB-BX008; Mobile Phase: A: n-Hexane B: EtOH; Conc. of Pump B: 20%; Flow rate: 1.0 ml/min; Column Temperature: 25 C.

Method-D: CHIRALPAK IG-3, 50*4.6 mm, 3 μm IG30CB-BW008; Mobile Phase: A: n-Hexane/DCM=5/1 B: EtOH (0.1% MIPA); Conc. of Pump B: 50%; Flow rate: 1.0 ml/min; Column Temperature: 25 C.

Method-E: Column: XA-RP-CHIRALPAK IB N—3 4.6*50 mm, 3 μm; IBN3CC-XD006; Mobile Phase A: Water (0.05% TFA), Mobile Phase B: Acetonitrile, Conc. of Pump B: 10.0%; Flow rate: 1.0 ml/min; Oven Temperature: 25 C.

Method-F: Column: CHIRALPAK IH-3, 50*4.6 mm, 3 μm 30CC-WH004; Mobile Phase A: n-Hexane/THF=4/1, Mobile Phase B: MeOH (0.5% FA), Conc. of Pump B: 5.0%; Flow rate: 1.0 ml/min; Oven Temperature: 25 C.

Method-G: Column: (R,R)-WHELK-O1 100*4.6 mm,3.5 μm 71749; Mobile Phase A: n-Hexane/DCM=3/1, Mobile Phase B: EtOH (0.1% EDA), Conc. of Pump B: 20.0%; Flow rate: 1.0 ml/min; Oven Temperature: 25 C.

Method-H: Column: CHIRALPAK IH-3, 100*4.6 mm, 3 μm IH30CC-BT002; Mobile Phase A: n-Hexane/DCM=5/1, Mobile Phase B: EtOH, Conc. of Pump B: 5.0%; Flow rate: 1.0 ml/min; Oven Temperature: 25 C.

Method-I (Chiral-HPLC): Column: CHIRALPAK IE-3, 50*4.6 mm, 3 μm IE30CB-BV004; Mobile Phase A: n-Hexane/DCM=3/1, Mobile Phase B: EtOH, Conc. of Pump B: 5.0%; Flow rate: 1.0 ml/min; Oven Temperature: 25 C.

Chiral SFC

Method-A: Column: CHIRALPAK IG-3, 50*3.0 mm, 3 μm; Co-Solvent: MeOH/DCM=1/1 (20 mM $NH_3$); Gradient (B): 10% to 50% in 2.0 min, hold 1.0 min at 50%. Flow rate: 3.0 ml/min; Column Temperature: 35 C.

Method-B: Column: (R,R)-WHELK CORE 50*3.0 mm,2.7 μm; Co-Solvent: MeOH/DCM=1/1 (10 mM $NH_3$); Gradient (B): 10% to 50% in 2.0 min, hold 1.0 min at 50%. Flow rate: 3.0 ml/min; Column Temperature: 35 C.

Method-C: Column: CHIRALPAK IG-U, 50*3.0 mm, 1.6 μm; Co-Solvent: MeOH/DCM=1/1 (20 mM $NH_3$); Gradient (B): 10% to 50% in 2.0 min, hold 1.0 min at 50%. Flow rate: 3.0 ml/min; Column Temperature: 35 C.

Method-D: Column: Cellulose-SC 100×4.6 mm 3.0 μm; Co-Solvent: MeOH+50% DCM+10 mM $NH_3$; Gradient (B): 0.01/10, 2.50/50, 3.70/50, 3.71/10; Flow rate: 3.0 ml/min; Column Temperature: 40 C.

Method-E: Column: CHIRALPAK IA-U, 50*3 mm, 1.6 μm; Co-Solvent: MeOH/DCM=1/1 (10 mM $NH_3$); Gradient (B): 10% to 50% in 2.0 min, hold 1.0 min at 50%. Flow rate: 1.0 ml/min; Column Temperature: 35 C.

Method-F: Column: CHIRALPAK IH—U, 50*3 mm, 1.6 μm; Co-Solvent: MeOH/DCM=1/1 (10 mM $NH_3$); Gradient (B): 10% to 50% in 2.0 min, hold 1.0 min at 50%. Flow rate: 1.0 ml/min; Column Temperature: 35 C.

Method-G: Column: (R,R)-WHELK-01 CORE 50*4.6 mm,3.5 μm; Co-Solvent: MeOH/DCM=1/1 (20 mM $NH_3$); Gradient (B): 10% to 50% in 2.5 min, hold 1.2 min at 50%. Flow rate: 3.0 ml/min; Column Temperature: 35 C.

Method-H: Column: CHIRALPAK IM-3, 50*3 mm, 3 μm; Co-Solvent: IPA+50% Hex=20 mM $NH_3$; Gradient (B): 10% to 50% in 2.0 min, hold 1.0 min at 50%. Flow rate: 3.0 ml/min; Column Temperature: 35 C.

Method-I: Column: CHIRALPAK IG-3, 50*3.0 mm, 3 μm; Co-Solvent: IPA+50% Hex+20 mM $NH_3$; Gradient (B): 10% to 50% in 2.0 min, hold 1.0 min at 50%. Flow rate: 3.0 ml/min; Column Temperature: 35 C.

HPLC:

Method-A: Cortecs C18+, 100*4.6 mm, 2.7 μm, Mobile Phase: A: 0.1% MSA in water; B: Acetonitrile, Flow Rate: 1.5 mL/min. Oven Temperature: 40 C, Gradient program (B %): 0.00/10.0, 1.50/40, 8.50/70, 10.0/95, 12.0/95.

1. Synthesis of rac-N-((4R,5R)-3-(2-aminopropan-2-yl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-671)

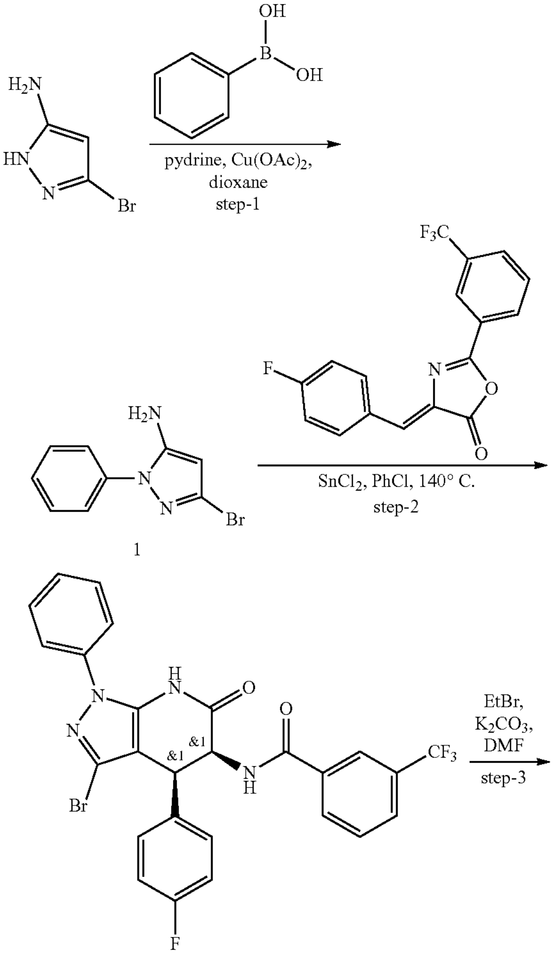

1

2

-continued

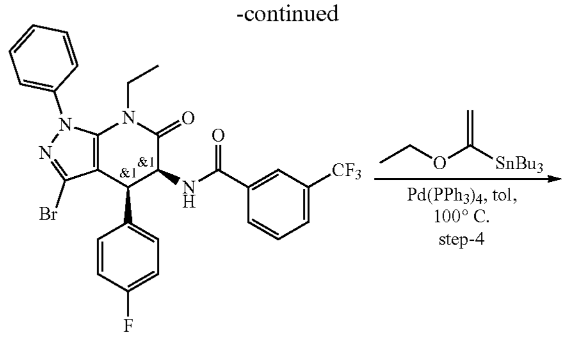

3

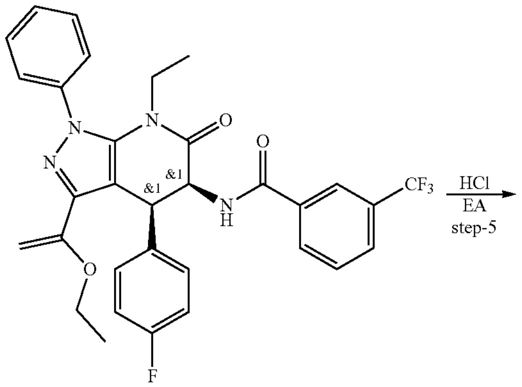

4

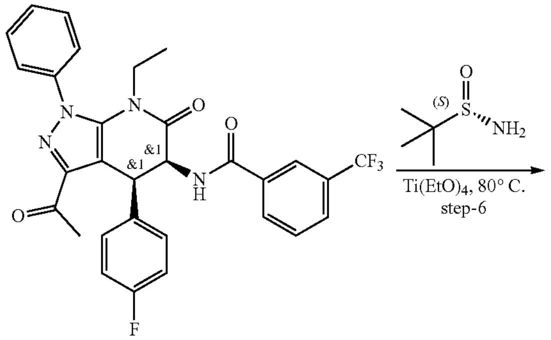

I-231

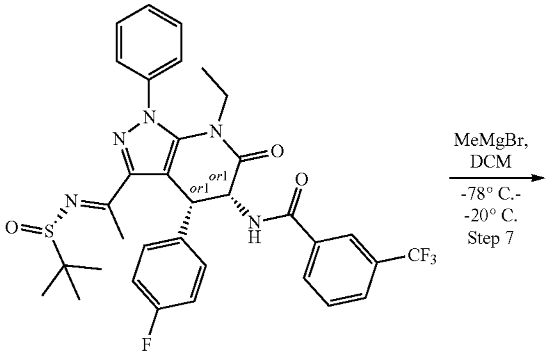

5

-continued

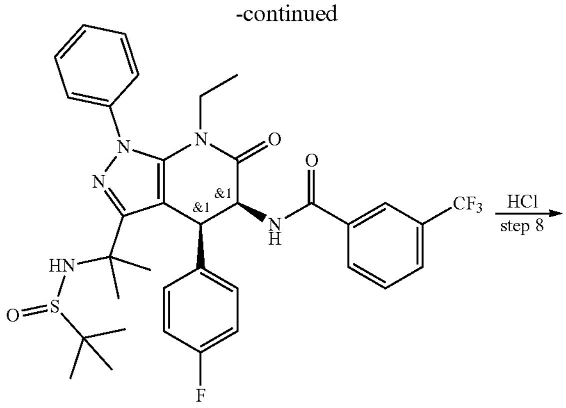

6

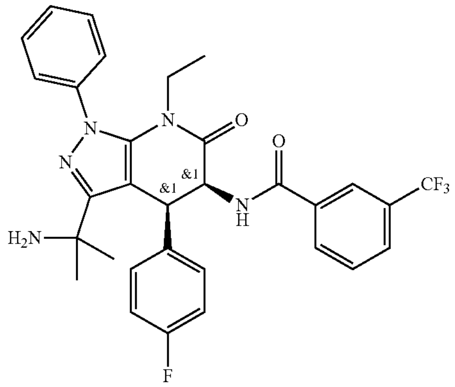

I-671

(1)

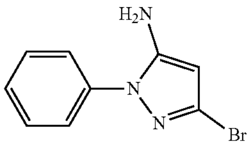

3-bromo-1-phenyl-1H-pyrazol-5-amine

A solution of 5-bromo-2H-pyrazol-3-amine (25.0 g, 154 mmol, 1.00 equiv), $Cu(OAc)_2$ (11.2 g, 61.7 mmol, 0.400 equiv), Pyridine (122 g, 1.54 mol, 10.0 equiv) and phenyl boronic acid (18.8 g, 154 mmol, 1.00 equiv) in dioxane (250 mL) was stirred for 5 h at 60° C. The mixture was allowed to cool down to room temperature. The resulting mixture was filtered, the filter cake was washed with DCM (2×100 mL). The filtrate was concentrated under reduced pressure. The resulting mixture was concentrated under reduced pressure. The residue was purified by silica gel column chromatography, eluted with petroleum ether/ethyl acetate (1:1) to afford 3-bromo-1-phenyl-1H-pyrazol-5-amine (13 g, 35%) as a yellow solid.

LCMS Calculated for $C_9H_8BrN_3$: 236.99; Observed: 237.90 $[M+H]^+$.

(2)

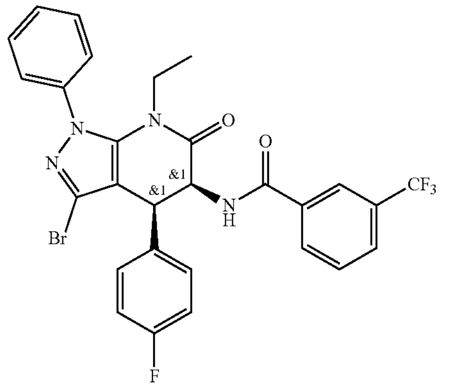 [SMILES: CCN1C(=O)[C@@H](NC(=O)c2cccc(C(F)(F)F)c2)[C@@H](c2ccc(F)cc2)c2c(Br)nn(-c3ccccc3)c21]

rac-N-((4R,5R)-3-bromo-4-(4-fluorophenyl)-6-oxo-1-phenyl-4,5,6,7-tetrahydro-1H-pyrazolo[3,4-b]pyridin-5-yl)-3-(trifluoromethyl)benzamide A solution of 3-bromo-1-phenyl-1H-pyrazol-5-amine (12.0 g, 50.4 mmol, 1.00 equiv), $SnCl_2$ (0.97 g, 5.04 mmol, 0.100 equiv) and (Z)-4-(4-fluorobenzylidene)-2-(3-(trifluoromethyl)phenyl)oxazol-5 (4H)-one (16.9 g, 50.4 mmol, 1.00 equiv) in chlorobenzene (120 mL) was stirred for 5 h at 140° C. The mixture was allowed to cool down to room temperature. The resulting mixture was filtered, the filter cake was washed with DCM (2×30 mL). The filtrate was concentrated under reduced pressure. The residue was purified by silica gel column chromatography, eluted with petroleum ether/ethyl acetate (1:1) to afford rac-N-((4R,5R)-3-bromo-4-(4-fluorophenyl)-6-oxo-1-phenyl-4,5,6,7-tetrahydro-1H-pyrazolo[3,4-b]pyridin-5-yl)-3-(trifluoromethyl)benzamide (17 g, 58.8%) as a yellow solid.

LCMS Calculated for $C_{26}H_{17}BrF_4N_4O_2$: 572.05; Observed: 573.05 $[M+H]^+$.

rac-N-((4R,5R)-3-bromo-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-493)

A solution of rac-N-((4R,5R)-3-bromo-4-(4-fluorophenyl)-6-oxo-1-phenyl-4,5,6,7-tetrahydro-1H-pyrazolo[3,4-b]pyridin-5-yl)-3-(trifluoromethyl)benzamide (14.0 g, 24.4 mmol, 1.00 equiv), ethyl bromide (3.95 g, 36.6 mmol, 1.50 equiv) and $K_2CO_3$ (6.75 g, 48.8 mmol, 2.00 equiv) in DMF (140 mL) was stirred overnight at room temperature. The resulting mixture was diluted with water (140 mL). The resulting mixture was extracted with Ethyl acetate (3×100 mL). The combined organic layers were washed with brine (1×100 mL), dried over anhydrous $Na_2SO_4$. After filtration, the filtrate was concentrated under reduced pressure. The residue was purified by silica gel column chromatography, eluted with petroleum ether/ethyl acetate (1:1) to afford rac-N-((4R,5R)-3-bromo-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (7.8 g, 53.1%) as a yellow solid and rac-N-((4S,5R)-3-bromo-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (500 mg) as a white solid.

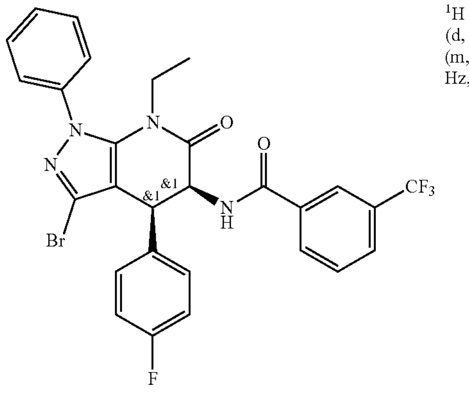

I-493

$^1H$ NMR (300 MHz, Chloroform-d) δ 8.05 (s, 1H), 7.90 (d, J = 7.8 Hz, 1H), 7.82 (d, J = 7.8 Hz, 1H), 7.66-7.50 (m, 6H), 6.99 (d, J = 6.8 Hz, 5H), 5.29 (dd, J = 7.3, 5.8 Hz, 1H), 4.81 (d, J = 7.3 Hz, 1H), 4.02 (dq, J = 14.3, 7.2 Hz, 1H), 3.21 (dq, J = 14.1, 7.0 Hz, 1H), 1.04 (t, J = 7.1 Hz, 3H).
LCMS Calculated for $C_{28}H_{21}BrF_4N_4O_2$: 600.08; Observed: (Method-AT): 601.0, 603.0 $[M + H]^+$, 98.5% at RT 2.468 min.

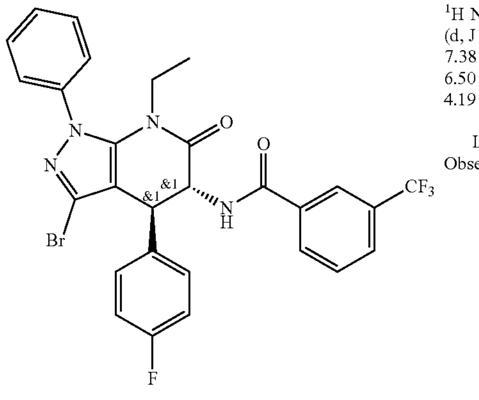

I-532

$^1H$ NMR (300 MHz, Chloroform-d) δ 7.90 (s, 1H), 7.83 (d, J = 7.9 Hz, 1H), 7.76 (d, J = 7.8 Hz, 1H), 7.56 (s, 6H), 7.38 (dd, J = 8.6, 5.2 Hz, 2H), 7.08 (t, J = 8.6 Hz, 2H), 6.50 (d, J = 9.0 Hz, 1H), 5.45 (dd, J = 12.5, 8.9 Hz, 1H), 4.19 (d, J = 12.5 Hz, 1H), 3.91 (dt, J = 14.2, 7.0 Hz, 1H), 3.29-3.11 (m, 1H), 0.95 (t, J = 7.1 Hz, 3H).
LCMS Calculated for $C_{28}H_{21}BrF_4N_4O_2$: 600.08; Observed: (Method-W): 601.0, 603.0 $[M + H]^+$, 95.7% at RT 1.967 min.

(4)

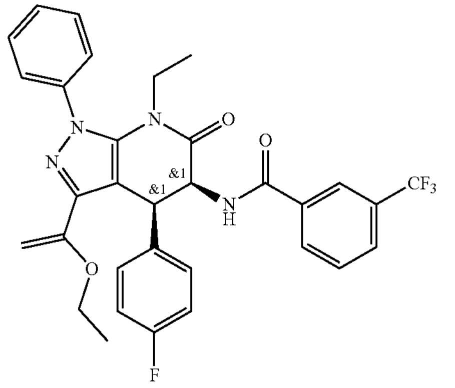

rac-N-((4R,5R)-3-(1-ethoxyvinyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide A solution of rac-N-((4R,5R)-3-bromo-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (10.0 g, 16.6 mmol, 1.00 equiv), $Pd(PPh_3)_4$ (3.84 g, 3.30 mmol, 0.200 equiv) and tributyl (1-ethoxyvinyl) stannane (9.01 g, 24.9 mmol, 1.50 equiv) in Toluene (100 mL) was stirred for 3 h at 100° C. under nitrogen atmosphere. The mixture was allowed to cool down to room temperature. The reaction was quenched by the addition of KF in $H_2O$ (100 mL) at room temperature. The resulting mixture was filtered, the filter cake was washed with ethyl acetate (2×200 mL). The resulting mixture was extracted with Ethyl acetate (3×100 mL). The combined organic layers were washed with water (1×100 mL), dried over anhydrous $Na_2SO_4$. After filtration, the filtrate was concentrated under reduced pressure. The residue was purified by silica gel column chromatography, eluted with petroleum ether/ethyl acetate (5:1) to afford rac-N-((4R,5R)-3-(1-ethoxyvinyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (6.0 g, 62.8%) as a yellow solid.

LCMS Calculated for $C_{32}H_{28}F_4N_4O_3$: 592.21; Observed: 593.22 $[M+H]^+$.

rac-N-((4R,5R)-3-acetyl-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-231)

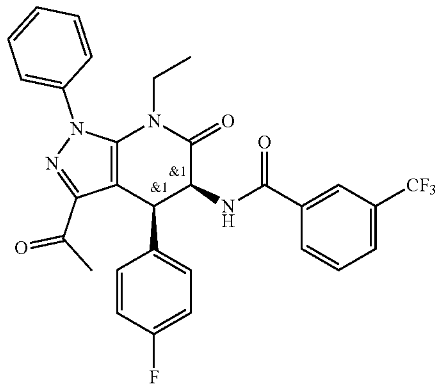

A solution of rac-N-((4R,5R)-3-(1-ethoxyvinyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (10.0 g, 16.9 mmol, 1.00 equiv) in ethyl acetate (100 mL) and HCl (0.5 M, 50 mL) was stirred for 1 h at room temperature. The resulting mixture was extracted with ethyl acetate (3×100 mL). The combined organic layers were washed with brine (2×50 mL), dried over anhydrous $Na_2SO_4$. After filtration, the filtrate was concentrated under reduced pressure. The residue was purified by silica gel column chromatography, eluted with petroleum ether/ethyl acetate (1:1) to afford rac-N-((4R,5R)-3-acetyl-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (9.0 g, 94%) as a white solid.

$^1H$ NMR (300 MHZ, DMSO-$d_6$) δ 8.60 (d, J=7.2 Hz, 1H), 8.20-8.11 (m, 2H), 7.93 (d, J=7.9 Hz, 1H), 7.86-7.77 (m, 2H), 7.76-7.59 (m, 4H), 7.10 (t, J=8.8 Hz, 2H), 7.05-6.95 (m, 2H), 5.54 (t, J=7.2 Hz, 1H), 4.94 (d, J=7.3 Hz, 1H), 3.98-3.81 (m, 1H), 3.09-2.94 (m, 1H), 2.45 (s, 3H), 0.90 (t, J=7.0 Hz, 3H).

LCMS Calculated for $C_{30}H_{24}F_4N_4O_3$: 564.18; Observed: (Method-E) 565.4 $[M+H]^+$, 99.7% at RT 1.336 min.

rac-N-((4R,5R)-3-((E)-1-((tert-butylsulfinyl)imino)ethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (5)

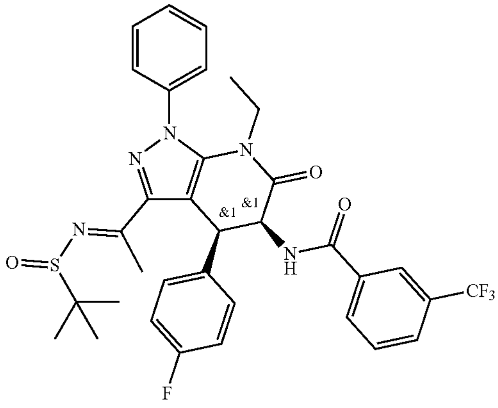

To a stirred solution of rac-N-((4R,5R)-3-acetyl-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (1.00 g, 1.71 mmol, 1.00 equiv) and $Ti(OEt)_4$ (1.21 g, 5.31 mmol, 3.00 equiv) in THF (10.0 mL) was added 2-methyl-propane-2-sulfinamide (0.32 g, 2.66 mmol, 1.5 equiv) in portions at room temperature under nitrogen atmosphere. The resulting mixture was stirred for 1 h at 80° C. under nitrogen atmosphere. The mixture was allowed to cool down to room temperature. The reaction was quenched with water at room temperature. The resulting mixture was extracted with ethyl acetate (2×10 mL). The combined organic layers were washed with brine (2×10 mL), dried over anhydrous $Na_2SO_4$. After filtration, the filtrate was concentrated under reduced pressure. The residue was purified by silica gel column chromatography, eluted with petroleum/ethyl acetate (1:1) to afford rac-N-((4R,5R)-3-((E)-1-((tert-butylsulfinyl)imino)ethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (800 mg, 67.64%) as a yellow solid LCMS Calculated for $C_{34}H_{33}F_4N_5O_3S$: 667.22; Observed: 668.2 $[M+H]^+$ rac-N-((4R,5R)-3-(2-((tert-butylsulfinyl)amino)propan-2-yl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (6)

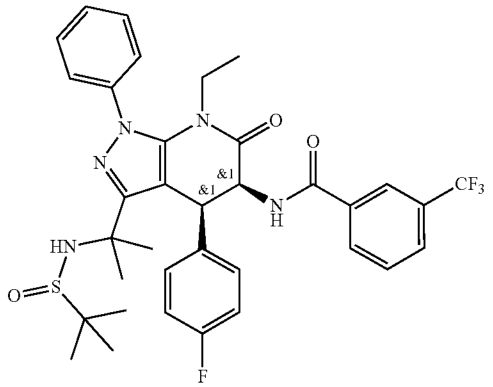

To a stirred solution of rac-N-((4R,5R)-3-((E)-1-((tert-butylsulfinyl)imino)ethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (300 mg, 0.449 mmol, 1.00 equiv) in DCM (3 mL) was added MeMgBr (1 M in $Et_2O$, 536 mg, 4.49 mmol, 10.0 equiv) dropwise at −78° C. under nitrogen atmosphere. The resulting mixture was stirred for 3 h at −20° C. under nitrogen atmosphere. The reaction was quenched with sat. $NH_4Cl$ (aq.) at room temperature. The resulting mixture was extracted with ethyl acetate (2×10 mL). The combined organic layers were washed with brine (2×10 mL), dried over anhydrous $Na_2SO_4$. After filtration, the filtrate was concentrated under reduced pressure. The residue was purified by silica gel column chromatography, eluted with petroleum ether/acetate(1:1) ethyl to afford rac-N-((4R,5R)-3-(2-((tert-butylsulfinyl)amino) propan-2-yl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (110 mg, 35.8%) as a yellow solid.

LCMS Calculated for $C_{35}H_{37}F_4N_5O_3S$: 683.26; Observed: 684.2 $[M+H]^+$ rac-N-((4R,5R)-3-(2-aminopropan-2-yl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-671)

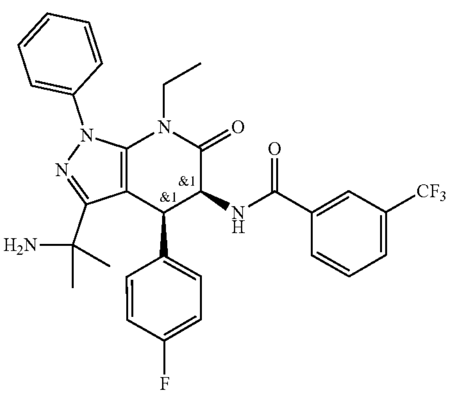

A solution of rac-N-((4R,5R)-3-(2-((tert-butylsulfinyl)amino) propan-2-yl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (100 mg, 0.146 mmol, 1.00 equiv) and hydrogen chloride (2 mL) in dioxane (2 mL) was stirred for 3 h at room temperature under nitrogen atmosphere. The mixture was neutralized to pH 7 with saturated $NaHCO_3$(aq.). The resulting mixture was concentrated under reduced pressure. The residue was purified to afford rac-N-((4R,5R)-3-(2-aminopropan-2-yl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (40 mg, 47%) as an off-white solid.

$^1H$ NMR (300 MHz, Chloroform-d) δ 8.07 (s, 1H), 7.90 (d, J=7.8 Hz, 1H), 7.81 (d, J=7.9 Hz, 1H), 7.59 (t, J=7.8 Hz, 1H), 7.57-7.47 (m, 5H), 7.06-6.92 (m, 5H), 5.27 (t, J=6.3 Hz, 1H), 5.06 (d, J=7.5 Hz, 1H), 4.04-3.88 (m, 1H), 3.26-3.13 (m, 1H), 1.51 (s, 3H), 1.34 (s, 3H), 1.01 (t, J=7.0 Hz, 3H).

LCMS Calculated for $C_{31}H_{29}F_4N_5O_2$: 579.23; Observed (Method-E): 580.5 $[M+H]^+$, 97.7% at RT 1.416 min.

2. Synthesis of rac-N-((4R,5R)-3-(1-aminocyclopropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-568)

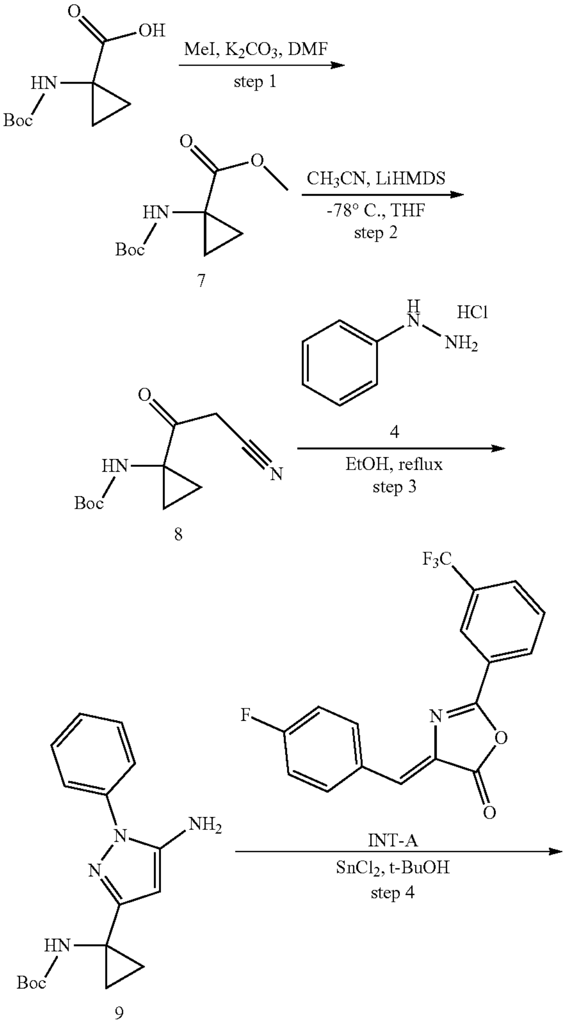

-continued

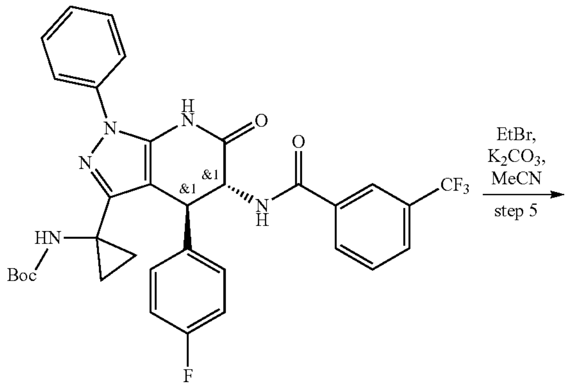

10

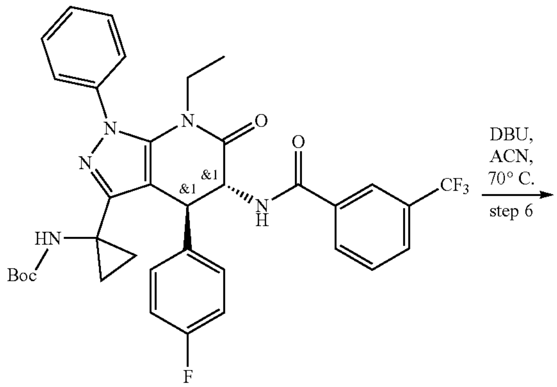

11

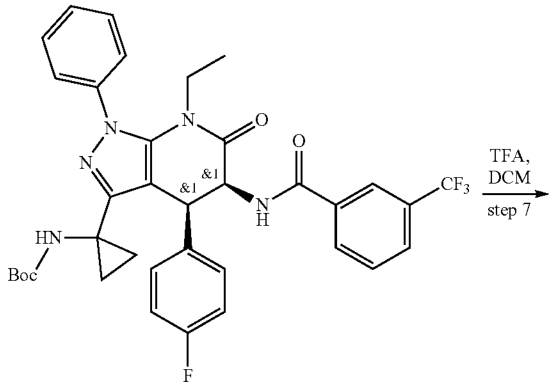

12

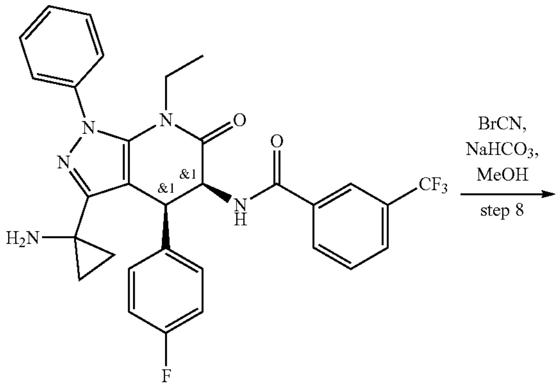

I-568

-continued

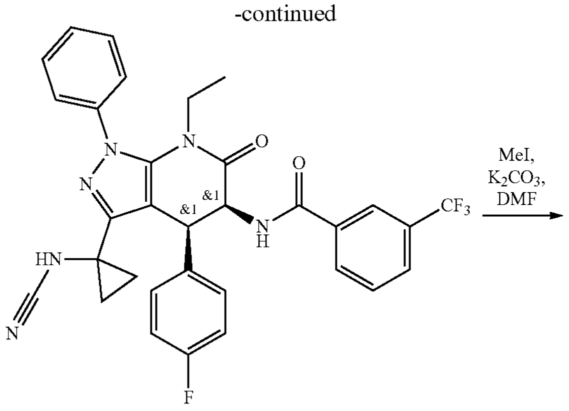

I-87

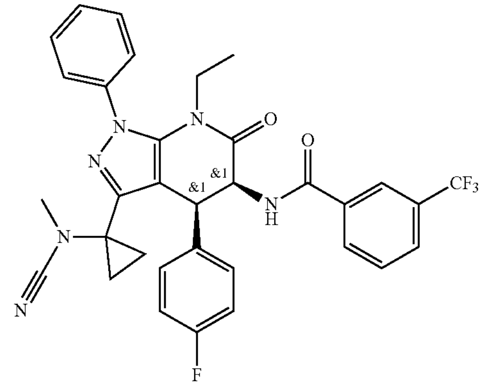

I-52 methyl 1-((tert-butoxycarbonyl)amino)cyclopropane-1-carboxylate (7)

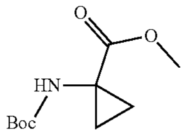

A solution of 1-[(tert-butoxycarbonyl)amino]cyclopropane-1-carboxylic acid (5.00 g, 24.8 mmol, 1.00 equiv), $K_2CO_3$ (8.59 g, 62.1 mmol, 2.50 equiv) and MeI (5.29 g, 37.3 mmol, 1.50 equiv) in DMF (60 mL) was stirred for 3 h at room temperature. The resulting mixture was diluted with $H_2O$ (100 mL). The resulting mixture was extracted with ethyl acetate (3×40 mL). The combined organic layers were washed with NaCl (3×30 mL), dried over anhydrous $Na_2SO_4$. After filtration, the filtrate was concentrated under reduced pressure. The residue was purified by silica gel column chromatography, eluted with petroleum ether/ethyl acetate (5:1) to afford methyl 1-((tert-butoxycarbonyl)amino)cyclopropane-1-carboxylate (5 g, 84%) as a yellow solid.

tert-butyl N-[1-(2-cyanoacetyl)cyclopropyl]carbamate (8)

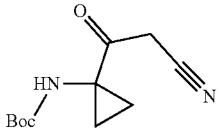

A solution of methyl 1-((tert-butoxycarbonyl)amino)cyclopropane-1-carboxylate (34.0 g, 158 mmol, 1.00 equiv) in THF (400 mL) was treated with $CH_3CN$ (9.73 g, 237 mmol, 1.50 equiv) for 1 h at −78° C. under nitrogen atmosphere followed by the addition of LiHMDS (1M, 474 mL, 474 mmol, 3.00 equiv) dropwise at −78° C. The reaction was quenched with sat. $NH_4Cl$ (aq.) (400 ml) at −78° C. The mixture was allowed to cool down to room temperature. The resulting mixture was extracted with ethyl acetate (3×200 mL). The combined organic layers were washed with brine (1×200 mL), dried over anhydrous $Na_2SO_4$. After filtration, the filtrate was concentrated under reduced pressure. The residue was purified by silica gel column chromatography, eluted with petroleum ether/ethyl acetate (5:1) to afford tert-butyl N-[1-(2-cyanoacetyl)cyclopropyl]carbamate (32 g, 83%) as a yellow solid.

tert-butyl N-[1-(5-amino-1-phenylpyrazol-3-yl)cyclopropyl]carbamate (9)

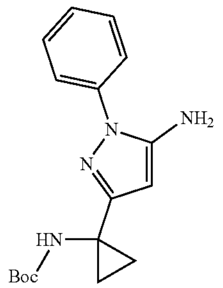

Into a 1 L round-bottom flask were added tert-butyl N-[1-(2-cyanoacetyl)cyclopropyl]carbamate (32 g, 144 mmol, 1.00 equiv), phenylhydrazine hydrochloride (15.4 g, 143 mmol, 1.00 equiv) and EtOH (400 mL). The mixture was stirred for 30 min at 80° C. The mixture was allowed to cool down to room temperature. The resulting mixture was diluted with $H_2O$ (300 mL). The resulting mixture was extracted with ethyl acetate (3×100 mL). The combined organic layers were washed with brine (1×100 mL), dried over anhydrous $Na_2SO_4$. After filtration, the filtrate was concentrated under reduced pressure. The residue was purified by silica gel column chromatography, eluted with petroleum ether/ethyl acetate (1:1) to afford tert-butyl N-[1-(5-amino-1-phenylpyrazol-3-yl)cyclopropyl]carbamate (26 g, 49%) as a yellow solid.

rac-tert-butyl (1-((4R,5S)-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)cyclopropyl)carbamate (10)

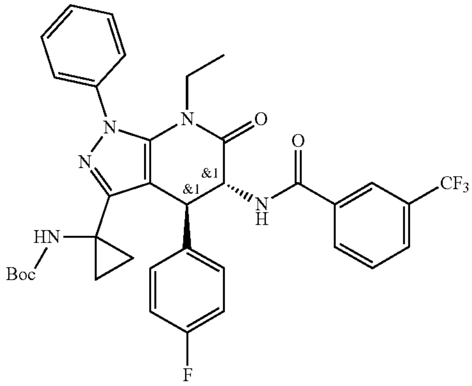

Into a 1 L round-bottom flask were added (4Z)-4-[(4-fluorophenyl)methylidene]-2-[3-(trifluoromethyl)phenyl]-1,3-oxazol-5-one (26.0 g, 77.6 mmol, 1.00 equiv), tert-butyl N-[1-(5-amino-1-phenylpyrazol-3-yl)cyclopropyl]carbamate (24.4 g, 77.6 mmol, 1.00 equiv), $SnCl_2$ (1.49 g, 7.76 mmol, 0.100 equiv) and t-BuOH (300 mL). The mixture was stirred for 36 h at 80° C. The mixture was allowed to cool down to room temperature. The resulting mixture was diluted with $H_2O$ (200 mL). The resulting mixture was extracted with ethyl acetate (3×200 mL). The combined organic layers were washed with brine (1×200 mL), dried over anhydrous $Na_2SO_4$. After filtration, the filtrate was concentrated under reduced pressure. The residue was purified by silica gel column chromatography, eluted with petroleum ether/ethyl acetate (1:1) to afford rac-tert-butyl (1-((4R,5S)-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)cyclopropyl)carbamate (20 g, 31%) as a yellow solid.

rac-tert-butyl (1-((4R,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)cyclopropyl)carbamate (11)

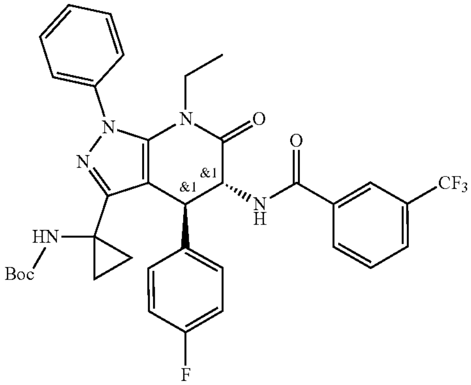

Into a 250 mL round-bottom flask were added rac-tert-butyl N-(1-[(4R,5S)-4-(4-fluorophenyl)-6-oxo-1-phenyl-5-[3-(trifluoromethyl)benzamido]-4H,5H, 7H-pyrazolo[3,4-b]pyridin-3-yl]cyclopropylcarbamate (10.0 g, 15.4 mmol, 1.00 equiv), $K_2CO_3$ (4.25 g, 30.8 mmol, 2.00 equiv), MeCN (150 mL) and bromoethane (2.01 g, 18.5 mmol, 1.20 equiv) at room temperature. The mixture was stirred for 16 h at room temperature. The resulting mixture was concentrated under reduced pressure. The residue was purified by silica gel column chromatography, eluted with petroleum ether/ethyl acetate (1:1) to afford rac-tert-butyl (1-((4R,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)cyclopropyl)carbamate (4 g, 34%) as a yellow solid.

LCMS Calculated for $C_{36}H_{35}F_4N_5O_5$: 677.26; Observed: 678.3 $[M+H]^+$ rac-tert-butyl (1-((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)cyclopropyl)carbamate (12)

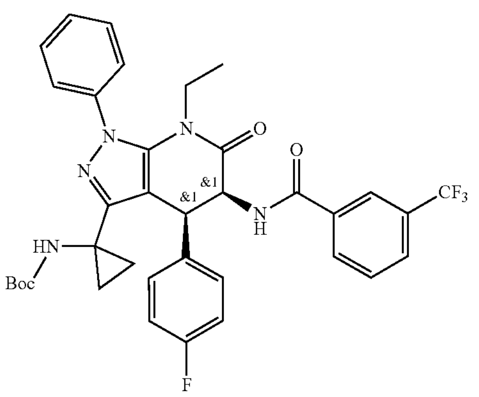

Into a 40 mL round-bottom flask were added rac-tert-butyl (1-((4R,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)cyclopropyl)carbamate (1.00 g, 1.48 mmol, 1.00 equiv), DBU (0.85 g, 5.61 mmol, 3.80 equiv) and ACN (12 mL). The mixture was stirred for 16 h at 70° C. The mixture was allowed to cool down to room temperature diluted with $H_2O$ (40 mL). The resulting mixture was extracted with ethyl acetate (3×20 mL). The combined organic layers were washed with brine (3×20 mL), dried over anhydrous $Na_2SO_4$. After filtration, the filtrate was concentrated under reduced pressure. The residue was purified by silica gel column chromatography, eluted with petroleum ether/ethyl acetate (0:1) to afford a mixture (600 mg, 69%, cis:trans=5:1) of rac-tert-butyl (1-((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)cyclopropyl)carbamate and rac-tert-butyl (1-((4R,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)cyclopropyl)carbamate as a yellow solid.

rac-N-((4R,5R)-3-(1-aminocyclopropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-568)

Into a 40 mL round-bottom flask were added rac-tert-butyl (1-((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)cyclopropyl)carbamate (900 mg, 1.33 mmol, 1.00 equiv), DCM (10 mL) and TFA (2 mL). The mixture was stirred for 1 h at room temperature. The mixture was basified to pH 8 with saturated $NaHCO_3$(aq.). The resulting mixture was diluted with $H_2O$ (30 mL). The resulting mixture was extracted with ethyl acetate (3×10 mL). The combined organic layers were washed with brine (3×10 mL), dried over anhydrous $Na_2SO_4$. After filtration, the filtrate was concentrated under reduced pressure. The residue was purified by silica gel column chromatography, eluted with petroleum ether/ethyl acetate (0:1) to afford crude product (600 mg mixture, 9:1). The crude product (150 mg) was purified by Prep-HPLC with the following conditions (Column: Xselect CSH-Prep C18 Column, 30*150 mm, 5 μm; Mobile Phase A: Water (0.1% FA), Mobile Phase B: ACN; Flow rate: 60 mL/min; Gradient: isocratic 55%-66% 11 min; Wave Length: 254 nm/220 nm) to afford rac-N-((4R,5R)-3-(1-aminocyclopropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-568) (76 mg) as a white solid and rac-N-((4R,5S)-3-(1-aminocyclopropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-449) (15 mg) as white solid.

| | |
|---|---|
| 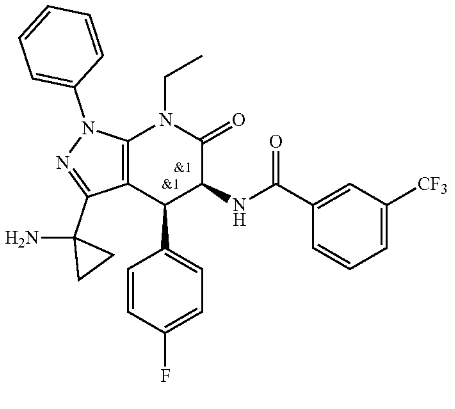 [SMILES: CCN1C(=O)[C@@H](NC(=O)c2cccc(C(F)(F)F)c2)[C@@H](c2ccc(F)cc2)c2c(C3(N)CC3)nn(-c3ccccc3)c21]<br>I-568 | $^1$H NMR (400 MHz, Chloroform-d) δ 8.05 (s, 1H), 7.89 (d, J = 7.8 Hz, 1H), 7.80 (d, J = 7.8 Hz, 1H), 7.59 (t, J = 7.8 Hz, 1H), 7.59-7.44 (m, 5H), 7.03 (d, J = 5.6 Hz, 1H), 6.99-6.91 (m, 4H), 5.25 (dd, J = 7.1, 5.6 Hz, 1H), 4.91 (d, J = 7.2 Hz, 1H), 3.97 (dq, J = 14.4, 7.2 Hz, 1H), 3.18 (dq, J = 14.0, 7.0 Hz, 1H), 1.13-1.05 (m, 1H), 1.01 (t, J = 7.1Hz, 3H), 0.98-0.88 (m, 2H), 0.91-0.80 (m, 1H). LCMS Calculated for $C_{31}H_{27}F_4N_5O_2$: 577.21; Observed: (Method-K): 578.4 $[M + H]^+$, 99.4% at RT 1.427 min. |

-continued

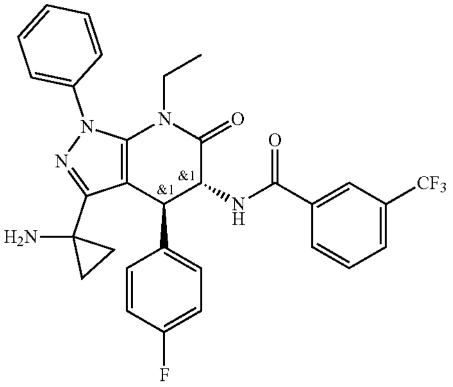 [SMILES: CCN1C(=O)[C@H](NC(=O)c2cccc(C(F)(F)F)c2)[C@@H](c2ccc(F)cc2)c2c(C3(N)CC3)nn(-c3ccccc3)c21]

$^1$H NMR (400 MHz, Chloroform-d) δ 7.88 (s, 1H), 7.80 (d, J = 7.8 Hz, 1H), 7.74 (d, J = 7.8 Hz, 1H), 7.57-7.50 (m, 5H), 7.50-7.41 (m, 3H), 7.09 (t, J = 8.5 Hz, 2H), 6.62 (d, J = 8.9 Hz, 1H), 5.39 (dd, J = 11.6, 8.8 Hz, 1H), 4.25 (d, J = 11.6 Hz, 1H), 3.81 (dd, J = 14.3, 7.2 Hz, 1H), 3.24 (dt, J = 14.1, 7.0 Hz, 1H), 1.20-1.13 (m, 1H), 0.91 (t, J = 7.0 Hz, 3H), 0.75-0.68 (m, 1H), 0.58-0.47 (m, 2H). LCMS Calculated for $C_{31}H_{27}F_4N_5O_2$: 577.21; Observed (Method-K): 578.4 [M + H]$^+$, 99.4% at RT 1.427 min.

I-449

3. Synthesis of rac-N-((4R,5R)-3-(2-cyanamidopropan-2-yl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-144) and rac-N-((4R,5R)-7-ethyl-4-(4-fluorophenyl)-3-(2-(N-methylcyanamido)propan-2-yl)-6-oxo-1-phenyl-4,5,6,7-tetrahydro-1H-pyrazolo[3,4-b]pyridin-5-yl)-3-(trifluoromethyl)benzamide (I-42)

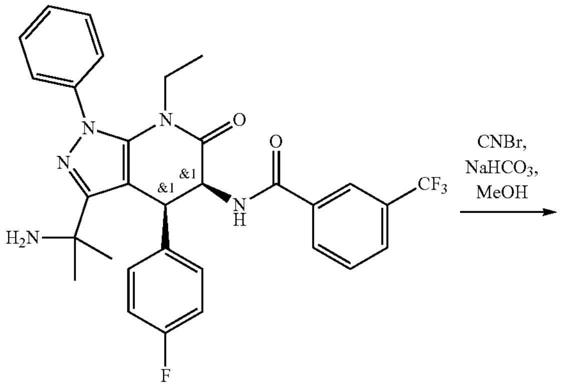

I-671

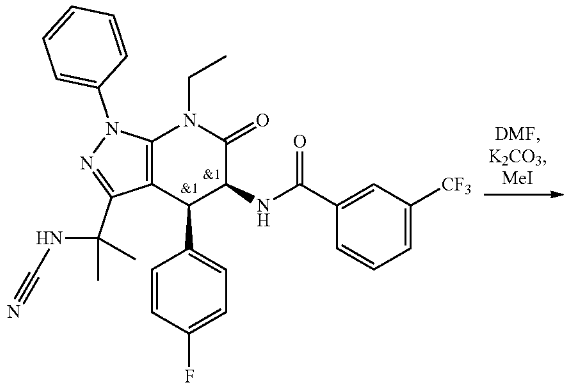

I-144

-continued

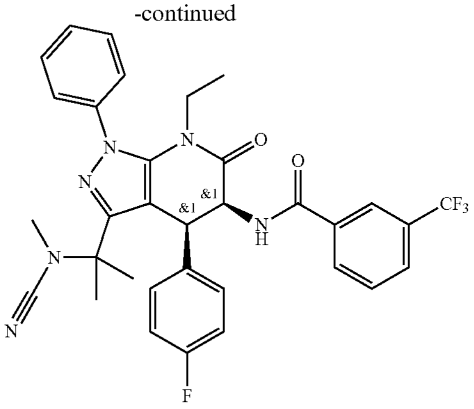

I-42 rac-N-((4R,5R)-3-(2-cyanamidopropan-2-yl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-144)

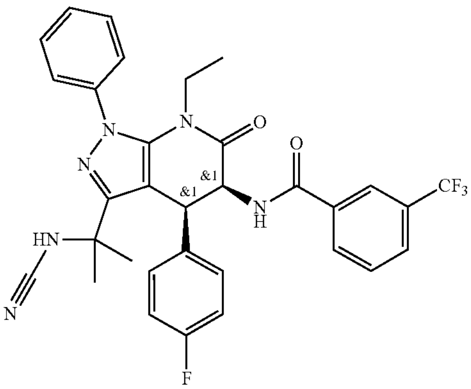

To a stirred solution of rac-N-((4R,5R)-3-(2-aminopropan-2-yl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (100 mg, 0.173 mmol, 1.00 equiv) and $NaHCO_3$ (29.0 mg, 0.346 mmol, 2.00 equiv) in MeOH (2.00 mL) was added BrCN (21.9 mg, 0.208 mmol, 1.2 equiv) in portions at room temperature under nitrogen atmosphere. The resulting mixture was stirred for 1 h at room temperature under nitrogen atmosphere. The resulting mixture was purified by reverse phase flash with the following conditions (Column: XBridge Prep OBD C18 Column, 30*150 mm, 5 μm; Mobile Phase A: Water (10 mmol/L $NH_4HCO_3$+0.1% $NH_3H_2O$), Mobile Phase B: ACN; Flow rate: 60 mL/min mL/min; Gradient: isocratic 50%-70% 12 min; Wave Length: 254 nm/220 nm nm; RT1(min): 7.83/9.02) to afford rac-N-((4R,5R)-3-(2-cyanamidopropan-2-yl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (30 mg, 28%) as a white solid.

rac-N-((4R,5R)-7-ethyl-4-(4-fluorophenyl)-3-(2-(N-methylcyanamido)propan-2-yl)-6-oxo-1-phenyl-4,5,6,7-tetrahydro-1H-pyrazolo[3,4-b]pyridin-5-yl)-3-(trifluoromethyl)benzamide (I-42)

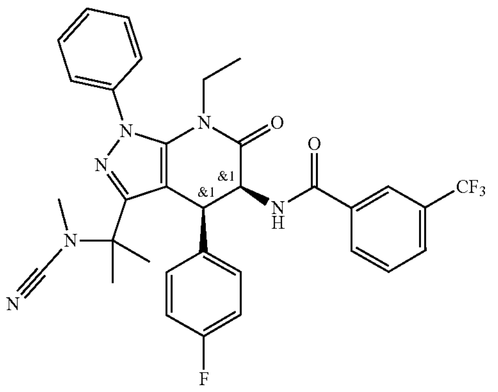

To a stirred solution of rac-N-((4R,5R)-3-(2-cyanamidopropan-2-yl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (100 mg, 0.166 mmol, 1.00 equiv) and $K_2CO_3$ (45.8 mg, 0.332 mmol, 2.00 equiv) in DMF (1 mL) was added MeI (28.2 mg, 0.199 mmol, 1.20 equiv) dropwise at room temperature under nitrogen atmosphere. The resulting mixture was stirred overnight at room temperature under nitrogen atmosphere. The resulting mixture was extracted with ethyl acetate (2×10 mL). The combined organic layers were washed with brine (2×10 mL), dried over anhydrous $Na_2SO_4$. After filtration, the filtrate was concentrated under reduced pressure. The residue was purified by reverse phase flash with the following conditions (Column: XBridge Prep OBD C18 Column, 30*150 mm, 5 μm; Mobile Phase A: Water (10 mmol/L $NH_4HCO_3$+0.1% $NH_3H_2O$), Mobile Phase B: ACN; Flow rate: 60 mL/min; Gradient: isocratic 55%-80% 11 min; Wave Length: 254 nm/220 nm) to afford rac-N-((4R,5R)-7-ethyl-4-(4-fluorophenyl)-3-(2-(N-methylcyanamido) propan-2-yl)-6-oxo-1-phenyl-4,5,6,7-tetrahydro-1H-pyrazolo[3,4-b]pyridin-5-yl)-3-(trifluoromethyl)benzamide (40 mg, 39%) as a white solid.

| | |
|---|---|
| 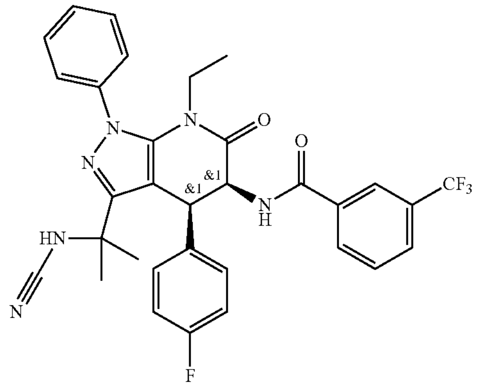 [SMILES: CCN1C(=O)[C@@H](NC(=O)c2cccc(C(F)(F)F)c2)[C@@H](c2ccc(F)cc2)c2c(C(C)(C)NC#N)nn(-c3ccccc3)c21]<br>I-144 | $^1$H NMR (400 MHz, DMSO-$d_6$) δ 8.51 (d, J = 7.3 Hz, 1H), 8.23-8.14 (m, 2H), 7.94 (d, J = 7.7 Hz, 1H), 7.83-7.71 (m, 1H), 7.70 (dd, J = 7.3, 1.9 Hz, 2H), 7.67-7.51 (m, 3H), 7.35 (s, 1H), 7.17-7.07 (m, 2H), 7.04-6.96 (m, 2H), 5.52 (t, J = 7.2 Hz, 1H), 4.77 (d, J = 7.0 Hz, 1H), 3.97-3.82 (m, 1H), 3.15-3.02 (m, 1H), 1.43 (s, 3H), 1.24 (s, 3H), 0.93 (t, J = 7.1 Hz, 3H). LCMS Calculated for $C_{32}H_{28}F_4N_6O_2$: 604.22; Observed (Method-C): 605.1 [M + H]$^+$, 90.6% at RT 1.385 min. |
| 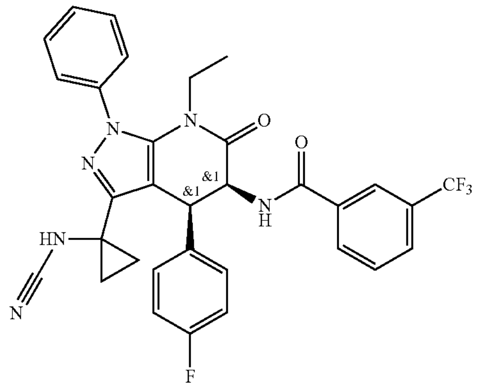 [SMILES: CCN1C(=O)[C@@H](NC(=O)c2cccc(C(F)(F)F)c2)[C@@H](c2ccc(F)cc2)c2c(C3(NC#N)CC3)nn(-c3ccccc3)c21]<br>I-87 | $^1$H NMR (400 MHz, Chloroform-d) δ 8.08 (s, 1H), 7.91 (d, J = 7.8 Hz, 1H), 7.83 (d, J = 7.8 Hz, 1H), 7.61 (dd, J = 14.7, 7.2 Hz, 2H), 7.55 (t, J = 6.4 Hz, 4H), 7.03-6.95 (m, 5H), 5.28 (t, J = 6.4 Hz, 1H), 4.94 (d, J = 7.0 Hz, 1H), 4.41 (s, 1H), 3.99 (dq, J = 14.4, 7.2 Hz, 1H), 3.20 (dq, J = 13.9, 6.8 Hz, 1H), 1.46-1.37 (m, 1H), 1.35-1.19 (m, 2H), 1.19-1.09 (m, 1H), 1.04 (t, J = 7.0 Hz, 3H). LCMS Calculated for $C_{32}H_{26}F_4N_6O_2$: 602.21; Observed (Method-AF): 603.4 [M + H]$^+$, 99.8% at RT 1.244 min. |

-continued

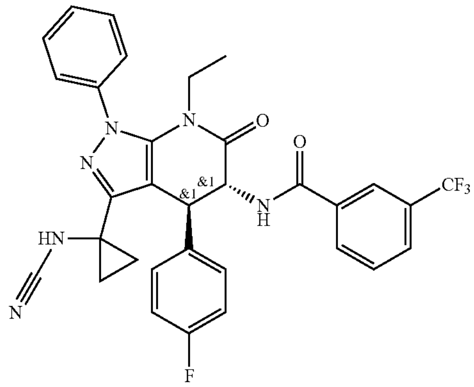 [SMILES: CCN1C(=O)[C@H](NC(=O)c2cccc(C(F)(F)F)c2)[C@@H](c2ccc(F)cc2)c2c(C3(NC#N)CC3)nn(-c3ccccc3)c21]

I-84

$^1$H NMR (400 MHz, Chloroform-d) δ 7.91 (s, 1H), 7.84 (d, J = 7.8 Hz, 1H), 7.76 (d, J = 7.8 Hz, 1H), 7.60-7.45 (m, 8H), 7.13 (t, J = 8.5 Hz, 2H), 6.85 (d, J = 8.6 Hz, 1H), 5.39 (dd, J = 11.7, 8.6 Hz, 1H), 4.34 (d, J = 11.7 Hz, 1H), 3.83 (dq, J = 14.3, 7.1 Hz, 1H), 3.29 (dq, J = 13.9, 6.9 Hz, 1H), 3.07 (s, 1H), 1.76-1.66 (m, 1H), 1.08-0.99 (m, 1H), 0.99-0.88 (m, 4H), 0.79-0.68 (m, 1H).
LCMS Calculated for $C_{32}H_{26}F_4N_6O_2$: 602.21; Observed (Method-K): 603.4 [M + H]$^+$, 97.9% at RT 1.169 min.

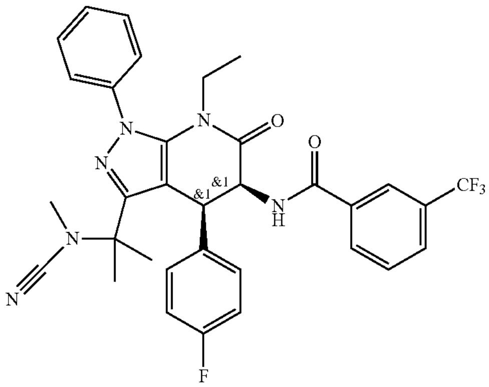 [SMILES: CCN1C(=O)[C@@H](NC(=O)c2cccc(C(F)(F)F)c2)[C@@H](c2ccc(F)cc2)c2c(C(C)(C)N(C)C#N)nn(-c3ccccc3)c21]

I-42

$^1$H NMR (400 MHz, DMSO-d$_6$) δ 8.54 (d, J = 7.1 Hz, 1H), 8.19 (s, 1H), 8.17 (d, J = 8.0 Hz, 1H), 7.93 (d, J = 7.8 Hz, 1H), 7.75-7.69 (m, 3H), 7.66-7.52 (m, 3H), 7.14 (t, J = 8.8 Hz, 2H), 7.01 (dd, J = 8.6, 5.5 Hz, 2H), 5.53 (t, J = 7.0 Hz, 1H), 4.67 (d, J = 7.0 Hz, 1H), 3.87 (dq, J = 14.3, 7.1 Hz, 1H), 3.09 (dq, J = 13.7, 6.8 Hz, 1H), 2.45 (s, 3H), 1.55 (s, 3H), 1.32 (s, 3H), 0.94 (t, J = 7.0 Hz, 3H).
LCMS Calculated for $C_{33}H_{30}F_4N_6O_2$: 618.24; Observed (Method-C): 619.1 [M + H]$^+$, 99.2% at RT 1.430 min.

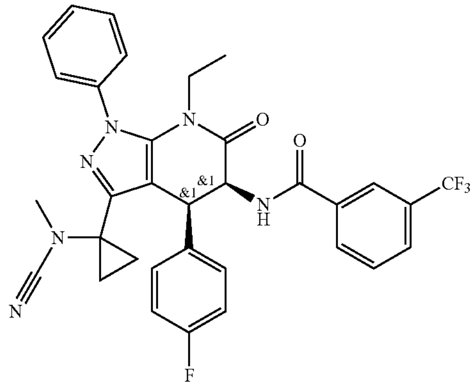 [SMILES: CCN1C(=O)[C@@H](NC(=O)c2cccc(C(F)(F)F)c2)[C@@H](c2ccc(F)cc2)c2c(C3(N(C)C#N)CC3)nn(-c3ccccc3)c21]

I-52

$^1$H NMR (400 MHz, Chloroform-d) δ 8.05 (s, 1H), 7.90 (d, J = 7.8 Hz, 1H), 7.80 (d, J = 7.8 Hz, 1H), 7.63-7.52 (m, 3H), 7.54-7.47 (m, 3H), 7.11-7.03 (m, 2H), 7.07 - 6.95 (m, 2H), 6.83 (d, J = 6.3 Hz, 1H), 5.35 (t, J = 6.7 Hz, 1H), 4.98 (d, J = 7.1 Hz, 1H), 3.95 (dq, J = 14.4, 7.2 Hz, 1H), 3.20 (dq, J = 13.9, 6.9 Hz, 1H), 2.52 (s, 3H), 1.43 - 1.32 (m, 2H), 1.29-1.18 (m, 1H), 1.18-1.06 (m, 1H), 1.03 (t, J = 7.1 Hz, 3H).
LCMS Calculated for $C_{33}H_{28}F_4N_6O_2$: 616.22; Observed (Method-AF): 617.4 [M + H]$^+$, 99.9% at RT 3.377 min.

-continued
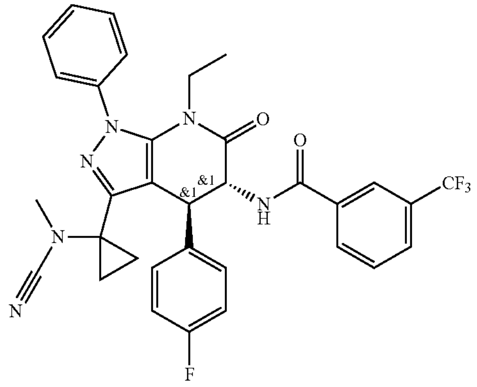 [SMILES: CCN1C(=O)[C@H](NC(=O)c2cccc(C(F)(F)F)c2)[C@@H](c2ccc(F)cc2)c2c(C3(N(C)C#N)CC3)nn(-c3ccccc3)c21]
I-76
$^1$H NMR (400 MHz, Chloroform-d) δ 8.00 (s, 1H), 7.93 (d, J = 7.9 Hz, 1H), 7.76 (d, J = 7.8 Hz, 1H), 7.60-7.45 (m, 6H), 7.32-7.26 (m, 2H), 7.05 (t, J = 8.6 Hz, 2H), 6.74 (d, J = 7.3 Hz, 1H), 5.16 (t, J = 7.0 Hz, 1H), 4.55 (d, J = 6.8 Hz, 1H), 3.72-3.59 (m, 1H), 3.45-3.31 (m, 1H), 2.69 (s, 3H), 1.26 (dd, J = 9.5, 4.9 Hz, 1H), 1.08-0.96 (m, 2H), 0.88 (t, J = 7.0 Hz, 3H), 0.83-0.73 (m, 1H). LCMS Calculated for $C_{33}H_{28}F_4N_6O_2$: 616.22; Observed (Method-AF): 617.4 $[M + H]^+$, 98.6% at RT 3.108 min.
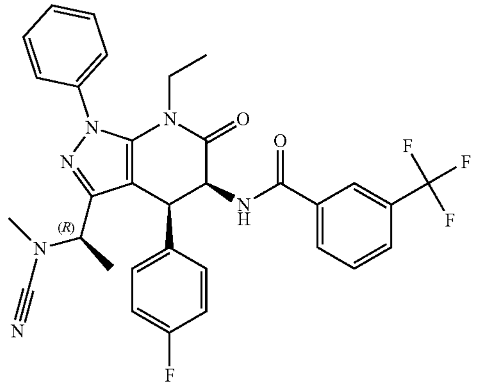
I-44
$^1$H NMR (400 MHz, DMSO-$d_6$) δ 8.57 (d, J = 7.4 Hz, 1H), 8.20-8.12 (m, 2H), 7.93 (d, J = 7.8 Hz, 1H), 7.76 - 7.68 (m, 3H), 7.61 (dd, J = 8.4, 6.4 Hz, 2H), 7.60-7.52 (m, 1H), 7.18-7.08 (m, 2H), 7.01 (dd, J = 8.5, 5.5 Hz, 2H), 5.55 (t, J = 7.2 Hz, 1H), 4.64 (d, J = 7.2 Hz, 1H), 4.26 (q, J = 6.9 Hz, 1H), 3.88 (dq, J = 14.3, 7.1 Hz, 1H), 3.09 (dq, J = 14.0, 7.0 Hz, 1H), 2.61 (s, 3H), 1.35 (d, J = 7.0 Hz, 3H), 0.93 (t, J = 7.1 Hz, 3H). LCMS Calculated for $C_{32}H_{28}F_4N_6O_2$: 604.22; Observed: (Method-D): 605.3 $[M + H]^+$, 99.9% at RT 2.204 min.

4. Synthesis of rac-N-((4R,5R)-3-(2-carbamoylallyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-105)
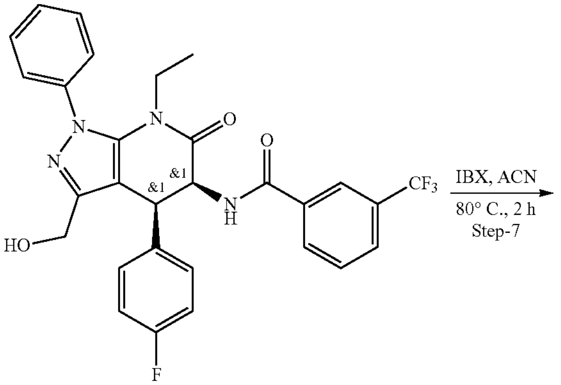
18
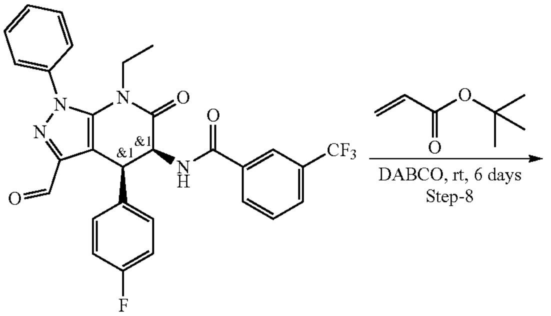
19
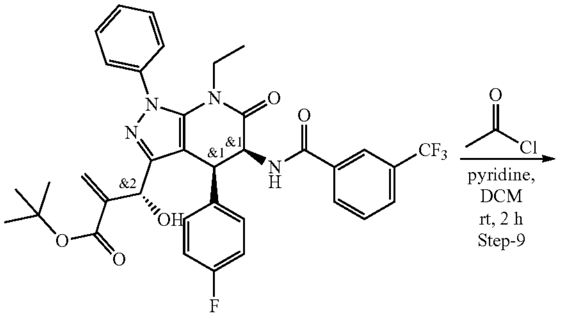
I-146
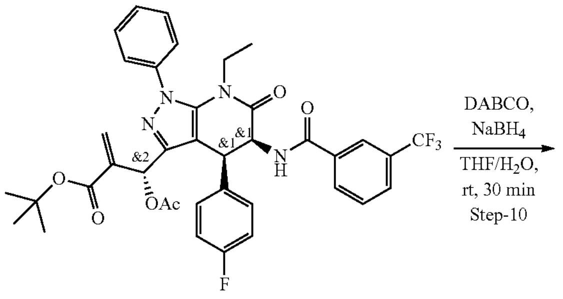
20
-continued
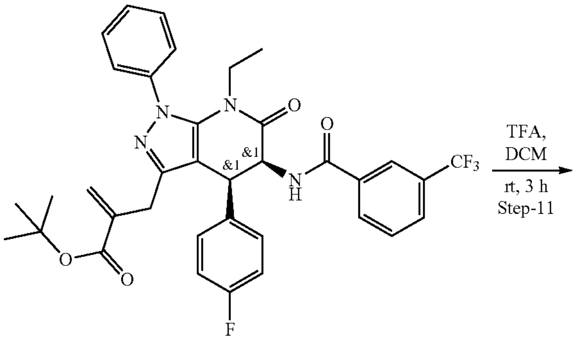
I-78
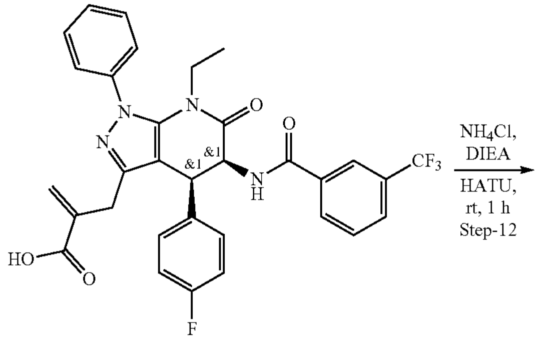
I-21
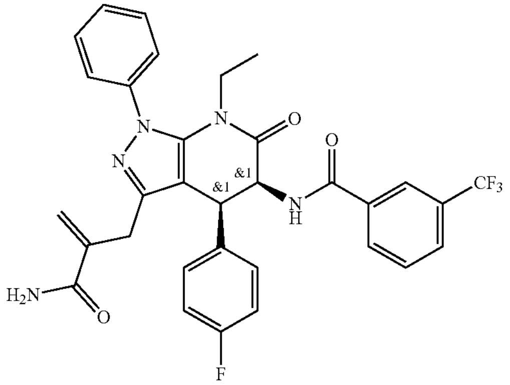
I-105
rac-N-((4R,5R)-7-ethyl-4-(4-fluorophenyl)-3-formyl-6-oxo-1-phenyl-4,5,6,7-tetrahydro-1H-pyrazolo[3,4-b]pyridin-5-yl)-3-(trifluoromethyl)benzamide (19)
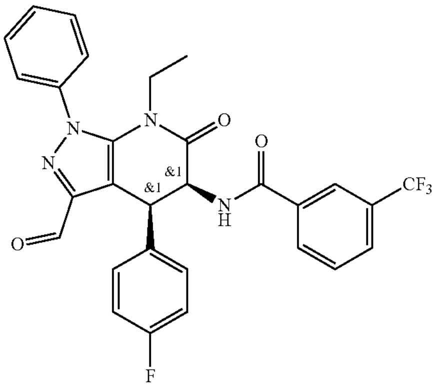

A solution of rac-N-((4R,5R)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-3-(trifluoromethyl)benzamide (5.00 g, 9.05 mmol, 1.00 equiv) and IBX (3.80 g, 13.6 mmol, 1.50 equiv) in ACN (100 mL) was stirred for 2 h at 80° C. The mixture was allowed to cool down to room temperature. The resulting mixture was filtered, the filter cake was washed with ethyl acetate (3×50 mL). The filtrate was concentrated under reduced pressure. This resulted in rac-N-((4R,5R)-7-ethyl-4-(4-fluorophenyl)-3-formyl-6-oxo-1-phenyl-4,5,6,7-tetrahydro-1H-pyrazolo[3,4-b]pyridin-5-yl)-3-(trifluoromethyl)benzamide (4.8 g, 96%) as a yellow solid.

LCMS Calculated for $C_{29}H_{22}F_4N_4O_3$: 550.16; Observed: 551.1 $[M+H]^+$ rac-tert-butyl 2-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)(hydroxy)methyl)acrylate (I-146)

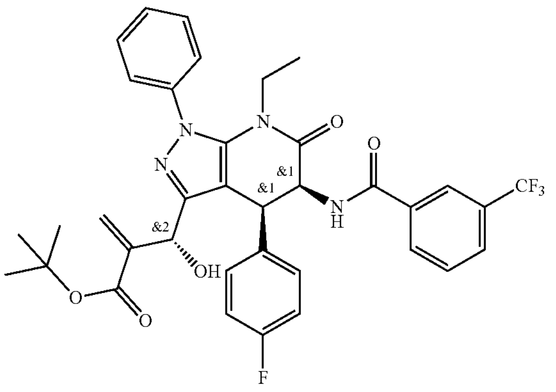

A solution of rac-N-((4R,5R)-7-ethyl-4-(4-fluorophenyl)-3-formyl-6-oxo-1-phenyl-4,5,6,7-tetrahydro-1H-pyrazolo[3,4-b]pyridin-5-yl)-3-(trifluoromethyl)benzamide (100 mg, 0.182 mmol, 1.0 equiv), tert-butyl prop-2-enoate (69.8 mg, 0.546 mmol, 3.00 equiv) and 1,4-diazabicyclo[2.2.2]octane (20.4 mg, 0.182 mmol, 1.00 equiv) was stirred for 6 days at 25° C. The reaction was quenched by the addition of Water (2 mL) at 25° C. The residue was purified by reversed-phase flash chromatography with the following conditions: (Column: Sunfire Prep C18 OBD Column, 19*150 mm, 5 μm; Mobile Phase A: Water (0.05% $NH_3 \cdot H_2O$), Mobile Phase B: ACN; Flow rate: 90 mL/min; Gradient: 40% B to 75% B in 11 min; Wave Length: 254 nm/220 nm) to afford rac-tert-butyl 2-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) (hydroxy)methyl) acrylate (40 mg, 32%) as a white solid.

$^1H$ NMR (400 MHZ, DMSO-$d_6$) δ 8.53-8.39 (m, 1H), 8.14 (t, J=7.9 Hz, 2H), 7.96-7.89 (m, 1H), 7.72 (t, J=7.8 Hz, 1H), 7.66-7.48 (m, 5H), 7.11 (t, J=8.8 Hz, 1H), 7.08-6.96 (m, 2H), 6.90-6.82 (m, 1H), 6.10-5.78 (m, 1H), 5.77-5.68 (m, 2H), 5.47 (dt, J=17.5, 7.2 Hz, 1H), 5.39-5.21 (m, 1H), 4.78-4.59 (m, 1H), 4.05-3.86 (m, 1H), 3.13-2.97 (m, 1H), 1.30 (d, J=6.4 Hz, 9H), 0.91 (t, J=7.1 Hz, 3H).

LCMS Calculated for $C_{36}H_{34}F_4N_4O_5$: 678.25; Observed (Method-D): 679.3 $[M+H]^+$, 97.5% at RT 2.039 min.

rac-tert-butyl 2-(acetoxy((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)acrylate (20)

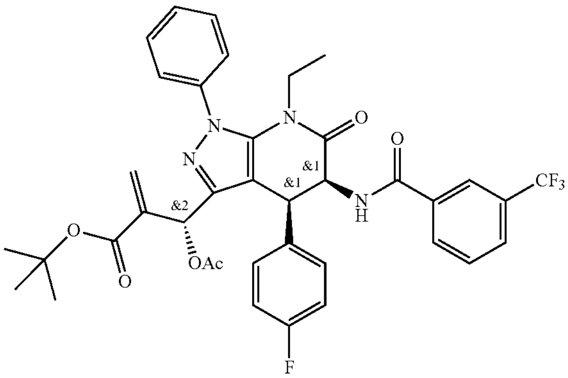

A solution of rac-tert-butyl 2-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) (hydroxy)methyl) acrylate (650 mg, 0.958 mmol, 1.00 equiv) in DCM (10 mL) was treated with Pyridine (152 mg, 1.92 mmol, 2.00 equiv) for 10 min at room temperature under nitrogen atmosphere followed by the addition of acetyl chloride (150 mg, 1.92 mmol, 2.00 equiv) dropwise at 0° C. The resulting mixture was stirred for additional 2 h at room temperature. The reaction was quenched by the addition of Water (20 mL) at 0° C. The resulting mixture was extracted with DCM (3×10 mL). The combined organic layers were washed with brine (1×10 mL), dried over anhydrous $Na_2SO_4$. After filtration, the filtrate was concentrated under reduced pressure. The residue was purified by silica gel column chromatography, eluted with petroleum ether/ethyl acetate (1:1) to afford rac-tert-butyl 2-(acetoxy ((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl) acrylate (500 mg, 72%) as a brown solid.

LCMS Calculated for $C_{38}H_{36}F_4N_4O_6$: 720.26; Observed: 721.5 $[M+H]^+$ rac-tert-butyl 2-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)acrylate (I-78)

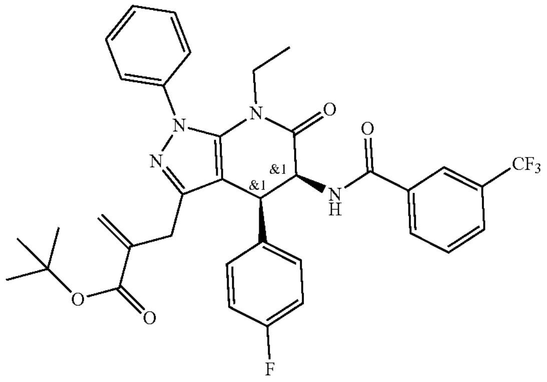

Into a 40 mL vial were added rac-tert-butyl 2-(acetoxy((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl) acrylate (500 mg, 0.694 mmol, 1.00 equiv), THF (3 mL), $H_2O$ (3 mL) and 1,4-diazabicyclo[2.2.2]octane (77.8 mg, 0.694 mmol, 1.00 equiv) at 25° C. The resulting mixture was stirred for 30 min at 25° C. To the above mixture was added $NaBH_4$ (26.2 mg, 0.694 mmol, 1.00 equiv) in portions over 1 min at 25° C. The resulting mixture was stirred for additional 30 min at 25° C. After completion of reaction, the reaction mixture was quenched by addition of water 5 mL. The aqueous layer was extracted with ethyl acetate (2*5 mL). The combined organic phase was washed with brine (5 mL), dried over anhydrous sodium sulfate and concentrated under reduced pressure. The residue was purified by column chromatography using 5 to 50 ethyl acetate in petroleum ether gradient to afford rac-tert-butyl 2-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl) acrylate (350 mg, 76%).

$^1H$ NMR (400 MHZ, DMSO-$d_6$) δ 8.52 (d, J=7.3 Hz, 1H), 8.17-8.08 (m, 2H), 7.92 (d, J=7.8 Hz, 1H), 7.71 (t, J=7.8 Hz, 1H), 7.67-7.62 (m, 2H), 7.62-7.55 (m, 2H), 7.55-7.48 (m, 1H), 7.09 (t, J=8.9 Hz, 2H), 6.95 (dd, J=8.6, 5.6 Hz, 2H), 5.88 (d, J=1.5 Hz, 1H), 5.59-5.36 (m, 2H), 4.48 (d, J=7.3 Hz, 1H), 3.91 (dd, J=14.3, 7.2 Hz, 1H), 3.41 (d, J=3.9 Hz, 2H), 3.07 (dt, J=14.2, 7.0 Hz, 1H), 1.36 (s, 9H), 0.92 (t, J=7.0 Hz, 3H).

LCMS Calculated for $C_{36}H_{34}F_4N_4O_4$: 662.25; Observed (Method-K): 663.5 $[M+H]^+$, 96.9% at RT 1.042 min.

rac-2-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)acrylic acid (I-21)

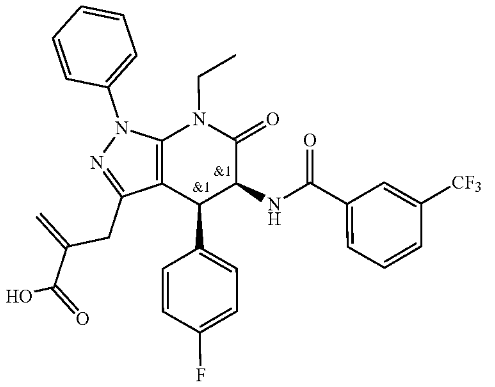

Into a 40 mL vial were added rac-tert-butyl 2-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl) acrylate (300 mg, 0.453 mmol, 1.00 equiv), DCM (5 mL) and TFA (1 mL) at 25° C. The resulting mixture was stirred for 3 h at 25° C. The resulting mixture was concentrated under reduced pressure. The residue was purified by reversed-phase flash chromatography with the following conditions: Column: Sunfire Prep C18 OBD Column, 19*150 mm, 5 μm; Mobile Phase A: Water (0.1% FA), Mobile Phase B: ACN; Flow rate: 30 mL/min; Gradient: 40% B to 60% B in 8 min; Wave Length: 254 nm/220 nm; This resulted in rac-2-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl) acrylic acid (250 mg, 91%) as a white solid.

$^1H$ NMR (400 MHZ, DMSO-$d_6$) δ 12.45 (s, 1H), 8.51 (d, J=7.3 Hz, 1H), 8.24-8.02 (m, 2H), 7.92 (d, J=7.8 Hz, 1H), 7.75-7.63 (m, 3H), 7.56 (dt, J=24.2, 7.3 Hz, 3H), 7.09 (t, J=8.8 Hz, 2H), 7.02-6.90 (m, 2H), 5.97 (s, 1H), 5.51 (t, J=7.3 Hz, 1H), 5.47-5.41 (m, 1H), 4.50 (d, J=7.3 Hz, 1H), 3.90 (dq, J=14.1, 7.0 Hz, 1H), 3.40 (s, 2H), 3.07 (dd, J=14.2, 7.1 Hz, 1H), 0.93 (t, J=7.1 Hz, 3H).

LCMS Calculated for $C_{32}H_{26}F_4N_4O_4$: 606.19; Observed (Method-D): 607.4 $[M+H]^+$, 97.5% at RT 2.039 min.

rac-N-((4R,5R)-3-(2-carbamoylallyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-105)

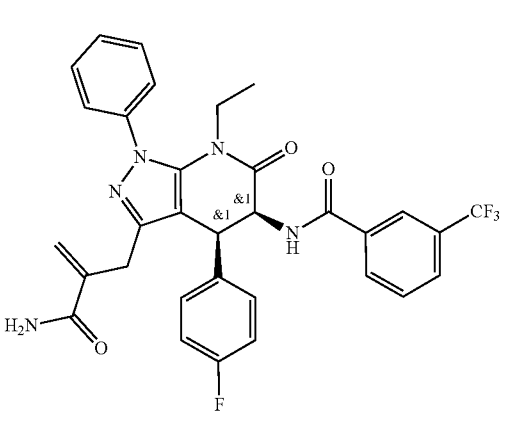

Into a 8 mL vial were added rac-2-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl) acrylic acid (100 mg, 0.165 mmol, 1.00 equiv), $NH_4Cl$ (10.6 mg, 0.198 mmol, 1.20 equiv), DIEA (42.6 mg, 0.330 mmol, 2.00 equiv), DMF (2 mL) and HATU (75.2 mg, 0.198 mmol, 1.20 equiv) at 25° C. The resulting mixture was stirred for 1 h at 25° C. The resulting mixture was diluted with water (2 mL). The mixture was purified by reversed-phase flash chromatography with the following conditions: Column: Sunfire Prep C18 OBD Column, 19*150 mm, 5 μm; Mobile Phase A: Water (0.1% FA), Mobile Phase B: ACN; Flow rate: 30 mL/min; Gradient: 37% B to 67% B in 8 min; Wave Length: 254 nm/220 nm; This resulted in rac-N-((4R,5R)-3-(2-carbamoylallyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (40 mg, 40%) as a white solid.

$^1H$ NMR (400 MHZ, DMSO-$d_6$) δ 8.50 (d, J=7.3 Hz, 1H), 8.18-8.08 (m, 2H), 7.92 (d, J=7.8 Hz, 1H), 7.77-7.63 (m, 3H), 7.59 (dd, J=8.4, 6.5 Hz, 2H), 7.56-7.48 (m, 1H), 7.42 (s, 1H), 7.15-7.04 (m, 2H), 6.97 (dd, J=8.5, 5.5 Hz, 3H), 5.71 (s, 1H), 5.50 (t, J=7.3 Hz, 1H), 5.17 (s, 1H), 4.50 (d, J=7.3 Hz, 1H), 3.90 (dd, J=14.3, 7.2 Hz, 1H), 3.38 (s, 2H), 3.07 (dd, J=14.2, 7.1 Hz, 1H), 0.93 (t, J=7.0 Hz, 3H).

LCMS Calculated for $C_{32}H_{27}F_4N_5O_3$: 605.21; Observed (Method-K): 606.5 $[M+H]^+$, 99.8% at RT 1.154 min.

1. Synthesis of rac-methyl (2E)-4-[(4R,5R)-7-ethyl-4-(4-fluorophenyl)-6-oxo-1-phenyl-5-[3-(trifluoromethyl)benzamido]-4H,5H-pyrazolo[3,4-b]pyridin-3-yl]but-2-enoate (I-131)

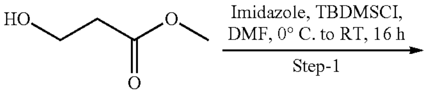

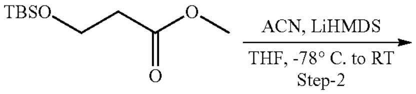

21

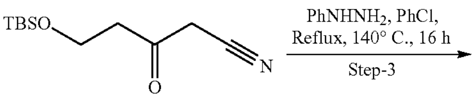

22

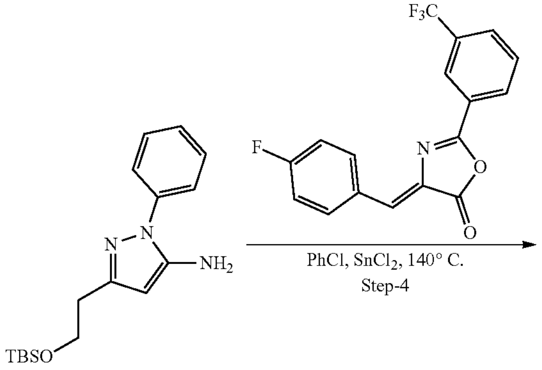

23

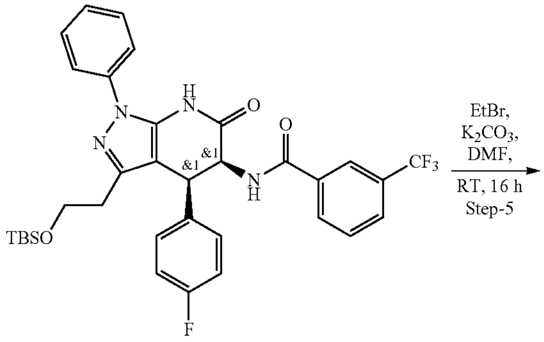

24

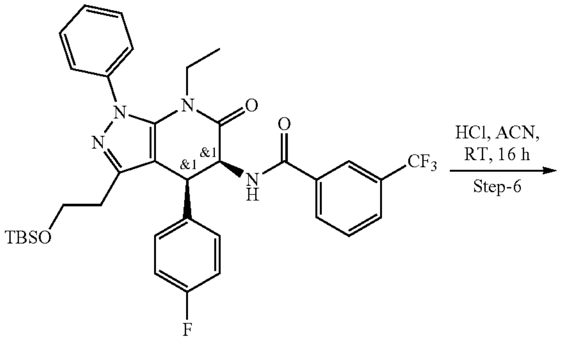

25

-continued

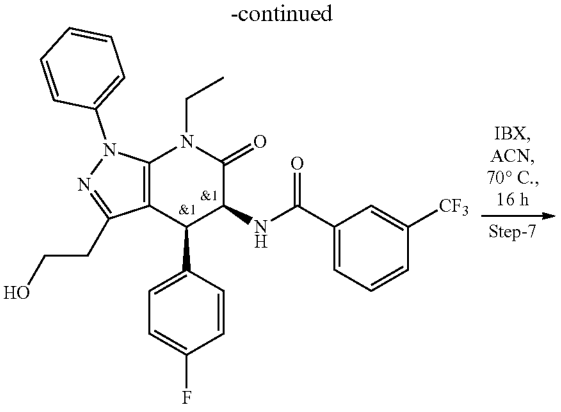

26

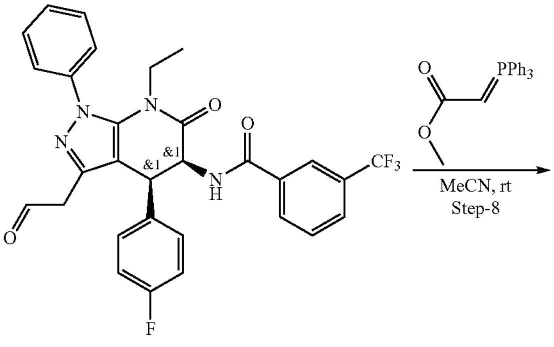

27

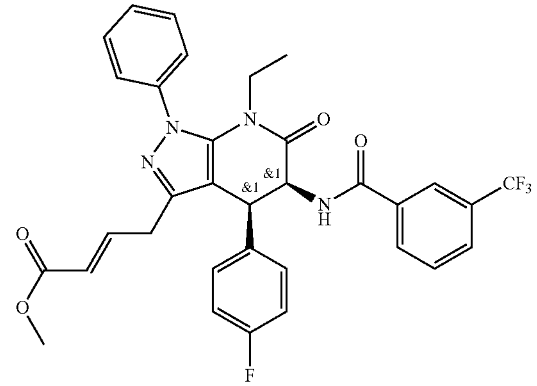

I-131-01 methyl 3-[(tert-butyldimethylsilyl)oxy]propanoate (21)

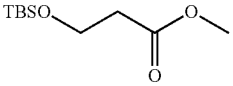

Into a 500 mL 3-necked round-bottom flask were added methyl 3-hydroxypropanoate (30.0 g, 288 mmol, 1.00 equiv), DMF (300 mL) and Imidazole (29.4 g, 432 mmol, 1.5 equiv) at room temperature. To the above mixture was added TBDMSCl (52.1 g, 346 mmol, 1.20 equiv) in portions over 0.5 h at room temperature. The resulting mixture was stirred overnight at room temperature. The resulting mixture was diluted with water (500 mL). The resulting mixture was extracted with EtOAc (2*200 mL). The combined organic layers were washed with brine (2×200 mL), dried over anhydrous $Na_2SO_4$. After filtration, the filtrate was concentrated under reduced pressure. The residue was purified by silica gel column chromatography, eluted with petroleum ether/EtOAc (10:1) to afford methyl 3-[(tert-butyldimethylsilyl)oxy]propanoate (45 g, 71%) as a white solid.

$^1$H NMR (400 MHZ, Chloroform-d) & 3.92 (t, J=6.4 Hz, 2H), 3.70 (s, 3H), 2.55 (t, J=6.4 Hz, 2H), 0.96-0.86 (m, 9H), 0.08 (s, 6H).

5-[(tert-butyldimethylsilyl)oxy]-3-oxopentanenitrile (22)

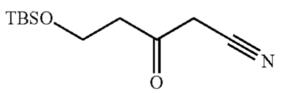

Into a 1000 mL 3-necked round-bottom flask were added ACN (12.7 g, 309 mmol, 1.50 equiv) and THF (500 mL) at room temperature. To the above mixture was added LiHMDS (44.8 g, 268 mmol, 1.30 equiv) dropwise over 0.5 h at −78° C. The resulting mixture was stirred for 2 h at −78° C. To the above mixture was added methyl 3-[(tert-butyldimethylsilyl)oxy]propanoate (45.0 g, 206 mmol, 1.00 equiv) dropwise over 0.5 h at −78° C. The resulting mixture was stirred for additional 1 h at −78° C. The mixture was allowed to warm up to room temperature. The resulting mixture was diluted with water (300 mL). The resulting mixture was extracted with EtOAc (2*200 mL). The combined organic layers were washed with brine (2*200 mL), dried over anhydrous $Na_2SO_4$. After filtration, the filtrate was concentrated under reduced pressure. The residue was purified by silica gel column chromatography, eluted with Petroleum ether/EtOAc (10:1) to afford 5-[(tert-butyldimethylsilyl)oxy]-3-oxopentanenitrile (40 g, 85%) as a white solid.

$^1$H NMR (400 MHZ, Chloroform-d) & 3.94 (t, J=5.9 Hz, 2H), 3.58 (s, 2H), 2.76 (t, J=5.9 Hz, 2H), 0.90 (s, 9H), 0.09 (s, 6H).

5-{2-[(tert-butyldimethylsilyl)oxy]ethyl}-2-ohenylpyrazol-3-amine (23)

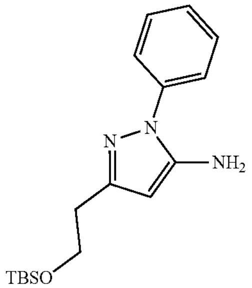

Into a 1000 mL round-bottom flask were added 5-[(tert-butyldimethylsilyl)oxy]-3-oxopentanenitrile (40.0 g, 176 mmol, 1.00 equiv), chlorobenzene (400 mL) and phenylhydrazine (19.0 g, 176 mmol, 1.00 equiv) at room temperature. The resulting mixture was stirred overnight at 140° C. under nitrogen atmosphere. The mixture was allowed to cool down to room temperature. The resulting mixture was concentrated under reduced pressure. The residue was purified by silica gel column chromatography, eluted with Petroleum ether/EtOAc (1:1) to afford 5-{2-[(tert-butyldimethylsilyl)oxy]ethyl}-2-phenylpyrazol-3-amine (25.0 g, 44%) as a yellow solid. $^1$H NMR (300 MHZ, DMSO-$d_6$) δ 7.56 (s, 2H), 7.45 (s, 1H), 7.28 (s, 1H), 5.39 (t, J=5.8 Hz, 1H), 5.25 (s, 2H), 3.81 (s, 2H), 2.62 (s, 2H), 1.17-0.40 (m, 9H), 0.18-0.17 (m, 6H).

LCMS Calculated for $C_{17}H_{27}N_3OSi$: 317.19; Observed: 318.20 $[M+H]^+$.

rac-N-((4R,5R)-3-(2-((tert-butyldimethylsilyl)oxy)ethyl)-4-(4-fluorophenyl)-3-(hydroxymethyl)-6-oxo1-phenyl-4,5,6,7-tetrahydro-1H-pyrazolo[3,4-b]pyridin-5-yl)-3-(trifluoromethyl)benzamide (24)

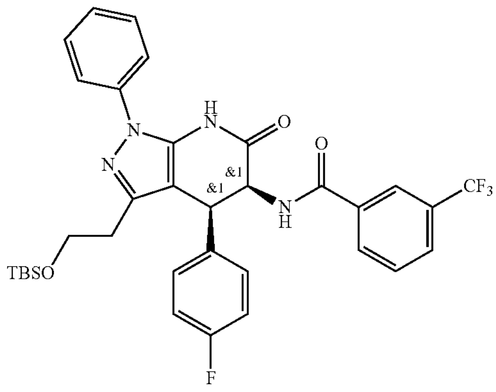

Into a 500 mL round-bottom flask were added 5-{2-[(tert-butyldimethylsilyl)oxy]ethyl}-2-phenylpyrazol-3-amine (18.0 g, 56.7 mmol, 1.00 equiv), (4Z)-4-[(4-fluorophenyl)methylidene]-2-[3-(trifluoromethyl)phenyl]-1,3-oxazol-5-one (19.0 g, 56.7 mmol, 1.00 equiv), chlorobenzene (200 mL) and $SnCl_2$ (1.09 g, 5.67 mmol, 0.1 equiv) at room temperature. The resulting mixture was stirred for 48 h at 140° C. under nitrogen atmosphere. The mixture was allowed to cool down to room temperature. The resulting mixture was concentrated under reduced pressure. The residue was purified by silica gel column chromatography, eluted with Petroleum ether/EtOAc (1:1) to afford rac-N-((4R,5R)-3-(2-((tert-butyldimethylsilyl)oxy)ethyl)-4-(4-fluorophenyl)-6-oxo-1-phenyl-4,5,6,7-tetrahydro-1H-pyrazolo[3,4-b]pyridin-5-yl)-3-(trifluoromethyl)benzamide (15 g, 40%) as a yellow solid. $^1$H NMR (400 MHZ, Chloroform-d) δ 8.00 (s, 1H), 7.86-7.78 (m, 3H), 7.63-7.55 (m, 5H), 7.44 (s, 1H), 7.00 (p, J=8.5 Hz, 4H), 6.73 (d, J=5.5 Hz, 1H), 5.32 (t, J=6.6 Hz, 1H), 4.94 (d, J=7.4 Hz, 1H), 3.71 (dt, J=12.2, 8.2 Hz, 2H), 2.81 (h, J=6.8 Hz, 2H), 2.07 (s, 1H), 1.32-1.24 (m, 2H), 0.84 (s, 9H), 0.09 (t, J=6.9 Hz, 1H).

rac-N-((4R,5R)-3-(2-((tert-butyldimethylsilyl)oxy)ethyl)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-3-(trifluoromethyl)benzamide (25)

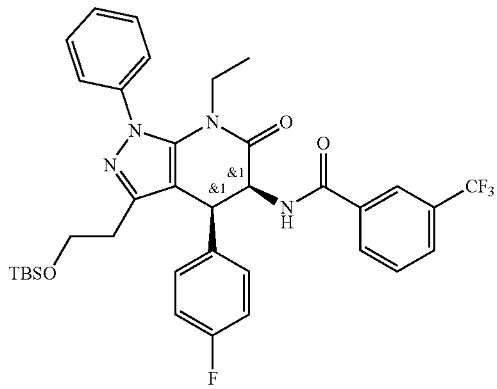

Into a 500 mL round-bottom flask were added rac-N-((4R,5R)-3-(2-((tert-butyldimethylsilyl)oxy)ethyl)-4-(4-fluorophenyl)-6-oxo-1-phenyl-4,5,6,7-tetrahydro-1H-pyrazolo[3,4-b]pyridin-5-yl)-3-(trifluoromethyl)benzamide (15.0 g, 22.9 mmol, 1.00 equiv), DMF (150 mL), $K_2CO_3$ (6.35 g, 45.9 mmol, 2.00 equiv) and bromoethane (3.00 g, 27.5 mmol, 1.20 equiv) at room temperature. The resulting mixture was stirred overnight at room temperature under nitrogen atmosphere. The resulting mixture was diluted with water (200 mL). The resulting mixture was extracted with EtOAc (2*200 mL). The combined organic layers were washed with brine (2*200 mL), dried over anhydrous $Na_2SO_4$. After filtration, the filtrate was concentrated under reduced pressure. The residue was purified by silica gel column chromatography, eluted with Petroleum ether EtOAc (1:1) to afford rac-N-((4R,5R)-3-(2-((tert-butyldimethylsilyl)oxy) ethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (15.0 g, 95%) as a yellow solid.

$^1$H NMR (400 MHZ, Chloroform-d) δ 8.07 (d, J=1.9 Hz, 1H), 7.90 (d, J=8.0 Hz, 1H), 7.85-7.78 (m, 1H), 7.65-7.45 (m, 6H), 7.03 (d, J=5.8 Hz, 1H), 7.01-6.92 (m, 4H), 5.25 (dd, J=7.2, 5.8 Hz, 1H), 4.83 (d, J=7.3 Hz, 1H), 4.00 (dq, J=14.4, 7.2 Hz, 1H), 3.76-3.61 (m, 2H), 3.21 (dq, J=14.0, 6.9 Hz, 1H), 2.91-2.71 (m, 2H), 1.03 (t, J=7.1 Hz, 3H), 0.82 (s, 9H), 0.06 (s, 6H).

rac-N-((4R,5R)-7-ethyl-4-(4-fluorophenyl)-3-(2-hydroxyethyl)-6-oxo-1-phenyl-4,5,6,7-tetrahydro-1H-pyrazolo[3,4-b]pyridin-5-yl)-3-(trifluoromethyl)benzamide (26)

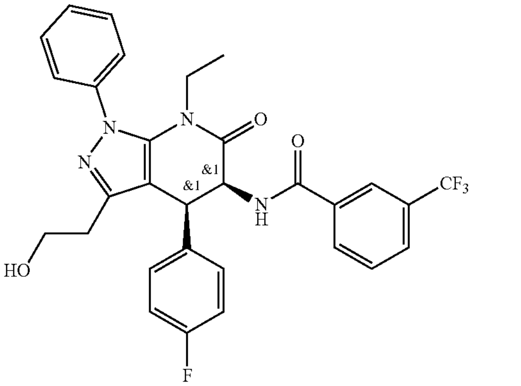

Into a 500 mL round-bottom flask were added rac-N-((4R,5R)-3-(2-((tert-butyldimethylsilyl)oxy)ethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (15 g, 22.0 mmol, 1.00 equiv), ACN (150 mL) and HCl (6M) (2.68 mL, 88.1 mmol, 4 equiv) at room temperature. The resulting mixture was stirred for 16 h at room temperature. The mixture was basified to pH 7 with saturated $NaHCO_3$ (aq.). The resulting mixture was extracted with EtOAc (2*100 mL). The combined organic layers were washed with brine (2*200 mL), dried over anhydrous $Na_2SO_4$. After filtration, the filtrate was concentrated under reduced pressure. The residue was purified by silica gel column chromatography, eluted with Petroleum ether/EtOAc (1:1) to afford rac-N-((4R,5R)-7-ethyl-4-(4-fluorophenyl)-3-(2-hydroxyethyl)-6-oxo-1-phenyl-4,5,6,7-tetrahydro-1H-pyrazolo[3,4-b]pyridin-5-yl)-3-(trifluoromethyl)benzamide (10 g, 80%) as a yellow solid.

$^1$H NMR (400 MHZ, Chloroform-d) δ 8.06 (d, J=1.9 Hz, 1H), 7.90 (dd, J=7.9, 1.8 Hz, 1H), 7.85-7.79 (m, 1H), 7.58 (dt, J=20.8, 7.5 Hz, 6H), 7.06 (d, J=5.3 Hz, 1H), 6.97 (d, J=6.8 Hz, 4H), 5.29-5.22 (m, 1H), 4.84 (d, J=7.1 Hz, 1H), 4.00 (dq, J=14.2, 7.1 Hz, 1H), 3.88 (dt, J=11.2, 5.7 Hz, 1H), 3.80 (dq, J=11.3, 6.5, 5.6 Hz, 1H), 3.23 (dq, J=13.8, 6.8 Hz, 1H), 2.87 (dt, J=12.4, 6.1 Hz, 1H), 2.71 (dt, J=15.3, 5.6 Hz, 1H), 2.54 (s, 1H), 1.04 (t, J=7.0 Hz, 3H).

rac-N-((4R,5R)-7-ethyl-4-(4-fluorophenyl)-6-oxo-3-(2-oxoethyl)-1-phenyl-4,5,6,7-tetrahydro-1H-pyrazolo[3,4-b]pyridin-5-yl)-3-(trifluoromethyl)benzamide (27)

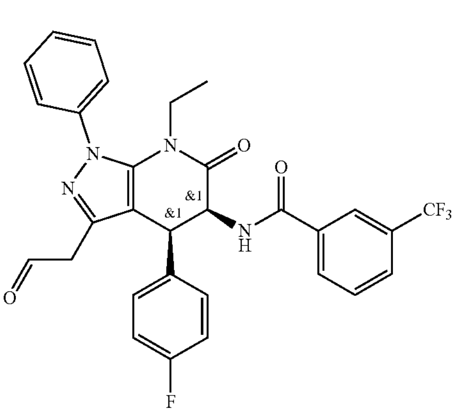

Into a 250 mL round-bottom flask were added rac-N-((4R,5R)-7-ethyl-4-(4-fluorophenyl)-3-(2-hydroxyethyl)-6-oxo-1-phenyl-4,5,6,7-tetrahydro-1H-pyrazolo[3,4-b]pyridin-5-yl)-3-(trifluoromethyl)benzamide (6.5 g, 11.5 mmol, 1.00 equiv), ACN (70 mL) and IBX (1.20 g, 4.29 mmol, 0.37 equiv) at room temperature. The resulting mixture was stirred for 16 h at 70° C. under nitrogen atmosphere. The mixture was allowed to cool down to room temperature. The resulting mixture was filtered, the filter cake was washed with MeCN (1*50 mL). The resulting mixture was used in the next step directly without further purification.

LCMS Calculated for $C_{30}H_{24}F_4N_4O_3$: 564.18; Observed: 565.18 $[M+H]^+$.

5. Synthesis of rac-methyl (E)-4-((4R,%R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)but-2-enoate (I-131)

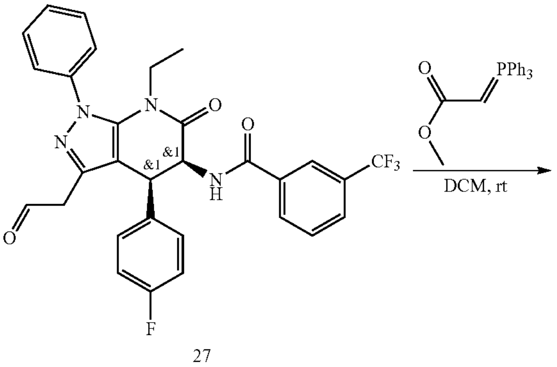

27

-continued

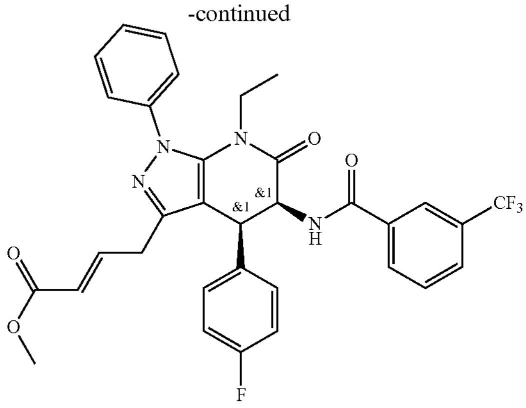

I-131

Into a 500 mL round-bottom flask were added rac-N-((4R,5R)-7-ethyl-4-(4-fluorophenyl)-6-oxo-3-(2-oxoethyl)-1-phenyl-4,5,6,7-tetrahydro-1H-pyrazolo[3,4-b]pyridin-5-yl)-3-(trifluoromethyl)benzamide (6.0 g, 10.6 mmol, 1.00 equiv), DCM (60 mL) and methyl 2-(triphenyl-lambda5-phosphanylidene)acetate (3.55 g, 10.6 mmol, 1.00 equiv) at room temperature. The resulting mixture was stirred for 5 h at room temperature. The resulting mixture was concentrated under reduced pressure. The residue was purified by silica gel column chromatography, eluted with petroleum ether/ethyl acetate (2:1) to afford rac-methyl (E)-4-((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) but-2-enoate (4.6 g, 69%) as a yellow solid.

$^1$H NMR (400 MHZ, Chloroform-d) δ 8.06 (s, 1H), 7.90 (d, J=7.8 Hz, 1H), 7.82 (d, J=7.8 Hz, 1H), 7.65-7.53 (m, 4H), 7.53 (d, J=7.1 Hz, 2H), 7.02 (d, J=5.5 Hz, 1H), 7.00-6.88 (m, 4H), 6.79 (dt, J=14.9, 6.8 Hz, 1H), 5.69 (d, J=15.5 Hz, 1H), 5.29-5.21 (m, 1H), 4.78 (d, J=7.2 Hz, 1H), 4.00 (dq, J=14.2, 7.0 Hz, 1H), 3.62 (s, 3H), 3.59-3.42 (m, 2H), 3.24 (dq, J=13.8, 6.8 Hz, 1H), 1.05 (t, J=7.0 Hz, 3H).

LCMS Calculated for $C_{33}H_{28}F_4N_4O_4$: 620.20; Observed (Method-K): 621.50 [M+H]$^+$, 96.6% at RT 1.325 min.

6. Synthesis of rac-(E)-4-((4R,5R)-7-ethyl-4-(4-fluorophenyl-6-oxo-1-phenyl-5-(3-(trifluoromethyl)benzamido)-4,5,6,7-tetrahydro-1H-pyrazolo-[3,4-b]pyridin-3-yl)but-2-enoic acid (I-83)

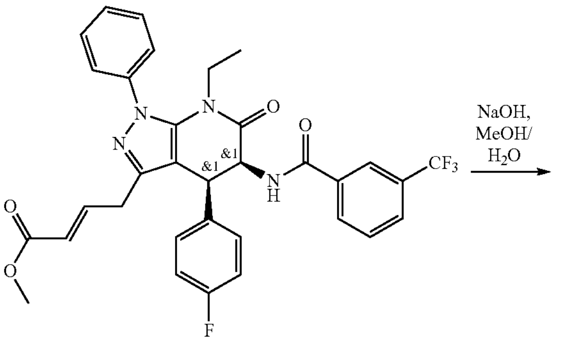

I-131

-continued

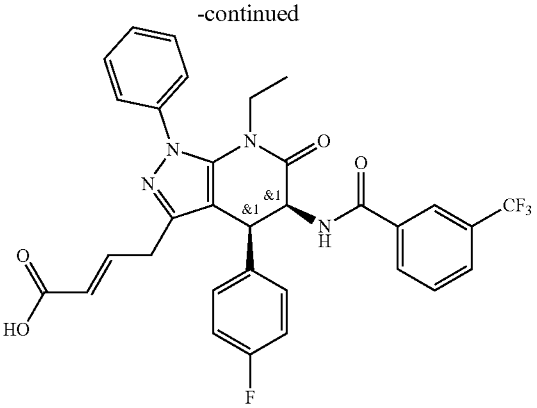

I-83

Into a 100 mL round-bottom flask were added rac-methyl (E)-4-((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) but-2-enoate (4.5 g, 7.25 mmol, 1.00 equiv), MeOH (40 mL), $H_2O$ (5 mL) and NaOH (0.44 g, 10.8 mmol, 1.50 equiv) at room temperature. The resulting mixture was stirred for 5 h at room temperature. The mixture was acidified to pH 5 with conc. HCl. The resulting mixture was extracted with ethyl acetate (2*100 mL). The combined organic layers were washed with brine (2*50 mL), dried over anhydrous $Na_2SO_4$. After filtration, the filtrate was concentrated under reduced pressure. The residue was purified by silica gel column chromatography, eluted with petroleum ether/ethyl acetate (0:1) to afford rac-(E)-4-((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) but-2-enoic acid (2.3 g, 52%) as a light yellow solid. $^1$H NMR (400 MHZ, DMSO-$d_6$) δ 12.24 (s, 1H), 8.58 (d, J=7.2 Hz, 1H), 8.20-8.12 (m, 2H), 7.93 (d, J=7.8 Hz, 1H), 7.76-7.68 (m, 3H), 7.65-7.59 (m, 2H), 7.59-7.51 (m, 1H), 7.17-7.07 (m, 2H), 7.07-6.97 (m, 2H), 6.38 (dt, J=16.3, 1.6 Hz, 1H), 6.00 (dt, J=16.2, 7.2 Hz, 1H), 5.54 (t, J=7.2 Hz, 1H), 4.62 (d, J=7.3 Hz, 1H), 3.91 (dq, J=14.3, 7.1 Hz, 1H), 3.11 (dt, J=7.1, 1.6 Hz, 2H), 3.03 (dt, J=13.8, 6.9 Hz, 1H), 0.93 (t, J=7.0 Hz, 3H).

LCMS Calculated for $C_{32}H_{26}F_4N_4O_4$: 606.19; Observed (Method-C): 607.1 [M+H]$^+$, 98.1% at RT 3.057 min.

Synthesis of rac-N-((4R,5R)-3-((E)-4-amino-4-oxobut-2-en-1-yl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-46)

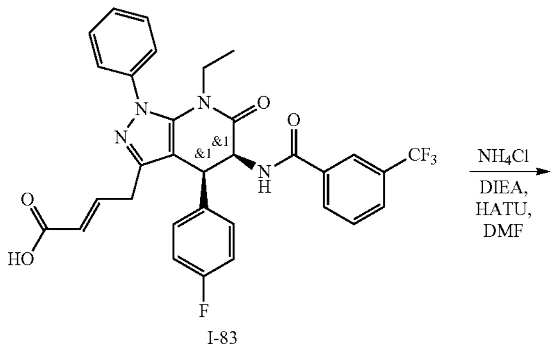

I-83

-continued

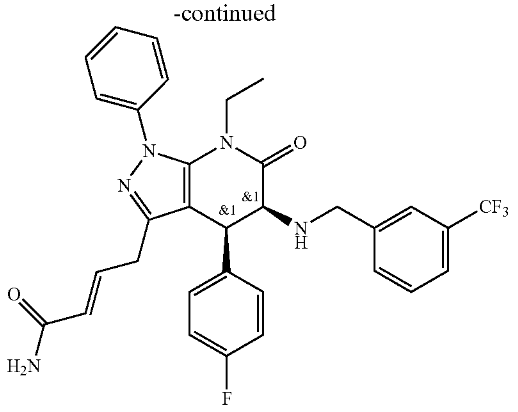

I-46

To a stirred solution of rac-(E)-4-((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) but-2-enoic acid (150 mg, 0.25 mmol, 1.00 equiv) and DIEA (80 mg, 0.62 mmol, 2.5 equiv) in DMF (1.5 mL) was added HATU (141 mg, 0.37 mmol, 1.5 equiv) for 10 min at 0° C. followed by the addition of $NH_4Cl$ (66.0 mg, 1.24 mmol, 5 equiv). The resulting mixture was stirred for 1 h at room temperature. The mixture was purified by prep HPLC to afford rac-N-((4R,5R)-3-((E)-4-amino-4-oxobut-2-en-1-yl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (70 mg, 46.7%) as white solid.

Following Compounds Prepared from the Above General Method Using the Intermediates Such as:

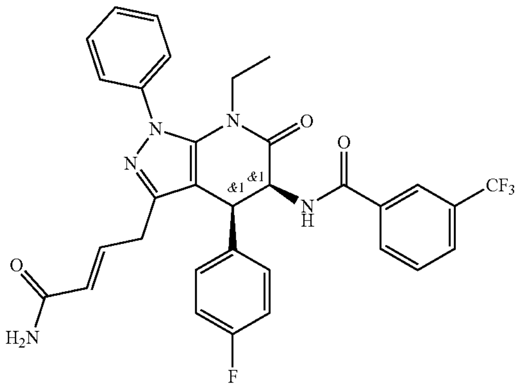 [SMILES: CCN1C(=O)[C@@H](NC(=O)c2cccc(C(F)(F)F)c2)[C@@H](c2ccc(F)cc2)c2c(C/C=C/C(N)=O)nn(-c3ccccc3)c21]

I-46

$^1$H NMR (400 MHz, DMSO-$d_6$) δ 8.56 (d, J = 7.2 Hz, 1H), 8.23-8.11 (m, 2H), 7.92 (d, J = 7.8 Hz, 1H), 7.75-7.68 (m, 3H), 7.63-7.51 (m, 3H), 7.27 (s, 1H), 7.17-7.09 (m, 2H), 7.00-7.04 (m, 2H), 6.77 (s, 1H), 6.32 (d, J = 16.2 Hz, 1H), 6.00-6.07 (m, 1H), 5.52 (t, J = 7.2 Hz, 1H), 4.61 (d, J = 7.2 Hz, 1H), 3.89 (q, J = 8.0 Hz, 1H), 3.01-3.06 (m, 1H), 2.91 (d, J = 7.2 Hz, 2H), 0.92 (t, J = 7.0 Hz, 3H). LCMS Calculated for $C_{32}H_{27}F_4N_5O_3$: 606.19; Observed (Method-C): 607.1 $[M + H]^+$, 98.6% at RT 1.168 min.

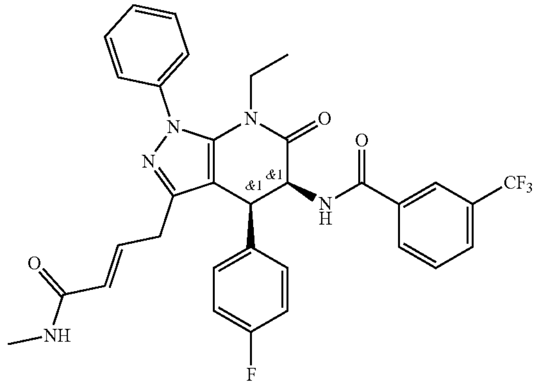 [SMILES: CCN1C(=O)[C@@H](NC(=O)c2cccc(C(F)(F)F)c2)[C@@H](c2ccc(F)cc2)c2c(C/C=C/C(=O)NC)nn(-c3ccccc3)c21]

I-38

$^1$H NMR (400 MHz, DMSO-$d_6$) δ 8.58 (d, J = 7.3 Hz, 1H), 8.20-8.12 (m, 2H), 7.93 (d, J = 7.8 Hz, 1H), 7.77-7.68 (m, 4H), 7.65-7.56 (m, 2H), 7.59-7.51 (m, 1H), 7.13 (t, J = 8.8 Hz, 2H), 7.02 (dd, J = 8.6, 5.5 Hz, 2H), 6.33 (dt, J = 15.9, 1.5 Hz, 1H), 6.03 (dt, J = 16.2, 7.1 Hz, 1H), 5.53 (t, J = 7.2 Hz, 1H), 4.61 (d, J= 7.3 Hz, 1H), 3.98-3.84 (m, 1H), 3.11-2.96 (m, 1H), 2.98-2.85 (m, 1H), 2.53 (s, 2H), 0.93 (t, J = 7.1 Hz, 3H).

LCMS Calculated for $C_{33}H_{29}F_4N_5O_3$: 619.22; Observed (Method-C): 620.1 $[M + H]^+$, 98.9% at 1.259 min.

-continued

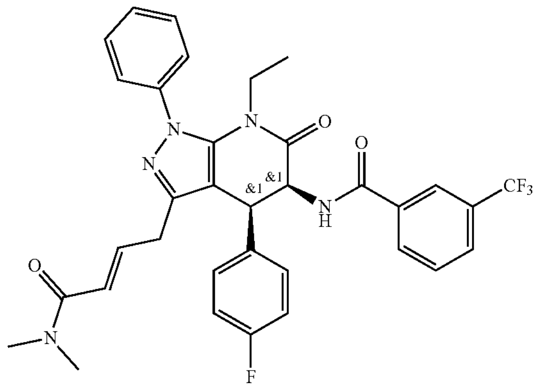 [SMILES: CCN1C(=O)[C@@H](NC(=O)c2cccc(C(F)(F)F)c2)[C@@H](c2ccc(F)cc2)c2c(C/C=C/C(=O)N(C)C)nn(-c3ccccc3)c21]

I-41

$^1H$ NMR (400 MHz, DMSO-$d_6$) δ 8.57 (d, J = 7.2 Hz, 1H), 8.19-8.12 (m, 2H), 7.93 (d, J = 7.9 Hz, 1H), 7.70-7.73 (m, 3H), 7.63-7.53 (m, 3H), 7.10-7.15 (m, 2H), 7.00-7.03 (m, 2H), 6.32 (d, J = 16.3 Hz, 1H), 5.96-5.04 (m, 1H), 5.54 (t, J = 7.2 Hz, 1H), 4.61 (d, J = 7.3 Hz, 1H), 3.89 (q, J = 8.0 Hz, 1H), 3.22-3.16 (m, 2H), 3.00-3.05 (m, 1H), 2.87 (s, 3H), 2.75 (s, 3H), 0.92 (t, J = 7.0 Hz, 3H). LCMS Calculated for $C_{34}H_{31}F_4N_5O_3$: 633.24; Observed (Method-C): 634.2 $[M + H]^+$, 99.1% at RT 1.268 min.

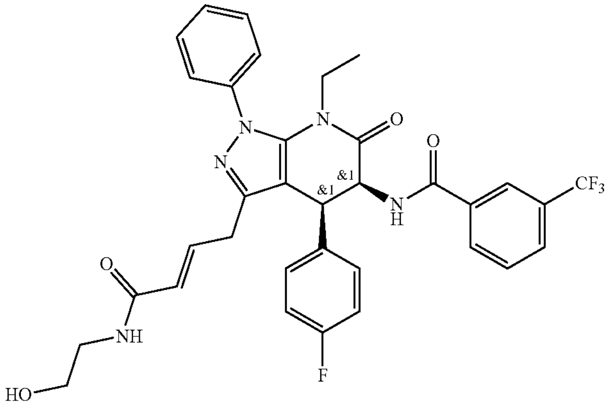 [SMILES: CCN1C(=O)[C@@H](NC(=O)c2cccc(C(F)(F)F)c2)[C@@H](c2ccc(F)cc2)c2c(C/C=C/C(=O)NCCO)nn(-c3ccccc3)c21]

I-36

$^1H$ NMR (400 MHz, DMSO-$d_6$) δ 8.56 (d, J = 7.2 Hz, 1H), 8.19-8.12 (m, 2H), 7.93 (d, J = 7.8 Hz, 1H), 7.82 (t, J = 5.4 Hz, 1H), 7.71 (d, J = 7.4 Hz, 3H), 7.65-7.51 (m, 3H), 7.12 (t, J= 8.8 Hz, 2H), 7.00-7.03 (m, 2H), 6.32 (d, J = 16.2 Hz, 1H), 6.09-5.98 (m, 1H), 5.52 (t, J = 7.2 Hz, 1H), 4.65-4.56 (m, 2H), 3.89 (q, J = 8.0 Hz, 1H), 3.37-3.33 (m, 2H), 3.09-2.98 (m, 3H), 2.98-2.90 (m, 2H), 0.92 (t, J = 7.0 Hz, 3H). LCMS Calculated for $C_{34}H_{31}F_4N_5O_4$: 649.23; Observed (Method-C): 650.3 $[M + H]^+$, 99.4% at RT 1.132 min.

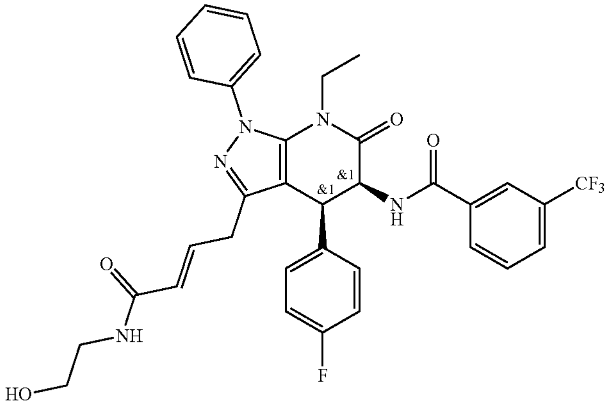 [SMILES: CCN1C(=O)[C@@H](NC(=O)c2cccc(C(F)(F)F)c2)[C@@H](c2ccc(F)cc2)c2c(C/C=C/C(=O)NCCO)nn(-c3ccccc3)c21]

I-24

$^1H$ NMR (400 MHz, DMSO-$d_6$) δ 8.58 (d, J = 7.2 Hz, 1H), 8.21-8.13 (m, 2H), 7.93 (d, J = 7.8 Hz, 1H), 7.80 (t, J = 5.5 Hz, 1H), 7.72 (d, J = 7.4 Hz, 3H), 7.64-7.53 (m, 3H), 7.12 (t, J= 8.8 Hz, 2H), 7.00-7.04 (m, 2H), 6.33 (d, J = 16.2 Hz, 1H), 5.98-6.06 (m, 1H), 5.53 (t, J = 7.2 Hz, 1H), 4.61 (d, J = 7.2 Hz, 1H), 4.38 (t, J = 5.2 Hz, 1H), 3.89 (q, J = 8.0 Hz, 1H), 3.39-3.35 (m, 2H), 3.04 (q, J = 6.7 Hz, 3H), 2.97-2.88 (m, 2H), 1.49 (m, 2H), 0.93 (t, J = 7.1 Hz, 3H). LCMS Calculated for $C_{35}H_{33}F_4N_5O_4$: 663.25; Observed (Method-C): 664.2 $[M + H]^+$, 99.4% at RT 1.151 min.

-continued

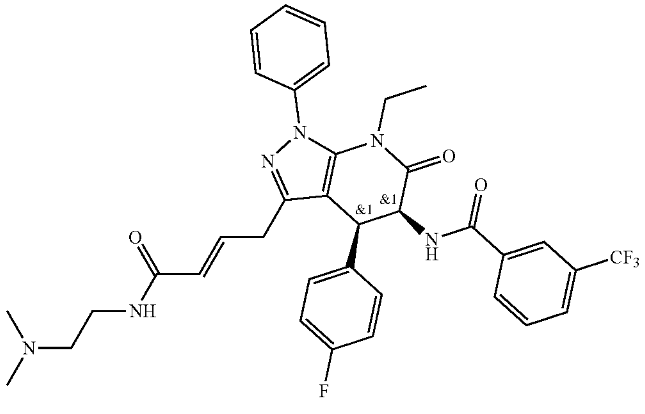 [SMILES: CCN1C(=O)[C@@H](NC(=O)c2cccc(C(F)(F)F)c2)[C@@H](c2ccc(F)cc2)c2c(C/C=C/C(=O)NCCN(C)C)nn(-c3ccccc3)c21]

I-118

$^1H$ NMR (400 MHz, DMSO-$d_6$) δ 8.57 (d, J = 7.2 Hz, 1H), 8.20-8.13 (m, 2H), 7.93 (d, J = 7.8 Hz, 1H), 7.72 (t, J = 7.7 Hz, 4H), 7.53-7.62 (m, 3H), 7.12 (t, J = 8.8 Hz, 2H), 7.05-6.98 (m, 2H), 6.33 (d, J = 16.2 Hz, 1H), 6.07-5.92 (m, 1H), 5.53 (t, J = 7.2 Hz, 1H), 4.60 (d, J = 7.3 Hz, 1H), 3.89 (q, J = 8.0 Hz, 1H), 3.14-2.98 (m, 3H), 2.98-2.87 (m, 2H), 2.20 (t, J = 6.8 Hz, 2H), 2.10 (s, 6H), 0.93 (t, J = 7.0 Hz, 3H).
LCMS Calculated for $C_{36}H_{36}F_4N_6O_3$: 676.28; Observed (Method-C): 677.3 $[M + H]^+$, 100.0% at RT 1.763 min.

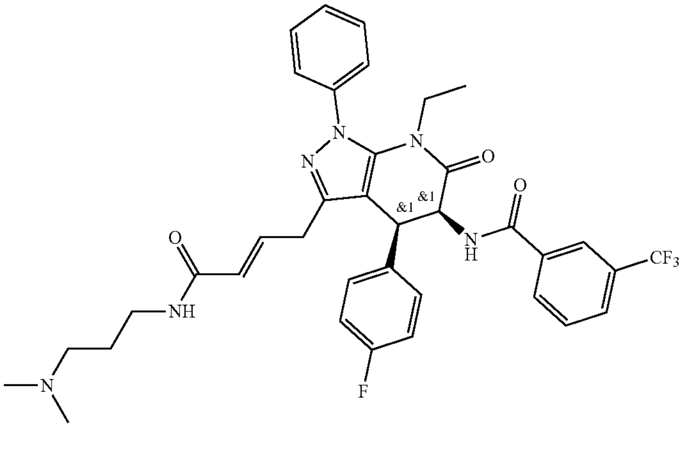 [SMILES: CCN1C(=O)[C@@H](NC(=O)c2cccc(C(F)(F)F)c2)[C@@H](c2ccc(F)cc2)c2c(C/C=C/C(=O)NCCCN(C)C)nn(-c3ccccc3)c21]

I-99

$^1H$ NMR (400 MHz, DMSO-$d_6$) δ 8.58 (d, J = 7.2 Hz, 1H), 8.20-8.13 (m, 2H), 7.93 (d, J = 7.8 Hz, 1H), 7.81 (t, J = 5.5 Hz, 1H), 7.72 (t, J = 7.8 Hz, 3H), 7.53-7.62 (m, 3H), 7.12 (t, J = 8.8 Hz, 2H), 7.06-6.98 (m, 2H), 6.33 (d, J = 16.2 Hz, 1H), 5.97-6.05 (m, 1H), 5.53 (t, J = 7.2 Hz, 1H), 4.60 (d, J = 7.2 Hz, 1H), 3.89 (q, J = 8.0 Hz, 1H), 3.09 - 2.96 (m, 3H), 2.96-2.88 (m, 2H), 2.14 (t, J = 7.1 Hz, 2H), 2.06 (s, 6H), 1.42-1.49 (m, 2H), 0.93 (t, J = 7.1 Hz, 3H).
LCMS Calculated for $C_{37}H_{38}F_4N_6O_3$: 690.29; Observed (Method-C): 691.3 $[M + H]^+$, 99.3% at RT 0.971 min.

8. Synthesis of rac-N-((4R, 5R)-3-(2-cyanamidoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-10)

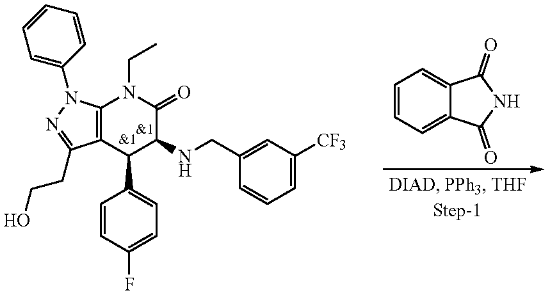

26

-continued

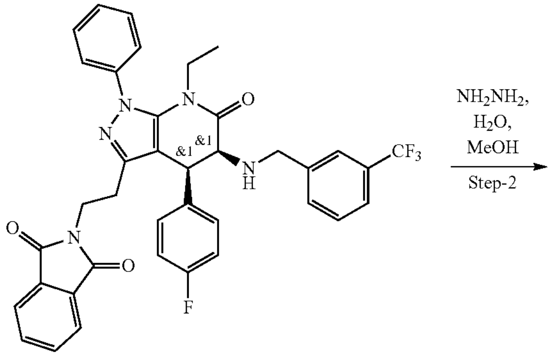

27

-continued

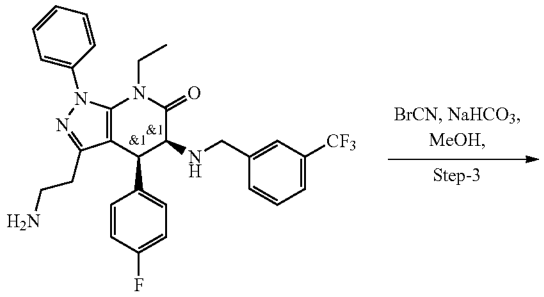

28

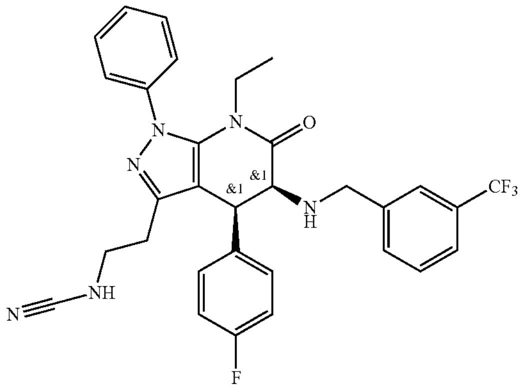

I-10-01 rac-N-((4R,5R)-3-(2-(1,3-dioxoisoindolin-2-yl)ethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (27)

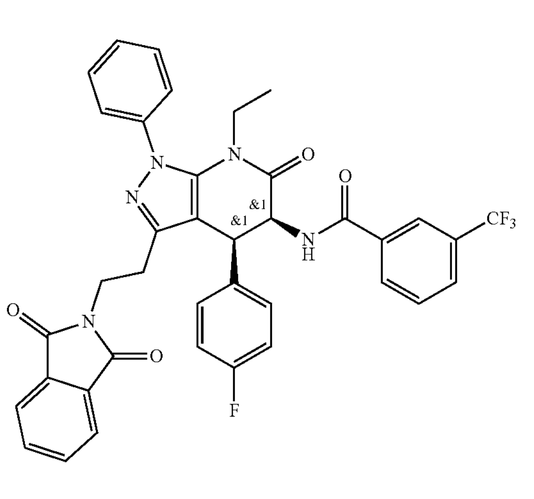

Into a 100 mL round-bottom flask were added rac-N-((4R,5R)-7-ethyl-4-(4-fluorophenyl)-3-(2-hydroxyethyl)-6-oxo-1-phenyl-4,5,6,7-tetrahydro-1H-pyrazolo[3,4-b]pyridin-5-yl)-3-(trifluoromethyl)benzamide (1.50 g, 2.65 mmol, 1.00 eq), THF (20 mL), phthalimide (0.47 g, 3.19 mmol, 1.20 equiv) and $PPh_3$ (1.39 g, 5.29 mmol, 2.00 eq) at room temperature. To the above mixture was added DIAD (0.64 g, 3.18 mmol, 1.20 eq) dropwise over 10 min at 0° C. The resulting mixture was stirred overnight at room temperature. The resulting mixture was diluted with water (20 mL). The resulting mixture was extracted with ethyl acetate (2×20 mL). The combined organic layers were washed with brine (2×20 mL), dried over anhydrous $Na_2SO_4$. After filtration, the filtrate was concentrated under reduced pressure. The residue was purified by silica gel column chromatography, eluted with petroleum ether/ethyl acetate (5:1) to afford rac-N-((4R,5R)-3-(2-(1,3-dioxoisoindolin-2-yl)ethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl) benzamide (1.7 g, 92%) as a white solid.

LCMS Calculated for $C_{38}H_{29}F_4N_5O_4$: 695.22; Observed: 696.2 $[M+H]^+$;

rac-N-((4R,5R)-3-(2-aminoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (28)

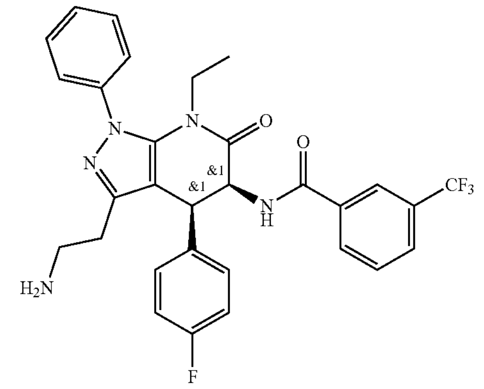

Into a 100 mL round-bottom flask were added rac-N-((4R,5R)-3-(2-(1,3-dioxoisoindolin-2-yl)ethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (1.70 g, 2.44 mmol, 1.00 equiv), MeOH (20 mL) and $NH_2NH_2 \cdot H_2O$ (0.49 g, 9.77 mmol, 4.00 equiv) at room temperature. The resulting mixture was stirred for 5 h at room temperature. The resulting mixture was concentrated under reduced pressure. The residue was purified by silica gel column chromatography, eluted with petroleum ether/ethyl acetate (1:1) to afford rac-N-((4R,5R)-3-(2-aminoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (0.9 g, 65%) as a white solid.

LCMS Calculated for $C_{30}H_{27}F_4N_5O_2$: 565.21; Observed: 566.22 $[M+H]^+$ rac-N-((4R,5R)-3-(2-cyanamidoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-10)

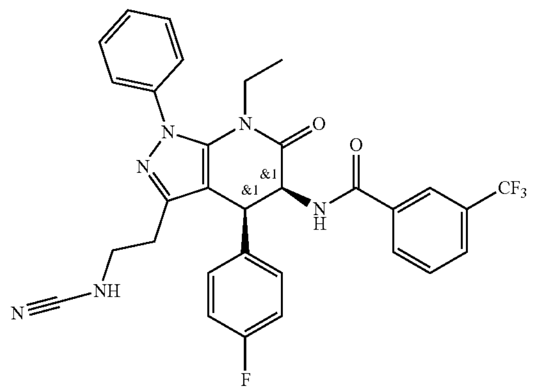

The compound (200 mg, 63%) was prepared in the same manner as I-144.

$^1$H NMR (400 MHZ, DMSO-$d_6$) δ 8.56 (d, J=7.4 Hz, 1H), 8.20-8.12 (m, 2H), 7.93 (d, J=7.8 Hz, 1H), 7.76-7.68 (m, 2H), 7.68 (t, J=1.4 Hz, 1H), 7.64-7.56 (m, 2H), 7.56-7.49 (m, 1H), 7.12 (t, J=8.8 Hz, 2H), 7.06-6.98 (m, 2H), 6.69 (t, J=5.4 Hz, 1H), 5.52 (t, J=7.4 Hz, 1H), 4.57 (d, J=7.3 Hz, 1H), 3.91 (dq, J=14.3, 7.1 Hz, 1H), 3.11-2.86 (m, 3H), 2.75-2.58 (m, 2H), 0.92 (t, J=7.0 Hz, 3H).

LCMS Calculated for $C_{31}H_{26}F_4N_6O_2$: 590.21; Observed (Method-C): 591.5 [M+H]$^+$; 98.4% at RT 1.276 min.

Synthesis of rac-N-((4R, 5R)-7-ethyl-4-(4-fluorophenyl)-3-(2-(N-methylcyanamido)ethyl)-6-oxo-1-phenyl-4,5,6,7-tetrahydro-1H-pyrazolo[3,4-b]pyridin-5-yl)-3-(trifluoromethyl)benzamide (I-151)

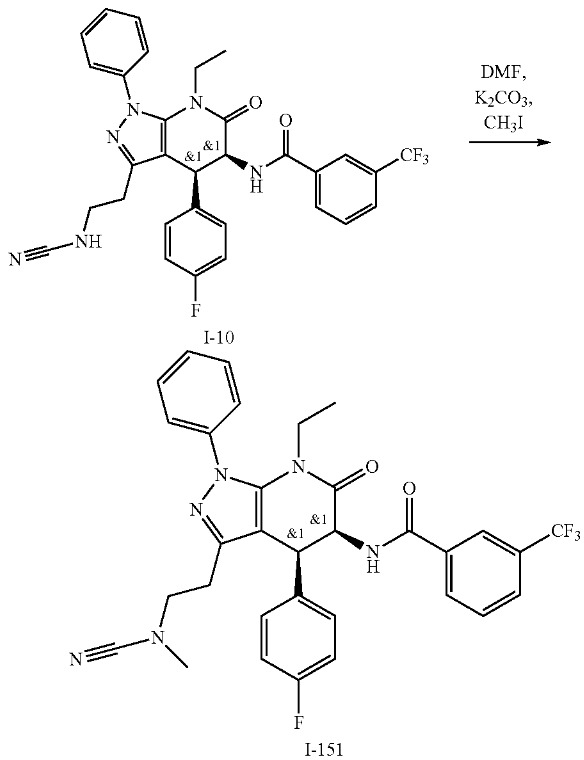

I-10

I-151

The compound (50 mg, 30.5%) was prepared in the same manner as I-42.

$^1$H NMR (300 MHZ, DMSO-$d_6$) δ 8.57 (d, J=7.4 Hz, 1H), 8.15 (d, J=10.0 Hz, 2H), 7.93 (d, J=7.8 Hz, 1H), 7.78-7.48 (m, 6H), 7.18-6.98 (m, 4H), 5.53 (t, J=7.3 Hz, 1H), 4.59 (d, J=7.3 Hz, 1H), 3.98-3.85 (m, 1H), 3.15-2.68 (m, 5H), 2.64 (s, 3H), 0.92 (t, J=7.0 Hz, 3H).

LCMS Calculated for $C_{32}H_{28}F_4N_6O_2$: 604.22; Observed (Method-C): 605.2 [M+H]$^+$, 99.8% at RT 1.323 min.

10. Synthesis of rac-methyl (E)-5-((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)pent-2-enoate (I-128)

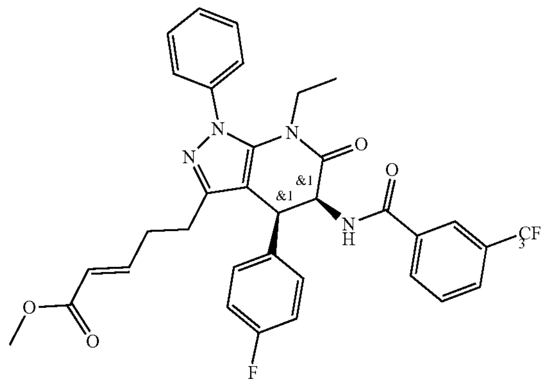

I-128

The compound (600 mg, 68%) was prepared in the same manner as I-131.

$^1$H NMR (300 MHZ, DMSO-$d_6$) δ 8.55 (d, J=7.5 Hz, 1H), 8.12 (d, J=9.7 Hz, 2H), 7.91 (d, J=7.9 Hz, 1H), 7.75-7.47 (m, 6H), 7.09 (t, J=8.7 Hz, 2H), 6.98 (t, J=7.0 Hz, 2H), 6.87-6.76 (m, 1H), 5.73 (d, J=15.7 Hz, 1H), 5.50 (t, J=7.3 Hz, 1H), 4.54 (d, J=7.3 Hz, 1H), 3.87 (dd, J=14.5, 7.3 Hz, 1H), 3.59 (s, 3H), 3.13-2.98 (m, 1H), 2.61 (dt, J=15.7, 7.4 Hz, 2H), 2.30 (q, J=7.8 Hz, 2H), 0.90 (t, J=7.0 Hz, 3H).

LCMS Calculated for $C_{34}H_{30}F_4N_4O_4$: 634.22; Observed (Method-C): 635.2 [M+H]$^+$, 99.9% at RT 1.397 min.

Synthesis of rac-(E)-5-((4R, 5R)-7-ethyl-4-fluorophenyl)-6-oxo-1-phenyl-5-(3-(trifluoromethyl)benzamido)-4,5,6,7-tetrahydro-1H-pyrazolo[3,4-b]pyridin-3-yl)pent-2-enoic acid (I-134) and rac-(Z)-5-((4R, 5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)pent-2-enoic acid (I-126)

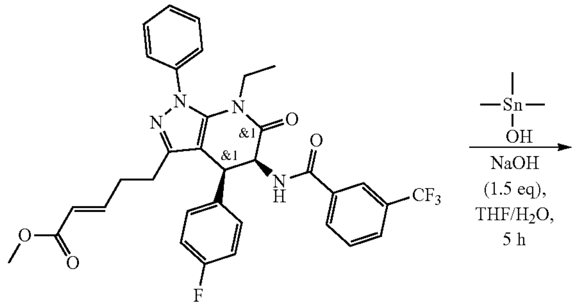

I-128

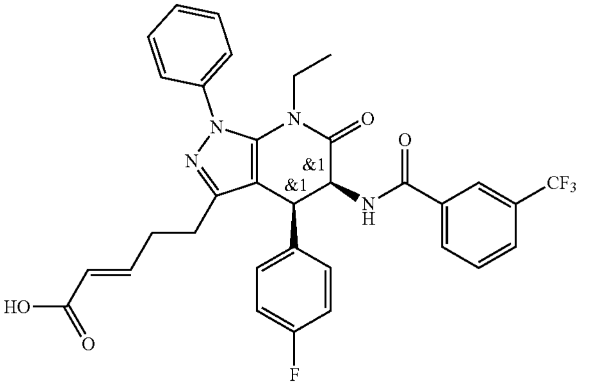

I-134

-continued

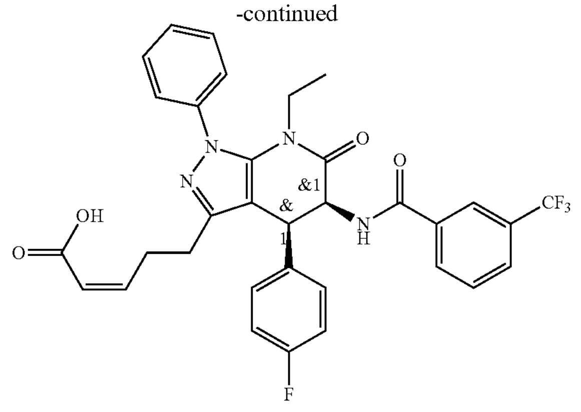

I-126

A solution of rac-methyl (E)-5-((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) pent-2-enoate (500 mg, 0.788 mmol, 1.00 equiv) and trimethyltin hydroxide (712 mg, 3.94 mmol, 5.00 equiv) in DCE (2 mL) was stirred overnight at 80° C. under nitrogen atmosphere. The mixture was allowed to cool down to room temperature. The resulting mixture was concentrated under reduced pressure. The residue was purified by silica gel column chromatography, eluted with petroleum ether/ethyl acetate (1:1) to afford rac-(E)-5-((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) pent-2-enoic acid (200 mg, 40.90%) as a white solid and rac-(Z)-5-((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) pent-2-enoic acid (270 mg, 55.22%) as a white solid. The 100 mg crude was purified by reverse phase flash with the following conditions (Column: Xselect CSH OBD C18 Column, 30*150 mm, 5 μm; Mobile Phase A: Water (0.1% FA), Mobile Phase B: ACN; Flow rate: 60 mL/min; Gradient: 5% B to 50% B in 10 min; Wave Length: 254 nm/220 nm) to afford pure rac-(E)-5-((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) pent-2-enoic acid (51 mg) as a white solid and rac-(Z)-5-((4R,5R)-7-ethyl-4-(4-fluorophenyl)-6-oxo-1-phenyl-5-(3-(trifluoromethyl) benzamido)-4,5,6,7-tetrahydro-1H-pyrazolo[3,4-b]pyridin-3-yl) pent-2-enoic acid (27 mg) as a white solid.

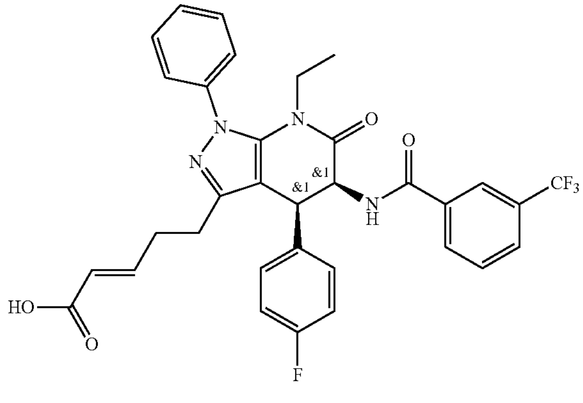 [SMILES: CCN1C(=O)[C@@H](NC(=O)c2cccc(C(F)(F)F)c2)[C@@H](c2ccc(F)cc2)c2c(CC/C=C/C(=O)O)nn(-c3ccccc3)c21]

I-134

$^1$H NMR (300 MHz, Chloroform-d) δ 8.04 (s, 1H), 7.89 (d, J = 7.8 Hz, 1H), 7.80 (d, J = 7.9 Hz, 1H), 7.64-7.46 (m, 6H), 7.08 (dd, J = 9.5, 5.4 Hz, 1H), 7.02-6.87 (m, 5H), 5.72 (dd, J = 18.3, 13.5 Hz, 1H), 5.23 (q, J = 7.5, 6.3 Hz, 1H), 4.81 (t, J = 6.0 Hz, 1H), 3.95 (dt, J = 14.1, 6.9 Hz, 1H), 3.21 (m, J = 13.5, 6.7 Hz, 1H), 2.85-2.60 (m, 2H), 2.42 (q, J = 7.2 Hz, 2H), 1.01 (q, J = 6.6, 6.0 Hz, 3H). LCMS Calculated for $C_{33}H_{28}F_4N_4O_4$: 620.20; Observed (Method-D): 621.3 [M + H]$^+$, 97.9% at RT 1.136 min.

-continued

| | |
|---|---|
| 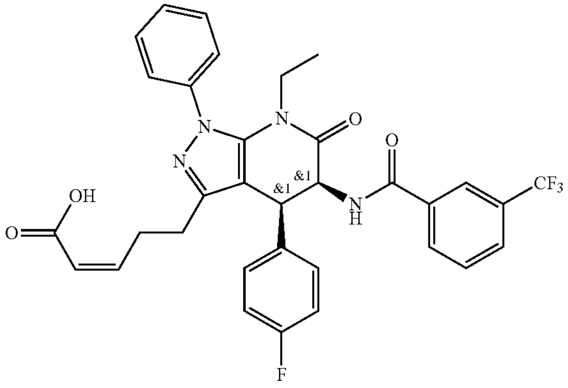 [SMILES: CCN1C(=O)[C@@H](NC(=O)c2cccc(C(F)(F)F)c2)[C@@H](c2ccc(F)cc2)c2c(CC/C=C\C(=O)O)nn(-c3ccccc3)c21]<br>I-126 | $^1$H NMR (300 MHz, Chloroform-d) δ 8.06 (s, 1H), 7.89 (d, J = 7.8 Hz, 1H), 7.81 (d, J = 7.8 Hz, 1H), 7.65-7.45 (m, 6H), 7.10 (d, J = 5.7 Hz, 1H), 6.95 (d, J = 6.9 Hz, 4H), 6.21-6.06 (m, 1H), 5.76 (d, J = 11.4 Hz, 1H), 5.25 (t, J = 6.3 Hz, 1H), 4.81 (d, J = 7.2 Hz, 1H), 3.94 (dq, J = 14.4, 7.2 Hz, 1H), 3.16 (m, 1H), 3.09-2.93 (m, 1H), 2.86-2.62 (m, 3H), 1.00 (t, J = 7.2 Hz, 3H). LCMS Calculated for $C_{33}H_{28}F_4N_4O_4$: 620.20; Observed (Method-D): 621.3 [M + H]$^+$, 98.4% at RT 1.154 min. |

12. The Compounds in the Table Below were Prepared in the Same Manner as I-46.

| | |
|---|---|
| 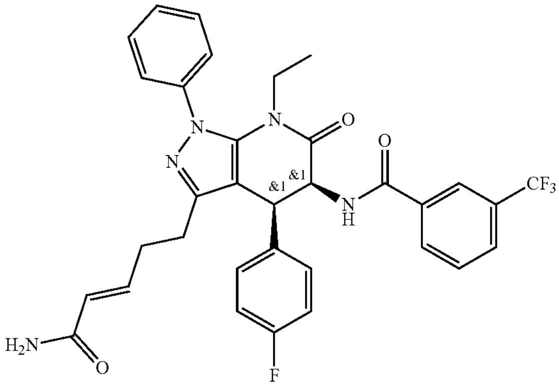 [SMILES: CCN1C(=O)[C@@H](NC(=O)c2cccc(C(F)(F)F)c2)[C@@H](c2ccc(F)cc2)c2c(CC/C=C/C(N)=O)nn(-c3ccccc3)c21]<br>I-124 | $^1$H NMR (400 MHz, DMSO-$d_6$): 8.56 (d, J = 7.4 Hz, 1H), 8.19-8.11 (m, 2H), 7.93 (d, J = 8.8 Hz, 1H), 7.74-7.66 (m, 3H), 7.62-7.49 (m, 3H), 7.29 (s, 1H), 7.12 (t, J = 8.8 Hz, 2H), 7.03-6.99 (m, 2H), 6.86 (s, 1H), 6.61-6.51 (m, 1H), 5.79 (d, J = 15.4 Hz, 1H), 5.52 (t, J = 7.4 Hz, 1H), 4.56 (d, J = 7.3 Hz, 1H), 3.89 (q, J = 8.0 Hz, 1H), 3.09-3.04 (m, 1H), 2.63-2.53 (m, 2H), 2.24 (q, J = 7.7 Hz, 2H), 0.92 (t, J = 7.0 Hz, 3H). LCMS Calculated for $C_{33}H_{29}F_4N_5O_3$: 619.22; Observed (Method-C): 620.1 [M + H]$^+$, 99.3% at RT 1.183 min. |
| 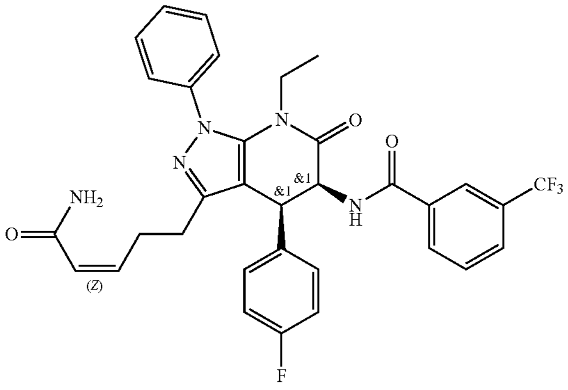 [SMILES: CCN1C(=O)[C@@H](NC(=O)c2cccc(C(F)(F)F)c2)[C@@H](c2ccc(F)cc2)c2c(CC/C=C\C(N)=O)nn(-c3ccccc3)c21]<br>I-142 | $^1$H NMR (400 MHz, DMSO-$d_6$): 8.53 (d, J = 7.3 Hz, 1H), 8.19-8.07 (m, 2H), 7.92 (d, J = 8.6 Hz, 1H), 7.73-7.66 (m, 3H), 7.60-7.50 (m, 3H), 7.30 (s, 1H), 7.10 (t, J = 8.8 Hz, 2H), 7.02-6.98 (m, 2H), 6.84 (s, 1H), 5.90-5.84 (m, 1H), 5.69 (d, J = 11.6 Hz, 1H), 5.51 (t, J = 7.3 Hz, 1H), 4.56 (d, J = 7.3 Hz, 1H), 3.89 (q, J = 8.0 Hz, 1H), 3.05 (q, J = 8.0 Hz, 1H), 2.76-2.67 (m, 2H), 0.92 (t, J = 7.1 Hz, 3H). LCMS Calculated for $C_{33}H_{29}F_4N_5O_3$: 619.22; Observed (Method-C): 620.1 [M + H]$^+$, 97.2% at RT 1.217 min. |

-continued

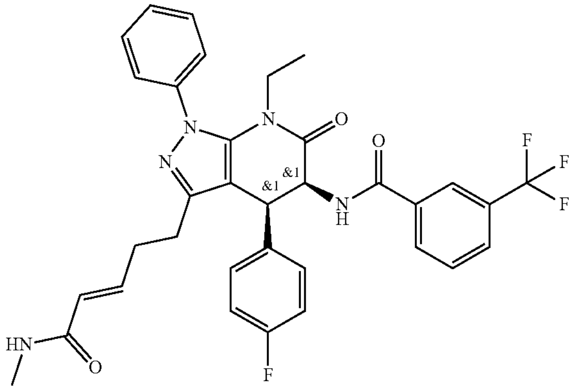 [SMILES: CCN1C(=O)[C@@H](NC(=O)c2cccc(C(F)(F)F)c2)[C@@H](c2ccc(F)cc2)c2c(CC/C=C/C(=O)NC)nn(-c3ccccc3)c21]

I-91

$^1$H NMR (400 MHz, DMSO-$d_6$) δ 8.56 (d, J = 7.3 Hz, 1H), 8.19-8.11 (m, 2H), 7.93 (d, J = 7.8 Hz, 1H), 7.77 (d, J = 4.8 Hz, 1H), 7.72 (t, J = 7.7 Hz, 1H), 7.69-7.64 (m, 2H), 7.59 (t, J = 7.5 Hz, 2H), 7.57-7.48 (m, 1H), 7.12 (t, J = 8.8 Hz, 2H), 7.05-6.97 (m, 2H), 6.61-6.49 (m, 1H), 5.78 (d, J = 15.5 Hz, 1H), 5.52 (t, J = 7.3 Hz, 1H), 4.56 (d, J = 7.3 Hz, 1H), 3.95-3.85 (m, 1H), 3.12-3.02 (m, 1H), 2.60 (d, J = 4.6 Hz, 3H), 2.58-2.53 (m, 2H), 2.24 (q, J = 7.5 Hz, 2H), 0.92 (t, J = 7.1 Hz, 3H). LCMS Calculated for $C_{34}H_{31}F_4N_5O_3$: 633; Observed (Method-C): 634.1 [M + H]$^+$, 99.4% at RT 1.230 min.

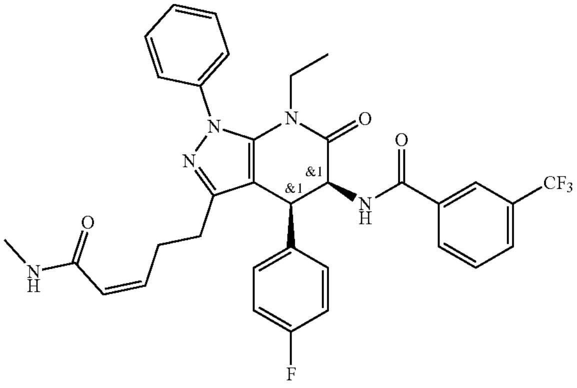 [SMILES: CCN1C(=O)[C@@H](NC(=O)c2cccc(C(F)(F)F)c2)[C@@H](c2ccc(F)cc2)c2c(CC/C=C\C(=O)NC)nn(-c3ccccc3)c21]

I-43

$^1$H NMR (400 MHz, DMSO-$d_6$) δ 8.53 (d, J = 7.3 Hz, 1H), 8.21-8.07 (m, 2H), 7.93 (d, J = 7.7 Hz, 1H), 7.83 (d, J= 4.5 Hz, 1H), 7.74-7.67 (m, 3H), 7.59 (t, J = 7.4 Hz, 2H), 7.52 (t, J = 7.3 Hz, 1H), 7.10 (t, J = 8.8 Hz, 2H), 7.02-6.99 (m, 2H), 5.88-5.81 (m, 1H), 5.67 (d, J = 11.5 Hz, 1H), 5.51 (t, J = 7.3 Hz, 1H), 4.56 (d, J = 7.3 Hz, 1H), 3.90 (q, J = 8.0 Hz 1H), 3.06 (dd, J = 14.0, 6.8 Hz, 1H), 2.78-2.71 (m, 2H), 2.55 (d, J = 4.7 Hz, 3H), 0.93 (t, J = 7.1 Hz, 3H).
LCMS Calculated for $C_{34}H_{31}F_4N_5O_3$: 633.24; Observed (Method-C): 634.1 [M + H]$^+$, 99.4% at RT 1.266 min.

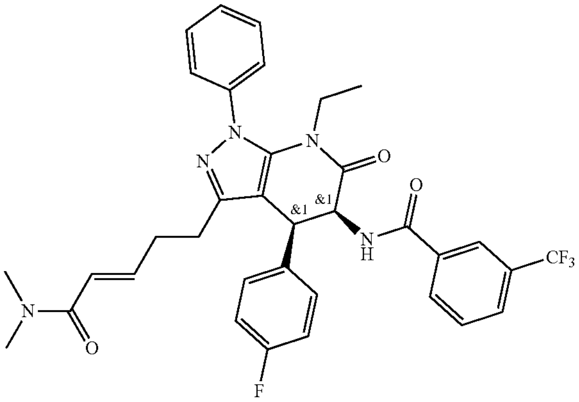 [SMILES: CCN1C(=O)[C@@H](NC(=O)c2cccc(C(F)(F)F)c2)[C@@H](c2ccc(F)cc2)c2c(CC/C=C/C(=O)N(C)C)nn(-c3ccccc3)c21]

I-48

$^1$H NMR (400 MHz, DMSO-$d_6$) δδ 8.55 (d, J = 7.4 Hz, 1H), 8.23-8.07 (m, 2H), 7.93 (d, J = 7.6 Hz, 1H), 7.75-7.63 (m, 3H), 7.61-7.51 (m, 3H), 7.12 (t, J = 8.8 Hz, 2H), 7.04-6.98 (m, 2H), 6.60-6.49 (m, 1H), 6.28 (d, J = 15.2 Hz, 1H), 5.52 (t, J = 7.3 Hz, 1H), 4.57 (d, J = 7.3 Hz, 1H), 3.89 (q, J = 8.0 Hz, 1H), 3.10-3.05 (m, 1H), 2.96 (s, 3H), 2.86-2.78 (m, 3H), 2.66-2.56 (m, 2H), 2.29 (q, J = 7.6 Hz, 2H), 0.92 (t, J = 7.0 Hz, 3H).
LCMS Calculated for $C_{35}H_{33}F_4N_5O_3$: 647.25; Observed (Method-E): 648.5 [M + H]$^+$, 91.9% at RT 1.259 min.

-continued

| | |
|---|---|
| 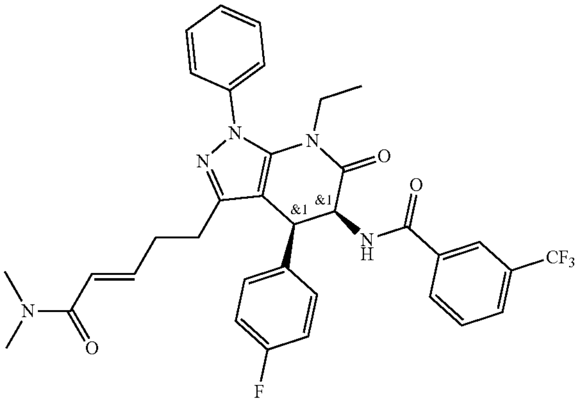 [SMILES: CCN1C(=O)[C@@H](NC(=O)c2cccc(C(F)(F)F)c2)[C@@H](c2ccc(F)cc2)c2c(CC/C=C/C(=O)N(C)C)nn(-c3ccccc3)c21]<br>I-69 | $^1H$ NMR (400 MHz, DMSO-$d_6$) δ 8.54 (d, J = 7.4 Hz, 1H), 8.22-8.09 (m, 2H), 7.93 (d, J = 7.9 Hz, 1H), 7.72 (t, J = 7.7 Hz, 1H), 7.67 (d, J = 7.4 Hz, 2H), 7.59 (t, J = 7.4 Hz, 2H), 7.53 (d, J = 7.1 Hz, 1H), 7.11 (t, J = 8.9 Hz, 2H), 7.02-6.98 (m, 2H), 6.00 (d, J = 11.6 Hz, 1H), 5.83-5.77 (m, 1H), 5.51 (t, J = 7.2 Hz, 1H), 4.54 (d, J = 7.2 Hz, 1H), 3.90 (q, J =8.0 Hz, 1H), 3.06 (dd, J = 14.0, 7.0 Hz, 1H), 2.85 (s, 3H), 2.78 (s, 3H), 2.54 (d, J = 8.8 Hz, 2H), 2.38 (q, J = 7.6 Hz, 2H), 0.92 (t, J = 7.0 Hz, 3H).<br>LCMS Calculated for $C_{35}H_{33}F_4N_5O_3$: 647.25; Observed (Method-C): 648.2 [M + H]$^+$, 99.8% at RT 1.286 min. |

Synthesis of rac-N-((4R, 5R)-7-ethyl-4-(4-fluorophenyl)-6-oxo-3-((Z)-(5-oxopyrrolidin-2-ylidene)methyl)-1-phenyl-4,5,6,7-tetrahydro-1H-pyrazolo[3,4-b]pyridin-5-yl)-3-(trifluoromethyl)benzamide (I-70) and rac-N-((4R, 5R)-7-ethyl-4-(4-fluorophenyl)-6-oxo-3-((E)-(5-oxopyrrolidin-2-ylidene)methyl)-1-phenyl-4,5,6,7-tetrahydro-1H-pyrazolo[3,4-b]pyridin-5-yl)-3-(trifluoromethyl)benzamide (I-39)

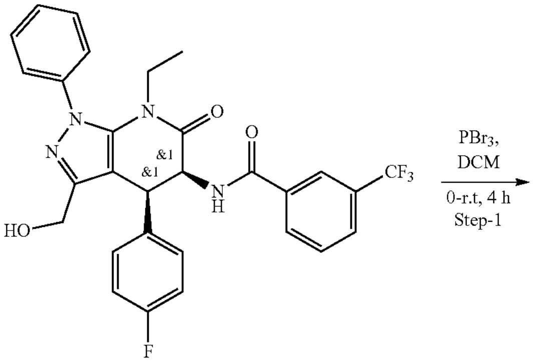

18

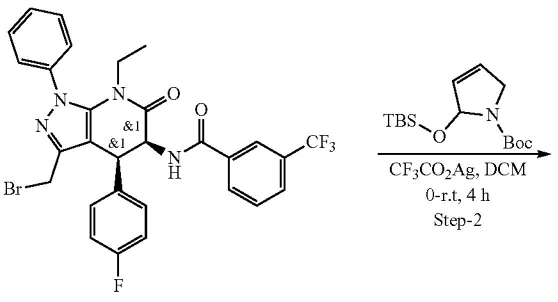

37

-continued

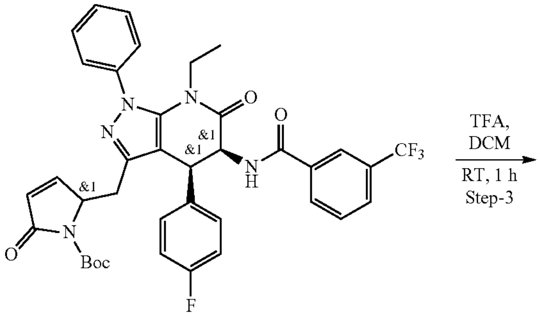

38

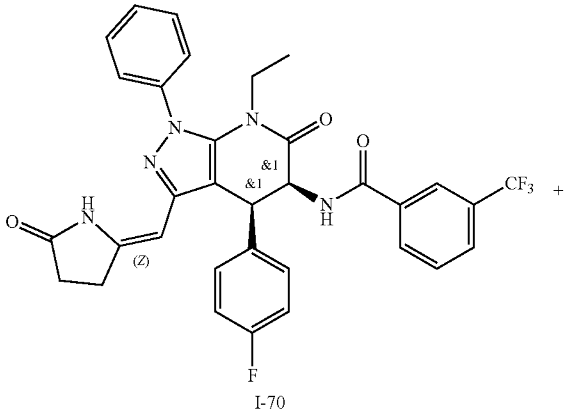

I-70

-continued

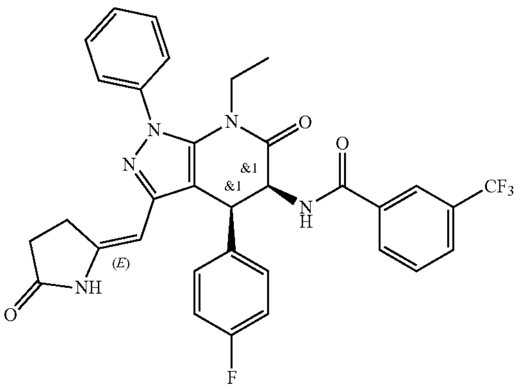

I-39 rac-N-((4R,5R)-3-(bromomethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (37)

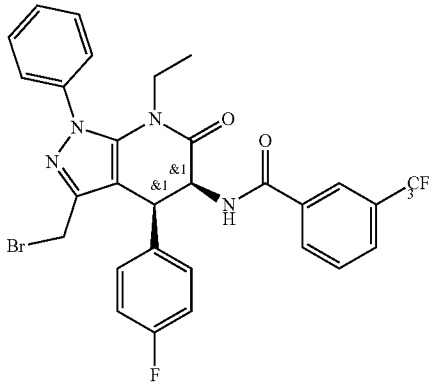

To a stirred solution of rac-N-((4R,5R)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-3-(trifluoromethyl)benzamide (1.00 g, 1.80 mmol, 1.00 equiv) in DCM (15.0 mL) were added $PBr_3$ (0.98 g, 3.60 mmol, 2.00 equiv) dropwise at 0° C. The reaction mixture was stirred for 4 hours at room temperature and diluted with water (20 mL). The mixture was extracted with DCM (50 mL×2). The combined organic phase was washed with brine (50 mL), dried over anhydrous sodium sulfate, filtered and concentrated in vacuum. The residue was purified by silica gel chromatography, eluted with petroleum ether/ethyl acetate (30% to 100%) to afford rac-N-((4R,5R)-3-(bromomethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (850 mg, 72%) as a white solid.

rac-tert-butyl 2-(((4R,5R)-7-ethyl-4-(4-fluorophenyl)-6-oxo-1-phenyl-5-(3-trifluoromethyl)benzamido)-4,5,6,7-tetrahydro-1H-pyrazolo[3,4-b]pyridin-3-yl)methyl)-5-oxo-2,5-dihydro-1H-pyrrole-1-carboxylate (38)

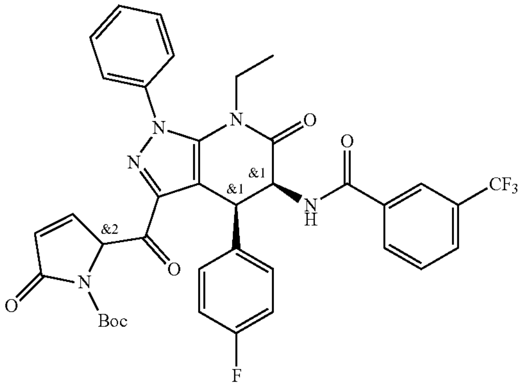

To a stirred solution of rac-N-((4R,5R)-3-(bromomethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (300 mg, 0.487 mmol, 1.00 equiv) and tert-butyl 2-[(tert-butyldimethylsilyl)oxy]-2,5-dihydropyrrole-1-carboxylate (1.45 g, 4.87 mmol, 10.0 equiv) in DCM (10 mL) were added $CF_3CO_2Ag$ (107 mg, 0.487 mmol, 1.00 equiv) at 0° C. The reaction mixture was stirred for 4 hours at room temperature and diluted with water (20 mL). The mixture was extracted with DCM (50 mL×2). The combined organic phase was washed with brine (50 mL), dried over anhydrous sodium sulfate, filtered and concentrated in vacuum. The residue was purified by silica gel chromatography, eluted with petroleum ether/ethyl acetate (60% to 100%) to afford rac-tert-butyl 2-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)-5-oxo-2,5-dihydro-1H-pyrrole-1-carboxylate (200 mg, 54%) as a light yellow oil.

rac-N-((4R,5R)-7-ethyl-4-(4-fluorophenyl)-6-oxo-3-((Z)-(5-oxopyrrolidin-2-ylidene)methyl)-1-phenyl-4,5,6,7-tetrahydro-1H-pyrazolo[3,4-b]pyridin-5-yl)-3-(trifluoromethyl)benzamide (I-70) and rac-N-((4R,5R)-7-ethyl-4-(4-fluorophenyl)-6-oxo-3-((E)-(5-oxopyrrolidin-2-ylidene)methyl)-1-phenyl-4,5,6,7-tetrahydro-1H-pyrazolo[3,4-b]pyridin-5-yl)-3-(trifluoromethyl)benzamide (I-39)

A solution of rac-tert-butyl 2-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)-5-oxo-2,5-dihydro-1H-pyrrole-1-carboxylate (200 mg, 0.279 mmol, 1.00 equiv) and TFA (1 mL) in DCM (5 mL). The reaction mixture was stirred for 1.0 hour at room temperature. The resulting mixture was concentrated in vacuum, the residue was purified by prep-HPLC ($NH_3 \cdot H_2O$ buffer) to give rac-N-((4R,5R)-7-ethyl-4-(4-fluorophenyl)-6-oxo-3-((Z)-(5-oxopyrrolidin-2-ylidene)methyl)-1-phenyl-4,5,6,7-tetrahydro-1H-pyrazolo[3,4-b]pyridin-5-yl)-3-(trifluoromethyl)benzamide (I-70) (40.0 mg, 23.2%) as a white solid and rac-N-((4R,5R)-7-ethyl-4-(4-fluorophenyl)-6-oxo-3-((E)-(5-oxopyrrolidin-2-ylidene)methyl)-1-phenyl-4,5,6,7-tetrahydro-1H-pyrazolo[3,4-b]pyridin-5-yl)-3-(trifluoromethyl)benzamide (I-39) (8.00 mg, 4.42%) as a white solid.

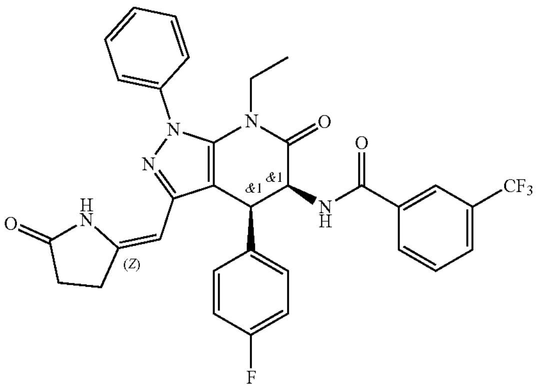 [SMILES: CCN1C(=O)[C@@H](NC(=O)c2cccc(C(F)(F)F)c2)[C@@H](c2ccc(F)cc2)c2c(/C=C3/CCC(=O)N3)nn(-c3ccccc3)c21]
I-70
$^1$H NMR-I-70 (300 MHz, DMSO-$d_6$) δ 9.59 (s, 1H), 8.59 (d, J = 7.2 Hz, 1H), 8.15-8.11 (m, 2H), 7.93 (d, J = 7.8 Hz, 1H), 7.84-7.68 (m, 3H), 7.68-7.52 (m, 3H), 7.12 (t, J = 8.8 Hz, 2H), 7.02-6.99 (m, 2H), 5.54 (t, J = 7.2 Hz, 1H), 5.24 (s, 1H), 4.59 (d, J = 7.2 Hz, 1H), 3.92-3.89 (m, 1H), 3.06-3.02 (m, 1H), 2.79-2.75 (m, 2H), 2.46-2.33 (m, 2H), 1.24 (s, 1H), 0.93 (t, J = 7.0 Hz, 3H).
LCMS Calculated for $C_{33}H_{27}F_4N_5O_3$: 617.21; Observed (Method-C): 618.1 [M + H]$^+$, 98.6% at RT 1.359 min.
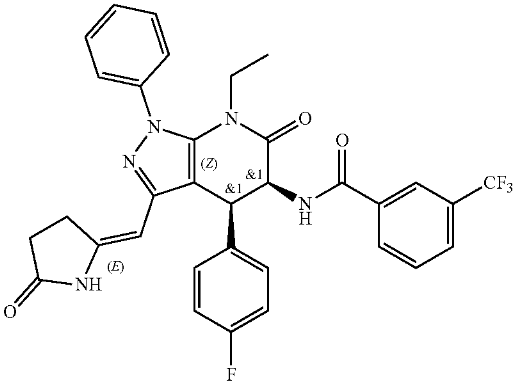 [SMILES: CCN1C(=O)[C@@H](NC(=O)c2cccc(C(F)(F)F)c2)[C@@H](c2ccc(F)cc2)c2c(/C=C3\CCC(=O)N3)nn(-c3ccccc3)c21]
I-39
$^1$H NMR (300 MHz, DMSO-$d_6$) : 10.07 (s, 1H), 8.57 (d, J = 7.1 Hz, 1H), 8.16 (d, J = 11.8 Hz, 2H), 7.93 (d, J = 7.8 Hz, 1H), 7.81-7.68 (m, 3H), 7.55-7.51 (m, 3H), 7.13 (t, J = 8.8 Hz, 2H), 6.99-6.96 (m, 2H), 5.50 (t, J = 7.1 Hz, 1H), 5.38 (s, 1H), 4.49 (d, J = 7.2 Hz, 1H), 3.93 (dd, J = 14.3, 7.2 Hz, 1H), 3.01-2.98 (m, 3H), 2.36-2.31 (m, 2H), 1.24 (s, 1H), 0.92 (t, J = 7.0 Hz, 3H).
LCMS Calculated $C_{33}H_{27}F_4N_5O_3$: 617.21; Observed (Method-C): 618.1 [M + H]$^+$, 97.1% at RT 1.277 min.

Synthesis of rac-N-((4R, 5R)-3-(2-cyanamido-1-hydroxyethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-9)

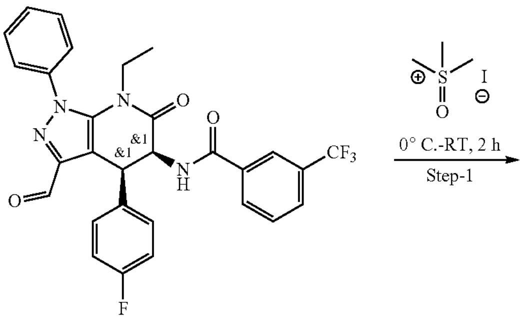

19

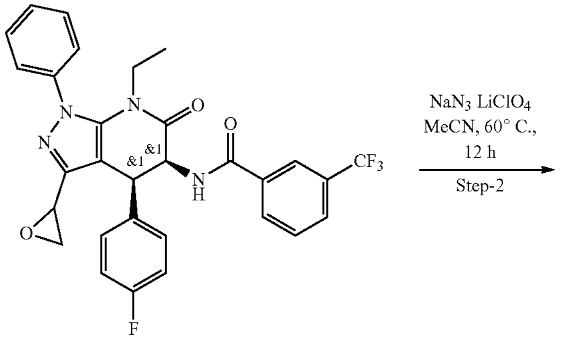

39

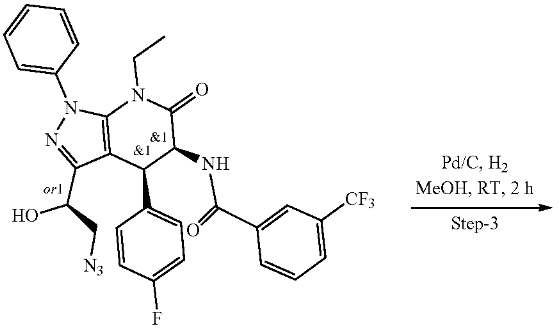

40

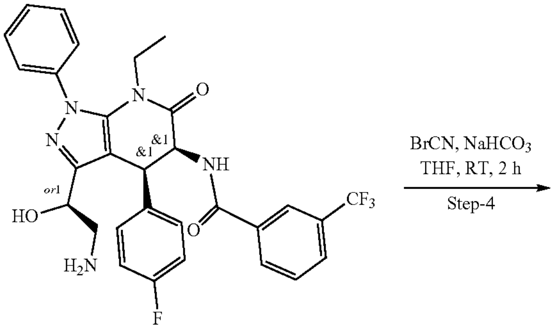

41

-continued

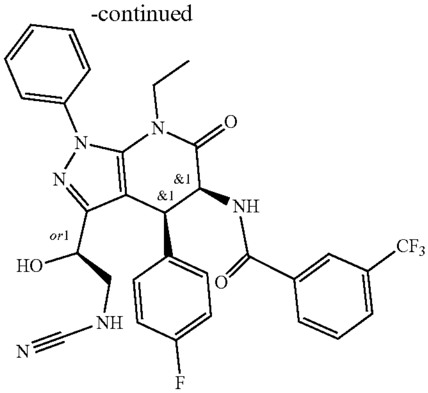

I-9 rac-N-((4R,5R)-7-ethyl-4-(4-fluorophenyl)-3-(oxiran-2-yl)-6-oxo-1-phenyl-4,5,6,7-tetrahydro-1H-pyrazolo[3,4-b]pyridin-5-yl)-3-(trifluoromethyl)benzamide (39)

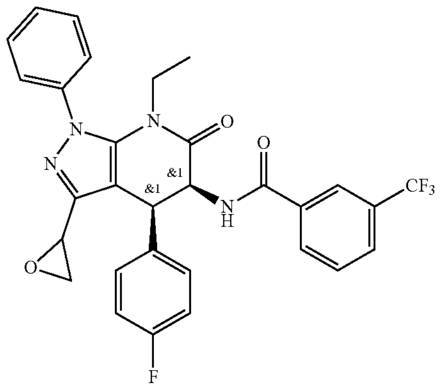

To a stirred solution of Iodotrimethyl-lamda6-sulfanone (2.24 g, 10.1 mmol, 2.00 equiv) in DMSO (30 mL) was added $Cs_2CO_3$ (3.65 g, 11.2 mmol, 2.20 equiv) in portions at 10° C. The resulting mixture was stirred for 30 min at room temperature. To the above mixture was added rac-N-((4R,5R)-7-ethyl-4-(4-fluorophenyl)-3-formyl-6-oxo-1-phenyl-4,5,6,7-tetrahydro-1H-pyrazolo[3,4-b]pyridin-5-yl)-3-(trifluoromethyl)benzamide (2.80 g, 5.09 mmol, 1.00 equiv) in portions over 10 min at room temperature. The resulting mixture was stirred for additional 1 hour at room temperature. The reaction was quenched with water (200 mL) at 0° C. The resulting mixture was extracted with ethyl acetate (3×100 ml). The combined organic layers were washed with brine (2×50 ml), dried over anhydrous $Na_2SO_4$. After filtration, the filtrate was concentrated under reduced pressure. The residue was purified by silica gel column chromatography, eluted with ethyl acetate/petroleum ether (111%, 20 min) to afford rac-N-((4R,5R)-7-ethyl-4-(4-fluorophenyl)-3-(oxiran-2-yl)-6-oxo-1-phenyl-4,5,6,7-tetrahydro-1H-pyrazolo[3,4-b]pyridin-5-yl)-3-(trifluoromethyl) benzamide (1.80 g, 53%) as a white solid.

rac-N-((4R,5R)-3-(2-azido-1-hydroxyethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (40)

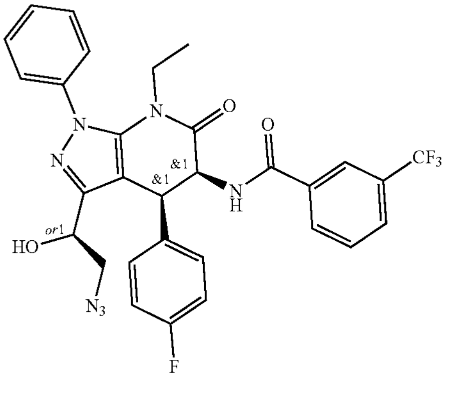

To a stirred solution of rac-N-((4R,5R)-7-ethyl-4-(4-fluorophenyl)-3-(oxiran-2-yl)-6-oxo-1-phenyl-4,5,6,7-tetrahydro-1H-pyrazolo[3,4-b]pyridin-5-yl)-3-(trifluoromethyl)benzamide (600 mg, 1.06 mmol, 1.00 equiv) and lithium perchlorate (565 mg, 5.32 mmol, 5.00 equiv) in MeCN (10 mL) was added azidosodium (138 mg, 2.13 mmol, 2.00 equiv) in portions at room temperature. The resulting mixture was stirred for 12 hours at 60° C. The resulting mixture was allowed to cool down to room temperature and filtered, the filter cake was washed with MeCN (2×20 ml). The filtrate was concentrated under reduced pressure. The residue was purified by silica gel column chromatography, eluted with ethyl acetate/petroleum ether (0-100%, 20 min) to afford rac-N-((4R,5R)-3-(2-azido-1-hydroxyethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (400 mg, 45%) as a white solid.

rac-N-((4R,5R)-3-(2-amino-1-hydroxyethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (41)

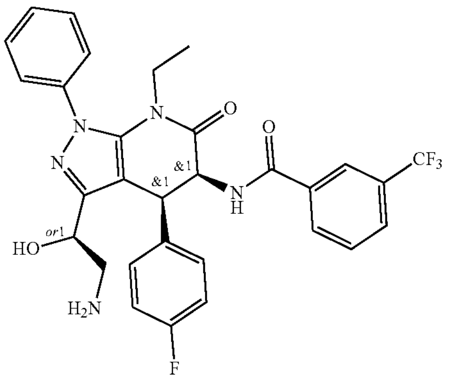

Into a 50 mL round-bottom flask, was placed rac-N-((4R,5R)-3-(2-azido-1-hydroxyethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (400 mg, 0.658 mmol, 1.00 equiv) in MeOH (10 mL) was added Pd/C (80 mg, 20% w/wt) at room temperature and then the reaction mixture was degassed and purged with hydrogen for three times. The mixture was stirred for 2.0 hours under hydrogen atmosphere (1 atm). The reaction mixture was filtered and the filtrate was concentrated in vacuum to give rac-N-((4R,5R)-3-(2-amino-1-hydroxyethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (300 mg, 62%) as a yellow solid.

rac-N-((4R,5R)-3-(2-cyanamido-1-hydroxyethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-9)

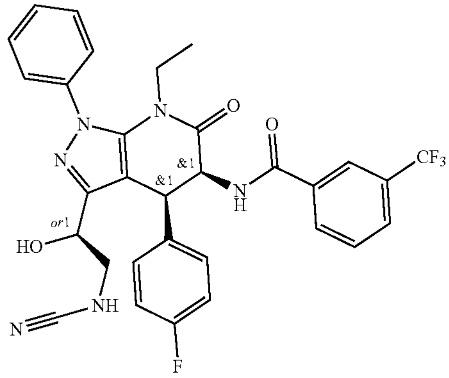

A mixture of rac-N-((4R,5R)-3-(2-amino-1-hydroxyethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (200 mg, 0.337 mmol, 1.00 equiv), $NaHCO_3$ (84.9 mg, 1.01 mmol, 3.00 equiv) and BrCN (53.6 mg, 0.506 mmol, 1.50 equiv) in THF (5 mL) was stirred for 2 hours at room temperature. The mixture was purified by reversed-phase flash chromatography with the following conditions: column, C18 silica gel; mobile phase, MeCN in water (0.05% $NH_4CO_3$), 10% to 50% gradient in 10 min; detector, UV 254 nm. This resulted in rac-N-((4R,5R)-3-(2-cyanamido-1-hydroxyethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (20.0 mg, 8%) as a white solid.

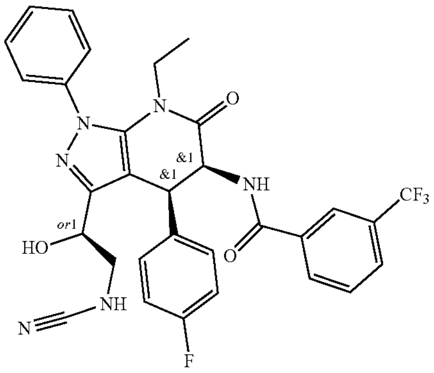 [SMILES: CCN1C(=O)[C@@H](NC(=O)c2cccc(C(F)(F)F)c2)[C@@H](c2ccc(F)cc2)c2c([C@H](O)CNC#N)nn(-c3ccccc3)c21]
I-9
$^1$H NMR (400 MHz, DMSO-$d_6$) δ 8.57-8.48 (m, 1H), 8.19-8.11 (m, 2H), 7.93 (d, J = 7.8 Hz, 1H), 7.76-7.67 (m, 3H), 7.65-7.57 (m, 3H), 7.14-7.06 (m, 2H), 7.02-6.93 (m, 2H), 5.58-5.52 (m, 1H), 5.44-5.30 (m, 1H), 4.63-4.55 (m, 1H), 3.95-3.83 (m, 1H), 3.83-3.70 (m, 1H), 3.20 (dd, J = 11.9, 7.7 Hz, 1H), 3.05 (dq, J = 13.8, 6.8 Hz, 1H), 0.97-0.89 (m, 3H).
LCMS Calculated for $C_{31}H_{26}F_4N_6O_3$: 606.20; Observed (Method-K): 607.5 $[M + H]^+$, 98.5% at RT 0.813 min.
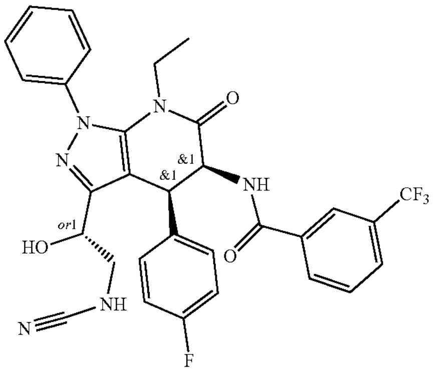 [SMILES: CCN1C(=O)[C@@H](NC(=O)c2cccc(C(F)(F)F)c2)[C@@H](c2ccc(F)cc2)c2c([C@@H](O)CNC#N)nn(-c3ccccc3)c21]
I-130
$^1$H NMR (300 MHz, DMSO-$d_6$) δ 9.13 (d, J = 8.2 Hz, 1H), 8.09-7.99 (m, 2H), 7.92 (d, J = 7.8 Hz, 1H), 7.76-7.68 (m, 3H), 7.64-7.50 (m, 3H), 7.44-7.35 (m, 2H), 7.21-7.12 (m, 2H), 5.32-5.17 (m, 1H), 5.07 (t, J = 8.5 Hz, 1H), 4.49 (d, J = 8.9 Hz, 1H), 3.98 (t, J = 6.3 Hz, 1H), 3.61-3.45 (m, 3H), 2.81 (qd, J = 13.2, 6.4 Hz, 1H), 0.81 (t, J = 7.0 Hz, 3H);
LCMS Calculated for $C_{31}H_{26}F_4N_6O_3$: 606.20; Observed (Method-AQ): 607.3 $[M + H]^+$, 83.3% at RT 2.027 min.

Synthesis of rac-methyl (E)-4-((((4R, 5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)amino)-2-methyl-4-oxobut-2-enoate (I-150)

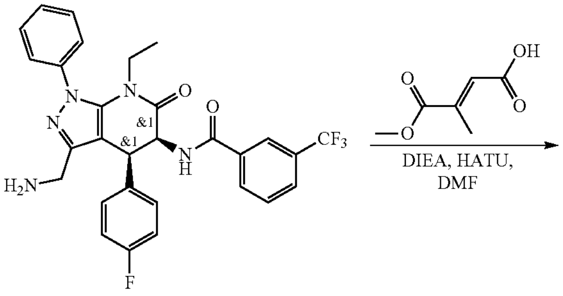

43

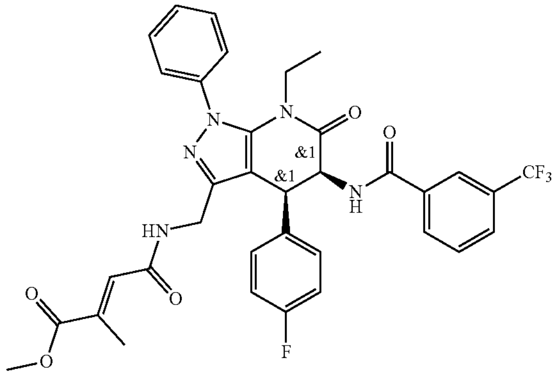

I-150

The compound 43 was prepared in the same manner as compound 28.

A mixture of rac-N-((4R,5R)-3-(aminomethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (150 mg, 0.272 mmol, 1.00 equiv) and DIEA (105 mg, 0.816 mmol, 3.00 equiv) in DMF (5 mL) was stirred at room temperature for 10 min. HATU (124 mg, 0.326 mmol, 1.20 equiv) was then added, and the reaction mixture was stirred for 1.0 hour at room temperature. The resulting mixture was concentrated in vacuum, the residue was purified by prep-HPLC ($NH_3 \cdot H_2O$ buffer) to give rac-methyl (E)-4-((((4R, 5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)amino)-2-methyl-4-oxobut-2-enoate (75.0 mg, 40%) as a white solid.

$^1$H NMR (300 MHZ, DMSO-$d_6$) δ 8.62 (d, J=6.3 Hz, 1H), 8.54 (d, J=7.4 Hz, 1H), 8.16-8.14 (m, 2H), 7.94 (d, J=7.8 Hz, 1H), 7.71-7.65 (m, 3H), 7.57-7.53 (m, 3H), 7.01-6.97 (m, 2H), 6.93-6.81 (m, 2H), 6.25 (d, J=1.8 Hz, 1H), 5.51 (t, J=7.3 Hz, 1H), 4.56-4.51 (m, 1H), 4.41-4.39 (m, 1H), 4.15-4.10 (m, 1H), 3.92-3.80 (m, 1H), 3.69 (s, 3H), 3.02-2.94 (m, 1H), 2.05 (d, J=1.5 Hz, 3H), 0.91 (t, J=7.0 Hz, 3H).

LCMS Calculated for $C_{35}H_{31}F_4N_5O_5$: 677.23; Observed (Method-G): 678.2 $[M+H]^+$, 99.8% at RT 1.157 min.

The compounds in the table below were prepared in the same manner as compound I-150.

| | |
|---|---|
| 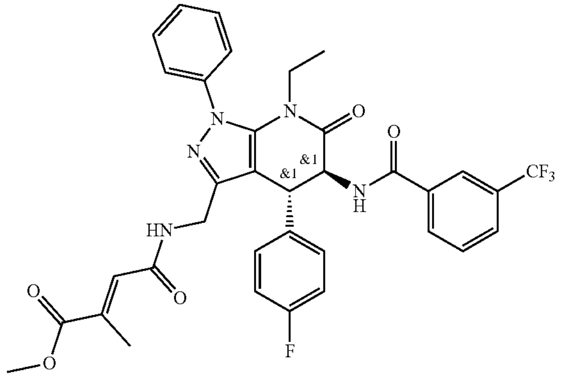 [SMILES: CCN1C(=O)[C@@H](NC(=O)c2cccc(C(F)(F)F)c2)[C@H](c2ccc(F)cc2)c2c(CNC(=O)/C=C(\C)C(=O)OC)nn(-c3ccccc3)c21]<br>I-104 | $^1$H NMR (300 MHz, DMSO-$d_6$) δ 9.05 (d, J = 8.6 Hz, 1H), 8.43 (t, J = 5.1 Hz, 1H), 8.01 (d, J = 5.5 Hz, 2H), 7.91 (d, J = 7.7 Hz, 1H), 7.76-7.65 (m, 3H), 7.63-7.48 (m, 3H), 7.38-7.34 (m, 2H), 7.11 (t, J = 8.8 Hz, 2H), 6.69 (d, J = 1.7 Hz, 1H), 5.20-5.14 (m, 1H), 4.46 (d, J = 11.1 Hz, 1H), 3.71 (s, 3H), 3.68-3.65 (m, 1H), 3.63 (d, J = 5.3 Hz, 2H), 3.21-3.19 (m, 1H), 2.09 (d, J = 1.5 Hz, 3H), 0.82 (t, J = 7.0 Hz, 3H).<br>LCMS Calculated for $C_{35}H_{31}F_4N_5O_5$: 677.23; Observed (Method-E): 678.2 $[M + H]^+$, 98.3% at RT 2.834 min. |

-continued

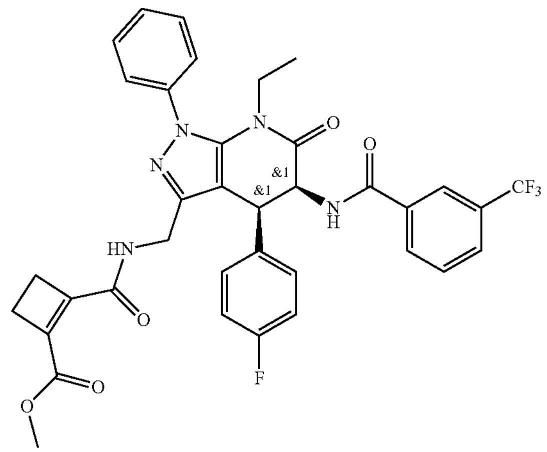 [SMILES: CCN1C(=O)[C@@H](NC(=O)c2cccc(C(F)(F)F)c2)[C@@H](c2ccc(F)cc2)c2c(CNC(=O)C3=C(C(=O)OC)CC3)nn(-c3ccccc3)c21]

$^1$H NMR (300 MHz, DMSO-$d_6$) δ 8.78-8.63 (m, 1H), 8.51 (d, J = 7.3 Hz, 1H), 8.27-8.11 (m, 2H), 7.93 (d, J = 7.8 Hz, 1H), 7.72-7.68 (m, 3H), 7.67-7.40 (m, 3H), 7.02-6.99 (m, 2H), 6.79-6.74 (m, 2H), 5.51 (t, J = 7.2 Hz, 1H), 4.77-4.73 (m, 1H), 4.42 (d, J = 7.2 Hz, 1H), 4.11-4.08 (m, 1H), 3.88-3.84 (m, 1H), 3.67 (s, 3H), 3.15-2.88 (m, 1H), 2.45-2.14 (m, 4H), 0.91 (t, J = 7.0 Hz, 3H). LCMS Calculated for $C_{36}H_{31}F_4N_5O_5$: 689.23; Observed (Method-C): 690.4 $[M + H]^+$, 95.9% at RT 1.280 min.

I-119

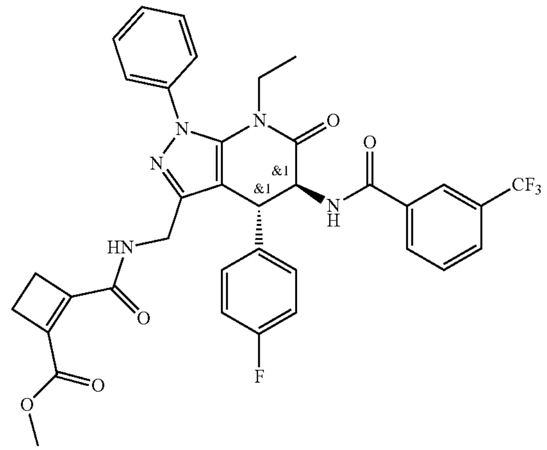 [SMILES: CCN1C(=O)[C@@H](NC(=O)c2cccc(C(F)(F)F)c2)[C@H](c2ccc(F)cc2)c2c(CNC(=O)C3=C(C(=O)OC)CC3)nn(-c3ccccc3)c21]

$^1$H NMR (300 MHz, DMSO-$d_6$) δ 9.10 (d, J = 8.5 Hz, 1H), 8.65 (d, J = 5.2 Hz, 1H), 8.02 (d, J = 6.1 Hz, 2H), 7.92 (d, J = 7.8 Hz, 1H), 7.79-7.67 (m, 3H), 7.57-7.51 (m, 3H), 7.35-7.31 (m, 2H), 7.13 (t, J = 8.8 Hz, 2H), 5.33-4.99 (m, 1H), 4.42-4.39 (m, 1H), 3.79-3.74 (m, 1H), 3.72 (s, 3H), 3.61-3.58 (m, 1H), 3.26-3.22 (m, 1H), 2.44-2.41 (m, 3H), 0.82 (t, J = 6.9 Hz, 3H). LCMS Calculated for $C_{36}H_{31}F_4N_5O_5$: 689.23; Observed (Method-C): 690.1 $[M + H]^+$, 95.7% at RT 2.381 min.

I-97

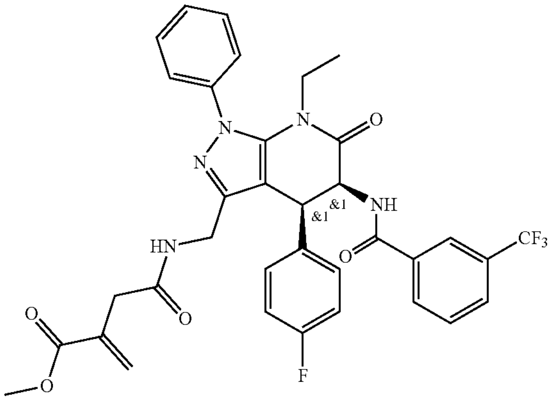 [SMILES: C=C(CC(=O)NCc1nn(-c2ccccc2)c2c1[C@H](c1ccc(F)cc1)[C@H](NC(=O)c1cccc(C(F)(F)F)c1)C(=O)N2CC)C(=O)OC]

$^1$H NMR (300 MHz, DMSO-$d_6$) δ 8.54 (d, J = 7.4 Hz, 1H), 8.18-8.15 (m, 3H), 7.93 (d, J = 7.8 Hz, 1H), 7.79-7.66 (m, 3H), 7.65-7.46 (m, 3H), 7.12 (t, J = 8.8 Hz, 1H), 6.94-6.90 (m, 2H), 6.05 (d, J = 1.4 Hz, 1H), 5.59-5.37 (m, 2H), 4.55 (d, J = 7.2 Hz, 1H), 4.26-4.22 (m, 1H), 4.11-4.08 (m, 1H), 3.92-3.89 (m, 1H), 3.72 (s, 3H), 3.15-2.89 (m, 1H), 2.74-2.72 (m, 1H), 2.61-2.59 (m, 1H), 0.91 (t, J = 7.0 Hz, 3H). LCMS Calculated for $C_{35}H_{31}F_4N_5O_5$: 677.23; Observed (Method-E): 678.3 $[M + H]^+$, 99.6% at RT 1.022 min.

I-4

-continued

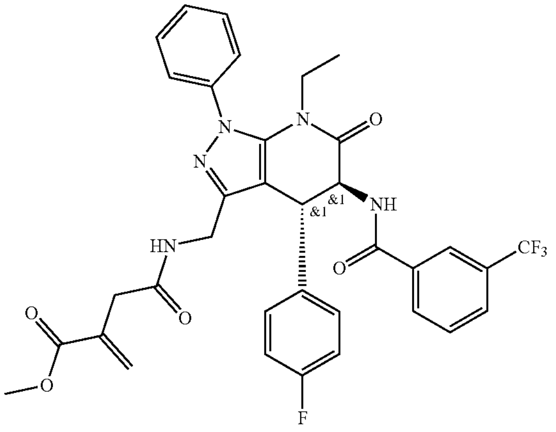 [SMILES: C=C(CC(=O)NCc1nn(-c2ccccc2)c2c1[C@@H](c1ccc(F)cc1)[C@H](NC(=O)c1cccc(C(F)(F)F)c1)C(=O)N2CC)C(=O)OC]

I-132

$^1$H NMR (300 MHz, DMSO-$d_6$) δ 9.04 (d, J = 8.8 Hz, 1H), 8.02 (d, J = 6.1 Hz, 2H), 7.92 (d, J = 7.0 Hz, 2H), 7.64-7.58 (m, 6H), 7.41-7.38 (m, 2H), 7.14 (t, J = 8.6 Hz, 2H), 6.09 (d, J = 1.5 Hz, 1H), 5.65 (s, 1H), 5.33-5.11 (m, 1H), 4.44 (d, J = 11.5 Hz, 1H), 3.82-3.66 (m, 1H), 3.63 (s, 3H), 3.48 (d, J = 4.9 Hz, 2H), 3.26-3.09 (m, 1H), 3.00 (s, 2H), 0.83 (t, J = 7.0 Hz, 3H).
LCMS Calculated for $C_{35}H_{31}F_4N_5O_5$: 677.23; Observed (Method-D): 678.3 [M + H]$^+$, 97.3% at RT 3.039 min.

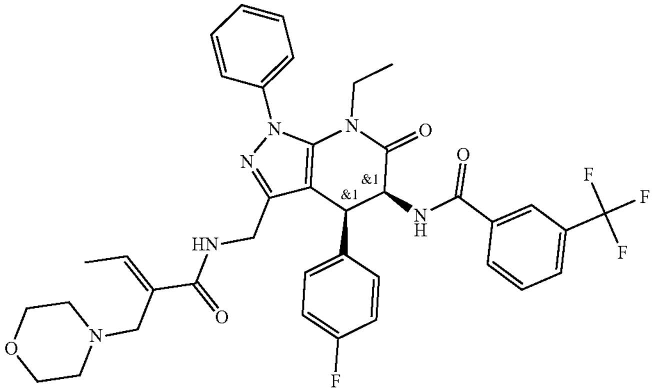 [SMILES: C/C=C(\CN1CCOCC1)C(=O)NCc1nn(-c2ccccc2)c2c1[C@H](c1ccc(F)cc1)[C@H](NC(=O)c1cccc(C(F)(F)F)c1)C(=O)N2CC]

I-14

$^1$H NMR (300 MHz, DMSO-$d_6$) δ 9.09 (s, 1H), 8.53 (d, J = 7.4 Hz, 1H), 8.14 (d, J = 9.4 Hz, 2H), 7.93 (d, J = 7.7 Hz, 1H), 7.77-7.64 (m, 3H), 7.63-7.49 (m, 3H), 7.08 (t, J = 8.8 Hz, 2H), 6.93 (t, J = 7.0 Hz, 2H), 6.55-6.37 (m, 1H), 5.51 (t, J = 7.3 Hz, 1H), 4.55 (d, J = 7.2 Hz, 1H), 4.32 (s, 1H), 4.20 (dd, J = 15.5, 4.4 Hz, 1H), 3.92 (dd, J = 14.4, 7.2 Hz, 1H), 3.13-2.96 (m, 2H), 2.98-2.85 (m, 1H), 2.31-2.10 (m, 4H), 1.67 (d, J = 7.2 Hz, 3H), 0.92 (t, J = 7.0 Hz, 3H).
LCMS Calculated for $C_{38}H_{38}F_4N_6O_4$: 718.29; Observed (Method-C): 719.2 [M + H]$^+$, 98.2% at RT 0.977 min.

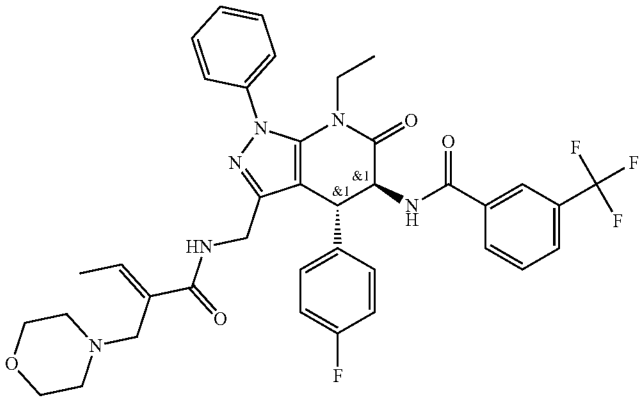 [SMILES: C/C=C(\CN1CCOCC1)C(=O)NCc1nn(-c2ccccc2)c2c1[C@@H](c1ccc(F)cc1)[C@H](NC(=O)c1cccc(C(F)(F)F)c1)C(=O)N2CC]

I-27

$^1$H NMR (300 MHz, DMSO-$d_6$) δ 9.16 (s, 1H), 9.01 (d, J = 8.8 Hz, 1H), 8.02 (s, 1H), 7.91 (d, J = 7.7 Hz, 1H), 7.63-7.54 (m, 6H), 7.43-7.40 (m, 2H), 7.17 (t, J = 8.6 Hz, 2H), 6.57-6.54 (m, 1H), 5.27-5.24 (m, 1H), 4.41 (d, J = 11.9 Hz, 1H), 3.71-3.68 (m, 2H), 3.52-3.35 (m, 4H), 3.10-3.08 (m, 1H), 2.30 (s, 4H), 1.72 (d, J = 7.2 Hz, 3H), 1.33-1.29 (m, 1H), 0.82 (t, J = 7.0 Hz, 3H).
LCMS Calculated for $C_{38}H_{38}F_4N_6O_4$: 718.29; Observed (Method-C): 719.2 [M + H]$^+$, 95.2% at RT 1.747 min.

-continued

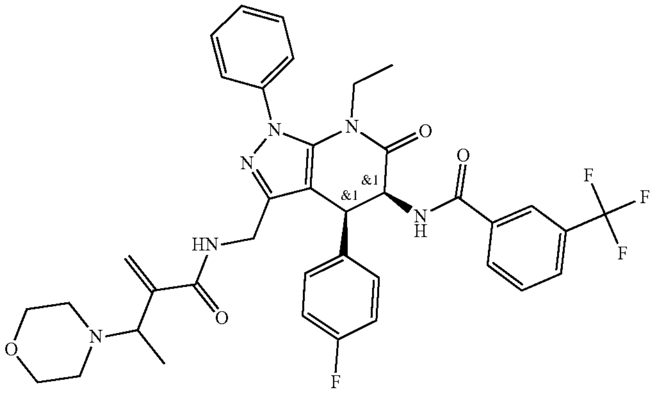 [SMILES: C=C(C(=O)NCc1nn(-c2ccccc2)c2c1[C@H](c1ccc(F)cc1)[C@H](NC(=O)c1cccc(C(F)(F)F)c1)C(=O)N2CC)C(C)N1CCOCC1]

I-89

$^1$H NMR (300 MHz, DMSO-$d_6$) δ 9.44 (d, J = 5.4 Hz, 1H), 8.54 (d, J = 3.3 Hz, 1H), 8.13-8.09 (m, 2H), 7.92 (d, J = 7.8 Hz, 1H), 7.80-7.64 (m, 3H), 7.65-7.48 (m, 3H), 7.18-7.03 (m, 2H), 6.96-6.92 (m, 2H), 5.75 (d, J = 2.6 Hz, 1H), 5.62-5.41 (m, 1H), 5.29 (s, 1H), 4.57-4.52 (m, 1H), 4.45-4.05 (m, 2H), 3.93-3.91 (m, 1H), 3.37-3.33 (m, 4H), 3.05-3.01 (m, 1H), 2.30-2.24 (m, 4H), 2.21-1.99 (m, 1H), 1.10-0.95 (m, 3H), 0.92 (t, J = 7.0 Hz, 3H).
LCMS Calculated for $C_{38}H_{38}F_4N_6O_4$: 718.29; Observed (Method-E): 719.2 $[M + H]^+$, 93.7% at RT 1.449 min.

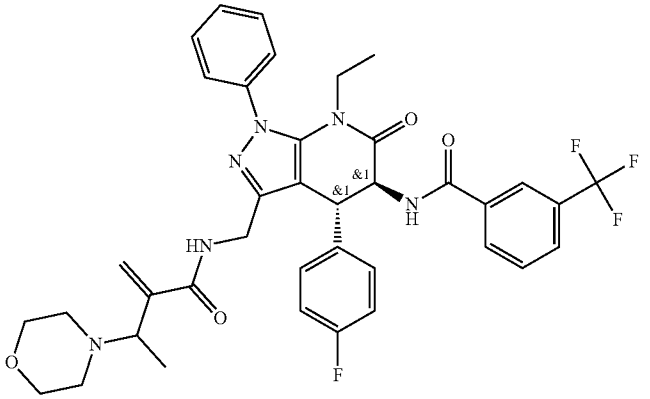 [SMILES: C=C(C(=O)NCc1nn(-c2ccccc2)c2c1[C@@H](c1ccc(F)cc1)[C@H](NC(=O)c1cccc(C(F)(F)F)c1)C(=O)N2CC)C(C)N1CCOCC1]

I-88

$^1$H NMR (300 MHz, DMSO-$d_6$) : 9.42 (d, J = 14.7 Hz, 1H), 9.01 (d, J = 6.2 Hz, 1H), 8.02-7.99 (m, 2H), 7.91 (d, J = 7.8 Hz, 1H), 7.71 (t, J = 8.0 Hz, 1H), 7.65-7.48 (m, 5H), 7.43-7.40 (m, 2H), 7.18 (t, J = 8.7 Hz, 2H), 5.94-5.75 (m, 1H), 5.41-5.14 (m, 2H), 4.42-4.38 (m, 1H), 3.97-3.34 (m, 6H), 3.13-3.11 (m, 2H), 2.55-2.51 (m, 1H), 2.37-2.34 (m, 2H), 2.29-2.25 (m, 2H), 1.24-1.21 (m, 1H), 1.10 (dd, J = 10.4, 6.7 Hz, 3H), 0.82 (t, J = 7.0 Hz, 3H).
LCMS Calculated for $C_{38}H_{38}F_4N_6O_4$: 718.29; Observed (Method-E): 719.2 $[M + H]^+$, 93.3% at RT 1.379 min.

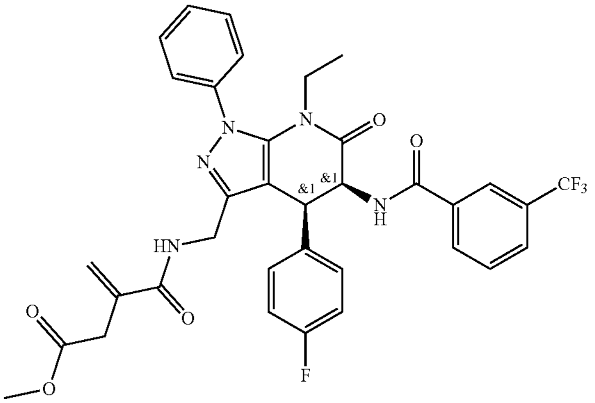 [SMILES: C=C(CC(=O)OC)C(=O)NCc1nn(-c2ccccc2)c2c1[C@H](c1ccc(F)cc1)[C@H](NC(=O)c1cccc(C(F)(F)F)c1)C(=O)N2CC]

I-17

$^1$H NMR (400 MHz, DMSO-$d_6$) δ 8.50 (d, J = 7.4 Hz, 1H), 8.36 (t, J = 5.9 Hz, 1H), 8.20-8.12 (m, 2H), 7.93 (d, J = 7.8 Hz, 1H), 7.73 (d, J = 7.8 Hz, 1H), 7.68 (d, J = 7.9 Hz, 2H), 7.60 (t, J = 7.5 Hz, 2H), 7.55 (d, J = 7.2 Hz, 1H), 7.05 (t, J = 8.8 Hz, 2H), 6.88 (dd, J = 8.5, 5.5 Hz, 2H), 5.50 (t, J = 7.3 Hz, 1H), 5.38 (s, 1H), 5.23 (s, 1H), 4.55 (d, J = 7.2 Hz, 1H), 4.40 (dd, J = 15.2, 6.6 Hz, 1H), 4.14 (dd, J = 15.2, 5.1 Hz, 1H), 3.92-3.87 (m, 1H), 3.52 (s, 3H), 3.09 (s, 1H), 3.06-2.99 (m, 2H), 0.91 (t, J = 7.0 Hz, 3H).
LCMS Calculated for $C_{35}H_{31}F_4N_5O_5$: 677.23; Observed (Method-D): 678.5 $[M + H]^+$, 97.9% at RT 1.674 min.

-continued

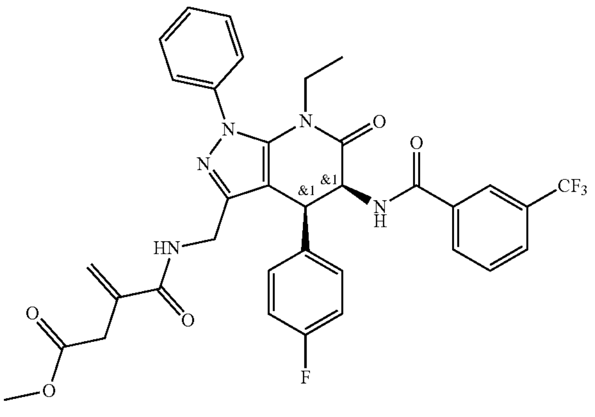 [SMILES: C=C(CC(=O)OC)C(=O)NCc1nn(-c2ccccc2)c2c1[C@H](c1ccc(F)cc1)[C@H](NC(=O)c1cccc(C(F)(F)F)c1)C(=O)N2CC]

I-103

$^1$H NMR (400 MHz, DMSO-$d_6$) δ 9.06 (d, J = 8.7 Hz, 1H), 8.10 (t, J = 6.8 Hz,, 1H), 8.02 (d, J = 6.7 Hz, 2H), 7.92 (d, J = 7.8 Hz, 1H), 7.73 (d, J = 8.1 Hz, 1H), 7.66 (d, J = 7.7 Hz, 2H), 7.59 (t, J = 7.6 Hz, 2H), 7.53 (d, J = 7.3 Hz, 1H), 7.39 (dd, J = 8.1, 5.2 Hz, 2H), 7.13 (t, J = 8.6 Hz, 2H), 5.74 (s, 1H), 5.44 (s, 1H), 5.20 (t, J = 9.7 Hz, 1H), 4.44 (d, J = 10.8 Hz, 1H), 3.61 (s, 3H), 3.53 (s, 3H), 3.28-3.20 (m, 1H), 3.18 (s, 2H), 0.82 (t, J = 7.0 Hz, 3H). LCMS Calculated for $C_{35}H_{31}F_4N_5O_5$: 677.23; Observed (Method-E): 678.5 $[M + H]^+$, 97.9% at RT 1.674 min.

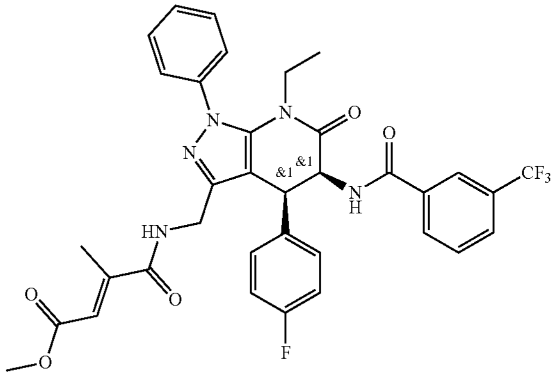 [SMILES: CCN1C(=O)[C@@H](NC(=O)c2cccc(C(F)(F)F)c2)[C@@H](c2ccc(F)cc2)c2c(CNC(=O)/C(C)=C/C(=O)OC)nn(-c3ccccc3)c21]

I-155

$^1$H NMR (400 MHz, DMSO-$d_6$) δ 8.51 (d, J = 7.1 Hz, 2H), 8.21-8.12 (m, 2H), 7.93 (d, J = 7.8 Hz, 1H), 7.71-7.66 (m, 3H), 7.63-7.53 (m, 3H), 7.01 (t, J = 8.7 Hz, 2H), 6.85 (t, J = 7.1 Hz, 2H), 5.79 (d, J = 1.6 Hz, 1H), 5.49 (t, J = 7.2 Hz, 1H), 4.58-4.48 (m, 2H), 4.16-4.12 (m, 1H), 3.98-3.88 (m, 1H), 3.63 (s, 3H), 3.02-2.99 (m, 1H), 1.87 (d, J = 1.5 Hz, 3H), 0.91 (t, J = 7.1 Hz, 3H). LCMS Calculated for $C_{35}H_{31}F_4N_5O_5$: 677.23; Observed (Method-D): 678.5 $[M + H]^+$, 96.4% at RT 2.003 min.

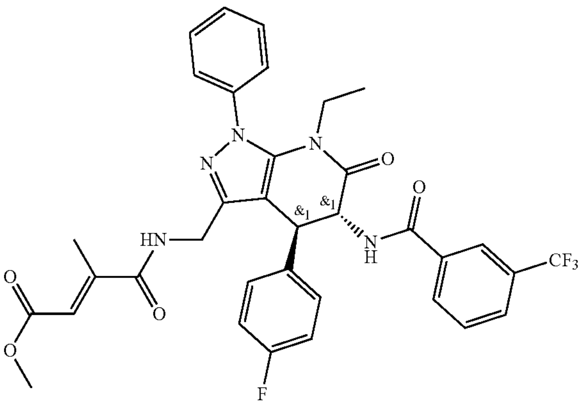 [SMILES: CCN1C(=O)[C@H](NC(=O)c2cccc(C(F)(F)F)c2)[C@@H](c2ccc(F)cc2)c2c(CNC(=O)/C(C)=C/C(=O)OC)nn(-c3ccccc3)c21]

I-108

$^1$H NMR (400 MHz, DMSO-$d_6$) δ 9.08 (d, J = 8.5 Hz, 1H), 8.32 (d, J = 5.5 Hz, 1H), 8.03 (d, J = 6.5 Hz, 2H), 7.92 (d, J = 7.7 Hz, 1H), 7.73 (d, J = 7.9 Hz, 1H), 7.67 (d, J = 7.7 Hz, 2H), 7.60 (t, J = 7.6 Hz, 2H), 7.54 (d, J = 7.2 Hz, 1H), 7.37 (dd, J = 8.5, 5.4 Hz, 2H), 7.13 (t, J = 8.7 Hz, 2H), 6.13 (d, J = 1.7 Hz, 1H), 5.19-5.14 (m, 1H), 4.45 (d, J = 10.2 Hz, 1H), 3.68-3.65 (m, 5H), 3.59-3.56 (m, 1H), 3.30-3.24 (m, 1H), 2.06 (d, J = 1.5 Hz, 3H), 0.82 (t, J = 7.0 Hz, 3H). LCMS Calculated for $C_{35}H_{31}F_4N_5O_5$: 677.23; Observed (Method-D): 678.5 $[M + H]^+$, 96.8% at RT 2.003 min.

-continued

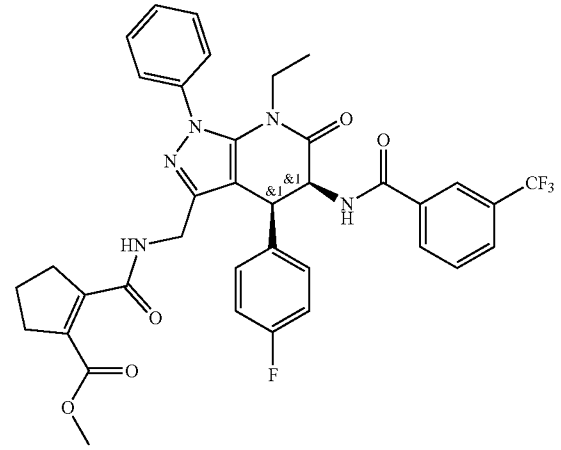 [SMILES: CCN1C(=O)[C@@H](NC(=O)c2cccc(C(F)(F)F)c2)[C@@H](c2ccc(F)cc2)c2c(CNC(=O)C3=C(C(=O)OC)CCC3)nn(-c3ccccc3)c21]

$^1$H NMR (300 MHz, Chloroform-d) δ 8.88 (s, 1H), 8.05 (s, 1H), 7.91 (d, J = 7.8 Hz, 1H), 7.81 (d, J = 7.8 Hz, 1H), 7.66-7.48 (m, 6H), 6.95-6.78 (m, 5H), 5.30 (t, J = 6.7 Hz, 1H), 4.82 (d, J = 7.2 Hz, 1H), 4.77-4.64 (m, 1H), 4.47-4.34 (m, 1H), 4.07-3.89 (m, 1H), 3.73 (s, 3H), 3.30-3.13 (m, 1H), 2.69 (t, J = 7.7 Hz, 4H), 1.80 (s, 2H), 1.03 (t, J = 7.1 Hz, 3H).
LCMS Calculated for $C_{37}H_{33}F_4N_5O_5$, 703.24; Observed (Method-E): 704.5 $[M + H]^+$, 99.0% at RT 1.291 min.

I-135

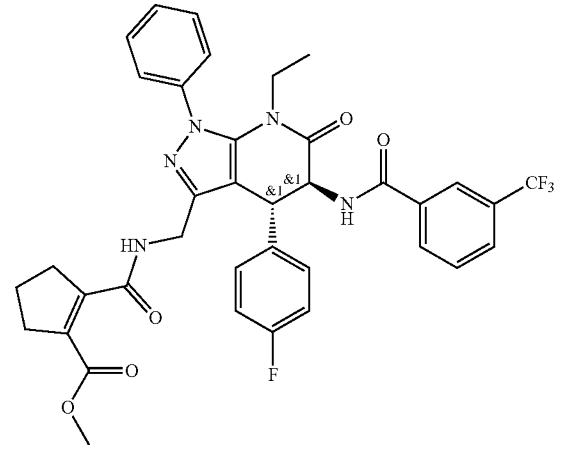 [SMILES: CCN1C(=O)[C@@H](NC(=O)c2cccc(C(F)(F)F)c2)[C@H](c2ccc(F)cc2)c2c(CNC(=O)C3=C(C(=O)OC)CCC3)nn(-c3ccccc3)c21]

$^1$H NMR (400 MHz, DMSO-$d_6$) δ 9.04 (d, J = 8.7 Hz, 1H), 8.12 (s, 1H), 8.02 (d, J = 6.5 Hz, 2H), 7.92 (d, J = 7.8 Hz, 1H), 7.70-7.65 (m, 3H), 7.64-7.51 (m, 3H), 7.44-7.36 (m, 2H), 7.16 (t, J = 8.7 Hz, 2H), 5.24-5.15 (m, 1H), 4.45 (d, J = 11.0 Hz, 1H), 3.66-3.63 (m, 1H), 3.62 (d, J = 5.3 Hz, 2H), 3.56 (s, 3H), 3.28-3.18 (m, 1H), 2.57-2.54 (m, 4H), 1.84-1.76 (m, 2H), 0.82 (t, J = 7.0 Hz, 3H).
LCMS Calculated for $C_{37}H_{33}F_4N_5O_5$: 703.24; Observed (Method-D): 704.5 $[M + H]^+$, 94.7% at RT 1.854 min.

I-71

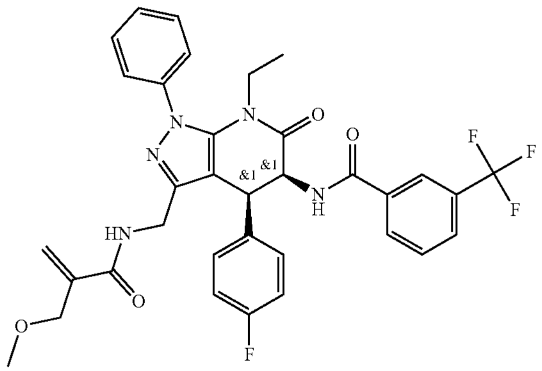 [SMILES: C=C(COC)C(=O)NCc1nn(-c2ccccc2)c2c1[C@H](c1ccc(F)cc1)[C@H](NC(=O)c1cccc(C(F)(F)F)c1)C(=O)N2CC]

$^1$H NMR (300 MHz, DMSO-$d_6$) δ 8.50 (d, J = 7.3 Hz, 1H), 8.26-8.11 (m, 3H), 7.93 (d, J = 7.8 Hz, 1H), 7.78-7.65 (m, 3H), 7.64-7.49 (m, 3H), 7.05 (t, J = 8.9 Hz, 2H), 6.94-6.84 (m, 2H), 5.49 (t, J = 7.2 Hz, 1H), 5.43 (d, J = 1.3 Hz, 1H), 5.26 (q, J = 1.5 Hz, 1H), 4.58 (d, J = 7.1 Hz, 1H), 4.40 (dd, J = 15.2, 6.6 Hz, 1H), 4.16 (dd, J = 15.2, 5.2 Hz, 1H), 3.98-3.84 (m, 1H), 3.77 (d, J = 1.5 Hz, 2H), 3.17 (s, 3H), 3.03 (dd, J = 14.2, 7.1 Hz, 1H), 0.91 (t, J = 7.0 Hz, 3H).
LCMS Calculated for $C_{34}H_{31}F_4N_5O_4$: 649.23; Observed (Method-C): 650.3 $[M + H]^+$ 97.5% at RT 1.258 min.

I-113

-continued

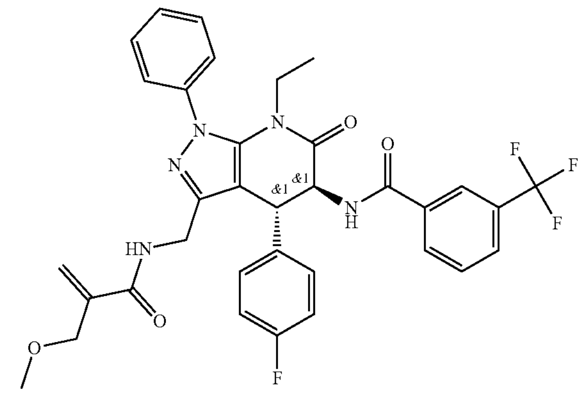 [SMILES: C=C(COC)C(=O)NCc1nn(-c2ccccc2)c2c1[C@@H](c1ccc(F)cc1)[C@H](NC(=O)c1cccc(C(F)(F)F)c1)C(=O)N2CC]

I-109

$^1$H NMR (400 MHz, DMSO-$d_6$) δ 9.03 (d, J = 8.6 Hz, 1H), 8.00 (d, J = 6.6 Hz, 2H), 7.95 (t, J = 5.1 Hz, 1H), 7.89 (d, J = 7.8 Hz, 1H), 7.69 (t, J = 8.0 Hz, 1H), 7.66-7.63 (m, 2H), 7.57 (t, J = 7.6 Hz, 2H), 7.52-7.50 (m, 1H), 7.39-7.34 (m, 2H), 7.12 (t, J = 8.8 Hz, 2H), 5.69 (d, J = 1.3 Hz, 1H), 5.41 (d, J = 1.5 Hz, 1H), 5.18 (dd, J = 10.8, 8.6 Hz, 1H), 4.42 (d, J = 10.7 Hz, 1H), 3.91 (d, J = 1.2 Hz, 2H), 3.68-3.54 (m, 3H), 3.23 (dd, J = 14.1, 7.1 Hz, 1H), 3.19 (s, 3H), 0.80 (t, J = 7.0 Hz, 3H). LCMS Calculated for $C_{34}H_{31}F_4N_5O_4$: 649.23; Observed (Method-D): 650.3 $[M + H]^+$ 98.7% at RT 1.807 min.

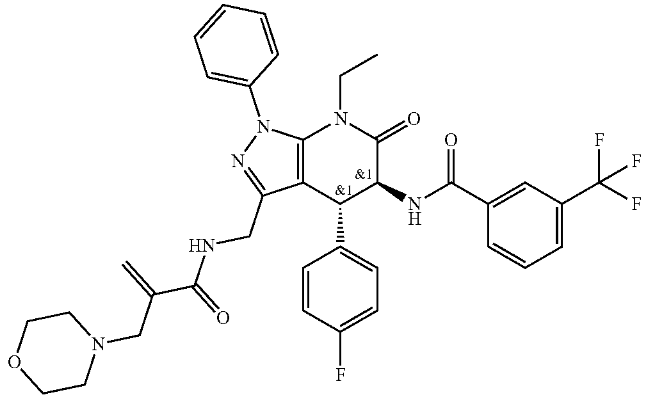 [SMILES: C=C(CN1CCOCC1)C(=O)NCc1nn(-c2ccccc2)c2c1[C@@H](c1ccc(F)cc1)[C@H](NC(=O)c1cccc(C(F)(F)F)c1)C(=O)N2CC]

I-58

$^1$H NMR (400 MHz, DMSO-$d_6$) δ 9.21 (t, J = 4.7 Hz, 1H), 9.01 (d, J = 8.8 Hz, 1H), 8.01 (d, J = 5.8 Hz, 2H), 7.91 (d, J = 7.8 Hz, 1H), 7.71 (t, J = 8.0 Hz, 1H), 7.67-7.64 (m, 2H), 7.59 (t, J = 7.5 Hz, 2H), 7.56-7.51 (m, 1H), 7.42 (dd, J = 8.6, 5.4 Hz, 2H), 7.17 (t, J = 8.9 Hz, 2H), 5.86 (d, J = 2.3 Hz, 1H), 5.38 (s, 1H), 5.27 (dd, J = 11.9, 8.8 Hz, 1H), 4.42 (d, J = 12.0 Hz, 1H), 3.75 (dd, J = 14.3, 7.2 Hz, 2H), 3.67-3.64 (m, 1H), 3.47-3.35 (m, 4H), 3.10-3.08 (m, 3H), 2.28-2.35 (m, 4H), 0.81 (t, J = 7.0 Hz, 3H). LCMS Calculated for $C_{37}H_{36}F_4N_6O_4$: 704.27; Observed (Method-D): 705.3 $[M + H]^+$, 95.0% at RT 1.426 min.

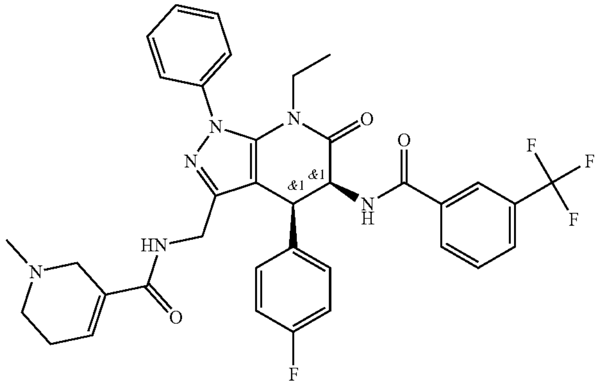 [SMILES: CCN1C(=O)[C@@H](NC(=O)c2cccc(C(F)(F)F)c2)[C@@H](c2ccc(F)cc2)c2c(CNC(=O)C3=CCCN(C)C3)nn(-c3ccccc3)c21]

I-28

$^1$H NMR (400 MHz, DMSO-$d_6$) δ 8.50 (d, J = 6.8 Hz, 1H), 8.25-8.08 (m, 2H), 7.94 (d, J = 7.8 Hz, 2H), 7.81-7.46 (m, 6H), 7.04 (t, J = 8.6 Hz, 2H), 6.93-6.75 (m, 2H), 6.04 (s, 1H), 5.49 (t, J = 7.1 Hz, 1H), 4.63-4.38 (m, 2H), 4.19-4.03 (m, 1H), 3.89 (q, J = 8.0 Hz, 1H), 3.04-2.99 (m, 1H), 2.71 (d, J = 16.6 Hz, 1H), 2.20 (d, J = 26.8 Hz, 5H), 2.01 (s, 2H), 0.91 (t, J = 6.8 Hz, 3H). LCMS Calculated for $C_{36}H_{34}F_4N_6O_3$: 674.26; Observed (Method-C): 675.2 $[M + H]^+$ 97.4% at RT 1.679 min.

Synthesis of rac-N-((4R, 5R)-7-ethyl-4-(4-fluorophenyl)-3-(((1-methylvinyl)sulfonamido)methyl)-6-oxo-1-phenyl-4,5,6,7-tetrahydro-1H-pyrazolo[3,4-b]pyridin-5-yl)-3-(trifluoromethyl)benzamide (I-54)

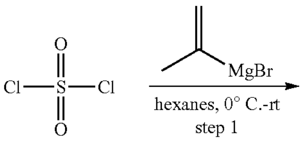

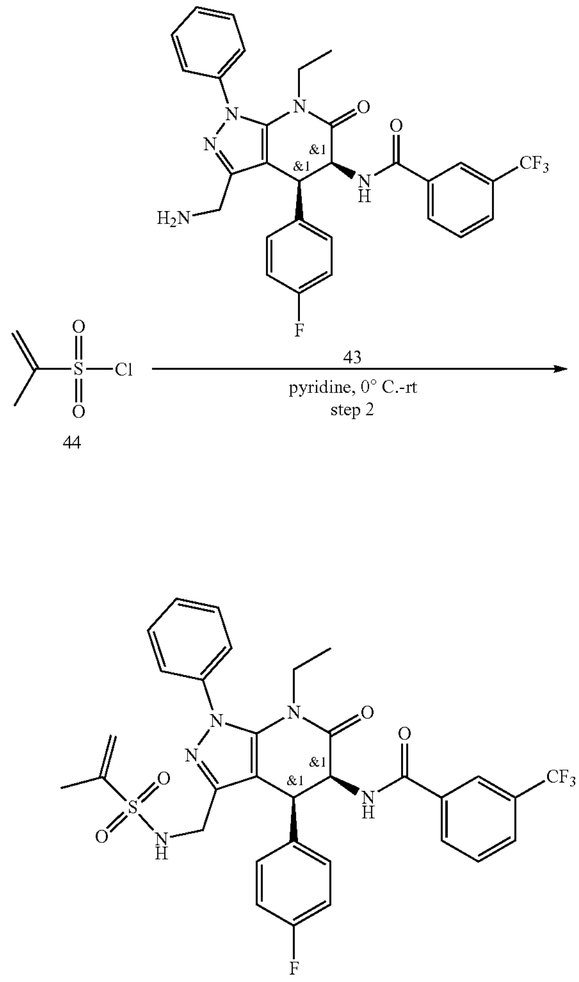

I-54 prop-1-ene-2-sulfonyl chloride (44)

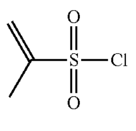

To a solution of sulfonyl chloride (2.00 g, 14.8 mmol, 2.00 equiv) in hexane (20 mL) was added prop-1-ene-2-sulfonyl chloride (20 mL, 0.5M in hexane) dropwise at 0° C. The resulting mixture was stirred for 16 h at room temperature. The reaction was quenched by the addition of ice water (10 mL) at 0° C. The resulting mixture was extracted with hexane (2×10 mL). The combined organic layers were washed with brine (1×20 mL), dried over anhydrous $Na_2SO_4$. The mixture was used in the next step directly without further purification.

rac-N-((4R,5R)-7-ethyl-4-(4-fluorophenyl)-3-(((1-methylvinyl)sulfonamido)methyl)-6-oxo-1-phenyl-4,5,6,7-tetrahydro-1H-pyrazolo[3,4-b]pyridin-5-yl)-3-(trifluoromethyl)benzamide (I-54)

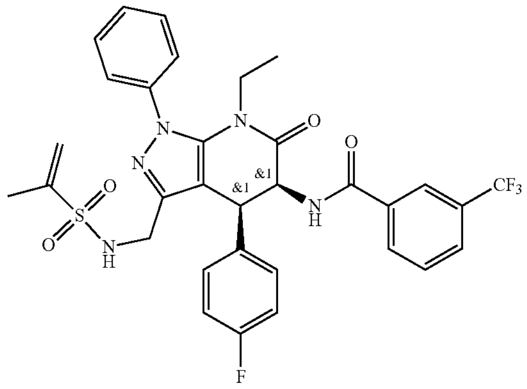

Into a 8 mL vial were added rac-N-((4R,5R)-3-(aminomethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (100 mg, 0.181 mmol, 1.00 equiv) and Pyridine (1.00 mL) at 25° C. To the above mixture was added prop-1-ene-2-sulfonyl chloride (3 ml, solution in hexane) dropwise over 2 min at 0° C. The resulting mixture was stirred for additional 30 min at 25° C. The reaction was quenched with water at 0° C. The resulting mixture was filtered, the filter cake was washed with MeCN (2×1 mL). The filtrate was concentrated under reduced pressure. The residue was purified by reversed-phase flash chromatography with the following conditions: Xselect CSH OBD C18 Column, 30*150 mm, 5 μm, Mobile Phase A: Water (0.1% FA), Mobile Phase B: ACN; Flow rate: 60 mL/min; Gradient: 50% B to 70% B in 7.4 min; This resulted in rac-N-((4R,5R)-7-ethyl-4-(4-fluorophenyl)-3-(((1-methylvinyl) sulfonamido)methyl)-6-oxo-1-phenyl-4,5,6,7-tetrahydro-1H-pyrazolo[3,4-b]pyridin-5-yl)-3-(trifluoromethyl)benzamide (7 mg, 5%) as a white solid.

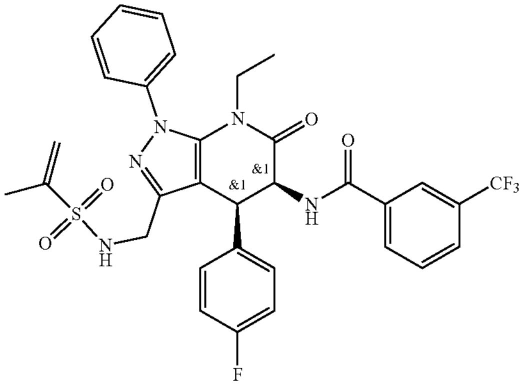 [SMILES: C=C(C)S(=O)(=O)NCc1nn(-c2ccccc2)c2c1[C@H](c1ccc(F)cc1)[C@H](NC(=O)c1cccc(C(F)(F)F)c1)C(=O)N2CC]

$^1$H NMR (400 MHz, Chloroform-d) δ 8.05 (s, 1H), 7.90 (d, J = 7.8 Hz, 1H), 7.82 (d, J = 7.8 Hz, 1H), 7.66-7.49 (m, 6H), 7.00-6.94 (m, 5H), 6.03 (d, J = 1.0 Hz, 1H), 5.62 (d, J = 1.6 Hz, 1H), 5.25 (dd, J = 7.3, 5.8 Hz, 1H), 4.93-4.69 (m, 2H), 4.16 (dd, J = 14.8, 5.5 Hz, 1H), 4.10-3.96 (m, 2H), 3.22 (dd, J = 14.2, 7.0 Hz, 1H), 2.03 (t, J = 1.1 Hz, 3H), 1.04 (t, J = 7.1 Hz, 3H). LCMS Calculated for $C_{32}H_{29}F_4N_5O_4S$: 655.19; Observed (Method-E): 656.4 $[M + H]^+$, 96.4% at RT 1.268 min.

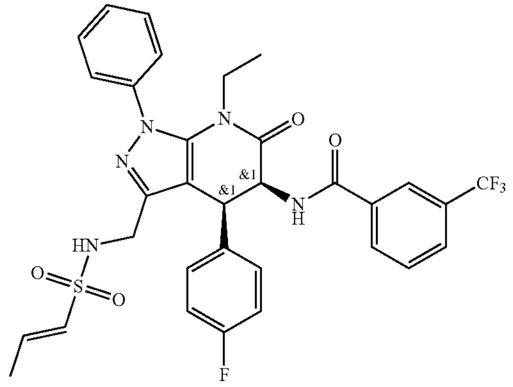 [SMILES: C/C=C/S(=O)(=O)NCc1nn(-c2ccccc2)c2c1[C@H](c1ccc(F)cc1)[C@H](NC(=O)c1cccc(C(F)(F)F)c1)C(=O)N2CC]

$^1$H NMR (400 MHz, Chloroform-d) δ 8.06 (s, 1H), 7.90 (d, J = 7.8 Hz, 1H), 7.82 (d, J = 7.8 Hz, 1H), 7.67-7.47 (m, 6H), 6.99 (dd, J = 8.0, 5.3 Hz, 5H), 6.77 (dq, J = 13.9, 6.9 Hz, 1H), 6.21-6.08 (m, 1H), 5.33-5.16 (m, 1H), 4.92-4.67 (m, 2H), 4.26-4.05 (m, 2H), 4.01 (dd, J = 14.3, 7.2 Hz, 1H), 3.22 (dd, J = 14.2, 7.1 Hz, 1H), 2.08 (dd, J = 7.3, 1.8 Hz, 1H), 1.91 (dd, J = 6.9, 1.7 Hz, 2H), 1.03 (t, J = 7.0 Hz, 3H). LCMS Calculated for $C_{32}H_{29}F_4N_5O_4S$: 655.19; Observed (Method-E): 656.5 $[M + H]^+$, 99.3% at RT 1.264 min.

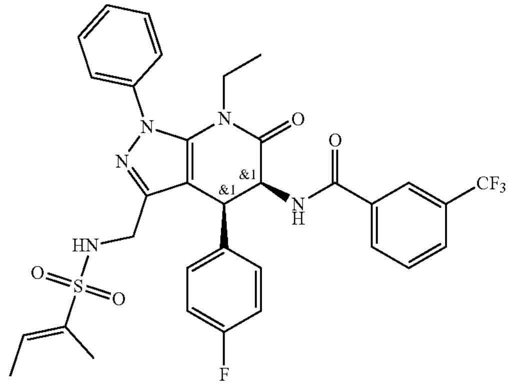 [SMILES: C/C=C(\C)S(=O)(=O)NCc1nn(-c2ccccc2)c2c1[C@H](c1ccc(F)cc1)[C@H](NC(=O)c1cccc(C(F)(F)F)c1)C(=O)N2CC]

$^1$H NMR (300 MHz, DMSO-$d_6$) δ 8.55 (d, J = 7.6 Hz, 1H), 8.14-8.11 (m, 2H), 7.93 (d, J = 8.0 Hz, 1H), 7.84-7.40 (m, 8H), 7.12 (t, J = 8.8 Hz, 2H), 7.00-6.94 (m, 2H), 6.03 (d, J = 7.3 Hz, 1H), 5.52 (t, J = 7.4 Hz, 1H), 4.71 (d, J = 7.3 Hz, 1H), 4.09-3.84 (m, 2H), 3.82-3.67 (m, 1H), 3.05-3.01 (m, 1H), 1.92-1.86 (m, 3H), 1.86-1.76 (m, 3H), 0.91 (t, J = 7.0 Hz, 3H). LCMS Calculated for $C_{33}H_{31}F_4N_5O_4S$: 669.20; Observed (Method-C): 670.1 $[M + H]^+$, 99.8% at RT 1.343 min.

Synthesis of rac-N-((4R, 5R)-7-ethyl-4-(4-fluorophenyl)-3-((2-(hydroxymethyl)acrylamido)methyl)-6-oxo-1-phenyl-4,5,6,7-tetrahydro-1H-pyrazolo[3,4-b]pyridin-5-yl)-3-(trifluoromethyl)benzamide (I-116)

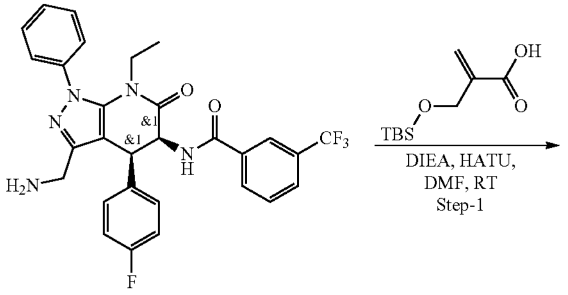

43

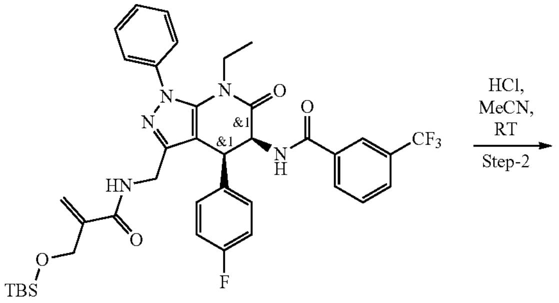

I-49

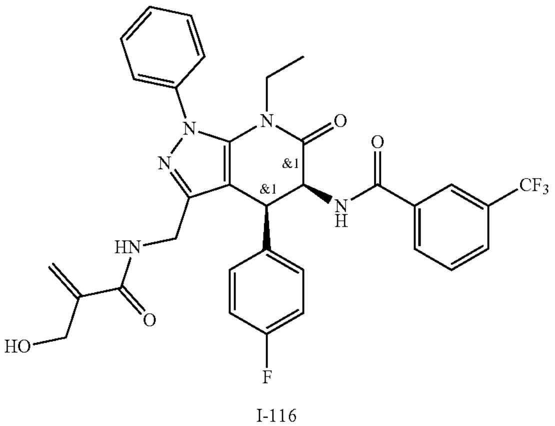

I-116 rac-N-((4R,5R)-3-((2-(((tert-butyldimethlsilyl)oxy)methyl)acrylamido)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (44)

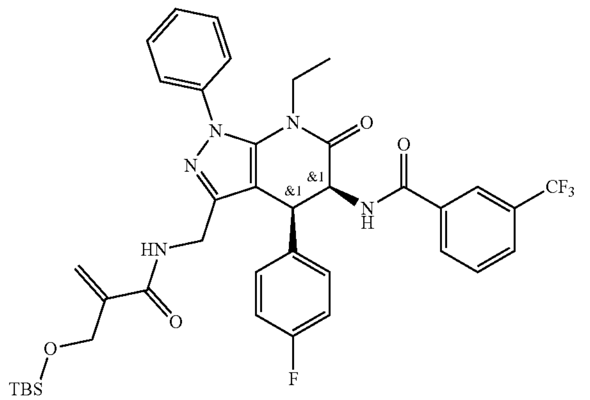

A mixture of rac-N-((4R,5R)-3-(aminomethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (150 mg, 0.272 mmol, 1.00 equiv), 2-(((tert-butyldimethylsilyl)oxy)methyl) acrylic acid (58.8 mg, 0.272 mmol, 1.00 equiv) and DIEA (105 mg, 0.816 mmol, 3.00 equiv) in DCM (20 mL) was stirred at room temperature for 10 min. HATU (124 mg, 0.326 mmol, 1.20 equiv) was then added, and the reaction mixture was stirred for 1 hour at room temperature. The resulting mixture was concentrated in vacuum and the residue was purified by prep-HPLC ($NH_3 \cdot H_2O$ buffer) to give rac-N-((4R,5R)-3-((2-(((tert-butyldimethylsilyl)oxy)methyl)acrylamido)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (200 mg, 98%) as a white solid.

rac-N-((4R,5R)-7-ethyl-4-(4-fluorophenyl)-3-((2-hydroxymethyl)acrylamido)methyl)-6-oxo-1-phenyl-4,5,6,7-tetrahydro-1H-pyrazolo[3,4-b]pyridin-5-yl)-3-(trifluoromethyl)benzamide (I-116)

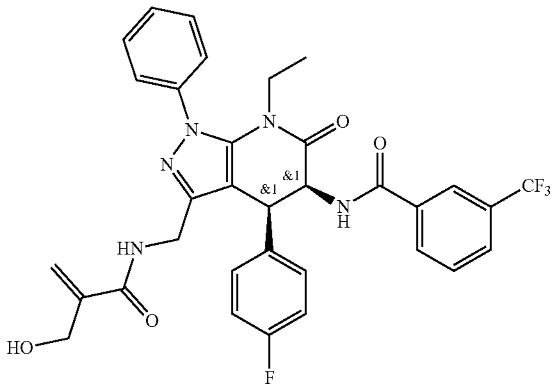 [SMILES: C=C(CO)C(=O)NCc1nn(-c2ccccc2)c2c1[C@H](c1ccc(F)cc1)[C@H](NC(=O)c1cccc(C(F)(F)F)c1)C(=O)N2CC]

A mixture of rac-N-((4R,5R)-3-((2-(((tert-butyldimethylsilyl)oxy)methyl)acrylamido)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (180 mg, 0.240 mmol, 1.00 equiv) and HCl (0.5 mL) in ACN (5 mL) was stirred for 2 hours at room temperature. The resulting mixture was concentrated in vacuum, the residue was purified by prep-HPLC ($NH_3 \cdot H_2O$ buffer) to give rac-N-((4R,5R)-7-ethyl-4-(4-fluorophenyl)-3-((2-(hydroxymethyl)acrylamido)methyl)-6-oxo-1-phenyl-4,5,6,7-tetrahydro-1H-pyrazolo[3,4-b]pyridin-5-yl)-3-(trifluoromethyl)benzamide (120 mg, 75%) as a white solid.

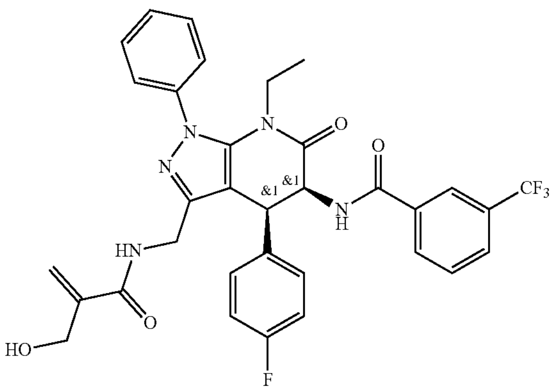

$^1$H NMR (300 MHz, DMSO-$d_6$) δ 8.51 (d, J = 7.4 Hz, 1H), 8.36-8.06 (m, 3H), 7.93 (d, J = 7.8 Hz, 1H), 7.82-7.43 (m, 6H), 7.05 (t, J = 8.8 Hz, 3H), 6.97-6.82 (m, 2H), 5.50 (t, J = 7.3 Hz, 1H), 5.38 (d, J = 1.5 Hz, 1H), 5.28 (d, J = 1.8 Hz, 1H), 4.86-4.83 (m, 1H), 4.59 (d, J = 7.2 Hz, 1H), 4.38-4.33 (m, 1H), 4.16-4.12 (m, 1H), 3.94-3.92 (m, 1H), 3.89 (d, J = 8.2 Hz, 2H), 3.03-3.01 (m, 1H), 0.91 (t, J = 7.0 Hz, 3H).
LCMS Calculated for $C_{33}H_{29}F_4N_5O_4$: 635.22; Observed (Method-E): 636.5 $[M + H]^+$ 99.9% at RT 1.106 min.

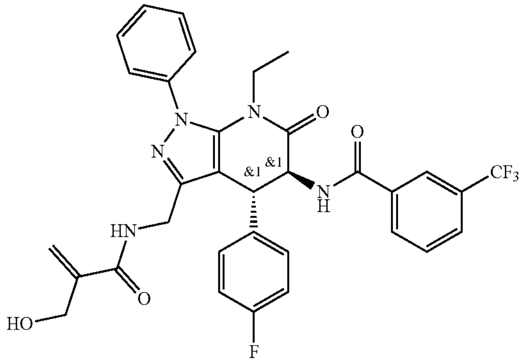 [SMILES: C=C(CO)C(=O)NCc1nn(-c2ccccc2)c2c1[C@@H](c1ccc(F)cc1)[C@H](NC(=O)c1cccc(C(F)(F)F)c1)C(=O)N2CC]

$^1$H NMR (300 MHz, DMSO-$d_6$) δ 9.05 (d, J = 8.6 Hz, 1H), 8.02 (d, J = 6.3 Hz, 2H), 7.92 (d, J = 8.9 Hz, 2H), 7.78-7.63 (m, 3H), 7.57-7.41 (m, 3H), 7.40-7.24 (m, 2H), 7.14 (t, J = 8.6 Hz, 2H), 5.65 (s, 1H), 5.42 (s, 1H), 5.30-5.16 (m, 1H), 5.01 (t, J = 5.5 Hz, 1H), 4.45 (d, J = 11.1 Hz, 1H), 4.01-3.94 (m, 3H), 3.73-3.54 (m, 2H), 3.22 (q, J = 7.1 Hz, 1H), 0.82 (t, J = 7.0 Hz, 3H).
LCMS Calculated for $C_{33}H_{29}F_4N_5O_4$: 635.22; Observed (Method-AR): 636.3 $[M + H]^+$, 97.02% at 1.026 min.

Synthesis of rac-N-((4R, 5R)-3-((2-(azetidin-1-ylmethyl)acrylamido)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-49)

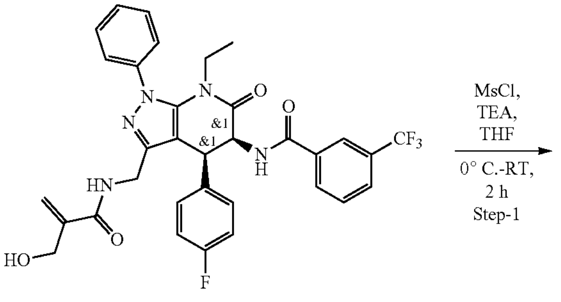

I-116

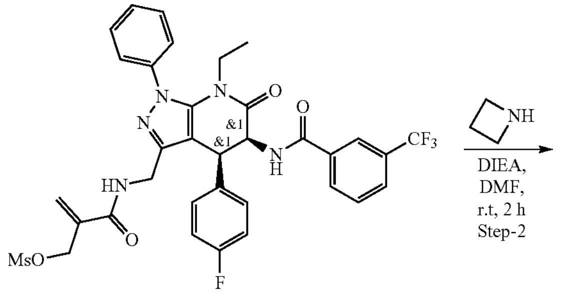

45

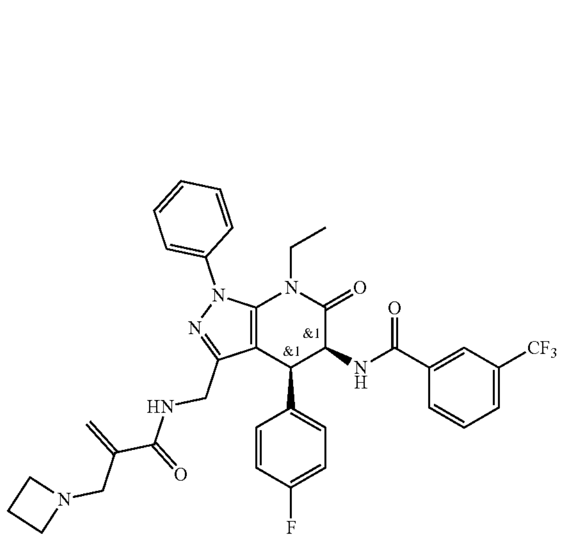

I-49 rac-2-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)carbamoyl)allyl methanesulfonate (45)

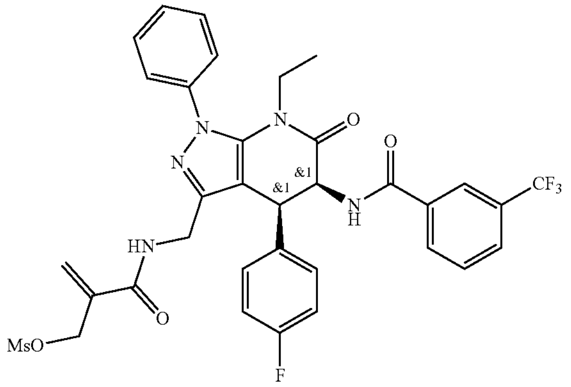

Into a 8 mL vial was placed rac-N-((4R,5R)-7-ethyl-4-(4-fluorophenyl)-3-((2-(hydroxymethyl)acrylamido) methyl)-6-oxo-1-phenyl-4,5,6,7-tetrahydro-1H-pyrazolo[3,4-b]pyridin-5-yl)-3-(trifluoromethyl)benzamide (50.0 mg, 0.079 mmol, 1.00 equiv) and TEA (15.9 mg, 0.158 mmol, 2.0 equiv) in DCM (5 mL) was added MsCl (13.5 mg, 0.118 mmol, 1.50 equiv) at 0° C. the reaction mixture was stirred for 2 hours at room temperature. The resulting mixture was diluted with water (10 mL) and extracted with ethyl acetate (20 mL×3). The combined organic phase was washed with brine (50 mL), dried over anhydrous sodium sulfate, filtered and concentrated in vacuum to afford rac-2-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b] pyridin-3-yl)methyl) carbamoyl) allyl methanesulfonate (50.0 mg, 89%) as a yellow solid.

rac-N-((4R,5R)-3-((2-(azetidin-1-ylmethyl)acrylamido)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-49)

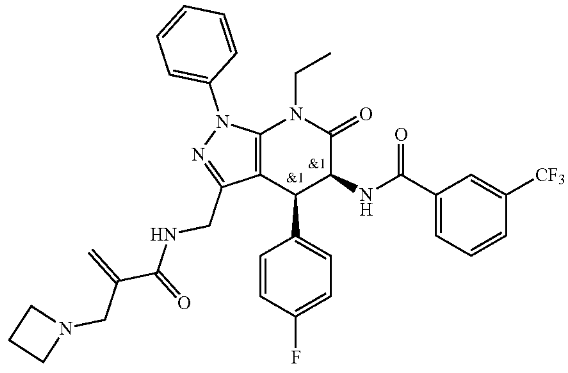

A mixture of rac-2-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl) carbamoyl) allyl methanesulfonate (50.0 mg, 0.07 mmol, 1.00 equiv), azetidine (4.80 mg, 0.084 mmol, 1.20 equiv) and DIEA (27.2 mg, 0.210 mmol, 3.00 equiv) in DMF (5 mL) was stirred for 2 hours at room temperature. The resulting mixture was purified by prep-HPLC ($NH_3 \cdot H_2O$ buffer) to give rac-N-((4R,5R)-3-((2-(azetidin-1-ylmethyl)acrylamido)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (15 mg, 31%) as a white solid. $^1$H NMR (300 MHZ, DMSO-$d_6$) δ 8.76 (t, J=5.8 Hz, 1H), 8.52 (d, J=7.4 Hz, 1H), 8.15-8.13 (m, 2H), 7.93 (d, J=7.9 Hz, 1H), 7.85-7.42 (m, 6H), 7.07 (t, J=8.7 Hz, 2H), 6.92-6.89 (m, 2H), 5.62-5.40 (m, 2H), 5.22 (s, 1H), 4.57 (d, J=7.2 Hz, 1H), 4.39-4.36 (m, 1H), 4.18-4.15 (m, 1H), 4.05-3.77 (m, 1H), 3.07 (d, J=7.2 Hz, 1H), 3.01-2.99 (m, 4H), 2.94-2.71 (m, 2H), 1.88-1.85 (m, 2H), 0.92 (t, J=7.0 Hz, 3H).

LCMS Calculated for $C_{36}H_{34}F_4N_6O_3$: 674.26; Observed (Method-C): 675.1 $[M+H]^+$, 99.2% at RT 0.899 min.

Following compounds were prepared according to I-49.

| | |
|---|---|
| 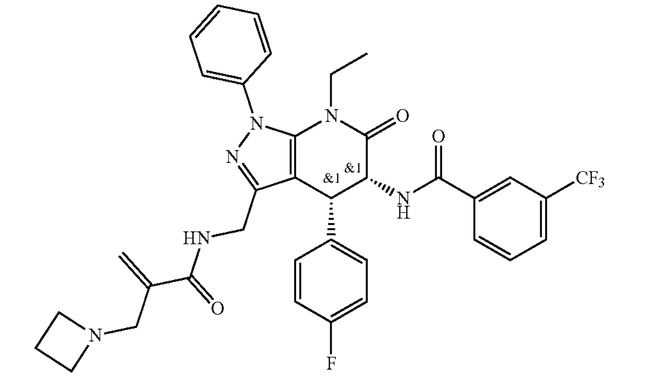 [SMILES: C=C(CN1CCC1)C(=O)NCc1nn(-c2ccccc2)c2c1[C@@H](c1ccc(F)cc1)[C@@H](NC(=O)c1cccc(C(F)(F)F)c1)C(=O)N2CC] | $^1$H NMR (300 MHz, DMSO-$d_6$) δ 9.75-9.70 (m, 1H), 9.08 (d, J = 8.5 Hz, 1H), 8.52 (s, 1H), 8.02-7.99 (m, 2H), 7.92 (d, J = 7.7 Hz, 1H), 7.77-7.49 (m, 6H), 7.40-7.33 (m, 2H), 7.15 (t, J = 8.8 Hz, 2H), 6.04 (d, J = 13.1 Hz, 1H), 5.80 (s, 1H), 5.20-5.11 (m, 1H), 4.45 (d, J = 10.9 Hz, 1H), 3.86 (d, J = 27.2 Hz, 4H), 3.66-3.54 (m, 4H), 2.27 (s, 1H), 1.26 (d, J = 9.2 Hz, 2H), 0.82 (t, J = 7.0 Hz, 3H). LCMS Calculated for $C_{36}H_{34}F_4N_6O_3$: 674.26; Observed (Method-F): 675.2 $[M + H]^+$, 90.36% at 1.904 min. |
| 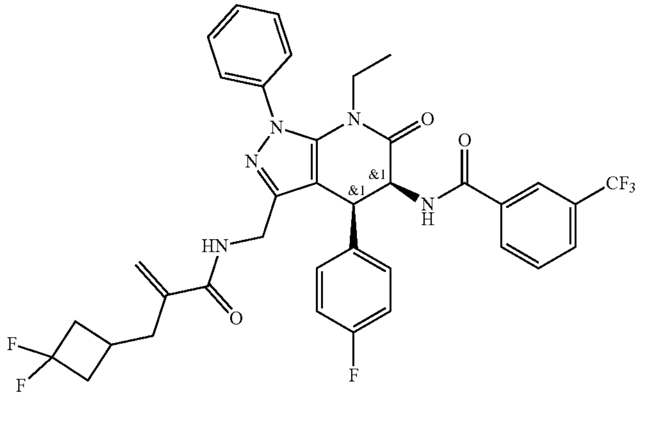 [SMILES: C=C(CC1CC(F)(F)C1)C(=O)NCc1nn(-c2ccccc2)c2c1[C@H](c1ccc(F)cc1)[C@H](NC(=O)c1cccc(C(F)(F)F)c1)C(=O)N2CC] | $^1$H NMR (300 MHz, DMSO-$d_6$) δ 8.51 (d, J = 7.4 Hz, 1H), 8.38 (t, J = 5.9 Hz, 1H), 8.21-8.11 (m, 2H), 7.93 (d, J = 7.9 Hz, 1H), 7.77-7.48 (m, 6H), 7.07 (t, J = 8.8 Hz, 2H), 6.91-6.82 (m, 2H), 5.58-5.41 (m, 2H), 5.25 (d, J = 1.5 Hz, 1H), 4.58 (d, J = 7.1 Hz, 1H), 4.38-4.30 (m, 1H), 4.18-4.07 (m, 1H), 4.01-3.80 (m, 1H), 3.50 (t, J = 12.6 Hz, 4H), 3.21-2.90 (m, 3H), 0.92 (q, J = 7.0 Hz, 3H). LCMS Calculated for $C_{36}H_{32}F_6N_6O_3$: 710.24; Observed (Method-C): 711.2 $[M + H]^+$, 99.01% at 0.935 min. |
| 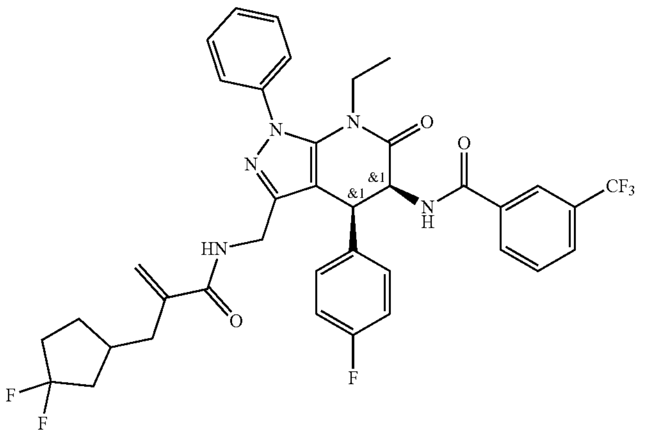 [SMILES: C=C(CC1CCC(F)(F)C1)C(=O)NCc1nn(-c2ccccc2)c2c1[C@H](c1ccc(F)cc1)[C@H](NC(=O)c1cccc(C(F)(F)F)c1)C(=O)N2CC] | 1H NMR (400 MHz, DMSO-$d_6$) δ 8.60-8.48 (m, 2H), 8.23-8.10 (m, 2H), 7.93 (d, J = 7.8 Hz, 1H), 7.77-7.65 (m, 3H), 7.64-7.50 (m, 3H), 7.07 (t, J = 8.8 Hz, 2H), 6.98-6.87 (m, 2H), 5.54 (d, J = 1.6 Hz, 1H), 5.50 (t, J = 7.2 Hz, 1H), 5.30 (d, J = 1.6 Hz, 1H), 4.58 (d, J = 7.2 Hz, 1H), 4.37 (dd, J = 15.3, 6.3 Hz, 1H), 4.20 (dd, J = 15.4, 5.0 Hz, 1H), 3.91 (dq, J = 14.2, 7.0 Hz, 1H), 3.12 (d, J = 13.8 Hz, 1H), 3.08-2.95 (m, 2H), 2.85-2.68 (m, 2H), 2.59 (t, J = 7.0 Hz, 2H), 2.22-2.02 (m, 2H), 0.91 (t, J = 7.0 Hz, 3H). LCMS Calculated for $C_{37}H_{34}F_6N_6O_3$: 724.26; Observed (Method-E): 725.4 $[M + H]^+$, 96.9% at RT 1.124 min. |

-continued

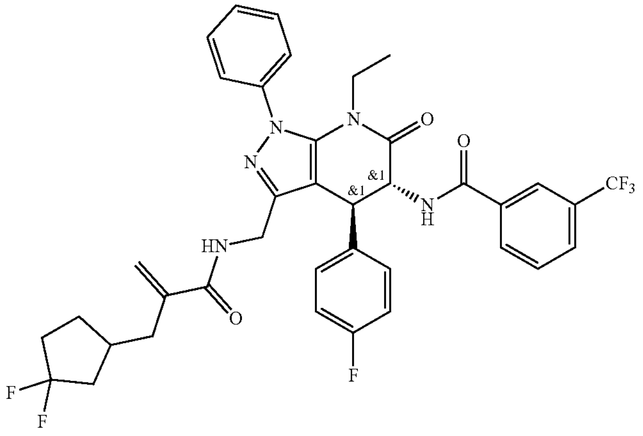 [SMILES: C=C(CC1CCC(F)(F)C1)C(=O)NCc1nn(-c2ccccc2)c2c1[C@H](c1ccc(F)cc1)[C@@H](NC(=O)c1cccc(C(F)(F)F)c1)C(=O)N2CC]

1H NMR (400 MHz, DMSO-d6) = δ 9.03 (d, J = 8.8 Hz, 1H), 8.61 (t, J = 5.0 Hz, 1H), 8.05-8.00 (m, 2H), 7.94-7.88 (m, 1H), 7.71 (t, J = 8.0 Hz, 1H), 7.67-7.62 (m, 2H), 7.58 (t, J = 7.5 Hz, 2H), 7.53 (d, J = 7.1 Hz, 1H), 7.45-7.38 (m, 2H), 7.16 (t, J = 8.7 Hz, 2H), 5.75 (s, 1H), 5.41 (s, 1H), 5.24 (dd, J = 11.5, 8.7 Hz, 1H), 4.42 (d, J = 11.6 Hz, 1H), 3.75-3.67 (m, 1H), 3.63 (d, J = 5.2 Hz, 1H), 3.54-3.45 (m, 1H), 3.21 (s, 1H), 3.21-3.11 (m, 1H), 2.89-2.75 (m, 2H), 2.70-2.58 (m, 2H), 2.16-2.00 (m, 2H), 0.81 (t, J = 7.0 Hz, 3H).
LCMS Calculated for $C_{37}H_{34}F_6N_6O_3$: 724.26; Observed (Method-E): 725.4 $[M + H]^+$, 97.6% at RT 1.069 min.

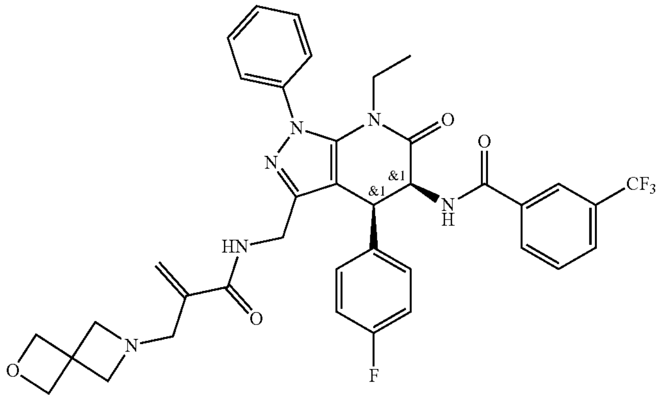 [SMILES: C=C(CN1CC2(COC2)C1)C(=O)NCc1nn(-c2ccccc2)c2c1[C@H](c1ccc(F)cc1)[C@H](NC(=O)c1cccc(C(F)(F)F)c1)C(=O)N2CC]

1H NMR (400 MHz, DMSO-d6) = δ 8.62 (t, J = 5.6 Hz, 1H), 8.53 (d, J = 7.4 Hz, 1H), 8.20-8.12 (m, 2H), 7.93 (d, J = 7.8 Hz, 1H), 7.77-7.66 (m, 3H), 7.64-7.57 (m, 2H)), 7.58-7.50 (m, 1H), 7.08 (t, J = 8.8 Hz, 2H), 6.95-6.87 (m, 2H), 5.54-5.46 (m, 2H), 5.20 (d, J = 1.8 Hz, 1H), 4.56 (d, J = 7.2 Hz, 1H), 4.48 (q, J = 6.6 Hz, 4H), 4.40-4.31 (m, 1H), 4.22-4.14 (m, 1H), 3.92 (dt, J = 14.2, 7.1 Hz, 1H), 3.17 (s, 4H), 3.04 (dt, J = 14.2, 6.9 Hz, 1H), 2.95-2.77 (m, 2H), 0.91 (t, J = 7.0 Hz, 3H)..
LCMS Calculated for $C_{38}H_{36}F_4N_6O_4$: 716.27; Observed (Method-E): 717.5 $[M + H]^+$, 97.3% at RT 1.402 min.

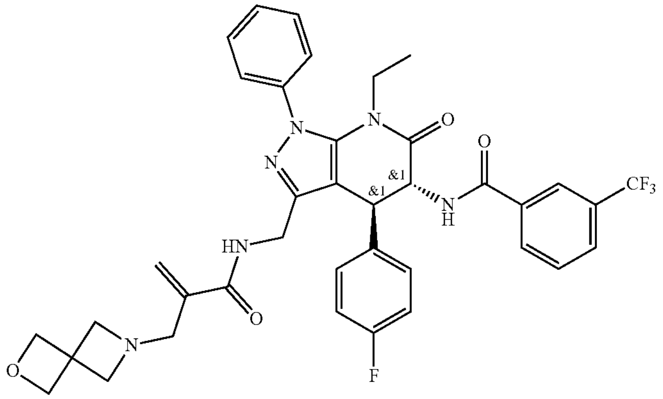 [SMILES: C=C(CN1CC2(COC2)C1)C(=O)NCc1nn(-c2ccccc2)c2c1[C@H](c1ccc(F)cc1)[C@@H](NC(=O)c1cccc(C(F)(F)F)c1)C(=O)N2CC]

$^1$H NMR (400 MHz, DMSO-$d_6$) δ 9.04 (d, J = 8.8 Hz, 1H), 8.76 (t, J = 5.0 Hz, 1H), 8.06-7.99 (m, 2H), 7.92 (d, J = 7.9 Hz, 1H), 7.76-7.65 (m, 3H), 7.61 (t, J = 7.5 Hz, 2H), 7.57-7.50 (m, 1H), 7.45-7.37 (m, 2H), 7.16 (t, J = 8.5 Hz, 2H), 5.70 (s, 1H), 5.32 (s, 1H), 5.28-5.19 (m, 1H), 4.49-4.39 (m, 5H), 3.74-3.60 (m, 2H), 3.55-3.46 (m, 1H), 3.25-3.13 (m, 5H), 3.05 (s, 2H), 0.82 (t, J = 6.9 Hz, 3H).
LCMS Calculated for $C_{38}H_{36}F_4N_6O_4$: 716.27; Observed (Method-E): 717.5 $[M + H]^+$, 89.8% at RT 1.333 min.

-continued

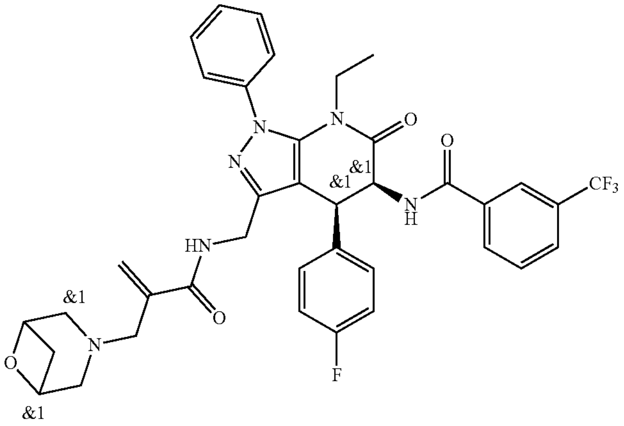 [SMILES: C=C(CN1CC2CC(C1)O2)C(=O)NCc1nn(-c2ccccc2)c2c1[C@H](c1ccc(F)cc1)[C@H](NC(=O)c1cccc(C(F)(F)F)c1)C(=O)N2CC]

$^1$H NMR (400 MHz, DMSO-$d_6$) δ 9.31-9.20 (m, 1H), 8.53 (d, J = 7.4 Hz, 1H), 8.19-8.12 (m, 2H), 7.93 (d, J = 7.8 Hz, 1H), 7.75-7.65 (m, 3H), 7.64-7.51 (m, 3H), 7.09 (t, J = 8.6 Hz, 2H), 6.99-6.90 (m, 2H), 5.69 (s, 1H), 5.51 (q, J = 7.0 Hz, 1H), 5.35 (s, 1H), 4.58 (d, J = 7.3 Hz, 1H), 4.37-4.19 (m, 3H), 3.91 (d, J = 12.9 Hz, 1H), 3.75-3.65 (m, 1H), 3.43-3.35 (m, 1H), 3.30-3.21 (m, 1H), 3.16 (s, 1H), 3.09-3.00 (m, 2H), 2.62-2.53 (m, 1H), 2.38-2.28 (m, 1H), 1.63 (d, J = 8.0 Hz, 1H), 1.43 (s, 1H), 0.92 (t, J = 7.0 Hz, 3H).
LCMS Calculated for $C_{38}H_{36}F_4N_6O_4$: 716.27; Observed: (Method-C) 717.4 $[M + H]^+$, 92.7% at RT 0.954 min.

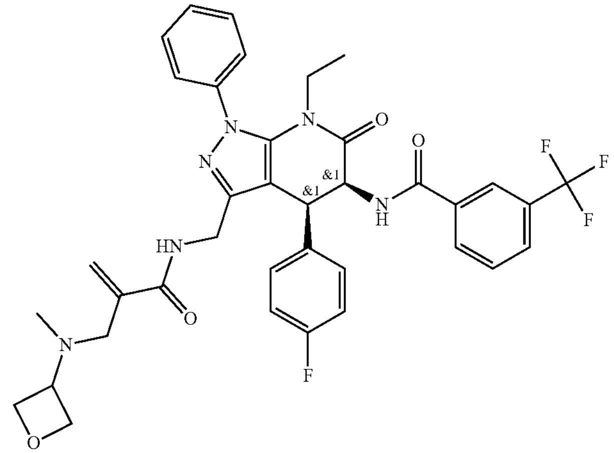 [SMILES: C=C(CN(C)C1COC1)C(=O)NCc1nn(-c2ccccc2)c2c1[C@H](c1ccc(F)cc1)[C@H](NC(=O)c1cccc(C(F)(F)F)c1)C(=O)N2CC]

$^1$H NMR (400 MHz, DMSO-$d_6$) δ 8.79 (s, 1H), 8.60-8.43 (m, 1H), 8.22-8.10 (m, 2H), 7.93 (d, J = 7.8 Hz, 1H), 7.77-7.64 (m, 3H), 7.63-7.48 (m, 3H), 7.07 (t, J = 8.7 Hz, 2H), 6.99-6.83 (m, 2H), 5.75 (s, 1H), 5.57 (s, 1H), 5.50 (t, J = 7.2 Hz, 1H), 5.29 (s, 1H), 4.57 (d, J = 7.2 Hz, 1H), 4.48-4.29 (m, 3H), 4.29-4.16 (m, 2H), 3.92 (dd, J = 14.3, 7.3 Hz, 1H), 3.50-3.35 (m, 1H), 3.03 (dd, J = 14.2, 7.1 Hz, 1H), 2.88 (d, J = 13.4 Hz, 1H), 2.73-2.55 (m, 2H) 1.89 (s, 2H), 0.91 (t, J = 7.0 Hz, 3H).
LCMS Calculated for C37H36F4N6O4: 704.27; Observed: (Method-C) 705.7 $[M + H]^+$, 98.3% at RT 0.946 min.

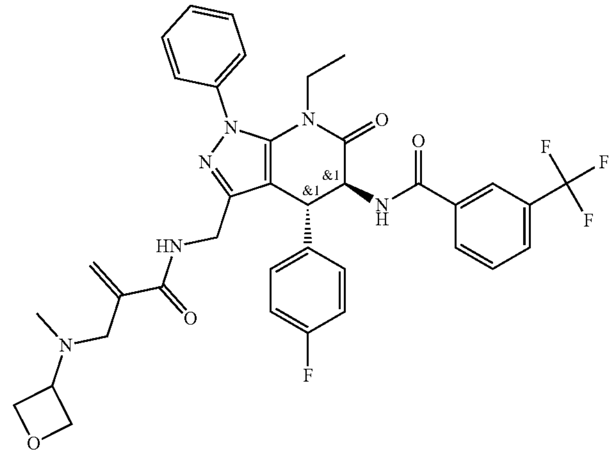 [SMILES: C=C(CN(C)C1COC1)C(=O)NCc1nn(-c2ccccc2)c2c1[C@@H](c1ccc(F)cc1)[C@H](NC(=O)c1cccc(C(F)(F)F)c1)C(=O)N2CC]

$^1$H NMR (400 MHz, DMSO-$d_6$) δ 9.03 (d, J = 8.8 Hz, 1H), 8.90-8.84 (m, 1H), 8.05-7.99 (m, 2H), 7.91 (d, J = 7.8 Hz, 1H), 7.72 (t, J = 7.9 Hz, 1H), 7.69-7.64 (m, 2H), 7.58 (t, J = 7.5 Hz, 2H), 7.52 (t, J = 7.0 Hz, 1H), 7.48-7.40 (m, 2H), 7.17 (t, J = 8.6 Hz, 2H), 5.80 (s, 1H), 5.39 (s, 1H), 5.31-5.33 (m, 1H), 4.49-4.30 (m, 5H), 3.79-3.61 (m, 2H), 3.58-3.46 (m, 2H), 3.18-3.09 (m, 1H), 3.06-2.92 (m, 2H), 1.95 (s, 3H), 0.82 (t, J = 7.0 Hz, 3H).
LCMS Calculated for $C_{37}H_{36}F_4N_6O_4$: 704.27, Observed: (Method-M) 705.3 $[M + H]^+$, 98.0% at RT 1.749 min.

-continued

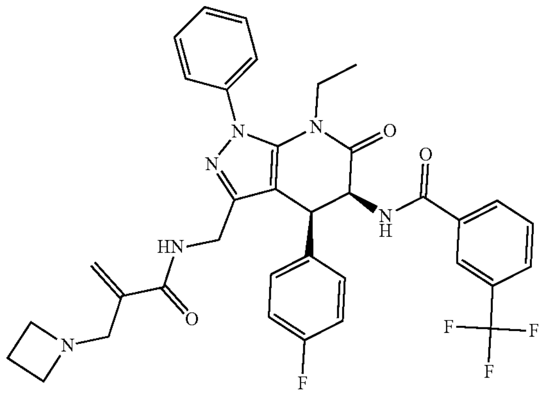 [SMILES: C=C(CN1CCC1)C(=O)NCc1nn(-c2ccccc2)c2c1[C@H](c1ccc(F)cc1)[C@H](NC(=O)c1cccc(C(F)(F)F)c1)C(=O)N2CC]

$^{1}$H NMR (300 MHz, DMSO-$d_6$) δ 8.76 (t, J = 5.7 Hz, 1H), 8.52 (d, J = 7.4 Hz, 1H), 8.15-8.12 (m, 2H), 7.93 (d, J = 7.8 Hz, 1H), 7.80-7.65 (m, 3H), 7.57-7.54 (m, 3H), 7.07 (t, J = 8.8 Hz, 2H), 6.93-6.88 (m, 2H), 5.62-5.43 (m, 2H), 5.22 (s, 1H), 4.58 (d, J = 7.2 Hz, 1H), 4.39-4.36 (m, 1H), 4.19-4.14 (m, 1H), 4.04-3.76 (m, 1H), 3.00-2.97 (m, 6H), 2.94-2.71 (m, 1H), 1.87-1.84 (m, 2H), 0.92 (t, J = 7.0 Hz, 3H).
LCMS Calculated for $C_{36}H_{34}F_4N_6O_3$: 674.26; Observed: (Method-M), 675.3 $[M + H]^+$, 99.1% at RT 2.031 min.

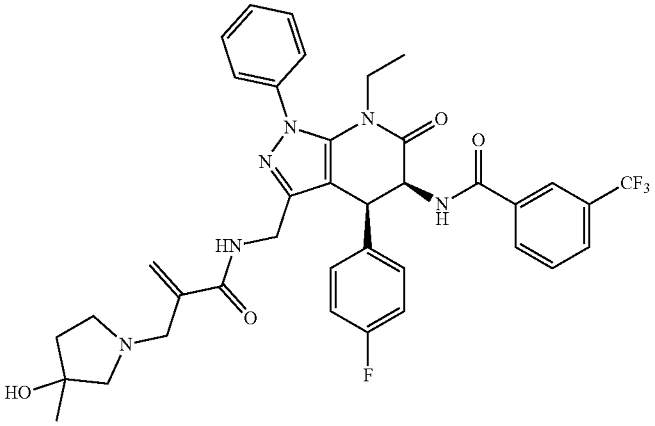 [SMILES: C=C(CN1CCC(C)(O)C1)C(=O)NCc1nn(-c2ccccc2)c2c1[C@H](c1ccc(F)cc1)[C@H](NC(=O)c1cccc(C(F)(F)F)c1)C(=O)N2CC]

$^{1}$H NMR (400 MHz, DMSO-$d_6$) δ 9.23-9.20 (m, 1H), 8.52 (t, J = 6.8 Hz, 1H), 8.22-8.06 (m, 2H), 7.93 (d, J = 7.9 Hz, 1H), 7.78-7.64 (m, 3H), 7.64-7.48 (m, 3H), 7.08-7.04 (m, 2H), 6.94-6.91 (m, 2H), 5.68 (dd, J = 13.4, 2.1 Hz, 1H), 5.51-5.48 (m, 1H), 5.30 (d, J = 11.0 Hz, 1H), 4.57 (dd, J = 7.2, 3.4 Hz, 1H), 4.51 (d, J = 1.6 Hz, 1H), 4.47-4.29 (m, 1H), 4.19-4.15 (m, 1H), 3.90-3.86 (m, 1H), 3.05-3.01 (m, 2H), 2.89-2.85 (m, 1H), 2.49-2.16 (m, 4H), 1.70-1.42 (m, 2H), 1.08 (d, J = 7.3 Hz, 3H), 0.91 (t, J = 6.7 Hz, 3H).
LCMS Calculated for $C_{38}H_{38}F_4N_6O_4$: 718.29; Observed: (Method-M) 719.4 $[M + H]^+$, 99.2% at RT 1.889 min.

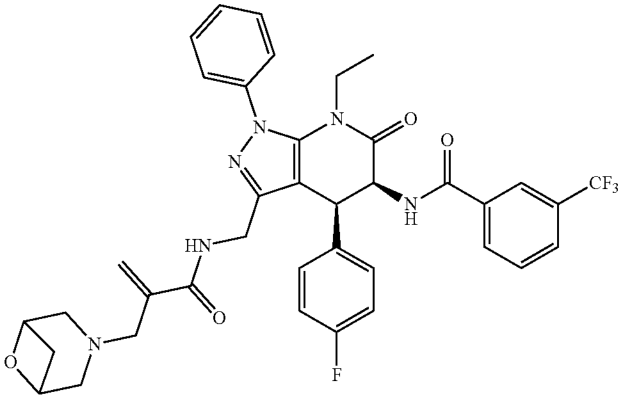 [SMILES: C=C(CN1CC2CC(C1)O2)C(=O)NCc1nn(-c2ccccc2)c2c1[C@H](c1ccc(F)cc1)[C@H](NC(=O)c1cccc(C(F)(F)F)c1)C(=O)N2CC]

$^{1}$H NMR (300 MHz, DMSO-$d_6$) δ 9.21 (t, J = 5.2 Hz, 1H), 8.55 (d, J = 7.4 Hz, 1H), 8.19-8.10 (m, 2H), 7.93 (d, J = 7.8 Hz, 1H), 7.72 (t, J = 7.8 Hz, 1H), 7.67-7.50 (m, 5H), 7.10 (t, J = 8.8 Hz, 2H), 6.96 (dd, J = 8.5, 5.5 Hz, 2H), 5.84 (d, J = 2.2 Hz, 1H), 5.50 (t, J = 7.3 Hz, 1H), 5.44 (s, 1H), 4.56 (d, J = 7.3 Hz, 1H), 4.34-4.24 (m, 3H), 4.17 (s, 1H), 3.92 (dd, J = 14.3, 7.2 Hz, 1H), 3.31-3.15 (m, 2H), 3.06 (dt, J = 14.3, 7.3 Hz, 1H), 2.96-2.88 (m, 1H), 2.87-2.77 (m, 1H), 2.54-2.42 (m, 3H), 1.96 (d, J = 8.1 Hz, 1H), 0.92 (t, J = 7.0 Hz, 3H).
LCMS Calculated for $C_{38}H_{36}F_4N_6O_4$: 716.27; Observed: (Method-M), 717.3 $[M + H]^+$, 97.1% at RT 1.903 min.

-continued

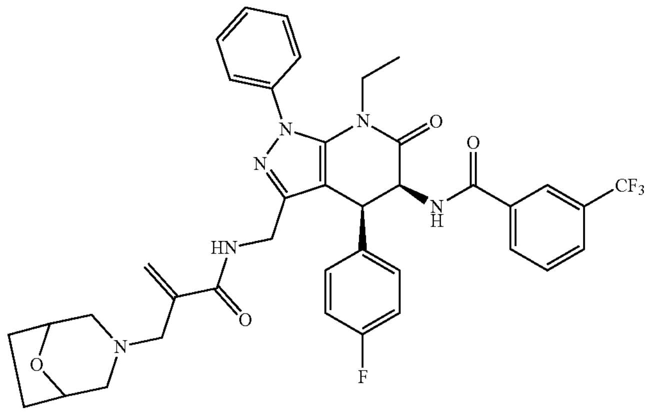 [SMILES: C=C(CN1CC2CCC(C1)O2)C(=O)NCc1nn(-c2ccccc2)c2c1[C@H](c1ccc(F)cc1)[C@H](NC(=O)c1cccc(C(F)(F)F)c1)C(=O)N2CC]

$^1$H NMR (300 MHz, DMSO-$d_6$) δ 9.07-8.95 (m, 1H), 8.52 (d, J = 7.2 Hz, 1H), 8.17-8.05 (m, 2H), 7.92 (d, J = 7.9 Hz, 1H), 7.71 (t, J = 7.9 Hz, 1H), 7.67-7.48 (m, 5H), 7.08 (t, J = 8.8 Hz, 2H), 6.92 (dd, J = 8.5, 5.5 Hz, 2H), 5.78 (d, J = 2.3 Hz, 1H), 5.48 (t, J = 7.2 Hz, 1H), 5.30 (s, 1H), 4.62-4.43 (m, 2H), 4.21-4.03 (m, 3H), 4.01-3.86 (m, 1H), 3.15-2.96 (m, 2H), 2.75 (d, J = 13.1 Hz, 1H), 2.61-2.54 (m, 1H), 2.09 (d, J = 11.0 Hz, 1H), 2.02 (d, J = 11.1 Hz, 1H), 1.91 (d, J = 11.0 Hz, 1H), 1.73-1.56 (m, 2H), 1.47 (t, J = 6.2 Hz, 1H), 1.36-1.20 (m, 1H), 0.93 (t, J = 7.0 Hz, 3H).
LCMS Calculated for $C_{39}H_{38}F_4N_6O_4$: 730.29; Observed (Method-V): 731.3 $[M+H]^+$, 99.73% at 1.941 min.

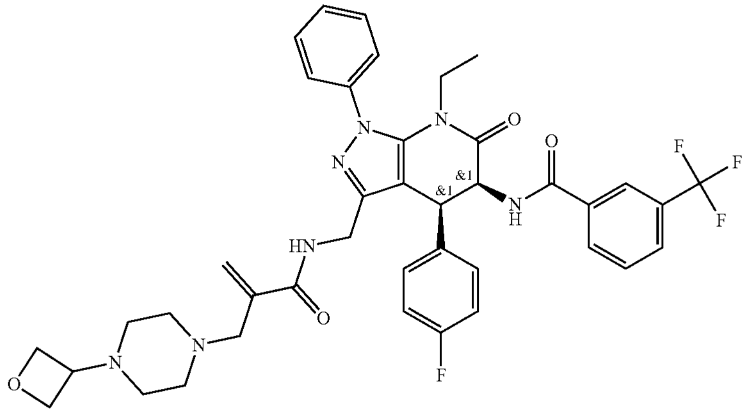 [SMILES: C=C(CN1CCN(C2COC2)CC1)C(=O)NCc1nn(-c2ccccc2)c2c1[C@H](c1ccc(F)cc1)[C@H](NC(=O)c1cccc(C(F)(F)F)c1)C(=O)N2CC]

$^1$H NMR (400 MHz, DMSO-$d_6$) δ 9.30 (s, 1H), 8.54 (d, J = 7.4 Hz, 1H), 8.14 (d, J = 11.8 Hz, 2H), 7.92 (d, J = 7.9 Hz, 1H), 7.70 (dd, J = 16.5, 7.9 Hz, 3H), 7.60 (dt, J = 14.2, 7.1 Hz, 3H), 7.09 (t, J = 8.8 Hz, 2H), 6.95 (s, 2H), 5.78 (s, 1H), 5.51 (t, J = 7.3 Hz, 1H), 5.33 (s, 1H), 4.55 (d, J = 7.2 Hz, 1H), 4.48-4.16 (m, 6H), 3.92 (dq, J = 14.4, 7.2 Hz, 1H), 3.11-2.92 (m, 4H), 2.38-2.16(m, 3H), 2.14-1.88 (m, 3H), 0.91 (t, J = 7.1 Hz, 3H).
LCMS Calculated for $C_{40}H_{41}F_4N_7O_4$: 759.32; Observed (Method-C): 760.8 $[M+H]^+$, 98.0% at RT 0.933 min.

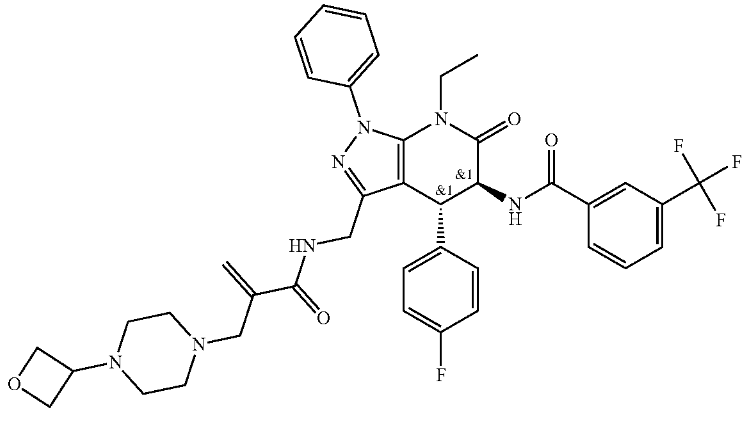 [SMILES: C=C(CN1CCN(C2COC2)CC1)C(=O)NCc1nn(-c2ccccc2)c2c1[C@@H](c1ccc(F)cc1)[C@H](NC(=O)c1cccc(C(F)(F)F)c1)C(=O)N2CC]

$^1$H NMR (400 MHz, DMSO-$d_6$) δ 9.23 (s, 1H), 8.99 (d, J = 8.9 Hz, 1H), 8.00-7.98 (m, 2H), 7.89 (d, J = 7.8 Hz, 1H), 7.70 (d, J = 7.9 Hz, 1H), 7.64 (d, J = 7.7 Hz, 2H), 7.58-7.53 (m, 3H), 7.44-7.36 (m, 2H), 7.15 (t, J = 8.7 Hz, 2H), 5.84 (s, 1H), 5.34 (s, 1H), 5.28-5.19 (m, 1H), 4.44-4.31 (m, 3H), 4.24 (d, J = 7.2 Hz, 2H), 3.69-3.66 (m, 2H), 3.44-3.42 (m, 2H), 3.09-3.05 (m, 3H), 2.87-2.85 (m, 1H), 2.66-2.64 (m, 3H), 2.32-2.30 (m, 2H), 1.98-1.96 (m, 2H), 0.79 (t, J = 7.1 Hz, 3H).
LCMS Calculated for $C_{40}H_{41}F_4N_7O_4$: 759.32; Observed (Method-G): 760.8 $[M+H]^+$, 97.4% at RT 1.699 min.

Synthesis of rac-N-(((4R, 5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)-1-methyl-2,5-dihydro-1H-pyrrole-3-carboxamide (I-86)

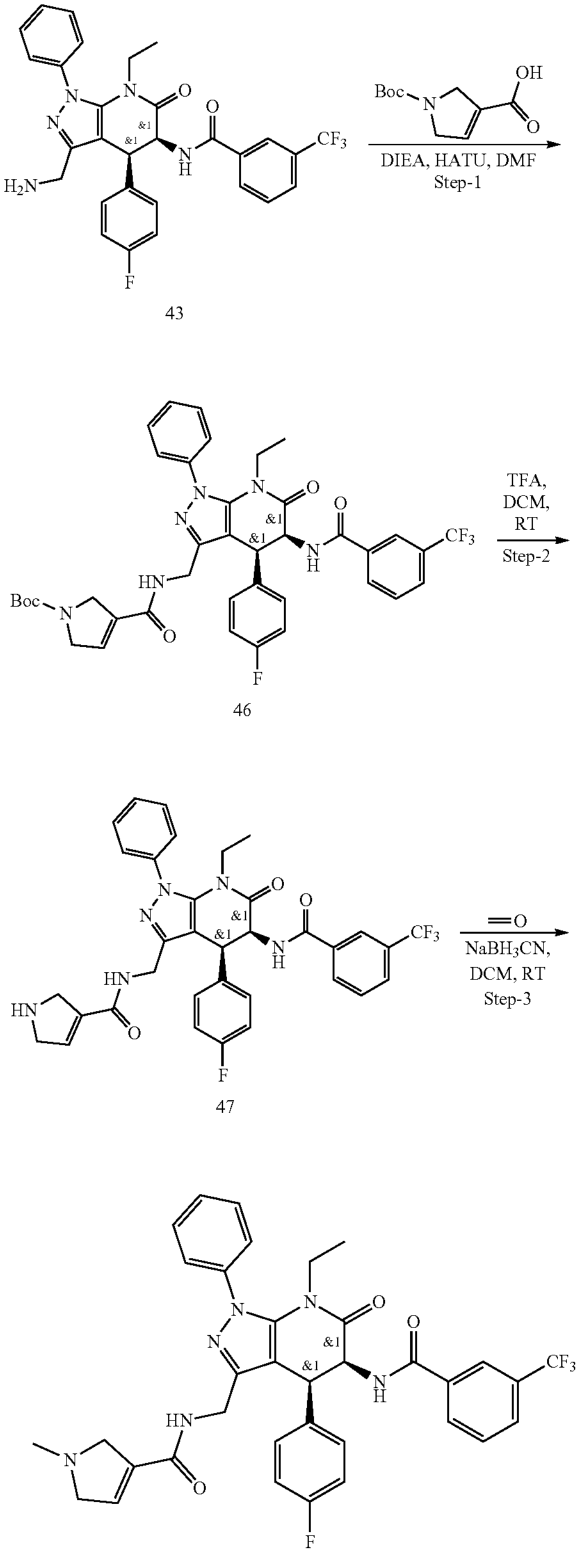

43

46

47

CY-2012376 rac-tert-butyl 3-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)carbamoyl)-2,5-dihydro-1H-pyrrole-1-carboxylate (46)

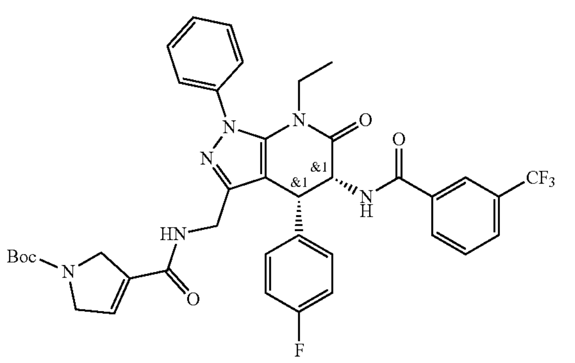

A mixture of rac-N-((4R,5R)-3-(aminomethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (150 mg, 0.272 mmol, 1.00 equiv), 1-(tert-butoxycarbonyl)-2,5-dihydropyrrole-3-carboxylic acid (57.9 mg, 0.272 mmol, 1.00 equiv) and DIEA (105 mg, 0.816 mmol, 3.00 equiv) in DMF (5 mL) was stirred at room temperature for 10 min. HATU (615 mg, 1.62 mmol) was then added, and the reaction mixture was stirred for 2 hours at room temperature. The resulting mixture was purified by prep-HPLC ($NH_3 \cdot H_2O$ buffer) to give rac-tert-butyl 3-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl) carbamoyl)-2,5-dihydro-1H-pyrrole-1-carboxylate (170 mg, 83%) as a white solid.

rac-N-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)carbamoyl)-2,5-dihydro-1H-pyrrole-1-carboxamide (47)

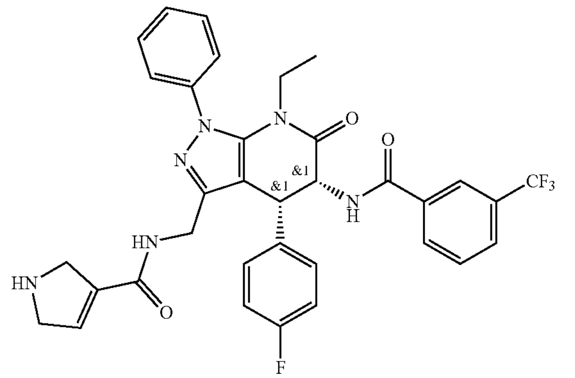

A solution of rac-tert-butyl 3-((((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl) carbamoyl)-2,5-dihydro-1H-pyrrole-1-carboxylate (170 mg, 0.228 mmol, 1.00 equiv) in TFA (1 mL) and DCM (4 mL) was stirred for 1 hour at room temperature. The resulting mixture was concentrated in vacuum to afford rac-N-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)-2,5-dihydro-1H-pyrrole-3-carboxamide (130 mg, 88%) as a yellow solid, which was used for next step directly.

rac-N-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)-1methyl-2,5-dihydro-1H-pyrrole-1-carboxamide (I-86)

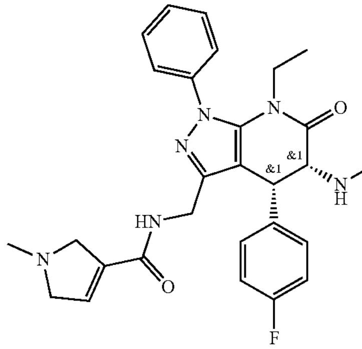

A mixture of rac-N-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)-2,5-dihydro-1H-pyrrole-3-carboxamide (130 mg, 0.201 mmol, 1.00 equiv), formaldehyde (18.1 mg, 0.603 mmol, 3.00 equiv) in DCM (5 mL) was stirred at room temperature for 30 min. $NaBH_3CN$ (37.9 mg, 0.603 mmol, 3.00 equiv) was then added, and the reaction mixture was stirred for 1 hour at room temperature. The resulting mixture was concentrated in vacuum, the residue was purified by prep-HPLC ($NH_3 \cdot H_2O$ buffer) to give rac-N-(((4R,5R)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)-1-methyl-2,5-dihydro-1H-pyrrole-3-carboxamide (20 mg, 15%) as a white solid.

$^1$H NMR (300 MHZ, DMSO-$d_6$) δ 8.49 (d, J=7.4 Hz, 1H), 8.17-8.14 (m, 2H), 8.06 (d, J=6.5 Hz, 1H), 7.94 (d, J=7.8 Hz, 1H), 7.79-7.64 (m, 3H), 7.66-7.51 (m, 3H), 7.04 (t, J=8.8 Hz, 2H), 6.85-6.81 (m, 2H), 6.04 (s, 1H), 5.49 (t, J=7.3 Hz, 1H), 4.55-4.46 (m, 2H), 4.08-4.02 (m, 1H), 3.92-3.90 (m, 1H), 3.32-3.27 (m, 2H), 3.15-2.89 (m, 3H), 2.26 (s, 3H), 0.91 (t, J=7.0 Hz, 3H).

LCMS Calculated for $C_{35}H_{32}F_4N_6O_3$: 660.25; Observed: (Method-C) 661.2 [M+H]$^+$, 97.0% at RT 1.674 min.

Synthesis of rac-N-((4R, 5R)-3-cyano-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-115)

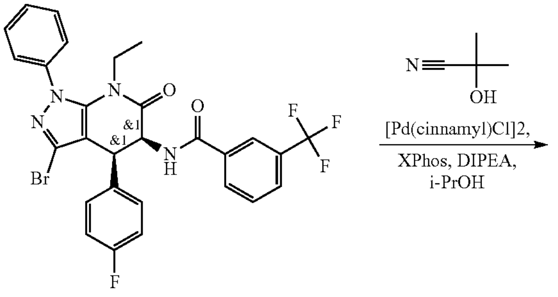

3

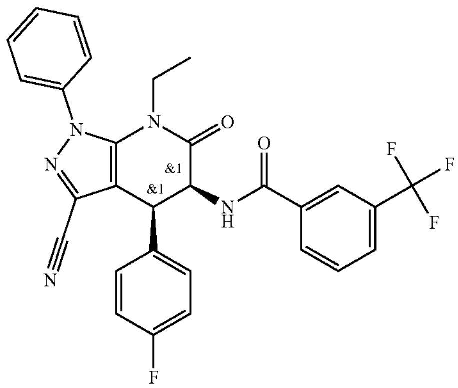

I-115

Into a 8 mL vial were added rac-N-((4R,5R)-3-bromo-7-ethyl-4-(4-fluorophenyl)-6-oxo-1-phenyl-4,5,6,7-tetrahydro-1H-pyrazolo[3,4-b]pyridin-5-yl)-3-(trifluoromethyl) benzamide (50.0 mg, 0.083 mmol, 1.00 equiv), acetone cyanohydrin (14.1 mg, 0.166 mmol, 2.00 equiv), (DiMeI-HeptCl)Pd(cinnamyl)Cl (9.71 mg, 0.008 mmol, 0.1 equiv), XPhos (7.93 mg, 0.017 mmol, 0.2 equiv), DIEA (21.49 mg, 0.166 mmol, 2 equiv) and i-PrOH (1 mL) at room temperature. The resulting mixture was stirred overnight at 80° C. under nitrogen atmosphere. The mixture was allowed to cool down to room temperature. The resulting mixture was concentrated under reduced pressure. The residue was purified by reversed-phase flash chromatography with the following conditions: column, C18 silica gel; mobile phase, MeCN in Water (0.1% FA), 10% to 50% gradient in 10 min; detector, UV 254 nm. This resulted in rac-N-((4R,5R)-3-cyano-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (4 mg, 8.79%) as a white solid.

$^1$H NMR (400 MHZ, DMSO-$d_6$) δ 8.73 (d, J=7.6 Hz, 1H), 8.20-8.12 (m, 2H), 7.93 (d, J=7.9 Hz, 1H), 7.82 (dd, J=6.6, 2.9 Hz, 2H), 7.72 (t, J=7.8 Hz, 1H), 7.69-7.63 (m, 3H), 7.16 (t, J=8.7 Hz, 2H), 7.07 (dd, J=8.6, 5.4 Hz, 2H), 5.67 (t, J=7.3 Hz, 1H), 4.68 (d, J=7.3 Hz, 1H), 3.83 (dd, J=14.3, 7.2 Hz, 1H), 3.03 (dd, J=14.4, 7.2 Hz, 1H), 0.89 (t, J=7.1 Hz, 3H).

LCMS Calculated for $C_{29}H_{21}F_4N_5O_2$: 547.16; Observed (Method-B): 548.2 [M+H]$^+$, 99.4% at RT 1.42 min.

Synthesis of N-((4S, 5S)-3-((R)-1-(N-(3-(dimethylamino)propyl)cyanamido)ethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-578) & N-((4S, 5R)-3-((R)-1-(N-(3-(dimethylamino)propyl)cyanamido)ethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide formate (I-609)

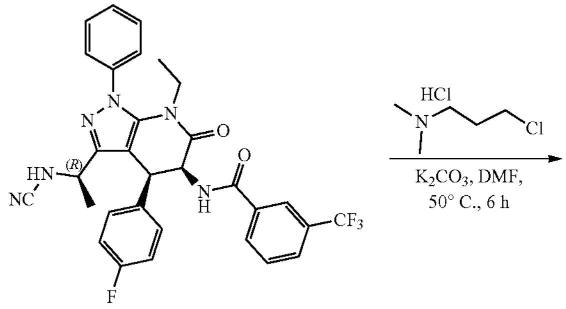

I-73

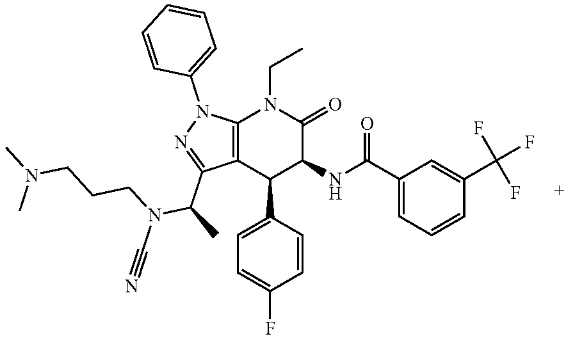

I-578

-continued

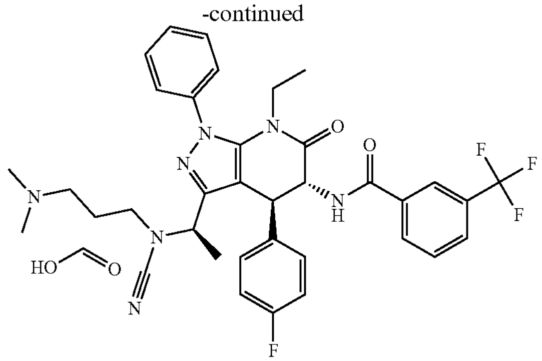

I-609

To a solution of 3-chloro-N,N-dimethylpropan-1-amine hydrochloride (22.7 mg, 0.170 mmol, 1.00 equiv) in DMF (1.00 mL) was added $K_2CO_3$ (70.2 mg, 0.58 mmol, 3.00 equiv), then to the above reaction mixture was added N-((4S,5S)-3-((R)-1-cyanamidoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (100 mg, 0.170 mmol, 1.00 equiv). The mixture was stirred at 50° C. for 6 hrs. The reaction mixture was purified directly by Prep-HPLC (Column: Uitimate-C18 Column, 30*250 mm, 10 μm; Mobile Phase A: Water (0.1% FA), Mobile Phase B: ACN; Flow rate: 35 mL/min; Gradient: isocratic 35%-56% 9 min; Wave Length: 254 nm/220 nm nm; RT1(min): 7.6) to afford N-((4S,5S)-3-((R)-1-(N-(3-(dimethylamino)propyl)cyanamido)ethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-578) (9.9 mg, 8.74%) as a white solid and N-((4S,5R)-3-((R)-1-(N-(3-(dimethylamino)propyl) cyanamido)ethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide formate (I-609) (7.4 mg, 6.5%) as a white solid.

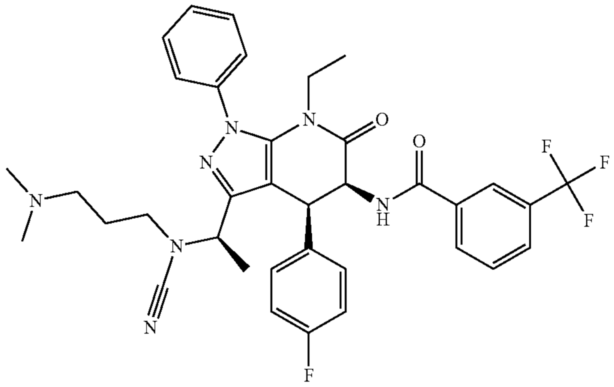 [SMILES: CCN1C(=O)[C@@H](NC(=O)c2cccc(C(F)(F)F)c2)[C@@H](c2ccc(F)cc2)c2c([C@@H](C)N(C#N)CCCN(C)C)nn(-c3ccccc3)c21]

$^1$H NMR (300 MHz, DMSO-$d_6$) δ 8.57 (d, J = 7.3 Hz, 1H), 8.25-8.12 (m, 2H), 7.93 (d, J = 7.8 Hz, 1H), 7.76-7.67 (m, 3H), 7.67-7.52 (m, 3H), 7.13 (t, J = 8.7 Hz, 2H), 7.00 (dd, J = 8.5, 5.5 Hz, 2H), 5.53 (t, J = 7.2 Hz, 1H), 4.65 (d, J = 7.2 Hz, 1H), 4.29 (q, J = 6.7 Hz, 1H), 3.98-3.81 (m, 1H), 3.16-3.02 (m, 1H), 2.96-2.83 (m, 1H), 2.82-2.69 (m, 1H), 2.17 (t, J = 6.9 Hz, 2H), 2.07 (s, 6H), 1.65-1.41 (m, 2H), 1.37 (d, J = 6.9 Hz, 3H), 0.93 (t, J = 7.0 Hz, 3H).
LCMS Calculated for $C_{36}H_{37}F_4N_7O_2$: 675.29; Observed (Method-B): 676.1 $[M + H]^+$, 95.3% at 0.999 min.

-continued

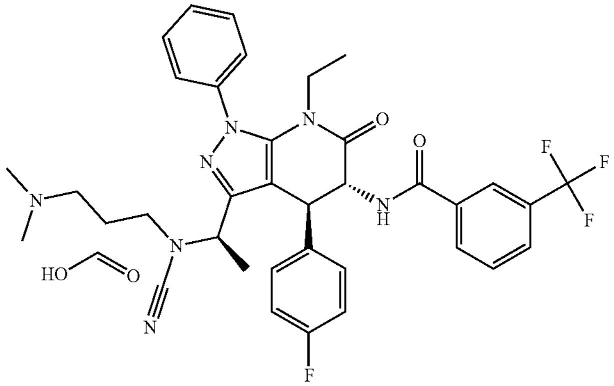

$^1H$ NMR (400 MHz, DMSO-$d_6$) δ 9.06 (d, J = 8.6 Hz, 1H), 8.29 (s, 1H), 8.06-7.99 (m, 2H), 7.92 (d, J = 7.8 Hz, 1H), 7.76-7.66 (m, 3H), 7.62 (t, J = 7.5 Hz, 2H), 7.55 (t, J = 7.3 Hz, 1H), 7.45 (dd, J = 8.5, 5.5 Hz, 2H), 7.20 (t, J = 8.6 Hz, 2H), 5.19 (dd, J = 11.2, 8.7 Hz, 1H), 4.47 (d, J = 11.2 Hz, 1H), 3.70 (dt, J = 14.0, 7.0 Hz, 1H), 3.35 (q, J = 6.6 Hz, 1H), 3.16 (dt, J = 13.9, 7.0 Hz, 1H), 2.76-2.64 (m, 1H), 2.16-2.09 (m, 2H), 2.08 (s, 6H), 1.46 (p, J = 7.2 Hz, 2H), 1.30 (d, J = 6.8 Hz, 3H), 0.80 (t, J = 7.0 Hz, 3H).
LCMS Calculated for $C_{36}H_{37}F_4N_7O_2$: 675.29; Observed (Method-B): 676.1 [M + H]$^+$, 99.6% at 1.074 min.

22. Synthesis of tert-butyl (E)-4-((((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)(methyl)amino)but-2-enoate (I-604)

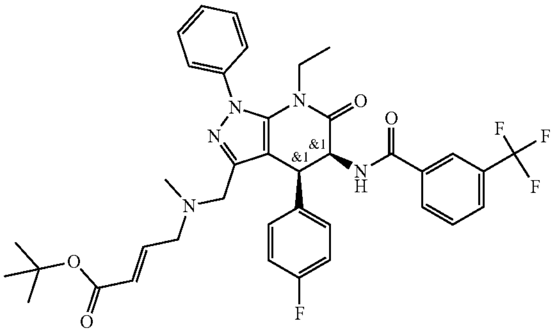

The product was prepared according to I-638.

$^1H$ NMR (400 MHZ, DMSO-$d_6$) δ 8.46 (d, J=7.1 Hz, 1H), 8.18-8.07 (m, 2H), 7.90 (d, J=7.8 Hz, 1H), 7.76-7.65 (m, 3H), 7.62-7.50 (m, 3H), 7.04 (t, J=8.6 Hz, 2H), 6.95 (dd, J=8.4, 5.5 Hz, 2H), 6.45 (dt, J=15.7, 5.8 Hz, 1H), 5.67 (d, J=15.7 Hz, 1H), 5.46 (t, J=7.1 Hz, 1H), 4.65 (d, J=7.2 Hz, 1H), 3.86 (dq, J=14.4, 7.1 Hz, 1H), 3.49-3.41 (m, 1H), 3.30-3.20 (m, 1H), 3.13-2.91 (m, 3H), 1.97 (s, 3H), 1.36 (s, 9H), 0.89 (t, J=7.1 Hz, 3H).

LCMS Calculated for $C_{38}H_{39}F_4N_5O_4$: 705.29; Observed (Method-K): 706.5 [M+H]$^+$, 99.8% at RT 1.039 min.

Synthesis of N-((4R, 5S)-3-(2-((cyanomethyl)amino)-2-oxoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide, (I-298)

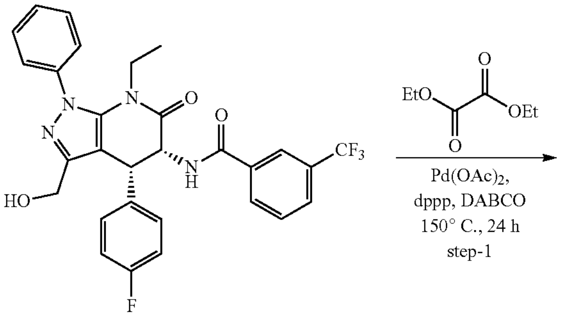

I-645

-continued

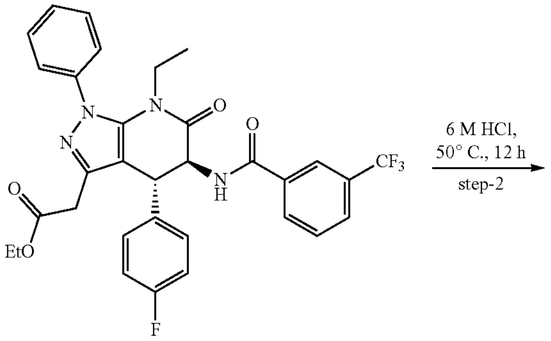

50

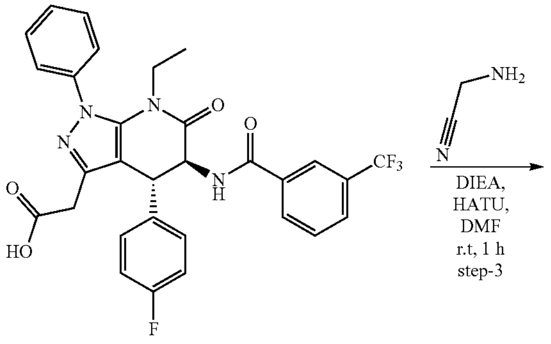

51

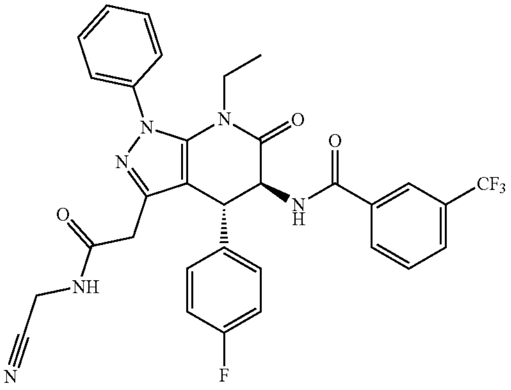

I-298

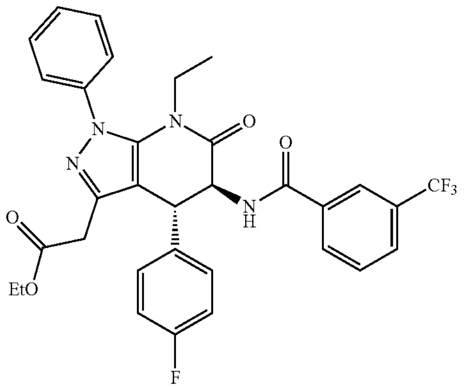

Ethyl2-((4R,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)acetate (50)

Into a 100 mL vial were added N-((4R,5R)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-3-(trifluoromethyl)benzamide (5.00 g, 9.05 mmol, 1.00 equiv), ethyl oxalate (1.59 g, 10.9 mmol, 1.20 equiv), $Pd(OAc)_2$ (0.10 g, 0.452 mmol, 0.05 equiv), DPPP (0.56 g, 1.36 mmol, 0.15 equiv) and 1,4-diazabicyclo[2.2.2]octane (0.100 g, 0.905 mmol, 0.100 equiv) in NMP (20 mL) at room temperature. The resulting mixture was stirred for 24 hours at 150° C. under nitrogen atmosphere. The mixture was allowed to cool down to room temperature, diluted with water (500 mL) and extracted with ethyl acetate (3×200 mL). The combined organic phase was washed with brine (300 mL), dried over anhydrous sodium sulfate, filtered and concentrated in vacuum. The residue was applied onto a silica gel column and eluted with ethyl acetate/petroleum ether (0-30%, 20 min) to afford ethyl 2-((4R,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)acetate (1.00 g, 15.4%) as a yellow solid.

LCMS Calculated for $C_{32}H_{28}F_4N_4O_4$: 608.20; Observed: 609.12 $[M+H]^+$.

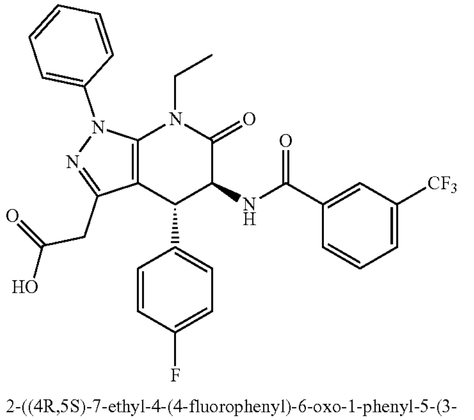

2-((4R,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)acetic acid (51)

To the solution of HCl (6M): 1,4-dioxane=1:2, 3 mL) was added ethyl 2-((4R,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)acetate (200 mg, 0.329 mmol, 1.00 equiv) at room temperature. The reaction mixture was stirred for 12 hours at 50° C. The mixture was allowed to cool down to room temperature. The resulting mixture was concentrated in vacuum to afford 2-((4R,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) acetic acid (120 mg, 51.6%) as a white solid, which was used for next step directly.

LCMS Calculated for $C_{30}H_{24}F_4N_4O_4$: 580.17; Observed: 581.21 $[M+H]^+$.

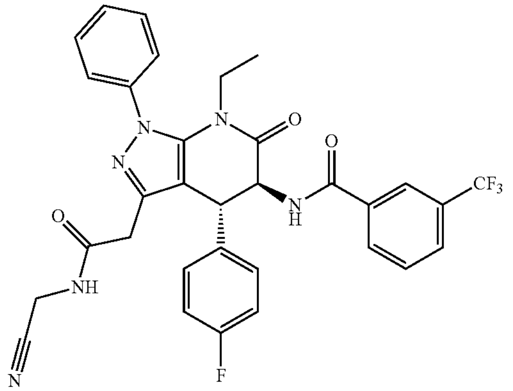

N-((4R,5S)-3-(2-((cyanomethyl)amino)-2-oxoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide, (I-298)

Into a 8 mL vial were added 2-((4R,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) acetic acid (100 mg, 0.172 mmol, 1.00 equiv), aminoacetonitrile (11.5 mg, 0.206 mmol, 1.20 equiv), DIEA (66.7 mg, 0.516 mmol, 3.00 equiv) and HATU (78.6 mg, 0.206 mmol, 1.20 equiv) in DMF (2 mL) at room temperature. The mixture was stirred at room temperature for 1 hour. The mixture was purified by Column: XBridge Prep RP C18 Column, 30*150 mm, 5 μm; Mobile Phase A: Water (10 mmol/L $NH_4HCO_3$), Mobile Phase B: ACN; Flow rate: 35 mL/min; Gradient: 42% B to 58% B in 10 min; Wave Length: 254 nm/220 nm; RT1(min): 6.58 to afford N-((4R,5S)-3-(2-((cyanomethyl)amino)-2-oxoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (22 mg, 19.3%) as a white solid.

$^1$H NMR (400 MHZ, DMSO-$d_6$) δ 8.96 (d, J=8.9 Hz, 1H), 8.16 (t, J=5.7 Hz, 1H), 8.03-7.98 (m, 2H), 7.90 (d, J=7.9 Hz, 1H), 7.71 (t, J=8.0 Hz, 1H), 7.66 (d, J=7.7 Hz, 2H), 7.59 (t, J=7.5 Hz, 2H), 7.53 (d, J=7.1 Hz, 1H), 7.41-7.33 (m, 2H), 7.11 (t, J=8.7 Hz, 2H), 5.27 (dd, J=12.3, 9.0 Hz, 1H), 4.39 (d, J=12.4 Hz, 1H), 3.98 (d, J=5.5 Hz, 2H), 3.79-3.67 (m, 1H), 3.22-3.11 (m, 1H), 3.04 (d, J=16.8 Hz, 1H), 2.54 (d, J=16.8 Hz, 1H), 0.84 (t, J=7.0 Hz, 3H).

LCMS Calculated for $C_{32}H_{26}F_4N_6O_3$: 618.20; Observed (Method-F): 619.0 $[M+H]^+$, 93.9% at RT 0.939 min.

Synthesis of N-((4R, 5S)-3-(2-((cyanomethyl)(methyl)amino)-2-oxoethyl)-7-ethyl-4-(4-fluorophenyl)-6-oxo-1-phenyl-4,5,6,7-tetrahydro-1H-pyrazolo[3,4-b]pyridin-5-yl)-4-(trifluoromethyl)pyrimidine-2-carboxamide (I-640)

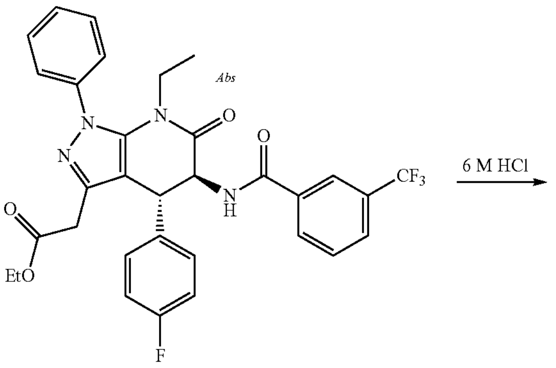

50

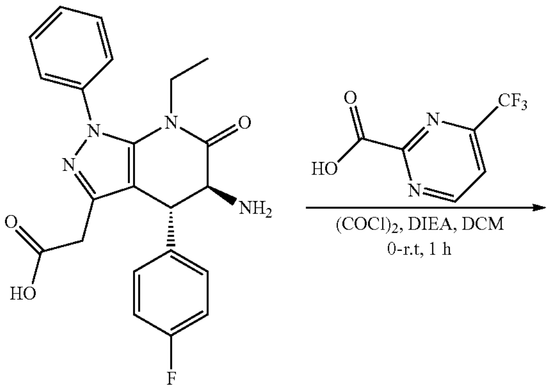

52

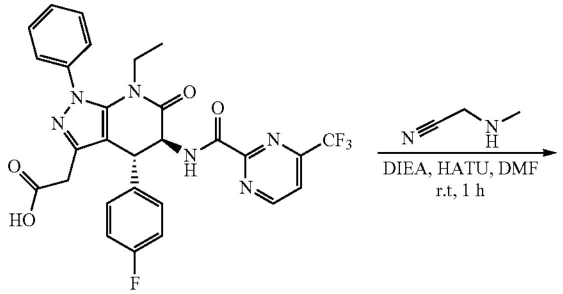

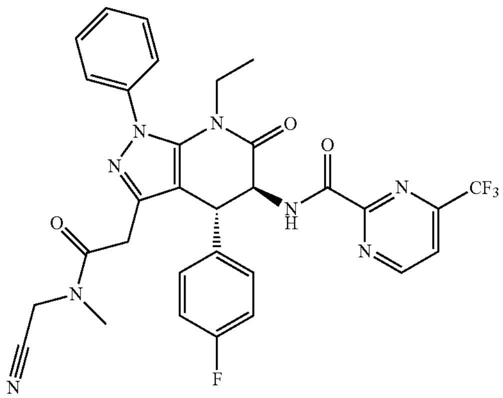

I-640

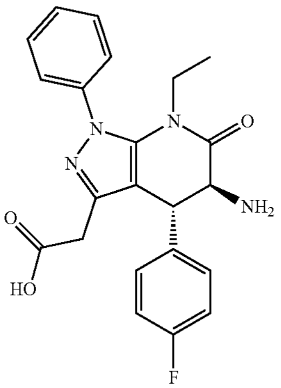

2-((4R,5S)-5-amino-7-ethyl-4-(4-fluorophenyl)-6-oxo-1-phenyl-4,5,6,7-tetrahydro-1H-pyrazolo[3,4-b]pyridin-3-yl)acetic acid (52)

A solution of ethyl 2-((4R,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)acetate (500 mg, 0.822 mmol, 1.00 equiv) in 6M HCl (5 mL) at room temperature. The reaction mixture was stirred for 14 hours at 100° C. The mixture was allowed to cool down to room temperature. The mixture was concentrated in vacuum to afford 2-((4R,5S)-5-amino-7-ethyl-4-(4-fluorophenyl)-6-oxo-1-phenyl-4,5,6,7-tetrahydro-1H-pyrazolo[3,4-b]pyridin-3-yl) acetic acid (150 mg, 39.3%) as a white solid, which was used for next step directly.

LCMS Calculated for $C_{22}H_{21}FN_4O_3$: 408.16; Observed: 409.2 [M+H].

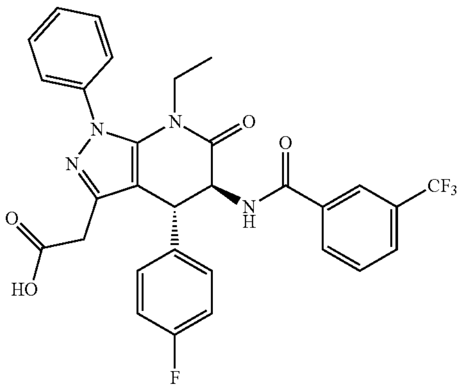

2-((4R,5S)-7-ethyl-4-(4-fluorophenyl)-6-oxo-1-phenyl-5-(4-(trifluoromethyl)pyrimidine-2-carboxamido)-4,5,6,7-tetrahydro-1H-pyrazolo[3,4-b]pyridin-3-yl)acetic acid (53)

To a degassed solution of 4-(trifluoromethyl)pyrimidine-2-carboxylic acid (112 mg, 0.588 mmol, 1.20 equiv) in DCM (3 mL) was added DMF (3.58 mg, 0.049 mmol, 0.10 equiv) followed by $(COCl)_2$ (124 mg, 0.980 mmol, 2.00 equiv) at room temperature. The mixture was stirred at room temperature for 30 min. The mixture was concentrated under vacuum. The residue was dissolved in DCM (1 mL) and added dropwise to a solution of 2-((4R,5S)-7-ethyl-4-(4-fluorophenyl)-6-oxo-1-phenyl-5-(4-(trifluoromethyl)pyrimidine-2-carboxamido)-4,5,6,7-tetrahydro-1H-pyrazolo[3,4-b]pyridin-3-yl) acetic acid (200 mg, 0.490 mmol, 1.00 equiv) and DIEA (189 mg, 1.470 mmol, 3.00 equiv). The mixture was stirred at room temperature for 1 h. The mixture was concentrated in vacuum. The crude product was purified by reverse phase flash with the following conditions Column, Sun Fire Prep C18 OBD Column, 19*150 mm, 5 μm; mobile phase, Water (0.1% $NH_3 \cdot H_2O$) and ACN (30% ACN up to 80% in 10 min); Detector, UV 220,254 nm) to afford 2-((4R,5S)-7-ethyl-4-(4-fluorophenyl)-6-oxo-1-phenyl-5-(4-(trifluoromethyl)pyrimidine-2-carboxamido)-4,5,6,7-tetrahydro-1H-pyrazolo[3,4-b]pyridin-3-yl) acetic acid (150 mg, 43.1%) as a white solid.

LCMS Calculated for $C_{28}H_{22}F_4N_6O_4$: 582.16; Observed: 583.2 [M+H].

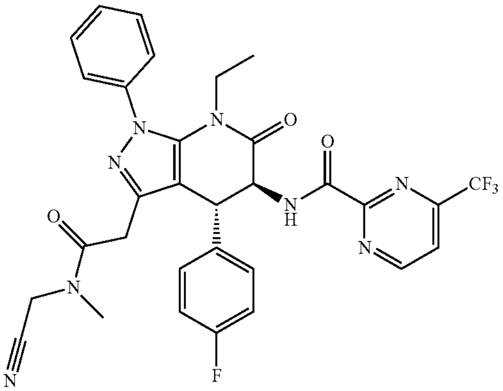

N-((4R,5S)-3-(2-((cyanomethyl)(methyl)amino)-2-oxoethyl)-7-ethyl-4-(4-fluorophenyl)-6-oxo-1-phenyl-4,5,6,7-tetrahydro-1H-pyrazolo[3,4-b]pyridin-5-yl)-4-(trifluoromethyl)pyridmidine-2-carboxamide (I-640)

Into a 8 mL vial were added 2-((4R,5S)-7-ethyl-4-(4-fluorophenyl)-6-oxo-1-phenyl-5-(4-(trifluoromethyl)pyrimidine-2-carboxamido)-4,5,6,7-tetrahydro-1H-pyrazolo[3,4-b]pyridin-3-yl) acetic acid (100 mg, 0.172 mmol, 1.00 equiv), 2-(methylamino) acetonitrile (14.4 mg, 0.206 mmol, 1.20 equiv), DIEA (66.5 mg, 0.516 mmol, 3.00 equiv) and HATU (78.3 mg, 0.206 mmol, 1.20 equiv) in DMF (2 mL) at room temperature. The mixture was stirred at room temperature for 1 hour. The reaction was purified by Column: YMC-Actus Triart C18 Column, 20*150 mm, 5 μm; Mobile Phase A: Water (10 mmol/L $NH_4HCO_3$), Mobile Phase B: ACN; Flow rate: 25 mL/min; Gradient: 36% B to 55% B in 10 min; Wave Length: 254 nm/220 nm; RT1(min): 7.18 to afford N-((4R,5S)-3-(2-((cyanomethyl)(methyl)amino)-2-oxoethyl)-7-ethyl-4-(4-fluorophenyl)-6-oxo-1-phenyl-4,5,6,7-tetrahydro-1H-pyrazolo[3,4-b]pyridin-5-yl)-4-(trifluoromethyl)pyrimidine-2-carboxamide (17 mg, 15.5%) as a white solid.

$^1$H NMR (400 MHZ, DMSO-$d_6$) δ 9.31 (d, J=6.1 Hz, 2H), 8.19 (d, J=5.1 Hz, 1H), 7.67-7.62 (m, 2H), 7.61-7.55 (m, 2H), 7.53-7.50 (m, 1H), 7.37-7.32 (m, 2H), 7.11 (t, J=8.6 Hz, 2H), 5.39-5.29 (m, 1H), 4.54 (d, J=12.7 Hz, 1H), 4.31 (d, J=17.5 Hz, 1H), 4.18 (d, J=17.3 Hz, 1H), 3.81-3.73 (m, 1H), 3.29-3.21 (m, 2H), 3.16-3.09 (m, 1H), 2.67 (s, 3H), 0.85 (t, J=6.9 Hz, 3H).

LCMS Calculated for $C_{31}H_{26}F_4N_8O_3$: 634.21; Observed (Method-C): 635.0 [M+H]. 99.81% at RT 1.007 min.

Chiral HPLC (Method-E): 96.744% at RT 3.644 min.

| | |
|---|---|
| 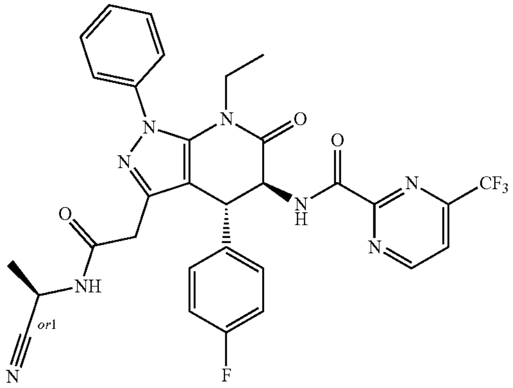 [SMILES: CCN1C(=O)[C@@H](NC(=O)c2nccc(C(F)(F)F)n2)[C@H](c2ccc(F)cc2)c2c(CC(=O)N[C@H](C)C#N)nn(-c3ccccc3)c21] | $^1$H NMR (400 MHz, DMSO-$d_6$) δ 9.35-9.26 (m, 2H), 8.25 (d, J = 7.0 Hz, 1H), 8.18 (d, J = 5.1 Hz, 1H), 7.65-7.59 (m, 2H), 7.59-7.52 (m, 2H), 7.52-7.45 (m, 1H), 7.34 (dd, J = 8.5, 5.5 Hz, 2H), 7.08 (t, J = 8.7 Hz, 2H), 5.29 (dd, J = 12.3, 9.2 Hz, 1H), 4.61-4.49 (m, 2H), 3.76-3.66 (m, 1H), 3.18-3.08 (m, 1H), 2.96 (d, J = 16.7 Hz, 1H), 2.39 (d, J = 16.7 Hz, 1H), 1.30 (d, J = 7.2 Hz, 3H), 0.81 (t, J = 7.0 Hz, 3H). LCMS Calculated for $C_{31}H_{26}F_4N_8O_3$: 634.21; Observed (Method-C): 635.1 $[M + H]^+$, 98.0% at RT 1.018 min. Chiral SFC (Method-G): 100% at RT 1.72 min. |
| 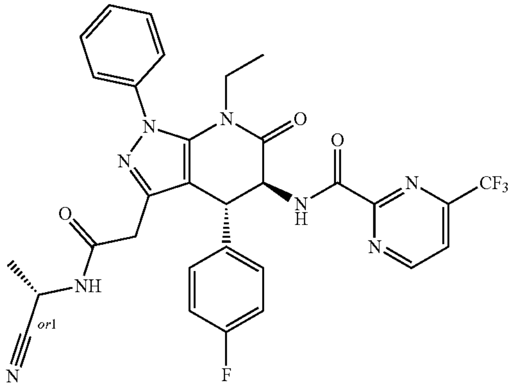 [SMILES: CCN1C(=O)[C@@H](NC(=O)c2nccc(C(F)(F)F)n2)[C@H](c2ccc(F)cc2)c2c(CC(=O)N[C@@H](C)C#N)nn(-c3ccccc3)c21] | $^1$H NMR (400 MHz, DMSO-$d_6$) δ 9.34-9.26 (m, 2H), 8.26 (d, J = 6.8 Hz, 1H), 8.18 (d, J = 5.1 Hz, 1H), 7.66-7.60 (m, 2H), 7.60-7.52 (m, 2H), 7.52-7.45 (m, 1H), 7.36-7.28 (m, 2H), 7.07 (t, J = 8.6 Hz, 2H), 5.29-5.20 (m, 1H), 4.59-4.44 (m, 2H), 3.77-3.67 (m, 1H), 3.17-3.07 (m, 1H), 3.00 (d, J = 16.7 Hz, 1H), 2.43 (d, J = 16.7 Hz, 1H), 1.29 (d, J = 7.2 Hz, 3H), 0.82 (t, J = 7.1 Hz, 3H). LCMS Calculated for $C_{31}H_{26}F_4N_8O_3$: 634.21; Observed: 635.1 $[M + H]^+$, 98.6% at RT 1.015 min. Chiral SFC (Method-G): 100% at RT 1.80 min. |

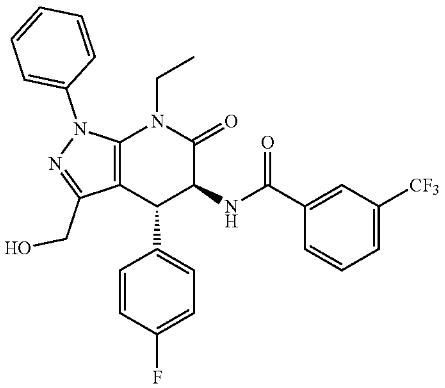

N-((4R,5S)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-3-(trifluoromethyl)benzamide (46)

A mixture of N-[(4R,5R)-7-ethyl-4-(4-fluorophenyl)-3-(hydroxymethyl)-6-oxo-1-phenyl-4H,5H-pyrazolo[3,4-b]pyridin-5-yl]-3-(trifluoromethyl)benzamide (6.00 g, 10.9 mmol, 1.00 equiv) and hydrazine hydrate (2.72 g, 54.3 mmol, 5.00 equiv) in EtOH (60 mL) was stirred for 16 h at 80° C. After completion of reaction, the resulting mixture was concentrated under reduced pressure and the residue was further purified by reverse phase flash with the method-A conditions to afford N-((4R,5S)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-3-(trifluoromethyl)benzamide (1.6 g, 26%) as an off-white solid.

LCMS Calculated for $C_{29}H_{24}F_4N_4O_3$: 552.2; Observed: 553.4 $[M+H]^+$.

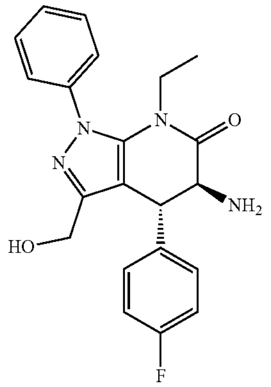

(4R,5S)-5-amino-7-ethyl-4-(4-fluorophenyl)-3-(hydroxymethyl)-1-phenyl-1,4,5,7-tetrahydro-6H-pyrazolo[3,4-b]pyridin-6-one (47)

To a solution of N-((4R,5S)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-3-(trifluoromethyl)benzamide (1.50 g, 2.72 mmol, 1.00 equiv) in dioxane (10 mL) was added conc·HCl (10 mL). Then the reaction mixture was stirred at 100° C. for 16 h. After completion of the reaction, the reaction mixture was quenched with saturated sodium bicarbonate 30 mL. The aqueous layer was extracted with ethyl acetate (30 mL). Then the combined organic phase was washed with brine, dried over anhydrous $Na_2SO_4$ and concentrated under reduced pressure to give crude product. The crude product (4R,5S)-5-amino-7-ethyl-4-(4-fluorophenyl)-3-(hydroxymethyl)-1-phenyl-4H,5H-pyrazolo[3,4-b]pyridin-6-one (1 g, crude) as a yellow oil, which was used in the next step directly without further purification.

LCMS Calculated for $C_{21}H_{21}FN_4O_2$: 380.1; Observed: 381.2 $[M+H]^+$.

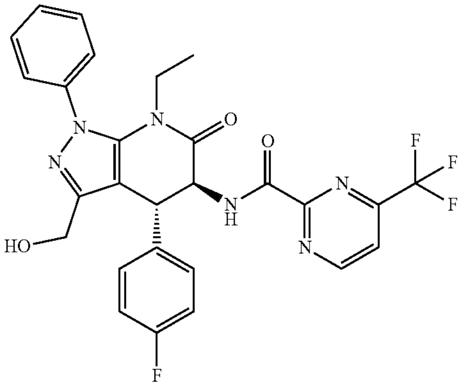

N-((4R,5S)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-4-(trifluoromethyl)pyrimidine-2-carboxamide (48)

To a stirred solution of 4-(trifluoromethyl)pyrimidine-2-carboxylic acid (505 mg, 2.63 mmol, 1.00 equiv), HATU (1.45 g, 3.94 mmol, 1.50 equiv) and DIEA (1.02 g, 7.89 mmol, 3.00 equiv) in anhydrous DMF (10 mL) was added (4R,5R)-5-amino-7-ethyl-4-(4-fluorophenyl)-3-(hydroxymethyl)-1-phenyl-4H,5H-pyrazolo[3,4-b]pyridin-6-one (1.00 g, 2.63 mmol, 1.00 equiv) at 25° C. The mixture was stirred for 3 h. After completion of reaction, the reaction mixture was diluted with water 30 mL. The aqueous layer was extracted with ethyl acetate (50 mL). The combined organic phase was washed with brine (30 mL), dried over anhydrous sodium sulfate and concentrated under reduced pressure to give crude product which was further purified by column chromatography using 70 to 75 ethyl acetate in petroleum ether gradient to afford desired compound N-((4R,5S)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-4-(trifluoromethyl)pyrimidine-2-carboxamide (650 mg, 44.6%) as a brown solid.

$^1H$ NMR (300 MHZ, Chloroform-$d_6$) δ 9.13 (d, J=5.1 Hz, 1H), 8.27 (d, J=9.6 Hz, 1H), 8.01 (s, 1H), 7.76 (d, J=5.1 Hz, 1H), 7.53 (d, J=4.2 Hz, 4H), 7.50-7.37 (m, 2H), 7.03 (t, J=8.4 Hz, 2H), 5.49 (dd, J=12.6, 9.6 Hz, 1H), 4.29 (d, J=12.6 Hz, 1H), 4.05-3.78 (m, 3H), 3.19 (dq, J=14.1, 7.2 Hz, 1H), 0.92 (t, J=7.2 Hz, 3H).

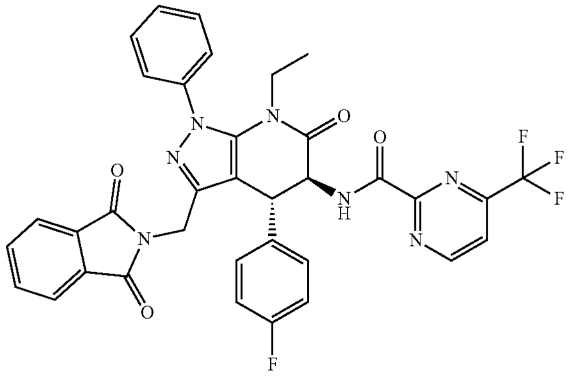

N-((4R,5S)-3-((1,3-dioxoisoindolin-2-yl)methyl)-7-ethyl-4-(4-fluorophenyl)-6-oxo-1-phenyl-4,5,6,7-tetrahydro-1H-pyrazolo[3,4-b]pyridin-5-yl)-4-(trifluoromethyl)pyridmidine-2-carboxamide (49)

To a degassed solution of N-((4R,5S)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-4-(trifluoromethyl) pyrimidine-2-carboxamide (650 mg, 1.17 mmol, 1.00 equiv), phthalimide (259 mg, 1.76 mmol, 1.50 equiv) and $PPh_3$ (922 mg, 3.52 mmol, 3.00 equiv) in THF (10 mL) was added DIAD (711 mg, 3.52 mmol, 3.00 equiv) at 0° C. Then the reaction mixture was stirred at 25° C. for 3 h. After completion of reaction, the reaction mixture was diluted with water 30 mL. The aqueous layer was extracted with ethyl acetate (50 mL). The combined organic phase was washed with brine (30 mL), dried over anhydrous sodium sulfate and concentrated under reduced pressure to give crude product which was further purified by column chromatography using 40 to 50 ethyl acetate in PE gradient to afford desired compound N-((4R,5S)-3-((1,3-dioxoisoindolin-2-yl)methyl)-7-ethyl-4-(4-fluorophenyl)-6-oxo-1-phenyl-4,5,6,7-tetrahydro-1H-pyrazolo[3,4-b]pyridin-5-yl)-4-(trifluoromethyl)pyrimidine-2-carboxamide (750 mg, 93%) as a yellow solid.

LCMS Calculated for $C_{35}H_{25}F_4N_7O_4$: 683.2; Observed: 684.1 $[M+H]^+$.

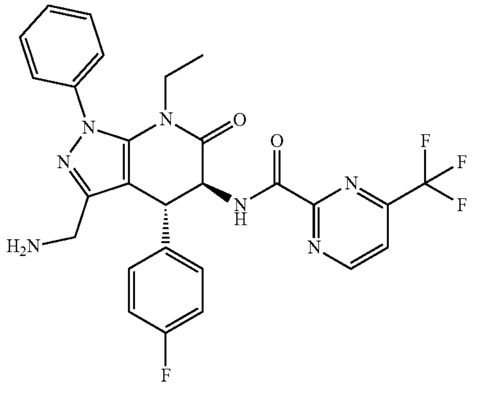

N-((4R,5S)-3-(aminomethyl)-7-ethyl-4-(4-fluorophenyl)-6-oxo-1-phenyl-4,5,6,7-tetrahydro-1H-pyrazolo[3,4-b]pyridin-5-yl)-4-(trifluoromethyl)pyridmidine-2-carboxamide (50)

To a stirred solution of N-((4R,5S)-3-((1,3-dioxoisoindolin-2-yl)methyl)-7-ethyl-4-(4-fluorophenyl)-6-oxo-1-phenyl-4,5,6,7-tetrahydro-1H-pyrazolo[3,4-b]pyridin-5-yl)-4-(trifluoromethyl)pyrimidine-2-carboxamide (700 mg, 1.03 mmol, 1.00 equiv) in EtOH (5 mL) was added hydrazine hydrate (321 mg, 5.14 mmol, 5.00 equiv, 80%). The reaction mixture was stirred at 25° C. for 16 h. After completion of reaction, the reaction mixture was quenched by addition of water 20 mL. The aqueous layer was extracted with ethyl acetate (30 mL). The combined organic phase was washed with brine (30 mL), dried over anhydrous sodium sulfate and concentrated under reduced pressure to give crude product which was purified by reverse phase flash with the condition (HCl solution, 0.36% %). The solution was basified to pH 8-9 with $NaHCO_3$. The resulting mixture was extracted with ethyl acetate (3×50 mL). The combined organic layers were washed with brine (1×50 mL), dried over anhydrous $Na_2SO_4$. After filtration, the filtrate was concentrated under reduced pressure to afford N-((4R,5S)-3-(aminomethyl)-7-ethyl-4-(4-fluorophenyl)-6-oxo-1-phenyl-4,5,6,7-tetrahydro-1H-pyrazolo[3,4-b]pyridin-5-yl)-4-(trifluoromethyl) pyrimidine-2-carboxamide (500 mg, 79%) as a brown solid.

$^1H$ NMR (300 MHZ, DMSO-$d_6$) δ 9.13 (d, J=5.1 Hz, 1H), 8.27 (d, J=9.6 Hz, 1H), 7.75 (d, J=5.1 Hz, 1H), 7.53 (d, J=4.2 Hz, 4H), 7.47-7.37 (m, 2H), 7.02 (t, J=8.7 Hz, 2H), 5.47 (dd, J=12.6, 9.6 Hz, 1H), 4.27 (d, J=12.6 Hz, 1H), 3.89 (dq, J=14.1, 7.2 Hz, 1H), 3.32-2.97 (m, 3H), 0.92 (t, J=6.9 Hz, 3H).

LCMS Calculated for: $C_{27}H_{23}F_4N_7O_2$: 553.1; Observed: 554.2 $[M+H]^+$.

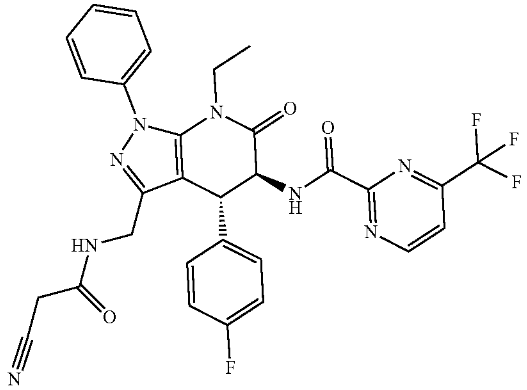

25. Synthesis of N-((4R,5S)-3-(cyanoacetamido)methyl)-7-ethyl-4-(4-fluorophenyl)-6-oxo-1-phenyl-4,5,6,7-tetrahydro-1H-pyrazolo[3,4-b]pyridin-5-yl)-4-(trifluoromethyl)pyrimidine-2-carboxamide (I-452)

$^1H$ NMR (300 MHZ, DMSO-$d_6$) δ 9.34 (d, J=9.1 Hz, 1H), 9.30 (d, J=5.0 Hz, 1H), 8.27 (d, J=4.9 Hz, 1H), 8.19 (d, J=5.1 Hz, 1H), 7.70-7.61 (m, 2H), 7.61-7.47 (m, 3H), 7.39 (dd, J=8.5, 5.5 Hz, 2H), 7.11 (t, J=8.6 Hz, 2H), 5.25 (dd, J=11.8, 9.1 Hz, 1H), 4.62 (d, J=11.8 Hz, 1H), 3.73 (dq, J=13.7, 6.7 Hz, 1H), 3.46 (s, 2H), 3.44 (d, J=4.7 Hz, 2H), 3.10 (dq, J=14.8, 7.8, 6.8 Hz, 1H), 0.80 (t, J=7.0 Hz, 3H).

LCMS Calculated for $C_{30}H_{24}F_4N_8O_3$: 620.19; Observed (Method-J): 621.3 $[M+H]^+$, 98.7% at RT 1.508 min.

26. Synthesis of N-((4R,5S)-3-((2-cyano-N-methylacetamido)methyl)-7-ethyl-4-(4-fluorophenyl)-6-oxo-1-phenyl-4,5,6,7-tetrahydro-1H-pyrazolo[3,4-b]pyridin-5-yl)-4-(trifluoromethyl)pyrimidine-2-carboxamide (I-402)

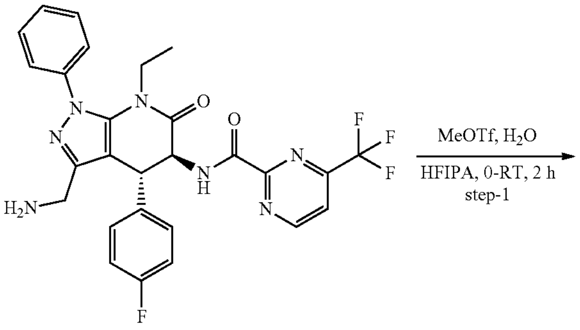

54

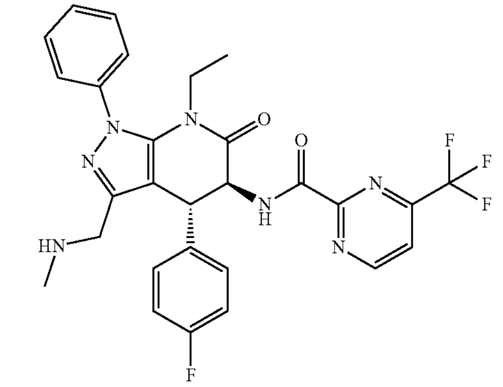

N-((4R,5S)-7-ethyl-4-(4-fluorophenyl)-3-((methylamino)methyl)-6-oxo-1-phenyl-4,5,6,7-tetrahydro-1H-pyrazolo[3,4-b]pyridin-5-yl)-4-(trifluoromethyl)pyridmidine-2-carboxamide (55)

To a stirred solution of N-((4R,5S)-3-(aminomethyl)-7-ethyl-4-(4-fluorophenyl)-6-oxo-1-phenyl-4,5,6,7-tetrahydro-1H-pyrazolo[3,4-b]pyridin-5-yl)-4-(trifluoromethyl) pyrimidine-2-carboxamide (150 mg, 0.271 mmol, 1.00 equiv) in hexafluoroisopropanol (2 mL) and $H_2O$ (9.76 mg, 0.542 mmol, 2.00 equiv) was added triflate ester (44.5 mg, 0.271 mmol, 1.00 equiv) at 0° C. Then the reaction mixture was stirred at 25° C. for 2 h. After completion of reaction, the resulting mixture was concentrated under reduced pressure to give crude product. The crude product N-((4R,5S)-7-ethyl-4-(4-fluorophenyl)-3-((methylamino)methyl)-6-oxo-1-phenyl-4,5,6,7-tetrahydro-1H-pyrazolo[3,4-b]pyridin-5-yl)-4-(trifluoromethyl)pyrimidine-2-carboxamide (150 mg, 97.5%) as a yellow oil, which was used in the next step directly without further purification.

LCMS Calculated for $C_{28}H_{25}F_4N_7O_2$: 567.2; Observed: 568.2 $[M+H]^+$.

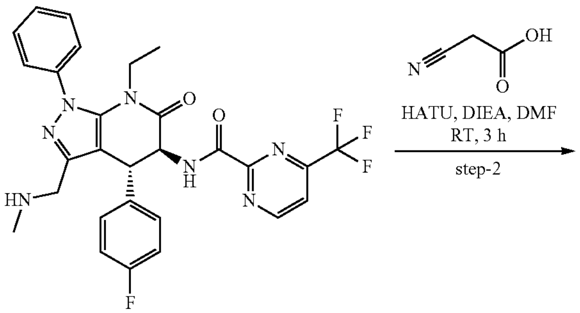

55

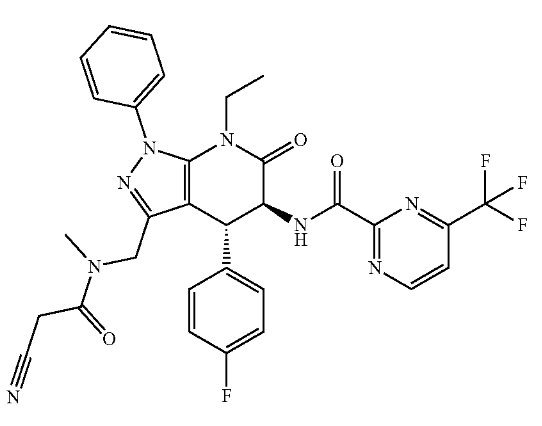

I-402

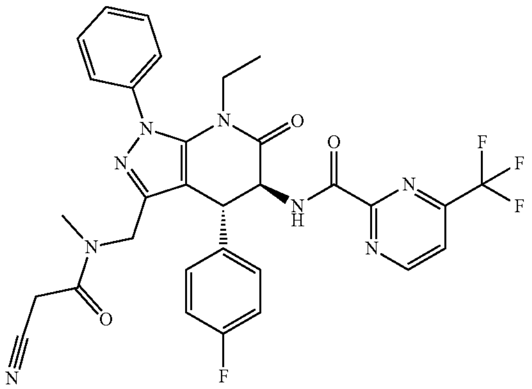

N-((4R,5S)-3-((2-cyano-N-methylacetamido)methyl)-7-ethyl-4-(4-fluorophenyl)-6-oxo-1-phenyl-4,5,6,7-tetrahydro-1H-pyrazolo[3,4-b]pyridin-5-yl)-4-(trifluoromethyl)pyridmidine-2-carboxamide (I-402)

To a stirred solution of cyanoacetic acid (43.2 mg, 0.507 mmol, 1.60 equiv), HATU (241 mg, 0.634 mmol, 2.00 equiv) and DIEA (164 mg, 1.27 mmol, 4.00 equiv) in anhydrous DMF (2 mL) was added N-((4R,5S)-7-ethyl-4-(4-fluorophenyl)-3-((methylamino)methyl)-6-oxo-1-phenyl-4,5,6,7-tetrahydro-1H-pyrazolo[3,4-b]pyridin-5-yl)-4-(trifluoromethyl)pyrimidine-2-carboxamide (180 mg, 0.317 mmol, 1.00 equiv) at 25° C. and stirred for 3 h. After completion of reaction, the reaction mixture was concentrated under reduced pressure to give crude product which was further purified by Prep-HPLC with the method-A conditions to afford N-((4R,5S)-3-((2-cyano-N-methylacetamido)methyl)-7-ethyl-4-(4-fluorophenyl)-6-oxo-1-phenyl-4,5,6,7-tetrahydro-1H-pyrazolo[3,4-b]pyridin-5-yl)-4-(trifluoromethyl)pyrimidine-2-carboxamide (29 mg, 14.4%) as a white solid.

$^1$H NMR (300 MHZ, DMSO-$d_6$) δ 9.42-9.26 (m, 2H), 8.19 (d, J=5.1 Hz, 1H), 7.70-7.62 (m, 2H), 7.62-7.31 (m, 5H), 7.26-7.04 (m, 2H), 5.32-5.06 (m, 1H), 4.67-4.48 (m, 1H), 3.98-3.44 (m, 5H), 3.28-3.05 (m, 1H), 2.79-2.55 (m, 3H), 0.80 (dt, J=7.7, 3.8 Hz, 3H).

LCMS Calculated for $C_{31}H_{26}F_4N_8O_3$: 634.2; Observed (Method-J): 635.3 [M+H]$^+$, 99.3% at RT 1.567 min.

| | |
|---|---|
| 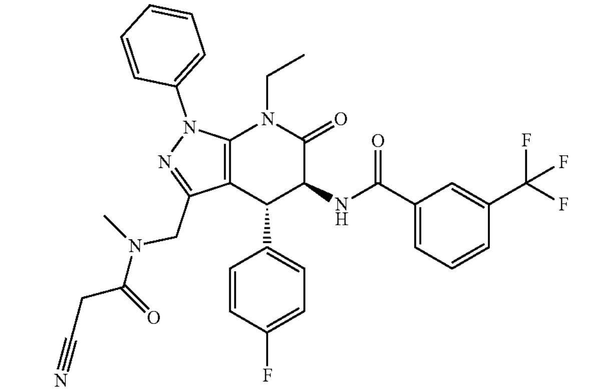 [SMILES: CCN1C(=O)[C@@H](NC(=O)c2cccc(C(F)(F)F)c2)[C@H](c2ccc(F)cc2)c2c(CN(C)C(=O)CC#N)nn(-c3ccccc3)c21] | $^1$H NMR (300 MHz, Chloroform-d) δ 7.93-7.68 (m, 3H), 7.61-7.31 (m, 8H), 7.18-7.00 (m, 2H), 6.80-6.64 (m, 1H), 5.50-5.29 (m, 1H), 4.30-3.80 (m, 3H), 3.77-3.11 (m, 4H), 3.06-2.68 (m, 3H), 0.92 (q, J = 7.2 Hz, 3H).<br>LCMS Calculated for $C_{33}H_{28}F_4N_6O_3$: 632.22; Observed (Method-AB): 633.5 [M + H]$^+$, 99.7% at 1.561 min. |

27. Synthesis of N-((4S, 5S)-3-((N-(cyanomethyl)acetamido)methyl)-7-ethyl-4-(4-fluorophenyl)-6-oxo-1-phenyl-4,5,6,7-tetrahydro-1H-pyrazolo[3,4-b]pyridin-5-yl)-3-(trifluorophenyl)benzamide (I-542)

-continued

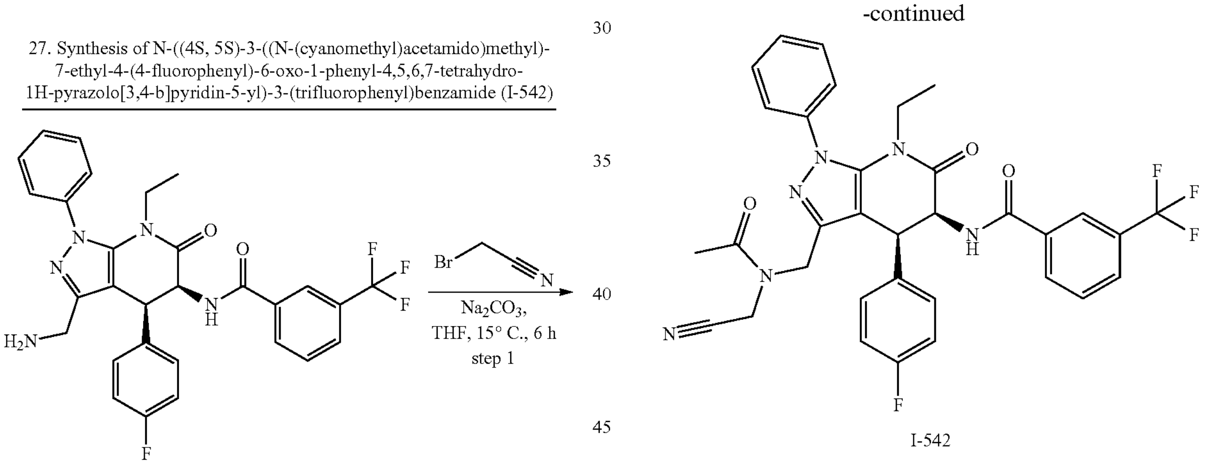

56

I-542

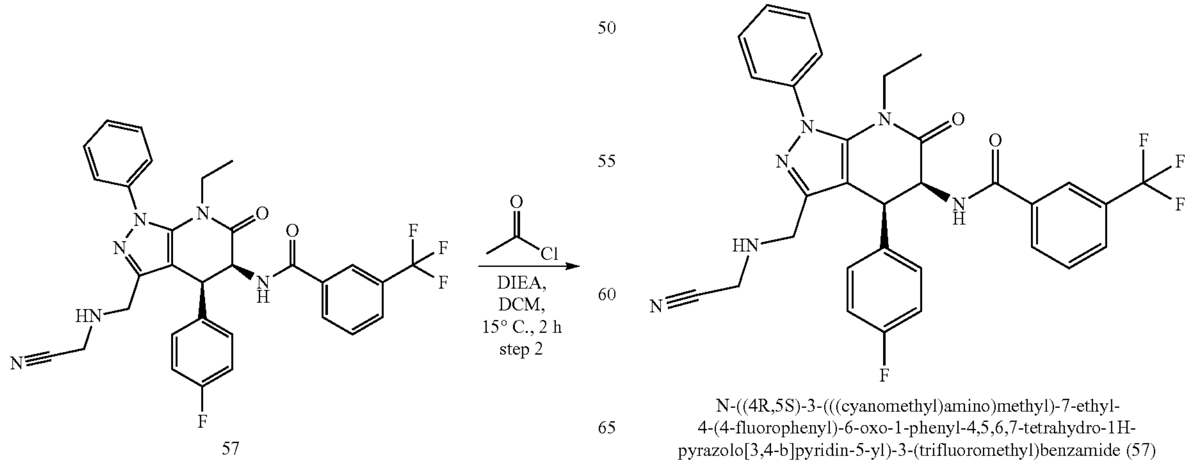

57

N-((4R,5S)-3-(((cyanomethyl)amino)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (57)

To a stirred solution of N-((4S,5S)-3-(aminomethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl) benzamide (400 mg, 0.435 mmol, 1.00 equiv, 60%) and $Na_2CO_3$ (184 mg, 1.74 mmol, 4.00 equiv) in anhydrous THF (4 mL) was added 2-bromoacetonitrile (57.4 mg, 0.479 mmol, 1.10 equiv) at 15° C. and the solution was stirred for 6 h. After completion of reaction, the reaction mixture was concentrated under reduced pressure to give crude product which was further purified by column chromatography, eluted with petroleum ether/ethyl acetate (70:30) to afford desired compound N-((4S,5S)-3-(((cyanomethyl)amino) methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (250 mg, 97.3%) as a brown solid.

$^1$H NMR (300 MHZ, DMSO-$d_6$) δ 8.54 (d, J=7.3 Hz, 1H), 8.11.07 (m, 2H), 7.92 (d, J=7.8 Hz, 1H), 7.81-7.47 (m, 7H), 7.23-6.91 (m, 5H), 5.52 (t, J=7.3 Hz, 1H), 4.67 (d, J=7.3 Hz, 1H), 3.91 (dd, J=14.3, 7.2 Hz, 1H), 3.63 (qd, J=13.7, 5.1 Hz, 2H), 3.52-3.44 (m, 2H), 3.05 (dq, J=12.6, 6.0, 5.6 Hz, 1H), 2.79 (t, J=6.4 Hz, 1H), 0.92 (t, J=7.0 Hz, 3H).

N-((4S,5S)-3-((N-(cyanomethyl)acetamido)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benazmide (I-542)

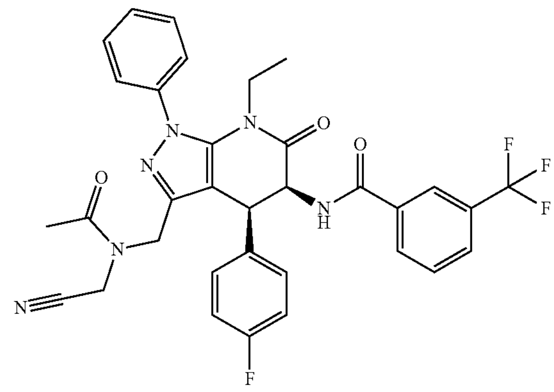

To a stirred solution of N-((4S,5S)-3-(((cyanomethyl) amino)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (100 mg, 0.169 mmol, 1.00 equiv) in anhydrous DCM (1 mL) was added DIEA (65.7 mg, 0.507 mmol, 3.00 equiv) and acetyl chloride (26.6 mg, 0.338 mmol, 2.00 equiv) at 15° C. and stirred for 2 h. After completion of reaction, the reaction mixture was concentrated under reduced pressure to give crude product. The crude was further purified by Prep-HPLC with the method-A conditions to afford N-[(4S,5S)-3-{[N-(cyanomethyl)acetamido]methyl}-7-ethyl-4-(4-fluorophenyl)-6-oxo-1-phenyl-4H,5H-pyrazolo[3,4-b]pyridin-5-yl]-3-(trifluoromethyl) benzamide (55 mg, 51.1%) as a brown solid.

$^1$H NMR (300 MHZ, DMSO-$d_6$) δ 8.62-8.47 (m, 1H), 8.24-8.09 (m, 2H), 7.91 (d, J=7.8 Hz, 1H), 7.78-7.65 (m, 3H), 7.64-7.48 (m, 3H), 7.15-6.80 (m, 4H), 5.61-5.38 (m, 1H), 5.02-4.35 (m, 3H), 4.33-4.05 (m, 2H), 3.96-3.81 (m, 1H), 3.09-2.89 (m, 1H), 1.95-1.48 (m, 3H), 0.88 (t, J=7.0 Hz, 3H).

LCMS Calculated for $C_{33}H_{28}F_4N_6O_3$: 632.2; Observed (Method-Q): 633.3 [M+H]$^+$, 99.6% at RT 1.643 min.

28. Synthesis of Ammonium (N-((R)-1-((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)ethyl)cyanamido)methyl hydrogen phosphate (I-160)

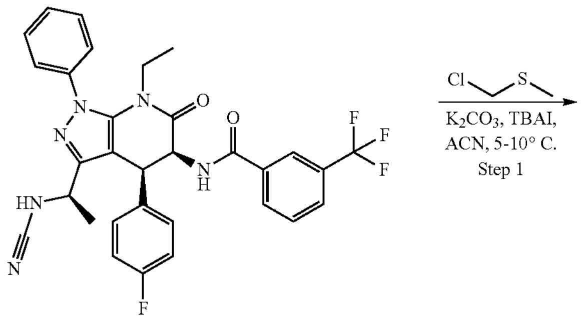

I-73

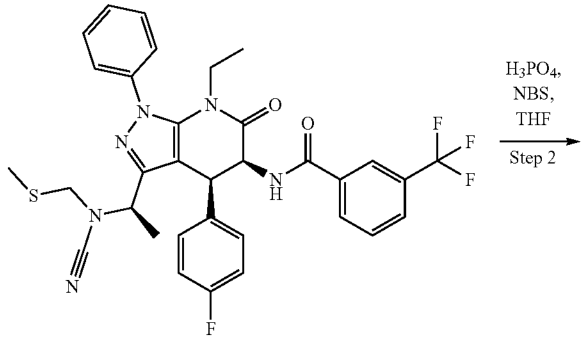

58

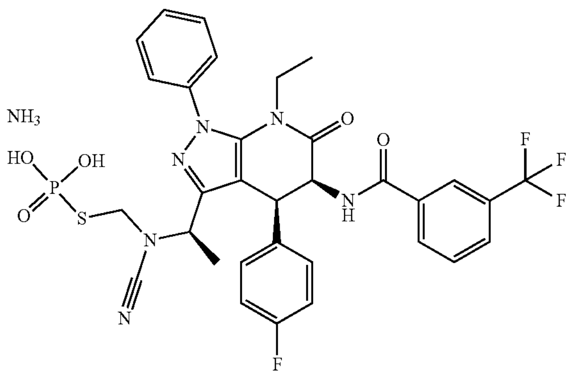

I-160

N-((4S,5S)-7-ethyl-4-(4-fluorophenyl)-3-((R)-1-(N-((methylthio)methyl)cyanamido)ethyl)-6-oxo-1-phenyl-4,5,6,7-tetrahydro-1H-pyrazolo[3,4-b]pyridin-5-yl)-3-(trifluoromethyl)benzamide (58)

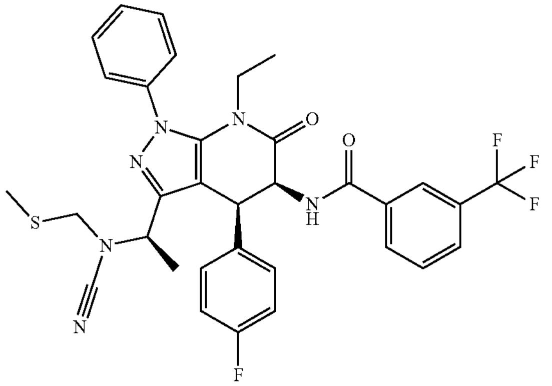

A solution of N-((4S,5S)-3-((R)-1-cyanamidoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (5.00 g, 8.47 mmol, 1 equiv), $K_2CO_3$ (1.76 g, 12.7 mmol, 1.50 equiv) and TBAI (6.25 g, 16.9 mmol, 2.0 equiv) in ACN (80 mL) was stirred for 15 min at 4° C. To the above mixture was added chloromethyl methyl sulfide (0.90 g, 9.31 mmol, 1.1 equiv) dropwise at 4° C. The resulting mixture was stirred for additional 7 h at 10° C. The reaction was monitored by LCMS and TLC. After completion of reaction, the resulting mixture was filtered, the filter cake was washed with ethyl acetate (3×15 mL). The filtrate was concentrated under reduced pressure. The residue was purified by silica gel column chromatography, eluted with petroleum ether/ethyl acetate=1/1 to afford N-((4S,5S)-7-ethyl-4-(4-fluorophenyl)-3-((R)-1-(N-((methylthio)methyl)cyanamido)ethyl)-6-oxo-1-phenyl-4,5,6,7-tetrahydro-1H-pyrazolo[3,4-b]pyridin-5-yl)-3-(trifluoromethyl)benzamide (4.68 g, 85%) as a yellow solid.

LCMS Calculated for $C_{33}H_{30}F_4N_6O_2S$: 650.21; Observed: 651.3 $[M+H]^+$.

Ammonium (N-((R)-1-((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)ethyl)cyanamido)methyl hydrogen phosphate (I-160)

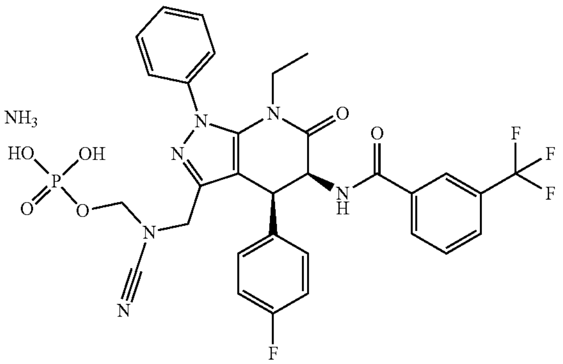

A solution of N-((4S,5S)-7-ethyl-4-(4-fluorophenyl)-3-((R)-1-(N-((methylthio)methyl) cyanamido)ethyl)-6-oxo-1-phenyl-4,5,6,7-tetrahydro-1H-pyrazolo[3,4-b]pyridin-5-yl)-3-(trifluoromethyl)benzamide (4.00 g, 6.15 mmol, 1.00 equiv), Phosphoric acid (3.00 g, 3.08 mmol, 5.00 equiv) and dry molecular sieve (4 g) in THF (80 mL) was stirred for 15 min at −50° C. under nitrogen atmosphere. To the above mixture was added NBS (5.47 g, 30.7 mmol, 5.00 equiv, solution in THF (50 mL)) dropwise at −50° C. The resulting mixture was stirred for additional 0.5 h at −50° C. The reaction was monitored by LCMS. After completion of the reaction, the resulting mixture was diluted with ACN (20 mL) at −40° C. The resulting mixture was filtered, the filter cake was washed with ACN (4×5 mL). The filtrate was basified to pH 7 with $NH_3{\cdot}H_2O/H_2O$ (V/V=1/1). The mixture was concentrated under reduced pressure. The crude product was purified by Prep-HPLC with the following conditions (Column: Ultimate XB-C18 Column, 50*250 mm, 10 μm; Mobile Phase A: Water (10 mmol/L $NH_4HCO_3$), Mobile Phase B: ACN; Flow rate: 90 mL/min; Gradient: isocratic 5%-95% 15 min; Wave Length: 254 nm/220 nm; RT1(min): 8.43) to afford Ammonium (N—((R)-1-((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)ethyl) cyanamido)methyl hydrogen phosphate (1.4 g, 31.7%) as a white solid.

$^1H$ NMR (400 MHZ, DMSO-$d_6$) δ 8.51 (d, J=7.4 Hz, 1H), 8.20-8.11 (m, 2H), 7.92 (d, J=7.8 Hz, 1H), 7.72 (d, J=7.6 Hz, 3H), 7.64-7.51 (m, 3H), 7.26 (s, 3H), 7.12 (t, J=8.7 Hz, 2H), 7.05-6.99 (m, 2H), 5.56 (t, J=7.3 Hz, 1H), 4.66-4.54 (m, 2H), 4.40 (t, J=9.4 Hz, 1H), 4.29 (t, J=9.7 Hz, 1H), 3.96-3.79 (m, 1H), 3.13-3.01 (m, 1H), 1.40 (d, J=7.0 Hz, 3H), 0.93 (t, J=7.0 Hz, 3H).

LCMS Calculated for $C_{32}H_{32}F_4N_7O_6P$: 717.21; Observed (Method-J): 699.2 $[M-NH_4]^-$, 95.0% at 0.997 min.

29. Synthesis of Sodium (N-((R)-1-((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl) ethyl)cyanamido) methyl hydrogen phosphate (I-160)

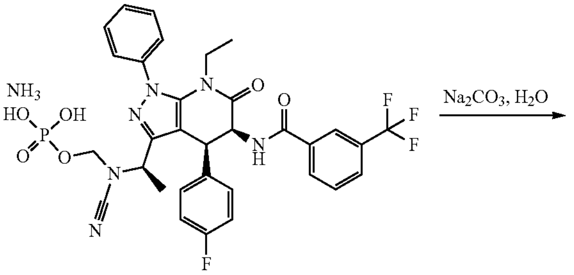

I-160

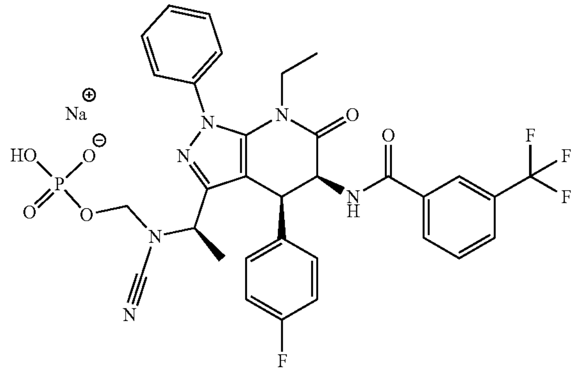

I-160

To a solution of Ammonium (N—((R)-1-((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)ethyl) cyanamido)methyl hydrogen phosphate (60.0 mg, 0.086 mmol, 1.00 equiv) in $H_2O$ (7 mL) was added $Na_2CO_3$ (18.2 mg, 0.172 mmol, 2.00 equiv) at 0° C. The mixture was stirred for 15 minutes and directly lyophilized to afford a white solid. The white solid was dissolved in ACN (3 mL). The mixture was purified by reversed-phase flash chromatography with the following conditions: column, C18 silica gel; mobile phase, $H_2O$ in ACN, 10% to 50% gradient in 10 min; detector, UV 254 nm. This resulted in sodium (N—((R)-1-((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)ethyl) cyanamido)methyl hydrogen phosphate (48 mg, 75%, IC shows 1.0 eq sodium salt) as a white solid.

$^1$H NMR (400 MHZ, Methanol-$d_4$) δ 8.13 (s, 1H), 8.04 (d, J=7.9 Hz, 1H), 7.88 (d, J=7.8 Hz, 1H), 7.75-7.54 (m, 6H), 7.15-6.98 (m, 4H), 5.49 (d, J=7.2 Hz, 1H), 4.88 (d, J=7.4 Hz, 1H), 4.68 (q, J=7.0 Hz, 1H), 4.61-4.54 (m, 1H), 4.51-4.45 (m, 1H), 4.00-3.89 (m, 1H), 3.30-3.21 (m, 1H), 1.62 (d, J=7.0 Hz, 3H), 1.02 (t, J=7.1 Hz, 3H).

LCMS Calculated for $C_{32}H_{28}F_4N_6NaO_6P$: 722.16; Observed (Method-J): 699.2 [M–Na—H]$^-$, 86.5% at RT 0.997 min.

30. Synthesis of sodium (N-((R)-1-((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)ethyl)cyanamido)methyl phosphate (I-160)

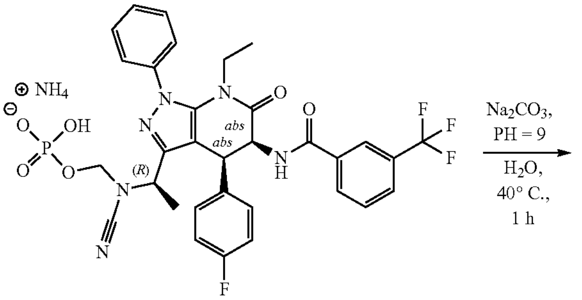

I-160

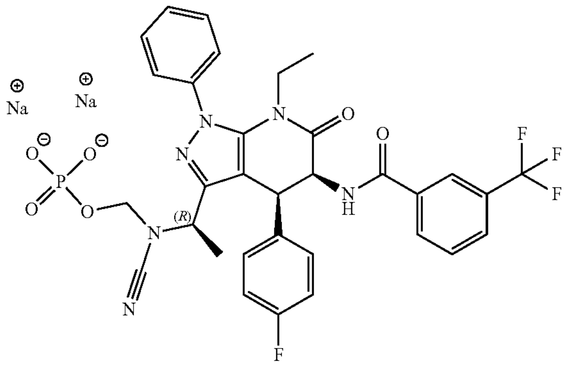

I-160

To a stirred solution of Ammonium (N—((R)-1-((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)ethyl) cyanamido)methyl hydrogen phosphate (2.00 g, 1.95 mmol, 1.00 equiv, 70%) in water (40 ml) was drop-wise added at 0° C. a saturated sodium carbonate aqueous solution until pH 9 was reached. The resulting mixture was stirred at 40° C. for 1 h. The resulting mixture was purified by reversed-phase flash chromatography with the following conditions: column, C18 silica gel; mobile phase, MeCN in Water, 10% to 50% gradient in 10 min; detector, UV 254 nm. This resulted in sodium (N—((R)-1-((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)ethyl) cyanamido)methyl phosphate (2.73 g, 90.73% yield, 99.7% purity) as a white solid.

$^1$H NMR (400 MHZ, Deuterium Oxide) δ 7.76-7.61 (m, 3H), 7.55-7.38 (m, 6H), 7.00-6.83 (m, 4H), 5.16 (d, J=7.3 Hz, 1H), 4.58 (t, J=7.4 Hz, 2H), 4.38-4.22 (m, 2H), 3.63-3.47 (m, 1H), 2.95-2.79 (m, 1H), 1.43 (d, J=7.0 Hz, 3H), 0.70 (t, J=7.0 Hz, 3H).

LCMS Calculated for $C_{32}H_{27}F_4N_6Na_2O_6P$: 744.15; Observed (Method-A): 699.2 [M–2Na—H]$^-$, 99.7% at RT 0.819 min.

2. Synthesis of N-((4S,5S)-3-((R)-1-cyanamido-3-hydroxypropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-567)

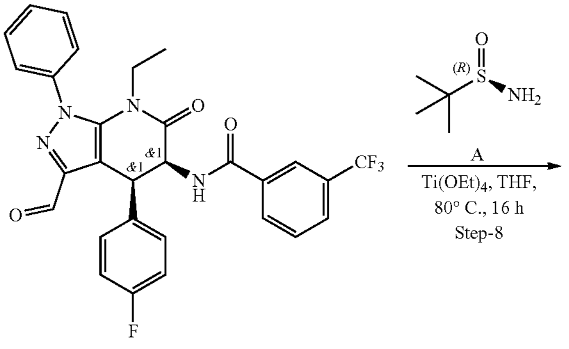

19

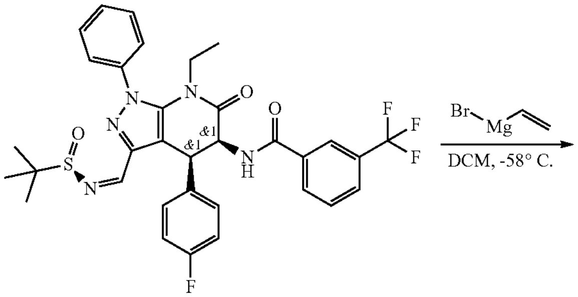

20

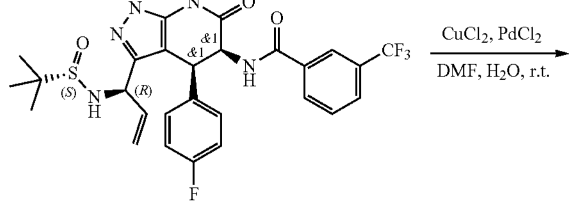

76

-continued

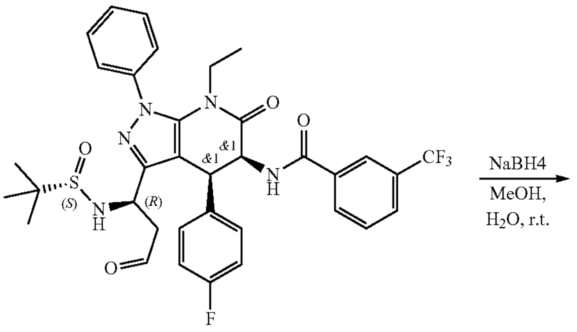

77

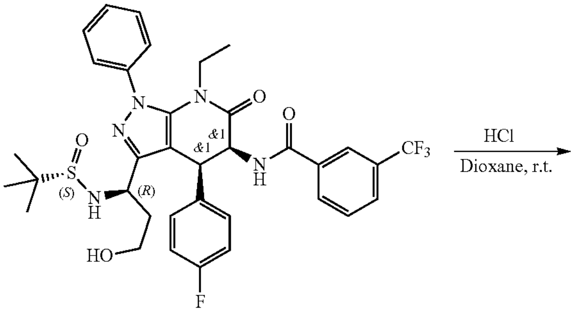

78

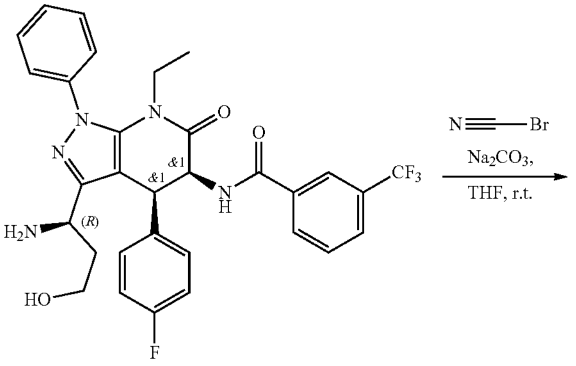

79

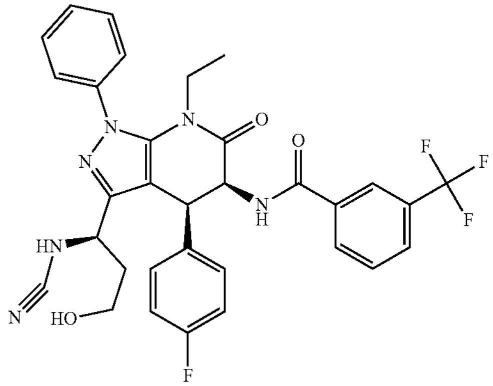

I-567

N-(rac-(4S,5S)-3-((E)-(((R)-tert-butylsulfinyl)imino)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (20)

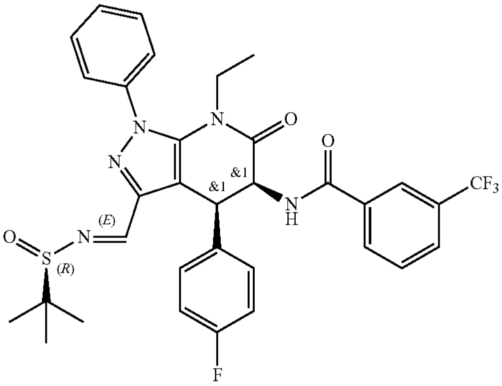

To a stirred solution of rac-N-((4R,5R)-7-ethyl-4-(4-fluorophenyl)-3-formyl-6-oxo-1-phenyl-4,5,6,7-tetrahydro-1H-pyrazolo[3,4-b]pyridin-5-yl)-3-(trifluoromethyl)benzamide (1.00 g, 1.82 mmol, 1.00 equiv) and $Ti(OEt)_4$ (1.24 g, 5.44 mmol, 3.00 equiv) in THF (10.0 mL) was added (R)-2-methylpropane-2-sulfinamide (330 mg, 2.72 mmol, 1.50 equiv) dropwise at room temperature under nitrogen atmosphere. The resulting mixture was stirred for 1 h at 80° C. under nitrogen atmosphere. The reaction was quenched with Water at room temperature. The resulting mixture was extracted with EtOAc (2×10 mL). The combined organic layers were washed with EtOAc (2×10 mL), dried over anhydrous $Na_2SO_4$. After filtration, the filtrate was concentrated under reduced pressure. The residue was purified by silica gel column chromatography, eluted with petroleum ether/ethyl acetate (1:1) to afford N-(rac-(4S,5S)-3-((E)-(((R)-tert-butylsulfinyl)imino)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (1 g, 84.2%) as a white solid. LCMS Calculated for $C_{33}H_{31}F_4N_5O_3S$: 653.21; Observed: 654.3 $[M+H]^+$ N-(rac-(4S,5S)-3-((R)-1-(((S)-tert-butylsulfinyl)amino)allyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (76)

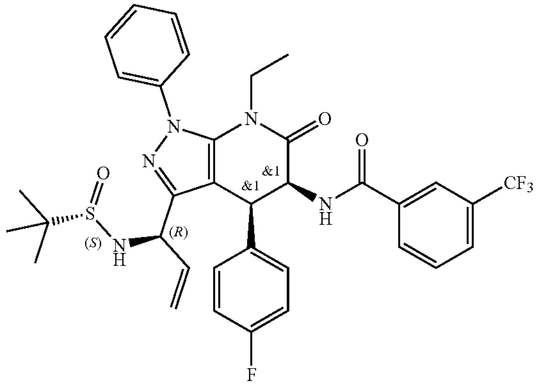

A solution of N-(rac-(4S,5S)-3-((Z)—(((S)-tert-butylsulfinyl)imino)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (1.00 g, 1.53 mmol, 1.00 equiv) in DCM (10.0 mL) was stirred for 10 min at −58° C. under nitrogen atmosphere followed by the addition of bromo (ethenyl) magnesium (15.3 mL, 124.6 mmol, 10.0 equiv) dropwise at −58° C. The solution was stirred for 2 h at −58° C. The reaction was quenched with water (30.0 mL) at −30° C. The resulting mixture was extracted with $CH_2Cl_2$ (30.0 mL). The combined organic layers were washed with brine (20.0 mL), dried over anhydrous $Na_2SO_4$. After filtration, the filtrate was concentrated under reduced pressure. The residue was purified by silica gel column chromatography, eluted with petroleum ether/THF (1:1) to afford N-(rac-(4S,5S)-3-((R)-1-(((S)-tert-butylsulfinyl)amino) allyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (550 mg, 48.5% yield, 92% purity)) as a white solid. LCMS Calculated for $C_{35}H_{35}F_4N_5O_3S$: 681.24; Observed: 682.3 [M+H]+.

N-(rac-(4S,5S)-3-((R)-1-(((S)-tert-butylsulfinyl)amino)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (77)

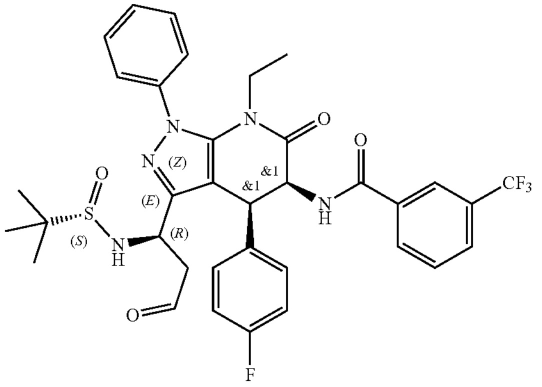

A solution of N-(rac-(4S,5S)-3-((R)-1-(((S)-tert-butylsulfinyl)amino) allyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (300 mg, 0.440 mmol, 1.00 equiv), $CuCl_2$ (4.36 mg, 0.044 mmol, 0.1 equiv) and $PdCl_2$ (78.0 mg, 0.440 mmol, 1.00 equiv) in DMF (5.25 mL) and $H_2O$ (0.75 mL) was stirred for 12 h at room temperature under nitrogen atmosphere. After completion of the reaction, the reaction mixture was quenched with $H_2O$ (50.0 mL). The resulting mixture was extracted with EtOAc (50.0 mL), dried over anhydrous $Na_2SO_4$. After filtration, the filtrate was concentrated under reduced pressure. The crude product N-(rac-(4S,5S)-3-((R)-1-(((S)-tert-butylsulfinyl)amino)-3-oxopropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (300 mg, crude) as a white solid was used in the next step directly without further purification.

LCMS Calculated for $C_{35}H_{35}F_4N_5O_4S$: 697.23; Observed: 698.3 [M+H]+.

N-(rac-(4S,5S)-3-((R)-1-(((S)-tert-butylsulfinyl)amino)-3-hydroxypropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (78)

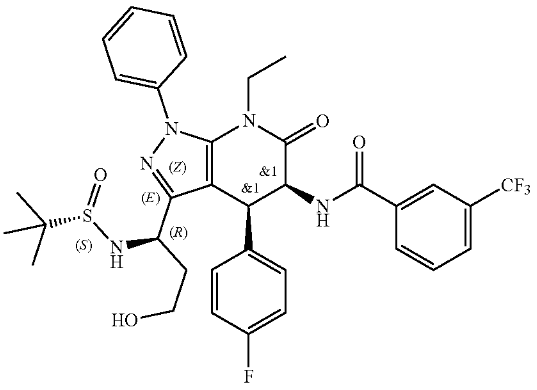

A solution of N-(rac-(4S,5S)-3-((R)-1-(((S)-tert-butylsulfinyl)amino)-3-oxopropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (200 mg, 0.287 mmol, 1.00 equiv) in MeOH (3.0 mL) was stirred for 10 min at 0° C. under air atmosphere. To the above mixture was added $NaBH_4$ (21.7 mg, 0.574 mmol, 2.00 equiv) in portions at 0° C. The resulting mixture was stirred for additional 1 h at room temperature. After completion of the reaction, the reaction mixture was quenched with $H_2O$ (2.0 mL). The resulting mixture was concentrated under reduced pressure. The residue was purified by silica gel column chromatography, eluted with Petroleum ether/ethyl acetate (1:9) to afford N-(rac-(4S,5S)-3-((R)-1-(((S)-tert-butylsulfinyl) amino)-3-hydroxypropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (100.0 mg, 32.4% yield, 65% purity) as a white solid.

LCMS Calculated for: $C_{35}H_{37}F_4N_5O_4S$: 699.25; Observed: 700.3 [M+H]+.

N-(rac-(4S,5S)-3-((R)-1-amino-3-hydroxypropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (79)

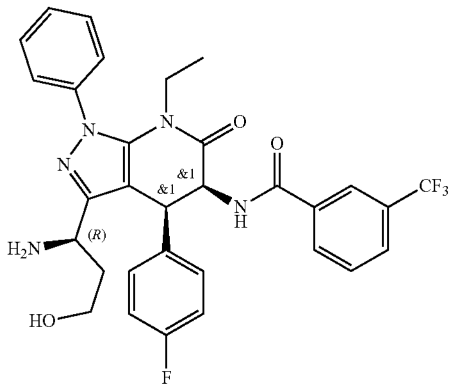

A solution of N-(rac-(4S,5S)-3-((R)-1-(((S)-tert-butylsulfinyl)amino)-3-hydroxypropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (100 mg, 0.143 mmol, 1.00 equiv) in 4M HClin 1,4-dioxane (2.0 mL) was stirred for 1 h at room temperature under air atmosphere. The resulting mixture was concentrated under reduced pressure. The crude product N-(rac-(4S,5S)-3-((R)-1-amino-3-hydroxypropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (100 mg, crude) as a white solid was used in the next step directly without further purification.

LCMS Calculated for $C_{31}H_{29}F_4N_5O_3$: 595.22; Observed: 596.3 $[M+H]^+$.

N-(rac-(4S,5S)-3-((R)-1-cyanamido-3-hydropropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-567)

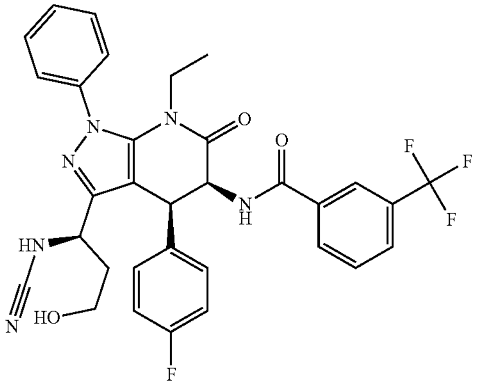

A solution of N-(rac-(4S,5S)-3-((R)-1-amino-3-hydroxypropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (100 mg, 0.168 mmol, 1.00 equiv) in THF (2.0 mL) was treated with $Na_2CO_3$ (71.1 mg, 0.672 mmol, 4.00 equiv) for 10 min at room temperature. To the above mixture was added cyanogen bromide (35.5 mg, 0.336 mmol, 2.00 equiv), the resulting mixture was stirred for additional 2 h at room temperature. The resulting mixture was concentrated under reduced pressure. The residue was purified by prep-HPLC (0.05% $NH_3 \cdot H_2O$ solution) to afford N-(rac-(4S,5S)-3-((R)-1-cyanamido-3-hydroxypropyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl) benzamide (10.0 mg, 9.4% yield, 98.4% purity) as a white solid.

$^1H$ NMR (300 MHZ, DMSO-$d_6$) δ 9.12-8.98 (m, 1H), 8.04-7.96 (m, 2H), 7.93-7.86 (m, 1H), 7.74-7.64 (m, 3H), 7.63-7.48 (m, 3H), 7.45-7.31 (m, 2H), 7.20-7.09 (m, 2H), 6.12-5.94 (m, 1H), 5.24-5.05 (m, 1H), 4.53-4.37 (m, 1H), 3.58-3.47 (m, 1H), 3.22-3.10 (m, 1H), 2.16-1.83 (m, 2H), 1.82-1.51 (m, 5H), 1.29-1.16 (m, 2H), 0.80 (q, J=7.7, 7.0 Hz, 3H).

LCMS Calculated for $C_{32}H_{28}F_4N_6O_3$: 620.22; Observed (Method-Z): 621.3 $[M+H]^+$, 98.4% at RT 1.987 min.

31. Synthesis of N-((4S,5R)-3-(((S)-2-cyano-5-oxopyrrolidin-1-yl)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-596) and N-((4S,5S)-3-(((S)-2-cyano-5-oxopyrrolidin-1-yl)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-622)

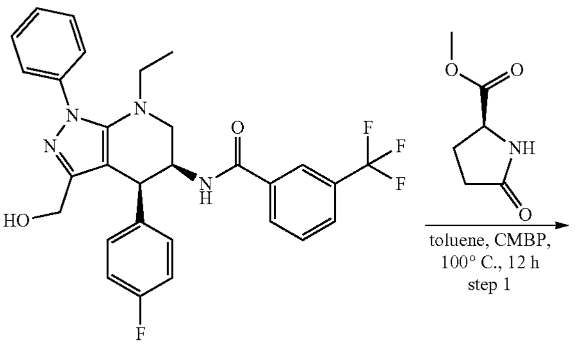

I-672

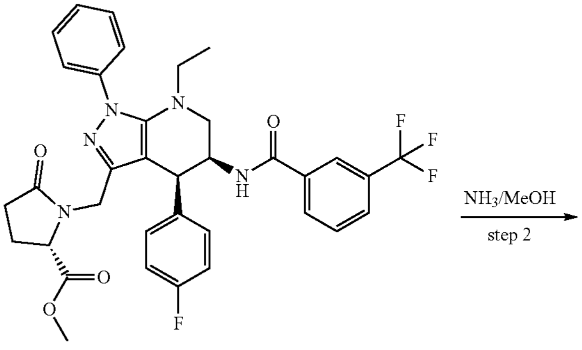

59

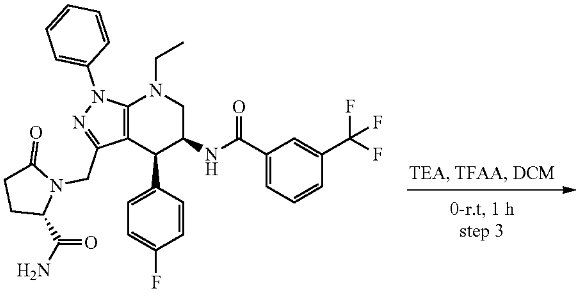

60

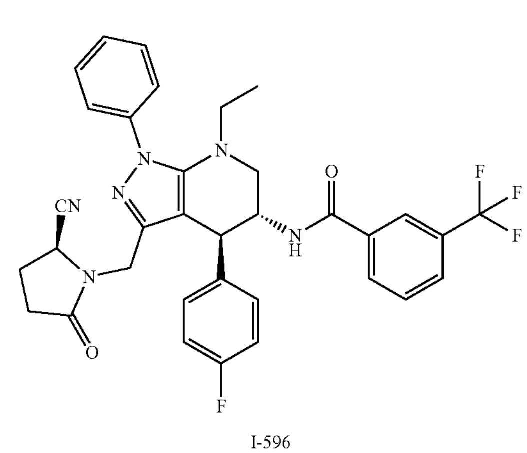

I-596

-continued

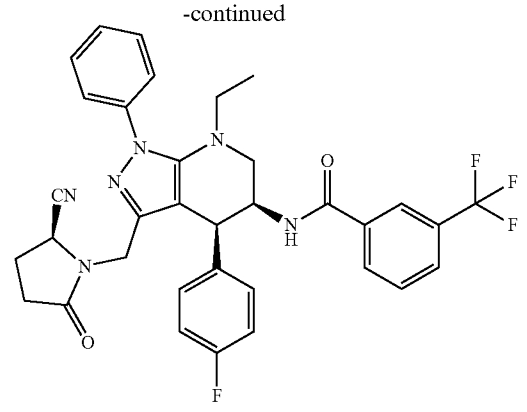

I-622 methyl (S)-1-(((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)-5-oxopyrrolidine-2-carboxylate (59)

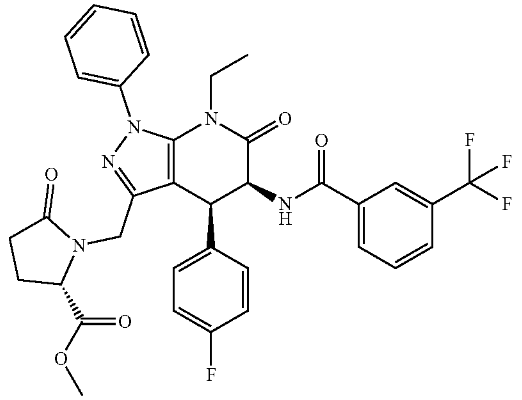

Into a 250 mL round-bottom flask, were added N-((4S,5S)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-3-(trifluoromethyl)benzamide (1.00 g, 1.81 mmol, 1.00 equiv), methyl (S)-5-oxopyrrolidine-2-carboxylate (0.39 g, 2.72 mmol, 1.50 equiv), 2-(tributylphosphanylidene)acetonitrile (0.66 g, 2.72 mmol, 1.50 equiv) in toluene (20 mL) at room temperature. The resulting mixture was stirred for 12 hours at 100° C. under nitrogen atmosphere. The mixture was allowed to cool down to room temperature, diluted with water (50 mL) and extracted with ethyl acetate (50 mL×3). The combined organic phase was washed with brine (50 mL), dried over anhydrous sodium sulfate, filtered and concentrated in vacuum. The residue was applied onto a silica gel column and eluted with petroleum ether/ethyl acetate (20% to 50% ethyl acetate) to afford methyl (S)-1-(((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)-5-oxopyrrolidine-2-carboxylate (400 mg, 96.2% purity) as a yellow solid.

LCMS Calculated for $C_{35}H_{31}F_4N_5O_5$: 677.23. Observed: 678.2 $[M+H]^+$.

(S)-1-(((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)-5-oxopyrrolidine-2-carboxamide (60)

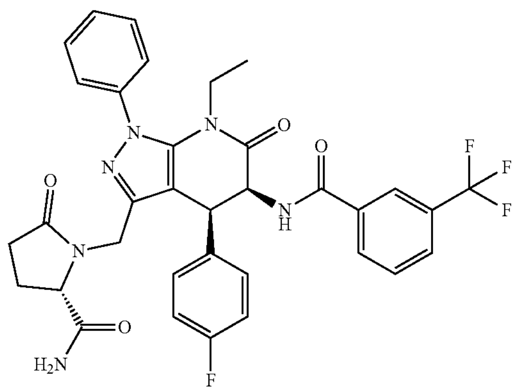

To a solution of Ammonia (7.0M in methanol) (3 mL) was added methyl (S)-1-(((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)-5-oxopyrrolidine-2-carboxylate (200 mg, 0.295 mmol, 1.00 equiv) at room temperature. The reaction mixture was stirred for 4 hours at room temperature. The resulting mixture was concentrated in vacuum to afford (S)-1-(((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)-5-oxopyrrolidine-2-carboxamide (140 mg, 90.0% purity) as a white solid, which was used for next step directly.

LCMS Calculated for $C_{34}H_{30}F_4N_6O_4$: 662.23; Observed: 663.2 $[M+H]^+$.

N-((4S,5R)-3-(((S)-2-cyano-5-oxopyrrolidin-1-yl)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-596) and N-((4S,5S)-3-(((S)-2-cyano-5-oxopyrrolidin-1-yl)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-622)

Into a 8 mL vial were added(S)-1-(((4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridin-3-yl)methyl)-5-oxopyrrolidine-2-carboxamide (130 mg, 0.196 mmol, 1.00 equiv), $Et_3N$ (79.41 mg, 0.784 mmol, 4.00 equiv) in DCM (2 mL) at room 0° C., Trifluoroacetic anhydride (82.41 mg, 0.392 mmol, 2.00 equiv) was added at 0° C. The mixture was stirred for 1 hour at 0° C., filtered and concentrated in vacuum. The residue was purified by Column: Uitimate-XB-C18 Column, 30*150 mm, 10 μm; Mobile Phase A: Water (10 mmol/L $NH_4HCO_3$+$0.05NH_3H_2O$), Mobile Phase B: ACN; Flow rate: 60 mL/min; Gradient: isocratic 35%-85% 10 min; Wave Length: 254 nm/220 nm; RT1(min): 9.2 to afford N-((4S,5R)-3-(((S)-2-cyano-5-oxopyrrolidin-1-yl)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-596) (15 mg, 99.1% purity) as a white solid and N-((4S,5S)-3-(((S)-2-cyano-5-oxopyrrolidin-1-yl)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (I-622) (24 mg, 99.9% purity) as a white solid.

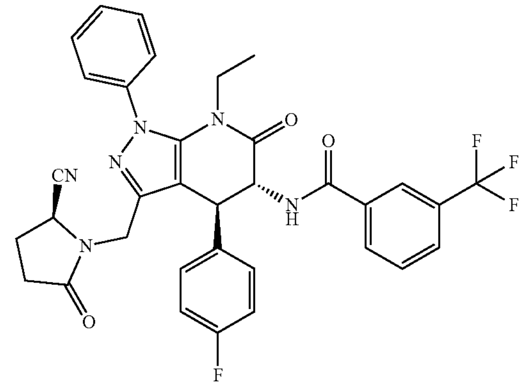 [SMILES: CCN1C(=O)[C@H](NC(=O)c2cccc(C(F)(F)F)c2)[C@@H](c2ccc(F)cc2)c2c(CN3C(=O)CC[C@H]3C#N)nn(-c3ccccc3)c21]

$^1$H NMR (400 MHz, DMSO-$d_6$) δ 9.06 (d, J = 8.5 Hz, 1H), 8.06-8.00 (m, 2H), 7.92 (d, J = 7.8 Hz, 1H), 7.75-7.65 (m, 3H), 7.64-7.51 (m, 3H), 7.46-7.38 (m, 2H), 7.17 (t, J = 8.7 Hz, 2H), 5.22-5.13 (m, 1H), 4.72-4.64 (m, 1H), 4.41 (d, J = 10.6 Hz, 1H), 3.84 (d, J = 15.7 Hz, 1H), 3.71 (d, J = 15.6 Hz, 1H), 3.67-3.57 (m, 1H), 3.28-3.18 (m, 1H), 2.34-2.23 (m, 1H), 2.19 (t, J = 7.8 Hz, 2H), 2.10-2.05 (m, 1H), 0.81 (t, J = 7.0 Hz, 3H).
LCMS Calculated for $C_{34}H_{28}F_4N_6O_3$: 644.22; Observed (Method-C): 645.2 [M + H], 99.17% at RT 1.114 min.
Chiral SFC (Method-F): 100% at RT 0.44 min.

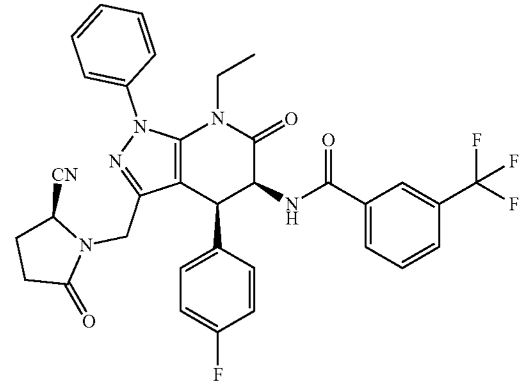 [SMILES: CCN1C(=O)[C@@H](NC(=O)c2cccc(C(F)(F)F)c2)[C@@H](c2ccc(F)cc2)c2c(CN3C(=O)CC[C@H]3C#N)nn(-c3ccccc3)c21]

$^1$H NMR (400 MHz, DMSO-$d_6$) δ 8.52 (d, J = 7.3 Hz, 1H), 8.20-8.12 (m, 2H), 7.93 (d, J = 7.8 Hz, 1H), 7.76-7.53 (m, 6H), 7.09 (t, J = 8.8 Hz, 2H), 6.98-6.90 (m, 2H), 5.49 (t, J = 7.2 Hz, 1H), 4.74-4.63 (m, 2H), 4.45 (d, J = 7.2 Hz, 1H), 4.14 (d, J = 15.1 Hz, 1H), 4.02-3.90 (m, 1H), 3.02-2.93 (m, 1H), 2.30-2.17 (m, 1H), 2.15-2.03 (m, 1H), 1.65-1.52 (m, 2H), 0.90 (t, J = 7.1 Hz, 3H).
LCMS Calculated for $C_{34}H_{28}F_4N_6O_3$: 644.22; Observed (Method-C): 645.2 [M + H], 99.95% at RT 1.276 min.
Chiral SFC (Method-A): 100% at RT 0.74 min.

Example 37: Synthesis of Compounds

1. Synthesis of (4S,5S)-N-((R*)-1-cyanoethyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamide (I-289) & (4S,5S)-N-((S*)-1-cyanoethyl)-7-ethyl-4-(4-fluorophenyl)-N-methyl-6-pxp-1-phenyl-5-(3(trifluoromethyl)benzamido)-4,5,6,7-tetrahydro-1H-pyrazolo[3,4-b]pyridine-3-carboxamide (I-300-)

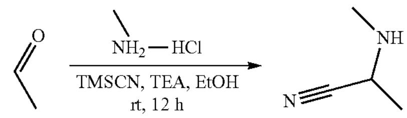

1

-continued

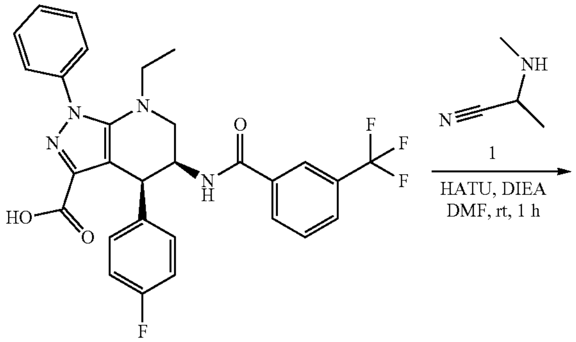

2

1

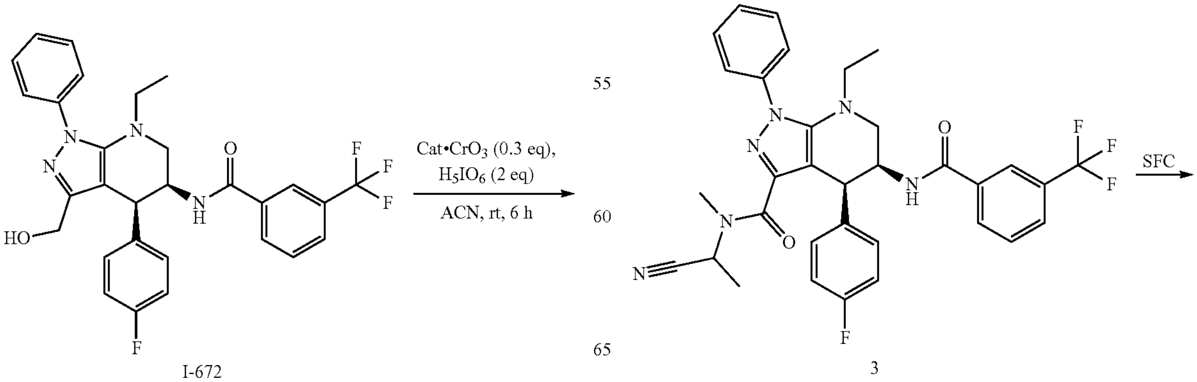

I-672

3

-continued

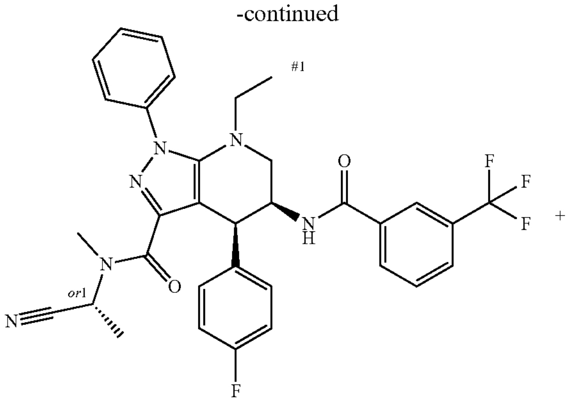

I-289

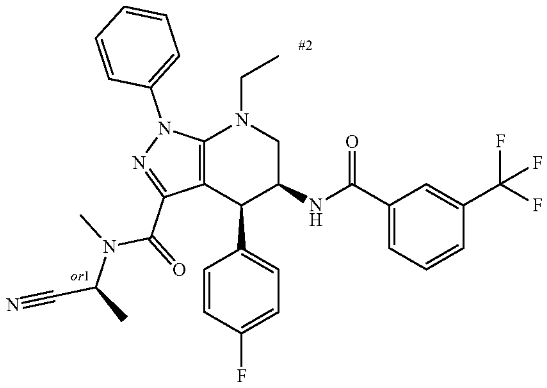

I-300

2-(methylamino)propanenitrile (1)

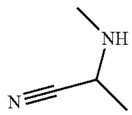

Into a 100 mL round-bottom flask were added acetaldehyde (2.00 g, 45.4 mmol, 1.00 equiv), methanamine hydrochloride (9.20 g, 136 mmol, 3.00 equiv), TEA (13.8 g, 136 mmol, 3.00 equiv), TMSCN (13.5 g, 136 mmol, 3.00 equiv) and EtOH (20 mL) at room temperature. The resulting mixture was stirred for 16 h at room temperature. The reaction was quenched with Water at room temperature. The resulting mixture was extracted with EtOAc (2×20 mL). The combined organic layers were washed with brine (2×20 mL), dried over anhydrous $Na_2SO_4$. After filtration, the filtrate was concentrated under reduced pressure. The residue was purified by silica gel column chromatography, eluted with PE/EA (0:1) to afford 2-(methylamino) propanenitrile (200 mg, 5.2%) as a light yellow oil.

(4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxylic acid (2)

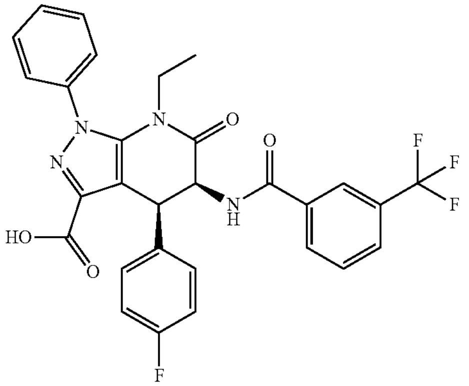

Into a 50 mL round-bottom flask were added N-((4S,5S)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-3-(trifluoromethyl)benzamide (2.00 g, 3.62 mmol, 1.00 equiv), $CrO_3$ (0.11 g, 1.087 mmol, 0.30 equiv), periodic acid (1.65 g, 7.24 mmol, 2.00 equiv) and $CH_3CN$ (20 mL) at room temperature. The resulting mixture was stirred for 2 h at room temperature. The resulting mixture was diluted with $H_2O$ (50 mL). The resulting mixture was extracted with EtOAc (3×30 mL). The combined organic layers were washed with brine (3×30 mL), dried over anhydrous $Na_2SO_4$. After filtration, the filtrate was concentrated under reduced pressure. The residue was purified by silica gel column chromatography, eluted with petroleum ether/ethyl acetate (0:1) to afford (4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxylic acid (1.5 g, 73.2%) as a yellow solid. LCMS Calculated for $C_{29}H_{22}F_4N_4O_4$: 566.16; Observed: 567.20 $[M+H]^+$.

(4S,5S)-N-(1-cyanoethyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamide (3)

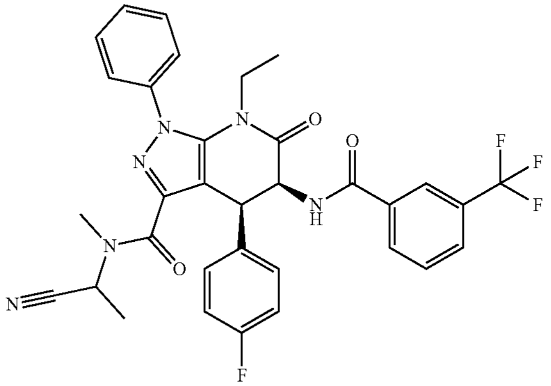

Into a 8 mL sealed tube were added (4S,5S)-7-ethyl-4-(4-fluorophenyl)-6-oxo-1-phenyl-5-[3-(trifluoromethyl) benzamido]-4H,5H-pyrazolo[3,4-b]pyridine-3-carboxylic acid (200 mg, 0.353 mmol, 1.00 equiv), DMF (2 mL), 2-(methylamino) propanenitrile (29.7 mg, 0.353 mmol, 1.00 equiv), DIEA (137 mg, 1.06 mmol, 3.00 equiv), HATU (161 mg, 0.424 mmol, 1.20 equiv) at room temperature. The resulting mixture was stirred for 2 h at room temperature. The reaction was quenched with Water at room temperature. The resulting mixture was extracted with EtOAc (2×20 mL). The combined organic layers were washed with brine (2×20 mL), dried over anhydrous $Na_2SO_4$. After filtration, the filtrate was concentrated under reduced pressure. The residue was purified by reversed-phase flash chromatography with the following conditions: Column: Sunfire Prep C18 OBD Column, 19*150 mm, 5 μm; Mobile Phase A: Water (0.1% FA), Mobile Phase B: ACN; Flow rate: 30 mL/min; Gradient: 50% B to 77% B in 8 min; Wave Length: 254 nm/220 nm; RT1(min): 7.32 to afford (4S,5S)—N-(1-cyanoethyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamide (100 mg, 44.8%) as an off-white solid.

LCMS Calculated for $C_{33}H_{28}F_4N_6O_3$: 632.22; Observed: 633.20 $[M+H]^+$.

(4S,5S)—N—((R*)-1-cyanoethyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamide (I-289) & (4S, 5S)—N—((S*)-1-cyanoethyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamide (I-300)

The 100 mg of (4S,5S)—N-(1-cyanoethyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamide was purified by Chiral-Prep-HPLC with the following conditions: Column: CHIRALPAKIH-3, 100*4.6 mm, 3 umIH30CB-BX002; Mobile Phase A: n-Hexane/THF=4/1, B: MeOH; Gradient: isocratic; Injection Volume: 1 uL. Finally, (4S,5S)—N-[(1R*)-1-cyanoethyl]-7-ethyl-4-(4-fluorophenyl)-N-methyl-6-oxo-1-phenyl-5-[3-(trifluoromethyl)benzamido]-4H,5H-pyrazolo[3,4-b]pyridine-3-carboxamide was obtained as an off-white solid (70 mg, 70.0%) and (4S,5S)—N—((S*)-1-cyanoethyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamide was obtained as an off-white solid (30 mg, 30.0%).

1. Synthesis of (4S,5S)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-545) and (4R,5R)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-575)

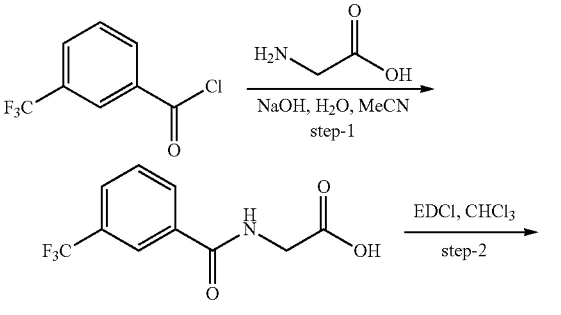

1

-continued

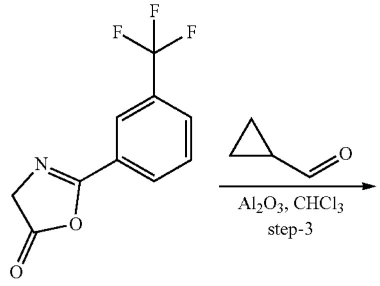

2

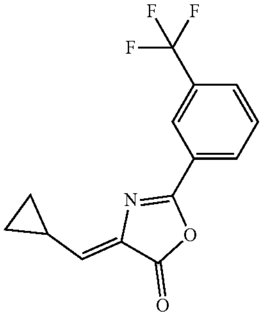

INT-B

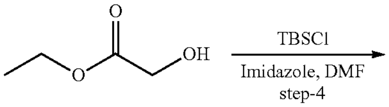

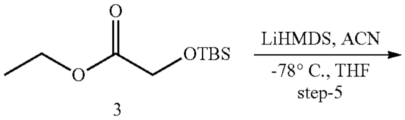

3

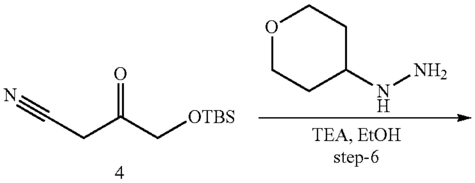

4

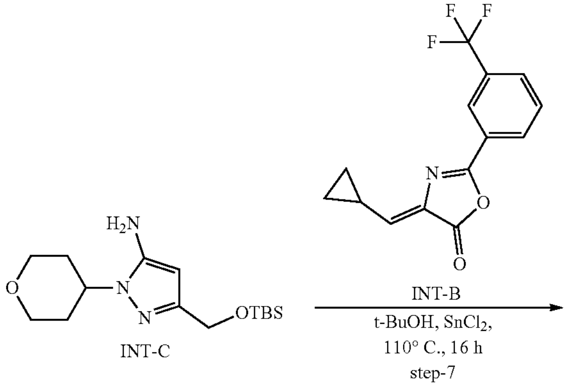

INT-C

-continued

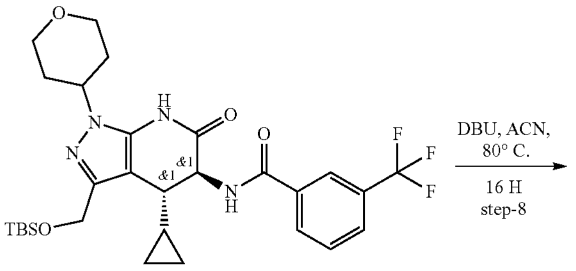

7

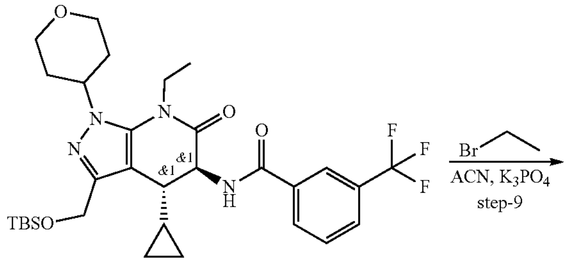

8

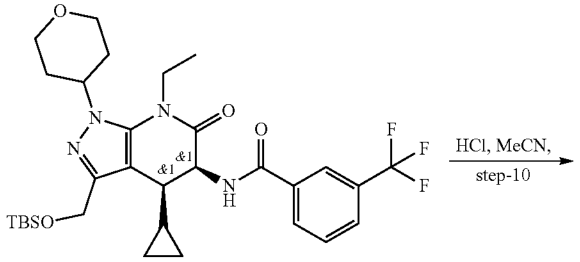

9

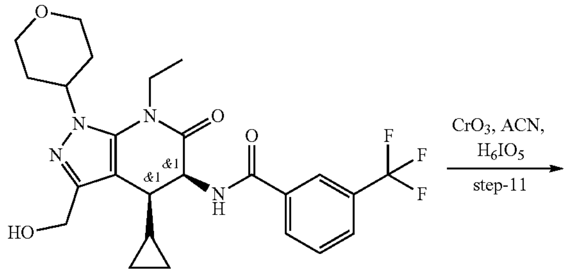

10

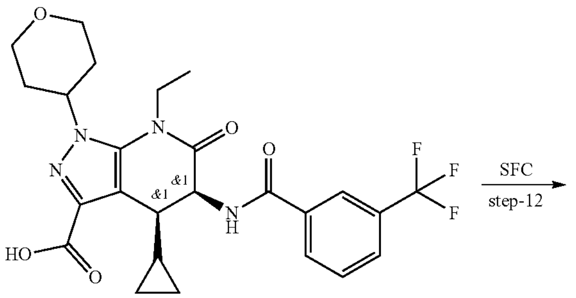

11

-continued

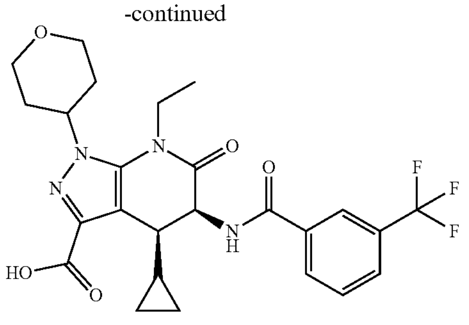

I-545

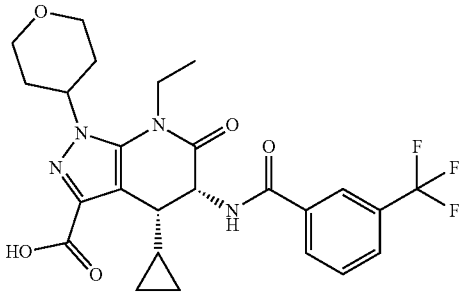 [SMILES: CCN1C(=O)[C@H](NC(=O)c2cccc(C(F)(F)F)c2)[C@H](C2CC2)c2c(C(=O)O)nn(C3CCOCC3)c21]

I-575

(3-(trifluoromethyl)benzoyl)glycine (1)

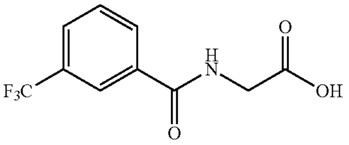

Into a 20 L 4-necked round-bottom flask were added glycine (378 g, 5.03 mol, 1.05 equiv), ACN (6 L), $H_2O$ (4 L) and NaOH (479 g, 12.0 mol, 2.50 equiv) at room temperature. To the above stirred mixture was added 3-(trifluoromethyl)benzoyl chloride (1.00 kg, 4.79 mol, 1.00 equiv) dropwise over 1 h at −5° C. The resulting mixture was stirred for additional 5 h at room temperature. The mixture was acidified to pH 6 with conc. HCl. The resulting mixture was extracted with EtOAc (2×2 L). The combined organic layers were washed with brine (2×2 L), dried over anhydrous $Na_2SO_4$. After filtration, the filtrate was concentrated under reduced pressure. The residue was purified by trituration with petroleum ether (2 L). This resulted in (3-(trifluoromethyl)benzoyl)glycine (990 g, 83%) as a white solid.

2-(3-(trifluoromethyl)phenyl)oxazol-5(4H)-one (2)

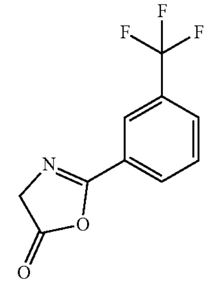

A solution of (3-(trifluoromethyl)benzoyl)glycine (350 g, 1.42 mol, 1.00 equiv) and (3-[[(ethylimino)methylidene]

amino]propyl)dimethylamine hydrochloride (299 g, 1.56 mol, 1.10 equiv) in trichloromethane (3.5 L) was stirred at room temperature for 1 h. The reaction was quenched with water (3 L) at room temperature. The resulting mixture was extracted with EtOAc (3×1 L). The combined organic layers were washed with brine (3×1 L), dried over anhydrous $Na_2SO_4$. The crude product was used in the next step directly without further purification.

2-(3-(trifluoromethyl)phenyl)oxazol-5(4H)-one (INT-B)

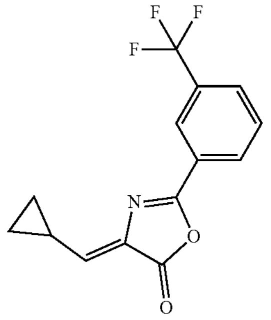

A solution of 2-(3-(trifluoromethyl)phenyl)oxazol-5 (4H)-one (300 g, 1.31 mol, 1.00 equiv) and $Al_2O_3$ (2.00 kg, 19.6 mol, 15.0 equiv), cyclopropanecarbaldehyde (82.6 g, 1.18 mol, 0.900 equiv) in trichloromethane (3 L) was stirred at room temperature for 1 h. The resulting mixture was filtered, the filter cake was washed with DCM (6×500 mL). The filtrate was concentrated under reduced pressure. The residue was purified by trituration with petroleum ether (100 mL). This resulted in (4Z)-4-(cyclopropylmethylidene)-2-[3-(trifluoromethyl)phenyl]-1,3-oxazol-5-one (93 g) as a white solid.

LCMS Calculated for $C_{14}H_{11}F_3NO_2$: 281.07; Observed: 282.1 $[M+H]^+$.

ethyl 2-((tert-butyldimethylsilyl)oxy)acetate (3)

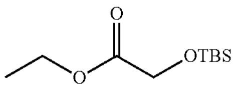

To a stirred solution of ethyl 2-hydroxyacetate (200 g, 1.92 mol, 1.00 equiv) and Imidazole (196 g, 2.88 mol, 1.50 equiv) in DMF (2 L) were added TBSCl (347 g, 2.31 mol, 1.20 equiv) at room temperature under nitrogen atmosphere. The reaction mixture was stirred for 2.0 hours at room temperature. The mixture was diluted with water (5 L). The mixture was extracted with EtOAc (2×5 L). The combined organic phase was washed with brine (5 L), dried over anhydrous sodium sulfate, filtered and concentrated in vacuum. The residue was purified by silica gel chromatography, eluted with petroleum ether:EtOAc=90:10 to afford ethyl 2-((tert-butyldimethylsilyl)oxy)acetate (320 g, 76%) as a light yellow oil.

4-((tert-butyldimethylsilyl)oxy)-3-oxobutanenitrile (4)

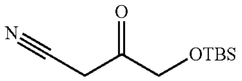

A solution of MeCN (11.3 g, 275 mmol, 1.20 equiv) in THF (500 mL) was treated with LiHMDS (59.6 mL, 298 mmol, 1.30 equiv) for 0.5 h at −78° C. under nitrogen atmosphere followed by the addition of ethyl 2-((tert-butyldimethylsilyl)oxy)acetate (50.0 g, 229 mmol, 1.00 equiv) dropwise at −78° C. The resulting mixture was stirred for 1 h at room temperature under nitrogen atmosphere. The reaction was quenched with sat. $NH_4Cl$ (aq.) at room temperature. The resulting mixture was extracted with EtOAc (2×500 mL). The combined organic layers were washed with brine (2×500 mL), dried over anhydrous $Na_2SO_4$. After filtration, the filtrate was concentrated under reduced pressure. This resulted in 4-((tert-butyldimethylsilyl)oxy)-3-oxobutanenitrile (48 g, 98%) as a yellow solid. The crude product was used in the next step directly without further purification.

3-(((tert-butyldimethylsilyl)oxy)methyl)-1-(tetrahydro-2H-pyran-4-yl)-1H-pyrazol-5-amine (INT-C)

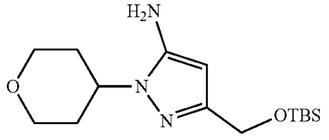

To a mixture of 4-((tert-butyldimethylsilyl)oxy)-3-oxobutanenitrile (50.0 g, 234 mmol, 1.00 equiv) and oxan-4-ylhydrazine (29.9 g, 257 mmol, 1.10 equiv) in EtOH (500 ml) was added TEA (47.4 g, 469 mmol, 2.00 equiv) at room temperature. The resulting mixture was stirred for 3 h at room temperature under air atmosphere. The resulting mixture was concentrated under vacuum. The residue was purified by silica gel column chromatography, eluted with petroleum ether/EtOAc (5:1) to afford 3-(((tert-butyldimethylsilyl)oxy)methyl)-1-(tetrahydro-2H-pyran-4-yl)-1H-pyrazol-5-amine (21 g, 28%) as a yellow oil.

LCMS Calculated for $C_{15}H_{29}N_3O_2Si$: 311.20; Observed: 312.2 $[M+H]^+$.

rac-N-((4R,5S)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (7)

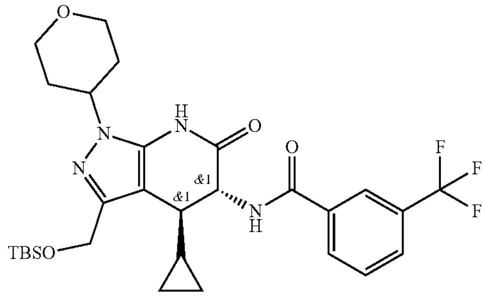

A solution of 3-(((tert-butyldimethylsilyl)oxy)methyl)-1-(tetrahydro-2H-pyran-4-yl)-1H-pyrazol-5-amine (9.00 g, 28.9 mmol, 1.00 equiv), $SnCl_2$ (0.550 g, 2.88 mmol, 0.100 equiv) and (Z)-4-(cyclopropylmethylene)-2-(3-(trifluoromethyl)phenyl)oxazol-5 (4H)-one (8.13 g, 28.9 mmol, 1.00 equiv) in t-BuOH (100 mL) was stirred at 110° C. for 16 h. The mixture was allowed to cool down to room temperature. The resulting mixture was concentrated under reduced pressure. The residue was purified by silica gel column chromatography, eluted with petroleum ether/EtOAc (2:1) to afford rac-N-((4R,5S)-3-(((tert-butyldimethylsilyl)oxy) methyl)-4-cyclopropyl-6-oxo-1-(tetrahydro-2H-pyran-4-yl)-4,5,6,7-tetrahydro-1H-pyrazolo[3,4-b]pyridin-55.2%) as a yellow oil. 5-yl)-3-(trifluoromethyl)benzamide (11.0 g, LCMS Calculated for $C_{29}H_{39}F_3N_4O_4Si$: 592.27; Observed: 593.4 $[M+H]^+$.

rac-N-((4R,5R)-3-(((tert-butyldimethylsilyl)oxy)methyl)-4-cyclopropyl-6-oxo-1-(tetrahydro-2H-pyran-4-yl)-4,5,6,6-tetrahydro-1H-pyrazolo[3,4-b]pyridin-5-yl)-3-(trifluoromethyl)benzamide (8)

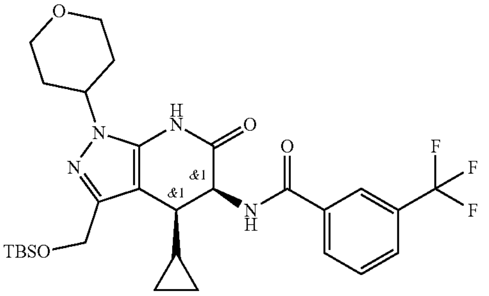

A solution of rac-N-((4R,5S)-3-(((tert-butyldimethylsilyl) oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (11.0 g, 18.5 mmol, 1.00 equiv) and DBU (10.7 g, 70.5 mmol, 3.80 equiv) in ACN (120 mL) was stirred at 80° C. for 16 h. The mixture was allowed to cool down to room temperature. The resulting mixture was concentrated under reduced pressure. The resulting mixture was diluted with $H_2O$ (200 mL). The resulting mixture was extracted with EtOAc (3x50 mL). The combined organic layers were washed with brine (1x50 mL), dried over anhydrous $Na_2SO_4$. After filtration, the filtrate was concentrated under reduced pressure. The residue was purified by silica gel column chromatography, eluted with petroleum ether/EtOAc (2:1) to afford rac-N-((4R,5R)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo [3,4-b]pyridin-5-yl)-3-(trifluoromethyl)benzamide (10.7 g, 87.5%) as a yellow oil.

LCMS Calculated for $C_{29}H_{39}F_3N_4O_4Si$: 592.27; Observed: 593.4 $[M+H]^+$.

rac-N-((4R,5R)-3-(((tert-butyldimethlsilyl)oxy)methyl)-4-cyclopropyl-7-ethyl-6-oxo-1-(tetrah ydro-2H-pyran-4-yl)-4,5,6,7-tetrahydro-1H-pyrazolo[3,4-b]pyridin-5-yl)-3-(trifluoromethyl)benzamide (9)

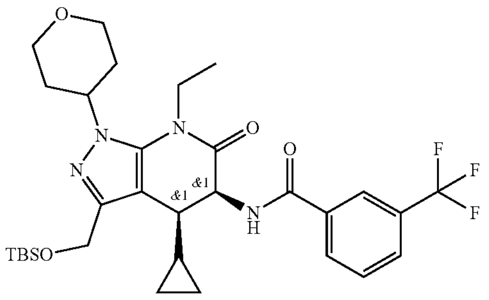

A solution of rac-N-((4R,5R)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (10.3 g, 17.3 mmol, 1.00 equiv), bromoethane (2.27 g, 20.8 mmol, 1.20 equiv) and $K_3PO_4$ (5.53 g, 26.0 mmol, 1.50 equiv) in ACN (110 mL) was stirred at 50° C. for 16 h. The mixture was allowed to cool down to room temperature. The mixture was allowed to cool down to room temperature. The resulting mixture was concentrated under reduced pressure. The residue was purified by silica gel column chromatography, eluted with petroleum ether/EtOAc (1:1) to afford rac-N-((4R,5R)-3-(((tert-butyldimethylsilyl)oxy)methyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl) benzamide (10.0 g, 83.4%) as a yellow solid.

LCMS Calculated for $C_{31}H_{43}F_3N_4O_4Si$: 620.30; Observed: 621.3 $[M+H]^+$.

rac-N-((4R,5R)-4-cyclopropyl-7-ethyl-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (10)

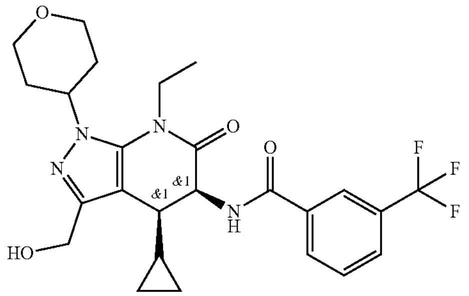

To a stirred mixture of rac-N-((4R,5R)-3-(((tert-butyldimethylsilyl)oxy)methyl)-4-cyclopropyl-7-ethyl-6-oxo-1-(tetrahydro-2H-pyran-4-yl)-4,5,6,7-tetrahydro-1H-pyrazolo [3,4-b]pyridin-5-yl)-3-(trifluoromethyl)benzamide (10.0 g, 16.1 mmol, 1.00 equiv) in MeCN (50 mL) was added HCl (50 mL, 2 mol/L in $H_2O$) in portions at room temperature. The mixture was stirred for 2 h at room temperature. The resulting mixture was concentrated under reduced pressure. The mixture was basified to pH 7 with saturated $NaHCO_3$ (aq.). The resulting mixture was extracted with EtOAc (3x100 mL). The combined organic layers were washed with $H_2O$ (1x100 mL), dried over anhydrous $Na_2SO_4$. After filtration, the filtrate was concentrated under reduced pressure. The residue was purified by silica gel column chromatography, eluted with petroleum ether/EtOAc (1:1) to afford rac-N-((4R,5R)-4-cyclopropyl-7-ethyl-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl) benzamide (7.00 g, 85.4%) as a yellow solid.

LCMS Calculated for $C_{25}H_{29}F_3N_4O_4$: 506.21; Observed: 507.2 $[M+H]^+$ rac-(4R,5R)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (11)

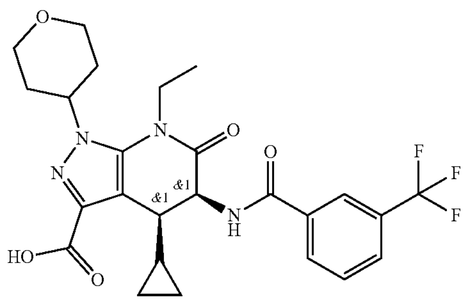

A solution of rac-N-((4R,5R)-4-cyclopropyl-7-ethyl-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (7.00 g, 13.8 mmol, 1.00 equiv), periodic acid (9.45 g, 41.4 mmol, 3.00 equiv) and $CrO_3$ (0.410 g, 4.14 mmol, 0.300 equiv) in MeCN (70 mL) was stirred at room temperature for 16 h. The reaction was quenched with $N_2S203$ (200 ml) at room temperature. The resulting mixture was extracted with EtOAc (3×100 mL). The combined organic layers were washed with brine (3×50 mL), dried over anhydrous $Na_2SO_4$. After filtration, the filtrate was concentrated under reduced pressure. The residue was purified by silica gel column chromatography, eluted with $CH_2Cl_2$/MeOH (10:1) to afford rac-(4R,5R)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (3.50 g, 47.2%) as a yellow solid.

(4S,5S)-4-cyclopropyl-7-ethyl-6-oxo-1-(tetrahydro-2H-pyran-4-yl)-5-(3-(trifluoromethyl) be nzamido)-4,5,6,7-tetrahydro-1H-pyrazolo[3,4-b]pyridine-3-carboxylic acid (I-545) and (4R, 5R)-4-cyclopropyl-7-ethyl-6-oxo-1-(tetrahydro-2H-pyran-4-yl)-5-(3-(trifluoromethyl)benza mido)-4,5,6,7-tetrahydro-1H-pyrazolo[3,4-b]pyridine-3-carboxylic acid (I-575)

The crude product rac-(4R,5R)-4-cyclopropyl-7-ethyl-6-oxo-1-(tetrahydro-2H-pyran-4-yl)-5-(3-(trifluoromethyl) benzamido)-4,5,6,7-tetrahydro-1H-pyrazolo[3,4-b]pyridine-3-carboxylic acid (3.50 g) was purified by PREP_CHIRAL_SFC with the following conditions (Column: XA-CHIRAL ART Cellulose-SC, 3*25 cm 5 um; Mobile Phase A: $CO_2$, Mobile Phase B: MEOH: DCM=2: 1 (0.1% 2M $NH_3$-MeOH); Flow rate: 80 mL/min; Gradient: isocratic 35% B; Column Temperature (C): 35; Back Pressure (bar): 100; Wave Length: 220 nm; RT1(min): 3.6; RT2(min): 4.6; Sample Solvent: MEOH; Injection Volume: 0.5 mL) to afford (4R,5R)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-575) (1.2 g, 30.4%) and (4S,5S)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-545) (0.800 g, 22.4%) as a yellow solid.

| | |
|---|---|
| 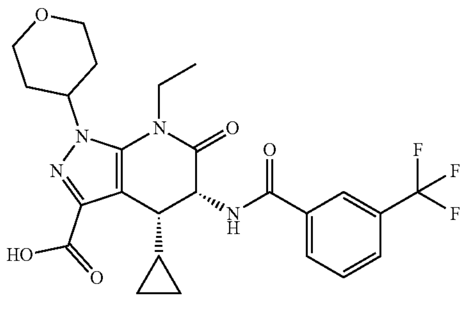 | $^1$H NMR (400 MHz, DMSO-$d_6$) δ 8.98 (d, J = 7.9 Hz, 1H), 8.31 (s, 1H), 8.25 (d, J = 7.9 Hz, 1H), 7.95 (d, J = 7.8 Hz, 1H), 7.80-7.71 (m, 1H), 5.06-4.98 (m, 1H), 4.44 (s, 1H), 4.24-4.00 (m, 2H), 3.94 (d, J = 11.5 Hz, 1H), 3.88-3.72 (m, 1H), 3.59-3.42 (m, 2H), 3.37 (m, J = 6.4 Hz, 1H), 2.50 (s, 1H), 2.26 (d, J = 12.5 Hz, 1H), 2.04 (d, J = 13.6 Hz, 1H), 1.95 (s, 1H), 1.84 (d, J = 12.8 Hz, 1H), 1.25 (t, J = 7.1 Hz, 3H), 0.91-0.44 (m, 1H), 0.29-0.12 (m, 1H), 0.12--0.25 (m, 3H). LCMS Calculated for $C_{25}H_{27}F_3N_4O_5$: 520.19; Observed (Method-J): 519.2 $[M-H]^-$, 97.1% at 0.980 min. Optical rotation: a = −10.9, (c = 0.1 g/100 mL in MeOH, T = 25° C.) |
| 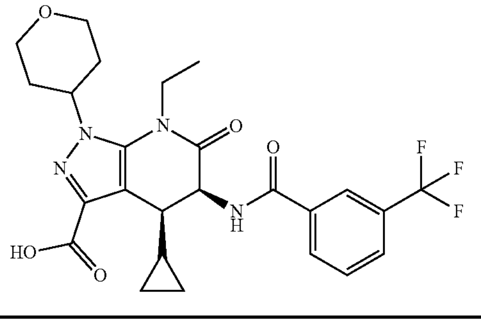 | $^1$H NMR (300 MHz, DMSO-$d_6$) δ 8.96 (d, J = 7.9 Hz, 1H), 8.31 (s, 1H), 8.24 (d, J = 7.9 Hz, 1H), 7.95 (d, J = 7.8 Hz, 1H), 7.75 (t, J = 7.8 Hz, 1H), 5.04-4.96 (m, 1H), 4.11-3.99 (m, 2H), 3.93 (d, J = 11.3 Hz, 1H), 3.87-3.77 (m, 1H), 3.58-3.38 (m, 4H), 2.28 (d, J = 13.4 Hz, 1H), 2.02 (d, J = 13.7 Hz, 2H), 1.82 (d, J = 12.6 Hz, 1H), 1.25 (t, J = 7.0 Hz, 4H), 0.85-0.76 (m, 1H), 0.46 (s, 1H), 0.18-0.10 (m, 2H), 0.08 (d, J = 7.5 Hz, 1H). LCMS Calculated for $C_{25}H_{27}F_3N_4O_5$: 520.19; Observed (Method-D): 519.2 $[M-H]^-$, 98.4% at 2.327 min. Optical rotation: a = +8.9, (c = 0.1 g/100 mL in MeOH, T = 25° C.) |

2. Synthesis of (4R,5R)-1-cyclopropyl-7-ethyl-4-(4-fluorophenyl)-6-oxo-5-(3-(trifluoromethyl)benzamido)-4,5,6,7-tetrahydro-1H-pyrazolo[3,4-b]pyridine-3-carboxylic acid (I-537) & (4S,5S)-1-cyclopropyl-7-ethyl-4-(4-fluorophenyl)-6-oxo-5-(3-(trifluoromethyl)benzamido)-4,5,6,7-tetrahydro-1H-pyrazolo[3,4-b]pyridine-3-carboxylic acid (I-477)
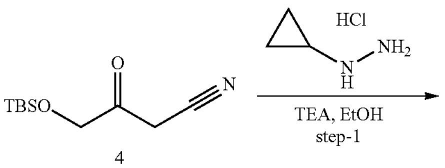
4
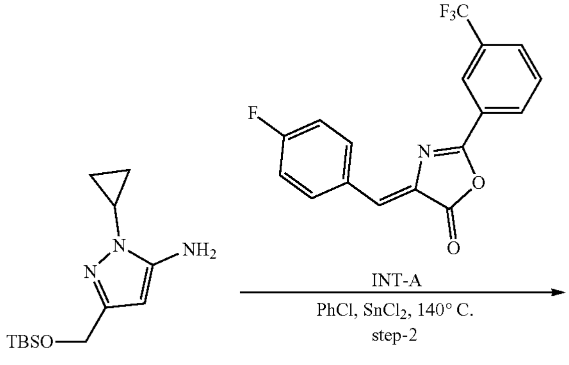
12
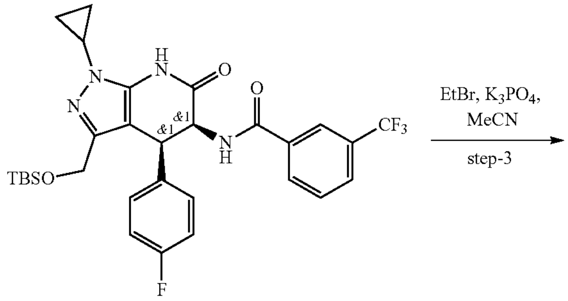
13
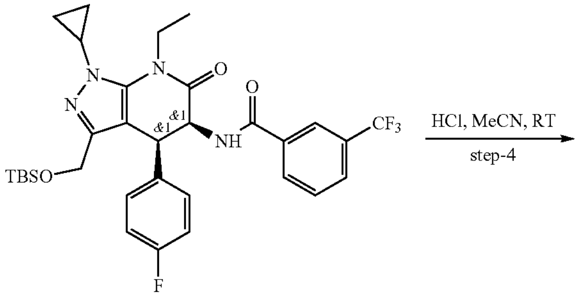
14
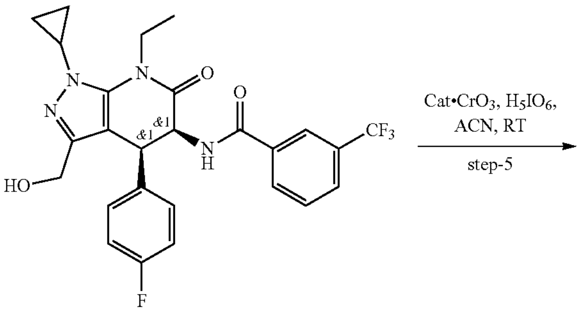
15
-continued
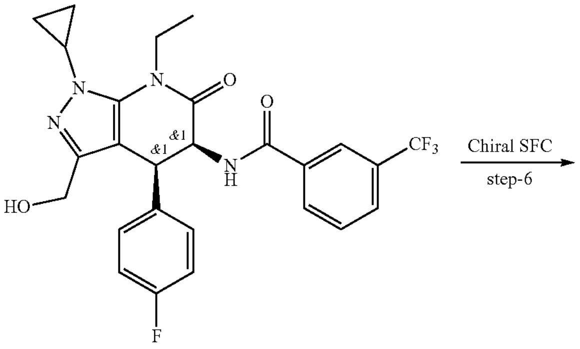
16
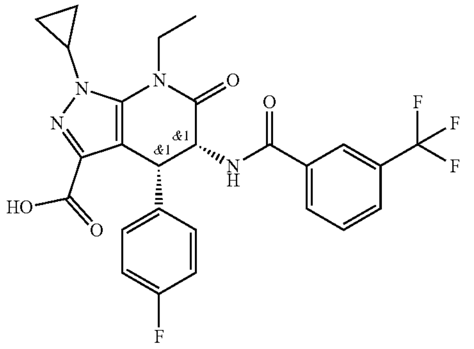
+
I-537
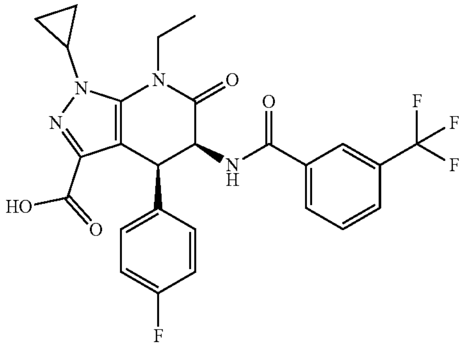
I-477
3-(((tert-butyldimethylsilyl)oxy)methyl)-1-cyclopropyl-1H-pyrazol-5-amine (12)
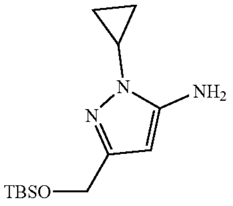

To a stirred solution of cyclopropylhydrazine hydrochloride (20.0 g, 277 mmol, 1.00 equiv) in anhydrous EtOH (400 mL) was added TEA (28.1 g, 277 mmol, 1.00 equiv) and 4-[(tert-butyldimethylsilyl)oxy]-3-oxobutanenitrile (71.0 g, 333 mmol, 1.20 equiv) at 0° C. The reaction was stirred at room temperature for 14 h. Add sodium bicarbonate (29.5 g, 351 mmol, 1.27 equiv) to the reaction solution again, and react for 6 h at 70° C. The resulting mixture was filtered and the filter cake was washed with DCM (3×200 mL). The filtrate was concentrated under reduced pressure. The residue was purified by silica gel column chromatography, eluted with petroleum ether/EtOAc (1:1) to afford 3-(((tert-butyldimethylsilyl)oxy)methyl)-1-cyclopropyl-1H-pyrazol-5-amine (17 g, 22.9%) as a yellow oil.

rac-N-((4R,5R)-3-(((tert-butyldimethylsilyl)oxy)methyl)-1-cyclopropyl-4-(4-fluorophenyl)-6-oxo-4,5,6,7-tetrahydro-1H-pyrazolo[3,4-b]pyridin-5-yl)-3-(trifluoromethyl)benzamide (13)

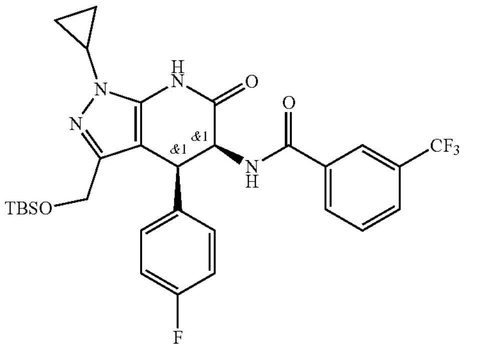

To a stirred solution of 3-(((tert-butyldimethylsilyl)oxy)methyl)-1-cyclopropyl-1H-pyrazol-5-amine (8.50 g, 31.8 mmol, 1.00 equiv) in anhydrous chlorobenzene (150 mL) was added (Z)-4-(4-fluorobenzylidene)-2-(3-(trifluoromethyl)phenyl)oxazol-5 (4H)-one (12.8 g, 38.1 mmol, 1.20 equiv) followed by catalytic amount of $SnCl_2$ (0.61 g, 3.19 mmol, 0.10 equiv) at room temperature. The reaction mixture was stirred at 140° C. for 6 h. After completion of reaction, the mixture was purified by silica gel column chromatography, eluted with petroleum ether/EtOAc (1:1) to afford rac-N-((4R,5R)-3-(((tert-butyldimethylsilyl)oxy)methyl)-1-cyclopropyl-4-(4-fluorophenyl)-6-oxo-4,5,6,7-tetrahydro-1H-pyrazolo[3,4-b]pyridin-5-yl)-3-(trifluoromethyl)benzamide (11 g, 57.4%) as a white solid.

LCMS Calculated for $C_{30}H_{34}F_4N_4O_3Si$: 602.23; Observed: 603.4 $[M+H]^+$.

rac-N-((4R,5S)-3-(((tert-butyldimethylsilyl)oxy)methyl)-1-cyclopropyl-7-ethyl-4-(4-fluorophenyl)-6-oxo-4,5,6,7-tetrahydro-1H-pyrazolo[3,4-b]pyridin-5-yl)-3-(trifluoromethyl)benzamide (14)

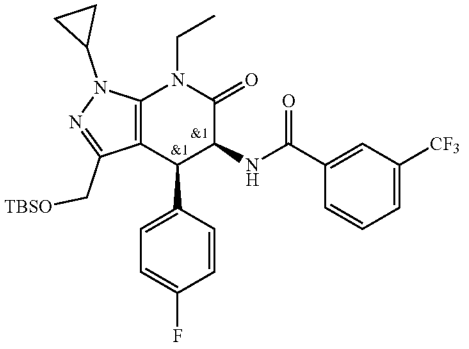

To a stirred solution of rac-N-((4R,5R)-3-(((tert-butyldimethylsilyl)oxy)methyl)-1-cyclopropyl-4-(4-fluorophenyl)-6-oxo-4,5,6,7-tetrahydro-1H-pyrazolo[3,4-b]pyridin-5-yl)-3-(trifluoromethyl)benzamide (11.0 g, 18.2 mmol, 1.00 equiv) in anhydrous MeCN (110 mL) was added $K_3PO_4$ (7.75 g, 36.5 mmol, 2.00 equiv) and bromoethane (2.39 g, 21.9 mmol, 1.20 equiv) at 0° C. The mixture was stirred at room temperature for 2 h. The resulting mixture was concentrated under reduced pressure. The residue was purified by silica gel column chromatography, eluted with petroleum ether/EtOAc (1:1) to afford rac-N-((4R,5R)-3-(((tert-butyldimethylsilyl)oxy)methyl)-1-cyclopropyl-7-ethyl-4-(4-fluorophenyl)-6-oxo-4,5,6,7-tetrahydro-1H-pyrazolo[3,4-b]pyridin-5-yl)-3-(trifluoromethyl)benzamide (8.4 g, 72.9%) as a white solid.

LCMS Calculated for $C_{32}H_{38}F_4N_4O_3Si$: 630.26; Observed: 631.3 $[M+H]^+$.

rac-N-((4R,5R)-1-cyclopropyl-7-ethyl-4-(4-fluorophenyl)-3-(hydroxymethyl)-6-oxo-4,5,6,7-tetrahydro-1H-pyrazolo[3,4-b]pyridin-5-yl)-3-(trifluoromethyl)benzamide (15)

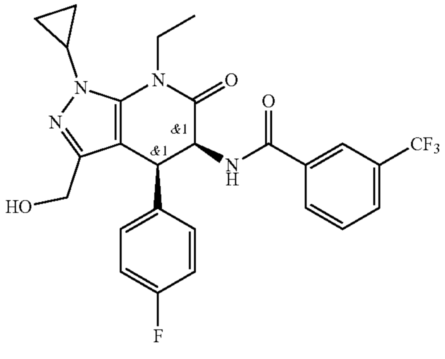

To a stirred solution of rac-N-((4R,5R)-3-(((tert-butyldimethylsilyl)oxy)methyl)-1-cyclopropyl-7-ethyl-4-(4-fluorophenyl)-6-oxo-4,5,6,7-tetrahydro-1H-pyrazolo[3,4-b]pyridin-5-yl)-3-(trifluoromethyl)benzamide (7.00 g, 11.1 mmol, 1.00 equiv) in anhydrous MeCN (70 mL) was added 6 M HCl (70 mL) at 0° C. The reaction mixture was stirred at room temperature for 2 h. The resulting mixture was concentrated under reduced pressure. The residue was neutralized to pH 9 with saturated $Na_2CO_3$ (aq.). The aqueous layer was extracted with $CH_2Cl_2$ (3×100 mL). The resulting mixture was concentrated under reduced pressure. This resulted in rac-N-((4R,5R)-1-cyclopropyl-7-ethyl-4-(4-fluorophenyl)-3-(hydroxymethyl)-6-oxo-4,5,6,7-tetrahydro-1H-pyrazolo[3,4-b]pyridin-5-yl)-3-(trifluoromethyl)benzamide (5.4 g, crude) as a white solid. LCMS Calculated for $C_{26}H_{24}F_4N_4O_3$: 516.18; Observed: 517.1 $[M+H]^+$.

rac-(4R,5R)-1-cyclopropyl-7-ethyl-4-(4-fluorophenyl)-6-oxo-5-(3-(trifluoromethyl)benzamido)-4,5,6,7-tetrahydro-1H-pyrazolo[3,4-b]pyridine-3-carboxylic acid (16)

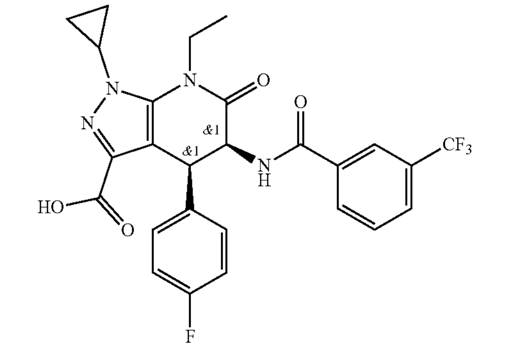

To a stirred solution of rac-N-((4R,5R)-1-cyclopropyl-7-ethyl-4-(4-fluorophenyl)-3-(hydroxymethyl)-6-oxo-4,5,6,7-tetrahydro-1H-pyrazolo[3,4-b]pyridin-5-yl)-3-(trifluoromethyl)benzamide (5.40 g, 10.5 mmol, 1.00 equiv) in anhydrous MeCN (54 mL) was added $H_5IO_6$ (4.77 g, 20.9 mmol, 2.00 equiv) followed by catalytic amount of $CrO_3$ (0.31 g, 3.13 mmol, 0.30 equiv) at room temperature. The reaction mixture was stirred at room temperature for 2 h. After completion of reaction, the reaction mixture was quenched by water 20 mL. 1M Sodium thiosulfate (25 mL) was added to the reaction solution at room temperature. The resulting mixture was filtered, the filter cake was washed with MeCN (3×20 mL). The filtrate was concentrated under reduced pressure. The mixture was acidified to pH 3 with HCl (aq.). The aqueous layer was extracted with ethyl acetate (3×50 mL). The combined organic phase was washed with brine (150 mL), dried over anhydrous sodium sulfate and concentrated under reduced pressure to give crude product. The residue was purified by reversed-phase flash chromatography with the following conditions: column, C18 silica gel; mobile phase, MeCN in water (0.1% TFA), 30% to 60% gradient in 18 min; detector, UV 254 nm. This resulted in rac-(4R,5R)-1-cyclopropyl-7-ethyl-4-(4-fluorophenyl)-6-oxo-5-(3-(trifluoromethyl)benzamido)-4,5,6,7-tetrahydro-1H-pyrazolo[3,4-b]pyridine-3-carboxylic acid (4.2 g, 75.7%) as a white solid.

(4R,5R)-1-cyclopropyl-7-ethyl-4-(4-fluorophenyl)-6-oxo-5-(3-(trifluoromethyl)benzamido)-4,5,6,7-tetrahydro-1H-pyrazolo[3,4-b]pyridine-3-carboxylic acid (I-537) & (4S,5S)-1-cyclopropyl-7-ethyl-4-(4-fluorophenyl)-6-oxo-5-(3-(trifluoromethyl)benzamido)-4,5,6,7-tetrahydro-1H-pyrazolo[3,4-b]pyridine-3-carboxylic acid (I-477)

Rac-(4R,5R)-1-cyclopropyl-7-ethyl-4-(4-fluorophenyl)-6-oxo-5-(3-(trifluoromethyl)benzamido)-4,5,6,7-tetrahydro-1H-pyrazolo[3,4-b]pyridine-3-carboxylic acid (4.2 g) was separated by Chiral-SFC with follow conditions: Column: XA-CHIRAL ART Cellulose-SC, 3*25 cm 5 μm; Mobile Phase A: $CO_2$, Mobile Phase B: MEOH: DCM=2: 1 (0.1% 2M $NH_3$-MeOH); Flow rate: 80 mL/min; Gradient: isocratic 40% B; Column Temperature (° C.): 35; Back Pressure (bar): 100; Wave Length: 254 nm; RT1(min): 2.24; RT2(min): 3.9; Sample Solvent: MeOH; Injection Volume: 4.5 mL to afford (4R,5R)-1-cyclopropyl-7-ethyl-4-(4-fluorophenyl)-6-oxo-5-(3-(trifluoromethyl)benzamido)-4,5,6,7-tetrahydro-1H-pyrazolo[3,4-b]pyridine-3-carboxylic acid (I-537) (2 g, 46.3%) and (4S,5S)-1-cyclopropyl-7-ethyl-4-(4-fluorophenyl)-6-oxo-5-(3-(trifluoromethyl)benzamido)-4,5,6,7-tetrahydro-1H-pyrazolo[3,4-b]pyridine-3-carboxylic acid (I-477) (2 g, 46.3%).

Data for I-537:

$^1H$ NMR (400 MHZ, DMSO-$d_6$) δ 12.80 (s, 1H), 8.53 (d, J=7.1 Hz, 1H), 8.14 (d, J=12.0 Hz, 2H), 7.92 (d, J=7.8 Hz, 1H), 7.71 (t, J=7.8 Hz, 1H), 7.08 (t, J=8.8 Hz, 2H), 7.00-6.89 (m, 2H), 5.27 (t, J=7.1 Hz, 1H), 4.81 (d, J=7.2 Hz, 1H), 4.43-4.29 (m, 1H), 4.29-4.16 (m, 1H), 3.84 (dt, J=7.0, 3.5 Hz, 1H), 1.44-1.07 (m, 7H).

LCMS Calculated for $C_{26}H_{22}F_4N_4O_4$: 530.16; Observed (Method-I): 529.2 [M−H]−, 95.5% at RT 1.483 min.

Optical rotation: a=−297, C=0.1 g/100 mL in MeOH.

Data for I-477:

$^1H$ NMR (400 MHZ, DMSO-$d_6$) δ 12.80 (s, 1H), 8.53 (d, J=7.1 Hz, 1H), 8.14 (d, J=12.0 Hz, 2H), 7.92 (d, J=7.8 Hz, 1H), 7.71 (t, J=7.8 Hz, 1H), 7.08 (t, J=8.8 Hz, 2H), 7.00-6.89 (m, 2H), 5.27 (t, J=7.1 Hz, 1H), 4.81 (d, J=7.2 Hz, 1H), 4.43-4.29 (m, 1H), 4.29-4.16 (m, 1H), 3.84 (dt, J=7.0, 3.5 Hz, 1H), 1.44-1.07 (m, 7H).

LCMS Calculated for $C_{26}H_{22}F_4N_4O_4$: 530.16; Observed (Method-J): 529.2 [M−H]−, 99.8% at RT 1.099 min.

Optical rotation: a=+240, C=0.1 g/100 mL in MeOH.

3. Synthesis of (4R,5R)-7-ethyl-4-(4-fluorophenyl)-6-oxo-1-propyl-5-(3-(trifluoromethyl)benzamido)-4,5,6,7-tetrahydro-1H-pyrazolo[3,4-b]pyridine-3-carboxylic acid (I-610) & (4S,5S)-7-ethyl-4-(4-fluorophenyl)-6-oxo-1-propyl-5-(3-(trifluoromethyl)benzamido)-4,5,6,7-tetrahydro-1H-pyrazolo[3,4-b]pyridine-3-carboxylic acid (I-675)

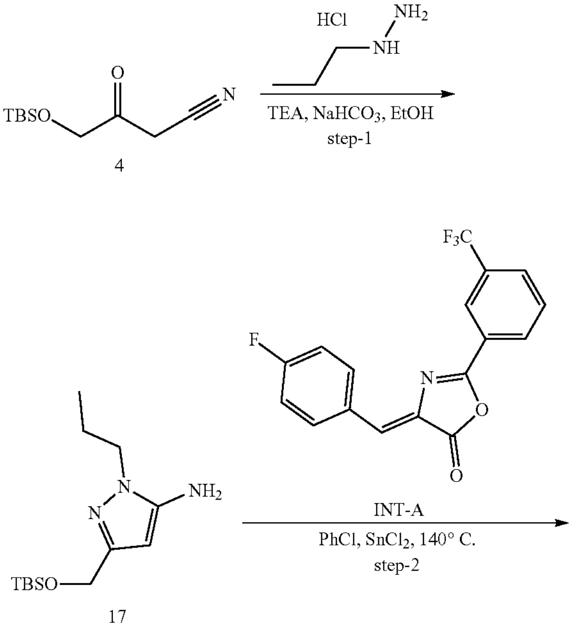

4

17

-continued

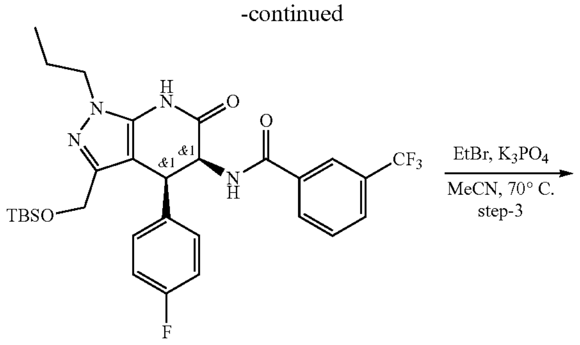

18
Exact Mass: 604.25

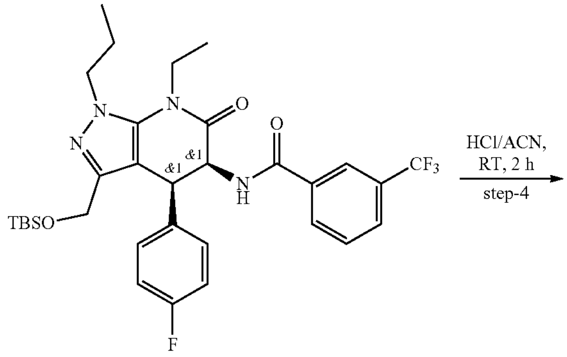

19
Exact Mass: 632.28

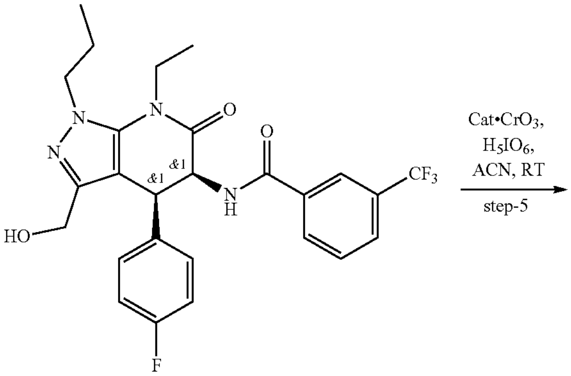

20

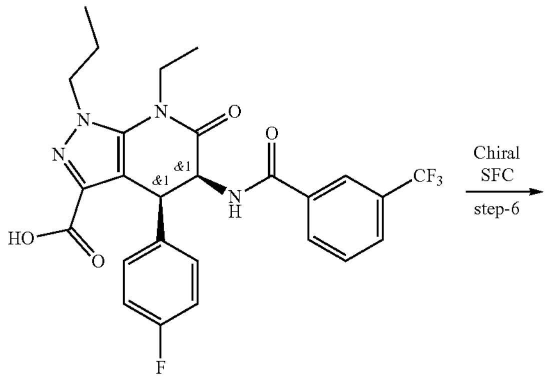

21

-continued

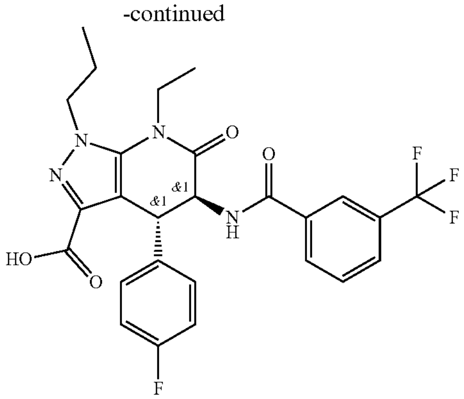

I-610

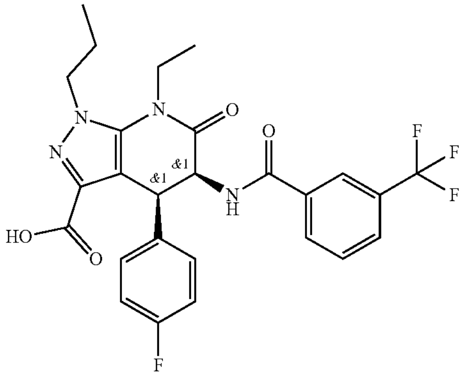

I-675

3-(((tert-butyldimethylsilyl)oxy)methyl)-1-propyl-1H-pyrazol-5-amine (17)

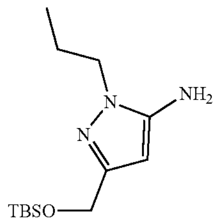

To a stirred solution of propylhydrazine hydrochloride (20.0 g, 181 mmol, 1.00 equiv) in anhydrous EtOH (20 mL) was added TEA (18.3 g, 181 mmol, 1.00 equiv) and 4-[(tert-butyldimethylsilyl)oxy]-3-oxobutanenitrile (46.3 g, 217 mmol, 1.20 equiv). The reaction mixture was stirred at room temperature for 16 h. The mixture was treated with $NaHCO_3$ (30.4 g, 362 mmol, 2.00 equiv) and then heated to 70° C. and stirred for 1 h. The mixture was cooled to room temperature and filtered. The filter was purified by silica gel column chromatography, eluted with EtOAc/petroleum ether from 0% to 40% to afford 3-(((tert-butyldimethylsilyl)oxy)methyl)-1-propyl-1H-pyrazol-5-amine (25 g, 51.3%) as a yellow oil.

rac-N-((4R,5R)-3-(((tert-butyldimethylsilyl)oxy)methyl)-4-(4-fluorophenyl)-6-oxo-1-propyl-4,5,6,7-tetrahydro-1H-pyrazolo[3,4-b]pyridin-5-yl)-3-(trifluoromethyl)benzamide (18)

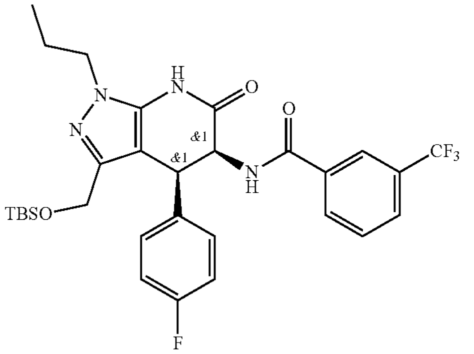

To a stirred solution of 3-(((tert-butyldimethylsilyl)oxy)methyl)-1-propyl-1H-pyrazol-5-amine (12.5 g, 46.4 mmol, 1.00 equiv) in chlorobenzene (200 mL) was added (4Z)-4-[(4-methylphenyl)methylidene]-2-[3-(trifluoromethyl)phenyl]-1,3-oxazol-5-one (18.4 g, 55.7 mmol, 1.20 equiv) followed by catalytic amount of $SnCl_2$ (0.89 g, 4.64 mmol, 0.10 equiv). The reaction mixture was stirred at 140° C. for 10 h. After completion of reaction, The resulting mixture was purified by silica gel column chromatography, eluted with petroleum ether/EtOAc (5/1) to afford rac-N-((4R,5R)-3-(((tert-butyldimethylsilyl)oxy)methyl)-4-(4-fluorophenyl)-6-oxo-1-propyl-4,5,6,7-tetrahydro-1H-pyrazolo[3,4-b]pyridin-5-yl)-3-(trifluoromethyl)benzamide (12.5 g, 44.6%) as a yellow solid.

rac-N-((4R,5R)-3-(((tert-butyldimethysilyl)oxy)methyl)-7-ethyl-4-(4-fluorophenyl)-6-oxo-1-propyl-4,5,6,7-tetrahydro-1H-pyrazolo[3,4-b]pyridin-5-yl)-3-(trifluoromethyl)benzamide (19)

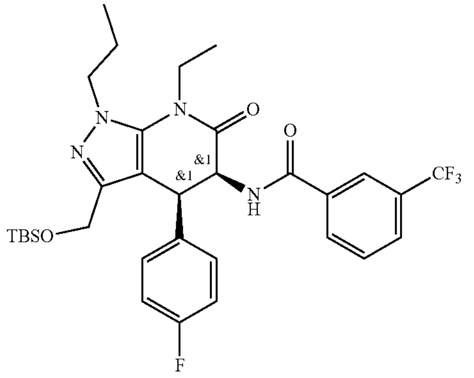

To a stirred mixture of rac-N-((4R,5R)-3-(((tert-butyldimethylsilyl)oxy)methyl)-4-(4-fluorophenyl)-6-oxo-1-propyl-4,5,6,7-tetrahydro-1H-pyrazolo[3,4-b]pyridin-5-yl)-3-(trifluoromethyl)benzamide (12.5 g, 20.7 mmol, 1.00 equiv) in MeCN (125 mL) were added $K_3PO_4$ (8.78 g, 41.3 mmol, 2.00 equiv) and bromoethane (2.70 g, 24.8 mmol, 1.20 equiv) at room temperature. The resulting mixture was stirred at 70° C. for additional 1 h. The resulting mixture was filtered; the filter cake was washed with MeCN (2×50 mL). The filtrate was concentrated under reduced pressure. The mixture was purified by silica gel column chromatography, eluted with petroleum ether/EtOAc (1:1) to afford rac-N-((4R,5R)-3-(((tert-butyldimethylsilyl)oxy)methyl)-7-ethyl-4-(4-fluorophenyl)-6-oxo-1-propyl-4,5,6,7-tetrahydro-1H-pyrazolo[3,4-b]pyridin-5-yl)-3-(trifluoromethyl)benzamide (6.7 g, 51.2%) as a yellow solid.

rac-N-((4R,5R)-7-ethyl-4-(4-fluorophenyl)-3-(hydroxymethyl)-6-oxo-1-propyl-4,5,6,7-tetrahydro-1H-pyrazolo[3,4-b]pyridin-5-yl)-3-(trifluoromethyl)benzamide (20)

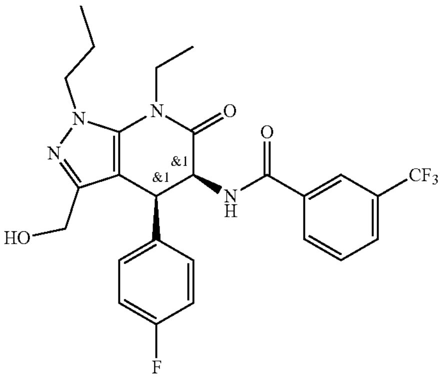

A mixture of rac-N-((4R,5R)-3-(((tert-butyldimethylsilyl)oxy)methyl)-7-ethyl-4-(4-fluorophenyl)-6-oxo-1-propyl-4,5,6,7-tetrahydro-1H-pyrazolo[3,4-b]pyridin-5-yl)-3-(trifluoromethyl)benzamide (6.70 g, 10.6 mmol, 1.00 equiv) in HCl (60 mL)/MeCN (60 mL) was stirred at room temperature for 2 h. The mixture was basified to pH 8~9 with saturated $K_2CO_3$ (aq.). The resulting mixture was extracted with EtOAc (2×20 mL). The combined organic layers were washed with saturated brine (2×20 mL), dried over anhydrous $Na_2SO_4$. After filtration, the filtrate was concentrated under reduced pressure. This resulted in rac-N-((4R,5R)-7-ethyl-4-(4-fluorophenyl)-3-(hydroxymethyl)-6-oxo-1-propyl-4,5,6,7-tetrahydro-1H-pyrazolo[3,4-b]pyridin-5-yl)-3-(trifluoromethyl)benzamide (5 g, crude) as a yellow solid. The crude product was used in the next step directly without further purification.

rac-((4R,5R)-7-ethyl-4-(4-fluorophenyl)-6-oxo-1-propyl-5-(3-trifluoromethyl)benzamido)-4,5,6,7-tetrahydro-1H-pyrazolo[3,4-b]pyridine-3-carboxylic acid (21)

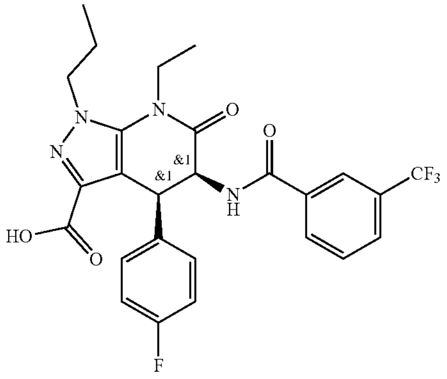

To a stirred mixture of rac-N-((4R,5R)-7-ethyl-4-(4-fluorophenyl)-3-(hydroxymethyl)-6-oxo-1-propyl-4,5,6,7-tetrahydro-1H-pyrazolo[3,4-b]pyridin-5-yl)-3-(trifluoromethyl) benzamide (5.00 g, 9.64 mmol, 1.00 equiv) in MeCN (50 mL) was added Periodic acid (4.40 g, 19.3 mmol, 2.00 equiv) at room temperature. Aftre 5 minutes, to the above mixture was added Chrormictrioxide (0.29 g, 2.89 mmol, 0.300 equiv) at room temperature. The resulting mixture was stirred at room temperature for additional 1 h. The resulting mixture was filtered, the filter cake was washed with MeCN (2×10 mL). The filtrate was treated with 20 mL of $Na_2S_2O_3$ (aq.). The mixture was extracted with EtOAc (2×50 mL). The combined organic layers were washed with saturated brine (2×20 mL), dried over anhydrous $Na_2SO_4$. After filtration, the filtrate was concentrated under reduced pressure. The residue was purified by silica gel column chromatography, eluted with petroleum ether/EtOAc (1:1) to afford rac-(4R,5R)-7-ethyl-4-(4-fluorophenyl)-6-oxo-1-propyl-5-[3-(trifluoromethyl)benzamido]-4H,5H-pyrazolo[3,4-b]pyridine-3-carboxylic acid (2.8 g, 54.5% yield, 90% purity) as a green solid.

(4R,5R)-7-ethyl-4-(4-fluorophenyl)-6-oxo-1-propyl-5-(3-(trifluoromethyl)benzamido)-4,5,6,7-tetrahydro-1H-pyrazolo[3,4-b]pyridine-3-carboxylic acid (1-610) & (4S,5S)-7-ethyl-4-(4-fluorophenyl)-6-oxo-1-propyl-5-(3-(trifluoromethyl)benzamido)-4,5,6,7-tetrahydro-1H-pyrazolo[3,4-b]pyridine-3-carboxylic acid (I-675)

The mixture of rac-(4R,5R)-7-ethyl-4-(4-fluorophenyl)-6-oxo-1-propyl-5-[3-(trifluoromethyl)benzamido]-4H,5H-pyrazolo[3,4-b]pyridine-3-carboxylic acid (2.8 g) was separated by Prep-Chiral SFC with the following conditions: Column: XA-CHIRAL ART Cellulose-SC, 3*25 cm, 5 μm; Mobile Phase A: $CO_2$, Mobile Phase B: MEOH: DCM=2: 1 (0.1% 2M $NH_3$-MeOH); Flow rate: 80 mL/min; Gradient: isocratic 45% B; Column Temperature (° C.): 35; Back Pressure (bar): 100; Wave Length: 254 nm; RT1(min): 1.99; RT2(min): 3.01; Sample Solvent: MEOH; Injection Volume: 2 mL. This resulted in (4R,5R)-7-ethyl-4-(4-fluorophenyl)-6-oxo-1-propyl-5-(3-(trifluoromethyl)benzamido)-4,5,6,7-tetrahydro-1H-pyrazolo[3,4-b]pyridine-3-carboxylic acid (I-610) (1.2 g, 42.8% purity) as a green solid & (4S,5S)-7-ethyl-4-(4-fluorophenyl)-6-oxo-1-propyl-5-(3-(trifluoromethyl)benzamido)-4,5,6,7-tetrahydro-1H-pyrazolo[3,4-b] pyridine-3-carboxylic acid (I-675) (1.1 g, 39.2% purity) as a green solid.

| | |
|---|---|
| 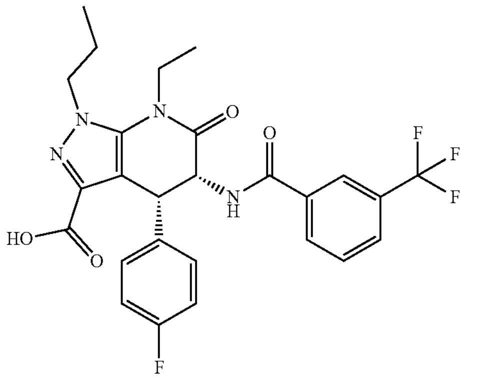 [SMILES: CCCn1nc(C(=O)O)c2c1N(CC)C(=O)[C@H](NC(=O)c1cccc(C(F)(F)F)c1)[C@@H]2c1ccc(F)cc1] | $^1$H NMR (300 MHz, DMSO-$d_6$) δ 8.48 (d, J = 6.9 Hz, 1H), 8.17-8.08 (m, 2H), 7.92 (d, J = 7.8 Hz, 1H), 7.71 (t, J = 7.8 Hz, 1H), 7.11-7.00 (m, 2H), 6.94 (dd, J = 8.5, 5.4 Hz, 2H), 5.18 (t, J = 7.0 Hz, 1H), 4.90 (d, J = 7.1 Hz, 1H), 4.31-4.13 (m, 3H), 3.88-3.73 (m, 1H), 1.93-1.75 (m, 2H), 1.27 (t, J = 7.1 Hz, 3H), 0.93 (t, J = 7.3 Hz, 3H).<br>LCMS Calculated for $C_{26}H_{24}F_4N_4O_4$: 532.17;<br>Observed (Method-J): 531.2 [M − H]$^-$, 98.7% at RT 1.117 min.<br>Chiral-SFC (Method-J): 100.0% at RT 1.324 min.<br>Optical rotation: a = −313.9 (C = 0.1 g/100 mL in MeOH, 25° C.). |
| 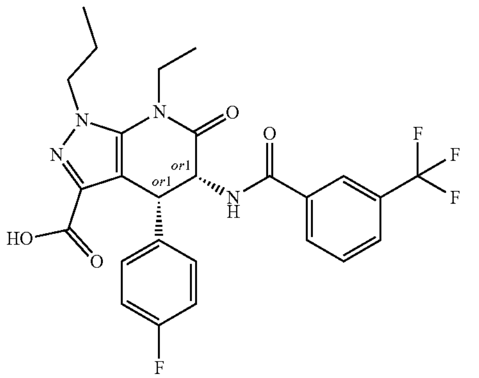 [SMILES: CCCn1nc(C(=O)O)c2c1N(CC)C(=O)[C@H](NC(=O)c1cccc(C(F)(F)F)c1)[C@@H]2c1ccc(F)cc1] | $^1$H NMR (300 MHz, DMSO-$d_6$) δ 8.47 (d, J = 7.0 Hz, 1H), 8.17-8.08 (m, 2H), 7.92 (d, J = 7.8 Hz, 1H), 7.70 (t, J = 7.8 Hz, 1H), 7.11-6.99 (m, 2H), 6.94 (dd, J = 8.5, 5.6 Hz, 2H), 5.18 (t, J = 7.1 Hz, 1H), 4.92 (d, J = 7.1 Hz, 1H), 4.32-4.13 (m, 3H), 3.89-3.74 (m, 1H), 1.93-1.73 (m, 2H), 1.26 (t, J = 7.0 Hz, 3H), 0.92 (t, J = 7.3 Hz, 3H).<br>LCMS Calculated for $C_{26}H_{24}F_4N_4O_4$: 532.17;<br>Observed (Method-J): 531.2 [M − H]$^-$, 99.4% at RT 1.115 min.<br>Chiral-SFC (Method-J): 100.0% at RT 1.852 min.<br>Optical rotation: a = +233.9, C = 0.1 g/100 mL in MeOH, 25° C. |

4. Synthesis of (4R,5R)-4-cyclopropyl-7-ethyl-6-oxo-1-propyl-5-(3-(trifluoromethyl)benzamido)-4,5,6,7-tetrahydro-1H-pyrazolo[3,4-b]pyridine-3-carboxylic acid (I-665) and (4S,5S)-4-cyclopropyl-7-ethyl-6-oxo-1-propyl-5-(3-(trifluoromethyl)benzamido)-4,5,6,7-tetrahydro-1H-pyrazolo[3,4-b]pyridine-3-carboxylic acid (I-651)

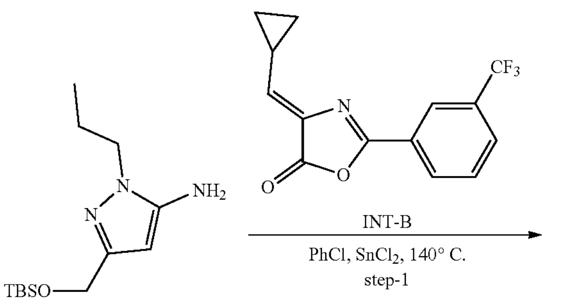

17

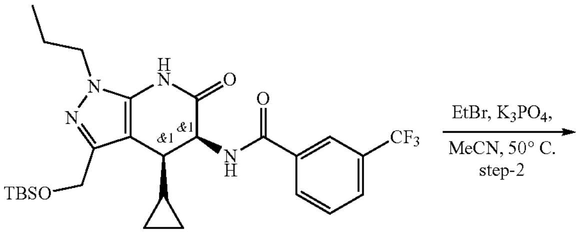

22

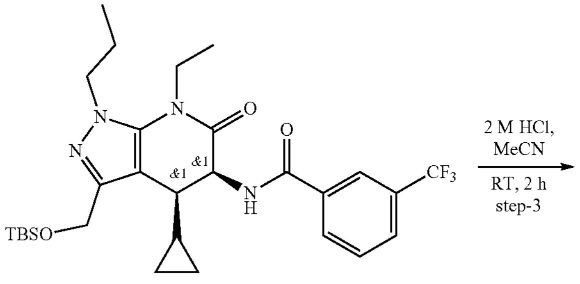

23

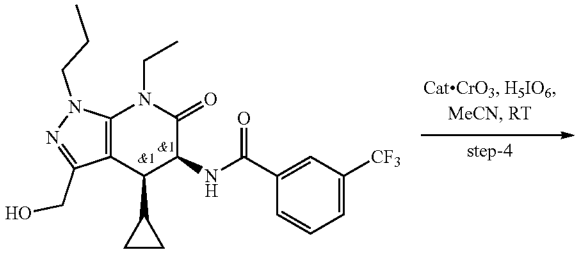

24

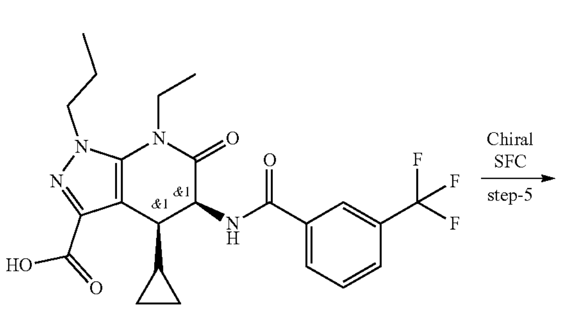

25

-continued

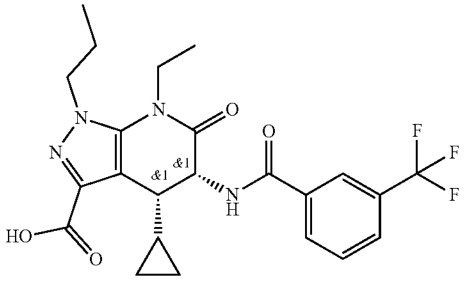

I-665

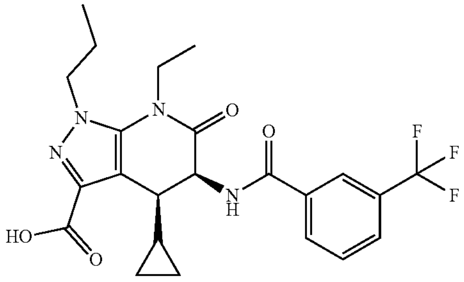

I-651 rac-N-((4R,5R)-3-(((tert-butyldimethylsilyl)oxy)methyl)-4-cyclopropyl-6-oxo-1-propyl-4,5,6,7-tetrahydro-1H-pyrazolo[3,4-b]pyridin-5-yl)-3-trifluoromethyl)benzamide (22)

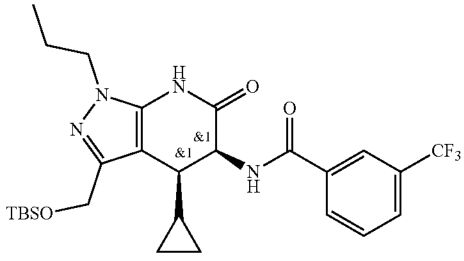

To a stirred solution of 3-(((tert-butyldimethylsilyl)oxy)methyl)-1-propyl-1H-pyrazol-5-amine (12.5 g, 46.4 mmol, 1.00 equiv) in chlorobenzene (200 mL) was added (Z)-4-(cyclopropylmethylene)-2-(3-(trifluoromethyl)phenyl)oxazol-5 (4H)-one (18.4 g, 55.7 mmol, 1.20 equiv) followed by catalytic amount of $SnCl_2$ (0.89 g, 4.64 mmol, 0.100 equiv). The reaction mixture was stirred at 140° C. for 10 h. After completion of reaction, the resulting mixture was purified by silica gel column chromatography, eluted with petroleum ether/EtOAc (5/1) to afford rac-N-((4R,5R)-3-(((tert-butyldimethylsilyl)oxy)methyl)-4-cyclopropyl-6-oxo-1-propyl-4,5,6,7-tetrahydro-1H-pyrazolo[3,4-b]pyridin-5-yl)-3-(trifluoromethyl)benzamide (6.10 g, 22.4%) as a yellow solid.

LCMS Calculated for $C_{27}H_{37}F_3N_4O_3Si$: 550.26; Observed: 551.2 $[M+H]^+$.

rac-N-((4R,5R)-3-(((tert-butyldimethylsilyl)oxy)methyl)-4-cyclopropyl-7-ethyl-6-oxo-1-propyl-4,5,6,7-tetrahydro-1H-pyrazolo[3,4-b]pyridin-5-yl)-3-trifluoromethyl)benzamide (23)

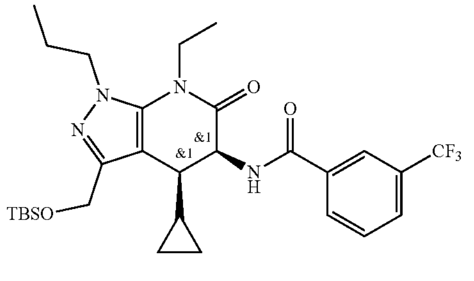

Into a 250 mL round-bottom flask were added rac-N-((4R,5R)-3-(((tert-butyldimethylsilyl)oxy)methyl)-4-cyclopropyl-6-oxo-1-propyl-4,5,6,7-tetrahydro-1H-pyrazolo[3,4-b]pyridin-5-yl)-3-(trifluoromethyl)benzamide (9.90 g, 18.0 mmol, 1.00 equiv), bromoethane (2.35 g, 21.6 mmol, 1.20 equiv), $K_3PO_4$ (7.63 g, 35.9 mmol, 2.00 equiv) in MeCN (100 mL) at room temperature. The resulting mixture was stirred for 12 hours at 50° C. The mixture was diluted with water (500 mL) and extracted with ethyl acetate (100 mL×3). The combined organic phase was washed with brine (300 mL), dried over anhydrous sodium sulfate, filtered and concentrated in vacuum. The residue was applied onto a silica gel column and eluted with EtOAc/petroleum ether (0-80%, 20 min) to afford rac-N-((4R,5R)-3-(((tert-butyldimethylsilyl)oxy)methyl)-4-cyclopropyl-7-ethyl-6-oxo-1-propyl-4,5,6,7-tetrahydro-1H-pyrazolo[3,4-b]pyridin-5-yl)-3-(trifluoromethyl)benzamide (7.00 g, 62.1%) as a yellow solid. LCMS Calculated for $C_{29}H_{41}F_3N_4O_3Si$: 578.29; Observed: 579.2 $[M+H]^+$.

rac-N-((4R,5R)-4-cyclopropyl-7-ethyl-3-(hydroxymethyl)-6-oxo-1-propyl-4,5,6,7-tetrahydro-1H-pyrazolo[3,4-b]pyridin-5-yl)-3-trifluoromethyl)benzamide (24)

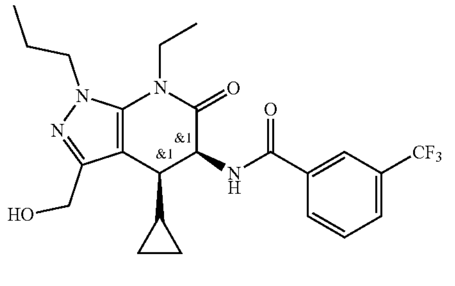

A solution of rac-N-((4R,5R)-3-(((tert-butyldimethylsilyl)oxy)methyl)-4-cyclopropyl-7-ethyl-6-oxo-1-propyl-4,5,6,7-tetrahydro-1H-pyrazolo[3,4-b]pyridin-5-yl)-3-(trifluoromethyl)benzamide (7.80 g, 13.5 mmol, 1.00 equiv) in HCl aq. (6M): MeCN=(1:1, 80 mL) at room temperature. The reaction mixture was stirred for 2 hours at room temperature. The resulting mixture was concentrated in vacuum to afford rac-N-((4R,5R)-4-cyclopropyl-7-ethyl-3-(hydroxymethyl)-6-oxo-1-propyl-4,5,6,7-tetrahydro-1H-pyrazolo[3,4-b]pyridin-5-yl)-3-(trifluoromethyl)benzamide (6.9 g, crude) as a white solid, which was used for next step directly.

LCMS Calculated for $C_{23}H_{27}F_3N_4O_3$: 464.20; Observed: 465.1 $[M+H]^+$.

rac-(4R,5R)-4-cyclopropyl-7-ethyl-6-oxo-1-propyl-5-(3-(trifluoromethyl)benzamido)-4,5,6,7-tetrahydro-1H-pyrazolo[3,4-b]pyridine-3-carboxylic acid (25)

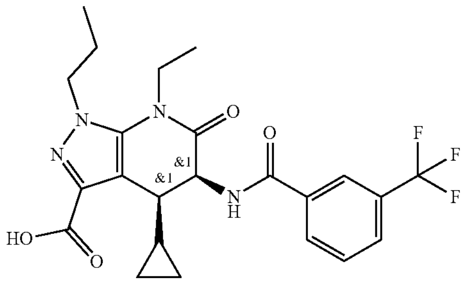

Into a 250 mL round-bottom flask were added rac-N-((4R,5R)-4-cyclopropyl-7-ethyl-3-(hydroxymethyl)-6-oxo-1-propyl-4,5,6,7-tetrahydro-1H-pyrazolo[3,4-b]pyridin-5-yl)-3-(trifluoromethyl)benzamide (5.90 g, 12.7 mmol, 1.00 equiv), $CrO_3$ (0.25 g, 2.54 mmol, 0.20 equiv) and periodic acid (8.69 g, 38.1 mmol, 3.00 equiv) in MeCN (60 mL) at room temperature. The mixture was stirred at room temperature for 1 hour. The mixture was purified by prep-HPLC ($NH_3 \cdot H_2O$ buffer) to afford rac-(4S,5S)-4-cyclopropyl-7-ethyl-6-oxo-1-propyl-5-(3-(trifluoromethyl)benzamido)-4,5,6,7-tetrahydro-1H-pyrazolo[3,4-b]pyridine-3-carboxylic acid (3.0 g, 46.9%) as a white solid.

LCMS Calculated for $C_{23}H_{25}F_3N_4O_4$: 478.18; Observed: 479.1 $[M+H]^+$.

(4R,5R)-4-cyclopropyl-7-ethyl-6-oxo-1-propyl-5-(3-(trifluoromethyl)benzamido)-4,5,6,7-tetrahydro-1H-pyrazolo[3,4-b]pyridine-3-carboxylic acid (I-665) and (4S,5S)-4-cyclopropyl-7-ethyl-6-oxo-1-propyl-5-(3-(trifluoromethyl)benzamido)-4,5,6,7-tetrahydro-1H-pyrazolo[3,4-b]pyridine-3-carboxylic acid (I-651)

The rac-(4S,5S)-4-cyclopropyl-7-ethyl-6-oxo-1-propyl-5-(3-(trifluoromethyl)benzamido)-4,5,6,7-tetrahydro-1H-pyrazolo[3,4-b]pyridine-3-carboxylic acid (50 mg) was separated by Chiral Prep-HPLC with the following condition: Column: XA-CHIRALPAK IH, 3*25 cm, 5 μm; Mobile Phase A: Hex: DCM=5: 1-HPLC, Mobile Phase B: MeOH: EtOH=1: 1-HPLC; Flow rate: 35 mL/min; Gradient: isocratic 5; Wave Length: 2554 nm; RT1(min): 8.3; RT2 (min): 9.8; Sample Solvent: Hex: EtOH=1: 1-HPLC; Injection Volume: 0.5 mL; Number Of Runs: 26 to afford (4R,5R)-4-cyclopropyl-7-ethyl-6-oxo-1-propyl-5-(3-(trifluoromethyl)benzamido)-4,5,6,7-tetrahydro-1H-pyrazolo[3,4-b]pyridine-3-carboxylic acid (I-665) (10 mg, 19.2%) as a white solid and (4S,5S)-4-cyclopropyl-7-ethyl-6-oxo-1-propyl-5-(3-(trifluoromethyl)benzamido)-4,5,6,7-tetrahydro-1H-pyrazolo[3,4-b]pyridine-3-carboxylic acid (I-651) (10 mg, 19.7%) as a white solid.

| | |
|---|---|
| 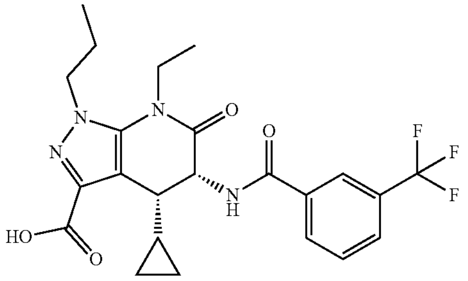 [SMILES: CCCn1nc(C(=O)O)c2c1N(CC)C(=O)[C@H](NC(=O)c1cccc(C(F)(F)F)c1)[C@@H]2C1CC1] | $^1H$ NMR (400 MHz, DMSO-$d_6$) δ 13.22-12.63 (m, 1H), 9.02 (d, J = 7.8 Hz, 1H), 8.31 (s, 1H), 8.25 (d, J = 7.9 Hz, 1H), 7.96 (d, J = 8.1 Hz, 1H), 7.76 (t, J = 7.8 Hz, 1H), 5.02 (dd, J = 7.8, 6.0 Hz, 1H), 4.27-4.10 (m, 3H), 3.80-3.70 (m, 1H), 3.39 (t, J = 6.2 Hz, 1H), 1.90-1.74 (m, 2H), 1.21 (t, J = 7.1 Hz, 3H), 1.18 (d, J = 6.5 Hz, 1H), 0.89 (t, J = 7.4 Hz, 3H), 0.53-0.44 (m, 1H), 0.21-0.17 (m, 1H), 0.03 (d, J = 5.4 Hz, 2H).<br>LCMS Calculated for $C_{23}H_{25}F_3N_4O_4$: 478.18;<br>Observed (Method-I): 477.2 $[M - H]^-$, 96.7% at RT 1.357 min.<br>Optical rotation: a = −38.453, (c = 0.096 g/100 mL in MeOH, 25° C.). |
| 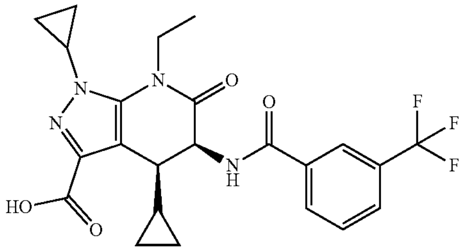 [SMILES: CCN1C(=O)[C@@H](NC(=O)c2cccc(C(F)(F)F)c2)[C@@H](C2CC2)c2c(C(=O)O)nn(C3CC3)c21] | $^1H$ NMR (400 MHz, DMSO-$d_6$) δ 13.06-12.67 (m, 1H), 9.02 (d, J = 7.8 Hz, 1H), 8.31 (s, 1H), 8.25 (d, J = 7.9 Hz, 1H), 7.96 (d, J = 7.8 Hz, 1H), 7.76 (t, J = 7.8 Hz, 1H), 5.02 (dd, J = 7.8, 6.0 Hz, 1H), 4.27-4.12 (m, 3H), 3.80-3.70 (m, 1H), 3.39 (t, J = 6.2 Hz, 1H), 1.90-1.75 (m, 2H), 1.21 (t, J = 7.1 Hz, 3H), 0.94-0.80 (m, 4H), 0.48 (t, J = 9.1 Hz, 1H), 0.19 (t, J = 9.1 Hz, 1H), 0.02 (d, J = 5.9 Hz, 2H).<br>LCMS Calculated for $C_{23}H_{25}F_3N_4O_4$: 478.18;<br>Observed (Method-C): 479.0 $[M + H]^+$, 98.7% at RT 1.139 min.<br>Optical rotation: a = +31.368, (c = 0.096 g/100 mL in MeOH, 25° C.). |

5. Synthesis of (4R,5R)-4-cyclopropyl-7-ethyl-6-oxo-1-phenyl-5-(3-(trifluoromethyl)benzamido)-4,5,6,7-tetrahydro-1H-pyrazolo[3,4-b]pyridine-3-carboxylic acid (I-404) and (4S,5S)-4-cyclopropyl-7-ethyl-6-oxo-1-phenyl-5-(3-(trifluoromethyl)benzamido)-4,5,6,7-tetrahydro-1H-pyrazolo[3,4-b]pyridine-3-carboxylic acid (I-587)

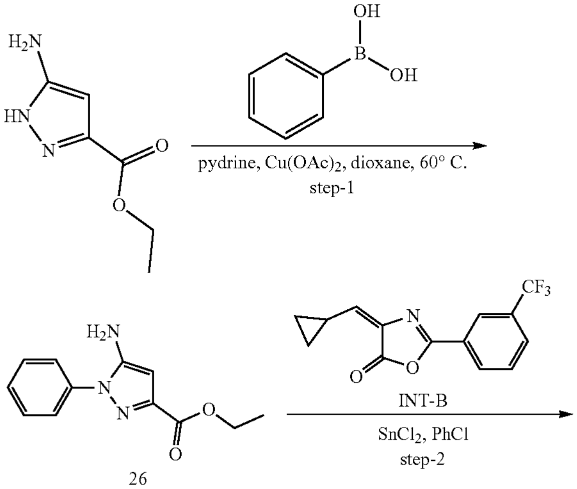

26

-continued

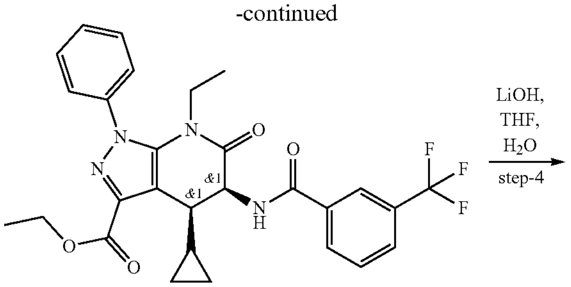

28

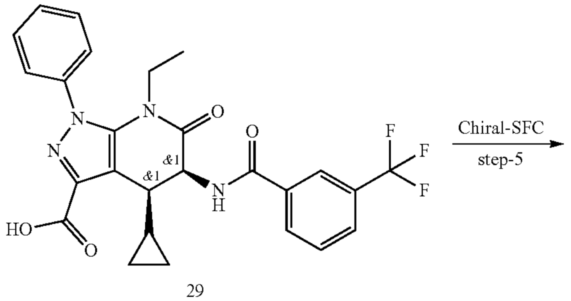

29

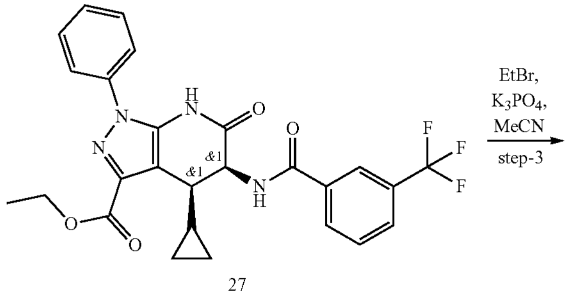

27

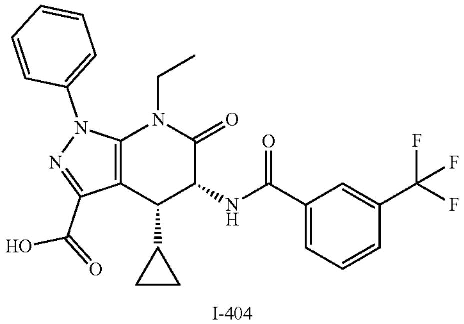

I-404

-continued

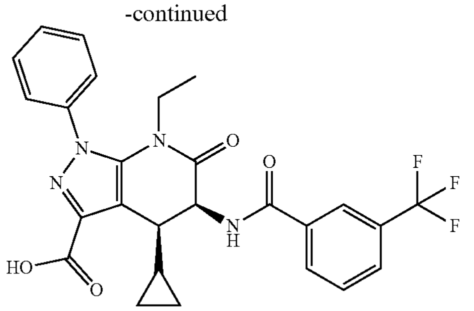

I-587 ethyl 4-amino-1-phenyl-1H-pyrazole-3-carboxylate (26)

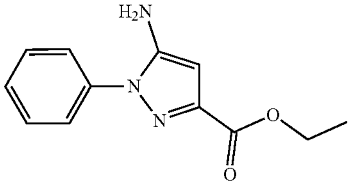

Into a 500 mL round-bottom flask were added ethyl 5-amino-1H-pyrazole-3-carboxylate (20.0 g, 129 mmol, 1.00 equiv), phenyl boronic acid (17.3 g, 141 mmol, 1.10 equiv), pyridine (61.2 g, 773 mmol, 6.00 equiv), $Cu(OAc)_2$ (14.1 g, 77.3 mmol, 0.600 equiv) and dioxane (200 mL). The resulting mixture was stirred overnight at 60° C. under nitrogen atmosphere. The mixture was allowed to cool down to room temperature. The reaction was quenched with sat. $NH_4Cl$ (aq.) (100 mL) at room temperature. The resulting mixture was extracted with EtOAc (3×200 mL). The combined organic phase was concentrated under reduced pressure. The residue was purified by silica gel column chromatography, eluted with petroleum ether/EtOAc (2:1) to afford ethyl 5-amino-1-phenylpyrazole-3-carboxylate (12.2 g, 40.9%) as a white solid.

(4R,5R)-4-cyclopropyl-6-oxo-1-phenyl-5-(3-(trifluoromethyl)benzamido)-4,5,6,7-tetrahydro-1H-pyrazolo[3,4-b]pyridine-3-carboxylate (27)

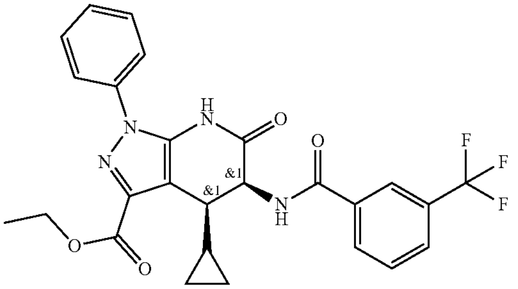

Into a 500 mL round-bottom flask were added ethyl 5-amino-1-phenylpyrazole-3-carboxylate (11.4 g, 49.3 mmol, 1.00 equiv), (4E)-4-(cyclopropylmethylidene)-2-[3-(trifluoromethyl)phenyl]-1,3-oxazol-5-one (13.8 g, 49.3 mmol, 1.00 equiv), $SnCl_2$ (0.94 g, 4.93 mmol, 0.100 equiv) and chlorobenzene (114 mL). The resulting mixture was stirred for 16 h at 140° C. The resulting mixture was allowed to cool down to room temperature and was purified by silica gel column chromatography, eluted with petroleum ether/EtOAc (2:1) to afford rac-ethyl (4R,5R)-4-cyclopropyl-6-oxo-1-phenyl-5-(3-(trifluoromethyl)benzamido)-4,5,6,7-tetrahydro-1H-pyrazolo[3,4-b]pyridine-3-carboxylate (6.5 g, 25.7%) as a white solid.

rac-ethyl (4R,5R)-4-cyclopropyl-6-oxo-1-phenyl-5-(3-(trifluoromethyl)benzamido)-4,5,6,7-tetrahydro-1H-pyrazolo[3,4-b]pyridine-3-carboxylate (28)

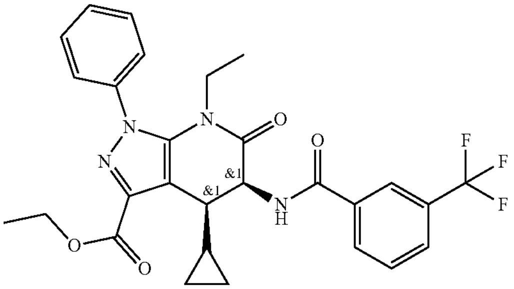

Into a 250 mL round-bottom flask were added rac-ethyl (4R,5R)-4-cyclopropyl-6-oxo-1-phenyl-5-(3-(trifluoromethyl)benzamido)-4,5,6,7-tetrahydro-1H-pyrazolo[3,4-b]pyridine-3-carboxylate (6.30 g, 12.3 mmol, 1.00 equiv), bromoethane (1.61 g, 14.7 mmol, 1.20 equiv), $K_3PO_4$ (3.91 g, 18.4 mmol, 1.50 equiv) and ACN (63 mL) at 60° C. The resulting mixture was stirred overnight at 60° C. The resulting mixture was concentrated under reduced pressure. The residue was purified by silica gel column chromatography, eluted with petroleum ether/EtOAc (5:1) to afford rac-ethyl (4R,5R)-4-cyclopropyl-7-ethyl-6-oxo-1-phenyl-5-(3-(trifluoromethyl)benzamido)-4,5,6,7-tetrahydro-1H-pyrazolo[3,4-b]pyridine-3-carboxylate (2.9 g, 43.6%) as a white solid.

rac-ethyl (4R,5R)-4-cyclopropyl-7-ethyl-6-oxo-1-phenyl-5-(3-(trifluoromethyl)benzamido)-4,5,6,7-tetrahydro-1H-pyrazolo[3,4-b]pyridine-3-carboxylic acid (29)

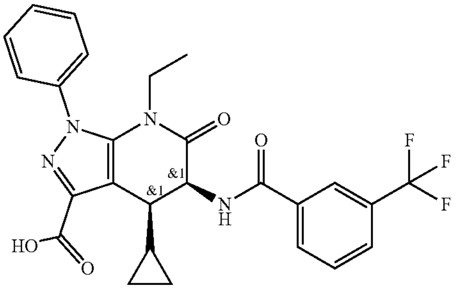

To a stirred solution of rac-ethyl (4R,5R)-4-cyclopropyl-7-ethyl-6-oxo-1-phenyl-5-(3-(trifluoromethyl)benzamido)-4,5,6,7-tetrahydro-1H-pyrazolo[3,4-b]pyridine-3-carboxylate (2.9 g, 5.37 mmol, 1.00 eq) in $H_2O$ (20 mL) and THF (30 mL) was added LiOH (0.257 g, 10.7 mmol, 2.00 equiv) in portions at room temperature. The resulting mixture was stirred at 40° C. for 2 h. The mixture was allowed to cool down to room temperature. The mixture was acidified to pH 5 with conc. HCl. The resulting mixture was extracted with EtOAc (3×50 mL). The combined organic layers were washed with $H_2O$ (1×100 mL), dried over anhydrous $Na_2SO_4$. After filtration, the filtrate was concentrated under reduced pressure. The residue was purified by trituration with ethyl ether (20 mL). This resulted in rac-ethyl (4R,5R)-4-cyclopropyl-7-ethyl-6-oxo-1-phenyl-5-(3-(trifluoromethyl)benzamido)-4,5,6,7-tetrahydro-1H-pyrazolo[3,4-b]pyridine-3-carboxylate (2.3 g, 98% purity) as a white solid.

(4R,5R)-4-cyclopropyl-7-ethyl-6-oxo-1-phenyl-5-(3-(trifluoromethyl)benzamido)-4,5,6,7-tetrahydro-1H-pyrazolo[3,4-b]pyridine-3-carboxylic acid (I-404) and (4S,5S)-4-cyclopropyl-7-ethyl-6-oxo-1-phenyl-5-(3-(trifluoromethyl)benzamido)-4,5,6,7-tetrahydro-1H-pyrazolo[3,4-b]pyridine-3-carboxylic acid (I-587)

rac-ethyl (4R,5R)-4-cyclopropyl-7-ethyl-6-oxo-1-phenyl-5-(3-(trifluoromethyl)benzamido)-4,5,6,7-tetr ahydro-1H-pyrazolo[3,4-b]pyridine-3-carboxylate (100 mg, 0.195 mmol, 1.00 equiv) was purified by Prep-SFC to afford (4R,5R)-4-cyclopropyl-7-ethyl-6-oxo-1-phenyl-5-(3-(trifluoromethyl)benzamido)-4,5,6,7-tetrahydro-1H-pyrazolo[3,4-b]pyridine-3-carboxylic acid (I-404) (40.0 mg, 40.0%) and (4S,5S)-4-cyclopropyl-7-ethyl-6-oxo-1-phenyl-5-(3-(trifluoromethyl)benzamido)-4,5,6,7-tetrahydro-1H-pyrazolo[3,4-b]pyridine-3-carboxylic acid (I-587) (40.0 mg, 40.0%) as a white solid.

| | |
|---|---|
| 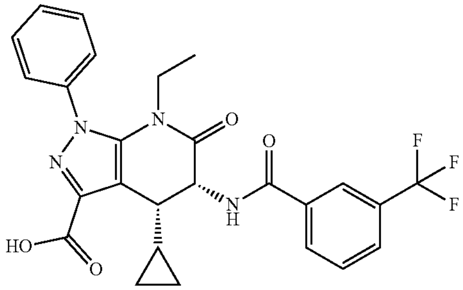 [SMILES: CCN1C(=O)[C@H](NC(=O)c2cccc(C(F)(F)F)c2)[C@H](C2CC2)c2c(C(=O)O)nn(-c3ccccc3)c21] I-404 | $^1$H NMR (400 MHz, DMSO-$d_6$) δ 13.05 (s, 1H), 9.08 (d, J = 8.0 Hz, 1H), 8.35 (s, 1H), 8.28 (d, J = 7.9 Hz, 1H), 7.96 (d, J = 7.8 Hz, 1H), 7.77 (t, J = 7.8 Hz, 1H), 7.73-7.68 (m, 2H), 7.61 (dd, J = 8.6, 4.1 Hz, 3H), 5.36 (dd, J = 7.9, 6.0 Hz, 1H), 3.88-3.90 (m, 1H), 3.42 (t, J = 6.5 Hz, 1H), 2.96-2.86 (m, 1H), 0.83 (t, J = 7.1 Hz, 4H), 0.58-0.51 (m, 1H), 0.24 (t, J = 4.4 Hz, 1H), 0.12-0.2 (m, 2H). LCMS Calculated for $C_{26}H_{23}F_3N_4O_4$: 512.17; Observed (Method-C): 513.1 [M + H]$^+$, 97.7% at RT 1.133 min. Optical rotation: a = −41.660, (c = 0.1 g/100 mL in MeOH, T = 25° C.). |
| 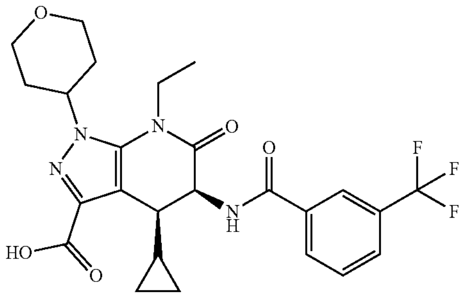 I-587 | $^1$H NMR (400 MHz, DMSO-$d_6$) δ 13.05 (s, 1H), 9.08 (d, J = 8.0 Hz, 1H), 8.35 (s, 1H), 8.28 (d, J = 7.9 Hz, 1H), 7.96 (d, J = 7.8 Hz, 1H), 7.77 (t, J = 7.8 Hz, 1H), 7.73-7.68 (m, 2H), 7.61 (dd, J = 8.6, 4.1 Hz, 3H), 5.36 (dd, J = 7.9, 6.0 Hz, 1H), 3.88-3.90 (m, 1H), 3.42 (t, J = 6.5 Hz, 1H), 2.96-2.86 (m, 1H), 0.83 (t, J = 7.1 Hz, 4H), 0.58-0.51 (m, 1H), 0.24 (t, J = 4.4 Hz, 1H), 0.12-0.20 (m, 2H). LCMS Calculated for $C_{26}H_{23}F_3N_4O_4$: 512.17; Observed (Method-C): 513.1 [M + H]$^+$, 99.7% at RT 1.137 min; Optical rotation: a = +32.328, (c = 0.1 g/100 mL in MeOH, T = 25° C.). |

6. Synthesis of (4R,5R)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-443) and (4S,5S)-7-ethyl-4-(4-flurophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-657)

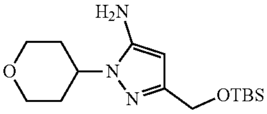
INT-C

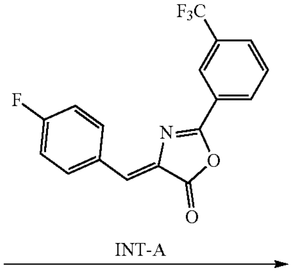
INT-A

SnCl$_2$, t-BuOH
step-1

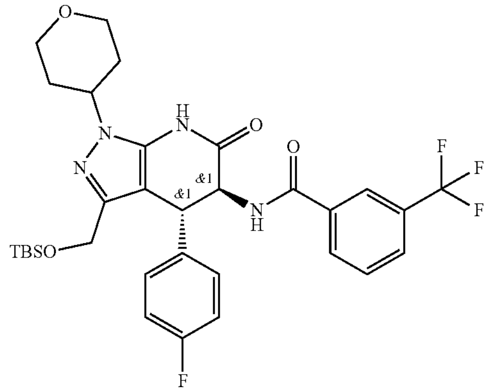
30
DBU,
ACN,
70° C.
step-2
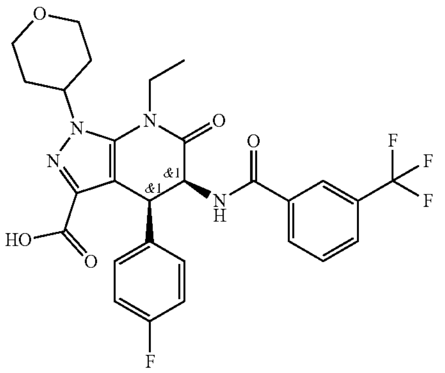
34
Chiral SFC
step-6
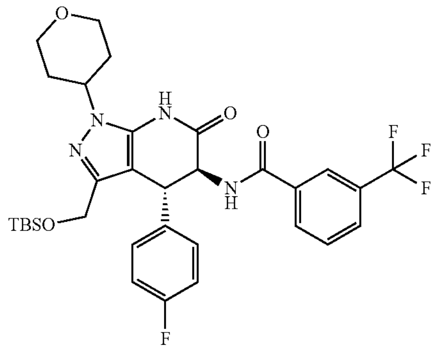
30
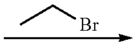
DMF, $K_2CO_3$
step-3
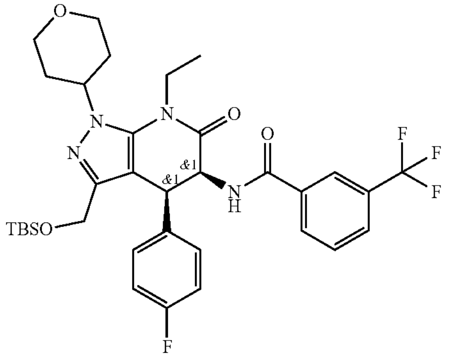
32
ACN, HCl
step-4
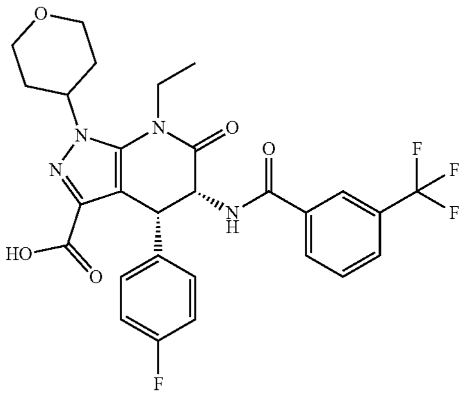
I-443
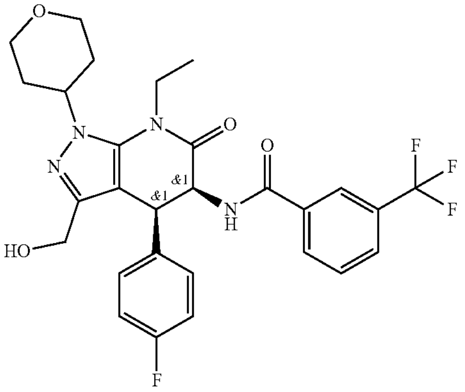
33
$CrO_3$,
ACN,
$H_6IO_5$
step-5
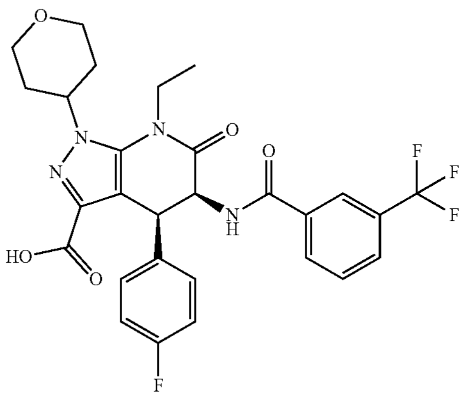
I-657 rac-N-((4R,5S)-3-(((tert-butyldimethylsilyl)oxy)methyl)-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (30)

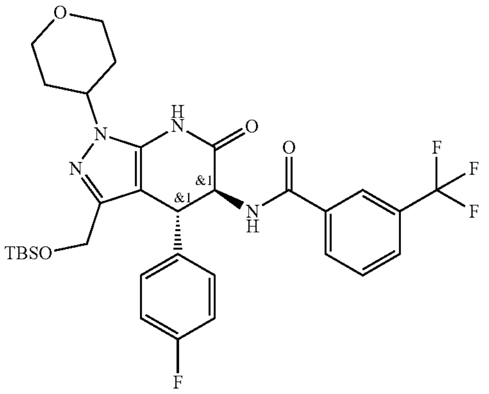

A solution of 3-(((tert-butyldimethylsilyl)oxy)methyl)-1-(tetrahydro-2H-pyran-4-yl)-1H-pyrazol-5-amine (10.0 g, 32.1 mmol, 1.00 equiv), (Z)-4-(4-fluorobenzylidene)-2-(3-(trifluoromethyl)phenyl)oxazol-5 (4H)-one (10.8 g, 32.1 mmol, 1.00 equiv) and $SnCl_2$ (0.61 g, 3.21 mmol, 0.100 equiv) in tert-Butanol (100 mL) was stirred at 110° C. for 16 h. The mixture was allowed to cool down to room temperature. The resulting mixture was concentrated under reduced pressure. The residue was purified by silica gel column chromatography, eluted with petroleum ether/EtOAc (5:1) to afford rac-N-((4R,5S)-3-(((tert-butyldimethylsilyl)oxy)methyl)-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (14 g, 80% purity) as a yellow solid.

rac-N-((4R,5R)-3-(((tert-butyldimethylsilyl)oxy)methyl)-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (31)

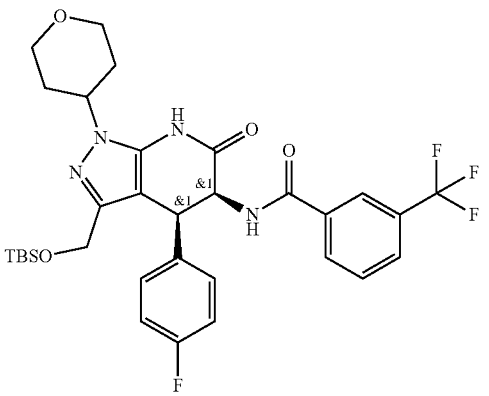

A solution of rac-N-((4R,5S)-3-(((tert-butyldimethylsilyl)oxy)methyl)-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (13.9 g, 21.5 mmol, 1.00 equiv) and DBU (12.4 g, 81.7 mmol, 3.80 equiv) in acetonitrile (130 mL) was stirred at 70° C. for 16 h. The resulting mixture was diluted with water (200 mL). The resulting mixture was extracted with EtOAc (3×100 mL). The combined organic layers were washed with water (2×50 mL), dried over anhydrous $Na_2SO_4$. After filtration, the filtrate was concentrated under reduced pressure. This resulted in rac-N-((4R,5R)-3-(((tert-butyldimethylsilyl)oxy)methyl)-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (13 g) as a yellow solid. The crude product was used in the next step directly without further purification.\ rac-N-((4R,5R)-3-(((tert-butyldimethylsilyl)oxy)methyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (32)

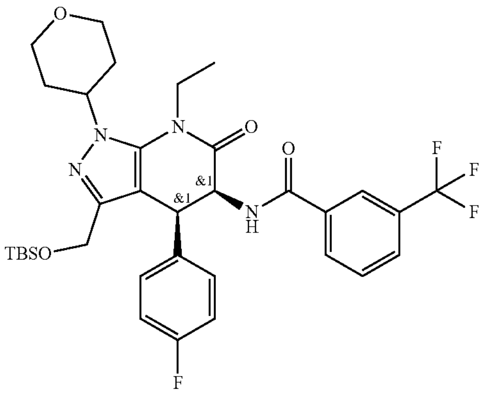

A solution of rac-N-((4R,5R)-3-(((tert-butyldimethylsilyl)oxy)methyl)-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (13.0 g, 20.1 mmol, 1.00 equiv), bromoethane (2.63 g, 24.1 mmol, 1.20 equiv) and $K_2CO_3$ (5.56 g, 40.2 mmol, 2.00 equiv) in DMF (130 mL) was stirred at room temperature for 1 h. The resulting mixture was diluted with water (200 mL). The resulting mixture was extracted with EtOAc (3×100 mL). The combined organic layers were washed with water (1×50 mL), dried over anhydrous $Na_2SO_4$. After filtration, the filtrate was concentrated under reduced pressure. The residue was purified by silica gel column chromatography, eluted with petroleum ether/EtOAc (5:1) to afford rac-N-((4R,5R)-3-(((tert-butyldimethylsilyl)oxy)methyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (9 g, 90% purity) as a yellow solid.

rac-N-((4R,5R)-7-ethyl-4-(4-fluorophenyl)-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (32)

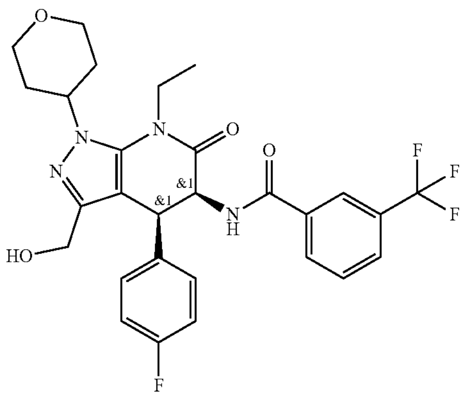

A solution of rac-N-((4R,5R)-3-(((tert-butyldimethylsilyl)oxy)methyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (8.90 g, 13.2 mmol, 1.00 equiv) in hydrochloric acide (6M, 90 mL) and acetonitrile (45 mL) was stirred at room temperature for 1 h. The mixture was neutralized to pH 7 with saturated $Na_2CO_3$ (aq.). The resulting mixture was extracted with EtOAc (3×100 mL). The combined organic layers were washed with brine (1×50 mL), dried over anhydrous $Na_2SO_4$. After filtration, the filtrate was concentrated under reduced pressure. This resulted in rac-N-((4R,5R)-7-ethyl-4-(4-fluorophenyl)-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (7.3 g, 90% purity) as a yellow solid.

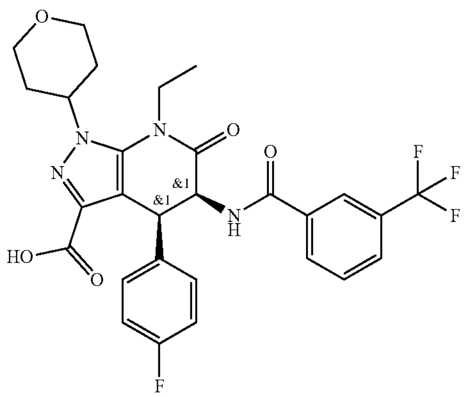

rel-(4R,5R)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (34)

A solution of rac-N-((4R,5R)-7-ethyl-4-(4-fluorophenyl)-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (7.00 g, 12.5 mmol, 1.00 equiv), Periodic acid (5.69 g, 25.0 mmol, 2.00 equiv) and $CrO_3$ (0.25 g, 2.50 mmol, 0.200 equiv) in MeCN (70 mL) was stirred at room temperature for 5 h. The reaction was quenched with $Na_2S_2O_3$ at 0° C. The mixture was acidified to pH 4 with HCl (aq.). The resulting mixture was extracted with EtOAc (3×50 mL). The combined organic layers were washed with water (2×20 mL), dried over anhydrous $Na_2SO_4$. After filtration, the filtrate was concentrated under reduced pressure. This resulted in rel-(4R,5R)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (4 g, crude) as a white solid.

(4R,5R)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-443) and (4S,5S)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-657)

The crude product (4 g) was purified by Chiral-SFC with the following conditions (Column: CHIRALPAK IA, 3*25 cm, 5 μm; Mobile Phase A: CO2, Mobile Phase B: IPA: DCM=2: 1 (0.1% IPAmine); Flow rate: 80 mL/min; Gradient: isocratic 35% B; Column Temperature (° C.): 35; Back Pressure (bar): 100; Wave Length: 220 nm; RT1(min): 3.6; RT2(min): 4.6; Sample Solvent: MEOH; Injection Volume: 1.5 mL) to afford (4R,5R)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-443) (1.8 g, 45%) as a white solid and (4S,5S)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-657) (1.8 g, 45%) as a white solid.

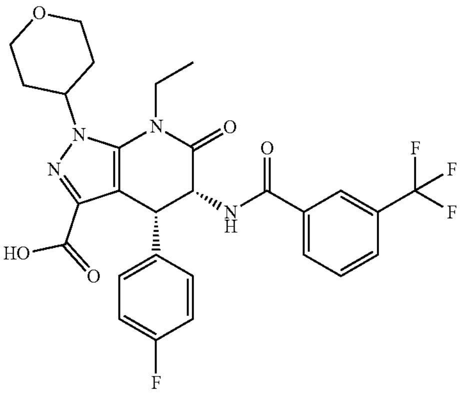 [SMILES: CCN1C(=O)[C@H](NC(=O)c2cccc(C(F)(F)F)c2)[C@H](c2ccc(F)cc2)c2c(C(=O)O)nn(C3CCOCC3)c21]

I-443

$^1$H NMR (300 MHz, DMSO-$d_6$) δ 12.84 (s, 1H), 8.53 (d, J = 7.1 Hz, 1H), 8.23-8.05 (m, 2H), 7.92 (d, J = 7.8 Hz, 1H), 7.71 (t, J = 7.8 Hz, 1H), 7.08 (t, J = 8.8 Hz, 2H), 6.95 (dd, J = 8.6, 5.6 Hz, 2H), 5.26 (t, J = 7.1 Hz, 1H), 4.84 (d, J = 7.1 Hz, 1H), 4.57 (d, J = 4.8 Hz, 0H), 4.09 (t, J = 9.4 Hz, 2H), 4.03-3.85 (m, 2H), 3.66-3.41 (m, 2H), 2.17 (s, 1H), 1.96 (d, J = 4.1 Hz, 2H), 1.32 (t, J = 7.0 Hz, 3H). LCMS Calculated for $C_{28}H_{26}F_4N_4O_5$: 574.18; Observed (Method-AO): 575.2 [M + H]$^+$, 98.2% at RT 1.282 min. Optical rotation: a = −262.9, (c = 0.1 g/100 mL in MeOH, T = 25° C.).

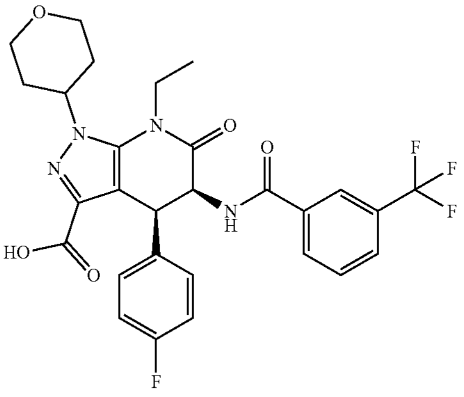 [SMILES: CCN1C(=O)[C@@H](NC(=O)c2cccc(C(F)(F)F)c2)[C@@H](c2ccc(F)cc2)c2c(C(=O)O)nn(C3CCOCC3)c21]

I-657

$^1$H NMR (300 MHz, DMSO-$d_6$) δ 12.83 (s, 1H), 8.53 (d, J = 7.0 Hz, 1H), 8.23-8.07 (m, 2H), 7.92 (d, J = 7.8 Hz, 1H), 7.71 (t, J = 7.8 Hz, 1H), 7.21-7.02 (m, 2H), 7.02-6.85 (m, 2H), 5.26 (t, J = 7.1 Hz, 1H), 4.84 (d, J = 7.1 Hz, 1H), 4.57 (s, 1H), 4.10 (td, J = 13.1, 11.4, 5.4 Hz, 2H), 4.02-3.86 (m, 2H), 3.65-3.45 (m, 2H), 2.41-2.24 (m, 1H), 2.15 (d, J = 13.0 Hz, 1H), 1.95 (t, J = 8.0 Hz, 2H), 1.32 (t, J = 7.0 Hz, 3H). LCMS Calculated for $C_{28}H_{26}F_4N_4O_5$: 574.18; Observed (Method-B): 575.2 [M + H]$^+$, 97.8% at RT 0.985 min. Optical rotation: a = +235.9, (c = 0.1 g/100 mL in MeOH, T = 25° C.).

7. Synthesis of (4R,5R)-1,4-dicyclopropyl-7-ethyl-6-oxo-5-(3-(trifluoromethyl)benzamido)-4,5,6,7-tetrahyde-1H-pyrazolo[3,4-b]pyridine-3-carboxylic acid (I-678) and (4S,5S)-1,4-dicyclopropyl-7-ethyl-6-oxo-5-(3-(trifluoromethyl)benzamido)-4,5,6,7-tetrahydro-1H-pyrazolo[3,4-b]pyridine-3-carboxylic acid (I-520)

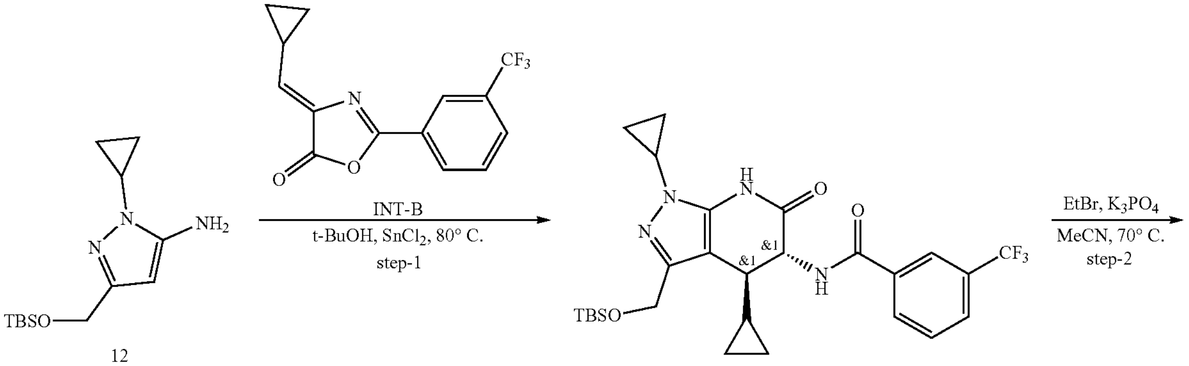

12

35

-continued

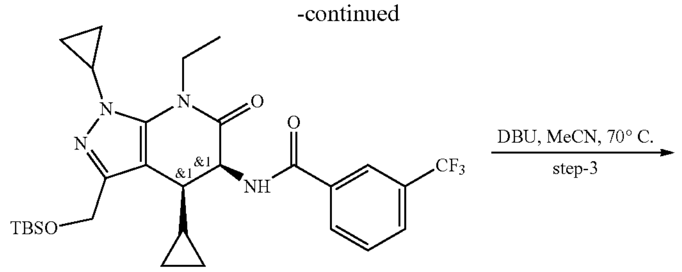

36

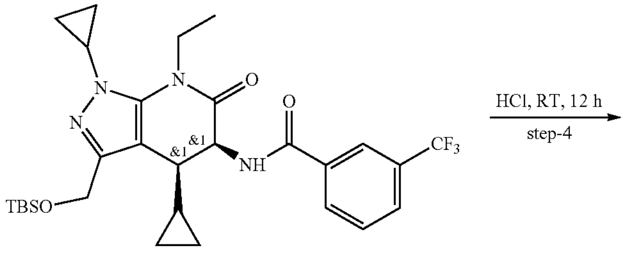

37

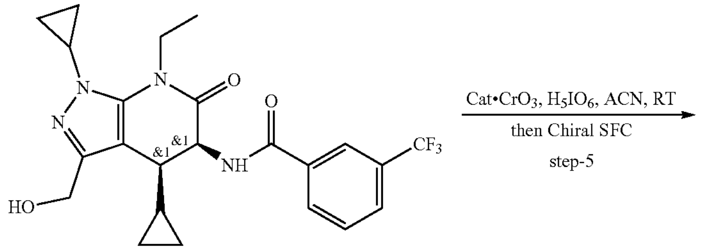

38

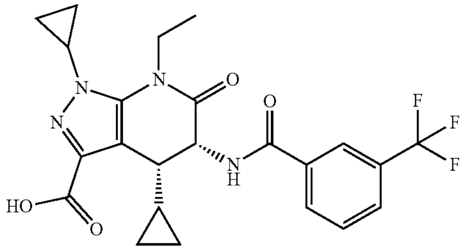 [SMILES: CCN1C(=O)[C@H](NC(=O)c2cccc(C(F)(F)F)c2)[C@H](C2CC2)c2c(C(=O)O)nn(C3CC3)c21]

I-628

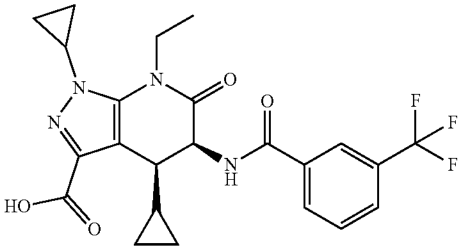 [SMILES: CCN1C(=O)[C@@H](NC(=O)c2cccc(C(F)(F)F)c2)[C@@H](C2CC2)c2c(C(=O)O)nn(C3CC3)c21]

I-520

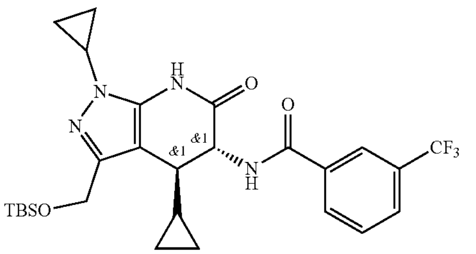

rac-N-((4R,5S)-3-(((tert-butyldimethlsilyl)oxy)methyl)-1,4-dicyclopropyl-6-oxo-4,5,6,7-tetrahydro-1H-pyrazolo[3,4-b]pyridin-5-yl)-3-(trifluoromethyl)benzamide (35)

Into a 500 mL 3-necked round-bottom flask were added t-BuOH (150 mL), 5-([(tert-butyldimethylsilyl)oxy]methyl-2-cyclopropylpyrazol-3-amine (8.00 g, 29.9 mmol, 1.00 equiv), (4Z)-4-(cyclopropylmethylidene)-2-[3-(trifluoromethyl)phenyl]-1,3-oxazol-5-one (10.1 g, 35.9 mmol, 1.20 equiv) and $SnCl_2$ (0.57 g, 2.99 mmol, 0.100 equiv) at room temperature. The resulting mixture was stirred for 4 h at 80° C. The mixture was allowed to cool down to room temperature. The resulting mixture was concentrated under reduced pressure. The residue was purified by silica gel column chromatography, eluted with petroleum ether/EtOAc (1:1) to afford rac-N-((4R,5S)-3-(((tert-butyldimethylsilyl)oxy)methyl)-1,4-dicyclopropyl-6-oxo-4,5,6,7-tetrahydro-1H-pyrazolo[3,4-b]pyridin-5-yl)-3-(trifluoromethyl)benzamide (11.5 g, 70%) as a light yellow solid.

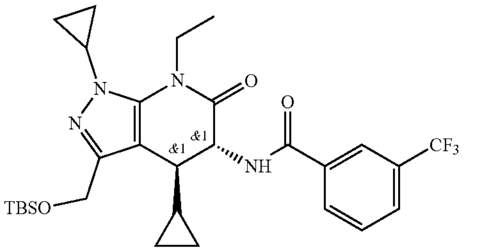

rac-N-((4R,5S)-3-(((tert-butyldimethlsilyl)oxy)methyl)-1,4-dicyclopropyl-7-ethyl-6-oxo-4,5,6,7-tetrahydro-1H-pyrazolo[3,4-b]pyridin-5-yl)-3-(trifluoromethyl)benzamide (36)

Into a 500 mL 3-necked round-bottom flask were added rac-N-((4R,5S)-3-(((tert-butyldimethylsilyl)oxy)methyl)-1,4-dicyclopropyl-6-oxo-4,5,6,7-tetrahydro-1H-pyrazolo[3,4-b]pyridin-5-yl)-3-(trifluoromethyl)benzamide (11.5 g, 20.9 mmol, 1.00 equiv), 1-bromopropane (3.09 g, 25.2 mmol, 1.20 equiv), $K_3PO_4$ (8.90 g, 41.9 mmol, 2.00 equiv) and MeCN (150 mL) at room temperature. The resulting mixture was stirred at 70° C. for 4 h. The mixture was allowed to cool down to room temperature. The reaction was quenched with Water at room temperature. The resulting mixture was extracted with EtOAc (3×100 mL). The combined organic layers were washed with brine (100 mL), dried over anhydrous $Na_2SO_4$. After filtration, the filtrate was concentrated under reduced pressure. The residue was purified by silica gel column chromatography, eluted with petroleum ether/EtOAc (1:1) to afford rac-N-((4R,5S)-3-(((tert-butyldimethylsilyl)oxy)methyl)-1,4-dicyclopropyl-7-ethyl-6-oxo-4,5,6,7-tetrahydro-1H-pyrazolo[3,4-b]pyridin-5-yl)-3-(trifluoromethyl)benzamide (11 g, 91%) as a colorless oil.

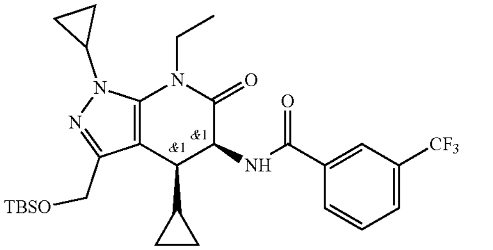

rac-N-((4R,5R)-3-(((tert-butyldimethlsilyl)oxy)methyl)-1,4-dicyclopropyl-7-ethyl-6-oxo-4,5,6,7-tetrahydro-1H-pyrazolo[3,4-b]pyridin-5-yl)-3-(trifluoromethyl)benzamide (37)

Into a 500 mL 3-necked round-bottom flask were added rac-N-((4R,5S)-3-(((tert-butyldimethylsilyl)oxy)methyl)-1,4-dicyclopropyl-7-ethyl-6-oxo-4,5,6,7-tetrahydro-1H-pyrazolo[3,4-b]pyridin-5-yl)-3-(trifluoromethyl)benzamide (11.0 g, 19.1 mmol, 1.00 equiv), DBU (8.71 g, 57.2 mmol, 3.00 equiv) and MeCN (150 mL) at room temperature. The resulting mixture was stirred at 70° C. for 16 h. The mixture was allowed to cool down to room temperature. The reaction was quenched with Water at room temperature. The resulting mixture was extracted with EtOAc (3×100 mL). The combined organic layers were washed with brine (100 mL), dried over anhydrous $Na_2SO_4$. After filtration, the filtrate was concentrated under reduced pressure. The residue was purified by silica gel column chromatography, eluted with petroleum ether/EtOAc (1:1) to afford rac-N-((4R,5R)-3-(((tert-butyldimethylsilyl)oxy)methyl)-1,4-dicyclopropyl-7-ethyl-6-oxo-4,5,6,7-tetrahydro-1H-pyrazolo[3,4-b]pyridin-5-yl)-3-(trifluoromethyl)benzamide (9.2 g, 83%) as a light yellow oil.

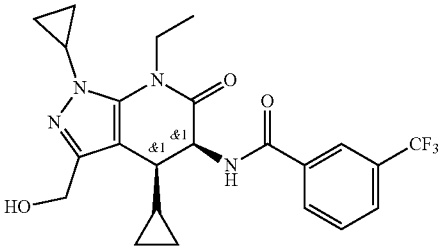

rac-N-((4R,5R)-1,4-dicyclopropyl-7-ethyl-3-(hydroxymethyl)-6-oxo-4,5,6,7-tetrahydro-1H-pyrazolo[3,4-b]pyridin-5-yl)-3-(trifluoromethyl)benzamide (38)

Into a 250 mL 3-necked round-bottom flask were added rac-N-((4R,5R)-3-(((tert-butyldimethylsilyl)oxy)methyl)-1,4-dicyclopropyl-7-ethyl-6-oxo-4,5,6,7-tetrahydro-1H-pyrazolo[3,4-b]pyridin-5-yl)-3-(trifluoromethyl)benzamide (9.20 g, 15.9 mmol, 1.00 equiv), HCl (38% in $H_2O$, 50 mL) and MeCN (50 mL) at room temperature. The resulting mixture was stirred at room temperature for 12 h. The mixture was neutralized to pH 7 with saturated $Na_2CO_3$ (aq.). The resulting mixture was extracted with EtOAc (3×100 mL). The combined organic layers were washed with brine (100 mL), dried over anhydrous $Na_2SO_4$. After filtration, the filtrate was concentrated under reduced pressure. This resulted in rac-N-((4R,5R)-1,4-dicyclopropyl-7-ethyl-3-(hydroxymethyl)-6-oxo-4,5,6,7-tetrahydro-1H-pyrazolo[3,4-b]pyridin-5-yl)-3-(trifluoromethyl)benzamide (7 g, 94%) as an off-white solid.

(4R,5R)-1,4-dicyclopropyl-7-ethyl-6-oxo-5-(3-(trifluoromethyl)benzamido)-4,5,6,7-tetrahydro-1H-pyrazolo[3,4-b]pyridine-3-carboxylic acid (I-678) and (4S,5S)-1,4-dicyclopropyl-7-ethyl-6-oxo-5-(3-(trifluoromethyl)benzamido)-4,5,6,7-tetrahydro-1H-pyrazolo[3,4-b]pyridine-3-carboxylic acid (I-520)

Into a 250 mL 3-necked round-bottom flask were added rac-N-((4R,5R)-1,4-dicyclopropyl-7-ethyl-3-(hydroxymethyl)-6-oxo-4,5,6,7-tetrahydro-1H-pyrazolo[3,4-b]pyridin-5-yl)-3-(trifluoromethyl)benzamide (7.00 g, 15.1 mmol, 1.00 equiv), MeCN (100 mL), $CrO_3$ (0.61 g, 6.05 mmol, 0.400 equiv) and $H_5IO_6$ (11.4 g, 49.9 mmol, 3.30 equiv) at room temperature. The resulting mixture was stirred at room temperature for 6 h. The reaction was quenched by the addition of $Na_2S_2O_3$ aq (200 mL) at room temperature. The resulting mixture was extracted with EtOAc (3×100 mL). The combined organic layers were washed with brine (1×100 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% FA), 10% to 50% gradient in 10 min; detector, UV 254 nm. This resulted in rac-(4R,5R)-1,4-dicyclopropyl-7-ethyl-6-oxo-5-(3-(trifluoromethyl)benzamido)-4,5,6,7-tetrahydro-1H-pyrazolo[3,4-b]pyridine-3-carboxylic acid (5.5 g). The product (5.5 g) was purified by Prep-Chiral-SFC to afford (4R,5R)-1,4-dicyclopropyl-7-ethyl-6-oxo-5-(3-(trifluoromethyl)benzamido)-4,5,6,7-tetrahydro-1H-pyrazolo[3,4-b]pyridine-3-carboxylic acid (I-678) (2.3 g, 31%) and (4S,5S)-1,4-dicyclopropyl-7-ethyl-6-oxo-5-(3-(trifluoromethyl)benzamido)-4,5,6,7-tetrahydro-1H-pyrazolo[3,4-b]pyridine-3-carboxylic acid (I-520) (2.2 g, 30%) as a white solid.

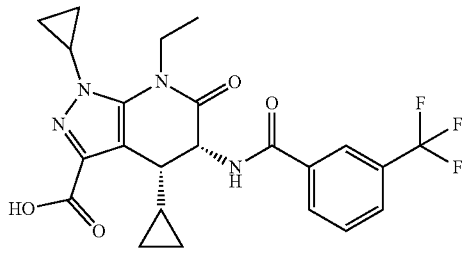

I-678

$^1$H NMR (400 MHz, DMSO-$d_6$) δ 12.84 (s, 1H), 9.01 (d, J = 7.9 Hz, 1H), 8.32 (s, 1H), 8.25 (d, J = 7.8 Hz, 1H), 7.95 (d, J = 7.8 Hz, 1H), 7.76 (t, J = 7.8 Hz, 1H), 5.07 (dd, J = 7.8, 6.0 Hz, 1H), 4.31 (dq, J = 14.3, 6.8 Hz, 1H), 4.17-4.08 (m, 1H), 3.75 (p, J = 3.4 Hz, 1H), 3.36 (t, J = 6.2 Hz, 1H), 1.30 (d, J = 7.1 Hz, 1H), 1.23 (t, J = 7.0 Hz, 4H), 1.15 (dd, J = 7.8, 5.7 Hz, 1H), 1.13-1.03 (m, 1H), 0.85 (d, J = 6.3 Hz, 1H), 0.48 (td, J = 8.8, 4.6 Hz, 1H), 0.24-0.13 (m, 1H), 0.08 (dd, J = 9.2, 4.5 Hz, 2H).
LCMS Calculated for $C_{23}H_{23}F_3N_4O_4$: 476.17; Observed (Method-B): 477.1 [M + H] $^+$, 98.7% at RT 0.943 min.
Optical rotation: a = −26, (c = 0.1 g/100 mL in MeOH, T = 25° C.).

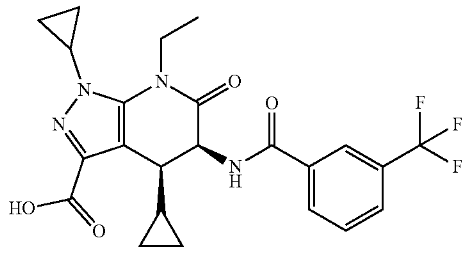

I-520

$^1$H NMR (400 MHz, DMSO-$d_6$) δ 12.83 (s, 1H), 9.02 (d, J = 7.9 Hz, 1H), 8.32 (s, 1H), 8.25 (d, J = 7.9 Hz, 1H), 7.95 (d, J = 7.9 Hz, 1H), 7.76 (t, J = 7.8 Hz, 1H), 5.07 (dd, J = 7.8, 6.0 Hz, 1H), 4.36-4.27 (m, 1H), 4.13 (dd, J = 14.2, 7.0 Hz, 1H), 3.75 (dt, J = 7.1, 3.4 Hz, 1H), 3.35 (t, J = 6.3 Hz, 1H), 1.31 (d, J = 8.1 Hz, 1H), 1.23 (t, J = 7.0 Hz, 4H), 1.18-1.12 (m, 1H), 1.10-1.03 (m, 1H), 0.85 (d, J = 6.2 Hz, 1H), 0.48 (t, J = 4.4 Hz, 1H), 0.23-0.16 (m, 1H), 0.07 (dd, J = 9.3, 4.4 Hz, 1H).
LCMS Calculated for $C_{23}H_{23}F_3N_4O_4$: 476.17; Observed (Method-B): 477.1 [M + H] $^+$, 99.3% at RT 1.101 min.
Optical rotation: a = +36, (c = 0.1 g/100 mL in MeOH, T = 25° C.).

Compounds below prepared from the acid intermediates described above and the method used to make I-289 and I-300.

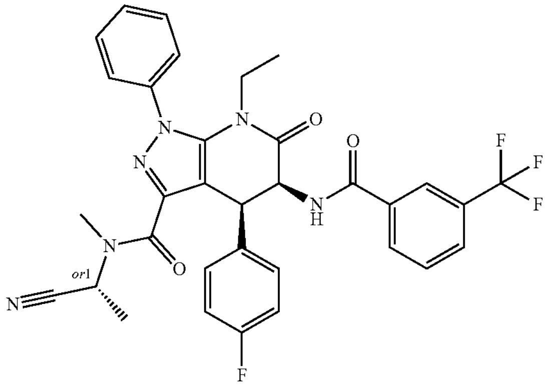 [SMILES: CCN1C(=O)[C@@H](NC(=O)c2cccc(C(F)(F)F)c2)[C@@H](c2ccc(F)cc2)c2c(C(=O)N(C)[C@H](C)C#N)nn(-c3ccccc3)c21]

I-289

$^1$H NMR (300 MHz, DMSO-$d_6$) δ 8.58 (d, J = 7.2 Hz, 1H), 8.15 (d, J = 9.8 Hz, 2H), 7.93 (d, J = 7.8 Hz, 1H), 7.82 (d, J = 7.0 Hz, 2H), 7.73 (d, J = 7.8 Hz, 1H), 7.70-7.54 (m, 3H), 7.08 (t, J = 8.7 Hz, 2H), 6.98 (t, J = 7.0 Hz, 2H), 5.56 (t, J = 7.2 Hz, 1H), 4.87 (d, J = 7.2 Hz, 1H), 3.98-3.70 (m, 2H), 3.17-2.77 (m, 2H), 2.12-1.57 (m, 2H), 1.43 (s, 3H), 0.92 (t, J = 7.0 Hz, 3H).
LCMS Calculated for $C_{33}H_{28}F_4N_6O_3$: 632.22; Observed (Method-A): 633.3 [M + H] $^+$, 99.6% at RT 1.298 min.

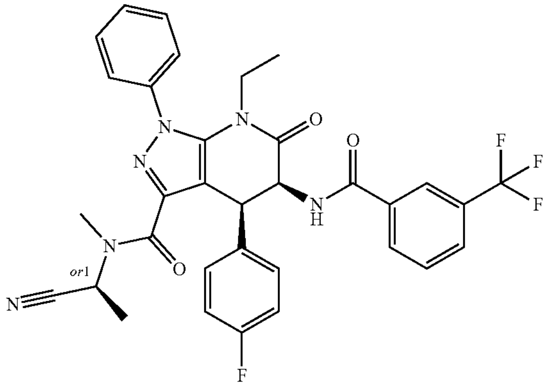 [SMILES: CCN1C(=O)[C@@H](NC(=O)c2cccc(C(F)(F)F)c2)[C@@H](c2ccc(F)cc2)c2c(C(=O)N(C)[C@@H](C)C#N)nn(-c3ccccc3)c21]

I-300

$^1$H NMR (300 MHz, DMSO-$d_6$) δ 8.58 (d, J = 7.2 Hz, 1H), 8.16 (d, J = 10.3 Hz, 2H), 7.93 (d, J = 7.8 Hz, 1H), 7.82 (s, 2H), 7.73 (d, J = 7.8 Hz, 1H), 7.64 (d, J = 7.5 Hz, 3H), 7.09 (t, J = 8.7 Hz, 2H), 6.99 (dd, J = 8.6, 5.5 Hz, 2H), 5.56 (t, J = 7.2 Hz, 1H), 4.86 (s, 1H), 3.99-3.75 (m, 1H), 3.13-2.85 (m, 2H), 1.60-1.48 (m, 3H), 1.24 (s, 3H), 0.92 (t, J = 7.0 Hz, 3H).
LCMS Calculated for $C_{33}H_{28}F_4N_6O_3$: 632.22; Observed (Method-B): 633.20 [M + H] $^+$, 99.1% at RT 1.406 min.

-continued

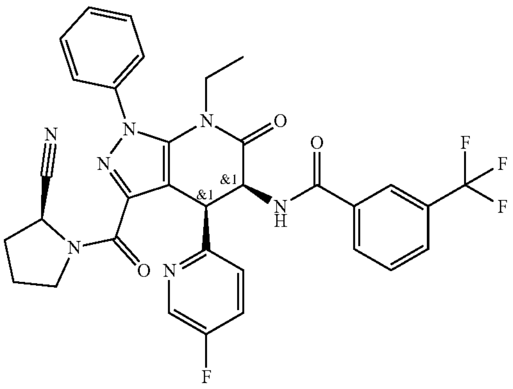 [SMILES: CCN1C(=O)[C@@H](NC(=O)c2cccc(C(F)(F)F)c2)[C@@H](c2ccc(F)cn2)c2c(C(=O)N3CCC[C@H]3C#N)nn(-c3ccccc3)c21]

I-409

$^1$H NMR (300 MHz, DMSO-$d_6$) δ 8.54-8.42 (m, 1H), 8.40-8.31 (m, 1H), 8.09-7.99 (m, 2H), 7.88 (d, J = 7.8 Hz, 1H), 7.81-7.54 (m, 7H), 7.37-7.25 (m, 1H), 5.66-5.32 (m, 1H), 5.23-4.71 (m, 2H), 4.13-3.88 (m, 2H), 3.71-3.40 (m, 1H), 3.08-2.80 (m, 1H), 2.32-2.05 (m, 2H), 2.04-1.80 (m, 2H), 0.88 (t, J = 6.9 Hz, 3H).
LCMS Calculated for $C_{33}H_{27}F_4N_7O_3$: 645.21; Observed (Method-J): 646.3 [M + H] $^+$, 96.3% at RT 2.085 min.

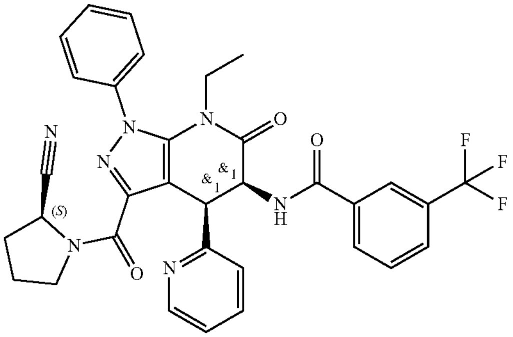

I-413

$^1$H NMR (300 MHz, DMSO-$d_6$) δ 8.46 (d, J = 8.1 Hz, 1H), 8.39 (s, 1H), 8.03 (s, 2H), 7.73-7.53 (m, 8H), 7.31-7.25 (m, 1H), 7.22 (d, J = 5.3 Hz, 1H), 5.47 (m, 1H), 5.20-4.94 (m, 2H), 3.99 (m, 2H), 3.90-3.42 (m, 1H), 2.94 (d, J = 8.7 Hz, 1H), 2.17 (m, 4H), 0.89 (d, J = 6.4 Hz, 3H).
LCMS Calculated for $C_{33}H_{28}F_3N_7O_3$: 627.22; Observed (Method-K): 628.4 [M + H] $^+$, 95.3% at RT 1.251 min.

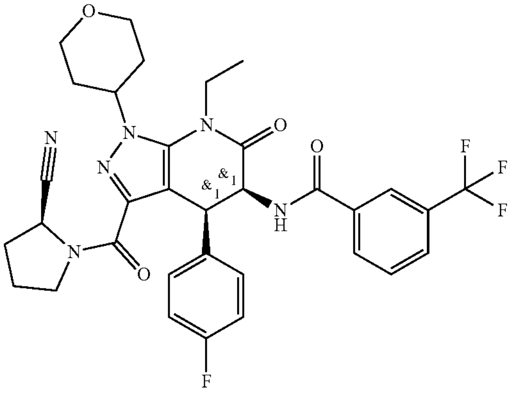 [SMILES: CCN1C(=O)[C@@H](NC(=O)c2cccc(C(F)(F)F)c2)[C@@H](c2ccc(F)cc2)c2c(C(=O)N3CCC[C@H]3C#N)nn(C3CCOCC3)c21]

I-292

$^1$H NMR (400 MHz, DMSO-$d_6$) δ 8.52 (q, J = 8.9, 7.9 Hz, 1H), 8.18-8.07 (m, 2H), 7.92 (d, J = 7.9 Hz, 1H), 7.71 (t, J = 7.9 Hz, 1H), 7.07 (t, J = 8.6 Hz, 2H), 7.00-6.84 (m, 2H), 5.71-4.95 (m, 2H), 4.85 (d, J = 6.1 Hz, 1H), 4.61 (s, 1H), 4.21-3.84 (m, 5H), 3.66-3.44 (m, 3H), 2.50-1.80 (m, 8H), 1.32 (t, J = 6.8 Hz, 3H).
LCMS Calculated for $C_{33}H_{32}F_4N_6O_4$: 652.2; Observed (Method-J): 651.2 [M − H] $^+$, 97.0% at RT 1.891 min.

-continued

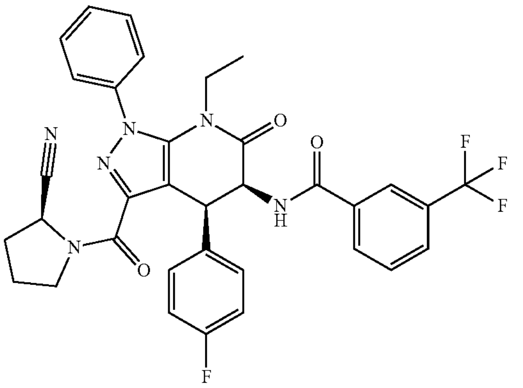 [SMILES: CCN1C(=O)[C@@H](NC(=O)c2cccc(C(F)(F)F)c2)[C@@H](c2ccc(F)cc2)c2c(C(=O)N3CCC[C@H]3C#N)nn(-c3ccccc3)c21]

I-278

$^1$H NMR (300 MHz, DMSO-$d_6$) δ 8.59 (dd, J = 10.4, 7.2 Hz, 1H), 8.22-8.12 (m, 2H), 7.93 (d, J = 7.9 Hz, 1H), 7.80 (dd, J = 7.5, 2.4 Hz, 2H), 7.76-7.55 (m, 4H), 7.09 (t, J = 8.7 Hz, 2H), 6.99 (dd, J = 8.6, 5.6 Hz, 2H), 5.70-4.81 (m, 3H), 4.12-3.84 (m, 2H), 3.65-3.39 (m, 1H), 3.06 (m, 1H), 2.32-1.84 (m, 4H), 0.98-0.85 (m, 3H).
LCMS Calculated for $C_{34}H_{28}F_4N_6O_3$: 644.22; Observed (Method-F): 645.1 [M + H] $^+$, 98.0% at RT 1.574 min.

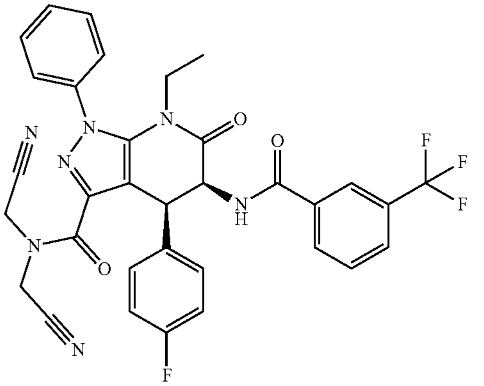 [SMILES: CCN1C(=O)[C@@H](NC(=O)c2cccc(C(F)(F)F)c2)[C@@H](c2ccc(F)cc2)c2c(C(=O)N(CC#N)CC#N)nn(-c3ccccc3)c21]

I-302

$^1$H NMR (400 MHz, DMSO-$d_6$) δ 8.60 (d, J = 7.2 Hz, 1H), 8.21-8.13 (m, 2H), 7.93 (d, J = 7.8 Hz, 1H), 7.86 (d, J = 7.5 Hz, 2H), 7.68 (m, 4H), 7.09 (t, J = 8.6 Hz, 2H), 7.00 (dd, J = 8.6, 5.4 Hz, 2H), 5.57 (t, J = 7.2 Hz, 1H), 5.17 (q, J = 18.3 Hz, 2H), 4.96 (d, J = 7.2 Hz, 1H), 4.67-4.51 (m, 2H), 3.91 (dd, J = 14.3, 7.4 Hz, 1H), 3.06 (dt, J = 14.4, 6.9 Hz, 1H), 0.92 (t, J = 7.0 Hz, 3H).
LCMS Calculated for $C_{33}H_{25}F_4N_7O_3$: 643.20; Observed (Method-C): 644.1 [M + H] $^+$, 99.1% at RT 1.325 min.

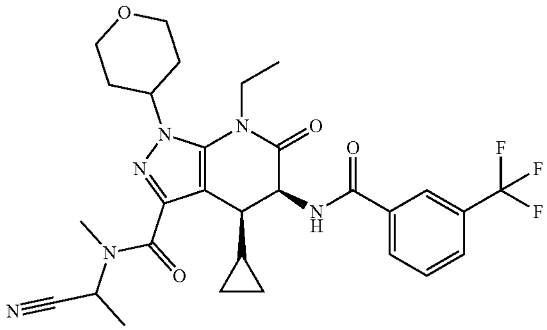 [SMILES: CCN1C(=O)[C@@H](NC(=O)c2cccc(C(F)(F)F)c2)[C@@H](C2CC2)c2c(C(=O)N(C)C(C)C#N)nn(C3CCOCC3)c21]

I-349

$^1$H NMR (400 MHz, DMSO-$d_6$) δ 9.01 (d, J = 7.9 Hz, 1H), 8.31 (s, 1H), 8.24 (d, J = 7.9 Hz, 1H), 7.99-7.92 (m, 1H), 7.76 (t, J = 7.8 Hz, 1H), 6.02 (s, 1H), 5.08 (s, 1H), 4.50 (s, 1H), 4.14-4.00 (m, 2H), 3.98-3.81 (m, 2H), 3.61-3.44 (m, 2H), 3.26 (d, J = 20.1 Hz, 3H), 3.01 (s, 1H), 2.25 (d, J = 12.4 Hz, 2H), 2.09 (d, J = 12.3 Hz, 1H), 1.92 (s, 2H), 1.69-1.47 (m, 3H), 1.26 (t, J = 7.0 Hz, 3H), 0.82 (s, 1H), 0.48 (t, J = 8.7 Hz, 1H), 0.21 (d, J = 9.0 Hz, 2H).
LCMS Calculated for $C_{29}H_{33}F_3N_6O_4$: 586.25; Observed (Method-A): 587.3 [M + H] +, 97.5% at RT 1.17 min.

-continued

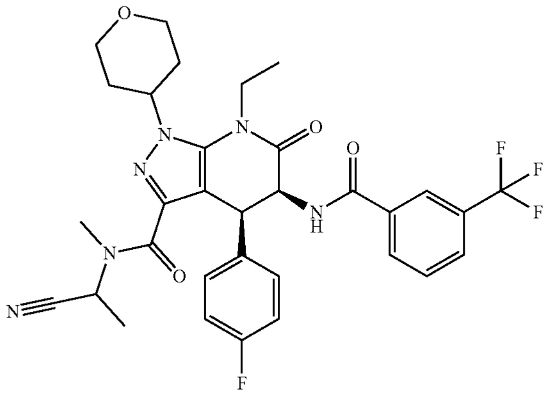 [SMILES: CCN1C(=O)[C@@H](NC(=O)c2cccc(C(F)(F)F)c2)[C@@H](c2ccc(F)cc2)c2c(C(=O)N(C)C(C)C#N)nn(C3CCOCC3)c21]

I-305

$^1$H NMR (300 MHz, DMSO-$d_6$) δ 8.49 (d, J = 7.1 Hz, 1H), 8.12 (d, J = 11.1 Hz, 2H), 7.92 (d, J = 7.8 Hz, 1H), 7.71 (t, J = 7.8 Hz, 1H), 7.11-7.01 (m, 2H), 6.99-6.90 (m, 2H), 5.91 (d, J = 211.5 Hz, 1H), 5.24 (t, J = 7.0 Hz, 1H), 4.80 (d, J = 7.0 Hz, 1H), 4.67-4.52 (m, 1H), 4.24-3.88 (m, 4H), 3.67-3.47 (m, 2H), 2.94 (s, 1H), 2.41-2.24 (m, 1H), 2.17 (d, J = 12.6 Hz, 1H), 1.99 (s, 2H), 1.70-1.39 (m, 3H), 1.32 (t, J = 7.1 Hz, 3H).
LCMS Calculated for $C_{32}H_{33}F_4N_6O_4$; 640.24; Observed (Method-K): 641.4 [M + H] $^+$, 98.6% at RT 1.179 min.

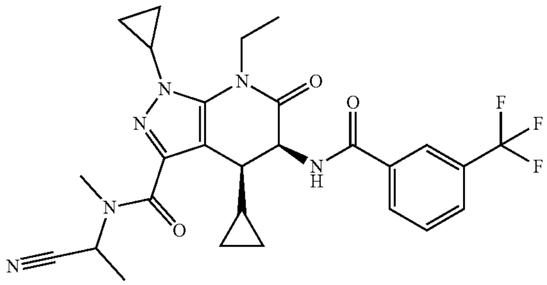 [SMILES: CCN1C(=O)[C@@H](NC(=O)c2cccc(C(F)(F)F)c2)[C@@H](C2CC2)c2c(C(=O)N(C)C(C)C#N)nn(C3CC3)c21]

I-492

$^1$H NMR (400 MHz, DMSO-$d_6$) δ 9.01 (d, J = 8.0 Hz, 1H), 8.31 (s, 1H), 8.25 (d, J = 7.8 Hz, 1H), 7.95 (d, J = 7.8 Hz, 1H), 7.76 (t, J = 7.8 Hz, 1H), 5.11 (ddd, J = 8.0, 6.2, 4.0 Hz, 1H), 4.32 (dq, J = 14.2, 7.1 Hz, 1H), 4.14 (dq, J = 13.9, 6.8 Hz, 1H), 3.76 (tt, J = 7.1, 3.5 Hz, 1H), 3.42-3.34 (m, 1H), 2.99 (s, 4H), 1.54 (d, J = 7.5 Hz, 3H), 1.24 (t, J = 7.0 Hz, 5H), 1.20-1.12 (m, 1H), 1.12-1.03 (m, 1H), 0.84 (s, 1H), 0.47 (t, J = 8.5 Hz, 1H), 0.20 (t, J = 8.9 Hz, 1H).
LCMS Calculated for $C_{27}H_{29}F_3N_6O_3$: 542.23; Observed (Method-A): 541.2 [M − H] $^-$, 99.5% at RT 1.198 min.

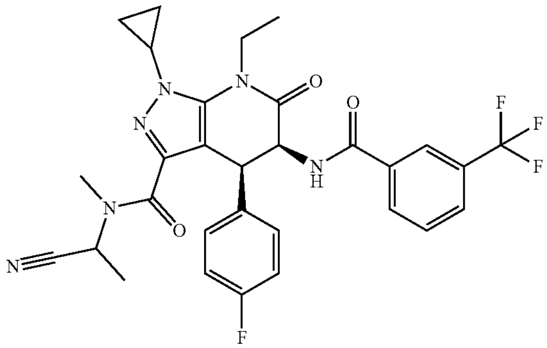 [SMILES: CCN1C(=O)[C@@H](NC(=O)c2cccc(C(F)(F)F)c2)[C@@H](c2ccc(F)cc2)c2c(C(=O)N(C)C(C)C#N)nn(C3CC3)c21]

I-306

$^1$H NMR (300 MHz, DMSO-$d_6$) δ 8.00 (s, 1H), 7.85 (d, J = 7.8 Hz, 1H), 7.78 (d, J = 7.8 Hz, 1H), 7.57 (t, J = 7.8 Hz, 1H), 7.00-6.88 (m, 4H), 6.86-6.41 (m, 1H), 5.15-4.94 (m, 2H), 4.46 (dq, J = 14.4, 7.1 Hz, 1H), 4.27 (dq, J = 14.1, 7.0 Hz, 1H), 3.62 (tt, J = 7.1, 3.7 Hz, 1H), 3.53-2.91 (m, 3H), 1.73-1.49 (m, 3H), 1.48-1.33 (m, 5H), 1.35-1.25 (m, 1H), 1.24-1.13 (m, 1H).
LCMS Calculated for $C_{30}H_{28}F_4N_6O_3$: 596.22; Observed (Method-L): 597.3 [M + H] $^+$, 98.9% at RT 1.899.

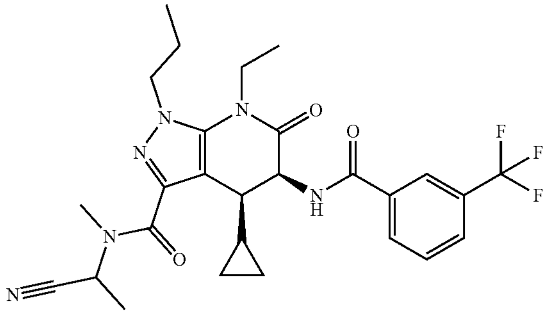 [SMILES: CCCn1nc(C(=O)N(C)C(C)C#N)c2c1N(CC)C(=O)[C@@H](NC(=O)c1cccc(C(F)(F)F)c1)[C@H]2C1CC1]

I-596

$^1$H NMR (400 MHz, DMSO-$d_6$) δ 9.02 (d, J = 7.9 Hz, 1H), 8.30 (s, 1H), 8.24 (d, J = 7.8 Hz, 1H), 7.95 (d, J = 8.0 Hz, 1H), 7.75 (t, J = 7.8 Hz, 1H), 6.18-5.53 (m, 1H), 5.10-5.01 (m, 1H), 4.23-4.09 (m, 3H), 3.82-3.72 (m, 1H), 3.31-3.23 (m, 4H), 3.02-2.97 (m, 1H), 1.86-1.82 (m, 2H), 1.53 (d, J = 7.3 Hz, 3H), 1.22 (t, J = 7.1 Hz, 3H), 0.94-0.71 (m, 4H), 0.52-0.41 (m, 1H), 0.21-0.17 (m, 1H), −0.01-−0.11 (m, 1H).
LCMS Calculated for $C_{27}H_{31}F_3N_6O_3$: 544.24; Observed (Method-A): 543.2 [M − H] $^-$, 99.3% at RT 1.242 min.

-continued

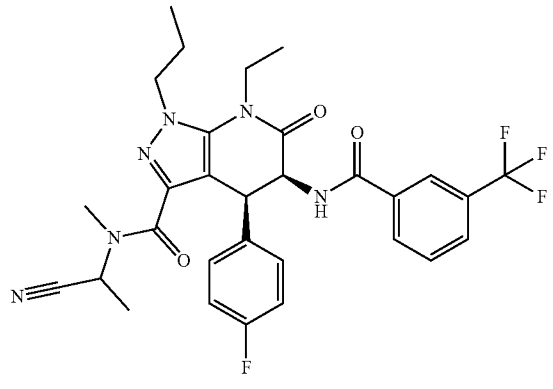 [SMILES: CCCn1nc(C(=O)N(C)C(C)C#N)c2c1N(CC)C(=O)[C@@H](NC(=O)c1cccc(C(F)(F)F)c1)[C@H]2c1ccc(F)cc1]

I-307

$^1$H NMR (400 MHz, Chloroform-d) δ 8.02 (s, 1H), 7.88 (d, J = 7.8 Hz, 1H), 7.80 (d, J = 7.8 Hz, 1H), 7.59 (t, J = 7.8 Hz, 1H), 6.96 (dd, J = 6.9, 1.1 Hz, 4H), 6.82 (s, 1H), 5.81 (s, 1H), 5.17-5.01 (m, 2H), 4.37-4.18 (m, 3H), 3.96-3.85 (m, 1H), 3.55-2.97 (m, 3H), 2.06-1.94 (m, 3H), 1.69-1.55 (m, 2H), 1.50 (s, 1H), 1.42 (t, J = 7.1 Hz, 3H), 1.04 (dd, J = 8.8, 6.4 Hz, 3H).
LCMS Calculated for $C_{30}H_{30}F_4N_6O_3$: 598.23; Observed (Method-M): 599.3 [M + H] $^+$, 99.8% at RT 1.519 min.

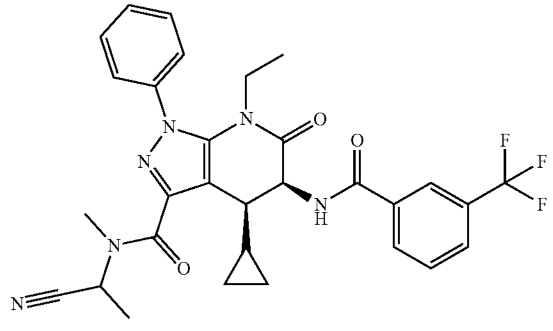 [SMILES: CCN1C(=O)[C@@H](NC(=O)c2cccc(C(F)(F)F)c2)[C@@H](C2CC2)c2c(C(=O)N(C)C(C)C#N)nn(-c3ccccc3)c21]

I-543

$^1$H NMR (300 MHz, DMSO-$d_6$) δ 9.09 (d, J = 8.0 Hz, 1H), 8.34 (d, J = 2.2 Hz, 1H), 8.28 (d, J = 7.8 Hz, 1H), 7.96 (d, J = 7.8 Hz, 1H), 7.85-7.67 (m, 3H), 7.68-7.52 (m, 3H), 5.84 (d, J = 149.5 Hz, 1H), 5.41 (ddd, J = 8.2, 6.2, 2.0 Hz, 1H), 3.95-3.81 (m, 1H), 3.30 (s, 3H), 3.06-2.89 (m, 2H), 1.55 (d, J = 7.1 Hz, 3H), 0.86 (q, J = 7.0, 5.5 Hz, 4H), 0.53 (t, J = 8.4 Hz, 1H), 0.25 (t, J = 9.1 Hz, 1H), 0.09--0.01 (m, 2H).
LCMS Calculated for $C_{30}H_{29}F_3N_6O_3$: 578.23; Observed (Method-A): 579.3 [M + H] $^+$, 99.1% at RT 1.282.

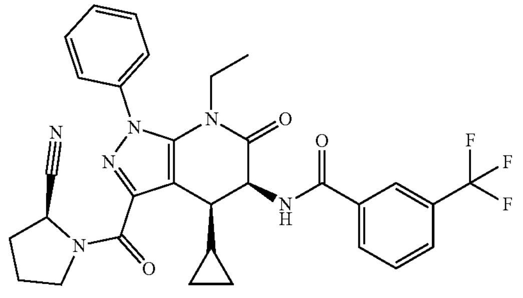 [SMILES: CCN1C(=O)[C@@H](NC(=O)c2cccc(C(F)(F)F)c2)[C@@H](C2CC2)c2c(C(=O)N3CCC[C@H]3C#N)nn(-c3ccccc3)c21]

I-686

1H NMR (300 MHz, DMSO-d6) δ 9.08 (t, J = 8.5 Hz, 1H), 8.34 (s, 1H), 8.28 (d, J = 7.8 Hz, 1H), 7.96 (d, J = 7.8 Hz, 1H), 7.82-7.69 (m, 3H), 7.68-7.49 (m, 3H), 5.73-4.79 (m, 2H), 4.10-3.81 (m, 2H), 3.76-3.40 (m, 2H), 3.11-2.70 (m, 1H), 2.41-2.11 (m, 2H), 2.02 (p, J = 6.7 Hz, 2H), 1.03-0.70 (m, 4H), 0.53 (d, J = 5.1 Hz, 1H), 0.29-0.03 (m, 3H).
LCMS Calculated for $C_{31}H_{29}F_3N_6O_3$: 590.23; Observed (Method-I): 589.2 [M − H] $^-$, 98.4% at RT 1.836 min.

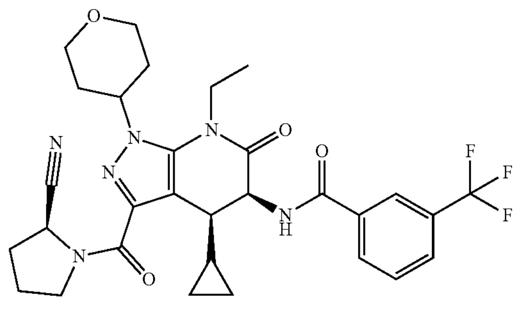 [SMILES: CCN1C(=O)[C@@H](NC(=O)c2cccc(C(F)(F)F)c2)[C@@H](C2CC2)c2c(C(=O)N3CCC[C@H]3C#N)nn(C3CCOCC3)c21]

I-348

$^1$H NMR (300 MHz, DMSO-$d_6$) δ 9.01 (t, J = 7.5 Hz, 1H), 8.34-8.20 (m, 2H), 7.95 (d, J = 7.9 Hz, 1H), 7.75 (t, J = 7.8 Hz, 1H), 5.62 (t, J = 4.8 Hz, 1H), 5.09-4.87 (m, 2H), 4.52 (s, 1H), 4.14-3.99 (m, 2H), 3.98-3.81 (m, 2H), 3.58 (d, J = 11.7 Hz, 2H), 3.38 (s, 3H), 2.31-2.26 (m, 1H), 2.26-2.15 (m, 2H), 2.08 (d, J = 8.6 Hz, 2H), 1.92 (s, 1H), 1.33-1.20 (m, 3H), 0.83 (s, 1H), 0.46 (s, 1H), 0.13 (s, 3H), 0.01 (d, J = 1.1 Hz, 1H).
LCMS Calculated for $C_{30}H_{33}F_3N_6O_4$: 598.25; Observed (Method-A): 597.3 [M − H] $^-$, 97.9% at RT 1.171.

-continued

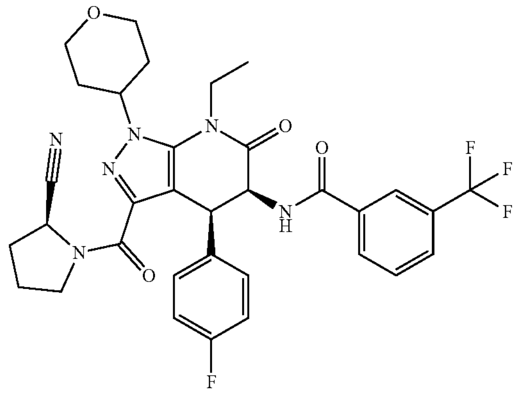 [SMILES: CCN1C(=O)[C@@H](NC(=O)c2cccc(C(F)(F)F)c2)[C@@H](c2ccc(F)cc2)c2c(C(=O)N3CCC[C@H]3C#N)nn(C3CCOCC3)c21]

I-350

$^1$H NMR (300 MHz, DMSO-$d_6$) δ 8.52 (t, J = 7.4 Hz, 1H), 8.13 (d, J = 8.4 Hz, 2H), 7.92 (d, J = 7.8 Hz, 1H), 7.71 (t, J = 7.8 Hz, 1H), 7.07 (t, J = 8.7 Hz, 2H), 6.96 (ddd, J = 8.7, 5.5, 2.6 Hz, 2H), 5.70-4.95 (m, 2H), 4.89-4.80 (m, 1H), 4.61 (s, 1H), 4.25-3.85 (m, 5H), 3.67-3.43 (m, 3H), 2.30 (ddt, J = 9.4, 7.2, 4.5 Hz, 2H), 2.24-1.78 (m, 6H), 1.33 (td, J = 7.0, 4.4 Hz, 3H).
LCMS Calculated for $C_{33}H_{31}F_4N_6O_4$: 652.24; Observed (Method-I): 651.2 [M − H]$^-$, 99.6% at RT 2.123 min.

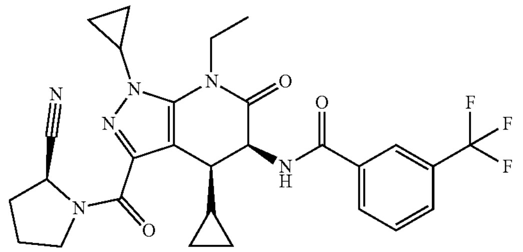 [SMILES: CCN1C(=O)[C@@H](NC(=O)c2cccc(C(F)(F)F)c2)[C@@H](C2CC2)c2c(C(=O)N3CCC[C@H]3C#N)nn(C3CC3)c21]

I-454

$^1$H NMR (400 MHz, DMSO-$d_6$) δ 9.02 (dd, J = 11.4, 7.9 Hz, 1H), 8.32 (s, 1H), 8.25 (d, J = 7.9 Hz, 1H), 7.95 (d, J = 7.8 Hz, 1H), 7.76 (t, J = 7.8 Hz, 1H), 5.62-4.88 (m, 2H), 4.31 (dt, J = 14.1, 7.1 Hz, 1H), 4.20-3.75 (m, 3H), 3.64-3.46 (m, 1H), 3.44-3.36 (m, 1H), 2.31-2.11 (m, 2H), 2.06 (q, J = 6.7 Hz, 2H), 1.52-1.19 (m, 5H), 1.18-1.03 (m, 2H), 0.84 (s, 1H), 0.50-0.43 (m, 1H), 0.21-0.04 (m, 3H).
LCMS Calculated for $C_{28}H_{29}F_3N_6O_3$: 554.23; Observed (Method-A): 553.3 [M − H]$^-$, 99.5% at RT 1.209 min.

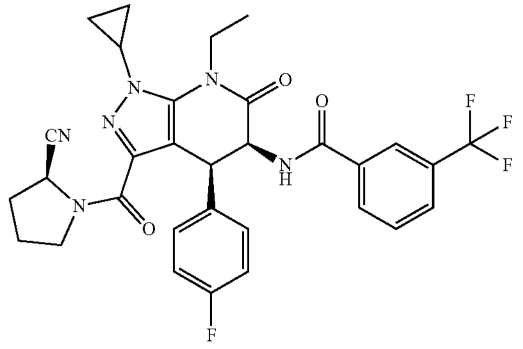 [SMILES: CCN1C(=O)[C@@H](NC(=O)c2cccc(C(F)(F)F)c2)[C@@H](c2ccc(F)cc2)c2c(C(=O)N3CCC[C@H]3C#N)nn(C3CC3)c21]

I-354

$^1$H NMR (300 MHz, DMSO-$d_6$) δ 8.58-8.47 (m, 1H), 8.21-8.08 (m, 2H), 7.92 (d, J = 8.0 Hz, 1H), 7.71 (t, J = 7.7 Hz, 1H), 7.07 (t, J = 8.8 Hz, 2H), 7.00-6.90 (m, 2H), 5.33-5.12 (m, 1H), 4.95 (d, J = 7.2 Hz, 1H), 4.82 (d, J = 6.5 Hz, 1H), 4.45-4.30 (m, 1H), 4.30-4.21 (m, 1H), 4.20-4.08 (m, 1H), 3.88 (d, J = 4.0 Hz, 1H), 3.48 (s, 1H), 2.17-1.93 (m, 3H), 1.43-1.01 (m, 7H).
LCMS Calculated for $C_{31}H_{28}F_4N_6O_3$: 608.22; Observed (Method-N): 607.2 [M − H]$^-$, 100% at 2.023 min.

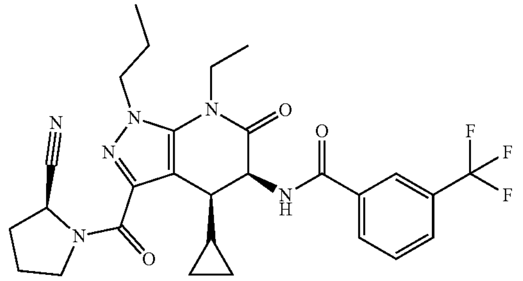 [SMILES: CCCn1nc(C(=O)N2CCC[C@H]2C#N)c2c1N(CC)C(=O)[C@@H](NC(=O)c1cccc(C(F)(F)F)c1)[C@H]2C1CC1]

I-467

$^1$H NMR (400 MHz, DMSO-$d_6$) δ 9.02 (t, J = 8.9 Hz, 1H), 8.31 (s, 1H), 8.25 (d, J = 7.7 Hz, 1H), 7.95 (d, J = 7.8 Hz, 1H), 7.76 (t, J = 7.8 Hz, 1H), 5.71-4.88 (m, 2H), 4.28-3.59 (m, 5H), 3.56-3.40 (m, 2H), 2.35-2.12 (m, 2H), 2.12-1.81 (m, 4H), 1.28-1.18 (m, 3H), 0.99-0.82 (m, 4H), 0.51-0.42 (m, 1H), 0.22-0.01 (m, 3H).
LCMS Calculated for $C_{28}H_{31}F_3N_6O_3$: 556.24; Observed (Method-O): 557.3 [M + H]$^+$, 99.4% at 5.816 min.

-continued

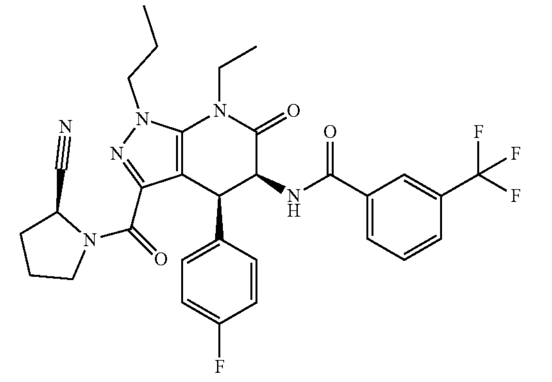 [SMILES: CCCn1nc(C(=O)N2CCC[C@H]2C#N)c2c1N(CC)C(=O)[C@@H](NC(=O)c1cccc(C(F)(F)F)c1)[C@H]2c1ccc(F)cc1]

I-428

$^1$H NMR (300 MHz, DMSO-$d_6$) δ 8.58-8.47 (m, 1H), 8.21-8.08 (m, 2H), 7.92 (d, J = 8.0 Hz, 1H), 7.71 (t, J = 7.7 Hz, 1H), 7.07 (t, J = 8.8 Hz, 2H), 7.00-6.90 (m, 2H), 5.33-5.12 (m, 1H), 4.95 (d, J = 7.2 Hz, 1H), 4.82 (d, J = 6.5 Hz, 1H), 4.45-4.30 (m, 1H), 4.30-4.21 (m, 1H), 4.20-4.08 (m, 1H), 3.88 (d, J = 4.0 Hz, 1H), 3.48 (s, 1H), 2.17-1.93 (m, 3H), 1.43-1.01 (m, 7H).
LCMS Calculated for: $C_{31}H_{28}F_4N_6O_3$: 610.23; Observed (Method-P): 609.3 [M − H]$^-$, 99.8% at RT 1.943 min.

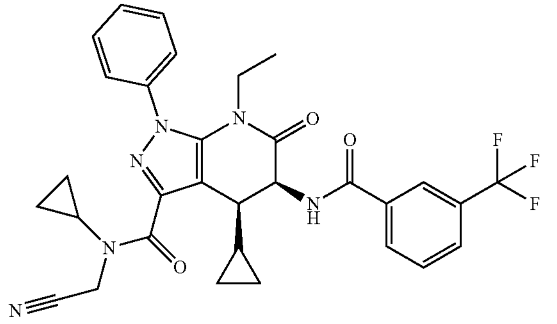 [SMILES: CCN1C(=O)[C@@H](NC(=O)c2cccc(C(F)(F)F)c2)[C@@H](C2CC2)c2c(C(=O)N(CC#N)C3CC3)nn(-c3ccccc3)c21]

I-619

1H NMR (300 MHz, DMSO-d6) δ 9.08 (d, J = 8.0 Hz, 1H), 8.34 (d, J = 2.1 Hz, 1H), 8.27 (d, J = 7.8 Hz, 1H), 7.96 (d, J = 7.8 Hz, 1H), 7.78 (d, J = 7.8 Hz, 1H), 7.75-7.66 (m, 2H), 7.64-7.50 (m, 3H), 5.40 (dd, J = 8.0, 6.2 Hz, 1H), 4.58 (s, 2H), 3.94 (dd, J = 14.4, 7.2 Hz, 1H), 3.14 (s, 2H), 2.95 (dt, J = 14.2, 6.9 Hz, 1H), 0.83 (td, J = 7.2, 4.1 Hz, 7H), 0.65-0.43 (m, 2H), 0.23 (td, J = 8.8, 4.5 Hz, 1H), 0.11-0.01 (m, 1H), −0.04 (s, 1H).
LCMS Calculated for $C_{31}H_{29}F_3N_6O_3$: 590.61; Observed (Method-I): 589.2 [M − H]$^-$, 98.5% at RT 1.759 min.

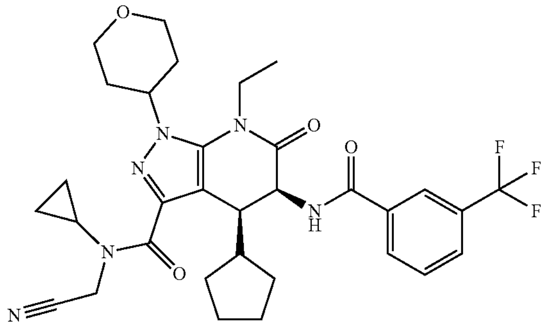 [SMILES: CCN1C(=O)[C@@H](NC(=O)c2cccc(C(F)(F)F)c2)[C@@H](C2CCCC2)c2c(C(=O)N(CC#N)C3CC3)nn(C3CCOCC3)c21]

I-682

$^1$H NMR (300 MHz, DMSO-$d_6$) δ 9.01 (d, J = 7.9 Hz, 1H), 8.31 (s, 1H), 8.24 (d, J = 7.9 Hz, 1H), 7.95 (d, J = 7.6 Hz, 1H), 7.75 (t, J = 7.8 Hz, 1H), 5.11-5.00 (m, 1H), 4.50 (s, 3H), 4.16-3.85 (m, 4H), 3.62-3.46 (m, 4H), 2.30-2.20 (m, 1H), 2.11-1.95 (m, 2H), 1.90 (s, 1H), 1.25 (t, J = 7.0 Hz, 3H), 0.83-0.68 (m, 4H), 0.58 (s, 1H), 0.51-0.45 (m, 1H), 0.23-0.15 (m, 1H), 0.11-0.11 (m, 2H).
LCMS Calculated for $C_{30}H_{33}F_3N_6O_4$: 598.25; Observed (Method-A): 597.3 [M − H]$^+$, 98.3% at RT 1.159.

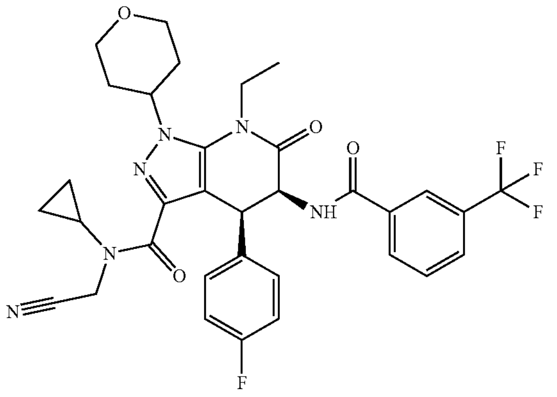 [SMILES: CCN1C(=O)[C@@H](NC(=O)c2cccc(C(F)(F)F)c2)[C@@H](c2ccc(F)cc2)c2c(C(=O)N(CC#N)C3CC3)nn(C3CCOCC3)c21]

I-351

1H NMR (300 MHz, DMSO-d6) δ 8.51 (d, J = 7.1 Hz, 1H), 8.20-8.09 (m, 2H), 7.92 (d, J = 7.9 Hz, 1H), 7.71 (t, J = 7.8 Hz, 1H), 7.07 (t, J = 8.8 Hz, 2H), 6.93 (dd, J = 8.5, 5.5 Hz, 2H), 5.24 (t, J = 7.0 Hz, 1H), 4.75 (d, J = 7.0 Hz, 1H), 4.65-4.54 (m, 2H), 4.21-3.88 (m, 4H), 3.66-3.47 (m, 2H), 3.08 (s, 1H), 2.43-2.09 (m, 2H), 2.10-2.06 (m, 1H), 1.98 (s, 2H), 1.32 (t, J = 7.0 Hz, 3H), 0.78 (d, J = 7.0 Hz, 2H), 0.67 (d, J = 9.5 Hz, 1H), 0.52 (s, 1H).
LCMS Calculated for $C_{33}H_{32}F_4N_6O_4$: 652.24 Observed (Method-B): 653.2 [M + H]$^+$, 99.1% at RT 1.125.

-continued

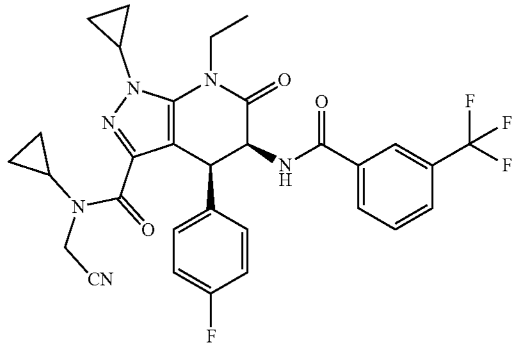 [SMILES: CCN1C(=O)[C@@H](NC(=O)c2cccc(C(F)(F)F)c2)[C@@H](c2ccc(F)cc2)c2c(C(=O)N(CC#N)C3CC3)nn(C3CC3)c21]

I-355

$^1$H NMR (300 MHz, DMSO-$d_6$) δ 8.52 (d, J = 7.1 Hz, 1H), 8.13 (m, 2H), 7.92 (d, J = 7.8 Hz, 1H), 7.71 (t, J = 7.8 Hz, 1H), 7.08 (t, J = 8.8 Hz, 2H), 6.93 (m, 2H), 5.26 (t, J = 7.1 Hz, 1H), 4.72-4.46 (m, 3H), 4.43-4.30 (m, 1H), 4.30-4.18 (m, 1H), 3.86 (m, 1H), 3.00 (s, 1H), 1.41 (m, 1H), 1.32 (t, J = 7.0 Hz, 4H), 1.24-1.07 (m, 2H), 0.75 (s, 2H), 0.64 (m, 1H), 0.45 (s, 1H).
LCMS Calculated for $C_{31}H_{28}F_4N_6O_3$: 608.22; Observed (Method-N): 609.3 [M + H] $^+$, 100% at RT 1.993.

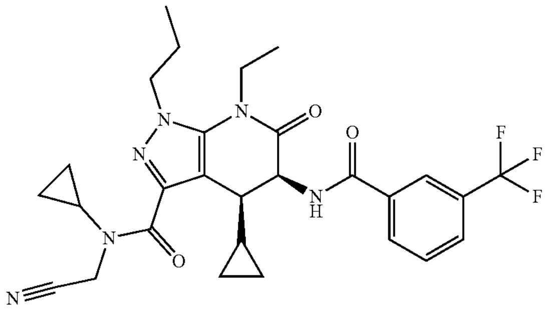 [SMILES: CCCn1nc(C(=O)N(CC#N)C2CC2)c2c1N(CC)C(=O)[C@@H](NC(=O)c1cccc(C(F)(F)F)c1)[C@H]2C1CC1]

I-427

$^1$H NMR (400 MHz, DMSO-$d_6$) δ 9.03 (d, J = 7.9 Hz, 1H), 8.31 (s, 1H), 8.24 (d, J = 7.9 Hz, 1H), 7.95 (d, J = 7.8 Hz, 1H), 7.76 (t, J = 7.8 Hz, 1H), 5.04 (dd, J = 7.9, 6.1 Hz, 1H), 4.58 (s, 2H), 4.27-4.12 (m, 3H), 3.83-3.73 (m, 1H), 3.18-3.00 (m, 2H), 1.90-1.77 (m, 2H), 1.22 (t, J = 7.0 Hz, 3H), 0.91 (t, J = 7.4 Hz, 3H), 0.85-0.69 (m, 4H), 0.51-0.42 (m, 1H), 0.24-0.16 (m, 1H), 0.07-0.02 (m, 1H), 8 0.08-0.03 (m, 1H), -0.01--0.13 (m, 1H).
LCMS Calculated for $C_{28}H_{31}F_3N_6O_3$: 556.24; Observed (Method-N): 557.3 [M + H] $^+$, 99.6% at RT 1.970 min.

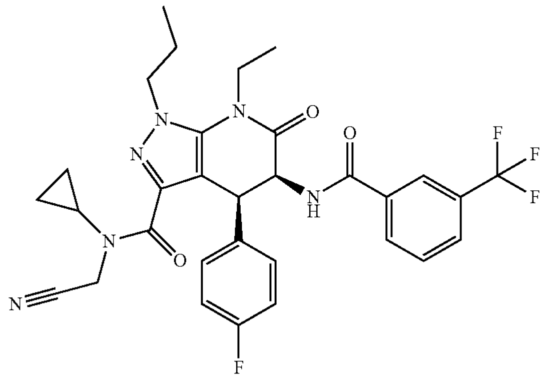 [SMILES: CCCn1nc(C(=O)N(CC#N)C2CC2)c2c1N(CC)C(=O)[C@@H](NC(=O)c1cccc(C(F)(F)F)c1)[C@H]2c1ccc(F)cc1]

I-356

$^1$H NMR (300 MHz, DMSO-$d_6$) δ 8.51 (d, J = 7.0 Hz, 1H), 8.17-8.08 (m, 2H), 7.92 (d, J = 7.8 Hz, 1H), 7.71 (t, J = 7.8 Hz, 1H), 7.13-7.02 (m, 2H), 6.97-6.87 (m, 2H), 5.22 (t, J = 7.0 Hz, 1H), 4.74 (d, J = 7.0 Hz, 1H), 4.57 (s, 2H), 4.35-4.12 (m, 3H), 3.87 (dq, J = 13.9, 6.7 Hz, 1H), 3.02 (s, 1H), 1.92 (h, J = 7.3 Hz, 2H), 1.29 (t, J = 7.0 Hz, 3H), 0.95 (t, J = 7.4 Hz, 3H), 0.82-0.40 (m, 4H).
LCMS Calculated for $C_{31}H_{30}F_4N_6O_3$: 610.23; Observed (Method-M): 611.3 [M + H] $^+$99.3% at RT 1.718 min.

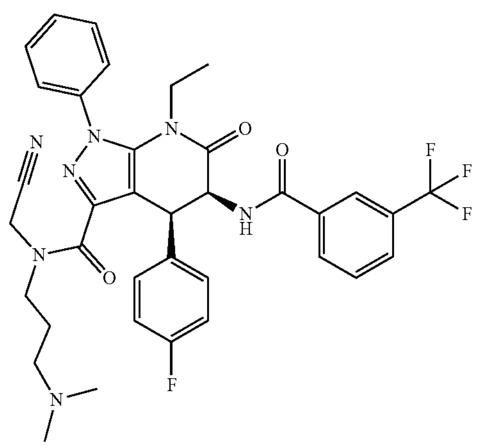 [SMILES: CCN1C(=O)[C@@H](NC(=O)c2cccc(C(F)(F)F)c2)[C@@H](c2ccc(F)cc2)c2c(C(=O)N(CC#N)CCCN(C)C)nn(-c3ccccc3)c21]

I-271

$^1$H NMR (400 MHz, DMSO-$d_6$) δ 8.57 (d, J = 7.1 Hz, 1H), 8.15 (d, J = 12.9 Hz, 2H), 7.93 (d, J = 7.6 Hz, 1H), 7.85-7.58 (m, 6H), 7.08 (t, J = 8.7 Hz, 2H), 6.98 (t, J = 7.1 Hz, 2H), 5.56 (t, J = 7.3 Hz, 1H), 5.04-4.86 (m, 2H), 4.46 (s, 1H), 3.91 (dd, J = 14.3, 7.2 Hz, 1H), 3.76-3.67 (m, 1H), 3.49-3.38 (m, 1H), 3.05 (d, J = 13.5 Hz, 1H), 2.07 (s, 4H), 1.95 (s, 4H), 1.69 (s, 2H), 0.91 (t, J = 7.1 Hz, 3H).
LCMS Calculated for $C_{36}H_{35}F_4N_7O_3$: 689.27; Observed (Method-C): 690.1 [M + H] $^+$, 95.5% at RT 0.987 min.

-continued

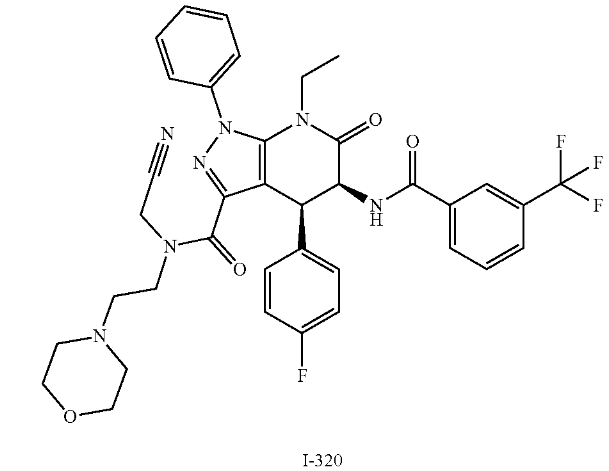

$^1$H NMR (400 MHz, DMSO-$d_6$) δ 9.87-9.39 (m, 1H), 8.61 (s, 1H), 8.19-8.12 (m, 2H), 7.93 (d, J = 7.7 Hz, 1H), 7.85 (d, J = 7.3 Hz, 2H), 7.76-7.59 (m, 4H), 7.10 (t, J = 8.5 Hz, 2H), 6.99 (s, 2H), 5.54 (t, J = 7.2 Hz, 1H), 5.07 (s, 1H), 4.95 (s, 1H), 4.50 (s, 1H), 4.43-4.06 (m, 1H), 3.93 (d, J = 14.0 Hz, 2H), 3.85-3.78 (m, 1H), 3.76-3.52 (m, 3H), 3.57 (s, 2H), 3.26-3.16 (m, 1H), 3.05 (s, 3H), 0.92 (t, J = 7.0 Hz, 3H).
LCMS Calculated for $C_{37}H_{35}F_4N_7O_4$: 717.27; Observed (Method-D): 718.3 [M + H] $^+$, 92.6% at RT 1.883.

I-320

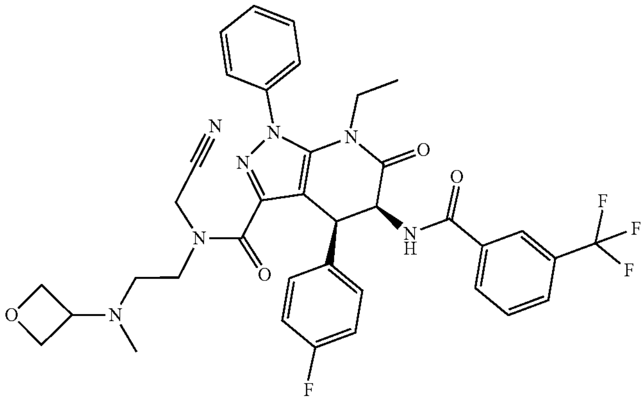 [SMILES: CCN1C(=O)[C@@H](NC(=O)c2cccc(C(F)(F)F)c2)[C@@H](c2ccc(F)cc2)c2c(C(=O)N(CC#N)CCN(C)C3COC3)nn(-c3ccccc3)c21]

$^1$H NMR (400 MHz, DMSO-$d_6$) δ 10.75-10.15 (m, 2H), 8.60 (s, 1H), 8.20-8.12 (m, 2H), 7.93 (d, J = 7.8 Hz, 1H), 7.84 (s, 2H), 7.75-7.59 (m, 4H), 7.10 (t, J = 8.7 Hz, 2H), 6.99 (t, J = 6.9 Hz, 2H), 5.54 (s, 1H), 5.16-4.73 (m, 2H), 4.58 (d, J = 67.1 Hz, 6H), 3.92 (dd, J = 14.9, 7.8 Hz, 2H), 3.69-3.52 (m, 1H), 3.05 (s, 1H), 2.76 (d, J = 15.2 Hz, 1H), 2.65-2.58 (m, 1H), 2.45-2.38 (m, 1H), 1.99 (s, 1H), 0.92 (t, J = 7.1 Hz, 3H).
LCMS Calculated for $C_{37}H_{35}F_4N_7O_4$: 717.27; Observed (Method-C): 718.2 [M + H] $^+$, 98.0% at RT 1.030 min.

I-321

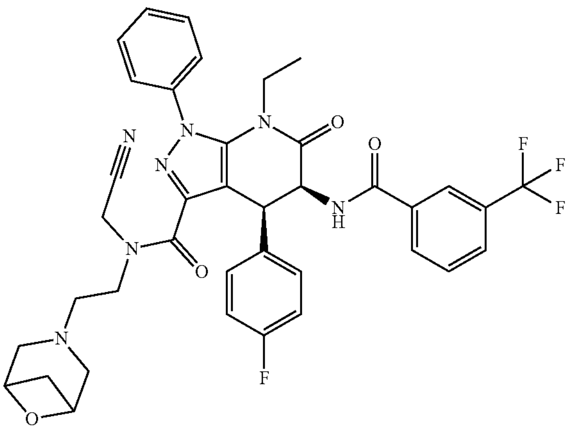 [SMILES: CCN1C(=O)[C@@H](NC(=O)c2cccc(C(F)(F)F)c2)[C@@H](c2ccc(F)cc2)c2c(C(=O)N(CC#N)CCN3CC4CC(C3)O4)nn(-c3ccccc3)c21]

$^1$H NMR (400 MHz, DMSO-$d_6$) δ 8.55 (d, J = 7.1 Hz, 1H), 8.19-8.11 (m, 2H), 7.93 (d, J = 7.8 Hz, 1H), 7.74 (dt, J = 15.6, 7.5 Hz, 3H), 7.67-7.56 (m, 3H), 7.08 (t, J = 8.6 Hz, 2H), 6.98 (t, J = 7.0 Hz, 2H), 5.59-4.78 (m, 2H), 4.38 (d, J = 63.8 Hz, 3H), 4.15-3.55 (m, 3H), 3.22-3.14 (m, 1H), 3.10-3.00 (m, 1H), 2.83 (d, J = 76.0 Hz, 4H), 2.54 (s, 2H), 2.00 (d, J = 7.7 Hz, 1H), 1.25 (s, 1H), 0.91 (t, J = 7.0 Hz, 3H).
LCMS Calculated for $C_{38}H_{35}F_4N_7O_4$: 729.27; Observed (Method-C): 730.5 [M + H] $^+$, 97.7% at RT 1.510 min.

I-322

-continued

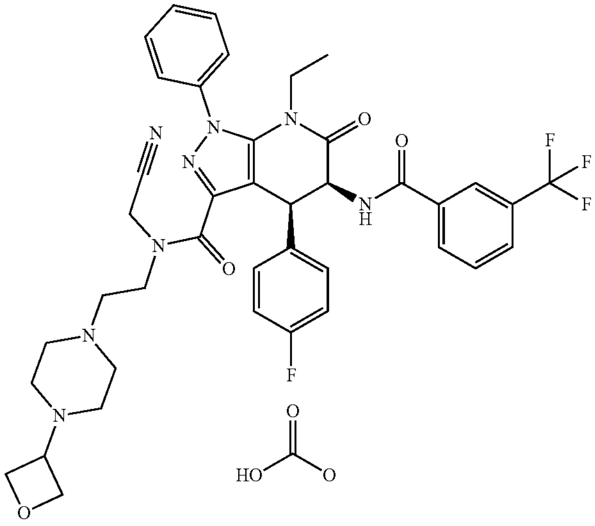

I-323

$^1$H NMR (400 MHz, DMSO-$d_6$) δ 8.58 (s, 1H), 8.16 (d, J = 13.1 Hz, 2H), 7.93 (d, J = 7.8 Hz, 1H), 7.74 (dd, J = 40.8, 33.0 Hz, 7H), 7.09 (t, J = 8.7 Hz, 2H), 6.99 (s, 2H), 5.53 (s, 1H), 4.92 (s, 1H), 4.75-4.26 (m, 5H), 3.92 (dd, J = 14.4, 7.3 Hz, 2H), 3.75-3.40 (m, 3H), 3.04 (d, J = 12.9 Hz, 2H), 2.65-2.57 (m, 2H), 2.41-2.23 (m, 2H), 2.08 (s, 3H), 0.92 (t, J = 7.1 Hz, 3H).
LCMS Calculated for $C_{40}H_{40}F_4N_8O_4$: 772.31; Observed (Method-D): 773.4 [M − HCOOH + H] $^+$, 95.5% at RT 1.530 min.

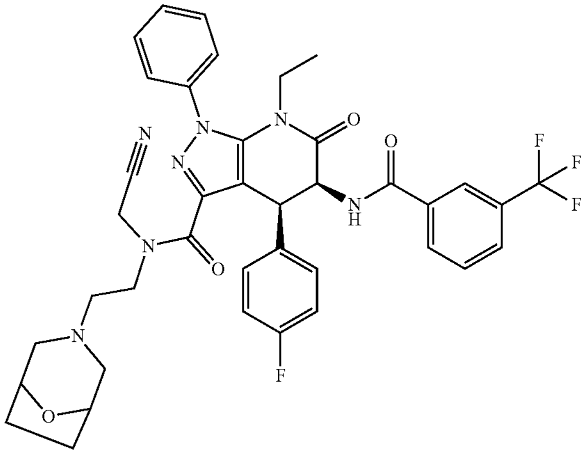 [SMILES: CCN1C(=O)[C@@H](NC(=O)c2cccc(C(F)(F)F)c2)[C@@H](c2ccc(F)cc2)c2c(C(=O)N(CC#N)CCN3CC4CCC(C3)O4)nn(-c3ccccc3)c21]

I-324

$^1$H NMR (400 MHz, DMSO-$d_6$) δ 8.55 (d, J = 7.2 Hz, 1H), 8.15 (d, J = 12.1 Hz, 2H), 7.93 (d, J = 8.0 Hz, 1H), 7.87-7.56 (m, 6H), 7.09 (t, J = 8.6 Hz, 2H), 6.99 (s, 2H), 5.54 (s, 1H), 5.10-4.87 (m, 2H), 4.45 (d, J = 10.6 Hz, 1H), 4.16-3.85 (m, 4H), 3.53 (s, 1H), 3.06 (s, 1H), 2.43 (s, 3H), 2.06 (d, J = 11.0 Hz, 2H), 1.60 (s, 4H), 0.92 (t, J = 7.1 Hz, 3H).
LCMS Calculated for $C_{39}H_{37}F_4N_7O_4$: 743.28; Observed (Method-F): 744.2 [M + H] $^+$, 99.0% at RT 1.284 min.

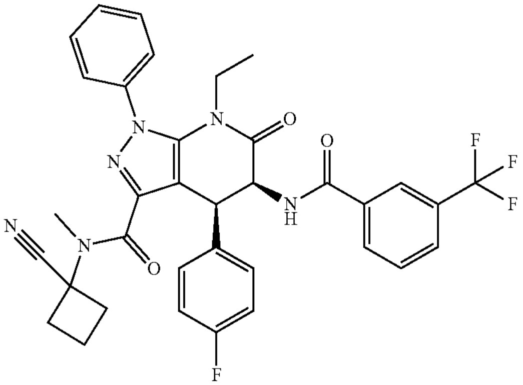 [SMILES: CCN1C(=O)[C@@H](NC(=O)c2cccc(C(F)(F)F)c2)[C@@H](c2ccc(F)cc2)c2c(C(=O)N(C)C3(C#N)CCC3)nn(-c3ccccc3)c21]

I-689

$^1$H NMR (400 MHz, DMSO-$d_6$) δ 8.57 (d, J = 7.3 Hz, 1H), 8.24-8.08 (m, 2H), 7.93 (d, J = 7.7 Hz, 1H), 7.83-7.77 (m, 2H), 7.72 (t, J = 7.8 Hz, 1H), 7.69-7.54 (m, 3H), 7.10 (t, J = 8.7 Hz, 2H), 7.00 (dd, J = 8.5, 5.5 Hz, 2H), 5.55 (t, J = 7.2 Hz, 1H), 4.87 (d, J = 7.2 Hz, 1H), 3.89 (dd, J = 14.4, 7.3 Hz, 1H), 3.19-2.95 (m, 4H), 2.87-2.65 (m,2H), 2.45-2.22 (m, 1H), 1.98 (q, J = 9.7 Hz, 1H), 1.82 (t, J = 10.1 Hz, 1H), 0.91 (t, J = 7.1 Hz, 3H).
LCMS Calculated for $C_{35}H_{30}F_4N_6O_3$: 658.2; Observed (Method-C): 659.1 [M + H] $^+$, 96.3% at RT 1.354 min.

-continued

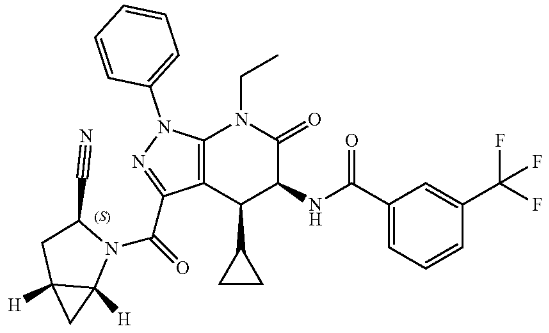

I-326

$^1$H NMR (400 MHz, DMSO-$d_6$) δ 9.13-9.04 (m, 1H), 8.35 (s, 1H), 8.28 (d, J = 7.8 Hz, 1H), 7.96 (d, J = 7.5 Hz, 1H), 7.76 (m, J = 18.3, 8.3 Hz, 3H), 7.64-7.54 (m, 3H), 5.45-5.33 (m, 1H), 4.94-4.86 (m, 1H), 4.37 (t, J = 5.8 Hz, 1H), 3.91-3.81 (m, 1H), 3.48 (t, J = 6.6 Hz, 1H), 3.01 (m, 1H), 2.45 (t, J = 7.0 Hz, 2H), 1.97-1.77 (m, 1H), 0.96-0.81 (m, 5H), 0.64 (s, 1H), 0.53 (t, J = 8.6 Hz, 1H), 0.22 (d, J = 8.9 Hz, 1H), 0.07 (d, J = 4.8 Hz, 2H).
LCMS Calculated for $C_{32}H_{29}F_3N_6O_3$: 602.23; Observed (Method-M): 603.3 [M + H] $^+$, 98.3% at RT 1.779 min.

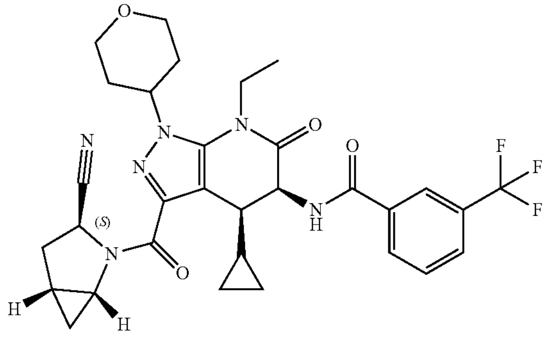

I-256

$^1$H NMR (400 MHz, DMSO-$d_6$) δ 9.01 (d, J = 8.0 Hz, 1H), 8.31 (s, 1H), 8.25 (d, J = 7.9 Hz, 1H), 7.96 (d, J = 7.8 Hz, 1H), 7.76 (t, J = 7.8 Hz, 1H), 5.61-4.90 (m, 1H), 4.51 (m, 1H), 4.34 (d, J = 6.4 Hz, 1H), 4.18-4.01 (m, 2H), 3.98-3.81 (m, 2H), 3.58-3.45 (m, 2H), 3.42 (t, J = 6.4 Hz, 1H), 2.59 (s, 1H), 2.49-2.34 (m, 2H), 2.31-2.23 (m, 1H), 2.10 (d, J = 13.8 Hz, 1H), 2.03-1.81 (m, 3H), 1.28 (t, J = 6.9 Hz, 3H), 0.93 (m, 1H), 0.84 (s, 1H), 0.62 (s, 1H), 0.51-0.46 (m, 1H), 0.28-0.12 (m, 3H).
LCMS Calculated for $C_{31}H_{33}F_3N_6O_4$: 610.25; Observed (Method-N): 611.4[M + H] $^+$, 99.2% at RT 1.507 min.

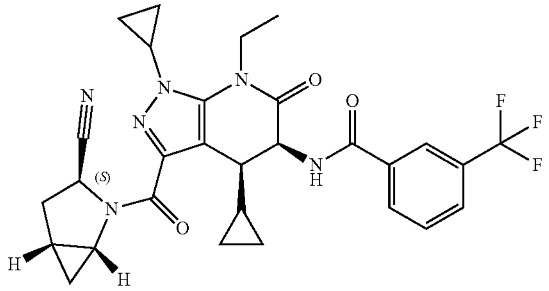

I-327

$^1$H NMR (400 MHz, DMSO-$d_6$) δ 9.02 (d, J = 8.1 Hz, 1H), 8.32 (s, 1H), 8.25 (d, J = 7.8 Hz, 1H), 7.95 (d, J = 7.8 Hz, 1H), 7.76 (t, J = 7.8 Hz, 1H), 5.11 (t, J = 7.0 Hz, 1H), 4.89-4.80 (m, 1H), 4.31 (d, J = 7.3 Hz, 2H), 4.14 (dd, J = 14.4, 7.2 Hz, 1H), 3.81 (dd, J = 7.1, 3.6 Hz, 1H), 3.43 (t, J = 6.4 Hz, 1H), 2.48-2.10 (m, 3H), 1.99-1.79 (m, 1H), 1.26 (t, J = 6.9 Hz, 5H), 1.19-1.05 (m, 2H), 0.89 (m, 2H), 0.60 (s, 1H), 0.46 (s, 1H), 0.18 (s, 2H).
LCMS Calculated for $C_{29}H_{29}F_3N_6O_3$: 566.23; Observed (Method-N): 567.3[M + H] $^+$, 98.8% at RT 1.59 min.

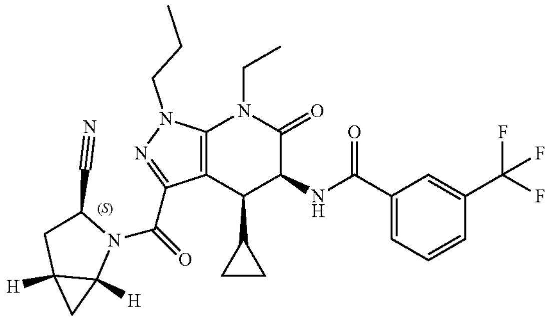

I-328

$^1$H NMR (400 MHz, DMSO-$d_6$) δ 9.01 (d, J = 7.8 Hz, 1H), 8.31 (s, 1H), 8.24 (d, J = 7.9 Hz, 1H), 7.95 (d, J = 7.8 Hz, 1H), 7.75 (t, J = 7.8 Hz, 1H), 5.67-4.79 (m, 2H), 4.39-3.74 (m, 5H), 3.47 (t, J = 6.3 Hz, 1H), 2.49-2.49 (m, 1H), 2.47-2.34 (m, 2H), 1.95-1.82 (m, 3H), 1.23 (t, J = 7.1 Hz, 3H), 0.95-0.86 (m, 6H), 0.61-0.56 (m, 1H), 0.46 (t, J = 9.1 Hz, 1H), 0.18 (t, J = 8.6 Hz, 1H).
LCMS Calculated for $C_{29}H_{31}F_3N_6O_3$: 568.24; Observed (Method-R): 569.4 [M + H] $^+$, 99.9% at RT 1.042 min.

-continued

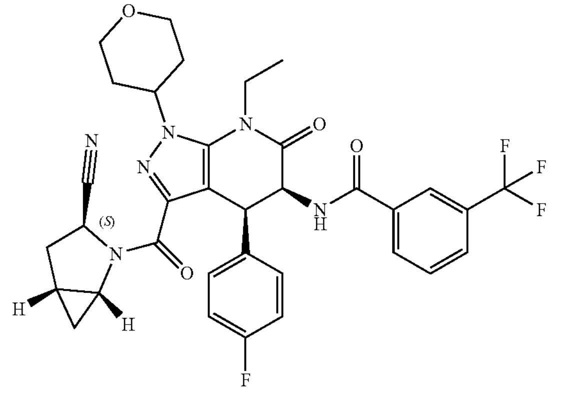

I-329

$^1$H NMR (400 MHz, DMSO-$d_6$) δ 8.55-8.47 (m, 1H), 8.18-8.10 (m, 2H), 7.92 (d, J = 7.8 Hz, 1H), 7.71 (t, J = 7.8 Hz, 1H), 7.07 (t, J = 8.7 Hz, 2H), 6.97 (d, J = 6.4 Hz, 2H), 5.71-5.14 (m, 2H), 4.99 (d, J = 7.2 Hz, 1H), 4.87-4.77 (m, 1H), 4.60 (s, 1H), 4.21-3.93 (m, 4H), 3.57 (m, 2H), 2.45-2.28 (m, 3H), 2.19 (d, J = 13.3 Hz, 1H), 1.99 (s, 3H), 1.34 (t, J = 6.9 Hz, 3H), 1.01-0.87 (m, 1H), 0.67-0.51 (m, 1H).
LCMS Calculated for $C_{34}H_{32}F_4N_6O_4$: 664,24; Observed (Method-M): 665.4[M + H] $^+$, 98.0% at RT 1.613 min.

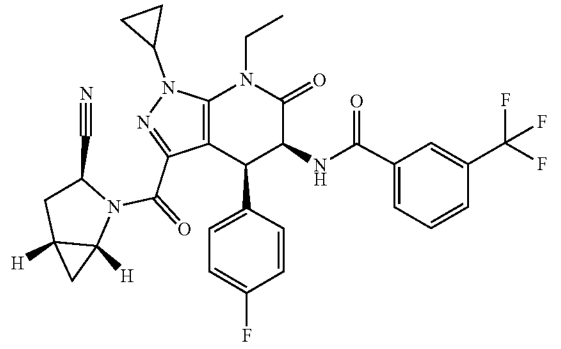 [SMILES: CCN1C(=O)[C@@H](NC(=O)c2cccc(C(F)(F)F)c2)[C@@H](c2ccc(F)cc2)c2c(C(=O)N3[C@H](C#N)C[C@H]4C[C@H]43)nn(C3CC3)c21]

I-330

$^1$H NMR (300 MHz, DMSO-$d_6$) δ 8.48 (d, J = 7.3 Hz, 1H), 8.11 (m, 2H), 7.90 (d, J = 7.8 Hz, 1H), 7.69 (t, J = 7.8 Hz, 1H), 7.05 (t, J = 8.7 Hz, 2H), 6.94 (t, J = 7.0 Hz, 2H), 5.65-5.21 (m, 1H), 5.19-4.88 (m, 1H), 4.76 (m, 1H), 4.32 (m, 2H), 4.21 (m, 1H), 3.94-3.81 (m, 1H), 2.42-2.19 (m, 2H), 1.92 (m, 1H), 1.42-1.25 (m, 5H), 1.25-1.02 (m, 3H), 0.86 (m, 1H).
LCMS Calculated for $C_{32}H_{28}F_4N_6O_3$: 620.22; Observed (Method-S): 621.3 [M + H] $^+$, 97.9% at RT 2.644 min.

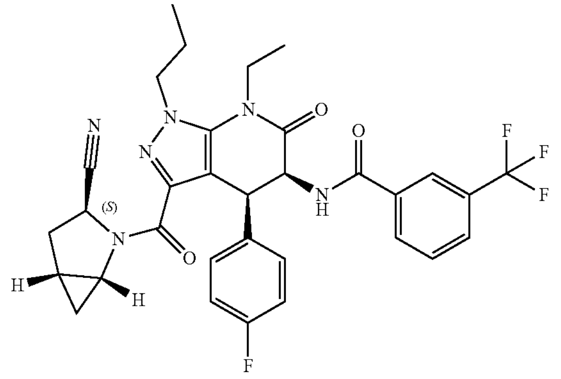

I-331

$^1$H NMR (300 MHz, DMSO-$d_6$) δ 8.50 (d, J = 7.1 Hz, 1H), 8.13 (d, J = 11.5 Hz, 2H), 7.92 (d, J = 7.8 Hz, 1H), 7.71 (t, J = 7.8 Hz, 1H), 7.12-7.01 (m, 2H), 6.95 (dd, J = 8.6, 5.6 Hz, 2H), 5.72-4.95 (m, 2H), 4.79 (dd, J = 8.9, 5.5 Hz, 1H), 4.45-4.12 (m, 4H), 3.89 (dq, J = 13.8, 6.7 Hz, 1H), 2.47-2.20 (m, 2H), 1.95 (q, J = 7.4 Hz, 3H), 1.31 (t, J = 7.0 Hz, 3H), 0.97 (t, J = 7.3 Hz, 3H), 0.86 (q, J = 6.8, 6.4 Hz, 1H), 0.73-0.46 (m, 1H).
LCMS Calculated for $C_{32}H_{30}F_4N_6O_3$: 622.23; Observed (Method-C): 623.2 [M + H] $^+$, 98.8% at 1.388 min.

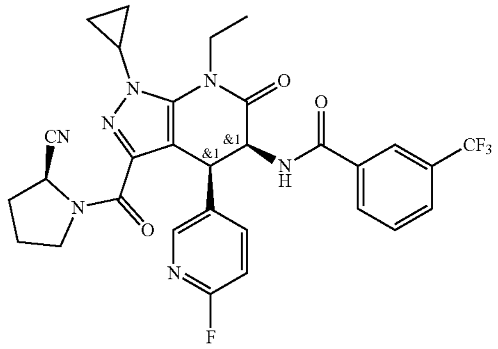 [SMILES: CCN1C(=O)[C@@H](NC(=O)c2cccc(C(F)(F)F)c2)[C@@H](c2ccc(F)nc2)c2c(C(=O)N3CCC[C@H]3C#N)nn(C3CC3)c21]

I-585

$^1$H NMR (400 MHz, DMSO-$d_6$) δ 8.74 (q, J = 8.7, 7.6 Hz, 1H), 8.17 (q, J = 7.5, 7.0 Hz, 2H), 7.93 (d, J = 7.8 Hz, 1H), 7.77 (d, J = 9.8 Hz, 1H), 7.72 (t, J = 7.8 Hz, 1H), 7.49 (td, J = 8.2, 2.5 Hz, 1H), 7.12-7.05 (m, 1H), 5.70-5.35 (m, 1H), 5.31-4.73 (m, 3H), 4.38 (dd, J = 13.8, 6.6 Hz, 1H), 4.26 (dt, J = 14.9, 7.5 Hz, 1H), 4.17-3.84 (m, 2H), 3.62-3.45 (m, 1H), 2.30-2.14 (m, 1H), 2.13 (t, J = 5.9 Hz, 1H), 2.08-1.86 (m, 2H), 1.51-1.26 (m, 5H), 1.26-1.06 (m, 2H).
LCMS Calculated for $C_{30}H_{27}F_4N_7O_3$: 609.21; Observed (Method-A): 610.2 [M + H] $^+$, 97.7% at RT 1.172 min.

-continued

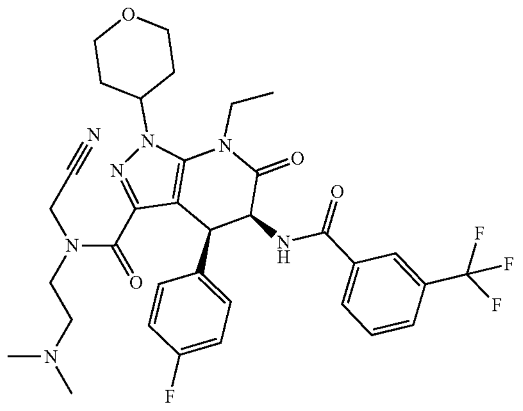 [SMILES: CCN1C(=O)[C@@H](NC(=O)c2cccc(C(F)(F)F)c2)[C@@H](c2ccc(F)cc2)c2c(C(=O)N(CC#N)CCN(C)C)nn(C3CCOCC3)c21]

I-352

$^1$H NMR (300 MHz, DMSO-$d_6$) δ 8.49 (d, J = 7.1 Hz, 1H), 8.11 (d, J = 11.2 Hz, 2H), 7.90 (d, J = 7.9 Hz, 1H), 7.69 (t, J = 7.8 Hz, 1H), 7.05 (t, J = 8.7 Hz, 2H), 6.92 (dd, J = 8.5, 5.5 Hz, 2H), 5.21 (t, J = 7.0 Hz, 1H), 5.02-4.67 (m, 2H), 4.57 (s, 1H), 4.40 (s, 1H), 4.19-3.86 (m, 6H), 3.64-3.38 (m, 3H), 2.41 (s, 2H), 2.22-1.84 (m, 10H), 1.30 (t, J = 7.0 Hz, 3H).

LCMS Calculated for $C_{34}H_{37}F_4N_7O_4$: 683.3; Observed (Method-T): 684.2 [M + H] $^+$, 97.8% at RT 1.854 min.

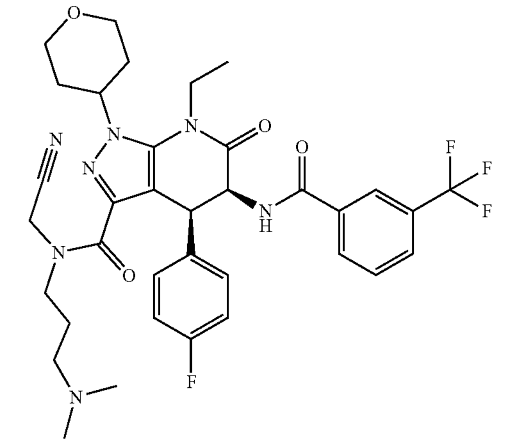 [SMILES: CCN1C(=O)[C@@H](NC(=O)c2cccc(C(F)(F)F)c2)[C@@H](c2ccc(F)cc2)c2c(C(=O)N(CC#N)CCCN(C)C)nn(C3CCOCC3)c21]

I-353

$^1$H NMR (300 MHz, DMSO-$d_6$) δ 8.48 (d, J = 7.0 Hz, 1H), 8.18-8.05 (m, 2H), 7.90 (d, J = 7.8 Hz, 1H), 7.69 (t, J = 7.7 Hz, 1H), 7.04 (t, J = 8.7 Hz, 2H), 6.92 (dd, J = 8.4, 5.5 Hz, 2H), 5.22 (t, J = 7.0 Hz, 1H), 4.97 (s, 1H), 4.80 (d, J = 7.5 Hz, 1H), 4.58 (s, 1H), 4.43 (s, 1H), 4.14-3.85 (m, 5H), 3.65-3.40 (m, 3H), 2.25 (s, 3H), 2.19-2.03 (m, 7H), 2.01-1.89 (m, 2H), 1.88-1.61 (m, 2H), 1.30 (t, J = 7.0 Hz, 3H).

LCMS Calculated for $C_{35}H_{39}F_4N_7O_4$: 697.3; Observed (Method-C): 698.2 [M + H] $^+$, 93.9% at RT 0.972 min.

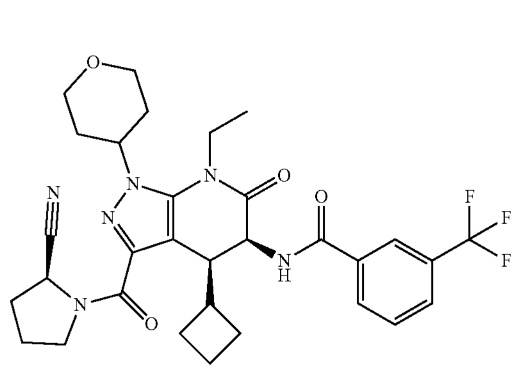 [SMILES: CCN1C(=O)[C@@H](NC(=O)c2cccc(C(F)(F)F)c2)[C@@H](C2CCC2)c2c(C(=O)N3CCC[C@H]3C#N)nn(C3CCOCC3)c21]

I-469

$^1$H NMR (400 MHz, DMSO-$d_6$) δ 8.90 (dd, J = 7.8, 5.2 Hz, 1H), 8.31-8.22 (m, 2H), 7.95 (d, J = 7.8 Hz, 1H), 7.76 (t, J = 7.8 Hz, 1H), 5.71-4.89 (m, 2H), 4.49 (dt, J = 10.3, 5.1 Hz, 1H), 4.17-3.70 (m, 6H), 3.68-3.44 (m, 3H), 2.45-2.12 (m, 3H), 2.12-1.74 (m, 8H), 1.51-1.21 (m, 8H), 1.20-0.84 (m, 2H).

LCMS Calculated for $C_{32}H_{37}F_3N_6O_4$: 626.28; Observed (Method-D): 625.3 [M − H] $^-$, 99.4% at RT 1.528 min.

Chiral-SFC (Method-A): 99.0% at RT 1.24 min

-continued

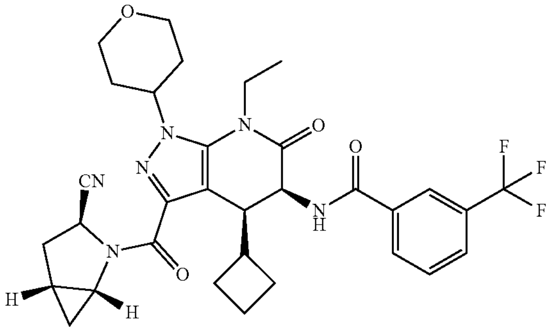 [SMILES: CCN1C(=O)[C@@H](NC(=O)c2cccc(C(F)(F)F)c2)[C@@H](C2CCC2)c2c(C(=O)N3[C@H](C#N)C[C@H]4C[C@H]43)nn(C3CCOCC3)c21]

I-593

$^1H$ NMR (400 MHz, DMSO-$d_6$) δ 8.77 (t, J = 8.3 Hz, 1H), 8.28 (s, 1H), 8.24 (d, J = 7.9 Hz, 1H), 7.95 (d, J = 7.8 Hz, 1H), 7.75 (t, J = 7.8 Hz, 1H), 4.99 (t, J = 6.8 Hz, 1H), 4.95-4.83 (m, 1H), 4.51 (ddt, J = 15.2, 10.7, 4.3 Hz, 1H), 4.37 (td, J = 6.3, 2.4 Hz, 1H), 4.11-3.98 (m, 2H), 3.97-3.90 (m, 1H), 3.83 (dt, J = 13.8, 6.9 Hz, 1H), 3.69 (t, J = 6.8 Hz, 1H), 3.65-3.59 (m, 1H), 3.60-3.45 (m, 2H), 2.48-2.36 (m, 2H), 2.29 (qd, J = 12.3, 4.5 Hz, 1H), 2.17-1.80 (m, 5H), 1.80-1.49 (m, 5H), 1.26 (q, J = 7.3 Hz, 3H), 1.09-0.87 (m, 1H), 0.71-0.50 (m, 1H).
LCMS Calculated for $C_{35}H_{35}F_3N_6O_4$: 624.27; Observed (Method-M): 625.65 [M + H] $^+$, 99.6% at RT 2.013 min.
Chiral-SFC (Method-A): 100.0% at RT 1.266 min

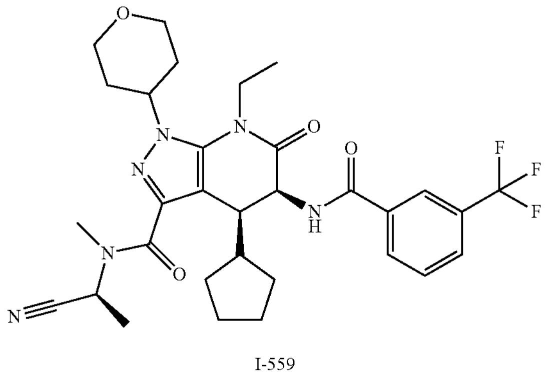

I-559

$^1H$ NMR (400 MHz, DMSO-$d_6$) δ 8.92 (d, J = 7.8 Hz, 1H), 8.31-8.21 (m, 2H), 7.95 (d, J = 7.8 Hz, 1H), 7.75 (t, J = 7.8 Hz, 1H), 5.69 (d, J = 84.2 Hz, 1H), 5.06 (t, J = 7.0 Hz, 1H), 4.46 (d, J = 8.9 Hz, 1H), 4.08-3.88 (m,3H), 3.87-3.77 (m, 1H), 3.59-3.41 (m, 3H), 3.28-2.96 (m, 3H), 2.26 (tt, J = 11.8, 6.1 Hz, 1H), 2.11 (s, 1H), 1.89 (s, 3H), 1.76-1.31 (m, 9H), 1.27 (t, J = 7.0 Hz, 3H), 0.94 (t, J = 10.3 Hz, 1H), 0.77 (t, J = 10.5 Hz, 1H).
LCMS Calculated for $C_{31}H_{37}F_3N_6O_4$: 614.28; Observed (Method-P): 613.3 [M − H] $^-$, 99.7% at RT 1.873 min.
Chiral-SFC (Method-B): 98.56% at RT 0.83 min

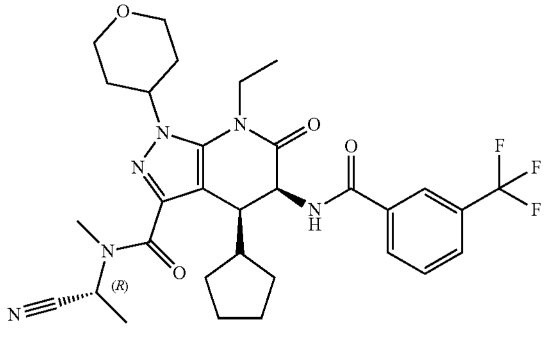

I-524

$^1H$ NMR (400 MHz, DMSO-$d_6$) δ 8.92 (s, 1H), 8.30-8.21 (m, 2H), 7.95 (d, J = 7.8 Hz, 1H), 7.76 (t, J = 7.8 Hz, 1H), 5.72 (d, J = 148.5 Hz, 1H), 5.06 (t, J = 7.2 Hz, 1H), 4.47 (s, 1H), 4.10-3.79 (m, 4H), 3.61-3.40 (m, 3H), 3.20 (s, 2H), 2.99 (s, 1H), 2.30 (d, J = 20.3 Hz, 1H), 2.10 (d, J = 13.0 Hz, 1H), 1.90 (s, 3H), 1.78-1.32 (m, 9H), 1.27 (t, J = 7.0 Hz, 3H), 1.00-0.70 (m, 2H).
LCMS Calculated for $C_{31}H_{37}F_3N_6O_4$: 614.28; Observed (Method-P): 613.3 [M − H] $^-$, 99.8% at RT 1.853 min.
Chiral-SFC (Method-C): 98.27% at RT 0.89 min.

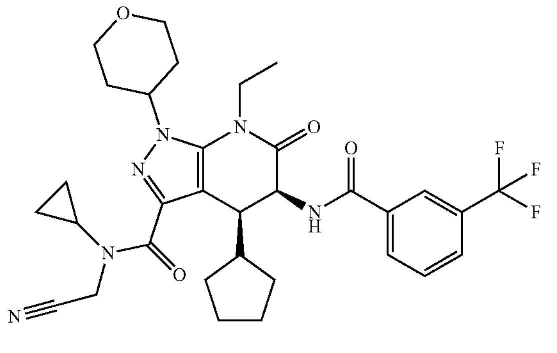 [SMILES: CCN1C(=O)[C@@H](NC(=O)c2cccc(C(F)(F)F)c2)[C@@H](C2CCCC2)c2c(C(=O)N(CC#N)C3CC3)nn(C3CCOCC3)c21]

I-478

$^1H$ NMR (400 MHz, DMSO-$d_6$) δ 8.92 (d, J = 7.7 Hz, 1H), 8.32-8.21 (m, 2H), 7.95 (d, J = 7.8 Hz, 1H), 7.76 (t, J = 7.8 Hz, 1H), 5.03 (dd, J = 7.7, 6.4 Hz, 1H), 4.70-4.38 (m, 3H), 4.07-3.77 (m, 4H), 3.61-3.43 (m, 3H), 3.14 (s, 1H), 2.35-2.22 (m, 1H), 2.08 (d, J = 12.9 Hz, 1H), 1.99-1.85 (m, 3H), 1.71 (d, J = 6.2 Hz, 1H), 1.51-1.32 (m, 5H), 1.28 (t, J = 7.0 Hz, 3H), 1.05-0.92 (m, 1H), 0.78 (q, J = 6.7, 4.8 Hz, 4H), 0.48 (s, 1H).
LCMS Calculated for: $C_{32}H_{37}F_3N_6O_4$: 626.28; Observed (Method-M): 625.3 [M − H] $^-$, 99.6% at RT 1.507 min.
Chiral-SFC (Method-A): 97.83% at RT 1.09 min -continued

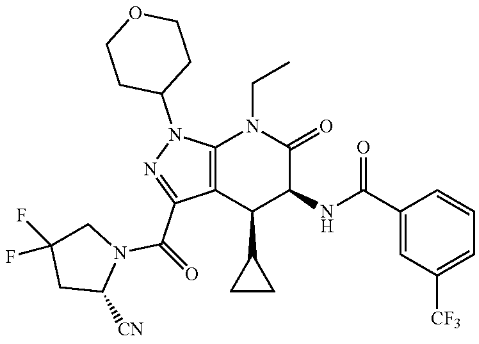 [SMILES: CCN1C(=O)[C@@H](NC(=O)c2cccc(C(F)(F)F)c2)[C@@H](C2CC2)c2c(C(=O)N3CC(F)(F)C[C@H]3C#N)nn(C3CCOCC3)c21]

I-378

$^1$H NMR (300 MHz, DMSO-$d_6$) δ 9.06 (dd, J = 11.3, 8.0 Hz, 1H), 8.32 (s, 1H), 8.25 (d, J = 7.8 Hz, 1H), 7.96 (d, J = 7.8 Hz, 1H), 7.76 (t, J = 7.9 Hz, 1H), 5.26 (dd, J = 9.0, 3.5 Hz, 1H), 5.12-4.95 (m, 1H), 4.64-4.41 (m, 2H), 4.18-3.78 (m, 5H), 3.64-3.36 (m, 3H), 3.15-2.76 (m, 2H), 2.30-1.88 (m, 4H), 1.27 (q, J = 7.4 Hz, 3H), 0.83 (d, J = 7.8 Hz, 1H), 0.49 (d, J = 5.4 Hz, 1H), 0.24-0.07 (m, 3H). LCMS Calculated for $C_{30}H_{31}F_5N_6O_4$: 634.23; Observed (Method-N): 633.2 [M − H] $^-$, 99.2% at RT 1.970 min.

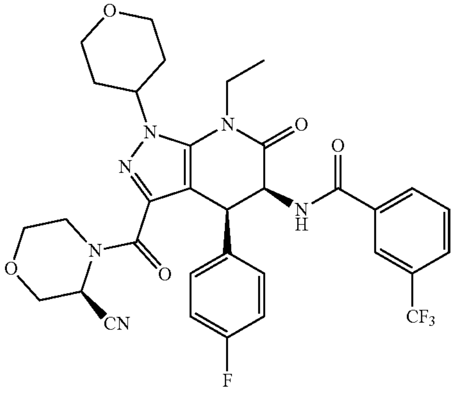 [SMILES: CCN1C(=O)[C@@H](NC(=O)c2cccc(C(F)(F)F)c2)[C@@H](c2ccc(F)cc2)c2c(C(=O)N3CCOC[C@@H]3C#N)nn(C3CCOCC3)c21]

I-624

$^1$H NMR (300 MHz, DMSO-$d_6$) δ 8.52 (d, J = 7.0 Hz, 1H), 8.13 (m, 2H), 7.92 (d, J = 7.8 Hz, 1H), 7.71 (t, J = 7.8 Hz, 1H), 7.07 (m, 2H), 7.00-6.86 (m, 2H), 5.60-4.46 (m, 4H), 4.21-3.87 (m, 6H), 3.71-3.48 (m, 4H), 3.02 (s, 1H), 2.53-2.25 (m, 2H), 2.22-1.89 (m, 3H), 1.32 (t, J = 7.0 Hz, 3H). LCMS Calculated for $C_{33}H_{32}F_4N_6O_5$: 668.24; Observed (Method-G): 669.2 [M + H] $^+$, 99.9% at RT 1.152 min.

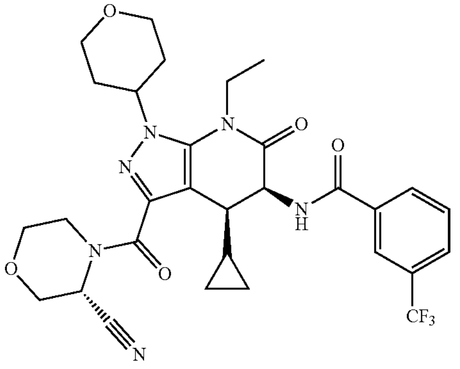 [SMILES: CCN1C(=O)[C@@H](NC(=O)c2cccc(C(F)(F)F)c2)[C@@H](C2CC2)c2c(C(=O)N3CCOC[C@H]3C#N)nn(C3CCOCC3)c21]

I-381

$^1$H NMR (300 MHz, DMSO-$d_6$) δ 9.03 (d, J = 7.8 Hz, 1H), 8.31 (s, 1H), 8.24 (d, J = 7.9 Hz, 1H), 7.96 (d, J = 7.8 Hz, 1H), 7.76 (t, J = 7.8 Hz, 1H), 6.24-5.55 (m, 1H), 5.16-5.02 (m, 1H), 4.98-4.78 (m, 1H), 4.61-4.44 (m, 1H), 4.39-4.22 (m, 1H), 4.20-3.76 (m, 6H), 3.77-3.42 (m, 5H), 3.26 (t, J = 6.3 Hz, 1H), 3.19-2.94 (m, 1H), 2.13-1.84 (m, 3H), 1.27 (t, J = 6.9 Hz, 3H), 0.93-0.76 (m, 1H), 0.56-0.43 (m, 1H), 0.20 (t, J = 8.9 Hz, 1H), 0.10 (s, 2H). LCMS Calculated for: $C_{30}H_{33}F_3N_6O_5$: 614.25; Observed: (Method-A): 615.3 [M + H] $^+$, 99.6% at RT 1.146 min.

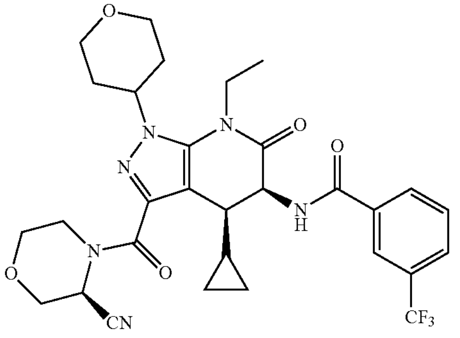 [SMILES: CCN1C(=O)[C@@H](NC(=O)c2cccc(C(F)(F)F)c2)[C@@H](C2CC2)c2c(C(=O)N3CCOC[C@@H]3C#N)nn(C3CCOCC3)c21]

I-551

$^1$H NMR (300 MHz, DMSO-$d_6$) δ 9.05 (d, J = 8.0 Hz, 1H), 8.32 (s, 1H), 8.25 (d, J = 7.8 Hz, 1H), 7.96 (d, J = 7.8 Hz, 1H), 7.76 (t, J = 7.8 Hz, 1H), 5.50 (s, 1H), 5.11 (t, J = 7.0 Hz, 1H), 4.73-4.25 (m, 2H), 4.16-4.03 (m, 6H), 3.76-3.39 (m, 5H), 3.31-3.20 (m, 3H), 2.13-2.03 (m, 1H), 2.13-1.82 (m, 3H), 1.26 (t, J = 7.0 Hz, 3H), 0.82 (s, 1H), 0.49 (d, J = 8.5 Hz, 1H), 0.22 (d, J = 8.5 Hz, 1H). LCMS Calculated for $C_{30}H_{33}F_3N_6O_5$: 614.25; Observed (Method-C): 615.2 [M + H] $^+$, 99.8% at RT 1.228 min.

-continued

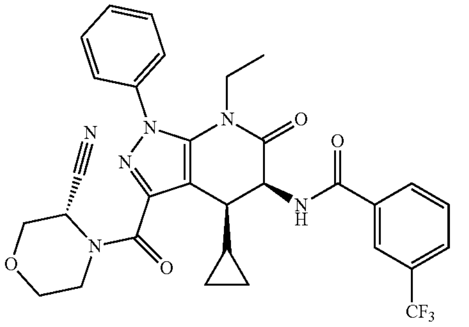 [SMILES: CCN1C(=O)[C@@H](NC(=O)c2cccc(C(F)(F)F)c2)[C@@H](C2CC2)c2c(C(=O)N3CCOC[C@@H]3C#N)nn(-c3ccccc3)c21]

I-658

$^1$H NMR (300 MHz, DMSO-$d_6$) δ 9.11 (d, J = 8.0 Hz, 1H), 8.35 (s, 1H), 8.28 (d, J = 7.9 Hz, 1H), 7.96 (d, J = 7.8 Hz, 1H), 7.86-7.70 (m, 3H), 7.68-7.52 (m, 3H), 5.51 (s, 1H), 5.42 (t, J = 7.1 Hz, 1H), 4.75 (d, J = 13.3 Hz, 1H), 4.54-4.31 (m, 1H), 4.19-3.79 (m, 4H), 3.77-3.38 (m, 3H), 3.02-2.85 (m, 1H), 0.84 (t, J = 6.9 Hz, 4H), 0.54 (t, J = 8.3 Hz, 1H), 0.25 (t, J = 9.0 Hz, 1H), 0.04-0.02 (m, 1H). LCMS Calculated for $C_{31}H_{29}F_3N_6O_4$: 606.22; Observed (Method-A): 607.3 [M + H] $^+$, 99.8% at RT 1.243 min.

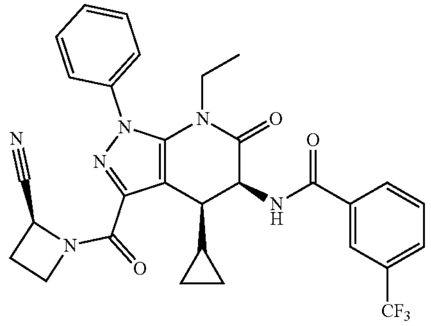 [SMILES: CCN1C(=O)[C@@H](NC(=O)c2cccc(C(F)(F)F)c2)[C@@H](C2CC2)c2c(C(=O)N3CC[C@H]3C#N)nn(-c3ccccc3)c21]

I-561

$^1$H NMR (300 MHz, DMSO-$d_6$) δ 9.09 (dd, J = 11.8, 7.9 Hz, 1H), 8.34 (s, 1H), 8.28 (d, J = 7.8 Hz, 1H), 7.96 (d, J = 7.8 Hz, 1H), 7.84-7.67 (m, 3H), 7.68-7.50 (m, 3H), 5.67-5.10 (m, 2H), 4.52 (t, J = 7.7 Hz, 1H), 4.19-3.99 (m, 1H), 3.98-3.79 (m, 1H), 3.44 (td, J = 6.5, 3.8 Hz, 1H), 3.06-2.84 (m, 1H), 2.80-2.53 (m, 2H), 0.83 (q, J = 6.7 Hz, 4H), 0.53 (tt, J = 8.6, 4.2 Hz, 1H), 0.33-0.03 (m, 3H). LCMS Calculated for $C_{30}H_{27}F_3N_6O_3$: 576.21; Observed: (Method-P): 575.2 [M − H] $^-$, 99.9% at RT 2.732 min.

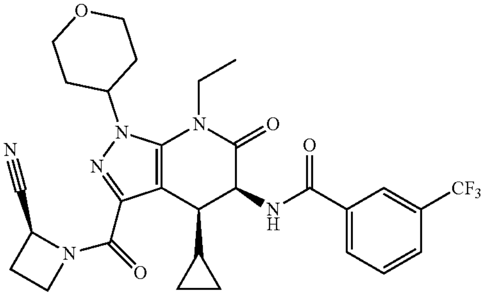 [SMILES: CCN1C(=O)[C@@H](NC(=O)c2cccc(C(F)(F)F)c2)[C@@H](C2CC2)c2c(C(=O)N3CC[C@H]3C#N)nn(C3CCOCC3)c21]

I-660

$^1$H NMR (300 MHz, DMSO-$d_6$) δ 9.04 (dd, J = 10.6, 7.9 Hz, 1H), 8.33-8.22 (m, 2H), 7.96 (d, J = 7.8 Hz, 1H), 7.76 (t, J = 7.8 Hz, 1H), 5.70-5.11 (m, 1H), 5.02 (td, J = 8.0, 6.0 Hz, 1H), 4.68-4.45 (m, 2H), 4.17-3.77 (m, 5H), 3.53 (q, J = 12.3 Hz, 2H), 2.81-2.55 (m, 2H), 2.44-1.84 (m, 5H), 1.25 (q, J = 7.4 Hz, 3H), 0.82 (t, J = 7.2 Hz, 1H), 0.48 (d, J = 6.0 Hz, 1H), 0.23-0.00 (m, 3H). LCMS Calculated for $C_{29}H_{31}F_3N_6O_4$: 584.24; Observed (Method-A): 583.3 [M − H] $^-$, 98.2% at RT 1.133 min.

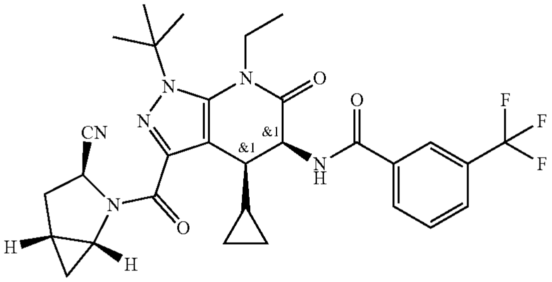 [SMILES: CCN1C(=O)[C@@H](NC(=O)c2cccc(C(F)(F)F)c2)[C@@H](C2CC2)c2c(C(=O)N3[C@H](C#N)C[C@H]4C[C@H]43)nn(C(C)(C)C)c21]

I-517

$^1$H NMR (400 MHz, DMSO-$d_6$) δ 8.92 (d, J = 8.3 Hz, 1H), 8.29 (s, 1H), 8.23 (d, J = 7.9 Hz, 1H), 7.96 (d, J = 7.9 Hz, 1H), 7.76 (t, J = 7.8 Hz, 1H), 5.05-4.81 (m, 2H), 4.58-4.44 (m, 1H), 4.28 (d, J = 7.4 Hz, 1H), 3.82-3.62 (m, 1H), 3.22-3.00 (m, 1H), 2.43-2.26 (m, 1H), 2.04-1.75 (m, 1H), 1.69 (d, J = 4.6 Hz, 9H), 1.51-1.40 (m, 1H), 1.12 (t, J = 6.9 Hz, 3H), 1.02-0.90 (m, 1H), 0.74-0.64 (m, 2H), 0.64-0.51 (m, 2H), 0.28-0.09 (m, 2H). LCMS Calculated for $C_{30}H_{33}F_3N_6O_3$: 582.26; Observed (Method-X): 583.26 [M + H] $^+$, 95.1% at RT 1.328 min.

-continued

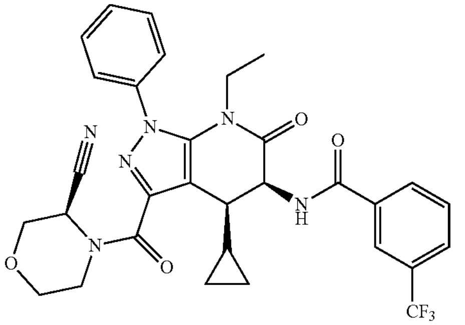 [SMILES: CCN1C(=O)[C@@H](NC(=O)c2cccc(C(F)(F)F)c2)[C@@H](C2CC2)c2c(C(=O)N3CCOC[C@H]3C#N)nn(-c3ccccc3)c21]

I-382

$^1$H NMR (300 MHz, DMSO-$d_6$) δ 9.09 (d, J = 7.7 Hz, 1H), 8.35 (s, 1H), 8.28 (d, J = 7.8 Hz, 1H), 7.97 (d, J = 7.8 Hz, 1H), 7.77 (t, J = 7.8 Hz, 3H), 7.68-7.53 (m, 3H), 6.35-5.66 (m, 1H), 5.41 (dd, J = 8.0, 6.2 Hz, 1H), 4.80 (s, 1H), 4.20-3.80 (m, 3H), 3.78-3.60 (m, 1H), 3.47 (s, 2H), 3.02 (d, J = 37.4 Hz, 2H), 0.85 (t, J = 6.8 Hz, 4H), 0.54 (t, J = 8.7 Hz, 1H), 0.27 (d, J = 8.7 Hz, 1H), 0.08 (d, J = 5.0 Hz, 2H). LCMS Calculated for $C_{31}H_{29}F_3N_6O_4$: 606.2; Observed: (Method-C): 607.2 [M + H] $^+$, 99.7% at RT 1.399 min.

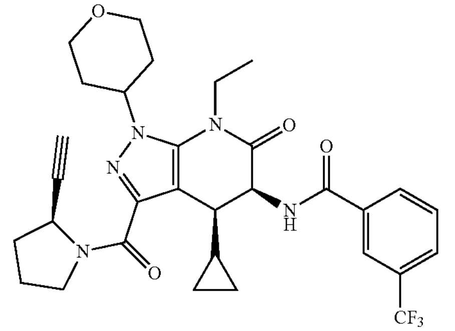 [SMILES: C#C[C@@H]1CCCN1C(=O)c1nn(C2CCOCC2)c2c1[C@H](C1CC1)[C@H](NC(=O)c1cccc(C(F)(F)F)c1)C(=O)N2CC]

I-594

$^1$H NMR (300 MHz, DMSO-$d_6$) δ 9.06-8.97 (m, 1H), 8.29 (s, 1H), 8.23 (d, J= 7.8 Hz, 1H), 7.94 (d, J = 7.8 Hz, 1H), 7.74 (t, J = 7.8 Hz, 1H), 5.63-4.96 (m, 2H), 4.81-4.66 (m, 1H), 4.57-4.38 (m, 1H), 4.19-3.70 (m, 5H), 3.63-3.35 (m, 4H), 3.17-3.01 (m, 1H), 2.35-2.13 (m, 2H), 2.11-1.78 (m, 5H), 1.39-1.16 (m, 3H), 0.86-0.71 (m, 1H), 0.54-0.37 (m, 1H), 0.20-0.01 (m, 3H). LCMS Calculated for $C_{31}H_{34}F_3N_5O_4$: 597.26; Observed: Method-C (LCMS-10): 598.2 [M + H] $^+$, 98.2% at RT 1.292 min.

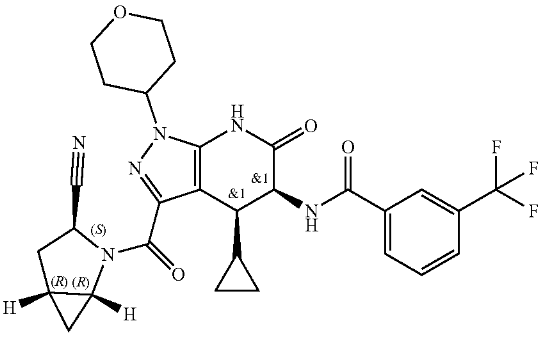

I-385

$^1$H NMR (400 MHz, DMSO-$d_6$) δ 11.27 (s, 1H), 9.05 (d, J = 7.3 Hz, 1H), 8.33 (s, 1H), 8.26 (d, J = 7.9 Hz, 1H), 7.96 (d, J = 7.8 Hz, 1H), 7.76 (t, J = 7.8 Hz, 1H), 5.26-4.83 (m, 2H), 4.54 (s, 1H), 4.37-4.16 (m, 1H), 4.03-3.95 (m, 2H), 3.43 (t, J = 11.6 Hz, 3H), 2.68 (s, 1H), 2.48-2.34 (m, 2H), 2.08-1.84 (m, 5H), 0.97-0.85 (m, 2H), 0.69-0.43 (m, 2H), 0.18 (d, J = 7.6 Hz, 1H), 0.07 (s, 1H). LCMS Calculated for $C_{29}H_{29}F_3N_6O_4$: 582.22; Observed (Method-R): 581.4 [M − H] $^-$, 99.1% at RT 1.002 min.

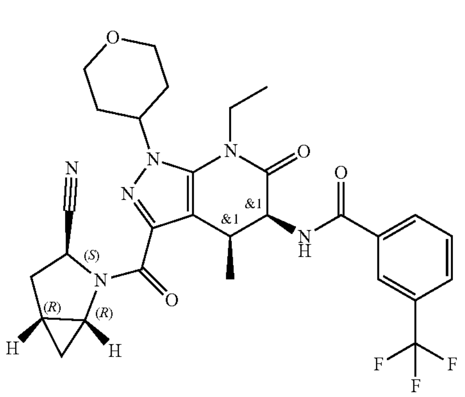

I-386

1H NMR (400 MHz, DMSO-$d_6$) δ 9.01 (t, J = 7.1 Hz, 1H), 8.34-8.29 (m, 1H), 8.24 (d, J = 7.8 Hz, 1H), 7.95 (d, J = 7.8 Hz, 1H), 7.76 (t, J = 7.8 Hz, 1H), 5.77-4.88 (m, 2H), 4.55 (s, 1H), 4.35 (m, 1H), 4.22 (dt, J = 14.2, 7.2 Hz, 1H), 4.02 (d, J = 11.4 Hz, 1H), 3.93 (d, J = 11.5 Hz, 1H), 3.81 (dd, J = 14.8, 7.5 Hz, 1H), 3.62-3.41 (m, 3H), 2.48-2.17 (m, 3H), 2.10-1.77 (m, 4H), 1.19 (td, J = 7.3, 2.6 Hz, 3H), 1.12-0.90 (m, 4H), 0.68 (s, 1H). LCMS Calculated for $C_{29}H_{31}F_3N_6O_4$: 584.24; Observed (Method-X): 583.3 [M − H] $^-$, 99.7% at RT 1.140 min.

-continued
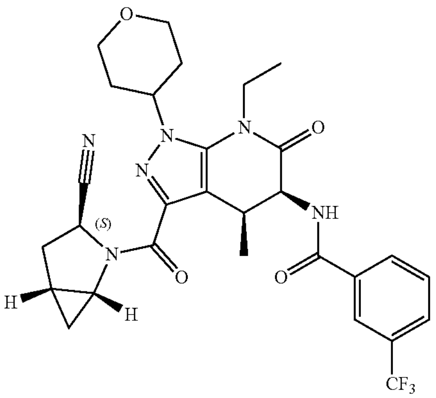
I-387
$^1$H NMR (400 MHz, DMSO-$d_6$) δ 9.02 (t, J = 9.9 Hz, 1H), 8.31 (s, 1H), 8.25 (d, J = 7.9 Hz, 1H), 7.95 (d, J = 7.7 Hz, 1H), 7.76 (t, J = 7.9 Hz, 1H), 5.64-4.98 (m, 1H), 4.97-4.85 (m, 1H), 4.53 (d, J = 10.8 Hz, 1H), 4.31-3.37 (m, 8H), 2.47-2.14 (m, 3H), 2.10-1.79 (m, 4H), 1.20 (t, J = 7.0 Hz, 3H), 1.12-0.95 (m, 4H), 0.67 (s, 1H).
LCMS Calculated for $C_{29}H_{31}F_3N_6O$: 584.24.; Observed (Method-N): 583.3 [M − H] $^-$, 99.2% at RT 1.868 min.
Chiral HPLC (Method-A): 100% at RT 0.697 min.
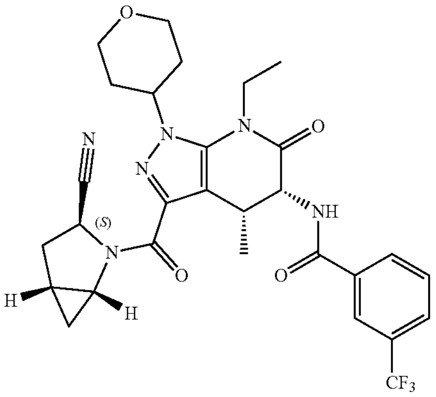
I-599
$^1$H NMR (400 MHz, DMSO-$d_6$) δ 9.02 (d, J = 8.2 Hz, 1H), 8.31 (s, 1H), 8.24 (d, J = 7.6 Hz, 1H), 7.96 (d, J = 7.8 Hz, 1H), 7.76 (t, J = 7.8 Hz, 1H), 5.77-4.84 (m, 2H), 4.55 (s, 1H), 4.50-3.36 (m, 8H), 2.49-2.18 (m, 3H), 2.17-1.79 (m, 4H), 1.19 (t, J = 7.0 Hz, 3H), 1.12-0.84 (m, 4H), 0.70-0.55 (m, 1H).
LCMS Calculated for $C_{29}H_{31}F_3N_6O_4$: 584.24; Observed (Method-N): 583.3 [M − H] $^-$, 99.7% at RT 1.877 min;
Chiral HPLC (Method-A): 99.3% at RT 0.986 min.

2. Synthesis of (4S,5S)-N-[(1R*)-1-cyano-3-hydroxypropyl]-7-ethyl-4-(4-fluorophenyl)-N-methyl-6-oxo-1-phenyl-5-[3-(trifluoromethyl)benzamido]-4H,5H-pyrazolo[3,4-b]pyridine-3-carboxamide (I-290) & (4S,5S)-N-[(1S*)-1-cyano-3-hydroxypropyl]-7-ethyl-4-(4-fluorophenyl)-N-methyl-6-oxo-1-phenyl-5-[3-(trifluoromethyl)benzamido]-4H,5H-pyrazolo[3,4-b]pyridine-3-carboxamide (I-301)

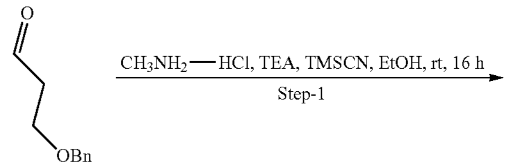

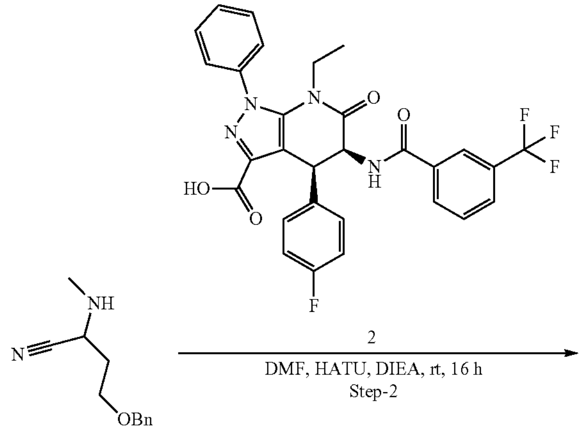

2

4

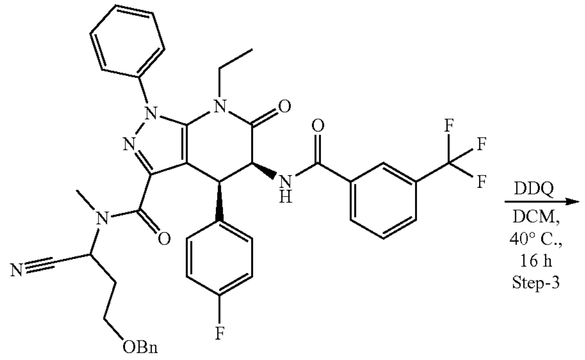

5

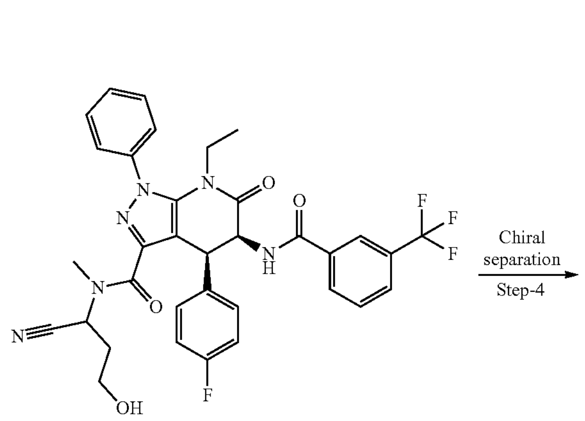

6

-continued

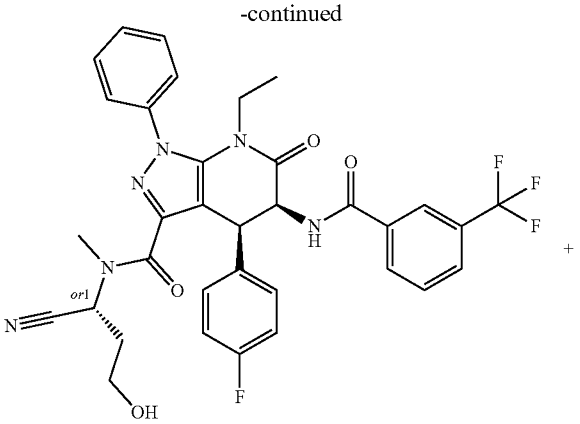

I-290

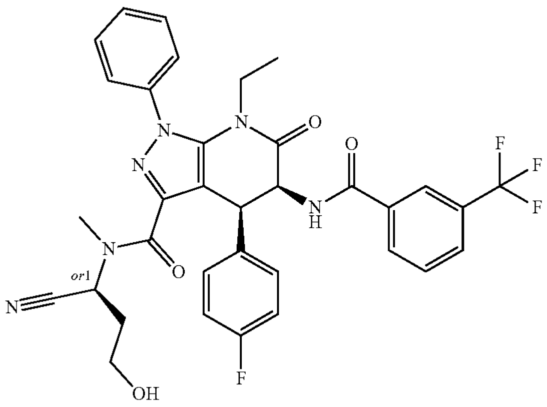

I-301

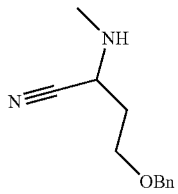

4-(benzyloxy)-2-(methylamino)butanenitrile (4)

A mixture of 3-(benzyloxy) propanal (15.0 g, 91.3 mmol, 1.00 equiv), $CH_3NH_2HCl$ (9.25 g, 137 mmol, 1.50 equiv) and TEA (27.7 g, 274 mmol, 3.00 equiv) in EtOH (150 mL) was stirred at room temperature for 10 min. TMSCN (13.6 g, 137 mmol, 1.50 equiv) was then added, and the reaction mixture was stirred for 16 h at room temperature. The reaction was quenched with water (15 mL) at room temperature. The resulting mixture was extracted with $CH_2Cl_2$ (3×20 mL). The combined organic layers were washed with brine (3×10 mL), dried over anhydrous $Na_2SO_4$. After filtration, the filtrate was concentrated under vacuum. The residue was purified by silica gel column chromatography, eluted with ethyl acetate:petroleum ether (1:5) to afford 4-(benzyloxy)-2-(methylamino) butanenitrile (12 g, 64.3%) as a colorless oil.

LCMS Calculated for $C_{12}H_{16}N_2O$: 204.13; Observed: 205.2 $[M+H]^+$.

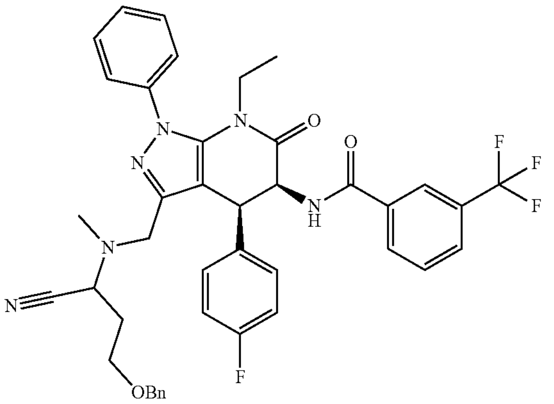

(4S,5S)-N-(3-(benzyloxy)-1-cyanopropyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4b]pyridine-3-carboxamide (5)

A mixture of 4-(benzyloxy)-2-(methylamino) butanenitrile (300 mg, 1.469 mmol, 1.00 equiv), DIEA (379.63 mg, 2.938 mmol, 2.00 equiv) and (4S,5S)-7-ethyl-4-(4-fluorophenyl)-6-oxo-1-phenyl-5-(3-(trifluoromethyl)benzamido)-4,5,6,7-tetrahydro-1H-pyrazolo[3,4-b]pyridine-3-carboxylic acid (832 mg, 1.47 mmol, 1.00 equiv) in DMF (10 mL) was stirred at room temperature for 10 min. HATU (670 mg, 1.76 mmol, 1.20 equiv) was then added, and the reaction mixture was stirred for 1.0 h at room temperature. The reaction was quenched with water (15 mL) at room temperature. The resulting mixture was extracted with $CH_2Cl_2$ (3×20 mL). The combined organic layers were washed with brine (3×10 mL), dried over anhydrous $Na_2SO_4$. After filtration, the filtrate was concentrated under vacuum. The residue was purified by silica gel column chromatography, eluted with petroleum ether/ethyl acetate (1:1) to afford (4S,5S)—N-(3-(benzyloxy)-1-cyanopropyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamide (600 mg, 54.2%) as a yellow solid.

LCMS Calculated for $C_{41}H_{36}F_4N_6O_4$: 752.27; Observed: 753.3 $[M+H]^+$.

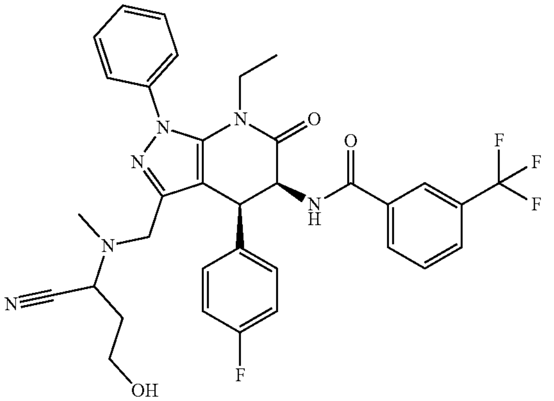

(4S,5S)-N-(1-cyano-3-hydroxypropyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4b]pyridine-3-carboxamide (5)

Into a 40 mL flask were added (4S,5S)—N-(3-(benzyloxy)-1-cyanopropyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamide (500 mg, 0.664 mmol, 1.00 equiv), DDQ (452 mg, 1.99 mmol, 3.00 equiv) and DCM (5 mL) at room temperature. The resulting mixture was stirred for 16 h at 40° C. The resulting mixture was diluted with DCM (10 mL). The resulting mixture was washed with $Na_2SO_3$ (aq.) (3×10 mL). The combined organic layers were washed with brine (1×10 mL), dried over anhydrous $Na_2SO_4$. The residue was purified by silica gel column chromatography, eluted with petroleum ether:ethyl acetate (1:1) to afford (4S,5S)—N-(1-cyano-3-hydroxypropyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamide (300 mg, 68.1%) as a yellow solid.

LCMS Calculated for $C_{34}H_{30}F_4N_6O_4$: 662.23; Observed: 663.3 $[M+H]^+$.

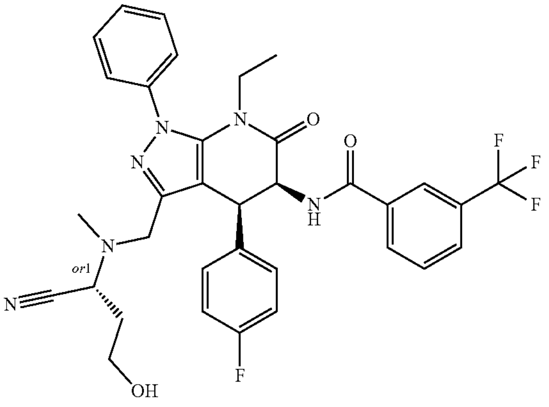

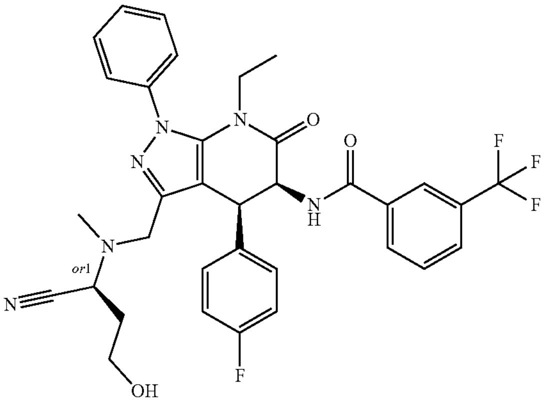

(4S,5S)-N-[(1R*)-1-cyano-3-hydroxypropyl]-7-ethyl-4-(4-fluorophenyl)-N-methyl-6-oxo-1-phenyl-5-[3-(trifluoromethyl)benzamido]-4H,5H-pyrazolo[3,4b]pyridine-3-carboxamide (I-290) & (4S,5S)-N-[(1S*)-1-cyano-3-hydroxypropyl]-7-ethyl-4-(4-fluorophenyl)-N-methyl-6-oxo-1-phenyl-5-[3-(trifluoromethyl)benzamido]-4H,5H-pyrazolo[3,4b]pyridine-3-carboxamide (I-301)

The crude product (4S,5S)—N-(1-cyano-3-hydroxypropyl)-7-ethyl-4-(4-fluorophenyl)-N-methyl-6-oxo-1-phenyl-5-[3-(trifluoromethyl)benzamido]-4H,5H-pyrazolo[3,4-b]pyridine-3-carboxamide (100 mg, 0.151 mmol, 1 equiv) was purified by Chiral-Prep-HPLC with the following conditions: Column: CHIRALPAKIH-3, 100*4.6 mm, 3 umIH30CB-BX002; Mobile Phase A: n-Hexane/THF=4/1, B: MeOH; Gradient: isocratic; Injection Volume: 1 uL. to afford (4S,5S)—N-[(1R*)-1-cyano-3-hydroxypropyl]-7-ethyl-4-(4-fluorophenyl)-N-methyl-6-oxo-1-phenyl-5-[3-(trifluoromethyl)benzamido]-4H,5H-pyrazolo[3,4-b]pyridine-3-carboxamide (I-290) (37 mg, 37%) as a white solid and (4S,5S)—N-[(1S*)-1-cyano-3-hydroxypropyl]-7-ethyl-4-(4-fluorophenyl)-N-methyl-6-oxo-1-phenyl-5-[3-(trifluoromethyl)benzamido]-4H,5H-pyrazolo[3,4-b]pyridine-3-carboxamide (I-301) (37 mg, 37%) as a white solid.

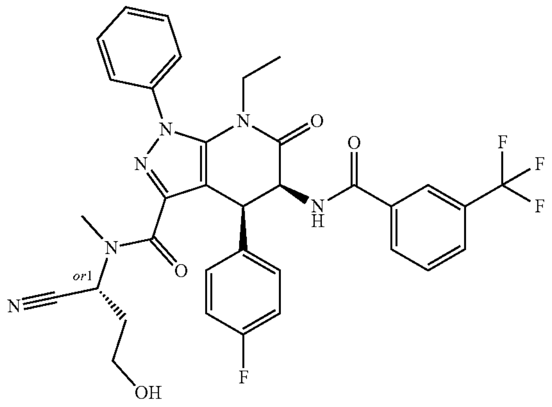 [SMILES: CCN1C(=O)[C@@H](NC(=O)c2cccc(C(F)(F)F)c2)[C@@H](c2ccc(F)cc2)c2c(C(=O)N(C)[C@@H](C#N)CCO)nn(-c3ccccc3)c21]

I-290

$^1$H NMR (300 MHz, Chloroform-d) δ 8.05 (s, 1H), 7.89 (d, J = 7.7 Hz, 1H), 7.82 (d, J = 7.8 Hz, 1H), 7.67-7.54 (m, 6H), 7.00 (d, J = 8.0 Hz, 4H), 6.85 (s, 1H), 5.34-5.33 (m, 1H), 5.08-5.07 (m, 1H), 4.01 (dd, J = 14.5, 7.3 Hz, 2H), 3.65-3.62 (m, 2H), 3.51 (s, 1H), 3.20 (s, 1H), 3.07 (s, 2H), 2.13 (s, 3H), 1.03 (t, J = 6.9 Hz, 3H).
LCMS Calculated for $C_{34}H_{30}F_4N_6O_4$: 662.23; Observed (Method-G): 663.2 [M + H] $^+$, 98.9% at RT 1.751 min.
Chiral HPLC (Method-B): 100% at RT 6.224 min.

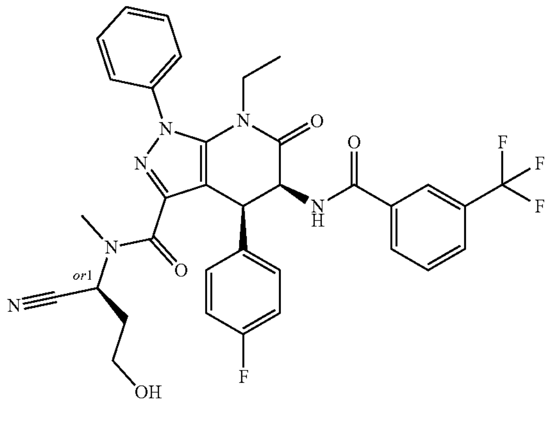 [SMILES: CCN1C(=O)[C@@H](NC(=O)c2cccc(C(F)(F)F)c2)[C@@H](c2ccc(F)cc2)c2c(C(=O)N(C)[C@H](C#N)CCO)nn(-c3ccccc3)c21]

I-301

$^1$H NMR (300 MHz, Chloroform-d) δ 8.05 (s, 1H), 7.85 (dd, J = 19.6, 7.8 Hz, 2H), 7.61 (s, 6H), 7.04-6.92 (m, 4H), 6.03 (s, 1H), 5.28-5.26 (s, 1H), 5.16-5.14 (s, 1H), 3.99 (s, 1H), 3.72 (s, 2H), 3.44 (s, 1H), 3.27-3.17 (m, 2H), 3.08 (s, 1H), 2.15-5.12 (m, 4H), 1.04 (t, J = 7.0 Hz, 3H).
LCMS Calculated for: $C_{34}H_{30}F_4N_6O_4$: 662.23; Observed (Method-B): 663.2 [M + H] $^+$, 98.8% at RT 1.153 min.
Chiral HPLC (Method-B): 100% at RT 7.402 min.

3. Synthesis of (4S,5S)-N-((S*)-1-cyano-3-*(dimethylamino)propyl-7-ethyl-4-(4-fluorophenyl)-N-methyl-6-oxo-1-phenyl-5-(3-(trifluoromethyl)benzamido)-4,5,6,7-tetrahyde-1H-pyrazolo[3,4-b]pyridine-3-carboxamide (I-303)& (4S,5S)-N-((R*)-1-cyano-3-(dimethylamino)propyl)-7-ethyl-4-(4-fluorophenyl)-N-methyl-6-oxo-1-phenyl-5-(3-(trifluoromethyl)benzamido)-4,5,6,7-tetrahyde-1H-pyrazolo[3,4-b]pyridine-3-carboxamide

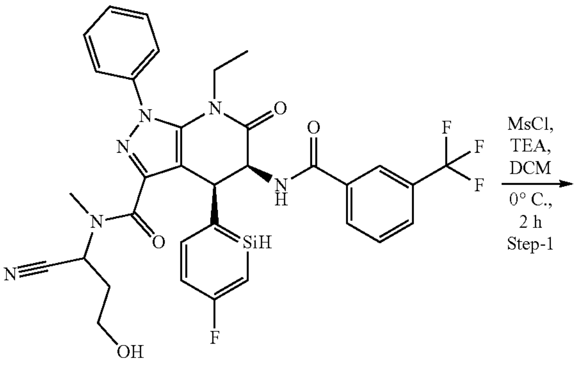

6

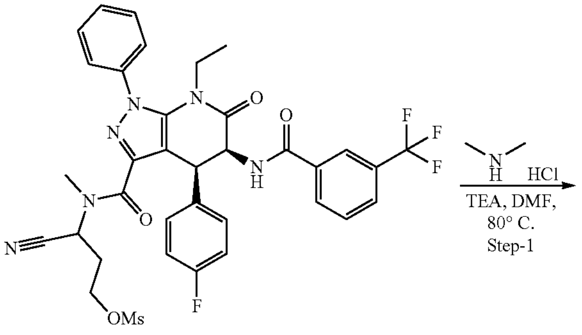

7

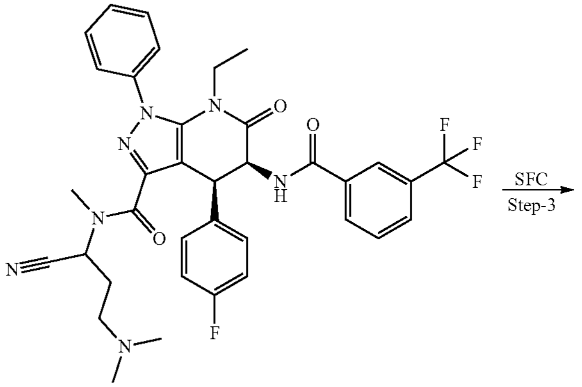

8

-continued

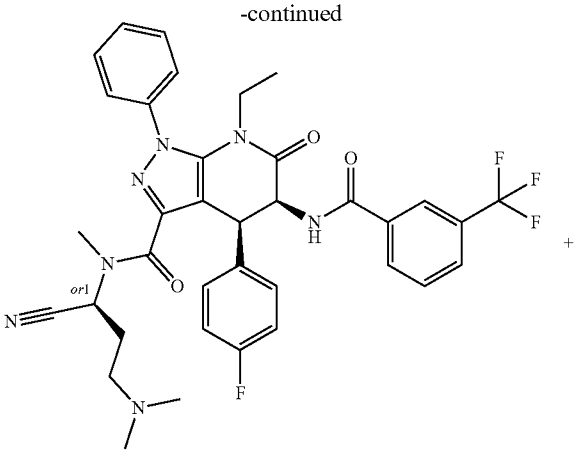

I-303

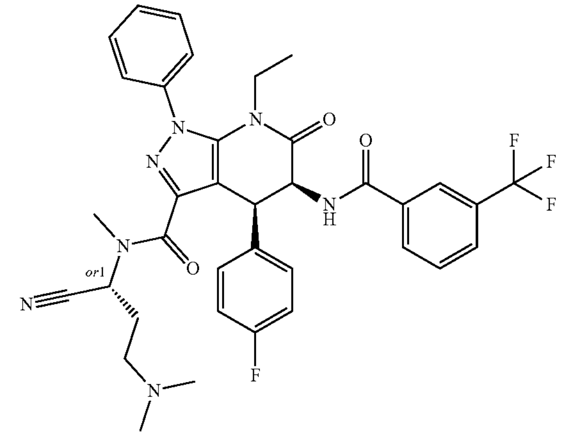

I-304

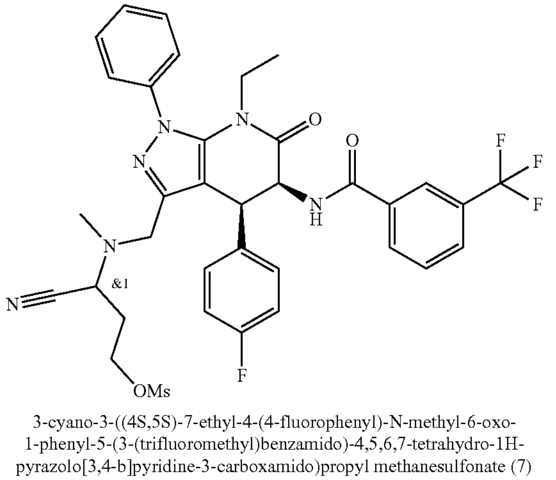 [SMILES: CCN1C(=O)[C@@H](NC(=O)c2cccc(C(F)(F)F)c2)[C@@H](c2ccc(F)cc2)c2c(CN(C)C(C#N)CCOS(C)(=O)=O)nn(-c3ccccc3)c21]

3-cyano-3-((4S,5S)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamido)propyl methanesulfonate (7)

A mixture of (4S,5S)—N-(1-cyano-3-hydroxypropyl)-7-ethyl-4-(5-fluorosilin-2-yl)-N-methyl-6-oxo-1-phenyl-5-(3-(trifluoromethyl)benzamido)-4,5,6,7-tetrahydro-1H-pyrazolo[3,4-b]pyridine-3-carboxamide (400 mg, 0.589 mmol, 1.00 equiv), TEA (119 mg, 1.18 mmol, 2.00 equiv) and DCM (4 mL) was stirred at 0° C. for 10 min. MsCl (81.0 mg, 0.707 mmol, 1.20 equiv) was then added, and the reaction mixture was stirred for 1.0 h at 0° C. The resulting mixture was diluted with DCM (10 mL). The resulting mixture was washed with $H_2O$ (3×10 mL). The combined organic layers were washed with brine (1×10 mL), dried over anhydrous $Na_2SO_4$. After filtration, the filtrate was concentrated under vacuum to give 3-cyano-3-((4S,5S)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamido)propyl methanesulfonate (350 mg, 80%) as a yellow solid.

LCMS Calculated for $C_{35}H_{32}F_4N_6O_6S$: 740.20; Observed: 741.3 $[M+H]^+$.

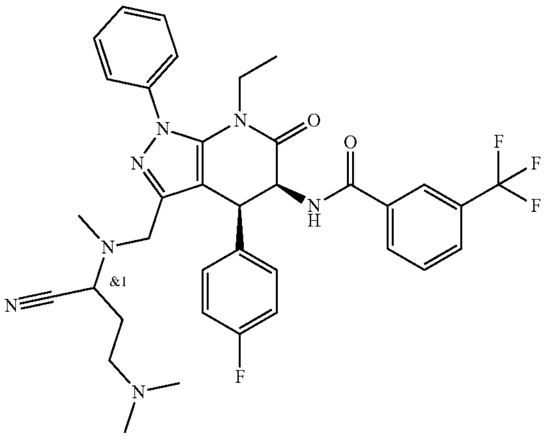

(4S,5S)-N-(1-cyano-3-(dimethylamino)propyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4b]pyridine-3-carboxamide (37-1)

A solution of 3-cyano-3-((4S,5S)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamido)propyl methanesulfonate (1.00 g, 1.35 mmol, 1.00 equiv), dimethylamine (0.18 g, 4.05 mmol, 3.00 equiv) and TEA (0.41 g, 4.05 mmol, 3.00 equiv) in THF (10 mL) was stirred for 16 h at 80° C. The resulting mixture was filtered, the filter cake was washed with EtOAc (2×20 mL). The filtrate was concentrated under reduced pressure. The residue was purified by silica gel column chromatography, eluted with petroleum ether/ethyl acetate (4:1) to afford (4S,5S)—N-(1-cyano-3-(dimethylamino)propyl)-7-ethyl-4-(4-fluorophenyl)-N-methyl-6-oxo-1-phenyl-5-(3-(trifluoromethyl)benzamido)-4,5,6,7-tetrahydro-1H-pyrazolo[3,4-b]pyridine-3-carboxamide (200 mg, 21.5%) as a white solid.

$^1H$ NMR (300 MHZ, DMSO-$d_6$) δ 8.57 (d, J=7.1 Hz, 1H), 8.19-8.09 (m, 2H), 7.92 (d, J=7.9 Hz, 1H), 7.85-7.55 (m, 6H), 7.14-6.92 (m, 4H), 5.54 (s, 1H), 4.87 (d, J=7.3 Hz, 1H), 3.88 (q, J=7.2 Hz, 1H), 3.26 (s, 1H), 3.03 (dt, J=13.6, 6.9 Hz, 1H), 2.93 (s, 1H), 2.53 (s, 3H), 2.12-1.86 (m, 9H), 0.91 (t, J=7.0 Hz, 3H).

LCMS Calculated for $C_{36}H_{35}F_4N_7O_3$: 689.27; Observed: 690.2 $[M+H]^+$.

(4S,5S)—N-[(1S*)-1-cyano-3-(dimethylamino)propyl]-7-ethyl-4-(4-fluorophenyl)-N-methyl-6-oxo-1-phenyl-5-[3-(trifluoromethyl)benzamido]-4H,5H-pyrazolo[3,4-b]pyridine-3-carboxamide (I-303) & (4S,5S)—N-[(1R*)-1-cyano-3-(dimethylamino)propyl]-7-ethyl-4-(4-fluorophenyl)-N-methyl-6-oxo-1-phenyl-5-[3-(trifluoromethyl)benzamido]-4H,5H-pyrazolo[3,4-b]pyridine-3-carboxamide (I-304)

The crude product (4S,5S)—N-[1-cyano-3-(dimethylamino)propyl]-7-ethyl-4-(4-fluorophenyl)-N-methyl-6-oxo-1-phenyl-5-[3-(trifluoromethyl)benzamido]-4H,5H-pyrazolo[3,4-b]pyridine-3-carboxamide (33 mg, 0.048 mmol, 1.00 equiv) was purified was purified by Chiral-Prep-HPLC with the following conditions: Column: CHIRALPAKIH-3, 100*4.6 mm, 3 umIH30CB-BX002; Mobile Phase A: n-Hexane/THF=4/1, B: MeOH; Gradient: isocratic; Injection Volume: 1 uL. to afford (4S,5S)—N-[(1S*)-1-cyano-3-(dimethylamino)propyl]-7-ethyl-4-(4-fluorophenyl)-N-methyl-6-oxo-1-phenyl-5-[3-(trifluoromethyl)benzamido]-4H,5H-pyrazolo[3,4-b]pyridine-3-carboxamide (13.7 mg, 41.5%) as a white solid and (4S,5S)—N-[(1R*)-1-cyano-3-(dimethylamino)propyl]-7-ethyl-4-(4-fluorophenyl)-N-methyl-6-oxo-1-phenyl-5-[3-(trifluoromethyl)benzamido]-4H,5H-pyrazolo[3,4-b]pyridine-3-carboxamide (12.6 mg, 38.1%) as a white solid.

The following compounds were prepared from the above general method using the intermediates such as:

| | |
|---|---|
| 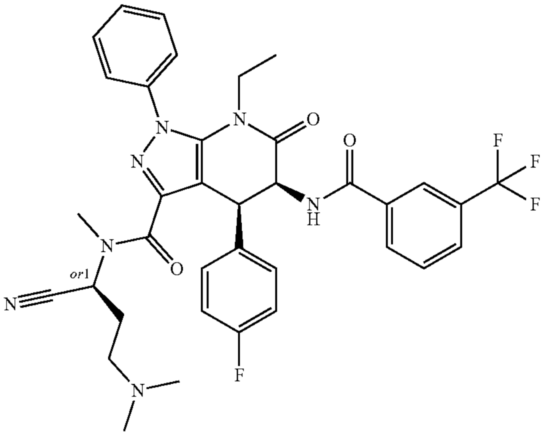 [SMILES: CCN1C(=O)[C@@H](NC(=O)c2cccc(C(F)(F)F)c2)[C@@H](c2ccc(F)cc2)c2c(C(=O)N(C)[C@H](C#N)CCN(C)C)nn(-c3ccccc3)c21]<br>I-303 | $^1H$ NMR (300 MHz, Chloroform-d) δ 8.03 (s, 1H), 7.88 (d, J = 7.8 Hz, 1H), 7.80 (d, J = 7.8 Hz, 1H), 7.67-7.50 (m, 6H), 7.07-6.90 (m, 4H), 6.85 (d, J = 6.2 Hz, 1H), 5.81 (s, 1H), 5.32 (t, J = 6.7 Hz, 1H), 5.18 (d, J = 11.1 Hz, 1H), 4.00 (dq, J = 14.4, 7.2 Hz, 1H), 3.49 (s, 1H), 3.22 (dq, J = 13.9, 6.9 Hz, 2H), 3.09 (s, 1H), 2.49-2.03 (m, 10H), 1.02 (t, J = 7.1 Hz, 3H).<br>LCMS Calculated for $C_{36}H_{35}F_4N_7O_3$: 689.27; Observed (Method-B): 690.2 $[M + H]^+$, 99.5% at RT 0.944 min.<br>Chiral SFC (Method-A): 100% at RT 0.643 min. |

-continued

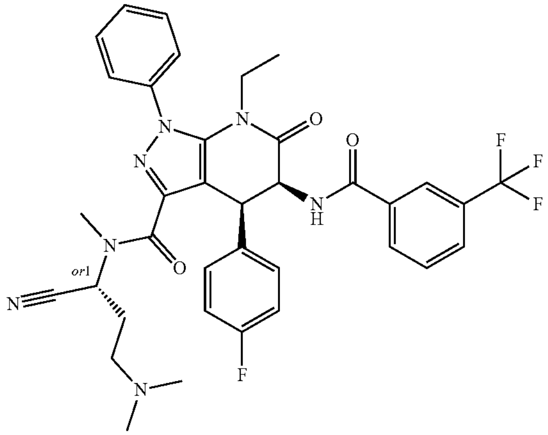 [SMILES: CCN1C(=O)[C@@H](NC(=O)c2cccc(C(F)(F)F)c2)[C@@H](c2ccc(F)cc2)c2c(C(=O)N(C)[C@@H](C#N)CCN(C)C)nn(-c3ccccc3)c21]

$^1$H NMR (300 MHz, Chloroform-d) δ 8.04 (s, 1H), 7.88 (d, J = 7.8 Hz, 1H), 7.80 (d, J = 7.8 Hz, 1H), 7.59 (q, J = 5.6, 4.7 Hz, 6H), 7.08-6.90 (m, 4H), 6.83 (d, J = 6.5 Hz, 1H), 5.75 (s, 1H), 5.33 (t, J = 6.8 Hz, 1H), 5.18 (s, 1H), 4.00 (dq, J = 14.3, 7.1 Hz, 1H), 3.46 (s, 1H), 3.22 (dq, J = 14.0, 6.9 Hz, 2H), 3.07 (s, 1H), 2.4-2.10 (m, 10H), 1.03 (t, J = 7.0 Hz, 3H).
LCMS Calculated for $C_{36}H_{35}F_4N_7O_3$: 689.27; Observed (Method-B): 690.2 [M + H] $^+$, 99.1% at RT 0.943 min.
Chiral SFC (Method-A): 100% at RT 0.779 min.

I-304

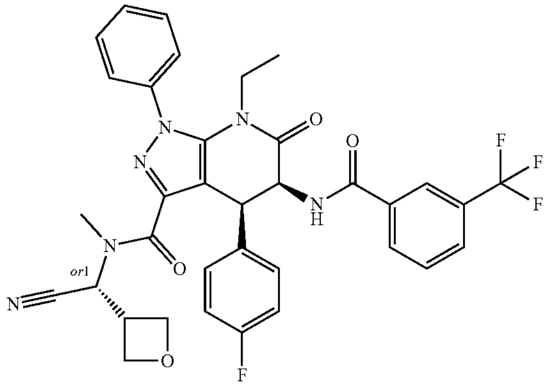 [SMILES: CCN1C(=O)[C@@H](NC(=O)c2cccc(C(F)(F)F)c2)[C@@H](c2ccc(F)cc2)c2c(C(=O)N(C)[C@@H](C#N)C3COC3)nn(-c3ccccc3)c21]

$^1$H NMR (300 MHz, Chloroform-d) δ 8.04 (d, J = 1.9 Hz, 1H), 7.91-7.86 (m, 1H), 7.81 (d, J = 7.7 Hz, 1H), 7.66-7.54 (m, 5H), 7.04-6.94 (m, 4H), 6.89 (d, J = 6.3 Hz, 1H), 5.33 (t, J = 6.8 Hz, 1H), 5.18 (d, J = 7.2 Hz, 1H), 4.88 (t, J = 7.3 Hz, 1H), 4.79-4.46 (m, 3H), 4.11-3.91 (m, 2H), 3.63-2.93 (m, 4H), 2.16-1.69 (m, 2H), 1.04 (t, J = 7.0 Hz, 3H).
LCMS Calculated for $C_{35}H_{30}F_4N_6O_4$: 674.20; Observed (Method-B): 675.1 [M + H] $^+$, 99.5% at RT 1.362.
Chiral HPLC (Method-F): 100% at RT 1.289 min.

I-291

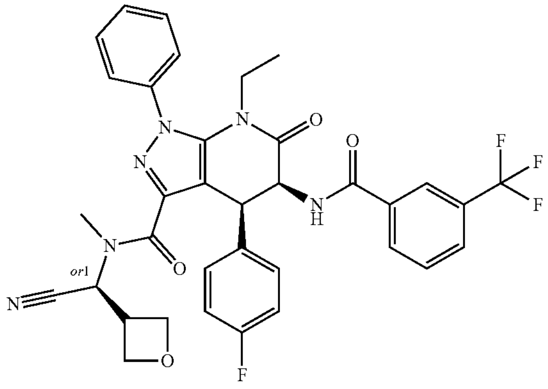 [SMILES: CCN1C(=O)[C@@H](NC(=O)c2cccc(C(F)(F)F)c2)[C@@H](c2ccc(F)cc2)c2c(C(=O)N(C)[C@H](C#N)C3COC3)nn(-c3ccccc3)c21]

$^1$H NMR (300 MHz, Chloroform-d) δ 8.04 (s, 1H), 7.93-7.78 (m, 2H), 7.68-7.53 (m, 5H), 7.06-6.93 (m, 4H), 6.86 (d, J = 6.2 Hz, 1H), 5.33 (t, J = 6.7 Hz, 1H), 5.15 (s, 1H), 4.86 (t, J = 7.3 Hz, 1H), 4.78-4.29 (m, 3H), 4.09-3.93 (m, 2H), 3.63-2.87 (m, 4H), 2.14-1.76 (m, 2H), 1.04 (t, J = 7.0 Hz, 3H).
LCMS Calculated for $C_{35}H_{30}F_4N_6O_4$: 674.20; Observed (Method-B): 675.1 [M + H] $^+$, 99.8% at RT 1.366 min.
Chiral HPLC (Method-F): 99.9% at RT 1.623 min.

I-294

-continued

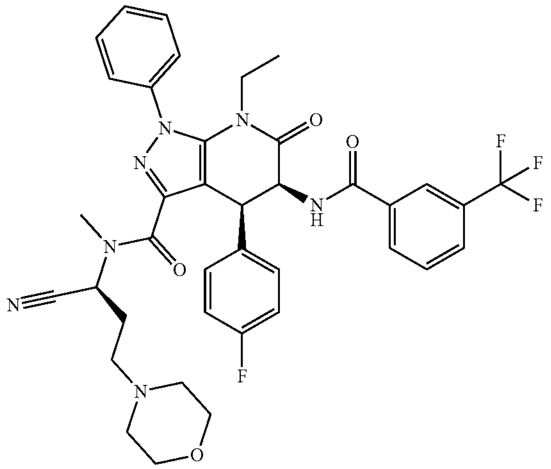 [SMILES: CCN1C(=O)[C@@H](NC(=O)c2cccc(C(F)(F)F)c2)[C@@H](c2ccc(F)cc2)c2c(C(=O)N(C)[C@H](C#N)CCN3CCOCC3)nn(-c3ccccc3)c21]

I-308

$^1$H NMR (400 MHz, DMSO-$d_6$) δ 8.58 (d, J = 7.0 Hz, 1H), 8.23-8.10 (m, 2H), 7.93 (d, J = 7.8 Hz, 1H), 7.81 (d, J = 7.4 Hz, 2H), 7.77-7.55 (m, 4H), 7.15-7.03 (m, 2H), 7.03-6.93 (m, 2H), 6.71-5.30 (m, 2H), 4.84 (d, J = 7.2 Hz, 1H), 3.89 (dt, J = 14.3, 7.2 Hz, 1H), 3.59-3.44 (m, 2H), 3.43-3.31 (m, 2H), 3.30-3.22 (m, 2H), 3.04 (dt, J = 13.9, 7.0 Hz, 1H), 2.99-2.86 (m, 1H), 2.35-1.99 (m, 8H), 0.92 (t, J = 7.0 Hz, 3H).
LCMS Calculated for $C_{38}H_{37}F_4N_7O_4$: 731.28; Observed (Method-E): 732.6 [M + H] $^+$, 99.6% at RT 1.523 min.

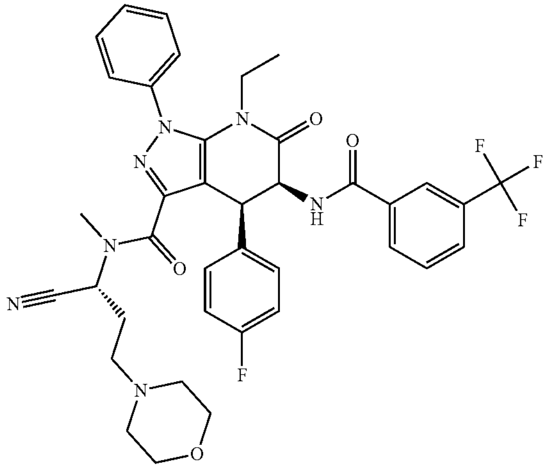 [SMILES: CCN1C(=O)[C@@H](NC(=O)c2cccc(C(F)(F)F)c2)[C@@H](c2ccc(F)cc2)c2c(C(=O)N(C)[C@@H](C#N)CCN3CCOCC3)nn(-c3ccccc3)c21]

I-309

$^1$H NMR (400 MHz, DMSO-$d_6$) δ 8.57 (d, J = 7.0 Hz, 1H), 8.20-8.09 (m, 2H), 7.93 (d, J = 7.8 Hz, 1H), 7.85-7.78 (m, 2H), 7.76-7.56 (m, 4H), 7.13-7.06 (m, 2H), 7.02-6.91 (m, 2H), 6.49-5.34 (m, 2H), 5.06-4.68 (m, 1H), 3.91 (s, 1H), 3.53 (s, 2H), 3.29-3.19 (m, 3H), 3.11-2.99 (m, 1H), 2.95 (s, 2H), 2.41-2.16 (m, 3H), 2.20-1.85 (m, 5H), 0.92 (t, J = 7.1 Hz, 3H).
LCMS Calculated for $C_{38}H_{37}F_4N_7O_4$: 731.28; Observed (Method-E): 732.6 [M + H] $^+$, 98.7% at RT 1.528 min.

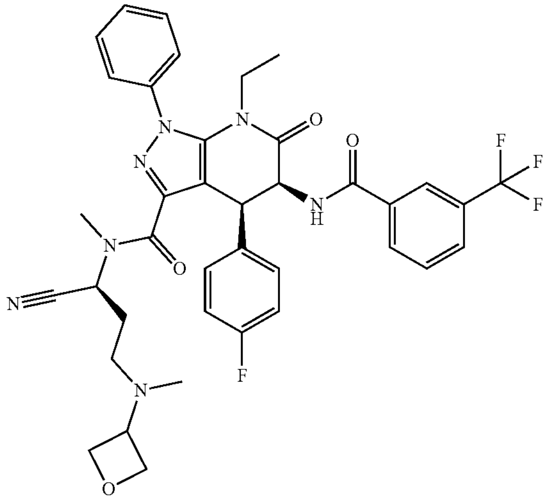 [SMILES: CCN1C(=O)[C@@H](NC(=O)c2cccc(C(F)(F)F)c2)[C@@H](c2ccc(F)cc2)c2c(C(=O)N(C)[C@H](C#N)CCN(C)C3COC3)nn(-c3ccccc3)c21]

I-310

$^1$H NMR (400 MHz, DMSO-$d_6$) δ 8.56 (d, J = 7.2 Hz, 1H), 8.20-8.11 (m, 2H), 7.93 (d, J = 7.8 Hz, 1H), 7.82 (s, 2H), 7.72 (t, J = 7.8 Hz, 1H), 7.69-7.57 (m, 3H), 7.09 (t, J = 8.8 Hz, 2H), 7.04-6.94 (m, 2H), 6.68-5.43 (m, 2H), 5.05-4.71 (m, 1H), 4.52-4.38 (m, 2H), 4.38-4.13 (m, 2H), 3.98-3.81 (m, 1H), 3.46-3.36 (m, 1H), 3.32-3.22 (m, 2H), 3.11-2.99 (m, 1H), 2.95 (s, 1H), 2.37-1.92 (m, 5H), 1.92-1.64 (m, 2H), 0.91 (t, J = 7.1 Hz, 3H).
LCMS Calculated for $C_{38}H_{37}F_4N_7O_4$: 731.28; Observed (Method-E): 732.6 [M + H] $^+$, 96.2% at RT 1.619 min.

-continued

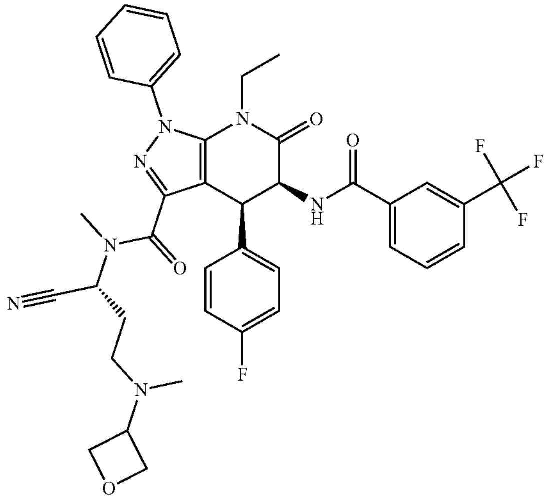 [SMILES: CCN1C(=O)[C@@H](NC(=O)c2cccc(C(F)(F)F)c2)[C@@H](c2ccc(F)cc2)c2c(C(=O)N(C)[C@@H](C#N)CCN(C)C3COC3)nn(-c3ccccc3)c21]

$^1$H NMR (400 MHz, DMSO-$d_6$) δ 8.54 (s, 1H), 8.19-8.09 (m, 2H), 7.90 (d, J = 7.8 Hz, 1H), 7.79 (d, J = 7.4 Hz, 2H), 7.70 (t, J = 7.8 Hz, 1H), 7.66-7.54 (m, 3H), 7.06 (t, J = 8.6 Hz, 2H), 6.95 (s, 2H), 6.53-6.28 (m, 1H), 5.63-5.48 (m, 1H), 4.87 (d, J = 7.2 Hz, 1H), 4.55-3.97 (m, 4H), 3.89 (s, 1H), 3.53-3.29 (m, 3H), 3.02 (dd, J = 14.2, 7.0 Hz, 1H), 2.93 (s, 1H), 2.28-1.57 (m, 7H), 0.89 (t, J = 7.0 Hz, 3H).
LCMS Calculated for $C_{38}H_{37}F_4N_7O_4$: 731.28; Observed (Method-E): 732.5 [M + H] $^+$, 99.8% at RT 1.626 min.

I-311

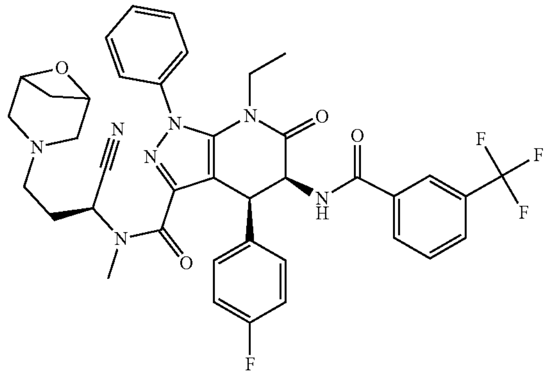 [SMILES: CCN1C(=O)[C@@H](NC(=O)c2cccc(C(F)(F)F)c2)[C@@H](c2ccc(F)cc2)c2c(C(=O)N(C)[C@H](C#N)CCN3CC4CC(C3)O4)nn(-c3ccccc3)c21]

$^1$H NMR (400 MHz, DMSO-$d_6$) δ 8.58 (s, 1H), 8.26-8.07 (m, 2H), 7.93 (d, J = 7.8 Hz, 1H), 7.87-7.69 (m, 3H), 7.69-7.55 (m, 3H), 7.08 (t, J = 8.8 Hz, 2H), 6.97 (dd, J = 8.5, 5.5 Hz, 2H), 6.71-5.18 (m, 2H), 4.81 (s, 1H), 4.48-4.18 (m, 2H), 3.88 (dq, J = 14.1, 6.9 Hz, 1H), 3.12-2.88 (m, 4H), 2.89-2.65 (m, 2H), 2.57-2.51 (m, 2H), 2.49-2.37 (m, 3H), 2.25-1.51 (m, 3H), 0.90 (t, J = 7.0 Hz, 3H).
LCMS Calculated for $C_{39}H_{37}F_4N_7O_4$: 743.28; Observed (Method-E): 744.6 [M + H] $^+$, 98.2% at RT 1.541 min.

I-312

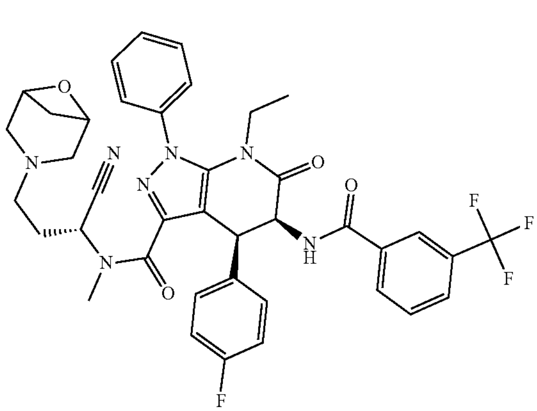 [SMILES: CCN1C(=O)[C@@H](NC(=O)c2cccc(C(F)(F)F)c2)[C@@H](c2ccc(F)cc2)c2c(C(=O)N(C)[C@@H](C#N)CCN3CC4CC(C3)O4)nn(-c3ccccc3)c21]

$^1$H NMR (400 MHz, DMSO-$d_6$) δ 8.52 (s, 1H), 8.19-8.05 (m, 2H), 7.90 (d, J = 7.8 Hz, 1H), 7.82-7.54 (m, 6H), 7.11-7.02 (m, 2H), 7.00-6.85 (m, 2H), 6.52-6.35 (m, 1H), 5.66-5.45 (m, 1H), 5.06-4.77 (m, 1H), 4.44-4.26 (m, 1H), 4.00-3.74 (m, 2H), 3.12-2.70 (m, 5H), 2.69-2.53 (m, 2H), 2.46-2.26 (m, 3H), 2.28-1.49 (m, 4H), 0.89 (t, J = 7.1 Hz, 3H).
LCMS Calculated for $C_{39}H_{37}F_4N_7O_4$: 743.28; Observed (Method-E): 744.5 [M + H] $^+$, 99.8% at RT 1.534 min.

I-313

-continued

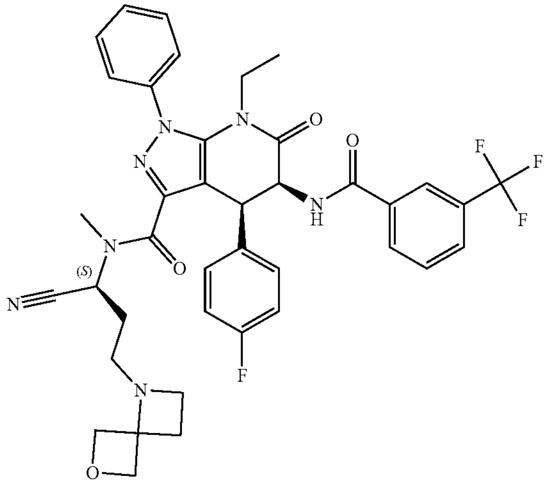

$^1$H NMR (300 MHz, DMSO-$d_6$) δ 8.58 (d, J = 7.2 Hz, 1H), 8.15 (d, J = 10.3 Hz, 2H), 7.98-7.55 (m, 7H), 7.09 (t, J = 8.7 Hz, 2H), 6.99 (d, J = 6.1 Hz, 2H), 5.49 (d, J = 28.5 Hz, 2H), 4.84 (d, J = 21.1 Hz, 1H), 4.49 (d, J = 22.5 Hz, 4H), 3.89 (dd, J = 15.0, 7.6 Hz, 1H), 3.25-2.81 (m, 8H), 2.37-1.68 (m, 4H), 0.91 (t, J = 7.0 Hz, 3H). LCMS Calculated for $C_{39}H_{37}F_4N_7O_4$: 743.28; Observed (Method-H): 744.2 [M + H] $^+$, 97.1% at RT 2.461 min.

I-314

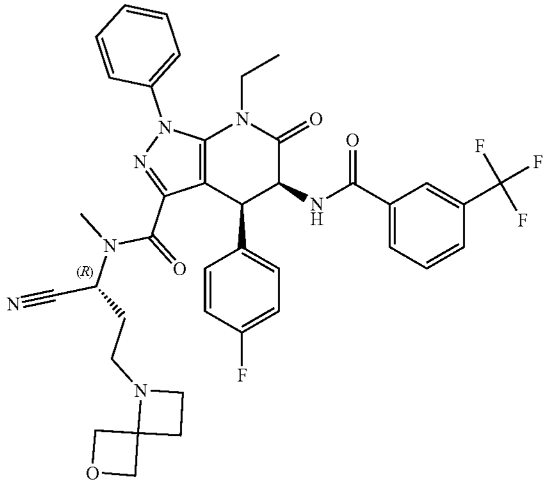

$^1$H NMR (400 MHz, DMSO-$d_6$) δ 8.55 (d, J = 7.2 Hz, 1H), 8.18-8.06 (m, 2H), 7.90 (d, J = 7.8 Hz, 1H), 7.79 (d, J = 7.5 Hz, 2H), 7.74-7.55 (m, 4H), 7.08 (t, J = 8.7 Hz, 2H), 6.95 (dd, J = 8.4, 5.4 Hz, 2H), 6.15 (s, 1H), 5.48 (d, J = 55.1 Hz, 1H), 4.85 (d, J = 7.2 Hz, 1H), 4.61-4.33 (m, 4H), 3.98-3.80 (m, 1H), 3.19 (s, 4H), 3.03 (d, J = 18.3 Hz, 2H), 2.88 (s, 2H), 2.26 (s, 1H), 2.11-1.95 (m, 1H), 1.90-1.70 (m, 2H), 0.91 (t, J = 6.7 Hz, 3H). LCMS Calculated for $C_{39}H_{37}F_4N_7O_4$: 743.28; Observed (Method-H): 744.2 [M + H] $^+$, 95.8% at RT 2.186 min.

I-315

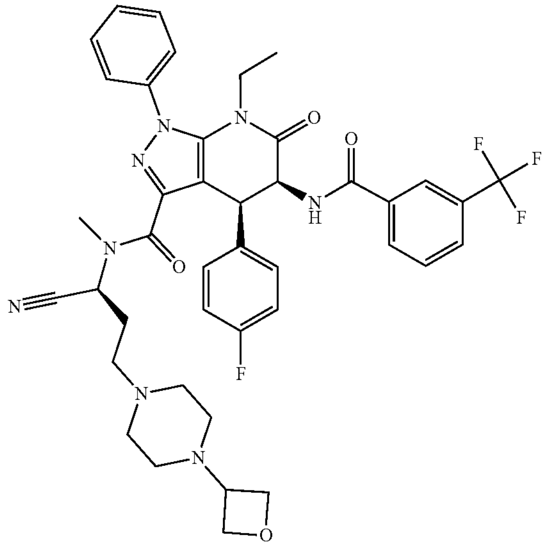 [SMILES: CCN1C(=O)[C@@H](NC(=O)c2cccc(C(F)(F)F)c2)[C@@H](c2ccc(F)cc2)c2c(C(=O)N(C)[C@H](C#N)CCN3CCN(C4COC4)CC3)nn(-c3ccccc3)c21]

$^1$H NMR (300 MHz, DMSO-$d_6$) δ 8.58 (d, J = 7.2 Hz, 1H), 8.15 (d, J = 10.4 Hz, 2H), 7.92 (d, J = 7.9 Hz, 1H), 7.84-7.76 (m, 2H), 7.75-7.57 (m, 4H), 7.08 (t, J = 8.7 Hz, 2H), 6.96 (dd, J = 8.3, 5.5 Hz, 2H), 5.52 (s, 2H), 4.84 (s, 1H), 4.50 (t, J = 6.5 Hz, 2H), 4.35 (s, 2H), 3.89 (dd, J = 14.3, 7.4 Hz, 1H), 3.15-2.88 (m, 5H), 2.45-1.54 (m, 12H), 0.90 (t, J = 7.1 Hz, 3H). LCMS Calculated for $C_{41}H_{42}F_4N_8O_4$: 786.33; Observed (Method-H): 787.2 [M + H] $^+$, 99.3% at RT 2.42 min.

I-316

-continued

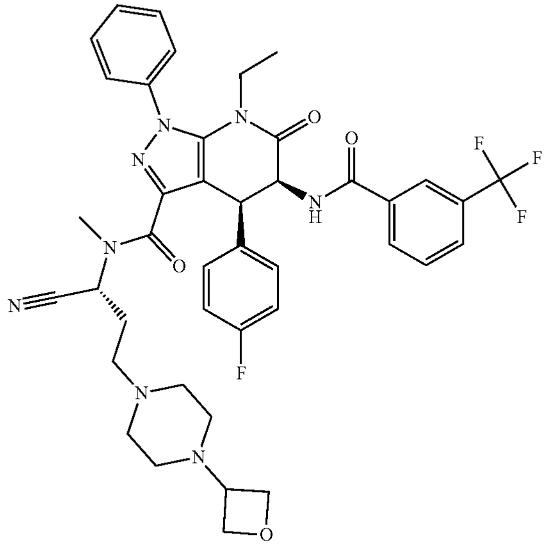 [SMILES: CCN1C(=O)[C@@H](NC(=O)c2cccc(C(F)(F)F)c2)[C@@H](c2ccc(F)cc2)c2c(C(=O)N(C)[C@@H](C#N)CCN3CCN(C4COC4)CC3)nn(-c3ccccc3)c21]

I-317

$^1$H NMR (300 MHz, DMSO-$d_6$) δ 8.58 (s, 1H), 8.14 (d, J = 9.2 Hz, 2H), 7.92 (d, J = 7.8 Hz, 1H), 7.80 (d, J = 6.6 Hz, 2H), 7.75-7.58 (m, 4H), 7.08 (t, J = 8.7 Hz, 2H), 6.95 (s, 2H), 5.57 (s, 2H), 4.88 (s, 1H), 4.47 (t, J = 6.2 Hz, 2H), 4.34 (s, 2H), 3.94-3.78 (m, 1H), 3.21-2.88 (m, 4H), 2.47-1.73 (m, 12H), 0.90 (t, J = 7.0 Hz, 3H). LCMS Calculated for $C_{41}H_{42}F_4N_8O_4$: 786.33; Observed (Method-H): 787.2 [M + H] $^+$, 96.9% at RT 2.367.

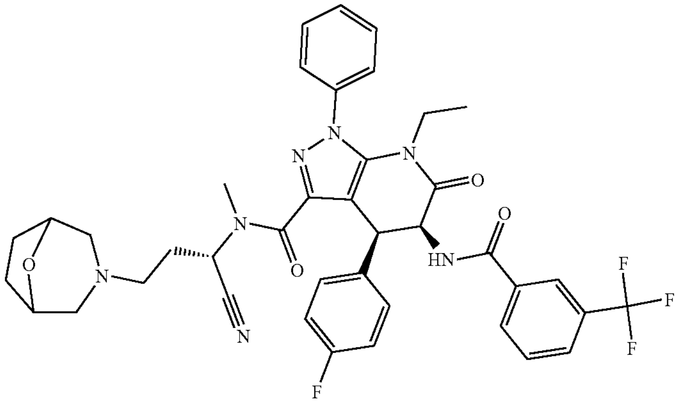 [SMILES: CCN1C(=O)[C@@H](NC(=O)c2cccc(C(F)(F)F)c2)[C@@H](c2ccc(F)cc2)c2c(C(=O)N(C)[C@H](C#N)CCN3CC4CCC(C3)O4)nn(-c3ccccc3)c21]

I-318

$^1$H NMR (400 MHz, DMSO-$d_6$) δ 8.58 (s, 1H), 8.30-8.09 (m, 2H), 7.93 (d, J = 7.8 Hz, 1H), 7.70 (ddt, J = 40.8, 14.9, 7.2 Hz, 6H), 7.09 (t, J = 8.7 Hz, 2H), 6.98 (d, J = 7.6 Hz, 2H), 5.84-5.24 (m, 2H), 4.83 (d, J = 16.8 Hz, 1H), 4.09 (d, J = 22.8 Hz, 2H), 3.90 (dt, J = 14.6, 7.3 Hz, 1H), 3.17 (s, 1H), 3.05 (dd, J = 14.5, 7.3 Hz, 1H), 2.92 (s, 1H), 2.47 (s, 1H), 2.42-1.91 (m, 7H), 1.91-1.72 (m, 2H), 1.71-1.41 (m, 3H), 0.91 (t, J = 7.0 Hz, 3H). LCMS Calculated for $C_{40}H_{39}F_4N_7O_4$: 757.30; Observed (Method-C): 758.2 [M + H] $^+$, 99.4% at RT 1.085 min.

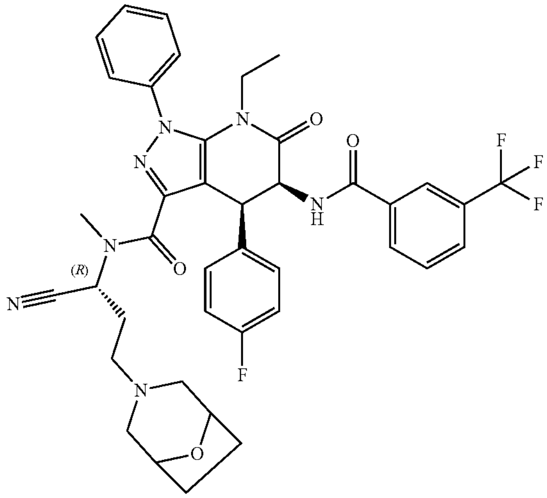

I-319

$^1$H NMR (300 MHz, DMSO-$d_6$) δ 8.58 (s, 1H), 8.13 (d, J = 8.4 Hz, 2H), 7.92 (d, J = 7.8 Hz, 1H), 7.84-7.55 (m, 6H), 7.09 (t, J = 8.7 Hz, 2H), 6.96 (dd, J = 8.5, 5.4 Hz, 2H), 5.59 (s, 2H), 5.08-4.74 (m, 1H), 4.12 (d, J = 17.2 Hz, 1H), 3.88 (dd, J = 14.7, 7.6 Hz, 1H), 3.64-3.50 (m, 1H), 3.15-2.86 (m, 3H), 2.48-1.50 (m, 11H), 1.34-1.10 (m, 1H), 0.91 (t, J = 7.0 Hz, 3H). LCMS Calculated for: $C_{40}H_{39}F_4N_7O_4$: 757.30; Observed (Method-F): 758.2 [M + H] $^+$, 99.8% at RT 1.444 min.

-continued

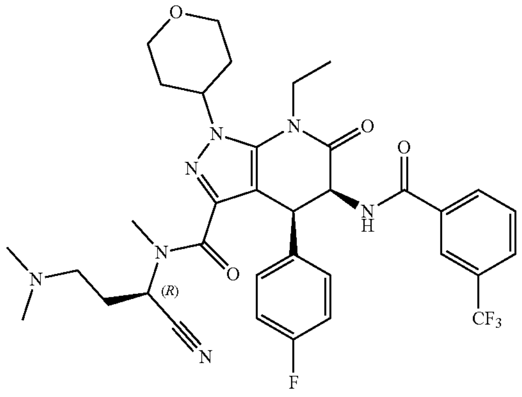

I-369

$^1$H NMR (400 MHz, Acetonitrile-$d_3$) δ 8.02 (s, 1H), 7.96 (d, J = 7.9 Hz, 1H), 7.86 (d, J = 7.8 Hz, 1H), 7.65 (t, J = 7.8 Hz, 1H), 7.14 (s, 1H), 6.98 (d, J = 7.1 Hz, 4H), 6.67-5.48 (m, 1H), 5.12 (s, 1H), 5.07-4.90 (m, 1H), 4.59-4.46 (m, 1H), 4.19-3.93 (m, 4H), 3.69-3.47 (m, 2H), 3.37 (s, 1H), 2.98 (s, 2H), 2.55-2.23 (m, 9H), 2.24-2.12 (m, 5H), 1.39 (t, J = 7.1 Hz, 3H). LCMS Calculated for $C_{35}H_{39}F_4N_7O_4$: 697.30; Observed (Method-A): 698.4 [M + H] $^+$, 99.4% at RT 1.208 min.

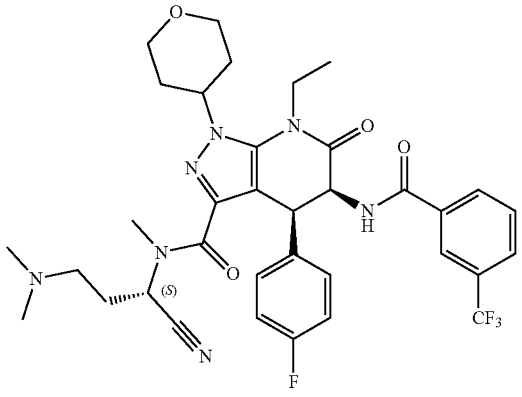

I-370

$^1$H NMR (400 MHz, Acetonitrile-$d_3$) δ 8.02 (s, 1H), 7.95 (d, J = 7.8 Hz, 1H), 7.86 (d, J = 7.8 Hz, 1H), 7.65 (t, J = 7.8 Hz, 1H), 7.14 (d, J = 6.5 Hz, 1H), 6.99 (d, J = 7.2 Hz, 4H), 6.70-5.46 (m, 1H), 5.09 (s, 1H), 4.87 (d, J = 6.9 Hz, 1H), 4.53 (s, 1H), 4.19-4.07 (m, 1H), 4.07-3.93 (m, 3H), 3.71-3.46 (m, 2H), 3.37 (s, 1H), 2.96 (s, 2H), 2.56-2.40 (m, 2H), 2.19-2.12 (m, 10H), 2.12-2.03 (m, 2H), 1.40 (t, J = 7.0 Hz, 3H). LCMS Calculated for $C_{35}H_{39}F_4N_7O_4$: 697.30; Observed (Method-A): 698.4 [M + H] $^+$, 99.1% at RT 1.214 min.

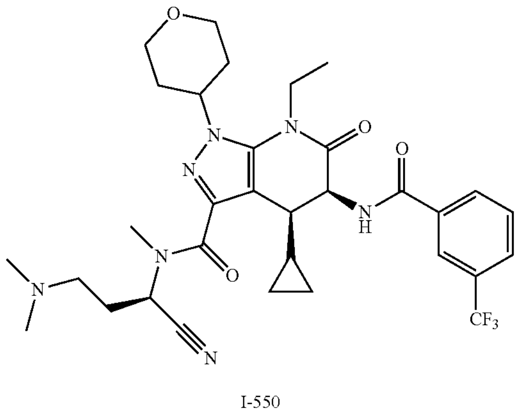

I-550

$^1$H NMR (300 MHz, DMSO-$d_6$) δ 9.03 (d, J = 8.0 Hz, 1H), 8.30 (s, 1H), 8.24 (d, J = 7.8 Hz, 1H), 7.96 (d, J = 7.8 Hz, 1H), 7.76 (t, J = 7.8 Hz, 1H), 6.44-5.44 (m, 1H), 5.05 (s, 1H), 4.50 (s, 1H), 4.18-3.78 (m, 4H), 3.67-3.40 (m, 2H), 3.23 (t, J = 6.3 Hz, 2H), 2.99 (s, 2H), 2.42-1.82 (m, 14H), 1.27 (s, 3H), 0.83 (s, 1H), 0.46 (t, J = 8.5 Hz, 1H), 0.28-0.05 (m, 3H). LCMS Calculated for $C_{32}H_{40}F_3N_7O_4$: 643.31; Observed (Method-I): 644.4 [M + H] $^+$, 99.8% at RT 1.969 min. Chiral SFC (Method-B): 91.52% at RT 1.05 min.

-continued

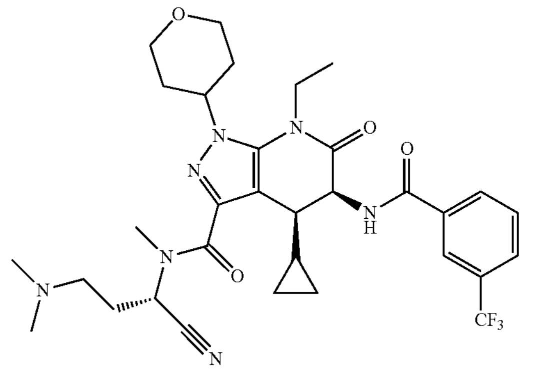 [SMILES: CCN1C(=O)[C@@H](NC(=O)c2cccc(C(F)(F)F)c2)[C@@H](C2CC2)c2c(C(=O)N(C)[C@H](C#N)CCN(C)C)nn(C3CCOCC3)c21]

I-589

$^{1}$H NMR (300 MHz, DMSO-$d_6$) δ 9.03 (d, J = 8.0 Hz, 1H), 8.30 (s, 1H), 8.24 (d, J = 7.8 Hz, 1H), 7.96 (d, J = 7.8 Hz, 1H), 7.76 (t, J = 7.8 Hz, 1H), 6.44-5.44 (m, 1H), 5.05 (s, 1H), 4.50 (s, 1H), 4.18-3.78 (m, 4H), 3.67-3.40 (m, 2H), 3.23 (t, J = 6.3 Hz, 2H), 2.99 (s, 2H), 2.42-1.82 (m, 14H), 1.27 (s, 3H), 0.83 (s, 1H), 0.46 (t, J = 8.5 Hz, 1H), 0.28-0.05 (m, 3H).
LCMS Calculated for $C_{32}H_{40}F_3N_7O_4$: 643.31; Observed (Method-I): 644.4 [M + H] $^+$, 99.9% at RT 1.946 min.
Chiral SFC (Method-B): 84.78% at RT 1.11 min.

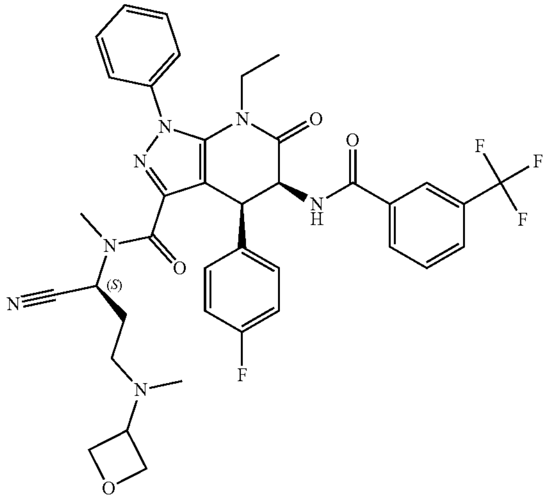

I-470

$^{1}$H NMR (400 MHz, Acetonitrile-$d_3$) δ 8.02 (s, 1H), 7.95 (d, J = 7.9 Hz, 1H), 7.86 (d, J = 7.8 Hz, 1H), 7.65 (t, J = 7.8 Hz, 1H), 7.17-7.07 (m, 1H), 6.99 (d, J = 7.2 Hz, 4H), 6.70-5.46 (m, 1H), 5.12 (t, J = 6.6 Hz, 1H), 4.90 (d, J = 7.0 Hz, 1H), 4.64-4.42 (m, 3H), 4.36 (s, 2H), 4.12 (s, 1H), 4.02 (d, J = 7.2 Hz, 3H), 3.71-3.41 (m, 3H), 3.37 (s, 1H), 3.05-2.85 (m, 2H), 2.58-2.36 (m, 1H), 2.35-2.27 (m, 2H), 2.23-2.17 (m, 4H), 2.07-1.98 (m, 4H), 1.40 (t, J = 7.1 Hz, 3H).
LCMS Calculated for $C_{37}H_{41}F_4N_7O_5$: 739.31; Observed (Method-K): 740.6 [M + H] $^+$, 99.3% at RT 1.505 min.

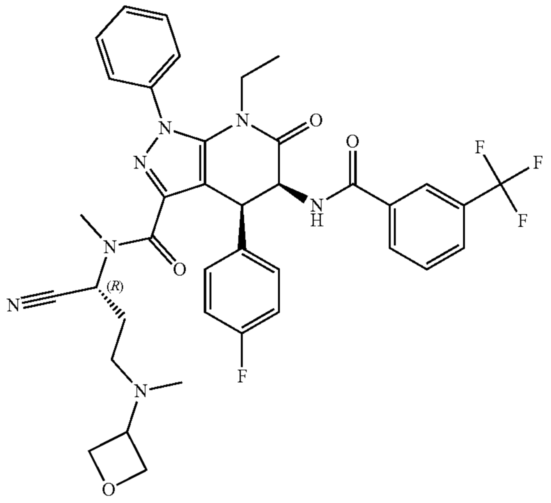

I-654

$^{1}$H NMR (400 MHz, Acetonitrile-$d_3$) δ 8.02 (s, 1H), 7.96 (d, J = 7.8 Hz, 1H), 7.86 (d, J = 7.8 Hz, 1H), 7.65 (t, J = 7.8 Hz, 1H), 7.15 (d, J = 6.4 Hz, 1H), 7.03-6.95 (m, 4H), 6.71-5.50 (m, 1H), 5.13 (s, 1H), 5.09-4.92 (m, 1H), 4.65-4.17 (m, 5H), 4.18-3.93 (m, 4H), 3.69-3.41 (m, 3H), 3.39-2.92 (m, 3H), 2.56-2.32 (m, 1H), 2.28-2.20 (m, 2H), 2.19-2.09 (m, 5H), 2.09-2.02 (m, 3H), 1.39 (t, J = 7.1 Hz, 3H).
LCMS Calculated for $C_{37}H_{41}F_4N_7O_5$: 739.31; Observed (Method-K): 740.6 [M + H] $^+$, 99.8% at RT 1.504 min.

-continued

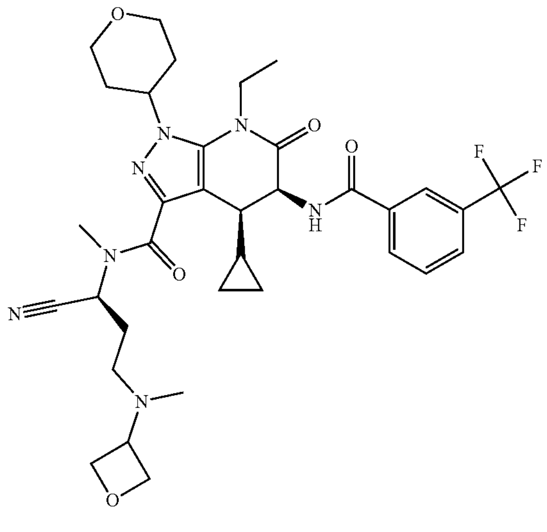 [SMILES: CCN1C(=O)[C@@H](NC(=O)c2cccc(C(F)(F)F)c2)[C@@H](C2CC2)c2c(C(=O)N(C)[C@H](C#N)CCN(C)C3COC3)nn(C3CCOCC3)c21]

I-429

$^1H$ NMR (300 MHz, DMSO-$d_6$) δ 9.06-8.99 (m, 1H), 8.30 (s, 1H), 8.24 (d, J = 7.7 Hz, 1H), 7.96 (d, J = 7.8 Hz, 1H), 7.76 (t, J = 7.8 Hz, 1H), 6.37-5.47 (m, 1H), 5.14-4.98 (m, 1H), 4.51 (t, J = 6.6 Hz, 3H), 4.47-4.26 (m, 2H), 4.18-3.78 (m, 4H), 3.64-3.42 (m, 3H), 3.25 (s, 1H), 3.07-2.93 (m, 1H), 2.40-1.82 (m, 12H), 1.40-1.16 (m, 4H), 0.93-0.73 (m, 1H), 0.56-0.40 (m, 1H), 0.27-0.15 (m, 1H), 0.13-0.01 (m, 2H). LCMS Calculated for $C_{34}H_{42}F_3N_7O_5$: 685.32; Observed (Method-I): 686.5 [M + H] $^+$, 99.5% at RT 1.818 min. Chiral SFC (Method-B): 99.74% at RT 1.14 min.

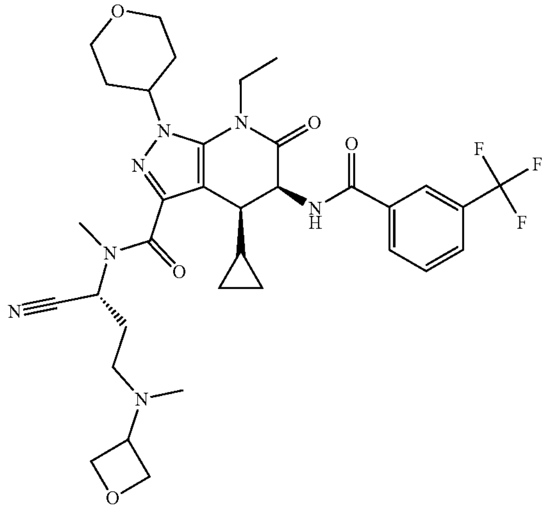 [SMILES: CCN1C(=O)[C@@H](NC(=O)c2cccc(C(F)(F)F)c2)[C@@H](C2CC2)c2c(C(=O)N(C)[C@@H](C#N)CCN(C)C3COC3)nn(C3CCOCC3)c21]

I-664

$^1H$ NMR (300 MHz, DMSO-$d_6$) δ 9.06-8.99 (m, 1H), 8.30 (s, 1H), 8.24 (d, J = 7.7 Hz, 1H), 7.96 (d, J = 7.8 Hz, 1H), 7.76 (t, J = 7.8 Hz, 1H), 6.37-5.47 (m, 1H), 5.14-4.98 (m, 1H), 4.61-3.78 (m, 9H), 3.64-3.42 (m, 3H), 3.40-3.21 (m, 3H), 3.12-2.95 (m, 1H), 2.43-1.87 (m, 11H), 1.35-1.18 (m, 3H), 0.89-0.75 (m, 1H), 0.55-0.45 (m, 1H), 0.30-0.11 (m, 1H), 0.10--0.89 (m, 2H). LCMS Calculated for $C_{34}H_{42}F_3N_7O_5$: 685.32; Observed (Method-I): 686.4 [M + H] $^+$, 99.9% at RT 1.807 min. Chiral SFC (Method-B): 97.16% at RT 1.20 min.

3. Synthesis of N-((4R,5R)-3-((S)-2-cyanopyrrolidine-1-carbonyl)-7-ethyl-4-(4-fluorophenyl)-1-(3-(3-(methyl(oxetan-3-yl)amino)propoxy)phenyl)-6-oxo-4,5,6,7-tetrahydro-1H-pyrazolo[3,4-b]pyridin-5-yl)-3-(trifluoromethyl)benzamide (I-480)

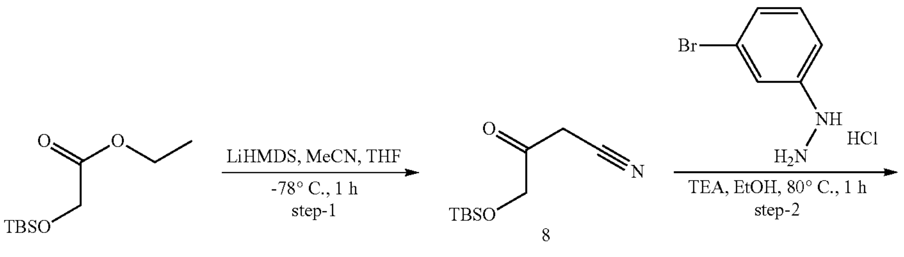

-continued
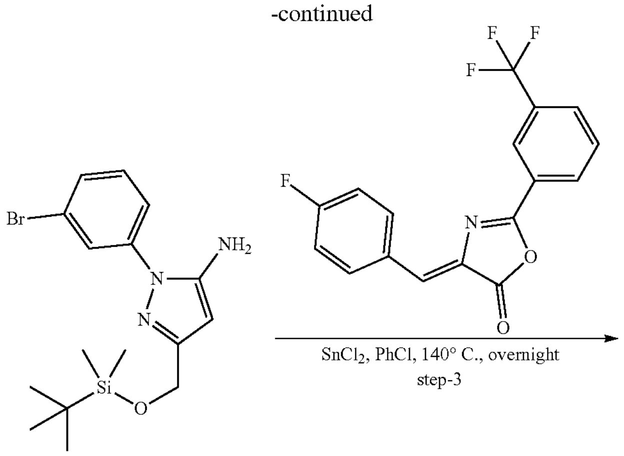
9
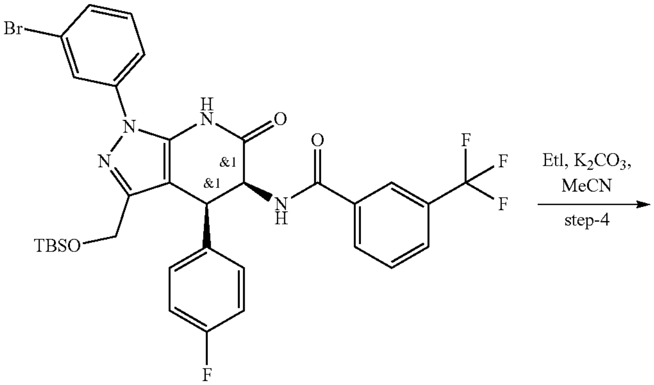
10
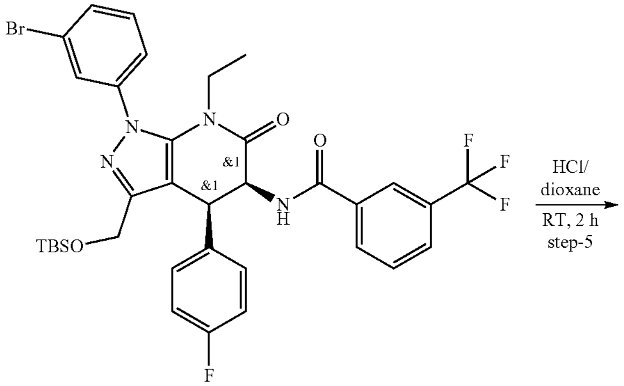
11
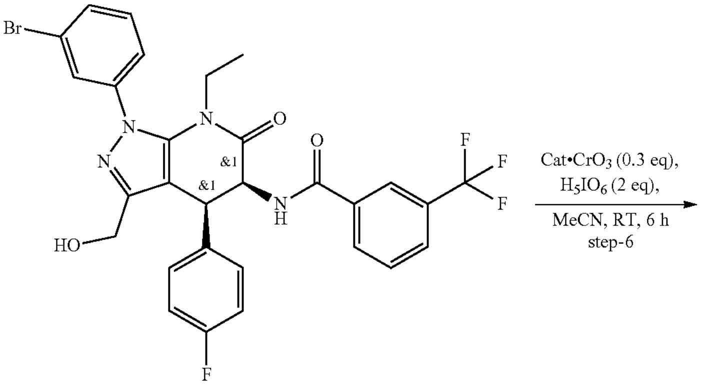
12

-continued
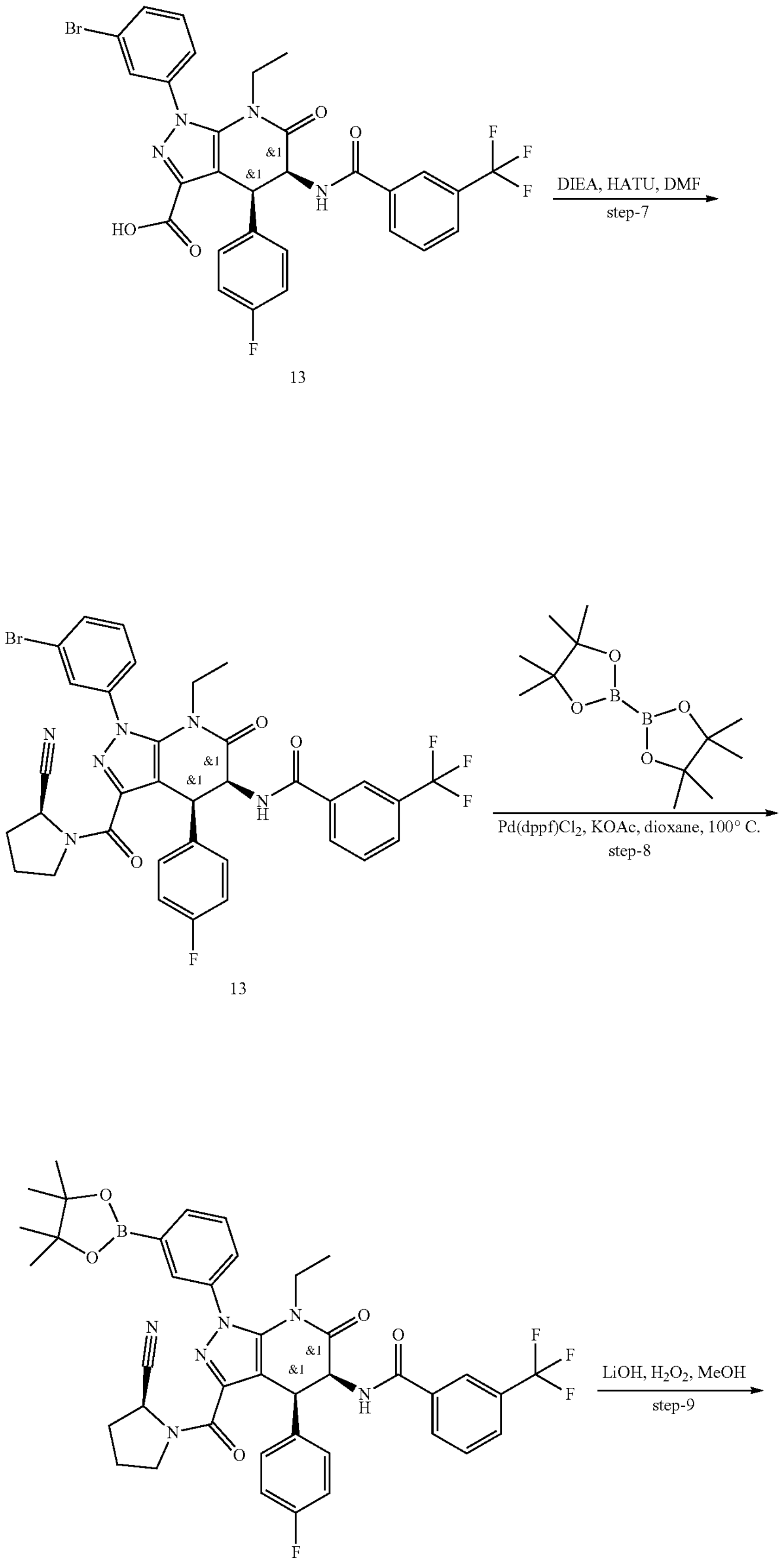
13
13
15

-continued
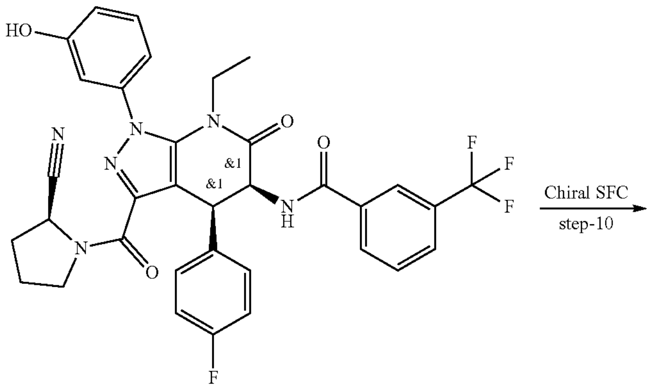
16
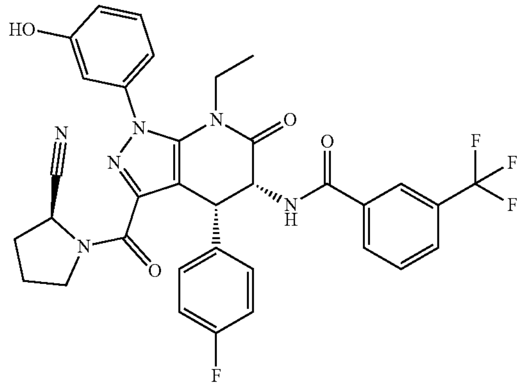
17A
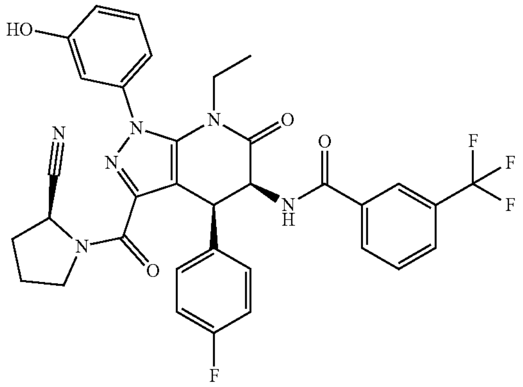
17B
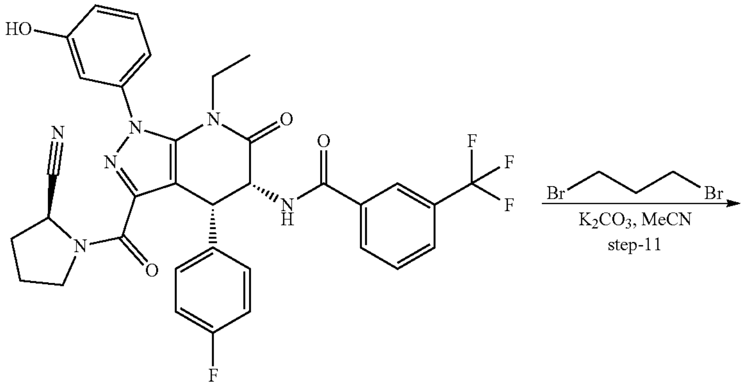
17A

-continued

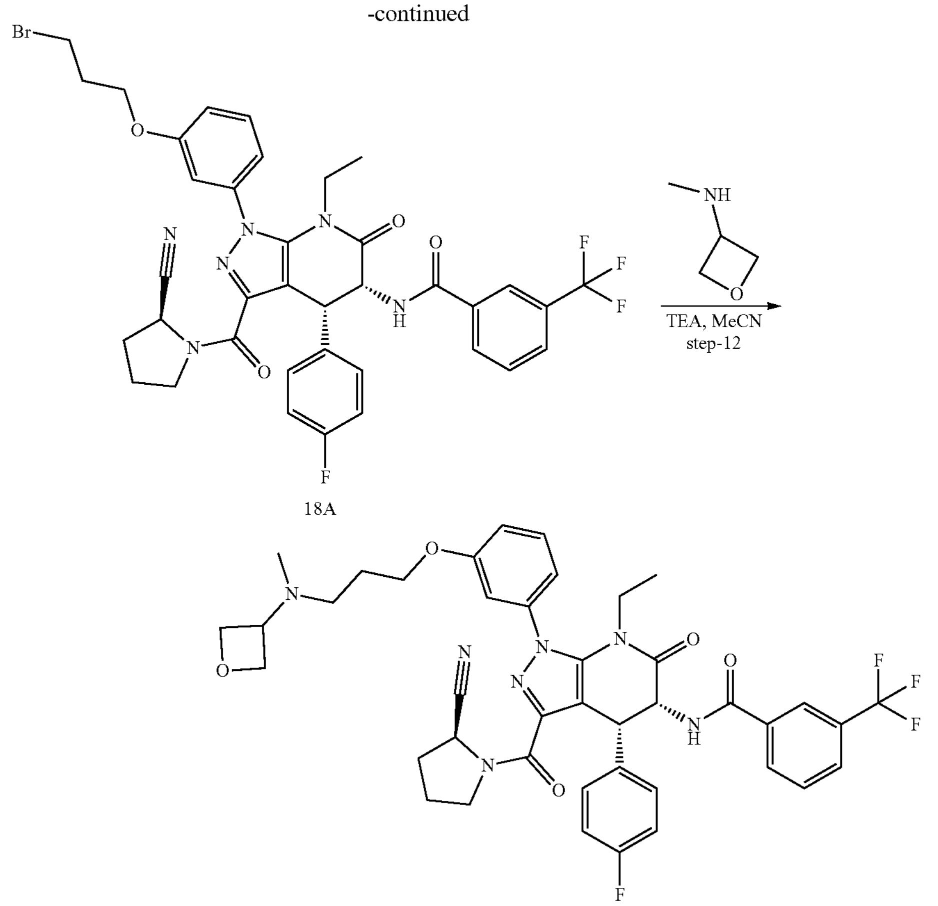

18A

I-480

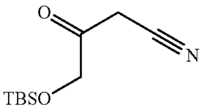

4-[(tert-butyldimethylsilyl)oxy]-3-oxobutanenitrile (8)

A solution of MeCN (11.3 g, 275 mmol, 1.20 equiv) in THF (500 mL) was treated with LiHMDS (59.6 mL, 298 mmol, 1.30 equiv) for 0.5 h at −78° C. under nitrogen atmosphere followed by the addition of ethyl 2-[(tert-butyldimethylsilyl)oxy]acetate (50.0 g, 229 mmol, 1.00 equiv) dropwise at −78° C. The resulting mixture was stirred for 1 h at room temperature under nitrogen atmosphere. The reaction was quenched with sat. $NH_4Cl$ (aq.) at room temperature. The resulting mixture was extracted with EtOAc (2×500 mL). The combined organic layers were washed with brine (2×500 mL), dried over anhydrous $Na_2SO_4$. After filtration, the filtrate was concentrated under reduced pressure. This resulted in 4-[(tert-butyldimethylsilyl)oxy]-3-oxobutanenitrile (48 g, 98%) as a yellow solid. The crude product was used in the next step directly without further purification.

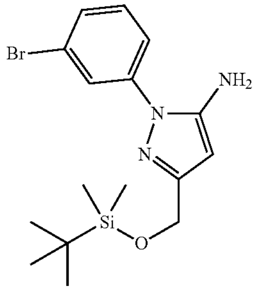

2-(3-bromophenyl)-5-([(tert-butyldimethylsilyl)oxy]methylpyrazol-3-amine (9)

To a stirred solution of 4-[(tert-butyldimethylsilyl)oxy]-3-oxobutanenitrile (48.0 g, 225 mmol, 1.00 equiv) and TEA (45.5 g, 450 mmol, 2.00 equiv) in EtOH (500 mL) was added (3-bromophenyl) hydrazine (42.1 g, 225 mmol, 1.00 equiv) dropwise at room temperature under nitrogen atmosphere. The resulting mixture was stirred at 80° C. for 1 h under nitrogen atmosphere. The resulting mixture was concentrated under reduced pressure. The mixture was allowed to cool down to room temperature. The resulting mixture was extracted with EtOAc (2×500 mL). The combined organic layers were washed with brine (2×500 mL), dried over anhydrous $Na_2SO_4$. After filtration, the filtrate was concentrated under reduced pressure. The residue was purified by silica gel column chromatography, eluted with petroleum ether/ethyl acetate (1:1) to afford 2-(3-bromophenyl)-5-([(tert-butyldimethylsilyl)oxy]methylpyrazol-3-amine (35.0 g, 40.7%) as a yellow solid.

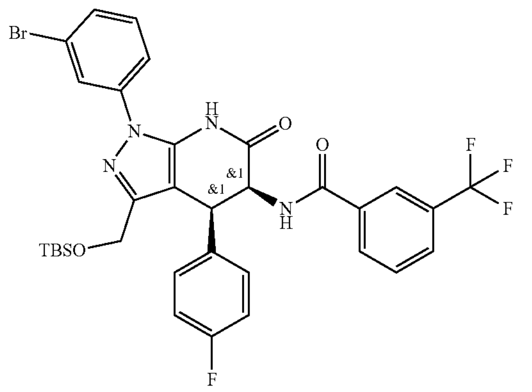

rac-N-((4R,5R)-1-(3-bromophenyl)-3-(((tert-butyldimethylsilyl)oxy)methyl)-4-(4-fluorophenyl)-6-oxo-4,5,6,7-tetrahydro-1H-pyrazolo[3,4-b]pyridin-5-yl)-3-(trifluoromethyl)benzamide (10)

To a stirred solution of 2-(3-bromophenyl)-5-([(tert-butyldimethylsilyl)oxy]methylpyrazol-3-amine (35.0 g, 91.5 mmol, 1.00 equiv) and $SnCl_2$ (3.51 g, 18.3 mmol, 0.200 equiv) in Ph-Cl (400 mL) was added (4Z)-4-[(4-fluorophenyl)methylidene]-2-[3-(trifluoromethyl)phenyl]-1,3-oxazol-5-one (33.8 g, 101 mmol, 1.10 equiv) dropwise at room temperature under nitrogen atmosphere. The resulting mixture was stirred at 140° C. overnight under nitrogen atmosphere. The mixture was allowed to cool down to room temperature. The resulting mixture was concentrated under reduced pressure. The residue was purified by silica gel column chromatography, eluted with petroleum ether/ethyl acetate (1:1) to afford rac-N-((4R,5R)-1-(3-bromophenyl)-3-(((tert-butyldimethylsilyl)oxy)methyl)-4-(4-fluorophenyl)-6-oxo-4,5,6,7-tetrahydro-1H-pyrazolo[3,4-b]pyridin-5-yl)-3-(trifluoromethyl)benzamide (20.0 g, 30%) as a white solid.

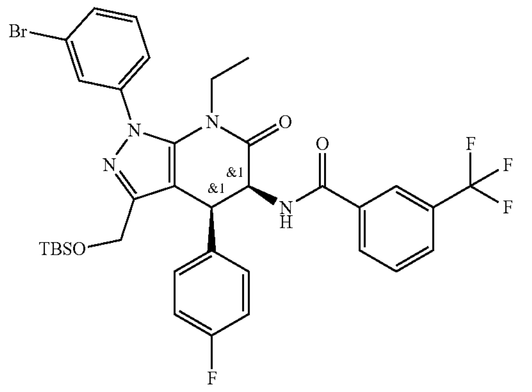

rac-N-((4R,5R)-1-(3-bromophenyl)-3-(((tert-butyldimethylsilyl)oxy)methyl)-7-ethyl-4-(4-fluorophenyl)-6-oxo-4,5,6,7-tetrahydro-1H-pyrazolo[3,4-b]pyridin-5-yl)-3-(trifluoromethyl)benzamide (11)

To a stirred solution of rac-N-((4R,5R)-1-(3-bromophenyl)-3-(((tert-butyldimethylsilyl)oxy)methyl)-4-(4-fluorophenyl)-6-oxo-4,5,6,7-tetrahydro-1H-pyrazolo[3,4-b]pyridin-5-yl)-3-(trifluoromethyl)benzamide (20.0 g, 27.9 mmol, 1.00 equiv) and $K_3PO_4$ (11.8 g, 55.7 mmol, 2.00 equiv) in ACN (200 mL) was added bromoethane (3.64 g, 33.4 mmol, 1.20 equiv) dropwise at room temperature under nitrogen atmosphere. The resulting mixture was stirred at 80° C. overnight under nitrogen atmosphere. The mixture was allowed to cool down to room temperature. The resulting mixture was concentrated under reduced pressure. The residue was purified by silica gel column chromatography, eluted with petroleum ether/ethyl acetate (1:1) to afford rac-N-((4R,5R)-1-(3-bromophenyl)-3-(((tert-butyldimethylsilyl)oxy)methyl)-7-ethyl-4-(4-fluorophenyl)-6-oxo-4,5,6,7-tetrahydro-1H-pyrazolo[3,4-b]pyridin-5-yl)-3-(trifluoromethyl)benzamide (15 g, 72%) as a yellow solid.

rac-N-((4R,5R)-1-(3-bromophenyl)-7-ethyl-4-(4-fluorophenyl)-3-(hydroxymethyl)-6-oxo-4,5,6,7-tetrahydro-1H-pyrazolo[3,4-b]pyridin-5-yl)-3-(trifluoromethyl)benzamide (12)

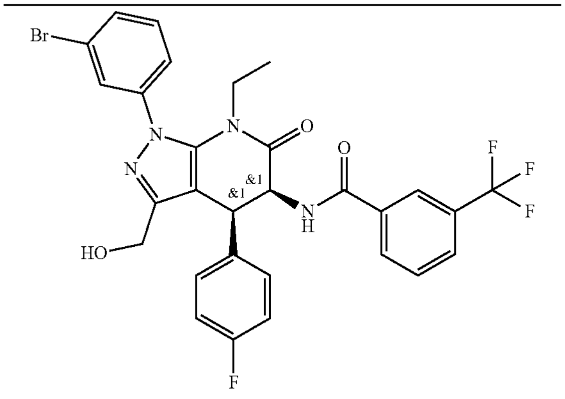

To a stirred solution of rac-N-((4R,5R)-1-(3-bromophenyl)-3-(((tert-butyldimethylsilyl)oxy)methyl)-7-ethyl-4-(4-fluorophenyl)-6-oxo-4,5,6,7-tetrahydro-1H-pyrazolo[3,4-b]pyridin-5-yl)-3-(trifluoromethyl)benzamide (10.0 g, 13.4 mmol, 1.00 equiv) in ACN (50.0 mL) was added HCl (2M) (50.0 mL, 1645 mmol, 123 equiv) dropwise at room temperature under nitrogen atmosphere. The resulting mixture was stirred at room temperature for 2 h under nitrogen atmosphere. The mixture was basified to pH 7 with saturated $NaHCO_3$(aq.). The resulting mixture was extracted with EtOAc (2×100 mL). The combined organic layers were washed with brine (2×100 mL), dried over anhydrous $Na_2SO_4$. After filtration, the filtrate was concentrated under reduced pressure. This resulted in rac-N-((4R,5R)-1-(3-bromophenyl)-7-ethyl-4-(4-fluorophenyl)-3-(hydroxymethyl)-6-oxo-4,5,6,7-tetrahydro-1H-pyrazolo[3,4-b]pyridin-5-yl)-3-(trifluoromethyl)benzamide (8.00 g, 94%) as a white solid. The crude product was used in the next step directly without further purification.

rac-(4R,5R)-1-(3-bromophenyl)-7-ethyl-4-(4-fluorophenyl)-6-oxo-5-[3-(trifluoromethyl)benzamido]-4H,5H-pyrazolo[3,4-b]pyridine-3-carboxylic acid (13)

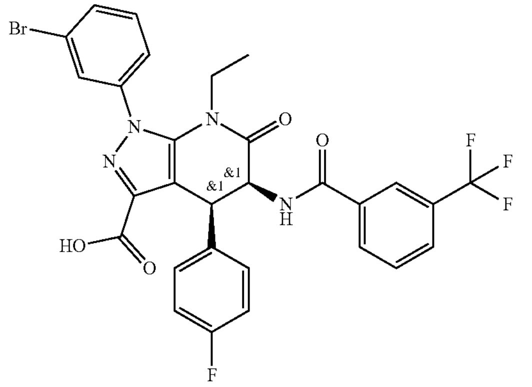

To a stirred solution of rac-N-[(4R,5R)-1-(3-bromophenyl)-7-ethyl-4-(4-fluorophenyl)-3-(hydroxymethyl)-6-oxo-4H,5H-pyrazolo[3,4-b]pyridin-5-yl]-3-(trifluoromethyl) benzamide (10 g, 15.8 mmol, 1.00 equiv) and periodic acid (7.22 g, 31.7 mmol, 2.00 equiv) in ACN (100 mL) were added $CrO_3$ (0.32 g, 3.17 mmol, 0.20 equiv) in portions at room temperature under nitrogen atmosphere. The resulting mixture was stirred at room temperature for 4 h under nitrogen atmosphere. The reaction was quenched with sat. $Na_2S_2O_3$ (aq.) at room temperature. The resulting mixture was extracted with EtOAc (2×100 mL). The combined organic layers were washed with brine (2×100 mL), dried over anhydrous $Na_2SO_4$. After filtration, the filtrate was concentrated under reduced pressure. This resulted in rac-(4R,5R)-1-(3-bromophenyl)-7-ethyl-4-(4-fluorophenyl)-6-oxo-5-[3-(trifluoromethyl)benzamido]-4H,5H-pyrazolo[3,4-b]pyridine-3-carboxylic acid (8.00 g, 78%) as a white solid. The crude product was used in the next step directly without further purification.

N-((4RS,5RS)-1-(3-bromophenyl)-3-((2S)-2-cyanopyrrolidine-1-carbonyl)-7-ethyl-4-(4-fluorophenyl)-6-oxo-4H,5H-pyrazolo(3,4-b)pyridin-5-yl)-3-(trifluoromethyl)benzamide (14)

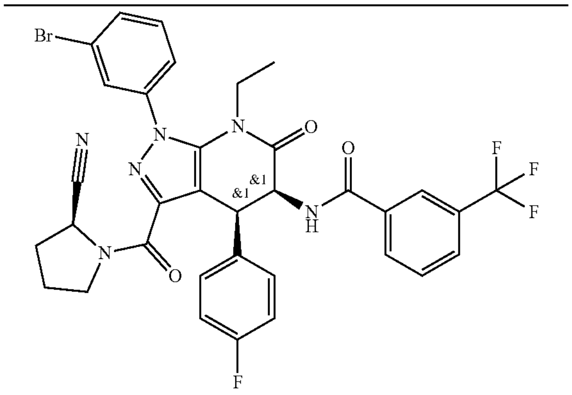

To a stirred solution of rac-(4R,5R)-1-(3-bromophenyl)-7-ethyl-4-(4-fluorophenyl)-6-oxo-5-[3-(trifluoromethyl) benzamido]-4H,5H-pyrazolo[3,4-b]pyridine-3-carboxylic acid (8.00 g, 12.4 mmol, 1.00 equiv) and HATU (6.13 g, 16.1 mmol, 1.30 equiv) in DMF (80 mL) was added (2S)-pyrrolidine-2-carbonitrile (1.31 g, 13.6 mmol, 1.10 equiv) in portions at room temperature under nitrogen atmosphere. The resulting mixture was stirred at room temperature for 1 h under nitrogen atmosphere. The mixture was quenched with water (200 mL). The resulting mixture was extracted with EtOAc (2×100 mL). The combined organic layers were washed with brine (2×100 mL), dried over anhydrous $Na_2SO_4$. After filtration, the filtrate was concentrated under reduced pressure. The residue was purified by silica gel column chromatography, eluted with petroleum ether/EtOAc (1:1) to afford N-((4RS,5RS)-1-(3-bromophenyl)-3-((2S)-2-cyanopyrrolidine-1-carbonyl)-7-ethyl-4-(4-fluorophenyl)-6-oxo-4H,5H-pyrazolo (3,4-b)pyridin-5-yl)-3-(trifluoromethyl)benzamide (6.6 g, 73%) as a yellow solid.

N-((4RS,5RS)-3-((2S)-2-cyanopyrrolidine-1-carbonyl)-7-ethyl-4-(4-fluorophenyl)-6-oxo-1-(3-(4,4,5,5-tetramethyl-1,3,2-dioxaborolan-2-yl) phenyl)-4H,5H-pyrazolo(3,4-b)pyridin-5-yl)-3-(trifluoromethyl) benzamide (15)

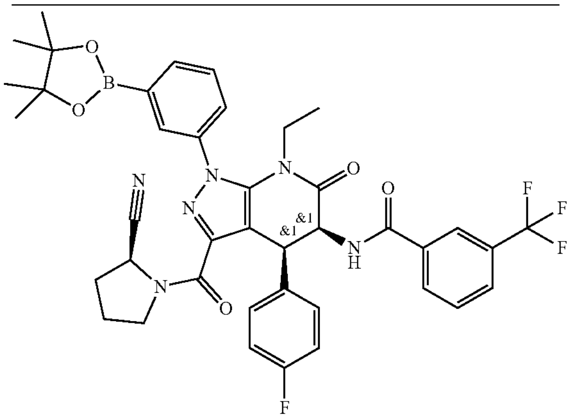

To a solution of N-[(4RS,5RS)-1-(3-bromophenyl)-3-[(2S)-2-cyanopyrrolidine-1-carbonyl]-7-ethyl-4-(4-fluorophenyl)-6-oxo-4H,5H-pyrazolo[3,4-b]pyridin-5-yl]-3-(trifluoromethyl)benzamide (6.40 g, 8.85 mmol, 1 equiv) and bis(pinacolato)diboron (2.70 g, 10.6 mmol, 1.20 equiv) in dioxane (60.0 mL, 708 mmol, 80.07 equiv) were added KOAc (1.74 g, 17.7 mmol, 2.00 equiv) and Pd(dppf)$Cl_2$ (647 mg, 0.885 mmol, 0.100 equiv). After stirring for 2 h at 100° C. under a nitrogen atmosphere, the resulting mixture was concentrated under reduced pressure. The residue was purified by silica gel column chromatography, eluted with petroleum ether/EtOAc (1:1) to afford N-((4RS,5RS)-3-((2R)-2-cyanopyrrolidine-1-carbonyl)-7-ethyl-4-(4-fluorophenyl)-6-oxo-1-(3-(4,4,5,5-tetramethyl-1,3,2-dioxaborolan-2-yl) phenyl)-4H,5H-pyrazolo (3,4-b)pyridin-5-yl)-3-(trifluoromethyl)benzamide (4.10 g, 60%) as a yellow solid.

N-((4RS,5RS)-3-((S)-2-cyanopyrrolidine-1-carbonyl)-7-ethyl-4-(4-fluorophenyl)-1-(3-hydroxyphenyl)-6-oxo-4,5,6,7-tetrahydro-1H-pyrazolo[3,4-b]pyridin-5-yl)-3-(trifluoromethyl)benzamide (16)

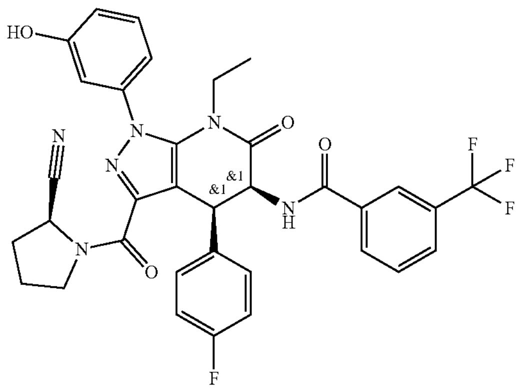

A solution of N-((4RS,5RS)-3-((2R)-2-cyanopyrrolidine-1-carbonyl)-7-ethyl-4-(4-fluorophenyl)-6-oxo-1-(3-(4,4,5,5-tetramethyl-1,3,2-dioxaborolan-2-yl)phenyl)-4H,5H-pyrazolo (3,4-b)pyridin-5-yl)-3-(trifluoromethyl)benzamide (4.10 g, 5.32 mmol, 1.00 equiv) and $NaHCO_3$ (0.130 g, 5.32 mmol, 1.00 equiv) in MeOH (40.0 mL) was stirred at room temperature for 1 h under nitrogen atmosphere. To the above mixture was added $H_2O_2$ (30%) (2.00 mL, 85.8 mmol, 16.1 equiv) dropwise at room temperature. The resulting mixture was stirred at room temperature for additional 1 h. The mixture was acidified to pH 7 with HCl (aq.). The resulting mixture was concentrated under reduced pressure. The residue was purified by silica gel column chromatography, eluted with petroleum ether/EtOAc (1:1) to afford N-((4RS,5RS)-3-((RS)-2-cyanopyrrolidine-1-carbonyl)-7-ethyl-4-(4-fluorophenyl)-1-(3-hydroxyphenyl)-6-oxo-4,5,6,7-tetrahydro-1H-pyrazolo[3,4-b]pyridin-5-yl)-3-(trifluoromethyl) benzamide (3.00 g, 85%) as a white solid.

N-((4R,5R)-3-((R)-2-cyanopyrrolidine-1-carbonyl)-7-ethyl-4-(4-fluorophenyl)-1-(3-hydroxyphenyl)-6-oxo-4,5,6,7-tetrahydro-1H-pyrazolo[3,4-b]pyridin-5-yl)-3-(trifluoromethyl)benzamide (17A) & N-((4S,5S)-3-((R)-2-cyanopyrrolidine-1-carbonyl)-7-ethyl-4-(4-fluorophenyl)-1-(3-hydroxyphenyl)-6-oxo-4,5,6,7-tetrahydro-1H-pyrazolo[3,4,b]pyridin-5-yl)-3-(trifluoromethyl)benzamide (17B)

17A

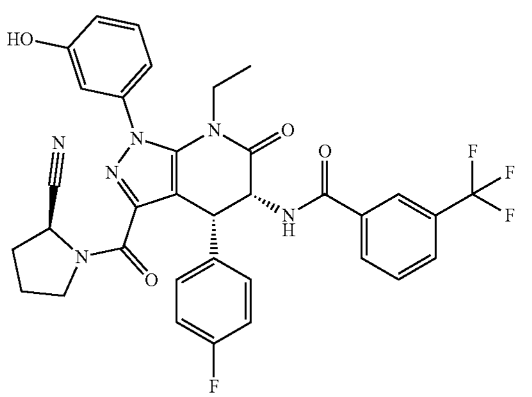

-continued

17B

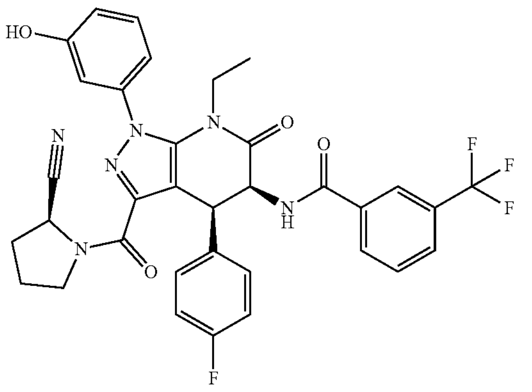

N-((4RS,5RS)-3-((S)-2-cyanopyrrolidine-1-carbonyl)-7-ethyl-4-(4-fluorophenyl)-1-(3-hydroxyphenyl)-6-oxo-4,5,6,7-tetrahydro-1H-pyrazolo[3,4-b]pyridin-5-yl)-3-(trifluoromethyl)benzamide (3.1 g, 4.692 mmol, 1 equiv) was purified by Chiral-Prep-HPLC to afford N-((4R,5R)-3-((S)-2-cyanopyrrolidine-1-carbonyl)-7-ethyl-4-(4-fluorophenyl)-1-(3-hydroxyphenyl)-6-oxo-4,5,6,7-tetrahydro-1H-pyrazolo[3,4-b]pyridin-5-yl)-3-(trifluoromethyl)benzamide (17A) (1.3 g, 41.9%) as a white solid and N-((4S,5S)-3-((S)-2-cyanopyrrolidine-1-carbonyl)-7-ethyl-4-(4-fluorophenyl)-1-(3-hydroxyphenyl)-6-oxo-4,5,6,7-tetrahydro-1H-pyrazolo[3,4-b]pyridin-5-yl)-3-(trifluoromethyl)benzamide (17B) (1.3 g, 41.9%) as a white solid.

N-((4R,5R)-1-(3-(3-bromopropoxy)phenyl)-3-((S)-2-cyanopyrrolidine-1-carbonyl)-7-ethyl-4-(4-fluorophenyl)-6-oxo-4,5,6,7-tetrahydro-1H-pyrazolo[3,4-b]pyridin-5-yl)-3-(trifluoromethyl)benzamide (18A)

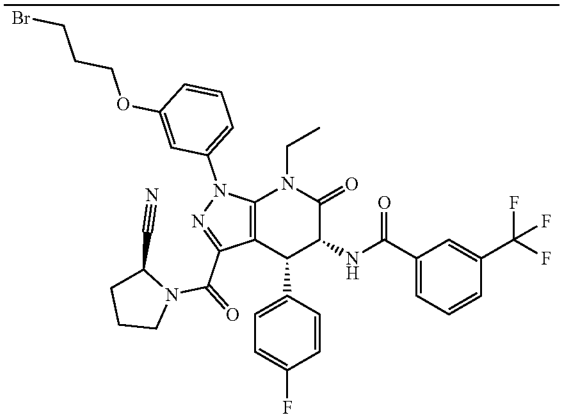

To a stirred solution of N-((4R,5R)-3-((S)-2-cyanopyrrolidine-1-carbonyl)-7-ethyl-4-(4-fluorophenyl)-1-(3-hydroxyphenyl)-6-oxo-4,5,6,7-tetrahydro-1H-pyrazolo[3,4-b]pyridin-5-yl)-3-(trifluoromethyl)benzamide (300 mg, 0.454 mmol, 1.00 equiv) and $K_2CO_3$ (313 mg, 2.27 mmol, 5.00 equiv) in ACN (5.00 mL) was added 1,3-dibromopropane (917 mg, 4.540 mmol, 10.0 equiv) dropwise at room temperature under nitrogen atmosphere. The resulting mixture was stirred at room temperature overnight under nitrogen atmosphere. The resulting mixture was concentrated under reduced pressure. The residue was purified by silica gel column chromatography, eluted with petroleum ether/ethyl acetate (1:1) to afford N-((4R,5R)-1-(3-(3-bromopropoxy)

phenyl)-3-((S)-2-cyanopyrrolidine-1-carbonyl)-7-ethyl-4-(4-fluorophenyl)-6-oxo-4,5,6,7-tetrahydro-1H-pyrazolo[3,4-b]pyridin-5-yl)-3-(trifluoromethyl)benzamide (300 mg, 84%) as a white solid.

N-((4R,5R)-3-((S)-2-cyanopyrrolidine-1-carbonyl)-7-ethyl-4-(4-fluorophenyl)-1-(3-(3-(methyl(oxetan-3-yl)amino)propoxy)phenyl-6-oxo-4,5,6,7-tetrahydro-1H-pyrazolo[3,4-b]pyridin-5-yl)-3-(trifluoromethyl)benzamide) (I-480)

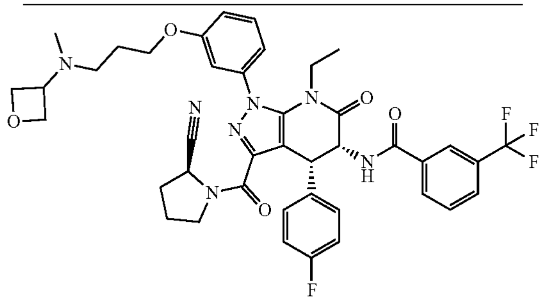

To a stirred solution of N-((4R,5R)-1-(3-(3-bromopropoxy)phenyl)-3-((S)-2-cyanopyrrolidine-1-carbonyl)-7-ethyl-4-(4-fluorophenyl)-6-oxo-4,5,6,7-tetrahydro-1H-pyrazolo[3,4-b]pyridin-5-yl)-3-(trifluoromethyl)benzamide (50.0 mg, 0.064 mmol, 1.00 equiv) and DIEA (24.8 mg, 0.192 mmol, 3.00 equiv) in ACN (2.00 mL) was added N-methyloxetan-3-amine (11.2 mg, 0.128 mmol, 2.00 equiv) dropwise at room temperature under nitrogen atmosphere. The resulting mixture was stirred overnight at 60° C. under nitrogen atmosphere. The mixture was allowed to cool down to room temperature. The resulting mixture was purified by reverse phase flash with the following conditions (Column: Sunfire Prep C18 OBD Column, 19*150 mm, 5 μm; Mobile Phase A: Water (0.1% FA), Mobile Phase B: ACN; Flow rate: 30 mL/min; Gradient: 25% B to 55% B in 8 min; Wave Length: 254 nm/220 nm; RT1(min): 5.99). This resulted in N-((4R,5R)-3-((S)-2-cyanopyrrolidine-1-carbonyl)-7-ethyl-4-(4-fluorophenyl)-1-(3-(3-(methyl(oxetan-3-yl)amino)propoxy)phenyl)-6-oxo-4,5,6,7-tetrahydro-1H-pyrazolo[3,4-b]pyridin-5-yl)-3-(trifluoromethyl)benzamide (15 mg, 29.8%) as a white solid.

$^1$H NMR (400 MHZ, DMSO-$d_6$) δ 8.56 (t, J=7.3 Hz, 1H), 8.15 (d, J=13.0 Hz, 2H), 7.93 (d, J=7.8 Hz, 1H), 7.72 (t, J=7.8 Hz, 1H), 7.57-7.46 (m, 1H), 7.45-7.32 (m, 2H), 7.17 (d, J=8.2 Hz, 1H), 7.09 (t, J=8.7 Hz, 2H), 7.04-6.96 (m, 2H), 5.79-4.89 (m, 3H), 4.51 (t, J=6.5 Hz, 2H), 4.40-4.33 (m, 2H), 4.16-3.82 (m, 4H), 3.65-3.42 (m, 2H), 3.16-3.05 (m, 1H), 2.32 (t, J=6.6 Hz, 2H), 2.26-2.07 (m, 2H), 2.06 (s, 3H), 2.00 (s, 2H), 1.87 (s, 2H), 0.94 (t, J=7.1 Hz, 3H).

LCMS Calculated for $C_{41}H_{41}F_4N_7O_5$: 787.31; Observed (Method-C): 788.2 [M+H]$^+$, 99.56% at RT0.977 min.

The compound in the table below were prepared according to I-480.

| | |
|---|---|
| 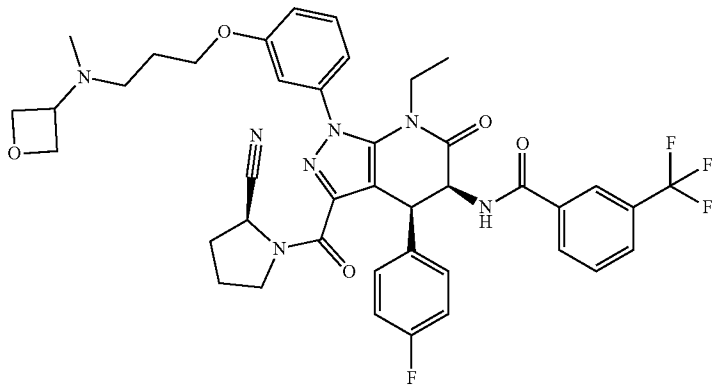 [SMILES: CCN1C(=O)[C@@H](NC(=O)c2cccc(C(F)(F)F)c2)[C@@H](c2ccc(F)cc2)c2c(C(=O)N3CCC[C@H]3C#N)nn(-c3cccc(OCCCN(C)C4COC4)c3)c21]<br>I-335 | $^1$H NMR (400 MHz, DMSO-$d_6$) δ 8.58 (dd, J = 13.5, 7.1 Hz, 1H), 8.21-8.12 (m, 2H), 7.93 (d, J = 7.7 Hz, 1H), 7.72 (t, J = 7.7 Hz, 1H), 7.55 (q, J = 8.0 Hz, 1H), 7.42 (s, 1H), 7.35 (d, J = 8.0 Hz, 1H), 7.18 (d, J = 8.8 Hz, 1H), 7.08 (t, J = 8.8 Hz, 2H), 6.99 (t, J = 7.0 Hz, 2H), 5.65-4.81 (m, 3H), 4.51 (t, J = 6.5 Hz, 2H), 4.37 (t, J = 6.1 Hz, 2H), 4.15-3.83 (m, 4H), 3.49 (t, J = 6.6 Hz, 2H), 3.22-3.03 (m, 1H), 2.31 (d, J = 7.0 Hz, 2H), 2.14 (s, 2H), 2.06 (s, 3H), 1.99 (s, 2H), 1.87 (s, 2H), 0.94 (t, J = 7.5 Hz, 3H).<br>LCMS Calculated for $C_{41}H_{41}F_4N_7O_5$: 787.31; Observed (Method-C): 788.2 [M + H]$^+$, 99.5% at RT 0.981 min. |
| 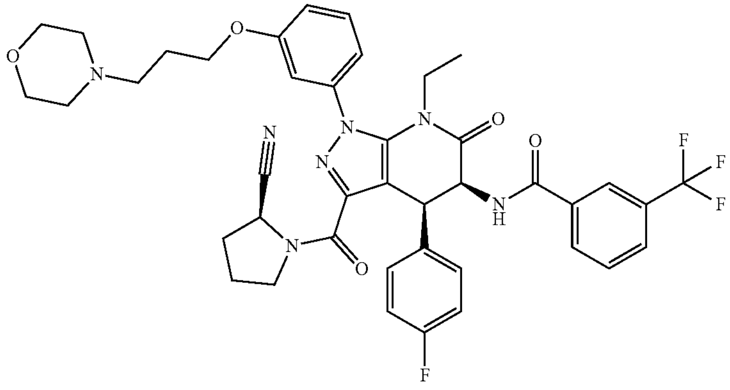 [SMILES: CCN1C(=O)[C@@H](NC(=O)c2cccc(C(F)(F)F)c2)[C@@H](c2ccc(F)cc2)c2c(C(=O)N3CCC[C@H]3C#N)nn(-c3cccc(OCCCN4CCOCC4)c3)c21]<br>I-338 | $^1$H NMR (400 MHz, DMSO-$d_6$) δ 8.58 (dd, J = 13.0, 7.2 Hz, 1H), 8.21-8.13 (m, 2H), 7.93 (d, J = 7.9 Hz, 1H), 7.72 (t, J = 7.8 Hz, 1H), 7.53 (t, J = 8.0 Hz, 1H), 7.41 (s, 1H), 7.35 (d, J = 8.1 Hz, 1H), 7.17 (d, J = 8.2 Hz, 1H), 7.08 (t, J = 8.9 Hz, 2H), 6.99 (t, J = 6.9 Hz, 2H), 5.60-5.49 (m, 1H), 5.05 (d, J = 7.1 Hz, 1H), 4.90-4.82 (m, 1H), 4.15-3.86 (m, 4H), 3.57 (t, J = 4.6 Hz, 5H), 3.12 (d, J = 14.4 Hz, 1H), 2.44 (t, J = 7.1 Hz, 2H), 2.30 (d, J = 51.4 Hz, 4H), 2.14 (d, J = 6.0 Hz, 2H), 2.00 (s, 2H), 1.90 (d, J = 7.5 Hz, 2H), 0.95 (q, J = 7.5 Hz, 3H).<br>LCMS Calculated for $C_{41}H_{41}F_4N_7O_5$: 787.31; Observed (Method-C): 788.2 [M + H]$^+$, 99.7% at RT 0.985 min. |

-continued

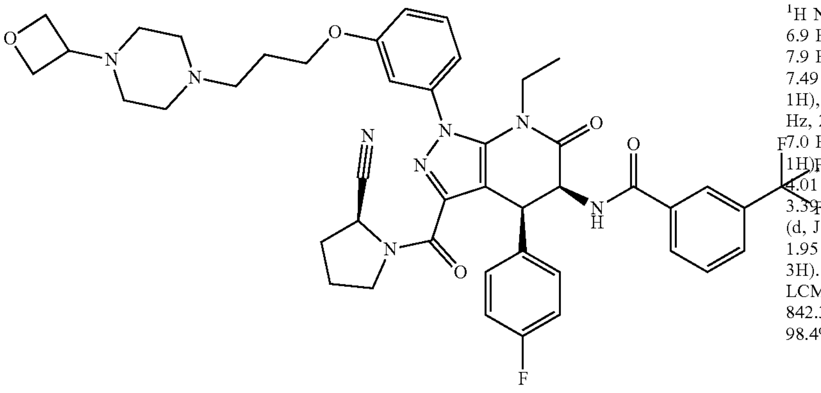

$^1$H NMR (400 MHz, DMSO-$d_6$) δ 8.56 (d, J = 6.9 Hz, 1H), 8.21-8.13 (m, 2H), 7.93 (d, J = 7.9 Hz, 1H), 7.72 (t, J = 8.1 Hz, 1H), 7.57-7.49 (m, 1H), 7.41 (s, 1H), 7.35 (d, J = 8.0 Hz, 1H), 7.16 (d, J = 8.5 Hz, 1H), 7.08 (t, J = 8.6 Hz, 2H), 6.99 (t, J = 7.0 Hz, 2H), 5.57 (d, J = 7.0 Hz, 1H), 5.05 (d, J = 7.4 Hz, 1H), 4.86 (s, 1H), 4.50 (q, J = 6.0 Hz, 2H), 4.40 (s, 2H), 4.01 (d, J = 66.3 Hz, 4H), 3.57-3.45 (m, 1H), 3.39-3.34 (m, 1H), 3.17-3.04 (m, 1H), 2.43 (d, J = 7.0 Hz, 6H), 2.20 (d, J = 31.1 Hz, 6H), 1.95 (d, J = 39.4 Hz, 4H), 0.94 (t, J = 7.5 Hz, 3H).
LCMS Calculated for $C_{44}H_{46}F_4N_8O_5$: 842.35; Observed (Method-C): 843.2 $[M + H]^+$ 98.4% at RT 0.977 min.

I-337

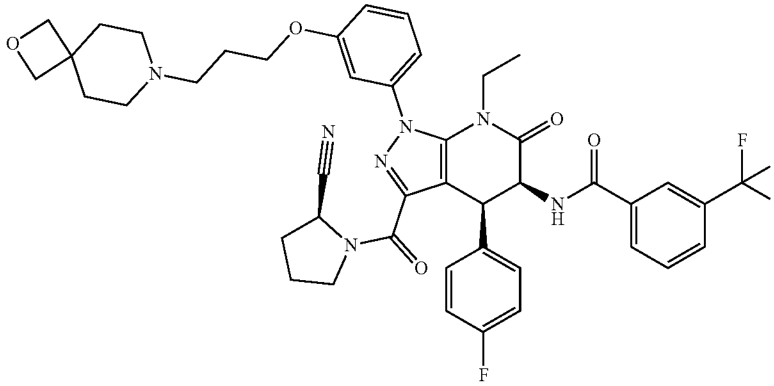

$^1$H NMR (400 MHz, DMSO-$d_6$) δ 8.56 (t, J = 7.4 Hz, 1H), 8.16 (d, J = 13.7 Hz, 2H), 7.93 (d, J = 7.8 Hz, 1H), 7.72 (s, 1H), 7.53 (s, 1H), 7.40 (s, 1H), 7.34 (d, J = 7.8 Hz, 1H), 7.16 (s, 1H), 7.08 (t, J = 8.8 Hz, 2H), 7.00 (d, J = 6.9 Hz, 2H), 5.69-5.42 (m, 1H), 5.19-4.75 (m, 2H), 4.25 (s, 4H), 4.08 (s, 3H), 3.98-3.85 (m, 2H), 2.37 (t, J = 6.4 Hz, 2H), 2.25 (s, 4H), 2.18-2.09 (m, 2H) , 1.99 (s, 2H), 1.88 (s, 2H), 1.74 (s, 4H), 0.94 (t, J = 7.4 Hz, 3H).
LCMS Calculated for $C_{44}H_{45}F_4N_7O_5$: 827.34; Observed (Method-C): 828.3 $[M + H]^+$, 99.7% at RT 0.984 min.

I-336

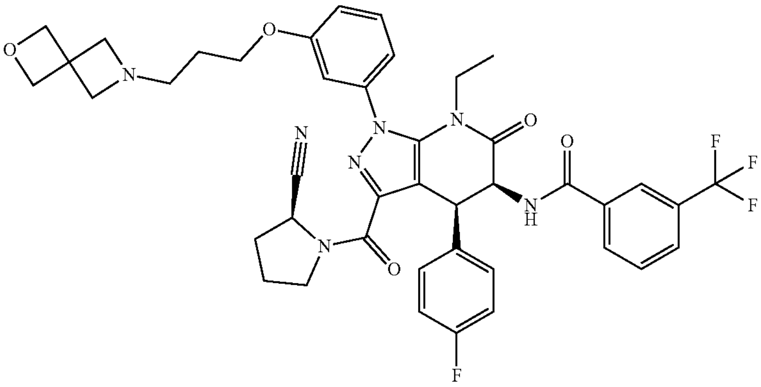 [SMILES: CCN1C(=O)[C@@H](NC(=O)c2cccc(C(F)(F)F)c2)[C@@H](c2ccc(F)cc2)c2c(C(=O)N3CCC[C@H]3C#N)nn(-c3cccc(OCCCN4CC5(COC5)C4)c3)c21]

$^1$H NMR (400 MHz, DMSO-$d_6$) δ 8.56 (t, J = 7.4 Hz, 1H), 8.19-8.11 (m, 2H), 7.93 (d, J = 7.5 Hz, 1H), 7.72 (t, J = 7.7 Hz, 1H), 7.55-7.44 (m, 1H), 7.42-7.32 (m, 2H), 7.18-7.04 (m, 3H), 7.04-6.96 (m, 2H), 5.79-5.55 (m, 1H), 5.49 (t, J = 7.0 Hz, 1H), 4.92 (d, J = 7.0 Hz, 1H), 4.03 (d, J = 8.5 Hz, 3H), 3.87 (s, 2H), 3.63-3.53 (m, 1H), 3.47-3.45 (m, 2H), 3.25 (s, 4H), 3.08 (s, 1H), 2.44 (d, J = 6.9 Hz, 3H), 2.29-2.09 (m, 2H), 2.00 (s, 2H), 1.72 (d, J = 6.4 Hz, 2H), 0.94 (t, J = 6.9 Hz, 3H).
LCMS Calculated for $C_{42}H_{41}F_4N_7O_5$: 799.31; Observed (Method-C): 800.2 $[M + H]^+$, 99.7% at RT 0.972 min.

I-615

-continued

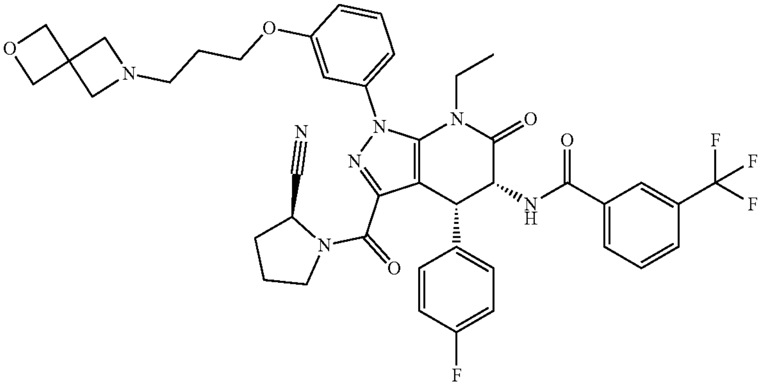 [SMILES: CCN1C(=O)[C@H](NC(=O)c2cccc(C(F)(F)F)c2)[C@H](c2ccc(F)cc2)c2c(C(=O)N3CCC[C@H]3C#N)nn(-c3cccc(OCCCN4CC5(COC5)C4)c3)c21]

I-293

$^1$H NMR (400 MHz, DMSO-$d_6$) δ 8.56 (t, J = 7.4 Hz, 1H), 8.16 (d, J = 14.7 Hz, 2H), 7.93 (d, J = 8.1 Hz, 1H), 7.72 (s, 1H), 7.54 (d, J = 7.8 Hz, 1H), 7.39 (s, 1H), 7.36-7.40 (m, 1H), 7.13 (s, 1H), 7.07 (d, J = 9.0 Hz, 2H), 7.03-6.95 (m, 2H), 5.70-5.47 (m, 1H), 5.07-4.86 (m, 1H), 4.58 (s, 4H), 4.09-3.89 (m, 4H), 3.39-3.34 (m, 1H), 3.31-3.24 (m, 4H), 2.47-2.37 (m, 3H), 2.26-1.94 (m, 5H), 1.71 (s, 1H), 0.94 (t, J = 7.5 Hz, 3H). LCMS Calculated for $C_{42}H_{41}F_4N_7O_5$: 799.31; Observed (Method-C): 800.2 [M + H]$^+$, 99.5% at RT 0.981 min.

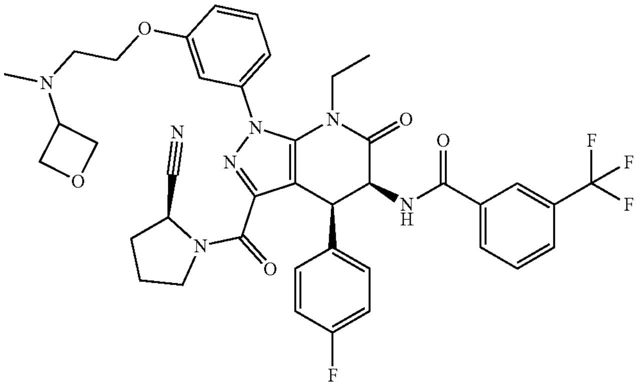 [SMILES: CCN1C(=O)[C@@H](NC(=O)c2cccc(C(F)(F)F)c2)[C@@H](c2ccc(F)cc2)c2c(C(=O)N3CCC[C@H]3C#N)nn(-c3cccc(OCCN(C)C4COC4)c3)c21]

I-347

$^1$H NMR (300 MHz, DMSO-$d_6$): δ 8.66- 8.52 (m, 1H), 8.17 (d, J = 11.7 Hz, 2H), 7.93 (d, J = 7.8 Hz, 1H), 7.72 (t, J = 7.8 Hz, 1H), 7.54 (t, J = 7.8 Hz, 1H), 7.48-7.33 (m, 2H), 7.19 (d, J = 8.4 Hz, 1H), 7.09 (t, J = 8.7 Hz, 2H), 6.99 (t, J = 6.9 Hz, 2H), 5.74-4.76 (m, 3H), 4.54 (t, J = 6.6 Hz, 2H), 4.43 (t, J = 6.0 Hz, 2H), 4.13 (t, J = 5.7 Hz, 2H), 4.07-3.83 (m, 2H), 3.73-3.40 (m, 2H), 3.27-3.02 (m, 1H), 2.67 (t, J = 4.8 Hz, 2H), 2.19 (s, 5H), 1.99 (t, J = 6.9 Hz, 2H), 0.95 (q, J = 6.8 Hz, 3H). LCMS Calculated for $C_{40}H_{39}F_4N_7O_5$: 773.3; Observed (Method-I): 774.4 [M + H]$^+$, 97.0% at RT 1.748 min.

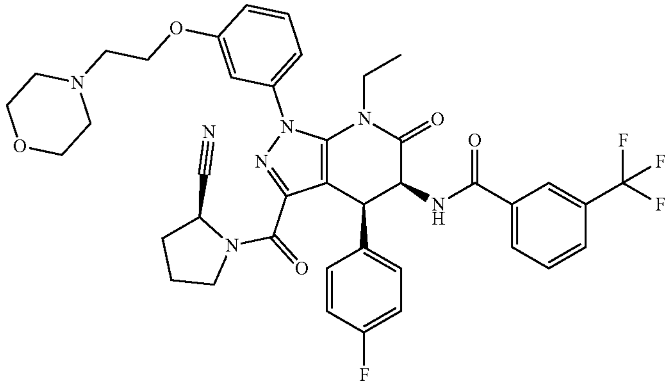 [SMILES: CCN1C(=O)[C@@H](NC(=O)c2cccc(C(F)(F)F)c2)[C@@H](c2ccc(F)cc2)c2c(C(=O)N3CCC[C@H]3C#N)nn(-c3cccc(OCCN4CCOCC4)c3)c21]

I-339

$^1$H NMR (300 MHz, DMSO-$d_6$): δ 8.66-8.54 (m, 1H), 8.16 (d, J = 11.4 Hz, 2H), 7.92 (d, J = 7.8 Hz, 1H), 7.72 (t, J = 7.8 Hz, 1H), 7.53 (t, J = 6.9 Hz, 1H), 7.42 (d, J = 2.7 Hz, 1H), 7.35 (d, J = 7.8 Hz, 1H), 7.18 (d, J = 8.4 Hz, 1H), 7.08 (t, J = 8.7 Hz, 2H), 6.98 (dd, J = 8.4, 5.4 Hz, 2H), 5.73-4.72 (m, 3H), 4.17 (t, J = 5.7 Hz, 2H), 4.11-3.42 (m, 7H), 3.13 (tt, J = 14.1, 6.6 Hz, 1H), 2.72 (m, 6H), 2.23 (d, J = 4.8 Hz, 1H), 2.13 (t, J = 7.2 Hz, 1H), 1.93 (dt, J = 34.5, 8.1 Hz, 2H), 0.94 (q, J = 6.9 Hz, 3H). LCMS Calculated for $C_{40}H_{39}F_4N_7O_5$: 773.3; Observed (Method-J): 774.4 [M + H]$^+$, 99.3% at RT 1.963 min.

-continued

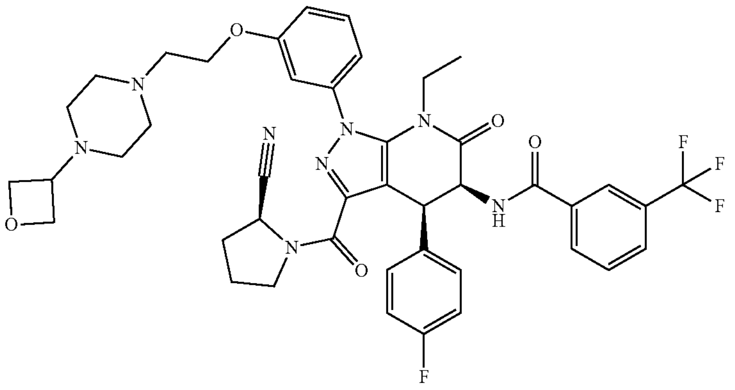 [SMILES: CCN1C(=O)[C@@H](NC(=O)c2cccc(C(F)(F)F)c2)[C@@H](c2ccc(F)cc2)c2c(C(=O)N3CCC[C@H]3C#N)nn(-c3cccc(OCCN4CCN(C5COC5)CC4)c3)c21]

I-340

$^1$H NMR (300 MHz, DMSO-$d_6$): δ 8.59 (t, J = 8.4 Hz, 1H), 8.16 (d, J = 11.4 Hz, 2H), 7.92 (d, J = 7.8 Hz, 1H), 7.71 (t, J = 7.8 Hz, 1H), 7.54 (td, J = 8.1, 6.0 Hz, 1H), 7.41 (d, J = 2.1 Hz, 1H), 7.35 (d, J = 7.8 Hz, 1H), 7.24-7.13 (m, 1H), 7.08 (t, J = 8.7 Hz, 2H), 6.98 (dd, J = 8.7, 5.7 Hz, 2H), 5.68-4.77 (m, 3H), 4.50 (t, J = 6.6 Hz, 2H), 4.40 (t, J = 6.0 Hz, 2H), 4.16 (t, J = 5.7 Hz, 2H), 4.09-3.33 (m, 3H), 3.13 (tt, J = 14.4, 7.2 Hz, 1H), 2.74 (d, J = 6.3 Hz, 2H), 2.51 (m, 4H), 2.39-2.02 (m, 6H), 2.05-1.81 (m, 2H), 0.94 (q, J = 6.9 Hz, 3H).
LCMS Calculated for $C_{43}H_{44}F_4N_8O_5$: 828.3; Observed (Method-C): 829.2 $[M + H]^+$, 99.5% at RT 0.976 min.

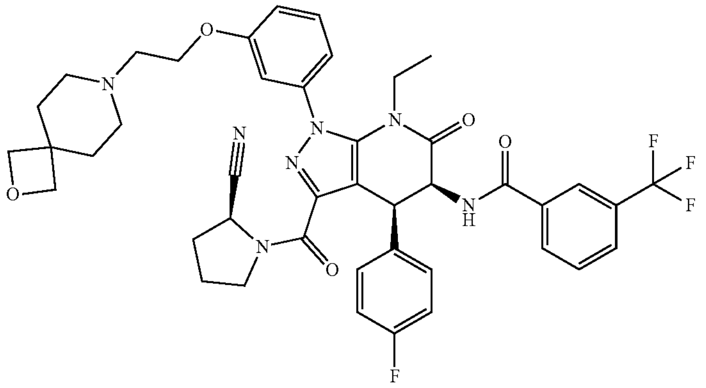 [SMILES: CCN1C(=O)[C@@H](NC(=O)c2cccc(C(F)(F)F)c2)[C@@H](c2ccc(F)cc2)c2c(C(=O)N3CCC[C@H]3C#N)nn(-c3cccc(OCCN4CCC5(CC4)COC5)c3)c21]

I-341

$^1$H NMR (300 MHz, DMSO-$d_6$): δ 8.58 (t, J = 8.1 Hz, 1H), 8.15 (d, J = 10.8 Hz, 2H), 7.92 (d, J = 7.8 Hz, 1H), 7.71 (t, J = 7.5 Hz, 1H), 7.53 (q, J = 7.5 Hz, 1H), 7.40 (d, J = 2.4 Hz, 1H), 7.34 (d, J = 8.1 Hz, 1H), 7.16 (d, J = 8.1 Hz, 1H), 7.07 (t, J = 8.7 Hz, 2H), 6.97 (dd, J = 8.7, 5.4 Hz, 2H), 5.76-4.68 (m, 3H), 4.47-3.75 (m, 9H), 3.49 (s, 1H), 3.21-2.99 (m, 1H), 2.69 (d, J = 20.7 Hz, 2H), 2.36 (s, 3H), 2.29-1.90 (m, 4H), 1.74 (t, J = 5.4 Hz, 4H), 0.94 (q, J = 6.9 Hz, 3H).
LCMS Calculated for $C_{43}H_{43}F_4N_7O_5$: 813.3; Observed (Method-C): 814.3 $[M + H]^+$, 97.1% at RT 0.997 min.

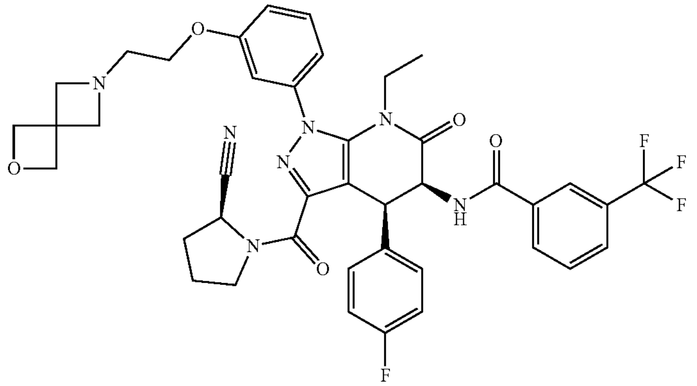 [SMILES: CCN1C(=O)[C@@H](NC(=O)c2cccc(C(F)(F)F)c2)[C@@H](c2ccc(F)cc2)c2c(C(=O)N3CCC[C@H]3C#N)nn(-c3cccc(OCCN4CC5(COC5)C4)c3)c21]

I-342

$^1$H NMR (300 MHz, DMSO-$d_6$): δ 8.62-8.52 (m, 1H), 8.14 (d, J = 11.3 Hz, 2H), 7.91 (d, J = 7.8 Hz, 1H), 7.70 (t, J = 7.8 Hz, 1H), 7.57-7.46 (m, 1H), 7.38-7.29 (m, 2H), 7.19-6.89 (m, 5H), 5.66-4.78 (m, 3H), 4.57 (s, 4H), 4.08-3.35 (m, 6H), 3.33 (s, 3H), 3.09 (dt, J = 14.1, 7.2 Hz, 1H), 2.69 (t, J = 5.5 Hz, 2H), 2.30-1.75 (m, 4H), 0.93 (q, J = 6.8 Hz, 3H).
LCMS Calculated for $C_{41}H_{39}F_4N_7O_5$: 785.2; Observed (Method-J): 786.4 $[M + H]^+$, 98.1% at RT 1.893 min.

4. Synthesis of (4S,5S)-7-ethyl-4-(4-fluorophenyl)-6-oxo-1-phenyl-5-(1-(trifluoromethyl)-1H-pyrazole-3-carboxamido)-4,5,6,7-tetrahydro-1H-pyrazolo[3,4-b]pyridine-3-carboxylic acid (I-580)

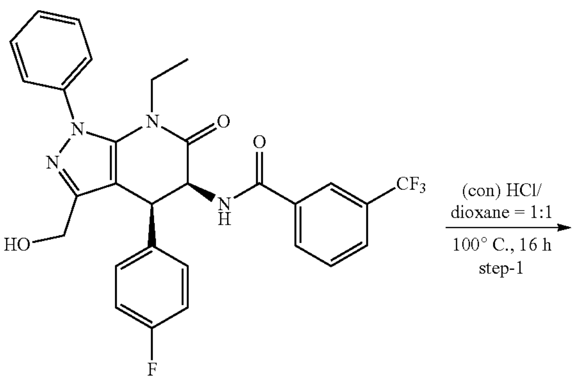

I-645

-continued

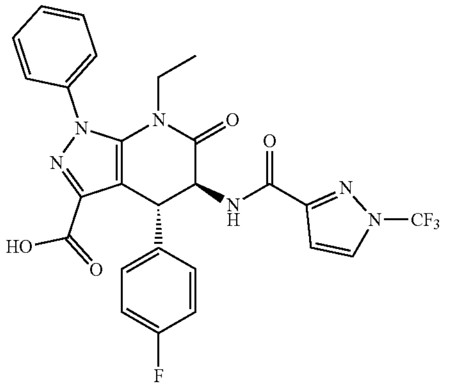

I-580

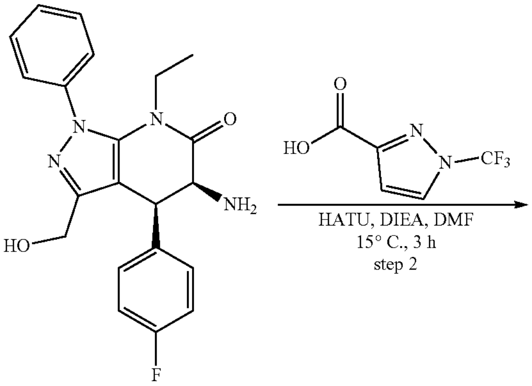

21

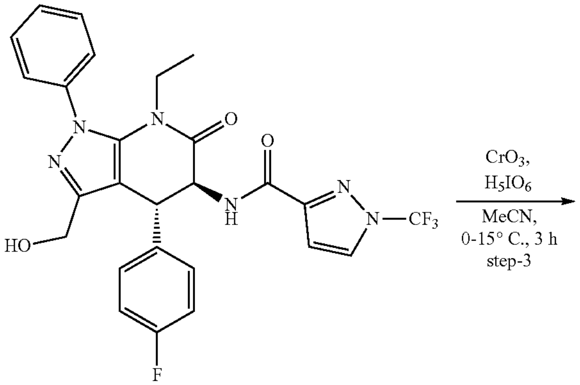

22

(4S,5S)-5-amino-7-ethyl-4-(4-fluorophenyl)-3-(hydroxymethyl)-1-phenyl-1,4,5,7-tetrahydro-6H-pyrazolo[3,4-b]pyridin-6-one (21)

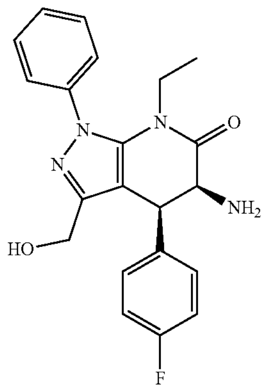

A solution of N-((4S,5S)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-3-(trifluoromethyl)benzamide (10.0 g, 18.1 mmol, 1.00 equiv) in conc. HCl (50 mL) and dioxane (50 mL) was stirred for 16 h at 100° C. After completion of reaction, the resulting mixture was quenched with $K_2CO_3$ (100 mL) to pH=10 and extracted with EtOAc (3×50 mL). The combined organic layers were washed with brine (2×30 mL), dried over anhydrous $Na_2SO_4$. After filtration, the filtrate was concentrated under reduced pressure to give crude product which was further purified by reverse phase flash with method-A conditions to afford (4S,5S)-5-amino-7-ethyl-4-(4-fluorophenyl)-3-(hydroxymethyl)-1-phenyl-4H,5H-pyrazolo[3,4-b]pyridin-6-one (4 g, 58%) as a yellow solid.

$^1$H NMR (300 MHZ, Chloroform-$d_6$) δ 7.53-7.44 (m, 5H), 7.10 (dd, J=8.6, 5.4 Hz, 2H), 6.97 (t, J=8.6 Hz, 2H), 4.65-4.48 (m, 2H), 4.44 (d, J=7.2 Hz, 1H), 4.09-3.88 (m, 2H), 3.12 (dq, J=13.8, 6.9 Hz, 1H), 0.96 (t, J=6.9 Hz, 3H).

LCMS Calculated for $C_{21}H_{21}FN_4O_2$: 380.1; Observed: 381.1 $[M+H]^+$.

N-((4S,5S)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-1-(trifluoromethyl)-1H-pyrazole-3-carboxamide (22)

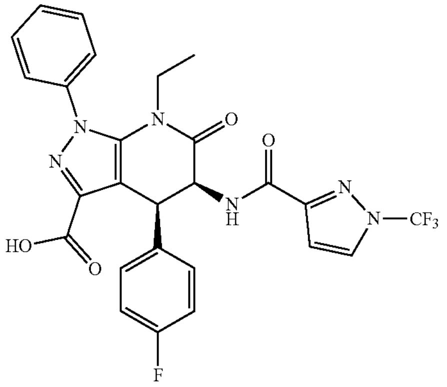

To a stirred solution of 1-(trifluoromethyl) pyrazole-3-carboxylic acid (2.05 g, 11.4 mmol, 1.20 equiv), HATU (5.40 g, 14.2 mmol, 1.50 equiv) and DIEA (2.45 g, 18.9 mmol, 2.00 equiv) in anhydrous DMF (40 mL) was added (4S,5S)-5-amino-7-ethyl-4-(4-fluorophenyl)-3-(hydroxymethyl)-1-phenyl-4H,5H-pyrazolo[3,4-b]pyridin-6-one (3.6 g, 9.46 mmol, 1 equiv) at 15° C. and stirred for 3 h. After completion of reaction, the reaction mixture was concentrated under reduced pressure to give crude product which was further purified by reverse phase flash with the following conditions ($NH_3 \cdot H_2O$ suffer) to afford N-((4S,5S)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-1-(trifluoromethyl)-1H-pyrazole-3-carboxamide (3.4 g, 66%) as a brown solid.

$^1$H NMR (300 MHZ, DMSO-$d_6$) δ 7.86 (d, J=2.7 Hz, 1H), 7.62 (d, J=6.6 Hz, 1H), 7.56-7.49 (m, 5H), 7.04-6.86 (m, 5H), 5.26 (d, J=6.9 Hz, 1H), 4.83 (d, J=6.9 Hz, 1H), 4.61 (s, 2H), 3.99 (dq, J=14.1, 6.9 Hz, 1H), 3.17 (dq, J=14.1, 6.9 Hz, 1H), 2.16 (s, 1H), 0.99 (t, J=6.9 Hz, 3H).

LCMS Calculated for $C_{26}H_{22}F_4N_6O_3$: 542.2; Observed: 543.1 [M+H]$^+$.

(4S,5S)-7-ethyl-4-(4-fluorophenyl)-6-oxo-1-phenyl-5-(1-(trifluoromethyl)-1H-pyrazole-3-carboxamide)-4,5,6,7-tetrahydro-1H-pyrazolo[3,4-b]pyridine-carboxylic acid (I-580)

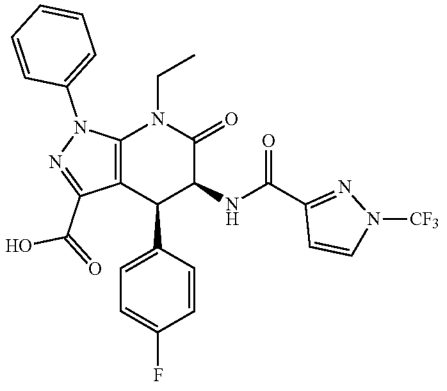

To a degassed solution of N-((4S,5S)-7-ethyl-4-(4-fluorophenyl)-3-(hydroxymethyl)-6-oxo-1-phenyl-4,5,6,7-tetrahydro-1H-pyrazolo[3,4-b]pyridin-5-yl)-1-(trifluoromethyl)-1H-pyrazole-3-carboxamide (2.4 g, 4.42 mmol, 1.00 equiv) in ACN (30 mL) was added $CrO_3$ (133 mg, 1.33 mmol, 0.30 equiv) followed by periodic acid (2.02 g, 8.85 mmol, 2.00 equiv) at 0° C. The reaction mixture was stirred at 15° C. for 3 h. After completion of the reaction, the reaction mixture was quenched with saturated $Na_2S_2O_3$ aqueous solution 50 mL. The aqueous layer was extracted with ethyl acetate (50 mL). Then the combined organic phase was washed with brine, dried over anhydrous $Na_2SO_4$. After filtration, the filtrate was concentrated under reduced pressure to give crude product which was further purified by reverse phase flash with the following conditions ($NH_4HCO_3$ suffer) to afford (4S,5S)-7-ethyl-4-(4-fluorophenyl)-6-oxo-1-phenyl-5-[1-(trifluoromethyl) pyrazole-3-amido]-4H,5H-pyrazolo[3,4-b]pyridine-3-carboxylic acid (2.1 g, 81%) as a yellow solid.

$^1$H NMR (300 MHZ, DMSO-$d_6$) δ 13.12 (s, 1H), 8.68 (d, J=2.7 Hz, 1H), 7.82-7.54 (m, 6H), 7.20-6.87 (m, 5H), 5.41 (t, J=6.6 Hz, 1H), 5.08 (d, J=7.2 Hz, 1H), 3.82 (dd, J=14.4, 7.2 Hz, 1H), 3.04 (dd, J=14.4, 7.2 Hz, 1H), 0.88 (t, J=7.2 Hz, 3H).

LCMS Calculated for $C_{26}H_{20}F_4N_6O_4$: 556.1; Observed (Method-F): 557.1 [M+H]$^+$, 95.4% at RT 1.566 min.

5. Synthesis of N-((4S,5S)-3-((S)-2-cyanopyrrolidine-1-carbonyl)-7-ethyl-4-(4-fluorophenyl)-6-oxo-1-phenyl-4,5,6,7-tetrahyde-1H-pyrazolo[3,4-b]pyridin-5-yl)-1-(trifluoromethyl)-1H-pyrazole-3-carboxamide (I-343)

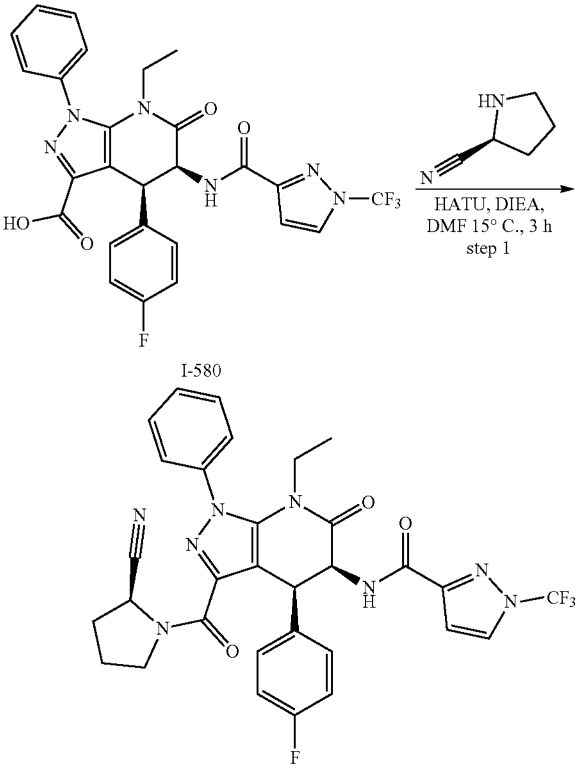

I-580

I-343

To a stirred solution of (4S,5S)-7-ethyl-4-(4-fluorophenyl)-6-oxo-1-phenyl-5-[1-(trifluoromethyl) pyrazole-3-amido]-4H,5H-pyrazolo[3,4-b]pyridine-3-carboxylic acid (100 mg, 0.18 mmol, 1.00 equiv), HATU (102 mg, 0.27 mmol, 1.50 equiv) and DIEA (69.7 mg, 0.54 mmol, 3.00 equiv) in anhydrous DMF (1 mL) was added (2S)-pyrrolidine-2-carbonitrile (22.5 mg, 0.234 mmol, 1.30 equiv) at 15° C. and stirred for 3 h. After completion of reaction, the reaction mixture was concentrated under reduced pressure to give crude product which was further purified by Prep-HPLC with the following conditions ($NH_3 \cdot H_2O$ suffer) to afford N-((4S,5S)-3-((S)-2-cyanopyrrolidine-1-carbonyl)-7-ethyl-4-(4-fluorophenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (60 mg, 52.5%).

Compounds below were prepared similarly I-343.

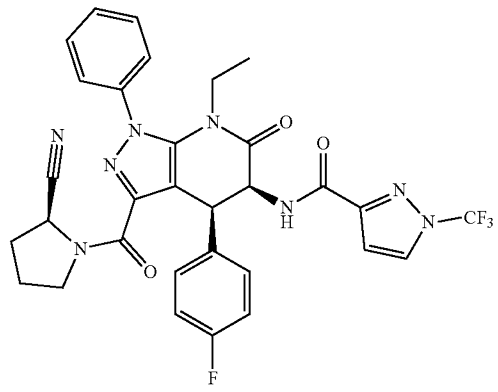 [SMILES: CCN1C(=O)[C@@H](NC(=O)c2ccn(C(F)(F)F)n2)[C@@H](c2ccc(F)cc2)c2c(C(=O)N3CCC[C@H]3C#N)nn(-c3ccccc3)c21]

I-343

$^1$H NMR (300 MHz, DMSO-$d_6$): δ 8.68 (d, J = 3.0 Hz, 1H), 7.78 (dd, J = 7.2, 2.4 Hz, 2H), 7.72-7.46 (m, 4H), 7.19-7.03 (m, 3H), 6.96 (dd, J = 8.4, 5.4 Hz, 2H), 5.75-4.78 (m, 3H), 4.14-3.43 (m, 3H), 3.10 (dq, J = 14.4, 7.2 Hz, 1H), 2.35-1.78 (m, 4H), 0.90 (q, J = 6.6 Hz, 3H).
LCMS Calculated for $C_{31}H_{26}F_4N_8O_3$: 634.2;
Observed (Method-I): 633.2 [M − H]$^+$, 99.7% at RT 1.841 min.

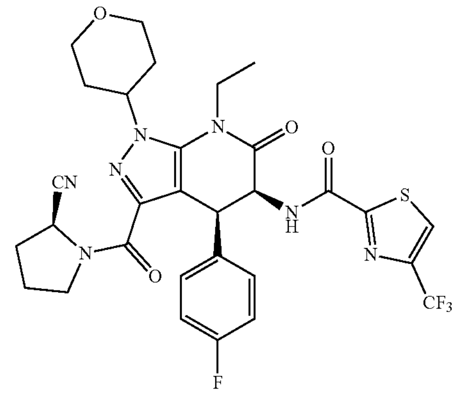 [SMILES: CCN1C(=O)[C@@H](NC(=O)c2nc(C(F)(F)F)cs2)[C@@H](c2ccc(F)cc2)c2c(C(=O)N3CCC[C@H]3C#N)nn(C3CCOCC3)c21]

I-586

$^1$H NMR (300 MHz, DMSO-$d_6$) δ 8.87 (s, 1H), 7.74 (s, 1H), 7.08 (t, J = 8.7 Hz, 2H), 7.02-6.87 (m, 2H), 5.65 (s, 1H), 5.10 (d, J = 32.7 Hz, 2H), 4.85 (t, J = 5.6 Hz, 1H), 4.60 (s, 1H), 4.23-3.83 (m, 5H), 3.68-3.46 (m, 3H), 2.30 (s, 1H), 2.23-1.87 (m, 6H), 1.40-1.27 (m, 3H).
LCMS Calculated for $C_{30}H_{29}F_4N_7O_4S$: 659.19;
Observed (Method-A): 658.2 [M − H]$^-$, 100% at RT 1.207 min.

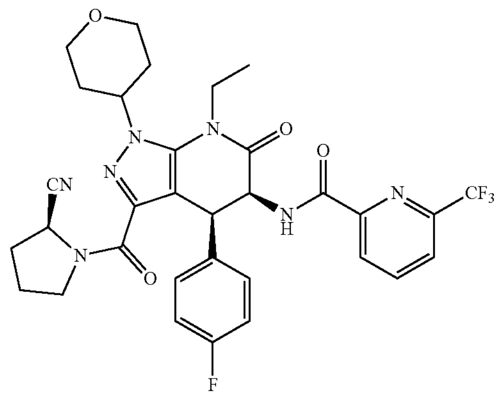 [SMILES: CCN1C(=O)[C@@H](NC(=O)c2cccc(C(F)(F)F)n2)[C@@H](c2ccc(F)cc2)c2c(C(=O)N3CCC[C@H]3C#N)nn(C3CCOCC3)c21]

I-332

$^1$H NMR (300 MHz, DMSO-$d_6$) δ 8.46-8.33 (m, 2H), 8.29 (d, J = 6.0 Hz, 1H), 8.18 (dd, J = 7.2, 1.6 Hz, 1H), 7.05 (t, J = 8.6 Hz, 2H), 6.99-6.88 (m, 2H), 5.65 (s, 1H), 5.15 (d, J = 3.2 Hz, 1H), 5.05 (d, J = 5.3 Hz, 1H), 4.89-4.80 (m, 1H), 4.60 (s, 1H), 4.22-3.87 (m, 5H), 3.70-3.43 (m, 3H), 2.31 (d, J = 4.9 Hz, 2H), 2.24-1.85 (m, 6H), 1.34 (q, J = 6.5 Hz, 3H).
LCMS Calculated for $C_{32}H_{31}F_4N_7O_4$: 653.24
Observed (Method-A): 652.3 [M − H]$^-$, 99.9% at RT 1.189 min.

-continued

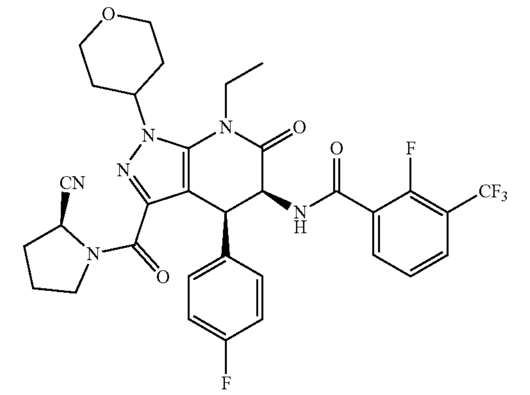 [SMILES: CCN1C(=O)[C@@H](NC(=O)c2cccc(C(F)(F)F)c2F)[C@@H](c2ccc(F)cc2)c2c(C(=O)N3CCC[C@H]3C#N)nn(C3CCOCC3)c21]

I-333

$^1$H NMR (300 MHz, DMSO-$d_6$) δ 8.37 (ddd, J = 10.5, 6.3, 3.5 Hz, 1H), 8.05-7.86 (m, 2H), 7.50 (t, J = 7.8 Hz, 1H), 7.14-6.93 (m, 4H), 5.71-4.80 (m, 3H), 4.59 (s, 1H), 4.26-3.85 (m, 5H), 3.68-3.46 (m, 3H), 2.48-2.24 (m, 2H), 2.23-1.82 (m, 6H), 1.32 (td, J = 7.0, 4.4 Hz, 3H).
LCMS Calculated for $C_{33}H_{30}F_5N_6O_4$: 670.23; Observed (Method-A): 669.3 $[M-H]^-$, 99.5% at RT 1.238 min.

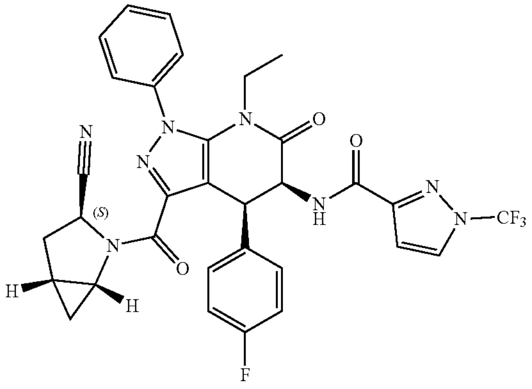

I-344

$^1$H NMR (400 MHz, DMSO-$d_6$) δ 8.69 (d, J = 2.8 Hz, 1H), 7.80 (d, J = 7.7 Hz, 2H), 7.69-7.59 (m, 3H), 7.53 (d, J = 6.4 Hz, 1H), 7.16-7.07 (m, 3H), 6.98 (m, 2H), 5.45 (t, J = 6.7 Hz, 1H), 5.21 (d, J = 7.1 Hz, 1H), 4.83 (m, 1H), 4.35 (d, J = 6.6 Hz, 1H), 3.82 (dd, J = 14.3, 7.2 Hz, 1H), 3.19-3.09 (m, 1H), 2.40 (dd, J = 12.6, 5.9 Hz, 1H), 2.35-2.24 (m, 1H), 1.91 (d, J = 7.2 Hz, 1H), 0.95-0.81 (m, 4H), 0.52 (s, 1H).
LCMS Calculated for $C_{32}H_{26}F_4N_8O_3$: 646.21; Observed (Method-U): 647.3$[M+H]^+$, 98.1% at RT 3.035 min.

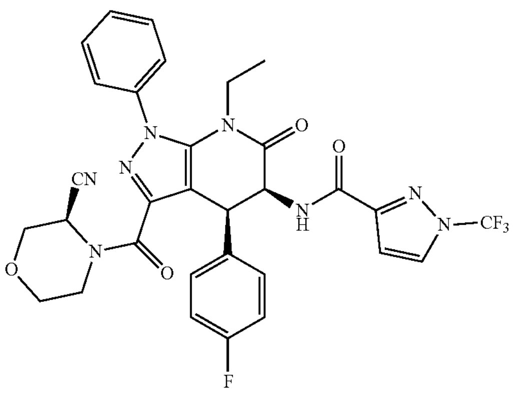 [SMILES: CCN1C(=O)[C@@H](NC(=O)c2ccn(C(F)(F)F)n2)[C@@H](c2ccc(F)cc2)c2c(C(=O)N3CCOC[C@H]3C#N)nn(-c3ccccc3)c21]

I-345

$^1$H NMR (300 MHz, DMSO-$d_6$): δ 8.67 (d, J = 3.0 Hz, 1H), 7.79 (d, J = 7.2 Hz, 2H), 7.71-7.48 (m, 4H), 7.17-6.91 (m, 5H), 6.46-5.25 (m, 2H), 4.99 (m, 2H), 4.09-3.33 (m, 5H), 3.30 (m, 1H), 3.13-2.86 (m, 1H), 0.88 (t, J = 6.9 Hz, 3H).
LCMS Calculated for $C_{31}H_{26}F_4N_8O_4$: 650.2; Observed (Method-J): 649.2 $[M-H]^-$, 99.4% at RT 1.936 min.

6. Synthesis of N-((4S,5S)-3-((S)-2-cyanopiperazine-1-carbonyl)-7-ethyl-4-)4-fluorophenyl)-6-oxo-1-phenyl-4,5,6,7-tetrahydro-1H-pyrazolo[3,4-b]pyridin-5-yl)-1-(trifluormethyl)-1H-pyrazole-3-carboxamide (I-346)

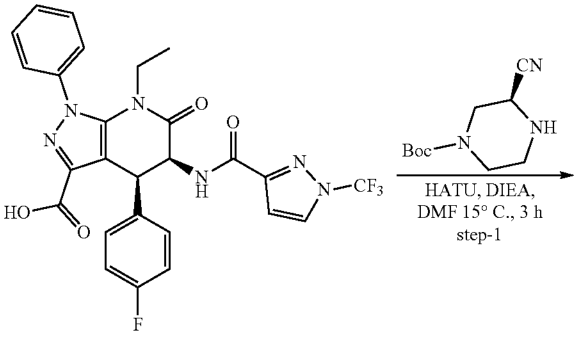

I-580

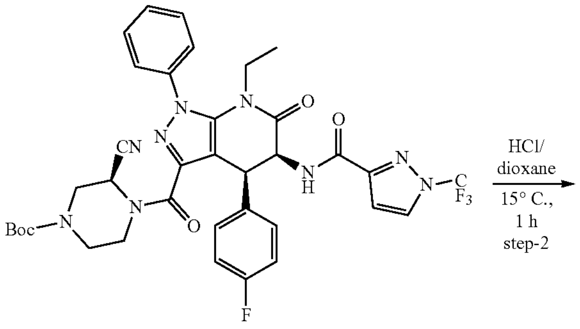

23

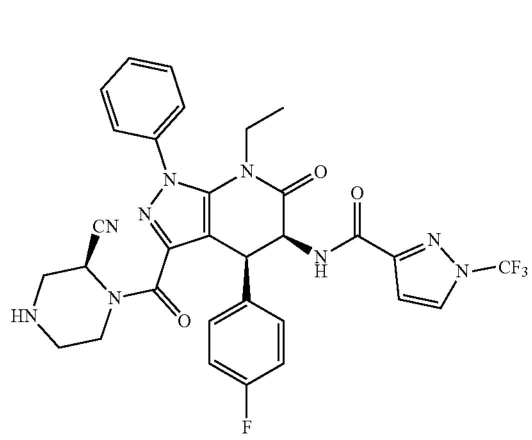

I-346 tert-butyl (S)-3-cyano-4-((4S,5S)-7-ethyl-4-(4-fluorophenyl)-6-oxo-1-phenyl-5-(1-(trifluoromethyl)-1H-pyrazole-3-carboxamido)-4,5,6,7-tetrahydro-1H-pyrazolo[3,4-b]pyridine-3-carbonyl)piperazine-1-carboxylate (23)

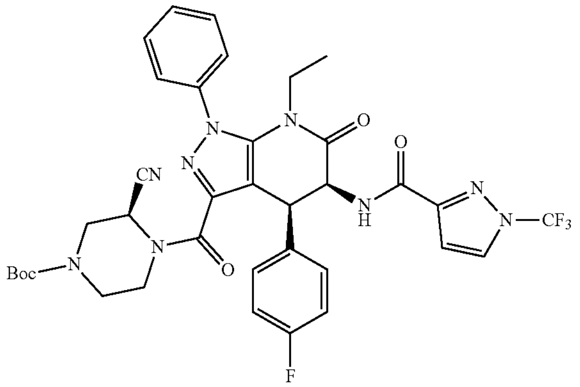

To a stirred solution of (4S,5S)-7-ethyl-4-(4-fluorophenyl)-6-oxo-1-phenyl-5-[1-(trifluoromethyl) pyrazole-3-amido]-4H,5H-pyrazolo[3,4-b]pyridine-3-carboxylic acid (400 mg, 0.719 mmol, 1.00 equiv), HATU (410 mg, 1.08 mmol, 1.50 equiv) and DIEA (279 mg, 2.16 mmol, 3.00 equiv) in anhydrous DMF (4 mL) was added tert-butyl (3S)-3-cyanopiperazine-1-carboxylate (197 mg, 0.935 mmol, 1.30 equiv) at 15° C. and stirred for 3 h. After completion of reaction, the reaction mixture was concentrated under reduced pressure to give crude product which was purified by silica gel column chromatography, eluted with petroleum ether/ethyl acetate (1:1) to afford tert-butyl (S)-3-cyano-4-((4S,5S)-7-ethyl-4-(4-fluorophenyl)-6-oxo-1-phenyl-5-(1-(trifluoromethyl)-1H-pyrazole-3-carboxamido)-4,5,6,7-tetrahydro-1H-pyrazolo[3,4-b]pyridine-3-carbonyl)piperazine-1-carboxylate (400 mg, 74%) as a brown solid.

LCMS Calculated for $C_{36}H_{35}F_4N_9O_5$: 749.2; Observed: 750.2 $[M+H]^+$.

N-((4S,5S)-3-((S)-2-cyanopiperazine-1-carbonyl)-7-ethyl-4-(4-fluorophenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (I-346)

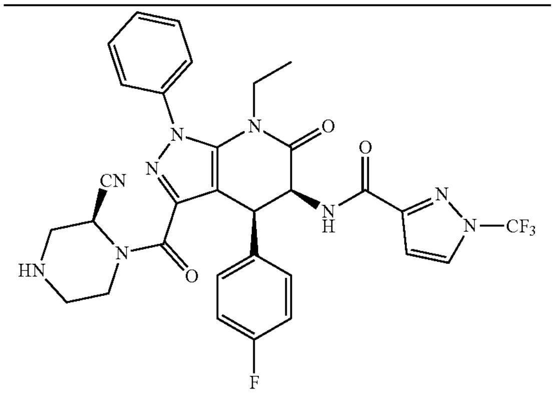

To a stirred solution of tert-butyl (S)-3-cyano-4-((4S,5S)-7-ethyl-4-(4-fluorophenyl)-6-oxo-1-phenyl-5-(1-(trifluoromethyl)-1H-pyrazole-3-carboxamido)-4,5,6,7-tetrahydro-1H-pyrazolo[3,4-b]pyridine-3-carbonyl)piperazine-1-carboxylate (400 mg, 0.534 mmol, 1.00 equiv) in anhydrous 1,4-dioxane (0.5 mL) was added HCl (0.5 mL) at 15° C. and stirred for 1 h. After completion of reaction, the reaction mixture was concentrated under reduced pressure to give crude product which was further purified by Prep-HPLC with the following conditions ($NH_3 \cdot H_2O$ suffer) to afford N-((4S,5S)-3-((S)-2-cyanopiperazine-1-carbonyl)-7-ethyl-4-(4-fluorophenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (316 mg, 91%) as a white solid.

$^1$H NMR (300 MHZ, DMSO-d$_6$) δ 8.67 (d, J=3.0 Hz, 1H), 7.78 (s, 2H), 7.71-7.48 (m, 4H), 7.15-7.04 (m, 3H), 6.94 (dd, J=8.4, 5.4 Hz, 2H), 6.38-4.57 (m, 3H), 3.95-3.71 (m, 1H), 3.24-2.53 (m, 7H), 2.26 (m, 1H), 0.88 (t, J=6.9 Hz, 3H).

LCMS Calculated for $C_{31}H_{27}F_4N_9O_3$: 649.2; Observed (Method V): 648.2 [M−H]$^-$, 95.3% at RT 1.812 min.

Compound below prepared similarly to I-343.

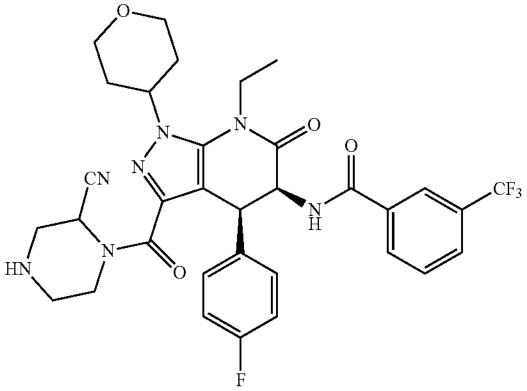 [SMILES: CCN1C(=O)[C@@H](NC(=O)c2cccc(C(F)(F)F)c2)[C@@H](c2ccc(F)cc2)c2c(C(=O)N3CCNCC3C#N)nn(C3CCOCC3)c21]

I-334

$^1$H NMR (400 MHz, DMSO-d$_6$) δ 8.50 (d, J = 7.0 Hz, 1H), 8.17-8.09 (m, 2H), 7.92 (d, J-7.8 Hz, 1H), 7.71 (t, J = 7.8 Hz, 1H), 7.07 (t, J = 8.8 Hz, 2H), 6.94 (t, J = 6.8 Hz, 2H), 5.25 (s, 1H), 4.74 (d, J = 7.0 Hz, 1H), 4.59 (s, 1H), 4.27-4.03 (m, 3H), 3.96 (s, 1H), 3.60-3.41 (m, 2H), 3.31 (s, 4H), 2.90-2.70 (m, 1H), 2.30-1.61 (m, 2H), 1.33 (t, J = 7.0 Hz, 3H).
LCMS Calculated for $C_{33}H_{33}F_4N_7O_4$: 667.25; Observed (Method-M): 668.4 [M + H]$^+$, 96.2% at RT 1.907 min.
Chiral SFC (Method-B): 58.03% at 1.055 min, 41.97% at 1.120 min.

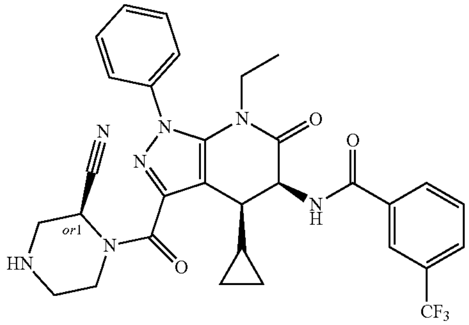 [SMILES: CCN1C(=O)[C@@H](NC(=O)c2cccc(C(F)(F)F)c2)[C@@H](C2CC2)c2c(C(=O)N3CCNC[C@H]3C#N)nn(-c3ccccc3)c21]

I-383

$^1$H NMR (300 MHz, DMSO-d$_6$) δ 9.11 (s, 1H), 8.34 (s, 1H), 8.27 (d, J = 7.8 Hz, 1H), 7.96 (d, J = 8.0 Hz, 1H), 7.87-7.69 (m, 3H), 7.66-7.53 (m, 2H), 5.46-5.35 (m, 1H), 4.71-4.76 (m, 1H), 4.07-3.03 (m, 1H), 3.30-3.11 (m, 2H), 3.10-2.60 (m, 5H), 2.48-2.34 (m, 3H), 0.84 (s, 4H), 0.53 (s, 1H), 0.25 (s, 1H).
LCMS Calculated for $C_{31}H_{30}F_3N_7O_3$: 605.24; Observed (Method-R): 606.5 [M + H]$^+$, 87.1% at RT 0.811 min.

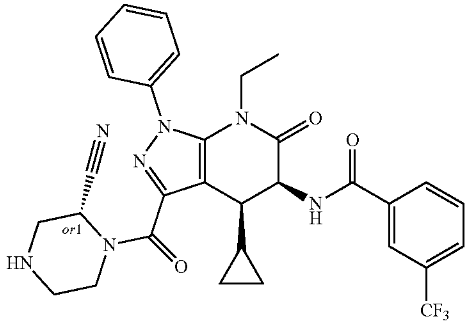 [SMILES: CCN1C(=O)[C@@H](NC(=O)c2cccc(C(F)(F)F)c2)[C@@H](C2CC2)c2c(C(=O)N3CCNC[C@@H]3C#N)nn(-c3ccccc3)c21]

I-518

$^1$H NMR (300 MHz, DMSO-d$_6$) δ 9.10 (d, J = 8.0 Hz, 1H), 8.34 (s, 1H), 8.27 (d, J = 7.6 Hz, 1H), 7.96 (d, J = 7.8 Hz, 1H), 7.86-7.68 (m, 3H), 7.60 (d, J = 7.5 Hz, 3H), 5.53-5.36 (m, 2H), 4.66-4.35 (m, 1H), 3.97-3.79 (m, 1H), 3.19 (s, 3H), 3.05-2.70 (m, 4H), 0.97-0.73 (m, 4H), 0.61-0.47 (m, 1H), 0.32-0.18 (m, 1H), 0.04--0.04 (m, 2H).
LCMS Calculated for $C_{31}H_{30}F_3N_7O_3$: 605.24; Observed (Method-R): 606.5 [M + H]$^+$, 98.8% at RT 0.807 min.

7. Synthesis of N-((4S,5S)-3-(2-cyano-4-methylpiperazine-1-carbonyl)-7-ethyl-4-(4-fluorophenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (I-684)

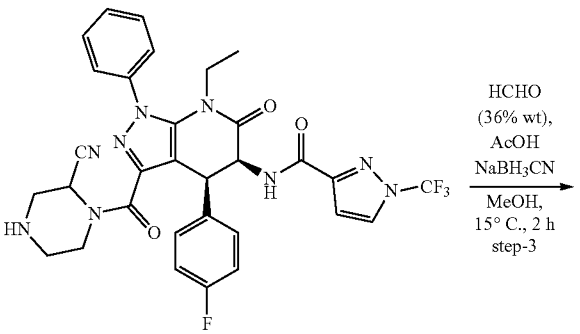

I-346

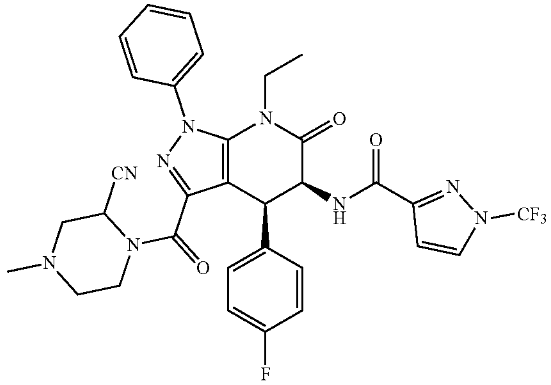

I-684

To a stirred solution of N-((4S,5S)-3-(2-cyanopiperazine-1-carbonyl)-7-ethyl-4-(4-fluorophenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (100 mg, 0.154 mmol, 1,00 equiv) in anhydrous $CH_3OH$ (5 mL) was added sodium cyanoboranuide (29.1 mg, 0.462 mmol, 3,00 equiv), AcOH (27.8 mg, 0.462 mmol, 3.00 equiv) and formaldehyde (46.4 mg, 1.54 mmol, 10.0 equiv) at 15° C. and stirred for 2 h. After completion of reaction, the reaction mixture was purified by Prep-HPLC with the following conditions (FA suffer) to afford N-((4S,5S)-3-(2-cyano-4-methylpiperazine-1-carbonyl)-7-ethyl-4-(4-fluorophenyl)-6-oxo-1-phenyl-4,5,6,7-tetrahydro-1H-pyrazolo[3,4-b]pyridin-5-yl)-1-(trifluoromethyl)-1H-pyrazole-3-carboxamide (23 mg, 22%) as a white solid.

$^1$H NMR (300 MHZ, DMSO-$d_6$) δ 8.68 (d, J=2.7 Hz, 1H), 7.91-7.74 (m, 2H), 7.70-7.49 (m, 4H), 7.18-7.03 (m, 3H), 6.95 (dd, J=8.4, 5.4 Hz, 2H), 5.82-4.16 (m, 3H), 3.96-3.68 (m, 1H), 3.20-2.64 (m, 4H), 2.50 (m, 2H), 2.10 (m, 4H), 0.89 (t, J=6.9 Hz, 3H).

LCMS Calculated for $C_{32}H_{29}F_4N_9O_3$: 663.2; Observed (Method-J): 662.2 [M−H]$^-$, 100% at RT 1.938 min.

Chiral SFC (Method-G): 58.23% at 1.101 min; 41.77% at 1.274 min.

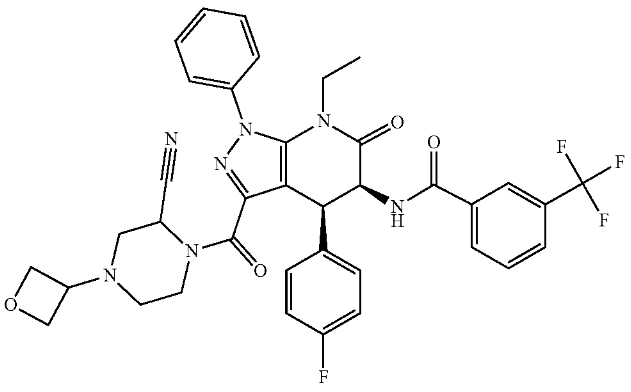 [SMILES: CCN1C(=O)[C@@H](NC(=O)c2cccc(C(F)(F)F)c2)[C@@H](c2ccc(F)cc2)c2c(C(=O)N3CCN(C4COC4)CC3C#N)nn(-c3ccccc3)c21]

I-357

$^1$H NMR (400 MHz, DMSO-$d_6$) δ 8.58 (d, J = 7.2 Hz, 1H), 8.20-8.10 (m, 2H), 7.93 (d, J = 7.7 Hz, 1H), 7.82 (s, 2H), 7.72 (t, J = 7.8 Hz, 1H), 7.68-7.59 (m, 3H), 7.09 (t, J = 8.7 Hz, 2H), 7.02-6.94 (m, 2H), 5.72-4.82 (m, 3H), 4.53 (t, J = 5.0 Hz, 2H), 4.47-4.35 (m, 2H), 3.92-3.84 (m, 1H), 3.50 (s, 1H), 3.10-2.99 (m, 2H), 2.83 (d, J = 11.9 Hz, 1H), 2.18-1.98 (m, 1H), 1.95-1.55 (m, 1H), 0.91 (t, J = 7.0 Hz, 3H). LCMS Calculated for $C_{37}H_{33}F_4N_7O_4$: 715.25; Observed (Method-X): 714.2 [M − H]$^-$, 99.7% at RT 1.660 min. Chiral HPLC (Method-G): 52.49% at 2.193 min; 47.51% at 2.480 min.

8. Synthesis of (4S,5S)-N-((S)-1-cyanoethyl)-4-cyclopropyl-7-ethyl-N-methyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxamide (I-549)

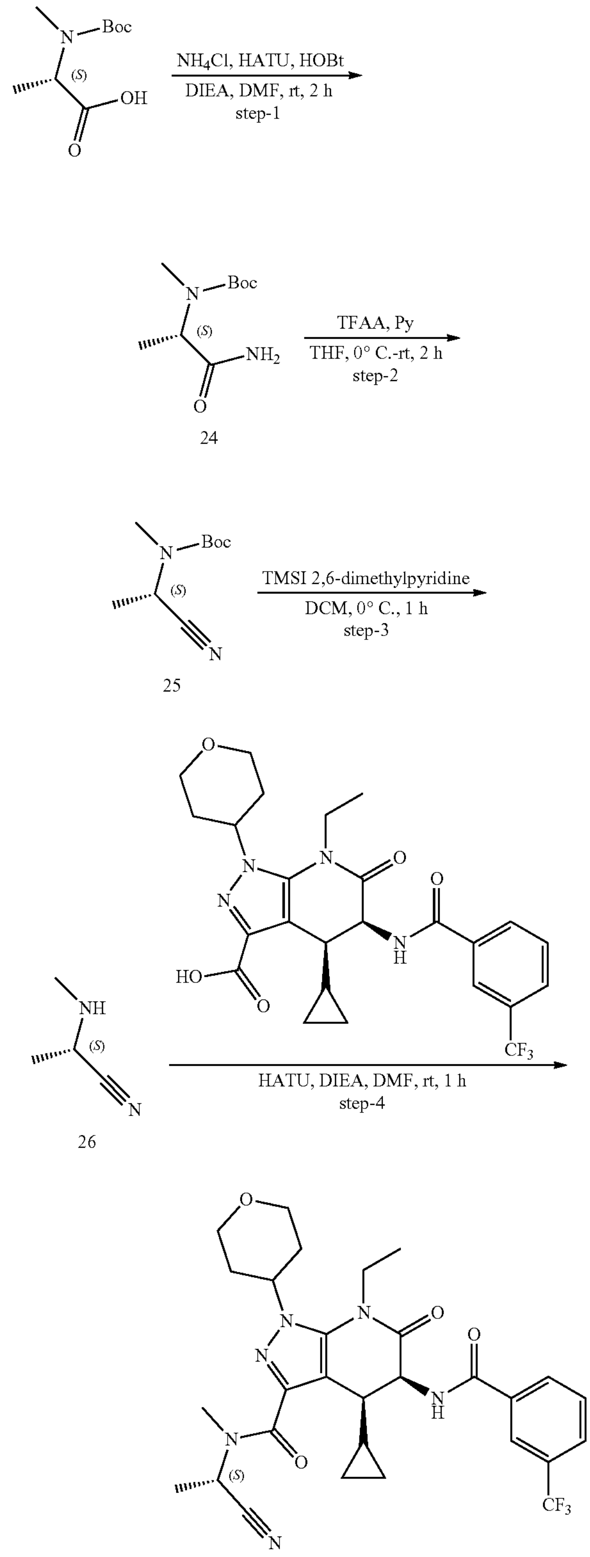

24

25

26

I-549 tert-butyl (S)-(1-amino-1-oxopropan-2-yl)(methyl)carbamate (24)

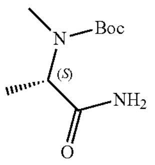

Into a 500 mL 3-necked round-bottom flask were added N-(tert-butoxycarbonyl)-N-methyl-L-alanine (13.0 g, 64.0 mmol, 1.00 equiv), DMF (200 mL), HATU (48.6 g, 128 mmol, 2.00 equiv), DIEA (41.3 g, 320 mmol, 5.00 equiv) and $NH_4Cl$ (5.13 g, 96.0 mmol, 1.50 equiv) at room temperature. The resulting mixture was stirred at room temperature for 2 h. The reaction was quenched by the addition of Water (300 mL) at 0° C. The resulting mixture was extracted with EtOAc (3×200 mL). The combined organic layers were washed with brine (1×200 mL), dried over anhydrous $Na_2SO_4$. After filtration, the filtrate was concentrated under reduced pressure. The residue was purified by silica gel column chromatography, eluted with PE/EtOAc (3:1) to afford tert-butyl (S)-(1-amino-1-oxopropan-2-yl)(methyl) carbamate (13 g, 85% yield, 90% purity) as a colorless oil.

tert-butyl (S)-(1-cyanoethyl)(methyl)carbamate (25)

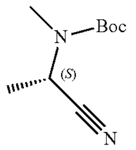

Into a 250 mL 3-necked round-bottom flask were added tert-butyl (S)-(1-amino-1-oxopropan-2-yl)(methyl)carbamate (5.00 g, 24.7 mmol, 1.0 equiv), THF (100 mL) and pyridine (7.80 g, 98.9 mmol, 4.00 equiv) at room temperature. To the above mixture was added 2,2,2-trifluoroacetyl 2,2,2-trifluoroacetate (10.4 g, 49.4 mmol, 2.00 equiv) dropwise over 10 min at 0° C. The resulting mixture was stirred at room temperature for additional 2 h. The resulting mixture was concentrated under reduced pressure. The resulting mixture was diluted with water (20 mL). The resulting mixture was extracted with EtOAc (3×20 mL). The combined organic layers were washed with brine (2×20 mL), dried over anhydrous $Na_2SO_4$. After filtration, the filtrate was concentrated under reduced pressure. The residue was purified by silica gel column chromatography, eluted with petroleum ether/ethyl acetate (3:1) to afford tert-butyl (S)-(1-cyanoethyl)(methyl)carbamate (3 g, 65% yield, 90% purity) as a colorless oil.

(S)-2-(methylamino)propanenitrile (26)

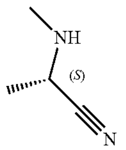

Into a 50 mL 3-necked round-bottom flask were added tert-butyl (S)-(1-cyanoethyl)(methyl)carbamate (500 mg, 2.70 mmol, 1.00 equiv), DCM (10 mL) and 2,6-dimethylpyridine (872 mg, 8.10 mmol, 3.00 equiv) at room temperature. To the above mixture was added iodotrimethylsilane (1.10 g, 5.40 mmol, 2.00 equiv) dropwise over 5 min at 0° C. The resulting mixture was stirred at 0° C. for additional 1 h. The resulting mixture was concentrated under vacuum. This resulted in(S)-2-(methylamino) propanenitrile (500 mg, crude) as a brown oil.

(4S,5S)-N-((S)-1-cyanoethyl)-4-cyclopropyl-7-ethyl-N-methyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxamide (I-549)

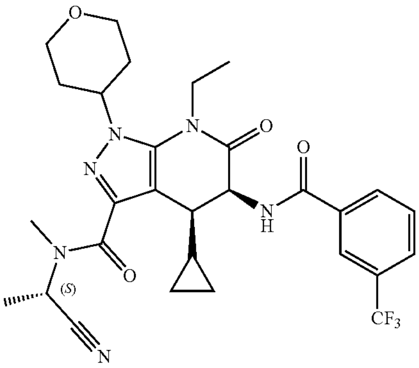

Into a 8 mL vial were added (4S,5S)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (100 mg, 0.190 mmol, 1.00 equiv), DMF (2 mL), HATU (88.0 mg, 0.230 mmol, 1.20 equiv), (S)-2-(methylamino) propanenitrile (32.0 mg, 0.380 mmol, 2.00 equiv) and DIEA (74.0 mg, 0.580 mmol, 3.00 equiv) at room temperature. The resulting mixture was stirred at room temperature for 1 h. The reaction was quenched by the addition of Water (0.5 mL) at room temperature. The residue was purified by reversed-phase flash chromatography with the following conditions: Column: SunFire Prep C18 OBD Column, 30*150 mm, 5 μm; Mobile Phase A: Water (0.1% FA), Mobile Phase B: ACN; Flow rate: 35 mL/min; Gradient: isocratic 55%-67% 10 min; Wave Length: 254 nm/220 nm; RT1(min): 9.7. This resulted in (4S,5S)—N-[(1S)-1-cyanoethyl]-4-cyclopropyl-7-ethyl-N-methyl-1-(oxan-4-yl)-6-oxo-5-[3-(trifluoromethyl)benzamido]-4H,5H-pyrazolo[3,4-b]pyridine-3-carboxamide (I-549) (20 mg, 17% yield, 98.2% purity) as a white solid.

Compounds below prepared similarly as I-343.

| | |
|---|---|
| 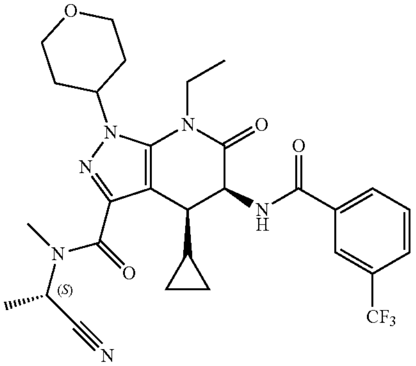<br>I-549 | $^1$H NMR (400 MHz, Acetonitrile-$d_3$) δ 8.18 (s, 1H), 8.15 (d, J = 7.8 Hz, 1H), 7.91 (d, J = 7.8 Hz, 1H), 7.73 (t, J = 7.8 Hz, 1H), 7.65 (d, J = 6.8 Hz, 1H), 6.25-5.51 (m, 1H), 4.96 (t, J = 6.3 Hz, 1H), 4.59-4.34 (m, 1H), 4.15-3.85 (m, 4H), 3.67-3.46 (m, 2H), 3.45-3.02 (m, 4H), 2.37 (qd, J = 12.1, 4.6 Hz, 1H), 2.14-2.03 (m, 1H), 1.95-1.87 (m, 2H), 1.76-1.53 (m, 3H), 1.33 (t, J = 7.0 Hz, 3H), 0.74 (s, 1H), 0.53 (dd, J = 9.8, 7.1 Hz, 1H), 0.31-0.22 (m, 1H), 0.16 (s, 2H). LCMS Calculated for $C_{29}H_{33}F_3N_6O_4$: 586.25; Observed (Method K): 585.3 [M − H]$^-$, 98.2% at RT 1.123 min. |
| 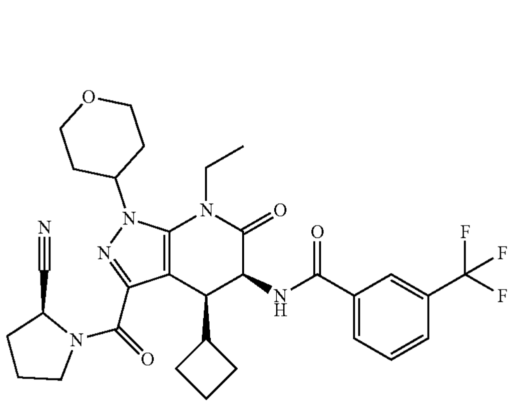 [SMILES: CCN1C(=O)[C@@H](NC(=O)c2cccc(C(F)(F)F)c2)[C@@H](C2CCC2)c2c(C(=O)N3CCC[C@H]3C#N)nn(C3CCOCC3)c21]<br>I-692 | $^1$H NMR (300 MHz, DMSO-$d_6$) δ 8.85-8.73 (m, 1H), 8.32-8.18 (m, 2H), 7.95 (d, J = 7.8 Hz, 1H), 7.75 (t, J = 7.8 Hz, 1H), 5.74-4.83 (m, 2H), 4.62-4.35 (m, 1H), 4.25-3.80 (m, 5H), 3.73-3.42 (m, 4H), 2.42-2.18 (m, 3H), 2.14-1.80 (m, 7H), 1.78-1.41 (m, 5H), 1.25 (d, J = 3.6 Hz, 3H). LCMS Calculated for $C_{31}H_{35}F_3N_6O_4$: 612.27; Observed (Method-M): 613.4 [M + H]$^+$, 99.1% at RT 1.767 min. Chiral-SFC (Method-F): 97.9% at RT 0.615 min |

-continued

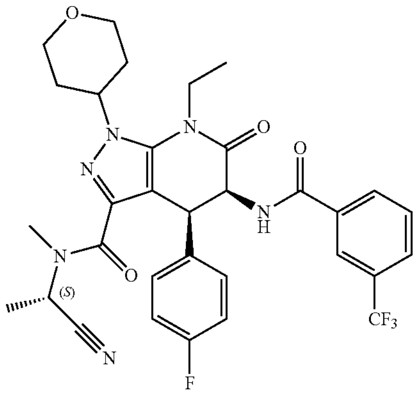

I-368

$^1$H NMR (400 MHz, Acetonitrile-$d_3$) δ 8.05 (s, 1H), 7.98 (d, J = 7.8 Hz, 1H), 7.92-7.85 (m, 1H), 7.68 (t, J = 7.8 Hz, 1H), 7.17 (d, J = 6.4 Hz, 1H), 7.02 (d, J = 7.2 Hz, 4H), 6.48-5.44 (m, 1H), 5.13 (t, J = 6.7 Hz, 1H), 5.04-4.86 (m, 1H), 4.67-4.42 (m, 1H), 4.23-3.94 (m, 4H), 3.77-3.46 (m, 2H), 3.50-2.85 (m, 3H), 2.45 (d, J = 11.8 Hz, 1H), 2.25-2.17 (m, 1H), 2.13-2.06 (m, 1H), 2.02-2.00 (m, 1H), 1.75-1.45 (m, 3H), 1.42 (t, J = 7.1 Hz, 3H). LCMS Calculated for $C_{32}H_{32}F_4N_6O_4$: 640.24; Observed (Method K): 639.4 $[M-H]^-$, 98.9% at RT 1.178 min.

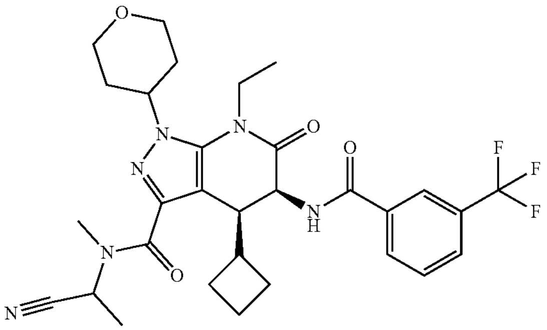 [SMILES: CCN1C(=O)[C@@H](NC(=O)c2cccc(C(F)(F)F)c2)[C@@H](C2CCC2)c2c(C(=O)N(C)C(C)C#N)nn(C3CCOCC3)c21]

I-375

$^1$H NMR (400 MHz, Chloroform-d) δ 8.09 (s, 1H), 8.00 (d, J = 7.8 Hz, 1H), 7.79 (d, J = 7.8 Hz, 1H), 7.60 (t, J = 7.8 Hz, 1H), 7.17-7.03 (m, 1H), 6.37-5.78 (m, 1H), 4.92-4.83 (m, 1H), 4.31 (dq, J = 11.3, 7.3, 5.6 Hz, 1H), 4.25-4.17 (m, 1H), 4.12 (d, J = 11.6 Hz, 1H), 4.08-3.76 (m, 3H), 3.62-3.45 (m, 2H), 3.44-3.06 (m, 3H), 2.61-2.38 (s, 1H), 2.33-1.93 (m, 4H), 1.92-1.64 (m, 7H), 1.61-1.52 (m, 2H), 1.36 (t, J = 7.1 Hz, 3H). LCMS Calculated for $C_{30}H_{35}F_3N_6O_4$: 600.27; Observed (Method-N): 601.4 $[M+H]^+$, 99.8% at RT 1.907 min.
Chiral-SFC (Method-G): 97.5% at RT 1.008 min

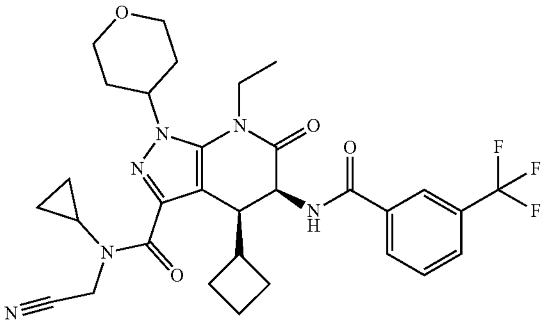 [SMILES: CCN1C(=O)[C@@H](NC(=O)c2cccc(C(F)(F)F)c2)[C@@H](C2CCC2)c2c(C(=O)N(CC#N)C3CC3)nn(C3CCOCC3)c21]

I-515

$^1$H NMR (300 MHz, DMSO-$d_6$) δ 8.77 (d, J = 7.5 Hz, 1H), 8.35-8.15 (m, 2H), 7.95 (d, J = 7.8 Hz, 1H), 7.75 (t, J = 7.8 Hz, 1H), 4.97 (dd, J = 7.5, 6.1 Hz, 1H), 4.79-4.41 (m, 3H), 4.16-3.98 (m, 2H), 3.97-3.88 (m, 1H), 3.88-3.74 (m, 1H), 3.63-3.40 (m, 3H), 3.14 (s, 1H), 2.47-2.18 (m, 2H), 2.15-1.82 (m, 4H), 1.80-1.43 (m, 5H), 1.24 (t, J = 7.0 Hz, 3H), 0.89-0.68 (m, 3H), 0.53 (s, 1H). LCMS Calculated for $C_{31}H_{35}F_3N_6O_4$: 612.27; Observed (Method-N): 613.4 $[M+H]^+$, 99.9% at RT 1.888 min.

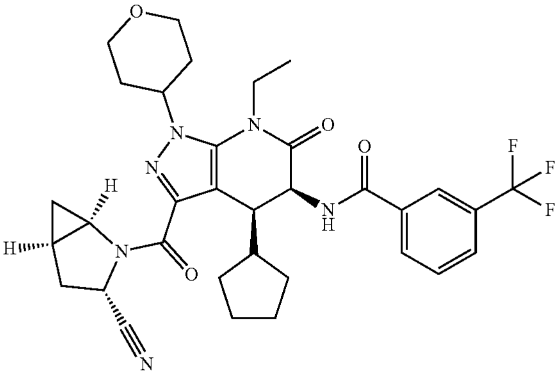 [SMILES: CCN1C(=O)[C@@H](NC(=O)c2cccc(C(F)(F)F)c2)[C@@H](C2CCCC2)c2c(C(=O)N3[C@H](C#N)C[C@H]4C[C@H]43)nn(C3CCOCC3)c21]

I-376

$^1$H NMR (300 MHz, DMSO-$d_6$) δ 8.92 (d, J = 7.7 Hz, 1H), 8.39-8.17 (m, 2H), 7.95 (d, J = 7.8 Hz, 1H), 7.76 (t, J = 7.8 Hz, 1H), 5.16-4.91 (m, 1H), 4.83 (dd, J = 8.7, 6.2 Hz, 1H), 4.49 (s, 1H), 4.34 (q, J = 5.6 Hz, 1H), 4.18-3.79 (m, 4H), 3.79-3.61 (m, 1H), 3.62-3.41 (m, 2H), 2.49-2.21 (m, 3H), 2.19-1.59 (m, 6H), 1.42 (s, 5H), 1.27 (d, J = 7.4 Hz, 3H), 1.12-0.75 (m, 3H), 0.72-0.39 (m, 1H). LCMS Calculated for $C_{33}H_{37}F_3N_6O_4$: 638.28; Observed (Method-AS): 639.69 $[M+H]^+$, 99.9% at RT 1.230 min.
Chiral-SFC (Method-E): 98.8% at RT 0.720 min 9. Synthesis of N-((4S,5S)-3-cyano-2-azabicyclo[3.1.0]hexane-2-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide-(I-703)

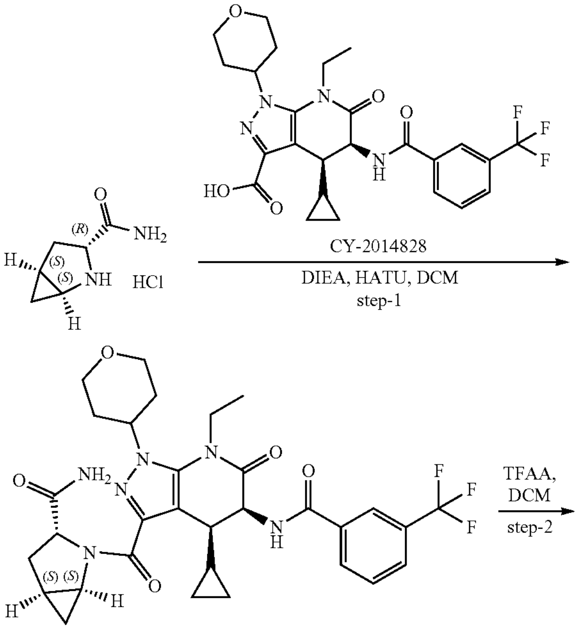

27

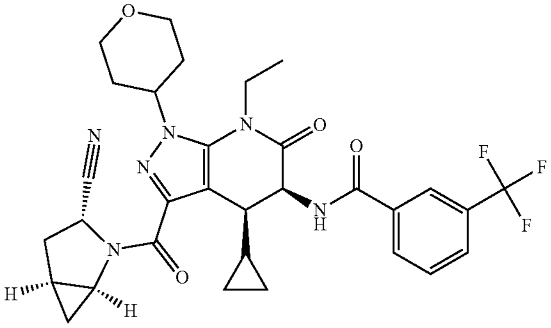

I-703

(1S,3R,5S)-2-((4S,5S)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carbonyl)-2-azabicyclo[3.1.0]hexane-3-carboxamide (27)

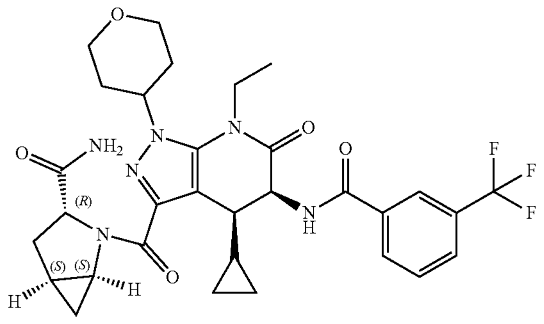

To the solution of (4S,5S)-4-cyclopropyl-7-ethyl-1-(oxan-4-yl)-6-oxo-5-[3-(trifluoromethyl)benzamido]-4H,5H-pyrazolo[3,4-b]pyridine-3-carboxylic acid (100 mg, 0.192 mmol, 1.00 equiv), DIEA (74.4 mg, 0.576 mmol, 3.00 equiv), HATU (87.6 mg, 0.230 mmol, 1.20 equiv) in DCM (1.50 mL) was added (1S,3R,5S)-2-azabicyclo[3.1.0]hexane-3-carboxamide (48.4 mg, 0.384 mmol, 2.00 equiv) in portions at room temperature. The resulting mixture was stirred at room temperature for 1 h. The resulting mixture was purified by silica gel column chromatography, eluted with $CH_2Cl_2$/MeOH (10:1) to afford (1S,3R,5S)-2-((4S,5S)-4-cyclopropyl-7-ethyl-6-oxo-1-(tetrahydro-2H-pyran-4-yl)-5-(3-(trifluorom ethyl)benzamido)-4,5,6,7-tetrahydro-1H-pyrazolo[3,4-b]pyridine-3-carbonyl)-2-azabicyclo[3.1.0]hexane-3-carboxamide (70 mg, 57.9% yield, 97.8% purity) as a white solid.

LCMS Calculated for $C_{31}H_{35}F_3N_6O_5$: 628.26; Observed: 629.3 $[M+H]^+$

N-((4S,5S)-3-((1S,3R,5S)-3-cyano-2-azabicyclo[3.1.0]hexane-2-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-703)

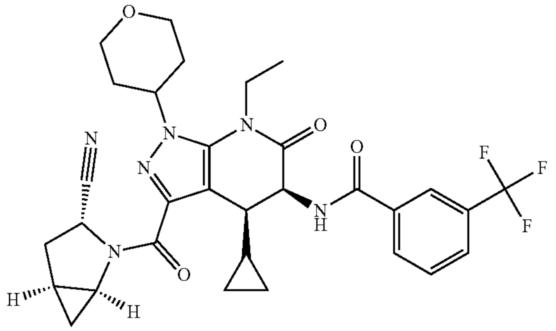

A solution of (1S,3R,5S)-2-((4S,5S)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carbonyl)-2-azabicyclo[3.1.0]hexane-3-carboxamide (70.0 mg, 0.111 mmol, 1.00 equiv), $Et_3N$ (45.0 mg, 0.444 mmol, 4.00 equiv) in DCM (1 mL) at 0° C. for 10 min followed by the addition of 2,2,2-trifluoroacetyl 2,2,2-trifluoroacetate (46.7 mg, 0.222 mmol, 2.00 equiv) in portions at 0° C. The resulting mixture was stirred at room temperature for 2 h. The mixture was basified to pH 7 with saturated $NaHCO_3$(aq.). The resulting mixture was extracted with $CH_2C_{12}$ (3×10 mL). The combined organic layers were washed with brine (3×20 mL), dried over anhydrous $Na_2SO_4$. After filtration, the filtrate was concentrated under reduced pressure. The crude product was purified by Prep-HPLC with the following conditions (Column: Uitimate-XB-C18 Column, 30*150 mm, 10 μm; Mobile Phase A: Water (10 mmol/L $NH_4HCO_3$+0.05$NH_3H_2O$), Mobile Phase B: ACN; Flow rate: 90 mL/min; Gradient: isocratic 35%-85% 11 min; Wave Length: 254 nm/220 nm; RT1(min): 10.5) to afford N-((4S,5S)-3-((1S,3R,5S)-3-cyano-2-azabicyclo[3.1.0]hexane-2-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (20 mg, 29.4% yield, 99.4% purity) as a white solid.

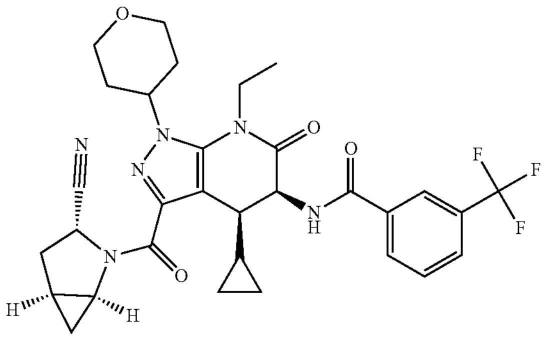 [SMILES: CCN1C(=O)[C@@H](NC(=O)c2cccc(C(F)(F)F)c2)[C@@H](C2CC2)c2c(C(=O)N3[C@@H](C#N)C[C@@H]4C[C@@H]43)nn(C3CCOCC3)c21]

I-703

$^1$H NMR (400 MHz, DMSO-$d_6$) δ 9.02 (t, J = 8.0 Hz, 1H), 8.31 (s, 1H), 8.24 (d, J = 7.8 Hz, 1H), 7.96 (d, J = 7.8 Hz, 1H), 7.76 (t, J = 7.8 Hz, 1H), 5.66-4.86 (m, 2H), 4.58-4.45 (m, 1H), 4.25-3.99 (m, 3H), 3.93 (d, J = 11.9 Hz, 1H), 3.85 (m, 7.0 Hz, 1H), 3.62-3.42 (m, 3H), 2.49-2.21 (m, 3H), 2.13-1.82 (m, 4H), 1.25 (m, 3.6 Hz, 3H), 1.02-0.87 (m, 1H), 0.82 (d, J = 6.5 Hz, 1H), 0.74-0.47 (m, 2H), 0.27-0.07 (m, 3H).
LCMS Calculated for: $C_{31}H_{33}F_3N_6O_4$, 610.25.; Observed (Method-A): 611.3[M + H]$^+$, 99.4% at RT 1.197 min,

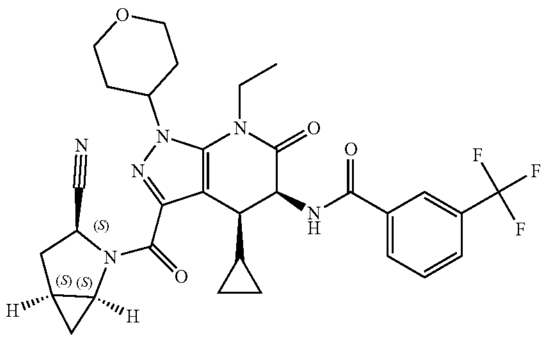

I-441

$^1$H NMR (300 MHz, DMSO-$d_6$) δ 9.04 (t, J = 7.4 Hz, 1H), 8.32 (s, 1H), 8.25 (d, J = 7.9 Hz, 1H), 7.96 (d, J = 7.9 Hz, 1H), 7.76 (t, J = 7.8 Hz, 1H), 5.91-5.24 (m, 1H), 5.14-4.96 (m, 1H), 4.69-4.45 (m, 2H), 4.20-3.78 (m, 5H), 3.64-3.46 (m, 2H), 3.43-3.36 (m, 1H), 2.43-2.18 (m, 2H), 2.15-1.67 (m, 5H), 1.26 (t, J = 6.8 Hz, 3H), 1.11-0.94 (m, 1H), 0.90-0.76 (m, 2H), 0.31-0.04 (m, 3H).
LCMS Calculated for $C_{31}H_{34}F_3N_6O_4$: 610.25 Observed (Method A): 611.4 [M + H]$^+$, 99.6% at RT 1.194 min.

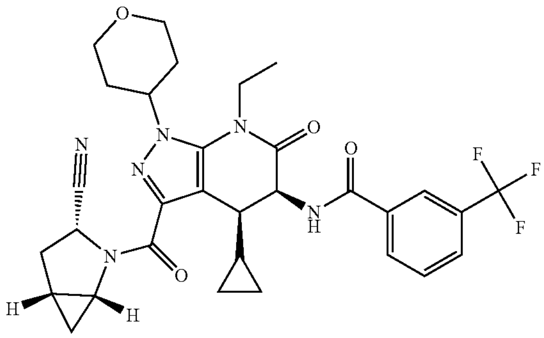 [SMILES: CCN1C(=O)[C@@H](NC(=O)c2cccc(C(F)(F)F)c2)[C@@H](C2CC2)c2c(C(=O)N3[C@@H]4C[C@@H]4C[C@@H]3C#N)nn(C3CCOCC3)c21]

I-442

$^1$H NMR (400 MHz, DMSO-$d_6$) δ 9.02 (dd, J = 10.5, 8.0 Hz, 1H), 8.31 (s, 1H), 8.25 (d, J = 7.5 Hz, 1H), 7.96 (d, J = 7.8 Hz, 1H), 7.76 (t, J = 7.8 Hz, 1H), 5.90-5.19 (m, 1H), 5.08 (m, 1H), 4.70-4.54 (m, 1H), 4.52 (s, 1H), 4.18-4.03 (m, 2H), 4.01-3.86 (m, 2H), 3.61-3.35 (m, 3H), 2.72-2.54 (m, 1H), 2.39 (d, J = 13.7 Hz, 1H), 2.25 (dd, J = 13.6, 2.0 Hz, 1H), 2.15-1.68 (m, 4H), 1.27 (m, 3H), 1.06-0.75 (m, 3H), 0.49 (dd, J = 11.6, 5.8 Hz, 1H), 0.27-0.03 (m, 3H).
LCMS Calculated for $C_{31}H_{33}F_3N_6O_4$: 610.25; Observed (Method-X): 611.3[M + H]$^+$, 97.5% at RT 1.426 min.

10. Synthesis of N-((4S,5S)-3-((2S,4R)-cyano-4-(methylamino)pyrrolidine-1-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-425)

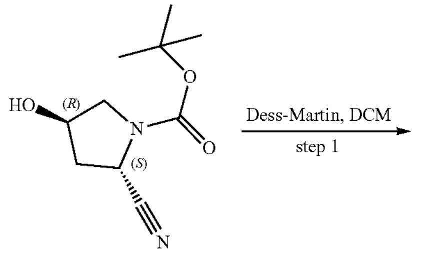

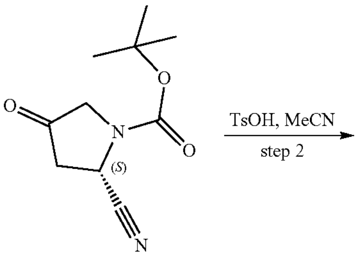

33

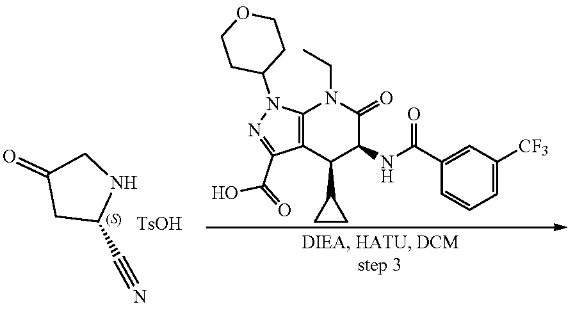

34

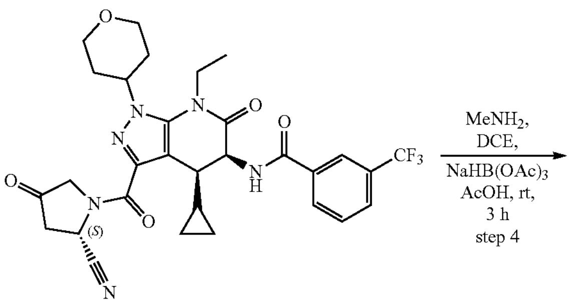

I-626

-continued

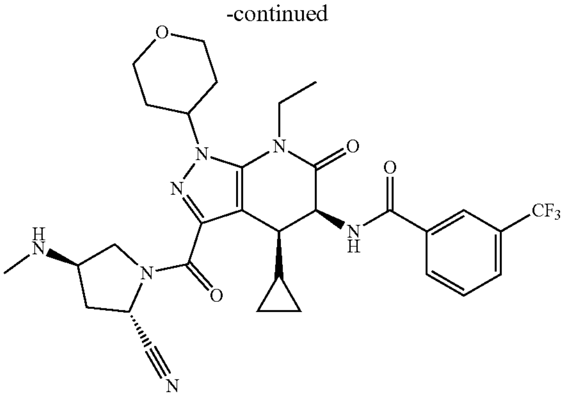
I-425

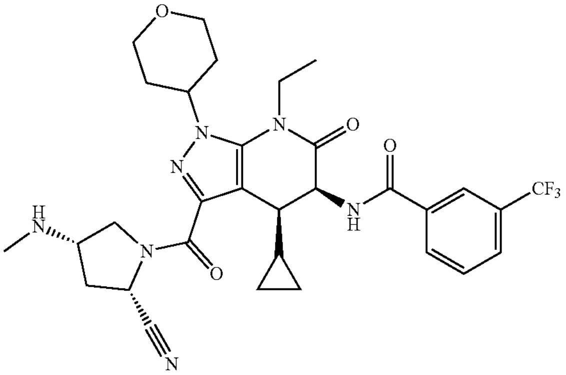
I-503

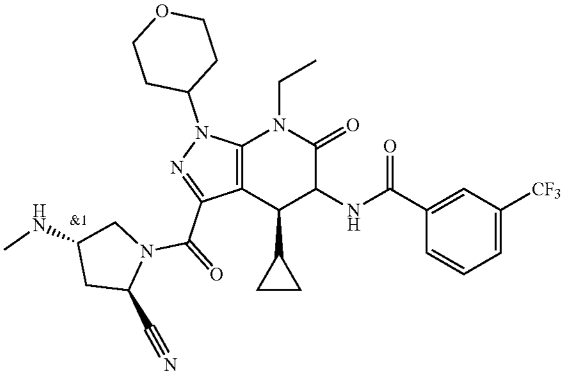
I-420 tert-butyl (S)-2-cyano-4-oxopyrrolidine-1-carboxylate (33)

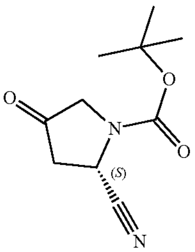

To a stirred solution of tert-butyl (2S,4R)-2-cyano-4-hydroxypyrrolidine-1-carboxylate (1.00 g, 4.71 mmol, 1.00 equiv) in DCM (10 mL) was added Dess-Martin (4.00 g, 9.42 mmol, 2.00 equiv) in portions at room temperature. The resulting mixture was stirred at room temperature for 2.5 h. The reaction was monitored by LCMS. After completion of reaction, the resulting mixture was filtered, the filter cake was washed with DCM (3×10 mL). The filtrate was extracted with DCM (3×10 mL). The combined organic layers were washed with saturated $NaHCO_3$ (3×15 mL), dried over anhydrous $Na_2SO_4$. After filtration, the filtrate was concentrated under reduced pressure. The residue was purified by silica gel column chromatography, eluted with PE/EtOAc=3/1 to afford tert-butyl (S)-2-cyano-4-oxopyrrolidine-1-carboxylate (860 mg, 86.8% yield) as an off-white solid.

LCMS Calculated for $C_{10}H_{14}N_2O_3$: 210.1; Observed: 211.2 $[M+H]^+$.

(S)-4-oxpyrrolidine-2-carbonitrile P-Toluenesulfonate (34)

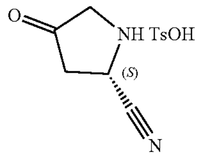

3

To a stirred solution of tert-butyl (S)-2-cyano-4-oxopyrrolidine-1-carboxylate (200 mg, 0.951 mmol, 1.00 equiv) in acetonitrile was added TsOH (361 mg, 1.90 mmol, 2.00 equiv) in portions at 0° C. The resulting mixture was stirred at room temperature for 0.5 h. The reaction was monitored by LCMS. After completion of reaction, the mixture was concentrated under reduced pressure. The resulting mixture was washed with 3×10 mL of anhydrous ether to afford (S)-4-oxopyrrolidine-2-carbonitrile P-Toluenesulfonate (164 mg) as white solid.

N-((4S,5S)-3-((S)-2-cyano-4-oxopyrrolidine-1-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-626)

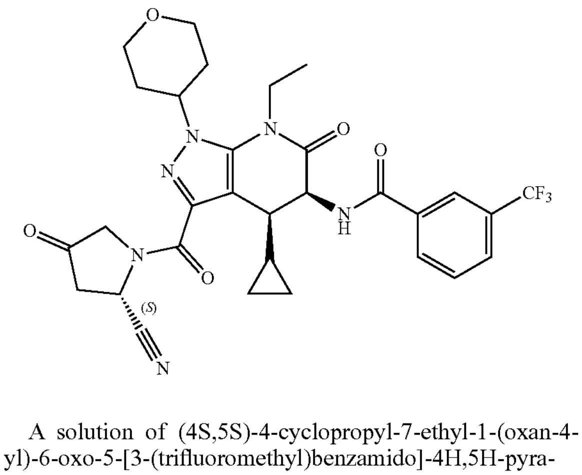

A solution of (4S,5S)-4-cyclopropyl-7-ethyl-1-(oxan-4-yl)-6-oxo-5-[3-(trifluoromethyl)benzamido]-4H,5H-pyrazolo[3,4-b]pyridine-3-carboxylic acid (100 mg, 0.190 mmol, 1.00 equiv) in DCM (1 mL) was treated with HATU (87.7 mg, 0.230 mmol, 1.20 equiv) at room temperature for 10 min followed by the addition of(S)-4-oxopyrrolidine-2-carbonitrile P-Toluenesulfonate (31.7 mg, 0.29 mmol, 1.50 equiv) in portions at room temperature. The resulting mixture was stirred at room temperature for 1 h. The reaction was monitored by LCMS. After completion of reaction, the resulting mixture was concentrated under reduced pressure. The residue was dissolved in ACN (2 mL). The crude product was purified by Prep-HPLC with the following conditions (Column: Sunfire-C18 Column, 30*150 mm, 5 μm; Mobile Phase A: Water (10 mmol/L $NH_4HCO_3$+ $0.05NH_3H_2O$), Mobile Phase B: ACN; Flow rate: 35 mL/min; Gradient: isocratic 25%-55% 10 min; Wave Length: 254 nm/220 nm; RT1(min): 6.8) to afford N-((4S,5S)-3-((S)-2-cyano-4-oxopyrrolidine-1-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (52 mg, 92.7% purity, 44.4% yield) as an off-white solid.

$^1$H NMR (300 MHZ, DMSO-$d_6$) δ 9.03 (d, J=7.8 Hz, 1H), 8.37-8.15 (m, 2H), 7.96 (d, J=7.9 Hz, 1H), 7.76 (t, J=7.9 Hz, 1H), 5.41-5.29 (m, 1H), 5.11-4.93 (m, 1H), 4.50 (s, 2H), 4.28-4.00 (m, 2H), 4.00-3.76 (m, 2H), 3.66-3.60 (m, 1H), 3.49 (t, J=6.5 Hz, 2H), 3.37 (d, J=7.1 Hz, 1H), 3.18-3.04 (m, 1H), 2.99-2.85 (m, 1H), 2.24 (s, 1H), 2.19-1.88 (m, 3H), 1.27 (q, J=7.9, 7.1 Hz, 3H), 0.84 (s, 1H), 0.49 (s, 1H), 0.14 (d, J=11.5 Hz, 3H).

LCMS Calculated for $C_{30}H_{31}F_3N_6O_5$: 612.2; Observed (Method-C): 613.2 $[M+H]^+$, 92.78% at RT 1.221 min.

N-((4S,5S)-3-((2S,4R)-2-cyano-4-(methylamino)pyrrolidine-1-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-425)

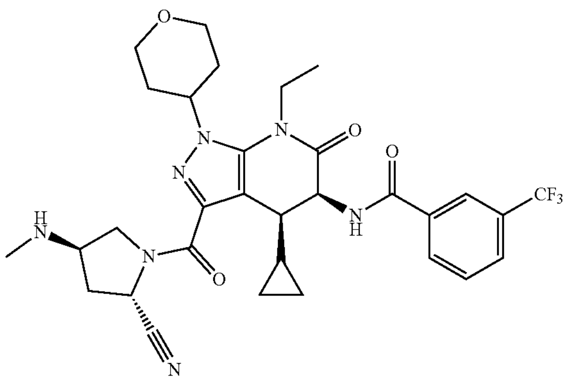

A solution of N-[(4S,5S)-3-[(2S)-2-cyano-4-oxopyrrolidine-1-carbonyl]-4-cyclopropyl-7-ethyl-1-(oxan-4-yl)-6-oxo-4H,5H-pyrazolo[3,4-b]pyridin-5-yl]-3-[(difluoromethyl)-lambda2-fluoranyl]benzamide (100 mg, 0.163 mmol, 1 equiv) in methanol (1 mL) was treated with Methylamine (3.11-1.5 M in Tetrahydrofuran) (7.16 mg, 0.230 mmol, 1.2 equiv) at room temperature for 0.5 h followed by the addition of sodium cyanoboranuide (24.2 mg, 0.384 mmol, 2 equiv) in portions at room temperature. The resulting mixture was stirred at room temperature for 4 h. The reaction was monitored by LCMS. After completion of reaction, the crude product was purified by Prep-HPLC with the following conditions (Column: Xselsect CSH OBD Column, 30*150 mm, 5 μm; Mobile Phase A: Water (0.1% FA), Mobile Phase B: MeOH; Flow rate: 35 mL/min; Gradient: isocratic 30%-68% 10 min; Wave Length: 254 nm/220 nm; RT1(min): 9.3) and by SFC with the following conditions (Column: XA-CHIRALPAK IG, 3*25 cm, 5 μm; Mobile Phase A: $CO_2$, Mobile Phase B: MeOH: DCM=2: 1 (0.1% 2M $NH_3$-MeOH); Flow rate: 80 mL/min; Gradient: isocratic 35% B; Column Temperature (° C.): 35; Back Pressure (bar): 100; Wave Length: 220 nm; RT1(min): 3.6; RT2(min): 5; Sample Solvent: MeOH; Injection Volume: 1.5 mL) to afford N-((4S,5S)-3-((2S,4R)-2-cyano-4-(methylamino) pyrrolidine-1-carbonyl)-4-cyclopropyl-7-ethyl-6-oxo-1-(tetrahydro-2H-pyran-4-yl)-4,5,6,7-tetrahydro-1H-pyrazolo [3,4-b]pyridin-5-yl)-3-(trifluoromethyl)benzamide (3 mg, 98.7% purity, 2.9% yield, (I-425) as a white solid, N-((4S, 5S)-3-((2S,4S)-2-cyano-4-(methylamino) pyrrolidine-1-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (3 mg, 97.1% purity, 2.9% yield, (I-503) as a white solid, N-[(4S,5S)-3-[(2S, 4R*)-2-cyano-4-(methylamino) pyrrolidine-1-carbonyl]-4-cyclopropyl-7-ethyl-1-(oxan-4-yl)-6-oxo-4H,5H-pyrazolo [3,4-b]pyridin-5-yl]-3-(trifluoromethyl)benzamide (3 mg, 96.0% purity, 2.9% yield, (I-420) as a white solid.

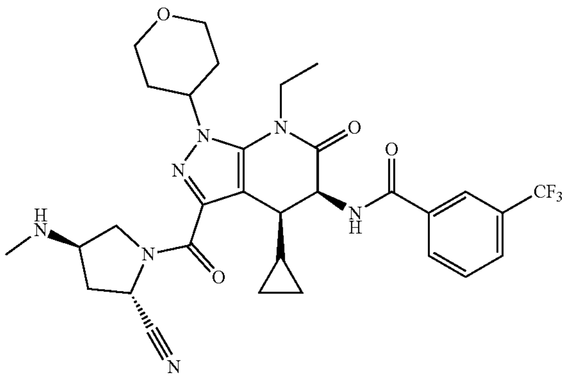 [SMILES: CCN1C(=O)[C@@H](NC(=O)c2cccc(C(F)(F)F)c2)[C@@H](C2CC2)c2c(C(=O)N3C[C@H](NC)C[C@H]3C#N)nn(C3CCOCC3)c21]

I-425

$^1$H NMR (400 MHz, DMSO-$d_6$) δ 9.01 (t, J = 8.1 Hz, 1H), 8.41-8.17 (m, 2H), 7.95 (d, J = 7.9 Hz, 1H), 7.75 (t, J = 7.8 Hz, 1H), 5.08-4.92 (m, 1H), 4.87 (t, J = 7.0 Hz, 1H), 4.51 (s, 1H), 4.15-3.98 (m, 2H), 3.94 (d, J = 7.6 Hz, 1H), 3.89-3.76 (m, 1H), 3.61-3.43 (m, 2H), 3.42 (d, J = 6.4 Hz, 2H), 2.38-2.12 (m, 5H), 2.12-1.85 (m, 4H), 1.40-1.16 (m, 5H), 0.84 (d, J = 11.1 Hz, 2H), 0.48 (s, 1H), 0.21-0.01 (m, 3H).
LCMS Calculated for $C_{31}H_{36}F_3N_7O_4$: 627.2; Observed (Method-C): 628.3 $[M + H]^+$, 98.7% at RT 0.925 min.

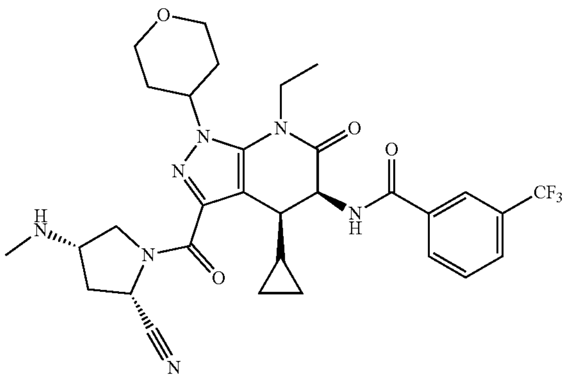 [SMILES: CCN1C(=O)[C@@H](NC(=O)c2cccc(C(F)(F)F)c2)[C@@H](C2CC2)c2c(C(=O)N3C[C@@H](NC)C[C@H]3C#N)nn(C3CCOCC3)c21]

I-503

$^1$H NMR (400 MHz, DMSO-$d_6$) δ 9.07-8.97 (m, 1H), 8.31 (s, 1H), 8.24 (d, J = 7.9 Hz, 1H), 7.95 (d, J = 7.9 Hz, 1H), 7.75 (t, J = 7.9 Hz, 1H), 5.64-4.81 (m, 2H), 4.51 (s, 1H), 4.18-3.76 (m, 6H), 3.66-3.35 (m, 4H), 2.44-2.18 (m, 5H), 2.12-1.86 (m, 4H), 1.26 (q, J = 6.7 Hz, 3H), 0.82 (s, 1H), 0.51-0.43 (m, 1H), 0.21-0.05 (m, 3H).
LCMS Calculated for $C_{31}H_{36}F_3N_7O_4$: 627.2; Observed (Method-P): 626.3 $[M - H]^+$, 97.136% at RT 1.398 min.

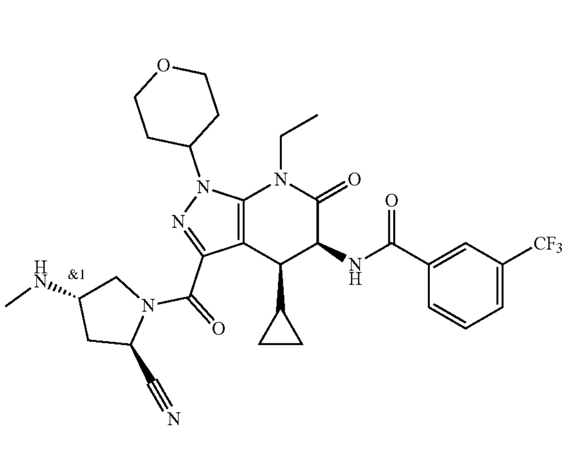 [SMILES: CCN1C(=O)[C@@H](NC(=O)c2cccc(C(F)(F)F)c2)[C@@H](C2CC2)c2c(C(=O)N3C[C@@H](NC)C[C@@H]3C#N)nn(C3CCOCC3)c21]

I-420

$^1$H NMR (400 MHz, DMSO-$d_6$) δ 9.02 (d, J = 8.1 Hz, 1H), 8.30 (s, 1H), 8.23 (d, J = 7.8 Hz, 1H), 7.95 (d, J = 8.0 Hz, 1H), 7.75 (t, J = 7.8 Hz, 1H), 5.25 (s, 1H), 5.02-4.92 (m, 1H), 4.58-4.45 (m, 2H), 4.17-3.99 (m, 3H), 3.98-3.90 (m, 1H), 3.90-3.77 (m, 1H), 3.62-3.44 (m, 3H), 3.06-2.76 (m, 3H), 2.36-2.11 (m, 2H), 2.11-1.83 (m, 4H), 1.31-1.19 (m, 4H), 0.89-0.75 (m, 2H), 0.54-0.41 (m, 1H), 0.32-0.03 (m, 3H).
LCMS Calculated for $C_{31}H_{36}F_3N_7O_4$: 627.2; Observed (Method-E): 628.6 $[M + H]^+$, 96.050% at RT 1.306 min.

11. Synthesis of N-((4S,5S)-3-((2S)-2-cyano-4-(methylamino) pyrrolidine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-509)

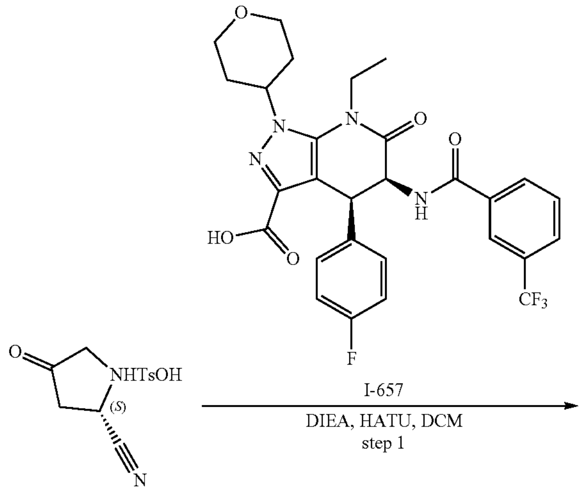

I-657

34

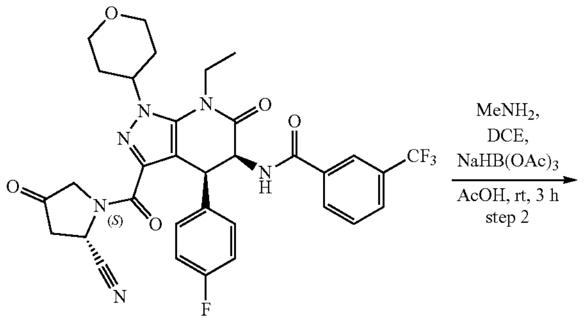

35

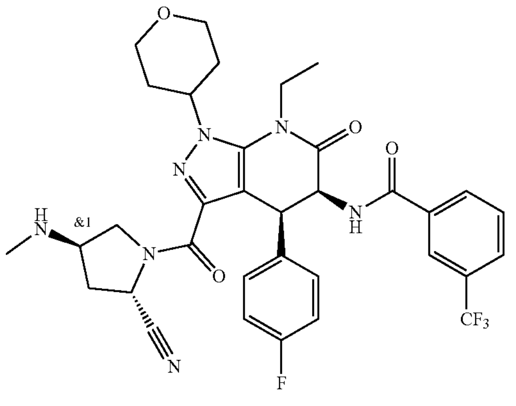

I-509

N-((4S,5S)-3-((S)-2-cyano-4-oxopyrrolidine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide( 35)

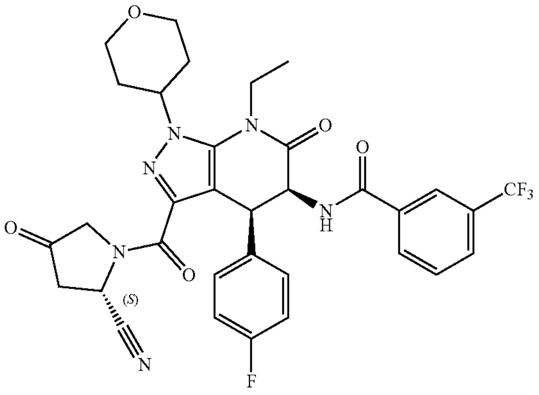

A solution of (4S,5S)-7-ethyl-4-(4-fluorophenyl)-1-(oxan-4-yl)-6-oxo-5-[3-(trifluoromethyl)benzamido]-4H,5H-pyrazolo[3,4-b]pyridine-3-carboxylic acid (250 mg, 0.435 mmol, 1.00 equiv) in DCM (3 mL) was treated with HATU (1989 mg, 0.522 mmol, 1.20 equiv) and DIEA (168 mg, 1.31 mmol, 3.00 equiv) at room temperature for 10 min followed by the addition of (2S)-4-oxopyrrolidine-2-carbonitrile (71.9 mg, 0.652 mmol, 1.50 equiv) in portions at room temperature. The resulting mixture was stirred at room temperature for 1 h. The reaction was monitored by LCMS. After completion of reaction, the resulting mixture was concentrated under reduced pressure. The residue was dissolved in ACN (2 mL). The crude product was purified by Prep-HPLC with the following conditions (Column: XBridge Prep OBD C18 Column, 30*150 mm, 5 μm; Mobile Phase A: Water (0.05% $NH_3H_2O$), Mobile Phase B: ACN; Flow rate: 35 mL/min; Gradient: isocratic 55%-63% 10 min; Wave Length: 254 nm/220 nm; RT1(min): 8.8) to afford N-((4S,5S)-3-((S)-2-cyano-4-oxopyrrolidine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (280 mg) as an off-white solid.

LCMS Calculated for $C_{33}H_{30}F_4N_6O_5$: 666.2; Observed: 667.3 $[M+H]^+$.

N-((4S,5S)-3-((2S,4R)-2-cyano-4-(methylamino)pyrrolidine-1-carbonyl)-7-ethyl-4-(fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-509)

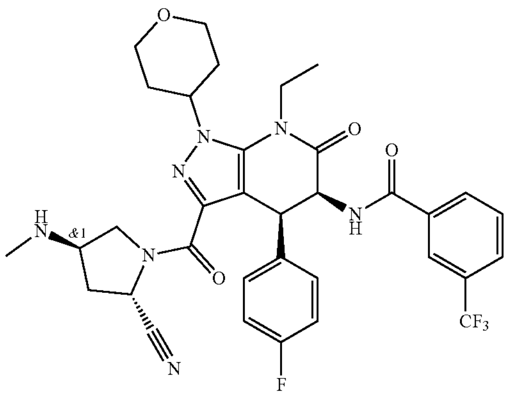

I-509

A solution of N-((4S,5S)-3-((S)-2-cyano-4-oxopyrrolidine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (100 mg, 0.150 mmol, 1.00 equiv) in methanol (1 mL) was treated with Methylamine (3.1-3.5M in Tetrahydrofuran) (5.58 mg, 0.180 mmol, 1.20 equiv) at room temperature for 0.5 h followed by the addition of sodium cyanoboranuide (18.8 mg, 0.300 mmol, 2.00 equiv) in portions at room temperature. The resulting mixture was stirred at room temperature for 4 h. The reaction was monitored by LCMS. After completion of reaction, the crude product was purified by Prep-HPLC with the following conditions (Column: YMC-Actus Triart C18 ExRS Column, 30*150 mm, 5 μm; Mobile Phase A: Water (0.1% FA), Mobile Phase B: ACN; Flow rate: 30 mL/min; Gradient: 25% B to 55% B in 8 min; Wave Length: 254 nm/220 nm; RT1(min): 3.91; 5.91; 9.63) to afford N-((4S,5S)-3-((2S,4R)-2-cyano-4-(methylamino)pyrrolidine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (5 mg, 99.8% purity, 4.9% yield) as a white solid.

$^1$H NMR (400 MHZ, DMSO-$d_6$) δ 8.63-8.51 (m, 1H), 8.19-8.08 (m, 2H), 7.92 (d, J=8.2 Hz, 1H), 7.71 (t, J=7.8 Hz, 1H), 7.07 (t, J=8.6 Hz, 2H), 6.95 (dd, J=8.5, 5.5 Hz, 2H), 5.87-5.09 (m, 2H), 5.03-4.77 (m, 2H), 4.71-4.52 (m, 1H), 4.32 (s, 1H), 4.20-3.68 (m, 6H), 3.68-3.39 (m, 3H), 3.20-2.53 (m, 3H), 2.47-1.88 (m, 6H), 1.32 (dt, J=7.0, 3.6 Hz, 3H).

LCMS Calculated for $C_{34}H_{35}F_4N_7O_4$: 681.2; Observed (Method-C): 682.2 [M+H]$^+$, 99.8% at RT 0.981 min.

12. Synthesis of N-((4S,5S)-3-(trans-(2S,3S)-2-cyano-3-(methylamino)pyrrolidine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-693)

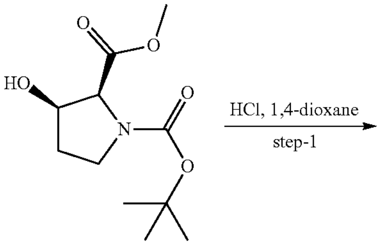

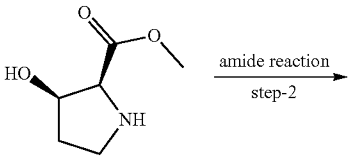

36

-continued

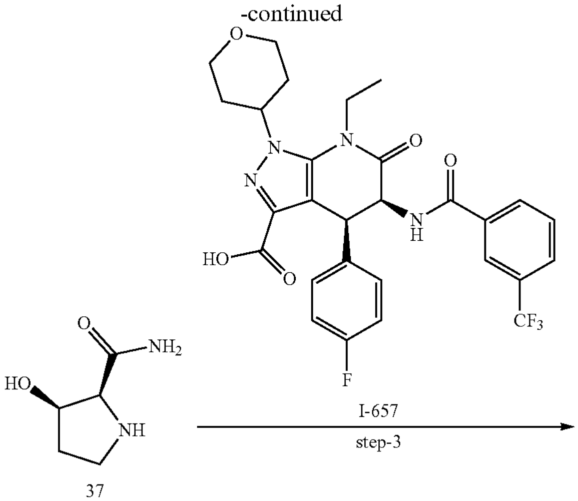

37

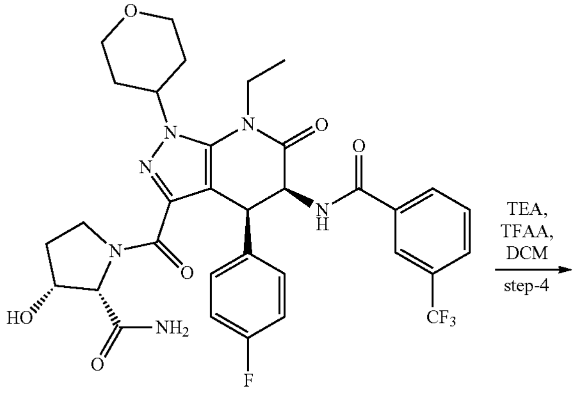

38

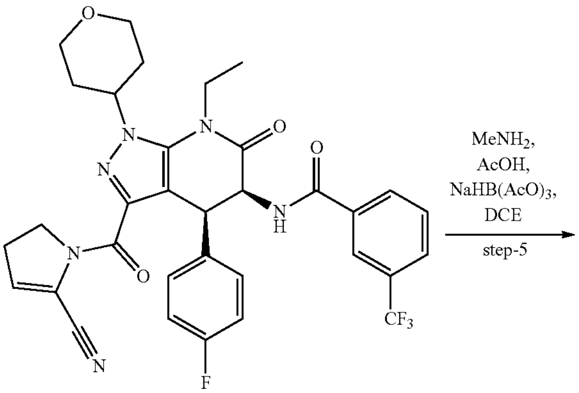

39

-continued

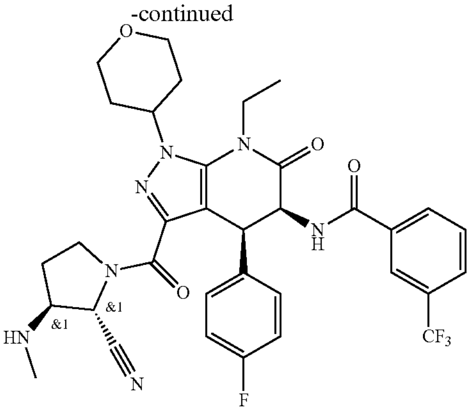

I-693 methyl (2S,3R)-3-hydroxypyrrolidine-2-carboxylate (36)

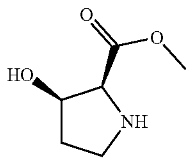

Into a 40 mL vial were added 1-tert-butyl 2-methyl (2S,3R)-3-hydroxypyrrolidine-1,2-dicarboxylate (1.00 g, 4.08 mmol, 1.00 equiv) and hydrogen chloride (4.0 M in 1,4-dioxane) (10 mL) at room temperature. The resulting mixture was stirred at room temperature for 5 h. The resulting mixture was concentrated under reduced pressure to afford methyl (2S,3R)-3-hydroxypyrrolidine-2-carboxylate (800 mg) as a yellow solid. The crude product was used in the next step directly without further purification.

(2S,3R)-3-hydroxypyrrolidine-2-carboxamide (37)

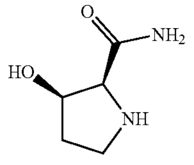

Into a 8 mL vial were added methyl (2S,3R)-3-hydroxypyrrolidine-2-carboxylate (800 mg, 5.51 mmol, 1.00 equiv) and Ammonia (2.0M in methanol) (5 mL) at room temperature. The resulting mixture was stirred at room temperature overnight. The resulting mixture was concentrated under reduced pressure. This resulted in (2S,3R)-3-hydroxypyrrolidine-2-carboxamide (700 mg) as an off-white solid. The crude product was used in the next step directly without further purification.

(2S,3R)-1-((4S,5S)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carbonyl)-3-hydroxypyrrolidine-2-carboxamide (38)

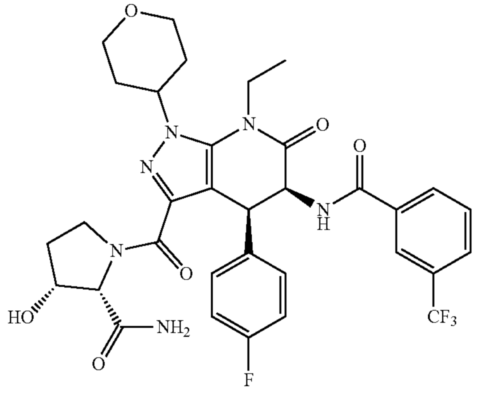

To a mixture of (4S,5S)-7-ethyl-4-(4-fluorophenyl)-1-(oxan-4-yl)-6-oxo-5-[3-(trifluoromethyl)benzamido]-4H,5H-pyrazolo[3,4-b]pyridine-3-carboxylic acid (500 mg, 0.870 mmol, 1.00 equiv) and HATU (496 mg, 1.31 mmol, 1.50 equiv) in DMF (5 mL) was added DIEA (337 mg, 2.61 mmol, 3.00 equiv) dropwise at room temperature. Then to the above solution was added (2S,3R)-3-hydroxypyrrolidine-2-carboxamide (125 mg, 0.957 mmol, 1.10 equiv). The resulting mixture was stirred at room temperature for 2 h. The resulting mixture was purified by reversed-phase flash chromatography with the following conditions: column, C18 silica gel; mobile phase, MeCN in Water (0.1% $NH_3 \cdot H_2O$), 50% to 80% gradient in 10 min; detector, UV 254 nm. This resulted in (2S,3R)-1-((4S,5S)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carbonyl)-3-hydroxypyrrolidine-2-carboxamide (350 mg, 58.57% yield, 90% purity) as a white solid.

N-((4S,5S)-3-(5-cyano-2,3-dihydro-1H-pyrrole-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-631)

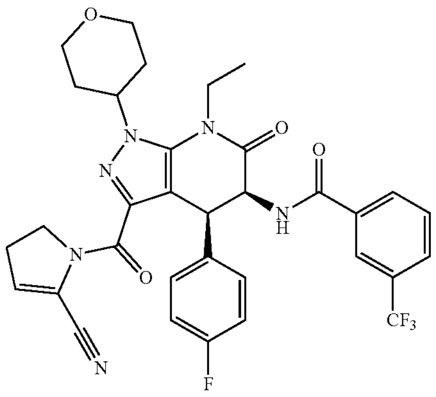 [SMILES: CCN1C(=O)[C@@H](NC(=O)c2cccc(C(F)(F)F)c2)[C@@H](c2ccc(F)cc2)c2c(C(=O)N3CCC=C3C#N)nn(C3CCOCC3)c21]

To a stirred solution of (2S,3R)-1-((4S,5S)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carbonyl)-3-hydroxypyrrolidine-2-carboxamide (110 mg, 0.160 mmol, 1.00 equiv) in DCM (2 mL) were added $Et_3N$ (97.3 mg, 0.960 mmol, 6.00 equiv) and Trifluoroacetic anhydride (135 mg, 0.640 mmol, 4.00 equiv) dropwise at room temperature. The resulting mixture was stirred at room temperature for 4 h. The resulting mixture was concentrated under reduced pressure. The crude product (60 mg) was used in the next step directly without further purification.

| | |
|---|---|
| 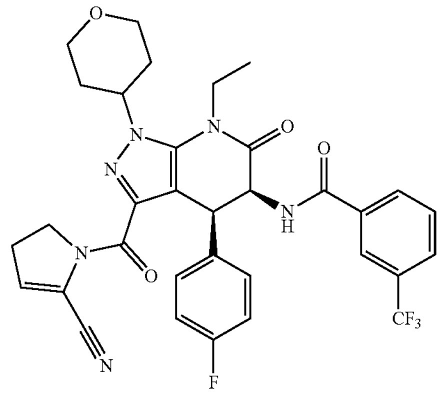<br>I-631 | $^1$H NMR (300 MHz, DMSO-d6) δ 8.54 (d, J = 7.1 Hz, 1H), 8.23-8.03 (m, 2H), 7.92 (d, J = 7.8 Hz, 1H), 7.71 (t, J = 7.8 Hz, 1H), 7.08 (t, J = 8.7 Hz, 2H), 6.99-6.88 (m, 2H), 6.69 (s, 1H), 5.23 (t, J = 7.1 Hz, 1H), 4.91 (s, 1H), 4.52 (d, J = 56.9 Hz, 3H), 4.06 (d, J = 12.3 Hz, 2H), 3.97 (d, J = 10.0 Hz, 2H), 3.68-3.49 (m, 2H), 2.86 (s, 2H), 2.18 (s, 1H), 1.99 (s, 2H), 1.32 (t, J = 6.9 Hz, 3H). LCMS Calculated for $C_{33}H_{30}F_4N_6O_4$: 650.2; Observed (Method-I): 649.3 $[M-H]^+$, 99.32% at RT 1.654 min. |
| 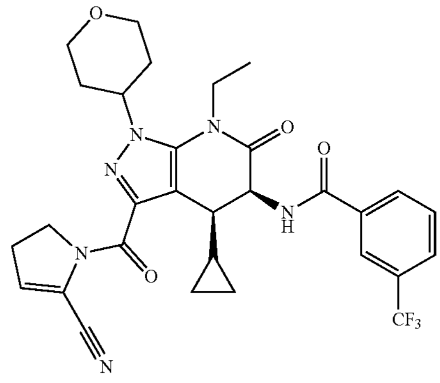 [SMILES: CCN1C(=O)[C@@H](NC(=O)c2cccc(C(F)(F)F)c2)[C@@H](C2CC2)c2c(C(=O)N3CCC=C3C#N)nn(C3CCOCC3)c21]<br>I-437 | $^1$H NMR (300 MHz, DMSO-$d_6$) δ 9.03 (d, J = 8.0 Hz, 1H), 8.31 (s, 1H), 8.24 (d, J = 7.8 Hz, 1H), 7.95 (d, J = 7.8 Hz, 1H), 7.75 (t, J = 7.8 Hz, 1H), 6.72 (s, 1H), 5.05 (t, J = 7.0 Hz, 1H), 4.66-4.27 (m, 3H), 4.19-3.79 (m, 4H), 3.52 (dt, J = 20.2, 11.3 Hz, 3H), 2.88 (s, 2H), 2.25 (d, J = 13.4 Hz, 1H), 2.12-1.86 (m, 3H), 1.25 (t, J = 6.8 Hz, 3H), 0.92-0.79 (m, 1H), 0.54-0.41 (m, 1H), 0.18 (d, J = 9.1 Hz, 1H). LCMS Calculated for $C_{30}H_{31}F_3N_6O_4$: 596.2; Observed (Method-J): 595.2 $[M-H]^+$, 98.27% at RT 1.814 min. |

N-((4S-5S)-3-(trans-(2S,3S)-2-cyano-3-(methylamino)pyrrolidine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-693)

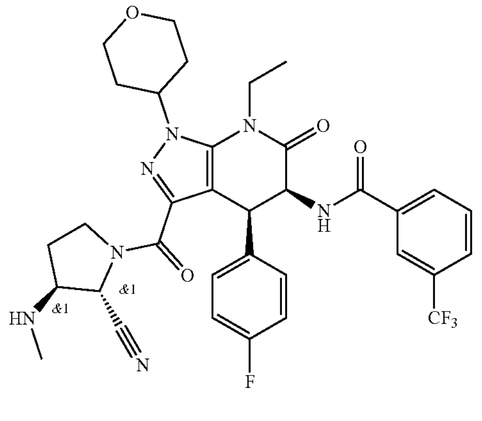

To a stirred solution of N-((4S,5S)-3-(5-cyano-2,3-dihydro-1H-pyrrole-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (40.0 mg, 0.061 mmol, 1.00 equiv) in THF (2 mL) was added methanamine (9.55 mg, 0.305 mmol, 5.00 equiv) dropwise at room temperature. The resulting mixture was stirred at room temperature for 3 h. The resulting mixture was concentrated under reduced pressure. The residue was purified by reversed-phase flash chromatography with the following conditions: column, C18 silica gel; mobile phase, MeCN in Water (0.1% $NH_3 \cdot H_2O$), 40% to 80% gradient in 10 min; detector, UV 254 nm. This resulted in N-((4S,5S)-3-(trans-(2S,3S)-2-cyano-3-(methylamino) pyrrolidine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (10 mg, 23.86% yield, 99.5% purity) as a white solid.

$^1$H NMR (300 MHZ, DMSO-$d_6$) δ 8.56-8.45 (m, 1H), 8.12 (d, J=10.7 Hz, 2H), 7.92 (d, J=7.8 Hz, 1H), 7.71 (t, J=7.7 Hz, 1H), 7.14-7.00 (m, 2H), 6.99-6.88 (m, 2H), 5.28-5.13 (m, 1H), 5.02-4.80 (m, 1H), 4.62-4.51 (m, 1H), 4.21-3.88 (m, 5H), 3.57 (d, J=16.7 Hz, 3H), 2.40-2.22 (m, 4H), 2.18 (s, 2H), 1.99 (s, 3H), 1.45-1.24 (m, 3H).

LCMS Calculated for $C_{34}H_{35}F_4N_7O_4$: 681.2; Observed (Method-N): 680.3 $[M-H]^-$, 99.59% at RT 1.862 min.

13. Synthesis of N-(4S,5S)-3-((2S*,3S*)-2-cyano-3-(methylamino)pyrrolidine-1-carbonyl-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-687) & N-((4S,5S)-3-((2R*,3R*)-2-cyano-3-(methylamino)pyrrolidine-1-carbonyl-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-421)

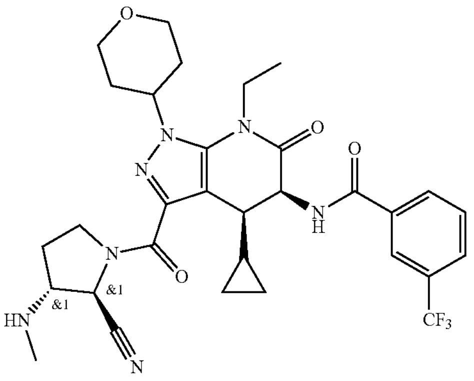

39

-continued

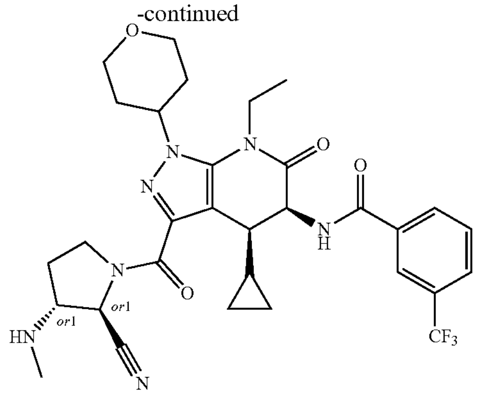

I-421-02

+

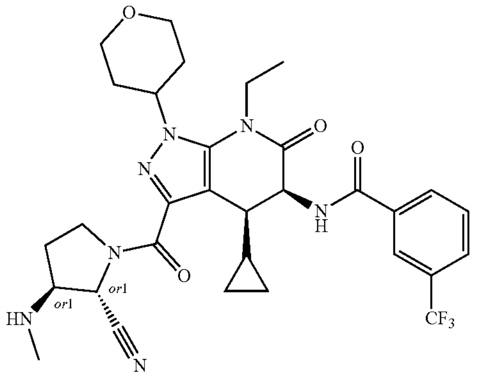 [SMILES: CCN1C(=O)[C@@H](NC(=O)c2cccc(C(F)(F)F)c2)[C@@H](C2CC2)c2c(C(=O)N3CC[C@H](NC)[C@H]3C#N)nn(C3CCOCC3)c21]

I-687-02

Compound 39 was prepared according to I-693.

The crude product (20 mg) was purified by Prep-Chiral-HPLC with the following conditions (Column: XA-CHIRALPAK IE, 3*25 cm, 5 μm; Mobile Phase A: Hex: DCM=1: 1, Mobile Phase B: EtOH (0.1% 2M $NH_3$-MeOH); Flow rate: 35 mL/min; Gradient: isocratic 10; Wave Length: 230 nm; RT1(min): 6.8; RT2(min): 10.1; Sample Solvent: EtOH; Injection Volume: 2.5 mL; Number Of Runs: 4) afford N-((4S,5S)-3-((2S*,3S*)-2-cyano-3-(methylamino)pyrrolidine-1-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-687) (5 mg, 25.0% yield, 99.85% purity) and N-((4S,5S)-3-((2R*,3R*)-2-cyano-3-(methylamino) pyrrolidine-1-carbonyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-421) (5 mg, 25.0% yield, 99.63% purity) as a white solid.

| | |
|---|---|
| 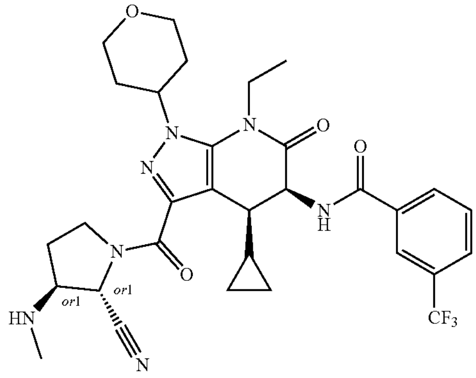<br>I-687 | 1H NMR (300 MHz, DMSO-d6) δ 9.11-8.97 (m, 1H), 8.31 (s, 1H), 8.25 (d, J = 7.9 Hz, 1H), 7.95 (d, J = 7.9 Hz, 1H), 7.76 (t, J = 7.8 Hz, 1H), 5.40-4.98 (m, 2H), 4.58-4.41 (m, 1H), 4.22-3.71 (m, 5H), 3.68-3.44 (m, 3H), 3.46-3.35 (m, 2H), 2.40-2.27 (m, 3H), 2.21 (d, J = 5.4 Hz, 2H), 2.18-1.70 (m, 5H), 1.25 (t, J = 7.0 Hz, 4H), 0.89-0.73 (m, 1H), 0.56-0.42 (m, 1H), 0.27-0.02 (m, 3H). LCMS Calculated for $C_{31}H_{36}F_3N_7O_4$: 627.2; Observed (Method-P): 626.3 $[M - H]^+$, 99.85% at RT 1.851 min. Chiral-HPLC (Method-I): 100% at RT 1.332 min. |

-continued

| | |
|---|---|
| 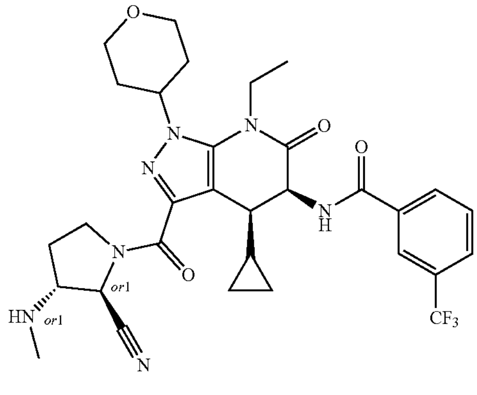 [SMILES: CCN1C(=O)[C@@H](NC(=O)c2cccc(C(F)(F)F)c2)[C@@H](C2CC2)c2c(C(=O)N3CC[C@@H](NC)[C@@H]3C#N)nn(C3CCOCC3)c21]<br>I-421 | $^{1}H$ NMR (300 MHz, DMSO-$d_6$) δ 9.05-8.98 (m, 1H), 8.31 (s, 1H), 8.24 (d, J = 7.9 Hz, 1H), 7.96 (d, J = 7.9 Hz, 1H), 7.76 (t, J = 7.8 Hz, 1H), 5.16-4.96 (m, 2H), 4.54-4.45 (m, 1H), 4.18-3.90 (m, 5H), 3.60-3.39 (m, 4H), 2.37-2.25 (m, 4H), 2.18-1.96 (m, 4H), 1.92 (s, 2H), 1.26 (d, J = 4.1 Hz, 4H), 0.84-0.76 (m, 1H), 0.49 (s, 1H), 0.26-0.08 (m, 3H).<br>LCMS Calculated for $C_{31}H_{36}F_3N_7O_4$: 627.2; Observed (Method-P): 626.3 [M − H]$^+$, 99.63% at RT 1.859 min.<br>Chiral-HPLC (Method-I): 100% at RT 1.735 min. |

Synthesis of N-((4S,5S)-3-((2R,3S)-2-cyano-3-fluoropyrrolidine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-trifluoromethyl)benzamide (I-694)

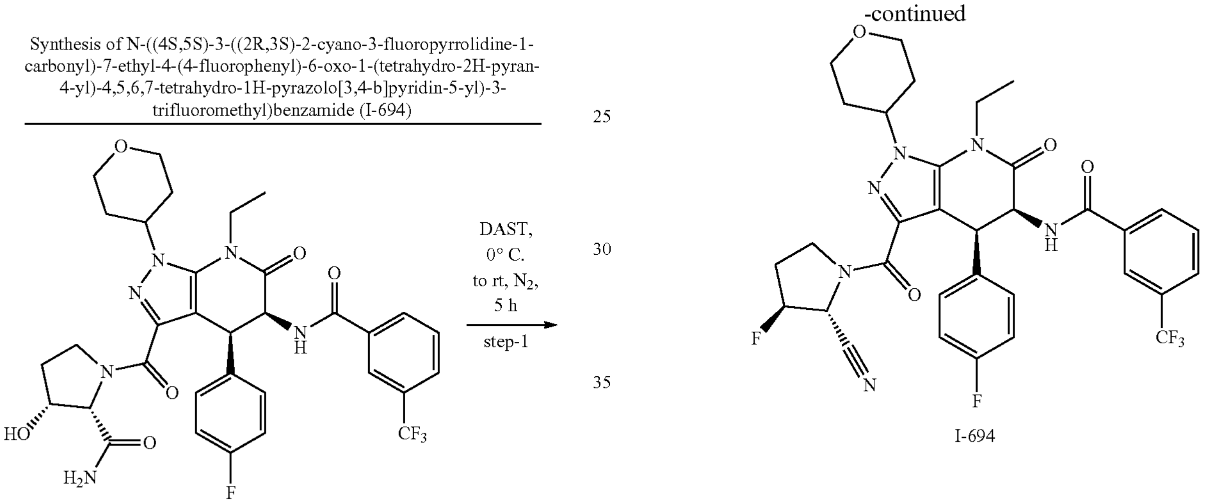

38

-continued

I-694

(2R,3S)-1-((4S,5S)-7-ethyl-4-(4-fluorophenyl)-6-oxo-1-(tetrahydro-2H-pyran-4-yl)-5-(3-trifluoromethyl)benzamido)-4,5,6,7-tetrahydro-1H-pyrazolo[3,4-b]pyridine-3-carbonyl)-3-fluoropyrrolidine-2-carboxamide (39)

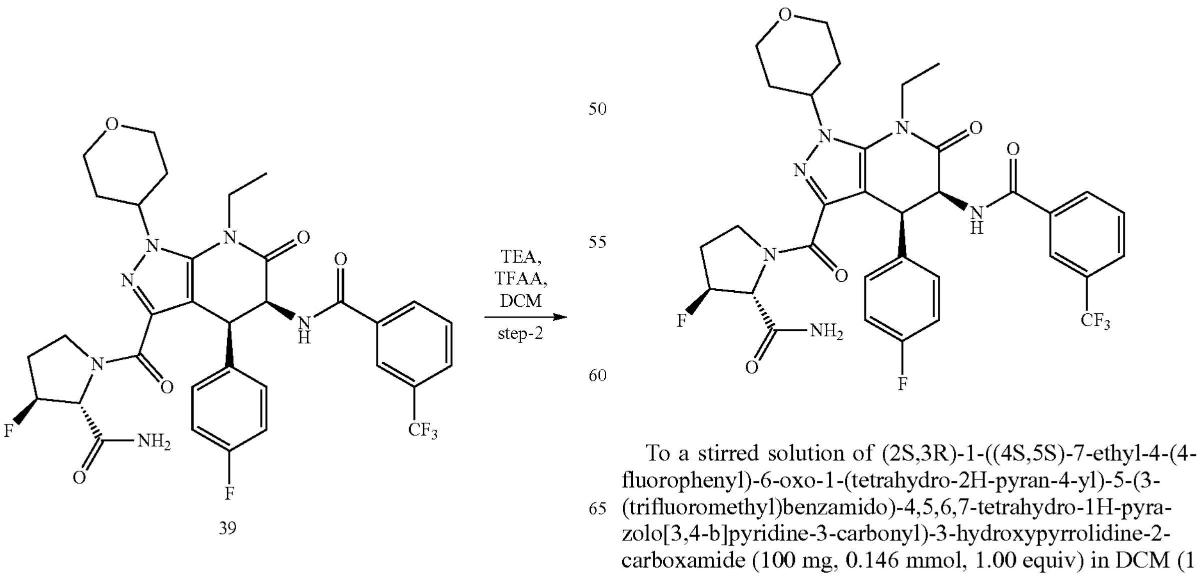

39

To a stirred solution of (2S,3R)-1-((4S,5S)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carbonyl)-3-hydroxypyrrolidine-2-carboxamide (100 mg, 0.146 mmol, 1.00 equiv) in DCM (1 mL) was added Diethylaminosulfur trifluoride (28.2 mg, 0.175 mmol, 1.20 equiv) dropwise at 0° C. under nitrogen atmosphere. The resulting mixture was stirred at room temperature for 5 h under nitrogen atmosphere. The reaction was poured into Water at room temperature. The resulting mixture was extracted with EtOAc (3x5 mL). The combined organic layers were washed with brine (2x3 mL), dried over anhydrous $Na_2SO_4$. After filtration, the filtrate was concentrated under reduced pressure. The residue was purified by silica gel column chromatography, eluted with petroleum ether/ethyl acetate (1:1) to afford (2R,3S)-1-((4S,5S)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carbonyl)-3-fluoropyrrolidine-2-carboxamide (40 mg, 39.88% yield, 90% purity) as a white solid.

N-((4S,5S)-3-((2R,3S)-2-cyano-3-flouoropyrrolidine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-694)

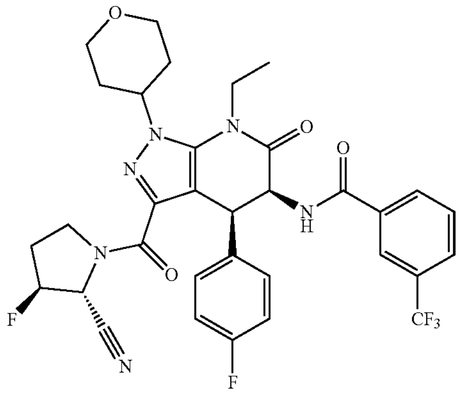

I-694

To a mixture of (2R,3S)-1-((4S,5S)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carbonyl)-3-fluoropyrrolidine-2-carboxamide (40.0 mg, 0.058 mmol, 1.00 equiv) and $Et_3N$ (5.88 mg, 0.058 mmol, 1.00 equiv) in DCM (1 mL) was added 2,2,2-trifluoroacetyl 2,2,2-trifluoroacetate (24.4 mg, 0.116 mmol, 2.00 equiv) dropwise at room temperature. The resulting mixture was stirred at room temperature for 3 h. The resulting mixture was extracted with EtOAc (3x5 mL). The combined organic layers were washed with brine (3x5 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% FA), 40% to 80% gradient in 10 min; detector, UV 254 nm. This resulted in N-((4S,5S)-3-((2R,3S)-2-cyano-3-fluoropyrrolidine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (8 mg, 20.54% yield, 96.8% purity) as a white solid.

$^1H$ NMR (400 MHZ, Chloroform-d) δ 8.03 (s, 1H), 7.87 (d, J=7.5 Hz, 1H), 7.81 (d, J=7.8 Hz, 1H), 7.60 (t, J=7.8 Hz, 1H), 7.07-6.89 (m, 4H), 6.80-6.68 (m, 1H), 5.70-5.11 (m, 4H), 4.49-3.84 (m, 7H), 3.72-3.53 (m, 2H), 2.63-1.91 (m, 6H), 1.53-1.42 (m, 3H).

LCMS Calculated for $C_{33}H_{31}F_5N_6O_4$: 670.23; Observed (Method-AT): 669.3 $[M-H]^-$, 96.87% at RT 2.356 min.

15. Synthesis of I-362

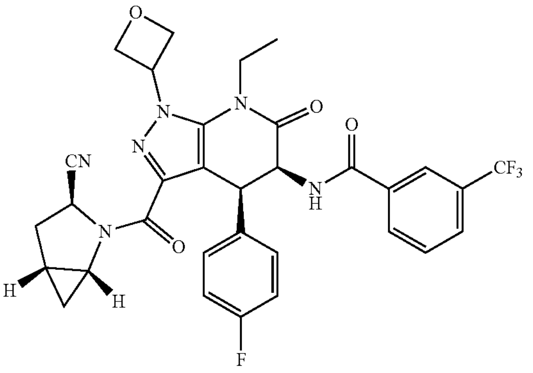

I-362

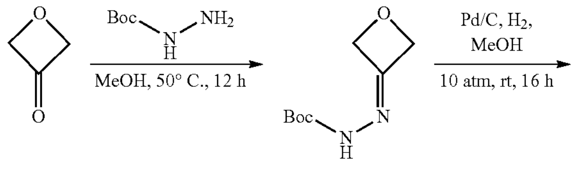

40

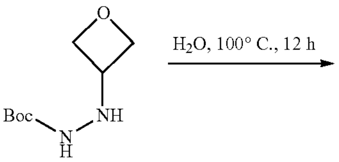

41

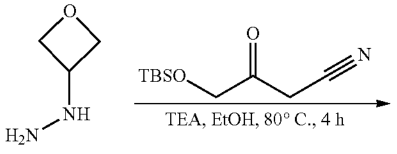

42

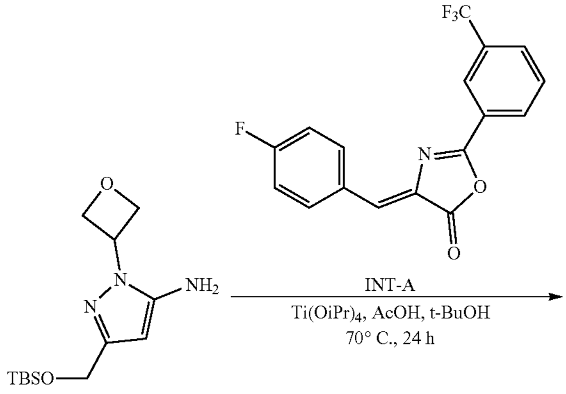

43

-continued
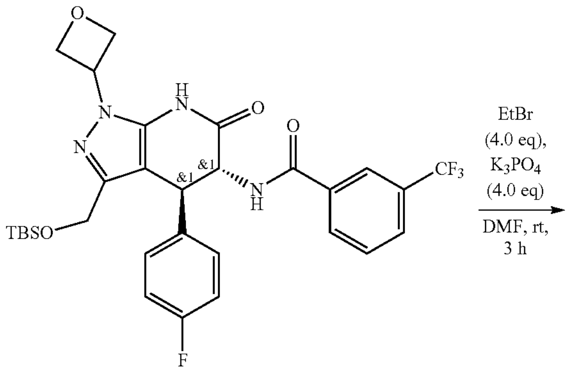
60
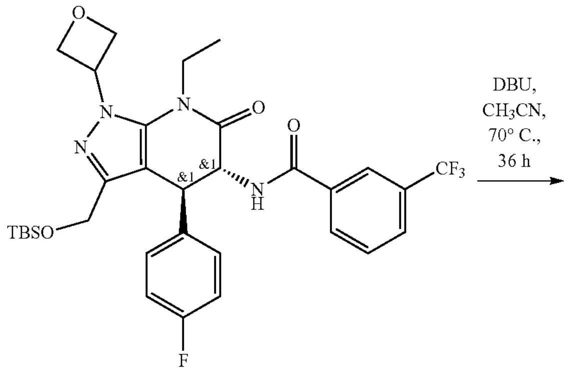
61
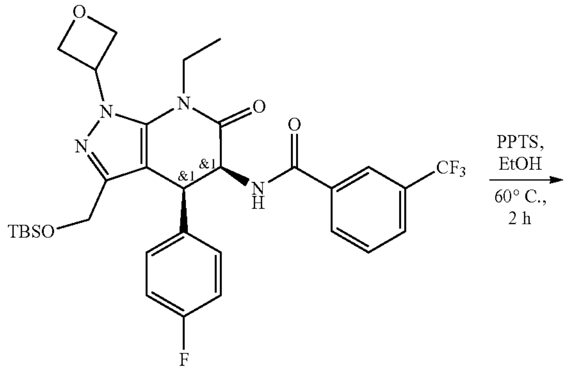
62
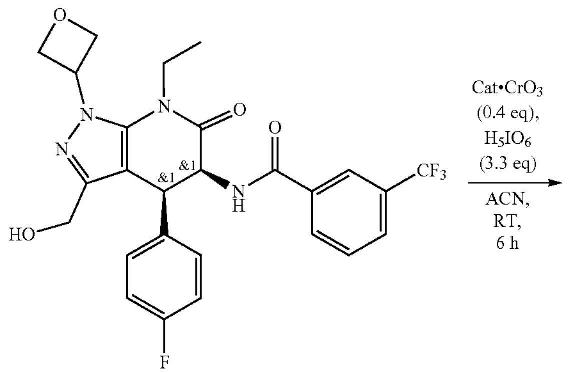
63
-continued
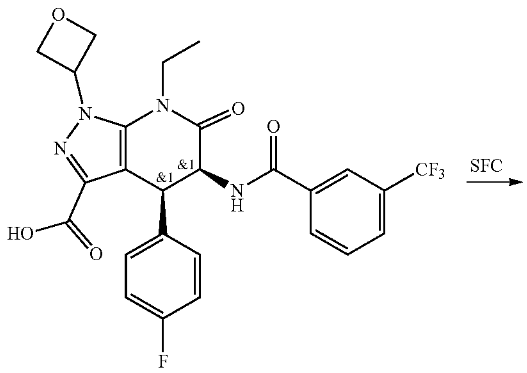
64
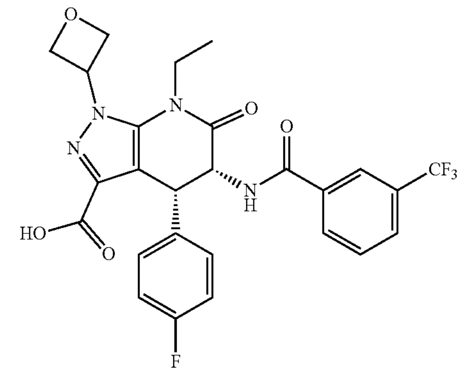
64A
+
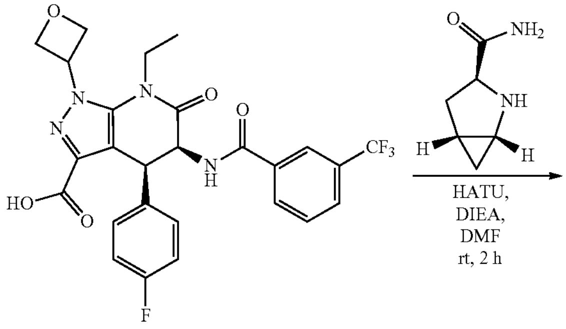
64B
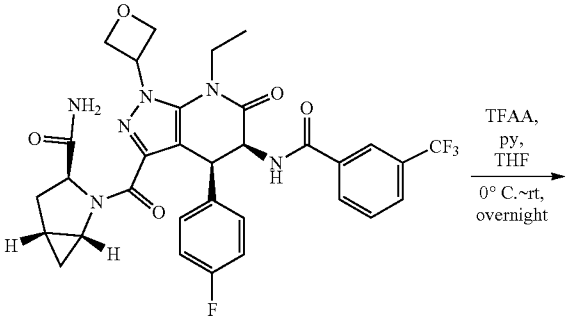
65

-continued

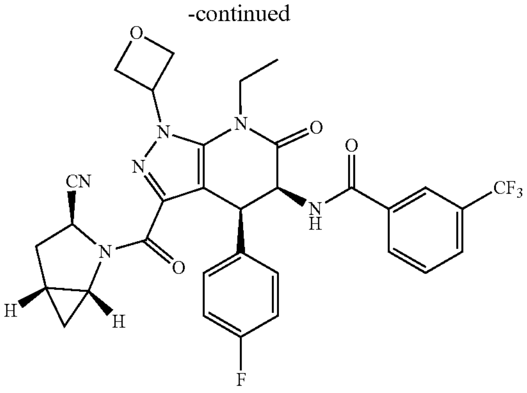

I-362 tert-butyl 2-(oxetan-3-ylidene)hydrazine-1-carboxylate (40)

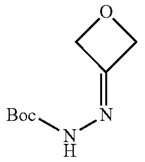

To a stirred solution of 3-oxetanone (25.0 g, 347 mmol, 1.00 equiv), tert-butoxycarbohydrazide (50.4 g, 382 mmol, 1.10 equiv) in methanol (500 mL) was stirred for 12 h at room temperature. After filtration, the filtrate was concentrated under reduced pressure. This resulted in N'-(oxetan-3-ylidene) tert-butoxycarbohydrazide (50.0 g, 77%) as a white solid.

LCMS Calculated for $C_8H_{14}N_2O_3$: 186.10; Observed (Method-G): 187.10 $[M+H]^+$, 90.1% at RT 0.635 min.

tert-butyl 2-(oxetan-3-yl)hydrazine-1-carboxylate (41)

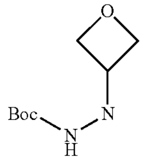

Into a 1000-mL round-bottom flask, were placed N'-(oxetan-3-ylidene) tert-butoxycarbohydrazide (50.0 g, 268 mmol, 1.00 equiv), methanol (500 mL), Pd/C (14.3 g, 134 mmol, 0.50 equiv). The mixture was hydrogenated at 35° C. under 10 atm of hydrogen pressure for 12 h. The resulting mixture was filtered. The filtrate was concentrated under vacuum to give N'-(oxetan-3-yl) tert-butoxycarbohydrazide (40 g, 79%) as a white solid.

LCMS Calculated for $C_8H_{16}N_2O_3$: 188.12; Observed (Method-G): 189.10 $[M+H]^+$, 92.5% at RT 0.720 min.

oxetan-3-ylhydrazine (42)

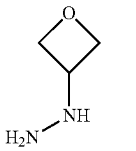

Into a 1000 mL round-bottom flask were added N'-(oxetan-3-yl) tert-butoxycarbohydrazide (40.0 g, 213 mmol, 1.00 equiv), $H_2O$ (400 mL) at 25° C. The resulting mixture was stirred for 12 h at 100° C. The resulting mixture was concentrated under reduced pressure. This resulted in oxetan-3-ylhydrazine (15 g crude) as a colorless oil.

LCMS Calculated for $C_3H_8N_2O$: 88.06; Observed (Method-G): 89.10 $[M+H]^+$, 91.5% at RT 0.320 min.

3-(((tert-butyldimethylsilyl)oxy)methyl)-1-(oxetan-3-yl)-1H-pyrazol-5-amine (43)

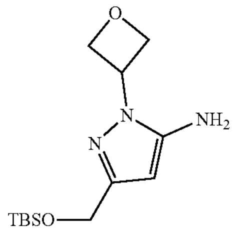

Into a 500 mL round-bottom flask were added oxetan-3-ylhydrazine (8.0 g, 91 mmol, 1.0 equiv), EtOH (200 mL), 4-[(tert-butyldimethylsilyl)oxy]-3-oxobutanenitrile (67.8 g, 318 mmol, 3.50 equiv) and $Et_3N$ (27.6 g, 272 mmol, 3.00 equiv) at room temperature. The resulting mixture was stirred for 4 h at 80° C. The reaction was quenched with water (100 mL) at room temperature. The resulting mixture was extracted with EtOAc (2×200 mL). The combined organic layers were washed with brine (2×200 mL), dried over anhydrous $Na_2SO_4$. After filtration, the filtrate was concentrated under reduced pressure. The residue was purified by silica gel column chromatography, eluted with DCM/MeOH (10:1) to afford 5-{[(tert-butyldimethylsilyl)oxy]methyl}-2-(oxetan-3-yl) pyrazol-3-amine (10.0 g, 38.86%) as an yellow oil.

LCMS Calculated for $C_{13}H_{25}N_3O_2Si$: 283.17; Observed (Method-G): 284.18 $[M+H]^+$, 90.2% at RT 1.051 min.

rac-N-((4R,5S)-3-(((tert-butylimethylsilyl)oxy)methyl)-4-(4-fluorophenyl)-1-(oxetan-3-yl)-6-oxo-4,5,6,7-tetrahydro-1H-pyrazolo[3,4-b]pyridin-5-yl)-3-(trifluoromethyl)benzamide (60)

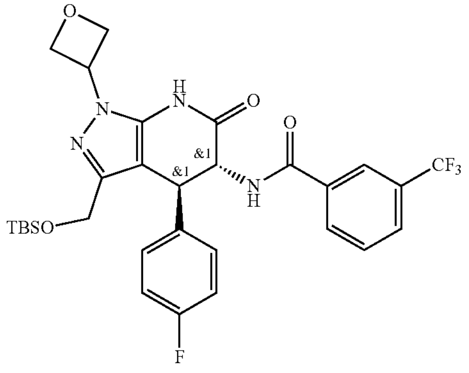

Into a 500 mL round-bottom flask were 5-{[(tert-added butyldimethylsilyl)oxy]methyl}-2-(oxetan-3-yl) pyrazol-3-amine (10.0 g, 35.3 mmol, 1.00 equiv), tert-Butanol (150 mL), (4Z)-4-[(4-fluorophenyl)methylidene]-2-[3-(trifluoromethyl)phenyl]-1,3-oxazol-5-one (17.7 g, 52.9 mmol, 1.5 equiv) and Acetic acid (0.21 g, 3.53 mmol, 0.1 equiv) at room temperature. The resulting mixture was stirred for 24 h at 70° C. The reaction was quenched with water (100 mL) at room temperature. The resulting mixture was extracted with EtOAc (2×200 mL). The combined organic layers were washed with brine (2×200 mL), dried over anhydrous $Na_2SO_4$. After filtration, the filtrate was concentrated under reduced pressure. The residue was purified by silica gel column chromatography, eluted with petroleum ether/ethyl acetate to afford rac-N-((4R,5S)-3-(((tert-butyldimethylsilyl)oxy)methyl)-4-(4-fluorophenyl)-1-(oxetan-3-yl)-6-oxo-4,5,6,7-tetrahydro-1H-pyrazolo[3,4-b]pyridin-5-yl)-3-(trifluoromethyl)benzamide (7.0 g, 32%) as an yellow solid.

LCMS Calculated for $C_{30}H_{34}F_4N_4O_4Si$: 618.23; Observed (Method-G): 619.2 $[M+H]^+$, 92.2% at RT 1.270 min.

rac-N-((4R,5S)-3-(((tert-butylimethylsilyl)oxy)methyl)-7-ethyl-4-(4-fluorophenyl)-1-(oxetan-3-yl)-6-oxo-4,5,6,7-tetrahydro-1H-pyrazolo[3,4-b]pyridin-5-yl)-3-(trifluoromethyl)benzamide (61)

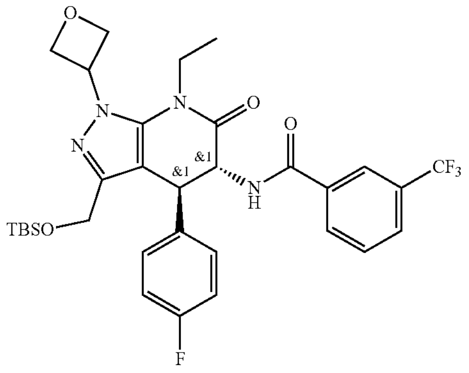

Into a 250 mL round-bottom flask were added rac-N-((4R, 5S)-3-(((tert-butyldimethylsilyl)oxy)methyl)-4-(4-fluorophenyl)-1-(oxetan-3-yl)-6-oxo-4,5,6,7-tetrahydro-1H-pyrazolo[3,4-b]pyridin-5-yl)-3-(trifluoromethyl)benzamide (7.0 g, 11.3 mmol, 1.00 equiv), DMF (70 mL), $K_3PO_4$ (9.61 g, 45.3 mmol, 4.00 equiv) and bromoethane (4.93 g, 45.3 mmol, 4.00 equiv) at room temperature. The resulting mixture was stirred for 3 h at room temperature. The reaction was quenched with water (100 mL) at room temperature. The resulting mixture was extracted with EtOAc (2×200 mL). The combined organic layers were washed with brine (2×200 mL), dried over anhydrous $Na_2SO_4$. After filtration, the filtrate was concentrated under reduced pressure. The residue was purified by silica gel column chromatography, eluted with petroleum ether/ethyl acetate to afford rac-N-((4R,5S)-3-(((tert-butyldimethylsilyl)oxy)methyl)-7-ethyl-4-(4-fluorophenyl)-1-(oxetan-3-yl)-6-oxo-4,5,6,7-tetrahydro-1H-pyrazolo[3,4-b]pyridin-5-yl)-3-(trifluoromethyl) benzamide (3.5 g, 47.83%) as an yellow oil.

LCMS Calculated for $C_{32}H_{38}F_4N_4O_4Si$: 646.26; Observed (Method-G): 647.3 $[M+H]^+$, 90.5% at RT 1.405 min.

rac-N-((4R,5R)-3-(((tert-butylimethylsilyl)oxy)methyl)-7-ethyl-4-(4-fluorophenyl)-1-(oxetan-3-yl)-6-oxo-4,5,6,7-tetrahydro-1H-pyrazolo[3,4-b]pyridin-5-yl)-3-(trifluoromethyl)benzamide (62)

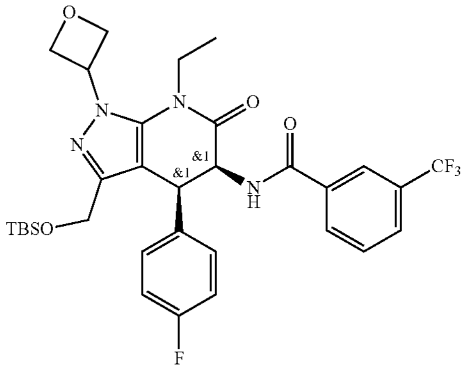

Into a 100 mL round-bottom flask were added rac-N-((4R, 5S)-3-(((tert-butyldimethylsilyl)oxy)methyl)-7-ethyl-4-(4-fluorophenyl)-1-(oxetan-3-yl)-6-oxo-4,5,6,7-tetrahydro-1H-pyrazolo[3,4-b]pyridin-5-yl)-3-(trifluoromethyl) benzamide (3.5 g, 5.41 mmol, 1.00 equiv), DBU (4.94 g, 32.5 mmol, 6.0 equiv) and MeCN (40 mL) at room temperature. The resulting mixture was stirred for 36 h at 70° C. The reaction was quenched with water (50 mL) at room temperature. The resulting mixture was extracted with EtOAc (2×50 mL). The combined organic layers were washed with brine (2×50 mL), dried over anhydrous $Na_2SO_4$. After filtration, the filtrate was concentrated under reduced pressure. The residue was purified by silica gel column chromatography, eluted with petroleum ether/ethyl acetate to afford rac-N-((4R,5R)-3-(((tert-butyldimethylsilyl)oxy)methyl)-7-ethyl-4-(4-fluorophenyl)-1-(oxetan-3-yl)-6-oxo-4,5,6,7-tetrahydro-1H-pyrazolo[3,4-b]pyridin-5-yl)-3-(trifluoromethyl)benzamide (1.3 g, 37.1%) as an yellow solid.

LCMS Calculated for $C_{32}H_{38}F_4N_4O_4Si$: 646.26; Observed (Method-G): 647.3 $[M+H]^+$, 91.5% at RT 1.441 min.

rac-N-((4R,5R)-7-ethyl-4-(4-fluorophenyl)-1-(oxetan-3-yl)-6-oxo-4,5,6,7-tetrahydro-1H-pyrazolo[3,4-b]pyridin-5-yl)-3-(trifluoromethyl)benzamide (63)

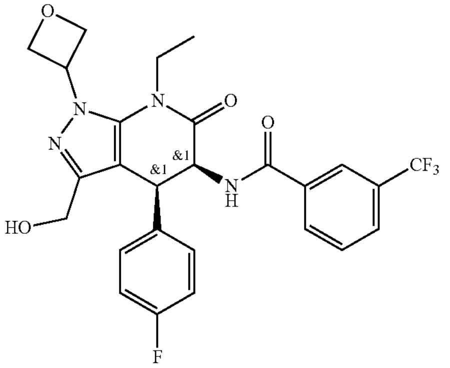

Into were added rac-N-((4R,5R)-3-(((tert-a 40 mL vial butyldimethylsilyl)oxy)methyl)-7-ethyl-4-(4-fluorophenyl)-1-(oxetan-3-yl)-6-oxo-4,5,6,7-tetrahydro-1H-pyrazolo[3,4-b]pyridin-5-yl)-3-(trifluoromethyl)benzamide (1.30 g, 2.01 mmol, 1.00 equiv), EtOH (15 mL), 4-methylbenzene-1-sulfonate; pyridin-1-ium (2.53 g, 10.0 mmol, 5.00 equiv) at room temperature. The resulting mixture was stirred for 2 h at 60° C. The reaction was quenched with water (20 mL) at room temperature. The resulting mixture was extracted with EtOAc (2×20 mL). The combined organic layers were washed with brine (2×20 mL), dried over anhydrous $Na_2SO_4$. After filtration, the filtrate was concentrated under reduced pressure. The residue was purified by silica gel column chromatography, eluted with petroleum ether/ethyl acetate (1:1) to afford rac-N-((4R,5R)-7-ethyl-4-(4-fluorophenyl)-3-(hydroxymethyl)-1-(oxetan-3-yl)-6-oxo-4,5,6,7-tetrahydro-1H-pyrazolo[3,4-b]pyridin-5-yl)-3-(trifluoromethyl)benzamide (850 mg, 79.41%) as a white solid.

LCMS Calculated for $C_{26}H_{24}F_4N_4O_4$: 532.17; Observed (Method-G): 533.3 $[M+H]^+$, 95.5% at RT 1.006 min.

rac-N-((4R,5R)-7-ethyl-4-(4-fluorophenyl)-1-(oxetan-3-yl)-6-oxo-4,5,6,7-tetrahydro-1H-pyrazolo[3,4-b]pyridine-3-carboxylic acid (64)

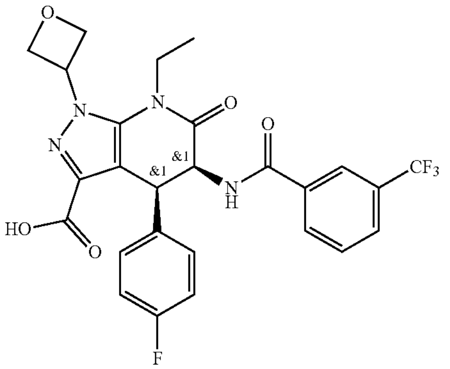

Into a 40 mL sealed tube were added rac-N-((4R,5R)-7-ethyl-4-(4-fluorophenyl)-3-(hydroxymethyl)-1-(oxetan-3-yl)-6-oxo-4,5,6,7-tetrahydro-1H-pyrazolo[3,4-b]pyridin-5-yl)-3-(trifluoromethyl)benzamide (850 mg, 1.60 mmol, 1.00 equiv), MeCN (10 mL), $H_2O$ (1 mL), Chrormictrioxide (63.9 mg, 0.638 mmol, 0.400 equiv) at 0° C. To the above mixture was added Periodic acid (1.20 g, 5.27 mmol, 3.30 equiv) dropwise over 5 min at 0° C. The resulting mixture was stirred for 3 h at 0° C. The resulting mixture was diluted with $H_2O$ (50 mL). The resulting mixture was extracted with EtOAc (2×50 mL). The combined organic layers were washed with brine (2×50 mL), dried over anhydrous $Na_2SO_4$. After filtration, the filtrate was concentrated under reduced pressure. The residue was purified by silica gel column chromatography, eluted with DCM/MeOH (10:1) to afford rac-(4R,5R)-7-ethyl-4-(4-fluorophenyl)-1-(oxetan-3-yl)-6-oxo-5-[3-(trifluoromethyl)benzamido]-4H,5H-pyrazolo[3,4-b]pyridine-3-carboxylic acid (750 mg, 85.98%) as a white solid.

LCMS Calculated for $C_{26}H_{22}F_4N_4O_5$: 546.15; Observed (Method-G): 547.1 $[M+H]^+$, 95.6% at RT 1.168 min.

(4R,5R)-7-ethyl-4-(4-fluorophenyl)-1-(oxetan-3-yl)-6-oxo-5-(3-trifluoromethyl)benzamido)-4,5,6,7-tetrahydro-1H-pyrazolo[3,4-b]pyridine-3-carboxylic acid (64A) & (4S,5S)-7-ethyl-4-(4-fluorophenyl)-1-(oxetan-3-yl)-6-oxo-5-(3-trifluoromethyl)benzamido)-4,5,6,7-tetrahydro-1H-pyrazolo[3,4-b]pyridine-3-carboxylic acid (64B)

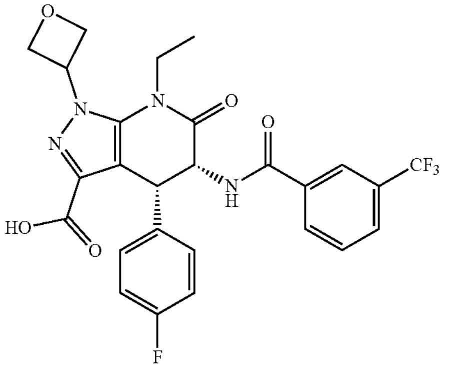

64A

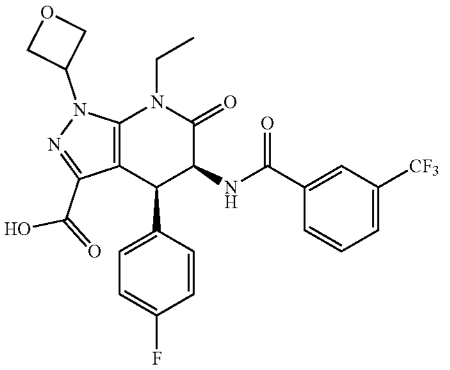

64B

The 550 mg of rac-(4R,5R)-7-ethyl-4-(4-fluorophenyl)-1-(oxetan-3-yl)-6-oxo-5-[3-(trifluoromethyl)benzamido]-4H,5H-pyrazolo[3,4-b]pyridine-3-carboxylic acid was purified by Chiral-Prep-SFC with the following conditions: Column: XA-(R, R)-WHELK-O, 3*25 cm, 5 μm; Mobile Phase A: $CO_2$, Mobile Phase B: MeOH: DCM=2: 1 (0.1% 2M $NH_3$-MeOH); Flow rate: 80 mL/min; Gradient: isocratic 35% B; Column Temperature (C): 35; Back Pressure (bar): 100; Wave Length: 220 nm; RT1(min): 3.04; RT2(min): 4.35; Sample Solvent: MeOH; Injection Volume: 2 mL.

Finally, (4R,5R)-7-ethyl-4-(4-fluorophenyl)-1-(oxetan-3-yl)-6-oxo-5-[3-(trifluoromethyl)benzamido]-4H,5H-pyrazolo[3,4-b]pyridine-3-carboxylic acid was obtained as a white solid (270 mg, 49.09%) & (4S,5S)-7-ethyl-4-(4-fluorophenyl)-1-(oxetan-3-yl)-6-oxo-5-[3-(trifluoromethyl)benzamido]-4H,5H-pyrazolo[3,4-b]pyridine-3-carboxylic acid was obtained as a white solid (260 mg, 47.27%).

Data for 64A:

LCMS Calculated for $C_{26}H_{22}F_4N_4O_5$: 546.15; Observed (Method-G): 547.17 $[M+H]^+$, 98.8% at RT 1.168 min.

Chiral SFC (Method-B): 100.00% at RT 1.16 min.

Optical rotation: a=−178 (c=0.1 g/100 mL in MeOH, T=25° C.)

Data for 64B:

LCMS Calculated for $C_{26}H_{22}F_4N_4O_5$: 546.15; Observed (Method-G): 547.17 $[M+H]^+$, 96.9% at RT 1.168 min.

Chiral SFC (Method-B): 97.96% at RT 1.29 min.

Optical rotation: a=+125 (c=0.1 g/100 mL in MeOH, T=25° C.)

(1R,3S,5R)-2-((4S,5S)-7-ethyl-4-(4-fluorophenyl)-1-(oxetan-3-yl)-6-oxo-5-(3-trifluoromethyl)benzamido)-4,5,6,7-tetrahydro-1H-pyrazolo[3,4-b]pyridine-3-carbonyl)-2-azabycyclo[3.1.0]hexane-3-carboxamide (65)

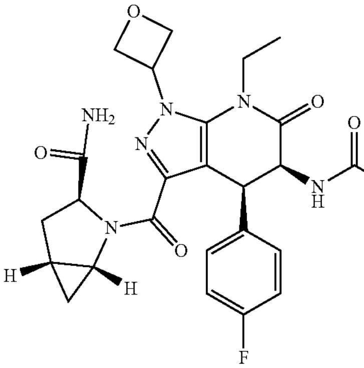

Into a 8 mL vial were added (4S,5S)-7-ethyl-4-(4-fluorophenyl)-1-(oxetan-3-yl)-6-oxo-5-[3-(trifluoromethyl)benzamido]-4H,5H-pyrazolo[3,4-b]pyridine-3-carboxylic acid was obtained as a white solid (150 mg, 0.274 mmol, 1.00 equiv), DMF (2 mL), (1R,3S,5R)-2-azabicyclo[3.1.0]hexane-3-carboxamide hydrochloride (89.3 mg, 0.548 mmol, 2.00 equiv), DIEA (70.9 mg, 0.548 mmol, 2.00 equiv) and HATU (125 mg, 0.329 mmol, 1.20 equiv) at room temperature. The resulting mixture was stirred for 2 h at room temperature. The reaction was quenched with water (20 mL) at room temperature. The resulting mixture was extracted with EtOAc (2×20 mL). The combined organic layers were washed with brine (2×20 mL), dried over anhydrous $Na_2SO_4$. After filtration, the filtrate was concentrated under reduced pressure. The residue was purified by silica gel column chromatography, eluted with DCM/MeOH (10:1) to afford (1R,3S,5R)-2-((4S,5S)-7-ethyl-4-(4-fluorophenyl)-1-(oxetan-3-yl)-6-oxo-5-(3-(trifluoromethyl)benzamido)-4,5,6,7-tetrahydro-1H-pyrazolo[3,4-b]pyridine-3-carbonyl)-2-azabicyclo[3.1.0]hexane-3-carboxamide (85 mg, 47.3%) as a white solid.

LCMS Calculated for $C_{32}H_{30}F_4N_6O_5$: 654.22; Observed (Method-G): 655.3 $[M+H]^+$, 91.2% at RT 0.989 min.

N-((4S,5S)-3-((1R,3S,5R)-3-cyano-2-azabicyclo[3.1.0]hexane-2-carbonyl)-7-ethyl-4-(4-fluorophenyl)-1-(oxetan-3-yl)-6-oxo-4,5,6,7-tetrahydro-1H-pyrazolo[3,4-b]pyridin-5-yl)-3-(trifluoromethyl)benzamide (I-362)

Into a 50 mL round-bottom flask were added (1R,3S,5R)-2-((4S,5S)-7-ethyl-4-(4-fluorophenyl)-1-(oxetan-3-yl)-6-oxo-5-(3-(trifluoromethyl)benzamido)-4,5,6,7-tetrahydro-1H-pyrazolo[3,4-b]pyridine-3-carbonyl)-2-azabicyclo[3.1.0]hexane-3-carboxamide (80 mg, 0.122 mmol, 1.00 equiv) and THF (1 mL), $Et_3N$ (37.1 mg, 0.366 mmol, 3.00 equiv) at 0° C. To the above mixture was added Trifluoroacetic anhydride (51.3 mg, 0.244 mmol, 2.00 equiv) dropwise over 2 min at 0° C. The resulting mixture was stirred for 2 h at room temperature. The reaction was quenched with water (20 mL) at room temperature. The resulting mixture was extracted with EtOAc (2×20 mL). The combined organic layers were washed with brine (2×20 mL), dried over anhydrous $Na_2SO_4$. After filtration, the filtrate was concentrated under reduced pressure. The residue was purified by reversed-phase flash chromatography with the following conditions: Column: XBridge Prep OBD C18 Column, 30*150 mm, 5 μm; Mobile Phase A: Water (0.05% $NH_3H_2O$), Mobile Phase B: ACN; Flow rate: 90 mL/min; Gradient: isocratic 30%-85% 10 min; Wave Length: 254 nm/220 nm; RT1(min): 9.8 to afford N-((4S,5S)-3-((1R,3S,5R)-3-cyano-2-azabicyclo[3.1.0]hexane-2-carbonyl)-7-ethyl-4-(4-fluorophenyl)-1-(oxetan-3-yl)-6-oxo-4,5,6,7-tetrahydro-1H-pyrazolo[3,4-b]pyridin-5-yl)-3-(trifluoromethyl)benzamide (15 mg, 19.2%) as a white solid.

$^1H$ NMR (300 MHz, DMSO-$d_6$) δ 8.54 (d, J=7.5 Hz, 1H), 8.18-8.09 (m, 2H), 7.92 (d, J=7.7 Hz, 1H), 7.71 (t, J=7.8 Hz, 1H), 7.07 (t, J=8.8 Hz, 2H), 7.01-6.91 (m, 2H), 5.84-5.74 (m, 1H), 5.33-4.82 (m, 7H), 4.43 (s, 1H), 4.04 (dd, J=14.5, 7.6 Hz, 1H), 3.85-3.74 (m, 1H), 2.48-2.22 (m, 2H), 2.02-1.96 (m, 1H), 1.28 (t, J=7.1 Hz, 3H), 0.98-0.90 (m, 1H), 0.60-0.54 (m, 1H).

LCMS Calculated for $C_{32}H_{28}F_4N_6O_4$: 636.21; Observed (Method-F): 637.20 $[M+H]^+$, 99.8% at RT 1.700 min.

4 Synthesis of 74A, 74B, 74C and 74D

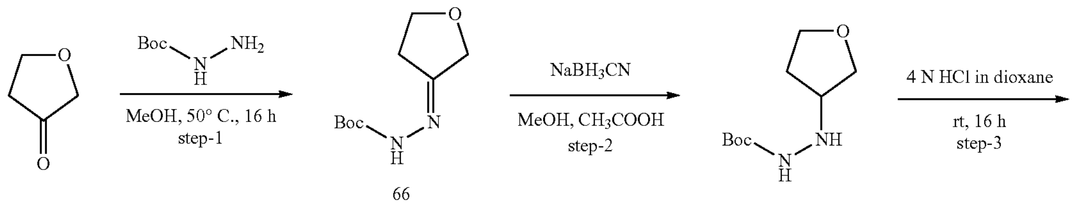

66

67

-continued
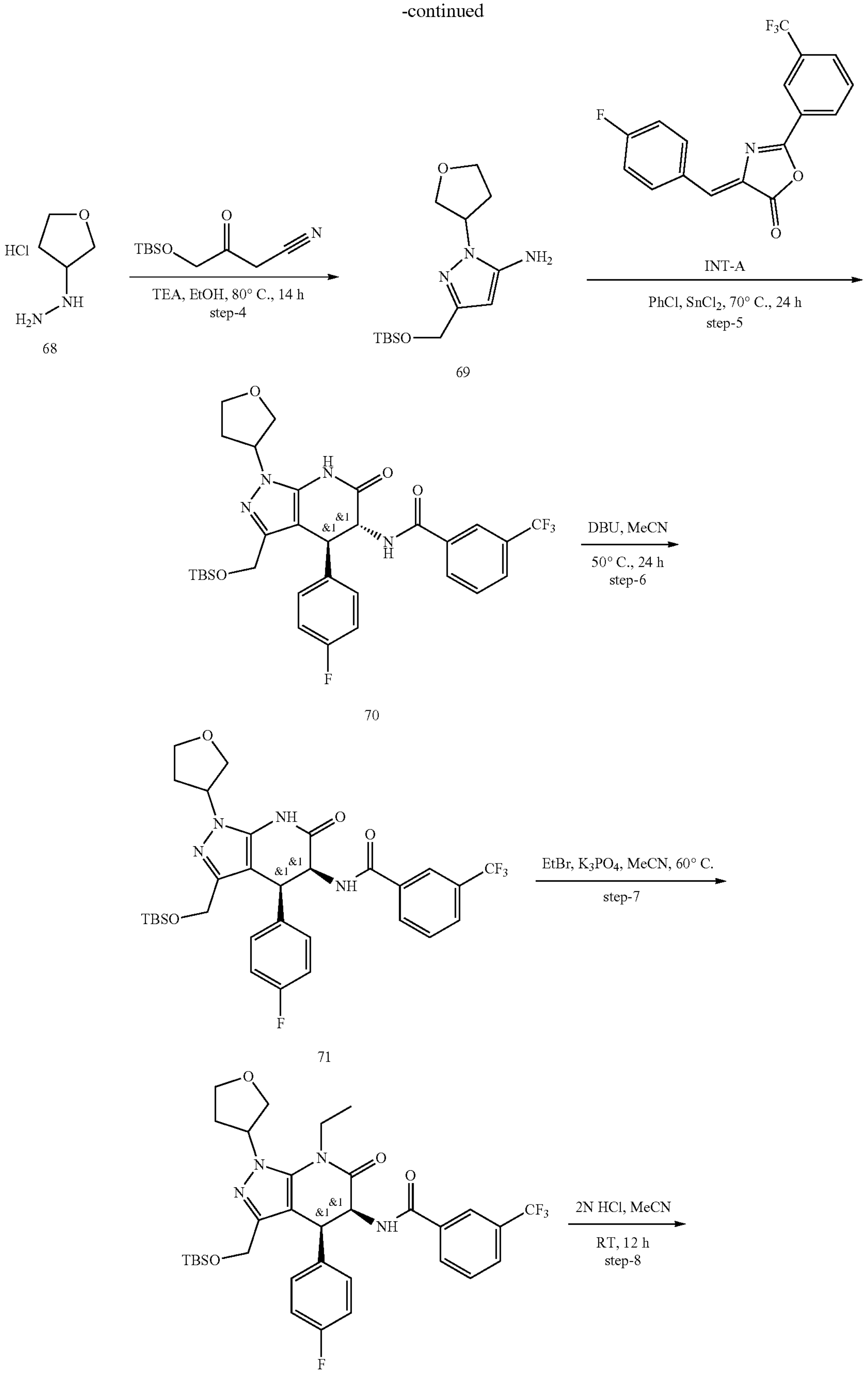
68
69
70
71
72

-continued

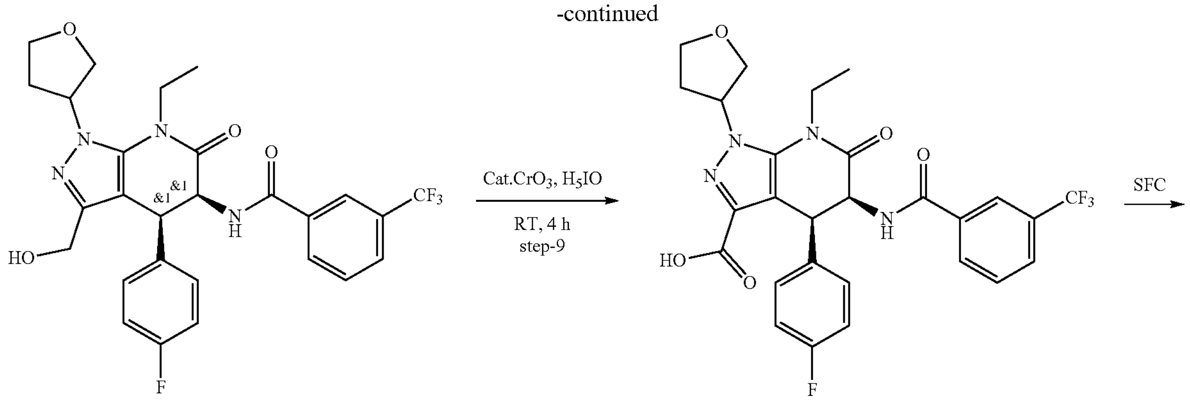

73 74

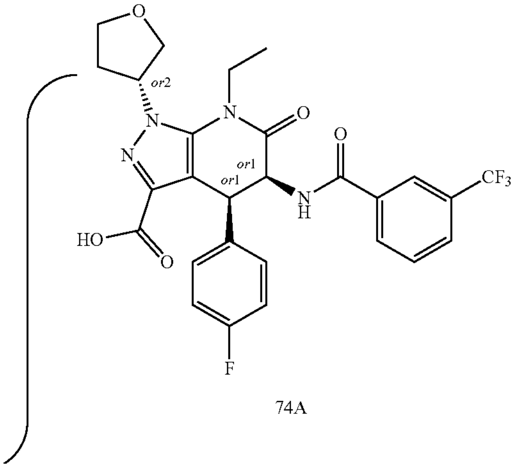

74A

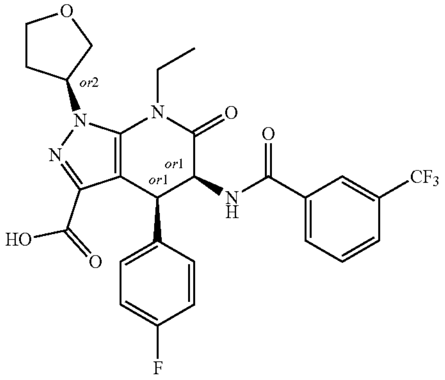

74B

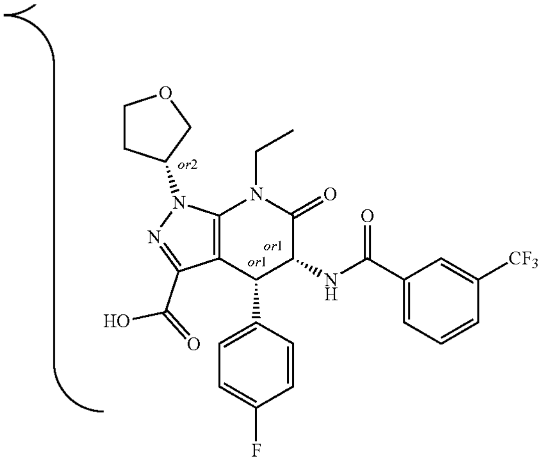

74C

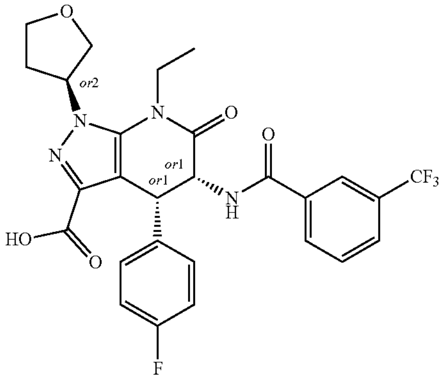

74D tert-butyl (E)2-(dihydrofuran-3(2H)-ylidene)hydrazine-1-carboxylate (66)

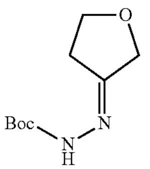

To a stirred solution of dihydrofuran-3 (2H)-one (50.0 g, 500 mmol, 1.00 equiv) in MeOH (500 mL) was added tert-butyl hydrazinecarboxylate (55 g, 500 mmol, 1.00 equiv) at room temperature under nitrogen atmosphere. The resulting mixture was stirred at 50° C. for 16 h under nitrogen atmosphere. The resulting mixture was concentrated under reduced pressure, to afford tert-butyl (E)-2-(dihydrofuran-3 (2H)-ylidene) hydrazine-1-carboxylate (51 g, 51.0%) as a yellow solid.

tert-butyl 2-(tetrahydrofuran-3-yl)hydrazine-1-carboxylate (67)

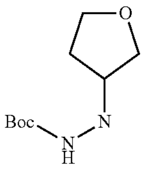

To a stirred solution of tert-butyl (E)-2-(dihydrofuran-3 (2H)-ylidene) hydrazine-1-carboxylate (50 g, 250 mmol, 1.00 equiv) and $CH_3COOH$ (75 g, 1.25 mol, 5.00 equiv) in MeOH (500 mL) was added $NaBH_3CN$ (42.1 g, 225 mmol, 1.00 equiv) at room temperature under nitrogen atmosphere. The resulting mixture was stirred at room temperature for 16 h under nitrogen atmosphere. The resulting mixture was concentrated under reduced pressure. The mixture was allowed to cool down to room temperature. The resulting mixture was extracted with EtOAc (2×500 mL). The combined organic layers were washed with brine (2×500 mL), dried over anhydrous $Na_2SO_4$. After filtration, the filtrate was concentrated under reduced pressure. The residue was purified by silica gel column chromatography, eluted with petroleum ether/EtOAc (1:1) to afford tert-butyl 2-(tetrahydrofuran-3-yl) hydrazine-1-carboxylate (40.0 g, 79.2%) as a yellow solid.

LCMS Calculated for $C_9H_{18}N_2O_3$: 202.13; Observed (Method B): 203.2 $[M+H]^+$, 64.7% at RT 1.29 min.

(tetrahydrofuran-3-yl)hydrazine hydrochloride (68)

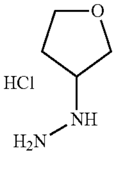

To a stirred solution of tert-butyl 2-(tetrahydrofuran-3-yl) hydrazine-1-carboxylate (40.0 g, 198 mmol, 1.00 equiv) in ethyl acetate (100 mL) was added 2 M HCl in ethyl acetate (300 mL) at room temperature under nitrogen atmosphere. The resulting mixture was stirred at room temperature for 16 h under nitrogen atmosphere. The resulting mixture was concentrated under reduced pressure to afford (tetrahydrofuran-3-yl) hydrazine hydrochloride (22.0 g, 80.2%) as a yellow solid.

3-(((tert-butyldimethylsilyl)oxy)methyl)-1-(tetrahydrofuran-3-yl)-1H-pyrazol-5-amine (69)

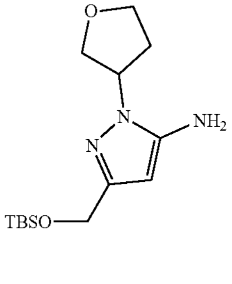

To a stirred solution of (tetrahydrofuran-3-yl) hydrazine hydrochloride (22 g, 215 mmol, 1.00 equiv) and TEA (43.4 g, 430 mmol, 2.00 equiv) in EtOH (500 mL) was added (3-bromophenyl) hydrazine (46.1 g, 21 5 mmol, 1.00 equiv) at room temperature under nitrogen atmosphere. The resulting mixture was stirred at 80° C. for 1 h under nitrogen atmosphere. The resulting mixture was concentrated under reduced pressure. The mixture was allowed to cool down to room temperature. The resulting mixture was extracted with EtOAc (2×500 mL). The combined organic layers were washed with brine (2×500 mL), dried over anhydrous $Na_2SO_4$. After filtration, the filtrate was concentrated under reduced pressure. The residue was purified by silica gel column chromatography, eluted with petroleum ether/ethyl acetate (1:1) to afford 3-(((tert-butyldimethylsilyl)oxy) methyl)-1-(tetrahydrofuran-3-yl)-1H-pyrazol-5-amine (14.0 g, 21.7%) as a yellow solid.

LCMS Calculated for $C_{14}H_{27}N_3O_2Si$: 297.19; Observed (Method-B): 298.3 $[M+H]^+$, 86.6% at RT 1.37 min.

rac-N-((4R,5S)-3-(((tert-butyldimethylsilyl)oxy)methyl)-4-(4-fluorphenyl)-6-oxo-1-(tetrahydrofuran-3-yl)-4,5,6,7-tetrahydro-1H-pyrazolo[3,4-b]pyridin-5-yl)-3-(trifluoromethyl)benzamide (70)

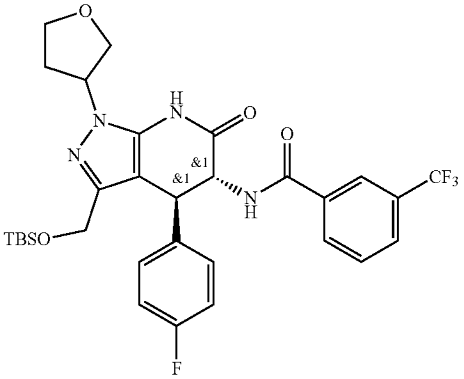

To a stirred solution of 3-(((tert-butyldimethylsilyl)oxy) methyl)-1-(tetrahydrofuran-3-yl)-1H-pyrazol-5-amine (14.0 g, 47.1 mmol, 1.00 equiv) and $SnCl_2$ (1.81 g, 9.4 mmol, 0.200 equiv) in Ph-Cl (400 mL) was added (4Z)-4-[(4-fluorophenyl)methylidene]-2-[3-(trifluoromethyl)phenyl]-1,3-oxazol-5-one (17.3 g, 51.8 mmol, 1.10 equiv) at room temperature under nitrogen atmosphere. The resulting mixture was stirred at 70° C. overnight under nitrogen atmosphere. The mixture was allowed to cool down to room temperature. The resulting mixture was concentrated under reduced pressure. The residue was purified by silica gel column chromatography, eluted with petroleum ether/ethyl acetate (1:1) to afford rac-N-((4R,5S)-3-(((tert-butyldimethylsilyl)oxy)methyl)-4-(4-fluorophenyl)-6-oxo-1-(tetrahydrofuran-3-yl)-4,5,6,7-tetrahydro-1H-pyrazolo[3,4-b]pyridin-5-yl)-3-(trifluoromethyl)benzamide (10.0 g, 30%) as a white solid.

LCMS Calculated for $C_{31}H_{36}N_4O_4F_4Si$: 632.24; Observed (Method-B): 633.3 $[M+H]^+$, 84.7% at RT 1.21 min.

rac-N-((4R,5R)-3-(((tert-butyldimethylsilyl)oxy)methyl)-4-(4-fluorophenyl)-6-oxo-1-(tetrahydrofuran-3-yl)-4,5,6,7-tetrahydro-1H-pyrazolo[3,4-b]pyridin-5-yl)-3-(trifluoromethyl)benzamide (71)

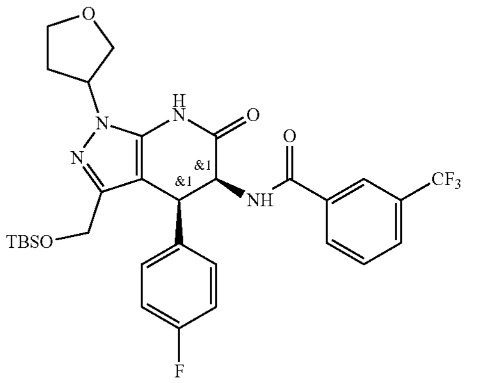

To a stirred solution of rac-N-((4R,5S)-3-(((tert-butyldimethylsilyl)oxy)methyl)-4-(4-fluorophenyl)-6-oxo-1-(tetrahydrofuran-3-yl)-4,5,6,7-tetrahydro-1H-pyrazolo[3,4-b]pyridin-5-yl)-3-(trifluoromethyl)benzamide (10.0 g, 15.8 mmol, 1.00 equiv) in ACN (200 mL) was added DBU (7.2 g, 47.4 mmol, 3.00 equiv) dropwise at room temperature under nitrogen atmosphere. The resulting mixture was stirred at 80° C. overnight under nitrogen atmosphere. The mixture was allowed to cool down to room temperature. The resulting mixture was concentrated under reduced pressure. The residue was purified by silica gel column chromatography, eluted with petroleum ether/ethyl acetate (1:1) to afford rac-N-((4R,5R)-3-(((tert-butyldimethylsilyl)oxy)methyl)-4-(4-fluorophenyl)-6-oxo-1-(tetrahydrofuran-3-yl)-4,5,6,7-tetrahydro-1H-pyrazolo[3,4-b]pyridin-5-yl)-3-(trifluoromethyl)benzamide (8 g, 80%) as a yellow solid.

rac-N-((4R,5R)-3-(((tert-butyldimethylsilyl)oxy)methyl)-7-ethyl-4-(4-fluorophenyl)-6-oxo-1-(tetrahydrofuran-3-yl)-4,5,6,7-tetrahydro-1H-pyrazolo[3,4-b]pyridin-5-yl)-3-(trifluoromethyl)benzamide (72)

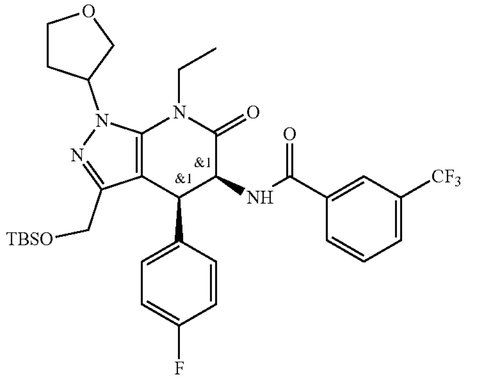

To a stirred solution of rac-N-((4R,5R)-3-(((tert-butyldimethylsilyl)oxy)methyl)-4-(4-fluorophenyl)-6-oxo-1-(tetrahydrofuran-3-yl)-4,5,6,7-tetrahydro-1H-pyrazolo[3,4-b]pyridin-5-yl)-3-(trifluoromethyl)benzamide (8.0 g, 12.6 mmol, 1.00 equiv) and $K_3PO_4$ (5.3 g, 25.3 mmol, 2.00 equiv) in ACN (200 mL) was added bromoethane (1.64 g, 15.1 mmol, 1.20 equiv) dropwise at room temperature under nitrogen atmosphere. The resulting mixture was stirred at 60° C. overnight under nitrogen atmosphere. The mixture was allowed to cool down to room temperature. The resulting mixture was concentrated under reduced pressure. The residue was purified by silica gel column chromatography, eluted with petroleum ether/ethyl acetate (1:1) to afford rac-N-((4R,5R)-3-(((tert-butyldimethylsilyl)oxy)methyl)-7-ethyl-4-(4-fluorophenyl)-6-oxo-1-(tetrahydrofuran-3-yl)-4,5,6,7-tetrahydro-1H-pyrazolo[3,4-b]pyridin-5-yl)-3-(trifluoromethyl)benzamide (7 g, 83%) as a yellow solid.

LCMS Calculated for $C_{33}H_{40}N_4O_4F_4Si$: 660.28; Observed (Method B): 661.2 $[M+H]^+$, 89.6% at RT 1.31 min.

rac-N-((4R,5R)-7-ethyl-4-(4-fluorophenyl)-3-(hydroxymethyl)-6-oxo-1-(tetrahydrofuran-3-yl)-4,5,6,7-tetrahydro-1H-pyrazolo[3,4-b]pyridin-5-yl)-3-(trifluoromethyl)benzamide (73)

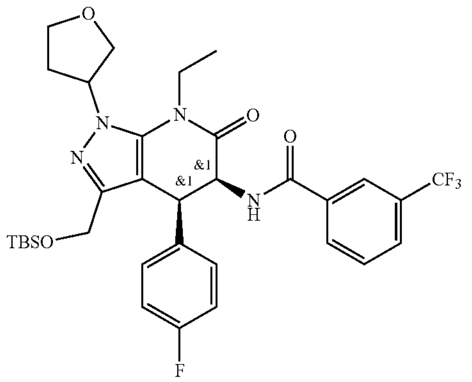

To a stirred solution of rac-N-((4R,5R)-3-(((tert-butyldimethylsilyl)oxy)methyl)-7-ethyl-4-(4-fluorophenyl)-6-oxo-1-(tetrahydrofuran-3-yl)-4,5,6,7-tetrahydro-1H-pyrazolo[3,4-b]pyridin-5-yl)-3-(trifluoromethyl)benzamide (7.0 g, 10.6 mmol, 1.00 equiv) in ACN (50.0 mL) was added HCl (2M) (50.0 mL) dropwise at room temperature under nitrogen atmosphere. The resulting mixture was stirred at room temperature for 2 h under nitrogen atmosphere. The mixture was basified to pH 7 with saturated $NaHCO_3$(aq.). The resulting mixture was extracted with EtOAc (2×100 mL). The combined organic layers were washed with brine (2×100 mL), dried over anhydrous $Na_2SO_4$. After filtration, the filtrate was concentrated under reduced pressure. This resulted in rac-N-((4R,5R)-7-ethyl-4-(4-fluorophenyl)-3-(hydroxymethyl)-6-oxo-1-(tetrahydrofuran-3-yl)-4,5,6,7-tetrahydro-1H-pyrazolo[3,4-b]pyridin-5-yl)-3-(trifluoromethyl)benzamide (5.5 g) as a white solid. The crude product was used in the next step directly without further purification.

LCMS Calculated for $C_{27}H_{26}N_4O_4F_4$: 546.19; Observed (Method-B): 547.3 $[M+H]^+$, 84.3% at RT 1.01 min.

rac-(4R,5R)-7-ethyl-4-(4-fluorophenyl)-6-oxo-1-(tetrahydrofuran-3-yl)-5-(3-(trifluoromethyl)benzamido)-4,5,6,7-tetrahydro-1H-pyrazolo[3,4,b]pyridine-3-carboxylic acid (74)

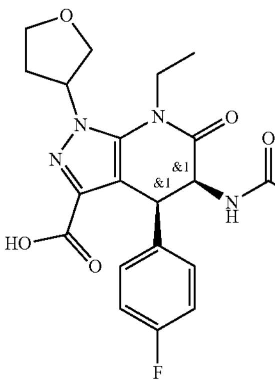

To a stirred solution of rac-N-((4R,5R)-7-ethyl-4-(4-fluorophenyl)-3-(hydroxymethyl)-6-oxo-1-(tetrahydrofuran-3-yl)-4,5,6,7-tetrahydro-1H-pyrazolo[3,4-b]pyridin-5-yl)-3-(trifluoromethyl)benzamide (5.5 g, 10.0 mmol, 1.00 equiv) and periodic acid (4.55 g, 20.0 mmol, 2.00 equiv) in ACN (100 mL) were added $CrO_3$ (0.2 g, 2.0 mmol, 0.20 equiv) in portions at room temperature under nitrogen atmosphere. The resulting mixture was stirred at room temperature for 4 h under nitrogen atmosphere. The reaction was quenched with sat. $Na_2S_2O_3$ (aq.) at room temperature. The resulting mixture was extracted with EtOAc (2×100 mL). The combined organic layers were washed with brine (2×100 mL), dried over anhydrous $Na_2SO_4$. After filtration, the filtrate was concentrated under reduced pressure. The residue was purified by reversed-phase flash chromatography with the following conditions: Column: X Bridge Prep RP C18 Column, 30*150 mm, 5 μm; Mobile Phase A: Water (0.1% TFA), Mobile Phase B: ACN; Flow rate: 35 mL/min; Gradient: 62% B to 92% B in 10 min; Wave Length: 254 nm/220 nm; RT1(min): 6.9 to afford (4S,5S)-7-ethyl-4-(4-fluorophenyl)-6-oxo-1-(tetrahydrofuran-3-yl)-5-(3-(trifluoromethyl)benzamido)-4,5,6,7-tetrahydro-1H-pyrazolo[3,4-b]pyridine-3-carboxylic acid (1.5 g, 26.5%) as a white solid.

LCMS Calculated for $C_{27}H_{26}N_4O_5F_4$: 560.17; Observed (Method-B): 561.2 $[M+H]^+$, 98.6% at RT 0.98 min.

rac-(4R,5R)-7-ethyl-4-(4-fluorophenyl)-6-oxo-1-(tetrahydrofuran-3-yl)-5-(3-(trifluoromethyl)benzamido)-4,5,6,7-tetrahydro-1H-pyrazolo[3,4-b]pyridine-3-carboxylic acid (1 g) was separated by Chiral-SFC with follow conditions: Column Name: Cellulose-SC 100×4.6 mm 3.0 um Co Solvent: MeOH+50% DCM (0.2% FA) to afford 74A (250 mg, 100.0% Chiral purity) and the mixture of 74B, 74C and 74D. The mixture of 74B, 74C and 74D (700 mg) was separated by Chiral-SFC with follow conditions: Column Name: Cellulose-SC 100×4.6 mm 3.0 um Co Solvent: MeOH+50% DCM (0.2% FA) to afford 74B (214 mg, 98.5% Chiral purity), 74C (189 mg, 95.7% Chiral purity) and 74D (218 mg, 89.4% Chiral purity).

Data for 74A:

LCMS Calculated for $C_{27}H_{24}F_4N_4O_5$: 560.17; Observed (Method-J): 561.3 $[M+H]^+$, 98.9% at RT 1.06 min.

Chiral-SFC (Method-K): 100.0% at RT 2.452 min

Optical rotation: [a]=−160.975 (C=0.1000 g/100 ml in MeOH, T=25° C.)

Data for 74B:

LCMS Calculated for $C_{27}H_{24}F_4N_4O_5$: 560.17; Observed (Method-J): 561.3 $[M+H]^+$, 98.8% at RT 1.05 min.

Chiral-SFC (Method-K): 98.5% at RT 2.744 min

Optical rotation: [a]=+170.663 (C=0.1160 g/100 ml in MeOH, T=25° C.)

Data for 74C:

LCMS Calculated for $C_{27}H_{24}F_4N_4O_5$ 560.17; Observed (Method-J): 561.3 $[M+H]^+$, 98.8% at RT 1.06 min.

Chiral-SFC (Method-K): 95.7% at RT 2.899 min

Optical rotation: [a]=−166.974 (C=0.1000 g/100 ml in MeOH, T=25° C.)

Data for 74D:

LCMS Calculated for $C_{27}H_{24}F_4N_4O_5$: 560.17; Observed (Method-J): 561.3 $[M+H]^+$, 99.3% at RT 1.07 min.

Chiral-SFC (Method-K): 89.4% at RT 3.285 min

Optical rotation: [a]=+136.253 (C=0.1020 g/100 ml in MeOH, T=25° C.)

N-((4S*,5S*)-3-((1R,3S,5R)-3-cyano-2-azabicyclo[3.1.0]hexane-2-carbonyl)-7-ethyl-4-(4-fluorophenyl)-6-oxo-1-((S**)-tetrahydro-1H-pyrazolo[3,4-b]pyridin-5-yl)-3-trifluoromethyl)benzamide (I-630)

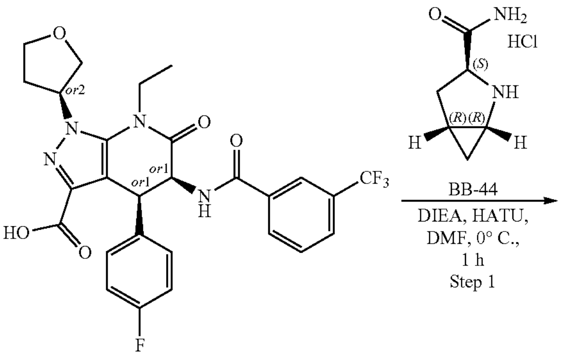

74B

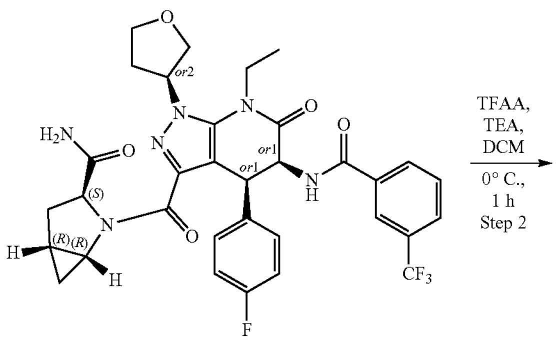

75

-continued

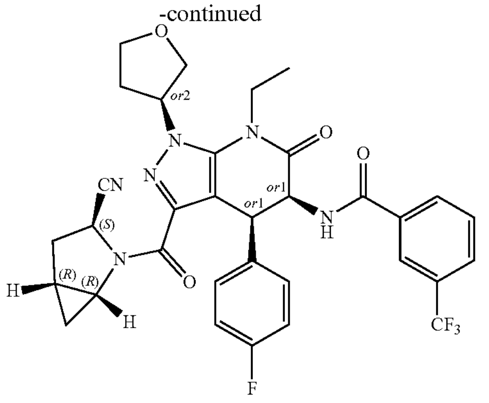

I-630

(1R,3S,5R)-2-((4S*,5S*)-7-ethyl-4-(4-fluorophenyl)-6-oxo-1-((S**)-tetrahydrofuran-3-yl)-5-(3-(trifluoromethyl)benzamido)-4,5,6,7-tetrahydro-1H-pyrazolo[3,4-b]pyridine-3-carbonyl)-2-azabicyclo[3.1.0]hexane-3-carboxamide (75)

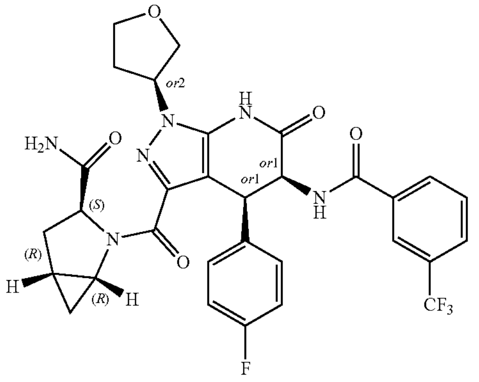

Into a 8 mL vial were added (4S*,5S*)-7-ethyl-4-(4-fluorophenyl)-6-oxo-1-((S**)-tetrahydrofuran-3-yl)-5-(3-(trifluoromethyl)benzamido)-4,5,6,7-tetrahydro-1H-pyrazolo[3,4-b]pyridine-3-carboxylic acid 74B (100 mg, 0.178 mmol, 1.00 equiv), DIEA (69.1 mg, 0.534 mmol, 3.00 equiv) and HATU (81.4 mg, 0.214 mmol, 1.20 equiv) in DMF (2 mL) at room temperature. The mixture was stirred at 0° C. for 10 minute, (1R,3S,5R)-2-azabicyclo[3.1.0]hexane-3-carboxamide hydrochloride (34.8 mg, 0.214 mmol, 1.20 equiv) was added and the mixture was allowed to stir for 1 hour at 0° C. The reaction was purified by Column: YMC-Actus Triart C18 Column, 50*250 mm, 5 μm; Mobile Phase A: Water (10 mmol/L $NH_4HCO_3$), Mobile Phase B: ACN; Flow rate: 90 mL/min; Gradient: 45% B to 75% B in 16 min; Wave Length: 254 nm/220 nm; RT1(min): 10 to afford (1R,3S,5R)-2-((4S*,5S*)-7-ethyl-4-(4-fluorophenyl)-6-oxo-1-((S**)-tetrahydrofuran-3-yl)-5-(3-(trifluoromethyl)benzamido)-4,5,6,7-tetrahydro-1H-pyrazolo[3,4-b]pyridine-3-carbonyl)-2-azabicyclo[3.1.0]hexane-3-carboxamide (95 mg, 85.3% purity) as a white solid.

LCMS Calculated for $C_{33}H_{32}F_4N_6O_5$: 668.24. Observed: 669.2 $[M+H]^+$.

N-((4S*,5S*)-3-((1R,3S,5R)-3-cyano-2-azabicyclo[3.1.0]hexane-2-carbonyl)-7-ethyl-4-(4-fluorophenyl)-6-oxo-1-((S**)-tetrahydrofuran-3-yl)-4,5,6,7-tetrahydro-1H-pyrazolo[3,4-b]pyridin-5-yl)-3-(trifluoromethyl)benzamide (I-630)

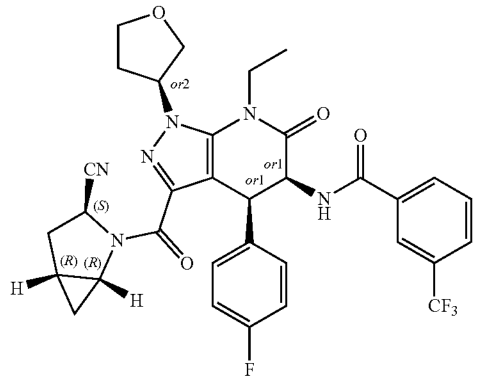

Into a 8 mL vial were added (1R,3S,5R)-2-((4S*,5S*)-7-ethyl-4-(4-fluorophenyl)-6-oxo-1-((S**)-tetrahydrofuran-3-yl)-5-(3-(trifluoromethyl)benzamido)-4,5,6,7-tetrahydro-1H-pyrazolo[3,4-b]pyridine-3-carbonyl)-2-azabicyclo[3.1.0]hexane-3-carboxamide (60 mg, 0.098 mmol, 1.00 equiv), $Et_3N$ (39.5 mg, 0.392 mmol, 4.00 equiv) in DCM (2 mL) at room temperature, Trifluoroacetic anhydride (41.0 mg, 0.196 mmol, 2.00 equiv) was added at 0° C. The mixture was stirred at room temperature for 1 hour, concentrated in vacuum. The reaction was purified by Column: Uitimate-XB-C18 Column, 30*150 mm, 10 μm; Mobile Phase A: Water (10 mmol/L $NH_4HCO_3$+0.05$NH_3H_2O$), Mobile Phase B: ACN; Flow rate: 60 mL/min; Gradient: isocratic 35%-85% 10 min; Wave Length: 254 nm/220 nm; RT1(min): 9.2 to afford N-((4S*,5S*)-3-((1R,3S,5R)-3-cyano-2-azabicyclo[3.1.0]hexane-2-carbonyl)-7-ethyl-4-(4-fluorophenyl)-6-oxo-1-((S**)-tetrahydrofuran-3-yl)-4,5,6,7-tetrahydro-1H-pyrazolo[3,4-b]pyridin-5-yl)-3-(trifluoromethyl)benzamide (2 mg, 99.5% purity) as a white solid.

$^1$H NMR (400 MHZ, DMSO-$d_6$) δ 8.51 (d, J=7.1 Hz, 1H), 8.19-8.10 (m, 2H), 7.92 (d, J=7.8 Hz, 1H), 7.71 (t, J=7.8 Hz, 1H), 7.07 (dd, J=10.0, 7.7 Hz, 2H), 7.01-6.93 (m, 2H), 5.70-5.16 (m, 2H), 4.98 (d, J=7.1 Hz, 1H), 4.82 (dd, J=9.0, 5.0 Hz, 1H), 4.37-4.30 (m, 1H), 4.27-4.21 (m, 1H), 4.17-4.11 (m, 1H), 4.01-3.91 (m, 3H), 2.48-2.24 (m, 4H), 2.02-1.94 (m, 1H), 1.32 (t, J=7.0 Hz, 3H), 0.95-0.86 (m, 1H), 0.58-0.53 (m, 2H).

LCMS Calculated for $C_{33}H_{30}F_4N_6O_4$: 650.23; Observed (Method-C): 651.2 $[M+H]^+$, 99.91% at RT 1.369 min.

Chiral SFC (Method-I): 100% at RT 1.56 min.

Using the Methodology Above, the Following Compounds were Prepared:

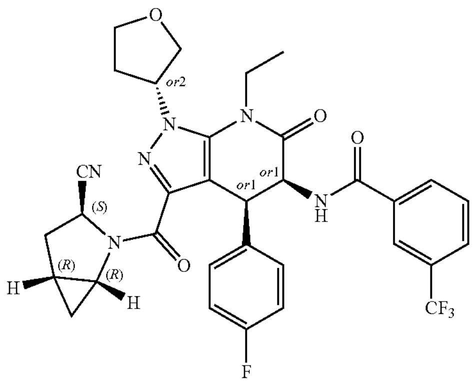

I-562

$^1H$ NMR (300 MHz, DMSO-$d_6$) δ 8.49 (d, J = 7.2 Hz, 1H), 8.20-8.03 (m, 2H), 7.90 (d, J = 7.6 Hz, 1H), 7.69 (t, J = 7.7 Hz, 1H), 7.05 (t, J = 8.7 Hz, 2H), 6.94 (t, J = 7.1 Hz, 2H), 5.34-5.11 (m, 2H), 4.95 (d, J = 7.2 Hz, 1H), 4.80 (dd, J = 8.7, 4.9 Hz, 1H), 4.37-3.80 (m, 7H), 3.58-3.36 (m, 1H), 2.41-2.17 (m, 2H), 2.08-1.89 (m, 1H), 1.29 (t, J = 6.5 Hz, 3H), 0.97-0.78 (m, 1H), 0.66-0.46 (m, 1H).
LCMS Calculated for $C_{33}H_{30}F_4N_6O_4$: 650.23; Observed (Method-P): 649.3 [M − H]$^-$, 99.90% at RT 1.737 min.
Chiral-SFC (Method-H): 97.74% at RT 1.74 min.

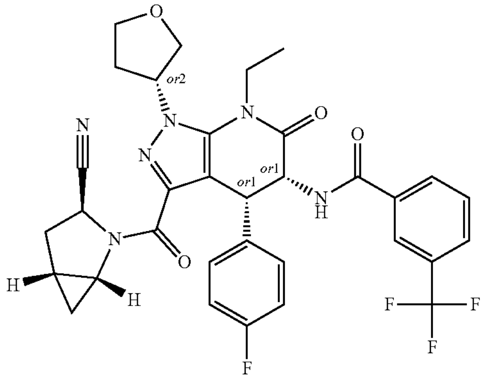 [SMILES: CCN1C(=O)[C@H](NC(=O)c2cccc(C(F)(F)F)c2)[C@H](c2ccc(F)cc2)c2c(C(=O)N3[C@H](C#N)C[C@H]4C[C@H]43)nn([C@@H]3CCOC3)c21]

I-704

1H NMR (300 MHz, DMSO-d6) δ 8.50 (d, J = 6.9 Hz, 1H), 8.20-8.07 (m, 2H), 7.92 (d, J = 7.8 Hz, 1H), 7.71 (t, J = 7.8 Hz, 1H), 7.08 (t, J = 8.8 Hz, 2H), 6.96 (tt, J = 5.7, 2.6 Hz, 2H), 5.79-4.67 (m, 4H), 4.38-4.16 (m, 1H), 4.07 (dd, J = 10.1, 7.2 Hz, 3H), 3.92 (td, J = 8.1, 4.7 Hz, 2H), 2.72 (s, 1H), 2.55-2.49 (m, 1H), 2.48-2.25 (m, 2H), 1.99 (d, J = 7.3 Hz, 1H), 1.30 (t, J = 6.8 Hz, 3H), 0.94 (dt, J = 14.3, 8.6 Hz, 1H), 0.58 (d, J = 85.6 Hz, 1H).
LCMS Calculated for $C_{30}H_{31}F_4N_5O_3$: 650.23; Observed (Method-D): 649.3 [M − H]$^-$, 99.7% at RT 1.712 min.
Chiral-SFC (Method-I): 100.00% at RT 0.88 min

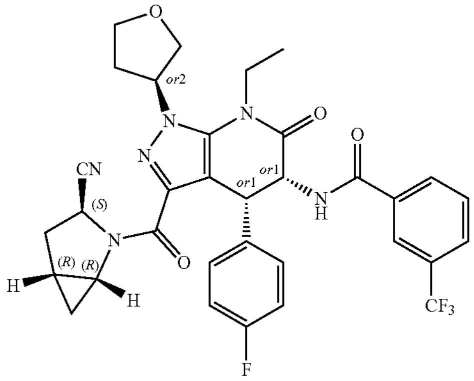

I-482

$^1H$ NMR (300 MHz, DMSO-$d_6$) δ 8.50 (d, J = 6.9 Hz, 1H), 8.10 (d, J = 10.2 Hz, 2H), 7.93-7.87 (m, 1H), 7.69 (t, J = 7.8 Hz, 1H), 7.11-6.99 (m, 2H), 6.99-6.88 (m, 2H), 5.30-5.14 (m, 2H), 4.88 (dd, J = 8.7, 5.3 Hz, 1H), 4.80 (d, J = 7.0 Hz, 1H), 4.34-4.03 (m, 4H), 4.02-3.85 (m, 3H), 2.45-2.29 (m, 4H), 2.03-1.89 (m, 1H), 1.29 (t, J = 7.0 Hz, 3H), 0.99-0.84 (m, 1H), 0.74-0.65 (m, 1H).
LCMS Calculated for $C_{33}H_{30}F_4N_6O_4$: 650.23; Observed (Method-P): 649.3 [M − H]$^-$, 99.90% at RT 1.737 min.
Chiral-SFC (Method-I): 100.0% at RT 1.80 min 16. Synthesis of N-((4S,5S)-3-(4-cyano-1,1-dioxidothizolidine-3-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-661).

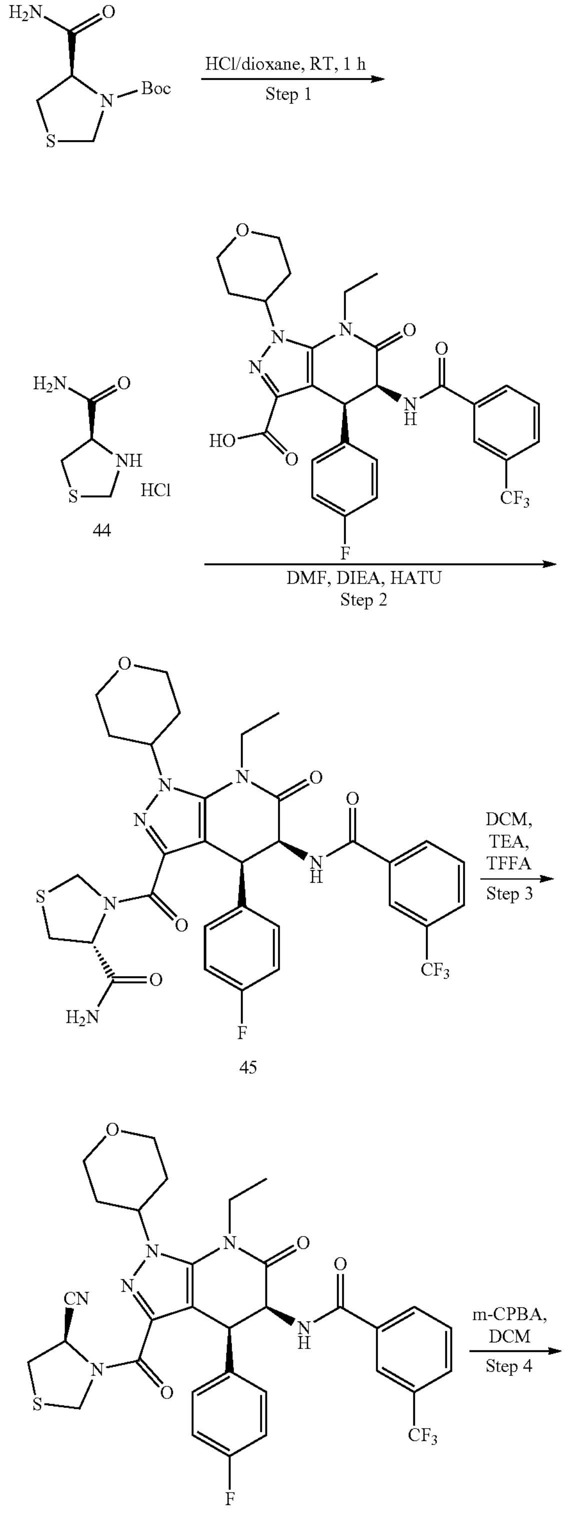

44

45

46

-continued

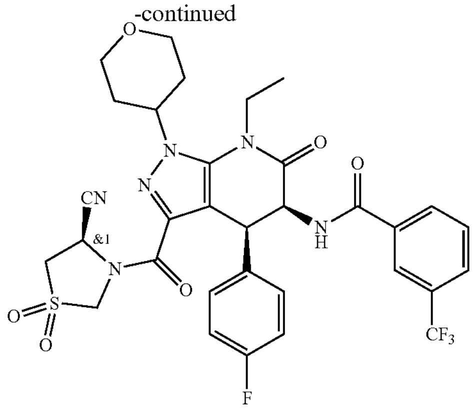

I-661

(R)-thiazolidine-4-carboxamide (44)

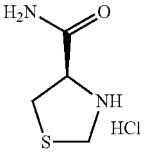

A solution of tert-butyl (4R)-4-carbamoyl-1,3-thiazolidine-3-carboxylate (581 mg, 2.50 mmol, 1.00 equiv) in DCM (6 mL) was treated with hydrochloric titrant (6 mL) at room temperature for 2 h under nitrogen atmosphere. The resulting mixture was concentrated under reduced pressure. The residue was purified by trituration with 2-methoxy-2-methylpropane (20 mL). The precipitated solids were collected by filtration and washed with 2-methoxy-2-methylpropane (3×10 mL). This resulted in (4R)-1,3-thiazolidine-4-carboxamide hydrochloride (500 mg, curde) as a yellow solid.

LCMS Calculated for $C_4H_8N_2OS$: 132.04; Observed: 132.18 $[M+H]^+$.

3-((4S,5S)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carbonyl)thiazolidine-4-carboxamide (45)

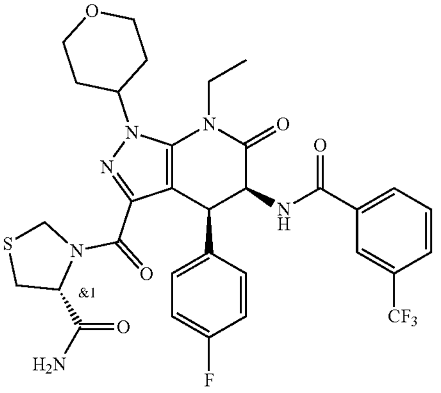

To a stirred solution of (4S,5S)-7-ethyl-4-(4-fluorophenyl)-1-(oxan-4-yl)-6-oxo-5-[3-(trifluoromethyl)benzam ido]-4H,5H-pyrazolo[3,4-b]pyridine-3-carboxylic acid (100 mg, 0.174 mmol, 1.00 equiv) in anhydrous DMF (1 mL) was added DIEA (89.9 mg, 0.696 mmol, 4.00 equiv) and HATU (99.3 mg, 0.261 mmol, 1.50 equiv) followed by (4R)-1,3-thiazolidine-4-carboxamide hydrochloride (44.0 mg, 0.261 mmol, 1.50 equiv) at 0° C. The reaction mixture was stirred at room temperature for 2 h. The reaction was quenched by the addition of water (0.3 mL) at room temperature. The residue was purified by reversed-phase flash chromatography with the following conditions: column, C18 silica gel; mobile phase, MeCN in water (0.1% $NH_3{\cdot}H_2O$), 10% to 90% gradient in 10 min; detector, UV 254 nm. This resulted in 3-((4S,5S)-7-ethyl-4-(4-fluorophenyl)-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carbonyl) thiazolidine-4-carboxamide (85 mg, 70.91% yield, 95% purity) as a white solid.

N-((4S,5S)-3-(4-cyanothiazolidine-3-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (46)

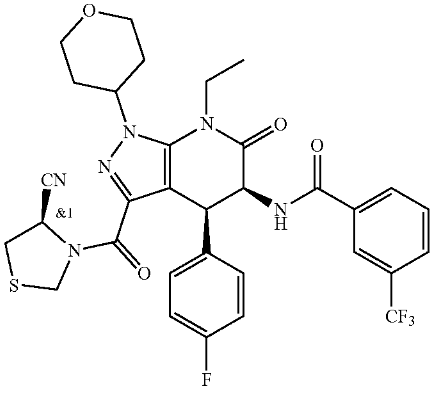

A solution of 3-((4S,5S)-7-ethyl-4-(4-fluorophenyl)-6-oxo-1-(tetrahydro-2H-pyran-4-yl)-5-(3-(trifluoromethyl) benzamido)-4,5,6,7-tetrahydro-1H-pyrazolo[3,4-b]pyridine-3-carbonyl) thiazolidine-4-carboxamide (85.0 mg, 0.123 mmol, 1.00 equiv) in DCM (1 mL) was treated with TEA (56.2 mg, 0.553 mmol, 4.50 equiv) at room temperature for 5 min under nitrogen atmosphere followed by the addition of Trifluoroacetic anhydride (51.8 mg, 0.246 mmol, 2.00 equiv) dropwise at room temperature. The resulting mixture was stirred at room temperature for 2 h under nitrogen atmosphere. The reaction was quenched by the addition of Water (1 mL) at room temperature. The resulting mixture was extracted with DCM (2×1 mL). The combined organic layers were washed with saturated sodium bicarbonate solution (1×2 mL) and saturated sodium solution (1×2 mL), dried over anhydrous $Na_2SO_4$. After filtration, the filtrate was concentrated under reduced pressure. This resulted in N-((4S,5S)-3-(4-cyanothiazolidine-3-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (72 mg) as a yellow solid.

LCMS Calculated for $C_{32}H_{30}F_4N_6O_4S$: 670.20; Observed: 671.68 $[M+H]^+$.

N-((4S,5S)-3-(4-cyano-1,1-dioxidothiazolidine-3-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl) benzamide (I-661)

A solution of N-((4S,5S)-3-(4-cyanothiazolidine-3-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (72.0 mg, 0.107 mmol, 1.00 equiv) in DCM (1.00 mL) was treated with 3-chlorobenzene-1-carboperoxoic acid (46.3 mg, 0.268 mmol, 2.50 equiv) at room temperature for 4 h. The reaction was quenched by the addition of $Na_2SO_3$ (1 mL) at room temperature. The mixture was basified to pH 9 with $K_2CO_3$. The resulting mixture was extracted with DCM (3×1 mL). The combined organic layers were washed with DCM (1 mL) (3×1 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% $NH_3{\cdot}H_2O$), 30% to 80% gradient in 10 min; detector, UV 254 nm. This resulted in N-((4S,5S)-3-(4-cyano-1,1-dioxidothiazolidine-3-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (15 mg, 19.8% yield) as a white solid.

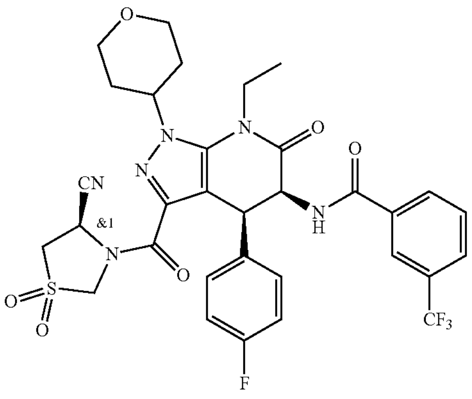 [SMILES: CCN1C(=O)[C@@H](NC(=O)c2cccc(C(F)(F)F)c2)[C@@H](c2ccc(F)cc2)c2c(C(=O)N3CS(=O)(=O)C[C@H]3C#N)nn(C3CCOCC3)c21]

I-661

$^1H$ NMR (300 MHz, DMSO-$d_6$) δ 8.59-8.46 (m, 1H), 8.18-8.06 (m, 2H), 7.90 (d, J = 7.8 Hz, 1H), 7.69 (t, J = 7.8 Hz, 1H), 7.05 (t, J = 8.8 Hz, 2H), 7.00-6.89 (m, 2H), 5.62-5.15 (m, 3H), 5.00-4.51 (m, 3H), 4.23-3.86 (m, 6H), 3.77 (dd, J = 13.6, 8.7 Hz, 1H), 3.55 (dt, J = 25.3, 11.6 Hz, 2H), 2.44-2.30 (m, 1H), 2.21-2.01 (m, 2H), 1.95 (d, J = 12.5 Hz, 1H), 1.31 (t, J = 7.0 Hz, 3H).
LCMS Calculated for $C_{32}H_{30}F_4N_6O_6S$: 702.19; Observed (Method-M): 701.2 $[M-H]^-$, 98.9% at RT 1.906 min.
Chiral-SFC (Method-Y): 81.4% at RT 1.71 min.

-continued

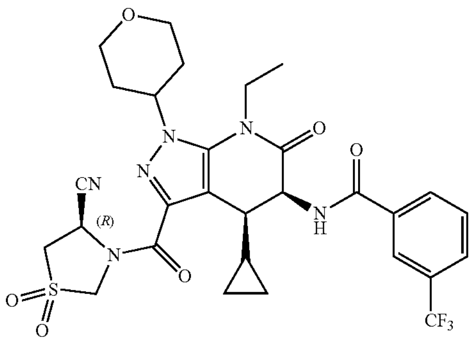

$^{1}$H NMR (300 MHz, DMSO-$d_6$) δ 9.11-8.97 (m, 1H), 8.31 (s, 1H), 8.25 (d, J = 7.9 Hz, 1H), 7.95 (d, J = 7.9 Hz, 1H), 7.76 (t, J = 7.8 Hz, 1H), 5.71-5.58 (m, 1H), 5.37-4.68 (m, 3H), 4.62-4.45 (m, 1H), 4.23-4.01 (m, 3H), 3.99-3.78 (m, 3H), 3.66-3.37 (m, 3H), 2.41-2.21 (m, 1H), 2.17-1.81 (m, 3H), 1.25 (t, J = 7.0 Hz, 3H), 0.91-0.77 (m, 1H), 0.57-0.43 (m, 1H), 0.26-0.04 (m, 3H).
LCMS Calculated for $C_{29}H_{31}F_3N_6O_6S$: 648.20; Observed (Method-AK): 649.3 $[M + H]^+$, 92.2% at RT 1.855 min.
Chiral-SFC (Method-H): 94.66% at RT 1.79 min

I-617

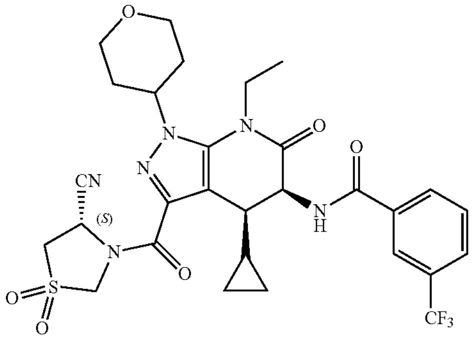

$^{1}$H NMR (300 MHz, Chloroform-d) δ 8.14 (s, 1H), 8.06 (d, J = 7.8 Hz, 1H), 7.83 (d, J = 7.8 Hz, 1H), 7.65 (t, J = 7.8 Hz, 1H), 7.35 (d, J = 6.6 Hz, 1H), 5.84 (t, J = 6.3 Hz, 1H), 5.69 (d, J = 12.3 Hz, 1H), 5.03-4.88 (m, 2H), 4.50-4.32 (m, 1H), 4.30-4.05 (m, 3H), 3.95-3.80 (m, 1H), 3.68-3.45 (m, 5H), 2.58-2.37 (m, 1H), 2.27-2.14 (m, 1H), 2.08 (d, J = 13.0 Hz, 1H), 1.90 (d, J = 13.2 Hz, 1H), 1.38 (t, J = 7.1 Hz, 4H), 0.94-0.83 (m, 1H), 0.68-0.50 (m, 3H), 0.40-0.23 (m, 2H).
LCMS Calculated for $C_{29}H_{31}F_3N_6O_6S$: 648.20; Observed (Method-AM): 647.4 $[M - H]^-$, 92.2% at RT 1.855 min.
Chiral-SFC (Method-H): 92.19% at RT 1.89 min

I-560

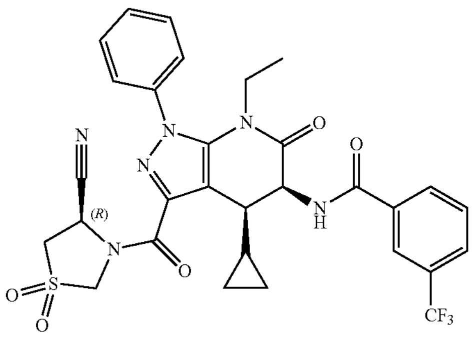

$^{1}$H NMR (300 MHz, DMSO-$d_6$) δ 9.13 (d, J = 7.9 Hz, 1H), 8.36 (s, 1H), 8.29 (d, J = 7.9 Hz, 1H), 7.97 (d, J = 7.8 Hz, 1H), 7.79 (q, J = 7.8, 7.3 Hz, 3H), 7.62 (d, J = 6.3 Hz, 3H), 5.71 (t, J = 7.3 Hz, 1H), 5.53 (d, J = 12.3 Hz, 1H), 5.46-5.38 (m, 1H), 5.17 (d, J = 12.4 Hz, 1H), 4.09-3.82 (m, 3H), 3.50 (t, J = 6.5 Hz, 1H), 3.02-2.85 (m, 1H), 0.85 (t, J = 7.0 Hz, 4H), 0.60-0.46 (m, 1H), 0.32-0.17 (m, 1H), 0.15-0.04 (m, 2H).
LCMS Calculated for $C_{30}H_{27}F_3N_6O_5S$: 640.17; Observed (Method-AS): 641.2 $[M + H]^+$, 99.7% at RT 1.192 min.
Chiral-SFC (Method-A): 97.68% at RT 1.63 min

I-519

-continued

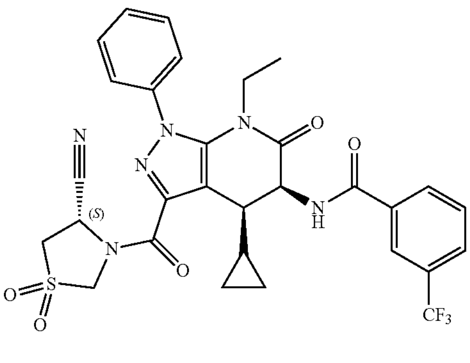

I-521

$^1$H NMR (300 MHz, DMSO-$d_6$) δ 9.13 (d, J = 8.0 Hz, 1H), 8.35 (s, 1H), 8.28 (d, J = 7.8 Hz, 1H), 7.97 (d, J = 7.8 Hz, 1H), 7.87-7.72 (m, 3H), 7.62 (d, J = 7.1 Hz, 3H), 5.64 (d, J = 8.4 Hz, 1H), 5.53-5.35 (m, 2H), 5.09 (d, J = 12.2 Hz, 1H), 4.09 (d, J = 13.8 Hz, 1H), 4.00-3.78 (m, 2H), 3.42 (t, J = 6.8 Hz, 1H), 3.03-2.84 (m, 1H), 0.85 (t, J = 7.0 Hz, 5H), 0.63-0.47 (m, 1H), 0.32-0.05 (m, 3H).
LCMS Calculated for $C_{30}H_{27}F_3N_6O_5S$: 640.17; Observed (Method-AN): 641.2 [M + H]$^+$, 97.9% at RT 1.186 min.
Chiral-SFC (Method-A): 96.68% at RT 1.75 min

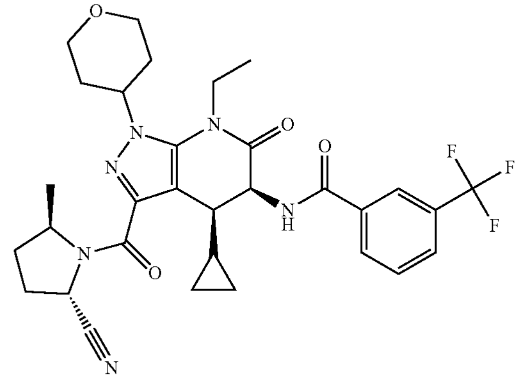 [SMILES: CCN1C(=O)[C@@H](NC(=O)c2cccc(C(F)(F)F)c2)[C@@H](C2CC2)c2c(C(=O)N3[C@H](C)CC[C@H]3C#N)nn(C3CCOCC3)c21]

I-621

$^1$H NMR (300 MHz, DMSO-$d_6$) δ 9.04 (dd, J = 8.1, 4.8 Hz, 1H), 8.32 (s, 1H), 8.25 (d, J = 7.8 Hz, 1H), 7.96 (d, J = 7.8 Hz, 1H), 7.76 (t, J = 7.8 Hz, 1H), 5.81-4.29 (m, 4H), 4.21-3.69 (m, 4H), 3.62-3.36 (m, 3H), 2.43-2.03 (m, 6H), 1.95-1.60 (m, 2H), 1.26 (td, J = 7.1, 2.7 Hz, 3H), 1.15 (m, 3H), 0.84 (s, 1H), 0.53-0.43 (m, 1H), 0.27-0.01 (m, 2H).
LCMS Calculated for $C_{31}H_{35}F_3N_6O_4$: 612.27; Observed (Method-D): 611.3 [M − H]$^-$, 99.9% at RT 1.958 min.
Chiral-SFC (Method-A): 99.7% at RT 1.26 min

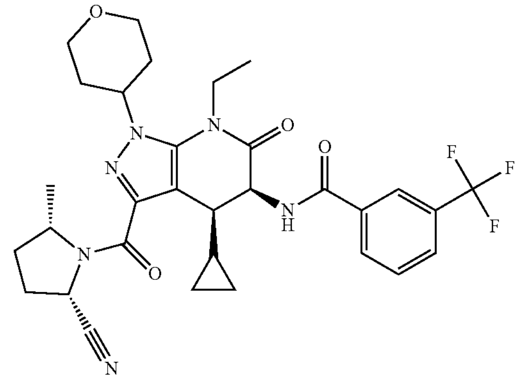 [SMILES: CCN1C(=O)[C@@H](NC(=O)c2cccc(C(F)(F)F)c2)[C@@H](C2CC2)c2c(C(=O)N3[C@H](C#N)CC[C@@H]3C)nn(C3CCOCC3)c21]

I-700

$^1$H NMR (300 MHz, DMSO-$d_6$) δ 9.03 (t, J = 7.2 Hz, 1H), 8.31 (s, 1H), 8.24 (d, J = 7.2 Hz, 1H), 7.96 (d, J = 7.8 Hz, 1H), 7.76 (t, J = 7.8 Hz, 1H), 5.63-4.52 (m, 3H), 4.26-3.78 (m, 5H), 3.54 (m, 2H), 3.41 (t, J = 6.6 Hz, 1H), 2.32 (m, 4H), 2.07 (d, J = 11.7 Hz, 2H), 1.93 (d, J = 9.9 Hz, 1H), 1.73 (m, 1H), 1.41-1.18 (m, 6H), 0.83 (m, 1H), 0.49 (m, 1H), 0.22 (m, 2H), 0.07 (m, 1H).
LCMS Calculated for $C_{31}H_{35}F_3N_6O_4$: 612.27; Observed (Method-P): 611.3 [M − H]$^-$, 99.8% at RT 2.247min.
Chiral-SFC (Method-D): 100% at RT 2.08 min Synthesis of N-((4S,5S))-3-((R)-3-cyano-1,1-dioxidothiomorphine-4-carbonyl)-4-cyclopropyl-7-ethyl-6-oxo-1-phenyl-4,5,6,7-tetrahydro-1H-pyrazolo[3,4-b]pyridin-5-yl)-3-(trifluoromethyl)benzamide (I-659) and N-((4S,5S))-3-((S)-3-cyano-1,1-dioxidothiomorphine-4-carbonyl)-4-cyclopropyl-7-ethyl-6-oxo-1-phenyl-4,5,6,7-tetrahydro-1H-pyrazolo[3,4-b]pyridin-5-yl)-3-(trifluoromethyl)benzamide (I-438)

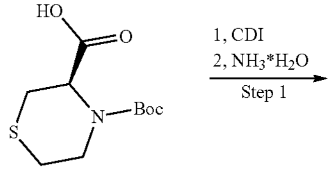

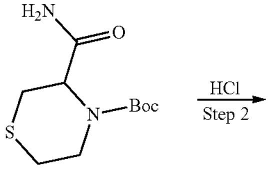

R:S = 3:1

1

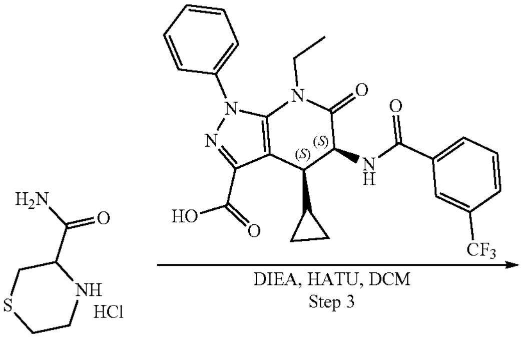

2

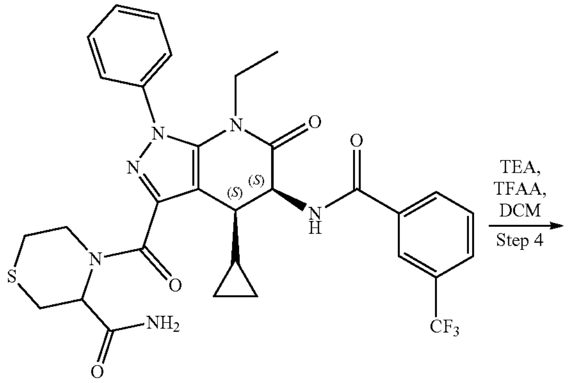

3

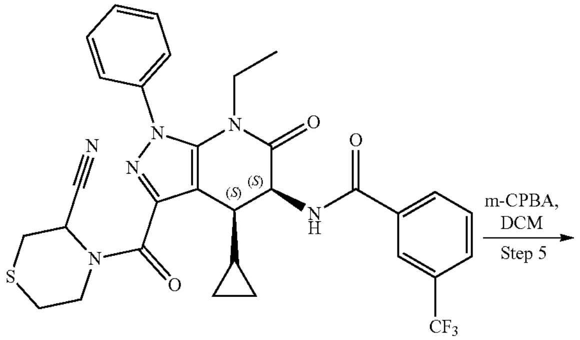

4

-continued

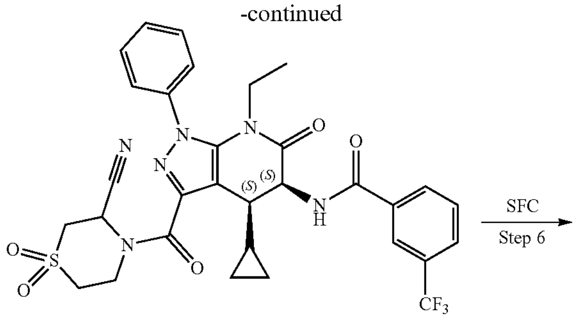

5

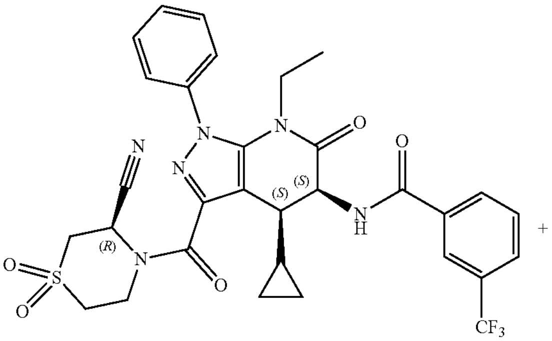

+

I-659

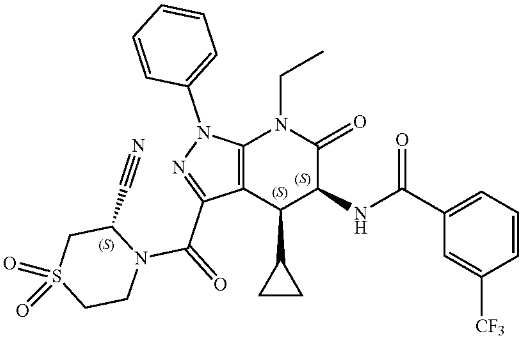

I-438 tert-butyl 3-carbamoylthiomorpholine-4-carboxylate (1)

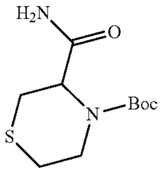

To a solution of THE (30 mL) was added (3R)-4-(tert-butoxycarbonyl)thiomorpholine-3-carboxylic acid (2.00 g, 8.09 mmol, 1.00 equiv) and 1-[(1H-imidazol-1-yl) carbonyl]-1H-imidazole (1.57 g, 9.70 mmol, 1.20 equiv) at 0° C. The mixture was stirred for 1 hour at 0° C. The mixture were dropwise added to ammonium hydroxide solution (9% in water) (10 mL) at 0° C. and the mixture was stirred for 1 hour. The solution was extracted with EtOAc (3×50 mL). The combined organic layers were washed with brine (2×50 mL), dried over anhydrous $Na_2SO_4$. After filtration, the filtrate was concentrated under reduced pressure to afford tert-butyl 3-carbamoylthiomorpholine-4-carboxylate (R:S=3:1) (1.8 g, 85.6% purity) as a colorless oil.

thiomorpholine-3-carboxamide hydrochloride (2)

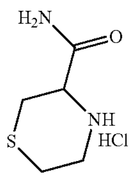

A solution of tert-butyl 3-carbamoylthiomorpholine-4-carboxylate (500 mg, 2.03 mmol, 1.00 equiv) in HCl in 1,4-dioxane (4.0 M) (5 mL) was stirred at room temperature for 30 min under nitrogen atmosphere. The resulting mixture was concentrated under reduced pressure. This resulted in thiomorpholine-3-carboxamide hydrochloride (R: S-3:1) (350 mg) as a yellow solid.

LCMS Calculated for $C_5H_{11}ClN_2OS$: 182.03; Observed: 147.1 $[M-HCl+H]^+$ 4-((4S,5S)-4-cyclopropyl-7-ethyl-6-oxo-1-phenyl-5-(3-(trifluromethyl) benzamido)-4,5,6,7-tetrahydro-1H-pyrazolo[3,4-b]pyridine-3-carbonyl) thiomorpholine-3-carboxamide (3)

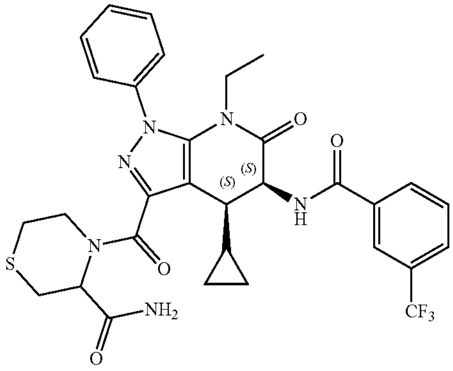

A solution of (4S,5S)-4-cyclopropyl-7-ethyl-6-oxo-1-phenyl-5-[3-(trifluoromethyl)benzamido]-4H,5H-pyrazolo [3,4-b]pyridine-3-carboxylic acid (245 mg, 0.479 mmol, 1.00 equiv) in DMF (2 mL) was treated with DIEA (248 mg, 1.92 mmol, 4.00 equiv) and HATU (18.2 mg, 0.048 mmol, 0.100 equiv) at 0° C. for 5 min under nitrogen atmosphere followed by the addition of thiomorpholine-3-carboxamide hydrochloride (R:S=3:1) (70 mg, 0.479 mmol, 1.00 equiv) at 0° C. for 30 min. The reaction was quenched by the addition of water (0.2 mL) at 0° C. The resulting mixture was purified by reversed-phase flash chromatography with the condition Method-A. This resulted in 4-((4S,5S)-4-cyclopropyl-7-ethyl-6-oxo-1-phenyl-5-(3-(trifluoromethyl)benzamido)-4,5,6,7-tetrahydro-1H-pyrazolo[3,4-b]pyridine-3-carbonyl) thiomorpholine-3-carboxamide (160 mg, 52.1% yield, 90% purity) as a white solid.

LCMS Calculated for $C_{31}H_{31}F_3N_6O_4S$: 640.21; Observed: 641.3 $[M+H]^+$

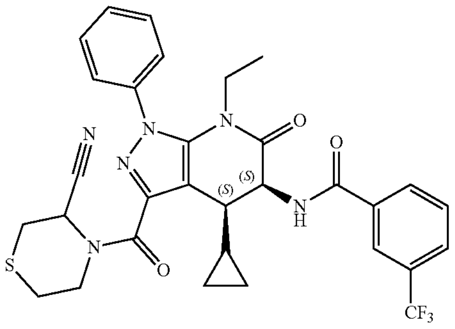

N-((4S,5S)-3-(3-cyanothiomorpholine-4-carbonyl)-4-cyclopropyl-7-ethyl-6-oxo-1-phenyl-4,5,6,7-tetrahydro-1H-pyrazolo[3,4-b]pyridin-5-yl)-3-(trifluoromethyl)benzamide (4)

A solution of 4-((4S,5S)-4-cyclopropyl-7-ethyl-6-oxo-1-phenyl-5-(3-(trifluoromethyl)benzamido)-4,5,6,7-tetrahydro-1H-pyrazolo[3,4-b]pyridine-3-carbonyl)thiomorpholine-3-carboxamide (160 mg, 0.250 mmol, 1.00 equiv) in DCM (3 mL) was treated with $Et_3N$ (75.8 mg, 0.750 mmol, 3.00 equiv) at 0° C. for 5 min under nitrogen atmosphere followed by the addition of TFAA (78.7 mg, 0.375 mmol, 1.50 equiv) dropwise at 0° C. The resulting mixture was stirred for 30 min at room temperature. The reaction was quenched by the addition of water (3 mL) at room temperature. The resulting mixture was extracted with DCM (3×3 mL). The combined organic layers were washed with brine (1×5 mL), dried over anhydrous $Na_2SO_4$. After filtration, the filtrate was concentrated under reduced pressure. The crude product (152 mg, a brown solid) was used in the next step directly without further purification.

LCMS Calculated for $C_{31}H_{29}F_3N_6O_3S$: 622.20; Observed: 623.3 $[M+H]^+$

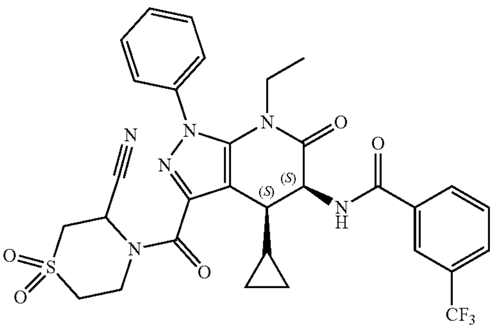

N-((4S,5S)-3-(3-cyano-1,1-dioxidothiomorpholine-4-carbonyl)-4-cyclopropyl-7-ethyl-6-oxo-1-phenyl-4,5,6,7-tetrahydro-1H-pyrazolo[3,4-b]pyridin-5-yl)-3-(trifluoromethyl)benzamide (4)

A solution of N-((4S,5S)-3-(3-cyanothiomorpholine-4-carbonyl)-4-cyclopropyl-7-ethyl-6-oxo-1-phenyl-4,5,6,7-tetrahydro-1H-pyrazolo[3,4-b]pyridin-5-yl)-3-(trifluoromethyl)benzamide (152 mg, 0.244 mmol, 1.00 equiv) in DCM (3 mL) was treated with m-CPBA (126 mg, 0.732 mmol, 3.00 equiv) at room temperature for 2 h under nitrogen atmosphere. The reaction was quenched by the addition of $Na_2S_2O_3$ aq. (5 mL) at 0° C. The resulting mixture was extracted with DCM (3×5 mL). The combined organic layers were washed with brine (1×10 mL), dried over anhydrous $Na_2SO_4$. After filtration, the filtrate was concentrated under reduced pressure. The residue was purified by reversed-phase flash chromatography with the condition (Method-A). This resulted in N-((4S,5S)-3-(3-cyano-1,1-dioxidothiomorpholine-4-carbonyl)-4-cyclopropyl-7-ethyl-6-oxo-1-phenyl-4,5,6,7-tetrahydro-1H-pyrazolo[3,4-b]pyridin-5-yl)-3-(trifluoromethyl)benzamide (80 mg, 50.0% yield, 95% purity) as a white solid.

LCMS Calculated for $C_{31}H_{29}F_3N_6O_5S$: 654.19; Observed: 655.2 $[M+H]^+$

Synthesis of N-((4S,5S)-3-((R)-3-cyano-1,1-dioxidothiomorpholine-4-carbonyl)-4-cycloprop yl-7-ethyl-6-oxo-1-phenyl-4,5,6,7-tetrahydro-1H-pyrazolo[3,4-b]pyridin-5-yl)-3-(trifluorom ethyl) benzamide (I-659) and N-((4S,5S)-3-((S)-3-cyano-1,1-dioxidothiomorpholine-4-carbon yl)-4-cyclopropyl-7-ethyl-6-oxo-1-phenyl-4,5,6,7-tetrahydro-1H-pyrazolo[3,4-b]pyridin-5-yl)-3-(trifluoromethyl)benzamide (I-438)

N-((4S,5S)-3-(3-cyano-1,1-dioxidothiomorpholine-4-carbonyl)-4-cyclopropyl-7-ethyl-6-oxo-1-phenyl-4,5,6,7-tetrahydro-1H-pyrazolo[3,4-b]pyridin-5-yl)-3-(trifluoromethyl) benzamide (80 mg) was separated by Chiral-SFC with follow conditions: Column Name: (R,R)-WHELK-O1 50×4.6 mm 3.5 μm Co Solvent: MeOH+50% DCM+20 mM $NH_3$, Gradient: isocratic 35% B. This resulted in N-((4S,5S)-3-((R)-3-cyano-1,1-dioxidothiomorpholine-4-carbonyl)-4-cyclopropyl-7-ethyl-6-oxo-1-phenyl-4,5,6,7-tetrahydro-1H-pyrazolo[3,4-b]pyridin-5-yl)-3-(trifluoromethyl)benzamide (30 mg, 37.50% yield, 98.4% purity) and N-((4S,5S)-3-((S)-3-cyano-1,1-dioxidothiomorpholine-4-carbonyl)-4-cyclopropyl-7-ethyl-6-oxo-1-phenyl-4,5,6,7-tetrahydro-1H-pyrazolo[3,4-b]pyridin-5-yl)-3-(trifluoromethyl)benzamide (10 mg, 12.5% yield, 98.7% purity).

Example 38: Synthesis of Compounds

Synthesis of (4R,5R)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-575) & (4S,5S)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-545)

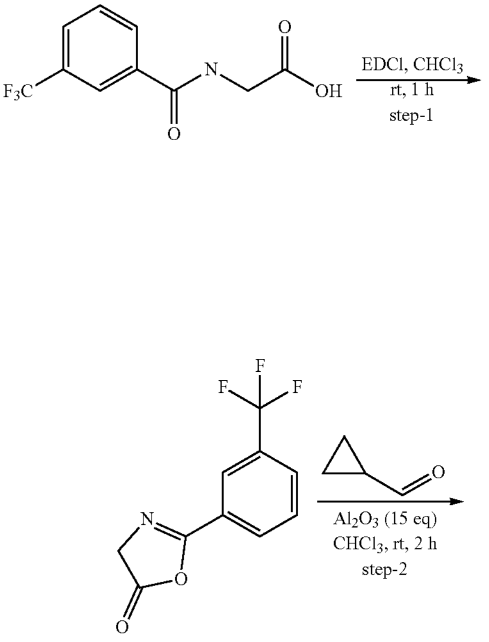

1

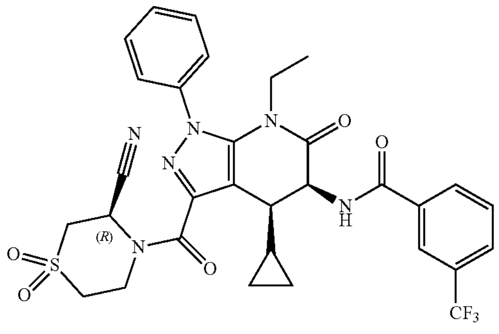

I-659

$^1H$ NMR (300 MHz, DMSO-$d_6$) δ 9.11 (s, 1H), 8.34 (s, 1H), 8.27 (d, J = 7.8 Hz, 1H), 7.97 (d, J = 7.9 Hz, 1H), 7.77 (t, J = 7.8 Hz, 3H), 7.68-7.53 (m, 3H), 5.58-4.82 (m, 2H), 4.01-3.54 (m, 4H), 3.48-3.33 (m, 4H), 2.95 (dd, J = 14.3, 7.1 Hz, 1H), 0.95-0.80 (m, 4H), 0.54 (t, J = 9.2 Hz, 1H), 0.34-0.06 (m, 3H).

LCMS Calculated for $C_{31}H_{29}F_3N_6O_5S$: 654.19; Observed (Method-G): 655.2 $[M + H]^+$, 98.4% at RT 1.74 min.

Chiral-SFC (Method-B): 97.00% at RT 1.22 min

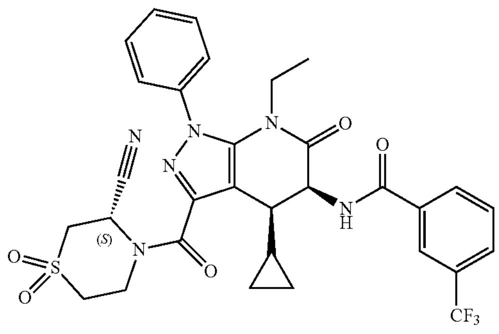

I-438

$^1H$ NMR (300 MHz, DMSO-$d_6$) δ 9.14 (d, J = 8.2 Hz, 1H), 8.35 (s, 1H), 8.28 (d, J = 7.8 Hz, 1H), 7.97 (d, J = 7.8 Hz, 1H), 7.83-7.71 (m, 3H), 7.69-7.54 (m, 3H), 6.38 (s, 1H), 5.53-5.37 (m, 1H), 5.33-4.89 (m, 1H), 3.98-3.55 (m, 4H), 3.50-3.30 (m, 4H), 3.06-2.88 (m, 1H), 0.96-0.77 (m, 5H), 0.65-0.50 (m, 1H), 0.33-0.19 (m, 1H).

LCMS Calculated for $C_{31}H_{29}F_3N_6O_5S$: 654.19; Observed (Method-G): 655.67 $[M + H]^+$, 98.7% at RT 1.75 min.

Chiral-SFC (Method-B): 91.80% at RT 1.29 min

-continued
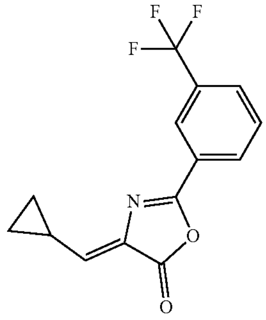
2
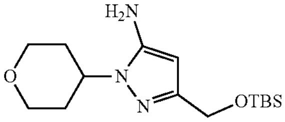
3
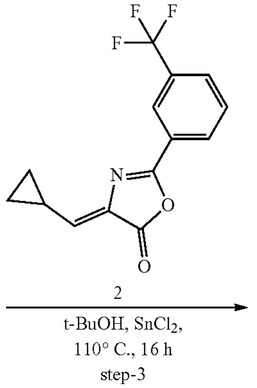
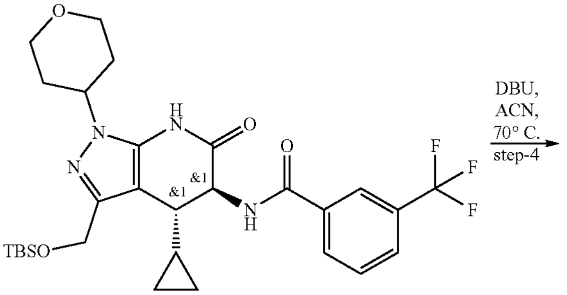
4
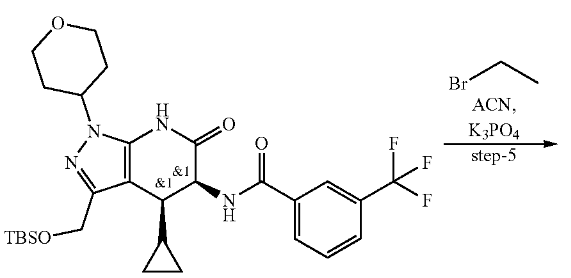
5
-continued
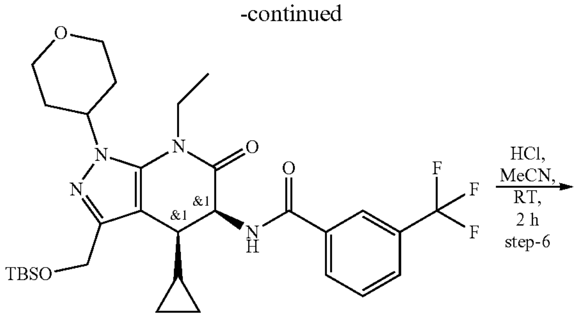
6
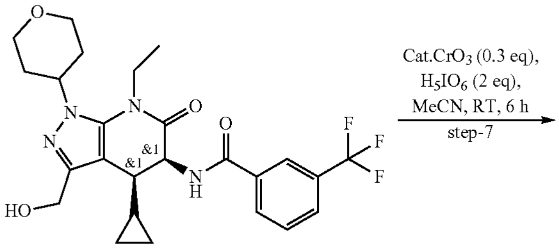
7
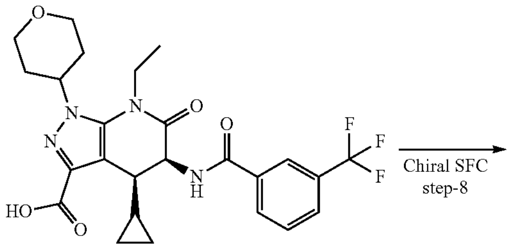
8
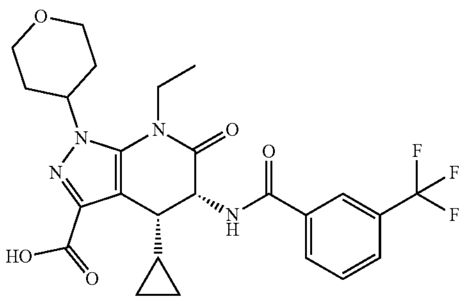
I-575
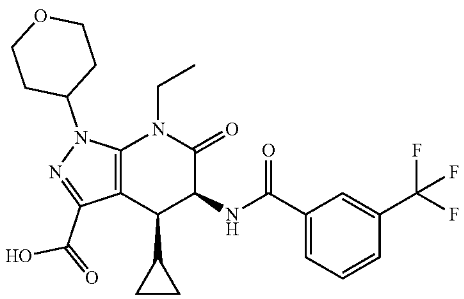
I-545

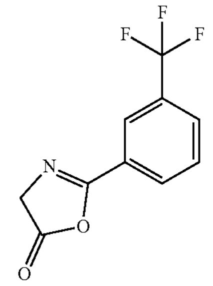

2-(3-(trifluoromethyl)phenyl)oxazol-5(4H)-one(1)

A solution of ([3-(trifluoromethyl)phenyl]formamido-acetic acid (350 g, 1.41 mol, 1.00 equiv) and (3-[[(ethyl-imino)methylidene]amino]propyl)dimethylamine hydro-chloride (298 g, 1.55 mol, 1.10 equiv) in trichloromethane (3.50 L) was stirred at room temperature for 1 h. The reaction was quenched with water (3 L) at room temperature. The resulting mixture was extracted with EtOAc (3×1 L). The combined organic layers were washed with brine (3×1 L), dried over anhydrous $Na_2SO_4$. Desired product could be detected by LCMS. The crude product was used in the next step directly without further purification.

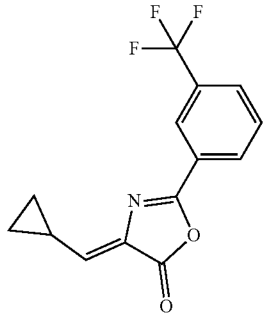

(Z)-4-(cyclopropylmethylene)-2-(3-(trifluoromethyl)phenyl)oxazol-5-(4H)-one (2)

A solution of 2-[3-(trifluoromethyl)phenyl]-4H-1,3-oxazol-5-one (300 g, 1.30 mol, 1 equiv) and $Al_2O_3$ (2002 g, 19.6 mol, 15.0 equiv), cyclopropanecarbaldehyde (82.6 g, 1.17 mol, 0.9 equiv) in trichloromethane (3 L) was stirred at room temperature for 1 h. The resulting mixture was filtered, the filter cake was washed with DCM (6×500 mL). The filtrate was concentrated under reduced pressure. The residue was purified by trituration with petroleum ether (100 mL). This resulted in (Z)-4-(cyclopropylmethylene)-2-(3-(trifluoromethyl)phenyl)oxazol-5 (4H)-one (93 g) as a white solid.

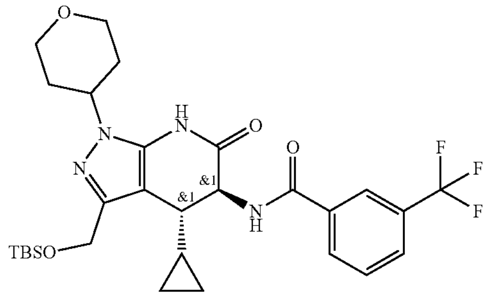

rac-N-((4R,5S)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (4)

A solution of 3-(((tert-butyldimethylsilyl)oxy)methyl)-1-(tetrahydro-2H-pyran-4-yl)-1H-pyrazol-5-amine (9.00 g, 28.9 mmol, 1.00 equiv), $SnCl_2$ (0.550 g, 2.88 mmol, 0.100 equiv) and (Z)-4-(cyclopropylmethylene)-2-(3-(trifluoromethyl)phenyl)oxazol-5 (4H)-one (8.13 g, 28.9 mmol, 1.00 equiv) in t-BuOH (100 mL) was stirred at 110° C. for 16 h. The mixture was allowed to cool down to room temperature. The resulting mixture was concentrated under reduced pressure. The residue was purified by silica gel column chromatography, eluted with petroleum ether/ethyl acetate (2:1) to afford rac-N-((4R,5S)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (11.0 g, 55.2%) as a yellow oil.

LCMS Calculated for $C_{29}H_{39}F_3N_4O_4Si$: 592.27; Observed: 593.4 $[M+H]^+$

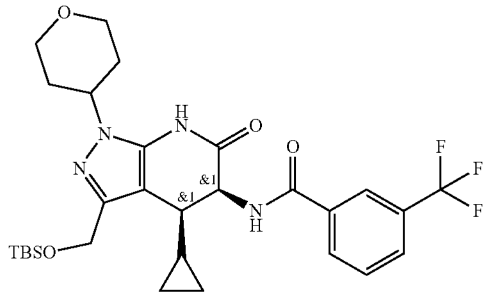

rac-N-((4R,5R)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (5)

A solution of rac-N-((4R,5S)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (11.0 g, 18.5 mmol, 1.00 equiv) and DBU (10.7 g, 70.5 mmol, 3.80 equiv) in ACN (120 mL) was stirred at 80° C. for 16 h. The mixture was allowed to cool down to room temperature. The resulting mixture was concentrated under reduced pressure. The resulting mixture was diluted with $H_2O$ (200 mL). The resulting mixture was extracted with EtOAc (3×100 mL). The combined organic layers were washed with brine (3×50 mL), dried over anhydrous $Na_2SO_4$. After filtration, the filtrate was concentrated under reduced pressure. The residue was purified by silica gel column chromatography, eluted with petroleum ether/ethyl acetate (2:1) to afford rac-N-((4R,5R)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (10.7 g, 87.5%) as a yellow oil.

LCMS Calculated for $C_{29}H_{39}F_3N_4O_4Si$: 592.27; Observed: 593.4 $[M+H]^+$

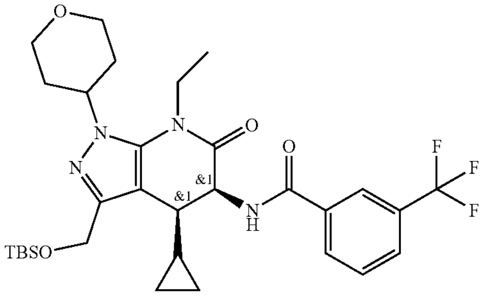

rac-N-((4R,5R)-3-(((tert-butyldimethylsilyl)oxy)methyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (6)

A solution of rac-N-((4R,5R)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (10.3 g, 17.3 mmol, 1.00 equiv), bromoethane (2.27 g, 20.8 mmol, 1.20 equiv) and $K_3PO_4$ (5.53 g, 26.0 mmol, 1.50 equiv) in ACN (110 mL) was stirred at 50° C. for 16 h. The mixture was allowed to cool down to room temperature. The mixture was allowed to cool down to room temperature. The resulting mixture was concentrated under reduced pressure. The residue was purified by silica gel column chromatography, eluted with petroleum ether/ethyl acetate (1:1) to afford rac-N-((4R,5R)-3-(((tert-butyldimethylsilyl)oxy)methyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (10.0 g, 83.4%) as a yellow solid.

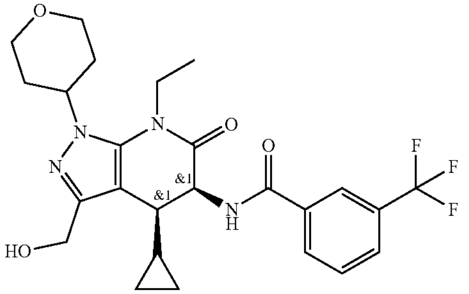

rac-N-((4R,5R)-4-cyclopropyl-7-ethyl-3-(hydroxymehtyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (7)

To a stirred mixture of rac-N-((4R,5R)-3-(((tert-butyldimethylsilyl)oxy)methyl)-4-cyclopropyl-7-ethyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (10.0 g, 16.1 mmol, 1.00 equiv) in MeCN (50 mL) was added HCl (50 mL) in portions at room temperature. The mixture was stirred at room temperature for 2 h. The resulting mixture was concentrated under reduced pressure. The mixture was basified to pH 7 with saturated $NaHCO_3$(aq.). The resulting mixture was extracted with EtOAc (3×100 mL). The combined organic layers were washed with NaCl (3×50 mL), dried over anhydrous $Na_2SO_4$. After filtration, the filtrate was concentrated under reduced pressure. The residue was purified by silica gel column chromatography, eluted with petroleum ether/ethyl acetate (1:1) to afford rac-N-((4R,5R)-4-cyclopropyl-7-ethyl-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (7.00 g, 85.4%) as a yellow solid.

LCMS Calculated for $C_{25}H_{29}F_3N_4O_4Si$: 506.21; Observed: 507.2 $[M+H]^+$

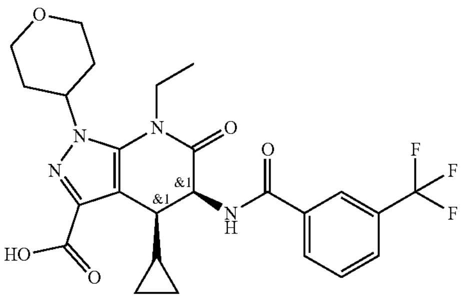

rac-(4R,5R)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (8)

A solution of rac-N-((4R,5R)-4-cyclopropyl-7-ethyl-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (7.00 g, 13.8 mmol, 1.00 equiv), periodic acid (9.45 g, 41.4 mmol, 3.00 equiv) and $CrO_3$ (0.410 g, 4.14 mmol, 0.300 equiv) in MeCN (70 mL) was stirred at room temperature for 16 h. The reaction was quenched with $N_2$S203 (200 ml) at room temperature. The resulting mixture was extracted with EtOAc (3×100 mL). The combined organic layers were washed with brine (3×50 mL), dried over anhydrous $Na_2SO_4$. After filtration, the filtrate was concentrated under reduced pressure. The residue was purified by silica gel column chromatography, eluted with $CH_2Cl_2$/MeOH (10:1) to afford rac-(4R,5R)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (3.50 g, 47.2%) as a yellow solid.

(4R,5R)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-575) & (4S,5S)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-545)

The crude product rac-(4R,5R)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (3.50 g, 6.72 mmol, 1.00 equiv) was purified by PREP_CHIRAL_SFC with the following conditions (Column: XA-CHIRAL ART Cellulose-SC, 3*25 cm 5 μm; Mobile Phase A: CO2, Mobile Phase B: MEOH: DCM=2: 1 (0.1% 2M $NH_3$-MeOH); Flow rate: 80 mL/min; Gradient: isocratic 35% B; Column Temperature (° C.): 35; Back Pressure (bar): 100; Wave Length: 220 nm; RT1(min): 3.6; RT2(min): 4.6; Sample Solvent: MEOH; Injection Volume: 0.5 mL) to afford (4R,5R)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-575) (1.2 g, 30.4%) and (4S,5S)-4-cyclopropyl-7-ethyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (I-545) (0.800 g, 22.4%) as a yellow solid.

General scheme for related acids
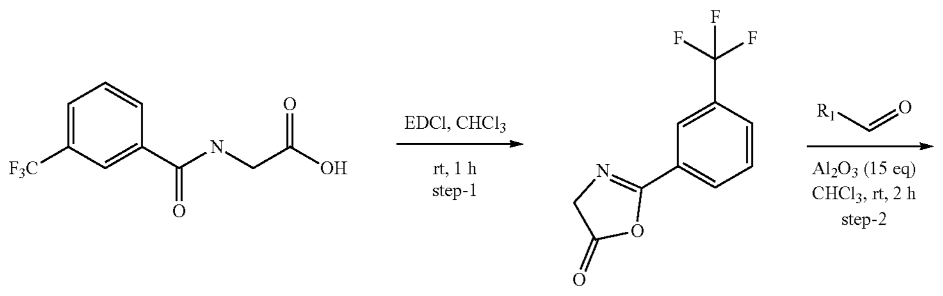
1
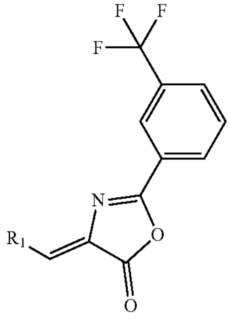
2
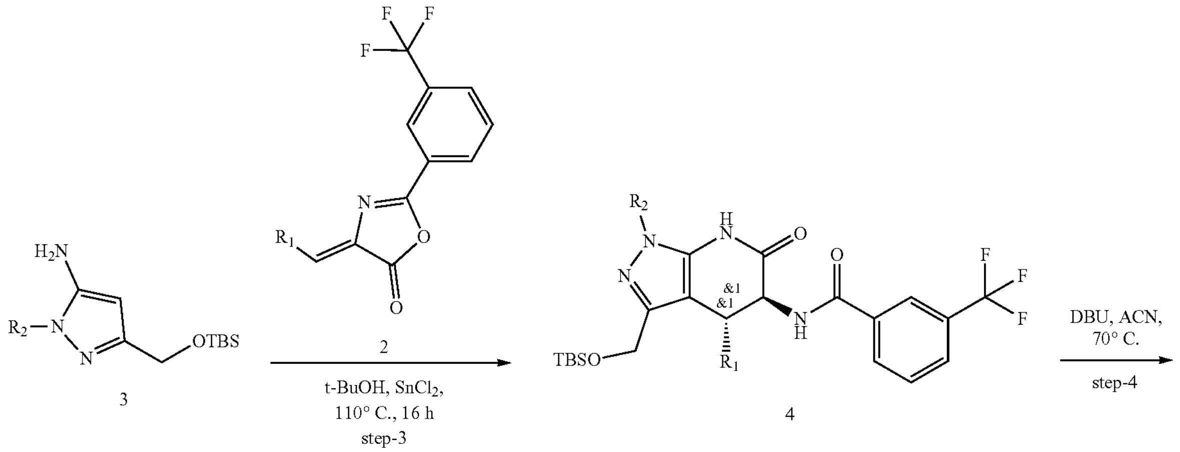
3
4
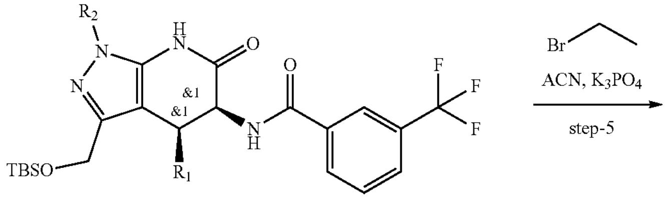
5

-continued
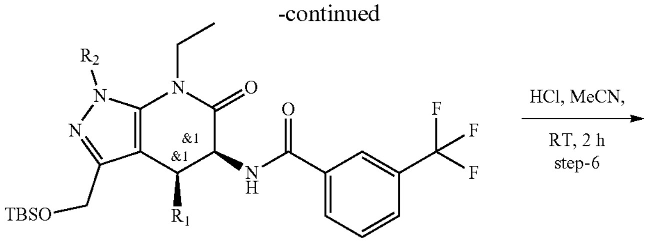
6
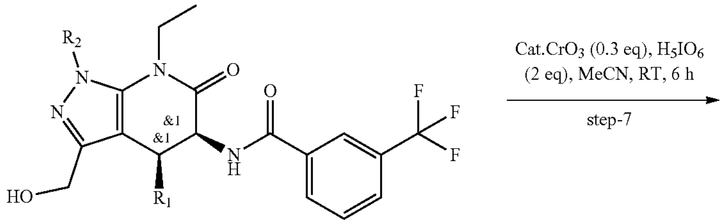
7
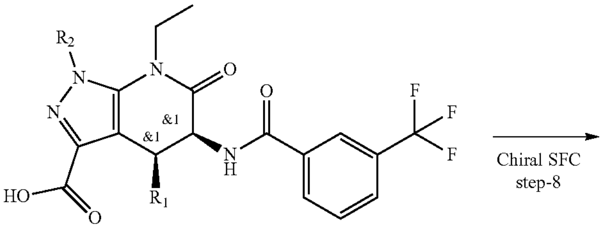
8
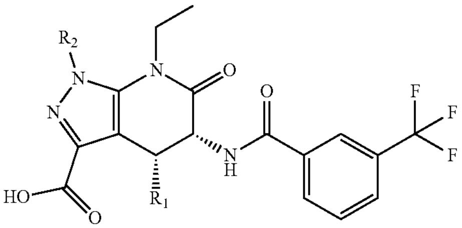
I-575
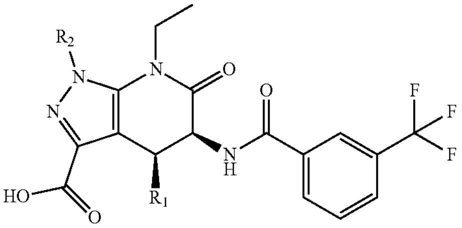
I-545
| | | |
|---|---|---|
| 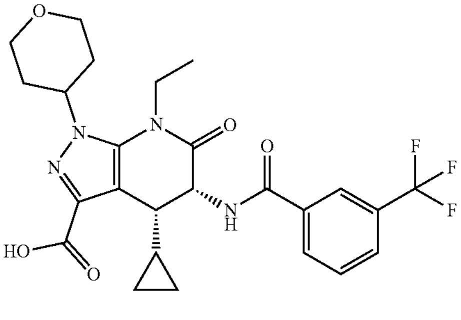 [SMILES: CCN1C(=O)[C@H](NC(=O)c2cccc(C(F)(F)F)c2)[C@H](C2CC2)c2c(C(=O)O)nn(C3CCOCC3)c21] I-575 | 1.2 g | $^1$H NMR (400 MHz, DMSO-$d_6$) δ 8.98 (d, J = 7.9 Hz, 1H), 8.31 (s, 1H), 8.25 (d, J = 7.9 Hz, 1H), 7.95 (d, J = 7.8 Hz, 1H), 7.80-7.71 (m, 1H), 5.06-4.98 (m, 1H), 4.44 (s, 1H), 4.24-4.00 (m, 2H), 3.94 (d, J = 11.5 Hz, 1H), 3.88-3.72 (m, 1H), 3.59-3.42 (m, 2H), 3.37 (m, J = 6.4 Hz, 1H), 2.50 (s, 1H), 2.26 (d, J = 12.5 Hz, 1H), 2.04 (d, J = 13.6 Hz, 1H), 1.95 (s, 1H), 1.84 (d, J = 12.8 Hz, 1H), 1.25 (t, J = 7.1 Hz, 3H), 0.91-0.44 (m, 1H), 0.29-0.12 (m, 1H), 0.12--0.25 (m, 3H). LCMS Calculated for $C_{25}H_{27}F_3N_4O_5$: 520.19; Observed (Method-J): 521.2 $[M + H]^+$, 97.1% at 0.980 min. a = −10.9, (c = 0.1 g/100 mL in MeOH, T = 25° C.) |

-continued

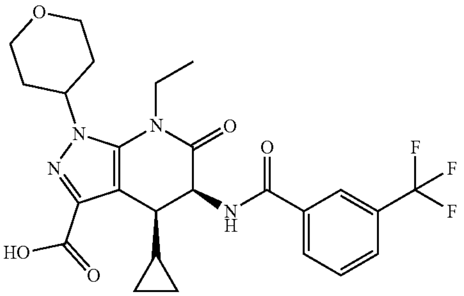 [SMILES: CCN1C(=O)[C@@H](NC(=O)c2cccc(C(F)(F)F)c2)[C@@H](C2CC2)c2c(C(=O)O)nn(C3CCOCC3)c21]

I-545

0.8 g $^1H$ NMR (300 MHz, DMSO-$d_6$) δ 8.96 (d, J = 7.9 Hz, 1H), 8.31 (s, 1H), 8.24 (d, J = 7.9 Hz, 1H), 7.95 (d, J = 7.8 Hz, 1H), 7.75 (t, J = 7.8 Hz, 1H), 5.04-4.96 (m, 1H), 4.11-3.99 (m, 2H), 3.93 (d, J = 11.3 Hz, 1H), 3.87-3.77 (m, 1H), 3.58-3.38 (m, 4H), 2.28 (d, J = 13.4 Hz, 1H), 2.02 (d, J = 13.7 Hz, 2H), 1.82 (d, J = 12.6 Hz, 1H), 1.25 (t, J = 7.0 Hz, 4H), 0.85-0.76 (m, 1H), 0.46 (s, 1H), 0.18-0.10 (m, 2H), 0.08 (d, J = 7.5 Hz, 1H). LCMS Calculated for $C_{25}H_{27}F_3N_4O_5$: 520.19; Observed (Method-D): 521.2 $[M + H]^+$, 97.1% at 2.327 min. a = +8.9, (c = 0.1 g/100 Ml in MeOH, T = 25° C.).

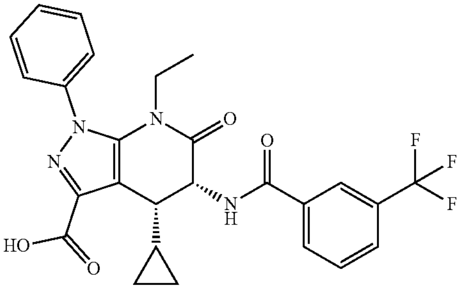 [SMILES: CCN1C(=O)[C@H](NC(=O)c2cccc(C(F)(F)F)c2)[C@H](C2CC2)c2c(C(=O)O)nn(-c3ccccc3)c21]

I-404

1 g $^1H$ NMR (400 MHz, DMSO-$d_6$) δ 13.05 (s, 1H), 9.08 (d, J = 8.0 Hz, 1H), 8.35 (s, 1H), 8.28 (d, J = 7.9 Hz, 1H), 7.96 (d, J = 7.8 Hz, 1H), 7.77 (t, J = 7.8 Hz, 1H), 7.73-7.68 (m, 2H), 7.61 (dd, J = 8.6, 4.1 Hz, 3H), 5.36 (dd, J = 7.9, 6.0 Hz, 1H), 3.88-3.90 (m, 1H), 3.42 (t, J = 6.5 Hz, 1H), 2.96-2.86 (m, 1H), 0.83 (t, J = 7.1 Hz, 4H), 0.58-0.51 (m, 1H), 0.24 (t, J = 4.4 Hz, 1H), 0.12-0.2 (m, 2H). LCMS Calculated for $C_{26}H_{23}F_3N_4O_4$: 512.17; Observed (Method-C): 513.1 $[M + H]^+$, 97.7% at RT 1.133 min.

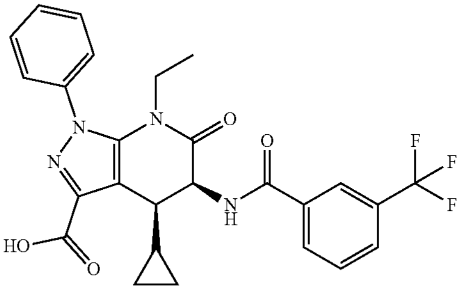 [SMILES: CCN1C(=O)[C@@H](NC(=O)c2cccc(C(F)(F)F)c2)[C@@H](C2CC2)c2c(C(=O)O)nn(-c3ccccc3)c21]

I-587

1 g $^1H$ NMR (400 MHz, DMSO-$d_6$) δ 13.05 (s, 1H), 9.08 (d, J = 8.0 Hz, 1H), 8.35 (s, 1H), 8.28 (d, J = 7.9 Hz, 1H), 7.96 (d, J = 7.8 Hz, 1H), 7.77 (t, J = 7.8 Hz, 1H), 7.73-7.68 (m, 2H), 7.61 (dd, J = 8.6, 4.1 Hz, 3H), 5.36 (dd, J = 7.9, 6.0 Hz, 1H), 3.88-3.90 (m, 1H), 3.42 (t, J = 6.5 Hz, 1H), 2.96-2.86 (m, 1H), 0.83 (t, J = 7.1 Hz, 4H), 0.58-0.51 (m, 1H), 0.24 (t, J = 4.4 Hz, 1H), 0.12-0.20 (m, 2H). LCMS Calculated for $C_{26}H_{23}F_3N_4O_4$: 512.17; Observed (Method-C): 513.1 $[M + H]^+$, 99.7% at RT 1.137 min.

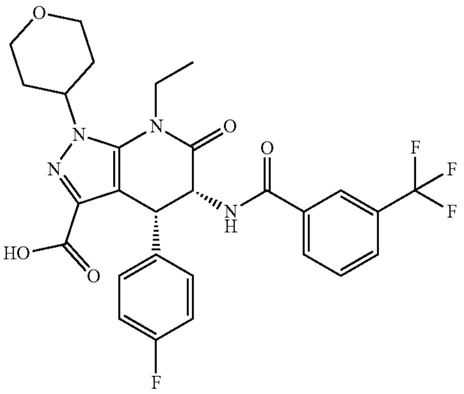 [SMILES: CCN1C(=O)[C@H](NC(=O)c2cccc(C(F)(F)F)c2)[C@H](c2ccc(F)cc2)c2c(C(=O)O)nn(C3CCOCC3)c21]

I-443

1.6 g $^1H$ NMR (300 MHz, DMSO-$d_6$) δ 12.84 (s, 1H), 8.53 (d, J = 7.1 Hz, 1H), 8.23-8.05 (m, 2H), 7.92 (d, J = 7.8 Hz, 1H), 7.71 (t, J = 7.8 Hz, 1H), 7.08 (t, J = 8.8 Hz, 2H), 6.95 (dd, J = 8.6, 5.6 Hz, 2H), 5.26 (t, J = 7.1 Hz, 1H), 4.84 (d, J = 7.1 Hz, 1H), 4.57 (d, J = 4.8 Hz, 0H), 4.09 (t, J = 9.4 Hz, 2H), 4.03-3.85 (m, 2H), 3.66-3.41 (m, 2H), 2.17 (s, 1H), 1.96 (d, J = 4.1 Hz, 2H), 1.32 (t, J = 7.0 Hz, 3H). LCMS Calculated for $C_{28}H_{26}F_4N_4O_5$: 574.2; Observed (Method-AO): 575.2 $[M + H]^+$, 98.2% at RT 1.282 min.

-continued

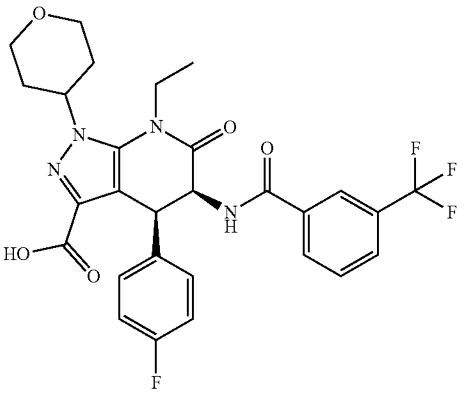 [SMILES: CCN1C(=O)[C@@H](NC(=O)c2cccc(C(F)(F)F)c2)[C@@H](c2ccc(F)cc2)c2c(C(=O)O)nn(C3CCOCC3)c21]

I-657

1.4 g $^1$H NMR (300 MHz, DMSO-$d_6$) δ 12.83 (s, 1H), 8.53 (d, J = 7.0 Hz, 1H), 8.23-8.07 (m, 2H), 7.92 (d, J = 7.8 Hz, 1H), 7.71 (t, J = 7.8 Hz, 1H), 7.21-7.02 (m, 2H), 7.02-6.85 (m, 2H), 5.26 (t, J = 7.1 Hz, 1H), 4.84 (d, J = 7.1 Hz, 1H), 4.57 (s, 1H), 4.10 (td, J = 13.1, 11.4, 5.4 Hz, 2H), 4.02-3.86 (m, 2H), 3.65-3.45 (m, 2H), 2.41-2.24 (m, 1H), 2.15 (d, J = 13.0 Hz, 1H), 1.95 (t, J = 8.0 Hz, 2H), 1.32 (t, J = 7.0 Hz, 3H).
LCMS Calculated for $C_{28}H_{26}F_4N_4O_5$: 574.2; Observed (Method-B): 575.2 $[M + H]^+$, 97.8% at RT 0.985 min.

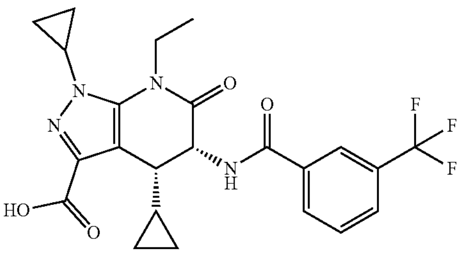 [SMILES: CCN1C(=O)[C@H](NC(=O)c2cccc(C(F)(F)F)c2)[C@H](C2CC2)c2c(C(=O)O)nn(C3CC3)c21]

I-678

2.3 g $^1$H NMR (400 MHz, DMSO-$d_6$) δ 12.84 (s, 1H), 9.01 (d, J = 7.9 Hz, 1H), 8.32 (s, 1H), 8.25 (d, J = 7.8 Hz, 1H), 7.95 (d, J = 7.8 Hz, 1H), 7.76 (t, J = 7.8 Hz, 1H), 5.07 (dd, J = 7.8, 6.0 Hz, 1H), 4.31 (dq, J = 14.3, 6.8 Hz, 1H), 4.17-4.08 (m, 1H), 3.75 (p, J = 3.4 Hz, 1H), 3.36 (t, J = 6.2 Hz, 1H), 1.30 (d, J = 7.1 Hz, 1H), 1.23 (t, J = 7.0 Hz, 4H), 1.15 (dd, J = 7.8, 5.7 Hz, 1H), 1.13-1.03 (m, 1H), 0.85 (d, J = 6.3 Hz, 1H), 0.48 (td, J = 8.8, 4.6 Hz, 1H), 0.24-0.13 (m, 1H), 0.08 (dd, J = 9.2, 4.5 Hz, 2H).
LCMS Calculated for $C_{23}H_{23}F_3N_4O_4$: 476.17; Observed (Method-B): 477.1 $[M + H]^+$, 98.7% at RT 0.943 min.

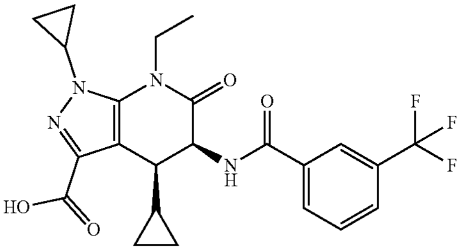 [SMILES: CCN1C(=O)[C@@H](NC(=O)c2cccc(C(F)(F)F)c2)[C@@H](C2CC2)c2c(C(=O)O)nn(C3CC3)c21]

I-520

2.2 g $^1$H NMR (400 MHz, DMSO-$d_6$) δ 12.83 (s, 1H), 9.02 (d, J = 7.9 Hz, 1H), 8.32 (s, 1H), 8.25 (d, J = 7.9 Hz, 1H), 7.95 (d, J = 7.9 Hz, 1H), 7.76 (t, J = 7.8 Hz, 1H), 5.07 (dd, J = 7.8, 6.0 Hz, 1H), 4.36-4.27 (m, 1H), 4.10-4.14 (m, 1H), 3.75 (dt, J = 7.1, 3.4 Hz, 1H), 3.35 (t, J = 6.3 Hz, 1H), 1.31 (d, J = 8.1 Hz, 1H), 1.23 (t, J = 7.0 Hz, 3H), 1.20-1.12 (m, 2H), 1.10-1.02 (m, 1H), 0.85 (d, J = 6.2 Hz, 1H), 0.48 (t, J = 4.4 Hz, 1H), 0.23-0.16 (m, 1H), 0.07 (dd, J = 9.3, 4.4 Hz, 1H).
LCMS Calculated for $C_{23}H_{23}F_3N_4O_4$: 476.17; Observed: (Method-C): 477.1 $[M + H]^+$, 99.3% at RT 1.101 min.

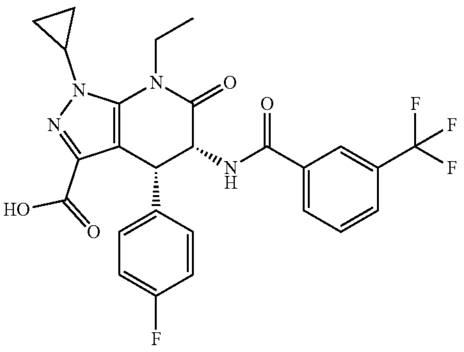 [SMILES: CCN1C(=O)[C@H](NC(=O)c2cccc(C(F)(F)F)c2)[C@H](c2ccc(F)cc2)c2c(C(=O)O)nn(C3CC3)c21]

I-537

1.8 g $^1$H NMR (400 MHz, DMSO-$d_6$) δ 12.80 (s, 1H), 8.53 (d, J = 7.1 Hz, 1H), 8.14 (d, J = 12.0 Hz, 2H), 7.92 (d, J = 7.8 Hz, 1H), 7.71 (t, J = 7.8 Hz, 1H), 7.08 (t, J = 8.8 Hz, 2H), 7.00-6.89 (m, 2H), 5.27 (t, J = 7.1 Hz, 1H), 4.81 (d, J = 7.2 Hz, 1H), 4.43-4.29 (m, 1H), 4.29-4.16 (m, 1H), 3.84 (dt, J = 7.0, 3.5 Hz, 1H), 1.44-1.07 (m, 7H).
LCMS Calculated for $C_{26}H_{22}F_4N_4O_4$: 530.16; Observed (Method-I): 529.2 $[M - H]^-$, 95.5% at RT 1.483 min.

-continued

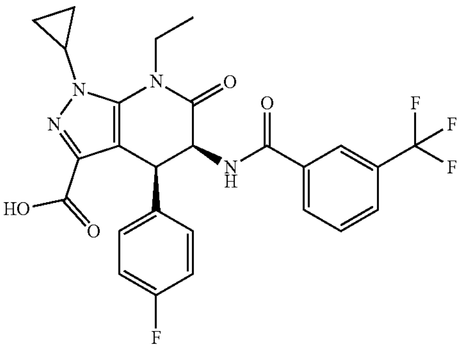 [SMILES: CCN1C(=O)[C@@H](NC(=O)c2cccc(C(F)(F)F)c2)[C@@H](c2ccc(F)cc2)c2c(C(=O)O)nn(C3CC3)c21]

1.8 g $^1H$ NMR (400 MHz, DMSO-$d_6$) δ 12.80 (s, 1H), 8.53 (d, J = 7.1 Hz, 1H), 8.14 (d, J = 12.0 Hz, 2H), 7.92 (d, J = 7.8 Hz, 1H), 7.71 (t, J = 7.8 Hz, 1H), 7.08 (t, J = 8.8 Hz, 2H), 7.00-6.89 (m, 2H), 5.27 (t, J = 7.1 Hz, 1H), 4.81 (d, J = 7.2 Hz, 1H), 4.43-4.29 (m, 1H), 4.29-4.16 (m, 1H), 3.84 (dt, J = 7.0, 3.5 Hz, 1H), 1.44-1.07 (m, 7H).
LCMS Calculated for $C_{26}H_{22}F_4N_4O_4$: 530.16; Observed (Method-J): 529.2 $[M - H]^-$, 99.8% at RT 1.099 min.

I-477

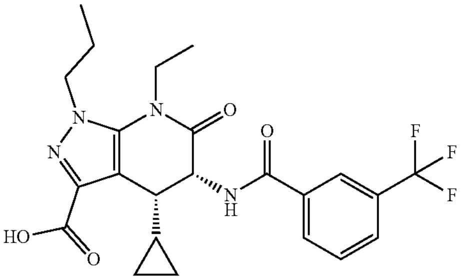 [SMILES: CCCn1nc(C(=O)O)c2c1N(CC)C(=O)[C@H](NC(=O)c1cccc(C(F)(F)F)c1)[C@@H]2C1CC1]

1.4 g $^1H$ NMR (400 MHz, DMSO-d6) δ 13.22-12.63 (m, 1H), 9.02 (d, J = 7.8 Hz, 1H), 8.31 (s, 1H), 8.25 (d, J = 7.9 Hz, 1H), 7.96 (d, J = 8.1 Hz, 1H), 7.76 (t, J = 7.8 Hz, 1H), 5.02 (dd, J = 7.8, 6.0 Hz, 1H), 4.27-4.10 (m, 3H), 3.80-3.70 (m, 1H), 3.39 (t, J = 6.2 Hz, 1H), 1.90-1.74 (m, 2H), 1.21 (t, J = 7.1 Hz, 3H), 1.18 (d, J = 6.5 Hz, 1H), 0.89 (t, J = 7.4 Hz, 3H), 0.53-0.44 (m, 1H), 0.21-0.17 (m, 1H), 0.03 (d, J = 5.4 Hz, 2H).
LCMS Calculated for $C_{23}H_{25}F_3N_4O_4$: 478.18; Observed (Method-I): 477.2 $[M - H]^-$, 96.7% at RT 1.357 min.

I-665

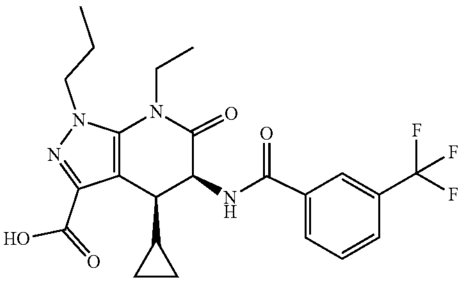 [SMILES: CCCn1nc(C(=O)O)c2c1N(CC)C(=O)[C@@H](NC(=O)c1cccc(C(F)(F)F)c1)[C@H]2C1CC1]

1.3 g $^1H$ NMR (400 MHz, DMSO-$d_6$) δ 13.06-12.67 (m, 1H), 9.02 (d, J = 7.8 Hz, 1H), 8.31 (s, 1H), 8.25 (d, J = 7.9 Hz, 1H), 7.96 (d, J = 7.8 Hz, 1H), 7.76 (t, J = 7.8 Hz, 1H), 5.02 (dd, J = 7.8, 6.0 Hz, 1H), 4.27-4.12 (m, 3H), 3.80-3.70 (m, 1H), 3.39 (t, J = 6.2 Hz, 1H), 1.90-1.75 (m, 2H), 1.21 (t, J = 7.1 Hz, 3H), 0.94-0.80 (m, 4H), 0.48 (t, J = 9.1 Hz, 1H), 0.19 (t, J = 9.1 Hz, 1H), 0.02 (d, J = 5.9 Hz, 2H).
LCMS Calculated for $C_{23}H_{25}F_3N_4O_4$: 478.18; Observed (Method-I): 479.0 $[M + H]^+$, 98.7% at RT 1.139 min.

I-651

-continued

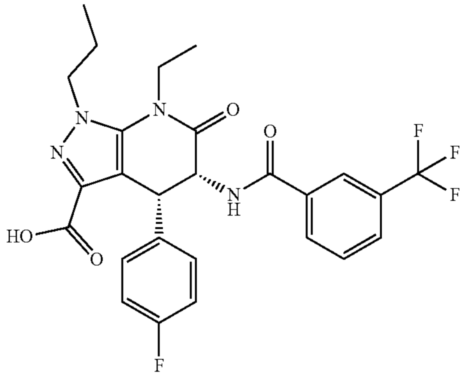 [SMILES: CCCn1nc(C(=O)O)c2c1N(CC)C(=O)[C@H](NC(=O)c1cccc(C(F)(F)F)c1)[C@@H]2c1ccc(F)cc1]

I-454

1.2 g $^1$H NMR (300 MHz, DMSO-$d_6$) δ 12.82 (s, 1H), 8.53 (d, J = 7.0 Hz, 1H), 8.20-8.08 (m, 2H), 7.92 (d, J = 7.8 Hz, 1H), 7.71 (t, J = 7.8 Hz, 1H), 7.15-7.03 (m, 2H), 6.99-6.86 (m, 2H), 5.23 (t, J = 7.0 Hz, 1H), 4.86 (d, J = 7.1 Hz, 1H), 4.41-4.12 (m, 3H), 3.84 (dq, J = 13.9, 6.7 Hz, 1H), 2.02-1.76 (m, 2H), 1.29 (t, J = 7.0 Hz, 4H), 0.94 (t, J = 7.3 Hz, 3H). LCMS Calculated for $C_{26}H_{24}F_4N_4O_4$: 532.17; Observed (Method-V): 531.2 $[M-H]^-$, 98.7% at RT 1.117 min.

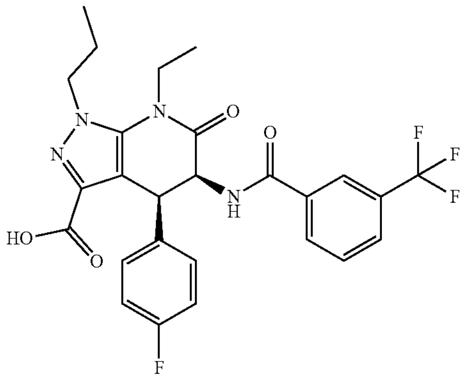 [SMILES: CCCn1nc(C(=O)O)c2c1N(CC)C(=O)[C@@H](NC(=O)c1cccc(C(F)(F)F)c1)[C@H]2c1ccc(F)cc1]

I-675

1.1 g $^1$H NMR (300 MHz, DMSO-$d_6$) δ 12.91 (s, 1H), 8.52 (d, J = 7.0 Hz, 1H), 8.20-8.07 (m, 2H), 7.96-7.88 (m, 1H), 7.71 (t, J = 7.8 Hz, 1H), 7.14-7.03 (m, 2H), 6.95 (ddd, J = 8.6, 5.4, 2.5 Hz, 2H), 5.23 (t, J = 7.1 Hz, 1H), 4.87 (d, J = 7.2 Hz, 1H), 4.39-4.14 (m, 3H), 3.84 (dq, J = 13.9, 6.8 Hz, 1H), 1.88 (ddt, J = 14.0, 10.2, 7.0 Hz, 2H), 1.29 (t, J = 7.0 Hz, 3H), 0.94 (t, J = 7.4 Hz, 3H). LCMS Calculated for $C_{26}H_{24}F_4N_4O_4$: 532.17; Observed (Method-V): 531.2 $[M-H]^-$, 99.4% at RT 1.115 min.

Synthesis of N-((4S,5S)-3-(2-cyano-4-methylpiperazine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (38-1)

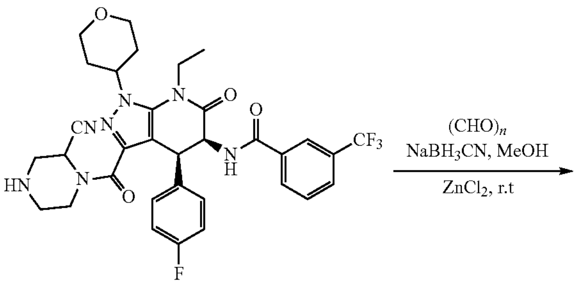

15-1

-continued

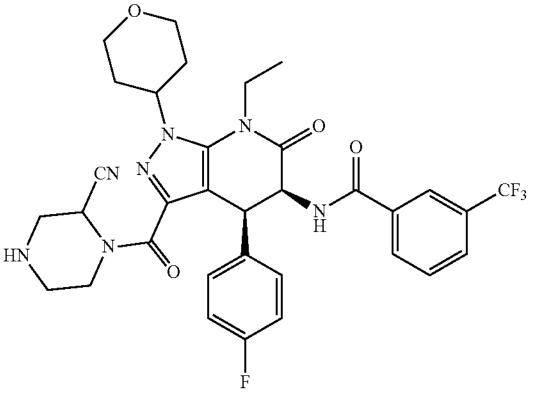

15-1

A solution of N-((4S,5S)-3-(2-cyanopiperazine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (35.0 mg, 0.052 mmol, 1.00 equiv), Paraformaldehyde (9.24 mg, 0.208 mmol, 4.00 equiv) in MeOH (4 mL) was treated with $ZnCl_2$ (7.14 mg, 0.052 mmol, 1.00 equiv) at room temperature for 5 min. The resulting mixture was stirred at room temperature for 30 min. And followed by the addition of sodium cyanoboranuide (6.59 mg, 0.104 mmol, 2.00 equiv) in portions at room temperature. The resulting mixture was stirred at room temperature for 16 h. The crude product was purified by Prep-HPLC with the following conditions (Column: Sunfire Prep C18 OBD Column, 19*150 mm, 5 μm; Mobile Phase A: Water (0.1% FA), Mobile Phase B: ACN; Flow rate: 30 mL/min; Gradient: 10% B to 40% B in 7 min/40% B; Wave Length: 254 nm/220 nm nm; RT1(min): 6.62; 9.46) to afford N-((4S,5S)-3-(2-cyano-4-methylpiperazine-1-carbonyl)-7-ethyl-4-(4-fluorophenyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (22 mg, 59.1%) as a white solid.

$^1H$ NMR (400 MHZ, DMSO-$d_6$) δ 8.46 (s, 1H), 8.11 (d, J=12.3 Hz, 2H), 7.92 (d, J=7.8 Hz, 1H), 7.71 (t, J=7.8 Hz, 1H), 7.06 (t, J=8.7 Hz, 2H), 6.93 (t, J=6.6 Hz, 2H), 5.40 (d, J=134.1 Hz, 2H), 4.73 (d, J=7.0 Hz, 2H), 4.58 (s, 2H), 4.15-4.03 (m, 2H), 3.94-3.88 (m, 2H), 3.59 (t, J=12.1 Hz, 2H), 2.95-2.85 (m, 2H), 2.33-1.95 (m, 9H), 1.32 (t, J=7.0 Hz, 3H).

LCMS Calculated for $C_{34}H_{35}F_4N_7O_4$: 681.27; Observed (Method-AG): 682.4 $[M+H]^+$, 96.0% at RT 2.046 min.

Synthesis of N-((4S,5S)-3-((1R,5R)-3-cyano-2-azabicyclo[3.1.0]hexane-2-carbonyl)-4-cyclopropyl-7-ethyl-5-methyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-516)

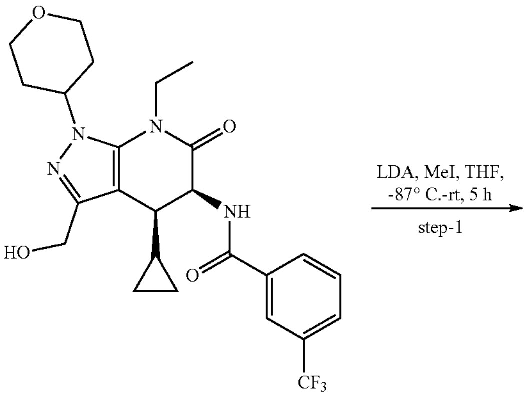

9

-continued

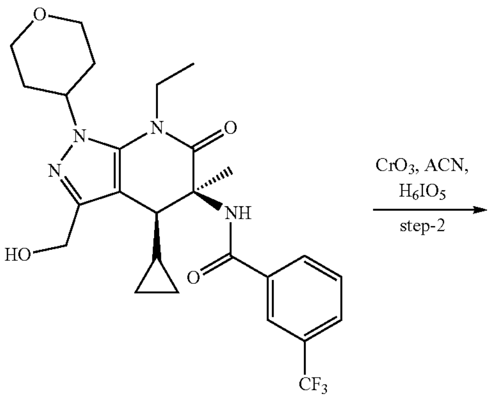

10

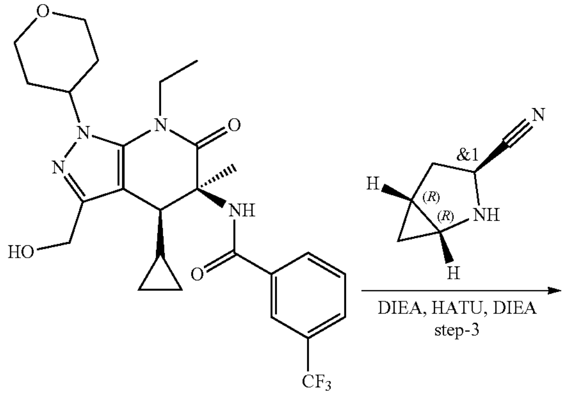

11

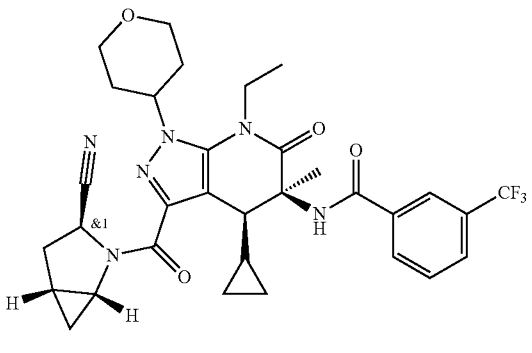

I-516

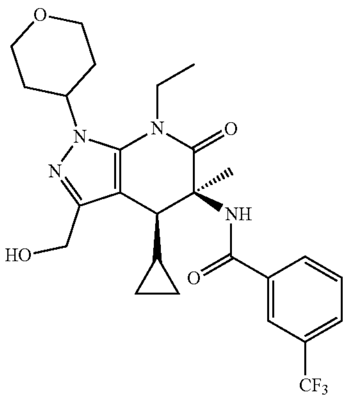

N-((4S,5S)-4-cyclopropyl-7-ethyl-3-(hydroxymethyl)-5-methyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (10)

A solution of N-((4S,5S)-4-cyclopropyl-7-ethyl-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (700 mg, 1.38 mmol, 1.00 equiv) in THF (10 mL) was treated with LDA (296 mg, 2.76 mmol, 2.00 equiv) at −78° C. for 30 min under nitrogen atmosphere followed by the addition of MeI (235 mg, 1.65 mmol, 1.20 equiv) in portions at −78° C. The resulting mixture was stirred at −78° C. for 1 h under nitrogen atmosphere. The reaction was quenched with sat. $NH_4Cl$ (aq.) at −78° C. The resulting mixture was extracted with EtOAc (3×20 mL). The combined organic layers were washed with brine (3×20 mL), dried over anhydrous $Na_2SO_4$. After filtration, the filtrate was concentrated under reduced pressure. The residue was purified by silica gel column chromatography, eluted with petroleum ether/ethyl acetate (1:1) to afford N-((4S,5S)-4-cyclopropyl-7-ethyl-3-(hydroxymethyl)-5-methyl-6-oxo-1-(tetrahydro-2H-pyran-4-yl)-4,5,6,7-tetrahydro-1H-pyrazolo[3,4-b]pyridin-5-yl)-3-(trifluoromethyl) benzamide (100 mg, 13.9% yield, 98% purity) as a yellow solid.

LCMS Calculated for $C_{26}H_{31}F_3N_4O_4$: 520.23; Observed: 521.2 $[M+H]^+$

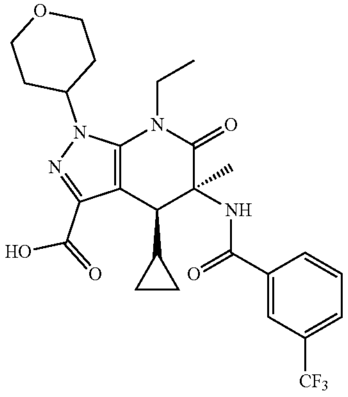

(4S,5S)-4-cyclopropyl-7-ethyl-5-methyl-6-oxo-(tetrahydro-2H-pyran-4-yl)-4,5,6,7-tetrahydro-1H-pyrazolo[3,4-b]pyridin-5-yl)-3-(trifluoromethyl)benzamide (10)

To a stirred solution of N-((4S,5S)-4-cyclopropyl-7-ethyl-3-(hydroxymethyl)-5-methyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (90.0 mg, 0.173 mmol, 1.00 equiv) and $NaIO_4$ (111 mg, 0.519 mmol, 3.00 equiv) in MeCN (2.00 mL) was added Chromium trioxide (5.19 mg, 0.052 mmol, 0.30 equiv) in portions at 0° C. under nitrogen atmosphere. The resulting mixture was stirred at room temperature for 2 h under nitrogen atmosphere. The reaction was quenched with sat. $Na_2S_2O_3$ (aq.) at 0° C. The resulting mixture was extracted with EtOAc (2×10 mL). The combined organic layers were washed with brine (2×10 mL), dried over anhydrous $Na_2SO_4$. After filtration, the filtrate was concentrated under reduced pressure. The residue was purified by silica gel column chromatography, eluted with $CH_2Cl_2$/MeOH (10:1) to afford (4S,5S)-4-cyclopropyl-7-ethyl-5-methyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (70 mg) as a brown yellow solid.

LCMS Calculated for $C_{26}H_{29}F_3N_4O_5$: 534.21; Observed: 533.2 $[M-H]^-$

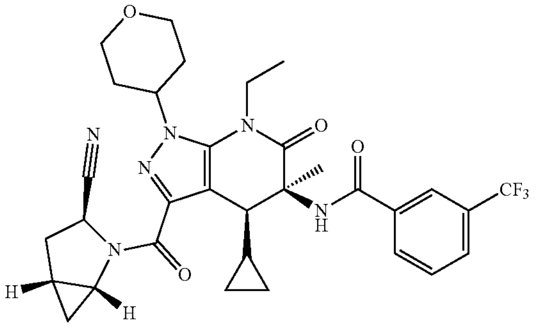

N-((4S,5S)-3-((1R,3S,5R)-3-cyano-2-azabicyclo[3.1.0]hexane-2-carbonyl)-4-cyclopropyl-7-ethyl-5-methyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-516)

A solution of (4S,5S)-4-cyclopropyl-7-ethyl-5-methyl-6-oxo-1-(tetrahydro-2H-pyran-4-yl)-5-(3-(trifluoromethyl) benzamido)-4,5,6,7-tetrahydro-1H-pyrazolo[3,4-b]pyridine-3-carboxylic acid (50.0 mg, 0.094 mmol, 1.00 equiv) in DMF (2.00 mL) was treated with HATU (42.7 mg, 0.113 mmol, 1.20 equiv) and DIEA (24.2 mg, 0.188 mmol, 2.00 equiv) at room temperature for 10 min under nitrogen atmosphere followed by the addition of (1R,5R)-2-azabicyclo[3.1.0]hexane-3-carbonitrile (10.1 mg, 0.094 mmol, 1.00 equiv) at room temperature. The resulting mixture was stirred at room temperature for 30 min under nitrogen atmosphere. The crude product was purified by Prep-HPLC with the following conditions: Column: Uitimate-XB-C18 Column, 30*150 mm, 10 μm; Mobile Phase A: Water (10 mmol/L $NH_4HCO_3$+$0.05NH_3H_2O$), Mobile Phase B: ACN; Flow rate: 90 mL/min; Gradient: isocratic 40%-90% in 11 min; Wave Length: 254 nm/220 nm; RT1(min): 10.5. This resulted in N-((4S,5S)-3-((1R,5R)-3-cyano-2-azabicyclo [3.1.0]hexane-2-carbonyl)-4-cyclopropyl-7-ethyl-5-methyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (11.0 mg, 18.8% yield, 99.9% purity) as a white solid.

| | |
|---|---|
| 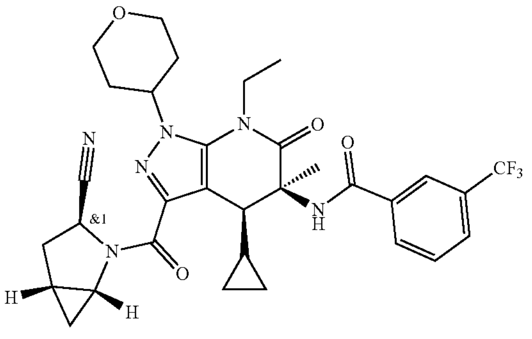 [SMILES: CCN1C(=O)[C@@](C)(NC(=O)c2cccc(C(F)(F)F)c2)[C@@H](C2CC2)c2c(C(=O)N3[C@H](C#N)C[C@H]4C[C@H]43)nn(C3CCOCC3)c21] I-516 | $^1$H NMR (400 MHz, DMSO-$d_6$) δ 8.12 (t, J = 8.9 Hz, 3H), 7.98 (d, J = 7.8 Hz, 1H), 7.79 (t, J = 7.8 Hz, 1H), 4.89 (dd, J = 8.8, 5.8 Hz, 1H), 4.56 (d, J = 10.8 Hz, 1H), 4.29 (q, J = 6.9 Hz, 1H), 4.14 (dt, J = 14.3, 6.4 Hz, 1H), 4.05 (t, J = 8.7 Hz, 2H), 4.00-3.88 (m, 2H), 3.65-3.43 (m, 2H), 2.63 (d, J = 14.3 Hz, 1H), 2.49-2.23 (m, 2H), 2.13 (d, J = 15.8 Hz, 1H), 2.08 (d, J = 7.5 Hz, 1H), 2.02-1.73 (m, 2H), 1.48-1.39 (m, 3H), 1.28 (dt, J = 10.0, 7.2 Hz, 4H), 1.04-0.78 (m, 2H), 0.59 (d, J = 5.2 Hz, 2H), 0.29 (t, J = 9.0 Hz, 1H), 0.20-0.01 (m, 3H). LCMS Calculated for $C_{32}H_{35}F_3N_6O_4$: 624.27; Observed (Method-N): 623.3 [M − H]$^-$, 99.9% at RT 1.561 min. |

Synthesis of N-((4S*,5S*)-3-((1R,3S,5R)-3-cyano-2-azabicyclo[3.1.0]hexane-2-carbonyl)-4-cyclopropyl-7-methyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-650) and N-((4R*,5R*)-3-((1R,3S,5R)-3-cyano-2-azabicyclo[3.1.0]hexane-2-carbonyl)-4-cyclopropyl-7-methyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-528)

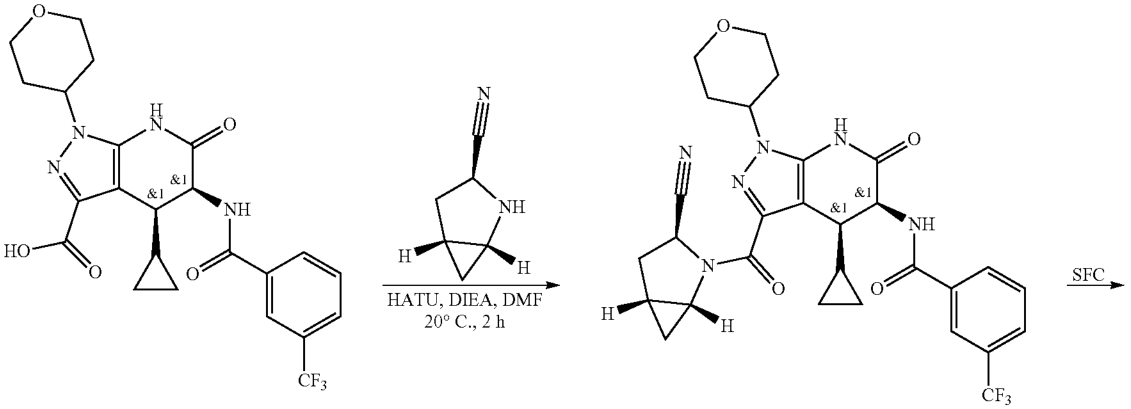

12

13

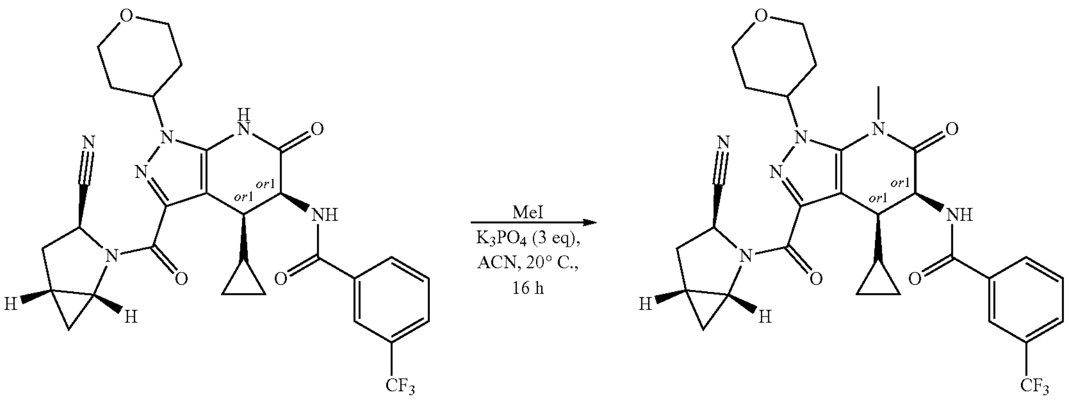

13A

I-650

-continued

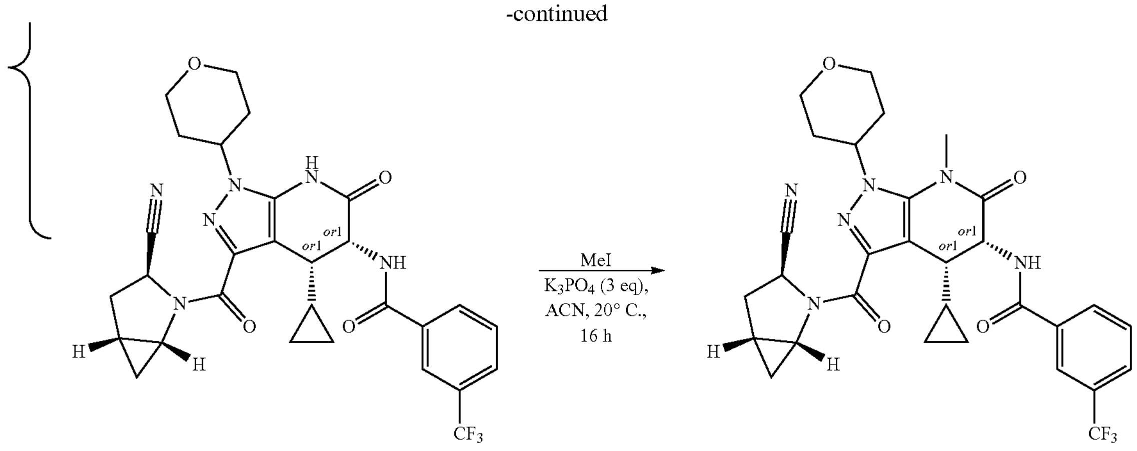

13B

I-528

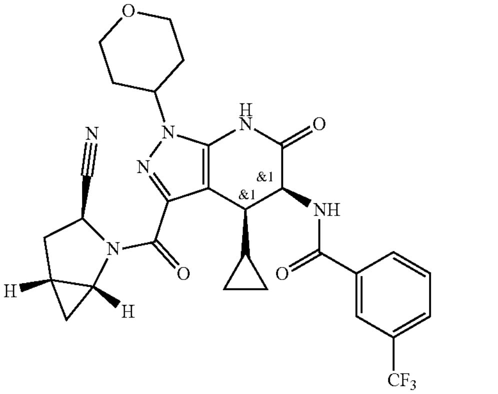

N-(rac-(4S,5S)-3-((1R,3S,5R)-3-cyano-2-azabicyclo[3.1.0]hexane-2-carbonyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-516)

Into a 8 mL vial were added rac-(4R,5R)-4-cyclopropyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (260 mg, 0.528 mmol, 1.00 equiv), DIEA (204 mg, 1.58 mmol, 3.00 equiv) and HATU (240 mg, 0.634 mmol, 1.20 equiv) in DMF (3 mL) at room temperature. The mixture was stirred at 0° C. for 10 minute, (1R,3S,5R)-2-azabicyclo[3.1.0]hexane-3-carbonitrile (68.5 mg, 0.634 mmol, 1.20 equiv) was added and the mixture was allowed to stirred for 1 hour at 0° C. The reaction was purified by Column: YMC-Actus Triart C18 Column, 50*250 mm, 5 μm; Mobile Phase A: Water (10 mmol/L $NH_4HCO_3$), Mobile Phase B: ACN; Flow rate: 90 mL/min; Gradient: 45% to 75% B in 16 min; Wave Length: 254 nm/220 nm; RT1(min): 10. This resulted in N-(rac-(4S,5S)-3-((1R,3S,5R)-3-cyano-2-azabicyclo[3.1.0]hexane-2-carbonyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (250 mg, 81.2% yield, 93.2% purity) as a white solid.

LCMS Calculated for $C_{29}H_{29}F_3N_6O_4$: 582.22; Observed: 583.2 $[M+H]^+$.

13A

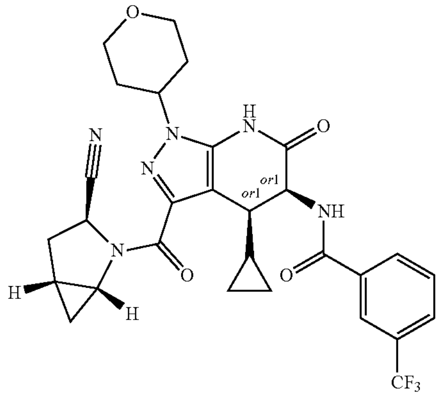

13B

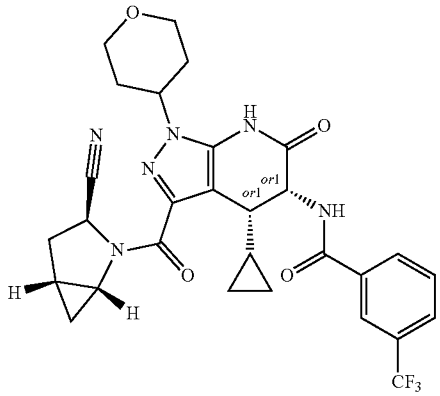

The N-(rac-(4S,5S)-3-((1R,3S,5R)-3-cyano-2-azabicyclo[3.1.0]hexane-2-carbonyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (250 mg, 0.446 mmol, 1.00 equiv) was separated by Column: CHIRALPAK IA, 3*25 cm, 5 μm; Mobile Phase A: CO2, Mobile Phase B: IPA (0.1% FA); Flow rate: 80 mL/min; Gradient: isocratic 25% B; Column Temperature (C): 35; Back Pressure (bar): 100; Wave Length: 220 nm; RT1(min): 2.6; RT2(min): 3.5; Sample Solvent: IPA; Injection Volume: 4 mL to afford N-((4S*,5S*)-3-((1R,3S,5R)-3-cyano-2-azabicyclo[3.1.0]hexane-2-carbonyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (13A) (63 mg, 96.2% purity) as a white solid and N-((4R*,5R*)-3-((1R,3S,5R)-3-cyano-2-azabicyclo[3.1.0]hexane-2-carbonyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (13B) (60 mg, 95.3% purity) as a white solid.

LCMS Calculated for $C_{29}H_{29}F_3N_6O_4$: 582.22; Observed: 583.2 $[M+H]^+$.

Chiral-SFC (Method-C): 13A: 100% at RT 1.001 min; 13B: 100% at RT 1.221 min.

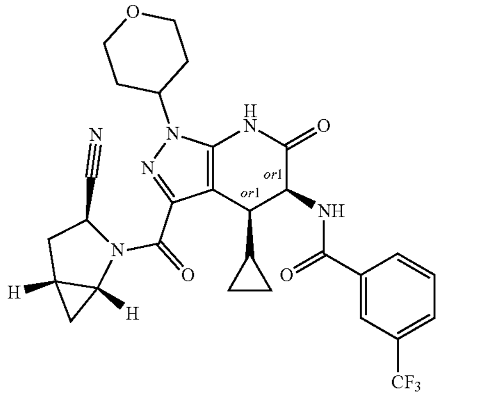

N-((4S*,5S*)-3-((1R,3S,5R)-3-cyano-2-azabicyclo[3.1.0]hexane-2-carbonyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-516)

Into a 8 mL vial were added N-((4S*,5S*)-3-((1R,3S,5R)-3-cyano-2-azabicyclo[3.1.0]hexane-2-carbonyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (15.0 mg, 0.026 mmol, 1.00 equiv), $K_3PO_4$ (16.4 mg, 0.078 mmol, 3.00 equiv) and $CH_3I$ (7.31 mg, 0.052 mmol, 2.00 equiv) in MeCN (1 mL) at room temperature. The mixture was stirred at room temperature for 1 hour. The mixture concentrated in vacuum. The residue was applied onto a silica gel column and eluted with petroleum ether/ethyl acetate (0% to 50% ethyl acetate) to afford N-((4R*,5R*)-3-((1R,3S,5R)-3-cyano-2-azabicyclo[3.1.0]hexane-2-carbonyl)-4-cyclopropyl-7-methyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (11.0 mg, 95.0% purity) as a white solid.

| | |
|---|---|
| 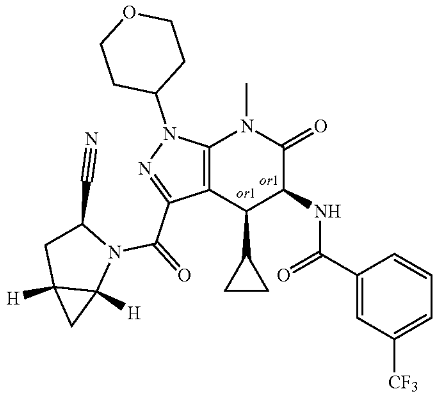 [SMILES: CN1C(=O)[C@@H](NC(=O)c2cccc(C(F)(F)F)c2)[C@@H](C2CC2)c2c(C(=O)N3[C@H](C#N)C[C@H]4C[C@H]43)nn(C3CCOCC3)c21] | $^1H$ NMR (400 MHz, DMSO-$d_6$) δ 9.05 (d, J = 8.0 Hz, 1H), 8.32 (s, 1H), 8.26 (d, J = 7.9 Hz, 1H), 7.96 (d, J = 7.8 Hz, 1H), 7.76 (t, J = 7.8 Hz, 1H), 5.69-4.84 (m, 2H), 4.75-4.61 (m, 1H), 4.39-3.46 (m, 9H), 2.19-2.15 (m, 2H), 2.10-2.06 (m, 1H), 2.04-1.95 (m, 2H), 1.92-1.82 (m, 2H), 0.92-0.82 (m, 3H), 0.65-0.56 (m, 1H), 0.48-0.41 (m, 1H), 0.21-0.14 (m, 1H), 0.12-0.08 (m, 1H).<br>LCMS Calculated for C30H31F3N6O4: 596.24. Observed (Method-AU): 597.2 $[M + H]^+$, 95.01% at RT 2.827 min.<br>Chiral SFC (Method-H): 96.63% at RT 1.89 min. |

I-650

-continued

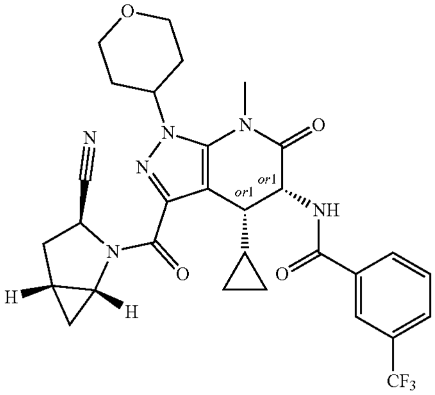 [SMILES: CN1C(=O)[C@H](NC(=O)c2cccc(C(F)(F)F)c2)[C@H](C2CC2)c2c(C(=O)N3[C@H](C#N)C[C@H]4C[C@H]43)nn(C3CCOCC3)c21]

I-528

$^1$H NMR (400 MHz, DMSO-$d_6$) δ 9.05 (d, J = 7.8 Hz, 1H), 8.32 (s, 1H), 8.25 (d, J = 7.9 Hz, 1H), 7.96 (d, J = 7.8 Hz, 1H), 7.76 (t, J = 7.8 Hz, 1H), 5.68-4.81 (m, 2H), 4.70-4.65 (m, 1H), 4.22-4.17 (m, 1H), 4.04-3.97 (m, 1H), 3.96-3.89 (m, 1H), 3.61-3.39 (m, 6H), 3.36-2.33 (m, 1H), 2.29-2.13 (m, 2H), 2.04-1.96 (m, 2H), 1.89 (d, J = 13.1 Hz, 1H), 1.01-0.92 (m, 1H), 0.92-0.81 (m, 2H), 0.73-0.69 (m, 1H), 0.60-0.45 (m, 1H), 0.23-0.13 (m, 2H), 0.13-0.04 (m, 1H).
LCMS Calculated for $C_{30}H_{31}F_3N_6O_4$: 596.24.
Observed (Method-X): 597.2 [M + H]$^+$, 99.44% at RT 1.712 min.
Chiral SFC (Method-H): 100% at RT 2.15 min.

Synthesis of N-((4S,5S)-3-((1R,3S,5R)-3-cyano-2-azabicyclo[3.1.0]hexane-2-carbonyl)-4,7-dicyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-388)

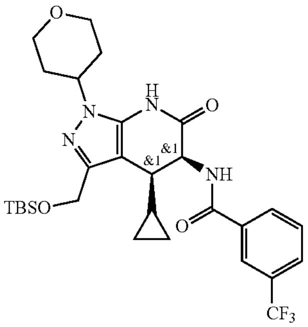

5

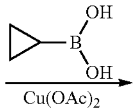

Cu(OAc)$_2$
(0.3 eq),
PY(3.0 eq),
DMF, 90° C.,
24 h
Step 1

-continued

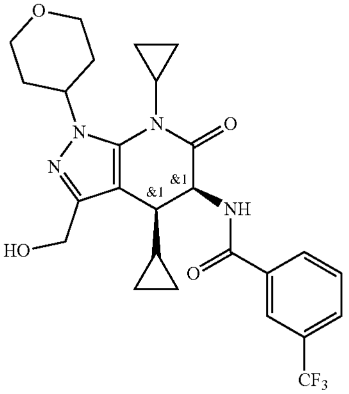

15

NaH$_2$PO$_4$ (11.5 eq),
NaClO (0.3 eq),
NaClO$_2$ (3 eq),
TEMPO (0.3 eq)
ACN, H$_2$O, 2 h
25° C.
Step 3

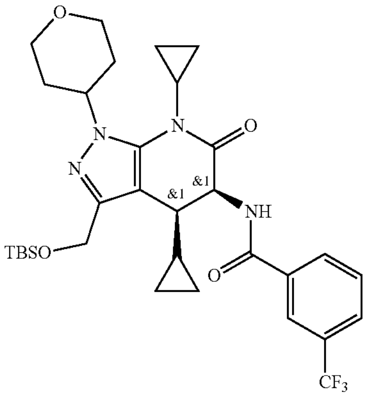

14

2M HCl,
ACN
25° C., 0.5 h
Step 2

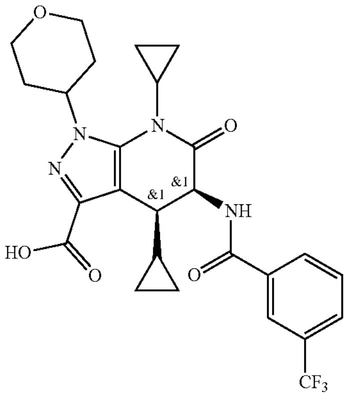

16

SFC
Step 4

-continued

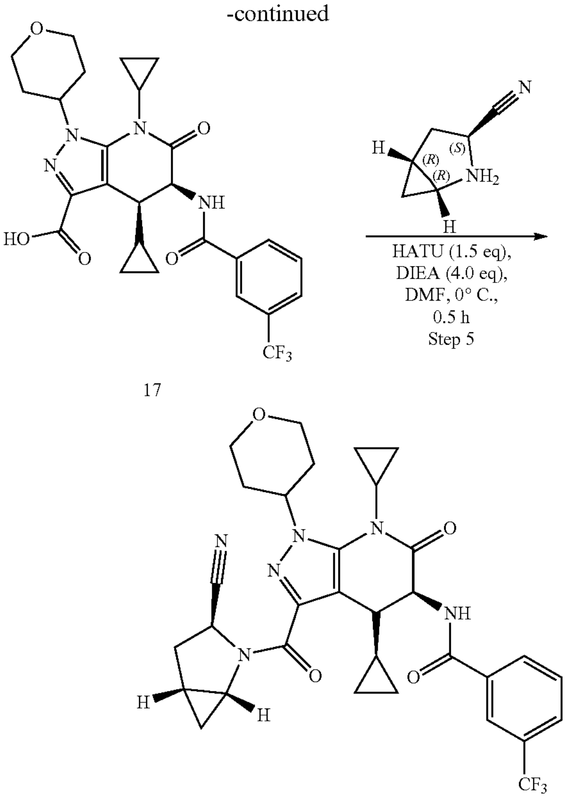

17

I-388 rac-N-((4R,5R)-3-(((tert-butyldimethylsilyl)oxy)methyl)-4,7-dicyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (14)

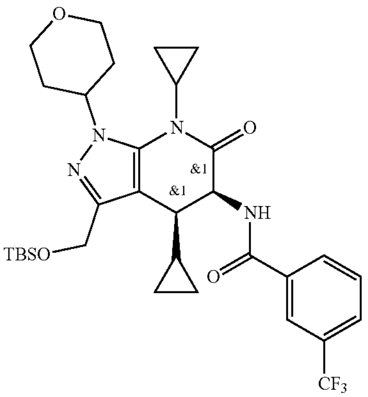

A solution of rac-N-((4R,5R)-3-(((tert-butyldimethylsilyl)oxy)methyl)-4-cyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (600 mg, 1.01 mmol, 1.00 equiv) and copper acetate (55.16 mg, 0.304 mmol, 0.3 equiv) in DMF (10 mL) was treated with pyridine (240 mg, 3.04 mmol, 3.00 equiv) at 20° C. under nitrogen atmosphere followed by the addition of cyclopropylboronic acid (130 mg, 1.52 mmol, 1.50 equiv) in portions at 20° C. The reaction mixture was stirred at 90° C. for a period of 24 h. The mixture was allowed to cool down to 20° C. The residue product was purified by reverse phase flash with the following conditions ($NH_3$) to afford rac-N-((4R,5R)-3-(((tert-butyldimethylsilyl)oxy)methyl)-4,7-dicyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (340 mg, 53.1% yield, 99.5% purity) as a white solid.

rac-N-((4R,5R)-4,7-dicyclopropyl-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (15)

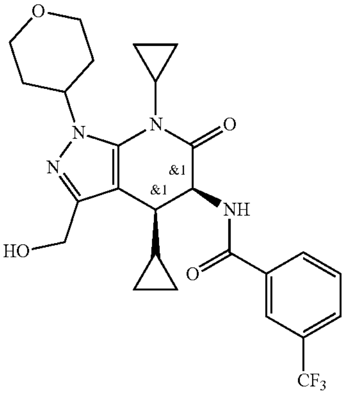

A solution of rac-N-((4R,5R)-3-(((tert-butyldimethylsilyl)oxy)methyl)-4,7-dicyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (340 mg, 0.537 mmol, 1.00 equiv) and HCl (3 mL) in MeCN (3 mL) was stirred at 20° C. for 2 h under nitrogen atmosphere. The resulting mixture was extracted with $CH_2Cl_2$ (3×10 mL). The combined organic layers were washed with brine (2×10 mL), dried over anhydrous $Na_2SO_4$. After filtration, the filtrate was concentrated under reduced pressure. The residue was purified by silica gel column chromatography, eluted with petroleum ether/ethyl acetate (1:1) to afford rac-N-((4R,5R)-4,7-dicyclopropyl-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (224 mg, 80% yield, 99.2% purity) as a white solid.

LCMS Calculated for $C_{26}H_{29}F_3N_4O_4$: 518.21; Observed: 519.3 $[M+H]^+$.

rac-((4R,5R)-4,7-dicyclopropyl-6-oxo-1-(tetrahydro-2H-pyran-4-yl)-5-(3-(trifluoromethyl)benzamido)-4,5,6,7-tetrahydro-1H-pyrazolo[3,4-b]pyridin-3-carboxylic acid (16)

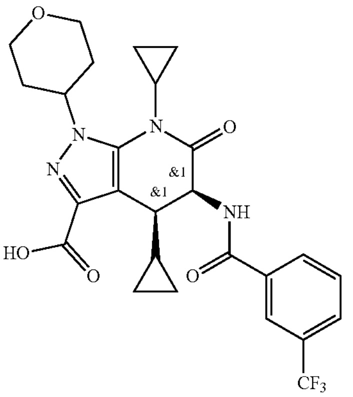

A solution of rac-N-((4R,5R)-4,7-dicyclopropyl-3-(hydroxymethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (214 mg, 0.413 mmol, 1.00 equiv) in MeCN (2 mL) was treated with $NaH_2PO_4$ (569 mg, 4.75 mmol, 11.5 equiv) and 2,2,6,6-tetramethylpiperidin-1-olate (19.4 mg, 0.124 mmol, 0.300 equiv) and sodium chlorite (112 mg, 1.24 mmol, 3.00 equiv) at 20° C. for 5 min under nitrogen atmosphere followed by the addition of sodium hypochlorite solution (9.22 mg, 0.124 mmol, 0.300 equiv) dropwise at 20° C. The resulting mixture was extracted with $CH_2Cl_2$ (3×10 mL). The combined organic layers were washed with brine (1×10 mL), dried over anhydrous $Na_2SO_4$. The residue was purified by silica gel column chromatography, eluted with petroleum ether/ethyl acetate (1:1) to afford rac-(4R,5R)-4,7-dicyclopropyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (200 mg, 91% yield, 100% purity) as a white solid.

LCMS Calculated for $C_{26}H_{27}F_3N_4O_5$: 532.19; Observed: 531.2 $[M-H]^-$ (4S,5S)-4,7-dicyclopropyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (17)

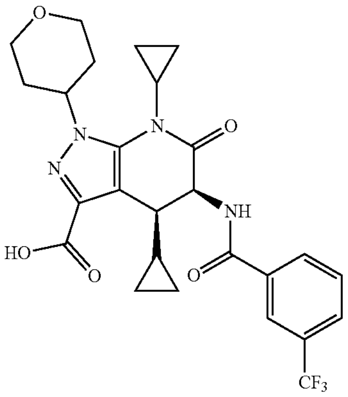

rac-(4R,5R)-4,7-dicyclopropyl-6-oxo-1-(tetrahydro-2H-pyran-4-yl)-5-(3-(trifluoromethyl)benzamido)-4,5,6,7-tetrahydro-1H-pyrazolo[3,4-b]pyridine-3-carboxylic acid (200 mg, 0.376 mmol, 1.00 equiv) was separated by Chiral-SFC with follow conditions: Column Name: CHIRALPAK IC-3 50×4.6 mm 3.0 μm Co Solvent: MeOH/DCM=1/1 (20 mM $NH_3$) to afford (4S,5S)-4,7-dicyclopropyl-1-(oxan-4-yl)-6-oxo-5-[3-(trifluoromethyl)benzamido]-4H,5H-pyrazolo[3,4-b]pyridine-3-carboxylic acid (75 mg, 37.5% yield, 97% purity).

LCMS Calculated for $C_{26}H_{27}F_3N_4O_5$: 532.1; Observed: 531.2 $[M-H]^-$

Chiral-SFC (Method-B): 98.5% at RT 1.79 min.

Optical rotation value: a=+2.381 (c=0.084 g/100 mL in MeOH, T=25° C.)

N-((4S,5S)-3-((1R,3S,5R)-3-2-azabicyclo[3.1.0]hexane-2-carbonyl)-4,7-dicyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (I-388)

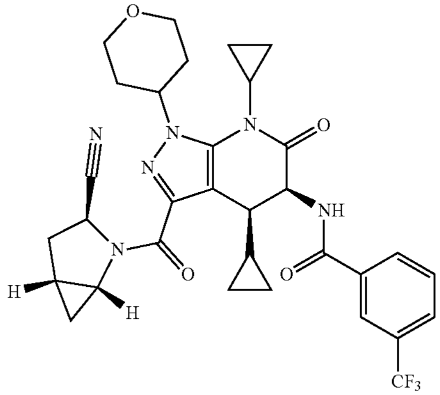

A solution of (4S,5S)-4,7-dicyclopropyl-1-(oxan-4-yl)-6-oxo-5-[3-(trifluoromethyl)benzamido]-4H,5H-pyrazolo[3,4-b]pyridine-3-carboxylic acid (30.0 mg, 0.056 mmol, 1.00 equiv) in DMF (1 mL) was treated with DIEA (29.1 mg, 0.224 mmol, 4.00 equiv) and HATU (32.1 mg, 0.084 mmol, 1.50 equiv) at 0° C. for 5 min under nitrogen atmosphere followed by the addition of (1R,3S,5R)-2-azabicyclo[3.1.0]hexane-3-carbonitrile (12.2 mg, 0.112 mmol, 2.00 equiv) dropwise at 0° C. The reaction mixture was stirred at 0° C. for 1 h. The resulting mixture was purified by reverse phase flash with the method-A conditions to afford N-((4S,5S)-3-((1R,3S,5R)-3-cyano-2-azabicyclo[3.1.0]hexane-2-carbonyl)-4,7-dicyclopropyl-6-oxo-1-(tetrahydro-2H-pyran-4-yl)-4,5,6,7-tetrahydro-1H-pyrazolo[3,4-b]pyridin-5-yl)-3-(trifluoromethyl)benzamide (8 mg, 22.8% yield, 99.8% purity) as a white solid.

$^1H$ NMR (300 MHZ, DMSO-$d_6$) δ 9.13 (t, J=7.2 Hz, 1H), 8.38-8.16 (m, 2H), 7.96 (d, J=7.8 Hz, 1H), 7.76 (t, J=7.8 Hz, 1H), 5.67-4.75 (m, 3H), 4.34 (d, J=6.9 Hz, 1H), 4.10-3.81 (m, 2H), 3.63-3.39 (m, 3H), 3.31-3.12 (m, 1H), 2.62-2.51 (m, 1H), 2.47-2.25 (m, 3H), 2.14-1.74 (m, 4H), 1.25 (d, J=6.3 Hz, 1H), 1.08 (d, J=9.3 Hz, 1H), 0.94 (dd, J=7.8, 5.7 Hz, 1H), 0.80 (s, 2H), 0.63 (s, 2H), 0.43 (d, J=4.5 Hz, 1H), 0.14 (s, 1H), −0.04-−0.28 (m, 1H).

LCMS Calculated for $C_{32}H_{33}F_3N_6O_4$: 622.25; Observed (Method-N): 621.3 $[M-H]^-$, 99.8% at RT 1.888 min.

Chiral-SFC (Method-B): 97.0% at RT 1.10 min.

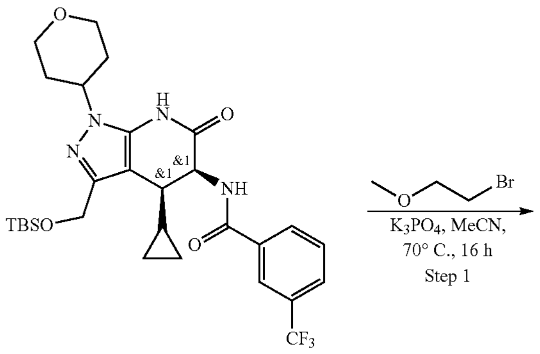

5

-continued

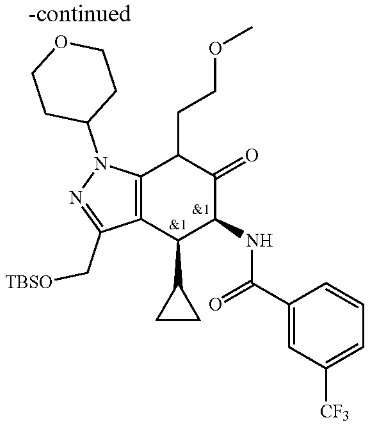

14A

A solution of rac-N-[(4R,5R)-3-{[(tert-butyldimethylsilyl)oxy]methyl}-4-cyclopropyl-1-(oxan-4-yl)-6-oxo-4H,5H,7H-pyrazolo[3,4-b]pyridin-5-yl]-3-(trifluoromethyl)benzamide (500 mg, 0.844 mmol, 1 equiv) in MeCN (5 mL) was treated with 2-bromoethyl methyl ether (176 mg, 1.27 mmol, 1.50 equiv) and $K_3PO_4$ (537 mg, 2.53 mmol, 3.00 equiv) at 20° C. for 5 min. The reaction mixture was stirred at 70° C. for a period of 16 h. The mixture was allowed to cool down to 20° C. The resulting mixture was purified by reverse phase flash with the following conditions ($NH_3$) to afford rac-N-((4R,5R)-3-(((tert-butyldimethylsilyl)oxy)methyl)-4-cyclopropyl-7-(2-methoxyethyl)-6-oxo-1-(tetrahydro-2H-pyran-4-yl)-4,5,6,7-tetrahydro-1H-pyrazolo[3,4-b]pyridin-5-yl)-3-(trifluoromethyl)benzamide (420 mg, 76.5% yield, 97% purity) as a white solid.

LCMS Calculated for $C_{32}H_{45}F_3N_4O_5Si$: 650.31; Observed: 651.3 $[M+H]^+$ The following compound was prepared according to the above methodology using 14A instead of 14.

Synthesis of N-(3-(aminomethyl)-7-ethyl-4-(4-fluorophenyl)-6-oxo-1-phenyl-6,7-dihydro-1H-pyrazolo[3,4-b]pyridin-5-yl)-3-(trifluoromethyl)benzamide (38-2)

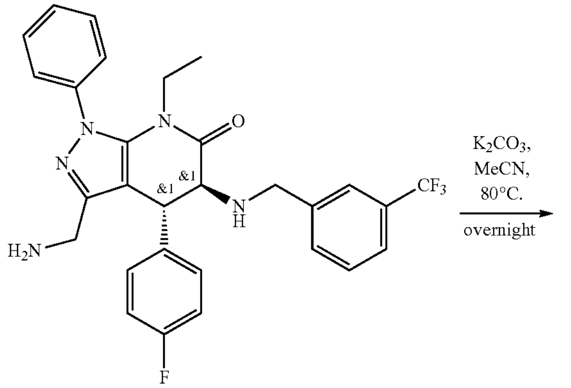

18

38-2

Compound 18 was prepared according to I-116.

A mixture of rac-N-((4R,5S)-3-(aminomethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (100 mg, 0.181 mmol, 1.00 equiv) and $K_2CO_3$ (75.2 mg, 0.543 mmol, 3.00 equiv) in MeCN (1 mL). and the reaction mixture was stirred overnight at 80° C. The resulting mixture was concentrated in vacuum, the residue was purified by Column: Sunfire Prep C18 OBD Column, 19*150 mm, 5 μm; Mobile Phase A: Water (0.1% FA), Mobile Phase B: ACN; Flow rate: 30 mL/min; Gradient: 15% B to 40% B in

| | |
|---|---|
| 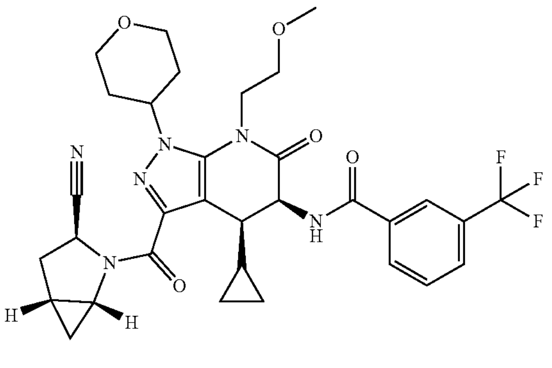 [SMILES: COCCN1C(=O)[C@@H](NC(=O)c2cccc(C(F)(F)F)c2)[C@@H](C2CC2)c2c(C(=O)N3[C@H](C#N)C[C@H]4C[C@H]43)nn(C3CCOCC3)c21]<br>I-474 | $^1H$ NMR (300 MHz, DMSO-$d_6$) δ 9.04 (d, J = 7.8 Hz, 1H), 8.31 (s, 1H), 8.24 (d, J = 7.8 Hz, 1H), 7.95 (d, J = 7.8 Hz, 1H), 7.76 (t, J = 7.8 Hz, 1H), 5.70-4.76 (m, 3H), 4.42-4.13 (m, 2H), 3.98 (q, J = 8.7, 6.0 Hz, 3H), 3.66 (s, 2H), 3.60-3.37 (m, 3H), 3.28-3.19 (m, 3H), 2.48-2.31 (m, 2H), 2.21 (d, J = 11.2 Hz, 1H), 2.16-1.91 (m, 3H), 1.86 (d, J = 12.0 Hz, 1H), 1.01-0.80 (m, 2H), 0.61 (d, J = 2.4 Hz, 1H), 0.54-0.41 (m, 1H), 0.37-0.02 (m, 3H).<br>LCMS Calculated for $C_{32}H_{35}F_3N_6O_5$: 640.26; Observed (Method-D): 639.3 $[M-H]^-$, 99.9% at RT 1.929 min.<br>Chiral-SFC (Method-B): 96.5% at RT 1.10 min. |

8 min; Wave Length: 254 nm/220 nm; RT1(min): 6.87. This resulted in N-(3-(aminomethyl)-7-ethyl-4-(4-fluorophenyl)-6-oxo-1-phenyl-6,7-dihydro-1H-pyrazolo[3,4-b]pyridin-5-yl)-3-(trifluoromethyl)benzamide (8.0 mg, 7.87%) as a white solid.

$^1$H NMR (300 MHZ, DMSO-$d_6$) δ 9.75 (s, 1H), 8.01 (s, 2H), 7.91 (d, J=7.9 Hz, 1H), 7.78-7.68 (m, 3H), 7.68-7.58 (m, 3H), 7.49-7.38 (m, 2H), 7.31 (t, J=8.7 Hz, 2H), 3.82 (d, J=7.2 Hz, 2H), 3.21 (s, 2H), 0.90 (t, J=7.0 Hz, 3H).

LCMS Calculated for $C_{29}H_{23}F_4N_5O_2$: 549.18; Observed (Method-AV): 550.2 [M+H]$^+$, 98.0% at RT 1.551 min.

Synthesis of rac-N-((4R,5R)-7-ethyl-4-(4-fluorophenyl)-3-(methylamino)-6-oxo-1-phenyl-4,5,6,7-tetrahydro-1H-pyrazolo[3,4-b]pyridin-5-yl)-3-(trifluoromethyl)benzamide (I-260)

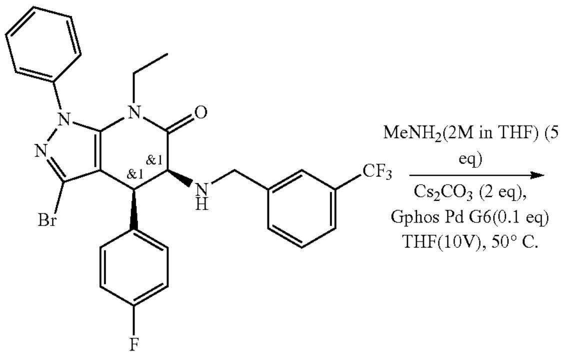

I-493

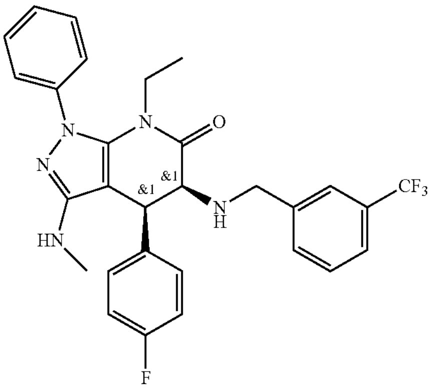

I-260

To a stirred solution of rac-N-((4R,5R)-3-bromo-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (100 mg, 0.166 mmol, 1.00 equiv) and methanamine (0.4 mL, 5 equiv) in THF (1 mL) were added $Cs_2CO_3$ (108 mg, 0.332 mmol, 2.00 equiv) and GPhos Pd G6 TES (15.7 mg, 0.017 mmol, 0.100 equiv) at room temperature under nitrogen atmosphere. The resulting mixture was stirred at 50° C. for 6 h under nitrogen atmosphere. The mixture was allowed to cool down to room temperature. The resulting mixture was concentrated under reduced pressure. The crude product was purified by reverse phase flash to afford rac-N-((4R,5R)-7-ethyl-4-(4-fluorophenyl)-3-(methylamino)-6-oxo-1-phenyl-4,5,6,7-tetrahydro-1H-pyrazolo[3,4-b]pyridin-5-yl)-3-(trifluoromethyl)benzamide (38 mg, 41.4%) as a white solid.

$^1$H NMR (300 MHZ, DMSO-$d_6$) δ 8.49 (d, J=7.1 Hz, 1H), 8.12 (d, J=9.0 Hz, 2H), 7.91 (d, J=7.8 Hz, 1H), 7.70 (t, J=7.8 Hz, 1H), 7.60-7.45 (m, 4H), 7.39 (t, J=7.0 Hz, 1H), 7.08 (t, J=8.8 Hz, 2H), 6.97 (dd, J=8.5, 5.6 Hz, 2H), 5.52-5.37 (m, 2H), 4.51 (d, J=7.2 Hz, 1H), 3.88 (dq, J=14.1, 6.9 Hz, 1H), 3.01 (dt, J=14.0, 7.0 Hz, 1H), 2.62 (d, J=4.9 Hz, 3H), 0.92 (t, J=7.0 Hz, 3H).

LCMS Calculated for $C_{29}H_{25}F_4N_5O_2$: 551.19; Observed (Method-B): 552.1 [M+H]$^+$, 99.7% at RT 1.300 min.

N-((4S,5S)-3-((S)-1-cyanamido-2,2,2-trifluoroethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (38-2)

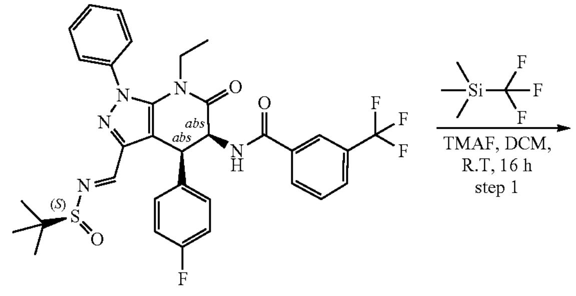

18

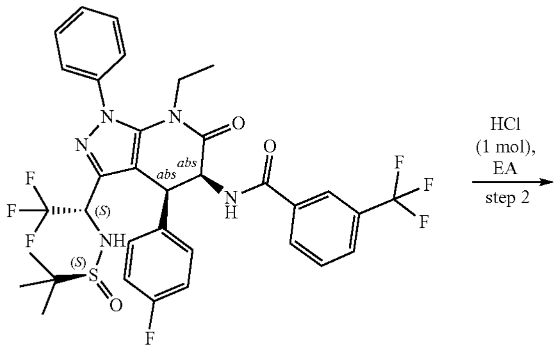

19

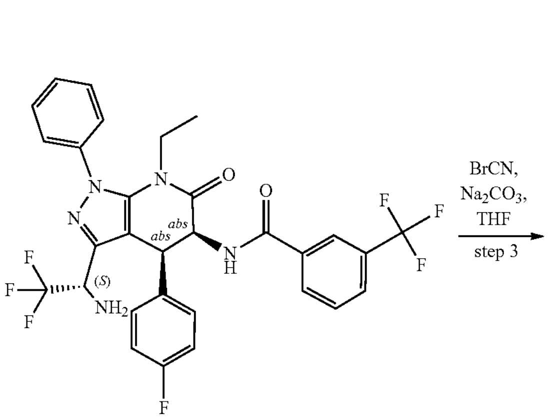

20

-continued

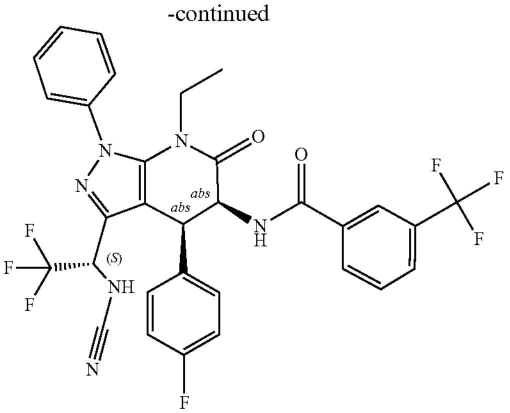

38-2

N-((4S,5S)-3-((S)-1-(((S)-tert-butylsulfinyl)amino)-2,2,2-trifluoroethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (77)

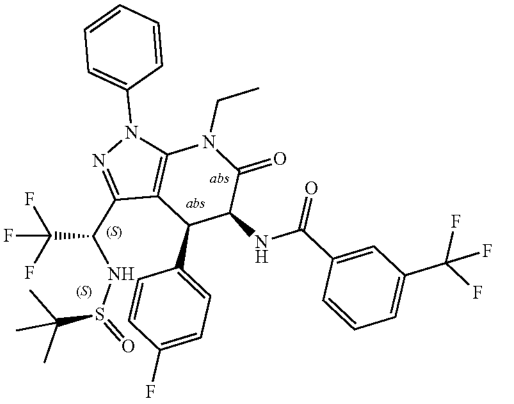

To a stirred solution of N-((4S,5S)-3-((E)-(((S)-tert-butylsulfinyl)imino)methyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (410 mg, 0.630 mmol, 1.00 equiv) and TMAF (175 mg, 1.88 mmol, 3.00 equiv) in DCM (5.00 mL) was added trifluoromethyltrimethylsilane (178 mg, 1.25 mmol, 2.00 equiv) dropwise at room temperature under nitrogen atmosphere. The resulting mixture was stirred at room temperature overnight under nitrogen atmosphere. The resulting mixture was concentrated under reduced pressure. The residue was purified by silica gel column chromatography, eluted with petroleum ether/ethyl acetate (1:1) to afford N-((4S,5S)-3-((S)-1-(((S)-tert-butylsulfinyl)amino)-2,2,2-trifluoroethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (120 mg, 26.5%) as a white solid.

LCMS Calculated for $C_{34}H_{32}F—N_5O_3S$: 723.21; Observed: 724.2 $[M+H]^+$

N-((4S,5S)-3-((S)-1-amino-2,2,2-trifluoroethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (20)

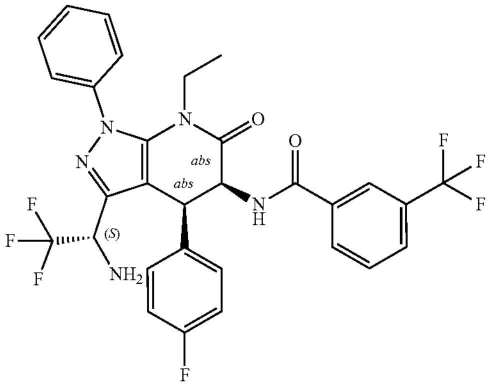

To a stirred solution of N-((4S,5S)-3-((S)-1-(((S)-tert-butylsulfinyl)amino)-2,2,2-trifluoroethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (120 mg, 0.166 mmol, 1.00 equiv) in EtOAc (1.00 mL) was added HCl (6M) (1.00 mL) dropwise at room temperature under nitrogen atmosphere. The resulting mixture was stirred at room temperature for 1 h under nitrogen atmosphere. The resulting mixture was concentrated under reduced pressure. The residue was used in the next step directly without further purification.

LCMS Calculated for $C_{30}H_{24}F_7N_5O_2$: 619.18; Observed: 619.18 $[M+H]^+$

N-((4S,5S)-3-((S)-1-cyanamido-2,2,2-trifluoroethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (38-2)

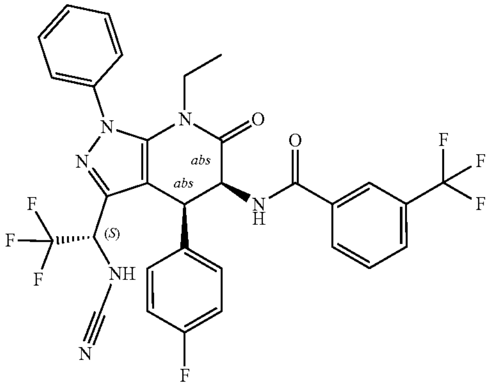

To a stirred solution of N-((4S,5S)-3-((S)-1-amino-2,2,2-trifluoroethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (100 mg, 0.161 mmol, 1.00 equiv) and $Na_2CO_3$ (27.1 mg, 0.322 mmol, 2.00 equiv) in THF (1.00 mL) was added BrCN (17.1 mg, 0.161 mmol, 1.00 equiv) in portions at room temperature under nitrogen atmosphere. The resulting mixture was stirred at room temperature for 2 h under nitrogen atmosphere. The resulting mixture was extracted with EtOAc (2×5 mL). The combined organic layers were washed with brine (2×5 mL), dried over anhydrous $Na_2SO_4$. After filtration, the filtrate was concentrated under reduced pressure. The crude product was purified by reverse phase flash with the following conditions: Column: Utimate XT-C18 Column, 30*150 mm, 10 μm; Mobile Phase A: Water (10 mmol/L $NH_4HCO_3$+

$0.05NH_3H_2O$), Mobile Phase B: ACN; Flow rate: 35 mL/min; Gradient: isocratic 60%-85% 9 min; Wave Length: 254 nm/220 nm; RT1(min): 7.2) to afford N-((4S,5S)-3-((S)-1-cyanamido-2,2,2-trifluoroethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (1.8 mg, 1.73%) as a white solid.

| | |
|---|---|
| 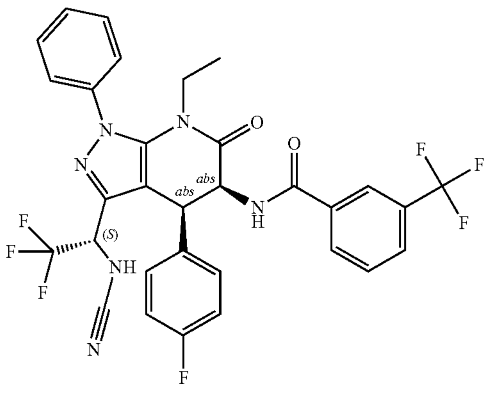<br>38-2 | $^1H$ NMR (300 MHz, DMSO-$d_6$) δ 8.55 (d, J = 7.5 Hz, 1H), 8.40 (s, 1H), 8.15 (d, J = 11.7 Hz, 2H), 7.92 (d, J = 7.9 Hz, 1H), 7.71 (t, J = 6.8 Hz, 3H), 7.60 (q, J = 7.0 Hz, 3H), 7.08 (t, J = 8.6 Hz, 2H), 6.96 (t, J = 7.0 Hz, 2H), 5.53 (t, J = 7.2 Hz, 1H), 5.46-5.26 (m, 1H), 4.78 (d, J = 7.1 Hz, 1H), 3.86 (s, 1H), 3.04 (dd, J = 14.5, 7.3 Hz, 2H), 0.88 (t, J = 7.0 Hz, 3H). LCMS Calculated for $C_{31}H_{23}F_7N_6O_2$: 644.18; Observed (Method-AW): 645.1 [M + H]$^+$, 89.8% at RT 2.394 min |

Synthesis of N-((4S,5S)-7-ethyl-4-(4-fluorophenyl)-6-oxo-1-phenyl-3-((R)-1-ureidoethyl)-4,5,6,7-tetrahydro-1H-pyrazolo[3,4-b]pyridin-5-yl)-3-(trifluoromethyl)benzamide (I-499)

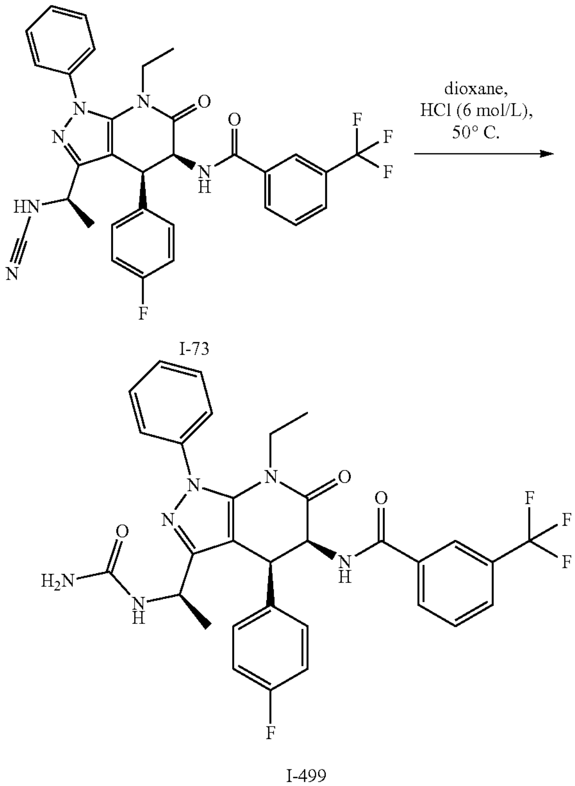

I-73

I-499

Into a 8 mL vial were added N-((4S,5S)-3-((R)-1-cyanamidoethyl)-7-ethyl-4-(4-fluorophenyl)-6-oxo-1-phenyl-4,5,6,7-tetrahydro-1H-pyrazolo[3,4-b]pyridin-5-yl)-3-(trifluoromethyl)benzamide (100 mg, 0.169 mmol, 1.00 equiv), dioxane (1 mL) and HCl (6 M) (0.5 mL) at room temperature. The resulting mixture was stirred for 4 h at 50° C. The mixture was allowed to cool down to room temperature. The residue was purified by reversed-phase flash chromatography with the following conditions: column, C18 silica gel; mobile phase, MeCN in Water (0.1% FA), 10% to 50% gradient in 10 min; detector, UV 254 nm. This resulted in N-((4S,5S)-7-ethyl-4-(4-fluorophenyl)-6-oxo-1-phenyl-3-((R)-1-ureidoethyl)-4,5,6,7-tetrahydro-1H-pyrazolo[3,4-b]pyridin-5-yl)-3-(trifluoromethyl)benzamide (61.0 mg, 59.1%) as a white solid. $^1H$ NMR (400 MHZ, DMSO-$d_6$) δ 8.55 (dd, J=10.6, 7.4 Hz, 1H), 8.20-8.11 (m, 2H), 7.93 (d, J=7.8 Hz, 1H), 7.76-7.66 (m, 3H), 7.64-7.50 (m, 3H), 7.11 (q, J=8.8 Hz, 2H), 6.99 (td, J=8.7, 5.5 Hz, 2H), 5.53 (td, J=7.4, 2.0 Hz, 1H), 5.48 (s, 1H), 5.27 (s, 1H), 4.74 (td, J=7.4, 4.1 Hz, 1H), 4.59 (t, J=6.5 Hz, 1H), 3.90 (dt, J=14.5, 7.4 Hz, 1H), 3.06 (dt, J=14.1, 7.0 Hz, 1H), 1.30-1.17 (m, 3H), 0.92 (td, J=7.1, 3.8 Hz, 3H), 0.85 (q, J=9.2, 7.7 Hz, 1H).

LCMS Calculated for $C_{31}H_{28}F_4N_6O_3$: 608.22; Observed (Method-B): 609.1 [M+H]$^+$, 99.9% at RT 1.197 min.

General experimental procedure

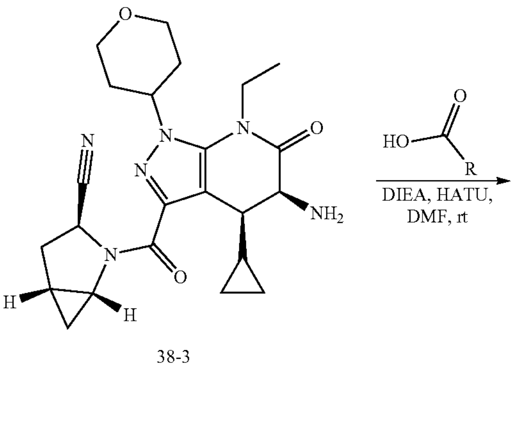

38-3

-continued

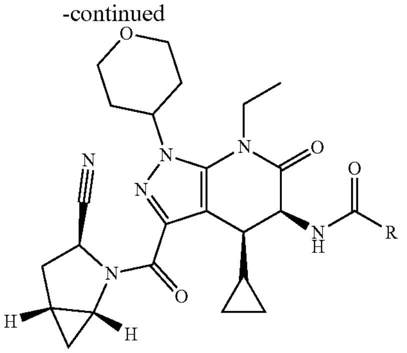

To a stirred mixture of (1R,3S,5R)-2-[5-amino-4-cyclopropyl-7-ethyl-1-(oxan-4-yl)-6-oxo-4H,5H-pyrazolo[3,4-b]pyridine-3-carbonyl]-2-azabicyclo[3.1.0]hexane-3-carbonitrile (50.0 mg, 1.00 equiv) and DIEA (2.00 equiv) in DMF (2 mL) were added acid (0.90 equiv) and HATU (1.20 equiv) in portions at room temperature under nitrogen atmosphere. The resulting mixture was stirred at room temperature for 1 h under nitrogen atmosphere. The mixture was purified by Prep-HPLC to give product.

| Compound Number | R group | % yield | Characterization data |
|---|---|---|---|
| I-633 | 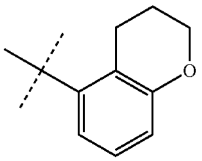 | 61.53 | $^1H$ NMR (300 MHz, DMSO-$d_6$) δ 8.33 (d, J = 7.9 Hz, 1H), 7.16 (t, J = 7.9 Hz, 1H), 6.99 (d, J = 6.8 Hz, 1H), 6.85 (d, J = 8.1 Hz, 1H), 4.88 (s, 1H), 4.33 (s, 1H), 4.15 (s, 3H), 4.01 (s, 4H), 3.55 (s, 1H), 3.45 (s, 3H), 2.84 (s, 3H), 1.92 (s, 6H), 1.26 (s, 3H), 0.62 (s, 1H), 0.47 (s, 2H), 0.20-0.08 (m, 3H), 0.14-0.01 (m, 3H). LCMS Calculated for $C_{33}H_{38}N_6O_5$: 598.29; Observed (Method-N): 597.3 $[M - H]^-$, 99.6% at RT 1.860 min. |
| I-445 | 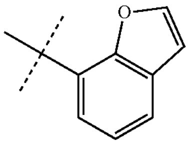 | 33.00 | $^1H$ NMR (300 MHz, DMSO-$d_6$) δ 8.63 (d, J = 6.6 Hz, 1H), 7.73 (d, J = 7.7 Hz, 1H), 7.47 (d, J = 7.2 Hz, 1H), 7.00 (t, J = 7.6 Hz, 1H), 4.94-4.76 (m, 3H), 4.51 (s, 1H), 4.32 (s, 1H), 4.04 (s, 2H), 3.92 (s, 2H), 3.44-3.51 (m, 2H), 3.28 (s, 1H), 2.48-2.36 (m, 6H), 1.94-1.99 (m, 3H), 1.27 (d, J = 7.2 Hz, 3H), 0.94 (s, 1H), 0.62 (s, 2H), 0.45 (s, 2H), 0.17 (s, 3H). LCMS Calculated for $C_{32}H_{36}N_6O_5$: 584.27; Observed (Method-N): 585.4 $[M + H]^+$, 99.9% at RT 1.827 min. |
| I-446 | 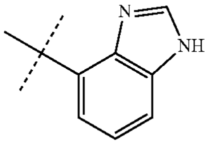 | 29.20 | $^1H$ NMR (300 MHz, DMSO-$d_6$) δ 12.99 (s, 1H), 10.76 (d, J = 7.1 Hz, 1H), 8.53 (s, 1H), 7.90 (t, J = 6.4 Hz, 1H), 7.78 (dd, J = 8.0, 1.1 Hz, 1H), 7.36 (t, J = 7.8 Hz, 1H), 5.67-4.79 (m, 2H), 4.50 (s, 1H), 4.31 (s, 1H), 4.20-3.89 (m, 4H), 3.61-3.39 (m, 3H), 2.45-2.20 (m, 3H), 2.15-1.85 (m, 4H), 1.26 (t, J = 6.9 Hz, 3H), 0.92 (d, J = 8.2 Hz, 1H), 0.68-0.60 (m, 2H), 0.42 (s, 1H), 0.30-0.01 (m, 3H). LCMS Calculated for $C_{31}H_{38}N_8O_4$: 582.27; Observed (Method-N): 581.3 $[M - H]^+$, 99.9% at RT 1.594 min. |

-continued

| Compound Number | R group | % yield | Characterization data |
|---|---|---|---|
| I-602 | 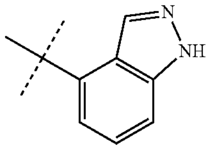 | 57.20 | $^1$H NMR (300 MHz, DMSO-$d_6$) δ 13.36 (s, 1H), 8.45-8.32 (m, 2H), 7.76 (m, J = 12.0, 7.7 Hz, 2H), 7.54-7.43 (m, 1H), 5.07 (s, 1H), 4.89 (s, 1H), 4.34 (m, 2H), 4.05 (m, 2H), 3.93 (s, 2H), 3.54 (m, J = 13.9 Hz, 4H), 2.49-2.37 (m, 1H), 2.13 (s, 1H), 1.96 (s, 4H), 1.34-1.23 (m, 3H), 0.81 (s, 1H), 0.62 (s, 1H), 0.47 (s, 1H), 0.19 (d, J = 7.8 Hz, 1H), 0.05 (m, J = 17.7 Hz, 3H). LCMS Calculated for $C_{31}H_{34}N_8O_4$: 582.27; Observed (Method-N): 581.3 $[M - H]^-$, 99.9% at RT 1.607 min. |
| I-565 | 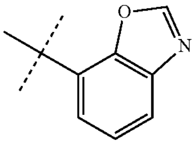 | 52.60 | $^1$H NMR (300 MHz, DMSO-$d_6$) δ 9.03 (s, 1H), 8.50 (d, J = 6.2 Hz, 1H), 8.04 (m, J = 20.1, 7.5 Hz, 2H), 7.58 (t, J = 7.8 Hz, 1H), 5.07-4.97 (m, 1H), 4.91 (d, J = 5.8 Hz, 0H), 4.53 (s, 1H), 4.33 (m, 4H), 4.05 (m, 2H), 3.93 (s, 1H), 3.54 (m, J = 17.2 Hz, 3H), 2.49-2.37 (m, 6H), 1.94 (t, 3H), 1.28 (s, 1H), 0.64 (s, 1H), 0.47 (s, 1H), 0.17 (s, 4H). LCMS Calculated for $C_{31}H_{33}N_7O_5$: 583.25; Observed (Method-N): 582.3 $[M - H]^-$, 98.9% at RT 1.700 min. |
| I-707 | 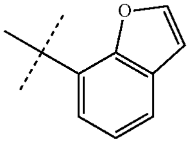 | 30.11 | $^1$H NMR (300 MHz, DMSO-$d_6$) δ 8.64 (d, J = 6.4 Hz, 1H), 8.28 (d, J = 2.3 Hz, 1H), 7.97-7.87 (m, 2H), 7.42 (t, J = 7.7 Hz, 1H), 7.17 (d, J = 2.2 Hz, 1H), 5.64-4.94 (m, 1H), 4.87 (dd, J = 8.7, 5.6 Hz, 1H), 4.51 (s, 1H), 4.32 (d, J = 5.7 Hz, 1H), 4.11-3.88 (m, 4H), 3.61-3.42 (m, 3H), 2.69-2.55 (m, 1H), 2.45-2.16 (m, 3H), 2.14-1.79 (m, 4H), 1.27 (d, J = 7.3 Hz, 3H), 0.97-0.86 (m, 1H), 0.62 (d, J = 4.7 Hz, 2H), 0.44 (s, 1H), 0.26-0.04 (m, 3H). LCMS Calculated for $C_{32}H_{34}N_6O_5$: 582.26; Observed (Method-N): 581.3 $[M - H]^-$, 99.5% at RT 1.865 min. |
| I-527 | 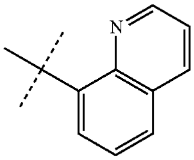 | 29.55 | $^1$H NMR (300 MHz, DMSO-$d_6$) δ 12.01 (d, J = 7.2 Hz, 1H), 9.14-9.07 (m, 1H), 8.73-8.57 (m, 2H), 8.26 (dd, J = 8.2, 1.6 Hz, 1H), 7.79 (t, J = 7.8 Hz, 1H), 7.72 (dd, J = 8.4, 4.3 Hz, 1H), 5.64-4.80 (m, 4H), 4.51 (s, 1H), 4.32 (t, J = 4.6 Hz, 1H), 4.17-3.80 (m, 4H), 3.61-3.35 (m, 3H), 2.45-2.17 (m, 3H), 2.14-1.78 (m, 4H), 1.26 (t, J = 7.0 Hz, 3H), 0.97-0.86 (m, 1H), 0.75-0.57 (m, 2H), 0.51 (d, J = 8.1 Hz, 1H), 0.22-0.16 (m, 2H). LCMS Calculated for $C_{33}H_{35}N_7O_4$: 593.28; Observed (Method-N): 594.4 $[M + H]^+$, 99.8% at RT 1.829 min. |
| I-600 | 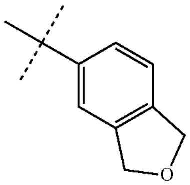 | 64.50 | $^1$H NMR (300 MHz, DMSO-$d_6$) δ 8.40 (d, J = 7.5 Hz, 1H), 7.88 (d, J = 11.6 Hz, 2H), 7.44 (d, J = 7.8 Hz, 1H), 5.07 (s, 4H), 5.05-4.96 (m, 2H), 4.51 (s, 2H), 4.33 (s, 1H), 4.03 (m, J = 12.2 Hz, 2H), 3.91 (s, 2H), 3.57 (m, J = 11.1 Hz, 2H), 2.48-2.36 (m, 2H), 1.96 (s, 4H), 1.27 (s, 3H), 0.94 (s, 1H), 0.79 (s, 1H), 0.62 (m, 2H), 0.47 (m, 2H), 0.16 (m, 2H). LCMS Calculated for $C_{32}H_{36}N_6O_5$: 584.27; Observed (Method-N): 583.3 $[M - H]^-$, 99.9% at RT 1.713 min. |

-continued

| Compound Number | R group | % yield | Characterization data |
|---|---|---|---|
| I-632 | 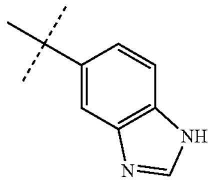 | 60.21 | $^1$H NMR (300 MHz, DMSO-$d_6$) δ 12.72 (m, J = 13.7 Hz, 1H), 8.36 (t, J = 9.2 Hz, 2H), 8.16 (s, 1H), 7.88-7.57 (m, 2H), 5.15-4.24 (m, 1H), 4.10-3.99 (m, 3H), 3.99-3.84 (m, 3H), 3.82-3.33 (m, 4H), 3.32-2.94 (m, 1H), 2.28-2.27 (m, 1H), 1.95 (s, 6H), 1.33-1.22 (m, 5H), 0.69-0.42 (m, 1H), 0.25--0.11 (m, 3H). LCMS Calculated for $C_{31}H_{34}N_8O_4$: 582.27; Observed (Method-N): 581.3 [M − H]$^-$, 99.8% at RT 1.473 min. |
| I-667 | 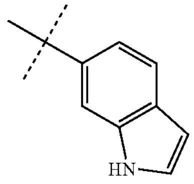 | 70.87 | $^1$H NMR (300 MHz, DMSO-$d_6$) δ 11.42 (s, 1H), 8.15 (d, J = 7.0 Hz, 1H), 8.04 (s, 1H), 7.63 (t, J = 8.1 Hz, 2H), 7.55 (t, J = 2.8 Hz, 1H), 6.52 (s, 1H), 4.99 (d, J = 6.6 Hz, 0H), 4.90 (d, J = 8.6 Hz, 1H), 4.52 (s, 2H), 4.33 (s, 1H), 4.04 (s, 3H), 3.92 (s, 1H), 3.53 (m, J = 17.0 Hz, 2H), 3.45 (d, J = 7.0 Hz, 1H), 3.31 (s, 0H), 2.48-2.36 (m, 1H), 1.94 (s, 4H), 1.27 (d, J = 7.4 Hz, 4H), 0.95 (s, 1H), 0.81 (s, 2H), 0.63 (s, 1H), 0.48 (s, 1H), 0.18 (s, 1H), 0.08 (s, 2H). LCMS Calculated for $C_{32}H_{35}N_7O_4$: 581.28; Observed (Method-N): 580.3 [M − H]$^-$, 99.8% at RT 1.767 min. |
| I-669 | 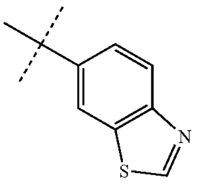 | 29.25 | $^1$H NMR (300 MHz, DMSO-$d_6$) δ 9.55 (s, 1H), 8.80 (s, 1H), 8.62 (d, J = 7.7 Hz, 1H), 8.17 (d, J = 8.5 Hz, 1H), 8.13-8.03 (m, 1H), 5.68-4.79 (m, 5H), 4.57-4.24 (m, 2H), 4.10-3.81 (m, 4H), 3.60-3.39 (m, 3H), 2.45-2.20 (m, 3H), 2.14-1.87 (m, 4H), 1.26 (t, J = 6.9 Hz, 3H), 1.08-0.88 (m, 2H), 0.82 (s, 1H), 0.60 (s, 1H), 0.47 (s, 1H), 0.21-0.02 (m, 3H). LCMS Calculated for $C_{31}H_{33}NO_4S$: 599.23; Observed (Method-N): 598.3 [M − H]$^-$, 99.8% at RT 1.695 min. |
| I-705 | 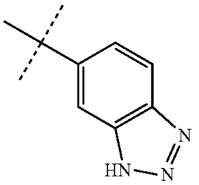 | 45.08 | $^1$H NMR (300 MHz, DMSO-$d_6$) δ 8.76 (d, J = 7.8 Hz, 1H), 8.60 (s, 1H), 7.98 (s, 2H), 5.66-4.84 (m, 2H), 4.58-4.30 (m, 3H), 4.11-3.85 (m, 4H), 3.63-3.48 (m, 3H), 2.45-2.19 (m, 2H), 2.17-1.87 (m, 4H), 1.27 (d, J = 7.2 Hz, 4H), 1.11 (d, J = 6.6 Hz, 1H), 1.00-0.81 (m, 2H), 0.62 (s, 1H), 0.52 (d, J = 8.9 Hz, 1H), 0.24-0.03 (m, 3H). LCMS Calculated for $C_{30}H_{33}N_9O_4$: 583.27; Observed (Method-N): 582.3 [M − H]$^-$, 99.9% at RT 1.164 min. |
| I-563 | 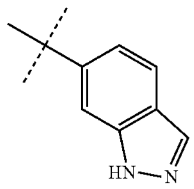 | 49.67 | $^1$H NMR (300 MHz, DMSO-$d_6$) δ 13.40 (s, 1H), 8.57 (d, J = 7.5 Hz, 1H), 8.17 (d, J = 3.9 Hz, 2H), 7.87 (d, J = 8.4 Hz, 1H), 7.66 (d, J = 8.5 Hz, 1H), 5.11-5.00 (m, 1H), 4.94-4.83 (m, 0H), 4.52 (s, 1H), 4.34 (s, 1H), 4.05 (s, 2H), 3.92 (s, 2H), 3.63-3.40 (m, 3H), 2.48-2.36 (m, 2H), 2.09 (s, 1H), 1.95 (s, 4H), 1.28 (s, 3H), 0.95 (s, 1H), 0.83 (s, 1H), 0.49 (m, 2H), 0.18 (m, 2H), 0.07 (m, 2H). LCMS Calculated for $C_{31}H_{34}N_8O_4$: 582.27; Observed (Method-N): 581.3 [M − H]$^-$, 99.9% at RT 1.607 min. |

-continued

| Compound Number | R group | % yield | Characterization data |
|---|---|---|---|
| I-444 | 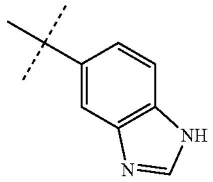 | 30.11 | $^1$H NMR (300 MHz, DMSO-$d_6$) δ 13.30 (s, 1H), 8.47 (s, 1H), 8.37 (d, J = 7.5 Hz, 1H), 8.23 (s, 1H), 7.91 (d, J = 8.8 Hz, 1H), 7.60 (d, J = 8.7 Hz, 1H), 5.63-4.98 (m, 1H), 4.96-4.82 (m, 1H), 4.50 (s, 1H), 4.31 (s, 1H), 14.16-3.79 (m, 4H), 3.60-3.40 (m, 3H), 2.46-2.14 (m, 3H), 1.99 (d, J = 45.2 Hz, 4H), 1.24 (d, J = 7.4 Hz, 3H), 0.97-0.71 (m, 2H), 0.60 (s, 1H), 0.47 (s, 1H), 0.15 (s, 3H). LCMS Calculated for $C_{31}H_{34}N_8O_4$: 582.27; Observed (Method-N): 581.3 $[M-H]^-$, 99.9% at RT 1.573 min. |
| I-483 | 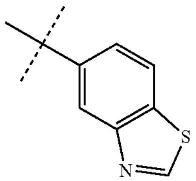 | 23.40 | $^1$H NMR (300 MHz, DMSO-$d_6$) δ 9.52 (s, 1H), 8.80 (s, 1H), 8.71 (s, 1H), 8.31 (d, J = 8.3 Hz, 1H), 8.05 (d, J = 9.1 Hz, 1H), 5.09 (s, 1H), 4.89 (s, 1H), 4.06 (s, 2H), 3.92 (s, 2H), 3.59-3.41 (m, 2H), 3.31 (s, 2H), 2.43 (m, 2H), 2.39(m, 1H), 2.31-2.24 (m, 2H), 2.17-2.10 (m, 2H), 1.98-1.91 (m, 3H), 1.28 (s, 1H), 0.86 (s, 1H), 0.62 (m, 2H), 0.18 (m, 2H), 0.07 (m, 2H). LCMS Calculated for $C_{31}H_{33}N_7O_4S$: 599.23; Observed (Method-N): 598.2 $[M-H]^-$, 99.9% at RT 1.700 min. |
| I-668 | 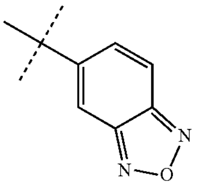 | 30.00 | $^1$H NMR (300 MHz, DMSO-$d_6$) δ 9.15 (d, J = 7.9 Hz, 1H), 8.67 (t, J = 1.3 Hz, 1H), 8.14 (dd, J = 9.4, 1.1 Hz, 1H), 7.96 (dd, J = 9.5, 1.4 Hz, 1H), 5.64-4.79 (m, 2H), 4.49 (s, 1H), 4.32 (t, J = 5.6 Hz, 1H), 4.11-3.78 (m, 4H), 3.60-3.37 (m, 3H), 2.46-2.16 (m, 3H), 2.15-1.75 (m, 4H), 1.26 (t, J = 7.0 Hz, 3H), 0.99-0.75 (m, 2H), 0.60 (s, 1H), 0.51 (d, J = 8.5 Hz, 1H), 0.29-0.03 (m, 3H). LCMS Calculated for $C_{30}H_{32}N_8O_5$: 584.25; Observed (Method-N): 583.3 $[M-H]^-$, 99.6% at RT 1.808 min. |
| I-526 | 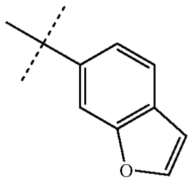 | 30.11 | $^1$H NMR (300 MHz, DMSO-$d_6$) δ 8.52 (d, J = 7.8 Hz, 1H), 8.22 (s, 1H), 8.16 (d, J = 2.2 Hz, 1H), 7.86 (d, J = 8.3 Hz, 1H), 7.75 (d, J = 8.2 Hz, 1H), 7.05 (dd, J = 2.2, 1.0 Hz, 1H), 5.63-4.81 (m, 2H), 4.51 (d, J = 10.5 Hz, 1H), 4.31 (s, 1H), 4.10-3.77 (m, 4H), 3.59-3.37 (m, 4H), 2.46-2.20 (m, 3H), 2.01 (dd, J = 43.9, 11.4 Hz, 4H), 1.31-1.20 (m, 3H), 0.97-0.73 (m, 2H), 0.60 (s, 1H), 0.47 (s, 1H), 0.15 (s, 3H). LCMS Calculated for $C_{32}H_{34}N_6O_5$: 582.26; Observed (Method-N): 581.3 $[M-H]^-$, 99.5% at RT 1.839 min. |
| I-564 | 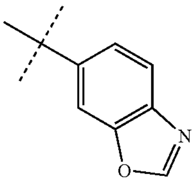 | 30.05 | $^1$H NMR (300 MHz, DMSO-$d_6$) δ 8.90 (s, 1H), 8.68 (d, J = 7.7 Hz, 1H), 8.38 (d, J = 1.5 Hz, 1H), 8.01 (dd, J = 8.3, 1.7 Hz, 1H), 7.90 (d, J = 8.3 Hz, 1H), 5.65-4.81 (m, 2H), 4.48 (d, J = 11.3 Hz, 1H), 4.35-4.27 (m, 1H), 4.10-3.80 (m, 4H), 3.59-3.36 (m, 3H), 2.46-2.16 (m, 3H), 2.14-1.76 (m, 4H), 1.26 (t, J= 6.1 Hz, 3H), 0.97-0.73 (m, 2H), 0.60 (d, J = 5.1 Hz, 1H), 0.48 (s, 1H), 0.21 (d, J = 29.3 Hz, 3H). LCMS Calculated for $C_{31}H_{33}N_7O_5$: 583.25; Observed (Method-N): 582.3 $[M-H]^-$, 97.6% at RT 1.563 min. |

-continued

| Compound Number | R group | % yield | Characterization data |
|---|---|---|---|
| I-601 | 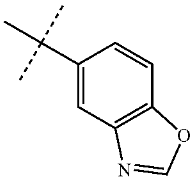 | 33.47 | $^1$H NMR (300 MHz, DMSO-$d_6$) δ 8.88 (s, 1H), 8.70 (d, J = 7.6 Hz, 1H), 8.44 (s, 1H), 8.06 (d, J = 8.6 Hz, 1H), 7.90 (d, J = 8.5 Hz, 1H), 5.08 (d, J = 6.9 Hz, 1H), 4.87 (d, J = 6.3 Hz, 1H), 4.52 (s, 1H), 4.34 (s, 1H), 4.05 (s, 3H), 3.92 (s, 1H), 3.53 (m, 2H), 2.41 (d, J = 10.7 Hz, 1H), 1.97 (s, 5H), 1.29 (d, J = 7.1 Hz, 3H), 0.86 (s, 3H), 0.62 (s, 1H), 0.49 (s, 1H), 0.18 (s, 2H), 0.07 (s, 2H). LCMS Calculated for $C_{31}H_{33}N_7O_5$: 583.25; Observed (Method-N): 582.3 $[M - H]^-$, 99.9% at RT 1.647 min. |
| I-706 | 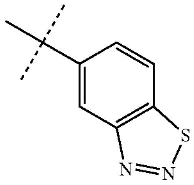 | 29.02 | $^1$H NMR (300 MHz, DMSO-$d_6$) δ 9.31 (s, 1H), 9.08 (d, J = 7.8 Hz, 1H), 8.51 (d, J = 8.5 Hz, 1H), 8.30 (d, J = 8.7 Hz, 1H), 5.66-4.76 (m, 2H), 4.51 (s, 1H), 4.33 (d, J= 6.1 Hz, 1H), 4.17-3.80 (m, 4H), 3.61-3.40 (m, 3H), 2.46-2.17 (m, 3H), 2.03 (d, J = 51.9 Hz, 4H), 1.32-1.22 (m, 3H), 0.97-0.76 (m, 2H), 0.61 (s, 1H), 0.51 (d, J = 8.8 Hz, 1H), 0.32-0.01 (m, 3H). LCMS Calculated for $C_{30}H_{32}N_8O_4S$: 600.23; Observed (Method-N): 599.2 $[M - H]^-$, 99.6% at RT 1.788 min. |
| I-504 | 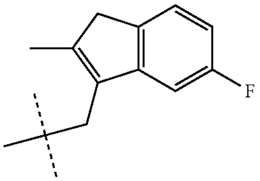 | 31.11 | LCMS Calculated for $C_{35}H_{39}FN_6O_4$: 626.3; Observed (Method-A): 627.3 $[M + H]^+$, 99.97% at RT 1.316 min. |
| I-507 | 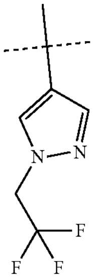 | 23.49 | $^1$H NMR (300 MHz, DMSO-$d_6$) δ 8.54 (s, 1H), 8.52-8.43 (m, 1H), 8.18 (s, 1H), 5.23 (q, J = 9.1 Hz, 2H), 5.08-4.80 (m, 2H), 4.65-4.44 (m, 1H), 4.37-4.25 (m, 1H), 4.18-3.72 (m, 4H), 3.67-3.37 (m, 2H), 2.49-1.76 (m, 8H), 1.26 (t, 3H), 1.14-0.71 (m, 2H), 0.68-0.41 (m, 2H), 0.29--0.07 (m, 3H). LCMS Calculated for $C_{29}H_{33}F_3N_8O_4$: 614.26; Observed (Method-A): 615.26 $[M + H]^+$, 99.56% at RT 1.123 min. |
| I-468 | 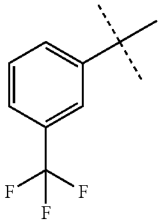 | 19.68 | LCMS Calculated for $C_{32}H_{35}F_3N_6O_4$: 624.27; Observed (Method-A): 625.27 $[M + H]^+$, 99.69% at RT 1.313 min. |
| I-618 | 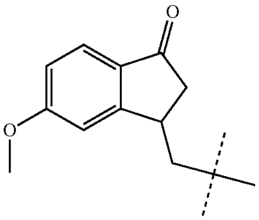 | 28.09 | LCMS Calculated for $C_{35}H_{40}N_6O_6$: 640.3; Observed (Method-A): 641.3 $[M + H]^+$, 100% at RT 1.134 min. |

-continued

| Compound Number | R group | % yield | Characterization data |
|---|---|---|---|
| I-691 | 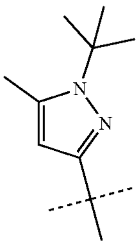 | 22.68 | $^1$H NMR (300 MHz, DMSO-$d_6$) δ 7.82 (d, J = 6.9 Hz, 1H), 6.51 (s, 1H), 4.96-4.84 (m, 1H), 4.83-4.65 (m, 1H), 4.59-4.44 (m, 1H), 4.37-4.28 (m, 1H), 4.16-3.79 (m, 4H), 3.66-3.43 (m, 2H), 2.48 (s, 3H), 2.45-1.79 (m, 8H), 1.63 (s, 9H), 1.25 (t, J = 6.7 Hz, 3H), 1.15-0.84 (m, 1H), 0.73-0.34 (m, 3H), 0.28-0.05 (m, 3H). LCMS Calculated for $C_{32}H_{42}N_8O_4$: 602.33; Observed (Method-A): 603.3 $[M + H]^+$, 100% at RT 1.310 min. |
| I-426 | 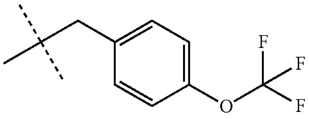 | 40.85 | $^1$H NMR (300 MHz, DMSO-$d_6$) δ 8.66-8.48 (m, 1H), 7.52-7.40 (m, 2H), 7.37-7.27 (m, 2H), 4.93-4.60 (m, 2H), 4.57-4.38 (m, 1H), 4.34-4.22 (m, 1H), 4.11-3.80 (m, 4H), 3.65-3.42 (m, 3H), 3.26-3.08 (m, 1H), 2.47-1.73 (m, 8H), 1.32-1.15 (m, 3H), 1.10-0.82 (m, 1H), 0.73-0.30 (m, 3H), 0.27--0.19 (m, 3H). LCMS Calculated for $C_{32}H_{35}F_3N_6O_5$: 640.26; Observed (Method-A): 641.26 $[M + H]^+$, 100% at RT 1.300 min. |
| I-423 | 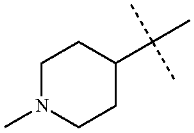 | 14.64 | LCMS Calculated for $C_{30}H_{41}N_7O_4$: 563.32; Observed (Method-A): 564.32 $[M + H]^+$, 99% at RT 1.081 min. |
| I-690 | 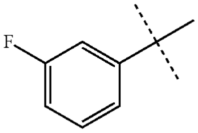 | 38.06 | 1H NMR (300 MHz, DMSO-d6) δ 8.77-8.64 (m, 1H), 7.79 (t, J= 9.7 Hz, 2H), 7.65-7.36 (m, 1H), 5.15-4.76 (m, 1H), 4.63-4.27 (m, 1H), 4.19-3.76 (m, 4H), 3.69-3.36 (m, 2H), 2.48-1.74 (m, 8H), 1.34-1.18 (m, 3H), 1.14-0.74 (m, 2H), 0.68-0.41 (m, 2H), 0.30--0.05 (m, 3H). LCMS Calculated for $C_{30}H_{33}FN_6O_4$: 560.25; Observed (Method-A): 561.25 $[M + H]^+$, 100% at RT 1.222 min. |
| I-510 | 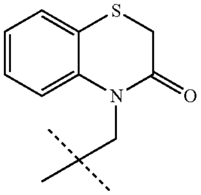 | 26.15 | LCMS Calculated for $C_{33}H_{37}N_7O_5S$: 643.26; Observed (Method-A): 644.26 $[M + H]^+$, 100% at RT 1.190 min. |
| I-695 | 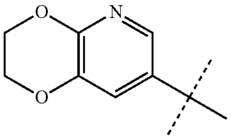 | 37.12 | LCMS Calculated for $C_{31}H_{35}N_7O_6$: 601.26; Observed (Method-A): 602.26 $[M + H]^+$, 100% at RT 1.067 min. |
| I-688 | 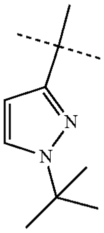 | 20.2 | $^1$H NMR (300 MHz, DMSO-$d_6$) δ 7.99 (d, J = 2.4 Hz, 1H), 7.89 (d, J = 6.9 Hz, 1H), 6.70 (d, J = 2.4 Hz, 1H), 4.96-4.67 (m, 2H), 4.61-4.25 (m, 2H), 4.21-3.79 (m, 4H), 3.66-3.43 (m, 2H), 2.47-1.78 (m, 8H), 1.59 (s, 9H), 1.26 (t, J = 6.2 Hz, 3H), 1.12-0.82 (m, 1H), 0.72-0.33 (m, 3H), 0.29-0.03 (m, 1H). LCMS Calculated for $C_{31}H_{40}N_8O_4$: 588.32; Observed (Method-A): 589.32 $[M + H]^+$, 99.10% at RT 1.262 min. |

-continued

| Compound Number | R group | % yield | Characterization data |
|---|---|---|---|
| I-466 | 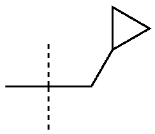 | 21.7 | LCMS Calculated for $C_{28}H_{36}N_6O_4$: 520.28; Observed (Method-A): 521.28 $[M + H]^+$, 99.69% at RT 1.138 min. |
| I-389 | 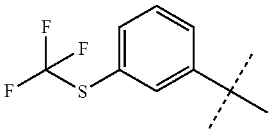 | 17.86 | $^1$H NMR (300 MHz, DMSO-$d_6$) δ 8.99-8.86 (m, 1H), 8.33-8.26 (m, 1H), 8.18 (d, J = 7.9 Hz, 1H), 7.93 (d, J = 7.7 Hz, 1H), 7.69 (t, J = 7.8 Hz, 1H), 5.17-4.81 (m, 2H), 4.63-4.27 (m, 1H), 4.20-3.79 (m, 4H), 3.67-3.43 (m, 3H), 2.48-1.78 (m, 8H), 1.27 (t, J = 7.0 Hz, 3H), 1.13-0.74 (m, 2H), 0.68-0.40 (m, 2H), 0.36--0.05 (m, 3H). LCMS Calculated for $C_{31}H_{33}F_3N_6O_4S$: 642.22; Observed (Method-A): 643.22 $[M + H]^+$, −99.80% at RT 1.352 min. |
| I-390 | 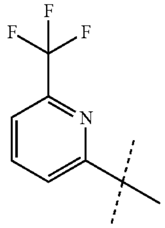 | 29.66 | LCMS Calculated for $C_{30}H_{32}F_3N_7O_4$: 611.25; Observed (Method-A): 612.25 $[M + H]^+$, 99.85% at RT 1.300 min. |
| I-588 | 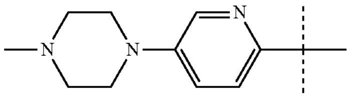 | 29.57 | LCMS Calculated for $C_{34}H_{43}N_9O_4$: 641.34; Observed (Method-A): 642.34 $[M + H]^+$, 99.56% at RT 1.151 min. |
| I-620 | 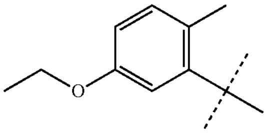 | 27.23 | LCMS Calculated for $C_{33}H_{40}N_6O_5$: 600.31; Observed (Method-A): 601.31 $[M + H]^+$, 94.37% at RT 1.304 min. |
| I-634 | 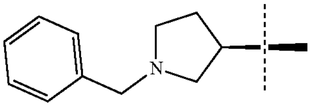 | 84.65 | LCMS Calculated for $C_{35}H_{43}N_7O_4$: 625.34; Observed (Method-C): 626.34 $[M + H]^+$, 97.59% at RT 0.792 min. |
| I-424 | 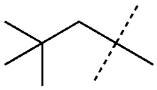 | 19.56 | LCMS Calculated for $C_{29}H_{40}N_6O_4$: 536.31; Observed (Method-A): 537.31 $[M + H]^+$, 99.95% at RT 1.223 min. |
| I-508 | 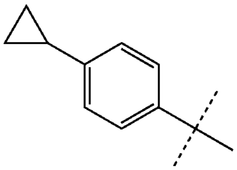 | 33.47 | LCMS Calculated for $C_{33}H_{38}N_6O_4$: 582.3; Observed (Method-A): 583.3 $[M + H]^+$, 100% at RT 1.315 min. |
| I-391 | 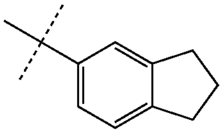 | 13.47 | LCMS Calculated for $C_{33}H_{38}N_6O_4$: 582.3; Observed (Method-A): 583.3 $[M + H]^+$, 98.12% at RT 1.344 min. |

-continued

| Compound Number | R group | % yield | Characterization data |
|---|---|---|---|
| I-623 | 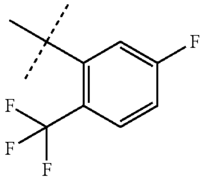 | 21.41 | $^1$H NMR (300 MHz, DMSO-$d_6$) δ 9.25-9.09 (m, 1H), 7.98-7.84 (m, 1H), 7.59-7.49 (m, 1H), 7.49-7.39 (m, 1H), 5.08-4.82 (m, 2H), 4.59-4.26 (m, 2H), 4.13-3.74 (m, 3H), 3.70-3.42 (m, 3H), 2.48-1.79 (m, 8H), 1.27 (t, J = 7.1 Hz, 3H), 1.11-0.73 (m, 2H), 0.72-0.36 (m, 2H), 0.31--0.07 (m, 3H). LCMS Calculated for $C_{31}H_{32}F_4N_6O_4$: 628.24; Observed (Method-A): 629.24 $[M + H]^+$, 99.70% at RT 1.253 min. |
| I-652 | 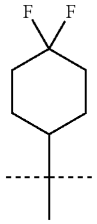 | 26.51 | LCMS Calculated for $C_{30}H_{38}F_2N_6O_4$: 584.29; Observed (Method-A): 585.29 $[M + H]^+$, 100% at RT 1.192 min. |
| I-655 | 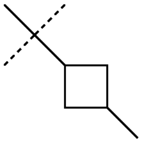 | 44.27 | LCMS Calculated for $C_{29}H_{38}N_6O_4$: 534.3; Observed (Method-A): 535.3 $[M + H]^+$, 100% at RT 1.22 min. |
| I-435 | 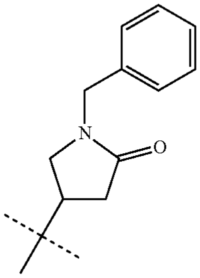 | 25.27 | LCMS Calculated for $C_{35}H_{41}N_7O_5$: 639.32; Observed (Method-A): 640.32 $[M + H]^+$, 100% at RT 1.118 min. |
| I-523 | 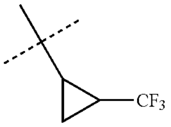 | 23.5 | LCMS Calculated for $C_{28}H_{33}F_3N_6O_4$: 574.25; Observed (Method-A): 575.25 $[M + H]^+$, 100% at RT 1.209 min. |
| I-471 | 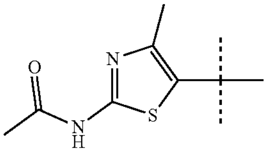 | 32.99 | LCMS Calculated for $C_{30}H_{36}N_8O_5S$: 620.25; Observed (Method-A): 621.25 $[M + H]^+$, 99.88% at RT 1.053 min. |
| I-392 | 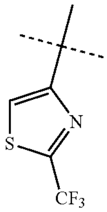 | 33.73 | LCMS Calculated for $C_{28}H_{30}F_3N_7O_4S$: 617.2; Observed (Method-A): 618.2 $[M + H]^+$, 100% at RT 1.314 min. |
| I-595 | 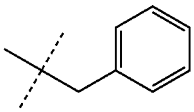 | 37.13 | LCMS Calculated for $C_{31}H_{36}N_6O_4$: 556.28; Observed (Method-A): 557.28 $[M + H]^+$, 100% at RT 1.193 min. |

-continued

| Compound Number | R group | % yield | Characterization data |
|---|---|---|---|
| I-511 | 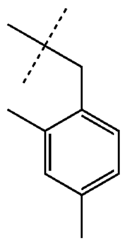 | 38.2 | LCMS Calculated for $C_{33}H_{40}N_6O_4$: 584.31; Observed (Method-A): 585.31 $[M+H]^+$, 100% at RT 1.301 min. |
| I-697 | 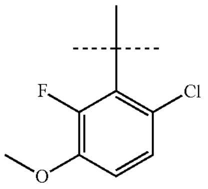 | 55.93 | LCMS Calculated for $C_{31}H_{34}ClFN_6O_5$: 624.23; Observed (Method-B): 625.23 $[M+H]^+$, 98.47% at RT 1.702 min. |
| I-472 | 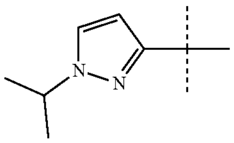 | 28.42 | LCMS Calculated for $C_{30}H_{38}N_8O_4$: 574.3; Observed (Method-A): 575.3 $[M+H]^+$, 100% at RT 1.216 min. |
| I-566 | 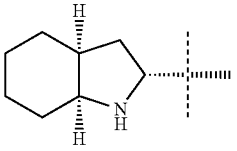 | 40.94 | LCMS Calculated for $C_{32}H_{43}N_7O_4$: 589.4; Observed (Method-B): 590.4 $[M+H]^+$, 95.93% at RT 1.781 min. |
| I-653 | 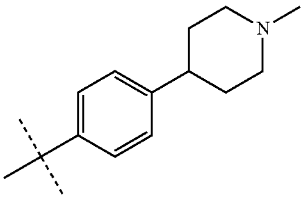 | 21.47 | LCMS Calculated for $C_{36}H_{45}N_7O_4$: 639.35; Observed (Method-A): 640.35 $[M+H]^+$, 99.31% at RT 1.243 min. |
| I-393 | 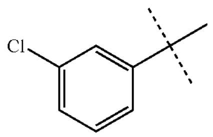 | 17.33 | LCMS Calculated for $C_{30}H_{33}ClN_6O_4$: 576.23; Observed (Method-A): 577.23 [M + H]+, 100% at RT 1.281 min. |
| I-590 | 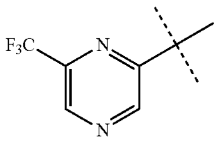 | 32.07 | LCMS Calculated for $C_{29}H_{31}F_3N_8O_4$: 612.24; Observed (Method-A): 613.24 $[M+H]^+$, 99.89% at RT 1.272 min. |
| I-512 | 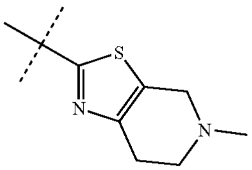 | 29.9 | LCMS Calculated for $C_{31}H_{38}N_8O_4S$: 618.27; Observed (Method-A): 619.27 $[M+H]^+$, 100% at RT 1.172 min. |

-continued

| Compound Number | R group | % yield | Characterization data |
|---|---|---|---|
| I-591 | 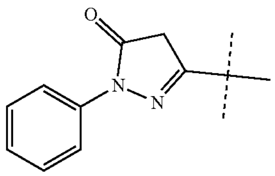 | 11.36 | LCMS Calculated for $C_{33}H_{36}N_8O_5$: 624.28; Observed (Method-A): 625.28 $[M + H]^+$, 98.99% at RT 0.85 min. |
| I-696 | 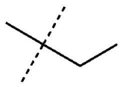 | 28.98 | LCMS Calculated for $C_{26}H_{34}N_6O_4$: 494.26; Observed (Method-A): 495.26 $[M + H]^+$, 100% at RT 1.087 min. |
| I-473 | 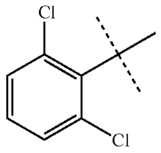 | 14.97 | LCMS Calculated for $C_{30}H_{32}C_{12}N_6O_4$: 610.19; Observed (Method-A): 611.19 [M + H]+, 99.85% at RT 1.223 min. |
| I-628 | 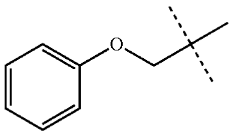 | 68.33 | LCMS Calculated for $C_{31}H_{36}N_6O_5$: 572.27; Observed (Method-B): 573.27 $[M + H]^+$, 98.64% at RT 1.749 min. |
| I-481 | 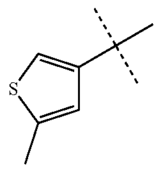 | 71.15 | LCMS Calculated for $C_{29}H_{34}N_6O_4S$: 562.24; Observed (Method-A): 563.24 $[M + H]^+$, 95.31% at RT 1.268 min. |
| I-476 | 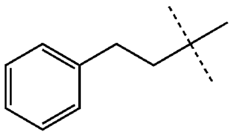 | 71.71 | LCMS Calculated for $C_{32}H_{38}N_6O_4$: 570.3; Observed (Method-A): 571.3 $[M + H]^+$, 99.00% at RT 1.259 min. |
| I-432 | 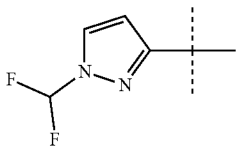 | 51.78 | LCMS Calculated for $C_{28}H_{32}F_2N_8O_4$: 582.25; Observed (Method-A): 583.25 $[M + H]^+$, 100% at RT 1.214 min. |
| I-433 | 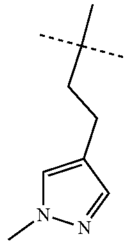 | 31.03 | LCMS Calculated for $C_{30}H_{38}N_8O_4$: 574.3; Observed (Method-A): 575.3 $[M + H]^+$, 100% at RT 1.016 min. |
| I-394 | 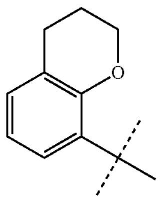 | 11.97 | LCMS Calculated for $C_{33}H_{38}N_6O_5$: 598.29; Observed (Method-A): 599.29 $[M + H]^+$, 100% at RT 1.258 min. |

-continued

| Compound Number | R group | % yield | Characterization data |
|---|---|---|---|
| I-553 | 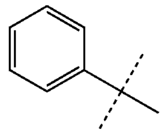 | 23.04 | LCMS Calculated for $C_{30}H_{34}N_6O_4$: 542.26; Observed (Method-A): 543.26 $[M + H]^+$, 100% at RT 1.23 min. |
| I-699 | 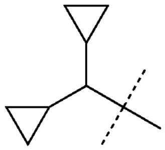 | 119.79 | LCMS Calculated for $C_{31}H_{40}N_6O_4$: 560.31; Observed (Method-A): 561.31 $[M + H]^+$, 98.76% at RT 1.276 min. |
| I-440 | 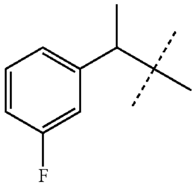 | 28.88 | LCMS Calculated for $C_{32}H_{37}FN_6O_4$: 588.29; Observed (Method-A): 589.29 $[M + H]^+$, 100% at RT 1.256 min. |
| I-656 | 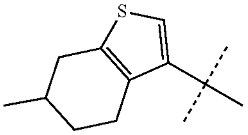 | 99.5 | LCMS Calculated for $C_{33}H_{40}N_6O_4S$: 616.28; Observed (Method-B): 617.28 $[M + H]^+$, 99.78% at RT 2.044 min. |
| I-629 | 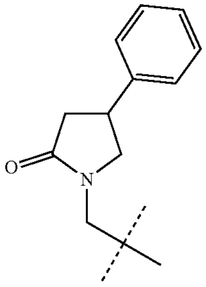 | 125.84 | LCMS Calculated for $C_{35}H_{41}N_7O_5$: 639.32; Observed (Method-A): 640.32 $[M + H]^+$, 100% at RT 1.166 min. |
| I-592 | 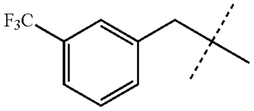 | 23.21 | LCMS Calculated for $C_{32}H_{35}F_3N_6O_4$: 624.27; Observed (Method-A): 625.27 $[M + H]^+$, 100% at RT 1.273 min. |
| I-513 | 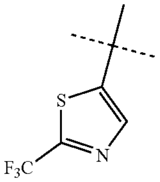 | 22.91 | LCMS Calculated for $C_{28}H_{30}F_3N_7O_4S$: 617.2; Observed (Method-A): 618.2 $[M + H]^+$, 99.85% at RT 1.274 min. |
| I-598 | 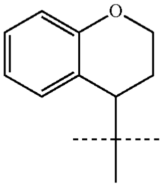 | 31.46 | LCMS Calculated for $C_{33}H_{38}N_6O_5$: 598.29; Observed (Method-A): 599.29 $[M + H]^+$, 100% at RT 1.229 min. |

-continued

| Compound Number | R group | % yield | Characterization data |
|---|---|---|---|
| I-554 | 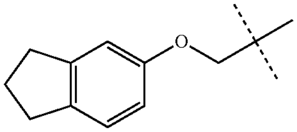 | 27.31 | LCMS Calculated for $C_{34}H_{40}N_6O_5$: 612.31; Observed (Method-A): 613.31 $[M + H]^+$, 99.39% at RT 1.375 min. |
| I-434 | 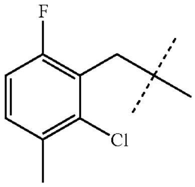 | 32.37 | LCMS Calculated for $C_{32}H_{36}ClFN_6O_4$: 622.25; Observed (Method-B): 623.25 $[M + H]^+$, 100% at RT 1.797 min. |
| I-395 | 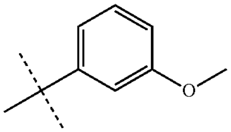 | 23.3 | LCMS Calculated for $C_{31}H_{36}N_6O_5$: 572.27; Observed (Method-A): 573.27 $[M + H]^+$, 95.28% at RT 1.209 min. |
| I-475 | 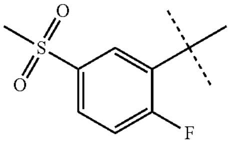 | 14.32 | LCMS Calculated for $C_{31}H_{35}FN_6O_6S$: 638.23; Observed (Method-A): 639.23 [M + H]+, 99.79% at RT 1.133 min. |
| I-663 | 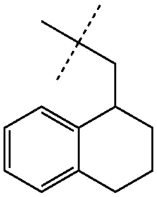 | 29.04 | LCMS Calculated for $C_{35}H_{42}N_6O_4$: 610.33; Observed (Method-A): 611.33 $[M + H]^+$, 99.45% at RT 1.325 min. |
| I-627 | 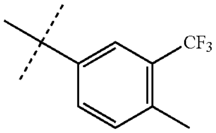 | 26.92 | LCMS Calculated for $C_{32}H_{35}F_3N_6O_4$: 624.27; Observed (Method-A): 625.27 $[M + H]^+$, 99.88% at RT 1.351 min. |
| I-698 | 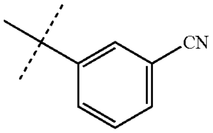 | 23.2 | LCMS Calculated for $C_{31}H_{33}N_7O_4$: 567.26; Observed (Method-A): 568.26 $[M + H]^+$, 100% at RT 1.165 min. |
| I-701 | 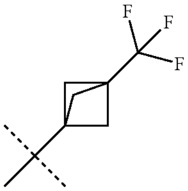 | 19.37 | LCMS Calculated for $C_{30}H_{35}F_3N_6O_4$: 600.27; Observed (Method-A): 601.27 $[M + H]^+$, 99.71% at RT 1.266 min. |
| I-555 | 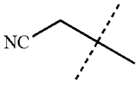 | 22.75 | LCMS Calculated for $C_{26}H_{31}N_7O_4$: 505.24; Observed (Method-A): 506.24 $[M + H]^+$, 100% at RT 1.035 min. |

-continued

| Compound Number | R group | % yield | Characterization data |
|---|---|---|---|
| I-396 | 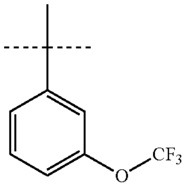 | 19.95 | LCMS Calculated for $C_{31}H_{33}F_3N_6O_5$: 626.25; Observed (Method-A): 627.25 $[M + H]^+$, 100% at RT 1.329 min. |
| I-556 | 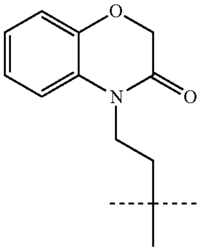 | 30.13 | LCMS Calculated for $C_{34}H_{39}N_7O_6$: 641.3; Observed (Method-A): 642.3 $[M + H]^+$, 100% at RT 1.144 min. |
| I-502 | 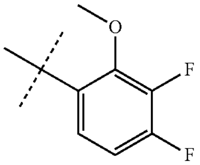 | 21.63 | LCMS Calculated for $C_{31}H_{34}F_2N_6O_5$: 608.26; Observed (Method-A): 609.26 $[M + H]^+$, 100% at RT 1.31 min. |
| I-552 | 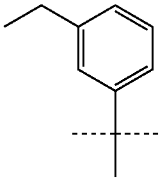 | 84.54 | $^1H$ NMR (300 MHz, DMSO-$d_6$) δ 8.46-8.36 (m, 1H), 7.84-7.71 (m, 1H), 7.46-7.40 (m, 2H), 5.11-4.98 (m, 1H), 4.96-4.84 (m, 1H), 4.61-4.27 (m, 2H), 4.17-3.79 (m, 4H), 3.64-3.37 (m, 2H), 2.70 (q, J = 7.6 Hz, 2H), 2.47-1.75 (m, 7H), 1.38-1.15 (m, 6H), 1.14-0.71 (m, 2H), 0.67-0.36 (m, 2H), 0.34--0.06 (m, 4H). LCMS Calculated for $C_{32}H_{38}N_6O_4$: 570.3; Observed (Method-B): 571.3 $[M + H]^+$, 97.46% at RT 1.886 min. |
| I-419 | 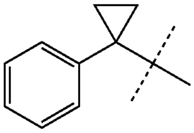 | 14.3 | LCMS Calculated for $C_{33}H_{38}N_6O_4$: 582.3; Observed (Method-A): 583.3 $[M + H]^+$, 100% at RT 1.307 min. |
| I-546 | 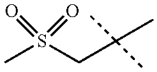 | 28.6 | LCMS Calculated for $C_{26}H_{34}N_6O_6S$: 558.23; Observed (Method-A): 559.23 $[M + H]^+$, 99.85% at RT 1.014 min. |
| I-397 | 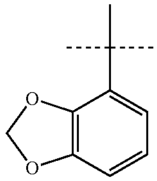 | 15.34 | LCMS Calculated for $C_{31}H_{34}N_6O_6$: 586.25; Observed (Method-A): 587.25 $[M + H]^+$, 100% at RT 1.248 min. |
| I-547 | 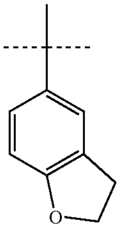 | 23.33 | LCMS Calculated for $C_{32}H_{36}N_6O_5$: 584.27; Observed (Method-A): 585.27 $[M + H]^+$, 99.79% at RT 1.196 min. |

-continued

| Compound Number | R group | % yield | Characterization data |
|---|---|---|---|
| I-505 | 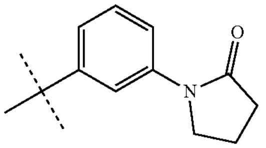 | 21.84 | LCMS Calculated for $C_{34}H_{39}N_7O_5$: 625.3; Observed (Method-A): 626.3 $[M + H]^+$, 100% at RT 1.120 min. |
| I-506 | 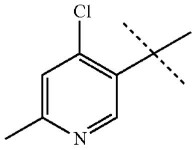 | 80.61 | LCMS Calculated for $C_{30}H_{34}ClN_7O_4$: 591.24; Observed (Method-D): 592.24 $[M + H]^+$, 99.77% at RT 2.668 min. |
| I-514 | 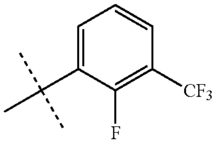 | 76.63 | LCMS Calculated for $C_{31}H_{32}F_4N_6O_4$: 628.24; Observed (Method-A): 629.24 $[M + H]^+$, 100% at RT 1.366 min. |
| I-548 | 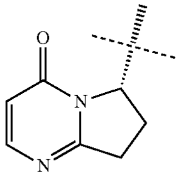 | 42.18 | LCMS Calculated for $C_{31}H_{36}N_8O_5$: 600.28; Observed (Method-A): 601.28 $[M + H]^+$, 100% at RT 0.986 min. |
| I-662 | 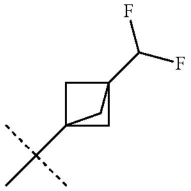 | 75.47 | LCMS Calculated for $C_{30}H_{36}F_2N_6O_4$: 582.28; Observed (Method-A): 583.28 $[M + H]^+$, 99.93% at RT 1.226 min. |
| I-625 | 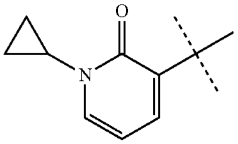 | 67.0 | LCMS Calculated for $C_{32}H_{37}N_7O_5$: 599.29; Observed (Method-B): 600.29 $[M + H]^+$, 98.79% at RT 1.51 min. |

The compound in the table below was prepared according to I-49.

| | |
|---|---|
| 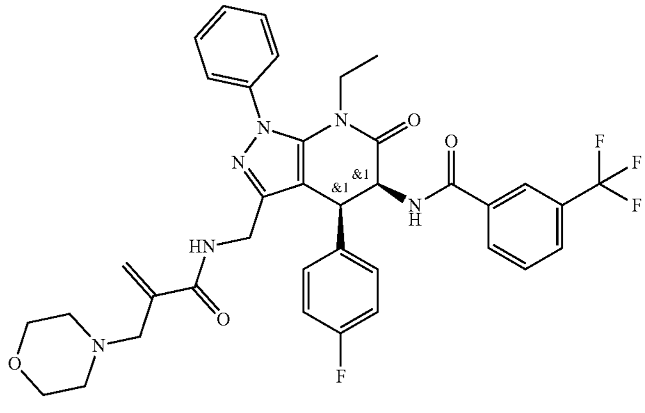 [SMILES: C=C(CN1CCOCC1)C(=O)NCc1nn(-c2ccccc2)c2c1[C@H](c1ccc(F)cc1)[C@H](NC(=O)c1cccc(C(F)(F)F)c1)C(=O)N2CC]<br>I-67 | $^1H$ NMR (400 MHz, DMSO-$d_6$) δ 9.16-9.11 (m, 1H), 8.54 (d, J = 7.5 Hz, 1H), 8.17-8.10 (m, 2H), 7.92 (d, J = 7.8 Hz, 1H), 7.75-7.65 (m, 3H), 7.63-7.51 (m, 3H), 7.08 (t, J = 8.7 Hz, 2H), 6.96-6.92 (m, 2H), 5.77-5.73 (m, 1H), 5.51 (t, J = 7.3 Hz, 1H), 5.32 (s, 1H), 4.56 (d, J = 7.2 Hz, 1H), 4.38-4.16 (m, 2H), 4.01-3.76 (m, 1H), 3.68 (s, 1H), 3.43-3.37 (m, 4H), 3.10-2.85 (m, 3H), 2.23-2.19 (m, 3H), 0.91 (t, J = 7.1 Hz, 3H). LCMS Calculated for $C_{37}H_{36}F_4N_6O_4$: 704.27; Observed (Method-AV): 705.4 [M + H]$^+$, 99.0% at RT 1.863 min. |

Example 39: Synthesis of Probe Compound

Synthesis of 2-((1E, 3E)-5-((E)-1-(6-(4-(3-(3-((4R, 5S)-7-ethyl-4-(3-(2-(morpholinomethyl)acrylamido)phenyl)-6-oxo-5-(3-(trifluoromethyl)benzamido)-4,5,6,7-tetrahydro-1H-pyrazolo[3, 4-b]pyridin-1yl)phenoxy)propyl)piperazin-1-yl)-6-oxohexyl)-3, 3-dimethyl-5-sulfindolin-2-ylidene)penta-1,3-dien-1-yl)-1,3,3-trimethyk-3H-indol-1-ium-5-sulfonate (P-1)

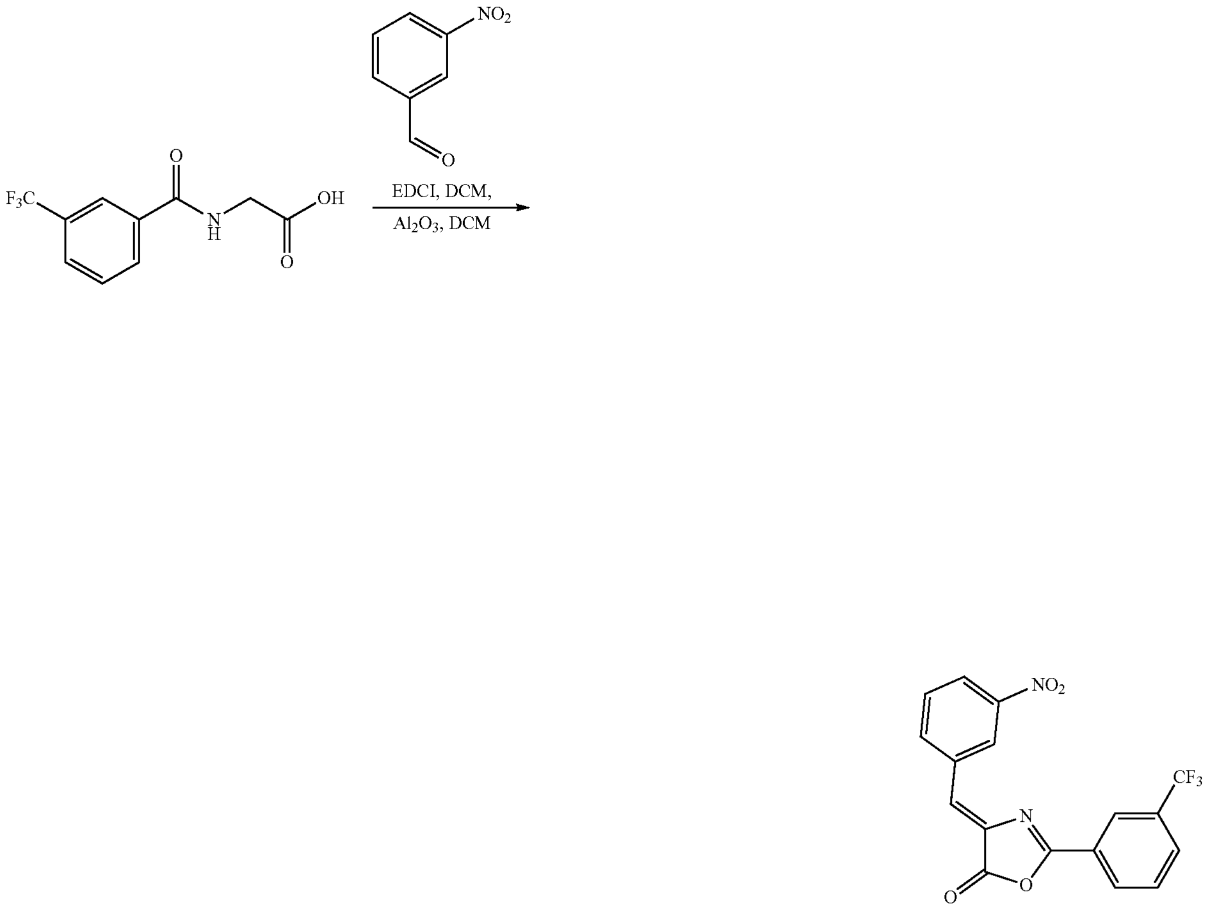

Int•A

-continued
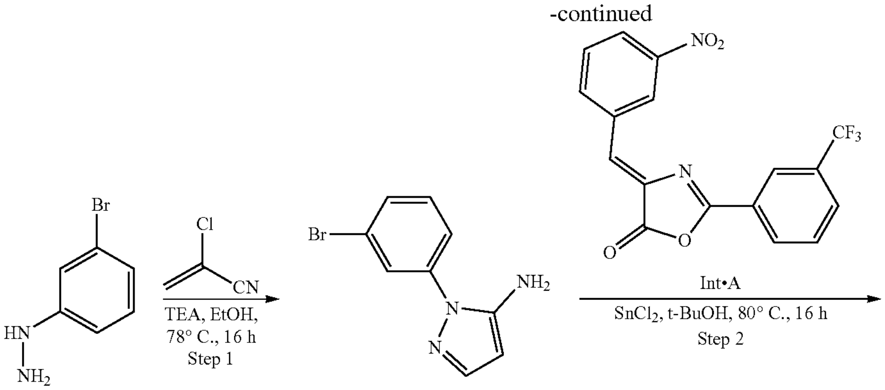
59
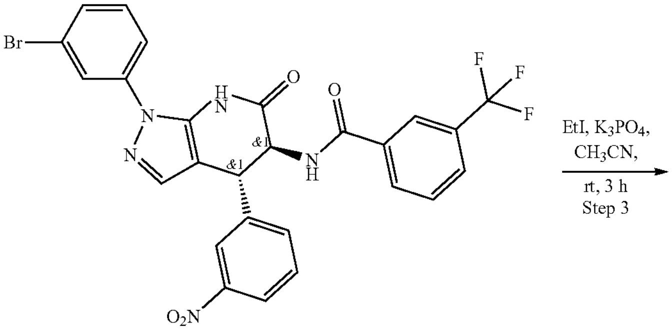
60
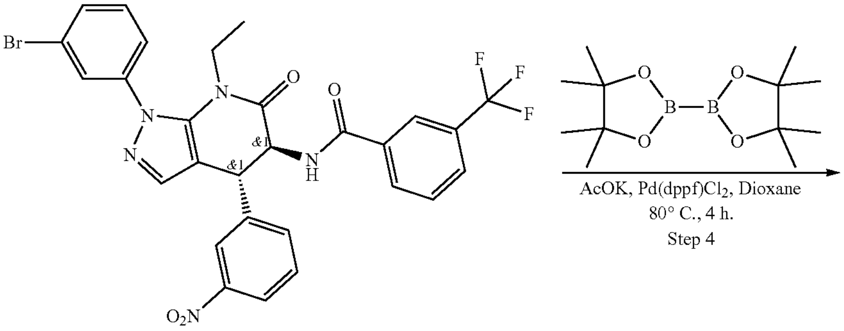
61
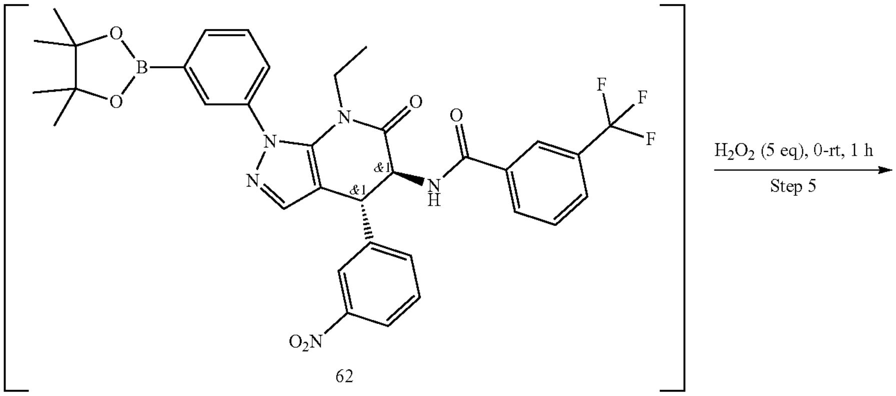
62

-continued
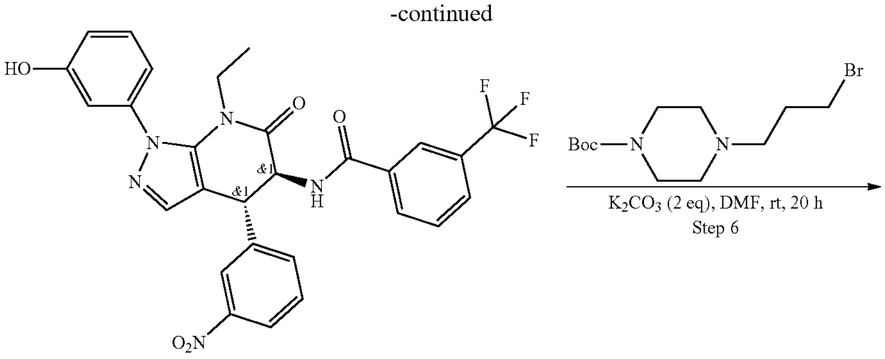
63
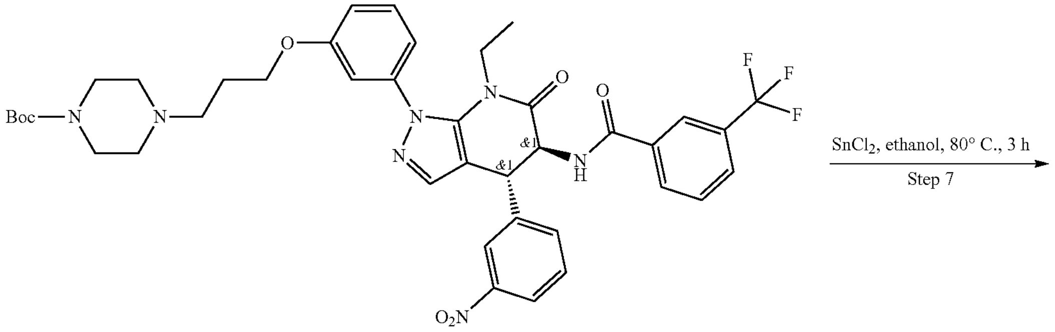
64
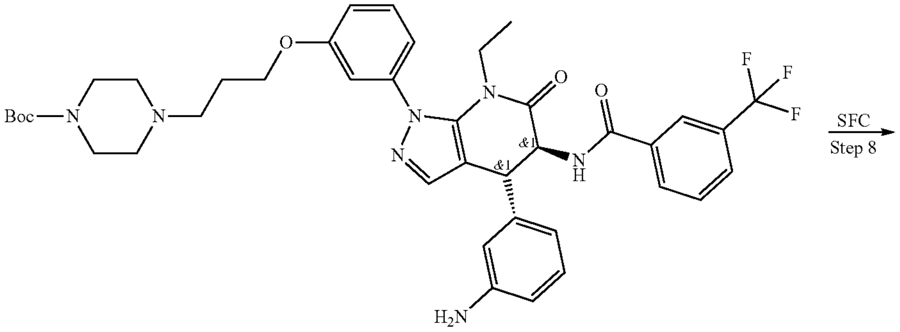
65
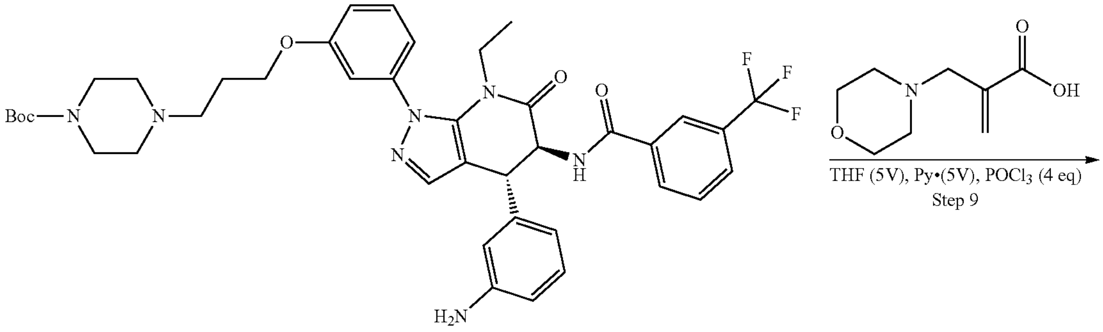
66

-continued
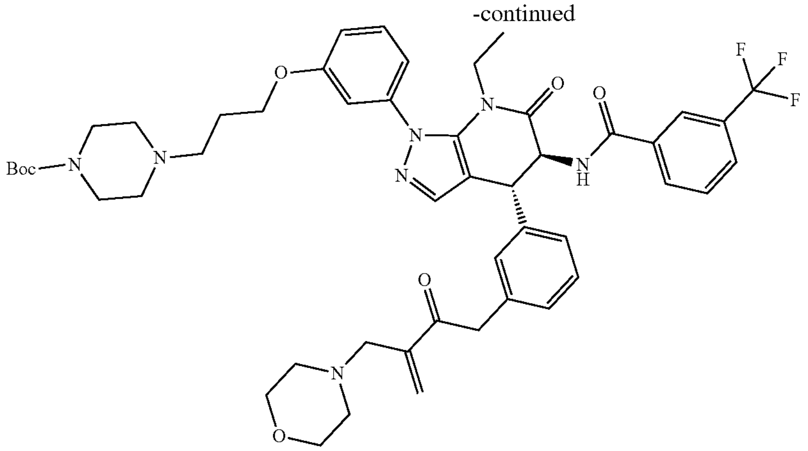
67
TMSI, 2, 6-dimethylpyridine
Step 10
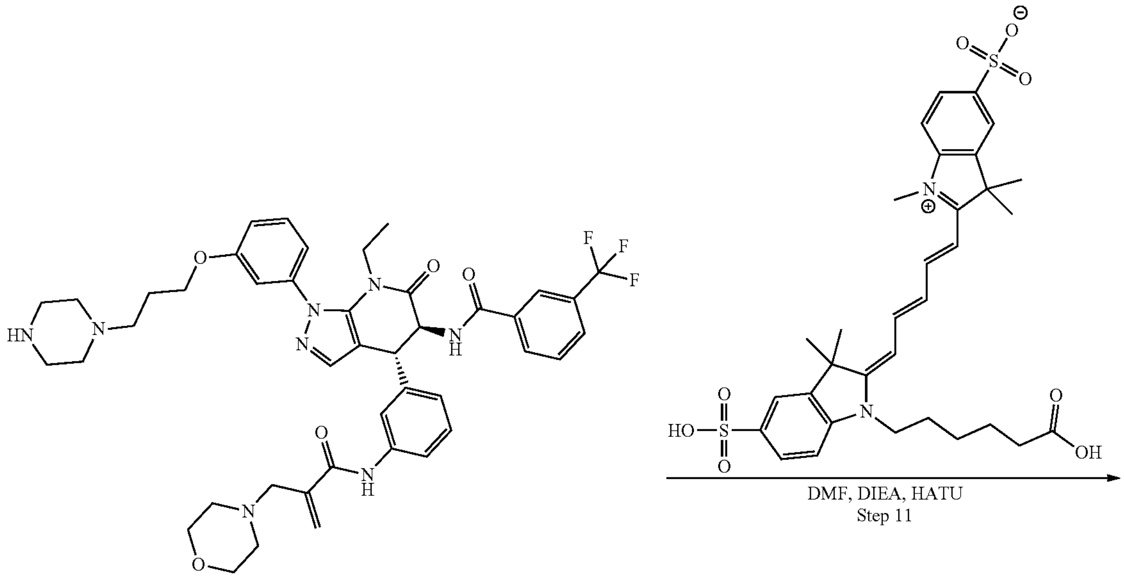
68
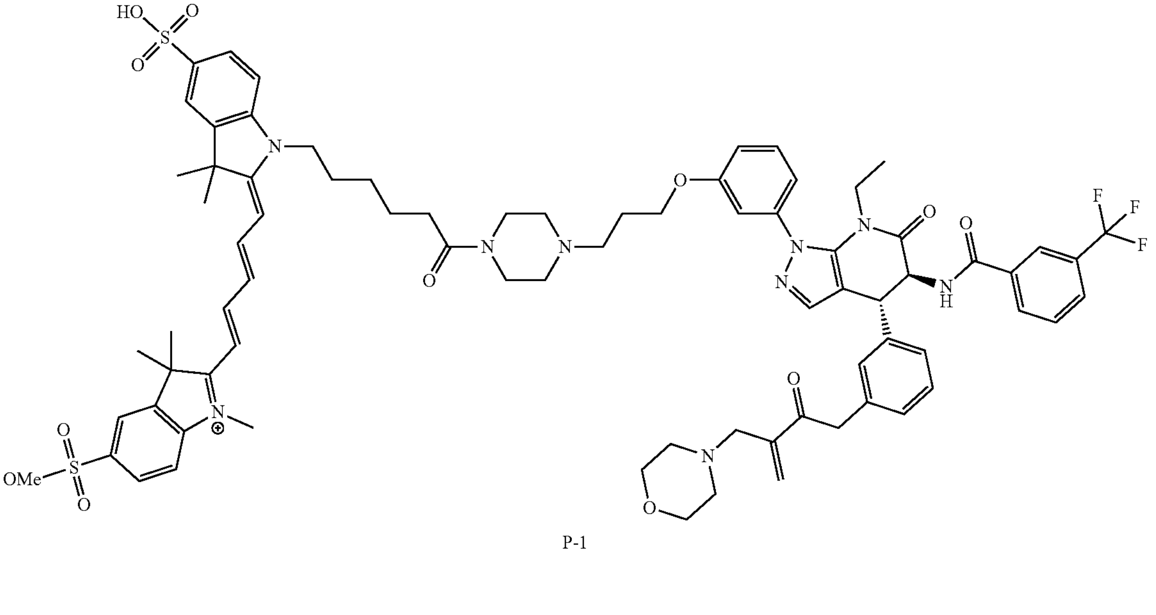
P-1

(4Z)-4-[(3-nitrophenyl)methylidene]-2-[3-(trifluoromethyl)phenyl]-1,3-oxazol-5-one (Int.A)

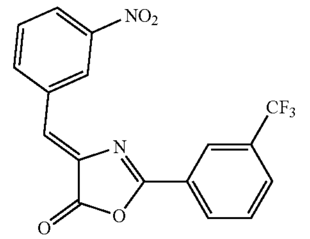

A solution of {[3-(trifluoromethyl)phenyl]formamido}acetic acid (200 g, 809 mmol, 1.00 equiv) in DCM (2000 mL) was treated with EDCI (138 g, 890 mmol, 1.10 equiv) at 0° C. for 40 min under nitrogen atmosphere. The resulting mixture was washed with $H_2O$ (3×1000 mL), dried over anhydrous $Na_2SO_4$. The filtration was treated with 3-nitrobenzaldehyde (122 g, 809 mmol, 1.00 equiv) and $Al_2O_3$ (825.01 g, 8091.500 mmol, 10 equiv) at 0° C. for 40 min under nitrogen atmosphere followed. The resulting mixture was filtered, the filter cake was washed with DCM (5×500 mL). The filtrate was concentrated under reduced pressure. The residue was treated with DCM:PE=1:5 (500 mL) for 1 h. The precipitated solids were collected by filtration and washed with DCM: Petroleum ether=1:5 (3×500 mL). This resulted in (4Z)-4-[(3-nitrophenyl)methylidene]-2-[3-(trifluoromethyl)phenyl]-1,3-oxazol-5-one (190 g, 64.8% yield, 90% purity) as a yellow solid.

$^1$H NMR (300 MHZ, DMSO-$d_6$) δ 9.22 (t, J=2.0 Hz, 1H), 8.70 (d, J=7.8 Hz, 1H), 8.42 (d, J=7.9 Hz, 1H), 8.33 (ddd, J=8.1, 2.4, 1.0 Hz, 2H), 8.14 (d, J=7.9 Hz, 1H), 7.93 (t, J=7.9 Hz, 1H), 7.84 (t, J=8.0 Hz, 1H), 7.62 (s, 1H).

LCMS Calculated for $C_{17}H_9F_3N_2O_4$: 362.05; Observed: 363.1 $[M+H]^+$ 1-(3-bromophenyl)-1H-pyrazol-5-amine (59)

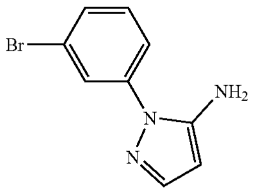

A solution of (3-bromophenyl) hydrazine (50.0 g, 267 mmol, 1.00 equiv) in EtOH (500 mL) was treated with 2-propenenitrile, 2-chloro-(23.4 g, 267 mmol, 1.00 equiv) at room temperature for 1 h. The resulting mixture was stirred at 70° C. for 16 h under nitrogen atmosphere. The resulting mixture was concentrated under reduced pressure. The residue was purified by silica gel column chromatography, eluted with petroleum ether/ethyl acetate (4:1) to afford 2-(3-bromophenyl) pyrazol-3-amine (30 g, 47.14% yield, 90% purity) as a red solid.

$^1$H NMR (400 MHZ, DMSO-$d_6$) δ 8.21 (d, J=2.6 Hz, 1H), 7.87 (t, J=2.0 Hz, 1H), 7.66 (ddd, J=8.1, 2.2, 1.1 Hz, 1H), 7.34 (t, J=8.0 Hz, 1H), 7.30-7.24 (m, 1H), 5.78 (d, J=2.6 Hz, 1H).

LCMS Calculated for $C_9H_8BrN_3$: 236.99; Observed: 238.0, 240.0 $[M+H]^+$.

rac-N-((4R,5S)-1-(3-bromophenyl)-4-(3-nitrophenyl)-6-oxo-4,5,6,7-tetrahydro-1H-pyrazolo[3,4-b]pyridin-5-yl)-3-(trifluoromethyl)benzamide (60)

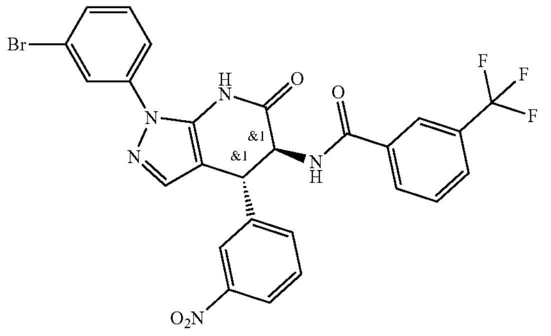

A solution of 2-(3-bromophenyl) pyrazol-3-amine (13.0 g, 54.6 mmol, 1.00 equiv) in t-BuOH (130 mL) was treated with $SnCl_2$ (1.04 g, 5.46 mmol, 0.10 equiv) at 80° C. for 16 h under nitrogen atmosphere. The resulting mixture was concentrated under reduced pressure. The residue was purified by silica gel column chromatography, eluted with petroleum ether/ethyl acetate (1:1) to afford rac-N-((4R,5S)-1-(3-bromophenyl)-4-(3-nitrophenyl)-6-oxo-4,5,6,7-tetrahydro-1H-pyrazolo[3,4-b]pyridin-5-yl)-3-(trifluoromethyl) benzamide (12 g, 47.14% yield, 90% purity) as a yellow solid.

$^1$H NMR (400 MHZ, DMSO-$d_6$) δ 11.19 (s, 1H), 9.04 (d, J=9.0 Hz, 1H), 8.33-8.29 (m, 1H), 8.15 (ddd, J=8.2, 2.4, 1.0 Hz, 1H), 8.03 (d, J=7.3 Hz, 2H), 7.94-7.86 (m, 2H), 7.84 (t, J=1.9 Hz, 1H), 7.72 (t, J=7.9 Hz, 1H), 7.69-7.61 (m, 3H), 7.52 (t, J=8.0 Hz, 1H), 7.16 (s, 1H), 5.15 (dd, J=12.8, 8.9 Hz, 1H), 4.63 (d, J=12.8 Hz, 1H).

LCMS Calculated for $C_{26}H_{17}BrF_3N_5O_4$: 599.04; Observed: 600.1, 602.1 $[M+H]^+$.

rac-N-((4R,5S)-1-(3-bromophenyl)-7-ethyl-4-(3-nitrophenyl)-6-oxo-4,5,6,7-tetrahydro-1H-pyrazolo[3,4-b]pyridin-5-yl)-3-(trifluoromethyl)benzamide (61)

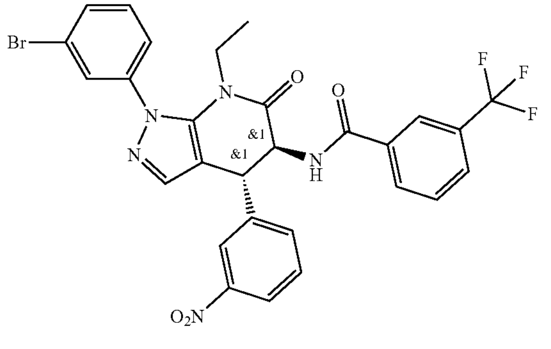

To a stirred mixture of rac-N-((4R,5S)-1-(3-bromophenyl)-4-(3-nitrophenyl)-6-oxo-4,5,6,7-tetrahydro-1H-pyrazolo[3,4-b]pyridin-5-yl)-3-(trifluoromethyl)benzamide (10.0 g, 16.7 mmol, 1.00 equiv) and iodoethane (3.12 g, 20.0 mmol, 1.20 equiv) in acetonitrile (100 mL) were added $K_3PO_4$ (10.6 g, 49.9 mmol, 3.00 equiv) at room temperature. The resulting mixture was stirred at room temperature for additional 3 h, then filtered. The filter cake was washed with acetonitrile (2×10 mL). The filtrate was concentrated under reduced pressure. The mixture was purified by silica gel column chromatography, eluted with petroleum ether/ethyl acetate (2:1) to afford rac-N-((4R,5S)-1-(3-bromophenyl)-7-ethyl-4-(3-nitrophenyl)-6-oxo-4,5,6,7-tetrahydro-1H-pyrazolo[3,4-b]pyridin-5-yl)-3-(trifluoromethyl)benzamide (7 g, 66.8% yield, 95% purity) as a yellow solid.

$^1$H NMR (400 MHZ, DMSO-$d_6$) δ 9.05 (d, J=9.1 Hz, 1H), 8.35-8.29 (m, 1H), 8.15 (ddd, J=8.2, 2.3, 1.0 Hz, 1H), 8.05-7.97 (m, 3H), 7.89 (t, J=7.7 Hz, 2H), 7.78-7.62 (m, 4H), 7.57 (t, J=8.0 Hz, 1H), 7.18 (s, 1H), 5.46-5.34 (m, 1H), 4.58 (d, J=12.9 Hz, 1H), 3.84 (dq, J=14.2, 7.1 Hz, 1H), 3.12 (dq, J=13.8, 6.8 Hz, 1H), 0.89 (t, J=7.0 Hz, 3H).

LCMS Calculated for $C_{28}H_{21}BrF_3N_5O_4$: 627.07; Observed: 628.1, 630.1 $[M+H]^+$.

rac-N-((4R,5S)-7-ethyl-1-(3-hydroxyphenyl)-4-(3-nitrophenyl)-6-oxo-4,5,6,7-tetrahydro-1H-pyrazolo[3,4-b]pyridin-5-yl)-3-(trifluoromethyl)benzamide (63)

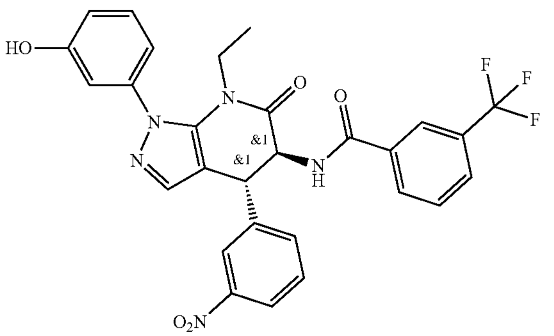

To a stirred solution of rac-N-((4R,5S)-1-(3-bromophenyl)-7-ethyl-4-(3-nitrophenyl)-6-oxo-4,5,6,7-tetrahydro-1H-pyrazolo[3,4-b]pyridin-5-yl)-3-(trifluoromethyl)benzamide (7.00 g, 11.1 mmol, 1.00 equiv) and bis(pinacolato) diboron (2.83 g, 11.1 mmol, 1.00 equiv) in 1,4-dioxane (70 mL) were added AcOK (3.28 g, 33.4 mmol, 3.00 equiv) and $Pd(dppf)Cl_2$ (0.82 g, 1.11 mmol, 0.1 equiv) at room temperature under nitrogen atmosphere. The resulting mixture was stirred at 80° C. for additional 4 h. The mixture was allowed to cool down to room temperature.

To the above reaction liquid added $H_2O_2$ (2 mL) dropwise at 0° C. The resulting mixture was stirred at room temperature for 1 h. The reaction was quenched by the addition of ice water (100 mL) at room temperature. The reaction added 20 mL $Na_2S_2O_3$ (aq.). The resulting mixture was extracted with EtOAc (2×100 mL). The combined organic layers were washed with saturated brine (2×100 mL), dried over anhydrous $Na_2SO_4$. The mixture was purified by reversed-phase flash chromatography with the following conditions: column, C18 silica gel; mobile phase, acetonitrile in water (0.05% $NH_3 \cdot H_2O$), 40% to 80% gradient in 30 min; detector, UV 254 nm. This resulted in rac-N-((4R,5S)-7-ethyl-1-(3-hydroxyphenyl)-4-(3-nitrophenyl)-6-oxo-4,5,6,7-tetrahydro-1H-pyrazolo[3,4-b]pyridin-5-yl)-3-(trifluoromethyl) benzamide (5 g, 95% purity) as a yellow solid.

LCMS Calculated for $C_{28}H_{22}F_3N_5O_5$: 565.16; Observed: 564.1 $[M-H]^-$.

rac-tert-butyl 4-(3-(3-((4R,5S)-7-ethyl-4-(3-nitrophenyl)-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (64)

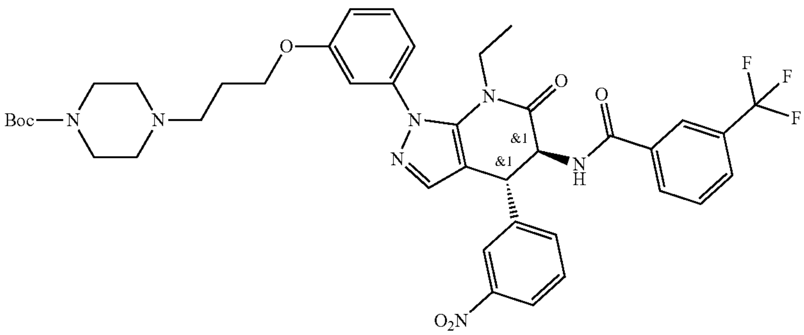

To a stirred mixture of rac-N-((4R,5S)-7-ethyl-1-(3-hydroxyphenyl)-4-(3-nitrophenyl)-6-oxo-4,5,6,7-tetrahydro-1H-pyrazolo[3,4-b]pyridin-5-yl)-3-(trifluoromethyl)benzamide (5.00 g, 8.84 mmol, 1.00 equiv) and tert-butyl 4-(3-bromopropyl)piperazine-1-carboxylate (3.26 g, 10.6 mmol, 1.20 equiv) in DMF (50 mL) was added $K_2CO_3$ (2.44 g, 17.7 mmol, 2.00 equiv) at room temperature. The resulting mixture was stirred at room temperature for 20 h. The resulting mixture was filtered, the filter cake was washed with EtOAc (2×50 mL). The filtrate was concentrated under reduced pressure. The solution was purified by reversed-phase flash chromatography with the following conditions: column, C18 silica gel; mobile phase, acetonitrile in water (0.05% $NH_3 \cdot H_2O$), 45% to 75% gradient in 25 min; detector, UV 254 nm. This resulted in rac-tert-butyl 4-(3-(3-((4R,5S)-7-ethyl-4-(3-nitrophenyl)-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (3.7 g, 52.8% yield, 95% purity) as a yellow solid.

LCMS Calculated for $C_{40}H_{44}F_3N_7O_7$: 791.33; Observed: 792.4 $[M+H]^+$ rac-tert-butyl 4-(3-(3-((4R,5S)-4-(3-aminophenyl)-7-ethyl-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (65)

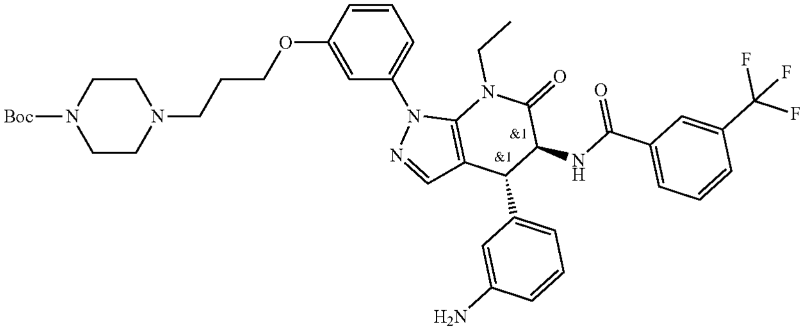

To a stirred mixture of rac-tert-butyl 4-(3-(3-((4R,5S)-7-ethyl-4-(3-nitrophenyl)-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (3.70 g, 4.67 mmol, 1.00 equiv) in EtOH (37 mL) were added $SnCl_2$ (4.43 g, 23.4 mmol, 5.00 equiv) at room temperature. The resulting mixture was stirred at 80° C. for 3 h. The resulting mixture was filtered and then washed with EtOH (2×5 mL). The filtrate was concentrated under reduced pressure. The residue was purified by reversed-phase flash chromatography with the following conditions: column, C18 silica gel; mobile phase, acetonitrile in water (0.05% $NH_3 \cdot H_2O$), 40% to 80% gradient in 30 min; detector, UV 254 nm. This resulted in rac-tert-butyl 4-(3-(3-((4R,5S)-4-(3-aminophenyl)-7-ethyl-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (1.5 g, 95% purity) as a yellow solid.

$^1H$ NMR (300 MHZ, DMSO-$d_6$) δ 8.96 (d, J=8.9 Hz, 1H), 8.06 (d, J=9.0 Hz, 2H), 7.91 (d, J=7.8 Hz, 1H), 7.72 (t, J=7.7 Hz, 1H), 7.47 (t, J=8.1 Hz, 1H), 7.27-7.15 (m, 2H), 7.09 (d, J=8.2 Hz, 1H), 7.04 (s, 1H), 6.95 (t, J=7.8 Hz, 1H), 6.59 (s, 1H), 6.54 (d, J=7.5 Hz, 1H), 6.43 (d, J=7.8 Hz, 1H), 5.09 (dd, J=12.7, 8.9 Hz, 1H), 5.04 (s, 2H), 4.21 (d, J=12.7 Hz, 1H), 4.09 (t, J=6.5 Hz, 2H), 3.89-3.74 (m, 1H), 3.32-3.25 (m, 4H), 3.20-3.05 (m, 1H), 2.45 (t, J=7.0 Hz, 2H), 2.33 (t, J=5.0 Hz, 4H), 1.90 (t, J=6.8 Hz, 2H), 1.39 (s, 9H), 0.85 (t, J=7.0 Hz, 3H).

LCMS Calculated for $C_{40}H_{46}F_3N_7O_5$: 761.35; Observed: 762.4 $[M+H]^+$.

The mixture rac-tert-butyl 4-(3-(3-((4R,5S)-4-(3-aminophenyl)-7-ethyl-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (1.5 g) was separated by Prep-Chiral SFC with the following conditions: Column: CHIRALPAKIG-U50*3.0 mm, 1.6 μm; Mobile Phase B: MeOH/DCM=1/1 (10 mM $NH_3$); Gradient: isocratic % B. This resulted in tert-butyl 4-(3-(3-((4R,5S)-4-(3-aminophenyl)-7-ethyl-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (650 mg, 45.6% yield, 98.5% purity) as a yellow solid.

LCMS Calculated for $C_{40}H_{46}F_3N_7O_5$: 761.35; Observed: 762.4 $[M+H]^+$.

Optical rotation value: a=−117.3 (C=0.1 g/100 mL in MeOH, T=25° C.).

Chiral-SFC (Method-A): 99.6% at RT 2.617 min tert-butyl 4-(3-(3-((4R,5S)-4-(3-aminophenyl)-7-ethyl-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (66)

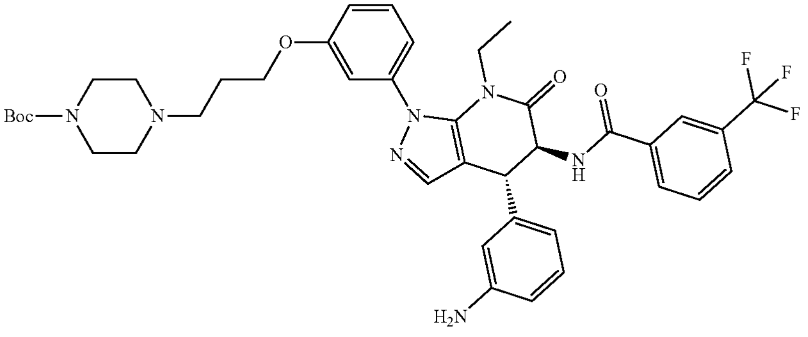

tert-butyl 4-(3-(3-((4R,5S)-7-ethyl-4-(3-(2-(morpholinomethyl)acrylamido)phenyl)-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (67)

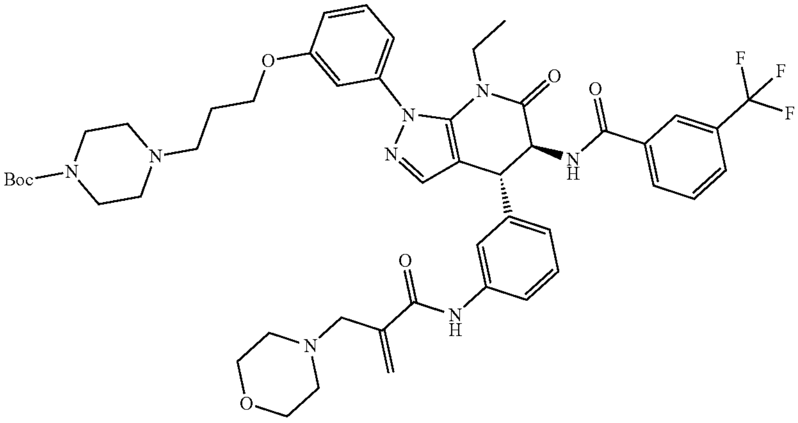

To a stirred mixture of 2-[(morpholin-4-yl)methyl]prop-2-enoic acid (119 mg, 0.697 mmol, 1.00 equiv) and tert-butyl 4-(3-(3-((4R,5S)-4-(3-aminophenyl)-7-ethyl-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (650 mg, 0.697 mmol, 1.00 equiv) in THF (6.5 mL) and pyridine (6.5 mL) were added phosphoroyl trichloride (267 mg, 1.74 mmol, 2.50 equiv) dropwise at 0° C. The resulting mixture was stirred at room temperature for 1 h. The reaction was quenched with water/ice (0.5 mL) at 0° C. The mixture was purified by reversed-phase flash chromatography with the following conditions: column, C18 silica gel; mobile phase, acetonitrile in water (0.05% $NH_3 \cdot H_2O$), 50% to 75% gradient in 25 min; detector, UV 254 nm. This resulted in tert-butyl 4-(3-(3-((4R,5S)-7-ethyl-4-(3-(2-(morpholinomethyl)acrylamido)phenyl)-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (170 mg, 26.6% yield, 95.0% purity) as a yellow solid.

LCMS Calculated for $C_{48}H_{57}F_3N_8O_7$: 914.43; Observed: 915.6 $[M+H]^+$.

N-((4R,5S)-7-ethyl-4-(3-(2-(morpholinomethyl)acrylamido)phenyl)-6-oxo-1-(3-(3-(piperazin-1-yl)propoxy)phenyl)-4,5,6,7-tetrahydro-1H-pyrazolo[3,4-b]pyridin-5-yl)-3-(trifluoromethyl)benzamide (68)

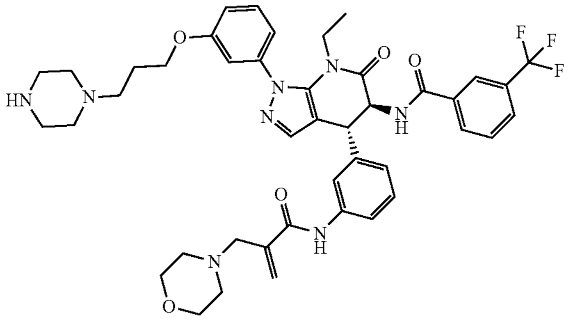

To a stirred mixture of tert-butyl 4-(3-(3-((4R,5S)-7-ethyl-4-(3-(2-(morpholinomethyl)acrylamido)phenyl)-6-oxo-5-(3-(trifluoromethyl)benzamido)-4,5,6,7-tetrahydro-1H-pyrazolo[3,4-b]pyridin-1-yl)phenoxy)propyl)piperazine-1-carboxylate (170 mg, 0.186 mmol, 1.00 equiv) in DCM (2.5 mL) were added 2,6-dimethylpyridine (79.6 mg, 0.744 mmol, 4.00 equiv) at 0° C. After 10 min, to the above mixture was added trimethylsulfanium iodide (114 mg, 0.558 mmol, 3.00 equiv) dropwise at 0° C. The resulting mixture was stirred at 0° C. for 1 h. After completion of reaction, the mixture reaction was concentrated under pressure to give N-((4R,5S)-7-ethyl-4-(3-(2-(morpholinomethyl)acrylamido)phenyl)-6-oxo-1-(3-(3-(piperazin-1-yl)propoxy)phenyl)-4,5,6,7-tetrahydro-1H-pyrazolo[3,4-b]pyridin-5-yl)-3-(trifluoromethyl)benzamide (350 mg, crude) which was used for next step directly.

LCMS Calculated for $C_{43}H_{49}F_3N_8O_5$: 814.38; Observed: 815.4 $[M+H]^+$.

2-((1E,3E)-5-((E)-1-(6-(4-(3-(3-((4R,5S)-7-ethyl-4-(3-(2-(morpholinomethyl)acrylamido)phenyl)-6-oxo-5-(3-(trifluoromethyl)benzamido)-4,5,6,7-tetrahydro-1H-pyrazolo[3,4-b]pyridin-1-yl)phenoxy)propyl)piperazin-1-yl)-6-oxohexyl)-3,3-dimethyl-5-sulfoindolin-2-ylidene)penta-1,3-dien-1-yl)-1,3,3-trimethyl-3H-indol-1-ium-5-sulfonate (P-1)

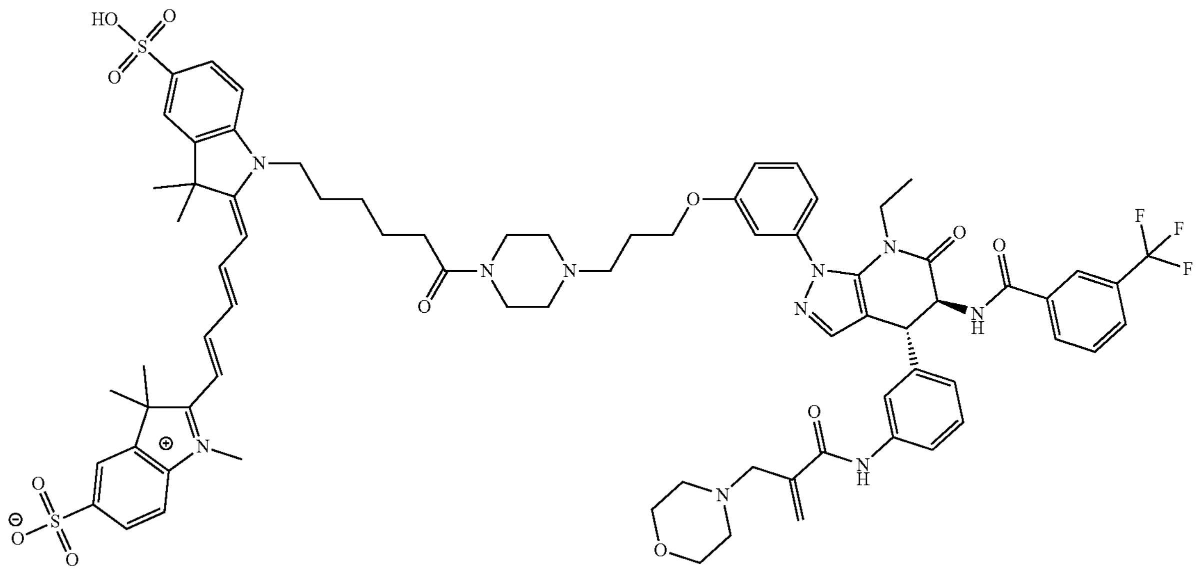

To a stirred mixture of sodium 1-(5-carboxypentyl)-3,3-dimethyl-2-[(1E,3E)-5-[(2E)-1,3,3-trimethyl-5-sulfo-2,3-dihydro-1H-indol-2-ylidene]penta-1,3-dien-(1-yl]-3H-indol-1-ium-5-sulfonate (173 mg, 0.261 mmol, 1.00 equiv) in DMF (5 mL) were added DIEA (101 mg, 0.783 mmol, 3.00 equiv) and HATU (119 mg, 0.313 mmol, 1.20 equiv) at 0° C. After 5 min, to the above mixture was added N-((4R, 5S)-7-ethyl-4-(3-(2-(morpholinomethyl)acrylamido)phenyl)-6-oxo-1-(3-(3-(piperazin-1-yl)propoxy)phenyl)-4,5,6,7-tetrahydro-1H-pyrazolo[3,4-b]pyridin-5-yl)-3-(trifluoromethyl)benzamide (380 mg, crude from last step) at room temperature. The resulting mixture was stirred at room temperature for additional 1 h. The reaction was quenched by the addition of water/ice (1 mL) at room temperature. The mixture was purified by reversed-phase flash chromatography with the following conditions: column: Ultimate—XB-C18 Column, 30*150 mm, 10 μm; Mobile Phase A: Water (0.05% $NH_3H_2O$), Mobile Phase B: ACN; Flow rate: 90 mL/min; Gradient: isocratic 5%-50% 12 min; Wave Length: 254 nm/220 nm; RT1(min): 11.5. This resulted in 2-((1E,3E)-5-((E)-1-(6-(4-(3-(3-((4R,5S)-7-ethyl-4-(3-(2-(morpholinomethyl)acrylamido)phenyl)-6-oxo-5-(3-(trifluoromethyl)benzamido)-4,5,6,7-tetrahydro-1H-pyrazolo[3,4-b]pyridin-1-yl)phenoxy)propyl)piperazin-1-yl)-6-oxohexyl)-3,3-dimethyl-5-sulfoindolin-2-ylidene)penta-1,3-dien-1-yl)-1,3,3-trimethyl-3H-indol-1-ium-5-sulfonate (109 mg, 29.0% yield, 97.4% purity) as a light blue solid.

$^1H$ NMR (400 MHZ, DMSO-$d_6$) δ 11.07 (s, 1H), 9.02 (d, J=9.0 Hz, 1H), 8.34 (t, J=13.1 Hz, 2H), 8.03 (d, J=4.0 Hz, 2H), 7.88 (d, J=7.8 Hz, 1H), 7.79 (d, J=1.5 Hz, 2H), 7.70-7.54 (m, 5H), 7.46-7.41 (m, 1H), 7.32-7.25 (m, 3H), 7.22-7.15 (m, 2H), 7.12 (d, J=7.8 Hz, 1H), 7.05 (d, J=9.6 Hz, 2H), 6.54 (t, J=12.3 Hz, 1H), 6.33-6.21 (m, 2H), 6.03 (d, J=1.9 Hz, 1H), 5.57 (s, 1H), 5.14 (dd, J=12.8, 9.0 Hz, 1H), 4.36 (d, J=12.8 Hz, 1H), 4.07 (t, J=6.7 Hz, 4H), 3.83 (dt, J=14.1, 7.0 Hz, 1H), 3.60 (t, J=4.7 Hz, 4H), 3.58-3.54 (m, 3H), 3.42-3.35 (m, 4H), 3.28-3.23 (m, 2H), 3.14-3.02 (m, 1H), 2.46-2.36 (m, 6H), 2.34-2.22 (m, 6H), 1.86 (q, J=7.6, 7.1 Hz, 2H), 1.75-1.63 (m, 14H), 1.50 (t, J=7.5 Hz, 2H), 1.38-1.27 (m, 2H), 0.93 (d, J=6.4 Hz, 1H), 0.83 (t, J=7.0 Hz, 3H).

LCMS Calculated for $C_{75}H_{85}F_3N_{10}O_{12}S_2$: 1438.57; Observed (Method A): 1438.1 $[M-H]^-$, 97.4% at RT 1.797 min.

Chiral-HPLC: 95.3% at RT 3.082 min.

Example 40: Assay to Measure the Off-Rate of Reversible Covalent Molecules

Description

A TR-FRET assay was performed to classify the compounds as an irreversible covalent binder, a reversible covalent binder or a reversible binder.

An assay to measure the off-rate of reversible covalent molecules was developed. A typical covalent compound is assumed to stay bound to a protein for at least the life of that protein in the cell. In reality, there is a range of how long a covalent compounds remains bound before a reverse reaction takes place. Thus, some covalent bonds can be labeled as reversible as their reverse reaction takes place in a measurable amount of time under physiological conditions. The assay capitalizes on the range of covalent binders by using a high affinity covalent binder as a probe to displace the more reversible binders in an adaptation of the jump dilution method.

In this version of the jump dilution method, the increase in covalent probe binding over time was measured through a TR-FRET reaction between the covalent probe and the biotinylated target protein.

Methods

Target Protein Preparation

The recombinant form of the DCN1 (DCUND1) protein PONY domain was produced using an *E. coli* expression system at Viva Biotech (China). The DCN1 protein was biotinylated (EZ sulfo-NHS-LC-biotin; Thermofisher) for labeling with streptavidin terbium (Tb) cryptate in the reaction. This biotinylated protein was used in two forms of the TR-FRET assay as described below.

TR-FRET with FAM Probe

This version of the TR-FRET assay was used to measure compound potency to the target, specifically to measure the potency of the Cy5 probe (P-1). A non-covalent DCN1 inhibitor (Zhou et al., 2017) labeled with carboxyfluorescein (FAM) was used as the FRET acceptor probe. Displacement of the covalent probe, and thus decrease in the FRET signal, was indicative of compound activity on the target protein. Buffer conditions were optimized to enhance compound and protein stability (200 mM NaCl, 25 mM Tris, 0.5 mM DTT, 0.05% Tween20, 5% DMSO, 5% PEG-3350, pH 7.5) and concentrations of protein (0.31 nM) and probe (100 nM labeled, 800 nM unlabeled) were optimized for detection of potent molecules. The TR-FRET ratio between Tb-DCN1 and the FAM-labeled probe was measured in a 384-well opti-plate (Perkin Elmer) using a plate reader (BMG) at 1, 5, and 24 hrs after treatment with compound. The ratio was normalized to the high (DCN1 and FAM-probe) and low (DCN1 and no probe) controls for a readout of % activity (=100*(x−low)/(high−low)).

TR-FRET with Cy5 Probe

This version of the TR-FRET assay was used to measure both the potency of the molecules to the target and the off-rate of the compounds from the target. All potency measurements in this assay condition were used to determine the concentrations used in the off-rate assay. A covalent probe labeled with Cy5 was used as the FRET acceptor. Similar conditions were used as for the TR-FRET with FAM probe. The only differences include, 0.625 nM protein, 2.5 nM probe, and detection timepoints at 0.5, 1, 2, 4, 24 hrs. Calculations were the same.

Off-Rate Measurement

The off-rate measurement is executed in two steps based on the jump dilution method. Step one, test compounds were incubated 1 hour at room temperature with Tb and 6 nM protein at a concentration 10-fold higher than the EC50 determined in the TR-FRET with Cy5 probe assay. Step two, the mixture in Step one was diluted into a new reaction buffer containing the Cy5 probe at a concentration of 150 nM>>its Kd (EC50 23.2 nM). The degree of dilution (20, 50, or 100-fold) was dependent on the EC50 of the test compound. The greatest dilution allowed within the constraints of the assay was chosen. These factors allow a competitive advantage for the covalent probe to replace the test compound when that compound releases from the target protein. The actual measure is the rate of increased TR-FRET signal as the covalent probe replaces the test compound over time. The TR-FRET signal is measured every 0.5 minutes up to 0.5 hours; every 5 minutes up to 2 hours; every 15 minutes up to 2 hours with a BMG Labtech plate reader (Optic module: LanthaScreen 337/665/620). The resulting time dependent curve of the TR-FRET signal is fit to the following equation:

$$Y=Y0+(\text{Plateau}-Y0)*(1-\exp(-K*x))$$

K is the rate constant (1/unit of time). The residence time is defined as the inverse of K, the rate constant. The half-life is calculated as ln(2)/K.

The structures of tool compounds 1 and 2 respectively are shown below.

TABLE 4

Assay

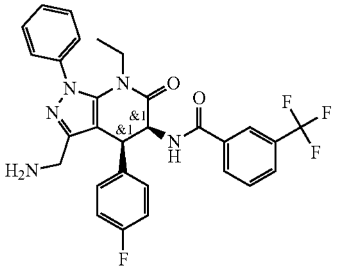

Tool compound 1

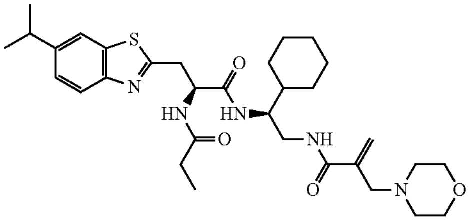

Tool compound 2

| Compound ID | Koff (min-1) | residence time (min) | half-life (min) | n | Category |
|---|---|---|---|---|---|
| Tool compound 1 | 0.344928571 | 3.32880461 | 2.30735153 | 7 | reversible |
| Tool compound 2 | ND | | | 7 | irreversible covalent |
| I-73 | ND | | | 4 | irreversible covalent |
| I-256 | 0.004774 | 219.4740553 | 152.1278227 | 3 | slow reversible covalent |
| I-348 | ND | | | 2 | slow reversible covalent |
| I-350 | 0.0015835 | 698.5365802 | 484.1886611 | 2 | slow reversible covalent |
| I-363 | ND | | | 2 | slow reversible covalent |
| I-369 | 0.025516667 | 39.37957455 | 27.29584107 | 3 | fast reversible covalent |
| I-370 | 0.01272 | 78.62728626 | 54.50028179 | 2 | fast reversible covalent |
| I-582 | ND | | | 2 | irreversible covalent |
| I-617 | 0.01509 | 66.28724649 | 45.94681801 | 2 | fast reversible covalent |
| I-379 | 0.012675 | 78.8998958 | 54.68924032 | 2 | reversible covalent |
| I-436 | 0.0143 | 76.67050555 | 53.14394476 | 2 | reversible covalent |
| I-380 | 0.0043415 | 437.761974 | 303.4334781 | 2 | reversible covalent |
| I-381 | 0.003371 | 296.6537527 | 205.6247123 | 2 | reversible covalent |
| I-430 | ND | | | 2 | slow reversible covalent |
| I-383 | ND | | | 2 | irreversible covalent |
| I-384 | 0.005523 | 183.6040915 | 127.2646583 | 2 | reversible covalent |
| I-660 | 0.003768 | 265.699393 | 184.1687851 | 2 | reversible covalent |
| I-560 | 0.0227 | 44.06005444 | 30.54010251 | 2 | fast reversible covalent |
| I-387 | 0.006934 | 144.268395 | 99.99923122 | 2 | reversible covalent |
| I-425 | 0.013155 | 76.01726178 | 52.69115068 | 2 | fast reversible covalent |
| I-552 | 0.004497667 | 224.4516017 | 155.5779949 | 3 | reversible covalent |

Example 41: Measurement of Kinact/KI in the DCN2 TR-FRET Assay

Methods

A TR-FRET Assay was performed to evaluate the ability of the compounds to bind DCN-2.

The time resolved-Forster's resonance energy transfer (TR-FRET) assay was designed following the protocol established in (Scott et al., Nat Chem Biol. 2017 August; 13 (8): 850-857). A recombinant form of the DCN2 (DCUND2) protein PONY domain was produced using an *E. coli* expression system at Viva Biotech China. The DCN2 protein was biotinylated (EZ sulfo-NHS-LC-biotin; Thermofisher) for labeling with 2.5 nM streptavidin terbium (Tb) cryptate in the reaction. The probe was changed to a non-covalent DCN1 inhibitor labeled with carboxyfluorescein (FAM; Zhou et al., *Nat Commun.* 2017; 8:1150). Buffer conditions were modified to enhance protein stability by replacing TritonX with 0.05% Tween20 and increasing NaCl to 200 mM. The compounds were screened against 0.31 nM DCN1 and 40 nM FAM-labeled probe in a 40 ul reaction volume. The TR-FRET ratio between Tb-DCN1 and the FAM-labeled probe was measured in a 384-well opti-plate (Perkin Elmer) using a plate reader (BMG) at after treatment with compound (final DMSO concentration of 0.1%). The ratio was normalized to the high (DCN1 and FAM-probe) and low (DCN1 and no probe) controls for a readout of % activity (=100*(x−low)/(high−low)).

The Kinact and KI measurements were taken to allow for continuous reads over 24 hrs. Plates were read every 5 min up to 1 hr, every 15 min up to 5 hr, and every hour up to 10 hours. Kinact and KI were calculated based on the following equations (Krippendorff B F, et al. Mechanism-based inhibition: deriving K(I) and k(inact) directly from time-dependent IC (50) values. J BiomolScreen. 2009; Mons E et al. A Comprehensive Guide for Assessing Covalent Inhibition in Enzymatic Assays Illustrated with Kinetic Simulations. CurrProtoc. 2022) where the KM of the probe against DCN2 is 21.62 nM. The Kinact and KI values could be estimated from the tight curves of the IC50 values over time.

$$IC_{50}(t) = K_I\left(1 + \frac{S}{K_M}\right)\cdot\left(\frac{2 - 2e^{-\eta_{IC_{50}}\cdot k_{inact}\cdot t}}{\eta_{IC_{50}}\cdot k_{inact}\cdot t} - 1\right) \text{ with}$$

$$\eta_{IC_{50}} = \frac{IC_{50}(t)}{K_I\left(1 + \frac{S}{K_M}\right) + IC_{50}(t)}.$$

The structure of C1 is shown below.

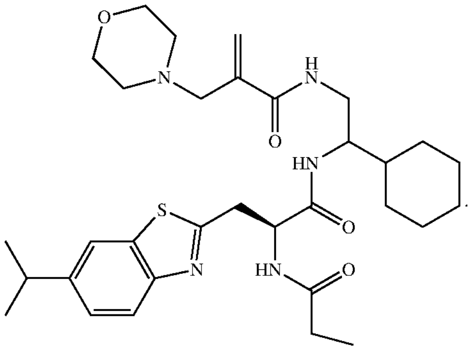 [SMILES: C=C(CN1CCOCC1)C(=O)NCC(NC(=O)[C@H](Cc1nc2ccc(C(C)C)cc2s1)NC(=O)CC)C1CCCCC1]

TABLE 5

| Measurement of Kinact/KI in the DCN2 TR-FRET Assay | | | |
|---|---|---|---|
| Compound ID | Kinact (min^-1) | KI (nM) | Kinact/KI (nM-1*min-1) |
| C1 | 0.3536 | 0.3546 | 0.9971 |
| I-73 | 0.2305 | 46.3808 | 0.0050 |
| I-256 | 0.4699 | 99.4300 | 0.0047 |
| I-350 | 0.2500 | 92.9011 | 0.0027 |
| I-363 | 0.2751 | 17.4033 | 0.0158 |
| I-369 | 0.0013 | 1.9990 | 0.0007 |
| I-370 | 0.0031 | 0.4878 | 0.0064 |
| I-372 | 0.1877 | 229.4000 | 0.0008 |
| I-377 | 0.2122 | 161.4000 | 0.0013 |
| I-383 | 0.2793 | 95.7500 | 0.0029 |
| I-387 | 0.4360 | 157.1000 | 0.0028 |
| I-425 | 0.0069 | 21.5900 | 0.0003 |
| I-552 | 0.3399 | 16.9833 | 0.0200 |

The invention claimed is:

1. A compound selected from one of the following:

I-3a

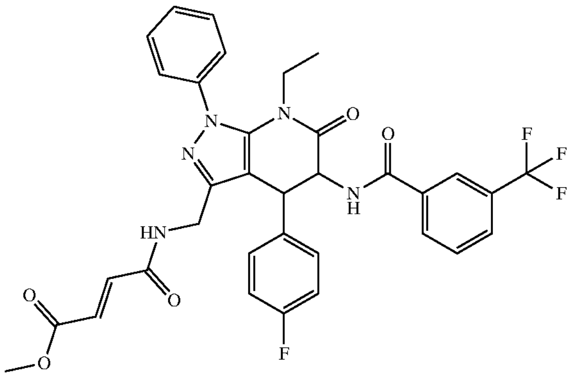

I-5a

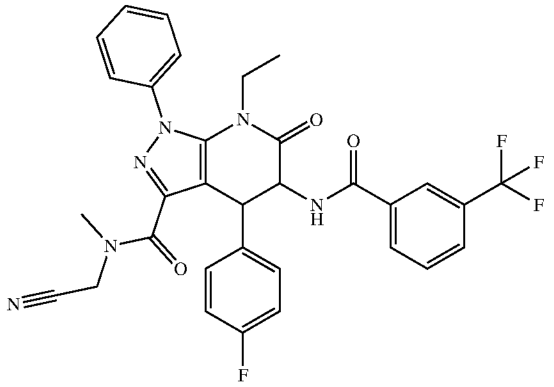

-continued
I-256a
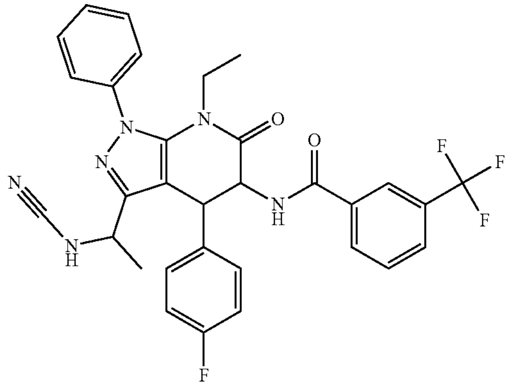
I-34a
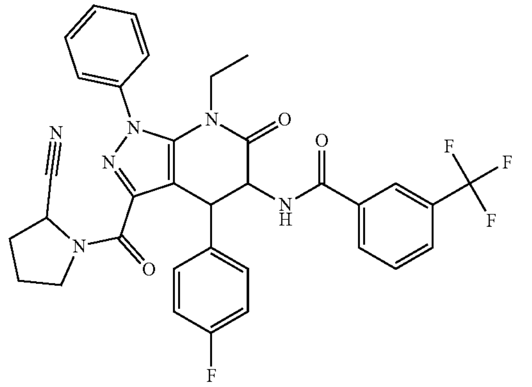
I-49a
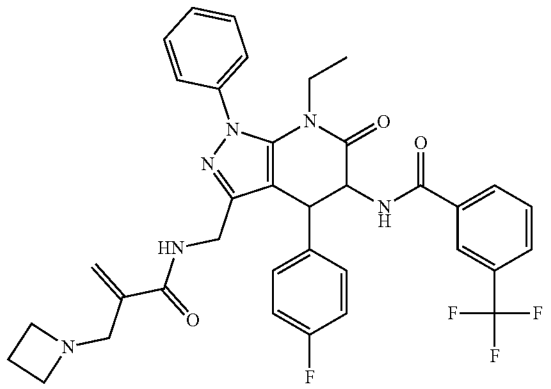
I-92a
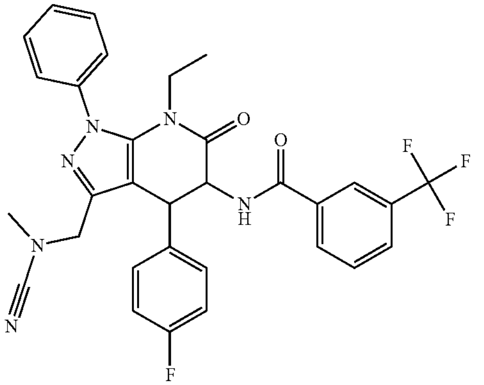
-continued
I-112a
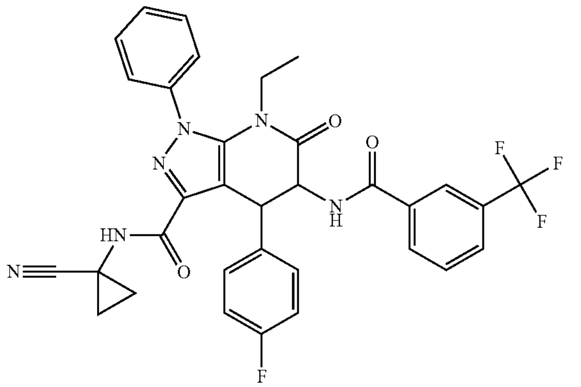
I-140a
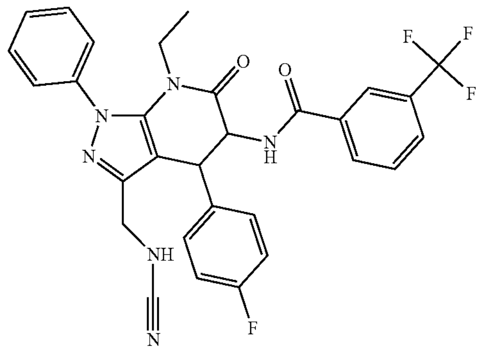
I-152a
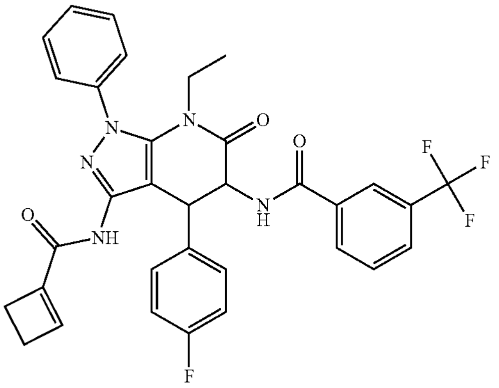
I-256b
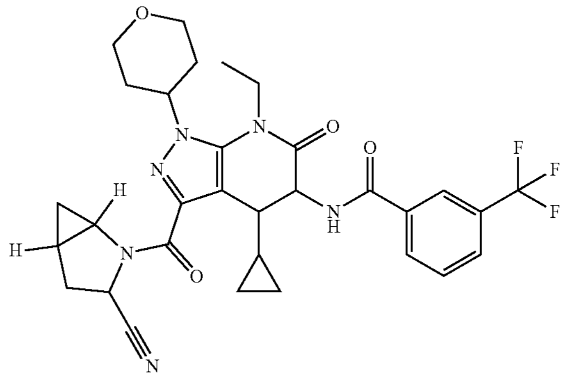

-continued
I-363a
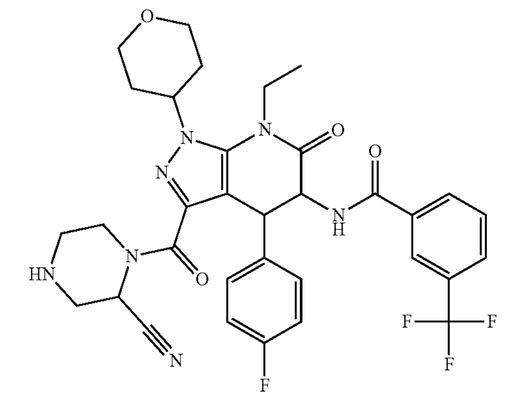
and
I-552a
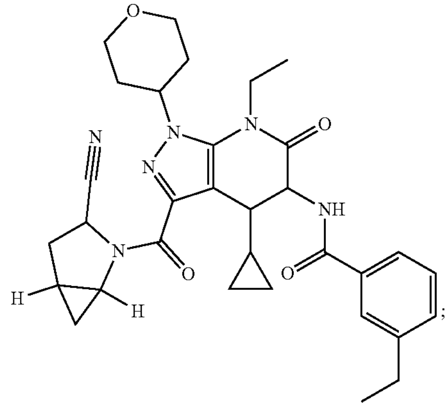
;
or a pharmaceutically acceptable salt thereof.
2. A compound selected from one of the following:
I-3
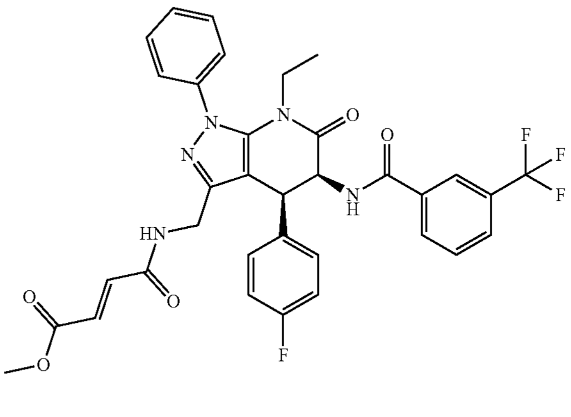
-continued
I-5
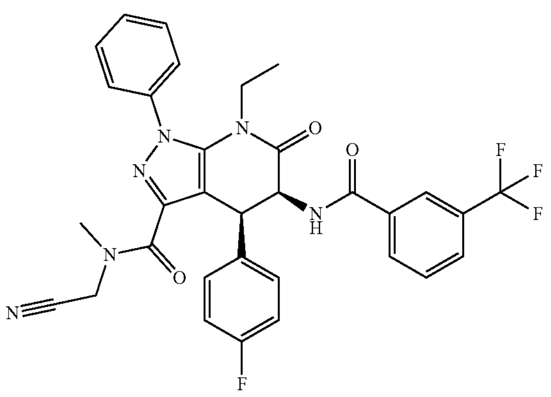
I-13
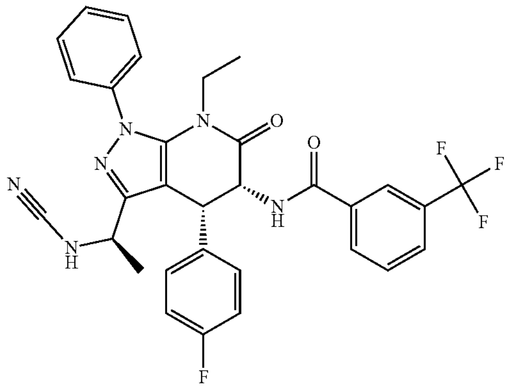
I-34
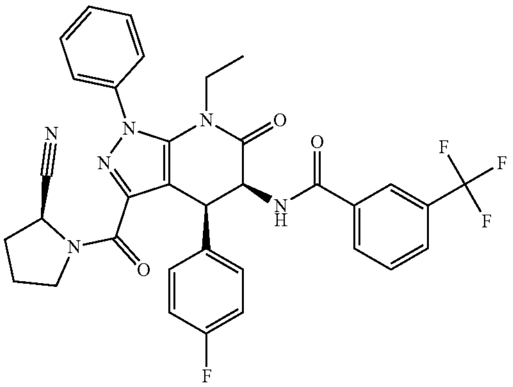
I-49
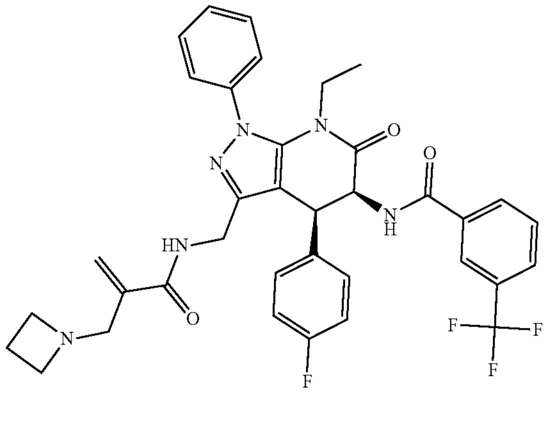

-continued
I-73
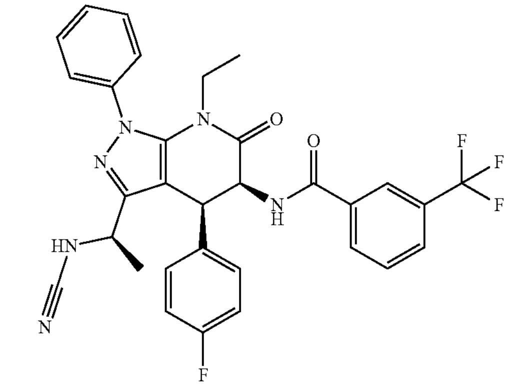
I-92
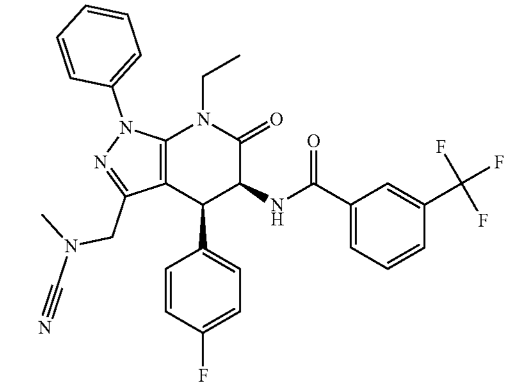
I-112
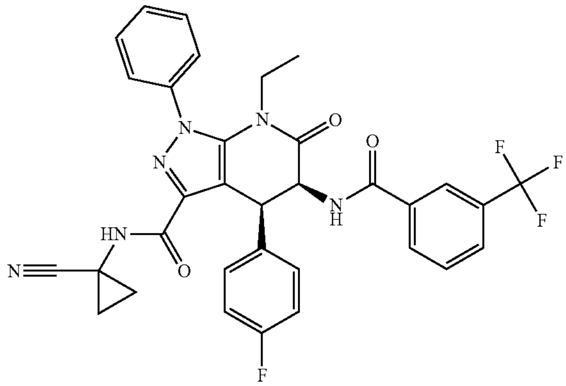
I-139
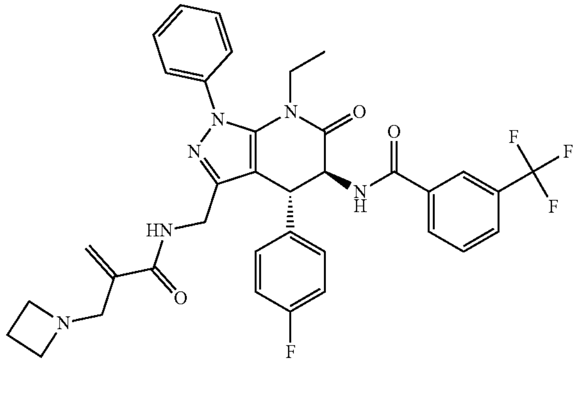
-continued
I-140
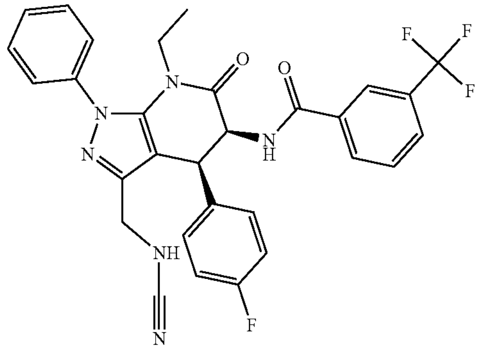
I-152
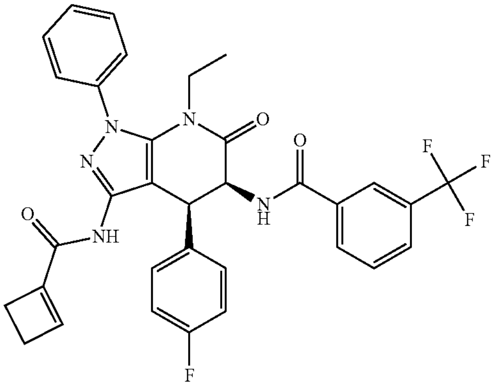
I-256
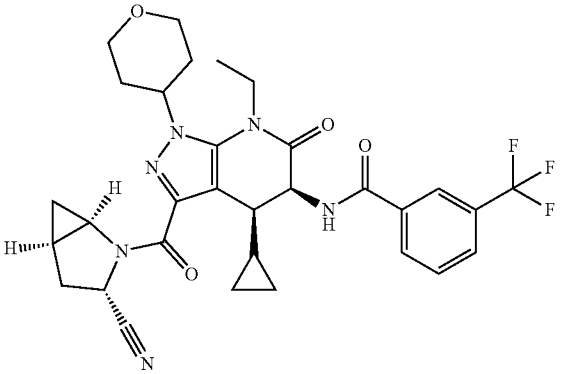
I-703
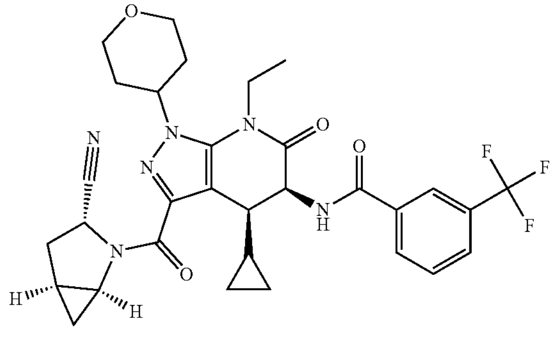

-continued

I-363

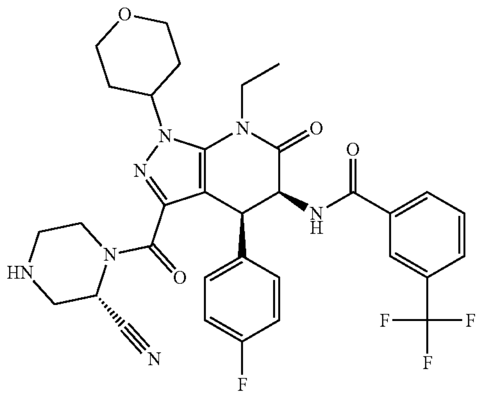

and

I-552

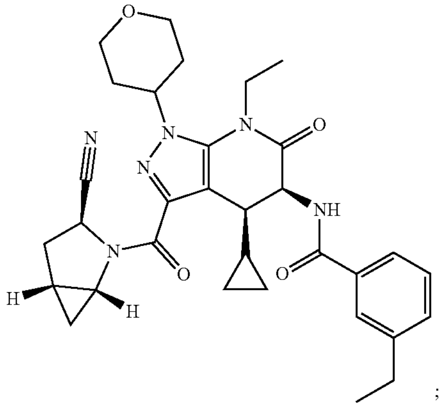

;

or a pharmaceutically acceptable salt thereof.

3. The compound of claim 1, wherein the compound is of the following structure:

I-3a

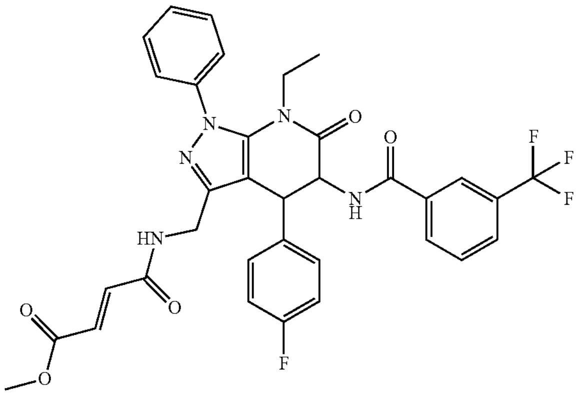

or a pharmaceutically acceptable salt thereof.

4. The compound of claim 1, wherein the compound is of the following structure:

I-5a

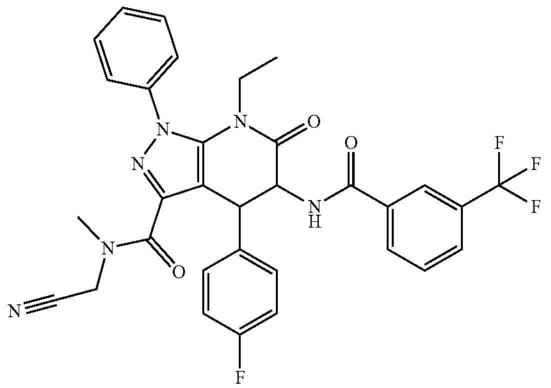

or a pharmaceutically acceptable salt thereof.

5. The compound of claim 1, wherein the compound is of the following structure:

I-256a

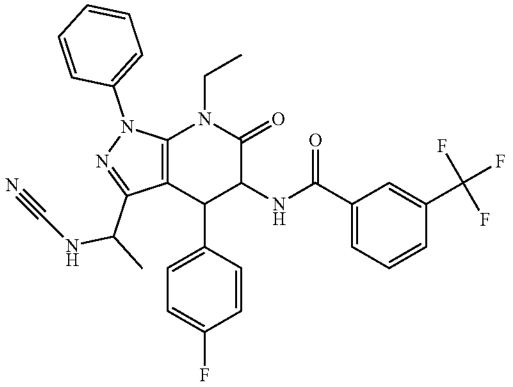

or a pharmaceutically acceptable salt thereof.

6. The compound of claim 1, wherein the compound is of the following structure:

I-34a

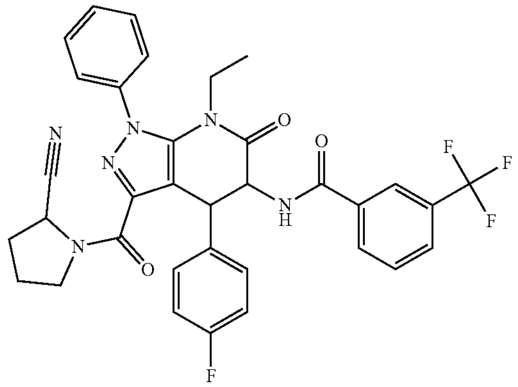

or a pharmaceutically acceptable salt thereof.

7. The compound of claim 1, wherein the compound is of the following structure:

I-49a

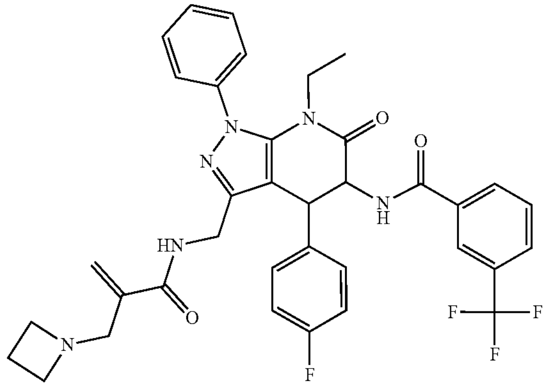

or a pharmaceutically acceptable salt thereof.

8. The compound of claim 1, wherein the compound is of the following structure:

I-92a

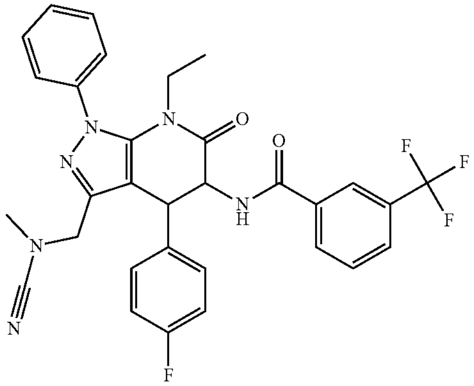

or a pharmaceutically acceptable salt thereof.

9. The compound of claim 1, wherein the compound is of the following structure:

I-112a

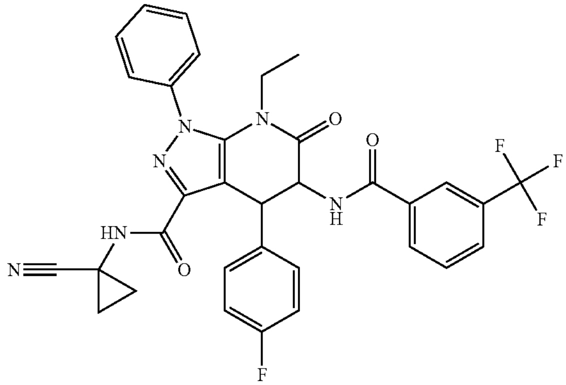

or a pharmaceutically acceptable salt thereof.

10. The compound of claim 1, wherein the compound is of the following structure:

I-140a

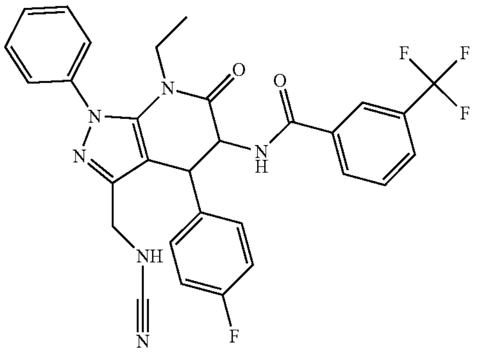

or a pharmaceutically acceptable salt thereof.

11. The compound of claim 1, wherein the compound is of the following structure:

I-152a

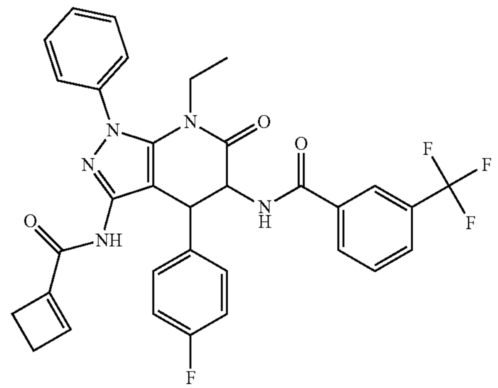

or a pharmaceutically acceptable salt thereof.

12. The compound of claim 1, wherein the compound is of the following structure:

I-256b

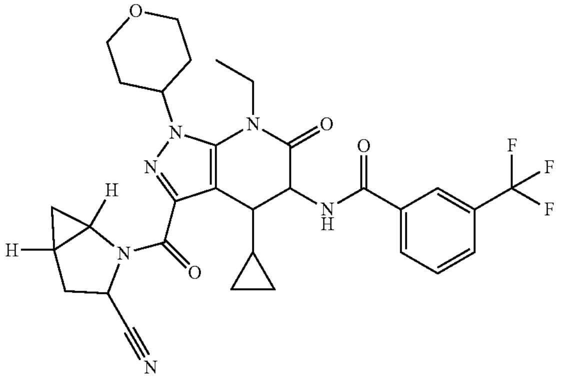

or a pharmaceutically acceptable salt thereof.

13. The compound of claim 1, wherein the compound is of the following structure:

I-363a

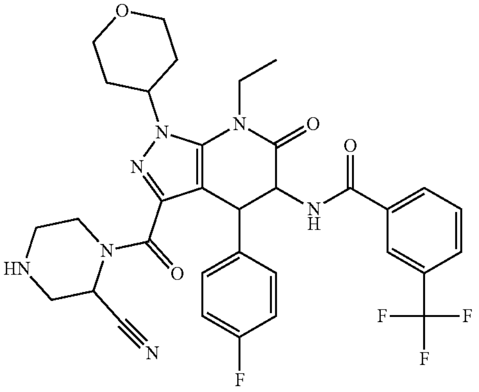

or a pharmaceutically acceptable salt thereof.

14. The compound of claim 1, wherein the compound is of the following structure:

I-552a

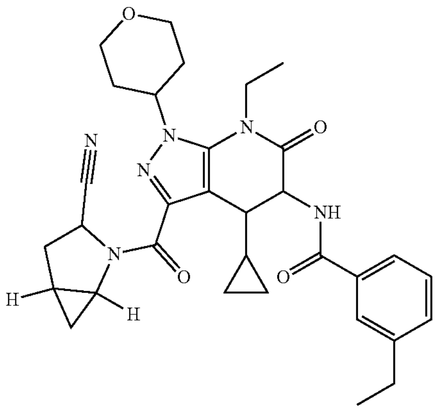

or a pharmaceutically acceptable salt thereof.

15. The compound of claim 2, wherein the compound is of the following structure:

I-3

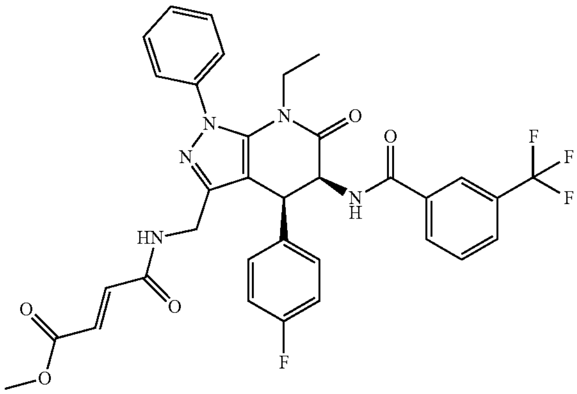

or a pharmaceutically acceptable salt thereof.

16. The compound of claim 2, wherein the compound is of the following structure:

I-5

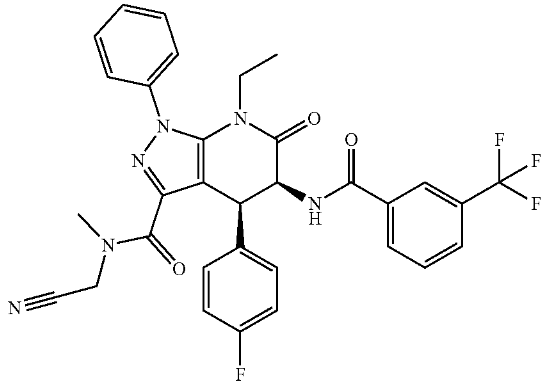

or a pharmaceutically acceptable salt thereof.

17. The compound of claim 2, wherein the compound is of the following structure:

I-13

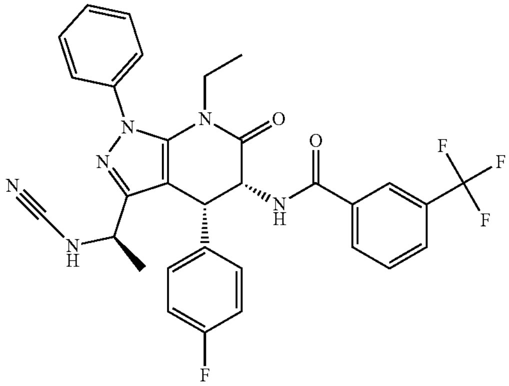

or a pharmaceutically acceptable salt thereof.

18. The compound of claim 2, wherein the compound is of the following structure:

I-34

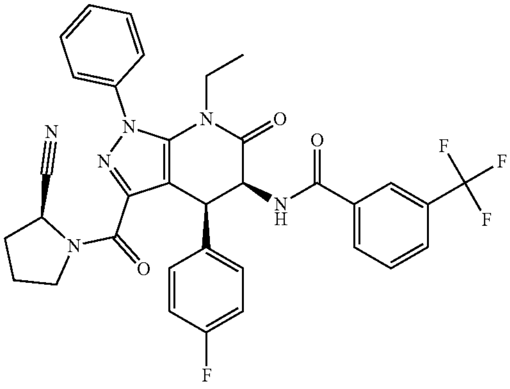

or a pharmaceutically acceptable salt thereof.

19. The compound of claim 2, wherein the compound is of the following structure:

I-49

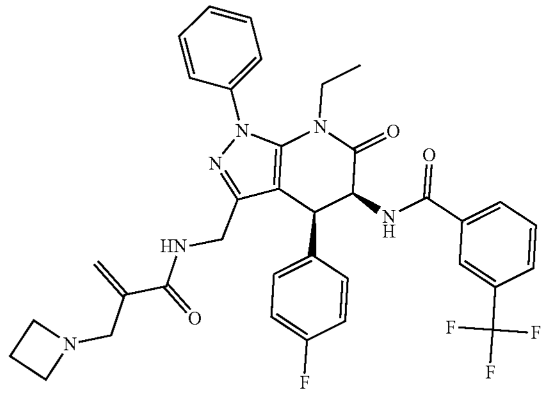

I-139

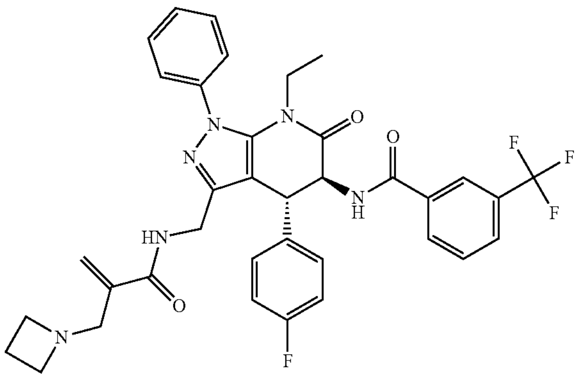

or a pharmaceutically acceptable salt thereof.

20. The compound of claim 2, wherein the compound is of the following structure:

I-73

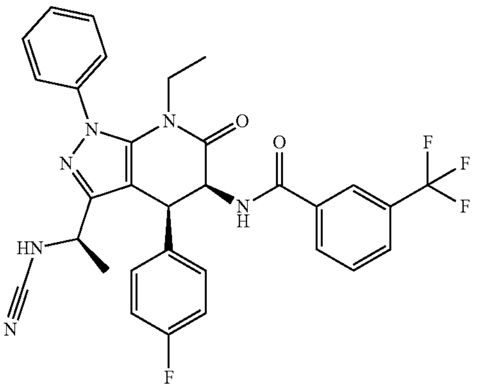

or a pharmaceutically acceptable salt thereof.

21. The compound of claim 2, wherein the compound is of the following structure:

I-92

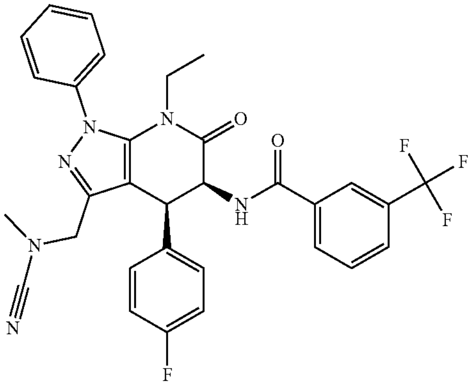

or a pharmaceutically acceptable salt thereof.

22. The compound of claim 2, wherein the compound is of the following structure:

I-112

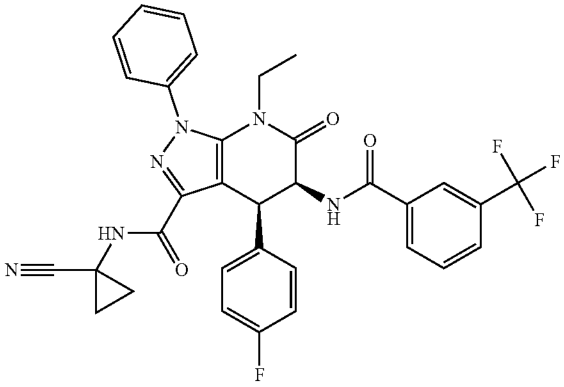

or a pharmaceutically acceptable salt thereof.

23. The compound of claim 2, wherein the compound is of the following structure:

I-140

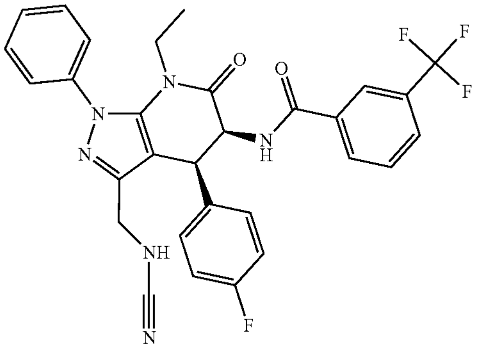

or a pharmaceutically acceptable salt thereof.

24. The compound of claim 2, wherein the compound is of the following structure:

I-152

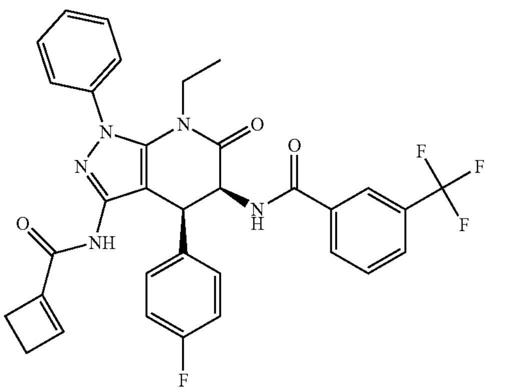

or a pharmaceutically acceptable salt thereof.

25. The compound of claim 2, wherein the compound is of the following structure:

I-256

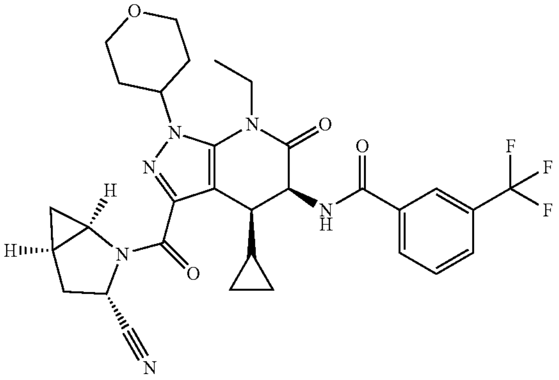

or a pharmaceutically acceptable salt thereof.

26. The compound of claim 2, wherein the compound is of the following structure:

I-703

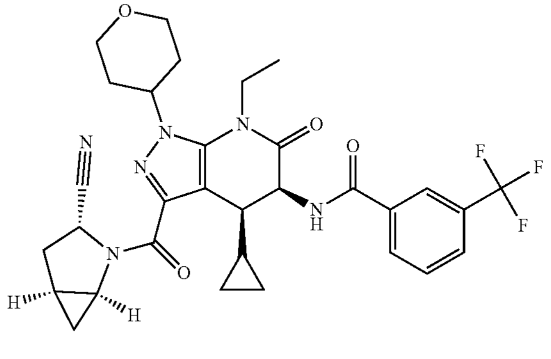

or a pharmaceutically acceptable salt thereof.

27. The compound of claim 2, wherein the compound is of the following structure:

I-363

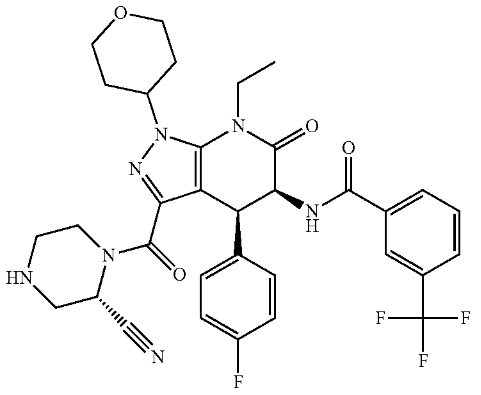

or a pharmaceutically acceptable salt thereof.

28. The compound of claim 2, wherein the compound is of the following structure:

I-552

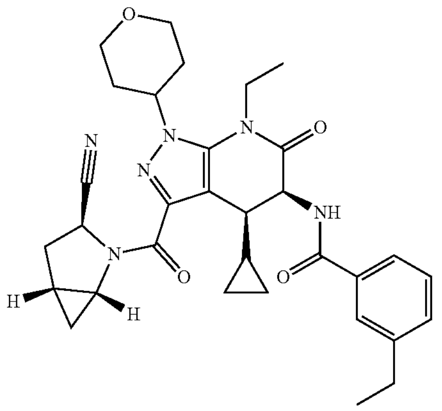

or a pharmaceutically acceptable salt thereof.

29. A pharmaceutical composition comprising the compound of claim 1, or a pharmaceutically acceptable salt thereof, and a pharmaceutically acceptable carrier.

30. A pharmaceutical composition comprising the compound of claim 2, or a pharmaceutically acceptable salt thereof, and a pharmaceutically acceptable carrier.

* * * * *